US010195213B2

(12) United States Patent
David

(10) Patent No.: US 10,195,213 B2
(45) Date of Patent: Feb. 5, 2019

(54) CHEMICAL ENTITIES THAT KILL SENESCENT CELLS FOR USE IN TREATING AGE-RELATED DISEASE

(71) Applicant: Unity Biotechnology, Inc., San Francisco, CA (US)

(72) Inventor: Nathaniel David, San Francisco, CA (US)

(73) Assignee: UNITY BIOTECHNOLOGY, INC., San Francisco, CA (US)

( * ) Notice: Subject to any disclaimer, the term of this patent is extended or adjusted under 35 U.S.C. 154(b) by 0 days.

(21) Appl. No.: 15/069,769

(22) Filed: Mar. 14, 2016

(65) Prior Publication Data

US 2017/0281649 A1    Oct. 5, 2017

Related U.S. Application Data

(60) Provisional application No. 62/177,434, filed on Mar. 13, 2015.

(51) Int. Cl.
| | | |
|---|---|---|
| *A61K 31/05* | (2006.01) | |
| *A61K 31/575* | (2006.01) | |
| *A61K 9/00* | (2006.01) | |
| *A61K 31/4025* | (2006.01) | |
| *A61K 31/365* | (2006.01) | |
| *A61K 31/167* | (2006.01) | |
| *A61K 31/541* | (2006.01) | |
| *A61K 31/4709* | (2006.01) | |
| *A61K 31/352* | (2006.01) | |
| *A61K 31/4741* | (2006.01) | |
| *A61K 31/426* | (2006.01) | |
| *A61K 31/427* | (2006.01) | |
| *A61K 31/433* | (2006.01) | |
| *A61K 31/496* | (2006.01) | |
| *A61K 31/138* | (2006.01) | |
| *A61K 31/4178* | (2006.01) | |
| *A61K 31/11* | (2006.01) | |
| *A61K 31/122* | (2006.01) | |
| *A61K 31/166* | (2006.01) | |

(52) U.S. Cl.
CPC .......... *A61K 31/575* (2013.01); *A61K 9/0019* (2013.01); *A61K 31/05* (2013.01); *A61K 31/11* (2013.01); *A61K 31/122* (2013.01); *A61K 31/138* (2013.01); *A61K 31/166* (2013.01); *A61K 31/167* (2013.01); *A61K 31/352* (2013.01); *A61K 31/365* (2013.01); *A61K 31/4025* (2013.01); *A61K 31/4178* (2013.01); *A61K 31/426* (2013.01); *A61K 31/427* (2013.01); *A61K 31/433* (2013.01); *A61K 31/4709* (2013.01); *A61K 31/4741* (2013.01); *A61K 31/496* (2013.01); *A61K 31/541* (2013.01)

(58) Field of Classification Search
None
See application file for complete search history.

(56) References Cited

U.S. PATENT DOCUMENTS

| | | |
|---|---|---|
| 6,277,844 B1 | 8/2001 | Spector et al. |
| 6,492,389 B1 | 12/2002 | Huang et al. |
| 6,703,382 B2 | 3/2004 | Wang et al. |
| 7,390,799 B2 | 6/2008 | Bruncko et al. |
| 7,642,260 B2 | 1/2010 | Bruncko et al. |
| 7,709,467 B2 | 5/2010 | Bruncko et al. |
| 7,714,005 B2 | 5/2010 | Chen et al. |
| 7,767,684 B2 | 8/2010 | Bruncko et al. |
| 7,842,681 B2 | 11/2010 | Elmore et al. |
| 7,857,804 B2 | 12/2010 | McCaffrey et al. |
| 7,906,505 B2 | 3/2011 | Bruncko et al. |
| 7,973,161 B2 | 7/2011 | Bruncko et al. |
| 8,034,779 B2 | 10/2011 | Distelhorst et al. |
| 8,039,668 B2 | 10/2011 | Pellecchia |
| 8,114,893 B2 | 2/2012 | Baell et al. |
| 8,168,645 B2 | 5/2012 | Baell et al. |
| 8,188,077 B2 | 5/2012 | Ding et al. |
| 8,232,273 B2 | 7/2012 | Baell et al. |
| 8,338,466 B2 | 12/2012 | Kunzer et al. |
| 8,343,967 B2 | 1/2013 | Ding et al. |
| 8,426,422 B2 | 4/2013 | Hexamer et al. |
| 8,501,992 B2 | 8/2013 | Kim et al. |
| 8,518,970 B2 | 8/2013 | Baell et al. |
| 8,546,399 B2 | 10/2013 | Bruncko et al. |
| 8,557,983 B2 | 10/2013 | Bruncko et al. |
| 8,563,735 B2 | 10/2013 | Bruncko et al. |
| 8,580,794 B2 | 11/2013 | Bruncko et al. |

(Continued)

FOREIGN PATENT DOCUMENTS

| | | |
|---|---|---|
| WO | WO-03028443 A1 | 4/2003 |
| WO | WO-2005112951 A1 | 12/2005 |

(Continued)

OTHER PUBLICATIONS

Iannitti, Tommaso. Intra-Articular Injections for the Treatment of Osteoarthritis. Drugs RD 11(1), (2011), 13-27.*
Billard. BH3 mimetics: status of the field and new developments. Mol Cancer Ther. Sep. 2013;12(9)1691-700. doi: 10.1158/1535-7163.MCT-13/0058. Epub Aug. 23, 2013.
Chang, et al. Clearance of senescent cells by ABT263 rejuvenates aged hematopoietic stem cells in mice. Nat Med. Dec. 14, 2015. doi: 10.1038/nm.4010.

(Continued)

*Primary Examiner* — Samantha L Shterengarts
(74) *Attorney, Agent, or Firm* — Michael Schiff; Wilson Sonsini Goodrich & Rosati

(57) ABSTRACT

Disclosed herein are compounds that are effective for treatment of various disease states associated with senescence. The disclosed compounds can be used to eliminate senescent cells for disease treatment. The dosing of the compounds includes both single administration and regimens of cycling dosages.

8 Claims, No Drawings

(56) References Cited

U.S. PATENT DOCUMENTS

| | | |
|---|---|---|
| 8,586,754 B2 | 11/2013 | Bruncko et al. |
| 8,614,318 B2 | 12/2013 | Bruncko et al. |
| 8,624,027 B2 | 1/2014 | Shah et al. |
| 8,759,520 B2 | 6/2014 | East et al. |
| 8,809,352 B2 | 8/2014 | Miller-Moslin et al. |
| 8,865,901 B2 | 10/2014 | Hockenbery et al. |
| 8,937,193 B2 | 1/2015 | Pellecchia et al. |
| 2004/0242886 A1 | 12/2004 | Gupta et al. |
| 2004/0248877 A1 | 12/2004 | Gupta et al. |
| 2006/0252801 A1 | 11/2006 | Chen et al. |
| 2009/0105319 A1* | 4/2009 | Pellecchia ............... C07C 39/14 514/367 |
| 2009/0124675 A1 | 5/2009 | Pellecchia |
| 2010/0160322 A1 | 6/2010 | Bruncko et al. |
| 2010/0292200 A1 | 11/2010 | Kile et al. |
| 2011/0091552 A1 | 4/2011 | McCaffrey et al. |
| 2011/0218155 A1 | 9/2011 | Walensky et al. |
| 2011/0251188 A1 | 10/2011 | Zhang et al. |
| 2012/0028925 A1 | 2/2012 | Tao et al. |
| 2012/0108590 A1 | 5/2012 | Birtalan et al. |
| 2012/0129853 A1 | 5/2012 | Elmore et al. |
| 2012/0172285 A1 | 7/2012 | Walensky et al. |
| 2012/0190688 A1 | 7/2012 | Bruncko et al. |
| 2012/0269901 A1 | 10/2012 | Reed et al. |
| 2012/0277210 A1 | 11/2012 | Catron et al. |
| 2013/0035304 A1 | 2/2013 | Walensky et al. |
| 2013/0096120 A1 | 4/2013 | Wang et al. |
| 2013/0096121 A1 | 4/2013 | Wang et al. |
| 2013/0184278 A1 | 7/2013 | Kunzer et al. |
| 2013/0267514 A1 | 10/2013 | Bruncko et al. |
| 2013/0267534 A1 | 10/2013 | Bruncko et al. |
| 2013/0295185 A1 | 11/2013 | Sebti et al. |
| 2013/0296295 A1 | 11/2013 | Bruncko et al. |
| 2014/0005190 A1 | 1/2014 | Baell et al. |
| 2014/0057889 A1 | 2/2014 | Bruncko et al. |
| 2014/0057890 A1 | 2/2014 | Bruncko et al. |
| 2014/0066621 A1 | 3/2014 | Bruncko et al. |
| 2014/0073640 A1 | 3/2014 | Judd et al. |
| 2014/0088106 A1 | 3/2014 | Bruncko et al. |
| 2014/0094471 A1 | 4/2014 | Bruncko et al. |
| 2014/0107119 A1 | 4/2014 | Bruncko et al. |
| 2014/0113910 A1 | 4/2014 | Bruncko et al. |
| 2014/0135318 A1 | 5/2014 | Borzilleri et al. |
| 2014/0275082 A1 | 9/2014 | Tao et al. |
| 2014/0343093 A1 | 11/2014 | Ford et al. |
| 2014/0350014 A1 | 11/2014 | Ford et al. |
| 2014/0357633 A1 | 12/2014 | Ford et al. |
| 2014/0357666 A1 | 12/2014 | Visser et al. |
| 2017/0056421 A1 | 3/2017 | Zhou et al. |

FOREIGN PATENT DOCUMENTS

| | | |
|---|---|---|
| WO | WO-2008017121 A1 | 2/2008 |
| WO | WO-2008017123 A1 | 2/2008 |
| WO | WO-2008030836 A2 | 3/2008 |
| WO | WO-2008061208 A2 | 5/2008 |
| WO | WO-2008113131 A1 | 9/2008 |
| WO | WO-2009036035 A1 | 3/2009 |
| WO | WO-2009036051 A1 | 3/2009 |
| WO | WO-2009039553 A1 | 4/2009 |
| WO | WO-2010024783 A1 | 3/2010 |
| WO | WO-2010065824 A2 | 6/2010 |
| WO | WO-2010065865 A2 | 6/2010 |
| WO | WO-2010067067 A1 | 6/2010 |
| WO | WO-2010080478 A1 | 7/2010 |
| WO | WO-2010080503 A1 | 7/2010 |
| WO | WO-2010083441 A2 | 7/2010 |
| WO | WO-2010083442 A1 | 7/2010 |
| WO | WO-2010138588 A2 | 12/2010 |
| WO | WO-2011029842 A1 | 3/2011 |
| WO | WO-2011068560 A1 | 6/2011 |
| WO | WO-2011068561 A1 | 6/2011 |
| WO | WO-2011119345 A2 | 9/2011 |
| WO | WO-2011146674 A2 | 11/2011 |
| WO | WO-2011149492 A1 | 12/2011 |
| WO | WO-2011150016 A1 | 12/2011 |
| WO | WO-2012009347 A2 | 1/2012 |
| WO | WO-2012031103 A2 | 3/2012 |
| WO | WO-2012058392 A1 | 5/2012 |
| WO | WO-2012071374 A1 | 5/2012 |
| WO | WO-2012121758 A1 | 9/2012 |
| WO | WO-2013052608 A1 | 4/2013 |
| WO | WO-2013055895 A1 | 4/2013 |
| WO | WO-2013055897 A1 | 4/2013 |
| WO | WO-2013096049 A1 | 6/2013 |
| WO | WO-2014028381 A1 | 2/2014 |
| WO | WO-2014047427 A2 | 3/2014 |
| WO | WO-2014110476 A2 | 7/2014 |
| WO | WO-2014158528 A1 | 10/2014 |
| WO | WO-2015031608 A1 | 3/2015 |
| WO | WO-2015116740 A1 | 8/2015 |
| WO | WO-2015171591 A1 | 11/2015 |

OTHER PUBLICATIONS

Siddiqui, et al. The mystery of BCL2 family: Bcl-2 proteins and apoptosis: an update. Arch Toxicol. Mar. 2015;89(3):289-317. doi: 10.1007/s00204-014-1448-7. Epub Jan. 25, 2015.

UAMS News Bureau. UAMS Research Findings Show Radiation, Aging Effects Can Be Cleared with Drug; Findings Published in Nature Medicine. www.uamshealth.com/news. Dec. 14, 2015. 2 pages.

Uraoka, et al. Loss of bcl-2 during the senescence exacerbates the impaired angiogenic functions in endothelial cells by deteriorating the mitochondrial redox state. Hypertension. Aug. 2011;58(2):254-63. doi: 10.1161/HYPERTENSIONAHA.111.176701. Epub Jul. 5, 2011.

Wang. Senescent human fibroblasts resist programmed cell death, and failure to suppress bcl2 is involved. Cancer Res. Jun. 1, 1995;55(11):2284-92.

* cited by examiner

CHEMICAL ENTITIES THAT KILL SENESCENT CELLS FOR USE IN TREATING AGE-RELATED DISEASE

CROSS-REFERENCE

This application claims the benefit of U.S. Provisional Patent Application No. 62/177,434, filed on Mar. 13, 2015, which is incorporated by reference in its entirety.

BACKGROUND

Cellular senescence is the irreversible growth arrest of mitotic cells that can lead to altered phenotypes, and consequently impair tissue function and predispose tissues to disease development. Senescent cells accumulate in tissues and organs as an individual ages, and are implicated in a variety of diseases and disorders, including aging-related diseases. The elimination of senescent cells can be a viable treatment for aging-related diseases.

SUMMARY OF THE INVENTION

In some embodiments, the invention provides a method for treating a senescent cell-associated condition, the method comprising administering to a subject in need thereof a therapeutically-effective amount of a compound described herein, or a pharmaceutically-acceptable salt thereof.

DETAILED DESCRIPTION

Aging is a risk factor for most chronic diseases, disabilities, and declining health. Senescent cells, which are cells in replicative arrest, accumulate as an individual ages and can contribute partially or significantly to cell and tissue deterioration that underlies aging and age related diseases. Cells can also become senescent after exposure to an environmental, chemical, or biological insult or as a result of a disease. Provided herein are methods and agents for selective killing of senescent cells that are associated with numerous pathologies and diseases, including age-related pathologies and diseases. As disclosed herein, senescent cell-associated diseases and disorders can be treated by administering a compound described herein, or a pharmaceutically-acceptable salt thereof.

A compound described herein can selectively destroy, kill, remove, or facilitate destruction of senescent cells. A compound described herein can destroy or kill a senescent cell in a biologically, clinically, or statistically-significant manner in contrast to a non-senescent cell. A compound described herein can be used in an amount and for a time sufficient that selectively kills established senescent cells but is insufficient to kill a non-senescent cell in a clinically significant or biologically significant manner. In some embodiments, a compound described herein alters at least one signaling pathway in a manner that induces, initiates, stimulates, triggers, activates, or promotes and results in death of the senescent cell. Assessment of the effectiveness of a compound described herein can include comparing the symptoms of the subject receiving treatment with a compound described herein with those of a subject without such treatment or with placebo treatment.

Indications.

The senescent cell associated disease or disorder treated by a compound described herein includes a cardiovascular disease or disorder, inflammatory disease or disorder, pulmonary disease or disorder, neurological disease or disorder, metabolic disease or disorder, dermatological disease or disorder, a metastasis, a chemotherapy or radiotherapy-induced side effect, age-related disease or disorder, a premature aging disease or disorder, and a sleep disorder.

Cardiovascular Conditions.

In some embodiments, the disclosure provides methods for treating a senescent cell-associated condition, the method comprising administering a therapeutically-effective amount of a compound described herein to a subject in need thereof, wherein the senescent cell-associated condition is a cardiovascular condition. Non-limiting examples of cardiovascular conditions, include, but are not limited to angina, arrhythmia, atherosclerosis, cardiomyopathy, congestive heart failure, coronary artery disease (CAD), carotid artery disease, endocarditis, heart attack, coronary thrombosis, myocardial infarction (MI), high blood pressure/hypertension, aortic aneurysm, brain aneurysm, cardiac fibrosis, cardiac diastolic dysfunction, hypercholesterolemia/hyperlipidemia, mitral valve prolapse, peripheral vascular disease, peripheral artery disease (PAD), cardiac stress resistance, and stroke.

A cardiovascular condition can be associated with or caused by arteriosclerosis. An atherosclerotic plaque can be stabilized by administering a compound described herein to a subject in need thereof. In some embodiments, the atherosclerotic plaque is stabilized in a blood vessel, for example, an artery, of a subject, thereby reducing the likelihood of occurrence or delaying the occurrence of a thrombotic event, such as a stroke or MI. A compound described herein can reduce the lipid content or fibrous cap thickness of an atherosclerotic plaque in a subject in need thereof. Fibrous cap formation can occur from the migration and proliferation of vascular smooth muscle cells and from matrix depositions. A thin fibrous cap can contribute to plaque instability and to increased risk of rupture. Such methods can reduce the likelihood of occurrence or delay the occurrence of a thrombotic event, such as a stroke or MI.

A compound described herein can inhibit, reduce, or cause a decrease in the formation of an atherosclerotic plaque in a subject in need thereof, or reduce, decrease, or diminish the amount, or level, of a plaque in a subject in need thereof. Reduction in the amount of a plaque in a blood vessel, for example, an artery, can be determined, for example, by a decrease in surface area of the plaque, or by a decrease in the extent, degree, or percent occlusion of a blood vessel, for example an artery, which can be determined by angiography or other visualizing methods.

A compound described herein can increase, improve, promote, or enhance stability of an atherosclerotic plaque in a subject in need thereof.

The effectiveness of a compound described herein in treating a cardiovascular disease or disorder can be assessed by one or any combination of diagnostic methods, including physical examination and assessment, monitoring of clinical symptoms, and performance of analytical tests and methods. Analytical tests and methods include, but are not limited to, angiography, electrocardiography, stress test, or non-stress test.

Inflammatory and Autoimmune Conditions.

In some embodiments, the disclosure provides methods for treating a senescent cell-associated condition, the method comprising administering a therapeutically-effective amount of a compound described herein to a subject in need thereof, wherein the senescent cell-associated condition is an inflammatory condition. Inflammatory conditions include, but are not limited to, osteoarthritis, osteoporosis, oral mucositis, rheumatoid arthritis, inflammatory bowel disease, kyphosis, herniated intervertebral disc, ulcerative colitis, Crohn's disease, ulcerative asthma, renal fibrosis, liver fibrosis, pancreatic fibrosis, cardiac fibrosis, skin wound healing, and oral submucous fibrosis.

In some embodiments, the disclosure provides methods for treating or reducing the likelihood of conditions resulting from a host immune response to an organ transplant in a subject in need thereof. Non-limiting examples of an organ transplant include a kidney organ transplant, a bone marrow transplant, a liver transplant, a lung transplant, and a heart transplant. In some embodiments, the disclosure provides methods for treating graft-vs-host disease in a subject in need thereof.

In some embodiments, the disclosure provides methods for reducing or inhibiting loss or erosion of proteoglycan layers in a joint in a subject in need thereof. The disclosure provides methods for reducing inflammation in an inflamed joint in a subject in need thereof. A compound described herein can stimulate, enhance, or induce production of collagen in a subject in need thereof, for example, type 2 collagen. A compound described herein can reduce an amount, or level, of an inflammatory cytokine in a subject in need thereof, for example, IL-6. A compound described herein can decrease, inhibit, or reduce the production of metalloproteinase 13 (MMP-13) in a subject in need thereof. A compound described herein can reduce the likelihood of, inhibit, or decrease the erosion of bone in a subject in need thereof. A compound described herein can be administered directly to an osteoarthritic joint, for example, intraarticularly, topically, transdermally, intradermally, or subcutaneously. A compound described herein can restore, improve, or inhibit deterioration of strength of a joint in a subject in need thereof. A compound described herein can reduce joint pain in a subject in need thereof. In some embodiments, the joint is an osteoarthritic joint.

The effectiveness of a compound described herein in treating an inflammatory condition can be assessed by one or any combination of diagnostic methods, including physical examination, assessment and monitoring of clinical symptoms, and performance of analytical tests to monitor the health status of a subject. Physical examination can include, for example, determining tenderness, swelling or redness of the affected joint, and assessment and monitoring of clinical symptoms. Performance of analytical tests and methods can include, for example, determining the level of inflammatory cytokines or chemokines, X-ray images to determine loss of cartilage as shown by a narrowing of space between the bones in a joint, magnetic resonance imaging (MRI), and providing detailed images of bone and soft tissues.

Pulmonary Conditions.

In some embodiments, the disclosure provides methods for treating a senescent cell-associated condition, the method comprising administering a therapeutically-effective amount of a compound described herein to a subject in need thereof, wherein the senescent cell-associated condition is a pulmonary condition. Pulmonary conditions include, but are not limited to, idiopathic pulmonary fibrosis (IPF), chronic obstructive pulmonary disease (COPD), asthma, cystic fibrosis, bronchiectasis, and emphysema.

In some embodiments, the subject has been exposed to environmental pollutants, for example, silica. A subject can be exposed to an occupational pollutant, for example, dust, smoke, asbestos, or fumes. In some embodiments, the subject has smoked cigarettes.

In some embodiments, the subject has a connective tissue disease. The connective tissue disease can be, for example, rheumatoid arthritis, systemic lupus erythematosus, scleroderma, sarcoidosis, or Wegener's granulomatosis. In some embodiments, the subject has an infection. In some embodiments, the subject has taken or is taking medication or has received radiation therapy to the chest. The medication can be, for example, amiodarone, bleomycin, busufan, methotrexate, or nitrofurantoin.

The effectiveness of a compound described herein in treating a pulmonary condition can be assessed by one or any combination of diagnostic methods including physical examination, determination of patient's medical history, determination of patient's family's medical history, chest X-ray, lung function test, spirometry test, blood test, arterial blood gas analysis, bronchoalveolar lavage, lung biopsy, CT scan, and exercise testing. Methods and techniques that evaluate mechanical functioning of the lung, for example, techniques that measure lung capacitance, elastance, and airway hypersensitivity can be performed. To determine lung function and to monitor lung function throughout treatment, any one of numerous measurements can be obtained, for example, expiratory reserve volume (ERV), forced vital capacity (FVC), forced expiratory volume (FEV) (e.g., FEV in one second, FEV1), FEV1/FEV ratio, forced expiratory flow 25% to 75%, maximum voluntary ventilation (MVV), peak expiratory flow (PEF), and slow vital capacity (SVC). Total lung volumes include total lung capacity (TLC), vital capacity (VC), residual volume (RV), and functional residual capacity (FRC). Gas exchange across alveolar capillary membrane can be measured using diffusion capacity for carbon monoxide (DLCO). Peripheral capillary oxygen saturation ($SpO_2$) can also be measured. Normal oxygen levels can be between 95% and 100%. An $SpO_2$ level below 90% can suggest that the subject has hypoxemia. Values below 80% can be critical and require intervention to maintain brain and cardiac function and avoid cardiac or respiratory arrest.

Neurological Conditions.

In some embodiments, the disclosure provides methods for treating a senescent cell-associated condition, the method comprising administering a therapeutically-effective amount of a compound described herein to a subject in need thereof wherein the senescent cell-associated condition is a neurological condition. Neurological conditions include, but are not limited to, Parkinson's disease, Alzheimer's disease, dementia, amyotrophic lateral sclerosis (ALS), bulbar palsy, pseudobulbar palsy, primary lateral sclerosis, motor neuron dysfunction (MND), mild cognitive impairment (MCI), Huntington's disease, ocular diseases, age-related macular degeneration, glaucoma, vision loss, presbyopia, cataracts, progressive muscular atrophy, lower motor neuron disease, spinal muscular atrophy (SMA), Werdnig-Hoffman Disease (SMA1), SMA2, Kugelberg-Welander Disease (SM3), Kennedy's disease, post-polio syndrome, and hereditary spastic paraplegia.

Non-limiting examples for monitoring the effect of a therapy on inhibiting progression of glaucoma include automated perimetry, gonioscopy, imaging technology, scanning laser tomography, HRT3, laser polarimetry, GDX, ocular coherence tomography, ophthalmoscopy, and pachymeter measurements that determine central corneal thickness.

A compound described herein can delay or inhibit the onset of cataracts, presbyopia, and macular degeneration in a subject in need thereof who is at risk for developing cataracts, presbyopia, and macular degeneration. In some embodiments, the subject is a human subject who is at least 40 years of age.

The effectiveness of a compound described herein in treating a neurological condition can be assessed by one or any combination of diagnostic methods including physical examination, assessment and monitoring of clinical symptoms, and performance of analytical tests and methods described herein Metabolic Conditions.

In some embodiments, the disclosure provides methods for treating a senescent cell-associated conditions, the method comprising administering a therapeutically-effective amount of a compound described herein to a subject in need thereof wherein the senescent cell-associated condition is a metabolic condition. Metabolic conditions include, but are not limited to, diabetes (Type 1 or Type 2), metabolic syndrome, diabetic ulcers, obesity, renal dysfunction, nephrological pathology, and glomerular disease.

The effectiveness of a compound described herein in treating a metabolic condition can be assessed by one or any combination of diagnostic methods including physical examination assessment and monitoring of clinical symptoms, and performance of analytical tests and methods, such as those described herein. A subject who is receiving a compound described herein for treatment or reduction in the likelihood of developing diabetes can be monitored, for example, by assaying glucose and insulin tolerance, energy expenditure, body composition, fat tissue, skeletal muscle, and liver inflammation, or lipotoxicity.

Dermatological Conditions.

In some embodiments, the disclosure provides methods for treating a senescent cell-associated condition, the method comprising administering a therapeutically-effective amount of a compound described herein to a subject in need thereof wherein the senescent cell-associated condition is a dermatological condition. Dermatological conditions include, but are not limited to, psoriasis, eczema, rhytides, pruritis, dysesthesia, papulosquamous disorders, erythroderma, lichen planus, lichenoid dermatosis, atopic dermatitis, eczematous eruptions, eosinophilic dermatosis, reactive neutrophilic dermatosis, pemphigus, pemphigoid, immunobullous dermatosis, fibrohistocytic proliferations of skin, cutaneous lymphomas, and cutaneous lupus.

The effectiveness of a compound described herein in treating a dermatological condition can be assessed by one or any combination of diagnostic methods including physical examination assessment and monitoring of clinical symptoms, and performance of analytical tests and methods, such as those described herein.

Metastasis.

In some embodiments, the disclosure provides methods for treating a senescent cell-associated condition, the method comprising administering a therapeutically-effective amount of a compound described herein to a subject in need thereof wherein the senescent cell-associated condition comprises metastasis, such as metastasis of a cancer.

A compound described herein can reduce the likelihood of metastasis in a subject in need thereof. The compound described herein can be administered one or more days within a window of treatment. In some embodiments, the treatment window is 1, 2, 3, 4, 5, 6, 7, 8, 9, 10, 11, 12, 13, 14, 15, 16, 17, 18, 19, 20, or 21 days. In some embodiments, a compound described herein is administered on two or more days within a treatment window of no longer than 7 days or 14 days; on 3 or more days within a treatment window of no longer than 7 days or 14 days; on 4 or more days within a treatment window of no longer than 7 days or 14 days; on 5 or more days within a treatment window of no longer than 7 days or 14 days; or on 6, 7, 8, 9, 10, 11, 12, 13, or 14 days within treatment window of no longer than 7 days or 14 days.

Chemotherapy and radiotherapy treatment regimens can comprise a finite number of cycles of on-drug therapy followed by off-drug therapy, or comprise a finite timeframe in which the chemotherapy or radiotherapy is administered. The protocols can be determined by clinical trials, drug labels, and clinical staff in conjunction with the subject to be treated. The number of cycles of a chemotherapy or radiotherapy or the total length of time of a chemotherapy or radiotherapy regimen can vary depending on the subject's response to the cancer therapy. A compound described herein can be administered after the treatment regimen of chemotherapy or radiotherapy has been completed.

In some embodiments, the metastasis is a solid tumor. In some embodiments, the metastasis is a liquid tumor. Cancers that are liquid tumors can be those that occur, for example, in blood, bone marrow, and lymph nodes, and can include, for example, leukemia, myeloid leukemia, lymphocytic leukemia, lymphoma, Hodgkin's lymphoma, melanoma, and multiple myeloma. Leukemias include, for example, acute lymphoblastic leukemia (ALL), acute myeloid leukemia (AML), chronic lymphocytic leukemia (CLL), chronic myelogenous leukemia (CML), and hairy cell leukemia. Cancers that are solid tumors include, for example, prostate cancer, testicular cancer, breast cancer, brain cancer, pancreatic cancer, colon cancer, thyroid cancer, stomach cancer, lung cancer, ovarian cancer, Kaposi's sarcoma, skin cancer, squamous cell skin cancer, renal cancer, head and neck cancers, throat cancer, squamous carcinomas that form on the moist mucosal linings of the nose, mouth, throat, bladder cancer, osteosarcoma, cervical cancer, endometrial cancer, esophageal cancer, liver cancer, and kidney cancer. In some embodiments, the condition treated by the methods described herein is metastasis of melanoma cells, prostate cancer cells, testicular cancer cells, breast cancer cells, brain cancer cells, pancreatic cancer cells, colon cancer cells, thyroid cancer cells, stomach cancer cells, lung cancer cells, ovarian cancer cells, Kaposi's sarcoma cells, skin cancer cells, renal cancer cells, head or neck cancer cells, throat cancer cells, squamous carcinoma cells, bladder cancer cells, osteosarcoma cells, cervical cancer cells, endometrial cancer cells, esophageal cancer cells, liver cancer cells, or kidney cancer cells.

The methods described herein can also be used for inhibiting progression of metastatic cancer tumors. Non-limiting examples of cancers include adrenocortical carcinoma, childhood adrenocortical carcinoma, aids-related cancers, anal cancer, appendix cancer, basal cell carcinoma, childhood basal cell carcinoma, bladder cancer, childhood bladder cancer, bone cancer, brain tumor, childhood astrocytomas, childhood brain stem glioma, childhood central nervous system atypical teratoid/rhabdoid tumor, childhood central nervous system embryonal tumors, childhood central nervous system germ cell tumors, childhood craniopharyngioma brain tumor, childhood ependymoma brain tumor, breast cancer, childhood bronchial tumors, carcinoid tumor, childhood carcinoid tumor, gastrointestinal carcinoid tumor, carcinoma of unknown primary, childhood carcinoma of unknown primary, childhood cardiac tumors, cervical cancer, childhood cervical cancer, childhood chordoma, chronic myeloproliferative disorders, colon cancer, colorectal cancer, childhood colorectal cancer, extrahepatic bile duct cancer, ductal carcinoma in situ (DCIS), endometrial cancer, esophageal cancer, childhood esophageal cancer, childhood esthesioneuroblastoma, eye cancer, malignant fibrous histiocytoma of bone, gallbladder cancer, gastric (stomach) cancer, childhood gastric cancer, gastrointestinal stromal tumors (GIST), childhood gastrointestinal stromal tumors (GIST), childhood extracranial germ cell tumor, extragonadal germ cell tumor, gestational trophoblastic tumor, glioma, head and neck cancer, childhood head and neck cancer, hepatocellular cancer, hypopharyngeal cancer, kidney cancer, renal cell kidney cancer, Wilms tumor, childhood kidney tumors, Langerhans cell histiocytosis, laryngeal cancer, childhood laryngeal cancer, leukemia, acute lymphoblastic leukemia (ALL), acute myeloid leukemia (AML), chronic lymphocytic leukemia (CLL), chronic myelogenous leukemia (cml), hairy cell leukemia, lip cancer, liver cancer (primary), childhood liver cancer (primary), lobular carcinoma in situ (LCIS), lung cancer, non-small cell lung cancer, small cell lung cancer, lymphoma, aids-related lymphoma, burkitt lymphoma, cutaneous t-cell lymphoma, Hodgkin lymphoma, non-Hodgkin lymphoma, primary central nervous system lymphoma (CNS), melanoma, childhood melanoma, intraocular melanoma, Merkel cell carcinoma, malignant mesothelioma, childhood malignant mesothelioma, metastatic squamous neck cancer with occult primary, midline tract carcinoma involving NUT gene, mouth cancer, childhood multiple endocrine neoplasia syndromes, mycosis fungoides, myelodysplastic syndromes, myelodysplastic neoplasms, myeloproliferative neoplasms, multiple myeloma, nasal cavity cancer, nasopharyngeal cancer, childhood nasopharyngeal cancer, neuroblastoma, oral cancer, childhood oral cancer, oropharyngeal cancer, ovarian cancer, childhood ovarian cancer, epithelial ovarian cancer, low malignant potential tumor ovarian cancer, pancreatic cancer, childhood pancreatic cancer, pancreatic neuroendocrine tumors (islet cell tumors), childhood papillomatosis, paraganglioma, paranasal sinus cancer, parathyroid cancer, penile cancer, pharyngeal cancer, pheochromocytoma, pituitary tumor, plasma cell neoplasm, childhood pleuropulmonary blastoma, prostate cancer, rectal cancer, renal pelvis transitional cell cancer, retinoblastoma, salivary gland cancer, childhood salivary gland cancer, Ewing sarcoma family of tumors, Kaposi Sarcoma, osteosarcoma, rhabdomyosarcoma, childhood rhabdomyosarcoma, soft tissue sarcoma, uterine sarcoma, Sézary syndrome, childhood skin cancer, nonmelanoma skin cancer, small intestine cancer, squamous cell carcinoma, childhood squamous cell carcinoma, testicular cancer, childhood testicular cancer, throat cancer, thymoma and thymic carcinoma, childhood thymoma and thymic carcinoma, thyroid cancer, childhood thyroid cancer, ureter transitional cell cancer, urethral cancer, endometrial uterine cancer, vaginal cancer, vulvar cancer, and Waldenström macroglobulinemia.

Chemotherapy and Radiotherapy Side Effects.

In some embodiments, the disclosure provides methods for treating a senescent cell-associated condition, the method comprising administering a therapeutically-effective amount of a compound described herein to a subject in need thereof wherein the senescent cell-associated condition is a chemotherapy-induced or radiotherapy-induced side effect. Non-limiting examples of chemotherapeutic agents include anthracyclines, doxorubicin, daunorubicin, taxols, paclitaxel, gemcitabine, pomalidomide, and lenalidomide. Chemotherapy-induced side effects or radiotherapy-induced side effects include, but art not limited to, weight loss, endocrine changes, hormone imbalance, changes in hormome signaling, changes is cardiotoxicity, body composition, reduced ability to be physically active, gastrointestinal toxicity, nausea, vomiting, constipation, anorexia, diarrhea, peripheral neuropathy, fatigue, malaise, low physical activity, hematological toxicity, anemia, hepatotoxicity, alopecia, pain, infection, mucositis, fluid retention, dermatological toxicity, rashes, dermatitis, hyperpigmentation, urticaria, photosensitivity, nail changes, mouth, gum or throat problems, and any toxic side effect caused by a chemotherapy or radiotherapy. In some embodiments, the disclosure provides methods for treating or reducing the likelihood of metastasis comprising administering a compound described herein during an off-chemotherapy or off-radiotherapy time interval or after the chemotherapy or radiotherapy treatment regimen has been completed.

In some embodiments, the chemotherapy-induced side effect is cardiotoxicity and is caused by anthracycline.

In some embodiments, the disclosure provides methods for treating chronic or long term chemotherapy-induced or radiotherapy-induced side effects. Certain toxic effects can appear long after treatment and can result from damage to an organ or system by the therapy. Organ dysfunction, for example, neurological, pulmonary, cardiovascular, and endocrine dysfunction, can be observed in subjects who were treated for cancers during childhood. Chronic or late toxic side effects that occur in subjects who received chemotherapy or radiation therapy include, for example, cardiomyopathy, congestive heart disease, inflammation, early menopause, osteoporosis, infertility, impaired cognitive function, peripheral neuropathy, secondary cancers, cataracts and other vision problems, hearing loss, chronic fatigue, reduced lung capacity, and lung disease.

Age-Related Conditions.

In some embodiments, the disclosure provides methods for treating a senescent cell-associated condition, the method comprising administering a therapeutically-effective amount of a compound described herein to a subject in need thereof wherein the senescent cell-associated condition is an age-related condition. In some embodiments, the age-related condition is caused by exposure to an agent or factor such as irradiation, chemotherapy, smoking tobacco, high-fat/high sugar diet, or other environmental factor. Age-related diseases and disorders include, but are not limited to, herniated intervertebral disc, frailty, hair loss, hearing loss, vision loss, muscle fatigue, skin conditions, skin nevi, wrinkly skin, hyperpigmentation, scarring, keloid, rosacea, vitiligo, ichthyosis vulgaris, dermatomyositis, actinic keratosis, and sarcopenia.

In some embodiments, the disclosure provides methods for extending the lifespan of a mammal comprising administering to a subject a compound described herein.

The effectiveness of a compound described herein in treating an age-related condition can be assessed by one or any combination of diagnostic methods including physical examination, patient self-assessment, assessment and monitoring of clinical symptoms, performance of analytical tests and methods, including clinical laboratory tests, physical tests, and exploratory surgery.

Erdheim-Chester Disease.

In some embodiments, the disclosure provides methods for treating a senescent cell-associated condition, the method comprising administering a compound described herein to a subject in need thereof wherein the senescent cell-associated condition is Erdheim-Chester Disease. Erdheim-Chester disease (ECD) (also known as Erdheim-Chester syndrome or polyostotic sclerosing histiocytosis) is a rare disease characterized by the abnormal multiplication of a specific type of white blood cells called histiocytes, or tissue macrophages. Usually, the onset of ECD is in middle age. ECD involves an infiltration of lipid-laden macrophages, multinucleated giant cells, an inflammatory infiltrate of lymphocytes and histiocytes in the bone marrow, and a generalized sclerosis of the long bones. Radiologic osteosclerosis and histology can be diagnostic features for ECD. Video-assisted thoracoscopic surgery can be used for diagnostic confirmation and also for therapeutic relief of recurrent pericardial fluid drainage.

Premature Aging Conditions.

In some embodiments, the disclosure provides methods for treating a senescent cell-associated condition, the method comprising administering a therapeutically-effective amount of a compound described herein to a subject in need thereof wherein the senescent cell-associated condition is a premature aging disease or disorder. Premature aging diseases and disorders include, but are not limited to Hutchinson-Gilford progeria or Werner's Syndrome.

Sleep Conditions.

In some embodiments, the disclosure provides methods for treating a senescent cell-associated condition, the method comprising administering a therapeutically-effective amount of a compound described herein to a subject in need thereof wherein the senescent cell-associated condition is a sleep condition. Sleep conditions include, but are not limited to, sleep apnea, hypersomnia, cataplexy, sleep fragmentation, sleeping sickness, sleepwalking, night terrors, bed wetting, bruxism, delayed sleep phase disorder (DSPD), hypopnea syndrome, idiopathic hypersomnia, insomnia, Kleine-Levin syndrome, narcolepsy, excessive daytime sleepiness, nocturia, parasomnias, periodic limb movement disorder, nocturnal myoclonus, hypnic jerk, rapid eye movement sleep behavior disorder, restless leg syndrome, obstructive sleep apnea, sleep paralysis, sleepwalking, somniphobia, situational circadian rhythm sleep disorder, shift worker sleep disorder, and jet lag.

Compounds.

In some embodiments, the compound is selected from the group consisting of:

(WEHI-539)

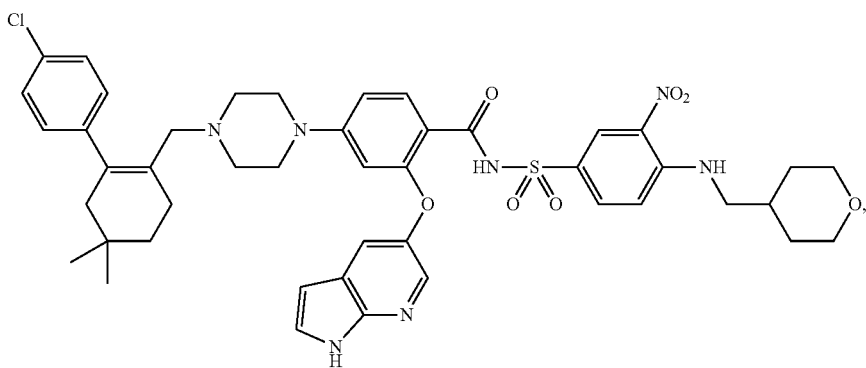

(ABT-199)

-continued
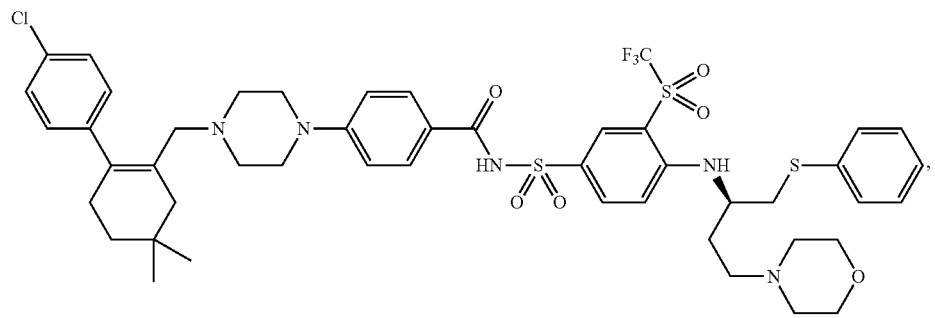
(Navitoclax)
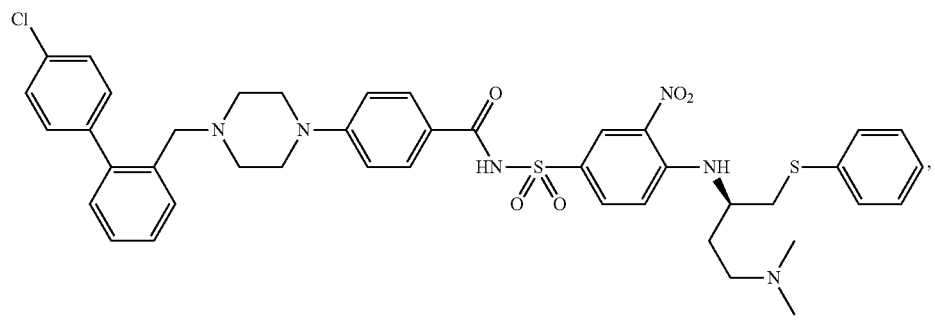
(ABT-737)
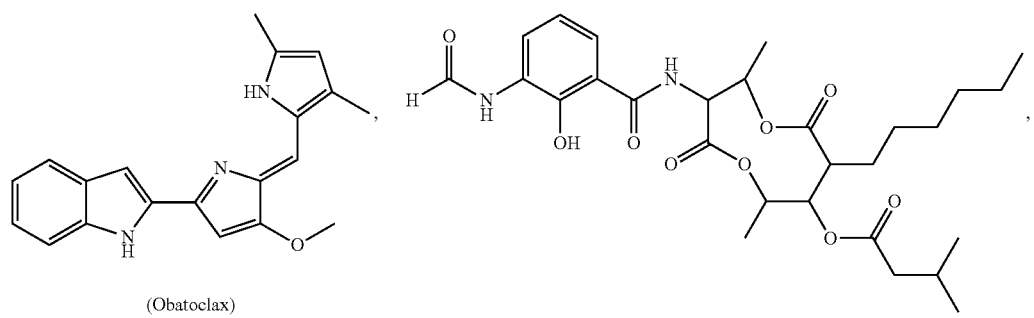
(Obatoclax)
(Antimycin A)
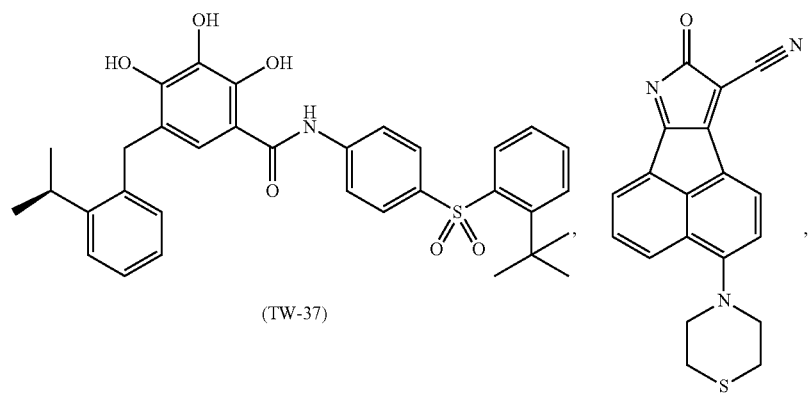
(TW-37)

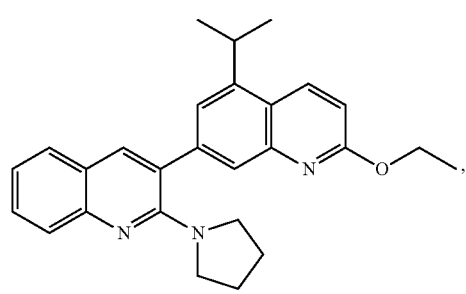
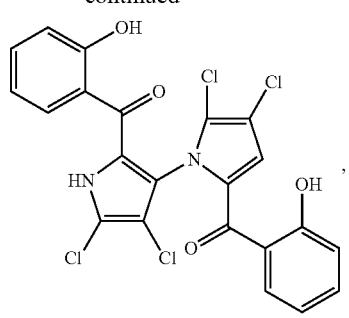
(Maritoclax)
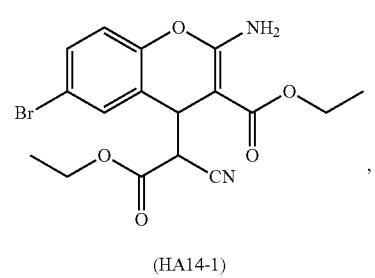
(HA14-1)
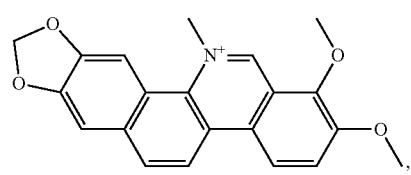
(Chelerythrine)
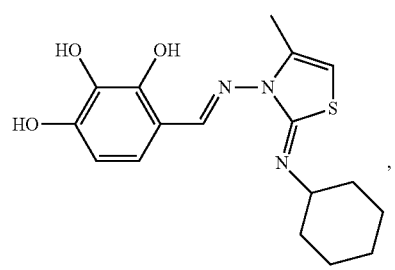
(MIM1)
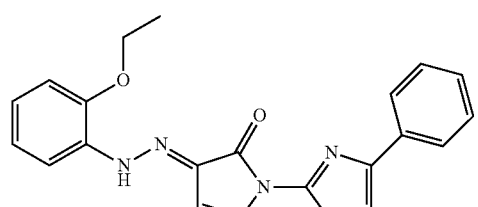
(BAM7)
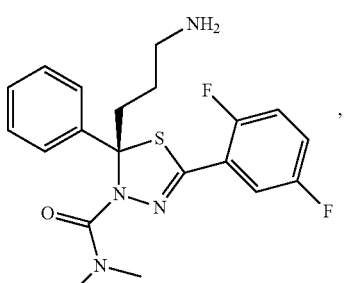
(ARRY 520)
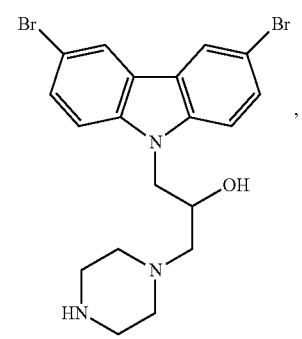
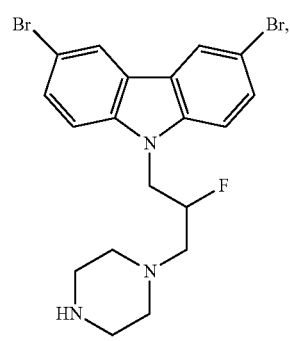
(iMAC2)
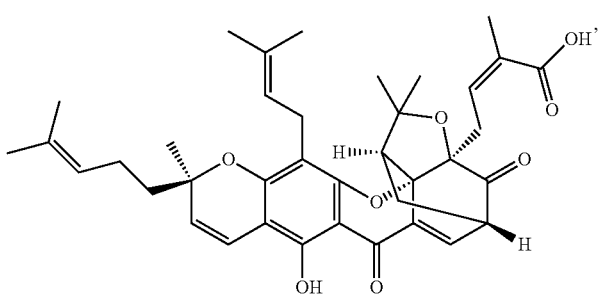
(Gambogic acid)

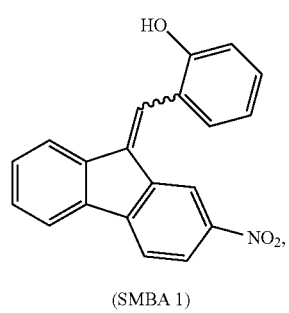
(SMBA 1)
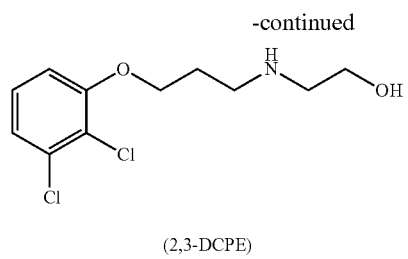
(2,3-DCPE)
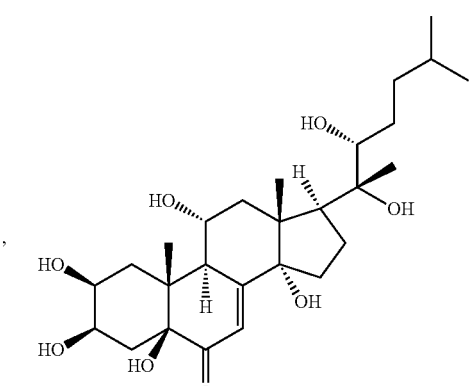
(Muristerone A)
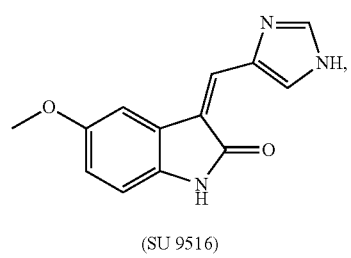
(SU 9516)
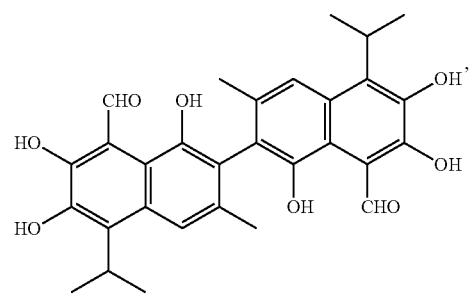
(gossypol)
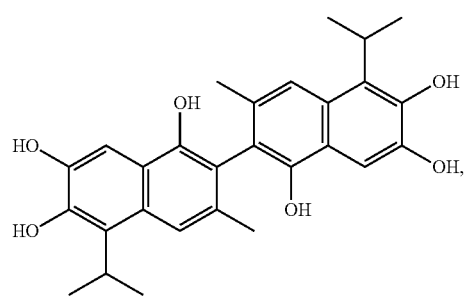
(apogossypol)
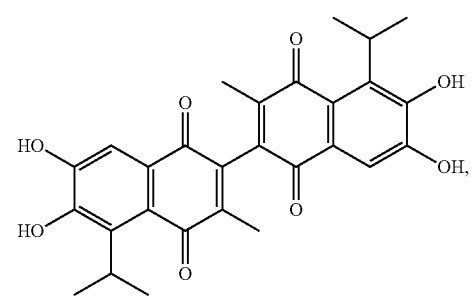
(apogossypolone)

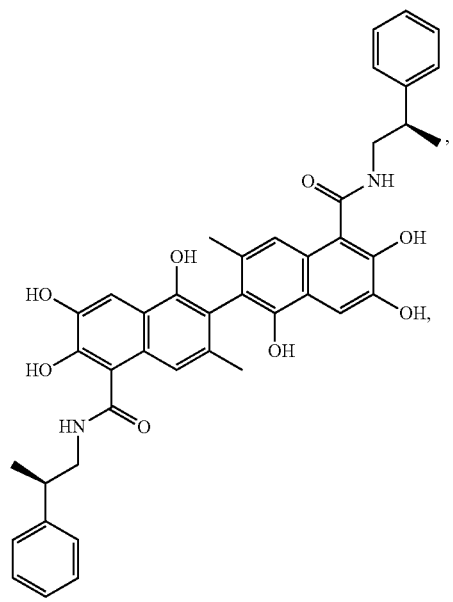
(Sabutoclax)
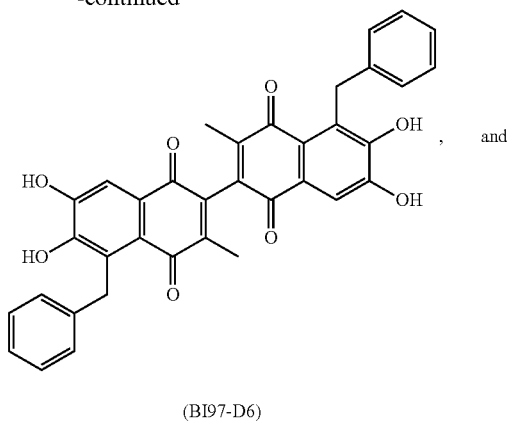
(BI97-D6), and
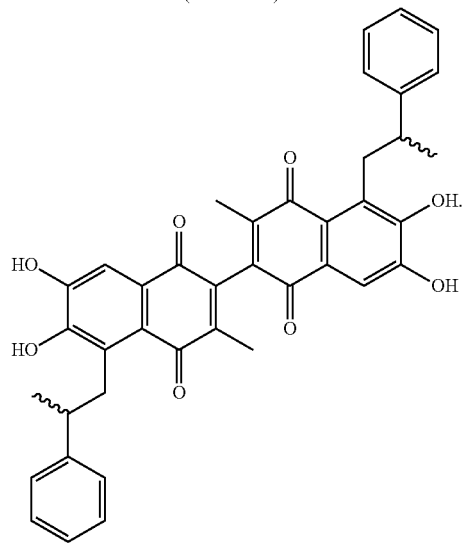
In some embodiments, the compound is selected from the group consisting of:
| Name | Structure |
|---|---|
| N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide | 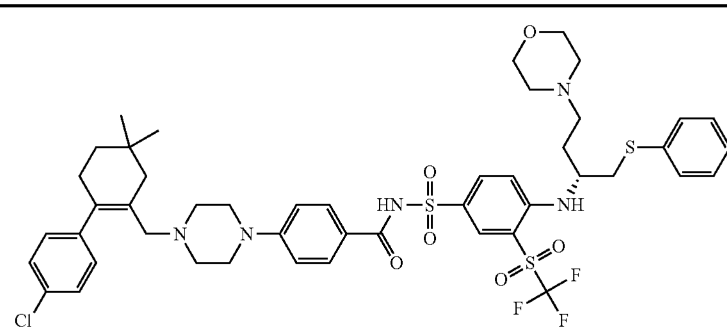 |

| Name | Structure |
|---|---|
| 3-((chloro(difluoro)methyl)sulfonyl)-N-(4-(4-((2-(4-chlorophenyl)-4,4-dimethylcyclohex-1-en-1-yl)methyl)piperazin-1-yl)benzoyl)-4-(((1R)-3-(morpholin-4-yl)-1-((phenylsulfanyl)methyl)propyl)amino)benzenesulfonamide, | 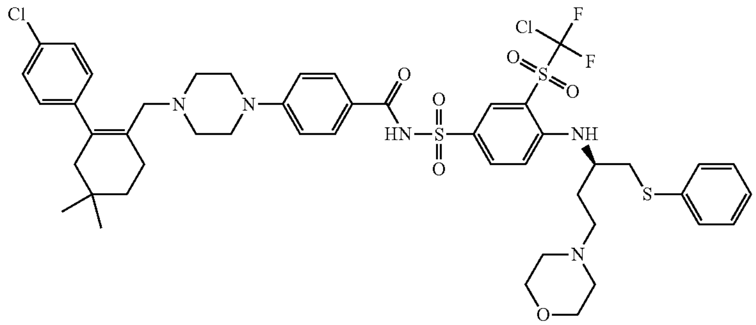 [SMILES: CC1(C)CCC(CN2CCN(c3ccc(C(=O)NS(=O)(=O)c4ccc(N[C@H](CCN5CCOCC5)CSc5ccccc5)c(S(=O)(=O)C(F)(F)Cl)c4)cc3)CC2)=C(c2ccc(Cl)cc2)C1] |
| 3-((chloro(difluoro)methyl)sulfonyl)-N-(4-(4-((2-(4-chlorophenyl)-1-cyclohex-1-en-1-yl)methyl)piperazin-1-yl)benzoyl)-4-(((1R)-3-(morpholin-4-yl)-1-((phenylsulfanyl)methyl)propyl)amino)benzenesulfonamide, | |
| N-(4-(4-((2-(4-chlorophenyl)-5,5-dimethylcyclohex-1-en-1-yl)methyl)piperazin-1-yl)benzoyl)-4-(((1R)-3-(isopropyl(methyl)amino)-1-((phenylsulfanyl)methyl)propyl)amino)-3-((trifluoromethyl)sulfonyl)benzenesulfonamide, | 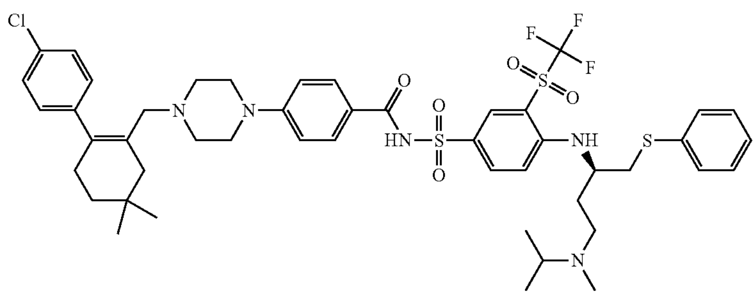 |
| N-(4-(4-((2-(4-chlorophenyl)-1-cyclohepten-1-yl)methyl)piperazin-1-yl)benzoyl)-4-(((1R)-3-(isopropyl(methyl)amino)-1-((phenylsulfanyl)methyl)propyl)amino)-3-((trifluoromethyl)sulfonyl)benzenesulfonamide, | 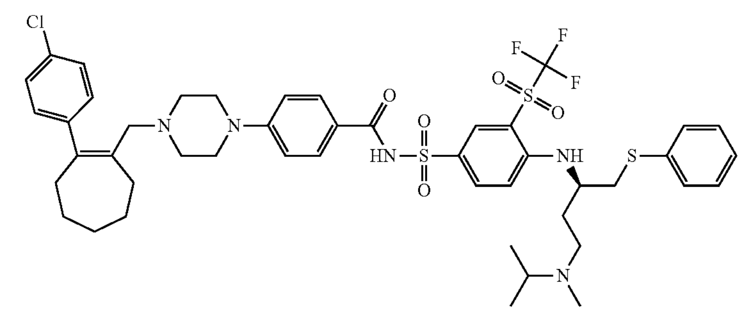 [SMILES: CC(C)N(C)CC[C@H](CSc1ccccc1)Nc1ccc(S(=O)(=O)NC(=O)c2ccc(N3CCN(CC4=C(c5ccc(Cl)cc5)CCCCC4)CC3)cc2)cc1S(=O)(=O)C(F)(F)F] |
| 3-((chloro(difluoro)methyl)sulfonyl)-N-(4-(4-((2-(4-chlorophenyl)cyclohex-1-en-1-yl)methyl)piperazin-1-yl)benzoyl)-4-(((1R)-3-((1S,4S)-2-oxa-5-azabicyclo[2.2.1]hept-5-yl)-1-((phenylsulfanyl)methyl)propyl)amino)benzenesulfonamide, | 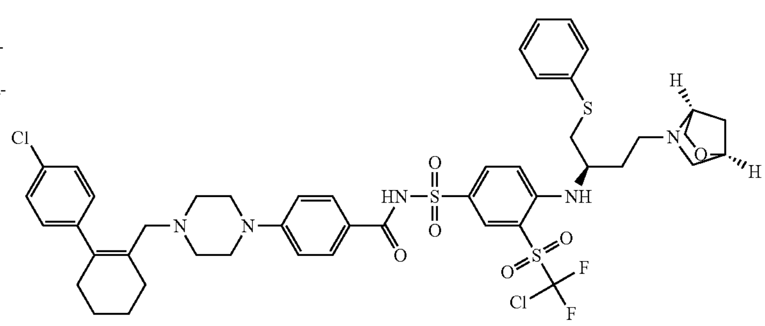 |

| Name | Structure |
|---|---|
| N-(4-(4-((2-(4-chlorophenyl)cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, | 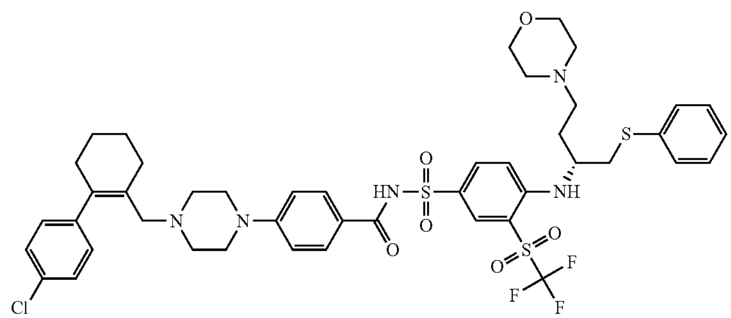 |
| 4-(((1R)-3-(7-azabicyclo[2.2.1]hept-7-yl)-1-((phenylsulfanyl)methyl)propyl)amino-N-(4-(4-((2-(4-chlorophenyl)cyclohex-1-en-1-yl)methyl)piperazin-1-yl)benzoyl)-3-((trifluoromethyl)sulfonyl)benzenesulfonamide, | |
| N-(4-(4-((2-(4-chlorophenyl)cyclohex-1-en-1-yl)methyl)piperazin-1-yl)benzoyl)-4-(((1R)-3-(2-oxa-5-azabicyclo[2.2.1]hept-5-yl)-1-((phenylsulfanyl)methyl)propyl)amino)-3-((trifluoromethyl)sulfonyl)benzenesulfonamide, | 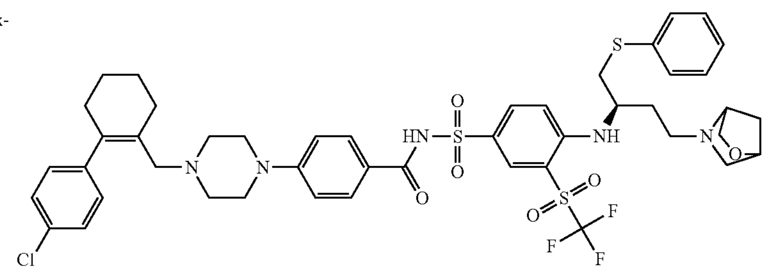 |
| N-(4-(4-((2-(4-chlorophenyl)-5,5-dimethylcyclohex-1-en-1-yl)methyl)piperazin-1-yl)benzoyl)-4-(((1R)-3-(2-oxa-5-azabicyclo[2.2.1]hept-5-yl)-1-((phenylsulfanyl)methyl)propyl)amino)-3-((trifluoromethyl)sulfonyl)benzenesulfonamide, | 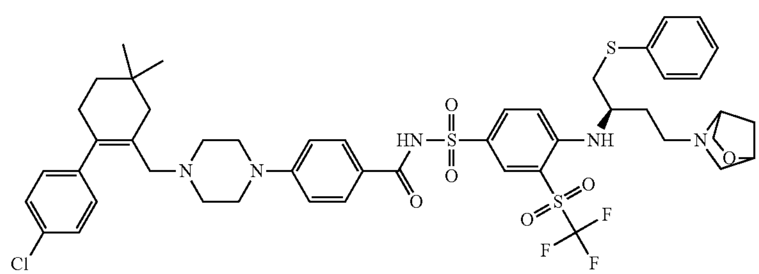 [SMILES: CC1(C)CCC(c2ccc(Cl)cc2)=C(CN2CCN(c3ccc(C(=O)NS(=O)(=O)c4ccc(N[C@H](CCN5CC6CC5CO6)CSc5ccccc5)c(S(=O)(=O)C(F)(F)F)c4)cc3)CC2)C1] |
| 3-((chloro(difluoro)methyl)sulfonyl)-N-(4-(4-((2-(4-chlorophenyl)-5,5-dimethylcyclohex-1-en-1-yl)methyl)piperazin-1-yl)benzoyl)-4-(((1R)-3-(2-oxa-5-azabicyclo[2.2.1]hept-5-yl)-1-((phenylsulfanyl)methyl)propyl)amino)benzenesulfonamide, | 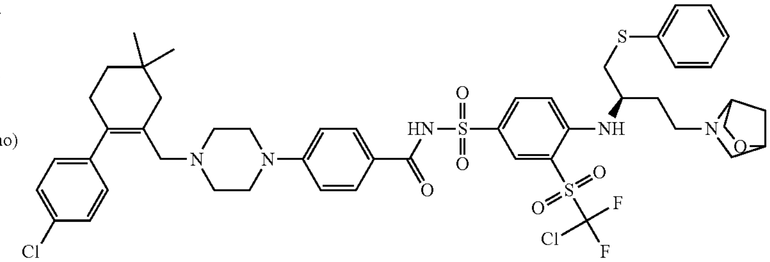 |

| Name | Structure |
|---|---|
| N-(4-(4-((2-(4-chlorophenyl)cyclohept-1-en-1-yl)methyl)piperazin-1-yl)benzoyl)-4-(((1R)-3-(2-oxa-5-azabicyclo[2.2.1]hept-5-yl) 1-((phenylsulfanyl)methyl)propyl)amino)-3-((trifluoromethyl)sulfonyl)benzenesulfonamide, | 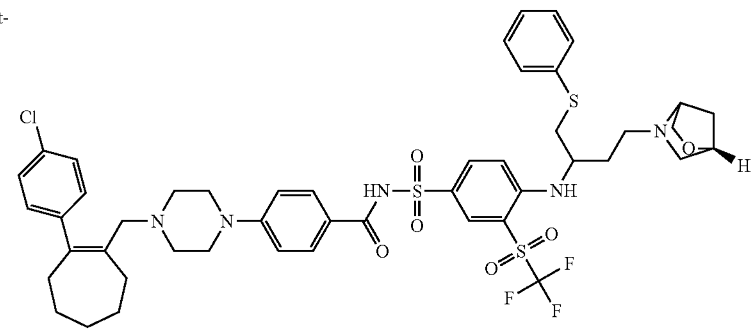 |
| 3-((chloro(difluoro)methyl)sulfonyl)-N-(4-(4-((2-(4-chlorophenyl)cyclohept-1-en-1-yl)methyl)piperazin-1-yl)benzoyl)-4-(((1R)-3-(2-oxa-5-axabicyclo[2.2.1]hept-5-yl)-1-((phenylsulfanyl)methyl)propyl)amino)benzenesulfonamide, | 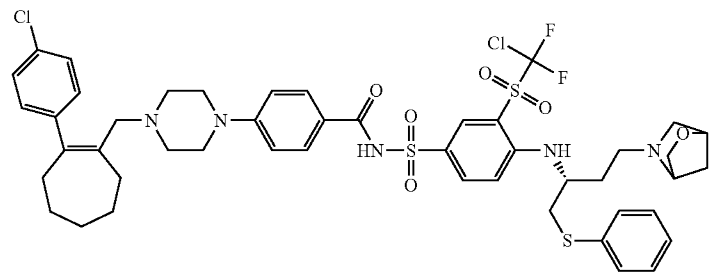 [SMILES: O=C(NS(=O)(=O)c1ccc(N[C@H](CCN2CC3CC2CO3)CSc2ccccc2)c(S(=O)(=O)C(F)(F)Cl)c1)c1ccc(N2CCN(CC3=C(c4ccc(Cl)cc4)CCCCC3)CC2)cc1] |
| N-(4-(4-((2-(4-chlorophenyl)-4,4-dimethylcyclohex-1-en-1-yl)methyl)piperazin-3-yl)benzoyl)-4-(((1R)-3-(isopropyl(methyl)amino)-1-((phenylsulfanyl)methyl)propyl)amino)-3-((trifluoromethyl)sulfonyl)benzenesulfonamide, | 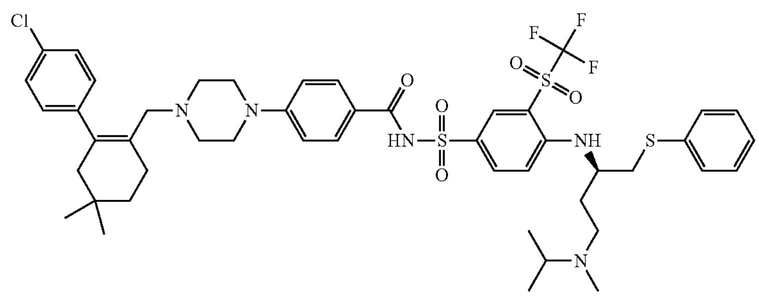 [SMILES: CC(C)N(C)CC[C@H](CSc1ccccc1)Nc1ccc(S(=O)(=O)NC(=O)c2ccc(N3CCN(CC4=C(c5ccc(Cl)cc5)CC(C)(C)CC4)CC3)cc2)cc1S(=O)(=O)C(F)(F)F] |
| N-(4-(4-((2-(4-chlorophenyl)cyclohex-1-en-1-yl)methyl)piperazin-1-yl)benzoyl)-4-(((1R)-3-(1,4-oxazepan-4-yl)-1-((phenylsulfanyl)methyl)propyl)amino)-3-((trifluoromethyl)sulfonyl)benzenesulfonamide, | 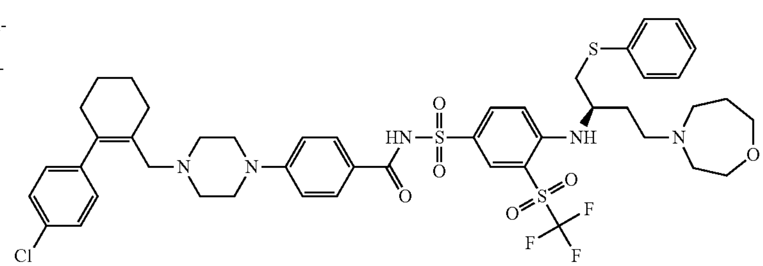 |
| 4-(((1R)-3-(azepan-1-yl)-1-((phenylsulfanyl)methyl)propyl)amino)-N-(4-(4-((2-(4-chlorophenyl)-1-cyclohex-1-en-1-yl)methyl)piperazin-1-yl)benzoyl)-3-((trifluoromethyl)sulfonyl)benzenesulfonamide, | 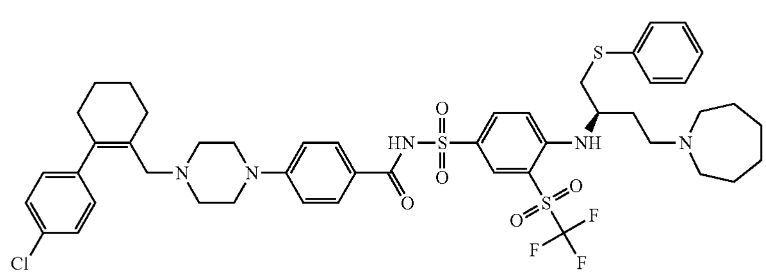 [SMILES: O=C(NS(=O)(=O)c1ccc(N[C@H](CCN2CCCCCC2)CSc2ccccc2)c(S(=O)(=O)C(F)(F)F)c1)c1ccc(N2CCN(CC3=C(c4ccc(Cl)cc4)CCCC3)CC2)cc1] |

| Name | Structure |
|---|---|
| N-(4-(4-((2-(4-chlorophenyl)cyclohept-1-en-1-yl)methyl)piperazin-1-yl)benzoyl-4-(((1R)-3-(dimethylamino)-1-((phenylsulfanyl)methyl)propyl)amino)-3-((trifluoromethyl)sulfonyl)benzenesulfonamide, | 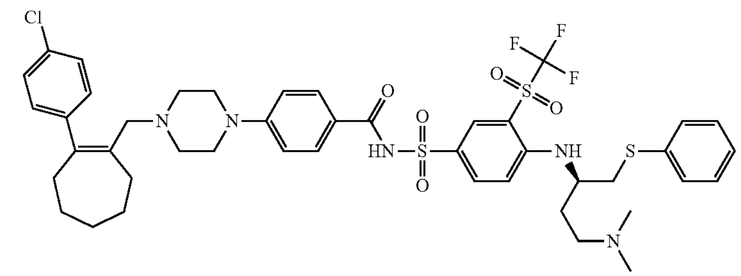 [SMILES: CN(C)CC[C@H](CSc1ccccc1)Nc1ccc(S(=O)(=O)NC(=O)c2ccc(N3CCN(CC4=C(c5ccc(Cl)cc5)CCCCC4)CC3)cc2)cc1S(=O)(=O)C(F)(F)F] |
| 3-((chloro(difluoro)methyl)sulfonyl)-N-(4-(4-((2-(4-chlorophenyl)cyclohex-1-en-1-yl)methyl)piperazin-1-yl)benzoyl)-4-(((1R)-3-(dimethylamino)-1-((phenylsulfanyl)methyl)propyl)amino)benzenesulfonamide, | 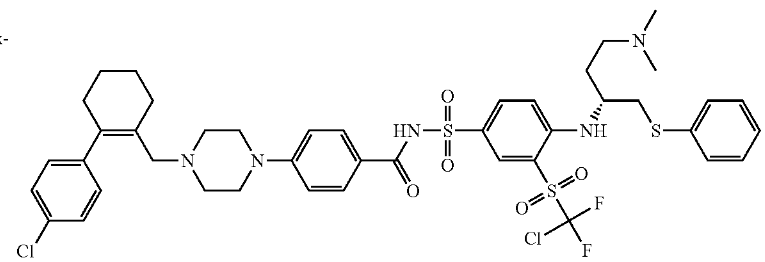 |
| 3-((chloro(difluoro)methyl)sulfonyl-N-(4-(4-((2-(4-chlorophenyl)-5,5-dimethylcyclohex-1-en-1-yl)methyl)piperazin-1-yl)benzoyl)-4-(((1R)-3-(morpholin-4-yl)-1-((phenylsulfanyl)methyl)propyl)amino)benzenesulfonamide, | 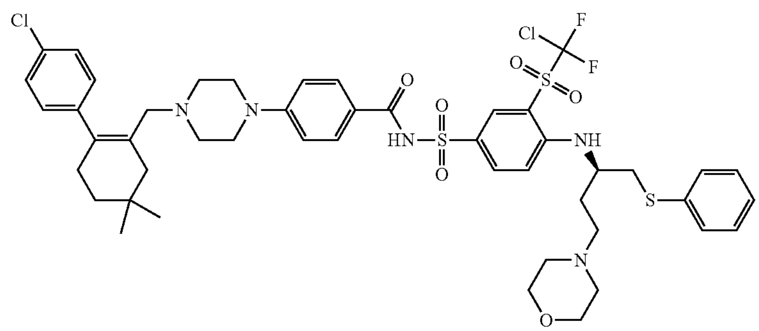 [SMILES: CC1(C)CCC(c2ccc(Cl)cc2)=C(CN2CCN(c3ccc(C(=O)NS(=O)(=O)c4ccc(N[C@H](CCN5CCOCC5)CSc5ccccc5)c(S(=O)(=O)C(F)(F)Cl)c4)cc3)CC2)C1] |
| N-(4-(4-((2-(4-chlorophenyl)-5,5-dimethyl-1-cyclohex-1-en-1-yl)methyl)piperazin-1-yl)benzoyl)-4-(((1R)-3-(dimethylamino)-1-((phenylsulfanyl)methyl)propyl)amino)-3-((trifluoromethyl)sulfonyl)benzenesulfonamide, | 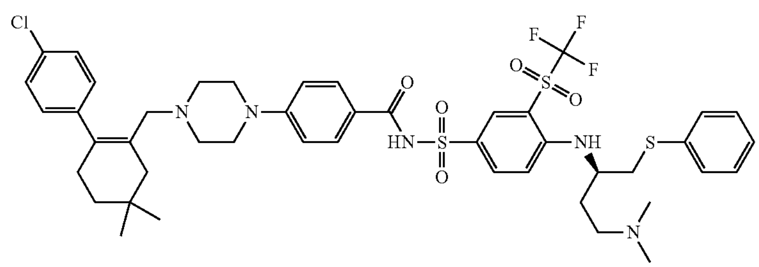 [SMILES: CN(C)CC[C@H](CSc1ccccc1)Nc1ccc(S(=O)(=O)NC(=O)c2ccc(N3CCN(CC4=C(c5ccc(Cl)cc5)CCC(C)(C)C4)CC3)cc2)cc1S(=O)(=O)C(F)(F)F] |
| N-(4-(4-((4-(4-chlorophenyl)-5,6-dihydro-2H-pyran-3-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, | 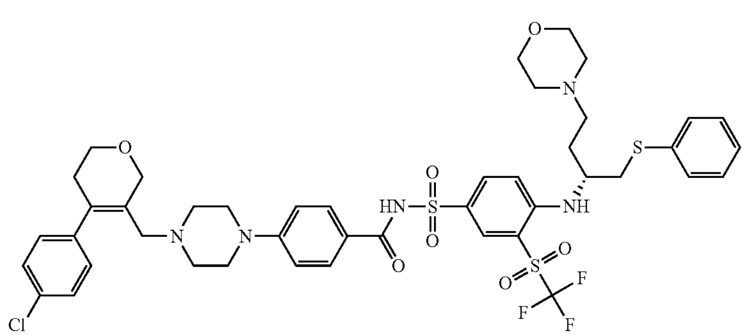 |

| Name | Structure |
|---|---|
| 3-((chloro(difluoro)methyl)sulfonyl)-N-(4-(4-((2-(4-chlorophenyl)-4,4-dimethylcyclohex-1-en-1-yl)methyl)piperazin-1-yl)benzoyl)-4-(((1R)-3-(isopropyl(methyl)amino)-1-((phenylsulfanyl)methyl)propyl)amino)benzenesulfonamide, | 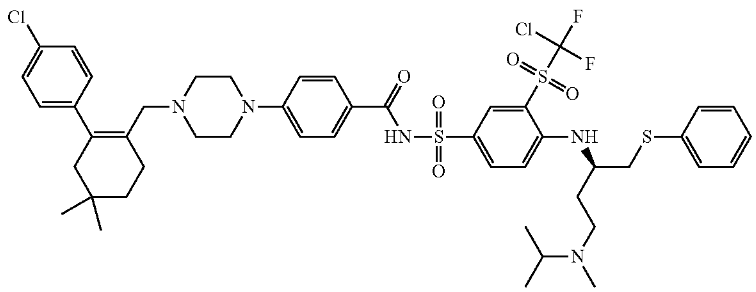 [SMILES: CC(C)N(C)CC[C@H](CSc1ccccc1)Nc1ccc(S(=O)(=O)NC(=O)c2ccc(N3CCN(CC4=C(c5ccc(Cl)cc5)CC(C)(C)CC4)CC3)cc2)cc1S(=O)(=O)C(F)(F)Cl] |
| 3-((chloro(difluoro)methyl)sulfonyl)-N-(4-(4-((2-(4-chlorophenyl)-5,5-dimethylcyclohex-1-en-1-yl)methyl)piperazin-3-yl)benzoyl)-4-(((1R)-3-(isopropyl(methyl)amino)-1-((phenylsulfanyl)methyl)propyl)amino)benzenesulfonamide, | 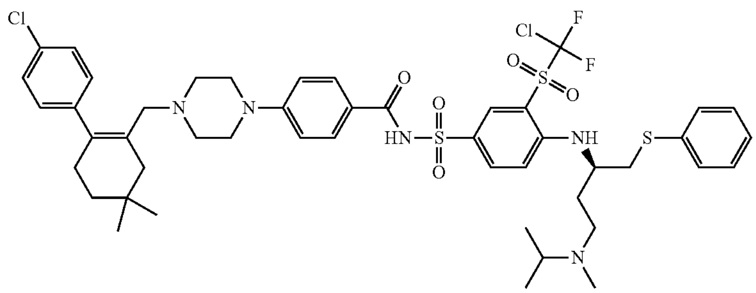 [SMILES: CC(C)N(C)CC[C@H](CSc1ccccc1)Nc1ccc(S(=O)(=O)NC(=O)c2ccc(N3CCN(CC4=C(c5ccc(Cl)cc5)CCC(C)(C)C4)CC3)cc2)cc1S(=O)(=O)C(F)(F)Cl] |
| N-(4-(4-((2-(4-chlorophenyl)-4,4-dimethylcyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, | 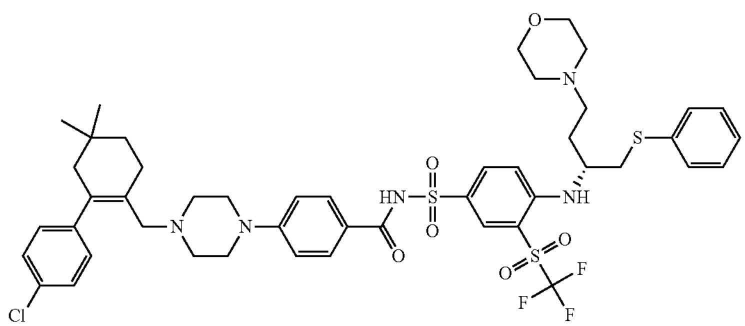 [SMILES: CC1(C)CCC(CN2CCN(c3ccc(C(=O)NS(=O)(=O)c4ccc(N[C@H](CCN5CCOCC5)CSc5ccccc5)c(S(=O)(=O)C(F)(F)F)c4)cc3)CC2)=C(c2ccc(Cl)cc2)C1] |
| 3-((chloro(difluoro)methyl)sulfonyl)-N-(4-(4-((2-(4-chlorophenyl)-4,4-dimethylcyclohex-1-en-1-yl)methyl)piperazin-1-yl)benzoyl)-4-(((1R)-3-((1S,4S)-2-oxa-5-azabicyclo[2.2.1]hept-5-yl)-1-((phenylsulfanyl)methyl)propyl)amino)benzenesulfonamide, | 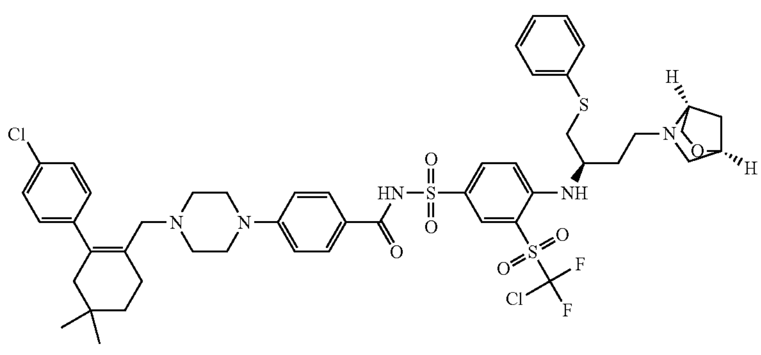 [SMILES: CC1(C)CCC(CN2CCN(c3ccc(C(=O)NS(=O)(=O)c4ccc(N[C@H](CCN5C[C@@H]6C[C@H]5CO6)CSc5ccccc5)c(S(=O)(=O)C(F)(F)Cl)c4)cc3)CC2)=C(c2ccc(Cl)cc2)C1] |
| N-(4-(4-((2-(4-chlorophenyl)cyclohex-1-en-1-yl)methyl)piperazin-1-yl)benzoyl)-4-(((1R)-3-(dimethylamino)-1-((phenylsulfanyl)methyl)propyl)amino)-3-((trifluoromethyl)sulfonyl)benzenesulfonamide, | 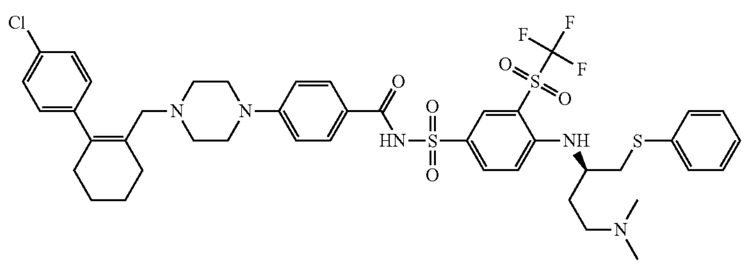 |

| Name | Structure |
|---|---|
| N-(4-(4-((2-(4-chlorophenyl)cyclohex-1-en-1-yl)methyl)piperazin-1-yl)benzoyl)-4-(((1R)-1-((phenylsulfanyl)methyl)-3-(pyrrolidin-1-yl)propyl)amino)-3-((trifluoromethyl)sulfonyl) benzenesulfonamide, | 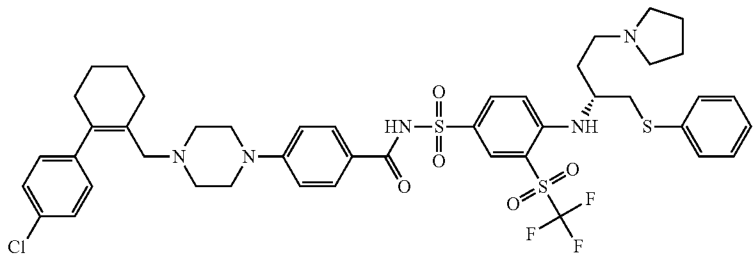 |
| 3-((chloro(difluoro)methyl)sulfonyl)-N-(4-(4-((2-(4-chlorophenyl)-4,4-dimethylcyclohex-1-en-1-yl)methyl)piperazin-1-yl)benzoyl)-4-(((1R)-3-(dimethylamino)-1-((phenylsulfanyl)methyl)propyl) amino)benzenesulfonamide, | 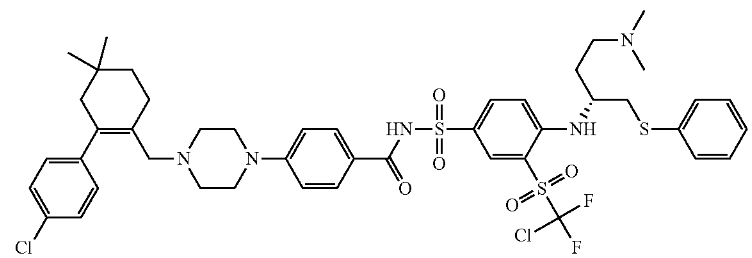 [SMILES: CN(C)CC[C@H](CSc1ccccc1)Nc1ccc(S(=O)(=O)NC(=O)c2ccc(N3CCN(CC4=C(c5ccc(Cl)cc5)CC(C)(C)CC4)CC3)cc2)cc1S(=O)(=O)C(F)(F)Cl] |
| N-(4-(4-((2-(4-chlorophenyl)cyclohept-1-en-1-yl)methyl)piperazin-1-yl)benzoyl)-4-(((1R)-1-((phenylsulfanyl)methyl)-3-(pyrrolidin-1-yl)propyl)amino)-3-((trifluoromethyl)sulfonyl) benzenesulfonamide, | 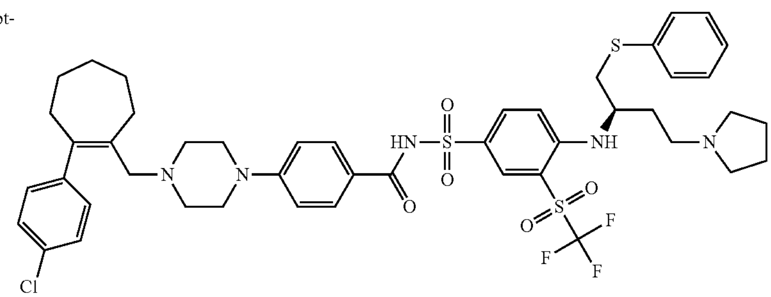 |
| 3-((chloro(difluoro)methyl)sulfonyl)-N-(4-(4-((2-(4-chlorophenyl)-5,5-dimethylcyclohex-1-en-1-yl)methyl)piperazin-1-yl)benzoyl)-4-(((1R)-1-((phenylsulfanyl)methyl)-3-(pyrrolidin-1-yl)propyl)amino) benzenesulfonamide, | 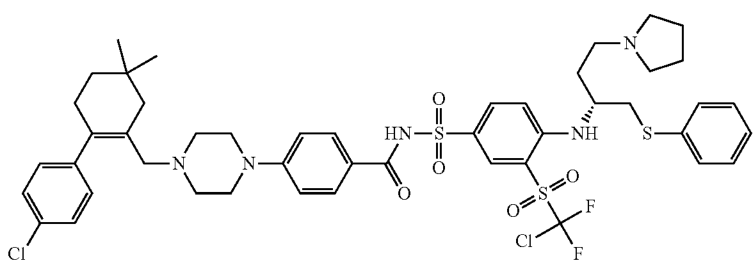 [SMILES: CC1(C)CCC(c2ccc(Cl)cc2)=C(CN2CCN(c3ccc(C(=O)NS(=O)(=O)c4ccc(N[C@H](CCN5CCCC5)CSc5ccccc5)c(S(=O)(=O)C(F)(F)Cl)c4)cc3)CC2)C1] |
| 3-((chloro(difluoro)methyl)sulfonyl)-N-(4-(4-((2-(4-chlorophenyl)-4,4-dimethylcyclohex-1-en-1-yl)methyl)piperazin-1-yl)benzoyl)-4-(((1R)-1-((phenylsulfanyl)methyl)-3-(pyrrolidin-1-yl)propyl)amino) benzenesulfonamide, | 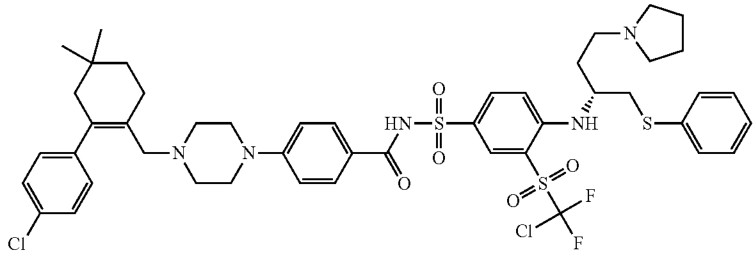 [SMILES: CC1(C)CCC(CN2CCN(c3ccc(C(=O)NS(=O)(=O)c4ccc(N[C@H](CCN5CCCC5)CSc5ccccc5)c(S(=O)(=O)C(F)(F)Cl)c4)cc3)CC2)=C(c2ccc(Cl)cc2)C1] |

-continued

| Name | Structure |
|---|---|
| 3-((chloro(difluoro)methyl)sulfonyl)-N-(4-(4-((2-(4-chlorophenyl)cyclohept-1-en-1-yl)methyl)piperazin-1-yl)benzoyl)-4-(((1R)-1-((phenylsulfanyl)methyl)-3-(pyrrolidin-1-yl)propyl)amino)benzenesulfonamide, | 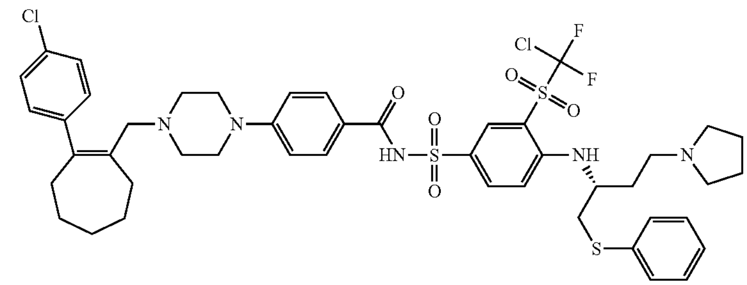 [SMILES: O=C(NS(=O)(=O)c1ccc(N[C@H](CCN2CCCC2)CSc2ccccc2)c(S(=O)(=O)C(F)(F)Cl)c1)c1ccc(N2CCN(CC3=C(c4ccc(Cl)cc4)CCCCC3)CC2)cc1] |
| N-(4-(4-((2-(4-chlorophenyl)cyclohex-1-en-1-yl)methyl)piperazin-1-yl)benzoyl)-4-(((1R)-3-(isopropyl(methyl)amino) 1-((phenylsulfanyl)methylpropyl)amino)-3-((trifluoromethyl)sulfonyl)benzenesulfonamide, | |
| N-(4-(4-((2-(4-chlorophenyl)-4,4-dimethylcyclohex-1-en-1-yl)methyl)piperazin-1-yl)benzoyl)-4-(((1R)-1-((phenylsulfanyl)methyl)-3-(pyrrolidin-1-yl)propyl)amino)-3-((trifluoromethyl)sulfonyl)benzenesulfonamide, | 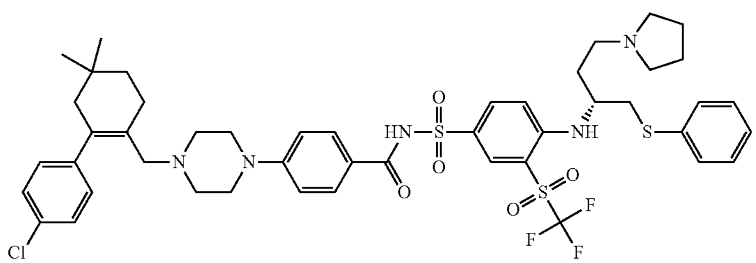 [SMILES: CC1(C)CCC(CN2CCN(c3ccc(C(=O)NS(=O)(=O)c4ccc(N[C@H](CCN5CCCC5)CSc5ccccc5)c(S(=O)(=O)C(F)(F)F)c4)cc3)CC2)=C(c2ccc(Cl)cc2)C1] |
| 3-((chloro(difluoro)methyl)sulfonyl)-N-(4-(4-((2-(4-chlorophenyl)cyclohex-1-en-1-yl)methyl)piperazin-1-yl)benzoyl)-4-(((1R)-1-((phenylsulfanyl)methyl)-3-(pyrrolidin-1-yl)propyl)amino)benzenesulfonamide, | 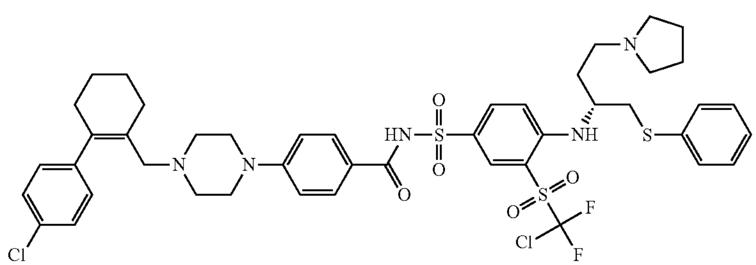 [SMILES: O=C(NS(=O)(=O)c1ccc(N[C@H](CCN2CCCC2)CSc2ccccc2)c(S(=O)(=O)C(F)(F)Cl)c1)c1ccc(N2CCN(CC3=C(c4ccc(Cl)cc4)CCCC3)CC2)cc1] |
| N-(4-(4-((2-(4-chlorophenyl)-4,4-dimethylcyclohex-1-en-1-yl)methyl)piperazin-1-yl)benzoyl)-4-(((1R)-3-(dimethylamino)-1-((phenylsulfanyl)methyl)propyl)amino)-3-((trifluoromethyl)sulfonyl)benzenesulfonamide, | 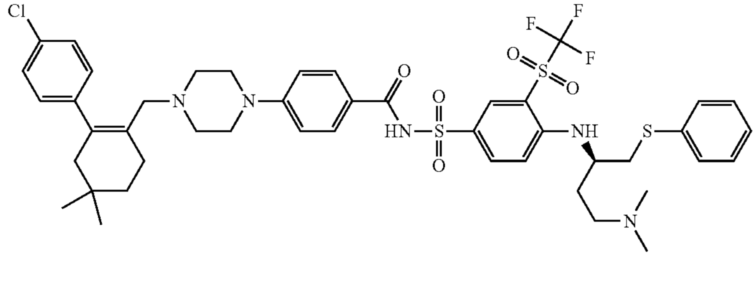 [SMILES: CN(C)CC[C@H](CSc1ccccc1)Nc1ccc(S(=O)(=O)NC(=O)c2ccc(N3CCN(CC4=C(c5ccc(Cl)cc5)CC(C)(C)CC4)CC3)cc2)cc1S(=O)(=O)C(F)(F)F] |

-continued

| Name | Structure |
|---|---|
| N-(4-(4-((2-(4-chlorophenyl)-4,4-dimethylcyclohex-1-en-1-yl)methyl)piperazin-1-yl)benzoyl)-4-(((1R)-3-((1S,4S)-2-oxa-5-azabicyclo[2.2.1]hept-5-yl)-1-((phenylsulfanyl)methyl)propyl)amino)-3-((trifluoromethyl)sulfonyl)benzenesulfonamide | 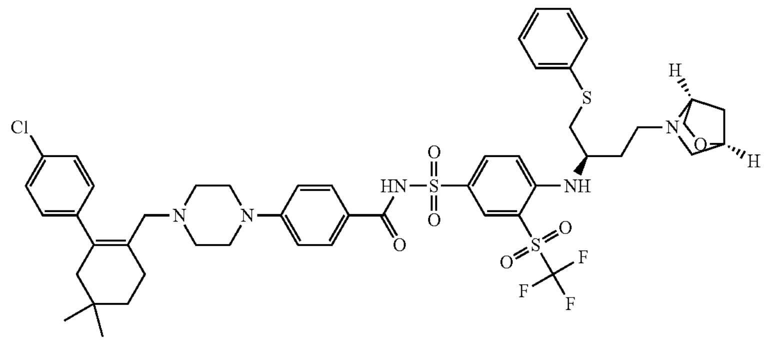 |
| N-(4-(4-((4'-chloro(1,1'-biphenyl)-2-yl)methyl)-1-piperazinyl)benzoyl)-4-(((1R)-3-(dimethylamino)-1-((phenylsulfanyl)methyl)propyl)amino)-3-((trifluoromethyl)sulfonyl)benzenesulfonamide and | 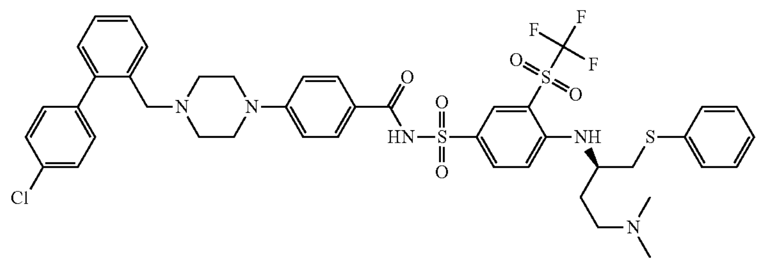 [SMILES: CN(C)CC[C@H](CSc1ccccc1)Nc1ccc(S(=O)(=O)NC(=O)c2ccc(N3CCN(Cc4ccccc4-c4ccc(Cl)cc4)CC3)cc2)cc1S(=O)(=O)C(F)(F)F] |
| N-(4-(4-((4'-chloro(1,1'-biphenyl)-2-yl)methyl)-1-piperazinyl)benzoyl)-4-(((1R)-3-(4-morpholinyl)-1-((phenylsulfanyl)methyl)propyl)amino)-3-((trifluoromethyl)sulfonyl)benzenesulfonamide | 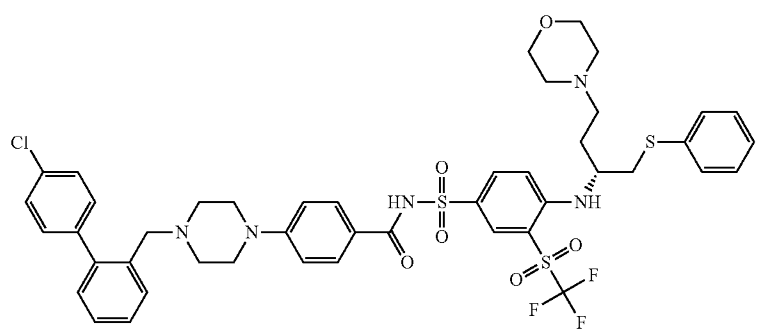 [SMILES: O=C(NS(=O)(=O)c1ccc(N[C@H](CCN2CCOCC2)CSc2ccccc2)c(S(=O)(=O)C(F)(F)F)c1)c1ccc(N2CCN(Cc3ccccc3-c3ccc(Cl)cc3)CC2)cc1] |

In some embodiments, the compound is selected from the group consisting of:

| Name | Structure |
|---|---|
| N-(4-(4-((1,1'-biphenyl)-2-ylmethyl)piperazin-1-yl)benzoyl)-4-(((1R)-3-(dimethylamino)-1-((phenylsulfanyl)methyl)propyl)ammo)-3-nicrobenzenesulfonamide, | 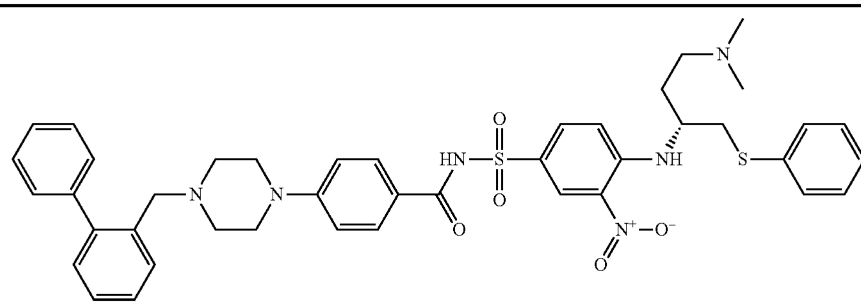 |

| Name | Structure |
|---|---|
| N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide, | 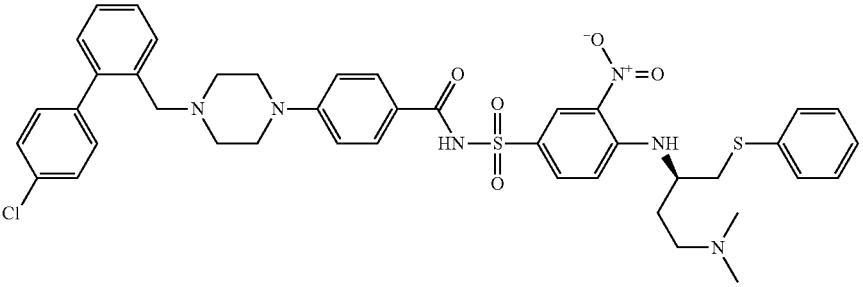 |
| 4-(((1R)-3-(dimethylamino)-1-((phenylsulfanyl)methyl)propyl)amino)-N-(4-(4-((4'-methoxy(1,1'-biphenyl)-2-yl)methyl.)piperazin-1-yl)benzoyl)-3-nitrobenzenesulfonamide, | 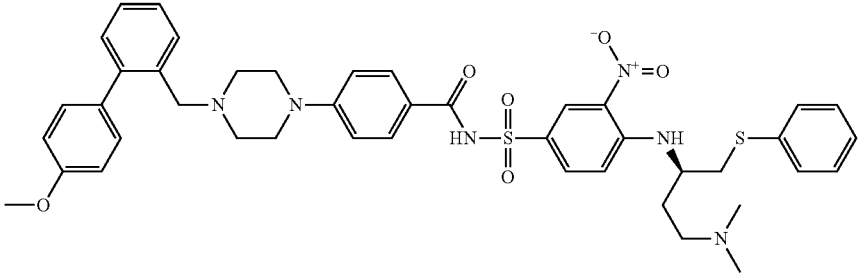 |
| 4-(((1R)-3-(dimethylamino)-1-((phenylsulfanyl)methyl)propyl)amino)-N-(4-(4-((4'-fluoro(1,1'-biphenyl)-2-yl)methyl)piperazin-1-yl)benzoyl)-3-nitrobenzenesulfonamide, | 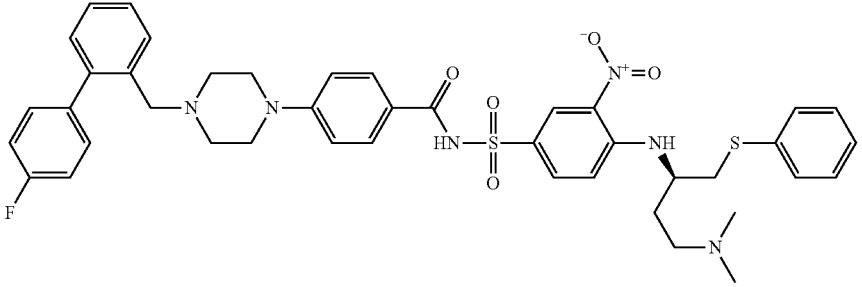 |
| 4-(((1R)-3-(dimethylamino)-1-((phenylsulfanyl)methyl)propyl)amino)-N-(4-(4-((4'-(methylsulfanyl)(1,1'-biphenyl)-2-yl)methyl)piperazin-1-yl)benzoyl)-3-nitrobenzenesulfonamide, | 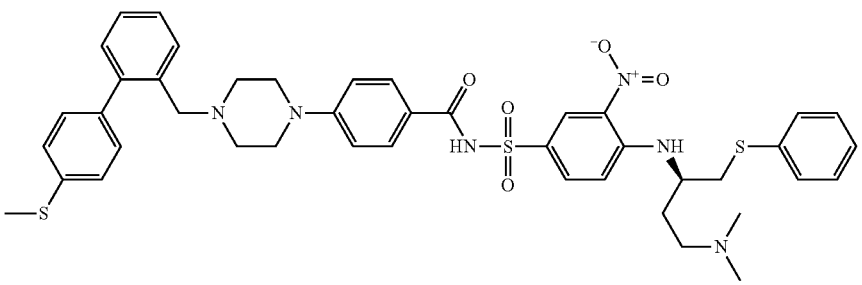 |
| N-((4-(((1R)-3-(dimethylamino)-1-((phenylsulfanyl)methyl)propyl)amino)-3-nitrophenyl)sulfonyl)-4-(4-(4'-phenyl-1,1'-biphenyl-2-ylmethyl)piperazin-1-yl)benzamide, | 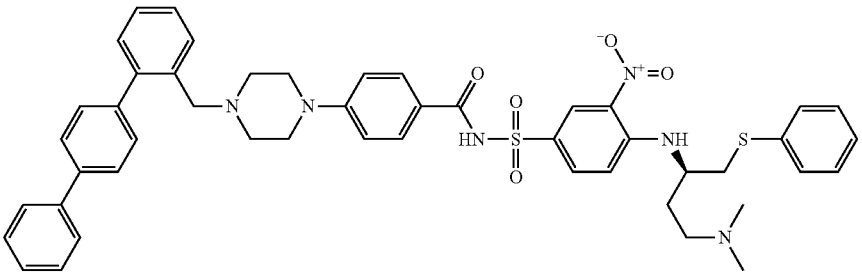 |

-continued

| Name | Structure |
|---|---|
| 4-(((1R)-3-(dimethylamino)-1-((phenylsulfanyl)methyl)propyl)amino)-3-nitro-N-(4-(4-((4'-phenoxy(1,1'-biphenyl)-2-yl)methyl)piperazin-1-yl)benzoyl)benzenesulfonamide, | 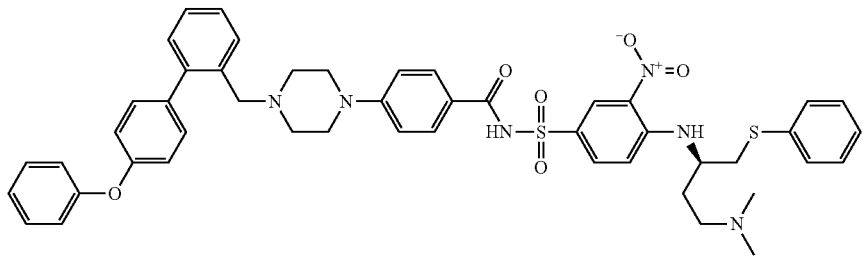 |
| N-(4-(4-((1,1'-biphenyl)-2-ylmethyl)piperazin-1-yl)benzoyl)-4-((1,1-dimethyl-2-(phenylsulfanyl)ethyl)amino)-3-nitrobenzenesulfonamide, | 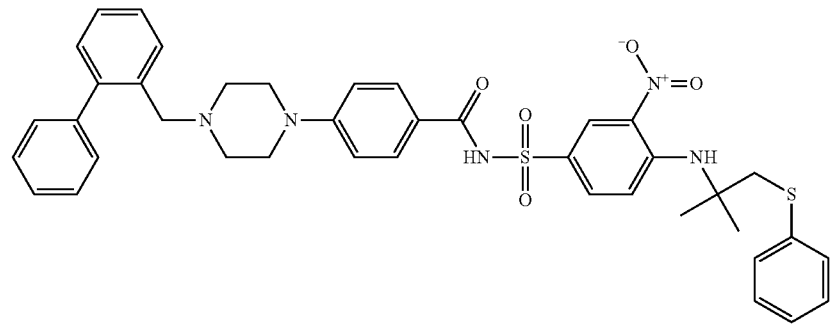 |
| N-(4-(4-((1,1'-biphenyl)-2-ylmethyl)piperazin-1-yl)benzoyl)-4-(((1R)-3-(morpholin-4-yl)-1-((phenylsulfanyl)methyl)propyl)amino)-3-nitrobenzenesulfonamide, | 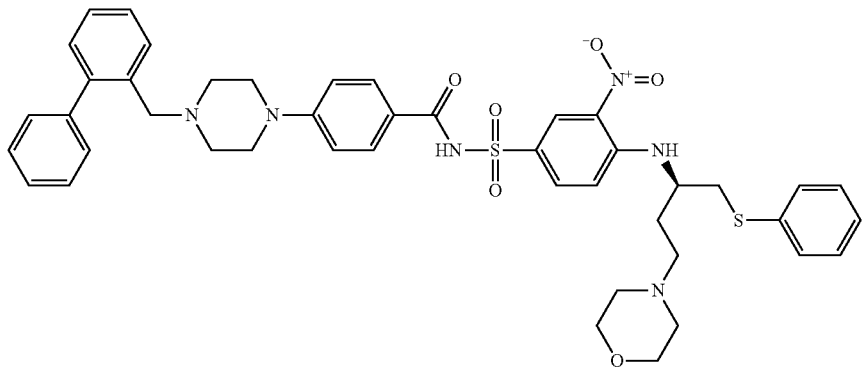 |
| N-(4-(4-((1,1'-biphenyl)-2-ylmethyl)piperazin-1-yl)benzoyl)-3-nitro-4-((2-(phenylsulfanyl)ethyl)amino)benzenesulfonamide, | 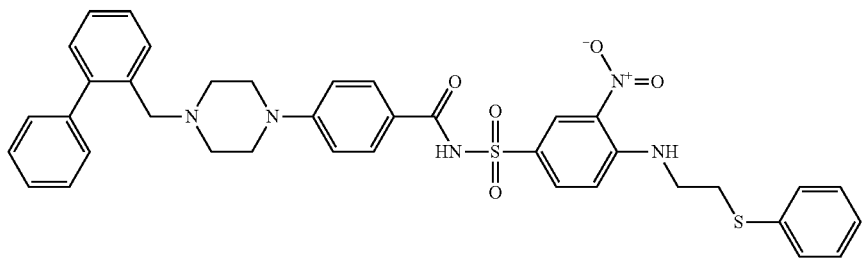 |
| N-(4-(4-((4'-chloro(1,1'-biphenyl)-2-yl)methyl)piperazin-1-yl)benzoyl)-3-nitro-4-((2-(phenylsulfanyl)ethyl)amino)benzenesulfonamide, | 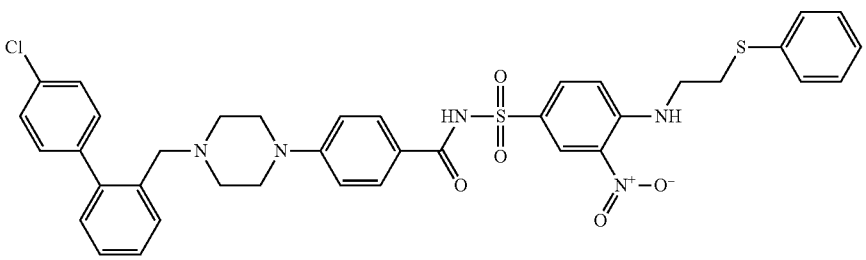 |

-continued

| Name | Structure |
|---|---|
| N-(4-(4-((4'-chloro(1,1'-biphenyl)-2-yl)methyl)piperazin-1-yl)benzoyl)-4-(((1R)-3-(morpholin-4-yl)-1-((phenylsulfanyl)methyl)propyl)amino)-3-nitrobenzenesulfonamide, | 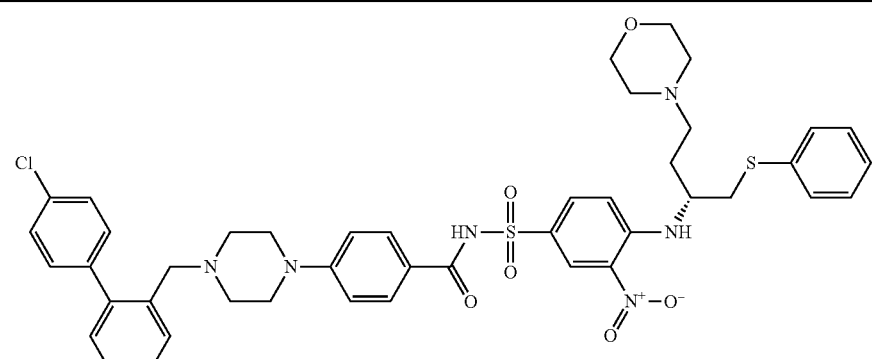 |
| N-(4-(4-((4'-chloro(1,1'-biphenyl)-2-yl)methyl)piperazin-1-yl)benzoyl)-4-((1,1-dimethyl-2-(phenylsulfanyl)ethyl)amino)-3-nitrobenzenesulfonamide, | 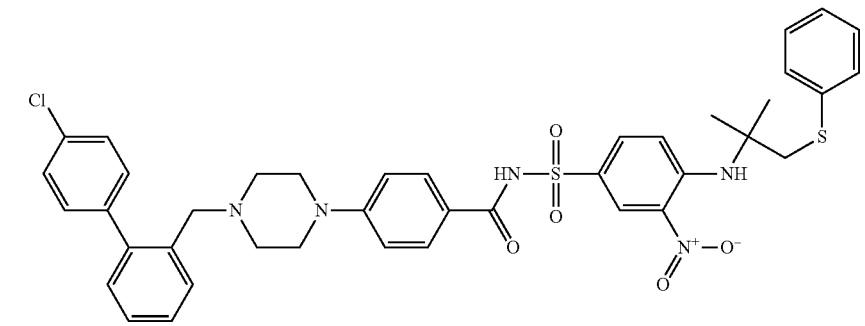 [SMILES: CC(C)(CSc1ccccc1)Nc1ccc(S(=O)(=O)NC(=O)c2ccc(N3CCN(Cc4ccccc4-c4ccc(Cl)cc4)CC3)cc2)cc1[N+](=O)[O-]] |
| N-(4-(4-((4'-chloro(1,1'-biphenyl)-2-yl)methyl)piperazin-1-yl)benzoyl)-4-(((1R)-4-(dimethylamino)-1-((phenylsulfanyl)methyl)butyl)amino)-3-nitrobenzenesulfonamide, | 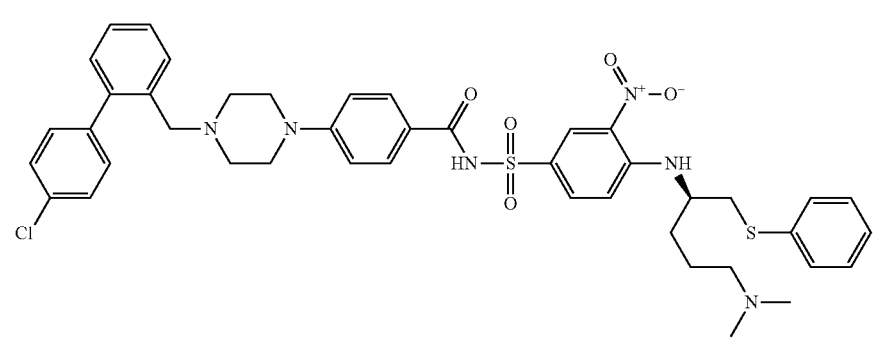 [SMILES: CN(C)CCC[C@H](CSc1ccccc1)Nc1ccc(S(=O)(=O)NC(=O)c2ccc(N3CCN(Cc4ccccc4-c4ccc(Cl)cc4)CC3)cc2)cc1[N+](=O)[O-]] |
| N-(4-(4-((4'-chloro(1,1'-biphenyl)-2-yl)methyl)piperazin-1-yl)benzoyl)-4-(((1R)-5-(dimethylamino)-1-((phenylsulfanyl)methyl)pentyl)amino)-3-nitrobenzenesulfonamide, | 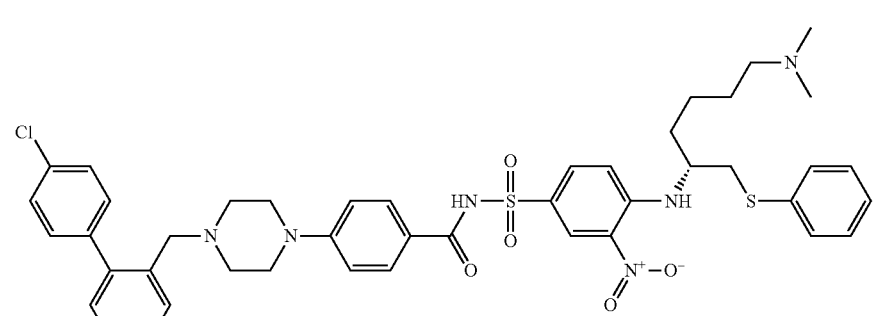 |

| Name | Structure |
|---|---|
| N-(4-(4-((4'-fluoro(1,1'-biphenyl)-2-yl)methyl)piperazin-1-yl)benzoyl)-4-(((1R)-3-(morpholin-4-yl)-1-((phenylsulfanyl)methyl)propyl)amino)-3-nitrobenzenesulfonamide, | 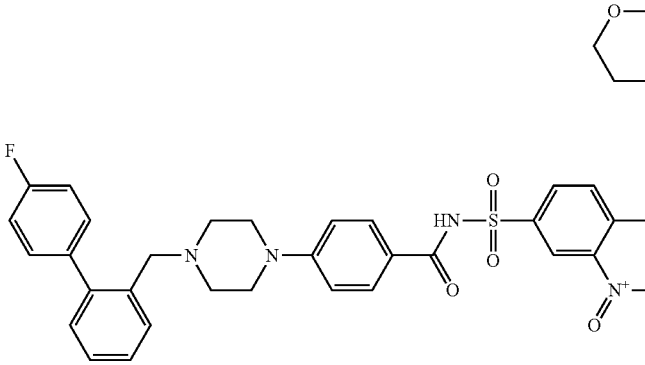 |
| N-(4-(4-((4'-chloro-4-fluoro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide, | 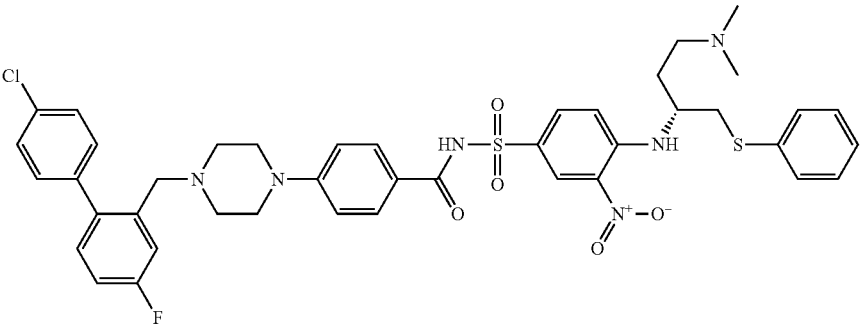 [SMILES: CN(C)CC[C@H](CSc1ccccc1)Nc1ccc(S(=O)(=O)NC(=O)c2ccc(N3CCN(Cc4cc(F)ccc4-c4ccc(Cl)cc4)CC3)cc2)cc1[N+](=O)[O-]] |
| N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-(trifluoromethyl)benzenesulfonamide, | 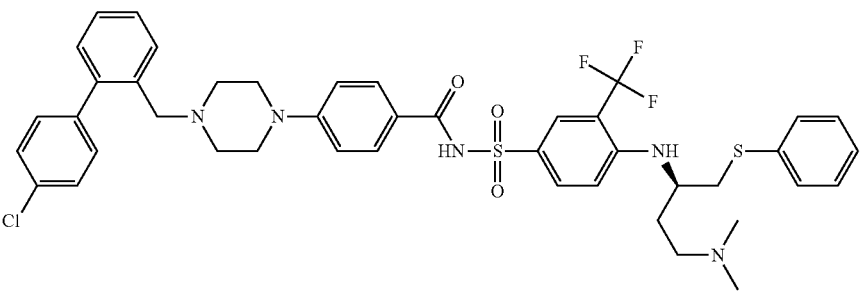 [SMILES: CN(C)CC[C@H](CSc1ccccc1)Nc1ccc(S(=O)(=O)NC(=O)c2ccc(N3CCN(Cc4ccccc4-c4ccc(Cl)cc4)CC3)cc2)cc1C(F)(F)F] |
| N-(4-(4-((4'-chloro(1,1'-biphenyl)-2-yl)methyl)piperazin-1-yl)benzoyl)-4-(((1R)-3-(morpholin-4-yl)-1-((phenylsulfanyl)methyl)propyl)amino)-3-(trifluoromethyl)benzenesulfonamide, | 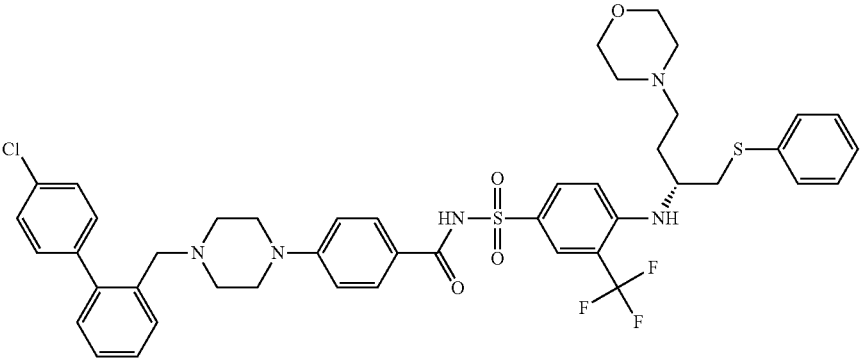 [SMILES: O=C(NS(=O)(=O)c1ccc(N[C@H](CCN2CCOCC2)CSc2ccccc2)c(C(F)(F)F)c1)c1ccc(N2CCN(Cc3ccccc3-c3ccc(Cl)cc3)CC2)cc1] |

-continued

| Name | Structure |
|---|---|
| N-(4-(4-((4'-chloro(1,1'-biphenyl)-2-yl)methyl)piperazin-1-yl)benzoyl)-3-nitro-4-(((1R)-1-((phenylsulfanyl)methyl)-3-(pyrrolidin-1-yl)propyl)amino)benzenesulfonamide, | |
| N-(4-(4-((4'-chloro(1,1'-biphenyl)-2-yl)methyl)piperazin-1-yl)benzoyl)-4-((1,1-dimethyl-2-(1,3-thiazol-2-ylsulfanyl)ethyl)amino)-3-nitrobenzenesulfonamide, | 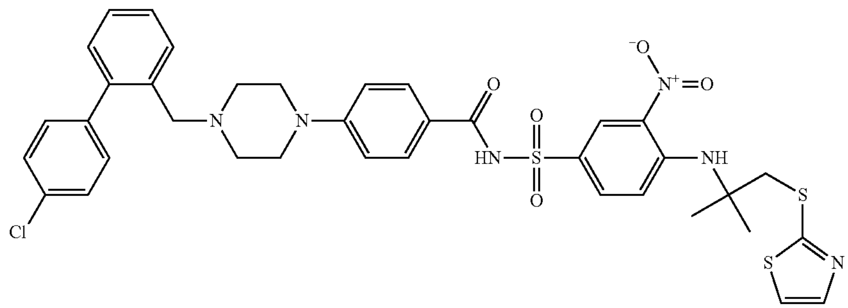 |
| N-(4-(4-((4'-chloro(1,1'-biphenyl)-2-yl)methyl)piperazin-1-yl)benzoyl)-4-(((1R)-3-(dimethylamino)-1-((1,3-thiazol-2-ylsulfanyl)methyl)propyl)amino)-3-nitrobenzenesulfonamide, | 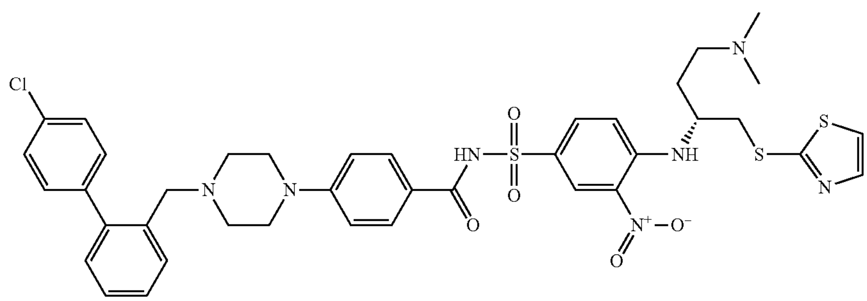 [SMILES: CN(C)CC[C@H](CSc1nccs1)Nc1ccc(S(=O)(=O)NC(=O)c2ccc(N3CCN(Cc4ccccc4-c4ccc(Cl)cc4)CC3)cc2)cc1[N+](=O)[O-]] |
| N-(4-(4-((4'-chloro(1,1'-biphenyl)-2-yl)methyl)piperazin-1-yl)benzoyl)-4-(((1R)-3-(dimethylamino)-1-((thien-2-ylsulfanyl)methyl)propyl)amino)-3-nitrobenzenesulfonamide, | 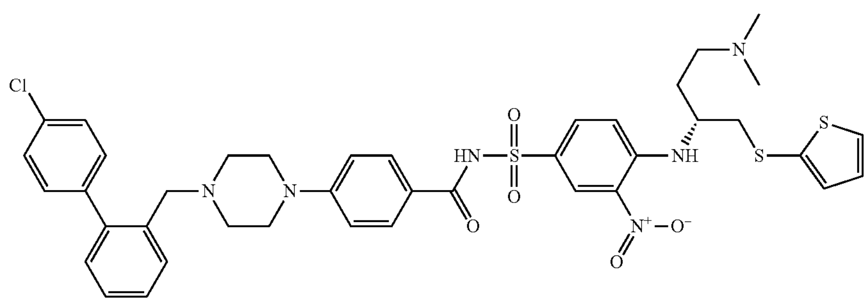 [SMILES: CN(C)CC[C@H](CSc1cccs1)Nc1ccc(S(=O)(=O)NC(=O)c2ccc(N3CCN(Cc4ccccc4-c4ccc(Cl)cc4)CC3)cc2)cc1[N+](=O)[O-]] |
| N-(4-(4-((4'-chloro(1,1'-biphenyl)-2-yl)methyl)piperazin-1-yl)benzoyl)-4-(((1R)-2-(2-(dimethylamino)ethoxy)-1-((phenylsulfanyl)methyl)ethyl)amino)-3-nitrobenzenesulfonamide, | 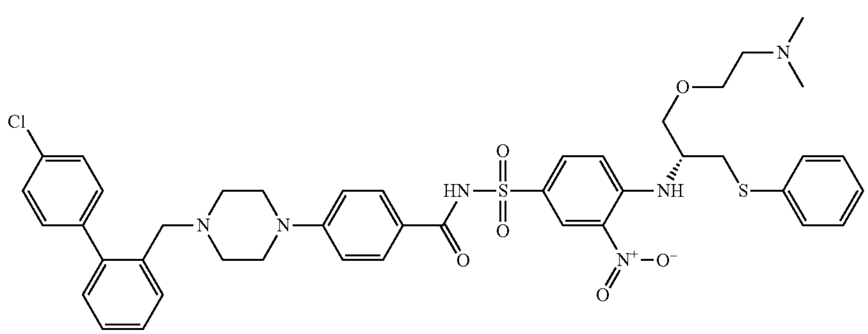 [SMILES: CN(C)CCOC[C@H](CSc1ccccc1)Nc1ccc(S(=O)(=O)NC(=O)c2ccc(N3CCN(Cc4ccccc4-c4ccc(Cl)cc4)CC3)cc2)cc1[N+](=O)[O-]] |

| Name | Structure |
|------|-----------|
| N-(4-(4-((4'-chloro(1,1'-biphenyl)-2-yl)methyl)piperazin-1-yl)benzoyl)-4-(((1S)-3-(dimethylamino)-1-methyl-1-((phenylsulfanyl)methyl)propyl)amino)-3-nitrobenzenesulfonamide, | 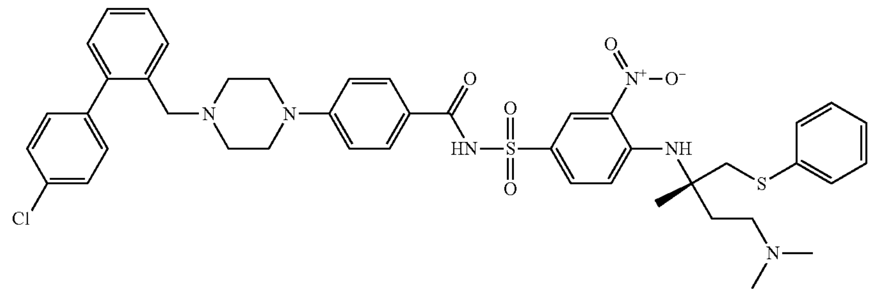 [SMILES: CN(C)CC[C@@](C)(CSc1ccccc1)Nc1ccc(S(=O)(=O)NC(=O)c2ccc(N3CCN(Cc4ccccc4-c4ccc(Cl)cc4)CC3)cc2)cc1[N+](=O)[O-]] |
| N-(4-(4-((4'-chloro(1,1'-biphenyl)-2-yl)methyl)piperazin-1-yl)benzoyl)-4-(((1R)-3-(methylamino)-1-((phenylsulfanyl)methyl)propyl)amino)-3-nitrobenzenesulfonamide, | 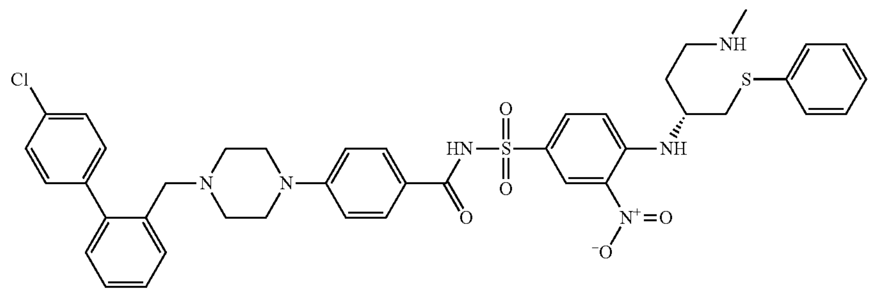 |
| (3R)-3-(4-(((4-(4-((4'-chloro(1,1'-biphenyl)-2-yl)methyl)piperazin-1-yl)benzoyl)amino)sulfonyl)-2-nitroanilino)-4-(phenylsulfanyl)butanoic acid, | 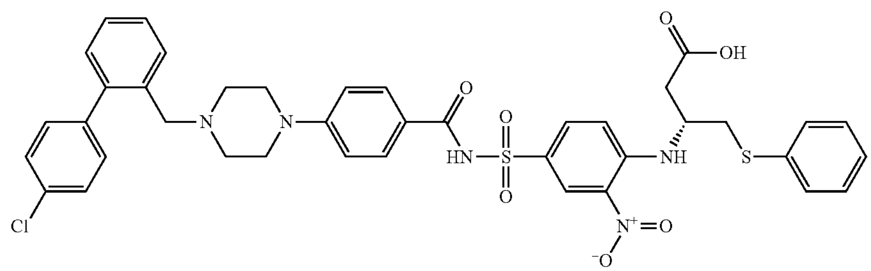 |
| (3R)-3-(4-(((4-(4-((4'-chloro(1,1'-biphenyl)-2-yl)methyl)piperazin-1-yl)benzoyl)amino)sulfonyl)-2-nitroanilino)-N-isopropyl-4-(phenylsulfanyl)butanamide, | 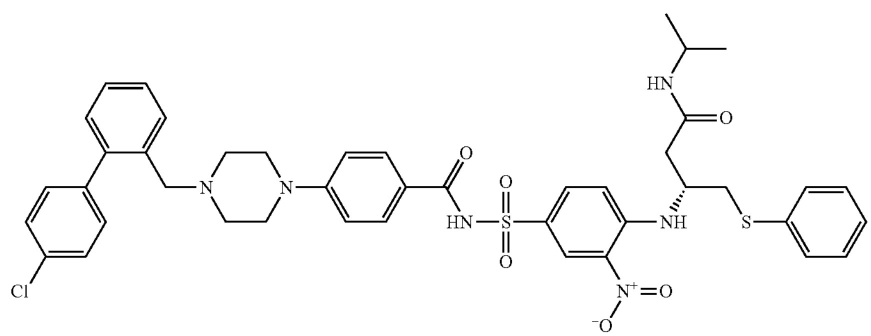 |
| N-(4-(4-((4'-chloro(1,1'-biphenyl)-2-yl)methyl)piperazin-1-yl)benzoyl)-4-(((1R)-3-(diisopropylamino)-1-((phenylsulfanyl)methyl)propyl)amino)-3-nitrobenzenesulfonamide, | 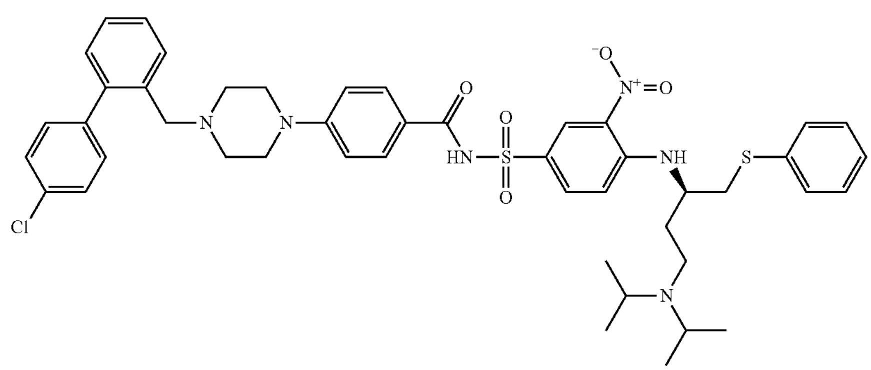 |

| Name | Structure |
|---|---|
| 4-(((1R)-3-(azetidin-1-yl)-1-((phenylsulfanyl)methyl)propyl)amino)-N-(4-(4-((4'-chloro(1,1'-biphenyl)-2-yl)methyl)piperazin-1-yl)benzoyl)-3-nitrobenzenesulfonamide, | 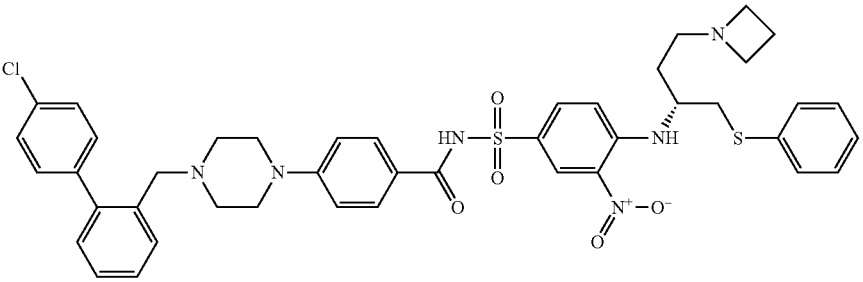 [SMILES: O=C(NS(=O)(=O)c1ccc(N[C@H](CCN2CCC2)CSc2ccccc2)c([N+](=O)[O-])c1)c1ccc(N2CCN(Cc3ccccc3-c3ccc(Cl)cc3)CC2)cc1] |
| N-(4-(4-((4'-chloro(1,1'-biphenyl)-2-yl)methyl)piperazin-1-yl)benzoyl)-3-nitro-4-((4-(phenylsulfanyl)tetrahydro-3-furanyl)amino)benzenesulfonamide, | 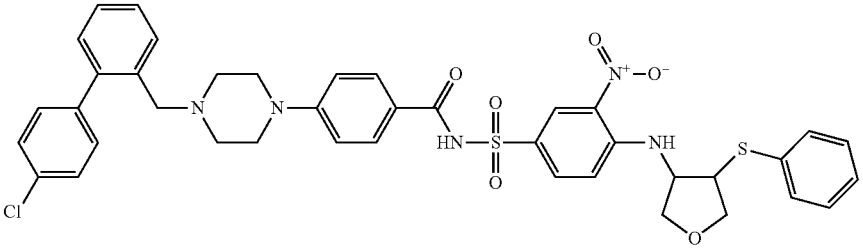 [SMILES: O=C(NS(=O)(=O)c1ccc(NC2COCC2Sc2ccccc2)c([N+](=O)[O-])c1)c1ccc(N2CCN(Cc3ccccc3-c3ccc(Cl)cc3)CC2)cc1] |
| N-(4-(4-((4'-chloro(1,1'-biphenyl)-2-yl)methyl)-4-methoxypiperidin-1-yl)benzoyl)-4-(((1R)-3-(dimethylamino)-1-((phenylsulfanyl)methyl)propyl)amino)-3-nitrobenzenesulfonamide, | 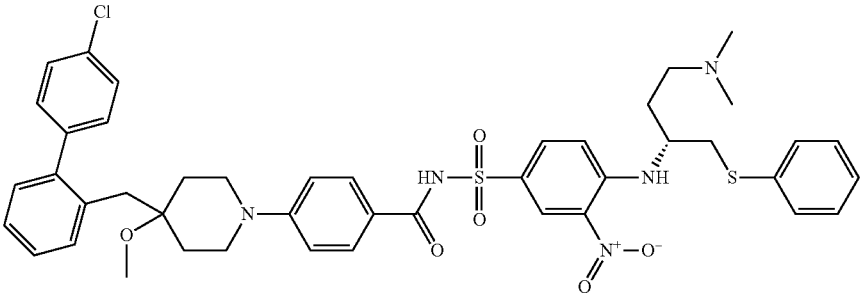 [SMILES: COC1(Cc2ccccc2-c2ccc(Cl)cc2)CCN(c2ccc(C(=O)NS(=O)(=O)c3ccc(N[C@H](CCN(C)C)CSc4ccccc4)c([N+](=O)[O-])c3)cc2)CC1] |
| N-(4-(4-((4'-chloro(1,1'-biphenyl)-2-yl)methyl)-4-methoxypiperidin-1-yl)benzoyl)-4-((1R)-3-(morpholin-4-yl)-1-((phenylsulfanyl)methyl)propyl)amino)-3-nitrobenzenesulfonamide | 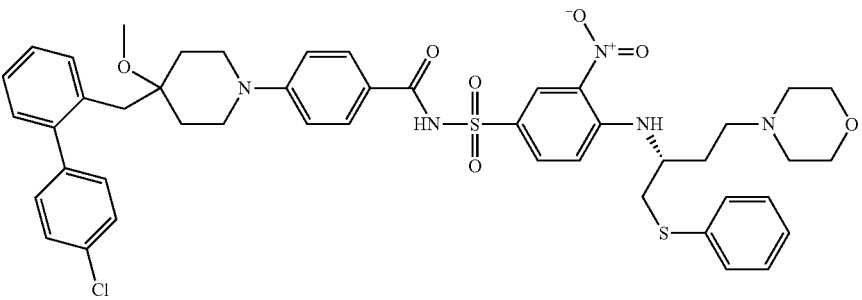 |
| N-(4-(4-((4'-chloro(1,1'-biphenyl)-2-yl)methyl)piperazin-1-yl)benzoyl)-4-(((1R)-3-hydroxy-1-((phenylsulfanyl)methyl)propyl)amino)-3-nitrobenzenesulfonamides | 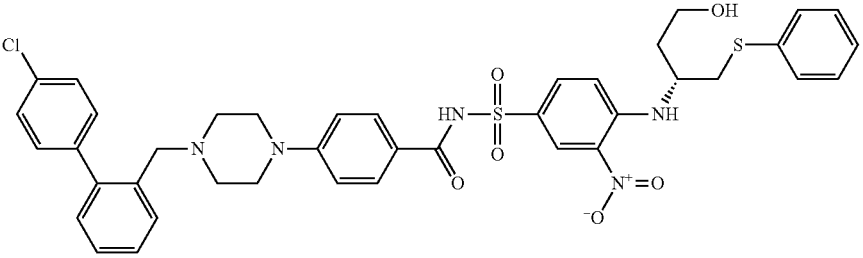 |

| Name | Structure |
|---|---|
| N-(4-(4-((4'-chloro(1,1'-biphenyl)-2-yl)methyl)piperazin-1-yl)benzoyl)-4-(((1R)-3-(isopropylamino)-1-((phenylsulfanyl)methyl)propyl)amino)-3-nitrobenzenesulfonamide, | 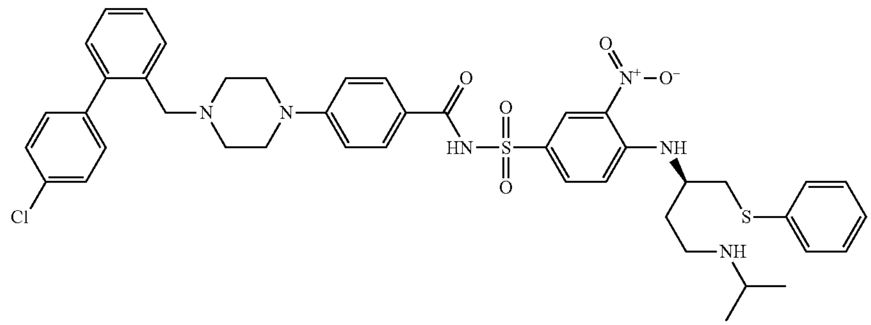 [SMILES: CC(C)NCC[C@H](CSc1ccccc1)Nc1ccc(S(=O)(=O)NC(=O)c2ccc(N3CCN(Cc4ccccc4-c4ccc(Cl)cc4)CC3)cc2)cc1[N+](=O)[O-]] |
| 4-(((1R)-3-(dimethylamino)-1-((phenylsulfanyl)methyl)propyl)amino)-N-(4-(4-(2-(2-naphthyl)benzyl)piperazin-1-yl)benzoyl)-3-nitrobenzenesulfonamide, | 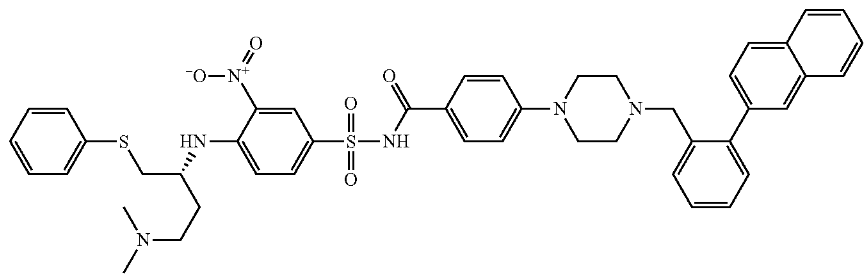 |
| 4-(((1R)-3-(dimethylamino)-1-((phenylsulfanyl)methyl)propyl)amino)-N-(4-(4-(2-(1-naphthyl)benzyl)piperazin-1-yl)benzoyl)-3-nitrobenzenesulfonamide, | 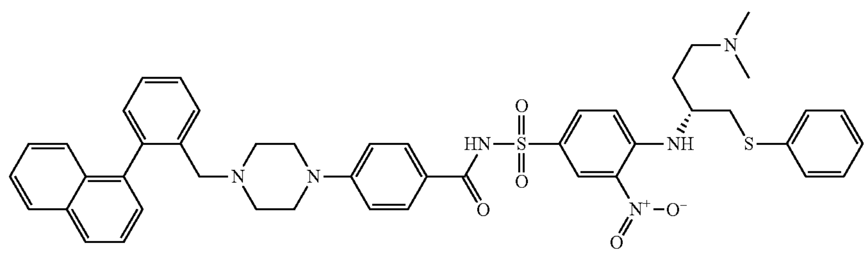 [SMILES: CN(C)CC[C@H](CSc1ccccc1)Nc1ccc(S(=O)(=O)NC(=O)c2ccc(N3CCN(Cc4ccccc4-c4cccc5ccccc45)CC3)cc2)cc1[N+](=O)[O-]] |
| N-(4-(4-((3'-cyano(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide, | 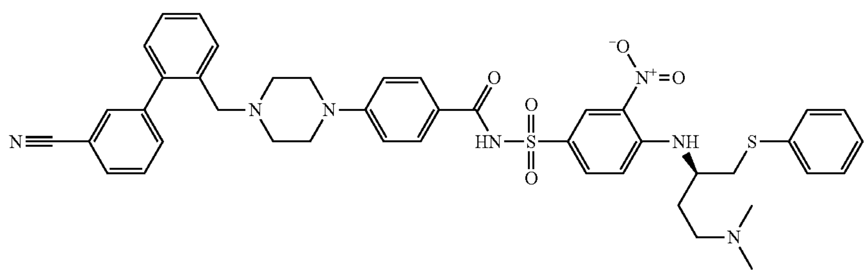 |
| 4-(((1R)-3-(dimethylamino)-1-((phenylsulfanyl)methyl)propyl)amino)-N-(4-(4-((3'-methoxy(1,1'-biphenyl)-2-yl)methyl)piperazin-1-yl)benzoyl)-3-nitrobenzenesulfonamide, | 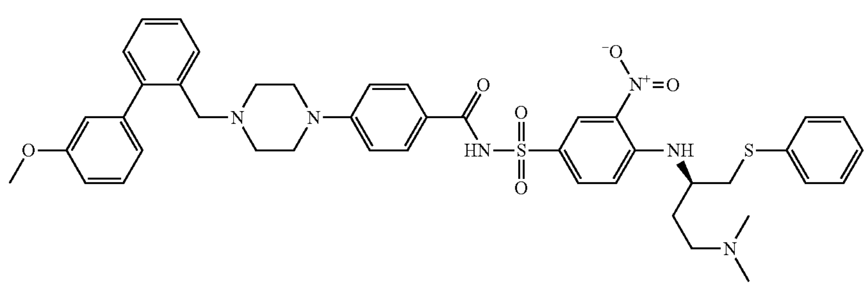 |

| Name | Structure |
|---|---|
| N-(4-(4-((3'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide | 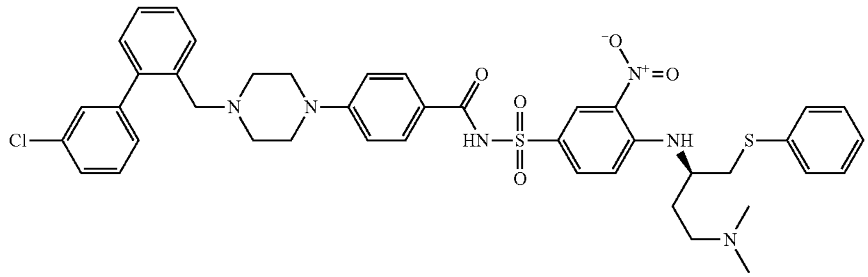 |
| N-(4-(4-((2'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide, | 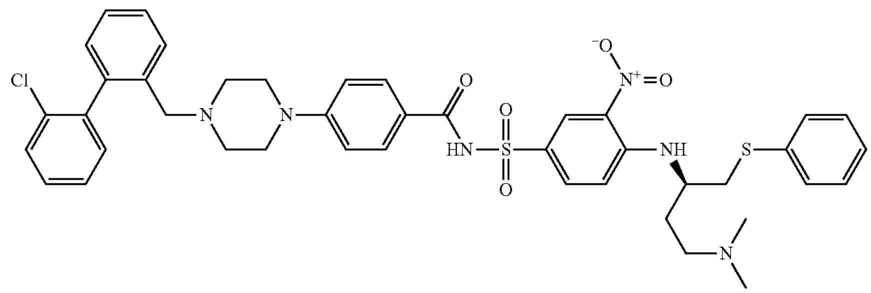 |
| N-(4-(4-(2-(1,3-benzodioxol-5-yl)benzyl)piperazin-1-yl)benzoyl)-4-(((1R)-3-(dimethylamino)-1-((phenylsulfanyl)methyl)propyl)amino)-3-nitrobenzenesulfonamide, | 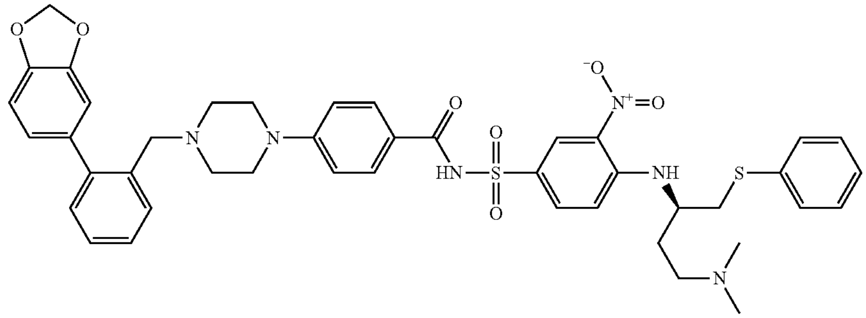 |
| 4-(((1R)-3-(dimethylamino)-1-((phenylsulfanyl)methyl)propyl)amino)-3-nitro-N-(4-(4-(2-(3-thienyl)benzyl)piperazin-1-yl)benzoyl)benzenesulfonamide, | 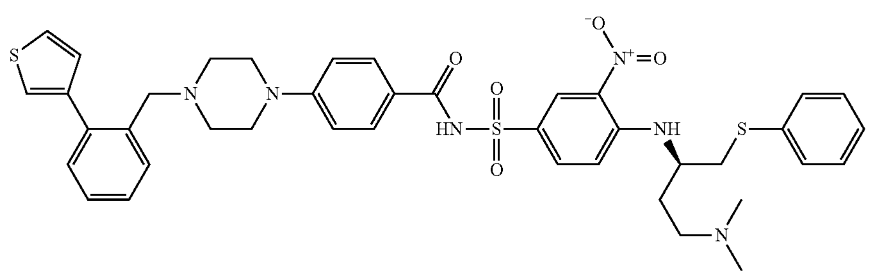 |
| 4-(((1R)-3-(dimethylamino)-1-((phenylsulfanyl)methyl)propyl)amino)-3-nitro-N-(4-(4-(2-(pyridin-3-yl)benzyl)piperazin-1-yl)benzoyl)benzenesulfonamide, | 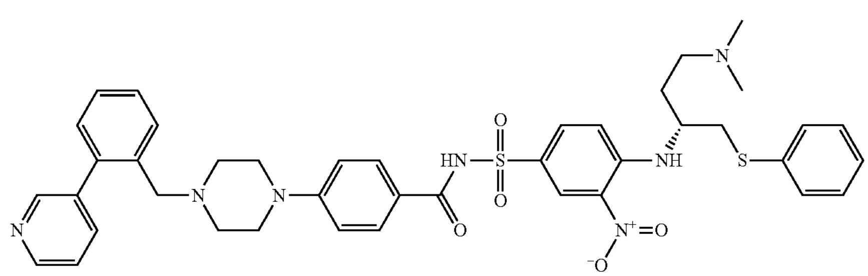 |

-continued

| Name | Structure |
|------|-----------|
| 4-(((1R)-3-(dimethylamino)-1-((phenylsulfanyl)methyl)propyl)amino)-3-nitro-N-(4-(4-(2-(quinolin-8-yl)benzyl)piperazin-1-yl)benzoyl)benzenesulfonamide, | 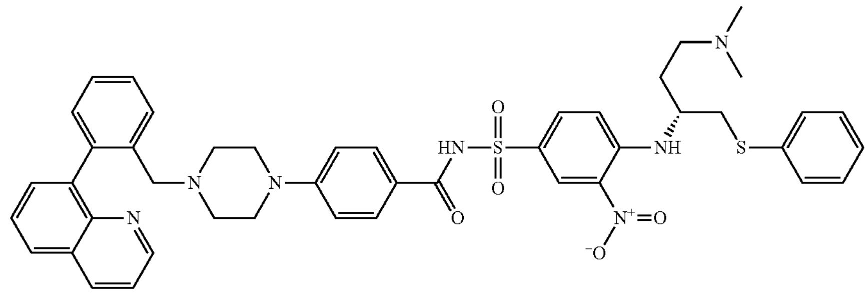 |
| N-(4-(4-(2-(1-benzofuran-2-yl)benzyl)piperazin-1-yl)benzoyl)-4-(((1R)-3-dimethylamino)-1-((phenylsulfanyl)methyl)propyl)amino)-3-nitrobenzenesulfonamide, | 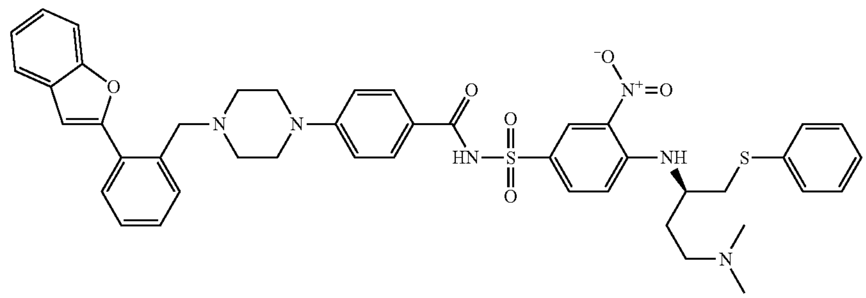 |
| 4-(((1R)-3-(dimethylamino)-1-((phenylsulfanyl)methyl)propyl)amino)-N-(4-(4-((2'-methyl(1,1'-biphenyl)-2-yl)methyl)piperazin-1-yl)benzoyl)-3-nitrobenzenesulfonamide, | 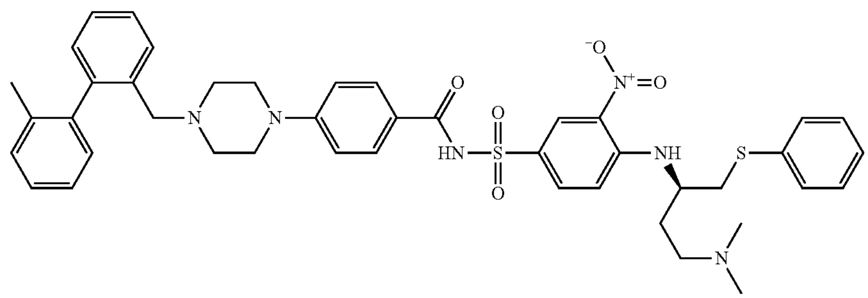 |
| 4-(((1R)-3-(dimethylamino)-1-((phenylsulfanyl)methyl)propyl)amino)-3-nitro-N-(4-(4-(2-(quinolin-3-yl)benzyl)piperazin-1-yl)benzoyl)benzenesulfonamide, | 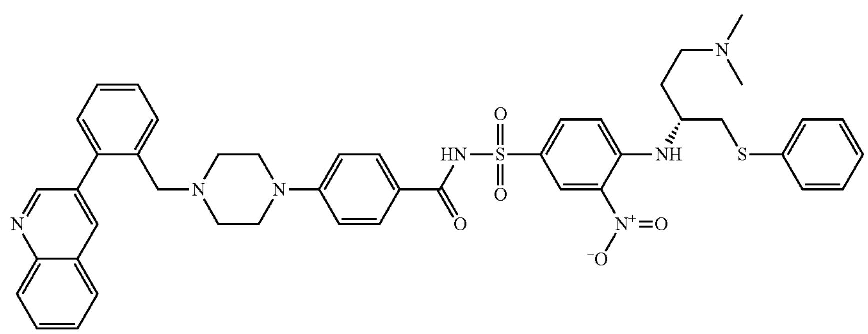 |
| N-(4-(4-((1-(4-chlorophenyl)-2-naphthyl)methyl)piperazin-1-yl)benzoyl)-3-nitro-4-((2-(phenylsulfanyl)ethyl)amino)benzenesulfonamide, | 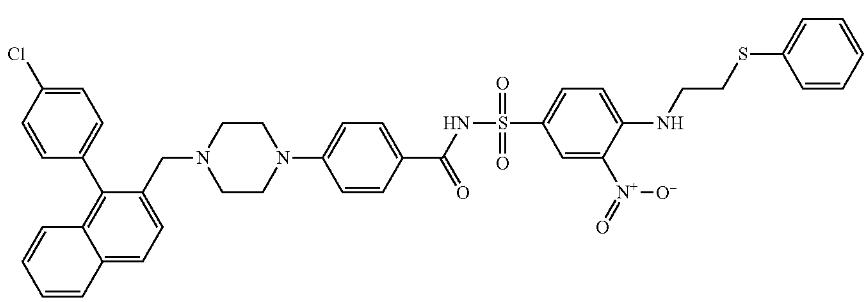 [SMILES: O=C(NS(=O)(=O)c1ccc(NCCSc2ccccc2)c([N+](=O)[O-])c1)c1ccc(N2CCN(Cc3ccc4ccccc4c3-c3ccc(Cl)cc3)CC2)cc1] |

-continued

| Name | Structure |
|---|---|
| N-(4-(4-((1-(4-chlorophenyl)-2-naphthyl)methyl)piperazin-1-yl)benzoyl)-4-(((1R)-3-(dimethylamino)-1-((phenylsulfanyl)methyl)propyl)amino)-3-nitrobenzenesulfonamide, | 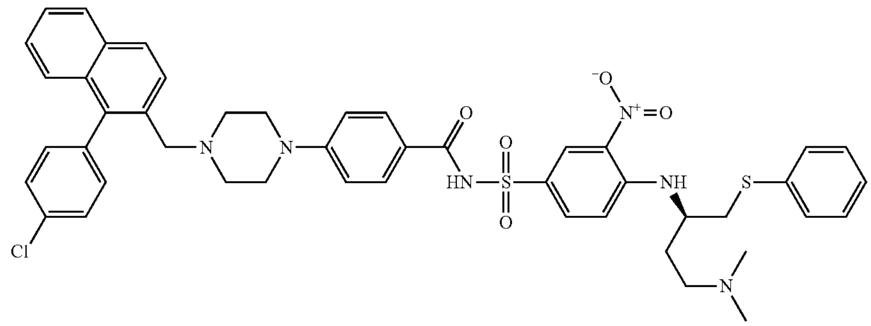 |
| N-(4-(4-((1-(4-chlorophenyl)-2-naphthyl)methyl)piperazin-1-yl)benzoyl)-4-(((1R)-3-(morpholin-4-yl)-1-((phenylsulfanyl)methyl)propyl)amino)-3-nitrobenzenesulfonamide, | 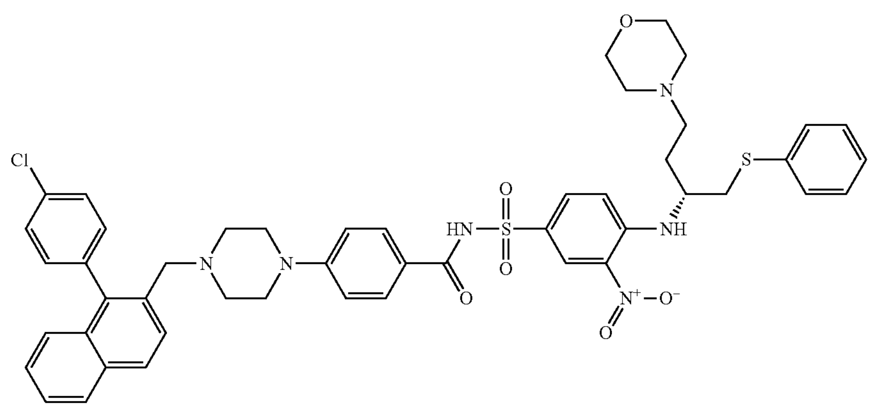 [SMILES: O=C(NS(=O)(=O)c1ccc(N[C@H](CCN2CCOCC2)CSc2ccccc2)c([N+](=O)[O-])c1)c1ccc(N2CCN(Cc3ccc4ccccc4c3-c3ccc(Cl)cc3)CC2)cc1] |
| N-(4-(4-((4'-chloro(1,1'-biphenyl)-2-yl)methyl)piperazin-1-yl)benzoyl)-3-nitro-4-((2-(phenylsulfanyl)cyclopentyl)amino)benzenesulfonamide, | 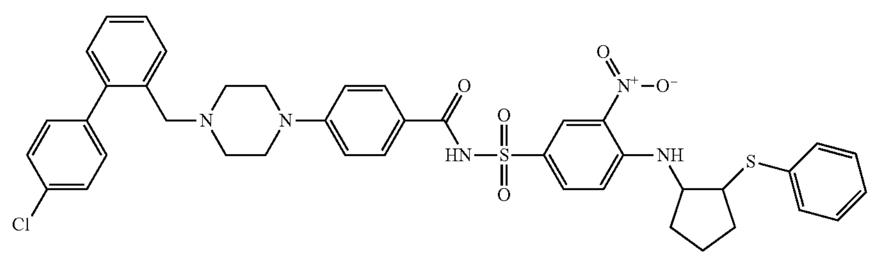 [SMILES: O=C(NS(=O)(=O)c1ccc(NC2CCCC2Sc2ccccc2)c([N+](=O)[O-])c1)c1ccc(N2CCN(Cc3ccccc3-c3ccc(Cl)cc3)CC2)cc1] |
| N-(4-(4-((1,1'-biphenyl)-2-ylmethyl)-4-methoxypiperidin-1-yl)benzoyl)-3-nitro-4-((2-(phenylsulfanyl)cyclopentyl)amino)benzenesulfonamide, | 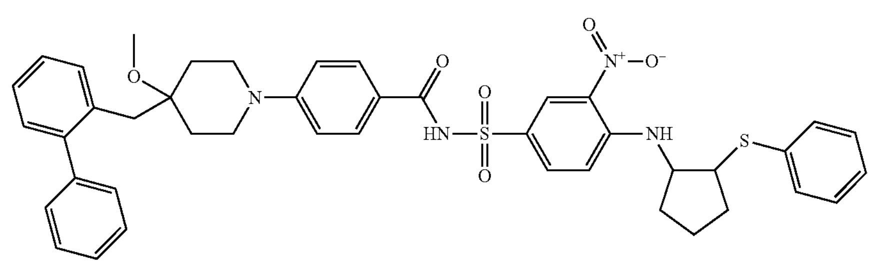 [SMILES: COC1(Cc2ccccc2-c2ccccc2)CCN(c2ccc(C(=O)NS(=O)(=O)c3ccc(NC4CCCC4Sc4ccccc4)c([N+](=O)[O-])c3)cc2)CC1] |
| N-(4-(4-((4'-fluoro(1,1'-biphenyl)-2-yl)methyl)piperazin-1-yl)benzoyl)-3-nitro-4-((2-(phenylsulfanyl)ethyl)amino)benzenesulfonamide, | 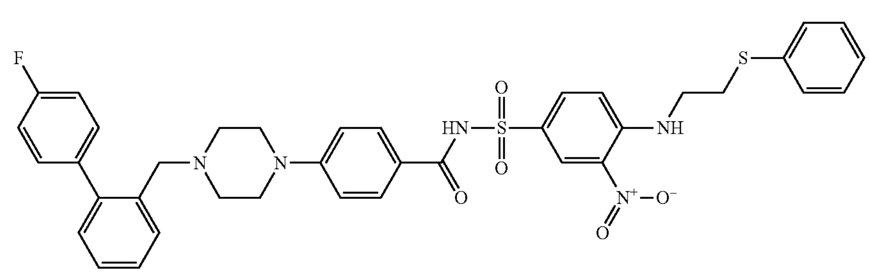 [SMILES: O=C(NS(=O)(=O)c1ccc(NCCSc2ccccc2)c([N+](=O)[O-])c1)c1ccc(N2CCN(Cc3ccccc3-c3ccc(F)cc3)CC2)cc1] |

-continued

| Name | Structure |
|---|---|
| N-(4-(4-((3',4'-dichloro(1,1'-biphenyl)-2-yl)methyl)piperazin-1-yl)benzoyl)-3-nitro-4-((2-(phenylsulfanyl)ethyl)amino)benzenesulfonamide, | 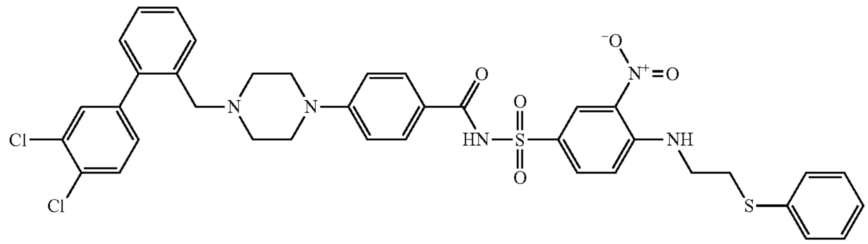 |
| N-(4-(4-((3',4'-dichloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide, | 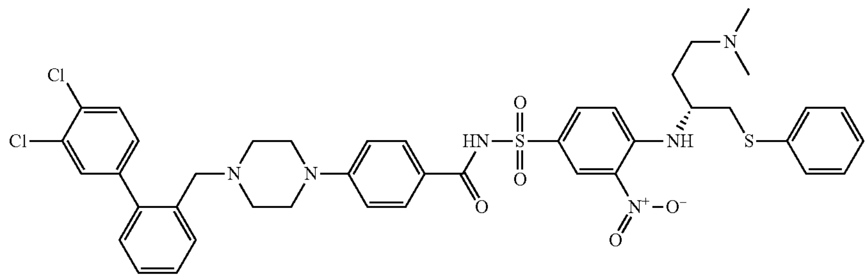 [SMILES: CN(C)CC[C@H](CSc1ccccc1)Nc1ccc(S(=O)(=O)NC(=O)c2ccc(N3CCN(Cc4ccccc4-c4ccc(Cl)c(Cl)c4)CC3)cc2)cc1[N+](=O)[O-]] |
| N-(4-(4-((3',4'-dichloro(1,1'-biphenyl)-2-yl)methyl)piperazin-1-yl)benzoyl)-4-(((1R)-3-(morpholin-4-yl)-1-((phenylsulfanyl)methyl)propyl)amino)-3-nitrobenzenesulfonamide, | 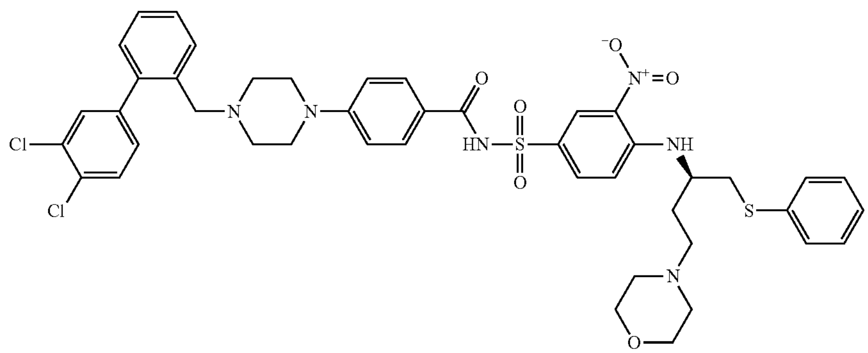 |
| 3-nitro-4-((2-(phenylsulfanyl)ethyl)amino)-N-(4-(4-((4'-(trifluoromethyl)(1,1'-biphenyl)-2-yl)methyl)piperazin-1-yl)benzoyl)benzenesulfonamide, | 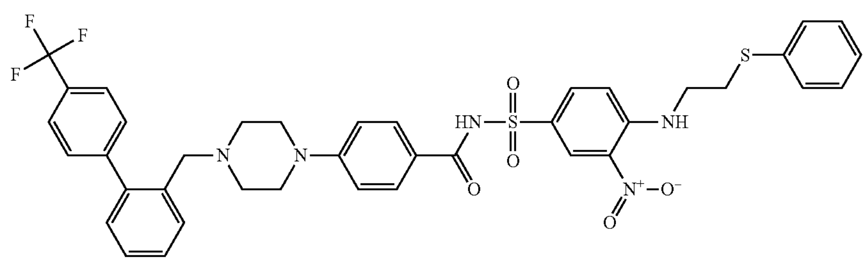 [SMILES: O=C(NS(=O)(=O)c1ccc(NCCSc2ccccc2)c([N+](=O)[O-])c1)c1ccc(N2CCN(Cc3ccccc3-c3ccc(C(F)(F)F)cc3)CC2)cc1] |
| 4-(((1R)-3-(dimethylamino)-1-((phenylsulfanyl)methyl)propyl)amino)-3-nitro-N-(4-(4-((4'-(trifluoromethyl)(1,1'-biphenyl)-2-yl)methyl)piperazin-1-yl)benzoyl)benzenesulfonamide, | 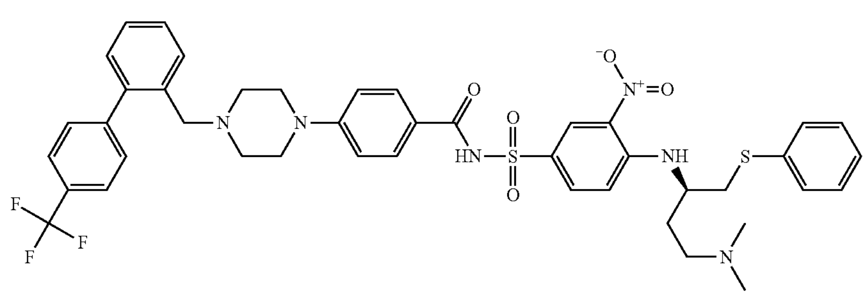 |

| Name | Structure |
|---|---|
| 4-(((1R)-3-(morpholin-4-yl)-1-((phenylsulfanyl)methyl)propyl)amino)-3-nitro-N-(4-(4-((4'-(trifluoromethyl)(1,1'-biphenyl)-2-yl)methyl)piperazin-1-yl)benzoyl)benzenesulfonamide, | 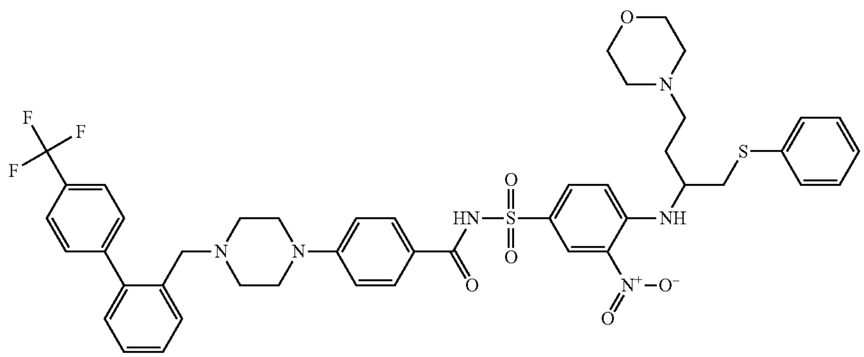 [SMILES: O=C(NS(=O)(=O)c1ccc(NC(CCN2CCOCC2)CSc2ccccc2)c([N+](=O)[O-])c1)c1ccc(N2CCN(Cc3ccccc3-c3ccc(C(F)(F)F)cc3)CC2)cc1] |
| 3-nitro-4-((2-(phenylsulfanyl)ethyl)amino)-N-(4-(4-((4'-(trifluoromethoxy)(1,1'-biphenyl)-2-yl)methyl)piperazin-1-yl)benzoyl)benzenesulfonamide, | |
| 3-nitro-4-((2-(phenylsulfanyl)ethyl)amino)-N-(4-(4-((4'-(trifluoromethoxy)(1,1'-biphenyl)-2-yl)methyl)piperazin-1-yl)benzoyl)benzenesulfonamide, | |
| 4-(((1R)-3-(morpholin-4-yl)-1-((phenylsulfanyl)methyl)propyl)amino)-3-nitro-N-(4-(4-((4'-(trifluoromethoxy)(1,1'-biphenyl)-2-yl)methyl)piperazin-1-yl)benzoyl)benzenesulfonamide, | 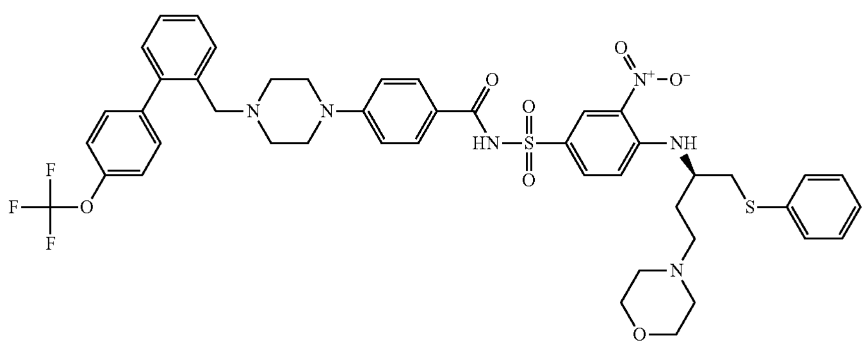 [SMILES: O=C(NS(=O)(=O)c1ccc(N[C@H](CCN2CCOCC2)CSc2ccccc2)c([N+](=O)[O-])c1)c1ccc(N2CCN(Cc3ccccc3-c3ccc(OC(F)(F)F)cc3)CC2)cc1] |
| 3-nitro-N-(4-(4-((4'-phenoxy(1,1'-biphenyl)-2-yl)methyl)piperazin-1-yl)benzoyl)-4-((2-(phenylsulfanyl)ethyl)amino)benzenesulfonamide, | 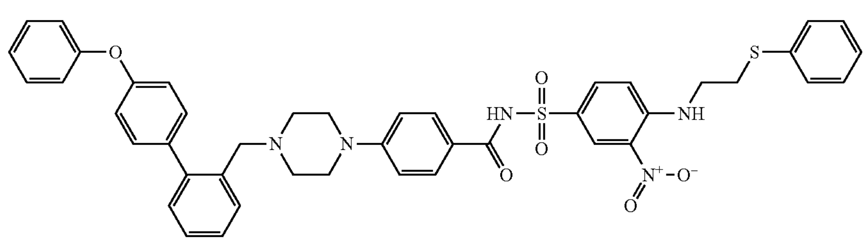 [SMILES: O=C(NS(=O)(=O)c1ccc(NCCSc2ccccc2)c([N+](=O)[O-])c1)c1ccc(N2CCN(Cc3ccccc3-c3ccc(Oc4ccccc4)cc3)CC2)cc1] |

| Name | Structure |
|---|---|
| 4-(((1R)-3-(morpholin-4-yl)-1-((phenylsulfanyl)methyl)propyl)amino)-3-nitro-N-(4-(4-((4'-phenoxy(1,1'-biphenyl)-2-yl)methyl)piperazin-1-yl)benzoyl)benzenesulfonamide, | 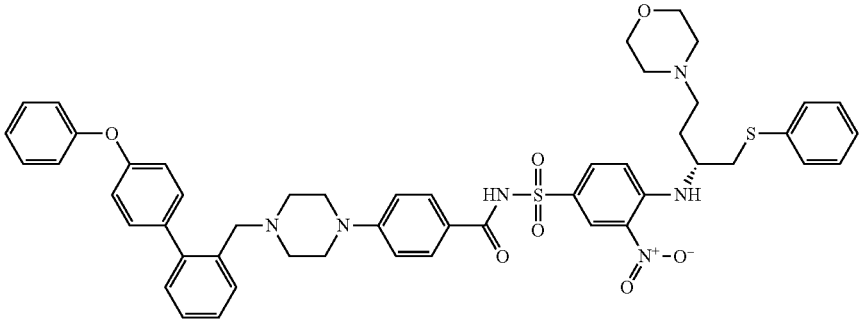 [SMILES: O=C(NS(=O)(=O)c1ccc(N[C@H](CCN2CCOCC2)CSc2ccccc2)c([N+](=O)[O-])c1)c1ccc(N2CCN(Cc3ccccc3-c3ccc(Oc4ccccc4)cc3)CC2)cc1] |
| N-(4-(4-((4'-chloro(1,1'-biphenyl)-2-yl)methyl)piperazin-1-yl)benzoyl)-4-(((1S)-3-(dimethylamino)-1-((phenylsulfanyl)methyl)propyl)amino)-3-nitrobenzenesulfonamide, | 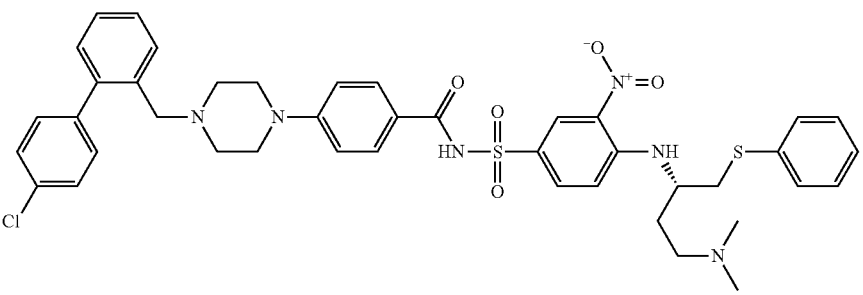 |
| N-(4-(4-((4'-chloro(1,1'-biphenyl)-2-yl)methyl)piperazin-1-yl)benzoyl)-4-((1,1-dimethyl-2-(phenylsulfonyl)ethyl)amino)-3-nitrobenzenesulfonamide, | 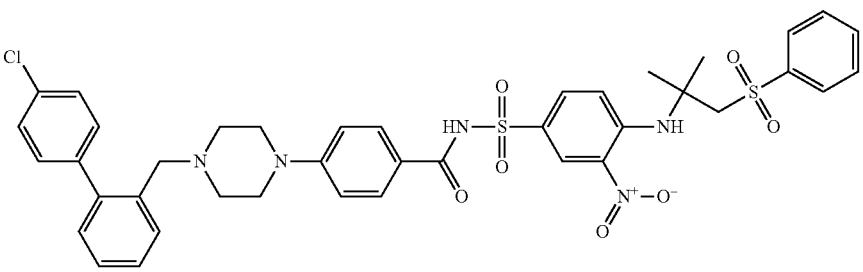 [SMILES: CC(C)(CS(=O)(=O)c1ccccc1)Nc1ccc(S(=O)(=O)NC(=O)c2ccc(N3CCN(Cc4ccccc4-c4ccc(Cl)cc4)CC3)cc2)cc1[N+](=O)[O-]] |
| N-(4-(4-((2',4'-dichloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide, | 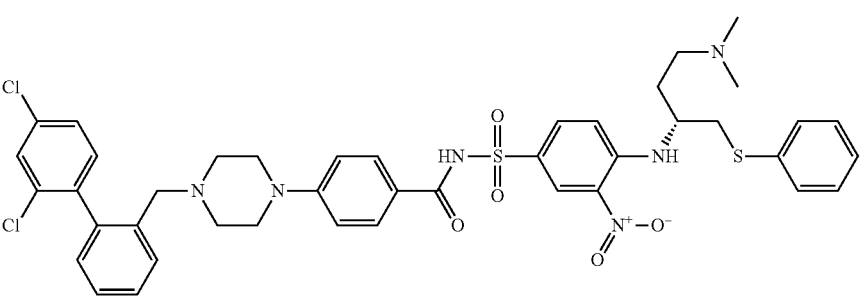 [SMILES: CN(C)CC[C@H](CSc1ccccc1)Nc1ccc(S(=O)(=O)NC(=O)c2ccc(N3CCN(Cc4ccccc4-c4ccc(Cl)cc4Cl)CC3)cc2)cc1[N+](=O)[O-]] |
| 4-(((1R)-3-(dimethylamino)-1-((phenylsulfanyl)methyl)propyl)amino)-3-nitro-N-(4-(4-(2-(2-thienyl)benzyl)piperazin-1-yl)benzoyl)benzenesulfonamide, | 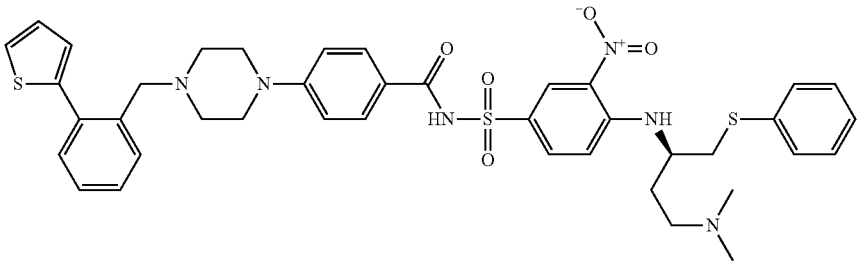 |

-continued

| Name | Structure |
|---|---|
| N-(4-(4-((4'-chloro-2'-methyl(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide, | 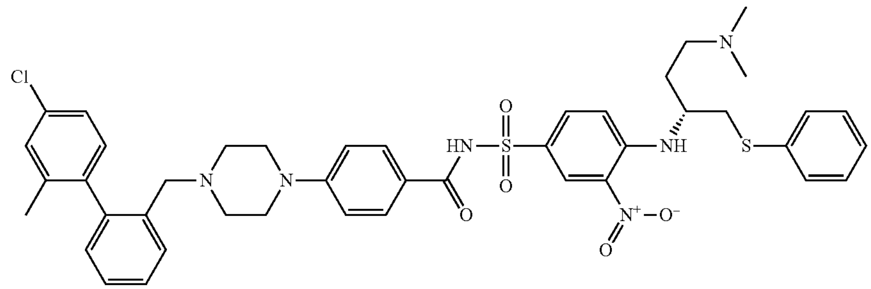 |
| N-(4-(4-((2',4'-difluoro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide, | 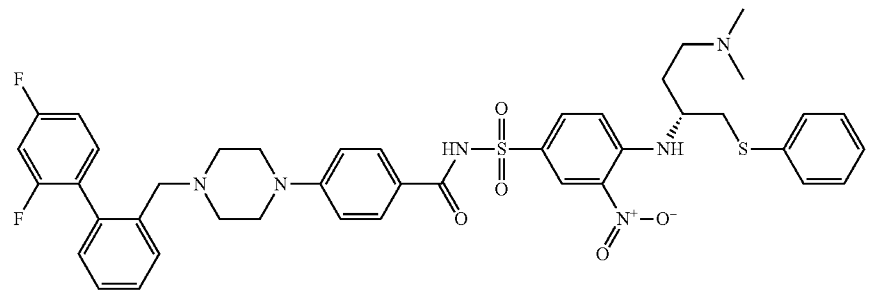 [SMILES: CN(C)CC[C@H](CSc1ccccc1)Nc1ccc(S(=O)(=O)NC(=O)c2ccc(N3CCN(Cc4ccccc4-c4ccc(F)cc4F)CC3)cc2)cc1[N+](=O)[O-]] |
| N-(4-(4-((1,1'-biphenyl)-2-ylmethyl)piperazin-1-yl)benzoyl)-3-nitro-4-((2-(phenylsulfonyl)ethyl)amino)benzenesulfonamide, | 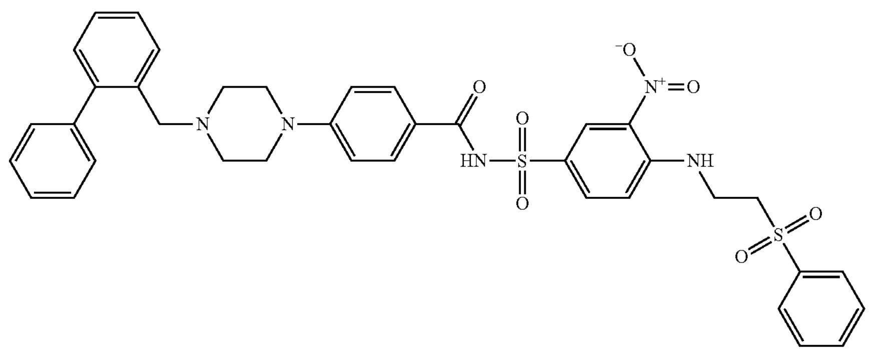 |
| N-(4-(4-((4,-chloro(1,1'-biphenyl)-2-yl)methyl)piperazin-1-yl)benzoyl)-3-nitro-4-((2-(phenylsulfonyl)ethyl)amino)benzenesulfonamide, | 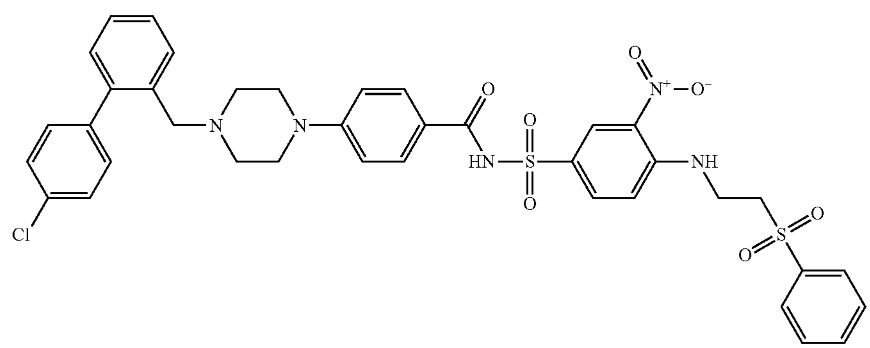 [SMILES: O=C(NS(=O)(=O)c1ccc(NCCS(=O)(=O)c2ccccc2)c([N+](=O)[O-])c1)c1ccc(N2CCN(Cc3ccccc3-c3ccc(Cl)cc3)CC2)cc1] |
| N-(4-(4-((1,1'-biphenyl)-2-ylmethyl)piperazin-1-yl)benzoyl)-3-nitro-4-((4-(phenylsulfanyl)tetrahydro-3-furanyl)amino)benzenesulfonamide, | |

-continued

| Name | Structure |
|---|---|
| 4-(((R)-3-(dimethylamino)-1-((phenylsulfanyl)methyl)propyl)amino)-N-(4-(4-(2-(5-methyl-2-thienyl)benzyl)piperazin-1-yl)benzoyl)-3-nitrobenzenesulfonamide, | 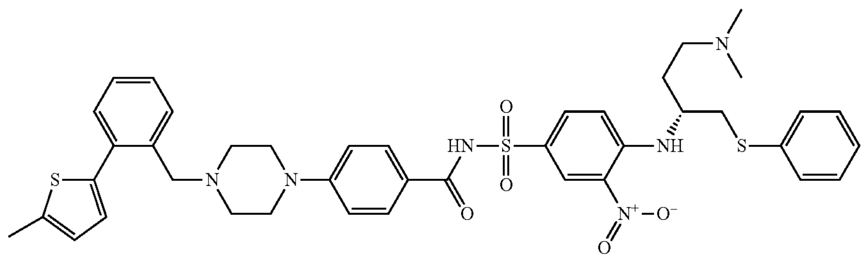 [SMILES: Cc1ccc(-c2ccccc2CN2CCN(c3ccc(C(=O)NS(=O)(=O)c4ccc(N[C@H](CCN(C)C)CSc5ccccc5)c([N+](=O)[O-])c4)cc3)CC2)s1] |
| N-(4-(4-((4'-chloro(1,1'-biphenyl)-2~yl)methyl)piperazin-1-yl)benzoyl)-3-nitro-4-((4-(phenylsulfonyl)tetrahydro-3-furanyl)amino)benzenesulfonamide, | 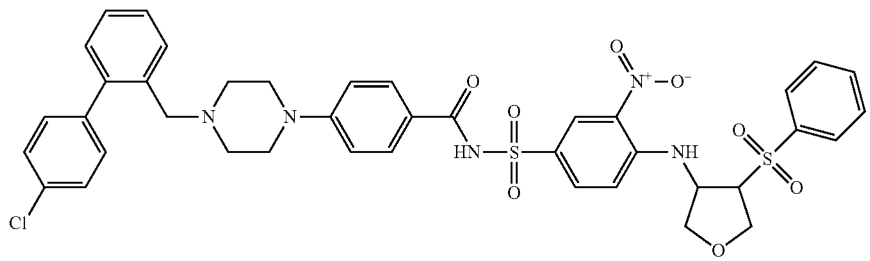 [SMILES: O=C(NS(=O)(=O)c1ccc(NC2COCC2S(=O)(=O)c2ccccc2)c([N+](=O)[O-])c1)c1ccc(N2CCN(Cc3ccccc3-c3ccc(Cl)cc3)CC2)cc1] |
| N-(4-(4-((1,1'-biphenyl)-2-ylmethyl)piperazin-1-yl)benzoyl)-3-nitro-4-((4-(phenylsulfonyl)tetrahydro-3-furanyl)amino)benzene-sulfonamide, | 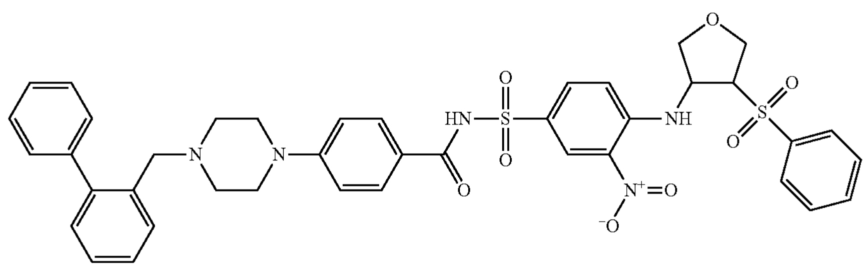 |
| N-(4-(4-((4'-chloro(1,1'-biphenyl)-2-yl)methyl)piperazin-1-yl)benzoyl)-4-((1-methyl-4-(phenylsulfanyl)pyrrolidin-3-yl)amino)-3-nitrobenzenesulfonamide. | 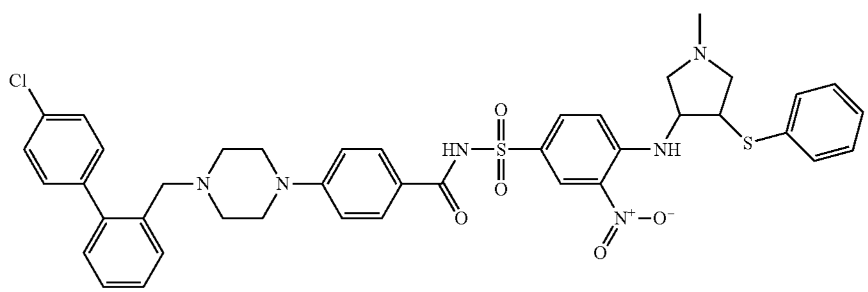 [SMILES: CN1CC(Nc2ccc(S(=O)(=O)NC(=O)c3ccc(N4CCN(Cc5ccccc5-c5ccc(Cl)cc5)CC4)cc3)cc2[N+](=O)[O-])C(Sc2ccccc2)C1] |
| N-(4-(4-((2-(4-chlorophenyl)-1-cyclohexen-1-yl)methyl)piperazin-1-yl)benzoyl)-4-(((1R)-3-(morpholin-4-yl)-1-((phenylsulfanyl)methyl)propyl)amino)-3-nitrobenzenesulfonamide, | 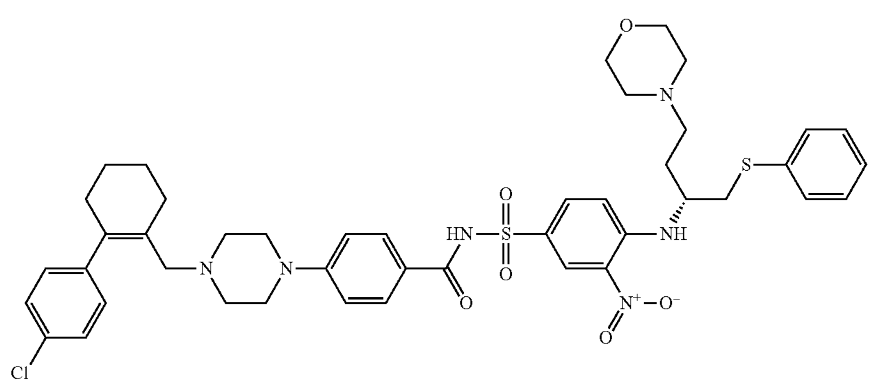 [SMILES: O=C(NS(=O)(=O)c1ccc(N[C@H](CCN2CCOCC2)CSc2ccccc2)c([N+](=O)[O-])c1)c1ccc(N2CCN(CC3=C(c4ccc(Cl)cc4)CCCC3)CC2)cc1] |

-continued

| Name | Structure |
|------|-----------|
| N-(4-(4-((2-(4-chlorophenyl)-1-cyclohexen-1-yl)methyl)piperazin-1-yl)benzoyl)-4-(((1R)-3-(morpholin-4-yl)-1-((phenylsulfanyl)methyl)propyl)amino)-3-nitrobenzenesulfonamide, | 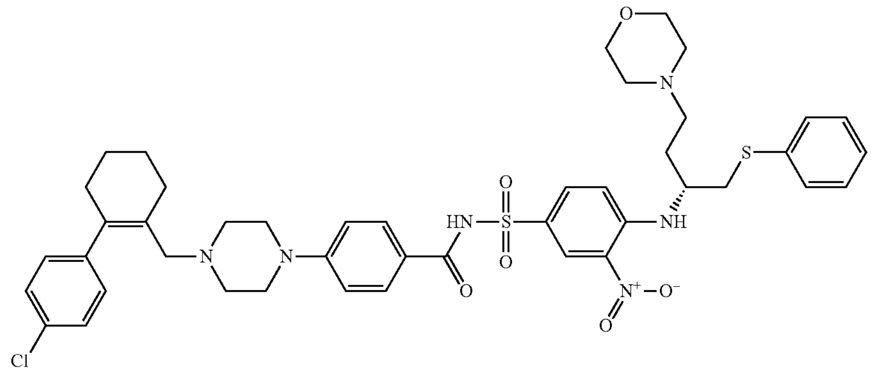 [SMILES: O=C(NS(=O)(=O)c1ccc(N[C@H](CCN2CCOCC2)CSc2ccccc2)c([N+](=O)[O-])c1)c1ccc(N2CCN(CC3=C(c4ccc(Cl)cc4)CCCC3)CC2)cc1] |
| N-(4-(4-((4'-bromo(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide, | 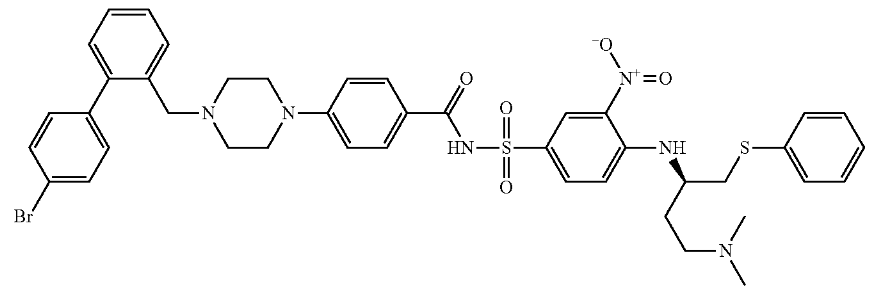 |
| N-(4-(4-(1-(4'-chloro(1,1'-biphenyl)-2-yl)cyclopropyl)piperazin-1-yl)benzoyl)-4-(((1R)-3-(dimethylamino)-1-((phenylsulfanyl)methyl)propyl)amino)-3-nitrobenzenesulfonamide, | 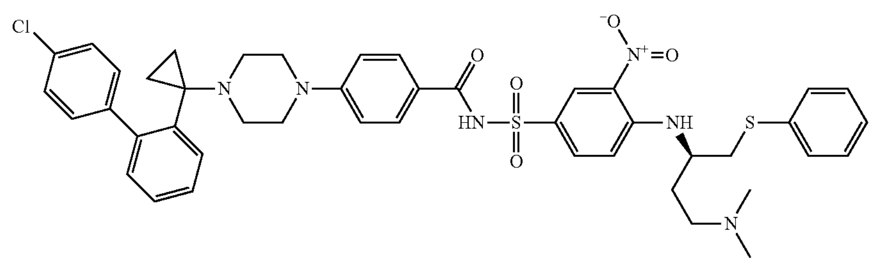 |
| N-(4-(4-((2-(4-chlorophenyl)-1-cyclohexen-1-yl)methyl)piperazin-1-yl)benzoyl)-4-(((1R)-2-(dimethylamino)-1-((phenylsulfanyl)methyl)ethyl)amino)-3-nitrobenzenesulfonamide, | 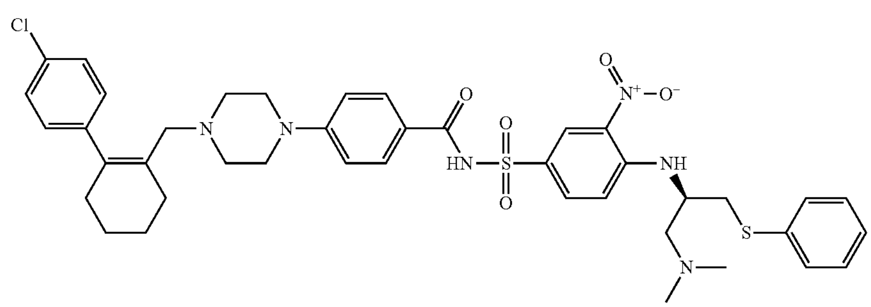 [SMILES: CN(C)C[C@H](CSc1ccccc1)Nc1ccc(S(=O)(=O)NC(=O)c2ccc(N3CCN(CC4=C(c5ccc(Cl)cc5)CCCC4)CC3)cc2)cc1[N+](=O)[O-]] |
| N-(4-(4-((4'-chloro(1,1'-biphenyl)-2-yl)methyl)piperazin-1-yl)benzoyl)-4-(((1R)-2-(dimethylamino)-1-((phenylsulfanyl)methyl)ethyl)amino)-3-nitrobenzenesulfonamide, | 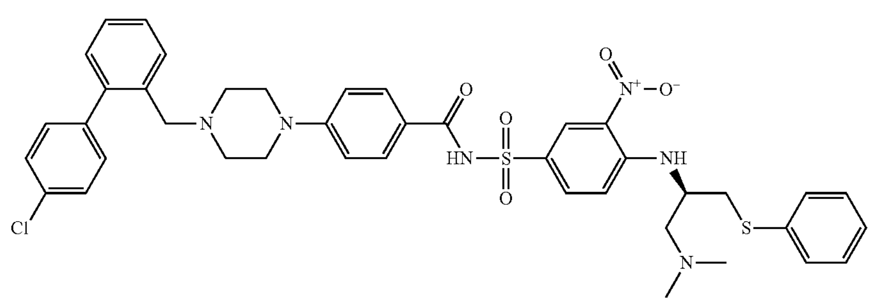 [SMILES: CN(C)C[C@H](CSc1ccccc1)Nc1ccc(S(=O)(=O)NC(=O)c2ccc(N3CCN(Cc4ccccc4-c4ccc(Cl)cc4)CC3)cc2)cc1[N+](=O)[O-]] |

-continued

| Name | Structure |
|---|---|
| N-(4-(4-((4'-chloro(1,1'-biphenyl)-2-yl)methyl)piperazin-1-yl)benzoyl)-4-(((1R)-2-(diethylamino)-1-((phenylsulfanyl)methyl)ethyl)amino)-3-nitrobenzenesulfonamide, | 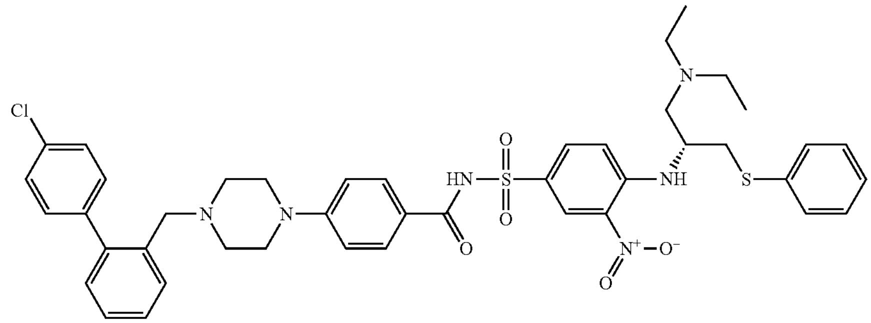 [SMILES: CCN(CC)C[C@H](CSc1ccccc1)Nc1ccc(S(=O)(=O)NC(=O)c2ccc(N3CCN(Cc4ccccc4-c4ccc(Cl)cc4)CC3)cc2)cc1[N+](=O)[O-]] |
| N-(4-(4-((4'-chloro(1,1'-biphenyl)-2-yl)methyl)piperazin-1-yl)benzoyl)-4-(((1R)-2-(morpholin-4-yl)-1-((phenylsulfanyl)methyl)ethyl)amino)-3-nitrobenzenesulfonamide, | 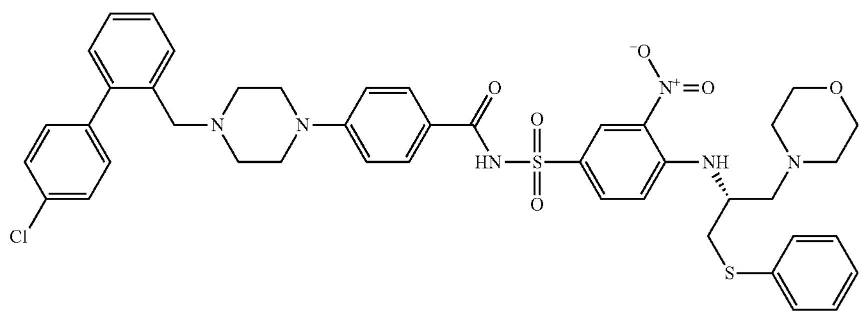 |
| N-(4-(4-((2-(4-chlorophenyl)-1-cyclohexen-1-yl)methyl)piperazin-1-yl)benzoyl)-4-(((1R)-2-(diethylamino)-1-((phenylsulfanyl)methyl)ethyl)amino)-3-nitrobenzenesulfonamide, | |
| N-(4-(4-((2-(4-chlorophenyl)-1-cyclohexen-1-yl)methyl)piperazin-1-yl)benzoyl)-4-(((1R)-2-(morpholin-4-yl)-1-((phenylsulfanyl)methyl)ethyl)amino)-3-nitrobenzenesulfonamide, | |

-continued

| Name | Structure |
|---|---|
| N-(4-(4-((4'-chloro(1,1'-biphenyl)-2-yl)methyl)piperazin-1-yl)benzoyl)-4-(((1R)-3-(cyclopropyl(methyl)amino)-1-((phenylsulfanyl)methyl)propyl)amino)-3-nitrobenzenesulfonamide, | 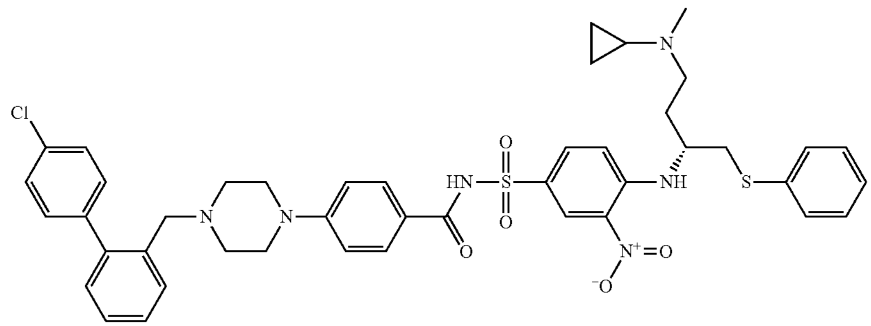 |
| N-(4-(4-((1,1'-biphenyl)-2-ylmethyl)-4-methoxypiperidin-1,-yl)benzoyl)-4-(((1R)-3-(dimethylamino)-1-((phenylsulfanyl)methyl)propyl)amino)-3-nitrobenzenesulfonamide, | 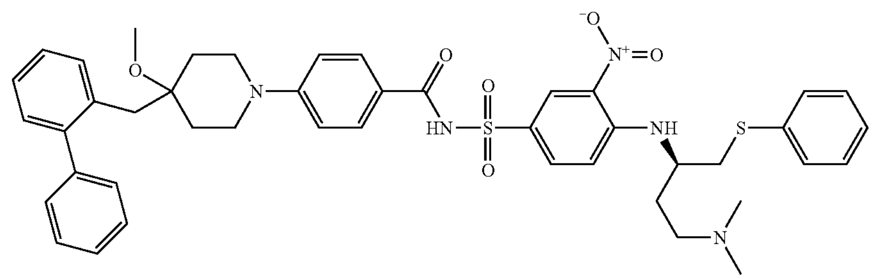 |
| 4-(((1R)-3-(dimethylamino)-1-((phenylsulfanyl)methyl)propyl)amino)-N-(4-(4-methoxy-4-(2-(pyridin-3-yl)benzyl)piperidin-1-yl)benzoyl)-3-nitrobenzenesulfonamide, | 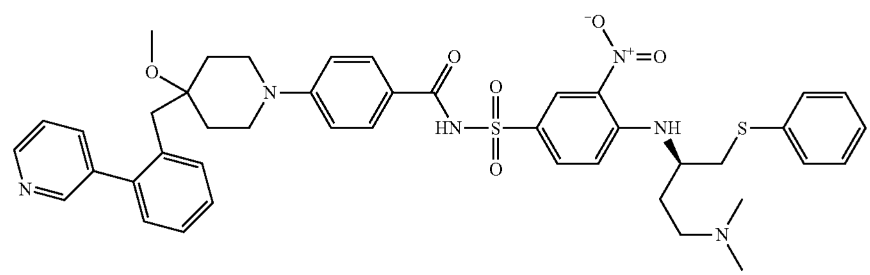 |
| 4-(((1R)-3-(dimethylamino)-1-((phenylsulfanyl)methyl)propyl)amino)-N-(4-(4-methoxy-4-(2-(pyridin-4-yl)benzyl)piperidin-1-yl)benzoyl)-3-nitrobenzenesulfonamide, | 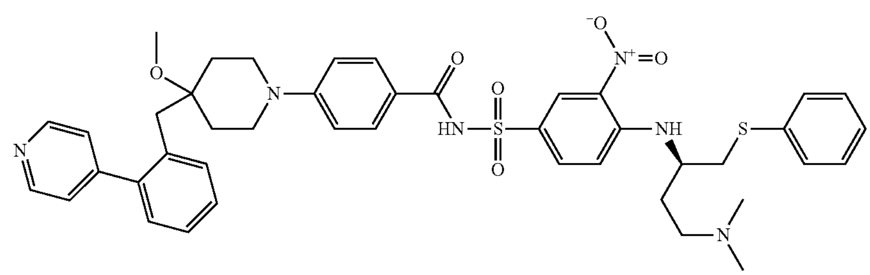 |
| 4-(((1R)-3-(dimethylamino)-1-((phenylsulfanyl)methyl)propyl)amino)-N-(4-(4-methoxy-4-(2-(2-thienyl)benzyl)piperidin-1-yl)benzoyl)-3-nitrobenzenesulfonamide, | 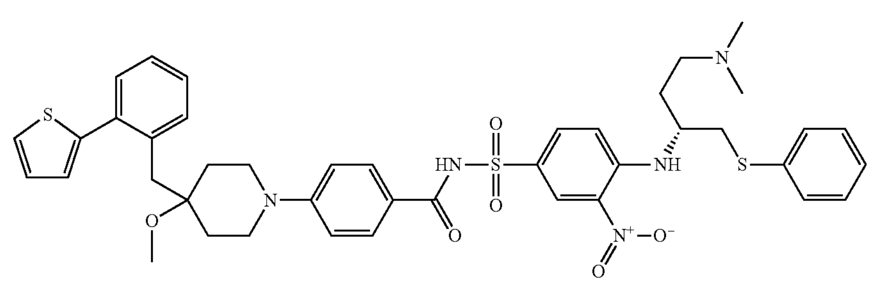 [SMILES: COC1(Cc2ccccc2-c2cccs2)CCN(c2ccc(C(=O)NS(=O)(=O)c3ccc(N[C@H](CCN(C)C)CSc4ccccc4)c([N+](=O)[O-])c3)cc2)CC1] |

-continued

| Name | Structure |
|---|---|
| 4-(((1R)-3-(dimethylamino)-1-((phenylsulfanyl)methyl)propyl)amino)-N-(4-(4-methoxy-4-(2-(3-thienyl)benzyl)piperidin-1-yl)benzoyl)-3-nitrobenzenesulfonamide, | 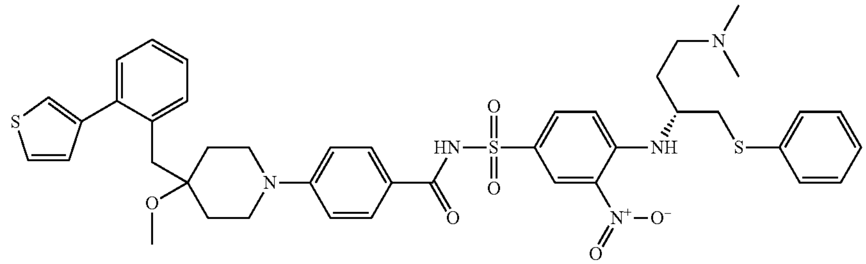 [SMILES: COC1(Cc2ccccc2-c2ccsc2)CCN(c2ccc(C(=O)NS(=O)(=O)c3ccc(N[C@H](CCN(C)C)CSc4ccccc4)c([N+](=O)[O-])c3)cc2)CC1] |
| 4-(((1R)-3-(azetidin-1-yl)-1-((phenylsulfanyl)methyl)propyl)amino)-N-(4-(4-((4'-chloro(1,1'-biphenyl)-2-yl)methyl)piperazin-1-yl)benzoyl)-3-nitrobenzenesulfonamide, | 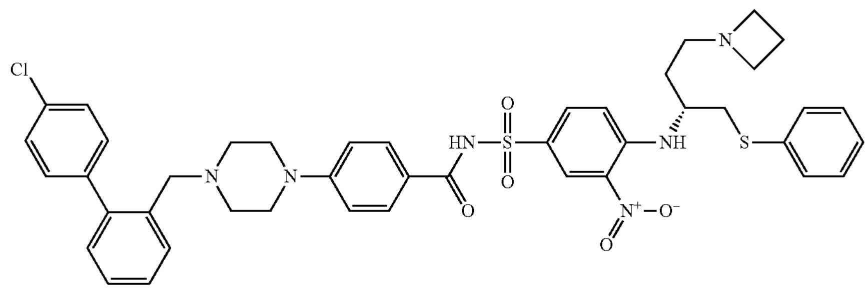 [SMILES: O=C(NS(=O)(=O)c1ccc(N[C@H](CCN2CCC2)CSc2ccccc2)c([N+](=O)[O-])c1)c1ccc(N2CCN(Cc3ccccc3-c3ccc(Cl)cc3)CC2)cc1] |
| N-(4-(4-((4'-chloro(1,1'-biphenyl)-2-yl)methyl)piperazin-1-yl)benzoyl)-3-nitro-4-(((1R)-1-((phenylsulfanyl)methyl)-3-((2,2,2-trifluoroethyl)amino)propyl)amino)benzenesulfonamide, | 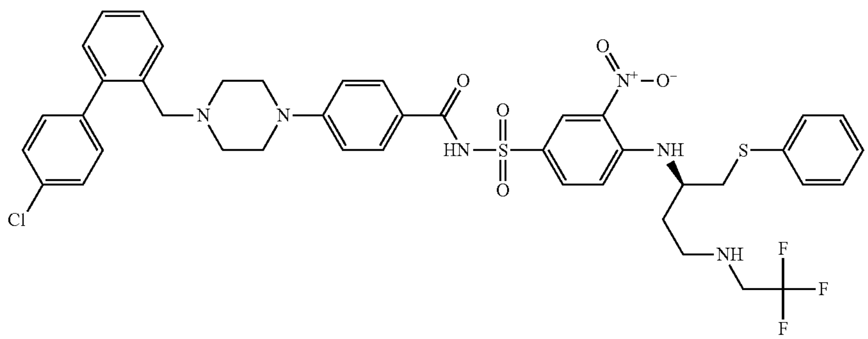 [SMILES: O=C(NS(=O)(=O)c1ccc(N[C@H](CCNCC(F)(F)F)CSc2ccccc2)c([N+](=O)[O-])c1)c1ccc(N2CCN(Cc3ccccc3-c3ccc(Cl)cc3)CC2)cc1] |
| N-(4-(4-((4'-chloro(1,1'-biphenyl)-2-yl)methyl)piperazin-1-yl)benzoyl)-4-(((1R)-3-(methyl(2,2,2-trifluoroethyl)amino)-1-((phenylsulfanyl)methyl)propyl)amino)-3-nitrobenzenesulfonamide, | 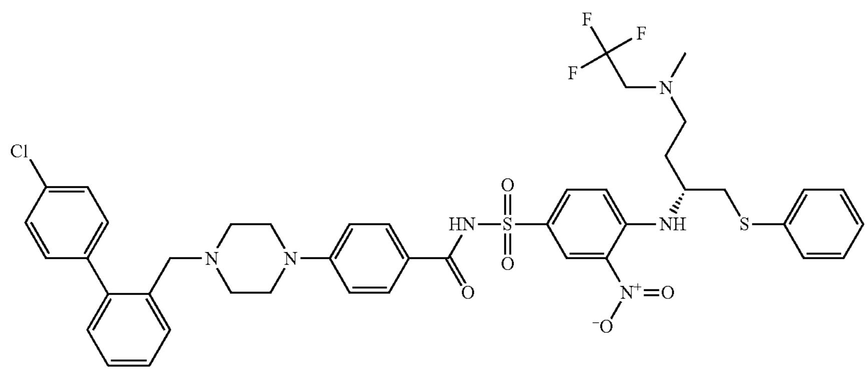 |
| N-(4-(4-((4'-chloro(1,1'-biphenyl)-2-yl)methyl)-4-methoxypiperidin-1-yl)benzoyl)-4-(((1R)-3-(morpholin-4-yl)-1-((phenylsulfanyl)methyl)propyl)amino)-3-nitrobenzenesulfonamide, | 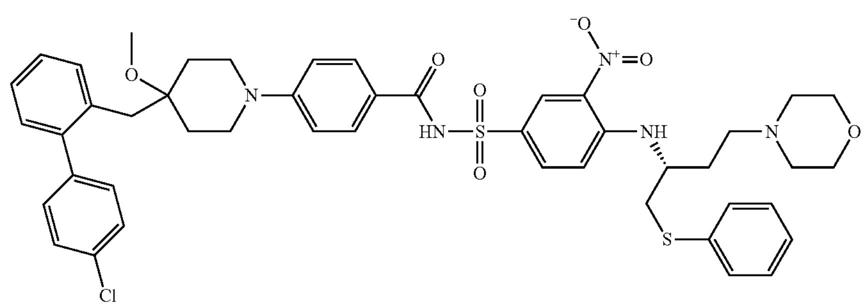 |

-continued

| Name | Structure |
|---|---|
| N-(4-(4-((4'-chloro(1,1'-biphenyl)-2-yl)methyl)-4-methoxypiperidin-1-yl)benzoyl)-3-nitro-4-((2-(phenylsulfanyl)ethyl)amino)benzenesulfonamide, | 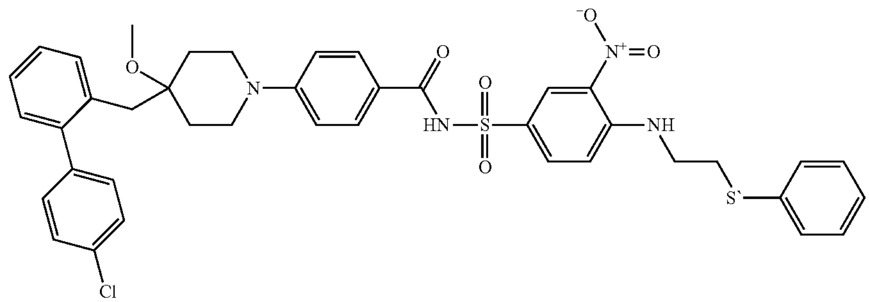 |
| N-(4-(4-((4'-chloro(1,1'-biphenyl)-2-yl)methyl)piperazin-1-yl)benzoyl)-4-(((1R)-3-(ethyl(2,2,2-trifluoroethyl)amino)-1-((phenylsulfanyl)methyl)propyl)amino)-3-nitrobenzenesulfonamide, | 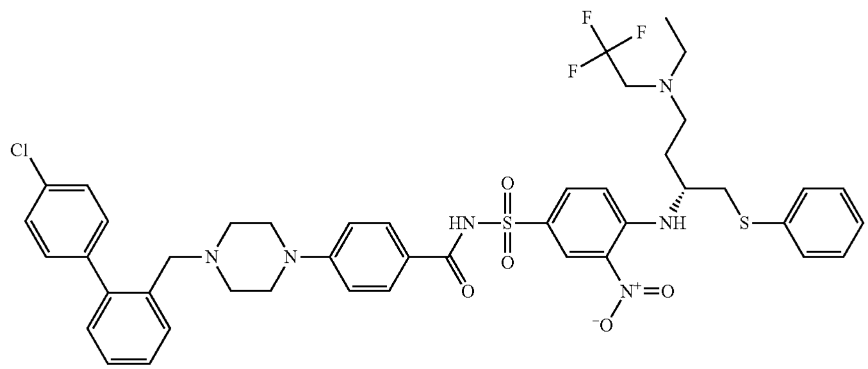 |
| N-(4-(4-((4'-chloro(1,1'-biphenyl)-2-yl)methyl)piperazin-1-yl)benzoyl)-4-(((1R)-3-((2-fluoroethyl)amino)-1-((phenylsulfanyl)methyl)propyl)amino)-3-nitrobenzenesulfonamide, | 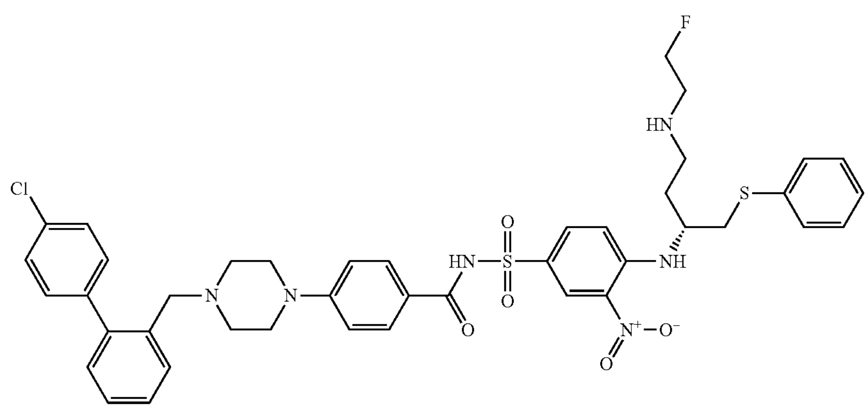 [SMILES: O=C(NS(=O)(=O)c1ccc(N[C@H](CCNCCF)CSc2ccccc2)c([N+](=O)[O-])c1)c1ccc(N2CCN(Cc3ccccc3-c3ccc(Cl)cc3)CC2)cc1] |
| N-(4-(4-((4'-chloro(1,1'-biphenyl)-2-yl)methyl)piperazin-1-yl)benzoyl)-4-(((1R)-3-((2,2-difluoroethyl)amino)-1-((phenylsulfanyl)methyl)propyl)amino)-3-nitrobenzenesulfonamide, | 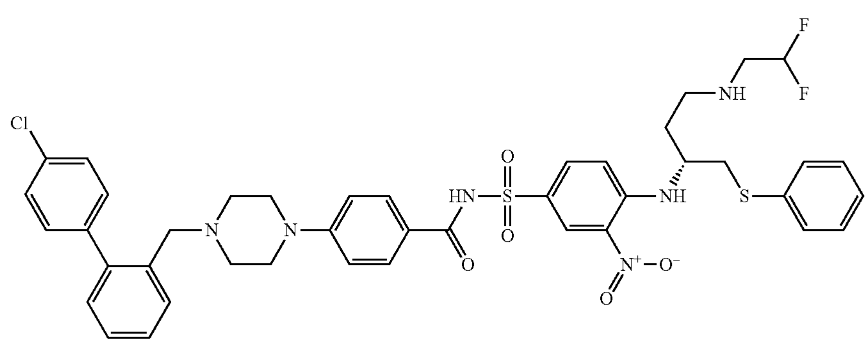 [SMILES: O=C(NS(=O)(=O)c1ccc(N[C@H](CCNCC(F)F)CSc2ccccc2)c([N+](=O)[O-])c1)c1ccc(N2CCN(Cc3ccccc3-c3ccc(Cl)cc3)CC2)cc1] |

-continued

| Name | Structure |
|---|---|
| N-(4-(4-((4'-chloro(1,1'-biphenyl)-2-yl)methyl)piperazin-1-yl)benzoyl)-1-((1R)-3-(dimethylamino)-1-((phenylsulfanyl)methyl)propyl)-1H-benzimidazole-5-sulfonamide, | 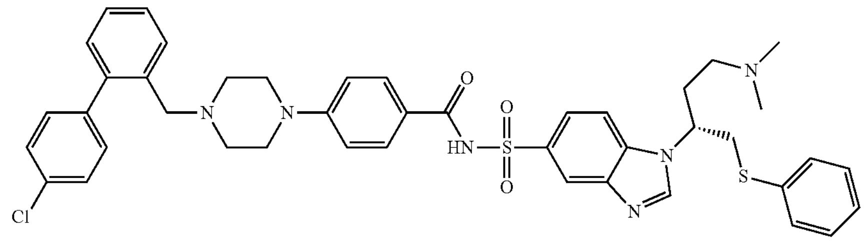 [SMILES: CN(C)CC[C@H](CSc1ccccc1)n1cnc2cc(S(=O)(=O)NC(=O)c3ccc(N4CCN(Cc5ccccc5-c5ccc(Cl)cc5)CC4)cc3)ccc21] |
| N-(4-(4-((4'-chloro(1,1'-biphenyl)-2-yl)methyl)piperazin-1-yl)benzoyl)-1-((1R)-3-(dimethylamino)-1-((phenylsulfanyl)methyl)propyl)-1H-1,2,3-benzotriazole-5-sulfonamide, | 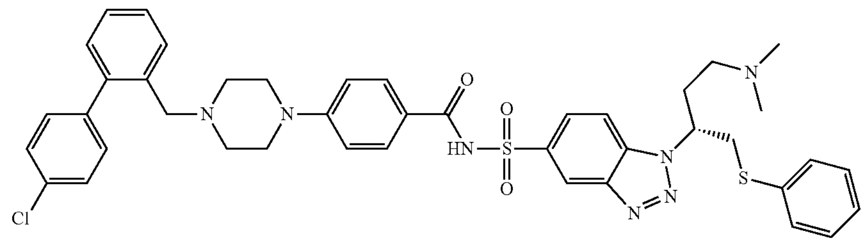 [SMILES: CN(C)CC[C@H](CSc1ccccc1)n1nnc2cc(S(=O)(=O)NC(=O)c3ccc(N4CCN(Cc5ccccc5-c5ccc(Cl)cc5)CC4)cc3)ccc21] |
| 5-(((4-(4-((4'-chloro(1,1'-biphenyl)-2-yl)methyl)piperazin-1-yl)benzoyl)amino)sulfonyl)-2-(((1R)-3-(dimethylamino)-1-((phenylsulfanyl)methyl)propyl)amino)benzamide, | 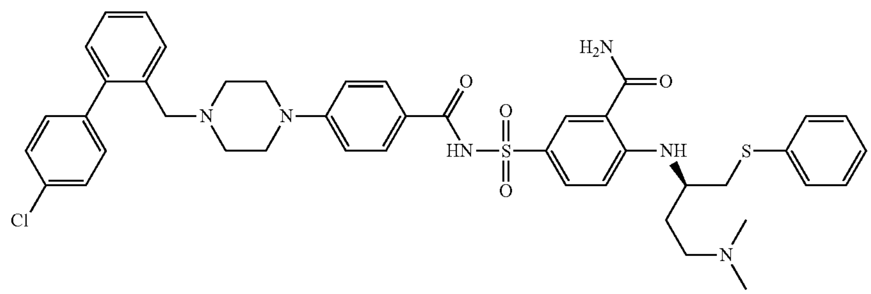 |
| N-(4-(4-((4'-(dimethylamino)(1,1'-biphenyl)-2-yl)carbonyl)piperazin-1-yl)benzoyl)-4-(((1R)-3-(dimethylamino)-1-((phenylsulfanyl)methyl)propyl)amino)-3-nitrobenzenesulfonamide, | 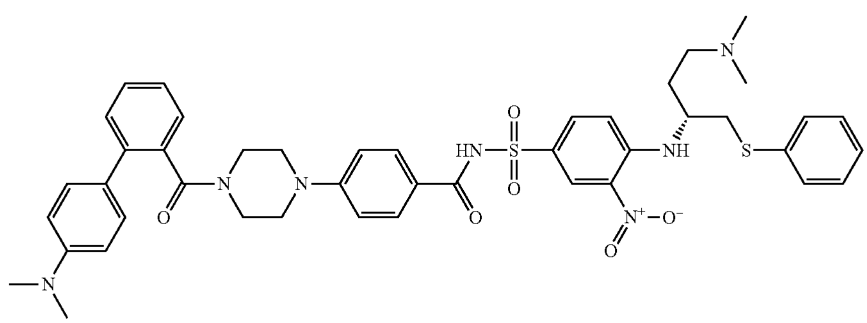 [SMILES: CN(C)CC[C@H](CSc1ccccc1)Nc1ccc(S(=O)(=O)NC(=O)c2ccc(N3CCN(C(=O)c4ccccc4-c4ccc(N(C)C)cc4)CC3)cc2)cc1[N+](=O)[O-]] |
| 4-(((1R)-3-(dimethylamino)-1-((phenylsulfanyl)methyl)propyl)amino)-N-(4-(4-((4'-(methylsulfanyl)(1,1'-biphenyl)-2-yl)carbonyl)piperazin-1-yl)benzoyl)-3-nitrobenzenesulfonamide, | 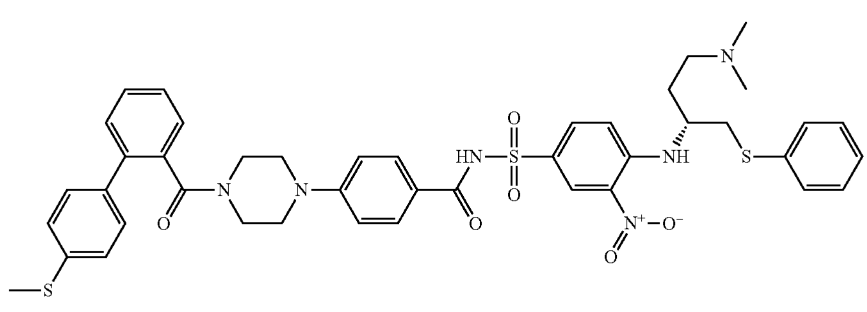 [SMILES: CSc1ccc(-c2ccccc2C(=O)N2CCN(c3ccc(C(=O)NS(=O)(=O)c4ccc(N[C@H](CCN(C)C)CSc5ccccc5)c([N+](=O)[O-])c4)cc3)CC2)cc1] |

-continued

| Name | Structure |
|---|---|
| 4-(((1R)-3-(dimethylamino)-1-((phenylsulfanyl)methyl)propyl)amino)-N-(4-(4-((4'-(methylsulfanyl)(1,1'-biphenyl)-2-yl)carbonyl)piperazin-1-yl)benzoyl)-3-nitrobenzenesulfonamide, | 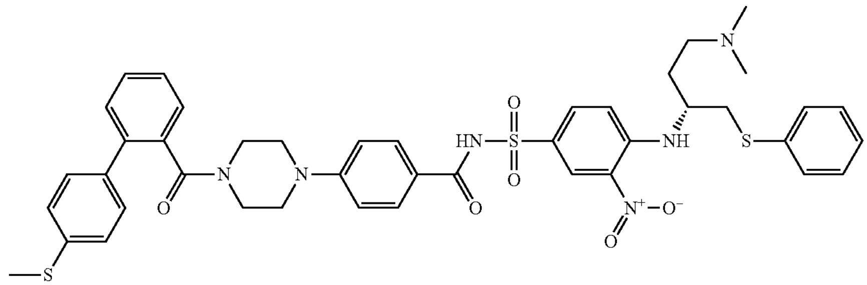 [SMILES: CSc1ccc(-c2ccccc2C(=O)N2CCN(c3ccc(C(=O)NS(=O)(=O)c4ccc(N[C@H](CCN(C)C)CSc5ccccc5)c([N+](=O)[O-])c4)cc3)CC2)cc1] |
| N-(4-(4-((4'-chloro(1,1'-biphenyl)-2-yl)methyl)piperazin-1-yl)benzoyl)-3-cyano-4-(((1R)-3-(dimethylamino)-1-((phenylsulfanyl)methyl)propyl)amino)benzenesulfonamide, | 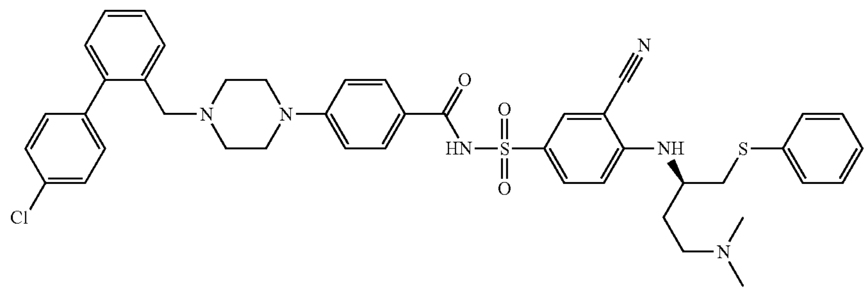 [SMILES: CN(C)CC[C@H](CSc1ccccc1)Nc1ccc(S(=O)(=O)NC(=O)c2ccc(N3CCN(Cc4ccccc4-c4ccc(Cl)cc4)CC3)cc2)cc1C#N] |
| N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)oxy)-3-nitrobenzenesulfonamide, | 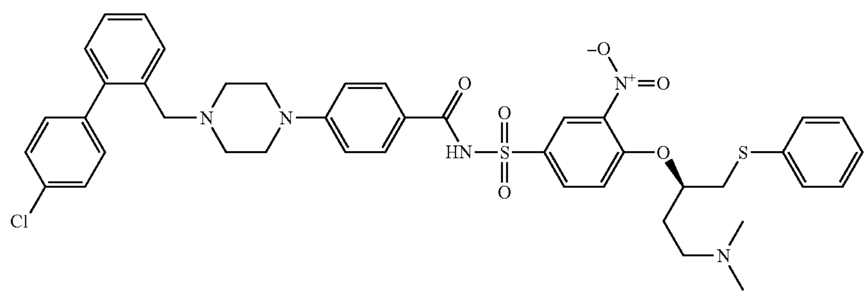 |
| N-(4-(4-((4'-chloro(1,1'-biphenyl)-2-yl)methyl)piperazin-1-yl)benzoyl)-4-(((1R)-3-(4,4-dimethyl-4,5-dihydro-1H-imidazol-1-yl)-1-((phenylsulfanyl)methyl)propyl)amino)-3-nitrobenzenesulfonamide, | 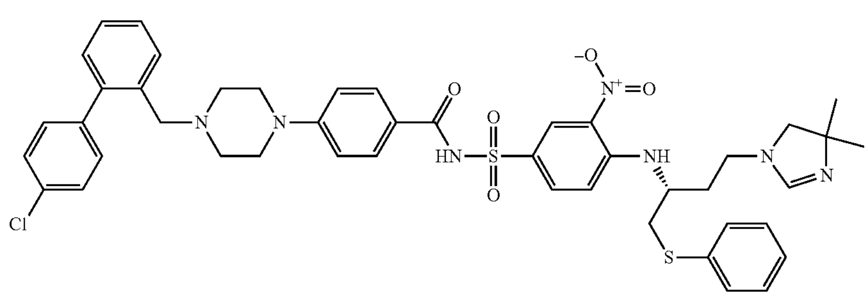 |
| N-(4-(4-((4'-chloro(1,1'-biphenyl)-2-yl)methyl)piperazin-1-yl)benzoyl)-4-(((1R)-3-(5,6-dihydro-1(4H)-pyrimidin-1-yl)-((phenylsulfany)methyl)propyl)amino)-3-nitrobenzenesulfonamide, | |

| Name | Structure |
|---|---|
| N-(4-(4-((4'-chloro(1,1'-biphenyl)-2-yl)methyl)piperazin-1-yl)benzoyl)-4-(((1R)-3-(2-methyl-4,5-dihydro-1H-imidazol-1-yl)-1-((phenylsulfanyl)methyl)propyl)amino)-3-nitrobenzenesulfonamide, | |
| N-(4-(4-((4'-chloro(1,1'-biphenyl)-2-yl)methyl)piperazin-1-yl)benzoyl)-4-(((1R)-3-(5,6-dihydro-1(4H)-pyrimidin-1-yl)-1-((phenylsulfanyl)methyl)propyl)amino)-3-(trifluoromethyl)benzenesulfonamide, | |
| N-(4-(4-((4'-chloro(1,1'-biphenyl)-2-yl)methyl)piperazin-1-yl)benzoyl)-4-(((1R)-3-(2,4-dimethyl-4,5-dihydro-1H-imidazol-1-yl)-1-((phenylsulfanyl)methyl)propyl)amino)-3-(trifluoromethyl)benzenesulfonamide, | |
| N-(4-(4-((4'-chloro(1,1'-biphenyl)-2-yl)methyl)piperazin-1-yl)benzoyl)-4-(((1R)-3-(2-methyl-4,5-dihydro-1H-imidazol-1-yl)-1-((phenylsulfanyl)methyl)propyl)amino)-3-(trifluoromethyl)benzenesulfonamide, | |
| N-(4-(4-((4'-chloro(1,1'-biphenyl)-2-yl)methyl)piperazin-1-yl)benzoyl)-4-(((1R)-3-(4,4-dimethyl-4,5-dihydro-1H-imidazol-1-yl)-1-((phenylsulfanyl)methyl)propyl)amino)-3-(trifluoromethyl)benzenesulfonamide. | |

-continued

| Name | Structure |
|---|---|
| N-(4-(4-((2-(4-chlorophenyl)-1-cyclohexen-1-yl)methyl)piperazin-1-yl)benzoyl)-4-(((1R)-3-(dimethylamino)-1-((phenylsulfanyl)methyl)propyl)oxy)-3-(trifluoromethyl)benzenesulfonamide, | |
| N-(4-(4-((2-(4-chlorophenyl)cyclohept-1-en-1-yl)methyl)piperazin-1-yl)benzoyl)-4-(((1R)-3-(dimethylamino)-1-((phenylsulfanyl)methyl)propyl)amino)-3-(trifluoromethyl)benzenesulfonamide, | |
| 4-(((1R)-3-(bis(2-methoxyethyl)amino)-1-((phenylsulfanyl)methyl)propyl)amino)-N-(4-(4-((4'-chloro(1,1'-biphenyl)-2-yl)methyl)piperazin-1-yl)benzoyl)-3-nitrobenzenesulfonamide, | |
| 4-(((1R)-3-(bis(2-methoxyethyl)amino)-1-((phenylsulfanyl)methyl)propyl)amino)-N-(4-(4-((4'-chloro(1,1'-biphenyl)-2-yl)methyl)piperazin-1-yl)benzoyl)-3-(trifluoromethyl)benzenesulfonamide, | |

| Name | Structure |
|---|---|
| 4-(((1R)-5-amino-1-((phenylsulfanyl)methyl)pentyl)amino)-N-(4-(4-((4'-chloro(1,1'-biphenyl)-4-yl)methyl)-1-piperazinyl)benzoyl)-3-nitrobenzenesulfonamide, | 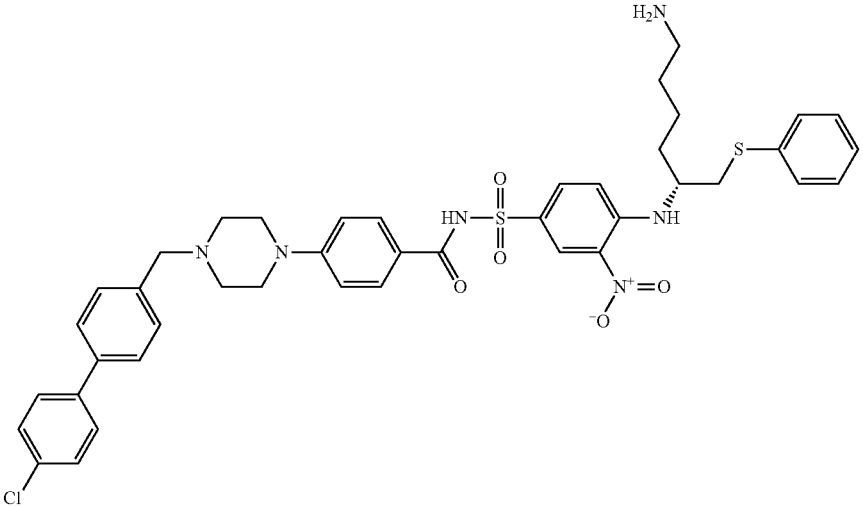 |
| N-(4-(4-((1,1'-biphenyl)-2-ylmethyl)piperazin-1-yl)benzoyl)-4-(((1R)-4-methyl-1-((phenylsulfanyl)methyl)pentyl)amino)-3-nitrobenzenesulfonamide, | 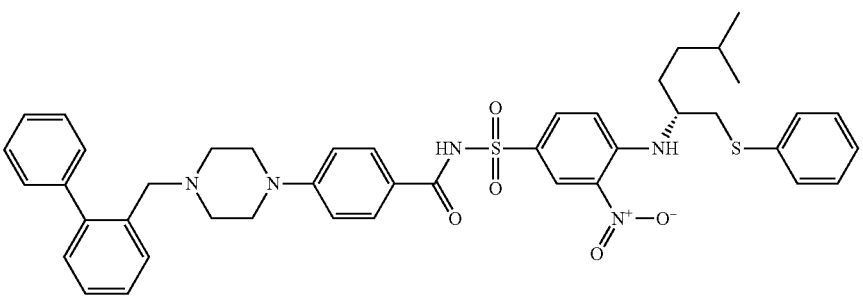 [SMILES: CC(C)CC[C@H](CSc1ccccc1)Nc1ccc(S(=O)(=O)NC(=O)c2ccc(N3CCN(Cc4ccccc4-c4ccccc4)CC3)cc2)cc1[N+](=O)[O-]] |
| tert-butyl(5R)-5-(4-(((4-(4-((4'-chloro(1,1'-biphenyl)-2-yl)methyl)piperazin-1-yl)benzoyl)amino)sulfonyl)-2-nitroanilino)-6-(phenylsulfanyl)hexylcarbamate, | 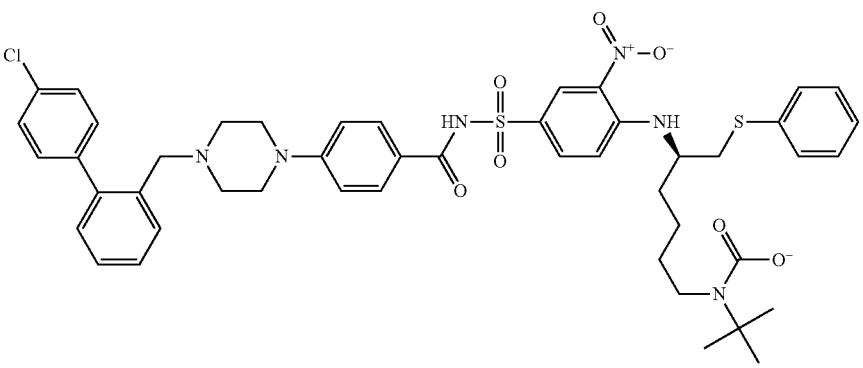 [SMILES: CC(C)(C)N(CCCC[C@H](CSc1ccccc1)Nc1ccc(S(=O)(=O)NC(=O)c2ccc(N3CCN(Cc4ccccc4-c4ccc(Cl)cc4)CC3)cc2)cc1[N+](=O)[O-])C(=O)[O-]] |
| 4-(((1R)-5-amino-1-((phenylsulfanyl)methyl)pentyl)amino)-N-(4-(4-((4'-chloro(1,1'-biphenyl)-2-yl)methyl)piperazin-1-yl)benzoyl)-3-nitrobenzenesulfonamide, | 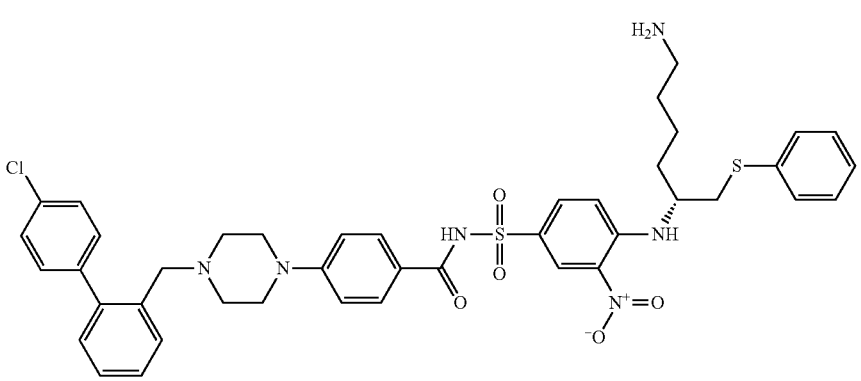 |

| Name | Structure |
|---|---|
| N-(4-(4-((4'-chloro(1,1'-biphenyl)-2-yl)methyl)piperazin-1-yl)benzoyl)-4-(((1R)-5-((methylsulfonyl)amino)-1-((phenylsulfanyl)methyl)pentyl)amino)-3-nitrobenzenesulfonamide, | 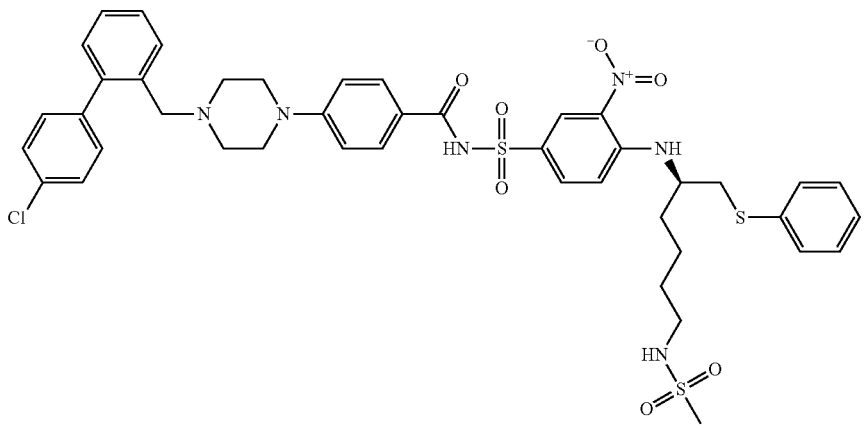 |
| 4-(((1R)-5-((aminocarbonyl)amino)-1-((phenylsulfanyl)methyl)pentyl)amino)-N-(4-(4-((4'-chloro(1,1'-biphenyl)-2-yl)methyl)piperazin-1-yl)benzoyl)-3-nitrobenzenesulfonamide, | 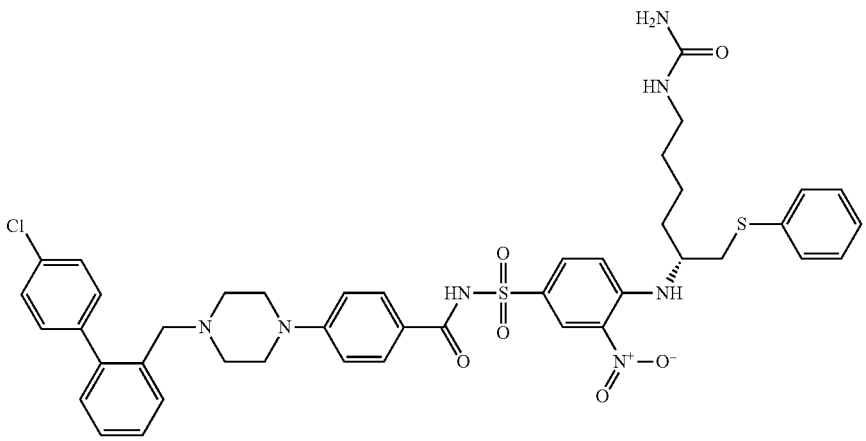 [SMILES: NC(=O)NCCCC[C@H](CSc1ccccc1)Nc1ccc(S(=O)(=O)NC(=O)c2ccc(N3CCN(Cc4ccccc4-c4ccc(Cl)cc4)CC3)cc2)cc1[N+](=O)[O-]] |
| 4-(((1R)-3-(dimethylamino)-1-((phenylsulfanyl)methyl)propyl)amino)-N-(4-(4-(2-(methylsulfanyl)benzyl)piperazin-1-yl)benzoyl)-3-nitrobenzenesulfonamide, | 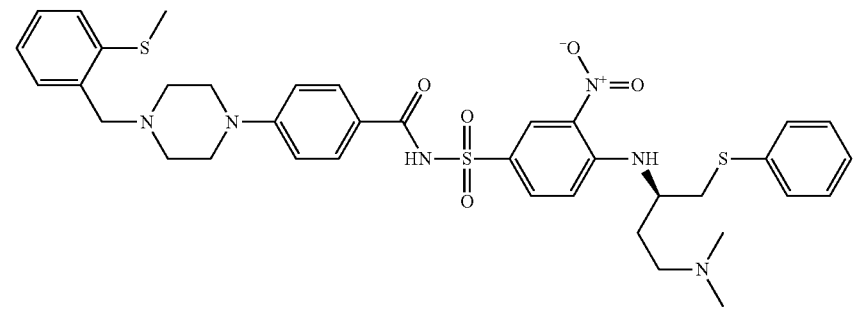 |
| 4-(((1R)-3-(dimethylamino)-1-((phenylsulfanyl)methyl)propyl)amino)-N-(4-(4-(2-(methylsulfonyl)benzyl)piperazin-1-yl)benzoyl)-3-nitrobenzenesulfonamide, | 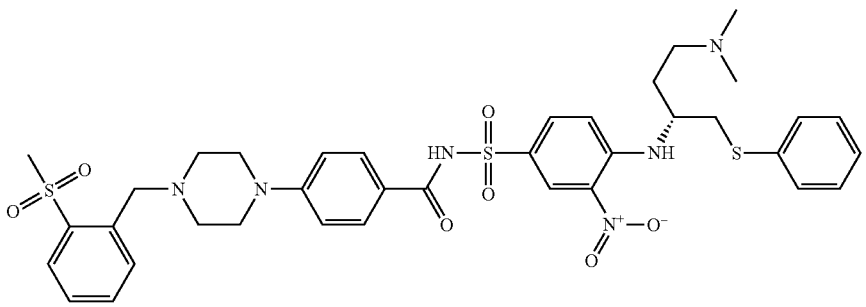 [SMILES: CN(C)CC[C@H](CSc1ccccc1)Nc1ccc(S(=O)(=O)NC(=O)c2ccc(N3CCN(Cc4ccccc4S(C)(=O)=O)CC3)cc2)cc1[N+](=O)[O-]] |

| Name | Structure |
|---|---|
| 4-(((1R)-3-(dimethylamino)-1-((phenylsulfanyl)methyl)propyl)amino)-N-(4-(4-(2-(5,5-dimethyl-2-oxo-1,3-oxazolidin-3-yl)benzyl)piperazin-1-yl)benzoyl)-3-nitrobenzenesulfonamide, | 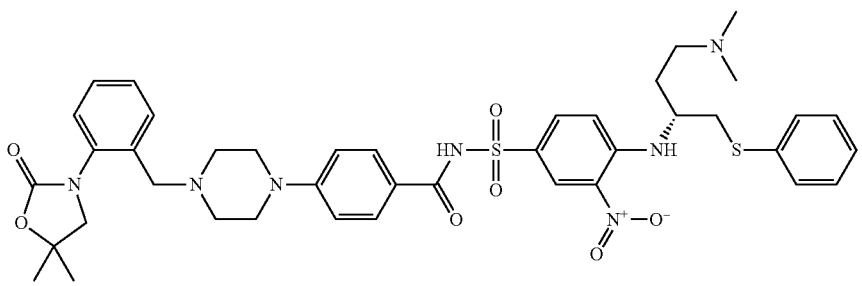 [SMILES: CN(C)CC[C@H](CSc1ccccc1)Nc1ccc(S(=O)(=O)NC(=O)c2ccc(N3CCN(Cc4ccccc4N4CC(C)(C)OC4=O)CC3)cc2)cc1[N+](=O)[O-]] |
| N-(4-(4-(2-cyclohexylbenzyl)piperazin-1-yl)benzoyl)-4-(((1R)-3-(dimethylamino)-1-((phenylsulfanyl)methyl)propyl)amino)-3-nitrobenzenesulfonamide, | 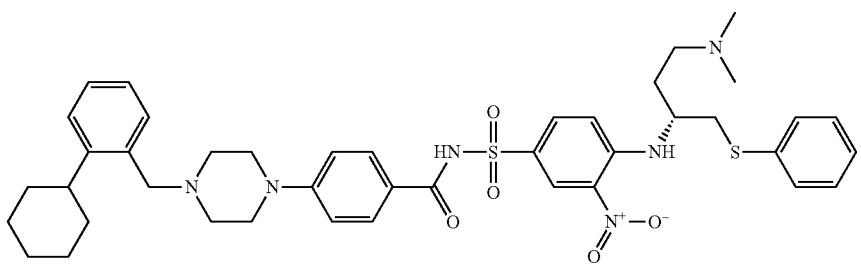 [SMILES: CN(C)CC[C@H](CSc1ccccc1)Nc1ccc(S(=O)(=O)NC(=O)c2ccc(N3CCN(Cc4ccccc4C4CCCCC4)CC3)cc2)cc1[N+](=O)[O-]] |
| 4-(((1R)-3-(dimethylammo)-1-((phenylsulfanyl)methyl)propyl)amino)-N-(4-(4-(2-(morpholin-4-yl)benzyl)piperazin-1-yl)benzoyl)-3-nitrobenzenesulfonamide, | 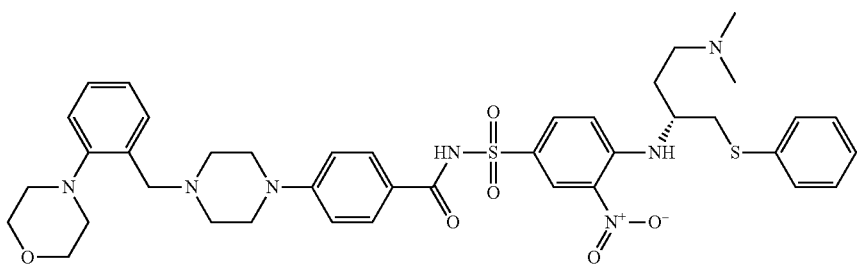 |
| 4-(((1R)-3-(dimethylamino)-1-((phenylsulfanyl)methyl)propyl)amino)-N-(4-(4-(2-(isopropylsulfanyl)benzyl)piperazin-1-yl)benzoyl)-3-nitrobenzenesulfonamide, | 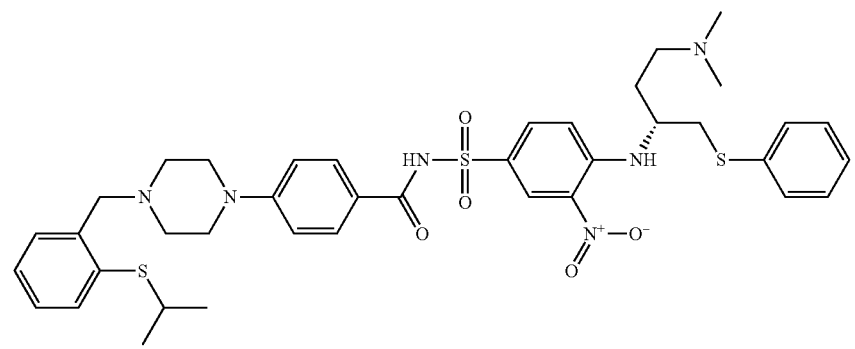 [SMILES: CC(C)Sc1ccccc1CN1CCN(c2ccc(C(=O)NS(=O)(=O)c3ccc(N[C@H](CCN(C)C)CSc4ccccc4)c([N+](=O)[O-])c3)cc2)CC1] |
| N-(4-(4-((2-(4-chlorophenyl)-1-cyclohexen-1-yl)methyl)piperazin-1-yl)benzoyl)-4-(((1R)-3-(isopropyl(methyl)amino)-1-((phenylsulfanyl)methyl)propyl)amino)-3-nitrobenzenesulfonamide, | 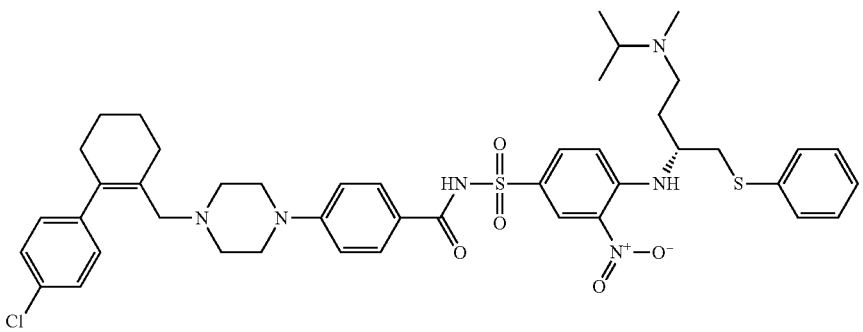 [SMILES: CC(C)N(C)CC[C@H](CSc1ccccc1)Nc1ccc(S(=O)(=O)NC(=O)c2ccc(N3CCN(CC4=C(c5ccc(Cl)cc5)CCCC4)CC3)cc2)cc1[N+](=O)[O-]] |

| Name | Structure |
|---|---|
| N-(4-(4-((2-(4-chlorophenyl)-1-cyclohexen-1-yl)methyl)piperazin-1-yl)benzoyl)-4-(((1R)-3-(dipropylamino)-1-((phenylsulfanyl)methyl)propyl)amino)-3-nitrobenzenesulfonamide, | 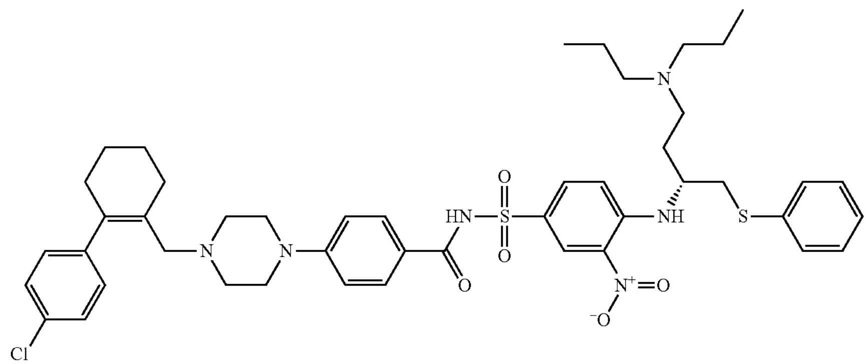 |
| N-(4-(4-((4'-chloro(1,1'-biphenyl)-2-yl)methyl)piperazin-1-yl)benzoyl)-4-(((1R)-3-(dipropylamino)-1-((phenylsulfanyl)methyl)propyl)amino)-3-nitrobenzenesulfonamide, | 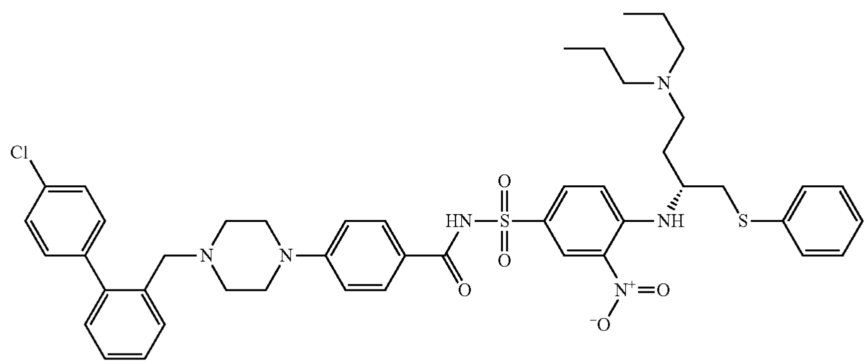 |
| N-(4-(4-((2-(4-chlorophenyl)-1-cyclohexen-1-yl)methyl)piperazin-1-yl)benzoyl)-4-(((1R)-3-(diethylamino)-1-((phenylsulfanyl)methyl)propyl)amino)-3-nitrobenzenesulfonamide, | 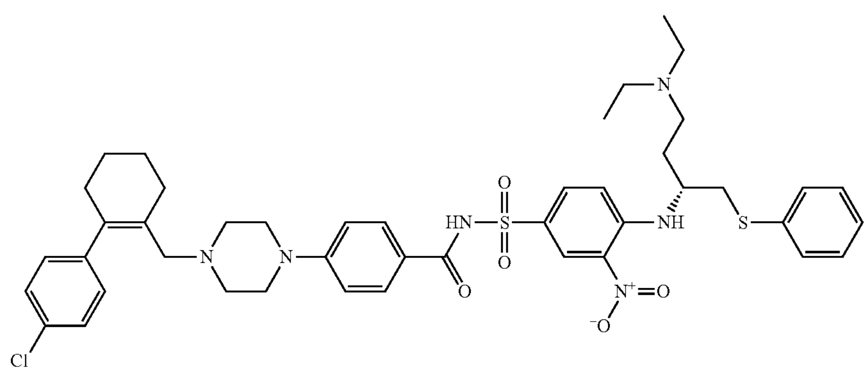 |
| N-(4-(4-((4'-chloro(1,1'-biphenyl)-2-yl)methyl)piperazm-1-yl)benzoyl)-4-(((1R)-3-(diethylamino)-1-((phenylsulfanyl)methyl)propyl)amino)-3-nitrobenzenesulfonamide, | 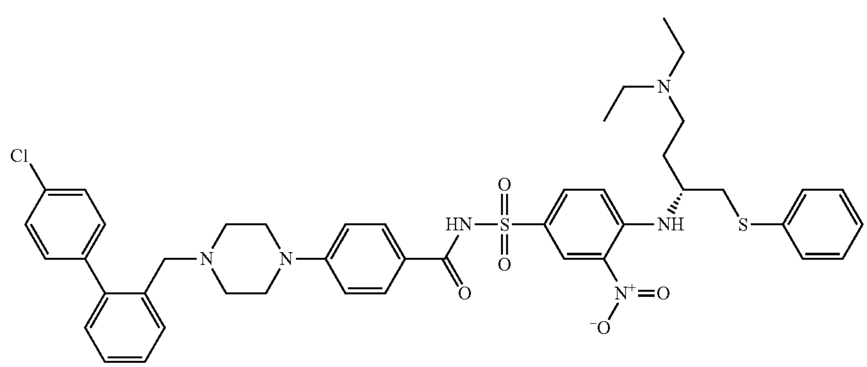 |

| Name | Structure |
|---|---|
| N-(4-(4-((1,1'-biphenyl)-3-ylmethyl)piperazin-1-yl)benzoyl)-3-nitro-4-((2-(phenylsulfanyl)ethyl)amino)benzenesulfonamide, | 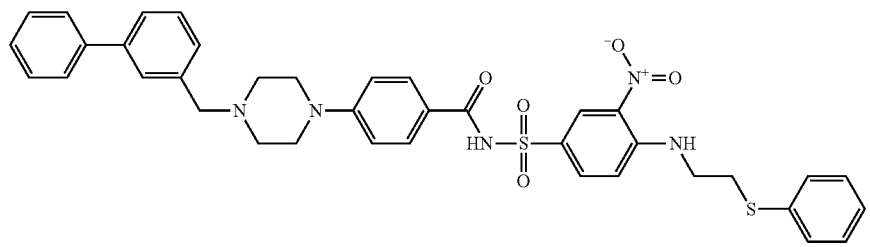 |
| N-(4-(4-((1,1'-biphenyl)-3-ylmethyl)piperazin-1-yl)benzoyl)-4-(((1R)-3-(dimethylamino)-1-((phenylsulfanyl)methyl)propyl)amino)-3-nitrobenzenesulfonamide, | 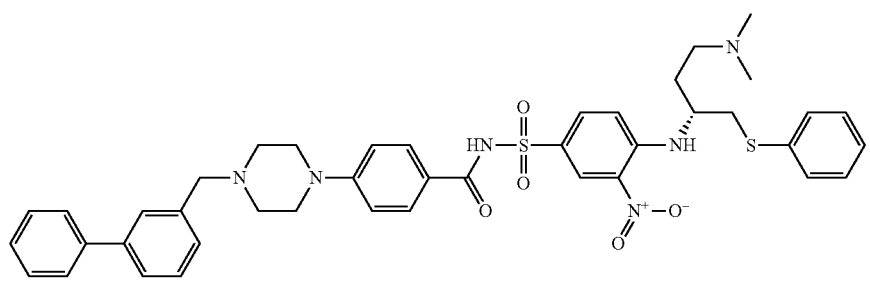 [SMILES: CN(C)CC[C@H](CSc1ccccc1)Nc1ccc(S(=O)(=O)NC(=O)c2ccc(N3CCN(Cc4cccc(-c5ccccc5)c4)CC3)cc2)cc1[N+](=O)[O-]] |
| N-(4-(4-((1,1'-biphenyl)-3-ylmethyl)piperazin-1-yl)benzoyl)-4-(((1R)-3-(morpholin-4-yl)-1-((phenylsulfanyl)methyl)propyl)amino)-3-nitrobenzenesulfonamide, | 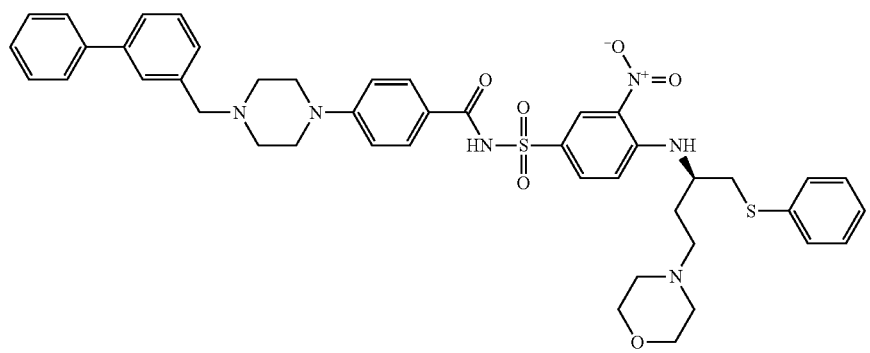 |
| N-(4-(4-((1,1'-biphenyl)-2-ylmethyl)piperazin-1-yl)-3-fluorobenzoyl)-4-(((1R)-3-(dimethylamino)-1-((phenylsulfanyl)methyl)propyl)amino)-3-nitrobenzenesulfonamide, | 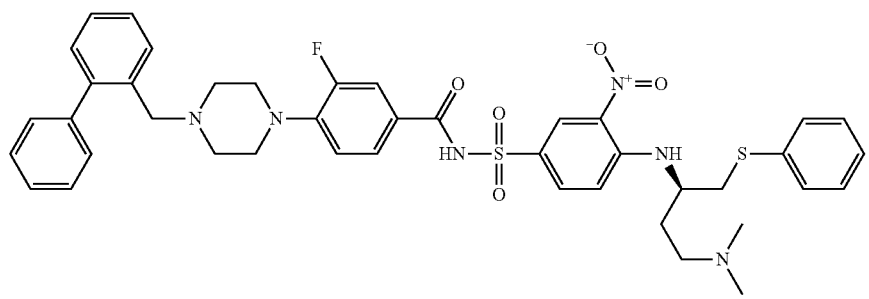 |
| N-(4-(4-((1,1'-biphenyl)-2-ylmethyl)piperazin-1-yl)-3-fluorobenzoyl)-3-nitro-4-((2-(phenylsulfanyl)ethyl)amino)benzenesulfonamide, | 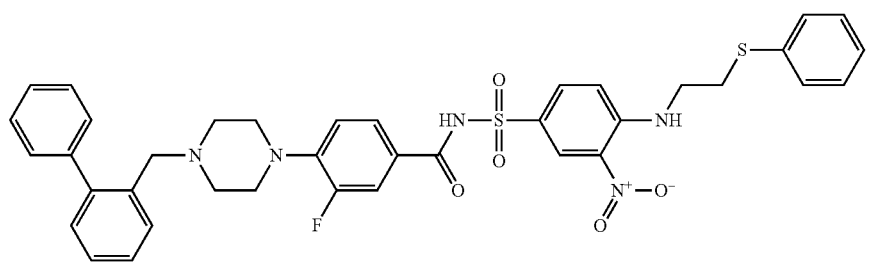 [SMILES: O=C(NS(=O)(=O)c1ccc(NCCSc2ccccc2)c([N+](=O)[O-])c1)c1ccc(N2CCN(Cc3ccccc3-c3ccccc3)CC2)c(F)c1] |

-continued

| Name | Structure |
|---|---|
| N-(4-(4-((1,1'-biphenyl)-2-ylmethyl)piperazin-1-yl)-3-fluorobenzoyl)-4-(((1R)-3-(morpholin-4-yl)-1-((phenylsulfanyl)methyl)propyl)amino)-3-nitrobenzenesulfonamide, | 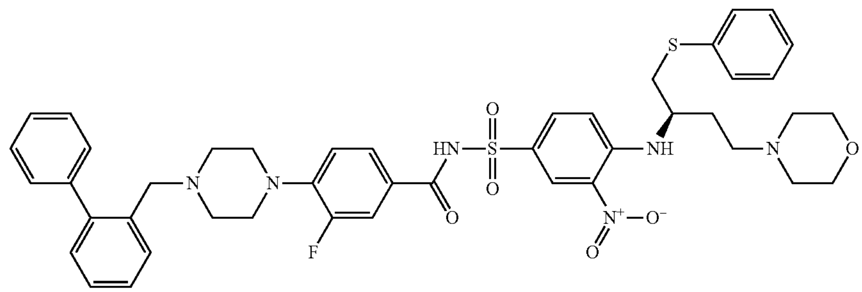 [SMILES: O=C(NS(=O)(=O)c1ccc(N[C@H](CCN2CCOCC2)CSc2ccccc2)c([N+](=O)[O-])c1)c1ccc(N2CCN(Cc3ccccc3-c3ccccc3)CC2)c(F)c1] |
| N-(4-(4-((1,1'-biphenyl)-2-ylmethyl)piperazin-1-yl)-3,5-difluorobenzoyl)-4-(((1R)-3-(dimethylamino)-1-((phenylsulfanyl)methyl)propyl)amino)-3-nitrobenzenesulfonamide | 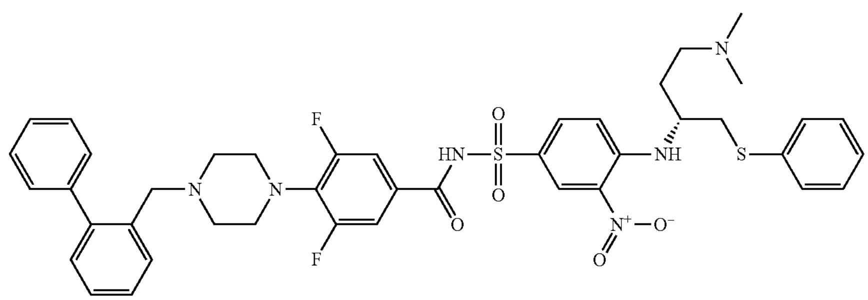 [SMILES: CN(C)CC[C@H](CSc1ccccc1)Nc1ccc(S(=O)(=O)NC(=O)c2cc(F)c(N3CCN(Cc4ccccc4-c4ccccc4)CC3)c(F)c2)cc1[N+](=O)[O-]] |
| N-(4-(4-((1,1'-biphenyl)-2-ylmethyl)piperazin-1-yl)-3,5-difluorobenzoyl)-3-nitro-4-((2-(phenylsulfanyl)ethyl)amino)benzenesulfonamide, | 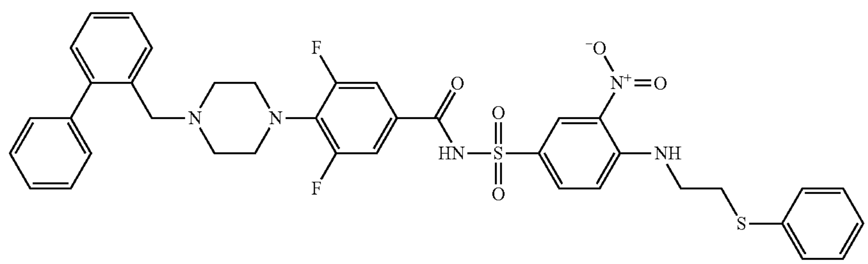 |
| N-(4-(4-((1,1'-biphenyl)-2-ylmethyl)piperazin-1-yl)-3,5-difluorobenzoyl)-4-(((1R)-3-(morpholin-4-yl)-1-((phenylsulfanyl)methyl)propyl)amino)-3-nitrobenzenesulfonamide, | 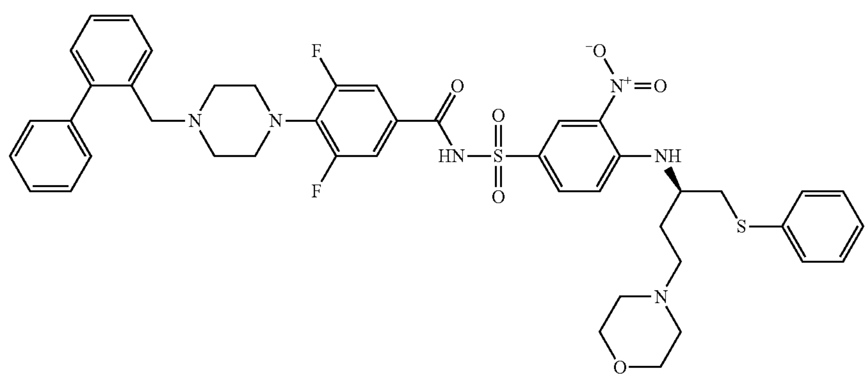 |
| 3-nitro-N-(4-(4-((1-phenyl-1H-imidazol-2-yl)methyl)piperazin-1-yl)benzoyl)-4-((2-(phenylsulfanyl)ethyl)amino)benzenesulfonamide, | 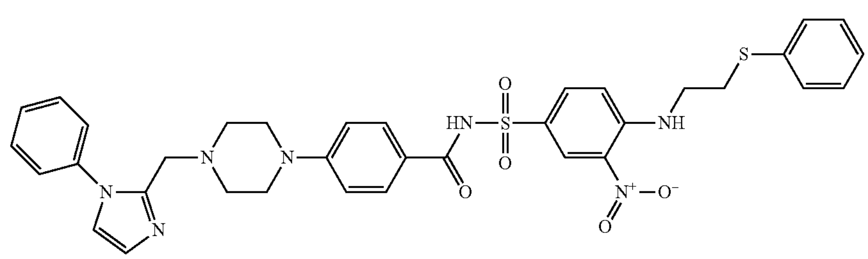 [SMILES: O=C(NS(=O)(=O)c1ccc(NCCSc2ccccc2)c([N+](=O)[O-])c1)c1ccc(N2CCN(Cc3nccn3-c3ccccc3)CC2)cc1] |

| Name | Structure |
|---|---|
| 4-(((1R)-3-(morpholin-4-yl)-1-((phenylsulfanyl)methyl)propyl)amino)-3-nitro-N-(4-(4-((1-phenyl-1H-imidazol-2-yl)methyl)piperazin-1-yl)benzoyl)benzenesulfonamide, | 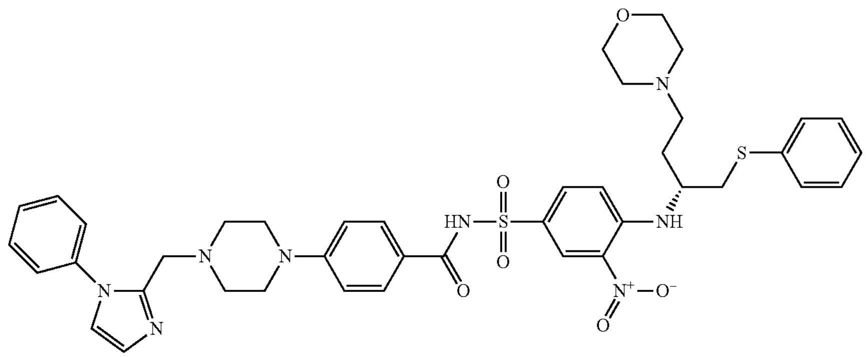 [SMILES: O=C(NS(=O)(=O)c1ccc(N[C@H](CCN2CCOCC2)CSc2ccccc2)c([N+](=O)[O-])c1)c1ccc(N2CCN(Cc3nccn3-c3ccccc3)CC2)cc1] |
| 3-nitro-N-(4-(4-((1-phenyl-1H-pyrazol-5-yl)methyl)piperazin-1-yl)benzoyl)-4-((2-(phenylsulfanyl)ethyl)amino)benzenesulfonamide, | 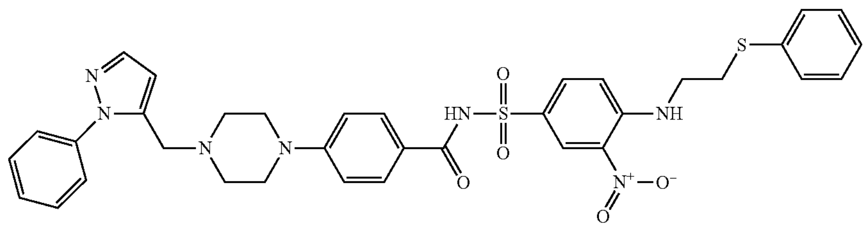 [SMILES: O=C(NS(=O)(=O)c1ccc(NCCSc2ccccc2)c([N+](=O)[O-])c1)c1ccc(N2CCN(Cc3ccnn3-c3ccccc3)CC2)cc1] |
| 4-(((1R)-3-(morpholin-4-yl)-1-((phenylsulfanyl)methyl)propyl)amino)-3-nitro-N-(4-(4-((1-phenyl-1H-pyrazol-5-yl)methyl)piperazin-1-yl)benzoyl)benzenesulfonamide, | 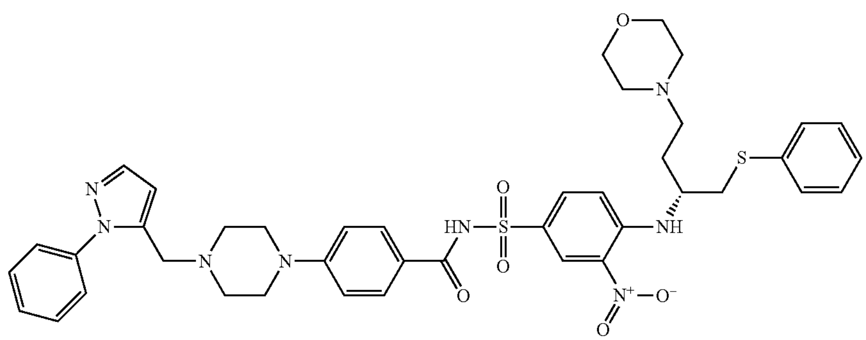 |
| 4-(((1R)-3-(morpholin-4-yl)-1-((phenylsulfanyl)methyl)propyl)amino)-3-nitro-N-(4-(4-((1-phenyl-1H-pyrazol-5-yl)methyl)piperazin-1-yl)benzoyl)benzenesulfonamide | 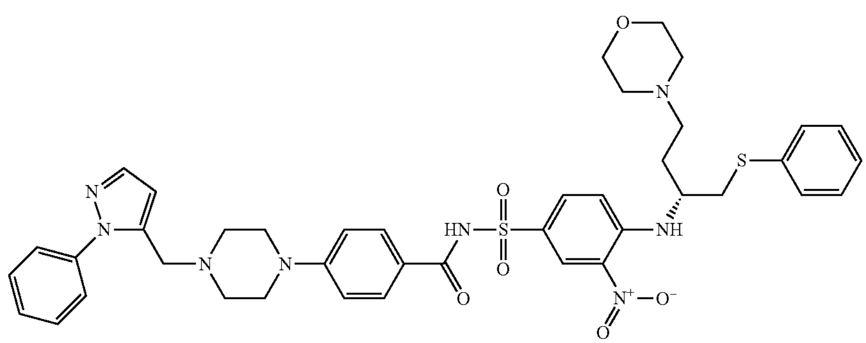 [SMILES: O=C(NS(=O)(=O)c1ccc(N[C@H](CCN2CCOCC2)CSc2ccccc2)c([N+](=O)[O-])c1)c1ccc(N2CCN(Cc3ccnn3-c3ccccc3)CC2)cc1] |
| 4-(((1R)-3-(morpholin-4-yl)-1-((phenylsulfanyl)methyl)propyl)amino)-3-nitro-N-(4-(4-((1-phenyl-1H-imidazol-5-yl)methyl)piperazin-1-yl)benzoyl)benzenesulfonamide, | 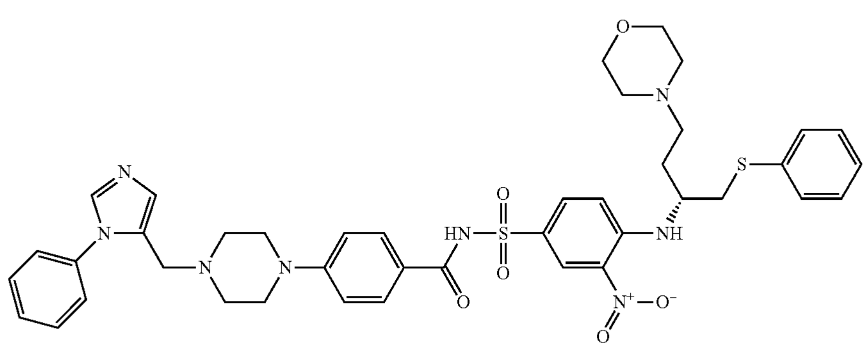 [SMILES: O=C(NS(=O)(=O)c1ccc(N[C@H](CCN2CCOCC2)CSc2ccccc2)c([N+](=O)[O-])c1)c1ccc(N2CCN(Cc3cncn3-c3ccccc3)CC2)cc1] |

| Name | Structure |
|---|---|
| 1-((3R)-3-(4-(((4-(4-((4'-chloro(1,1'-biphenyl)-2-yl)methyl)piperazin-1-yl)benzoyl)amino)sulfonyl)-2-nitroanilino)-4-(phenylsulfanyl)butyl)-3-azetidinecarboxylic acid, | 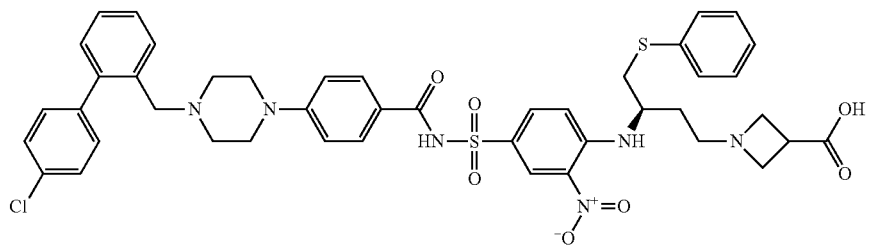 |
| N-(4-(4-((4'-chloro(1,1'-biphenyl)-2-yl)methyl)piperazin-1-yl)benzoyl-4-(((1R)-3-((2-hydroxy-2-methylpropyl)amino)-1-((phenylsulfanyl)methyl)propyl)amino)-3-nitrobenzenesulfonamide, | 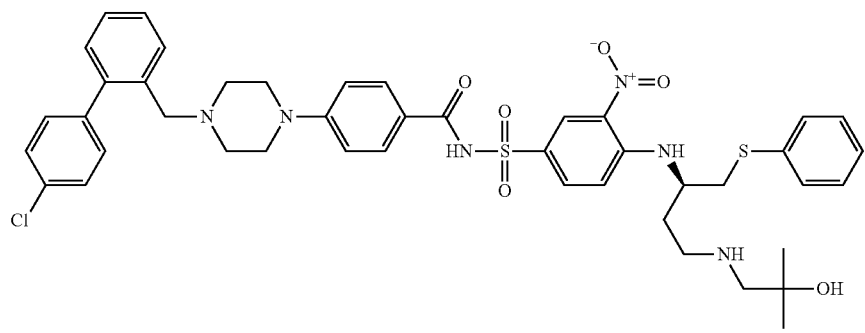 |
| (((3R)-3-(4-(((4-(4-((4'-chloro(1,1'-biphenyl)-2-yl)methyl)piperazin-1-yl)benzoyl)amino)suffonyl)-2-nitroanilino)-4-(phenylsulfanyl)butyl)(methyl)amino)acetic acid, | 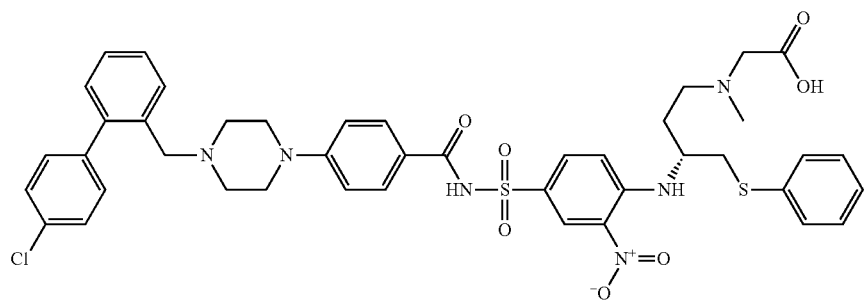 |
| (2R)-1-((3R)-3-(4-(((4-(4-((4'-chloro(1,1'-biphenyl)-2-yl)methyl)piperazin-1-yl)benzoyl)amino)sulfonyl)-2-nitroanilino)-4-(phenylsulfanyl)butyl)-2-pyrrolidinecarboxylic acid | 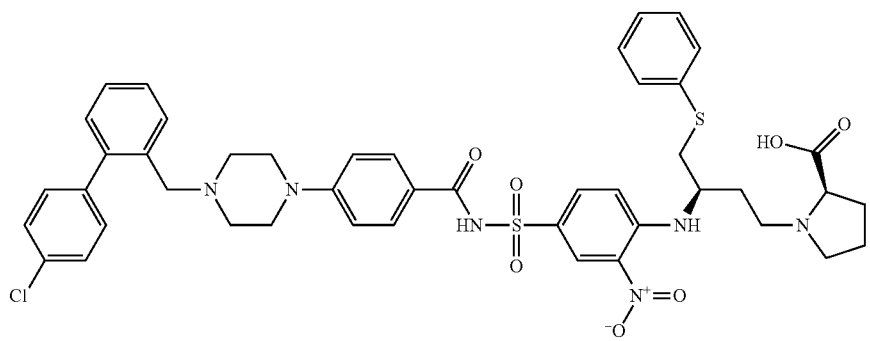 |
| 1-((3R)-3-(4-(((4-(4-((4'-chloro(1,1'-biphenyl)-2-yl)methyl)piperazin-1-yl)benzoyl)amino)sulfonyl)-2-nitroanilino)-4-(phenylsulfanyl)butyl)-4-piperidinecarboxylic acid | 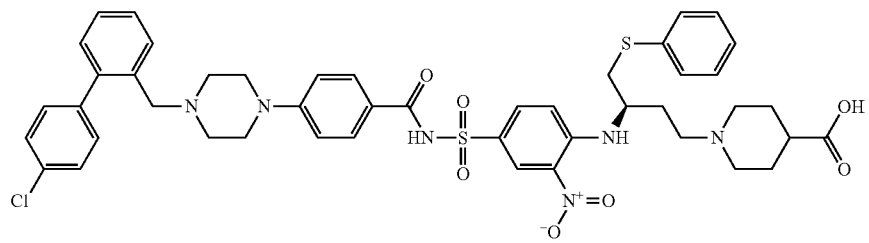 |

| Name | Structure |
|---|---|
| N-(4-(4-((4'-chloro(1,1'-biphenyl)-2-yl)methyl)piperazin-1-yl)benzoyl)-4-(((1R)-3-((2-hydroxyethyl)(methyl)amino)-1-((phenylsulfanyl)methyl)propyl)amino)-3-nitrobenzenesulfonamide, | 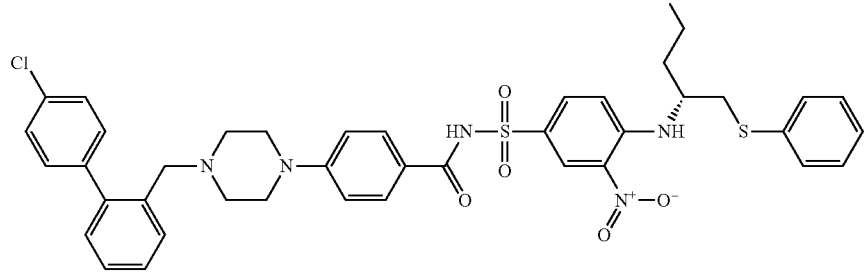 |
| (2S)-1-((3R)-3-(4-(((4-(4-((4'-chloro(1,1'-biphenyl)-2-yl)methyl)piperazin-1-yl)benzoyl)amino)sulfonyl)-2-nitroanilino)-4-(phenylsulfanyl)butyl)-2-pyrrolidinecarboxylic acid, | 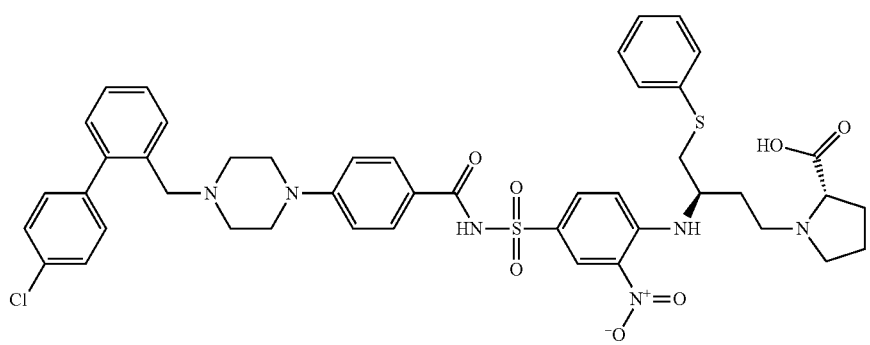 |
| N-(4-(4-((4'-chloro(1,1'-biphenyl)-2-yl)methyl)piperazin-1-yl)benzoyl)-3-nitro-4-(((1R)-1-((phenylsulfanyl)methyl)-3-(3-(2H-tetrazol-5-yl)azetidin-1-yl)propyl)amino)benzenesulfonamide, | 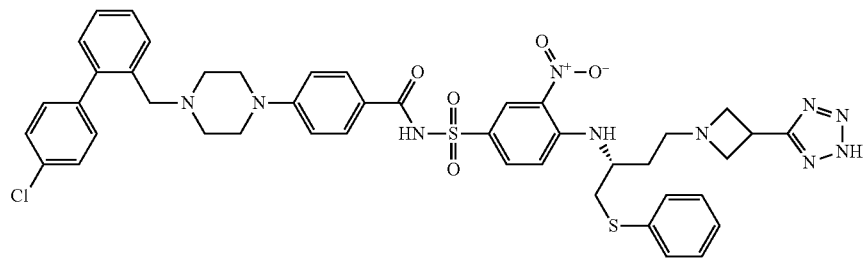 [SMILES: O=C(NS(=O)(=O)c1ccc(N[C@H](CCN2CC(c3nn[nH]n3)C2)CSc2ccccc2)c([N+](=O)[O-])c1)c1ccc(N2CCN(Cc3ccccc3-c3ccc(Cl)cc3)CC2)cc1] |
| (2S)-2-aimno-N-((1S)-2-(((3R)-3-(4-(((4-(4-((4'-chloro(1,1'-biphenyl)-2-yl)methyl)piperazin-1-yl)benzoyl)amino)sulfonyl)-2-nitroanilino)-4-(phenylsulfanyl)butyl)amine)-1-methyl-2-oxoethyl)propanamide, | 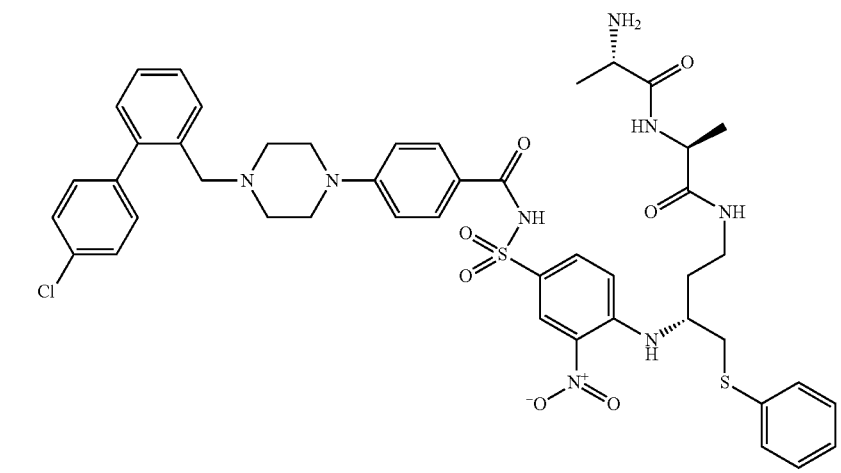 |

-continued

| Name | Structure |
|---|---|
| N-(4-(4-((4'-chloro(1,1'-biphenyl)-2-yl)methyl)piperazin-1-yl)benzoyl)-3-nitro-4-(((1R)-1-((phenylsulfanyl)methyl)-3-(2-(2H-tetrazol-5-yl)pyrrolidin-1-yl)propyl)amino)benzenesulfonamide, | |
| N-(4-(4-((4'-chloro(1,1'-biphenyl)-2-yl)methyl)piperazin-1-yl)benzoyl)-4-(((1R)-3-(4-(((methylsulfonyl)amino)carbonyl)piperidin-1-yl)-1-((phenylsulfanyl)methyl)propyl)amino)-3-nitrobenzenesulfonamide, | 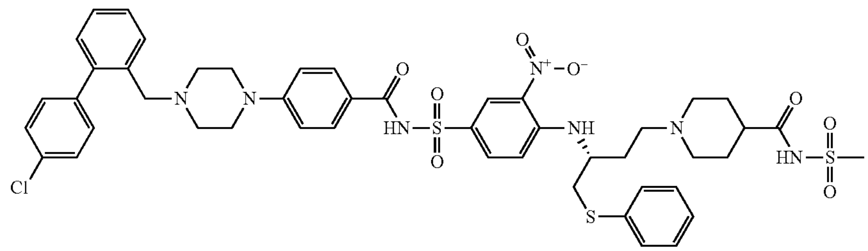 [SMILES: CS(=O)(=O)NC(=O)C1CCN(CC[C@H](CSc2ccccc2)Nc2ccc(S(=O)(=O)NC(=O)c3ccc(N4CCN(Cc5ccccc5-c5ccc(Cl)cc5)CC4)cc3)cc2[N+](=O)[O-])CC1] |
| N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)benzenesulfonamide, | 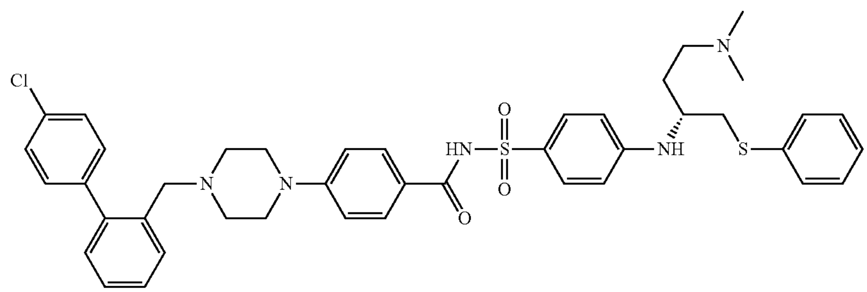 [SMILES: CN(C)CC[C@H](CSc1ccccc1)Nc1ccc(S(=O)(=O)NC(=O)c2ccc(N3CCN(Cc4ccccc4-c4ccc(Cl)cc4)CC3)cc2)cc1] |
| 1-((3R)-3-(4-(((4-(4-((4'-chloro(1,1'-biphenyl)-2-yl)methyl)piperazin-1-yl)benzoyl)amino)sulonyl)-2-nitroanilino)-4-(phenylsulfanyl)butyl)-N-hydroxy-4-piperidinecarboxamide, | 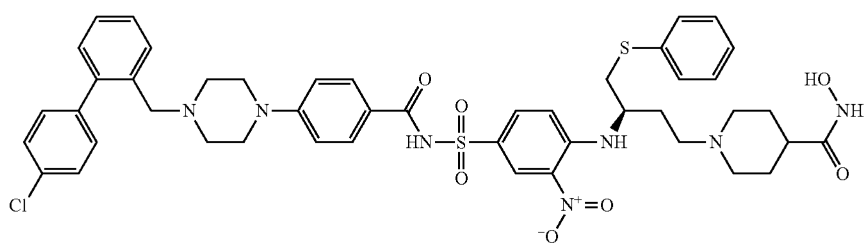 |
| 2-chloro-N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)benzenesulfonamide, | 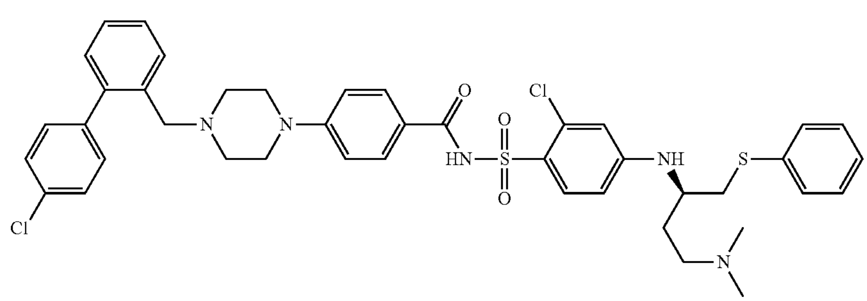 |

-continued

| Name | Structure |
|---|---|
| 2,6-dichloro-N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)benzenesulfonamide, | 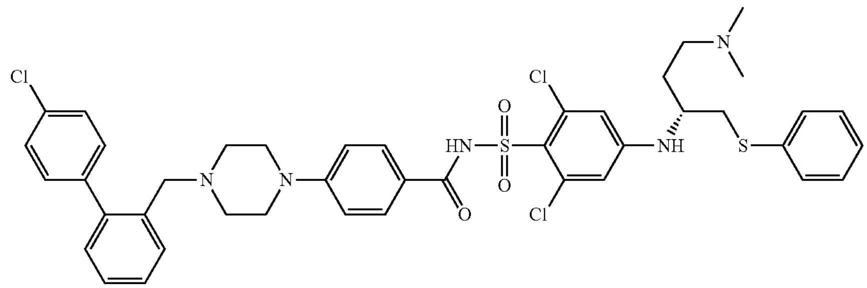 [SMILES: CN(C)CC[C@H](CSc1ccccc1)Nc1cc(Cl)c(S(=O)(=O)NC(=O)c2ccc(N3CCN(Cc4ccccc4-c4ccc(Cl)cc4)CC3)cc2)c(Cl)c1] |
| 4-(((1R)-3-((1R,5S)-8-azabicyclo[3.2.1]oct-8-yl)-1-((phenylsulfanyl)methyl)propyl)amino)-N-(4-(4-((4'-chloro(1,1'-biphenyl)-2-yl)methyl)piperazin-1-yl)benzoyl)-3-nitrobenzenesulfonamide, | 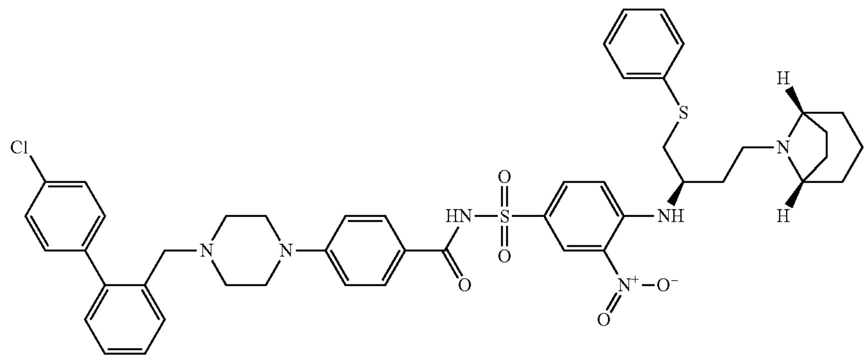 [SMILES: O=C(NS(=O)(=O)c1ccc(N[C@H](CCN2[C@@H]3CCC[C@H]2CC3)CSc2ccccc2)c([N+](=O)[O-])c1)c1ccc(N2CCN(Cc3ccccc3-c3ccc(Cl)cc3)CC2)cc1] |
| 4-(((1R)-3-(7-azabicyclo[2.2.1]hept-7-yl)-1-((phenylsulfanyl)methyl)propyl)amino)-N-(4-(4-((4'-chloro(1,1'-biphenyl)-2-yl)methyl)piperazin-1-yl)benzoyl)-3-nitrobenzenesulfonamide, | 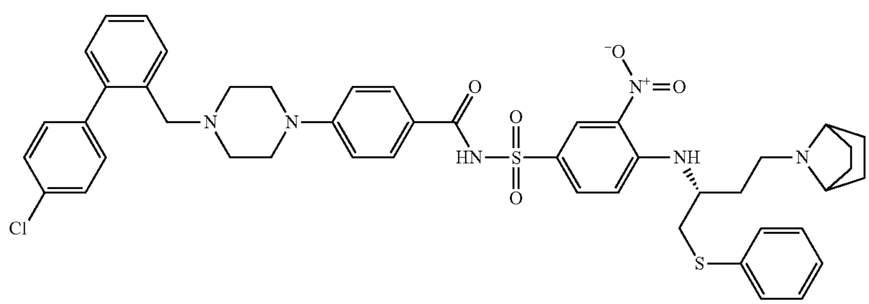 |
| N-(4-(4-((4'-chloro(1,1'-biphenyl)-2-yl)methyl)piperazin-1-yl)benzoyl)-3-nitro-4-(2-(phenylsulfanyl)ethoxy)benzenesulfonamide, | 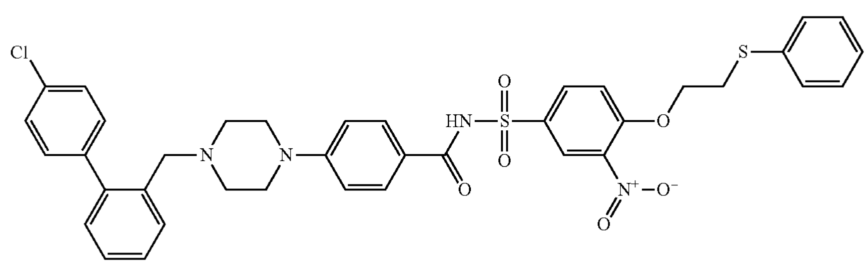 [SMILES: O=C(NS(=O)(=O)c1ccc(OCCSc2ccccc2)c([N+](=O)[O-])c1)c1ccc(N2CCN(Cc3ccccc3-c3ccc(Cl)cc3)CC2)cc1] |
| N-(4-(4-((4'-chloro(1,1'-biphenyl)-2-yl)methyl)piperazin-1-yl)benzoyl)-4-(2-(phenylsulfanyl)ethoxy)-3-(trifluoromethyl)benzenesulfonamide, | |

-continued

| Name | Structure |
|---|---|
| N-(4-(4-((4'-chloro(1,1'-biphenyl)-2-yl)methyl)piperazin-1-yl)benzoyl)-3-nitro-4-(((1R)-3-((1S,4S)-2-oxa-5-azabicyclo[2.2.1]hept-5-yl)-1-((phenylsulfanyl)methyl)propyl)amino)benzenesulfonamide, | 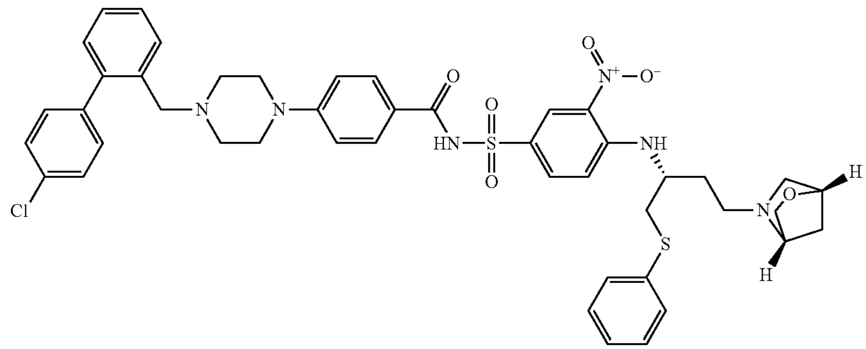 [SMILES: O=C(NS(=O)(=O)c1ccc(N[C@H](CCN2C[C@@H]3C[C@H]2CO3)CSc2ccccc2)c([N+](=O)[O-])c1)c1ccc(N2CCN(Cc3ccccc3-c3ccc(Cl)cc3)CC2)cc1] |
| N-(4-(4-((4'-chloro(1,1'-biphenyl)-2-yl)methyl)piperazin-1-yl)benzoyl)-3-nitro-4-(((1R)-3-((1R,4R)-2-oxa-5-azabicyclo[2.2.1]hept-5-yl)-1-((phenylsulfanyl)methyl)propyl)amino)benzenesulfonamide, | 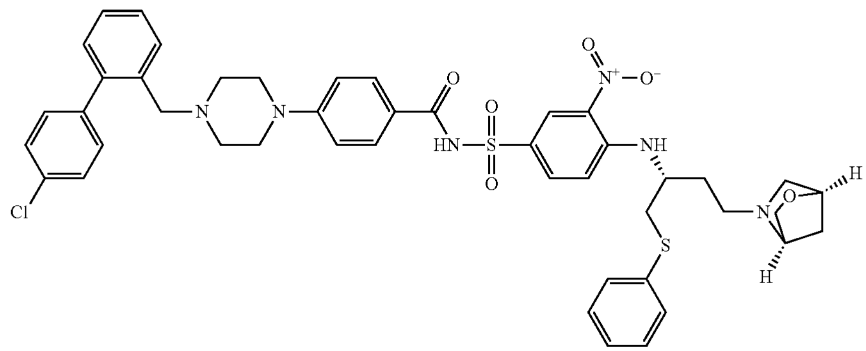 [SMILES: O=C(NS(=O)(=O)c1ccc(N[C@H](CCN2C[C@H]3C[C@@H]2CO3)CSc2ccccc2)c([N+](=O)[O-])c1)c1ccc(N2CCN(Cc3ccccc3-c3ccc(Cl)cc3)CC2)cc1] |
| N-(4-(4-((2-(4-chlorophenyl)-1-cyclohexen-1-yl)methyl)piperazin-1-yl)benzoyl)-3-nitro-4-(((1R)-3-((1S,4S)-2-oxa-5-azabicyclo[2.2.1]hept-5-yl)-1-((phenylsulfanyl)methyl)propyl)amino)benzenesulfonamide, | 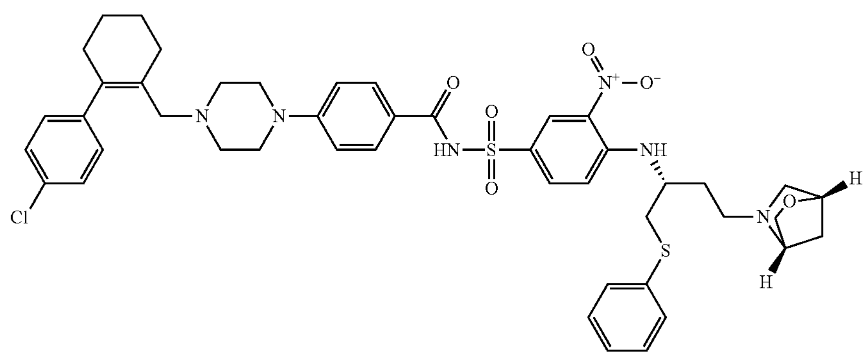 [SMILES: O=C(NS(=O)(=O)c1ccc(N[C@H](CCN2C[C@@H]3C[C@H]2CO3)CSc2ccccc2)c([N+](=O)[O-])c1)c1ccc(N2CCN(CC3=C(c4ccc(Cl)cc4)CCCC3)CC2)cc1] |
| N-(4-(4-((2-(4-chlorophenyl)-1-cyclohexen-1-yl)methyl)piperazin-1-yl)benzoyl)-3-nitro-4-(((1R)-3-((1R,4R)-2-oxa-5-azabicyclo[2.2.1]hept-5-yl)-1-((phenylsulfanyl)methyl)propyl)amino)benzenesulfonamide, | 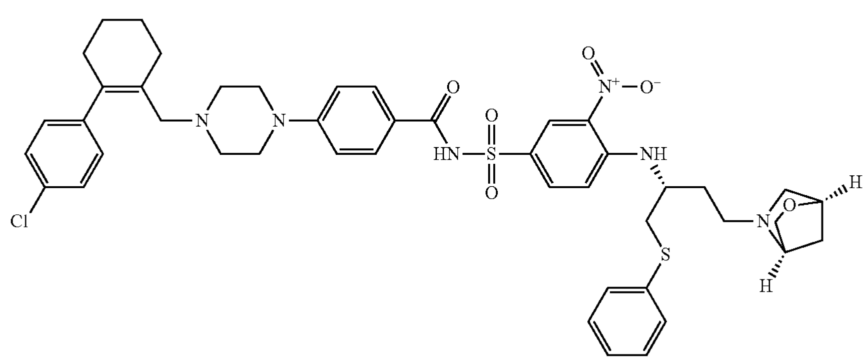 [SMILES: O=C(NS(=O)(=O)c1ccc(N[C@H](CCN2C[C@H]3C[C@@H]2CO3)CSc2ccccc2)c([N+](=O)[O-])c1)c1ccc(N2CCN(CC3=C(c4ccc(Cl)cc4)CCCC3)CC2)cc1] |

| Name | Structure |
|---|---|
| 4-(((1R)-3-(7-azabicyclo[2.2.1]hept-7-yl)-1-((phenylsulfanyl)methyl)propyl)amino)-N-(4-(4-((2-(4-chlorophenyl)-1-cyclohexen-1-yl)methyl)piperazin-1-yl)benzoyl)-3-nitrobenzenesulfonamide, | 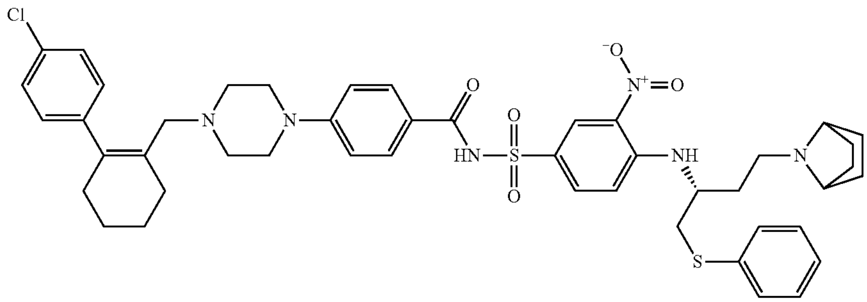 |
| N-(4-(4-((2-(4-chlorophenyl)-1-cyclohexen-1-yl)methyl)piperazin-1-yl)benzoyl)-4-(((1R)-3-((2R,5S)-2,5-dimethylpyrrolidin-1-yl)-1-((phenylsulfanyl)methyl)propyl)amino)-3-nitrobenzenesulfonamide, | 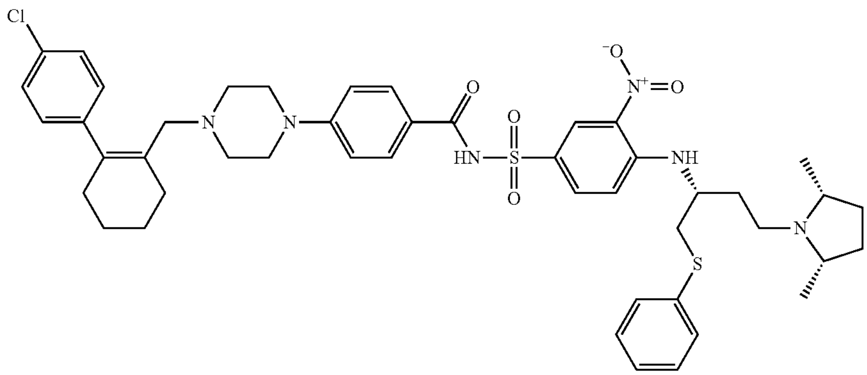 |
| N-(4-(4-((4'-chloro(1,1'-biphenyl)-2-yl)methyl)piperazin-1-yl)benzoyl)-3-nitro-4-(((1R)-3-((1R,4R)-2-oxa-5-azabicyclo[2.2.1]hept-5-yl)-1-((phenylsulfanyl)methyl)propyl)amino)benzenesulfonamide, | 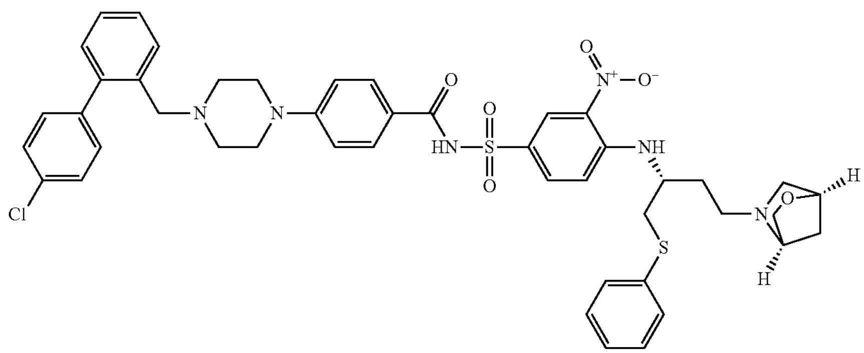 [SMILES: O=C(NS(=O)(=O)c1ccc(N[C@H](CCN2C[C@H]3C[C@@H]2CO3)CSc2ccccc2)c([N+](=O)[O-])c1)c1ccc(N2CCN(Cc3ccccc3-c3ccc(Cl)cc3)CC2)cc1] |
| N-(4-(4-((1,1'-biphenyl)-2-ylmethyl)piperazin-1-yl)benzoyl)-4-(cyclohexyloxy)-3-nitrobenzenesulfonamide, | 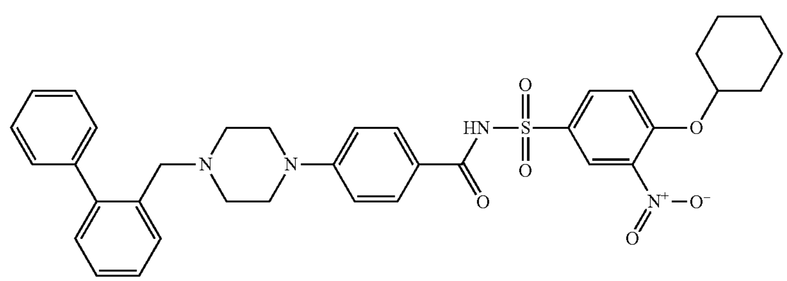 [SMILES: O=C(NS(=O)(=O)c1ccc(OC2CCCCC2)c([N+](=O)[O-])c1)c1ccc(N2CCN(Cc3ccccc3-c3ccccc3)CC2)cc1] |
| N-(4-(4-((1,1'-biphenyl)-2-ylmethyl)piperazin-1-yl)benzoyl)-4-(cyclohexylmethoxy)-3-nitrobenzenesulfonamide, | 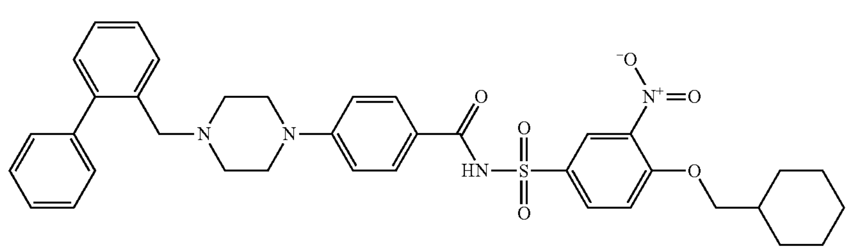 |

| Name | Structure |
|---|---|
| N-(4-(4-((1,1'-biphenyl)-2-ylmethyl)piperazin-1-yl)benzoyl)-4-(2-cyclohexylethoxy)-3-nitrobenzenesulfonamide, | 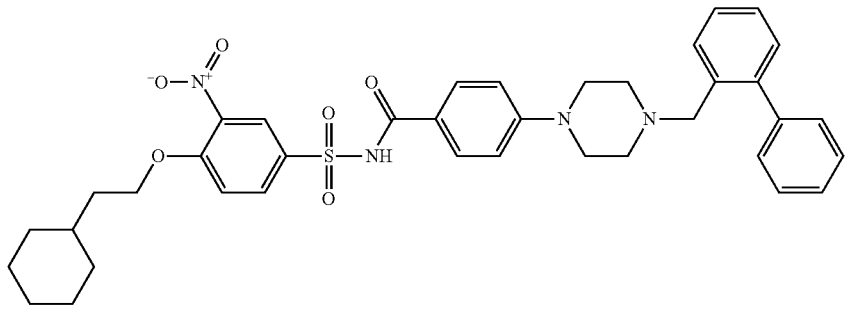 |
| N-(4-(4-((1,1'-biphenyl)-2-ylmethyl)piperazin-1-yl)benzoyl)-3-nitro-4-(tetrahydro-2H-pyran-4-ylamino)benzenesulfonamide, | 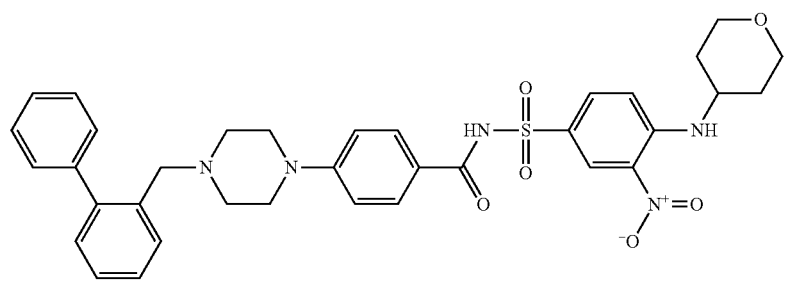 |
| N-(4-(4-((1,1'-biphenyl)-2-ylmethyl)piperazin-1-yl)benzoyl)-4-((2-cyclohexylethyl)amino)-3-nitrobenzenesulfonamide, | 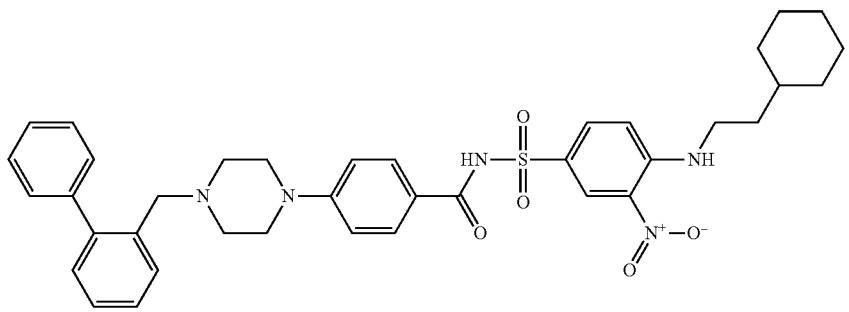 [SMILES: O=C(NS(=O)(=O)c1ccc(NCCC2CCCCC2)c([N+](=O)[O-])c1)c1ccc(N2CCN(Cc3ccccc3-c3ccccc3)CC2)cc1] |
| N-(4-(4-((1,1'-biphenyl)-2-ylmethyl)piperazin-1-yl)benzoyl)-4-(cyclohexyl)methyl)amino)-3-nitrobenzenesulfonamide, | 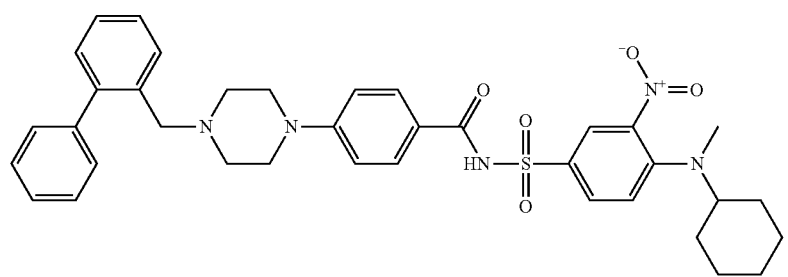 |
| N-(4-(4-((1,1'-biphenyl)-2-ylmethyl)piperazin-1-yl)benzoyl)-4-(4,4-dimethylpiperidin-1-yl)-3-nitrobenzenesulfonamide, | 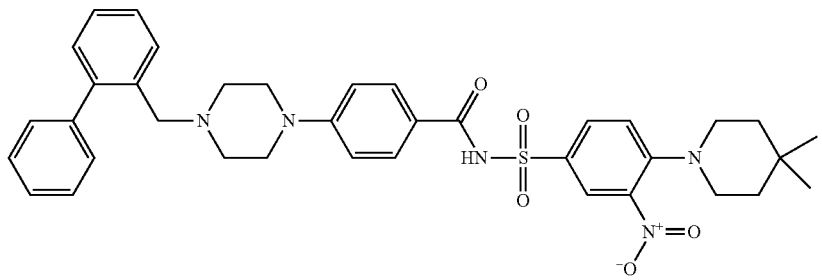 |

| Name | Structure |
|---|---|
| tert-butyl 4-(4-(((4-(4-((1,1'-biphenyl)-2-ylmethyl)piperazin-1-yl)benzoyl)amino)sulfonyl)-2-nitrophenoxy)-1-piperidinecarboxylate, | 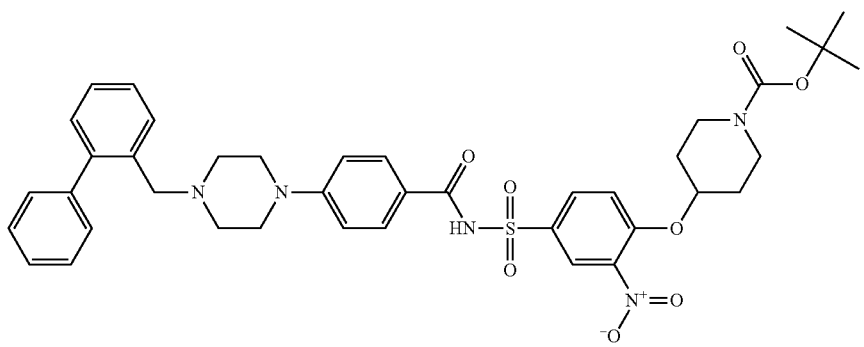 |
| N-(4-(4-((1,1'-biphenyl)-2-ylmethyl)piperazin-1-yl)benzoyl)-3-nitro-4-(piperidin-4-yloxy)benzenesulfonamide, | 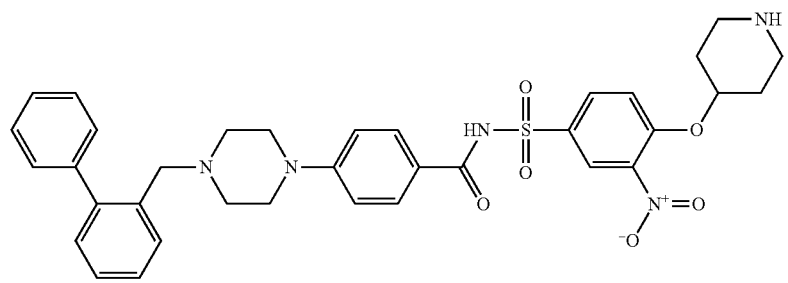 |
| N-(4-(4-((1,1'-biphenyl)-2-ylmethyl)piperazin-1-yl)benzoyl)-4-((1-methylpiperidin-4-yl)oxy)-3-nitrobenzenesulfonamide, | 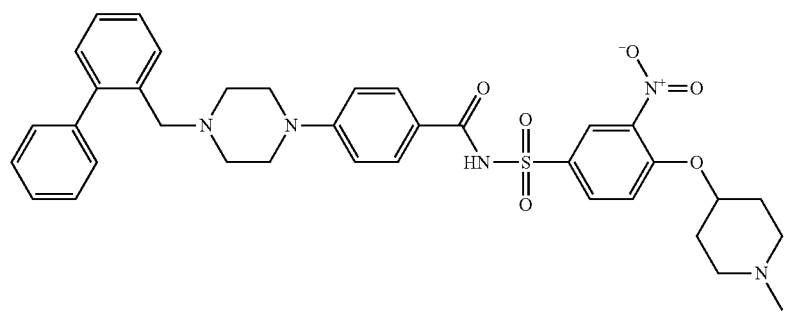 |
| N-(4-(4-((4'-chloro(1,1'-biphenyl)-2-yl)methyl)piperazin-1-yl)benzoyl)-4-((cyclohexylmethyl)amino)-3-nitrobenzenesulfonamide, | 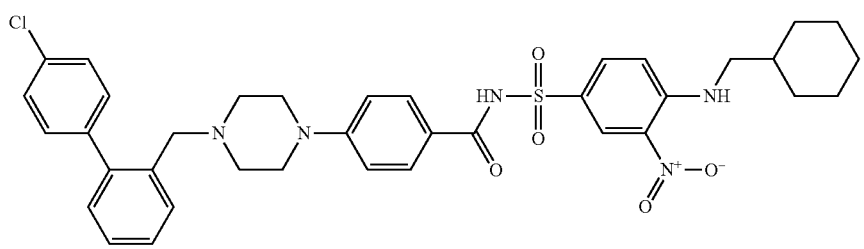 [SMILES: O=C(NS(=O)(=O)c1ccc(NCC2CCCCC2)c([N+](=O)[O-])c1)c1ccc(N2CCN(Cc3ccccc3-c3ccc(Cl)cc3)CC2)cc1] |
| N-(4-(4-((4'-chloro(1,1'-biphenyl)-2-yl)methyl)piperazin-1-yl)benzoyl)-4-((cyclohexylmethyl(propyl)amino)-3-nitrobenzenesulfonamide, | 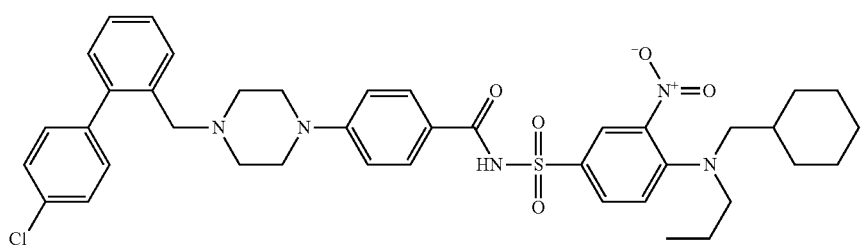 |

| Name | Structure |
|---|---|
| 4-(((1-benzylpiperidin-4-yl)methyl)amino)-N-(4-(4-((1,1'-biphenyl)-2-ylmethy)piperazin-1-yl)benzoyl)-3-nitrobenzenesulfonamide, | 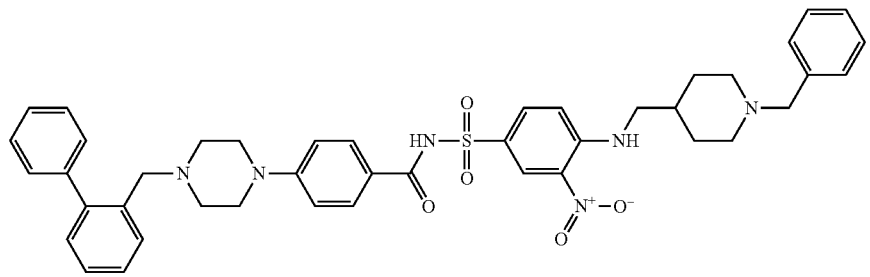 [SMILES: O=C(NS(=O)(=O)c1ccc(NCC2CCN(Cc3ccccc3)CC2)c([N+](=O)[O-])c1)c1ccc(N2CCN(Cc3ccccc3-c3ccccc3)CC2)cc1] |
| N-(4-(4-((1,1'-biphenyl)-2-ylmethyl)piperazin-1-yl)benzoyl)-4-((cyclohexylmethyl)(methyl)amino)-3-nitrobenzenesulfonamide, | 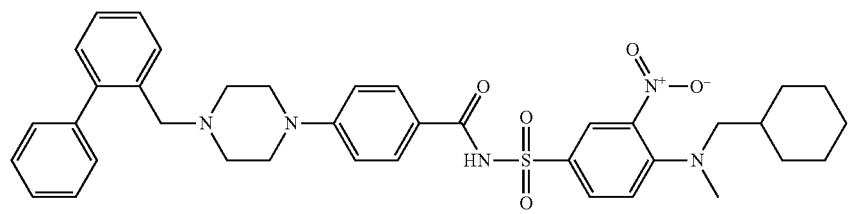 [SMILES: CN(CC1CCCCC1)c1ccc(S(=O)(=O)NC(=O)c2ccc(N3CCN(Cc4ccccc4-c4ccccc4)CC3)cc2)cc1[N+](=O)[O-]] |
| 4-((1-benzylpiperidin-4-yl)amino)-N-(4-(4-((1,1'-biphenyl)-2-ylmethyl)piperazin-1-yl)benzoyl)-3-nitrobenzenesulfonamide, | 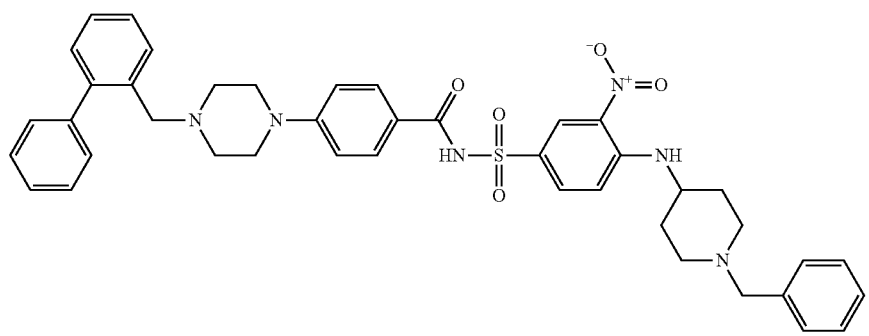 |
| N-(4-(4-((1,1'-biphenyl)-2-ylmethyl)piperazin-1-yl)benzoyl)-3-nitro-4-(tetrahydro-2H-sulfanylpyran-4-ylamino)benzenesulfonamide, | 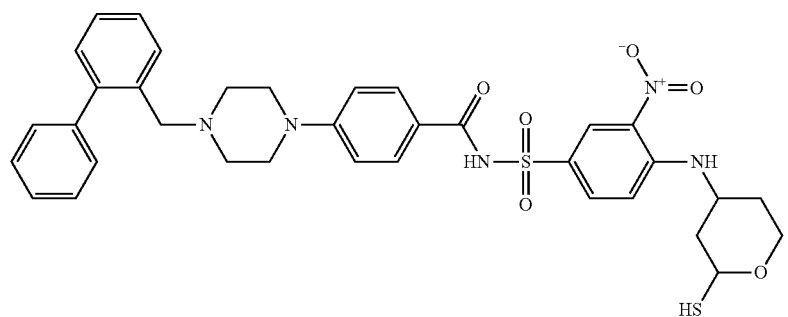 |
| ethyl 4-(4-(((4-(4-((1,1'-biphenyl)-2-ylmethyl)piperazin-1-yl)benzoyl)amino)sulfonyl)-2-nitroanilino)-1-piperidinecarboxylate, | 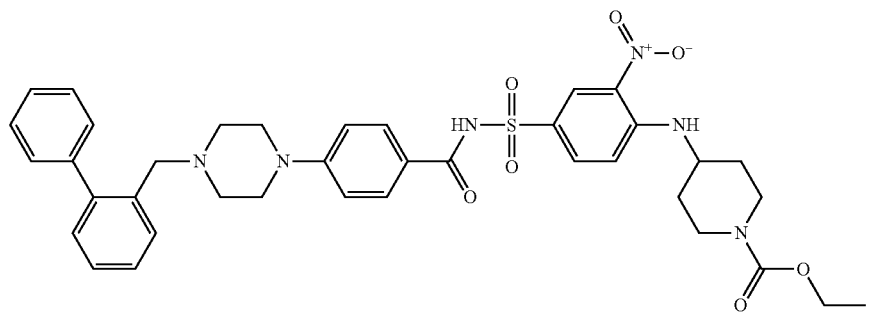 [SMILES: CCOC(=O)N1CCC(Nc2ccc(S(=O)(=O)NC(=O)c3ccc(N4CCN(Cc5ccccc5-c5ccccc5)CC4)cc3)cc2[N+](=O)[O-])CC1] |

| Name | Structure |
|---|---|
| N-(4-(4-((1,1'-biphenyl)-2-ylmethyl)piperazin-1-yl)benzoyl)-3-nitro-4-(((1-propylpiperidin-4-yl)methyl)amino)benzenesulfonamide, | 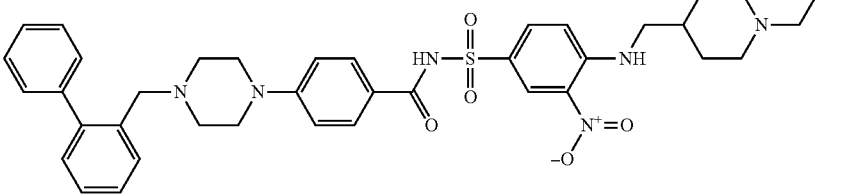 |
| N-(4-(4-((1,1'-biphenyl)-2-ylmethyl)piperazin-1-yl)benzoyl)-4-(isopropylamino)-3-nitrobenzenesulfonamide, | 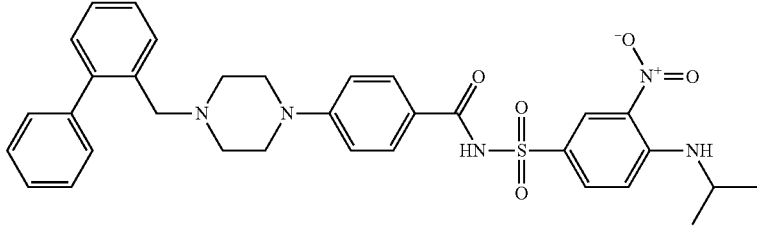 |
| N-(4-(4-((1,1'-biphenyl)-2-ylmethyl)piperazin-1-yl)benzoyl)-3-nitro-4-((2-(1,3-thiazol-2-ylsulfanyl)ethyl)amino)benzenesulfonamide, | 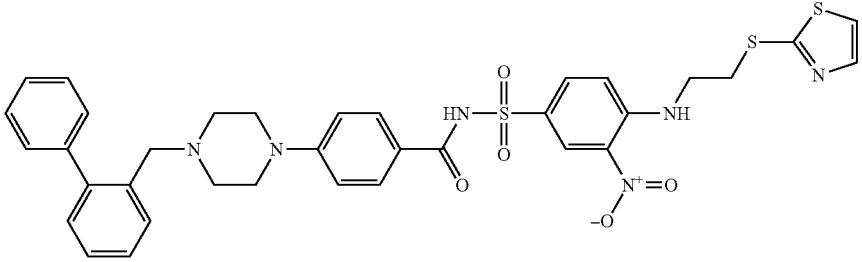 |
| N-(4-(4-((1,1'-biphenyl)-2-ylmethyl)piperazin-1-yl)benzoyl)-3-nitro-4-((2-((4-phenyl-1,3-thiazol-2-yl)sulfanyl)ethyl)amino)benzenesulfonamide, |  |
| 4-((2-(1,3-benzothiazol-2-ylsulfanyl)ethyl)amino)-N-(4-(4-((1,1'-biphenyl)-2-ylmethyl)piperazin-1-yl)benzoyl)-3-nitrobenzenesulfonamide, | 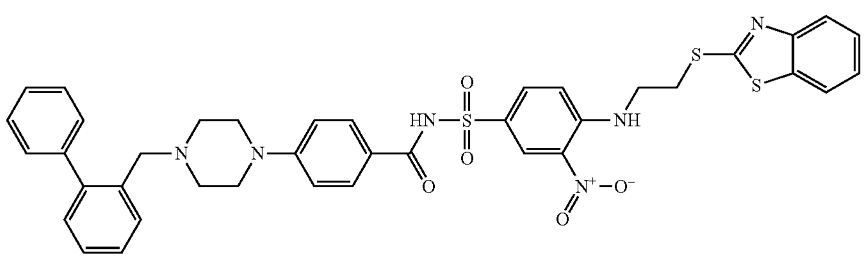 [SMILES: O=C(NS(=O)(=O)c1ccc(NCCSc2nc3ccccc3s2)c([N+](=O)[O-])c1)c1ccc(N2CCN(Cc3ccccc3-c3ccccc3)CC2)cc1] |
| N-(4-(4-((4'-chloro(1,1'-biphenyl)-2-yl)methyl)piperazin-1-yl)benzoyl)-3-nitro4-((2-(1,3-thiazol-2-ylsulfanyl)ethyl)amino)benzenesulfonamide, | 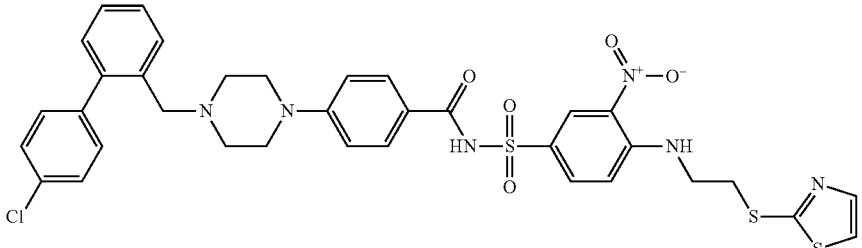 |

-continued

| Name | Structure |
|---|---|
| 4-((2-(1,3-benzoxazol-2-ylsulfanyl)ethyl)amino)-N-(4-(4-((4'-chloro(1,1'-biphenyl)-2-yl)methyl)piperazin-1-yl)benzoyl)-3-nitrobenzenesulfonamide, | 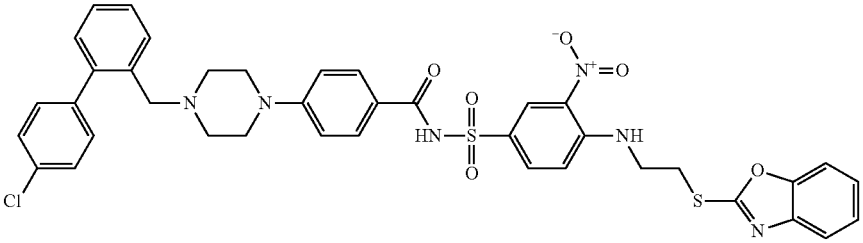 |
| 4-((2-(1,3-benzothiazol-2-ylsulfanyl)ethyl)amino)-N-(4-(4-((4'-chloro(1,1'-biphenyl)-2-yl)methyl)piperazin-1-yl)benzoyl)-3-nitrobenzenesulfonamide, | 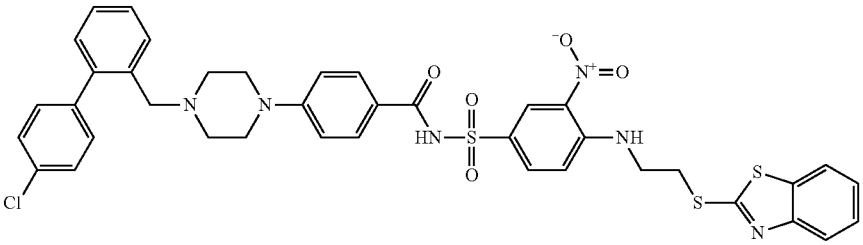 |
| N-(4-(4-((4'-chloro(1,1'-biphenyl)-2-yl)methyl)piperazin-1-yl)benzoyl)-3-nitro-4-((2-(pyrimidin-2-ylsulfanyl)ethyl)amino)benzenesulfonamide, | 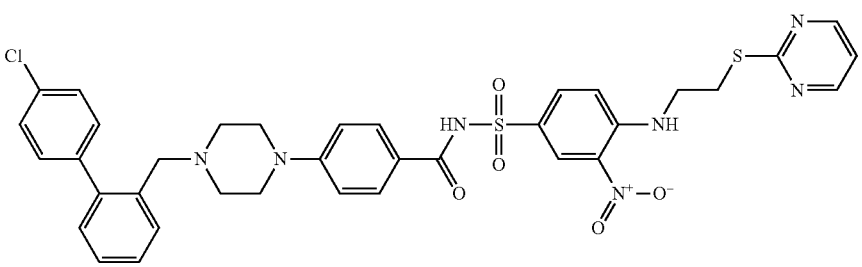 [SMILES: O=C(NS(=O)(=O)c1ccc(NCCSc2ncccn2)c([N+](=O)[O-])c1)c1ccc(N2CCN(Cc3ccccc3-c3ccc(Cl)cc3)CC2)cc1] |
| 4-(((1R)-3-(morpholin-4-yl)-1-((phenylsulfanyl)methyl)propyl)amino)-3-nitro-N-(4-(4-((1-phenyl-1H-pyrazol-5-yl)methyl)piperazin-1-yl)benzoyl)benzenesulfonamide, | 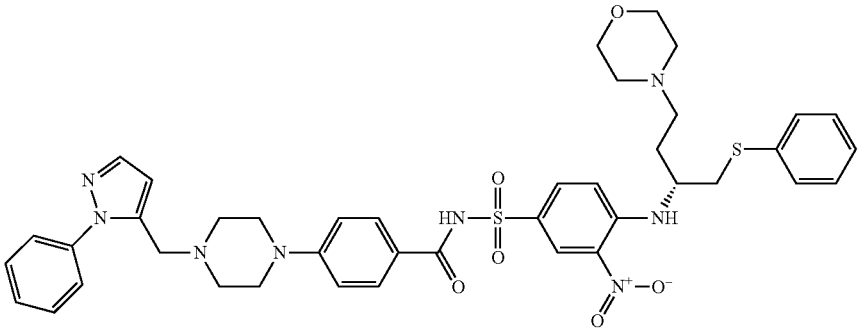 |
| 4-(((1-benzylpiperidin-4-yl)methyl)amino)-N-(4-(4-((4'-chloro(1,1'-biphenyl)-2-yl)methyl)piperazin-1-yl)benzoyl)-3-nitrobenzenesulfonamide, | 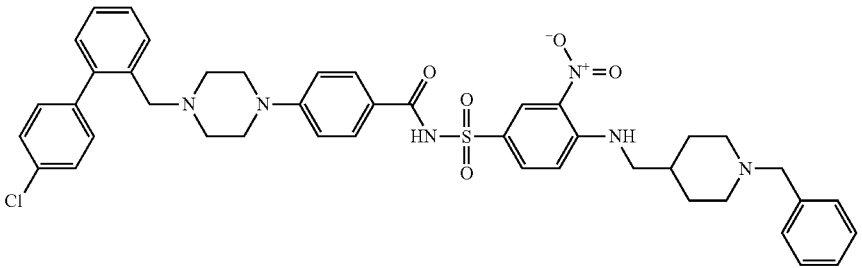 |

-continued

| Name | Structure |
|---|---|
| N-(4-(4-((1,1'-biphenyl)-2-ylmethyl)piperazin-1-yl)benzoyl)-4-((2-bromoethyl)amino)-3-nitrobenzenesulfonamide, | 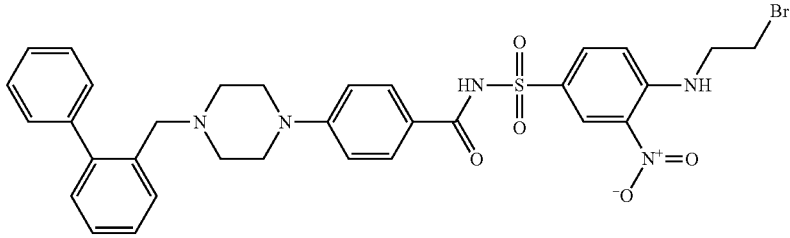 |
| N-(4-(4-((4'-chloro(1,1'-biphenyl)-2-yl)methyl)piperazin-1-yl)benzoyl)-4-((2-((4-methyl-1,3-thiazol-2-yl)sulfanyl)ethyl)amino)-3-nitrobenzenesulfonamide, | 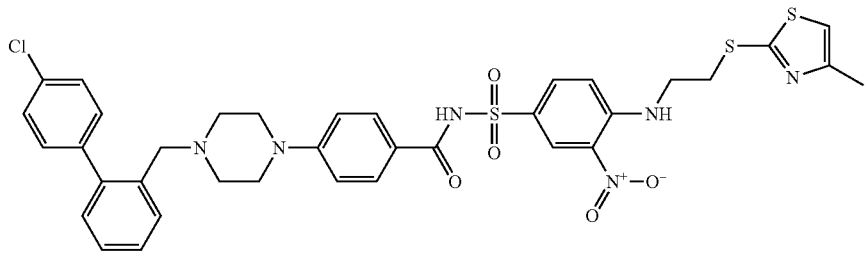 [SMILES: Cc1csc(SCCNc2ccc(S(=O)(=O)NC(=O)c3ccc(N4CCN(Cc5ccccc5-c5ccc(Cl)cc5)CC4)cc3)cc2[N+](=O)[O-])n1] |
| N-(4-(4-((4'-chloro(1,1'-biphenyl)-2-yl)methyl)piperazin-1-yl)benzoyl)-4-(((4-methoxycyclohexyl)methyl)amino)-3-nitrobenzenesulfonamide, | 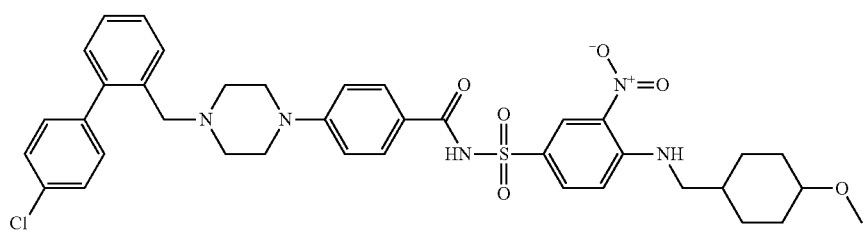 |
| N-(4-(4-((1,1'-biphenyl)-2-ylmethyl)piperazin-1-yl)benzoyl)-3-nitro-4-((2-(2-thienylsulfanyl)ethyl)amino)benzenesulfonamide, | 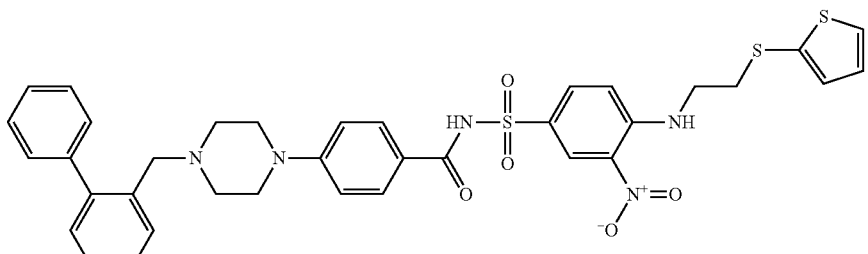 |
| N-(4-(4-((4'-chloro(1,1'-biphenyl)-2-yl)methyl)piperazin-1-yl)benzoyl)-4-((1,1-dimethyl-2-(2-thienylsulfanyl)ethyl)amino)-3-nitrobenzenesulfonamide, | 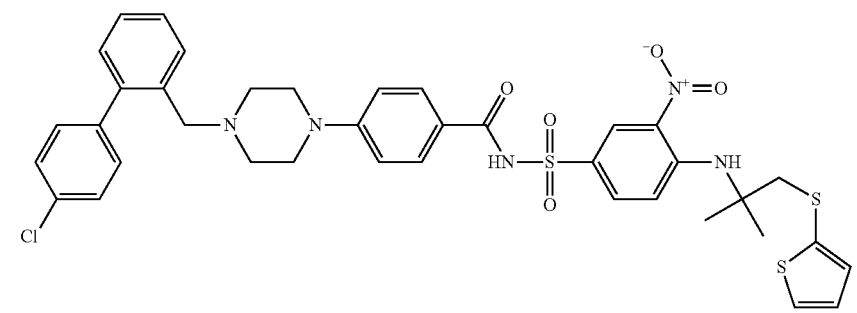 |

-continued

| Name | Structure |
|---|---|
| N-(4-(4-((4'-chloro(1,1'-biphenyl)-2-yl)methyl)piperazin-1-yl)benzoyl)-4-(((1R)-3-(morpholin-4-yl)-1-((1,3-thiazol-2-ylsulfanyl)methyl)propyl)amino)-3-nitrobenzenesulfonamide, | 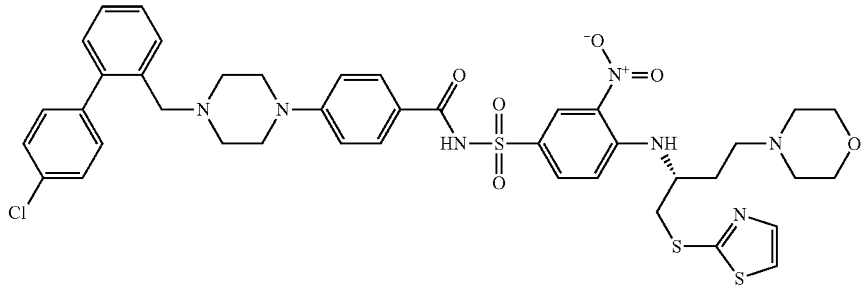 |
| (3R)-3-(4-(((4-(4-((4'-chloro(1,1'-biphenyl)-2-yl)methyl)piperazin-1-yl)benzoyl)amino)sulfonyl)-2-nitroanilino)-N,N-dimethyl-4-(pyrimidin-2-ylsulfanyl)butanamide, | 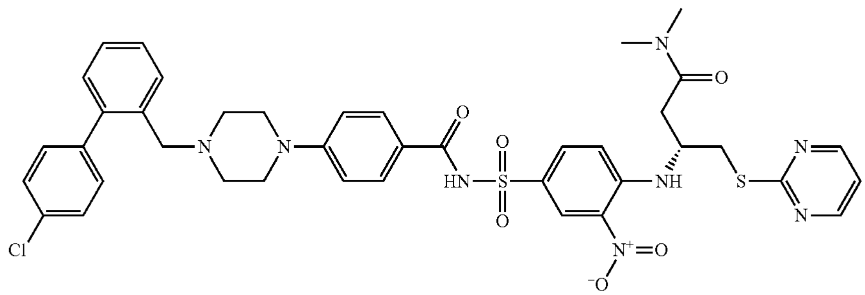 |
| N-(4-(4-((4'-chloro(1,1'-biphenyl)-2-yl)methyl)piperazin-1-yl)benzoyl)-4-(((1R)-3-(morpholin-4-yl)-3-oxo-1-((2-thienylsulfanyl)methyl)propyl)amino)-3-nitrobenzenesulfonamide, | 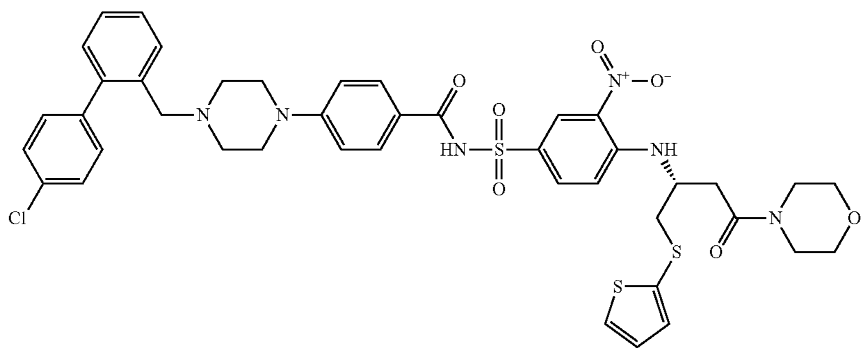 [SMILES: O=C(NS(=O)(=O)c1ccc(N[C@@H](CSc2cccs2)CC(=O)N2CCOCC2)c([N+](=O)[O-])c1)c1ccc(N2CCN(Cc3ccccc3-c3ccc(Cl)cc3)CC2)cc1] |
| N-(4-(4-((4'-chloro(1,1'-biphenyl)-2-yl)methyl)piperazin-1-yl)benzoyl)-4-((1,1-dimethyl-2-(pyrimidin-2-ylsulfanyl)ethyl)amino)-3-nitrobenzenesulfonamide, | 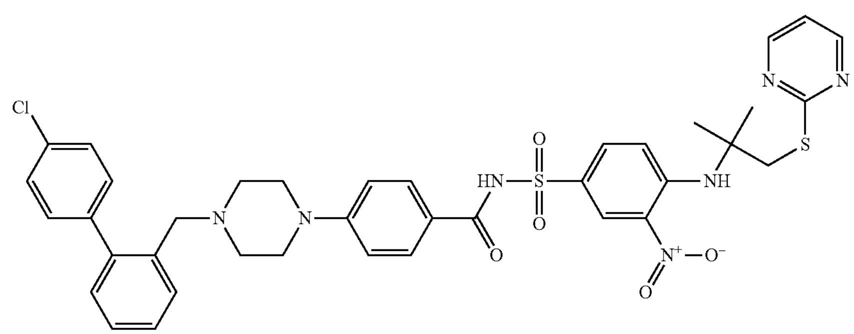 [SMILES: CC(C)(CSc1ncccn1)Nc1ccc(S(=O)(=O)NC(=O)c2ccc(N3CCN(Cc4ccccc4-c4ccc(Cl)cc4)CC3)cc2)cc1[N+](=O)[O-]] |
| (3R)-3-(4-(((4-(4-((4'-chloro(1,1'-biphenyl)-2-yl)methyl)piperazin-1-yl)benzoyl)amine)sulfonyl)-2-nitroanilino)-N,N-dimethyl-4-(1,3-thiazol-2-ylsulfanyl)butanamide, | 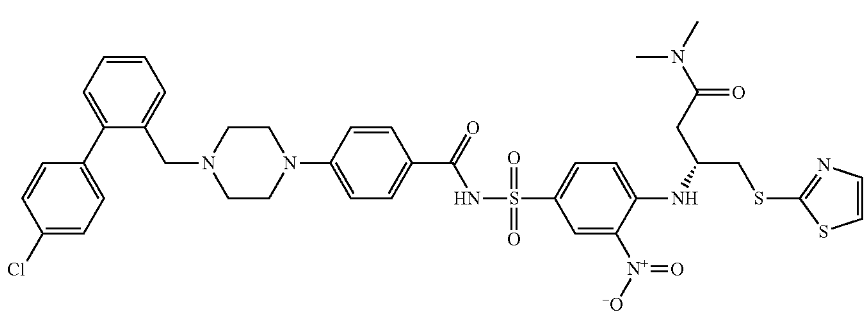 |

| Name | Structure |
|---|---|
| N-(4-(4-((4'-chloro(1,1'-biphenyl)-2-yl)methyl)piperazin-1-yl)benzoyl)-4-(((1R)-3-(morpholin-4-yl)-1-((2-thienylsulfanyl)methyl)propyl)amino)-3-nitrobenzenesulfonamide, | 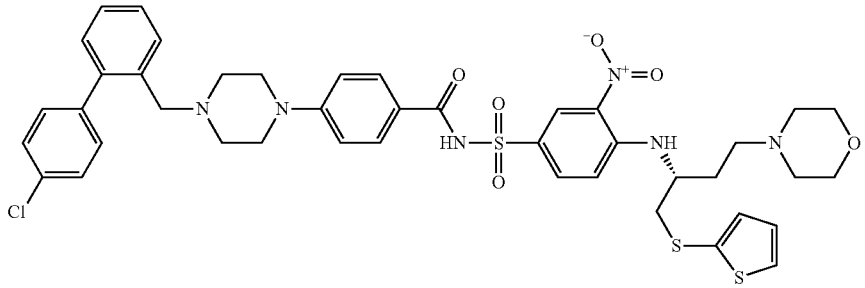 |
| N-(4-(4-((4'-chloro(1,1'-biphenyl)-2-yl)methyl)piperazin-1-yl)benzoyl)-4-(((1R)-3-(dimethylamino)-1-(((4-(trifluoromethoxy)phenyl)sulfanyl)methyl)propyl)amino)-3-nitrobenzenesulfonamide, | 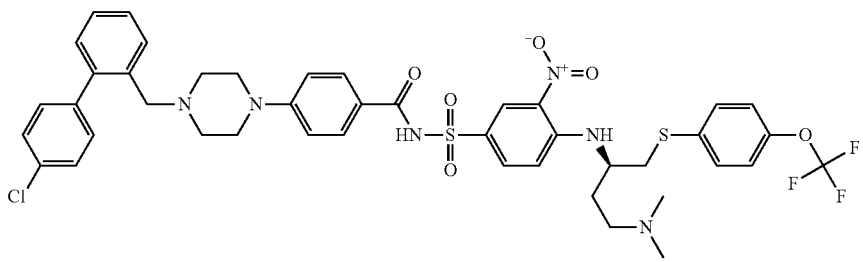 |
| N-(4-(4-((4'-chloro(1,1'-biphenyl)-2-yl)methyl)piperazin-1-yl)benzoyl)-3-nitro-4-((2-phenoxyethyl)amino)benzene-sulfonamide, | 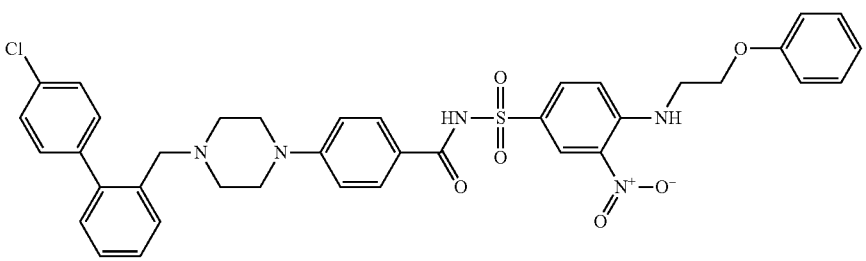 |
| N-(4-(4-((4'-chloro(1,1'-biphenyl)-2-yl)methyl)piperazin-1-yl)benzoyl)-4-(((1R)-3-(morpholin-4-yl)-1-(((4-(trifluoromethoxy)phenyl)sulfanyl)methyl)propyl)amino)-3-nitrobenzenesulfonamide, | 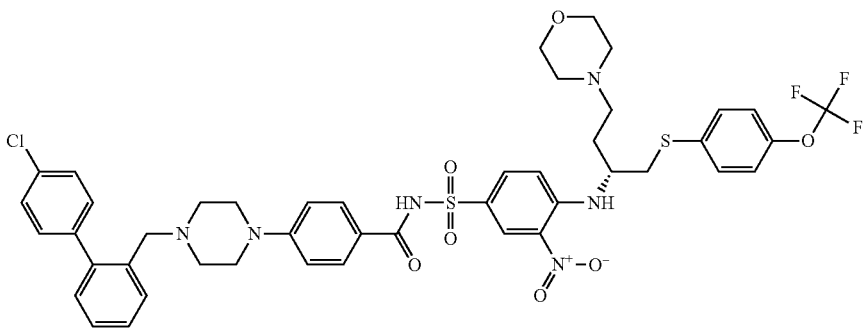 [SMILES: O=C(NS(=O)(=O)c1ccc(N[C@H](CCN2CCOCC2)CSc2ccc(OC(F)(F)F)cc2)c([N+](=O)[O-])c1)c1ccc(N2CCN(Cc3ccccc3-c3ccc(Cl)cc3)CC2)cc1] |
| N-(4-(4-((4'-chloro(1,1'-biphenyl)-2-yl)methyl)piperazin-1-yl)benzoyl)-4-(((1R)-1-(((4-methoxyphenyl)sulfanyl)methyl)-3-(morpholin-4-yl)propyl)amino)-3-nitrobenzenesulfonamide, | 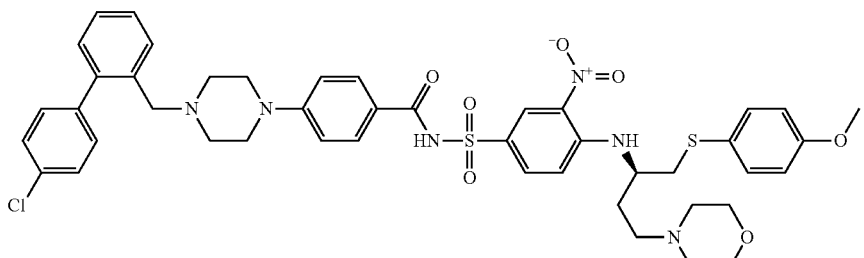 |

-continued

| Name | Structure |
|---|---|
| N-(4-(4-((4'-chloro(1,1'-biphenyl)-2-yl)methyl)piperazin-1-yl)benzoyl)-4-(((1R)-1-(((4-methylphenyl)sulfanyl)methyl)-3-(morpholin-4-yl)propyl)amino)-3-nitrobenzenesulfonamide, | 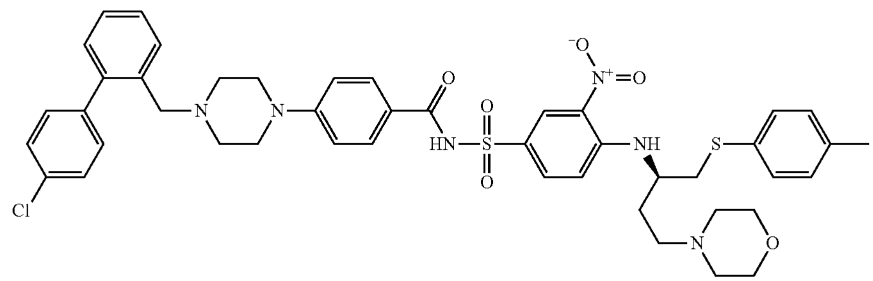 |
| N-(4-(4-((4'-chloro(1,1'-biphenyl)-2-yl)methyl)piperazin-1-yl)benzoyl)-4-(((1R)-3-(dimethylamino)-1-((2-thienylsulfanyl)methyl)propyl)amino)-3-(trifluoromethyl)benzene-sulfonamide, | 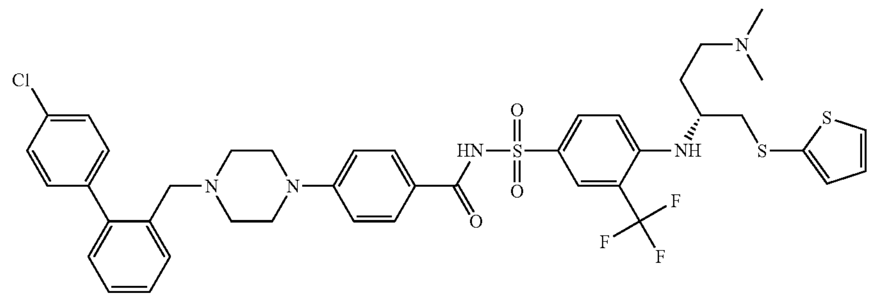 [SMILES: CN(C)CC[C@H](CSc1cccs1)Nc1ccc(S(=O)(=O)NC(=O)c2ccc(N3CCN(Cc4ccccc4-c4ccc(Cl)cc4)CC3)cc2)cc1C(F)(F)F] |
| N-(4-(4-((4'-chloro(1,1'-biphenyl)-2-yl)methyl)piperazin-1-yl)benzoyl)-4-(((1R)-1-(((4-chlorophenyl)sulfanyl)methyl)-3-(morpholin-4-yl)propyl)amino)-3-nitrobenzenesulfonamide, | 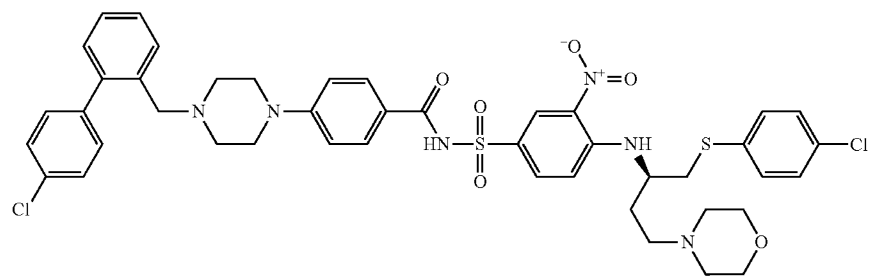 |
| N-(4-(4-((4'-chloro(1,1'-biphenyl)-2-yl)methyl)piperazin-1-yl)benzoyl)-4-(((1R)-3-(dimethylamino)-1-(((4-fluorophenyl)sulfanyl)methyl)propyl)amino)-3-nitrobenzenesulfonamide, | 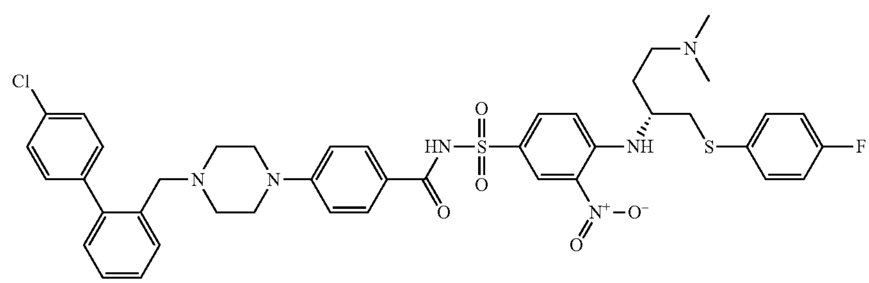 [SMILES: CN(C)CC[C@H](CSc1ccc(F)cc1)Nc1ccc(S(=O)(=O)NC(=O)c2ccc(N3CCN(Cc4ccccc4-c4ccc(Cl)cc4)CC3)cc2)cc1[N+](=O)[O-]] |
| N-(4-(4-((4'-chloro(1,1'-biphenyl)-2-yl)methyl)piperazin-1-yl)benzoyl)-4-(((1R)-1-(((4-fluorophenyl)sulfanyl)methyl)-3-(morpholin-4-yl)propyl)amino)-3-nitrobenzenesulfonamide, | 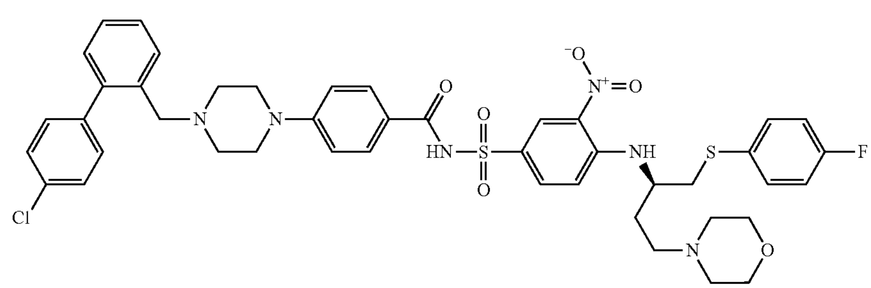 |

-continued

| Name | Structure |
|---|---|
| N-(4-(4-((4'-chloro(1,1'-biphenyl)-2-yl)methyl)piperazin-1-yl)-2-fluorobenzoyl)-4-(((1R)-3-(dimethylamino)-1-((phenylsulfanyl)methyl)propyl)amino)-3-nitrobenzenesulfonamide, | 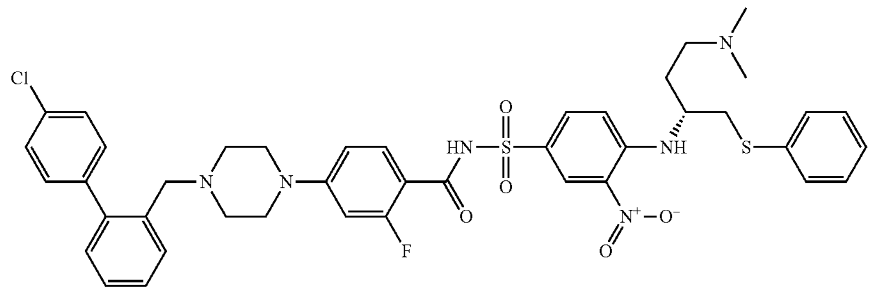 [SMILES: CN(C)CC[C@H](CSc1ccccc1)Nc1ccc(S(=O)(=O)NC(=O)c2ccc(N3CCN(Cc4ccccc4-c4ccc(Cl)cc4)CC3)cc2F)cc1[N+](=O)[O-]] |
| N-(4-(1-((4'-chloro(1,1'-biphenyl)-2-yl)methyl)-1,2,3,6-tetrahydropyridin-4-yl)benzoyl)-4-(((1R)-3-dimethylamino)-1-((phenylsulfanyl)methyl)propyl)amino)-3-nitrobenzenesulfonamide, | 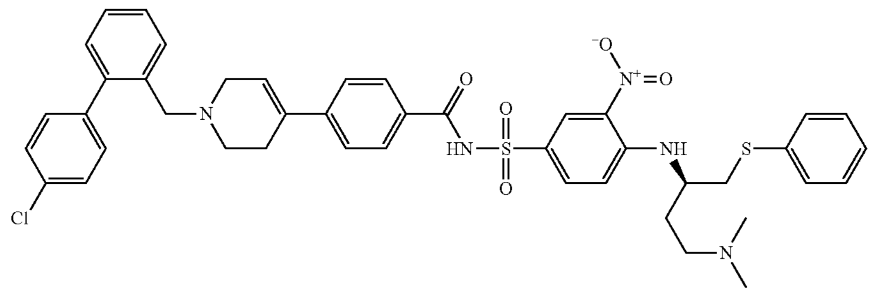 |
| N-(4-(1-((4'-chloro(1,1'-biphenyl)-2-yl)methyl)-1,2,3,6-tetrahydropyridin-4-yl)benzoyl)-4-(((1R)-3-(morpholin-4-yl)-1-((phenylsulfanyl)methyl)propyl)amino)-3-nitrobenzenesulfonamide, | 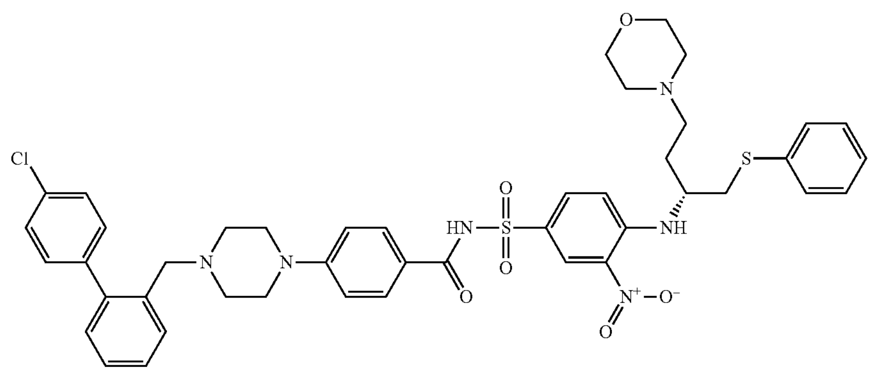 |
| N-(4-(4-((4'-chloro(1,1'-biphenyl)-2-yl)methyl)piperazin-1-yl)-2-fluorobenzoyl)-4-(((1R)-3-(dimethylamino)-1-((phenylsulfany)methyl)propyl)amino)-3-(trifluoromethyl)benzene-sulfonamide, | 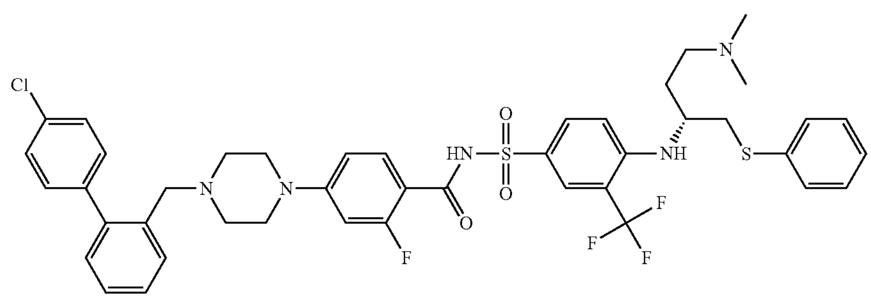 [SMILES: CN(C)CC[C@H](CSc1ccccc1)Nc1ccc(S(=O)(=O)NC(=O)c2ccc(N3CCN(Cc4ccccc4-c4ccc(Cl)cc4)CC3)cc2F)cc1C(F)(F)F] |
| N-((6-(4-((4'-chloro(1,1'-biphenyl)-2-yl)methyl)piperazin-1-yl)pyridin-3-yl)carbonyl)-4-(((1R)-3-(dimethylamino)-1-((phenylsulfanyl)methyl)propyl)amino)-3-nitrobenzenesulfonamide, | 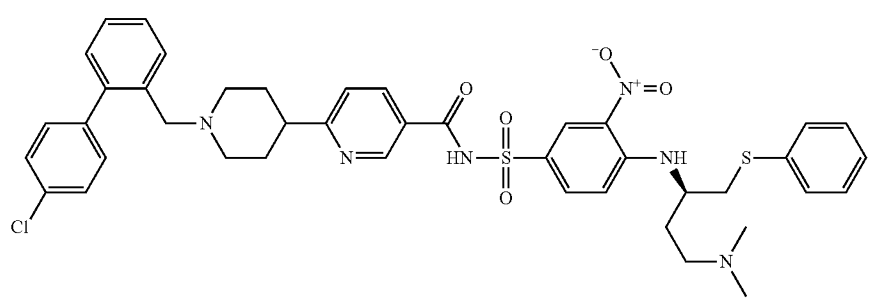 |

| Name | Structure |
|---|---|
| N-(4-(1-((4'-chloro(1,1'-biphenyl)-2-yl)methyl)piperidin-4-yl)benzoyl)-4-(((1R)-3-(dimethylamino)-1-({phenylsulfanyl}methyl)propyl)amino)-3-nitrobenzenesulfonamide, | |
| N-(4-(1-((4'-chloro(1,1'-biphenyl)-2-yl)methyl)piperidin-4-yl)benzoyl)-4-(((1R)-3-(morpholin-4-yl)-1-((phenylsulfanyl)methyl)propyl)amino)-3-nitrobenzenesulfonamide, | 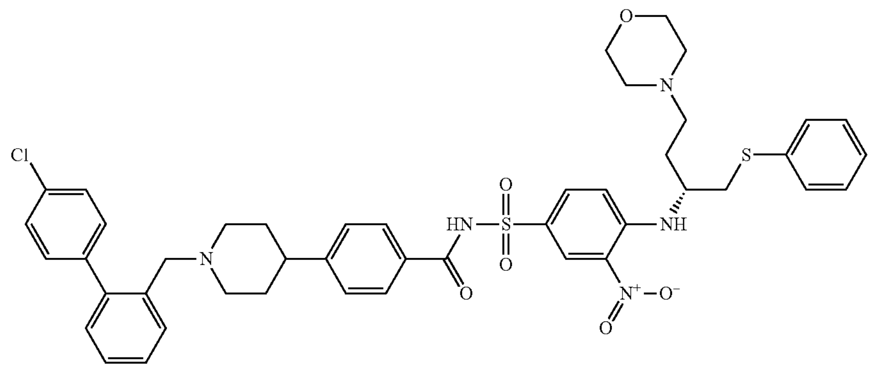 [SMILES: O=C(NS(=O)(=O)c1ccc(N[C@H](CCN2CCOCC2)CSc2ccccc2)c([N+](=O)[O-])c1)c1ccc(C2CCN(Cc3ccccc3-c3ccc(Cl)cc3)CC2)cc1] |
| N-(4-(1-((4'-chloro(1,1'-biphenyl)-2-yl)methyl)-1,2,3,6-tetrahydropyridin-4-yl)benzoyl)-4-(((1R)-3-(dimethylamino)-1-((phenylsulfanyl)methyl)propyl)amino)-3-(trifluoromethyl)benzene-sulfonamide, | |
| N-((6-(4-((4'-chloro(1,1'-biphenyl)-2-yl)methyl)piperazin-1-yl)pyridin-3-yl)carbonyl)-4-(((1R)-3-(morpholin-4-yl)-1-((phenylsulfanyl)methyl)propyl)amino)-3-nitrobenzenesulfonamide, | 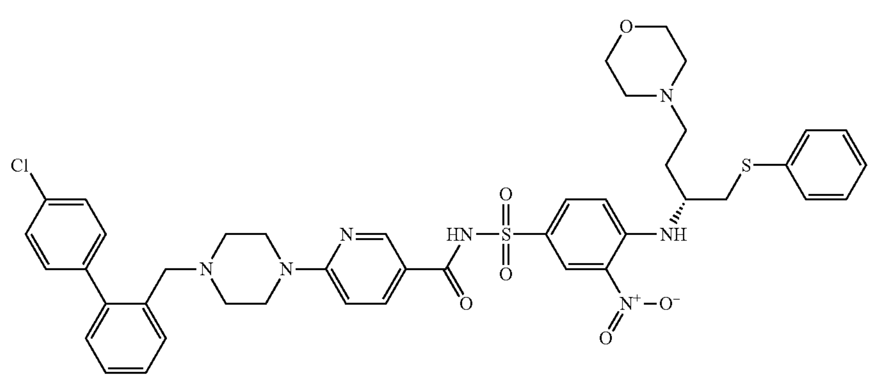 [SMILES: O=C(NS(=O)(=O)c1ccc(N[C@H](CCN2CCOCC2)CSc2ccccc2)c([N+](=O)[O-])c1)c1ccc(N2CCN(Cc3ccccc3-c3ccc(Cl)cc3)CC2)nc1] |

-continued

| Name | Structure |
|---|---|
| N-((6-(4-((4'-chloro(1,1'-biphenyl)-2-yl)methyl)piperazin-1-yl)pyridin-3-yl)carbonyl)-4-(((1R)-3-(dimethylamino)-1-((phenylsulfanyl)methyl)propyl)amino)-3-(trifluoromethyl)benzene-sulfonamide, | 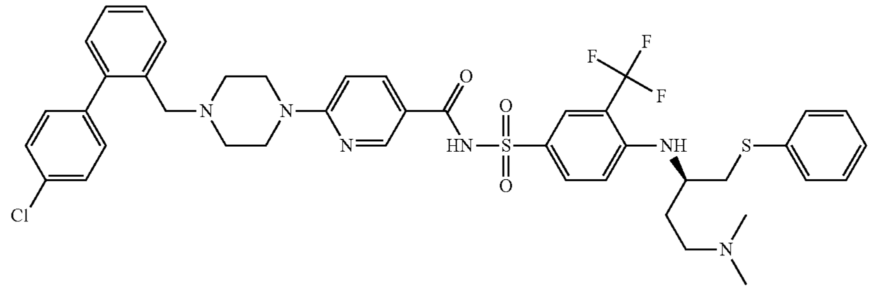 [SMILES: CN(C)CC[C@H](CSc1ccccc1)Nc1ccc(S(=O)(=O)NC(=O)c2ccc(N3CCN(Cc4ccccc4-c4ccc(Cl)cc4)CC3)nc2)cc1C(F)(F)F] |
| N-(4-(4-((4'-chloro(1,1'-biphenyl)-2-yl)methyl)piperidin-1-yl)benzoyl)-4-(((1R)-3-(dimethylamino)-1-((phenylsulfanyl)methyl)propyl)amino)-3-nitrobenzenesulfonamide, | 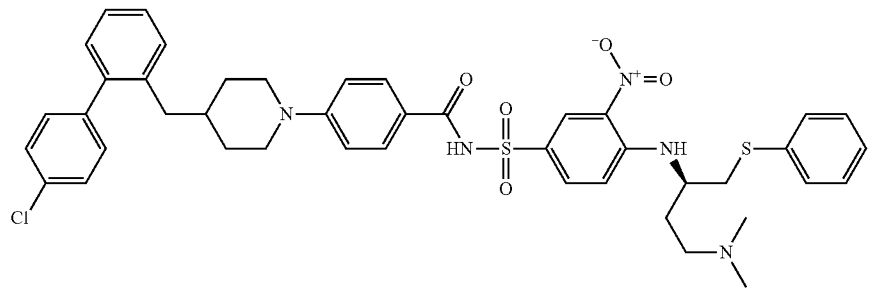 |
| N-(4-(4-((4'-chloro(1,1'-biphenyl)-2-yl)methyl)piperidin-1-yl)benzoyl)-4-(((1R)-3-(morpholin-4-yl)-1-((phenylsulfanyl)methyl)propyl)amino)-3-nitrobenzenesulfonamide, | 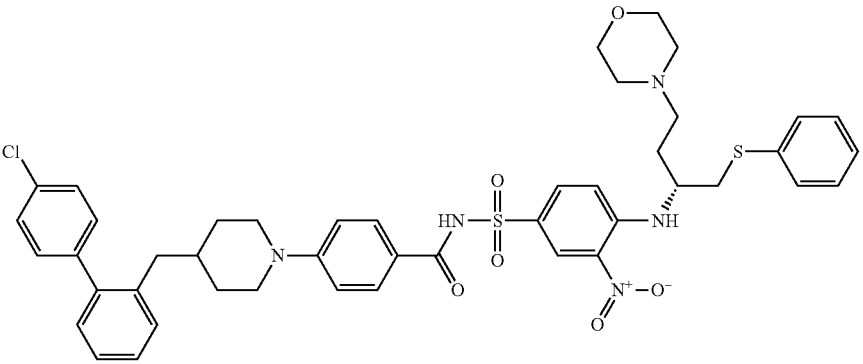 |
| N-((5-(4-((4'-chloro(1,1'-biphenyl)-2-yl)methyl)piperazin-1-yl)pyridin-2-yl)carbonyl)-4-(((1R)-3-(dimethylamino)-1-((phenylsulfanyl)methyl)propyl)amino)-3-nitrobenzenesulfonamide, | 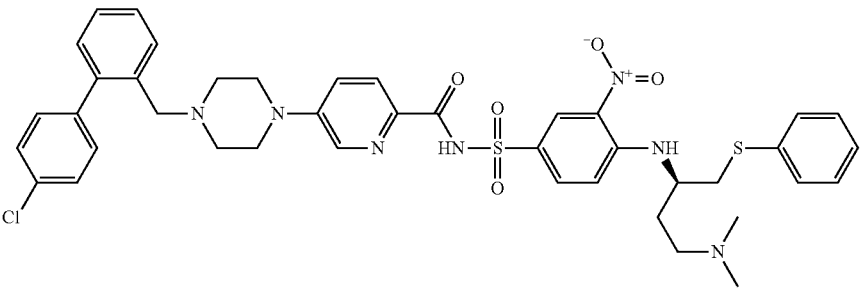 |

| Name | Structure |
|---|---|
| N-((5-(4-((4'-chloro(1,1'-biphenyl)-2-yl)methyl)piperazin-1-yl)pyridin-2-yl)carbonyl)-4-(((1R)-3-(morpholin-4-yl)-1-((phenylsulfanyl)methyl)propyl)amino)-3-nitrobenzenesulfonamide, | 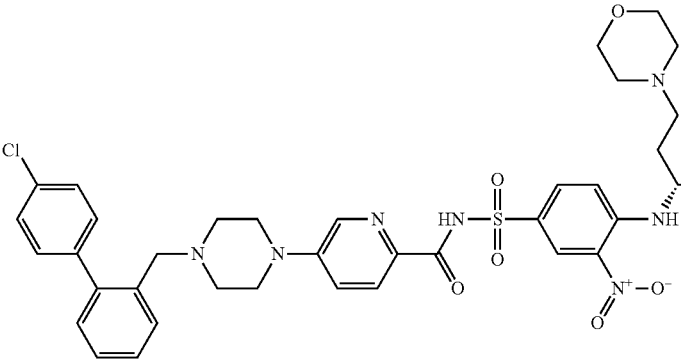 |
| N-(4-(1-((2-(4-chlorophenyl)-5,5-dimethyl-1-cyclohexen-1-yl)methyl)-1,2,3,6-tetrahydropyridin-4-yl)benzoyl)-4-(((1R)-3-dimethylamino)-1-((phenylsulfanyl)methyl)propyl)amino)-3-nitrobenzenesulfonamide, | 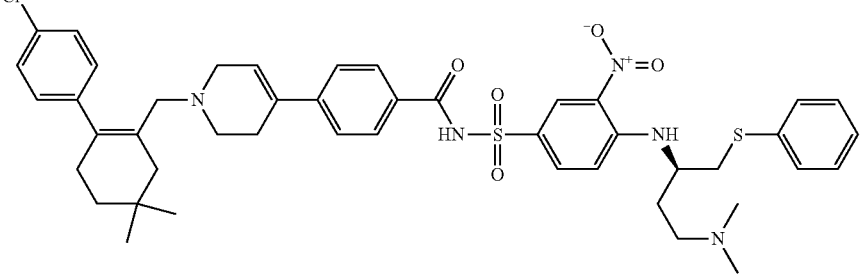 |
| N-(4-(1-((2-(4-chlorophenyl)-1-cyclohexen-1-yl)methyl)-1,2,3,6-tetrahydropyridin-4-yl)benzoyl)-4-(((1R)-3-(dimethylamino)-1-((phenylsulfanyl)methyl)propyl)amino)-3-nitrobenzenesulfonamide, | 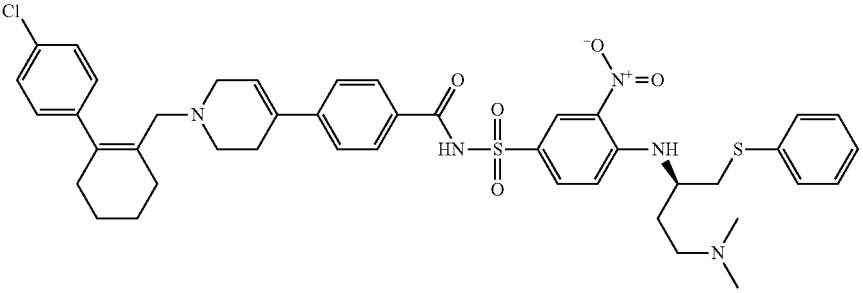 |
| N-(4-(1-((2-(4-chlorophenyl)-1-cyclohexen-1-yl)methyl)-1,2,3,6-tetrahydropyridin-4-yl)benzoyl)-4-(((1R)-3-(morpholin-4-yl)-1-((phenylsulfanyl)methyl)propyl)amino)-3-nitrobenzenesulfonamide, | 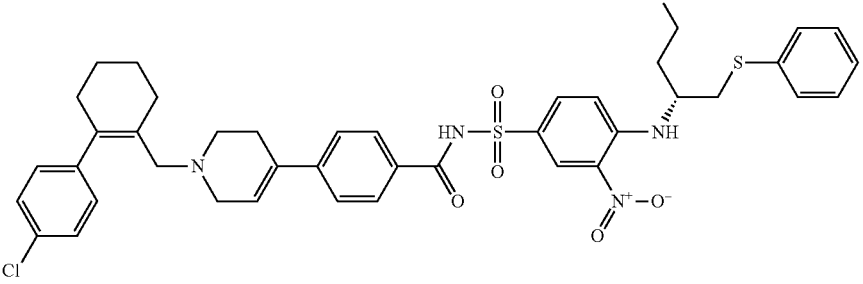 |

| Name | Structure |
|---|---|
| N-(4-(1-((2-(4-chlorophenyl)-5,5-dimethyl-1-cyclohexen-1-yl)methyl)-1,2,3,6-tetrahydropyridin-4-yl)benzoyl)-4-(((1R)-3-(morpholin-4-yl)-1-((phenylsulfanyl)methyl)propyl)amino)-3-nitrobenzenesulfonamide, | 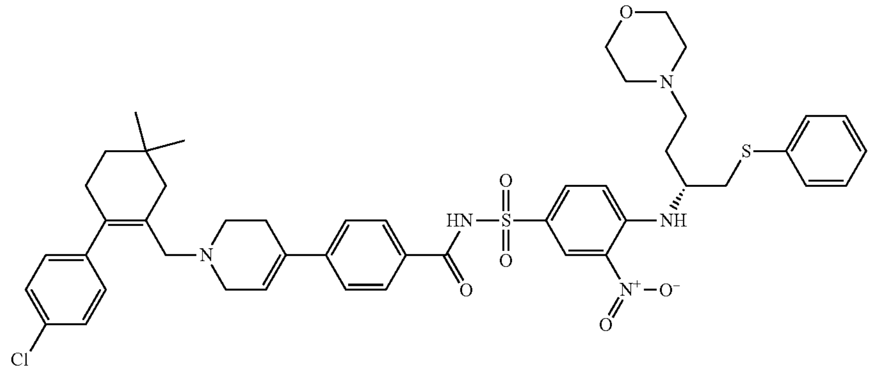 [SMILES: CC1(C)CCC(c2ccc(Cl)cc2)=C(CN2CC=C(c3ccc(C(=O)NS(=O)(=O)c4ccc(N[C@H](CCN5CCOCC5)CSc5ccccc5)c([N+](=O)[O-])c4)cc3)CC2)C1] |
| N-(4-(4-((4'-chloro(1,1'-biphenyl)-2-yl)methyl)-1-cyclohexen-1-yl)benzoyl)-4-(((1R)-3-(dimethylamino)-1-((phenylsulfanyl)methyl)propyl)amino)-3-nitrobenzenesulfonamide, | 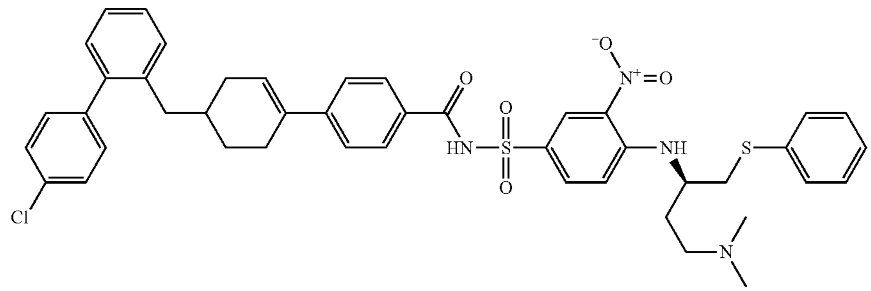 |
| N-(4-(4-((4'-chloro(1,1'-biphenyl)-2-yl)methyl)-1-cyclohexen-1-yl)benzoyl)-4-(((1R)-3-(morpholin-4-yl)-1-((phenylsulfanyl)methyl)propyl)amino)-3-nitrobenzenesulfonamide, | 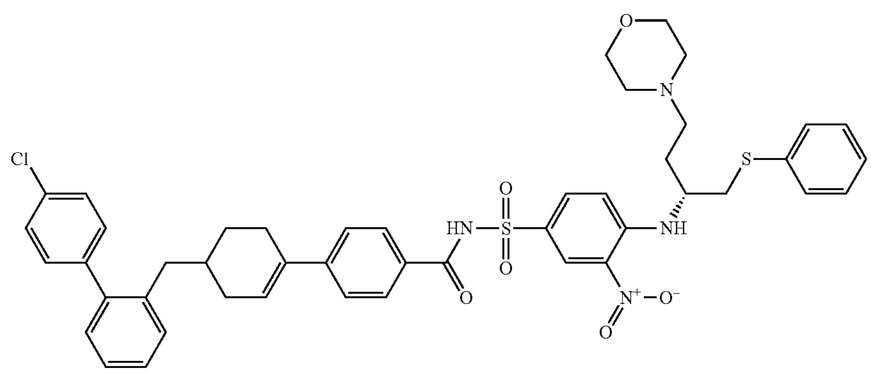 |
| N-(4-((3aR,6aS)-5-((4'-chloro(1,1'-biphenyl)-2-yl)methyl)hexahydropyrrolo[3,4-c]pyrrol-2(1H)-yl)benzoyl)-4-(((1R)-3-(dimethylamino)-1-((phenylsulfanyl)methyl)propyl)amino)-3-nitrobenzenesulfonamide, | 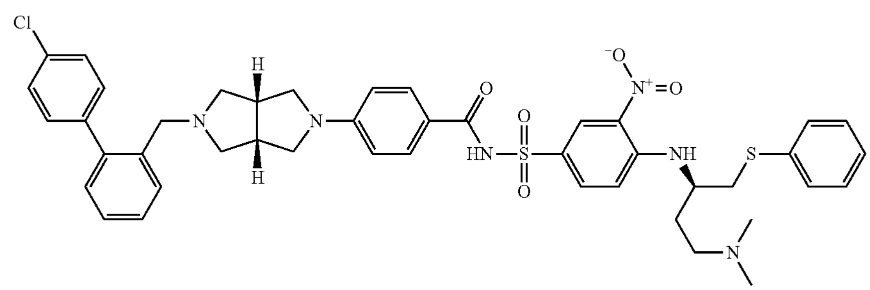 |

-continued

| Name | Structure |
|---|---|
| N-(4-(4-((1,1'-biphenyl)-2-ylmethyl)piperazin-1-yl)benzoyl)-4-(methyl((methyl-4-(trifluoromethoxy)anilino)carbonyl)amino)-3-nitrobenzenesulfonamide, | 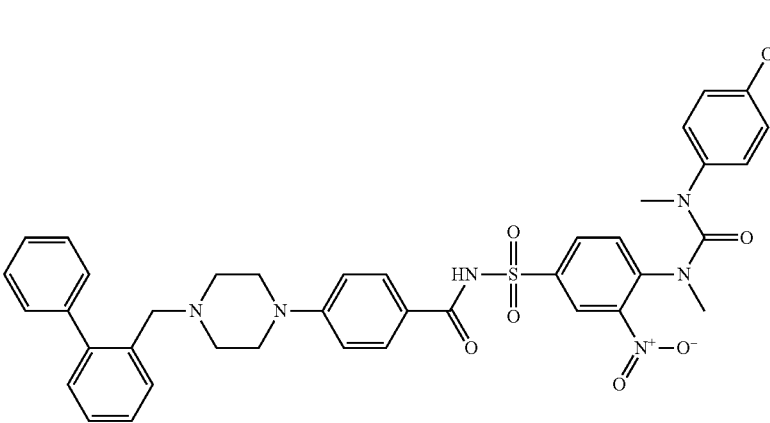 |
| N-(4-(4-((1,1'-biphenyl)-2-ylmethyl)piperazin-1-yl)benzoyl)-4-(((2-dimethylanilino)carbonyl)(methyl)amino)-3-nitrobenzenesulfonamide, | |
| N-(4-(4-((1,1'-biphenyl)-2-ylmethyl)piperazin-1-yl)benzoyl)-4-(((4-methoxy(methyl)anilino)carbonyl)(methyl)amino)-3-nitrobenzenesulfonamide, | 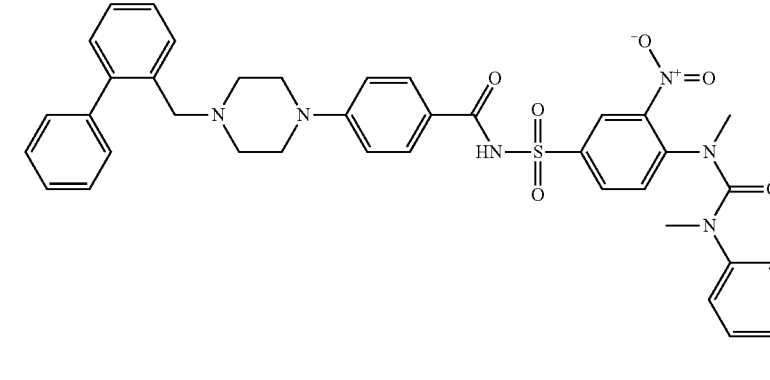 |
| N-(4-(4-((1,1'-biphenyl)-2-ylmethyl)piperazin-1-yl)benzoyl)-4-(((4-dimethylanilino)carbonyl)(methyl)amino)-3-nitrobenzenesulfonamide, | 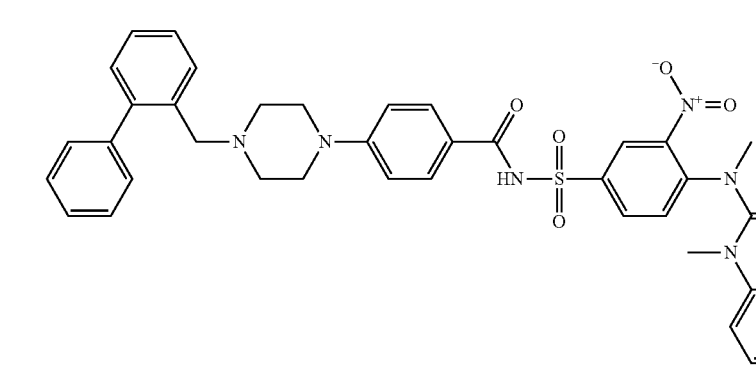 |

| Name | Structure |
|---|---|
| 4-(((benzhydryl(methyl)amino) carbonyl)(methyl)amino)-N-(4-(4-((1,1'-biphenyl)-2-ylmethyl)piperazin-1-yl)benzoyl)-3-nitrobenzenesulfonamide, | 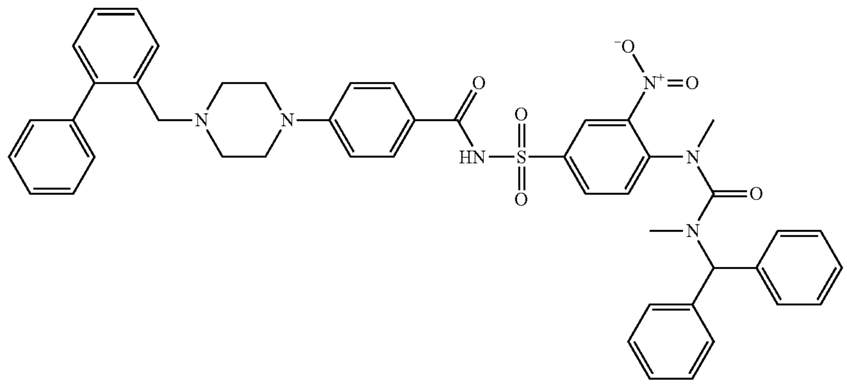 |
| N-(4-(4-((1,1'-biphenyl)-2-ylmethyl)piperazin-1-yl)benzoyl)-4-(methyl((methyl((1S)-1-phenylethyl)amino)carbonyl)amino)-3-nitrobenzenesulfonamide, | 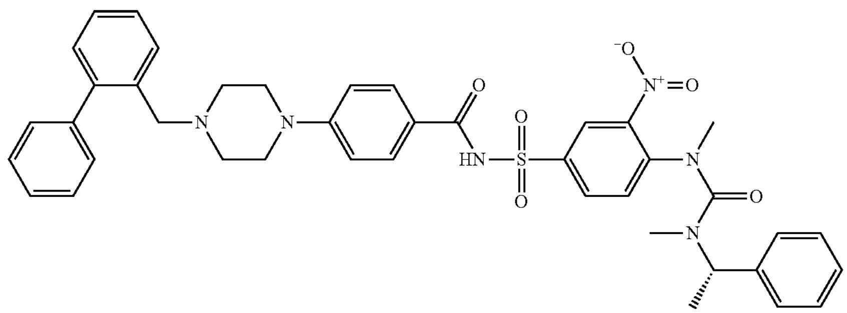 |
| N-(4-(4-((1,1'-biphenyl)-2-ylmethyl)piperazin-1-yl)benzoyl)-4-(methyl((methyl(2-(4-methylpiperazin-1-yl)-1-phenylethyl)amino)carbonyl)amino)-3-nitrobenzenesulfonamide, | 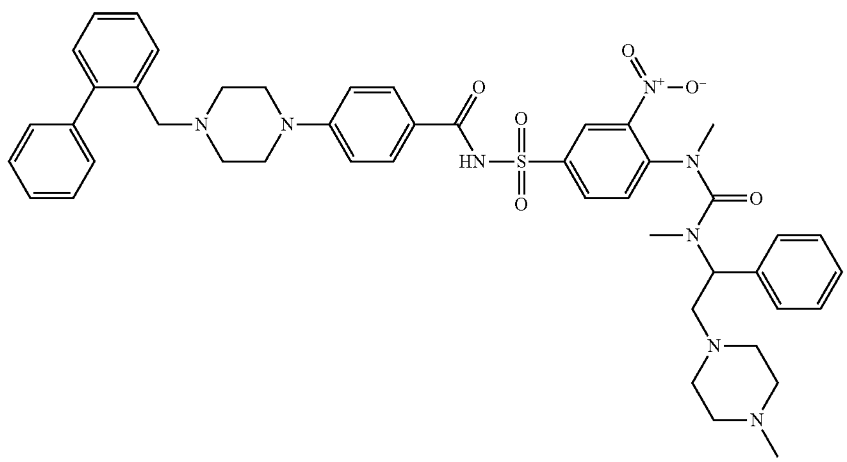 [SMILES: CN1CCN(CC(c2ccccc2)N(C)C(=O)N(C)c2ccc(S(=O)(=O)NC(=O)c3ccc(N4CCN(Cc5ccccc5-c5ccccc5)CC4)cc3)cc2[N+](=O)[O-])CC1] |
| N-(4-(4-((1,1'-biphenyl)-2-ylmethyl)piperazin-1-yl)benzoyl)-4-(methyl((methyl(2-(morpholin-4-yl)-1-phenylethyl)amino)carbonyl)amino)-3-nitrobenzenesulfonamide, | 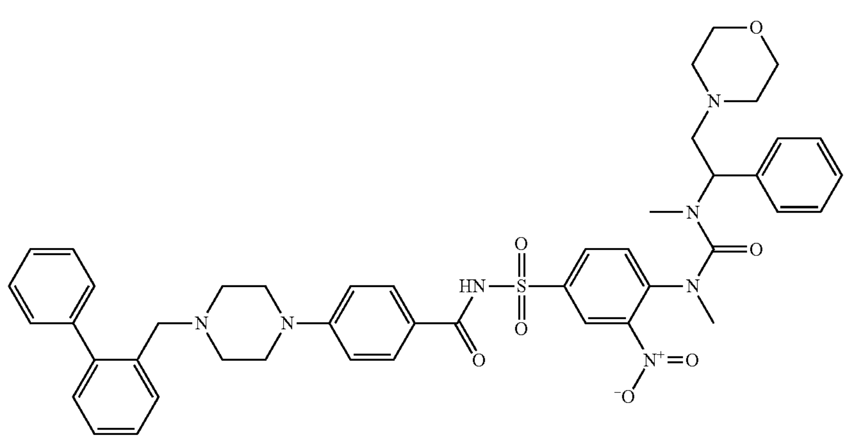 |

-continued

| Name | Structure |
|---|---|
| N-(4-(4-((1,1'-biphenyl)-2-ylmethyl)piperazin-1-yl)benzoyl)-4-((((1,2-diphenylethyl)(methyl)amino)carbonyl)(methyl)amino)-3-nitrobenzenesulfonamide, | 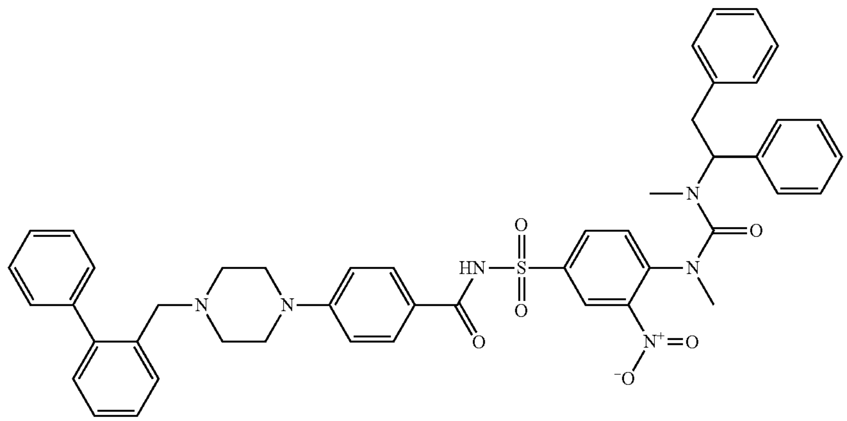 |
| N-(4-(4-((1,1'-biphenyl)-2-ylmethyl)piperazin-1-yl)benzoyl)-4-((((2-(dimethylamino)-1-phenylethyl)(methyl)amino)carbonyl)(methyl)amino)-3-nitrobenzenesulfonamide, | 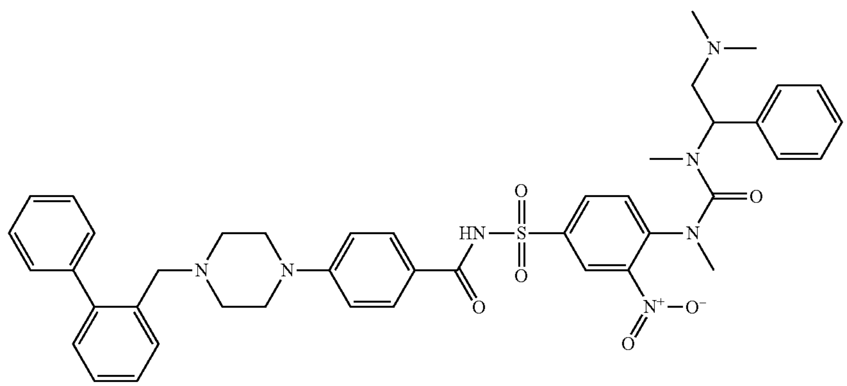 [SMILES: CN(C)CC(c1ccccc1)N(C)C(=O)N(C)c1ccc(S(=O)(=O)NC(=O)c2ccc(N3CCN(Cc4ccccc4-c4ccccc4)CC3)cc2)cc1[N+](=O)[O-]] |
| 3-amino-N-(4-(4-((4'-chloro(1,1'-biphenyl)-2-yl)methyl)piperazin-1-yl)benzoyl)-4-((2-(phenylsulfanyl)ethyl)amino)benzenesulfonamide, | 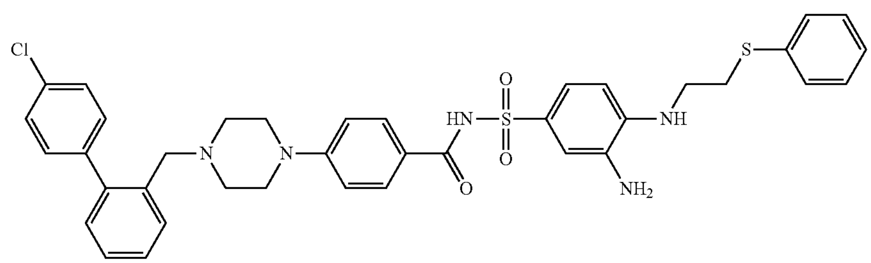 |
| N-(4-(4-((4'-chloro(1,1'-biphenyl)-2-yl)methyl)piperazin-1-yl)benzoyl)-1-(2-(phenylsulfanyl)ethyl)-1H-1,2,3-benzotriazole-5-sulfonamide, | 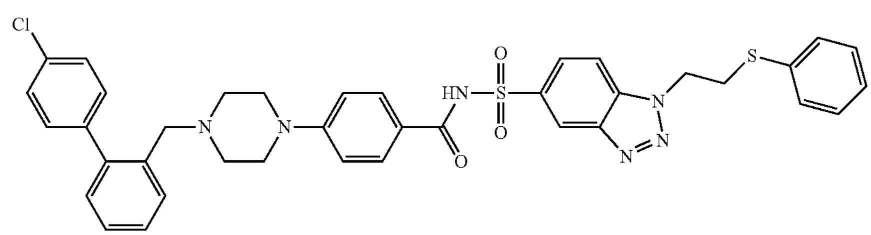 [SMILES: O=C(NS(=O)(=O)c1ccc2c(c1)nnn2CCSc1ccccc1)c1ccc(N2CCN(Cc3ccccc3-c3ccc(Cl)cc3)CC2)cc1] |
| N-(4-(4-((4'-chloro(1,1'-biphenyl)-2-yl)methyl)piperazin-1-yl)benzoyl)-1-(2-(phenylsulfanyl)ethyl)-1H-benzimidazole-5-sulfonamide, | 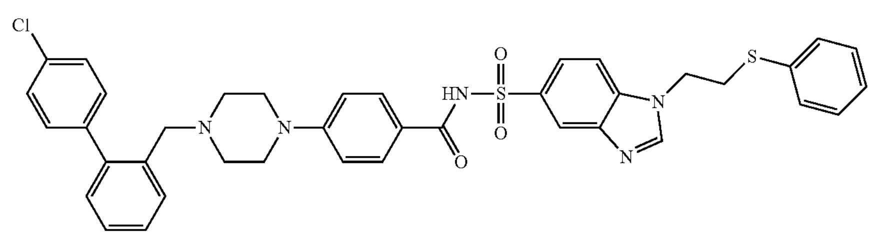 [SMILES: O=C(NS(=O)(=O)c1ccc2c(c1)ncn2CCSc1ccccc1)c1ccc(N2CCN(Cc3ccccc3-c3ccc(Cl)cc3)CC2)cc1] |

| Name | Structure |
|---|---|
| N-(4-(4-((1,1'-biphenyl)-2-ylmethyl)-4-methoxypiperidin-1-yl)benzoyl)-4-((cyclohexylmethyl)amino)-3-nitrobenzenesulfonamide, | 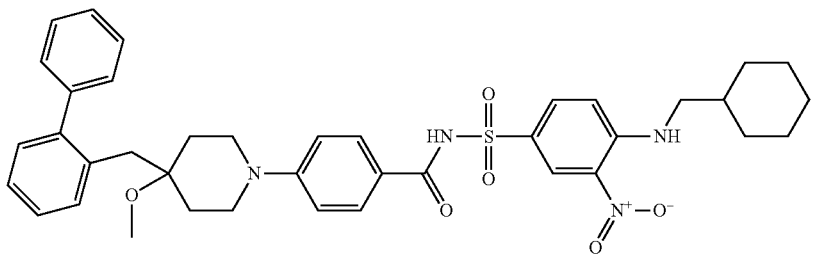 [SMILES: COC1(Cc2ccccc2-c2ccccc2)CCN(c2ccc(C(=O)NS(=O)(=O)c3ccc(NCC4CCCCC4)c([N+](=O)[O-])c3)cc2)CC1] |
| N-(4-(4-((1,1'-biphenyl)-2-ylmethyl)-4-methoxypiperidin-1-yl)benzoyl)-4-(cyclohexylamino)-3-nitrobenzenesulfonamide, | 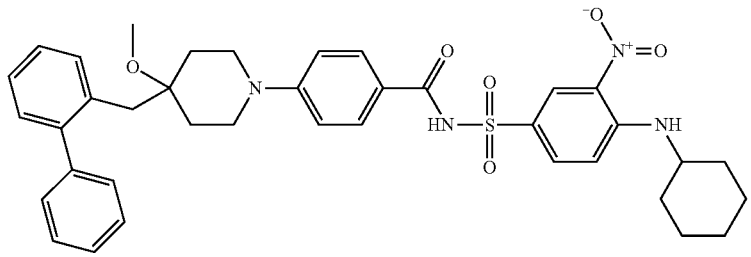 |
| N-(4-(4-((1,1'-biphenyl)-2-ylmethyl)-4-methoxypiperidin-1-l)benzoyl)-4-((1,1-dimethyl-2-(phenylsulfanyl)ethyl)amino)-3-nitrobenzenesulfonamide, | 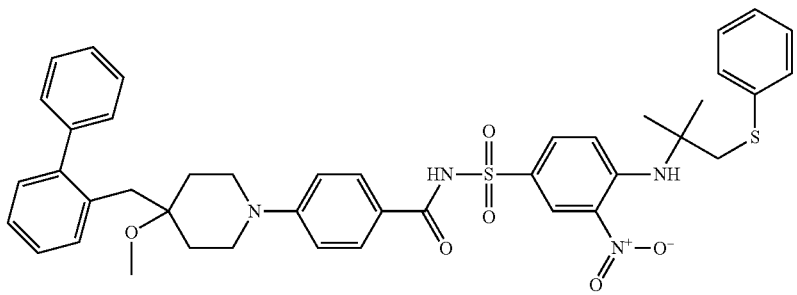 [SMILES: COC1(Cc2ccccc2-c2ccccc2)CCN(c2ccc(C(=O)NS(=O)(=O)c3ccc(NC(C)(C)CSc4ccccc4)c([N+](=O)[O-])c3)cc2)CC1] |
| N-(4-(4-((1,1'-biphenyl)-2-ylmethyl)piperazin-1-yl)benzoyl)-3-nitro-4-((1-((phenylsulfanyl)methyl)cyclopentyl)amino)benzenesulfonamide, | 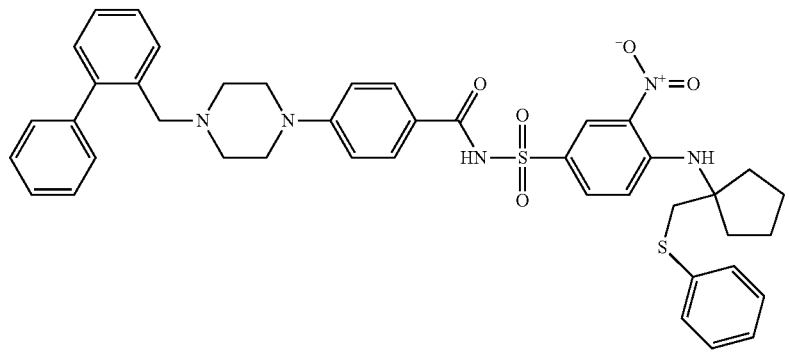 |
| N-(4-(4-((1,1'-biphenyl)-2-ylmethyl)-4-methoxypiperidin-1-yl)benzoyl)-3-nitro-4-((1-((phenylsulfanyl)methyl)cyclopentyl)amino)benzenesulfonamide, | 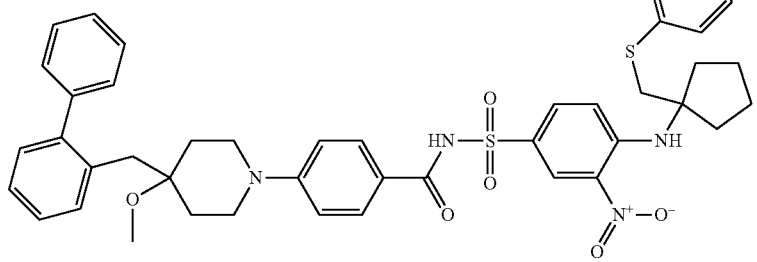 |

| Name | Structure |
|---|---|
| N-(4-(4-((4'-chloro(1,1'-biphenyl)-2-yl)methyl)piperazin-1-yl)benzoyl)-3-nitro-4-((1-((phenylsulfanyl)methyl)cyclopentyl)amino)benzenesulfonamide, | 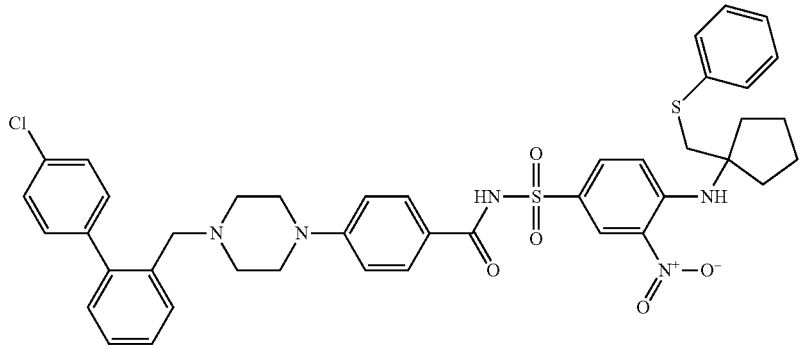 [SMILES: O=C(NS(=O)(=O)c1ccc(NC2(CSc3ccccc3)CCCC2)c([N+](=O)[O-])c1)c1ccc(N2CCN(Cc3ccccc3-c3ccc(Cl)cc3)CC2)cc1] |
| N-(4-(4-((4'-chloro(1,1'-biphenyl)-2-yl)methyl)piperazin-1-yl)benzoyl)-3-nitro-4-(((1S)-1-((phenylsulfanyl)methyl)propyl)amino)benzenesulfonamide, | 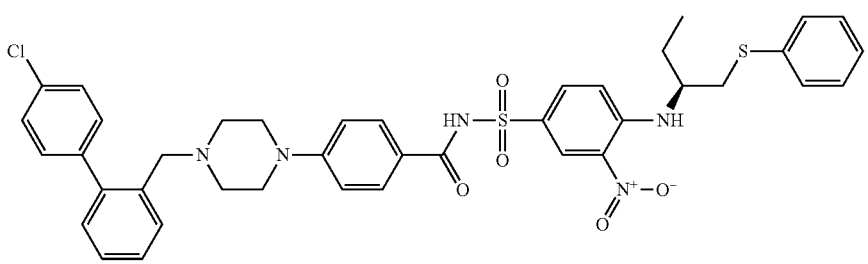 |
| N-(4-(4-((1,1'-biphenyl)-2-ylmethyl)-4-methoxypiperidin-1-yl)benzoyl)-3-nitro-4-(((1S)-1-((phenylsulfanyl)methyl)propyl)amino)benzenesulfonamide, | 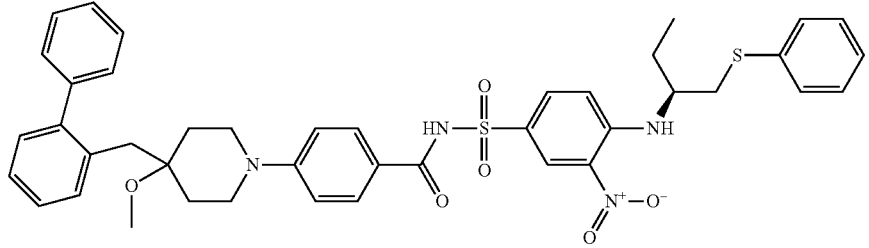 [SMILES: CC[C@@H](CSc1ccccc1)Nc1ccc(S(=O)(=O)NC(=O)c2ccc(N3CCC(Cc4ccccc4-c4ccccc4)(OC)CC3)cc2)cc1[N+](=O)[O-]] |
| N-(4-(4-((4'-chloro(1,1'-biphenyl)-2-yl)methyl)piperazin-1-yl)benzoyl)-4-(((1R)-3-(morpholin-4-yl)-1-((phenylsulfanyl)methyl)propyl)amino)-3-nitrobenzenesulfonamide, | 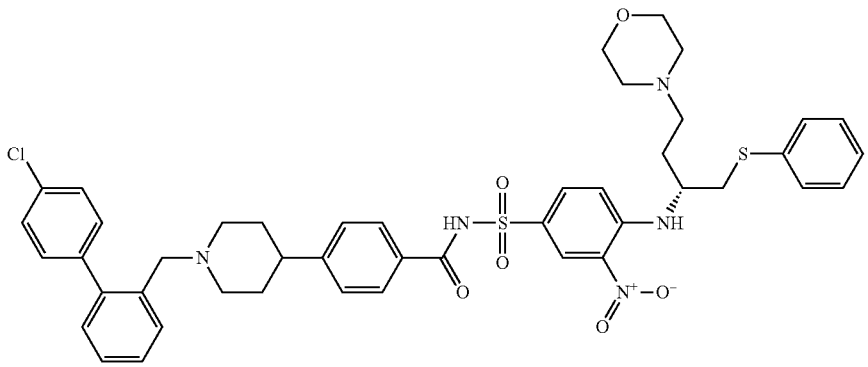 |
| N-(4-(4-((4'-chloro(1,1'-biphenyl)-2-yl)methyl)piperazin-1-yl)benzoyl)-4-(((1S)-3-methyl-1-((phenylsulfanyl)methyl)butyl)amino)-3-nitrobenzenesulfonamide, | 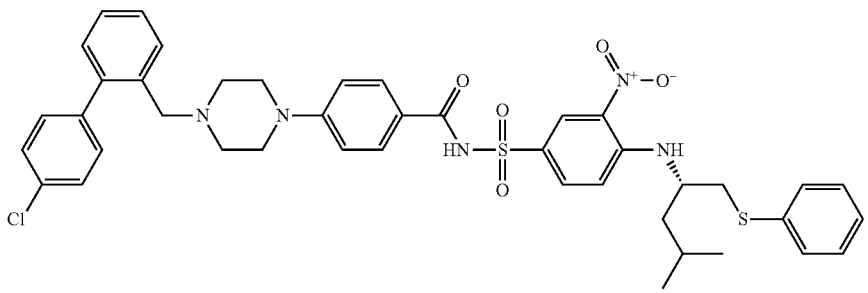 [SMILES: CC(C)C[C@@H](CSc1ccccc1)Nc1ccc(S(=O)(=O)NC(=O)c2ccc(N3CCN(Cc4ccccc4-c4ccc(Cl)cc4)CC3)cc2)cc1[N+](=O)[O-]] |

| Name | Structure |
|---|---|
| N-(4-(4-((1,1'-biphenyl)-2-ylmethyl)-4-methoxypiperidin-1-yl)benzoyl)-4-(((1S)-3-methyl-1-((phenylsulfanyl)methyl)butyl)amino)-3-nitrobenzenesulfonamide, | 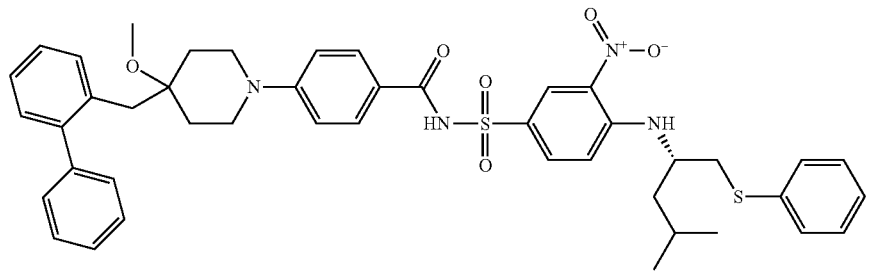 [SMILES: COC1(Cc2ccccc2-c2ccccc2)CCN(c2ccc(C(=O)NS(=O)(=O)c3ccc(N[C@H](CSc4ccccc4)CC(C)C)c([N+](=O)[O-])c3)cc2)CC1] |
| N-(4-(4-((4'-chloro(1,1'-biphenyl)-2-yl)methyl)piperazin-1-yl)benzoyl)-3-nitro-4-((1-((phenylsulfanyl)methyl)cyclopropyl)amino)benzenesulfonamide, | 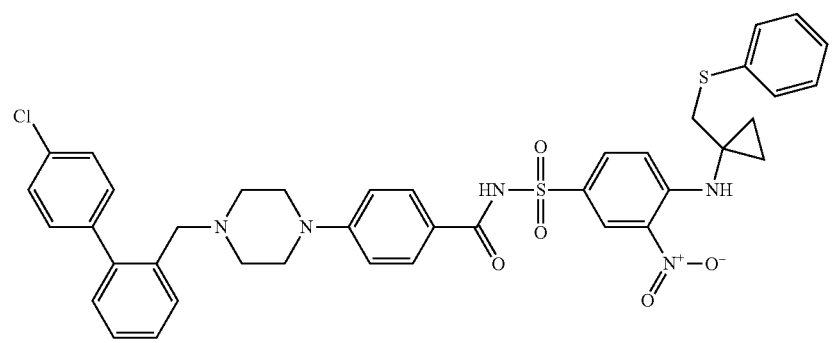 [SMILES: O=C(NS(=O)(=O)c1ccc(NC2(CSc3ccccc3)CC2)c([N+](=O)[O-])c1)c1ccc(N2CCN(Cc3ccccc3-c3ccc(Cl)cc3)CC2)cc1] |
| N-(4-(4-((4'-chloro(1,1'-biphenyl)-2-yl)methyl)piperazin-1-yl)benzoyl)-3-nitro-4-((1-((phenylsulfanyl)methyl)cyclohexyl)amino)benzenesulfonamide, | 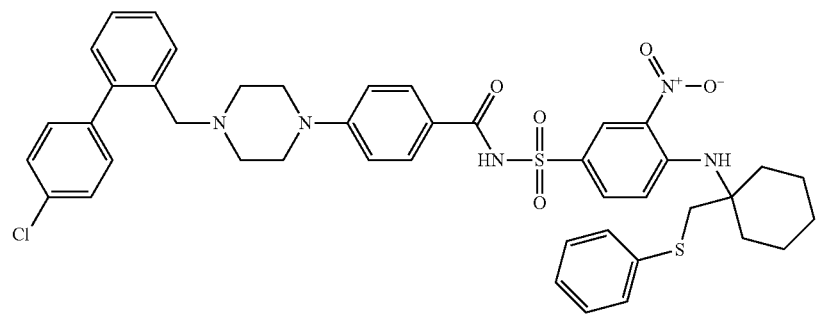 [SMILES: O=C(NS(=O)(=O)c1ccc(NC2(CSc3ccccc3)CCCCC2)c([N+](=O)[O-])c1)c1ccc(N2CCN(Cc3ccccc3-c3ccc(Cl)cc3)CC2)cc1] |
| N-(4-(4-((4'-chloro(1,1'-biphenyl)-2-yl)methyl)piperazin-1-yl)benzoyl)-4-(((1R)-1-methyl-2-(phenylsulfanyl)ethyl)amino)-3-nitrobenzenesulfonamide, | 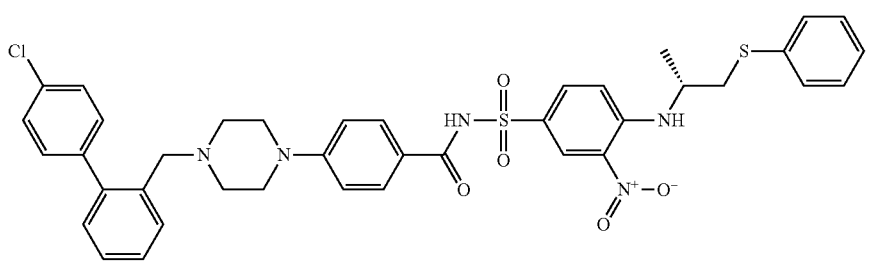 [SMILES: C[C@H](CSc1ccccc1)Nc1ccc(S(=O)(=O)NC(=O)c2ccc(N3CCN(Cc4ccccc4-c4ccc(Cl)cc4)CC3)cc2)cc1[N+](=O)[O-]] |
| N-(4-(4-((1,1'-biphenyl)-2-ylmethyl)piperazin-1-yl)benzoyl)-4-(((1S)-1-methyl-2-(phenylsulfanyl)ethyl)amino)-3-nitrobenzenesulfonamide, | 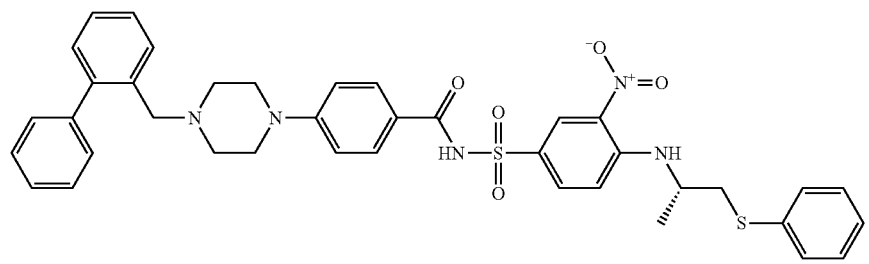 |

-continued

| Name | Structure |
|---|---|
| N-(4-(4-((1,1'-biphenyl)-2-ylmethyl)piperazin-1-yl)benzoyl)-3-nitro-4-(((1R,2S)-2-(phenylsulfanyl)cyclohexyl)amino)benzenesulfonamide, | 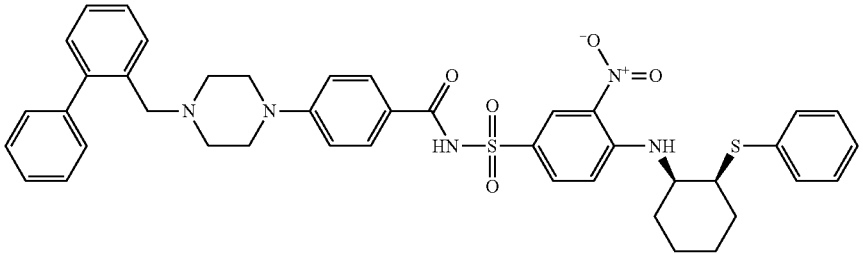 |
| N-(4-(4-((4,-chloro(1,1'-biphenyl)-2-yl)methyl)piperazin-1-yl)benzoyl)-4-(((1R)-3-(dimethylamino)-1-((phenylsulfanyl)methyl)propyl)amino)-3-(trifluoromethyl)benzenesulfonamide, | 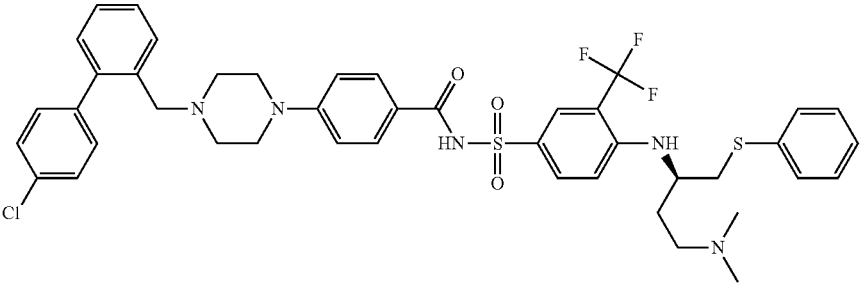 |
| 4-(((1R)-5-amino-1-((phenyl sulfanyl)methyl)pentyl)amino)-N-(4-(4-((4'-chloro(1,1'-biphenyl)-2-yl)methyl)piperazin-1-yl)benzoyl)-3-nitrobenzenesulfonamide, | 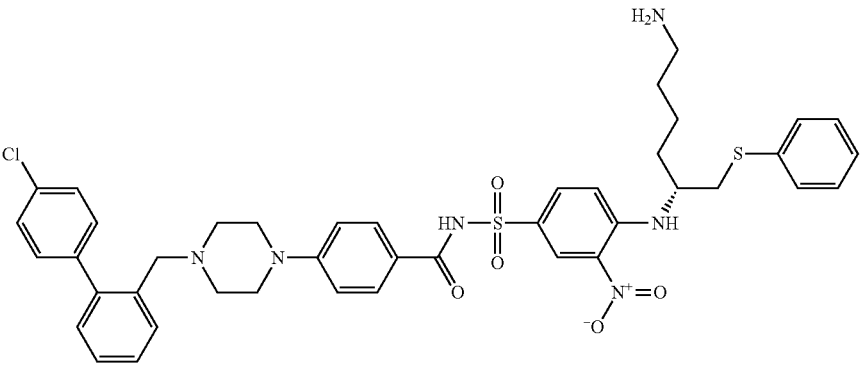 |
| N-(4-(4-((1,1'-biphenyl)-2-ylmethyl)piperazin-1-yl)benzoyl)-3-nitro-4-(((1S)-2-(phenylsulfanyl)-1-(pyridin-3-ylmethyl)ethyl)amino)benzenesulfonamide, | 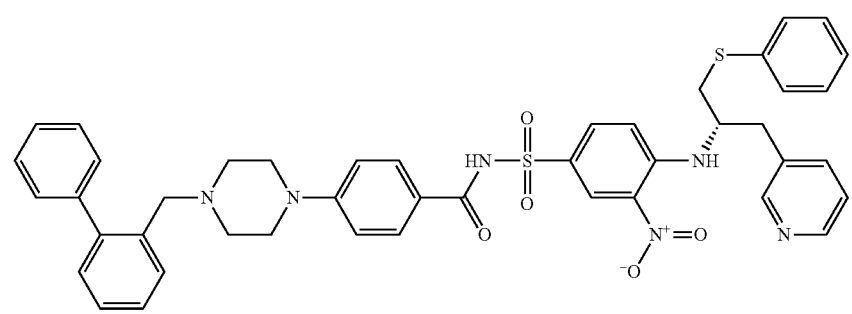 |
| N-(4-(4-((1,1'-biphenyl)-2-ylmethyl)-4-methoxypiperidin-1-yl)benzoyl)-3-nitro-4-(((1S)-2-(phenylsulfanyl)-1-(pyridin-3-ylmethyl)ethyl)amino)benzenesulfonamide, | 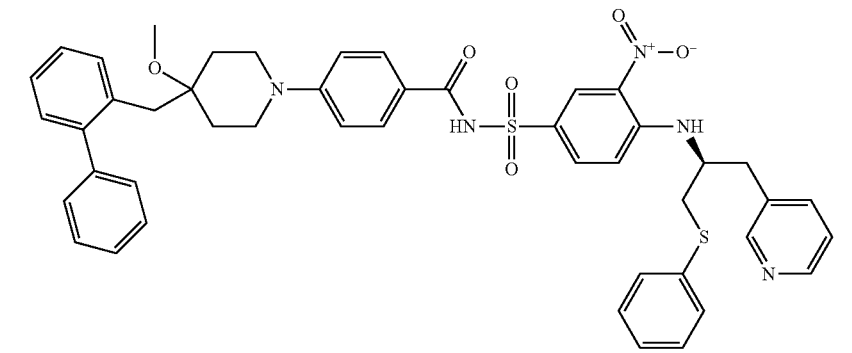 [SMILES: COC1(Cc2ccccc2-c2ccccc2)CCN(c2ccc(C(=O)NS(=O)(=O)c3ccc(N[C@H](CSc4ccccc4)Cc4cccnc4)c([N+](=O)[O-])c3)cc2)CC1] |

| Name | Structure |
|---|---|
| N-(4-(4-((1,1'-biphenyl)-2-ylmethyl)piperazin-1-yl)benzoyl)-3-nitro-4-(((1S,2R)-2-(phenylsulfanyl)cyclohexyl)amino)benzenesulfonamide, | 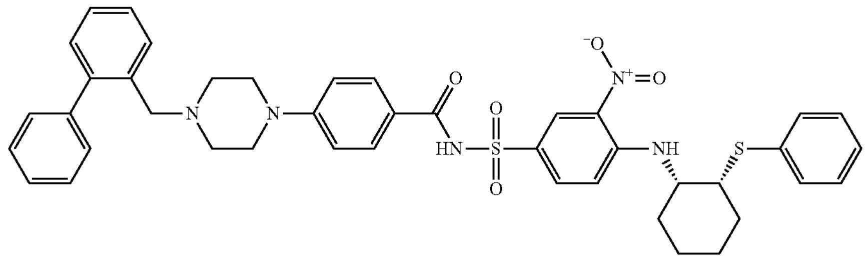 |
| N-(4-(4-((1,1'-biphenyl)-2-ylmethylpiperazin-1-yl)benzoyl)-4-((1-(((2-methyl-3-furyl)sulfanyl)methyl)cyclopentyl)amino)-3-nitrobenzenesulfonamide, | 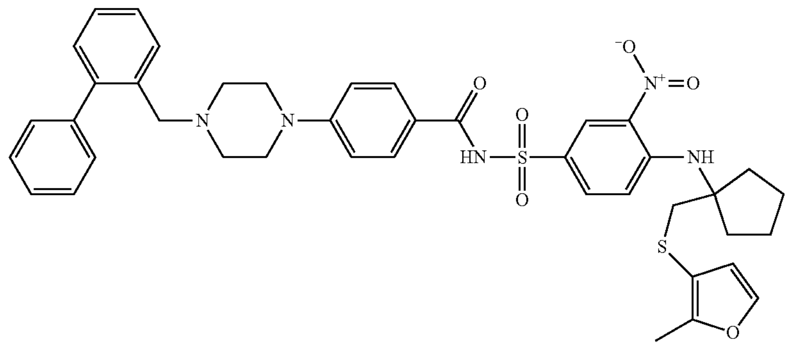 |
| N-(4-(4-((4'-chloro(1,1'-biphenyl)-2-yl)methyl)piperazin-1-yl)benzoyl-4-((1-(((2-methyl-3-furyl)sulfanyl)methyl)cyclopentyl)amino)-3-nitrobenzenesulfonamide, | 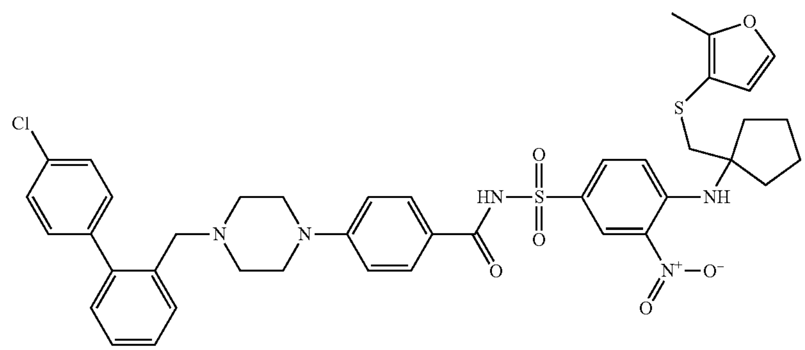 [SMILES: Cc1occc1SCC1(Nc2ccc(S(=O)(=O)NC(=O)c3ccc(N4CCN(Cc5ccccc5-c5ccc(Cl)cc5)CC4)cc3)cc2[N+](=O)[O-])CCCC1] |
| N-(4-(4-((4'-chloro(1,1'-biphenyl)-2-yl)methyl)piperazin-1-yl)benzoyl)-3-nitro-4-(((1S)-2-(phenylsulfanyl)-1-(pyridin-3-ylmethyl)ethyl)amino)benzenesulfonamide, | |
| N-(4-(4-((2-(4-chlorophenyl)-3-pyridin-3-yl)methyl)piperazin-1-yl)benzoyl)-4-(((1R)-1-(dimethylamino)-1-((phenylsulfanyl)methyl)propyl)amino)-3-nitrobenzenesulfonamide, | |

| Name | Structure |
|---|---|
| N-(4-(4-((2-(4-chlorophenyl)pyridin-3-yl)methyl)piperazin-1-yl)benzoyl)-3-nitro-4-((2-(phenylsulfanyl)ethyl)amino)benzenesulfonamide, | 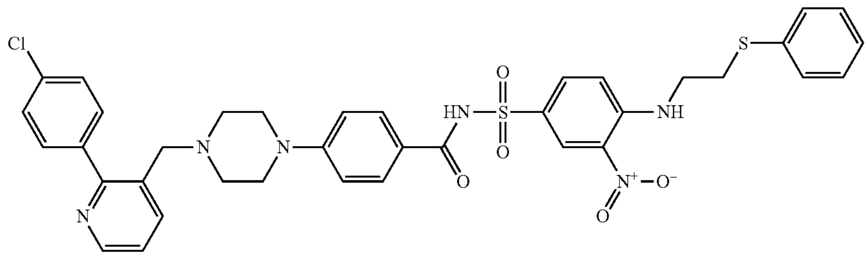 |
| N-(4-(4-((2-(4-chlorophenyl)pyridin-3-yl)methyl)piperazin-1-yl)benzoyl)-4-(((1R)-3-(morpholin-4-yl)-1-((phenylsulfanyl)methyl)propyl)aimno)-3-nitrobenzenesulfonamide, | 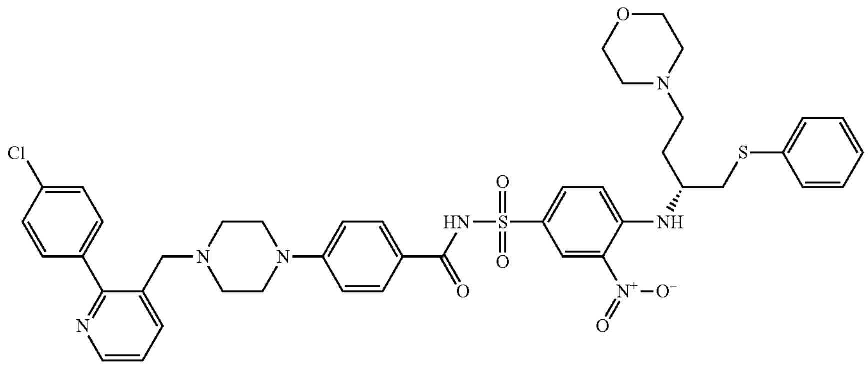 |
| 3-nitro-N-(4-(4-((2-phenylpyridin-3-yl)methyl)piperazin-1-yl)benzoyl)-4-((2-(phenylsulfanyl)ethyl)amino)benzenesulfonamide, | 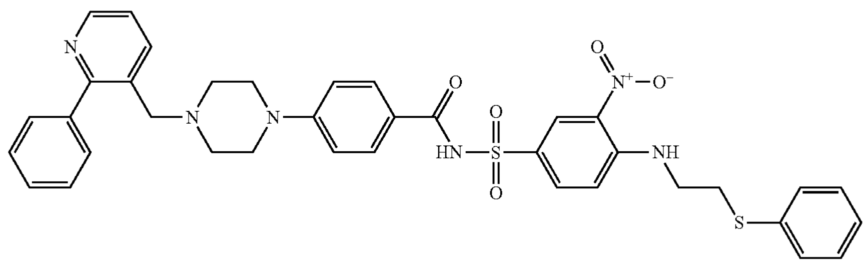 |
| 4-(((1R)-3-(morpholin-4-yl)-1-((phenylsulfanyl)methyl)propyl)amino)-3-nitro-N-(4-(4-((2-phenylpyridin-3-yl)methyl)piperazin-1-yl)benzoyl)benzenesulfonamide, | 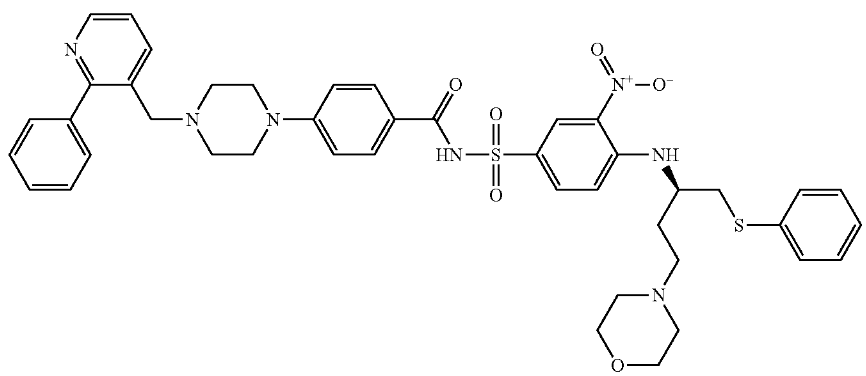 [SMILES: O=C(NS(=O)(=O)c1ccc(N[C@H](CCN2CCOCC2)CSc2ccccc2)c([N+](=O)[O-])c1)c1ccc(N2CCN(Cc3cccnc3-c3ccccc3)CC2)cc1] |
| 4-(((1R)-3-(dimethylamino)-1-((phenylsulfanyl)methyl)propyl)amino)-3-nitro-N-(4-(4-((2-phenylpyridin-3-yl)methyl)piperazin-1-yl)benzoyl)benzenesulfonamide, | 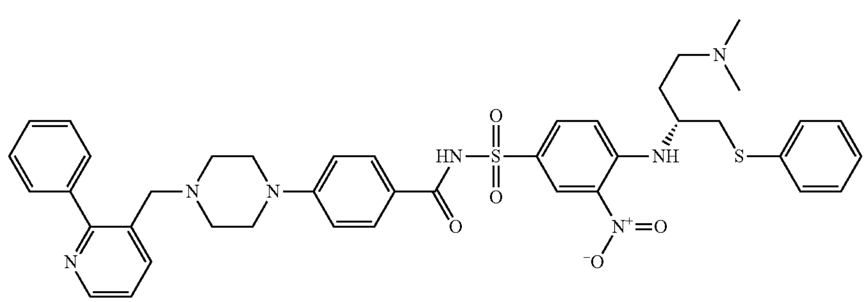 |

| Name | Structure |
|---|---|
| 4-(((1R)-3-(dimethylamino)-1-((phenylsulfanyl)methyl)propyl)amino)-N-(4-(4-((2-(4-(methylsulfanyl)phenyl)pyridin-3-yl)methyl)piperazin-1-yl)benzoyl)-3-nitrobenzenesulfonamide, | 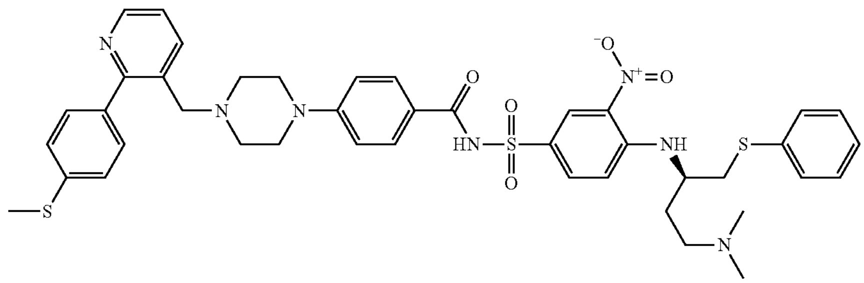 |
| 4-(((1R)-3-(dimethylamino)-1-((phenylsulfanyl)methyl)propyl)amino)-N-(4-(4-((2-(4-methoxyphenyl)pyridin-3-yl)methyl)piperazin-1-yl)benzoyl)-3-nitrobeiizenesulfonamide, | 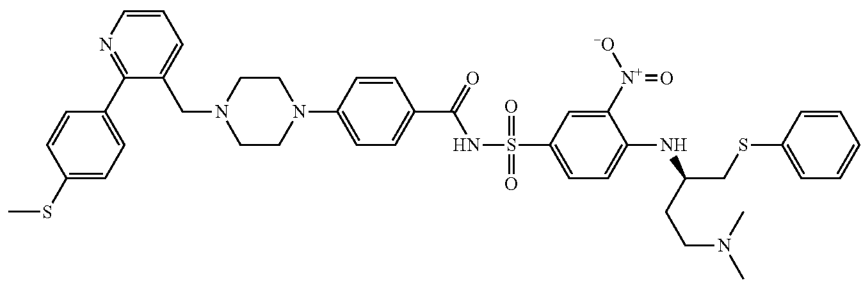 |
| N-(4-(4-((2-(4-(dimethylamino)phenyl)pyridin-3-yl)methyl)piperazin-1-yl)benzoyl)-4-(((1R)-3-(dimethylamino)-1-((phenylsulfanyl)methyl)propyl)amino)-3-nitrobenzenesulfonamide, | 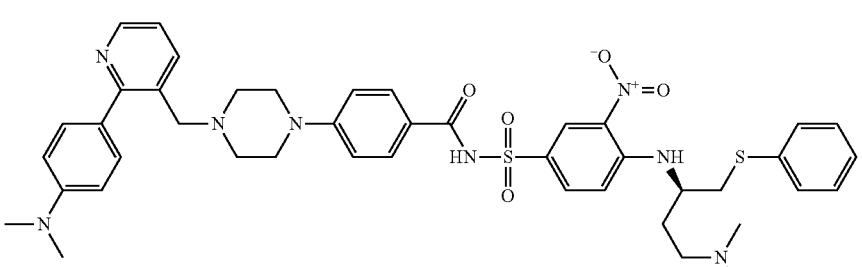 |
| 4-(((1R)-3-(dimethylamino)-1-((phenylsulfanyl)methyl)propyl)amino)-N-(4-(4-((2-(4-fluorophenyl)pyridin-3-yl)methyl)piperazin-1-yl)benzoyl)-3-nitrobenzenesulfonamide, | 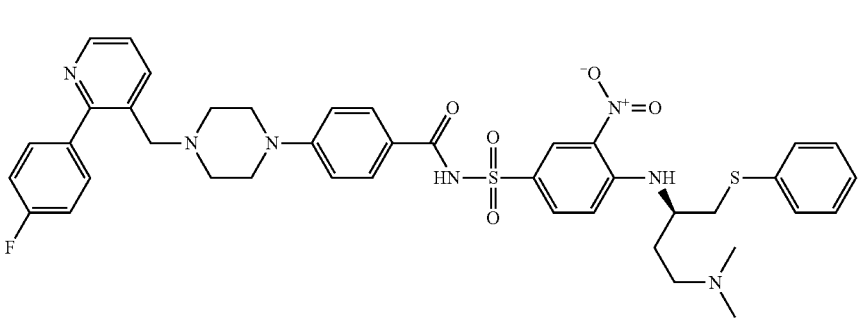 |
| 4-(((1R)-3-(dimethylamino)-1-((phenylsulfanyl)methyl)propyl)amino)-N-(4-(4-((2-(4-(methylsulfonyl)phenyl)pyridin-3-yl)methyl)piperazin-1-yl)benzoyl)-3-nitrobenzenesulfonamide, | 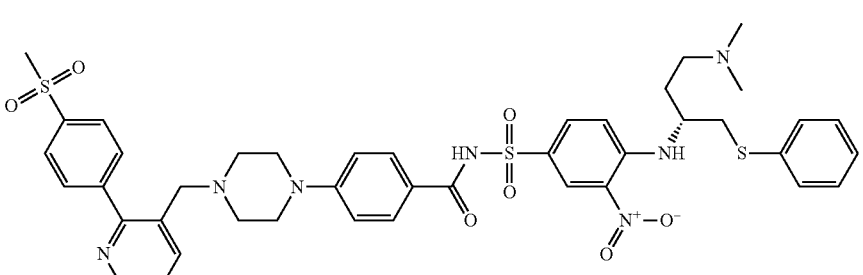 |

-continued

| Name | Structure |
|---|---|
| N-(4-(4-((4'-chloro(1,1'-biphenyl)-2-yl)methyl)piperazin-1-yl)benzoyl)-3-nitro-4-((2-(pyridin-4-ylsulfanyl)ethyl)amino)benzenesulfonamide, | 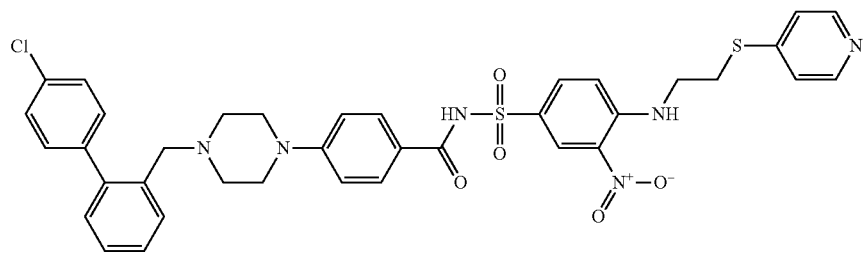 |
| 4-(((1R)-3-(dimethylamino)-1-((phenylsulfanyl)methyl)propyl)amino)-N-(4-(4-((4'-(methylsulfonyl)(1,1'-biphenyl)-2-yl)methyl)piperazin-1-yl)benzoyl)-3-nitrobenzenesulfonamide, | 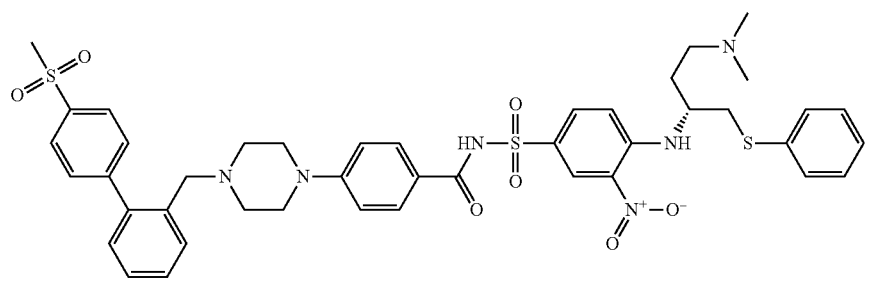 [SMILES: CN(C)CC[C@H](CSc1ccccc1)Nc1ccc(S(=O)(=O)NC(=O)c2ccc(N3CCN(Cc4ccccc4-c4ccc(S(C)(=O)=O)cc4)CC3)cc2)cc1[N+](=O)[O-]] |
| N-(4-(4-((4'-(methylsulfonyl)(1,1'-biphenyl)-2-yl)methyl)piperazin-1-yl)benzoyl)-4-(((1R)-3-(morpholin-4-yl)-1-((phenylsulfanyl)methyl)propyl)amino)-3-nitrobenzenesulfonamide, | 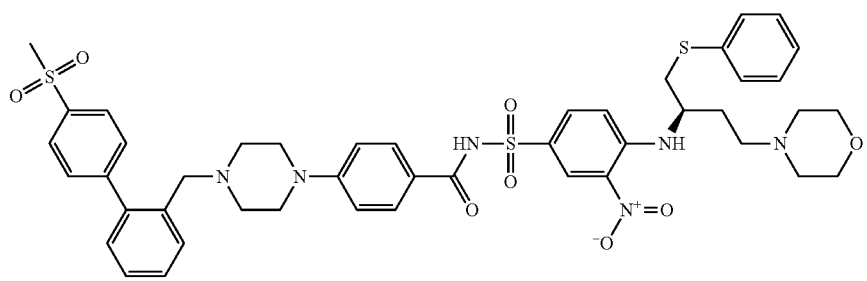 |
| N-(4-(4-((4'-chloro(1,1'-biphenyl)-2-yl)methyl)piperazin-1-yl)benzoyl)-4-(((1R)-3-(morpholin-4-yl)-1-((phenylsulfonyl)methyl)propyl)amino)-3-nitrobenzenesulfonamide, | 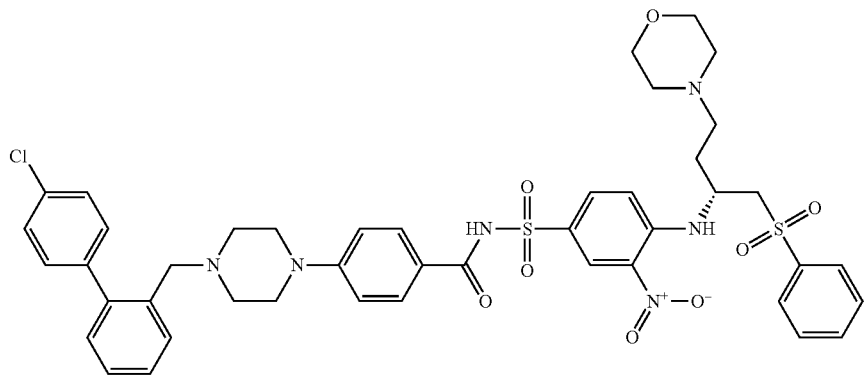 [SMILES: O=C(NS(=O)(=O)c1ccc(N[C@H](CCN2CCOCC2)CS(=O)(=O)c2ccccc2)c([N+](=O)[O-])c1)c1ccc(N2CCN(Cc3ccccc3-c3ccc(Cl)cc3)CC2)cc1] |
| N-(4-(4-((4'-(dimethylamino)(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide, | 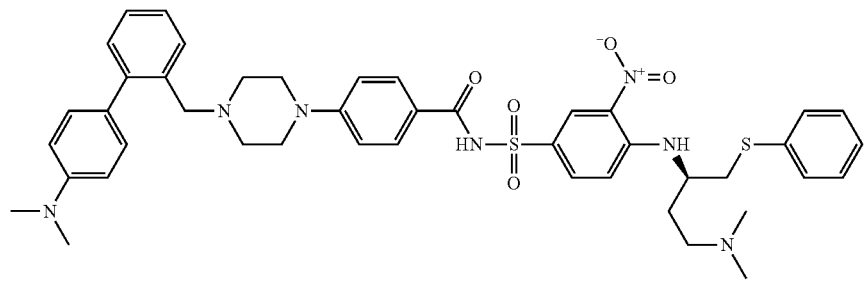 |

-continued

| Name | Structure |
|---|---|
| (3R)-3-(4-(((4-(4-((4'-chloro(1,1'-biphenyl)-2-yl)methyl)piperazin-1-yl)benzoyl)amino)sulfonyl)-2-nitroamino)-N,N-dimethyl-4-(phenylsulfonyl)butanamide, | 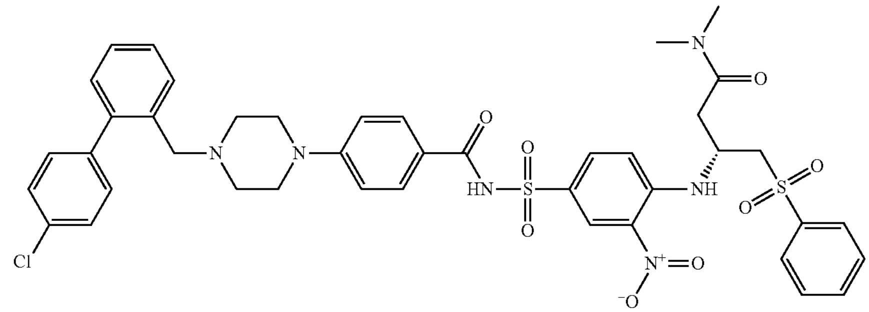 |
| N-(4-(4-((4'-chloro(1,1'-biphenyl)-2-yl)methyl)piperazin-1-yl)benzoyl)-3-nitro-4-(((3S,4R)-(phenylsulfanyl)pyrrolidin-4-yl)amino)benzenesulfonamide, | 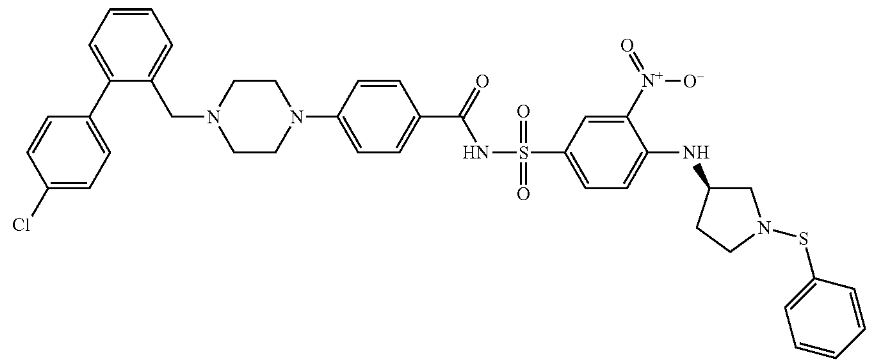 [SMILES: O=C(NS(=O)(=O)c1ccc(N[C@@H]2CCN(Sc3ccccc3)C2)c([N+](=O)[O-])c1)c1ccc(N2CCN(Cc3ccccc3-c3ccc(Cl)cc3)CC2)cc1] |
| N-(4-(4-((4'-chloro(1,1'-biphenyl)-2-yl)methyl)piperazin-1-yl)benzoyl)-3-nitro-4-(((1R)-1-((phenylsulfanyl)methyl)-3-(pyridin-4-ylsulfanyl)propyl)amino)benzenesulfonamide, | |
| N-(4-(4-((3-(4-chlorophenyl)pyridin-4-yl)methyl)piperazin-1-yl)benzoyl)-4-(((1R)-3-(dimethylamino)-1-((phenylsulfanyl)methyl)propyl)amino)-3-nitrobenzenesulfonamide, | 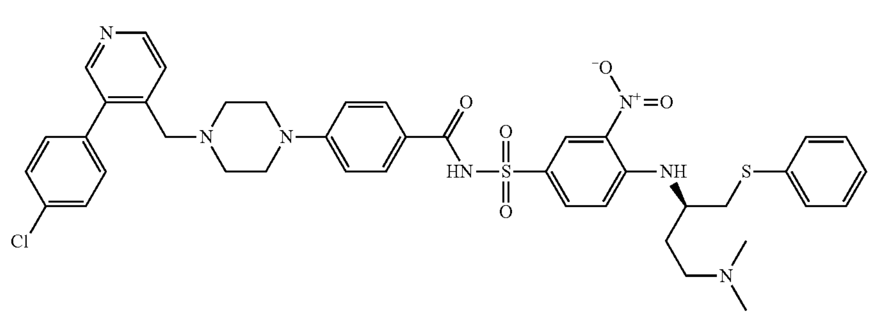 |

| Name | Structure |
|---|---|
| N-(4-(4-((3-(4-chlorophenyl)pyridin-4-yl)methyl)piperazin-1-yl)benzoyl)-3-nitro-4-((2-(phenylsulfanyl)ethyl)amino)benzenesulfonamide, | 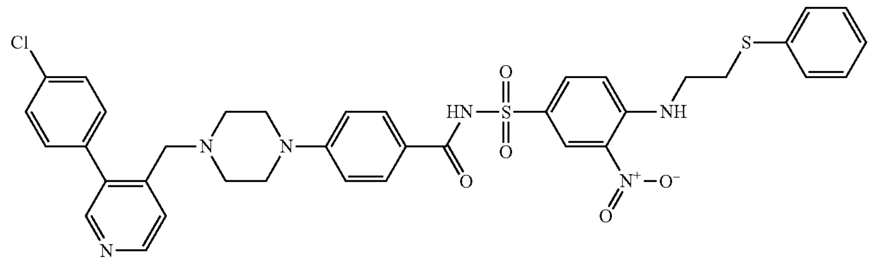 [SMILES: O=C(NS(=O)(=O)c1ccc(NCCSc2ccccc2)c([N+](=O)[O-])c1)c1ccc(N2CCN(Cc3ccncc3-c3ccc(Cl)cc3)CC2)cc1] |
| N-(4(4-((2-(4-chlorophenyl)-1-cyclopenten-1-yl)methyl)piperazin-1-yl)benzoyl)-4-(((1R)-3-(dimethylamino)-1-((phenylsulfanyl)methyl)propyl)amino)-3-nitrobenzenesulfonamide, | 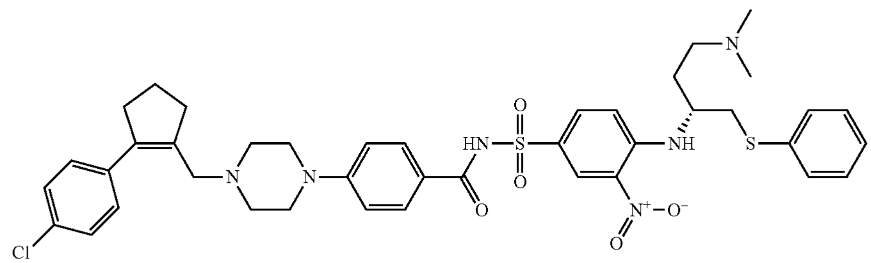 [SMILES: CN(C)CC[C@H](CSc1ccccc1)Nc1ccc(S(=O)(=O)NC(=O)c2ccc(N3CCN(CC4=C(c5ccc(Cl)cc5)CCC4)CC3)cc2)cc1[N+](=O)[O-]] |
| N-(4-(4-((2-(4-chlorophenyl)-1-cyclohexen-1-yl)methyl)piperazin-1-yl)benzoyl)-4-(((1R)-3-(dimethylamino)-1-((phenylsulfanyl)methyl)propyl)amino)-3-nitrobenzenesulfonamide, | 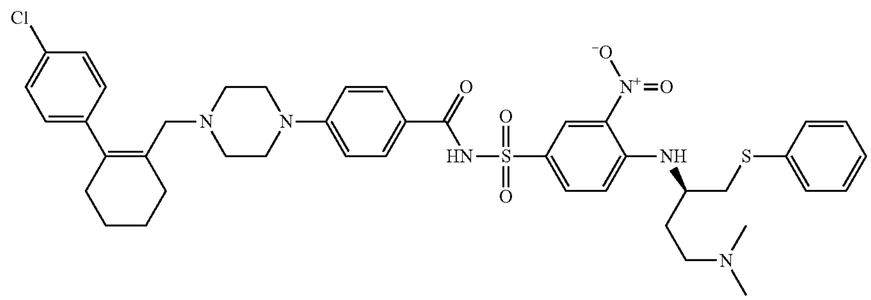 |
| N-(4-(4-((2-bromo-1-cyclopenten-1-yl)methyl)piperazin-1-yl)benzoyl)-4-(((1R)-3-(dimethylamino)-1-((phenylsulfanyl)methyl)propyl)amino)-3-nitrobenzenesulfonamide, | 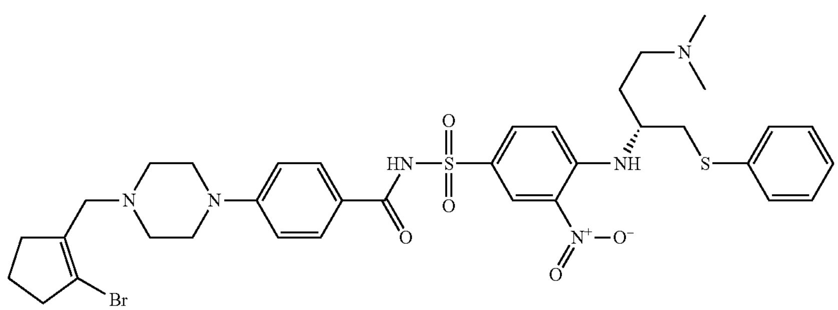 [SMILES: CN(C)CC[C@H](CSc1ccccc1)Nc1ccc(S(=O)(=O)NC(=O)c2ccc(N3CCN(CC4=C(Br)CCC4)CC3)cc2)cc1[N+](=O)[O-]] |
| N-(4-(4-((2-(4-chlorophenyl)-1-cyclohexen-1-yl)methyl)piperazin-1-yl)benzoyl)-4-(((1R)-3-(morpholin-4-yl)-1-((phenylsulfanyl)methyl)propyl)amino)-3-nitrobenzenesulfonamide, | 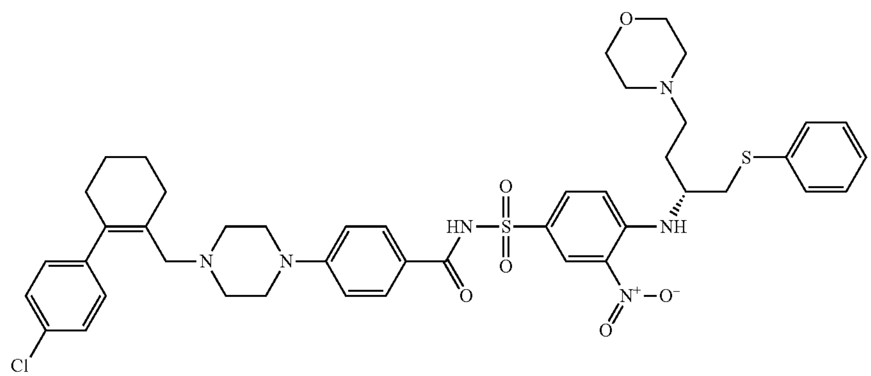 [SMILES: O=C(NS(=O)(=O)c1ccc(N[C@H](CCN2CCOCC2)CSc2ccccc2)c([N+](=O)[O-])c1)c1ccc(N2CCN(CC3=C(c4ccc(Cl)cc4)CCCC3)CC2)cc1] |

-continued

| Name | Structure |
|---|---|
| N-(4-(4-((2-(4-chlorophenyl)-1-cyclohexen-1-yl)methyl)piperazin-1-yl)benzoyl)-4-(((1R)-3-(dimethylamino)-1-((phenylsulfanyl)methyl)propyl)amino)-3-(trifluoromethyl)benzenesulfonamide, | 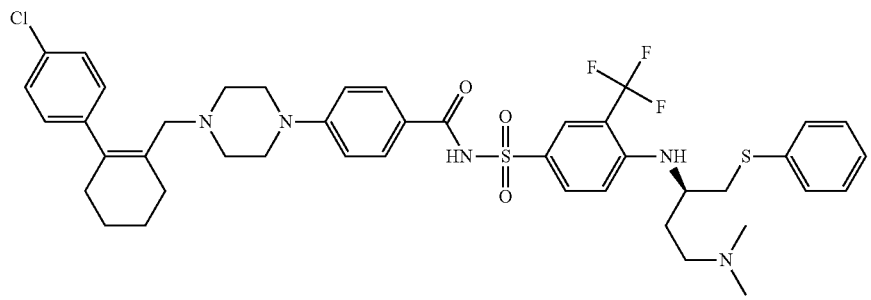 [SMILES: CN(C)CC[C@H](CSc1ccccc1)Nc1ccc(S(=O)(=O)NC(=O)c2ccc(N3CCN(CC4=C(c5ccc(Cl)cc5)CCCC4)CC3)cc2)cc1C(F)(F)F] |
| N-(4-(4-((2-bromo-1-cyclohexen-1-yl)methyl)piperazin-1-yl)benzoyl)-4-(((1R)-3-(dimethylamino)-1-((phenylsulfanyl)methyl)propyl)amino)-3-nitrobenzenesulfonamide, | 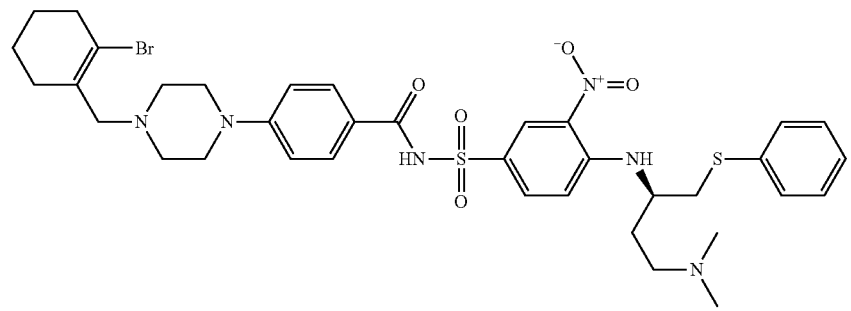 |
| N-(4-(4-((4-(4-chlorophenyl)-5,6-dihydro-2H-pyran-3-yl)methyl)piperazin-1-yl)benzoyl)-4-(((1R)-3-(dimethylamino)-1-((phenylsulfanyl)methyl)propyl)amino)-3-nitrobenzenesulfonamide, | 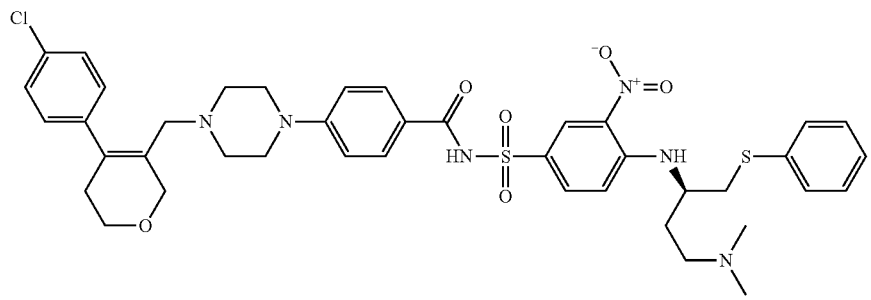 |
| 4-(((1R)-3-(dimethylamino)-1-((phenylsulfanyl)methyl)propyl)amino)-N-(4-(4-((2-(4-methoxyphenyl)-1-cyclohexen-1-yl)methyl)piperazin-1-yl)benzoyl)-3-nitrobenzenesulfonamide, | 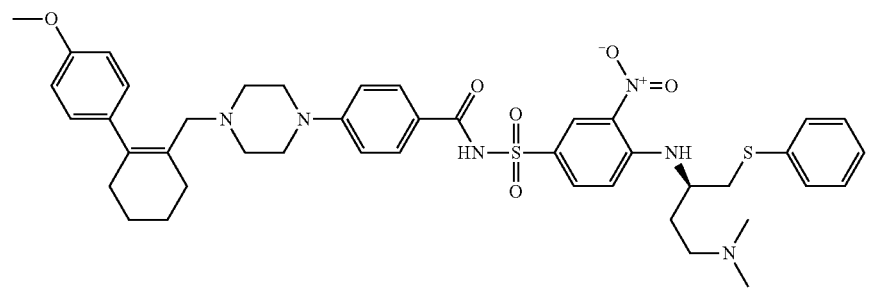 |
| 4-(((1R)-3-(dimethylamino)-1-((phenylsulfanyl)methyl)propyl)amino)-N-(4-(4-((2-(4-fluorophenyl)-1-cyclohexen-1-yl)methyl)piperazin-1-yl)benzoyl)-3-nitrobenzenesulfonamide, | 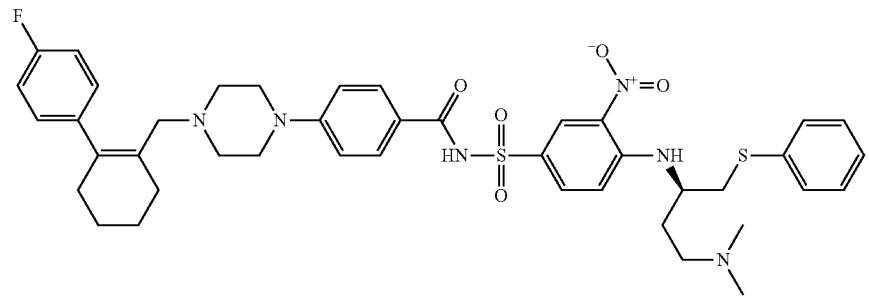 |

-continued

| Name | Structure |
|---|---|
| 4-(((1R)3-(dimethylamino)-1-((phenylsulfanyl)methyl)propyl)amino)-3-nitro-N-(4-(4-((2-phenyl-1-cyclohexen-1-yl)methyl)piperazin-1-yl)benzoyl)benzenesulfonamide, | 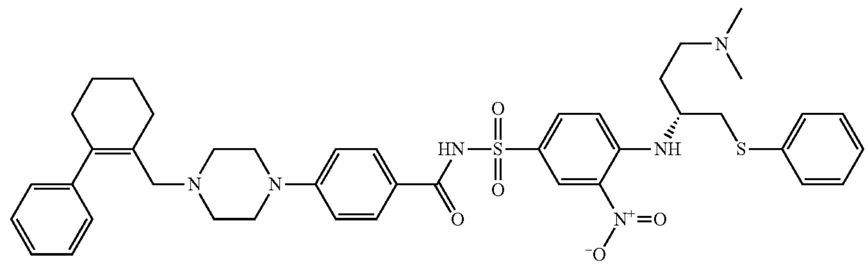 |
| N-(4-(4-((2-(4-chlorophenyl)-1-cycloocten-1-yl)methyl)piperazin-1-yl)benzoyl)-4-(((1R)-3-(dimethylamino)-1-((phenylsulfanyl)methyl)propyl)amino)-3-nitrobenzenesulfonamide, | 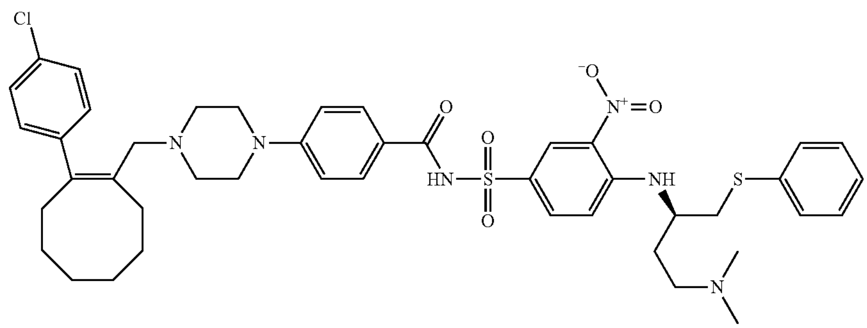 |
| 4-(((1R)-3-(dimethylamino)-1-((phenylsulfanyl)methyl)propyl)amino)-N-(4-(4-((2-(4-(methylsulfanyl)phenyl)-1-cyclohexen-1-yl)methyl)piperazin-1-yl)benzoyl)-3-nitrobenzenesulfonamide, | |
| N-(4-(4-((2-(4-chlorophenyl)-1-cyclohepten-1-yl)methyl)piperazin-1-yl)benzoyl)-4-(((1R)-3-(dimethylamino)-1-((phenylsulfanyl)methyl)propyl)amino)-3-nitrobenzenesulfonamide, | 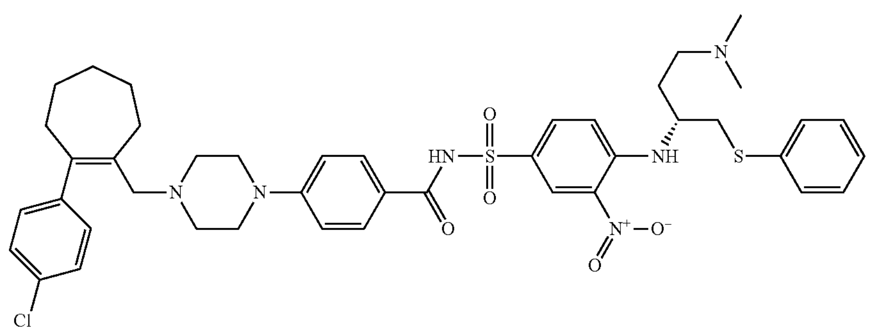 [SMILES: CN(C)CC[C@H](CSc1ccccc1)Nc1ccc(S(=O)(=O)NC(=O)c2ccc(N3CCN(CC4=C(c5ccc(Cl)cc5)CCCCC4)CC3)cc2)cc1[N+](=O)[O-]] |
| N-(4-(4-((2-(4-chlorophenyl)-1-cyclohepten-1-yl)methyl)piperazin-1-yl)benzoyl)-4-(((1R)-3-(morpholin-4-yl)-1-((phenylsulfanyl)methyl)propyl)amino)-3-nitrobenzenesulfonamide, | 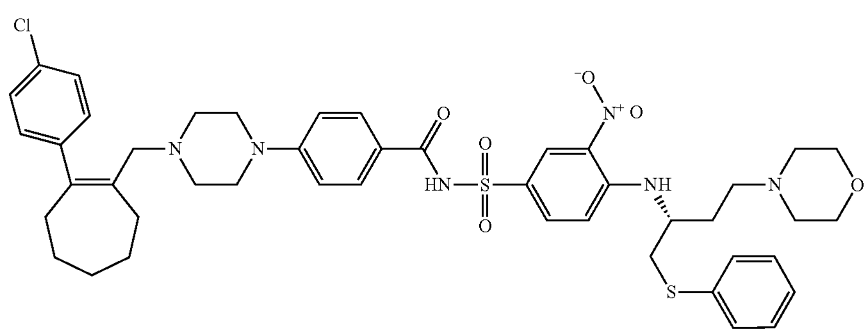 |

| Name | Structure |
|---|---|
| N-(4-(4-((2-(4-chlorophenyl)-5,5-dimethyl-1-cyclohexen-1-yl)methyl)piperazin-1-yl)benzoyl)-4-(((1R)-3-(dimethylamino)-1-((phenylsulfanyl)methyl)propyl)amino)-3-nitrobenzenesulfonamide, | 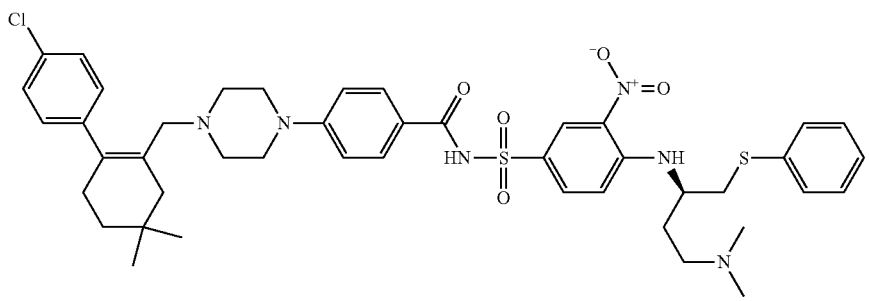 |
| N-(4-(4-((2-(4-chlorophenyl)-5,5-dimethyl-1-cyclohexen-1-yl)methyl)piperazin-1-yl)benzoyl)-4-(((1R)-3-(morpholin-4-yl)-1-((phenylsulfanyl)methyl)propyl)amino)-3-nitrobenzenesulfonamide, | 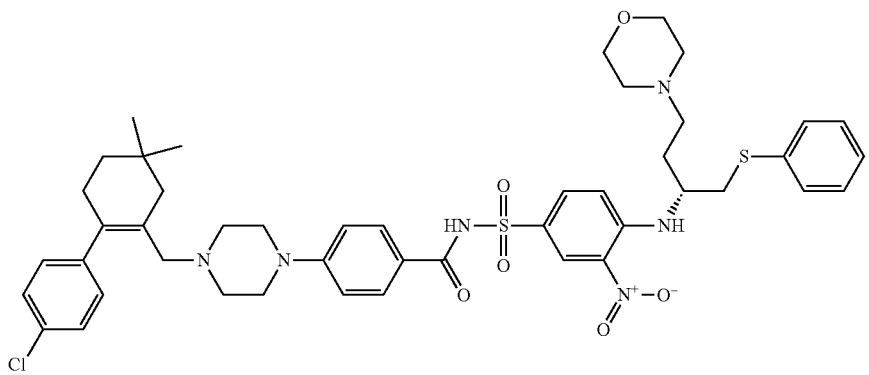 |
| N-(4-(4-((1,1'-biphenyl)-2-ylmethyl)-4-(2-(morpholin-4-yl)ethoxy)piperidin-1-yl)benzoyl)-4-((1,1-dimethyl-2-(phenylsulfanyl)ethyl)amino)-3-nitrobenzenesulfonamide, | 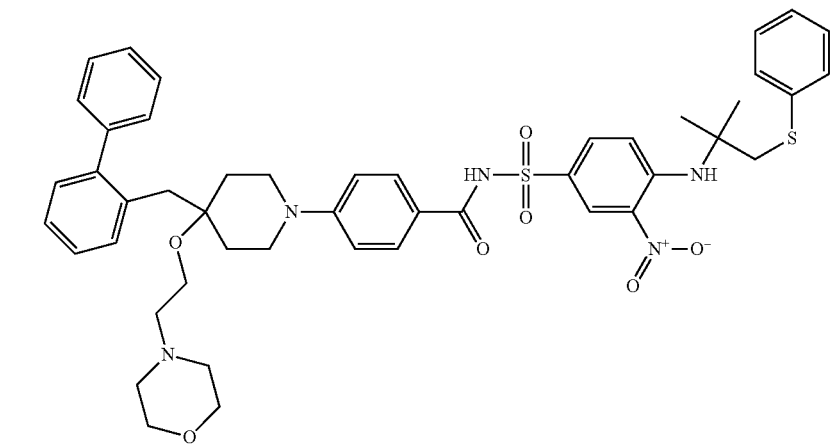 [SMILES: CC(C)(CSc1ccccc1)Nc1ccc(S(=O)(=O)NC(=O)c2ccc(N3CCC(Cc4ccccc4-c4ccccc4)(OCCN4CCOCC4)CC3)cc2)cc1[N+](=O)[O-]] |
| N-(4-(4-((1,1'-biphenyl)-2-ylmethyl)-4-(2-(morpholin-4-yl)ethoxy)piperidin-1-yl)benzoyl)-3-nitro-4-((2-(phenylsulfanyl)ethyl)amino)benzenesulfonamide, | 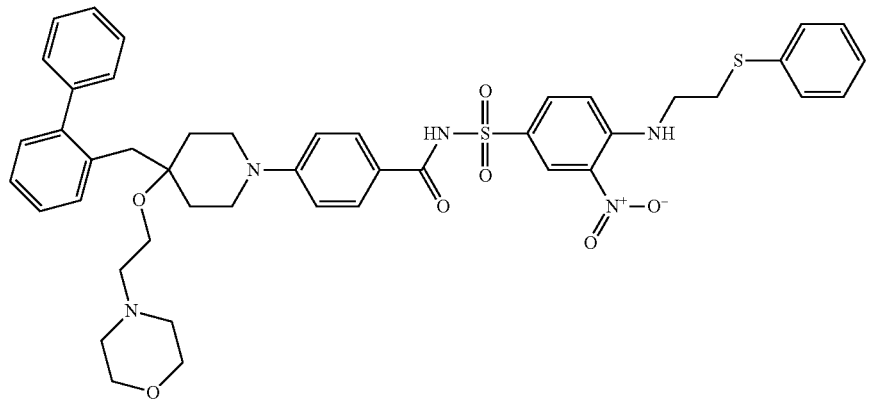 [SMILES: O=C(NS(=O)(=O)c1ccc(NCCSc2ccccc2)c([N+](=O)[O-])c1)c1ccc(N2CCC(Cc3ccccc3-c3ccccc3)(OCCN3CCOCC3)CC2)cc1] |

-continued

| Name | Structure |
|---|---|
| N-(4-(4-((1,1'-biphenyl)-2-ylmethyl)-4-(2-(pyrrolidin-1-yl)ethoxy)piperidin-1-yl)benzoyl)-4-((1,1-dimethyl-2-(phenylsulfanyl)ethyl)amino-3-nitrobenzenesulfonamide, | 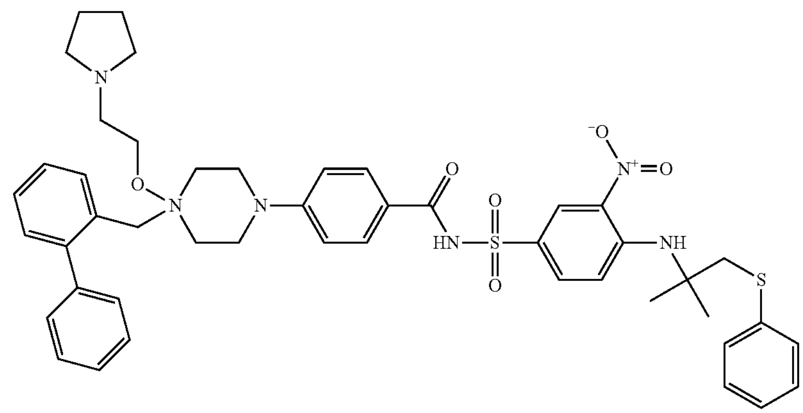 |
| N-(4-(4-((1,1'-biphenyl)-2-ylmethyl)-4-(2-(pyrrolidin-1-yl)ethoxy)piperidin-1-yl)benzoyl)-3-nitro-4-((2-(phenylsulfanyl)ethyl)amino)benzenesulfonamide, | 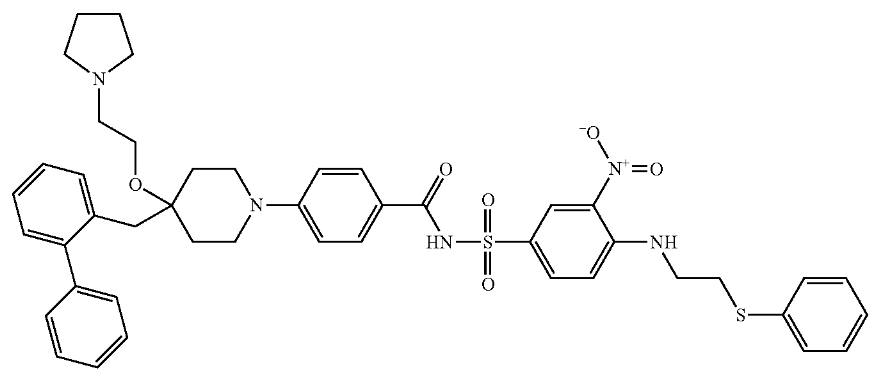 |
| N-(4-(4-((1,1'-biphenyl)-2-ylmethyl)-4-(2-(pyrrolidin-1-yl)ethoxy)piperidin-1-yl)benzoyl)-3-nitro-4-((1-((phenylsulfanyl)methyl)cyclopentyl)amino)benzenesulfonamide, | |
| N-(4-(4-((1,1'-biphenyl)-2-ylmethyl)-4-(2-(dimethylamino)ethoxy)piperidin-1-yl)benzoyl)-4-((1,1-dimethyl-2-(phenylsulfanyl)ethyl)amino)-3-nitrobenzenesulfonamide, | 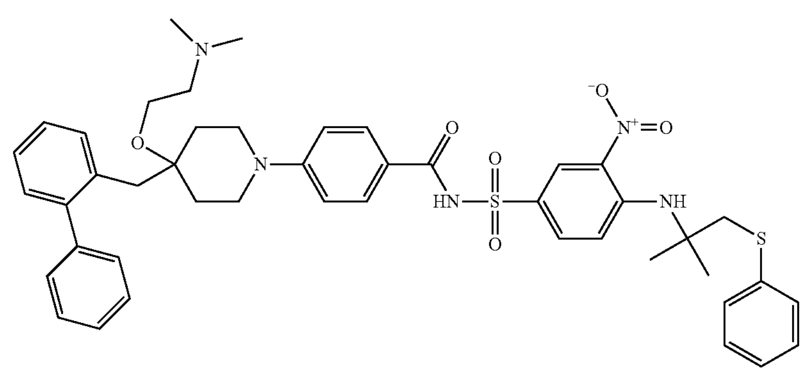 |

| Name | Structure |
|---|---|
| N-(4-(4-((1,1'-biphenyl)-2-ylmethyl)-4-(2-(dimethylamino)ethoxy)piperidin-1-yl)benzoyl)-3-nitro-4-((2-(phenylsulfanyl)ethyl)amino)benzenesulfonamide, | 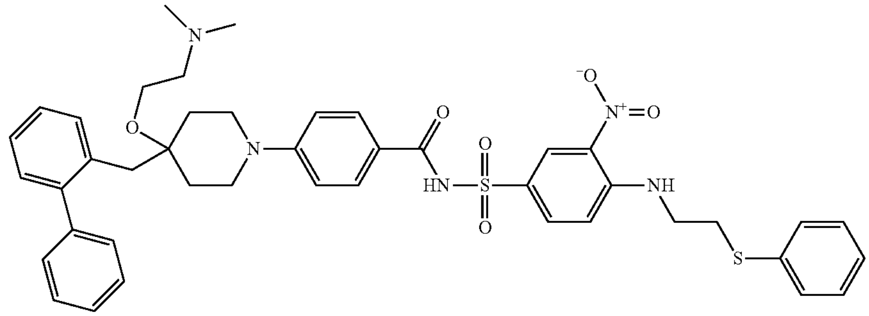 |
| N-(4-(4-((1,1'-biphenyl)-2-ylmethyl)-4-(2-(dimethylamino)ethoxy)piperidin-1-yl)benzoyl)-3-nitro-4-((1-((phenylsulfanyl)methyl)cyclopentyl)amino)benzenesulfonamide, | |
| N-(4-(4-((1,1'-biphenyl)-2-ylmethyl)-4-(2-(piperidin-1-yl)ethoxy)piperidin-1-yl)benzoyl)-4-((1,1-dimethyl-2-(phenylsulfanyl)ethyl)amino)-3-nitrobenzenesulfonamide, | 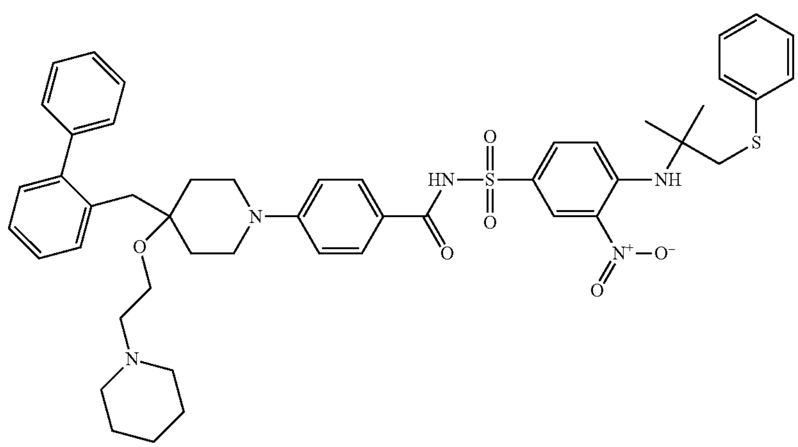 [SMILES: CC(C)(CSc1ccccc1)Nc1ccc(S(=O)(=O)NC(=O)c2ccc(N3CCC(Cc4ccccc4-c4ccccc4)(OCCN4CCCCC4)CC3)cc2)cc1[N+](=O)[O-]] |
| N-(4-(4-((1,1'-biphenyl)-2-ylmethyl)-4-(2-(piperidin-1-yl)ethoxy)piperidin-1-yl)benzoyl)-3-nitro-4-((2-(phenylsulfanyl)ethyl)amino)benzenesulfonamide, | 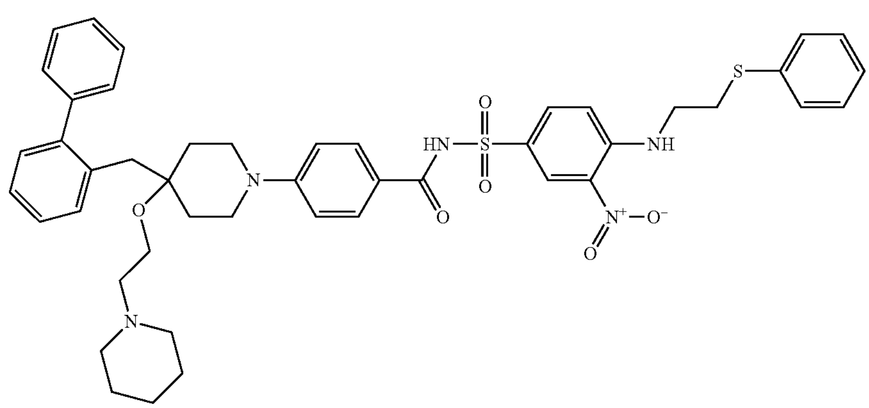 [SMILES: O=C(NS(=O)(=O)c1ccc(NCCSc2ccccc2)c([N+](=O)[O-])c1)c1ccc(N2CCC(Cc3ccccc3-c3ccccc3)(OCCN3CCCCC3)CC2)cc1] |

| Name | Structure |
|---|---|
| N-(4-(4-((1,1'-biphenyl)-2-ylmethyl)-4-(2-(piperidin-1-yl)ethoxy)piperidin-1-yl)benzoyl)-3-nitro-4-((1-((phenylsulfanyl)methyl)cyclopentyl)amino)benzenesulfonamide, | 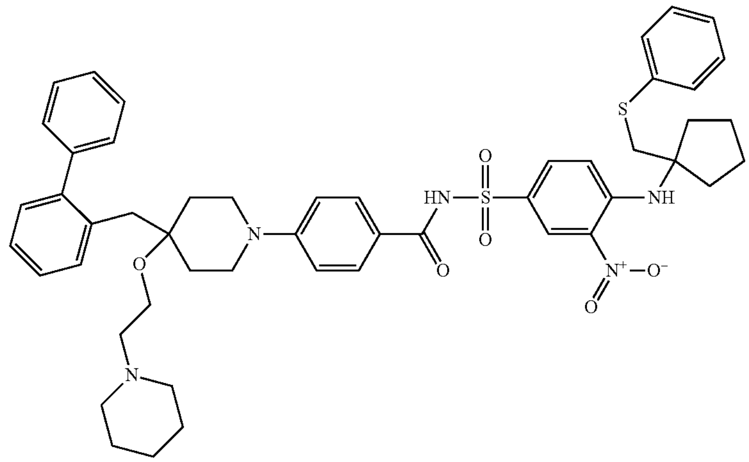 [SMILES: O=C(NS(=O)(=O)c1ccc(NC2(CSc3ccccc3)CCCC2)c([N+](=O)[O-])c1)c1ccc(N2CCC(Cc3ccccc3-c3ccccc3)(OCCN3CCCCC3)CC2)cc1] |
| N-(4-(4-((1,1'-biphenyl)-2-ylmethyl)piperazin-1-yl)benzoyl)-4-(((1S)-3-(morpholin-4-yl)-1-((phenylsulfanyl)methyl)propyl)amino)-3-nitrobenzenesulfonamide, | 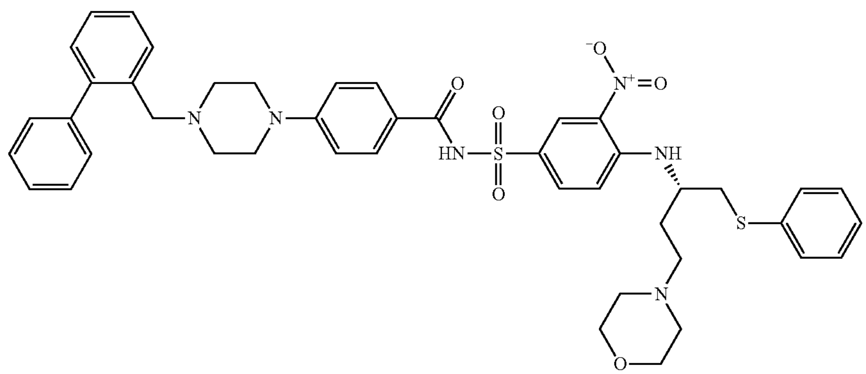 |
| N-(4-(4-((4'-(2-(dimethylamino)ethoxy)(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide, | 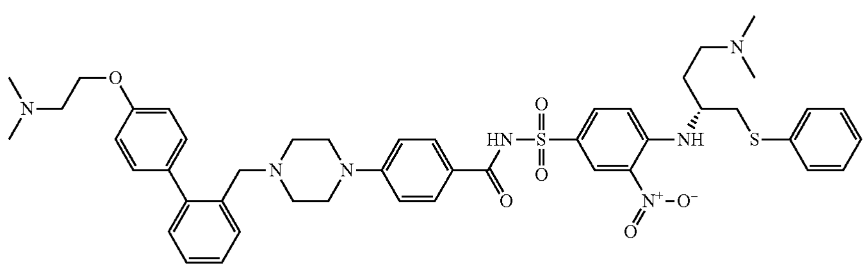 [SMILES: CN(C)CCOc1ccc(-c2ccccc2CN2CCN(c3ccc(C(=O)NS(=O)(=O)c4ccc(N[C@H](CCN(C)C)CSc5ccccc5)c([N+](=O)[O-])c4)cc3)CC2)cc1] |
| N-(4-(4-((4'-(2-(dimethylamino)ethoxy)(1,1'-biphenyl)-2-yl)methyl)piperazin-1-yl)benzoyl)-4-(((1R)-3-(morpholin-4-yl)-1-((phenylsulfanyl)methyl)propyl)amino)-3-nitrobenzenesulfonamide, | 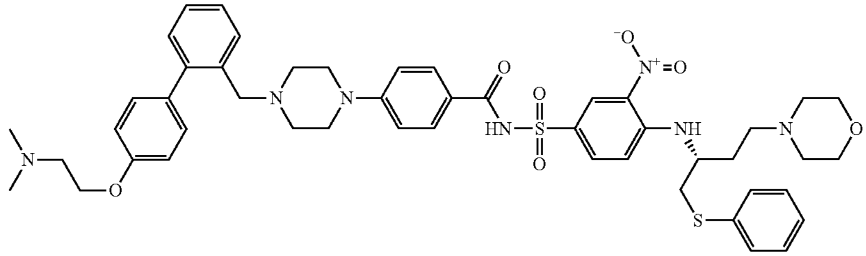 |

-continued

| Name | Structure |
|---|---|
| N-(4-(4-((4'-(2-(dimethylamino)ethoxy)(1,1'-biphenyl)-2-yl)methyl)piperazin-1-yl)benzoyl)-4-((1,1-dimethyl-2-(phenylsulfanyl)ethyl)amino)-3-nitrobenzenesulfonamide, | 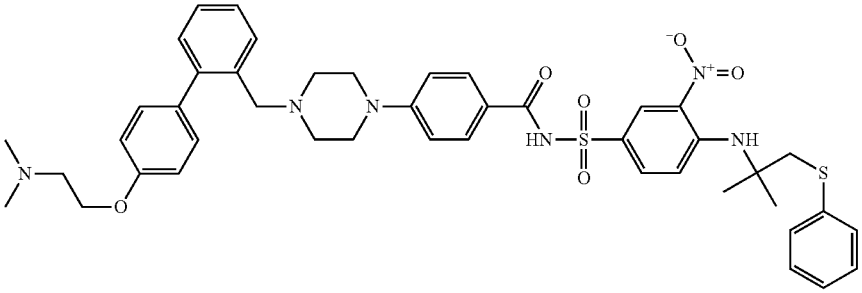 |
| N-(4-(4-((4'-(2-(dimethylamino)ethoxy)(1,1'-biphenyl)-2-yl)methyl)piperazin-1-yl)benzoyl)-3-nitro-4-((2-(phenylsulfanyl)ethyl)amino)benzenesulfonamide, | 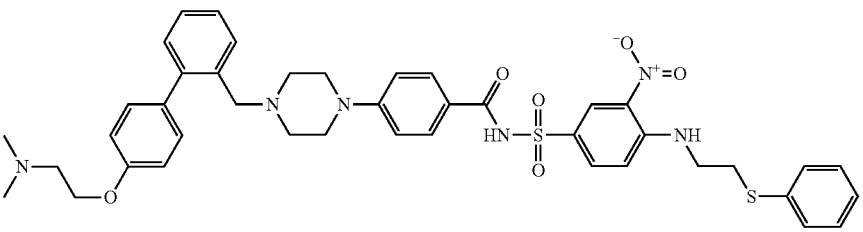 |
| 4-(((1R)-3-(dimethylamino)-1-((phenylsulfanyl)methyl)propyl)amino)-N-(4-(4-((4'-(2-(morpholin-4-yl)ethoxy)(1,1'-biphenyl)-2-yl)methyl)piperazin-1-yl)benzoyl)-3-nitrobenzenesulfonamide, | 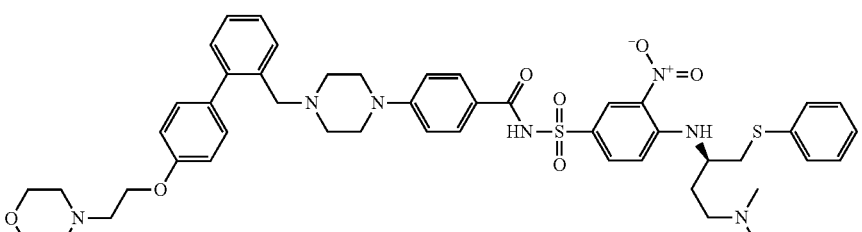 |
| N-(4-(4-((4'-(2-(morpholin-4-yl)ethoxy)(1,1'-biphenyl)-2-yl)methyl)piperazin-1-yl)benzoyl)-4-(((1R)-3-(morpholin-4-yl)-1-((phenylsulfanyl)methyl)propyl)amino)-3-nitrobenzenesulfonamide, | 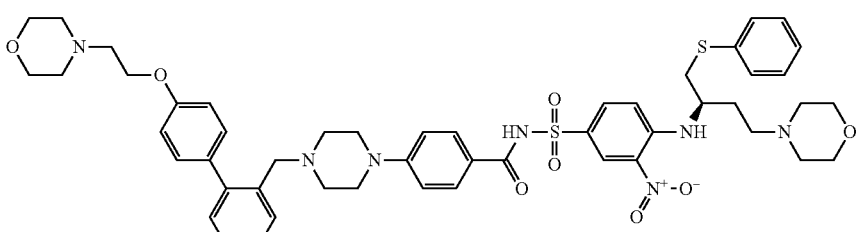 |
| 4-((1,1-dimethyl-2-(phenylsulfanyl)ethyl)amino)-N-(4-(4-((4'-(2-(morpholin-4-yl)ethoxy)(1,1'-biphenyl)-2-yl)methyl)piperazin-1-yl)benzoyl)-3-nitrobenzenesulfonamide, | 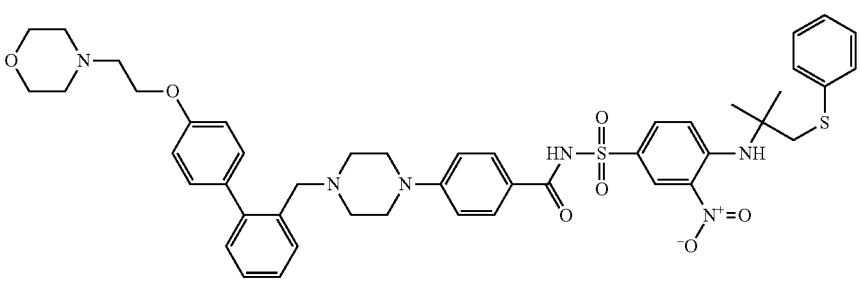 |
| N-(4-(4-((4'-(2-(morpholin-4-yl)ethoxy)(1,1'-biphenyl)-2-yl)methyl)piperazin-1-yl)benzoyl)-3-nitro-4-((2-(phenylsulfanyl)ethyl)amino)benzenesulfonamide, | 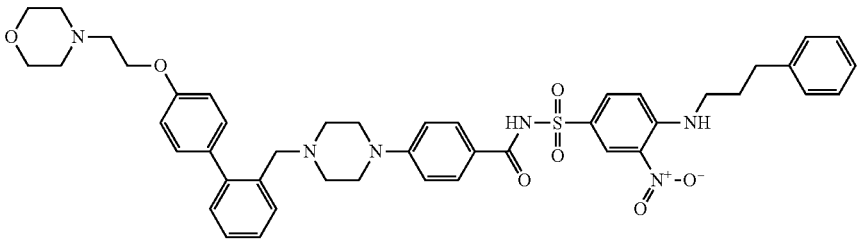 [SMILES: O=C(NS(=O)(=O)c1ccc(NCCCc2ccccc2)c([N+](=O)[O-])c1)c1ccc(N2CCN(Cc3ccccc3-c3ccc(OCCN4CCOCC4)cc3)CC2)cc1] |

-continued

| Name | Structure |
|---|---|
| N-(4-(4-((4'-chloro(1,1'-biphenyl)-2-yl)methyl)piperazin-1-yl)benzoyl)-4-(((1R)-3-(1H-imidazol-1-yl)-1-((phenylsulfanyl)methyl)propyl)amino)-3-nitrobenzenesulfonamide, | 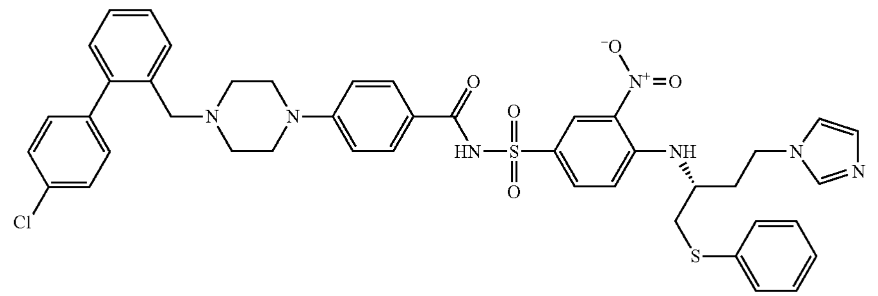 |
| N-(4-(4-((1,1'-biphenyl)-2-ylmethyl)piperazin-1-yl)benzoyl)-4-(((1R)-3-(1H-imidazol-1-yl)-1-((phenylsulfanyl)methyl)propyl)amino)-3-nitrobenzenesulfonamide, | 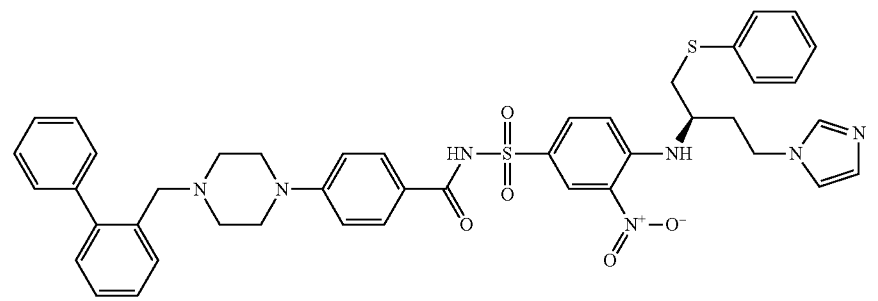 [SMILES: O=C(NS(=O)(=O)c1ccc(N[C@H](CCn2ccnc2)CSc2ccccc2)c([N+](=O)[O-])c1)c1ccc(N2CCN(Cc3ccccc3-c3ccccc3)CC2)cc1] |
| N-(4-(4-((1,1'-biphenyl)-2-ylmethyl)-4-methoxypiperidin-1-yl)benzoyl)-4-(((1R)-3-(1H-imidazol-1-yl)-1-((phenylsulfanyl)methyl)propyl)amino)-3-nitrobenzenesulfonamide, | 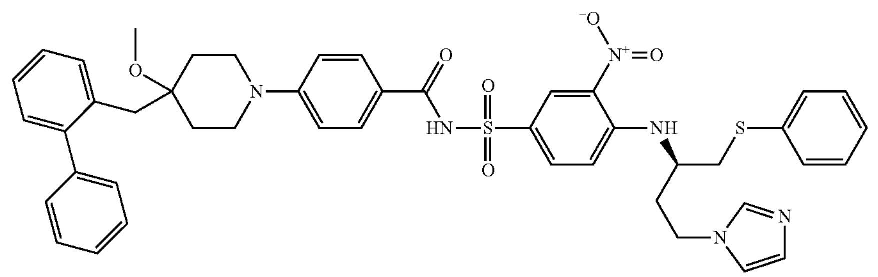 |
| N-(4-(4-((4'-chloro(1,1'-biphenyl)-2-yl)methyl)piperazin-1-yl)benzoyl)-4-(((1R)-4-(4-methylpiperazin-1-yl)-1-((phenylsulfanyl)methyl)butyl)amino)-3-nitrobenzenesulfonamide, | 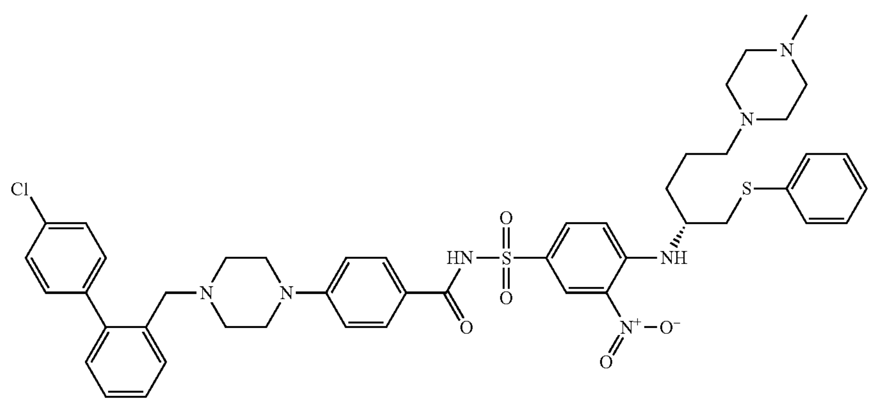 [SMILES: CN1CCN(CCC[C@H](CSc2ccccc2)Nc2ccc(S(=O)(=O)NC(=O)c3ccc(N4CCN(Cc5ccccc5-c5ccc(Cl)cc5)CC4)cc3)cc2[N+](=O)[O-])CC1] |
| N-(4-(4-((4'-chloro(1,1'-biphenyl)-2-yl)methyl)piperazin-1-yl)benzoyl)-4-(((1R)-2-((2-(dimethylamino)ethyl)(methyl)amino)-1-((phenylsulfanyl)methyl)ethyl)amino)-3-nitrobenzenesulfonamide, | 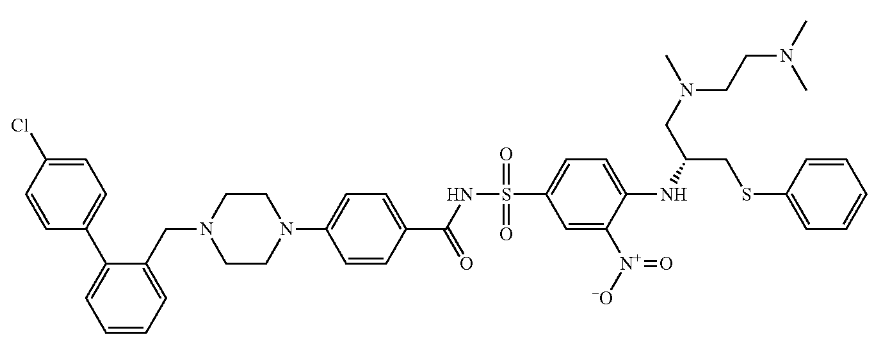 |

| Name | Structure |
|---|---|
| (4R)-4-(4-(((4-(4-((4'-chloro(1,1'-biphenyl)-2-yl)methyl)piperazin-1-yl)benzoyl)aniino)sulfonyl)-2-nitroanilino)-N,N-dimethyl-5-(phenylsulfanyl)pentanamide, | 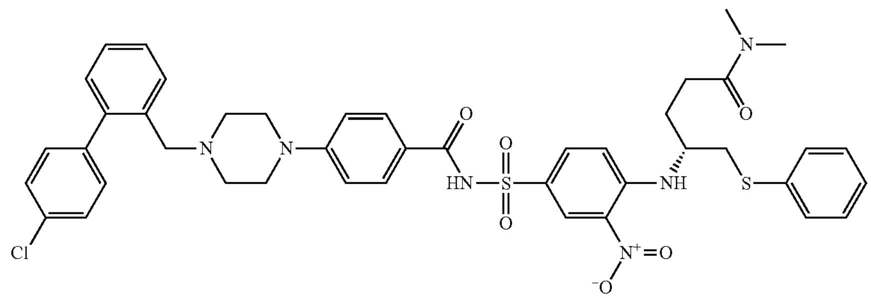 |
| N-(4-(4-((4'-chloro(1,1'-biphenyl)-2-yl)methyl)piperazin-1-yl)benzoyl)-4-(((1R)-4-(dimethylamino)-1-((phenylsulfonyl)methyl)butyl)amino)-3-nitrobenzenesulfonamide, | 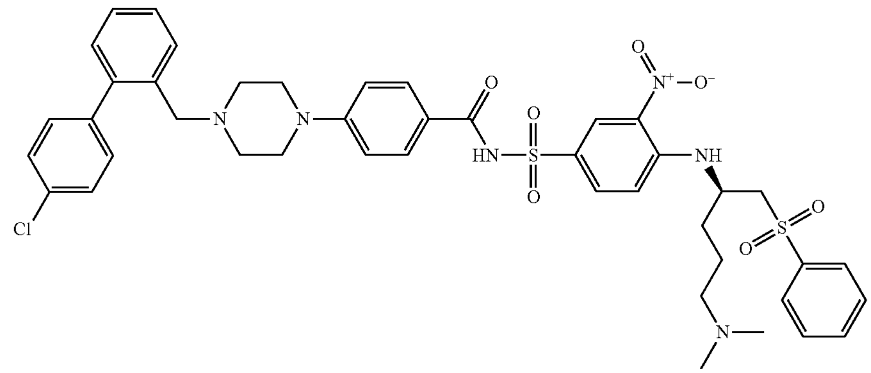 [SMILES: CN(C)CCC[C@H](CS(=O)(=O)c1ccccc1)Nc1ccc(S(=O)(=O)NC(=O)c2ccc(N3CCN(Cc4ccccc4-c4ccc(Cl)cc4)CC3)cc2)cc1[N+](=O)[O-]] |
| 2-(((3R)-3-(4-(((4-(4-((4'-chloro(1,1'-biphenyl)-2-yl)methyl)piperazin-1-yl)benzoyl)amino)sulfonyl)-2-nitroanilino)-4-(phenylsulfanyl)butyl)(methyl)amino)-N,N-dimethylacetamide, | 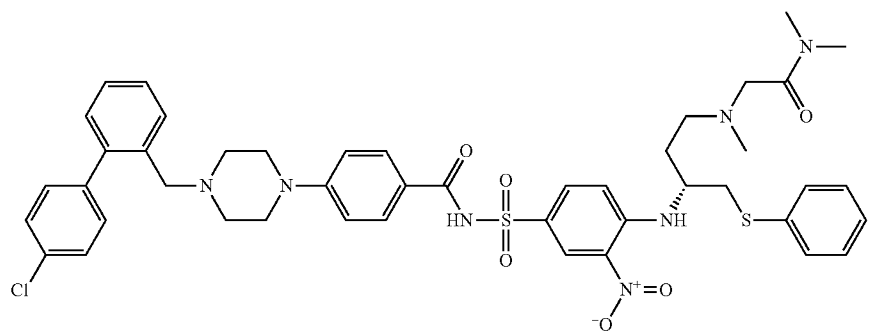 |
| (3R)-N-(tert-butyl)-3-(4-(((4-(4-((4'-chloro(1,1'-biphenyl)-2-yl)methyl)piperazin-1-yl)benzoyl)amino)sulfonyl)-2-nitroanilino)-4-(phenylsulfanyl)butanamide, | 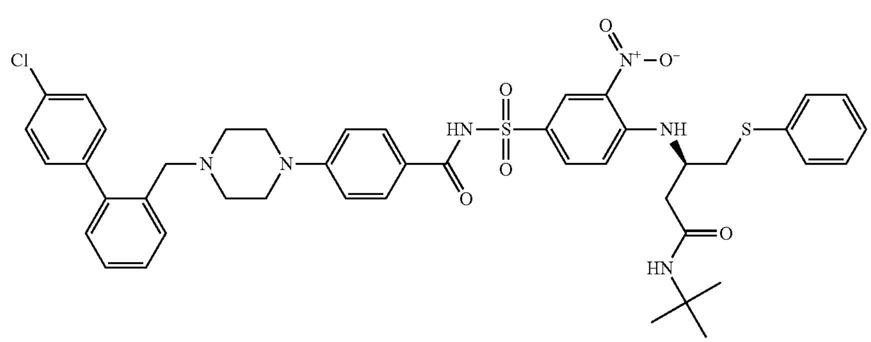 [SMILES: CC(C)(C)NC(=O)C[C@H](CSc1ccccc1)Nc1ccc(S(=O)(=O)NC(=O)c2ccc(N3CCN(Cc4ccccc4-c4ccc(Cl)cc4)CC3)cc2)cc1[N+](=O)[O-]] |

-continued

| Name | Structure |
|---|---|
| (3R)-3-(4-(((4-(4-((4'-chloro(1,1'-biphenyl)-2-yl)methyl)piperazin-1-yl)benzoyl)amino)sulfonyl)-2-nitroanilino)-N,N-diisopropyl-4-(phenylsulfanyl)butanamide, | 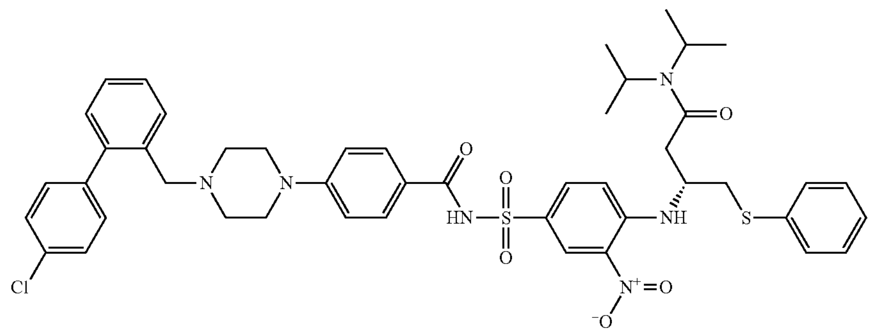 |
| (3R)-N-(tert-butyl)-3-(4-(((4-(4-((4'-chloro(1,1'-biphenyl)-2-yl)methyl)piperazin-1-yl)benzoyl)amino)sulfonyl)-2-nitroanilino)-N-methyl-4-(phenylsulfanyl)butanamide, | 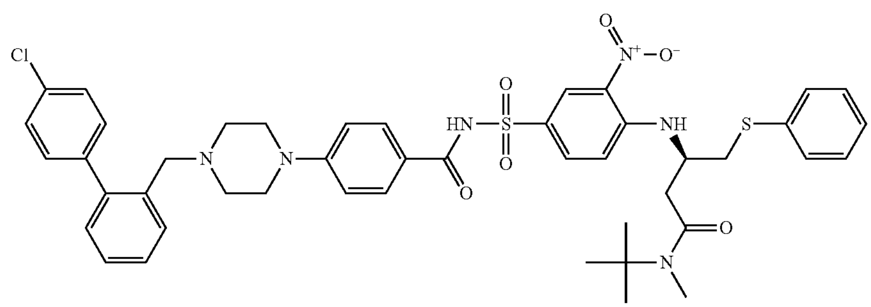 [SMILES: CN(C(=O)C[C@H](CSc1ccccc1)Nc1ccc(S(=O)(=O)NC(=O)c2ccc(N3CCN(Cc4ccccc4-c4ccc(Cl)cc4)CC3)cc2)cc1[N+](=O)[O-])C(C)(C)C] |
| (3R)-3-(4-(((4-(4-((4'-chloro(1,1'-biphenyl)-2-yl)methyl)piperazin-1-yl)benzoyl)amino)sulfonyl)-2-nitroanilino)-N-isopropyl-N-methyl-4-(phenylsulfanyl)butanamide, | 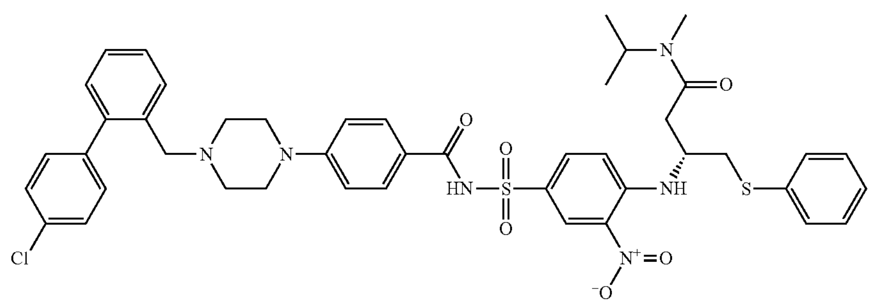 |
| N-(4-(4-((4'-chloro(1,1'-biphenyl)-2-yl)methyl)piperazin-1-yl)benzoyl)-3-nitro-4-(((1R)-3-oxo-1-((phenylsulfanyl)methyl)-3-(piperidin-1-yl)propyl)amino)benzene-sulfonamide, | |

-continued

| Name | Structure |
|---|---|
| N-((5R)-5-(4-(((4-(4-((4'-chloro(1,1'-biphenyl)-2-yl)methyl)piperazin-1-yl)benzoyl)amino)sulfonyl)-2-nitroanilino)-6-(phenylsulfanyl)hexyl)-2-(dimethylamino)acetamide, | 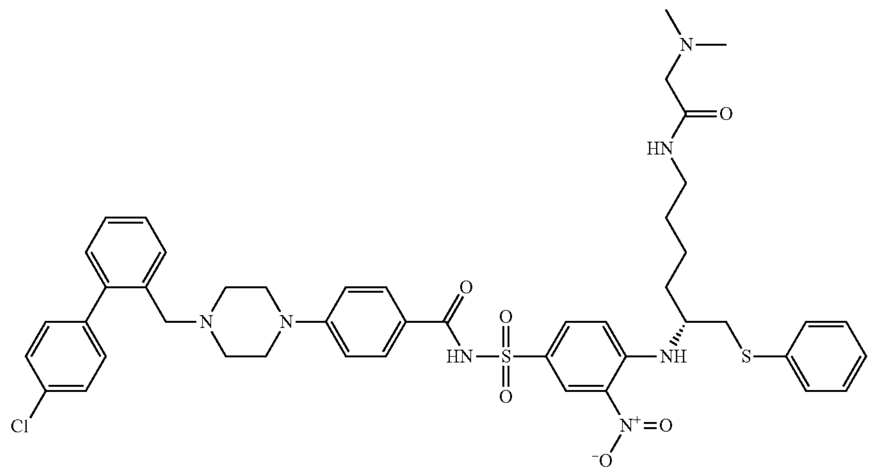 |
| (3R)-3-(4-(((4-(4-((4'-chloro(1,1'-biphenyl)-2-yl)methyl)piperazin-1-yl)benzoyl)amino)sulfonyl)-2-nitroanilino)-N,N-dimethyl-4-(phenylsulfanyl)butanamide, | 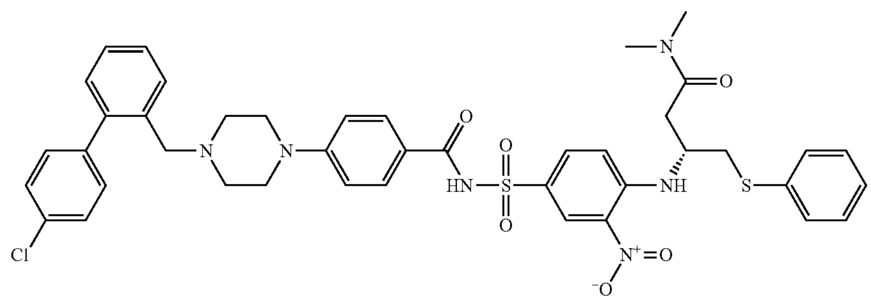 |
| N-(4-(4-((4'-chloro(1,1'-biphenyl)-2-yl)methyl)piperazin-1-yl)benzoyl)-4-(((1R)-3-(1,1-dioxidothiomorpholin-4-yl)-3-oxo-1-((phenylsulfanyl)methyl)propyl)amino)-3-nitrobenzenesulfonamide, | 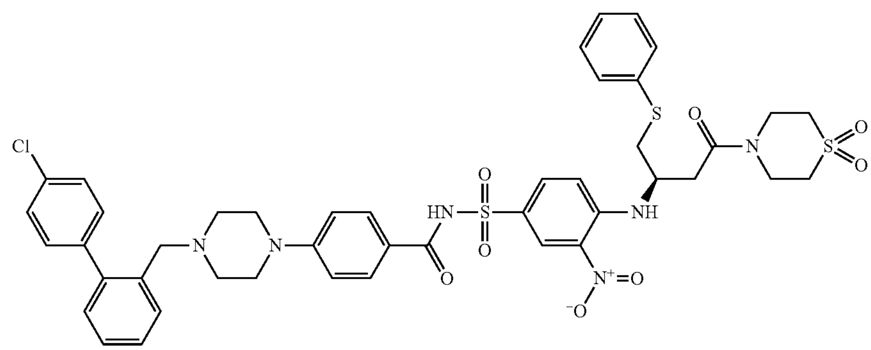 |
| (3R)-3-(4-(((4-(4-((4'-chloro(1,1'-biphenyl)-2-yl)methyl)piperazin-1-yl)benzoyl)amino)sulfonyl)-2-nitroanilino)-4-(phenylsulfanyl)butanamide, | 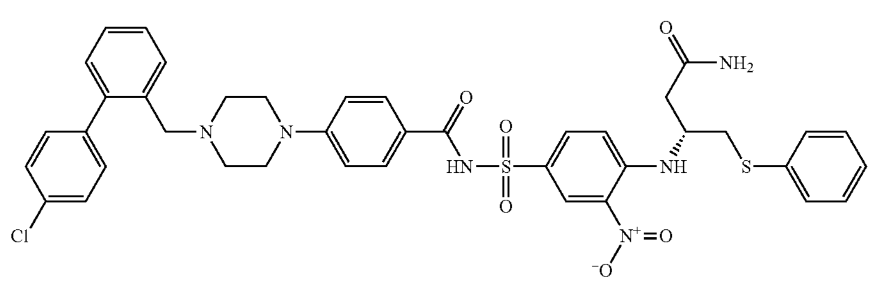 |

-continued

| Name | Structure |
|---|---|
| (3R)-3-(4-(((4-(4-((4'-chloro(1,1'-biphenyl)-2-yl)methyl)piperazin-1-yl)benzoyl)amino)sulfonyl)-2-nitroanilino)-N-cyclopropyl-4-(phenylsulfanyl)butanamide, | 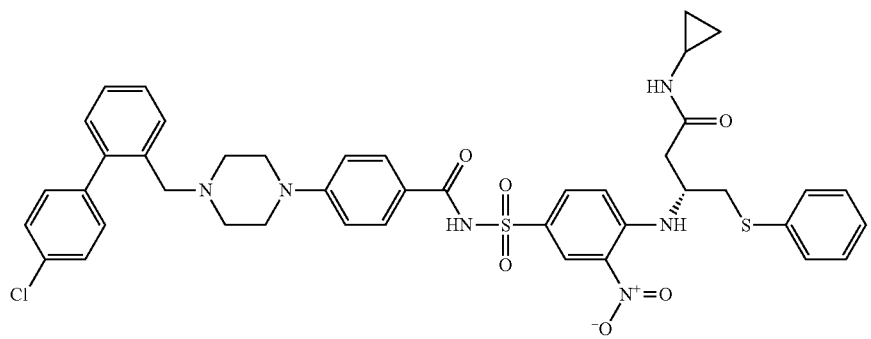 |
| (3R)-3-(4-(((4-(4-((4'-chloro(1,1'-biphenyl)-2-yl)methyl)piperazin-1-yl)benzoyl)amino)sulfonyl)-2-nitroanilino)-N-cyclobutyl-4-(phenylsulfanyl)butanamide, | 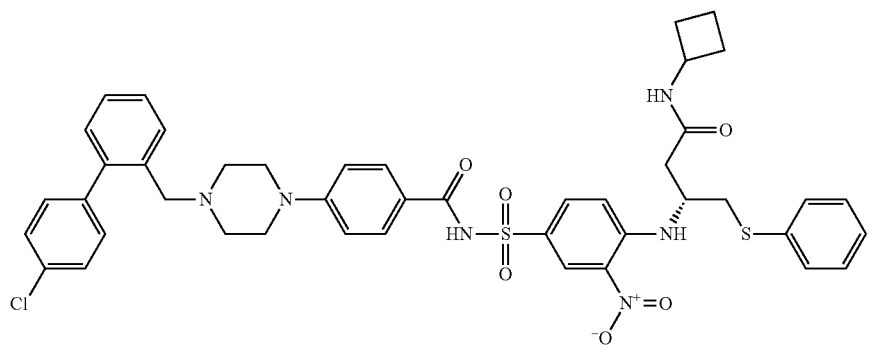 |
| N-(4-(4-((4'-chloro(1,1'-biphenyl)-2-yl)methyl)piperazin-1-yl)benzoyl)-4-(((1R)-3-(4-methylpiperazin-1-yl)-3-oxo-1-((phenylsulfanyl)(methyl)propyl)amino)-3-nitrobenzenesulfonamide, | 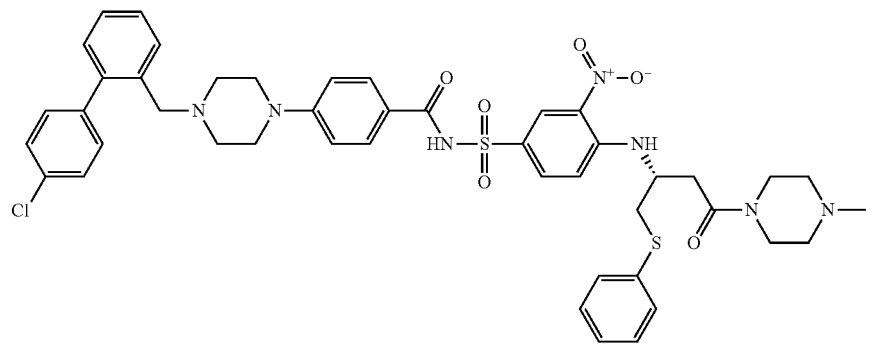 [SMILES: CN1CCN(C(=O)C[C@H](CSc2ccccc2)Nc2ccc(S(=O)(=O)NC(=O)c3ccc(N4CCN(Cc5ccccc5-c5ccc(Cl)cc5)CC4)cc3)cc2[N+](=O)[O-])CC1] |
| N-(4-(4-((4'-chloro(1,1'-biphenyl)-2-yl)methyl)piperazin-1-yl)benzoyl)-4-(((1R)-3-(morpholin-4-yl)-3-oxo-1-((phenylsulfanyl)methyl)propyl)amino)-3-nitrobenzenesulfonamide, | 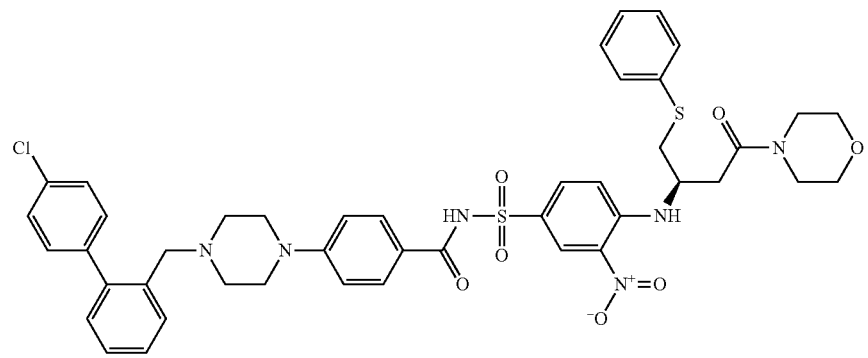 |

-continued

| Name | Structure |
|---|---|
| 4-(((1R)-3-(azetidin-1-yl)-3-oxo-1-((phenylsulfanyl)methyl)propyl)amino)-N-(4-(4-((4'-chloro(1,1'-biphenyl)-2-yl)methyl)piperazin-1-yl)benzoyl)-3-nitrobenzenesulfonamide, | 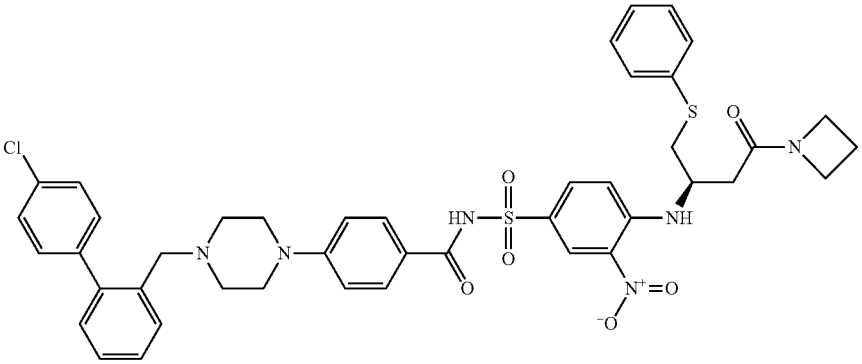 |
| (3R)-3-(4-(((4-(4-((4'-chloro(1,1'-biphenyl)-2-yl)methyl)piperazin-1-yl)benzoyl)amino)sulfonyl)-2-nitroanilino)-N-(2-(morpholin-4-yl)ethyl)-4-(phenylsulfanyl)butanamide, | 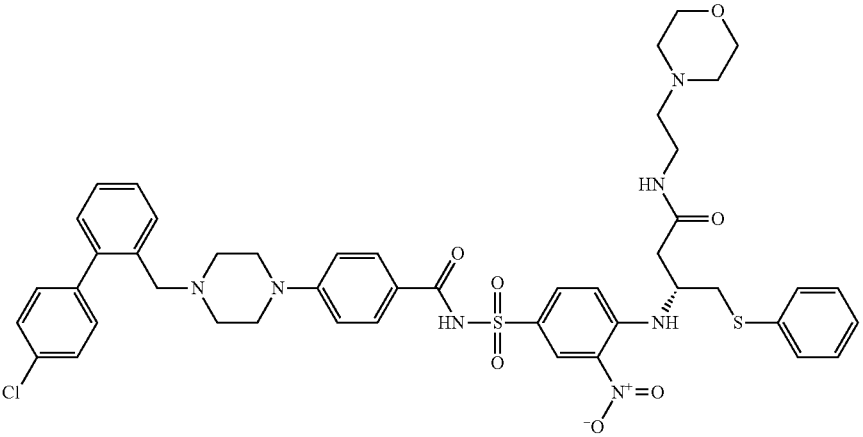 |
| (3R)-3-(4-(((4-(4-((4'-chloro(1,1'-biphenyl)-2-yl)methyl)piperazin-1-yl)benzoyl)amino)sulfonyl)-2-nitroanilino)-N-methyl-4-(phenylsulfanyl)butanamide, | 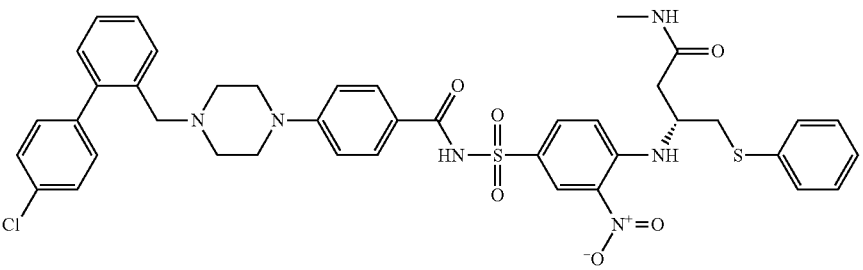 |
| 4-(((1R)-3-amino-1-((phenylsulfanyl)methyl)propyl)amino)-N-(4-(4-((4'-chloro(1,1'-biphenyl)-2-yl)methyl)piperazin-1-yl)benzoyl)-3-nitrobenzenesulfonamide, | 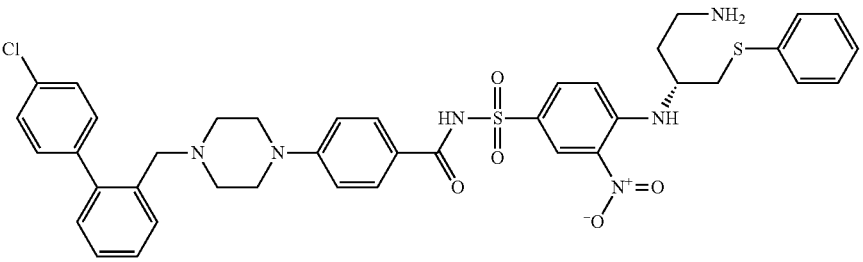 |
| N-(4-(4-((4'-chloro(1,1'-biphenyl)-2-yl)methyl)piperazin-1-yl)benzoyl)-4-(((1R)-3-cyano-1-((phenylsulfanyl)methyl)propyl)amino)-3-nitrobenzenesulfonamide, | 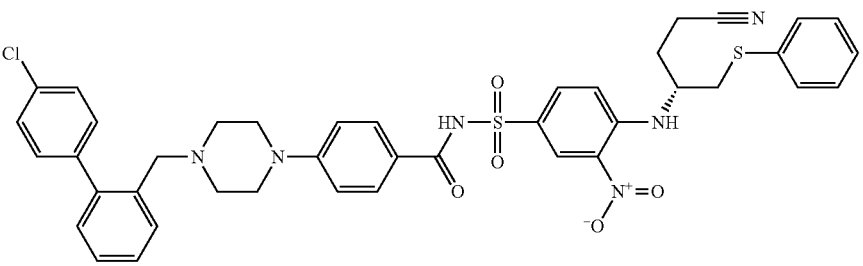 |

| Name | Structure |
|---|---|
| 4-(((1R)-3-(tert-butylamino)-1-((phenylsulfanyl)methyl)propyl)amino)-N-(4-(4-((4'-chloro(1,1'-biphenyl)-2-yl)methyl)piperazin-1-yl)benzoyl)-3-nitrobenzenesulfonamide, | 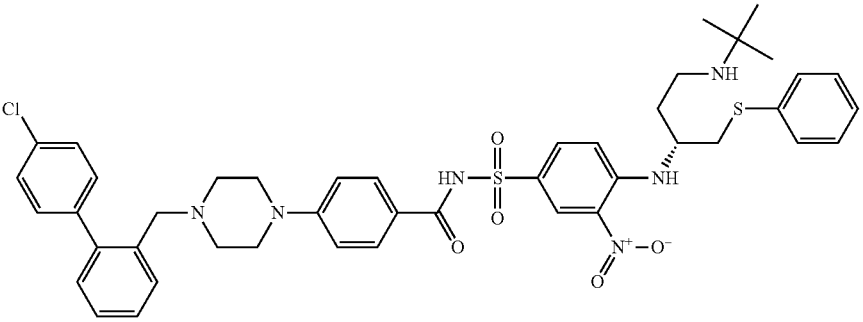 [SMILES: CC(C)(C)NCC[C@H](CSc1ccccc1)Nc1ccc(S(=O)(=O)NC(=O)c2ccc(N3CCN(Cc4ccccc4-c4ccc(Cl)cc4)CC3)cc2)cc1[N+](=O)[O-]] |
| N-(4-(4-((4'-chloro(1,1'-biphenyl)-2-yl)methyl)piperazin-1-yl)benzoyl)-4-(((1R)-3-(cyclopropylamino)-1-((phenylsulfanyl)methyl)propyl)amino)-3-nitrobenzenesulfonamide, | 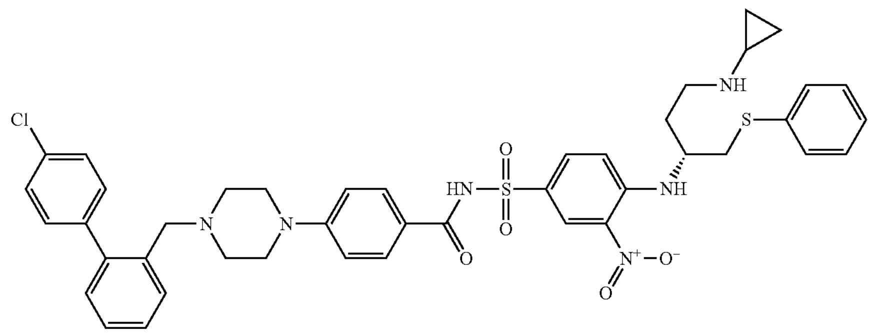 [SMILES: O=C(NS(=O)(=O)c1ccc(N[C@H](CCNC2CC2)CSc2ccccc2)c([N+](=O)[O-])c1)c1ccc(N2CCN(Cc3ccccc3-c3ccc(Cl)cc3)CC2)cc1] |
| N-(4-(4-((4'-chloro(1,1'-biphenyl)-2-yl)methyl)piperazin-1-yl)benzoyl)-4-(((1R)-3-(cyclobutylamino)-1-((phenylsulfanyl)methyl)propyl)amino)-3-nitrobenzenesulfonamide, | 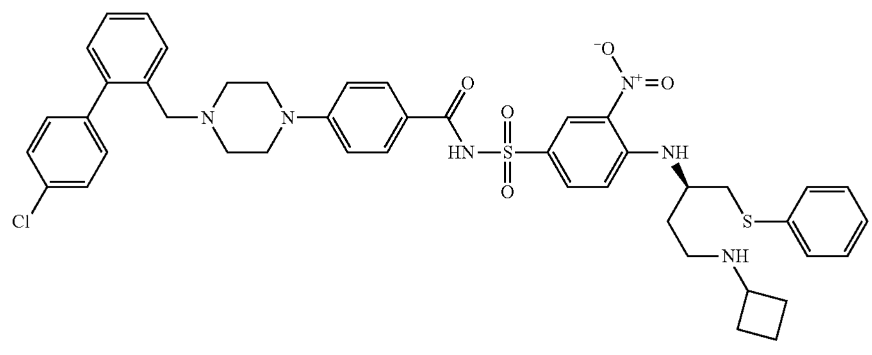 |
| N-(4-(4-((4'-chloro(1,1'-biphenyl)-2-yl)methyl)piperazin-1-yl)benzoyl)-4-(((1R)-3-(diethylamino)-1-((phenylsulfanyl)methyl)propyl)amino)-3-nitrobenzenesulfonamide, | 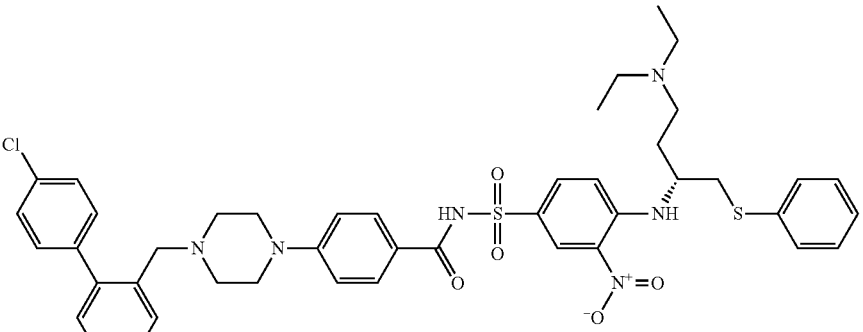 |

| Name | Structure |
|---|---|
| N-(4-(4-((4'-chloro(1,1'-biphenyl)-2-yl)methyl)piperazin-1-yl)benzoyl)-4-(((1R)-3-(isopropyl(methyl)amino)-1-((phenylsulfanyl)methyl)propyl)amino)-3-nitrobenzenesulfonamide, | 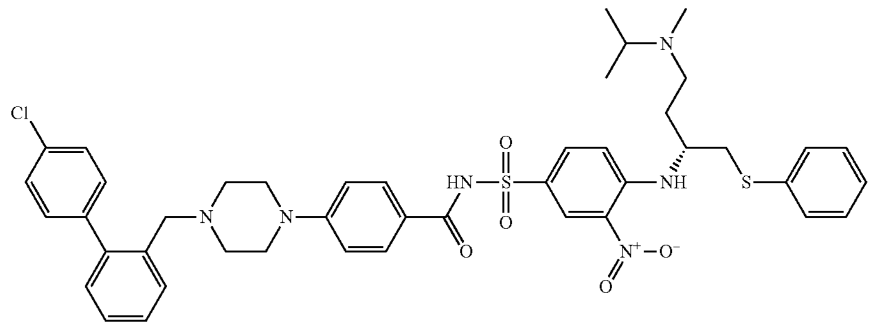 [SMILES: CC(C)N(C)CC[C@H](CSc1ccccc1)Nc1ccc(S(=O)(=O)NC(=O)c2ccc(N3CCN(Cc4ccccc4-c4ccc(Cl)cc4)CC3)cc2)cc1[N+](=O)[O-]] |
| 4-(((1R)-3-(tert-butyl(methyl)amino)-1-((phenylsulfanyl)methyl)propyl)amino)-N-(4-(4-((4'-chloro(1,1'-biphenyl)-2-yl)methyl)piperazin-1-yl)benzoyl)-3-nitrobenzenesulfonamide, | 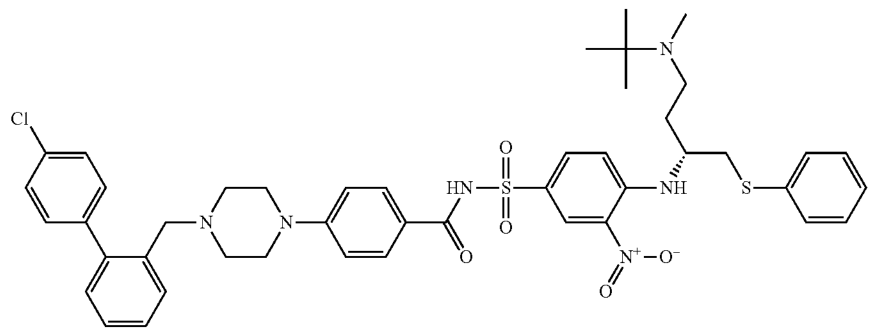 [SMILES: CN(CC[C@H](CSc1ccccc1)Nc1ccc(S(=O)(=O)NC(=O)c2ccc(N3CCN(Cc4ccccc4-c4ccc(Cl)cc4)CC3)cc2)cc1[N+](=O)[O-])C(C)(C)C] |
| N-(4-(4-((4'-chloro(1,1'-biphenyl)-2-yl)methyl)piperazin-1-yl)benzoyl)-3-nitro-4-(((1R)-1-((phenylsulfanyl)methyl)-3-(piperidin-1-yl)propyl)amino)benzenesulfonamide, | |
| N-(4-(4-((4'-chloro(1,1'-biphenyl)-2-yl)methyl)piperazin-1-yl)benzoyl)-4-(((1R)-3-(4-hydroxypiperidin-1-yl)-1-((phenylsulfanyl)methyl)propyl)amino)-3-nitrobenzenesulfonamide, | 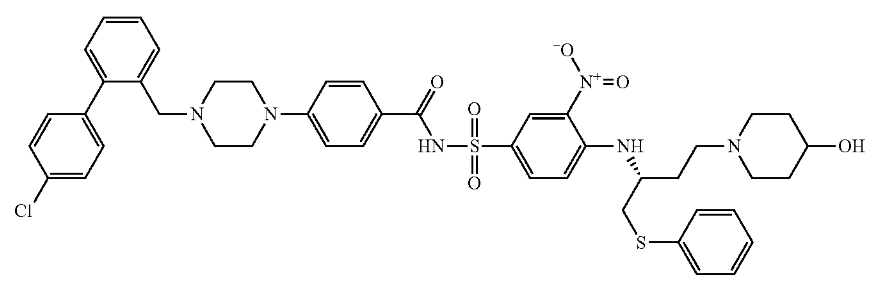 |
| 4-(((1R)-3-(4-acetylpiperazin-1-yl-1-((phenylsulfanyl)methyl)propyl)amino)-N-(4-(4-((4'-chloro(1,1'-biphenyl)-2-yl)methyl)piperazin-1-yl)benzoyl)-3-nitrobenzenesulfonamide, | 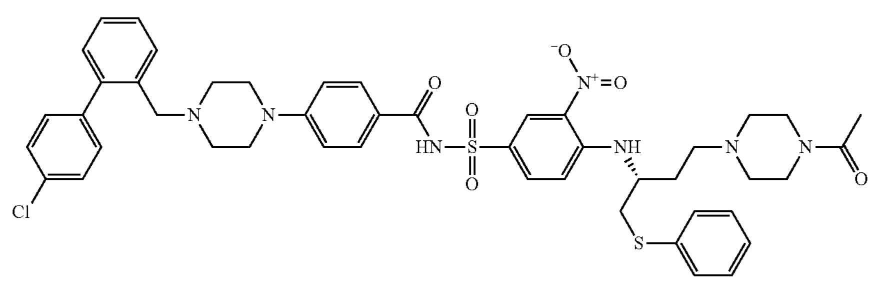 |

| Name | Structure |
|---|---|
| N-(4-(4-((4'-chloro(1,1'-biphenyl)-2-yl)methyl)piperazin-1-yl)benzoyl)-3-nitro-4-(((1R)-1-((phenylsulfanyl)methyl)-3-(thiomorpholin-4-yl)propyl)amino)benzenesulfonamide, | |
| N-(4-(4-((4'-chloro(1,1'-biphenyl)-2-yl)methyl)piperazin-1-yl)benzoyl)-4-(((1R)-3-((2-(morpholin-4-yl)ethyl)amino)-1-((phenylsulfanyl)methyl)propyl)amino)-3-nitrobenzenesulfonamide, | |
| N-(4-(4-((4'-chloro(1,1'-biphenyl)-2-yl)methyl)piperazin-1-yl)benzoyl)-3-nitro-4-(((1R)-1-((phenylsulfanyl)methyl)-3-(piperidin-1-yl)propyl)amino)benzenesulfonamide, | |
| N-(4-(4-((4'-chloro(1,1'-biphenyl)-2-yl)methyl)piperazin-1-yl)benzoyl)-4-(((1R)-3-((3R)-3-hydroxypiperidin-1-yl)-1-((phenylsulfanyl)methyl)propyl)amino)-3-nitrobenzenesulfonamide, | |
| 4-(((1R)-3-((3R)-3-aminopyrrolidin-1-yl)-1-((phenylsulfanyl)methyl)propyl)amino)-N-(4-(4-((4'-chloro(1,1'-biphenyl)-2-yl)methyl)piperazin-1-yl)benzoyl)-3-nitrobenzenesulfonamide, | |

| Name | Structure |
|---|---|
| N-(4-(4-((4'-chloro(1,1'-biphenyl)-2-yl)methyl)piperazin-1-yl)benzoyl)-4-(((1R)-3-(3-hydroxyazetidin-1-yl)-1-((phenylsulfanyl)methyl)propyl)amino)-3-nitrobenzenesulfonamide, | 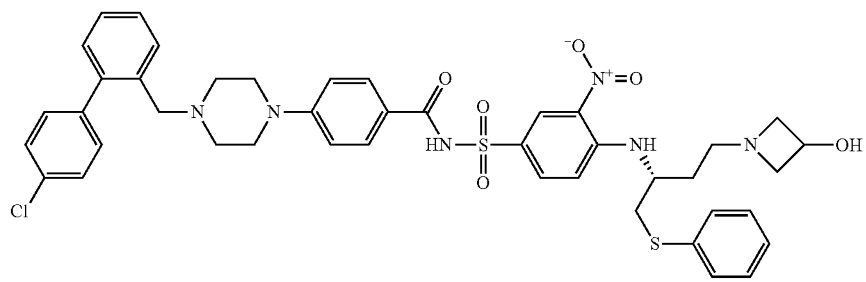 |
| N-(4-(4-((4'-chloro(1,1'-biphenyl)-2-yl)methyl)piperazin-1-yl)benzoyl)-4-(((1R)-3-(4-methylpiperazin-1-yl)-1-((phenylsulfanyl)methyl)propyl)amino)-3-nitrobenzenesulfonamide, | 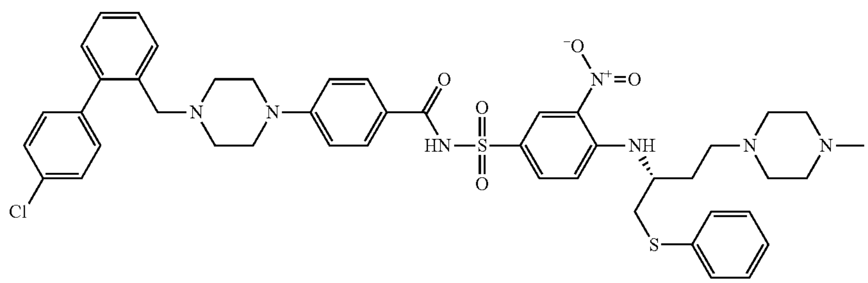 |
| N-(4-(4-((4'-chloro(1,1'-biphenyl)-2-yl)methyl)piperazin-1-yl)benzoyl)-4-(((1R)-3-(1,1'-dioxidothiomorpholin-4-yl)-1-((phenylsulfanyl)methyl)propyl)amino)-3-nitrobenzenesulfonamide, | 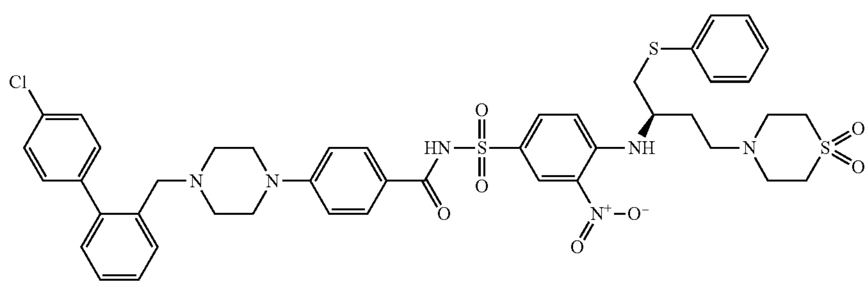 [SMILES: O=C(NS(=O)(=O)c1ccc(N[C@H](CCN2CCS(=O)(=O)CC2)CSc2ccccc2)c([N+](=O)[O-])c1)c1ccc(N2CCN(Cc3ccccc3-c3ccc(Cl)cc3)CC2)cc1] |
| 4-(((1R)-3-(1,3-benzodioxol-5-ylamino)-1-((phenylsulfanyl)methyl)propyl)amino)-N-(4-(4-((4'-chloro(1,1'-biphenyl)-2-yl)methyl)piperazin-1-yl)benzoyl)-3-nitrobenzenesulfonamide, | 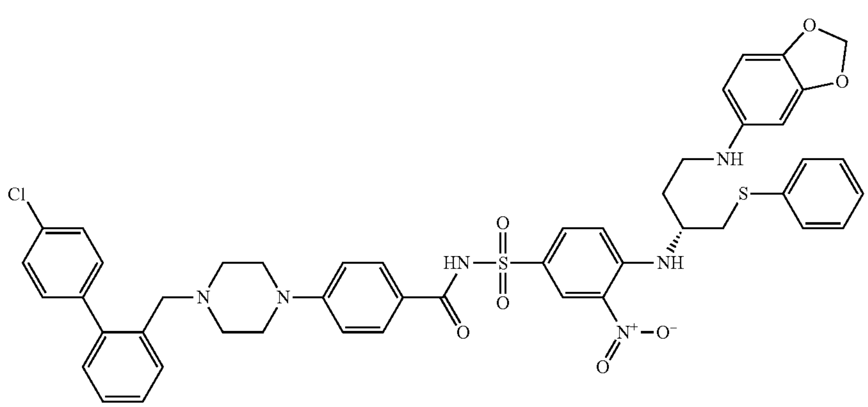 [SMILES: O=C(NS(=O)(=O)c1ccc(N[C@H](CCNc2ccc3c(c2)OCO3)CSc2ccccc2)c([N+](=O)[O-])c1)c1ccc(N2CCN(Cc3ccccc3-c3ccc(Cl)cc3)CC2)cc1] |

| Name | Structure |
|---|---|
| 4-(((1R)-3-((1,3-benzodioxol-4-yl methyl)amino)-1-((phenylsulfanyl)methyl)propyl) amino)-N-(4-(4-((4'-chloro(1,1'-biphenyl)-2-yl)methyl)piperazin-1-yl)benzoyl)-3-nitrobenzenesulfonamide, | 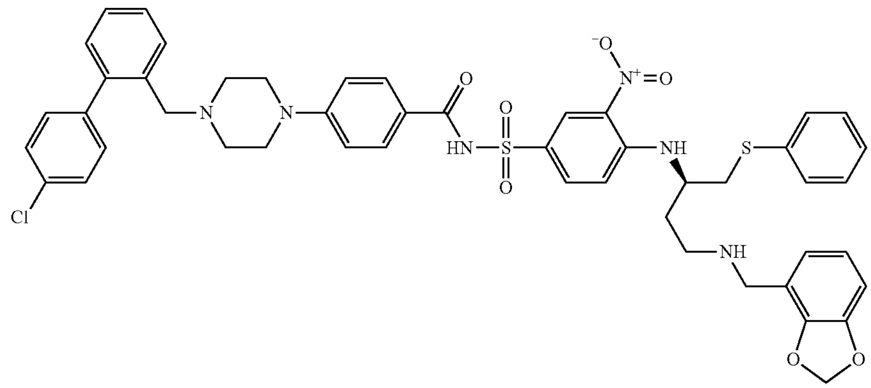 |
| N-(4-(4-((4'-chloro(1,1'-biphenyl)-2-yl)methyl)piperazin-1-yl)benzoyl)-3-nitro-4-(((1R)-1-((phenylsulfanyl)methyl)-3-((pyridin-2-ylmethyl)amino)propyl)amino) benzenesulfonamide, | 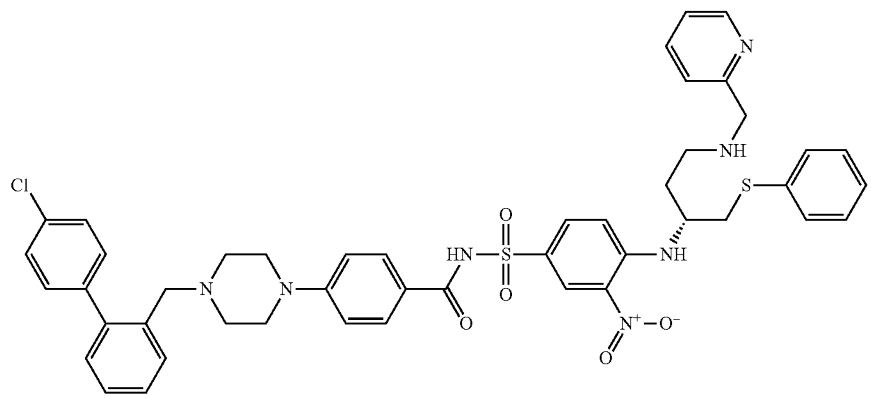 [SMILES: O=C(NS(=O)(=O)c1ccc(N[C@H](CCNCc2ccccn2)CSc2ccccc2)c([N+](=O)[O-])c1)c1ccc(N2CCN(Cc3ccccc3-c3ccc(Cl)cc3)CC2)cc1] |
| N-(4-(4-((4'-chloro(1,1'-biphenyl)-2-yl)methyl)piperazin-1-yl)benzoyl)-3-nitro-4-(((1R)-1-((phenylsulfanyl)methyl)-3-((2-(pyridin-2-yl)ethyl)amino)propyl)amino) benzenesulfonamide, | 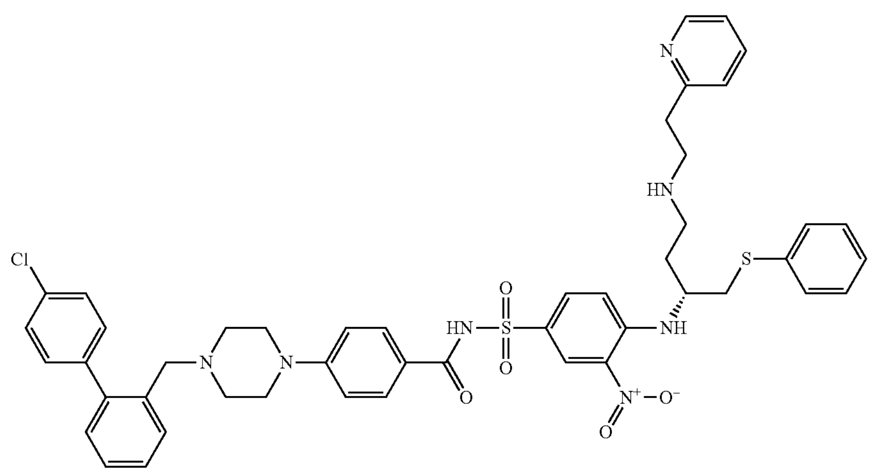 [SMILES: O=C(NS(=O)(=O)c1ccc(N[C@H](CCNCCc2ccccn2)CSc2ccccc2)c([N+](=O)[O-])c1)c1ccc(N2CCN(Cc3ccccc3-c3ccc(Cl)cc3)CC2)cc1] |

| Name | Structure |
|---|---|
| N-(4-(4-((4'-chloro(1,1'-biphenyl)-2-yl)methyl)piperazin-1-yl)benzoyl)-3-nitro-4-(((1R)-1-((phenylsulfanyl)methyl)-3-((pyridin-4-ylmethyl)amino)propyl)amino)benzenesulfonamide, | 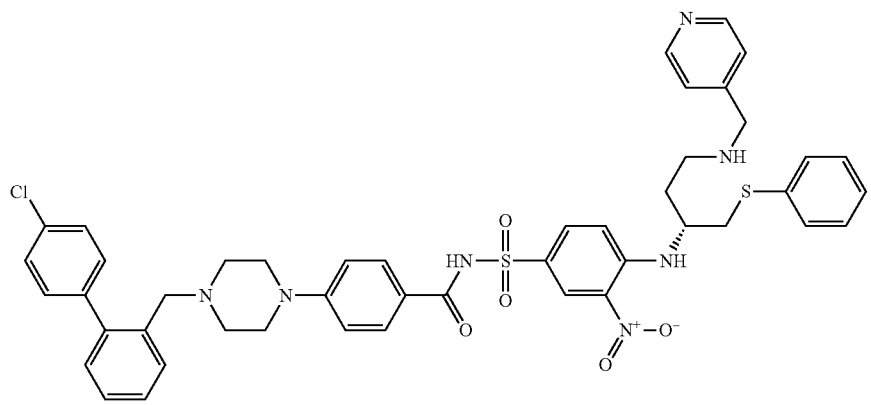 [SMILES: O=C(NS(=O)(=O)c1ccc(N[C@H](CCNCc2ccncc2)CSc2ccccc2)c([N+](=O)[O-])c1)c1ccc(N2CCN(Cc3ccccc3-c3ccc(Cl)cc3)CC2)cc1] |
| N-(4-(4-((4'-chloro(1,1'-biphenyl)-2-yl)methyl)piperazin-1-yl)benzoyl)-4-(((1R)-3-(morpholin-4-ylamino)-1-((phenylsulfanyl)methyl)propyl)amino)-3-nitrobenzenesulfonamide, | 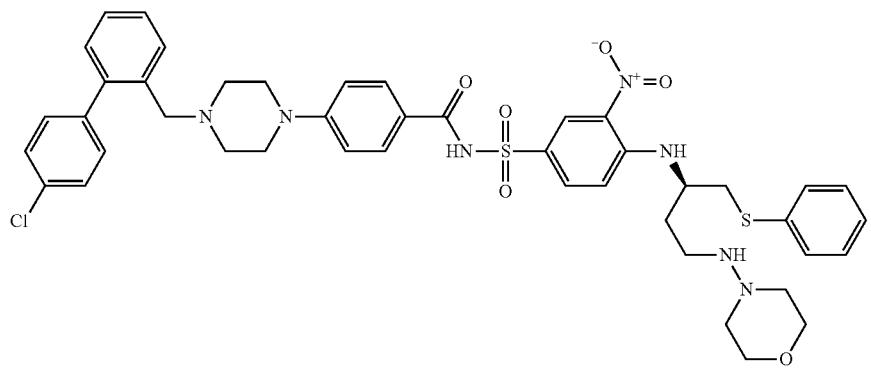 |
| N-(4-(4-((4'-chloro(1,1'-biphenyl)-2-yl)methyl)piperazin-1-yl)benzoyl)-4-(((1R)-3-(methyl(pyridin-4-yl)amino)-1-((phenylsulfanyl)methyl)propyl)amino)-3-nitrobenzenesulfonamide, | 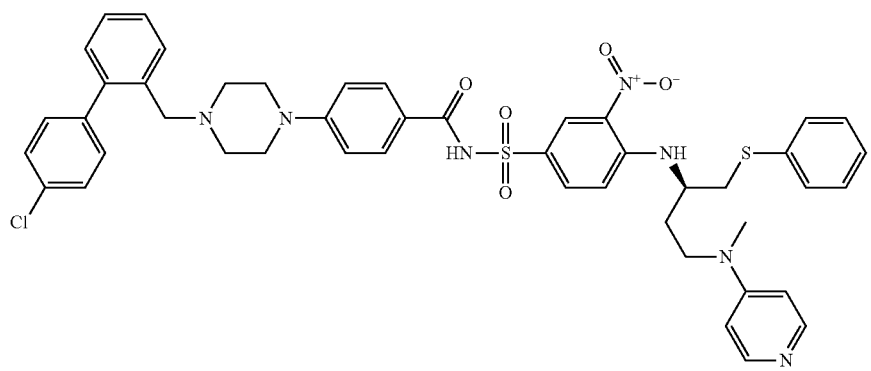 [SMILES: CN(CC[C@H](CSc1ccccc1)Nc1ccc(S(=O)(=O)NC(=O)c2ccc(N3CCN(Cc4ccccc4-c4ccc(Cl)cc4)CC3)cc2)cc1[N+](=O)[O-])c1ccncc1] |
| N-(4-(4-((4'-chloro(1,1'-biphenyl)-2-yl)methyl)piperazin-1-yl)benzoyl)-3-nitro-4-(((1R)-1-((phenylsulfanyl)methyl)-3-(pyridin-3-ylamino)propyl)amino)benzenesulfonamide, | 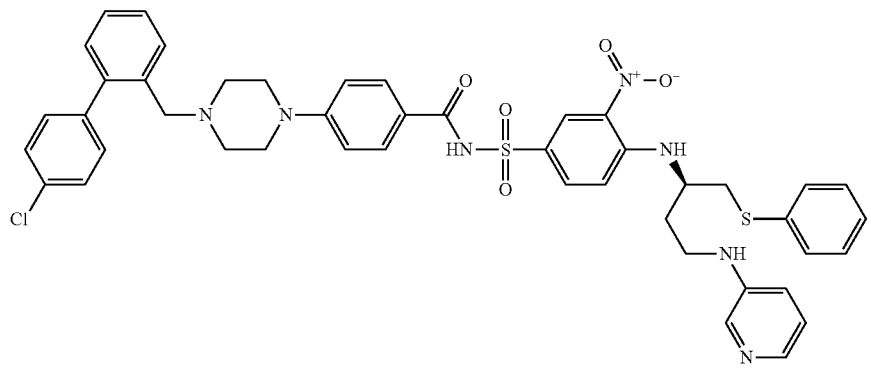 [SMILES: O=C(NS(=O)(=O)c1ccc(N[C@H](CCNc2cccnc2)CSc2ccccc2)c([N+](=O)[O-])c1)c1ccc(N2CCN(Cc3ccccc3-c3ccc(Cl)cc3)CC2)cc1] |

-continued

| Name | Structure |
|---|---|
| N-(4-(4-((4'-chloro(1,1'-biphenyl)-2-yl)methyl)piperazin-1-yl)benzoyl)-4-(((1R)-3-(2,6-dimethylpiperidin-1-yl)-1-((phenylsulfanyl)methyl)propyl)amino)-3-nitrobenzenesulfonamide, | 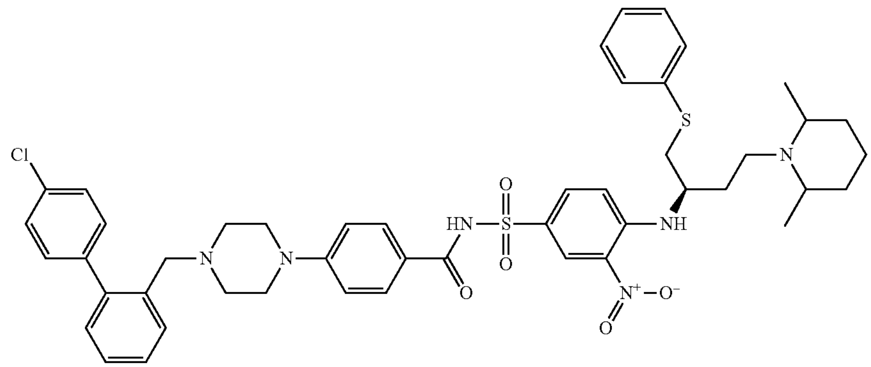 [SMILES: CC1CCCC(C)N1CC[C@H](CSc1ccccc1)Nc1ccc(S(=O)(=O)NC(=O)c2ccc(N3CCN(Cc4ccccc4-c4ccc(Cl)cc4)CC3)cc2)cc1[N+](=O)[O-]] |
| N-(4-(4-((4'-chloro(1,1'-biphenyl)-2-yl)methyl)piperazin-1-yl)benzoyl)-4-(((1R)-3-((2R,6S)-2,6-dimethylpiperidin-1-yl)-1-((phenylsulfanyl)methyl)propyl)amino)-3-nitrobenzenesulfonamide, | 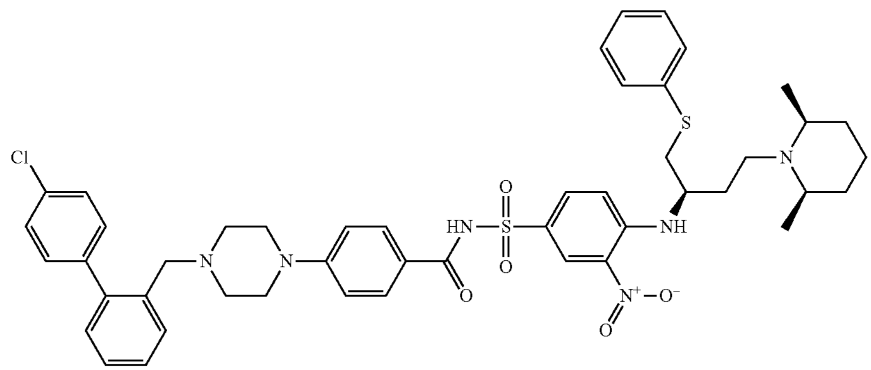 [SMILES: C[C@@H]1CCC[C@H](C)N1CC[C@H](CSc1ccccc1)Nc1ccc(S(=O)(=O)NC(=O)c2ccc(N3CCN(Cc4ccccc4-c4ccc(Cl)cc4)CC3)cc2)cc1[N+](=O)[O-]] |
| N-(4-(4-((4'-chloro(1,1'-biphenyl)-2-yl)methyl)piperazin-1-yl)benzoyl)-3-nitro-4-(((1R)-1-((phenylsulfanyl)methyl)-3-(pyrrolidin-1-ylamino)propyl)amino)benzenesulfonamide, | |
| N-(4-(4-((4'-chloro(1,1'-biphenyl)-2-yl)methyl)piperazin-1-yl)benzoyl)-4-(((1R)-3-(4-(methoxyimino)piperidin-1-yl)-1-((phenylsulfanyl)methyl)propyl)amino)-3-nitrobenzenesulfonamide, | 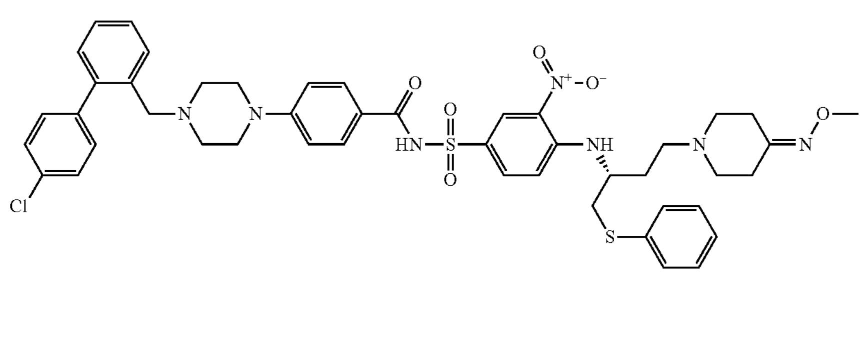 [SMILES: CON=C1CCN(CC[C@H](CSc2ccccc2)Nc2ccc(S(=O)(=O)NC(=O)c3ccc(N4CCN(Cc5ccccc5-c5ccc(Cl)cc5)CC4)cc3)cc2[N+](=O)[O-])CC1] |

| Name | Structure |
|---|---|
| N-(4-(4-((4'-chloro(1,1'-biphenyl)-2-yl)methyl)piperazin-1-yl)benzoyl)-3-nitro-4-(((1R)-1-((phenylsulfanyl)methyl)-3-(2H-tetrazol-5-yl)propyl)amino)benzenesulfonamide, | |
| N-4-(4-((4'-chloro(1,1'-biphenyl)-2-yl)methyl)piperazin-1-yl)benzoyl)-4-(((1R)-3-(diisopropylamino)-1-((phenylsulfanyl)methyl)propyl)amino)-3-(trifluoromethyl)benzenesulfonamide. | |
| N-(4-(4-((4'-chloro(1,1'-biphenyl)-2-yl)rnethyl)piperazin-1-yl)benzoyl)-4-(((1R)-3-(isopropylamino)-1-((phenylsulfanyl)methyl)propyl)amino)-3-(trifluoromethyl)benzenesulfonamide, | |
| 4-(((1R)-3-(bis(2-hydroxyethyl)amino)-1-((phenylsulfanyl)methyl)propyl)amino)-N-(4-(4-((4'-chloro(1,1'-biphenyl)-2-yl)methyl)piperazin-1-yl)benzoyl)-3-nitrobenzenesulfonamide, | |

| Name | Structure |
|---|---|
| N-(4-(4-((4'-chloro(1,1'-biphenyl)-2-yl)methyl)piperazin-1-yl)benzoyl)-3-(((1R)-3-(dimethylamino)-1-((phenylsulfanyl)methyl)propyl)amino)-4-(trifluoromethoxy)benzenesulfonamide, | 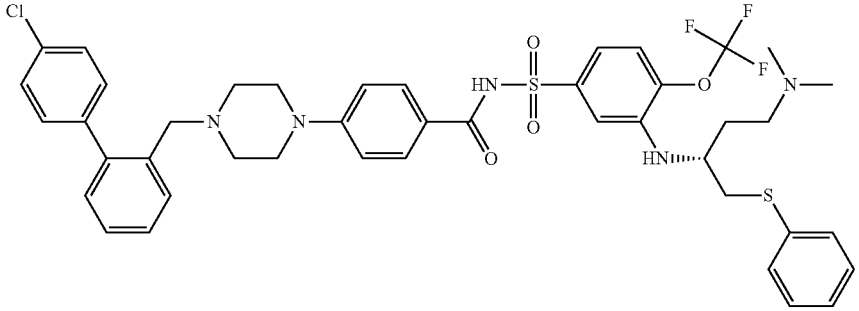 [SMILES: CN(C)CC[C@H](CSc1ccccc1)Nc1cc(S(=O)(=O)NC(=O)c2ccc(N3CCN(Cc4ccccc4-c4ccc(Cl)cc4)CC3)cc2)ccc1OC(F)(F)F] |
| N-(4-(4-((4'-chloro(1,1'-biphenyl)-2-yl)methyl)piperazin-1-yl)benzoyl)-4-(((1R)-3-(isopropyl(methyl)amino)-1-((phenylsulfanyl)methyl)propyl)amino)-3-(trifluoromethyl)benzenesulfonamide, | 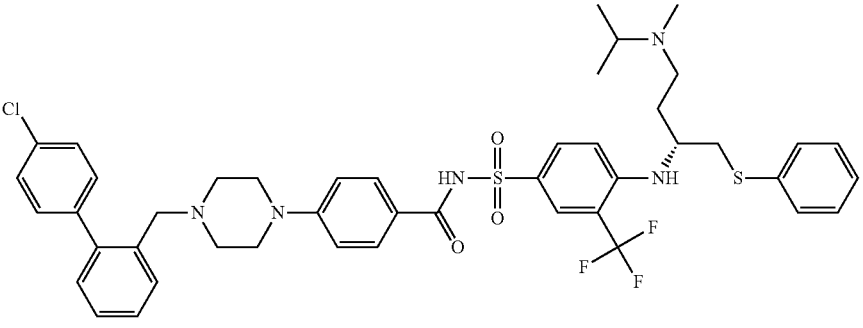 [SMILES: CC(C)N(C)CC[C@H](CSc1ccccc1)Nc1ccc(S(=O)(=O)NC(=O)c2ccc(N3CCN(Cc4ccccc4-c4ccc(Cl)cc4)CC3)cc2)cc1C(F)(F)F] |
| N-(4-(4-((4''-chloro(1,1'-biphenyl)-2-yl)methyl)piperazin-1-yl)benzoyl)-4-(((1R)-3-(diethylamino)-1-((phenylsulfanyl)methyl)propyl)amino)-3-(trifluoromethyl)benzenesulfonamide, | 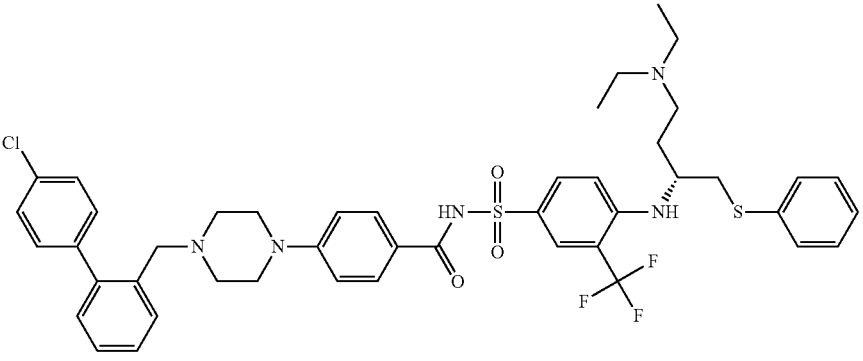 [SMILES: CCN(CC)CC[C@H](CSc1ccccc1)Nc1ccc(S(=O)(=O)NC(=O)c2ccc(N3CCN(Cc4ccccc4-c4ccc(Cl)cc4)CC3)cc2)cc1C(F)(F)F] |
| N-(4-(4-((4'-chloro(1,1'-biphenyl)-2-yl)methyl)piperazin-1-yl)benzoyl)-4-(((1R)-3-(2,5-dimethylpyrrolidin-1-yl)-1-((phenylsulfanyl)methyl)propyl)amino)-3-nitrobenzenesulfonamide, | 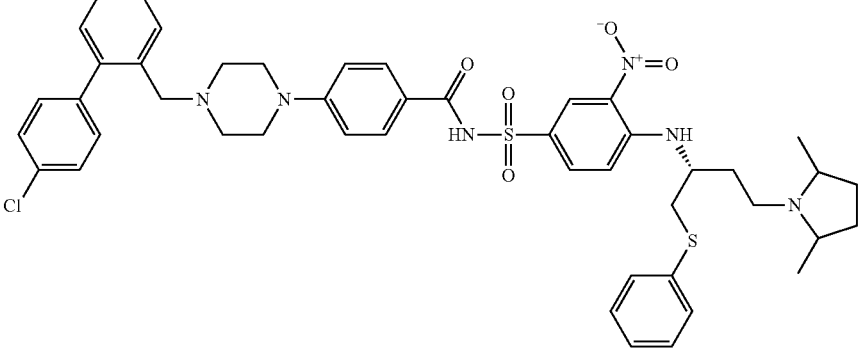 |

| Name | Structure |
|---|---|
| 4-(((1R)-3-amino-1-((phenylsulfanyl)methyl)propyl)amino)-N-(4-(4-((4'-chloro(1,1'-biphenyl)-2-yl)methyl)piperazin-1-yl)benzoyl)-3-(trifluoromethyl)benzenesulfonamide, | 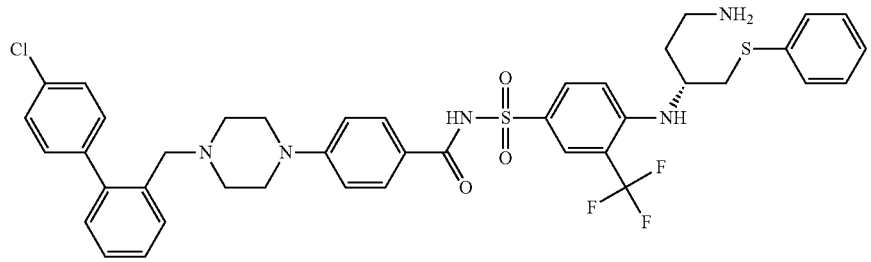 [SMILES: NCC[C@H](CSc1ccccc1)Nc1ccc(S(=O)(=O)NC(=O)c2ccc(N3CCN(Cc4ccccc4-c4ccc(Cl)cc4)CC3)cc2)cc1C(F)(F)F] |
| N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-2-(trifluoromethyl)benzenesulfonamide, | 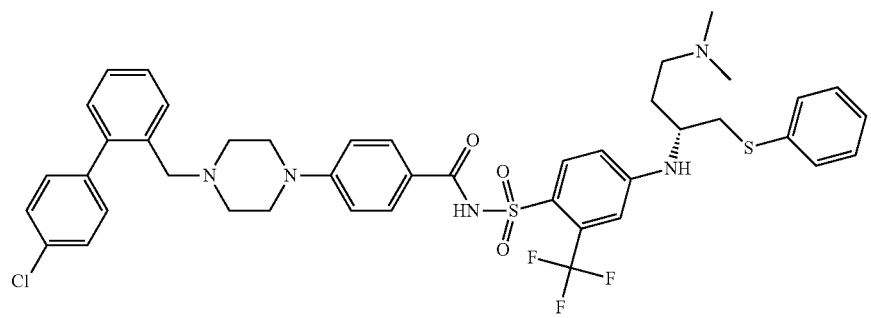 [SMILES: CN(C)CC[C@H](CSc1ccccc1)Nc1ccc(S(=O)(=O)NC(=O)c2ccc(N3CCN(Cc4ccccc4-c4ccc(Cl)cc4)CC3)cc2)c(C(F)(F)F)c1] |
| N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-fluorobenzenesulfonamide, |  |
| N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-2-(trifluoromethoxy)benzenesulfonamide, | 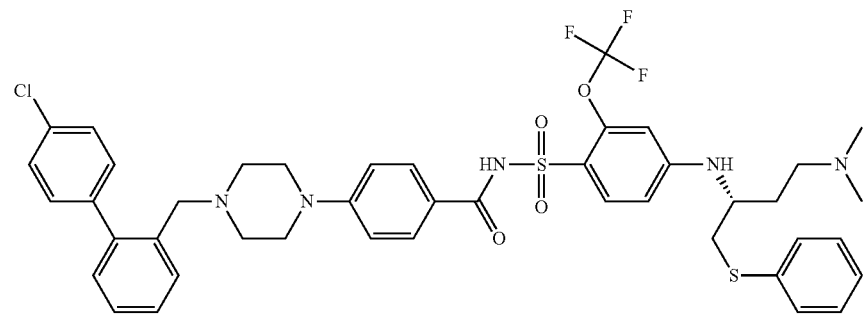 [SMILES: CN(C)CC[C@H](CSc1ccccc1)Nc1ccc(S(=O)(=O)NC(=O)c2ccc(N3CCN(Cc4ccccc4-c4ccc(Cl)cc4)CC3)cc2)c(OC(F)(F)F)c1] |
| N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-2,5-difluorobenzenesulfonamide, | 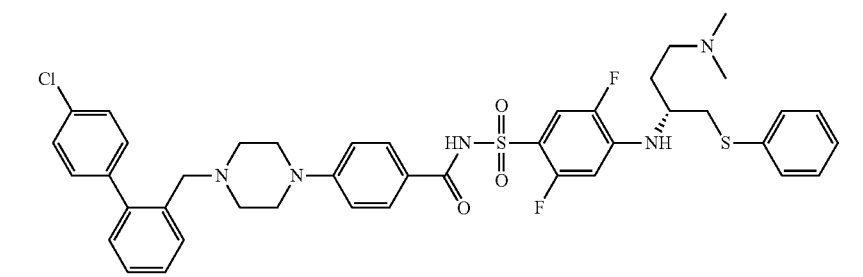 |

| Name | Structure |
|---|---|
| N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-methylbenzenesulfonamide, | 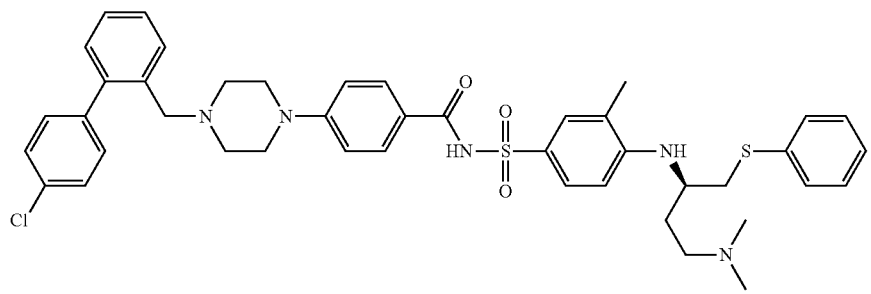 [SMILES: Cc1cc(S(=O)(=O)NC(=O)c2ccc(N3CCN(Cc4ccccc4-c4ccc(Cl)cc4)CC3)cc2)ccc1N[C@H](CCN(C)C)CSc1ccccc1] |
| N-(4-(4-((2-(4-chlorophenyl)-1-cyclohexen-1-yl)methyl)piperazin-1-yl)benzoyl)-4-(((1R)-3-(diisopropylamino)-1-((phenylsulfanyl)methyl)propyl)amino)-3-nitrobenzenesulfonamide, | 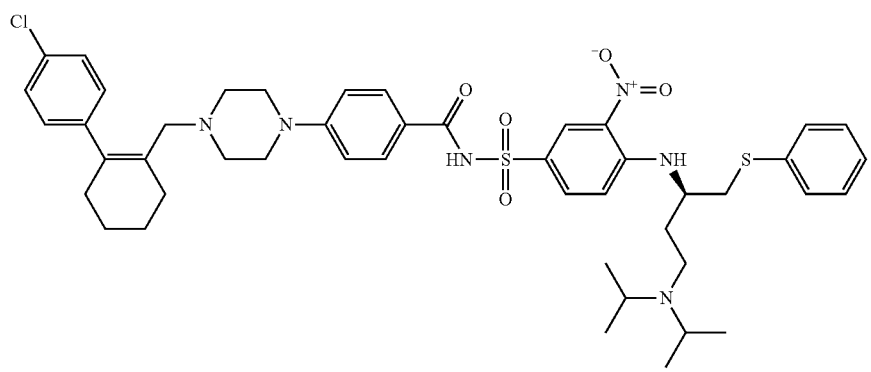 |
| N-(4-(4-((4'-chloro(1,1'-biphenyl)-2-yl)methyl)piperazin-1-yl)benzoyl)-4-(((1R)-3-((2R,5R)-2,5-dimethylpyrrolidin-1-yl)-1-((phenylsulfanyl)methyl)propyl)amino)-3-nitrobenzenesulfonamide, | 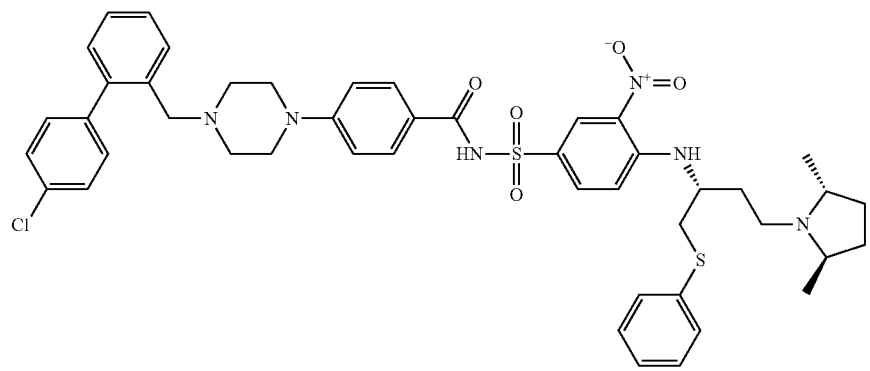 |
| N-(4-(4-((4'-chloro(1,1'-biphenyl)-2-yl)methyl)piperazin-1-yl)benzoyl)-4-(((1R)-3-((2S,5S)-2,5-dimethylpyrrolidin-1-yl)-1-((phenylsulfanyl)methyl)propyl)amino)-3-nitrobenzenesulfonamide, | 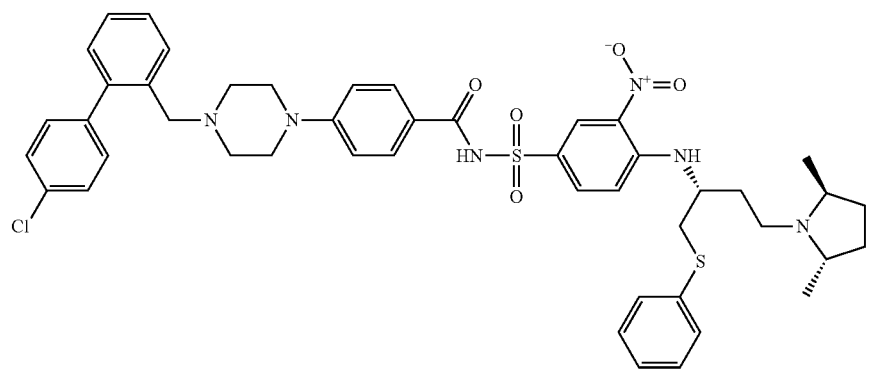 |

-continued

| Name | Structure |
|---|---|
| N-(4-(4-((4'-chloro(1,1'-biphenyl)-2-yl)methyl)piperazin-1-yl)benzoyl)-4-(((1R)-3-((2R,5S)-2,5-dimethylpyrrolidin-1-yl)-1-((phenylsulfanyl)methyl)propyl)amino)-3-nitrobenzenesulfonamide, | 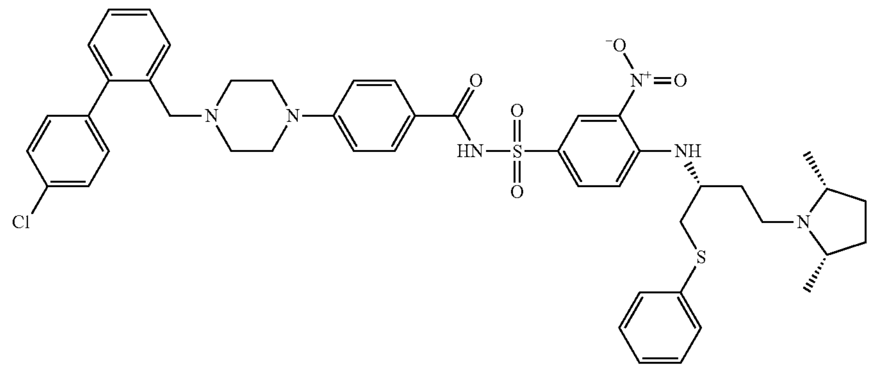 |
| N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitro-5-(trifluoromethyl)benzene-sulfonamide, | 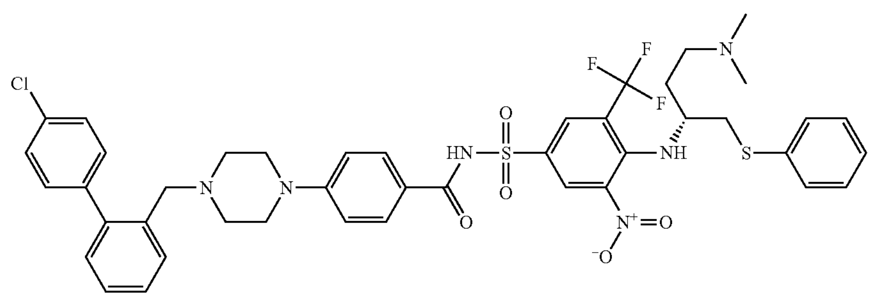 |
| N-(4-(4-((2-(4-chlorophenyl)-1-cyclohexen-1-yl)methyl)piperazin-1-yl)benzoyl)-4-(((1R)-3-(dimethylamino)-1-((phenylsulfanyl)methyl)propyl)amino)-3-nitro-5-(trifluoromethyl)benzene-sulfonamide, | 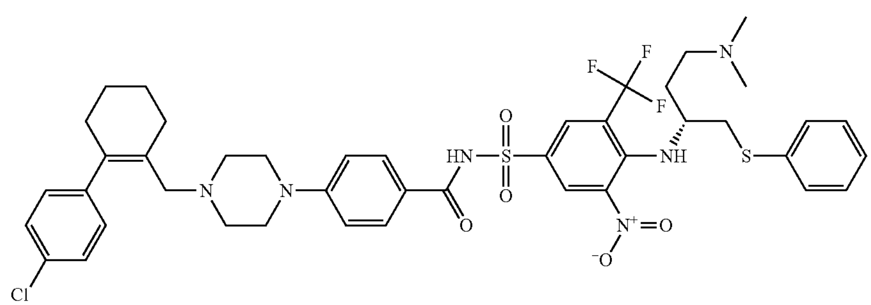 |
| N-(4-(4-((2-(4-chlorophenyl)-1-cyclohepten-1-yl)methyl)piperazin-1-yl)benzoyl)-4-(((1R)-3-(dimethylamino)-1-((phenylsulfanyl)methyl)propyl)amino)-3-nitro-5-(trifluoromethyl)benzene-sulfonamide, | 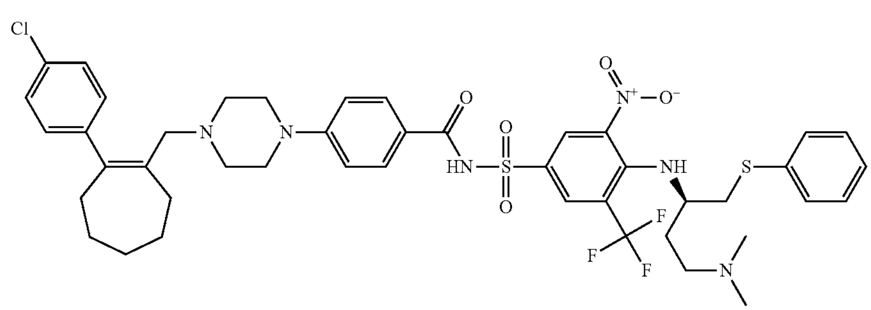 [SMILES: CN(C)CC[C@H](CSc1ccccc1)Nc1c([N+](=O)[O-])cc(S(=O)(=O)NC(=O)c2ccc(N3CCN(CC4=C(c5ccc(Cl)cc5)CCCCC4)CC3)cc2)cc1C(F)(F)F] |

US 10,195,213 B2

215 216

-continued

| Name | Structure |
|---|---|
| N-(4-(4-((4'-chloro(1,1'-biphenyl)-2-yl)methyl)piperazin-1-yl)benzoyl)-3-(((1R)-3-(dimethylamino)-1-((phenylsulfanyl)methyl)propyl)amino)-4-nitrobenzenesulfonamide, | 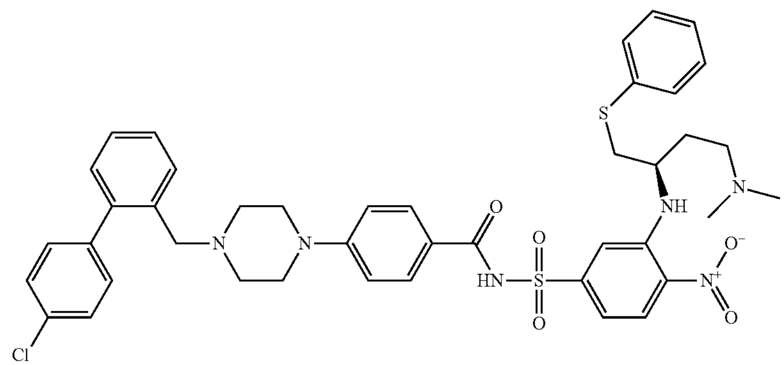 [SMILES: CN(C)CC[C@H](CSc1ccccc1)Nc1cc(S(=O)(=O)NC(=O)c2ccc(N3CCN(Cc4ccccc4-c4ccc(Cl)cc4)CC3)cc2)ccc1[N+](=O)[O-]] |
| N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3,5-difluorobenzenesulfonamide, | 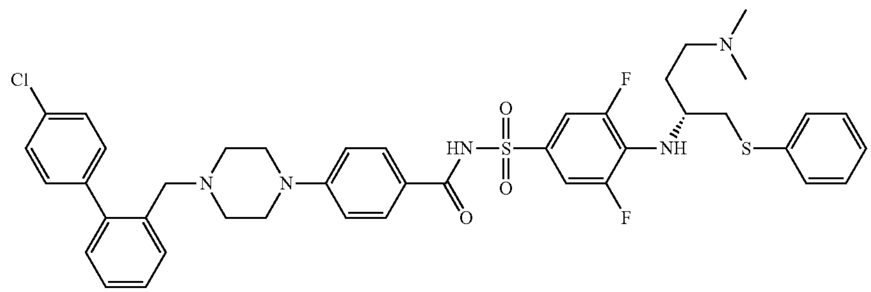 |
| methyl 5-(((4-(4-((4'-chloro(1,1'-biphenyl)-2-yl)methyl)piperazin-1-yl)benzoyl)amino)sulfonyl)-2-(((1R)-3-(dimethylamino)-1-((phenylsulfanyl)methyl)propyl)amino)-3-nitrobenzoate, | 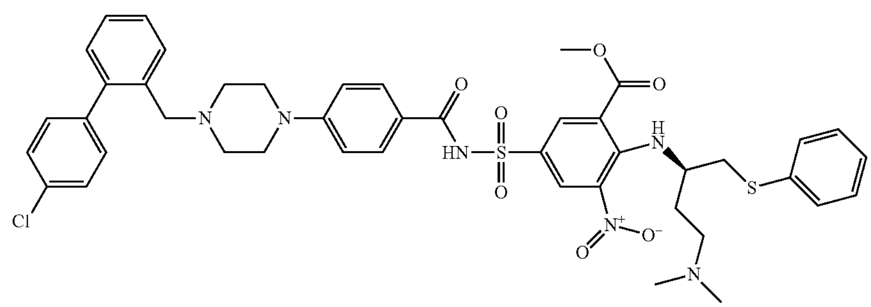 [SMILES: COC(=O)c1cc(S(=O)(=O)NC(=O)c2ccc(N3CCN(Cc4ccccc4-c4ccc(Cl)cc4)CC3)cc2)cc([N+](=O)[O-])c1N[C@H](CCN(C)C)CSc1ccccc1] |
| 5-(((4-(4-((4'-chloro(1,1'-biphenyl)-2-yl)methyl)piperazin-1-yl)benzoyl)amino)sulfonyl)-2-(((1R)-3-(dimethylamino)-1-((phenylsulfanyl)methyl)propyl)amino)-3-nitrobenzoic acid, | |
| 5-(((4-(4-((4'-chloro(1,1'-biphenyl)-2-yl)methyl)piperazin-1-yl)benzoyl)amino)sulfonyl)-2-(((1R)-3-(dimethylamino)-1-((phenylsulfanyl)methyl)propyl)amino)-3-nitrobenzoic acid, | |

-continued

| Name | Structure |
|---|---|
| 5-(((4-(4-((2-(4-chlorophenyl)-1-cyclohexen-1-yl)methyl)piperazin-1-yl)benzoyl)amino)sulfonyl)-2-(((1R)-3-(dimethylamino)-1-((phenylsulfanyl)methyl)propyl)amino)-3-nitrobenzoic acid, | 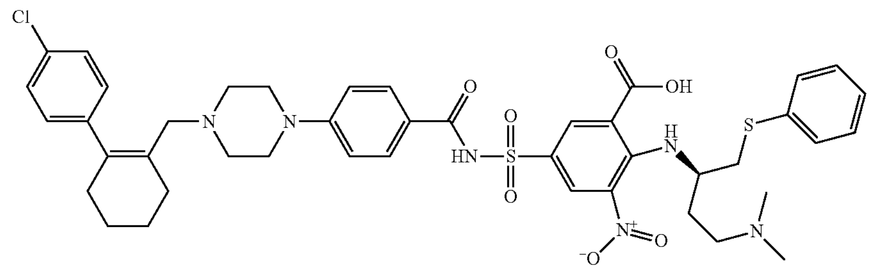 |
| 5-(((4-(4-((2-(4-chlorophenyl)-1-cyclohexen-1-yl)methyl)piperazin-1-yl)benzoyl)amino)sulfonyl)-2-(((1R)-3-(dimethylamino)-1-((phenylsulfanyl)methyl)propyl)amino)-3-nitrobenzamide, | 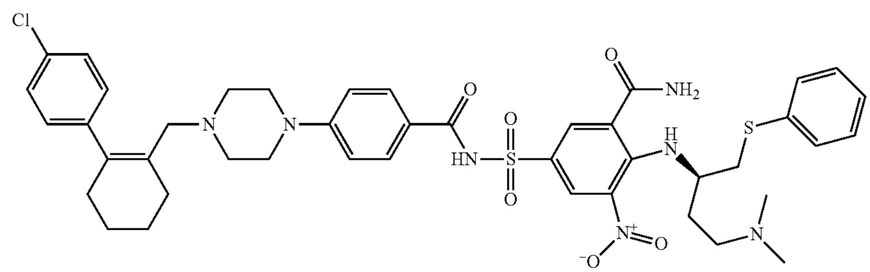 |
| 5-(((4-(4-((4'-chloro(1,1'-biphenyl)-2-yl)methyl)piperazin-1-yl)benzoyl)amino)sulfonyl)-2-(((1R)-3-(dimethylamino)-1-((phenylsulfanyl)methyl)propyl)amino)-3-nitrobenzamide, | 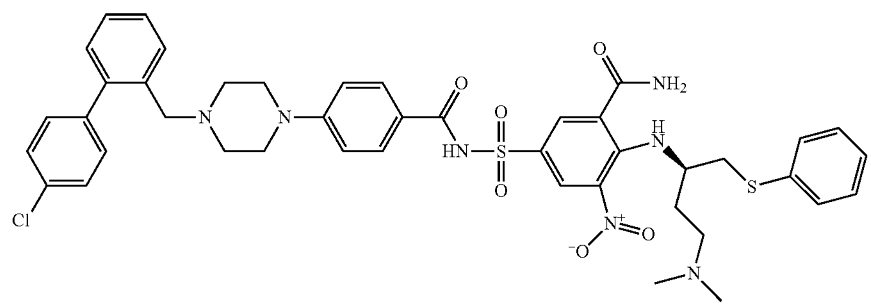 |
| methyl 5-(((4-(4-((2-(4-cblorophenyl)-1-cyclohexen-1-yl)methyl)piperazin-1-yl)benzoyl)amino)sulfonyl)-2-(((1R)-3-(dimethylamino)-1-((phenylsulfanyl)methyl)propyl)amino)-3-(trifluoromethyl)benzoate, | 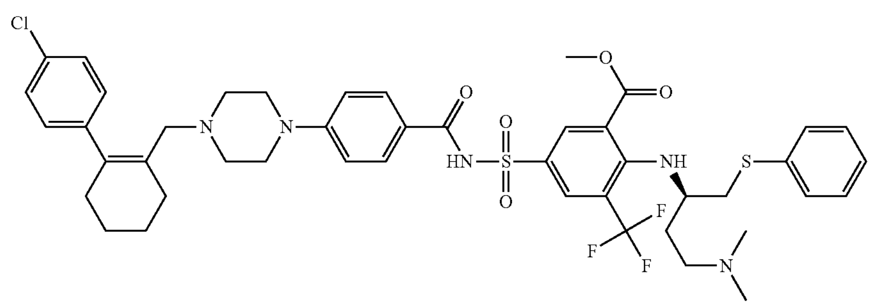 [SMILES: COC(=O)c1cc(S(=O)(=O)NC(=O)c2ccc(N3CCN(CC4=C(c5ccc(Cl)cc5)CCCC4)CC3)cc2)cc(C(F)(F)F)c1N[C@H](CCN(C)C)CSc1ccccc1] |
| methyl 5-(((4-(4-((4-(4-chlorophenyl)-5,6-dihydro-2H-pyran-3-yl)methyl)piperazin-1-yl)benzoyl)amino)sulfonyl)-2-(((1R)-3-(dimethylamino)-1-((phenylsulfanyl)methyl)propyl)amino)-3-(trifluoromethyl)benzoate, | 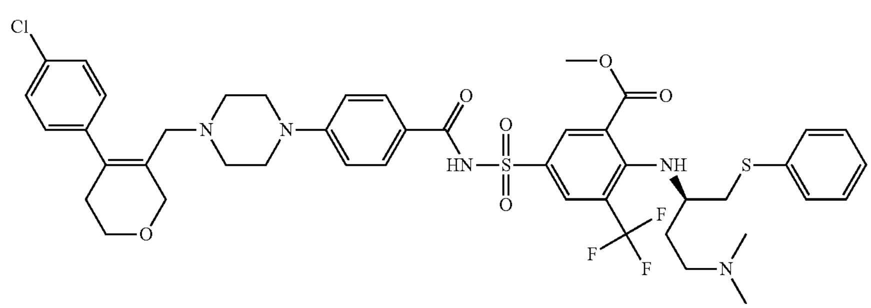 [SMILES: COC(=O)c1cc(S(=O)(=O)NC(=O)c2ccc(N3CCN(CC4=C(c5ccc(Cl)cc5)CCOC4)CC3)cc2)cc(C(F)(F)F)c1N[C@H](CCN(C)C)CSc1ccccc1] |

-continued

| Name | Structure |
|---|---|
| methyl 5-(((4-(4-((4'-chloro(1,1'-biphenyl)-2-yl)methyl)piperazin-1-yl)benzoyl)amino)sulfonyl)-2-(((1R)-3-(dimethylamino)-1-((phenylsulfanyl)methyl)propyl)amino)-3-(trifluoromethyl)benzoate, | 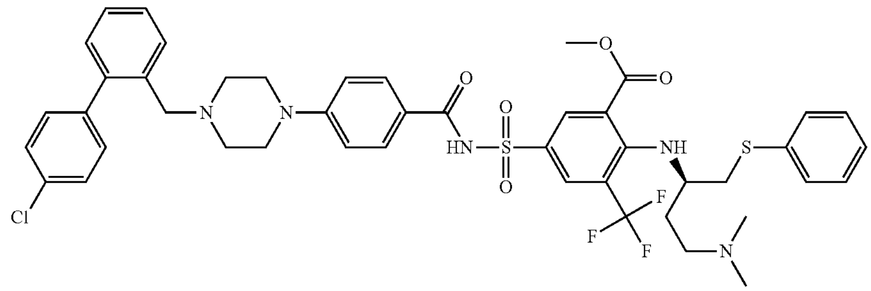 [SMILES: COC(=O)c1cc(S(=O)(=O)NC(=O)c2ccc(N3CCN(Cc4ccccc4-c4ccc(Cl)cc4)CC3)cc2)cc(C(F)(F)F)c1N[C@H](CCN(C)C)CSc1ccccc1] |
| N-(4-(4-((2-(4-chlorophenyl)-1-cyclohexen-1-yl)methyl)piperazin-1-yl)benzoyl)-4-(((1R)-4-((2R,5S)-2,5-dimethylpyrrolidin-1-yl)-1-((phenylsulfanyl)methyl)butyl)amino)-3-nitrobenzenesulfonamide, | 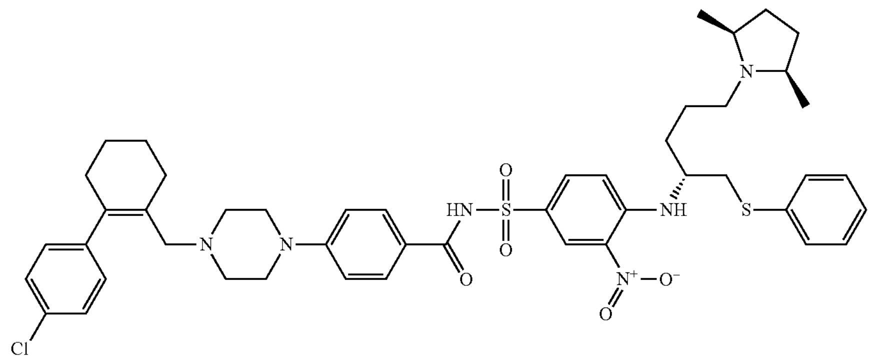 [SMILES: C[C@@H]1CC[C@H](C)N1CCC[C@H](CSc1ccccc1)Nc1ccc(S(=O)(=O)NC(=O)c2ccc(N3CCN(CC4=C(c5ccc(Cl)cc5)CCCC4)CC3)cc2)cc1[N+](=O)[O-]] |
| N-(4-(4-((4-(4-chlorophenyl)-5,6-dihydro-2H-pyran-3-yl)methyl)piperazin-1-yl)benzoyl)-4-(((1R)-4-((2R,5S)-2,5-dimethylpyrrolidin-1-yl)-1-((phenylsulfanyl)methyl)butyl)amino)-3-nitrobenzenesulfonamide, | 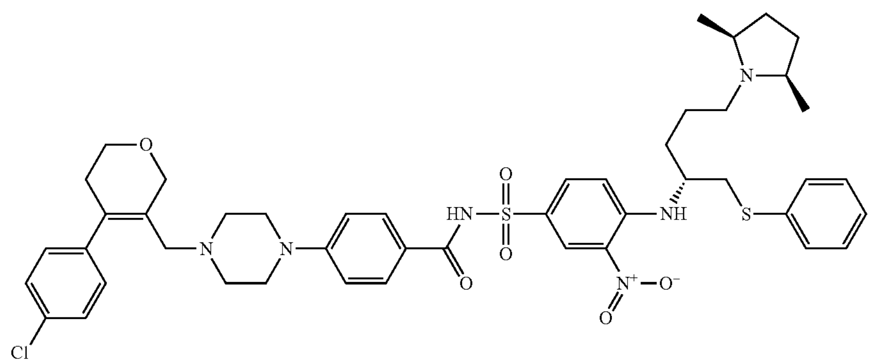 [SMILES: C[C@@H]1CC[C@H](C)N1CCC[C@H](CSc1ccccc1)Nc1ccc(S(=O)(=O)NC(=O)c2ccc(N3CCN(CC4=C(c5ccc(Cl)cc5)CCOC4)CC3)cc2)cc1[N+](=O)[O-]] |
| tert-butyl 3-((4-(4-((((4-(((1R)-3-(dimethylamino)-1-((phenylsulfanyl)methyl)propyl)amino)-3-nitrophenyl)sulfonyl)amino)carbonyl)phenyl)piperazin-1-yl)carbonyl)phenylcarbamate, | 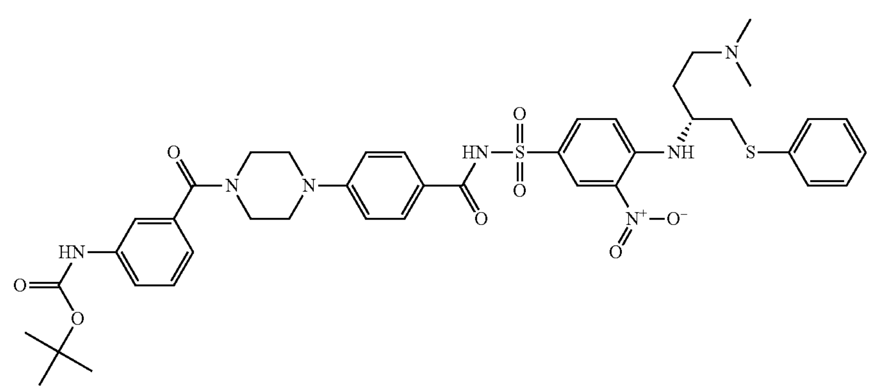 [SMILES: CN(C)CC[C@H](CSc1ccccc1)Nc1ccc(S(=O)(=O)NC(=O)c2ccc(N3CCN(C(=O)c4cccc(NC(=O)OC(C)(C)C)c4)CC3)cc2)cc1[N+](=O)[O-]] |

-continued

| Name | Structure |
|---|---|
| N-(4-(4-(3-(dimethylamino)benzoyl)piperazin-1-yl)benzoyl)-4-(((1R)-3-(dimethylamino)-1-((phenylsulfanyl)methyl)propyl)amino)-3-nitrobenzenesulfonamide, | 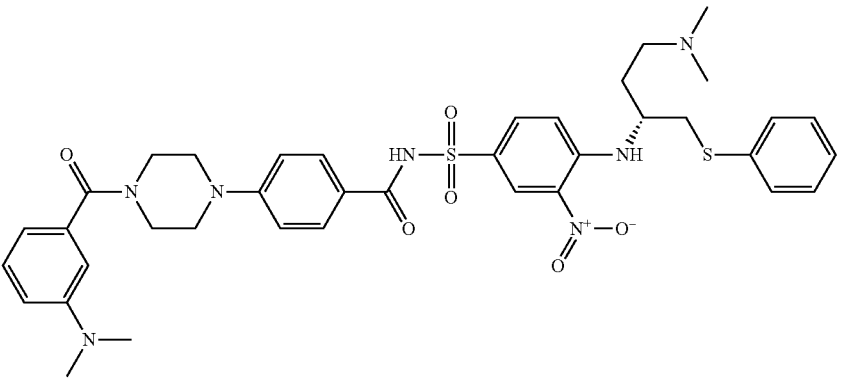 [SMILES: CN(C)CC[C@H](CSc1ccccc1)Nc1ccc(S(=O)(=O)NC(=O)c2ccc(N3CCN(C(=O)c4cccc(N(C)C)c4)CC3)cc2)cc1[N+](=O)[O-]] |
| N-(4-(4-((1,1'-biphenyl)-2-ylmethyl)piperazin-1-yl)benzoyl)-4-(((1R)-3-(dimethylamino)-1-methyl-1-((phenylsulfanyl)methyl)propyl)amino)-3-nitrobenzenesulfonamide, | 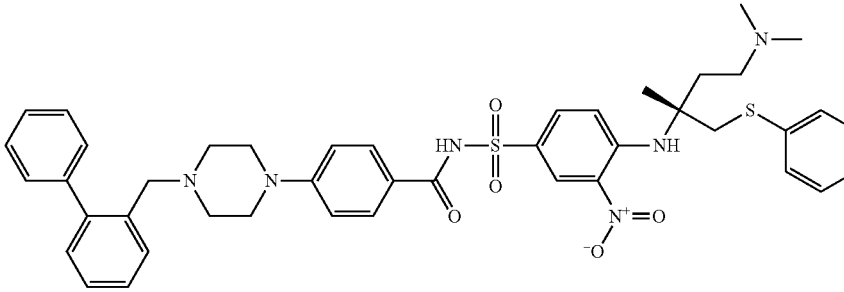 |
| N-(4-(4-((1,1'-biphenyl)-2-ylmethyl)piperazin-1-yl)benzoyl)-4-(((1S)-3-(dimethylamino)-1-methyl-1-((phenylsulfanyl)methyl)propyl)amino)-3-nitrobenzenesulfonamide, | 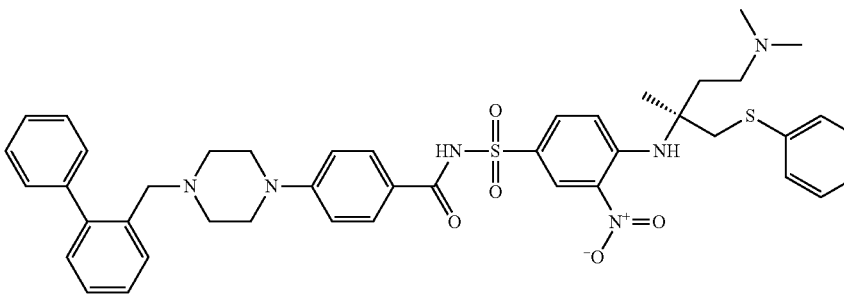 |
| N-(4-(4-(2-(1,3-dihydro-2H-isoindol-2-yl)benzyl)piperazin-1-yl)benzoyl)-4-(((1R)-3-(dimethylamino)-1-((phenylsulfanyl)methyl)propyl)amino)-3-nitrobenzenesulfonamide, | 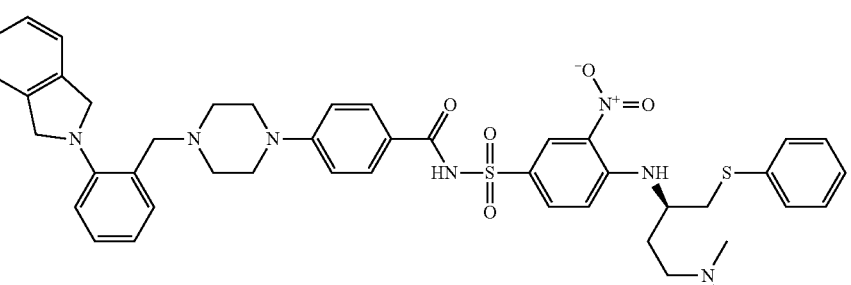 |

| Name | Structure |
|---|---|
| N-(4-(4-(2-(cyclohexylamino)benzyl)piperazin-1-yl)benzoyl)-4-(((1R)-3-(dimethylamino)-1-((phenylsulfanyl)methyl)propyl)amino)-3-nitrobenzenesulfonamide, | 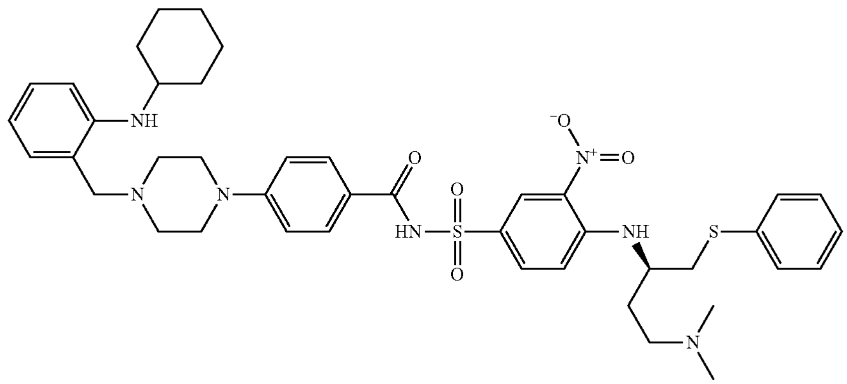 |
| 4-(((1R)-3-(dimethylamino)-1-((phenylsulfanyl)methyl)propyl)amino)-N-(4-(4-(2-(isopropylamino)benzyl)piperazin-1-yl)benzoyl)-3-nitrobenzenesullbnamide, | 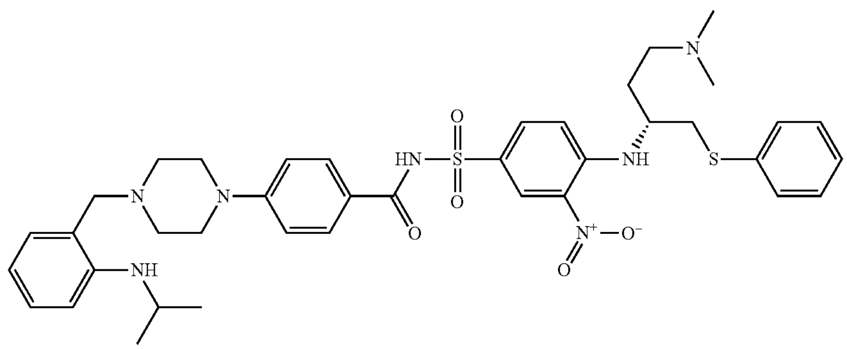 [SMILES: CC(C)Nc1ccccc1CN1CCN(c2ccc(C(=O)NS(=O)(=O)c3ccc(N[C@H](CCN(C)C)CSc4ccccc4)c([N+](=O)[O-])c3)cc2)CC1] |
| N-(4-(4-(2-(benzylamino)benzyl)piperazin-1-yl)benzoyl)-4-(((1R)-3-(dimethylamino)-1-((phenylsulfanyl)methyl)propyl)amino)-3-nitrobenzenesulfonamide, | 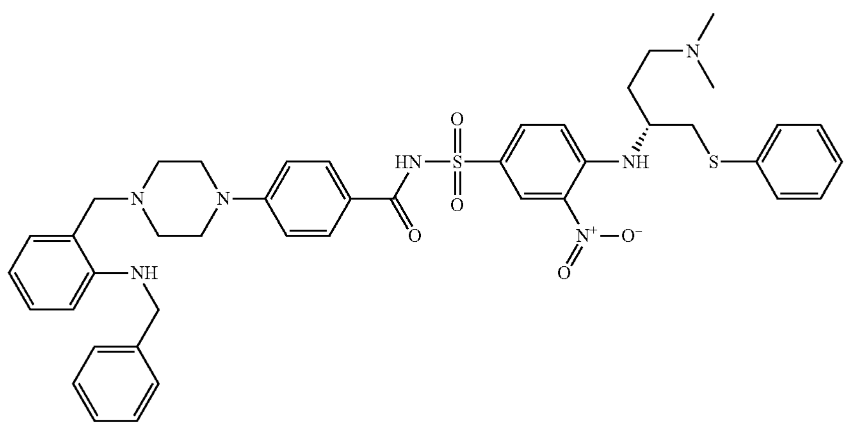 [SMILES: CN(C)CC[C@H](CSc1ccccc1)Nc1ccc(S(=O)(=O)NC(=O)c2ccc(N3CCN(Cc4ccccc4NCc4ccccc4)CC3)cc2)cc1[N+](=O)[O-]] |
| 4-(((1R)-3-(dimethylamine)-1-((phenylsulfanyl)methyl)propyl)amino)-3-nitro-N-(4-(4-(2-(piperidin-1-yl)benzyl)piperazin-1-yl)benzoyl)benzenesulfonamide, | 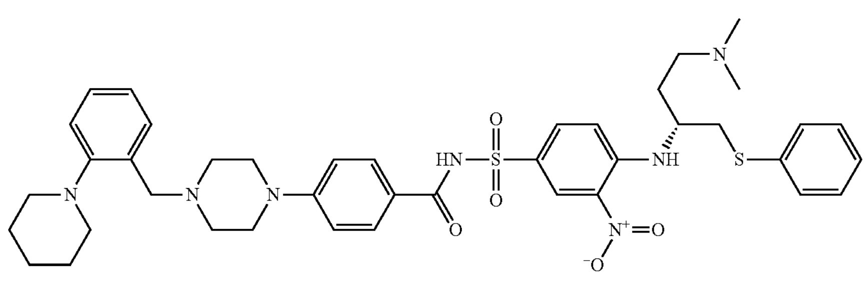 |

| Name | Structure |
|---|---|
| N-(4-(4-((1,1'-biphenyl)-2-ylmethyl)piperazin-1-yl)benzoyl)-3-nitro-4-((2-(phenylsulfanyl)ethyl)amino)benzenesulfonamide, | 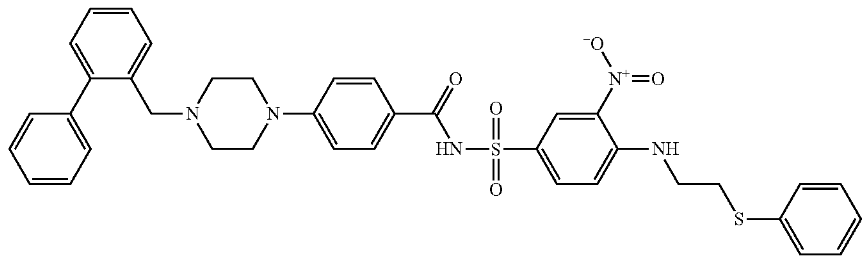 |
| N-(4-(4-((1,1'-biphenyl)-2-ylmethyl)piperazin-1-yl)benzoyl)-4-((cyclohexylmethyl)amino)-3-nitrobenzenesulfonamide, | 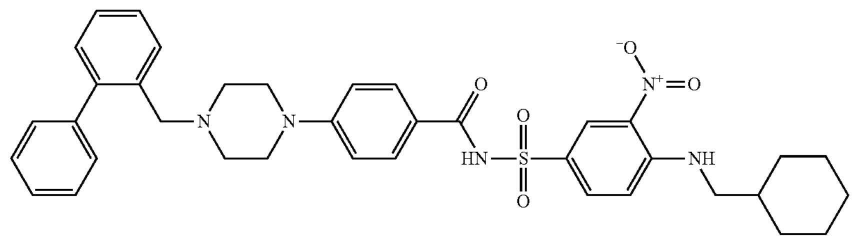 |
| N-(4-(4-((1,1'-biphenyl)-2-ylmethyl)-4-methoxypiperidin-1-yl)benzoyl)-4-(((1R)-3-(morpholin-4-yl)-1-((phenylsulfanyl)methyl)propyl)amino)-3-nitrobenzenesulfonamide, | 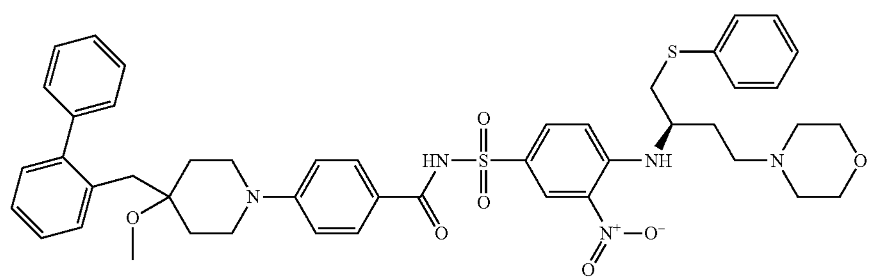 [SMILES: COC1(Cc2ccccc2-c2ccccc2)CCN(c2ccc(C(=O)NS(=O)(=O)c3ccc(N[C@H](CCN4CCOCC4)CSc4ccccc4)c([N+](=O)[O-])c3)cc2)CC1] |
| N-(4-(4-((1,1'-biphenyl)-2-ylmethyl)-4-methoxypiperidin-1-yl)benzoyl)-3-nitro-4-((2-(phenylsulfanyl)ethyl)amino)benzenesulfonamide, | 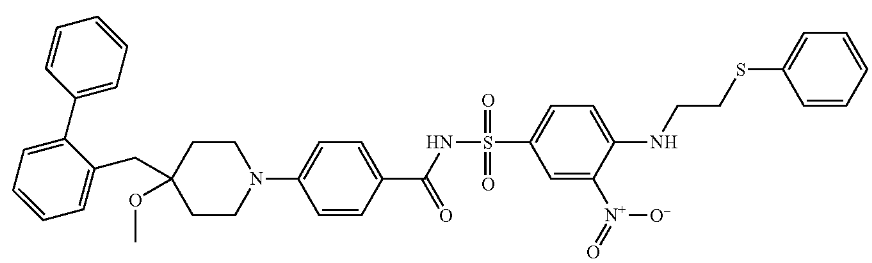 [SMILES: COC1(Cc2ccccc2-c2ccccc2)CCN(c2ccc(C(=O)NS(=O)(=O)c3ccc(NCCSc4ccccc4)c([N+](=O)[O-])c3)cc2)CC1] |
| N-(4-(4-((4'-chloro(1,1'-biphenyl)-2-yl)methyl)piperazin-1-yl)benzoyl)-4-(((1S)-3-(dimethylamino)-1-((phenylsulfanyl)methyl)propyl)amino)-3-nitrobenzenesulfonamide, | 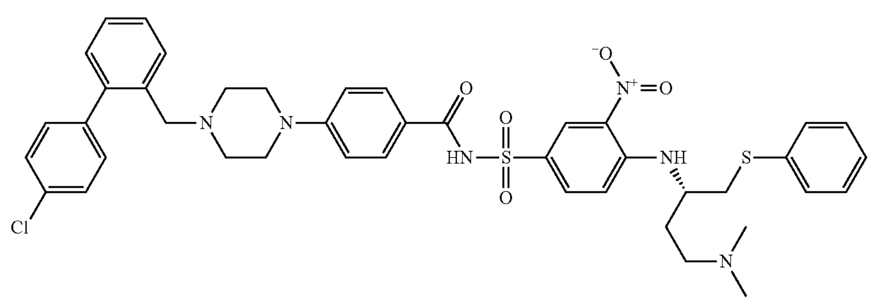 |

| Name | Structure |
|---|---|
| N-(4-(4-((4'-chloro(1,1'-biphenyl)-2-yl)methyl)piperazin-1-yl)benzoyl)-4-(((1R)-1-((phenylsulfanyl)methyl)-3-(pyrrolidin-1-yl)propyl)amino)-3-(trifluoromethyl)benzenesulfonamide. | |
| N-(4-(4-((4-(4-chlorophenyl)pyridin-3-yl)methyl)piperazin-1-yl)benzoyl)-4-(((1R)-3-(dimethylamino)-1-((phenylsulfanyl)methyl)propyl)amino)-3-nitrobenzenesulfonamide, | 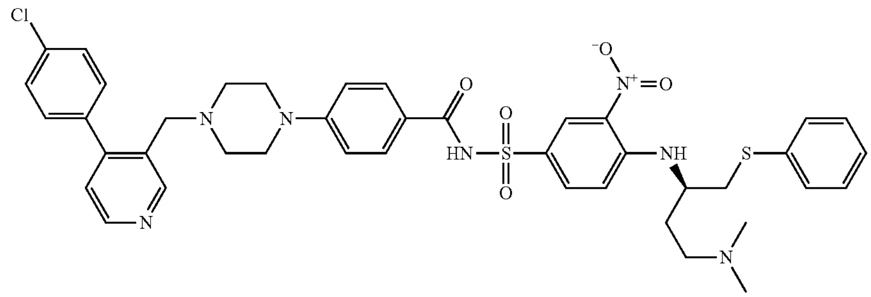 |
| N-(4-(4-((4-(4-chlorophenyl)pyridin-3-yl)methyl)piperazin-1-yl)benzoyl)-4-(((1R)-3-(morpholin-4-yl)-1-((phenylsulfanyl)methyl)propyl)amino)-3-nitrobenzenesulfonamide, | 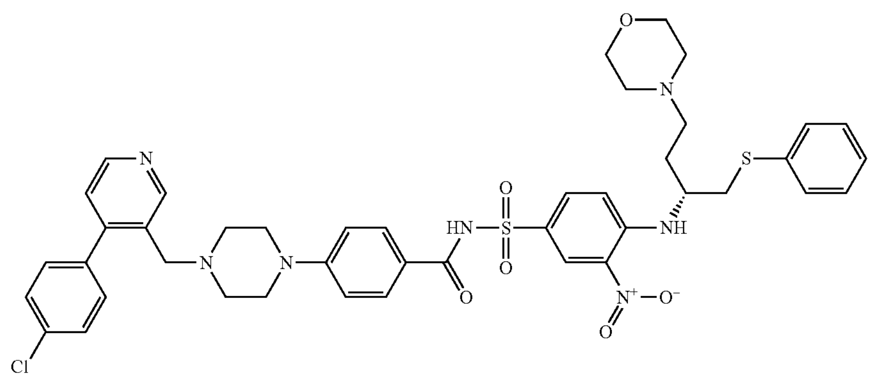 [SMILES: O=C(NS(=O)(=O)c1ccc(N[C@H](CCN2CCOCC2)CSc2ccccc2)c([N+](=O)[O-])c1)c1ccc(N2CCN(Cc3cnccc3-c3ccc(Cl)cc3)CC2)cc1] |
| N-(4-(4-((4'chloro(1,1'-biphenyl)-2-yl)methyl)piperazin-3-yl)benzoyl)-4-(((1R)-3-dimethylamino)-1-((phenylsulfanyl)methyl)propyl)amino)-2-fluoro-3-(trifluoromethyl)benzenesulfonamide, | |
| N-(6-(4-((4'-chloro(1,1'-biphenyl)-2-yl)methyl)piperazin-1-yl)-1,2-benzisoxazol-3-yl)-3-nitro-4-((2-(phenylsulfanyl)ethyl)amino)benzenesulfonamide, | 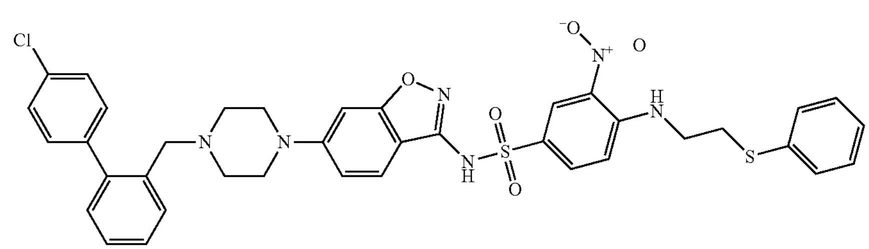 |

| Name | Structure |
|---|---|
| N-(6-(4-((4'-chloro(1,1'-biphenyl)-2-yl)methyl)piperazin-1-yl)-1,2-benzisoxazol-3-yl)-4-(((1R)-3-(morpholin-4-yl)-1-((phenylsulfanyl)methyl)propyl)amino)-3-nitrobenzenesulfonamide, | 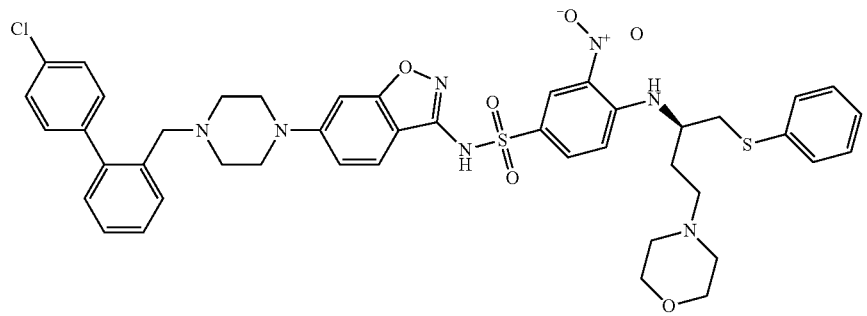 |
| N-(6-(4,4-dimethylpiperidin-1-yl)-1,2-benzisoxazol-3-yl)-3-nitro-4-((2-(phenylsulfanyl)ethyl)amino)benzenesulfonamide, | 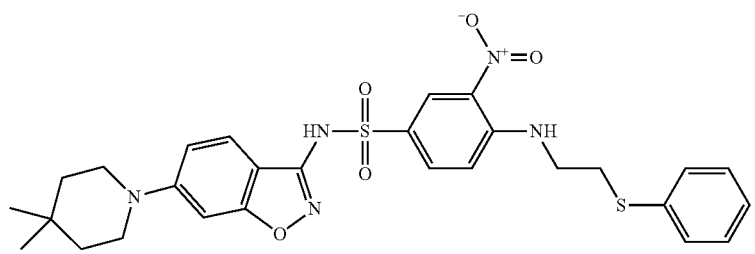 |
| N-(6-(4,4-dimethylpiperidm-1-yl)-1,2-benzisoxazol-3-yl)-4-(((1R)-3-(morpholin-4-yl)-1-((phenylsulfanyl)methyl)propyl)amino)-3-nitrobenzenesulfonamide, | 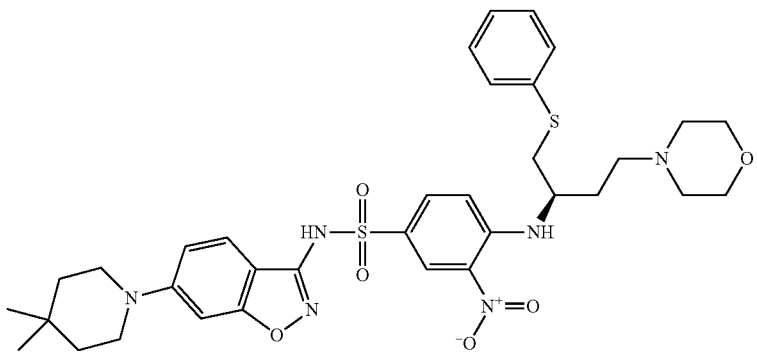 |
| N-(6-(4-(3,3-diphenylpropen-2-yl)piperazin-1-yl)-1,2-benzisoxazol-3-yl)-4-(((1R)-3-(morpholin-4-yl)-1-((phenylsulfanyl)methyl)propyl)aimno)-3-nitrobenzenesulfonamide, | 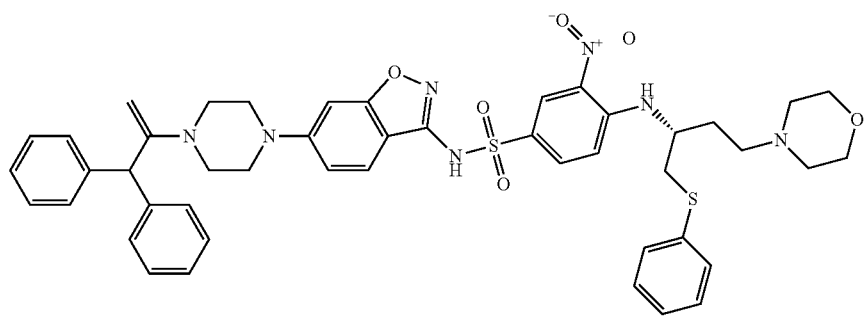 |
| N-(6-(4-(3,3-diphenylpropen-2-yl)piperazin-1-yl)-1,2-benzisoxazol-3-yl)-3-nitro-4-((2-(phenylsulfanyl)ethyl)amino)benzenesulfonamide, | 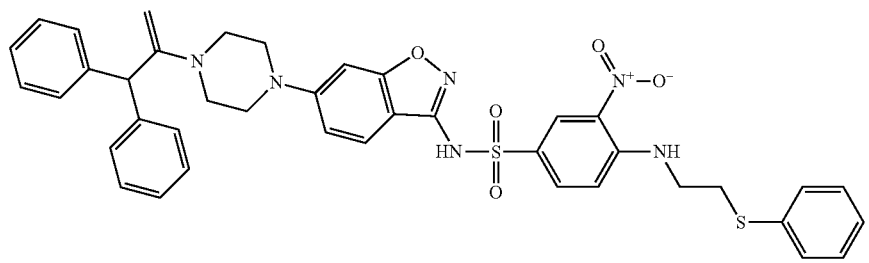 [SMILES: C=C(C(c1ccccc1)c1ccccc1)N1CCN(c2ccc3c(NS(=O)(=O)c4ccc(NCCSc5ccccc5)c([N+](=O)[O-])c4)noc3c2)CC1] |

-continued

| Name | Structure |
|---|---|
| N-(6-(4-((4'-chloro(1,1-biphenyl)-2-yl)methyl)piperazin-1-yl)-1,2-benzisoxazol-3-yl)-4-(((1R)-3-(dimethylamino)-1-((phenylsulfanyl)methyl)propyl)aimno)-3-nitrobenzenesulfonamide, | 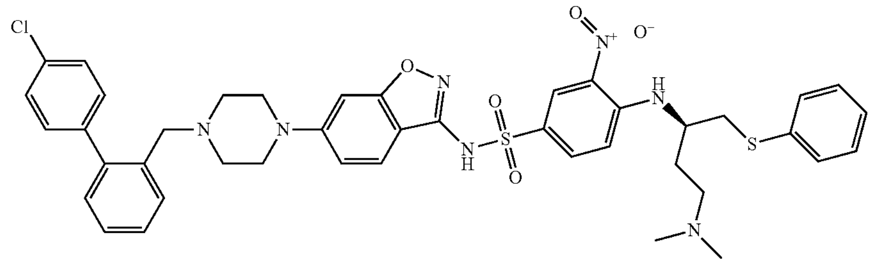 |
| 4-(((1R)-3-(dimethylamino)-1-((phenylsulfanyl)methyl)propyl)amino)-N-(6-(4,4-dimethylpiperidin-1-yl)-1,2-benzisoxazol-3-yl)-3-nitrobenzenesulfonamide, | 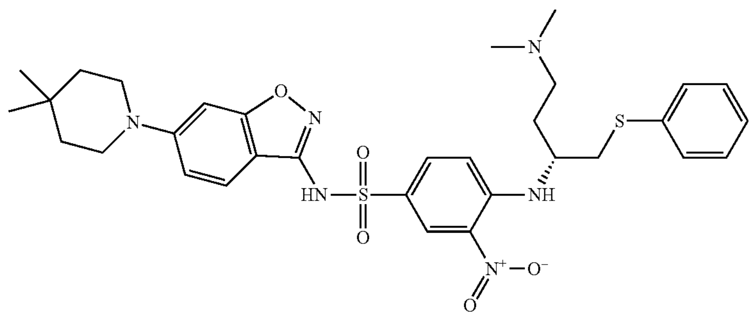 [SMILES: CN(C)CC[C@H](CSc1ccccc1)Nc1ccc(S(=O)(=O)Nc2noc3cc(N4CCC(C)(C)CC4)ccc23)cc1[N+](=O)[O-]] |
| N-(6-(4-((4'-chloro(1,1'-biphenyl)-2-yl)methyl)piperazin-1-yl)-1-methyl-1H-indazol-3-yl)-3-nitro-4-((2-(phenylsulfanyl)ethyl)amino)benzenesulfonamide, | 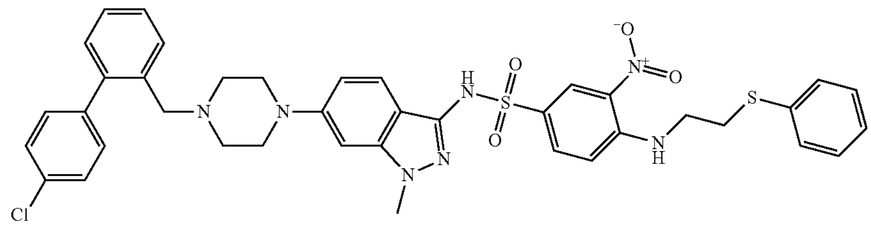 |
| N-(6-(4-((4'-chloro(1,1'-biphenyl)-2-yl)methyl)piperazin-1-yl)-1-methyl-1H-indazol-3-yl)-4-((1,1-dimethyl-2-(phenylsulfanyl)ethyl)amino)-3-nitrobenzenesulfonamide, | 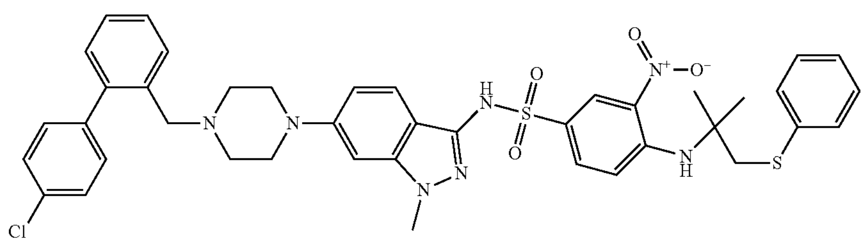 [SMILES: Cn1nc(NS(=O)(=O)c2ccc(NC(C)(C)CSc3ccccc3)c([N+](=O)[O-])c2)c2ccc(N3CCN(Cc4ccccc4-c4ccc(Cl)cc4)CC3)cc21] |
| N-(6-(4-((4'-chloro(1,1'-biphenyl)-2-yl)methyl)piperazin-1-yl)-1-methyl-1H-indazol-3-yl)-4-(((1R)-3-(dimethylamino)-1-((phenylsulfanyl)methyl)propyl)amino)-3-nitrobenzenesulfonamide, | 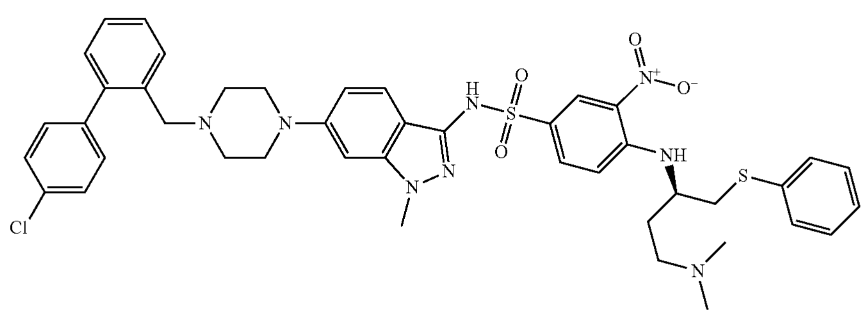 [SMILES: CN(C)CC[C@H](CSc1ccccc1)Nc1ccc(S(=O)(=O)Nc2nn(C)c3cc(N4CCN(Cc5ccccc5-c5ccc(Cl)cc5)CC4)ccc23)cc1[N+](=O)[O-]] |

-continued

| Name | Structure |
|---|---|
| N-(6-(4-((4'-chloro(1,1'-biphenyl)-2-yl)methyl)piperazin-1-yl)-1-methyl-1H-indazol-3-yl)-4-(((1R)-3-(morpholin-4-yl)-1-((phenylsulfanyl)methyl)propyl)amino)-3-ditrobenzenesulfonamide, | 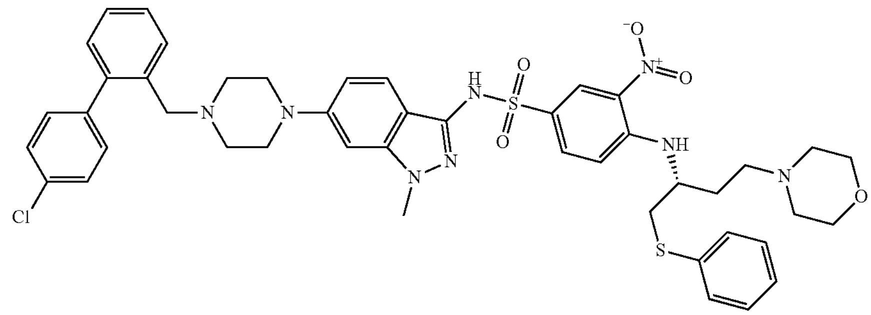 |
| N-(6-(4-((4'-chloro(1,1'-biphenyl)-2-yl)methyl)piperazin-1-yl)-1H-indazol-3-yl)-3-nitro-4-((2-(phenylsulfanyl)ethyl)amino)benzenesulfonamide, | 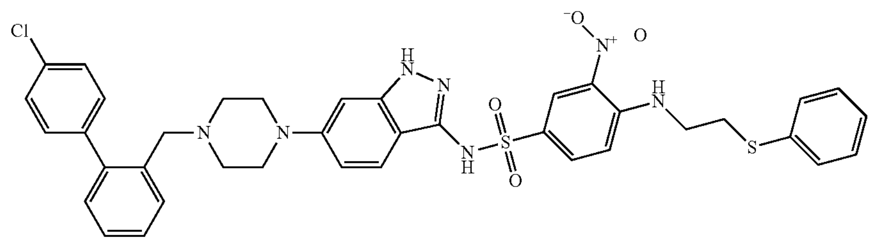 |
| N-(6-(4-((4'-chloro(1,1'-biphenyl)-2-yl)methyl)piperazin-1-yl)-1H-indazol-3-yl)-4-(((1R)-3-(dimethylamino)-1-((phenylsulfanyl)methyl)propyl)amino)-3-nitrobenzenesulfonamide, | 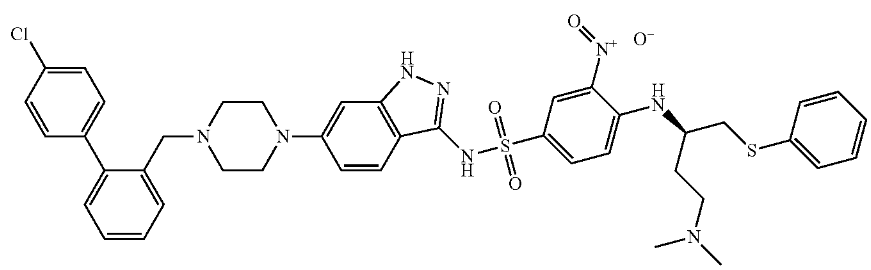 |
| N-(6-(4-((4'-chloro(1,1'-biphenyl)-2-yl)methyl)piperazin-1-yl)-1H-indazol-3-yl)-4-(((1R)-3-(morpholin-4-yl)-1-((phenylsulfanyl)methyl)propyl)amino)-3-nitrobenzenesulfonamide, | 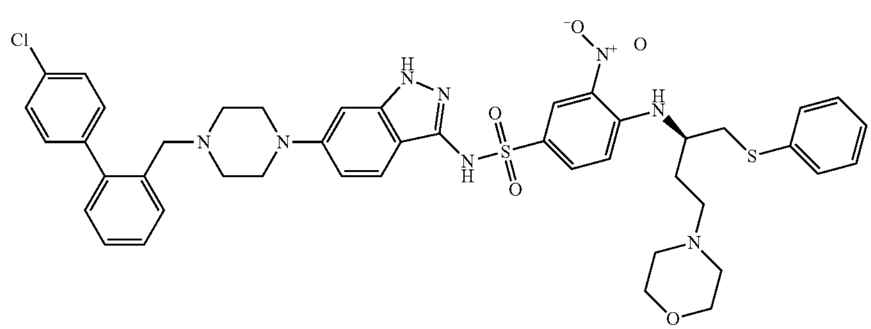 |

In some embodiments, the compound is selected from the group consisting of:

| Name | Structure |
|---|---|
| 4-(4-{[2-(4-chlorophenyl)-4,4-dimethylcyclohex-1-en-1-yl]methyl}piperazin-1-yl)-N-[(4-{[(2R)-1,4-dioxan-2-ylmethyl]amino}-3-nitrophenyl)sulfonyl]-2-(1H-pyrrolo[2,3-b]pyridin-5-yloxy)benzamide | 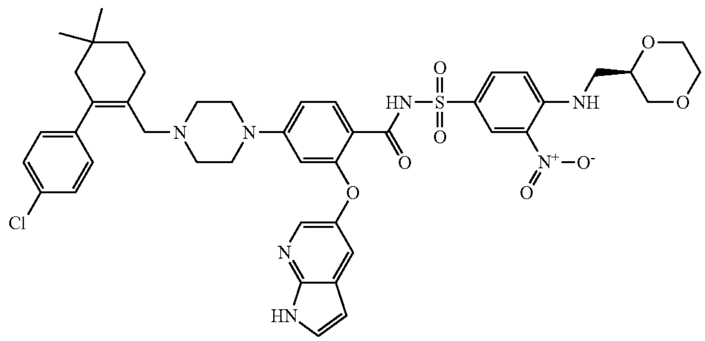 [SMILES: CC1(C)CCC(CN2CCN(c3ccc(C(=O)NS(=O)(=O)c4ccc(NC[C@@H]5COCCO5)c([N+](=O)[O-])c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-[(3-nitro-4-{[(1S)-1-(tetrahydro-2H-pyran-4-yl)ethyl]amino}phenyl)sulfonyl]-2-(1H-pyrrolo[2,3-b]pyridin-5-yloxy)benzamide | 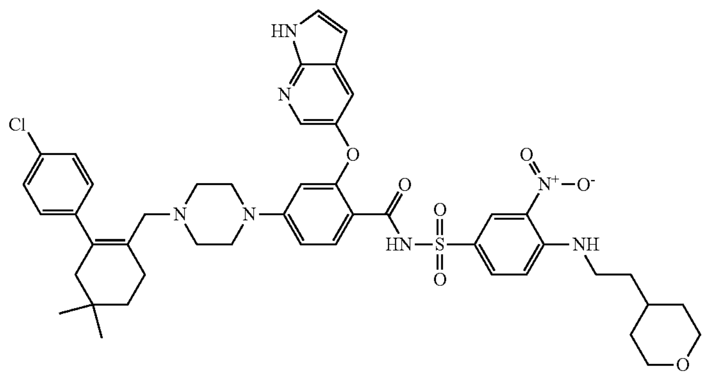 [SMILES: CC1(C)CCC(CN2CCN(c3ccc(C(=O)NS(=O)(=O)c4ccc(NCCC5CCOCC5)c([N+](=O)[O-])c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-[(3-nitro-4-{[(1R)-1-(tetrahydro-2H-pyran-4-yl)ethyl]amino}phenyl)sulfonyl]-2-(1H-pyrrolo[2,3-b]pyridin-5-yloxy)benzamide | 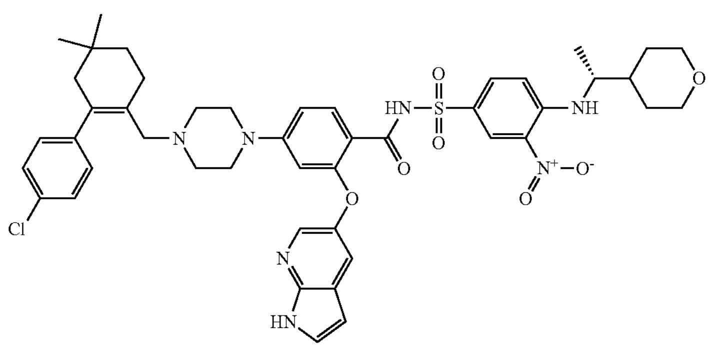 [SMILES: C[C@@H](Nc1ccc(S(=O)(=O)NC(=O)c2ccc(N3CCN(CC4=C(c5ccc(Cl)cc5)CC(C)(C)CC4)CC3)cc2Oc2cnc3[nH]ccc3c2)cc1[N+](=O)[O-])C1CCOCC1] |
| 4-(4-{[2-(4-chlorophenyl)-4,4-dimethylcyclohex-1-en-1-yl]methyl}piperazin-1-yl)-N-[(3-nitro-4-{[(5s,8s)-1-oxaspiro[4.5]dec-8-ylmethyl]amino}phenyl)sulfonyl]-2-(1H-pyrrolo[2,3-b]pyridin-5-yloxy)benzamide | 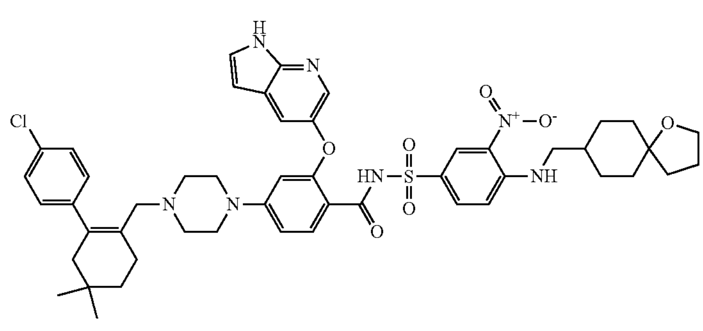 [SMILES: CC1(C)CCC(CN2CCN(c3ccc(C(=O)NS(=O)(=O)c4ccc(NCC5CCC6(CCCO6)CC5)c([N+](=O)[O-])c4)c(Oc4cnc5[nH]ccc5c4)c3)CC2)=C(c2ccc(Cl)cc2)C1] |

| Name | Structure |
|---|---|
| 4-(4-{[2-(4-chlorophenyl)-4,4-dimethylcyclohex-1-en-1-yl]methyl}piperazin-1-yl)-N-[(3-nitro-4-{[(5r,8r)-1-oxaspiro[4.5]dec-8-ylmethyl]amino}phenyl)sulfonyl]-2-(1H-pyrrolo[2,3-b]pyridin-5-yloxy)benzamide | 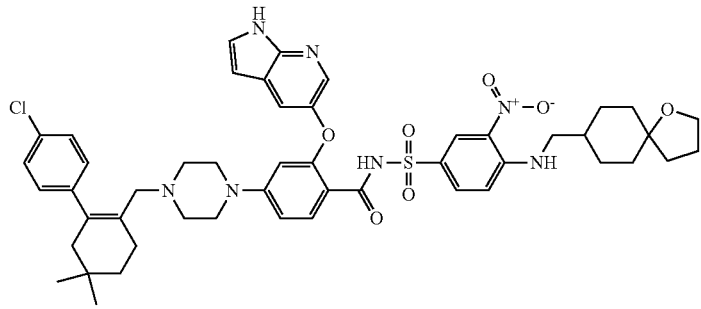 [SMILES: CC1(C)CCC(CN2CCN(c3ccc(C(=O)NS(=O)(=O)c4ccc(NCC5CCC6(CCCO6)CC5)c([N+](=O)[O-])c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-n-[(4-{[(4-hydroxytetrahydro-2h-pyran-4-yl)methyl]amino}-3-nitrophenyl)sulfonyl]-2-(1h-pyrrolo[2,3-b]pyridin-5-yloxy)benzamide | 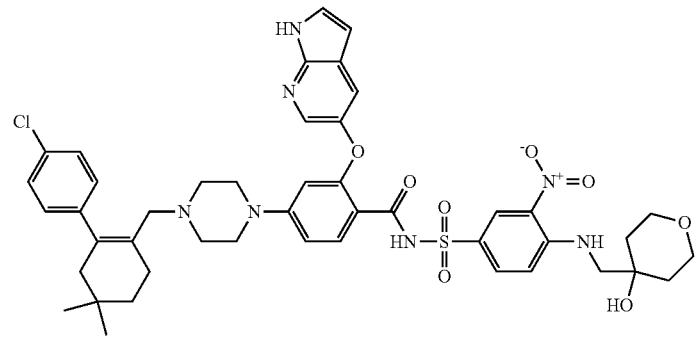 |
| 4-(4-{[2-(4-chlorophenyl)-4,4-dimethylcyclohex-1-en-1-yl]methyl}piperazin-1-yl)-N-({4-[(1,4-dioxaspiro[4.5]dec-8-ylmethyl)amino]-3-nitrophenyl}sulfonyl)-2-(1H-pyrrolo[2,3-b]pyridin-5-yloxy)benzamide | 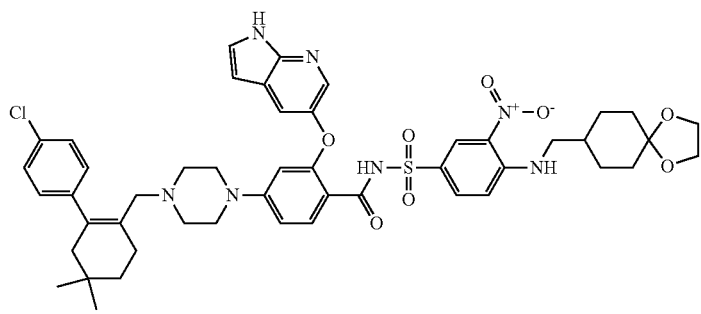 [SMILES: CC1(C)CCC(CN2CCN(c3ccc(C(=O)NS(=O)(=O)c4ccc(NCC5CCC6(CC5)OCCO6)c([N+](=O)[O-])c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-{[4-(morpholin-4-yl)-3-nitrophenyl]sulfonyl}-2-(1H-pyrrolo[2,3-b]pyridin-5-yloxy)benzamide | 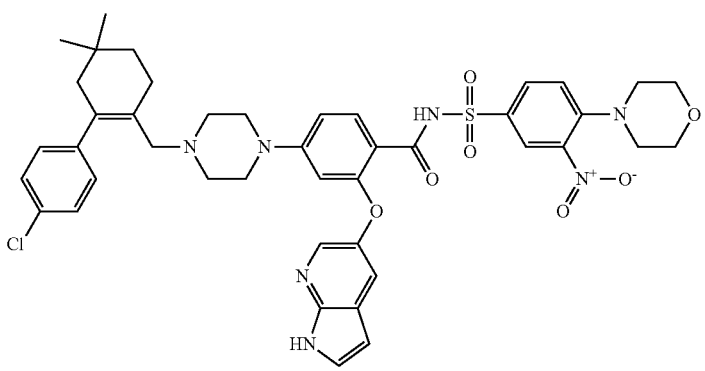 [SMILES: CC1(C)CCC(CN2CCN(c3ccc(C(=O)NS(=O)(=O)c4ccc(N5CCOCC5)c([N+](=O)[O-])c4)c(Oc4cnc5[nH]ccc5c4)c3)CC2)=C(c2ccc(Cl)cc2)C1] |

| Name | Structure |
|---|---|
| 4-(4-{[2-(4-chlorophenyl)-4,4-dimethylcyclohex-1-en-1-yl]methyl}piperazin-1-yl)-N-[(4-{[(2S)-1,4-dioxan-2-ylmethyl]amino}-3-nitrophenyl)sulfonyl]-2-(1H-pyrrolo[2,3-b]pyridin-5-yloxy)benzamide | 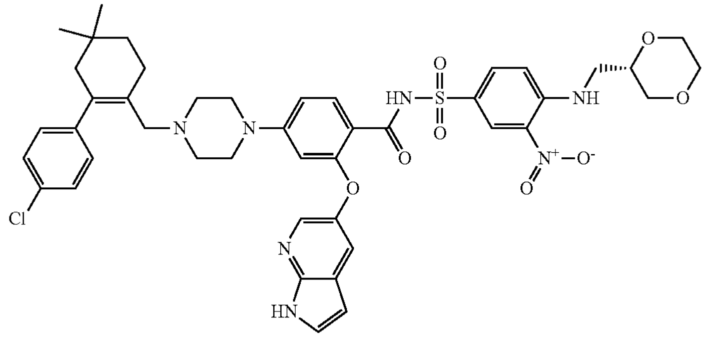 [SMILES: CC1(C)CCC(CN2CCN(c3ccc(C(=O)NS(=O)(=O)c4ccc(NC[C@H]5COCCO5)c([N+](=O)[O-])c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-{[4-({[4-(hydroxymethyl)tetrahydro-2H-pyran-4-yl]methyl}amino)-3-nitrophenyl]sulfonyl}-2-(1H-pyrrolo[2,3-b]pyridin-5-yloxy)benzamide | 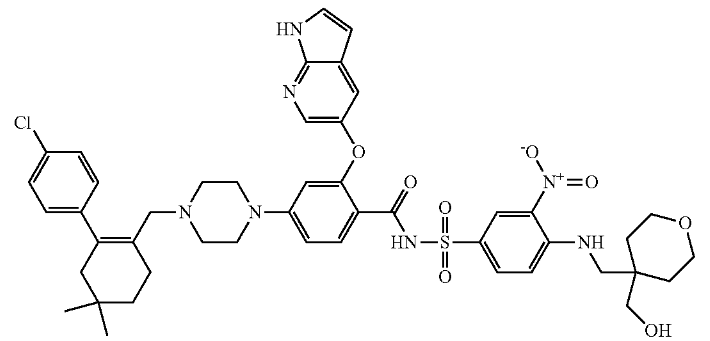 |
| 4-(4-{[2-(4-chlorophenyl)-4,4-dimethylcyclohex-1-en-1-yl]methyl}piperazin-1-yl)-N-{[4-({[3-(hydroxymethyl)oxetan-3-yl]methyl}amino)-3-nitrophenyl]sulfonyl}-2-(1H-pyrrolo[2,3-b]pyridin-5-yloxy)benzamide | 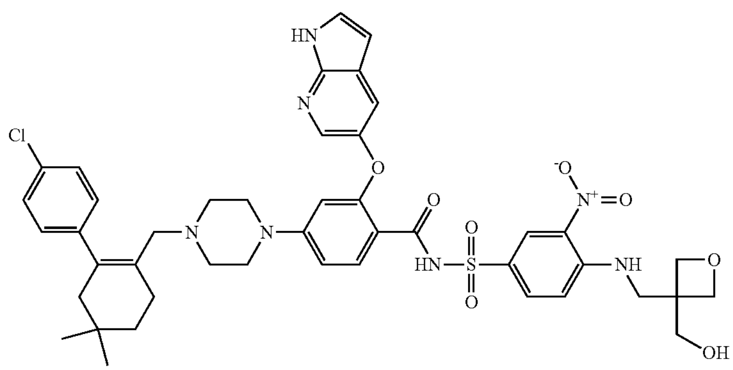 |
| 4-(4-{[2-(4-chlorophenyl)-4,4-dimethylcyclohex-1-en-1-yl]methyl}piperazin-1-yl)-N-({4-[(3-hydroxy-3-methylbutyl)amino]-3-nitrophenyl}sulfonyl)-2-(1H-pyrrolo[2,3-b]pyridin-5-yloxy)benzamide | 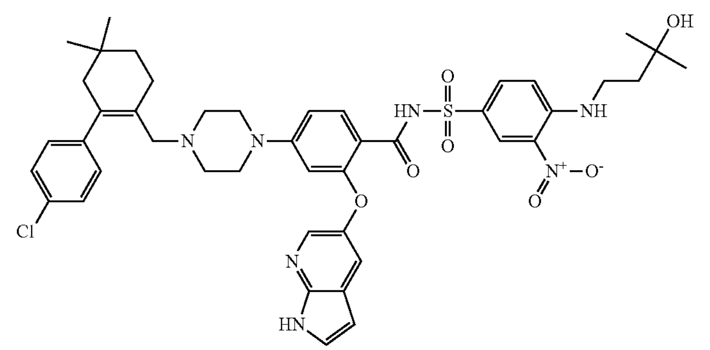 [SMILES: CC(C)(O)CCNc1ccc(S(=O)(=O)NC(=O)c2ccc(N3CCN(CC4=C(c5ccc(Cl)cc5)CC(C)(C)CC4)CC3)cc2Oc2cnc3[nH]ccc3c2)cc1[N+](=O)[O-]] |
| 4-(4-{[2-(4-chlorophenyl)-4,4-dimethylcyclohex-1-en-1-yl]methyl}piperazin-1-yl)-N-({4-[(3-hydroxytricyclo[3.3.1.1$^{3,7}$]dec-1-yl)amino]-3-nitrophenyl}sulfonyl)-2-(1H-pyrrolo[2,3-£]pyridin-5-yloxy)benzamide | |

-continued

| Name | Structure |
|---|---|
| 4-(4-{[2-(4-chlorophenyl)-4,4-dimethylcyclohex-1-en-1-yl]methyl}piperazin-1-yl)-N-[(3-nitro-4-{[(1R,5S,6S)-3-oxabicyclo[3.1.0]hex-6-ylmethyl]amino}phenyl)sulfonyl]-2-(1H-pyrrolo[2,3-b]pyridin-5-yloxy)benzamide | 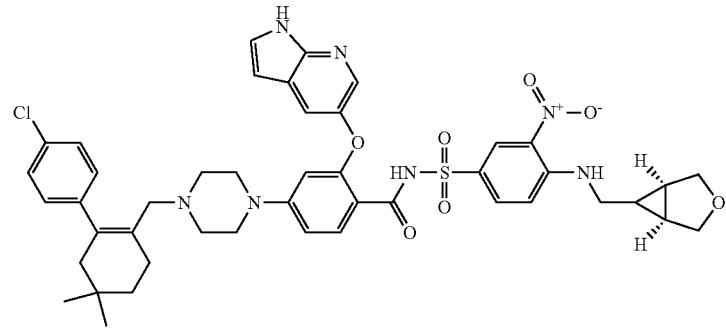 [SMILES: CC1(C)CCC(CN2CCN(c3ccc(C(=O)NS(=O)(=O)c4ccc(NCC5[C@H]6COC[C@@H]56)c([N+](=O)[O-])c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-[(4-{[(3-hydroxyoxetan-3-yl)methyl]amino}-3-nitrophenyl)sulfonyl]-2-(1H-pyrrolo[2,3-b]pyridin-5-yloxy)benzamide | 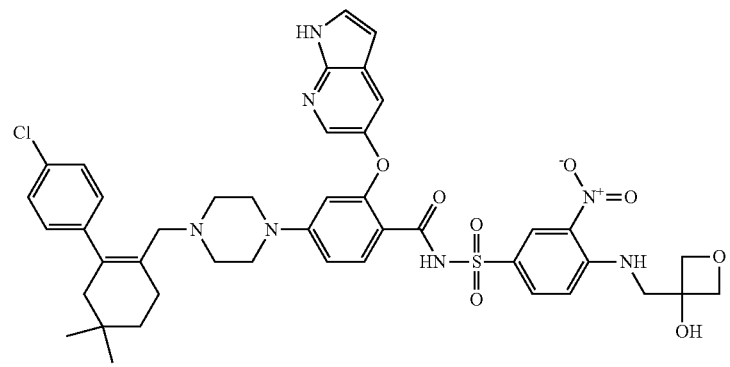 |
| 4-(4-{[2-(4-chlorophenyl)-4,4-dimethylcyclohex-1-en-1-yl]methyl}piperazin-1-yl)-N-{[4-(morpholin-4-ylamino)-3-nitrophenyl]sulfonyl}-2-(1H-pyrrolo[2,3-b]pyridin-5-yloxy)benzamide | 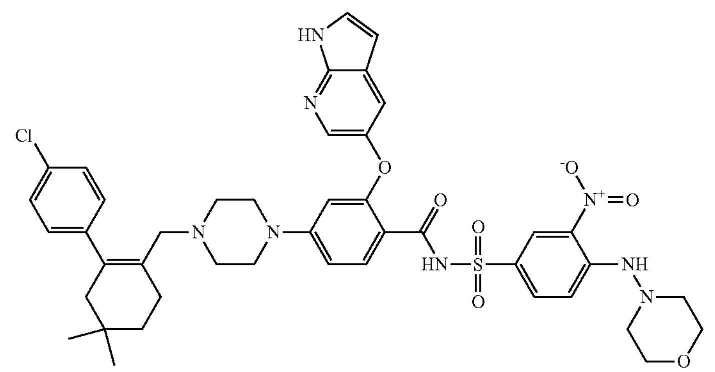 |
| methyl 4-{[(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)amino]methyl}tetrahydro-2H-pyran-4-carboxylate | 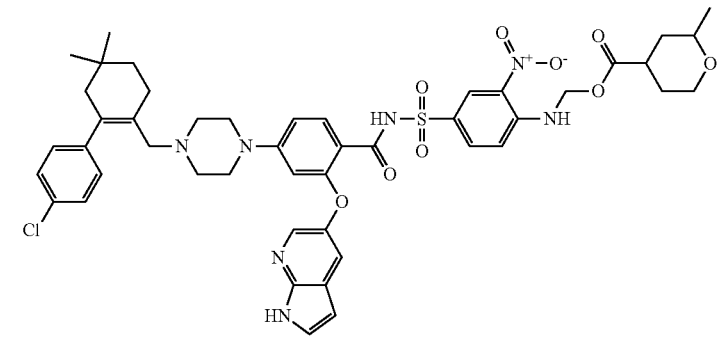 [SMILES: CC1CC(C(=O)OCNc2ccc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2[N+](=O)[O-])CCO1] |

| Name | Structure |
|---|---|
| 4-(4-{[2-(4-chlorophenyl)-4,4-dimethylcyclohex-1-en-1-yl]methyl}piperazin-1-yl)-N-({3-nitro-4-[2-(tetrahydro-2H-pyran-4-yl)hydrazinyl]phenyl}sulfonyl)-2-(1H-pyrrolo[2,3-b]pyridin-5-yloxy)benzamide | 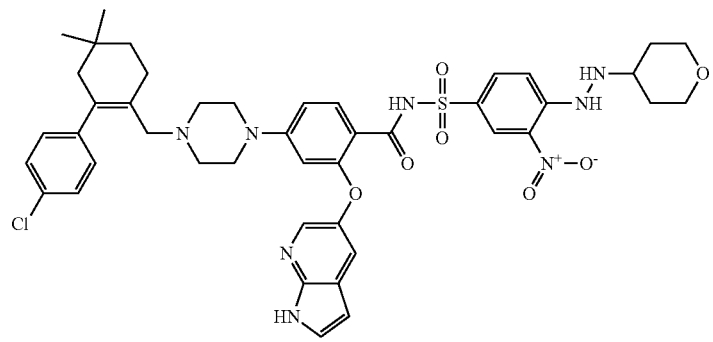 [SMILES: CC1(C)CCC(CN2CCN(c3ccc(C(=O)NS(=O)(=O)c4ccc(NNC5CCOCC5)c([N+](=O)[O-])c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-[(3-nitro-4-{[(4R)-oxepan-4-ylmethyl]amino}phenyl)sulfonyl]-2-(1H-pyrrolo[2,3-b]pyridin-5-yloxy)benzamide | 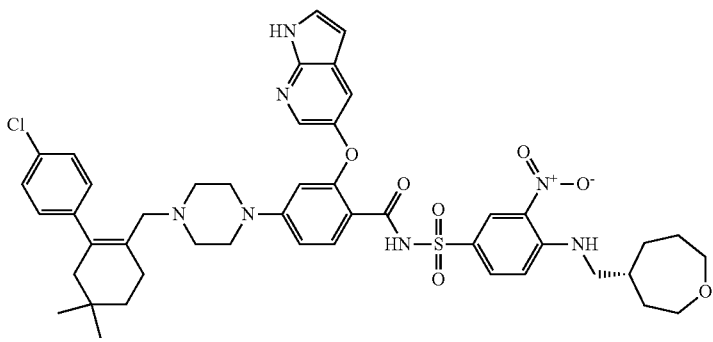 [SMILES: CC1(C)CCC(CN2CCN(c3ccc(C(=O)NS(=O)(=O)c4ccc(NC[C@@H]5CCCOCC5)c([N+](=O)[O-])c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-[(3-nitro-4-{[(4S)-oxepan-4-ylmethyl]amino}phenyl)sulfonyl]-2-(1H-pyrrolo[2,3-b]pyridin-5-yloxy)benzamide | 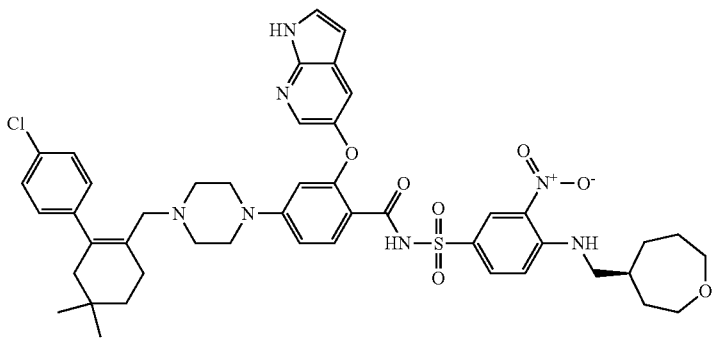 [SMILES: CC1(C)CCC(CN2CCN(c3ccc(C(=O)NS(=O)(=O)c4ccc(NC[C@H]5CCCOCC5)c([N+](=O)[O-])c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-[(4-{[(4-methyltetrahydro-2H-pyran-4-yl)methyl]amino}-3-nitrophenyl)sulfonyl]-2-(1H-pyrrolo[2,3-b]pyridin-5-yloxy)benzamide | 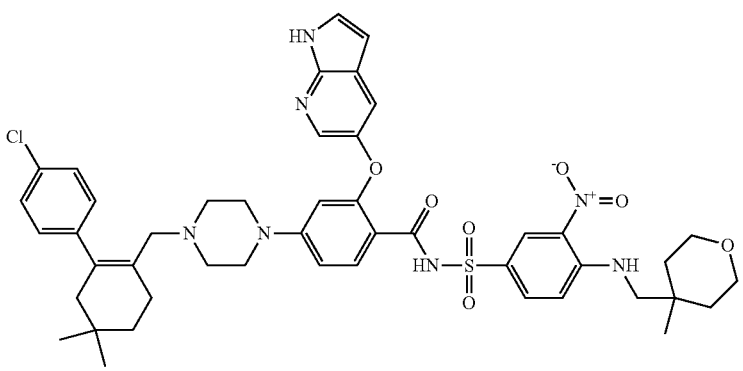 |

| Name | Structure |
|---|---|
| 4-(4-{[2-(4-chlorophenyl)-4,4-dimethylcyclohex-1-en-1-yl]methyl}piperazin-1-yl)-N-({3-nitro-4-[(tetrahydro-2H-thiopyran-4-ylmethyl)amino]phenyl}sulfonyl)-2-(1H-pyrrolo[2,3-b]pyridin-5-yloxy)benzamide | 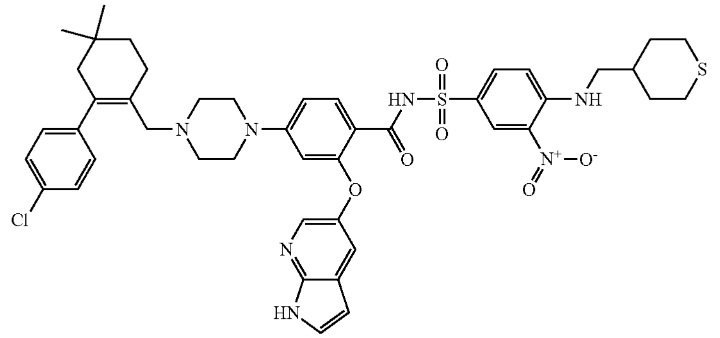 [SMILES: CC1(C)CCC(CN2CCN(c3ccc(C(=O)NS(=O)(=O)c4ccc(NCC5CCSCC5)c([N+](=O)[O-])c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-({3-nitro-4-[(oxetan-3-ylmethyl)amino]phenyl}sulfonyl)-2-(1H-pyrrolo[2,3-b]pyridin-5-yloxy)benzamide | 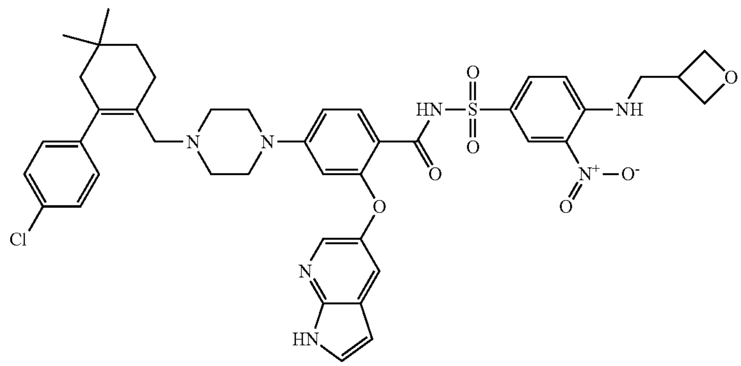 [SMILES: CC1(C)CCC(CN2CCN(c3ccc(C(=O)NS(=O)(=O)c4ccc(NCC5COC5)c([N+](=O)[O-])c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-{[4-({[(2R,5R)-5-methyl-1,4-dioxan-2-yl]methyl}amino)-3-nitrophenyl]sulfonyl}-2-(1H-pyrrolo[2,3-b]pyridin-5-yloxy)benzamide | 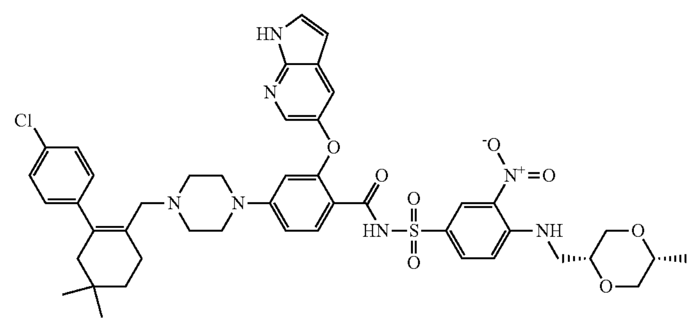 |
| 4-(4-{[2-(4-chlorophenyl)-4,4-dimethylcyclohex-1-en-1-yl]methyl}piperazin-1-yl)-N-[(4-{[(6-hydroxy-1,4-dioxepan-6-yl)methyl]amino}-3-nitrophenyl)sulfonyl]-2-(1H-pyrrolo[2,3-b]pyridin-5-yloxy)benzamide | 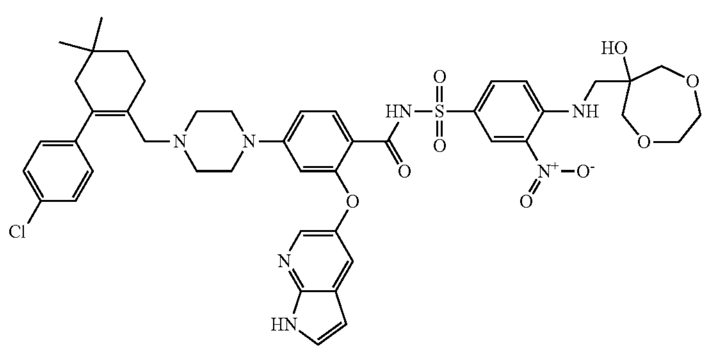 [SMILES: CC1(C)CCC(CN2CCN(c3ccc(C(=O)NS(=O)(=O)c4ccc(NCC5(O)COCCOC5)c([N+](=O)[O-])c4)c(Oc4cnc5[nH]ccc5c4)c3)CC2)=C(c2ccc(Cl)cc2)C1] |

-continued

| Name | Structure |
|---|---|
| 4-(4-{[2-(4-chlorophenyl)-4,4-dimethylcyclohex-1-en-1-yl]methyl}piperazin-1-yl)-N-[(4-{[(4,4-difluoro-1-hydroxycyclohexyl)methyl]amino}-3-nitrophenyl)sulfonyl]-2-(1H-pyrrolo[2,3-b]pyridin-5-yloxy)benzamide | 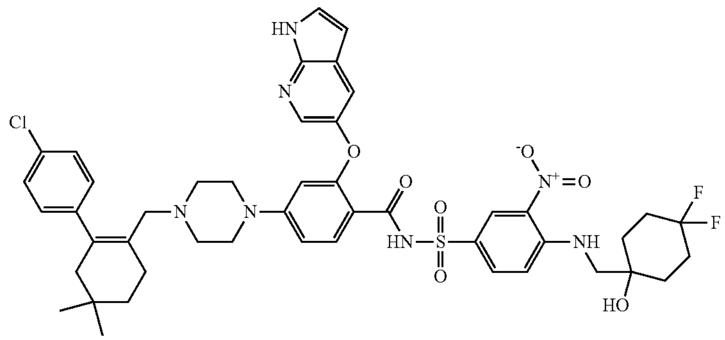 |
| 4-(4-{[2-(4-chlorophenyl)-4,4-dimethylcyclohex-1-en-1-yl]methyl}piperazin-1-yl)-N-[(4-{[(4-methoxytetrahydro-2H-pyran-4-yl)methyl]amino}-3-nitrophenyl)sulfonyl]-2-(1H-pyrrolo[2,3-b]pyridin-5-yloxy)benzamide | 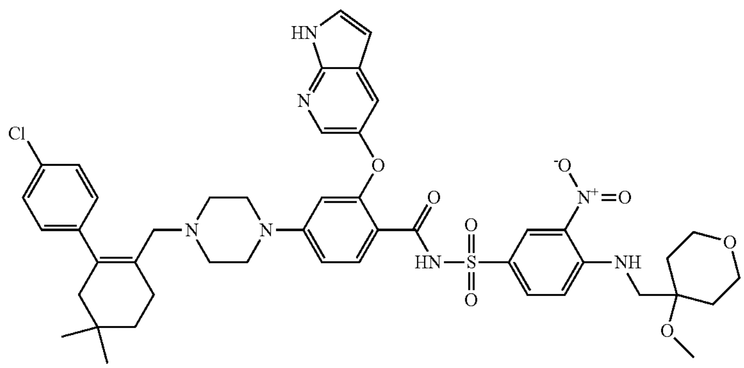 |
| 4-(4-{[2-(4-chlorophenyl)-4,4-dimethylcyclohex-1-en-1-yl]methyl}piperazin-1-yl)-N-[(4-{[(3,3-difluorocyclobutyl)methyl]amino}-3-nitrophenyl)sulfonyl]-2-(1H-pyrrolo[2,3-b]pyridin-5-yloxy)benzamide | 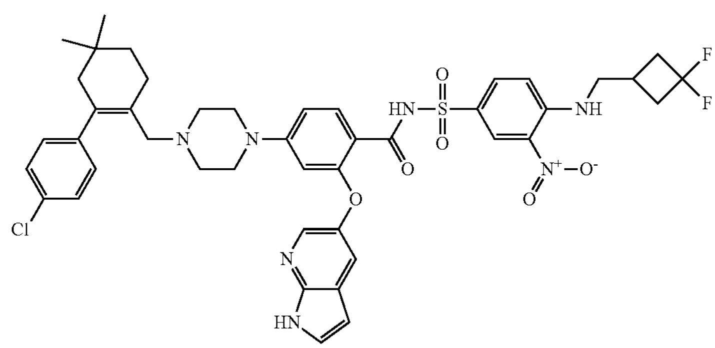 [SMILES: CC1(C)CCC(CN2CCN(c3ccc(C(=O)NS(=O)(=O)c4ccc(NCC5CC(F)(F)C5)c([N+](=O)[O-])c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-({3-nitro-4-[({1-[(trifluoromethyl)sulfonyl]piperidin-4-yl}methyl)amino]phenyl}sulfonyl)-2-(1H-pyrrolo[2,3-b]pyridin-5-yloxy)benzamide | 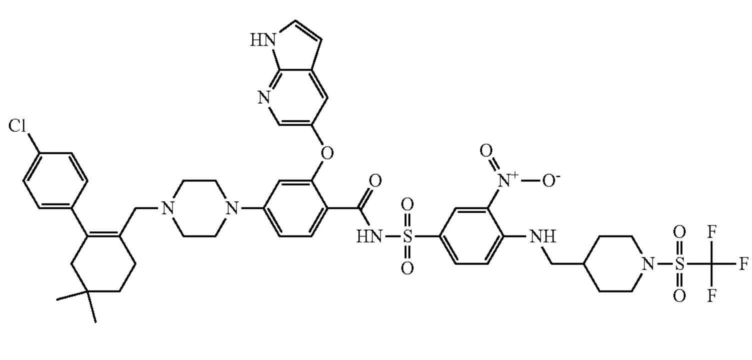 [SMILES: CC1(C)CCC(CN2CCN(c3ccc(C(=O)NS(=O)(=O)c4ccc(NCC5CCN(S(=O)(=O)C(F)(F)F)CC5)c([N+](=O)[O-])c4)c(Oc4cnc5[nH]ccc5c4)c3)CC2)=C(c2ccc(Cl)cc2)C1] |

| Name | Structure |
|---|---|
| 4-(4-{[2-(4-chlorophenyl)-4,4-dimethylcyclohex-1-en-1-yl]methyl}piperazin-1-yl)-N-{[4-({[1-(methylsulfonyl)piperidin-4-yl]methyl}amino)-3-nitrophenyl]sulfonyl}-2-(1H-pyrrolo[2,3-b]pyridin-5-yloxy)benzamide | 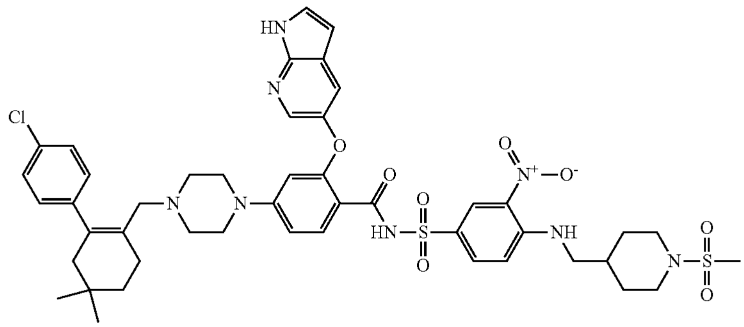 [SMILES: CC1(C)CCC(CN2CCN(c3ccc(C(=O)NS(=O)(=O)c4ccc(NCC5CCN(S(C)(=O)=O)CC5)c([N+](=O)[O-])c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-{[4-({[(2R,4R,6S)-2,6-dimethyltetrahydro-2H-pyran-4-yl]methyl}amino)-3-nitrophenyl]sulfonyl}-2-(1H-pyrrolo[2,3-b]pyridin-5-yloxy)benzamide | 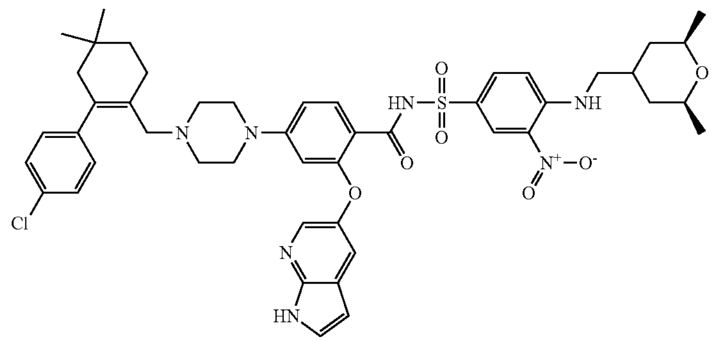 [SMILES: C[C@@H]1CC(CNc2ccc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2[N+](=O)[O-])C[C@H](C)O1] |
| 4-(4-{[2-(4-chlorophenyl)-4,4-dimethylcyclohex-1-en-1-yl]methyl}piperazin-1-yl)-N-[(3-nitro-4-{[(1-oxidotetrahydro-2H-thiopyran-4-yl)methyl]amino}phenyl)sulfonyl]-2-(1H-pyrrolo[2,3-b]pyridin-5-yloxy)benzamide | 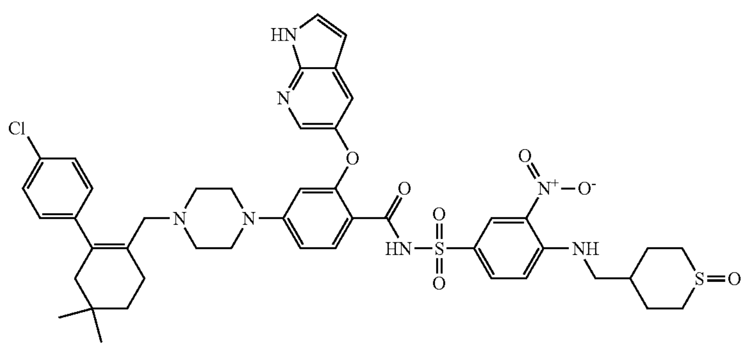 [SMILES: CC1(C)CCC(CN2CCN(c3ccc(C(=O)NS(=O)(=O)c4ccc(NCC5CCS(=O)CC5)c([N+](=O)[O-])c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-{[4-({[(4S)-2,2-dimethyltetrahydro-2H-pyran-4-yl]methyl}amino)-3-nitrophenyl]sulfonyl}-2-(1H-pyrrolo[2,3-b]pyridin-5-yloxy)benzamide | 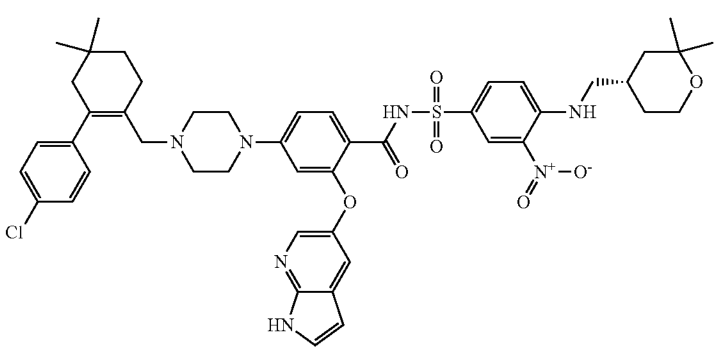 [SMILES: CC1(C)CCC(CN2CCN(c3ccc(C(=O)NS(=O)(=O)c4ccc(NC[C@H]5CCOC(C)(C)C5)c([N+](=O)[O-])c4)c(Oc4cnc5[nH]ccc5c4)c3)CC2)=C(c2ccc(Cl)cc2)C1] |

| Name | Structure |
|---|---|
| 4-(4-{[2-(4-chlorophenyl)-4,4-dimethylcyclohex-1-en-1-yl]methyl}piperazin-1-yl)-N-{[4-({[(4R)-2,2-dimethyltetrahydro-2H-pyran-4-yl]methyl}amino)-3-nitrophenyl]sulfonyl}-2-(1H-pyrrolo[2,3-b]pyridin-5-yloxy)benzamide | 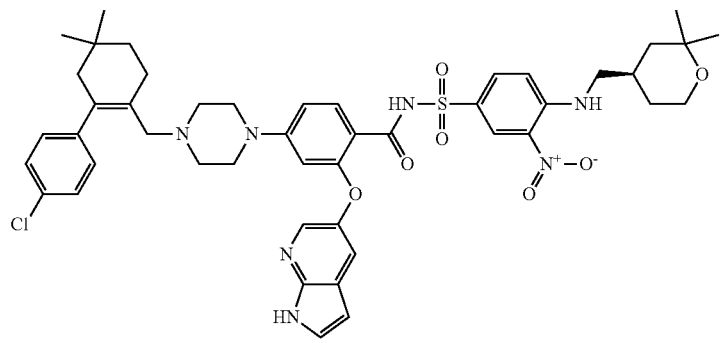 [SMILES: CC1(C)CCC(CN2CCN(c3ccc(C(=O)NS(=O)(=O)c4ccc(NC[C@@H]5CCOC(C)(C)C5)c([N+](=O)[O-])c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-{[4-({[(2S,6R)-6-methyl-1,4-dioxan-2-yl]methyl}amino)-3-nitrophenyl]sulfonyl}-2-(1H-pyrrolo[2,3-b]pyridin-5-yloxy)benzamide | 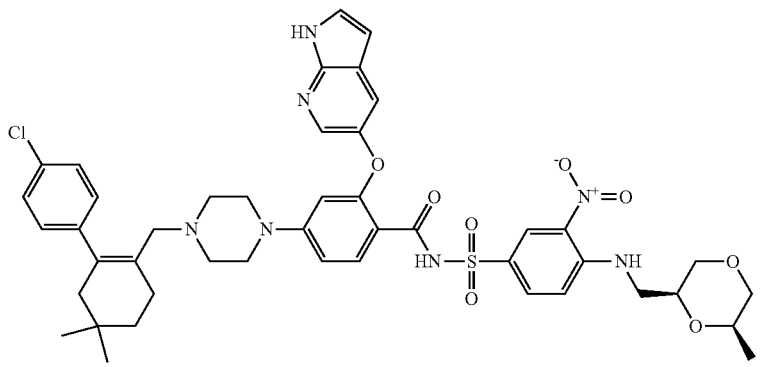 |
| 4-(4-{[2-(4-chlorophenyl)-4,4-dimethylcyclohex-1-en-1-yl]methyl}piperazin-1-yl)-N-[(3-nitro-4-{[(3S)-tetrahydrofuran-3-ylmethyl]amino}phenyl)sulfonyl]-2-(1H-pyrrolo[2,3-b]pyridin-5-yloxy)benzamide | 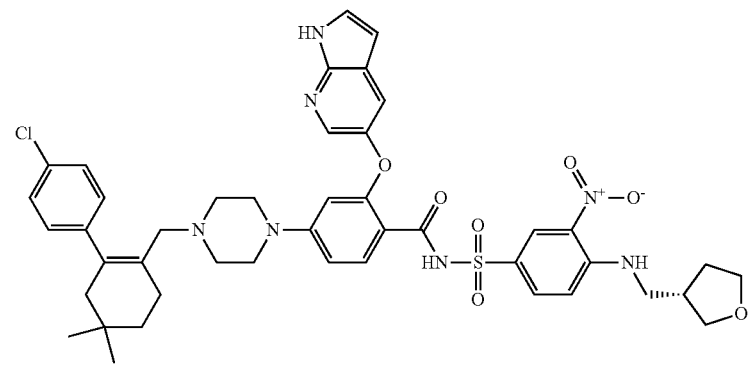 [SMILES: CC1(C)CCC(CN2CCN(c3ccc(C(=O)NS(=O)(=O)c4ccc(NC[C@@H]5CCOC5)c([N+](=O)[O-])c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-{[4-({[(2S)-6,6-dimethyl-1,4-dioxan-2-yl]methyl}amino)-3-nitrophenyl]sulfonyl}-2-(1H-pyrrolo[2,3-b]pyridin-5-yloxy)benzamide | 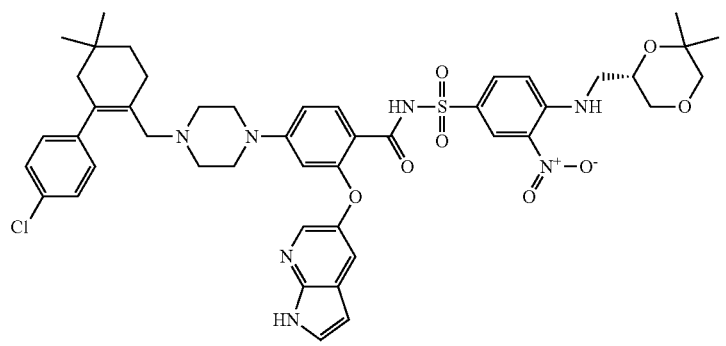 [SMILES: CC1(C)CCC(CN2CCN(c3ccc(C(=O)NS(=O)(=O)c4ccc(NC[C@H]5COCC(C)(C)O5)c([N+](=O)[O-])c4)c(Oc4cnc5[nH]ccc5c4)c3)CC2)=C(c2ccc(Cl)cc2)C1] |

-continued

| Name | Structure |
|---|---|
| 4-(4-{[2-(4-chlorophenyl)-4,4-dimethylcyclohex-1-en-1-yl]methyl}piperazin-1-yl)-N-[(4-{[(3-methyloxetan-3-yl)methyl]amino}-3-nitrophenyl)sulfonyl]-2-(1H-pyrrolo[2,3-b]pyridin-5-yloxy)benzamide | 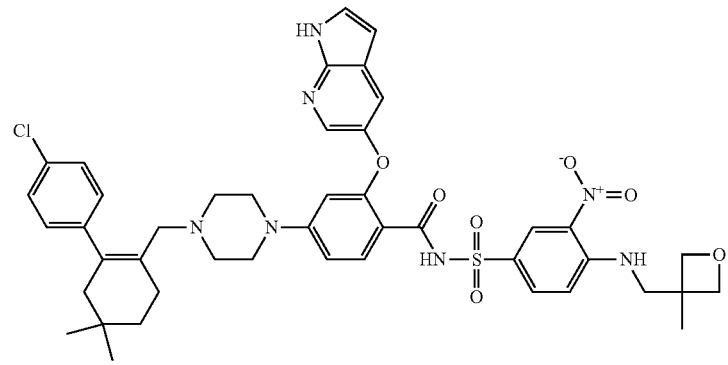 |
| 4-(4-{[2-(4-chlorophenyl)-4,4-dimethylcyclohex-1-en-1-yl]methyl}piperazin-1-yl)-N-[(4-{[(6-fluoro-1,4-dioxepan-6-yl)methyl]amino}-3-nitrophenyl)sulfonyl]-2-(1H-pyrrolo[2,3-b]pyridin-5-yloxy)benzamide | 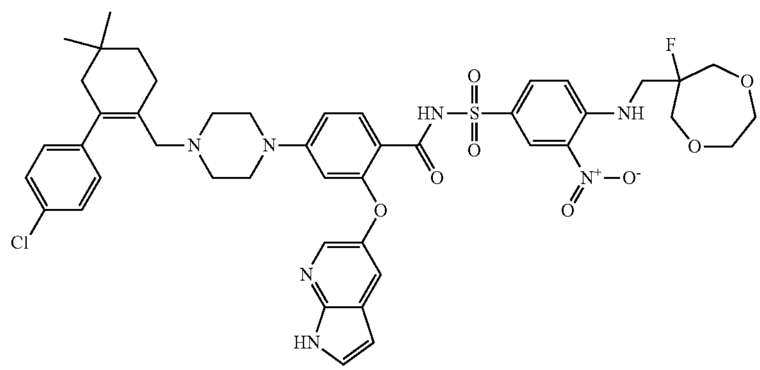 [SMILES: CC1(C)CCC(CN2CCN(c3ccc(C(=O)NS(=O)(=O)c4ccc(NCC5(F)COCCOC5)c([N+](=O)[O-])c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-n-[(4-{[(6-methoxy-1,4-dioxepan-6-yl)methyl]amino}-3-nitrophenyl]sulfonyl]-2-(1h-pyrrolo[2,3-b]pyridin-5-yloxy)benzamide |  |
| 4-(4-{[2-(4-chlorophenyl)-4,4-dimethylcyclohex-1-en-1-yl]methyl}piperazin-1-yl)-N-[(4-{[(trans-3-cyanocyclobutyl)methyl]amino}-3-nitrophenyl)sulfonyl]-2-(1H-pyrrolo[2,3-b]pyridin-5-yloxy)benzamide | 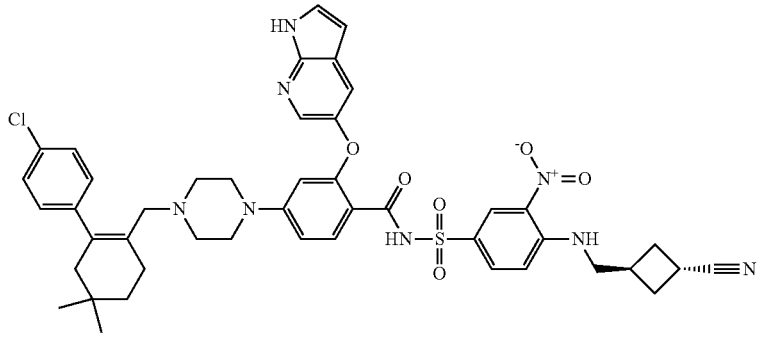 |

| Name | Structure |
|---|---|
| 4-(4-{[2-(4-chlorophenyl)-4,4-dimethylcyclohex-1-en-1-yl]methyl}piperazin-1-yl)-n-[(4-{[(cis-3-cyanocyclobutyl)methyl]amino}-3-nitrophenyl)sulfonyl]-2-(1h-pyrrolo[2,3-b]pyridin-5-yloxy)benzamide | 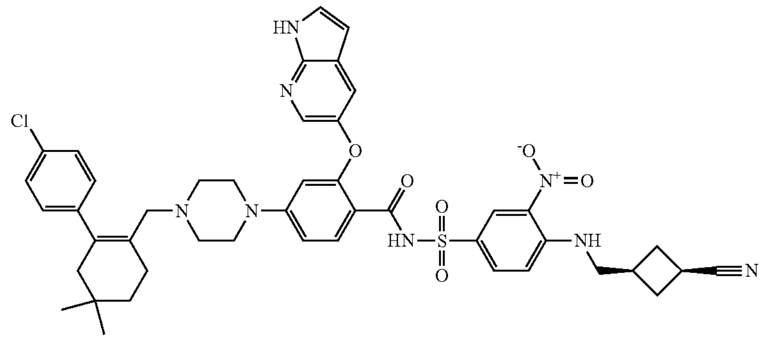 |
| 4-(4-{[2-(4-chlorophenyl)-4,4-dimethylcyclohex-1-en-1-yl]methyl}piperazin-1-yl)-N-[(4-{[(1,1-dioxidotetrahydro-2H-thiopyran-4-yl)methyl]amino}-3-nitrophenyl)sulfonyl]-2-(1H-pyrrolo[2,3-b]pyridin-5-yloxy)benzamide | 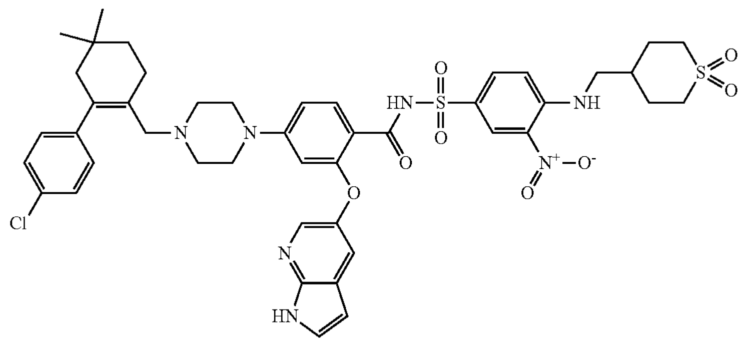 [SMILES: CC1(C)CCC(CN2CCN(c3ccc(C(=O)NS(=O)(=O)c4ccc(NCC5CCS(=O)(=O)CC5)c([N+](=O)[O-])c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-{[4-({[(2S,5R)-5-methyl-1,4-dioxan-2-yl]methyl}amino)-3-nitrophenyl]sulfonyl}-2-(1H-pyrrolo[2,3-b]pyridin-5-yloxy)benzamide | 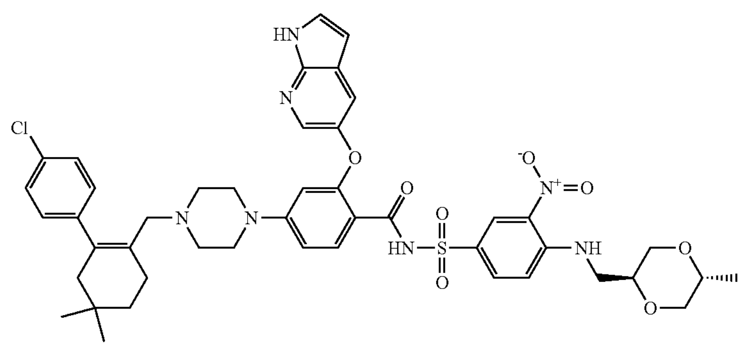 |
| 4-(4-{[2-(4-chlorophenyl)-4,4-dimethylcyclohex-1-en-1-yl]methyl}piperazin-1-yl)-N-{[4-({[(2S,5S)-5-methyl-1,4-dioxan-2-yl]methyl}amino)-3-nitrophenyl]sulfonyl}-2-(1H-pyrrolo[2,3-b]pyridin-5-yloxy)benzamide | 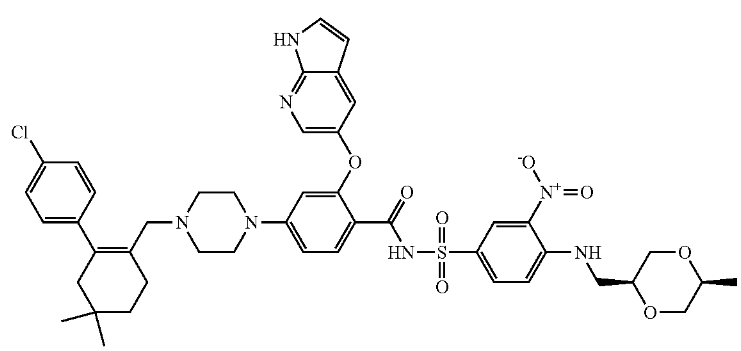 |

| Name | Structure |
|---|---|
| 4-(4-{[2-(4-chlorophenyl)-4,4-dimethylcyclohex-1-en-1-yl]methyl}piperazin-1-yl)-N-[(4-{[(4-cyanotetrahydro-2H-pyran-4-yl)methyl]amino}-3-nitrophenyl)sulfonyl]-2-(1H-pyrrolo[2,3-b]pyridin-5-yloxy)benzamide | 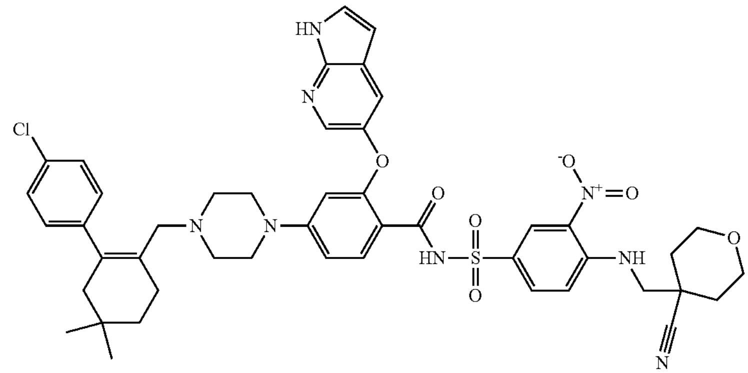 |
| N-[(4-{[(1-acetylpiperidin-4-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | 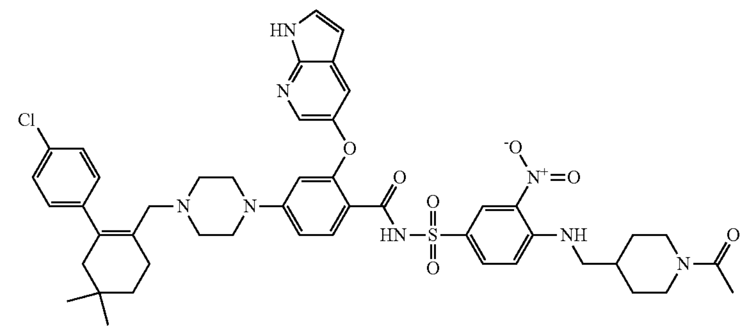 |
| 4-(4-{[2-(4-chloro-2-fluorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide | 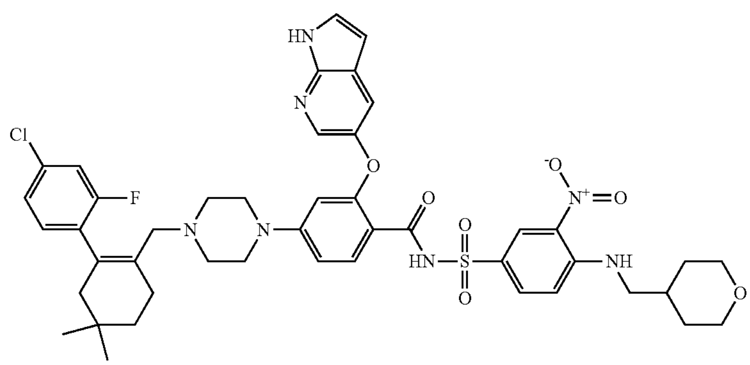 |
| 4-(4-{[2-(4-chloro-3-fluorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide | 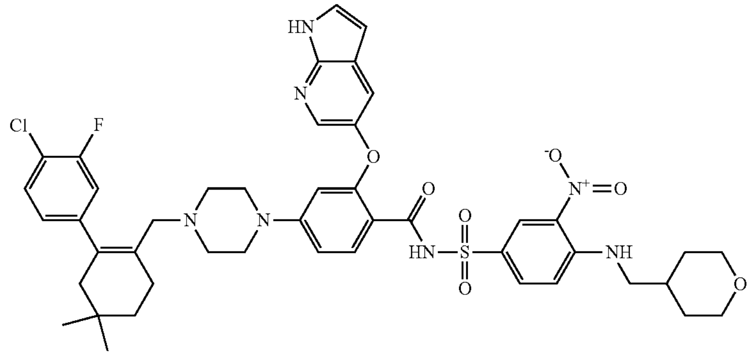 |

| Name | Structure |
|---|---|
| 4-(4-{[2-(4-chlorophenyl)-4,4-dimethylcyclohex-1-en-1-yl]methyl}piperazin-1-yl)-N-[(4-{[(4-ethyltetrahydro-2H-pyran-4-yl)methyl]amino}-3-nitrophenyl)sulfonyl]-2-(1H-pyrrolo[2,3-b]pyridin-5-yloxy)benzamide | 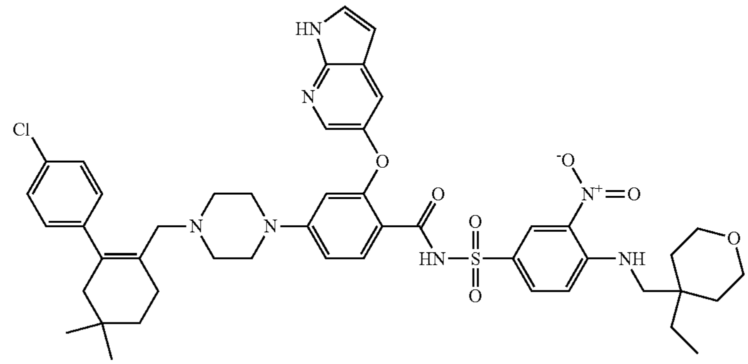 |
| 4-(4-{[2-(4-chlorophenyl)-4,4-dimethylcyclohex-1-en-1-yl]methyl}piperazin-1-yl)-N-({4-[(1,4-dioxepan-6-ylmethyl)amino]-3-nitrophenyl}sulfonyl)-2-(1H-pyrrolo[2,3-b]pyridin-5-yloxy)benzamide | 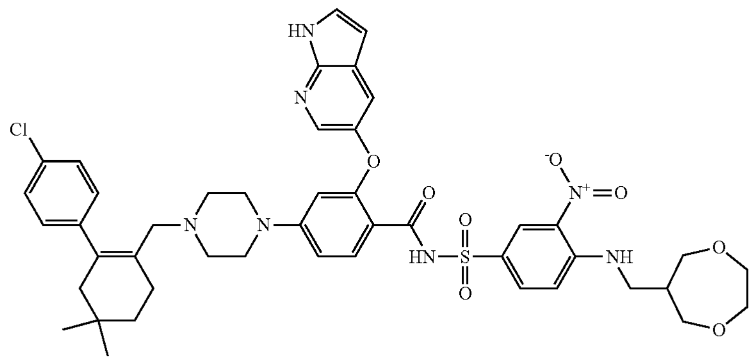 |
| 4-(4-{[2-(4-cyclopropylphenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide | 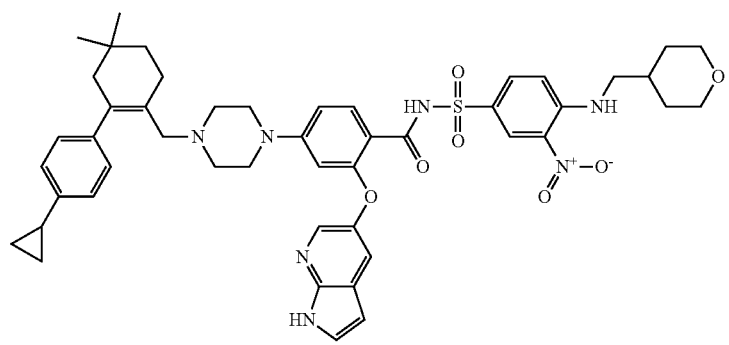 [SMILES: CC1(C)CCC(CN2CCN(c3ccc(C(=O)NS(=O)(=O)c4ccc(NCC5CCOCC5)c([N+](=O)[O-])c4)c(Oc4cnc5[nH]ccc5c4)c3)CC2)=C(c2ccc(C3CC3)cc2)C1] |
| 4-(4-{[2-(3,4-dichlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide | 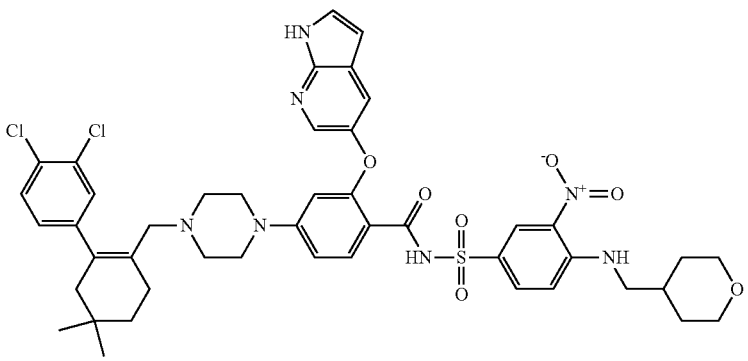 |

| Name | Structure |
|---|---|
| 4-[4-({2-[4-(difluoromethyl)phenyl]-4,4-dimethylcyclohex-1-en-1-yl}methyl)piperazin-1-yl]-N-({3-nitro-4-[(tetrahydro-2H-pyran-4-ylmethyl)amino]phenyl}sulfonyl)-2-(1H-pyrrolo[2,3-b]pyridin-5-yloxy)benzamide | 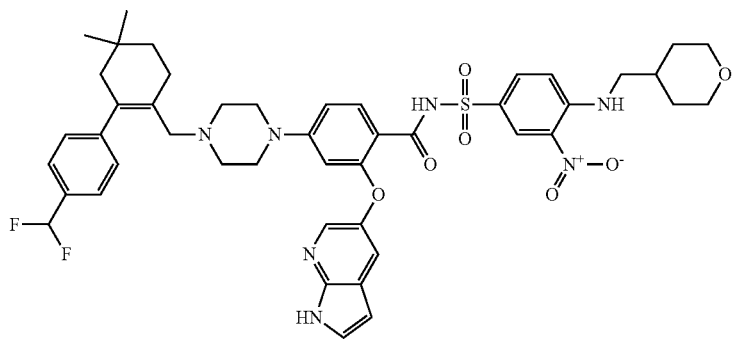 [SMILES: CC1(C)CCC(CN2CCN(c3ccc(C(=O)NS(=O)(=O)c4ccc(NCC5CCOCC5)c([N+](=O)[O-])c4)c(Oc4cnc5[nH]ccc5c4)c3)CC2)=C(c2ccc(C(F)F)cc2)C1] |

In some embodiments, the compound is selected from the group consisting of:

| Name | Structure |
|---|---|
| N-(1,3-benzothiazol-2-yl)-2-(4-{[(4-{[(2R)-4-(dimethylamino)-1-(phenylsulfanyl)butan-2-yl]amino}-3-nitrophenyl)sulfonyl]carbamoyl}-1,3-thiazol-2-yl)-1,2,3,4-tetrahydroisoquinoline-8-carboxamide; | 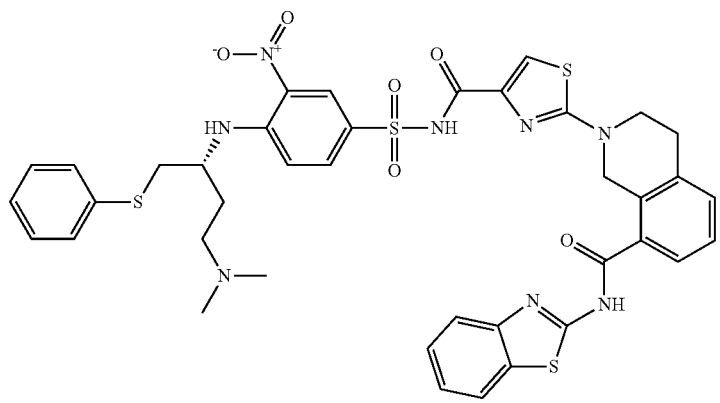 |
| N-(1,3-benzothiazol-2-yl)-2-(4-{[(4-{[(2R)-4-(morpholin-4-yl)-1-(phenylsulfanyl)butan-2-yl]amino}-3-[(trifluoromethyl)sulfonyl]phenyl)sulfonyl]carbamoyl}-1,3-thiazol-2-yl)-1,2,3,4-tetrahydroisoquinoline-8-carboxamide; | 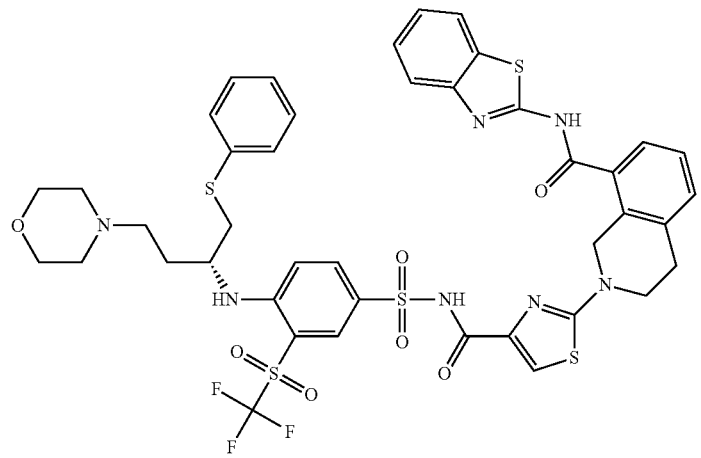 [SMILES: O=C(NS(=O)(=O)c1ccc(N[C@H](CCN2CCOCC2)CSc2ccccc2)c(S(=O)(=O)C(F)(F)F)c1)c1csc(N2CCc3cccc(C(=O)Nc4nc5ccccc5s4)c3C2)n1] |

| Name | Structure |
|---|---|
| N-(1,3-benzothiazol-2-yl)-2-(6-{[(4-{[(2R)-4-(morpholin-4-yl)-1-(phenyl-sulfanyl)butan-2-yl]amino}-3-[(trifluoromethyl)sulfonyl]phenyl)sulfonyl]carbamoyl}pyridin-2-yl)-1,2,3,4-tetrahydroisoquinoline-8-carboxamide; | 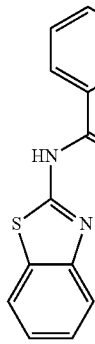 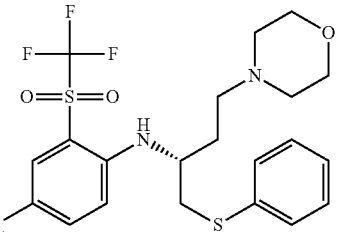 |
| N-(1,3-benzothiazol-2-yl)-2-[6-{[(4-{[3-(dimethylamino)propyl]amino}-3-[(trifluoromethyl)sulfonyl]phenyl)sulfonyl]carbamoyl}-5-(3-phenylpropyl)pyridin-2-yl]-1,2,3,4-tetrahydroisoquinoline-8-carboxamide; | 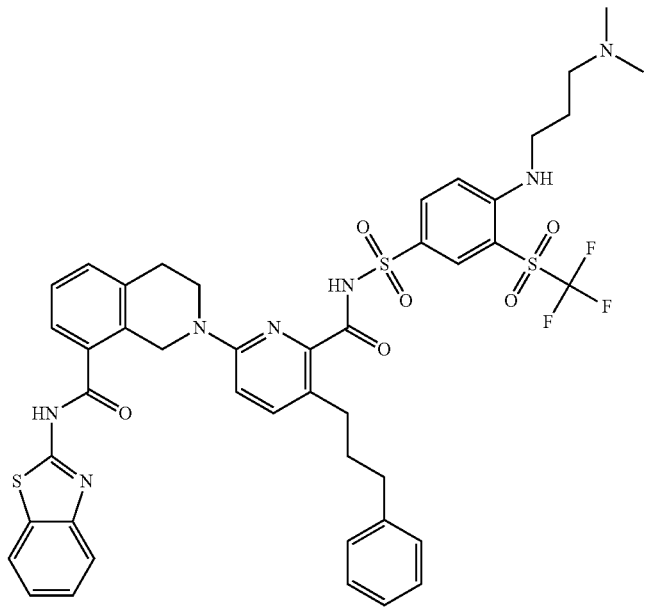 [SMILES: CN(C)CCCNc1ccc(S(=O)(=O)NC(=O)c2nc(N3CCc4cccc(C(=O)Nc5nc6ccccc6s5)c4C3)ccc2CCCc2ccccc2)cc1S(=O)(=O)C(F)(F)F] |

| Name | Structure |
|---|---|
| N-(1,3-benzothiazol-2-yl)-2-[6-{[(4-{[3-(dimethylamino)propyl]amino}-3-nitrophenyl)sulfonyl]carbamoyl}-5-(2-phenylethyl)pyridin-2-yl]-1,2,3,4-tetrahydroisoquinoline-8-carboxamide; | 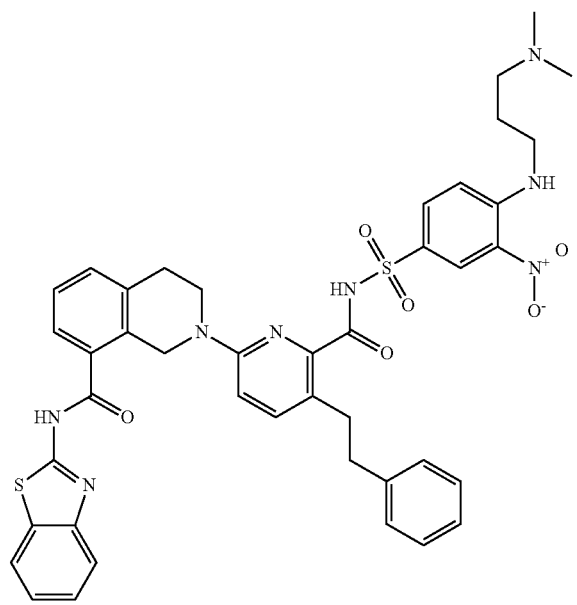 |
| N-(1,3-benzothiazol-2-yl)-2-(4-{[(4-{[3-(dimethylamino)propyl]amino}-3-[(trifluoromethyl)sulfonyl]phenyl)sulfonyl]carbamoyl}-1,3-thiazol-2-yl)-1,2,3,4-tetrahydroisoquinoline-8-carboxamide; | 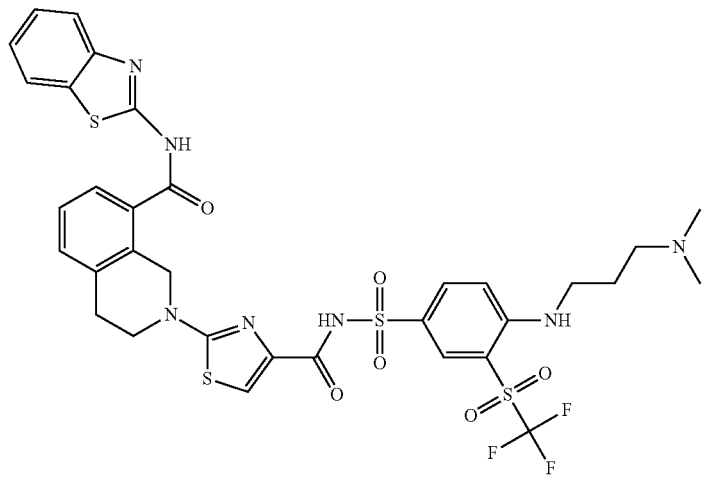 [SMILES: CN(C)CCCNc1ccc(S(=O)(=O)NC(=O)c2csc(N3CCc4cccc(C(=O)Nc5nc6ccccc6s5)c4C3)n2)cc1S(=O)(=O)C(F)(F)F] |

| Name | Structure |
|---|---|
| N-(1,3-benzothiazol-2-yl)-2-(5-benzyl-4-{[(4-{[3-(dimethylamino)propyl]amino}-3-[(trifluoromethyl)sulfonyl]phenyl)sulfonyl]carbamoyl}-1,3-thiazol-2-yl)-1,2,3,4-tetrahydroisoquinoline-8-carboxamide; | 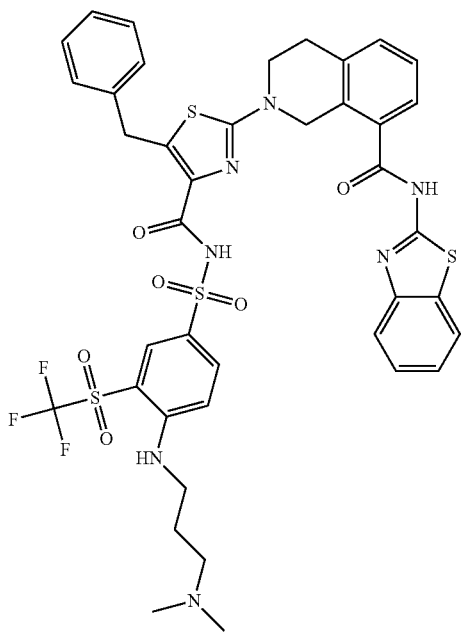 [SMILES: CN(C)CCCNc1ccc(S(=O)(=O)NC(=O)c2nc(N3CCc4cccc(C(=O)Nc5nc6ccccc6s5)c4C3)sc2Cc2ccccc2)cc1S(=O)(=O)C(F)(F)F] |
| N-(1,3-benzothiazol-2-yl)-2-(5-benzyl-4-{[(4-{[3-(dimethylamino)propyl]amino}-3-nitrophenyl)sulfonyl]carbamoyl}-1,3-thiazol-2-yl)-1,2,3,4-tetrahydroisoquinoline-8-carboxamide; | 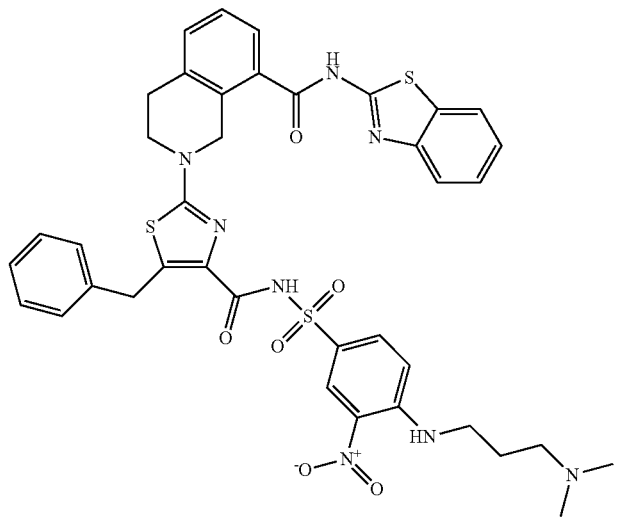 |
| N-(1,3-benzothiazol-2-yl)-2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-1,2,3,4-tetrahydroisoquinolin-8-carboxamide; | 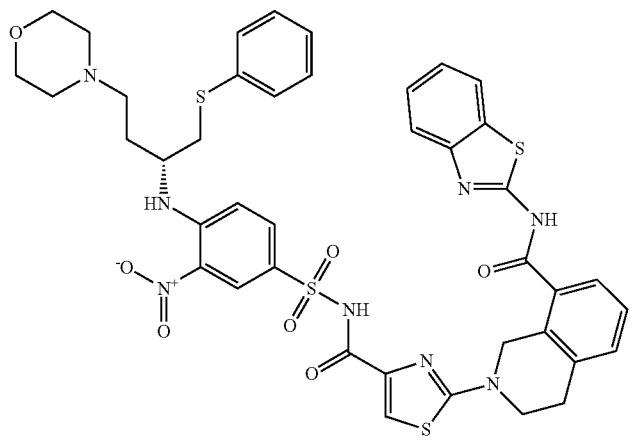 |

| Name | Structure |
|---|---|
| N-(1,3-benzothiazol-2-yl)-2-[4-{[(4-{[3-(dimethylamino)propyl]amino}-3-[(trifluoromethyl)sulfonyl]phenyl)sulfonyl]carbamoyl}-5-(2-phenylethyl)-1,3-thiazol-2-yl]-1,2,3,4-tetrahydroisoquinoline-8-carboxamide; | 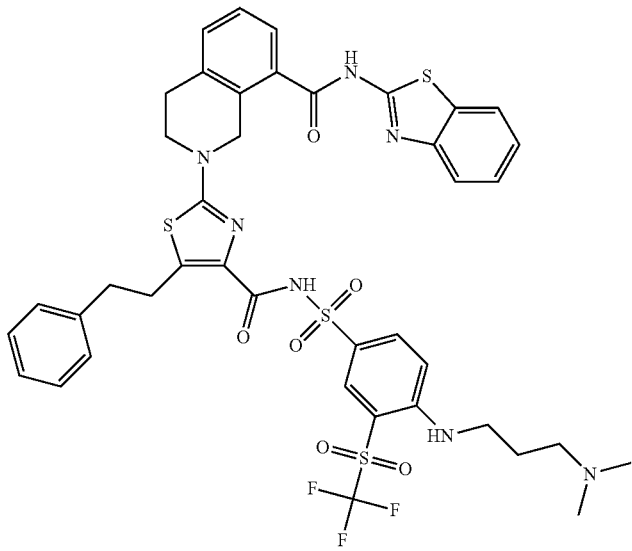 [SMILES: CN(C)CCCNc1ccc(S(=O)(=O)NC(=O)c2nc(N3CCc4cccc(C(=O)Nc5nc6ccccc6s5)c4C3)sc2CCc2ccccc2)cc1S(=O)(=O)C(F)(F)F] |
| N-(1,3-benzothiazol-2-yl)-2-(4-{[(4-{[(2R)-4-(dimethylamino)-1-(phenylsulfanyl)butan-2-yl]amino}-3-[(trifluoroemthyl)sulfonyl]phenyl)sulfonyl]carbamoyl}-1,3-thiazol-2-yl)-1,2,3,4-tetrahydroisoquinoline-8-carboxamide; | 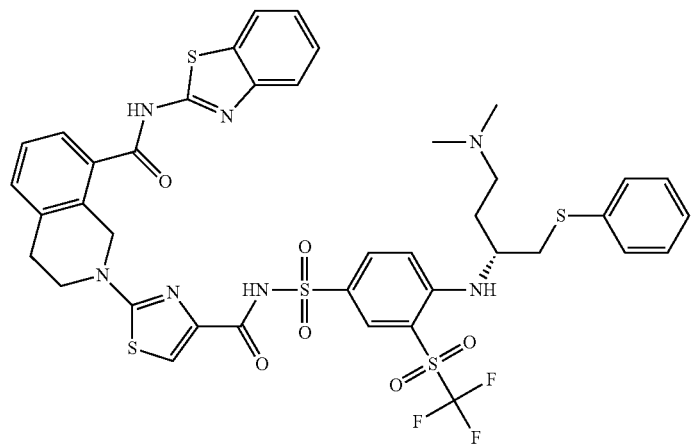 [SMILES: CN(C)CC[C@H](CSc1ccccc1)Nc1ccc(S(=O)(=O)NC(=O)c2csc(N3CCc4cccc(C(=O)Nc5nc6ccccc6s5)c4C3)n2)cc1S(=O)(=O)C(F)(F)F] |
| N-(1,3-benzothiazol-2-yl)-2-[4-{[(4-{[3-(dimethylamino)propyl]amino}-3-nitrophenyl)sulfonyl]carbamoyl}-5-(2-phenylethyl)-1,3-thiazol-2-yl]-1,2,3,4-tetrahydroisoquinoline-8-carboxamide; | 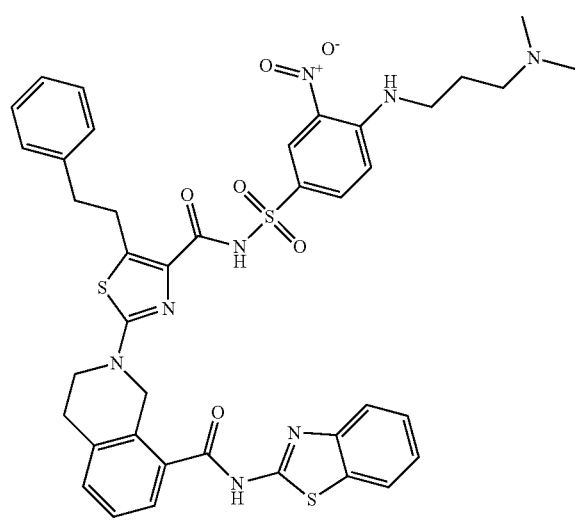 |

| Name | Structure |
|---|---|
| N-(1,3-benzothiazol-2-yl)-2-(4-{[(4-{[(2R)-4-hydroxy-1-(phenylsulfanyl)butan-2-yl]amino}-3-[(trifluoromethyl)sulfonyl]phenyl)sulfonyl]carbamoyl}-1,3-thiazol-2-yl)-1,2,3,4-tetrahydroisoquinoline-8-carboxamide; | 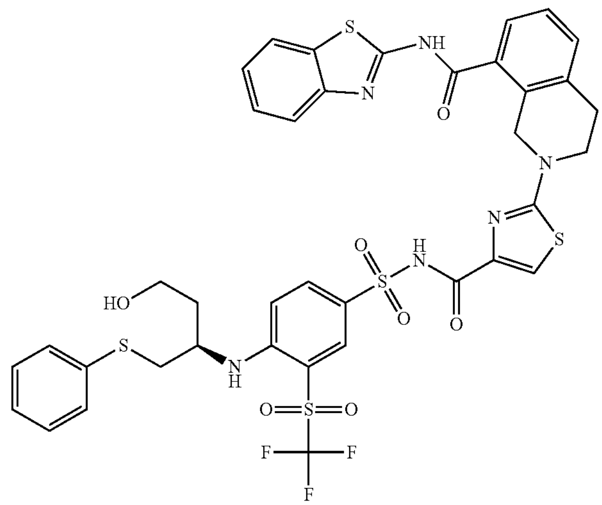 [SMILES: O=C(NS(=O)(=O)c1ccc(N[C@H](CCO)CSc2ccccc2)c(S(=O)(=O)C(F)(F)F)c1)c1csc(N2CCc3cccc(C(=O)Nc4nc5ccccc5s4)c3C2)n1] |
| N-(1,3-benzothiazol-2-yl)-2-[4-{[(4-{[3-(dimethylamino)propyl]amino}-3-nitrophenyl)sulfonyl]carbamoyl}-5-(3-phenylpropyl)-1,3-thiazol-2-yl]-1,2,3,4-tetrahydroisoquinoline-8-carboxamide; | 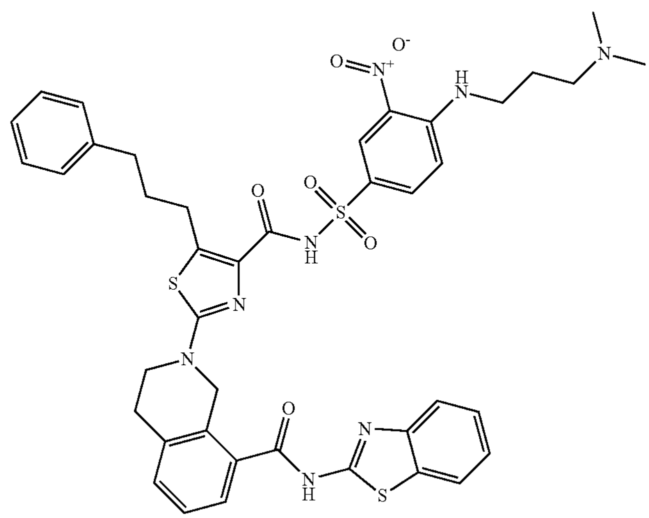 |
| 2-(6-{[(4-{[(2R)-4-(morpholin-4-yl)-1-(phenylsulfanyl)butan-2-yl]amino}-3-nitrophenyl)sulfonyl]carbamoyl}pyridin-2-yl)-N-([1,3]thiazolo[5,4-b]pyridin-2-yl)-1,2,3,4-tetrahydroisoquinoline-8-carboxamide; | 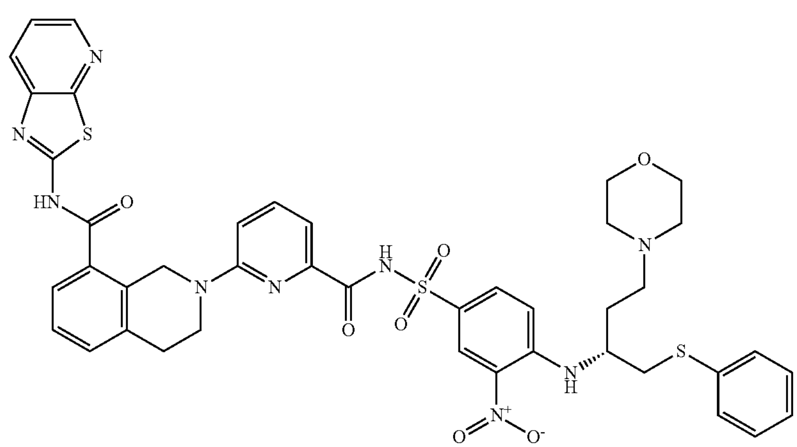 [SMILES: O=C(NS(=O)(=O)c1ccc(N[C@H](CCN2CCOCC2)CSc2ccccc2)c([N+](=O)[O-])c1)c1cccc(N2CCc3cccc(C(=O)Nc4nc5cccnc5s4)c3C2)n1] |

| Name | Structure |
|---|---|
| 2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-N-([1,3]thiazolo[5,4-b]pyridin-2-yl)-1,2,3,4-tetrahydroisoquinoline-8-carboxamide; | 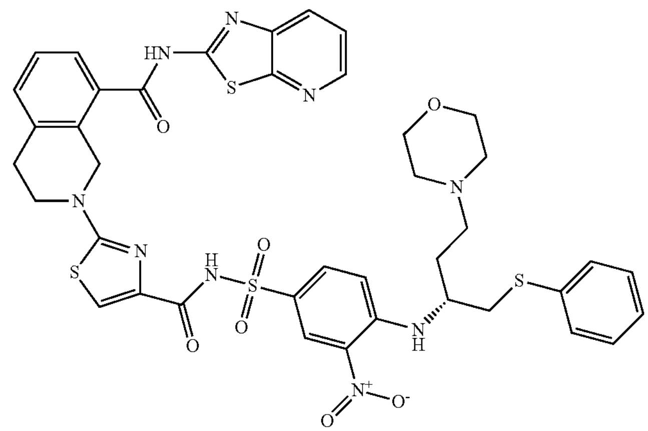 [SMILES: O=C(NS(=O)(=O)c1ccc(N[C@H](CCN2CCOCC2)CSc2ccccc2)c([N+](=O)[O-])c1)c1csc(N2CCc3cccc(C(=O)Nc4nc5cccnc5s4)c3C2)n1] |
| 2-(6-{[(4-{[(2R)-4-(morpholin-4-yl)-1-(phenylsulfanyl)butan-2-yl]amino}-3-nitrophenyl)sulfonyl]carbamoyl}pyridin-2-yl)-N-([1,3]thiazolo[5,4-c]pyridin-2-yl)-1,2,3,4-tetrahydroisoquinoline-8-carboxamide; | 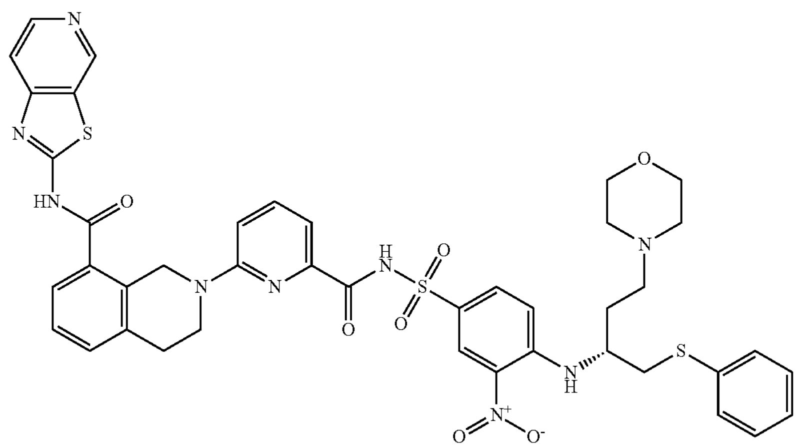 [SMILES: O=C(NS(=O)(=O)c1ccc(N[C@H](CCN2CCOCC2)CSc2ccccc2)c([N+](=O)[O-])c1)c1cccc(N2CCc3cccc(C(=O)Nc4nc5ccncc5s4)c3C2)n1] |
| 2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-N-([1,3]thiazolo[5,4-c]pyridin-2-yl)-1,2,3,4-tetrahydroisoquinoline-8-carboxamide; | 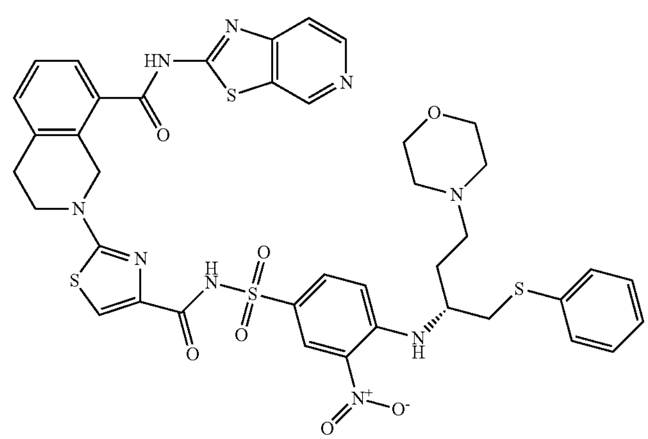 [SMILES: O=C(NS(=O)(=O)c1ccc(N[C@H](CCN2CCOCC2)CSc2ccccc2)c([N+](=O)[O-])c1)c1csc(N2CCc3cccc(C(=O)Nc4nc5ccncc5s4)c3C2)n1] |

-continued

| Name | Structure |
|---|---|
| 2-(6-{[(4-{[(2R)-4-(morpholin-4-yl)-1-(phenylsulfanyl)butan-2-yl]amino}-3-nitrophenyl)sulfonyl]carbamoyl}pyridin-2-yl)-N-([1,3]thiazolo[4,5-c]pyridin-2-yl)-1,2,3,4-tetrahydroisoquinoline-8-carboxamide; | 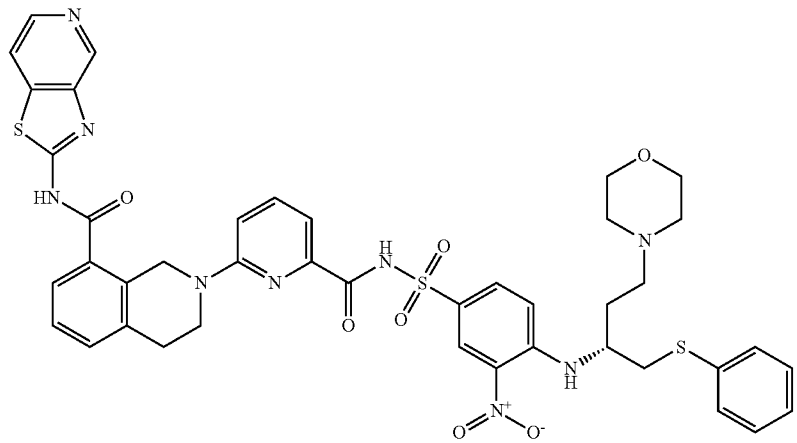 [SMILES: O=C(NS(=O)(=O)c1ccc(N[C@H](CCN2CCOCC2)CSc2ccccc2)c([N+](=O)[O-])c1)c1cccc(N2CCc3cccc(C(=O)Nc4nc5cnccc5s4)c3C2)n1] |
| 2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-N-([1,3]thiazolo[4,5-c]pyridin-2-yl)-1,2,3,4-tetrahydroisoquinoline-8-carboxamide; | 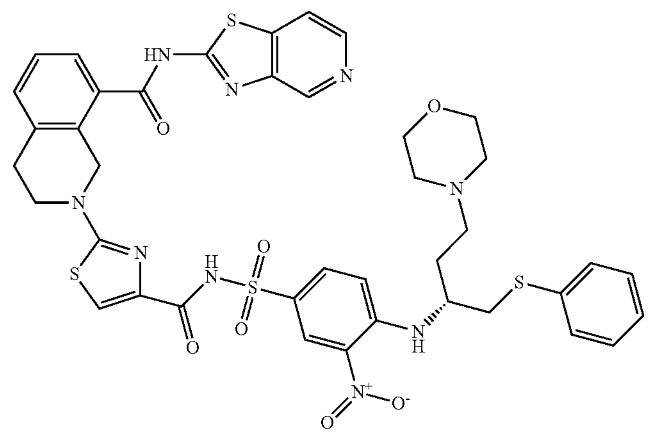 [SMILES: O=C(NS(=O)(=O)c1ccc(N[C@H](CCN2CCOCC2)CSc2ccccc2)c([N+](=O)[O-])c1)c1csc(N2CCc3cccc(C(=O)Nc4nc5cnccc5s4)c3C2)n1] |
| N-(imidazo[1,2-a]pyridin-2-yl)-2-(6-{[(4-{[(2R)-4-(morpholin-4-yl)-1-(phenylsulfanyl)butan-2-yl]amino}-3-nitrophenyl)sulfonyl]carbamoyl}pyridin-2-yl)-1,2,3,4-tetrahydroisoquinoline-8-carboxamide; | 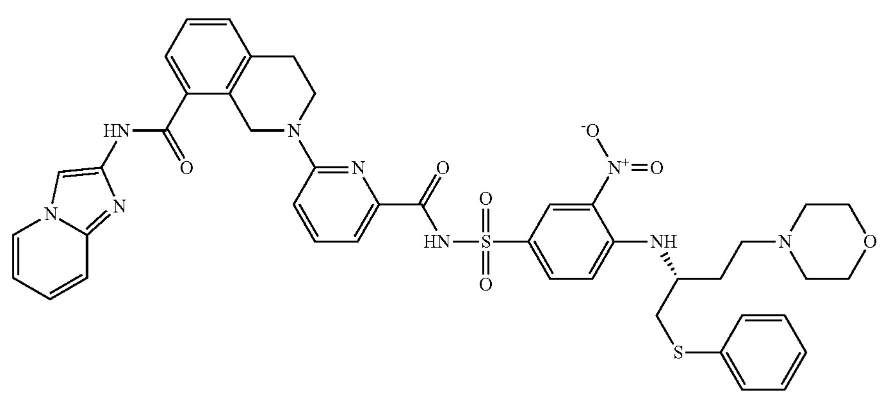 |

| Name | Structure |
|---|---|
| N-(imidazo[1,2-a]pyridin-2-yl)-2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-1,2,3,4-tetrahydroisoquinoline-8-carboxamide; | 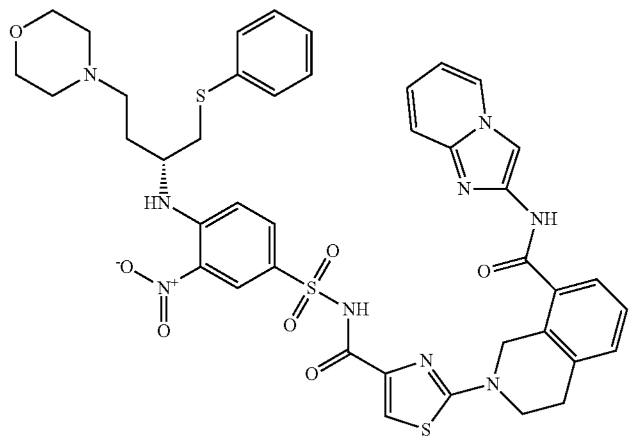 |
| N-(imidazo[1,2-a]pyrazin-2-yl)-2-(6-{[(4-{[(2R)-4-(morpholin-4-yl)-1-(phenylsulfanyl)butan-2-yl]amino}-3-nitrophenyl)sulfonyl]carbamoyl}pyridin-2-yl)-1,2,3,4-tetrahydroisoquinoline-8-carboxamide; | 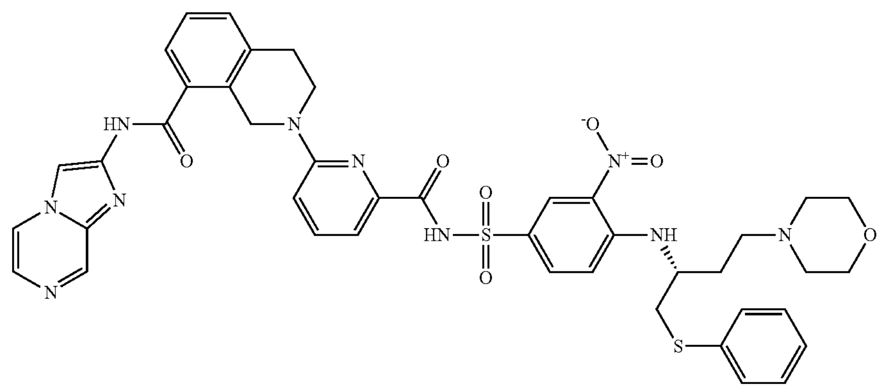 |
| N-(imidazo[1,2-a]pyrazin-2-yl)-2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-1,2,3,4-tetrahydroisoquinoline-8-carboxamide; | 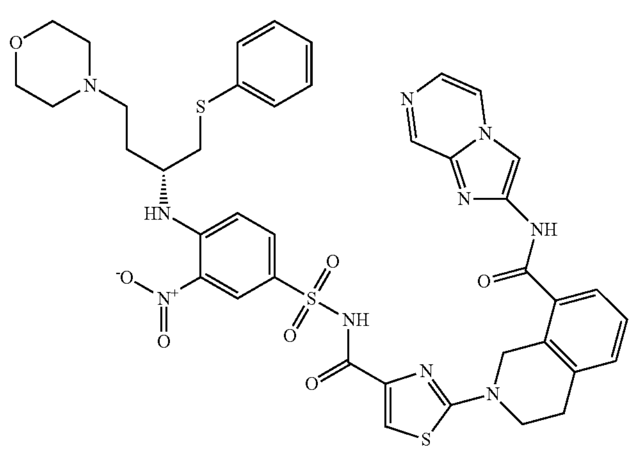 |

| Name | Structure |
|---|---|
| N-(imidazo[1,2-b]pyridazin-2-yl)-2-(6-{[(4-{[(2R)-4-(morpholin-4-yl)-1-(phenylsulfanyl)butan-2-yl]amino}-3-nitrophenyl)sulfonyl]carbamoyl}pyridin-2-yl)-1,2,3,4-tetrahydroisoquinoline-8-carboxamide; | 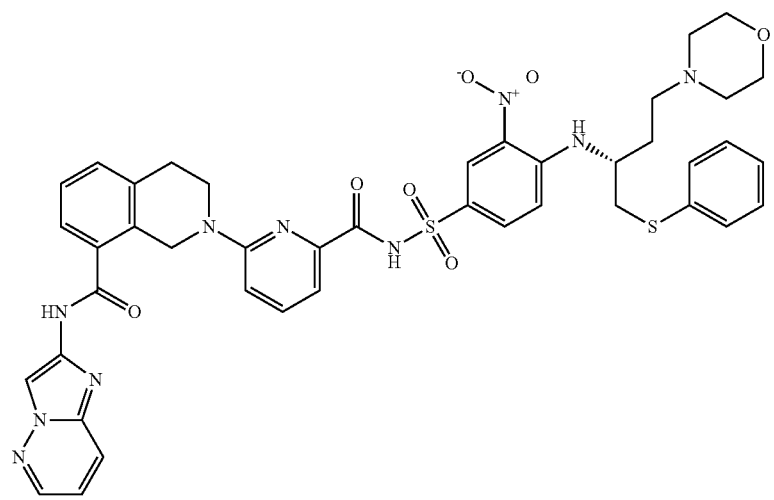 |
| N-(imidazo[1,2-b]pyridazin-2-yl)-2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-1,2,3,4-tetrahydroisoquinoline-8-carboxamide; | 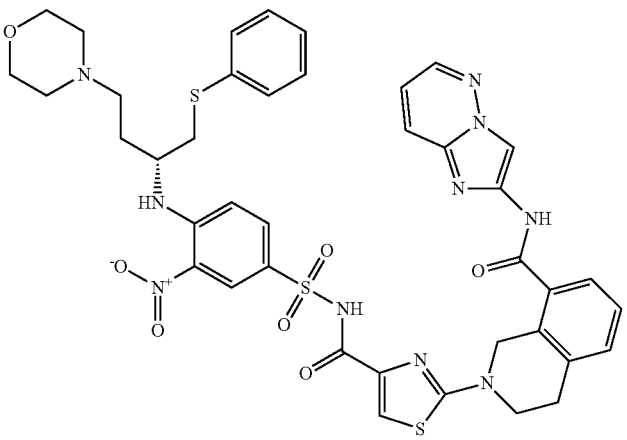 |
| N-(6-fluoro-1,3-benzothiazol-2-yl)-2-(6-{[(4-{[(2R)-4-(morpholin-4-yl)-1-(phenylsulfanyl)butan-2-yl]amino}-3-nitrophenyl)sulfonyl]carbamoyl}pyridin-2-yl)-1,2,3,4-tetrahydroisoquinoline-8-carboxamide; | 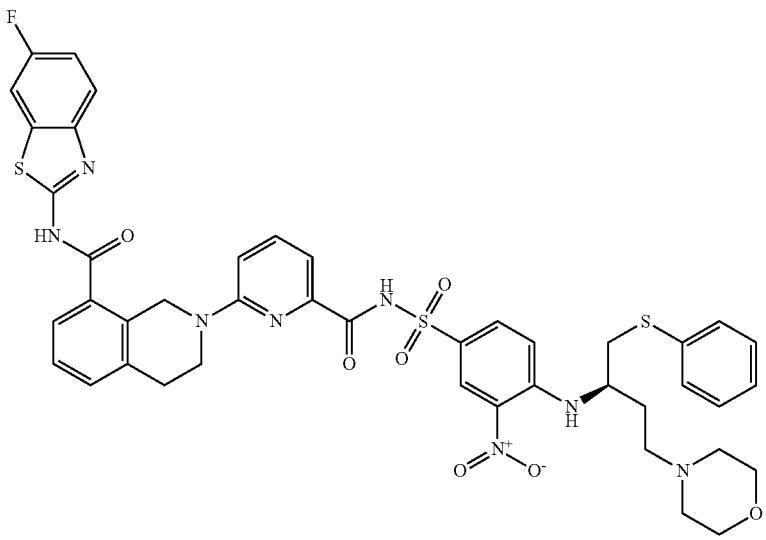 [SMILES: O=C(NS(=O)(=O)c1ccc(N[C@H](CCN2CCOCC2)CSc2ccccc2)c([N+](=O)[O-])c1)c1cccc(N2CCc3cccc(C(=O)Nc4nc5ccc(F)cc5s4)c3C2)n1] |

| Name | Structure |
|---|---|
| N-(6-fluoro-1,3-benzothiazol-2-yl)-2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-1,2,3,4-tetrahydroisoquinoline-8-carboxamide; | 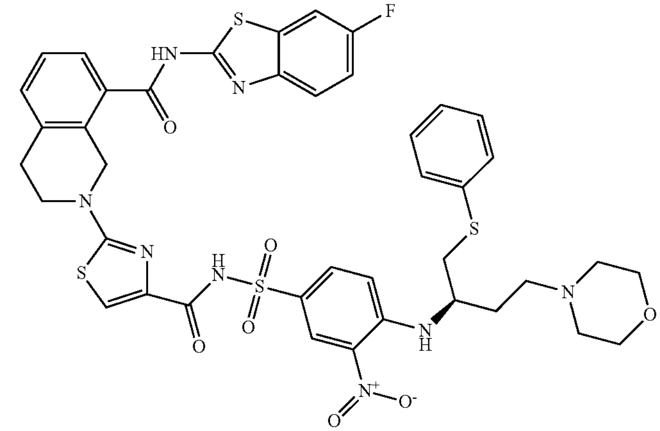 [SMILES: O=C(NS(=O)(=O)c1ccc(N[C@H](CCN2CCOCC2)CSc2ccccc2)c([N+](=O)[O-])c1)c1csc(N2CCc3cccc(C(=O)Nc4nc5ccc(F)cc5s4)c3C2)n1] |
| N-(1,3-benzothiazol-2-yl)-2-(6-{[(4-{[(2R)-4-(dimethylamino)-1-(phenylsulfanyl)butan-2-yl]amino}-3-[(trifluoromethyl)sulfonyl]phenyl)sulfonyl]carbamoyl}pyridin-2-yl)-1,2,3,4-tetrahydroisoquinoline-8-carboxamide; | 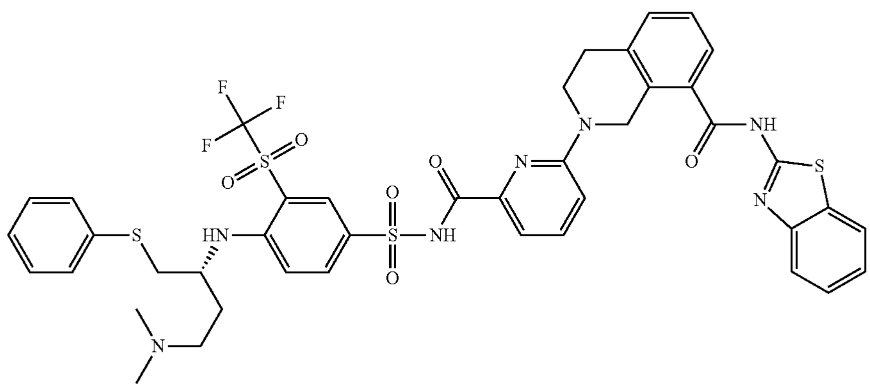 [SMILES: CN(C)CC[C@H](CSc1ccccc1)Nc1ccc(S(=O)(=O)NC(=O)c2cccc(N3CCc4cccc(C(=O)Nc5nc6ccccc6s5)c4C3)n2)cc1S(=O)(=O)C(F)(F)F] |
| N-(1,3-benzothiazol-2-yl)-2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-1,2,3,4-tetrahydroisoquinoline-8-carboxamide; | 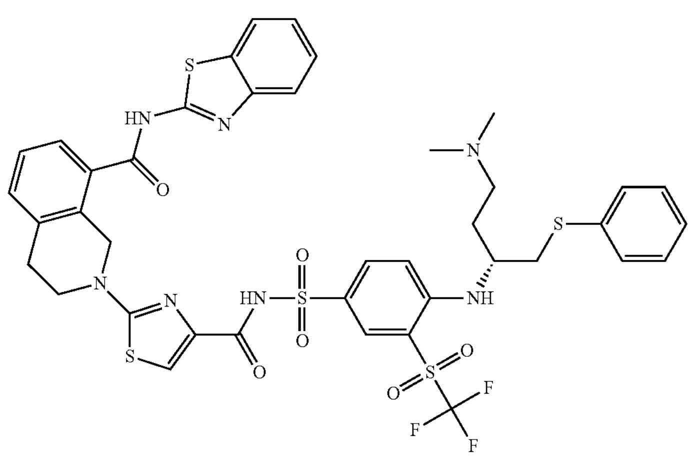 [SMILES: CN(C)CC[C@H](CSc1ccccc1)Nc1ccc(S(=O)(=O)NC(=O)c2csc(N3CCc4cccc(C(=O)Nc5nc6ccccc6s5)c4C3)n2)cc1S(=O)(=O)C(F)(F)F] |

| Name | Structure |
|---|---|
| 2-(6-{[(4-{[(2R)-4-(dimethylamino)-1-(phenylsulfanyl)butan-2-yl]amino}-3-[(trifluoromethyl)sulfonyl]phenyl)sulfonyl]carbamoyl}pyridin-2-yl)-N-([1,3]thiazolo[5,4-b]pyridin-2-yl)-1,2,3,4-tetrahydroisoquinoline-8-carboxamide; | 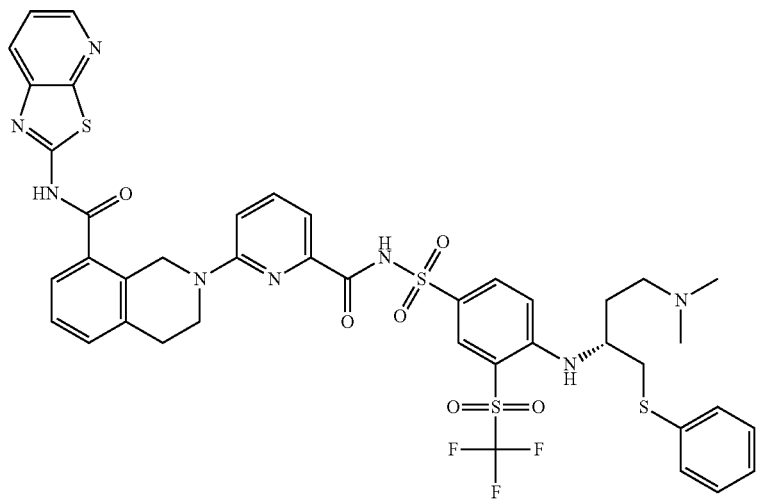 [SMILES: CN(C)CC[C@H](CSc1ccccc1)Nc1ccc(S(=O)(=O)NC(=O)c2cccc(N3CCc4cccc(C(=O)Nc5nc6cccnc6s5)c4C3)n2)cc1S(=O)(=O)C(F)(F)F] |
| 2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-N-([1,3]thiazolo[5,4-b]pyridin-2-yl)-1,2,3,4-tetrahydroisoquinoline-8-carboxamide; | 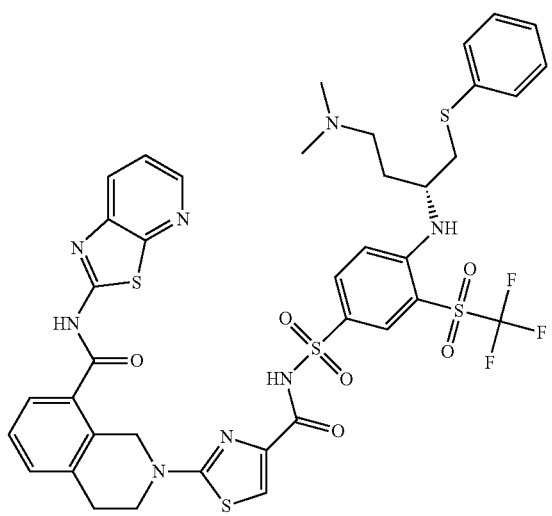 [SMILES: CN(C)CC[C@H](CSc1ccccc1)Nc1ccc(S(=O)(=O)NC(=O)c2csc(N3CCc4cccc(C(=O)Nc5nc6cccnc6s5)c4C3)n2)cc1S(=O)(=O)C(F)(F)F] |
| 2-(6-{[(4-{[(2R)-4-(dimethylamino)-1-(phenylsulfanyl)butan-2-yl]amino}-3-[(trifluoromethyl)sulfonyl]phenyl)sulfonyl]carbamoyl}pyridin-2-yl)-N-([1,3]thiazolo[5,4-c]pyridin-2-yl)-1,2,3,4-tetrahydroisoquinoline-8-carboxamide; | 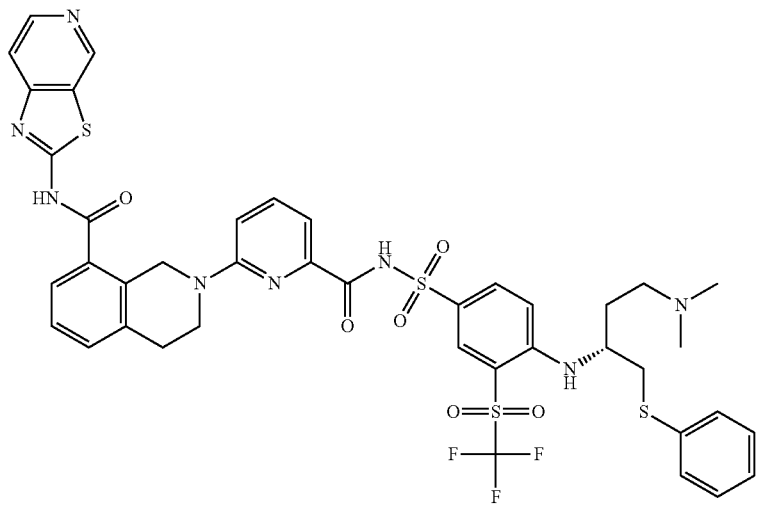 [SMILES: CN(C)CC[C@H](CSc1ccccc1)Nc1ccc(S(=O)(=O)NC(=O)c2cccc(N3CCc4cccc(C(=O)Nc5nc6ccncc6s5)c4C3)n2)cc1S(=O)(=O)C(F)(F)F] |

| Name | Structure |
| --- | --- |
| 2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-N-([1,3]thiazolo[5,4-c]pyridin-2-yl)-1,2,3,4-tetrahydroisoquinoline-8-carboxamide; | 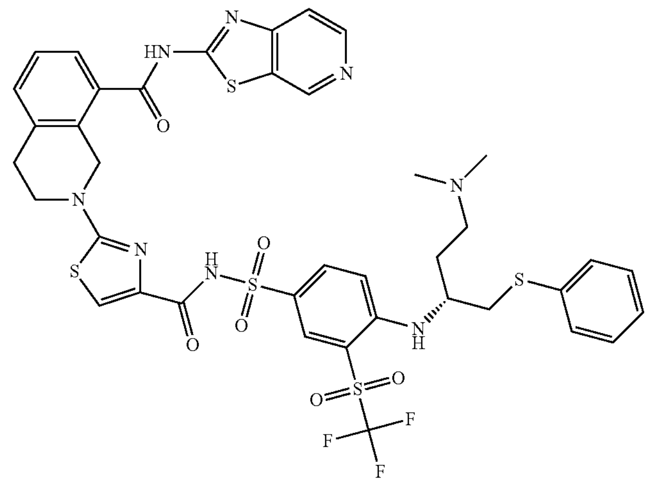 [SMILES: CN(C)CC[C@H](CSc1ccccc1)Nc1ccc(S(=O)(=O)NC(=O)c2csc(N3CCc4cccc(C(=O)Nc5nc6ccncc6s5)c4C3)n2)cc1S(=O)(=O)C(F)(F)F] |
| 2-(6-{[(4-{[(2R)-4-(dimethylamino)-1-(phenylsulfanyl)butan-2-yl]amino}-3-[(trifluoromethyl)sulfonyl]phenyl)sulfonyl]carbamoyl}pyridin-2-yl)-N-([1,3]thiazolo[4,5-c]pyridin-2-yl)-1,2,3,4-tetrahydroisoquinoline-8-carboxamide; | 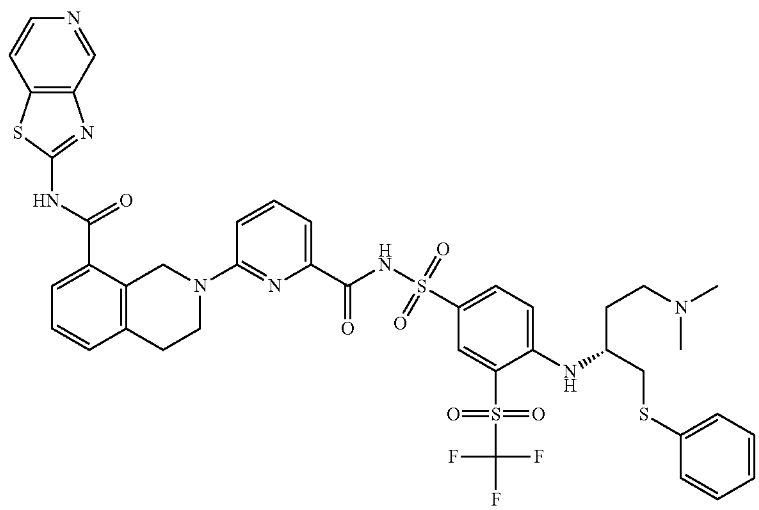 [SMILES: CN(C)CC[C@H](CSc1ccccc1)Nc1ccc(S(=O)(=O)NC(=O)c2cccc(N3CCc4cccc(C(=O)Nc5nc6cnccc6s5)c4C3)n2)cc1S(=O)(=O)C(F)(F)F] |
| 2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-N-([1,3]thiazolo[4,5-c]pyridin-2-yl)-1,2,3,4-tetrahydroisoquinoline-8-carboxamide; | 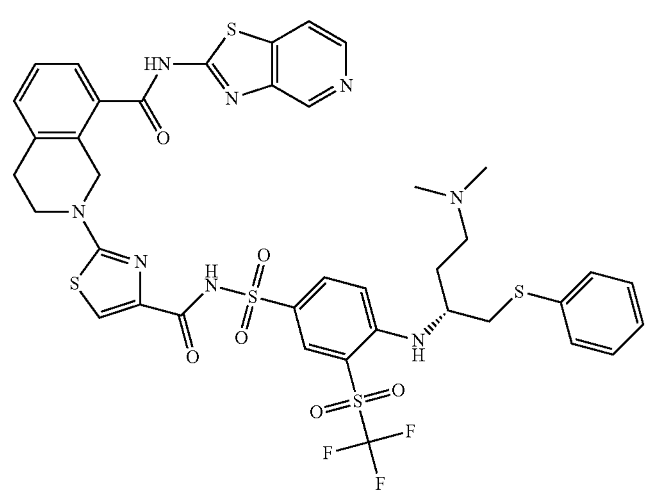 [SMILES: CN(C)CC[C@H](CSc1ccccc1)Nc1ccc(S(=O)(=O)NC(=O)c2csc(N3CCc4cccc(C(=O)Nc5nc6cnccc6s5)c4C3)n2)cc1S(=O)(=O)C(F)(F)F] |

| Name | Structure |
|---|---|
| 2-(6-{[(4-{[(2R)-4-(dimethylamino)-1-(phenylsulfanyl)butan-2-yl]amino}-3-[(trifluoromethyl)sulfonyl]phenyl)sulfonyl]carbamoyl}pyridin-2-yl)-N-(imidazo[1,2-a]pyridin-2-yl)-1,2,3,4-tetrahydroisoquinoline-8-carboxamide; | 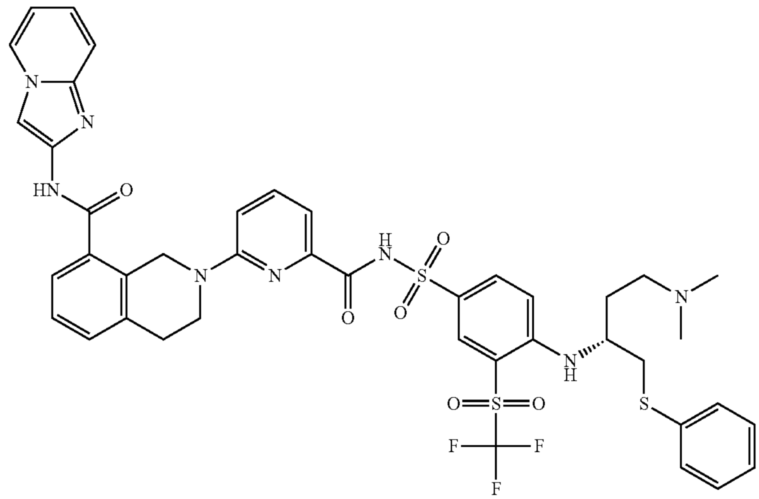 [SMILES: CN(C)CC[C@H](CSc1ccccc1)Nc1ccc(S(=O)(=O)NC(=O)c2cccc(N3CCc4cccc(C(=O)Nc5cn6ccccc6n5)c4C3)n2)cc1S(=O)(=O)C(F)(F)F] |
| 2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-N-(imidazo[1,2-a]pyridin-2-yl)-1,2,3,4-tetrahydroisoquinoline-8-carboxamide; | 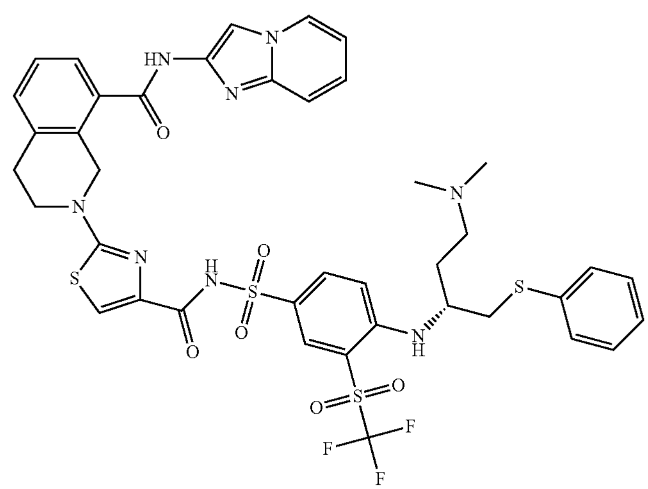 [SMILES: CN(C)CC[C@H](CSc1ccccc1)Nc1ccc(S(=O)(=O)NC(=O)c2csc(N3CCc4cccc(C(=O)Nc5cn6ccccc6n5)c4C3)n2)cc1S(=O)(=O)C(F)(F)F] |
| 2-(6-{[(4-{[(2R)-4-(dimethylamino)-1-(phenylsulfanyl)butan-2-yl]amino}-3-[(trifluoromethyl)sulfonyl]phenyl)sulfonyl]carbamoyl}pyridin-2-yl)-N-(imidazo[1,2-a]pyrazin-2-yl)-1,2,3,4-tetrahydroisoquinoline-8-carboxamide; | 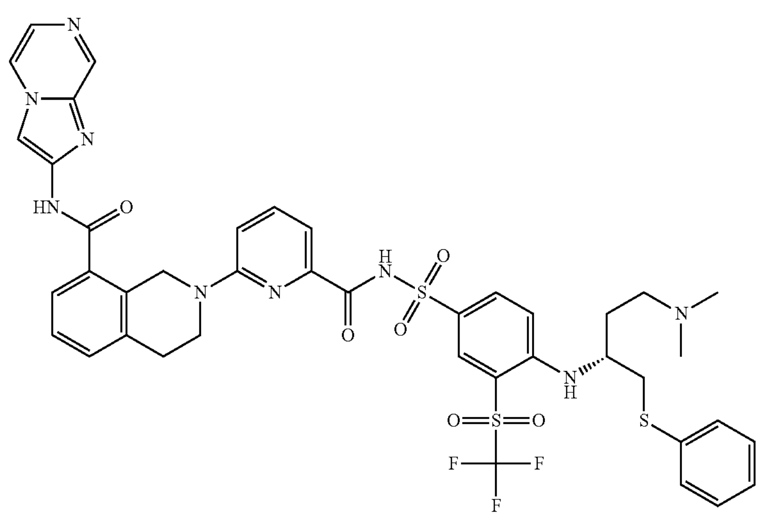 [SMILES: CN(C)CC[C@H](CSc1ccccc1)Nc1ccc(S(=O)(=O)NC(=O)c2cccc(N3CCc4cccc(C(=O)Nc5cn6ccncc6n5)c4C3)n2)cc1S(=O)(=O)C(F)(F)F] |

| Name | Structure |
|---|---|
| 2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-N-(imidazo[1,2-a]pyrazin-2-yl)-1,2,3,4-tetrahydroisoquinoline-8-carboxamide; | 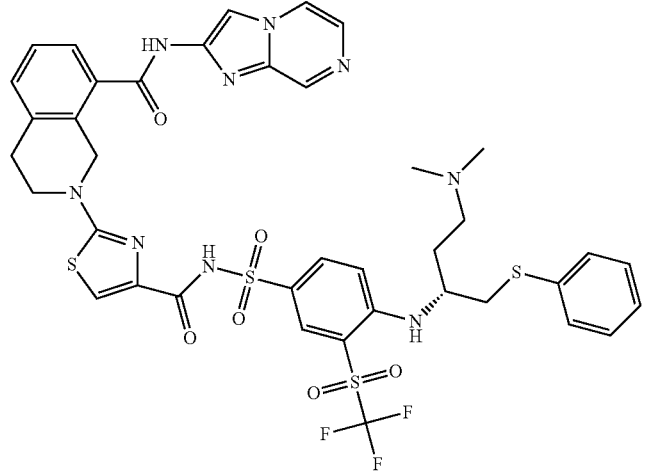 [SMILES: CN(C)CC[C@H](CSc1ccccc1)Nc1ccc(S(=O)(=O)NC(=O)c2csc(N3CCc4cccc(C(=O)Nc5cn6ccncc6n5)c4C3)n2)cc1S(=O)(=O)C(F)(F)F] |
| 2-(6-{[(4-{[(2R)-4-(dimethylamino)-1-(phenylsulfanyl)butan-2-yl]amino}-3-[(trifluoromethyl)sulfonyl]phenyl)sulfonyl]carbamoyl}pyridin-2-yl)-N-(imidazo[1,2-b]pyridazin-2-yl)-1,2,3,4-tetrahydroisoquinoline-8-carboxamide; | 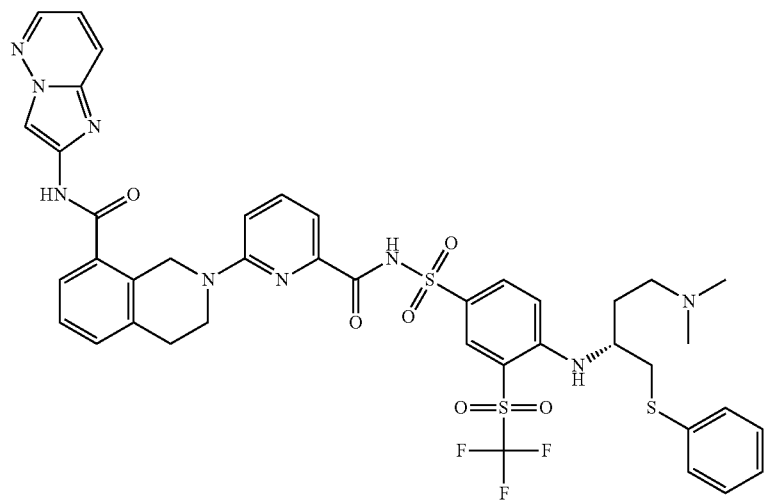 [SMILES: CN(C)CC[C@H](CSc1ccccc1)Nc1ccc(S(=O)(=O)NC(=O)c2cccc(N3CCc4cccc(C(=O)Nc5cn6ncccc6n5)c4C3)n2)cc1S(=O)(=O)C(F)(F)F] |
| 2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-N-(imidazo[1,2-b]pyridazin-2-yl)-1,2,3,4-tetrahydroisoquinoline-8-carboxamide; | 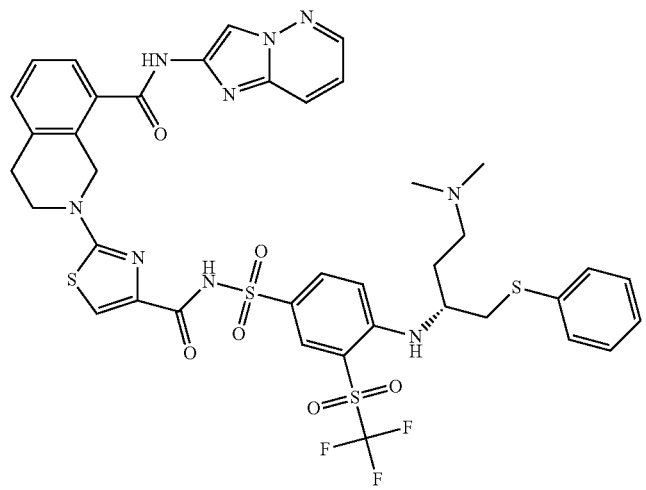 [SMILES: CN(C)CC[C@H](CSc1ccccc1)Nc1ccc(S(=O)(=O)NC(=O)c2csc(N3CCc4cccc(C(=O)Nc5cn6ncccc6n5)c4C3)n2)cc1S(=O)(=O)C(F)(F)F] |

| Name | Structure |
|---|---|
| 2-(6-{[(4-{[(2R)-4-(dimethylamino)-1-(phenylsulfanyl)butan-2-yl]amino}-3-[(trifluoromethyl)sulfonyl]phenyl)sulfonyl]carbamoyl}pyridin-2-yl)-N-(6-fluoro-1,3-benzothiazol-2-yl)-1,2,3,4-tetrahydroisoquinoline-8-carboxamide; | 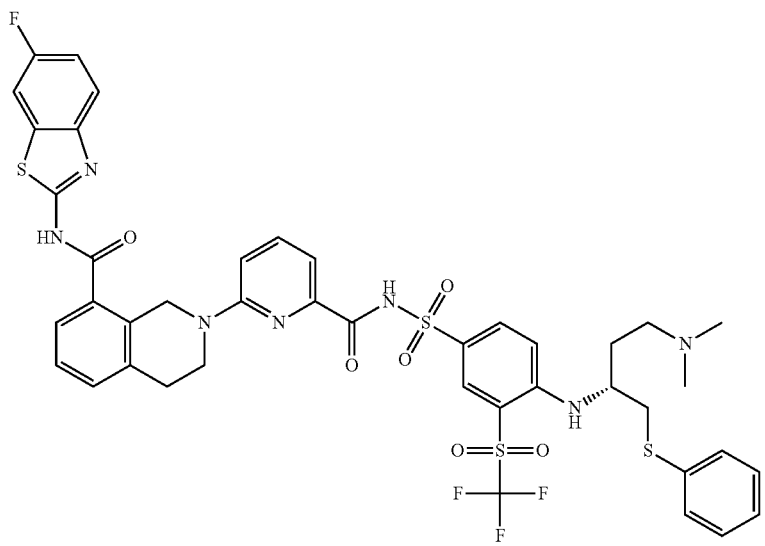 [SMILES: CN(C)CC[C@H](CSc1ccccc1)Nc1ccc(S(=O)(=O)NC(=O)c2cccc(N3CCc4cccc(C(=O)Nc5nc6ccc(F)cc6s5)c4C3)n2)cc1S(=O)(=O)C(F)(F)F] |
| 2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-N-(6-fluoro-1,3-benzothiazol-2-yl)-1,2,3,4-tetrahydroisoquinoline-8-carboxamide; | 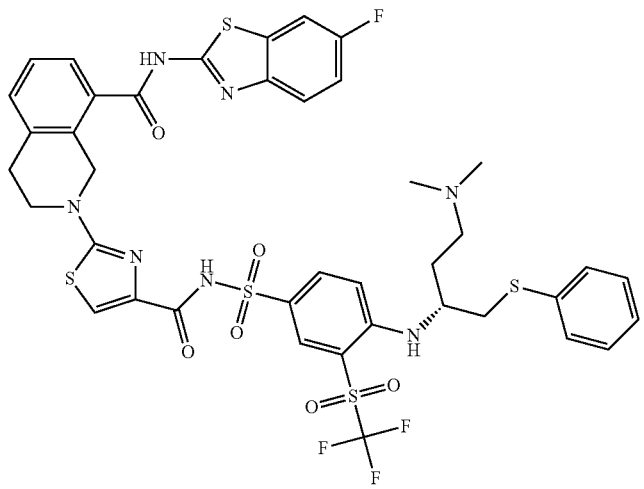 [SMILES: CN(C)CC[C@H](CSc1ccccc1)Nc1ccc(S(=O)(=O)NC(=O)c2csc(N3CCc4cccc(C(=O)Nc5nc6ccc(F)cc6s5)c4C3)n2)cc1S(=O)(=O)C(F)(F)F] |
| N-(1,3-benzothiazol-2-yl)-2-(6-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}pyridin-2-yl)-1,2,3,4-tetrahydroisoquinoline-8-carboxamide; | 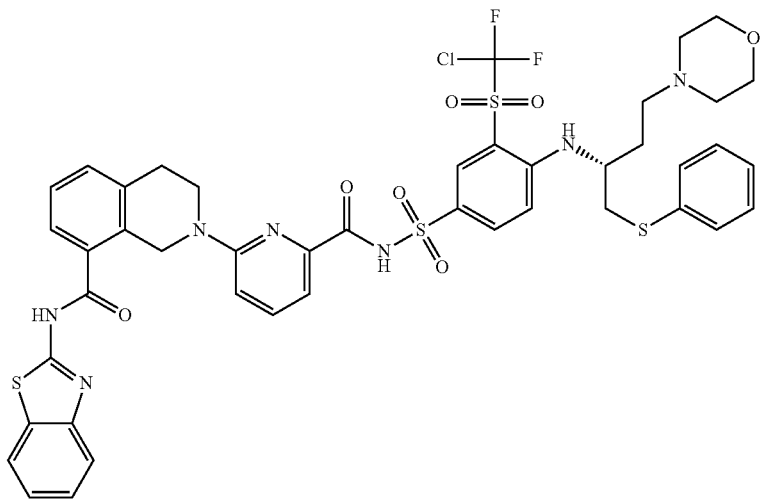 [SMILES: O=C(NS(=O)(=O)c1ccc(N[C@H](CCN2CCOCC2)CSc2ccccc2)c(S(=O)(=O)C(F)(F)Cl)c1)c1cccc(N2CCc3cccc(C(=O)Nc4nc5ccccc5s4)c3C2)n1] |

| Name | Structure |
| --- | --- |
| N-(1,3-benzothiazol-2-yl)-2-(4-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}-1,3-thiazol-2-yl)-1,2,3,4-tetrahydroisoquinoline-8-carboxamide; | |
| 2-(6-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}pyridin-2-yl)-N-([1,3]thiazolo[5,4-b]pyridin-2-yl)-1,2,3,4-tetrahydroisoquinoline-8-carboxamide; | 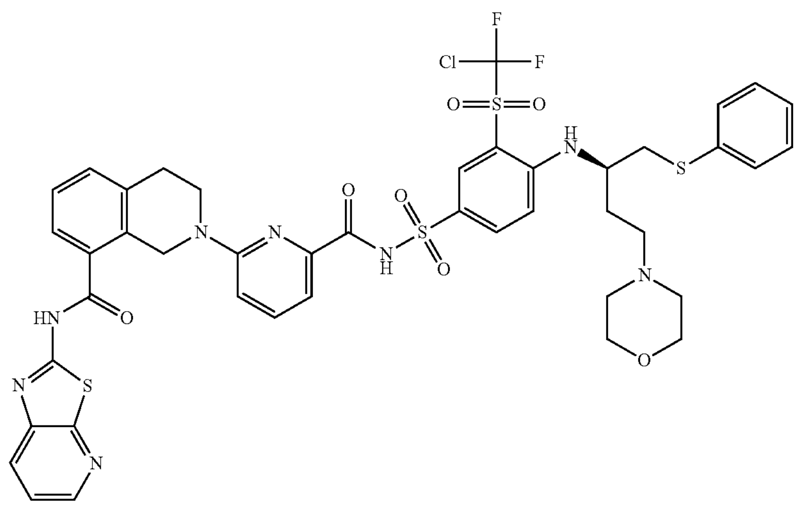 [SMILES: O=C(NS(=O)(=O)c1ccc(N[C@H](CCN2CCOCC2)CSc2ccccc2)c(S(=O)(=O)C(F)(F)Cl)c1)c1cccc(N2CCc3cccc(C(=O)Nc4nc5cccnc5s4)c3C2)n1] |
| 2-(4-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}-1,3-thiazol-2-yl)-N-([1,3]thiazolo[5,4-b]pyridin-2-yl)-1,2,3,4-tetrahydroisoquinoline-8-carboxamide; | 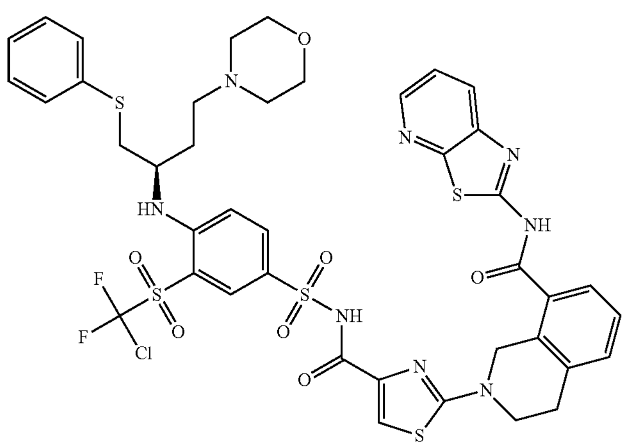 [SMILES: O=C(NS(=O)(=O)c1ccc(N[C@H](CCN2CCOCC2)CSc2ccccc2)c(S(=O)(=O)C(F)(F)Cl)c1)c1csc(N2CCc3cccc(C(=O)Nc4nc5cccnc5s4)c3C2)n1] |

| Name | Structure |
|---|---|
| 2-(6-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}pyridin-2-yl)-N-([1,3]thiazolo[5,4-c]pyridin-2-yl)-1,2,3,4-tetrahydroisoquinoline-8-carboxamide; | 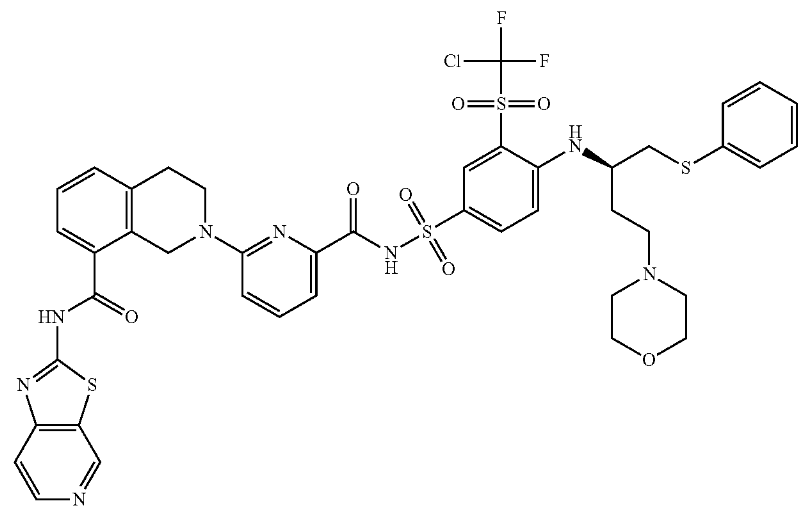 [SMILES: O=C(NS(=O)(=O)c1ccc(N[C@H](CCN2CCOCC2)CSc2ccccc2)c(S(=O)(=O)C(F)(F)Cl)c1)c1cccc(N2CCc3cccc(C(=O)Nc4nc5ccncc5s4)c3C2)n1] |
| 2-(4-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}-1,3-thiazol-2-yl)-N-([1,3]thiazolo[5,4-c]pyridin-2-yl)-1,2,3,4-tetrahydroisoquinoline-8-carboxamide; | 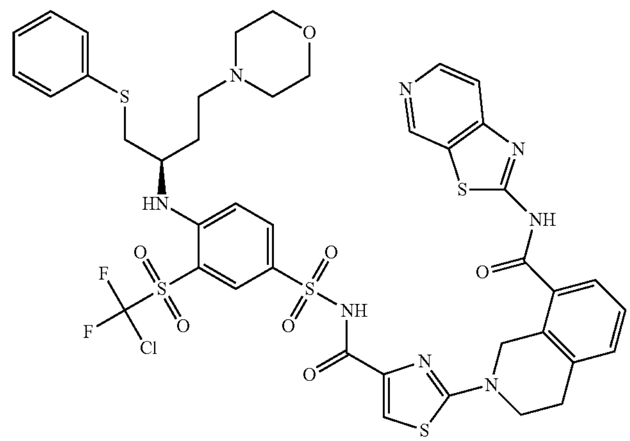 [SMILES: O=C(NS(=O)(=O)c1ccc(N[C@H](CCN2CCOCC2)CSc2ccccc2)c(S(=O)(=O)C(F)(F)Cl)c1)c1csc(N2CCc3cccc(C(=O)Nc4nc5ccncc5s4)c3C2)n1] |
| 2-(6-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}pyridin-2-yl)-N-([1,3]thiazolo[4,5-c]pyridin-2-yl)-1,2,3,4-tetrahydroisoquinoline-8-carboxamide; | 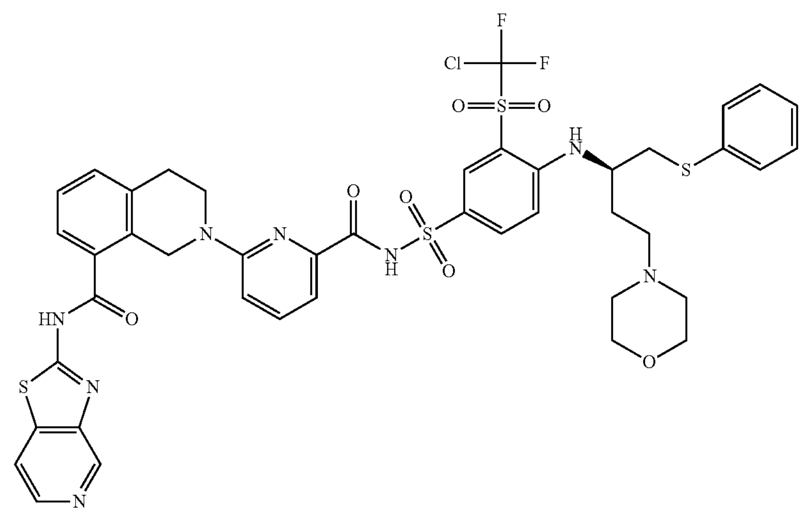 [SMILES: O=C(NS(=O)(=O)c1ccc(N[C@H](CCN2CCOCC2)CSc2ccccc2)c(S(=O)(=O)C(F)(F)Cl)c1)c1cccc(N2CCc3cccc(C(=O)Nc4nc5cnccc5s4)c3C2)n1] |

| Name | Structure |
|---|---|
| 2-(4-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}-1,3-thiazol-2-yl)-N-([1,3]thiazolo[4,5-c]pyridin-2-yl)-1,2,3,4-tetrahydroisoquinoline-8-carboxamide; | 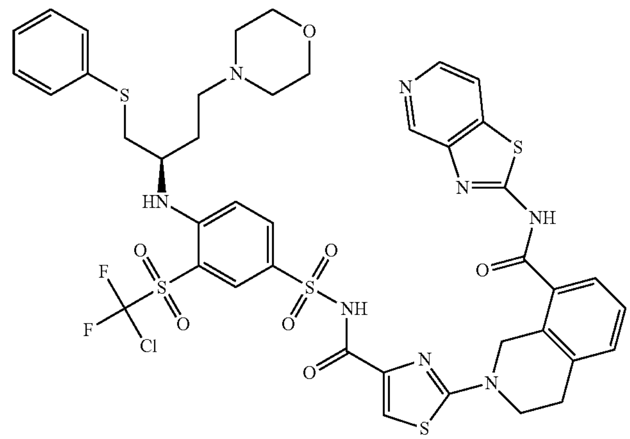 [SMILES: O=C(NS(=O)(=O)c1ccc(N[C@H](CCN2CCOCC2)CSc2ccccc2)c(S(=O)(=O)C(F)(F)Cl)c1)c1csc(N2CCc3cccc(C(=O)Nc4nc5cnccc5s4)c3C2)n1] |
| 2-(6-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}pyridin-2-yl)-N-(imidazo[1,2-a]pyridin-2-yl)-1,2,3,4-tetrahydroisoquinoline-8-carboxamide; | 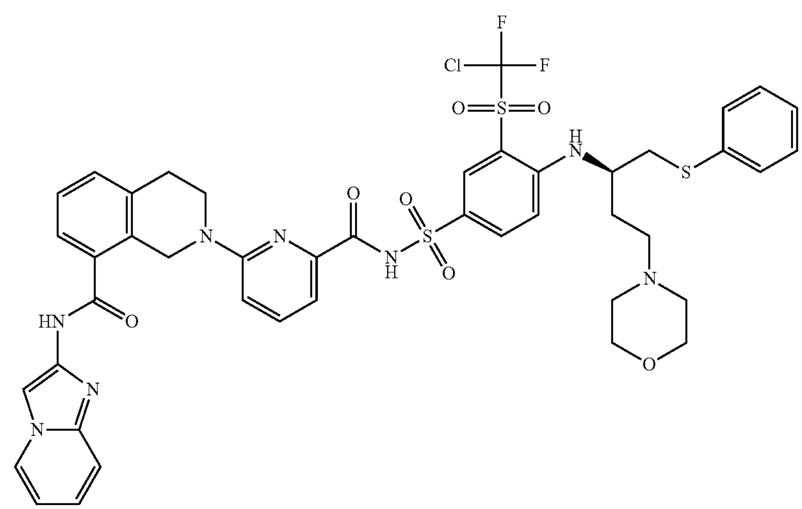 [SMILES: O=C(NS(=O)(=O)c1ccc(N[C@H](CCN2CCOCC2)CSc2ccccc2)c(S(=O)(=O)C(F)(F)Cl)c1)c1cccc(N2CCc3cccc(C(=O)Nc4cn5ccccc5n4)c3C2)n1] |
| 2-(4-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}-1,3-thiazol-2-yl)-N-(imidazo[1,2-a]pyridin-2-yl)-1,2,3,4-tetrahydroisoquinoline-8-carboxamide; | 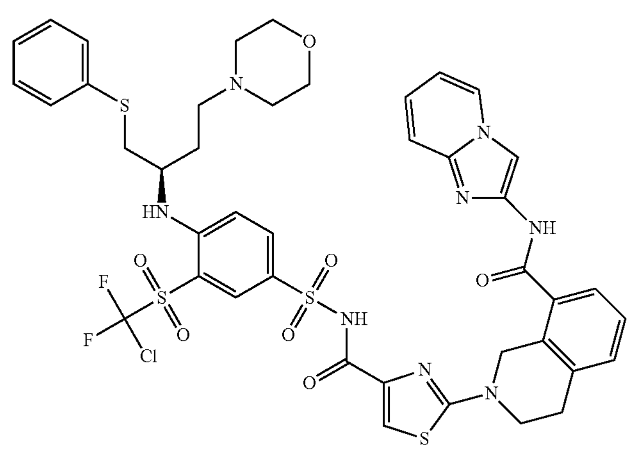 [SMILES: O=C(NS(=O)(=O)c1ccc(N[C@H](CCN2CCOCC2)CSc2ccccc2)c(S(=O)(=O)C(F)(F)Cl)c1)c1csc(N2CCc3cccc(C(=O)Nc4cn5ccccc5n4)c3C2)n1] |

| Name | Structure |
|---|---|
| 2-(6-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}pyridin-2-yl)-N-(imidazo[1,2-a]pyrazin-2-yl)-1,2,3,4-tetrahydroisoquinoline-8-carboxamide; | 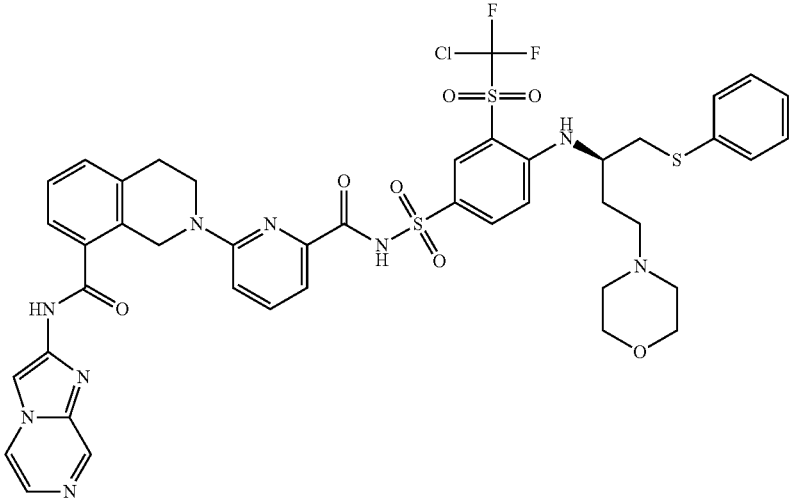 [SMILES: O=C(NS(=O)(=O)c1ccc(N[C@H](CCN2CCOCC2)CSc2ccccc2)c(S(=O)(=O)C(F)(F)Cl)c1)c1cccc(N2CCc3cccc(C(=O)Nc4cn5ccncc5n4)c3C2)n1] |
| 2-(4-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}-1,3-thiazol-2-yl)-N-(imidazo[1,2-a]pyrazin-2-yl)-1,2,3,4-tetrahydroisoquinoline-8-carboxamide; | 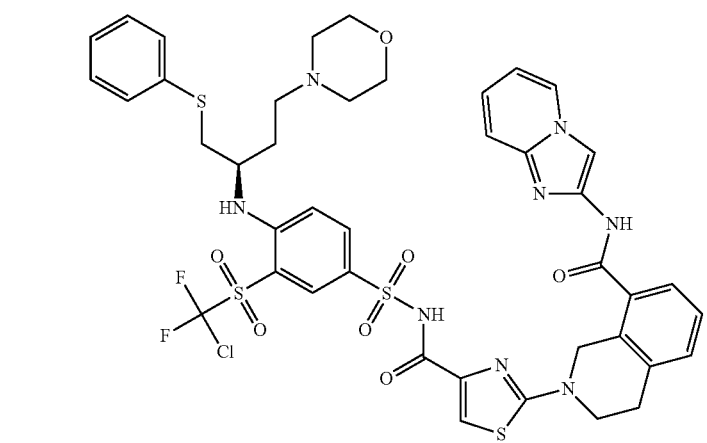 [SMILES: O=C(NS(=O)(=O)c1ccc(N[C@H](CCN2CCOCC2)CSc2ccccc2)c(S(=O)(=O)C(F)(F)Cl)c1)c1csc(N2CCc3cccc(C(=O)Nc4cn5ccccc5n4)c3C2)n1] |
| 2-(6-{[(3-{[chloro(difluoro)methyl]sulfonyl}-4-{[(2R)-4-(morpholin-4-yl)-1-(phenysulfanyl)butan-2-yl]amino}phenyl)sulfonyl]carbamoyl}pyridin-2-yl)-N-(imidazo[1,2-b]pyridazin-2-yl)-1,2,3,4-tetrahydroisoquinoline-8-carboxamide; | 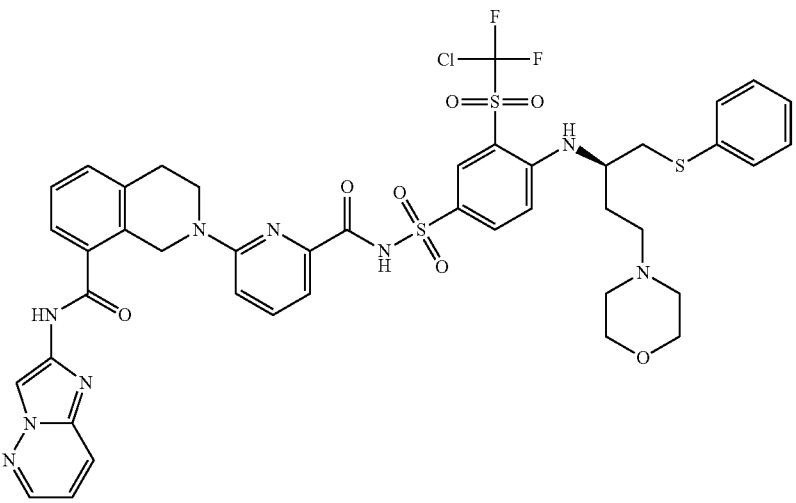 [SMILES: O=C(NS(=O)(=O)c1ccc(N[C@H](CCN2CCOCC2)CSc2ccccc2)c(S(=O)(=O)C(F)(F)Cl)c1)c1cccc(N2CCc3cccc(C(=O)Nc4cn5ncccc5n4)c3C2)n1] |

| Name | Structure |
|---|---|
| 2-(4-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}-1,3-thiazol-2-yl)-N-(imidazo[1,2-b]pyridazin-2-yl)-1,2,3,4-tetrahydroisoquinoline-8-carboxamide; | 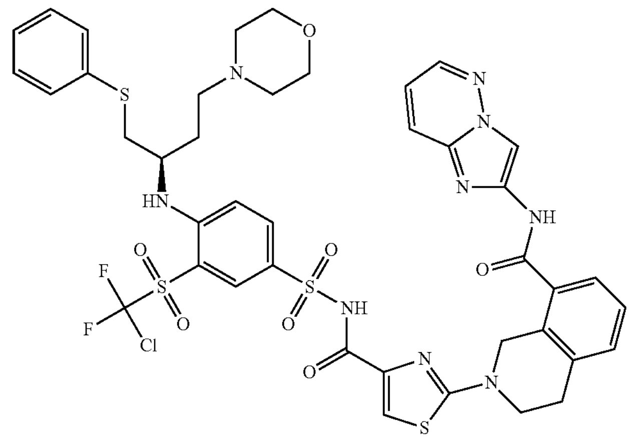 [SMILES: O=C(NS(=O)(=O)c1ccc(N[C@H](CCN2CCOCC2)CSc2ccccc2)c(S(=O)(=O)C(F)(F)Cl)c1)c1csc(N2CCc3cccc(C(=O)Nc4cn5ncccc5n4)c3C2)n1] |
| 2-(6-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}pyridin-2-yl)-N-(6-fluoro-1,3-benzothiazol-2-yl)-1,2,3,4-tetrahydroisoquinoline-8-carboxamide; | 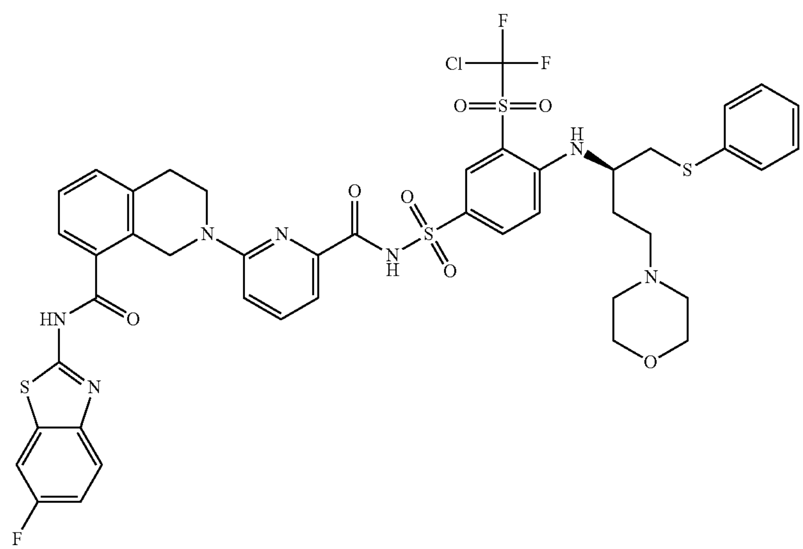 [SMILES: O=C(NS(=O)(=O)c1ccc(N[C@H](CCN2CCOCC2)CSc2ccccc2)c(S(=O)(=O)C(F)(F)Cl)c1)c1cccc(N2CCc3cccc(C(=O)Nc4nc5ccc(F)cc5s4)c3C2)n1] |
| 2-(4-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}-1,3-thiazol-2-yl)-N-(6-fluoro-1,3-benzothiazol-2-yl)-1,2,3,4-tetrahydroisoquinoline-8-carboxamide; | 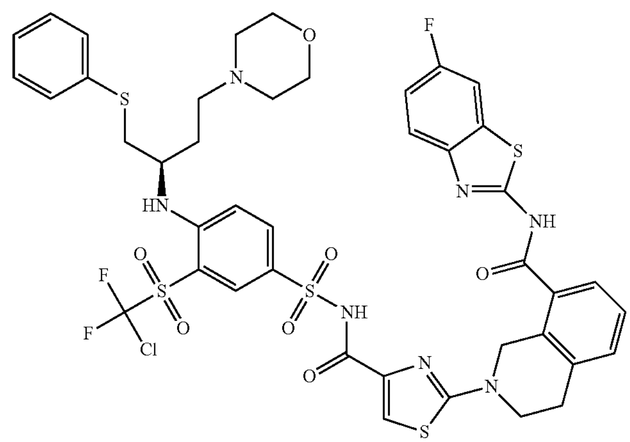 [SMILES: O=C(NS(=O)(=O)c1ccc(N[C@H](CCN2CCOCC2)CSc2ccccc2)c(S(=O)(=O)C(F)(F)Cl)c1)c1csc(N2CCc3cccc(C(=O)Nc4nc5ccc(F)cc5s4)c3C2)n1] |

| Name | Structure |
|---|---|
| N-(1,3-benzothiazol-2-yl)-2-[6-({[3-(methylsulfonyl)-4-{[(2R)-4-(morpholin-4-yl)-1-(phenylsulfanyl)butan-2-yl]amino}phenyl]sulfonyl}carbamoyl)pyridin-2-yl]-1,2,3,4-tetrahydroisoquinoline-8-carboxamide; | 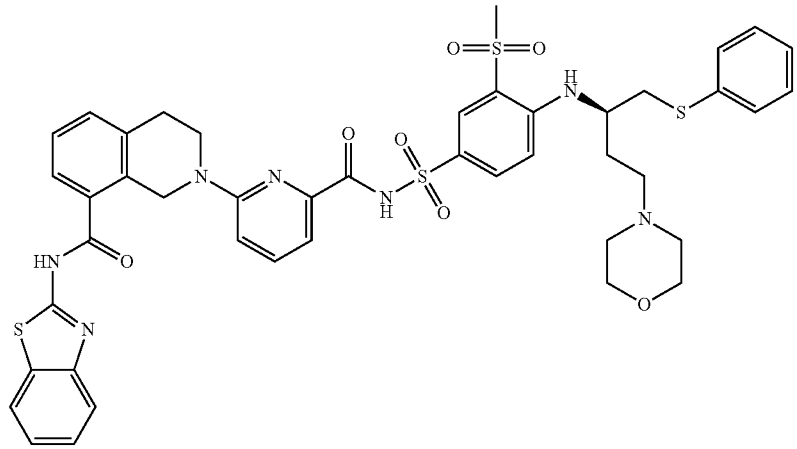 [SMILES: CS(=O)(=O)c1cc(S(=O)(=O)NC(=O)c2cccc(N3CCc4cccc(C(=O)Nc5nc6ccccc6s5)c4C3)n2)ccc1N[C@H](CCN1CCOCC1)CSc1ccccc1] |
| N-(1,3-benzothiazol-2-yl)-2-[4-({[3-(methylsulfonyl)-4-{[(2R)-4-(morpholin-4-yl)-1-(phenylsulfanyl)butan-2-yl]amino}phenyl]sulfonyl}carbamoyl)-1,3-thiazol-2-yl]-1,2,3,4-tetrahydroisoquinoline-8-carboxamide; | 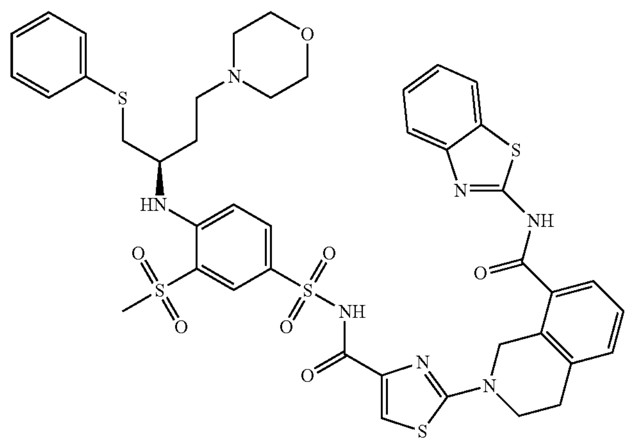 [SMILES: CS(=O)(=O)c1cc(S(=O)(=O)NC(=O)c2csc(N3CCc4cccc(C(=O)Nc5nc6ccccc6s5)c4C3)n2)ccc1N[C@H](CCN1CCOCC1)CSc1ccccc1] |
| 2-[6-({[3-(methylsulfonyl)-4-{[(2R)-4-(morpholin-4-yl)-1-(phenylsulfanyl)butan-2-yl]amino}phenyl]sulfonyl}carbamoyl)pyridin-2-yl]-N-([1,3]thiazolo[5,4-b]pyridin-2-yl)-1,2,3,4-tetrahydroisoquinoline-8-carboxamide; | 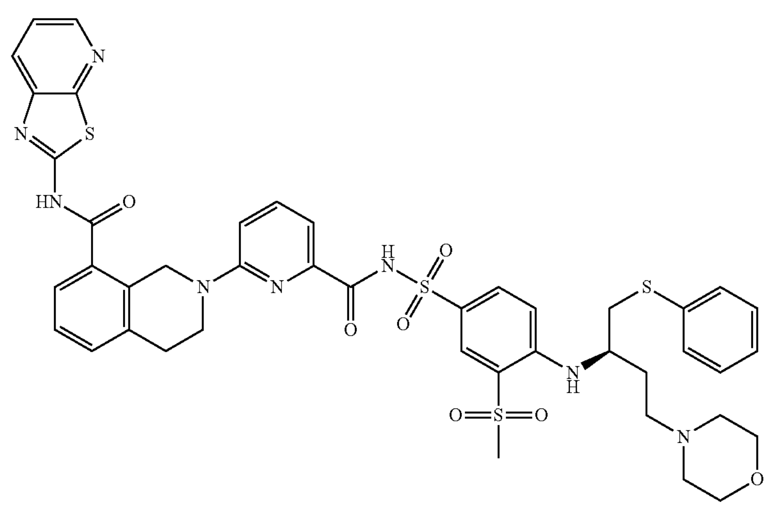 [SMILES: CS(=O)(=O)c1cc(S(=O)(=O)NC(=O)c2cccc(N3CCc4cccc(C(=O)Nc5nc6cccnc6s5)c4C3)n2)ccc1N[C@H](CCN1CCOCC1)CSc1ccccc1] |

-continued

| Name | Structure |
|---|---|
| 2-[4-({[3-(methylsulfonyl)-4-{[(2R)-4-(morpholin-4-yl)-1-(phenylsulfanyl)butan-2-yl]amino}phenyl]sulfonyl}carbamoyl)-1,3-thiazol-2-yl]-N-([1,3]thiazolo[5,4-b]pyridin-2-yl)-1,2,3,4-tetrahydroisoquinoline-8-carboxamide; | 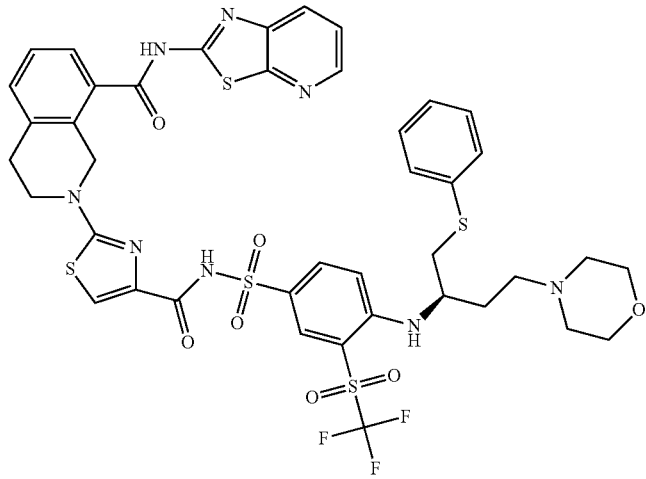 [SMILES: O=C(NS(=O)(=O)c1ccc(N[C@H](CCN2CCOCC2)CSc2ccccc2)c(S(=O)(=O)C(F)(F)F)c1)c1csc(N2CCc3cccc(C(=O)Nc4nc5cccnc5s4)c3C2)n1] |
| 2-[6-({[3-(methylsulfonyl)-4-{[(2R)-4-(morpholin-4-yl)-1-(phenylsulfanyl)butan-2-yl]amino}phenyl]sulfonyl}carbamoyl)pyridin-2-yl]-N-([1,3]thiazolo[5,4-c]pyridin-2-yl)-1,2,3,4-tetrahydroisoquinoline-8-carboxamide; | 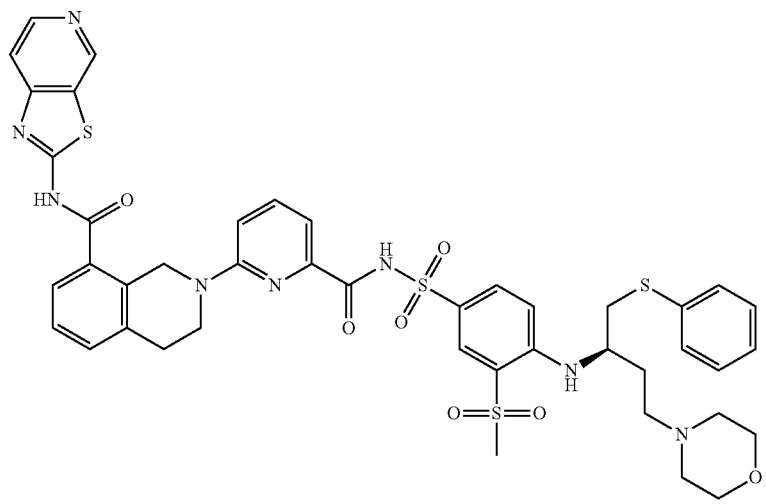 [SMILES: CS(=O)(=O)c1cc(S(=O)(=O)NC(=O)c2cccc(N3CCc4cccc(C(=O)Nc5nc6ccncc6s5)c4C3)n2)ccc1N[C@H](CCN1CCOCC1)CSc1ccccc1] |
| 2-[4-({[3-(methylsulfonyl)-4-{[(2R)-4-(morpholin-4-yl)-1-(phenylsulfanyl)butan-2-yl]amino}phenyl]sulfonyl}carbamoyl)-1,3-thiazol-2-yl]-N-([1,3]thiazolo[5,4-c]pyridin-2-yl)-1,2,3,4-tetrahydroisoquinoline-8-carboxamide; | 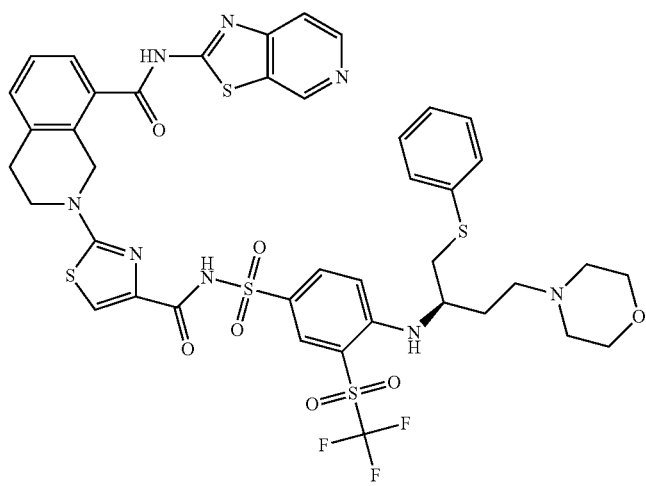 [SMILES: O=C(NS(=O)(=O)c1ccc(N[C@H](CCN2CCOCC2)CSc2ccccc2)c(S(=O)(=O)C(F)(F)F)c1)c1csc(N2CCc3cccc(C(=O)Nc4nc5ccncc5s4)c3C2)n1] |

-continued

| Name | Structure |
|---|---|
| 2-[6-({[3-(methylsulfonyl)-4-{[(2R)-4-(morpholin-4-yl)-1-(phenylsulfanyl)butan-2-yl]amino}phenyl]sulfonyl}carbamoyl)pyridin-2-yl]-N-([1,3]thiazolo[4,5-c]pyridin-2-yl)-1,2,3,4-tetrahydroisoquinoline-8-carboxamide; | 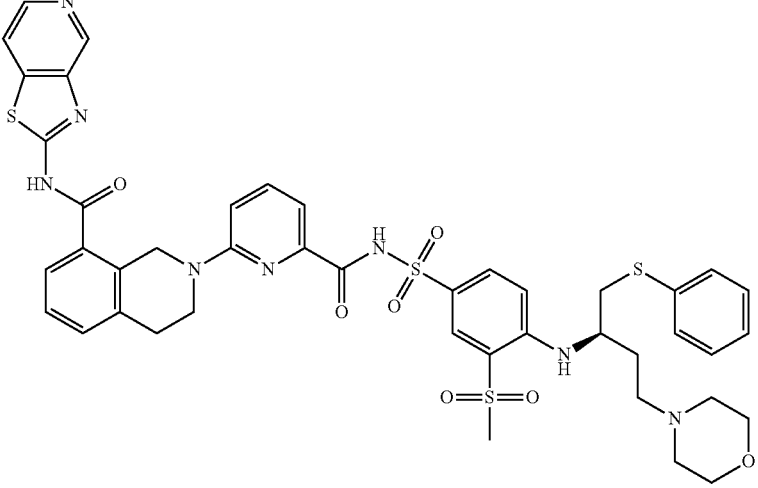 |
| 2-[4-({[3-(methylsulfonyl)-4-{[(2R)-4-(morpholin-4-yl)-1-(phenylsulfanyl)butan-2-yl]amino}phenyl]sulfonyl}carbamoyl)-1,3-thiazol-2-yl]-N-([1,3]thiazolo[4,5-c]pyridin-2-yl)-1,2,3,4-tetrahydroisoquinoline-8-carboxamide; | 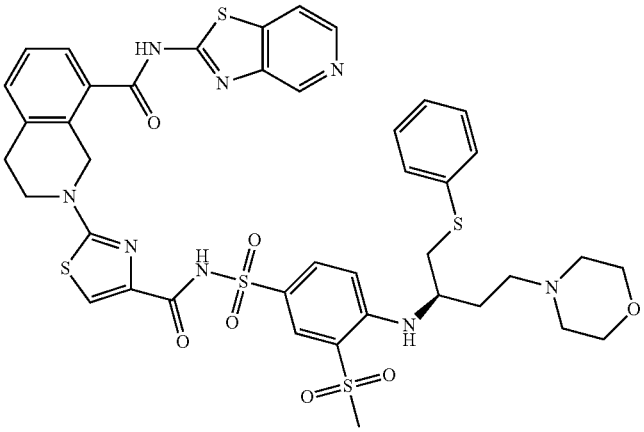 [SMILES: CS(=O)(=O)c1cc(S(=O)(=O)NC(=O)c2csc(N3CCc4cccc(C(=O)Nc5nc6cnccc6s5)c4C3)n2)ccc1N[C@H](CCN1CCOCC1)CSc1ccccc1] |
| N-(imidazo[1,2-a]pyridin-2-yl)-2-[6-({[3-(methylsulfonyl)-4-{[(2R)-4-(morpholin-4-yl)-1-(phenylsulfanyl)butan-2-yl]amino}phenyl]sulfonyl}carbamoyl)pyridin-2-yl]-1,2,3,4-tetrahydroisoquinoline-8-carboxamide; | 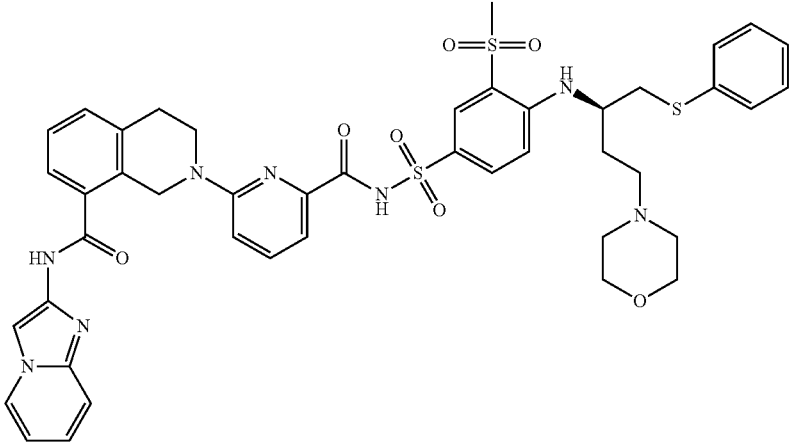 [SMILES: CS(=O)(=O)c1cc(S(=O)(=O)NC(=O)c2cccc(N3CCc4cccc(C(=O)Nc5cn6ccccc6n5)c4C3)n2)ccc1N[C@H](CCN1CCOCC1)CSc1ccccc1] |

| Name | Structure |
|---|---|
| N-(imidazo[1,2-a]pyridin-2-yl)-2-[4-({[3-(methylsulfonyl)-4-{[(2R)-4-(morpholin-4-yl)-1-(phenylsulfanyl)butan-2-yl]amino}phenyl]sulfonyl}carbamoyl)-1,3-thiazol-2-yl]-1,2,3,4-tetrahydroisoquinoline-8-carboxamide; | 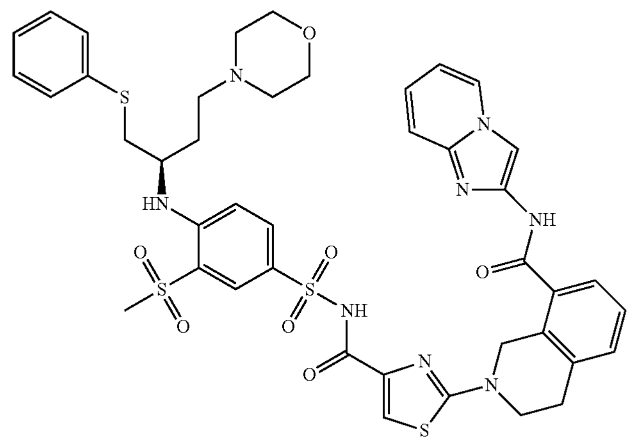 [SMILES: CS(=O)(=O)c1cc(S(=O)(=O)NC(=O)c2csc(N3CCc4cccc(C(=O)Nc5cn6ccccc6n5)c4C3)n2)ccc1N[C@H](CCN1CCOCC1)CSc1ccccc1] |
| N-(imidazo[1,2-a]pyrazin-2-yl)-2-[6-({[3-(methylsulfonyl)-4-{[(2R)-4-(morpholin-4-yl)-1-(phenylsulfanyl)butan-2-yl]amino}phenyl]sulfonyl}carbamoyl)pyridin-2-yl]-1,2,3,4-tetrahydroisoquinoline-8-carboxamide; | 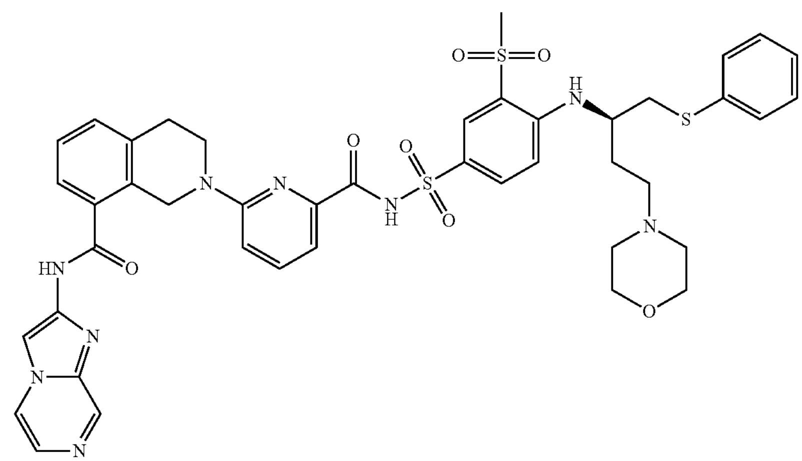 [SMILES: CS(=O)(=O)c1cc(S(=O)(=O)NC(=O)c2cccc(N3CCc4cccc(C(=O)Nc5cn6ccncc6n5)c4C3)n2)ccc1N[C@H](CCN1CCOCC1)CSc1ccccc1] |
| N-(imidazo[1,2-a]pyrazin-2-yl)-2-[4-({[3-(methylsulfonyl)-4-{[(2R)-4-(morpholin-4-yl)-1-(phenylsulfanyl)butan-2-yl]amino}phenyl]sulfonyl}carbamoyl)-1,3-thiazol-2-yl]-1,2,3,4-tetrahydroisoquinoline-8-carboxamide; | 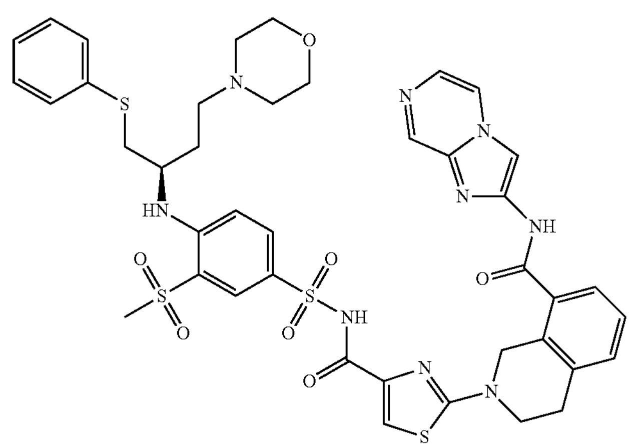 [SMILES: CS(=O)(=O)c1cc(S(=O)(=O)NC(=O)c2csc(N3CCc4cccc(C(=O)Nc5cn6ccncc6n5)c4C3)n2)ccc1N[C@H](CCN1CCOCC1)CSc1ccccc1] |

| Name | Structure |
|---|---|
| N-(imidazo[1,2-b]pyridazin-2-yl)-2-[6-({[3-(methylsulfonyl)-4-{[(2R)-4-(morpholin-4-yl)-1-(phenylsulfanyl)butan-2-yl]amino}phenyl]sulfonyl}carbamoyl)pyridin-2-yl]-1,2,3,4-tetrahydroisoquinoline-8-carboxamide; | 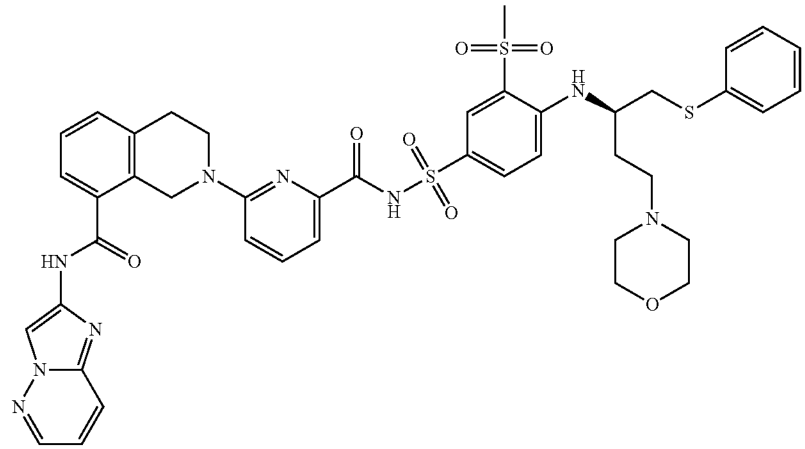 [SMILES: CS(=O)(=O)c1cc(S(=O)(=O)NC(=O)c2cccc(N3CCc4cccc(C(=O)Nc5cn6ncccc6n5)c4C3)n2)ccc1N[C@H](CCN1CCOCC1)CSc1ccccc1] |
| N-(imidazo[1,2-b]pyridazin-2-yl)-2-[4-({[3-(methylsulfonyl)-4-{[(2R)-4-(morpholin-4-yl)-1-(phenylsulfanyl)butan-2-yl]amino}phenyl]sulfonyl}carbamoyl)-1,3-thiazol-2-yl]-1,2,3,4-tetrahydroisoquinoline-8-carboxamide; | 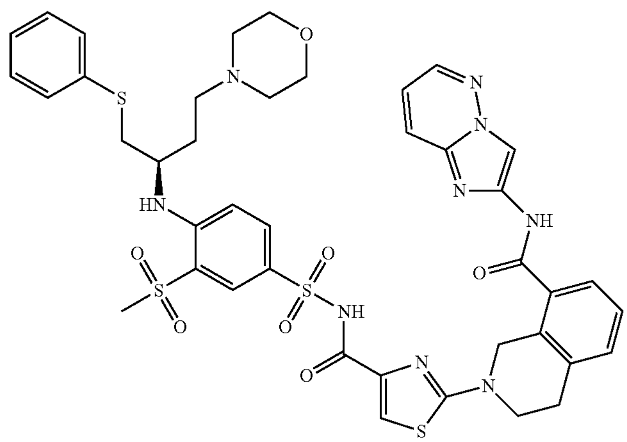 [SMILES: CS(=O)(=O)c1cc(S(=O)(=O)NC(=O)c2csc(N3CCc4cccc(C(=O)Nc5cn6ncccc6n5)c4C3)n2)ccc1N[C@H](CCN1CCOCC1)CSc1ccccc1] |
| N-(6-fluoro-1,3-benzothiazol-2-yl)-2-[6-({[3-(methylsulfonyl)-4-{[(2R)-4-(morpholin-4-yl)-1-(phenylsulfanyl)butan-2-yl]amino}phenyl]sulfonyl}carbamoyl)pyridin-2-yl]-1,2,3,4-tetrahydroisoquinoline-8-carboxamide; | 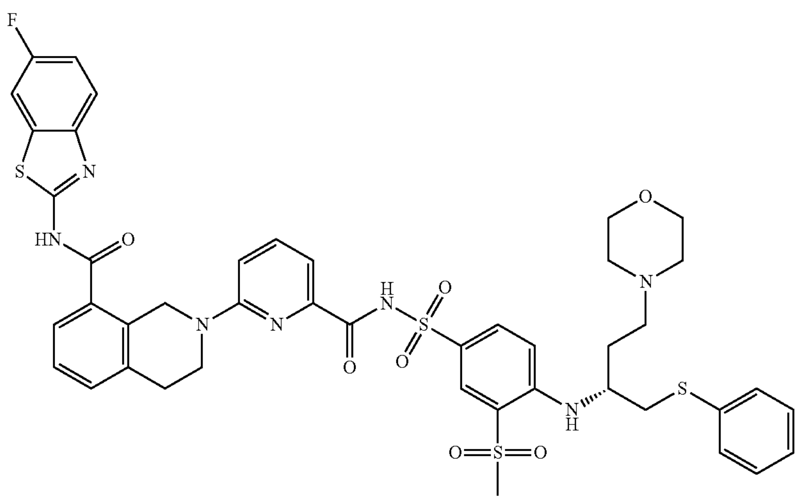 [SMILES: CS(=O)(=O)c1cc(S(=O)(=O)NC(=O)c2cccc(N3CCc4cccc(C(=O)Nc5nc6ccc(F)cc6s5)c4C3)n2)ccc1N[C@H](CCN1CCOCC1)CSc1ccccc1] |

| Name | Structure |
|---|---|
| N-(6-fluoro-1,3-benzothiazol-2-yl)-2-[4-({[3-(methylsulfonyl)-4-{[(2R)-4-(morpholin-4-yl)-1-(phenylsulfanyl)butan-2-yl]amino}phenyl]sulfonyl}carbamoyl)-1,3-thiazol-2-yl]-1,2,3,4-tetrahydroisoquinoline-8-carboxamide; | 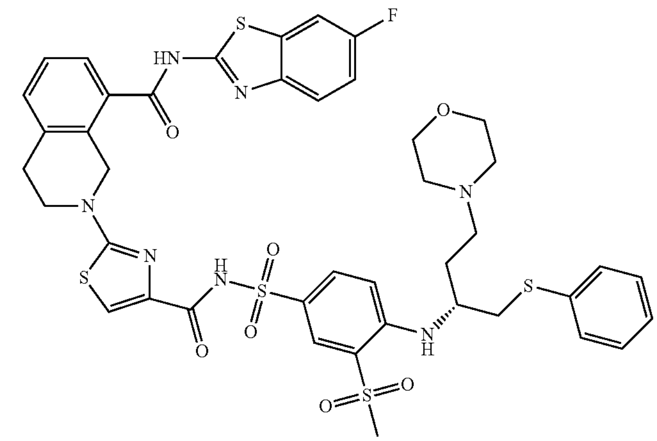 [SMILES: CS(=O)(=O)c1cc(S(=O)(=O)NC(=O)c2csc(N3CCc4cccc(C(=O)Nc5nc6ccc(F)cc6s5)c4C3)n2)ccc1N[C@H](CCN1CCOCC1)CSc1ccccc1] |
| N-(1,3-benzothiazol-2-yl)-2-(6-{[(3-fluoro-4-{[(2R)-4-(morpholin-4-yl)-1-(phenylsulfanyl)butan-2-yl]amino}phenyl)sulfonyl]carbamoyl}pyridin-2-yl)-1,2,3,4-tetrahydroisoquinoline-8-carboxamide; | 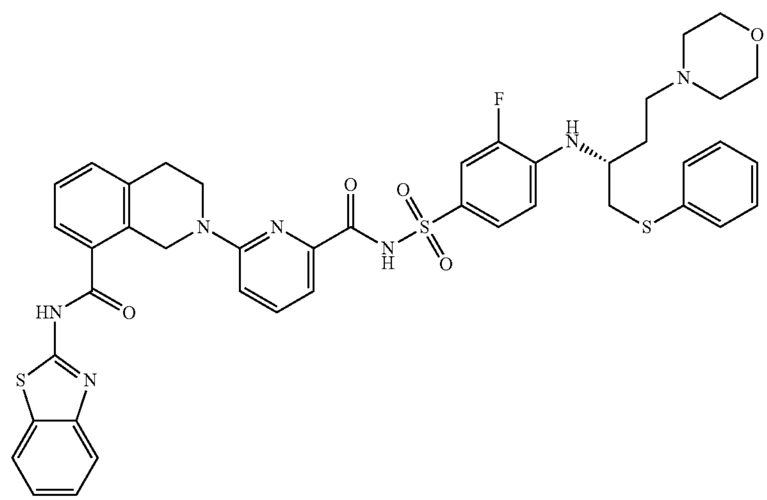 [SMILES: O=C(NS(=O)(=O)c1ccc(N[C@H](CCN2CCOCC2)CSc2ccccc2)c(F)c1)c1cccc(N2CCc3cccc(C(=O)Nc4nc5ccccc5s4)c3C2)n1] |
| N-(1,3-benzothiazol-2-yl)-2-(4-{[(3-fluoro-4-{[(2R)-4-(morpholin-4-yl)-1-(phenylsulfanyl)butan-2-yl]amino}phenyl)sulfonyl]carbamoyl}-1,3-thiazol-2-yl)-1,2,3,4-tetrahydroisoquinoline-8-carboxamide; | 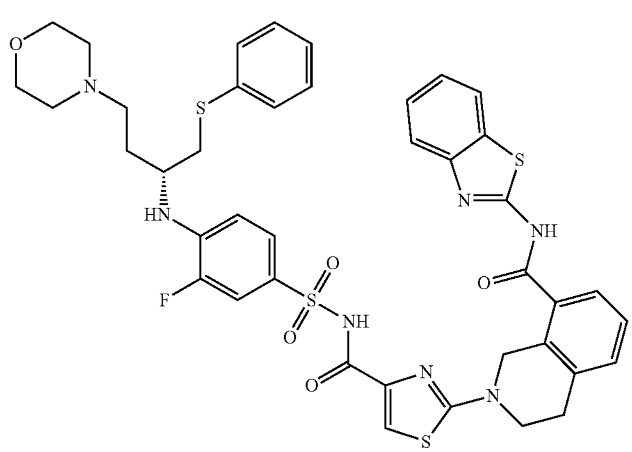 [SMILES: O=C(NS(=O)(=O)c1ccc(N[C@H](CCN2CCOCC2)CSc2ccccc2)c(F)c1)c1csc(N2CCc3cccc(C(=O)Nc4nc5ccccc5s4)c3C2)n1] |

| Name | Structure |
|---|---|
| 2-(6-{[(3-fluoro-4-{[(2R)-4-(morpholin-4-yl)-1-(phenylsulfanyl)butan-2-yl]amino}phenyl)sulfonyl]carbamoyl}pyridin-2-yl)-N-([1,3]thiazolo[5,4-b]pyridin-2-yl)-1,2,3,4-tetrahydroisoquinoline-8-carboxamide; | 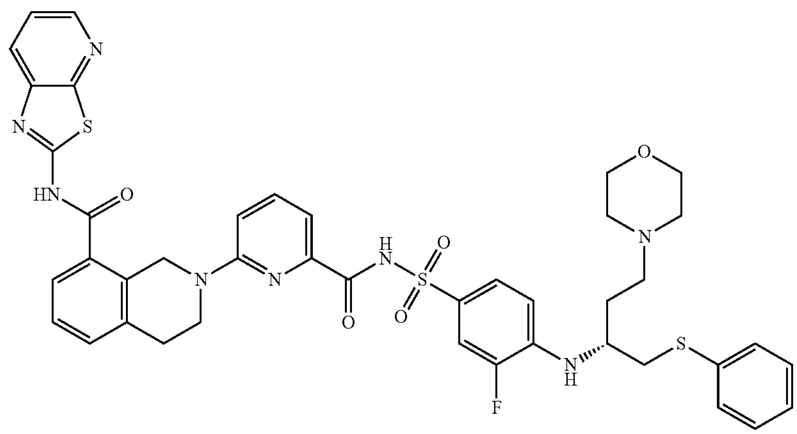 [SMILES: O=C(NS(=O)(=O)c1ccc(N[C@H](CCN2CCOCC2)CSc2ccccc2)c(F)c1)c1cccc(N2CCc3cccc(C(=O)Nc4nc5cccnc5s4)c3C2)n1] |
| 2-(4-{[(3-fluoro-4-{[(2R)-4-(morpholin-4-yl)-1-(phenylsulfanyl)butan-2-yl]amino}phenyl)sulfonyl]carbamoyl}-1,3-thiazol-2-yl)-N-([1,3]thiazolo[5,4-b]pyridin-2-yl)-1,2,3,4-tetrahydroisoquinoline-8-carboxamide; | 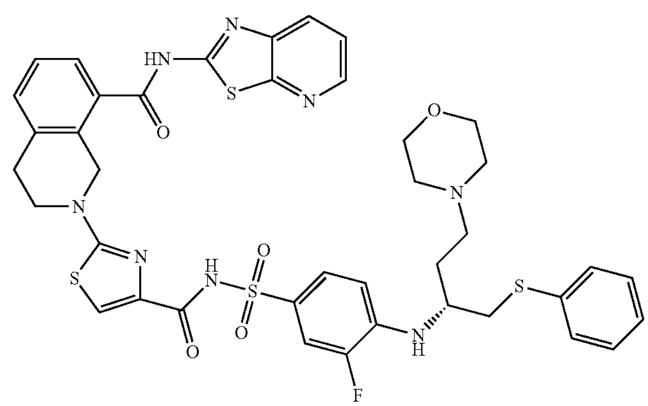 [SMILES: O=C(NS(=O)(=O)c1ccc(N[C@H](CCN2CCOCC2)CSc2ccccc2)c(F)c1)c1csc(N2CCc3cccc(C(=O)Nc4nc5cccnc5s4)c3C2)n1] |
| 2-(6-{[(3-fluoro-4-{[(2R)-4-(morpholin-4-yl)-1-(phenylsulfanyl)butan-2-yl]amino}phenyl)sulfonyl]carbamoyl}pyridin-2-yl)-N-([1,3]thiazolo[5,4-c]pyridin-2-yl)-1,2,3,4-tetrahydroisoquinoline-8-carboxamide; | 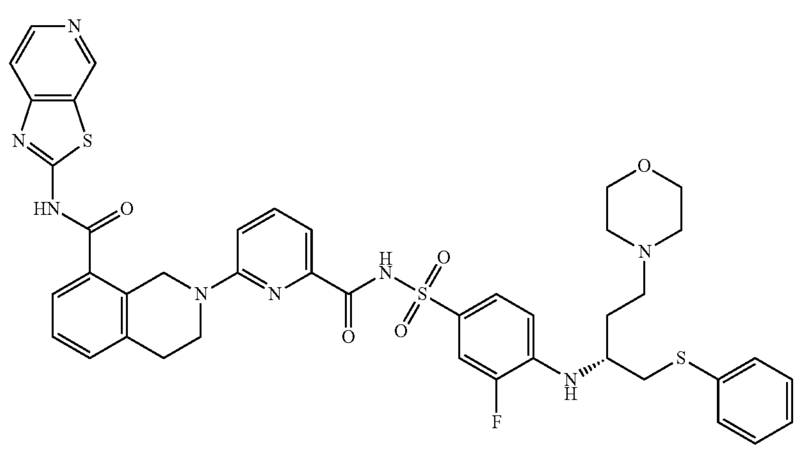 [SMILES: O=C(NS(=O)(=O)c1ccc(N[C@H](CCN2CCOCC2)CSc2ccccc2)c(F)c1)c1cccc(N2CCc3cccc(C(=O)Nc4nc5ccncc5s4)c3C2)n1] |

| Name | Structure |
|---|---|
| 2-(4-{[(3-fluoro-4-{[(2R)-4-(morpholin-4-yl)-1-(phenylsulfanyl)butan-2-yl]amino}phenyl)sulfonyl]carbamoyl}-1,3-thiazol-2-yl)-N-([1,3]thiazolo[5,4-c]pyridin-2-yl)-1,2,3,4-tetrahydroisoquinoline-8-carboxamide; | 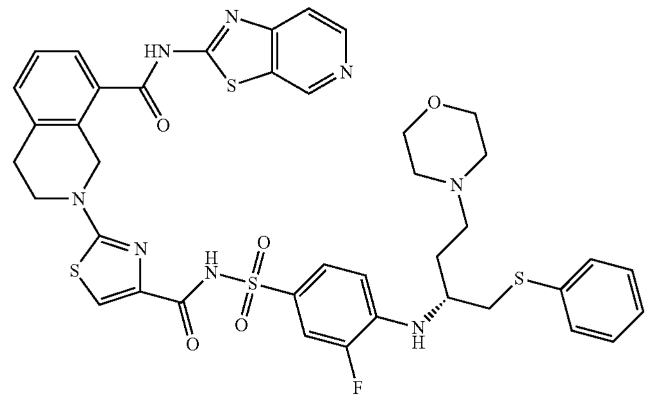 [SMILES: O=C(NS(=O)(=O)c1ccc(N[C@H](CCN2CCOCC2)CSc2ccccc2)c(F)c1)c1csc(N2CCc3cccc(C(=O)Nc4nc5ccncc5s4)c3C2)n1] |
| 2-(6-{[(3-fluoro-4-{[(2R)-4-(morpholin-4-yl)-1-(phenylsulfanyl)butan-2-yl]amino}phenyl)sulfonyl]carbamoyl}pyridin-2-yl)-N-([1,3]thiazolo[4,5-c]pyridin-2-yl)-1,2,3,4-tetrahydroisoquinoline-8-carboxamide; | 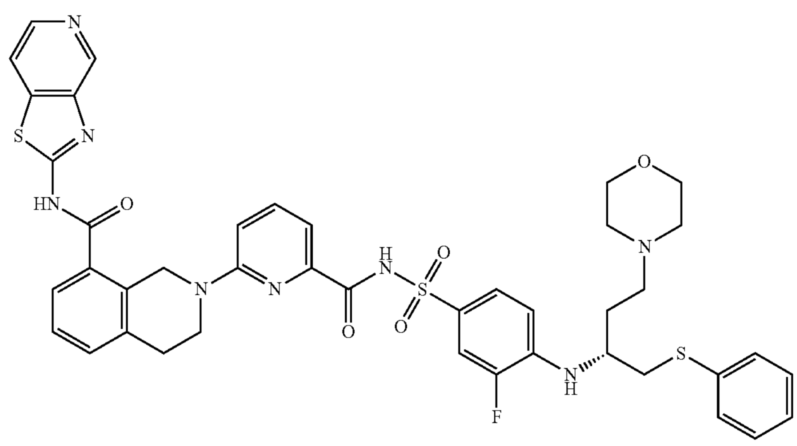 [SMILES: O=C(NS(=O)(=O)c1ccc(N[C@H](CCN2CCOCC2)CSc2ccccc2)c(F)c1)c1cccc(N2CCc3cccc(C(=O)Nc4nc5cnccc5s4)c3C2)n1] |
| 2-(4-{[(3-fluoro-4-{[(2R)-4-(morpholin-4-yl)-1-(phenylsulfanyl)butan-2-yl]amino}phenyl)sulfonyl]carbamoyl}-1,3-thiazol-2-yl)-N-([1,3]thiazolo[4,5-c]pyridin-2-yl)-1,2,3,4-tetrahydroisoquinoline-8-carboxamide; | 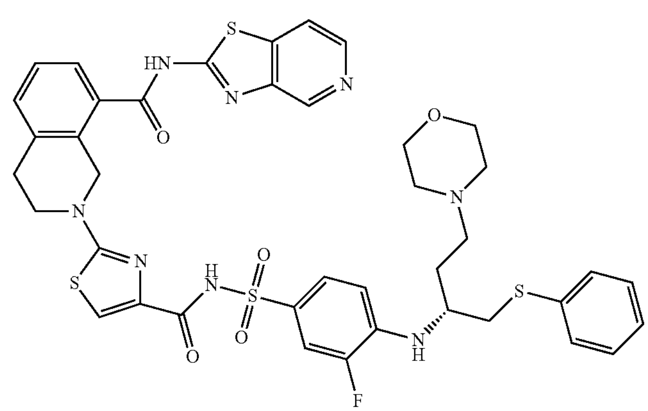 [SMILES: O=C(NS(=O)(=O)c1ccc(N[C@H](CCN2CCOCC2)CSc2ccccc2)c(F)c1)c1csc(N2CCc3cccc(C(=O)Nc4nc5cnccc5s4)c3C2)n1] |

| Name | Structure |
| --- | --- |
| 2-(6-{[(3-fluoro-4-{[(2R)-4-(morpholin-4-yl)-1-(phenylsulfanyl)butan-2-yl]amino}phenyl)sulfonyl]carbamoyl}pyridin-2-yl)-N-(imidazo[1,2-a]pyridin-2-yl)-1,2,3,4-tetrahydroisoquinoline-8-carboxamide; | 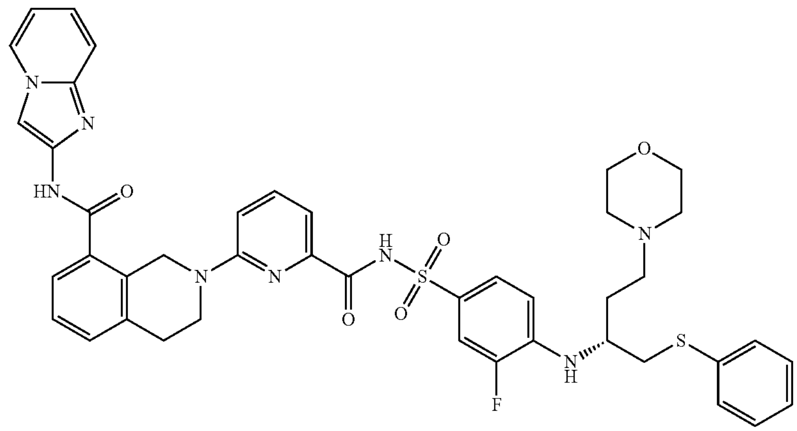 [SMILES: O=C(NS(=O)(=O)c1ccc(N[C@H](CCN2CCOCC2)CSc2ccccc2)c(F)c1)c1cccc(N2CCc3cccc(C(=O)Nc4cn5ccccc5n4)c3C2)n1] |
| 2-(4-{[(3-fluoro-4-{[(2R)-4-(morpholin-4-yl)-1-(phenylsulfanyl)butan-2-yl]amino}phenyl)sulfonyl]carbamoyl}-1,3-thiazol-2-yl)-N-(imidazo[1,2-a]pyridin-2-yl)-1,2,3,4-tetrahydroisoquinoline-8-carboxamide; | 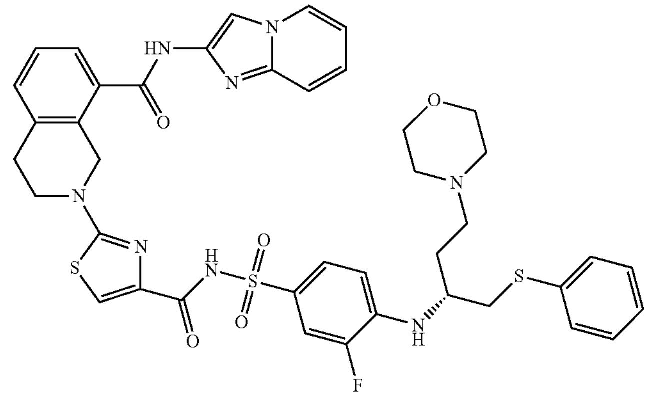 [SMILES: O=C(NS(=O)(=O)c1ccc(N[C@H](CCN2CCOCC2)CSc2ccccc2)c(F)c1)c1csc(N2CCc3cccc(C(=O)Nc4cn5ccccc5n4)c3C2)n1] |
| 2-(6-{[(3-fluoro-4-{[(2R)-4-(morpholin-4-yl)-1-(phenylsulfanyl)butan-2-yl]amino}phenyl)sulfonyl]carbamoyl}pyridin-2-yl)-N-(imidazo[1,2-a]pyrazin-2-yl)-1,2,3,4-tetrahydroisoquinoline-8-carboxamide; | 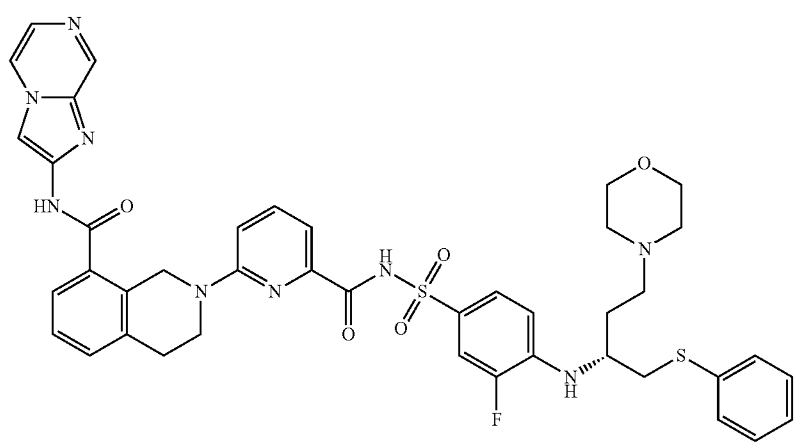 [SMILES: O=C(NS(=O)(=O)c1ccc(N[C@H](CCN2CCOCC2)CSc2ccccc2)c(F)c1)c1cccc(N2CCc3cccc(C(=O)Nc4cn5ccncc5n4)c3C2)n1] |

-continued

| Name | Structure |
|---|---|
| 2-(4-{[(3-fluoro-4-{[(2R)-4-(morpholin-4-yl)-1-(phenylsulfanyl)butan-2-yl]amino}phenyl)sulfonyl]carbamoyl}-1,3-thiazol-2-yl)-N-(imidazo[1,2-a]pyrazin-2-yl)-1,2,3,4-tetrahydroisoquinoline-8-carboxamide; | 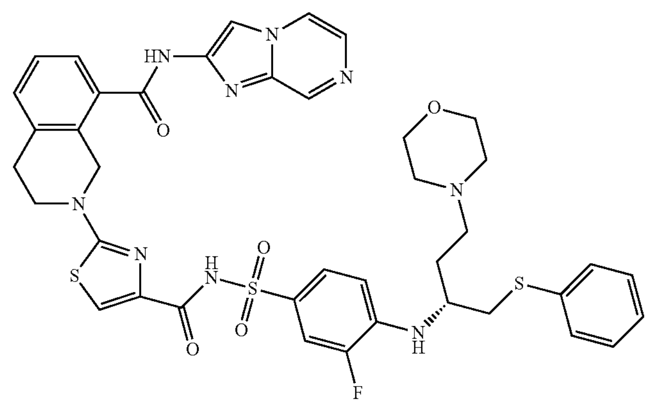 [SMILES: O=C(NS(=O)(=O)c1ccc(N[C@H](CCN2CCOCC2)CSc2ccccc2)c(F)c1)c1csc(N2CCc3cccc(C(=O)Nc4cn5ccncc5n4)c3C2)n1] |
| 2-(6-{[(3-fluoro-4-{[(2R)-4-(morpholin-4-yl)-1-(phenylsulfanyl)butan-2-yl]amino}phenyl)sulfonyl]carbamoyl}pyridin-2-yl)-N-(imidazo[1,2-b]pyridazin-2-yl)-1,2,3,4-tetrahydroisoquinoline-8-carboxamide; | 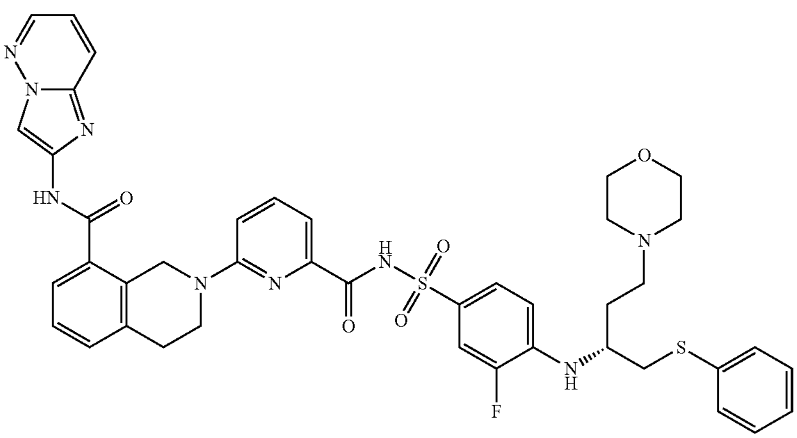 [SMILES: O=C(NS(=O)(=O)c1ccc(N[C@H](CCN2CCOCC2)CSc2ccccc2)c(F)c1)c1cccc(N2CCc3cccc(C(=O)Nc4cn5ncccc5n4)c3C2)n1] |
| 2-(4-{[(3-fluoro-4-{[(2R)-4-(morpholin-4-yl)-1-(phenylsulfanyl)butan-2-yl]amino}phenyl)sulfonyl]carbamoyl}-1,3-thiazol-2-yl)-N-(imidazo[1,2-b]pyridazin-2-yl)-1,2,3,4-tetrahydroisoquinoline-8-carboxamide; | 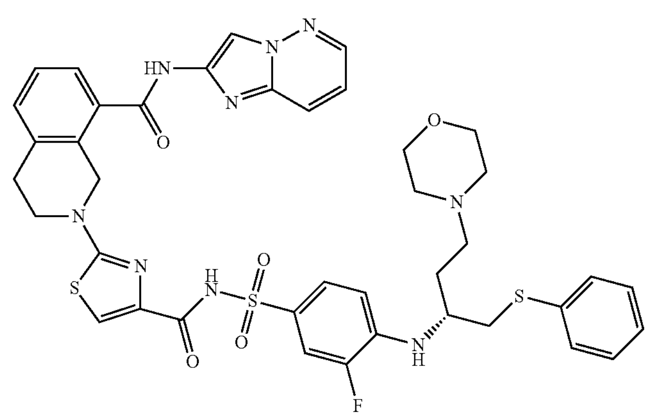 [SMILES: O=C(NS(=O)(=O)c1ccc(N[C@H](CCN2CCOCC2)CSc2ccccc2)c(F)c1)c1csc(N2CCc3cccc(C(=O)Nc4cn5ncccc5n4)c3C2)n1] |

| Name | Structure |
|---|---|
| N-(6-fluoro-1,3-benzothiazol-2-yl)-2-(6-{[(3-fluoro-4-{[(2R)-4-(morpholin-4-yl)-1-(phenylsulfanyl)butan-2-yl]amino}phenyl)sulfonyl]carbamoyl}pyridin-2-yl)-1,2,3,4-tetrahydroisoquinoline-8-carboxamide; | 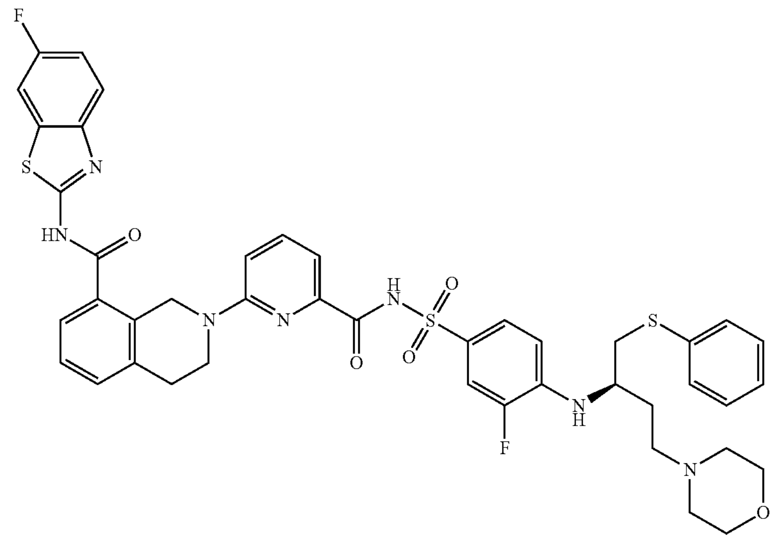 [SMILES: O=C(NS(=O)(=O)c1ccc(N[C@H](CCN2CCOCC2)CSc2ccccc2)c(F)c1)c1cccc(N2CCc3cccc(C(=O)Nc4nc5ccc(F)cc5s4)c3C2)n1] |
| N-(6-fluoro-1,3-benzothiazol-2-yl)-2-(4-{[(3-fluoro-4-{[(2R)-4-(morpholin-4-yl)-1-(phenylsulfanyl)butan-2-yl]amino}phenyl)sulfonyl]carbamoyl}-1,3-thiazol-2-yl)-1,2,3,4-tetrahydroisoquinoline-8-carboxamide; | 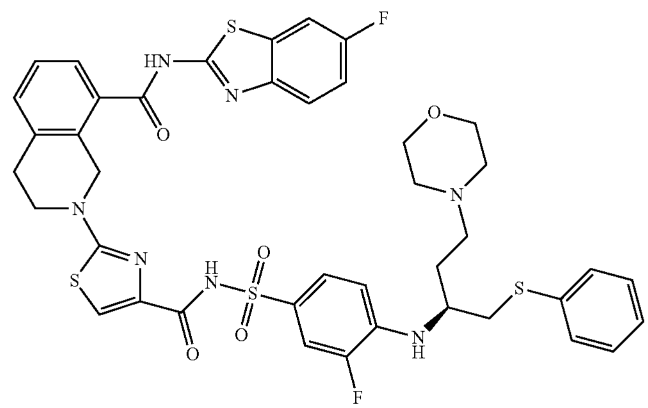 [SMILES: O=C(NS(=O)(=O)c1ccc(N[C@@H](CCN2CCOCC2)CSc2ccccc2)c(F)c1)c1csc(N2CCc3cccc(C(=O)Nc4nc5ccc(F)cc5s4)c3C2)n1] |
| N-(1,3-benzothiazol-2-yl)-2-[6-({[4-{[(2R)-4-(morpholin-4-yl)-1-(phenylsulfanyl)butan-2-yl]amino}-3-(trifluoromethyl)phenyl]sulfonyl}carbamoyl)pyridin-2-yl]-1,2,3,4-tetrahydroisoquinoline-8-carboxamide; | 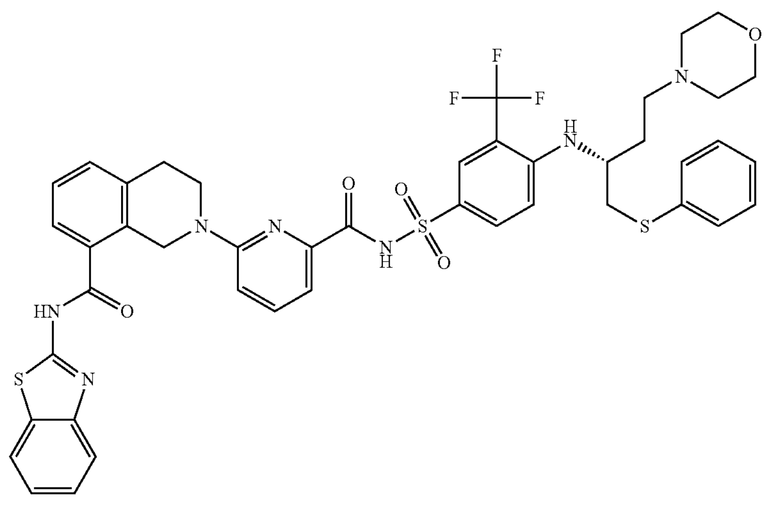 [SMILES: O=C(NS(=O)(=O)c1ccc(N[C@H](CCN2CCOCC2)CSc2ccccc2)c(C(F)(F)F)c1)c1cccc(N2CCc3cccc(C(=O)Nc4nc5ccccc5s4)c3C2)n1] |

-continued

| Name | Structure |
|---|---|
| N-(1,3-benzothiazol-2-yl)-2-[4-({[4-{[(2R)-4-(morpholin-4-yl)-1-(phenylsulfanyl)butan-2-yl]amino}-3-(trifluoromethyl)phenyl]sulfonyl}carbamoyl)-1,3-thiazol-2-yl]-1,2,3,4-tetrahydroisoquinoline-8-carboxamide | 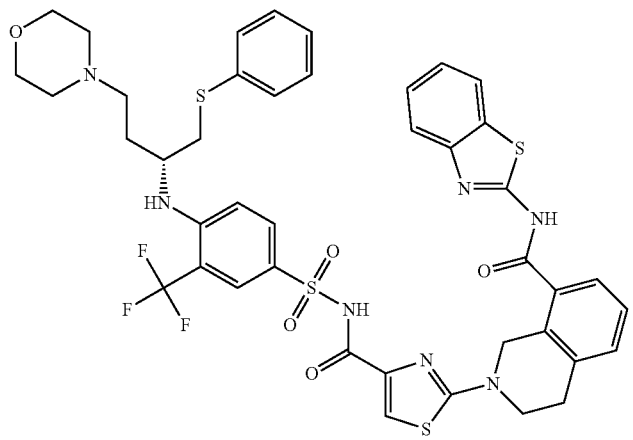 [SMILES: O=C(NS(=O)(=O)c1ccc(N[C@H](CCN2CCOCC2)CSc2ccccc2)c(C(F)(F)F)c1)c1csc(N2CCc3cccc(C(=O)Nc4nc5ccccc5s4)c3C2)n1] |
| 2-[6-({[4-{[(2R)-4-(morpholin-4-yl)-1-(phenylsulfanyl)butan-2-yl]amino}-3-(trifluoromethyl)phenyl]sulfonyl}carbamoyl)pyridin-2-yl]-N-([1,3]thiazolo[5,4-b]pyridin-2-yl)-1,2,3,4-tetrahydroisoquinoline-8-carboxamide; | 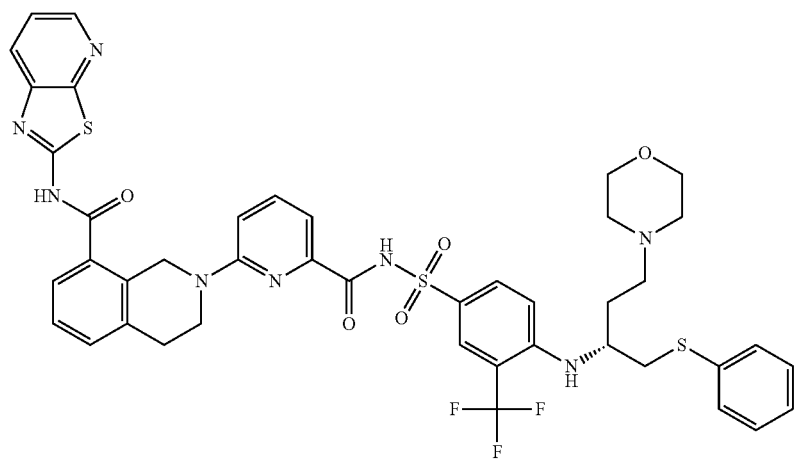 [SMILES: O=C(NS(=O)(=O)c1ccc(N[C@H](CCN2CCOCC2)CSc2ccccc2)c(C(F)(F)F)c1)c1cccc(N2CCc3cccc(C(=O)Nc4nc5cccnc5s4)c3C2)n1] |
| 2-[4-({[4-{[(2R)-4-(morpholin-4-yl)-1-(phenylsulfanyl)butan-2-yl]amino}-3-(trifluoromethyl)phenyl]sulfonyl}carbamoyl)-1,3-thiazol-2-yl]-N-([1,3]thiazolo[5,4-b]pyridin-2-yl)-1,2,3,4-tetrahydroisoquinoline-8-carboxamide; | 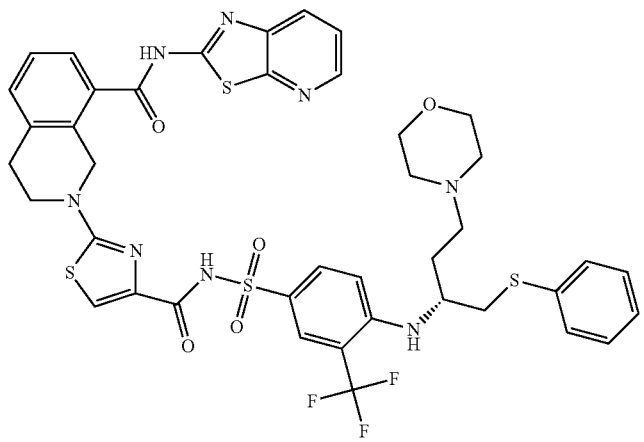 [SMILES: O=C(NS(=O)(=O)c1ccc(N[C@H](CCN2CCOCC2)CSc2ccccc2)c(C(F)(F)F)c1)c1csc(N2CCc3cccc(C(=O)Nc4nc5cccnc5s4)c3C2)n1] |

| Name | Structure |
|---|---|
| 2-[6-({[4-{[(2R)-4-(morpholin-4-yl)-1-(phenylsulfanyl)butan-2-yl]amino}-3-(trifluoromethyl)phenyl]sulfonyl}carbamoyl)pyridin-2-yl]-N-([1,3]thiazolo[5,4-c]pyridin-2-yl)-1,2,3,4-tetrahydroisoquinoline-8-carboxamide; | |
| 2-[4-({[4-{[(2R)-4-(morpholin-4-yl)-1-(phenylsulfanyl)butan-2-yl]amino}-3-(trifluoromethyl)phenyl]sulfonyl}carbamoyl)-1,3-thiazol-2-yl]-N-([1,3]thiazolo[5,4-c]pyridin-2-yl)-1,2,3,4-tetrahydroisoquinoline-8-carboxamide; | 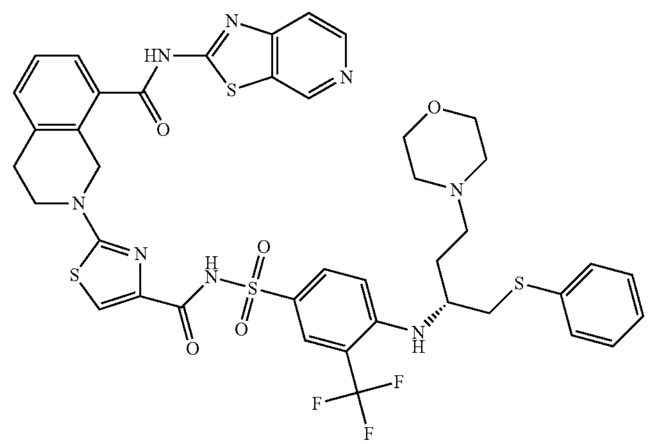 [SMILES: O=C(NS(=O)(=O)c1ccc(N[C@H](CCN2CCOCC2)CSc2ccccc2)c(C(F)(F)F)c1)c1csc(N2CCc3cccc(C(=O)Nc4nc5ccncc5s4)c3C2)n1] |
| 2-[6-({[4-{[(2R)-4-(morpholin-4-yl)-1-(phenylsulfanyl)butan-2-yl]amino}-3-(trifluoromethyl)phenyl]sulfonyl}carbamoyl)pyridin-2-yl]-N-([1,3]thiazolo[4,5-c]pyridin-2-yl)-1,2,3,4-tetrahydroisoquinoline-8-carboxamide; | 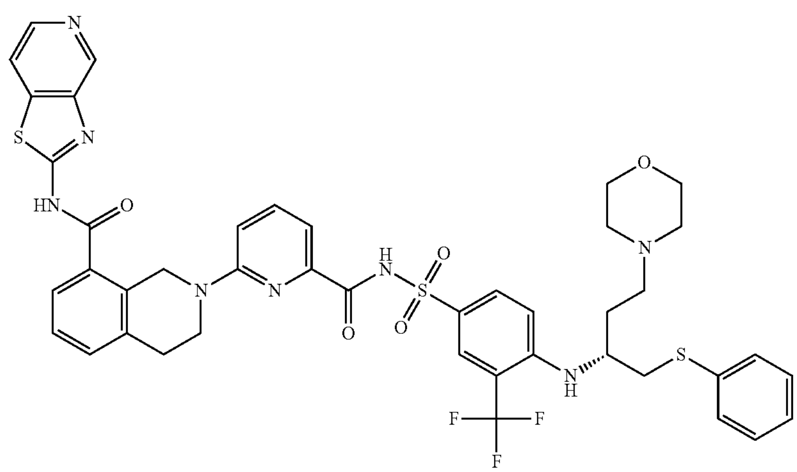 [SMILES: O=C(NS(=O)(=O)c1ccc(N[C@H](CCN2CCOCC2)CSc2ccccc2)c(C(F)(F)F)c1)c1cccc(N2CCc3cccc(C(=O)Nc4nc5cnccc5s4)c3C2)n1] |

| Name | Structure |
|---|---|
| 2-[4-({[4-{[(2R)-4-(morpholin-4-yl)-1-(phenylsulfanyl)butan-2-yl]amino}-3-(trifluoromethyl)phenyl]sulfonyl}carbamoyl)-1,3-thiazol-2-yl]-N-([1,3]thiazolo[4,5-c]pyridin-2-yl)-1,2,3,4-tetrahydroisoquinoline-8-carboxamide; | 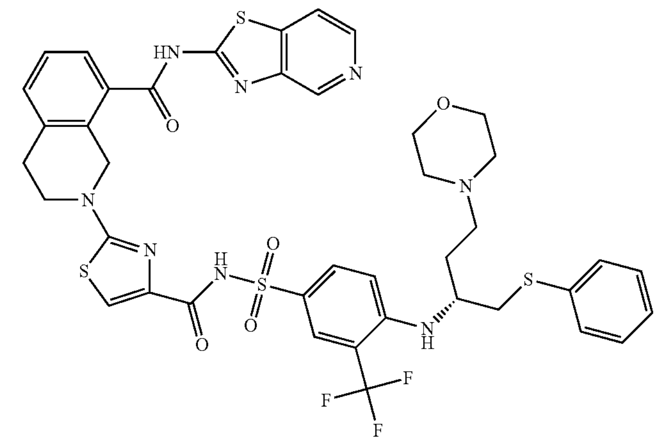 [SMILES: O=C(NS(=O)(=O)c1ccc(N[C@H](CCN2CCOCC2)CSc2ccccc2)c(C(F)(F)F)c1)c1csc(N2CCc3cccc(C(=O)Nc4nc5cnccc5s4)c3C2)n1] |
| N-(imidazo[1,2-a]pyridin-2-yl)-2-[6-({[4-{[(2R)-4-(morpholin-4-yl)-1-(phenylsulfanyl)butan-2-yl]amino}-3-(trifluoromethyl)phenyl]sulfonyl}carbamoyl)pyridin-2-yl]-1,2,3,4-tetrahydroisoquinoline-8-carboxamide; | 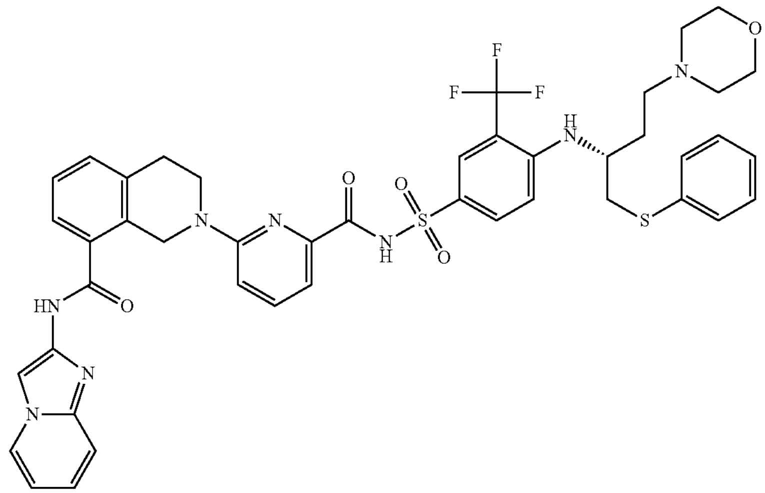 [SMILES: O=C(NS(=O)(=O)c1ccc(N[C@H](CCN2CCOCC2)CSc2ccccc2)c(C(F)(F)F)c1)c1cccc(N2CCc3cccc(C(=O)Nc4cn5ccccc5n4)c3C2)n1] |
| N-(imidazo[1,2-a]pyridin-2-yl)-2-[4-({[4-{[(2R)-4-(morpholin-4-yl)-1-(phenylsulfanyl)butan-2-yl]amino}-3-(trifluoromethyl)phenyl]sulfonyl}carbamoyl)-1,3-thiazol-2-yl]-1,2,3,4-tetrahydroisoquinoline-8-carboxamide; | 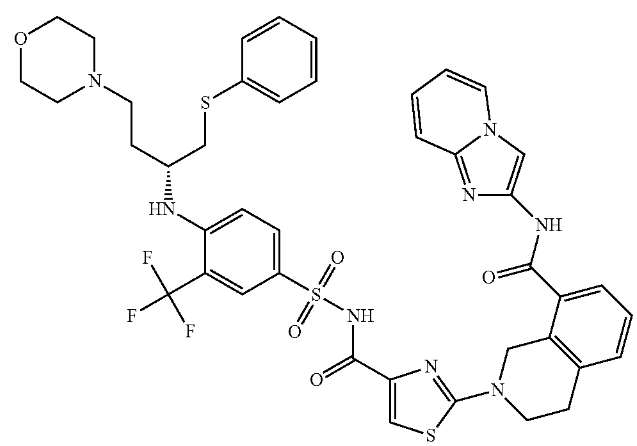 [SMILES: O=C(NS(=O)(=O)c1ccc(N[C@H](CCN2CCOCC2)CSc2ccccc2)c(C(F)(F)F)c1)c1csc(N2CCc3cccc(C(=O)Nc4cn5ccncc5n4)c3C2)n1] |

| Name | Structure |
|---|---|
| N-(imidazo[1,2-a]pyrazin-2-yl)-2-[6-({[4-{[(2R)-4-(morpholin-4-yl)-1-(phenylsulfanyl)butan-2-yl]amino}-3-(trifluoromethyl)phenyl]sulfonyl}carbamoyl)pyridin-2-yl]-1,2,3,4-tetrahydroisoquinoline-8-carboxamide; | 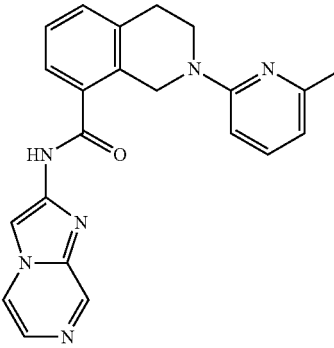 |
| N-(imidazo[1,2-a]pyrazin-2-yl)-2-[4-({[4-{[(2R)-4-(morpholin-4-yl)-1-(phenylsulfanyl)butan-2-yl]amino}-3-(trifluoromethyl)phenyl]sulfonyl}carbamoyl)-1,3-thiazol-2-yl]-1,2,3,4-tetrahydroisoquinoline-8-carboxamide; | 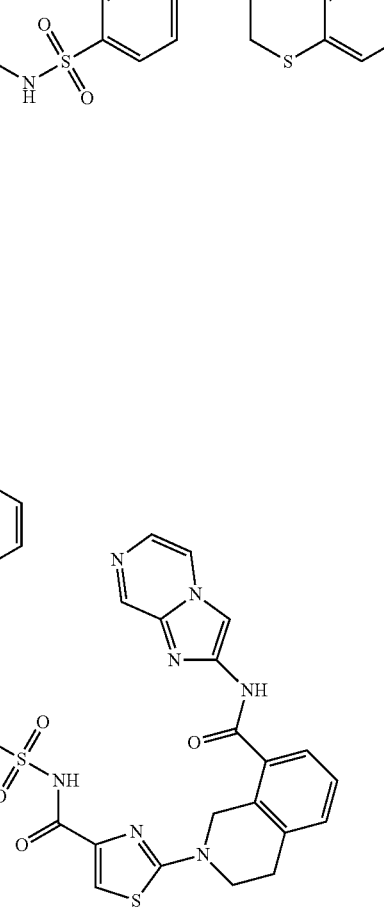 |
| N-(imidazo[1,2-b]pyridazin-2-yl)-2-[6-({[4-{[(2R)-4-(morpholin-4-yl)-1-(phenylsulfanyl)butan-2-yl]amino}-3-(trifluoromethyl)phenyl]sulfonyl}carbamoyl)pyridin-2-yl]-1,2,3,4-tetrahydroisoquinoline-8-carboxamide; | 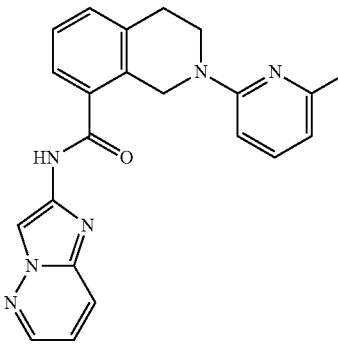 |

-continued

| Name | Structure |
|---|---|
| N-(imidazo[1,2-b]pyridazin-2-yl)-2-[4-({[4-{[(2R)-4-(morpholin-4-yl)-1-(phenylsulfanyl)butan-2-yl]amino}-3-(trifluoromethyl)phenyl]sulfonyl}carbamoyl)-1,3-thiazol-2-yl]-1,2,3,4-tetrahydroisoquinoline-8-carboxamide; | 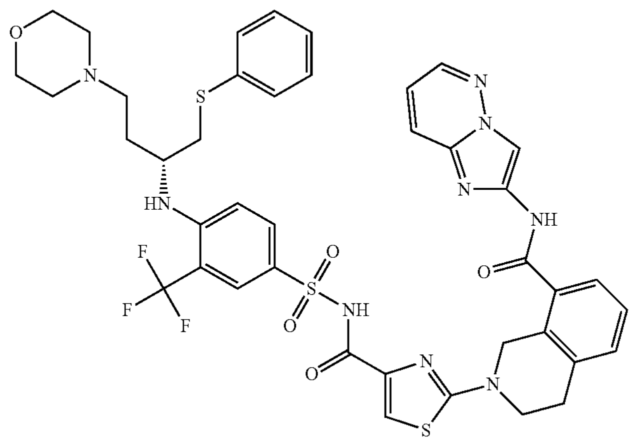 [SMILES: O=C(NS(=O)(=O)c1ccc(N[C@H](CCN2CCOCC2)CSc2ccccc2)c(C(F)(F)F)c1)c1csc(N2CCc3cccc(C(=O)Nc4cn5ncccc5n4)c3C2)n1] |
| N-(6-fluoro-1,3-benzothiazol-2-yl)-2-[6-({[4-{[(2R)-4-(morpholin-4-yl)-1-(phenylsulfanyl)butan-2-yl]amino}-3-(trifluoromethyl)phenyl]sulfonyl}carbamoyl)pyridin-2-yl]-1,2,3,4-tetrahydroisoquinoline-8-carboxamide; | 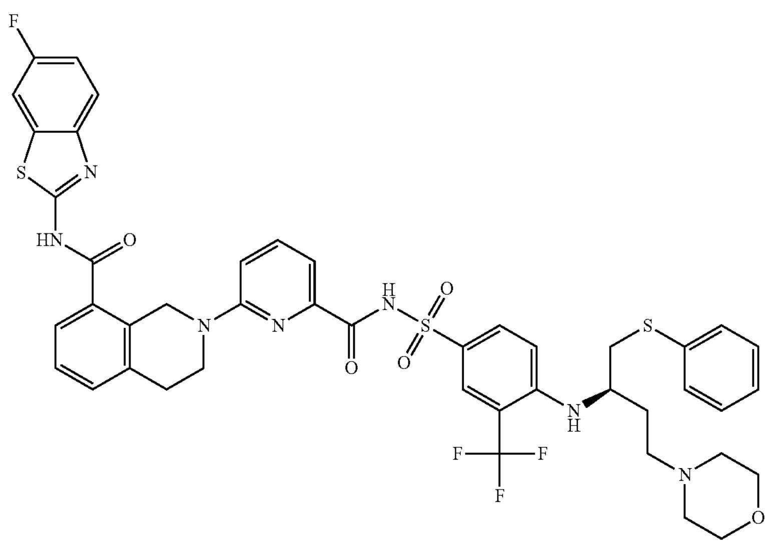 [SMILES: O=C(NS(=O)(=O)c1ccc(N[C@H](CCN2CCOCC2)CSc2ccccc2)c(C(F)(F)F)c1)c1cccc(N2CCc3cccc(C(=O)Nc4nc5ccc(F)cc5s4)c3C2)n1] |
| N-(6-fluoro-1,3-benzothiazol-2-yl)-2-[4-({[4-{[(2R)-4-(morpholin-4-yl)-1-(phenylsulfanyl)butan-2-yl]amino}-3-(trifluoromethyl)phenyl]sulfonyl}carbamoyl)-1,3-thiazol-2-yl]-1,2,3,4-tetrahydroisoquinoline-8-carboxamide; | 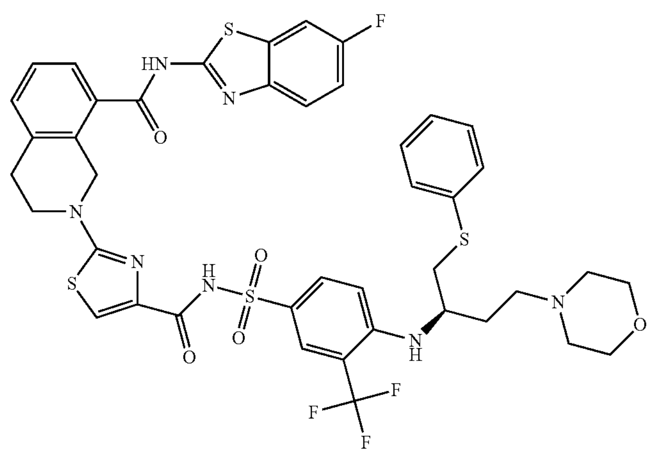 [SMILES: O=C(NS(=O)(=O)c1ccc(N[C@H](CCN2CCOCC2)CSc2ccccc2)c(C(F)(F)F)c1)c1csc(N2CCc3cccc(C(=O)Nc4nc5ccc(F)cc5s4)c3C2)n1] |

| Name | Structure |
|---|---|
| N-(1,3-benzothiazol-2-yl)-2-(6-{[(4-{[(2R)-4-(dimethylamino)-1-phenoxybutan-2-yl]amino}-3-nitrophenyl)sulfonyl]carbamoyl}pyridin-2-yl)-1,2,3,4-tetrahydroisoquinoline-8-carboxamide; | 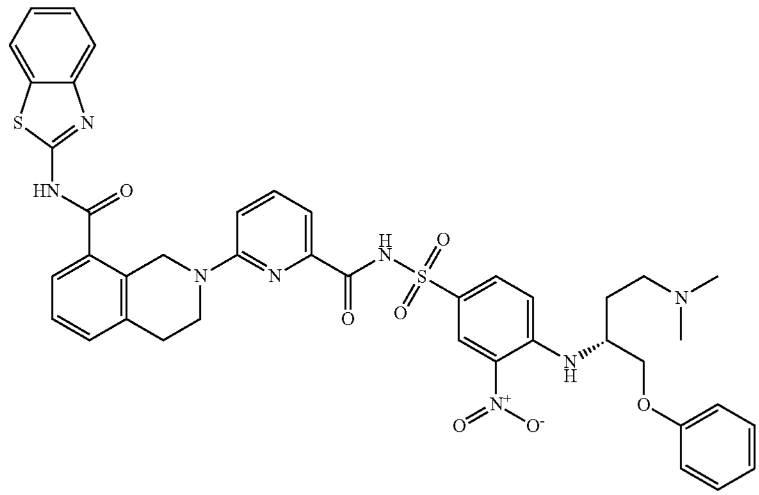 [SMILES: CN(C)CC[C@H](COc1ccccc1)Nc1ccc(S(=O)(=O)NC(=O)c2cccc(N3CCc4cccc(C(=O)Nc5nc6ccccc6s5)c4C3)n2)cc1[N+](=O)[O-]] |
| N-(1,3-benzothiazol-2-yl)-2-(4-{[(4-{[(2R)-4-(dimethylamino)-1-phenoxybutan-2-yl]amino}-3-nitrophenyl)sulfonyl]carbamoyl}-1,3-thiazol-2-yl)-1,2,3,4-tetrahydroisoquinoline-8-carboxamide; | 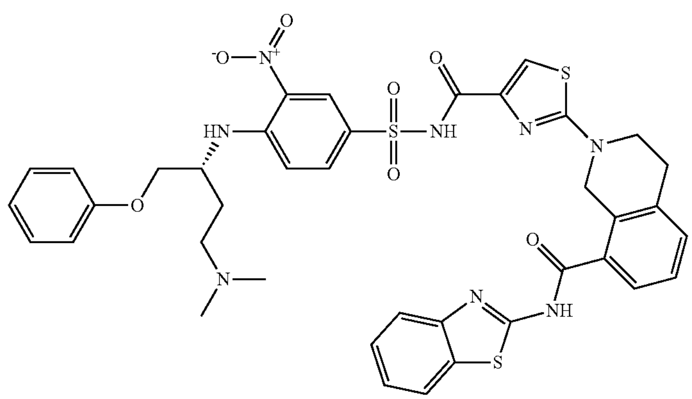 |
| 2-(6-{[(4-{[(2R)-4-(dimethylamino)-1-phenoxybutan-2-yl]amino}-3-nitrophenyl)sulfonyl]carbamoyl}pyridin-2-yl)-N-([1,3]thiazolo[5,4-b]pyridin-2-yl)-1,2,3,-tetrahydroisoquinoline-8-carboxamide; | 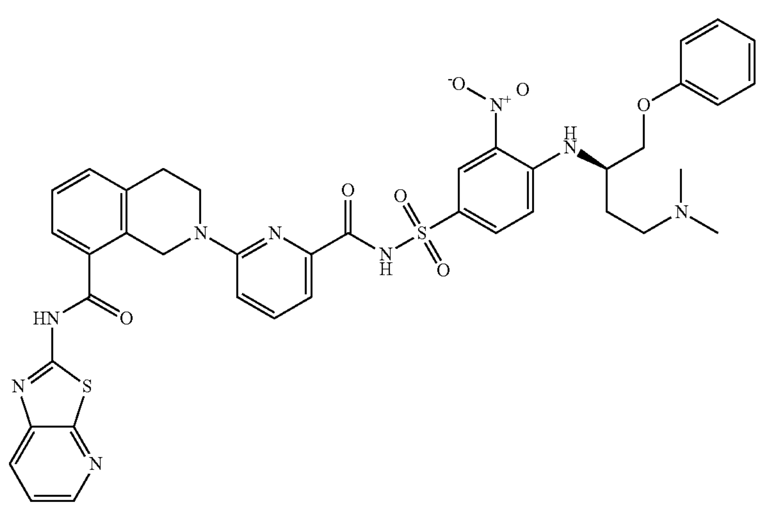 |

-continued

| Name | Structure |
|---|---|
| 2-(4-{[(4-{[(2R)-4-(dimethylamino)-1-phenoxybutan-2-yl]amino}-3-nitrophenyl)sulfonyl]carbamoyl}-1,3-thiazol-2-yl)-N-([1,3]thiazolo[5,4-b]pyridin-2-yl)-1,2,3,4-tetrahydroisoquinoline-8-carboxamide; | 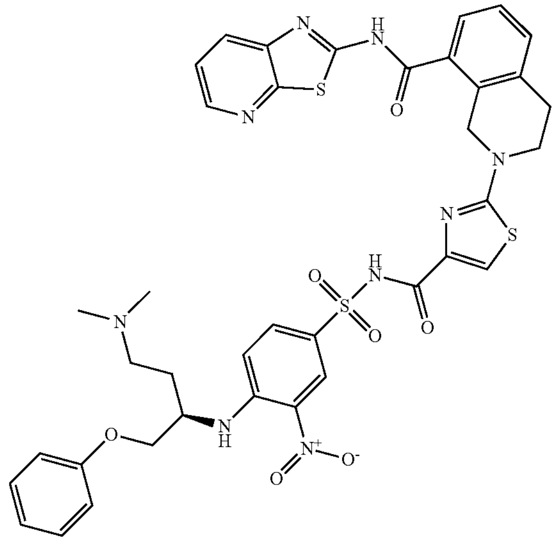 [SMILES: CN(C)CC[C@H](COc1ccccc1)Nc1ccc(S(=O)(=O)NC(=O)c2csc(N3CCc4cccc(C(=O)Nc5nc6cccnc6s5)c4C3)n2)cc1[N+](=O)[O-]] |
| 2-(6-{[(4-{[(2R)-4-(dimethylamino)-1-phenoxybutan-2-yl]amino}-3-nitrophenyl)sulfonyl]carbamoyl}pyridin-2-yl)-N-([1,3]thiazolo[5,4-c]pyridin-2-yl)-1,2,3,4-tetrahydroisoquinoline-8-carboxamide; | 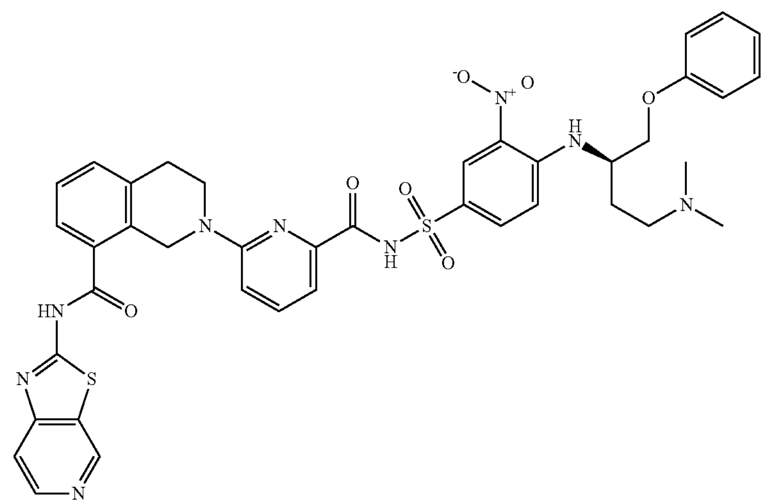 |
| 2-(4-{[(4-{[(2R)-4-(dimethylamino)-1-phenoxybutan-2-yl]amino}-3-nitrophenyl)sulfonyl]carbamoyl}-1,3-thiazol-2-yl)-N-([1,3]thiazolo[5,4-c]pyridin-2-yl)-1,2,3,4-tetrahydroisoquinoline-8-carboxamide; | 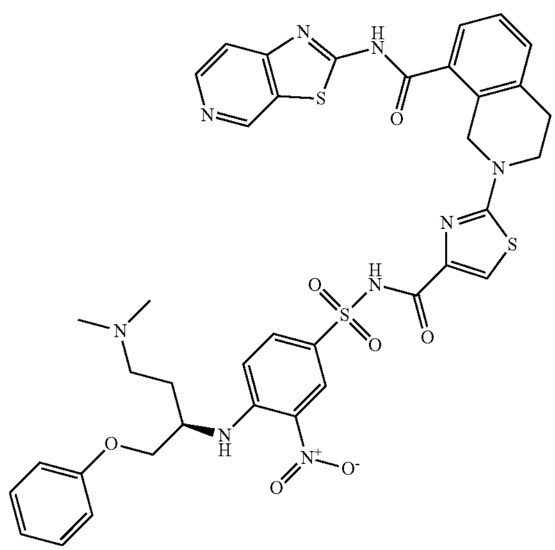 [SMILES: CN(C)CC[C@H](COc1ccccc1)Nc1ccc(S(=O)(=O)NC(=O)c2csc(N3CCc4cccc(C(=O)Nc5nc6ccncc6s5)c4C3)n2)cc1[N+](=O)[O-]] |

| Name | Structure |
|---|---|
| 2-(6-{[4-{[(2R)-4-(dimethylamino)-1-phenoxybutan-2-yl]amino}-3-nitrophenyl)sulfonyl]carbamoyl}pyridin-2-yl)-N-([1,3]thiazolo[4,5-c]pyridin-2-yl)-1,2,3,4-tetrahydroisoquinoline-8-carboxamide; | 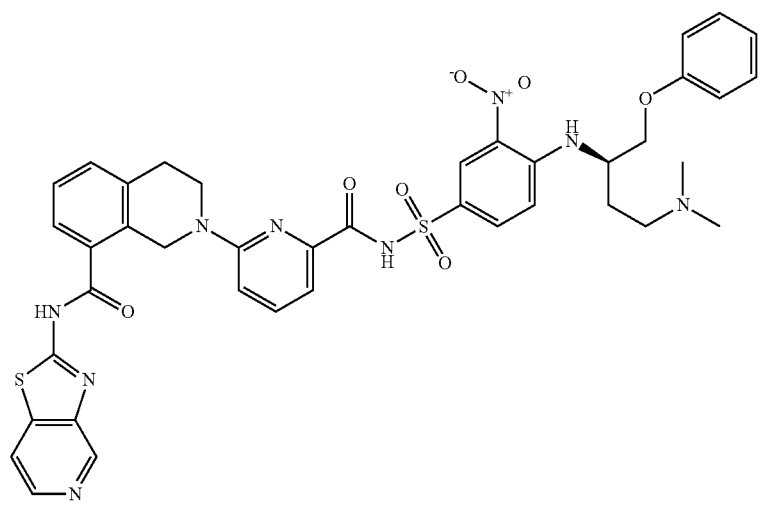 |
| 2-(4-{[(4-{[(2R)-4-(dimethylamino)-1-phenoxybutan-2-yl]amino}-3-nitrophenyl)sulfonyl]carbamoyl}-1,3-thiazol-2-yl)-N-([1,3]thiazolo[4,5-c]pyridin-2-yl)-1,2,3,4-tetrahydroisoquinoline-8-carboxamide; | 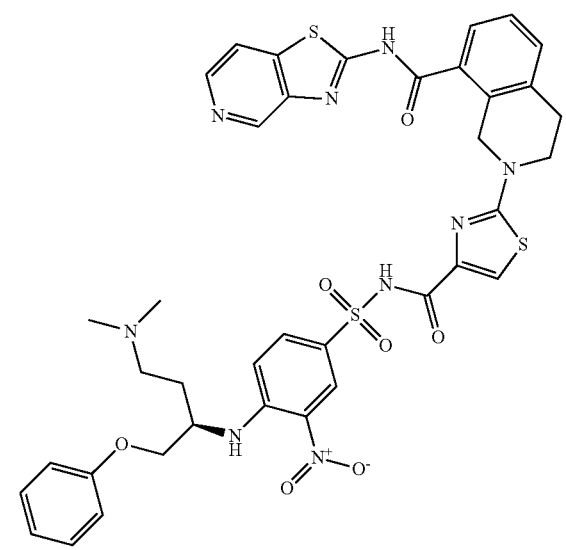 [SMILES: CN(C)CC[C@H](COc1ccccc1)Nc1ccc(S(=O)(=O)NC(=O)c2csc(N3CCc4cccc(C(=O)Nc5nc6cnccc6s5)c4C3)n2)cc1[N+](=O)[O-]] |
| 2-(6-{[(4-{[(2R)-4-(dimethylamino)-1-phenoxybutan-2-yl]amino}-3-nitrophenyl)sulfonyl]carbamoyl}pyridin-2-yl)-N-(imidazo[1,2-a]pyridin-2-yl)-1,2,3,4-tetrahydroisoquinoline-8-carboxamide; | 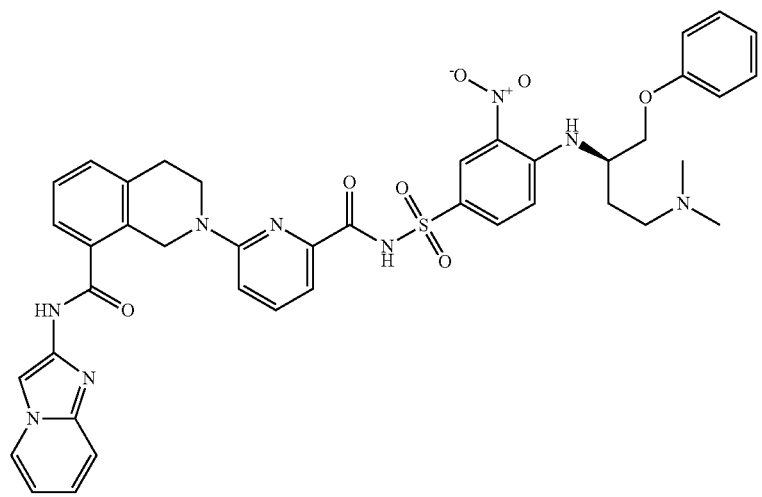 |

| Name | Structure |
|---|---|
| 2-(4-{[4-{[(2R)-4-(dimethylamino)-1-phenoxybutan-2-yl]amino}-3-nitrophenyl)sulfonyl]carbamoyl}-1,3-thiazol-2-yl)-N-(imidazo[1,2-a]pyridin-2-yl)-1,2,3,4-tetrahydroisoquinoline-8-carboxamide; | 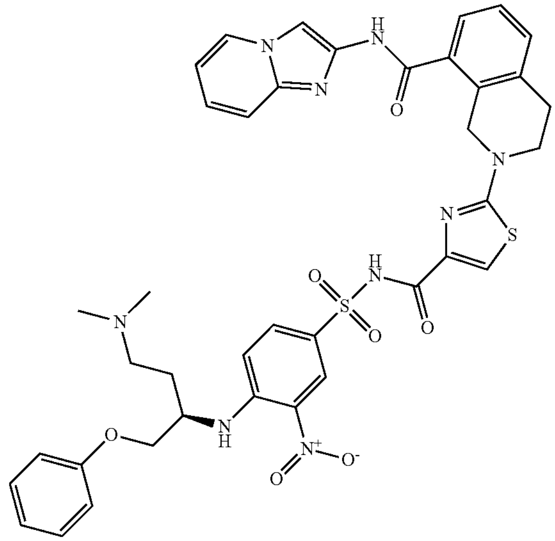 |
| 2-(6-{[4-{[(2R)-4-(dimethylamino)-1-phenoxybutan-2-yl]amino}-3-nitrophenyl)sulfonyl]carbamoyl}pyridin-2-yl)-N-(imidazo[1,2-a]pyrazin-2-yl)-1,2,3,4-tetrahydrisoquinoline-8-carboxamide; | 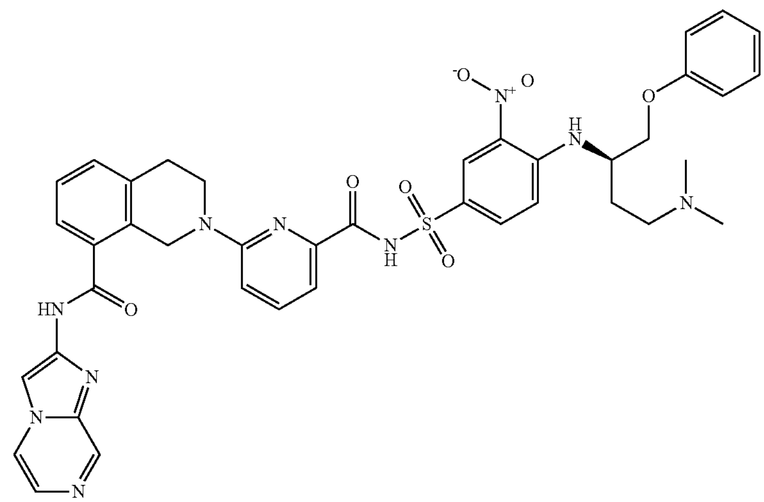 |
| 2-(4-{[(4-{[(2R)-4-(dimethylamino)-1-phenoxybutan-2-yl]amino}-3-nitrophenyl)sulfonyl]carbamoyl}-1,3-thiazol-2-yl)-N-(imidazo[1,2-a]pyrazin-2-yl)-1,2,3,4-tetrahydroisoquinoline-8-carboxamide; | 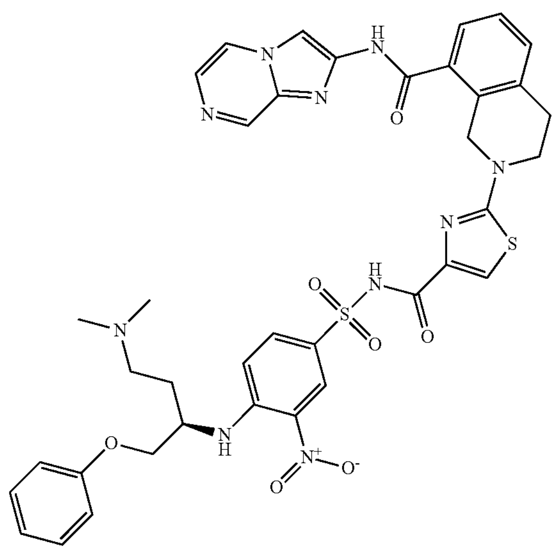 |

| Name | Structure |
|------|-----------|
| 2-(6-{[(4-{[(2R)-4-(dimethylamino)-1-phenoxybutan-2-yl]amino}-3-nitrophenyl)sulfonyl]carbamoyl}pyridin-2-yl)-N-(imidazo[1,2-a]pyridazin-2-yl)-1,2,3,4-tetrahydroisoquinoline-8-carboxamide; | 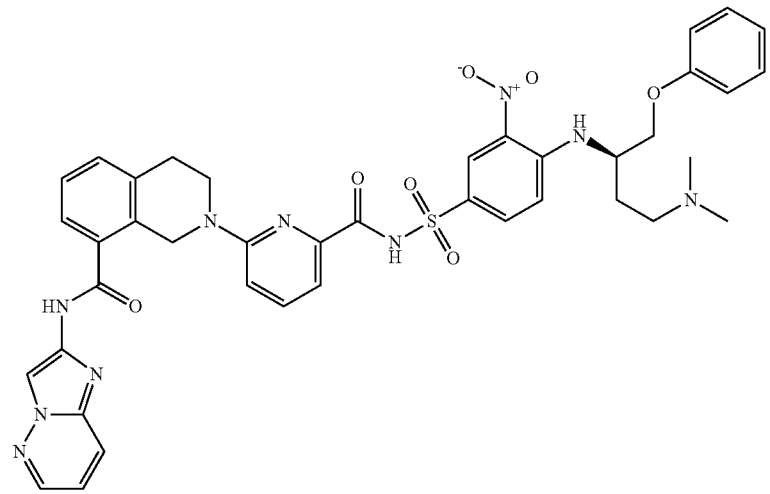 |
| 2-(4-{[(4-{[(2R)-4-(dimethylamino)-1-phenoxybutan-2-yl]amino}-3-nitrophenyl)sulfonyl]carbamoyl}-1,3-thiazol-2-yl)-N-(imidazo[1,2-b]pyridazin-2-yl)-1,2,3,4-tetrahydroisoquinoline-8-carboxamide; | 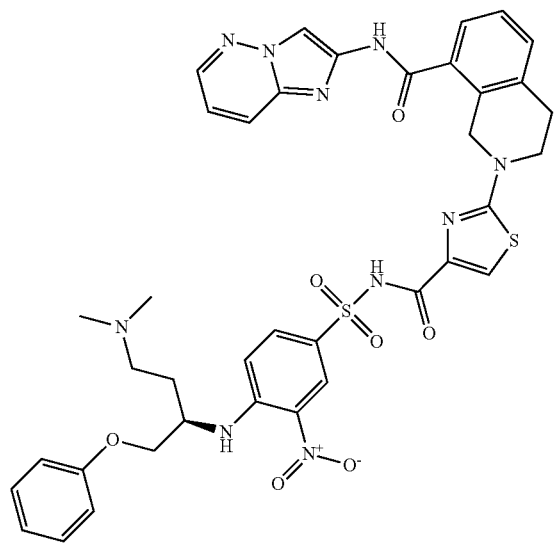 [SMILES: CN(C)CC[C@H](COc1ccccc1)Nc1ccc(S(=O)(=O)NC(=O)c2csc(N3CCc4cccc(C(=O)Nc5cn6ncccc6n5)c4C3)n2)cc1[N+](=O)[O-]] |
| 2-(6-{[(4-{[(2R)-4-(dimethylamino)-1-phenoxybutan-2-yl]amino}-3-nitrophenyl)sulfonyl]carbamoyl}pyridin-2-yl)-N-(6-fluoro-1,3-benzothiazol-2-yl)-1,2,3,4-tetrahydroisoquinoline-8-carboxamide; | 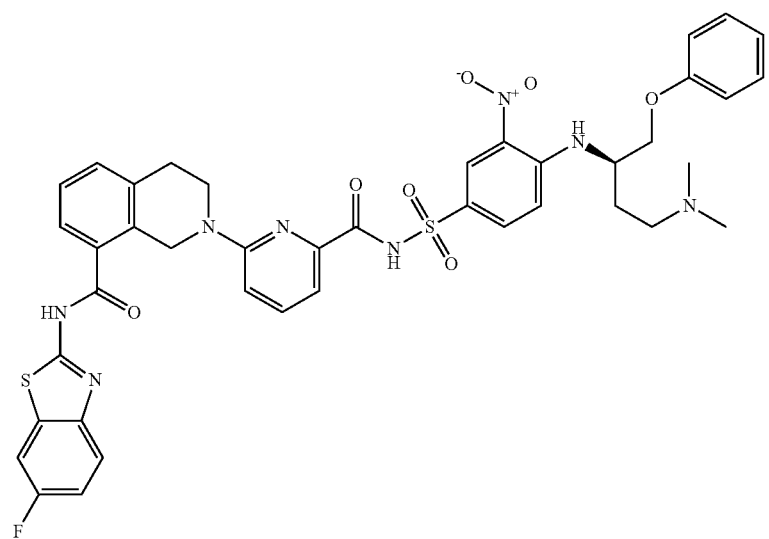 |

-continued

| Name | Structure |
|---|---|
| 2-(4-{[(4-{[(2R)-4-(dimethylamino)-1-phenoxybutan-2-yl]amino}-3-nitrophenyl)sulfonyl]carbamoyl}-1,3-thiazol-2-yl)-N-(6-fluoro-1,3-benzothiazol-2-yl)-1,2,3,4-tetrahydroisoquinoline-8-carboxamide; | 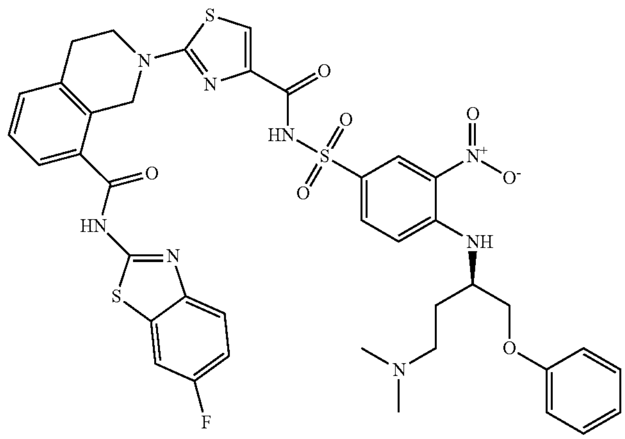 [SMILES: CN(C)CC[C@H](COc1ccccc1)Nc1ccc(S(=O)(=O)NC(=O)c2csc(N3CCc4cccc(C(=O)Nc5nc6ccc(F)cc6s5)c4C3)n2)cc1[N+](=O)[O-]] |
| N-(1,3-benzothiazol-2-yl)-2-(6-{[(6-{[(2R)-4-(dimethylamino)-1-(phenylsulfanyl)butan-2-yl]amino}-5-nitropyridin-3-yl)sulfonyl]carbamoyl}pyridin-2-yl)-1,2,3,4-tetrahydroisoquinoline-8-carboxamide; | 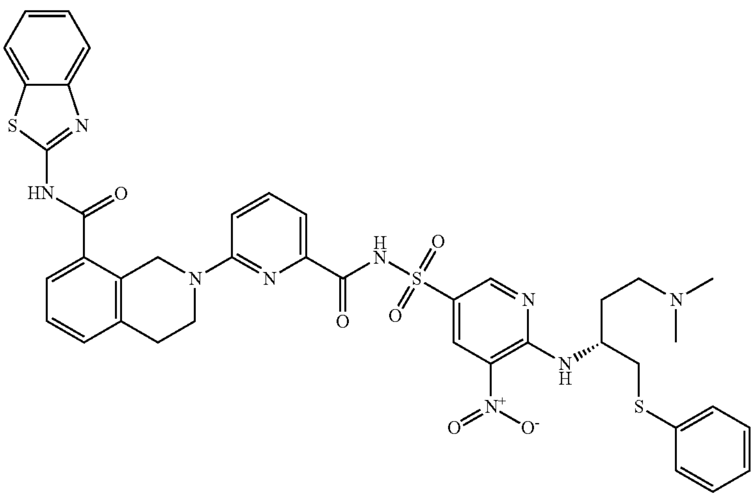 [SMILES: CN(C)CC[C@H](CSc1ccccc1)Nc1ncc(S(=O)(=O)NC(=O)c2cccc(N3CCc4cccc(C(=O)Nc5nc6ccccc6s5)c4C3)n2)cc1[N+](=O)[O-]] |
| N-(1,3-benzothiazol-2-yl)-2-(4-{[(6-{[(2R)-4-(dimethylamino)-1-(phenylsulfanyl)butan-2-yl]amino}-5-nitropyridin-3-yl)sulfonyl]carbamoyl}-1,3-thiazol-2-yl)-1,2,3,4-tetrahydroisoquinoline-8-carboxamide; | |

| Name | Structure |
| --- | --- |
| 2-(6-{[(6-{[(2R)-4-(dimethylamino)-1-(phenylsulfanyl)butan-2-yl]amino}-5-nitropyridin-3-yl)sulfonyl]carbamoyl}pyridin-2-yl)-N-([1,3]thiazolo[5,4-b]pyridin-2-yl)-1,2,3,4-tetrahydroisoquinoline-8-carboxamide; | 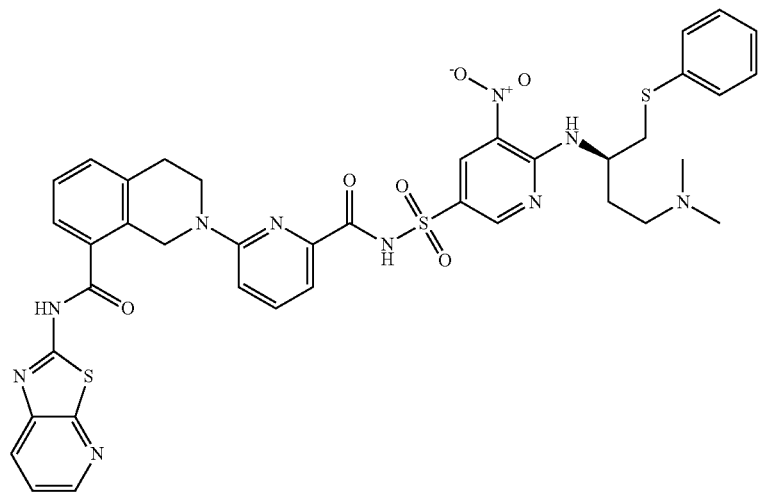 |
| 2-(4-{[(6-{[(2R)-4-(dimethylamino)-1-(phenyl-sulfanyl)butan-2-yl]amino}-5-nitropyridin-3-yl)sulfonyl]carbamoyl}-1,3-thiazol-2-yl)-N-([1,3]thiazolo[5,4-b]pyridin-2-yl)-1,2,3,4-tetrahydroisoquinoline-8-carboxamide; | 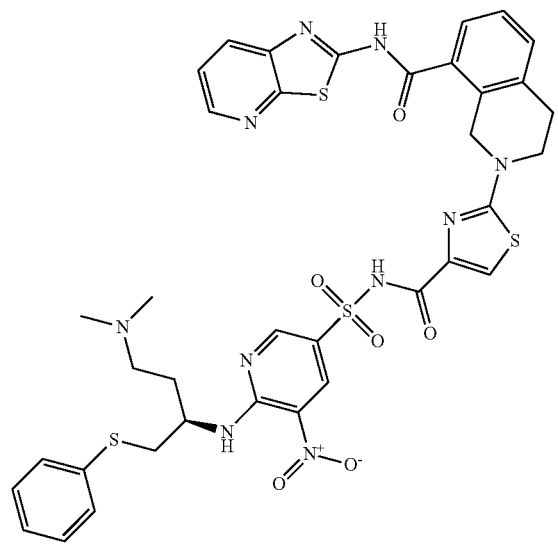 [SMILES: CN(C)CC[C@H](CSc1ccccc1)Nc1ncc(S(=O)(=O)NC(=O)c2csc(N3CCc4cccc(C(=O)Nc5nc6cccnc6s5)c4C3)n2)cc1[N+](=O)[O-]] |
| 2-(6-{[(6-{[(2R)-4-(dimethylamino)-1-(phenylsulfanyl)butan-2-yl]amino}-5-nitropyridin-3-yl)sulfonyl]carbamoyl}pyridin-2-yl)-N-([1,3]thiazolo[5,4-c]pyridin-2-yl)-1,2,3,4-tetrahydroisoquinoline-8-carboxamide; | 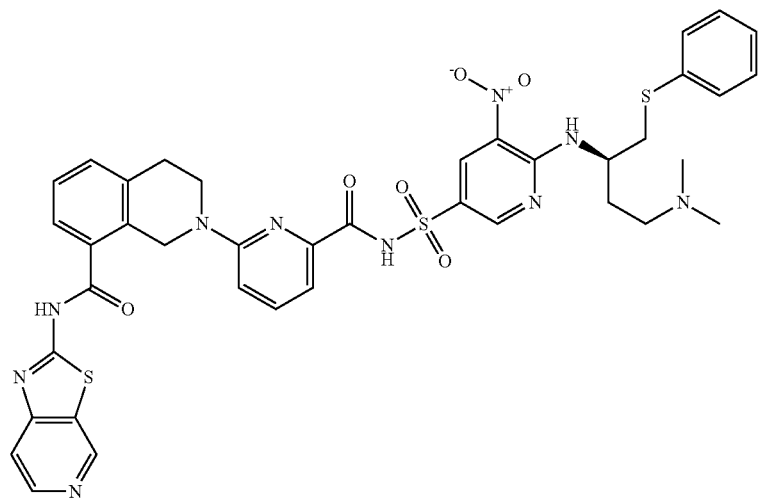 |

| Name | Structure |
|---|---|
| 2-(4-{[(6-{[(2R)-4-(dimethylamino)-1-(phenyl-sulfanyl)butan-2-yl]amino}-5-nitropyridin-3-yl)sulfonyl]carbamyl}-1,3-thiazol-2-yl)-N-([1,3]thiazolo[5,4-c]pyridin-2-yl)-1,2,3,4-teterahydroisoquinoline-8-carboxamide; | 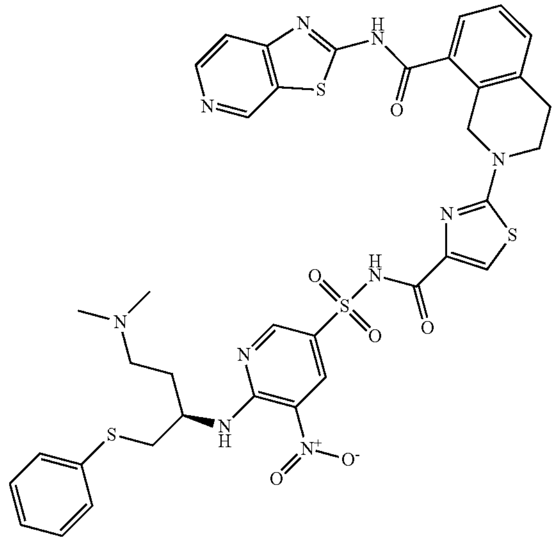 [SMILES: CN(C)CC[C@H](CSc1ccccc1)Nc1ncc(S(=O)(=O)NC(=O)c2csc(N3CCc4cccc(C(=O)Nc5nc6ccncc6s5)c4C3)n2)cc1[N+](=O)[O-]] |
| 2-(6-{[(6-{[(2R)-4-(dimethylamino)-1-(phenylsulfanyl)butan-2-yl]amino}-5-nitropyridin-3-yl)sulfonyl]carbamoyl}pyridin-2-yl)-N-([1,3]thiazolo[4,5-c]pyridin-2-yl)-1,2,3,4-tetrahydroisoquinoline-8-carboxamide; | 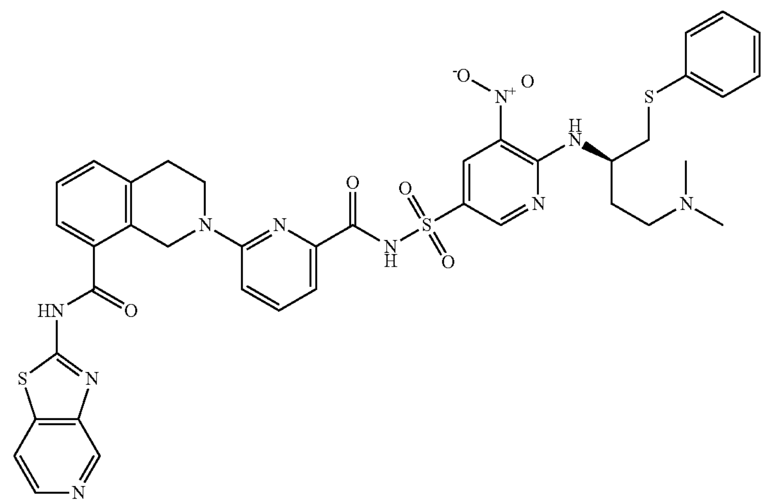 |
| 2-(4-{[(6-{[(2R)-4-(dimethylamino)-1-(phenyl-sulfanyl)butan-2-yl]amino}-5-nitropyridin-3-yl)sulfonyl]carbamoyl}-1,3-thiazol-2-yl)-N-([1,3]thiazolo[4,5-c]pyridin-2-yl)-1,2,3,4-tetra-hydroisoquinoline-8-carboxamide; | 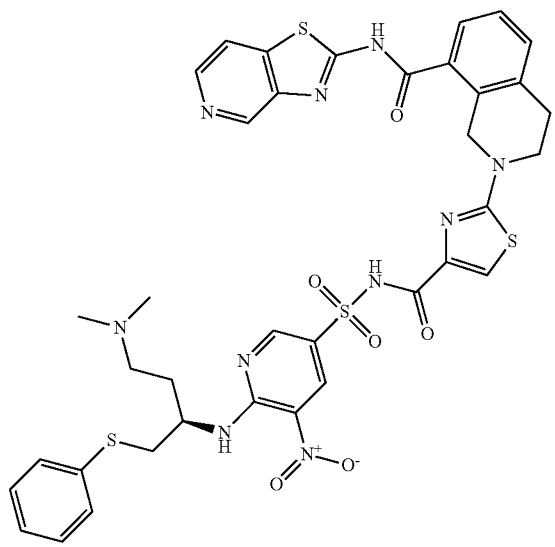 [SMILES: CN(C)CC[C@H](CSc1ccccc1)Nc1ncc(S(=O)(=O)NC(=O)c2csc(N3CCc4cccc(C(=O)Nc5nc6cnccc6s5)c4C3)n2)cc1[N+](=O)[O-]] |

| Name | Structure |
|---|---|
| 2-(6-{[(6-{[(2R)-4-(dimethylamino)-1-(phenyl-sulfanyl)butan-2-yl]amino}-5-nitropyridin-3-yl)sulfonyl]carbamoyl}pyridin-2-yl)-N-(imidazo[1,2-a]pyridin-2-yl)-1,2,3,4-tetrahydroisoquinoline-8-carboxamide; | 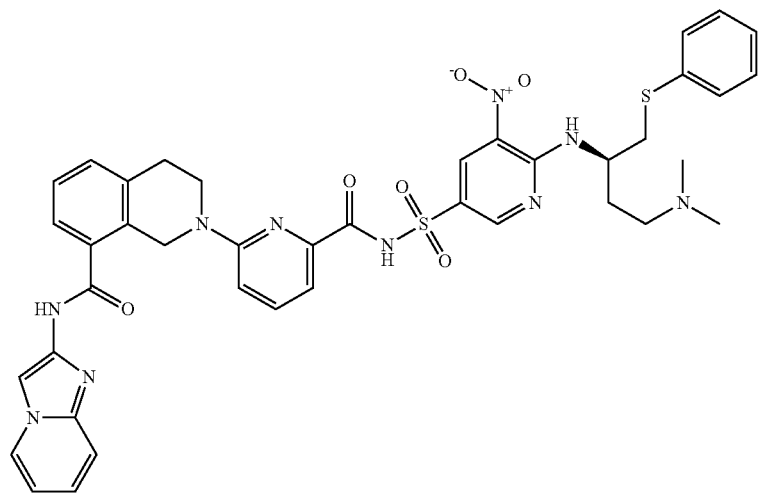 |
| 2-(4-{[(6-{[(2R)-4-(dimethylamino)-1-(phenyl-sulfanyl)butan-2-yl]amino}-5-nitropyridin-3-yl)sulfonyl]carbamoyl}-1,3-thiazol-2-yl)-N-(imidazo[1,2-a]pyridin-2-yl)-1,2,3,4-tetrahydroisoquinoline-8-carboxamide; | 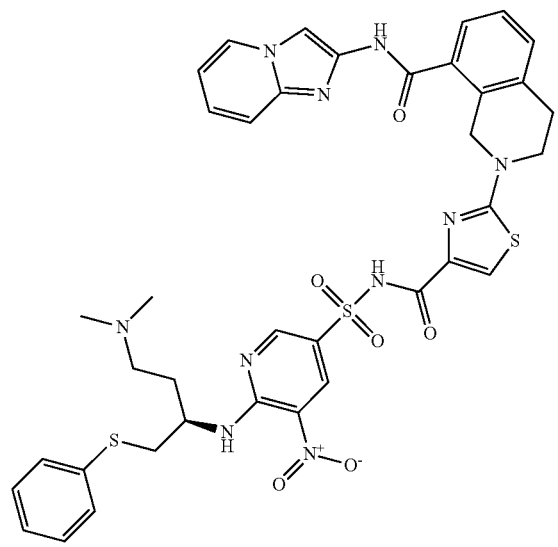 [SMILES: CN(C)CC[C@H](CSc1ccccc1)Nc1ncc(S(=O)(=O)NC(=O)c2csc(N3CCc4cccc(C(=O)Nc5cn6ccccc6n5)c4C3)n2)cc1[N+](=O)[O-]] |
| 2-(6-{[(6-{[(2R)-4-(dimethylamino)-1-(phenyl-sulfanyl)butan-2-yl]amino}-5-nitropyridin-3-yl)sulfonyl]carbamoyl}pyridin-2-yl)-N-(imidazo[1,2-a]pyrazin-2-yl)-1,2,3,4-tetrahydro-isoquinoline-8-carboxamide; | 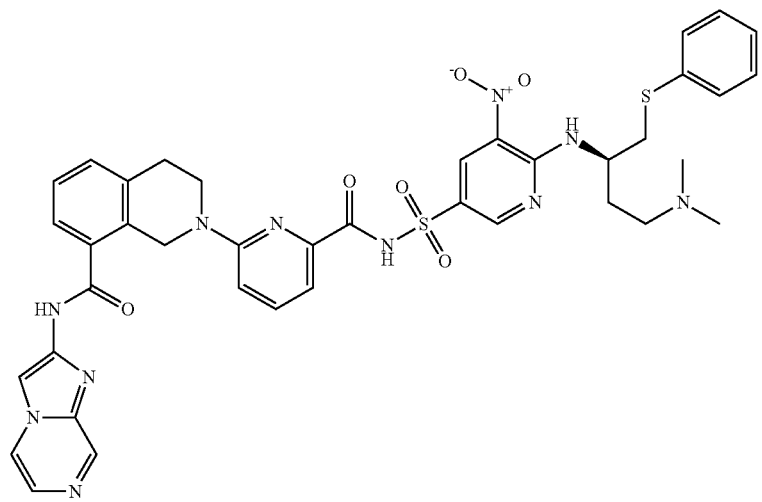 |

| Name | Structure |
|---|---|
| 2-(4-{[(6-{[(2R)-4-(dimethylamino)-1-(phenylsulfanyl)butan-2-yl]amino}-5-nitropyridin-3-yl)sulfonyl]carbamoyl}-1,3-thiazol-2-yl)-N-(imidazo[1,2-a]pyrazin-2-yl)-1,2,3,4-tetrahydroisoquinoline-8-carboxamide; | 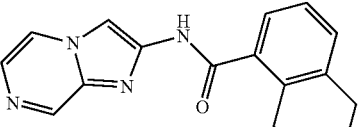 |
| 2-(6-{[(6-{[(2R)-4-(dimethylamino)-1-(phenylsulfanyl)butan-2-yl]amino}-5-nitropyridin-3-yl)sulfonyl]carbamoyl}pyridin-2-yl)-N-(imidazo[1,2-b]pyridazin-2-yl)-1,2,3,4-tetrahydroisoquinoline-8-carboxamide; | 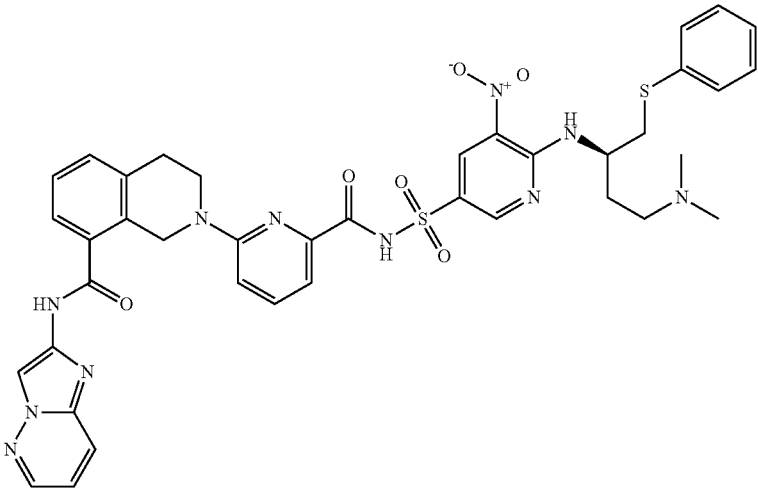 |
| 2-(4-{[(6-{[(2R)-4-(dimethylamino)-1-(phenyl-sulfanyl)butan-2-yl]amino}-5-nitropyridin-3-yl)sulfonyl]carbamoyl}-1,3-thiazol-2-yl)-N-(imidazo[1,2-b]pyridazin-2-yl)-1,2,3,4-tetrahydroisoquinoline-8-carboxamide; | 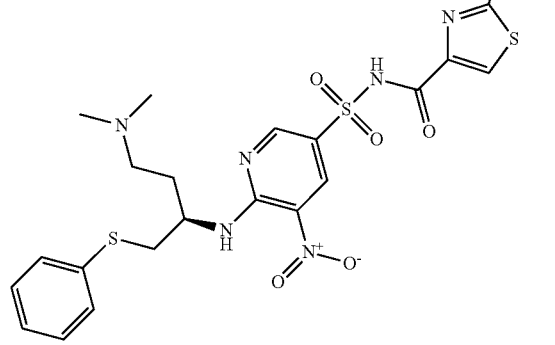 |

| Name | Structure |
|---|---|
| 2-(6-{[(6-{[(2R)-4-(dimethylamino)-1-(phenyl-sulfanyl)butan-2-yl]amino}-5-nitropyridin-3-yl)sulfonyl]carbamoyl}pyridin-2-yl)-N-(6-fluoro-1,3-benzothiazol-2-yl)-1,2,3,4-tetra-hydroisoquinoline-8-carboxamide; | 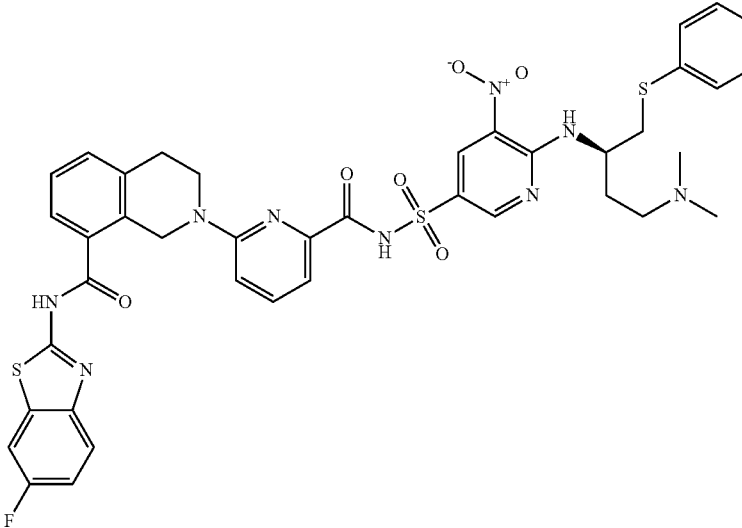 |
| 2-(4-{[(6-{[(2R)-4-(dimethylamino)-1-(phenyl-sulfanyl)butan-2-yl]amino}-5-nitropyridin-3-yl)sulfonyl]carbamoyl}-1,3-thiazol-2-yl)-N-(6-fluoro-1,3-benzothiazol-2-yl)-1,2,3,4-tetrahydroisoquinoline-8-carboxamide; | 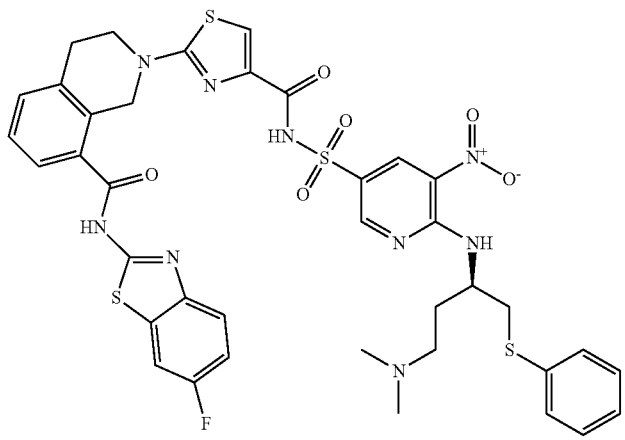 [SMILES: CN(C)CC[C@H](CSc1ccccc1)Nc1ncc(S(=O)(=O)NC(=O)c2csc(N3CCc4cccc(C(=O)Nc5nc6ccc(F)cc6s5)c4C3)n2)cc1[N+](=O)[O-]] |
| N-(1,3-benzothiazol-2-yl)-2-(6-{[(4-{[(2R)-4-(morpholin-4-yl)-1-(phenylsulfanyl)butan-2-yl]amino}-3-nitrophenyl)sulfonyl]carbamoyl}pyridin-2-yl)-1,2,3,4-tetrahydroisoquinoline-8-carboxamide; and | 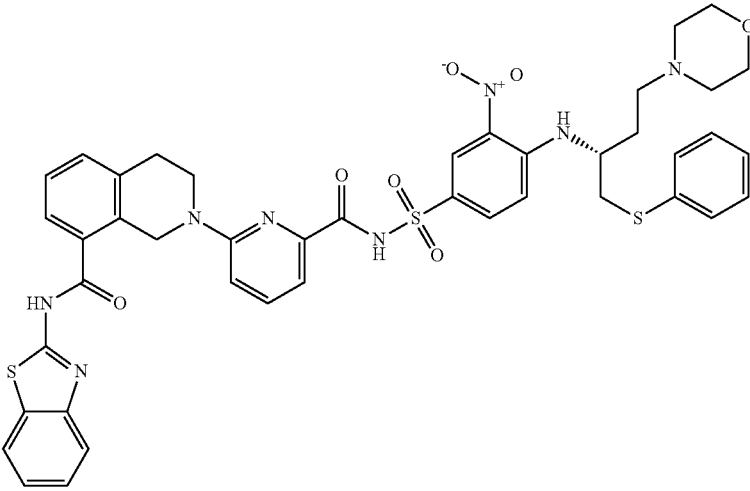 |

| Name | Structure |
|---|---|
| N-(1,3-benzothiazol-2-yl)-2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-1,2,3,4-tetrahydroisoquinoline-8-carboxamide | 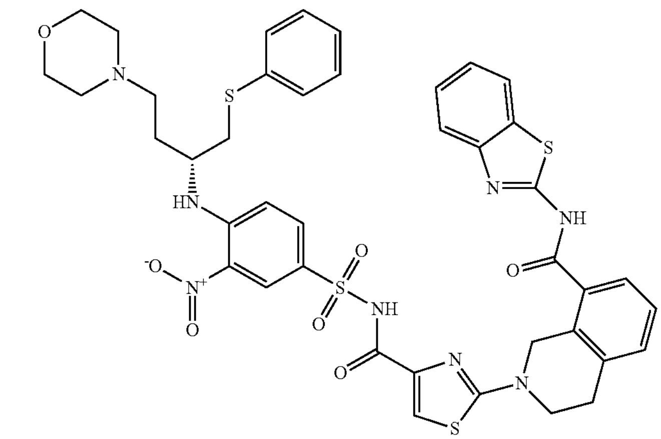 |
| N-(1,3-benzothiazol-2-yl)-2-(4-{[(4-{[(2R)-4-(dimethylamino)-1-(phenylsulfanyl)butan-2-yl]amino}-3-nitrophenyl)sulfonyl]carbamoyl}-1,3-thiazol-2-yl)-1,2,3,4-tetrahydroisoquinoline-8-carboxamide; | 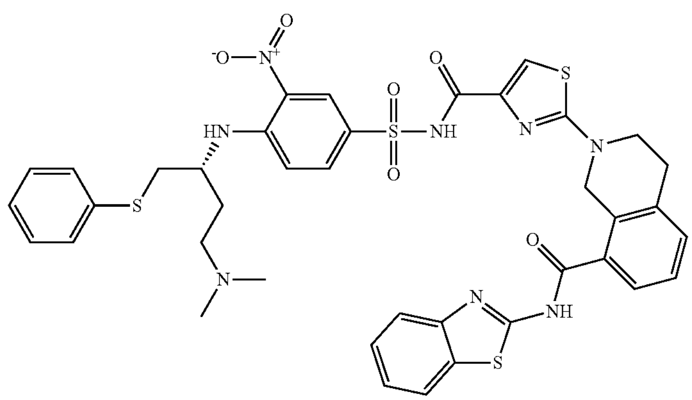 |
| N-(1,3-benzothiazol-2-yl)-2-(4-{[(4-{[(2R)-4-(morpholin-4-yl)-1-(phenylsulfanyl)butan-2-yl]amino}-3-[(trifluoromethyl)sulfonyl]phenyl)sulfonyl]carbamoyl}-1,3-thiazol-2-yl)-1,2,3,4-tetrahydroisoquinoline-8-carboxamide; | 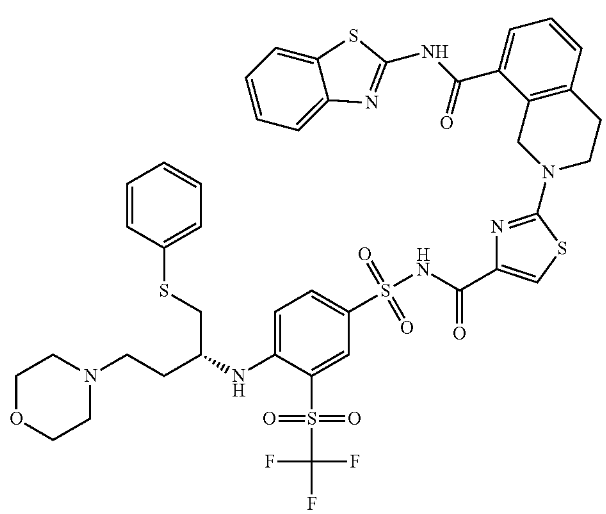 |

| Name | Structure |
|---|---|
| N-(1,3-benzothiazol-2-yl)-2-(6-{[(4-{[(2R)-4-(morpholin-4-yl)-1-(phenylsulfanyl)butan-2-yl]amino}-3-[(trifluoromethyl)sulfonyl]phenyl)sulfonyl]carbamoyl}pyridin-2-yl)-1,2,3,4-tetrahydroisoquinoline-8-carboxamide; | |
| N-(1,3-benzothiazol-2-yl)-2-[6-{[(4-{[3-(dimethylamino)propyl]amino}-3-nitrophenyl)sulfonyl]carbamoyl}-5-(3-phenylpropyl)pyridin-2-yl]-1,2,3,4-tetrahydroisoquinoline-8-carboxamide; | |
| N-(1,3-benzothiazol-2-yl)-2-[6-{[(4-{[3-(dimethylamino)propyl]amino}-3-[(trifluoromethyl)sulfonyl)phenyl)sulfonyl]carbamoyl}-5-(3-phenylpropyl)pyridin-2-yl]-1,2,3,4-tetrahydroisoquinoline-8-carboxamide; | |

| Name | Structure |
|---|---|
| N-(1,3-benzothiazol-2-yl)-2-[6-{[(4-{[3-(dimethylamino)propyl]amino}-3-nitrophenyl)sulfonyl]carbamoyl}-5-(2-phenylethyl)pyridin-2-yl]-1,2,3,4-tetrahydroisoquinoline-8-carboxamide; | 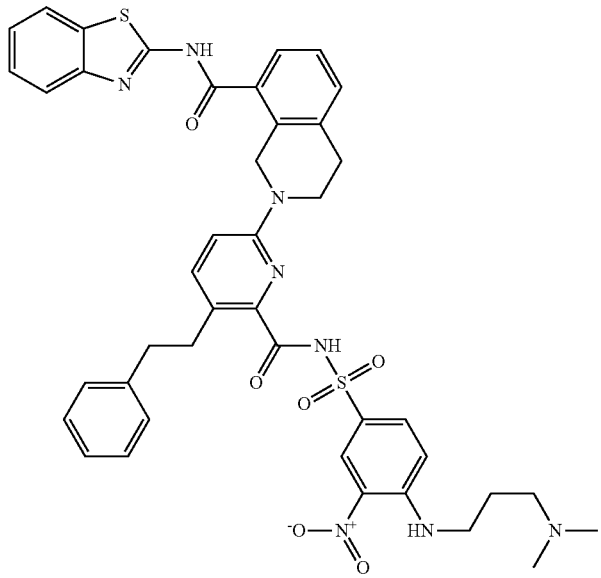 |
| N-(1,3-benzothiazol-2-yl)-2-(4-{[(4-{[3-(dimethylamino)propyl]amino}-3-[(trifluoromethyl)sulfonyl]phenyl)sulfonyl]carbamoyl}-1,3-thiazol-2-yl)-1,2,3,4-tetrahydroisoquinoline-8-carboxamide; | 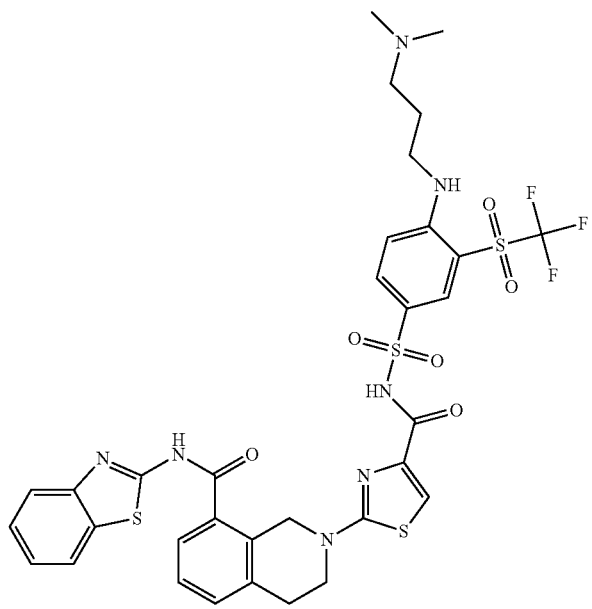 [SMILES: CN(C)CCCNc1ccc(S(=O)(=O)NC(=O)c2csc(N3CCc4cccc(C(=O)Nc5nc6ccccc6s5)c4C3)n2)cc1S(=O)(=O)C(F)(F)F] |

-continued

| Name | Structure |
|---|---|
| N-(1,3-benzothiazol-2-yl)-2-(5-benzyl-4-{[(4-{[3-(dimethylamino)propyl]amino}-3-[(trifluoromethyl)sulfonyl]phenyl)sulfonyl]carbamoyl}-1,3-thiazol-2-yl)-1,2,3,4-tetrahydroisoquinoline-8-carboxamide; | 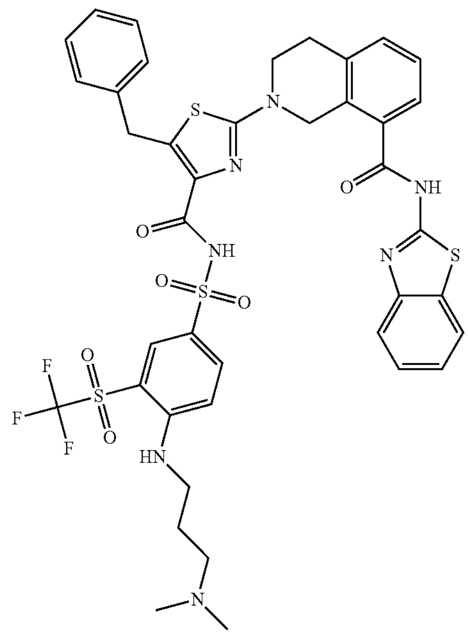 [SMILES: CN(C)CCCNc1ccc(S(=O)(=O)NC(=O)c2nc(N3CCc4cccc(C(=O)Nc5nc6ccccc6s5)c4C3)sc2Cc2ccccc2)cc1S(=O)(=O)C(F)(F)F] |
| N-(1,3-benzothiazol-2-yl)-2-(5-benzyl-4-{[(4-{[3-(dimethylamino)propyl]amino}-3-nitrophenyl)sulfonyl]carbamoyl}-1,3-thiazol-2-yl)-1,2,3,4-tetrahydroisoquinoline-8-carboxamide; | 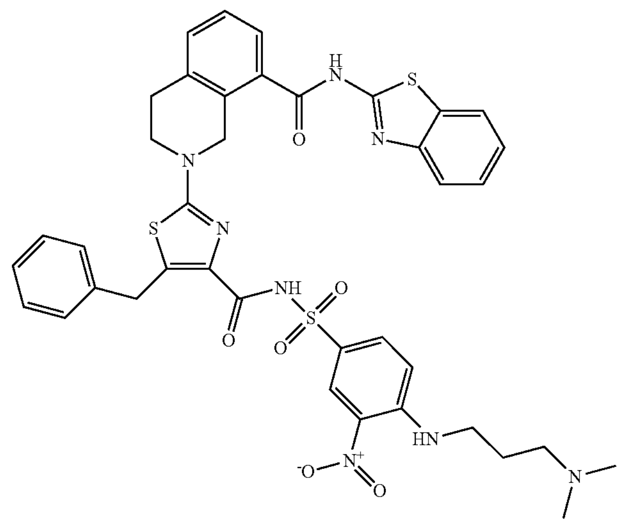 |
| N-(1,3-benzothiazol-2-yl)-2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-1,2,3,4-tetrahydroisoquinoline-8-carboxamide; | 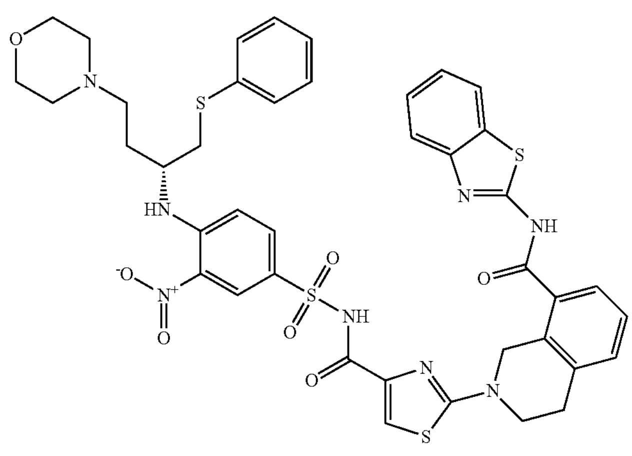 |

| Name | Structure |
|---|---|
| N-(1,3-benzothiazol-2-yl)-2-([4-{[(4-{[3-(dimethyl-amino)propyl]amino}-3-[(trifluoromethyl)sulfonyl]phenyl)sulfonyl]carbamoyl}-5-(2-phenylethyl)-1,3-thiazol-2-yl]-1,2,3,4-tetra-hydroisoquinoline-8-carboxamide; | 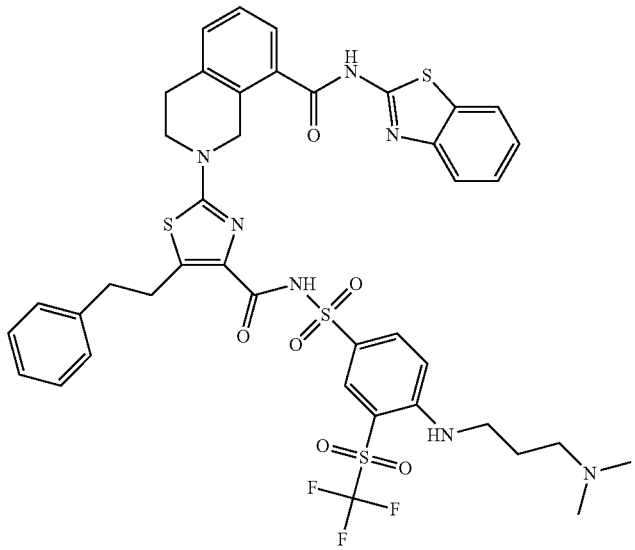 [SMILES: CN(C)CCCNc1ccc(S(=O)(=O)NC(=O)c2nc(N3CCc4cccc(C(=O)Nc5nc6ccccc6s5)c4C3)sc2CCc2ccccc2)cc1S(=O)(=O)C(F)(F)F] |
| N-(1,3-benzothiazol-2-yl)-2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-1,2,3,4-tetrahydroisoquinoline-8-carboxamide; | 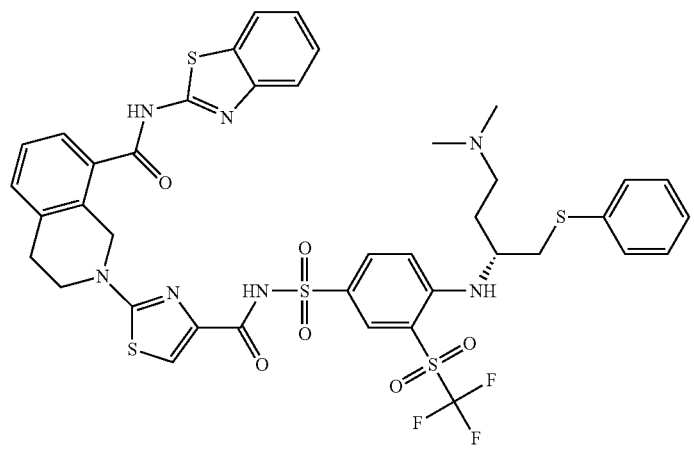 [SMILES: CN(C)CC[C@H](CSc1ccccc1)Nc1ccc(S(=O)(=O)NC(=O)c2csc(N3CCc4cccc(C(=O)Nc5nc6ccccc6s5)c4C3)n2)cc1S(=O)(=O)C(F)(F)F] |
| N-(1,3-benzothiazol-2-yl)-2-[4-{[(4-{[3-(dimethylamino)propyl]amino}-3-nitrophenyl)sulfonyl]carbamoyl}-5-(2-phenyl-ethyl)-1,3-thiazol-2-yl]-1,2,3,4-tetrahydroisoquinoline-8-carboxamide; | 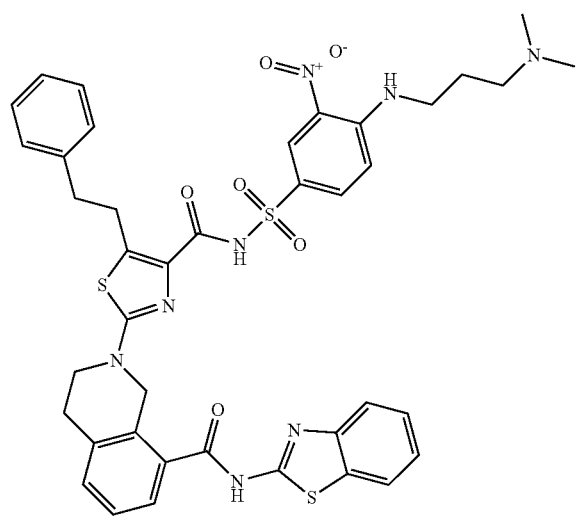 |

-continued

| Name | Structure |
|---|---|
| N-(1,3-benzothiazol-2-yl)-2-(4-{[(4-{[(2R)-4-hydroxy-1-(phenylsulfanyl)butan-2-yl]amino}-3-[(trifluoromethyl)sulfonyl]phenyl)sulfonyl]carbamoyl}-1,3-thiazol-2-yl)-1,2,3,4-tetrahydroisoquinoline-8-carboxamide; | 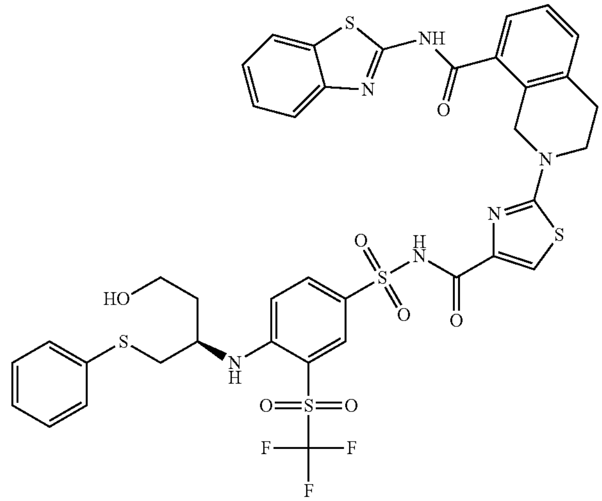 [SMILES: O=C(NS(=O)(=O)c1ccc(N[C@H](CCO)CSc2ccccc2)c(S(=O)(=O)C(F)(F)F)c1)c1csc(N2CCc3cccc(C(=O)Nc4nc5ccccc5s4)c3C2)n1] |
| N-(1,3-benzothiazol-2-yl)-2-[4-{[(4-{[3-(dimethylamino)propyl]amino}-3-nitrophenyl)sulfonyl]carbamoyl}-5-(3-phenylpropyl)-1,3-thiazol-2-yl]-1,2,3,4-tetrahydroisoquinoline-8-carboxamide. | 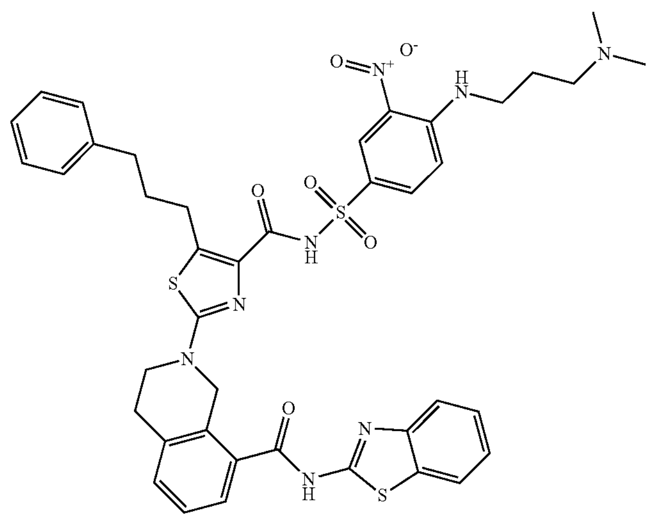 |

In some embodiments, the compound is selected from the group consisting of:

| Name | Structure |
|---|---|
| 6-[8-(1,3-benzothiazol-2-ylcarbamoyl)-3,4-dihydroisoquinolin-2(1H)-yl]-3-{1-[tricyclo[3.3.1.1³,⁷]dec-1-ylmethyl]-1H-pyrazol-4-yl}pyridine-2-carboxylic acid; | |

-continued

| Name | Structure |
|---|---|
| 6-[8-(1,3-benzothiazol-2-ylcarbamoyl)-3,4-dihydroisoquinolin-2(1H)-yl]-3-[3,5-dimethyl-1-(tricyclo[3.3.1.1³,⁷]dec-1-ylmethyl)-1H-pyrazol-4-yl]pyridine-2-carboxylic acid; | |
| 6-[8-(1,3-benzothiazol-2-ylcarbamoyl)-3,4-dihydroisoquinolin-2(1H)-yl]-3-[5-methyl-1-(tricyclo[3.3.1.1³,⁷]dec-1-ylmethyl)-1H-pyrazol-4-yl]pyridine-2-carboxylic acid; | |
| 6-[8-(1,3-benzothiazol-2-ylcarbamoyl)-3,4-dihydroisoquinolin-2(1H)-yl]-3-[1-(spiro[3.5]non-7-ylmethyl)-1H-pyrazol-4-yl]pyridine-2-carboxylic acid; | |
| 6-[8-(1,3-benzothiazol-2-ylcarbamoyl)-3,4-dihydroisoquinolin-2(1H)-yl]-3-(1-{[3,5-dimethyltricyclo[3.3.1.1³,⁷]dec-1-yl]methyl}-1H-pyrazol-4-yl)pyridine-2-carboxylic acid; | |
| 6-[8-(1,3-benzothiazol-2-ylcarbamoyl)-3,4-dihydroisoquinolin-2(1H)-yl]-3-(1-{[3-hydroxytricyclo[3.3.1.1³,⁷]dec-1-yl]methyl}-1H-pyrazol-4-yl)pyridine-2-carboxylic acid; | |

-continued

| Name | Structure |
|---|---|
| 6-[8-(1,3-benzothiazol-2-ylcarbamoyl)-3,4-dihydroisoquinolin-2(1H)-yl]-3-(1-{[3-methoxytricyclo[3.3.1.1³,⁷]dec-1-yl]methyl}-1H-pyrazol-4-yl)pyridine-2-carboxylic acid; | |
| 6-[8-(1,3-benzothiazol-2-ylcarbamoyl)-3,4-dihydroisoquinolin-2(1H)-yl]-3-(1-{[3-(2-methoxyethoxy)tricyclo[3.3.1.1³,⁷]dec-1-yl]methyl}-1H-pyrazol-4-yl)pyridine-2-carboxylic acid; | |
| 6-[8-(1,3-benzothiazol-2-ylcarbamoyl)-3,4-dihydroisoquinolin-2(1H)-yl]-3-{1-[(3,5,7-trimethyltricyclo[3.3.1.1³,⁷]dec-1-yl)methyl]-1H-pyrazol-4-yl}pyridine-2-carboxylic acid; | |
| 6-[8-(1,3-benzothiazol-2-ylcarbamoyl)-3,4-dihydroisoquinolin-2(1H)-yl]-3-[1-(tricyclo[3.3.1.1³,⁷]dec-2-ylmethyl)-1H-pyrazol-4-yl]pyridine-2-carboxylic acid; | |
| 6-[8-(1,3-benzothiazol-2-ylcarbamoyl)-3,4-dihydroisoquinolin-2(1H)-yl]-3-(1-{[3-bromotricyclo[3.3.1.1³,⁷]dec-1-yl]methyl}-1H-pyrazol-4-yl)pyridine-2-carboxylic acid; | |
| 6-[8-(1,3-benzothiazol-2-ylcarbamoyl)-3,4-dihydroisoquinolin-2(1H)-yl]-3-(1-{[3-(propan-2-yloxy)tricyclo[3.3.1.1³,⁷]dec-1-yl]methyl}-1H-pyrazol-4-yl)pyridine-2-carboxylic acid; | |

| Name | Structure |
|---|---|
| 6-[8-(1,3-benzothiazol-2-ylcarbamoyl)-3,4-dihydroisoquinolin-2(1H)-yl]-3-[1-(2-oxatricyclo[3.3.1.1³,⁷]dec-1-ylmethyl)-1H-pyrazol-4-yl]pyridine-2-carboxylic acid; | |
| 6-[8-(1,3-benzothiazol-2-ylcarbamoyl)-4,4-dimethyl-3,4-dihydroisoquinolin-2(1H)-yl]-3-[5-methyl-1-(tricyclo[3.3.1.1³,⁷]dec-1-ylmethyl)-1H-pyrazol-4-yl]pyridine-2-carboxylic acid; | |
| 6-[8-(1,3-benzothiazol-2-ylcarbamoyl)-3,4-dihydroisoquinolin-2(1H)-yl]-3-(1-{[3-(morpholin-4-yl)tricyclo[3.3.1.1³,⁷]dec-1-yl]methyl}-1H-pyrazol-4-yl)pyridine-2-carboxylic acid; | |
| 6-[8-(1,3-benzothiazol-2-ylcarbamoyl)-3,4-dihydroisoquinolin-2(1H)-yl]-3-(1-{[3-methoxytricyclo[3.3.1.1³,⁷]dec-1-yl]methyl}-5-methyl-1H-pyrazol-4-yl)pyridine-2-carboxylic acid; | |
| N-(1,3-benzothiazol-2-yl)-2-{6-[(methylsulfonyl)carbamoyl]-5-[5-methyl-1-(tricyclo[3.3.1.1³,⁷]dec-1-ylmethyl)-1H-pyrazol-4-yl]pyridin-2-yl}-1,2,3,4-tetrahydroisoquinoline-8-carboxamide; | |

| Name | Structure |
|---|---|
| N-(1,3-benzothiazol-2-yl)-2-{6-[(cyclopropylsulfonyl)carbamoyl]-5-[5-methyl-1-(tricyclo[3.3.1.1^{3,7}]dec-1-ylmethyl)-1H-pyrazol-4-yl]pyridin-2-yl}-1,2,3,4-tetrahydroisoquinoline-8-carboxamide; | 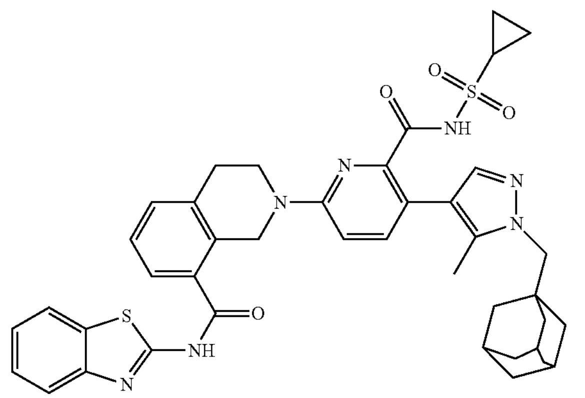 [SMILES: Cc1c(-c2ccc(N3CCc4cccc(C(=O)Nc5nc6ccccc6s5)c4C3)nc2C(=O)NS(=O)(=O)C2CC2)cnn1CC12CC3CC(CC(C3)C1)C2] |
| N-(1,3-benzothiazol-2-yl)-2-{5-[5-methyl-1-(tricyclo[3.3.1.1^{3,7}]dec-1-ylmethyl)-1H-pyrazol-4-yl]-6-(2H-tetrazol-5-yl)pyridin-2-yl}-1,2,3,4-tetrahydroisoquinoline-8-carboxamide; | 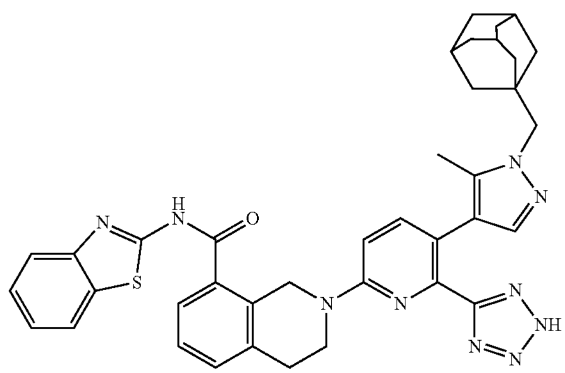 [SMILES: Cc1c(-c2ccc(N3CCc4cccc(C(=O)Nc5nc6ccccc6s5)c4C3)nc2-c2nn[nH]n2)cnn1CC12CC3CC(CC(C3)C1)C2] |
| 6-[8-(1,3-benzothiazol-2-ylcarbamoyl)-3,4-dihydroisoquinolin-2(1H)-yl]-3-{2-methyl-4-[tricyclo[3.3.1.1^{3,7}]dec-1-ylmethoxy]phenyl}pyridine-2-carboxylic acid; | 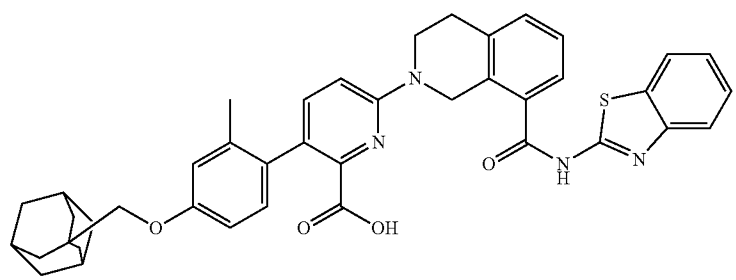 [SMILES: Cc1cc(OCC23CC4CC(CC(C4)C2)C3)ccc1-c1ccc(N2CCc3cccc(C(=O)Nc4nc5ccccc5s4)c3C2)nc1C(=O)O] |
| 6-[8-(1,3-benzothiazol-2-ylcarbamoyl)-3,4-dihydroisoquinolin-2(1H)-yl]-3-{2-methyl-3-[tricyclo[3.3.1.1^{3,7}]dec-1-ylmethoxy]phenyl}pyridine-2-carboxylic acid; | 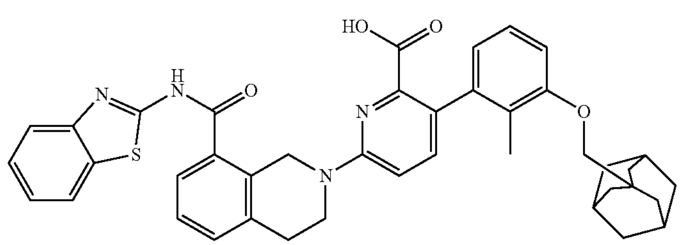 [SMILES: Cc1c(OCC23CC4CC(CC(C4)C2)C3)cccc1-c1ccc(N2CCc3cccc(C(=O)Nc4nc5ccccc5s4)c3C2)nc1C(=O)O] |
| 6-[8-(1,3-benzothiazol-2-ylcarbamoyl)-3,4-dihydroisoquinolin-2(1H)-yl]-3-{3-[tricyclo[3.3.1.1^{3,7}]dec-1-ylmethoxy]phenyl}pyridine-2-carboxylic acid; | 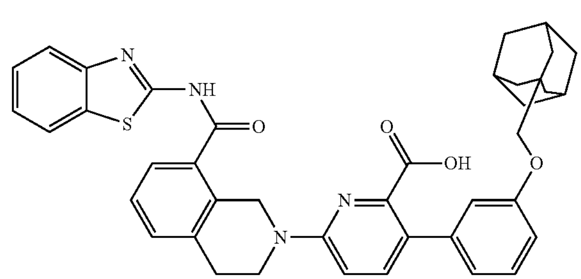 [SMILES: O=C(Nc1nc2ccccc2s1)c1cccc2c1CN(c1ccc(-c3cccc(OCC45CC6CC(CC(C6)C4)C5)c3)c(C(=O)O)n1)CC2] |

| Name | Structure |
|---|---|
| 6-[8-(1,3-benzothiazol-2-ylcarbamoyl)-3,4-dihydroisoquinolin-2(1H)-yl]-3-[5-cyano-2-methyl-1-(tricyclo[3.3.1.1³,⁷]dec-1-ylmethyl)-1H-pyrrol-3-yl]pyridine-2-carboxylic acid; | |
| 3-[5-methyl-1-(tricyclo[3.3.1.1³,⁷]dec-1-ylmethyl)-1H-pyrazol-4-yl]-6-[8-([1,3]thiazolo[5,4-b]pyridin-2-ylcarbamoyl)-3,4-dihydroisoquinolin-2(1H)-yl]pyridine-2-carboxylic acid; | |
| 6-[8-(1,3-benzothiazol-2-ylcarbamoyl)-3,4-dihydroisoquinolin-2(1H)-yl]-2'-(tricyclo[3.3.1.1³,⁷]dec-1-ylmethoxy)-3,4'-bipyridine-2-carboxylic acid; | |
| 6-[8-(1,3-benzothiazol-2-ylcarbamoyl)-3,4-dihydroisoquinolin-2(1H)-yl]-3-[1-({3-[2-(morpholin-4-yl)ethoxy]tricyclo[3.3.1.1³,⁷]dec-1-yl}methyl)-1H-pyrazol-4-yl]pyridine-2-carboxylic acid; | |
| 6-[8-(1,3-benzothiazol-2-ylcarbamoyl)-3,4-dihydroisoquinolin-2(1H)-yl]-3'-methyl-2'-(tricyclo[3.3.1.1³,⁷]dec-1-ylmethoxy)-3,4'-bipyridine-2-carboxylic acid; | |

| Name | Structure |
|---|---|
| 6-[8-(1,3-benzothiazol-2-ylcarbamoyl)-3,4-dihydroisoquinolin-2(1H)-yl]-3-{2-methyl-3-[tricyclo[3.3.1.1³,⁷]dec-1-yloxy]phenyl}pyridine-2-carboxylic acid; | |
| 6-[8-(1,3-benzothiazol-2-ylcarbamoyl)-3,4-dihydroisoquinolin-2(1H)-yl]-3-{5-cyano-1-[tricyclo[3.3.1.1³,⁷]dec-1-ylmethyl]-1H-pyrazol-4-yl}pyridine-2-carboxylic acid; | |
| 3-[5-methyl-1-(tricyclo[3.3.1.1³,⁷]dec-1-ylmethyl)-1H-pyrazol-4-yl]-6-[8-([1,3]thiazolo[4,5-b]pyridin-2-ylcarbamoyl)-3,4-dihydroisoquinolin-2(1H)-yl]pyridine-2-carboxylic acid; | |
| 3-[5-methyl-1-(tricyclo[3.3.1.1³,⁷]dec-1-ylmethyl)-1H-pyrazol-4-yl]-6-[8-([1,3]thiazolo[4,5-c]pyridin-2-ylcarbamoyl)-3,4-dihydroisoquinolin-2(1H)-yl]pyridine-2-carboxylic acid; | |
| 6-[8-(1,3-benzothiazol-2-ylcarbamoyl)-3,4-dihydroisoquinolin-2(1H)-yl]-3-(1-{[3,5-dimethyltricyclo[3.3.1.1³,⁷]dec-1-yl]methyl}-5-methyl-1H-pyrazol-4-yl)pyridine-2-carboxylic acid; | |

-continued

| Name | Structure |
|---|---|
| 6-[8-(1,3-benzothiazol-2-ylcarbamoyl)-3,4-dihydroisoquinolin-2(1H)-yl]-3-(1-{[3-(1,1-dioxidothiomorpholin-4-yl)tricyclo[3.3.1.1³,⁷]dec-1-yl]methyl}-1H-pyrazol-4-yl)pyridine-2-carboxylic acid; | |
| 6-[8-(1,3-benzothiazol-2-ylcarbamoyl)-3,4-dihydroisoquinolin-2(1H)-yl]-3-{5-cyano-2-methyl-[2-(tricyclo[3.3.1.1³,⁷]dec-1-yl)ethyl]-1H-pyrrol-3-yl}pyridine-2-carboxylic acid; | |
| N-(1,3-benzothiazol-2-yl)-2-{5-[5-cyano-2-methyl-1-(tricyclo[3.3.1.1³,⁷]dec-1-ylmethyl)-1H-pyrrol-3-yl]-6-[(methylsulfonyl)carbamoyl]pyridin-2-yl}-1,2,3,4-tetrahydroisoquinoline-8-carboxamide; | |
| N-(1,3-benzothiazol-2-yl)-2-{5-[5-cyano-2-methyl-1-(tricyclo[3.3.1.1³,⁷]dec-1-ylmethyl)-1H-pyrrol-3-yl]-6-[(cyclopropyl-sulfonyl)carbamoyl]pyridin-2-yl}-1,2,3,4-tetrahydroisoquinoline-8-carboxamide; | |

| Name | Structure |
|---|---|
| N-(1,3-benzothiazol-2-yl)-2-{5-(1-{[3-methoxytricyclo[3.3.1.1³,⁷]dec-1-yl]methyl}-5-methyl-1H-pyrazol-4-yl)-6-[(methylsulfonyl)carbamoyl]pyridin-2-yl}-1,2,3,4-tetrahydroisoquinoline-8-carboxamide; | |
| 6-[8-(1,3-benzothiazol-2-ylcarbamoyl)-3,4-dihydroisoquinolin-2(1H)-yl]-3-(1-{[3-methoxy-5,7-dimethyltricyclo[3.3.1.1³,⁷]dec-1-yl]methyl}-5-methyl-H-pyrazol-4-yl)pyridine-2-carboxylic acid; | |
| N-(1,3-benzothiazol-2-yl)-2-{5-(1-{[3-methoxytricyclo[3.3.1.1³,⁷]dec-1-yl]methyl}-5-methyl-1H-pyrazol-4-yl)-6-[(morpholin-4-ylsulfonyl)carbamoyl]pyridin-2-yl}-1,2,3,4-tetrahydroisoquinoline-8-carboxamide; | |
| N-(1,3-benzothiazol-2-yl)-2-[5-(1-{[3-methoxytricyclo[3.3.1.1³,⁷]dec-1-yl]methyl}-5-methyl-1H-pyrazol-4-yl)-6-{[(trifluoromethyl)sulfonyl]carbamoyl}pyridin-2-yl]-1,2,3,4-tetrahydroisoquinoline-8-carboxamide; | |

| Name | Structure |
|---|---|
| N-(1,3-benzothiazol-2-yl)-2-{6-[(cyclopropylsulfonyl)carbamoyl]-5-(1-{[3-methoxytricyclo[3.3.1.1³,⁷]dec-1-yl]methyl}-5-methyl-1H-pyrazol-4-yl)pyridin-2-yl}-1,2,3,4-tetrahydroisoquinoline-8-carboxamide; | |
| 6-[8-(1,3-benzothiazol-2-ylcarbamoyl)-3,4-dihydroisoquinolin-2(1H)-yl]-3-{5-chloro-1-[tricyclo[3.3.1.1³,⁷]dec-1-ylmethyl]-1H-pyrazol-4-yl}pyridine-2-carboxylic acid; | |
| 6-[8-(1,3-benzothiazol-2-ylcarbamoyl)-1-methyl-3,4-dihydroisoquinolin-2(1H)-yl]-3-[5-methyl-1-(tricyclo[3.3.1.1³,⁷]dec-1-ylmethyl)-1H-pyrazol-4-yl]pyridine-2-carboxylic acid; | |
| 6-[8-(1,3-benzothiazol-2-ylcarbamoyl)(1,1-²H₂)-3,4-dihydroisoquinolin-2(1H)-yl]-3-[5-methyl-1-(tricyclo[3.3.1.1³,⁷]dec-1-ylmethyl)-1H-pyrazol-4-yl]pyridine-2-carboxylic acid; | |
| 6-[8-(1,3-benzothiazol-2-ylcarbamoyl)-3,4-dihydroisoquinolin-2(1H)-yl]-3-(1-{[3-(2-methoxyethoxy)tricyclo[3.3.1.1³,⁷]dec-1-yl]methyl}-5-methyl-1H-pyrazol-4-yl)pyridine-2-carboxylic acid; | |

| Name | Structure |
|---|---|
| 6-[8-(1,3-benzothiazol-2-ylcarbamoyl)-3,4-dihydroisoquinolin-2(1H)-yl]-3-(1-{[1-(2-methoxyethyl)cyclooctyl]methyl}-5-methyl-1H-pyrazol-4-yl)pyridine-2-carboxylic acid; | 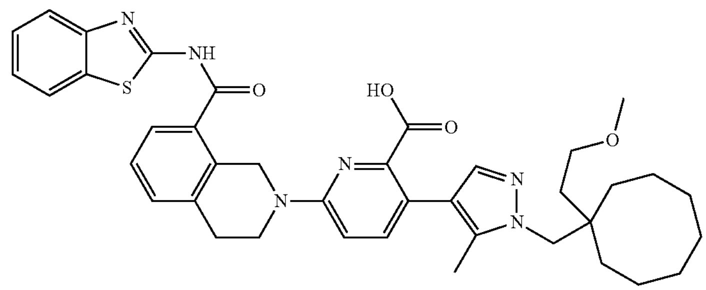 [SMILES: COCCC1(Cn2ncc(-c3ccc(N4CCc5cccc(C(=O)Nc6nc7ccccc7s6)c5C4)nc3C(=O)O)c2C)CCCCCCC1] |
| 6-[8-(1,3-benzothiazol-2-ylcarbamoyl)-3,4-dihydroisoquinolin-2(1H)-yl]-3-{2-cyano-3-[tricyclo[3.3.1.1$^{3,7}$]dec-1-ylamino]phenyl}pyridine-2-carboxylic acid; | 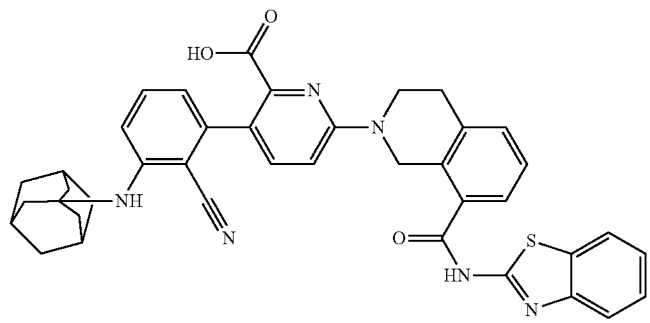 [SMILES: N#Cc1c(NC23CC4CC(CC(C4)C2)C3)cccc1-c1ccc(N2CCc3cccc(C(=O)Nc4nc5ccccc5s4)c3C2)nc1C(=O)O] |
| 6-[8-(1,3-benzothiazol-2-ylcarbamoyl)-3,4-dihydroisoquinolin-2(1H)-yl]-3-{2-cyano-3-[tricyclo[3.3.1.1$^{3,7}$]dec-1-ylsulfanyl]phenyl}pyridine-2-carboxylic acid; | 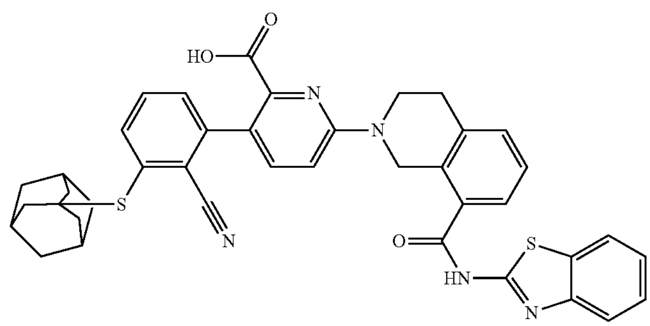 [SMILES: N#Cc1c(SC23CC4CC(CC(C4)C2)C3)cccc1-c1ccc(N2CCc3cccc(C(=O)Nc4nc5ccccc5s4)c3C2)nc1C(=O)O] |
| 6-[8-(imidazo[1,2-a]pyridin-2-ylcarbamoyl)-3,4-dihydroisoquinolin-2(1H)-yl]-3-[5-methyl-1-(tricyclo[3.3.1.1$^{3,7}$]dec-1-ylmethyl)-1H-pyrazol-4-yl]pyridine-2-carboxylic acid; | 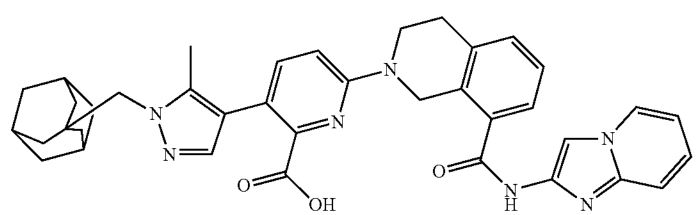 [SMILES: Cc1c(-c2ccc(N3CCc4cccc(C(=O)Nc5cn6ccccc6n5)c4C3)nc2C(=O)O)cnn1CC12CC3CC(CC(C3)C1)C2] |
| 6-[8-(1,3-benzothiazol-2-ylcarbamoyl)-3,4-dihydroisoquinolin-2(1H)-yl]-3-(2-methyl-3-{[tricyclo[3.3.1.1$^{3,7}$]dec-1-ylcarbonyl]amino}phenyl)pyridine-2-carboxylic acid; | 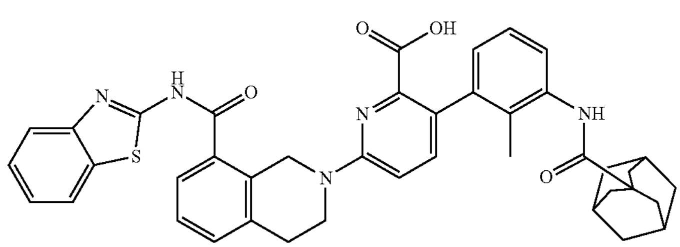 [SMILES: Cc1c(NC(=O)C23CC4CC(CC(C4)C2)C3)cccc1-c1ccc(N2CCc3cccc(C(=O)Nc4nc5ccccc5s4)c3C2)nc1C(=O)O] |

| Name | Structure |
|---|---|
| 6-[8-(1,3-benzothiazol-2-ylcarbamoyl)-3,4-dihydroisoquinolin-2(1H)-yl]-3-{2-methyl-3-[tricyclo[3.3.1.1³,⁷]dec-1-ylsulfamoyl]phenyl}pyridine-2-carboxylic acid; | |
| 6-[8-(1,3-benzothiazol-2-ylcarbamoyl)-3,4-dihydroisoquinolin-2(1H)-yl]-3-(2-methyl-3-{methyl[tricyclo[3.3.1.1³,⁷]dec-1-ylcarbonyl]amino}phenyl)pyridine-2-carboxylic acid; | |
| 6-[8-(1,3-benzothiazol-2-ylcarbamoyl)-3,4-dihydroisoquinolin-2(1H)-yl]-3-(5-methyl-1-{[3-(tetrahydro-2H-pyran-4-ylmethoxy)tricyclo[3.3.1.1³,⁷]dec-1-yl]methyl}-1H-pyrazol-4-yl)pyridine-2-carboxylic acid; | |
| 6-[8-(1,3-benzothiazol-2-ylcarbamoyl)-3,4-dihydroisoquinolin-2(1H)-yl]-3-{2-methyl-3-[tricyclo[3.3.1.1³,⁷]dec-1-ylcarbamoyl]phenyl}pyridine-2-carboxylic acid; | |
| 6-[8-(1,3-benzothiazol-2-ylcarbamoyl)-3,4-dihydroisoquinolin-2(1H)-yl]-3-(2-methyl-3-{methyl[tricyclo[3.3.1.1³,⁷]dec-1-ylmethyl]amino}phenyl)pyridine-2-carboxylic acid; | |

| Name | Structure |
|---|---|
| 6-[8-(1,3-benzothiazol-2-ylcarbamoyl)-3,4-dihydroisoquinolin-2(1H)-yl]-3-(1-{[2-(2-methoxyethyl)tricyclo[3.3.1.1³,⁷]dec-2-yl]methyl}-1H-pyrazol-4-yl)pyridine-2-carboxylic acid; | 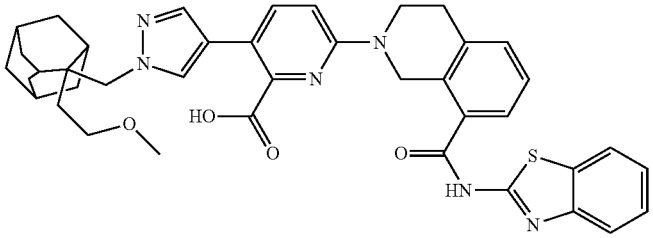 [SMILES: COCCC1(Cn2cc(-c3ccc(N4CCc5cccc(C(=O)Nc6nc7ccccc7s6)c5C4)nc3C(=O)O)cn2)C2CC3CC(C2)CC1C3] |
| 6-[8-(1,3-benzothiazol-2-ylcarbamoyl)-3,4-dihydroisoquinolin-2(1H)-yl]-3-[5-methyl-1-(tricyclo[3.3.1.1³,⁷]dec-1-ylmethyl)-1H-1,2,3-triazol-4-yl]pyridine-2-carboxylic acid; | 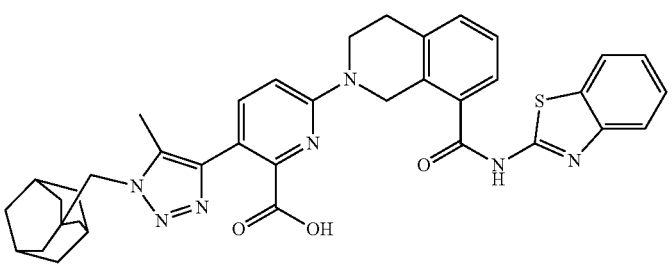 [SMILES: Cc1c(-c2ccc(N3CCc4cccc(C(=O)Nc5nc6ccccc6s5)c4C3)nc2C(=O)O)nnn1CC12CC3CC(CC(C3)C1)C2] |
| 6-[8-(1,3-benzothiazol-2-ylcarbamoyl)-3,4-dihydroisoquinolin-2(1H)-yl]-3-(5-cyano-1-{[3-methoxytricyclo[3.3.1.1³,⁷]dec-1-yl]methyl}-2-methyl-1H-pyrrol-3-yl)pyridine-2-carboxylic acid; | 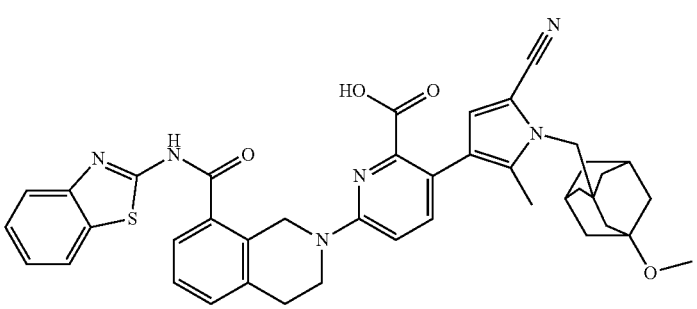 [SMILES: COC12CC3CC(CC(Cn4c(C#N)cc(-c5ccc(N6CCc7cccc(C(=O)Nc8nc9ccccc9s8)c7C6)nc5C(=O)O)c4C)(C3)C1)C2] |
| 6-[8-(1,3-benzothiazol-2-ylcarbamoyl)-3,4-dihydroisoquinolin-2(1H)-yl]-3-[5-methyl-1-(2-oxatricyclo[3.3.1.1³,⁷]dec-1-ylmethyl)-1H-pyrazol-4-yl]pyridine-2-carboxylic acid; | 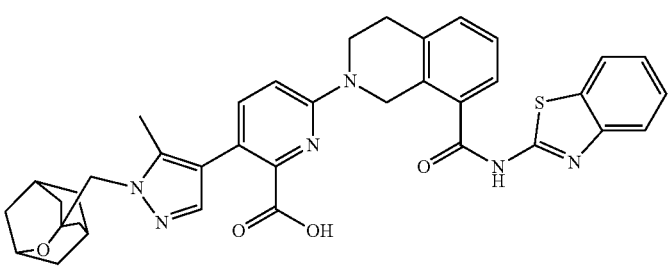 [SMILES: Cc1c(-c2ccc(N3CCc4cccc(C(=O)Nc5nc6ccccc6s5)c4C3)nc2C(=O)O)cnn1CC12CC3CC(CC(C3)O1)C2] |
| 6-[8-(1,3-benzothiazol-2-ylcarbamoyl)-3,4-dihydroisoquinolin-2(1H)-yl]-3-[2-cyano-3-(tricyclo[3.3.1.1³,⁷]dec-1-ylsulfonyl)phenyl]pyridine-2-carboxylic acid; | 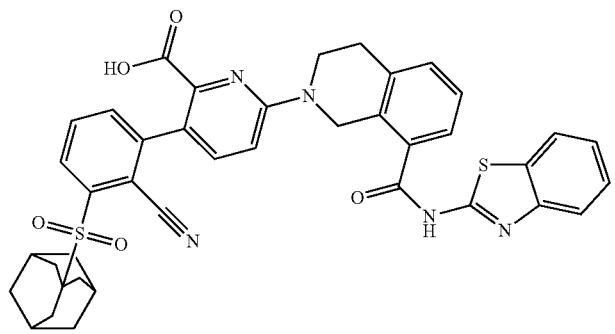 [SMILES: N#Cc1c(-c2ccc(N3CCc4cccc(C(=O)Nc5nc6ccccc6s5)c4C3)nc2C(=O)O)cccc1S(=O)(=O)C12CC3CC(CC(C3)C1)C2] |

| Name | Structure |
|---|---|
| 6-[8-(1,3-benzothiazol-2-ylcarbamoyl)-3,4-dihydroisoquinolin-2(1H)-yl]-2'-[cyclooctyl(methyl)amino]-3'-methyl-3,4'-bipyridine-2-carboxylic acid; | 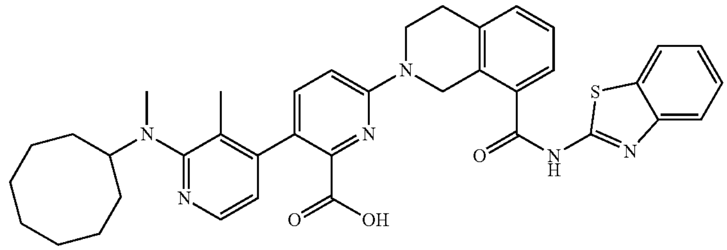 [SMILES: Cc1c(-c2ccc(N3CCc4cccc(C(=O)Nc5nc6ccccc6s5)c4C3)nc2C(=O)O)ccnc1N(C)C1CCCCCCC1] |
| 6-[8-(1,3-benzothiazol-2-ylcarbamoyl)-3,4-dihydroisoquinolin-2(1H)-yl]-3-[5-methyl-1-(tricyclo[3.3.1.1$^{3,7}$]dec-2-ylmethyl)-1H-pyrazol-4-yl]pyridine-2-carboxylic acid; | 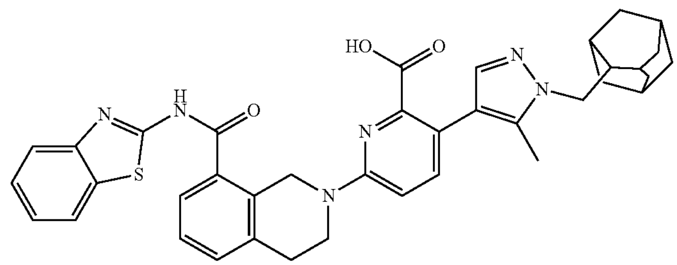 [SMILES: Cc1c(-c2ccc(N3CCc4cccc(C(=O)Nc5nc6ccccc6s5)c4C3)nc2C(=O)O)cnn1CC1C2CC3CC(C2)CC1C3] |
| 6-[8-(1,3-benzothiazol-2-ylcarbamoyl)-3,4-dihydroisoquinolin-2(1H)-yl]-3-[1-({3-[2-(2-methoxyethoxy)ethoxy]tricyclo[3.3.1.1$^{3,7}$]dec-1-yl}methyl)-5-methyl-1H-pyrazol-4-yl]pyridine-2-carboxylic acid; | |
| 6-[8-(1,3-benzothiazol-2-ylcarbamoyl)-3,4-dihydroisoquinolin-2(1H)-yl]-3-(2-methyl-3-{methyl[(tricyclo[3.3.1.1$^{3,7}$]dec-2-yl]carbamoyl}phenyl)pyridine-2-carboxylic acid; | |
| 6-[8-(1,3-benzothiazol-2-ylcarbamoyl)-3,4-dihydroisoquinolin-2(1H)-yl]-3-[5-methyl-1-({1-[2-(methylsulfonyl)ethoxy]cyclooctyl}methyl)-1H-pyrazol-4-yl]pyridine-2-carboxylic acid; | 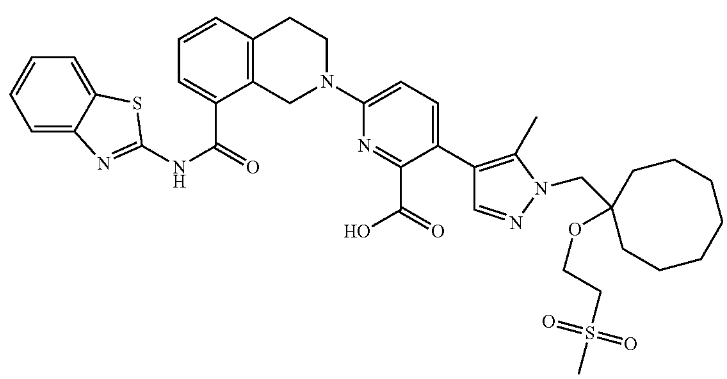 [SMILES: Cc1c(-c2ccc(N3CCc4cccc(C(=O)Nc5nc6ccccc6s5)c4C3)nc2C(=O)O)cnn1CC1(OCCS(C)(=O)=O)CCCCCCC1] |
| 6-[8-(1,3-benzothiazol-2-ylcarbamoyl)-3,4-dihydroisoquinolin-2(1H)-yl]-3-[5-methyl-1-(2-oxatricyclo[3.3.1.1$^{3,7}$]dec-1-ylmethyl)-1H-1,2,3-triazol-4-yl]pyridine-2-carboxylic acid; | 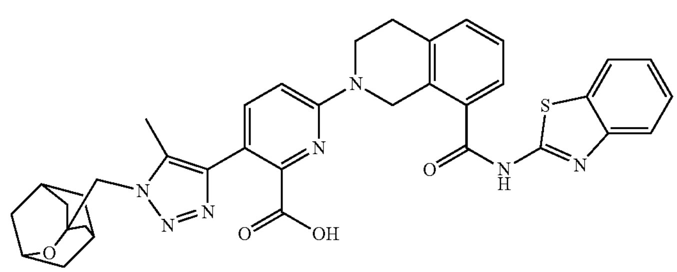 [SMILES: Cc1c(-c2ccc(N3CCc4cccc(C(=O)Nc5nc6ccccc6s5)c4C3)nc2C(=O)O)nnn1CC12CC3CC(CC(C3)O1)C2] |

-continued

| Name | Structure |
|---|---|
| 3-[5-methyl-1-(2-oxatricyclo[3.3.1.1³,⁷]dec-1-ylmethyl)-1H-pyrazol-4-yl]-6-[8-([1,3]thiazolo[5,4-b]pyridin-2-ylcarbamoyl)-3,4-dihydroisoquinolin-2(1H)-yl]pyridine-2-carboxylic acid; | |
| 6-[8-(1,3-benzothiazol-2-ylcarbamoyl)-3,4-dihydroisoquinolin-2(1H)-yl]-3-{2-methyl-3-[methyl(2-oxatricyclo[3.3.1.1³,⁷]dec-1-ylcarbonyl)amino]phenyl}pyridine-2-carboxylic acid; | |
| 6-[8-(1,3-benzothiazol-2-ylcarbamoyl)-3,4-dihydroisoquinolin-2(1H)-yl]-3-(2-methyl-3-{methyl[tricyclo[3.3.1.1³,⁷]dec-2-yl]sulfamoyl}phenyl)pyridine-2-carboxylic acid; | |
| 6-[8-(1,3-benzothiazol-2-ylcarbamoyl)-3,4-dihydroisoquinolin-2(1H)-yl]-3'-methyl-2'-(tricyclo[3.3.1.1³,⁷]dec-1-ylsulfonyl)-3,4'-bipyridine-2-carboxylic acid; | |
| 6-[8-(1,3-benzothiazol-2-ylcarbamoyl)-3,4-dihydroisoquinolin-2(1H)-yl]-3-[5-cyano-2-methyl-1-(2-oxatricyclo[3.3.1.1³,⁷]dec-1-ylmethyl)-1H-pyrrol-3-yl]pyridine-2-carboxylic acid; | |
| 6-[8-(1,3-benzothiazol-2-ylcarbamoyl)-3,4-dihydroisoquinolin-2(1H)-yl]-3-{5-cyano-2-methyl-1-[(3-methyl-2-oxatricyclo[3.3.1.1³,⁷]dec-1-yl)methyl]-1H-pyrrol-3-yl}pyridine-2-carboxylic acid; | |

| Name | Structure |
|---|---|
| 6-[8-(imidazo[1,2-a]pyrazin-2-ylcarbamoyl)-3,4-dihydroisoquinolin-2(1H)-yl]-3-[5-methyl-1-(tricyclo[3.3.1.1³,⁷]dec-1-ylmethyl)-1H-pyrazol-4-yl]pyridine-2-carboxylic acid; | |
| 6-[8-(1,3-benzothiazol-2-ylcarbamoyl)-3,4-dihydroisoquinolin-2(1H)-yl]-3'-methyl-2'-(tricyclo[3.3.1.1³,⁷]dec-1-ylsulfanyl)-3,4'-bipyridine-2-carboxylic acid; | |
| 2-{6-[(methylsulfonyl)carbamoyl]-5-[5-methyl-1-(tricyclo[3.3.1.1³,⁷]dec-1-ylmethyl)-1H-pyrazol-4-yl]pyridin-2-yl}-N-([1,3]thiazolo[5,4-b]pyridin-2-yl)-1,2,3,4-tetrahydroisoquinoline-8-carboxamide; | |
| 6-[8-(1,3-benzothiazol-2-ylcarbamoyl)-3,4-dihydroisoquinolin-2(1H)-yl]-3'-methyl-2'-(tricyclo[3.3.1.1³,⁷]dec-1-ylamino)-3,4'-bipyridine-2-carboxylic acid; | |
| 6-[8-(imidazo[1,2-b]pyridazin-2-ylcarbamoyl)-3,4-dihydroisoquinolin-2(1H)-yl]-3-[5-methyl-1-(tricyclo[3.3.1.1³,⁷]dec-1-ylmethyl)-1H-pyrazol-4-yl]pyridine-2-carboxylic acid; | |
| 3-[5-methyl-1-(tricyclo[3.3.1.1³,⁷]dec-1-ylmethyl)-1H-pyrazol-4-yl]-6-[8-([1,3]thiazolo[5,4-c]pyridin-2-ylcarbamoyl)-3,4-dihydroisoquinolin-2(1H)-yl]pyridine-2-carboxylic acid; | |

| Name | Structure |
|---|---|
| 6-[8-(1,3-benzothiazol-2-ylcarbamoyl)-3,4-dihydroisoquinolin-2(1H)-yl]-3-{1-[(5-methoxyspiro[2.5]oct-5-yl)methyl]-5-methyl-1H-pyrazol-4-yl}pyridine-2-carboxylic acid; | 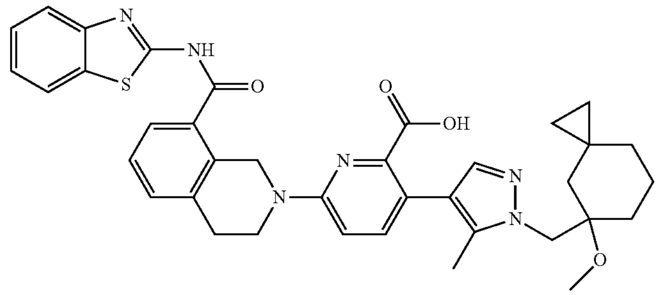 [SMILES: COC1(Cn2ncc(-c3ccc(N4CCc5cccc(C(=O)Nc6nc7ccccc7s6)c5C4)nc3C(=O)O)c2C)CCCC2(CC2)C1] |
| 6-[8-(1,3-benzothiazol-2-ylcarbamoyl)-3,4-dihydroisoquinolin-2(1H)-yl]-3-(1-{[3-{2-[2-(2-methoxyethoxy)ethoxy]ethoxy}tricyclo[3.3.1.1$^{3,7}$]dec-1-yl]methyl}-5-methyl-1H-pyrazol-4-yl)pyridine-2-carboxylic acid; | 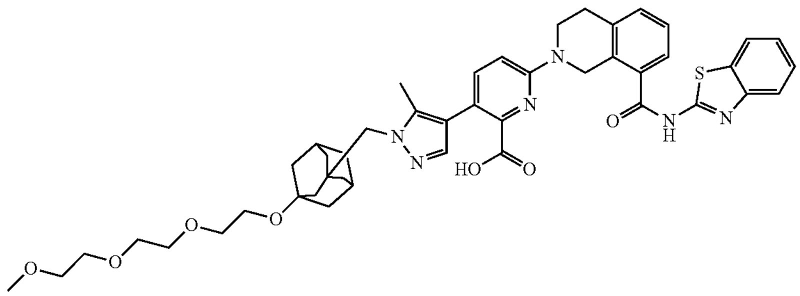 [SMILES: COCCOCCOCCOC12CC3CC(CC(Cn4ncc(-c5ccc(N6CCc7cccc(C(=O)Nc8nc9ccccc9s8)c7C6)nc5C(=O)O)c4C)(C3)C1)C2] |
| 6-[8-(1,3-benzothiazol-2-ylcarbamoyl)-3,4-dihydroisoquinolin-2(1H)-yl]-3-(5-methyl-1-{[3-(methylsulfonyl)tricyclo[3.3.1.1$^{3,7}$]dec-1-yl]methyl}-1H-pyrazol-4-yl)pyridine-2-carboxylic acid; | 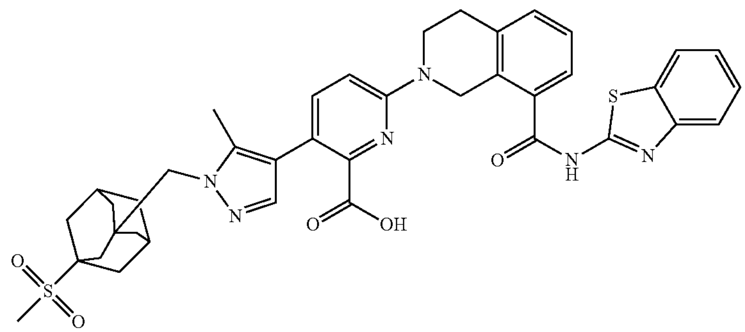 [SMILES: Cc1c(-c2ccc(N3CCc4cccc(C(=O)Nc5nc6ccccc6s5)c4C3)nc2C(=O)O)cnn1CC12CC3CC(C1)CC(S(C)(=O)=O)(C3)C2] |
| 6-[8-(1,3-benzothiazol-2-ylcarbamoyl)-3,4-dihydroisoquinolin-2(1H)-yl]-3-[1-({3,5-dimethyl-7-[2-(methylamino)ethoxy]tricyclo[3.3.1.1$^{3,7}$]dec-1-yl}methyl)-5-methyl-1H-pyrazol-4-yl]pyridine-2-carboxylic acid; | 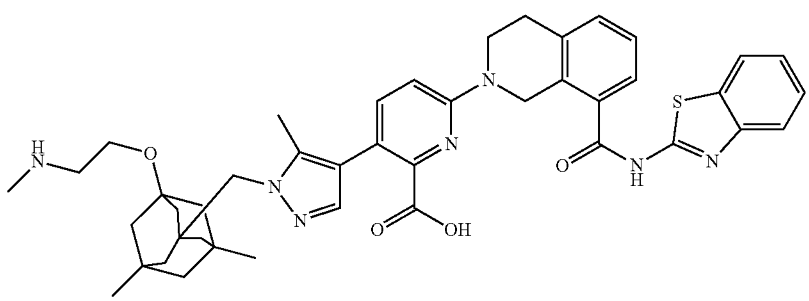 [SMILES: CNCCOC12CC3(C)CC(C)(CC(Cn4ncc(-c5ccc(N6CCc7cccc(C(=O)Nc8nc9ccccc9s8)c7C6)nc5C(=O)O)c4C)(C3)C1)C2] |
| 6-[8-(1,3-benzothiazol-2-ylcarbamoyl)-3,4-dihydroisoquinolin-2(1H)-yl]-3-(5-methyl-1-{[3-(2-{2-[2-(methylamino)ethoxy]ethoxy}ethoxy)tricyclo[3.3.1.1$^{3,7}$]dec-1-yl]methyl}-1H-pyrazol-4-yl)pyridine-2-carboxylic acid; | 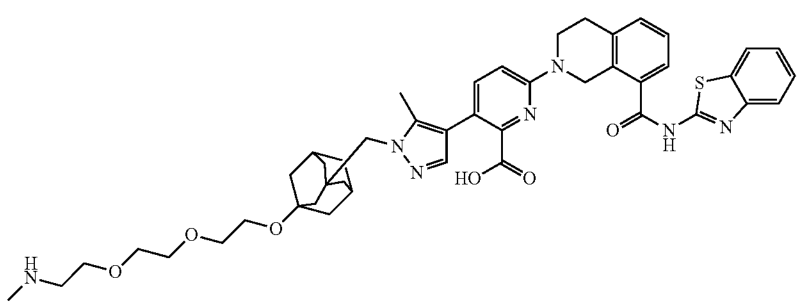 [SMILES: CNCCOCCOCCOC12CC3CC(CC(Cn4ncc(-c5ccc(N6CCc7cccc(C(=O)Nc8nc9ccccc9s8)c7C6)nc5C(=O)O)c4C)(C3)C1)C2] |

| Name | Structure |
|---|---|
| 6-[8-(1,3-benzothiazol-2-ylcarbamoyl)-3,4-dihydroisoquinolin-2(1H)-yl]-3-[1-({8-[(benzyloxy)carbonyl]-8-azabicyclo[3.2.1]oct-3-yl}methyl)-1H-pyrazol-4-yl]pyridine-2-carboxylic acid; | 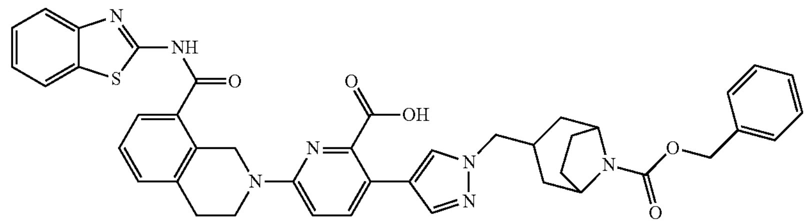 [SMILES: O=C(Nc1nc2ccccc2s1)c1cccc2c1CN(c1ccc(-c3cnn(CC4CC5CCC(C4)N5C(=O)OCc4ccccc4)c3)c(C(=O)O)n1)CC2] |
| 6-[8-(1,3-benzothiazol-2-ylcarbamoyl)-3,4-dihydroisoquinolin-2(1H)-yl]-6'-oxo-1'-(tricyclo[3.3.1.1$^{3,7}$]dec-1-ylmethyl)-1',6'-dihydro-3,3'-bipyridine-2-carboxylic acid; | 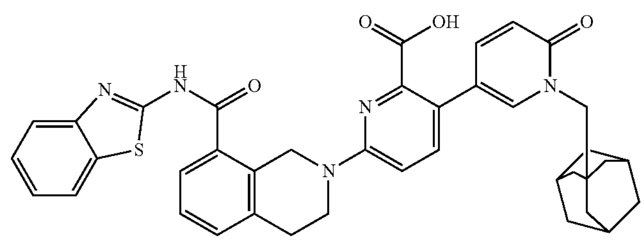 [SMILES: O=C(Nc1nc2ccccc2s1)c1cccc2c1CN(c1ccc(-c3ccc(=O)n(CC45CC6CC(CC(C6)C4)C5)c3)c(C(=O)O)n1)CC2] |
| 6-[8-(1,3-benzothiazol-2-ylcarbamoyl)-3,4-dihydroisoquinolin-2(1H)-yl]-3-(1-{[3,5-dimethyl-7-(2-{2-[2-(methylamino)ethoxy]ethoxy}ethoxy)tricyclo[3.3.1.1$^{3,7}$]dec-1-yl]methyl}-5-methyl-1H-pyrazol-4-yl)pyridine-2-carboxylic acid | 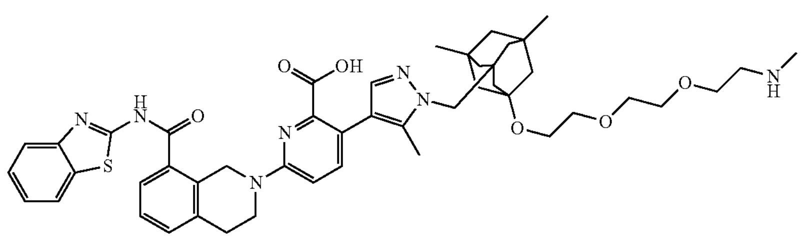 [SMILES: CNCCOCCOCCOC12CC3(C)CC(C)(CC(Cn4ncc(-c5ccc(N6CCc7cccc(C(=O)Nc8nc9ccccc9s8)c7C6)nc5C(=O)O)c4C)(C3)C1)C2] |

45

In some embodiments, the compound is selected from the group consisting of:

| Name | Structure |
|---|---|
| N-({5-chloro-6-[(4-fluorotetrahydro-2H-pyran-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-[(6-fluoro-1H-indazol-4-yl)oxy]benzamide | 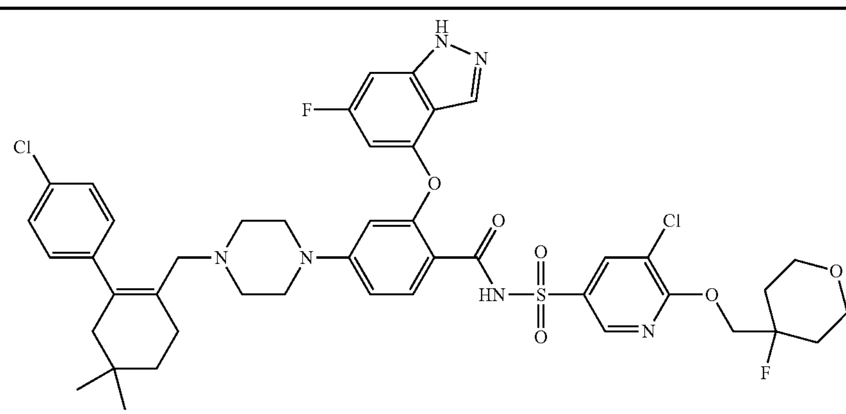 |

-continued

| Name | Structure |
|---|---|
| 4-(4-{[2-(4-chlorophenyl)-4,4-dimethylcyclohex-1-en-1-yl]methyl}piperazin-1-yl)-N-{4-({[(2S)-4-cyclopropylmorpholin-2-yl]methyl}amino)-3-nitrophenyl]sulfonyl}-2-(1H-pyrrolo[2,3-b]pyridin-5-yloxy)benzamide | |
| N-({5-chloro-6-[(4-fluorotetrahydro-2H-pyran-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide | 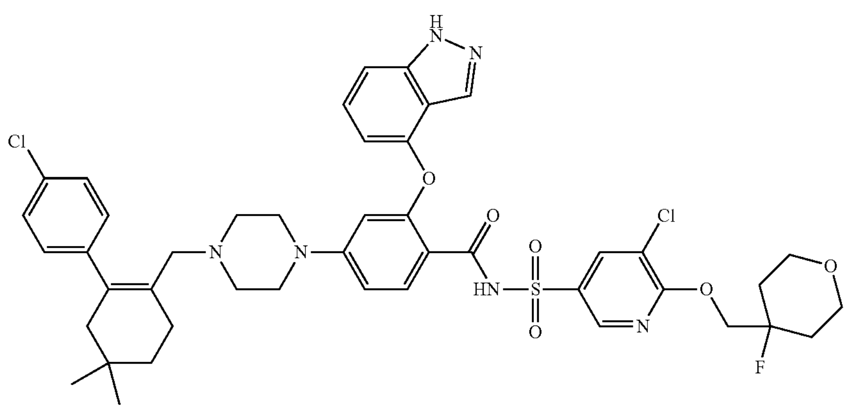 [SMILES: CC1(C)CCC(CN2CCN(c3ccc(C(=O)NS(=O)(=O)c4cnc(OCC5(F)CCOCC5)c(Cl)c4)c(Oc4cccc5[nH]ncc45)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-2-[(6-fluoro-1H-indol-5-yl)oxy]-N-({4-[(4-fluorotetrahydro-2H-pyran-4-yl)methoxy]-3-nitrophenyl}sulfonyl)benzamide | 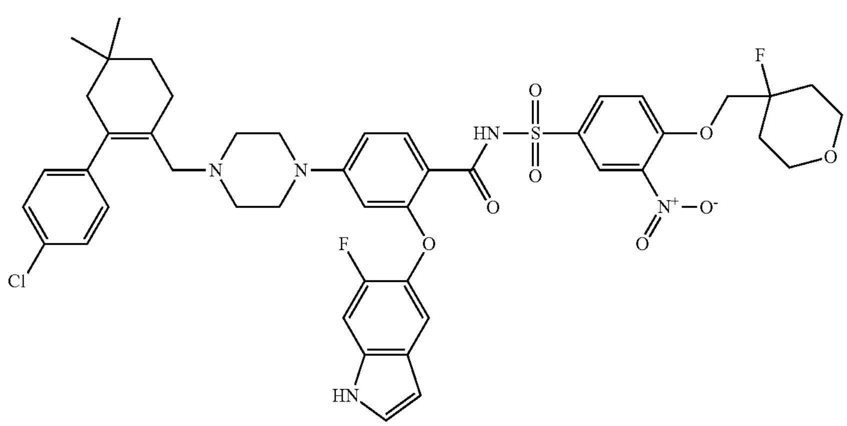 [SMILES: CC1(C)CCC(CN2CCN(c3ccc(C(=O)NS(=O)(=O)c4ccc(OCC5(F)CCOCC5)c([N+](=O)[O-])c4)c(Oc4cc5cc[nH]c5cc4F)c3)CC2)=C(c2ccc(Cl)cc2)C1] |

| Name | Structure |
|---|---|
| 4-(4-{[2-(4-chlorophenyl)-4,4-dimethylcyclohex-1-en-1-yl]methyl}piperazin-1-yl)-N-[(4-{[(4,4-difluorocyclohexyl)methyl]amino}-3-nitrophenyl)sulfonyl]-2-(1H-pyrrolo[2,3-b]pyridin-5-yloxy)benzamide | 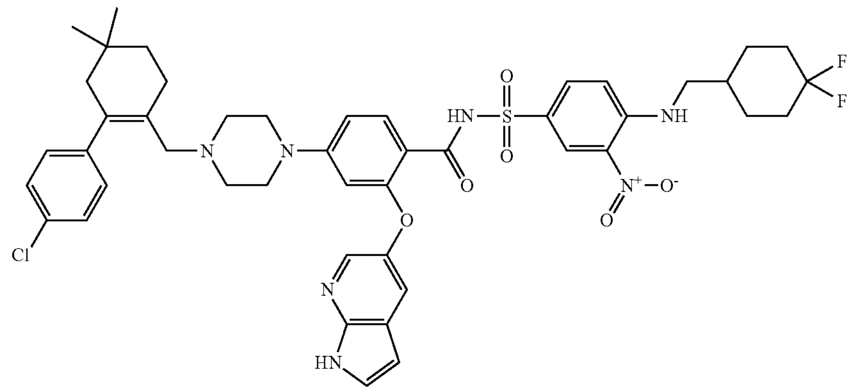 [SMILES: CC1(C)CCC(CN2CCN(c3ccc(C(=O)NS(=O)(=O)c4ccc(NCC5CCC(F)(F)CC5)c([N+](=O)[O-])c4)c(Oc4cnc5[nH]ccc5c4)c3)CC2)=C(c2ccc(Cl)cc2)C1] |
| 2-(1H-benzimidazol-4-yloxy)-4-(4-{[2-(4-chlorophenyl)-4,4-dimethylcyclohex-1-en-1-yl]methyl}piperazin-1-yl)-N-({5-fluoro-6-[(4-fluorotetrahydro-2H-pyran-4-yl)methoxy]pyridin-3-yl}sulfonyl)benzamide | 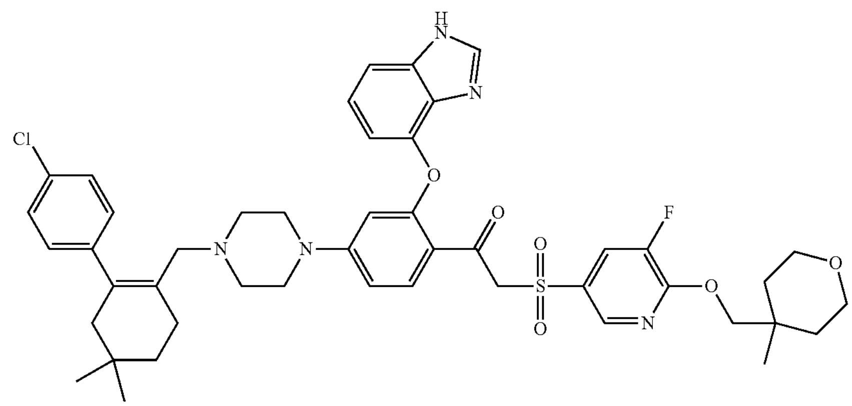 [SMILES: CC1(C)CCC(CN2CCN(c3ccc(C(=O)CS(=O)(=O)c4cnc(OCC5(C)CCOCC5)c(F)c4)c(Oc4cccc5[nH]cnc45)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide | 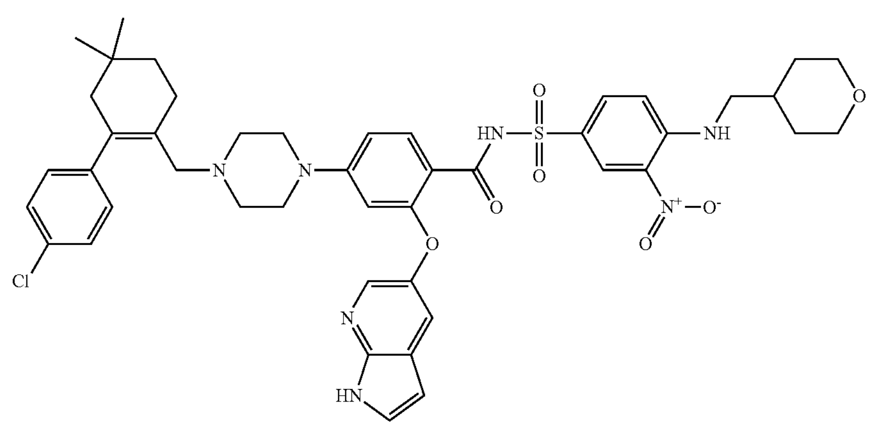 [SMILES: CC1(C)CCC(CN2CCN(c3ccc(C(=O)NS(=O)(=O)c4ccc(NCC5CCOCC5)c([N+](=O)[O-])c4)c(Oc4cnc5[nH]ccc5c4)c3)CC2)=C(c2ccc(Cl)cc2)C1] |

| Name | Structure |
|---|---|
| N-({3-chloro-4-[(4-fluorotetrahydro-2H-pyran-4-yl)methoxy]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | 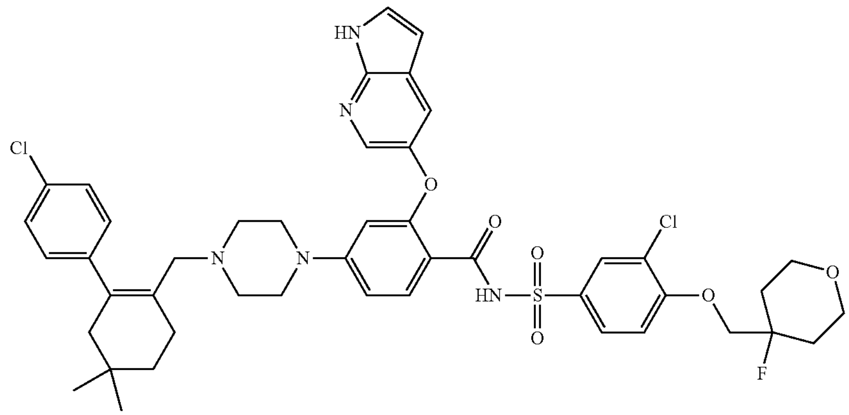 [SMILES: CC1(C)CCC(CN2CCN(c3ccc(C(=O)NS(=O)(=O)c4ccc(OCC5(F)CCOCC5)c(Cl)c4)c(Oc4cnc5[nH]ccc5c4)c3)CC2)=C(c2ccc(Cl)cc2)C1] |
| 2-(1H-benzimidazol-4-yloxy)-4-(4-{[2-(4-chlorophenyl)-4,4-dimethylcyclohex-1-en-1-yl]methyl}piperazin-1-yl)-N-[(4-{[(4-cyanocyclohexyl)methyl]amino}-3-nitrophenyl)sulfonyl]benzamide | 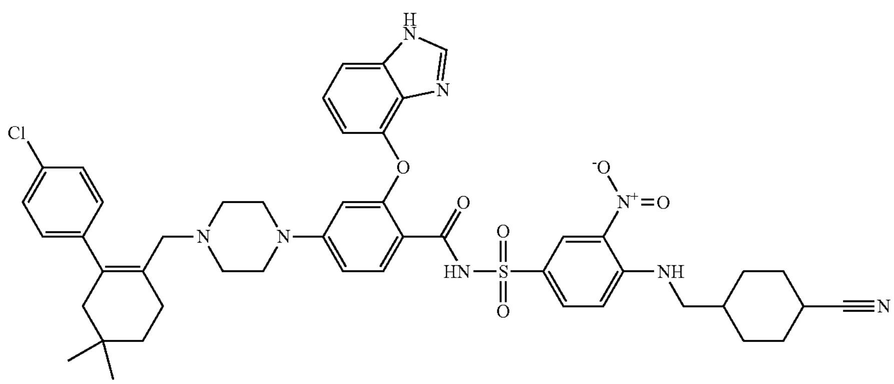 |
| N-({5-chloro-6-[(cis-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide | 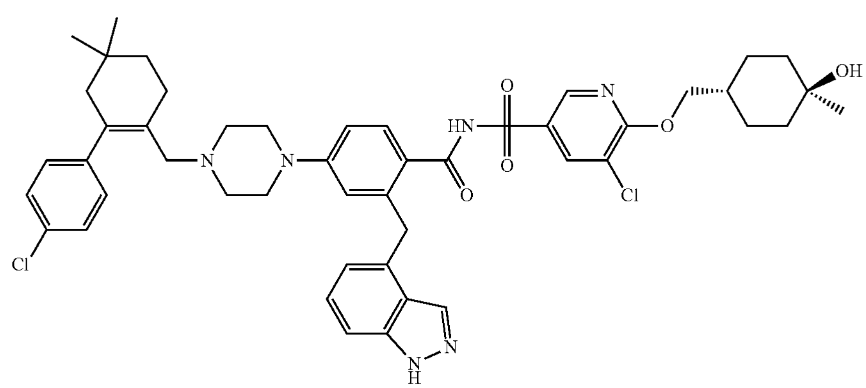 |
| N-[(3-chloro-4-{[4-fluoro-1-(oxetan-3-yl)piperidin-4-yl]methoxy}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | 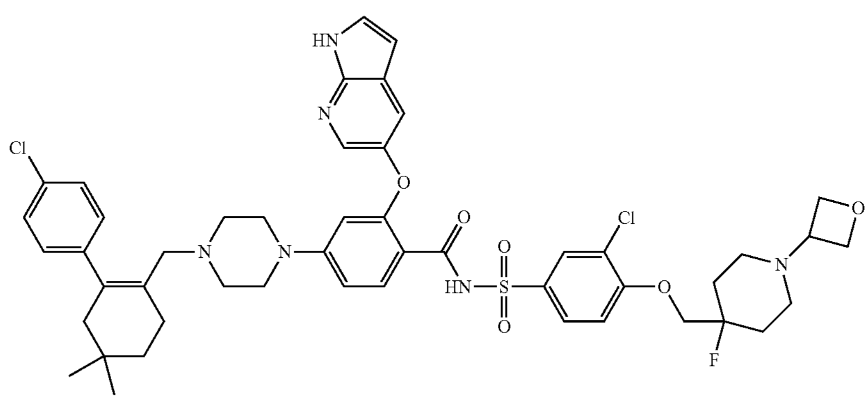 [SMILES: CC1(C)CCC(CN2CCN(c3ccc(C(=O)NS(=O)(=O)c4ccc(OCC5(F)CCN(C6COC6)CC5)c(Cl)c4)c(Oc4cnc5[nH]ccc5c4)c3)CC2)=C(c2ccc(Cl)cc2)C1] |

-continued

| Name | Structure |
|---|---|
| 4-(4-{[2-(4-chlorophenyl)-4,4-dimethylcyclohex-1-en-1-yl]methyl}piperazin-1-yl)-N-({5-cyano-6-R-[(4-fluorotetrahydro-2H-pyran-4-yl)methoxy]pyridin-3-yl}sulfonyl)-2-(1H-indol-4-yloxy)benzamide | 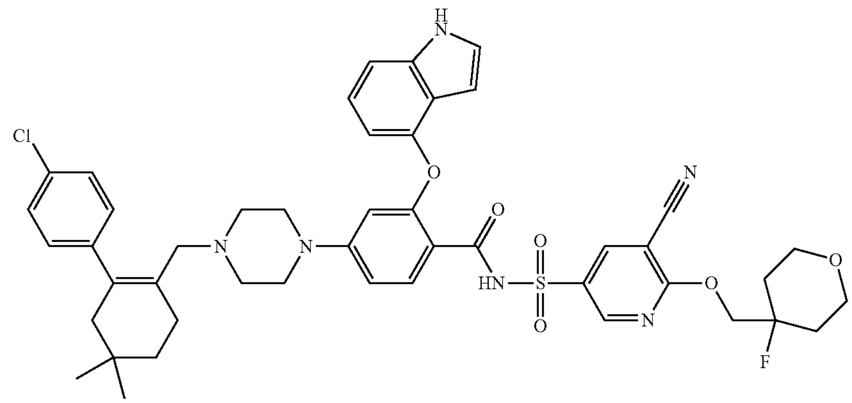 [SMILES: CC1(C)CCC(CN2CCN(c3ccc(C(=O)NS(=O)(=O)c4cnc(OCC5(F)CCOCC5)c(C#N)c4)c(Oc4cccc5[nH]ccc45)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-[(4-{[(4-fluorotetrahydro-2H-pyran-4-yl)methyl]amino}-3-nitrophenyl)sulfonyl]-2-(1H-pyrrolo[2,3-b]pyridin-5-yloxy)benzamide | 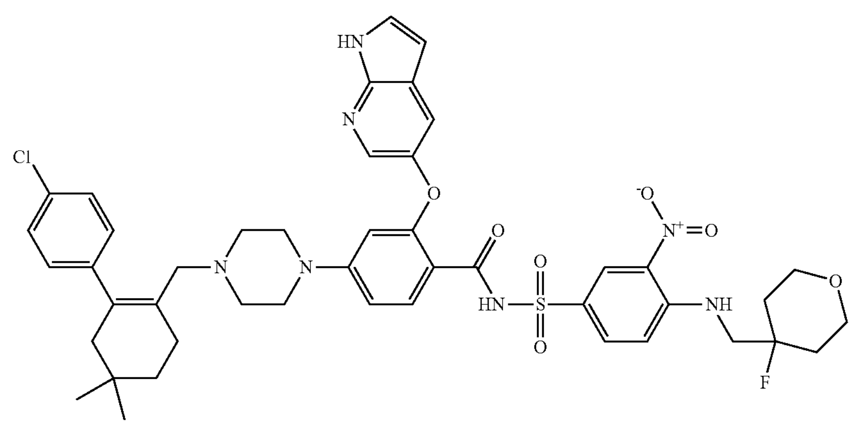 |
| N-({3-chloro-4-[(4-fluorotetrahydro-2H-pyran-4-yl)methoxy]phenyl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide | 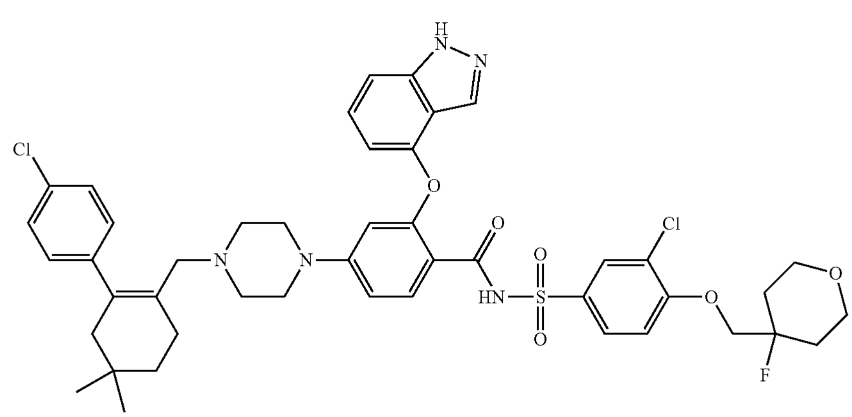 [SMILES: CC1(C)CCC(CN2CCN(c3ccc(C(=O)NS(=O)(=O)c4cnc(OCC5(F)CCOCC5)c(F)c4)c(Oc4cccc5[nH]ncc45)c3)CC2)=C(c2ccc(Cl)cc2)C1] |

| Name | Structure |
|---|---|
| 4-(4-{[2-(4-chlorophenyl)-4,4-dimethylcyclohex-1-en-1-yl]methyl}piperazin-1-yl)-N-({5-fluoro-6-[(4-fluorotetrahydro-2H-pyran-4-yl)methoxy]pyridin-3-yl}sulfonyl)-2-(1H-indazol-4-yloxy)benzamide | |
| 4-(4-{[2-(4-chlorophenyl)-4,4-dimethylcyclohex-1-en-1-yl]methyl}piperazin-1-yl)-N-{[4-({[(2R)-4-cyclopropylmorpholin-2-yl]methyl}amino)-3-nitrophenyl]sulfonyl}-2-(1H-pyrrolo[2,3-b]pyridin-5-yloxy)benzamide | |
| 4-(4-{[2-(4-chlorophenyl)-4,4-dimethylcyclohex-1-en-1-yl]methyl}piperazin-1-yl)-N-[(4-{[(trans-4-cyanocyclohexyl)methyl]amino}-3-nitrophenyl)sulfonyl]-2-(1H-pyrrolo[2,3-b]pyridin-5-yloxy)benzamide | |

| Name | Structure |
|---|---|
| Trans-2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl)sulfonyl)benzamide | |
| 4-(4-{[2-(4-chlorophenyl)-4,4-dimethylcyclohex-1-en-1-yl]methyl}piperazin-1-yl)-N-{[4-({(3R)-1-[2-fluoro-1-(fluoromethyl)ethyl]pyrrolidin-3-yl}amino)-3-nitrophenyl]sulfonyl}-2-(1H-pyrrolo[2,3-b]pyridin-5-yloxy)benzamide | |
| Trans-N-({5-chloro-6-[(4-hydroxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide | |

| Name | Structure |
|---|---|
| N-({3-chloro-4-[(trans-4-hydroxycyclohexyl)methoxy]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | 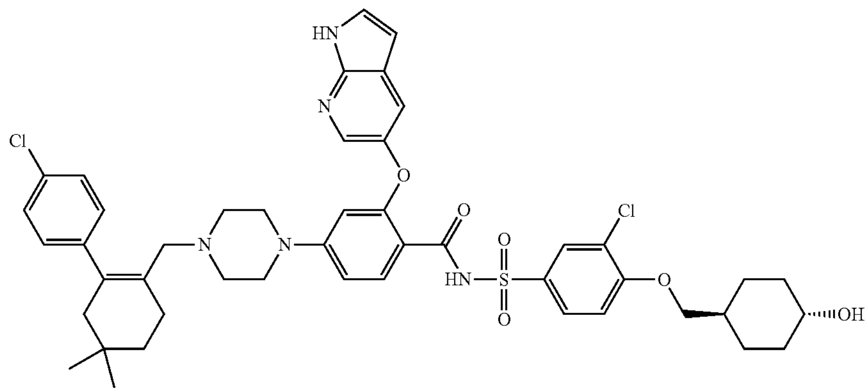 [SMILES: CC1(C)CCC(CN2CCN(c3ccc(C(=O)NS(=O)(=O)c4ccc(OC[C@H]5CC[C@H](O)CC5)c(Cl)c4)c(Oc4cnc5[nH]ccc5c4)c3)CC2)=C(c2ccc(Cl)cc2)C1] |
| N-({5-chloro-6-[(trans-4-hydroxycyclohexyl)methoxy]pyridin-3-yl)sulfonyl)-4-(4-{[2-(4-chlorophenyl)-4,4-dimethylcyclohex-1-en-1-yl]methyl}piperazin-1-yl)-2-[(6-fluoro-1H-indazol-4-yl)oxy]benzamide | 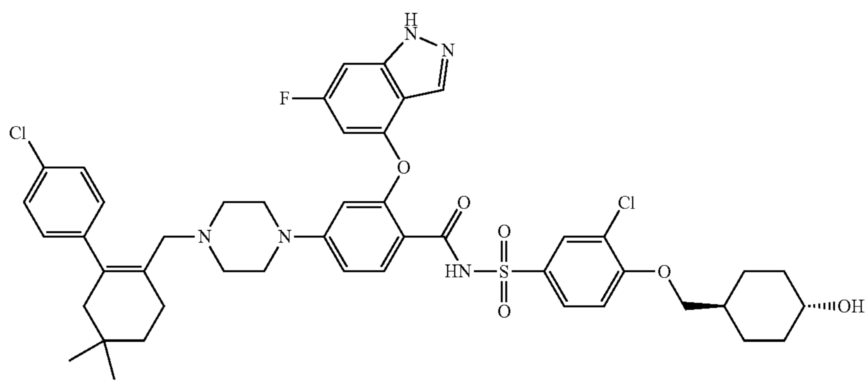 [SMILES: CC1(C)CCC(CN2CCN(c3ccc(C(=O)NS(=O)(=O)c4ccc(OC[C@H]5CC[C@H](O)CC5)c(Cl)c4)c(Oc4cc(F)cc5[nH]ncc45)c3)CC2)=C(c2ccc(Cl)cc2)C1] |
| 2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[trans-4-(morpholin-4-yl)cyclohexyl]amino}-3-nitrophenyl)sulfonyl]benzamide | 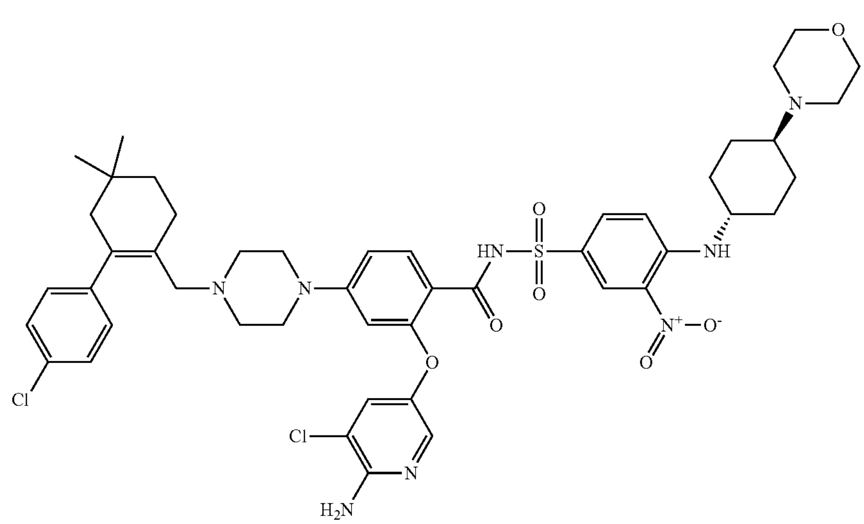 [SMILES: CC1(C)CCC(CN2CCN(c3ccc(C(=O)NS(=O)(=O)c4ccc(N[C@H]5CC[C@H](N6CCOCC6)CC5)c([N+](=O)[O-])c4)c(Oc4cnc(N)c(Cl)c4)c3)CC2)=C(c2ccc(Cl)cc2)C1] |

| Name | Structure |
|---|---|
| 4-(4-{[2-(4-chlorophenyl)-4,4-dimethylcyclohex-1-en-1-yl]methyl}piperazin-1-yl)-N-[(4-{[(cis-4-hydroxy-4-methylcyclohexyl)methyl]amino}-3-nitrophenyl)sulfonyl]-2-(1H-pyrrolo[2,3-b]pyridin-5-yloxy)benzamide | |
| 4-(4-{[2-(4-chlorophenyl)-4,4-dimethylcyclohex-1-en-1-yl]methyl}piperazin-1-yl)-N-({5-cyano-6-[(4-fluorotetrahydro-2H-pyran-4-yl)methoxy]pyridin-3-yl}sulfonyl)-2-(1H-indazol-4-yloxy)benzamide | |
| N-[(5-chloro-6-{[4-fluoro-1-(oxetan-3-yl)piperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | |
| 2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({3-nitro-4-(tetrahydro-2H-pyran-4-ylmethyl)amino]phenyl}sulfonyl)benzamide | |

| Name | Structure |
|---|---|
| 4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)-2-(1H-pyrrolo[2,3-b]pyridin-5-yloxy)benzamide | 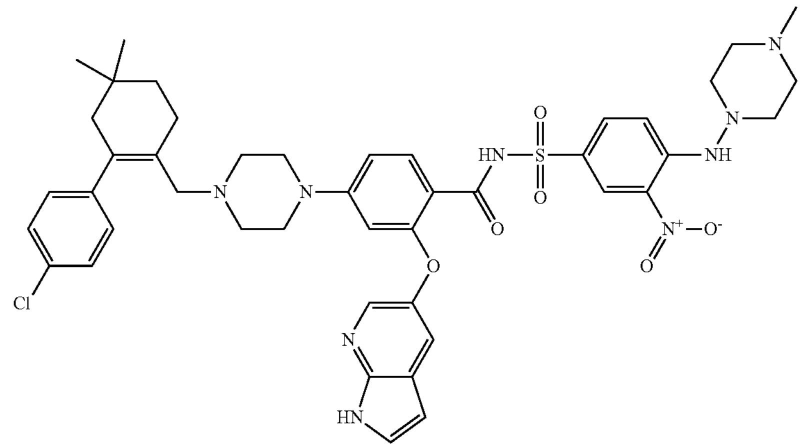 [SMILES: CN1CCN(Nc2ccc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2[N+](=O)[O-])CC1] |
| Trans-4-(4-{[2-(4-chlorophenyl)-4,4-dimethylcyclohex-1-en-1-yl]methyl)piperazin-1-yl)-N-[(4-{[(4-methoxycyclohexyl)methyl]amino}-3-nitrophenyl)sulfonyl]-2-(1H-pyrrolo[2,3-b]pyridin-5-yloxy)benzamide | 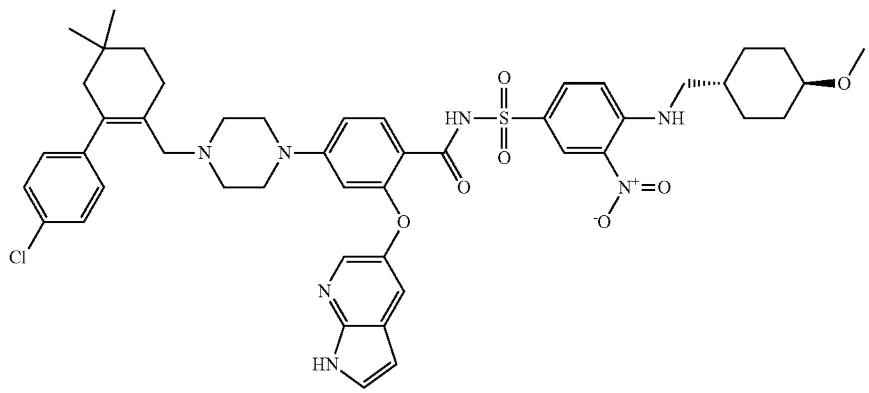 |
| Trans-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl)sulfonyl)-2-(1H-pyrrolo2,3-b]pyridin-5-yloxy)benzamide | |

| Name | Structure |
|---|---|
| 4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-nitrophenyl}sulfonyl)-2-(1H-pyrrolo[2,3-b]pyridin-5-yloxy)benzamide | 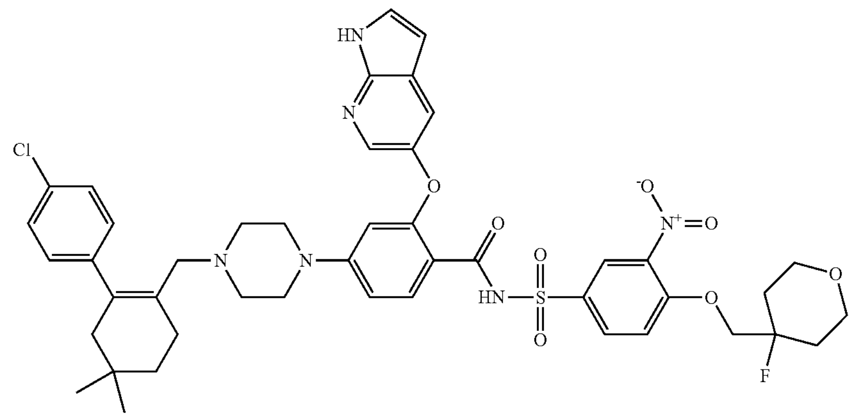 |
| 2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(3R)-1-(2,2-difluoroethyl)pyrrolidin-3-yl]amino-3-nitrophenyl)sulfonyl]benzamide | 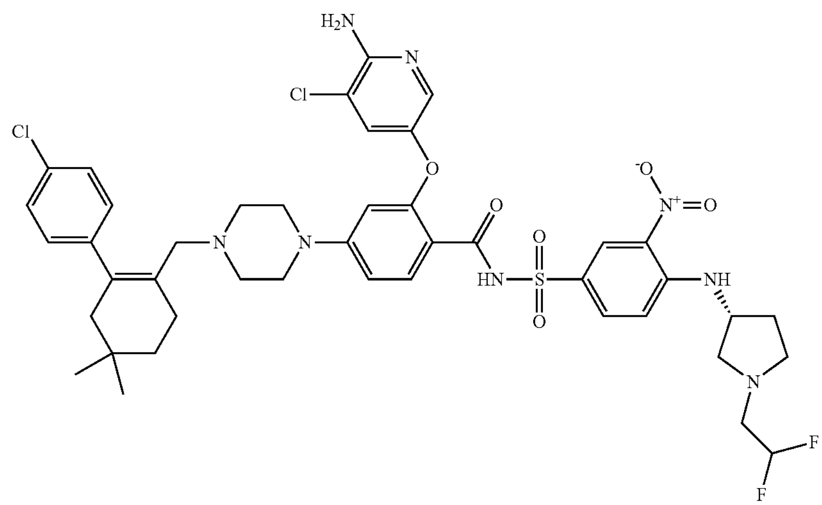 |
| N-({5-chloro-6-[(trans-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide | |

-continued

| Name | Structure |
|---|---|
| N-({5-chloro-6-[(cis-1-fluoro-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide | |
| 2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(4-methoxycyclohexyl)methyl]amino}-3-nitrophenyl)sulfonyl]benzamide | 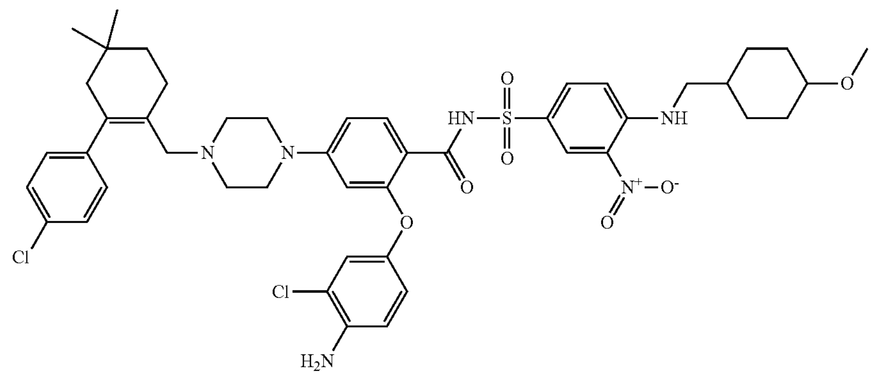 |
| N-({5-chloro-6-[(trans-1-fluoro-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide | 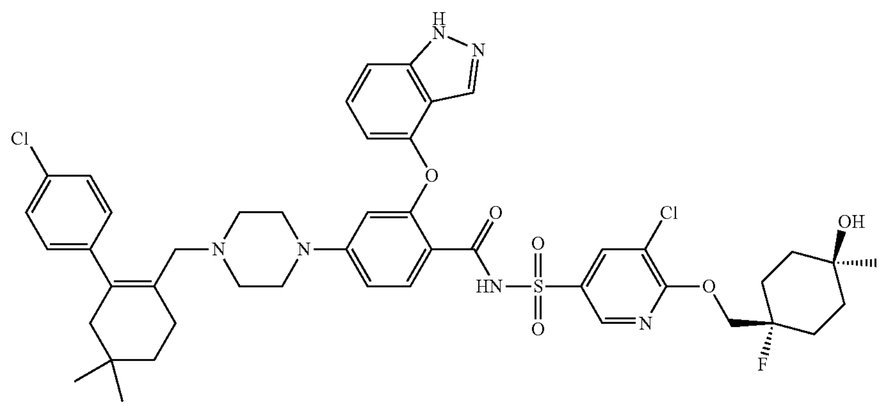 [SMILES: CC1(C)CCC(CN2CCN(c3ccc(C(=O)NS(=O)(=O)c4cnc(OC[C@]5(F)CC[C@](C)(O)CC5)c(Cl)c4)c(Oc4cccc5[nH]ncc45)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-[(4-{[(trans-4-hydroxy-4-methylcyclohexyl)methyl]amino}-3-nitrophenyl)sulfonyl]-2-(1H-pyrrolo[2,3-b]pyridin-5-yloxy)benzamide | 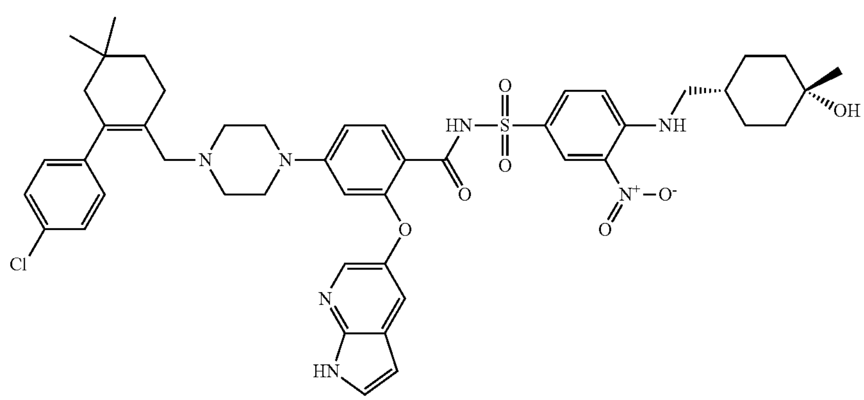 |

| Name | Structure |
|---|---|
| 2-[(3-amino-1H-indazol-4-yl)oxy)-4-(4-{[2-(4-chlorophenyl)-4,4-dimethylcyclohex-1-en-1-yl]methyl)piperazin-1-yl)-N-[(4-{[(trans-4-methoxycyclohexyl)methyl]amino}-3-nitrophenyl)sulfonyl]benzamide | |
| 4-(4-{[2-(4-chlorophenyl)-4,4-dimethylcyclohex-1-en-1-yl]methyl}piperazin-1-yl)-N-({3-nitro-4-[(2-oxaspiro[3;5]non-7-ylmethyl)amino]phenyl}sulfonyl)-2-(1H-pyrrolo[2,3-b]pyridin-5-yloxy)benzamide; | |
| 4-(4-{[2-(4-chlorophenyl)-4,4-dimethylcyclohex-1-en-1-yl]methyl)piperazin-1-yl)-N-({5-cyano-6-[(trans-4-hydroxy-4-methylcyclohexyl)methoxy]pyridin-3-yl}sulfonyl)-2-(1H-indazol-4-yloxy)benzamide | 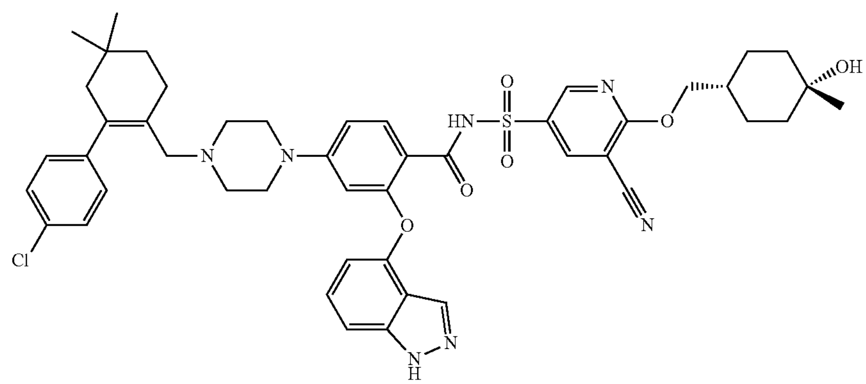 [SMILES: CC1(C)CCC(CN2CCN(c3ccc(C(=O)NS(=O)(=O)c4cnc(OC[C@H]5CC[C@@](C)(O)CC5)c(C#N)c4)c(Oc4cccc5[nH]ncc45)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-2-[(6-fluoro-1H-indol-5-yl)oxy]-N-{[3-nitro-4-({[4-(oxetan-3-yl)morpholin-2-yl]methyl}amino)phenyl)sulfonyl}benzamide | 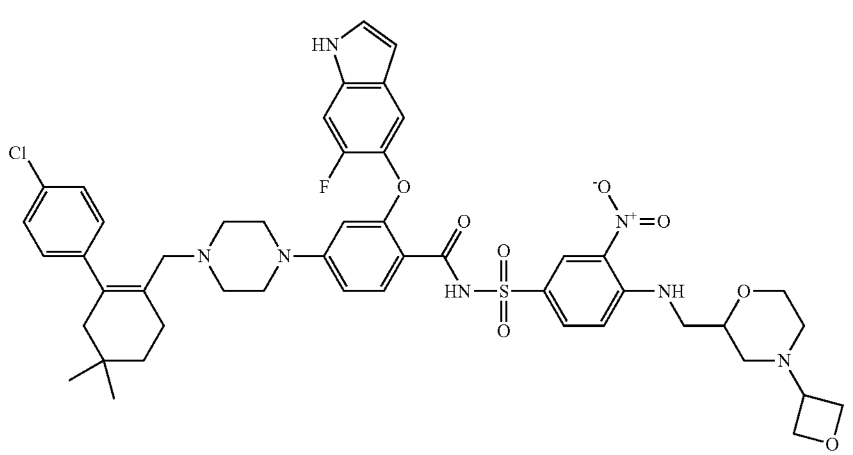 |

| Name | Structure |
|---|---|
| N-({5-chloro-6-[(trans-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-[(6-fluoro-1H-indazol-4-yl)oxy]benzamide | |
| 4-(4-{[2-(4-chlorophenyl)-4,4-dimethylcyclohex-1-en-1-yl]methyl}piperazin-1-yl)-N-[(5-cyano-6-{[4-fluoro-1-(oxetan-3-yl)piperidin-4-yl]methoxy}pyridin-3-yl)sulfonyl]-2-(1H-pyrrolo[2,3-b]pyridin-5-yloxy)benzamide | |
| 2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(4-hydroxycyclohexyl)methyl]amino}-3-nitrophenyl)sulfonyl]benzamide | 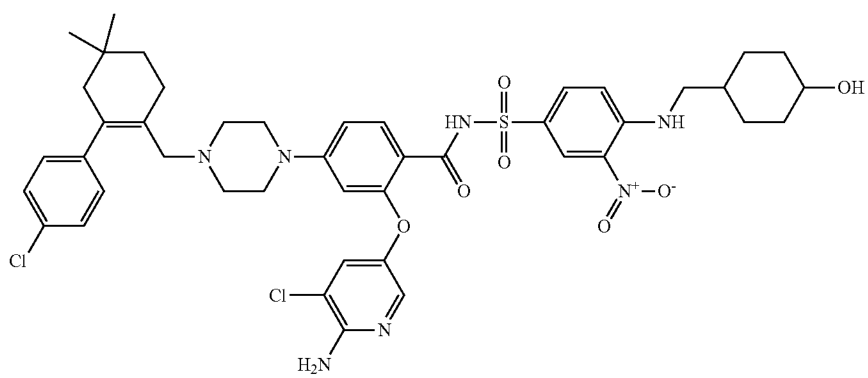 [SMILES: CC1(C)CCC(CN2CCN(c3ccc(C(=O)NS(=O)(=O)c4ccc(NCC5CCC(O)CC5)c([N+](=O)[O-])c4)c(Oc4cnc(N)c(Cl)c4)c3)CC2)=C(c2ccc(Cl)cc2)C1] |
| N-({5-chloro-6-[(trans-4-hydroxy-4-methylcyclohexyl)methoxy]pyridin-3-yl}sulfonyl)-2-[(3-chloro-1H-indazol-4-yl)oxy]-4-(4-{[2-(4-chlorophenyl)-4,4-dimethylcyclohex-1-en-1-yl]methyl}piperazin-1-yl)benzamide | 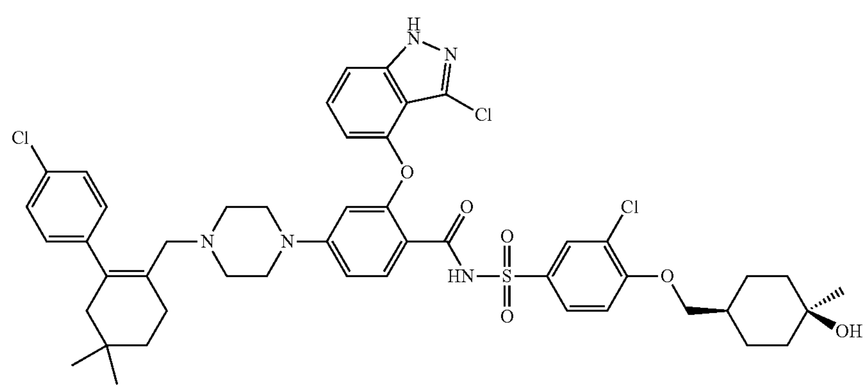 [SMILES: CC1(C)CCC(CN2CCN(c3ccc(C(=O)NS(=O)(=O)c4ccc(OC[C@H]5CC[C@@](C)(O)CC5)c(Cl)c4)c(Oc4cccc5[nH]nc(Cl)c45)c3)CC2)=C(c2ccc(Cl)cc2)C1] |

| Name | Structure |
|---|---|
| 4-[4-{[2-(4-chlorophenyl)-4,4-dimethylcyclohex-1-en-1-yl]methyl}piperazin-1-yl]-N-({3-nitro-4-[(tetrahydro-2H-pyran-4-ylmethyl)amino]phenyl}sulfonyl)-2-(1H-pyrrolo[2,3-b]pyridin-5-yloxy)benzamide | 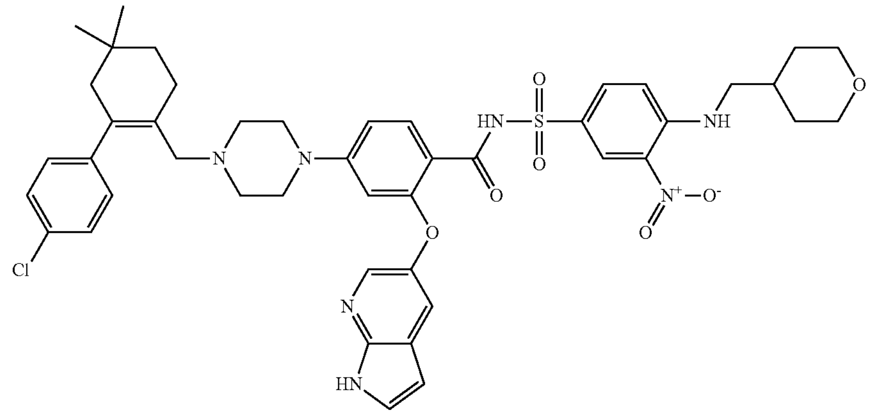 |
| N-({5-chloro-6-[(trans-1-fluoro-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | 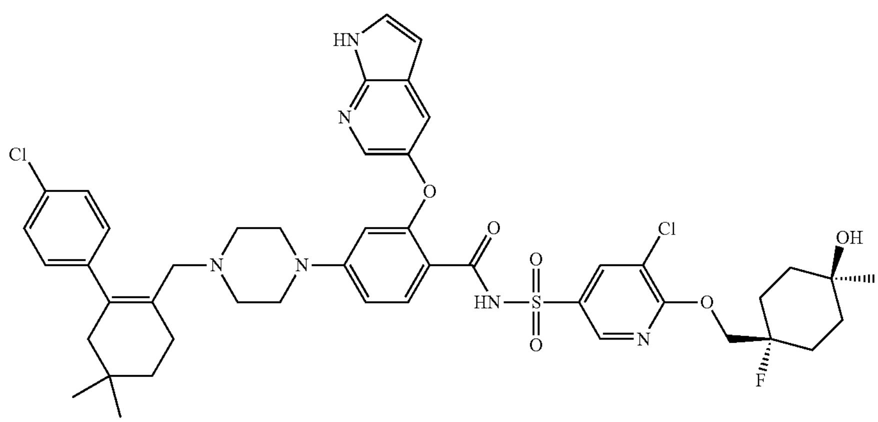 [SMILES: CC1(C)CCC(CN2CCN(c3ccc(C(=O)NS(=O)(=O)c4cnc(OC[C@]5(F)CC[C@](C)(O)CC5)c(Cl)c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-[(6-{[(cis-4-hydroxy-4-methylcyclohexyl)methyl]amino}-5-nitropyridin-3-yl)sulfonyl]-2-(1H-pyrrolo[2,3-b]pyridin-5-yloxy)benzamide | 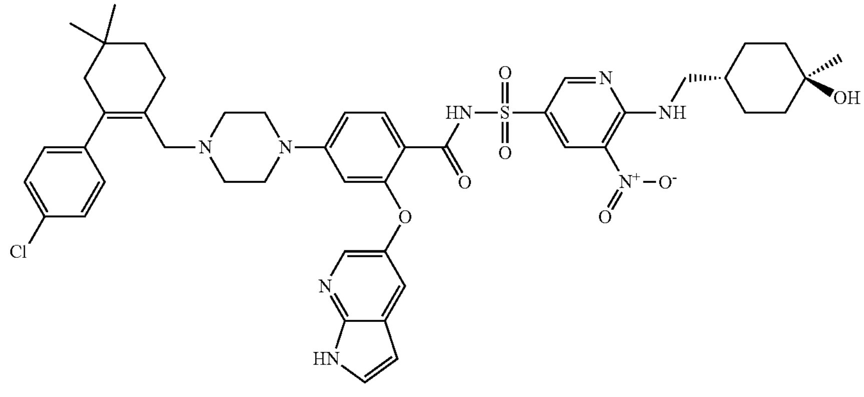 [SMILES: CC1(C)CCC(CN2CCN(c3ccc(C(=O)NS(=O)(=O)c4cnc(NC[C@H]5CC[C@](C)(O)CC5)c([N+](=O)[O-])c4)c(Oc4cnc5[nH]ccc5c4)c3)CC2)=C(c2ccc(Cl)cc2)C1] |

| Name | Structure |
|---|---|
| 4-(4-{[2-(4-chlorophenyl)-4,4-dimethylcyclohex-1-en-1-yl]methyl}piperazin-1-yl)-N-({5-nitro-6-[(tetrahydro-2H-pyran-4-ylmethyl)aimno]pyridin-3-yl}sulfonyl)-2-(1H-pyrrolo[2,3-b]pyridin-5-yloxy)benzamide | |
| 4-(4-{[2-(4-chlorophenyl)-4,4-dimethylcyclohex-1-en-1-yl]methyl}piperazin-1-yl)-N-({6-[(trans-4-hydroxy-4-methylcyclohexyl)methoxy]-5-(trifluoromethyl)pyridin-3-yl}sulfonyl)-2-(1H-indazol-4-yloxy)benzamide | |
| 4-(4-{[2-(4-chlorophenyl)-4,4-dimethylcyclohex-1-en-1-yl]methyl}piperazin-1-yl)-N-[(4-{[(cis-4-ethyl-4-hydroxycyclohexyl)methyl]amino}-3-nitrophenyl)sulfonyl]-2-(1H-pyrrolo[2,3-b]pyridin-5-yloxy)benzamide | |

| Name | Structure |
|---|---|
| 4-(4-{[2-(4-chlorophenyl)-4,4-dimethylcyclohex-1-en-1-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide | 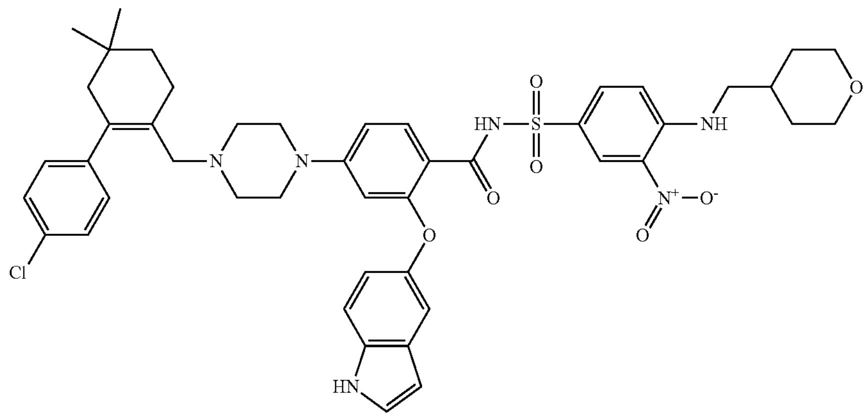 [SMILES: CC1(C)CCC(CN2CCN(c3ccc(C(=O)NS(=O)(=O)c4ccc(NCC5CCOCC5)c([N+](=O)[O-])c4)c(Oc4ccc5[nH]ccc5c4)c3)CC2)=C(c2ccc(Cl)cc2)C1] |

In some embodiments, the compound is selected from the group consisting of:

| Name | Structure |
|---|---|
| 4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)-2-(1H-pyrrolo[2,3-b]pyridin-5-yloxy)benzamide | |
| 4-{4-[(4'-chloro-1,1'-biphenyl-2-yl)methyl]piperazin-1-yl}-N-({4-[(3-morpholin-4-ylpropyl)amino]-3-nitrophenyl}sulfonyl)-2-(1H-pyrrolo[2,3-b]pyridin-5-yloxy)benzamide | 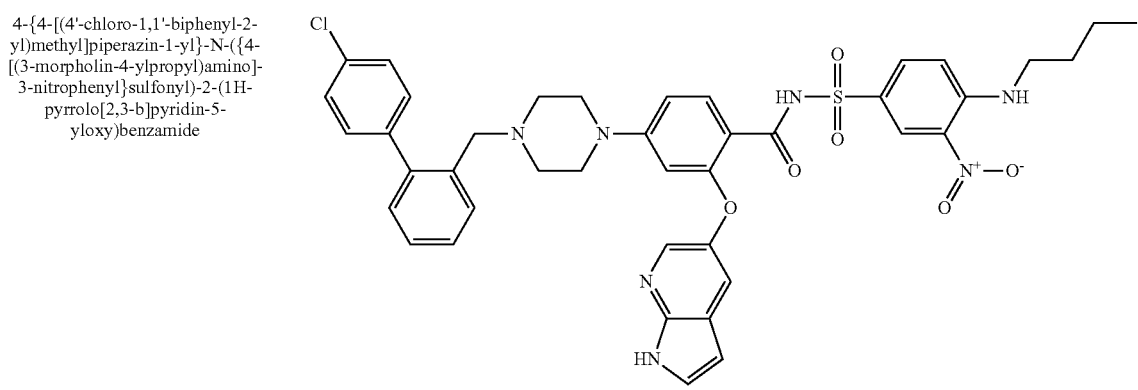 |

| Name | Structure |
|---|---|
| 4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)-2-(1H-pyrrolo[2,3-b]pyridin-5-yloxy)benzamide | 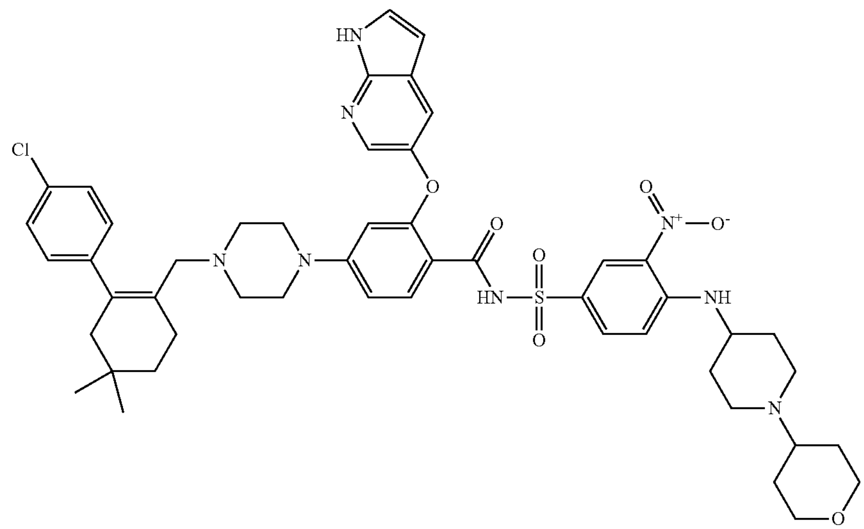 [SMILES: CC1(C)CCC(CN2CCN(c3ccc(C(=O)NS(=O)(=O)c4ccc(NC5CCN(C6CCOCC6)CC5)c([N+](=O)[O-])c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)-2-(1H-pyrrolo[2,3-b]pyridin-5-yloxy)benzamide | 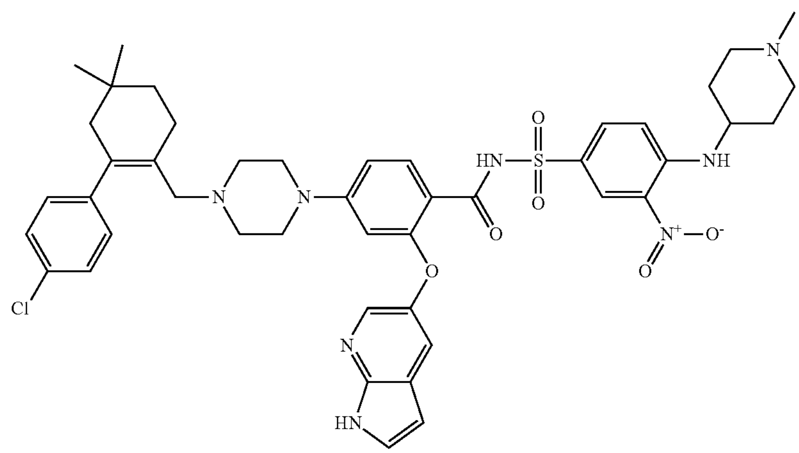 |
| 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide | 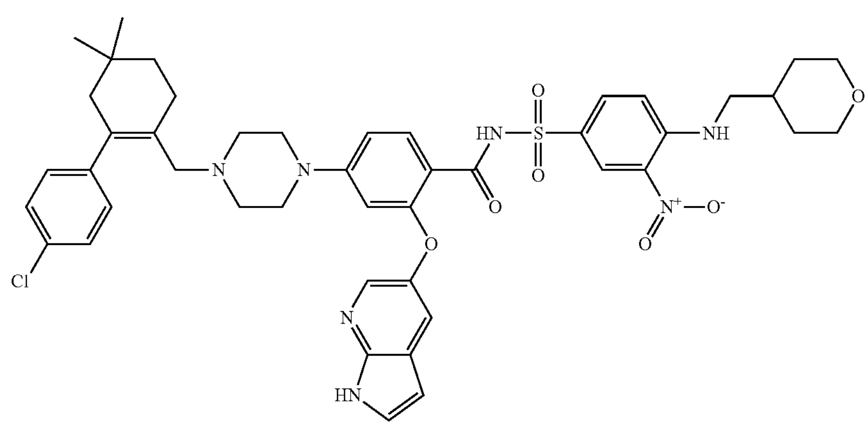 |

-continued

| Name | Structure |
|---|---|
| 4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)-2-(1H-pyrrolo[2,3-b]pyridin-5-yloxy)benzamide | 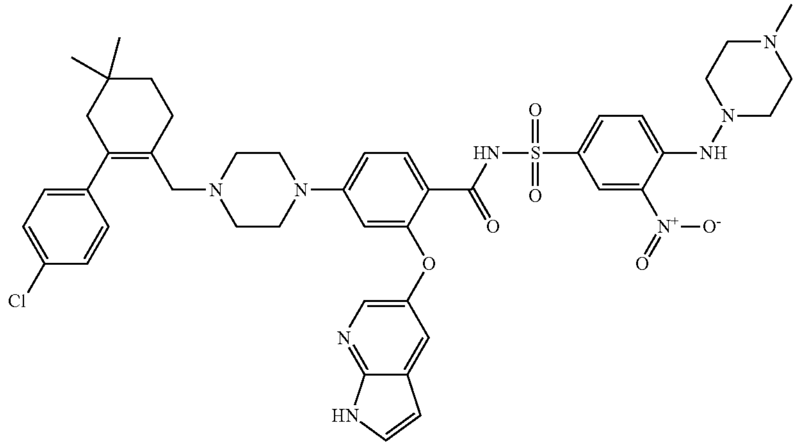 [SMILES: CN1CCN(Nc2ccc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2[N+](=O)[O-])CC1] |
| 2-(9H-carbazol-4-yloxy)-4-(4-{[2-(4-chlorophenyl)-4,4-dimethyleyclohex-1-en-1-yl]methyl}piperazin-1-yl)-N-({4-[(1-methylpiperidin-4-yl)amino]-3-nitrophenyl}sulfonyl)benzamide | 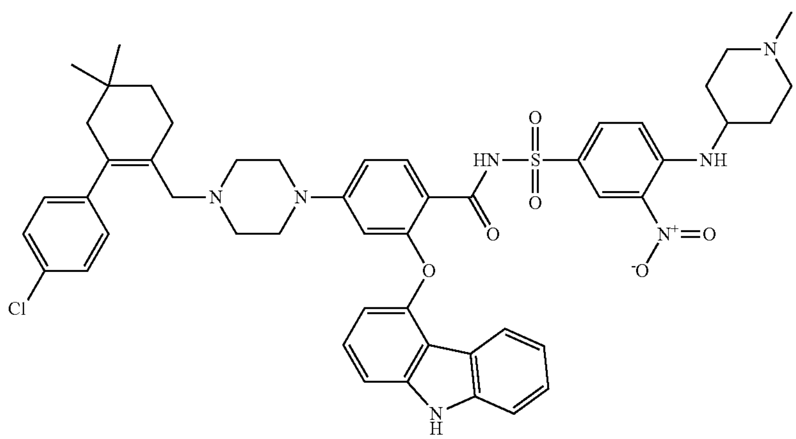 |
| 2-(9H-carbazol-4-yloxy)-4-(4-{[2-(4-chlorophenyl)-4,4-dimethyleyclohex-1-en-1-yl]methyl}piperazin-1-yl)-N-({3-nitro-4-[(3-pyrrolidin-1-ylpropyl)amino]phenyl}sulfonyl)benzamide | 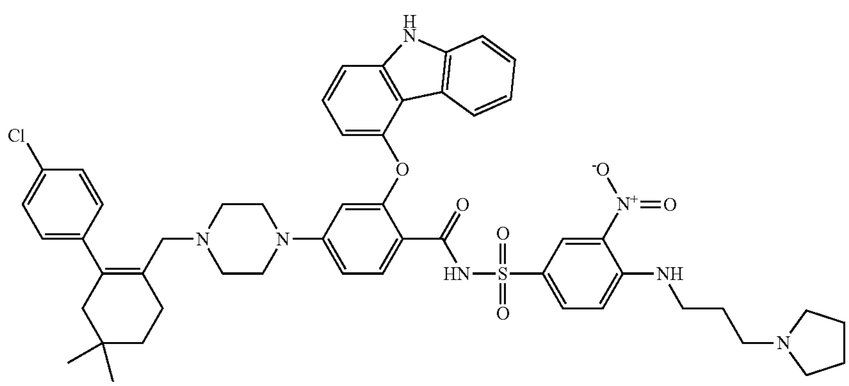 |

| Name | Structure |
|---|---|
| Trans-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)-2-(1H-pyrrolo[2,3-b]pyridin-5-yloxy)benzamide | 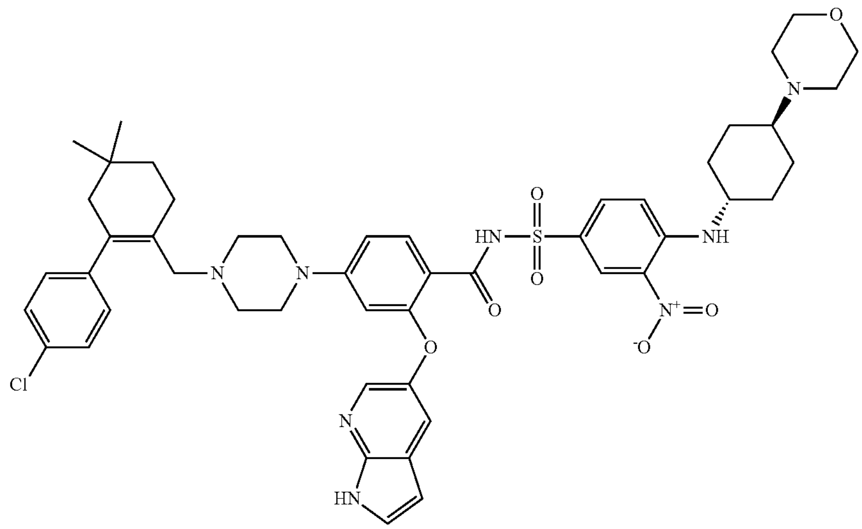 |
| 4-(4-{[2-(4-chlorophenyl)-4,4-dimethylcyclohex-1-en-1-yl]methyl}piperazin-1-yl)-N-({4-[(2-methoxyethyl)amino]-3-nitrophenyl}sulfonyl)-2-(1H-pyrrolo[2,3-b]pyridin-5-yloxy)benzamide | 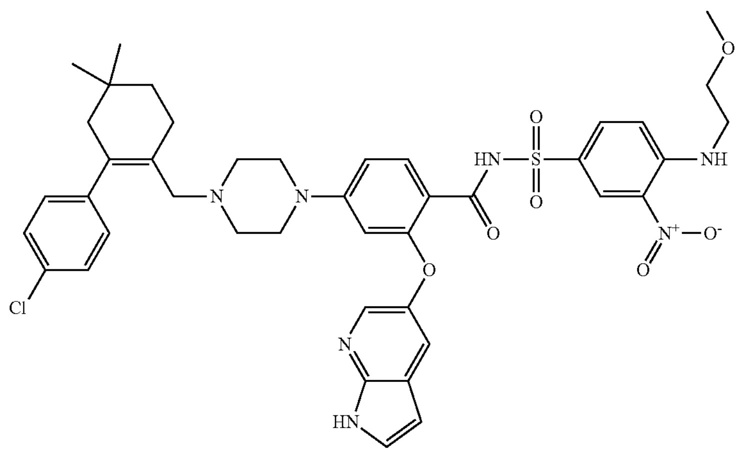 [SMILES: COCCNc1ccc(S(=O)(=O)NC(=O)c2ccc(N3CCN(CC4=C(c5ccc(Cl)cc5)CC(C)(C)CC4)CC3)cc2Oc2cnc3[nH]ccc3c2)cc1[N+](=O)[O-]] |
| 4-(4-{[2(4-chlorophenyl)-4,4-dimethylcyclohex-1-en-1-yl]methyl}piperazin-1-yl)-N-[(3-nitro-4-{[(3S)-tetrahydro-2H-pyran-3-ylmethyl]amino}phenyl)sulfonyl]-2-(1H-pyrrolo[2,3-b]pyridin-5-yloxy)benzamide | |

| Name | Structure |
|---|---|
| 4-(4-{[2-(4-chlorophenyl)-4,4-dimethylcyclohex-1-en-1-yl]methyl}piperazin-1-yl)-N-{[4-(1,4-dioxan-2-ylmethoxy)-3-nitrophenyl]sulfonyl}-2-(1H-pyrrolo[2,3-b]pyridin-5-yloxy)benzamide | |
| 4-(4-{[2-(4-chlorophenyl)-4,4-dimethylclohex-1-en-1-yl]methyl}piperazin-1-yl)-N-[(3-nitro-4-{[(3R)-tetrahydro-2H-pyran-3-ylmethyl]amino}[phenyl)sulfonyl]-2-(1H-pyrrolo[2,3-b]pyridin-5-yloxy)benzamide | 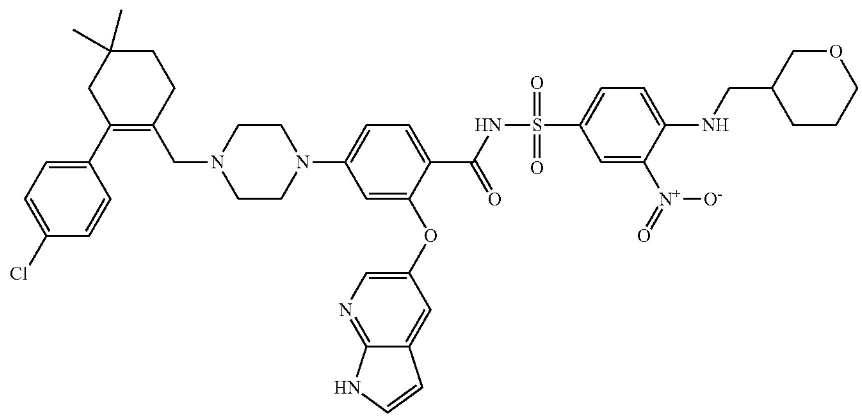 [SMILES: CC1(C)CCC(CN2CCN(c3ccc(C(=O)NS(=O)(=O)c4ccc(NCC5CCCOC5)c([N+](=O)[O-])c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-2-(2 naphthylsulfonyl-2-(1H-pyrrolo[2,3-b]pyridin-5-yloxy)benzamide | 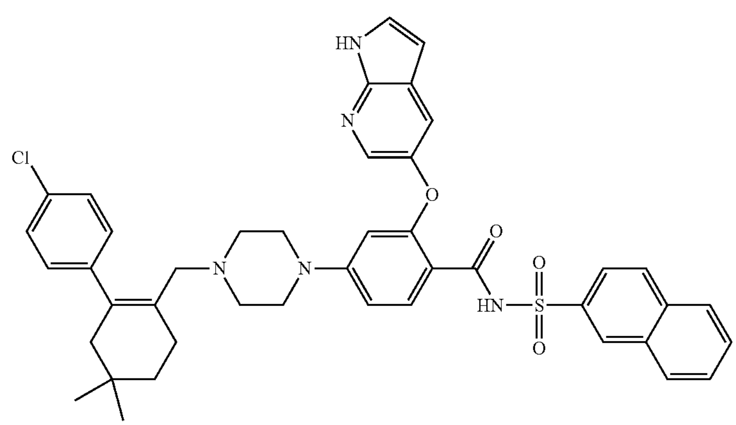 [SMILES: CC1(C)CCC(CN2CCN(c3ccc(C(=O)NS(=O)(=O)c4ccc5ccccc5c4)c(Oc4cnc5[nH]ccc5c4)c3)CC2)=C(c2ccc(Cl)cc2)C1] |

| Name | Structure |
|---|---|
| 4-(4-{[4-(4-chlorophenyl)-6,6-dimethyl-5,6-dihydro-2H-pyran-3-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide | 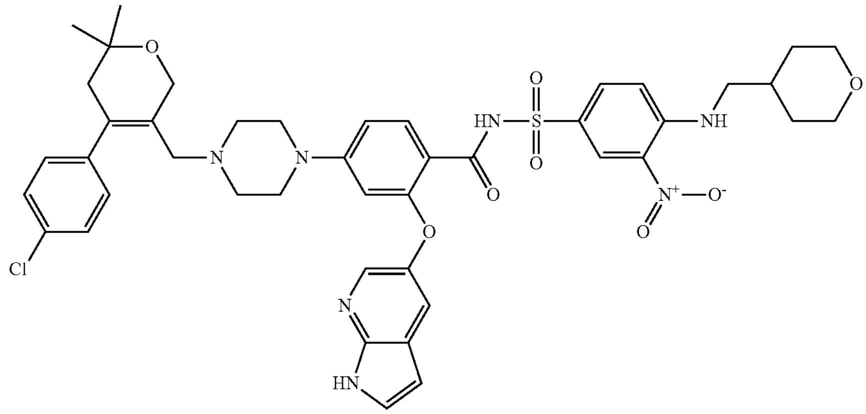 |
| 4-(4-{[2-(4-chlorophenyl)-4,4-dimethylcyclohex-1-en-1-yl]methyl}piperazin-1-yl)-N-([4-[(2-methoxyethyl)amino]-3-[(trifluoromethyl)sulfonyl]phenyl}sulfonyl)-2-(1H-pyrrolo[2,3-b]pyridin-5-yloxy)benzamide | |
| 4-(4-{[2-(4-chlorophenyl)-4,4-dimethylcyclohex-1-en-1-yl]methyl]piperazin-1-yl)-2-(1H-pyrrolo[2,3-b]pyridin-5-yloxy)-N-({4-[(tetrahydro-2H-pyran-4-ylmethyl)arnino]-3-[(trifluoromethyl)sulfonyl]phenyl}sulfonyl)benzamide | 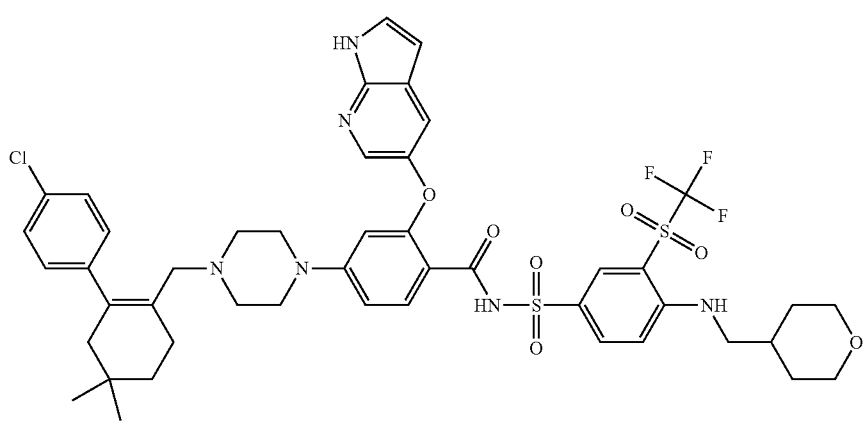 [SMILES: CC1(C)CCC(CN2CCN(c3ccc(C(=O)NS(=O)(=O)c4ccc(NCC5CCOCC5)c(S(=O)(=O)C(F)(F)F)c4)c(Oc4cnc5[nH]ccc5c4)c3)CC2)=C(c2ccc(Cl)cc2)C1] |

| Name | Structure |
|---|---|
| 4-(4-{[2-(4-chlorophenyl)-4,4-dimethyleyclohex-1-en-1-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide | 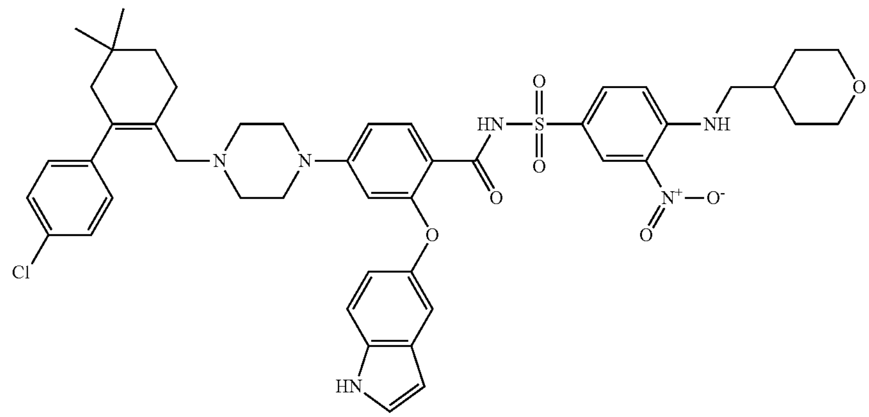 [SMILES: CC1(C)CCC(CN2CCN(c3ccc(C(=O)NS(=O)(=O)c4ccc(NCC5CCOCC5)c([N+](=O)[O-])c4)c(Oc4ccc5[nH]ccc5c4)c3)CC2)=C(c2ccc(Cl)cc2)C1] |
| Trans-4-(4-{[2-(4-chlorophenyl)-4,4-dimethylcyclohex-1-en-1-yl]methyl}piperazin-1-yl)-2-(1H-indol-5-yloxy)-N-({4-[(4-morpholin-4-ylcyclohexyl)amino]-3-nitrophenyl}sulfonyl)benzamide | 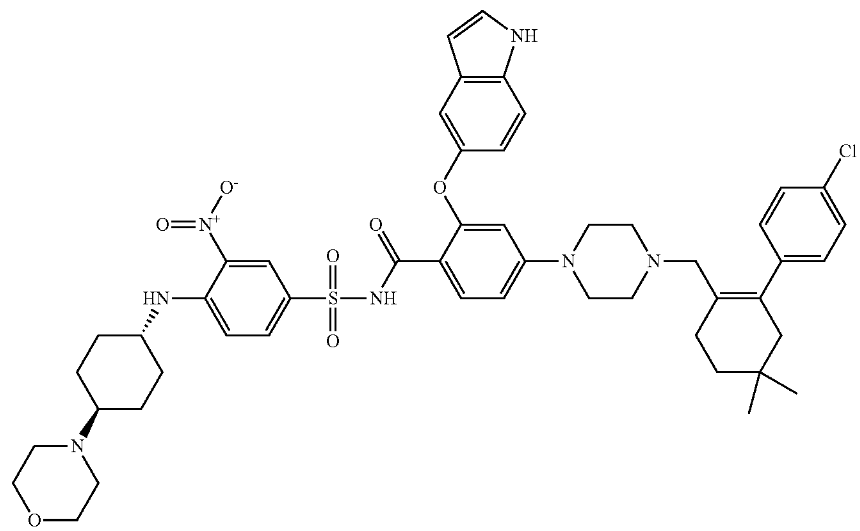 [SMILES: CC1(C)CCC(CN2CCN(c3ccc(C(=O)NS(=O)(=O)c4ccc(N[C@H]5CC[C@H](N6CCOCC6)CC5)c([N+](=O)[O-])c4)c(Oc4ccc5[nH]ccc5c4)c3)CC2)=C(c2ccc(Cl)cc2)C1] |
| 4-(4{[2-(4-chlorophenyl)-4,4-dimethylcyclohex-1-en-1-yl]methyl}piperazin-1-yl)-2-(1H-indol-5-yloxy-N-({4-[(2-methoxyethyl)amino]-3-nitrophenyl}sulfonyl)benzamide | |

-continued

| Name | Structure |
|---|---|
| 4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[(3S)-tetrahydro-2H-pyran-3-ylmethyl]amino}phenyl)sulfonyl]benzamide | 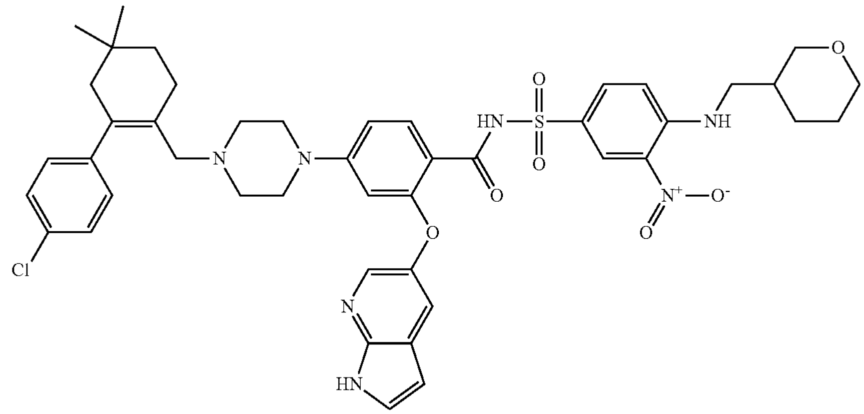 |
| 4-(4-{[2-(4-chlorophenyl)-4,4-dimethylcyclohex-1-en-1-yl]methyl}piperazin-1-yl)-2-(1H-indol-5-yloxy)-N-[3-nitro-4-{[(3R)-tetrahydro-2H-pyran-3-ylmethyl]amino}phenyl)sulfonyl]benzamide | |
| 4-(4-{[4-(4-chlorophenyl)-6,6-dimethyl-5,6-dihydro-2H-pyran-3-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide | 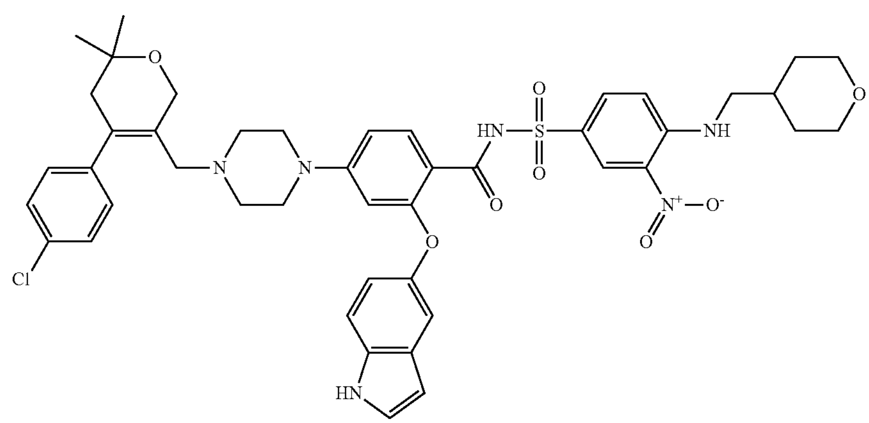 |

| Name | Structure |
|---|---|
| 4-(4-{[2-(4-chlorophenyl)-4,4-dimethylcyclohex-1-en-1-yl]methyl)piperazin-1-yl)-N-{[3-nitro-4-(tetrahydro-2H-pyran-4-ylmethoxy)phenyl]sulfonyl}-2-(1H-pyrrolo[2,3-b]pyridin-5-yloxy)benzamide | 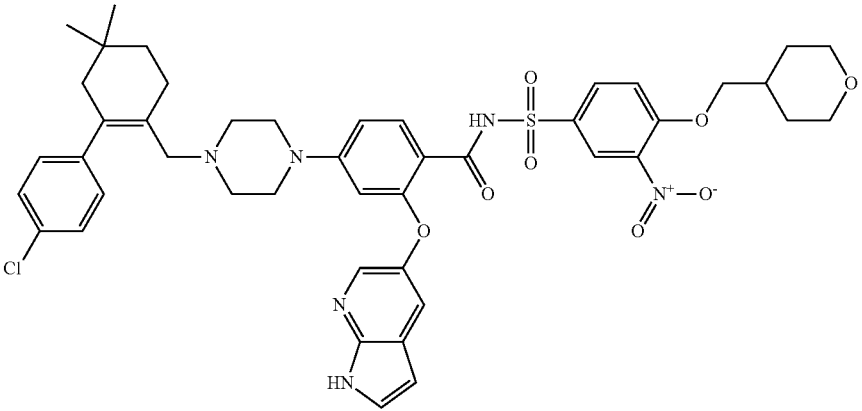 |
| 4-(4-{[2-(4-chlorophenyl)-4,4-dimethylcyclohex-1-en-1-yl]methyl}piperazin-1-yl)-N-({4-[(1,4-dioxan-2-ylmethyl)amino]-3-nitrophenyl}sulfonyl)-2-(1H-pyrrolo[2,3-b]pyridin-5-yloxy)benzamide | 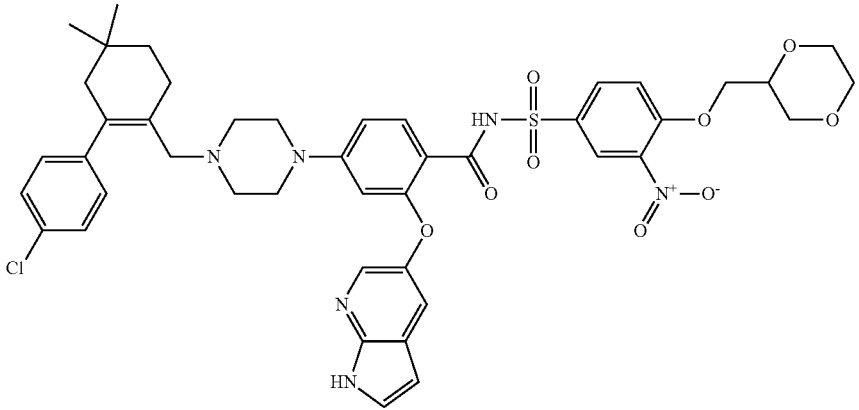 |
| 4-(4-{[2-(4-chlorophenyl)-4,4-dimethylcyclohex-1-en-1-yl]methyl}piperazin-1-yl)-N-({3-nitro-4-[(2,2,2-trifluoroethyl)amino]phenyl}sulfonyl)-2-(1H-pyrrolo[2,3-b]pyridin-5-yloxy)benzamide | 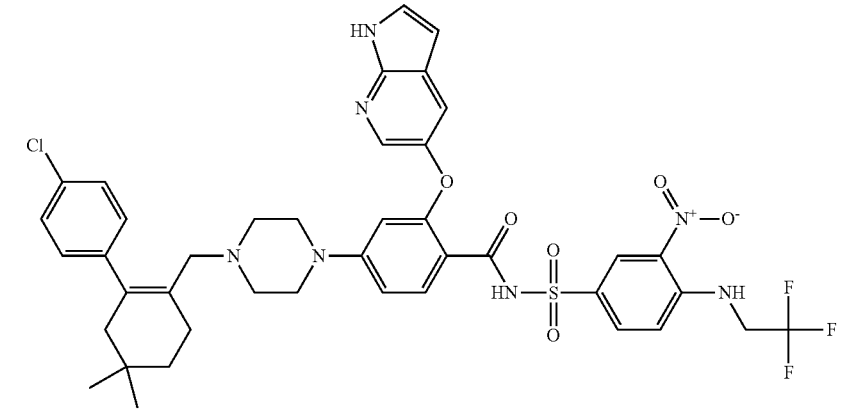 [SMILES: CC1(C)CCC(CN2CCN(c3ccc(C(=O)NS(=O)(=O)c4ccc(NCC(F)(F)F)c([N+](=O)[O-])c4)c(Oc4cnc5[nH]ccc5c4)c3)CC2)=C(c2ccc(Cl)cc2)C1] |

| Name | Structure |
|---|---|
| 4-(4-{[2-(4-chlorophenyl)-4,4-dimethylcyclohex-1-en-1-yl]methyl)piperazin-1-yl)-N-({3-nitro-4-[(3,3,3-trifluoropropyl)amino]phenyl}sulfonyl)-2-(1H-pyrrolo[2,3-b]pyridin-5-yloxy)benzamide | 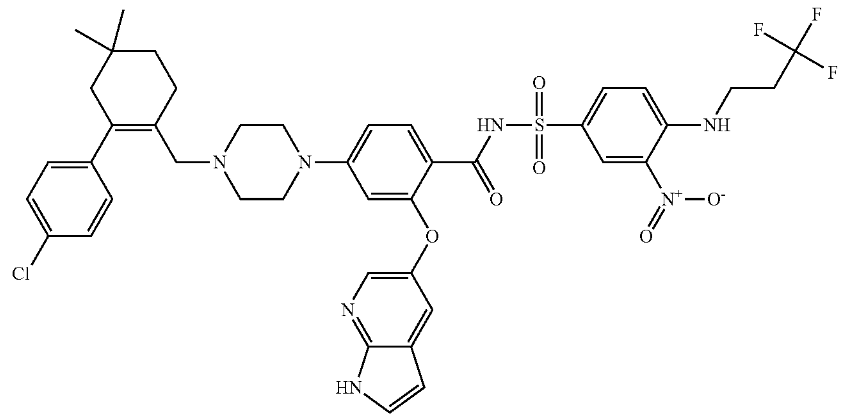 [SMILES: CC1(C)CCC(CN2CCN(c3ccc(C(=O)NS(=O)(=O)c4ccc(NCCC(F)(F)F)c([N+](=O)[O-])c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-({4-[(2S)-1,4-dioxan-2-ylmethoxy]-3-nitrophenyl}sulfonyl)-2-(1H-pyrrolo[2,3-1-]pyridin-5-yloxy)benzamide | 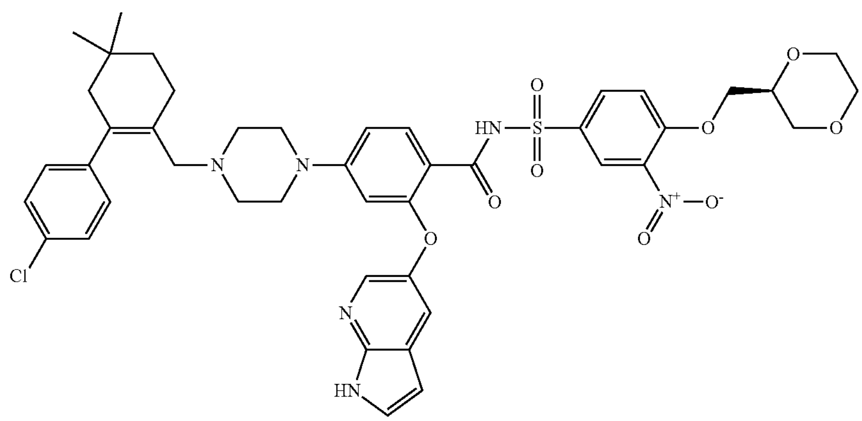 [SMILES: CC1(C)CCC(CN2CCN(c3ccc(C(=O)NS(=O)(=O)c4ccc(OC[C@@H]5COCCO5)c([N+](=O)[O-])c4)c(Oc4cnc5[nH]ccc5c4)c3)CC2)=C(c2ccc(Cl)cc2)C1] |
| Cis-4-(4-{[2-(4-chlorophenyl)-4,4-dimethylcyclohex-1-en-1-yl]methyl}piperazin-1-yl)-N-[(4-{[(4-methoxycyclohexyl)methyl]amino}-3-nitrophenyl)sulfonyl]-2-(1H-pyrrolo[2,3-b]pyridin-5-yloxy)benzamide | 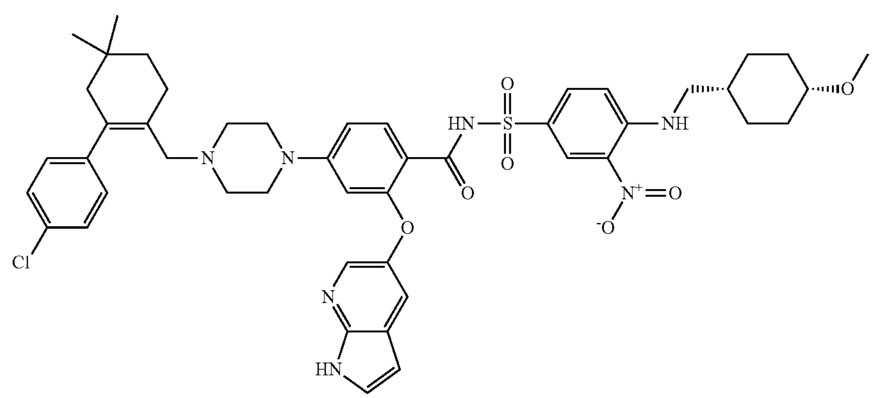 |

| Name | Structure |
|---|---|
| 4-(4-{[2-(4-chlorophenyl)-4,4-dimethylcyclohex-1-en-1-yl]methyl}piperazin-1-yl)-N-({4-[(2R)-1,4-dioxan-2-ylmethoxy]-3-nitrophenyl}sulfonyl)-2-(1H-pyrrolo[2,3-b]pyridin-5-yloxy)benzamide | 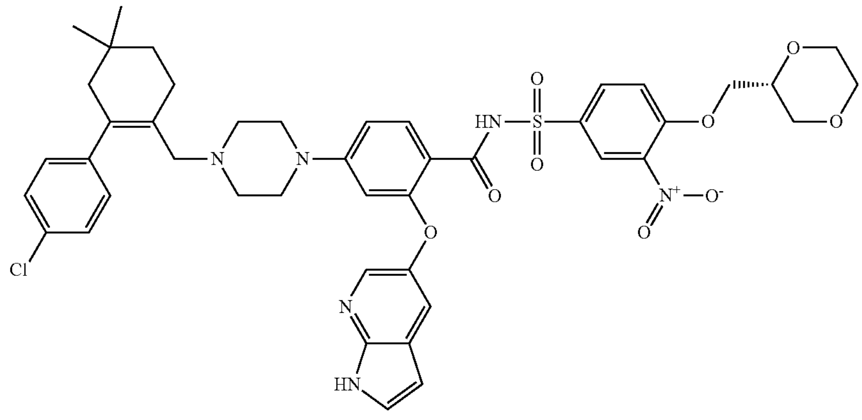 |
| 4-(4-{[4-(4-chlorophenyl)-6,6-dimethyl-5,6-dihydro-2H-pyran-3-yl]methyl}piperazin-1-yl)-N-({4-(1,4-dioxan-2-ylmethyl)amino]-3-nitrophenyl}sulfonyl)-2-1H-pyrrolo[2,3-b]pyridin-5-yloxy)benzamide | 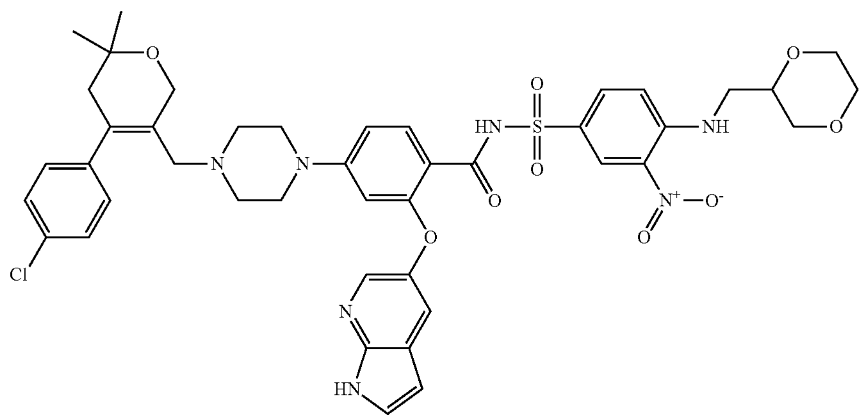 |
| 4-(4-{[4-(4-chlorophenyl)-6,6-dimethyl-5,6-dihydro-2H-pyran-3-yl]methyl}piperazin-1-yl)-N-{[4-(1,4-dioxan-2-ylmethoxy)-3-nitrophenyl]sulfonyl}-2-(1H-pyrrolo[2,3-b]pyridin-5-yloxy)benzamide | 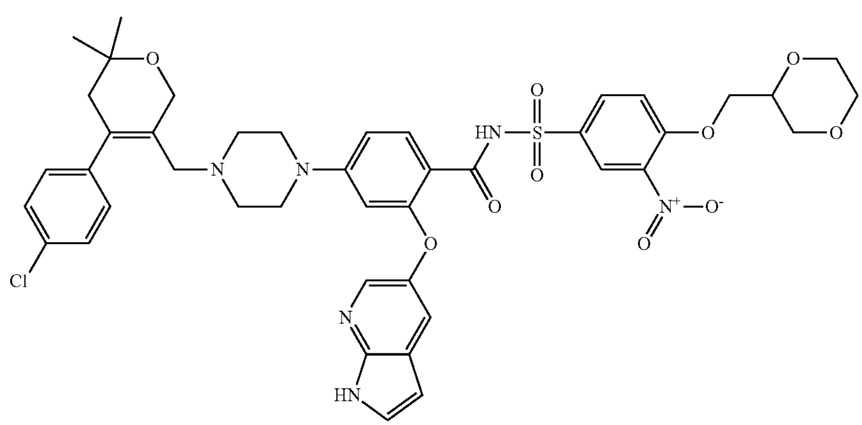 [SMILES: CC1(C)CCC(CN2CCN(c3ccc(C(=O)NS(=O)(=O)c4ccc(OC[C@H]5COCCO5)c([N+](=O)[O-])c4)c(Oc4cnc5[nH]ccc5c4)c3)CC2)=C(c2ccc(Cl)cc2)C1] |

-continued

| Name | Structure |
|---|---|
| Trans-4-(4-{[4-(4-chlorophenyl)-6,6-dimethyl-5,6-dihydro-2H-pyran-3-yl]methyl}piperazin-1-yl)-N-({4-[(4-morpholin-4-ylcyclohexyl)amino]-3-nitrophenyl)sulfonyl)-2-(1H-pyrrolo[2,3-b]pyridin-5-yloxy)benzamide | 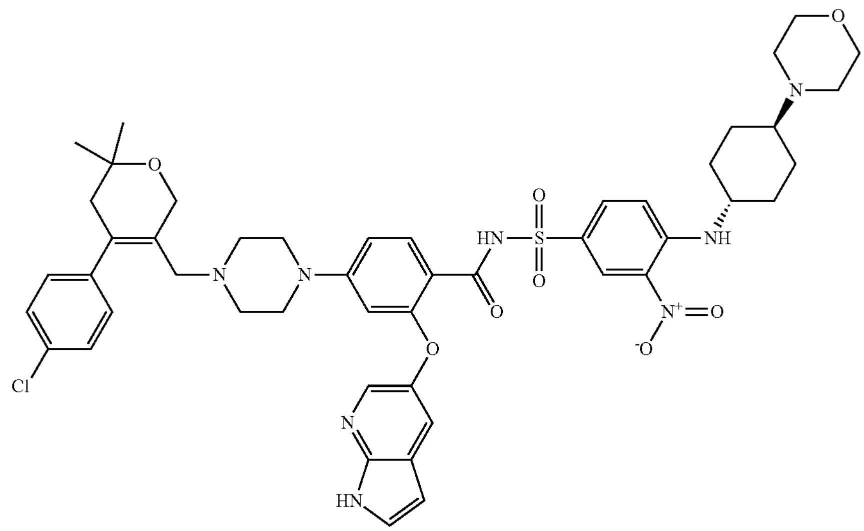 |
| Trans-4-(4-{[2-(-4-chlorophenyl)-4,4-dimethylcyclohex-1-en-1-yl]methyl)piperazin-1-yl)-N-[(4-{[(4-methoxycyclohexyl)methyl]amino}-3-nitrophenyl)sulfonyl]-2-(1H-pyrrolo[2,3-b]pyridin-5-yloxy)benzamide | 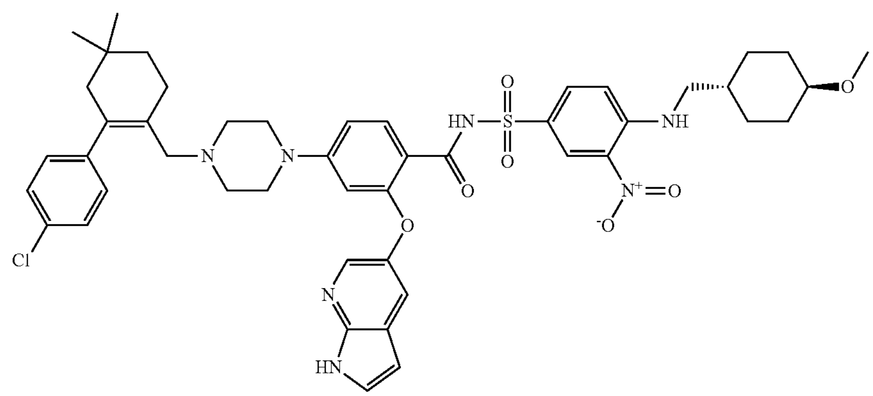 |
| 4-(4-{[4-(4-chlorophenyl)-6,6-dimethyl-5,6-dihydro-2H-pyran-3-yl]methyl}piperazin-1-yl)-N-{[5-cyano-6-(tetrahydro-2H-pyran-4-ylmethoxy)pyridin-3-yl]sulfonyl}-2-(1H-pyrrolo[2,3-b]pyridin-5-yloxy)benzamide | 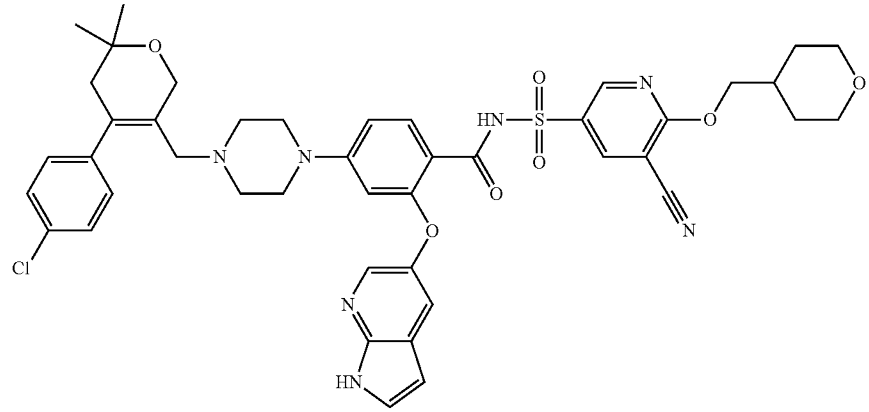 |

| Name | Structure |
|---|---|
| 4-(4-{[2-(4-chlorophenyl)-4,4-dimethylcyclohex-1-en-1-yl]methyl}piperazin-1-yl)-N-{[5-cyano-6-(tetrahydro-2H-pyran-4-ylmethoxy)pyridin-3-yl]sulfonyl}-2-(1H-pyrrolo[2,3-b]pyridin-5-yloxy)benzamide | 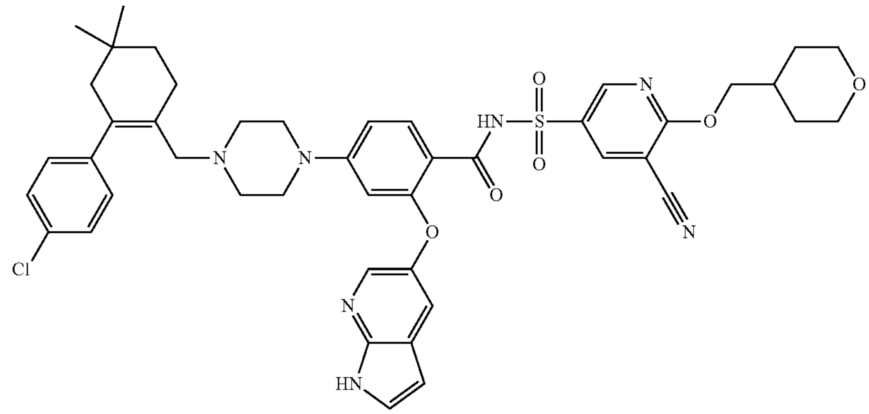 [SMILES: CC1(C)CCC(CN2CCN(c3ccc(C(=O)NS(=O)(=O)c4cnc(OCC5CCOCC5)c(C#N)c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-({4-[4-fluorotetrahydro-2H-pyran-4-yl)methoxy]-3-nitrophenyl}sulfonyl)-2-(1H-pyrrolo[2,3-b]pyridin-5-yloxy)benzamide | 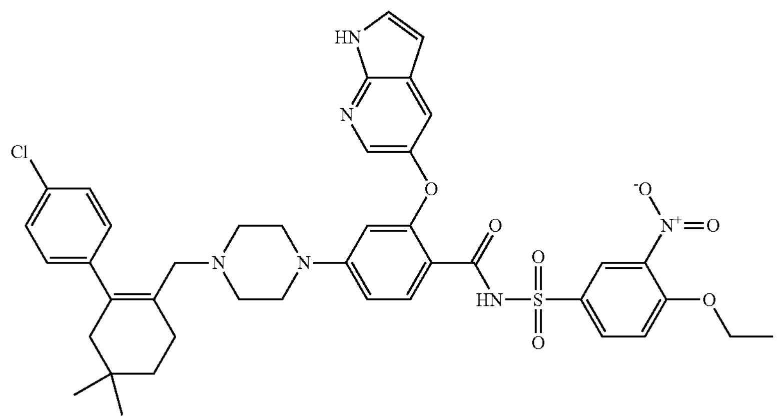 |
| N-{[3-(aminocarbonyl)-4-(tetrahydro-2H-pyran-4-ylmethoxy)phenyl]sulfonyl}-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | 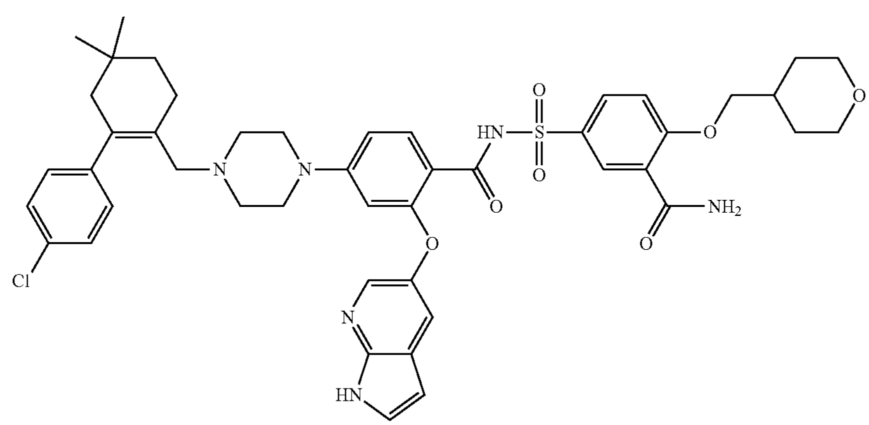 [SMILES: CC1(C)CCC(CN2CCN(c3ccc(C(=O)NS(=O)(=O)c4ccc(OCC5CCOCC5)c(C(N)=O)c4)c(Oc4cnc5[nH]ccc5c4)c3)CC2)=C(c2ccc(Cl)cc2)C1] |

| Name | Structure |
|---|---|
| Cis-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)-2-(1H-pyrrolo[2,3-b]pyridin-5-yloxy)benzamide | 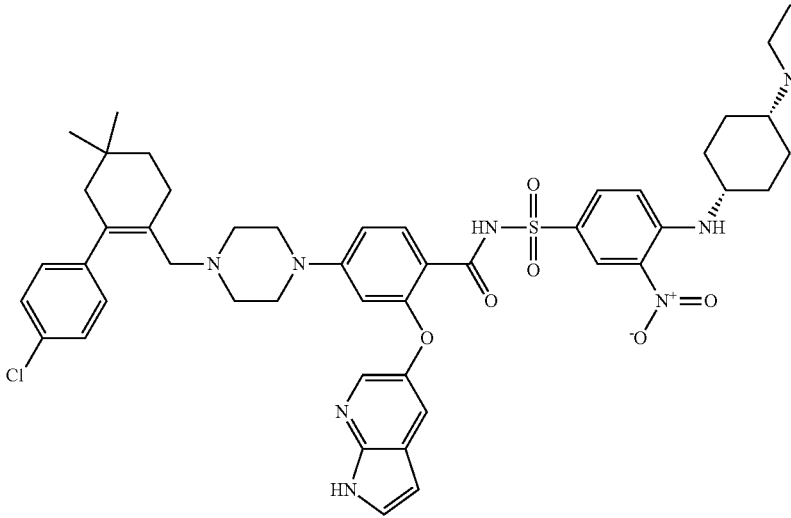 |
| 4-(4-{[2-(4-chlorophenyl)-4,4-dimethylcyclohex-1-en-1-yl]methyl}piperazin-1-yl)-N-{[5-chloro-6-(tetrahydro-2H-pyran-4-ylmethoxy)pyridin-3-yl]sulfonyl}-2-(1H-pyrrolo[2,3-b]pyridin-5-yloxy)benzamide | 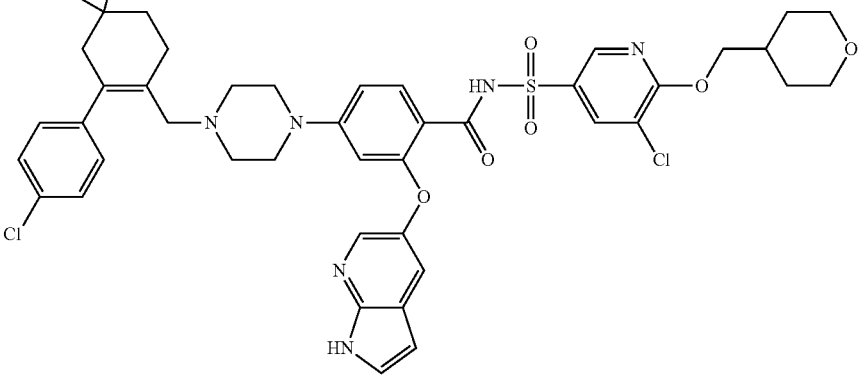 |
| 4-{4-{[4-(4-chlorophenyl)-6,6-dimethyl-5,6-dihydro-2H-pyran-3-yl]methyl}piperazin-1-yl)-N-{[5-chloro-6-(tetrahydro-2H-pyran-4-ylmethoxy)pyridin-3-yl]sulfonyl}-2-(1H-pyrrolo[2,3-b]pyridin-5-yloxy)benzamide | 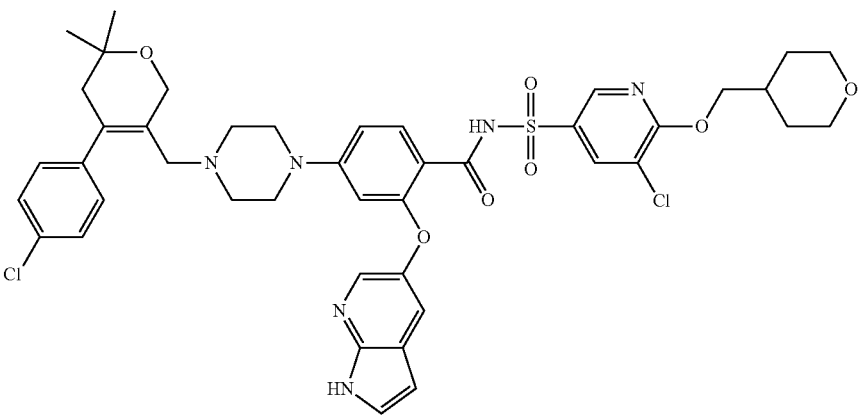 [SMILES: CC1(C)CCC(CN2CCN(c3ccc(C(=O)NS(=O)(=O)c4cnc(OCC5CCOCC5)c(Cl)c4)c(Oc4cnc5[nH]ccc5c4)c3)CC2)=C(c2ccc(Cl)cc2)C1] |

| Name | Structure |
|---|---|
| 4-(4-{[4-(4-chlorophenyl)-6,6-dimethyl-5,6-dihydro-2H-pyran-3-yl]methyl}piperazin-1-yl)-2-(1H-pyrrolo[2,3-b]pyridin-5-yloxy)-N-{[4-[(tetrahydro-2H-pyran-4-ylmethyl)amino]-3-(trifluoromethyl)phenyl]sulfonyl}benzamide | |
| 4-(4-{[4-(4-chlorophenyl)-6,6-dimethyl-5,6-dihydro-2H-pyran-3-yl]methyl}piperazin-1-yl)-2-(1H-pyrrolo[2,3-b]pyridin-yloxy)-N-({4-[(tetrahydro-2H-pyran-4-ylmethyl)amino]-3-[(trifluoromethyl)sulfonyl]phenyl}sulfonyl)benzamide | 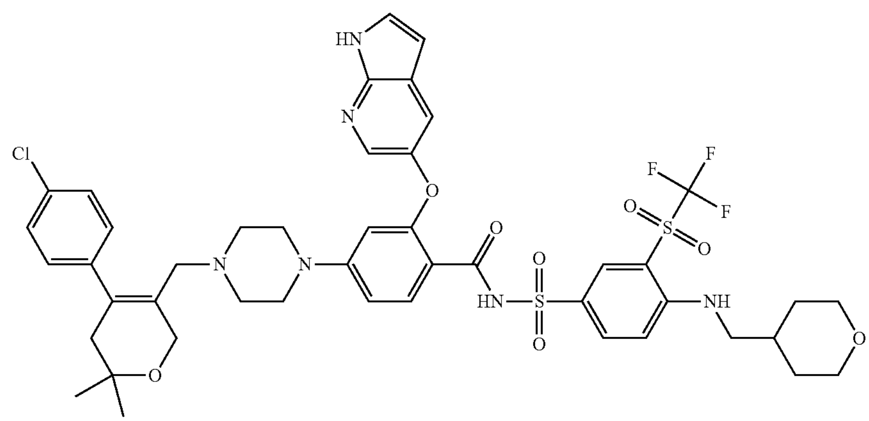 |
| Trans-4-(4-{[4-(4-chlorophenyl)-6,6-dimethyl-5,6-dihydro-2H-pyran-3-yl]methyl}piperazin-1-yl)-N-({4-[(4-morpholin-4-ylcyclohexyl)amino]-3-[(trifluoromethyl)sulfonyl]phenyl}sulfonyl)-2-(1H-pyrrolo[2,3-b]pyridin-5-yloxy)benzamide | 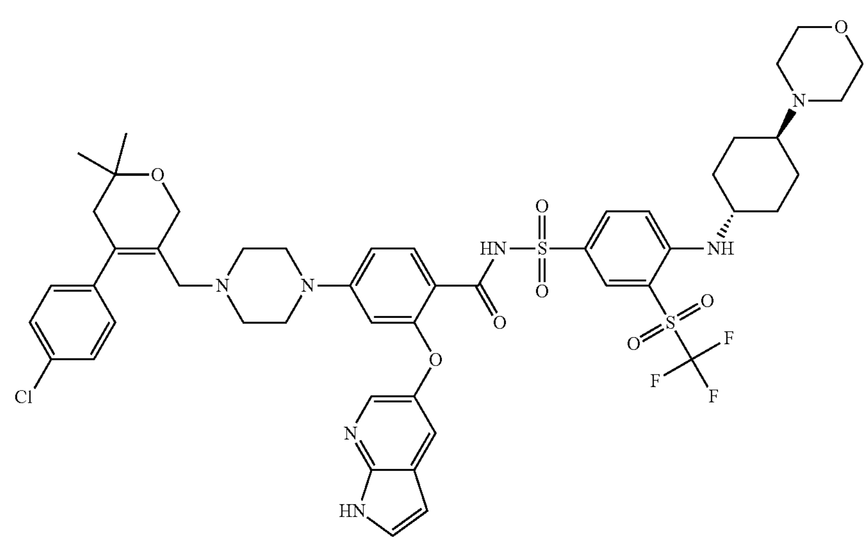 [SMILES: CC1(C)CC(c2ccc(Cl)cc2)=C(CN2CCN(c3ccc(C(=O)NS(=O)(=O)c4ccc(N[C@H]5CC[C@H](N6CCOCC6)CC5)c(S(=O)(=O)C(F)(F)F)c4)c(Oc4cnc5[nH]ccc5c4)c3)CC2)CO1] |

| Name | Structure |
|---|---|
| 4-(4-{[4-(4-chlorophenyl)-6,6-dimethyl-5,6-dihydro-2H-pyran-3-yl]methyl}piperazin-1-yl)-N-({4-[(1-methylpiperidin-4-yl)amino]-3-[(trifluoromethyl)sulfonyl]phenyl}sulfonyl)-2-(1H-pyrrolo[2,3-b]pyridin-5-yloxy)benzamide | 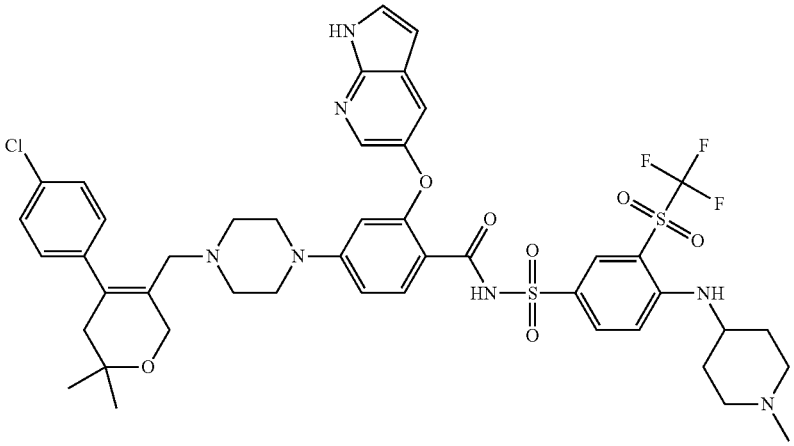 [SMILES: CN1CCC(Nc2ccc(S(=O)(=O)NC(=O)c3ccc(N4CCN(CC5=C(c6ccc(Cl)cc6)CC(C)(C)OC5)CC4)cc3Oc3cnc4[nH]ccc4c3)cc2S(=O)(=O)C(F)(F)F)CC1] |
| 5-({[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]amino}sulfonyl)-2-(tetrahydro-2H-pyran-4-ylmethoxy)nicotinamide | 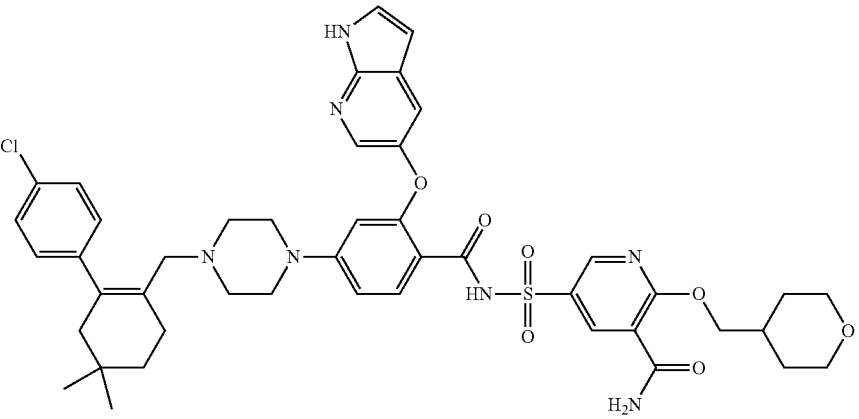 [SMILES: CC1(C)CCC(CN2CCN(c3ccc(C(=O)NS(=O)(=O)c4cnc(OCC5CCOCC5)c(C(N)=O)c4)c(Oc4cnc5[nH]ccc5c4)c3)CC2)=C(c2ccc(Cl)cc2)C1] |
| N-({5-bromo-6-[(1-methylpiperidin-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | 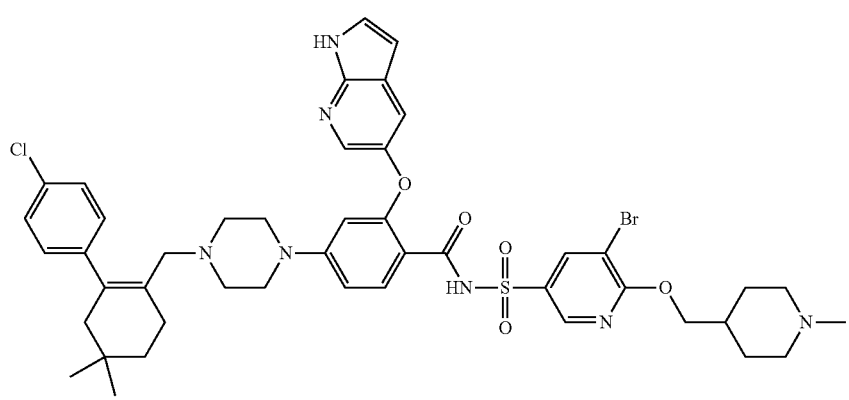 [SMILES: CN1CCC(COc2ncc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2Br)CC1] |

| Name | Structure |
|---|---|
| 4-(4-{[2-(4-chlorophenyl)-4,4-dimethylcyclohex-1-en-1-yl]methyl}piperazin-1-yl)-N-({4-[(1-methylpiperidin-4-yl)methoxy]-3-nitrophenyl}sulfonyl)-2-(1H-pyrrolo[2,3-b]pyridin-5-yloxy)benzamide | 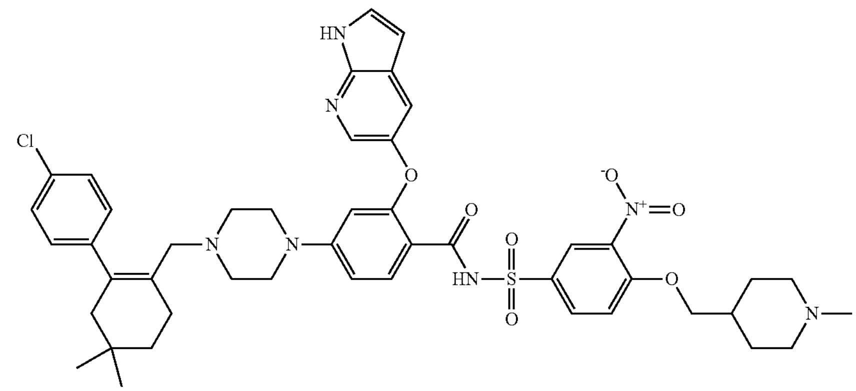 |
| 4-(4-{[2-(4-chlorophenyl)-4,4-dimethylcyclohex-1-en-1-yl]methyl}piperazin-1-yl)-N-{[5-cyano-6-(1,4-dioxan-2-ylmethoxy)pyridin-3-yl]sulfonyl}-2-(1H-pyrrolo[2,3-b]pyridin-5-yloxy)benzamide | 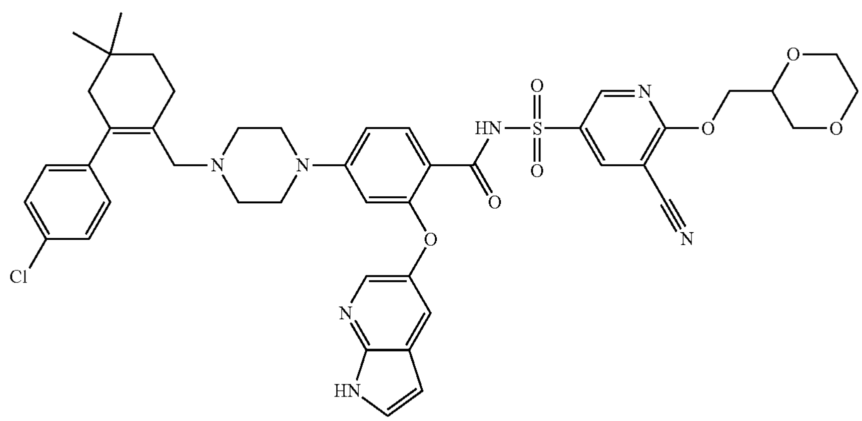 [SMILES: CC1(C)CCC(CN2CCN(c3ccc(C(=O)NS(=O)(=O)c4cnc(OCC5COCCO5)c(C#N)c4)c(Oc4cnc5[nH]ccc5c4)c3)CC2)=C(c2ccc(Cl)cc2)C1] |
| N-{[5-bromo-6-(1,4-dioxan-2-ylmethoxy)pyridin-3-yl]sulfonyl}-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | 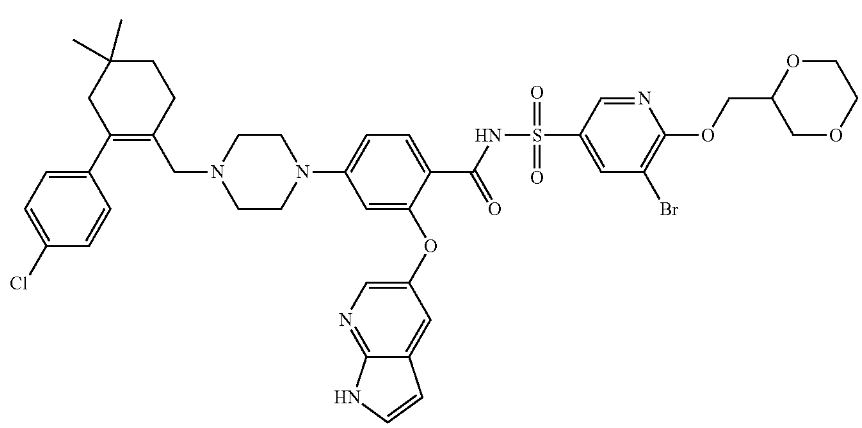 [SMILES: CC1(C)CCC(CN2CCN(c3ccc(C(=O)NS(=O)(=O)c4cnc(OCC5COCCO5)c(Br)c4)c(Oc4cnc5[nH]ccc5c4)c3)CC2)=C(c2ccc(Cl)cc2)C1] |

| Name | Structure |
|---|---|
| 4-(4-{[2-(4-chlorophenyl)-4,4-dimethylcyclohex-1-en-1-yl]methyl)piperazin-1-yl)-N-({4-[(2,2-dimethyltetrahydro-2H-pyran-4-yl)methoxy]-3-nitrophenyl}sulfonyl)-2-(1H-pyrrolo[2,3-b]pyridin-5-yloxy)benzamide | 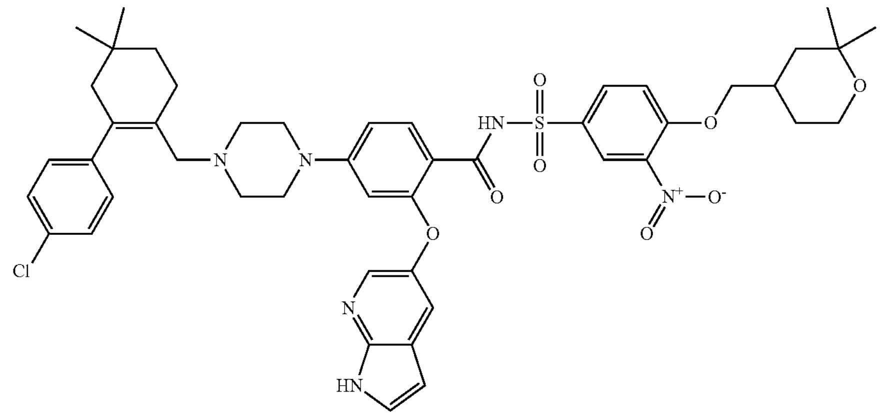 [SMILES: CC1(C)CCC(CN2CCN(c3ccc(C(=O)NS(=O)(=O)c4ccc(OCC5CCOC(C)(C)C5)c([N+](=O)[O-])c4)c(Oc4cnc5[nH]ccc5c4)c3)CC2)=C(c2ccc(Cl)cc2)C1] |
| N-({3-chloro-5-cyano-4-[(tetrahydro-2H-pyran-4-ylmethyl)amino]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | 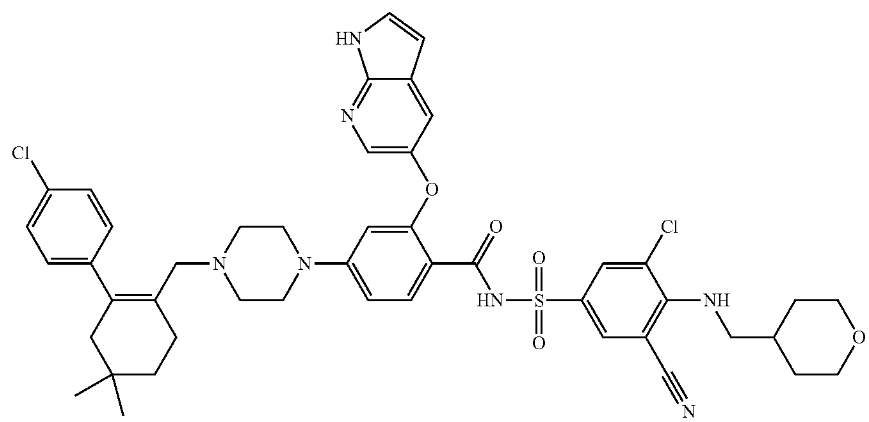 [SMILES: CC1(C)CCC(CN2CCN(c3ccc(C(=O)NS(=O)(=O)c4cc(Cl)c(NCC5CCOCC5)c(C#N)c4)c(Oc4cnc5[nH]ccc5c4)c3)CC2)=C(c2ccc(Cl)cc2)C1] |
| N-({4-[(1-acetylpiperidin-4-yl)amino]-3-nitrophenyl}sulfonyl)-4-(4-{[2-(4-chlorophenyl)-4,4-dimethylcyclohex-1-en-1-yl]methyl}piperazin-1-yl)-2-(1H-pyrrolo[2,3-bipyridin-5-yloxy)benzamide | |

| Name | Structure |
|---|---|
| N-({2-chloro-5-fluoro-4-[(tetrahydro-2H-pyran-4-ylmethyl)amino]phenyl}sulfonyl)-4-(4-{[2-(4-chlorophenyl-4,4-dimethylcyclohex-1-en-1-yl]methyl}piperazin-1-yl)-2-(1H-pyrrolo[2,3-b]pyridin-5-yloxy)benzamide | 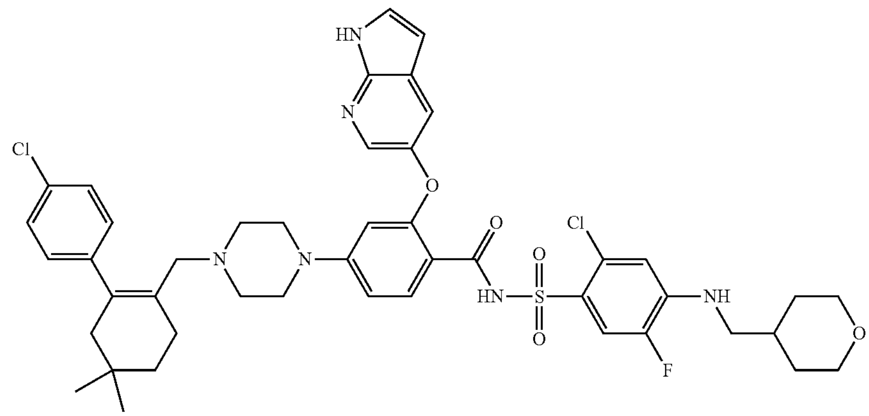 [SMILES: CC1(C)CCC(CN2CCN(c3ccc(C(=O)NS(=O)(=O)c4cc(F)c(NCC5CCOCC5)cc4Cl)c(Oc4cnc5[nH]ccc5c4)c3)CC2)=C(c2ccc(Cl)cc2)C1] |
| 4-(4-{[2-(4-chlorophenyl)-4,4-dimethylcyctohex-1-en-1-yl]methyl}piperazin-1-yl)-N-({4-(3-morpholin-4-ylpropyl)amino]-3-nitrophenyl}sulfonyl)-2-(1H-pyrrolo[2,3-b]pyridin-5-yloxy)benzamide | 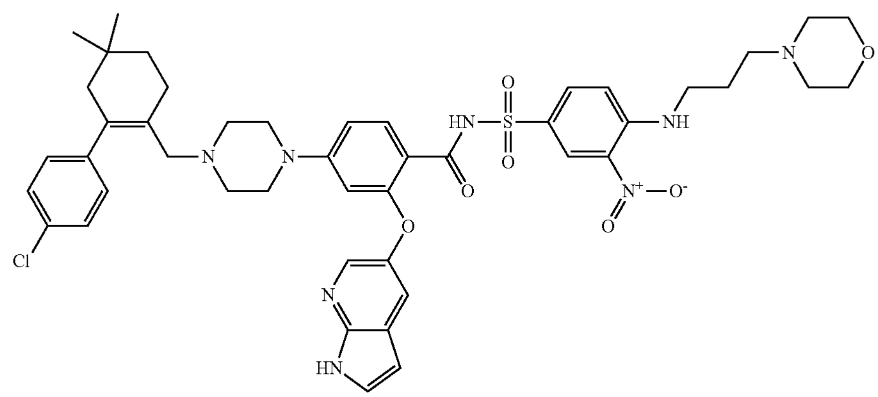 [SMILES: CC1(C)CCC(CN2CCN(c3ccc(C(=O)NS(=O)(=O)c4ccc(NCCCN5CCOCC5)c([N+](=O)[O-])c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-({5-cyano-6-[(4-fluorotetrahydro-2H-pyran-4-yl)methoxy]pyridin-3-yl}sulfonyl)-2-(1H-pyrrolo[2,3-b]pyridin-5-yloxy)benzamide | 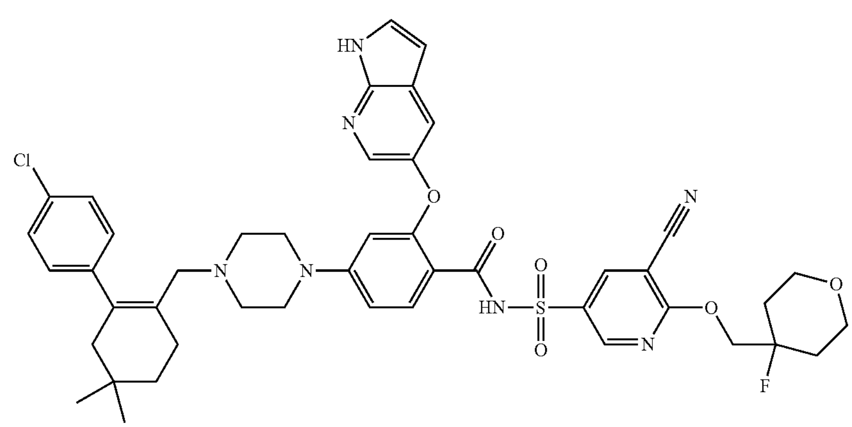 [SMILES: CC1(C)CCC(CN2CCN(c3ccc(C(=O)NS(=O)(=O)c4cnc(OCC5(F)CCOCC5)c(C#N)c4)c(Oc4cnc5[nH]ccc5c4)c3)CC2)=C(c2ccc(Cl)cc2)C1] |

-continued

| Name | Structure |
|---|---|
| 4-(4-{[2-(4-chlorophenyl)-4,4-dimethylcyclohex-1-en-1-yl]methyl}piperazin-1-yl)-N-{[5-cyano-6-(2-mopholin-4-ylethoxy)pyridin-3-yl]sulfonyl}-2-(1H-pyrrolo[2,3-b]pyridin-5-yloxy)benzamide | 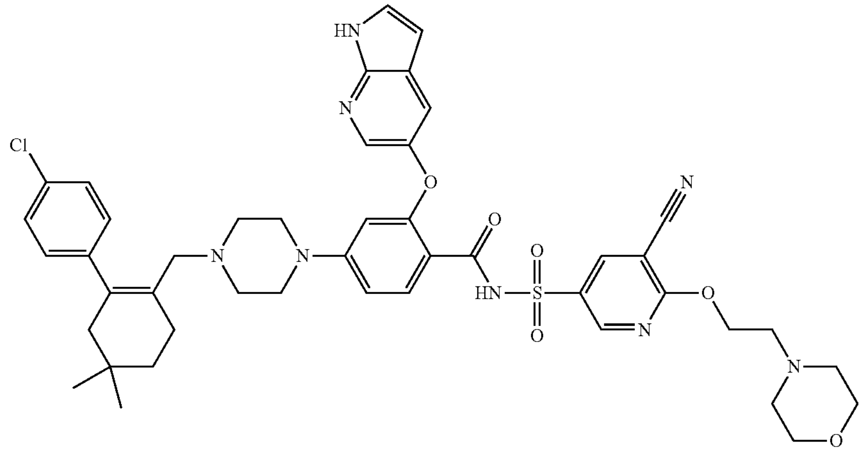 [SMILES: CC1(C)CCC(CN2CCN(c3ccc(C(=O)NS(=O)(=O)c4cnc(OCCN5CCOCC5)c(C#N)c4)c(Oc4cnc5[nH]ccc5c4)c3)CC2)=C(c2ccc(Cl)cc2)C1] |
| N-[(3-chloro-4-{[2-(2-methoxyethoxy)ethyl]sulfonyl}phenyl)sulfonyl]-4-(4-{[2-(4-chlorophenyl)-4,4-dimethylcyclohex-1-en-1-yl]methyl}piperazin-1-yl)-2-1H-pyrrolo[2,3-b]pyridin-5-yloxy)benzamide | 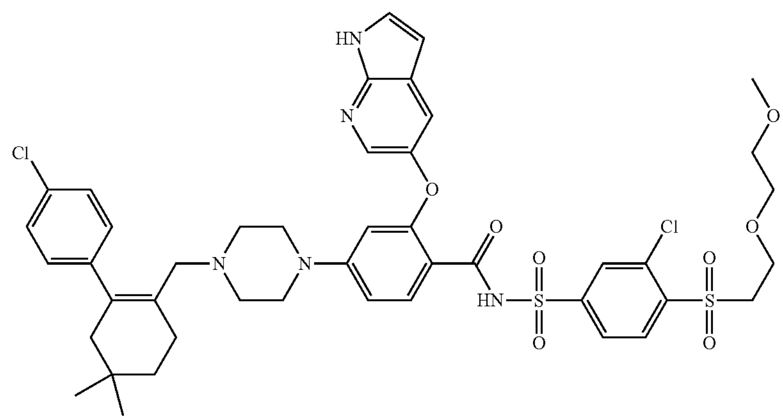 [SMILES: COCCOCCS(=O)(=O)c1ccc(S(=O)(=O)NC(=O)c2ccc(N3CCN(CC4=C(c5ccc(Cl)cc5)CC(C)(C)CC4)CC3)cc2Oc2cnc3[nH]ccc3c2)cc1Cl] |
| 4-(4-{[2(4-chlorophenyl)-4,4-dimethylcyclohex-1-en-1-yl]methyl}piperazin-1-yl)-N-[(4-{[2-(2-methoxyethoxy)ethyl]sulfonyl}-3-nitrophenyl)sulfonyl]-2-(1H-pyrroro[2,3-b]pyridin-5-yloxy)benzamide | 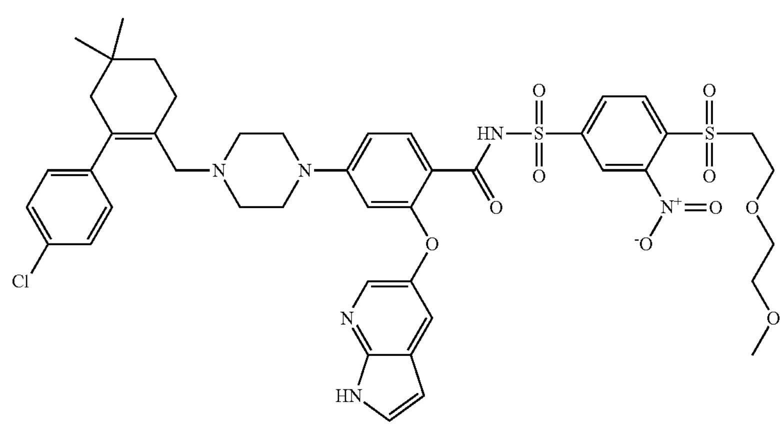 |

-continued

| Name | Structure |
|---|---|
| Trans-4-(4-{[2-(4-chlorophenyl)-4,4-dimethylcyclohex-1-en-1-yl]methyl}piperazin-1-yl)-N-({4-[(4-morpholin-4-ylcyclohexyl)oxy]-3-nitrophenyl}sulfonyl)-2-(1H-pyrrolo[2,3-b]pyridin-5-yloxy)benzamide | 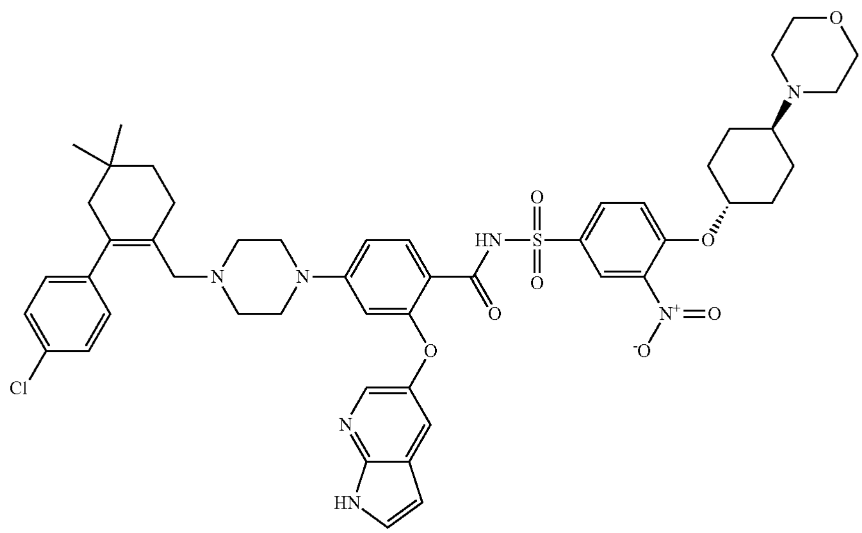 |
| N-({5-bromo-6-[(1-tetrahydro-2H-pyran-4-ylpiperidin-4-yl)amino]pyridin-3-yl}sulfonyl-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | 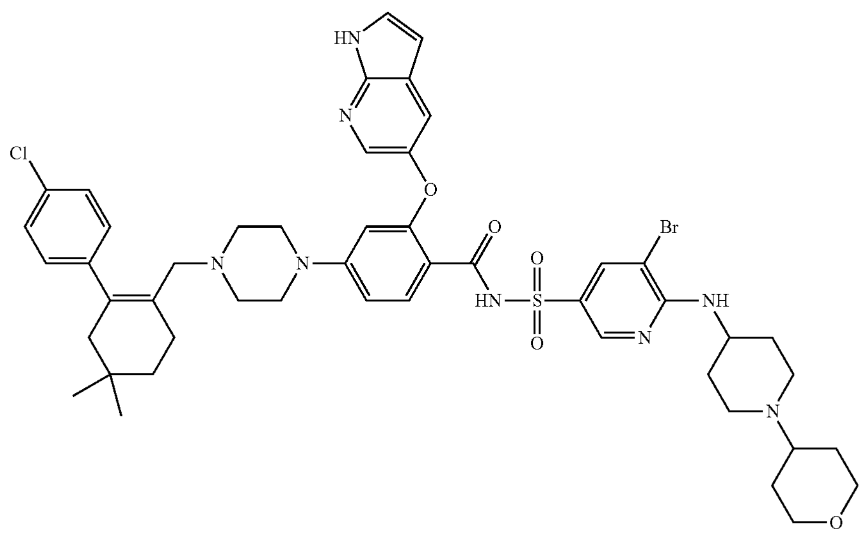 [SMILES: CC1(C)CCC(CN2CCN(c3ccc(C(=O)NS(=O)(=O)c4cnc(NC5CCN(C6CCOCC6)CC5)c(Br)c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-({4-[(2-cyano ethyl)amino]-3-nitrophenyl}sulfonyl)-2-(1H-pyrrolo[2,3-b]pyridin-5-yloxy)benzamide | 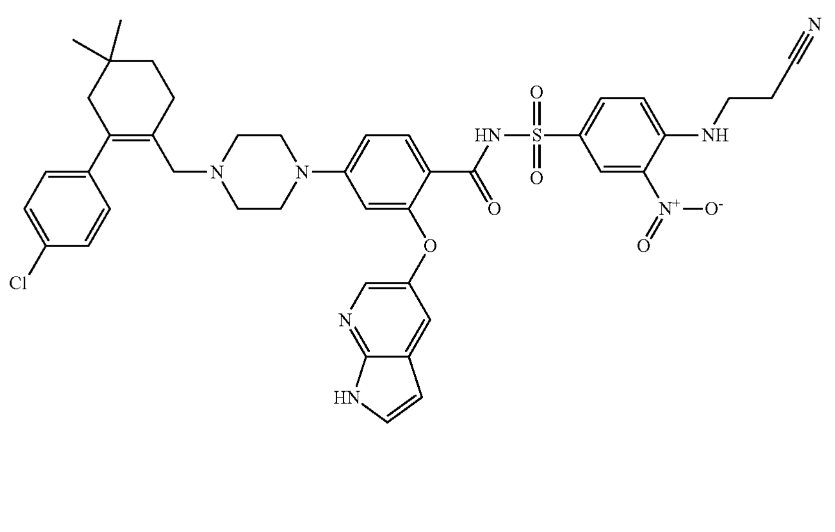 [SMILES: CC1(C)CCC(CN2CCN(c3ccc(C(=O)NS(=O)(=O)c4ccc(NCCC#N)c([N+](=O)[O-])c4)c(Oc4cnc5[nH]ccc5c4)c3)CC2)=C(c2ccc(Cl)cc2)C1] |

| Name | Structure |
|---|---|
| Cis-4-(4-{[4-(4-chlorophenyl)-6,6-dimethyl-5,6-dihydro-2H-pyran-3-yl]methyl}piperazin-1-yl)-N-({4-[(4-morpholin-4-ylcyclohexyl)amino]-3-nitrophenyl}sulfonyl)-2-(1H-pyrrolo[2,3-b]pyridin-5-yloxy)benzamide | 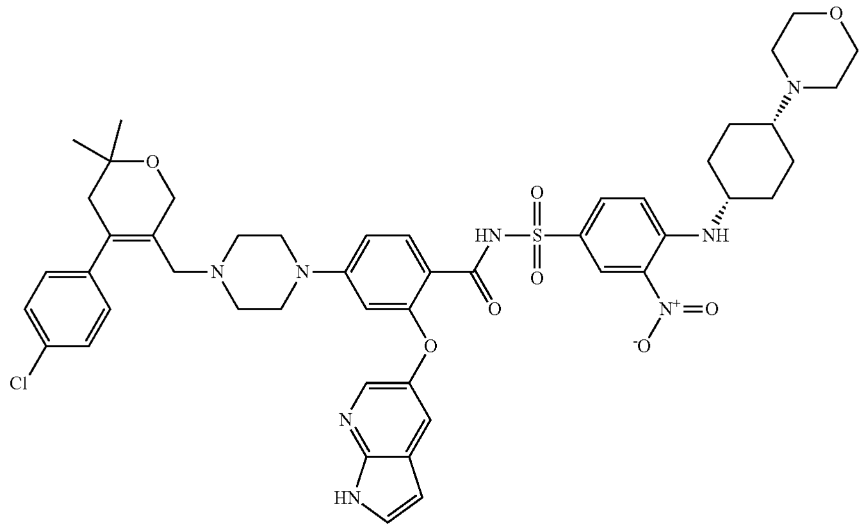 |
| Trans-N-{[4-({4-[bis(cyclopropylmethyl)amino]cyclohexyl}amino)-3-nitrophenyl]sulfonyl}-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | 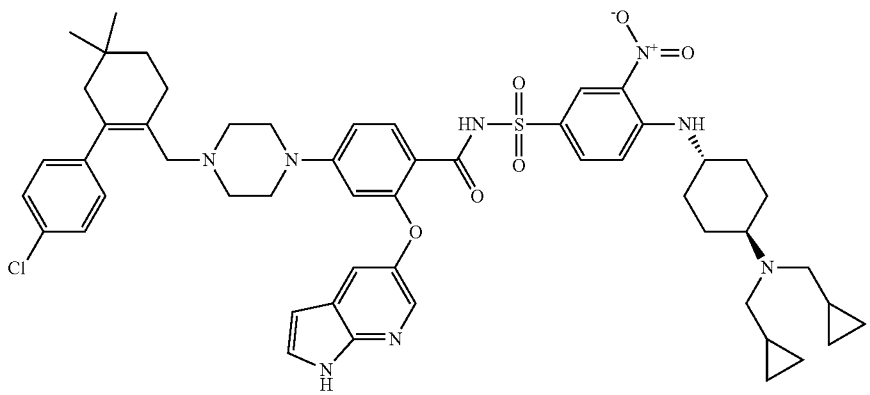 |
| 4-(4-{[2-(4-chlorophenyl)-4,4-dimethylcyclohex-1-en-1-yl]methyl}piperazin-1-yl)-N-[(4-{[(1-methylpiperidin-4-yl)methyl]amino}-3-nitrophenyl)sulfonyl]-2-(1H-pyrrolo[2,3-b]pyridin-5-yloxy)benzamide | 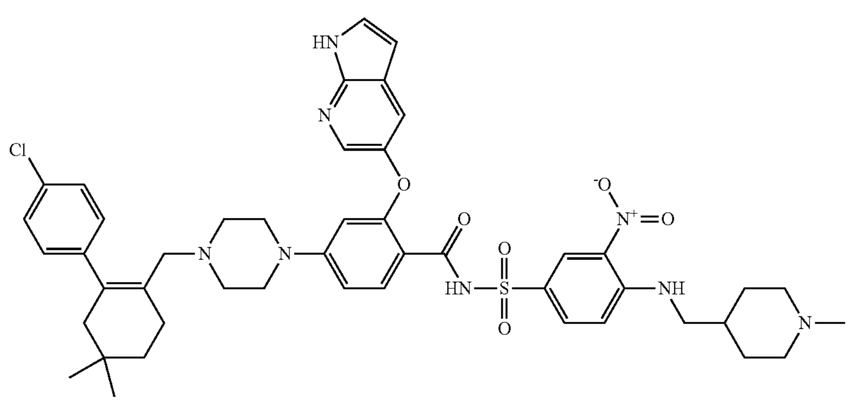 |

| Name | Structure |
|---|---|
| 4-(4-{[2(4-chlorophenyl)-4,4-dimethylcyclohex-1-en-1-yl]methyl}piperazin-1-yl)-N-([4-[(morpholin-3-ylmethyl)amino-]-3-nitrophenyl}sulfonyl)-2-(1H-pyrrolo[2,3-b]pyridin-5-yloxy)benzamide | 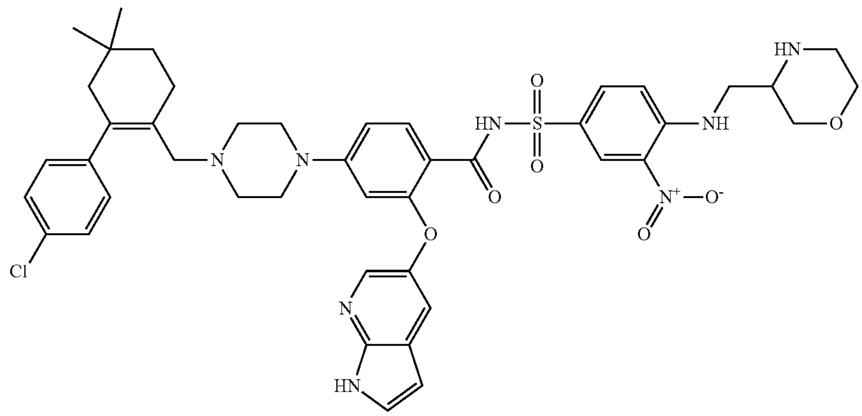 [SMILES: CC1(C)CCC(CN2CCN(c3ccc(C(=O)NS(=O)(=O)c4ccc(NCC5COCCN5)c([N+](=O)[O-])c4)c(Oc4cnc5[nH]ccc5c4)c3)CC2)=C(c2ccc(Cl)cc2)C1] |
| 4-(4-{[4-(4-chlorophenyl)-6,6-dimethyl-5,6-dihydro-2H-pyran-3-yl]methyl}piperazin-1-yl)-N-({4-(4-methylpiperazin-1-yl)amino]-3-nitrophenyl}sulfonyl)-2-(1H-pyrrolo[2,3-b]pyridin-5-yloxy)benzamide | 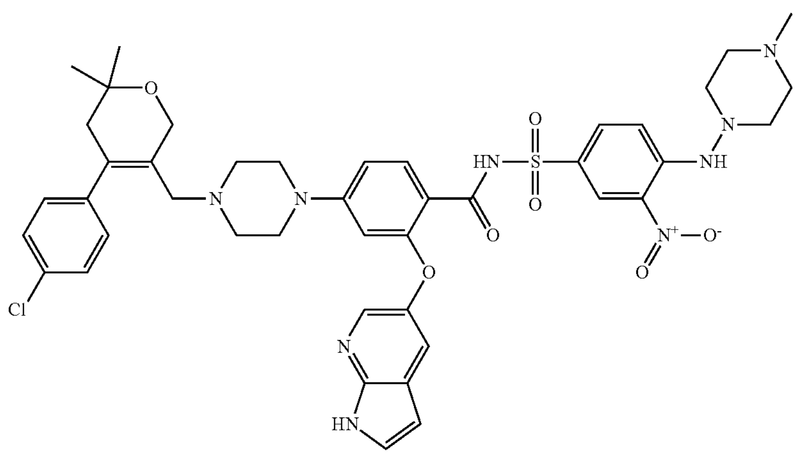 |
| 4-(4-{[2-(4-chlorophenyl)-4,4-dimethylcyclohex-1-en-1-yl]methyl}piperazin-1-yl)-N-({4-[(4-morpholin-4-ylbut-2-ynyl)oxy]-3-nitrophenyl}sulfonyl)-2-(1H-pyrrolo[2,3-b]pyridin-5-yloxy)benzamide | 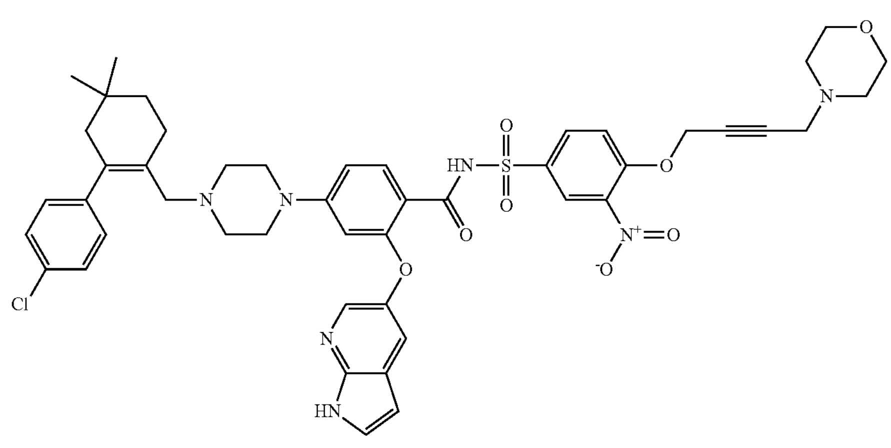 |

-continued

| Name | Structure |
|---|---|
| 4-(4-{[2-(4-chlorophenyl)-4,4-dimethylcyclohex-1-en-1-yl]methyl}piperazin-1-yl)-N-{[5-ethynyl-6-(tetrahydro-2H-pyran-4-ylmethoxy)pyridin-3-yl]sulfonyl}-2-(1H-pyrrolo[2,3-b]pyridin-5-yloxy)benzamide | 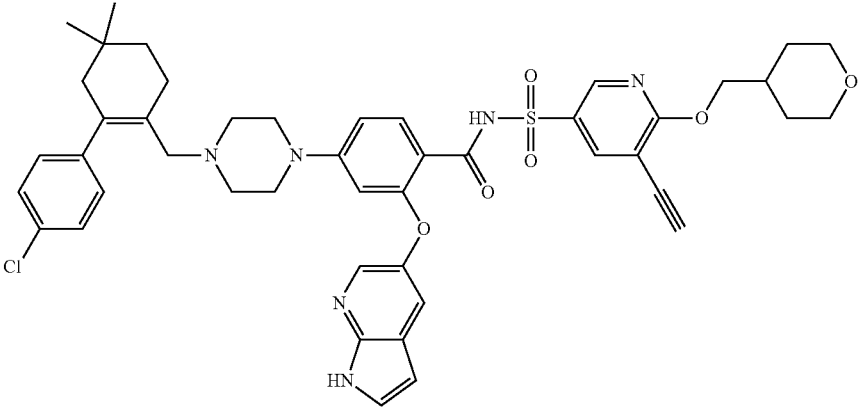 [SMILES: C#Cc1cc(S(=O)(=O)NC(=O)c2ccc(N3CCN(CC4=C(c5ccc(Cl)cc5)CC(C)(C)CC4)CC3)cc2Oc2cnc3[nH]ccc3c2)cnc1OCC1CCOCC1] |
| 4-(4-{[2-(4-chlorophenyl)-4,4-dimethylcyclohex-1-en-1-yl]methyl}piperazin-1-yl)-N-[(4-oxo-3,4-dihydroquinazolin-6-yl)sulfonyl]-2-(1H-pyrrolo[2,3-b]pyridin-5-yloxy)benzamide | 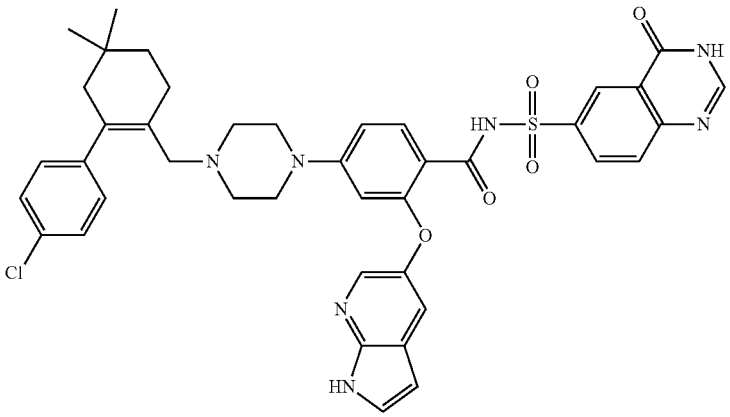 [SMILES: CC1(C)CCC(CN2CCN(c3ccc(C(=O)NS(=O)(=O)c4ccc5nc[nH]c(=O)c5c4)c(Oc4cnc5[nH]ccc5c4)c3)CC2)=C(c2ccc(Cl)cc2)C1] |
| Trans-4-(4-{[8-(4-chlorophenyl)spiro[4.5]dec-7-en-7-yl]methyl}piperazin-1-yl)-N-({4-[(4-morpholin-4-ylcyclohexyl)amino]-3-nitrophenyl}sulfonyl)-2-(1H-pyrroloo2,3-b]pyridin-5-yloxy)benzamide | 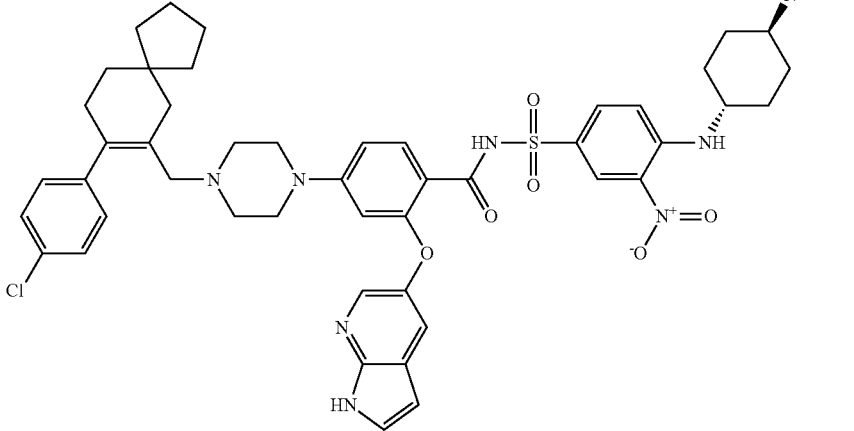 |

-continued

| Name | Structure |
|---|---|
| Cis-4-(4-{[4-(4-chlorophenyl)-6,6-dimethyl-5,6-dihydro-2H-pyran-3-yl]methyl}piperazin-1-yl)-N-[(4-{[(4-methoxycyclohexyl)methyl]amino}-3-nitrophenyl)sulfonyl]-2-(1H-pyrrolo[2,3-b]pyridin-5-yloxy)benzamide | 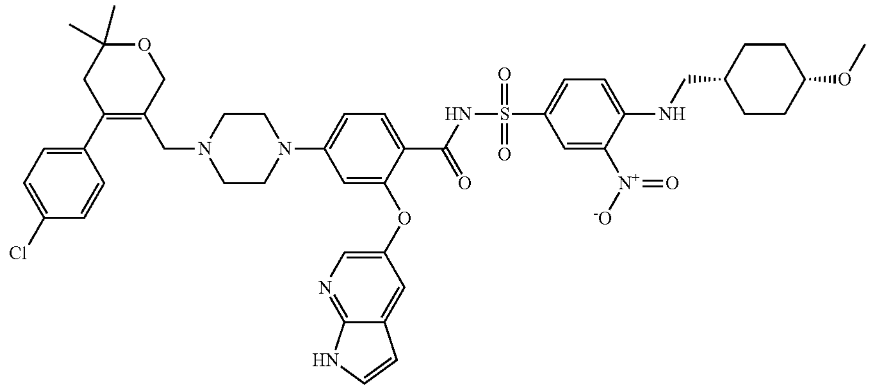 |
| 4-(4-{[-(4-chlorophenyl)spiro[4.5]dec-7-en-7-yl]methyl}piperazin-1-yl)-N-({4-[(4-fluorotetrahydro-2H-pyran-4-yl)methoxy]-3-nitrophenyl}sulfonyl)-2-(1H-pyrrolo[2,3-b]pyridin-5-yloxy)benzamide | 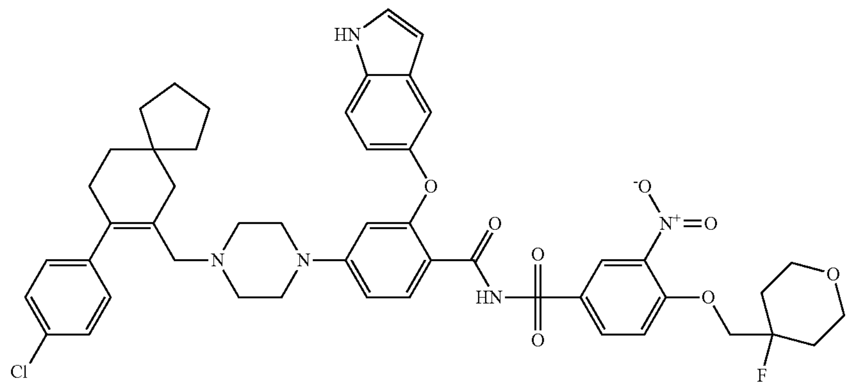 |
| Trans-4-(4-{[8-(4-chlorophenyl)spiro[4.5]dec-7-en-7-yl]methyl}piperazin-4-yl)-N-[(4-{[(4-methoxycyclohexyl)methyl]amino}-3-nitrophenyl)sulfonyl]-2-(1H-pyrrolo[2,3-b]pyridin-5-yloxy)benzamide | 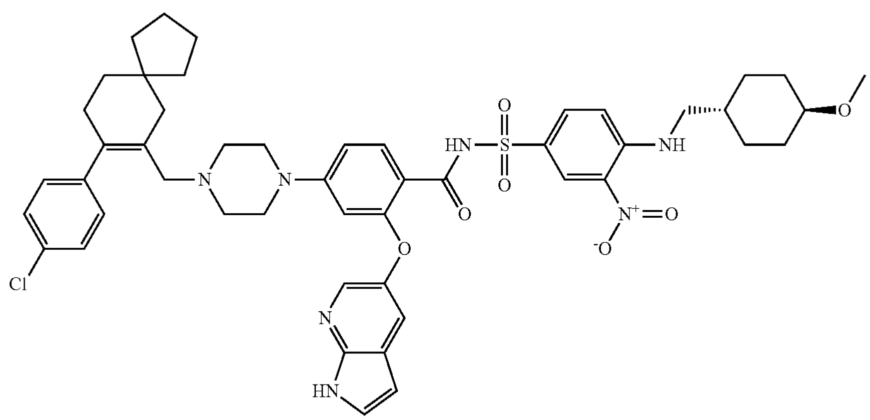 |
| 4-(4-{[2-(4-chlorophenyl)-5,5-dimethylcyclohex-1-en-1-yl]methyl}piperazin-1-yl)-N-({3-nitro-4-(tetrahydro-2H-pyran-4-ylmethyl)amino]phenyl}sulfonyl)-2-(1H-pyrrolo[2,3-b]pyridin-5-yloxy)benzamide | |

| Name | Structure |
|---|---|
| 4-(4-{[2-(4-chlorophenyl)-5,5-dimethylcyclohex-1-en-1-yl]methyl}piperazin-1-yl)-N-{[5-cyano-6-(tetrahydro-2H-pyran-4-ylmethoxy)pyridin-3-yl]sulfonyl]-2-(1H-pyrrolo[2,3-b]pyridin-5-yloxy)benzamide | 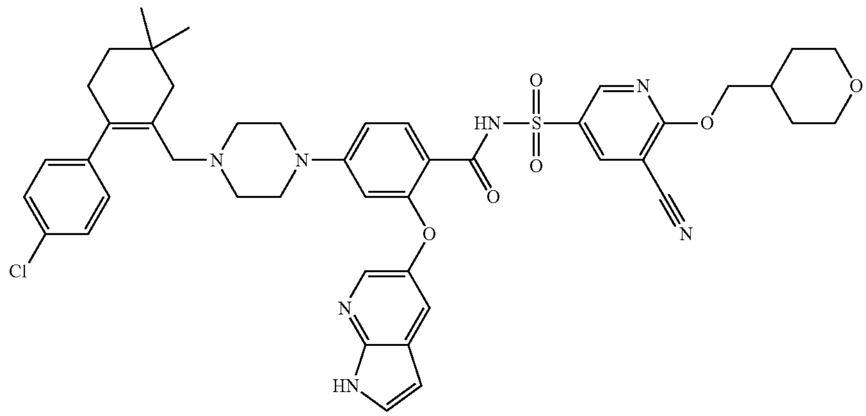 [SMILES: CC1(C)CCC(c2ccc(Cl)cc2)=C(CN2CCN(c3ccc(C(=O)NS(=O)(=O)c4cnc(OCC5CCOCC5)c(C#N)c4)c(Oc4cnc5[nH]ccc5c4)c3)CC2)C1] |
| tert-butyl 3-{[4-({[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]amino}sulfonyl)-2-nitrophenoxy]methyl}morpholine-4-carboxylate | |
| 4(4-{[2-(4-chlorophenyl)-4,4-dimethylcyclohex-1-en-1-yl]methyl}piperazin-1-yl)-N-{[4-(morpholin-3-ylmethoxy)-3-nitrophenyl]sulfonyl}-2-(1H-pyrrolo[2,3-b]pyridin-5-yloxy)benzamide | 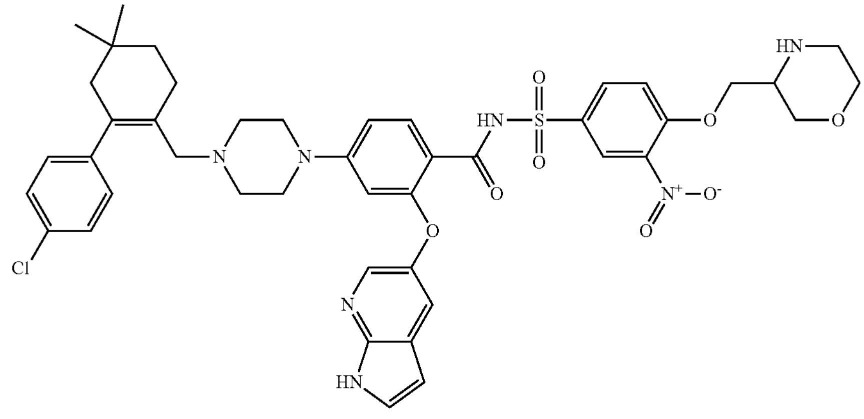 |

-continued

| Name | Structure |
|---|---|
| 4-(4-{[8-(4-chlorophenyl)spiro[4.5]dec-7-en-7-yl]methyl}piperazin-1-yl)-N-([3-nitro-4-[(tetrahydro-2H-pyran-4-ylmethyl)amino]phenyl}sulfonyl)-2-(1H-pyrrolo[2,3-b]pyridin-5-yloxy)benzamide | |
| 4-(4-{[2-(4-chlorophenyl)-4,4-dimethylcyclohex-1-en-1-yl]methyl}piperazin-1-yl)-N-[(4-{[1-(methylsulfonyl)piperidin-4-yl]amino}-3-nitrophenyl)sulfonyl]-2-(1H-pyrrolo[2,3-b]pyridin-5-yloxy)benzamide | |
| 4-(4-{[2-(4-chlorophenyl)-4,4-dimethylcyclohex-1-en-1-yl]methyl}piperazin-1-yl)-N-({4-[(1,1-dioxidotetrahydro-2H-thiopyran-4-yl)amino]-3-nitrophenyl}sulfonyl)-2-(1H-pyrrolo[2,3-b]pyridin-5-yloxy)benzamide | |

| Name | Structure |
|---|---|
| N-[(4-chloro-3-nitrophenyl)sulfonyl]-4-(4-{[2-(4-chlorophenyl)-4,4-dimethylcyclohex-1-en-1-yl]methyl]piperazin-1-yl)-2-(1H-pyrrolo[2,3-b]pyridin-5-yloxy)benzamide | |
| 4-(4-{[2-(4-chlorophenyl)-4,4-dimethylcyclohex-1-en-1-yl]methyl}piperazin-1-yl)-N-[(3-nitro-4-{[1-(2,2,2-trifluoroethyl)piperidin-4-yl]amino}phenyl)sulfonyl]-2-(1H-pyrrolo[2,3-b]pyridin-5-yloxy)benzamide | 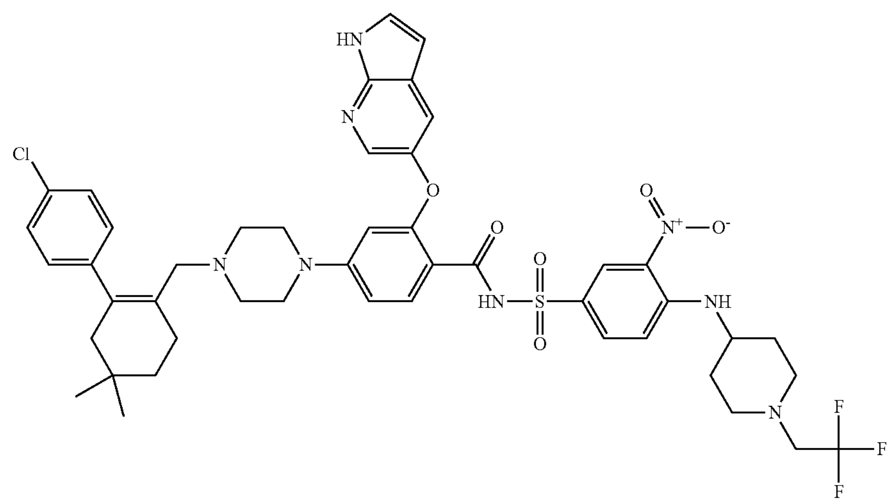 [SMILES: CC1(C)CCC(CN2CCN(c3ccc(C(=O)NS(=O)(=O)c4ccc(NC5CCN(CC(F)(F)F)CC5)c([N+](=O)[O-])c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-({5-cyano-6-[(1-tetrahydro-2H-pyran-4-ylpiperidin-4-yl)oxy]pyridin-3-yl}sulfonyl)-2-(1H-pyrrolo[2,3-b]pyridin-5-yloxy)benzamide | 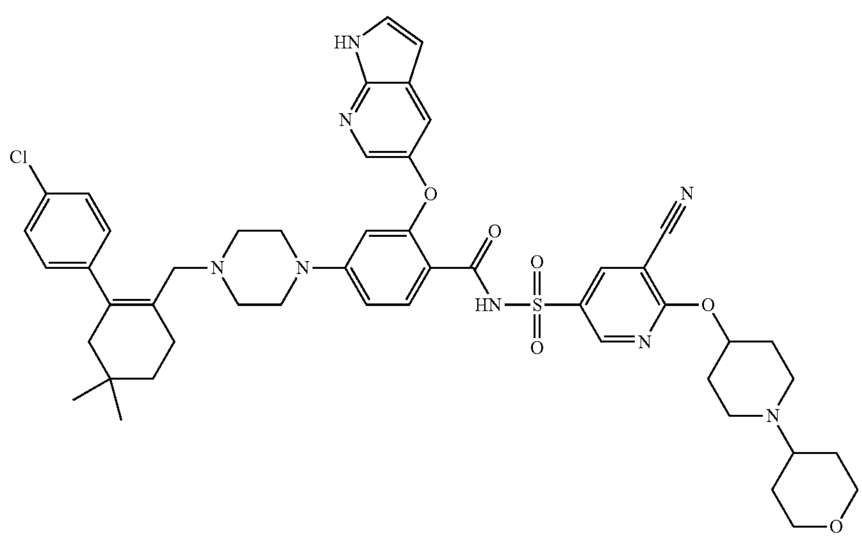 [SMILES: CC1(C)CCC(CN2CCN(c3ccc(C(=O)NS(=O)(=O)c4cnc(OC5CCN(C6CCOCC6)CC5)c(C#N)c4)c(Oc4cnc5[nH]ccc5c4)c3)CC2)=C(c2ccc(Cl)cc2)C1] |

-continued

| Name | Structure |
|---|---|
| 4-(4-{[2-(4-chlorophenyl)-4,4-dimethylcyclohex-1-en-1-yl]methyl}piperazin-1-yl)-N-{[5-isopropyl-6-(tetrahydro-2H-pyran-4-ylmethoxy)pyridin-3-yl]sulfonyl}-2-(1H-pyrrolo[2,3-b]pyridin-5-yloxy)benzamide | 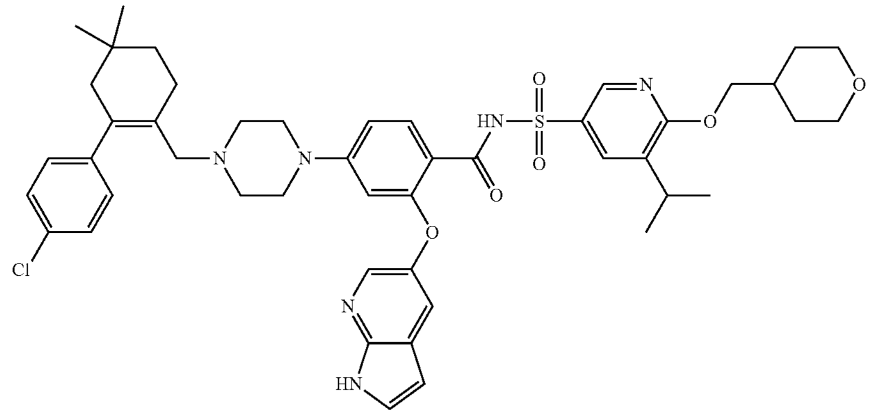 [SMILES: CC(C)c1cc(S(=O)(=O)NC(=O)c2ccc(N3CCN(CC4=C(c5ccc(Cl)cc5)CC(C)(C)CC4)CC3)cc2Oc2cnc3[nH]ccc3c2)cnc1OCC1CCOCC1] |
| N-({3-chloro-5-fluoro-4-[(tetrahydro-2H-pyran-4-ylmethyl)annno]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | 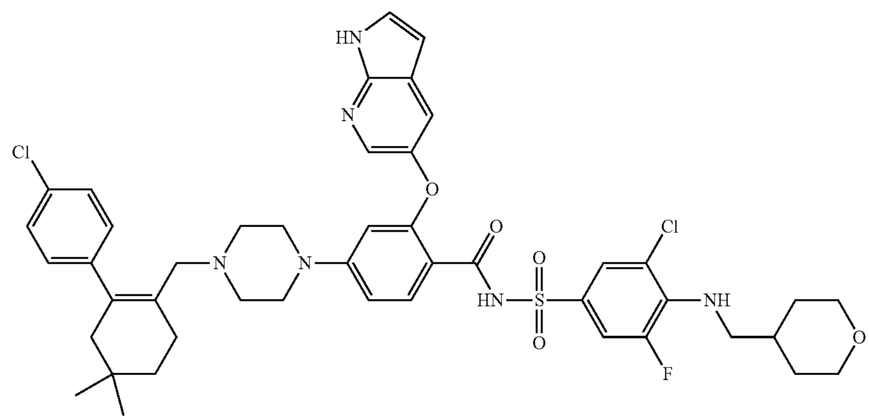 [SMILES: CC1(C)CCC(CN2CCN(c3ccc(C(=O)NS(=O)(=O)c4cc(F)c(NCC5CCOCC5)c(Cl)c4)c(Oc4cnc5[nH]ccc5c4)c3)CC2)=C(c2ccc(Cl)cc2)C1] |
| 4-{4-[(4'-chloro-1,1-biphenyl-2-yl)methyl]piperazin-1-yl}-2-(1H-indol-5-yloxy)-N-({3-nitro-4-[(tetrahydro-2H-pyran-4-ylmethyl)amino]phenyl}sulfonyl)benzamide | 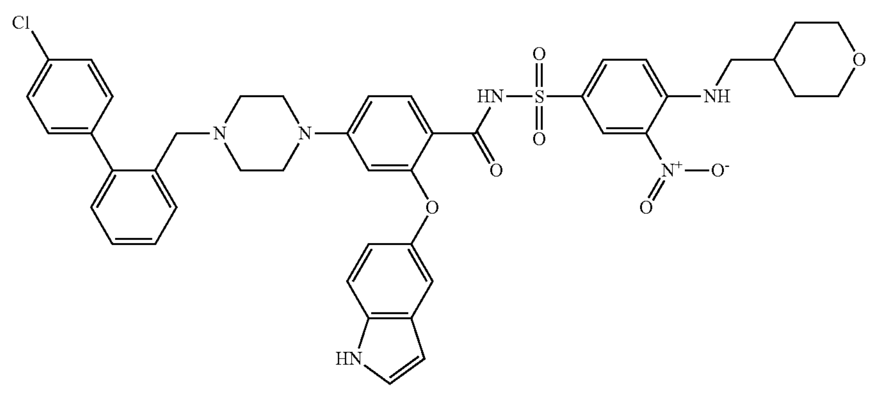 [SMILES: O=C(NS(=O)(=O)c1ccc(NCC2CCOCC2)c([N+](=O)[O-])c1)c1ccc(N2CCN(Cc3ccccc3-c3ccc(Cl)cc3)CC2)cc1Oc1ccc2[nH]ccc2c1] |
| 4-{4-[(4'-chloro-1,1'-biphenyl-2-yl)methyl]piperazin-1-yl}-2-(1H-indol-5-yloxy)-N-({4-[(3-morpholin-4-ylpropyl)amino]-3-nitrophenyl}sulfonyl)benzamide | 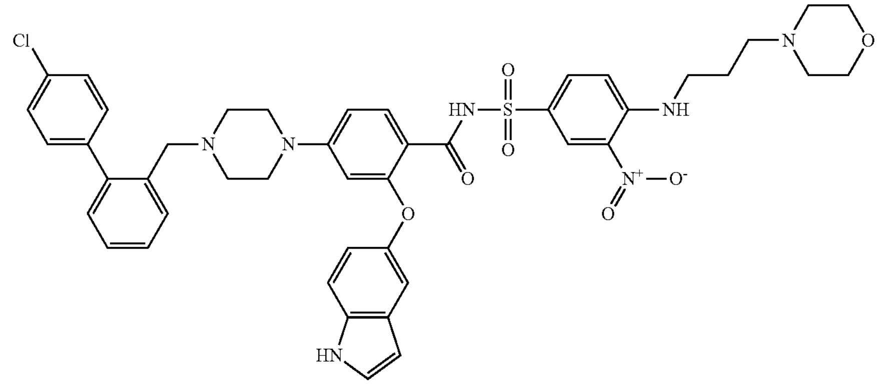 [SMILES: O=C(NS(=O)(=O)c1ccc(NCCCN2CCOCC2)c([N+](=O)[O-])c1)c1ccc(N2CCN(Cc3ccccc3-c3ccc(Cl)cc3)CC2)cc1Oc1ccc2[nH]ccc2c1] |

-continued

| Name | Structure |
|---|---|
| 4-(4-{[2-(4-chlorophenyl)-4,4-dimethylcyclohex-1-en-1-yl]methyl}piperazin-1-yl)-2-(1H-indol-5-yloxy)-N-({3-nitro-4-[(1-tetrahydro-2H-pyran-4-ylpiperidin-4-yl)amino]phenyl}sulfonyl)benzamide | 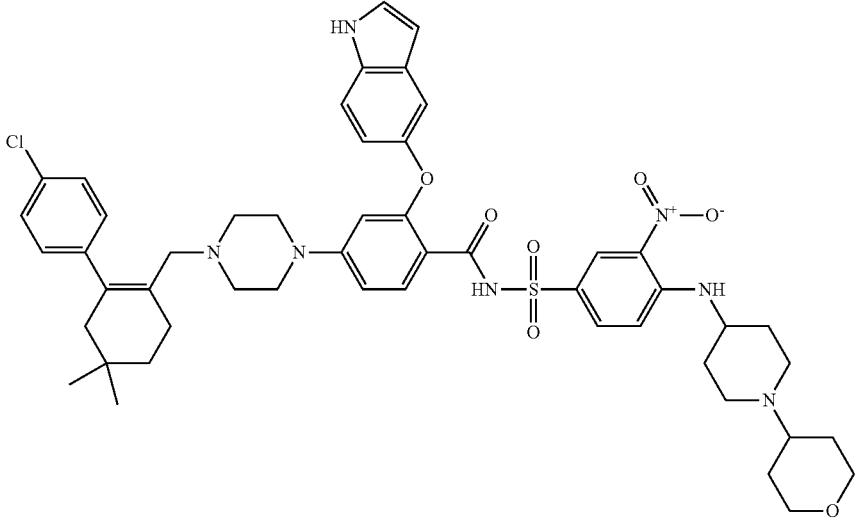 [SMILES: CC1(C)CCC(CN2CCN(c3ccc(C(=O)NS(=O)(=O)c4ccc(NC5CCN(C6CCOCC6)CC5)c([N+](=O)[O-])c4)c(Oc4ccc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-2-(1H-indol-5-yloxy)-N-({4-[(1-methylpiperidin-4-yl)amino]-3-nitrophenyl}sulfonyl)benzamide | 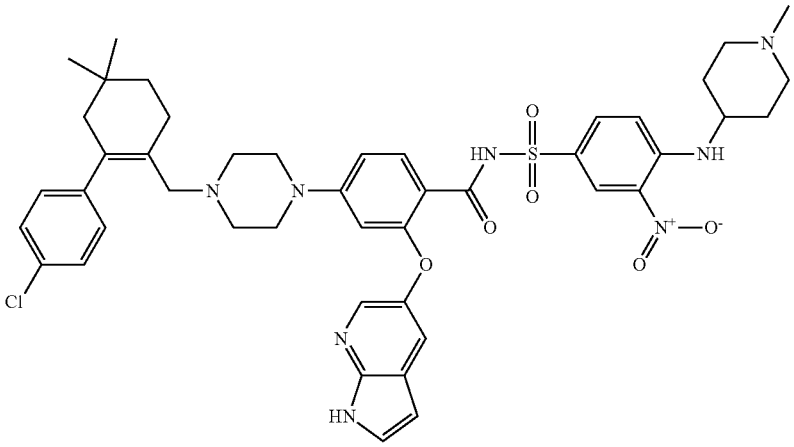 |
| 4-(4-{[2-(4-chlorophenyl)-4,4-dimethylcyclohex-1-en-1-yl]methyl}piperazin-1-yl)-2-(1H-indol-5-yloxy)-N-({4-[(4-methylpiperazin-1-yl)amino]-3-nitrophenyl}sulfonyl)benzamide | 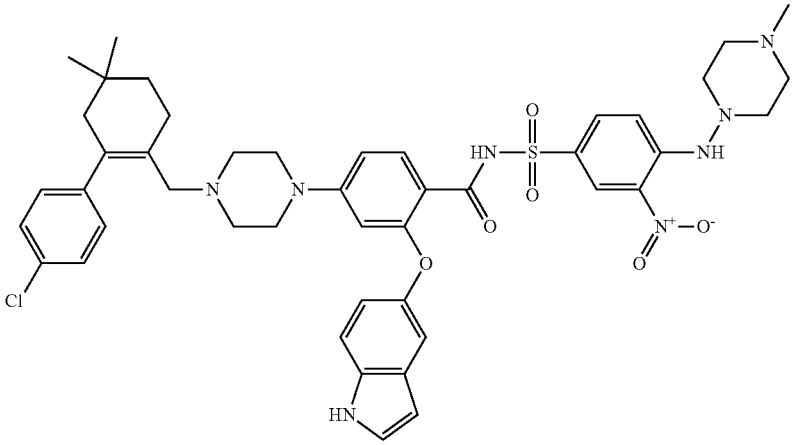 [SMILES: CN1CCN(Nc2ccc(S(=O)(=O)NC(=O)c3ccc(N4CCN(CC5=C(c6ccc(Cl)cc6)CC(C)(C)CC5)CC4)cc3Oc3ccc4[nH]ccc4c3)cc2[N+](=O)[O-])CC1] |

| Name | Structure |
|---|---|
| 4-(4-{[2-(4-chlorophenyl)-4,4-dimethylcyclohex-1-en-1-yl]methyl}piperazin-1-yl)-N-{[4-(1,4-dioxan-2-ylmethoxy)-3-nitrophenyl]sulfonyl}-2-(1H-indol-5-yloxy)benzamide | |
| 4-(4-{[2-{4-chlorophenyl)-4,4-dimethylcyclohex-1-en-1-yl]methyl}piperazin-1-yl)-2-(1H-indol-5-yloxy)-N-({4-[(2-methoxyethyl)amino]-3-[(trifluoromethyl)sulfonyl]phenyl}sulfonyl)benzamide | |
| 4-(4-{[2-(4-chlorophenyl)-4,4-dimethylcyclohex-1-en-1-yl]methyl}piperazin-1-yl)-2-(1H-indol-5-yloxy)-N-({4-[(tetrahydro-2H-pyran-4-ylmethyl)amino]-3-[(trifluoromethyl)sulfonyl]phenyl}sulfonyl)benzamide | |

| Name | Structure |
|---|---|
| 4-(4-{[2-(4-chlorophenyl)-4,4-dimethylcyclohex-1-en-1-yl]methyl}piperazin-1-yl)-N-{[4-({1-[2-fluoro-1-(fluoromethyl)ethyl]piperidin-4-yl}amino)-3-nitrophenyl]sulfonyl}-2-(1H-pyrrolo[2,3-b]pyridin-5-yloxy)benzamide | 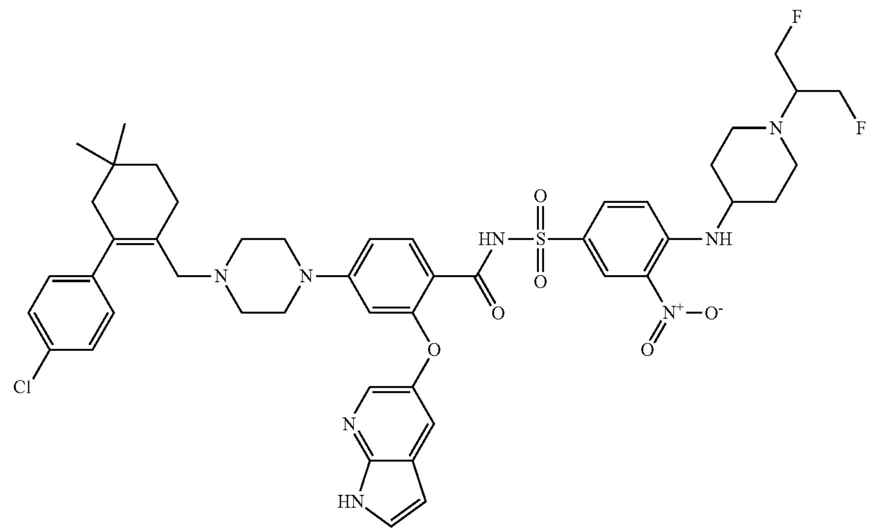 [SMILES: CC1(C)CCC(CN2CCN(c3ccc(C(=O)NS(=O)(=O)c4ccc(NC5CCN(C(CF)CF)CC5)c([N+](=O)[O-])c4)c(Oc4cnc5[nH]ccc5c4)c3)CC2)=C(c2ccc(Cl)cc2)C1] |
| N-({5-chloro-6-[(4-fluorotetrahydro-2H-pyran-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | 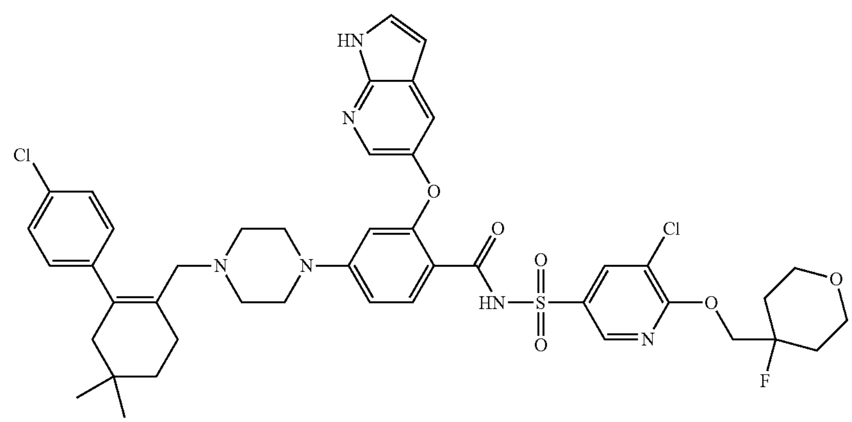 |
| 4-{4-{[2-{4-chlorophenyl)-4,4-dimethylcyclohex-1-en-1-yl]methyl}pipeaazin-1-yl)-N-[(4-{[1-(2,2-difloroethyl)piperidin-4-yl]amino}-3-nitrophenyl)sulfonyl]-2-(1H-pyrrolo[2,3-b]pyridin-5-yloxy)benzamide | 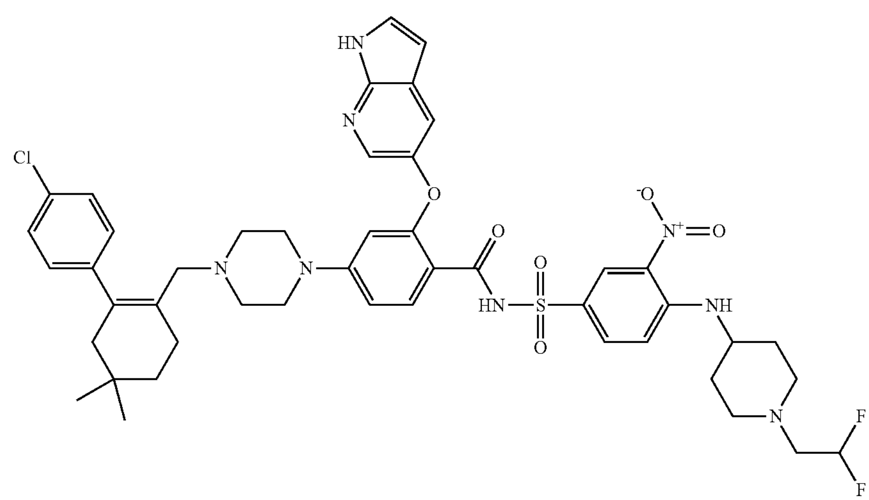 |

-continued

| Name | Structure |
|---|---|
| 4-(4-{[2-(4-chlorophenyl)-4,4-dimethylcyclohex-1-en-1-yl]methyl}piperazin-1-yl)-N-({4-[(1-cyclopropylpiperidin-4-yl)amino]-3-nitrophenyl)sulfonyl]-2-(1H-pyrrolo[2,3-b]pyridin-5-yloxy)benzamide | |
| 4-(4-{[2-(4-chlorophenyl)-4,4-dimethylcyclohex-1-en-1-yl]methyl}piperazin-1-yl)-N-({4-[(1-morpholin-4-ylcyclohexyl)methyl]amino}-3-nitrophenyl)sulfonyl]-2-(1H-pyrrolo[2,3-b]pyridin-5-yloxy)benzamide | 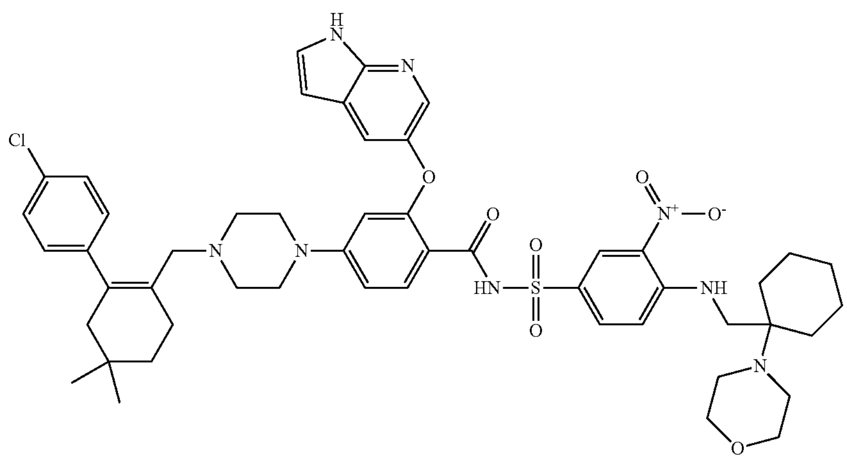 [SMILES: CC1(C)CCC(CN2CCN(c3ccc(C(=O)NS(=O)(=O)c4ccc(NCC5(N6CCOCC6)CCCCC5)c([N+](=O)[O-])c4)c(Oc4cnc5[nH]ccc5c4)c3)CC2)=C(c2ccc(Cl)cc2)C1] |
| Trans-4-(4-{[2-(4-chlorophenyl)-4,4-dimethylcyclohex-1-en-1-yl]methyl}piperazin-1-yl)-N-[(4-{[4-(dicyclopropylamino)cyclohexyl]amino}-3-nitrophenyl)sulfonyl]-2-(1H-pyrrolo[2,3-b]pyridin-5-yloxy)benzamide | 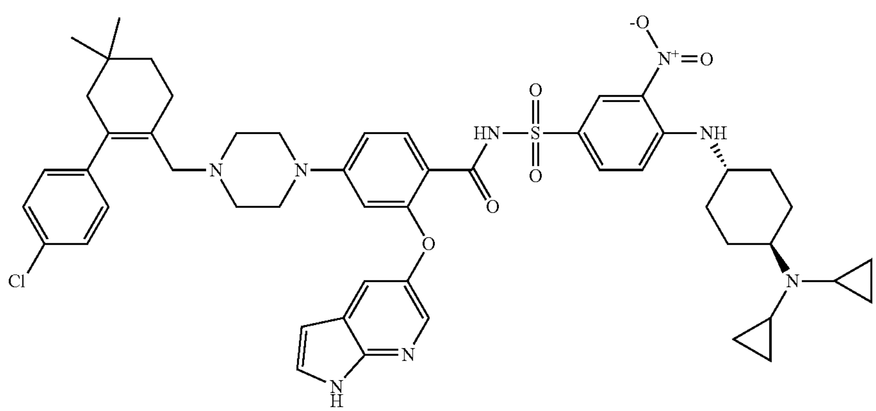 |

| Name | Structure |
|---|---|
| 4-(4-{[2-(4-chlorophenyl)-6,6-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide | 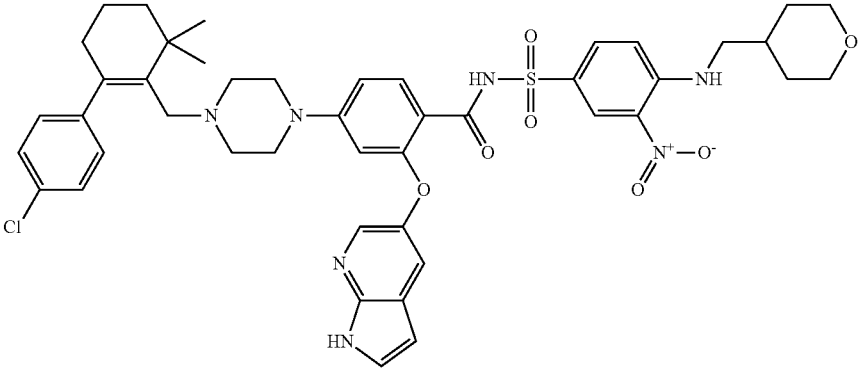 [SMILES: CC1(C)CCCC(c2ccc(Cl)cc2)=C1CN1CCN(c2ccc(C(=O)NS(=O)(=O)c3ccc(NCC4CCOCC4)c([N+](=O)[O-])c3)c(Oc3cnc4[nH]ccc4c3)c2)CC1] |
| N-([5-bromo-6-[(4-ethylmorpholin-3-yl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide |  |
| 4-(4-{[2-(4-chlorophenyl)-4,4-dimethylcyclohex-1-en-1-yl]methyl}piperazin-1-yl)-N-({4-[(4-ethylmorpholin-3-yl)methoxy]-3-nitrophenyl}sulfonyl)-2-(1H-pyrrolo[2,3-b]pyridin-5-yloxy)benzamide | 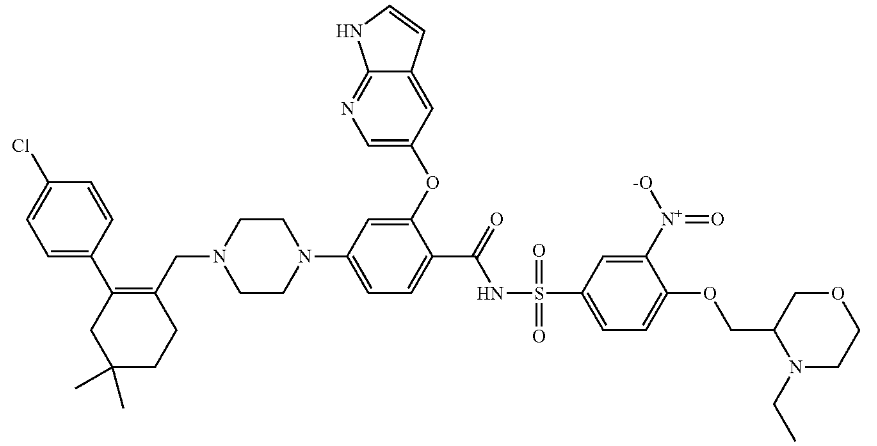 |

| Name | Structure |
|---|---|
| 4-(4-{[2-(4-chlorophenyl)-4,4-dimethylcyclohex-1-en-1-yl]methyl}piperazin-1-yl)-N-({3-nitro-4-[(4-tetrahydro-2H-pyran-4-ylmorpholin-3-yl)methoxy]phenyl}sulfonyl)-2-(1H-pyrrolo[2,3-b]pyridin-5-yloxy)benzamide | 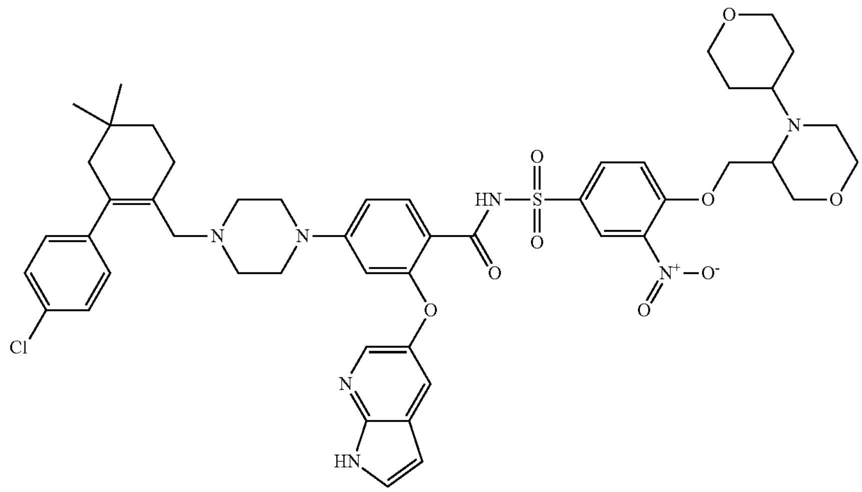 [SMILES: CC1(C)CCC(CN2CCN(c3ccc(C(=O)NS(=O)(=O)c4ccc(OCC5COCCN5C5CCOCC5)c([N+](=O)[O-])c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-[(3-nitro-4-{[(3S)-1-tetrahydro-2H-pyran-4-ylpiperidin-3-yl]amino}phenyl)sulfonyl]-2-(1H-pyrrolo[2,3-b]pyridin-5-yloxy)benzamide | 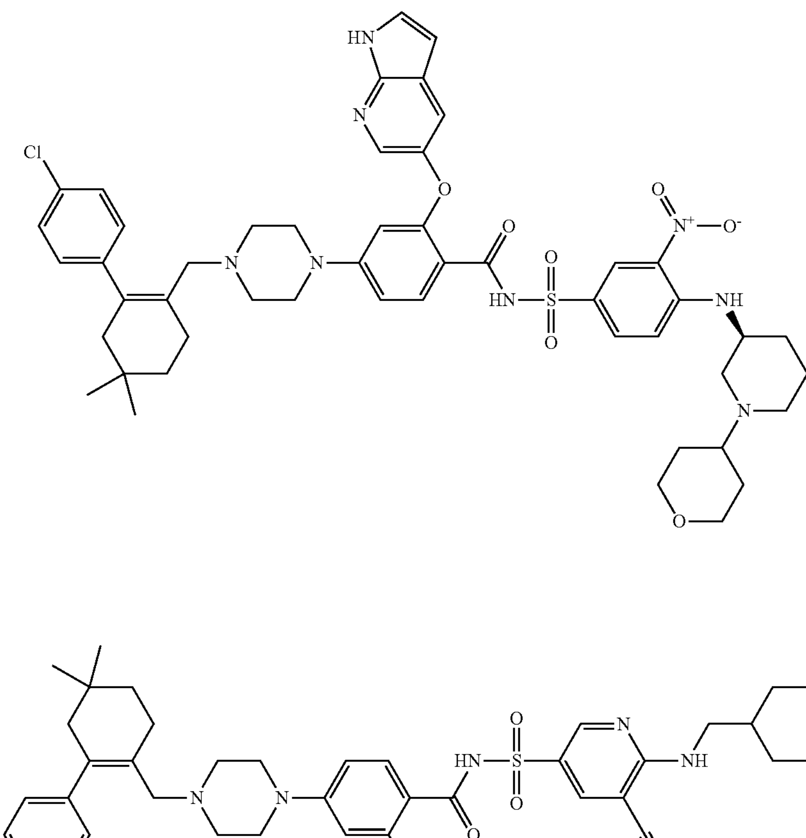 |
| 4-(4-{[2-(4-chlorophenyl)-4,4-dimethylcyclohex-1-en-1-yl]methyl}piperazin-1-yl)-N-({5-cyano-6-[(tetrahydro-2H-pyran-4-ylmethyl)amino]pyridin-3-yl}sulfonyl)-2-(1H-pyrrolo[2,3-b]pyridin-5-yloxy)benzamide | 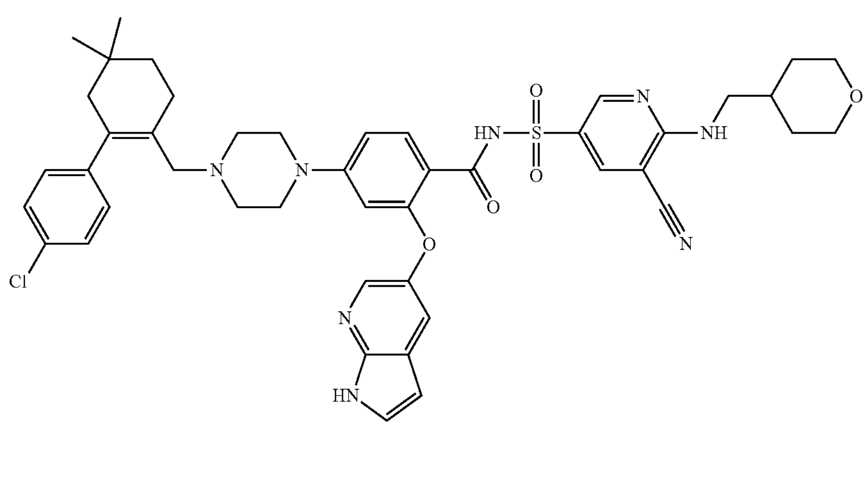 [SMILES: CC1(C)CCC(CN2CCN(c3ccc(C(=O)NS(=O)(=O)c4cnc(NCC5CCOCC5)c(C#N)c4)c(Oc4cnc5[nH]ccc5c4)c3)CC2)=C(c2ccc(Cl)cc2)C1] |

| Name | Structure |
|---|---|
| Trans-4-(4-{[2-(4-chlorophenyl)-4,4-dimethylcyclohex-1-en-1-yl]methyl}piperazin-1-yl)-N-({4-[(1,1-dioxidothiomorpholin-4-yl)amino]-3-nitrophenyl}sulfonyl)-2-(1H-pyrrolo[2,3-b]pyridin-5-yloxy)benzamide | 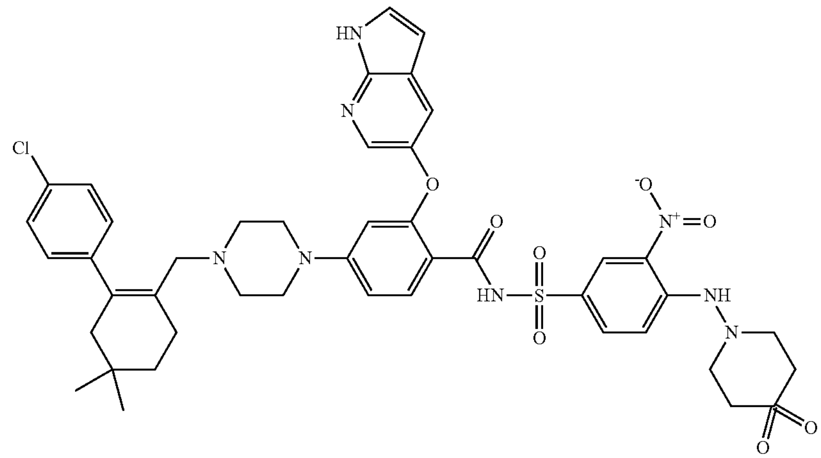 |
| N-[(4-{[(4-aminotetrahydro-2H-pyran-4-yl)methyl]amino}-3-nitrophenyl)sulfonyl]-4-(4-{(2-(4-chlorophenyl)-4,4-dimethylcyclohex-1-en-1-yl]methyl}piperazin-1-yl)-2-(1H-pyrrolo[2,3-b]pyridin-5-yloxy)benzamide | 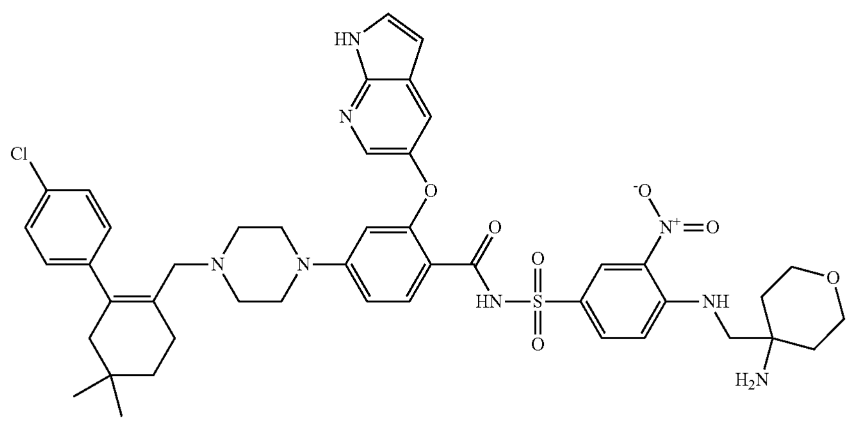 |
| Trans-4-(4-{[2-(4-chlorophenyl)-4,4-dimethylcyclohex-1-en-1-yl]methyl}piperazin-1-yl)-N-({5-cyano-6-[(4-morpholin-4-ylcyclohexyl)amino]pyridin-3-yl}sulfonyl)-2-(1H-pyrrolo[2,3-b]pyiidin-5-yloxy)benzamide | 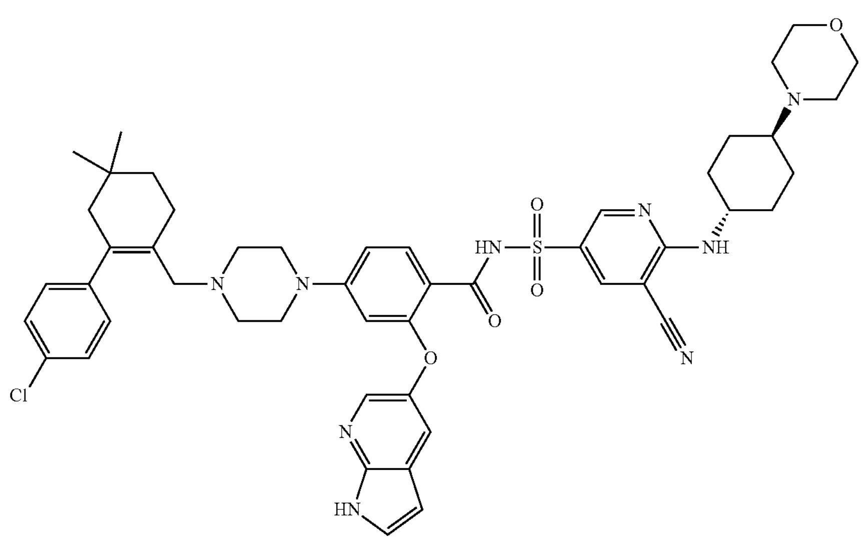 [SMILES: CC1(C)CCC(CN2CCN(c3ccc(C(=O)NS(=O)(=O)c4cnc(N[C@H]5CC[C@H](N6CCOCC6)CC5)c(C#N)c4)c(Oc4cnc5[nH]ccc5c4)c3)CC2)=C(c2ccc(Cl)cc2)C1] |

| Name | Structure |
|---|---|
| 4-(4-{[2-{4-chlorophenyl)-4,4-dimethylcyclohex-1-en-1-yl]methyl}piperazin-1-yl)-N-({3-cyano-4-[(tetrahydro-2H-pyran-4-ylmethyl)amino]phenyl}sulfonyl)-2-(1H-pyrrolo[2,3-b]pyridin-5-yloxy)benzamide | 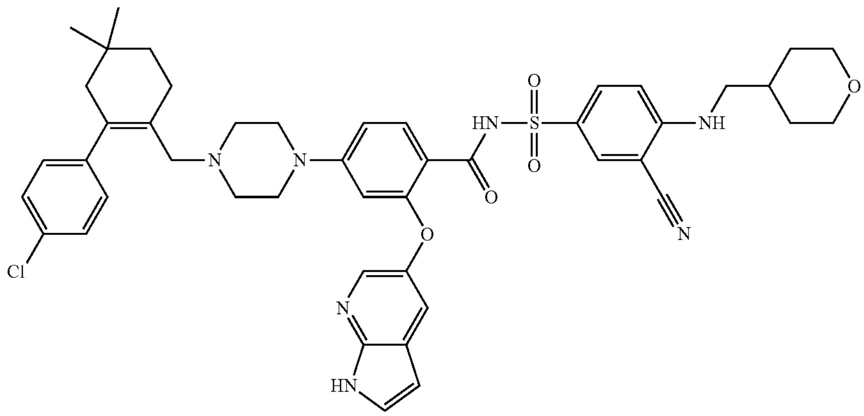 [SMILES: CC1(C)CCC(CN2CCN(c3ccc(C(=O)NS(=O)(=O)c4ccc(NCC5CCOCC5)c(C#N)c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-[(4-{[(1S,3R)-3-morpholin-4-ylcyclopentyl]arnino}-3-nitrophenyl)sulfonyl]-2-(1H-pyrrolo[2,3-b]pyridin-5-yloxy)benzamide | 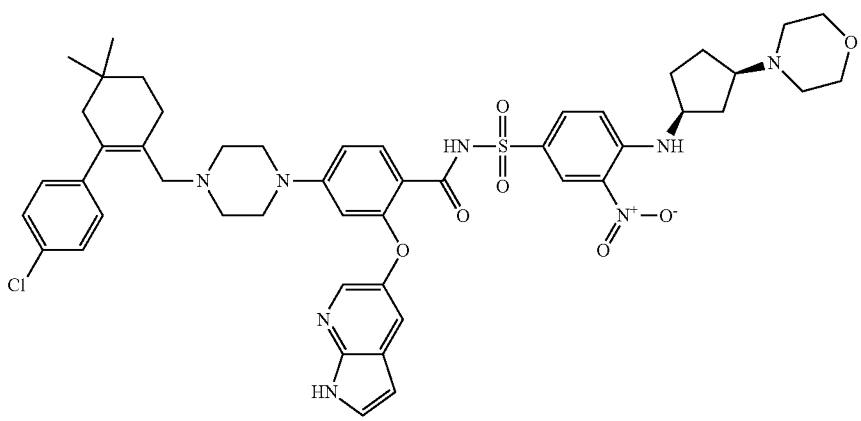 [SMILES: CC1(C)CCC(CN2CCN(c3ccc(C(=O)NS(=O)(=O)c4ccc(N[C@H]5CC[C@@H](N6CCOCC6)C5)c([N+](=O)[O-])c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-[(4-{[(1R,3S)-3-morpholin-4-ylcyclopentyl]amino}-3-nitrophenyl)sulfonyl]-2-(1H-pyrrolo[2,3-b]pyiridin-5-yloxy)benzamide | 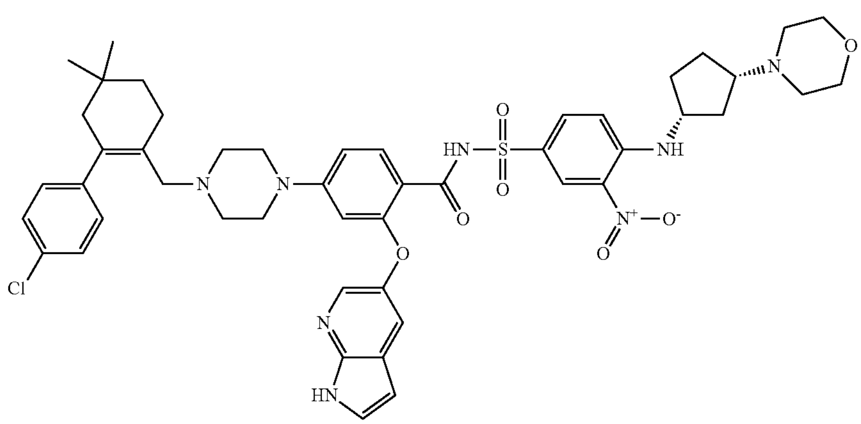 [SMILES: CC1(C)CCC(CN2CCN(c3ccc(C(=O)NS(=O)(=O)c4ccc(N[C@@H]5CC[C@H](N6CCOCC6)C5)c([N+](=O)[O-])c4)c(Oc4cnc5[nH]ccc5c4)c3)CC2)=C(c2ccc(Cl)cc2)C1] |

| Name | Structure |
|---|---|
| 4-(4-{[2-(4-chlorophenyl)-4,4-dimethylcyclohex-1-en-1-yl]methyl}piperazin-1-yl)-N-({4-[(morpholin-2-ylmethyl)amino]-3-nitrophenyl}sulfonyl)-2-(1H-pyrrolo[2,3-b]pyridin-5-yloxy)benzamide | 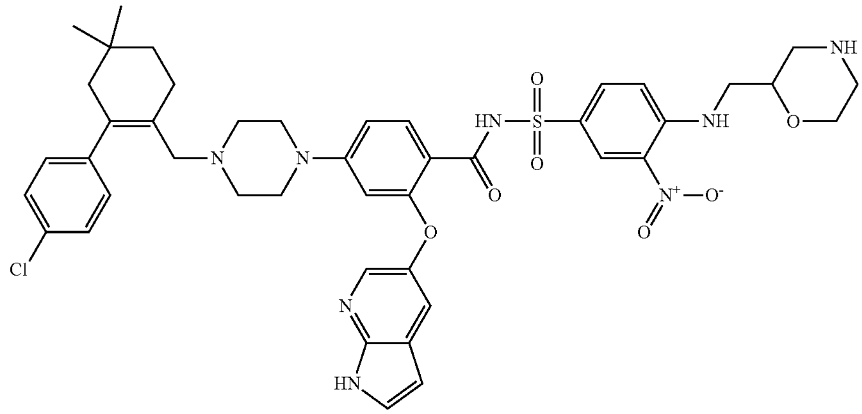 [SMILES: CC1(C)CCC(CN2CCN(c3ccc(C(=O)NS(=O)(=O)c4ccc(NCC5CNCCO5)c([N+](=O)[O-])c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-({3-nitro-4-[(tetrahydrofuran-3-ylmethyl)amino]phenyl}sulfonyl)-2-(1H-pyrrolo[2,3-b]pyridin-5-yloxy)benzamide | 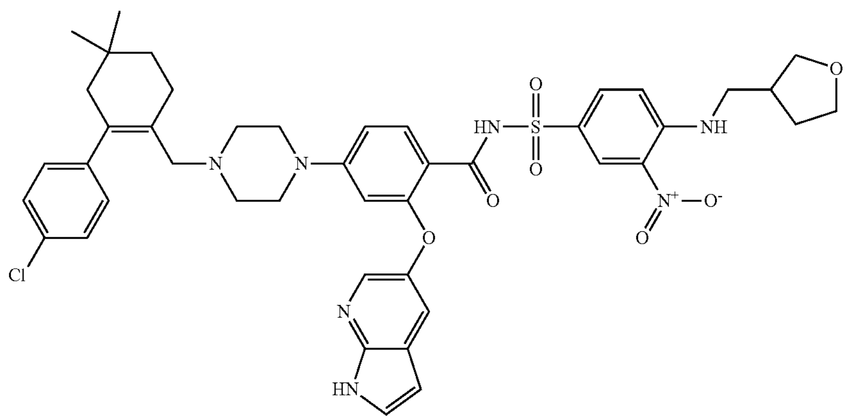 [SMILES: CC1(C)CCC(CN2CCN(c3ccc(C(=O)NS(=O)(=O)c4ccc(NCC5CCOC5)c([N+](=O)[O-])c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-{[4-({1-[cis-3-fluorotetrahydro-2H-pyran-4-yl]piperidin-4-yl}amino)-3-nitrophenyl]sulfonyl}-2-(1H-pyrrolo[2,3-b]pyridin-5-yloxy)benzamide | 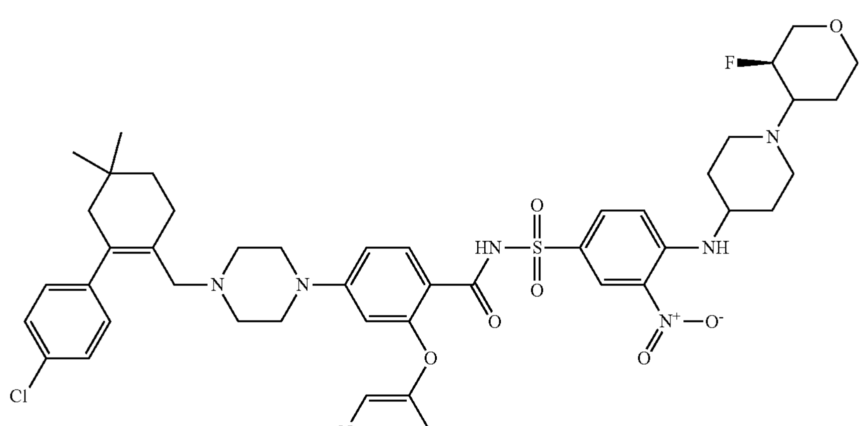 |

| Name | Structure |
|---|---|
| 4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylazetidin-3-yl)amino]phenyl}sulfonyl)-2-(1H-pyrrolo[2,3-b]pyridin-5-yloxy)benzamide | 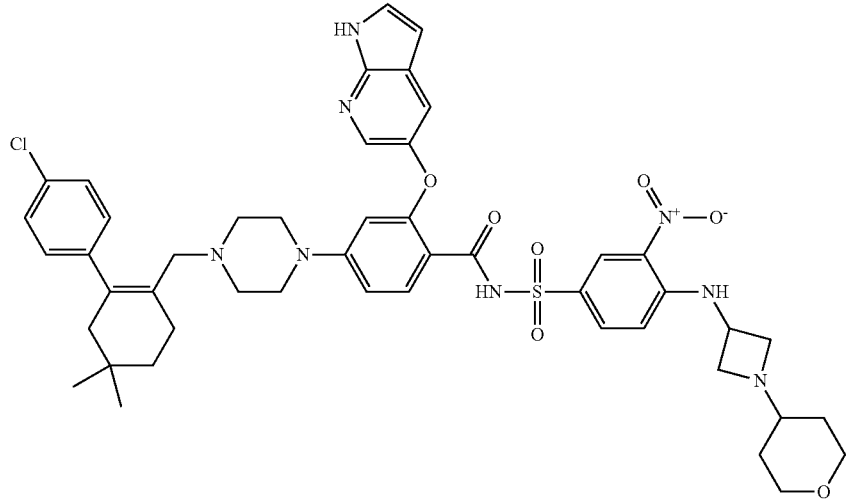 [SMILES: CC1(C)CCC(CN2CCN(c3ccc(C(=O)NS(=O)(=O)c4ccc(NC5CN(C6CCOCC6)C5)c([N+](=O)[O-])c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-({3-nitro-4-[(1-tetrahydro furan-3-ylazetidin-3-yl)amino]phenyl}sulfonyl)-2-(1H-pyrrolo[2,3-b]pyridin-5-yloxy)benzamide | 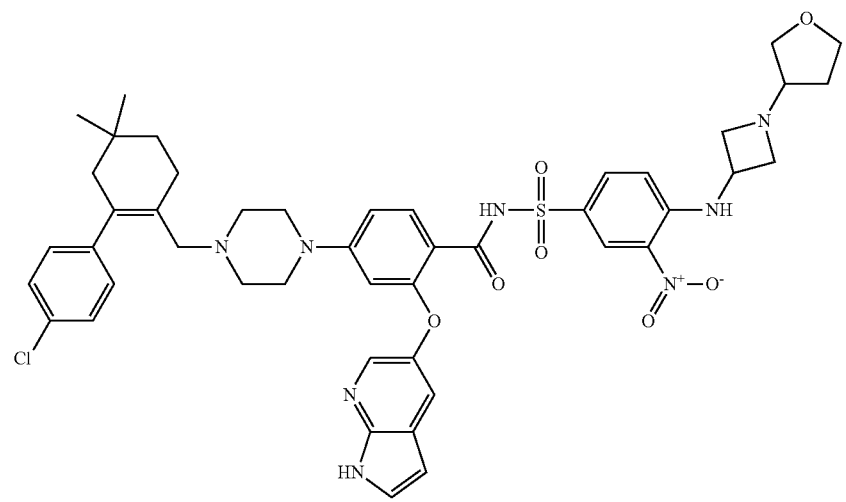 [SMILES: CC1(C)CCC(CN2CCN(c3ccc(C(=O)NS(=O)(=O)c4ccc(NC5CN(C6CCOC6)C5)c([N+](=O)[O-])c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-{[3-nitro-4-({[(3R)-1-tetrahydro-2H-pyran-4-ylpyrrolidin-3-yl]methyl}amino)phenyl]sulfonyl}-2-(1H-pyrrolo[2,3-b]pyridin-5-yloxy)benzamide | 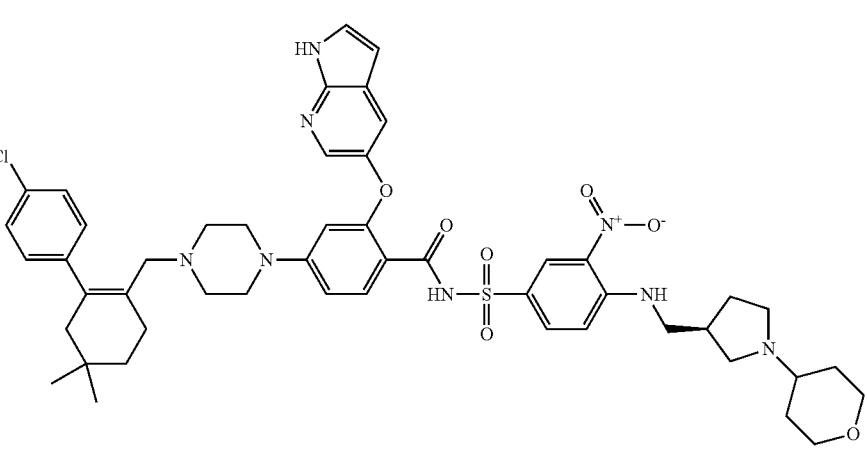 |

| Name | Structure |
|---|---|
| 4-(4-{[2-(4-chlorophenyl)-5,5-dimethylcyclohex-1-en-1-yl]methyl}piperazin-1-yl)-N-({4-[(4-fluorotetrahydro-2H-pyran-4-yl)methoxy]-3-nitrophenyl}sulfonyl)-2-(1H-pyrrolo[2,3-b]pyridin-5-yloxy)benzamide | 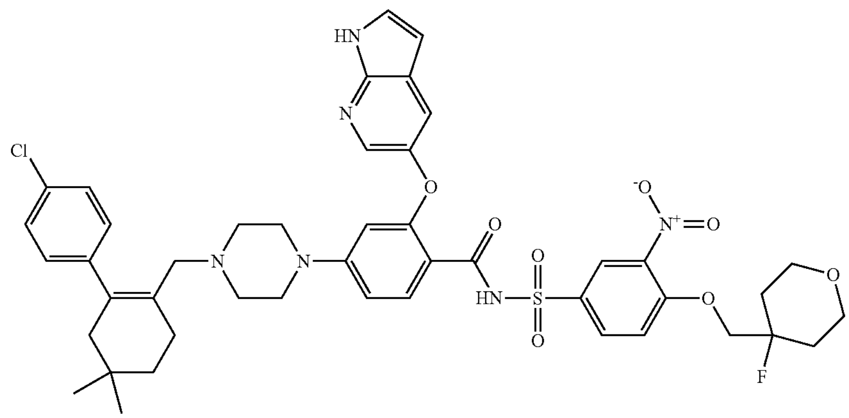 |
| 2-(1H-pyrrolo[2,3-b]pyridin-5-yloxy)-4-(4-((2-(4-chlorophenyl)-4,4-dimethylcyclohex-1-enyl)methyl)piperazine-1-yl)-N-(4-((trans-4-hydroxycyclohexyl)methoxy)-3-nitrophenylsulfonyl)benzamide | 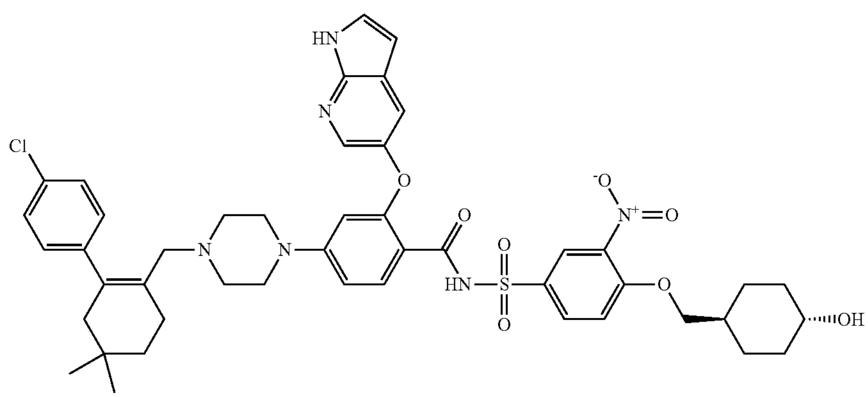 |
| 2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(4-((cis-4-methoxycyclohexyl)methoxy)-3-nitrophenylsulfonyl)benzamide | 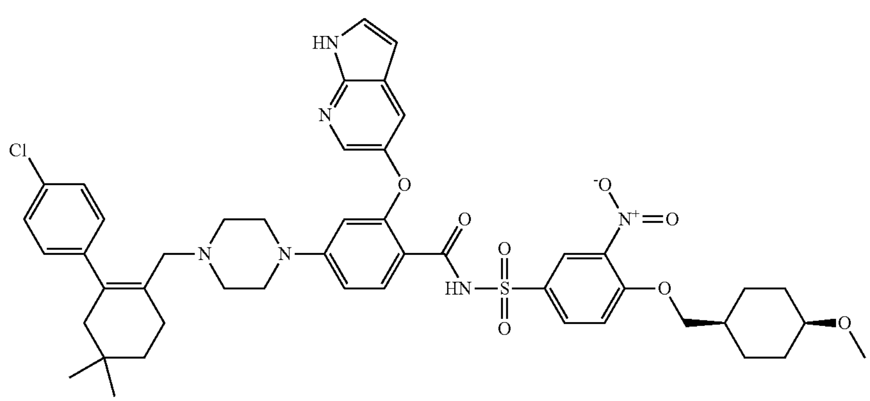 |

-continued

| Name | Structure |
|---|---|
| Cis-4-(4-{[2-(4-chlorophenyl)-4,4-dimethylcyclohex-1-en-1-yl]methyl}piperazin-1-yl)-N-[(4-{[4-(cyclopropylamino)cyclohexyl]amino}-3-nitrophenyl)sulfonyl]-2-(1H-pyrrolo[2,3-b]pyridin-5-yloxy)benzamide | 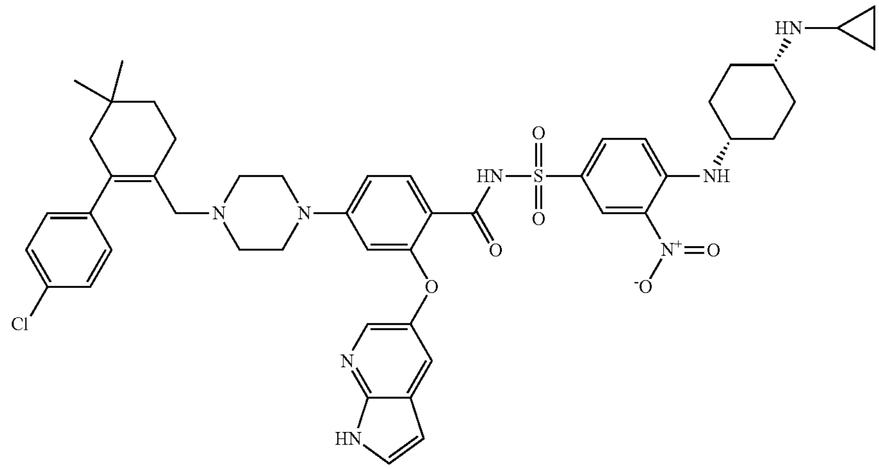 |
| Trans-4-(4-{[2-(4-chlorophenyl)-4,4-dimethylcyclohex-1-en-1-yl]methyl}piperazin-1-yl)-N-[(3-nitro-4-{[4-(tetrahydro-2H-pyran-4-ylamino)cyclohexyl]amino}phenyl)sulfonyl]-2-(1H-pyrrolo[2,3-b]pyridin-5-yloxy)benzamide | 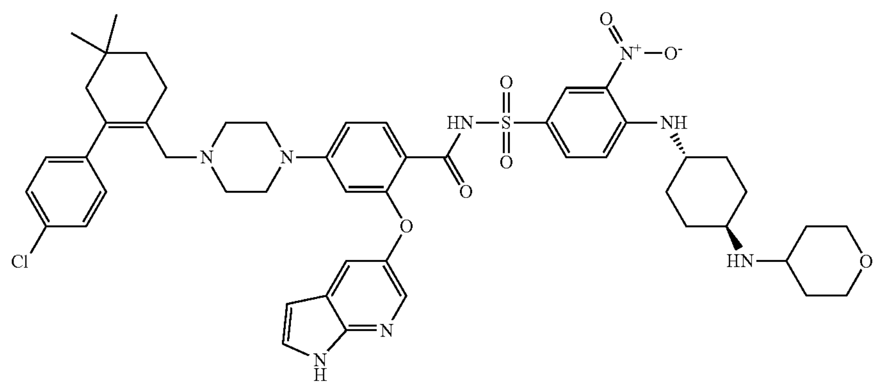 [SMILES: CC1(C)CCC(CN2CCN(c3ccc(C(=O)NS(=O)(=O)c4ccc(N[C@H]5CC[C@H](NC6CCOCC6)CC5)c([N+](=O)[O-])c4)c(Oc4cnc5[nH]ccc5c4)c3)CC2)=C(c2ccc(Cl)cc2)C1] |
| Trans-N-({5-bromo-6-[(4-morpholin-4-ylcyclohexyl)oxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | 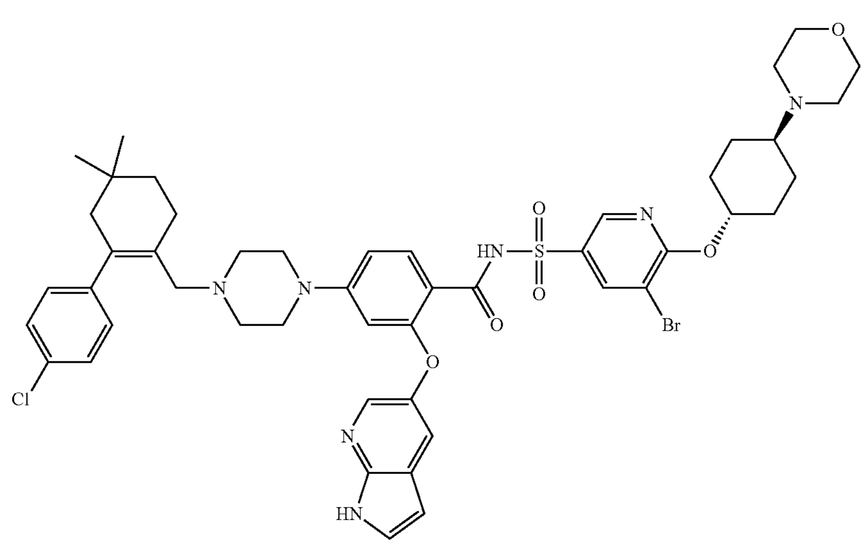 [SMILES: CC1(C)CCC(CN2CCN(c3ccc(C(=O)NS(=O)(=O)c4cnc(O[C@H]5CC[C@H](N6CCOCC6)CC5)c(Br)c4)c(Oc4cnc5[nH]ccc5c4)c3)CC2)=C(c2ccc(Cl)cc2)C1] |

| Name | Structure |
|---|---|
| Trans-4-(4-{[2-(4-chlorophenyl)-4,4-dimethylcyclohex-1-en-1-yl]methyl}piperazin-1-yl)-N-({4-[(4-methoxycyclohexyl)methoxy]-3-nitrophenyl}sulfonyl)-2-(1H-pyrrolo[2,3-b]pyridin-5-yloxy)benzamide | 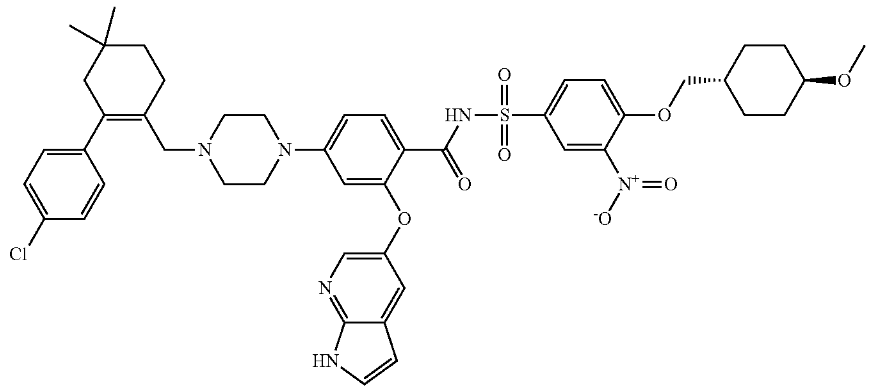 |
| tert-butyl 4-{[4-({[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]amino}sulfonyl)-2-nitrophenoxy]methyl}-4-fluoropiperidine-1-carboxylate | 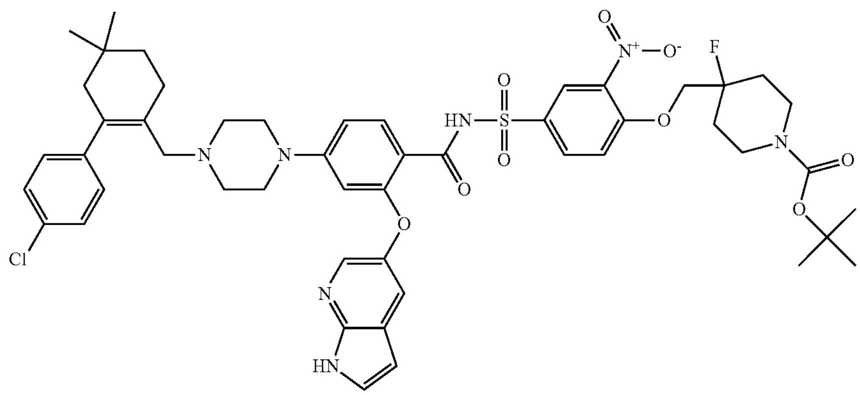 [SMILES: CC1(C)CCC(CN2CCN(c3ccc(C(=O)NS(=O)(=O)c4ccc(OCC5(F)CCN(C(=O)OC(C)(C)C)CC5)c([N+](=O)[O-])c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-({4-[(4-fluoropiperidin-4-yl)methoxy]-3-nitrophenyl}sulfony)-2-(1H-pyrrolo[2,3-b]pyridin-5-yloxy)benzamide | 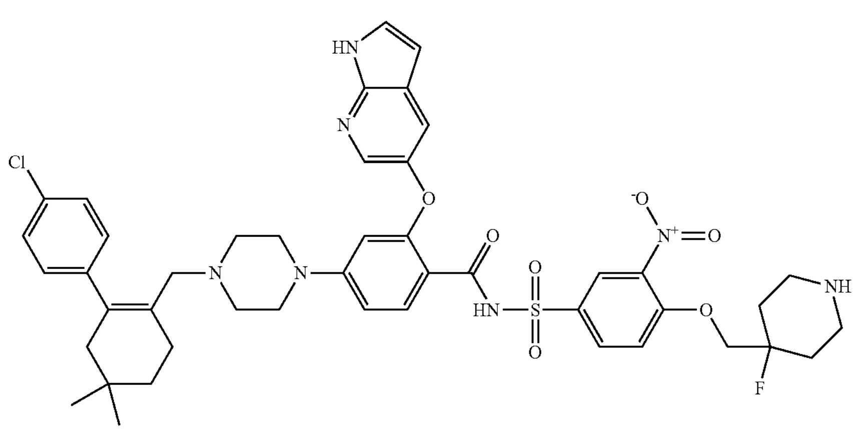 |

| Name | Structure |
|---|---|
| Trans-4-(4-{[2-(4-chlorophenyl)-4,4-dimethylcyclohex-1-en-1-yl]methyl}piperazin-1-yl)-N-[(3-nitro-4-{[4-(4-tetrahydro-2H-pyran-4-ylpiperazin-1-yl)cyclohexyl]amino}phenyl)sulfonyl]-2-(1H-pyrrolo[2,3-b]pyridin-5-yloxy)benzamide | 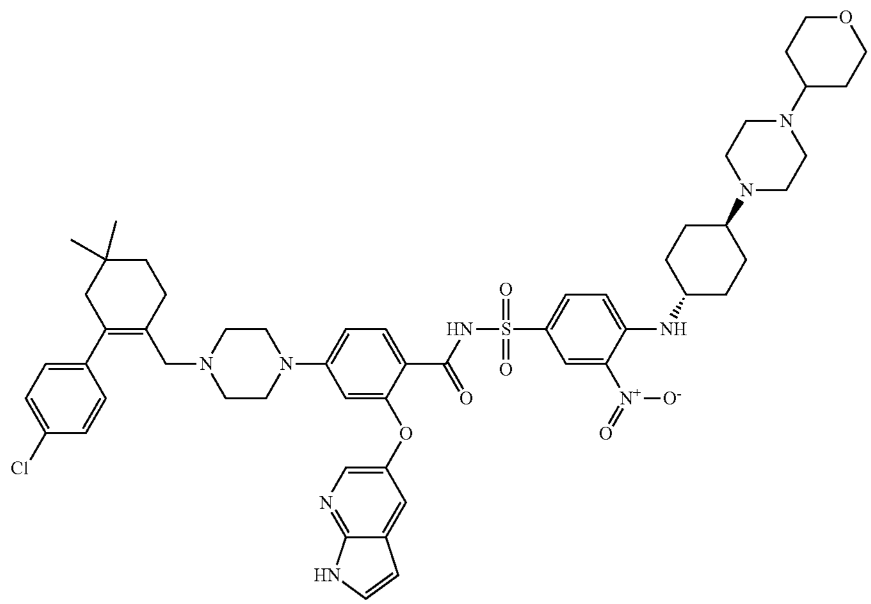 [SMILES: CC1(C)CCC(CN2CCN(c3ccc(C(=O)NS(=O)(=O)c4ccc(N[C@H]5CC[C@H](N6CCN(C7CCOCC7)CC6)CC5)c([N+](=O)[O-])c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-{[4-({1-[2-fluoro-1-(fluoromethyl)ethyl]piperidin-4-yl}methoxy)-3-nitrophenyl]sulfonyl}-2-(1H-pyrrolo[2,3-b]pyridin-5-yloxy)benzamide | 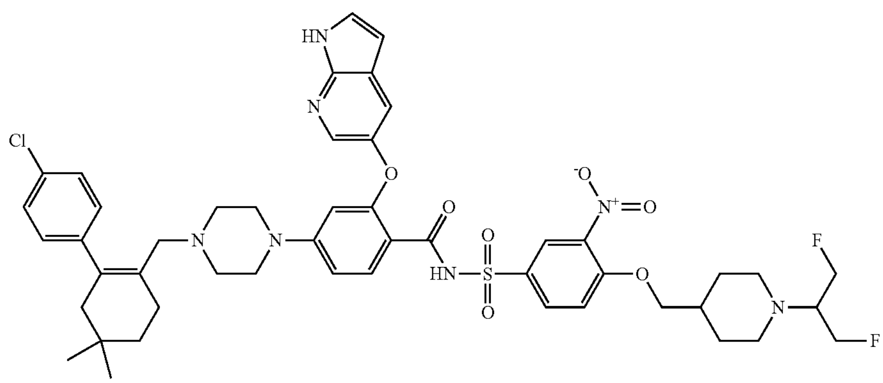 |
| 4-(4-{[2-{4-chlorophenyl)-4,4-dimethylcyclohex-1-en-1-yl]methyl}piperazin-1-yl)-N-[(3-nitro-4-{[(3R)-1-tetrahydro-2H-pyran-4-ylpyrrolidin-3-yl]amino}phenyl)sulfonyl]-2-(1H-pyrrolo[2,3-b])pyridin-5-yloxy)benzamide | |

-continued

| Name | Structure |
|---|---|
| 4-(4-{[2-(4-chlorophenyl)-4,4-dimethylcyclohex-1-en-1-yl]methyl}piperazin-1-yl)-N-[(4-{[(3R)-1-(2,2-dimethyltetrahydro-2H-pyran-4-yl)pyrrolidin-3-yl]amino}-3-nitrophenyl)sulfonyl]-2-(1H-pyrrolo[2,3-b]pyridin-5-yloxy)benzamide | |
| 4-(4-{[2-(4-chlorophenyl)-4,4-dimethylcyclohex-1-en-1-yl]methyl}piperazin-1-yl)-N-[(3-nitro-4-{[(3S)-1-tetrahydro-2H-pyran-4-ylpyrrolidin-3-yl]amino}phenyl)sulfonyl]-2-(1H-pyrrolo[2,3-b]pyridin-5-yloxy)benzamide | 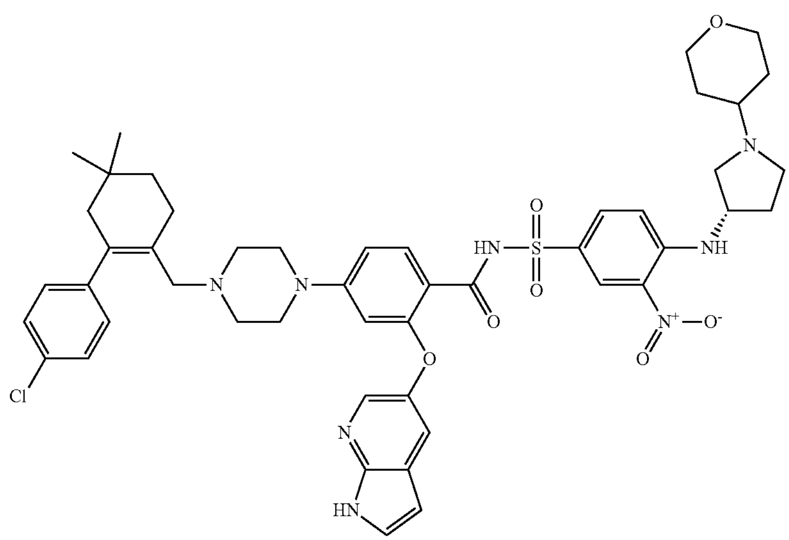 [SMILES: CC1(C)CCC(CN2CCN(c3ccc(C(=O)NS(=O)(=O)c4ccc(N[C@H]5CCN(C6CCOCC6)C5)c([N+](=O)[O-])c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-[(4-{[(3S)-1-(2,2-dimethyltetrahydro-2H-pytan-4-yl)pyrrolidin-3-yl]amino}-3-nitrophenyl)sulfonyl]-2-(1H-pyrrolo[2,3-b]pyridin-5-yloxy)benzamide | 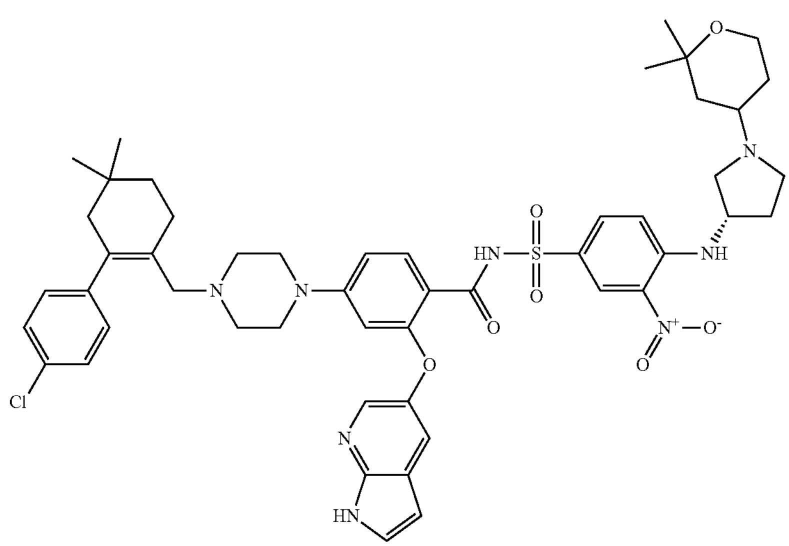 [SMILES: CC1(C)CCC(CN2CCN(c3ccc(C(=O)NS(=O)(=O)c4ccc(N[C@H]5CCN(C6CCOC(C)(C)C6)C5)c([N+](=O)[O-])c4)c(Oc4cnc5[nH]ccc5c4)c3)CC2)=C(c2ccc(Cl)cc2)C1] |

| Name | Structure |
|---|---|
| 4-{4-{[2-(4-chlorophenyl)-4,4-dimethylcyclohex-1-en-1-yl]methyl}piperazin-1-yl)-N-[(4-{[(4-methylmorpholin-2-yl)methyl]amino}-3-nitrophenyl)sulfonyl]-2-(1H-pyrrolo[2,3-b]pyridin-5-yloxy)benzamide | 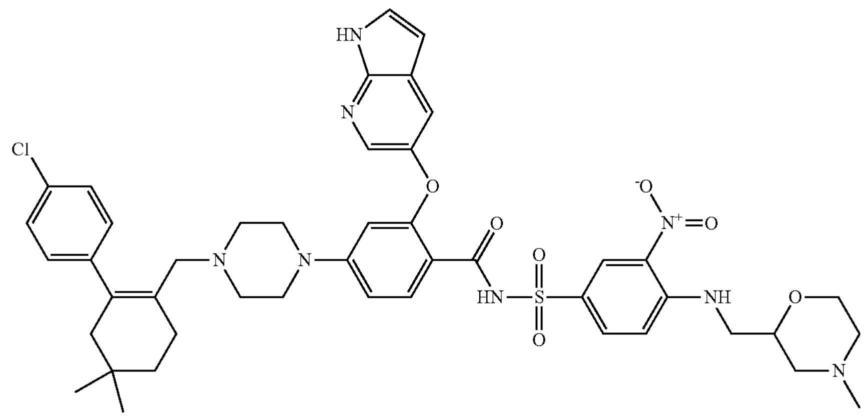 |
| 4-(4-{[2-(4-chlorophenyl)-4,4-dimethylcyclohex-1-en-1-yl]methyl}piperazin-1-yl)-N-{[4-({[4-(2-methoxyethyl)morpholin-2-yl]methyl}amino)-3-nitrophenyl]sulfonyl}-2-(1H-pyrrolo[2,3-b]pyridin-5-yloxy)benzamide | 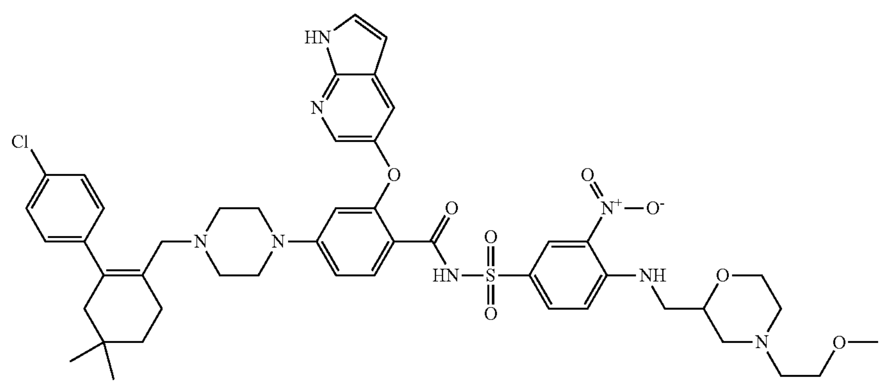 [SMILES: COCCN1CCOC(CNc2ccc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2[N+](=O)[O-])C1] |
| N-[(4-{[(4-acetylmorpholin-2-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | |

| Name | Structure |
|---|---|
| 4-(4-{[2-(4-chlorophenyl)-4,4-dimethylcyclohex-1-en-1-yl]methyl}piperazin-1-yl)-N-[(4-{[trans-4-(fluoromethyl)-1-oxetan-3-ylpyrrolidin-3-yl]methoxy}-3-nitrophenyl)sulfonyl]-2-(1H-pyrrolo[2,3-b]pyridin-5-yloxy)benzamide | |
| 4-(4-{[2-(4-chlorophenyl)-4,4-dimethylcyclohex-1-en-1-yl]methyl}piperazin-1-yl)-N-[(4-{[(4-fluorotetrahydro-2H-pyran-4-yl)methyl]amino}-3-nitrophenyl)sulfonyl]-2-(1H-pyrrolo[2,3-b]pyridin-5-yloxy)benzamide | |
| 4-(4-{[2-(4-chlorophenyl)-4,4-dimethylcyclohex-1-en-1-yl]methyl}piperazin-1-yl)-N-({3-nitro-4-[(1-oxetan-3-ylpiperidin-4-yl)amino]phenyl}sulfonyl)-2-(1H-pyrrolo[2,3-b]pyridin-5-yloxy)benzamide | |

| Name | Structure |
|---|---|
| 4-(4-{[2-(4-chlorophenyl)-4,4-dimethylcyclohex-1-en-1-yl]methyl}piperazin-1-yl)-N-({4-[(1-cyclobutylpiperidin-4-yl)amino]-3-nitrophenyl}sulfonyl)-2-(1H-pyrrolo[2,3-b]pyridin-5-yloxy)benzamide | 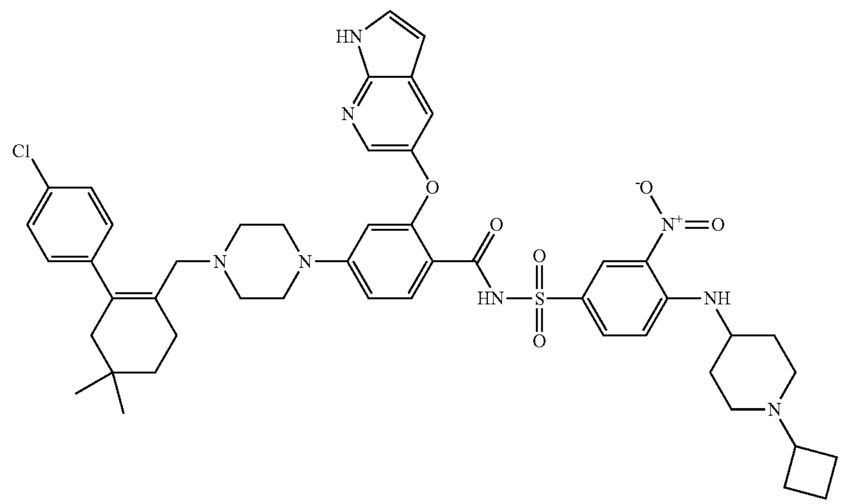 |
| 4-(4-{[2-(4-chlorophenyl)-4,4-dimethylcyclohex-1-en-1-yl]methyl}piperazin-1-yl)-N-[(4-{[1-(2,2-dimethyltetrahydro-2H-pyran-4-yl)piperidin-4-yl]amino}-3-nitrophenyl)sulfonyl]-2-(1H-pyrrolo[2,3-b]pyridin-5-yloxy)benzamide | 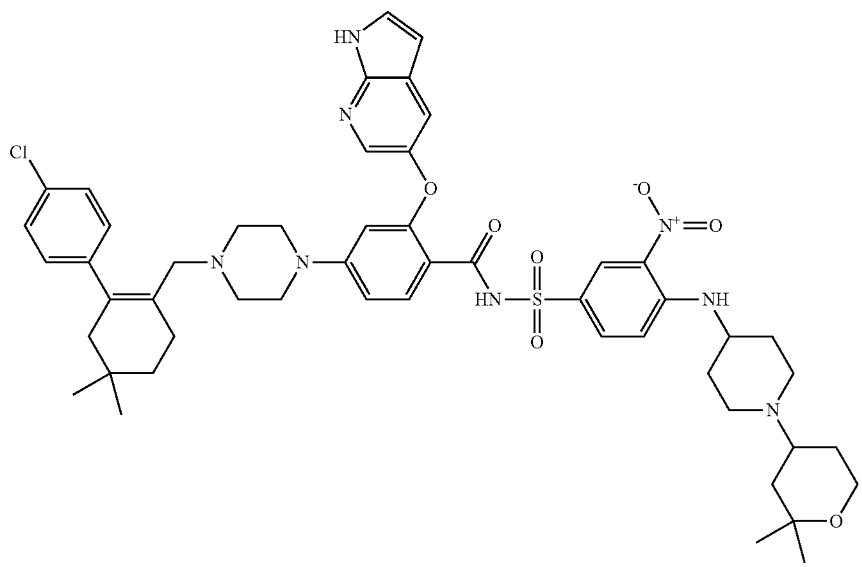 |
| 4-(4-{[2-(4-chlorophenyl)-4,4-dimethylcyclohex-1-en-1-yl]methyl}piperazin-1-yl)-N-[(4-{[(3S)-1-cyclopropylpyrrolidin-3-yl]amino}-3-nitrophenyl)sulfonyl]-2-(1H-pyrrolo[2,3-b]pyridin-5-yloxy)benzamide | 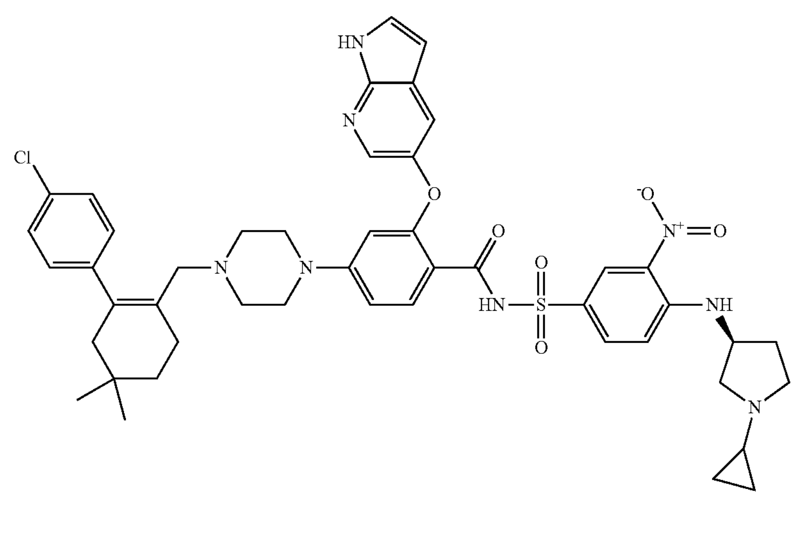 |

-continued

| Name | Structure |
|---|---|
| 4-(4-{[2-{4-chlorophenyl}-4,4-dimethylcyclohex-1-en-1-yl]methyl}piperazin-1-yl)-N-({3-nitro-4-[(1-tetrahydrofuran-3-ylpiperidin-4-yl)amino]phenyl}sulfonyl)-2-(1H-pyrrolo[2,3-b]pyridin-5-yloxy)benzamide | 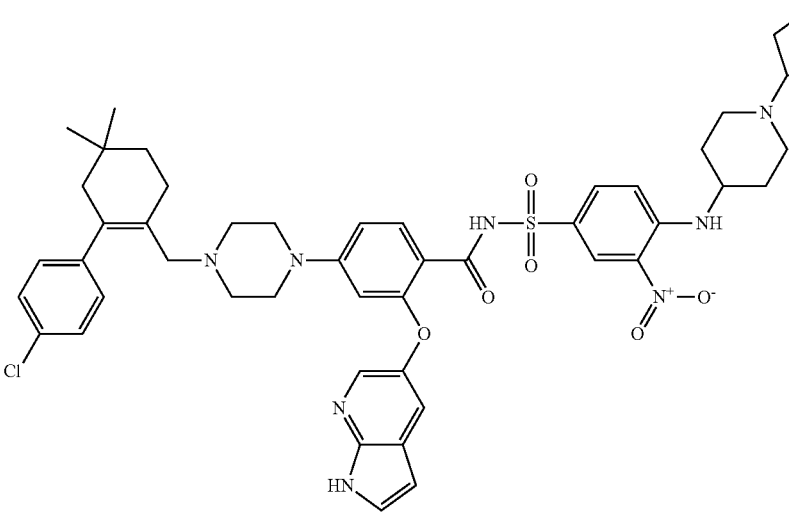 |
| 4-(4-{[2-(4-chlorophenyl)-4,4-dimethylcyclohex-1-en-1-yl]methyl}piperazin-1-yl)-N-[(4-{[(3R)-1-cyclopropylpyrrolidin-3-yl]amino}-3-nitrophenyl)sulfonyl]-2-(1H-pyrrolo[2,3-b]pyridin-5-yloxy)benzamide | 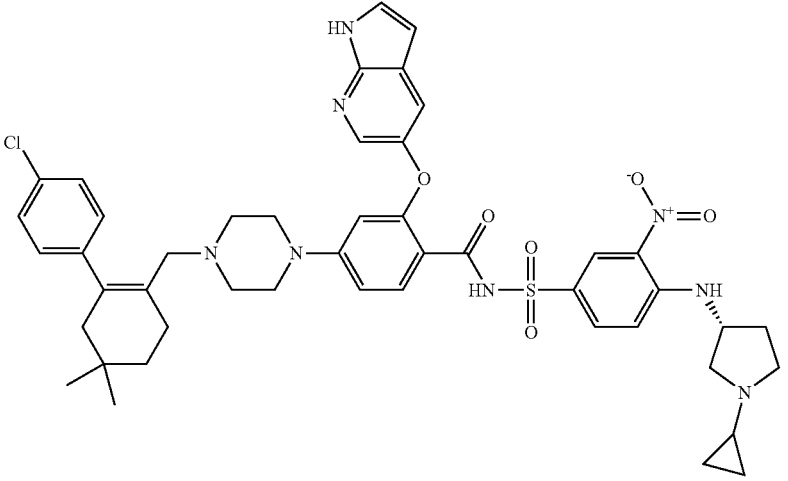 |
| 4-(4-{[2-(4-chlorophenyl)-4,4-dimethylcyclohex-1-en-1-yl]methyl}piperazin-1-yl)-N-{[3-nitro-4-({[(3S)-1-tetrahydro-2H-pyran-4-ylpyrrolidin-3-yl]methyl}amino)phenyl]sulfonyl}-2-(1H-pyrrolo[2,3-b]pyridin-5-yloxy)benzamide | 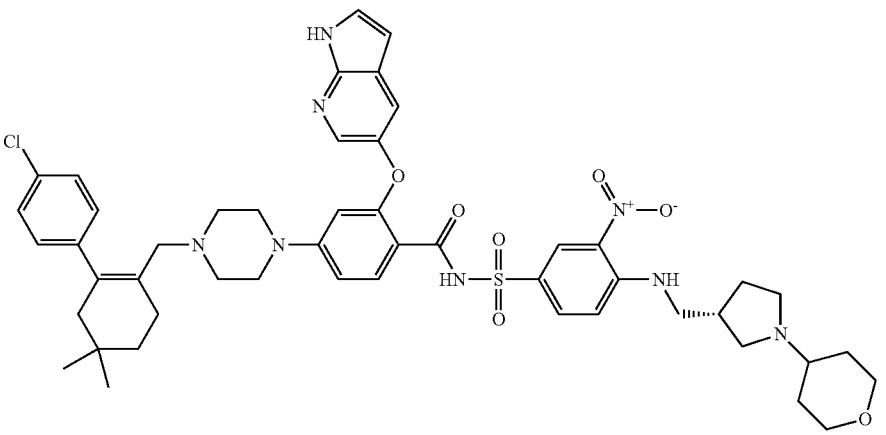 [SMILES: CC1(C)CCC(CN2CCN(c3ccc(C(=O)NS(=O)(=O)c4ccc(NC[C@@H]5CCN(C6CCOCC6)C5)c([N+](=O)[O-])c4)c(Oc4cnc5[nH]ccc5c4)c3)CC2)=C(c2ccc(Cl)cc2)C1] |

| Name | Structure |
|---|---|
| 4-(4-{[2-(4-chlorophenyl)-4,4-dimethylcyclohex-1-en-1-yl]methyl}piperazin-1-yl)-N-({4-[(3-hydroxy-2,2-dimethylpropyl)amino]-3-nitrophenyl}sulfonyl)-2-(1H-pyrrolo[2,3-b]pyridin-5-yloxy)benzamide | 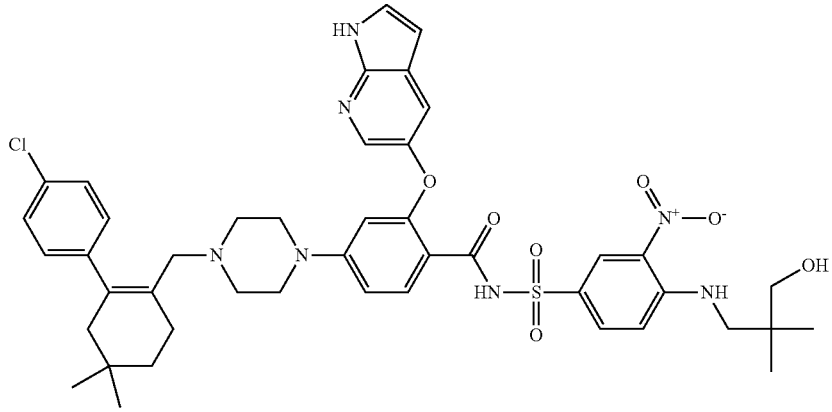 [SMILES: CC(C)(CO)CNc1ccc(S(=O)(=O)NC(=O)c2ccc(N3CCN(CC4=C(c5ccc(Cl)cc5)CC(C)(C)CC4)CC3)cc2Oc2cnc3[nH]ccc3c2)cc1[N+](=O)[O-]] |
| 4-(4-{[2-(4-chlorophenyl)-4,4-dimethylcyclohex-1-en-1-yl]methyl}piperazin-1-yl)-N-{[4-({[1-(methylsulfonyl)piperidin-3-yl]methyl}amino)-3-nitrophenyl]sulfonyl}-2-(1H-pyrrolo[2,3-b]pyridin-5-yloxy)benzamide | 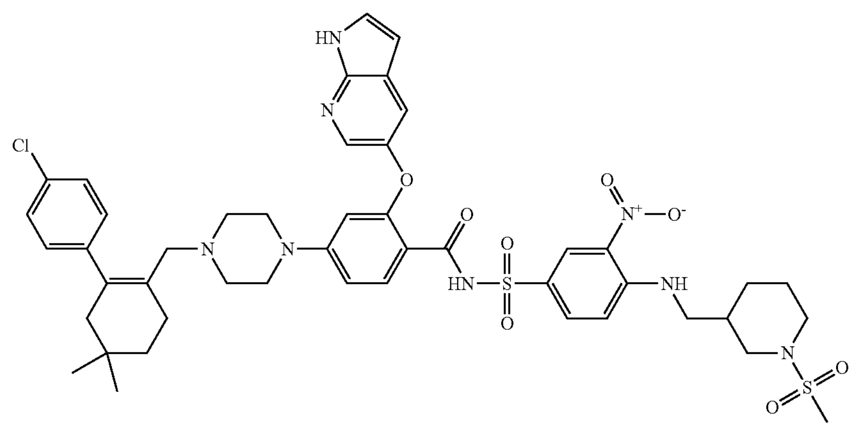 [SMILES: CC1(C)CCC(CN2CCN(c3ccc(C(=O)NS(=O)(=O)c4ccc(NCC5CCCN(S(C)(=O)=O)C5)c([N+](=O)[O-])c4)c(Oc4cnc5[nH]ccc5c4)c3)CC2)=C(c2ccc(Cl)cc2)C1] |
| N-[(4-{[(1-acetylpiperidin-3-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | 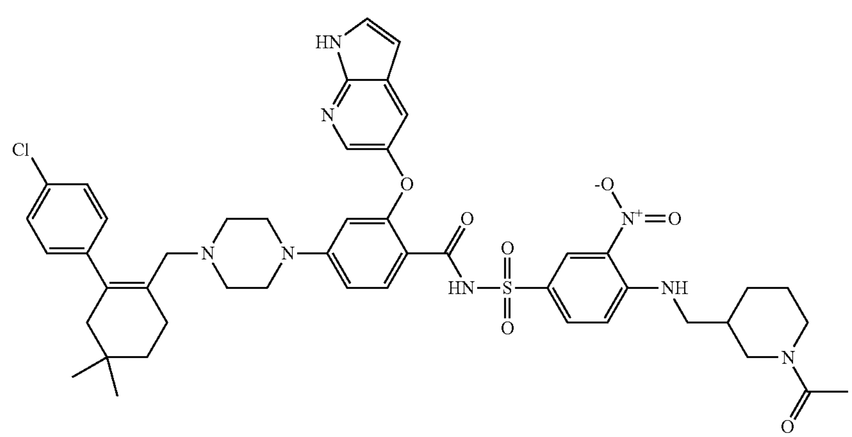 |

| Name | Structure |
|---|---|
| 4-(4-{[2-(4-chlorophenyl)-4,4-dimethylcyclohex-1-en-1-yl]methyl}piperazin-1-yl)-N-[(4-{[(3R)-1-(methylsulfonyl)pyrrolidin-3-yl]amino}-3-nitrophenyl)sulfonyl]-2-(1H-pyrrolo[2,3-b]pyridin-5-yloxy)benzamide | |
| 4-(4-{[2-(4-chlorophenyl)-3,3-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide | 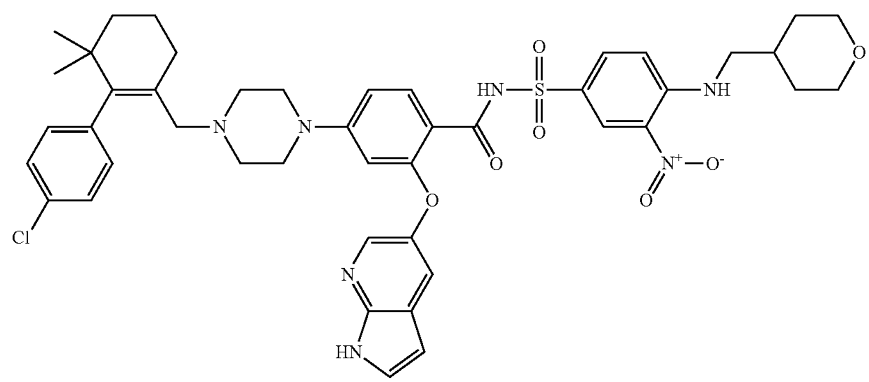 [SMILES: CC1(C)CCCC(CN2CCN(c3ccc(C(=O)NS(=O)(=O)c4ccc(NCC5CCOCC5)c([N+](=O)[O-])c4)c(Oc4cnc5[nH]ccc5c4)c3)CC2)=C1c1ccc(Cl)cc1] |
| 4-(4-{[2-(4-chlorophenyl)-4,4-dimethylcyclohex-1-en-1-yl]methyl}piperazin-1-yl)-N-{[4-({1-[2-fluoro-1-(fluoromethyl)ethyl]azetidin-3-yl}amino)-3-nitrophenyl]sulfonyl}-2-(1H-pyrrolo[2,3-b]pyridin-5-yloxy)benzamide | 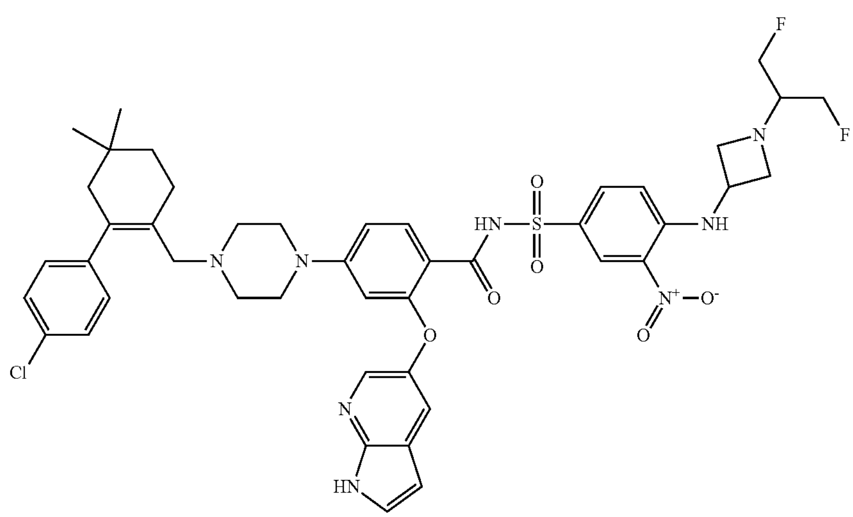 [SMILES: CC1(C)CCC(CN2CCN(c3ccc(C(=O)NS(=O)(=O)c4ccc(NC5CN(C(CF)CF)C5)c([N+](=O)[O-])c4)c(Oc4cnc5[nH]ccc5c4)c3)CC2)=C(c2ccc(Cl)cc2)C1] |

-continued

| Name | Structure |
|---|---|
| 4-(4-{[2-(4-chlorophenyl)-4,4-dimethylcyclohex-1-en-1-yl]methyl}piperazin-1-yl)-N-{[4-({[1-(methylsulfonyl)pyrrolidin-3-yl]methyl}amino)-3-nitrophenyl]sulfonyl}-2-(1H-pyrrolo[2,3-b]pyridin-5-yloxy)benzamide | 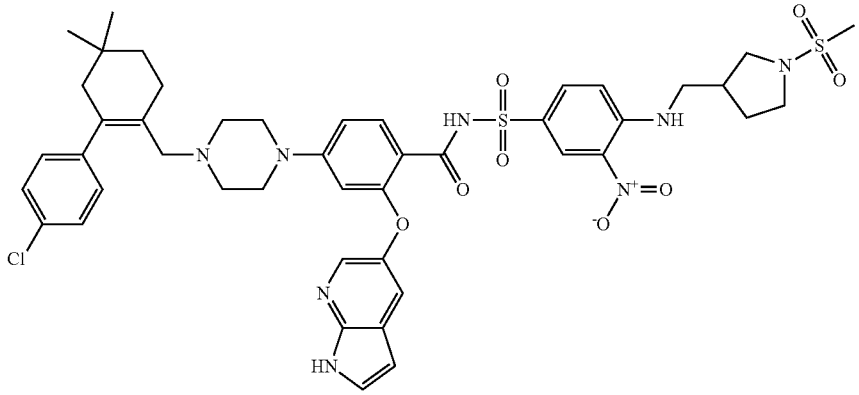 |
| N-[(4-{[(1-acetylpyrrolidin-3-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | 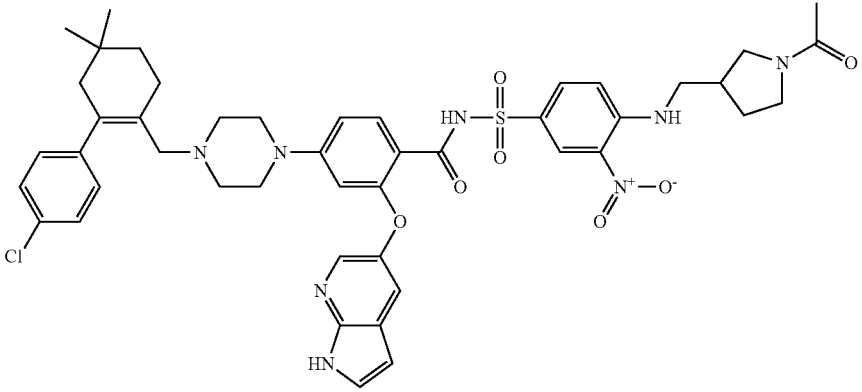 [SMILES: CC(=O)N1CCC(CNc2ccc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2[N+](=O)[O-])C1] |
| N-[(4-{[(3R)-1-acetylpyrrolidin-3-yl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | 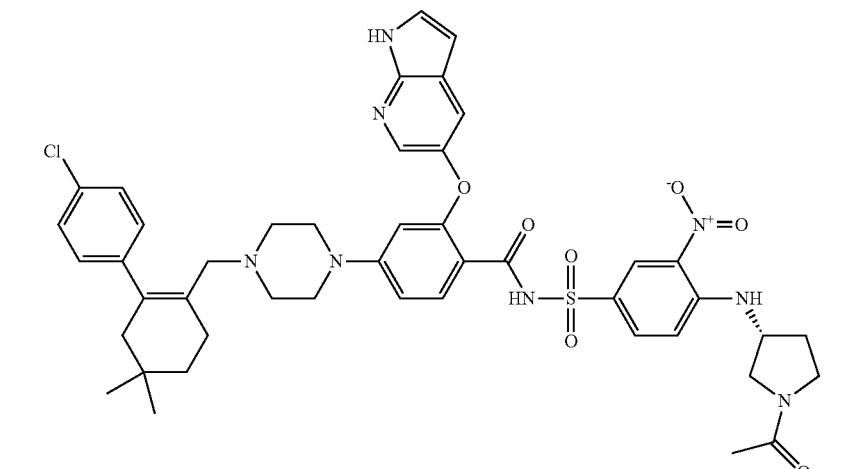 |

| Name | Structure |
|---|---|
| 4-(4-{[2-(4-chlorophenyl)-4,4-dimethylcyclohex-1-en-1-yl]methyl}piperazin-1-yl)-N-({4-[(3-methoxy-2,2-dimethylpropyl)amino]-3-nitrophenyl}sulfonyl)-2-(1H-pyrrolo[2,3-b]pyridin-5-yloxy)benzamide | 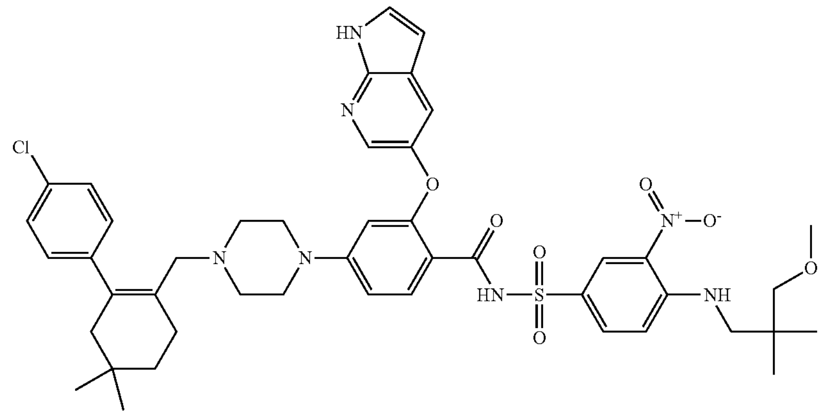 [SMILES: COCC(C)(C)CNc1ccc(S(=O)(=O)NC(=O)c2ccc(N3CCN(CC4=C(c5ccc(Cl)cc5)CC(C)(C)CC4)CC3)cc2Oc2cnc3[nH]ccc3c2)cc1[N+](=O)[O-]] |
| 4-(4-{[2-(4-chlorophenyl)-4,4-dimethylcyclohex-1-en-1-yl]methyl}piperazin-1-yl)-N-{[4-({[(1R,3R)-3-hydroxycyclopentyl]methyl}amino)-3-nitrophenyl]sulfonyl}-2-(1H-pyrrolo[2,3-b]pyridin-5-yloxy)benzamide | 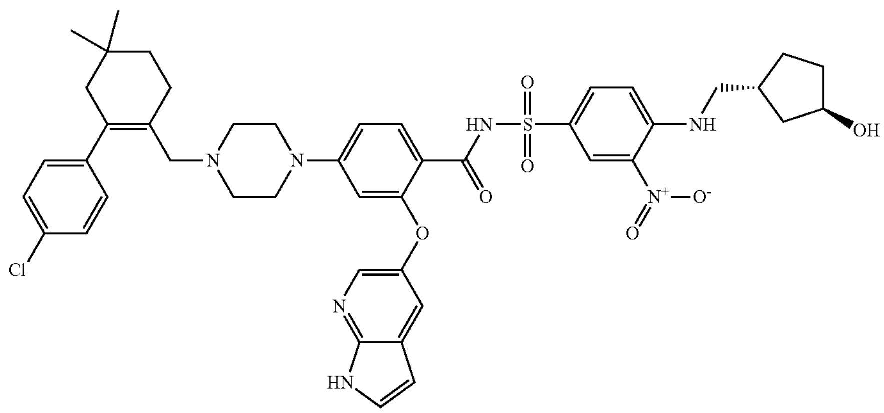 [SMILES: CC1(C)CCC(CN2CCN(c3ccc(C(=O)NS(=O)(=O)c4ccc(NC[C@@H]5CC[C@@H](O)C5)c([N+](=O)[O-])c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-{[4-({[(1S,3S)-3-hydroxycyclopentyl]methyl}amino)-3-nitrophenyl]sulfonyl}-2-{1H-pyrrolo[2,3-b]pyridin-5-yloxy)benzamide | 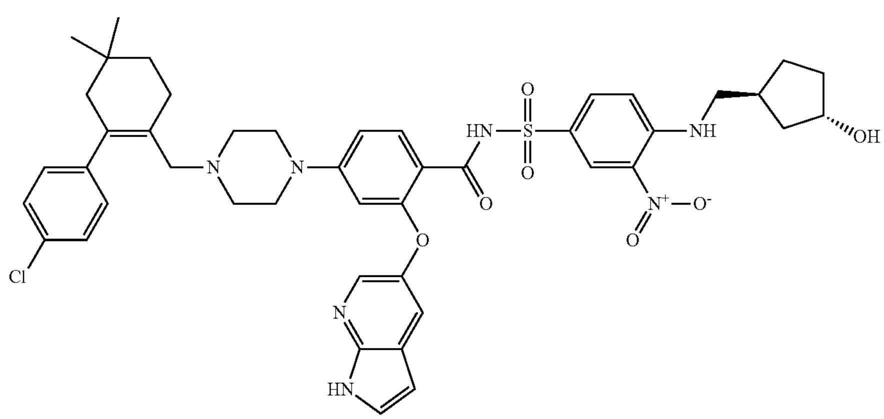 [SMILES: CC1(C)CCC(CN2CCN(c3ccc(C(=O)NS(=O)(=O)c4ccc(NC[C@H]5CC[C@H](O)C5)c([N+](=O)[O-])c4)c(Oc4cnc5[nH]ccc5c4)c3)CC2)=C(c2ccc(Cl)cc2)C1] |

| Name | Structure |
|---|---|
| 4-(4-{[2-(4-chlorophenyl)-4,4-dimethylcyclohex-1-en-1-yl]methyl}piperazin-1-yl)-N-{[4-({[(1S,3R)-3-hydroxycyclopentyl]methyl}amino)-3-nitrophenyl]sulfonyl}-2-(1H-pyrrolo[2,3-b]pyridin-5-yloxy)benzamide | 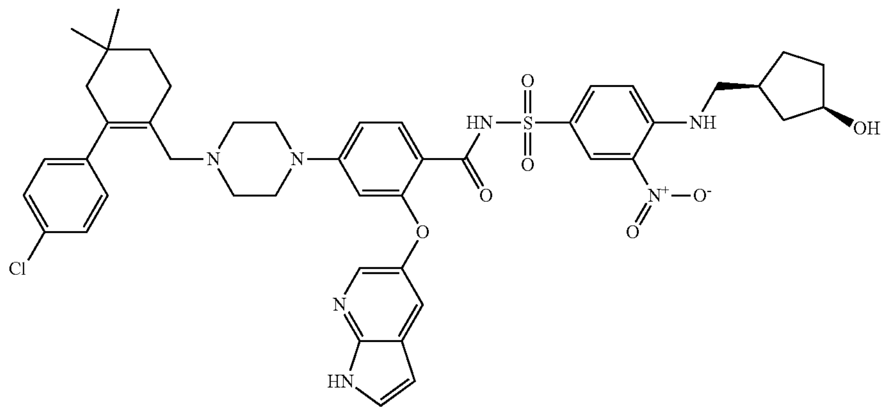 [SMILES: CC1(C)CCC(CN2CCN(c3ccc(C(=O)NS(=O)(=O)c4ccc(NC[C@H]5CC[C@@H](O)C5)c([N+](=O)[O-])c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-{[4-({[(1R,3S)-3-hydroxycyclopentyl]methyl}amino)-3-nitrophenyl]sulfonyl}-2-(1H-pyrrolo[2,3-b]pyridin-5-yloxy)benzamide | 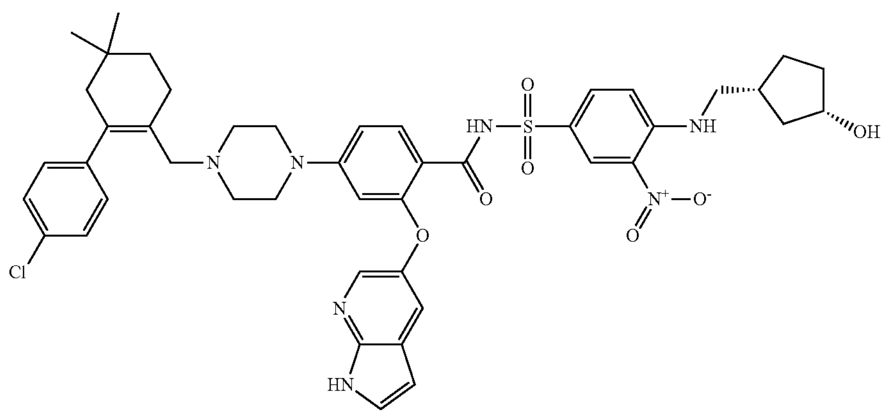 [SMILES: CC1(C)CCC(CN2CCN(c3ccc(C(=O)NS(=O)(=O)c4ccc(NC[C@@H]5CC[C@H](O)C5)c([N+](=O)[O-])c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-[(3-nitro-4-{[(3S)-2-oxopiperidin-3-yl]amino}phenyl)sulfonyl]-2-(1H-pyrrolo[2,3-b]pyridin-5-yloxy)benzamide | 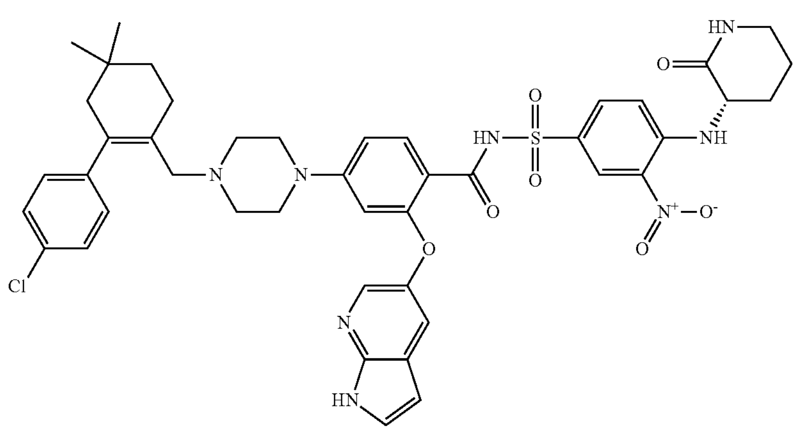 [SMILES: CC1(C)CCC(CN2CCN(c3ccc(C(=O)NS(=O)(=O)c4ccc(N[C@H]5CCCNC5=O)c([N+](=O)[O-])c4)c(Oc4cnc5[nH]ccc5c4)c3)CC2)=C(c2ccc(Cl)cc2)C1] |

| Name | Structure |
|---|---|
| 4-(4-{[2-(4-chlorophenyl)-4,4-dimethylcyclohex-1-en-1-yl]methyl}piperazin-1-yl)-N-({4-[({1-[2-fluoro-(fluoromethyl)ethyl]azetidin-3-yl}methyl)amino]-3-nitrophenyl}sulfonyl)-2-(1H-pyrrolo[2,3-b]pyridin-5-yloxy)benzamide | |
| 4-(4-{[2-{4-chlorophenyl)-4,4-dimethylcyclohex-1-en-1-yl]methyl}piperazin-1-yl)-N-[(3-nitro-4-{[(1-oxetan-3-ylazetidin-3-yl)methyl]amino}phenyl)sulfonyl]-2-(1H-pyrrolo[2,3-b]pyridin-5-yloxy)benzamide | 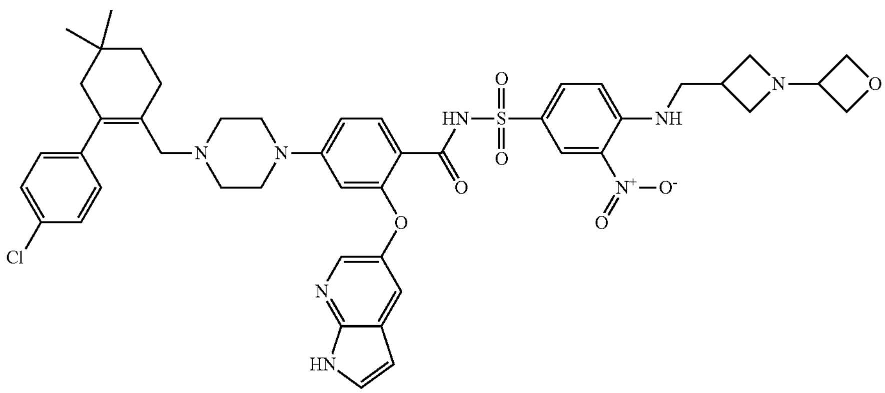 [SMILES: CC1(C)CCC(CN2CCN(c3ccc(C(=O)NS(=O)(=O)c4ccc(NCC5CN(C6COC6)C5)c([N+](=O)[O-])c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-[(3-nitro-4-{[(1-oxetan-3-ylpiperidin-4-yl)methyl]amino}phenyl)sulfonyl]-2-(1H-pyrrolo[2,3-b]pyridin-5-yloxy)benzamide | 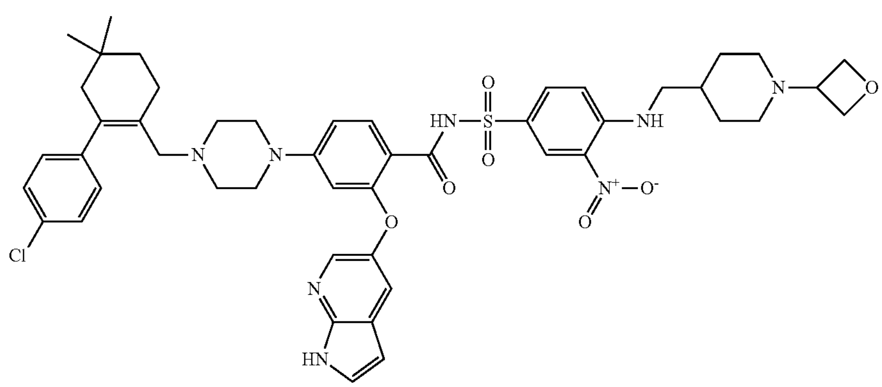 [SMILES: CC1(C)CCC(CN2CCN(c3ccc(C(=O)NS(=O)(=O)c4ccc(NCC5CCN(C6COC6)CC5)c([N+](=O)[O-])c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-[(4-{[(1-cyclopropylpiperidin-4-yl)methyl]amino}-3-nitrophenyl)sulfonyl]-2-(1H-pyrrolo[2,3-b]pyridin-5-yloxy)benzamide | 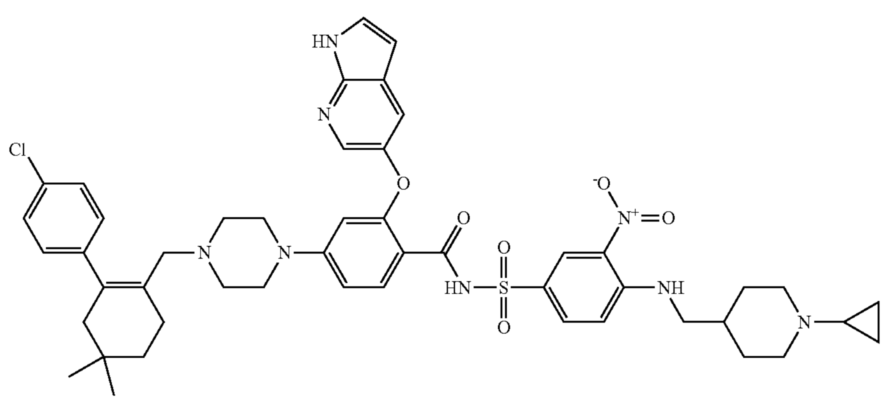 |

| Name | Structure |
|---|---|
| 4-(4-{[2-(4-chlorophenyl)-4,4-dimethylcyclohex-1-en-1-yl]methyl}piperazin-1-yl)-N-{[4-({[4-(2-fluoroethyl)morpholin-2-yl]methyl}amino)-3-nitrophenyl]sulfonyl}-2-(1H-pyrrolo[2,3-b]pyridin-5-yloxy)benzamide | |
| 4-(4-{[2-(4-chlorophenyl)-4,4-dimethylcyclohex-1-en-1-yl]methyl}piperazin-1-yl)-N-{[4-({[4-(2,2-difluoroethyl)morpholin-2-yl]methyl}amino)-3-nitrophenyl]sulfonyl}-2-(1H-pyrrolo[2,3-b]pyridin-5-yloxy)benzamide | |
| 4-(4-{[2-(4-chlorophenyl)-4,4-dimethylcyclohex-1-en-1-yl]methyl}piperazin-1-yl)-N-({4-[(4-fluoro-1-oxetan-3-ylpiperidin-4-yl)methoxy]-3-nitrophenyl}sulfonyl)-2-{1H-pyrrolo[2,3-b]pyridin-5-yloxy)benzamide | |

-continued

| Name | Structure |
|---|---|
| 4-(4-{[2-(4-chlorophenyl)-4,4-dimethylcyclohex-1-en-1-yl]methyl}piperazin-1-yl)-N-[(4-{[(2S)-4,4-difluor-1-oxetan-3-ylpyrrolidin-2-yl]methoxy}-3-nitrophenyl)sulfonyl]-2-(1H-pyrrolo[2,3-b]pyridin-5-yloxy)benzamide | 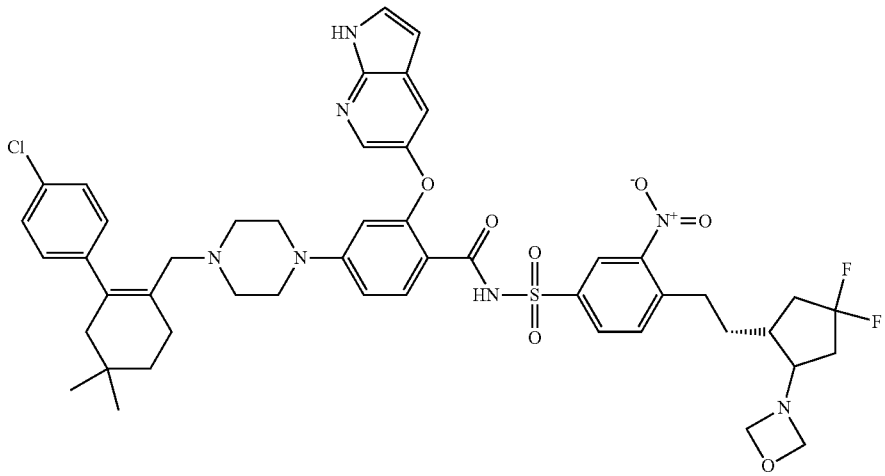 |
| 4-(4-{[2-(4-chlorophenyl)-4,4-dimethylcyclohex-1-en-1-yl]methyl}piperazin-1-yl)-N-[(3-nitro-4-{[(4-tetrahydro-2H-pyran-4-ylmorpholin-3-yl)methyl]amino}phenyl)sulfonyl]-2-(1H-pyrrolo[2,3-b]pyridin-5-yloxy)benzamide | 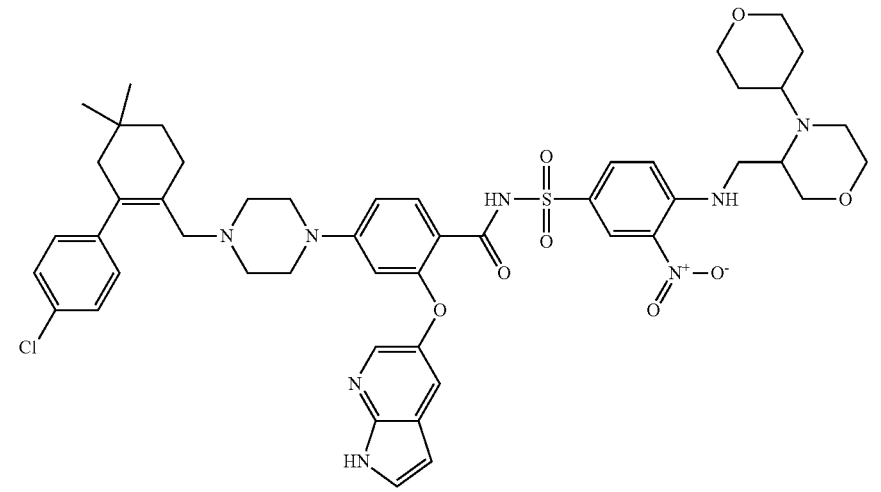 [SMILES: CC1(C)CCC(CN2CCN(c3ccc(C(=O)NS(=O)(=O)c4ccc(NCC5COCCN5C5CCOCC5)c([N+](=O)[O-])c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-[(4-{[(4-cyclobutylmorpholin-3-yl)methyl]amino}-3-nitrophenyl)sulfonyl]-2-(1H-pyrrolo[2,3-b]pyridin-5-yloxy)benzamide | 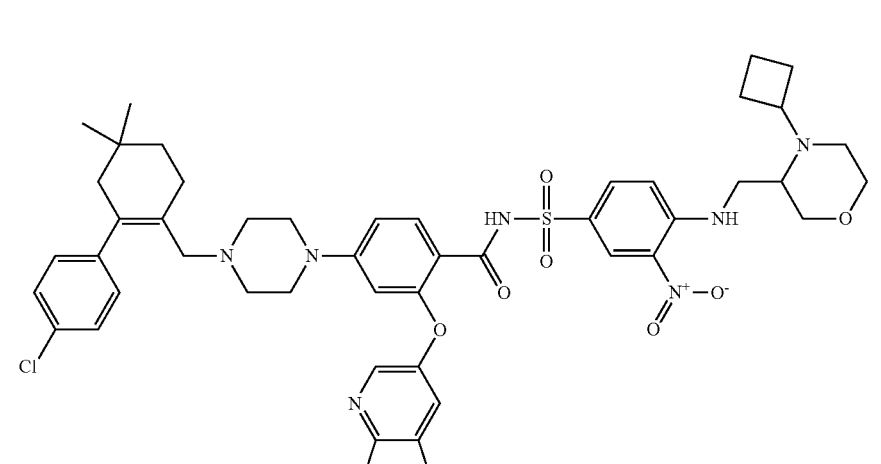 |

| Name | Structure |
|---|---|
| 4-(4-{[2-(4-chlorophenyl)-4,4-dimethylcyclohex-1-en-1-yl]methyl}piperazin-1-yl)-N-[(3-nitro-4-{[(4-tetrahydrofuran-3-ylmorpholin-3-yl)methyl]amino}phenyl)sulfonyl]-2-(1H-pyrrolo[2,3-b]pyridin-5-yloxy)benzamide | 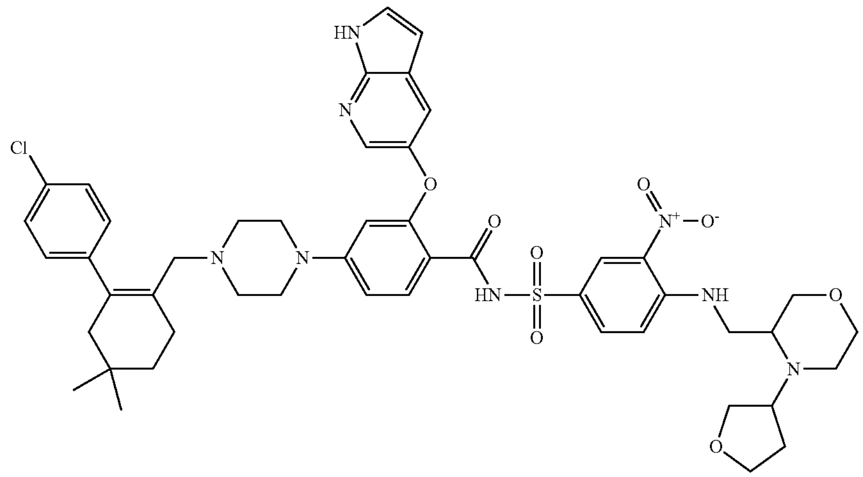 [SMILES: CC1(C)CCC(CN2CCN(c3ccc(C(=O)NS(=O)(=O)c4ccc(NCC5COCCN5C5CCOC5)c([N+](=O)[O-])c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-({4-[({1-[2-fluoro-1-(fluoromethyl)ethyl]piperidin-4-yl}methyl)amino]-3-nitrophenyl}sulfonyl)-2-(1H-pyrrolo[2,3-b]pyridin-5-yloxy)benzamide | 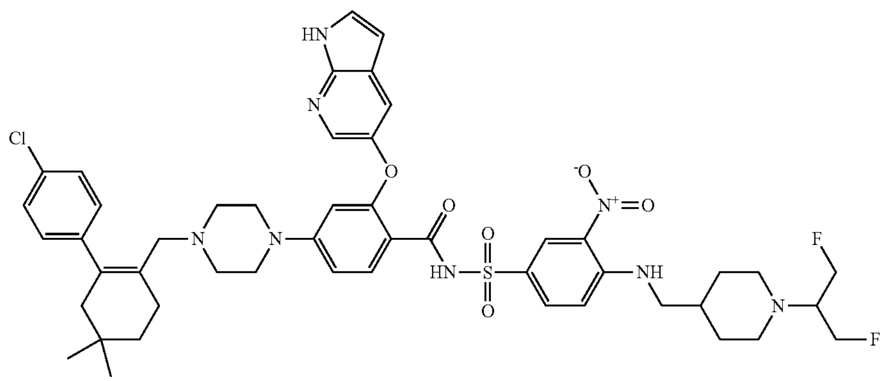 |
| 4-(4-{[2-(4-chlorophenyl)-4,4-dimethylcyclohex-1-en-1-yl]methyl}piperazin-1-yl)-N-({4-[(1-cyclopropyl-4-fluoropiperidin-4-yl)methoxy]-3-nitrophenyl}sulfonyl)-2-(1H-pyrrolo[2,3-b]pyridin-5-yloxy)benzamide | |

-continued

| Name | Structure |
|---|---|
| 4-(4-{[2-(4-chlorophenyl)-4,4-dimethylcyclohex-1-en-1-yl]methyl}piperazin-1-yl)-N-({4-[(4-methoxybenzyl)amino]-3-nitrophenyl}sulfonyl)-2-(1H-pyrrolo[2,3-b]pyridin-5-yloxy)benzamide | 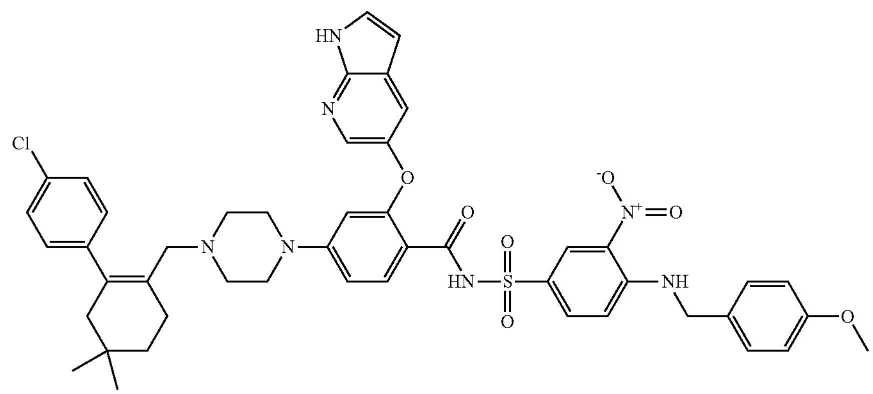 |
| 4-(4-{[2-(4-chlorophenyl)-4,4-dimethylcyclohex-1-en-1-yl]methyl}piperazin-1-yl)-N-[(3-nitro-4-{[3-(trifluoromethoxy)benzyl]amino}phenyl)sulfonyl]-2-(1H-pyrrolo[2,3-b]pyridin-5-yloxy)benzamide | 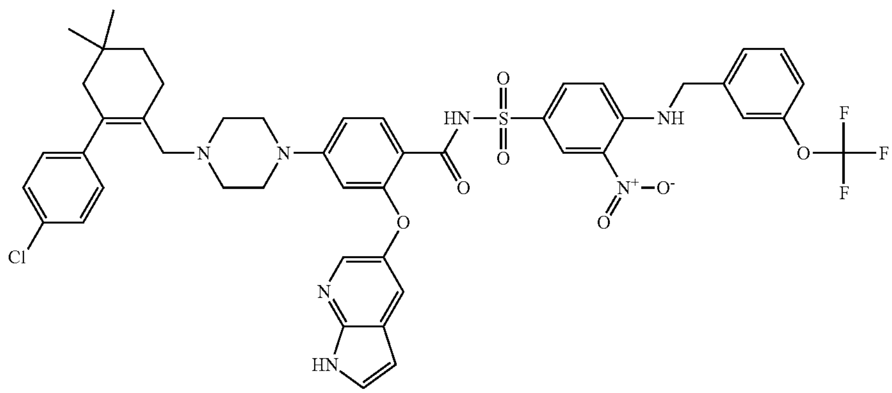 [SMILES: CC1(C)CCC(CN2CCN(c3ccc(C(=O)NS(=O)(=O)c4ccc(NCc5cccc(OC(F)(F)F)c5)c([N+](=O)[O-])c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-({4-[(3-methoxybenzyl)amino]-3-nitrophenyl)sulfonyl)-2-(1H-pyrrolo[2,3-b]pyridin-5-yloxy)benzamide | 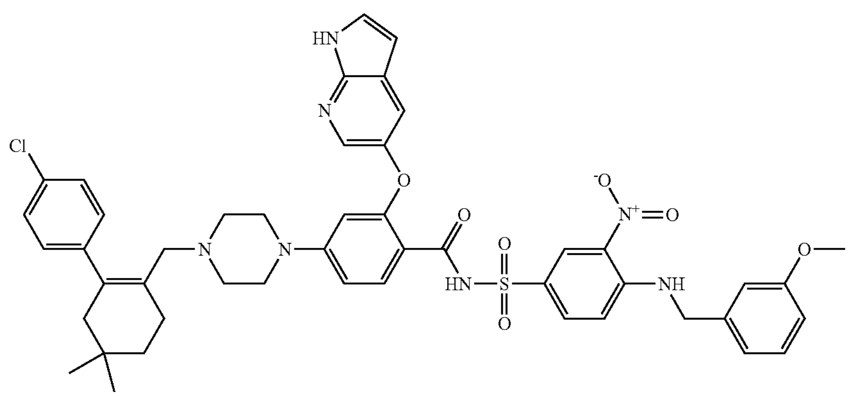 |
| 4-(4-{[2-(4-chlorophenyl)-4,4-dimethylcyclohex-1-en-1-yl]methyl}piperazin-1-yl)-N-[(4-{[4-(difluoromethoxy)benzyl]amino}-3-nitrophenyl)sulfonyl]-2-(1H-pyrrolo[2,3-b]pyridin-5-yloxy)benzamide | 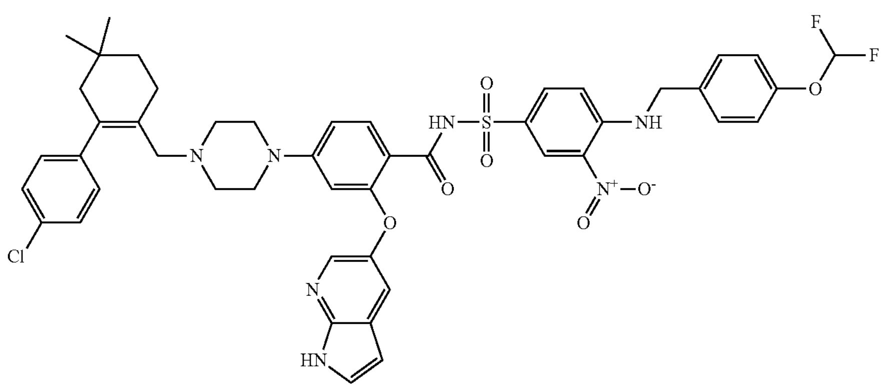 [SMILES: CC1(C)CCC(CN2CCN(c3ccc(C(=O)NS(=O)(=O)c4ccc(NCc5ccc(OC(F)F)cc5)c([N+](=O)[O-])c4)c(Oc4cnc5[nH]ccc5c4)c3)CC2)=C(c2ccc(Cl)cc2)C1] |

| Name | Structure |
|---|---|
| 4-(4-{[2-(4-chlorophenyl)-4,4-dimethylcyclohex-1-en-1-yl]methyl}piperazin-1-yl)-N-{[4-(1,4-dioxaspiro[4.5]dec-8-ylamino)-3-nitrophenyl]sulfonyl}-2-(1H-pyrrolo[2,3-b]pyridin-5-yloxy)benzamide | 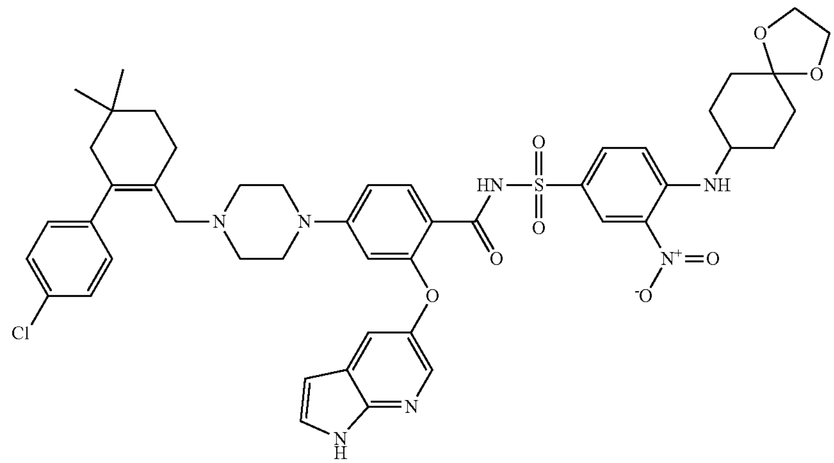 |
| Trans-N-[(4-{[4-(acetylamino)cyclohexyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | 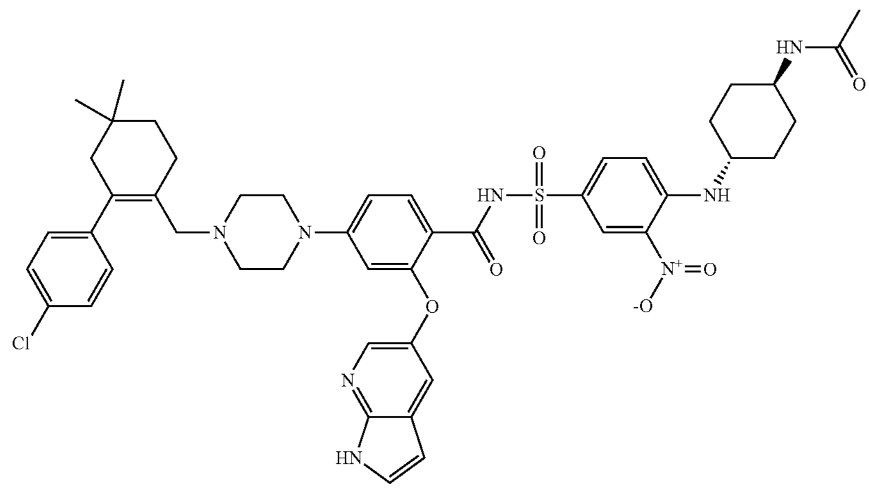 |
| 4-(4-{[2-(4-chlorophenyl)-4,4-dimethylcyclohex-1-en-1-yl]methyl}piperazin-1-yl)-N-[(4-{[(3R)-1-(2,2-difluoroethyl)pyrrolidin-3-yl]amino}-3-nitrophenyl)sulfonyl]-2-(1H-pyrrolo[2,3-b]pyridin-5-yioxy)benzamide | 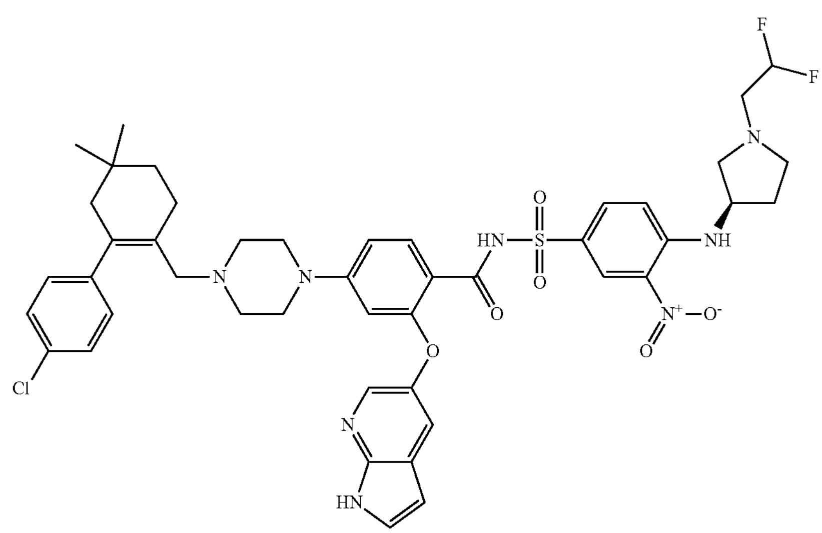 [SMILES: CC1(C)CCC(CN2CCN(c3ccc(C(=O)NS(=O)(=O)c4ccc(N[C@@H]5CCN(CC(F)F)C5)c([N+](=O)[O-])c4)c(Oc4cnc5[nH]ccc5c4)c3)CC2)=C(c2ccc(Cl)cc2)C1] |

| Name | Structure |
|---|---|
| 4-(4-{[2-(4-chlorophenyl)-4,4-dimethylcyclohex-1-en-1-yl]methyl}piperazin-1-yl)-N-[(4-{[(3S)-1-(2-fluoroethyl)pyrrolidin-3-yl]aimno}-3-nitrophenyl)sulfonyl]-2-(1H-pyrrolo[2,3-b]pyridin-5-yloxy)benzamide | 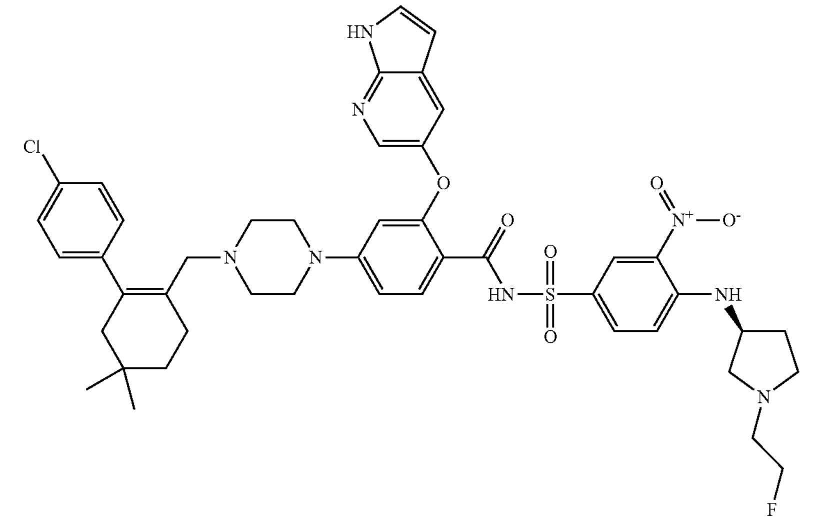 [SMILES: CC1(C)CCC(CN2CCN(c3ccc(C(=O)NS(=O)(=O)c4ccc(N[C@H]5CCN(CCF)C5)c([N+](=O)[O-])c4)c(Oc4cnc5[nH]ccc5c4)c3)CC2)=C(c2ccc(Cl)cc2)C1] |
| 4-(4-{[2-{4-chlorophenyl}-4,4-dimethylcyclohex-1-en-1-yl]methyl}piperazin-1-yl)-N-[(4-{[(3S)-1-(2,2-difluoroethyl)pyrrolidin-3-yl]amino}-3-nitrophenyl)sulfonyl]-2-(1H-pyrrolo[2,3-b]pyridin-5-yloxy)benzamide | |
| 4-(4-{[2-(4-chlorophenyl)-4,4-dimethylcyclohex-1-en-1-yl]methyl}piperazin-1-yl)-N-[(4-{[(3R)-1-(2-fluoroethyl)pyrrolidin-3-yl]amino}-3-nitrophenyl)sulfonyl]-2-(1H-pyrrolo[2,b]pyridin-5-yloxy)benzamide | |
| 4-(4-{[2-(4-chlorophenyl)-4,4-dimethylcyclohex-1-en-1-yl]methyl}piperazin-1-yl)-N-[(3-nitro-4-([(3S)-1-oxetan-3-ylpyrrolidin-3-yl]methoxy]phenyl)sulfonyl]-2-(1H-pyrrolo[2,3-b]pyridin-5-yloxy)benzamide | 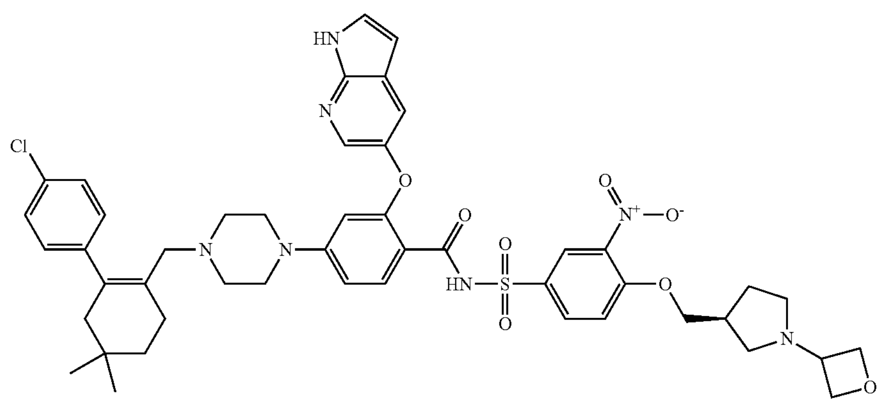 [SMILES: CC1(C)CCC(CN2CCN(c3ccc(C(=O)NS(=O)(=O)c4ccc(OC[C@H]5CCN(C6COC6)C5)c([N+](=O)[O-])c4)c(Oc4cnc5[nH]ccc5c4)c3)CC2)=C(c2ccc(Cl)cc2)C1] |

| Name | Structure |
|---|---|
| 4-(4-{[2-(4-chlorophenyl)-4,4-dimethylcyclohex-1-en-1-yl]methyl}piperazin-1-yl)-N-(4-[(4-hydroxybenzyl)amino]-3-nitrophenyl}sulfonyl)-2-(1H-pyrrolo[2,3-b]pyridin-5-yloxy)benzamide | 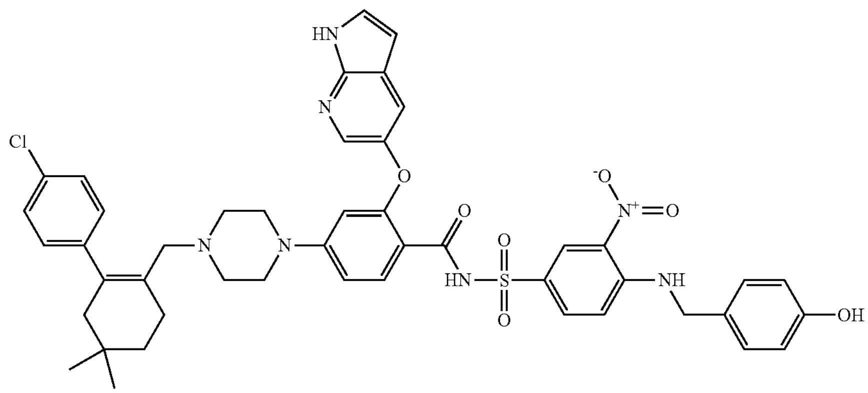 |
| 4-(4-{[2-(4-chlorophenyl)-4,4-dimethylcyclohex-1-en-1-yl]methyl}piperazin-1-yl)-N-({4-[(3-hydroxybenzyl)amino}-3-nitrophenyl}sulfonyl)-2-(1H-pyrrolo[2,3-b]pyridin-5-yloxy)benzamide | 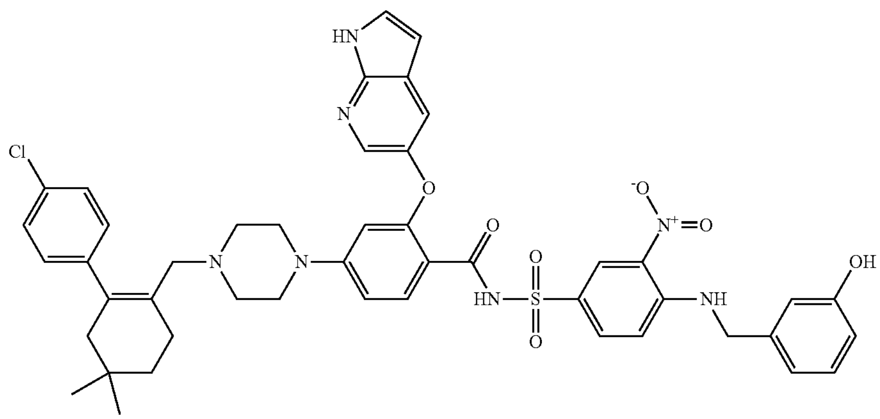 |
| 4-(4-{[2-(4-chlorophenyl)-4,4-dimethylcyclohex-1-en-1-yl]methyl}piperazin-1-yl)-N-[(4-{[3-(difluoromethoxy)benzyl]amino}-3-nitrophenyl)sulfonyl]-2-(1H-pyrrolo[2,3-b]pyridin-5-yloxy)benzamide | |
| 4-(4-{[2-(4-chlorophenyl)-4,4-dimethylcyclohex-1-en-1-yl]methyl}piperazin-1-yl)-N-{[4-({[cis-3-morpholin-4-ylcyclopentyl]methyl}amino)-3-nitrophenyl]sulfonyl}-2-(1H-pyrrolo[2,3-b]pyridin-5-yloxy)benzamide | 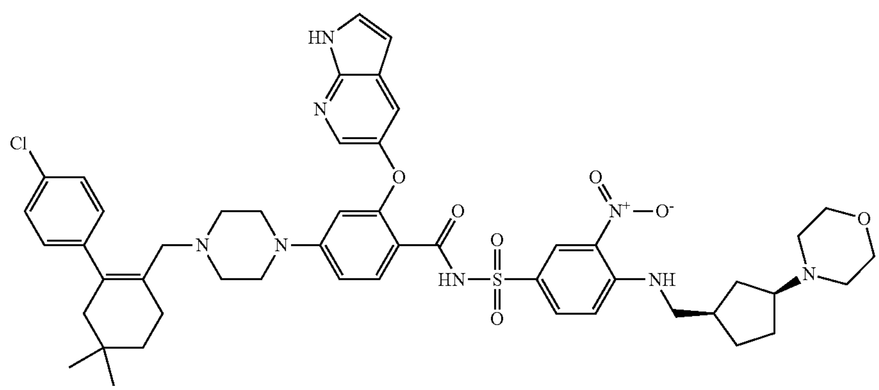 [SMILES: CC1(C)CCC(CN2CCN(c3ccc(C(=O)NS(=O)(=O)c4ccc(NC[C@@H]5CC[C@H](N6CCOCC6)C5)c([N+](=O)[O-])c4)c(Oc4cnc5[nH]ccc5c4)c3)CC2)=C(c2ccc(Cl)cc2)C1] |

| Name | Structure |
|---|---|
| Trans-4-(4-([2-(4-chlorophenyl)-4,4-dimethylcyclohex-1-en-1-yl]methyl}piperazin-1-yl)-N-{[4-({4-[(methylsulfonyl)amino]cyclohexyl}amino)-3-nitrophenyl]sulfonyl}2-(1H-pyrrolo[2,3-b]pyridin-5-yloxy)benzamide | |
| 4-(4-{[2-(4-chlorophenyl)-4,4-dimethylcyclohex-1-en-1-yl]methyl}piperazin-1-yl)-N-({4-[(1-cyclopropylpiperidin-4-yl)amino]-3-[(trifluoromethyl)sulfonyl]phenyl}sulfonyl)-2-(1H-pyrrolo[2,3-b]pyridin-5-yloxy)benzamide | |
| 4-(4-{[2-(4-chlorophenyl)-4,4-dimethylcyclohex-1-en-1-yl]methyl}piperazin-1-yl)-N-({3-nitro-4-[(1-oxetan-3-ylpiperidin-4-yl)methoxy]phenyl}sulfonyl)-2-(1H-pyrrolo[2,3-b]pyridin-5-yloxy)benzamide | |

| Name | Structure |
|---|---|
| 4-(4-{[2-(4-chlorophenyl)-4,4-dimethylcyclohex-1-en-1-yl]methyl}piperazin-1-yl)-N-({4-[(4-fluoro-1-tetrahydro-2H-pyran-4-ylpiperidin-4-yl)methoxy]-3-nitrophenyl}sulfonyl)-2-(1H-pyrrolo[2,3-b]pyridin-5-yloxy)benzamide | 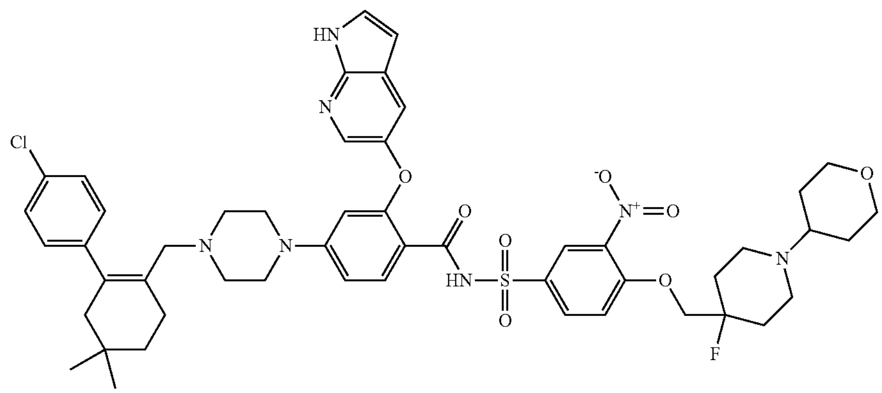 |
| 4-(4-{[2-(4-chlorophenyl)-4,4-dimethylcyclohex-1-en-1-yl]methyl}piperazin-1-yl)-N-({4-[(4-fluoro-1-tetrahydrofuran-3-ylpiperidin-4-yl)methoxy]-3-nitrophenyl}sulfonyl)-2-(1H-pyrrolo[2,3-b]pyridin-5-yloxy)benzamide | 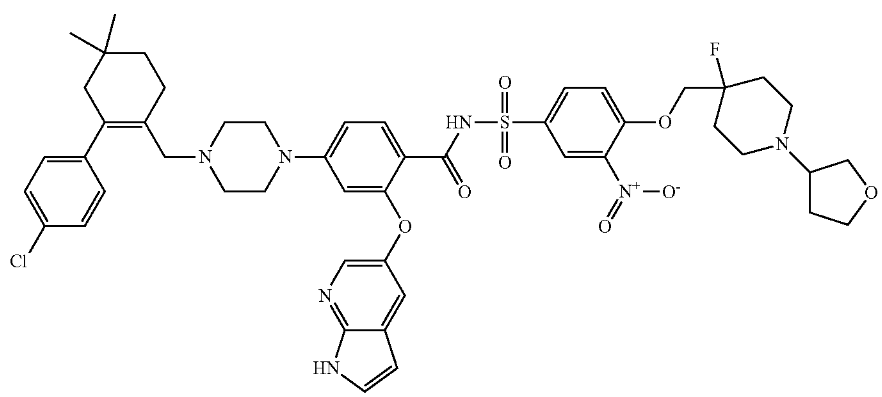 [SMILES: CC1(C)CCC(CN2CCN(c3ccc(C(=O)NS(=O)(=O)c4ccc(OCC5(F)CCN(C6CCOC6)CC5)c([N+](=O)[O-])c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-[(4-{[4-fluoro-1-(methylsulfonyl)piperidin-4-yl]methoxy}-3-nitrophenyl)sulfonyl]-2-(1H-pyrrolo[2,3-b]pyridin-5-yloxy)benzamide | 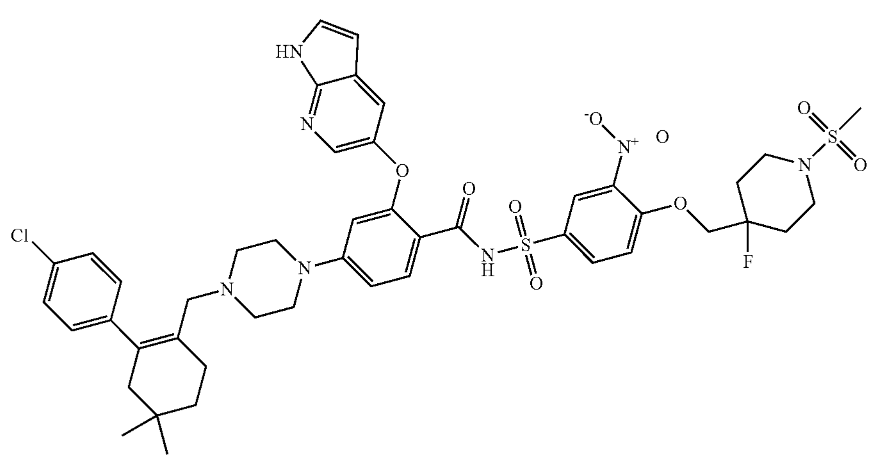 |

-continued

| Name | Structure |
|---|---|
| 4-(4-{[2-(4-chlorophenyl)-4,4-dimethylcyclohex-1-en-1-yl]methyl}piperazin-1-yl)-N-{[3-nitro-4-({[(3R)-1-oxetan-3-ylpyrrolidin-3-yl]methyl}amino)phenyl]sulfonyl}-2-(1H-pyrrolo[2,3-b]pyridin-5-yloxy)benzamide | 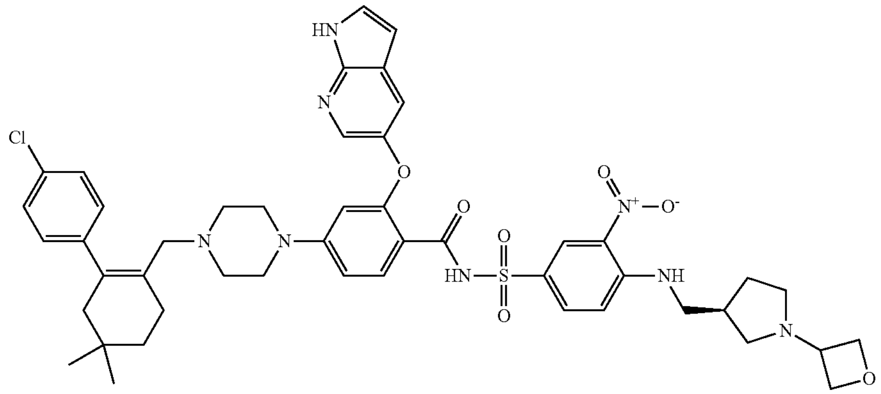 [SMILES: CC1(C)CCC(CN2CCN(c3ccc(C(=O)NS(=O)(=O)c4ccc(NC[C@H]5CCN(C6COC6)C5)c([N+](=O)[O-])c4)c(Oc4cnc5[nH]ccc5c4)c3)CC2)=C(c2ccc(Cl)cc2)C1] |
| Trans-4-(4-{[2-(4-chlorophenyl)-4,4-dimethylcyclohex-1-en-1-yl]methyl}piperazin-1-yl)-N-({4-[(4-hydroxycyclohexyl)methoxy]-3-nitrophenyl}sulfonyl)-2-(1H-pyrrolo[2,3-b]pyridin-5-yloxy)benzamide | 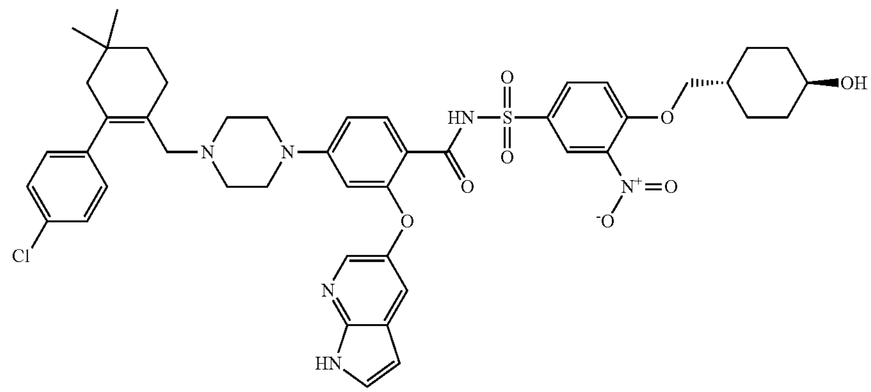 |
| 4-(4-{[2-(4-chlorophenyl)-4,4-dimethylcyclohex-1-en-1-yl]methyl}piperazin-1-yl)-N-{[4-({4-[3-(dimethylamino)propoxy]benzyl}amino)-3-nitrophenyl]sulfonyl}-2-(1H-pyrrolo[2,3-b]pyridin-5-yloxy)benzamide | 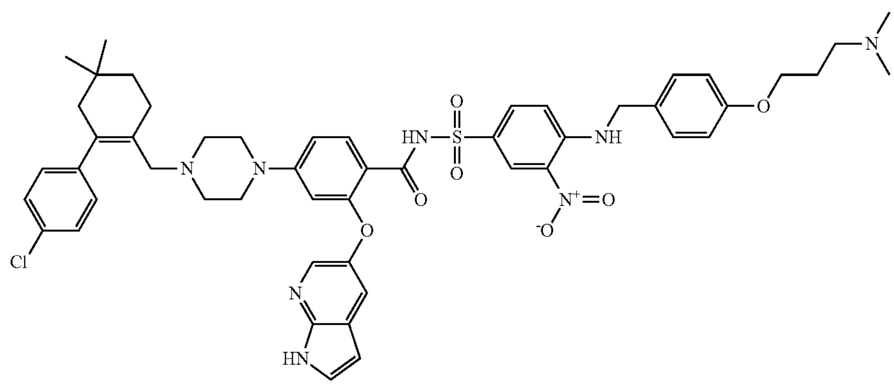 |
| 4-(4-([2-(4-chlorophenyl)-4,4-dimethylcyclohex-1-en-1-yl]methyl}piperazin-1-yl)-N-[(4-{[4-(2-morpholin-4-ylethoxy)benzyl]amino}-3-nitrophenyl)sulfonyl]-2-(1H-pyrrolo[2,3-b]pyridin-5-yloxy)benzamide | 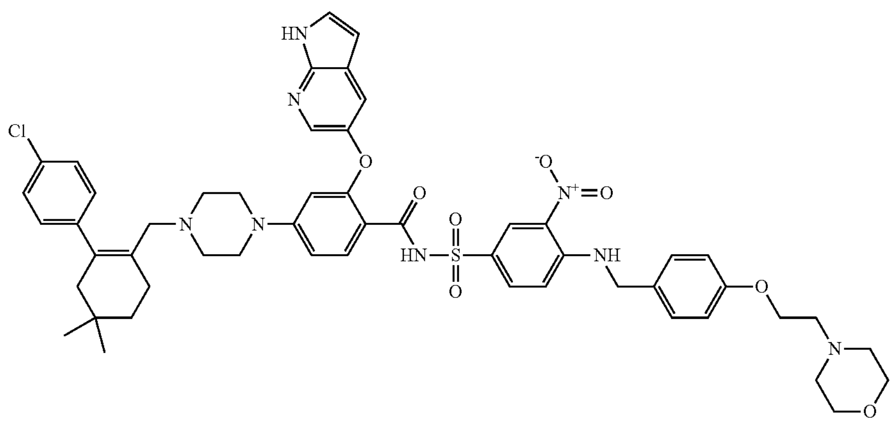 |

| Name | Structure |
|---|---|
| 4-(4-{[2-(4-chlorophenyl)-4,4-dimethylcyclohex-1-en-1-yl]methyl}piperazin-1-yl)-N-{[4-({[(E)-4-hydroxy-1-adamantyl]methyl}amino)-3-nitrophenyl]sulfonyl}-2-(1H-pyrrolo[2,3-b]pyridin-5-yloxy)benzamide | 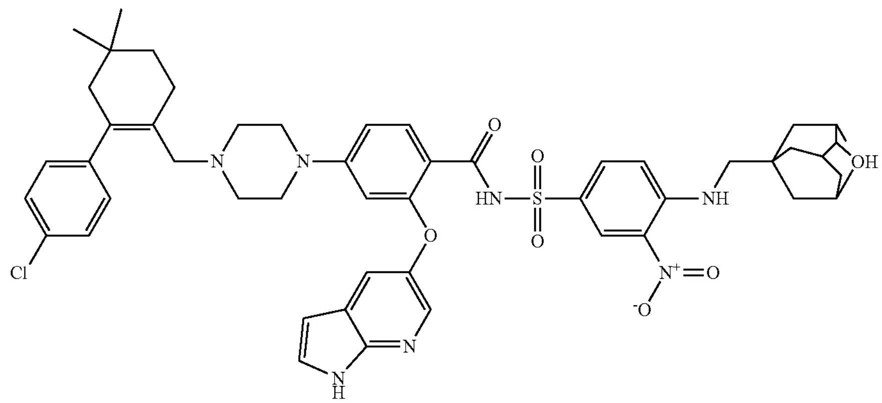 |
| 4-(4-{[2-(4-chlorophenyl)-4,4-dimethylcyclohex-1-en-1-yl]methyl}piperazin-1-yl)-N-{[4-({[(Z)-4-hydroxy-1-adamantyl]methyl}amino)-3-nitrophenyl]sulfonyl}-2-(1H-pyrrolo[2,3-b]pyridin-5-yloxy)benzamide | 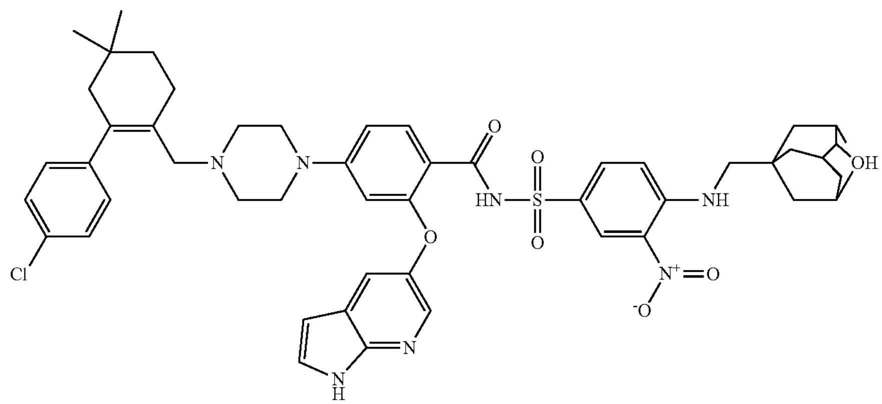 |
| N-({4-[(1S,4S)-bicyclo[2.2.1]hept-5-en-2-ylmethoxy]-3-nitrophenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | 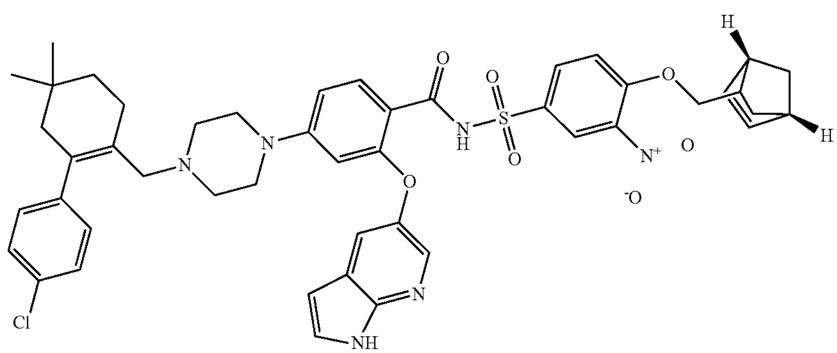 |
| 4-(4-{[2-(4-chlorophenyl)-4,4-dimethylcyclohex-1-en-1-yl]methyl}piperazin-1-yl)-N-({4-[(1-methyl-5-oxopyrrolidin-3-yl)amino]-3-nitrophenyl}sulfonyl)-2-(1H-pyrrolo[2,3-b]pyridin-5-yloxy)benzamide | 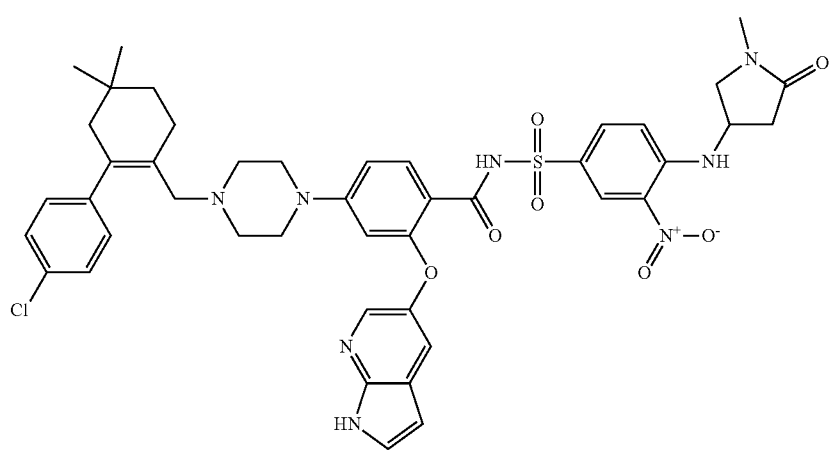 [SMILES: CN1CC(Nc2ccc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2[N+](=O)[O-])CC1=O] |

| Name | Structure |
|---|---|
| 4-(4-([2-(4-chlorophenyl)-4,4-dimethylcyclohex-1-en-1-yl]methyl}piperazin-1-yl)-N-[(4-{[(1R,4R,5R,6S)-5,6-dihydroxybicyclo[2.2.1]hept-2-yl]methoxy)-3-nitrophenyl)sulfonyl]-2-(1H-pyrrolo[2,3-b]pyridin-5-yloxy)benzamide | 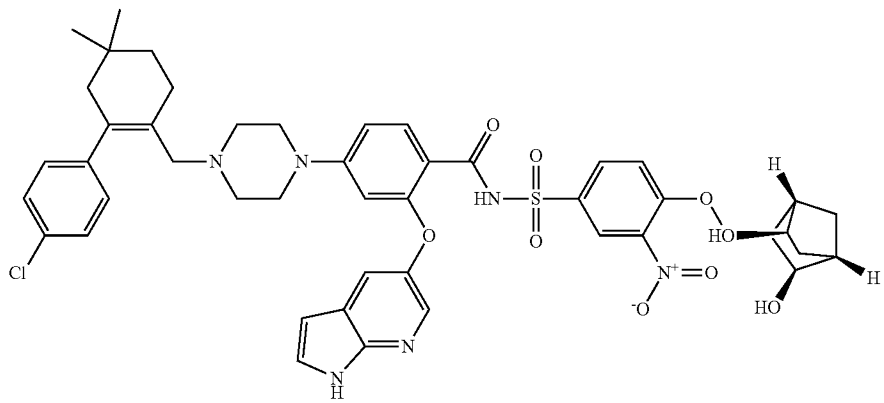 |
| 4-(4-{[2-(4-chlorophenyl)-4,4-dimethylcyclohex-1-en-1-yl]methyl}piperazin-1-yl)-N-[(4-{[(1R,4R,5S,6R)-5,6-dihydroxybicyclo[2.2.1]hept-2-yl]methoxy}-3-nitrophenyl)sulfonyl]-2-(1H-pyrrolo[2,3-b]pyridin-5-yloxy)benzamide | 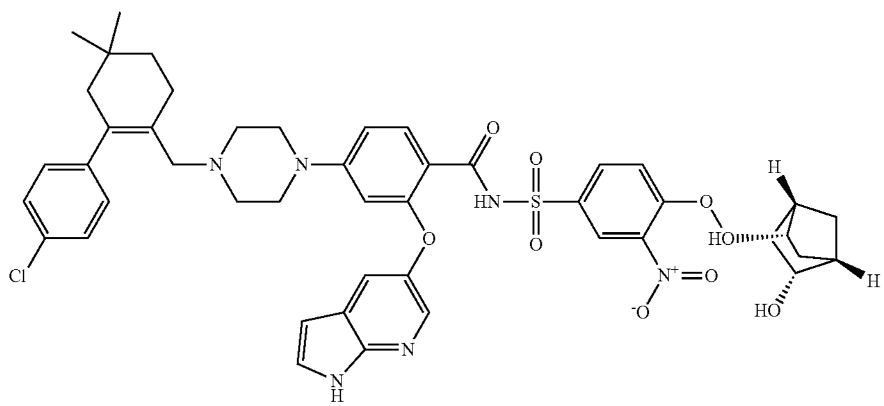 |
| 4-(4-{[2-(4-chlorophenyl)-4,4-dimethylcyclohex-1-en-1-yl]methyl}piperazin-1-yl)-N-({3-nitro-4-[(3-oxocyclohexyl)methoxy]phenyl}sulfonyl)-2-(1H-pyrrolo[2,3-b]pyridin-5-yloxy)benzamide | 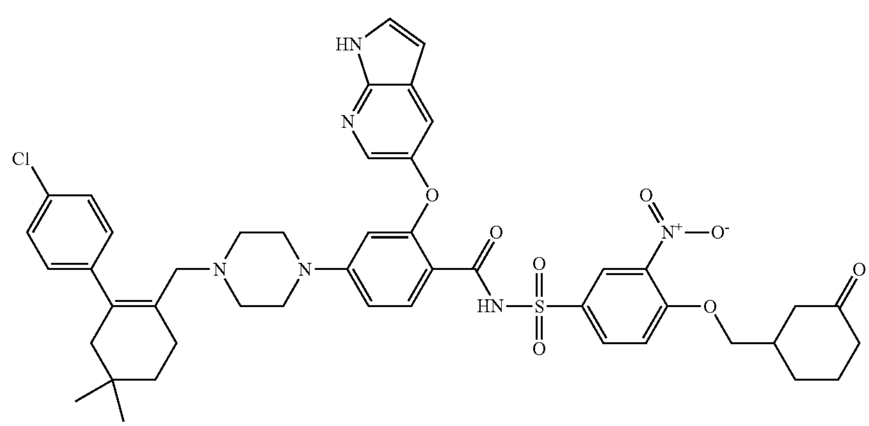 [SMILES: CC1(C)CCC(CN2CCN(c3ccc(C(=O)NS(=O)(=O)c4ccc(OCC5CCCC(=O)C5)c([N+](=O)[O-])c4)c(Oc4cnc5[nH]ccc5c4)c3)CC2)=C(c2ccc(Cl)cc2)C1] |

| Name | Structure |
|---|---|
| 4-(4-([2-(4-chlorophenyl)-5,5-dimethylcyclohexa-1,3-dien-1-yl]methyl}piperazin-1-yl)-N-({3-nitro-4-[(tettrahydro-2H-pyran-4-ylmethyl)amino]phenyl}sulfonyl)-2-(1H-pyrrolo[2,3-b]pyridin-5-yloxy)benzamide | 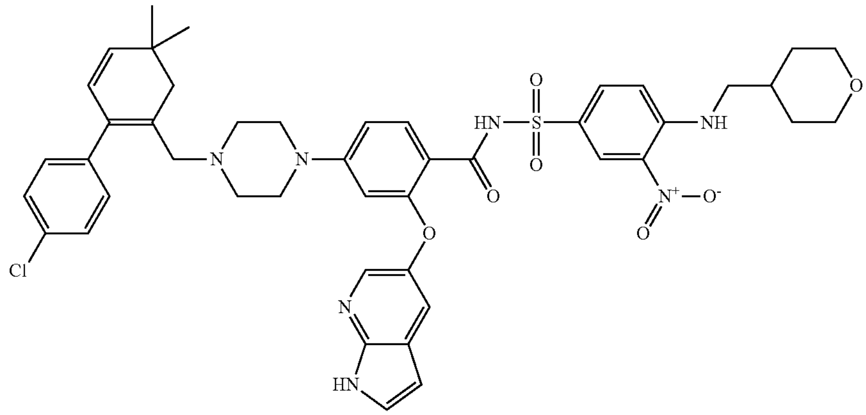 [SMILES: CC1(C)C=CC(c2ccc(Cl)cc2)=C(CN2CCN(c3ccc(C(=O)NS(=O)(=O)c4ccc(NCC5CCOCC5)c([N+](=O)[O-])c4)c(Oc4cnc5[nH]ccc5c4)c3)CC2)C1] |
| 4-(4-{[2-(4-chlorophenyl)-4,4-dimethylcyclohex-1-en-1-yl]methyl}piperazin-1-yl)-N-{[4-({(3R)-1-[2-fluoro-1-(fluoromethyl)ethyl[pyrrolidin-3-yl}amino)-3-nitrophenyl]sulfonyl}-2-(1H-pyrrolo[2,3-b]pyridin-5-yloxy)benzamide | 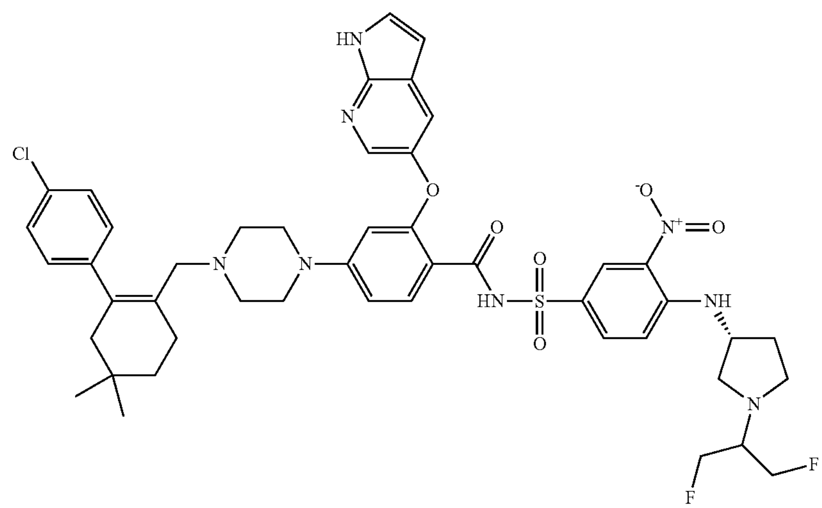 |
| 4-(4-{[2-(4-chlorophenyl)-4,4-dimethylcyclohex-1-en-1-yl]methyl{piperazin-1-yl)-N-{[6-[(4-fluorotetrahydro-2H-pyran-4-yl)methoxy]-5-(trifluoromethyl)pyridin-3-yl]sulfonyl}-2-(1H-pyrrolo[2,3-b]pyridin-5-yloxy)benzamide | 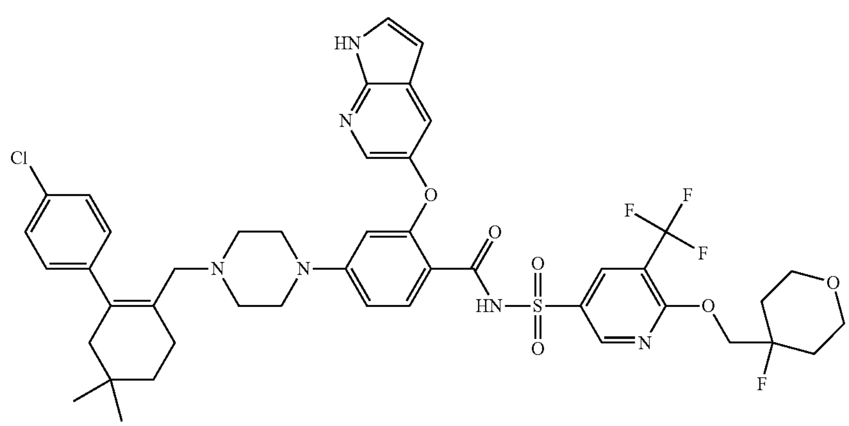 [SMILES: CC1(C)CCC(CN2CCN(c3ccc(C(=O)NS(=O)(=O)c4cnc(OCC5(F)CCOCC5)c(C(F)(F)F)c4)c(Oc4cnc5[nH]ccc5c4)c3)CC2)=C(c2ccc(Cl)cc2)C1] |

-continued

| Name | Structure |
|---|---|
| 4-(4-{[2-(4-chlorophenyl)-4,4-dimethylcyclohex-1-en-1-yl]methyl}piperazin-1-yl)-N-{[3-nitro-4-({[(3S)-1-oxetan-3-ylpyrrolidin-3-yl]methyl}amino)phenyl]sulfonyl}-2-(1H-pyrrolo[2,3-b]pyridin-5-yloxy)benzamide | 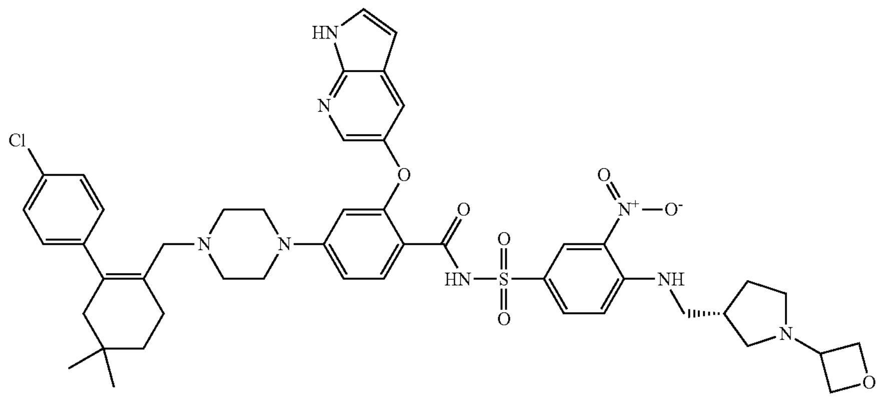 [SMILES: CC1(C)CCC(CN2CCN(c3ccc(C(=O)NS(=O)(=O)c4ccc(NC[C@@H]5CCN(C6COC6)C5)c([N+](=O)[O-])c4)c(Oc4cnc5[nH]ccc5c4)c3)CC2)=C(c2ccc(Cl)cc2)C1] |
| Trans-N-({5-chloro-6-[(4-methoxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | 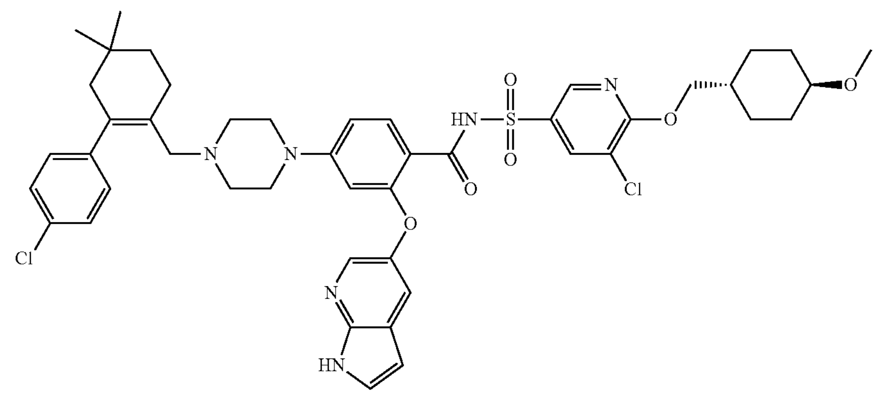 [SMILES: CO[C@H]1CC[C@H](COc2ncc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2Cl)CC1] |
| Cis-N-({5-chloro-6-[(4-methoxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | 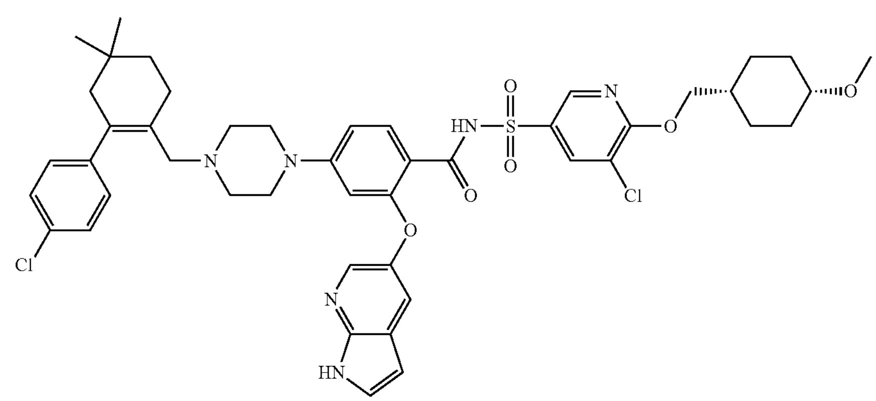 [SMILES: CO[C@H]1CC[C@@H](COc2ncc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2Cl)CC1] |

| Name | Structure |
|---|---|
| 4-(4-{[2-(4-chlorophenyl)-4,4-dimethylcyclohex-1-en-1-yl]methyl}piperazin-1-yl)-N-[(3-nitro-4-{[(3S)-1-oxetan-3-ylpyrrolidin-3-yl]amino}phenyl)sulfonyl]-2-(1H-pyrrolo[2,3-b]pyridin-5-yloxy)benzamide | |
| 4-(4-([2-(4-chlorophenyl)-4,4-dimethylcyclohex-1-en-1-yl)methyl}piperazin-1-yl)-N-({4-[({4-[2-(2-methoxyethoxy)ethyl]morpholin-2-yl}methyl)amino]-3-nitrophenyl}sulfonyl)-2-(1H-pyrrolo[2,3-b]pyridin-5-yloxy)benzamide | 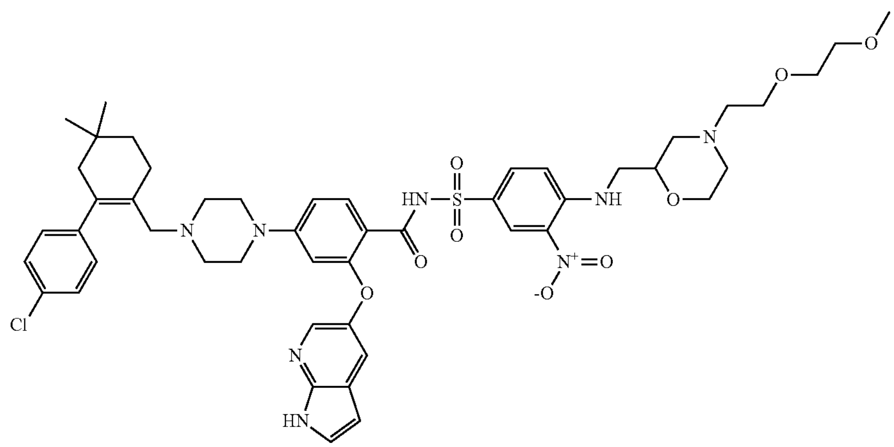 |
| 4-(4-{[2-(4-chlorophenyl)-4,4-dimethylcyclohex-1-en-1-yl]methyl}piperazin-1-yl)-N-{[4-({[4-(cyanomethyl)morpholin-2-yl]methyl}amino)-3-nitrophenyl]sulfonyl}-2-(1H-pyrrolo[2,3-b]pyridin-5-yloxy)benzamide | 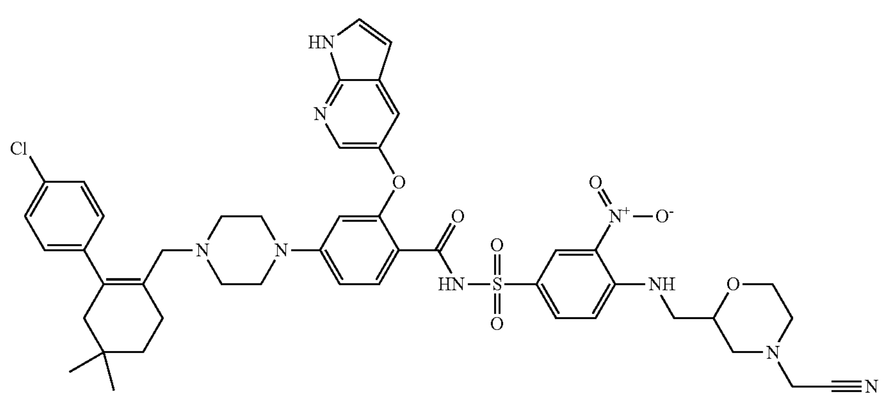 |

| Name | Structure |
|---|---|
| 4-(4-{[2-(4-chlorophenyl)-4,4-dimethylcyclohex-1-en-1-yl]methyl}piperazin-1-yl)-N-{[4-({[4-(N,N-dimethylglycyl)morpholin-2-yl]methyl}amino)-3-nitrophenyl]sulfonyl}-2-(1H-pyrrolo[2,3-b]pyridin-5-yloxy)benzamide | 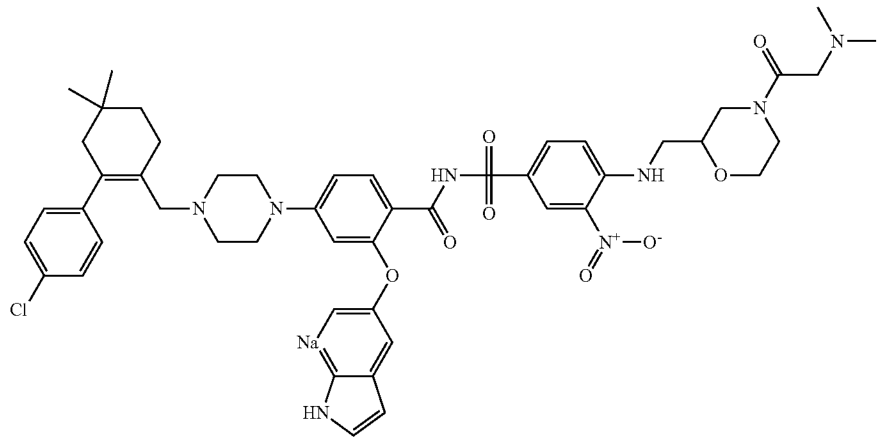 |
| (2-{[(4-{[4-(4-{[2-(4-chlorophenyl)-4,4-dimethylcyclohex-1-en-1-yl]methyl(piperazin-1-yl)-2-(1H-pyrrolo[2,3-b]pyridin-5-yloxy)benzoyl]sulfamoyl}-2-nitrophenyl)amino]methyl}morpholin-4-yl)acetic acid | 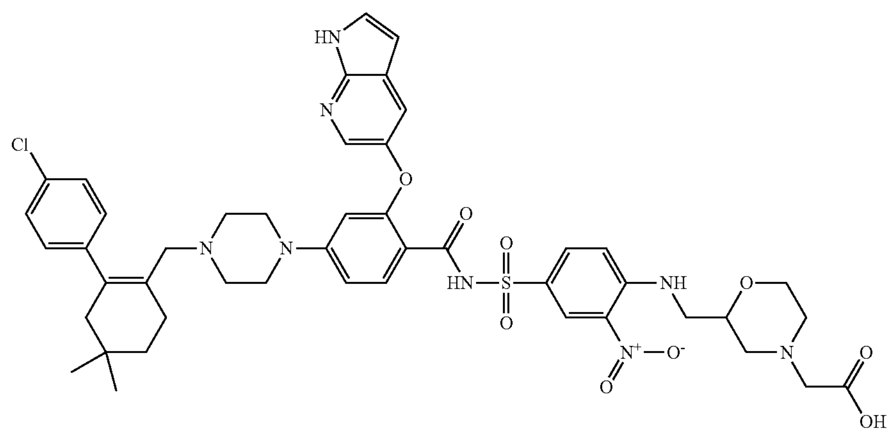 [SMILES: CC1(C)CCC(CN2CCN(c3ccc(C(=O)NS(=O)(=O)c4ccc(NCC5CN(CC(=O)O)CCO5)c([N+](=O)[O-])c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-{[3-nitro-4-({[4-(oxetan-3-yl)morpholin-2-yl]methyl}amino)phenyl]sulfonyl}-2-(1H-pyrrolo[2,3-b]pyridin-5-yloxy)benzamide | 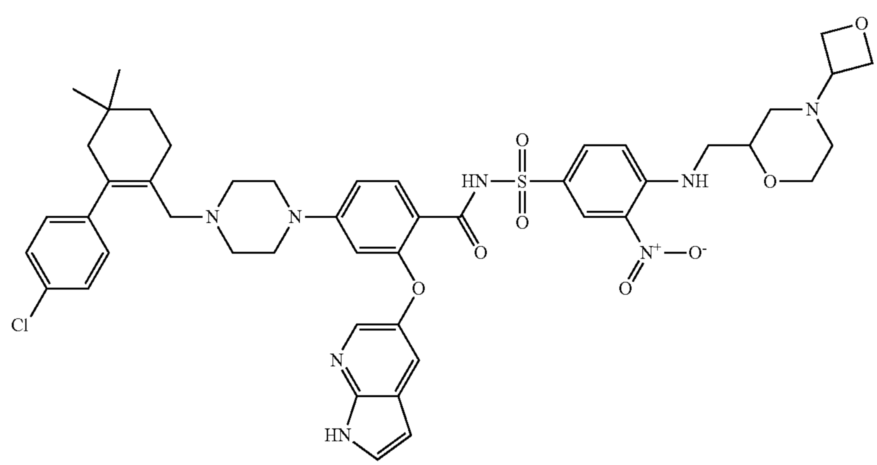 [SMILES: CC1(C)CCC(CN2CCN(c3ccc(C(=O)NS(=O)(=O)c4ccc(NCC5CN(C6COC6)CCO5)c([N+](=O)[O-])c4)c(Oc4cnc5[nH]ccc5c4)c3)CC2)=C(c2ccc(Cl)cc2)C1] |

-continued

| Name | Structure |
|---|---|
| 4-(4-{[2-(4-chlorophenyl)-4,4-dimethylcylohex-1-en-1-yl]methyl}piperazin-1-yl)-N-[(4-{[(4-cyclopropylmorpholin-2-yl)methyl]amino)-3-nitrophenyl)sulfonyl]-2-(1H-pyrrolo[2,3-b]pyridin-5-yloxy)benzamide | 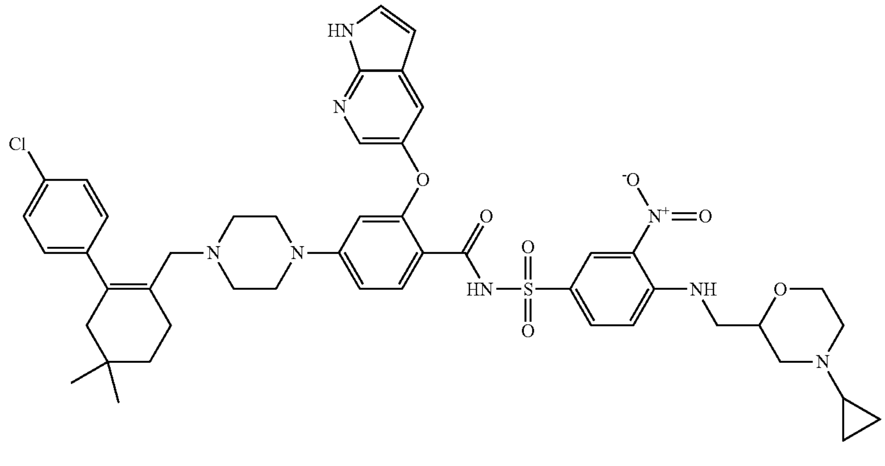 |
| 4-(4-{[2-(4-chlorophenyl)-4,4-dimethylcyclohex-1-en-1-yl]methyl}piperazin-1-yl)-N-{[5-(methylsulfonyl)-6-(tetrahydro-2H-pyran-4-ylmethoxy)pyridin-3-yl]sulfonyl}-2-(1H-pyrrolo[2,3-b]pyridin-5-yloxy)benzamide | 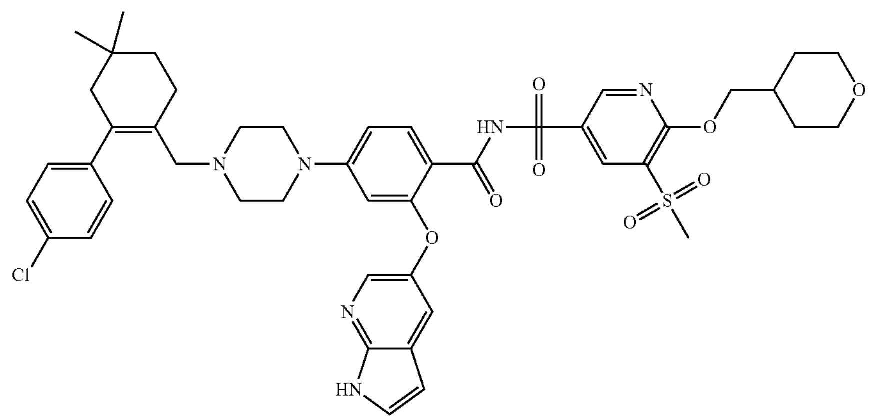 |
| 4-(4-{[2-(4-chlorophenyl)-4,4-dimethylcyclohex-1-en-1-yl]methyl}piperazin-1-yl)-N-({4-[(4-fluorotetiahydro-2H-pyran-4-yl)methoxy]-3-[(trifluoromethyl)sulfonyl]phenyl}sulfonyl)-2-(1H-pyrrolo[2,3-b]pyridin-5-yloxy)benzamide | 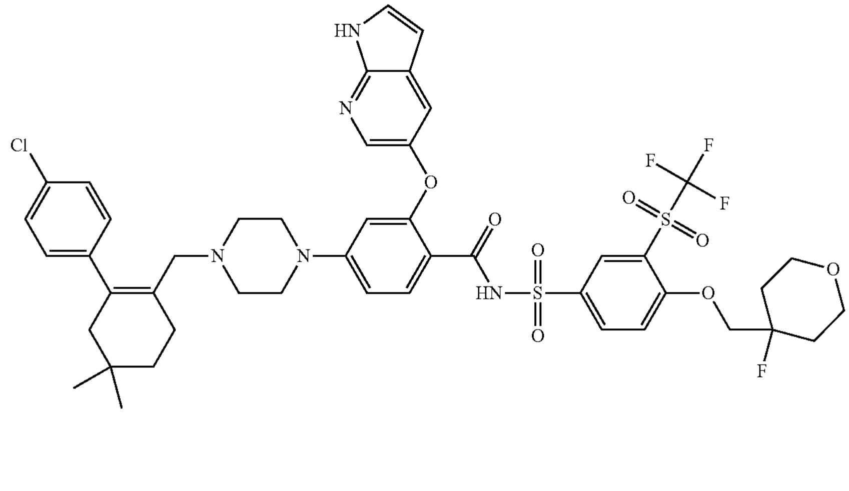 [SMILES: CC1(C)CCC(CN2CCN(c3ccc(C(=O)NS(=O)(=O)c4ccc(OCC5(F)CCOCC5)c(S(=O)(=O)C(F)(F)F)c4)c(Oc4cnc5[nH]ccc5c4)c3)CC2)=C(c2ccc(Cl)cc2)C1] |

| Name | Structure |
|---|---|
| 4-(4-{[2-{4-chlorophenyl)-4,4-dimethylcyclohex-1-en-1-yl]methyl}piperazin-1-yl)-N-({4-[(4-methyltetrahydro-2H-pyran-4-yl)methoxy]-3-nitrophenyl}sulfonyl)-2-(1H-pyrrolo[2,3-b]pyridin-5-yloxy)benzamide | 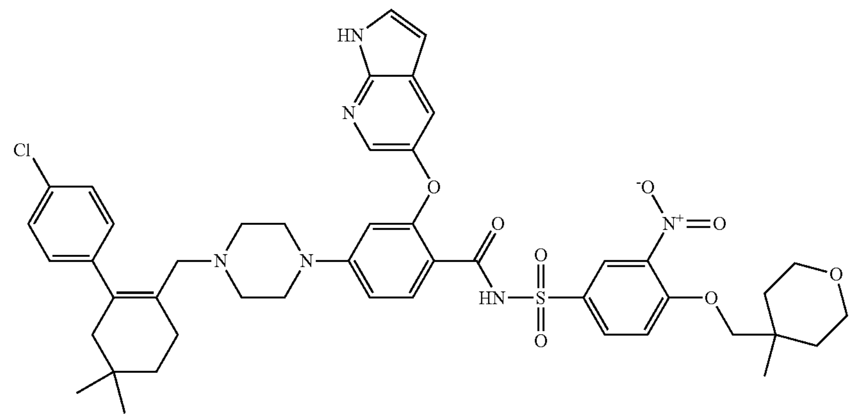 |
| ethyl 4-(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)piperazine-1-carboxylate | 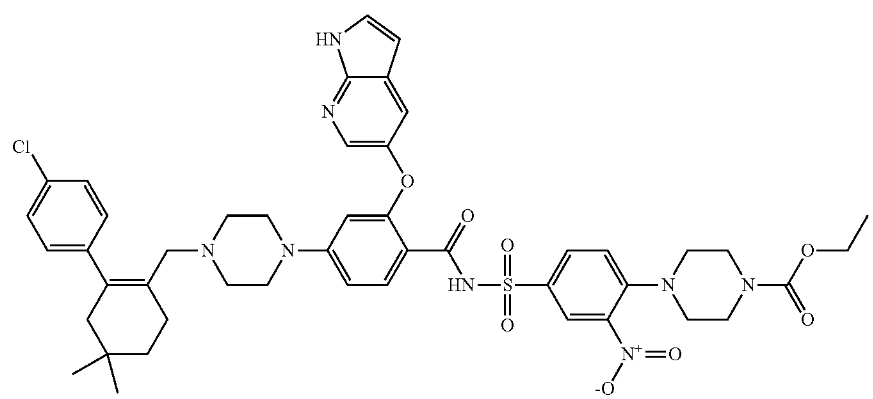 |
| 4-(4-{[2-(4-chlorophenyl)-4,4-dimethylcyclohex-1-en-1-yl]methyl}piperazin-1-yl)-N-{{4-[4-(morpholin-4-yl)piperidin-1-yl]-3-nitrophenyl}sulfonyl]-2-(1H-pyrrolo[2,3-b]pyridin-5-yloxy)benzamide | |

-continued

| Name | Structure |
|---|---|
| 4-(4-{[2-(4-chlorophenyl)-4,4-dimethylcyclohex-1-en-1-yl]methyl}piperazin-1-yl)-N-[(3-nitro-4-{[(3R)-1-(oxetan-3-yl)pyrrolidin-3-yl]amino}phenyl)sulfonyl]-2-(1H-pyrrolo[2,3-b]pyridin-5-yloxy)benzamide | 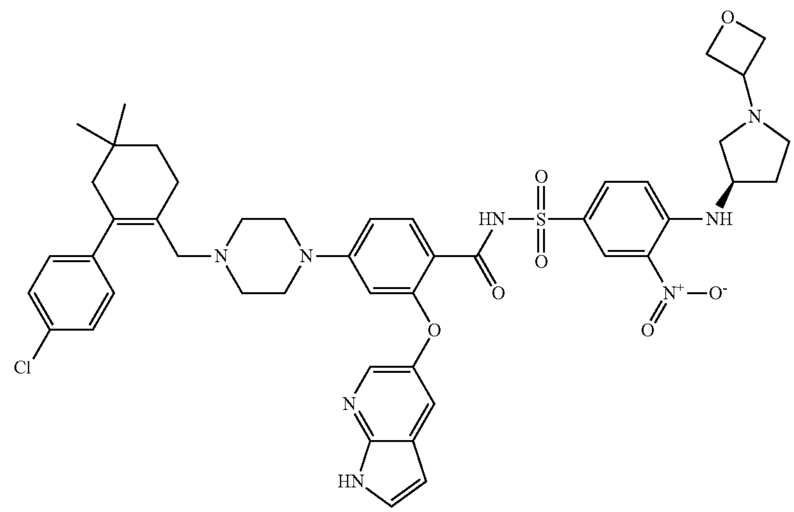 [SMILES: CC1(C)CCC(CN2CCN(c3ccc(C(=O)NS(=O)(=O)c4ccc(N[C@@H]5CCN(C6COC6)C5)c([N+](=O)[O-])c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-[(4-{[(3R)-1-(1,3-difluoropropan-2-yl)pyrrolidin-3-yl]amino}-3-[(trifluoromethyl)sulfonyl]phenyl)sulfonyl]-2-(1H-pyrrolo[2,3-b]pyridin-5-yloxy)benzamide | 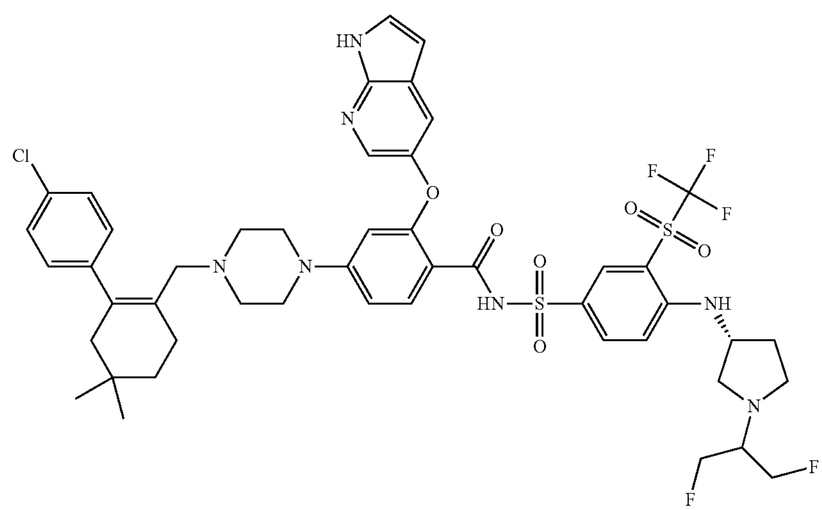 [SMILES: CC1(C)CCC(CN2CCN(c3ccc(C(=O)NS(=O)(=O)c4ccc(N[C@@H]5CCN(C(CF)CF)C5)c(S(=O)(=O)C(F)(F)F)c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-({4-[(1-isopropylpiperidin-4-yl)amino]-3-nitrophenyl}sulfonyl)-2-(1H-pyrrolo[2,3-b]pyridin-5-yloxy)benzamide | 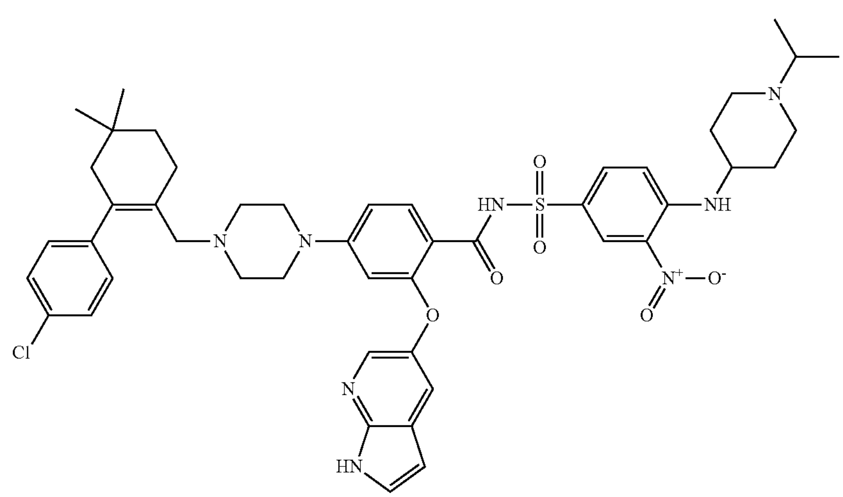 [SMILES: CC(C)N1CCC(Nc2ccc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2[N+](=O)[O-])CC1] |

| Name | Structure |
|---|---|
| N-({4-[(1-tert-butylpiperidin-4-yl)amino]-3-nitrophenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | 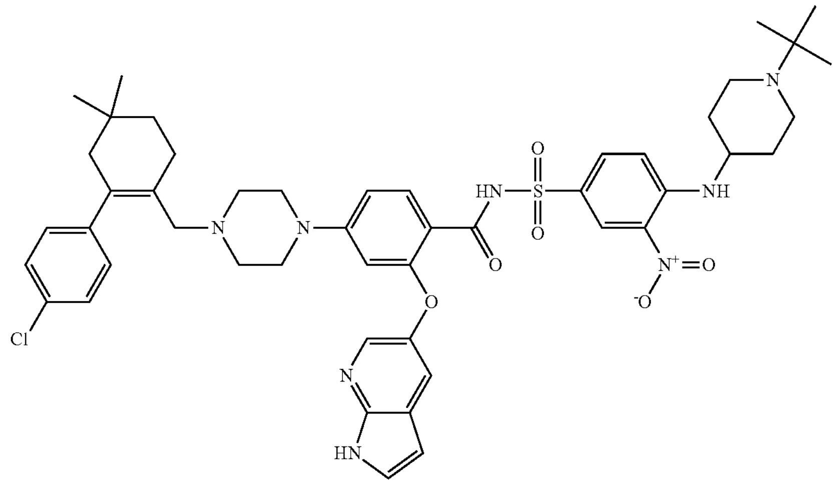 |
| 4-(4-{[2-(4-chlorophenyl)-4,4-dimethylcyclohex-1-en-1-yl]methyl}piperazin-1-yl)-N-{[4-({[1-(2-methoxyethyl)piperidin-3-yl]methyl}amino)-3-nitrophenyl]sulfonyl}-2-(1H-pyrrolo[2,3-b]pyridin-5-yloxy)benzamide | |
| 4-(4-{[2-{4-chlorophenyl)-4,4-dimethylcyclohex-1-en-1-yl]methyl}piperazin-1-yl)-N-{[4-({[1-(cyanomethyl)piperidin-3-yl]methyl}amino)-3-nitrophenyl]sulfonyl}-2-(1H-pyrrolo[2,3-b]pyridin-5-yloxy)benzamido | 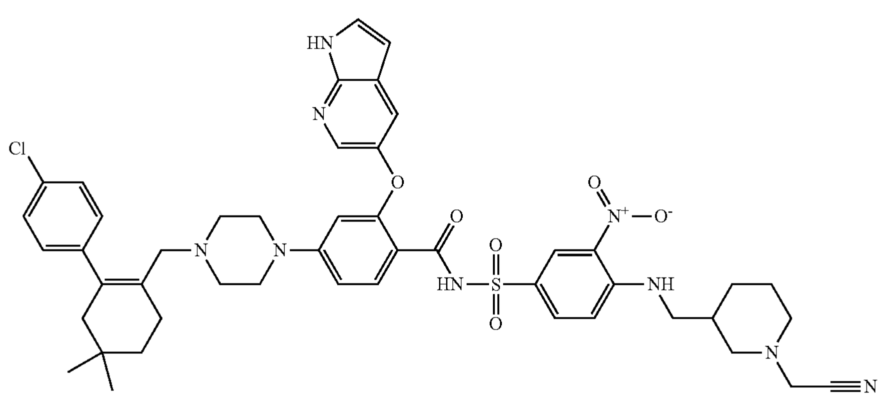 [SMILES: CC1(C)CCC(CN2CCN(c3ccc(C(=O)NS(=O)(=O)c4ccc(NCC5CCCN(CC#N)C5)c([N+](=O)[O-])c4)c(Oc4cnc5[nH]ccc5c4)c3)CC2)=C(c2ccc(Cl)cc2)C1] |

-continued

| Name | Structure |
|---|---|
| 4-(4-{[2-(4-chlorophenyl)-4,4-dimethylcyclohex-1-en-1-yl]methyl}piperazin-1-yl)-N-({4-[(4-fluoro-1-methylpiperidin-4-yl)methoxy]-3-[(trifluoromethyl)sulfonyl]phenyl}sulfonyl)-2-(1H-pyrrolo[2,3-b]pyridin-5-yloxy)benzamide | 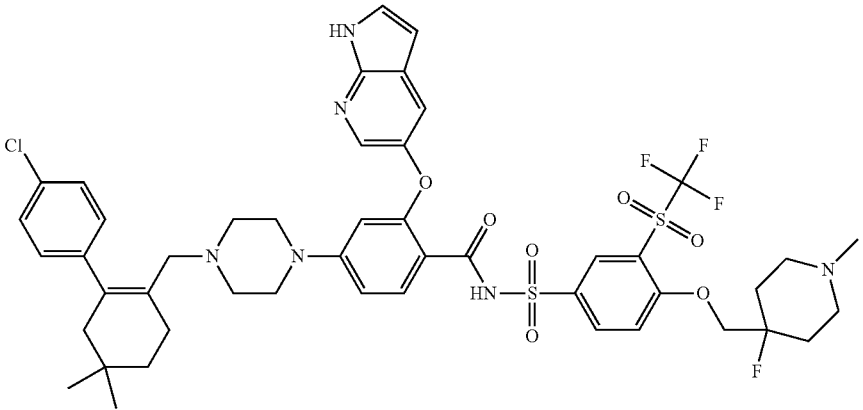 [SMILES: CN1CCC(F)(COc2ccc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2S(=O)(=O)C(F)(F)F)CC1] |
| N-[(5-chloro-6-{[(3R)-1l(1,3-difluoropropan-2-yl)pyrrolidin-3-yl]amino}pyridin-3-yl)sulfonyl]-4-(4-{(2-{4-chlorophenyl)-4,4-dimethylcyclohex-1-en-1-yl]methyl)piperazin-1-yl)-2-(1H-pyrrolo[2,3-b]pyridin-5-yloxy)benzamide | 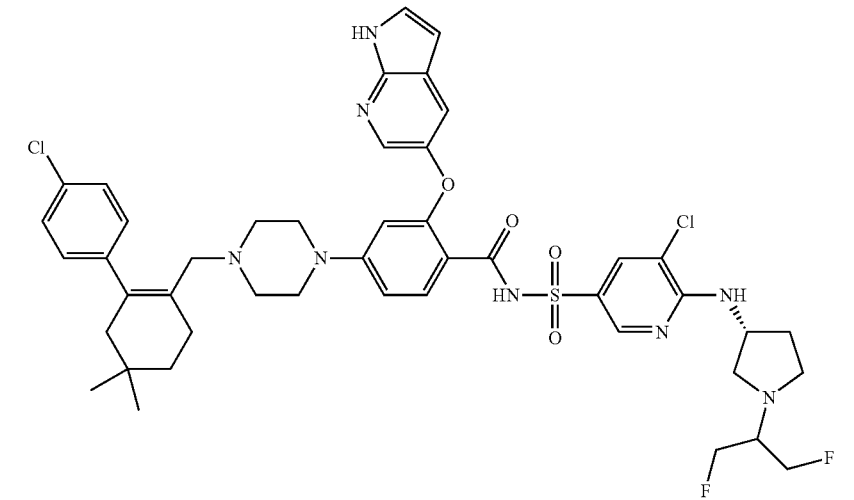 |
| tert-butyl 4-[(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)amino]piperazine-1-carboxylate | 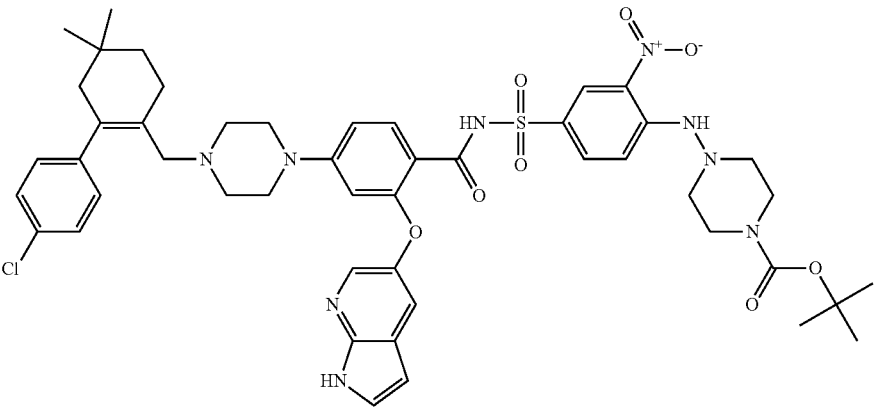 [SMILES: CC1(C)CCC(CN2CCN(c3ccc(C(=O)NS(=O)(=O)c4ccc(NN5CCN(C(=O)OC(C)(C)C)CC5)c([N+](=O)[O-])c4)c(Oc4cnc5[nH]ccc5c4)c3)CC2)=C(c2ccc(Cl)cc2)C1] |

-continued

| Name | Structure |
|---|---|
| 4-(4-{[2-(4-chlorophenyl)-4,4-dimethylcyclohex-1-en-1-yl(methyl)piperazin-1-yl)-N-{{3-(pentafluoro-lambda-6-sulfanyl)-4-[(tetrahydro-2H-pyran-4-ylmethyl)amino]phenyl}sulfonyl)-2-(1H-pyrrolo[2,3-b]pyridin-5-yloxy)benzamide | 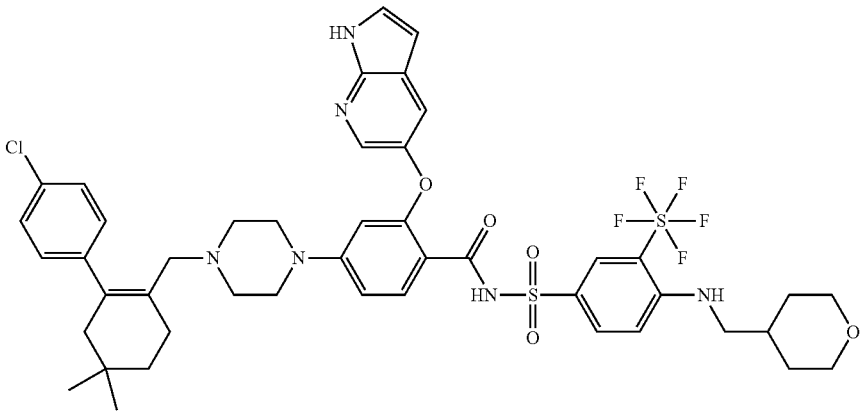 [SMILES: CC1(C)CCC(CN2CCN(c3ccc(C(=O)NS(=O)(=O)c4ccc(NCC5CCOCC5)c(S(F)(F)(F)(F)F)c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-({4-[(4-methoxytetrahydro-2H-pyran-4-yl)methoxy]-3-nitrophenyl}sulfonyl)-2-(1H-pyrrolo[2,3-b]pyridin-5-yloxy)benzamide | 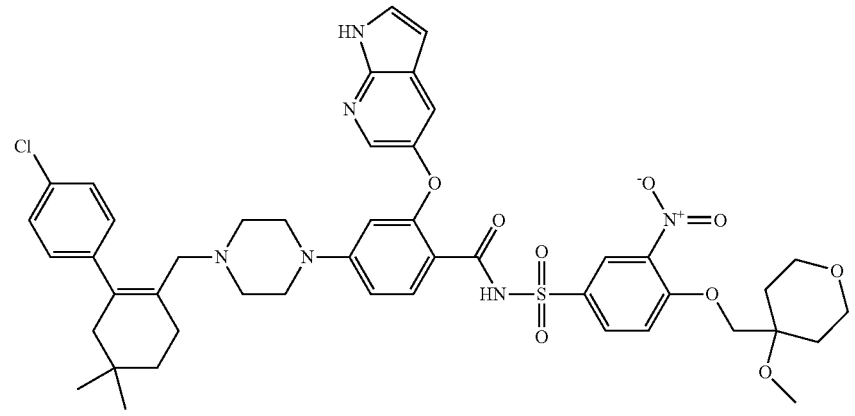 |
| 4-(4-{[2-(4-chlorophenyl)-4,4-dimethylcyclohex-1-en-1-yl]methyl}piperazin-1-yl)-N-[(4-{[(3R)-1-(1,3-difluoropropan-2-yl)pyrrolidin-3-yl]oxy}-3-nitrophenyl)sulfonyl]-2-(1H-pyrrolo[2,3-b]pyridin-5-yloxy)benzamide | 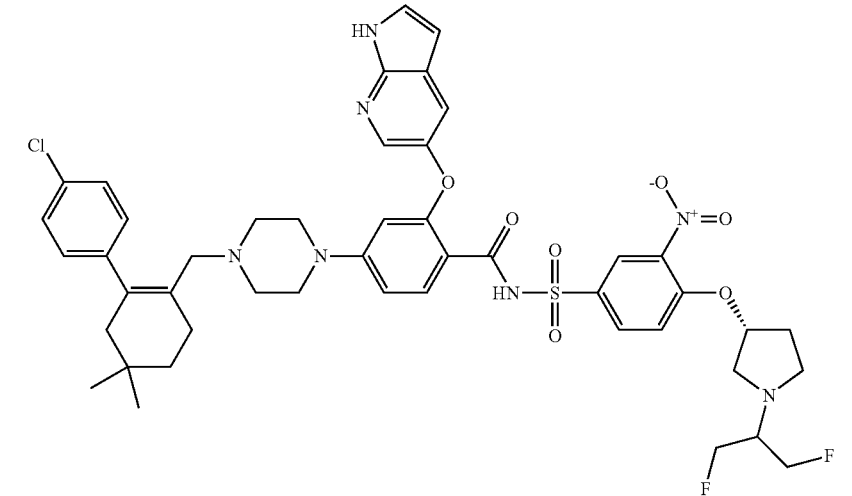 |

| Name | Structure |
|---|---|
| 4-(4-{[2-(4-chlorophenyl)-4,4-dimethylcyclohex-1-en-1-yl]methyl}piperazin-1-yl)-N-[(3-nitro-4-{[4-(oxetan-3-yl)piperazin-1-yl]amino}phenyl)sulfonyl]-2-(1H-pyrrolo[2,3-b]pyridin-5-yloxy)benzamide | |
| 4-(4-{[2-(4-chlorophenyl)-4,4-dimethylcyclohex-1-en-1-yl(methyl}piperazin-1-yl)-N-[(3-nitro-4-{[4-(tetrahydro-2H-pyran-4-yl)piperazin-1-yl]amino}phenyl)sulfonyl]-2-(1H-pyrrolo[2,3-b]pyridin-5-yloxy)benzamide | 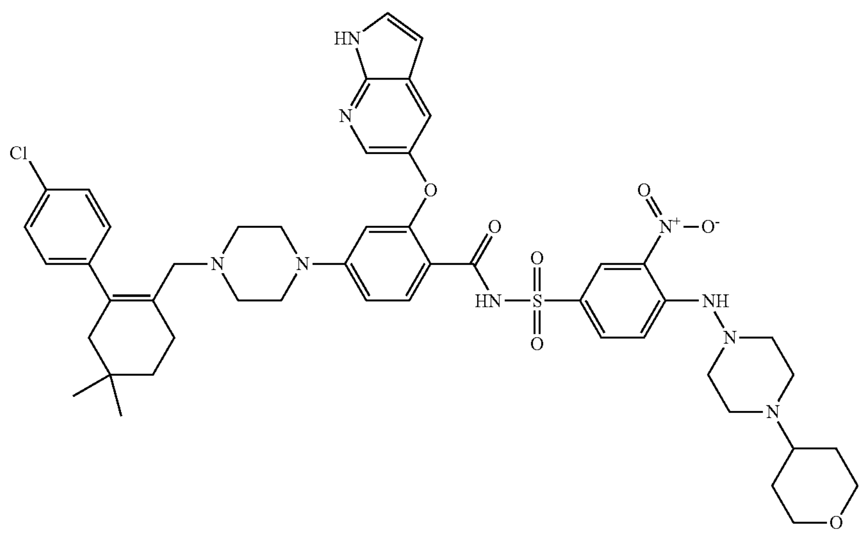 |
| 4-(4-{[2-(4-chlorophenyl)-4,4-dimethylcyclohex-1-en-1-yl]methyl}piperazin-1-yl)-N-({3-nitro-4-[(3R)-tetrahydrofuran-3-ylamino]phenyl}sulfonyl)-2-(1H-pyrrolo[2,3-b]pyridin-5-yloxy)benzamide | 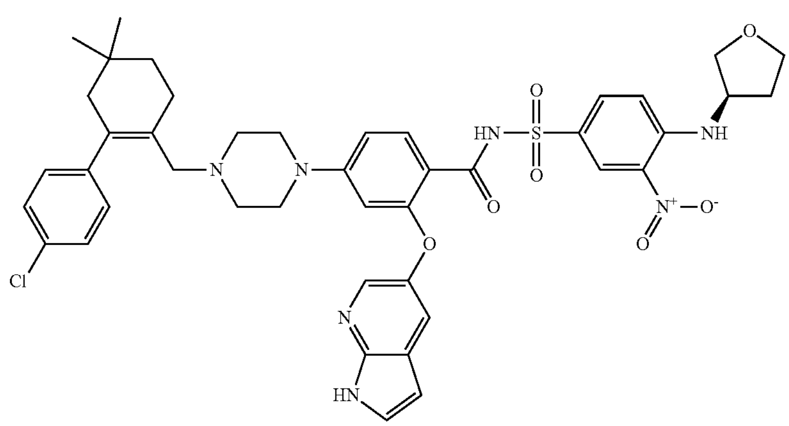 [SMILES: CC1(C)CCC(CN2CCN(c3ccc(C(=O)NS(=O)(=O)c4ccc(N[C@@H]5CCOC5)c([N+](=O)[O-])c4)c(Oc4cnc5[nH]ccc5c4)c3)CC2)=C(c2ccc(Cl)cc2)C1] |

-continued

| Name | Structure |
|---|---|
| 4-(4-{[2-(4-chlorophenyl)-4,4-dimethylcyclohex-1-en-1-yl]methyl}piperazin-1-yl)-N-[(4-{[(4,4-difluorocyclohexyl)methyl]amino}-3-nitrophenyl)sulfonyl]-2-(1H-pyrrolo[2,3-b]pyridin-5-yloxy)benzamide | 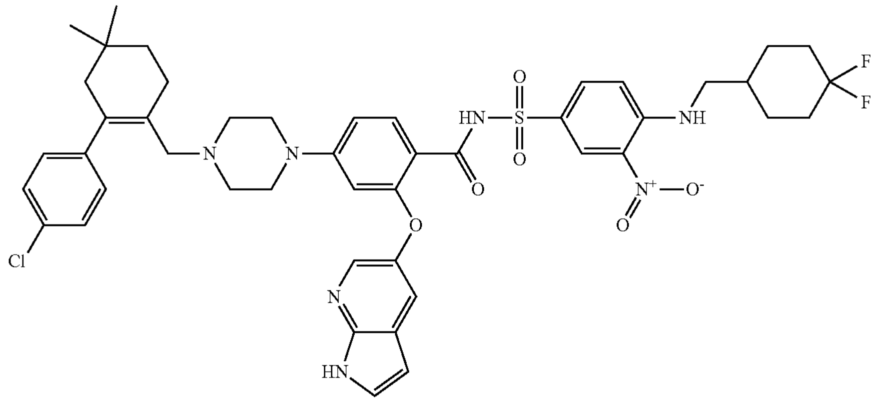 [SMILES: CC1(C)CCC(CN2CCN(c3ccc(C(=O)NS(=O)(=O)c4ccc(NCC5CCC(F)(F)CC5)c([N+](=O)[O-])c4)c(Oc4cnc5[nH]ccc5c4)c3)CC2)=C(c2ccc(Cl)cc2)C1] |
| N-({4-[(1-tert-butylpiperidin-4-yl)amino]-3-[(trifluoromethyl)sulfonyl]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | 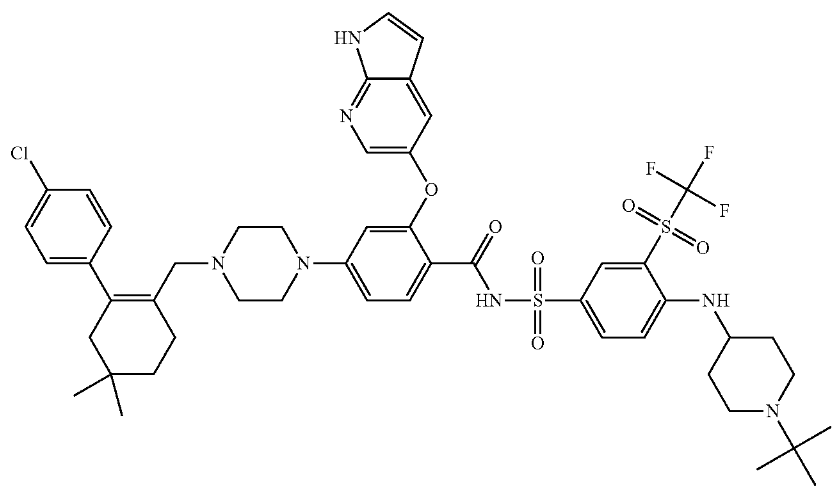 [SMILES: CC1(C)CCC(CN2CCN(c3ccc(C(=O)NS(=O)(=O)c4ccc(NC5CCN(C(C)(C)C)CC5)c(S(=O)(=O)C(F)(F)F)c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-({4-({[4-(oxetan-3-yl)morpholin-2-yl]methyl}amino)-3-[(trifluoromethyl)sulfonyl]phenyl}sulfonyl)-2-(1H-pyrrolo[2,3-b]pyridin-5-yloxy)benzamide | 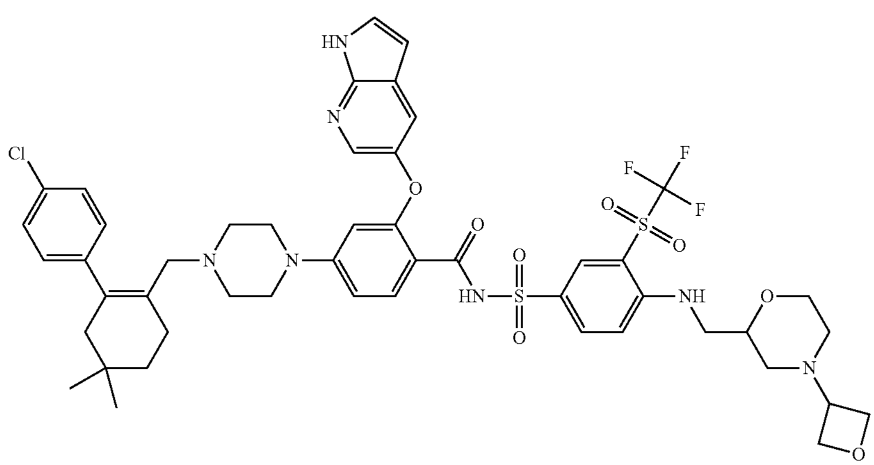 [SMILES: CC1(C)CCC(CN2CCN(c3ccc(C(=O)NS(=O)(=O)c4ccc(NCC5CN(C6COC6)CCO5)c(S(=O)(=O)C(F)(F)F)c4)c(Oc4cnc5[nH]ccc5c4)c3)CC2)=C(c2ccc(Cl)cc2)C1] |

| Name | Structure |
|---|---|
| N-[(5-chloro-6-{[(4-fluorotetrahydro-2H-pyran-4-yl)methyl]amino}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | 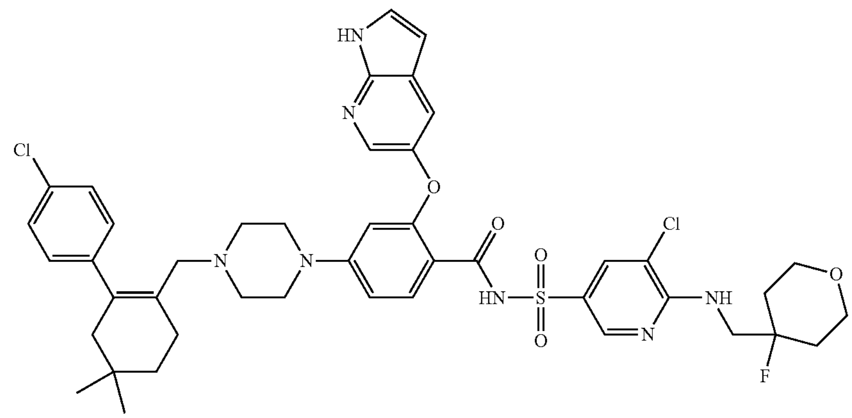 [SMILES: CC1(C)CCC(CN2CCN(c3ccc(C(=O)NS(=O)(=O)c4cnc(NCC5(F)CCOCC5)c(Cl)c4)c(Oc4cnc5[nH]ccc5c4)c3)CC2)=C(c2ccc(Cl)cc2)C1] |
| N-({5-chloro-6-[(1-cyclopropylpiperidin-4-yl)amino]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | 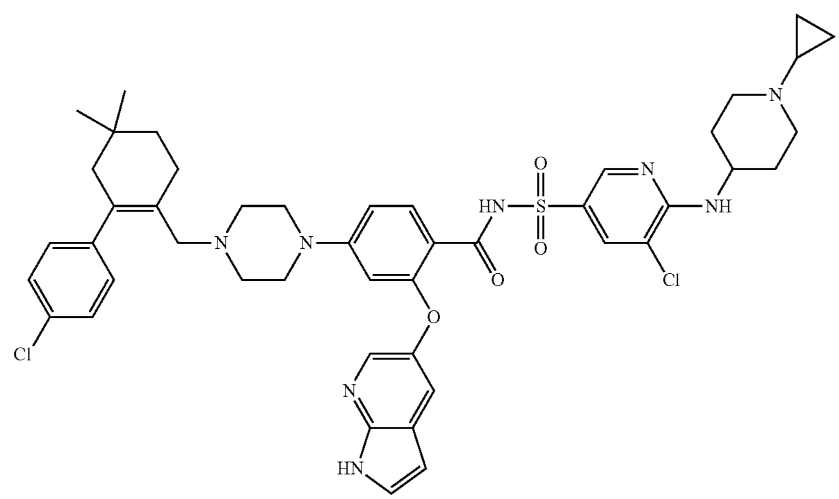 [SMILES: CC1(C)CCC(CN2CCN(c3ccc(C(=O)NS(=O)(=O)c4cnc(NC5CCN(C6CC6)CC5)c(Cl)c4)c(Oc4cnc5[nH]ccc5c4)c3)CC2)=C(c2ccc(Cl)cc2)C1] |
| N-[(5-chloro-6-{[(2S)-4-(cyanomethyl)morpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | 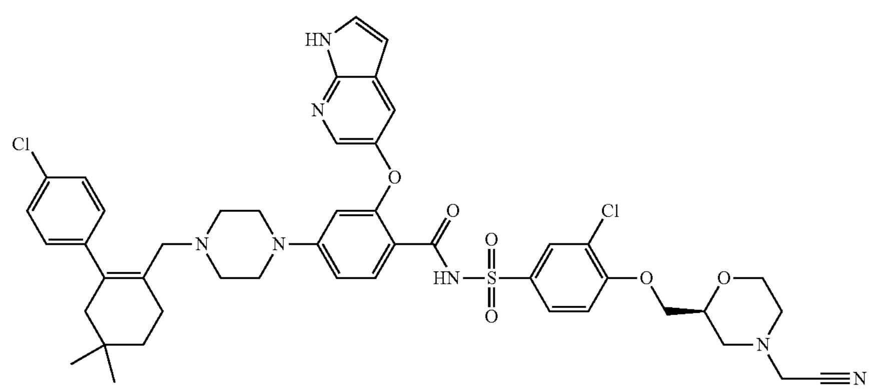 [SMILES: CC1(C)CCC(CN2CCN(c3ccc(C(=O)NS(=O)(=O)c4ccc(OC[C@@H]5CN(CC#N)CCO5)c(Cl)c4)c(Oc4cnc5[nH]ccc5c4)c3)CC2)=C(c2ccc(Cl)cc2)C1] |

-continued

| Name | Structure |
|---|---|
| N-[(5-chloro-6-{[(2S)-4-(N,N-dimethylglycyl)morpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | |
| N-[(5-chloro-6-{[(2R)-4-(cyanomethyl)morpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | |
| N-[(5-chloro-6-{[(2R)-4-(N,N-dimethylglycyl)morpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | |

| Name | Structure |
|---|---|
| 4-(4-{[2-(4-chlorophenyl)-4,4-dimethylcyclohex-1-en-1-yl]methyl}piperazin-1-yl)-N-({5-fluoro-6-[(4-fluorotetrahydro-2H-pyran-4-yl)methoxy]pyridin-3-yl}sulfonyl)-2-(1H-pyrrolo[2,3-b]pyridin-5-yloxy)benzamide | 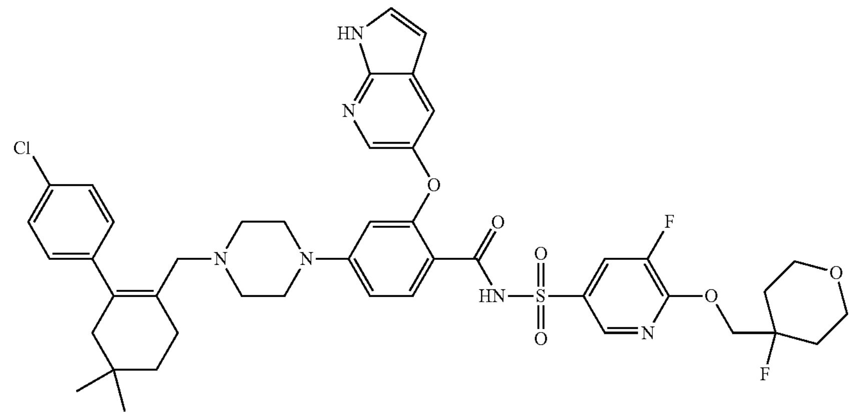 [SMILES: CC1(C)CCC(CN2CCN(c3ccc(C(=O)NS(=O)(=O)c4cnc(OCC5(F)CCOCC5)c(F)c4)c(Oc4cnc5[nH]ccc5c4)c3)CC2)=C(c2ccc(Cl)cc2)C1] |
| N-({5-chloro-6-[3-hydroxy-2-(hydroxymethyl)-2-methylpropoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | 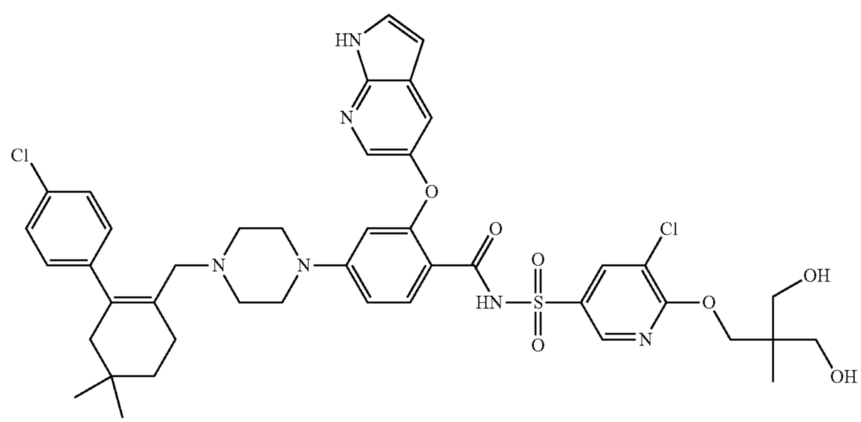 [SMILES: CC1(C)CCC(CN2CCN(c3ccc(C(=O)NS(=O)(=O)c4cnc(OCC(C)(CO)CO)c(Cl)c4)c(Oc4cnc5[nH]ccc5c4)c3)CC2)=C(c2ccc(Cl)cc2)C1] |
| 4-(4-{[[2-(4-chlorophenyl)-4,4-dimethylcyclohex-1-en-1-yl]methyl}piperazin-1-yl)-N-({6-[(4-fluorotetrahydro-2H-pyran-4-yl)methoxy]pyridin-3-yl)sulfonyl)-2-(1H-pyrrolo[2,3-b]pyridin-5-yloxy)benzamide | 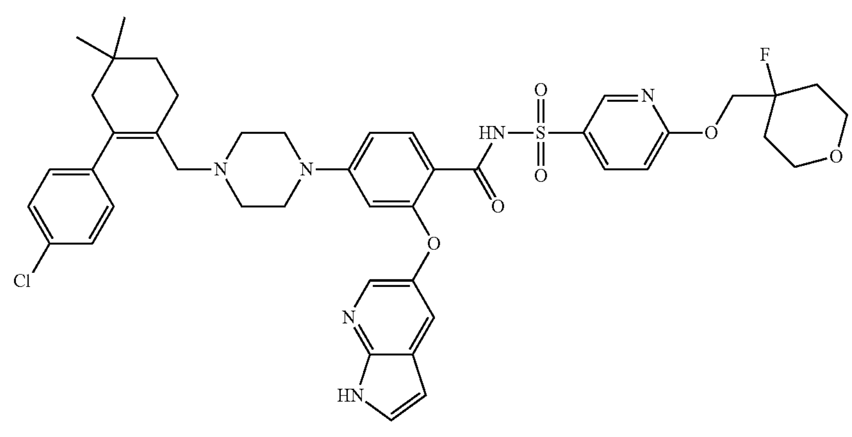 [SMILES: CC1(C)CCC(CN2CCN(c3ccc(C(=O)NS(=O)(=O)c4ccc(OCC5(F)CCOCC5)nc4)c(Oc4cnc5[nH]ccc5c4)c3)CC2)=C(c2ccc(Cl)cc2)C1] |

| Name | Structure |
|---|---|
| 4-(4-{[2-(4-chlorophenyl)-4,4-dimethylcyclohex-1-en-1-yl]methyl}piperazin-1-yl)-N-{[4-({[4-(1,3-difluoropropan-2-yl)morpholin-2-yl]methyl}amino)-3-nitrophenyl]sulfonyl}-2-(1H-pyrrolo[2,3-b]pyridin-5-yloxy)benzamide | 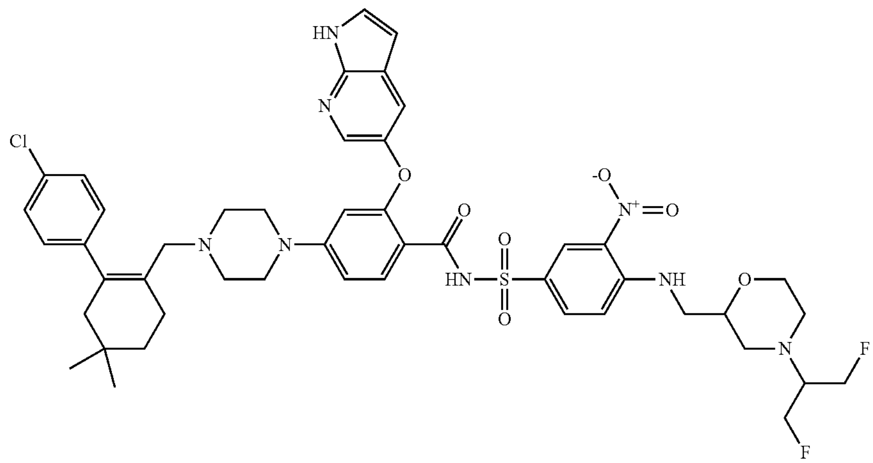 |
| N-[(5-chloro-6-{[1-(cyanomethyl)piperidin-4-yl]methoxy}pyridin-3-yl)sulfonyl]4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | 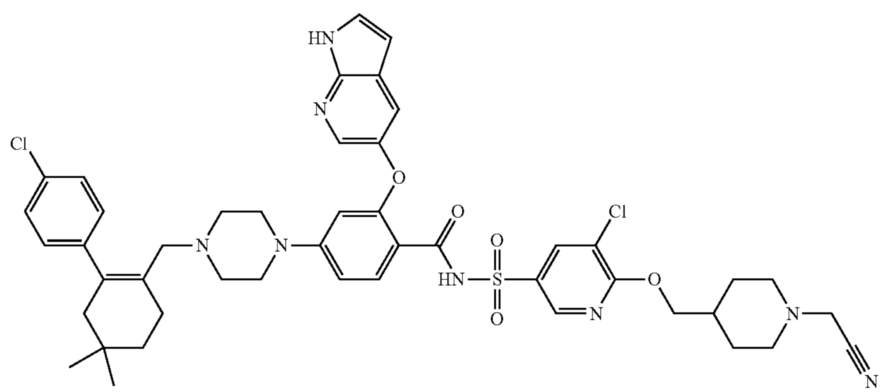 [SMILES: CC1(C)CCC(CN2CCN(c3ccc(C(=O)NS(=O)(=O)c4cnc(OCC5CCN(CC#N)CC5)c(Cl)c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-{[4-({(3R)-1-[2-(2-methoxyethoxy)ethyl]pyrrolidin-3-yl}amino)-3-nitrophenyl]sulfonyl}-2-(1H-pyrrolo[2,3-b]pyridin-5-yl-oxy)benzamide | |

| Name | Structure |
|---|---|
| 4-(4-{[2-(4-chlorophenyl)-4,4-dimethylcyclohex-1-en-1-yl]methyl}piperazin-1-yl)-N-[(4-{[(3R)-1-(N,N-dimethylglycyl)pyrrolidin-3-yl]amino}-3-nitrophenyl)sulfonyl]-2-(1H-pyrrolo[2,3-b]pyridin-5-yloxy)benzamide | 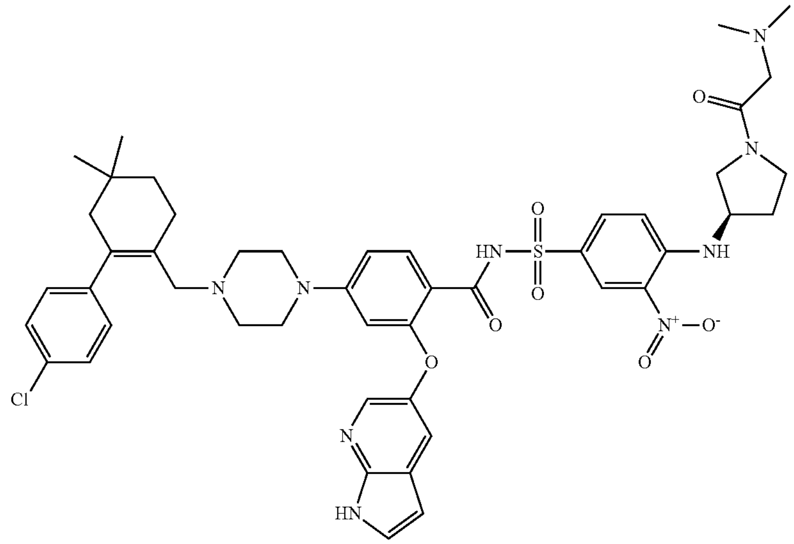 [SMILES: CN(C)CC(=O)N1CC[C@@H](Nc2ccc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2[N+](=O)[O-])C1] |
| 4-(4-{[2-(4-chlorophenyl)-4,4-dimethylcyclohex-1-en-1-yl]methyl}piperazin-1-yl)-N-[(3-nitro-4-{[1-(oxetan-3-yl)azetidin-3-yl]amino}phenyl)sulfonyl]-2-(1H-pyrrolo[2,3-b]pyridin-5-yloxy)benzamide | 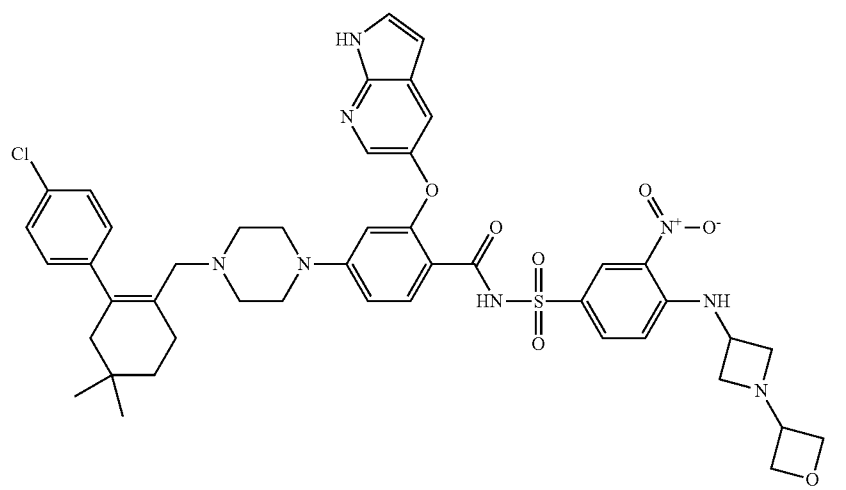 [SMILES: CC1(C)CCC(CN2CCN(c3ccc(C(=O)NS(=O)(=O)c4ccc(NC5CN(C6COC6)C5)c([N+](=O)[O-])c4)c(Oc4cnc5[nH]ccc5c4)c3)CC2)=C(c2ccc(Cl)cc2)C1] |
| N-[(5-chloro-6-{[1-(cyanomethyl)-4-fluoropiperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | 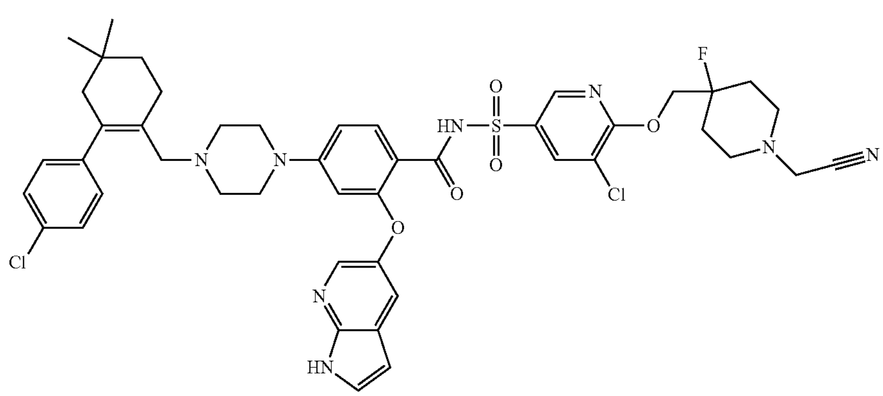 [SMILES: CC1(C)CCC(CN2CCN(c3ccc(C(=O)NS(=O)(=O)c4cnc(OCC5(F)CCN(CC#N)CC5)c(Cl)c4)c(Oc4cnc5[nH]ccc5c4)c3)CC2)=C(c2ccc(Cl)cc2)C1] |

| Name | Structure |
|---|---|
| 4-(4-{[2-(4-chlorophenyl)-4,4-dimethylcyclohex-1-en-1-yl]methyl}piperazin-1-yl)-N-{[4-({[(2R)-4-(N,N-dimethylglycyl)morpholin-2-yl]methyl}amino)-3-nitrophenyl]sulfonyl}-2-(1H-pyrrolo[2,3-b]pyridin-5-yloxy)benzamide | 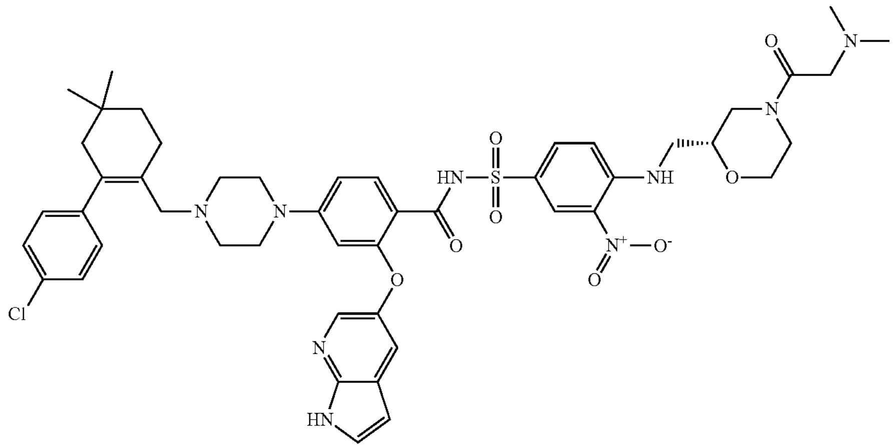 [SMILES: CN(C)CC(=O)N1CCO[C@H](CNc2ccc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2[N+](=O)[O-])C1] |
| 4-(4-{[2-(4-chlorophenyl)-4,4-dimethylcyclohex-1-en-1-yl]methyl}piperazin-1-yl)-N-{(4-({[(2S)-4-(N,N-dimethylglycyl)morpholin-2-yl]methyl}amino)-3-nitrophenyl]sulfonyl}-2-(1H-pyrrolo[2,3-b]pyridin-5-yloxy)benzamide | 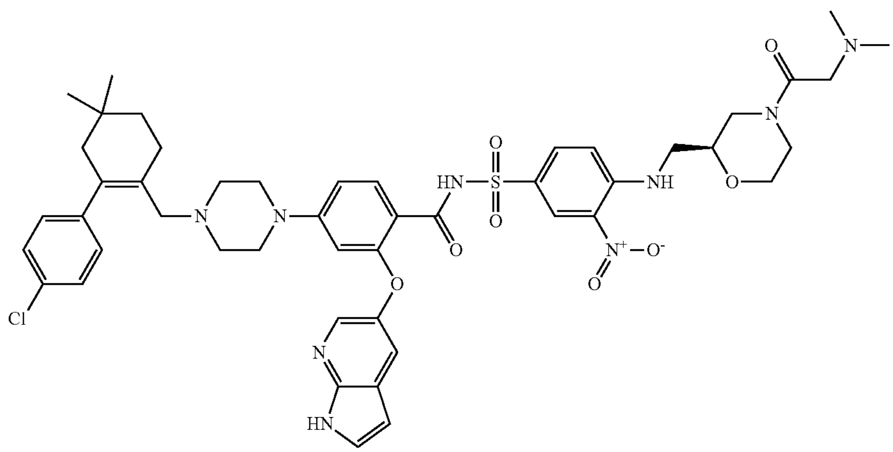 [SMILES: CN(C)CC(=O)N1CCO[C@@H](CNc2ccc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2[N+](=O)[O-])C1] |
| N-[(5-chloro-6-{[1-(N,N-dimethylglycyl)piperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | 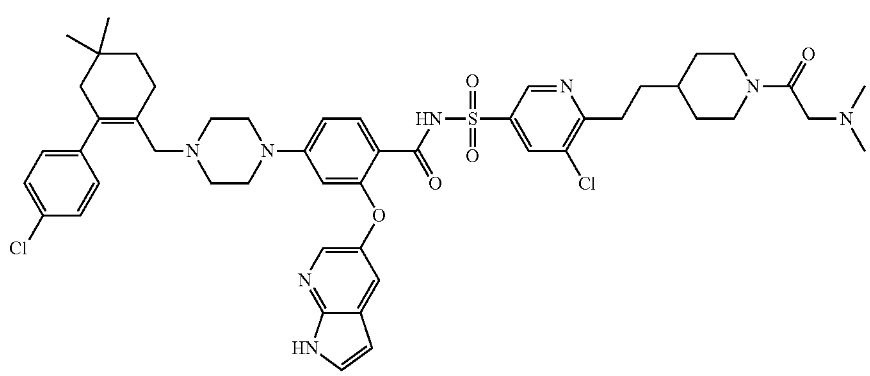 [SMILES: CN(C)CC(=O)N1CCC(CCc2ncc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2Cl)CC1] |

-continued

| Name | Structure |
|---|---|
| N-[(5-chloro-6-{[(3R)-1-(2,2-difluoroethyl)pyrrolidin-3-yl]oxy}pyridin-3-yl)sulfonyl]-4-(4-{[2-(4-chlorophenyl)-4,4-dimethylcyclohex-3-en-1-yl]methyl}piperazin-1-yl)-2-(1H-pyrrolo[2,3-b]pyridin-5-yloxy)benzamide | 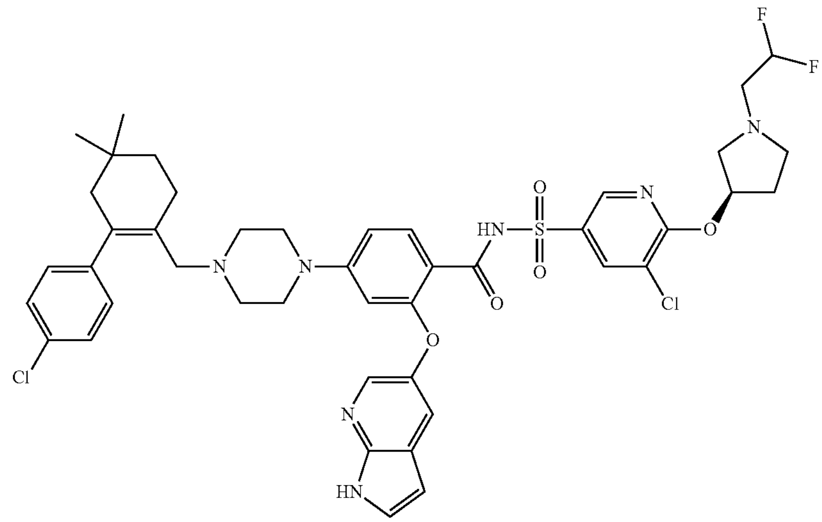 [SMILES: CC1(C)CCC(CN2CCN(c3ccc(C(=O)NS(=O)(=O)c4cnc(O[C@@H]5CCN(CC(F)F)C5)c(Cl)c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-[(4-{[(3R)-1-(cyanomethyl)pyrrolidin-3-yl]amino}-3-nitrophenyl)sulfonyl]-2-(1H-pyrrolo[2,3-b]pyridin-5-yloxy)benzamide | 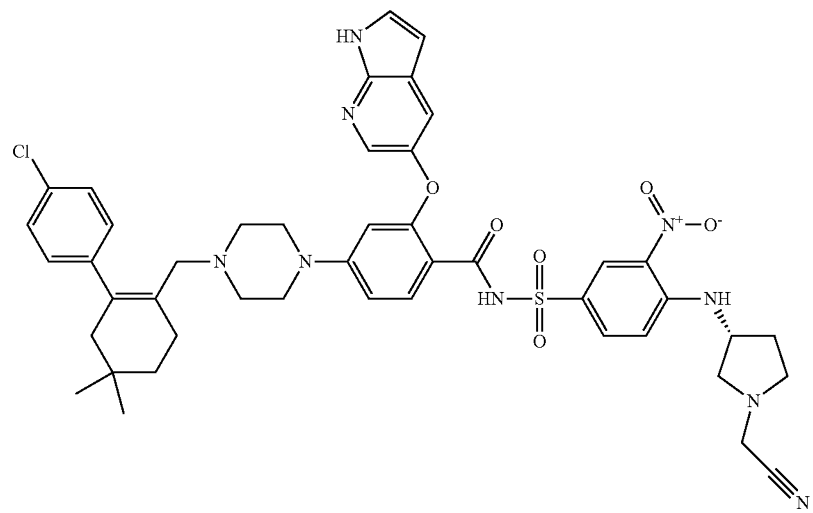 [SMILES: CC1(C)CCC(CN2CCN(c3ccc(C(=O)NS(=O)(=O)c4ccc(N[C@@H]5CCN(CC#N)C5)c([N+](=O)[O-])c4)c(Oc4cnc5[nH]ccc5c4)c3)CC2)=C(c2ccc(Cl)cc2)C1] |
| 4-{4-[(4'-chlorobiphenyl-2-yl)methyl]-4-methoxypiperidin-1-yl}-N-({5-chloro-6-[(4-fluorotetrahydro-2H-pyran-4-yl)methoxy]pyridin-3-yl}sulfonyl)-2-(1H-pyrrolo[2,3-b]pyridin-5-yloxy)benzamide | 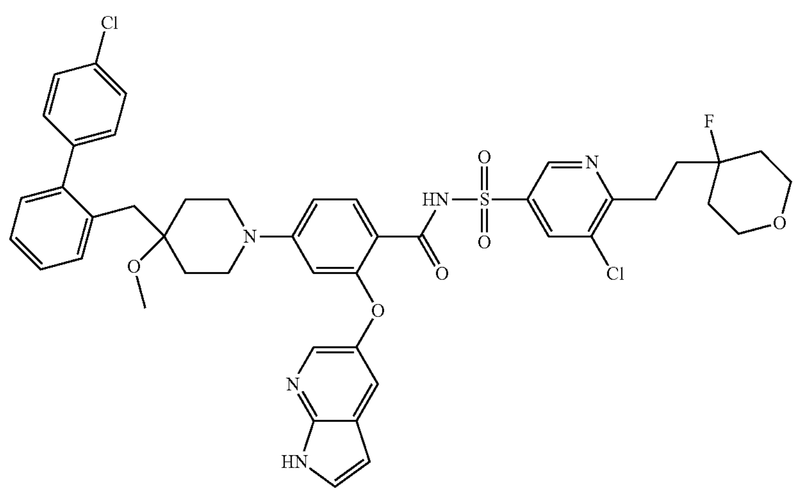 [SMILES: COC1(Cc2ccccc2-c2ccc(Cl)cc2)CCN(c2ccc(C(=O)NS(=O)(=O)c3cnc(CCC4(F)CCOCC4)c(Cl)c3)c(Oc3cnc4[nH]ccc4c3)c2)CC1] |

| Name | Structure |
|---|---|
| 4-4-[(4'-chlorobiphenyl-2-yl)methyl]-4-methoxypiperidin-1-yl}-N-({3-nitro-4-[(tetrahydro-2H-pyran-4-ylmethyl)amino]phenyl}sulfonyl)-2-(1H-pyrrolo[2,3-b]pyridin-5-yloxy)benzamide | 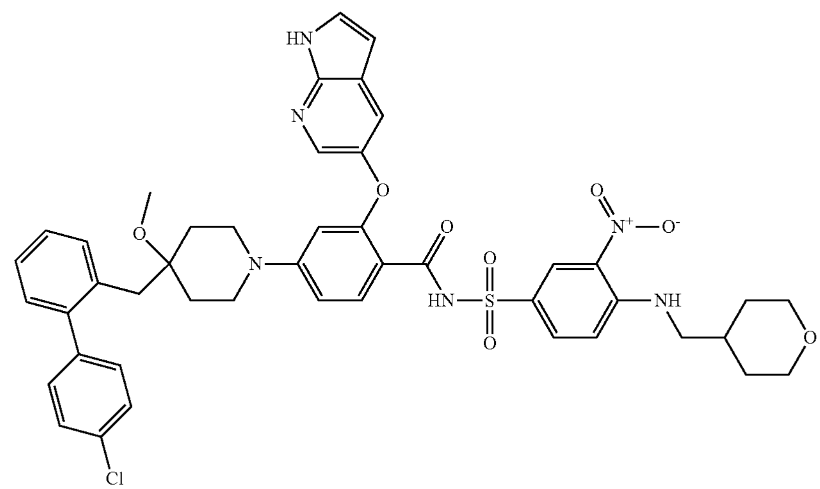 [SMILES: COC1(Cc2ccccc2-c2ccc(Cl)cc2)CCN(c2ccc(C(=O)NS(=O)(=O)c3ccc(NCC4CCOCC4)c([N+](=O)[O-])c3)c(Oc3cnc4[nH]ccc4c3)c2)CC1] |
| 4-(4-{[9-(4-chlorophenyl)-3-(1,3-difluoropropan-2-yl)-3-azaspiro[5.5]undec-8-en-8-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide | 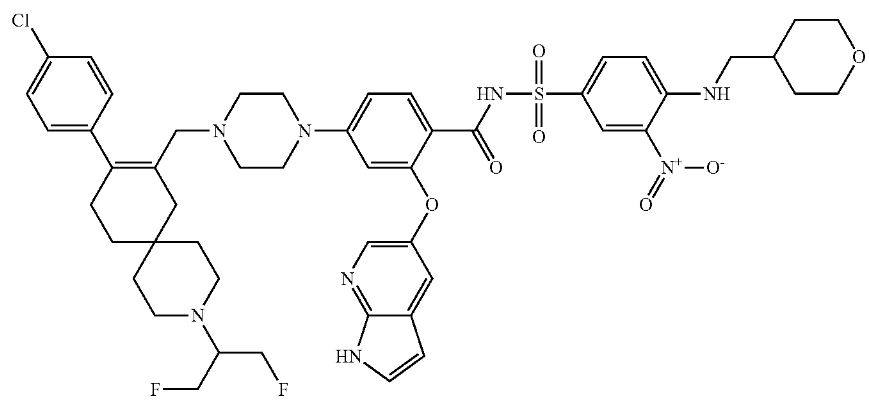 [SMILES: O=C(NS(=O)(=O)c1ccc(NCC2CCOCC2)c([N+](=O)[O-])c1)c1ccc(N2CCN(CC3=C(c4ccc(Cl)cc4)CCC4(CCN(C(CF)CF)CC4)C3)CC2)cc1Oc1cnc2[nH]ccc2c1] |
| 4-(4-{[9-{4-chlorophenyl)-3-isopropyl-3-azaspiro[5.5]undec-8-en-8-yl]methyl}piperazin-1-yl)-N-({3-nitro-4-[(tetrahydro-2H-ylmethyl)amino]phenyl}sulfonyl)-2-(1H-pyrrolo[2,3-b]pyridin-5-yloxy)benzamide | |

| Name | Structure |
|---|---|
| 4-(4-{[9-(4-chlorophenyl)-3-(1,3-difluoropropan-2-yl)-3-azaspiro[5.5]undec-8-en-8-yl]methyl}piperazin-1-yl)-N-{[5-chloro-6-(tetrahydro-2H-pyran-4-ylmethoxy)pyridin-3-yl]sulfonyl}-2-(1H-pyrrolo[2,3-b]pyridin-5-yloxy)benzamide | 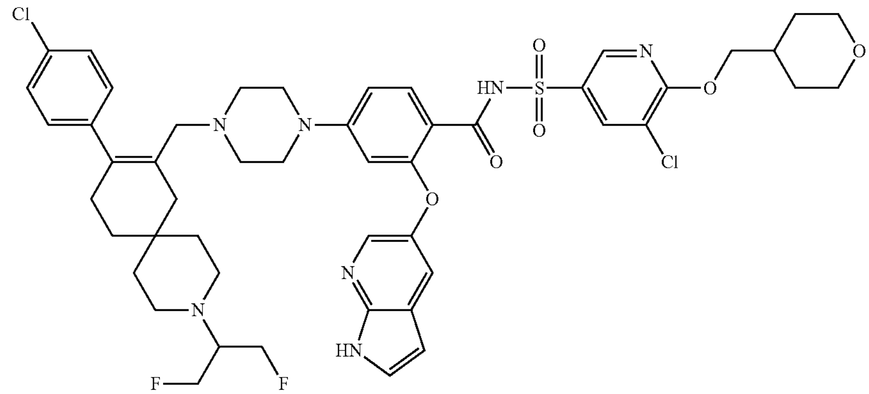 [SMILES: O=C(NS(=O)(=O)c1cnc(OCC2CCOCC2)c(Cl)c1)c1ccc(N2CCN(CC3=C(c4ccc(Cl)cc4)CCC4(CCN(C(CF)CF)CC4)C3)CC2)cc1Oc1cnc2[nH]ccc2c1] |
| 4-(4-{[9-(4-chlorophenyl)-3-isopropyl-3-azaspiro[5.5]undec-8-en-8-yl]methyl}piperazin-1-yl)-N-{[5-chloro-6-(tetrahydro-2H-pyran-4-ylmethoxy)pyridin-3-yl]sulfonyl}-2-(1H-pyrrolo[2,3-b]pyridin-5-yloxy)benzamide | |
| N-({5-chloro-6-[(4-fluoro-1-methylpiperidin-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | 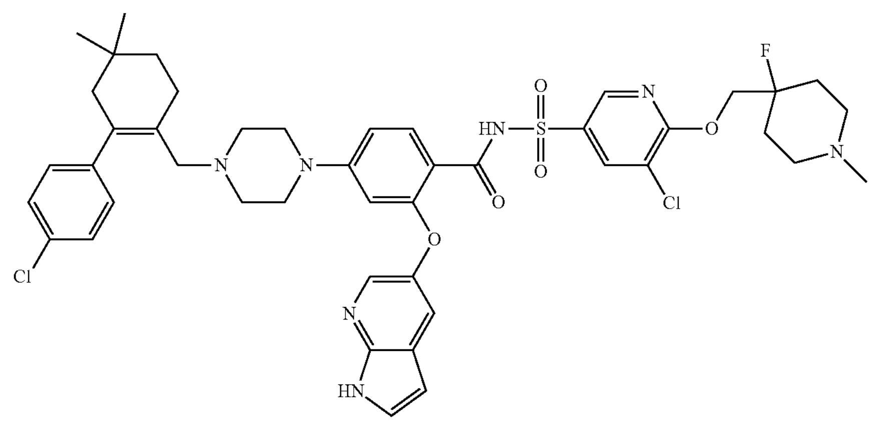 [SMILES: CN1CCC(F)(COc2ncc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2Cl)CC1] |
| N-[(5-chloro-6-{[1-(N,N-dimethylglycyl)-4-fluoropiperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | 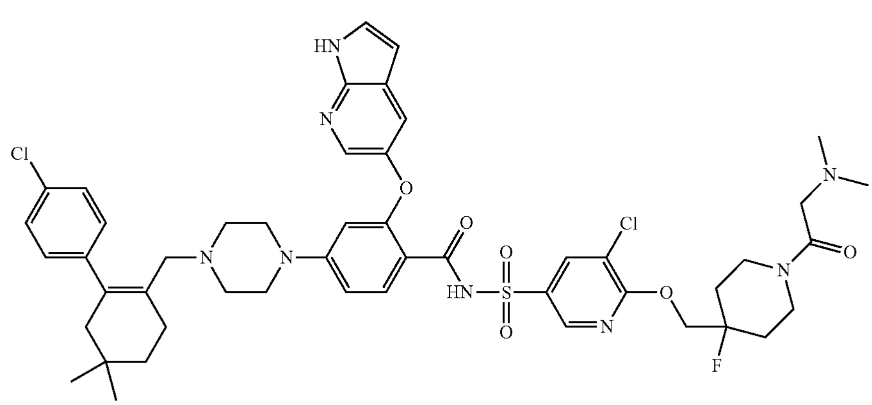 [SMILES: CN(C)CC(=O)N1CCC(F)(COc2ncc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2Cl)CC1] |

| Name | Structure |
|---|---|
| 4-{4-[(4'-chlorobiphenyl-2-yl)methyl]-4-fluoropiperidin-1-yl}-N-({3-nitro-4-[(tetrahydro-2H-pyran-4-ylmethyl)amino]phenyl}sulfonyl)-2-(1H-pyrrolo[2,3-b]pyridin-5-yloxy)benzamide | 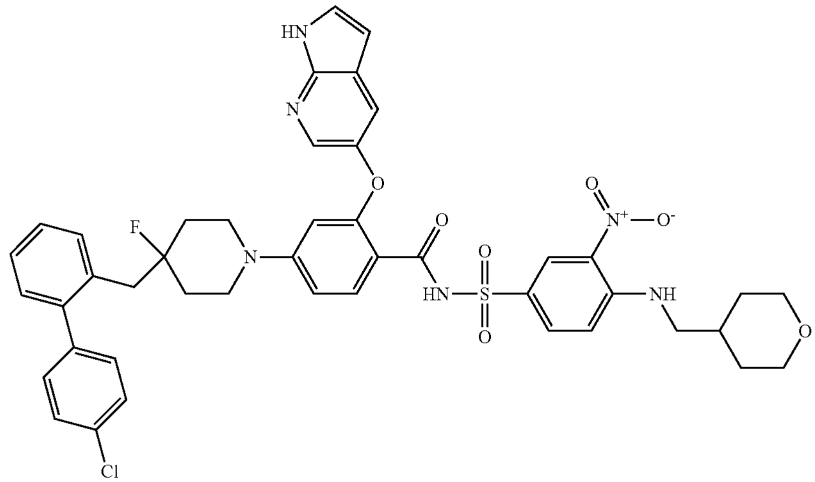 [SMILES: O=C(NS(=O)(=O)c1ccc(NCC2CCOCC2)c([N+](=O)[O-])c1)c1ccc(N2CCC(F)(Cc3ccccc3-c3ccc(Cl)cc3)CC2)cc1Oc1cnc2[nH]ccc2c1] |
| 4-{4-[(4'-chlorobiphenyl-2-yl)methyl]-4-fluoropiperidin-1-yl}-N-({5-chloro-6-[(4-fluorotetrahydro-2H-pyran-4-yl)methoxy]pyridin-3-yl}sulfonyl)-2-(1H-pyrrolo[2,3-b]pyridin-5-yloxy)benzamide | 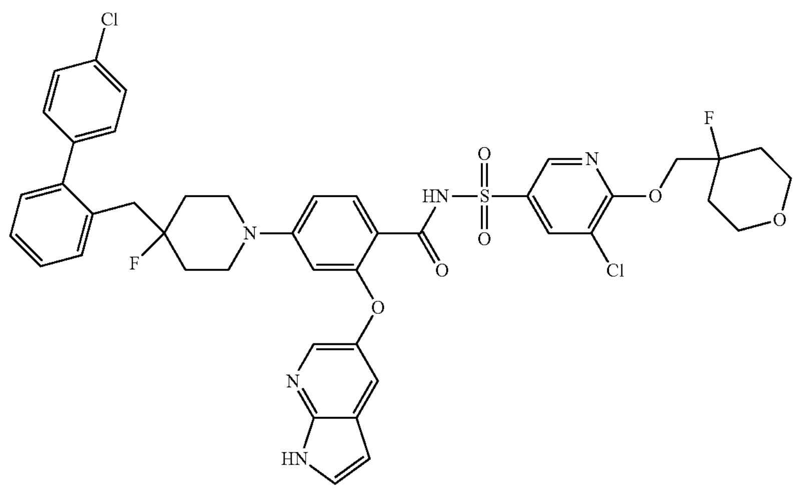 [SMILES: O=C(NS(=O)(=O)c1cnc(OCC2(F)CCOCC2)c(Cl)c1)c1ccc(N2CCC(F)(Cc3ccccc3-c3ccc(Cl)cc3)CC2)cc1Oc1cnc2[nH]ccc2c1] |
| 4-(4-{[9-(4-chlorophenyl)-3-isopropyl-3-azaspiro[5,5]undec-8-en-8-yl]methyl}piperazin-1-yl)-2-(1H-pyrrolo[2,3-b]pyridin-5-yloxy)-N-({4-[(tetrahydro-2H-pyran-4-ylmethyl)amino]-3-(trifluoromethyl)phenyl}sulfonyl)benzamide | 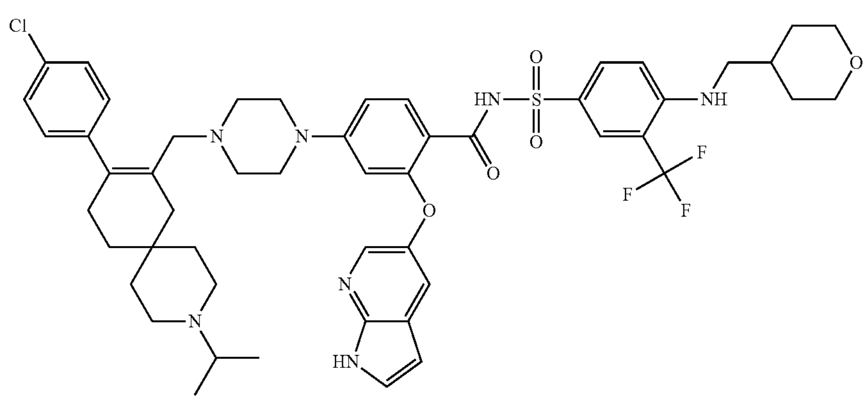 [SMILES: CC(C)N1CCC2(CCC(c3ccc(Cl)cc3)=C(CN3CCN(c4ccc(C(=O)NS(=O)(=O)c5ccc(NCC6CCOCC6)c(C(F)(F)F)c5)c(Oc5cnc6[nH]ccc6c5)c4)CC3)C2)CC1] |

| Name | Structure |
|---|---|
| N-[(5-chloro-6-{[(3R)-1-(1,3-difluoropropan-2-yl)pyrrolidin-3-yl]oxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | 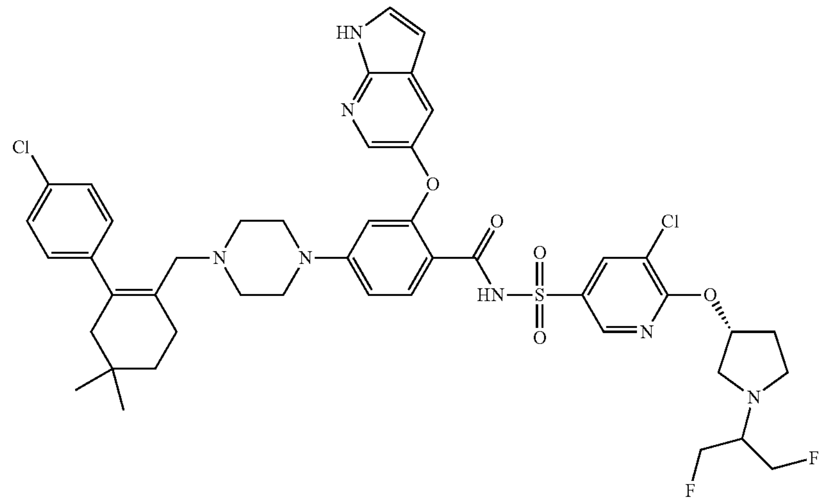 [SMILES: CC1(C)CCC(CN2CCN(c3ccc(C(=O)NS(=O)(=O)c4cnc(O[C@@H]5CCN(C(CF)CF)C5)c(Cl)c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-({3-nitro-4-[2-(tetrahydrofuran-3-yloxy)ethoxy]phenyl}sulfonyl)-2-(1H-pyrrolo[2,3-b]pyridin-5-yloxy)benzamide | 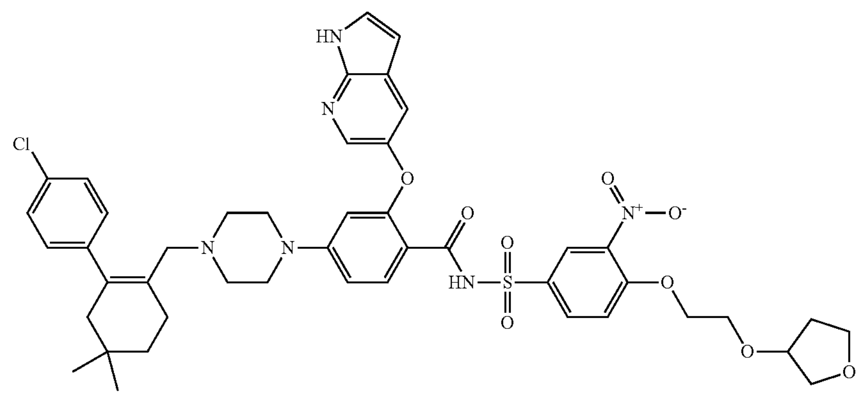 [SMILES: CC1(C)CCC(CN2CCN(c3ccc(C(=O)NS(=O)(=O)c4ccc(OCCOC5CCOC5)c([N+](=O)[O-])c4)c(Oc4cnc5[nH]ccc5c4)c3)CC2)=C(c2ccc(Cl)cc2)C1] |
| 4-(4-{[2-{4-chlorophenyl)-4,4-dimethylcyclohex-1-en-1-yl]methyl}piperazin-1-yl)-N-{(4-{[(trans-4-cyanocyclohexyl)methyl]amino}-3-nitrophenyl)sulfonyl]-2-(1H-pyrrolo[2,3-b]pyridin-5-yloxy)benzamide | 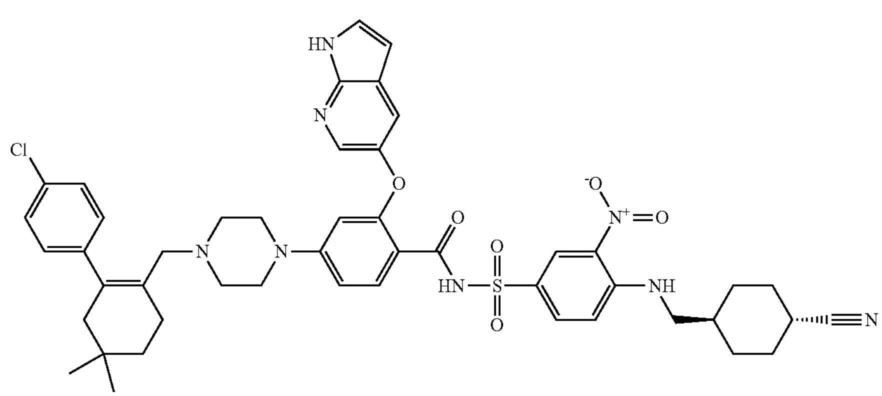 |

-continued

| Name | Structure |
|---|---|
| N-[(5-chloro-6-{[4-fluoro-1-(oxetan-3-yl)piperidn-4-yl]methoxy}pyridin-3-yl)sulfonyl]-4-(4-{(2-(4-chlorophenyl)-4,4-dimethylcyclohex-1-en-1-yl]methyl}piperazin-1-yl)-2-(1H-pyrrolo[2,3-b]pyridin-5-yloxy)benzamide | 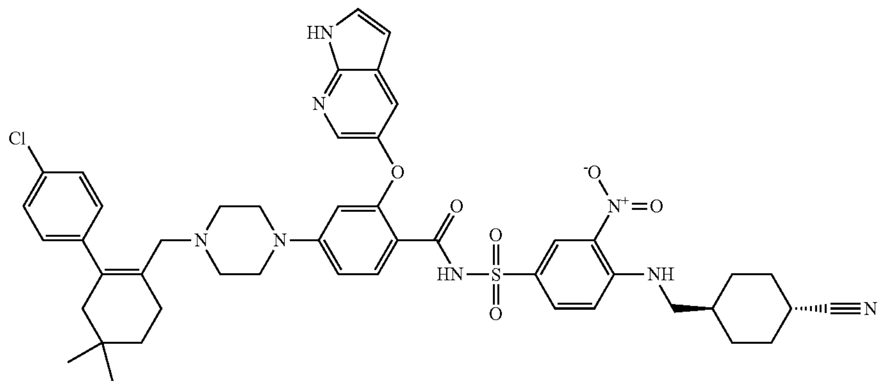 |
| 4-(4-{[2-(4-chlorophenyl)-4,4-(dimethylcyclohex-1-en-1-yl]methyl}piperazin-1-yl)-N-({5-cyano-6-[2-(tetrahydro-2H-pyran-4-yl)ethoxy]pyridin-3-yl]sulfonyl)-2-(1H-pyrrolo[2,3-b]pyridin-5-yloxy)benzamide | 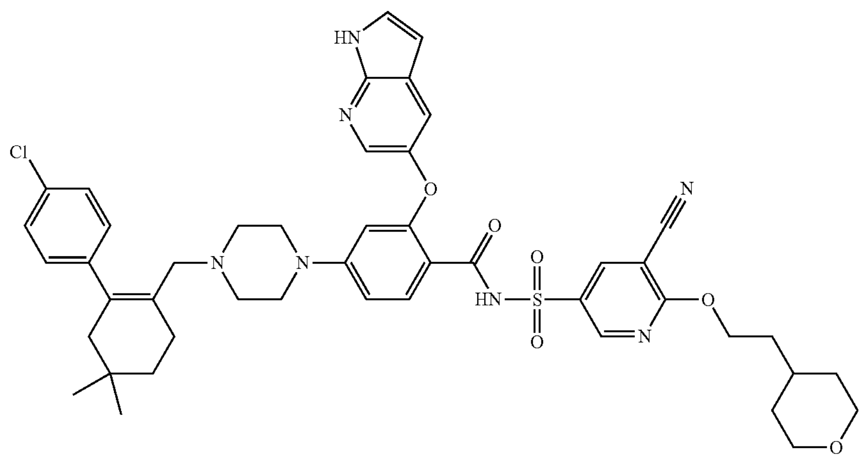 |
| 4-(4-{[2-(4-chlorophenyl)-4,4-dimethylcyclohex-1-en-1-yl(methyl}piperazin-1-yl)-N-{[4-(3-furylmethoxy)-3-nitrophenyl]sulfonyl}-2-(1H-pyrrolo[2,3-b]pyridin-5-yloxy)benzamide | 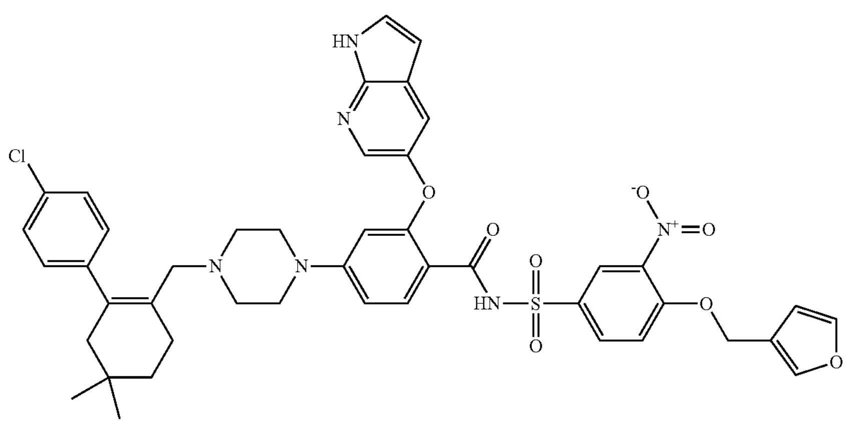 |

| Name | Structure |
|---|---|
| N-[(5-chloro-6-{[(3R)-1-(1,3-difluoropropan-2-yl)pyrrolidin-3-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5~yloxy)benzamide | 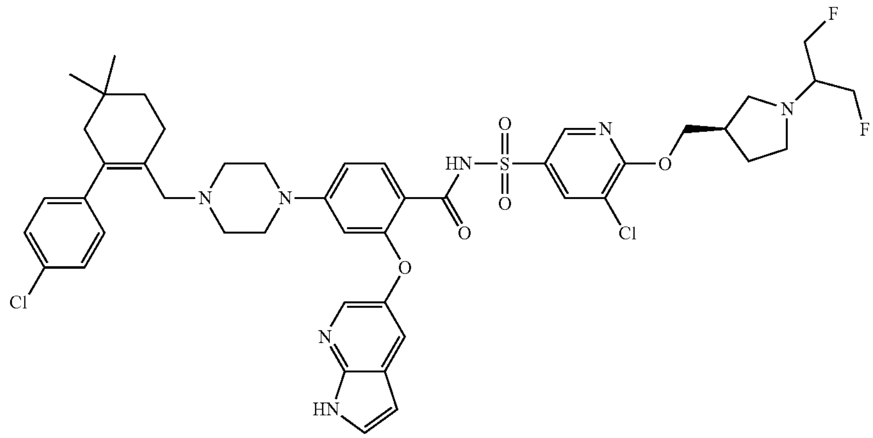 [SMILES: CC1(C)CCC(CN2CCN(c3ccc(C(=O)NS(=O)(=O)c4cnc(OC[C@@H]5CCN(C(CF)CF)C5)c(Cl)c4)c(Oc4cnc5[nH]ccc5c4)c3)CC2)=C(c2ccc(Cl)cc2)C1] |
| N-[(5-chloro-6-{[(3R)-1-(2,2-difluoroethyl)pyrrolidin-3-yl]methoxy}pyridin-3-yl)sulfonyl]-4-(4-{[2-(4-chlorophenyl)-4,4-(dimethylcyclohex-1-en-1-yl]methyl}piperazin-1-yl)-2-(1H-pyrrolo[2,3-b]pyridin-5-yloxy)benzamide | 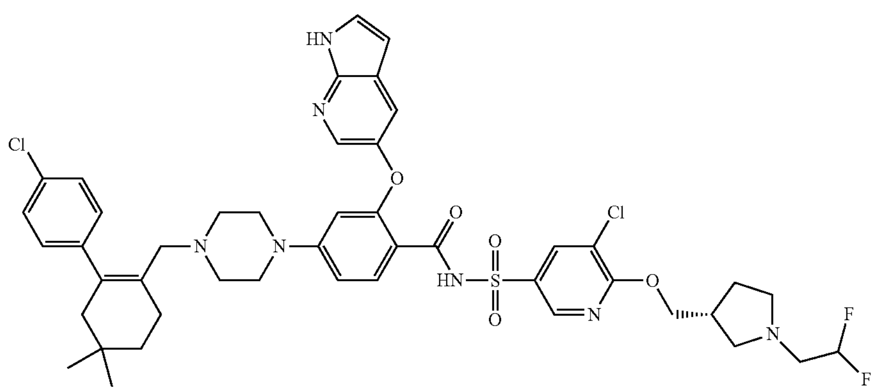 [SMILES: CC1(C)CCC(CN2CCN(c3ccc(C(=O)NS(=O)(=O)c4cnc(OC[C@@H]5CCN(CC(F)F)C5)c(Cl)c4)c(Oc4cnc5[nH]ccc5c4)c3)CC2)=C(c2ccc(Cl)cc2)C1] |
| N-[(5-chloro-6-{[1-(1,3-difluoropropan-2-yl)-4-fluoropiperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | 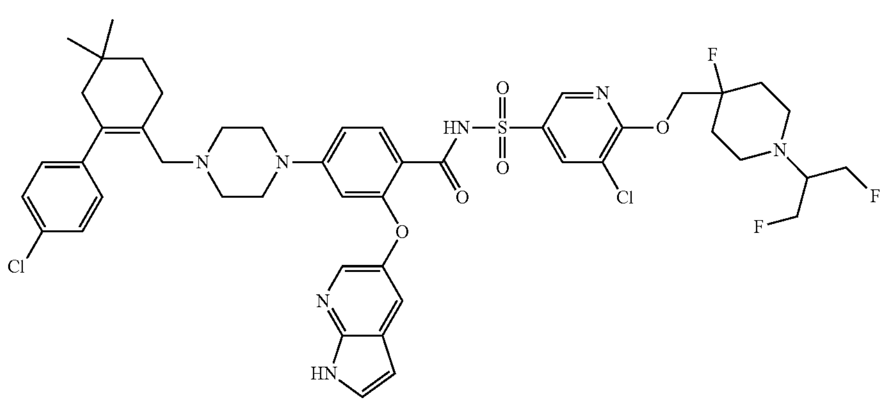 [SMILES: CC1(C)CCC(CN2CCN(c3ccc(C(=O)NS(=O)(=O)c4cnc(OCC5(F)CCN(C(CF)CF)CC5)c(Cl)c4)c(Oc4cnc5[nH]ccc5c4)c3)CC2)=C(c2ccc(Cl)cc2)C1] |

| Name | Structure |
|---|---|
| N-({3-chloro-4-[(4-fluoro-1-methylpiperidin-4-yl)methoxy]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | 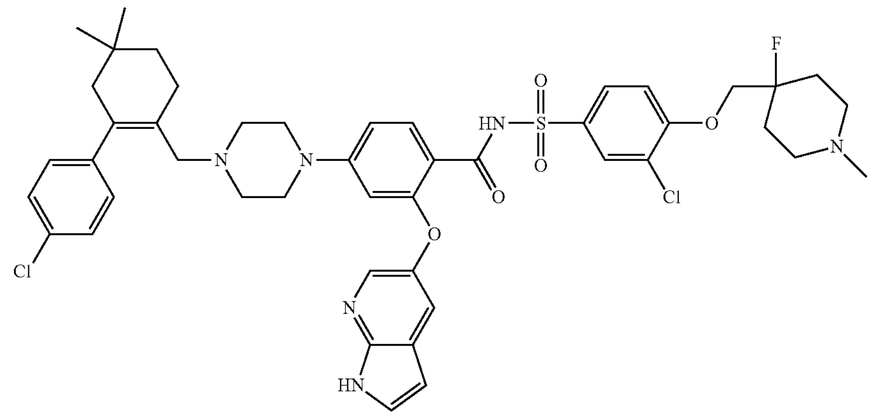 [SMILES: CN1CCC(F)(COc2ccc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2Cl)CC1] |
| 4-(4-{[2-(4-chlorophenyl)-4,4-dimethylcyclohex-1-en-1-yl]methyl}piperazin-1-yl)-N-{[3-cyano-4-(tetrahydro-2H-pyran-4-ylmethoxy)phenyl]sulfonyl}-2-(1H-pyrrolo[2,3-b]pyridin-5-yloxy)benzamide | 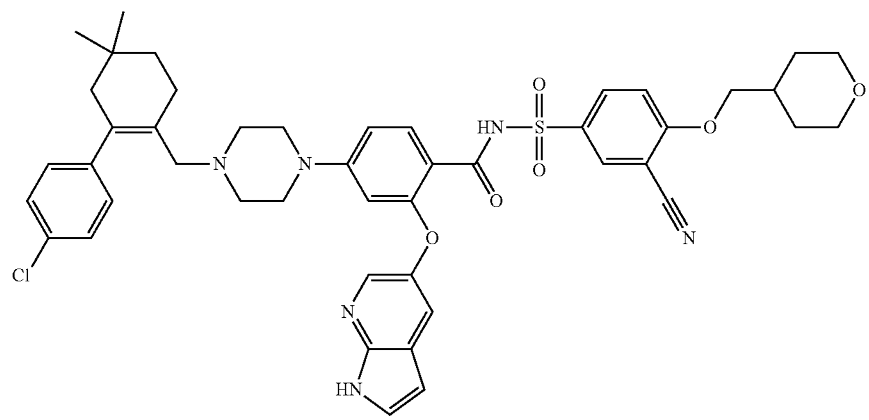 [SMILES: CC1(C)CCC(CN2CCN(c3ccc(C(=O)NS(=O)(=O)c4ccc(OCC5CCOCC5)c(C#N)c4)c(Oc4cnc5[nH]ccc5c4)c3)CC2)=C(c2ccc(Cl)cc2)C1] |
| N-[(5-chloro-6-{1-(2,2-difluoroethyl)-4-fluoropiperidin-4-yl]methoxy}pyridin-3-yl)sulfonyl]-4(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | |

-continued

| Name | Structure |
|---|---|
| N-({3-chloro-4-[(4-fluorotetrahydro-2H-pyran-4-yl)methoxy]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | 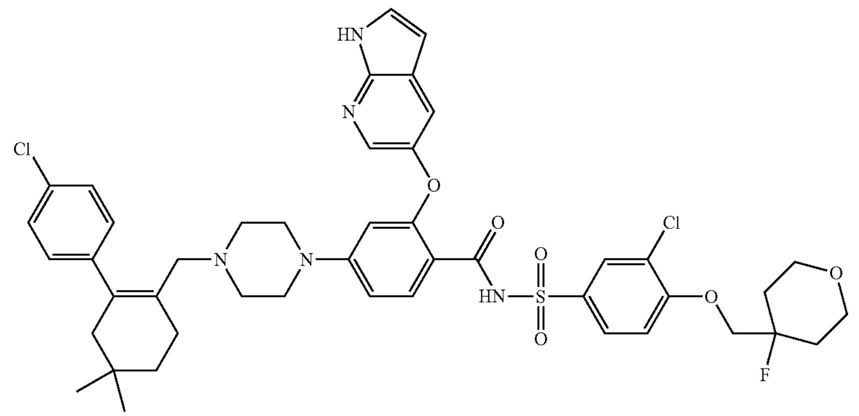 [SMILES: CC1(C)CCC(CN2CCN(c3ccc(C(=O)NS(=O)(=O)c4ccc(OCC5(F)CCOCC5)c(Cl)c4)c(Oc4cnc5[nH]ccc5c4)c3)CC2)=C(c2ccc(Cl)cc2)C1] |
| N-({5-chloro-6-[(4,4-difluorocyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | 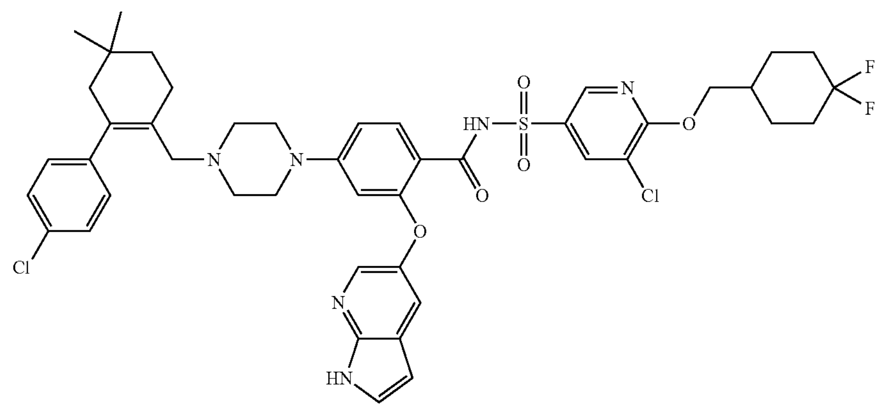 [SMILES: CC1(C)CCC(CN2CCN(c3ccc(C(=O)NS(=O)(=O)c4cnc(OCC5CCC(F)(F)CC5)c(Cl)c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-{[6-{[1-(1,3-difluoropropan-2-yl)-4-fluoropiperidin-4-yl]methoxy}-5-(trifluoromethyl)pyridin-3-yl]sulfonyl}-2-(1H-pyrrolo[2,3-b]pyridin-5-yloxy)benzamide | 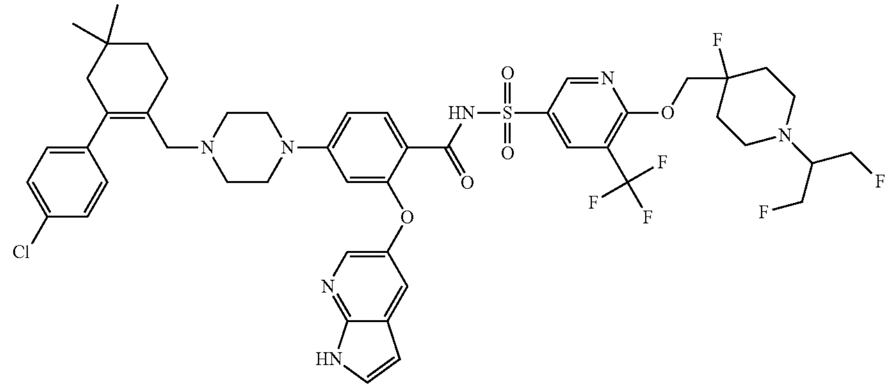 [SMILES: CC1(C)CCC(CN2CCN(c3ccc(C(=O)NS(=O)(=O)c4cnc(OCC5(F)CCN(C(CF)CF)CC5)c(C(F)(F)F)c4)c(Oc4cnc5[nH]ccc5c4)c3)CC2)=C(c2ccc(Cl)cc2)C1] |

| Name | Structure |
|---|---|
| 4-(4-{[2-(4-chlorophenyl)-4,4-dimethylcyclohex-1-en-1-yl]methyl}piperazin-1-yl)-N-{[5-chloro-6-[2-(tetrahydrofuran-2-yl)ethoxy]pyridin-3-yl(sulfonyl)-2-(1H-pyrrolo[2,3-b]pyridin-5-yloxy)benzamide | 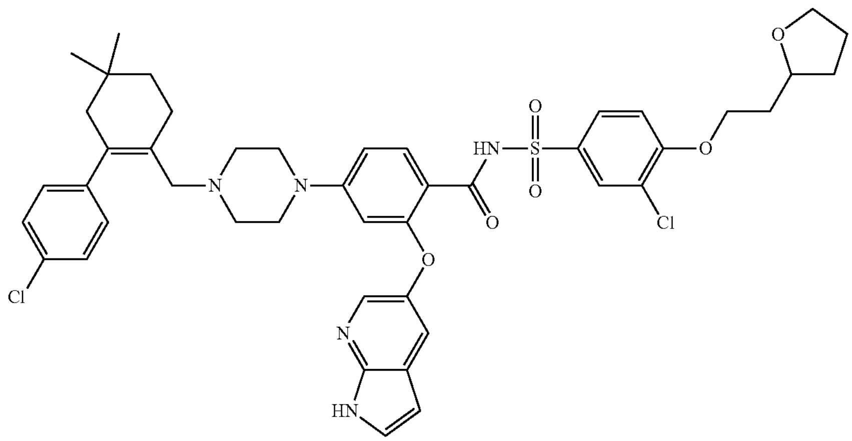 [SMILES: CC1(C)CCC(CN2CCN(c3ccc(C(=O)NS(=O)(=O)c4ccc(OCCC5CCCO5)c(Cl)c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}-3-methylpiperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide | 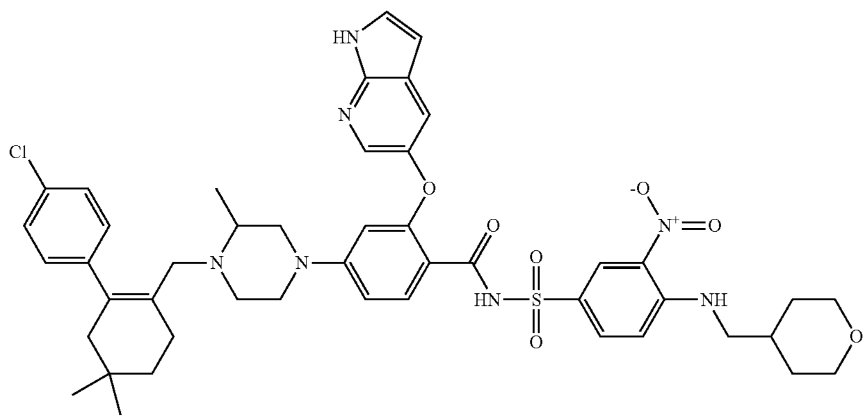 |
| 4-(4-{[2-(4-chlorophenyl)-4,4-dimethylcyclohex-1-en-1-yl]methyl}piperazin-1-yl)-N-[(4-{[3-(cyclopropylamino)propyl]amino}-3-nitrophenyl)sulfonyl]-2-(1H-pyrrolo[2,3-b]pyridin-5-yloxy)benzamide | 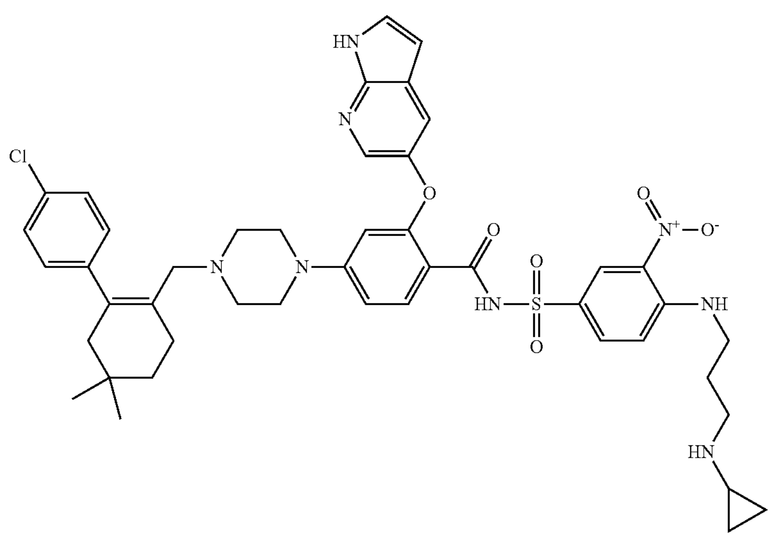 [SMILES: CC1(C)CCC(CN2CCN(c3ccc(C(=O)NS(=O)(=O)c4ccc(NCCCNC5CC5)c([N+](=O)[O-])c4)c(Oc4cnc5[nH]ccc5c4)c3)CC2)=C(c2ccc(Cl)cc2)C1] |

-continued

| Name | Structure |
|---|---|
| N-{[5-chloro-6-(2-methoxyethoxy)pyridin-3-yl]sulfonyl}-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | |
| 4-(4-{[2-(4-chlorophenyl)-4,4-dimethylcyclohex-1-en-1-yl(methyl}piperazin-1-yl)-N-{[5-fluoro-6-(tetrahydro-2H-pyran-4-ylmethoxy)pyridin-3-yl]sulfonyl}-2-(1H-pyrrolo[2,3-b]pyridin-5-yloxy)benzamide | 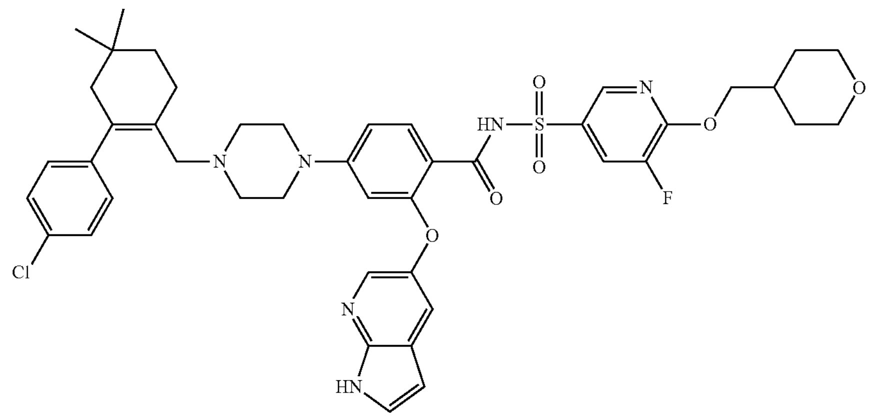 |
| N-[(3-chloro-4-{[1-(methoxyacetyl)piperidin-4-yl]methoxy}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | 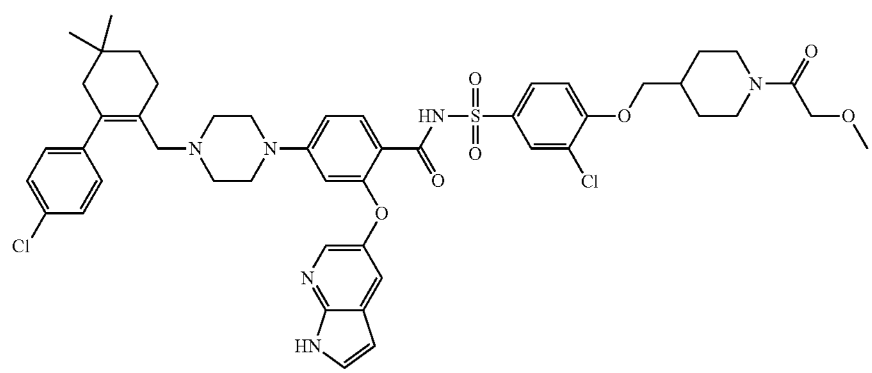 [SMILES: COCC(=O)N1CCC(COc2ccc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2Cl)CC1] |
| N-[(3-chloro-4-{[1-(N,N-dimethylglycyl)piperidin-4-yl]methoxy}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | 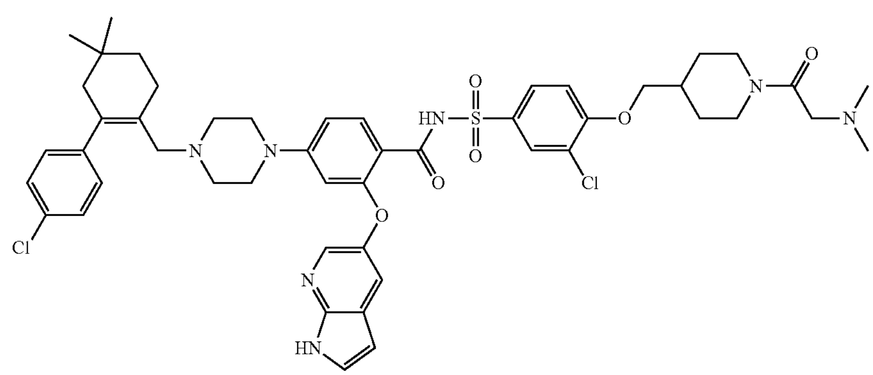 [SMILES: CN(C)CC(=O)N1CCC(COc2ccc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2Cl)CC1] |

-continued

| Name | Structure |
|---|---|
| 4-(4-{[2-{4-chlorophenyl}-4,4-dimethylcyclohexyl]methyl}piperidin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide | |
| 4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)-N-{[6-(tetrahydro-2H-pyran-4-ylmethoxy)-5-(trifluoromethyl)pyridin-3-yl]sulfonyl}benzamide | |
| N-({5-chloro-6-[(trans-4-hydroxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | |

-continued

| Name | Structure |
|---|---|
| 4(4-{[2-(4-chlorophenyl)-4,4-dimethylcyclohex-1-en-1-yl]methyl}piperazin-1-yl)-N-({3-cyano-4-[(4-fluorotetrahydro-2H-pyran-4-yl)methoxy]phenyl}sulfonyl)-2-(1H-pyrrolo[2,3-b]pyridin-5-yloxy)benzamide | 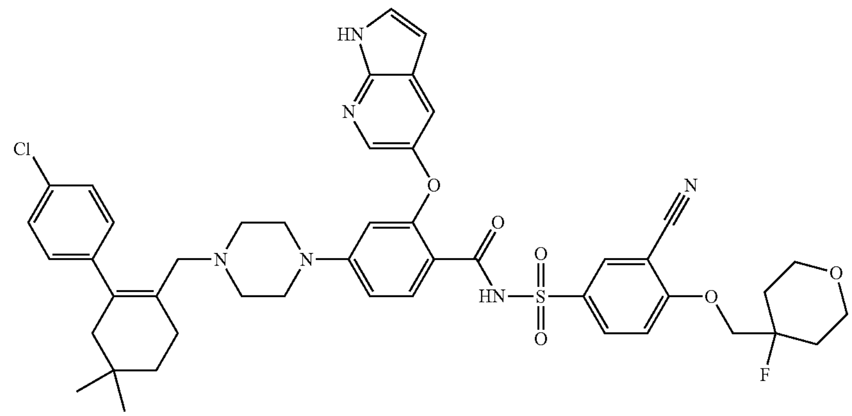 [SMILES: CC1(C)CCC(CN2CCN(c3ccc(C(=O)NS(=O)(=O)c4ccc(OCC5(F)CCOCC5)c(C#N)c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-({6-[(trans-4-methoxycyclohexyl)methoxy]-5-(trifluoromethyl)pyridin-3-y}sulfonyl)-2-(1H-pyrrolo[2,3-b]pyridin-5-yloxy)benzamide | 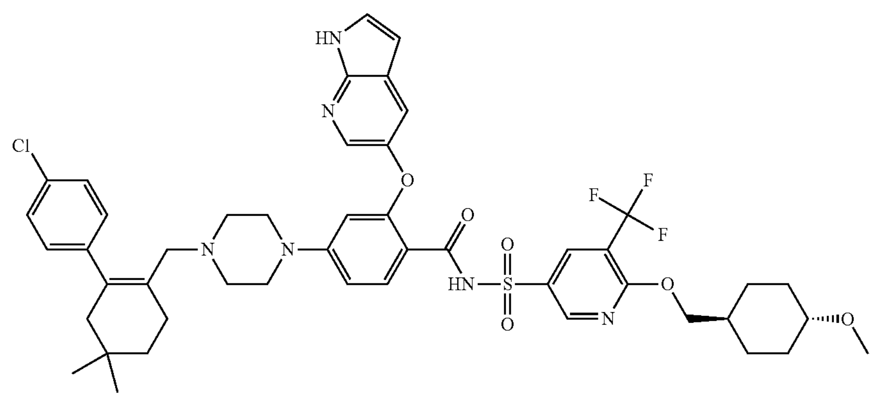 [SMILES: CO[C@H]1CC[C@H](COc2ncc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2C(F)(F)F)CC1] |
| 4-(4-{[2-(4-chlorophenyl)-4,4-dimethylcyclohex-1-en-1-yl]methyl}piperazin-1-yl)-N-({6-[(cis-4-methoxycyclohexyl)methoxy]-5-(trifluoromethyl)pyridin-3-yl)sulfonyl)-2-(1H-pyrrolo[2,3-b]pyridin-5-yloxy)benzamide | |
| N-({5-chloro-6-[(4,4-difluoro-1-hydroxycyclohexyl)methoxy]pyridin-3-yl)sulfonyl)-4-(4-([2-(4-chlorophenyl)-4,4-dimethylcyclohex-1-en-1-yl]methyl}piperidin-1-yl)-2-(1H-pyrrolo[2,3-b]pyridin-5-yloxy)benzamide | 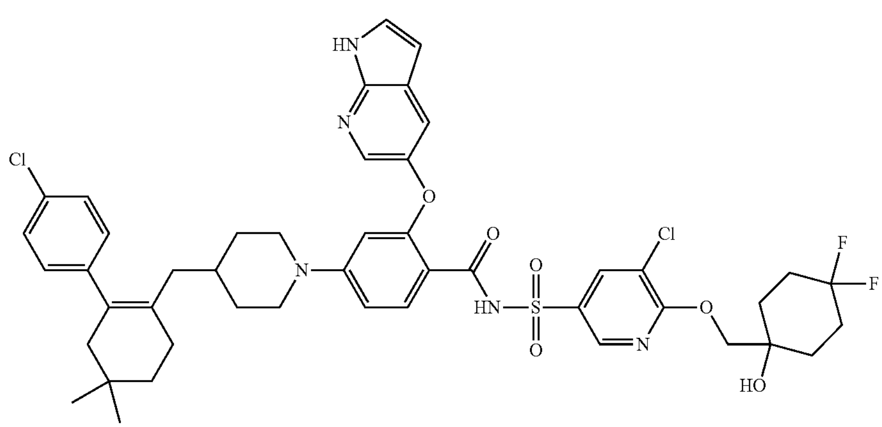 [SMILES: CC1(C)CCC(CC2CCN(c3ccc(C(=O)NS(=O)(=O)c4cnc(OCC5(O)CCC(F)(F)CC5)c(Cl)c4)c(Oc4cnc5[nH]ccc5c4)c3)CC2)=C(c2ccc(Cl)cc2)C1] |

| Name | Structure |
|---|---|
| N-[(3-chloro-4-{[trans-4-(morpholin-4-yl)cyclohexyl]methoxy}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | 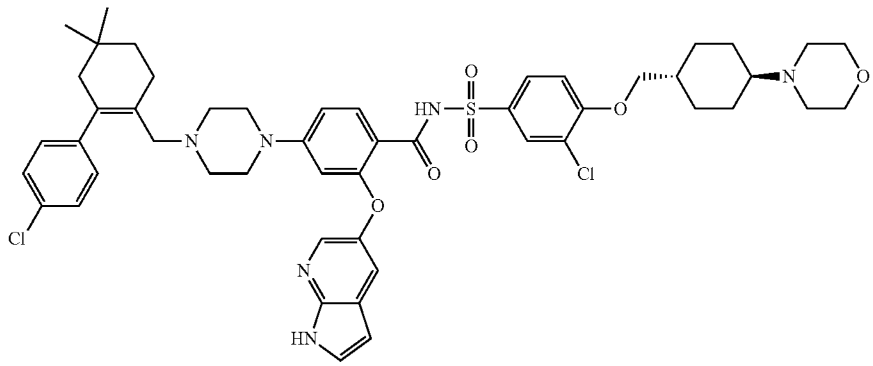 [SMILES: CC1(C)CCC(CN2CCN(c3ccc(C(=O)NS(=O)(=O)c4ccc(OC[C@H]5CC[C@H](N6CCOCC6)CC5)c(Cl)c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-{[4-({3-[cyclopropyl(1,3-thiazol-5-ylmethyl)amino]propyl}-amino)-3-nitrophenyl]sulfonyl}-2-(1H-pyrrolo[2,3-b]pyridin-5-yloxy)benzamide | 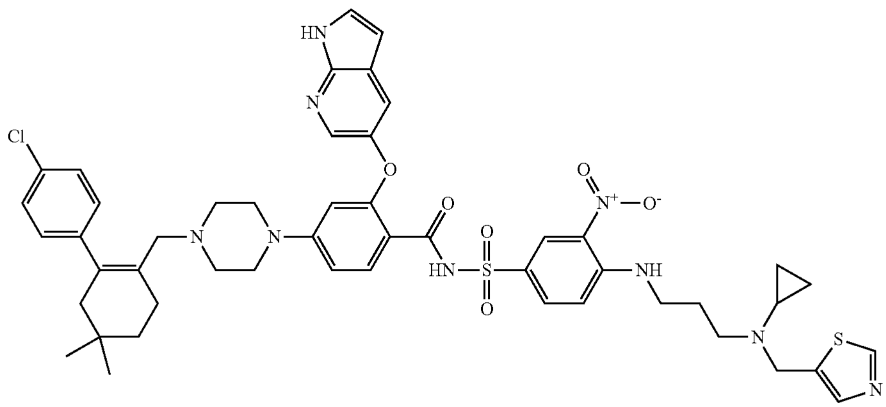 [SMILES: CC1(C)CCC(CN2CCN(c3ccc(C(=O)NS(=O)(=O)c4ccc(NCCCN(Cc5cncs5)C5CC5)c([N+](=O)[O-])c4)c(Oc4cnc5[nH]ccc5c4)c3)CC2)=C(c2ccc(Cl)cc2)C1] |
| N-({3-chloro-4-[(trans-4-hydroxycyclohexyl)methoxy]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | 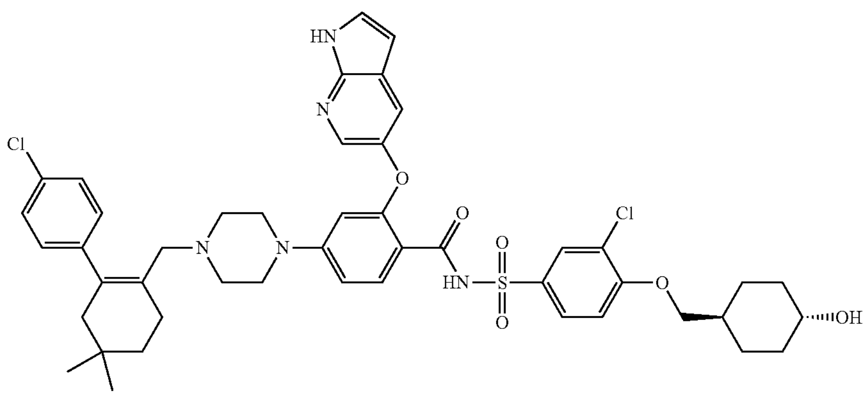 [SMILES: CC1(C)CCC(CN2CCN(c3ccc(C(=O)NS(=O)(=O)c4ccc(OC[C@H]5CC[C@H](O)CC5)c(Cl)c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-({3-chloro-4-[(tetrahydro-2H-pyran-4-ylmethyl)amino]phenyl}sulfonyl)-2-(1H-pyrrolo[2,3-b]pyridin-5-yloxy)benzamide | 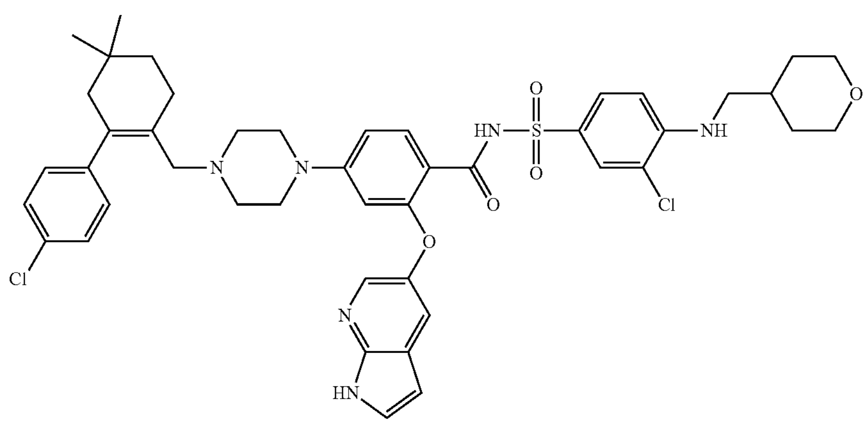 [SMILES: CC1(C)CCC(CN2CCN(c3ccc(C(=O)NS(=O)(=O)c4ccc(NCC5CCOCC5)c(Cl)c4)c(Oc4cnc5[nH]ccc5c4)c3)CC2)=C(c2ccc(Cl)cc2)C1] |

| Name | Structure |
|---|---|
| 4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-(trifluoromethyl)phenyl}sulfonyl)-2-(1H-pyrrolo[2,3-b]pyridin-5-yloxy)benzamide | 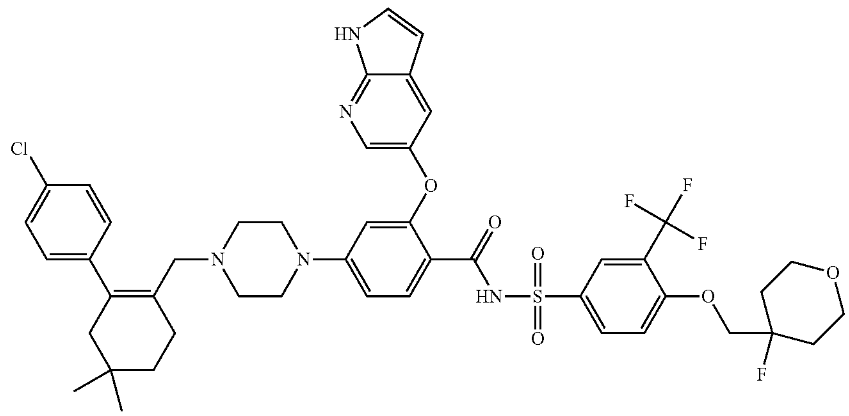 [SMILES: CC1(C)CCC(CN2CCN(c3ccc(C(=O)NS(=O)(=O)c4ccc(OCC5(F)CCOCC5)c(C(F)(F)F)c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-{[4-({3-[cyclopropyl(2,2,2-trifluoroethyl)amino]propyl}amino)-3-nitrophenyl]sulfonyl}-2-(1H-pyrrolo[2,3-b]pyridin-5-yloxy)benzamide | 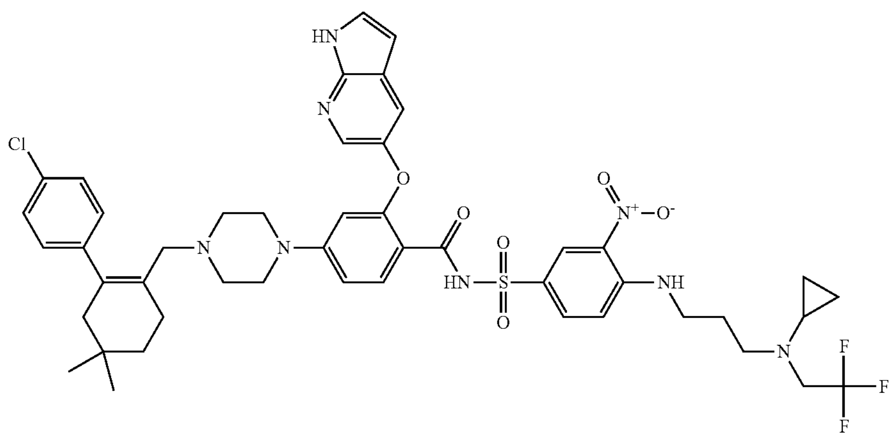 [SMILES: CC1(C)CCC(CN2CCN(c3ccc(C(=O)NS(=O)(=O)c4ccc(NCCCN(CC(F)(F)F)C5CC5)c([N+](=O)[O-])c4)c(Oc4cnc5[nH]ccc5c4)c3)CC2)=C(c2ccc(Cl)cc2)C1] |
| N-[(3-chloro-4-{[1-(oxetan-3-yl)piperidin-4-yl]methoxy}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | 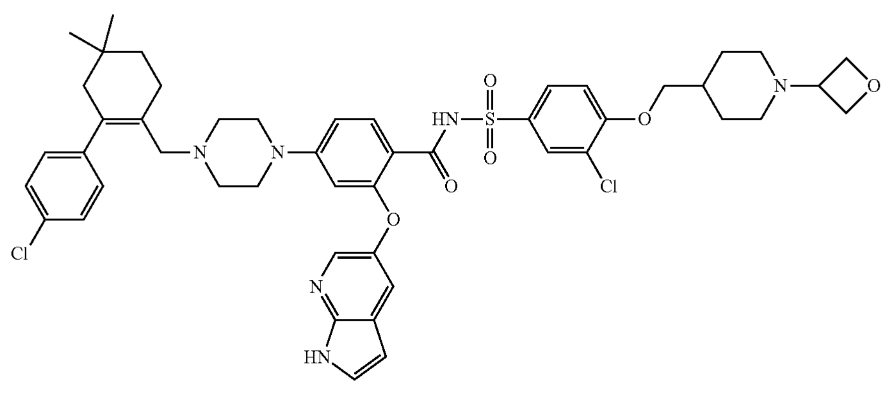 [SMILES: CC1(C)CCC(CN2CCN(c3ccc(C(=O)NS(=O)(=O)c4ccc(OCC5CCN(C6COC6)CC5)c(Cl)c4)c(Oc4cnc5[nH]ccc5c4)c3)CC2)=C(c2ccc(Cl)cc2)C1] |

| Name | Structure |
|---|---|
| 4-(4-{[2-{4-chlorophenyl)-4,4-dimethylcyclohex-1-en-1-yl]methyl}piperazin-1-yl)-N-({3,5-difluoro-4-[(4-fluorotetrahydro-2H-pyran-4-yl)methoxy]phenyl}sulfonyl)-2-(1H-pyrrolo[2,3-b]pyridin-5-yloxy)benzamide | |
| 4-(4-{[2-(4-chlorophenyl)-4,4-dimethylcyclohex-1-en-1-yl]methyl}piperazin-1-yl)-N-{[4-({3-[cyctopropyl(oxetan-3-yl)amino]propyl}amino)-3-nitrophenyl]sulfonyl}-2-(1H-pyrrolo[2,3-b]pyridin-5-yloxy)benzamide | 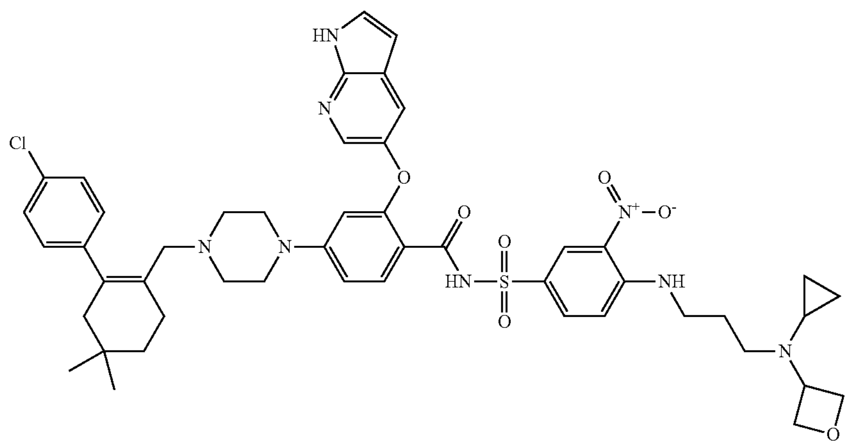 [SMILES: CC1(C)CCC(CN2CCN(c3ccc(C(=O)NS(=O)(=O)c4ccc(NCCCN(C5CC5)C5COC5)c([N+](=O)[O-])c4)c(Oc4cnc5[nH]ccc5c4)c3)CC2)=C(c2ccc(Cl)cc2)C1] |
| N-[(3-chloro-4-{[1-(1-methyl-L-prolyl)piperidin-4-yl]methoxy}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | 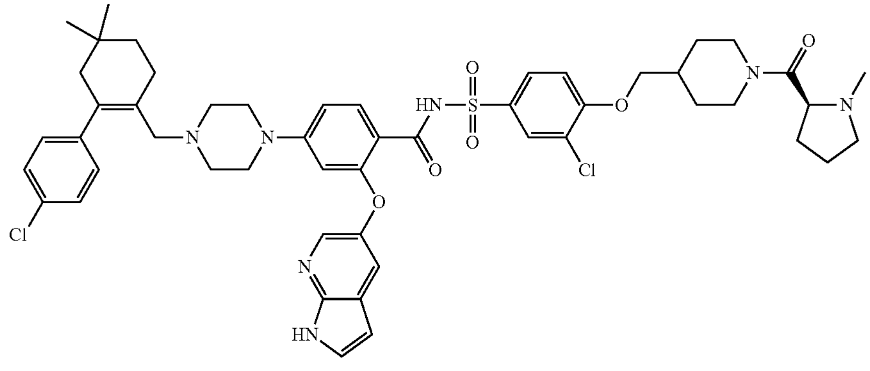 [SMILES: CN1CCC[C@H]1C(=O)N1CCC(COc2ccc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2Cl)CC1] |

-continued

| Name | Structure |
|---|---|
| 4-(4-{[2-(4-chlorophenyl)-4,4-dimethylcyclohex-1-en-1-yl]methyl}piperazin-1-yl)-N-({3,4-difluoro-5-[(4-fluorotetrahydro-2H-pyran-4-yl)methoxy]phenyl}sulfonyl)-2-(1H-pyrrolo[2,3-b]pyridin-5-yloxy)benzamide | 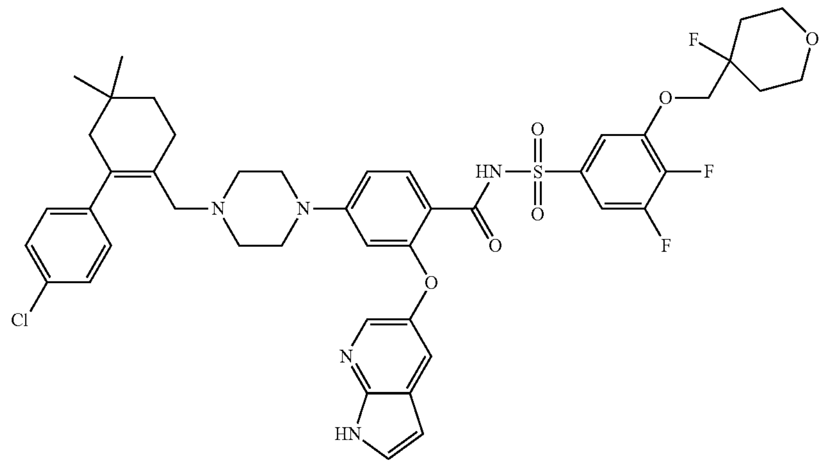 [SMILES: CC1(C)CCC(CN2CCN(c3ccc(C(=O)NS(=O)(=O)c4cc(F)c(F)c(OCC5(F)CCOCC5)c4)c(Oc4cnc5[nH]ccc5c4)c3)CC2)=C(c2ccc(Cl)cc2)C1] |
| N-[(5-chloro-6-{[(2S)-4-cyclopropylmorpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | 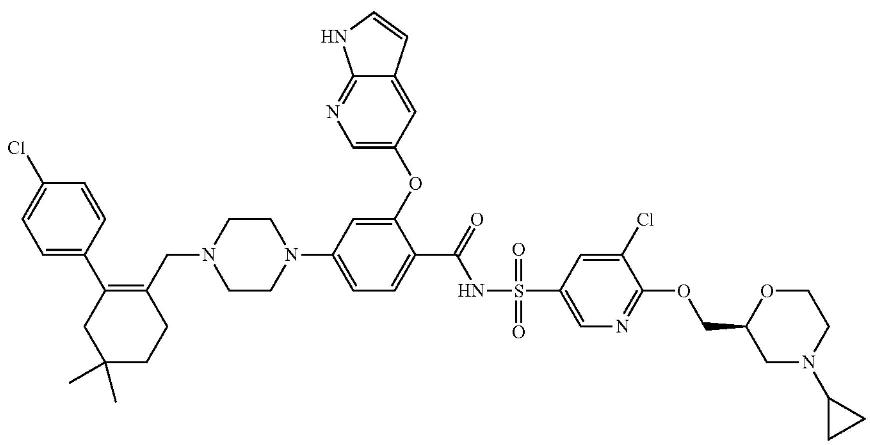 [SMILES: CC1(C)CCC(CN2CCN(c3ccc(C(=O)NS(=O)(=O)c4cnc(OC[C@@H]5CN(C6CC6)CCO5)c(Cl)c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperidin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide | 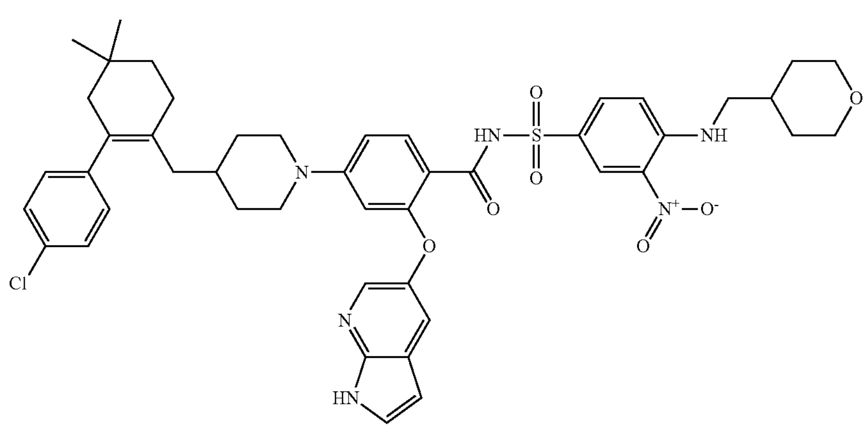 |

-continued

| Name | Structure |
|---|---|
| 4-(4-{[2-(4-chlorophenyl)-4,4-dimethylcyclohex-1-en-1-yl]methyl}piperidin-1-yl)-N-{[3-chloro-4-(tetrahydro-2H-pyran-4-ylmethoxy)phenyl]sulfonyl}-2-(1H-pyrrolo[2,3-b]pyridin-5-yloxy)benzamide | 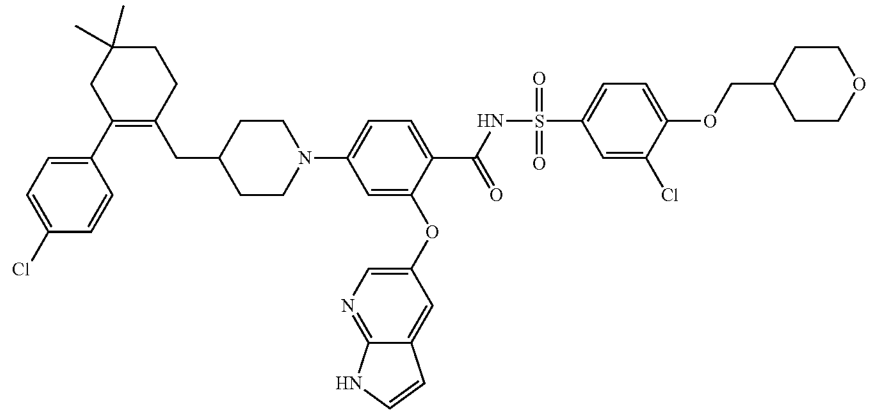 [SMILES: CC1(C)CCC(CC2CCN(c3ccc(C(=O)NS(=O)(=O)c4ccc(OCC5CCOCC5)c(Cl)c4)c(Oc4cnc5[nH]ccc5c4)c3)CC2)=C(c2ccc(Cl)cc2)C1] |
| methyl 2-{[(4-{[4-(4-([2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)amino]methyl}morpholine-4-carboxylate | 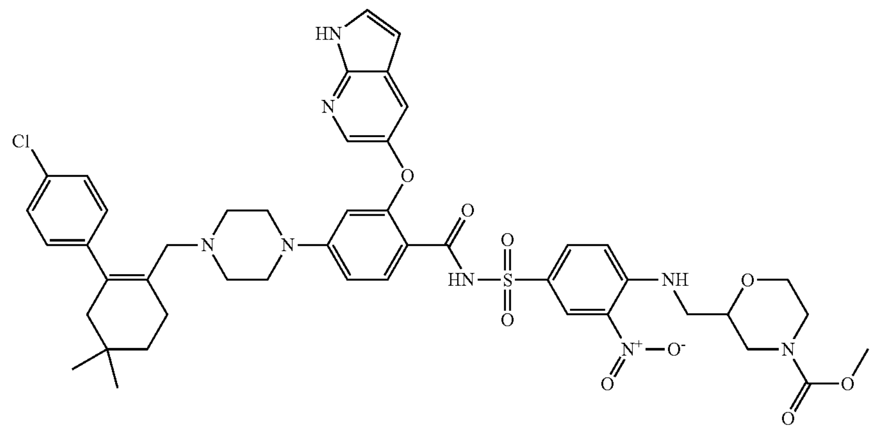 [SMILES: COC(=O)N1CCOC(CNc2ccc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2[N+](=O)[O-])C1] |
| 2-{[(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)amino]methyl}-N-ethyl-N-methylmorpholine-4-carboxamide | 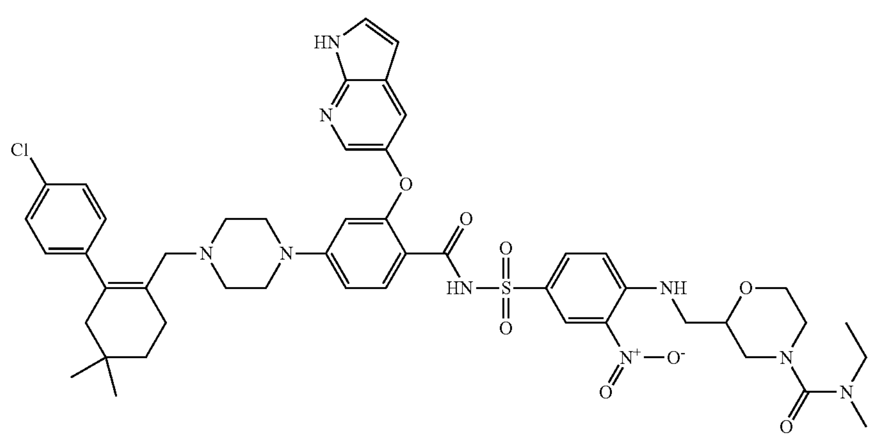 [SMILES: CCN(C)C(=O)N1CCOC(CNc2ccc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2[N+](=O)[O-])C1] |

| Name | Structure |
|---|---|
| 4-(4-{[2-(4-chlorophenyl)-4,4-dimethylcyclohex-1-en-1-yl]methyl}piperazin-1-yl)-N-{[4-({[4-(methylsulfonyl)morpholin-2-yl]methyl}amino)-3-nitrophenyl]sulfonyl}-2-(1H-pyrrolo[2,3-b]pyridin-5-yloxy)benzamide | |
| 4-(4-{[2-{4-chlorophenyl}-4,4-dimethylcyclohex-1-en-1-yl]methyl}piperazin-1-yl)-N-{[4-({3-[cyclobutyl(cyclopropyl)amino]propyl}amino)-3-nitrophenyl]sulfonyl}-2-(1H-pyrrolo[2,3-b]pyridin-5-yloxy)benzamide | |
| 4-(4-{[2-{4-chlorophenyl}-5,5-difluorocyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide | |

| Name | Structure |
|---|---|
| N-[(3-chloro-4-{[4-fluoro-1-(oxetan-3-yl)piperidin-4-yl]methoxy}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | |
| 4-(4-{[2-(4-chlorophenyl)-4,4-dimethylcyclohex-1-en-1-yl](methyl)piperazin-1-yl)-N-{[3-chloro-4-(tetrahydrofuran-3-ylmethoxy)phenyl]sulfonyl}-2-(1H-pyrrolo[2,3-b]pyridin-5-yloxy)benzamide | |
| 4-(4-[(2-(4-chlorophenyl)-5,5-difluorocyclohex-1-en-1-yl]methyl}piperazin-1-yl)-N-[(4-{[(trans-4-hydroxycyclohexyl)methyl]amino}-3-nitrophenyl)sulfonyl]-2-(1H-pyrrolo[2,3-b]pyridin-5-yloxy)benzamide | |

| Name | Structure |
|---|---|
| N-({3-chloro-4-[(4-fluorotetrahydro-2H-pyran-4-yl)methoxy]phenyl}sulfonyl)-4-(4-{[9-(4-chlorophenyl)-3-(oxetan-3-yl)-3-azaspiro[5.5]undec-8-en-8-yl]methyl}piperazin-1-yl)-2-(1H-pyrrolo[2,3-b]pyridin-5-yloxy)benzamide | 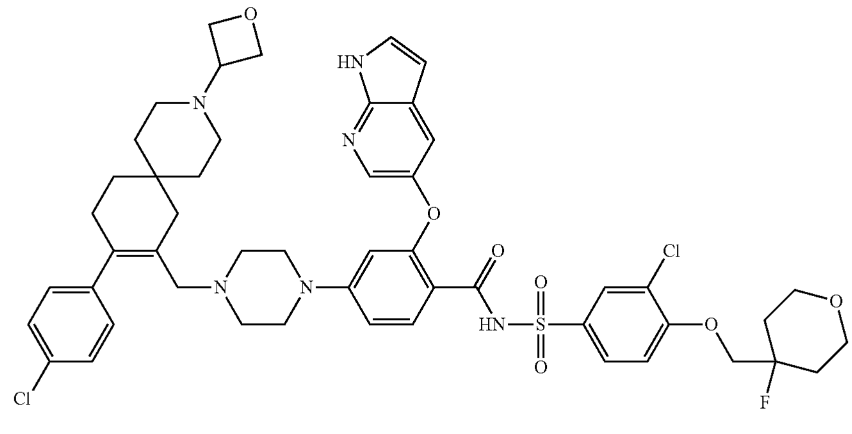 [SMILES: O=C(NS(=O)(=O)c1ccc(OCC2(F)CCOCC2)c(Cl)c1)c1ccc(N2CCN(CC3=C(c4ccc(Cl)cc4)CCC4(CCN(C5COC5)CC4)C3)CC2)cc1Oc1cnc2[nH]ccc2c1] |
| 4-(4-{[2-(4-chlorophenyl)-4,4-dimethylcyclohex-1-en-1-yl]methyl}piperazin-1-yl)-N-{[4-({[(2R)-4-cyclopropylmorpholin-2-yl]methyl}amino)-3-nitrophenyl]sulfonyl}-2-(1H-pyrrolo[2,3-b]pyridin-5-yloxy)benzamide | |
| 4-(4-{[2-(4-chlorophenyl)-4,4-dimethylcyclohex-1-en-1-yl]methyl}piperazin-1-yl)-N-{[4-({[(2S)-4-cyclopropylmorpholin-2-yl]methyl}amino)-3-nitrophenyl]sulfonyl}-2-(1H-pyrrolo[2,3-b]pyridin-5-yloxy)benzamide | 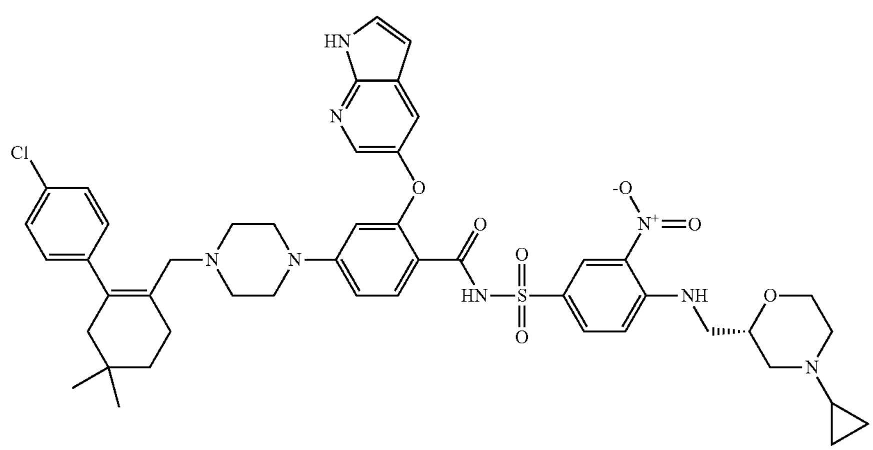 |

| Name | Structure |
|---|---|
| 4-(4-{[5-(4-chlorophenyl)spiro[2.5]oct-5-en-6-yl]methyl}piperazin-1-yl)-N-{{3-nitro-4-[(tetrahydro-2H-pyran-4-ylmethyl)amino]phenyl}sulfonyl)-2-(1H-pyrrolo[2,3-b]pyridin-5-yloxy)benzamide | 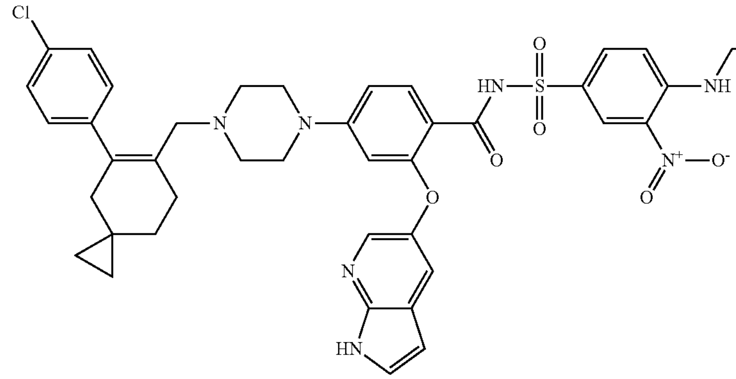 |
| N-{[5-chloro-6-{{4-[cyclopropyl(oxetan-3-yl)amino]cyclohexyl}methoxy)pyridin-3-yl]sulfonyl}-4-(4-[2-(4-chlorophenyl)-4,4-dimethylcyclohex-1-en-1-yl]methyl}piperazin-1-yl)-2-(1H-pyrrolo[2,3-bpyrklin-5-yloxy)benzamide | |
| 4-(4-{[5-(4-chlorophenyl)spiro[2.5]oct-5-en-6-yl]methyl}piperazin-1yl)-N-(4-{(4-cyclopropylmorpholin-2-yl)methyl]amino}-3-nitrophenyl)sulfonyl]-2-(1H pyrrolo[2,3-b]pyridin-5-yloxy)benzamide | 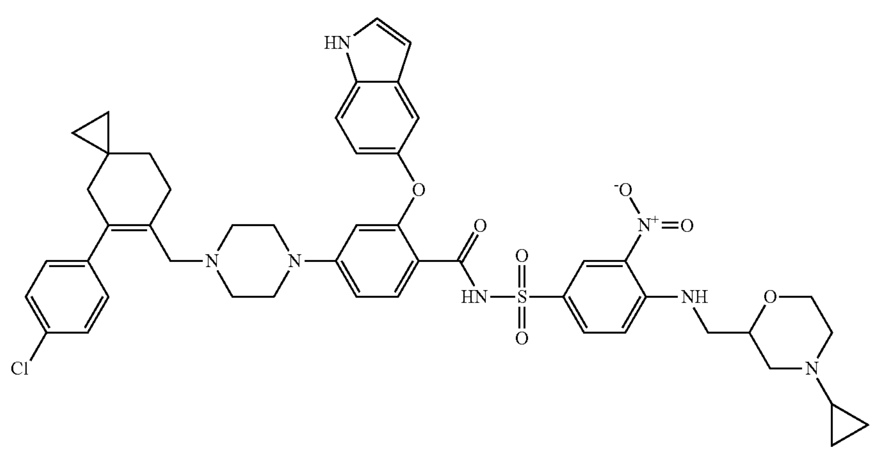 |

| Name | Structure |
|---|---|
| N-({3-chloro-4-[(4-cyclopropylmorpholin-2-yl)methoxy]phenyl}sulfonyl)-4-(4-{[2-(4-chlorophenyl)-4,4-dimethylcyctohex-1-en-1-yl]methyl}piperazin-1-yl)-2-(1H-pyrrolo[2,3-b]pyridin-5-yloxy)benzamide | 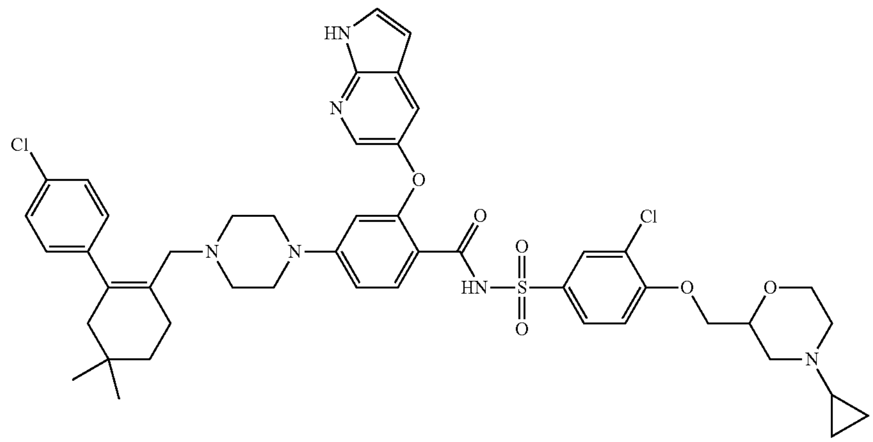 [SMILES: CC1(C)CCC(CN2CCN(c3ccc(C(=O)NS(=O)(=O)c4ccc(OCC5CN(C6CC6)CCO5)c(Cl)c4)c(Oc4cnc5[nH]ccc5c4)c3)CC2)=C(c2ccc(Cl)cc2)C1] |
| N-[(3-chloro-4-[(4-cyclopropylmorpholin-2-yl)methyl]amino}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | 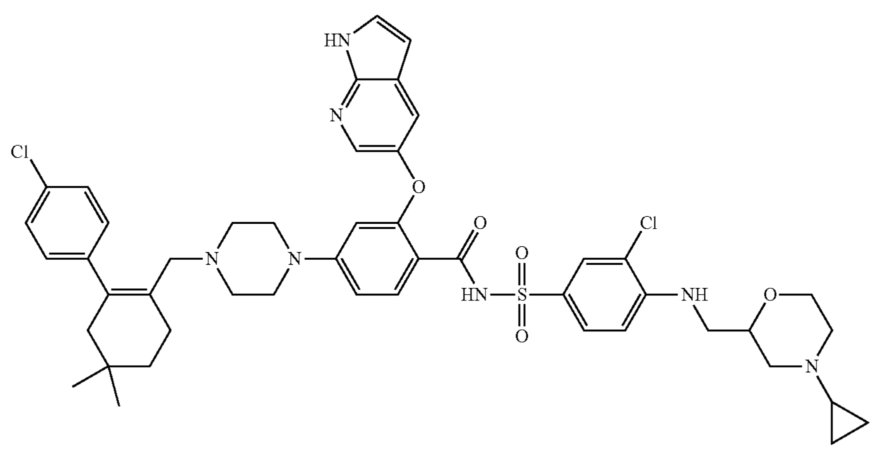 |
| 2-{[(2-chloro-4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}phenyl)amino]methyl}-N-ethyl-N-methylmorpholine-4-carboxamide | 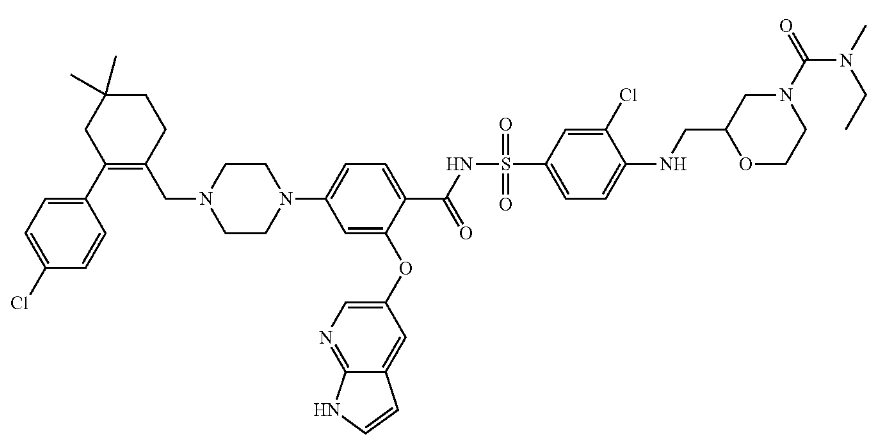 [SMILES: CCN(C)C(=O)N1CCOC(CNc2ccc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2Cl)C1] |

-continued

| Name | Structure |
|---|---|
| (2S)-2-{[(3-chloro-5-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}pyridin-2-yl)oxy]methyl)-N-ethyl-N-methylmorpholine-4-carboxamide | 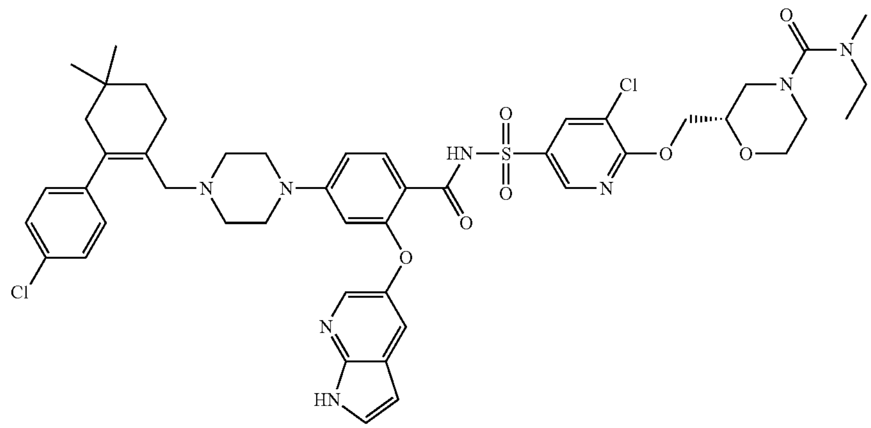 [SMILES: CCN(C)C(=O)N1CCO[C@H](COc2ncc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2Cl)C1] |
| N-[(5-chloro-6-{[(4-cyclopropylmorpholin-2-yl)methyl]amino}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | 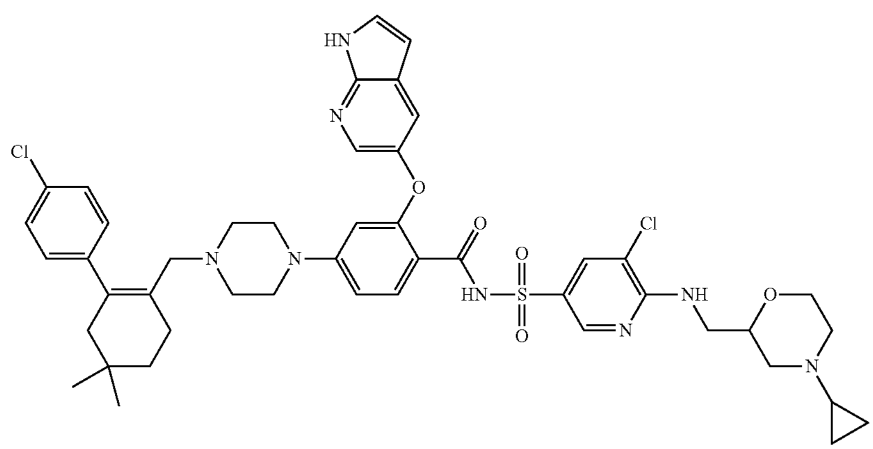 [SMILES: CC1(C)CCC(CN2CCN(c3ccc(C(=O)NS(=O)(=O)c4cnc(NCC5CN(C6CC6)CCO5)c(Cl)c4)c(Oc4cnc5[nH]ccc5c4)c3)CC2)=C(c2ccc(Cl)cc2)C1] |
| 2{[(3-chloro-5-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}pyridin-2-yl)amino]methyl}-N-ethyl-N-methylmorpholine-4-carboxamide | 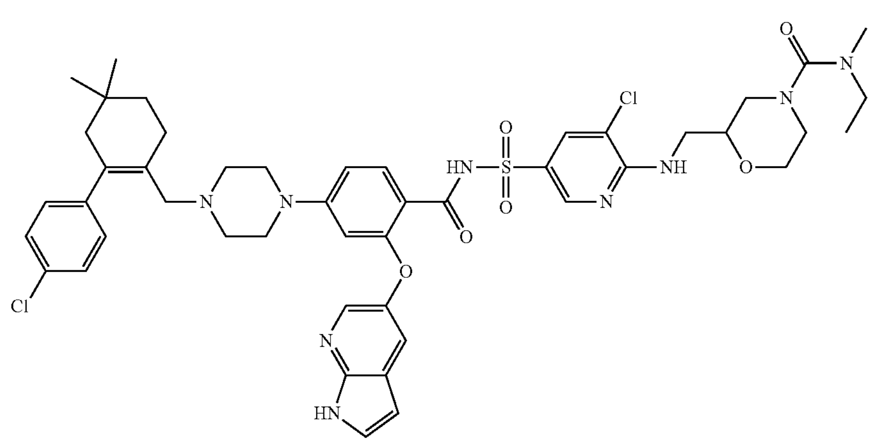 [SMILES: CCN(C)C(=O)N1CCOC(CNc2ncc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2Cl)C1] |

| Name | Structure |
|---|---|
| 4-(4-{[2-(4-chlorophenyl)-4,4-dimethylcyclohex-1-en-1-yl]methyl}piperazin-1-yl)-N-[(4-{[(trans-4-hydroxy-4-methylcyclohexyl)methyl]amino}-3-nitrophenyl)sulfonyl]-2-(1H-pyrrolo[2,3-b]pyridin-5-yloxy)benzamide | |
| 4-(4-{[2-(4-chlorophenyl)-4,4-dimethylcyclohex-1-en-1-yl(methyl}piperazin-1-yl)-N-[(4-{[(cis-4-hydroxy-4-methylcyclohexyl)methyl]amino}-3-nitrophenyl)sulfonyl]-2-(1H-pyrrolo[2,3-b]pyridin-5-yloxy)benzamide | 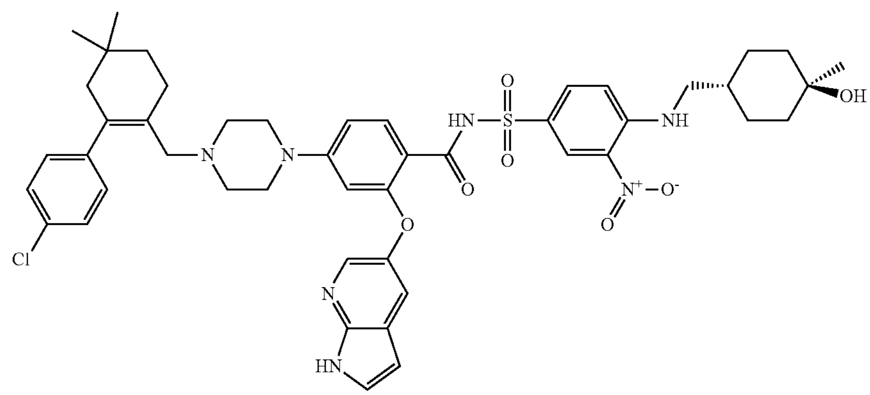 [SMILES: CC1(C)CCC(CN2CCN(c3ccc(C(=O)NS(=O)(=O)c4ccc(NC[C@H]5CC[C@](C)(O)CC5)c([N+](=O)[O-])c4)c(Oc4cnc5[nH]ccc5c4)c3)CC2)=C(c2ccc(Cl)cc2)C1] |
| N-[(5-chloro-6-{[(1R,2R,4R,5R)-5-hydroxy-5-methylbicyclo[2.2.1]hept-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | 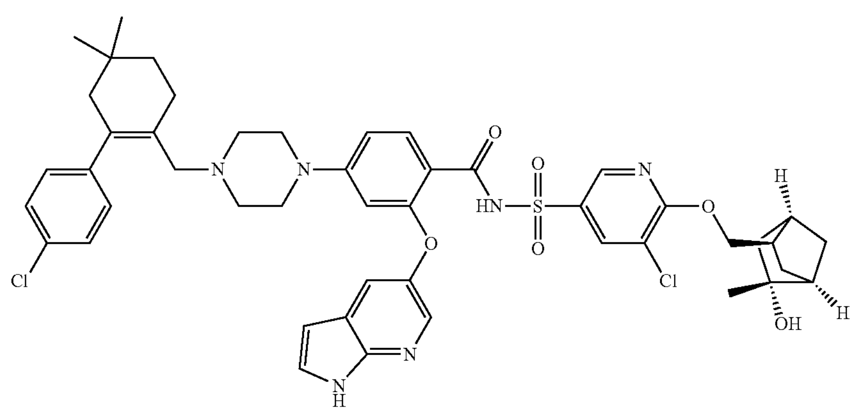 [SMILES: CC1(C)CCC(CN2CCN(c3ccc(C(=O)NS(=O)(=O)c4cnc(OC[C@@H]5C[C@H]6C[C@@H]5C[C@@]6(C)O)c(Cl)c4)c(Oc4cnc5[nH]ccc5c4)c3)CC2)=C(c2ccc(Cl)cc2)C1] |

| Name | Structure |
|---|---|
| 4-(4-{[2-(4-chlorophenyl)-4,4-dimethylcyclohex-1-en-1-yl]methyl}piperazin-1-yl)-N-{[4-({4-[(2-cyanoethyl)(cyclopropyl)amino]cyclohexyl}amino)-3-nitrophenyl]sulfonyl}-2-(1H-pyrrolo[2,3-b]pyridin-5-yloxy)benzamide | |
| N-({5-chloro-6-[(trans-4-hydroxy-4-methylcyclohexyl)methoxy]pyridin-3-yl}sulfonyl)-4-(4-{[5-(4-chlorophenyl)spiro[2.5]oct-5-en-6-yl]methyl}piperazin-1-yl)-2-(1H-pyrrolo[2,3-b]pyridin-5-yloxy)benzamide | |
| 4-(4-{[2-(4-chlorophenyl)-4,4-dimethylcyclohex-1-en-1-yl]methyl}piperazin-1-yl)-N-{[5-chloro-6-(5,6,7,8-tetrahydroimidazo[1,2-a]pyridin-6-ylmethoxy)pyridin-3-yl]sulfonyl}-2-(1H-pyrrolo[2,3-b]pyridin-5-yloxy)benzamide | |

-continued

| Name | Structure |
|---|---|
| N-[(5-chloro-6-({[(1R,2S,4R,5R)-5-hydroxy-5-methylbicyclo[2.2.1]hept-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | |
| 4-(4-{[2-(4-chlorophenyl)-4,4-dimethylcyclohex-1-en-1-yl]methyl}piperazin-1-yl)-N-({4-[(cis-4-hydroxy-4-methylcyclohexyl)methoxy]-3-nitrophenyl}sulfonyl)-2-(1H-pyrrolo[2,3-b]pyridin-5-yloxy)benzamide | |
| N-[(5-chloro-6-{[4-fluoro-1-(oxetan-3-yl)piperidin-4-yl]methoxy}pyridin-3-yl)sulfonyl]-4-(4-{[5-(4-chlorophenyl)spiro[2.5]oct-5-en-6-yl]methyl}piperazin-1-yl)-2-(1H-pyrrolo[2,3-b]pyridin-5-yloxy)benzamide | |

| Name | Structure |
|---|---|
| 4-(4-{[2-(4-chlorophenyl)-4,4-dimethylcyclohex-3-en-1-yl]methyl}piperazin-1-yl)-N-[(4-{[4-(3,3-difluoropyridin-1-yl)cyclohexyl]amino}-3-nitrophenyl)sulfonyl]-2-(1H-pyrrolo[2,3-b]pyridin-5-yloxy)benzamide | 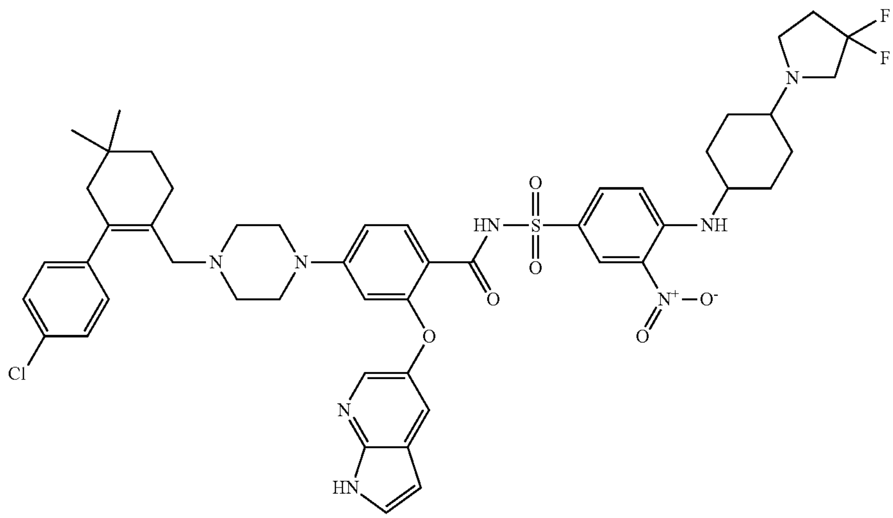 [SMILES: CC1(C)CCC(CN2CCN(c3ccc(C(=O)NS(=O)(=O)c4ccc(NC5CCC(N6CCC(F)(F)C6)CC5)c([N+](=O)[O-])c4)c(Oc4cnc5[nH]ccc5c4)c3)CC2)=C(c2ccc(Cl)cc2)C1] |
| N-({5-chloro-6-[(trans-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | |
| N-({5-chloro-6-[(cis-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | 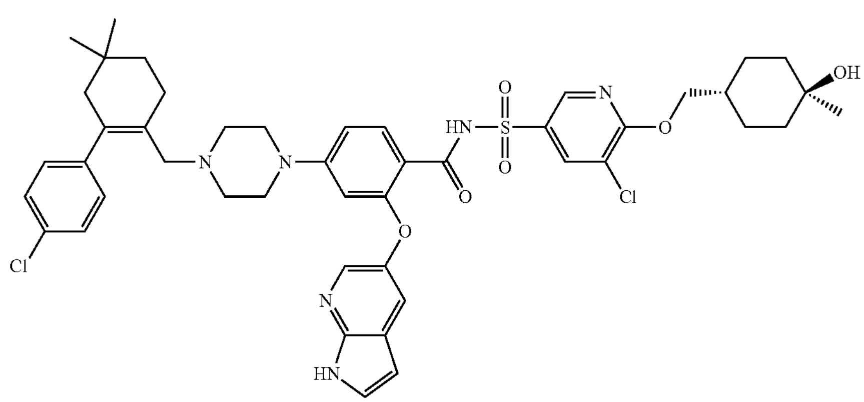 [SMILES: CC1(C)CCC(CN2CCN(c3ccc(C(=O)NS(=O)(=O)c4cnc(OC[C@H]5CC[C@](C)(O)CC5)c(Cl)c4)c(Oc4cnc5[nH]ccc5c4)c3)CC2)=C(c2ccc(Cl)cc2)C1] |

| Name | Structure |
|---|---|
| 4-(4-{[2-{4-chlorophenyl)-4,4-dimethylcyclohex-1-en-1-yl]methyl}piperazin-1-yl)-N-{[4-({4-[(2,2-difluorocyclopropyl)amino]cyclohexyl}amino)-3-nitrophenyl]sulfonyl}-2-(1H-pyrrolo[2,3-b]pyridin-5-yloxy)benzamide | 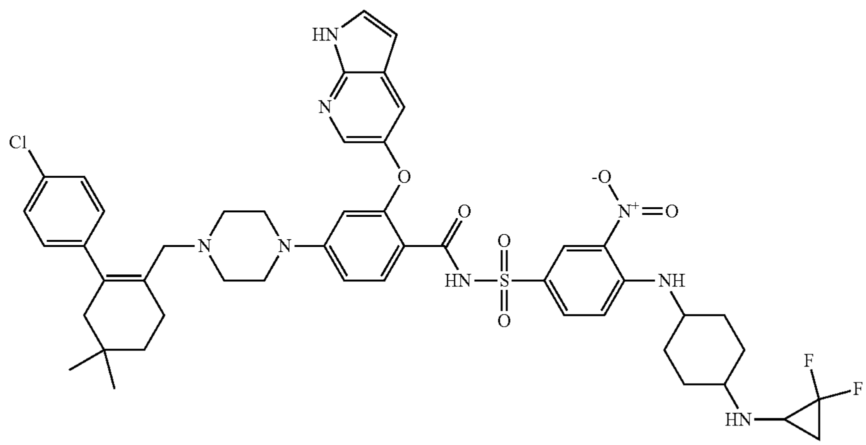 |
| N-({5-chloro-6-[(cis-1-fluoro-4-hydroxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | 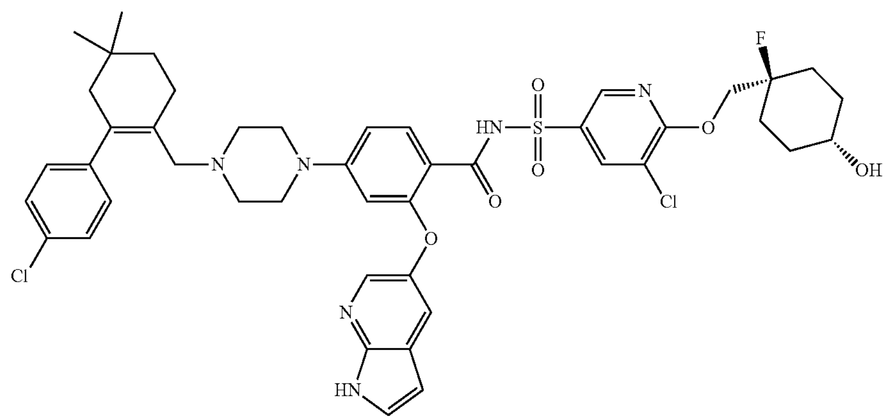 [SMILES: CC1(C)CCC(CN2CCN(c3ccc(C(=O)NS(=O)(=O)c4cnc(OC[C@]5(F)CC[C@H](O)CC5)c(Cl)c4)c(Oc4cnc5[nH]ccc5c4)c3)CC2)=C(c2ccc(Cl)cc2)C1] |
| 4-(4-{[2-{4-chlorophenyl)-4,4-dimethylcyclohex-1-en-1-yl]methyl}piperazin-1-yl)-N-{[3-nitro-4-(2-oxaspiro[3.5]non-7-ylmethoxy)phenyl]sulfonyl}-2-(1H-pyrrolo[2,3-b]pyridin-5-yloxy)benzamide | 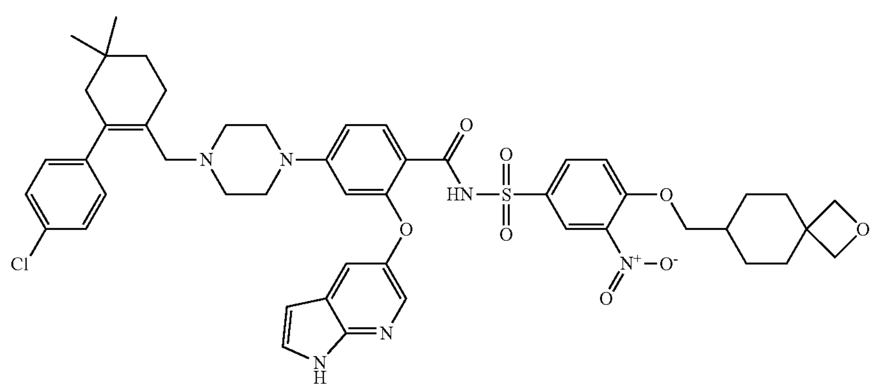 [SMILES: CC1(C)CCC(CN2CCN(c3ccc(C(=O)NS(=O)(=O)c4ccc(OCC5CCC6(CC5)COC6)c([N+](=O)[O-])c4)c(Oc4cnc5[nH]ccc5c4)c3)CC2)=C(c2ccc(Cl)cc2)C1] |

| Name | Structure |
|---|---|
| 4-(4-{[2-(4-chlorophenyl)-4,4-dimethylcyclohex-1-en-1-yl]methyl}piperazin-1-yl)-N-{{4-[(trans-4-hydroxy-4-methylcyclohexyl)methoxy]-3-nitrophenyl}sulfonyl)-2-(1H-pyrrolo[2,3-b]pyridin-5-yloxy)benzamide | 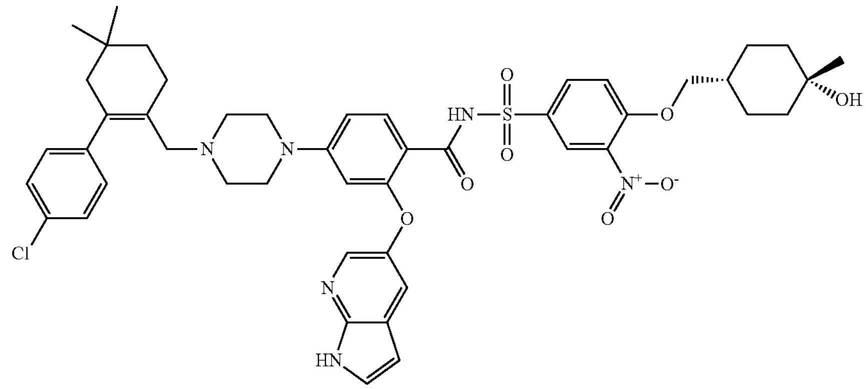 [SMILES: CC1(C)CCC(CN2CCN(c3ccc(C(=O)NS(=O)(=O)c4ccc(OC[C@H]5CC[C@@](C)(O)CC5)c([N+](=O)[O-])c4)c(Oc4cnc5[nH]ccc5c4)c3)CC2)=C(c2ccc(Cl)cc2)C1] |
| 4-(4-{[2-(4-chlorophenyl)-5,5-bis(fluoromethyl)cyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide | 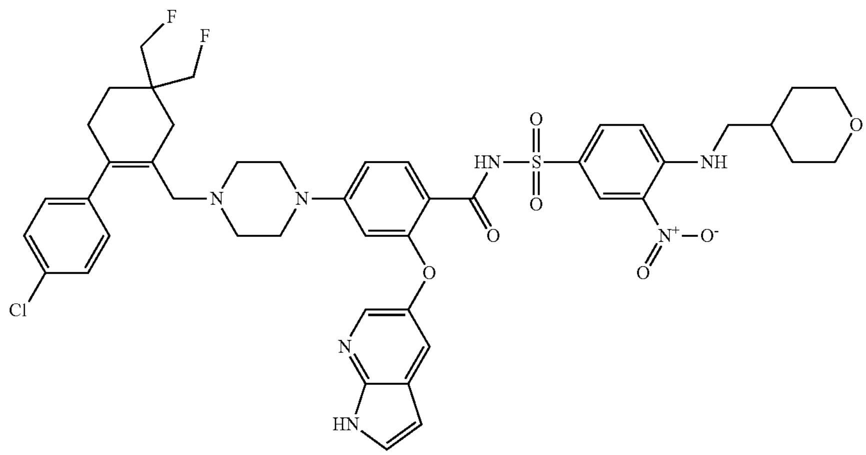 [SMILES: O=C(NS(=O)(=O)c1ccc(NCC2CCOCC2)c([N+](=O)[O-])c1)c1ccc(N2CCN(CC3=C(c4ccc(Cl)cc4)CCC(CF)(CF)C3)CC2)cc1Oc1cnc2[nH]ccc2c1] |
| 4-(4-{[2-(4-chlorophenyl)-4,4-dimethylcyclohex-1-en-1-yl]methyl}piperazin-1-yl)-N-({4-[(4-cyclopropylmorpholin-2-yl)methoxy]-3-nitrophenyl}sulfonyl)-2-(1H-pyrrolo[2,3-b]pyridin-5-yloxy)benzamide | 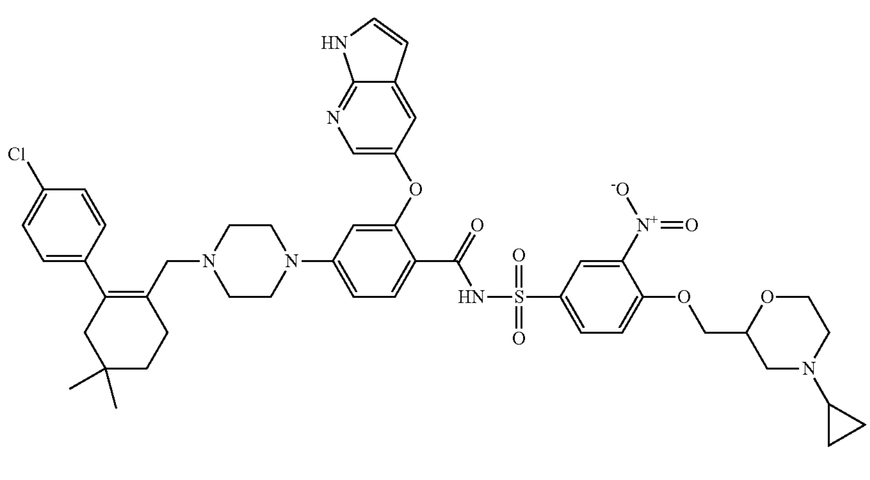 |

-continued

| Name | Structure |
|---|---|
| N-({5-chloro-6-[(trans-1-fluoro-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | 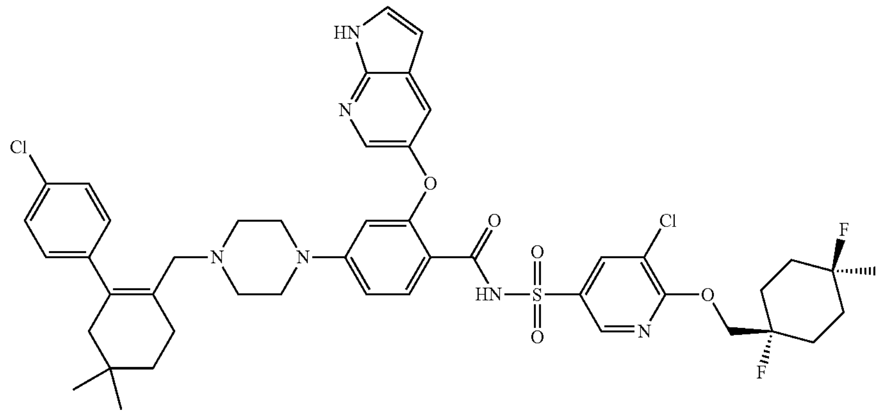 [SMILES: CC1(C)CCC(CN2CCN(c3ccc(C(=O)NS(=O)(=O)c4cnc(OC[C@]5(F)CC[C@](C)(F)CC5)c(Cl)c4)c(Oc4cnc5[nH]ccc5c4)c3)CC2)=C(c2ccc(Cl)cc2)C1] |
| N-({5-chloro-6-[(cis-1-fluoro-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | 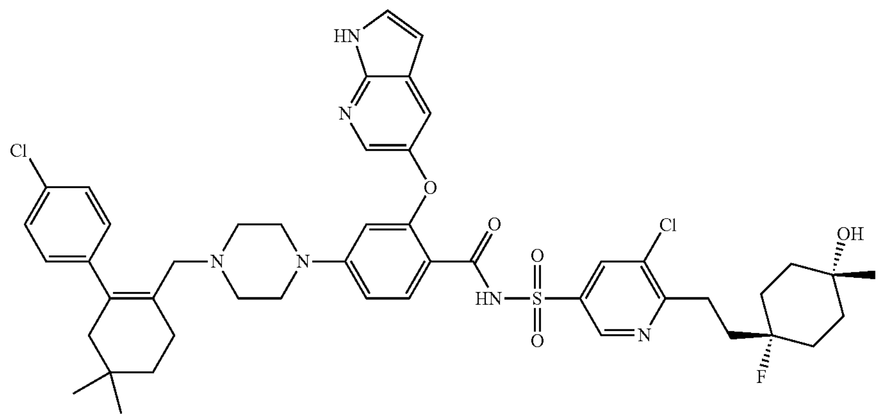 [SMILES: CC1(C)CCC(CN2CCN(c3ccc(C(=O)NS(=O)(=O)c4cnc(CC[C@]5(F)CC[C@@](C)(O)CC5)c(Cl)c4)c(Oc4cnc5[nH]ccc5c4)c3)CC2)=C(c2ccc(Cl)cc2)C1] |
| 4-{4-{[2-(4-chlorophenyl)-4,4-dimethylcyclohex-1-en-1-yl]methyl}piperazin-1-yl)-N-[(3-cyano-4-{[4-fluoro-1-(oxetan-3-yl)piperidin-4-yl]methoxy}phenyl)sulfonyl]-2-(1H-pyrrolo[2,3-b]pyridin-5-yloxy)benzamide | 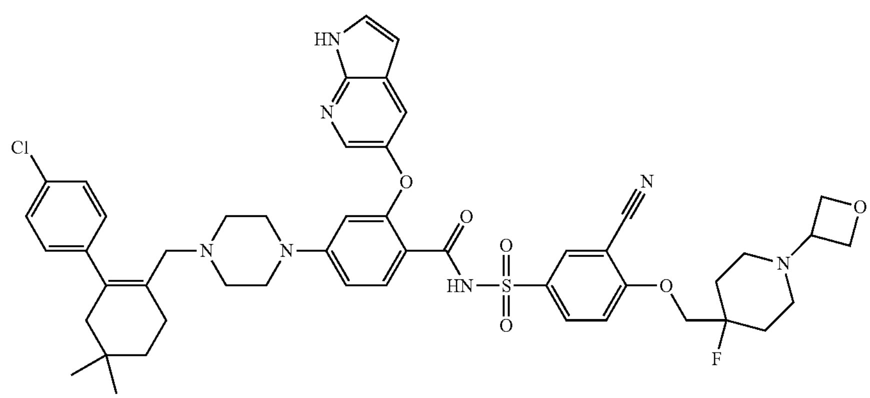 [SMILES: CC1(C)CCC(CN2CCN(c3ccc(C(=O)NS(=O)(=O)c4ccc(OCC5(F)CCN(C6COC6)CC5)c(C#N)c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-[(4-{[(trans-4-ethyl-4-hydroxycyclohexyl)methyl]amino}-3-nitrophenyl)sulfonyl]-2-(1H-pyrrolo[2,3-b]pyridin-5-yloxy)benzamide | |

| Name | Structure |
|---|---|
| 4-(4-{[2-(4-chlorophenyl)-4,4-dimethylcyclohex-1-en-1-yl]methyl}piperazin-1-yl)-N-[(4-{[(cis-4-ethyl-4-hydroxycyclohexyl)methyl]amino}-3-nitrophenyl)sulfonyl]-2-(1H-pyrrolo[2,3-b]pyridin-5-yloxy)benzamide | 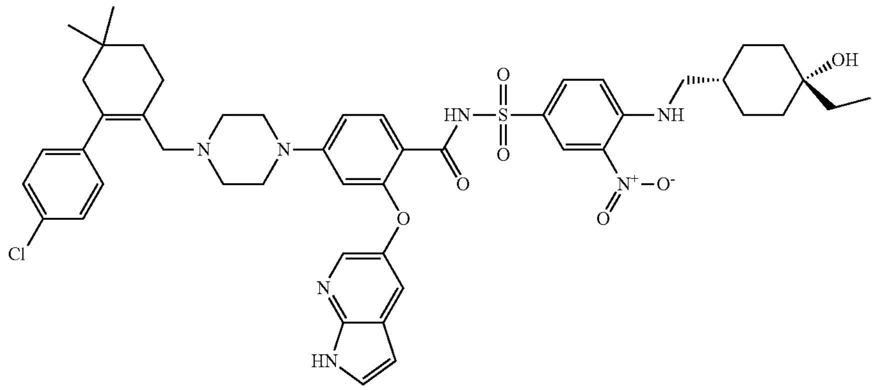 [SMILES: CC[C@]1(O)CC[C@@H](CNc2ccc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2[N+](=O)[O-])CC1] |
| 4-(4-{[2-(4-chlorophenyl)-5-(methoxymethyl)-5-methylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide | 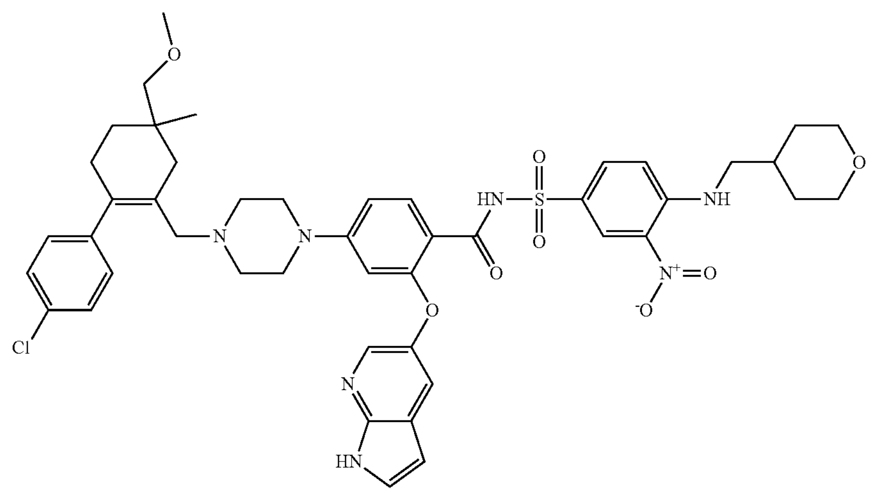 |
| 4-(4-{[2-(4-chlorophenyl)-4,4-dimethylcyclohex-1-en-1-yl]methyl}piperazin-1-yl)-N-{[3-nitro-4-({[(2S)-4-(oxetan-3-yl)morpholin-2-yl]methyl}amino)phenyl]sulfonyl}-2-(3H-pyrrolo[2,3-b]pyridin-3-yloxy)benzamide | 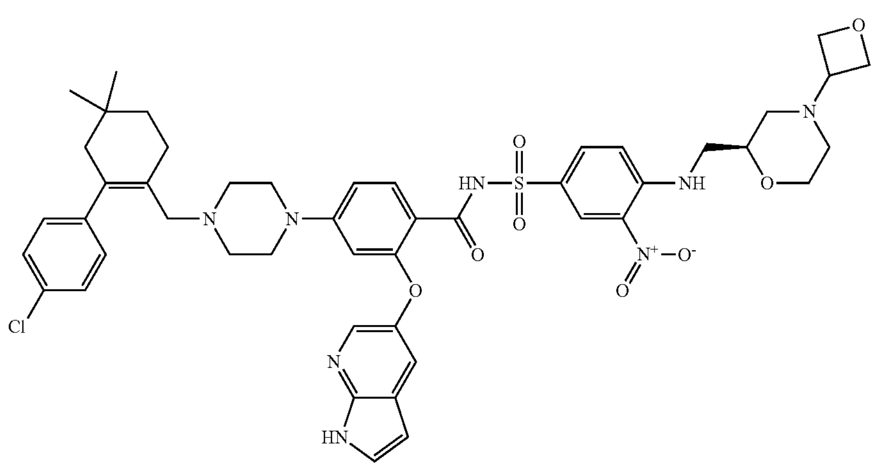 [SMILES: CC1(C)CCC(CN2CCN(c3ccc(C(=O)NS(=O)(=O)c4ccc(NC[C@H]5CN(C6COC6)CCO5)c([N+](=O)[O-])c4)c(Oc4cnc5[nH]ccc5c4)c3)CC2)=C(c2ccc(Cl)cc2)C1] |

| Name | Structure |
|---|---|
| N-({3-chloro-4-[(trans-4-hydroxy-4-methylcyclohexyl)methoxy]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide | 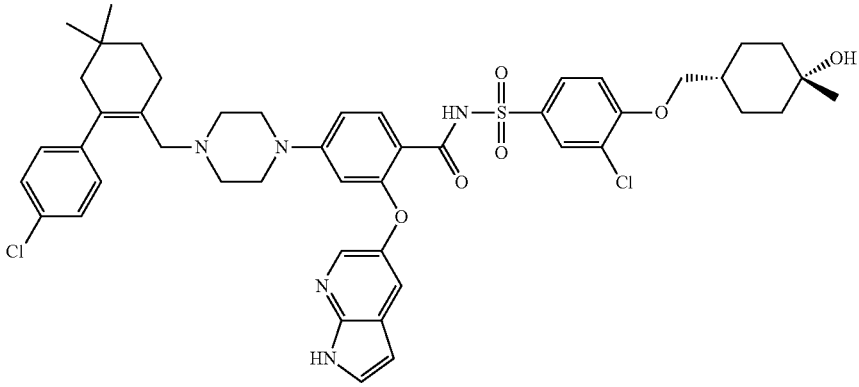 [SMILES: CC1(C)CCC(CN2CCN(c3ccc(C(=O)NS(=O)(=O)c4ccc(OC[C@H]5CC[C@@](C)(O)CC5)c(Cl)c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-{[4-({4-[(2-cyanoethyl)(cyclopropyl)amino]-1-fluorocyclohexyl}methoxy)-3-nitrophenyl]sulfonyl}-2-(1H-pyrrolo[2,3-b]pyridin-5-yloxy)benzamide | 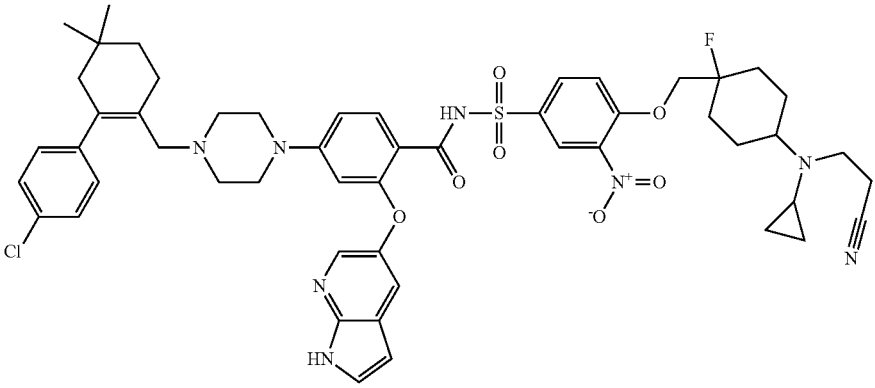 |
| 4-(4-{[2-{4-chlorophenyl}-4,4-dimethylcyclohex-1-en-1-yl]methyl}piperazin-1-yl)-N-({5-nitro-6-[(tetrahydro-2H-pyran-4-ylmethyl)amino]pyridin-3-yl}sulfonyl)-2-(1H-pyrrolo[2,3-b]pyridin-5-yloxy)benzamide | 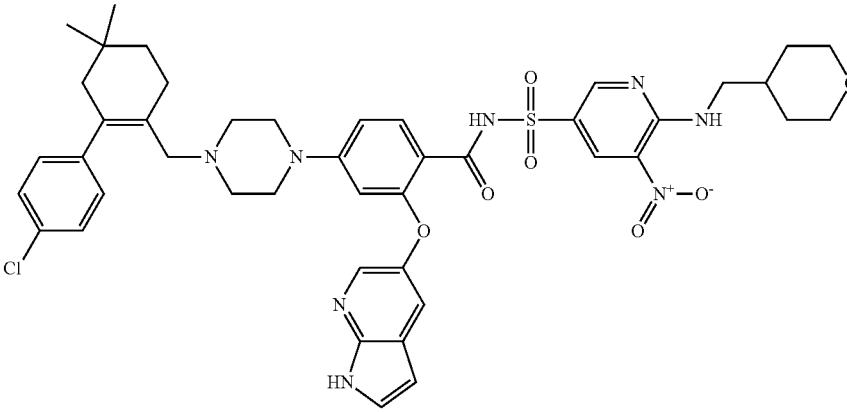 |
| 4-(4-{[2-{4-chlorophenyl}-4,4-dimethylcyclohex-1-en-1-yl]methyl}piperazin-1-yl)-N-({3-nitro-4-[(2-oxaspiro[3.5]non-7-ylmethyl)amino]phenyl}sulfonyl)-2-(1H-pyrrolo[2,3-b]pyridin-5-yloxy)benzamide | 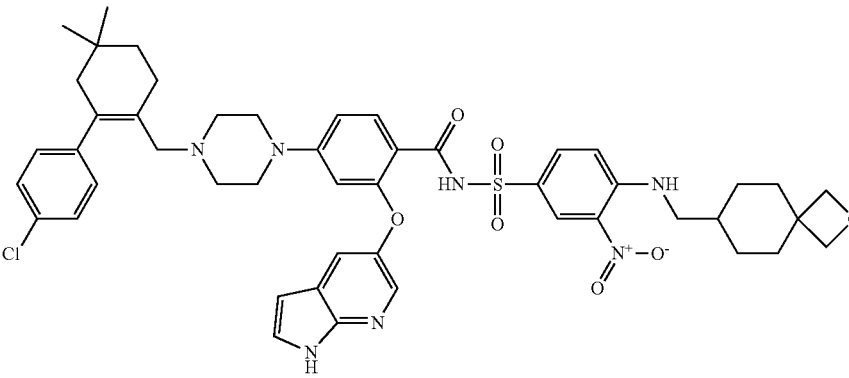 |

-continued
| Name | Structure |
|---|---|
| 4-(4-{[2-{4-chlorophenyl)-4,4-dimethylcyclohex-1-en-1-yl]methyl}piperazin-1-yl)-N-[(4-{[(4-cyano-4-methylcyclohexyl)methyl]amino}-3-nitrophenyl)sulfonyl]-2-(1H-pyrrolo[2,3-b]pyridin-5-yloxy)benzamide | 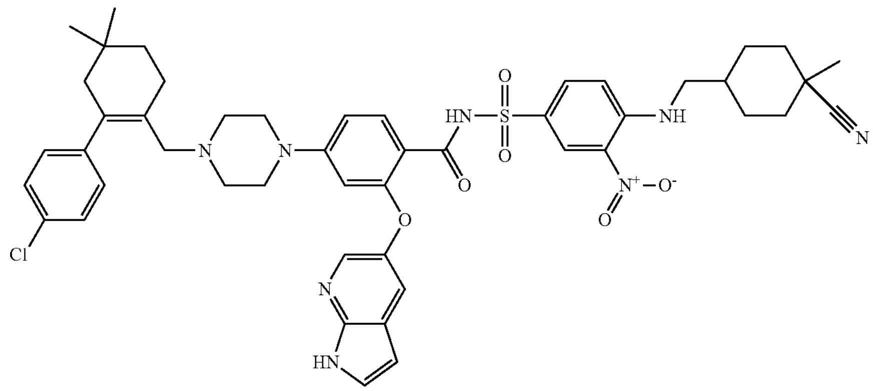 [SMILES: CC1(C)CCC(CN2CCN(c3ccc(C(=O)NS(=O)(=O)c4ccc(NCC5CCC(C)(C#N)CC5)c([N+](=O)[O-])c4)c(Oc4cnc5[nH]ccc5c4)c3)CC2)=C(c2ccc(Cl)cc2)C1] |
| ([4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]({4-[(4-fluorotetrahydro-2H-pyran-4-yl)methoxy]-3-nitrophenyl}sulfonyl)amino} methyl pivalate | 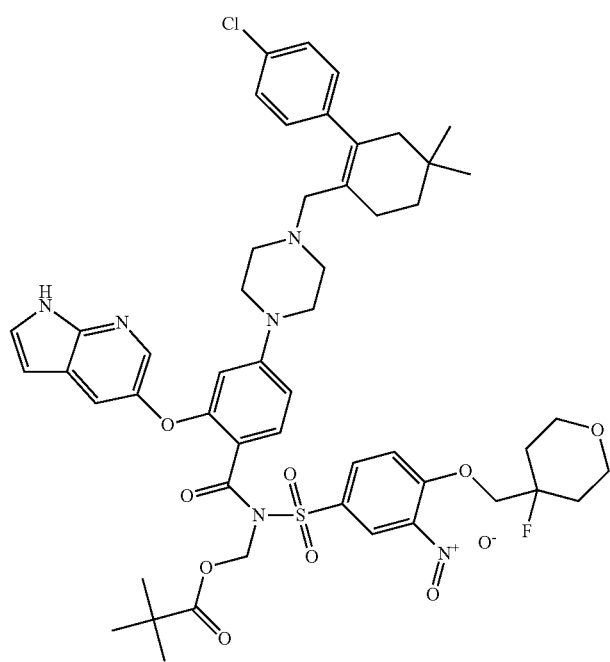 |

| Name | Structure |
|---|---|
| {[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]([4-[(4-fluorotetrahydro-2H-pyran-4-yl)methoxy]-3-nitrophenyl}sulfonyl)amino} methyl butyrate | 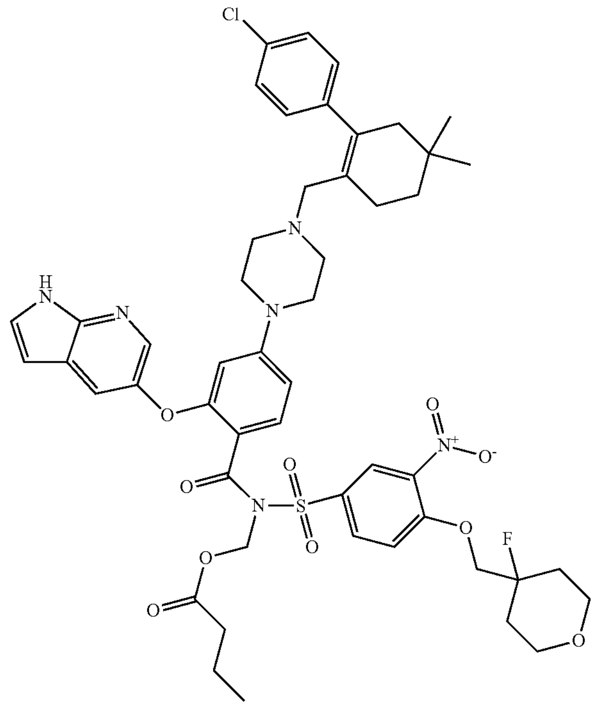 [SMILES: CCCC(=O)OCN(C(=O)c1ccc(N2CCN(CC3=C(c4ccc(Cl)cc4)CC(C)(C)CC3)CC2)cc1Oc1cnc2[nH]ccc2c1)S(=O)(=O)c1ccc(OCC2(F)CCOCC2)c([N+](=O)[O-])c1] |
| 4-[4-{[2-{4-chlorophenyl)-4,4-dimethylcyclohex-1-en-1-yl]methyl}(²H₈)piperazin-1-yl]-N-({3-nitro-4-[(tetrahydro-2H-pyran-4-ylmethyl)amino]phenyl}sulfonyl)-2-(1H-pyrrolo[2,3-b]pyridin-5-yloxy)benzamide | |
| 4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)-N-{[3-(tetrahydro-2H-pyran-4-ylmethyl)-3H-[1,2,3]triazolo[4,5-b]pyridin-6-yl]sulfonyl}benzamide | 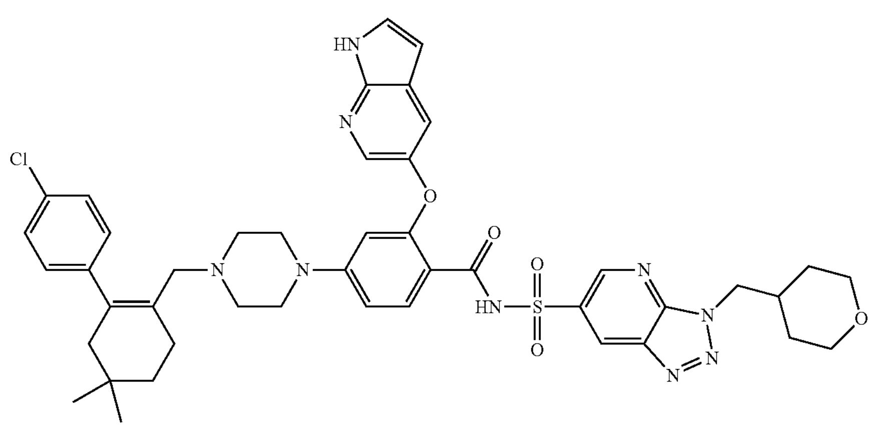 [SMILES: CC1(C)CCC(CN2CCN(c3ccc(C(=O)NS(=O)(=O)c4cnc5c(c4)nnn5CC4CCOCC4)c(Oc4cnc5[nH]ccc5c4)c3)CC2)=C(c2ccc(Cl)cc2)C1] |

-continued

| Name | Structure |
|---|---|
| 4-(4-{[2-(4-chlorophenyl)-4,4-dimethylcyclohex-1-en-1-yl]methyl}piperazin-1-yl)-N--[(6-{[(trans-4-hydroxy-4-methylcyclohexyl)methyl]amino}-5-nitropyridin-3-yl)sulfonyl]-2-(1H-pyrrolo[2,3-b]pyridin-5-yloxy)benzamide | 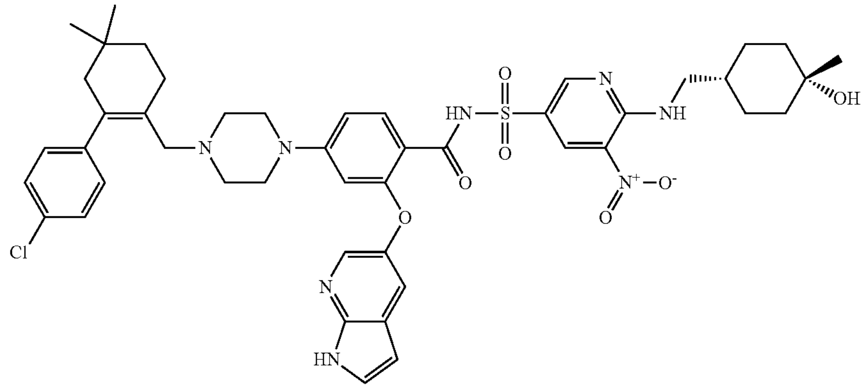 [SMILES: CC1(C)CCC(CN2CCN(c3ccc(C(=O)NS(=O)(=O)c4cnc(NC[C@H]5CC[C@@](C)(O)CC5)c([N+](=O)[O-])c4)c(Oc4cnc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1l-yl)-N-[(5-cyano-6-{[4-fluoro-1-(oxetan-3-yl)piperidin-4-yl]methoxy}pyridin-3-yl)sulfonyl]-2-(1H-pyrrolo[2,3-b]pyridin-5-yloxy)benzamide | 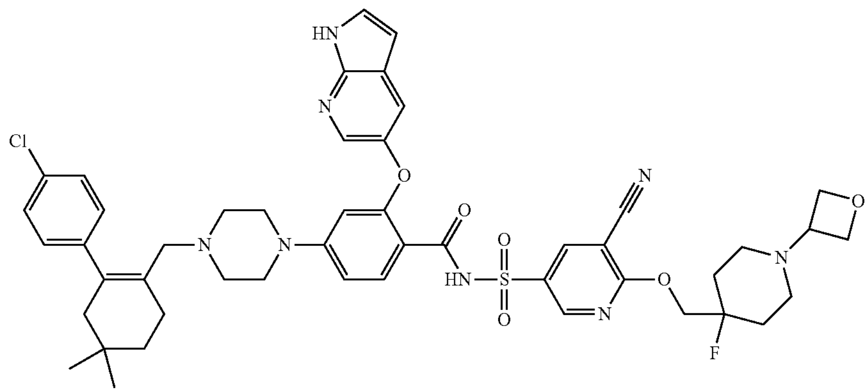 [SMILES: CC1(C)CCC(CN2CCN(c3ccc(C(=O)NS(=O)(=O)c4cnc(OCC5(F)CCN(C6COC6)CC5)c(C#N)c4)c(Oc4cnc5[nH]ccc5c4)c3)CC2)=C(c2ccc(Cl)cc2)C1] |
| N-(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)morpholine-4-carboxamide | 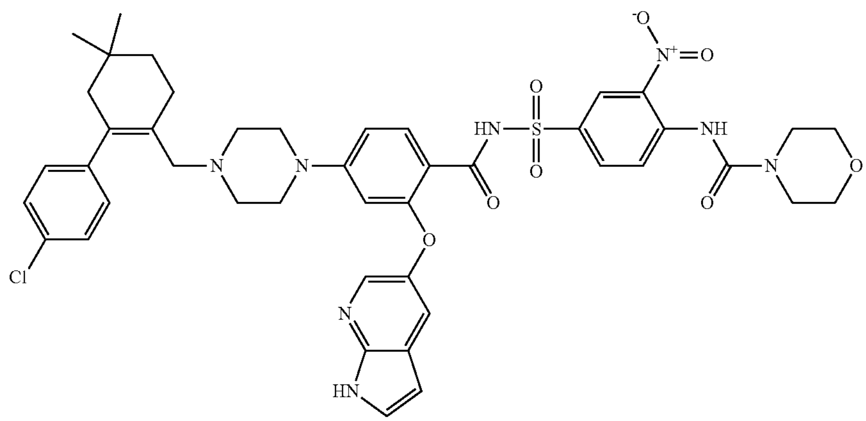 |
| 4-{4-{[2-(4-chlorophenyl)-4,4-dimethylcyclohex-1-en-1-yl]methyl}piperazin-1-yl)-N-{[4-({[4-(methoxymethyl)cyclohexyl]methyl}amino)-3-nitrophenyl]sulfonyl}-2-(1H-pyyrolo[2,3-b]pyridin-5-yloxy)benzamide | 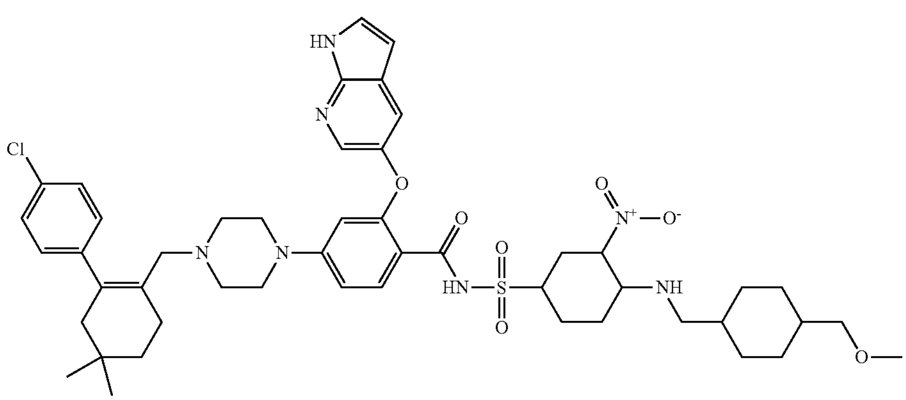 [SMILES: COCC1CCC(CNC2CCC(S(=O)(=O)NC(=O)c3ccc(N4CCN(CC5=C(c6ccc(Cl)cc6)CC(C)(C)CC5)CC4)cc3Oc3cnc4[nH]ccc4c3)CC2[N+](=O)[O-])CC1] |

| Name | Structure |
|---|---|
| 4-(4-{[2-(4-chlorophenyl)-4,4-dimethylcyclohex-1-en-1-yl]methyl}piperazin-1-yl)-N-[(5-chloro-6-{[1-(1,3-thiazol-2-yl)piperidin-4-yl]methoxy}pyridin-3-yl)sulfonyl]-2-(1H-pyrrolo[2,3-b]pyridin-5-yloxy)benzamide | |
| 4-(4-{[2-(4-chlorophenyl)-4,4-dimethylcyclohex-1-en-1-yl]methyl}piperazin-1-yl)-N-[(6-{[(cis-4-hydroxy-4-methylcyclohexyl)methyl]amino}-5-nitropyridin-3-yl)sulfonyl]-2-(1H-pyrrolo[2,3-b]pyridin-5-yloxy)benzamide | 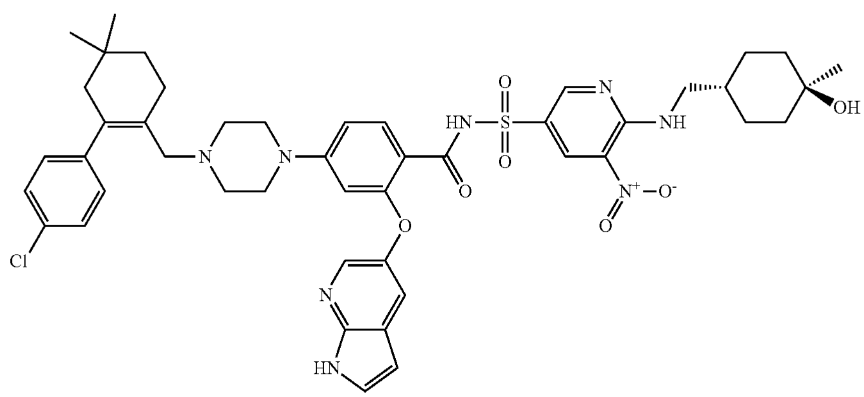 [SMILES: CC1(C)CCC(CN2CCN(c3ccc(C(=O)NS(=O)(=O)c4cnc(NC[C@H]5CC[C@](C)(O)CC5)c([N+](=O)[O-])c4)c(Oc4cnc5[nH]ccc5c4)c3)CC2)=C(c2ccc(Cl)cc2)C1] |
| 4-(4-{[2-(4-chlorophenyl)-5-methoxy-5-methylcyclohex-1-en-1-yl]methyl}piperazin-1-yl)-N-[(4-{[(trans-4-hydroxy-4-methylcyclohexyl)methyl]amino}-3-nitrophenyl)sulfonyl]-2-(1H-pyrrolo[2,3-b]pyridin-5-yloxy)benzamide | 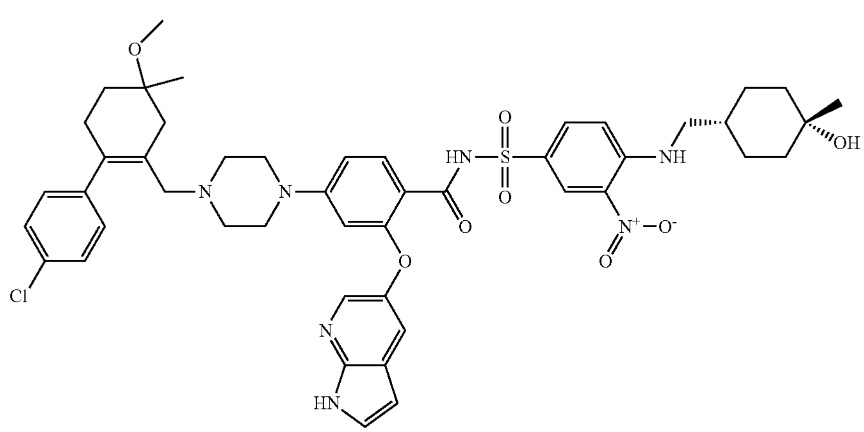 [SMILES: COC1(C)CCC(c2ccc(Cl)cc2)=C(CN2CCN(c3ccc(C(=O)NS(=O)(=O)c4ccc(NC[C@H]5CC[C@@](C)(O)CC5)c([N+](=O)[O-])c4)c(Oc4cnc5[nH]ccc5c4)c3)CC2)C1] |

-continued

| Name | Structure |
|---|---|
| 4-(4-{[2-(4-chlorophenyl)-5-methoxy-5-methylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide | 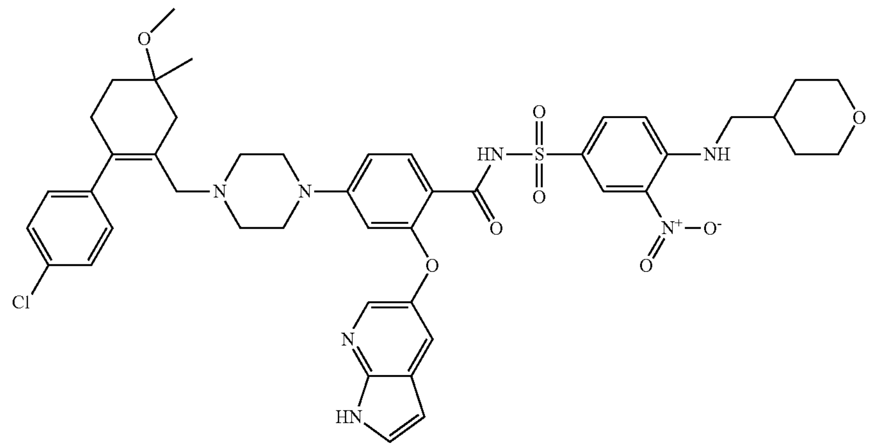 [SMILES: COC1(C)CCC(c2ccc(Cl)cc2)=C(CN2CCN(c3ccc(C(=O)NS(=O)(=O)c4ccc(NCC5CCOCC5)c([N+](=O)[O-])c4)c(Oc4cnc5[nH]ccc5c4)c3)CC2)C1] |

In some embodiments, the compound is selected from the group consisting of:

| Name | Structure |
|---|---|
| {5-[5-(4-{[2-(4-chlorophenyl)-4,4-dimethylcyclohex-1-en-1-yl]methyl}piperazin-1-yl)-2-{[(4-{[(trans-4-methoxycyclohexyl)methyl]amino}-3-nitrophenyl)sulfonyl]carbamoyl}phenoxy]-7H-pyrrolo[2,3-b]pyridin-7-yl}methyl dihydrogen phosphate | |
| (5-{5-(4-{[2-(4-chlorophenyl)-4,4-dimethylcyclohex-1-en-1-yl]methyl}piperazin-1-yl)-2-[({3-nitro-4-[tetrahydro-2H-pyran-4-ylmethyl)amino]phenyl}sulfonyl)carbamoyl]phenoxy}-7H-pyrrolo[2,3-b]pyridin-7-yl)methyl dihydrogen phosphate | |

-continued

| Name | Structure |
|---|---|
| (5-{5-(4-{[2-(4-chlorophenyl)-4,4-dimethylcyclohex-1-en-1-yl]methyl}piperazin-1-yl)-2-[({4-[(4-fluorotetrahydro-2H-pyran-4-yl)methoxy]-3-nitrophenyl}sulfonyl)carbamoyl]phenoxy}-7H-pyrrolo[2,3-b]pyridin-7-yl)methyl dihydrogen phosphate | |
| 3-[(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)amino]-2,2-dimethylpropyl dihydrogen phosphate | |
| trans-4-[(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenoxy)methyl]cyclohexyl dihydrogen phosphate | |

-continued

| Name | Structure |
|---|---|
| 4-(4-{[2-(4-chloro-phenyl)-4,4-dimethyl-cyclohex-1-en-1-yl]methyl}piperazin-1-yl)-N-({4-[(3-hydroxy-2,2-dimethylpropyl)amino]-3-nitrophenyl}sulfonyl)-2-(1H-pyrrolo[2,3-b]pyridin-5-yloxy)benzamide | 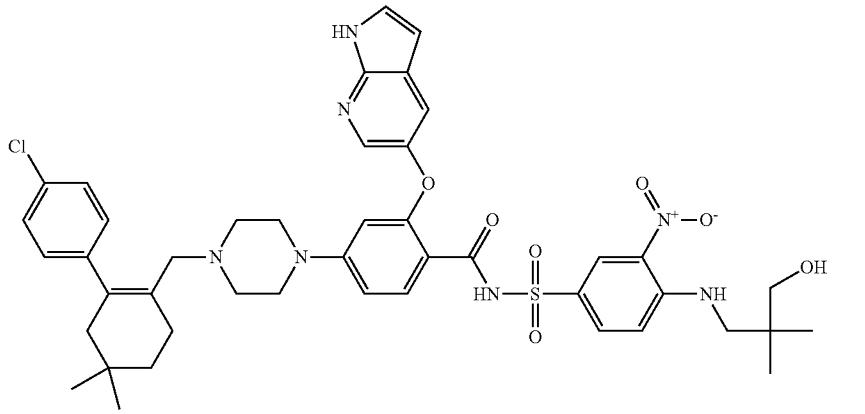 [SMILES: CC(C)(CO)CNc1ccc(S(=O)(=O)NC(=O)c2ccc(N3CCN(CC4=C(c5ccc(Cl)cc5)CC(C)(C)CC4)CC3)cc2Oc2cnc3[nH]ccc3c2)cc1[N+](=O)[O-]] |
| Trans-4-(4-{[2-(4-chloro-phenyl)-4,4-dimethyl-cyclohex-1-en-1-yl]methyl}piperazin-1-yl)-N-({4-[(4-hydroxy-cyclohexyl)methoxy]-3-nitrophenyl}sulfonyl)-2-(1H-pyrrolo[2,3-b]pyridin-5-yloxy)benzamide | 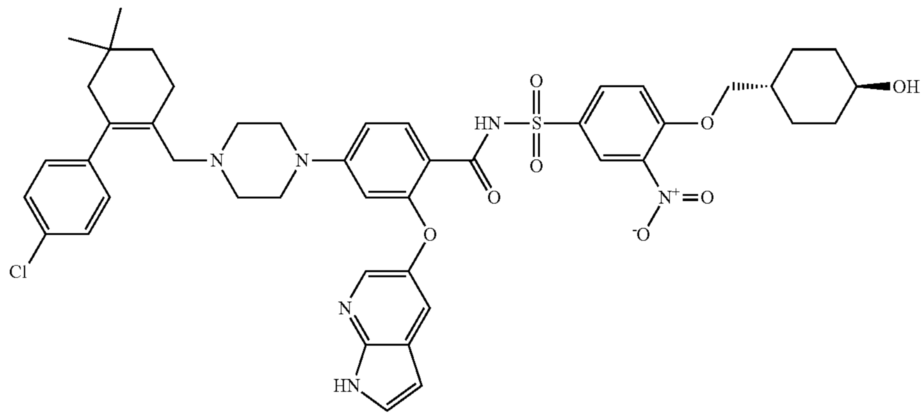 |

In some embodiments, the compound is selected from the group consisting of:

| Name | Structure |
|---|---|
| 4-{4-[(4'-chlorobiphenyl-2-yl)methyl]piperazin-1-yl}-N-[(3-nitro-4-{[(1R,2R,3R,5S)-2,6,6-trimethylbicyclo[3.1.1]hept-3-yl]amino}phenyl)sulfonyl]benzamide | 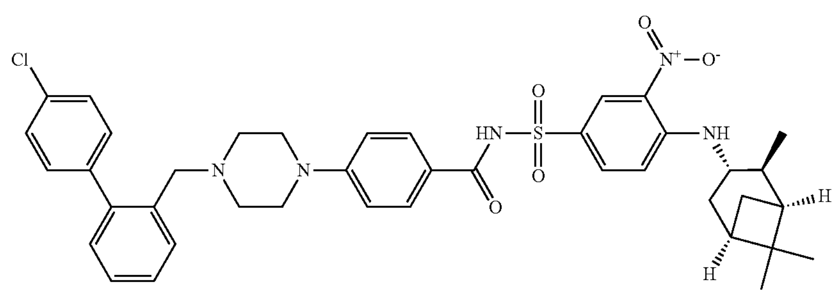 [SMILES: C[C@@H]1[C@@H](Nc2ccc(S(=O)(=O)NC(=O)c3ccc(N4CCN(Cc5ccccc5-c5ccc(Cl)cc5)CC4)cc3)cc2[N+](=O)[O-])C[C@H]2C[C@@H]1C2(C)C] |
| 4-(4-{acetyl[(1S,2S,3S,5R)-2,6,6-trimethyl-bicyclo[3.1.1]hept-3-yl]amino}piperidin-1-yl)-N-({4-[(cyclohexyl-methyl)amino]-3-nitrophenyl}sulfonyl)benzamide | 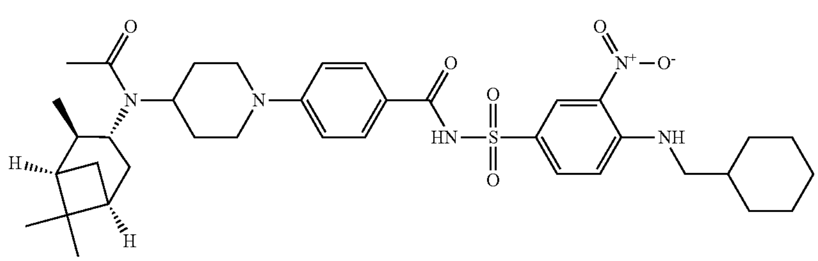 [SMILES: CC(=O)N(C1CCN(c2ccc(C(=O)NS(=O)(=O)c3ccc(NCC4CCCCC4)c([N+](=O)[O-])c3)cc2)CC1)[C@@H]1C[C@@H]2C[C@H]([C@H]1C)C2(C)C] |

-continued

| Name | Structure |
|---|---|
| 4-(4-{benzoyl[(1S,2S,3S,5R)-2,6,6-trimethylbicyclo[3.1.1]hept-3-yl]amino}piperidin-1-yl)-N-({4-[(cyclohexylmethyl)amino]-3-nitrophenyl}sulfonyl)benzamide | 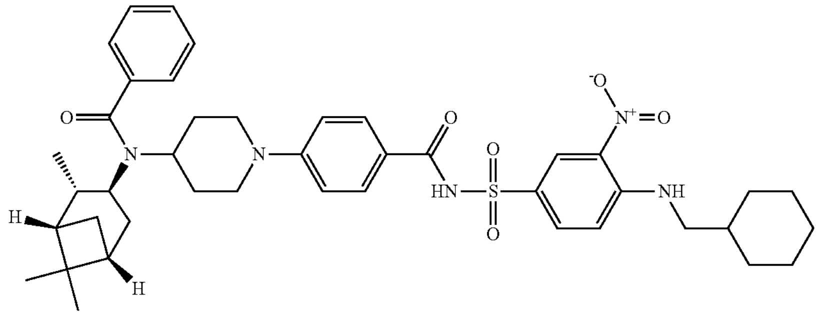 |
| N-({4-[(cyclohexylmethyl)amino]-3-nitrophenyl}sulfonyl)-3'-{[(1S,2S,3S,5R)-2,6,6-trimethylbicyclo[3.1.1]hept-3-yl]amino}biphenyl-4-carboxamide | 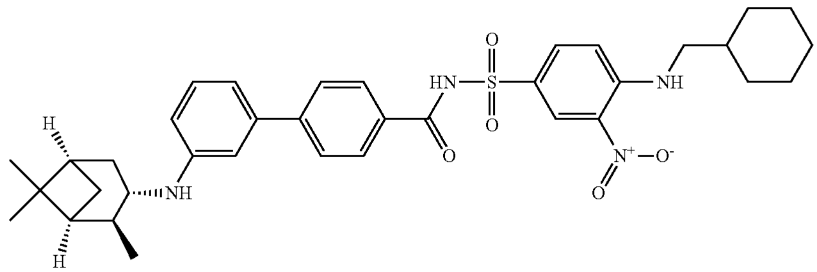 [SMILES: C[C@@H]1[C@@H](Nc2cccc(-c3ccc(C(=O)NS(=O)(=O)c4ccc(NCC5CCCCC5)c([N+](=O)[O-])c4)cc3)c2)C[C@H]2C[C@@H]1C2(C)C] |
| N-({4-[(cyclohexylmethyl)amino]-3-nitrophenyl}sulfonyl)-4-(4-{(phenylacetyl)[(1S,2S,3S,5R)-2,6,6-trimethylbicyclo[3.1.1]hept-3-yl]amino}piperidin-1-yl)benzamide | 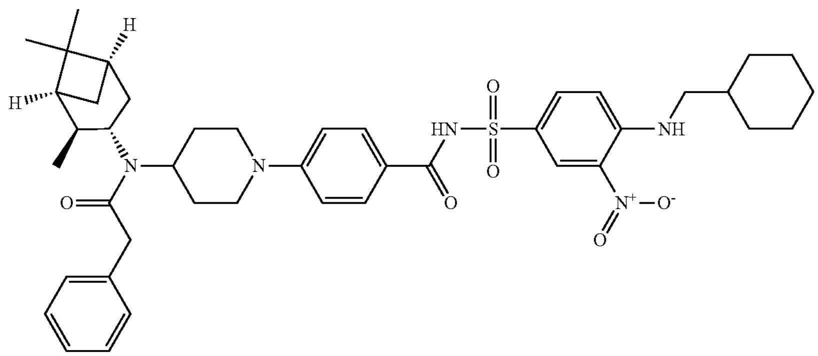 [SMILES: C[C@@H]1[C@@H](N(C(=O)Cc2ccccc2)C2CCN(c3ccc(C(=O)NS(=O)(=O)c4ccc(NCC5CCCCC5)c([N+](=O)[O-])c4)cc3)CC2)C[C@H]2C[C@@H]1C2(C)C] |
| N-({4-[(cyclohexylmethyl)amino]-3-nitrophenyl}sulfonyl)-4'-{[(1S,2S,3S,5R)-2,6,6-trimethylbicyclo[3.1.1]hept-3-yl]amino}biphenyl-4-carboxamide | 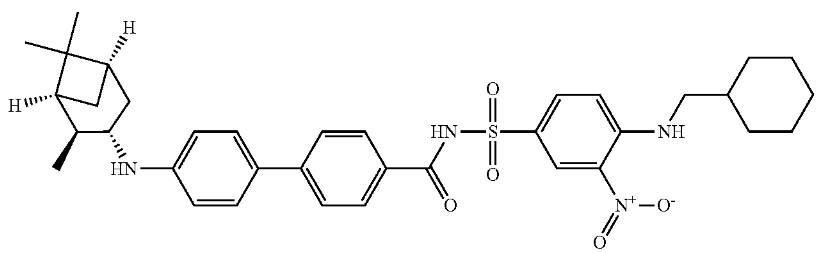 [SMILES: C[C@@H]1[C@@H](Nc2ccc(-c3ccc(C(=O)NS(=O)(=O)c4ccc(NCC5CCCCC5)c([N+](=O)[O-])c4)cc3)cc2)C[C@H]2C[C@@H]1C2(C)C] |
| N-({4-[(cyclohexylmethyl)amino]-3-nitrophenyl}sulfonyl)-4'-{(3-phenylpropyl)[(1S,2S,3S,5R)-2,6,6-trimethylbicyclo[3.1.1]hept-3-yl]amino}biphenyl-4-carboxamide | 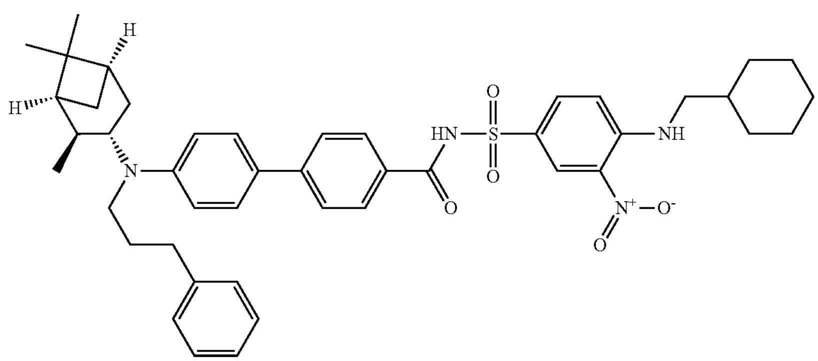 [SMILES: C[C@@H]1[C@@H](N(CCCc2ccccc2)c2ccc(-c3ccc(C(=O)NS(=O)(=O)c4ccc(NCC5CCCCC5)c([N+](=O)[O-])c4)cc3)cc2)C[C@H]2C[C@@H]1C2(C)C] |

-continued

| Name | Structure |
|---|---|
| 4-{6-[adamantan-1-ylmethyl]-2,6-diazabicyclo[3.2.1]oct-2-yl}-N-({4-[(cyclohexylmethyl)amino]-3-nitrophenylsulfonyl)benzamide | 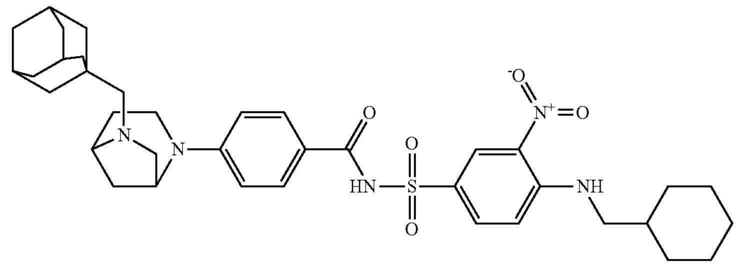 |
| N-[(4-{[(2R)-4-(morpholin-4-yl)-1-(phenylthio)butan-2-yl]amino}-3-[(trifluoromethyl)sulfonyl]phenyl)sulfonyl]-4-(4-{(3-phenylpropanoyl)[(1S,2S,3S,5R)-2,6,6-trimethylbicyclo[3.1.1]hept-3-yl]amino}piperidin-1-yl)benzamide | 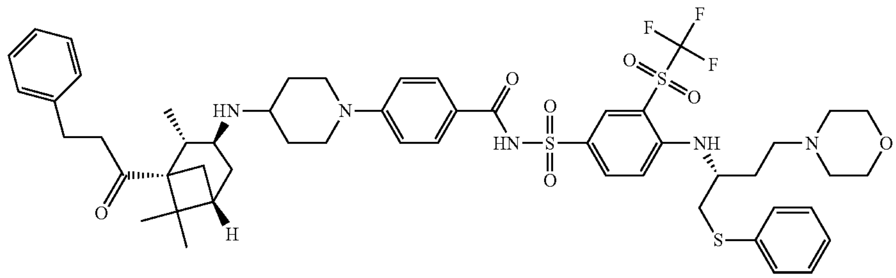 [SMILES: C[C@@H]1[C@@H](NC2CCN(c3ccc(C(=O)NS(=O)(=O)c4ccc(N[C@H](CCN5CCOCC5)CSc5ccccc5)c(S(=O)(=O)C(F)(F)F)c4)cc3)CC2)C[C@H]2C[C@@]1(C(=O)CCc1ccccc1)C2(C)C] |
| 4-{4-[adamantan-1-ylmethyl]piperazin-1-yl}-N-[(4-{[(2R)-4-(morpholin-4-yl)-1-(phenylthio)butan-2-yl]amino}-3-nitrophenyl)sulfonyl]benzamide | 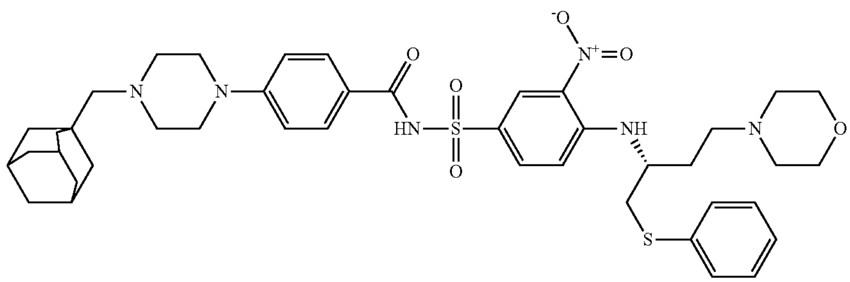 |
| 4-{(1S,4S)-5-[adamantan-1-ylmethyl]-2,5-diazabicyclo[2.2.1]hept-2-yl}-N-({4-[(cyclohexylmethyl)amino]-3-nitrophenyl}sulfonyl)benzamide | 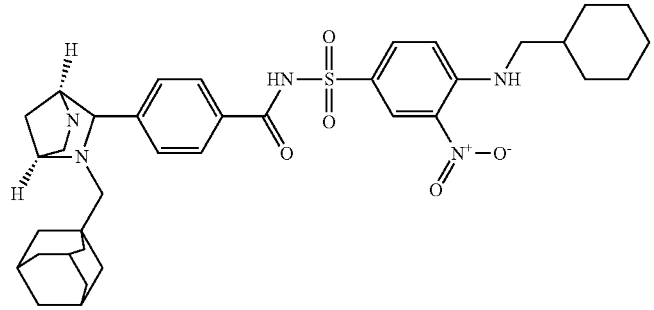 [SMILES: O=C(NS(=O)(=O)c1ccc(NCC2CCCCC2)c([N+](=O)[O-])c1)c1ccc(C2[C@@H]3C[C@@H](CN3)N2CC23CC4CC(CC(C4)C2)C3)cc1] |
| 4-(4-{[3-bromo-5-methyladamantan-1-yl]methyl}piperazin-1-yl)-N-({4-[(cyclohexylmethyl)amino]-3-nitrophenyl}sulfonyl)benzamide | 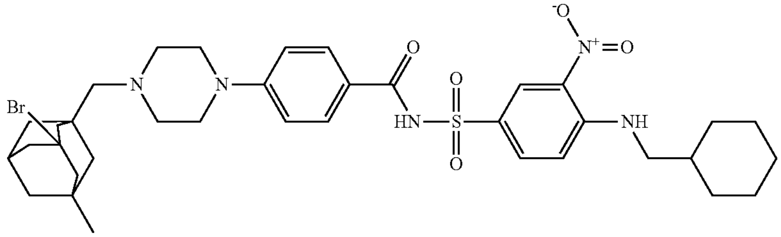 |

| Name | Structure |
|---|---|
| N-({4-[(cyclohexyl-methyl)amino]-3-nitrophenyl}sulfonyl)-4-(4-{[3,5-dimethyladamantan-1-yl]methyl]piperazin-1-yl)benzamide | 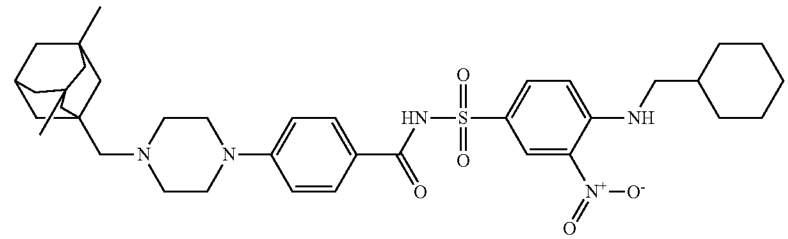 [SMILES: CC12CC3CC(C)(C1)CC(CN1CCN(c4ccc(C(=O)NS(=O)(=O)c5ccc(NCC6CCCCC6)c([N+](=O)[O-])c5)cc4)CC1)(C3)C2] |
| 4-{4-[(4'-chlorobiphenyl-2-yl)methyl]piperazin-1-yl}-N-{[4-(1-methyl-2-oxo-3-azabicyclo[3.1.1]hept-3-yl)phenyl]sulfonyl}benzamide | |
| N-({3-nitro-4-[(tetra-hydro-2H-pyran-4-ylmethyl)amino]phenyl}sulfonyl)-4-(4-{2-[(1R,4R)-1,7,7-trimethylbicyclo[2.2.1]hept-2-en-2-yl]benzyl}piperazin-1-yl)benzamide | 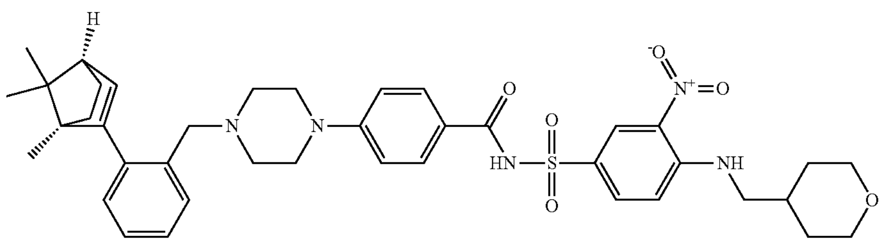 |
| N-({3-nitro-4-[(tetra-hydro-2H-pyran-4-ylmethyl)amino]phenyl}sulfonyl)-4-(4-{2-octahydro-1H-4,7-methanoinden-5-ylamino]benzyl}piperazin-1-yl)benzamide | |
| N-({3-nitro-4-[(tetra-hydro-2H-pyran-4-ylmethyl)amino]phenyl}sulfonyl)-4-(4-(2-{[(1R,4R,6S)-5,5,6-trimethylbicyclo[2.2.1]hept-2-yl]amino}benzyl)piperazin-1-yl]benzamide | 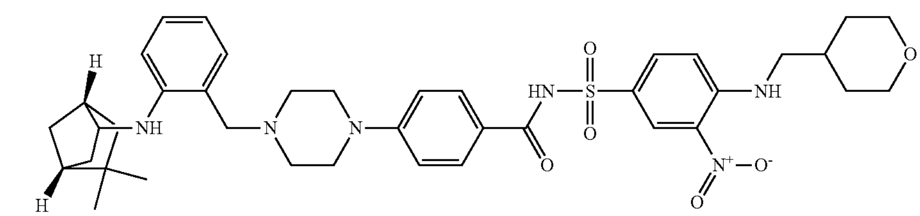 [SMILES: CC1(C)C[C@H]2C[C@@H]1CC2Nc1ccccc1CN1CCN(c2ccc(C(=O)NS(=O)(=O)c3ccc(NCC4CCOCC4)c([N+](=O)[O-])c3)cc2)CC1] |
| 4-[4-(2-{[(1R,5S)-6,6-dimethylbicyclo[3.1.1]hept-2-yl]amino}benzyl)piperazin-1-yl]-N-({3-nitro-4-[(tetra-hydro-2H-pyran-4-ylmethyl)amino]phenyl}sulfonyl)benzamide | 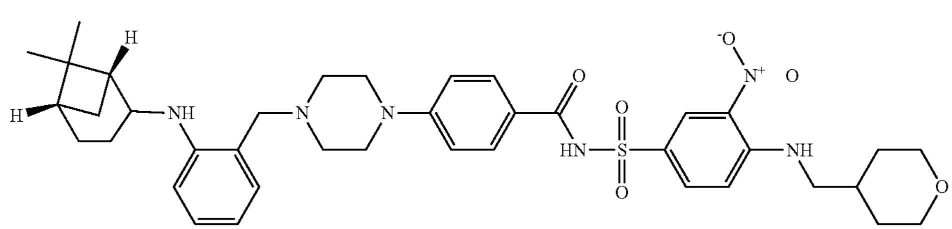 |

| Name | Structure |
|---|---|
| 4-(4-{[(1R,5R)-2-(4-chlorophenyl)-6,6-dimethylbicyclo[3.1.1]hept-2-en-3-yl]methyl}piperazin-1-yl)-N-({4-[(cyclohexylmethyl)amino]-3-nitrophenyl}sulfonyl)benzamide | 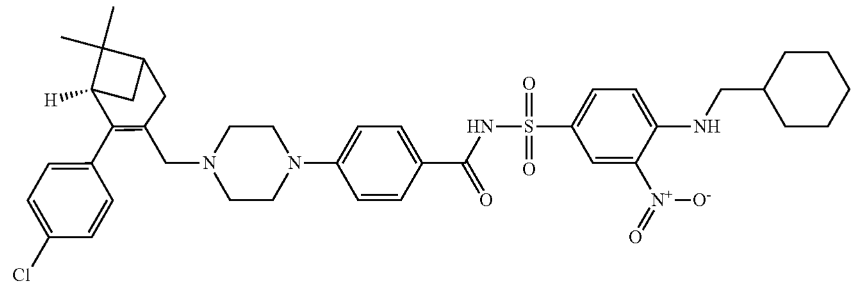 [SMILES: CC1(C)C2CC(CN3CCN(c4ccc(C(=O)NS(=O)(=O)c5ccc(NCC6CCCCC6)c([N+](=O)[O-])c5)cc4)CC3)=C(c3ccc(Cl)cc3)[C@@H]1C2] |
| 4-{4-[2-{[adamantan-2-ylmethyl]amino}-5,5-dimethylcyclohexyl)methyl]piperazin-1-yl}-N-({3-nitro-4-[(tetrahydro-2H-pyran-4-ylmethyl)amino]phenyl}sulfonyl)benzamide | 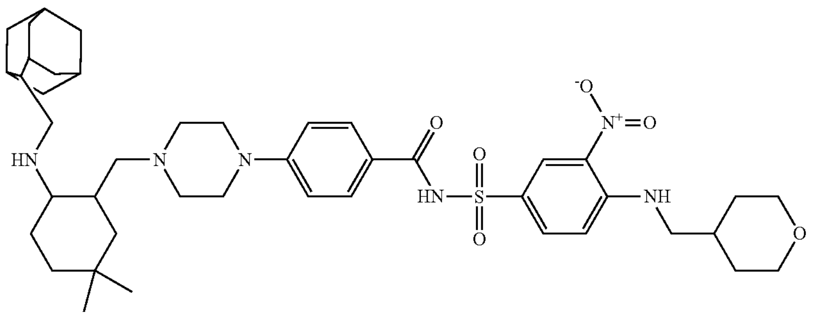 |
| 4-{4-[(5,5-dimethyl-2-{[(1R,2S,3S,5S)-2,6,6-trimethylbicyclo[3.1.1]hept-3-yl]amino}cyclohexyl)methyl]piperazin-1-yl}-N-({3-nitro-4-[(tetrahydro-2H-pyran-4-ylmethyl)amino]phenyl}sulfonyl)benzamide | 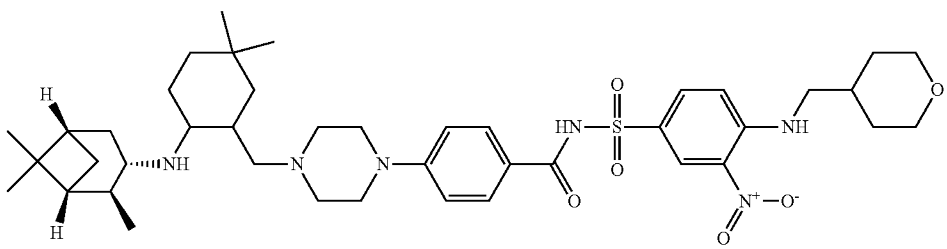 [SMILES: C[C@@H]1[C@@H](NC2CCC(C)(C)CC2CN2CCN(c3ccc(C(=O)NS(=O)(=O)c4ccc(NCC5CCOCC5)c([N+](=O)[O-])c4)cc3)CC2)C[C@@H]2C[C@H]1C2(C)C] |
| 4-{4-[2-(3-azabicyclo[3.2.2]non-3-yl)-5-nitrobenzyl]piperazin-1-yl}-N-({3-nitro-4-[(tetrahydro-2H-pyran-4-ylmethyl)amino]phenyl}sulfonyl)benzamide | 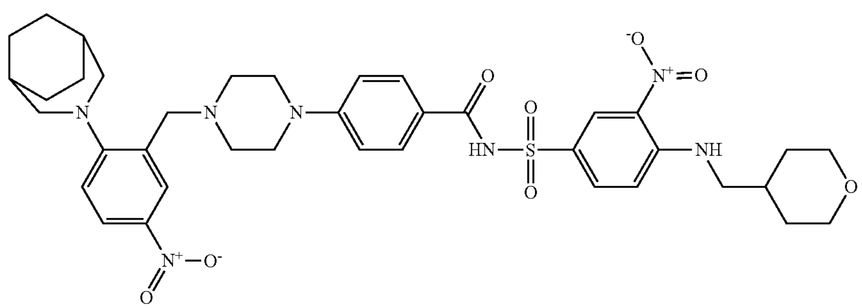 |
| 4-(4-{2-[2,3,3a,4,7,7a-hexahydro-1H-4,7-methanoinden-5-yl]benzyl}piperazin-1-yl)-N-({3-nitro-4-[(tetrahydro-2H-pyran-4-ylmethyl)amino]phenyl}sulfonyl)benzamide | 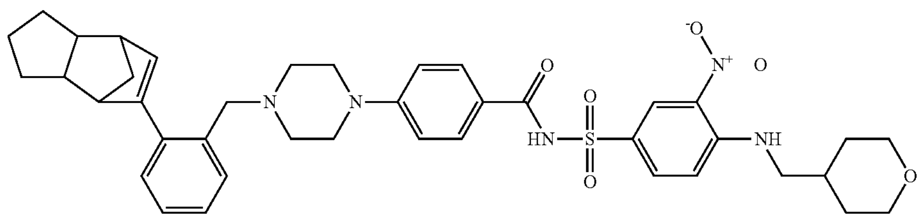 |

-continued

| Name | Structure |
|---|---|
| 1-[adamantan-1-yl]-4-{2-[(4-{4-[({3-nitro-4-[(tetrahydro-2H-pyran-4-ylmethyl)amino]phenyl}sulfonyl)carbamoyl]phenyl}piperazin-1-yl)methyl]phenyl}-N,N-diphenyl-1H-pyrazole-3-carboxamide | 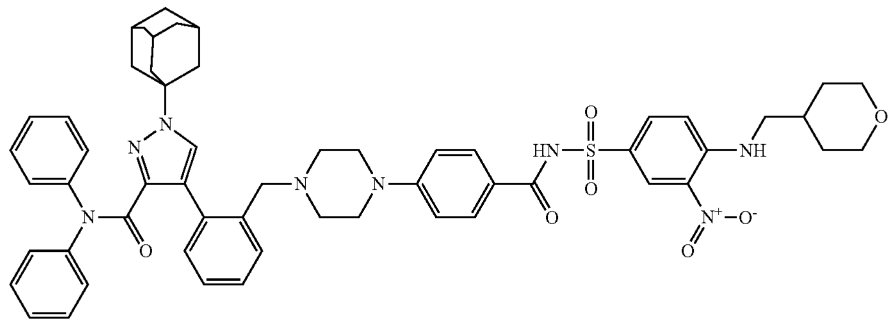 [SMILES: O=C(NS(=O)(=O)c1ccc(NCC2CCOCC2)c([N+](=O)[O-])c1)c1ccc(N2CCN(Cc3ccccc3-c3cn(C45CC6CC(CC(C6)C4)C5)nc3C(=O)N(c3ccccc3)c3ccccc3)CC2)cc1] |
| 4-(4-{2-[2-(adamantan-1-yl)-6-methylimidazo[1,2-a]pyridin-8-yl]benzyl}piperazin-1-yl)-N-({3-nitro-4-[(tetrahydro-2H-pyran-4-ylmethyl)amino]phenyl}sulfonyl)benzamide | 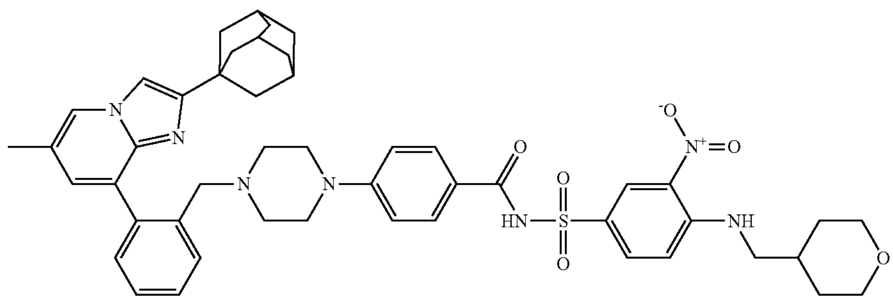 |
| N-(adamantan-2-yl)-6-methyl-8-{2-[(4-{4-[({3-nitro-4-[(tetrahydro-2H-pyran-4-ylmethyl)amino]phenyl}sulfonyl)carbamoyl]phenyl}piperazin-1-yl)methyl]phenyl}imidazo[1,2-a]pyridine-2-carboxamide | 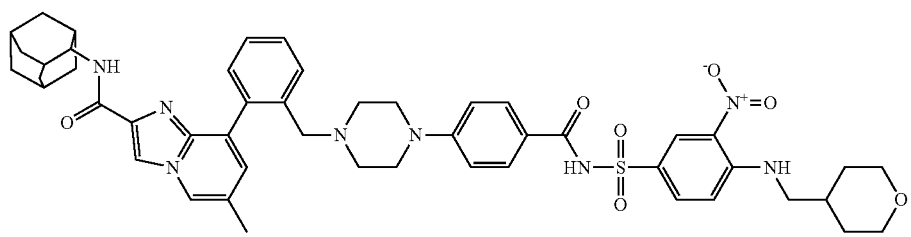 |
| 4-(4-{2-[(1R,5S)-6,6-dimethylbicyclo[3.1.1]hept-2-en-2-yl]benzyl]piperazin-1-yl)-N-({3-nitro-4-[(tetrahydro-2H-pyran-4-ylmethyl)amino]phenyl}sulfonyl)benzamide | |
| N-({3-nitro-4-[(tetrahydro-2H-pyran-4-ylmethyl)amino]phenyl}sulfonyl)-4-(4-{2-[5,5,6-trimethylbicyclo[2.2.1]hept-2-en-2-yl]benzyl}piperazin-1-yl)benzamide | 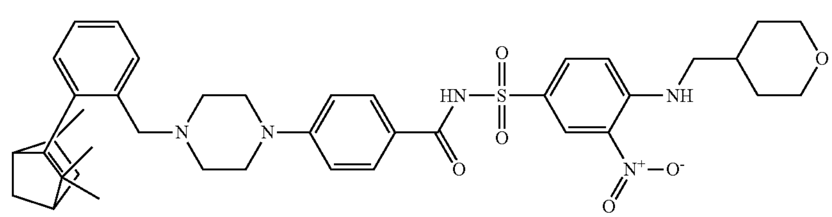 |
| N-cyclooctyl-5-{2-[(4-{4-[({3-nitro-4-[(tetrahydro-2H-pyran-4-ylmethyl)amino]phenyl}sulfonyl)carbamoyl]phenyl}piperazin-1-yl)methyl]phenyl}-2-furamide | 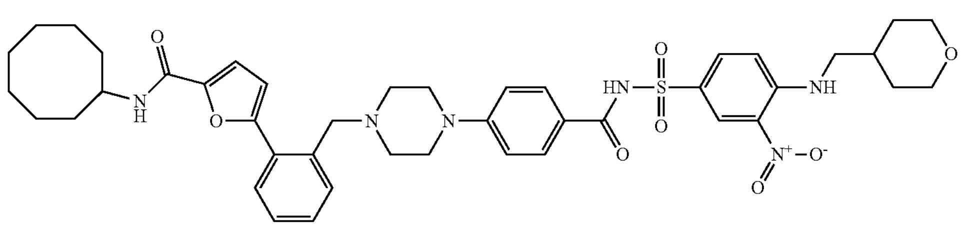 [SMILES: O=C(NS(=O)(=O)c1ccc(NCC2CCOCC2)c([N+](=O)[O-])c1)c1ccc(N2CCN(Cc3ccccc3-c3ccc(C(=O)NC4CCCCCCC4)o3)CC2)cc1] |

-continued

| Name | Structure |
|---|---|
| N-benzyl-7,7-dimethyl-2-{2-[(4-{4-[({3-nitro-4-[(tetrahydro-2H-pyran-4-ylmethyl)amino]phenyl}sulfonyl)carbamoyl]phenyl}piperazin-1-yl)methyl]phenyl}bicyclo[2.2.1]hept-2-ene-1-carboxamide | 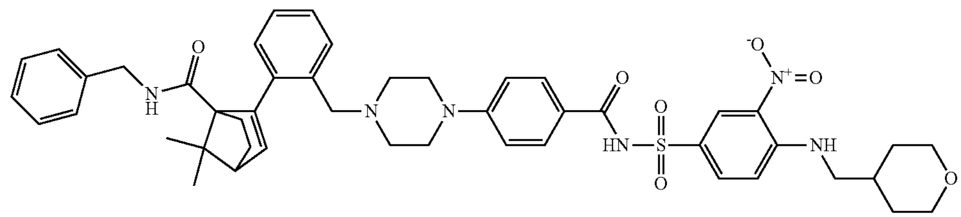 |
| 4-[4-(2-{[(1R,5S)-8-methyl-8-azabicyclo[3.2.1]oct-3-yl]amino}benzyl)piperazin-1-yl]-N-({3-nitro-4-[(tetrahydro-2H-pyran-4-ylmethyl)amino]phenyl}sulfonyl)benzamide | 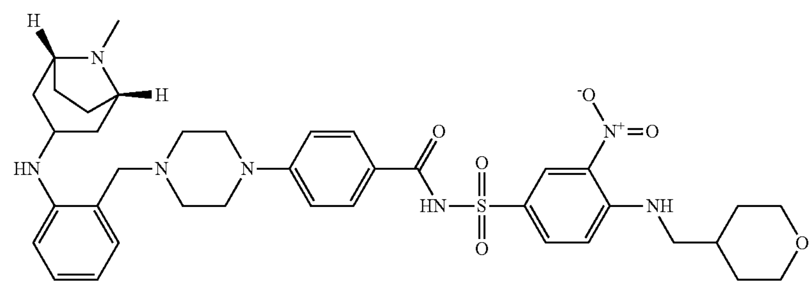 |
| N-({3-nitro-4-[(tetrahydro-2H-pyran-4-ylmethyl)amino]phenyl}sulfonyl)-4-[4-(2-{[(1R,2S,3S,5S)-2,6,6-trimethylbicyclo[3.1.1]hept-3-yl]amino}benzyl)piperazin-1-yl]benzamide | 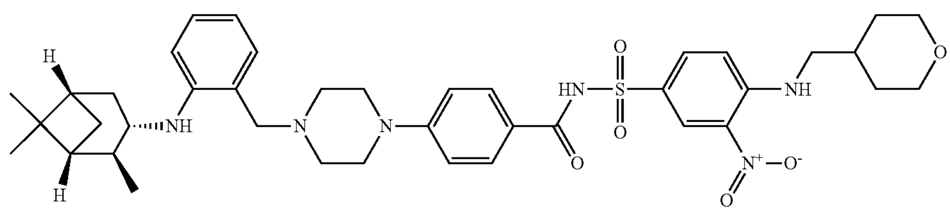 [SMILES: C[C@@H]1[C@@H](Nc2ccccc2CN2CCN(c3ccc(C(=O)NS(=O)(=O)c4ccc(NCC5CCOCC5)c([N+](=O)[O-])c4)cc3)CC2)C[C@@H]2C[C@H]1C2(C)C] |
| 4-(4-{2-[3-azabicyclo[3.2.2]non-3-yl]benzyl}piperazin-1-yl)-N-({3-nitro-4-[(tetrahydro-2H-pyran-4-ylmethyl)amino]phenyl}sulfonyl)benzamide | 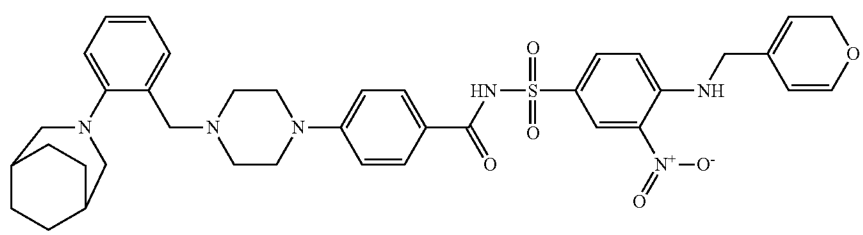 [SMILES: O=C(NS(=O)(=O)c1ccc(NCC2=CCOC=C2)c([N+](=O)[O-])c1)c1ccc(N2CCN(Cc3ccccc3N3CC4CCC(CC4)C3)CC2)cc1] |
| N-({3-nitro-4-[(tetrahydro-2H-pyran-4-ylmethyl)amino]phenyl}sulfonyl)-4-(4-{2-[tricyclo[4.3.1.1³,⁸]undec-4-en-4-yl]benzyl}piperazin-1-yl)benzamide | |
| 7,7-dimethyl-2-{2-[(4-{4-[({3-nitro-4-[(tetrahydro-2H-pyran-4-ylmethyl)amino]phenyl}sulfonyl)carbamoyl]phenyl]piperazin-1-yl)methyl]phenyl}-N-phenylbicyclo[2.2.1]hept-2-ene-1-carboxamide | 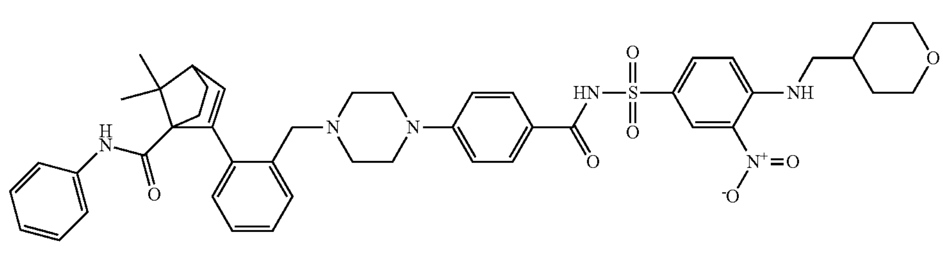 |

-continued

| Name | Structure |
|---|---|
| 7,7-dimethyl-2-{2-[(4-{4-[({3-nitro-4-[(tetrahydro-2H-pyran-4-ylmethyl)amino]phenyl}sulfonyl)carbamoyl]phenyl}piperazin-1-yl)methyl]phenyl}-N-[(1S,2S,3S,5R)-2,6,6-trimethylbicyclo[3.1.1]hept-3-yl]bicyclo[2.2.1]hept-2-ene-1-carboxamide | 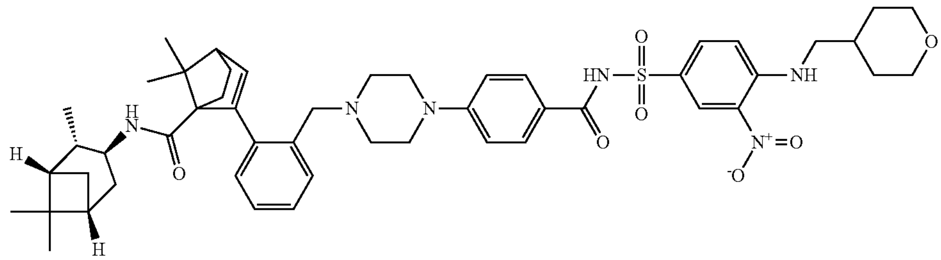 |
| N-(adamantan-1-ylmethyl)-7,7-dimethyl-2-{2-[(4-{4-[({3-nitro-4-[(tetrahydro-2H-pyran-4-ylmethyl)amino]phenyl}sulfonyl)carbamoyl]phenyl}piperazin-1-yl)methyl]phenyl}bicyclo[2.2.1]hept-2-ene-1-carboxamide | 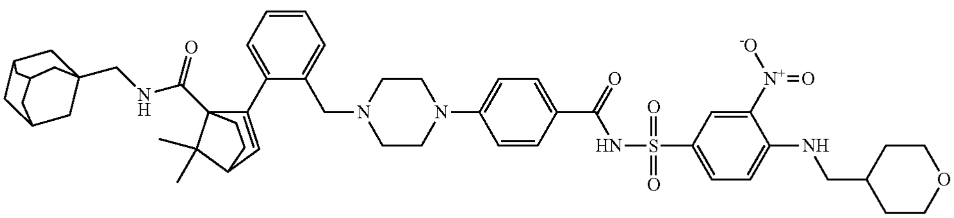 |
| N-cyclopropyl-7,7-dimethyl-2-{2-[(4-{4-[({3-nitro-4-[(tetrahydro-2H-pyran-4-ylmethyl)amino]phenyl}sulfonyl)carbamoyl]phenyl}piperazin-1-yl)methyl]phenyl}bicyclo[2.2.1]hept-2-ene-1-carboxamide | 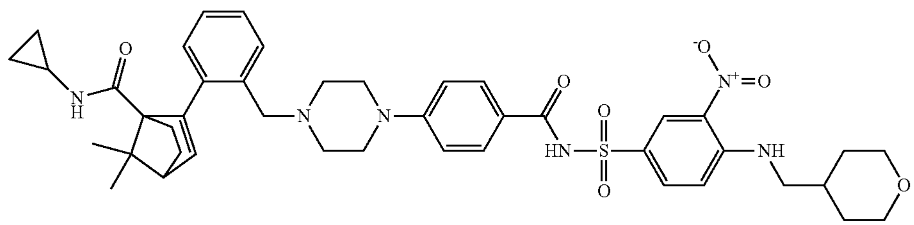 |
| 7,7-dimethyl-2-{2-[(4-{4-[({3-nitro-4-[(tetrahydro-2H-pyran-4-ylmethyl)amino]phenyl}sulfonyl)carbamoyl]phenyl}piperazin-1-yl)methyl]phenyl}bicyclo[2.2.1]hept-2-ene-1-carboxylic acid | 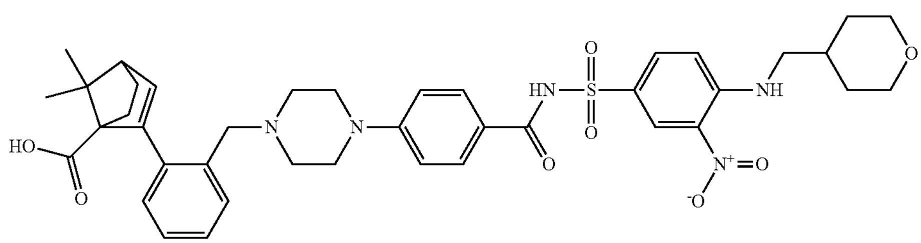 |
| 4-[4-(2-{5-[8-azabicyclo[3.2.1]oct-8-ylmethyl]-2-thienyl}benzyl)piperazin-1-yl]-N-({3-nitro-4-[(tetrahydro-2H-pyran-4-ylmethyl)amino]phenyl}sulfonyl)benzamide | 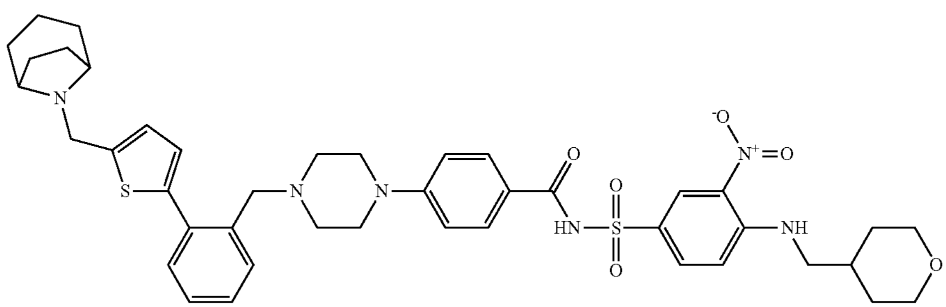 |
| 4-{4-[adamantan-1-ylcarbonyl]piperazin-1-yl}-N-{[3-nitro-4-(tetrahydro-2H-pyran-4-ylamino)phenyl]sulfonyl}benzamide | 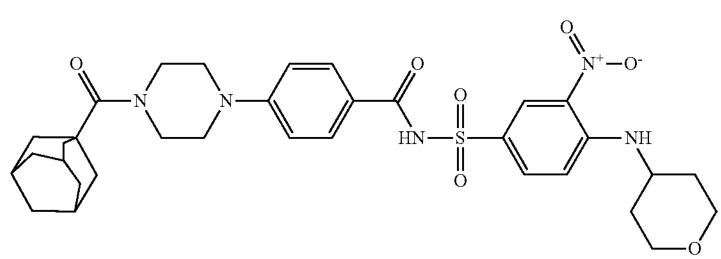 [SMILES: O=C(NS(=O)(=O)c1ccc(NC2CCOCC2)c([N+](=O)[O-])c1)c1ccc(N2CCN(C(=O)C34CC5CC(CC(C5)C3)C4)CC2)cc1] |

| Name | Structure |
|---|---|
| 4-{4-[adamantan-2-ylcarbonyl]piperazin-1-yl}-n-{[3-nitro-4-(tetrahydro-2h-pyran-4-ylamino)phenyl]sulfonyl}benzamide | 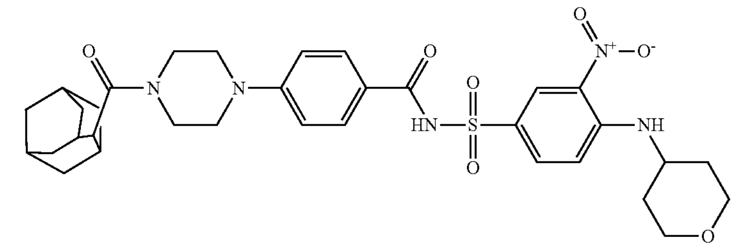 [SMILES: O=C(NS(=O)(=O)c1ccc(NC2CCOCC2)c([N+](=O)[O-])c1)c1ccc(N2CCN(C(=O)C3C4CC5CC(C4)CC3C5)CC2)cc1] |
| 4-{5-[adamantan-1-ylcarbonyl]-2,5-diazabicyclo[2.2.1]hept-2-yl}-N-{[3-nitro-4-(tetrahydro-2H-pyran-4-ylamino)phenyl]sulfonyl}benzamide | 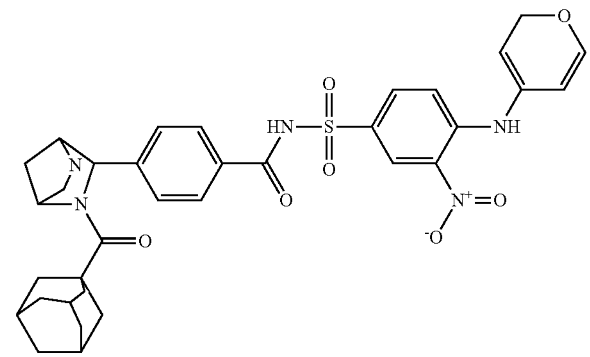 |
| 4-{(1S,5S)-3-[adamantan-1-ylcarbonyl]-3,6-diazabicyclo[3.2.0]hept-6-yl}-N-{[3-nitro-4-(tetrahydro-2H-pyran-4-ylamino)phenyl]sulfonyl}benzamide | 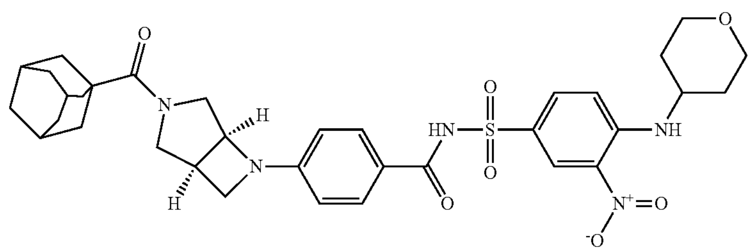 |
| N-{[3-nitro-4-(tetrahydro-2H-pyran-4-ylamino)phenyl]sulfonyl}-4-(4-{(3-phenylpropyl)[(1S,2S,3S,5R)-2,6,6-trimethylbicyclo[3.1.1]hept-3-yl]amino}piperidin-1-yl)benzamide | 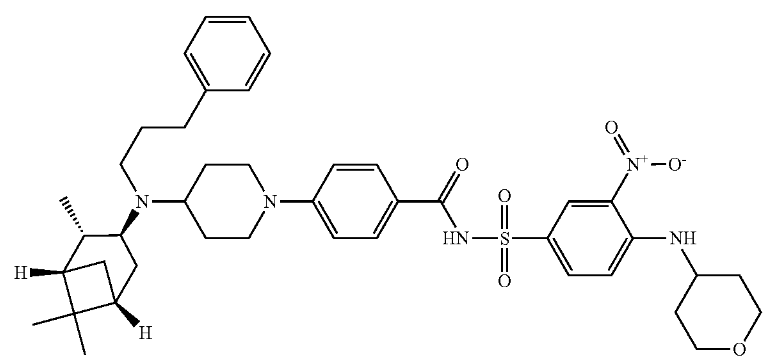 [SMILES: C[C@@H]1[C@@H](N(CCCc2ccccc2)C2CCN(c3ccc(C(=O)NS(=O)(=O)c4ccc(NC5CCOCC5)c([N+](=O)[O-])c4)cc3)CC2)C[C@H]2C[C@@H]1C2(C)C] |
| N-({4-[(cyclohexylmethyl)amino]-3-nitrophenyl}sulfonyl)-4-(4-{(3-phenylpropanoyl)[(1S,2S,3S,5R)-2,6,6-trimethylbicyclo[3.1.1]hept-3-yl]amino}piperidin-1-yl)benzamide | 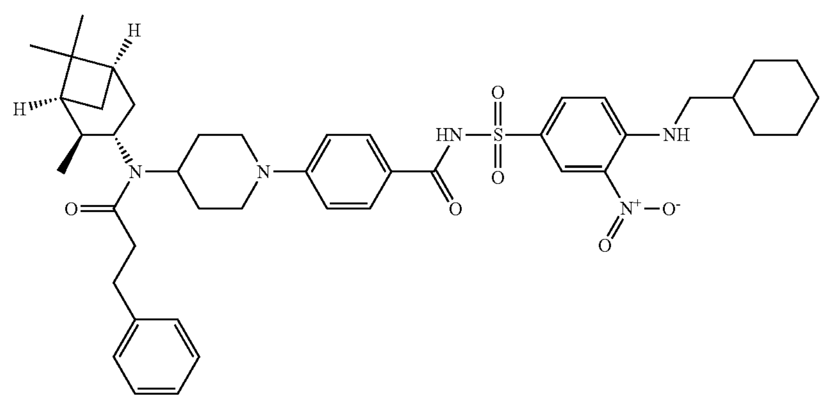 [SMILES: C[C@@H]1[C@@H](N(C(=O)CCc2ccccc2)C2CCN(c3ccc(C(=O)NS(=O)(=O)c4ccc(NCC5CCCCC5)c([N+](=O)[O-])c4)cc3)CC2)C[C@H]2C[C@@H]1C2(C)C] |

| Name | Structure |
|---|---|
| 4-{4-[adamantan-1-ylmethyl]piperazin-1-yl}-n-({4-[(cyclohexylmethyl)amino]-3-nitrophenyl}sulfonyl)benzamide | 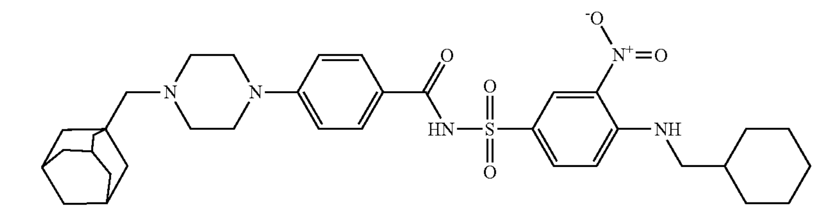 |
| 6-{3-[adamantan-1-yl]-4-hydroxyphenyl}-N-({4-[(cyclohexyl-methyl)amino]-3-nitrophenyl}sulfonyl)-2-naphthamide | 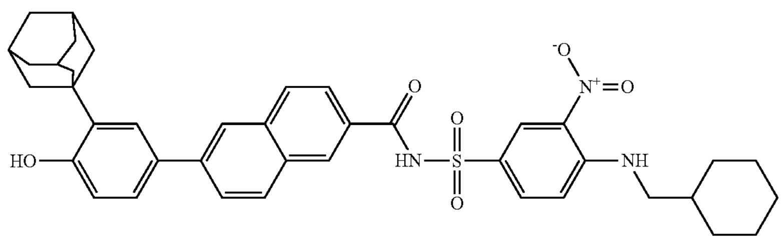 |
| 4-(4-{2-[adamantan-1-yl]-2-oxoethyl}piperazin-1-yl)-N-({4-[(cyclohexyl-methyl)amino]-3-nitrophenyl}sulfonyl)benzamide | 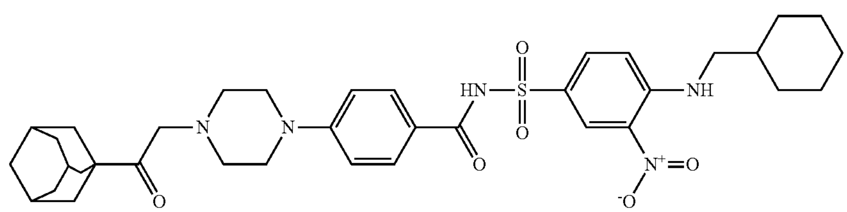 |
| 4-{[adamantan-2-yl-methyl]amino}-N-{[3-nitro-4-(tetrahydro-2H-pyran-4-ylamino)phenyl]sulfonyl}benzamide | 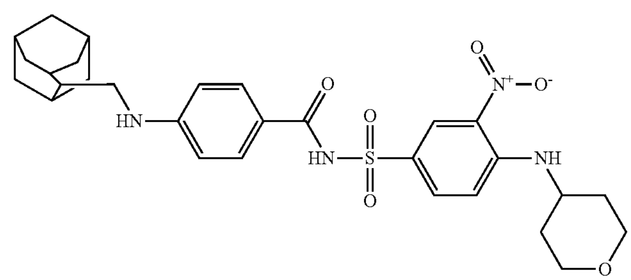 [SMILES: O=C(NS(=O)(=O)c1ccc(NC2CCOCC2)c([N+](=O)[O-])c1)c1ccc(NCC2C3CC4CC(C3)CC2C4)cc1] |
| 4-{2-[adamantan-1-yl]ethoxy)-N-{[3-nitro-4-(tetrahydro-2H-pyran-4-ylamino)phenyl]sulfonyl)benzamide | 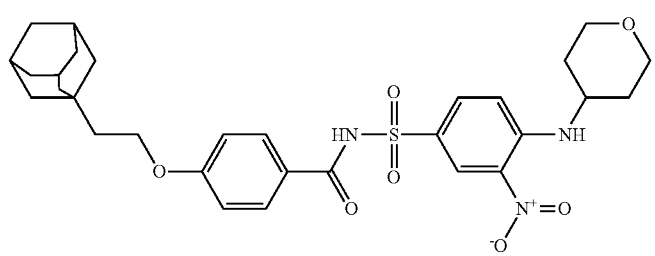 |
| N3-[adamantan-1-yl-acetyl]-N3-benzyl-N-({4-[(cyclohexyl-methyl)amino]-3-nitrophenyl}sulfonyl)-beta-alaninamide | 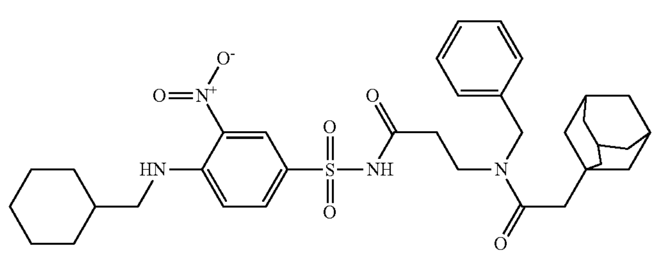 [SMILES: O=C(CCN(Cc1ccccc1)C(=O)CC12CC3CC(CC(C3)C1)C2)NS(=O)(=O)c1ccc(NCC2CCCCC2)c([N+](=O)[O-])c1] |

| Name | Structure |
|---|---|
| N-({4-[(cyclohexyl-methyl)amino]-3-nitrophenyl}sulfonyl)-4-{4-[(1S,2S,3S,5R)-2,6,6-trimethylbicyclo[3.1.1]hept-3-yl]piperazin-1-yl}benzamide | 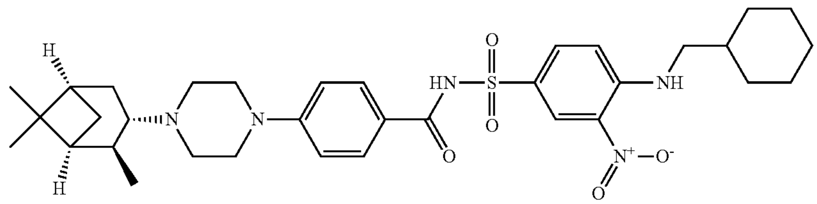 [SMILES: C[C@@H]1[C@@H](N2CCN(c3ccc(C(=O)NS(=O)(=O)c4ccc(NCC5CCCCC5)c([N+](=O)[O-])c4)cc3)CC2)C[C@H]2C[C@@H]1C2(C)C] |
| 4-{4-[adamantan-1-yl]piperazin-1-yl}-N-({4-[(cyclohexyl-methyl)amino]-3-nitrophenyl}sulfonyl)benzamide | |
| N-({4-[(cyclohexyl-methyl)amino]-3-nitrophenyl}sulfonyl)-4-{4-[3,5-dimethyl-adamantan-1-yl]piperazin-1-yl}benzamide | 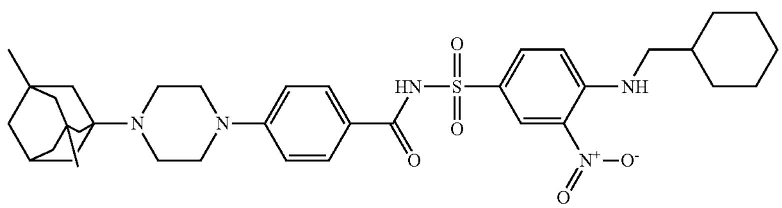 [SMILES: CC12CC3CC(C)(C1)CC(N1CCN(c4ccc(C(=O)NS(=O)(=O)c5ccc(NCC6CCCCC6)c([N+](=O)[O-])c5)cc4)CC1)(C3)C2] |
| [(3aS,5aR,8aR,8bS)-2,2,7,7-tetramethyl-tetrahydro-3aH-bis[1,3]dioxolo[4,5-b:4',5'-d]pyran-3a-yl]methyl(4-{4-[(4'-chlorobiphenyl-2-yl)methyl]piperazin-1-yl}benzoyl)sulfamate | 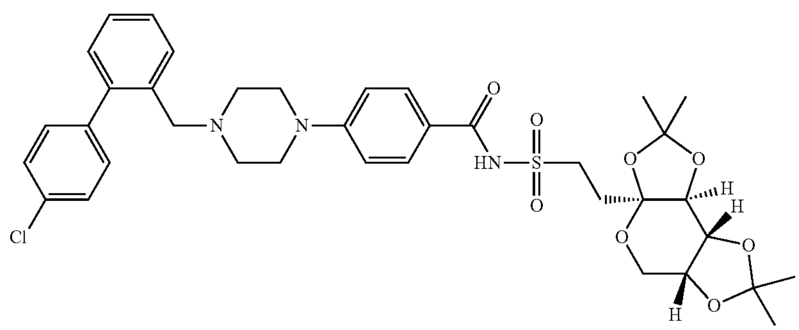 [SMILES: CC1(C)O[C@@H]2[C@@H](CO[C@@]3(CCS(=O)(=O)NC(=O)c4ccc(N5CCN(Cc6ccccc6-c6ccc(Cl)cc6)CC5)cc4)OC(C)(C)O[C@@H]23)O1] |
| 4-{4-[(4'-chlorobi-phenyl-2-yl)methyl]piperazin-1-yl}-N-({[(1R,4S)-7,7-dimethyl-2-oxobicyclo[2.2.1]hept-1-yl]methyl}sulfonyl)benzamide | |
| 4-(4-{2-[adamantan-1-yl]ethyl}piperazin-1-yl)-N-({4-[(cyclohexyl-methyl)amino]-3-nitrophenyl}sulfonyl)benzamide | 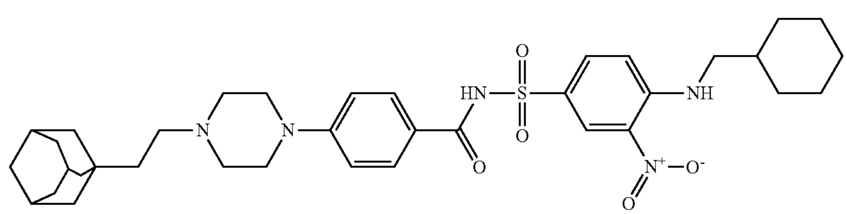 [SMILES: O=C(NS(=O)(=O)c1ccc(NCC2CCCCC2)c([N+](=O)[O-])c1)c1ccc(N2CCN(CCC34CC5CC(CC(C5)C3)C4)CC2)cc1] |

-continued

| Name | Structure |
|---|---|
| 4-{4-[(4'-chlorobiphenyl-2-yl)methyl]piperazin-1-yl}-N-({[(1S,4R)-7,7-dimethyl-2-oxobicyclo[2.2.1]hept-1-yl]methyl}sulfonyl)benzamide | 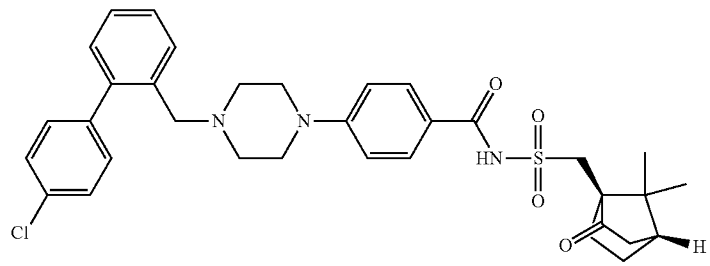 [SMILES: CC1(C)[C@@H]2CC[C@@]1(CS(=O)(=O)NC(=O)c1ccc(N3CCN(Cc4ccccc4-c4ccc(Cl)cc4)CC3)cc1)C(=O)C2] |
| N-({4-[(cyclohexylmethyl)amino]-3-nitrophenyl}sulfonyl)-4'-({(3-phenylpropanoyl)[(1S,2S,3S,5R)-2,6,6-trimethylbicyclo[3.1.1]hept-3-yl]amino}methyl)biphenyl-4-carboxamide | 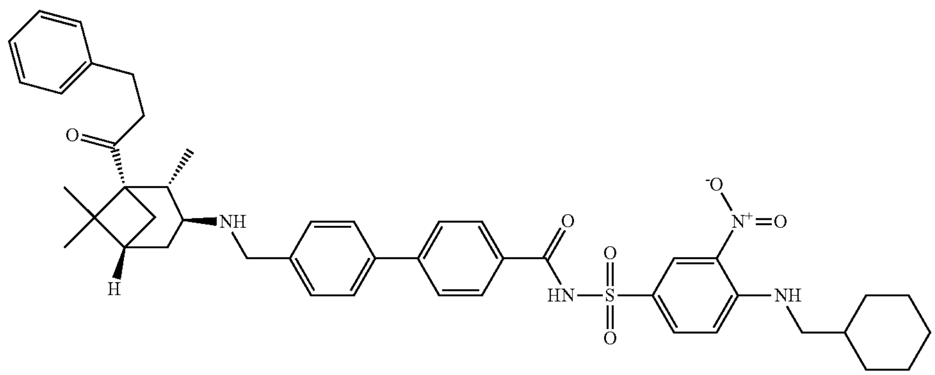 |
| N-({3-nitro-4-[(tetrahydro-2H-pyran-4-ylmethyl)amino]phenyl}sulfonyl)-4-(4-{2-[(1R,4R)-1,7,7-trimethylbicyclo[2.2.1]hept-2-en-2-yl]benzylidene}piperidin-1-yl)benzamide | 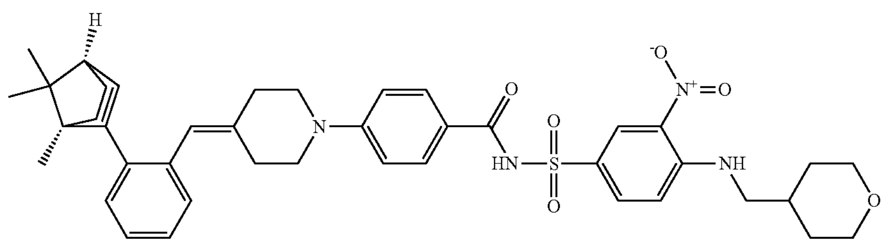 |
| N-({3-nitro-4-[(tetrahydro-2H-pyran-4-ylmethyl)amino]phenyl}sulfonyl)-4-(4-{2-[5-(4-phenyl-1,3-thiazol-2-yl)-2-thienyl]benzyl}piperazin-1-yl)benzamide | 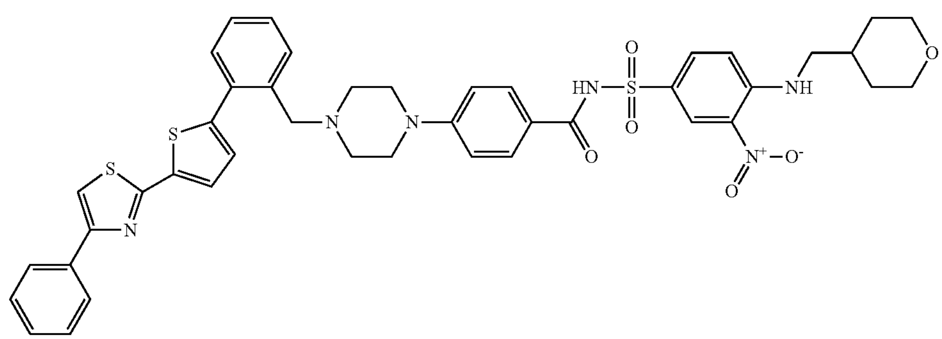 [SMILES: O=C(NS(=O)(=O)c1ccc(NCC2CCOCC2)c([N+](=O)[O-])c1)c1ccc(N2CCN(Cc3ccccc3-c3ccc(-c4nc(-c5ccccc5)cs4)s3)CC2)cc1] |
| 4-[4-(2-{5-[4-(adamantan-1-yl)-1,3-thiazol-2-yl]-2-thienyl}benzyl)piperazin-1-yl]-N-({3-nitro-4-[(tetrahydro-2H-pyran-4-ylmethyl)amino]phenyl}sulfonyl)benzamide | 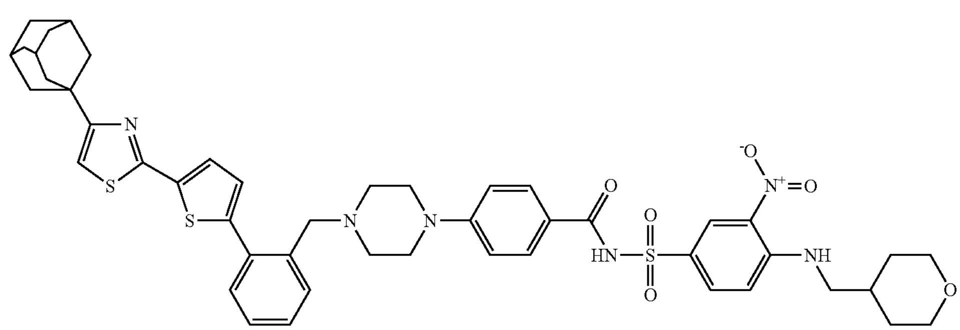 |

-continued

| Name | Structure |
|---|---|
| 5-{2-[(4-{4-[({3-nitro-4-[(tetrahydro-2H-pyran-4-ylmethyl)amino]phenyl}sulfonyl)carbamoyl]phenyl}piperazin-1-yl)methyl]phenyl}-N-(2-phenyl-1,3-benzoxazol-5-yl)-2-furamide | 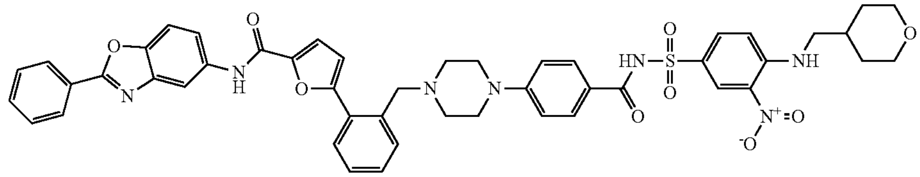 |
| N-({3-nitro-4-[(tetrahydro-2H-pyran-4-yl-methyl)amino]phenyl}sulfonyl)-4-{4-[2-(triphenylvinyl)benzyl]piperazin-1-yl}benzamide | |
| 4-{4-[2-(5-methyl-5,6-dihydrophenanthridin-6-yl)benzyl]piperazin-1-yl}-N-({3-nitro-4-[(tetrahydro-2H-pyran-4-ylmethyl)amino]phenyl}sulfonyl)benzamide | 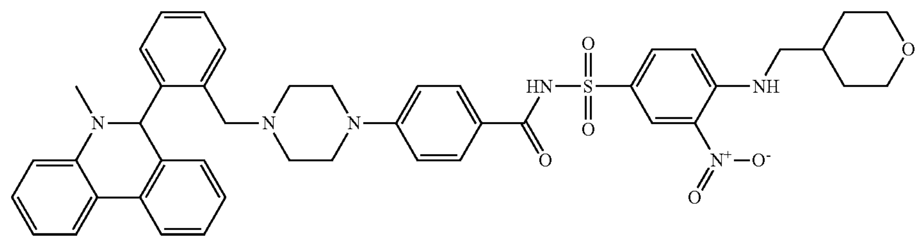 [SMILES: CN1c2ccccc2-c2ccccc2C1c1ccccc1CN1CCN(c2ccc(C(=O)NS(=O)(=O)c3ccc(NCC4CCOCC4)c([N+](=O)[O-])c3)cc2)CC1] |
| N-({3-nitro-4-[(tetrahydro-2H-pyran-4-yl-methyl)amino]phenyl}sulfonyl)-4-{4-[2-(4,4,5,5-tetramethyl-1,3,2-dioxaborolan-2-yl)benzyl]piperazin-1-yl}benzamide | |
| 4-(4-{2-[2-(2,6-dimethoxybenzoyl)-3-thienyl]benzylidene}piperidin-1-yl)-N-({3-nitro-4-[(tetrahydro-2H-pyran-4-ylmethyl)amino]phenyl}sulfonyl)benzamide | 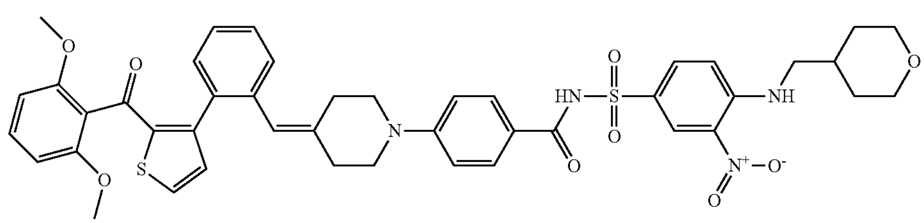 [SMILES: COc1cccc(OC)c1C(=O)c1sccc1-c1ccccc1C=C1CCN(c2ccc(C(=O)NS(=O)(=O)c3ccc(NCC4CCOCC4)c([N+](=O)[O-])c3)cc2)CC1] |
| 1-[adamantan-1-yl]-4-{2-[(1-{4-[({3-nitro-4-[(tetrahydro-2H-pyran-4-ylmethyl)amino]phenyl}sulfonyl)carbamoyl]phenyl}piperidin-4-ylidene)methyl]phenyl}-N,N-diphenyl-1H-pyrazole-3-carboxamide | 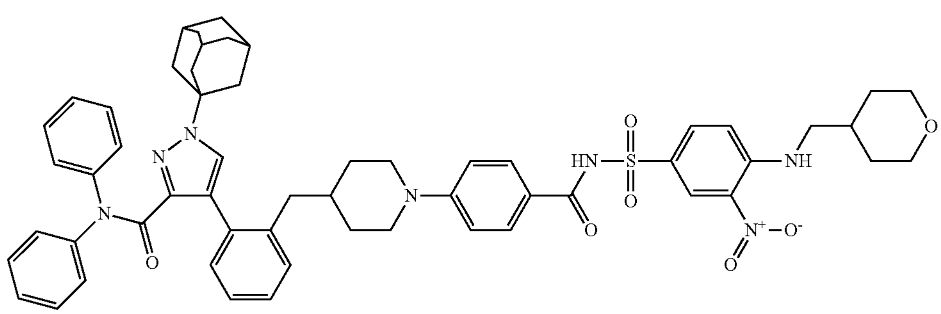 [SMILES: O=C(NS(=O)(=O)c1ccc(NCC2CCOCC2)c([N+](=O)[O-])c1)c1ccc(N2CCC(Cc3ccccc3-c3cn(C45CC6CC(CC(C6)C4)C5)nc3C(=O)N(c3ccccc3)c3ccccc3)CC2)cc1] |

| Name | Structure |
|---|---|
| N-({3-nitro-4-[(tetra-hydro-2H-pyran-4-ylmethyl)amino]phenyl}sulfonyl)-4-(4-{2-[octahydro-1H-4,7-methanoinden-5-yl(3-phenylpropanoyl)amino]benzyl}piperazin-1-yl)benzamide | 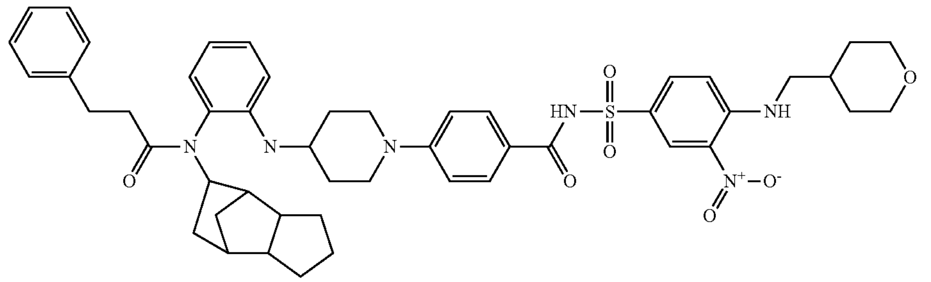 [SMILES: O=C(NS(=O)(=O)c1ccc(NCC2CCOCC2)c([N+](=O)[O-])c1)c1ccc(N2CCC(Nc3ccccc3N(C(=O)CCc3ccccc3)C3CC4CC3C3CCCC43)CC2)cc1] |
| 4-[4-(2-{5-[8-aza-bicyclo[3.2.1]oct-8-ylmethyl]-2-thienyl}benzylidene)piperidin-1-yl]-N-({3-nitro-4-[(tetrahydro-2H-pyran-4-ylmethyl)amino]phenyl}sulfonyl)benzamide | 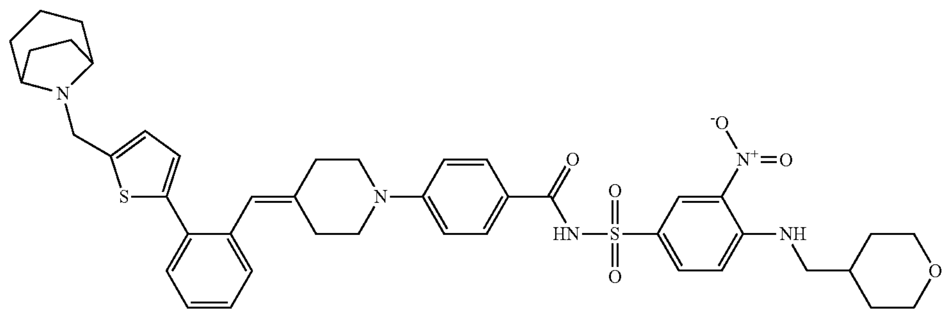 |
| N-({3-nitro-4-[(tetra-hydro-2H-pyran-4-ylmethyl)amino]phenyl}sulfonyl)-4-[4-(4-{[(1S,2S,3S,5R)-2,6,6-trimethyl-bicyclo[3.1.1]hept-3-yl]amino}benzylidene)piperidin-1-yl]benzamide | 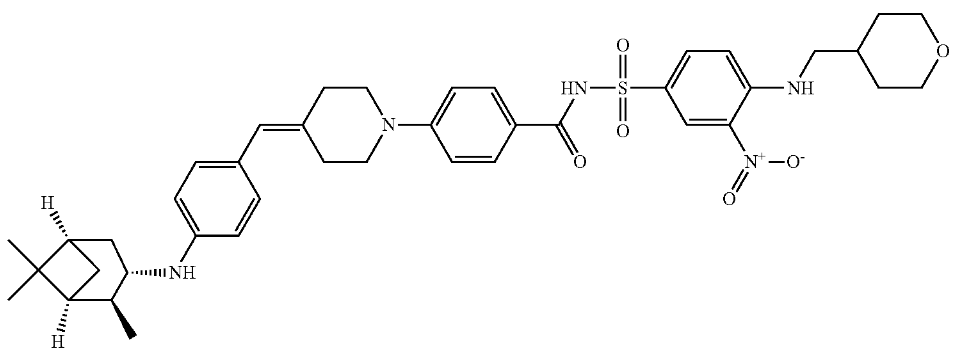 [SMILES: C[C@@H]1[C@@H](Nc2ccc(C=C3CCN(c4ccc(C(=O)NS(=O)(=O)c5ccc(NCC6CCOCC6)c([N+](=O)[O-])c5)cc4)CC3)cc2)C[C@H]2C[C@@H]1C2(C)C] |
| N-({3-nitro-4-[(tetra-hydro-2H-pyran-4-ylmethyl)amino]phenyl}sulfonyl)-4-[4-(3-{[(1S,2S,3S,5R)-2,6,6-trimethyl-bicyclo[3.1.1]hept-3-yl]amino}benzylidene)piperidin-1-yl]benzamide | 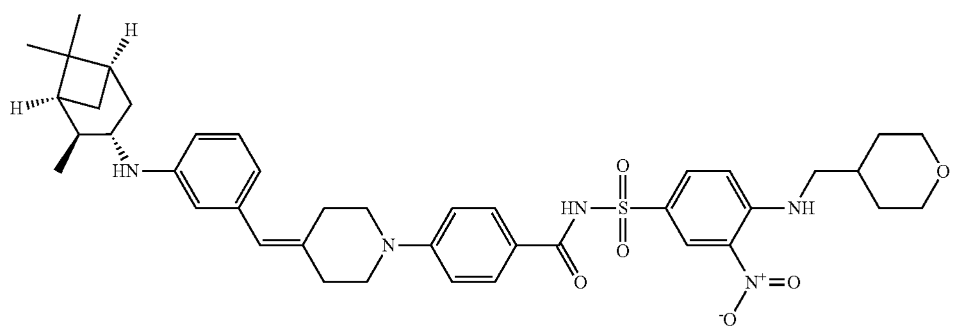 |
| 4-[4-(2-{5-[4-(adamantan-1-yl)-1,3-thiazol-2-yl]-2-thienyl}benzylidene)piperidin-1-yl]-N-({3-nitro-4-[(tetrahydro-2H-pyran-4-ylmethyl)amino]phenyl}sulfonyl)benzamide | 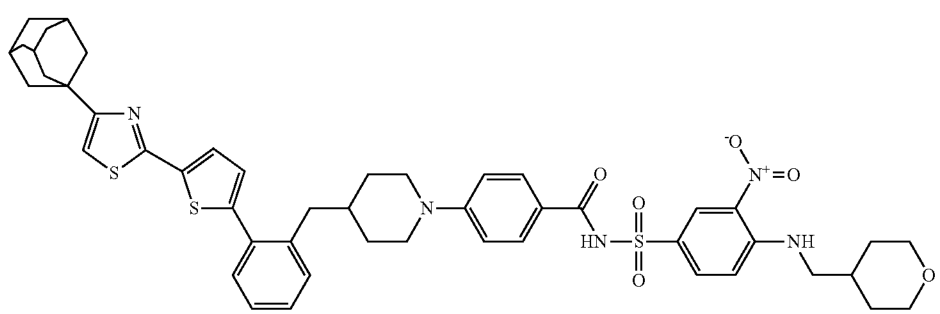 |

| Name | Structure |
|---|---|
| N-({3-nitro-4-[(tetra-hydro-2H-pyran-4-ylmethyl)amino]phenyl}sulfonyl)-4-(4-{2-[5-(4-phenyl-1,3-thiazol-2-yl)-2-thienyl]benzyl-idene}piperidin-1-yl)benzamide | 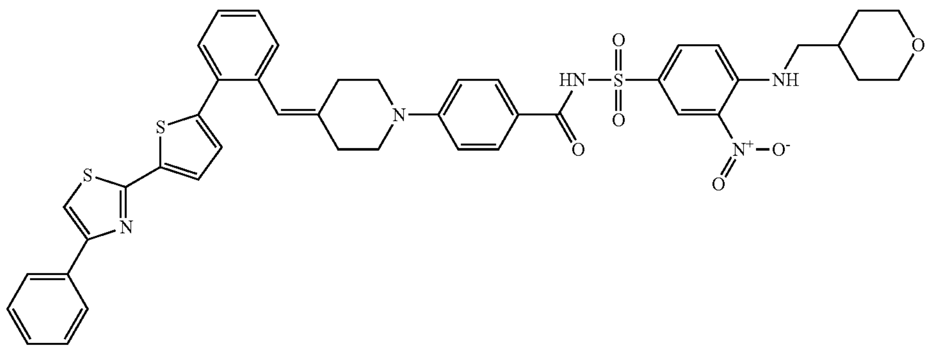 [SMILES: O=C(NS(=O)(=O)c1ccc(NCC2CCOCC2)c([N+](=O)[O-])c1)c1ccc(N2CCC(=Cc3ccccc3-c3ccc(-c4nc(-c5ccccc5)cs4)s3)CC2)cc1] |
| N-[(4-{[adamantan-1-ylmethyl]amino}-3-nitrophenyl)sulfonyl]-4-(4-oxo-4H-chromen-6-yl)benzamide | 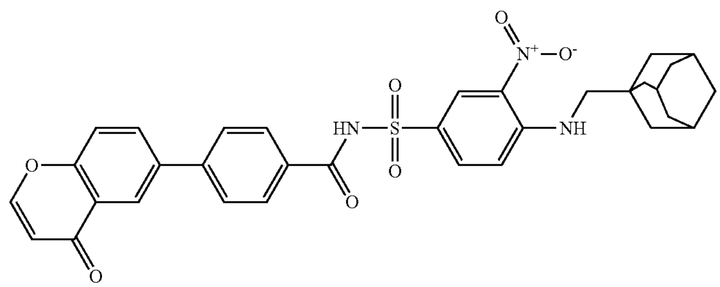 [SMILES: O=C(NS(=O)(=O)c1ccc(NCC23CC4CC(CC(C4)C2)C3)c([N+](=O)[O-])c1)c1ccc(-c2ccc3occc(=O)c3c2)cc1] |
| N-[(4-{[adamantan-1-ylmethyl]amino}-3-nitrophenyl)sulfonyl]-4-(1-octyl-1H-pyrazol-4-yl)benzamide | 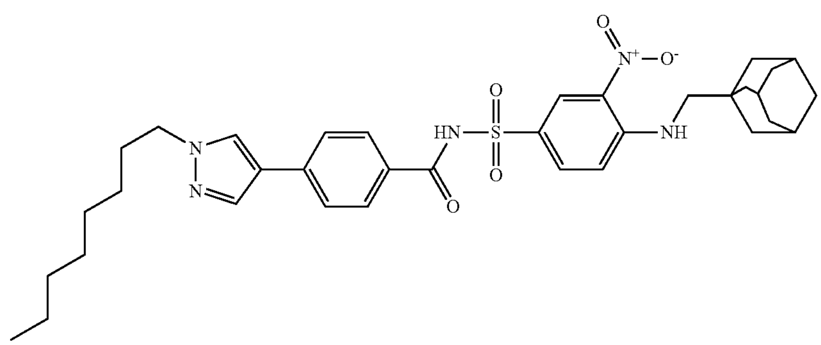 [SMILES: CCCCCCCCn1cc(-c2ccc(C(=O)NS(=O)(=O)c3ccc(NCC45CC6CC(CC(C6)C4)C5)c([N+](=O)[O-])c3)cc2)cn1] |
| 4-[5-(4-{[(4-{[adamantan-1-ylmethyl]amino}-3-nitrophenyl)sulfonyl]carbamoyl}phenyl)-1,3-benzothiazol-2-yl]butanoic acid | 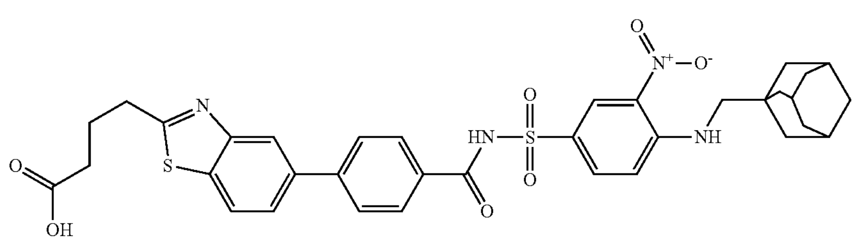 [SMILES: O=C(O)CCCc1nc2cc(-c3ccc(C(=O)NS(=O)(=O)c4ccc(NCC56CC7CC(CC(C7)C5)C6)c([N+](=O)[O-])c4)cc3)ccc2s1] |
| N-{[3-nitro-4-(tetra-hydro-2H-pyran-4-ylamino)phenyl]sulfonyl}-4-[(1R,5S)-1,8,8-trimethyl-3-azabicyclo[3.2.1]oct-3-yl]benzamide | 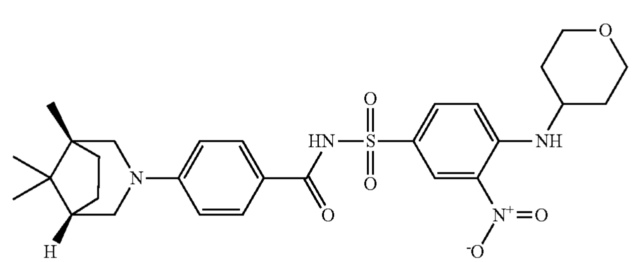 |

-continued

| Name | Structure |
|---|---|
| 6-{3-[adamantan-1-yl]-4-methoxyphenyl}-N-({4-[(cyclohexylmethyl)amino]-3-nitrophenyl}sulfonyl)-2-naphthamide | |
| 4-{4-[adamantan-1-ylacetyl]piperazin-1-yl}-N-{[3-nitro-4-(tetrahydro-2H-pyran-4-ylamino)phenyl]sulfonyl}benzamide | |
| 4-{[adamantan-1-ylmethyl]amino}-N-{[3-nitro-4-(tetrahydro-2H-pyran-4-ylamino)phenyl]sulfonyl}benzamide | |
| N-{1-[4-({[3-nitro-4-(tetrahydro-2H-pyran-4-ylamino)phenyl]sulfonyl}carbamoyl)phenyl]piperidin-4-yl}adamantane-1-carboxamide | |
| 4-[adamantan-2-ylamino]-N-{[3-nitro-4-(tetrahydro-2H-pyran-4-ylamino)phenyl]sulfonyl}benzamide | |
| N-{[3-nitro-4-(tetrahydro-2H-pyran-4-ylamino)phenyl]sulfonyl}-4-{[(1R,2R,3R,5S)-2,6,6-trimethylbicyclo[3.1.1]hept-3-yl]oxy}benzamide | |

In some embodiments, the compound is selected from the group consisting of:

| Name | Structure |
|---|---|
| 4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)-2-phenoxybenzamide | 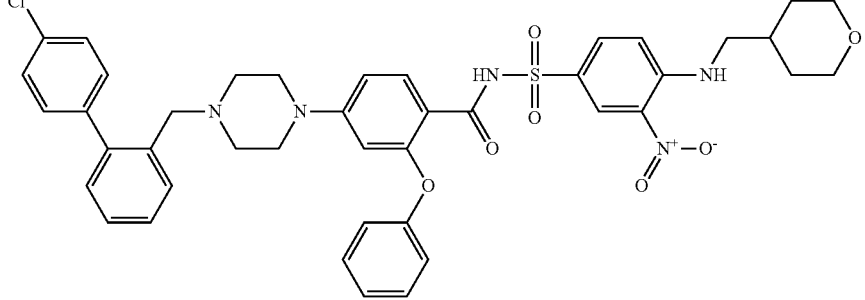 |
| 4-{4-[(4'-chloro-1,1'-biphenyl-2-yl)methyl]piperazin-1-yl}-2-phenoxy-N-({4-[(tetrahydro-2H-pyran-4-ylmethyl)amino]phenyl}sulfonyl)benzamide | 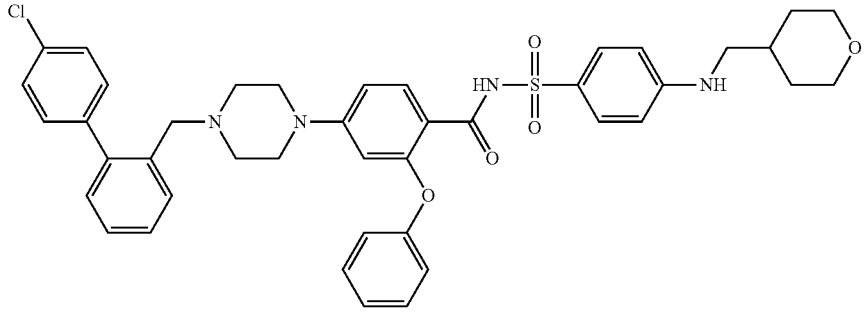 |
| 2-(benzyloxy)-4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)benzamide | 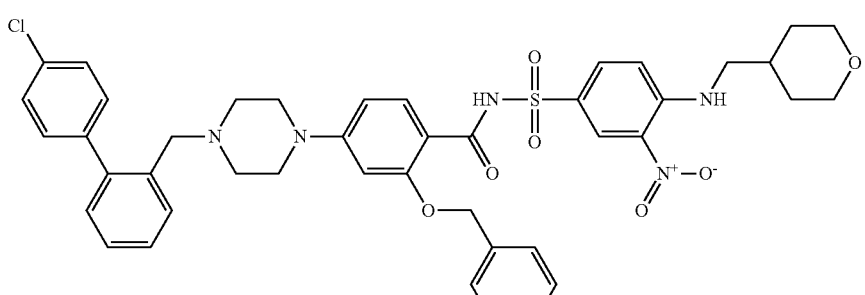 |
| 4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)-2-(2-phenylethoxy)benzamide | 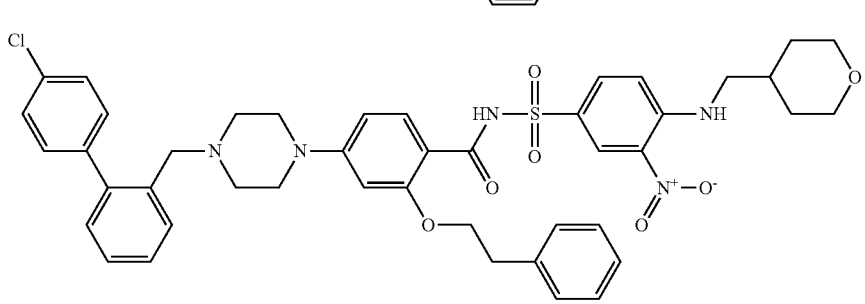 |
| 4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)-2-(phenylthio)benzamide | 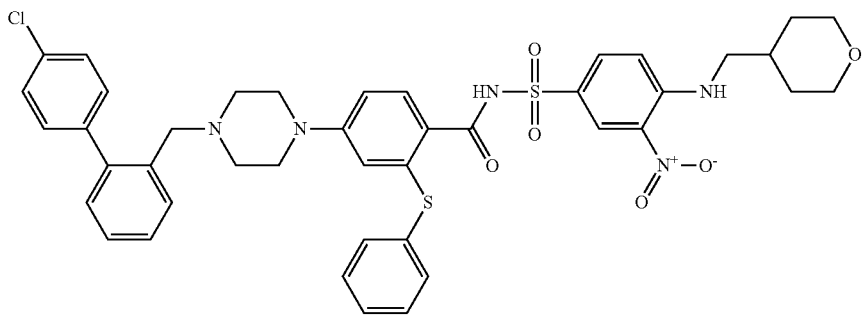 |

| Name | Structure |
|---|---|
| 4-{4-[(4'-chloro-1,1'-biphenyl-2-yl)methyl]piperazin-1-yl}-2-(phenylthio)-N-({4-[(tetrahydro-2H-pyran-4-ylmethyl)amino]phenyl}sulfonyl)benzamide | 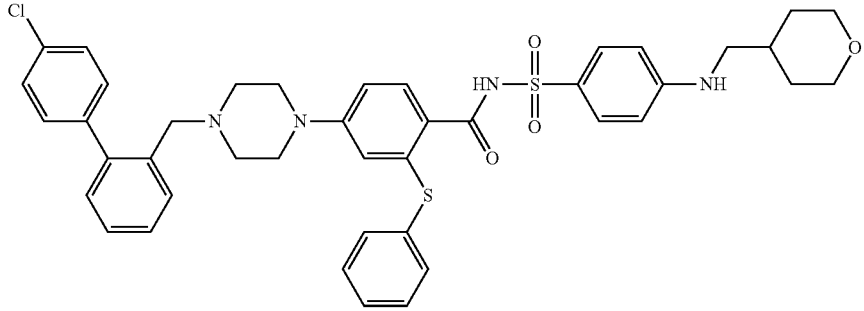 [SMILES: O=C(NS(=O)(=O)c1ccc(NCC2CCOCC2)cc1)c1ccc(N2CCN(Cc3ccccc3-c3ccc(Cl)cc3)CC2)cc1Oc1ccccc1] |
| 4-{4-[(4'-chloro-1,1'-biphenyl-2-yl)methyl]piperazin-1-yl}-N-({4-[(3-morpholin-4-ylpropyl)amino]-3-nitrophenyl}sulfonyl)-2-(phenylthio)benzamide | 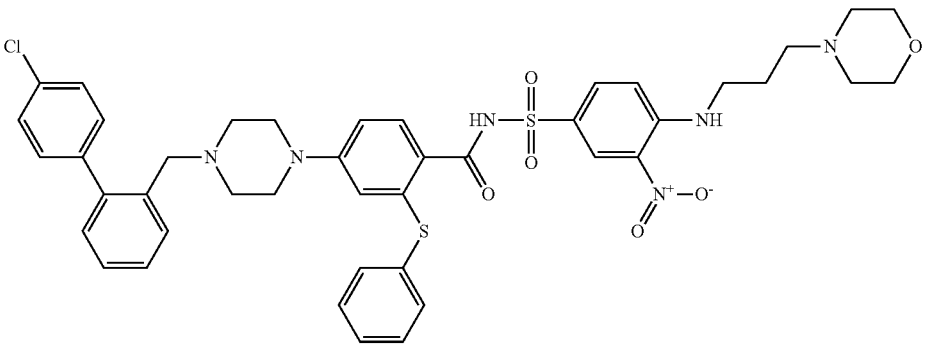 [SMILES: O=C(NS(=O)(=O)c1ccc(NCCCN2CCOCC2)c([N+](=O)[O-])c1)c1ccc(N2CCN(Cc3ccccc3-c3ccc(Cl)cc3)CC2)cc1Sc1ccccc1] |
| 4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)-2-(phenylsulfonyl)benzamide | 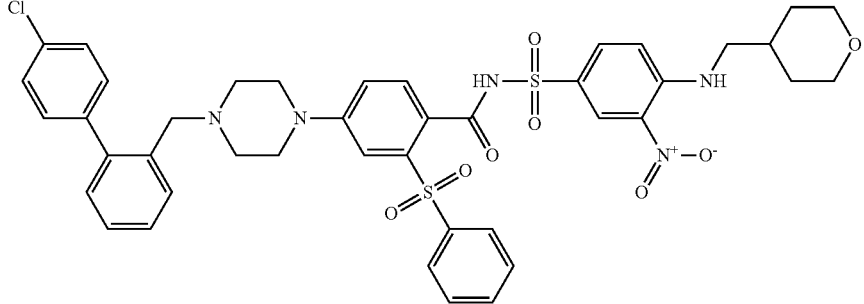 [SMILES: O=C(NS(=O)(=O)c1ccc(NCC2CCOCC2)c([N+](=O)[O-])c1)c1ccc(N2CCN(Cc3ccccc3-c3ccc(Cl)cc3)CC2)cc1S(=O)(=O)c1ccccc1] |
| 4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)-2-(phenylsulfinyl)benzamide | 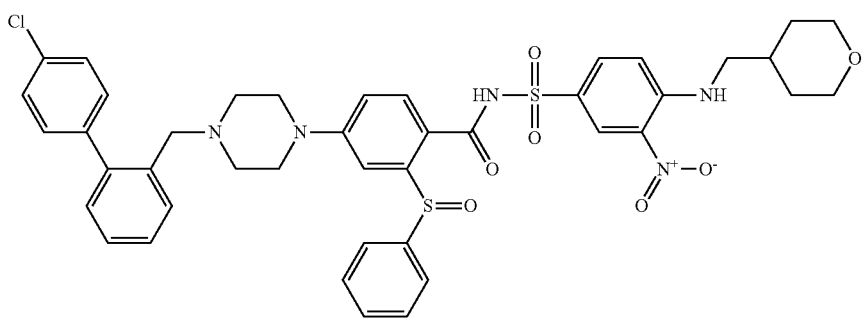 [SMILES: O=C(NS(=O)(=O)c1ccc(NCC2CCOCC2)c([N+](=O)[O-])c1)c1ccc(N2CCN(Cc3ccccc3-c3ccc(Cl)cc3)CC2)cc1S(=O)c1ccccc1] |

-continued

| Name | Structure |
|---|---|
| 2-benzyl-4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)benzamide | 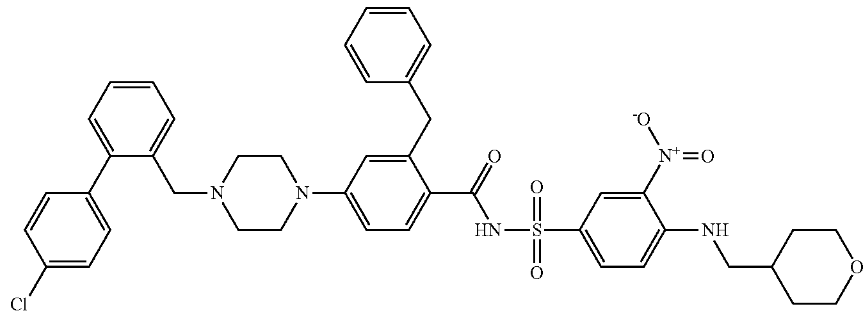 |
| 2-benzyl-4-{4-[(4'-chloro-1,1'-biphenyl-2-yl)methyl]piperazin-1-yl}-N-({4-[(tetrahydro-2H-pyran-4-ylmethyl)amino]phenyl}sulfonyl)benzamide | 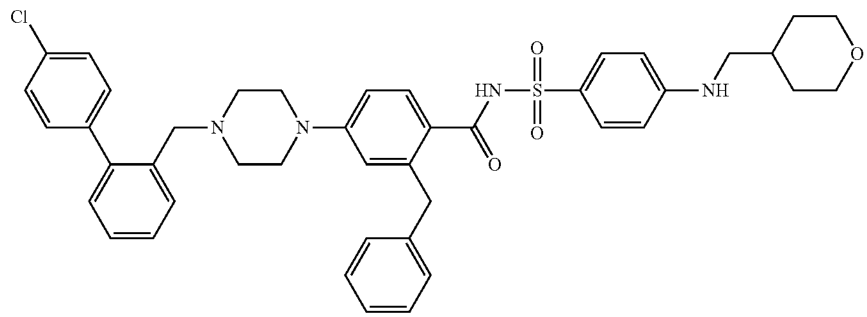 |
| 2-benzyl-4-{4-[(4'-chloro-1,1'-biphenyl-2-yl)methyl]piperazin-1-yl}-N-({4-[(3-morpholin-4-ylpropyl)amino]-3-nitrophenyl}sulfonyl)benzamide | 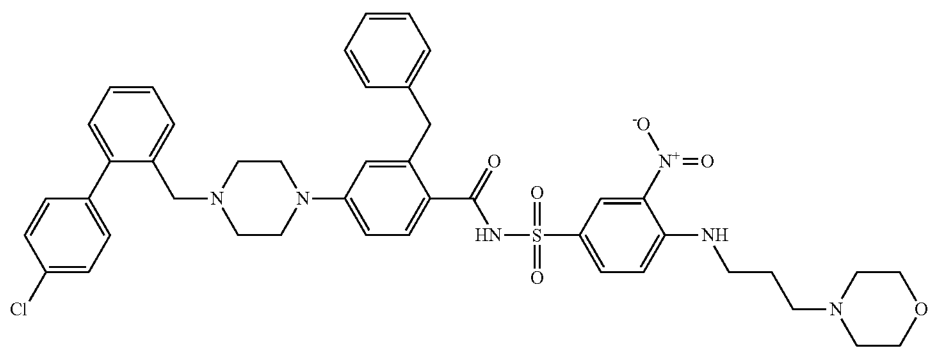 |
| 4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)-2-(2-phenylethyl)benzamide | 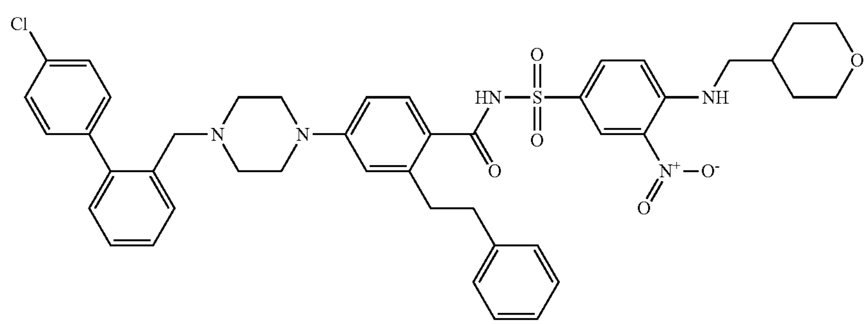 [SMILES: O=C(NS(=O)(=O)c1ccc(NCC2CCOCC2)c([N+](=O)[O-])c1)c1ccc(N2CCN(Cc3ccccc3-c3ccc(Cl)cc3)CC2)cc1CCc1ccccc1] |
| 2-(benzylamino)-4-{4-[(4'-chloro-1,1'-biphenyl-2-yl)methyl]piperazin-1-yl}-N-(3-nitro-4-[(tetrahydro-2H-pyran-4-ylmethyl)amino]phenyl}sulfonyl)benzamide | 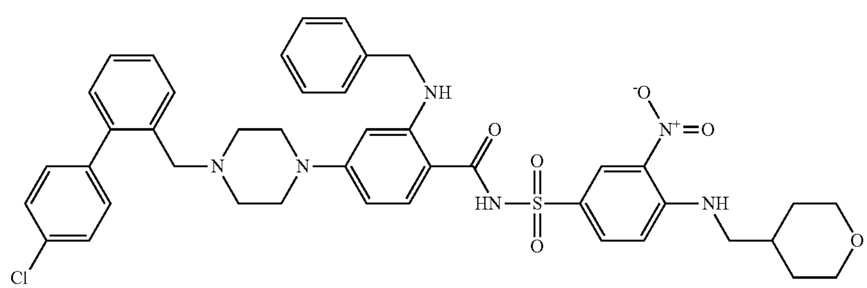 |

-continued

| Name | Structure |
|---|---|
| 2-anilino-4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)benzamide | 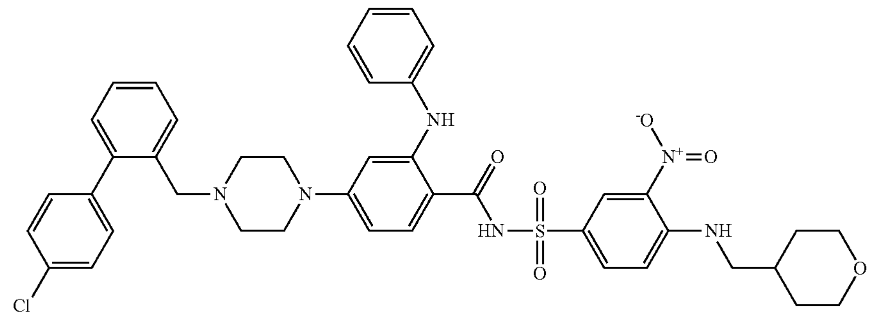 |
| 2-anilino-4-{4-[(4'-chloro-1,1'-biphenyl-2-yl)methyl]piperazin-1-yl}-N-({4-[(tetrahydro-2H-pyran-4-ylmethyl)amino]phenyl}sulfonyl)benzamide | 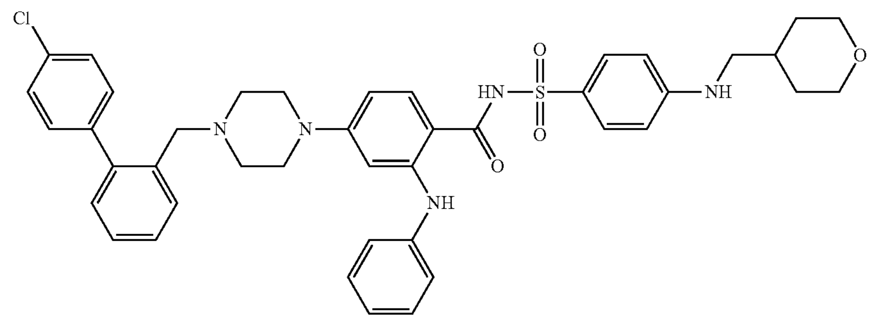 |
| 4-{4-[(4'-chloro-1,1'-biphenyl-2-yl)methyl]piperazin-1-yl}-2-methoxy-N-({3-nitro-4-[(tetrahydro-2H-pyran-4-ylmethyl)amino]phenyl}sulfonyl)benzamide | 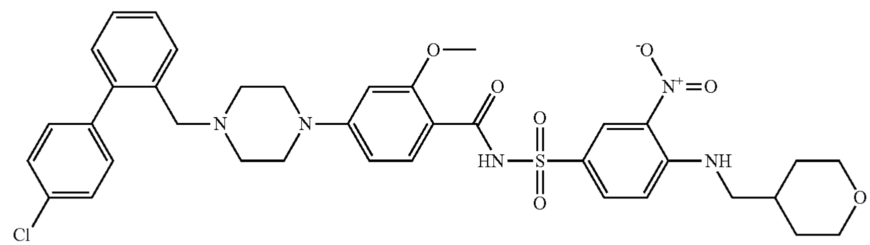 |
| 4-(4-{[2-(4-chlorophenyl)-4,4-dimethylcyclohex-1-en-1-yl]methyl]piperazin-1-yl)-N-({4-[(3-morpholin-4-ylpropyl)amino]-3-nitrophenyl}sulfonyl)-2-phenoxybenzamide | |
| 4-(4-{[2-(4-chlorophenyl)-5,5-dimethylcyclohex-1-en-1-yl]methyl}piperazin-1-yl)-N-({4-[(3-morpholin-4-ylpropyl)amino]-3-nitrophenyl}sulfonyl)-2-phenoxybenzamide | 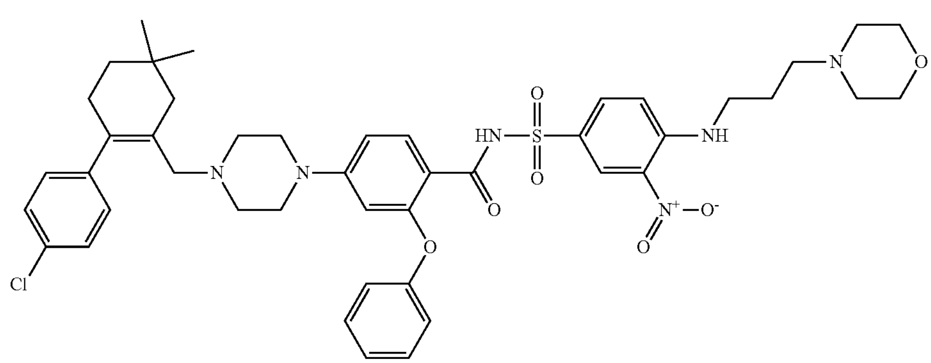 [SMILES: CC1(C)CCC(c2ccc(Cl)cc2)=C(CN2CCN(c3ccc(C(=O)NS(=O)(=O)c4ccc(NCCCN5CCOCC5)c([N+](=O)[O-])c4)c(Oc4ccccc4)c3)CC2)C1] |

-continued

| Name | Structure |
|---|---|
| 4-(4-{[2-(4-chlorophenyl)-4,4-dimethylcyclohex-1-en-1-yl]methyl}piperazin-1-yl)-2-(1H-indazol-5-yloxy)-N-({4-[(3-morpholin-4-ylpropyl)amino]-3-nitrophenyl}sulfonyl)benzamide | |
| 4-(4-{[2-(4-chlorophenyl)-4,4-dimethylcyclohex-1-en-1-yl]methyl}piperazin-1-yl)-2-(1H-indazol-5-yloxy)-N-({4-[(1-methylpiperidin-4-yl)amino]-3-nitrophenyl}sulfonyl)benzamide | |
| 4-(4-{[2-(4-chlorophenyl)-4,4-dimethylcyclohex-1-en-1-yl]methyl}piperazin-1-yl)-N-({4-[(3-morpholin-4-ylpropyl)amino]-3-nitrophenyl}sulfonyl)-2-(1,2,3,4-tetrahydroquinolin-6-yloxy)benzamide | |

| Name | Structure |
|---|---|
| 4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)-2-(1,2,3,4-tetrahydroquinolin-6-yloxy)benzamide | |
| 4-(4-{[4'-chloro-4-(pyrrolidin-1-ylmethyl)-1,1'-biphenyl-2-yl]methyl}piperazin-1-yl)-2-(1H-indol-4-yloxy)-N-({3-nitro-4-[(tetrahydro-2H-pyran-4-ylmethyl)amino]phenyl}sulfonyl)benzamide | |
| 4-(4-{[4'-chloro-4-(2-pyrrolidin-1-ylethyl)-1,1'-biphenyl-2-yl]methyl]piperazin-1-yl)-2-(1H-indol-4-yloxy)-N-({3-nitro-4-[(tetrahydro-2H-pyran-4-ylmethyl)amino]phenyl}sulfonyl)benzamide | |

-continued

| Name | Structure |
|---|---|
| 4-(4-{[2-(4-chlorophenyl)-4,4-dimethylcyclohex-1-en-1-yl]methyl}piperazin-1-yl)-N-({4-[(1-cyclopentylpiperidin-4-yl)amino]-3-nitrophenyl}sulfonyl)-2-(1H-indol-5-yloxy)benzamide | |
| 4-{4-[(4'-chloro-1,1'-biphenyl-2-yl)methyl]-3-isobutyl-piperazin-1-yl}-N-({3-nitro-4-[(tetrahydro-2H-pyran-4-ylmethyl)amino]phenyl}sulfonyl)-2-phenoxybenzamide | |
| 4-{4-[(4'-chloro-1,1'-biphenyl-2-yl)methyl]piperazin-1-yl}-N-{[4-(2,4-dioxo-3-azabicyclo[3.2.0]hept-3-yl)phenyl]sulfonyl}-2-phenoxybenzamide | 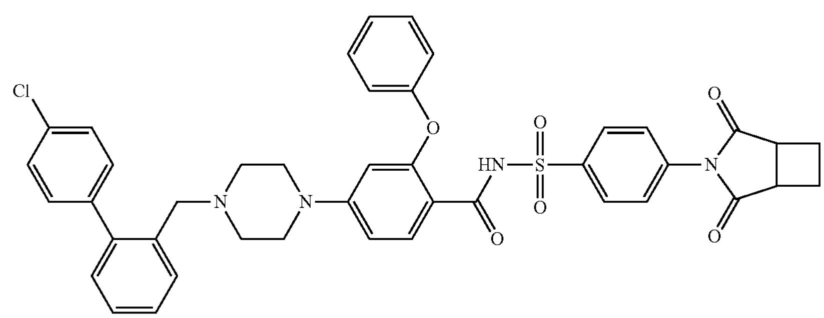 [SMILES: O=C(NS(=O)(=O)c1ccc(N2C(=O)C3CCC3C2=O)cc1)c1ccc(N2CCN(Cc3ccccc3-c3ccc(Cl)cc3)CC2)cc1Oc1ccccc1] |
| 4-{4-[(4'-chloro-1,1'-biphenyl-2-yl)methyl]piperazin-1-yl}-N-{[4-(4-methyl-6-oxo-1,4,5,6-tetrahydropyridazin-3-yl)phenyl]sulfonyl}-2-phenoxybenzamide | 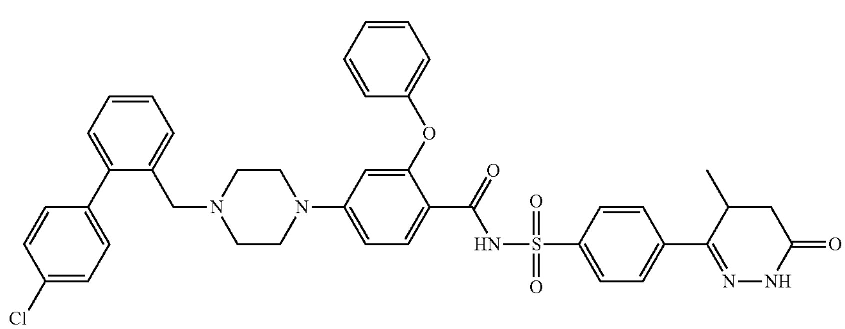 [SMILES: CC1CC(=O)NN=C1c1ccc(S(=O)(=O)NC(=O)c2ccc(N3CCN(Cc4ccccc4-c4ccc(Cl)cc4)CC3)cc2Oc2ccccc2)cc1] |

-continued

| Name | Structure |
|---|---|
| 4-{4-[(4'-chloro-1,1'-biphenyl-2-yl)methyl]piperazin-1-yl}-N-{[4-(3,3-dimethyl-2-oxoazetidin-1-yl)phenyl]sulfonyl}-2-phenoxybenzamide | 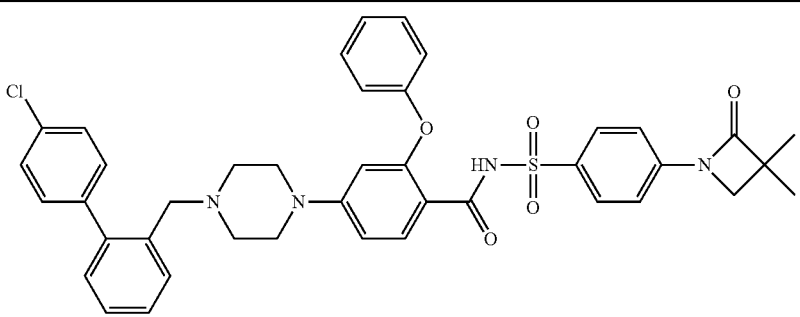 |
| 4-{4-[(4'-chloro-1,1'-biphenyl-2-yl)methyl]piperazin-1-yl}-N-{[4-(4-nitro-2H-1,2,3-triazol-2-yl)phenyl]sulfonyl}-2-phenoxybenzamide | 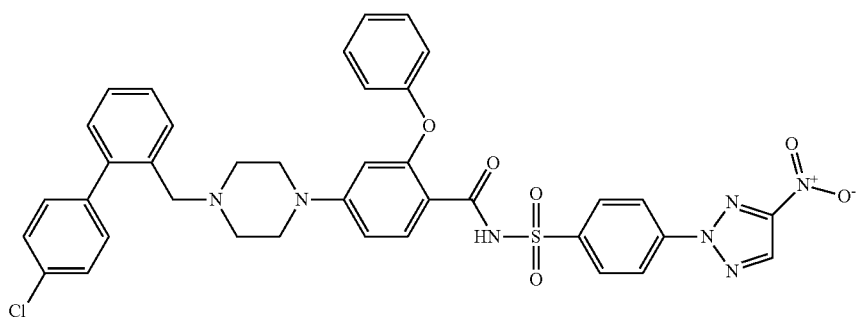 [SMILES: O=C(NS(=O)(=O)c1ccc(-n2ncc([N+](=O)[O-])n2)cc1)c1ccc(N2CCN(Cc3ccccc3-c3ccc(Cl)cc3)CC2)cc1Oc1ccccc1] |
| 4-{4-[(4'-chloro-1,1'-biphenyl-2-yl)methyl]piperazin-1-yl}-2-phenoxy-N-{[2-(2-piperidin-1-ylethoxy)phenyl]sulfonyl}benzamide | 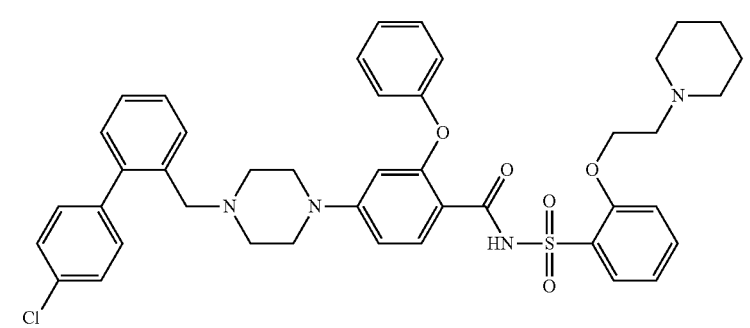 [SMILES: O=C(NS(=O)(=O)c1ccccc1OCCN1CCCCC1)c1ccc(N2CCN(Cc3ccccc3-c3ccc(Cl)cc3)CC2)cc1Oc1ccccc1] |
| 4-{4-[(4'-chloro-1,1'-biphenyl-2-yl)methyl]piperazin-1-yl}-N-{[3-({[(1-ethylpyrrolidin-2-yl)methyl]amino}carbonyl)-4-methoxyphenyl]sulfonyl}-2-phenoxybenzamide | 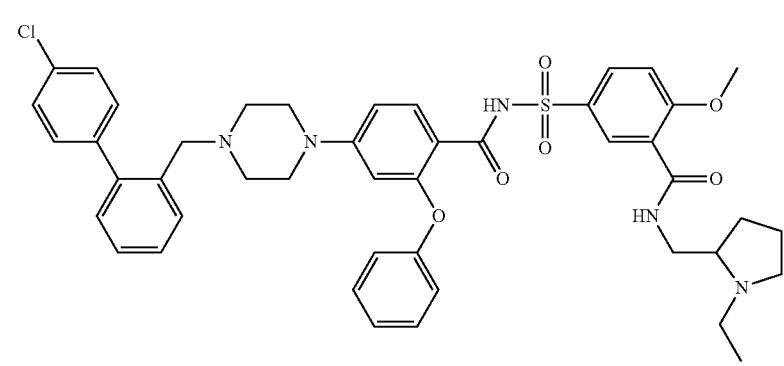 [SMILES: CCN1CCCC1CNC(=O)c1cc(S(=O)(=O)NC(=O)c2ccc(N3CCN(Cc4ccccc4-c4ccc(Cl)cc4)CC3)cc2Oc2ccccc2)ccc1OC] |

| Name | Structure |
|---|---|
| 4-{4-[(4'-chloro-1,1'-biphenyl-2-yl)methyl]piperazin-1-yl}-2-(1-naphthyloxy)-N-({3-nitro-4-[(tetrahydro-2H-pyran-4-ylmethyl)amino]phenyl}sulfonyl)benzamide | 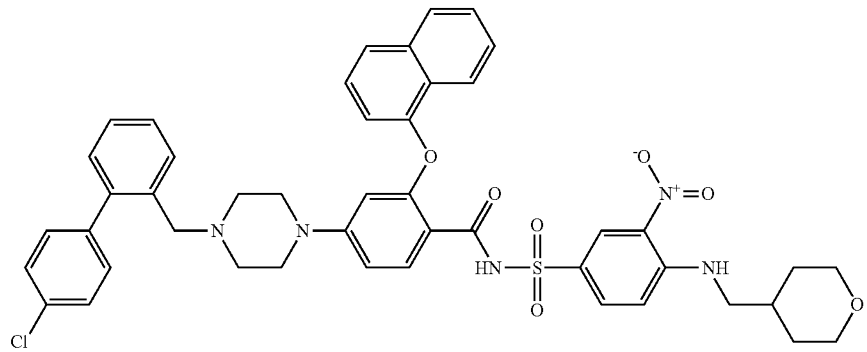 |
| 4-{4-[(4'-chloro-1,1'-biphenyl-2-yl)methyl]piperazin-1-yl}-2-(2-naphthyloxy)-N-({3-nitro-4-[(tetrahydro-2H-pyran-4-ylmethyl)amino]phenyl}sulfonyl)benzamide | 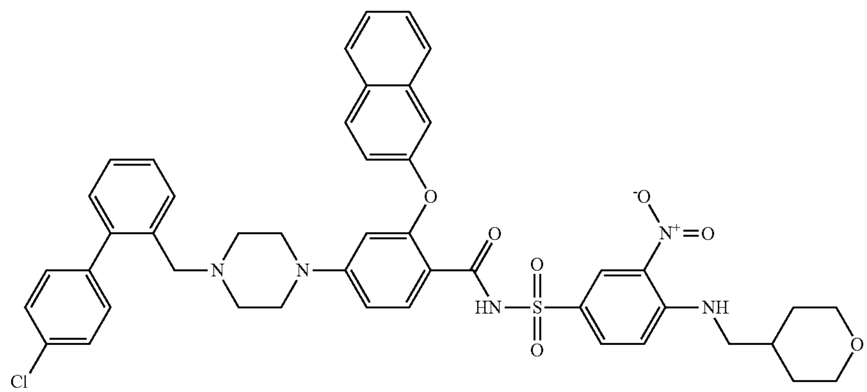 |
| 4-{4-[(4'-chloro-1,1'-biphenyl-2-yl)methyl]piperazin-1-yl}-N-({4-[(3-morpholin-4-ylpropyl)amino]-3-nitrophenyl}sulfonyl)-2-(2-naphthyloxy)benzamide | 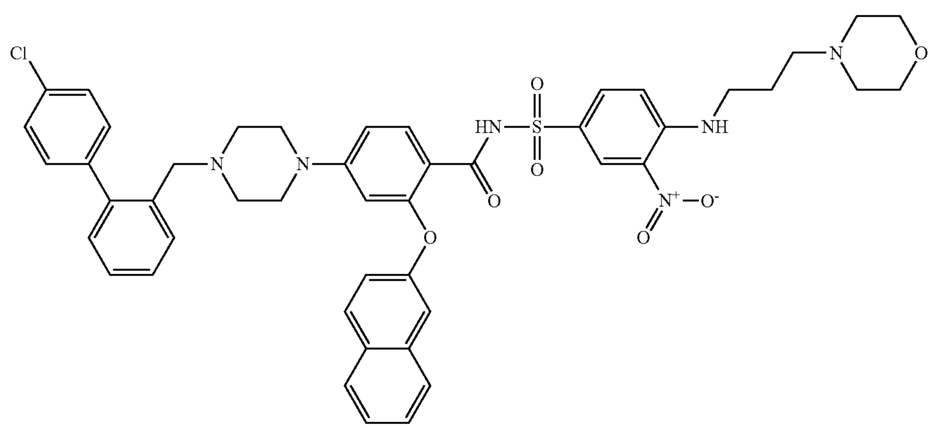 [SMILES: O=C(NS(=O)(=O)c1ccc(NCCCN2CCOCC2)c([N+](=O)[O-])c1)c1ccc(N2CCN(Cc3ccccc3-c3ccc(Cl)cc3)CC2)cc1Oc1ccc2ccccc2c1] |
| 4-{4-[(4'-chloro-1,1'-biphenyl-2-yl)methyl]piperazin-1-yl}-2-(2-naphthyloxy)-N-({4-[(tetrahydro-2H-pyran-4-ylmethyl)amino]-3-[(trifluoromethyl)sulfonyl]phenyl}sulfonyl)benzamide | 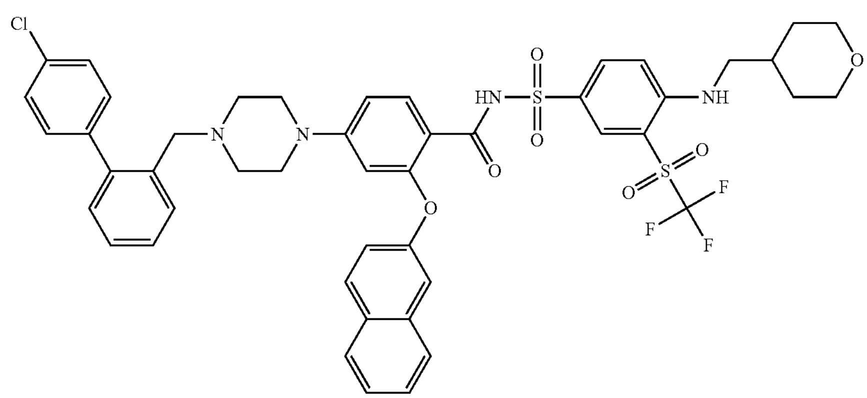 [SMILES: O=C(NS(=O)(=O)c1ccc(NCC2CCOCC2)c(S(=O)(=O)C(F)(F)F)c1)c1ccc(N2CCN(Cc3ccccc3-c3ccc(Cl)cc3)CC2)cc1Oc1ccc2ccccc2c1] |

| Name | Structure |
|---|---|
| 4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)-2-(quinolin-7-yloxy)benzamide | 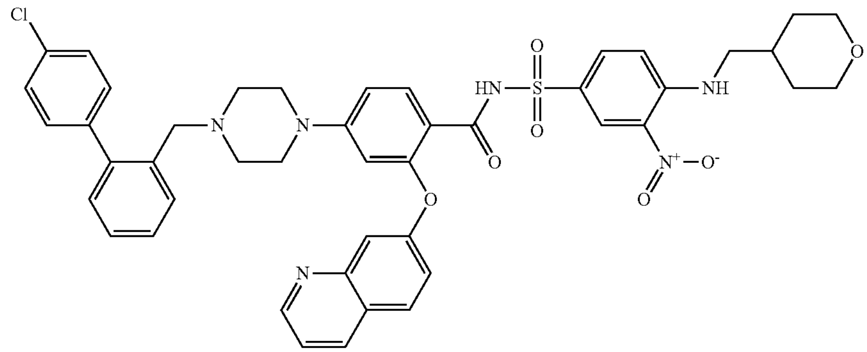 [SMILES: O=C(NS(=O)(=O)c1ccc(NCC2CCOCC2)c([N+](=O)[O-])c1)c1ccc(N2CCN(Cc3ccccc3-c3ccc(Cl)cc3)CC2)cc1Oc1ccc2cccnc2c1] |
| 4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)-2-(quinolin-6-yloxy)benzamide | 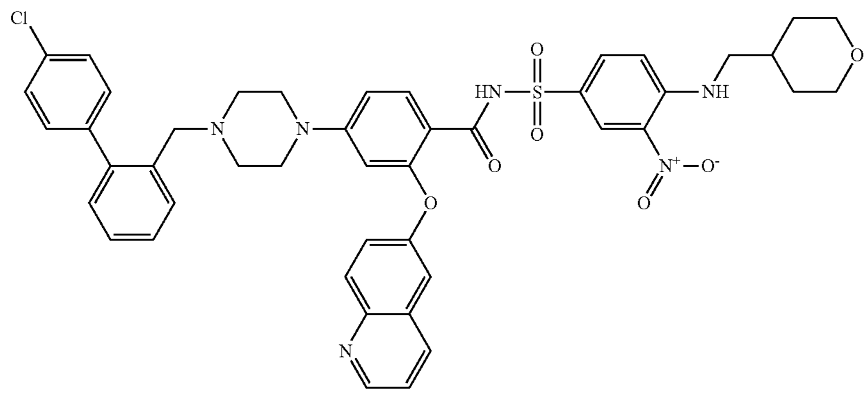 [SMILES: O=C(NS(=O)(=O)c1ccc(NCC2CCOCC2)c([N+](=O)[O-])c1)c1ccc(N2CCN(Cc3ccccc3-c3ccc(Cl)cc3)CC2)cc1Oc1ccc2ncccc2c1] |
| 4-{4-[(4'-chloro-1,1'-biphenyl-2-yl)methyl]piperazin-1-yl}-2-(1H-indol-5-yloxy)-N-({3-nitro-4-[(tetrahydro-2H-pyran-4-ylmethyl)amino]phenyl}sulfonyl)benzamide | 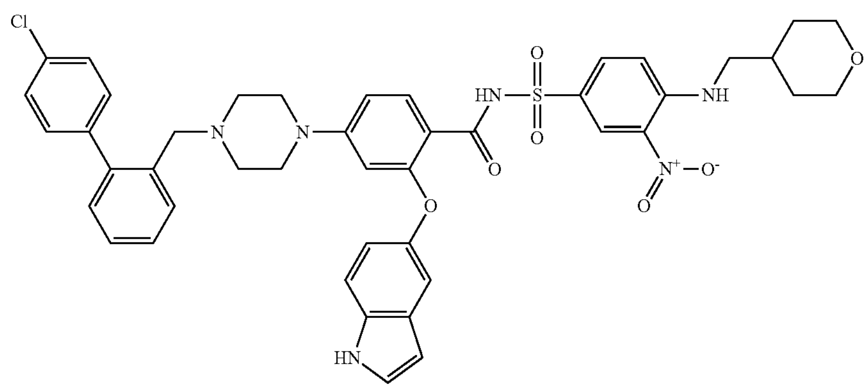 [SMILES: O=C(NS(=O)(=O)c1ccc(NCC2CCOCC2)c([N+](=O)[O-])c1)c1ccc(N2CCN(Cc3ccccc3-c3ccc(Cl)cc3)CC2)cc1Oc1ccc2[nH]ccc2c1] |
| 4-{4-[(4'-chloro-1,1'-biphenyl-2-yl)methyl]piperazin-1-yl}-2-(isoquinolin-5-yloxy)-N-({3-nitro-4-[(tetrahydro-2H-pyran-4-ylmethyl)amino]phenyl}sulfonyl)benzamide | 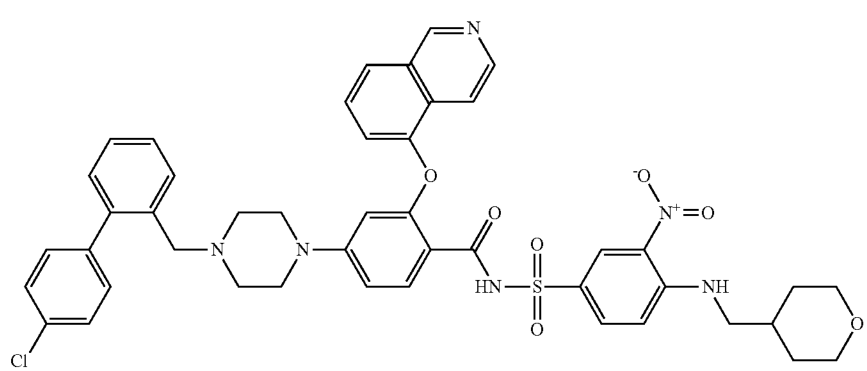 |

| Name | Structure |
|---|---|
| 4-{4-[(4'-chloro-1,1'-biphenyl-2-yl)methyl]piperazin-1-yl}-N-[(4-{[3-(dimethylamino)propyl]amino}-3-nitrophenyl)sulfonyl]-2-(isoquinolin-5-yloxy)benzamide | 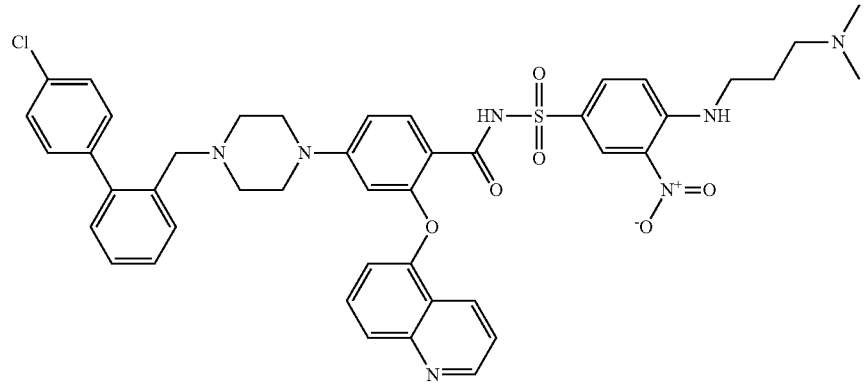 |
| 4-{4-[(4'-chloro-1,1'-biphenyl-2-yl)methyl]piperazin-1-yl}-N-[(4-{[3-(dimethylamino)propyl]amino}-3-nitrophenyl)sulfonyl]-2-(quinolin-6-yloxy)benzamide | 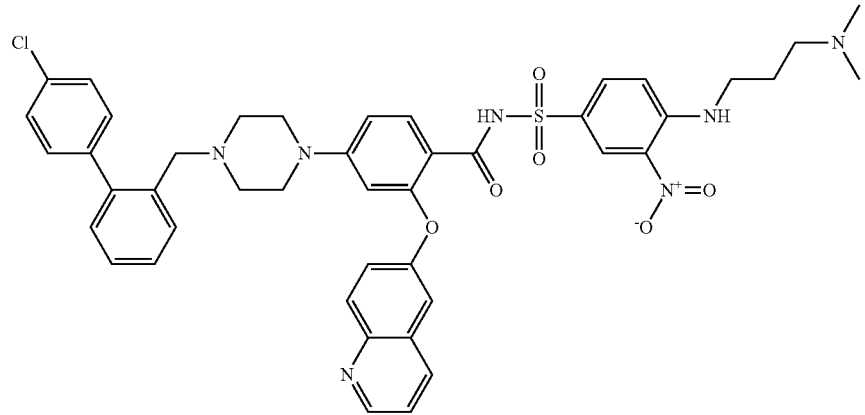 |
| 4-{4-[(4'-chloro-1,1'-biphenyl-2-yl)methyl]piperazin-1-yl}-N-[(4-{[3-(dimethylamino)propyl]amino}-3-nitrophenyl)sulfonyl]-2-(1H-indol-5-yloxy)benzamide | 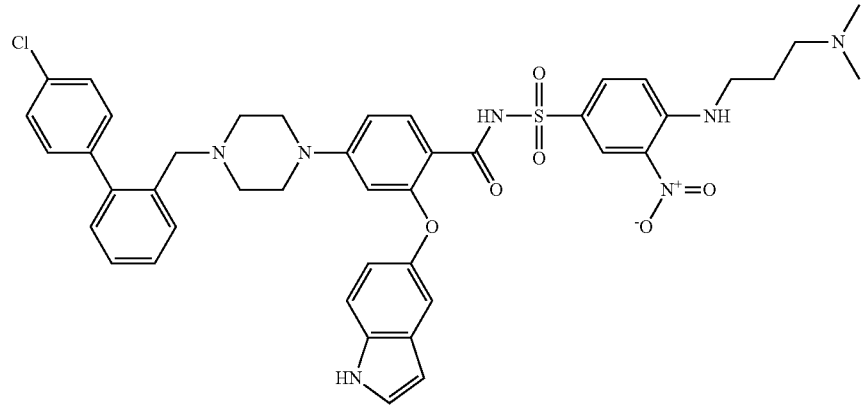 |
| 4-{4-[(4'-chloro-1,1'-biphenyl-2-yl)methyl]piperazin-1-yl}-2-(1H-indol-4-yloxy)-N-({3-nitro-4-[(tetrahydro-2H-pyran-4-ylmethyl)amino]phenyl}sulfonyl)benzamide | 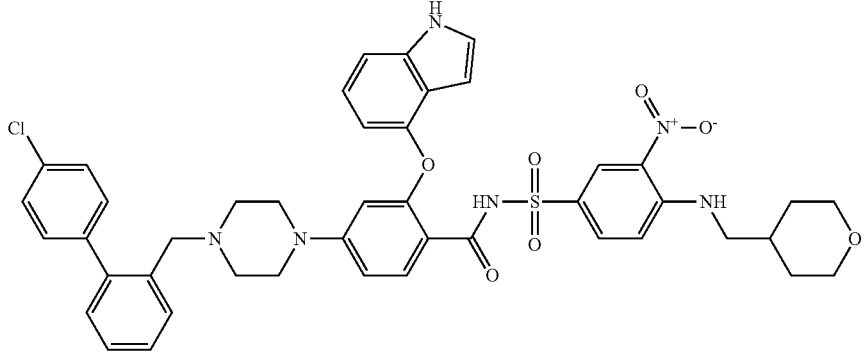 [SMILES: O=C(NS(=O)(=O)c1ccc(NCC2CCOCC2)c([N+](=O)[O-])c1)c1ccc(N2CCN(Cc3ccccc3-c3ccc(Cl)cc3)CC2)cc1Oc1cccc2[nH]ccc12] |

-continued

| Name | Structure |
|---|---|
| 4-{4-[(4'-chloro-1,1'-biphenyl-2-yl)methyl]piperazin-1-yl}-N-[(4-{[3-(dimethylamino)propyl]amino}-3-nitrophenyl)sulfonyl]-2-(1H-indol-4-yloxy)benzamide | 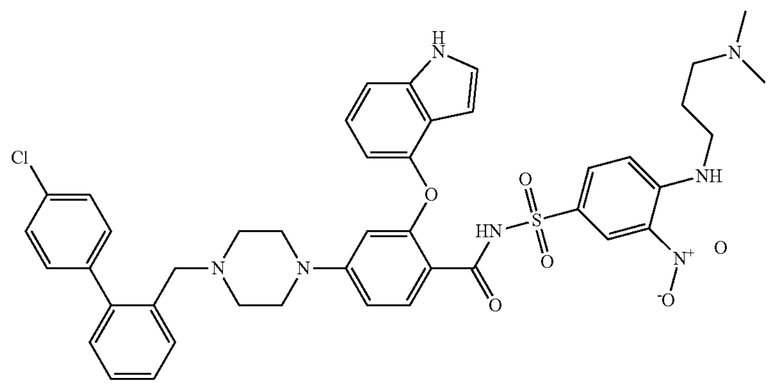 |
| 4-{4-[(4'-chloro-1,1'-biphenyl-2-yl)methyl]piperazin-1-yl}-N-[(4-{[3-(dimethylamino)propyl]amino}-3-nitrophenyl)sulfonyl]-2-(1H-indol-6-yloxy)benzamide | 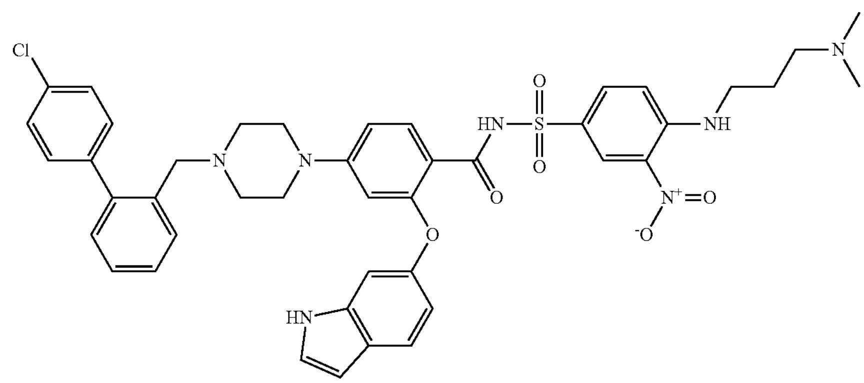 |
| 4-{4-[(4'-chloro-1,1'-biphenyl-2-yl)methyl]piperazin-1-yl}-2-(isoquinolin-7-yloxy)-N-({4-[(3-morpholin-4-ylpropyl)amino]-3-nitrophenyl}sulfonyl)benzamide | 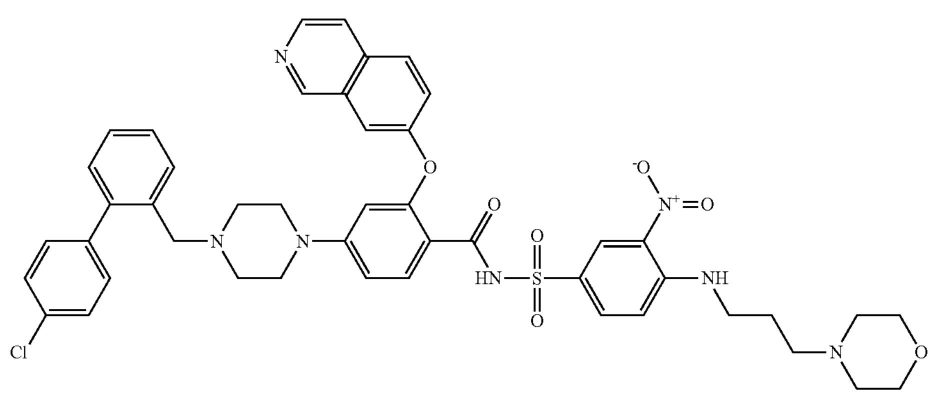 |
| 4-{4-[(4'-chloro-1,1'-biphenyl-2-yl)methyl]piperazin-1-yl}-N-[(4-{[3-(dimethylamino)propyl]amino}-3-nitrophenyl)sulfonyl]-2-(isoquinolin-7-yloxy)benzamide | 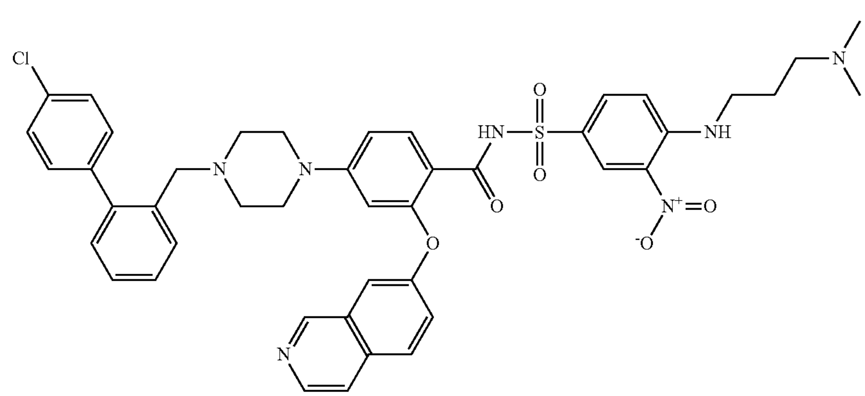 |

| Name | Structure |
|---|---|
| 4-(4-{[2-(4-chlorophenyl)-5,5-dimethylcyclohex-1-en-1-yl]methyl}piperazin-1-yl)-2-(1H-indol-5-yloxy)-N-({4-[(3-morpholin-4-ylpropyl)amino]-3-nitrophenyl}sulfonyl)benzamide | |
| 4-(4-{[2-(4-chlorophenyl)-5,5-dimethylcyclohex-1-en-1-yl]methyl}piperazin-1-yl)-N-[(4-{[3-(dimethylamino)propyl]amino}-3-nitrophenyl)sulfonyl]-2-(1H-indol-5-yloxy)benzamide | |
| 4-(4-{[2-(4-chlorophenyl)-4,4-dimethylcyclohex-1-en-1-yl]methyl}piperazin-1-yl)-2-(1H-indol-5-yloxy)-N-({4-[(3-morpholin-4-ylpropyl)amino]-3-nitrophenyl}sulfonyl)benzamide | |

| Name | Structure |
|---|---|
| 4-(4-{[2-(4-chlorophenyl)-4,4-dimethylcyclohex-1-en-1-yl]methyl}piperazin-1-yl)-N-[(4-{[3-(dimethylamino)propyl]amino}-3-nitrophenyl)sulfonyl]-2-(1H-indol-5-yloxy)benzamide | |
| 4-(4-{[2-(4-chlorophenyl)-5,5-dimethylcyclohex-1-en-1-yl]methyl}piperazin-1-yl)-2-(1H-indol-4-yloxy)-N-({4-[(3-morpholin-4-ylpropyl)amino]-3-nitrophenyl}sulfonyl)benzamide | |
| 4-(4-{[2-(4-chlorophenyl)-4,4-dimethylcyclohex-1-en-1-yl]methyl}piperazin-1-yl)-2-(1H-indol-4-yloxy)-N-({4-[(3-morpholin-4-ylpropyl)amino]-3-nitrophenyl}sulfonyl)benzamide | |

| Name | Structure |
|---|---|
| 4-(4-{[2-(4-chloro-phenyl)-5,5-dimethylcyclohex-1-en-1-yl]methyl]piperazin-1-yl)-N-[(4-{[3-(dimethylamino)propyl]amino}-3-nitrophenyl)sulfonyl]-2-(1H-indol-4-yloxy)benzamide | |
| 4-(4-{[2-(4-chloro-phenyl)-4,4-dimethylcyclohex-1-en-1-yl]methyl}piperazin-1-yl)-N-[(4-{[3-(dimethylamino)propyl]amino}-3-nitrophenyl)sulfonyl]-2-(1H-indol-4-yloxy)benzamide | 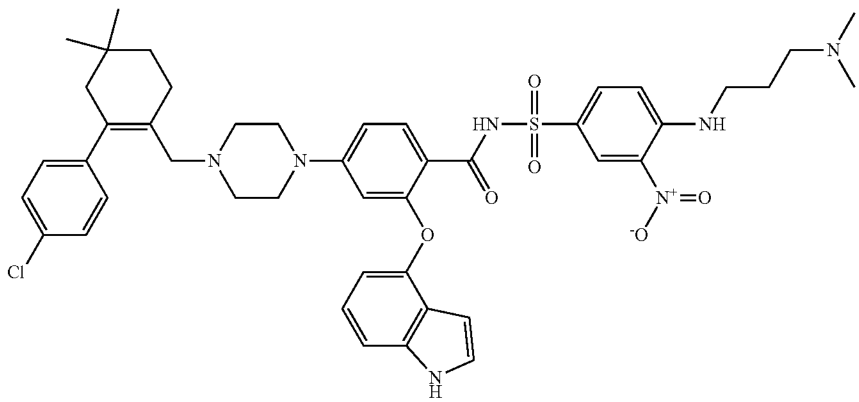 |
| 4-{4-[(4'-chloro-1,1'-biphenyl-2-yl)methyl]piperazin-1-yl}-2-(1H-indol-4-yloxy)-N-({4-[(3-morpholin-4-ylpropyl)amino]-3-nitrophenyl}sulfonyl)benzamide | 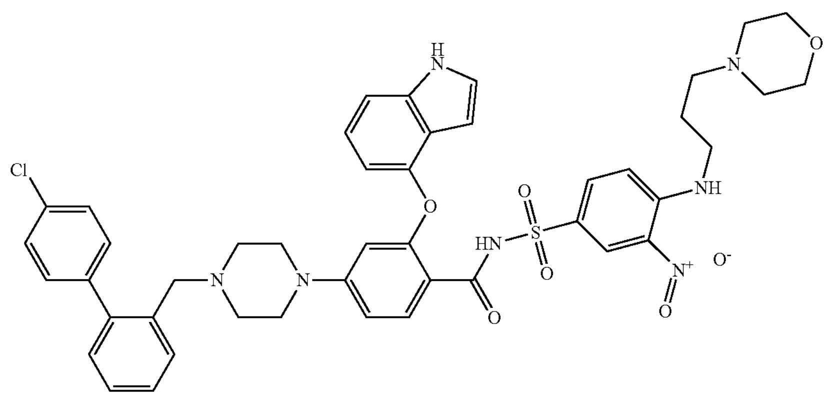 |
| 4-{4-[(4'-chloro-1,1'-biphenyl-2-yl)methyl]piperazin-1-yl}-2-(1H-indol-5-yloxy)-N-({4-[(3-morpholin-4-ylpropyl)amino]-3-nitrophenyl}sulfonyl)benzamide | 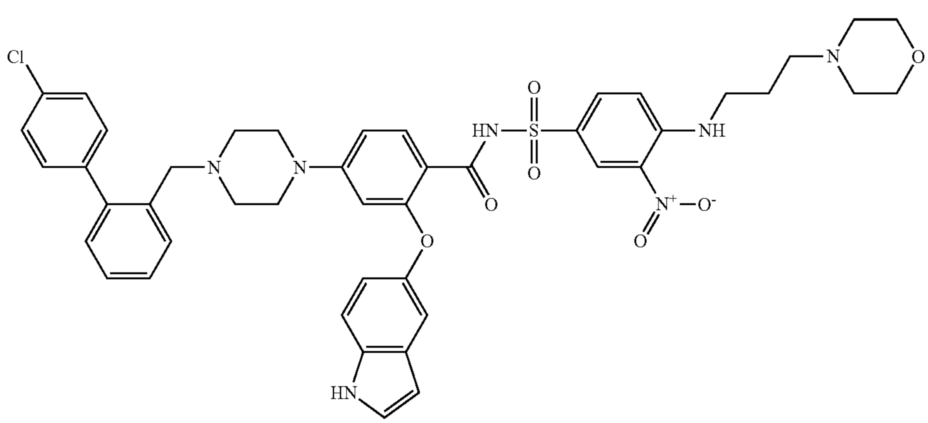 [SMILES: O=C(NS(=O)(=O)c1ccc(NCCCN2CCOCC2)c([N+](=O)[O-])c1)c1ccc(N2CCN(Cc3ccccc3-c3ccc(Cl)cc3)CC2)cc1Oc1ccc2[nH]ccc2c1] |

-continued

| Name | Structure |
|---|---|
| 4-{4-[(4'-chloro-1,1'-biphenyl-2-yl)methyl]piperazin-1-yl}-N-[(4-methoxyphenyl)sulfonyl]-2-phenoxybenzamide | 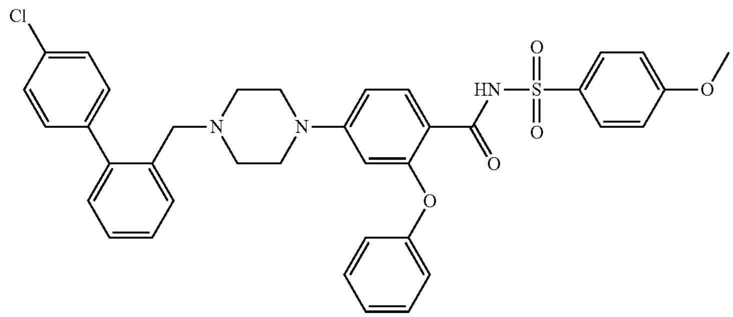 [SMILES: COc1ccc(S(=O)(=O)NC(=O)c2ccc(N3CCN(Cc4ccccc4-c4ccc(Cl)cc4)CC3)cc2Oc2ccccc2)cc1] |
| 4-{4-[(4'-chloro-1,1'-biphenyl-2-yl)methyl]piperazin-1-yl}-N-[(4-methylphenyl)sulfonyl]-2-phenoxybenzamide | 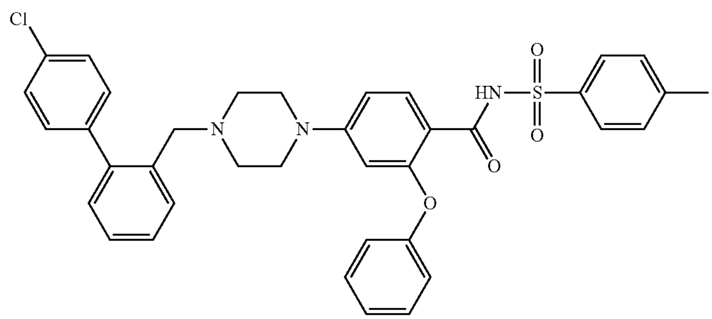 [SMILES: Cc1ccc(S(=O)(=O)NC(=O)c2ccc(N3CCN(Cc4ccccc4-c4ccc(Cl)cc4)CC3)cc2Oc2ccccc2)cc1] |
| 4-{4-[(4'-chloro-1,1'-biphenyl-2-yl)methyl]piperazin-1-yl}-2-(1H-indol-5-yloxy)-N-({4-[(tetrahydro-2H-pyran-4-ylmethyl)amino]-3-[(trifluoromethyl)sulfonyl]phenyl}sulfonyl)benzamide | 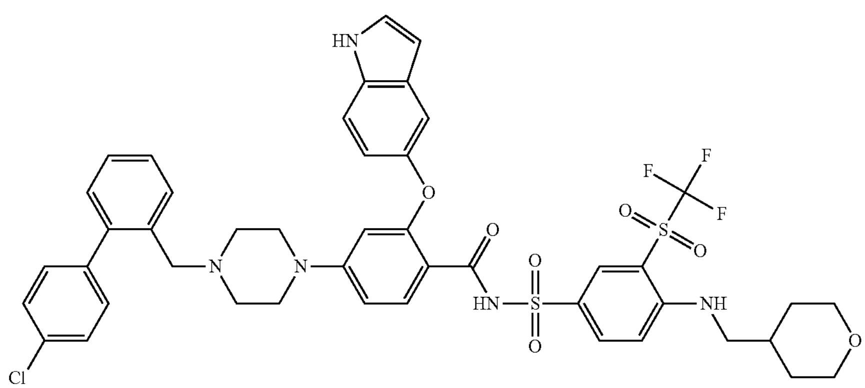 [SMILES: O=C(NS(=O)(=O)c1ccc(NCC2CCOCC2)c(S(=O)(=O)C(F)(F)F)c1)c1ccc(N2CCN(Cc3ccccc3-c3ccc(Cl)cc3)CC2)cc1Oc1ccc2[nH]ccc2c1] |
| 4-{4-[(4'-chloro-1,1'-biphenyl-2-yl)methyl]piperazin-1-yl}-2-(1H-indol-4-yloxy)-N-({4-[(tetrahydro-2H-pyran-4-ylmethyl)amino]-3-[(trifluoromethyl)sulfonyl]phenyl}sulfonyl)benzamide | 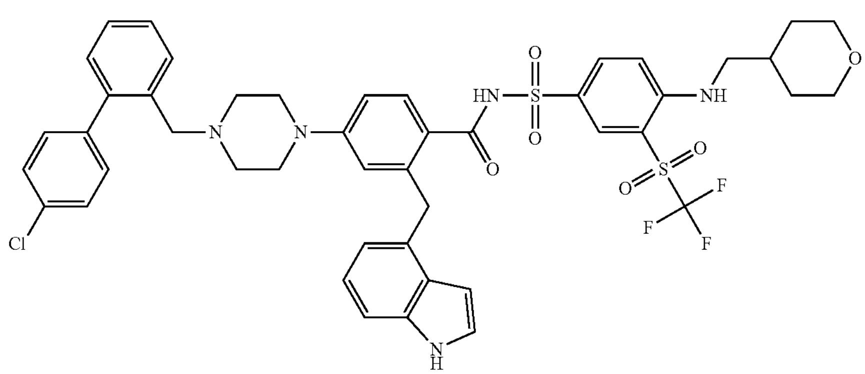 [SMILES: O=C(NS(=O)(=O)c1ccc(NCC2CCOCC2)c(S(=O)(=O)C(F)(F)F)c1)c1ccc(N2CCN(Cc3ccccc3-c3ccc(Cl)cc3)CC2)cc1Cc1cccc2[nH]ccc12] |

-continued

| Name | Structure |
|---|---|
| 4-{4-[(4'-chloro-1,1'-biphenyl-2-yl)methyl]piperazin-1-yl}-N-({4-{[3-(dimethylamino)propyl]amino}-3-[(trifluoromethyl)sulfonyl]phenyl}sulfonyl)-2-(1H-indol-5-yloxy)benzamide | 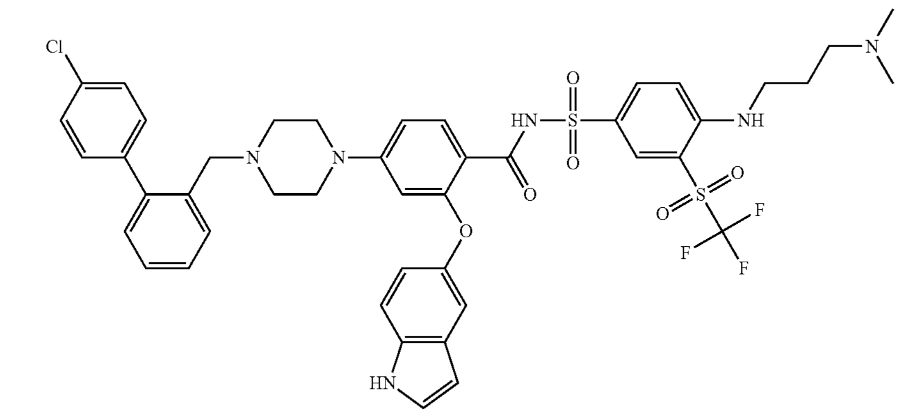 [SMILES: CN(C)CCCNc1ccc(S(=O)(=O)NC(=O)c2ccc(N3CCN(Cc4ccccc4-c4ccc(Cl)cc4)CC3)cc2Oc2ccc3[nH]ccc3c2)cc1S(=O)(=O)C(F)(F)F] |
| 4-{4-[(4'-chloro-1,1'-biphenyl-2-yl)methyl]piperazin-1-yl}-2-(1H-indol-4-yloxy)-N-({4-[(3-morpholin-4-ylpropyl)amino]-3-[(trifluoromethyl)sulfonyl]phenyl}sulfonyl)benzamide | 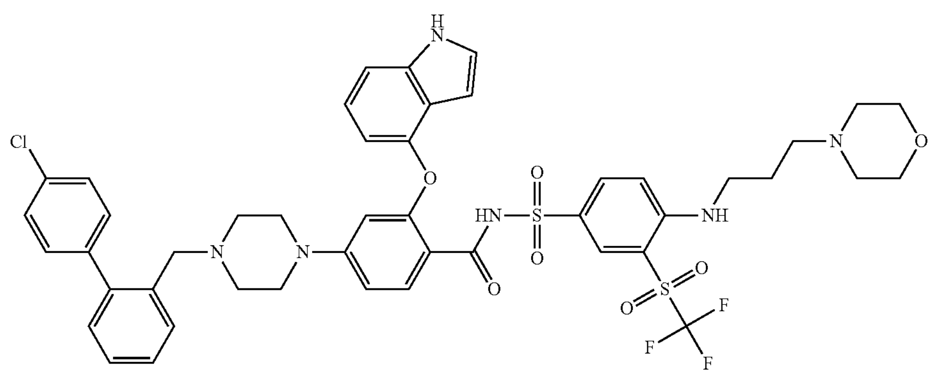 [SMILES: O=C(NS(=O)(=O)c1ccc(NCCCN2CCOCC2)c(S(=O)(=O)C(F)(F)F)c1)c1ccc(N2CCN(Cc3ccccc3-c3ccc(Cl)cc3)CC2)cc1Oc1cccc2[nH]ccc12] |
| N-[(3-{[chloro(difluoro)methyl]sulfonyl}-4-{[3-(dimethylamino)propyl]amino}phenyl)sulfonyl]-4-(4-{[2-(4-chlorophenyl)-4,4-dimethylcyclohex-1-en-1-yl]methyl}piperazin-1-yl)-2-(1H-indol-4-yloxy)benzamide | |
| N-[(3-{[chloro(difluoro)methyl]sulfonyl}-4-{[3-(dimethylamino)propyl]amino}phenyl)sulfonyl]-4-(4-{[2-(4-chlorophenyl)-4,4-dimethylcyclohex-1-en-1-yl]methyl}piperazin-1-yl)-2-(1H-indol-5-yloxy)benzamide | 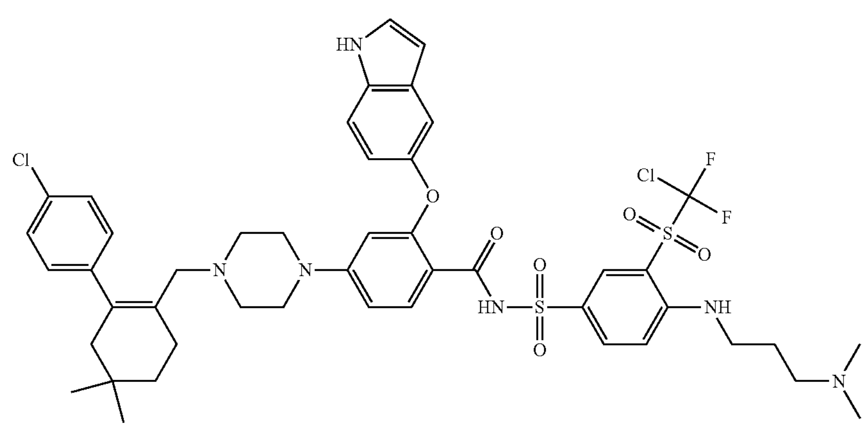 [SMILES: CN(C)CCCNc1ccc(S(=O)(=O)NC(=O)c2ccc(N3CCN(CC4=C(c5ccc(Cl)cc5)CC(C)(C)CC4)CC3)cc2Oc2ccc3[nH]ccc3c2)cc1S(=O)(=O)C(F)(F)Cl] |

-continued

| Name | Structure |
|---|---|
| 2-(1H-indol-4-yloxy)-4-(4-{[2-(4-methoxyphenyl)-4,4-dimethylcyclohex-1-en-1-yl]methyl}piperazin-1-yl)-N-({3-nitro-4-[(3-pyrrolidin-1-ylpropyl)amino]phenyl}sulfonyl)benzamide | 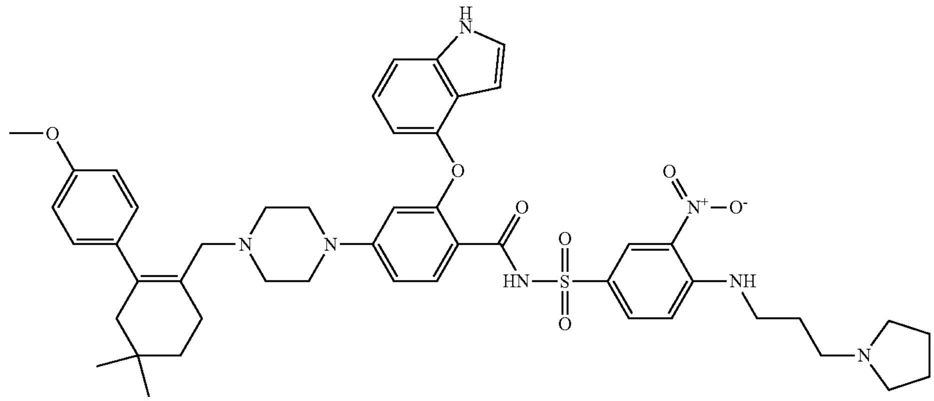 [SMILES: COc1ccc(C2=C(CN3CCN(c4ccc(C(=O)NS(=O)(=O)c5ccc(NCCCN6CCCC6)c([N+](=O)[O-])c5)c(Oc5cccc6[nH]ccc56)c4)CC3)CCC(C)(C)C2)cc1] |
| 4-[4-({4,4-dimethyl-2-[4-(trifluoromethyl)phenyl]cyclohex-1-en-1-yl}methyl)piperazin-1-yl]-2-(1H-indol-4-yloxy)-N-({3-nitro-4-[(3-pyrrolidin-1-ylpropyl)amino]phenyl}sulfonyl)benzamide | 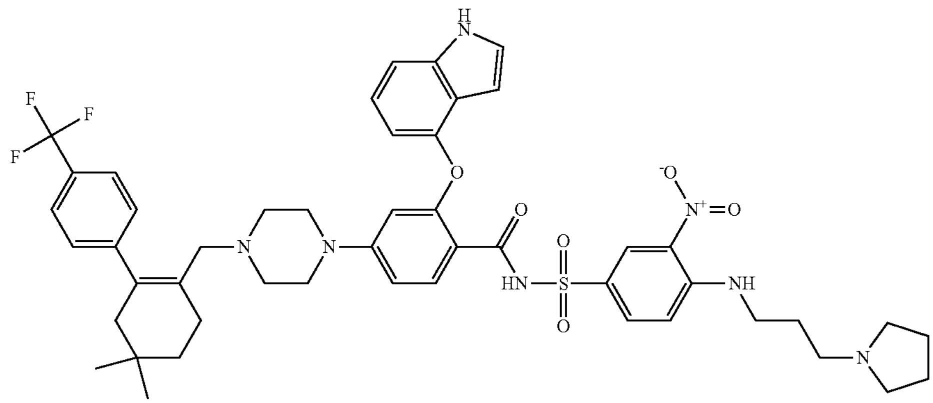 |
| 4-[4-({4,4-dimethyl-2-[4-(trifluoromethoxy)phenyl]cyclohex-1-en-1-yl}methyl)piperazin-1-yl]-2-(1H-indol-4-yloxy)-N-({3-nitro-4-[(3-pyrrolidin-1-ylpropyl)amino]phenyl}sulfonyl)benzamide | 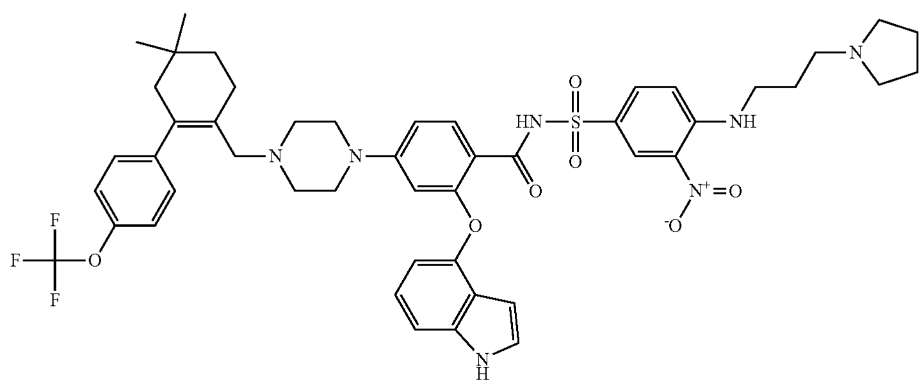 |
| 4-[4-({4,4-dimethyl-2-[3-(trifluoromethyl)phenyl]cyclohex-1-en-1-yl}methyl)piperazin-1-yl]-2-(1H-indol-4-yloxy)-N-({3-nitro-4-[(3-pyrrolidin-1-ylpropyl)amino]phenyl}sulfonyl)benzamide | 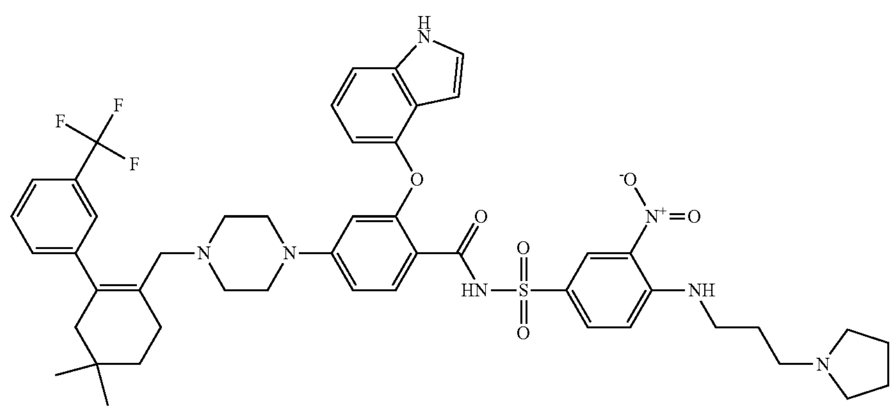 |

| Name | Structure |
|---|---|
| 4-(4-{[2-(3-fluoro-phenyl)-4,4-dimethylcyclohex-1-en-1-yl]methyl}piperazin-1-yl)-2-(1H-indol-4-yloxy)-N-({3-nitro-4-[(3-pyrrolidin-1-ylpropyl)amino]phenyl}sulfonyl)benzamide | 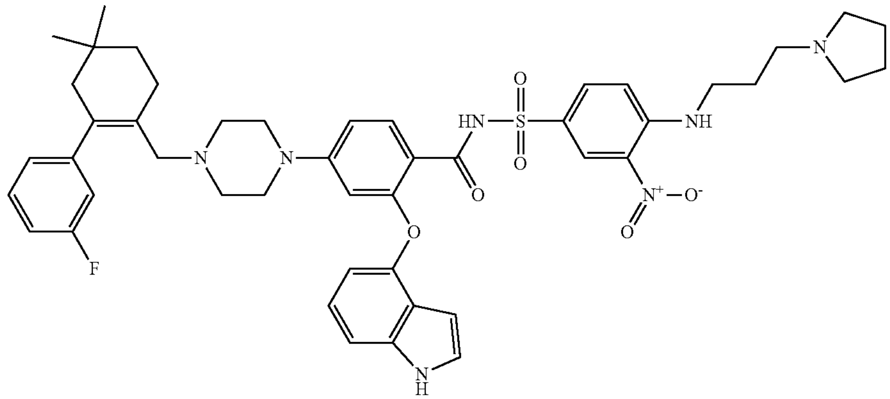 [SMILES: CC1(C)CCC(CN2CCN(c3ccc(C(=O)NS(=O)(=O)c4ccc(NCCCN5CCCC5)c([N+](=O)[O-])c4)c(Oc4cccc5[nH]ccc45)c3)CC2)=C(c2cccc(F)c2)C1] |
| 4-(4-{[2-(4-fluoro-phenyl)-4,4-dimethyl-cyclohex-1-en-1-yl]methyl}piperazin-1-yl)-2-(1H-indol-4-yloxy)-N-({3-nitro-4-[(3-pyrrolidin-1-ylpropyl)amino]phenyl}sulfonyl)benzamide | 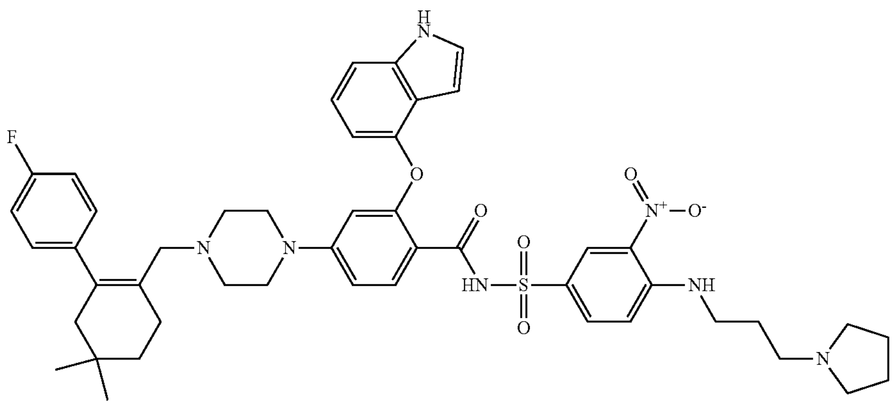 [SMILES: CC1(C)CCC(CN2CCN(c3ccc(C(=O)NS(=O)(=O)c4ccc(NCCCN5CCCC5)c([N+](=O)[O-])c4)c(Oc4cccc5[nH]ccc45)c3)CC2)=C(c2ccc(F)cc2)C1] |
| N-({3-{[chloro(difluoro)methyl]sulfonyl}-4-[(1-methylpiperidin-4-yl)amino]phenyl}sulfonyl)-4-(4-{[2-(4-chlorophenyl)-4,4-dimethylcyclohex-1-en-1-yl]methyl}piperazin-1-yl)-2-(1H-indol-5-yloxy)benzamide | 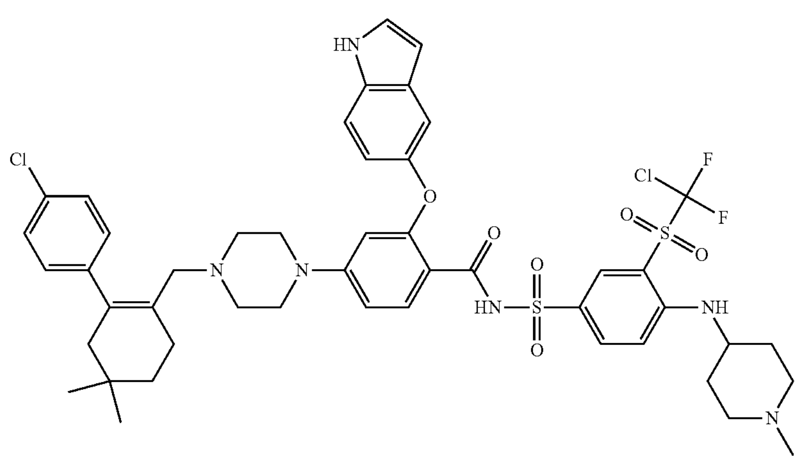 [SMILES: CN1CCC(Nc2ccc(S(=O)(=O)NC(=O)c3ccc(N4CCN(CC5=C(c6ccc(Cl)cc6)CC(C)(C)CC5)CC4)cc3Oc3ccc4[nH]ccc4c3)cc2S(=O)(=O)C(F)(F)Cl)CC1] |

| Name | Structure |
|---|---|
| 4-(4-{[2-(4-chloro-phenyl)cyclohex-1-en-1-yl]methyl}piperazin-1-yl)-2-(1H-indol-5-yloxy)-N-({4-[(1-methylpiperidin-4-yl)amino]-3-nitrophenyl}sulfonyl)benzamide | |
| 4-(4-{[2-(4-chloro-phenyl)-4,4-dimethyl-cyclohex-1-en-1-yl]methyl}piperazin-1-yl)-2-(1H-indol-5-yloxy)-N-({4-[(1-methylpiperidin-4-yl)amino]-3-[(trifluoromethyl)sulfonyl]phenyl}sulfonyl)benzamide | |
| 4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)-2-(phenoxymethyl)benzamide | 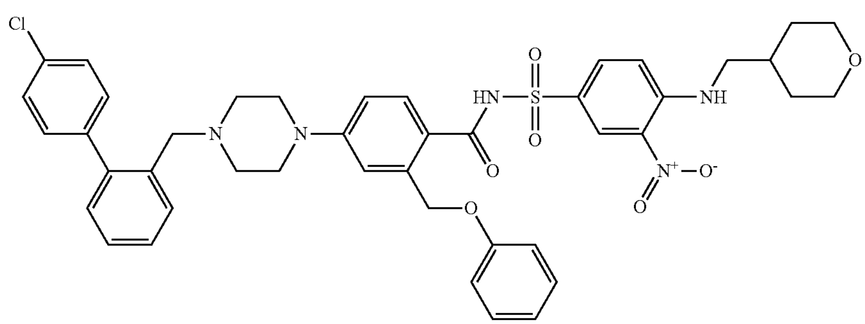 |
| 4-{4-[(4'-chloro-1,1'-biphenyl-2-yl)methyl]piperazin-1-yl}-N-({4-[(3-morpholin-4-ylpropyl)amino]phenyl}sulfonyl)-2-phenoxybenzamide | 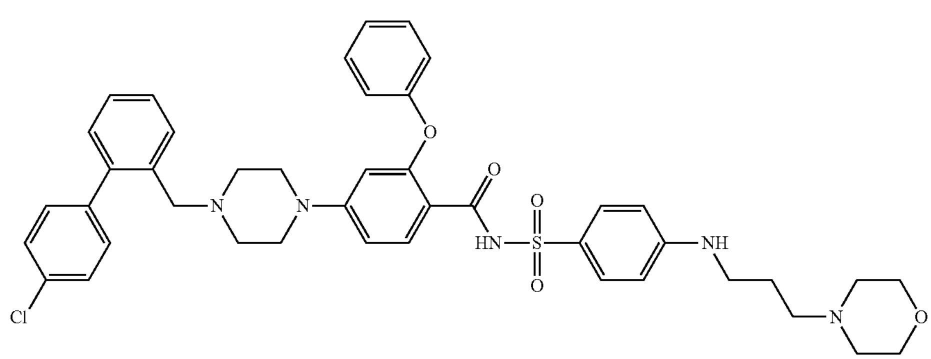 [SMILES: O=C(NS(=O)(=O)c1ccc(NCCCN2CCOCC2)cc1)c1ccc(N2CCN(Cc3ccccc3-c3ccc(Cl)cc3)CC2)cc1Oc1ccccc1] |

-continued

| Name | Structure |
|---|---|
| 4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)-2-(pyridin-3-yloxy)benzamide | 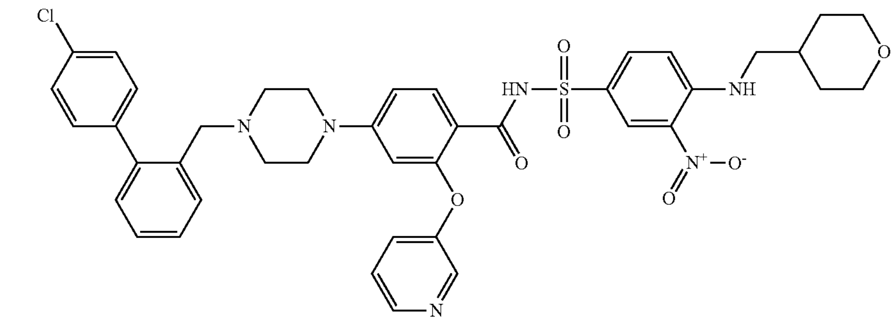 [SMILES: O=C(NS(=O)(=O)c1ccc(NCC2CCOCC2)c([N+](=O)[O-])c1)c1ccc(N2CCN(Cc3ccccc3-c3ccc(Cl)cc3)CC2)cc1Oc1cccnc1] |
| 4-{4-[(4'-chloro-1,1'-biphenyl-2-yl)methyl]piperazin-1-yl}-2-(pyridin-3-yloxy)-N-({4-[(tetrahydro-2H-pyran-4-ylmethyl)amino]phenyl}sulfonyl)benzamide | 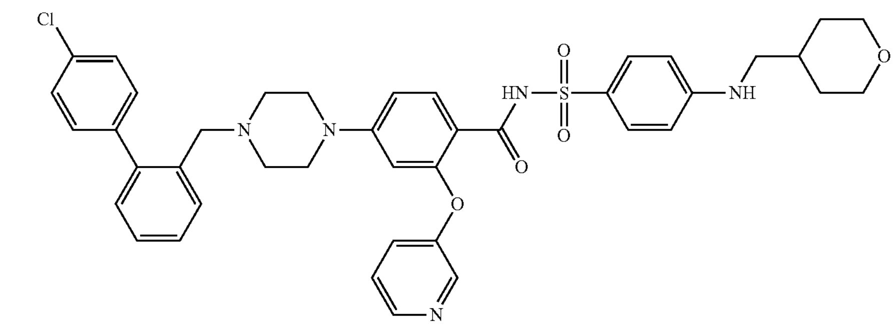 [SMILES: O=C(NS(=O)(=O)c1ccc(NCC2CCOCC2)cc1)c1ccc(N2CCN(Cc3ccccc3-c3ccc(Cl)cc3)CC2)cc1Oc1cccnc1] |
| 4-{4-[(4'-chloro-1,1'-biphenyl-2-yl)methyl]piperazin-1-yl}-N-{[4-({(1R)-3-(dimethylamino)-1-[(phenylthio)methyl]propyl}amino)-3-nitrophenyl]sulfonyl}-2-phenoxybenzamide | 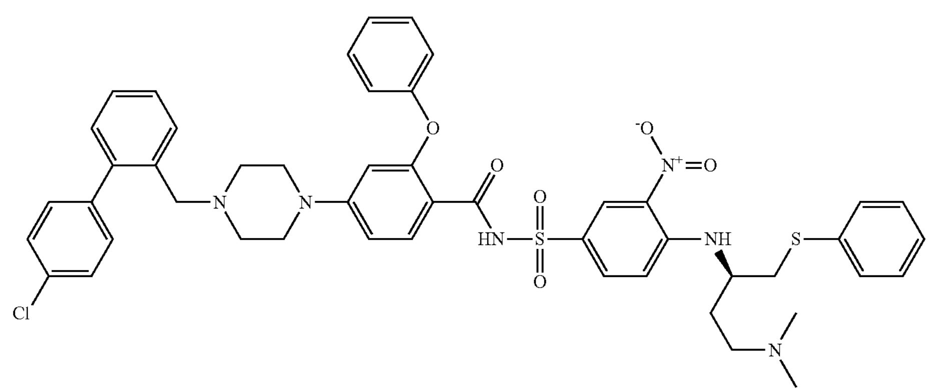 |
| 4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)-2-(pyridin-4-yloxy)benzamide | 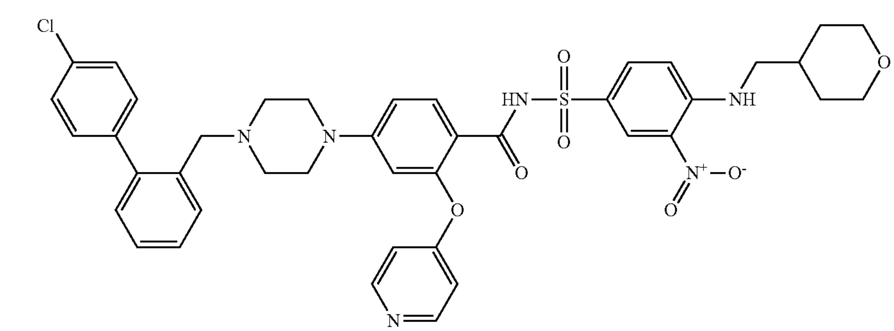 [SMILES: O=C(NS(=O)(=O)c1ccc(NCC2CCOCC2)c([N+](=O)[O-])c1)c1ccc(N2CCN(Cc3ccccc3-c3ccc(Cl)cc3)CC2)cc1Oc1ccncc1] |

| Name | Structure |
|---|---|
| 4-{4-[(4'-chloro-1,1'-biphenyl-2-yl)methyl]piperazin-1-yl}-N-({4-[(3-morpholin-4-ylpropyl)amino]-3-nitrophenyl}sulfonyl)-2-(pyridin-3-yloxy)benzamide | 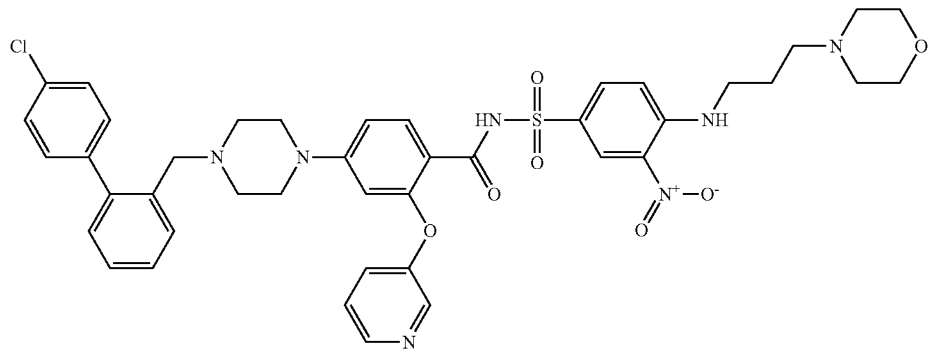 [SMILES: O=C(NS(=O)(=O)c1ccc(NCCCN2CCOCC2)c([N+](=O)[O-])c1)c1ccc(N2CCN(Cc3ccccc3-c3ccc(Cl)cc3)CC2)cc1Oc1cccnc1] |
| 4-{4-[(4'-chloro-1,1'-biphenyl-2-yl)methyl]piperazin-1-yl}-N-({4-[(3-morpholin-4-ylpropyl)amino]-3-nitrophenyl}sulfonyl)-2-(pyridin-4-yloxy)benzamide | 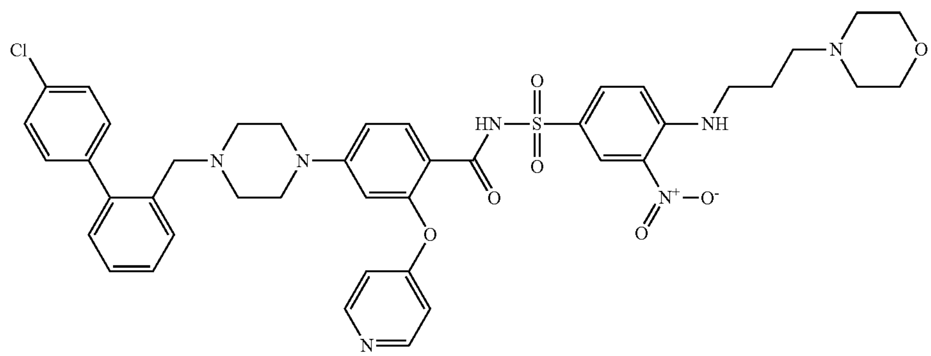 [SMILES: O=C(NS(=O)(=O)c1ccc(NCCCN2CCOCC2)c([N+](=O)[O-])c1)c1ccc(N2CCN(Cc3ccccc3-c3ccc(Cl)cc3)CC2)cc1Oc1ccncc1] |
| 4-{4-[(4'-chloro-1,1'-biphenyl-2-yl)methyl]piperazin-1-yl}-N-[(4-{[2-(4-methylpiperazin-1-yl)ethyl]amino}-3-nitrophenyl)sulfonyl]-2-phenoxybenzamide | 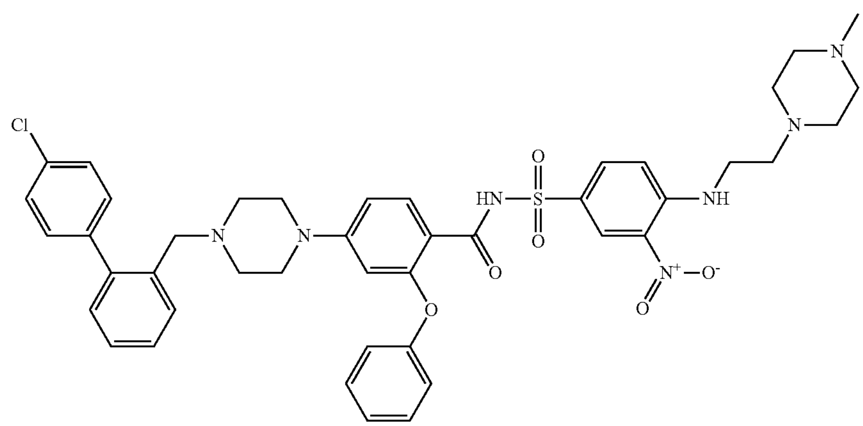 [SMILES: CN1CCN(CCNc2ccc(S(=O)(=O)NC(=O)c3ccc(N4CCN(Cc5ccccc5-c5ccc(Cl)cc5)CC4)cc3Oc3ccccc3)cc2[N+](=O)[O-])CC1] |
| 4-{4-[(4'-chloro-1,1'-biphenyl-2-yl)methyl]piperazin-1-yl}-N-[(4-{[3-(4-methylpiperazin-1-yl)propyl]amino}-3-nitrophenyl)sulfonyl]-2-phenoxybenzamide | 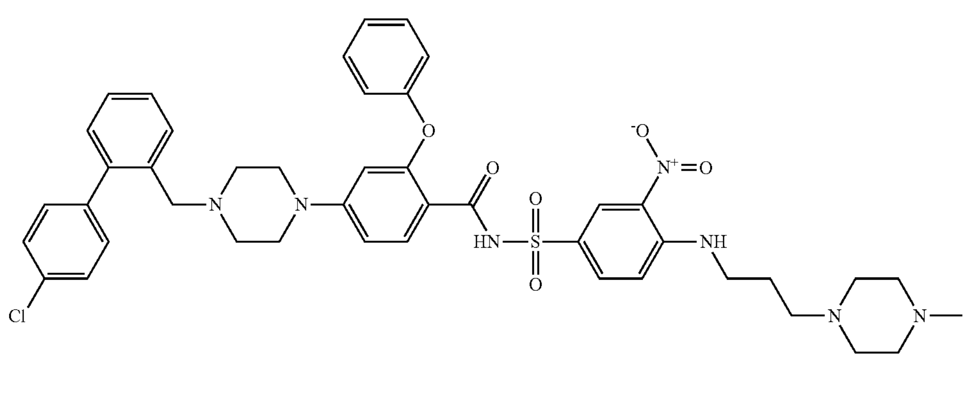 |

-continued

| Name | Structure |
|---|---|
| 4-{4-[(4'-chloro-1,1'-biphenyl-2-yl)methyl]piperazin-1-yl}-N-({4-[[3-(dimethylamino)propyl](methyl)amino]-3-nitrophenyl}sulfonyl)-2-phenoxybenzamide | 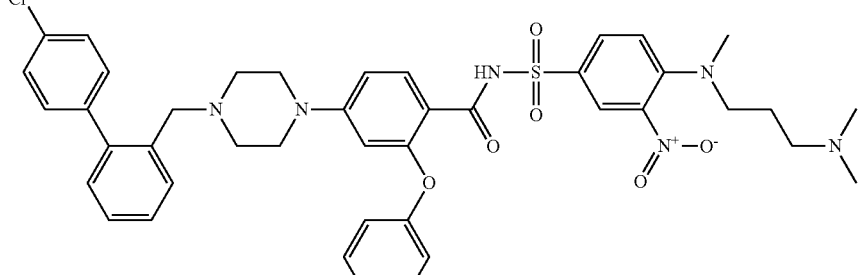 |
| 4-{4-[(4'-chloro-1,1'-biphenyl-2-yl)methyl]piperazin-1-yl}-N-[(4-{[(1-methylpiperidin-4-yl)methyl]amino}-3-nitrophenyl)sulfonyl]-2-phenoxybenzamide | 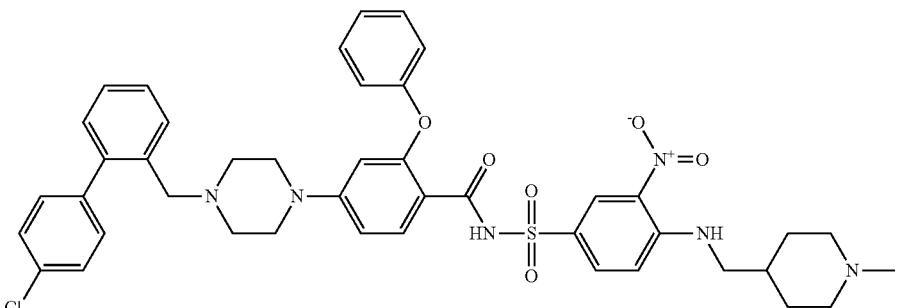 |
| 4-{4-[(4'-chloro-1,1'-biphenyl-2-yl)methyl]piperazin-1-yl}-N-({4-[(1-methylpiperidin-4-yl)amino]-3-nitrophenyl}sulfonyl)-2-phenoxybenzamide | 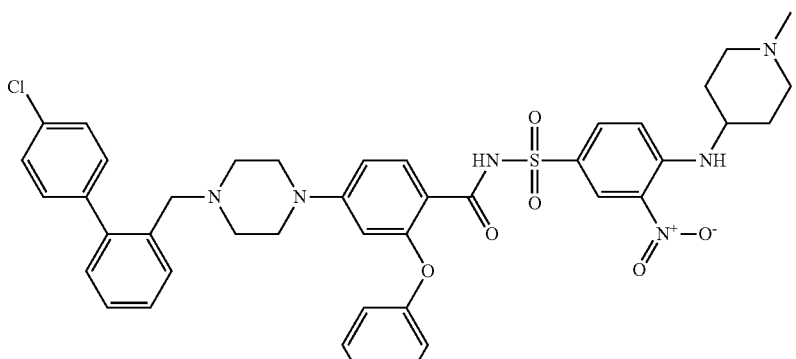 |
| 4-{4-[(4'-chloro-1,1'-biphenyl-2-yl)methyl]piperazin-1-yl}-N-[(3-cyano-4-{[3-(dimethylamino)propyl]amino}phenyl)sulfonyl]-2-phenoxybenzamide | 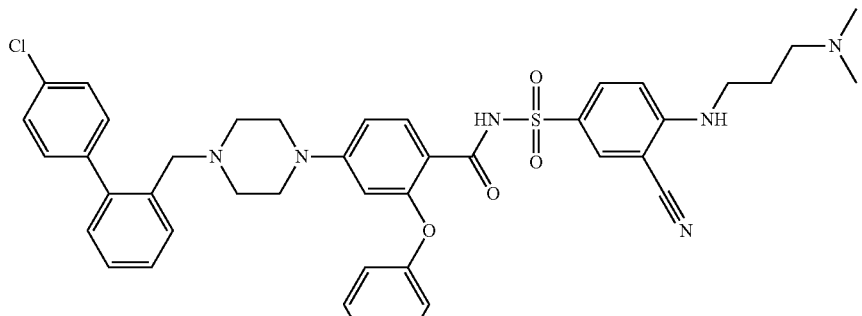 |

| Name | Structure |
|---|---|
| 4-{4-[(4'chloro-1,1'-biphenyl-2-yl)methyl]piperazin-1-yl}-N-({3-nitro-4-[(3-pyrrolidin-1-ylpropyl)amino]phenyl}sulfonyl)-2-phenoxybenzamide | 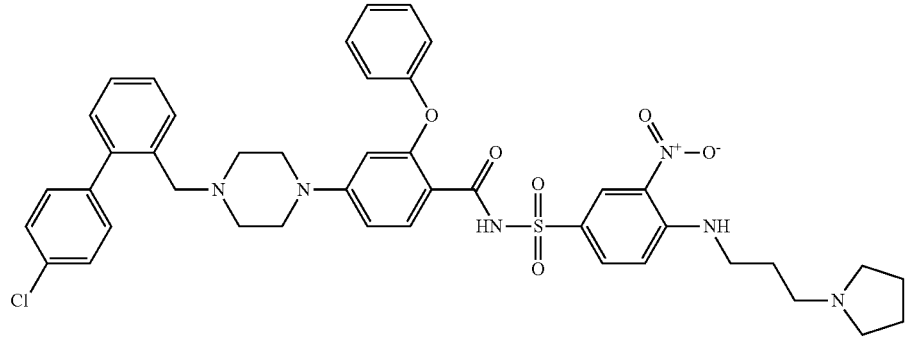 [SMILES: O=C(NS(=O)(=O)c1ccc(NCCCN2CCCC2)c([N+](=O)[O-])c1)c1ccc(N2CCN(Cc3ccccc3-c3ccc(Cl)cc3)CC2)cc1Oc1ccccc1] |
| 4-{4-[(4'-chloro-1,1'-biphenyl-2-yl)methyl]piperazin-1-yl}-N-{[4-{[3-(dimethylamino)propyl]amino 1-3-(trifluoromethyl)phenyl]sulfonyl}-2-phenoxybenzamide | 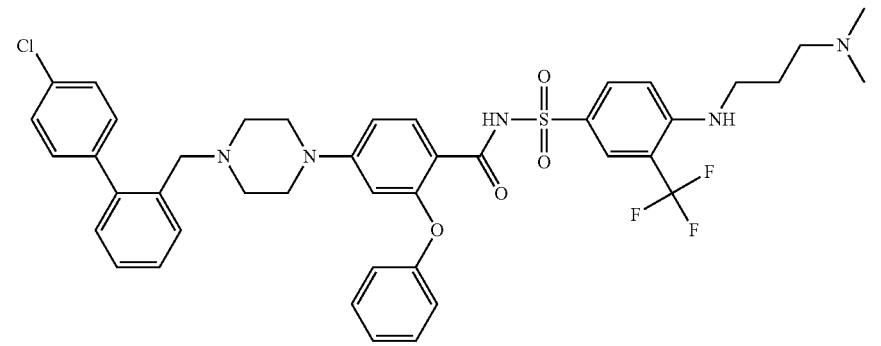 [SMILES: CN(C)CCCNc1ccc(S(=O)(=O)NC(=O)c2ccc(N3CCN(Cc4ccccc4-c4ccc(Cl)cc4)CC3)cc2Oc2ccccc2)cc1C(F)(F)F] |
| 4-{4-[(4'-chloro-1,1'-biphenyl-2-yl)methyl]piperazin-1-yl}-N-{[4-({3-[isopropyl(methyl)amino]propyl}amino)-3-nitrophenyl]sulfonyl}-2-phenoxybenzamide | 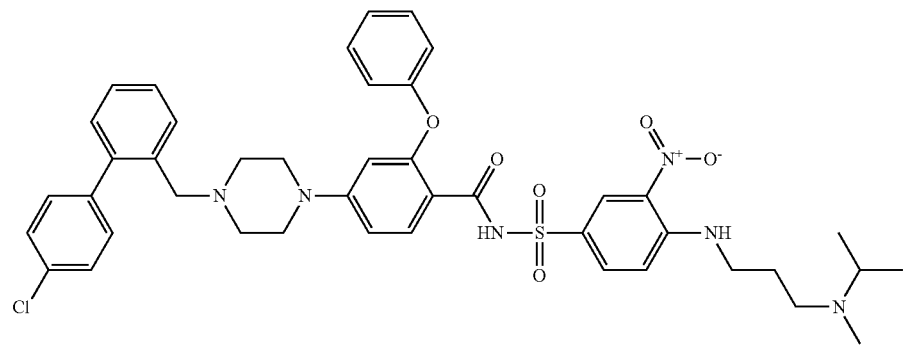 [SMILES: CC(C)N(C)CCCNc1ccc(S(=O)(=O)NC(=O)c2ccc(N3CCN(Cc4ccccc4-c4ccc(Cl)cc4)CC3)cc2Oc2ccccc2)cc1[N+](=O)[O-]] |
| 4-{4-[(4'chloro-1,1'-biphenyl-2-yl)methyl]piperazin-1-yl}-N-({4-[3-(dimethylamino)propoxy]-3-nitrophenyl}sulfonyl)-2-phenoxybenzamide | 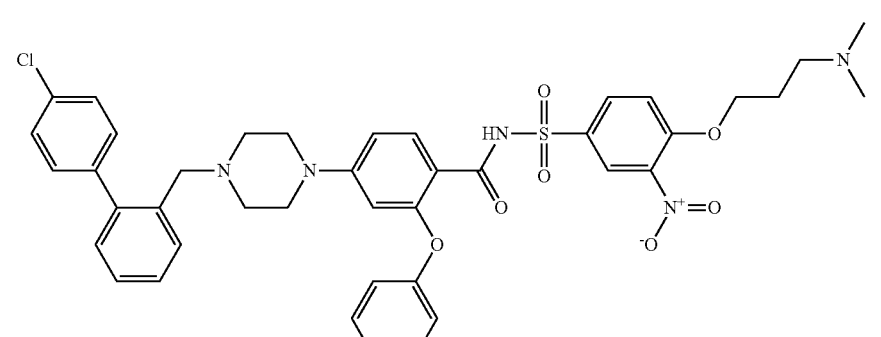 |

-continued

| Name | Structure |
|---|---|
| 4-(4-{[2-(4-chlorophenyl)-4,4-dimethylcyclohex-1-en-1-yl]methyl}piperazin-1-yl)-2-(1H-indol-5-yloxy)-N-[(4-{[2-(4-methylpiperazin-1-yl)ethyl]amino}-3-nitrophenyl)sulfonyl]benzamide | |
| 4-(4-{[2-(4-chlorophenyl)-4,4-dimethylcyclohex-1-en-1-yl]methyl}piperazin-1-yl)-2-(1H-indol-5-yloxy)-N-[(4-{[3-(4-methylpiperazin-1-yl)propyl]amino}-3-nitrophenyl)sulfonyl]benzamide | |
| 4-(4-{[2-(4-chlorophenyl)-4,4-dimethylcyclohex-1-en-1-yl]methyl}piperazin-1-yl)-2-(1H-indol-5-yloxy)-N-({3-nitro-4-[(3-pyrrolidin-1-ylpropyl)amino]phenyl}sulfonyl)benzamide | |

-continued

| Name | Structure |
|---|---|
| 4-(4-{[2-(4-chloro-phenyl)-4,4-dimethylcyclohex-1-en-1-yl]methyl}piperazin-1-yl)-2-(1H-indol-5-yloxy)-N-({4-[(1-methyl-piperidin-4-yl)amino]-3-nitrophenyl}sulfonyl)benzamide | 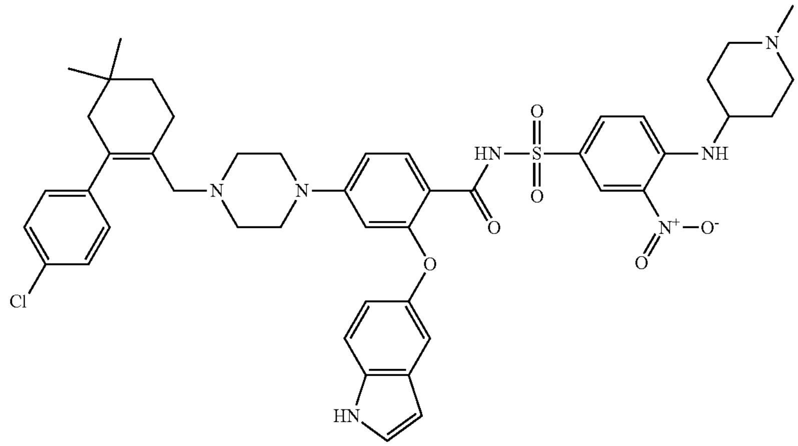 [SMILES: CN1CCC(Nc2ccc(S(=O)(=O)NC(=O)c3ccc(N4CCN(CC5=C(c6ccc(Cl)cc6)CC(C)(C)CC5)CC4)cc3Oc3ccc4[nH]ccc4c3)cc2[N+](=O)[O-])CC1] |
| 4-(4-{[2-(4-chloro-phenyl)-4,4-dimethylcyclohex-1-en-1-yl]methyl}piperazin-1-yl)-2-(1H-indol-4-yloxy)-N-[(4-{3-(4-methyl-piperazin-1-yl)propyl]amino}-3-nitrophenyl)sulfonyl]benzamide | |
| 4-(4-{[2-(4-chloro-phenyl)-4,4-dimethylcyclohex-1-en-1-yl]methyl}piperazin-1-yl)-N-({4-[3-(dimethyl-amino)propoxy]-3-nitrophenyl}sulfonyl)-2-(1H-indol-5-yloxy)benzamide | 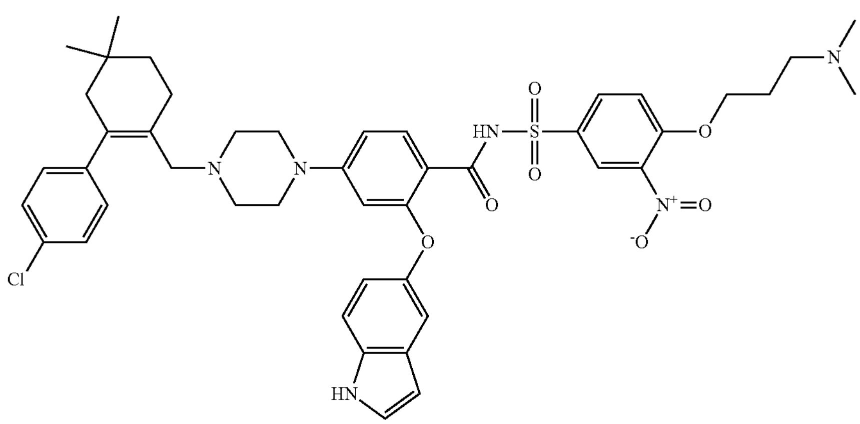 |

| Name | Structure |
|------|-----------|
| 4-(4-{[2-(4-chloro-phenyl)-4,4-dimethylcyclohex-1-en-1-yl]methyl}piperazin-1-yl)-2-(1H-indol-4-yloxy)-N-[(4-{[2-(4-methyl-piperazin-1-yl)ethyl]amino}-3-nitrophenyl)sulfonyl]benzamide | 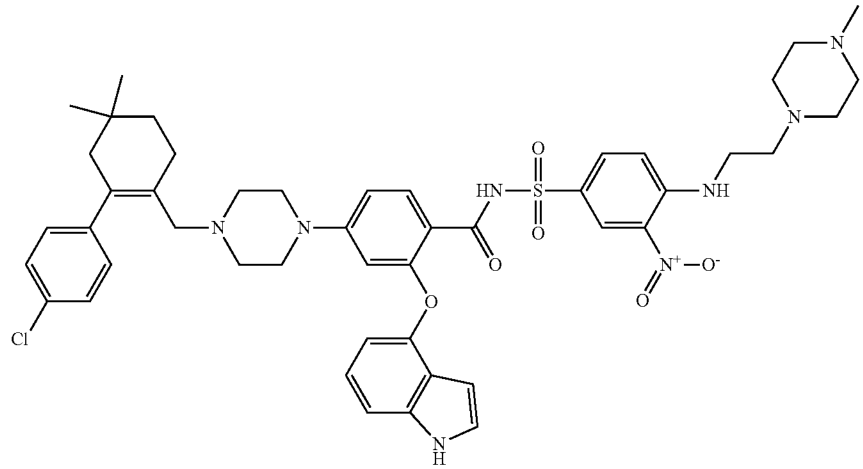 [SMILES: CN1CCN(CCNc2ccc(S(=O)(=O)NC(=O)c3ccc(N4CCN(CC5=C(c6ccc(Cl)cc6)CC(C)(C)CC5)CC4)cc3Oc3cccc4[nH]ccc34)cc2[N+](=O)[O-])CC1] |
| 4-(4-{[2-(4-chloro-phenyl)-4,4-dimethylcyclohex-1-en-1-yl]methyl}piperazin-1-yl)-2-(1H-indol-4-yloxy)-N-({3-nitro-4-[(3-pyrrolidin-1-ylpropyl)amino]phenyl}sulfonyl)benzamide | 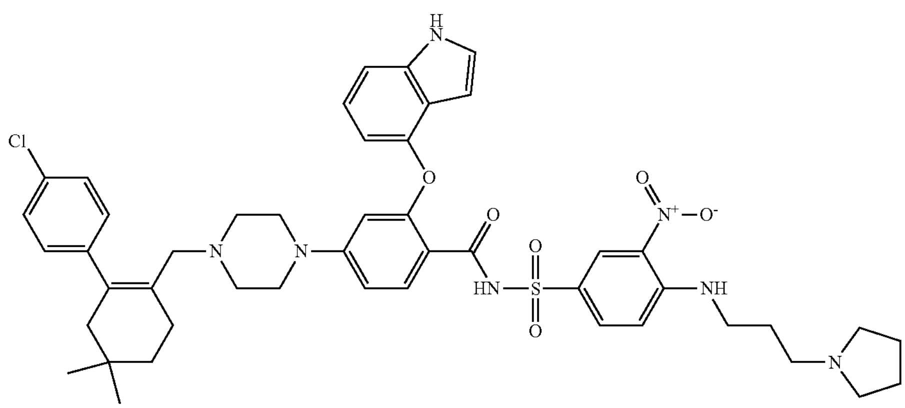 [SMILES: CC1(C)CCC(CN2CCN(c3ccc(C(=O)NS(=O)(=O)c4ccc(NCCCN5CCCC5)c([N+](=O)[O-])c4)c(Oc4cccc5[nH]ccc45)c3)CC2)=C(c2ccc(Cl)cc2)C1] |
| 4-(4-{[2-(4-chloro-phenyl)-4,4-dimethylcyclohex-1-en-1-yl]methyl}piperazin-1-yl)-2-(1H-indol-4-yloxy)-N-({4-[(1-methyl-piperidin-4-yl)amino]-3-nitrophenyl}sulfonyl)benzamide | 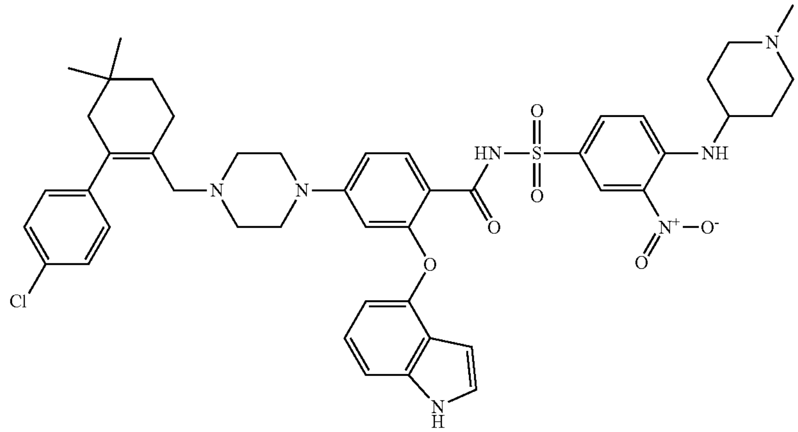 [SMILES: CN1CCC(Nc2ccc(S(=O)(=O)NC(=O)c3ccc(N4CCN(CC5=C(c6ccc(Cl)cc6)CC(C)(C)CC5)CC4)cc3Oc3cccc4[nH]ccc34)cc2[N+](=O)[O-])CC1] |

-continued

| Name | Structure |
|---|---|
| 4-(4-{[2-(4-chlorophenyl)-4,4-dimethylcyclohex-1-en-1-yl]methyl}piperazin-1-yl)-2-(1H-indol-5-yloxy)-N-[(4-{[(1-methylpiperidin-4-yl)methyl]amino}-3-nitrophenyl)sulfonyl]benzamide | |
| 4-(4-{[2-(4-chlorophenyl)-4,4-dimethylcyclohex-1-en-1-yl]methyl}piperazin-1-yl)-2-(1H-indol-4-yloxy)-N-[(4-{[(1-methylpiperidin-4-yl)methyl]amino}-3-nitrophenyl)sulfonyl]benzamide | |
| 4-(4-{[2-(4-chlorophenyl)-4,4-dimethylcyclohex-1-en-1-yl]methyl]piperazin-1-yl)-N-({4-[3-(dimethylamino)propoxy]-3-nitrophenyl}sulfonyl)-2-(1H-indol-4-yloxy)benzamide | |

| Name | Structure |
|---|---|
| 4-(4-{[2-(4-chlorophenyl)-4,4-dimethylcyclohex-1-en-1-yl]methyl}piperazin-1-yl)-2-(1H-indol-5-yloxy)-N-{[4-(4-methylpiperazin-1-yl)-3-nitrophenyl]sulfonyl}benzamide | |
| 4-(4-{[2-(4-chlorophenyl)-4,4-dimethylcyclohex-1-en-1-yl]methyl}piperazin-1-yl)-2-(1H-indol-4-yloxy)-N-[(3-nitro-4-{[1-(2,2,2-trifluoroethyl)piperidin-4-yl]amino}phenyl)sulfonyl]benzamide | |
| 4-(4-{[2-(4-chlorophenyl)-4,4-dimethylcyclohex-1-en-1-yl]methyl}piperazin-1-yl)-N-{[4-({[4-(dimethylamino)-1-methylpiperidin-4-yl]methyl}amino)-3-nitrophenyl]sulfonyl}-2-(1H-indol-5-yloxy)benzamide | |

-continued

| Name | Structure |
|---|---|
| 4-{4-[(4'-chloro-1,1'-biphenyl-2-yl)methyl]piperazin-1-yl}-2-(2,3-dihydro-1,4-benzodioxin-5-yloxy)-N-({3-nitro-4-[(tetrahydro-2H-pyran-4-ylmethyl)amino]phenyl}sulfonyl)benzamide | 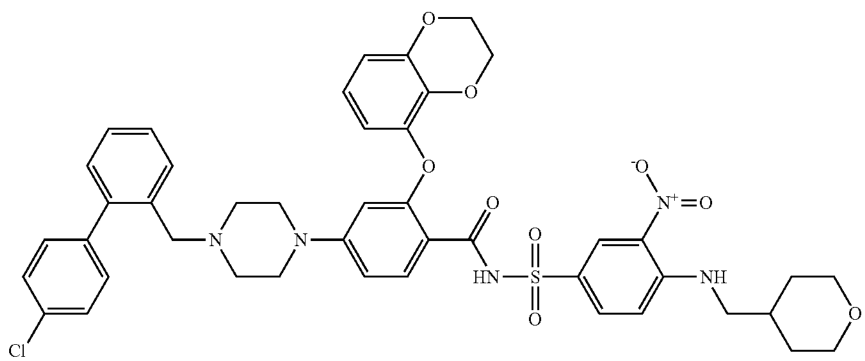 |
| 5-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)-1,1'-biphenyl-2-carboxamide | |
| 5-{4-[(4'-chloro-1,1'-biphenyl-2-yl)methyl]piperazin-1-yl}-N-[(4-{[3-(dimethylamino)propyl]amino}-3-nitrophenyl)sulfonyl]-1,1'-biphenyl-2-carboxamide | 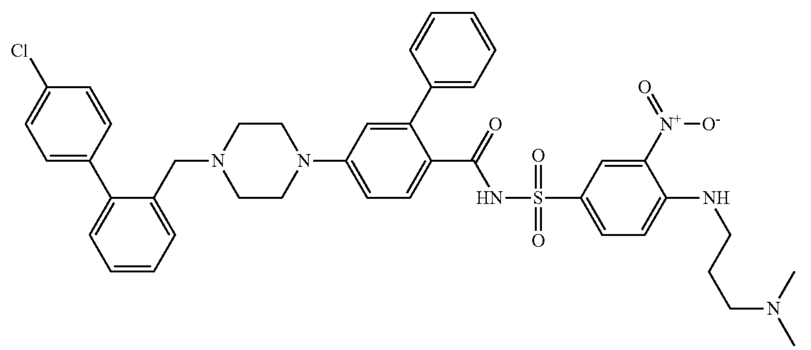 [SMILES: CN(C)CCCNc1ccc(S(=O)(=O)NC(=O)c2ccc(N3CCN(Cc4ccccc4-c4ccc(Cl)cc4)CC3)cc2-c2ccccc2)cc1[N+](=O)[O-]] |
| 4-[4-({4'-chloro-4-[2-(dimethylamino)ethoxy]-1,1'-biphenyl-2-yl}methyl)piperazin-1-yl]-N-({3-nitro-4-[(tetrahydro-2H-pyran-4-ylmethyl)amino]phenyl}sulfonyl)-2-phenoxybenzamide | 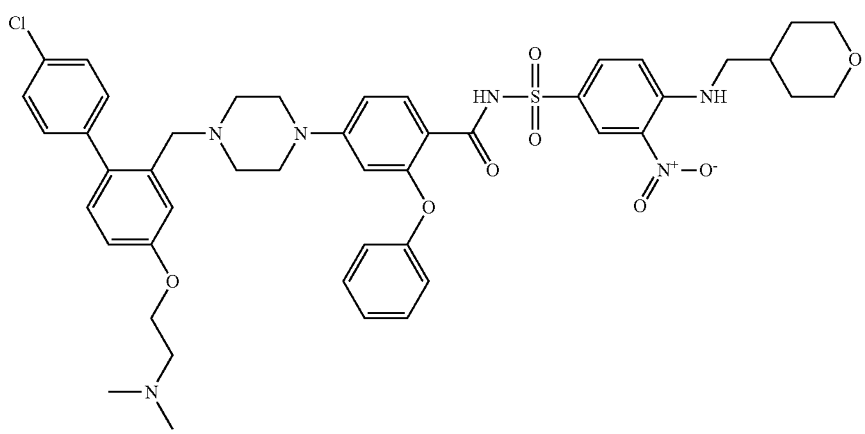 [SMILES: CN(C)CCOc1ccc(-c2ccc(Cl)cc2)c(CN2CCN(c3ccc(C(=O)NS(=O)(=O)c4ccc(NCC5CCOCC5)c([N+](=O)[O-])c4)c(Oc4ccccc4)c3)CC2)c1] |

| Name | Structure |
|---|---|
| 4-(4-{[4'-chloro-4-(3-piperidin-1-ylpropoxy)-1,1'-biphenyl-2-yl]methyl]piperazin-1-yl)-N-({3-nitro-4-[(tetrahydro-2H-pyran-4-ylmethyl)amino]phenyl}\sulfonyl)-2-phenoxybenzamide | 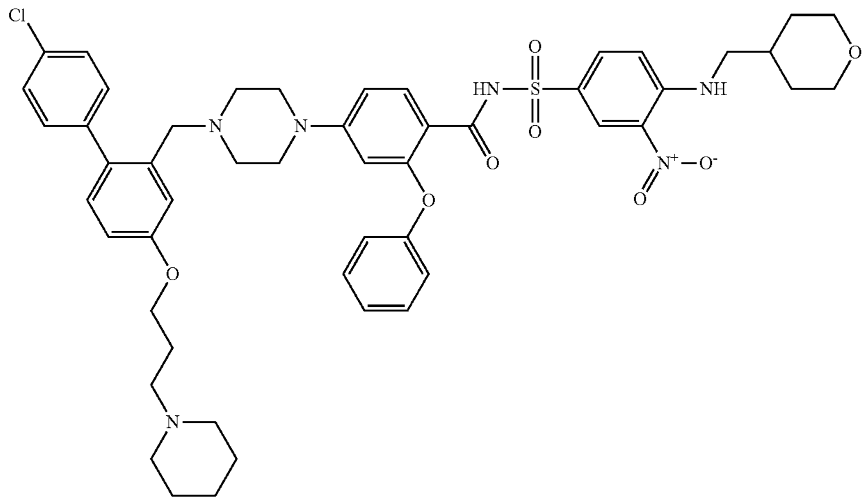 [SMILES: O=C(NS(=O)(=O)c1ccc(NCC2CCOCC2)c([N+](=O)[O-])c1)c1ccc(N2CCN(Cc3cc(OCCCN4CCCCC4)ccc3-c3ccc(Cl)cc3)CC2)cc1Oc1ccccc1] |
| 4-(4-{[4'-chloro-4-(2-morpholin-4-ylethoxy)-1,1'-biphenyl-2-yl]methyl]piperazin-1-yl)-N-({3-nitro-4-[(tetrahydro-2H-pyran-4-ylmethyl)amino]phenyl}sulfonyl)-2-phenoxybenzamide | 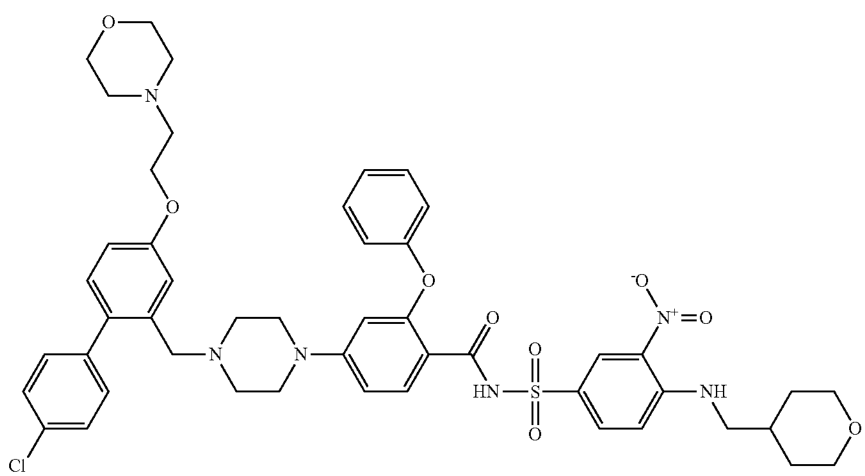 |
| 4-[4-({4'-chloro-4-[3-(dimethylamino)propoxy]-1,1'-biphenyl-2-yl}methyl)piperazin-1-yl]-N-({3-nitro-4-[(tetrahydro-2H-pyran-4-ylmethyl)amino]phenyl}sulfonyl)-2-phenoxybenzamide | 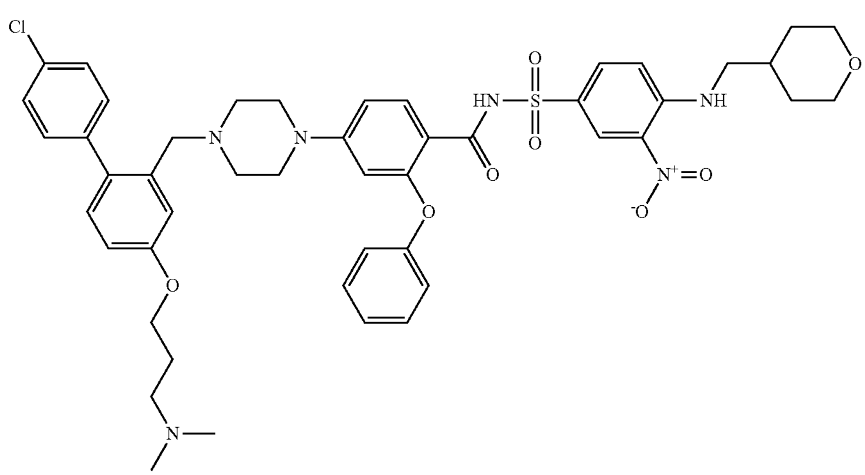 |

-continued

| Name | Structure |
|---|---|
| 4-(4-{[4'-chloro-4-(2-morpholin-4-ylethoxy)-1,1'-biphenyl-2-yl]methyl]piperazin-1-yl)-2-phenoxy-N-({4-[(tetrahydro-2H-pyran-4-ylmethyl)amino]-3-[(trifluoromethyl)sulfonyl]phenyl}sulfonyl)benzamide | 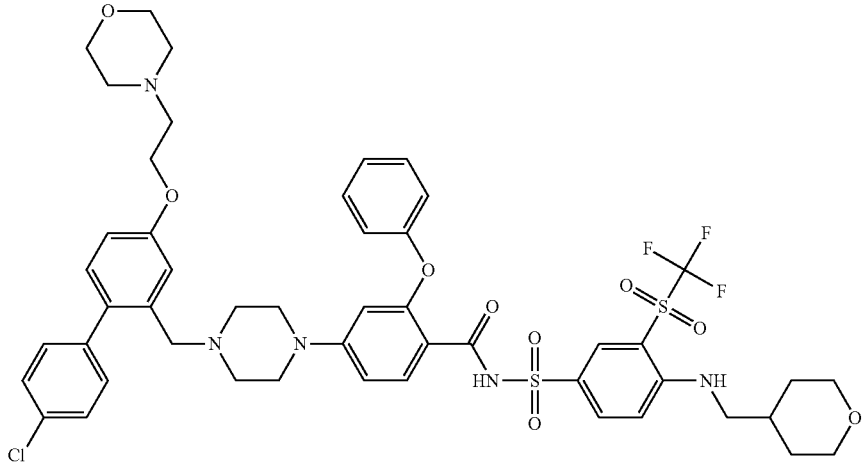 [SMILES: O=C(NS(=O)(=O)c1ccc(NCC2CCOCC2)c(S(=O)(=O)C(F)(F)F)c1)c1ccc(N2CCN(Cc3cc(OCCN4CCOCC4)ccc3-c3ccc(Cl)cc3)CC2)cc1Oc1ccccc1] |
| 4-(4-{[4'-chloro-4-(3-piperidin-1-ylpropoxy)-1,1'-biphenyl-2-yl]methyl}piperazin-1-yl)-2-phenoxy-N-({4-[(tetrahydro-2H-pyran-4-ylmethyl)amino]-3-[(trifluoromethyl)sulfonyl]phenyl}sulfonyl)benzamide | 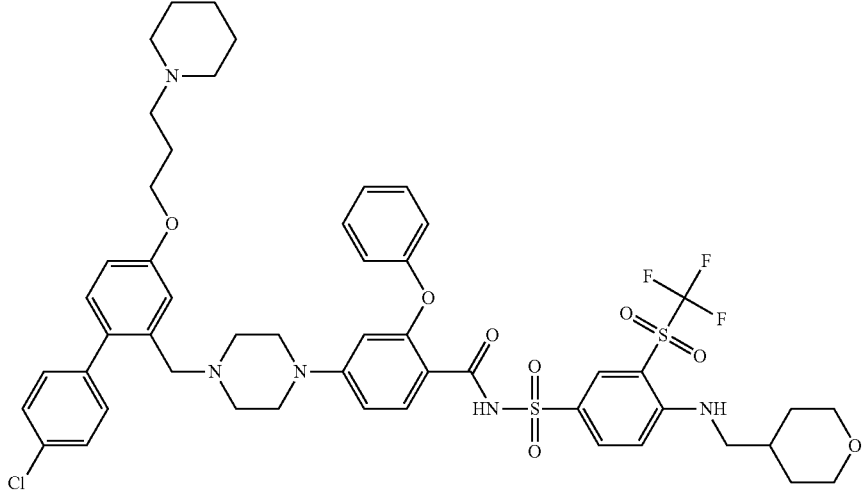 [SMILES: O=C(NS(=O)(=O)c1ccc(NCC2CCOCC2)c(S(=O)(=O)C(F)(F)F)c1)c1ccc(N2CCN(Cc3cc(OCCCN4CCCCC4)ccc3-c3ccc(Cl)cc3)CC2)cc1Oc1ccccc1] |
| 4-[4-({4'-chloro-4-[3-(dimethylamino)propoxy]-1,1'-biphenyl-2-yl}methyl)piperazin-1-yl]-2-phenoxy-N-({4-[(tetrahydro-2H-pyran-4-ylmethyl)amino]-3-[(trifluoromethyl)sulfonyl]phenyl}sulfonyl)benzamide | 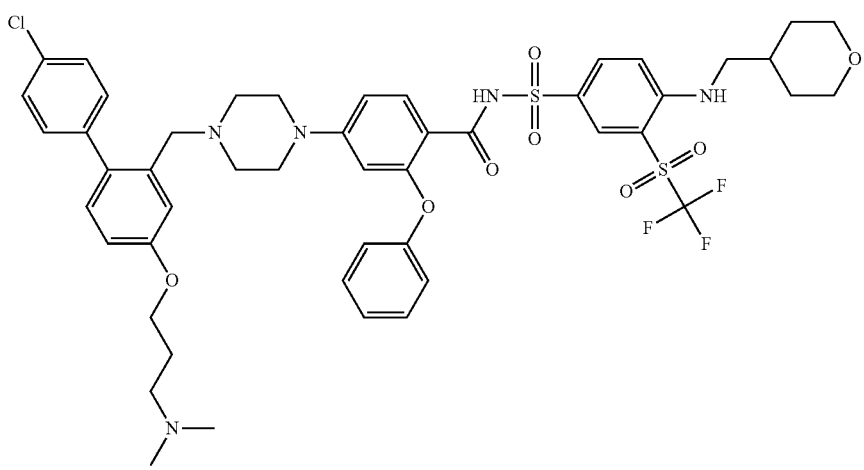 [SMILES: CN(C)CCCOc1ccc(-c2ccc(Cl)cc2)c(CN2CCN(c3ccc(C(=O)NS(=O)(=O)c4ccc(NCC5CCOCC5)c(S(=O)(=O)C(F)(F)F)c4)c(Oc4ccccc4)c3)CC2)c1] |

| Name | Structure |
|---|---|
| 4-[4-({4'-chloro-4-[2-(dimethylamino)ethoxy]-1,1'-biphenyl-2-yl}methyl)piperazin-1-yl]-2-phenoxy-N-({4-[(tetxahydro-2H-pyran-4-ylmethyl)amino]-3-[(trifluoromethyl)sulfonyl]phenyl}sulfonyl)benzamide | 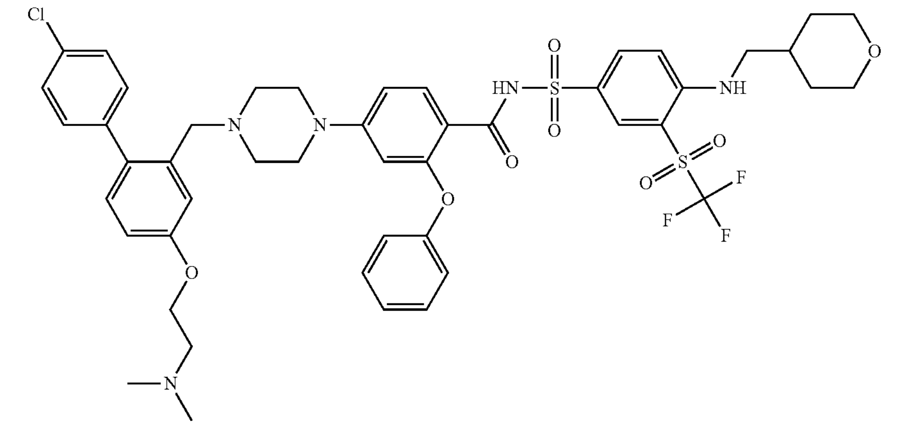 [SMILES: CN(C)CCOc1ccc(-c2ccc(Cl)cc2)c(CN2CCN(c3ccc(C(=O)NS(=O)(=O)c4ccc(NCC5CCOCC5)c(S(=O)(=O)C(F)(F)F)c4)c(Oc4ccccc4)c3)CC2)c1] |
| 4-[4-({4'-chloro-4-[2-(dimethylamino)ethoxyl-1,1'-biphenyl-2-yl}methyl)piperazin-1-yl]-N-({3-nitro-4-[(3-pyrrolidin-1-ylpropyl)amino]phenyl}sulfonyl)-2-phenoxybenzamide | |
| 4-[4-({4'-chloro-3-[2-(dimethylamino)ethoxy]-1,1'-biphenyl-2-yl}methyl)piperazin-1-yl]-N-({3-nitro-4-[(tetrahydro-2H-pyran-4-ylmethyl)amino]phenyl}sulfonyl)-2-phenoxybenzamide | 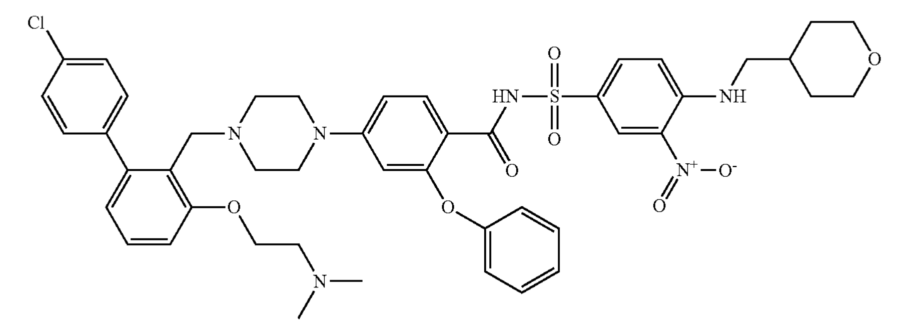 [SMILES: CN(C)CCOc1cccc(-c2ccc(Cl)cc2)c1CN1CCN(c2ccc(C(=O)NS(=O)(=O)c3ccc(NCC4CCOCC4)c([N+](=O)[O-])c3)c(Oc3ccccc3)c2)CC1] |
| 4-[4-({4'-chloro-3-[2-(dimethylamino)ethoxy]-1,1'-biphenyl-2-yl}methyl)piperazin-1-yl]-N-({3-nitro-4-[(3-pyrrolidin-1-ylpropyl)amino]phenyl}sulfonyl)-2-phenoxybenzamide | 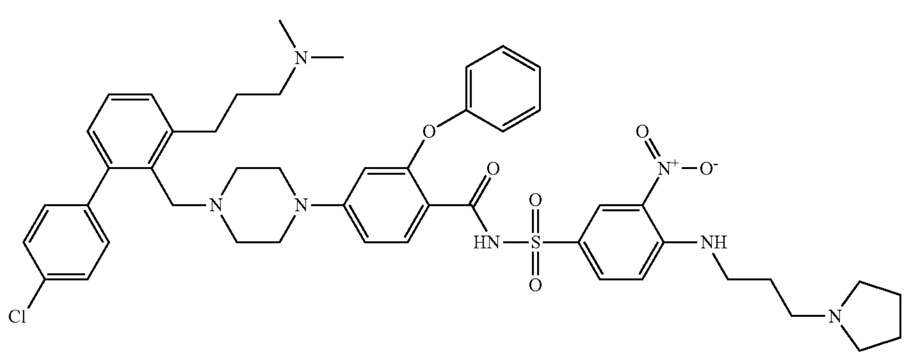 [SMILES: CN(C)CCCc1cccc(-c2ccc(Cl)cc2)c1CN1CCN(c2ccc(C(=O)NS(=O)(=O)c3ccc(NCCCN4CCCC4)c([N+](=O)[O-])c3)c(Oc3ccccc3)c2)CC1] |

| Name | Structure |
|---|---|
| 4-[4-({4'-chloro-3-[2-(dimethylamino)ethoxy]-1,1'-biphenyl-2-yl}methyl)piperazin-1-yl]-2-phenoxy-N-({4-[(tetrahydro-2H-pyran-4-ylmethyl)amino]-3-[(trifluoromethyl)sulfonyl]phenyl}sulfonyl)benzamide | 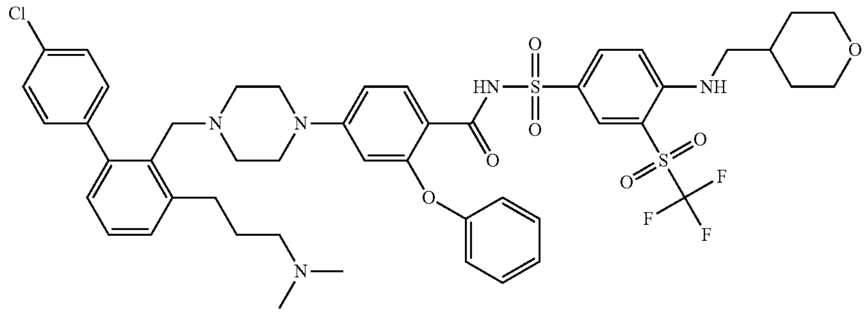 [SMILES: CN(C)CCCc1cccc(-c2ccc(Cl)cc2)c1CN1CCN(c2ccc(C(=O)NS(=O)(=O)c3ccc(NCC4CCOCC4)c(S(=O)(=O)C(F)(F)F)c3)c(Oc3ccccc3)c2)CC1] |
| 4-[4-({4'-chloro-4-[2-(dimethylamino)ethoxy]-1,1'-biphenyl-2-yl}methyl)piperazin-1-yl]-2-(1H-indol-4-yloxy)-N-({3-nitro-4-[(tetrahydro-2H-pyran-4-ylmethyl)amino]phenyl}sulfonyl)benzamide | 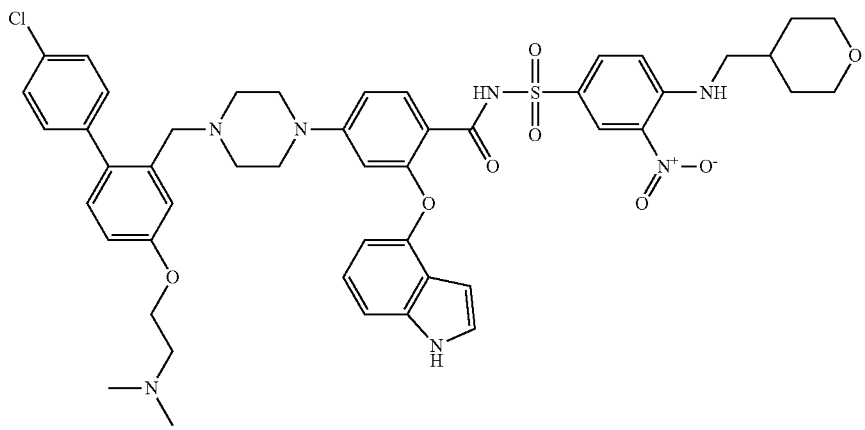 [SMILES: CN(C)CCOc1ccc(-c2ccc(Cl)cc2)c(CN2CCN(c3ccc(C(=O)NS(=O)(=O)c4ccc(NCC5CCOCC5)c([N+](=O)[O-])c4)c(Oc4cccc5[nH]ccc45)c3)CC2)c1] |
| 4-[4-({4'-chloro-4-[2-(dimethylamino)ethoxy]-1,1'-biphenyl-2-yl}methyl)piperazin-1-yl]-2-(1H-indol-5-yloxy)-N-({3-nitro-4-[(tetrahydro-2H-pyran-4-ylmethyl)amino]phenyl}sulfonyl)benzamide | 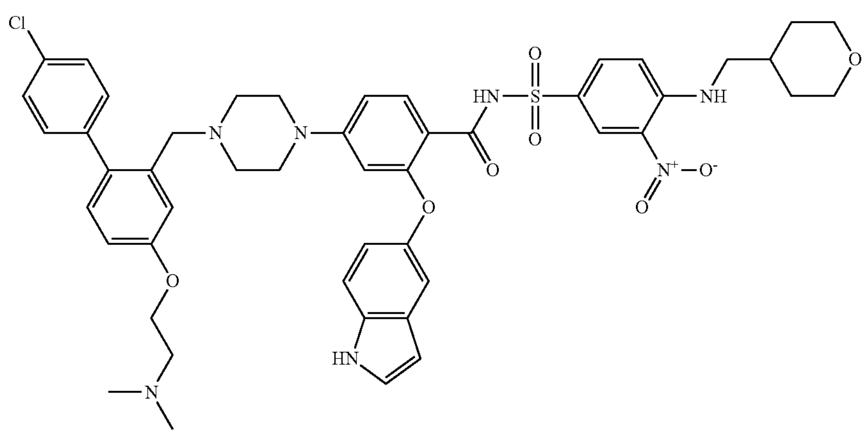 [SMILES: CN(C)CCOc1ccc(-c2ccc(Cl)cc2)c(CN2CCN(c3ccc(C(=O)NS(=O)(=O)c4ccc(NCC5CCOCC5)c([N+](=O)[O-])c4)c(Oc4ccc5[nH]ccc5c4)c3)CC2)c1] |

-continued

| Name | Structure |
|---|---|
| 4-(4-{[4'-chloro-4-(2-morpholin-4-ylethoxy)-1,1'-biphenyl-2-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide | 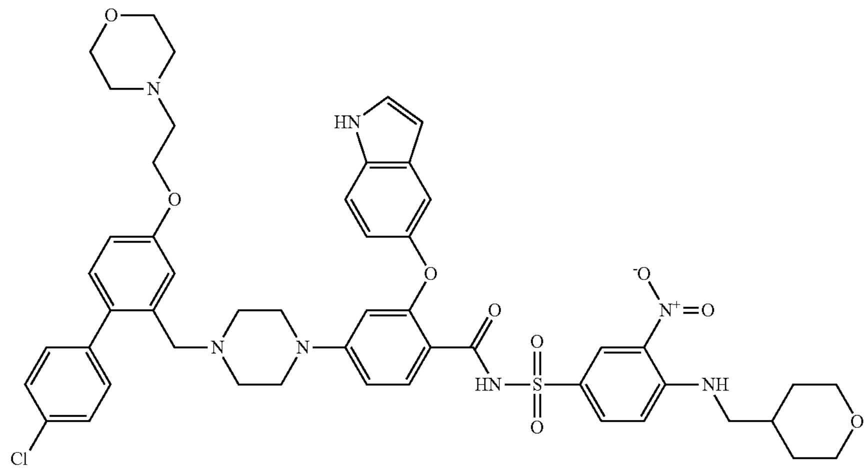 |
| 4-[4-({4'-chloro-3-[2-(dimethylamino)ethoxy]-1,1'-biphenyl-2-yl}methyl)piperazin-1-yl]-2-(1H-indol-4-yloxy)-N-({3-nitro-4-[(tetrahydro-2H-pyran-4-ylmethyl)amino]phenyl}sulfonyl)benzamide | 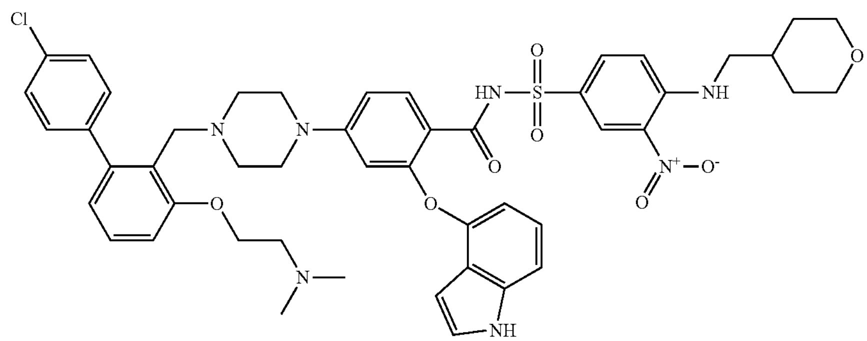 |
| 4-[4-({4'-chloro-3-[2-(dimethylamino)ethoxy]-1,1'-biphenyl-2-yl]methyl)piperazin-1-yl]-2-(1H-indol-5-yloxy)-N-({3-nitro-4-[(tetrahydro-2H-pyran-4-ylmethyl)amino]phenyl}sulfonyl)benzamide | |
| 4-(4-{[4'-chloro-4-(2-morpholin-4-ylethoxy)-1,1'-biphenyl-2-yl]methyl}piperazin-1-yl)-2-(1H-indol-4-yloxy)-N-({3-nitro-4-[(tetrahydro-2H-pyran-4-ylmethyl)amino]phenyl}sulfonyl)benzamide | 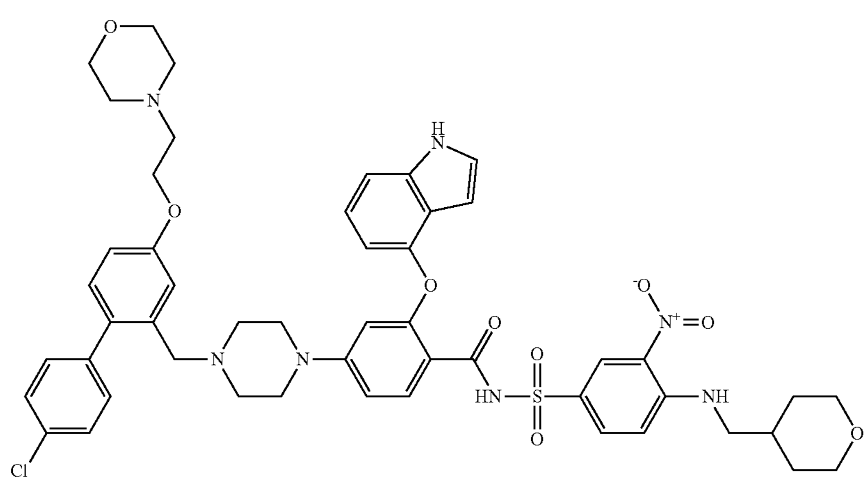 |

| Name | Structure |
|---|---|
| 4-(4-{[4'-chloro-3-(2-morpholin-4-ylethoxy)-1,1'-biphenyl-2-yl]methyl}piperazin-1-yl)-2-(1H-indol-4-yloxy)-N-({3-nitro-4-[(tetrahydro-2H-pyran-4-ylmethyl)amino]phenyl}sulfonyl)benzamide | 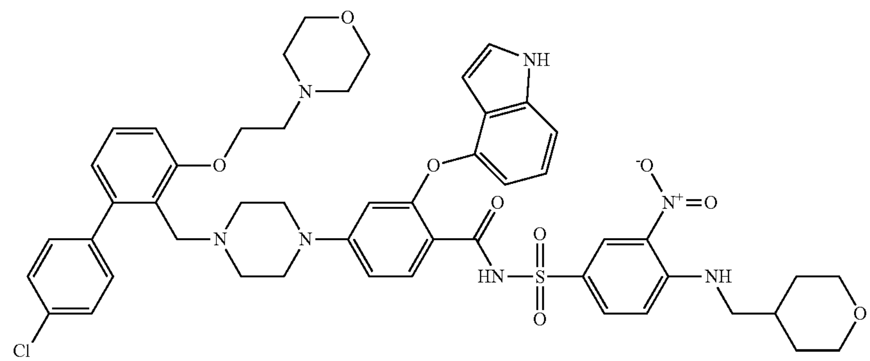 |
| 4-(4-{[4'-chloro-3-(2-morpholin-4-ylethoxy)-1,1'-biphenyl-2-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide | 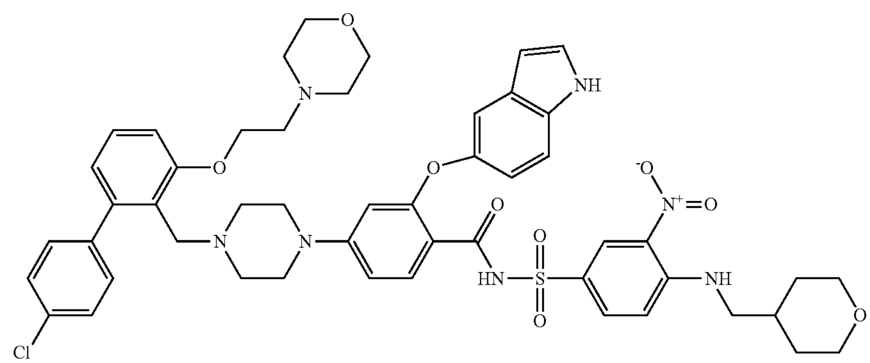 |
| 4-[4-({4'-chloro-4-[2-(dimethylamino)ethoxy]-1,1'-biphenyl-2-yl}methyl)piperazin-1-yl]-N-({4-[(1-methylpiperidin-4-yl)amino]-3-nitrophenyl}sulfonyl)-2-phenoxybenzamide | 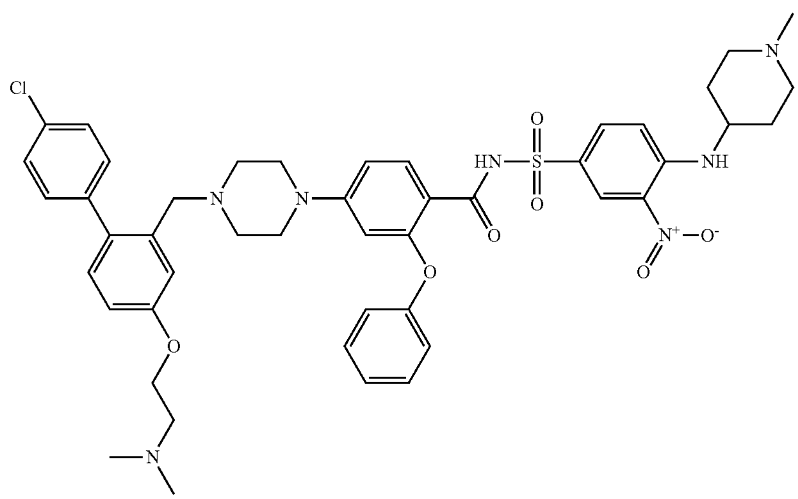 [SMILES: CN(C)CCOc1ccc(-c2ccc(Cl)cc2)c(CN2CCN(c3ccc(C(=O)NS(=O)(=O)c4ccc(NC5CCN(C)CC5)c([N+](=O)[O-])c4)c(Oc4ccccc4)c3)CC2)c1] |
| 4-[4-({4'-chloro-3-[2-(dimethylamino)ethoxy]-1,1'-biphenyl-2-yl}methyl)piperazin-1-yl]-2-(1H-indol-5-yloxy)-N-({3-nitro-4-[(3-pyrrolidin-1-ylpropyl)amino]phenyl}sulfonyl)benzamide | 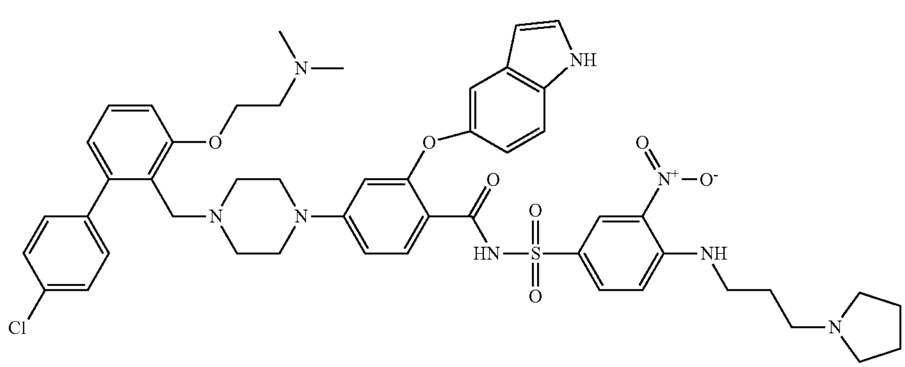 [SMILES: CN(C)CCOc1cccc(-c2ccc(Cl)cc2)c1CN1CCN(c2ccc(C(=O)NS(=O)(=O)c3ccc(NCCCN4CCCC4)c([N+](=O)[O-])c3)c(Oc3ccc4[nH]ccc4c3)c2)CC1] |

-continued

| Name | Structure |
|---|---|
| 4-[4-({4'-chloro-4-[2-(dimethylamino)ethoxy]-1,1'-biphenyl-2-yl}methyl)piperazin-1-yl]-2-(1H-indol-5-yloxy)-N-({3-nitro-4-[(3-pyrrolidin-1-ylpropyl)amino]phenyl}sulfonyl)benzamide | 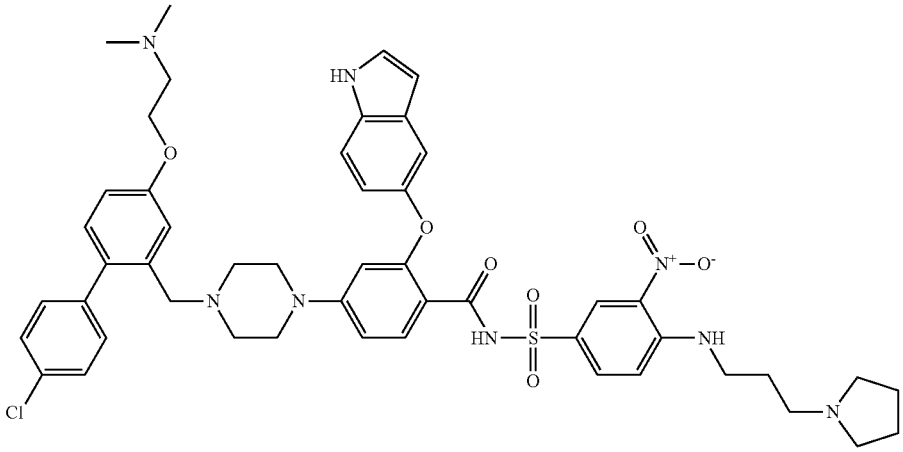 [SMILES: CN(C)CCOc1ccc(-c2ccc(Cl)cc2)c(CN2CCN(c3ccc(C(=O)NS(=O)(=O)c4ccc(NCCCN5CCCC5)c([N+](=O)[O-])c4)c(Oc4ccc5[nH]ccc5c4)c3)CC2)c1] |
| 4-(4-{[4'-chloro-4-(2-morpholin-4-ylethoxy)-1,1'-biphenyl-2-yl]methyl]piperazin-1-yl)-2-(1H-indol-5-yloxy)-N-({3-nitro-4-[(3-pyrrolidin-1-ylpropyl)amino]phenyl}sulfonyl)benzamide | 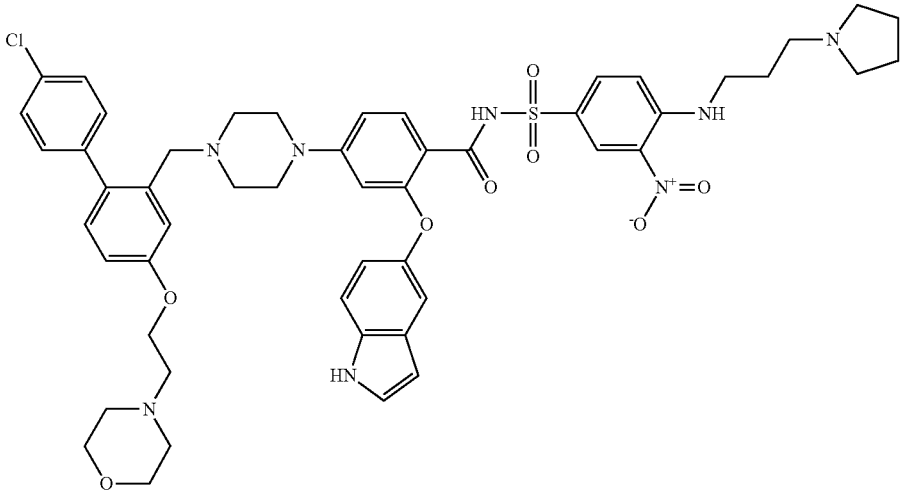 |
| 4-[4-({4'-chloro-4-[2-(dimethylamino)ethoxy]-1,1'-biphenyl-2-yl}methyl)piperazin-1-yl]-N-[(3-nitro-4-{[1-(2,2,2-trifluoroethyl)piperidin-4-yl]amino}phenyl)sulfonyl]-2-phenoxybenzamide | 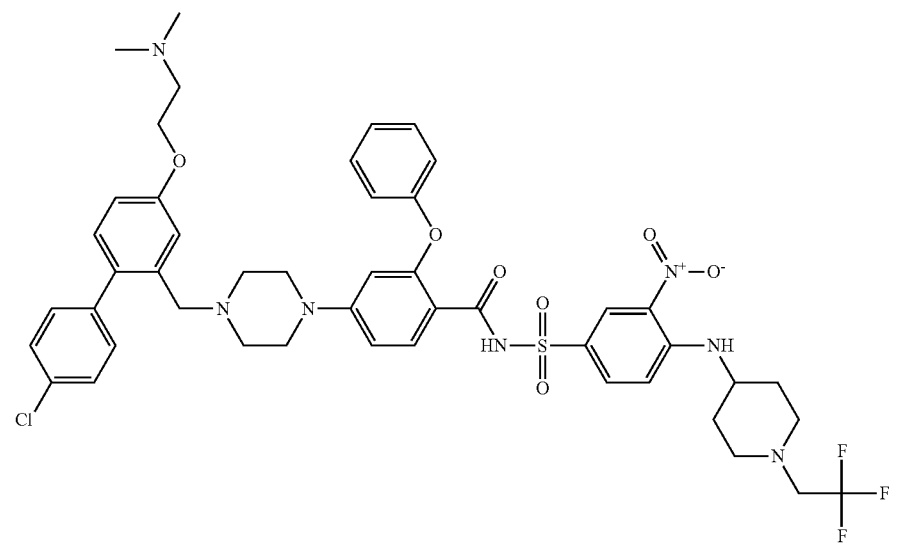 [SMILES: CN(C)CCOc1ccc(-c2ccc(Cl)cc2)c(CN2CCN(c3ccc(C(=O)NS(=O)(=O)c4ccc(NC5CCN(CC(F)(F)F)CC5)c([N+](=O)[O-])c4)c(Oc4ccccc4)c3)CC2)c1] |

| Name | Structure |
|---|---|
| 4-(4-{[4'-chloro-4-(2-pyrrolidin-1-ylethoxy)-1,1'-biphenyl-2-yl]methyl}piperazin-1-yl)-N-({3-nitro-4-[(tetrahydro-2H-pyran-4-ylmethyl)amino]phenyl}sulfonyl)-2-phenoxybenzamide | 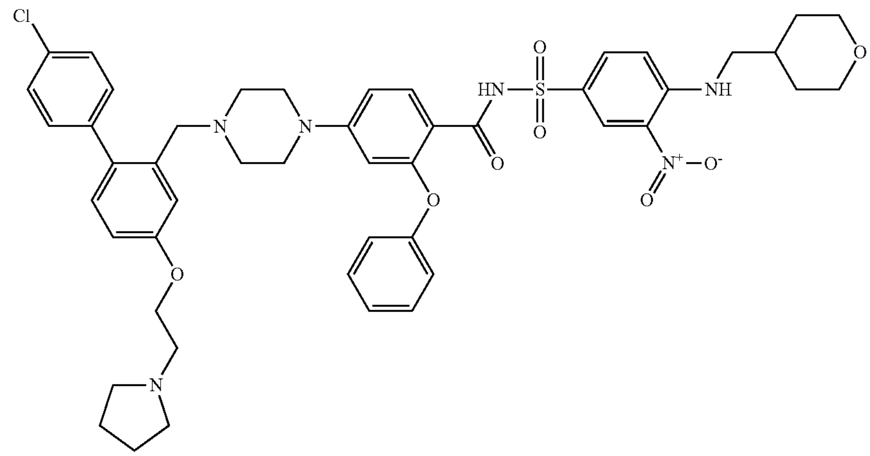 [SMILES: O=C(NS(=O)(=O)c1ccc(NCC2CCOCC2)c([N+](=O)[O-])c1)c1ccc(N2CCN(Cc3cc(OCCN4CCCC4)ccc3-c3ccc(Cl)cc3)CC2)cc1Oc1ccccc1] |
| 4-[4-({4'-chloro-4-[2-(diisopropylamino)ethoxy]-1,1'-biphenyl-2-yl}methyl)piperazin-1-yl]-N-({3-nitro-4-[(tetrahydro-2H-pyran-4-ylmethyl)amino]phenyl}sulfonyl)-2-phenoxy-benzamide | 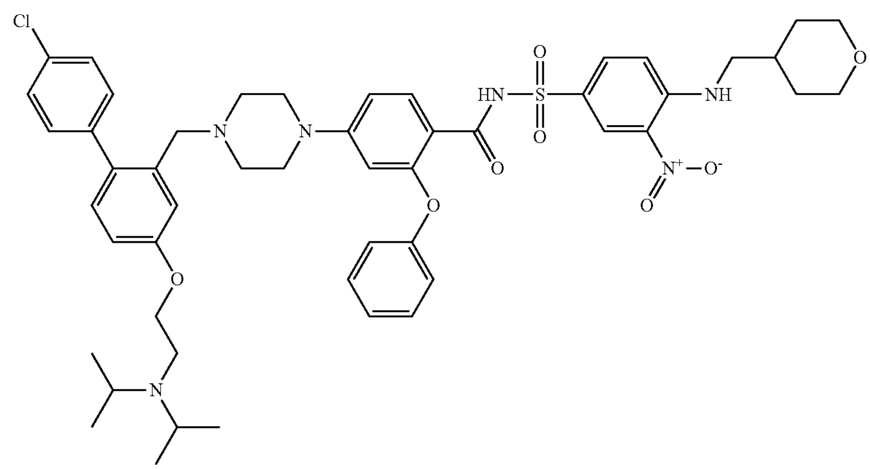 [SMILES: CC(C)N(CCOc1ccc(-c2ccc(Cl)cc2)c(CN2CCN(c3ccc(C(=O)NS(=O)(=O)c4ccc(NCC5CCOCC5)c([N+](=O)[O-])c4)c(Oc4ccccc4)c3)CC2)c1)C(C)C] |
| 4-{4-[(4'-chloro-1,1'-biphenyl-2-yl)methyl]piperazin-1-yl}-2-(2,3-dihydro-1H-indol-5-yloxy)-N-({3-nitro-4-[(tetrahydro-2H-pyran-4-ylmethyl)amino]phenyl}sulfonyl)benzamide | 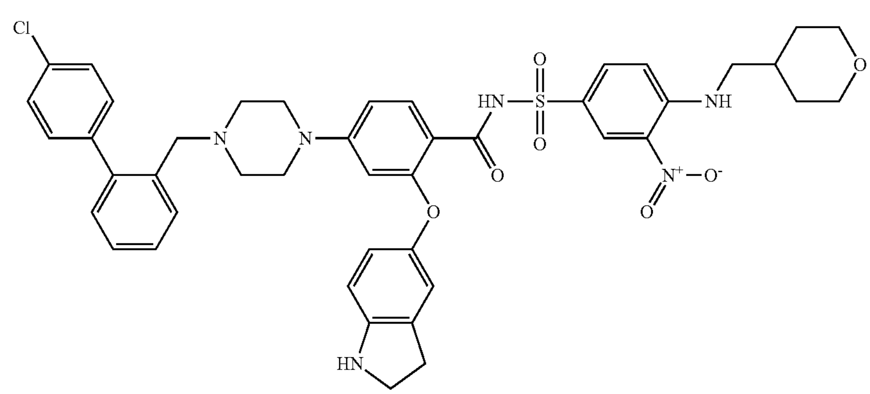 |

| Name | Structure |
|---|---|
| 4-(4-{[2-(4-chloro-phenyl)cyclohept-1-en-1-yl]methyl}piperazin-1-yl)-2-(1H-indol-4-yloxy)-N-({3-nitro-4-[(3-pyrrolidin-1-ylpropyl)amino]phenyl}sulfonyl)benzamide | |
| 4-(4-{[2-(4-chloro-phenyl)cyclooct-1-en-1-yl]methyl}piperazin-1-yl)-2-(1H-indol-4-yloxy)-N-({3-nitro-4-[(3-pyrrolidin-1-ylpropyl)amino]phenyl}sulfonyl)benzamide | |
| 4-(4-{[2-(4-chloro-phenyl)cyclopent-1-en-1-yl]methyl}piperazin-1-yl)-2-(1H-indol-4-yloxy)-N-({3-nitro-4-[(3-pyrrolidin-1-ylpropyl)amino]phenyl}sulfonyl)benzamide | |

| Name | Structure |
|---|---|
| 4-(4-{[2-(4-chloro-phenyl)-4,4-dimethylcyclopent-1-en-1-yl]methyl}piperazin-1-yl)-2-(1H-indol-4-yloxy)-N-({4-[(1-methyl-piperidin-4-yl)amino]-3-nitrophenyl}sulfonyl)benzamide | |
| 4-(4-{[4-(4-chloro-phenyl)-6,6-dimethyl-5,6-dihydro-2H-pyran-3-yl]methyl}piperazin-1-yl)-2-(1H-indol-4-yloxy)-N-({4-[(1-methylpiperidin-4-yl)amino]-3-nitrophenyl}sulfonyl)benzamide | |
| 4-(4-{[2-(4-chloro-phenyl)cycloct-1-en-1-yl]methyl}piperazin-1-yl)-2-(1H-indol-4-yloxy)-N-({4-[(1-methylpiperidin-4-yl)amino]-3-nitrophenyl}sulfonyl)benzamide | |

-continued

| Name | Structure |
|---|---|
| 4-(4-{[2-(4-chlorophenyl)cyclohept-1-en-1-yl]methyl}piperazin-1-yl)-2-(1H-indol-4-yloxy)-N-({4-[(1-methylpiperidin-4-yl)amino]-3-nitrophenyl}sulfonyl)benzamide | 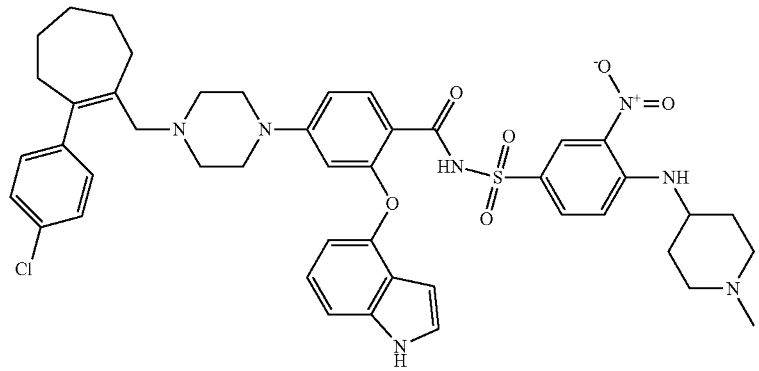 |
| 4-(4-{[2-(4-chlorophenyl)cyclopent-1-en-1-yl]methyl}piperazin-1-yl)-2-(1H-indol-4-yloxy)-N-({4-[(1-methylpiperidin-4-yl)amino]-3-nitrophenyl}sulfonyl)benzamide | 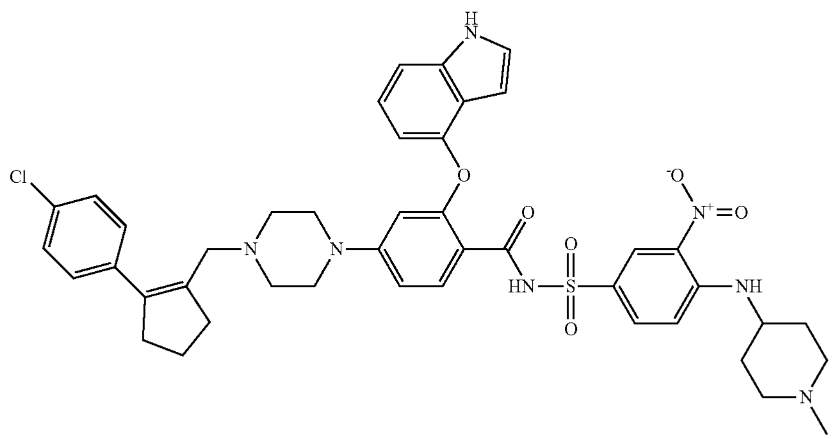 |
| 4-(4-{[2-(4-chlorophenyl)cyclohex-1-en-1-yl]methyl}piperazin-1-yl)-2-(1H-indol-4-yloxy)-N-({4-[(1-methylpiperidin-4-yl)amino]-3-nitrophenyl}sulfonyl)benzamide | 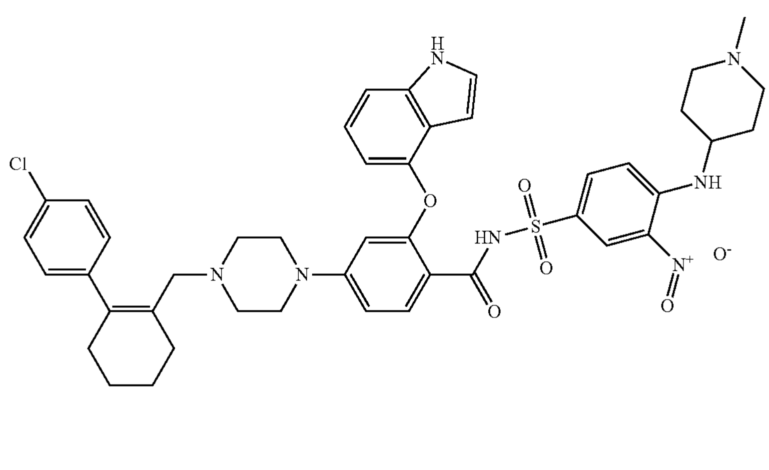 |

| Name | Structure |
|---|---|
| 4-(4-{[4-(4-chloro-phenyl)-6,6-dimethyl-5,6-dihydro-2H-pyran-3-yl]methyl}piperazin-1-yl)-2-(1H-indol-5-yloxy)-N-({4-[1-methylpiperidin-4-yl)amino]-3-nitrophenyl}sulfonyl)benzamide | 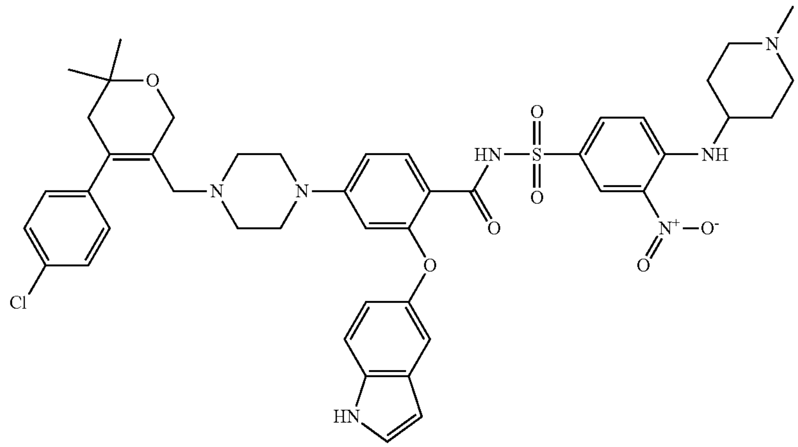 [SMILES: CN1CCC(Nc2ccc(S(=O)(=O)NC(=O)c3ccc(N4CCN(CC5=C(c6ccc(Cl)cc6)CC(C)(C)OC5)CC4)cc3Oc3ccc4[nH]ccc4c3)cc2[N+](=O)[O-])CC1] |
| 4-(4-{[2-(4-chloro-phenyl)cyclohept-1-en-1-yl]methyl}piperazin-1-yl)-2-(1H-indol-5-yloxy)-N-({4-[(1-methylpiperidin-4-yl)amino]-3-nitrophenyl}sulfonyl)benzamide | |
| 4-(4-{[2-(4-chloro-phenyl)-4,4-dimethylcyclohex-1-en-1-yl]methyl}piperazin-1-yl)-N-({4-[(1-methylpiperidin-4-yl)amino]-3-nitrophenyl}sulfonyl)-2-phenoxybenzamide | 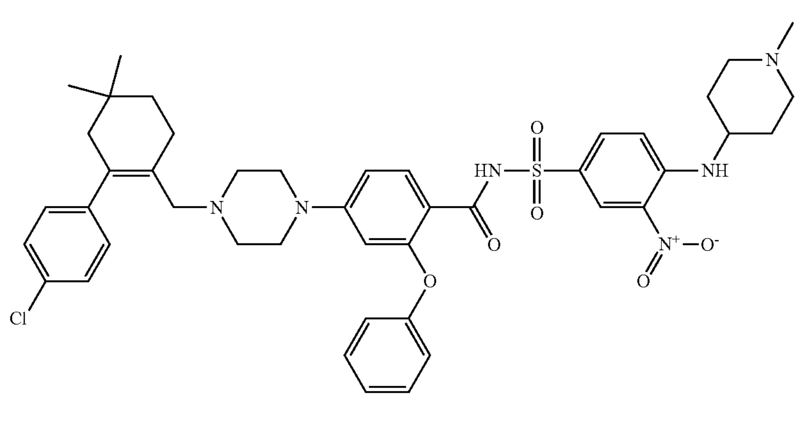 [SMILES: CN1CCC(Nc2ccc(S(=O)(=O)NC(=O)c3ccc(N4CCN(CC5=C(c6ccc(Cl)cc6)CC(C)(C)CC5)CC4)cc3Oc3ccccc3)cc2[N+](=O)[O-])CC1] |

-continued

| Name | Structure |
|---|---|
| 4-{4-[(4'-chloro-1,1'-biphenyl-2-yl)methyl]piperazin-1-yl}-N-[(4-{[2-(dimethylamino)ethyl]amino}-3-nitrophenyl)sulfonyl]-2-phenoxybenzamide | |
| 4-{4-[(4'-chloro-1,1'-biphenyl-2-yl)methyl]piperazin-1-yl}-N-[(4-{[3-(dimethylamino)propyl]amino}-3-nitrophenyl)sulfonyl]-2-phenoxybenzamide | |
| 4-{4-[(4'-chloro-1,1'-biphenyl-2-yl)methyl]piperazin-1-yl}-N-({4-[(3-morpholin-4-ylpropyl)amino]-3-nitrophenyl}sulfonyl)-2-phenoxybenzamide | 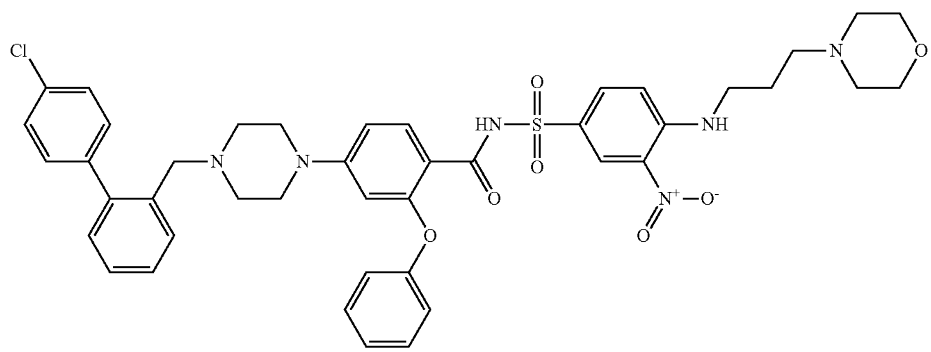 [SMILES: O=C(NS(=O)(=O)c1ccc(NCCCN2CCOCC2)c([N+](=O)[O-])c1)c1ccc(N2CCN(Cc3ccccc3-c3ccc(Cl)cc3)CC2)cc1Oc1ccccc1] |
| 4-{4-[(4'-chloro-1,1'-biphenyl-2-yl)methyl]piperazin-1-yl}-N-[(4-{[4-(dimethylamino)butyl]amino}-3-nitrophenyl)sulfonyl]-2-phenoxybenzamide | 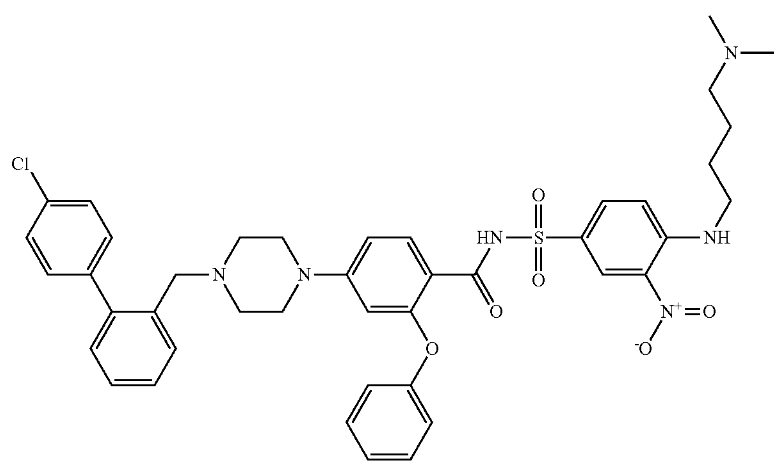 |

-continued

| Name | Structure |
|---|---|
| 4-{4-[(4'-chloro-1,1'-biphenyl-2-yl)methyl]piperazin-1-yl}-N-[(3-nitro-4-{[1-(phenylsulfonyl)piperidin-4-yl]amino}phenyl)sulfonyl]-2-phenoxybenzamide | 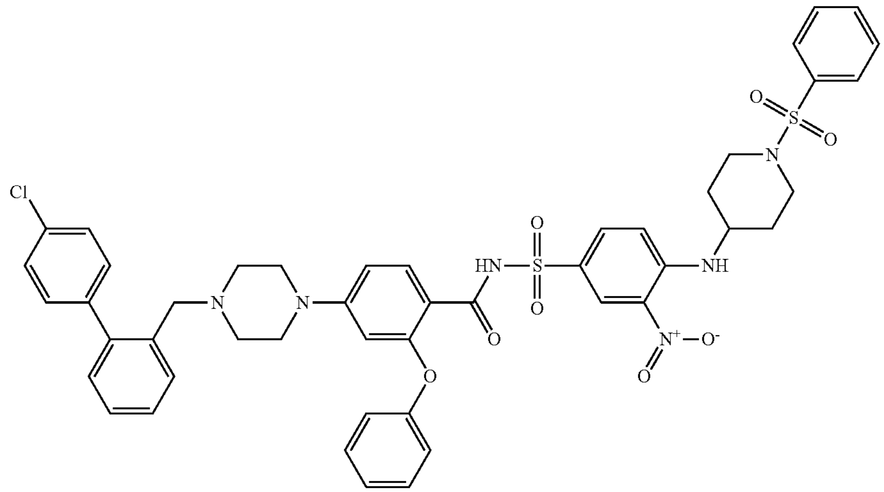 [SMILES: O=C(NS(=O)(=O)c1ccc(NC2CCN(S(=O)(=O)c3ccccc3)CC2)c([N+](=O)[O-])c1)c1ccc(N2CCN(Cc3ccccc3-c3ccc(Cl)cc3)CC2)cc1Oc1ccccc1] |
| 4-{4-[(4'-chloro-1,1'-biphenyl-2-yl)methyl]piperazin-1-yl}-N-[(3-nitro-4-{[1-(quinolin-8-ylsulfonyl)piperidin-4-yl]amino}phenyl)sulfonyl]-2-phenoxybenzamide | 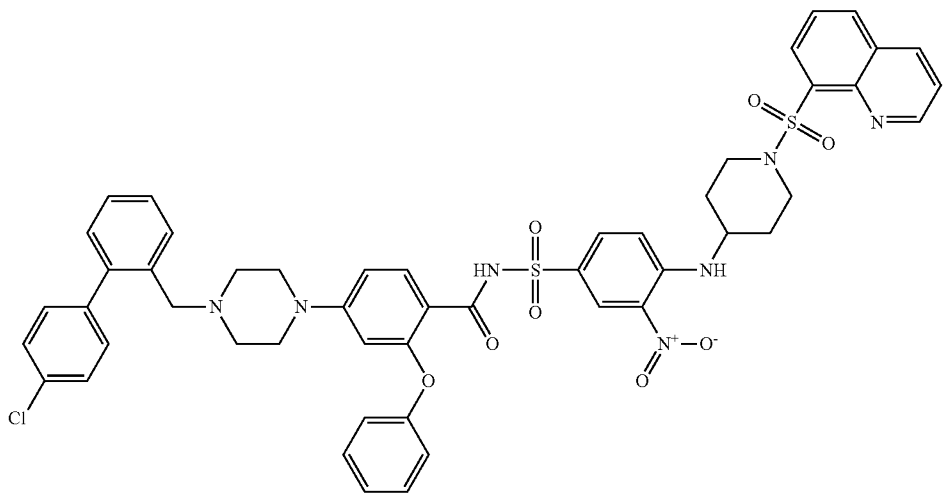 [SMILES: O=C(NS(=O)(=O)c1ccc(NC2CCN(S(=O)(=O)c3cccc4cccnc34)CC2)c([N+](=O)[O-])c1)c1ccc(N2CCN(Cc3ccccc3-c3ccc(Cl)cc3)CC2)cc1Oc1ccccc1] |
| 4-{4-[(4'-chloro-1,1'-biphenyl-2-yl)methyl]piperazin-1-yl}-2-phenoxy-N-({4-{[1-(phenylsulfonyl)piperidin-4-yl]amino}-3-[(trifluoromethyl)sulfonyl]phenyl]sulfonyl)benzamide | |

| Name | Structure |
|---|---|
| 4-{4-[(4'-chloro-1,1'-biphenyl-2-yl)methyl]piperazin-1-yl}-2-phenoxy-N-({4-{[1-(quinolin-8-ylsulfonyl)piperidin-4-yl]amino}-3-[(trifluoromethyl)sulfonyl]phenyl}sulfonyl)benzamide | 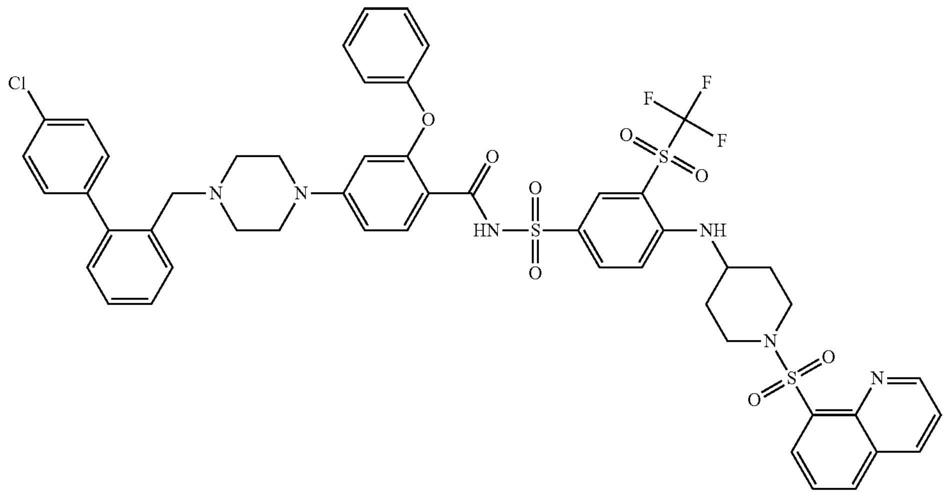 [SMILES: O=C(NS(=O)(=O)c1ccc(NC2CCN(S(=O)(=O)c3cccc4cccnc34)CC2)c(S(=O)(=O)C(F)(F)F)c1)c1ccc(N2CCN(Cc3ccccc3-c3ccc(Cl)cc3)CC2)cc1Oc1ccccc1] |
| 4-{4-[(4'-chloro-1,1'-biphenyl-2-yl)methyl]piperazin-1-yl}-N-[(4-{[(1S)-3-(dimethylamino)-1-thien-2-ylpropyl]amino}-3-nitrophenyl)sulfonyl]-2-phenoxybenzamide | 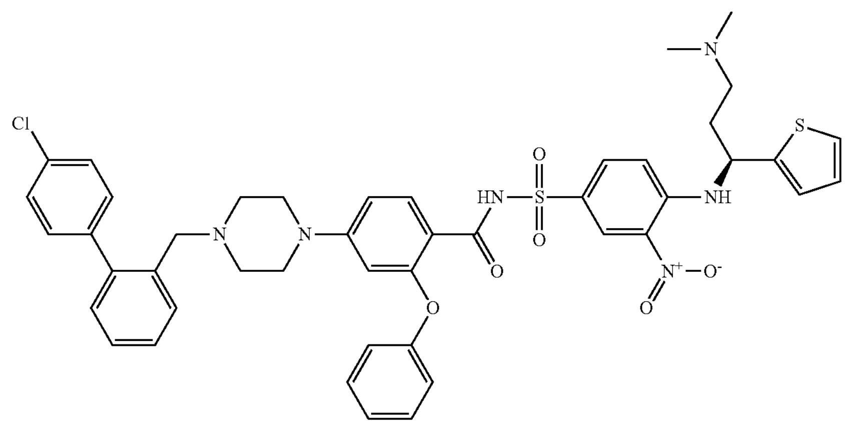 [SMILES: CN(C)CC[C@H](Nc1ccc(S(=O)(=O)NC(=O)c2ccc(N3CCN(Cc4ccccc4-c4ccc(Cl)cc4)CC3)cc2Oc2ccccc2)cc1[N+](=O)[O-])c1cccs1] |
| 4-{4-[(4'-chloro-1,1'-biphenyl-2-yl)methyl]piperazin-1-yl}-N-({3-nitro-4-[(thien-2-ylmethyl)amino]phenyl}sulfonyl)-2-phenoxybenzamide | 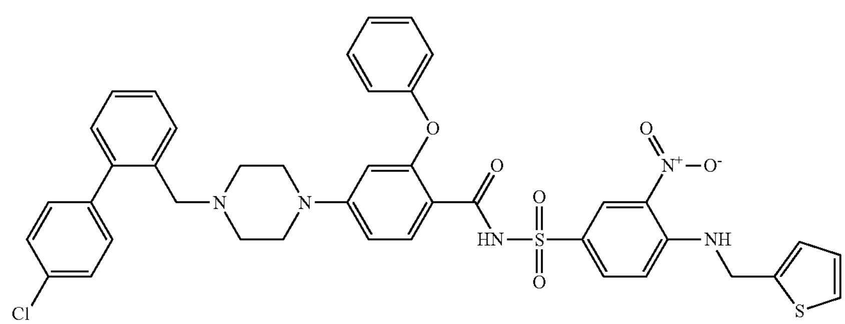 [SMILES: O=C(NS(=O)(=O)c1ccc(NCc2cccs2)c([N+](=O)[O-])c1)c1ccc(N2CCN(Cc3ccccc3-c3ccc(Cl)cc3)CC2)cc1Oc1ccccc1] |
| 4-{4-[(4'-chloro-1,1'-biphenyl-2-yl)methyl]piperazin-1-yl}-2-phenoxy-N-({4-[(tetrahydro-2H-pyran-4-ylmethyl)amino]-3-[(trifluoromethyl)sulfonyl]phenyl}sulfonyl)benzamide | |

| Name | Structure |
|------|-----------|
| 4-{4-[(4'-chloro-1,1'-biphenyl-2-yl)methyl]piperazin-1-yl}-N-[(3-nitro-4-{[2-(1H-1,2,3-triazol-1-yl)ethyl]amino}phenyl)sulfonyl]-2-phenoxybenzamide | 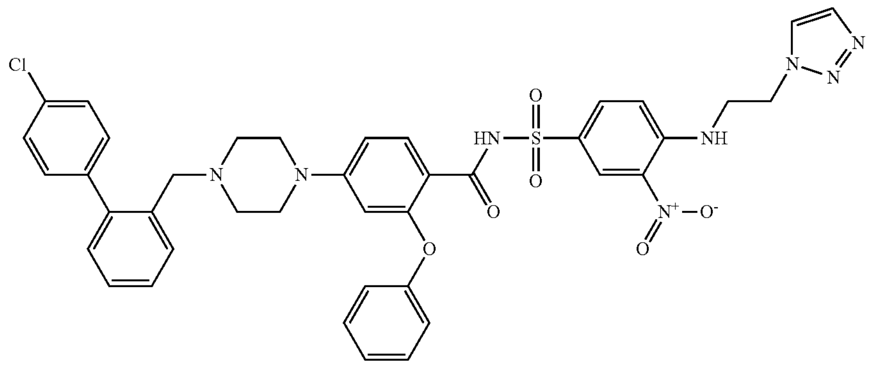 [SMILES: O=C(NS(=O)(=O)c1ccc(NCCn2ccnn2)c([N+](=O)[O-])c1)c1ccc(N2CCN(Cc3ccccc3-c3ccc(Cl)cc3)CC2)cc1Oc1ccccc1] |
| 4-{4-[(4'-chloro-1,1'-biphenyl-2-yl)methyl]piperazin-1-yl}-N-[(3-nitro-4-{[2-(2H-1,2,3-triazol-2-yl)ethyl]amino}phenyl)sulfonyl]-2-phenoxybenzamide | 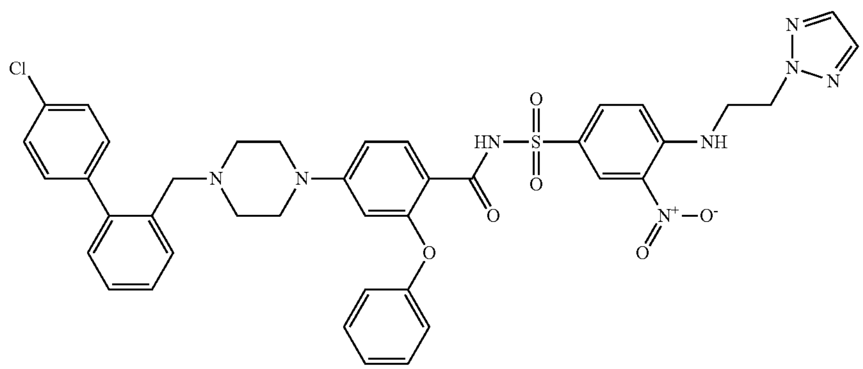 [SMILES: O=C(NS(=O)(=O)c1ccc(NCCn2nccn2)c([N+](=O)[O-])c1)c1ccc(N2CCN(Cc3ccccc3-c3ccc(Cl)cc3)CC2)cc1Oc1ccccc1] |
| 4-{4-[(4'-chloro-1,1'-biphenyl-2-yl)methyl]piperazin-1-yl}-N-[(4-{[3-(dimethylamino)propyl]amino}-3-nitrophenyl)sulfonyl]-2-(2-naphthyloxy)benzamide | 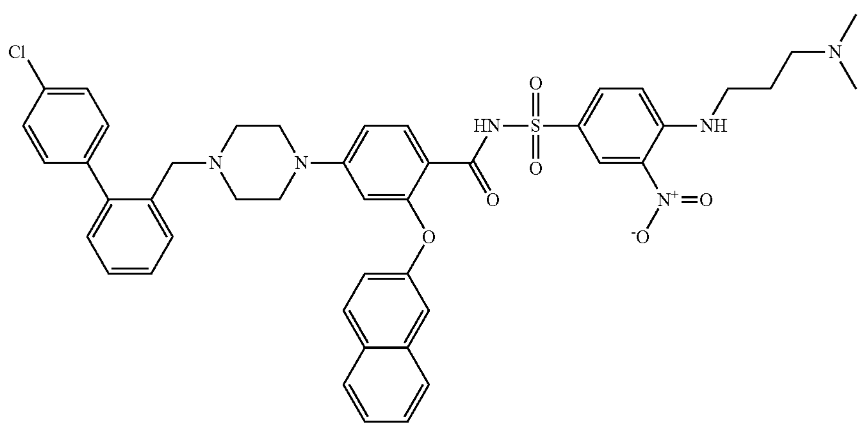 |
| 4-{4-[(4'-chloro-1,1'-biphenyl-2-yl)methyl]piperazin-1-yl}-N-[(3-nitro-4-{[2-(2-oxopyridin-1(2H)-yl)ethyl]amino}phenyl)sulfonyl]-2-phenoxybenzamide | 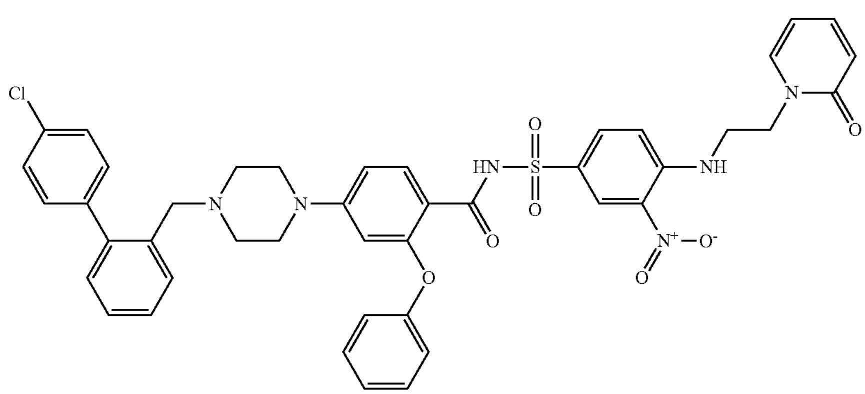 [SMILES: O=C(NS(=O)(=O)c1ccc(NCCn2ccccc2=O)c([N+](=O)[O-])c1)c1ccc(N2CCN(Cc3ccccc3-c3ccc(Cl)cc3)CC2)cc1Oc1ccccc1] |

| Name | Structure |
|---|---|
| 4-{4-[(4'-chloro-1,1'-biphenyl-2-yl)methyl]piperazin-1-yl}-N-[(3-nitro-4-{[2-(pyridin-2-yloxy)ethyl]amino}phenyl)sulfonyl]-2-phenoxybenzamide | 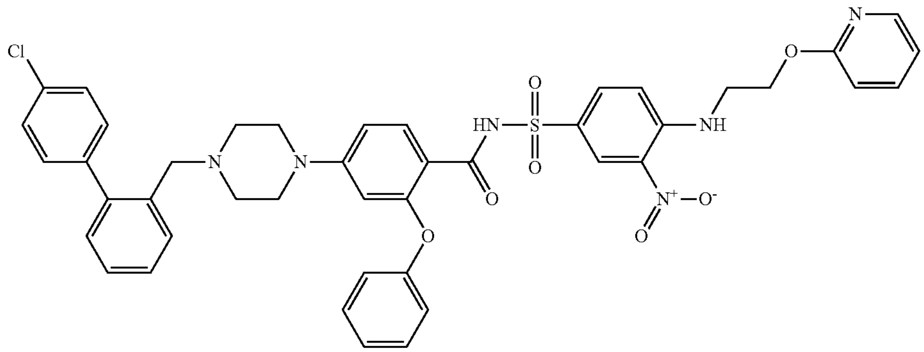 [SMILES: O=C(NS(=O)(=O)c1ccc(NCCOc2ccccn2)c([N+](=O)[O-])c1)c1ccc(N2CCN(Cc3ccccc3-c3ccc(Cl)cc3)CC2)cc1Oc1ccccc1] |
| 4-{4-[(4'-chloro-1,1'-biphenyl-2-yl)methyl]piperazin-1-yl}-N-({3-nitro-4-[(2-pyridin-4-ylethyl)amino]phenyl}sulfonyl)-2-phenoxybenzamide | 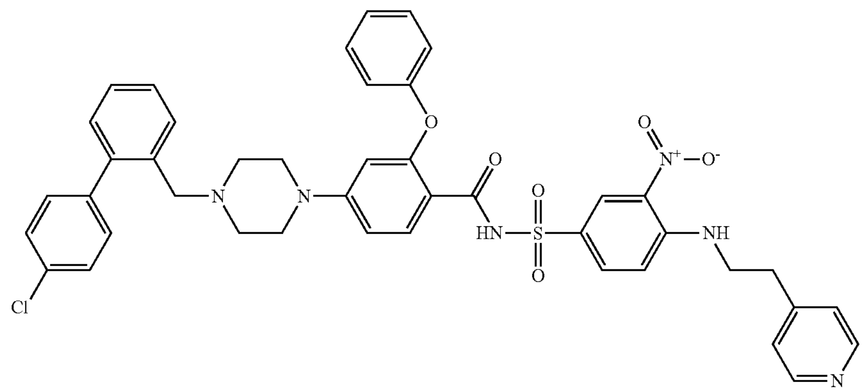 [SMILES: O=C(NS(=O)(=O)c1ccc(NCCc2ccncc2)c([N+](=O)[O-])c1)c1ccc(N2CCN(Cc3ccccc3-c3ccc(Cl)cc3)CC2)cc1Oc1ccccc1] |
| 4-(4-{[2-(4-chlorophenyl)-4,4-dimethylcyclohex-1-en-1-yl]methyl}piperazin-1-yl)-N-({4-{[3-(dimethylamino)propyl]amino}-3-[(trifluoromethyl)sulfonyl]phenyl}sulfonyl)-2-(1H-indol-5-yloxy)benzamide | |
| 4-(4-{[2-(4-chlorophenyl)-4,4-dimethylcyclohex-1-en-1-yl]methyl}piperazin-1-yl)-N-{[4-{[3-(dimethylamino)propyl]amino}-3-(trifluoromethyl)phenyl]sulfonyl}-2-(1H-indol-5-yloxy)benzamide | |

| Name | Structure |
|---|---|
| 4-(4-{[2-(4-chlorophenyl)-4,4-dimethylcyclohex-1-en-1-yl]methyl}piperazin-1-yl)-N-[(3-cyano-4-{[3-(dimethylamino)propyl]amino}phenyl)sulfonyl]-2-(1H-indol-5-yloxy)benzamide | |
| 4-(4-{[2-(4-chlorophenyl)-4,4-dimethylcyclohex-1-en-1-yl]methyl}piperazin-1-yl)-2-(1H-indol-5-yloxy)-N-({3-nitro-4-[(1-tetrahydro-2H-pyran-4-yl-piperidin-4-yl)amino]phenyl}sulfonyl)benzamide | |
| 4-(4-{[2-(4-chlorophenyl)-4,4-dimethylcyclohex-1-en-1-yl]methyl}piperazin-1-yl)-2-(1H-indol-5-yloxy)-N-({4-[(4-methylpiperazin-1-yl)amino]-3-nitrophenyl}sulfonyl)benzamide | |

| Name | Structure |
|---|---|
| 4-{4-[1-(4'-chloro-1,1'-biphenyl-2-yl)ethyl]piperazin-1-yl}-2-(1H-indol-4-yloxy)-N-({3-nitro-4-[(tetrahydro-2H-pyran-4-ylmethyl)amino]phenyl}sulfonyl)benzamide | 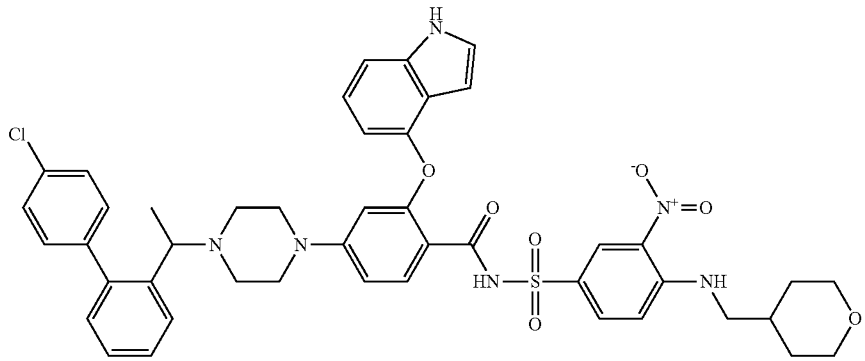 |
| N-[(4-{[(4-amino-tetrahydro-2H-pyran-4-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-indol-4-yloxy)benzamide | 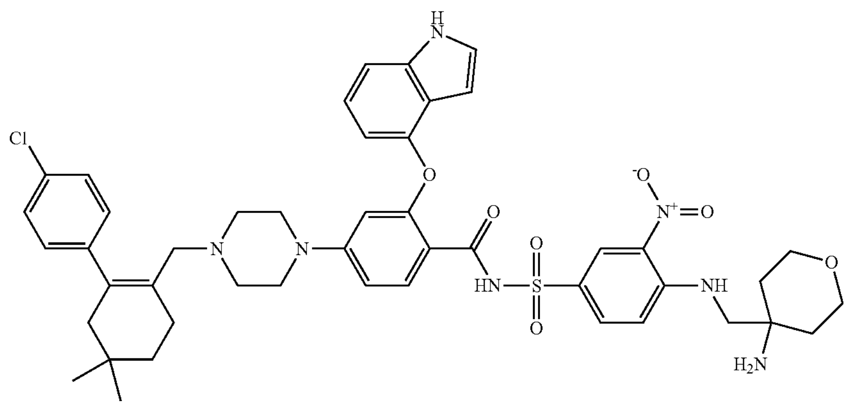 |
| 4-(4-{[2-(4-chlorophenyl)-4,4-dimethylcyclohex-1-en-1-yl]methyl]piperazin-1-yl)-2-(1H-indol-5-yloxy)-N-({3-nitro-4-[(tetrahydro-2H-pyran-4-ylmethyl)amino]phenyl}sulfonyl)benzamide | |

| Name | Structure |
|---|---|
| Trans-4-(4-{[2-(4-chlorophenyl)-4,4-dimethylcyclohex-1-en-1-yl]methyl}piperazin-1-yl)-2-(1H-indol-5-yloxy)-N-({4-[(4-morpholin-4-ylcyclohexyl)amino]-3-nitrophenyl}sulfonyl)benzamide | |
| 4-(4-{[2-(4-chlorophenyl)-4,4-dimethylcyclohex-1-en-1-yl]methyl}piperazin-1-yl)-2-(1H-indol-5-yloxy)-N-({4-[(2-methoxyethyl)amino]-3-nitrophenyl}sulfonyl)benzamide | |
| 4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[(3S)-tetrahydro-2H-pyran-3-ylmethyl]amino}phenyl)sulfonyl]benzamide | |

Caution: Stereochemical terms discarded: 3s

-continued

| Name | Structure |
|---|---|
| 4-(4-{[2-(4-chloro-phenyl)-4,4-dimethylcyclohex-1-en-1-yl]methyl}piperazin-1-yl)-2-(1H-indol-5-yloxy)-N-[(3-nitro-4-{[(3R)-tetrahydro-2H-pyran-3-ylmethyl]amino}phenyl)sulfonyl]benzamide | 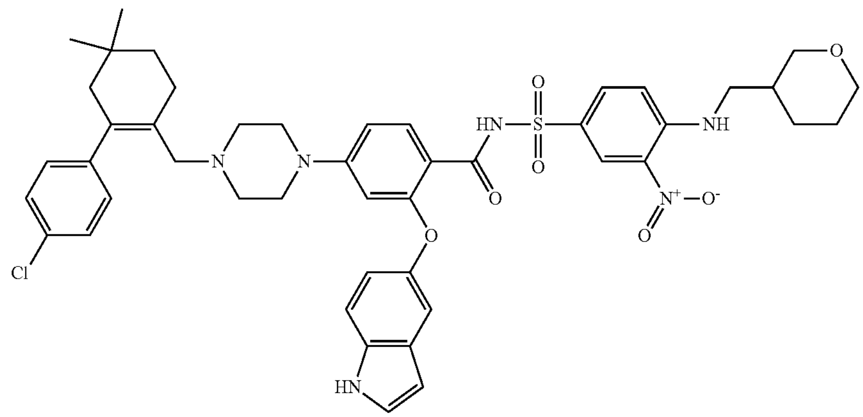 [SMILES: CC1(C)CCC(CN2CCN(c3ccc(C(=O)NS(=O)(=O)c4ccc(NCC5CCCOC5)c([N+](=O)[O-])c4)c(Oc4ccc5[nH]ccc5c4)c3)CC2)=C(c2ccc(Cl)cc2)C1] |

Caution: Stereochemical terms discarded: 3r

| 4-(4-{[4-(4-chloro-phenyl)-6,6-dimethyl-5,6-dihydro-2H-pyran-3-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide | 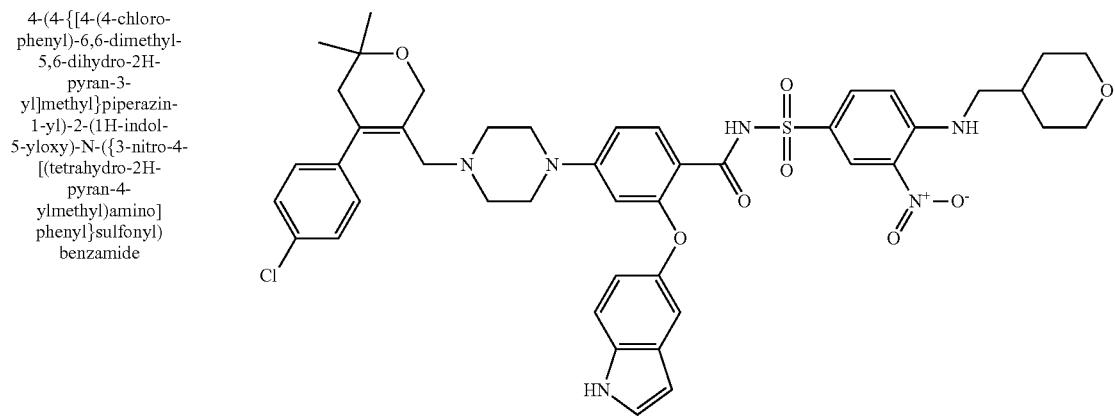 |
| 4-(4-{[2-(4-chloro-phenyl)-4,4-dimethylcyclohex-1-en-1-yl]methyl}piperazin-1-yl)-N-[(4-{[(4-hydroxy-1-methyl-piperidin-4-yl)methyl]amino}-3-nitrophenyl)sulfonyl]-2-(1H-indol-5-yloxy)benzamide | 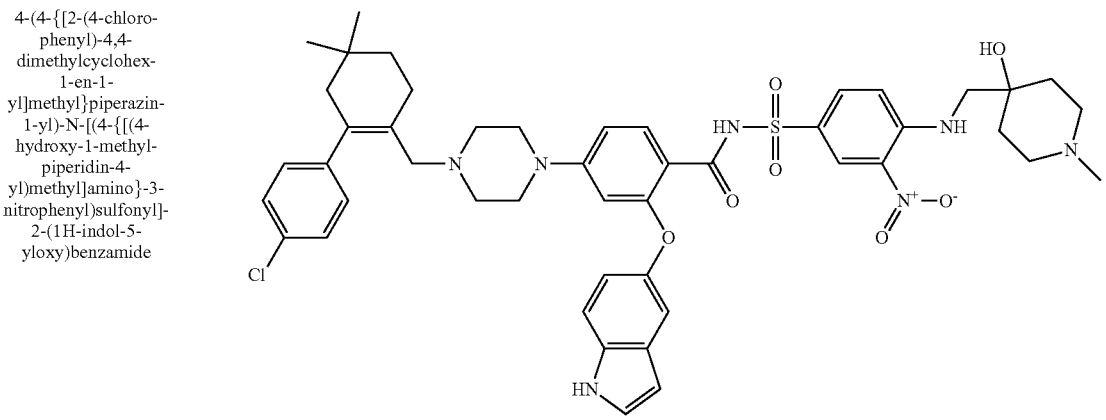 |

-continued

| Name | Structure |
|---|---|
| 4-(4-{[2-(4-chlorophenyl)-4,4-dimethylcyclohex-1-en-1-yl]methyl}piperazin-1-yl)-3-fluoro-2-(1H-indol-5-yloxy)-N-({4-[(1-methylpiperidin-4-yl)amino]-3-nitrophenyl}sulfonyl)benzamide | 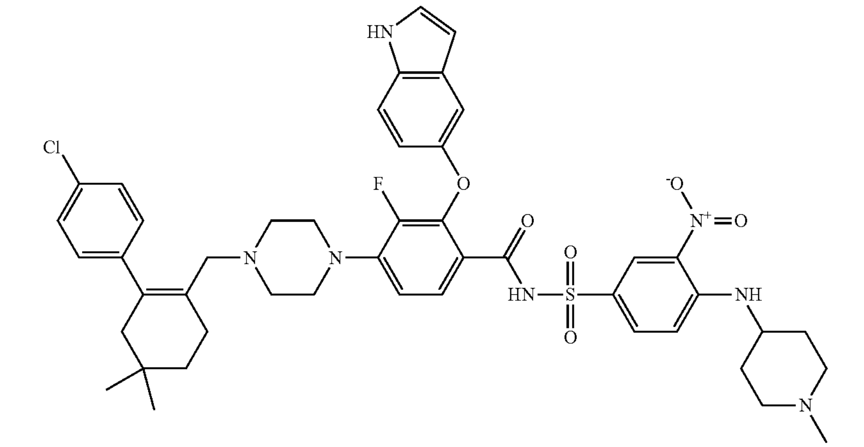 |
| 4-(4-{[2-(4-chlorophenyl)-4,4-dimethylcyclohex-1-en-1-yl]methyl}piperazin-1-yl)-3-fluoro-2-(1H-indol-5-yloxy)-N-({3-nitro-4-[(1-tetrahydro-2H-pyran-4-ylpiperidin-4-yl)amino]phenyl}sulfonyl)benzamide | 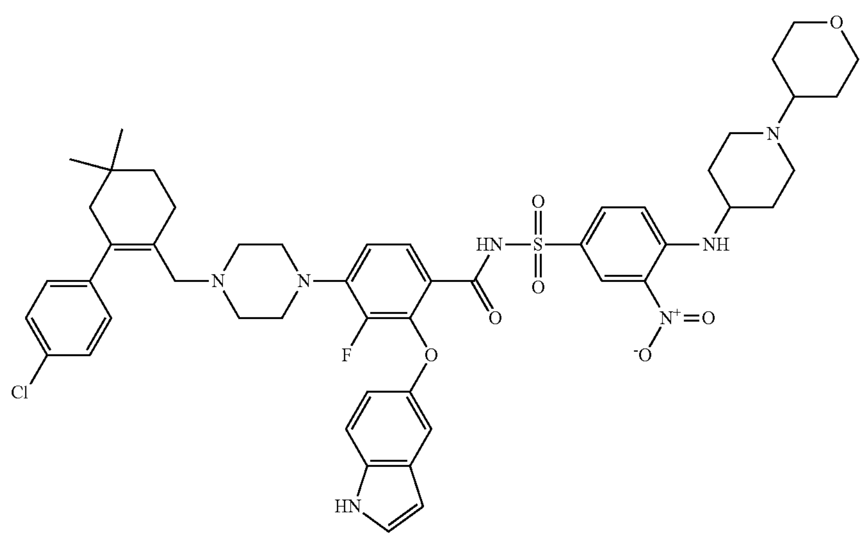 |
| 4-(4-{[2-(4-chlorophenyl)-4,4-dimethylcyclohex-1-en-1-yl]methyl}piperazin-1-yl)-N-[(4-{[(4-hydroxy-1-methylpiperidin-4-yl)methyl]amino}-3-nitrophenyl)sulfonyl]-2-(1H-indol-4-yloxy)benzamide | 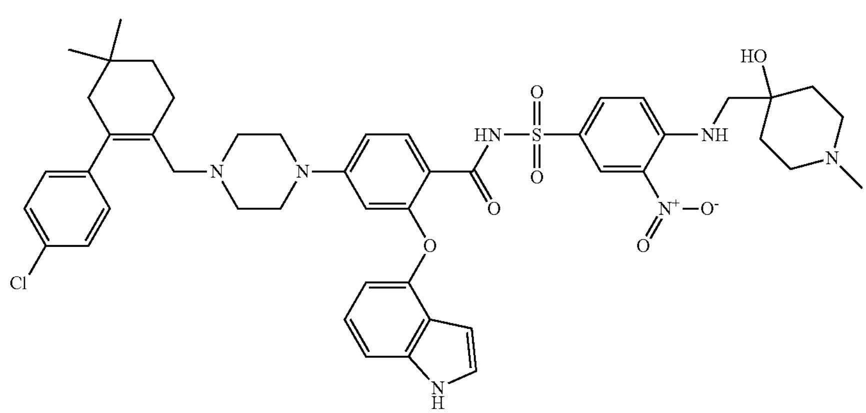 [SMILES: CN1CCC(O)(CNc2ccc(S(=O)(=O)NC(=O)c3ccc(N4CCN(CC5=C(c6ccc(Cl)cc6)CC(C)(C)CC5)CC4)cc3Oc3cccc4[nH]ccc34)cc2[N+](=O)[O-])CC1] |

-continued

| Name | Structure |
|---|---|
| N-[(4-{[(3S,4R)-1-benzyl-3-hydroxypiperidin-4-yl]amino}-3-nitrophenyl)sulfonyl]-4-(4-{[2-(4-chlorophenyl)-4,4-dimethylcyclohex-1-en-1-yl]methyl}piperazin-1-yl)-2-(1H-indol-5-yloxy)benzamide | |
| N-[(4-{[(4-amino-tetrahydro-2H-pyran-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-indol-5-yloxy)benzamide | |
| 4-(4-{[2-(4-chlorophenyl)-4,4-dimethylcyclohex-1-en-1-yl]methyl}piperazin-1-yl)-2-(1H-indol-5-yloxy)-N-[(4-{[1-(2-methoxyethyl)piperidin-4-yl]amino}-3-nitrophenyl)sulfonyl]benzamide | |

| Name | Structure |
|---|---|
| 4-(4-{[2-(4-chlorophenyl)-4,4-dimethylcyclohex-1-en-1-yl]methyl}piperazin-1-yl)-2-(1H-indol-4-yloxy)-N-({4-[(4-methylpiperazin-1-yl)amino]-3-nitrophenyl}sulfonyl)benzamide | |
| 4-(4-{[2-(4-chlorophenyl)-4,4-dimethylcyclohex-1-en-1-yl]methyl}piperazin-1-yl)-N-[(4-{[1-(2-hydroxyethyl)piperidin-4-yl]amino}-3-nitrophenyl)sulfonyl]-2-(1H-indol-4-yloxy)benzamide | |
| 4-(4-{[2-(4-chlorophenyl)-4,4-dimethylcyclohex-1-en-1-yl]methyl}piperazin-1-yl)-2-(1H-indol-4-yloxy)-N-[(4-{[1-(2-methoxyethyl)piperidin-4-yl]amino}-3-nitrophenyl)sulfonyl]benzamide | |

| Name | Structure |
|---|---|
| 4-(4-{[2-(4-chlorophenyl)-4,4-dimethylcyclohex-1-en-1-yl]methyl}piperazin-1-yl)-N-[(4-{[1-(3-hydroxypropyl)piperidin-4-yl]amino}-3-nitrophenyl)sulfonyl]-2-(1H-indol-4-yloxy)benzamide | |
| 4-[4-({4'-chloro-3-[3-(dimethylamino)propyl]-1,1'-biphenyl-2-yl}methyl)piperazin-1-yl]-2-(1H-indol-4-yloxy)-N-({3-nitro-4-[(tetrahydro-2H-pyran-4-ylmethyl)amino]phenyl}sulfonyl)benzamide | 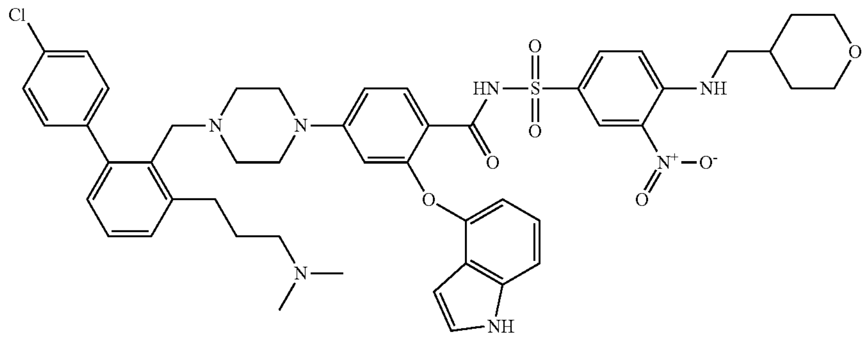 [SMILES: CN(C)CCCc1cccc(-c2ccc(Cl)cc2)c1CN1CCN(c2ccc(C(=O)NS(=O)(=O)c3ccc(NCC4CCOCC4)c([N+](=O)[O-])c3)c(Oc3cccc4[nH]ccc34)c2)CC1] |
| 4-(4-{[2-(4-chlorophenyl)-4,4-dimethylcyclohex-1-en-1-yl]methyl}piperazin-1-yl)-N-[(4-{[1-(3-hydroxypropyl)piperidin-4-yl]amino}-3-nitrophenyl)sulfonyl]-2-(1H-indol-5-yloxy)benzamide | |
| 4-{4-[(4'-chloro-4-morpholin-4-yl-1,1'-biphenyl-2-yl)methyl]piperazin-1-yl}-2-(1H-indol-4-yloxy)-N-({3-nitro-4-[(tetrahydro-2H-pyran-4-ylmethyl)amino]phenyl}sulfonyl)benzamide | 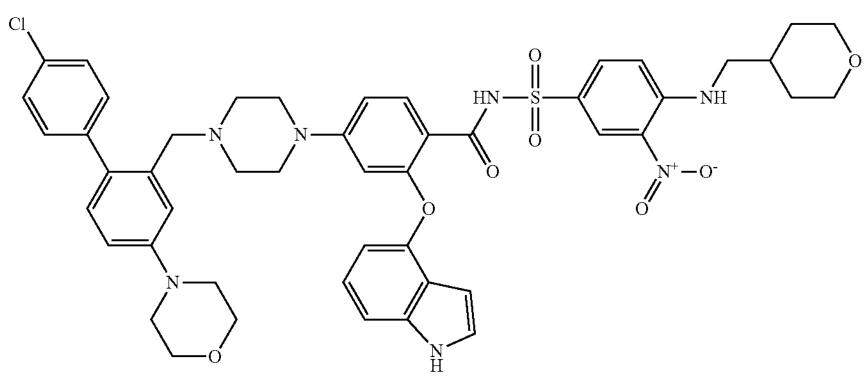 [SMILES: O=C(NS(=O)(=O)c1ccc(NCC2CCOCC2)c([N+](=O)[O-])c1)c1ccc(N2CCN(Cc3cc(N4CCOCC4)ccc3-c3ccc(Cl)cc3)CC2)cc1Oc1cccc2[nH]ccc12] |

-continued

| Name | Structure |
|---|---|
| 4-[4-({4'-chloro-3-[2-(dimethylamino)ethoxy]-1,1'-biphenyl-2-yl}methyl)piperazin-1-yl]-2-(1H-indol-4-yloxy)-N-({3-nitro-4-[(1-tetrahydro-2H-pyran-4-ylpiperidin-4-yl)amino]phenyl}sulfonyl)benzamide | 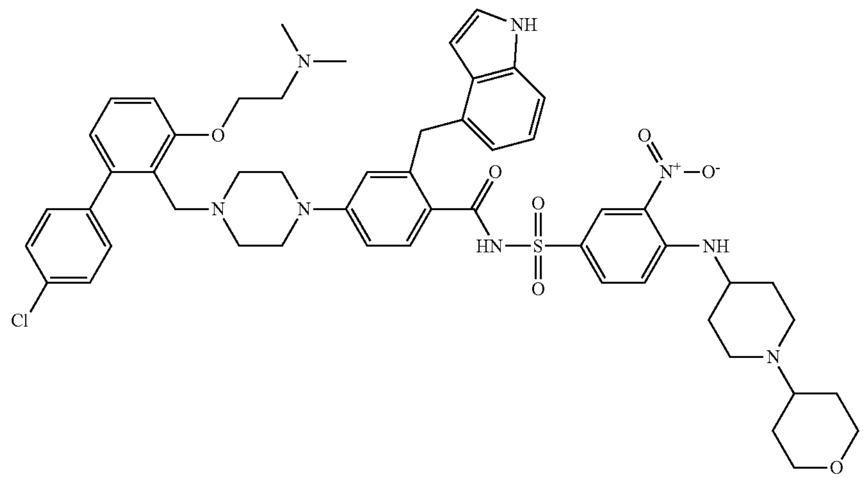 [SMILES: CN(C)CCOc1cccc(-c2ccc(Cl)cc2)c1CN1CCN(c2ccc(C(=O)NS(=O)(=O)c3ccc(NC4CCN(C5CCOCC5)CC4)c([N+](=O)[O-])c3)c(Cc3cccc4[nH]ccc34)c2)CC1] |
| 4-{4-[1-(4'-chloro-1,1'-biphenyl-2-yl)ethyl]piperazin-1-yl}-2-(1H-indol-4-yloxy)-N-({3-nitro-4-[(tetrahydro-2H-pyran-4-ylmethyl)amino]phenyl}sulfonyl)benzamide; | 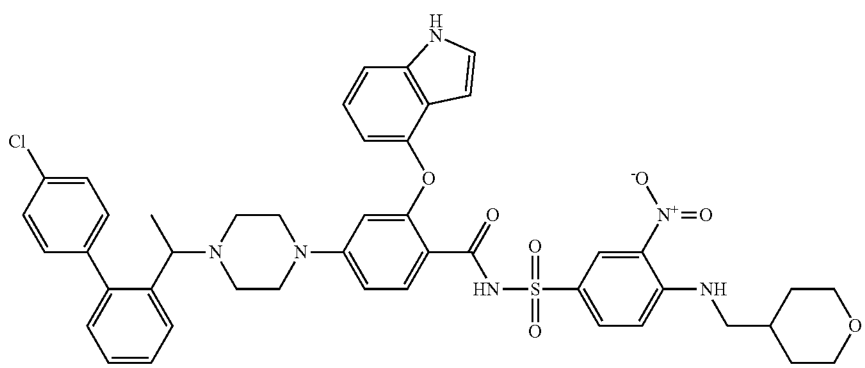 |
| 4-(4-{[2-(4-chlorophenyl)-4,4-dimethylcyclohex-1-en-1-yl]methyl]piperazin-1-yl)-N-[(4-{[4-(diethylamino)cyclohexyl]amino}-3-nitrophenyl)sulfonyl]-2-(1H-indol-5-yloxy)benzamide | |

-continued

| Name | Structure |
|---|---|
| 4-(4-{[2-(4-chlorophenyl)-4,4-dimethylcyclohex-1-en-1-yl]methyl}piperazin-1-yl)-N-[(4-{[4-(dimethylamino)cyclohexyl]amino}-3-nitrophenyl)sulfonyl]-2-(1H-indol-4-yloxy)benzamide | |
| 4-(4-{[2-(4-chlorophenyl)-4,4-dimethylcyclohex-1-en-1-yl]methyl}piperazin-1-yl)-N-[(4-{[4-(diethylamino)cyclohexyl]amino}-3-nitrophenyl)sulfonyl]-2-(1H-indol-4-yloxy)benzamide | |
| Trans-4-(4-{[2-(4-chlorophenyl)-4,4-dimethylcyclohex-1-en-1-yl]methyl}piperazin-1-yl)-2-(1H-indol-4-yloxy)-N-({4-[(4-morpholin-4-ylcyclohexyl)amino]-3-nitrophenyl}sulfonyl)benzamide | |

| Name | Structure |
|---|---|
| 4-[4-({4'-chloro-3-[2-(dimethylamino)ethoxy]-1,1'-biphenyl-2-yl}methyl)piperazin-1-yl]-2-(1H-indol-4-yloxy)-N-({4-[(1-methylpiperidin-4-yl)amino]-3-nitrophenyl}sulfonyl)benzamide | |
| 4-{4-[1-(4'-chloro-1,1'-biphenyl-2-yl)ethyl]piperazin-1-yl}-2-(1H-indol-4-yloxy)-N-({4-[(1-methylpiperidin-4-yl)amino]-3-nitrophenyl}sulfonyl)benzamide | |
| 4-(4-{[2-(4-chlorophenyl)-4,4-dimethylcyclohex-1-en-1-yl]methyl}piperazin-1-yl)-N-{[4-({[4-(dimethylamino)tetrahydro-2H-pyran-4-yl]methyl}amino)-3-nitrophenyl]sulfonyl}-2-(1H-indol-5-yloxy)benzamide | |

| Name | Structure |
|---|---|
| N-({4-[(2-amino-cyclohexyl)amino]-3-nitrophenyl}sulfonyl)-4-(4-{[2-(4-chlorophenyl)-4,4-dimethylcyclohex-1-en-1-yl]methyl]piperazin-1-yl)-2-(1H-indol-5-yloxy)benzamide | |
| 4-[4-({4'-chloro-4-[3-(dimethylamino)prop-1-ynyl]-1,1'-biphenyl-2-yl}methyl)piperazin-1-yl]-2-(1H-indol-4-yloxy)-N-({3-nitro-4-[(tetrahydro-2H-pyran-4-ylmethyl)amino]phenyl}sulfonyl)benzamide | 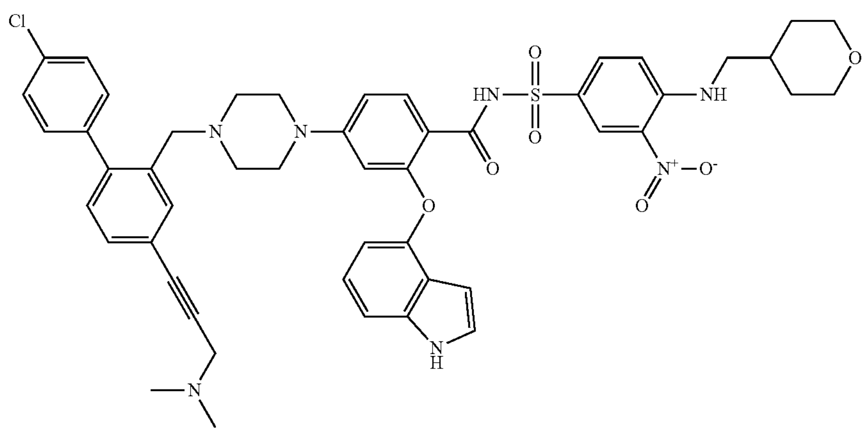 [SMILES: CN(C)CC#Cc1ccc(-c2ccc(Cl)cc2)c(CN2CCN(c3ccc(C(=O)NS(=O)(=O)c4ccc(NCC5CCOCC5)c([N+](=O)[O-])c4)c(Oc4cccc5[nH]ccc45)c3)CC2)c1] |
| 4-(4-{[2-(4-chloro-phenyl)-4,4-dimethylcyclohex-1-en-1-yl]methyl}piperazin-1-yl)-2-(1H-indol-4-yloxy)-N-[(3-nitro-4-{[1-(4,4,4-trifluorobutyl)piperidin-4-yl]amino}phenyl)sulfonyl]benzamide | 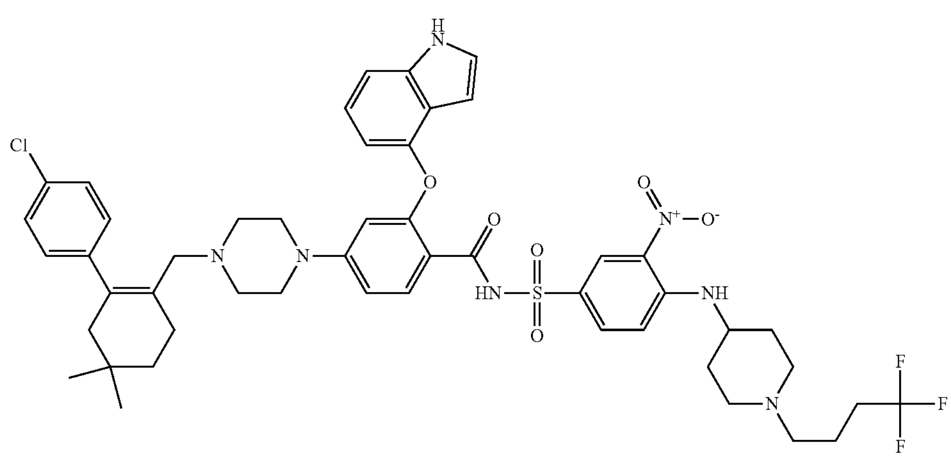 [SMILES: CC1(C)CCC(CN2CCN(c3ccc(C(=O)NS(=O)(=O)c4ccc(NC5CCN(CCCC(F)(F)F)CC5)c([N+](=O)[O-])c4)c(Oc4cccc5[nH]ccc45)c3)CC2)=C(c2ccc(Cl)cc2)C1] |

| Name | Structure |
|---|---|
| 4-(4-{[2-(4-chlorophenyl)-4,4-dimethylcyclohex-1-en-1-yl]methyl}piperazin-1-yl)-N-[(4-{[2-(4-hydroxy-1-methylpiperidin-4-yl)ethyl]amino}-3-nitrophenyl)sulfonyl]-2-(1H-indol-5-yloxy)benzamide | |
| 4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[1-(1,3-thiazol-2-yl)piperidin-4-yl]amino}phenyl)sulfonyl]benzamide | |
| 4-(4-{[4'-chloro-4-(2-hydroxyethoxy)-1,1'-biphenyl-2-yl]methyl}piperazin-1-yl)-2-(1H-indol-4-yloxy)-N-({3-nitro-4-[(tetrahydro-2H-pyran-4-ylmethyl)amino]phenyl}sulfonyl)benzamide | |

-continued

| Name | Structure |
|---|---|
| 4-(4-{[2-(4-chlorophenyl)-4,4-dimethylcyclohex-1-en-1-yl]methyl}piperazin-1-yl)-N-[(4-{[1-(cyclopropylmethyl)piperidin-4-yl]amino}-3-nitrophenyl)sulfonyl]-2-(1H-indol-5-yloxy)benzamide | |
| 4-(4-{[2-(4-chlorophenyl)-4,4-dimethylcyclohex-1-en-1-yl]methyl}piperazin-1-yl)-2-(1H-indol-4-yloxy)-N-({4-[(4-methylpiperazin-1-yl)amino]-3-[(trifluoromethyl)sulfonyl]phenyl}sulfonyl)benzamide | |
| 4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[1-(4,4,4-trifluorobutyl)piperidin-4-yl]amino}phenyl)sulfonyl]benzamide | |

-continued

| Name | Structure |
|------|-----------|
| 4-{4-[1-(4'-chloro-1,1'-biphenyl-2-yl)ethyl]piperazin-1-yl}-2-(1H-indol-4-yloxy)-N-({4-[(4-methylpiperazin-1-yl)amino]-3-nitrophenyl}sulfonyl)benzamide | |
| 4-[4-{[2-(4-chlorophenyl)-4,4-dimethylcyclohex-1-en-1-yl]methyl}-3-(hydroxymethyl)piperazin-1-yl]-2-(1H-indol-5-yloxy)-N-({4-[(1-methylpiperidin-4-yl)amino]-3-nitrophenyl}sulfonyl)benzamide | |
| 4-[4-{[2-(4-chlorophenyl)-4,4-dimethylcyclohex-1-en-1-yl]methyl}-3-(hydroxymethyl)piperazin-1-yl]-2-(1H-indol-5-yloxy)-N-({3-nitro-4-[(1-tetrahydro-2H-pyran-4-ylpiperidin-4-yl)amino]phenyl}sulfonyl)benzamide | |

-continued

| Name | Structure |
|---|---|
| 4-(4-{[2-(4-chlorophenyl)-4,4-dimethylcyclohex-1-en-1-yl]methyl}piperazin-1-yl)-2-(1H-indol-5-yloxy)-N-({4-[(4-methylpiperazin-1-yl)amino]-3-[(trifluoromethyl)sulfonyl]phenyl}sulfonyl)benzamide | 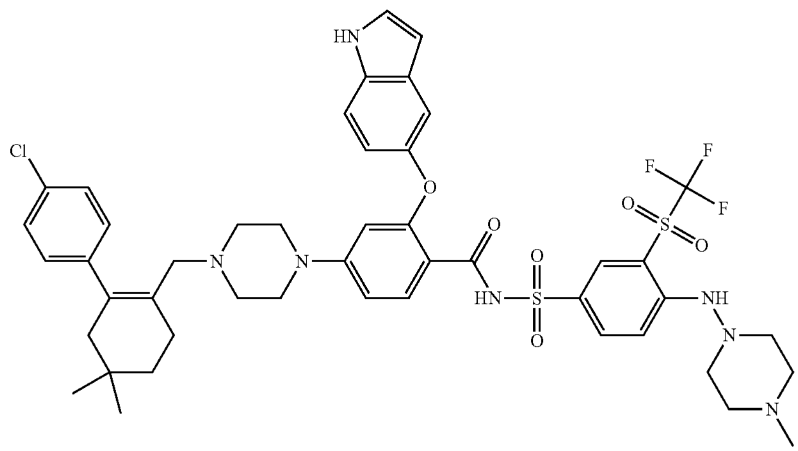 |
| 4-(4-{[4'-chloro-4-(2-hydroxyethoxy)-1,1'-biphenyl-2-yl]methyl}piperazin-1-yl)-2-(1H-indol-4-yloxy)-N-({4-[(1-methylpiperidin-4-yl)amino]-3-nitrophenyl}sulfonyl)benzamide | 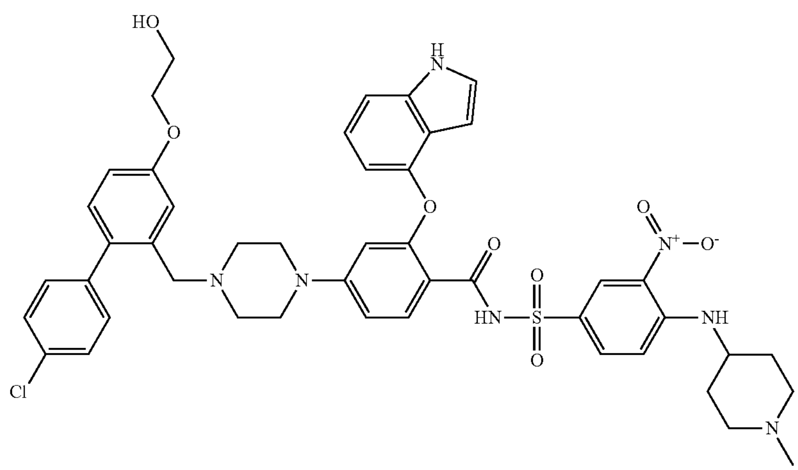 [SMILES: CN1CCC(Nc2ccc(S(=O)(=O)NC(=O)c3ccc(N4CCN(Cc5cc(OCCO)ccc5-c5ccc(Cl)cc5)CC4)cc3Oc3cccc4[nH]ccc34)cc2[N+](=O)[O-])CC1] |
| 4-(4-{[2-(4-chlorophenyl)-4,4-dimethylcyclohex-1-en-1-yl]methyl}piperazin-1-yl)-2-(1H-indol-5-yloxy)-N-[(3-nitro-4-{3-[3-(3-oxopiperazin-1-yl)propyl]amino}phenyl)sulfonyl]benzamide | |

| Name | Structure |
|---|---|
| 4-(4-{[2-(4-chloro-phenyl)-4,4-dimethylcyclohex-1-en-1-yl]methyl}piperazin-1-yl)-2-(1H-indol-4-yloxy)-N-[(3-nitro-4-{[3-(3-oxopiperazin-1-yl)propyl]amino}phenyl)sulfonyl]benzamide | 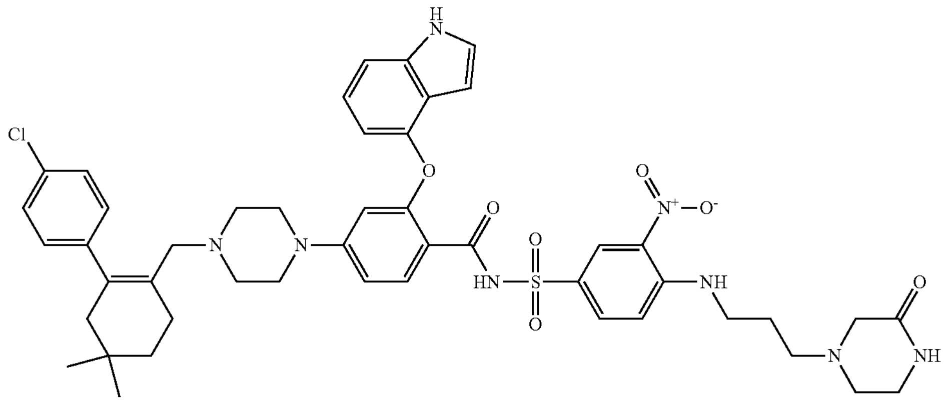 [SMILES: CC1(C)CCC(CN2CCN(c3ccc(C(=O)NS(=O)(=O)c4ccc(NCCCN5CCNC(=O)C5)c([N+](=O)[O-])c4)c(Oc4cccc5[nH]ccc45)c3)CC2)=C(c2ccc(Cl)cc2)C1] |
| 4-(4-{[2-(4-chloro-phenyl)-5-hydroxycyclohex-1-en-1-yl]methyl]piperazin-1-yl)-2-(1H-indol-5-yloxy)-N-({4-[(1-methylpiperidin-4-yl)amino]-3-nitrophenyl}sulfonyl)benzamide | |
| 4-(4-{[2-(4-chloro-phenyl)-5-hydroxycyclohex-1-en-1-yl]methyl}piperazin-1-yl)-2-(1H-indol-5-yloxy)-N-({3-nitro-4-[(1-tetrahydro-2H-pyran-4-yl-piperidin-4-yl)amino]phenyl}sulfonyl)benzamide | 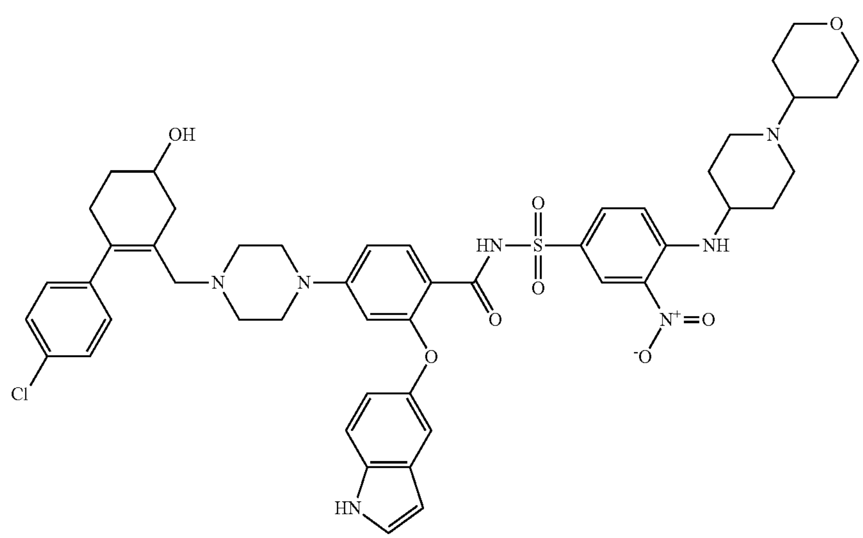 |

| Name | Structure |
|---|---|
| 4-(4-{[2-(4-chlorophenyl)-5-hydroxycyclohex-1-en-1-yl]methyl}piperazin-1-yl)-2-(1H-indol-5-yloxy)-N-({4-[(4-methylpiperazin-1-yl)amino]-3-nitrophenyl}sulfonyl)benzamide | |
| 4-(4-{[2-(4-chlorophenyl)-4,4-dimethylcyclohex-1-en-1-yl]methyl}piperazin-1-yl)-N-[(4-{[1-(2,3-dihydro-1H-inden-2-yl)piperidin-4-yl]amino}-3-nitrophenyl)sulfonyl]-2-(1H-indol-4-yloxy)benzamide | |
| 4-(4-{[2-(4-chlorophenyl)-4,4-dimethylcyclohex-1-en-1-yl]methyl}piperazin-1-yl)-N-[(4-{[1-(2,3-dihydro-1H-inden-2-yl)piperidin-4-yl]amino}-3-nitrophenyl)sulfonyl]-2-(1H-indol-5-yloxy)benzamide | |

| Name | Structure |
|---|---|
| 4-(4-{[2-(4-chloro-phenyl)-4,4-dimethylcyclohex-1-en-1-yl]methyl}piperazin-1-yl)-2-(1H-indol-5-yloxy)-N-[(4-{[(1-morpholin-4-ylcyclohexyl)methyl]amino}-3-nitrophenyl)sulfonyl]benzamide | 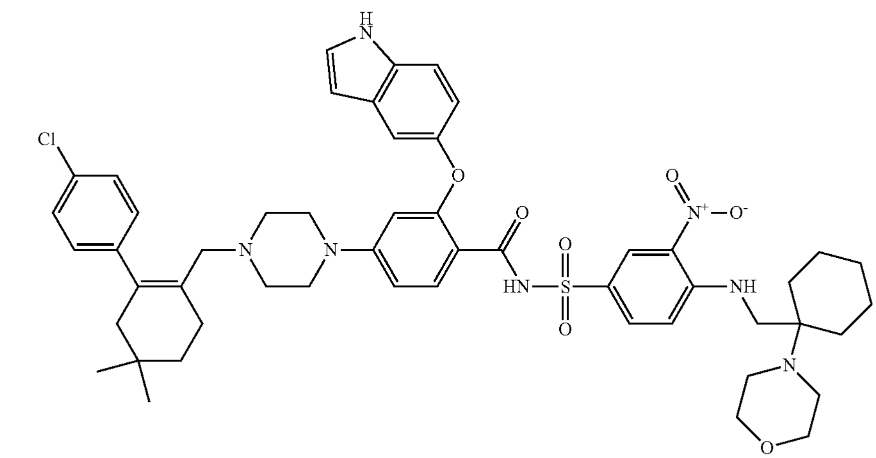 [SMILES: CC1(C)CCC(CN2CCN(c3ccc(C(=O)NS(=O)(=O)c4ccc(NCC5(N6CCOCC6)CCCCC5)c([N+](=O)[O-])c4)c(Oc4ccc5[nH]ccc5c4)c3)CC2)=C(c2ccc(Cl)cc2)C1] |
| 4-(4-{[2-(4-chloro-phenyl)-4,4-dimethylcyclohex-1-en-1-yl]methyl}piperazin-1-yl)-2-(1H-indol 5-yloxy)-N-[(3-nitro-4-{[1-(1,3-thiazol-2-ylmethyl)piperidin-4-yl]amino}phenyl)sulfonyl]benzamide | 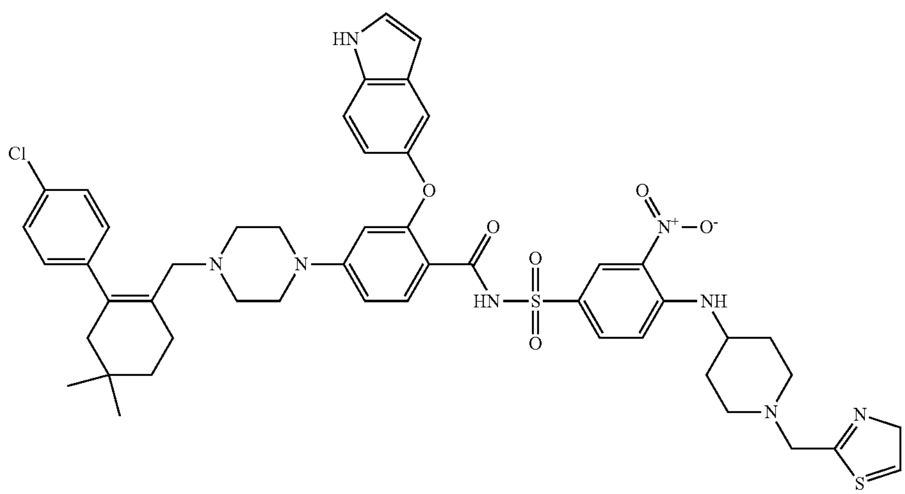 |
| 4-(4-{[2-(4-chloro-phenyl)-4,4-dimethylcyclohex-1-en-1-yl]methyl}piperazin-1-yl)-2-(1H-indol-5-yloxy)-N-[(3-nitro-4-{[1-(1,3-thiazol-4-ylmethyl)piperidin-4-yl]amino}phenyl)sulfonyl]benzamide | 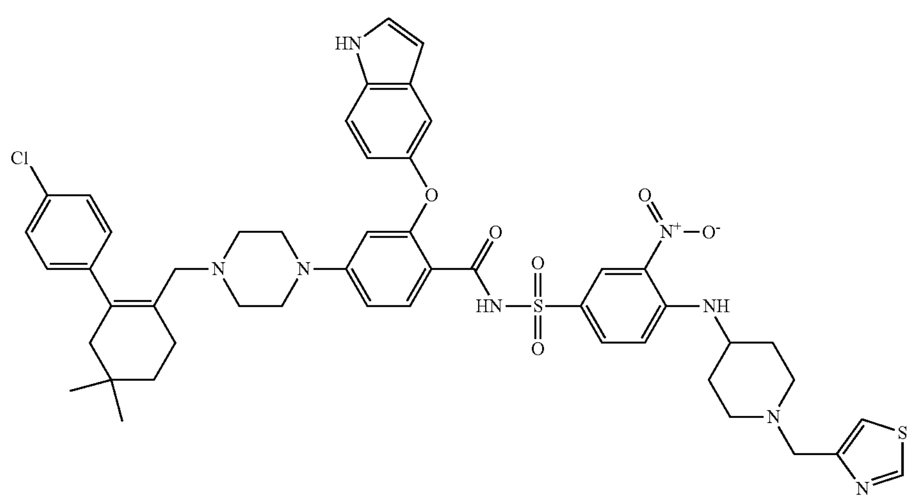 [SMILES: CC1(C)CCC(CN2CCN(c3ccc(C(=O)NS(=O)(=O)c4ccc(NC5CCN(Cc6cscn6)CC5)c([N+](=O)[O-])c4)c(Oc4ccc5[nH]ccc5c4)c3)CC2)=C(c2ccc(Cl)cc2)C1] |

| Name | Structure |
|---|---|
| 4-(4-{[2-(4-chlorophenyl)-4,4-dimethylcyclohex-1-en-1-yl]methyl}piperazin-1-yl)-N-{[4-({[4-(hydroxymethyl)tetrahydro-2H-pyran-4-yl]methyl}amino)-3-nitrophenyl]sulfonyl}-2-(1H-indol-5-yloxy)benzamide | |
| 4-(4-{[2-(4-chlorophenyl)-4,4-dimethylcyclohex-1-en-1-yl]methyl}piperazin-1-yl)-N-[(4-{[4-(2-hydroxyethyl)piperazin-1-yl]amino}-3-nitrophenyl)sulfonyl]-2-(1H-indol-5-yloxy)benzamide | |
| 4-(4-{[2-(4-chlorophenyl)-4,4-dimethylcyclohex-1-en-1-yl]methyl}piperazin-1-yl)-2-(1H-indol-5-yloxy)-N-[(4-{[(3S)-1-methylpyrrolidin-3-yl]amino}-3-nitrophenyl)sulfonyl]benzamide | |

-continued

| Name | Structure |
|---|---|
| 4-(4-{[2-(4-chloro-phenyl)-4,4-dimethylcyclohex-1-en-1-yl]methyl]piperazin-1-yl)-N-[(4-{[1-(3-fluoropropyl)piperidin-4-yl]amino}-3-nitrophenyl)sulfonyl]-2-(1H-indol-5-yloxy)benzamide | 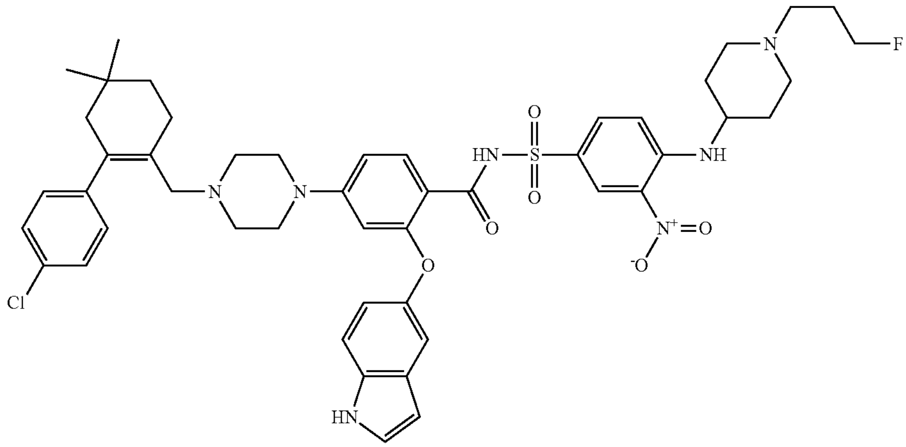 |
| 4-[4-{[2-(4-chloro-phenyl)-4,4-dimethylcyclohex-1-en-1-yl]methyl}-3-(hydroxymethyl)piperazin-1-yl]-2-(1H-indol-5-yloxy)-N-({3-nitro-4-[(tetrahydro-2H-pyran-4-ylmethyl)amino]phenyl}sulfonyl)benzamide | 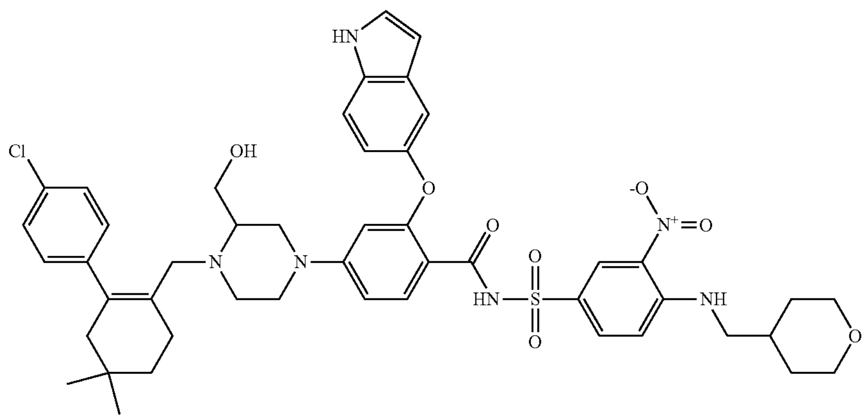 |
| N-[(4-{[(4-amino-tetrahydro-2H-pyran-4-yl)methyl]amino}-3-nitrophenyl)sulfonyl]-4-[4-{[2-(4-chlorophenyl)-4,4-dimethylcyclohex-1-en-1-yl]methyl}-3-(hydroxymethyl)piperazin-1-yl]-2-(1H-indol-5-yloxy)benzamide | 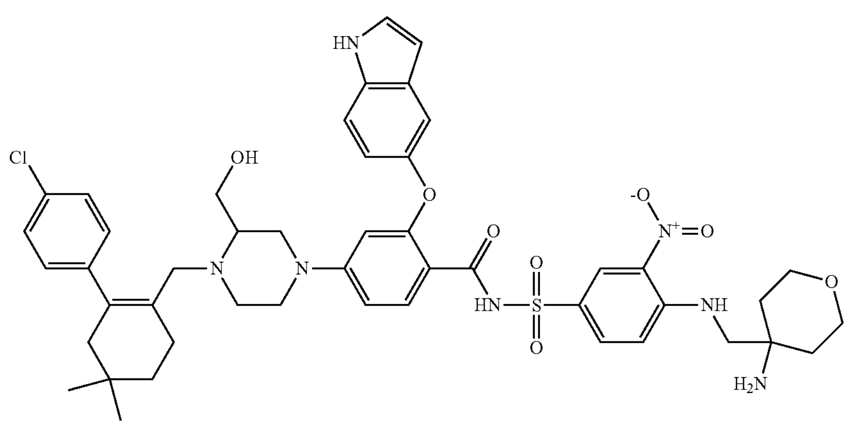 |

| Name | Structure |
|---|---|
| 4-(4-{[2-(4-chloro-phenyl)-4,4-dimethylcyclohex-1-en-1-yl]methyl}piperazin-1-yl)-N-[(4-{[(1-hydroxycyclohexyl)methyl]amino}-3-nitrophenyl)sulfonyl]-2-(1H-indol-5-yloxy)benzamide | 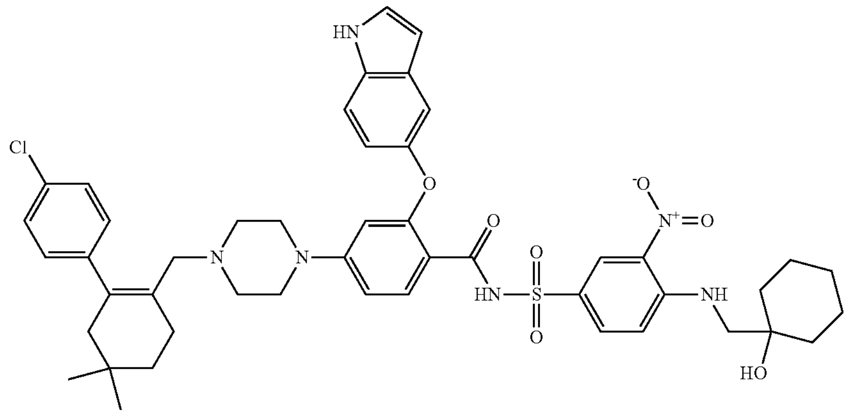 |
| 4-(4-{[2-(4-chloro-phenyl)-4,4-dimethylcyclohex-1-en-1-yl]methyl]piperazin-1-yl)-2-(1H-indol-4-yloxy)-N-({4-[(2-methoxyethyl)amino]-3-nitrophenyl}sulfonyl)benzamide | 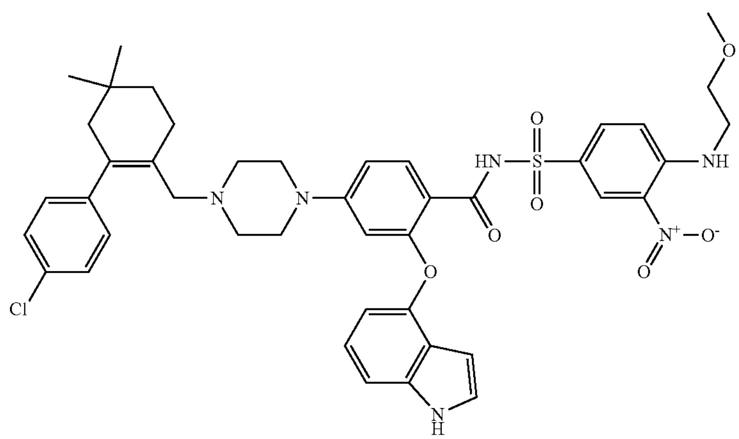 [SMILES: COCCNc1ccc(S(=O)(=O)NC(=O)c2ccc(N3CCN(CC4=C(c5ccc(Cl)cc5)CC(C)(C)CC4)CC3)cc2Oc2cccc3[nH]ccc23)cc1[N+](=O)[O-]] |
| 4-(4-{[2-(4-chloro-phenyl)-4,4-dimethylcyclohex-1-en-1-yl]methyl}piperazin-1-yl)-N-[(4-{[4-(hydroxymethyl)tetrahydro-2H-pyran-4-yl]amino}-3-nitrophenyl)sulfonyl]-2-(1H-indol-5-yloxy)benzamide | |

| Name | Structure |
|---|---|
| 4-(4-{[2-(4-chlorophenyl)-4,4-dimethylcyclohex-1-en-1-yl]methyl}piperazin-1-yl)-N-[(4-{[4-(hydroxymethyl)tetrahydro-2H-pyran-yl]amino}-3-nitrophenyl)sulfonyl]-2-(1H-indol-4-yloxy)benzamide | |
| 4-(4-{[2-(4-chlorophenyl)-4,4-dimethylcyclohex-1-en-1-yl]methyl}piperazin-1-yl)-N-({4-[(2-hydroxy-1-tetrahydro-2H-pyran-4-ylethyl)amino]-3-nitrophenyl}sulfonyl)-2-(1H-indol-5-yloxy)benzamide | |
| 4-(4-{[2-(4-chlorophenyl)-4,4-dimethylcyclohex-1-en-1-yl]methyl}piperazin-1-yl)-2-(1H-indol-5-yloxy)-N-{[3-nitro-4-({1-[2-(1H-pyrazol-1-yl)ethyl]piperidin-4-yl}amino)phenyl]sulfonyl}benzamide | |

| Name | Structure |
|---|---|
| 4-(4-{[2-(4-chlorophenyl)-4,4-dimethylcyclohex-1-en-1-yl]methyl}piperazin-1-yl)-2-(1H-indol-4-yloxy)-N-({3-nitro-4-[(tetrahydro-2H-pyran-4-ylmethyl)amino]phenyl}sulfonyl)benzamide | |
| 4-(4-{[2-(4-chlorophenyl)-4,4-dimethylcyclohex-1-en-1-yl]methyl}piperazin-1-yl)-2-(1H-indol-5-yloxy)-N-{[4-(methylamino)-3-nitrophenyl]sulfonyl}benzamide | |
| 4-(4-{[2-(4-chlorophenyl)-4,4-dimethylcyclohex-1-en-1-yl]methyl}piperazin-1-yl)-2-(1H-indol-4-yloxy)-N-{[4-(methylamino)-3-nitrophenyl]sulfonyl}benzamide | |

| Name | Structure |
|---|---|
| 4-{4-[1-(4'-chloro-1,1'-biphenyl-2-yl)ethyl]piperazin-1-yl}-2-(1H-indol-4-yloxy)-N-({4-[(3-morpholin-4-ylpropyl)amino]-3-nitrophenyl}sulfonyl)benzamide | |
| 4-(4-{[2-(4-chlorophenyl)-5-hydroxycyclohex-1-en-1-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide | |
| 4-(4-{[2-(4-chlorophenyl)-5-morpholin-4-ylcyclohex-1-en-1-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide | |

| Name | Structure |
|---|---|
| N-[(4-{[(1-aminocyclohexyl)methyl]amino}-3-nitrophenyl)sulfonyl]-4-(4-{[2-(4-chlorophenyl)-4,4-dimethylcyclohex-1-en-1-yl]methyl]piperazin-1-yl)-2-(1H-indol-5-yloxy)benzamide | |
| 4-(4-{[2-(4-chlorophenyl)-4,4-dimethylcyclohex-1-en-1-yl]methyl]piperazin-1-yl)-2-(1H-indol-5-yloxy)-N-[(3-nitro-4-{[2-(2-oxopyrrolidin-1-yl)ethyl]amino}phenyl)sulfonyl]benzamide | |
| 4-{4-[1-(4'-chloro-1,1'-biphenyl-2-yl)ethyl]piperazin-1-yl}-2-(1H-indol-5-yloxy)-N-({3-nitro-4-[(tetrahydro-2H-pyran-4-ylmethyl)amino]phenyl}sulfonyl)benzamide | |

| Name | Structure |
|---|---|
| 4-(4-{1-[2-(4-chlorophenyl)-4,4-dimethylcyclohex-1-en-1-yl]ethyl}piperazin-1-yl)-2-(1H-indol-5-yloxy)-N-({3-nitro-4-[(tetrahydro-2H-pyran-4-ylmethyl)amino]phenyl}sulfonyl)benzamide | |
| 4-(4-{1-[2-(4-chlorophenyl)-4,4-dimethylcyclohex-1-en-1-yl]ethyl}piperazin-1-yl)-2-(1H-indol-5-yloxy)-N-({4[(4-methylpiperazin-1-yl)amino]-3-nitrophenyl}sulfonyl)benzamide | |
| 4-{4-[(1R)-1-(4'-chloro-1,1'-biphenyl-2-yl)ethyl]piperazin-1-yl}-2-(1H-indol-4-yloxy)-N-({3-nitro-4-[(tetrahydro-2H-pyran-4-ylmethyl)amino]phenyl}sulfonyl)benzamide | 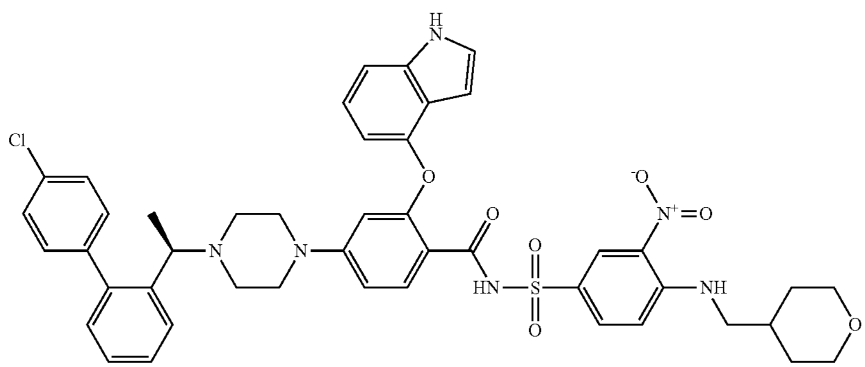 |
| 4-{4-[(1S)-1-(4'-chloro-1,1'-biphenyl-2-yl)ethyl]piperazin-1-yl}-2-(1H-indol-4-yloxy)-N-({3-nitro-4-[(tetrahydro-2H-pyran-4-ylmethyl)amino]phenyl}sulfonyl)benzamide | 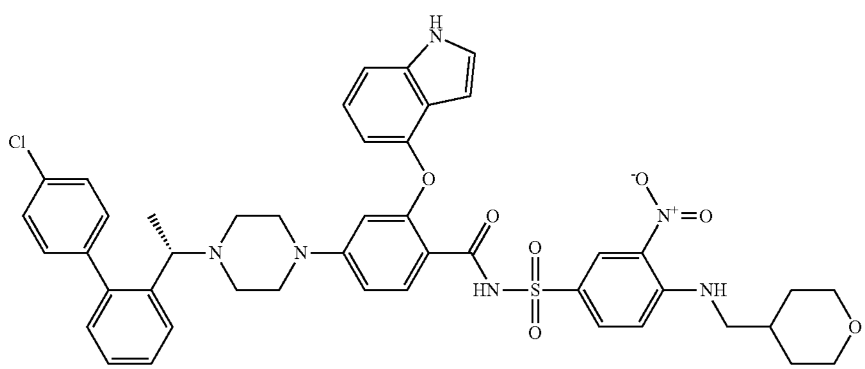 |

| Name | Structure |
|---|---|
| 4-(4-{1-[2-(4-chlorophenyl)-4,4-dimethylcyclohex-1-en-1-yl]ethyl}piperazin-1-yl)-2-(1H-indol-5-yloxy)-N-({4-[(3-morpholin-4-ylpropyl)amino]-3-nitrophenyl}sulfonyl)benzamide | |
| 4-(4-{1-[2-(4-chlorophenyl)-4,4-dimethylcyclohex-1-en-1-yl]ethyl}piperazin-1-yl)-2-(1H-indol-5-yloxy)-N-({3-nitro-4-[(1-tetrahydro-2H-pyran-4-ylpiperidin-4-yl)amino]phenyl}sulfonyl)benzamide | |
| 4-(4-{[2-(4-chlorophenyl)-4,4-dimethylcyclohex-1-en-1-yl]methyl}piperazin-1-yl)-N-({4-[(cyclohexylmethyl)amino]-3-nitrophenyl}sulfonyl)-2-(1H-indol-5-yloxy)benzamide | |

| Name | Structure |
|---|---|
| 4-(4-{[2-(4-chlorophenyl)-4,4-dimethylcyclohex-1-en-1-yl]methyl}piperazin-1-yl)-2-(1H-indol-5-yloxy)-N-{[4-(morpholin-4-ylamino)-3-nitrophenyl]sulfonyl}benzamide | |
| 4-(4-{[2-(4-chlorophenyl)-4,4-dimethylcyclohex-1-en-1-yl]methyl}piperazin-1-yl)-2-(1H-indol-5-yloxy)-N-({3-nitro-4-[(tetrahydro-2H-pyran-3-ylmethyl)amino]phenyl}sulfonyl)benzamide | |
| 4-(4-{[2-(4-chlorophenyl)-4,4-dimethylcyclohex-1-en-1-yl]methyl}piperazin-1-yl)-2-(1H-indol-4-yloxy)-N-{[4-(morpholin-4-ylamino)-3-nitrophenyl]sulfonyl}benzamide | |

-continued

| Name | Structure |
|---|---|
| 4-(4-{[2-(4-chlorophenyl)-4,4-dimethylcyclohex-1-en-1-yl]methyl}piperazin-1-yl)-2-(1H-indol-5-yloxy)-N-{[3-nitro-4-(tetrahydro-2H-pyran-4-ylamino)phenyl]sulfonyl}benzamide | |
| 4-(4-{[2-(4-chlorophenyl)-4,4-dimethylcyclohex-1-en-1-yl]methyl}piperazin-1-yl)-2-(1H-indol-5-yloxy)-N-[(4-{[(3-methyloxetan-3-yl)methyl]amino}-3-nitrophenyl)sulfonyl]benzamide | |
| 4-(4-{[2-(4-chlorophenyl)-4,4-dimethylcyclohex-1-en-1-yl]methyl}piperazin-1-yl)-2-(1H-indol-5-yloxy)-N-({4-[(4-methoxycyclohexyl)amino]-3-nitrophenyl}sulfonyl)benzamide | |

| Name | Structure |
|------|-----------|
| 4-(4-{[2-(4-chlorophenyl)-4,4-dimethylcyclohex-1-en-1-yl]methyl}piperazin-1-yl)-N-[(4-{[3-(1,1-dioxidothiomorpholin-4-yl)propyl]amino}-3-nitrophenyl)sulfonyl]-2-(1H-indol-5-yloxy)benzamide | |
| 4-(4-{[2-(4-chlorophenyl)-4,4-dimethylcyclohex-1-en-1-yl]methyl}piperazin-1-yl)-2-(1H-indol-5-yloxy)-N-[(3-nitro-4-{2-(2-oxopiperidin-1-yl)ethyl]amino}phenyl)sulfonyl]benzamide | |
| 4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[2-(2-oxoimidazolidin-1-yl)ethyl]amino}phenyl)sulfonyl]benzamide | |

| Name | Structure |
|---|---|
| 4-(4-{[2-(4-chlorophenyl)-4,4-dimethylcyclohex-1-en-1-yl]methyl}piperazin-1-yl)-2-(1H-indol-5-yloxy)-N-({3-nitro-4-[(2-pyridin-4-ylethyl)amino]phenyl}sulfonyl)benzamide | |
| 4-(4-{[2-(4-chlorophenyl)-4,4-dimethylcyclohex-1-en-1-yl]methyl}piperazin-1-yl)-2-(1H-indol 5-yloxy)-N-[(4-morpholin-4-yl-3-nitrophenyl)sulfonyl]benzamide | |
| 4-(4-{[2-(4-chlorophenyl)-4,4-dimethylcyclohex-1-en-1-yl]methyl}piperazin-1-yl)-2-(1H-indol 5-yloxy)-N-{[4-(4-methoxypiperidin-1yl)-3-nitrophenyl]sulfonyl}benzamide | |

| Name | Structure |
|---|---|
| 4-(4-{[2-(4-chloro-phenyl)-5-pyrrolidin-1-ylcyclohex-1-en-1-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide | 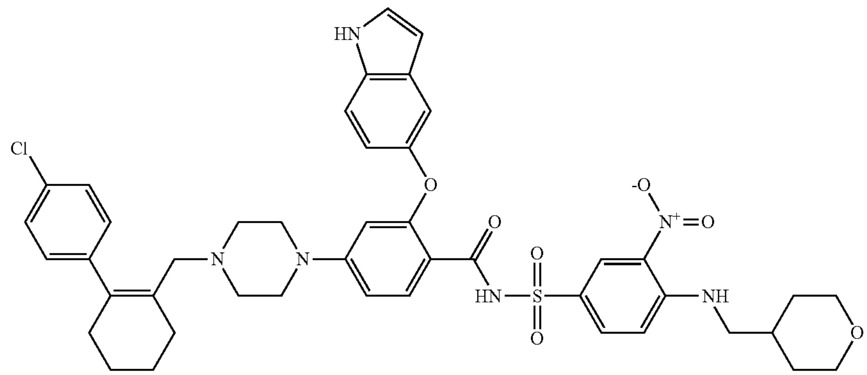 |
| 4-(4-{[2-(4-chloro-phenyl)-4,4-dimethylcyclohex-1-en-1-yl]methyl}piperazin-1-yl)-2-(1H-indol-5-yloxy)-N-[(3-nitro-4-{2-(3-oxopiperazin-1-yl)ethyl]amino}phenyl)sulfonyl]benzamide | |
| 4-[4-({4'-chloro-4-[2-(dimethylamino)ethoxy]-1,1'-biphenyl-2-yl}methyl)piperazin-1-yl]-2-(1H-indol-4-yloxy)-N-({4-[(4-methylpiperazin-1-yl)amino]-3-nitrophenyl}sulfonyl)benzamide | 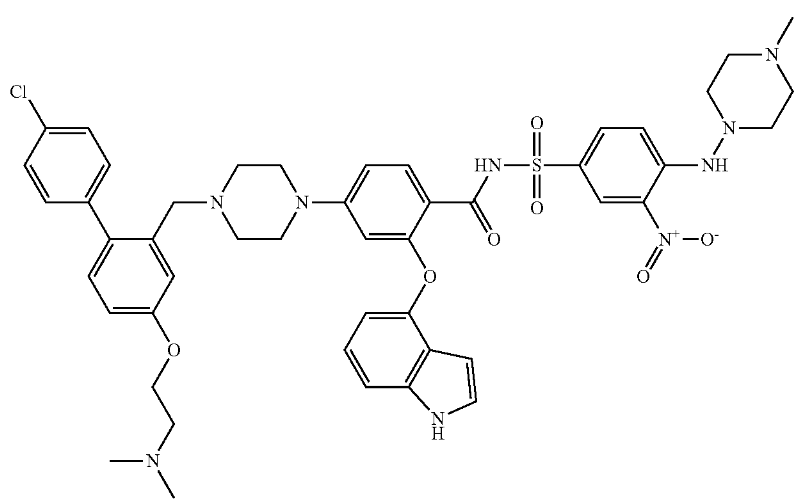 [SMILES: CN(C)CCOc1ccc(-c2ccc(Cl)cc2)c(CN2CCN(c3ccc(C(=O)NS(=O)(=O)c4ccc(NN5CCN(C)CC5)c([N+](=O)[O-])c4)c(Oc4cccc5[nH]ccc45)c3)CC2)c1] |

| Name | Structure |
|---|---|
| 4-(4-{[2-(4-chlorophenyl)-4,4-dimethylcyclohex-1-en-1-yl]methyl}piperazin-1-yl)-N-[(4-{[(1,1-dioxidotetrahydrothien-3-yl)methyl]amino}-3-nitrophenyl)sulfonyl]-2-(1H-indol-5-yloxy)benzamide | |
| 4-(4-{[2-(4-chlorophenyl)-4,4-dimethylcyclohex-1-en-1-yl]methyl}piperazin-1-yl)-N-({4-[(1,1-dioxidotetrahydrothien-3-yl)amino]-3-nitrophenyl}sulfonyl)-2-(1H-indol-5-yloxy)benzamide | |
| 4-(4-{[2-(4-chlorophenyl)-4,4-dimethylcyclohex-1-en-1-yl]methyl}piperazin-1-yl)-2-(1H-indol-5-yloxy)-N-{4-[(tetrahydro-2H-pyran-4-ylmethyl)amino]-3-(trifluoromethyl)phenyl]sulfonyl}benzamide | |

-continued

| Name | Structure |
|------|-----------|
| 4-(4-{[2-(4-chlorophenyl)-4,4-dimethylcyclohex-1-en-1-yl]methyl}piperazin-1-yl)-N-({4-[2-(1,3-dioxolan-2-yl)ethyl]-3-nitrophenyl}sulfonyl)-2-(1H-indol-5-yloxy)benzamide | |
| 4-(4-{[2-(4-chlorophenyl)-4,4-dimethylcyclohex-1-en-1-yl]methyl}piperazin-1-yl)-2-(1H-indol-5-yloxy)-N-{[3-nitro-4-(tetrahydro-2H-pyran-4-ylmethoxy)phenyl]sulfonyl}benzamide | |
| 4-(4-{[2-(4-chlorophenyl)-4,4-dimethylcyclohex-1-en-1-yl]methyl}piperazin-1-yl)-2-(1H-indol-4-yloxy)-N-[(3-nitro-4-{2-(3-oxopiperazin-1-yl)ethyl]amino}phenyl)sulfonyl]benzamide | |

| Name | Structure |
|---|---|
| 4-(4-{[2-(4-chloro-phenyl)-4,4-dimethylcyclohex-1-en-1-yl]methyl}piperazin-1-yl)-2-(1H-indol-5-yloxy)-N-({4-[(1-methyl-5-oxopyrrolidin-3-yl)amino]-3-nitrophenyl}sulfonyl)benzamide | |
| 4-(4-{[2-(4-chloro-phenyl)-4,4-dimethylcyclohex-1-en-1-yl]methyl}piperazin-1-yl)-2-(1H-indol-5-yloxy)-N-({4-[(1-methyl-6-oxopiperidin-3-yl)amino]-3-nitrophenyl}sulfonyl)benzamide | |
| 4-(4-{[2-(4-chloro-phenyl)-4,4-dimethylcyclohex-1-en-1-yl]methyl}piperazin-1-yl)-2-(1H-indol-4-yloxy)-N-{[3-nitro-4-(piperidin-1-ylamino)phenyl]sulfonyl}benzamide | |

| Name | Structure |
|---|---|
| 4-(4-{[2-(4-chlorophenyl)-4,4-dimethylcyclohex-1-en-1-yl]methyl}piperazin-1-yl)-2-(1H-indol-5-yloxy)-N-{[3-nitro-4-(piperidin-1-ylamino)phenyl]sulfonyl}benzamide | |
| 4-(4-{[4-(4-chlorophenyl)-1-methyl-1H-pyrazol-5-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide | |
| 4-(4-{[2-(4-chlorophenyl)-4,4-dimethylcyclohex-1-en-1-yl]methyl}piperazin-1-yl)-2-(1H-indol-5-yloxy)-N-({4-[(3-methyloxetan-3-yl)methoxy]-3-nitrophenyl}sulfonyl)benzamide | |

| Name | Structure |
|---|---|
| 4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[(1-oxidotetrahydro-2H-thiopyran-4-yl)methyl]amino}phenyl)sulfonyl]benzamide | |
| 4-(4-{[2-(4-chlorophenyl)-4,4-dimethylcyclohex-1-en-1-yl]methyl}piperazin-1-yl)-2-(1H-indol-5-yloxy)-N-({3-nitro-4-[(1,3-thiazol-5-ylmethyl)amino]phenyl}sulfonyl)benzamide | |
| 4-(4-{[2-(4-chlorophenyl)-4,4-dimethylcyclohex-1-en-1-yl]methyl}piperazin-1-yl)-2-(1H-indol-4-yloxy)-N-{[3-nitro-4-(tetrahydro-2H-pyran-4-ylmethoxy)phenyl]sulfonyl}benzamide | |

| Name | Structure |
|---|---|
| 4-(4-{[2-(4-chloro-phenyl)-5,5-dimethylcyclohex-1-en-1-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide | 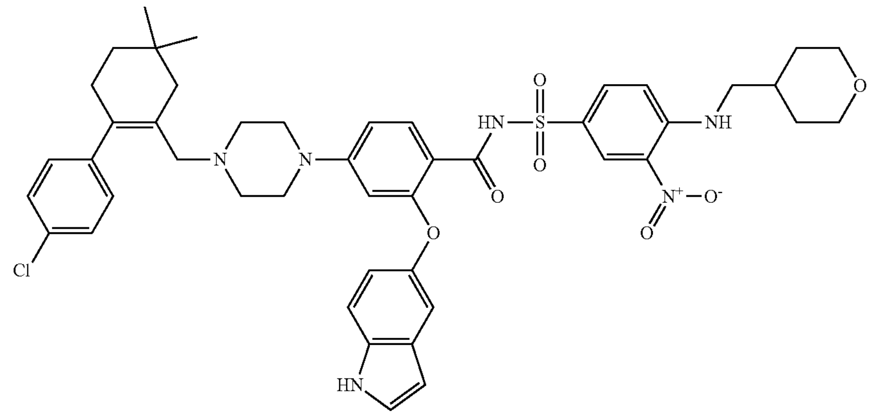 [SMILES: CC1(C)CCC(c2ccc(Cl)cc2)=C(CN2CCN(c3ccc(C(=O)NS(=O)(=O)c4ccc(NCC5CCOCC5)c([N+](=O)[O-])c4)c(Oc4ccc5[nH]ccc5c4)c3)CC2)C1] |
| 4-(4-{[2-(4-chloro-phenyl)-4,4-dimethylcyclohex-1-en-1-yl]methyl}piperazin-1-yl)-2-(1H-indol-5-yloxy)-N-({3-nitro-4-[(2-tetrahydro-2H-pyran-4-ylethyl)amino]phenyl}sulfonyl)benzamide | 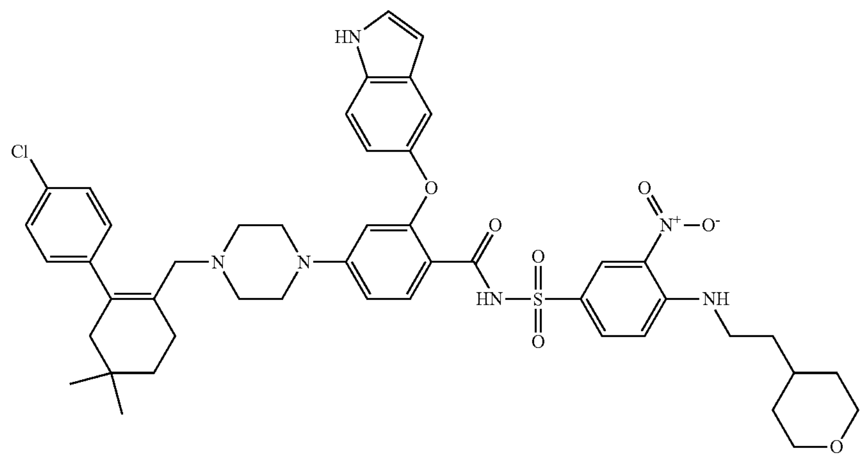 [SMILES: CC1(C)CCC(CN2CCN(c3ccc(C(=O)NS(=O)(=O)c4ccc(NCCC5CCOCC5)c([N+](=O)[O-])c4)c(Oc4ccc5[nH]ccc5c4)c3)CC2)=C(c2ccc(Cl)cc2)C1] |
| 4-(4-{[2-(4-chloro-phenyl)-4,4-dimethylcyclohex-1-en-1-yl]methyl}piperazin-1-yl)-2-(1H-indol-4-yloxy)-N-[(3-nitro-4-{[2-(trifluoromethoxy)ethyl]amino}phenyl)sulfonyl]benzamide | 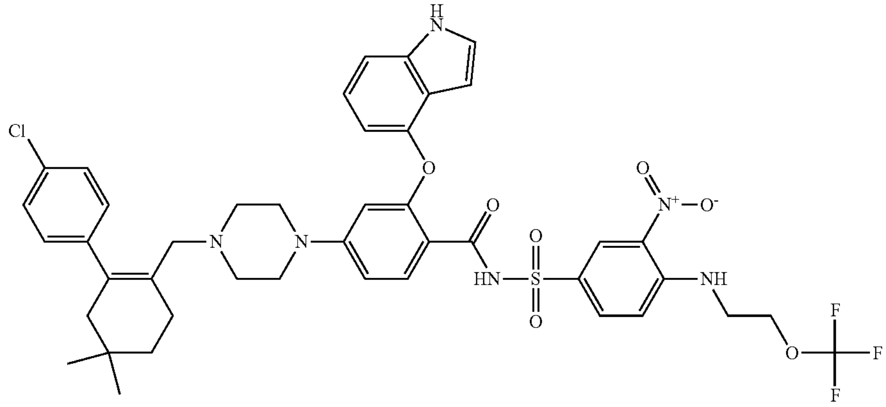 [SMILES: CC1(C)CCC(CN2CCN(c3ccc(C(=O)NS(=O)(=O)c4ccc(NCCOC(F)(F)F)c([N+](=O)[O-])c4)c(Oc4cccc5[nH]ccc45)c3)CC2)=C(c2ccc(Cl)cc2)C1] |

-continued

| Name | Structure |
|---|---|
| 4-(4-{[2-(4-chlorophenyl)-4,4-dimethylcyclohex-1-en-1-yl]methyl}piperazin-1-yl)-2-(1H-indol-4-yloxy)-N-[(4-{[2-(2-methoxyethoxy)ethyl]amino}-3-nitrophenyl)sulfonyl]benzamide | 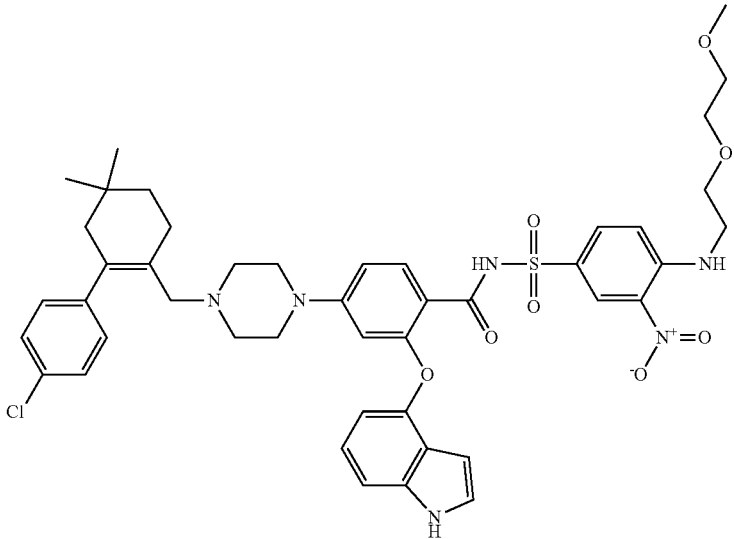 |
| 4-(4-{[2-(4-chlorophenyl)-4,4-dimethylcyclohex-1-en-1-yl]methyl}piperazin-1-yl)-2-(1H-indol-4-yloxy)-N-[(4-{[3-(methylsulfonyl)propyl]amino}-3-nitrophenyl)sulfonyl]benzamide | 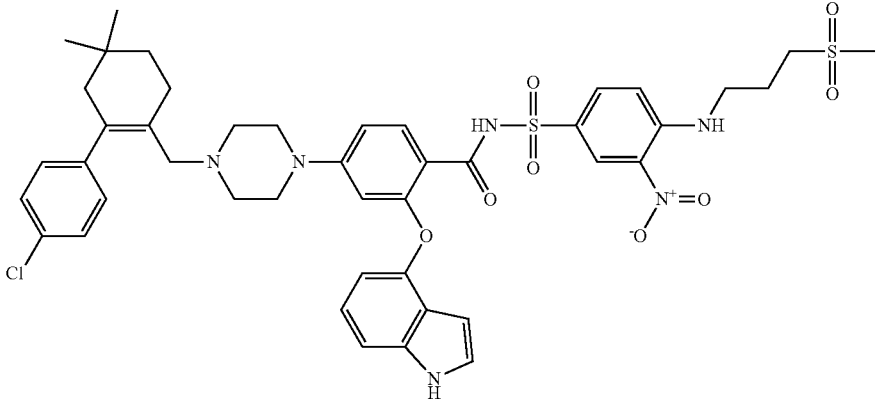 |
| 4-(4-{[2-(4-chlorophenyl)-4,4-dimethylcyclohex-1-en-1-yl]methyl}piperazin-1-yl)-N-[(4-{[3-(1,1-dioxidothiomorpholin-4-yl)propyl]amino)-3-nitrophenyl)sulfonyl]-2-(1H-indol-4-yloxy)benzamide | 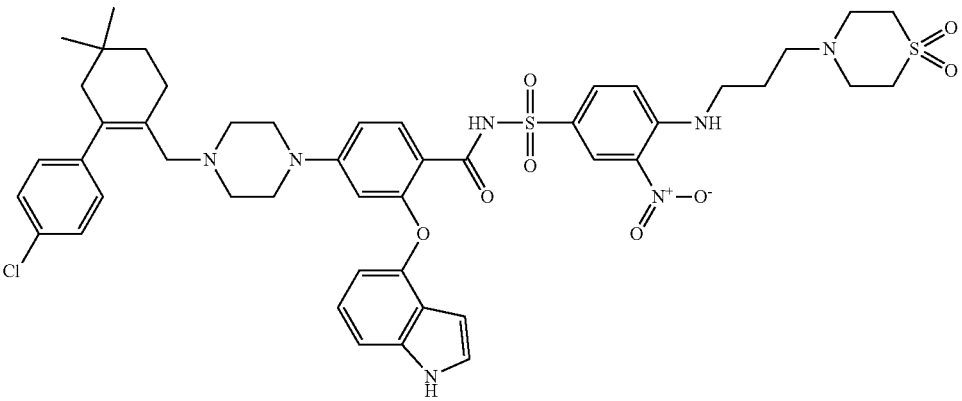 [SMILES: CC1(C)CCC(CN2CCN(c3ccc(C(=O)NS(=O)(=O)c4ccc(NCCCN5CCS(=O)(=O)CC5)c([N+](=O)[O-])c4)c(Oc4cccc5[nH]ccc45)c3)CC2)=C(c2ccc(Cl)cc2)C1] |

| Name | Structure |
|---|---|
| 4-(4-{[2-(4-chlorophenyl)-4,4-dimethylcyclohex-1-en-1-yl]methyl}piperazin-1-yl)-2-(1H-indol-5-yloxy)-N-{[3-nitro-4-(2-tetrahydro-2H-pyran-4-ylethyl)phenyl]sulfonyl}benzamide | |
| 4-(4-{[2-(4-chlorophenyl)-4,4-dimethylcyclohex-1-en-1-yl]methyl}piperazin-1-yl)-N-{[4-(1,4-dioxan-2-ylmethoxy)-3-nitrophenyl]sulfonyl}-2-(1H-indol-5-yloxy)benzamide | |
| 4-(4-{[2-(4-chlorophenyl)-4,4-dimethylcyclohex-1-en-1-yl]methyl}piperazin-1-yl)-2-(1H-indol-5-yloxy)-N-[(4-{[2-(2-methoxyethoxy)ethyl]amino}-3-nitrophenyl)sulfonyl]benzamide | |

-continued

| Name | Structure |
|---|---|
| 4-(4-{[2-(4-chlorophenyl)-4,4-dimethylcyclohex-1-en-1-yl]methyl]piperazin-1-yl)-N-({4-[(1,1-dioxidotetrahydrothien-3-yl)amino]-3-nitrophenyl}sulfonyl)-2-(1H-indol-4-yloxy)benzamide | 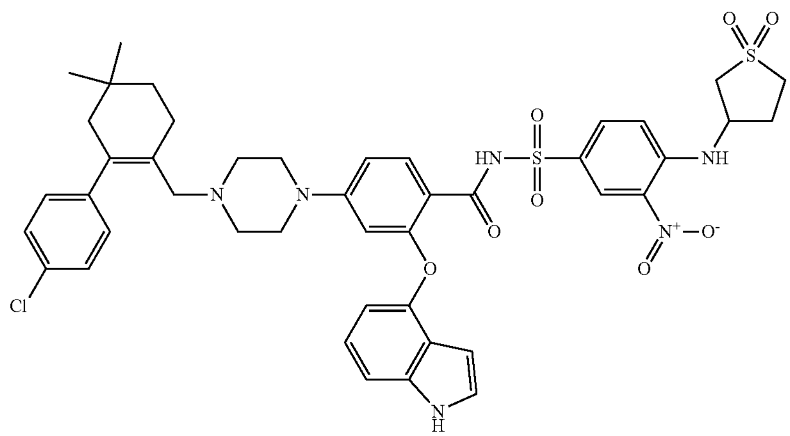 [SMILES: CC1(C)CCC(CN2CCN(c3ccc(C(=O)NS(=O)(=O)c4ccc(NC5CCS(=O)(=O)C5)c([N+](=O)[O-])c4)c(Oc4cccc5[nH]ccc45)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[2-(trifluoromethoxy)ethyl]amino}phenyl)sulfonyl]benzamide | 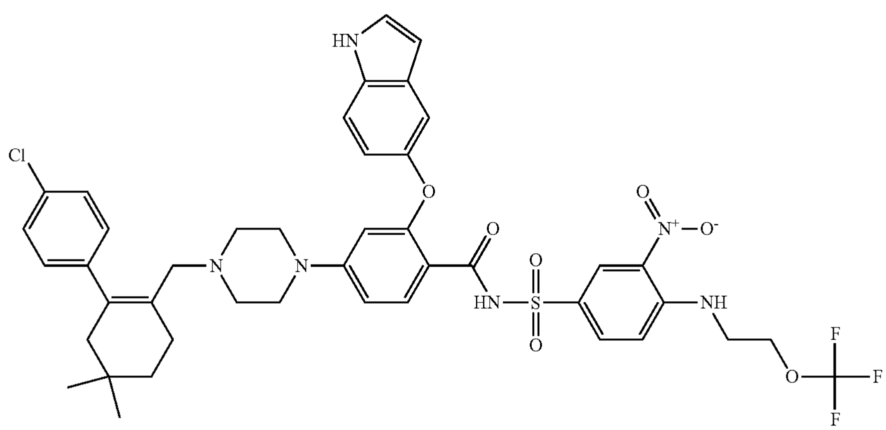 [SMILES: CC1(C)CCC(CN2CCN(c3ccc(C(=O)NS(=O)(=O)c4ccc(NCCOC(F)(F)F)c([N+](=O)[O-])c4)c(Oc4ccc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-[(4-{[(1,1-dioxidotetrahydro-2H-thiopyran-4-yl)methyl]amino}-3-nitrophenyl)sulfonyl]-2-(1H-indol-4-yloxy)benzamide | 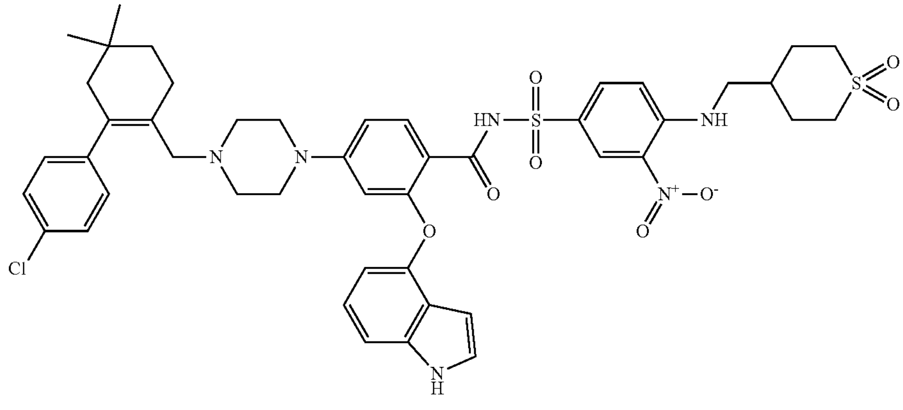 [SMILES: CC1(C)CCC(CN2CCN(c3ccc(C(=O)NS(=O)(=O)c4ccc(NCC5CCS(=O)(=O)CC5)c([N+](=O)[O-])c4)c(Oc4cccc5[nH]ccc45)c3)CC2)=C(c2ccc(Cl)cc2)C1] |

| Name | Structure |
|---|---|
| 4-(4-{[2-(4-chlorophenyl)-4,4-dimethylcyclohex-1-en-1-yl]methyl}piperazin-1-yl)-N-({4-[(2,2-difluoroethyl)amino]-3-nitrophenyl}sulfonyl)-2-(1H-indol-5-yloxy)benzamide | |
| 4-(4-{[2-(4-chlorophenyl)-4,4-dimethylcyclohex-1-en-1-yl]methyl}piperazin-1-yl)-2-(1H-indol-4-yloxy)-N-({4-[(tetrahydro-2H-pyran-4-ylmethyl)amino]-3-[(trifluoromethyl)sulfonyl]phenyl}sulfonyl)benzamide | |
| 4-(4-{[2-(4-chlorophenyl)-4,4-dimethylcyclohex-1-en-1-yl]methyl}piperazin-1-yl)-2-(1H-indol-5-yloxy)-N-({4-[(tetrahydro-2H-pyran-4-ylmethyl)amino]-3-[(trifluoromethyl)sulfonyl]phenyl}sulfonyl)benzamide | |

-continued

| Name | Structure |
|---|---|
| 4-(4-{[2-(4-chlorophenyl)-4,4-dimethylcyclohex-1-en-1-yl]methyl}piperazin-1-yl)-N-({4-[(4,4-difluorocyclohexyl)amino]-3-nitrophenyl}sulfonyl)-2-(1H-indol-5-yloxy)benzamide | |
| 4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-nitrophenyl}sulfonyl)-2-(1H-indol-4-yloxy)benzamide | |
| 4-(4-{[4-(4-chlorophenyl)-1-isopropyl-6-oxo-1,6-dihydropyridin-3-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide | |

| Name | Structure |
|---|---|
| 4-(4-{[2-(4-chlorophenyl)-4,4-dimethylcyclohex-1-en-1-yl]methyl}piperazin-1-yl)-2-(1H-indol-5-yloxy)-N-[(4-{[(tetrahydro-2H-pyran-4-ylmethyl)amino]carbonyl}phenyl)sulfonyl]benzamide | |
| 4-(4-{[2-(4-chlorophenyl)-4,4-dimethylcyclohex-1-en-1-yl]methyl}piperazin-1-yl)-2-(1H-indol-4-yloxy)-N-({4-[(2-methoxyethyl)amino]-3-[(trifluoromethyl)sulfonyl]phenyl}sulfonyl)benzamide | |
| Trans-4-(4-{[2-(4-chlorophenyl)-4,4-dimethylcyclohex-1-en-1-yl]methyl}piperazin-1-yl)-N-[(4-{[(4-hydroxycyclohexyl)methyl]amino}-3-nitrophenyl)sulfonyl]-2-(1H-indol-5-yloxy)benzamide | |

| Name | Structure |
|---|---|
| Trans-4-(4-{[2-(4-chloro-phenyl)-4,4-dimethylcyclohex-1-en-1-yl]methyl}piperazin-1-yl)-2-(1H-indol-5-yloxy)-N-[(4-{[(4-methoxycyclohexyl)methyl]amino}-3-nitrophenyl)sulfonyl]benzamide | 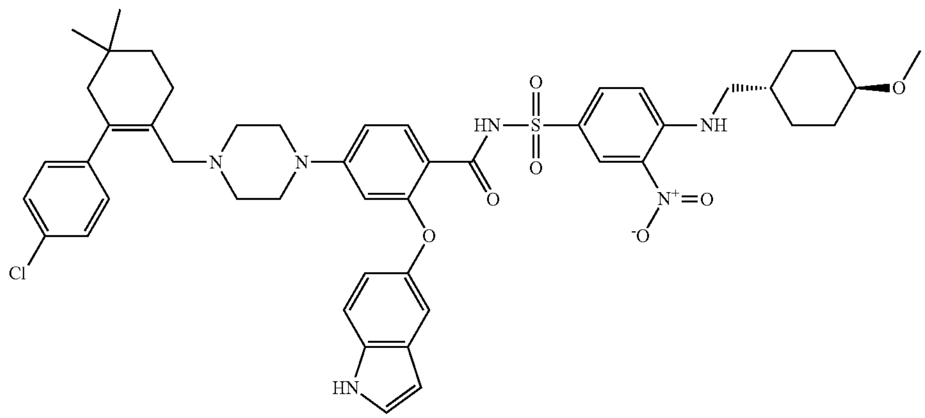 |
| Cis-4-(4-{[2-(4-chlorophenyl)-4,4-dimethylcyclohex-1-en-1-yl]methyl}piperazin-1-yl)-N-[(4-{[(4-hydroxycyclohexyl)methyl]amino}-3-nitrophenyl)sulfonyl]-2-(1H-indol-5-yloxy)benzamide | 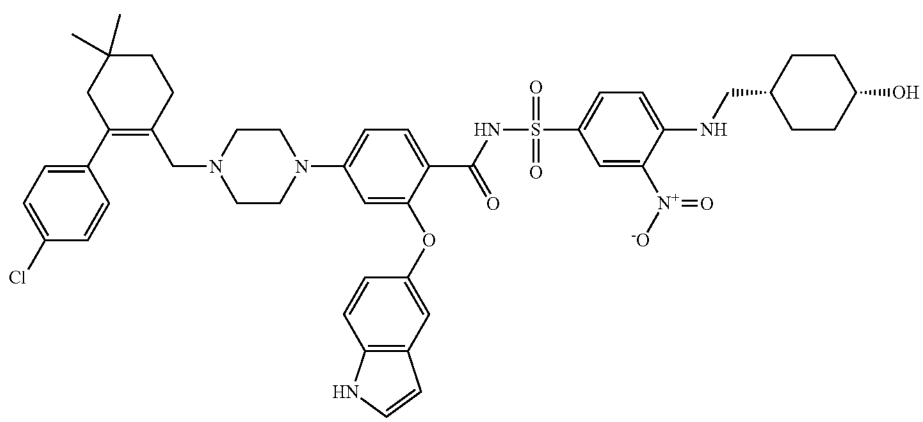 |
| Cis-4-(4-{[2-(4-chlorophenyl)-4,4-dimethylcyclohex-1-en-1-yl]methyl}piperazin-1-yl)-2-(1H-indol-5-yloxy)-N-[(4-{[(4-methoxycyclohexyl)methyl]amino}-3-nitrophenyl)sulfonyl]benzamide | 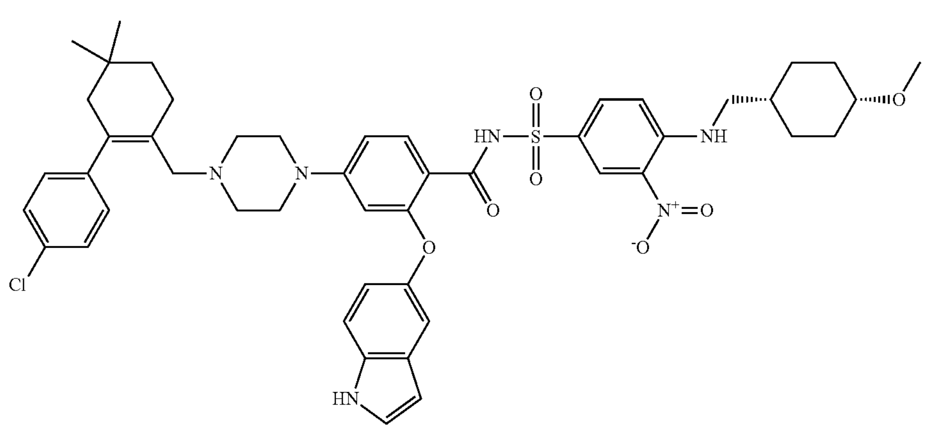 |

| Name | Structure |
|---|---|
| 4-(4-{[2-(4-chloro-phenyl)-4,4-dimethylcyclohex-1-en-1-yl]methyl}piperazin-1-yl)-2-(1H-indol-4-yloxy)-N-{[3-nitro-4-(2-tetrahydro-2H-pyran-4-ylethoxy)phenyl]sulfonyl}benzamide | 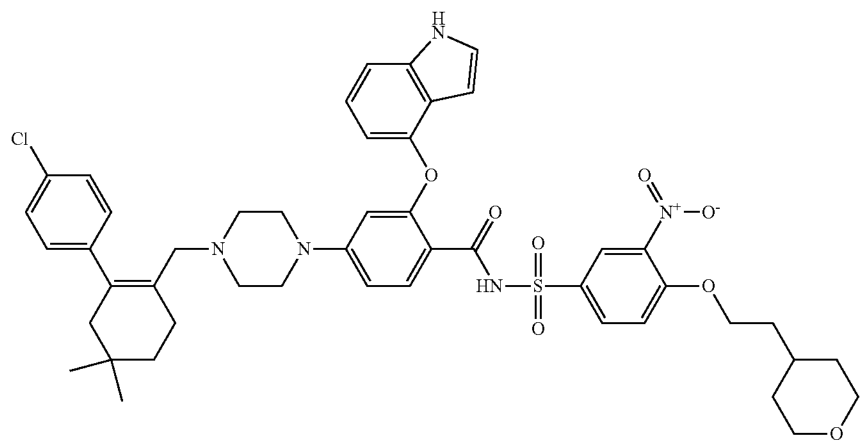 [SMILES: CC1(C)CCC(CN2CCN(c3ccc(C(=O)NS(=O)(=O)c4ccc(OCCC5CCOCC5)c([N+](=O)[O-])c4)c(Oc4cccc5[nH]ccc45)c3)CC2)=C(c2ccc(Cl)cc2)C1] |
| 4-(4-{[2-(4-chloro-phenyl)-4,4-dimethylcyclohex-1-en-1-yl]methyl}piperazin-1-yl)-2-(1H-indol-5-yloxy)-N-({4-[(2-methoxyethyl)amino]-3-[(trifluoromethyl)sulfonyl]phenyl}sulfonyl)benzamide | 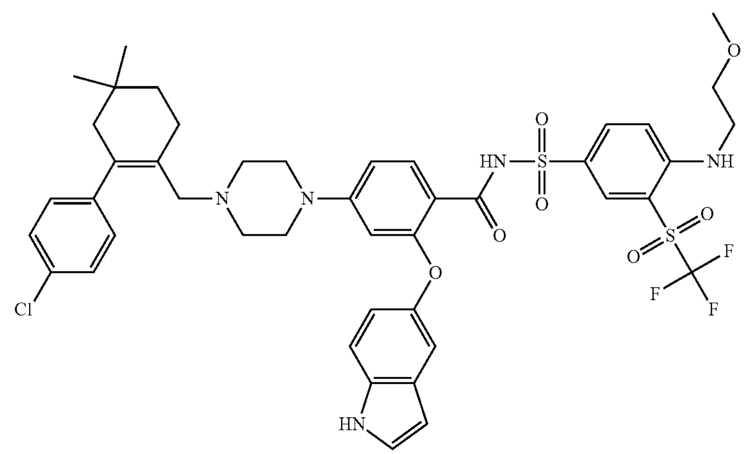 [SMILES: COCCNc1ccc(S(=O)(=O)NC(=O)c2ccc(N3CCN(CC4=C(c5ccc(Cl)cc5)CC(C)(C)CC4)CC3)cc2Oc2ccc3[nH]ccc3c2)cc1S(=O)(=O)C(F)(F)F] |
| 4-(4-{[2-(4-chloro-phenyl)-4,4-dimethylcyclohex-1-en-1-yl]methyl}piperazin-1-yl)-2-(1H-indol-4-yloxy)-N-({4-[3-(methylsulfonyl)propoxy]-3-nitrophenyl}sulfonyl)benzamide | 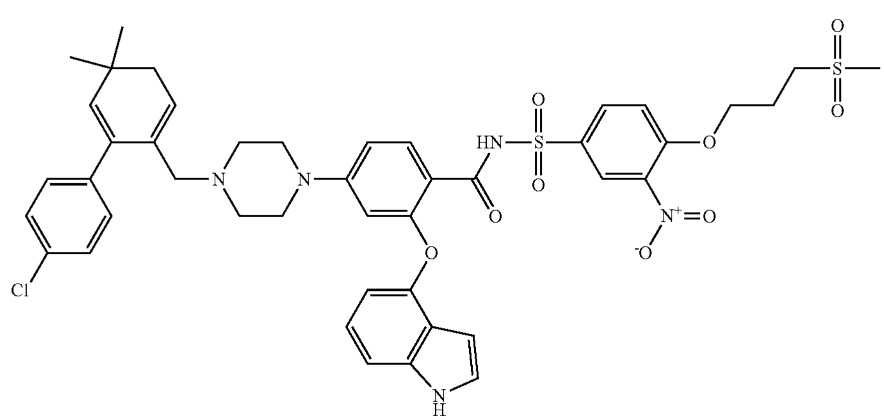 |

| Name | Structure |
|---|---|
| 4-(4-{[2-(4-chlorophenyl)-4,4-dimethylcyclohex-1-en-1-yl]methyl}piperazin-1-yl)-2-(1H-indol-5-yloxy)-N-({4-[(3-methoxypropyl)amino]-3-nitrophenyl}sulfonyl)benzamide | |
| 4-(4-{[2-(4-chlorophenyl)-4,4-dimethylcyclohex-1-en-1-yl]methyl}piperazin-1-yl)-2-(1H-indol-4-yloxy)-N-({4-[(3-methoxypropyl)amino]-3-nitrophenyl}sulfonyl)benzamide | |
| 4-(4-{[2-(4-chlorophenyl)-4,4-dimethylcyclohex-1-en-1-yl]methyl}piperazin-1-yl)-N-({4-[(2-cyanoethyl)amino]-3-nitrophenyl}sulfonyl)-2-(1H-indol-5-yloxy)benzamide | |

| Name | Structure |
|---|---|
| 4-(4-{[2-(4-chlorophenyl)-4,4-dimethylcyclohex-1-en-1-yl]methyl}piperazin-1-yl)-N-({4-[(2-cyanoethyl)amino]-3-nitrophenyl}sulfonyl)-2-(1H-indol-4-yloxy)benzamide | |
| 4-(4-{[2-(4-chlorophenyl)-4,4-dimethylcyclohex-1-en-1-yl]methyl}piperazin-1-yl)-N-{[4-({[(3R)-4-hydroxy-1-adamantyl]methyl}amino)-3-nitrophenyl]sulfonyl}-2-(1H-indol-5-yloxy)benzamide | |
| 4-(4-{[2-(4-chlorophenyl)-4,4-dimethylcyclohex-1-en-1-yl]methyl}piperazin-1-yl)-N-{14-({[Cis-4-hydroxy-1-adamantyl]methyl}amino)-3-nitrophenyl]sulfonyl}-2-(1H-indol-5-yloxy)benzamide | |
| 4-(4-{[2-(4-chlorophenyl)-4,4-dimethylcyclohex-1-en-1-yl]methyl}piperazin-1-yl)-2-(1H-indol-4-yloxy)-N-({3-nitro-4-[(3,3,3-trifluoropropyl)amino]phenyl}sulfonyl)benzamide | |

| Name | Structure |
|---|---|
| 4-(4-{[2-(4-chloro-phenyl)-4,4-dimethylcyclohex-1-en-1-yl]methyl}piperazin-1-yl)-2-(1H-indol-5-yloxy)-N-({3-nitro-4-[(3,3,3-trifluoropropyl)amino]phenyl}sulfonyl)benzamide | 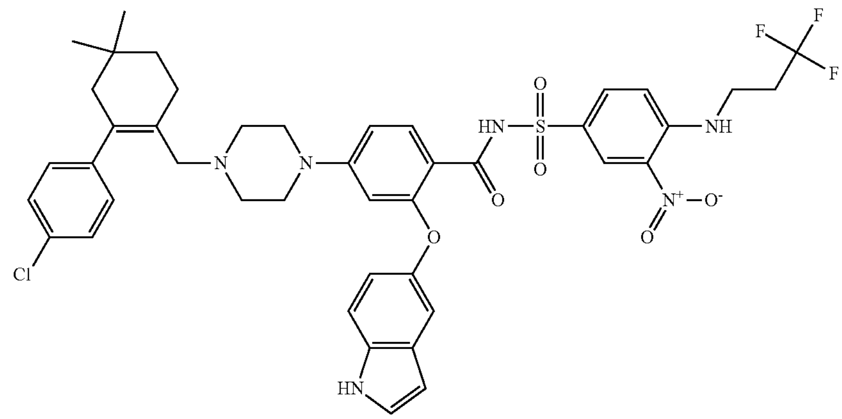 [SMILES: CC1(C)CCC(CN2CCN(c3ccc(C(=O)NS(=O)(=O)c4ccc(NCCC(F)(F)F)c([N+](=O)[O-])c4)c(Oc4ccc5[nH]ccc5c4)c3)CC2)=C(c2ccc(Cl)cc2)C1] |
| N-({5-bromo-6-[(tetra-hydro-2H-pyran-4-ylmethyl)amino]pyridin-3-yl}sulfonyl)-4-(4-{[2-(4-chloro-phenyl)-4,4-dimethylcyclohex-1-en-1-yl]methyl}piperazin-1-yl)-2-(1H-indol-4-yloxy)benzamide | 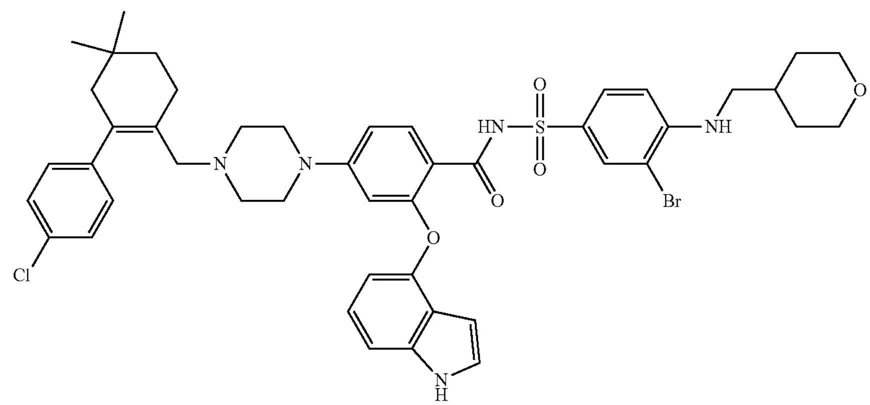 |
| 4-(4-{[2-(4-chloro-phenyl)-4,4-dimethylcyclohex-1-en-1-yl]methyl}piperazin-1-yl)-N-[(4-{[(1,1-dioxidotetrahydro-thien-3-yl)methyl]amino}-3-nitrophenyl)sulfonyl]-2-(1H-indol-4-yloxy)benzamide | 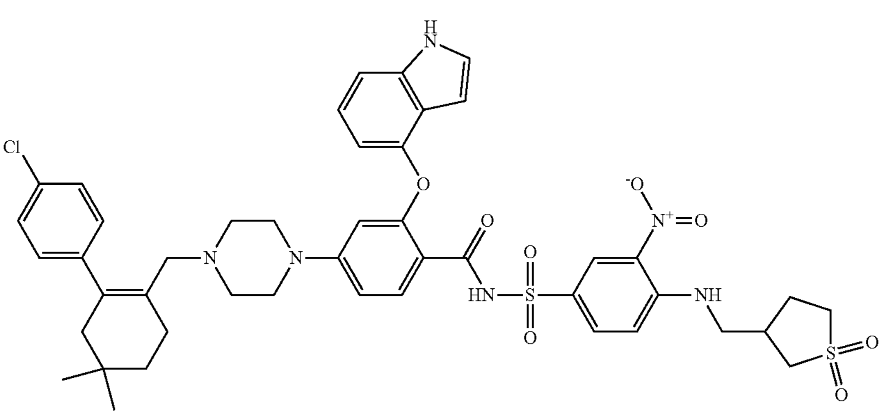 |

| Name | Structure |
|---|---|
| 4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-nitrophenyl}sulfonyl)-2-(1H-indol-5-yloxy)benzamide | |
| 4-(4-{[2-(4-chlorophenyl)-4,4-dimethylcyclohex-1-en-1-yl]methyl}piperazin-1-yl)-2-(1H-indol-5-yloxy)-N-({4-(methylamino)-3-[(trifluoromethyl)sulfonyl]phenyl}sulfonyl)benzamide | |
| N-{[5-bromo-6-(tetrahydro-2H-pyran-4-ylmethoxy)pyridin-3-yl]sulfonyl}-4-(4-{[2-(4-chlorophenyl)-4,4-dimethylcyclohex-1-en-1-yl]methyl]piperazin-1-yl)-2-(1H-indol-5-yloxy)benzamide | |

-continued

| Name | Structure |
|------|-----------|
| 4-(4-{[4-(4-chloro-phenyl)-6-isopropoxypyridin-3-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide | 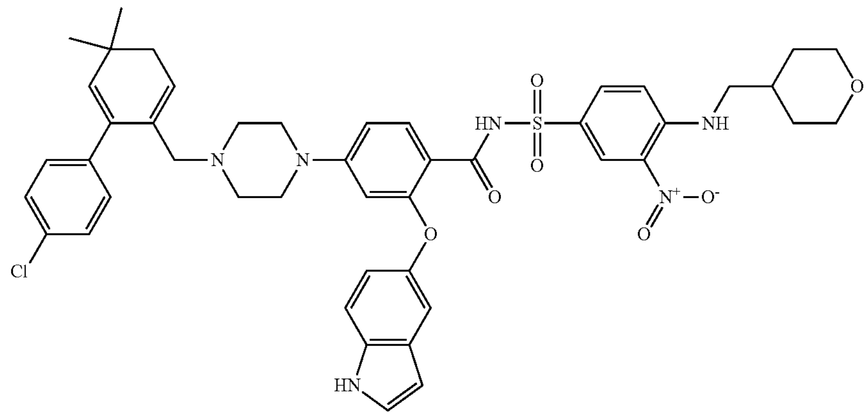 [SMILES: CC1(C)C=C(c2ccc(Cl)cc2)C(CN2CCN(c3ccc(C(=O)NS(=O)(=O)c4ccc(NCC5CCOCC5)c([N+](=O)[O-])c4)c(Oc4ccc5[nH]ccc5c4)c3)CC2)=CC1] |
| 4-(4-{[2-(4-chloro-phenyl)-4,4-dimethylcyclohex-1-en-1-yl]methyl}piperazin-1-yl)-2-(1H-indol-5-yloxy)-N-{[6-(tetrahydro-2H-pyran-4-ylmethoxy)-5-(1,3-thiazol-2-yl)pyridin-3-yl]sulfonyl}benzamide | 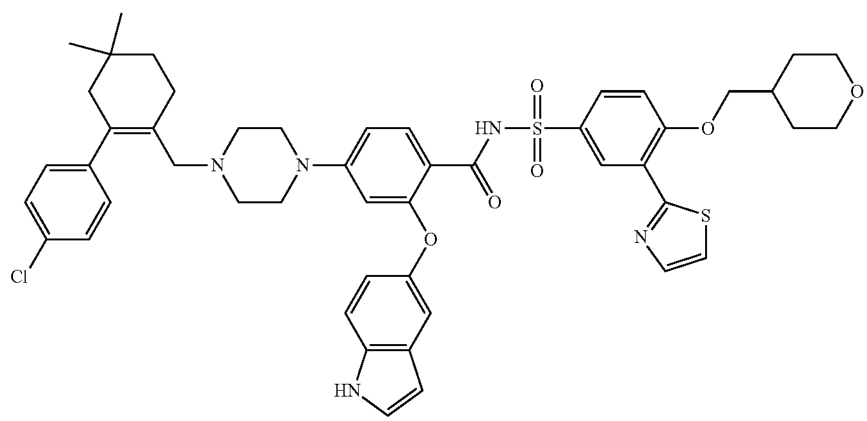 [SMILES: CC1(C)CCC(CN2CCN(c3ccc(C(=O)NS(=O)(=O)c4ccc(OCC5CCOCC5)c(-c5nccs5)c4)c(Oc4ccc5[nH]ccc5c4)c3)CC2)=C(c2ccc(Cl)cc2)C1] |
| 4-(4-{[2-(4-chloro-phenyl)-4,4-dimethylcyclohex-1-en-1-yl]methyl}piperazin-1-yl)-2-(1H-indol-5-yloxy)-N-[(4-{[(2-methoxyethyl)amino]carbonyl}phenyl)sulfonyl]benzamide | 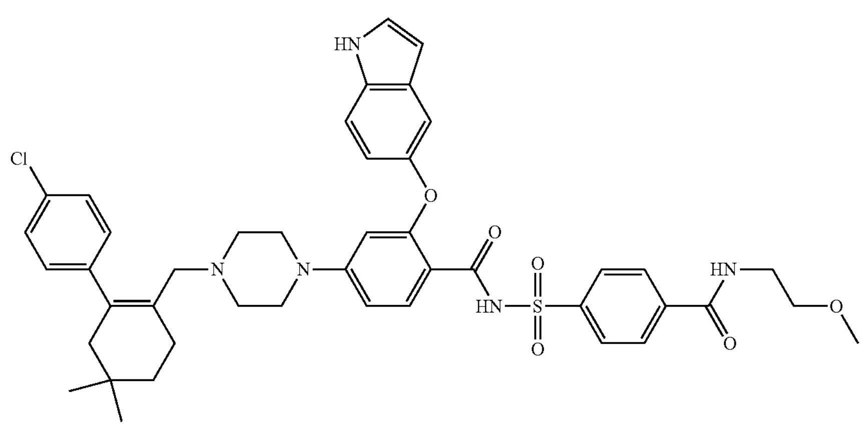 [SMILES: COCCNC(=O)c1ccc(S(=O)(=O)NC(=O)c2ccc(N3CCN(CC4=C(c5ccc(Cl)cc5)CC(C)(C)CC4)CC3)cc2Oc2ccc3[nH]ccc3c2)cc1] |

| Name | Structure |
|---|---|
| 4-(4-{[2-(4-chlorophenyl)-4,4-dimethylcyclohex-1-en-1-yl]methyl}piperazin-1-yl)-N-{[5-cyano-6-(tetrahydro-2H-pyran-4-ylmethoxy)pyridin-3-yl]sulfonyl}-2-(1H-indol-5-yloxy)benzamide | |
| N-({4-[(1-acetylpiperidin-4-yl)amino]-3-nitrophenyl}sulfonyl)-4-(4-{[2-(4-chlorophenyl)-4,4-dimethylcyclohex-1-en-1-yl]methyl}piperazin-1-yl)-2-(1H-indol-5-yloxy)benzamide | |
| 4-(4-{[2-(4-chlorophenyl)-4,4-dimethylcyclohex-1-en-1-yl]methyl}piperazin-1-yl)-2-(1H-indol-5-yloxy)-N-[(4-{[1-(methylsulfonyl)piperidin-4-yl]amino}-3-nitrophenyl)sulfonyl]benzamide | |

-continued

| Name | Structure |
|---|---|
| 4-(4-{[2-(4-chlorophenyl)-4,4-dimethylcyclohex-1-en-1-yl]methyl}piperazin-1-yl)-N-({4-[(1,4-dioxan-2-ylmethyl)amino]-3-nitrophenyl}sulfonyl)-2-(1H-indol-5-yloxy)benzamide | |
| N-({4-[(1-acetylpiperidin-4-yl)amino]-3-nitrophenyl}sulfonyl)-4-(4-{[2-(4-chlorophenyl)-4,4-dimethylcyclohex-1-en-1-yl]methyl}piperazin-1-yl)-2-(1H-indol-4-yloxy)benzamide | |
| 4-(4-{[2-(4-chlorophenyl)-4,4-dimethylcyclohex-1-en-1-yl]methyl}piperazin-1-yl)-2-(1H-indol-4-yloxy)-N-[(4-{[1-(methylsulfonyl)piperidin-4-yl]amino}-3-nitrophenyl)sulfonyl]benzamide | |

-continued

| Name | Structure |
|---|---|
| 4-(4-{[4'-chloro-5-(trifluoromethyl)-1,1'-biphenyl-2-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide | 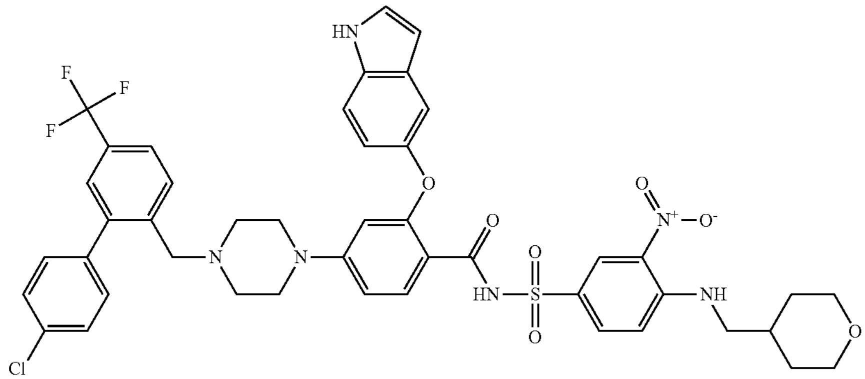 |
| 4-(4-{[4'-chloro-5-(trifluoromethyl)-1,1'-biphenyl-2-yl]methyl}piperazin-1-yl)-2-(1H-indol-5-yloxy)-N-{[3-nitro-4-(tetrahydro-2H-pyran-4-ylmethoxy)phenyl]sulfonyl}benzamide | 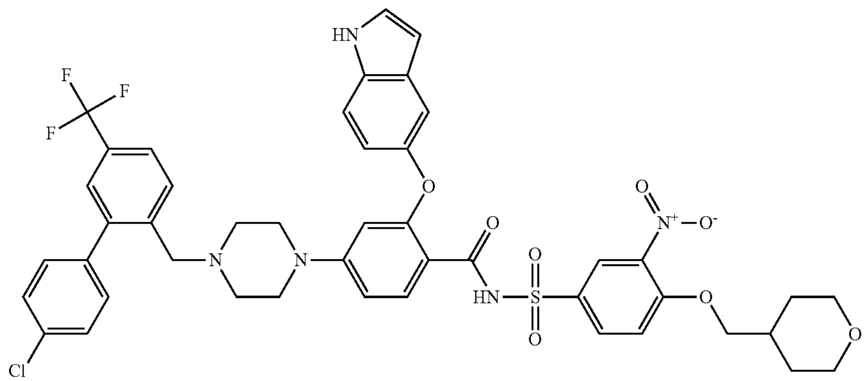 [SMILES: O=C(NS(=O)(=O)c1ccc(OCC2CCOCC2)c([N+](=O)[O-])c1)c1ccc(N2CCN(Cc3ccc(C(F)(F)F)cc3-c3ccc(Cl)cc3)CC2)cc1Oc1ccc2[nH]ccc2c1] |
| 4-{4-[(5-tert-butyl-4'-chloro-1,1'-biphenyl-2-yl)methyl]piperazin-1-yl}-2-(1H-indol-5-yloxy)-N-({3-nitro-4-[(tetrahydro-2H-pyran-4-ylmethyl)amino]phenyl}sulfonyl)benzamide | 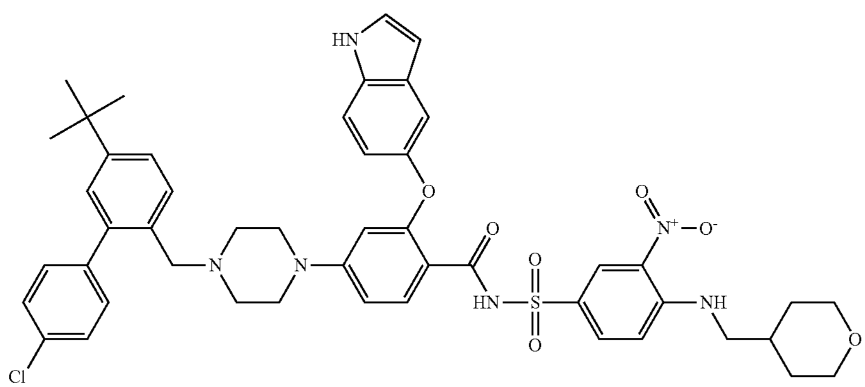 [SMILES: CC(C)(C)c1ccc(CN2CCN(c3ccc(C(=O)NS(=O)(=O)c4ccc(NCC5CCOCC5)c([N+](=O)[O-])c4)c(Oc4ccc5[nH]ccc5c4)c3)CC2)c(-c2ccc(Cl)cc2)c1] |
| 4-{4-[(5-tert-butyl-4'-chloro-1,1'-biphenyl-2-yl)methyl]piperazin-1-yl}-2-(1H-indol-5-yloxy)-N-{[3-nitro-4-(tetrahydro-2H-pyran-4-ylmethoxy)phenyl]sulfonyl}benzamide | 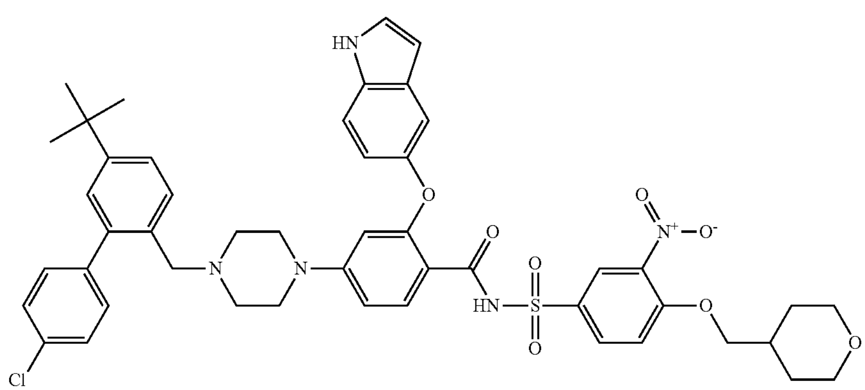 [SMILES: CC(C)(C)c1ccc(CN2CCN(c3ccc(C(=O)NS(=O)(=O)c4ccc(OCC5CCOCC5)c([N+](=O)[O-])c4)c(Oc4ccc5[nH]ccc5c4)c3)CC2)c(-c2ccc(Cl)cc2)c1] |

| Name | Structure |
|---|---|
| 4-(4-{[2-(4-chlorophenyl)-4,4-dimethylcyclohex-1-en-1-yl]methyl}piperazin-1-yl)-2-(1H-indol-4-yloxy)-N-({3-nitro-4-[(2,2,2-trifluoroethyl)amino]phenyl}sulfonyl)benzamide | |
| 4-(4-{[2-(4-chlorophenyl)-4,4-dimethylcyclohex-1-en-1-yl]methyl}piperazin-1-yl)-2-(1H-indol-5-yloxy)-N-({3-nitro-4-[(2,2,2-trifluoroethyl)amino]phenyl}sulfonyl)benzamide | |
| 4-(4-{[2-(4-chlorophenyl)-4,4-dimethylcyclohex-1-en-1-yl]methyl}piperazin-1-yl)-2-(1H-indol-5-yloxy)-N-[(3-{[(tetrahydro-2H-pyran-4-ylmethyl)amino]carbonyl}phenyl)sulfonyl]benzamide | |

| Name | Structure |
|---|---|
| 4-(4-{[2-(4-chloro-phenyl)-4,4-dimethylcyclohex-1-en-1-yl]methyl}piperazin-1-yl)-N-({4-[(2R)-1,4-dioxan-2-yl-methoxy]-3-nitrophenyl}sulfonyl)-2-(1H-indol-5-yloxy)benzamide | |
| 4-(4-{[2-(4-chloro-phenyl)-4,4-dimethylcyclohex-1-en-1-yl]methyl}piperazin-1-yl)-N-({4-[(2S)-1,4-dioxan-2-yl-methoxy]-3-nitrophenyl}sulfonyl)-2-(1H-indol-5-yloxy)benzamide | 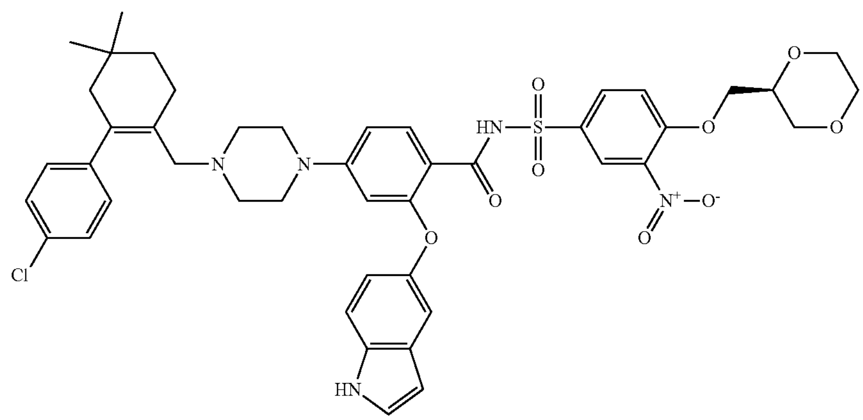 [SMILES: CC1(C)CCC(CN2CCN(c3ccc(C(=O)NS(=O)(=O)c4ccc(OC[C@@H]5COCCO5)c([N+](=O)[O-])c4)c(Oc4ccc5[nH]ccc5c4)c3)CC2)=C(c2ccc(Cl)cc2)C1] |
| 4-(4-{[2-(4-chloro-phenyl)-4,4-dimethylcyclohex-1-en-1-yl]methyl}piperazin-1-yl)-2-(1H-indol-5-yloxy)-N-({4-[(3-morpholin-4-ylpropyl)amino]-3-[(trifluoromethyl)sulfonyl]phenyl}sulfonyl)benzamide | 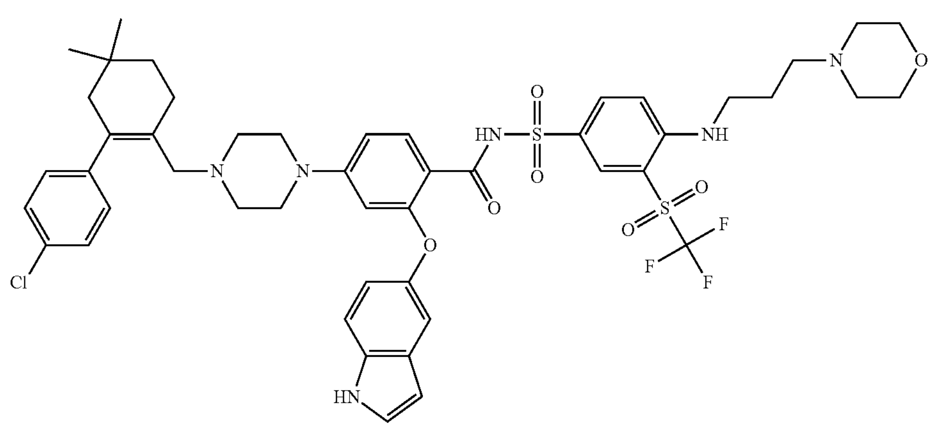 [SMILES: CC1(C)CCC(CN2CCN(c3ccc(C(=O)NS(=O)(=O)c4ccc(NCCCN5CCOCC5)c(S(=O)(=O)C(F)(F)F)c4)c(Oc4ccc5[nH]ccc5c4)c3)CC2)=C(c2ccc(Cl)cc2)C1] |

| Name | Structure |
|---|---|
| 4-(4-{[2-(4-chloro-phenyl)-4,4-dimethylcyclohex-1-en-1-yl]methyl}piperazin-1-yl)-2-(1H-indol-4-yloxy)-N-({4-[(3-morpholin-4-ylpropyl)amino]-3-[(trifluoromethyl)sulfonyl]phenyl}sulfonyl)benzamide | |
| N-({5-bromo-6-[(tetra-hydro-2H-pyran-4-ylmethyl)amino]pyridin-3-yl}sulfonyl)-4-(4-{[2-(4-chloro-phenyl)-4,4-dimethylcyclohex-1-en-1-yl]methyl}piperazin-1-yl)-2-(1H-indol-5-yloxy)benzamide | |
| 4-(4-{[2-(4-chloro-phenyl)-4,4-dimethylcyclohex-1-en-1-yl]methyl}piperazin-1-yl)-2-(1H-indol-5-yloxy)-N-({4-[(2-morpholin-4-ylethyl)amino]-3-[(trifluoromethyl)sulfonyl]phenyl}sulfonyl)benzamide | |

| Name | Structure |
|---|---|
| 4-(4-{[2-(4-chlorophenyl)-4,4-dimethylcyclohex-1-en-1-yl]methyl}piperazin-1-yl)-N-({5-cyano-6-[(tetrahydro-2H-pyran-4-ylmethyl)amino]pyridin-3-yl}sulfonyl)-2-(1H-indol-5-yloxy)benzamide | |
| 4-(4-{[2-(4-chlorophenyl)-4,4-dimethylcyclohex-1-en-1-yl]methyl}piperazin-1-yl)-2-(1H-indol-5-yloxy)-N-({4-[(1-methylpiperidin-4-yl)oxy]-3-nitrophenyl}sulfonyl)benzamide | |
| 4-(4-{[2-(4-chlorophenyl)-4,4-dimethylcyclohex-1-en-1-yl]methyl}piperazin-1-yl)-2-(1H-indol-5-yloxy)-N-({4-[(1-methylpiperidin-4-yl)methoxy]-3-nitrophenyl}sulfonyl)benzamide | |

| Name | Structure |
|---|---|
| 4-(4-{[4-(4-chlorophenyl)-1-(3-hydroxypropyl)-1,2,5,6-tetrahydropyridin-3-yl]methyl]piperazin-1-yl)-2-(1H-indol-4-yloxy)-N-({3-nitro-4-[(tetrahydro-2H-pyran-4-ylmethyl)amino]phenyl}sulfonyl)benzamide | |
| benzyl 4-({[4-({[4-(4-{[2-(4-chlorophenyl)-4,4-dimethylcyclohex-1-en-1-yl]methyl}piperazin-1-yl)-2-(1H-indol-5-yloxy)benzoyl]amino}sulfonyl)-2-nitrophenyl]amino}methyl)piperidine-1-carboxylate | |
| N-{[3-(aminocarbonyl)-4-(tetrahydro-2H-pyran-4-ylmethoxy)phenyl]sulfonyl}-4-(4-{[2-(4-chlorophenyl)-4,4-dimethylcyclohex-1-en-1-yl]methyl}piperazin-1-yl)-2-(1H-indol-5-yloxy)benzamide | |

| Name | Structure |
|---|---|
| 4-(4-{[4'-chloro-5-(trifluoromethyl)-1,1'-biphenyl-2-yl]methyl]piperazin-1-yl)-2-(1H-indol-5-yloxy)-N-({3-nitro-4-[(1-tetrahydro-2H-pyran-4-ylpiperidin-4-yl)amino]phenyl}sulfonyl)benzamide | |
| 4-{4-[(5-tert-butyl-4'-chloro-1,1'-biphenyl-2-yl)methyl]piperazin-1-yl}-2-(1H-indol-5-yloxy)-N-({3-nitro-4-[(1-tetrahydro-2H-pyran-4-ylpiperidin-4-yl)amino]phenyl}sulfonyl)benzamide | |
| 4-(4-{[2-(4-chlorophenyl)-4,4-dimethylcyclohex-1-en-1-yl]methyl}piperazin-1-yl)-2-(1H-indol-5-yloxy)-N-[(4-{[(1-methyl-1H-imidazol-5-yl)methyl]amino}-3-nitrophenyl)sulfonyl]benzamide | |

| Name | Structure |
|---|---|
| 4-(4-{[2-(4-chloro-phenyl)-4,4-dimethylcyclohex-1-en-1-yl]methyl}piperazin-1-yl)-2-(1H-indol-5-yloxy)-N-{[4-(morpholin-4-ylsulfonyl)phenyl]sulfonyl}benzamide | 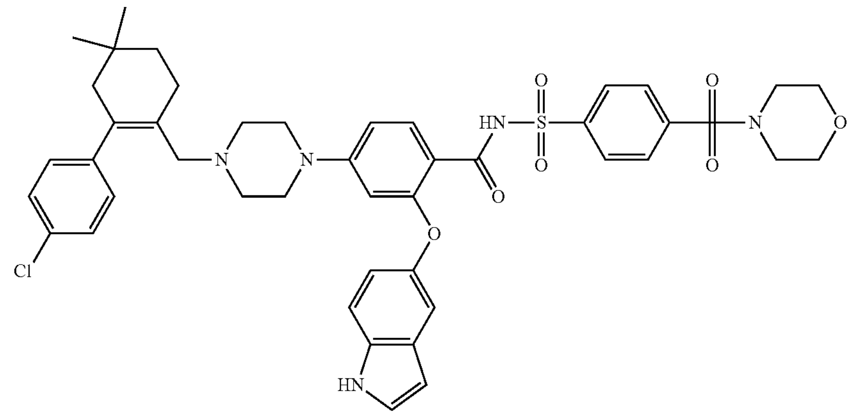 |
| 4-(4-{[2-(4-chloro-phenyl)-4,4-dimethylcyclohex-1-en-1-yl]methyl}piperazin-1-yl)-N-({4-[(1,1-dioxidothiomorpholin-4-yl)amino]-3-nitrophenyl}sulfonyl)-2-(1H-indol-5-yloxy)benzamide | 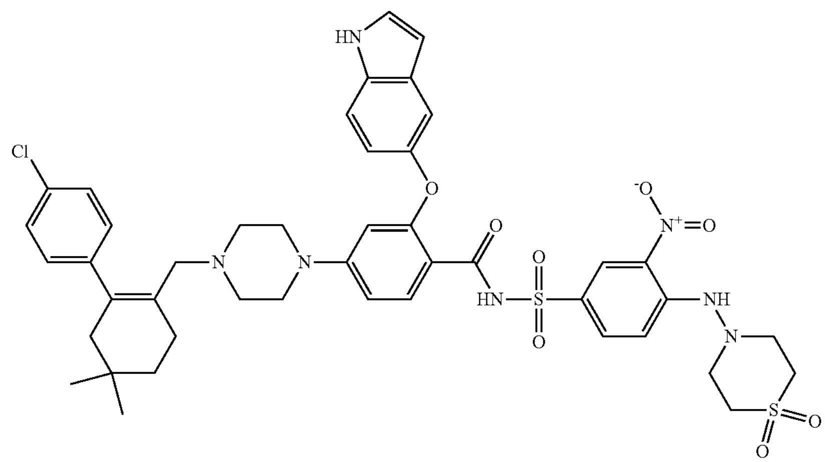 |
| 4-(4-{[2-(4-chloro-phenyl)-4,4-dimethylcyclohex-1-en-1-yl]methyl}piperazin-1-yl)-2-(1H-indol-5-yloxy)-N-({4-[(4-morpholin-4-ylcyclohexyl)amino]-3-nitrophenyl}sulfonyl)benzamide | 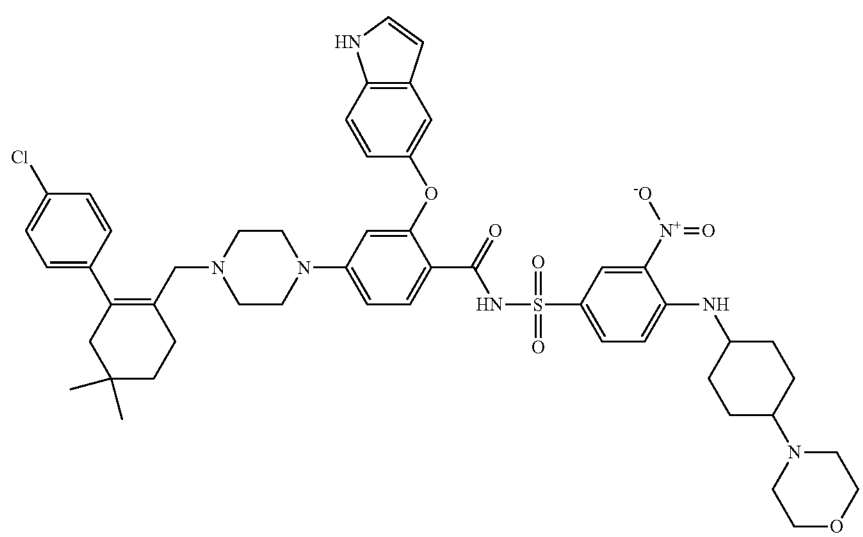 |

| Name | Structure |
|---|---|
| N-{[5-bromo-6-(tetrahydro-2H-pyran-4-ylmethoxy)pyridin-3-yl]sulfonyl}-4-(4-{[2-(4-chlorophenyl)-4,4-dimethylcyclohex-1-en-1-yl]methyl}piperazin-1-yl)-2-(1H-indol-4-yloxy)benzamide | 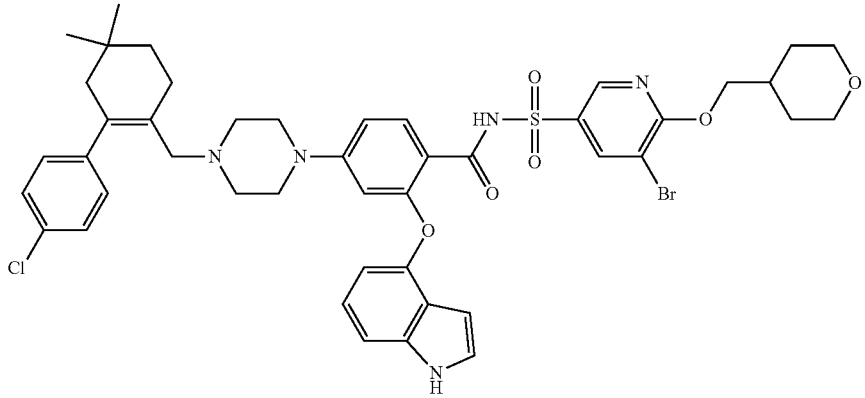 |
| 4-(4-{[2-(4-chlorophenyl)-4,4-dimethylcyclohex-1-en-1-yl]methyl}piperazin-1-yl)-2-(1H-indol-4-yloxy)-N-{[6-[(tetrahydro-2H-pyran-4-ylmethyl)amino]-5-(1,3-thiazol-2-yl)pyridin-3-yl]sulfonyl}benzamide | 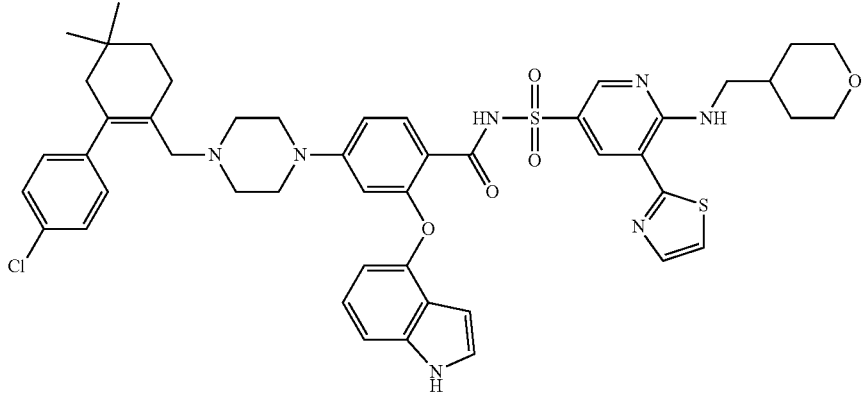 [SMILES: CC1(C)CCC(CN2CCN(c3ccc(C(=O)NS(=O)(=O)c4cnc(NCC5CCOCC5)c(-c5nccs5)c4)c(Oc4cccc5[nH]ccc45)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-({3-cyano-4-[(tetrahydro-2H-pyran-4-ylmethyl)amino]phenyl}sulfonyl)-2-(1H-indol-4-yloxy)benzamide | 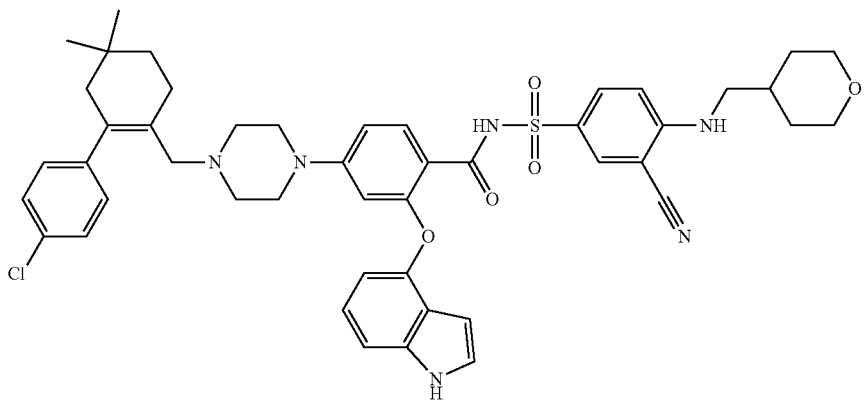 [SMILES: CC1(C)CCC(CN2CCN(c3ccc(C(=O)NS(=O)(=O)c4ccc(NCC5CCOCC5)c(C#N)c4)c(Oc4cccc5[nH]ccc45)c3)CC2)=C(c2ccc(Cl)cc2)C1] |

| Name | Structure |
|---|---|
| 4-(4-{[2-(4-chloro-phenyl)-4,4-dimethylcyclohex-1-en-1-yl]methyl]piperazin-1-yl)-N-({3-cyano-4-[(tetrahydro-2H-pyran-4-ylmethyl)amino]phenyl}sulfonyl)-2-(1H-indol-5-yloxy)benzamide | |
| 4-(4-{[2-(4-chloro-phenyl)-4,4-dimethylcyclohex-1-en-1-yl]methyl]piperazin-1-yl)-N-({4-[(3,3-dimethylbutyl)amino]-3-nitrophenyl}sulfonyl)-2-(1H-indol-5-yloxy)benzamide | |
| 4-(4-{[2-(4-chloro-phenyl)-4,4-dimethylcyclohex-1-en-1-yl]methyl]piperazin-1-yl)-N-[(4-{[(1S)-1-(hydroxymethyl)-3-methylbutyl]amino}-3-nitrophenyl)sulfonyl]-2-(1H-indol-5-yloxy)benzamide | |

-continued

| Name | Structure |
|---|---|
| 4-(4-{[2-(4-chlorophenyl)-4,4-dimethylcyclohex-1-en-1-yl]methyl]piperazin-1-yl)-2-(1H-indol-5-yloxy)-N-[(3-nitro-4-{[(2R)-tetrahydrofuran-2-ylmethyl]amino}phenyl)sulfonyl]benzamide | |
| 4-(4-{[2-(4-chlorophenyl)-4,4-dimethylcyclohex-1-en-1-yl]methyl}piperazin-1-yl)-N-[(4-{[(1R)-1-(hydroxymethyl)-2-methylpropyl]amino}-3-nitrophenyl)sulfonyl]-2-(1H-indol-5-yloxy)benzamide | |
| 4-(4-{[2-(4-chlorophenyl)-4,4-dimethylcyclohex-1-en-1-yl]methyl}piperazin-1-yl)-2-(1H-indol-5-yloxy)-N-({4-[(4-methoxyphenyl)amino]-3-nitrophenyl}sulfonyl)benzamide | |

-continued

| Name | Structure |
|---|---|
| N-[(4-{[2-(1,3-benzodioxol-5-yl)ethyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-indol-5-yloxy)benzamide | |
| 4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[3-(2-oxopyrrolidin-1-yl)propyl]amino}phenyl)sulfonyl]benzamide | 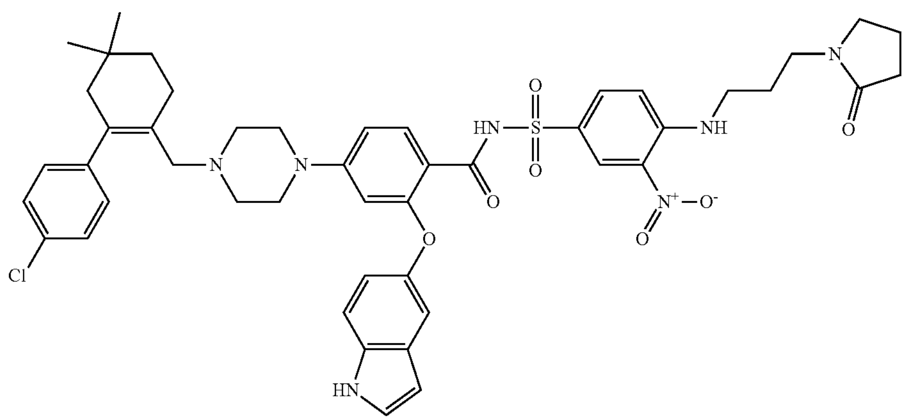 [SMILES: CC1(C)CCC(CN2CCN(c3ccc(C(=O)NS(=O)(=O)c4ccc(NCCCN5CCCC5=O)c([N+](=O)[O-])c4)c(Oc4ccc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-({4-[(4-hydroxyphenyl)amino]-3-nitrophenyl}sulfonyl)-2-(1H-indol-5-yloxy)benzamide | 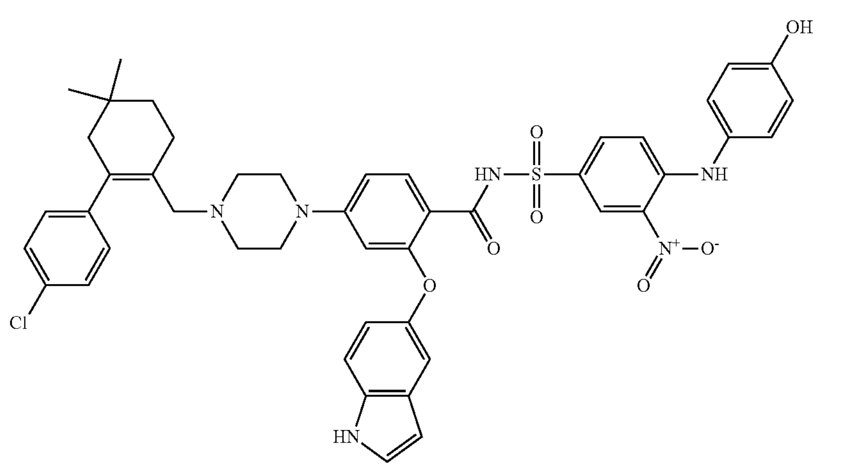 [SMILES: CC1(C)CCC(CN2CCN(c3ccc(C(=O)NS(=O)(=O)c4ccc(Nc5ccc(O)cc5)c([N+](=O)[O-])c4)c(Oc4ccc5[nH]ccc5c4)c3)CC2)=C(c2ccc(Cl)cc2)C1] |

| Name | Structure |
|---|---|
| N-{[4-({2-[4-(aminosulfonyl)phenyl]ethyl}amino)-3-nitrophenyl]sulfonyl}-4-(4-{[2-(4-chlorophenyl)-4,4-dimethylcyclohex-1-en-1-yl]methyl}piperazin-1-yl)-2-(1H-indol-5-yloxy)benzamide | 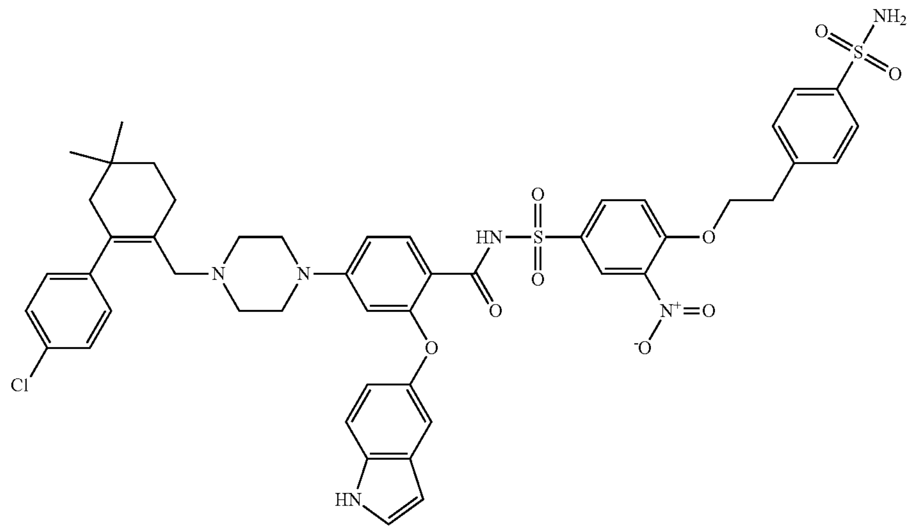 |
| 4-(4-{[2-(4-chlorophenyl)-4,4-dimethylcyclohex-1-en-1-yl]methyl}piperazin-1-yl)-N-[(4-{[3-(1H-imidazol-1-yl)propyl]amino}-3-nitrophenyl)sulfonyl]-2-(1H-indol-5-yloxy)benzamide | 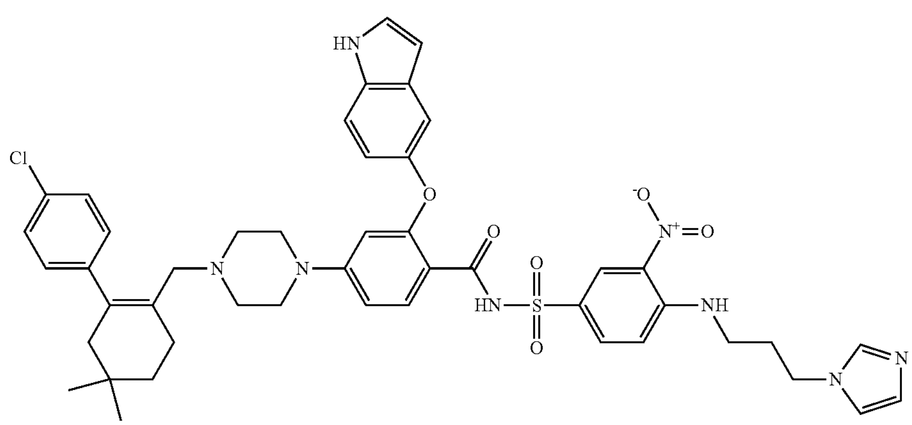 |
| 4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[(1S)-1-phenylethyl]amino}phenyl)sulfonyl]benzamide | 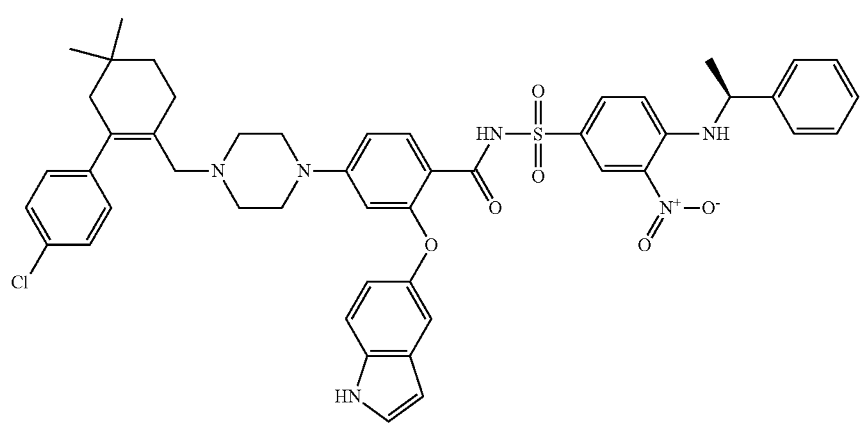 [SMILES: C[C@H](Nc1ccc(S(=O)(=O)NC(=O)c2ccc(N3CCN(CC4=C(c5ccc(Cl)cc5)CC(C)(C)CC4)CC3)cc2Oc2ccc3[nH]ccc3c2)cc1[N+](=O)[O-])c1ccccc1] |

| Name | Structure |
|---|---|
| N-({2-chloro-5-fluoro-4-[(tetrahydro-2H-pyran-4-ylmethyl)amino]phenyl}sulfonyl)-4-(4-{[2-(4-chlorophenyl)-4,4-dimethylcyclohex-1-en-1-yl]methyl}piperazin-1-yl)-2-(1H-indol-5-yloxy)benzamide | |
| 4-(4-{[2-(4-chlorophenyl)-4,4-dimethylcyclohex-1-en-1-yl]methyl}piperazin-1-yl)-2-(1H-indol-5-yloxy)-N-[(4-{[2-(2-methoxyethoxy)ethyl]thio}-3-nitrophenyl)sulfonyl]benzamide | |
| 4-(4-{[2-(4-chlorophenyl)-4,4-dimethylcyclohex-1-en-1-yl]methyl]piperazin-1-yl)-2-(1H-indol-4-yloxy)-N-[(4-{[2-(2-methoxyethoxy)ethyl]thio}-3-nitrophenyl)sulfonyl]benzamide | |

| Name | Structure |
|---|---|
| 4-(4-{[2-(4-chloro-phenyl)-4,4-dimethylcyclohex-1-en-1-yl]methyl}piperazin-1-yl)-2-(1H-indol-5-yloxy)-N-{[4-(methylsulfonyl)phenyl]sulfonyl}benzamide | 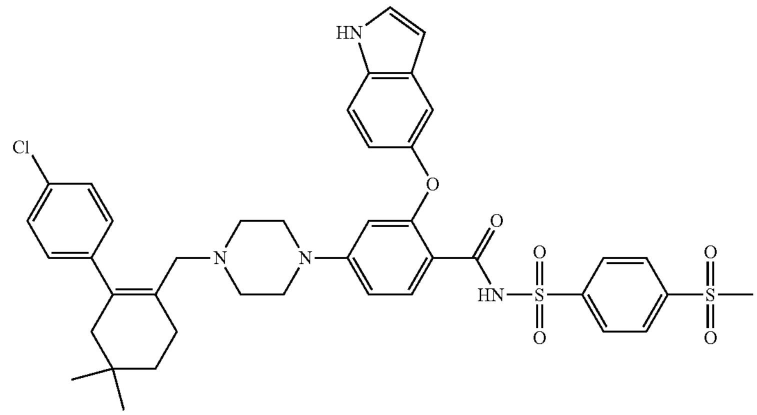 [SMILES: CC1(C)CCC(CN2CCN(c3ccc(C(=O)NS(=O)(=O)c4ccc(S(C)(=O)=O)cc4)c(Oc4ccc5[nH]ccc5c4)c3)CC2)=C(c2ccc(Cl)cc2)C1] |
| 4-(4-{[2-(4-chloro-phenyl)-4,4-dimethylcyclohex-1-en-1-yl]methyl}piperazin-1-yl)-2-(1H-indol-4-yloxy)-N-{[4-(methylsulfonyl)phenyl]sulfonyl}benzamide | 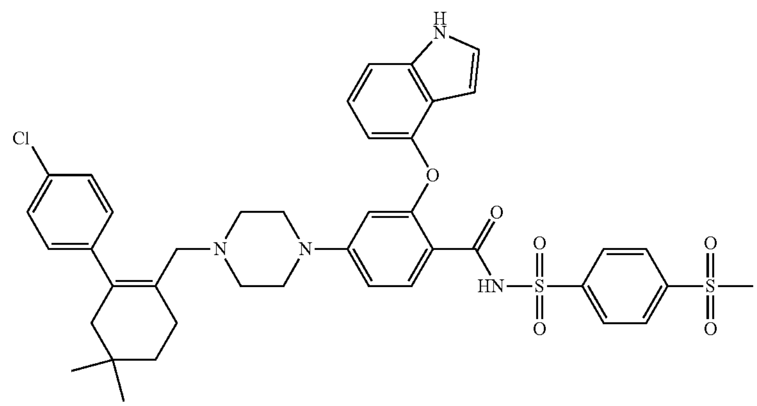 [SMILES: CC1(C)CCC(CN2CCN(c3ccc(C(=O)NS(=O)(=O)c4ccc(S(C)(=O)=O)cc4)c(Oc4cccc5[nH]ccc45)c3)CC2)=C(c2ccc(Cl)cc2)C1] |
| 4-(4-{[2-(4-chloro-phenyl)-4,4-dimethylcyclohex-1-en-1-yl]methyl}piperazin-1-yl)-N-({4-[(2,2-dimethyltetrahydro-2H-pyran-4-yl)methoxy]-3-nitrophenyl}sulfonyl)-2-(1H-indol-5-yloxy)benzamide | |

-continued

| Name | Structure |
|---|---|
| 4-(4-{[2-(4-chlorophenyl)-4,4-dimethylcyclohex-1-en-1-yl]methyl}piperazin-1-yl)-N-({5-cyano-6-[(4-fluorotetrahydro-2H-pyran-4-yl)methoxy]pyridin-3-yl}sulfonyl)-2-(1H-indol-5-yloxy)benzamide | |
| 4-(4-{[2-(4-chlorophenyl)-4,4-dimethylcyclohex-1-en-1-yl]methyl}piperazin-1-yl)-N-{[5-cyano-6-(tetrahydro-2H-pyran-4-ylmethoxy)pyridin-3-yl]sulfonyl}-2-(1H-indol-4-yloxy)benzamide | |
| 4-(4-{[2-(4-chlorophenyl)-4,4-dimethylcyclohex-1-en-1-yl]methyl}piperazin-1-yl)-N-{[5-chloro-6-(tetrahydro-2H-pyran-4-ylmethoxy)pyridin-3-yl]sulfonyl}-2-(1H-indol-4-yloxy)benzamide | |

| Name | Structure |
|---|---|
| 4-(4-{[2-(4-chlorophenyl)-4,4-dimethylcyclohex-1-en-1-yl]methyl}piperazin-1-yl)-N-{[5-cyano-6-(2-morpholin-4-ylethoxy)pyridin-3-yl]sulfonyl}-2-(1H-indol-5-yloxy)benzamide | |
| 4-(4-{[2-(4-chlorophenyl)-4,4-dimethylcyclohex-1-en-1-yl]methyl}piperazin-1-yl)-2-(1H-indol-5-yloxy)-N-({3-nitro-4-[(1-tetrahydro-2H-pyran-4-yl-piperidin-4-yl)oxy]phenyl}sulfonyl)benzamide | |
| 4-(4-{[2-(4-chlorophenyl)-4,4-dimethylcyclohex-1-en-1-yl]methyl}piperazin-1-yl)-2-(1H-indol-5-yloxy)-N-({4-[(4-morpholin-4-ylbut-2-ynyl)oxy]-3-nitrophenyl}sulfonyl)benzamide | |

| Name | Structure |
|---|---|
| 4-(4-{[2-(4-chlorophenyl)-4,4-dimethylcyclohex-1-en-1-yl]methyl}piperazin-1-yl)-N-{[5-ethynyl-6-(tetrahydro-2H-pyran-4-ylmethoxy)pyridin-3-yl]sulfonyl}-2-(1H-indol-4-yloxy)benzamide | |
| 4-(4-{[2-(4-chlorophenyl)-4,4-dimethylcyclohex-1-en-1-yl]methyl}piperazin-1-yl)-N-{[5-cyano-6-(2-morpholin-4-ylethoxy)pyridin-3-yl]sulfonyl}-2-(1H-indol-4-yloxy)benzamide | |
| 4-(4-{[2-(4-chlorophenyl)-4,4-dimethylcyclohex-1-en-1-yl]methyl}piperazin-1-yl)-N-({5-cyano-6-r(4-fluorotetrahydro-2H-pyran-4-yl)methoxy]pyridin-3-yl}sulfonyl)-2-(1H-indol-4-yloxy)benzamide | |

| Name | Structure |
|---|---|
| 4-(4-{[2-(4-chlorophenyl)-4,4-dimethylcyclohex-1-en-1-yl]methyl}piperazin-1-yl)-N-({4-[(3-hydroxy-4-methoxyphenyl)amino]-3-nitrophenyl}sulfonyl)-2-(1H-indol-5-yloxy)benzamide | |
| 4-(4-{[2-(4-chlorophenyl)-4,4-dimethylcyclohex-1-en-1-yl]methyl}piperazin-1-yl)-2-(2,3-dihydro-1H-indol-4-yloxy)-N-({4-[(1-methylpiperidin-4-yl)amino]-3-nitrophenyl}sulfonyl)benzamide | |
| 4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)-2-(pyridin-3-ylamino)benzamide | |

-continued

| Name | Structure |
|---|---|
| 4-(4-{[2-(4-chloro-phenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)-2-(pyridin-3-ylamino)benzamide | 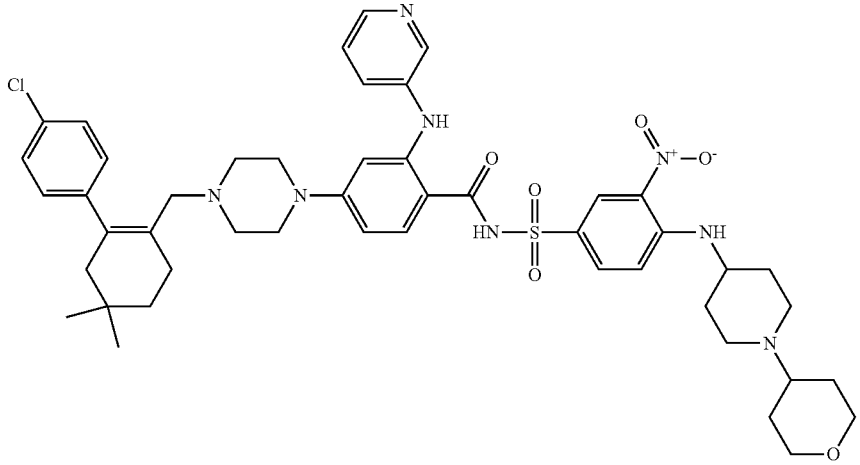 [SMILES: CC1(C)CCC(CN2CCN(c3ccc(C(=O)NS(=O)(=O)c4ccc(NC5CCN(C6CCOCC6)CC5)c([N+](=O)[O-])c4)c(Oc4cccnc4)c3)CC2)=C(c2ccc(Cl)cc2)C1] |
| 4-(4-{[2-(4-chloro-phenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)-2-(pyridin-3-yloxy)benzamide | 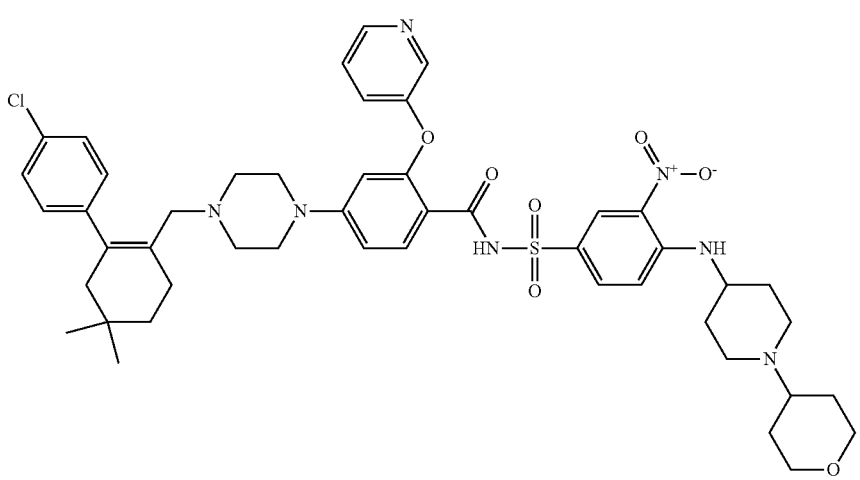 |
| 4-(4-{[2-(4-chloro-phenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1,2,3,4-tetrahydro-isoquinolin-5-yloxy)benzamide | 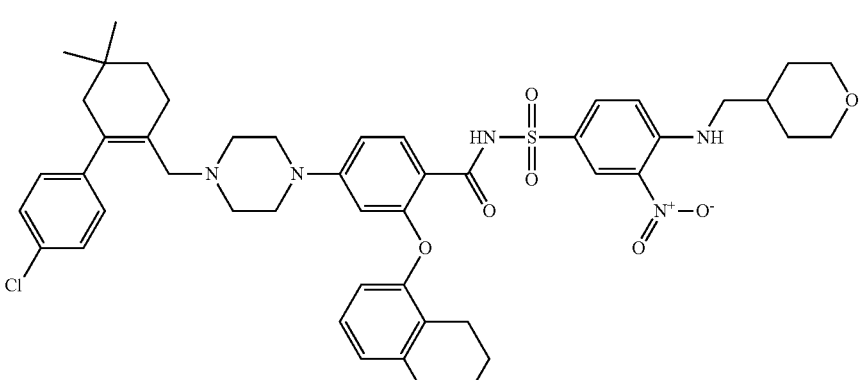 |

-continued

| Name | Structure |
|---|---|
| 4-(4-{[2-(4-chlorophenyl)-4,4-dimethylcyclohex-1-en-1-yl]methyl}piperazin-1-yl)-2-(1H-indazol-4-yloxy)-N-({3-nitro-4-[(tetrahydro-2H-pyran-4-ylmethyl)amino]phenyl}sulfonyl)benzamide | |
| 4-(4-{[2-(4-chlorophenyl)-4,4-dimethylcyclohex-1-en-1-yl]methyl}piperazin-1-yl)-2-(1H-indazol-4-yloxy)-N-({3-nitro-4-[(1-tetrahydro-2H-pyran-4-ylpiperidin-4-yl)amino]phenyl}sulfonyl)benzamide | |
| Trans-4-(4-{[2-(4-chlorophenyl)-4,4-dimethylcyclohex-1-en-1-yl]methyl}piperazin-1-yl)-2-(1H-indazol-4-yloxy)-N-({4-[(4-morpholin-4-ylcyclohexyl)amino]-3-nitrophenyl}sulfonyl)benzamide | |

| Name | Structure |
|---|---|
| 2-(1H-benzimidazol-4-yloxy)-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide | 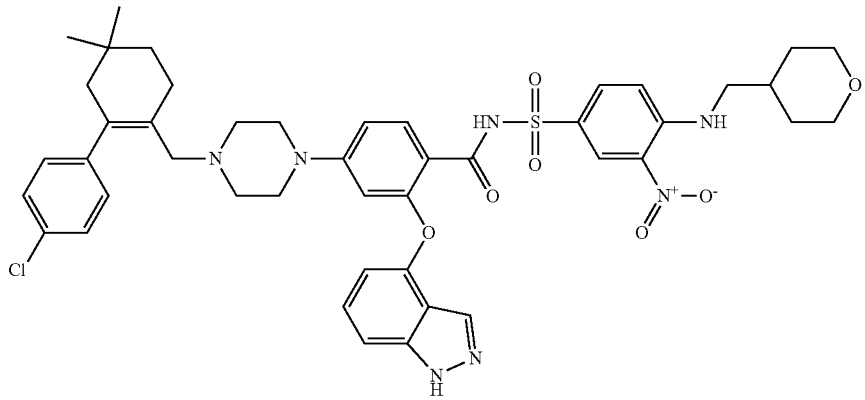 |
| N-({5-chloro-6-[(4-fluorotetrahydro-2H-pyran-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide | 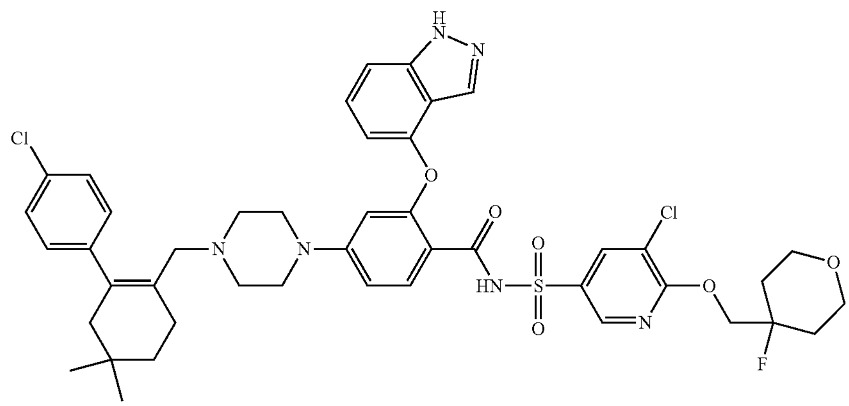 [SMILES: CC1(C)CCC(CN2CCN(c3ccc(C(=O)NS(=O)(=O)c4cnc(OCC5(F)CCOCC5)c(Cl)c4)c(Oc4cccc5[nH]ncc45)c3)CC2)=C(c2ccc(Cl)cc2)C1] |
| N-({5-chloro-6-[(4-fluorotetrahydro-2H-pyran-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indol-4-yloxy)benzamide | 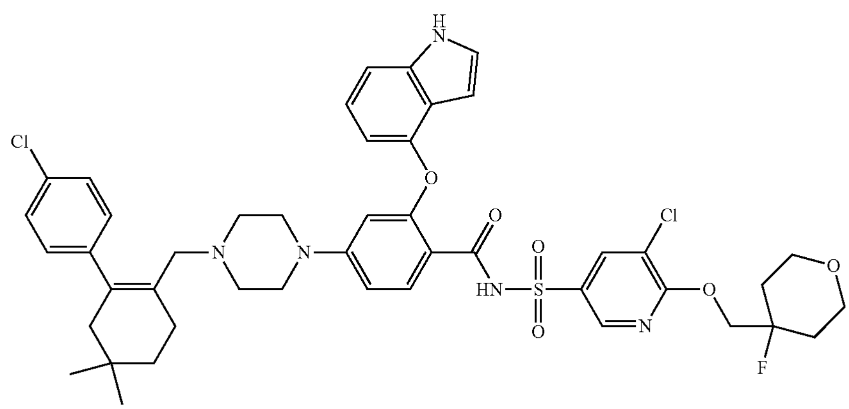 |
| 4-(4-{[2-(4-chlorophenyl)-4,4-dimethylcyclohex-1-en-1-yl]methyl}piperazin-1-yl)-N-({5-cyano-6-[(4-fluorotetrahydro-2H-pyran-4-yl)methoxy]pyridin-3-yl}sulfonyl)-2-(1H-indazol-4-yloxy)benzamide | 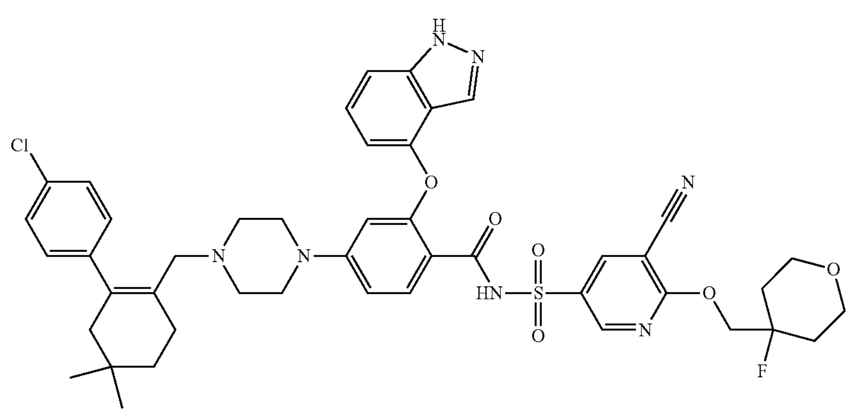 [SMILES: CC1(C)CCC(CN2CCN(c3ccc(C(=O)NS(=O)(=O)c4cnc(OCC5(F)CCOCC5)c(C#N)c4)c(Oc4cccc5[nH]ncc45)c3)CC2)=C(c2ccc(Cl)cc2)C1] |

| Name | Structure |
|---|---|
| 2-(1H-benzimidazol-4-yloxy)-4-(4-{[2-(4-chlorophenyl)-4,4-dimethylcyclohex-1-en-1-yl]methyl}piperazin-1-yl)-N-[(4-{[(3R)-1-(2,2-difluoroethyl)pyrrolidin-3-yl]amino}-3-nitrophenyl)sulfonyl]benzamide | |
| 2-(1H-benzimidazol-4-yloxy)-4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-nitrophenyl}sulfonyl)benzamide | |
| 4-(4-{[2-(4-chlorophenyl)-4,4-dimethylcyclohex-1-en-1-yl]methyl}piperazin-1-yl)-N-[(4-{[(4-fluorotetrahydro-2H-pyran-4-yl)methyl]amino}-3-nitrophenyl)sulfonyl]-2-(1H-indazol-4-yloxy)benzamide | |

| Name | Structure |
|---|---|
| 4-(4-{[2-(4-chlorophenyl)-4,4-dimethylcyclohex-1-en-1-yl]methyl}piperazin-1-yl)-N-{6-[(4-fluorotetrahydro-2H-pyran-4-yl)methoxy]-5-(trifluoromethyl)pyridin-3-yl]sulfonyl}-2-(1H-indazol-4-yloxy)benzamide | |
| 4-(4-{[2-(4-chlorophenyl)-4,4-dimethylcyclohex-1-en-1-yl]methyl}piperazin-1-yl)-N-[(4-{[(4-cyclopropylmorpholin-2-yl)methyl]amino}-3-nitrophenyl)sulfonyl]-2-(1H-indazol-4-yloxy)benzamide | |
| 4-(4-{[2-(4-chlorophenyl)-4,4-dimethylcyclohex-1-en-1-yl]methyl}piperazin-1-yl)-N-[(4-{[(4,4-difluorocyclohexyl)methyl]amino}-3-nitrophenyl)sulfonyl]-2-(1H-indazol-4-yloxy)benzamide | |

| Name | Structure |
|---|---|
| N-[(5-chloro-6-{[(4-fluorotetrahydro-2H-pyran-4-yl)methyl]amino}pyridin-3-yl)sulfonyl]-4-(4-{[2-(4-chlorophenyl)-4,4-dimethylcyclohex-1-en-1-yl]methyl}piperazin-1-yl)-2-(1H-indazol-4-yloxy)benzamide | 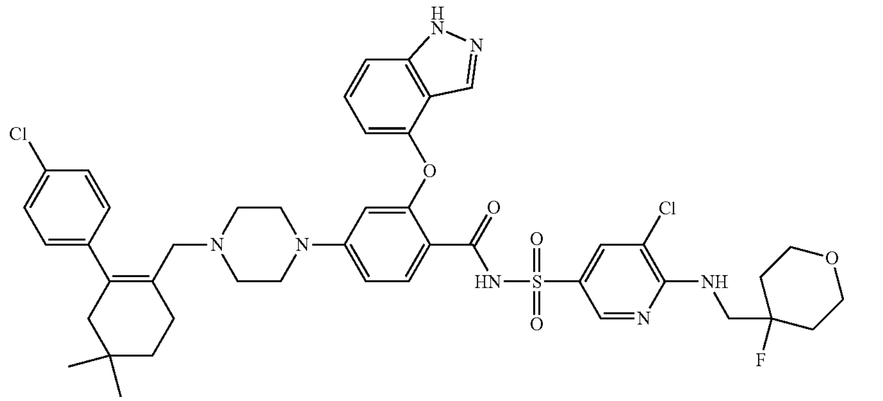 [SMILES: CC1(C)CCC(CN2CCN(c3ccc(C(=O)NS(=O)(=O)c4cnc(NCC5(F)CCOCC5)c(Cl)c4)c(Oc4cccc5[nH]ncc45)c3)CC2)=C(c2ccc(Cl)cc2)C1] |
| Trans-N-({5-chloro-6-[(4-methoxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide | 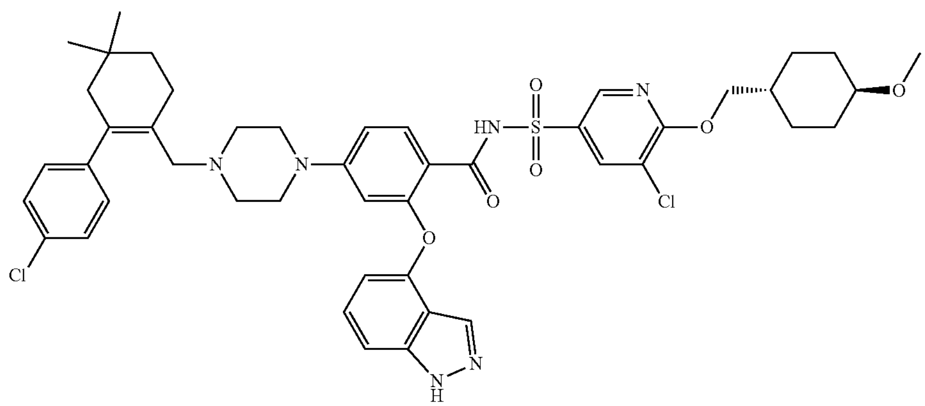 [SMILES: CO[C@H]1CC[C@H](COc2ncc(S(=O)(=O)NC(=O)c3ccc(N4CCN(CC5=C(c6ccc(Cl)cc6)CC(C)(C)CC5)CC4)cc3Oc3cccc4[nH]ncc34)cc2Cl)CC1] |
| 2-(1H-benzimidazol-4-yloxy)-4-(4-{[2-(4-chlorophenyl)-4,4-dimethylcyclohex-1-en-1-yl]methyl}piperazin-1-yl)-N-{[4-({[4-(2,2-difluoroethyl)morpholin-2-yl]methyl}amino)-3-nitrophenyl]sulfonyl}benzamide | 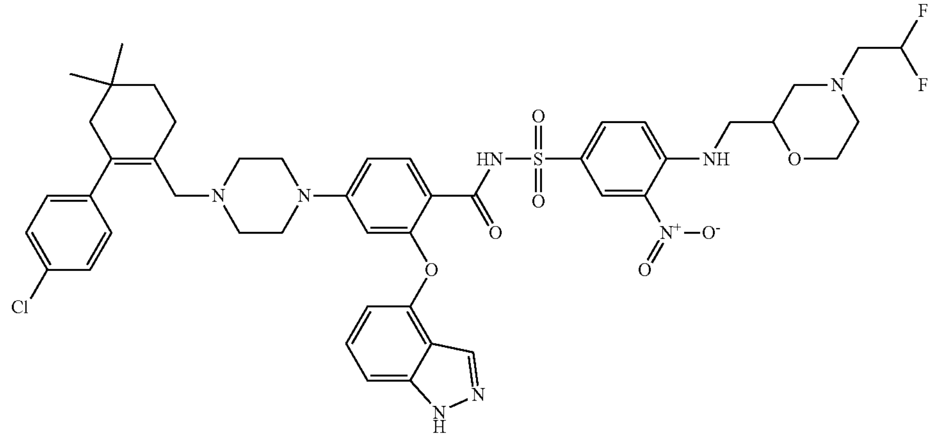 [SMILES: CC1(C)CCC(CN2CCN(c3ccc(C(=O)NS(=O)(=O)c4ccc(NCC5CN(CC(F)F)CCO5)c([N+](=O)[O-])c4)c(Oc4cccc5[nH]ncc45)c3)CC2)=C(c2ccc(Cl)cc2)C1] |

| Name | Structure |
|---|---|
| 4-(4-{[2-(4-chloro-phenyl)-4,4-dimethylcyclohex-1-en-1-yl]methyl]piperazin-1-yl)-N-({5-fluoro-6-[(4-fluorotetra-hydro-2H-pyran-4-yl)methoxy]pyridin-3-yl}sulfonyl)-2-(1H-indazol-4-yloxy)benzamide | 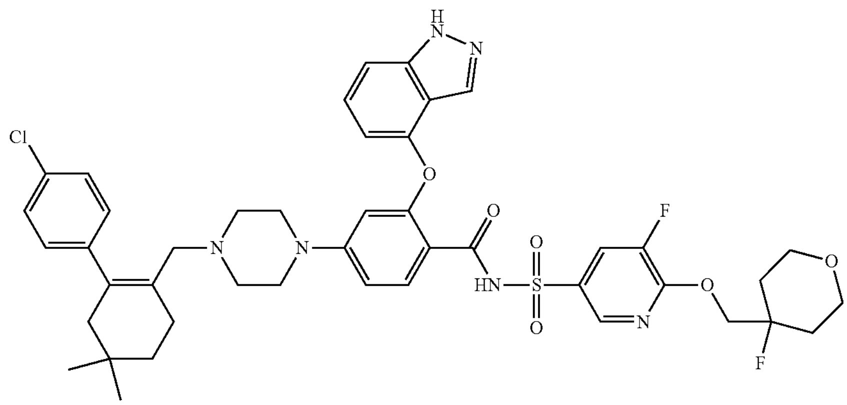 [SMILES: CC1(C)CCC(CN2CCN(c3ccc(C(=O)NS(=O)(=O)c4cnc(OCC5(F)CCOCC5)c(F)c4)c(Oc4cccc5[nH]ncc45)c3)CC2)=C(c2ccc(Cl)cc2)C1] |
| 2-(1H-benzimidazol-4-yloxy)-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide | 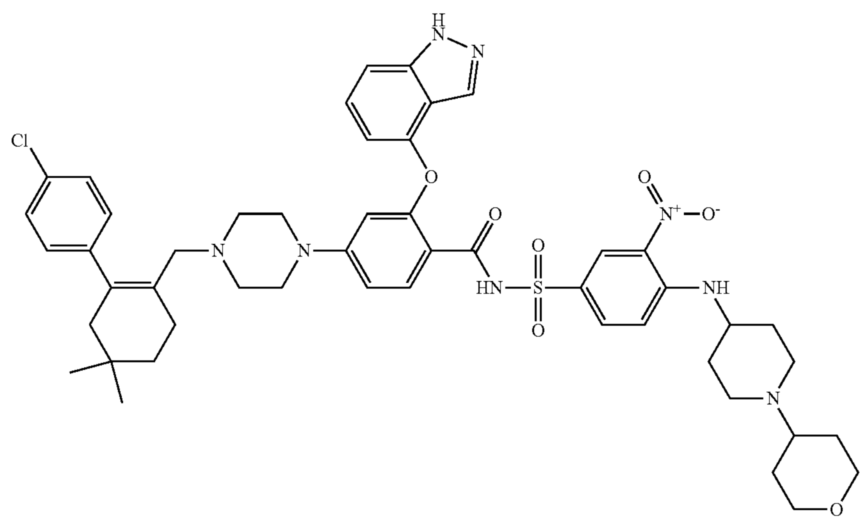 [SMILES: CC1(C)CCC(CN2CCN(c3ccc(C(=O)NS(=O)(=O)c4ccc(NC5CCN(C6CCOCC6)CC5)c([N+](=O)[O-])c4)c(Oc4cccc5[nH]ncc45)c3)CC2)=C(c2ccc(Cl)cc2)C1] |
| 2-(1H-benzimidazol-4-yloxy)-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide | 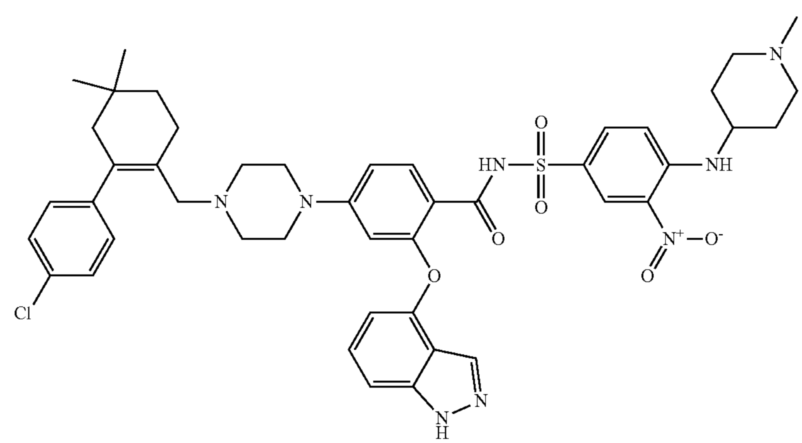 [SMILES: CN1CCC(Nc2ccc(S(=O)(=O)NC(=O)c3ccc(N4CCN(CC5=C(c6ccc(Cl)cc6)CC(C)(C)CC5)CC4)cc3Oc3cccc4[nH]ncc34)cc2[N+](=O)[O-])CC1] |

| Name | Structure |
|---|---|
| N-[(5-chloro-6-{[1-(cyanomethyl)-4-fluoropiperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-indazol-4-yloxy)benzamide | 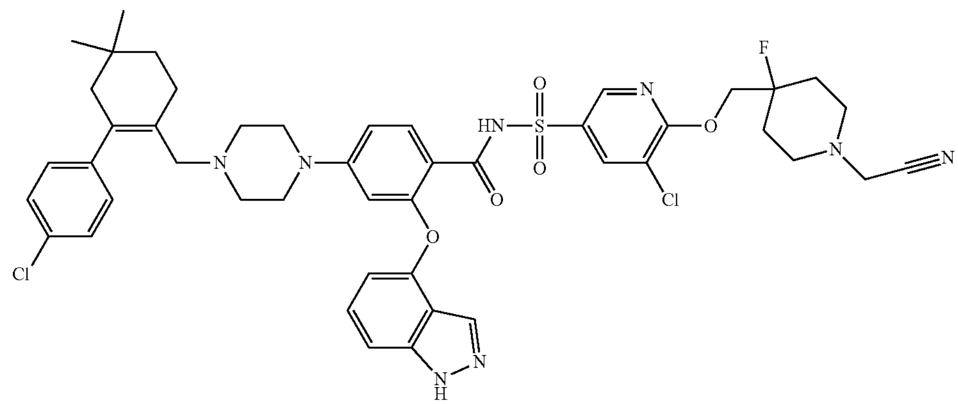 [SMILES: CC1(C)CCC(CN2CCN(c3ccc(C(=O)NS(=O)(=O)c4cnc(OCC5(F)CCN(CC#N)CC5)c(Cl)c4)c(Oc4cccc5[nH]ncc45)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-{[5-chloro-6-(tetrahydrofuran-3-ylmethoxy)pyridin-3-yl]sulfonyl}-2-(1H-indazol-4-yloxy)benzamide | |
| Trans-N-({5-chloro-6-[(4-hydroxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide | 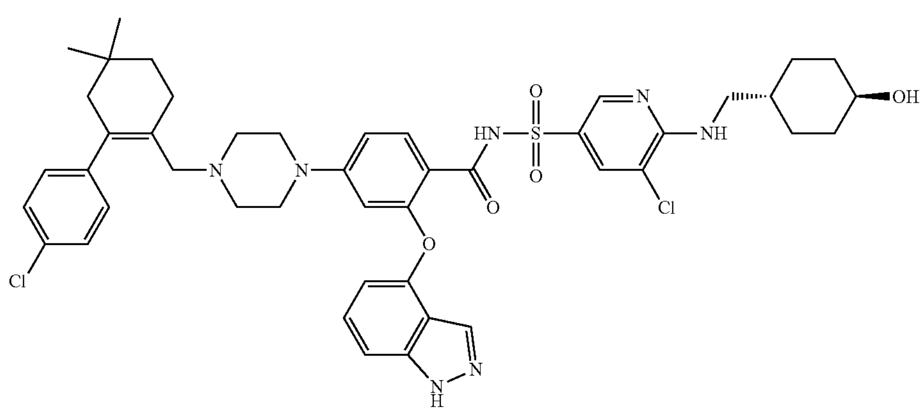 [SMILES: CC1(C)CCC(CN2CCN(c3ccc(C(=O)NS(=O)(=O)c4cnc(NC[C@H]5CC[C@H](O)CC5)c(Cl)c4)c(Oc4cccc5[nH]ncc45)c3)CC2)=C(c2ccc(Cl)cc2)C1] |

| Name | Structure |
|---|---|
| N-[(5-chloro-6-{[(3R)-1-(2,2-difluoroethyl)pyrrolidin-3-yl]oxy}pyridin-3-yl)sulfonyl]-4-(4-{[2-(4-chlorophenyl)-4,4-dimethylcyclohex-1-en-1-yl]methyl}piperazin-1-yl)-2-(1H-indazol-4-yloxy)benzamide | 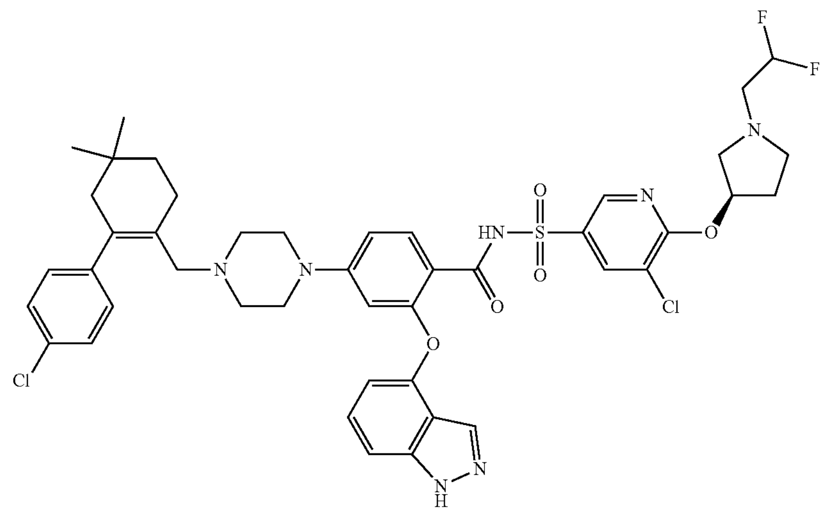 [SMILES: CC1(C)CCC(CN2CCN(c3ccc(C(=O)NS(=O)(=O)c4cnc(O[C@@H]5CCN(CC(F)F)C5)c(Cl)c4)c(Oc4cccc5[nH]ncc45)c3)CC2)=C(c2ccc(Cl)cc2)C1] |
| 2-(1H-benzimidazol-4-yloxy)-N-[(5-chloro-6-{[(2S)-4-(N,N-dimethylglycyl)morpholin-2-yl]methoxy}pyridin-3-yl)sulfonyl]-4-(4-{[2-(4-chlorophenyl)-4,4-dimethylcyclohex-1-en-1-yl]methyl]piperazin-1-yl)benzamide | |
| 2-(1H-benzimidazol-4-yloxy)-N-[(5-chloro-6-{[(2R)-4-(N,N-dimethylglycyl)morpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)benzamide | 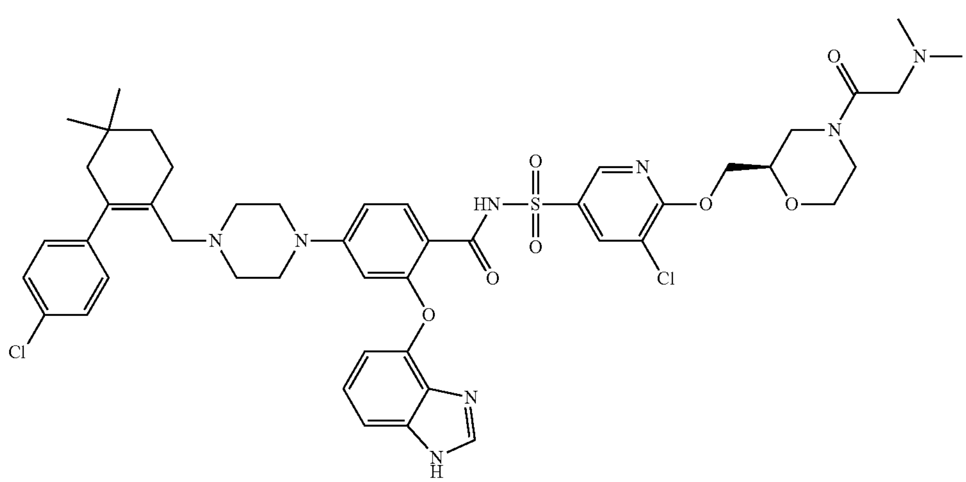 [SMILES: CN(C)CC(=O)N1CCO[C@@H](COc2ncc(S(=O)(=O)NC(=O)c3ccc(N4CCN(CC5=C(c6ccc(Cl)cc6)CC(C)(C)CC5)CC4)cc3Oc3cccc4[nH]cnc34)cc2Cl)C1] |

-continued

| Name | Structure |
|---|---|
| N-[(5-chloro-6-{[(2S)-4-(N,N-dimethylglycyl)morpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-indazol-4-yloxy)benzamide | 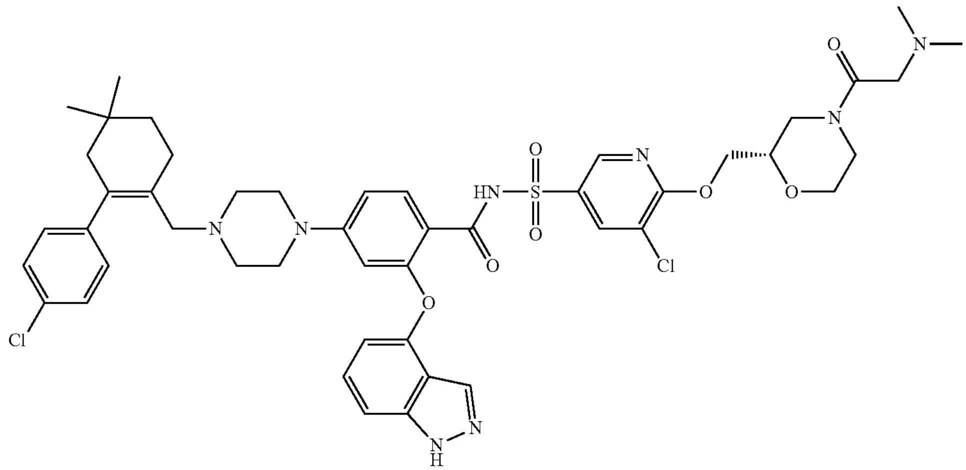 [SMILES: CN(C)CC(=O)N1CCO[C@H](COc2ncc(S(=O)(=O)NC(=O)c3ccc(N4CCN(CC5=C(c6ccc(Cl)cc6)CC(C)(C)CC5)CC4)cc3Oc3cccc4[nH]ncc34)cc2Cl)C1] |
| N-[(5-chloro-6-([(2R)-4-(N,N-dimethylglycyl)morpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-indazol-4-yloxy)benzamide | 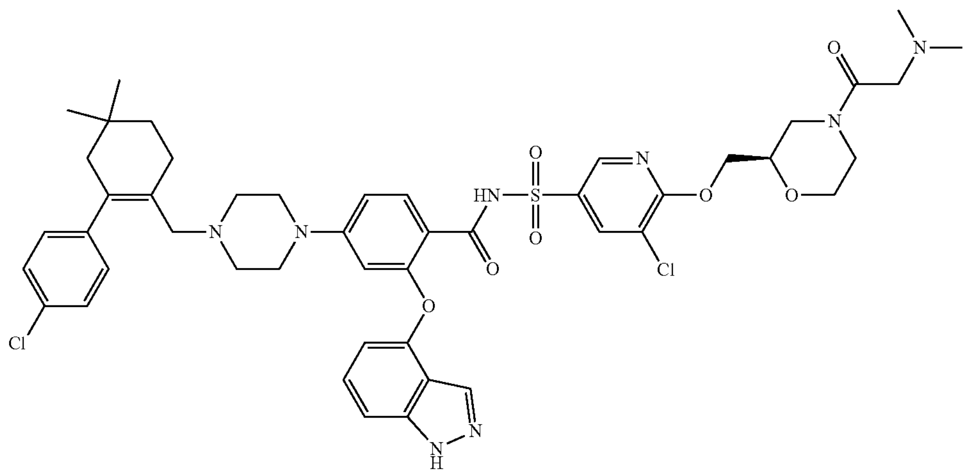 [SMILES: CN(C)CC(=O)N1CCO[C@@H](COc2ncc(S(=O)(=O)NC(=O)c3ccc(N4CCN(CC5=C(c6ccc(Cl)cc6)CC(C)(C)CC5)CC4)cc3Oc3cccc4[nH]ncc34)cc2Cl)C1] |
| 4-(4-{[2-(4-chlorophenyl)-4,4-dimethylcyclohex-1-en-1-yl]methyl}piperazin-1-yl)-N-{[5-chloro-6-(tetrahydro-2H-pyran-4-ylmethoxy)pyridin-3-yl]sulfonyl}-2-(1H-indazol-4-yloxy)benzamide | 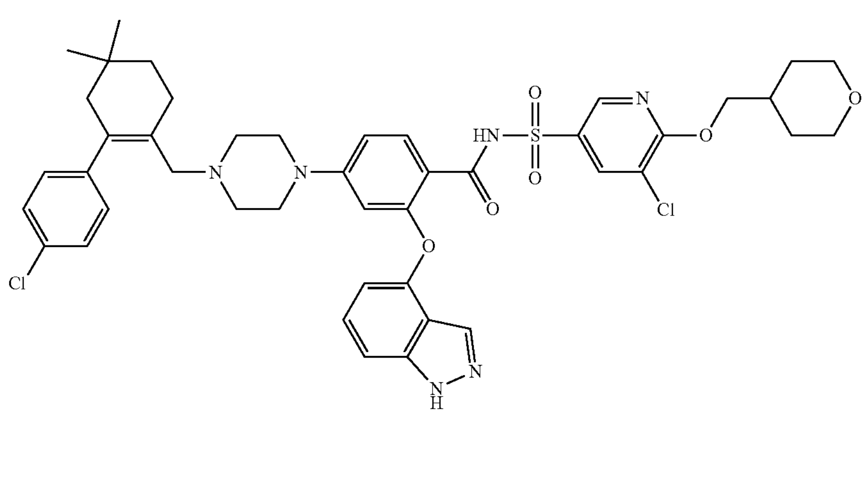 |

| Name | Structure |
|---|---|
| 2-(1H-benzimidazol-4-yloxy)-4-(4-{[2-(4-chlorophenyl)-4,4-dimethylcyclohex-1-en-1-yl]methyl}piperazin-1-yl)-N-[(4-{[(3R)-1-(cyanomethyl)pyrrolidin-3-yl]amino}-3-nitrophenyl)sulfonyl]benzamide | 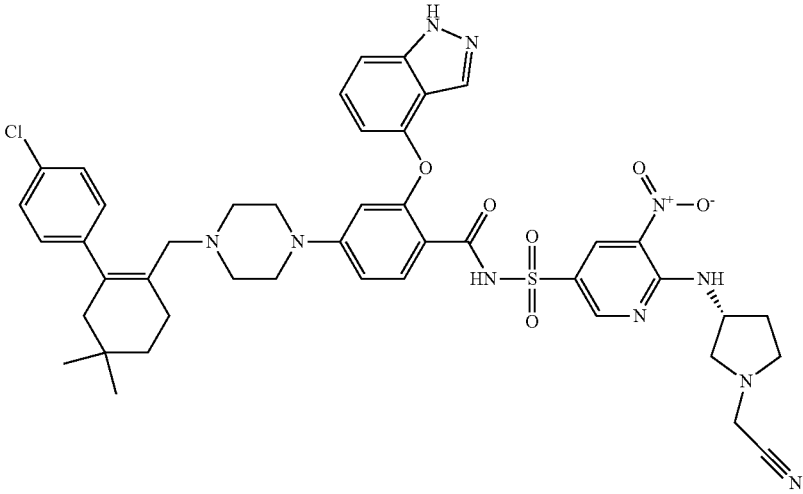 [SMILES: CC1(C)CCC(CN2CCN(c3ccc(C(=O)NS(=O)(=O)c4cnc(N[C@@H]5CCN(CC#N)C5)c([N+](=O)[O-])c4)c(Oc4cccc5[nH]ncc45)c3)CC2)=C(c2ccc(Cl)cc2)C1] |
| 2-(1H-benzimidazol-4-yloxy)-4-(4-{[2-(4-chlorophenyl)-4,4-dimethylcyclohex-1-en-1-yl]methyl}piperazin-1-yl)-N-{[4-({(3R)-1-[2-(2-methoxyethoxy)ethyl]pyrrolidin-3-yl}amino)-3-nitrophenyl]sulfonyl}benzamide | 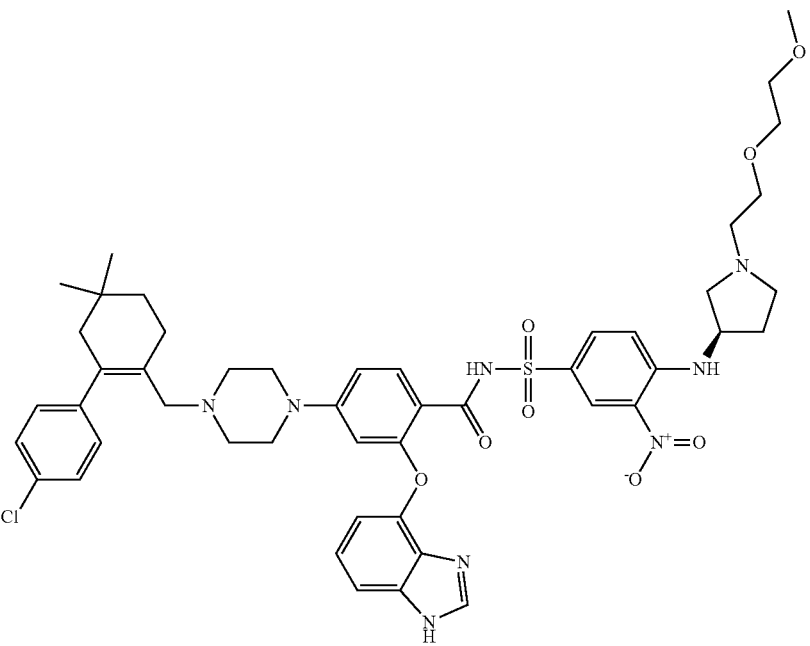 |

| Name | Structure |
|---|---|
| 2-(1H-benzimidazol-4-yloxy)-4-(4-{[2-(4-chlorophenyl)-4,4-dimethylcyclohex-1-en-1-yl]methyl}piperazin-1-yl)-N-[(4-{[(3R)-1-(N,N-dimethylglycyl)pyrrolidin-3-yl]amino}-3-nitrophenyl)sulfonyl]benzamide | 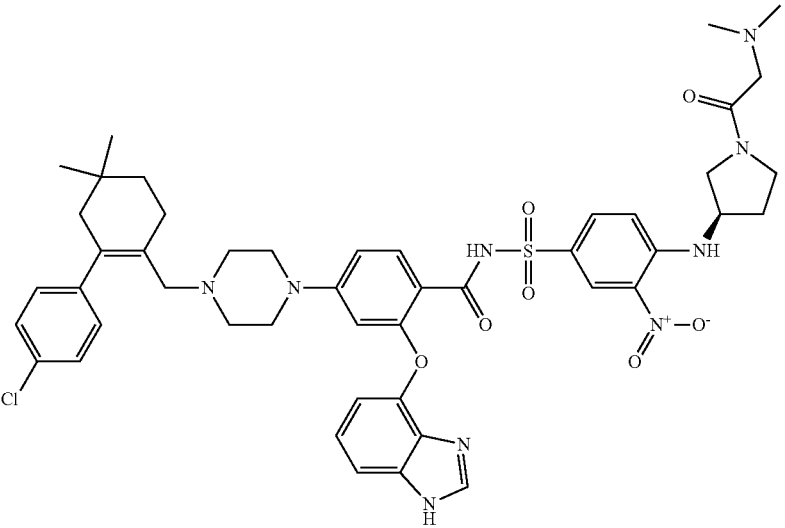 [SMILES: CN(C)CC(=O)N1CC[C@@H](Nc2ccc(S(=O)(=O)NC(=O)c3ccc(N4CCN(CC5=C(c6ccc(Cl)cc6)CC(C)(C)CC5)CC4)cc3Oc3cccc4[nH]cnc34)cc2[N+](=O)[O-])C1] |
| 2-(1H-benzimidazol-4-yloxy)-4-(4-{[2-(4-chlorophenyl)-4,4-dimethylcyclohex-1-en-1-yl]methyl}piperazin-1-yl)-N-{[4-({[4-(cyanomethyl)morpholin-2-yl]methyl}amino)-3-nitrophenyl]sulfonyl}benzamide | 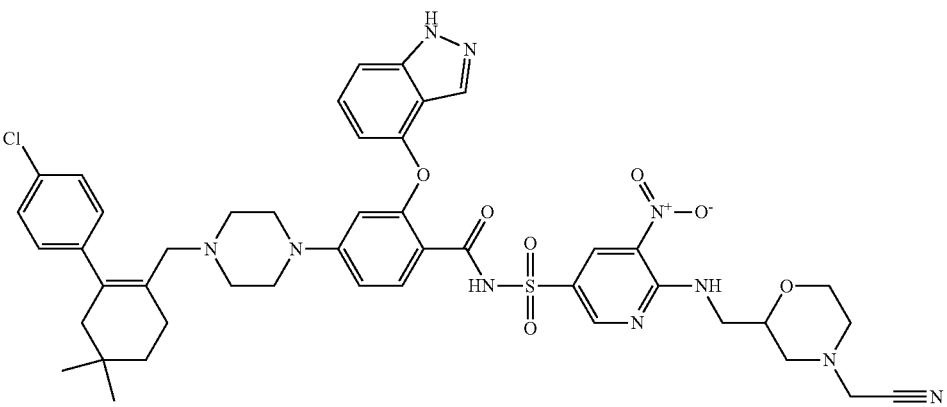 [SMILES: CC1(C)CCC(CN2CCN(c3ccc(C(=O)NS(=O)(=O)c4cnc(NCC5CN(CC#N)CCO5)c([N+](=O)[O-])c4)c(Oc4cccc5[nH]ncc45)c3)CC2)=C(c2ccc(Cl)cc2)C1] |
| 2-(1H-benzimidazol-4-yloxy)-4-(4-{[2-(4-chlorophenyl)-4,4-dimethylcyclohex-1-en-1-yl]methyl}piperazin-1-yl)-N-[(4-{[(4-cyclopropyl-morpholin-2-yl)methyl]amino}-3-nitrophenyl)sulfonyl]benzamide | 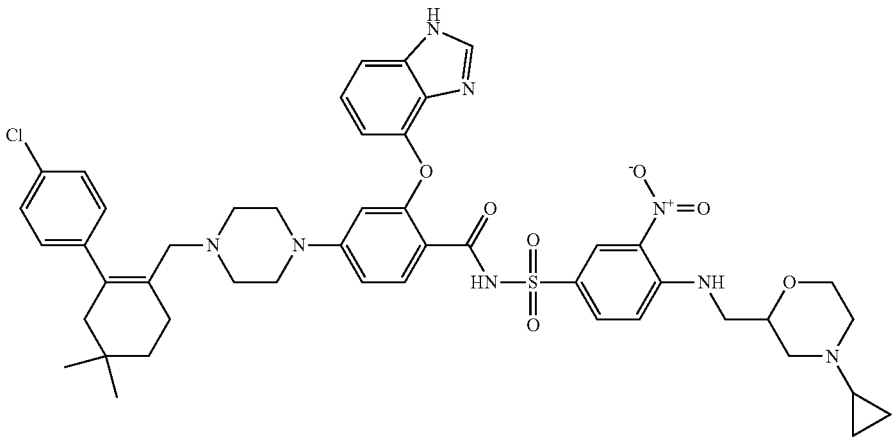 |

-continued

| Name | Structure |
|---|---|
| 2-(1H-benzimidazol-4-yloxy)-4-(4-{[2-(4-chlorophenyl)-4,4-dimethylcyclohex-1-en-1-yl]methyl}piperazin-1-yl)-N-[(3-nitro-4-{[(4-oxetan-3-ylmorpholin-2-yl)methyl]amino}phenyl)sulfonyl]benzamide | 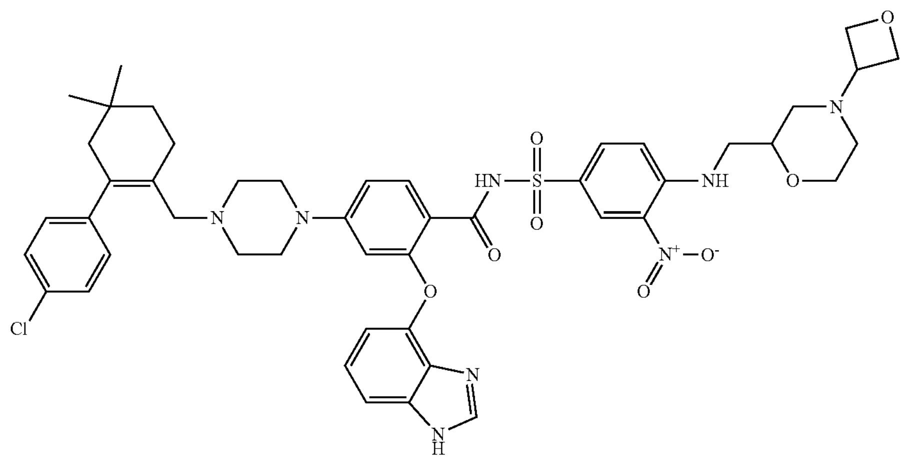 [SMILES: CC1(C)CCC(CN2CCN(c3ccc(C(=O)NS(=O)(=O)c4ccc(NCC5CN(C6COC6)CCO5)c([N+](=O)[O-])c4)c(Oc4cccc5[nH]cnc45)c3)CC2)=C(c2ccc(Cl)cc2)C1] |
| N-{[5-chloro-6-({(3R)-1-[2-fluoro-1-(fluoromethyl)ethyl]pyrrolidin-3-yl}oxy)pyridin-3-yl]sulfonyl}-4-(4-{[2-(4-chlorophenyl)-4,4-dimethylcyclohex-1-en-1-yl]methyl}piperazin-1-yl)-2-(1H-indazol-4-yloxy)benzamide | 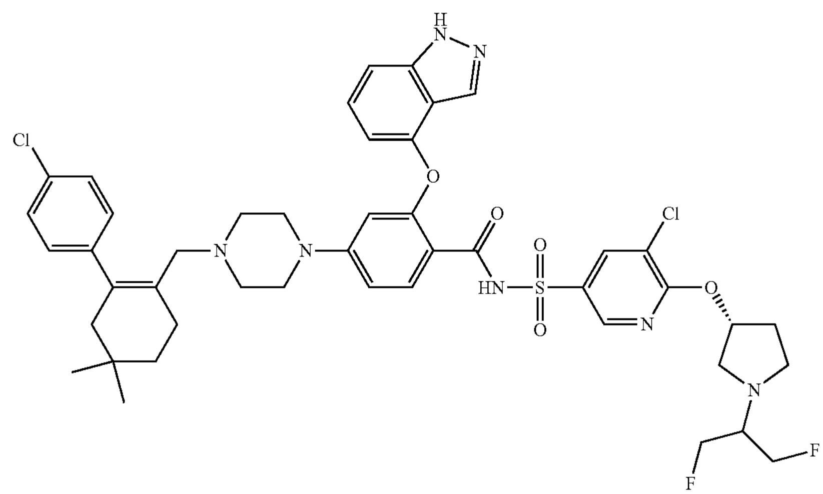 [SMILES: CC1(C)CCC(CN2CCN(c3ccc(C(=O)NS(=O)(=O)c4cnc(O[C@@H]5CCN(C(CF)CF)C5)c(Cl)c4)c(Oc4cccc5[nH]ncc45)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-{[4-({(3R)-1-[2-fluoro-1-(fluoromethyl)ethyl]pyrrolidin-3-yl}amino)-3-nitrophenyl]sulfonyl}-2-(1H-indazol-4-yloxy)benzamide | |

-continued

| Name | Structure |
|---|---|
| 4-(4-{[2-(4-chlorophenyl)-4,4-dimethylcyclohex-1-en-1-yl]methyl}piperazin-1-yl)-N-({4-[(1-cyclopropylpiperidin-4-yl)amino]-3-nitrophenyl}sulfonyl)-2-(1H-indazol-4-yloxy)benzamide | |
| 2-(1H-benzimidazol-4-yloxy)-4-(4-{[2-(4-chlorophenyl)-4,4-dimethylcyclohex-1-en-1-yl]methyl}piperazin-1-yl)-N-{[4-({[(2R)-4-(N,N-dimethylglycyl)morpholin-2-yl]methyl}amino)-3-nitrophenyl]sulfonyl}benzamide | 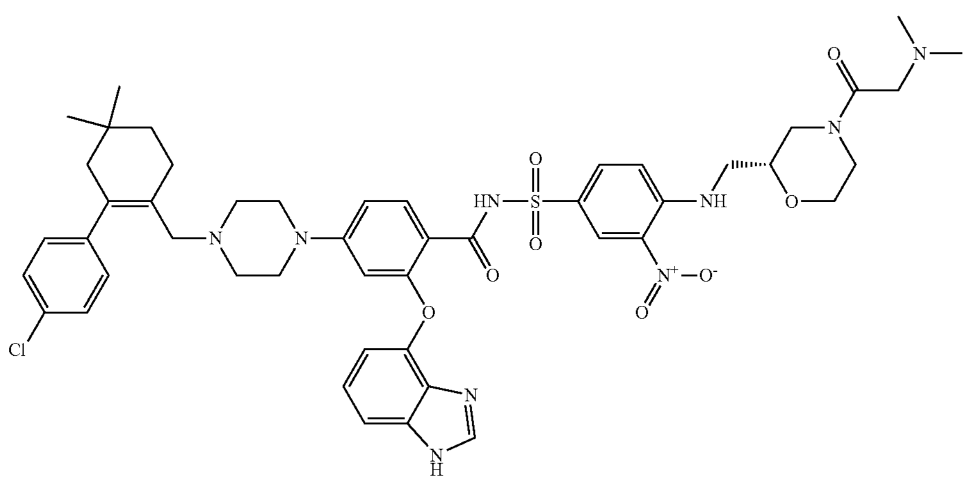 [SMILES: CN(C)CC(=O)N1CCO[C@H](CNc2ccc(S(=O)(=O)NC(=O)c3ccc(N4CCN(CC5=C(c6ccc(Cl)cc6)CC(C)(C)CC5)CC4)cc3Oc3cccc4[nH]cnc34)cc2[N+](=O)[O-])C1] |
| 2-(1H-benzimidazol-4-yloxy)-4-(4-{[2-(4-chlorophenyl)-4,4-dimethylcyclohex-1-en-1-yl]methyl}piperazin-1-yl)-N-{14-({[(2S)-4-(N,N-dimethylglycyl)morpholin-2-yl]methyl}amino)-3-nitrophenyl]sulfonyl]benzamide | 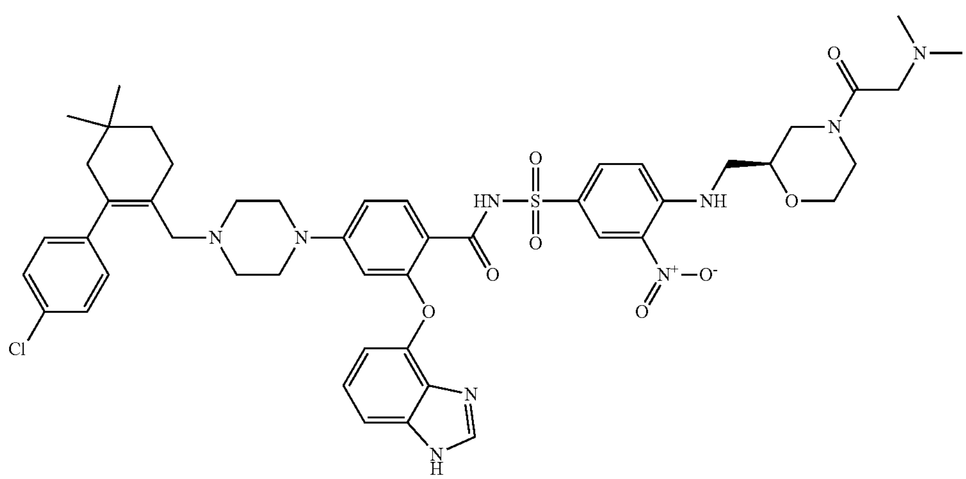 [SMILES: CN(C)CC(=O)N1CCO[C@@H](CNc2ccc(S(=O)(=O)NC(=O)c3ccc(N4CCN(CC5=C(c6ccc(Cl)cc6)CC(C)(C)CC5)CC4)cc3Oc3cccc4[nH]cnc34)cc2[N+](=O)[O-])C1] |

| Name | Structure |
|---|---|
| 2-(1H-benzimidazol-4-yloxy)-4-(4-{[2-(4-chlorophenyl)-4,4-dimethylcyclohex-1-en-1-yl]methyl}piperazin-1-yl)-N-({3-nitro-4-[(tetrahydrofuran-3-ylmethyl)amino]phenyl}sulfonyl)benzamide | |
| Trans-2-(1H-benzimidazol-4-yloxy)-4-(4-{[2-(4-chlorophenyl)-4,4-dimethylcyclohex-1-en-1-yl]methyl}piperazin-1-yl)-N-[(4-{[(4-methoxycyclohexyl)methyl]amino}-3-nitrophenyl)sulfonyl]benzamide | |
| 2-(1H-benzimidazol-4-yloxy)-4-(4-{[2-(4-chlorophenyl)-4,4-dimethylcyclohex-1-en-1-yl]methyl}piperazin-1-yl)-N-[(4-{[(4-fluorotetrahydro-2H-pyran-4-yl)methyl]amino}-3-nitrophenyl)sulfonyl]benzamide | |
| 2-(1H-benzimidazol-4-yloxy)-4-(4-{[2-(4-chlorophenyl)-4,4-dimethylcyclohex-1-en-1-yl]methyl}piperazin-1-yl)-N-({5-fluoro-6-[(4-fluorotetrahydro-2H-pyran-4-yl)methoxy]pyridin-3-yl}sulfonyl)benzamide | |

| Name | Structure |
|---|---|
| 2-(1H-benzimidazol-4-yloxy)-N-({5-chloro-6-[(4-fluorotetrahydro-2H-pyran-4-yl)methoxy]pyridin-3-yl}sulfonyl)-4-(4-{[2-(4-chlorophenyl)-4,4-dimethylcyclohex-1-en-1-yl]methyl}piperazin-1-yl)benzamide | |
| N-{[5-chloro-6-({(3R)-1-[2-fluoro-1-(fluoromethyl)ethyl]pyrrolidin-3-yl}methoxy)pyridin-3-yl]sulfonyl}-4-(4-{[2-(4-chlorophenyl)-4,4-dimethylcyclohex-1-en-1-yl]methyl}piperazin-1-yl)-2-(1H-indazol-4-yloxy)benzamide | |
| N-[(5-chloro-6-{[(3R)-1-(2,2-difluoroethyl)pyrrolidin-3-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-indazol-4-yloxy)benzamide | |

| Name | Structure |
|---|---|
| Trans-4-(4-{[2-(4-chlorophenyl)-4,4-dimethylcyclohex-1-en-1-yl]methyl}piperazin-1-yl)-2-(1H-indazol-4-yloxy)-N-[(4-{[(4-methoxycyclohexyl)methyl]amino}-3-nitrophenyl)sulfonyl]benzamide | 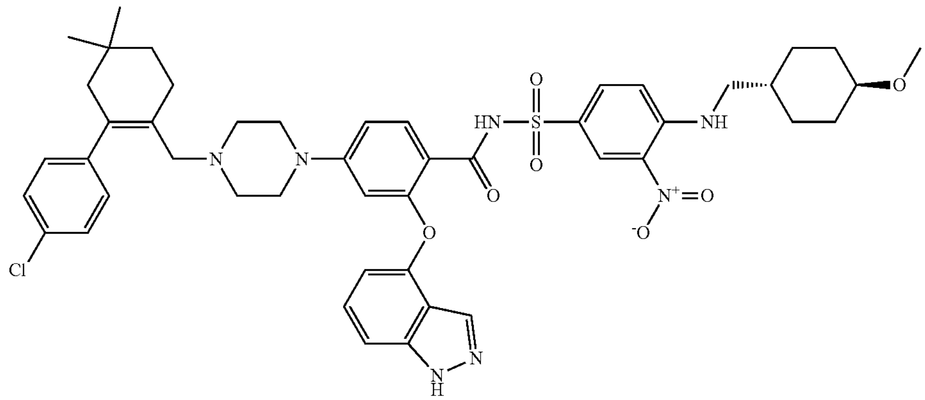 |
| 4-(4-{[2-(4-chloro-phenyl)-4,4-dimethylcyclohex-1-en-1-yl]methyl]piperazin-1-yl)-N-{[4-(1,4-dioxan-2-ylmethoxy)-3-nitrophenyl]sulfonyl}-2-(1H-indazol-4-yloxy)benzamide | 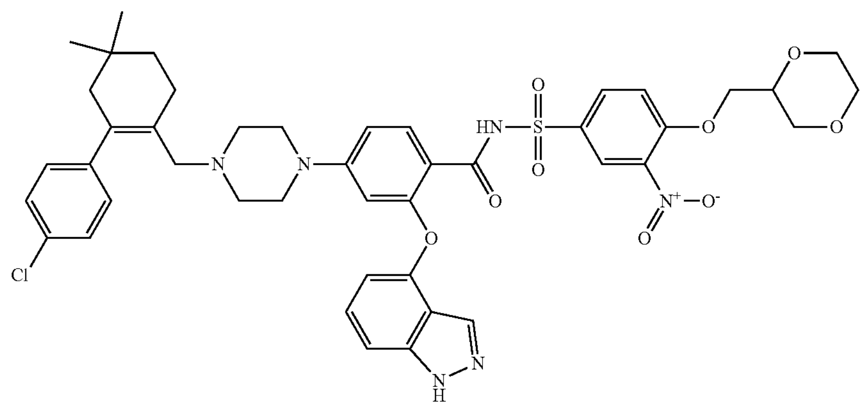 [SMILES: CC1(C)CCC(CN2CCN(c3ccc(C(=O)NS(=O)(=O)c4ccc(OCC5COCCO5)c([N+](=O)[O-])c4)c(Oc4cccc5[nH]ncc45)c3)CC2)=C(c2ccc(Cl)cc2)C1] |
| N-({5-chloro-6-[(1-cyclopropylpiperidin-4-yl)amino]pyridin-3-yl}sulfonyl)-4-(4-{[2-(4-chlorophenyl)-4,4-dimethylcyclohex-1-en-1-yl]methyl]piperazin-1-yl)-2-(1H-indazol-4-yloxy)benzamide | 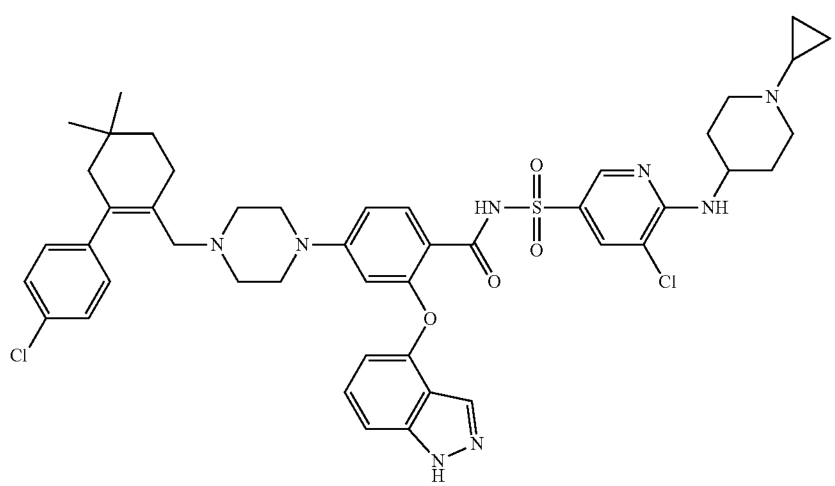 [SMILES: CC1(C)CCC(CN2CCN(c3ccc(C(=O)NS(=O)(=O)c4cnc(NC5CCN(C6CC6)CC5)c(Cl)c4)c(Oc4cccc5[nH]ncc45)c3)CC2)=C(c2ccc(Cl)cc2)C1] |

| Name | Structure |
|---|---|
| 2-(1H-benzimidazol-4-yloxy)-N-({5-chloro-6-[(1-cyclopropylpiperidin-4-yl)amino]pyridin-3-yl}sulfonyl)-4-(4-{[2-(4-chlorophenyl)-4,4-dimethylcyclohex-1-en-1-yl]methyl}piperazin-1-yl)benzamide | 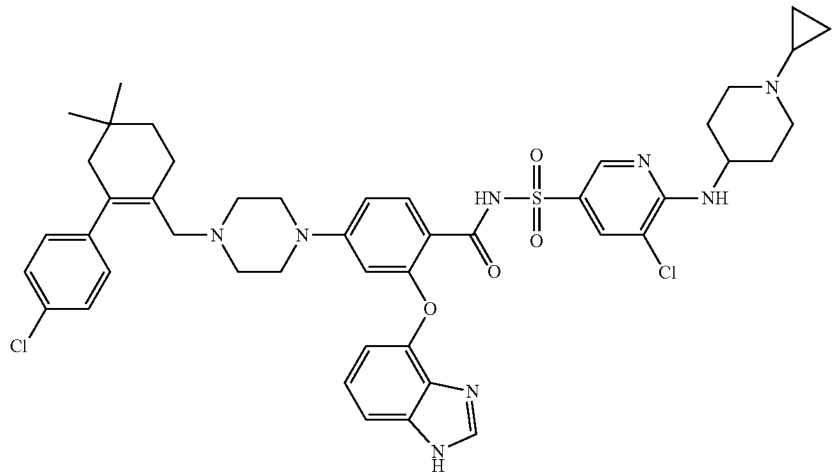 [SMILES: CC1(C)CCC(CN2CCN(c3ccc(C(=O)NS(=O)(=O)c4cnc(NC5CCN(C6CC6)CC5)c(Cl)c4)c(Oc4cccc5[nH]cnc45)c3)CC2)=C(c2ccc(Cl)cc2)C1] |
| 2-(1H-benzimidazol-4-yloxy)-4-(4-{[2-(4-chlorophenyl)-4,4-dimethylcyclohex-1-en-1-yl]methyl}piperazin-1-yl)-N-({4-[(1,4-dioxan-2-ylmethyl)amino]-3-nitrophenyl}sulfonyl)benzamide | 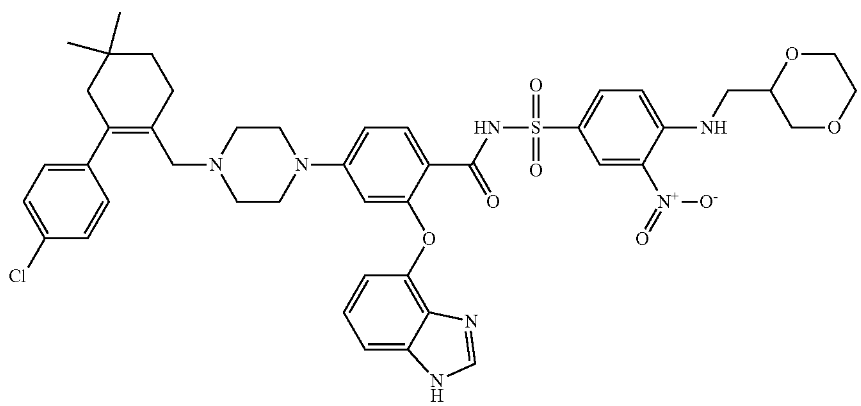 [SMILES: CC1(C)CCC(CN2CCN(c3ccc(C(=O)NS(=O)(=O)c4ccc(NCC5COCCO5)c([N+](=O)[O-])c4)c(Oc4cccc5[nH]cnc45)c3)CC2)=C(c2ccc(Cl)cc2)C1] |
| 2-(1H-benzimidazol-4-yloxy)-4-(4-{[2-(4-chlorophenyl)-4,4-dimethylcyclohex-1-en-1-yl]methyl}piperazin-1-yl)-N-({4-[(1-cyclopropylpiperidin-4-yl)amino]-3-nitrophenyl}sulfonyl)benzamide | 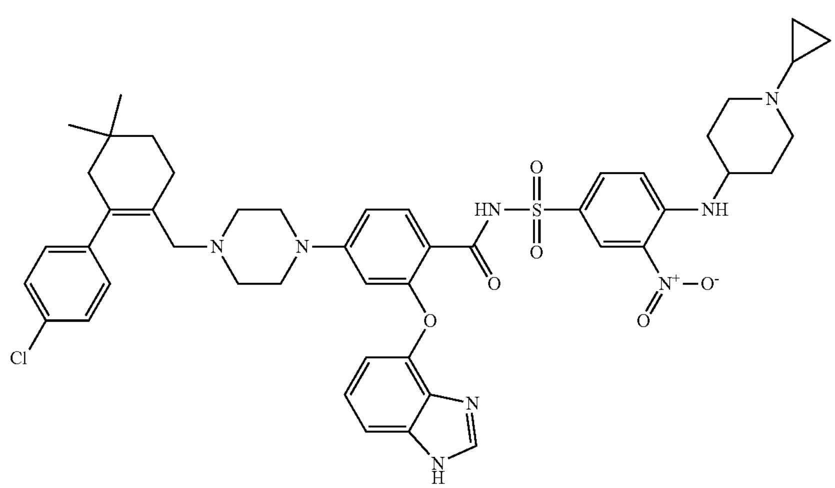 [SMILES: CC1(C)CCC(CN2CCN(c3ccc(C(=O)NS(=O)(=O)c4ccc(NC5CCN(C6CC6)CC5)c([N+](=O)[O-])c4)c(Oc4cccc5[nH]cnc45)c3)CC2)=C(c2ccc(Cl)cc2)C1] |

-continued

| Name | Structure |
|---|---|
| Trans-2-(1H-benzimidazol-4-yloxy)-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)benzamide | |
| 2-(1H-benzimidazol-4-yloxy)-4-(4-{[2-(4-chlorophenyl)-4,4-dimethylcyelohex-1-en-1-yl]methyl}piperazin-1-yl)-N-({4-[(4-methylpiperazin-1-yl)amino]-3-nitrophenyl}sulfonyl)benzamide | 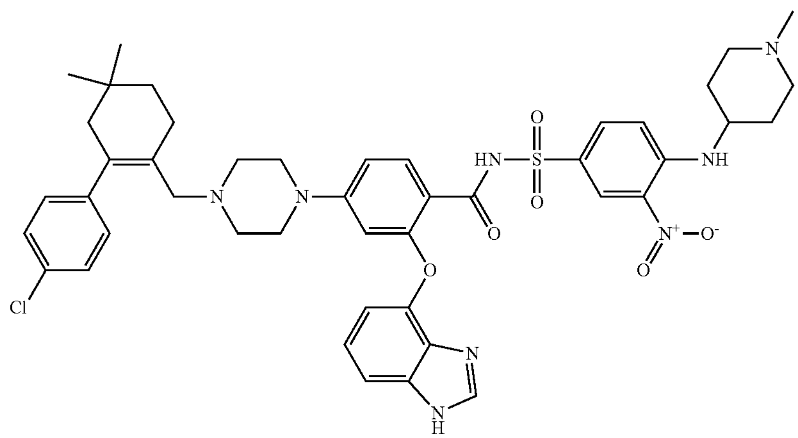 [SMILES: CN1CCC(Nc2ccc(S(=O)(=O)NC(=O)c3ccc(N4CCN(CC5=C(c6ccc(Cl)cc6)CC(C)(C)CC5)CC4)cc3Oc3cccc4[nH]cnc34)cc2[N+](=O)[O-])CC1] |
| 2-(1H-benzimidazol-4-yloxy)-4-(4-{[2-(4-chlorophenyl)-4,4-dimethylcyclohex-1-en-1-yl]methyl}piperazin-1-yl)-N-[(4-{[(1-methylpiperidin-4-yl)methyl]amino}-3-nitrophenyl)sulfonyl]benzamide | 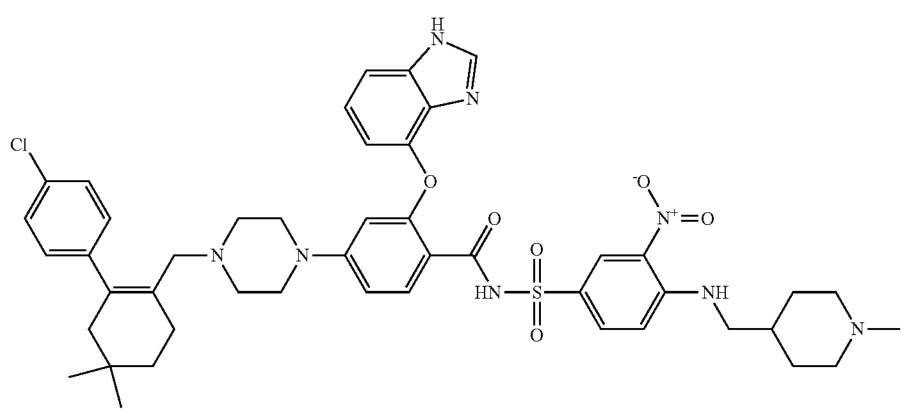 |

| Name | Structure |
|---|---|
| 2-(1H-benzimidazol-4-yloxy)-4-(4-{[2-(4-chlorophenyl)-4,4-dimethylcyclohex-1-en-1-yl]methyl}piperazin-1-yl)-N-({4-[({(2R)-4-[2-(2-methoxyethoxy)ethyl]morpholin-2-yl}methyl)amino]-3-nitrophenyl}sulfonyl)benzamide | 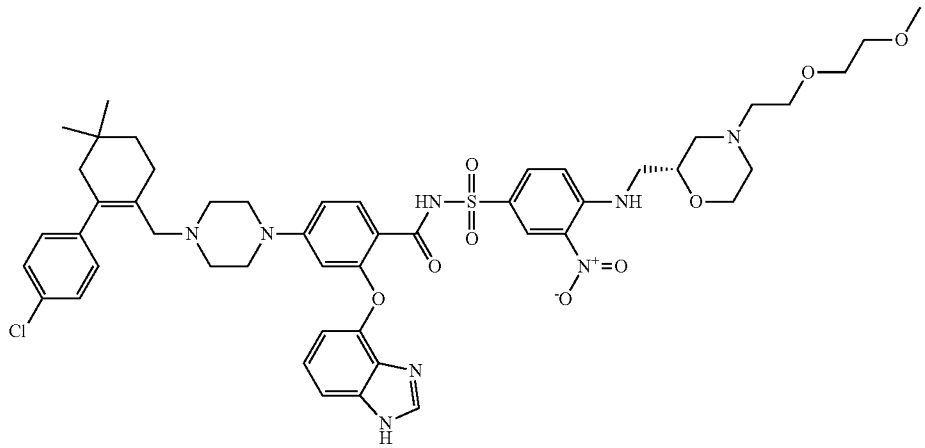 |
| 2-(1H-benzimidazol-4-yloxy)-4-(4-{[2-(4-chlorophenyl)-4,4-dimethylcyclohex-1-en-1-yl]methyl}piperazin-1-yl)-N-[(4-{[(4,4-difluorocyclohexyl)methyl]amino}-3-nitrophenyl)sulfonyl]benzamide | 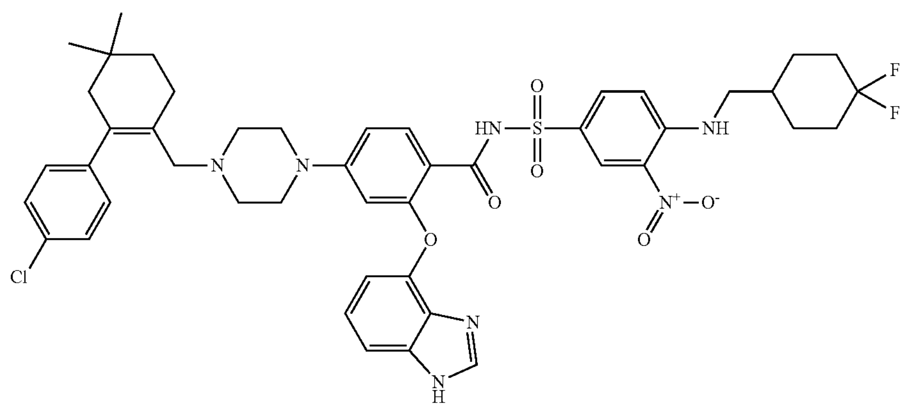 [SMILES: CC1(C)CCC(CN2CCN(c3ccc(C(=O)NS(=O)(=O)c4ccc(NCC5CCC(F)(F)CC5)c([N+](=O)[O-])c4)c(Oc4cccc5[nH]cnc45)c3)CC2)=C(c2ccc(Cl)cc2)C1] |
| N-[(4-{[(4-acetylmorpholin-2-yl)methyl]amino}-3-nitrophenyl)sulfonyl]-2-(1H-benzimidazol-4-yloxy)-4-(4-{[2-(4-chlorophenyl)-4,4-dimethylcyclohex-1-en-1-yl]methyl}piperazin-1-yl)benzamide | 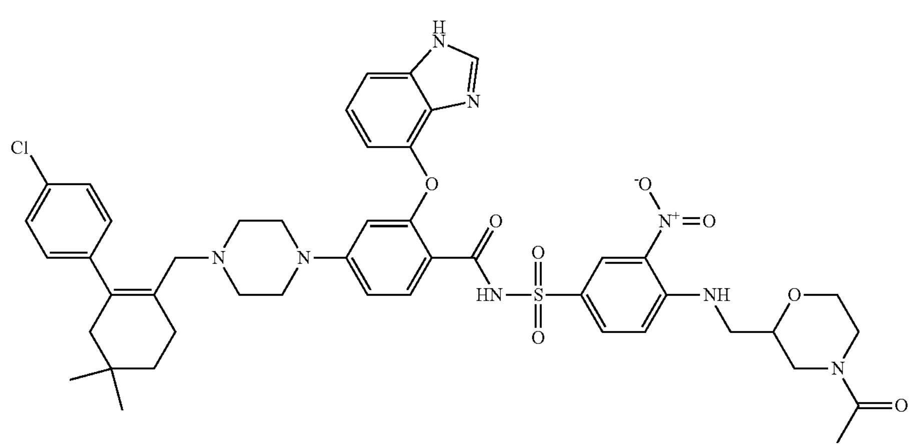 |

-continued

| Name | Structure |
|---|---|
| 2-(1H-benzimidazol-4-yloxy)-4-(4-{[2-(4-chlorophenyl)-4,4-dimethylcyclohex-1-en-1-yl]methyl}piperazin-1-yl)-N-{[4-({[4-(methylsulfonyl)morpholin-2-yl]methyl}amino)-3-nitrophenyl]sulfonyl}benzamide | |
| 4-(4-{[2-(4-chlorophenyl)-4,4-dimethylcyclohex-1-en-1-yl]methyl}piperazin-1-yl)-N-{16-({4-fluoro-1-[2-fluoro-1-(fluoromethyl)ethyl]piperidin-4-yl}methoxy)-5-(trifluoromethyl)pyridin-3-yl]sulfonyl}-2-(1H-indazol-4-yloxy)benzamide | |
| 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-phenoxybenzamide | |
| 4-(4-{[2-(4-chlorophenyl)-4,4-dimethylcyclohex-1-en-1-yl]methyl}piperazin-1-yl)-N-{[5-chloro-6-(2-tetrahydrofuran-2-ylethoxy)pyridin-3-yl]sulfonyl}-2-(1H-indazol-4-yloxy)benzamide | |

| Name | Structure |
|---|---|
| Trans-2-(1H-benzimidazol-4-yloxy)-4-(4-{[2-(4-chlorophenyl)-4,4-dimethylcyclohex-1-en-1-yl]methyl}piperazin-1-yl)-N-[(4-{[(4-cyanocyclohexyl)methyl]amino}-3-nitrophenyl)sulfonyl]benzamide | |
| 2-(1H-benzimidazol-4-yloxy)-N-({5-chloro-6-[(4,4-difluorocyclohexyl)methoxy]pyridin-3-yl}sulfonyl)-4-(4-{[2-(4-chlorophenyl)-4,4-dimethylcyclohex-1-en-1-yl]methyl}piperazin-1-yl)benzamide | |
| N-({3-chloro-4-[(4-fluorotetrahydro-2H pyran-4-yl)methoxy]phenyl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide | |

| Name | Structure |
|---|---|
| N-({5-chloro-6-[(4-fluorotetrahydro-2H pyran-4-yl)methoxy]pyridin-3-yl}sulfonyl)-4-(4-{[4-(4-chlorophenyl)-6,6-dimethyl-5,6-dihydro-2H-pyran-3-yl]methyl}piperazin-1-yl)-2-(1H-indazol-4-yloxy)benzamide | 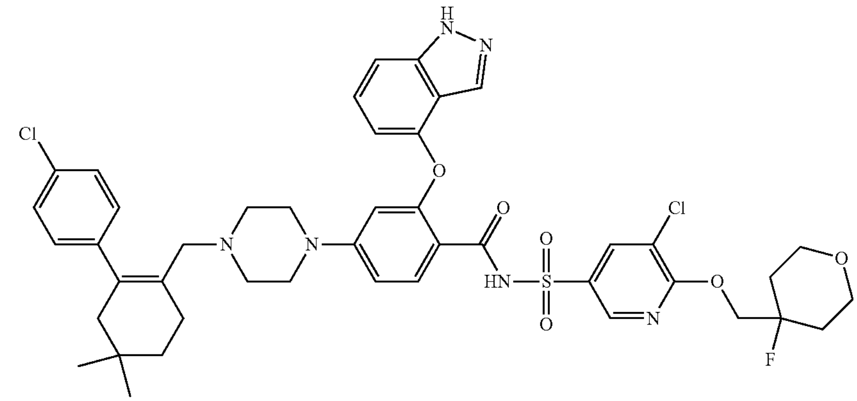 |
| 4-(4-{[2-(4-chloro-phenyl)-4,4-dimethylcyclohex-1-en-1-yl]methyl}piperazin-1-yl)-N-{[5-cyano-6-(2-tetrahydro-2H-pyran-4-ylethoxy)pyridin-3-yl]sulfonyl}-2-(1H-indazol-4-yloxy)benzamide | 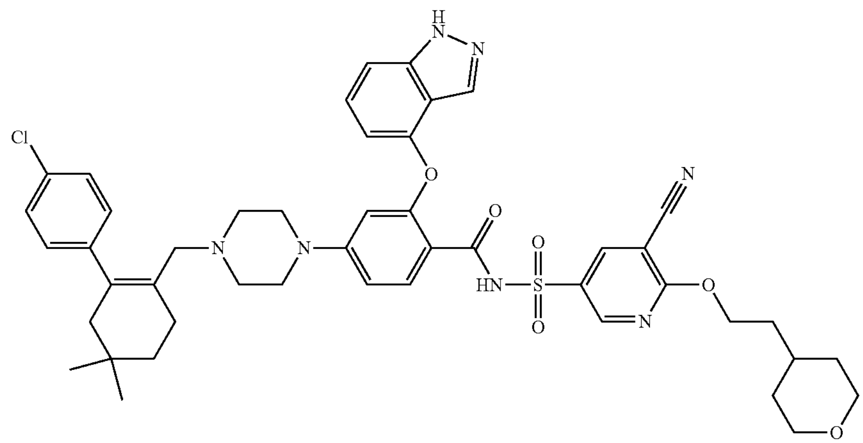 |
| 4-(4-{[2-(4-chloro-phenyl)-4,4-dimethylcyclohex-1-en-1-yl]methyl}piperazin-1-yl)-2-(1H-indol-5-yloxy)-N-[(4-{[(1R,5S)-8-methyl-8-azabicyclo[3.2.1]oct-3-yl]amino}-3-nitrophenyl)sulfonyl]benzamide | 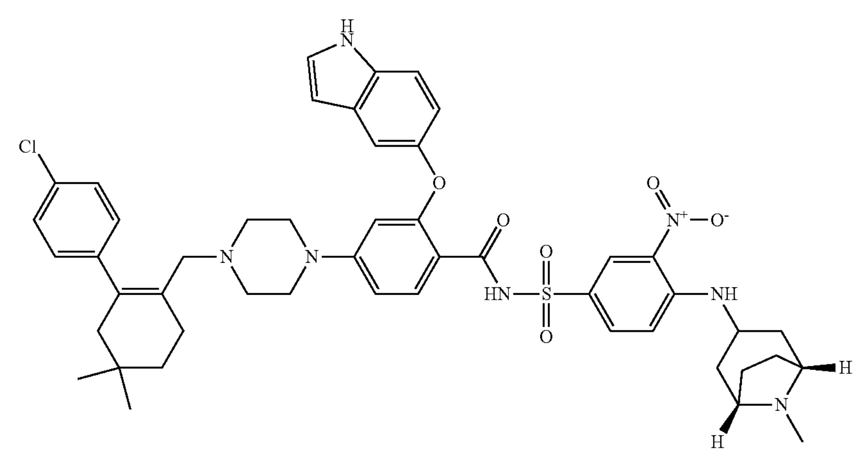 [SMILES: CN1[C@@H]2CC[C@H]1CC(Nc1ccc(S(=O)(=O)NC(=O)c3ccc(N4CCN(CC5=C(c6ccc(Cl)cc6)CC(C)(C)CC5)CC4)cc3Oc3ccc4[nH]ccc4c3)cc1[N+](=O)[O-])C2] |

| Name | Structure |
|---|---|
| N-({3-nitro-4-[(tetrahydro-2H-pyran-4-ylmethyl)amino]phenyl}sulfonyl)-2-phenoxy-4-(4-{(3-phenylpropanoyl)[(1S,2S,3S,5R)-2,6,6-trimethylbicyclo[3.1.1]hept-3-yl]amino}piperidin-1-yl)benzamide | |
| N-({4-[(3-morpholin-4-ylpropyl)amino]-3-nitrophenyl}sulfonyl)-2-phenoxy-4-(4-{(3-phenylpropanoyl)[(1S,2S,3S,5R)-2,6,6-trimethylbicyclo[3.1.1]hept-3-yl]amino}piperidin-1-yl)benzamide | 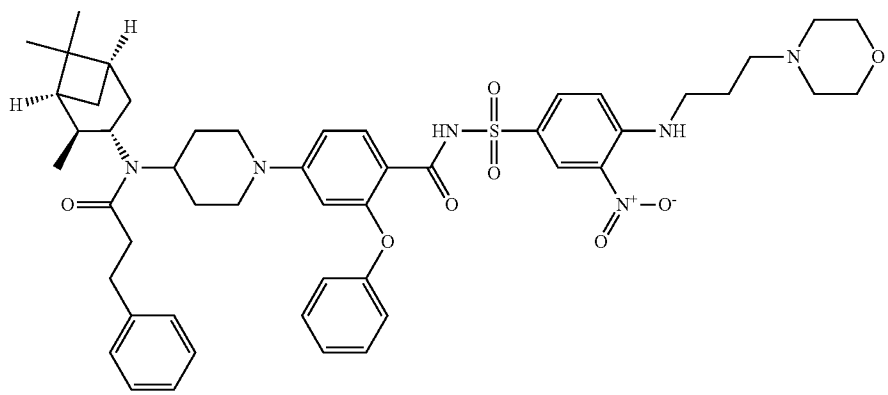 [SMILES: C[C@@H]1[C@@H](N(C(=O)CCc2ccccc2)C2CCN(c3ccc(C(=O)NS(=O)(=O)c4ccc(NCCCN5CCOCC5)c([N+](=O)[O-])c4)c(Oc4ccccc4)c3)CC2)C[C@H]2C[C@@H]1C2(C)C] |
| N-({3-nitro-4-[(tetrahydro-2H-pyran-4-ylmethyl)amino]phenyl}sulfonyl)-2-phenoxy-4-(4-{(3-phenylpropyl)[(1S,2S,3S,5R)-2,6,6-trimethylbicyclo[3.1.1]hept-3-yl]amino}piperidin-1-yl)benzamide | |
| N-({4-[(3-morpholin-4-ylpropyl)amino]-3-nitrophenyl}sulfonyl)-2-phenoxy-4-(4-{(3-phenylpropyl)[(1S,2S,3S,5R)-2,6,6-trimethylbicyclo[3.1.1]hept-3-yl]amino}piperidin-1-yl)benzamide | 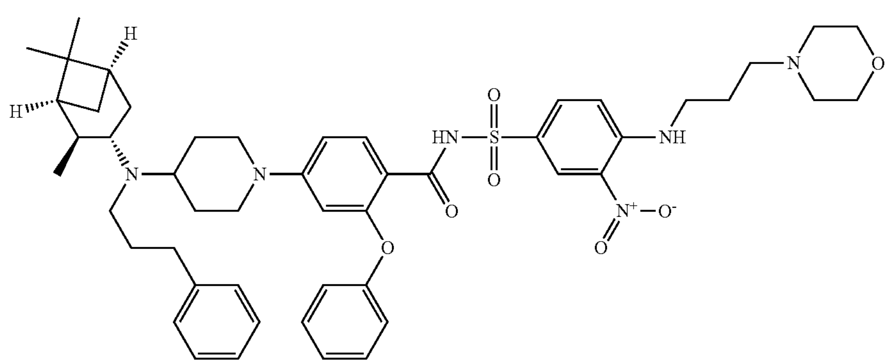 [SMILES: C[C@@H]1[C@@H](N(CCCc2ccccc2)C2CCN(c3ccc(C(=O)NS(=O)(=O)c4ccc(NCCCN5CCOCC5)c([N+](=O)[O-])c4)c(Oc4ccccc4)c3)CC2)C[C@H]2C[C@@H]1C2(C)C] |

| Name | Structure |
|---|---|
| 4-[4-(2-{[(1R,5S)-8-methyl-8-azabicyclo[3.2.1]oct-3-yl]amino}benzyl)piperazin-1-yl]-N-({4-[(3-morpholin-4-ylpropyl)amino]-3-nitrophenyl}sulfonyl)-2-phenoxybenzamide | 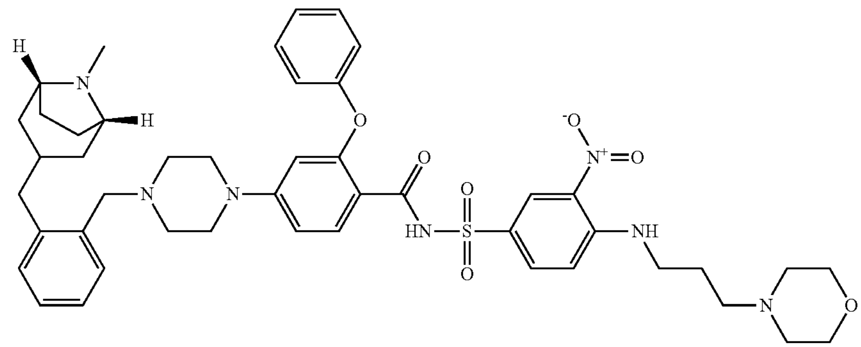 |
| 4-[4-(2-{[(1R,5S)-8-methyl-8-azabicyclo[3.2.1]oct-3-yl]amino}benzyl)piperazin-1-yl]-N-({3-nitro-4-[(tetrahydro-2H-pyran-4-ylmethyl)amino]phenyl}sulfonyl)-2-phenoxybenzamide | 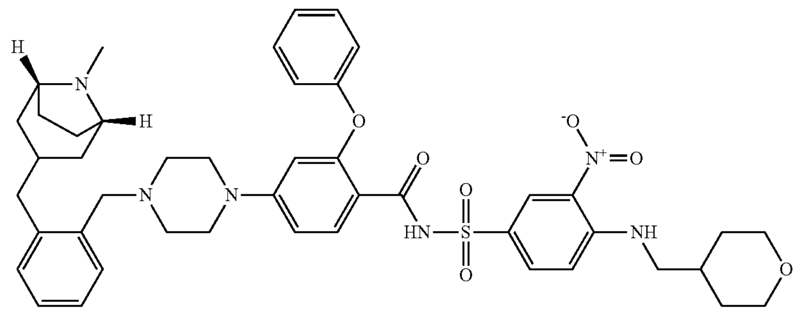 |
| 4-{4-[2-(3-azabicyclo[3.2.2]non-3-yl)benzyl]piperazin-1-yl}-N-({3-nitro-4-[(tetrahydro-2H-pyran-4-ylmethyl)amino]phenyl}sulfonyl)-2-phenoxybenzamide | |
| 4-{4-[2-(3-azabicyclo[3.2.2]non-3-yl)benzyl]piperazin-1-yl}-2-phenoxy-N-({4-[(tetrahydro-2H-pyran-4-ylmethyl)amino]-3-[(trifluoromethyl)sulfonyl]phenyl}sulfonyl)benzamide | 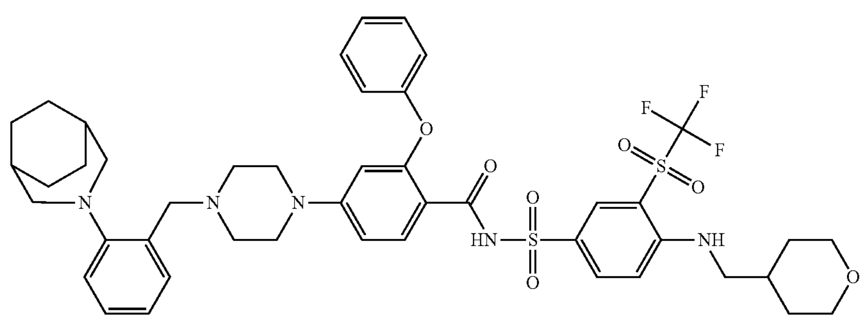 [SMILES: O=C(NS(=O)(=O)c1ccc(NCC2CCOCC2)c(S(=O)(=O)C(F)(F)F)c1)c1ccc(N2CCN(Cc3ccccc3N3CC4CCC(CC4)C3)CC2)cc1Oc1ccccc1] |
| 4-{4-[2-(3-azabicyclo[3.2.2]non-3-yl)benzyl]piperazin-1-yl}-2-phenoxy-N-({4-[(tetrahydro-2H-pyran-4-ylmethyl)amino]phenyl}sulfonyl)benzamide | 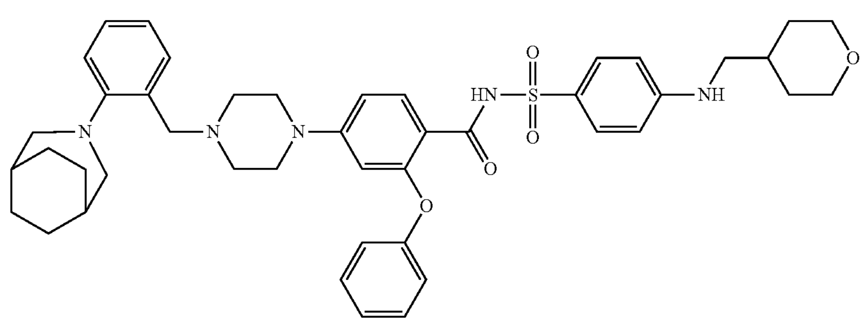 [SMILES: O=C(NS(=O)(=O)c1ccc(NCC2CCOCC2)cc1)c1ccc(N2CCN(Cc3ccccc3N3CC4CCC(CC4)C3)CC2)cc1Oc1ccccc1] |

-continued

| Name | Structure |
|---|---|
| 4-{4-[2-(3-azabicyclo[3.2.2]non-3-yl)benzyl]piperazin-1-yl}-N-({4-[(3-morpholin-4-ylpropyl)amino]-3-nitrophenyl}sulfonyl)-2-phenoxybenzamide | 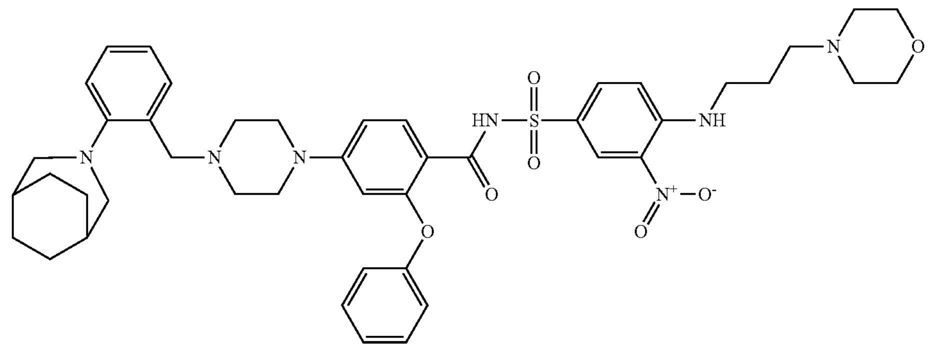 [SMILES: O=C(NS(=O)(=O)c1ccc(NCCCN2CCOCC2)c([N+](=O)[O-])c1)c1ccc(N2CCN(Cc3ccccc3N3CC4CCC(CC4)C3)CC2)cc1Oc1ccccc1] |
| 4-(4-{2-[(4R,7S)-2,3,3a,4,7,7a-hexahydro-1H-4,7-methanoinden-5-yl]benzyl}piperazin-1-yl)-N-({3-nitro-4-[(tetrahydro-2H-pyran-4-ylmethyl)amino]phenyl}sulfonyl)-2-phenoxybenzamide | 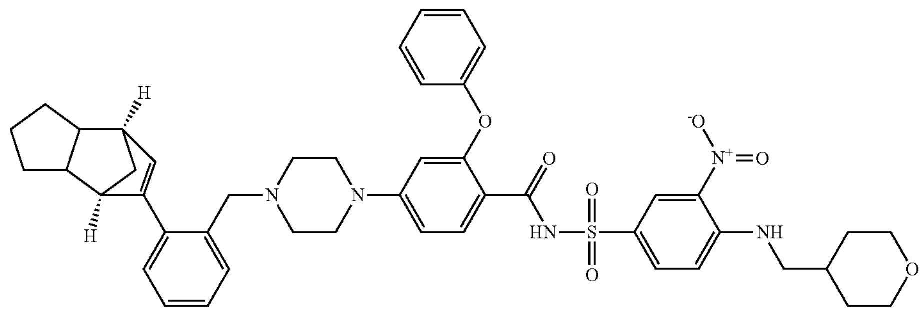 |
| 4-[4-(2-{5-[(1R,5S)-8-azabicyclo[3.2.1]oct-8-ylmethyl]thien-2-yl}benzyl)piperazin-1-yl]-N-({3-nitro-4-[(tetrahydro-2H-pyran-4-ylmethyl)amino]phenyl}sulfonyl)-2-phenoxybenzamide | 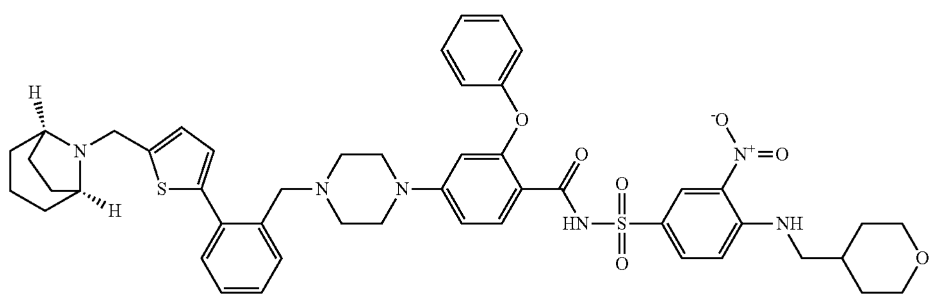 |
| 4-[4-(2-{5-[(1R,5S)-8-azabicyclo[3.2.1]oct-8-ylmethyl]thien-2-yl}benzylidene)piperidin-1-yl]-N-({3-nitro-4-[(tetrahydro-2H-pyran-4-ylmethyl)amino]phenyl}sulfonyl)-2-phenoxybenzamide | 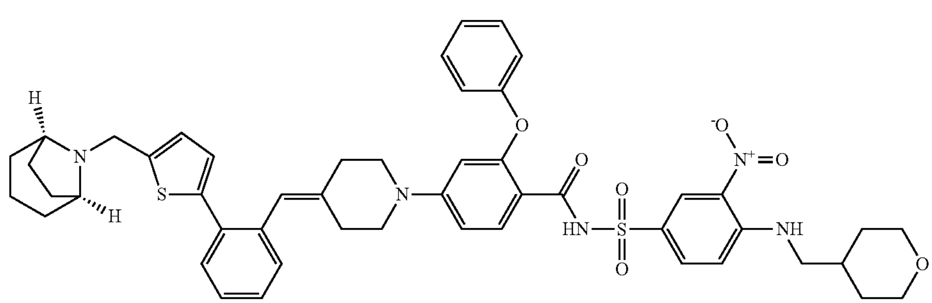 |

-continued

| Name | Structure |
|---|---|
| 4-[4-(3-{5-[(1R,5S)-8-azabicyclo[3.2.1]oct-8-ylmethyl]thien-2-yl}benzyl)piperazin-1-yl]-N-({3-nitro-4-[(tetrahydro-2H-pyran-4-ylmethyl)amino]phenyl}sulfonyl)-2-phenoxybenzamide | 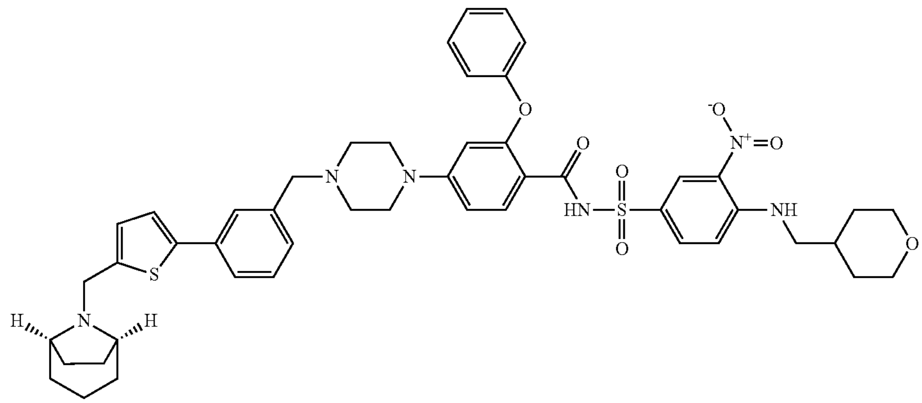 |
| N-({5-chloro-6-[(4,4-difluorocyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide | 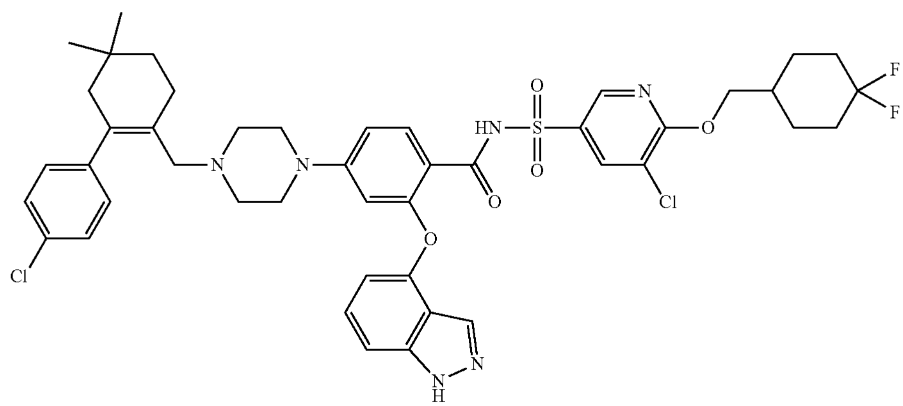 [SMILES: CC1(C)CCC(CN2CCN(c3ccc(C(=O)NS(=O)(=O)c4cnc(OCC5CCC(F)(F)CC5)c(Cl)c4)c(Oc4cccc5[nH]ncc45)c3)CC2)=C(c2ccc(Cl)cc2)C1] |
| N-({6-[(trans-4-carbamoylcyclohexyl)methoxy]-5-chloropyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide | 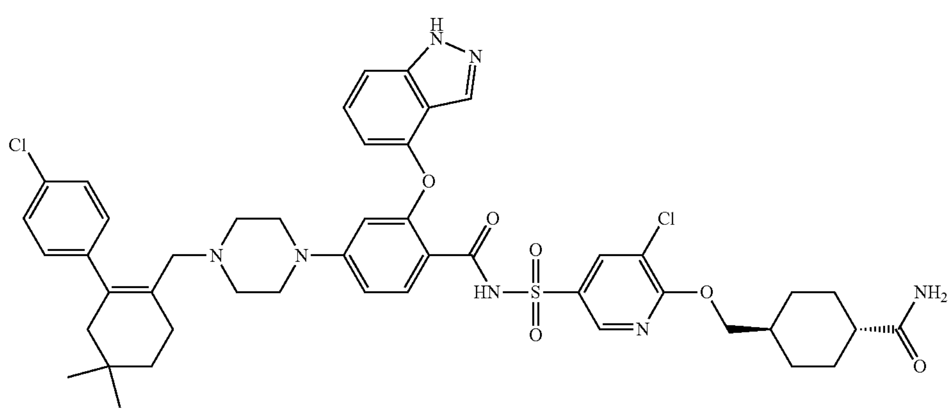 [SMILES: CC1(C)CCC(CN2CCN(c3ccc(C(=O)NS(=O)(=O)c4cnc(OC[C@H]5CC[C@H](C(N)=O)CC5)c(Cl)c4)c(Oc4cccc5[nH]ncc45)c3)CC2)=C(c2ccc(Cl)cc2)C1] |

| Name | Structure |
|---|---|
| 4-(4-{[2-(4-chloro-phenyl)-4,4-dimethylcyclohex-1-en-1-yl]methyl}piperazin-1-yl)-N-[(4-{[(trans-4-cyanocyclohexyl)methyl]amino}-3-nitrophenyl)sulfonyl]-2-(1H-indazol-4-yloxy)benzamide | 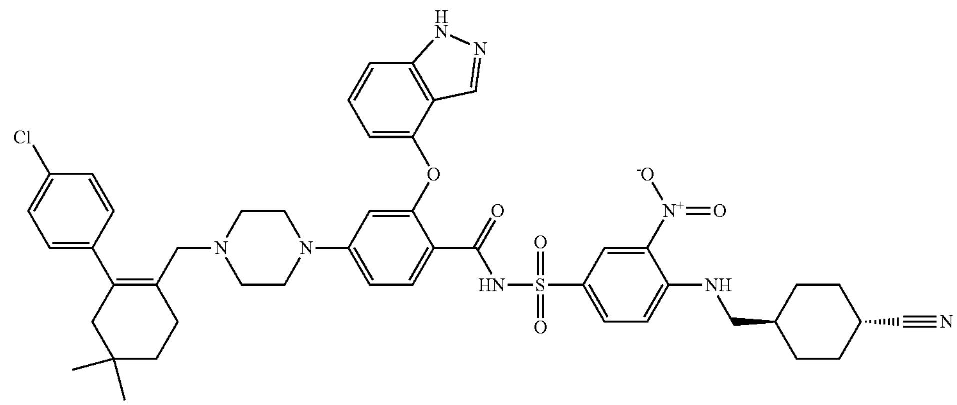 |
| N-({5-chloro-6-[2-(1H-imidazol-1-yl)ethoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide | 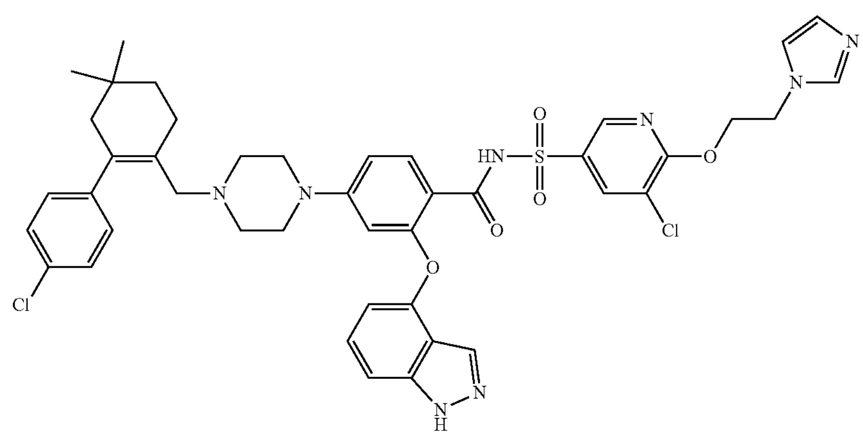 [SMILES: CC1(C)CCC(CN2CCN(c3ccc(C(=O)NS(=O)(=O)c4cnc(OCCn5ccnc5)c(Cl)c4)c(Oc4cccc5[nH]ncc45)c3)CC2)=C(c2ccc(Cl)cc2)C1] |
| N-({5-chloro-6-[(1-methyl-1H-imidazol-5-yl)methoxy]pyridin-3-yl}sulfonyl)-4-(4-{[2-(4-chloro-phenyl)-4,4-dimethylcyclohex-1-en-1-yl]methyl}piperazin-1-yl)-2-(1H-indazol-4-yloxy)benzamide | 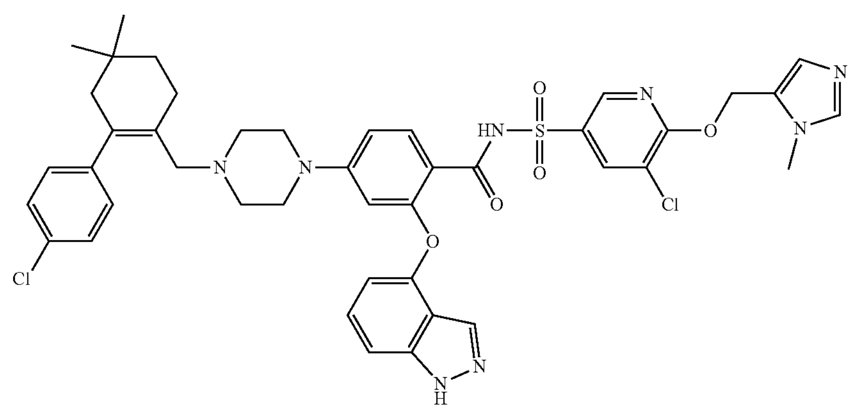 [SMILES: Cn1cncc1COc1ncc(S(=O)(=O)NC(=O)c2ccc(N3CCN(CC4=C(c5ccc(Cl)cc5)CC(C)(C)CC4)CC3)cc2Oc2cccc3[nH]ncc23)cc1Cl] |

| Name | Structure |
|---|---|
| 4-(4-{[2-(4-chlorophenyl)-4,4-dimethylcyclohex-1-en-1-yl]methyl}piperazin-1-yl)-N-{[5-fluoro-6-(tetrahydro-2H-pyran-4-ylmethoxy)pyridin-3-yl]sulfonyl}-2-(1H-indazol-4-yloxy)benzamide | |
| N-{[5-chloro-6-(1,4-dioxan-2-ylmethoxy)pyridin-3-yl]sulfonyl}-4-(4-{[2-(4-chlorophenyl)-4,4-dimethylcyclohex-1-en-1-yl]methyl}piperazin-1-yl)-2-(1H-indazol-4-yloxy)benzamide | 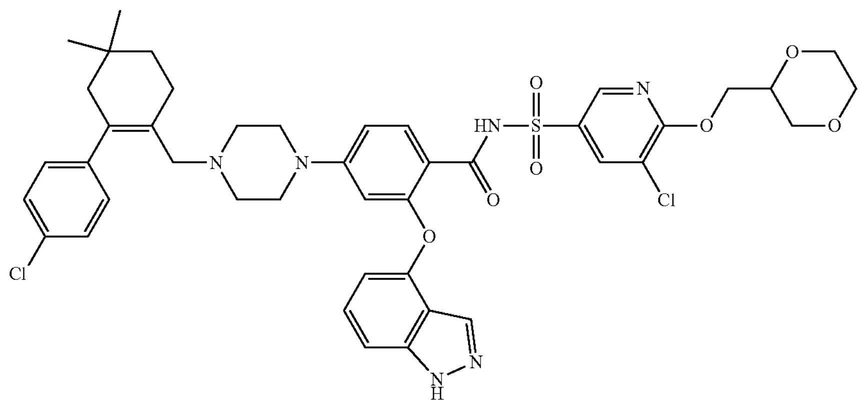 [SMILES: CC1(C)CCC(CN2CCN(c3ccc(C(=O)NS(=O)(=O)c4cnc(OCC5COCCO5)c(Cl)c4)c(Oc4cccc5[nH]ncc45)c3)CC2)=C(c2ccc(Cl)cc2)C1] |
| N-({5-chloro-6-[(4,4-difluoro-1-hydroxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide | 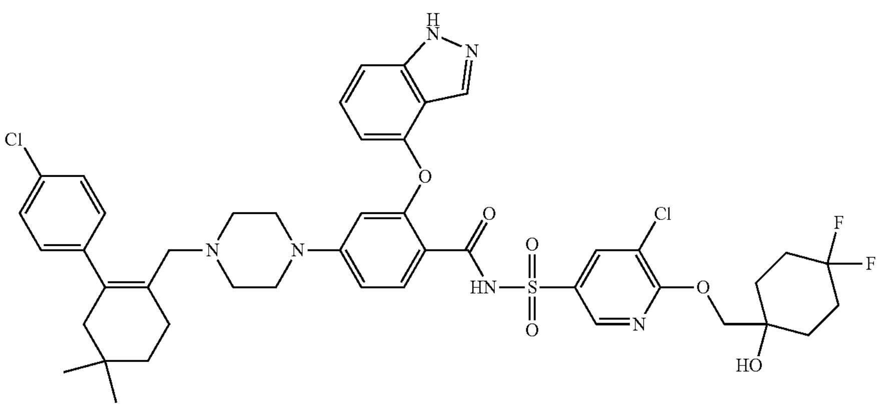 [SMILES: CC1(C)CCC(CN2CCN(c3ccc(C(=O)NS(=O)(=O)c4cnc(OCC5(O)CCC(F)(F)CC5)c(Cl)c4)c(Oc4cccc5[nH]ncc45)c3)CC2)=C(c2ccc(Cl)cc2)C1] |
| N-({5-chloro-6-[(2,2-difluorocyclopropyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide | |

| Name | Structure |
|---|---|
| N-({5-chloro-6-[(trans-4-cyanocyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide | 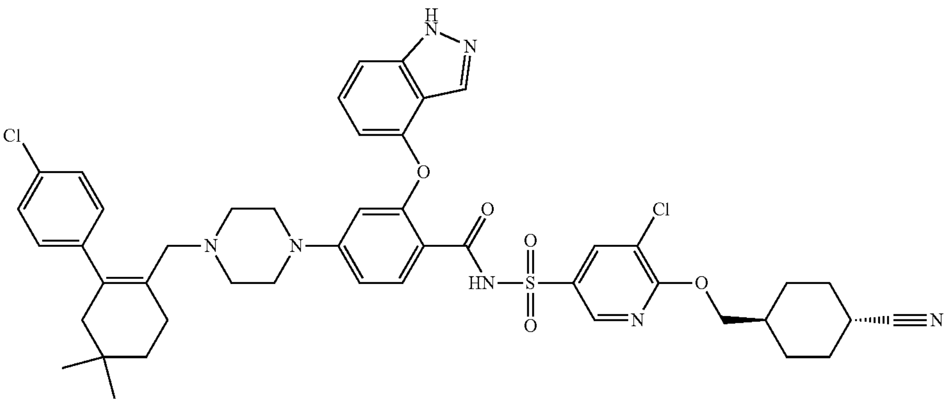 [SMILES: CC1(C)CCC(CN2CCN(c3ccc(C(=O)NS(=O)(=O)c4cnc(OC[C@H]5CC[C@H](C#N)CC5)c(Cl)c4)c(Oc4cccc5[nH]ncc45)c3)CC2)=C(c2ccc(Cl)cc2)C1] |
| N-({5-chloro-6-[(cis-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide | 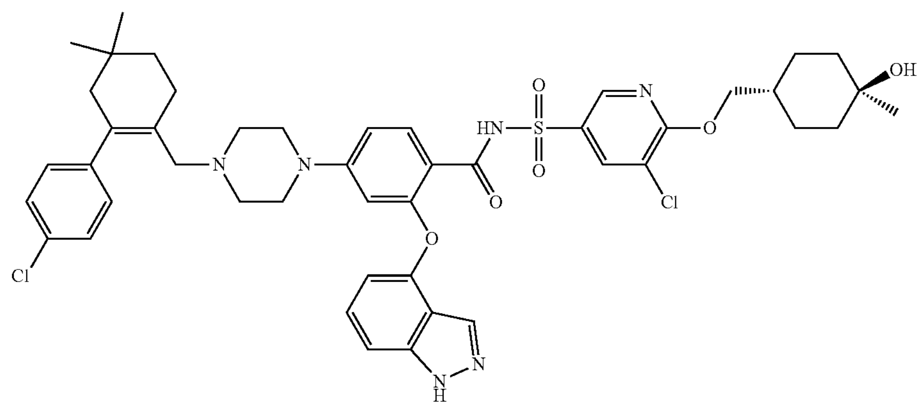 [SMILES: CC1(C)CCC(CN2CCN(c3ccc(C(=O)NS(=O)(=O)c4cnc(OC[C@H]5CC[C@](C)(O)CC5)c(Cl)c4)c(Oc4cccc5[nH]ncc45)c3)CC2)=C(c2ccc(Cl)cc2)C1] |
| N-({5-chloro-6-[(trans-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide | |

| Name | Structure |
|---|---|
| N-({3-chloro-4-[(4-fluorotetrahydro-2H-pyran-4-yl)methoxy]phenyl}sulfonyl)-4-(4-{[4-(4-chlorophenyl)-6,6-dimethyl-5,6-dihydro-2H-pyran-3-yl]methyl}piperazin-1-yl)-2-(1H-indazol-4-yloxy)benzamide | 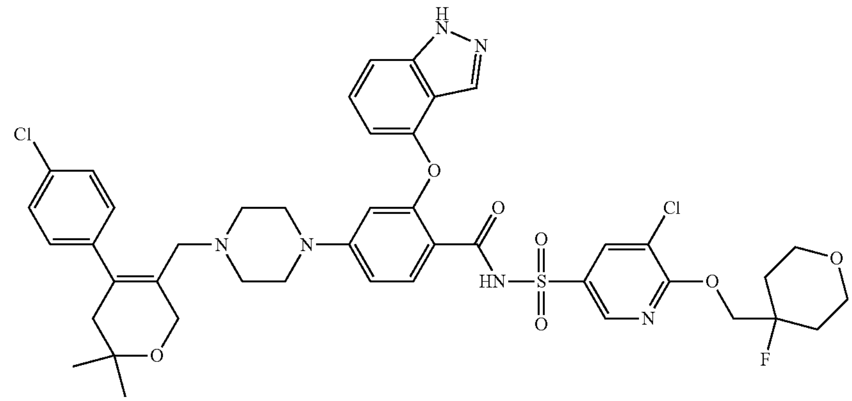 |
| 4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-(trifluoromethyl)phenyl}sulfonyl)-2-(1H-indazol-4-yloxy)benzamide | 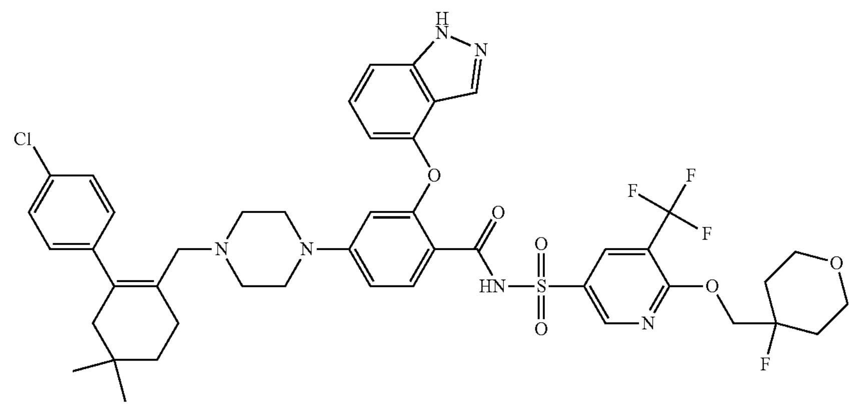 [SMILES: CC1(C)CCC(CN2CCN(c3ccc(C(=O)NS(=O)(=O)c4cnc(OCC5(F)CCOCC5)c(C(F)(F)F)c4)c(Oc4cccc5[nH]ncc45)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-{[3-chloro-4-(tetrahydro-2H-pyran-4-ylmethoxy)phenyl]sulfonyl}-2-(1H-indazol-4-yloxy)benzamide | 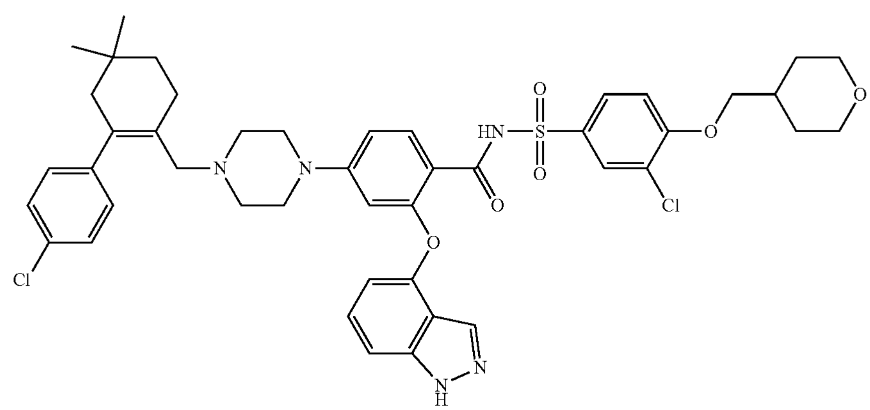 [SMILES: CC1(C)CCC(CN2CCN(c3ccc(C(=O)NS(=O)(=O)c4ccc(OCC5CCOCC5)c(Cl)c4)c(Oc4cccc5[nH]ncc45)c3)CC2)=C(c2ccc(Cl)cc2)C1] |
| 2-(1H-benzimidazol-4-yloxy)-N-({3-chloro-4-[(4-fluorotetrahydro-2H-pyran-4-yl)methoxy]phenyl}sulfonyl)-4-(4-{[2-(4-chlorophenyl)-4,4-dimethylcyclohex-1-en-1-yl]methyl}piperazin-1-yl)benzamide | 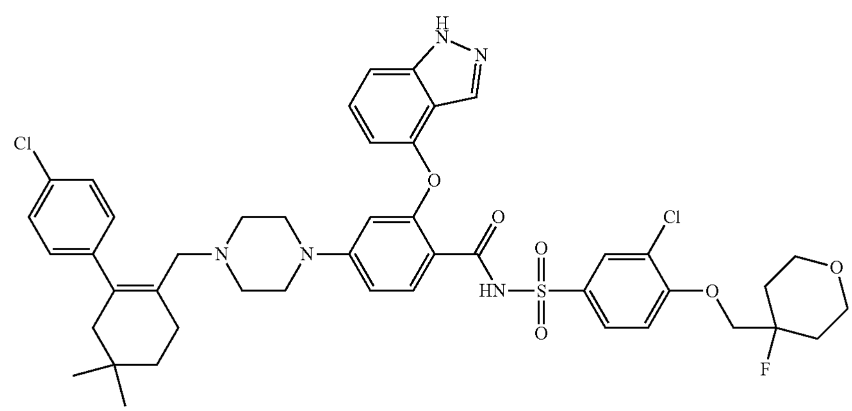 [SMILES: CC1(C)CCC(CN2CCN(c3ccc(C(=O)NS(=O)(=O)c4ccc(OCC5(F)CCOCC5)c(Cl)c4)c(Oc4cccc5[nH]ncc45)c3)CC2)=C(c2ccc(Cl)cc2)C1] |

| Name | Structure |
|---|---|
| 2-(1H-benzimidazol-4-yloxy)-4-(4-{[2-(4-chlorophenyl)-4,4-dimethylcyclohex-1-en-1-yl]methyl}piperazin-1-yl)-N-{[5-chloro-6-(tetrahydro-2H-pyran-4-ylmethoxy)pyridin-3-yl]sulfonyl}benzamide | 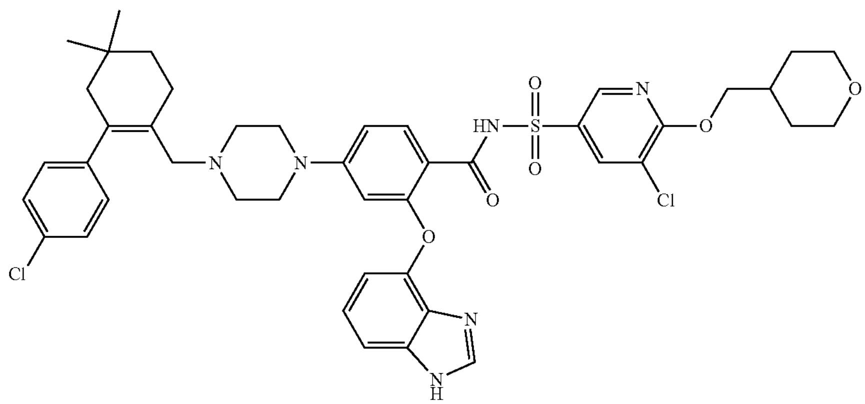 [SMILES: CC1(C)CCC(CN2CCN(c3ccc(C(=O)NS(=O)(=O)c4cnc(OCC5CCOCC5)c(Cl)c4)c(Oc4cccc5[nH]cnc45)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-({3-cyano-4-[(4-fluorotetrahydro-2H-pyran-4-yl)methoxy]phenyl}sulfonyl)-2-(1H-indazol-4-yloxy)benzamide | 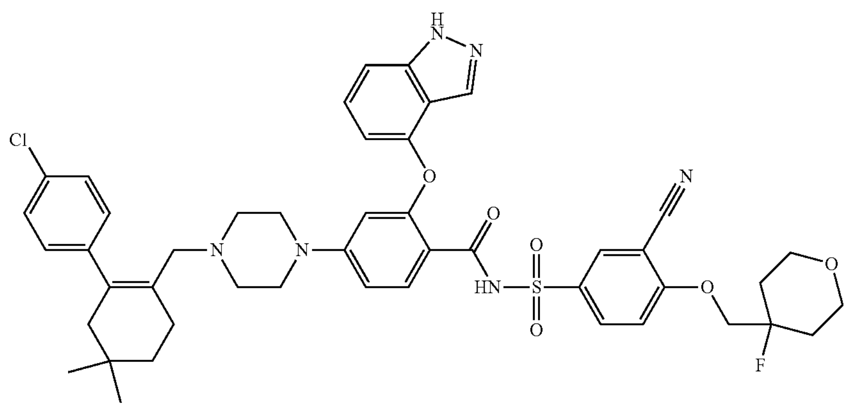 [SMILES: CC1(C)CCC(CN2CCN(c3ccc(C(=O)NS(=O)(=O)c4ccc(OCC5(F)CCOCC5)c(C#N)c4)c(Oc4cccc5[nH]ncc45)c3)CC2)=C(c2ccc(Cl)cc2)C1] |
| N-([3-chloro-4-(1,4-dioxan-2-ylmethoxy)phenyl]sulfonyl]-4-(4-{[2-(4-chlorophenyl)-4,4-dimethylcyclohex-1-en-1-yl]methyl}piperazin-1-yl)-2-(1H-indazol-4-yloxy)benzamide | |

-continued

| Name | Structure |
|------|-----------|
| 2-(1H-benzimidazol-4-yloxy)-N-[(5-chloro-6-{[(2S)-4-cyclopropylmorpholin-2-yl]methoxy}pyridin-3-yl)sulfonyl]-4-(4-{[2-(4-chlorophenyl)-4,4-dimethylcyclohex-1-en-1-yl]methyl)piperazin-1-yl)benzamide | 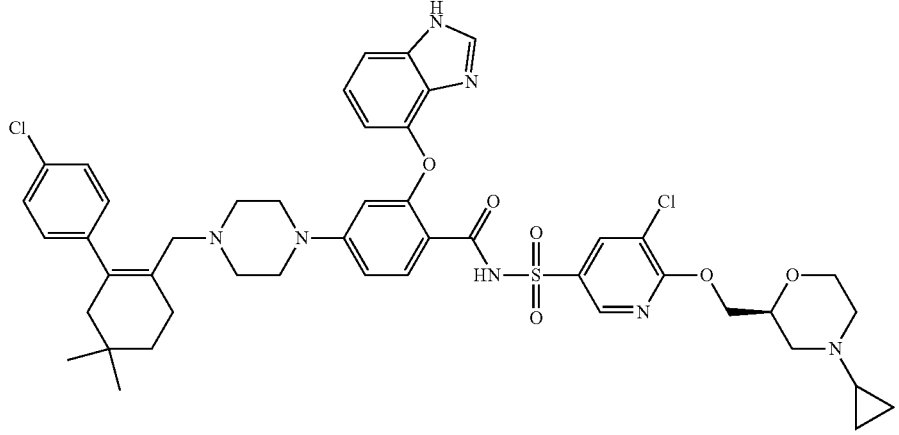 [SMILES: CC1(C)CCC(CN2CCN(c3ccc(C(=O)NS(=O)(=O)c4cnc(OC[C@@H]5CN(C6CC6)CCO5)c(Cl)c4)c(Oc4cccc5[nH]cnc45)c3)CC2)=C(c2ccc(Cl)cc2)C1] |
| N-[(5-chloro-6-{[(2S)-4-cyclopropyl-morpholin-2-yl]methoxy}pyridin-3-yl)sulfonyl]-4-(4-{[2-(4-chloro-phenyl)-4,4-dimethylcyclohex-1-en-1-yl]methyl}piperazin-1-yl)-2-(1H-indazol-4-yloxy)benzamide | 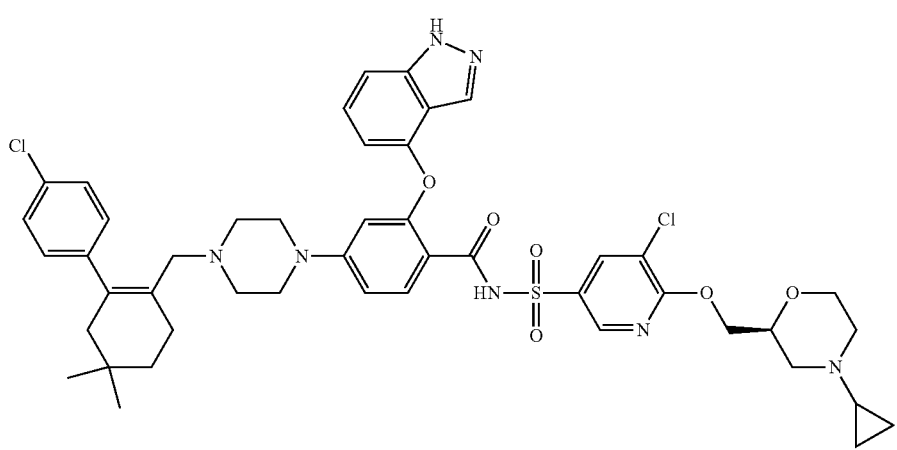 [SMILES: CC1(C)CCC(CN2CCN(c3ccc(C(=O)NS(=O)(=O)c4cnc(OC[C@@H]5CN(C6CC6)CCO5)c(Cl)c4)c(Oc4cccc5[nH]ncc45)c3)CC2)=C(c2ccc(Cl)cc2)C1] |
| methyl 2-{[(4-{[4-(4-{[2-(4-chlorophenyl)-4,4-dimethylcyclohex-1-en-1-yl]methyl}piperazin-1-yl)-2-(1H-indazol-4-yloxy)benzoyl]sulfamoyl}-2-nitrophenyl)amino]methyl}morpholine-4-carboxylate | 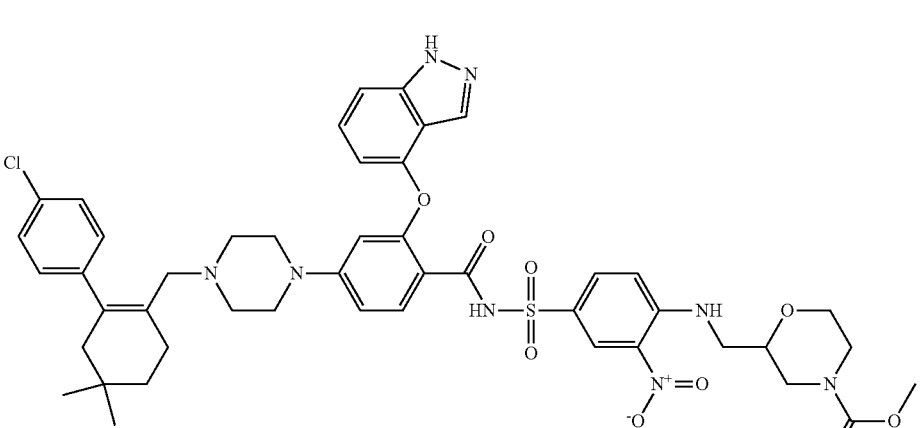 |

| Name | Structure |
|---|---|
| 2-{[(4-([4-(4-([2-(4-chlorophenyl)-4,4-dimethylcyclohex-1-en-1-yl]methyl}piperazin-1-yl)-2-(1H-indazol-4-yloxy)benzoyl]sulfamoyl}-2-nitrophenyl)amino]methyl}-N-ethyl-N-methylmorpholine-4-carboxamide | 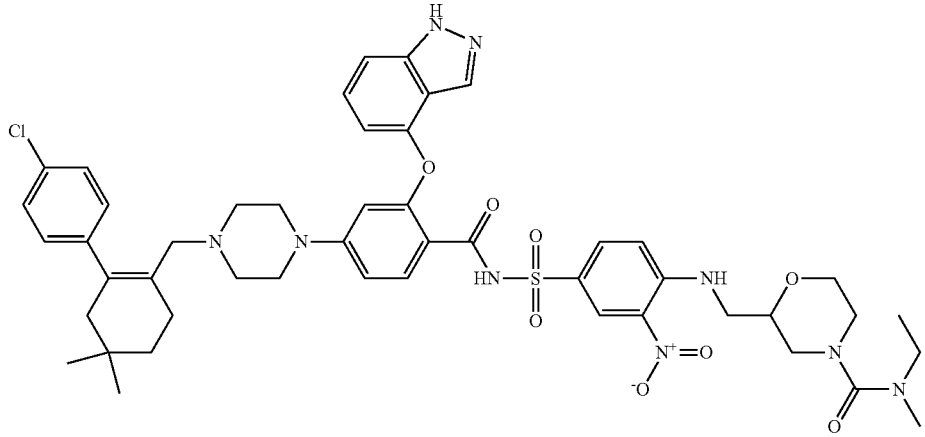 |
| 2-{[(4-{[2-(1H-benzimidazol-4-yloxy)4-(4-{[2-(4-chloro-phenyl)-4,4-dimethylcyclohex-1-en-1-yl]methyl}piperazin-1-yl)benzoyl]sulfamoyl}-2-nitrophenyl)amino]methyl}-N-ethyl-N-methylmorpholine-4-carboxamide | 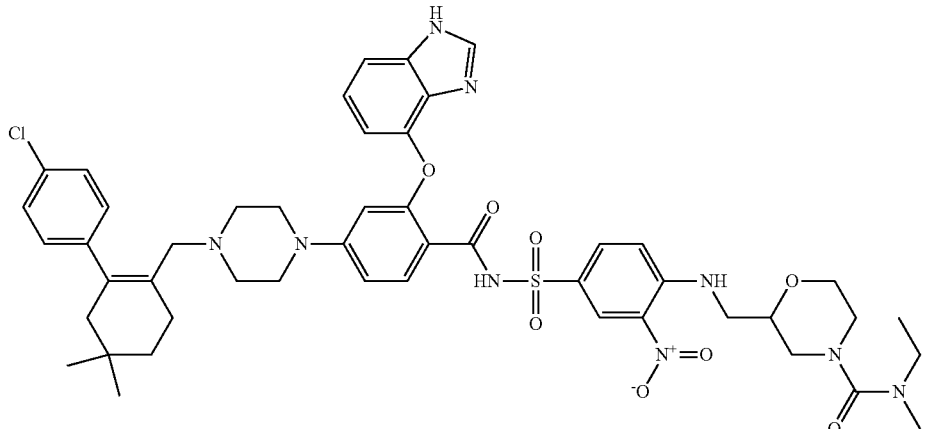 |
| N-({5-chloro-6-[(trans-4-ethyl-4-hydroxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide | 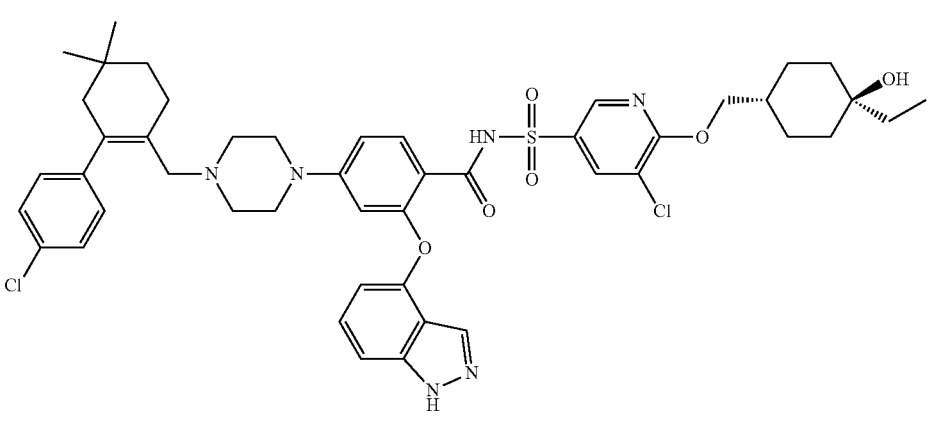 [SMILES: CC[C@]1(O)CC[C@H](COc2ncc(S(=O)(=O)NC(=O)c3ccc(N4CCN(CC5=C(c6ccc(Cl)cc6)CC(C)(C)CC5)CC4)cc3Oc3cccc4[nH]ncc34)cc2Cl)CC1] |

| Name | Structure |
|---|---|
| N-{{5-chloro-6-[(cis-4-ethyl-4-hydroxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide | 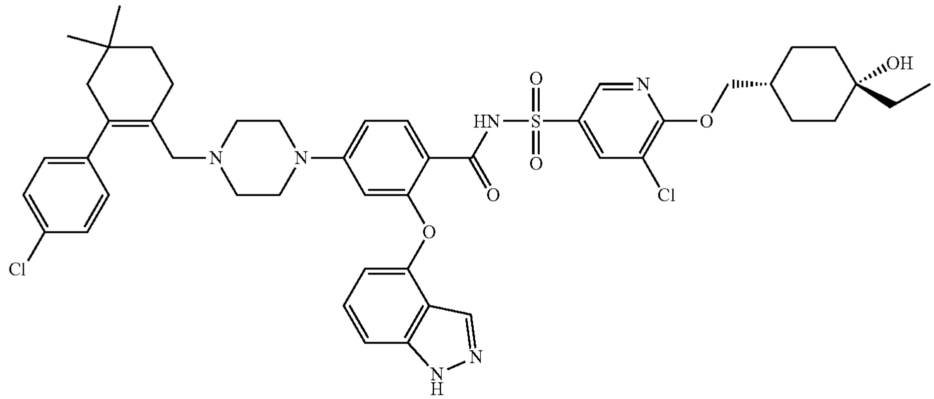 [SMILES: CC[C@]1(O)CC[C@@H](COc2ncc(S(=O)(=O)NC(=O)c3ccc(N4CCN(CC5=C(c6ccc(Cl)cc6)CC(C)(C)CC5)CC4)cc3Oc3cccc4[nH]ncc34)cc2Cl)CC1] |
| 5-chloro-N-({5-chloro-6-[(4-fluorotetrahydro-2H-pyran-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide | 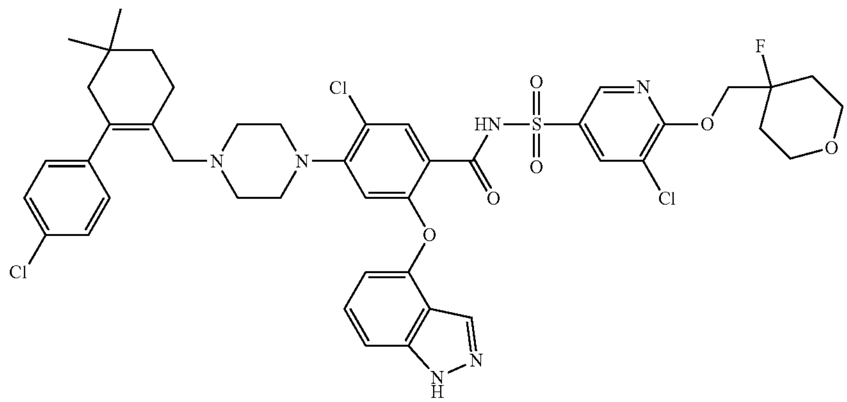 [SMILES: CC1(C)CCC(CN2CCN(c3cc(Oc4cccc5[nH]ncc45)c(C(=O)NS(=O)(=O)c4cnc(OCC5(F)CCOCC5)c(Cl)c4)cc3Cl)CC2)=C(c2ccc(Cl)cc2)C1] |
| 5-chloro-4-(4-{[2-(4-chlorophenyl)-4,4-dimethylcyclohex-1-en-1-yl]methyl}piperazin-1-yl)-N-[(4-{[(4-fluorotetrahydro-2H-pyran-4-yl)methyl]amino}-3-nitrophenyl)sulfonyl]-2-(1H-indazol-4-yloxy)benzamide | 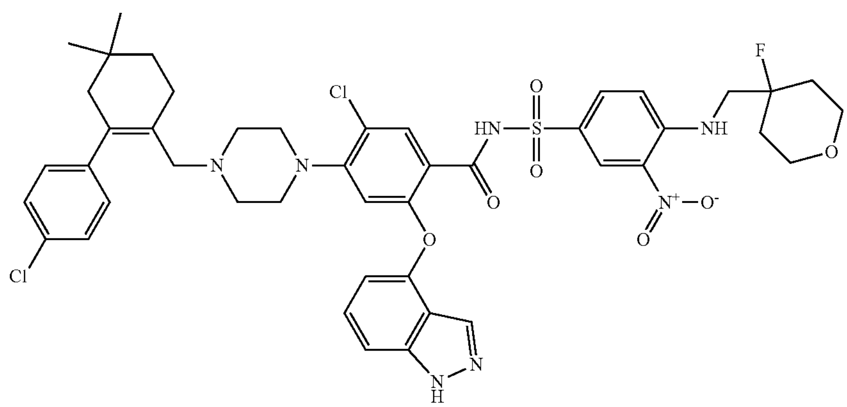 [SMILES: CC1(C)CCC(CN2CCN(c3cc(Oc4cccc5[nH]ncc45)c(C(=O)NS(=O)(=O)c4ccc(NCC5(F)CCOCC5)c([N+](=O)[O-])c4)cc3Cl)CC2)=C(c2ccc(Cl)cc2)C1] |
| N-({5-chloro-6-[(cis-1-fluoro-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide | |

| Name | Structure |
|---|---|
| N-({5-chloro-6-[(trans-1-fluoro-4-hydroxy-4-methylcyclohexyl)methoxy]pyridin-3-yl}sulfonyl)-4-(4-{[2-(4-chlorophenyl)-4,4-dimethyl-cyclohex-1-en-1-yl]methyl]piperazin-1-yl)-2-(1H-indazol-4-yloxy)benzamide | 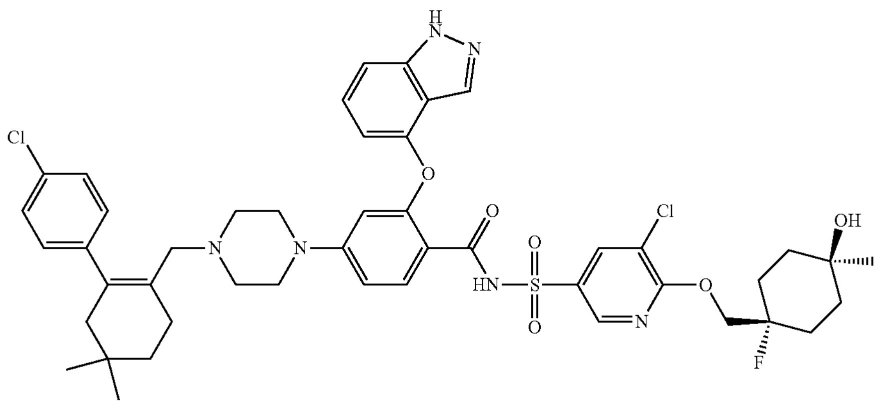 [SMILES: CC1(C)CCC(CN2CCN(c3ccc(C(=O)NS(=O)(=O)c4cnc(OC[C@]5(F)CC[C@](C)(O)CC5)c(Cl)c4)c(Oc4cccc5[nH]ncc45)c3)CC2)=C(c2ccc(Cl)cc2)C1] |
| 2-(1H-benzotriazol-4-yloxy)-4-(4-{[2-(4-chlorophenyl)-4,4-dimethylcyclohex-1-en-1-yl]methyl}piperazin-1-yl)-N-[(4-{[(4-fluorotetra-hydro-2H-pyran-4-yl)methyl]amino}-3-nitrophenyl)sulfonyl]benzamide | |
| 2-(1H-benzotriazol-4-yloxy)-N-({5-chloro-6-[(4-fluoro-tetrahydro-2H-pyran-4-yl)methoxy]pyridin-3-yl}sulfonyl)-4-(4-{[2-(4-chloro-phenyl)-4,4-dimethylcyclohex-1-en-1-yl]methyl}piperazin-1-yl)benzamide | 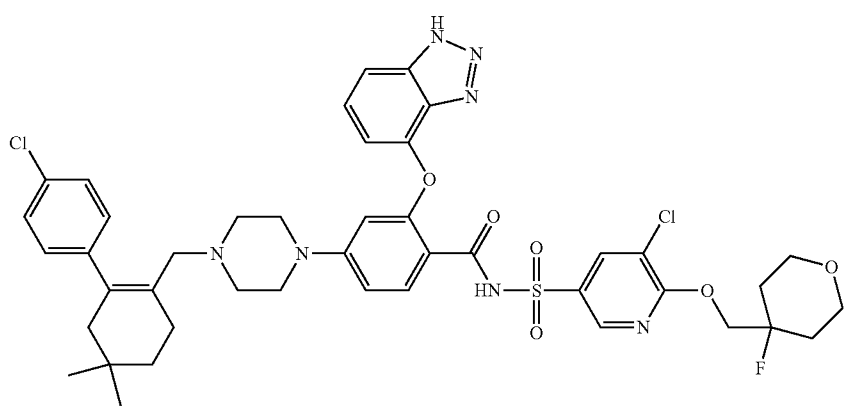 [SMILES: CC1(C)CCC(CN2CCN(c3ccc(C(=O)NS(=O)(=O)c4cnc(OCC5(F)CCOCC5)c(Cl)c4)c(Oc4cccc5[nH]nnc45)c3)CC2)=C(c2ccc(Cl)cc2)C1] |

-continued

| Name | Structure |
|---|---|
| 2-(1H-benzimidazol-4-yloxy)-4-(4-{[2-(4-chlorophenyl)-4,4-dimethylcyclohex-1-en-1-yl]methyl}piperazin-1-yl)-N-{[3-chloro-4-(tetrahydro-2H-pyran-4-ylmethoxy)phenyl]sulfonyl}benzamide | |
| N-[(3-chloro-4-{[4-fluoro-1-(oxetan-3-yl)piperidin-4-yl]methoxy}phenyl)sulfonyl]-4-(4-([2-(4-chlorophenyl)-4,4-dimethylcyclohex-1-en-1-yl]methyl}piperazin-1-yl)-2-{1H-indazol-4-yloxy)benzamide | 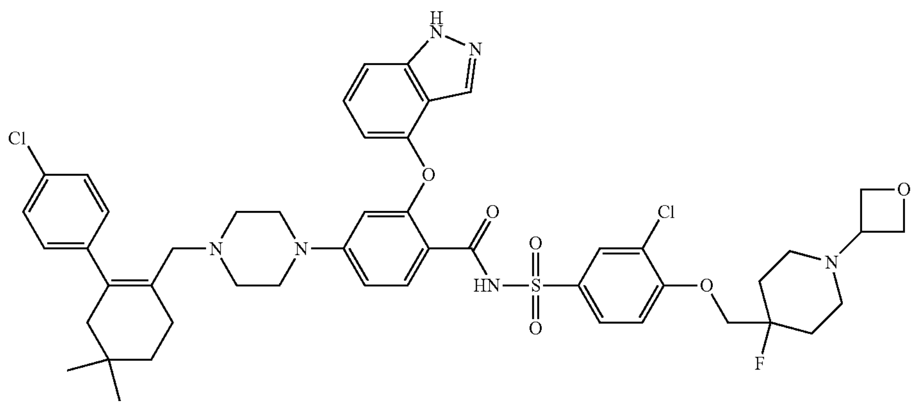 [SMILES: CC1(C)CCC(CN2CCN(c3ccc(C(=O)NS(=O)(=O)c4ccc(OCC5(F)CCN(C6COC6)CC5)c(Cl)c4)c(Oc4cccc5[nH]ncc45)c3)CC2)=C(c2ccc(Cl)cc2)C1] |
| N-({5-chloro-6-[(cis-1-fluoro-4-hydroxycyclohexyl)methoxy]pyridin-3-yl}sulfonyl)-4-(4-{[2-(4-chlorophenyl)-4,4-dimethyl-cyclohex-1-en-1-yl]methyl}piperazin-1-yl)-2-(1H-indazol-4-yloxy)benzamide | 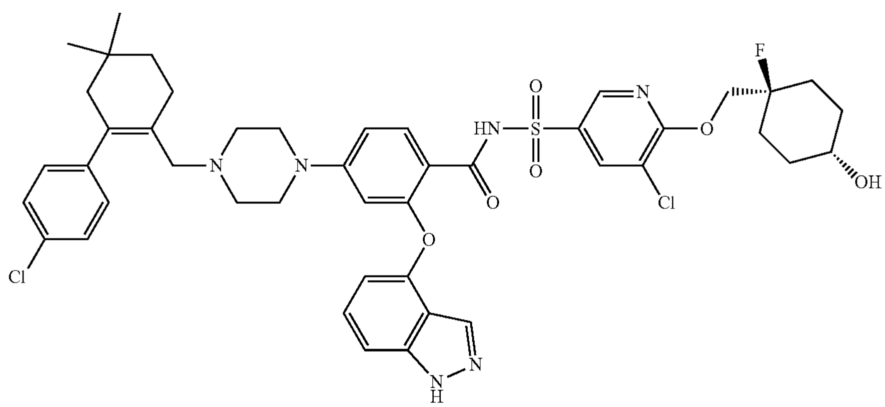 [SMILES: CC1(C)CCC(CN2CCN(c3ccc(C(=O)NS(=O)(=O)c4cnc(OC[C@]5(F)CC[C@H](O)CC5)c(Cl)c4)c(Oc4cccc5[nH]ncc45)c3)CC2)=C(c2ccc(Cl)cc2)C1] |
| 2-(1H-benzotriazol-4-yloxy)-4-(4-{[2-(4-chlorophenyl)-4,4-dimethylcyclohex-1-en-1-yl]methyl}piperazin-1-yl)-N-({4-[(4-fluoro-tetrahydro-2H-pyran-4-yl)methoxy]-3-nitrophenyl)sulfonyl)benzamide | 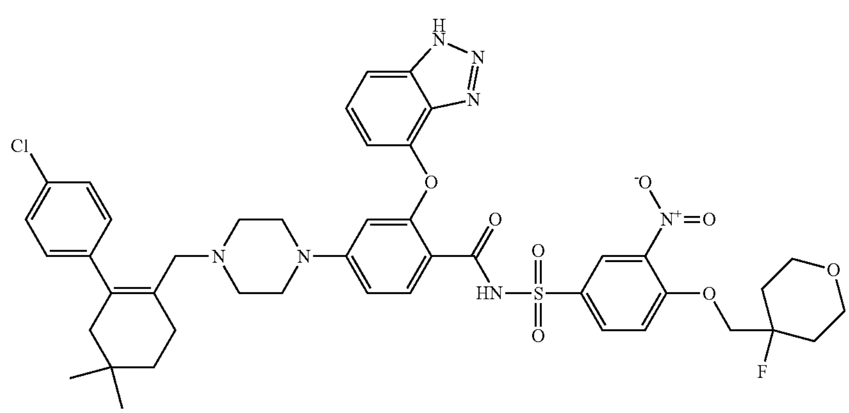 |

-continued

| Name | Structure |
|---|---|
| N-[(5-chloro-6-{[(1R,2R,4R,5R)-5-hydroxy-5-methyl-bicyclo[2.2.1]hept-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-indazol-4-yloxy)benzamide | 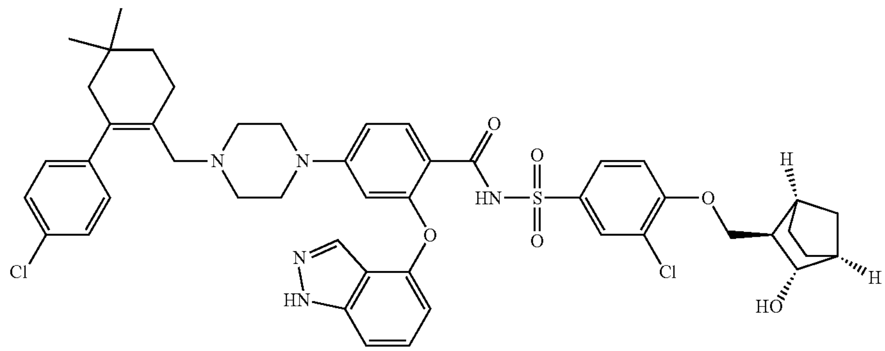 [SMILES: CC1(C)CCC(CN2CCN(c3ccc(C(=O)NS(=O)(=O)c4ccc(OC[C@H]5[C@@H]6CC[C@@H](C6)[C@@H]5O)c(Cl)c4)c(Oc4cccc5[nH]ncc45)c3)CC2)=C(c2ccc(Cl)cc2)C1] |
| N-({5-chloro-6-[(4-fluorotetrahydro-2H-pyran-4-yl)methoxy]pyridin-3-yl}sulfonyl)-4-(4-{[2-(4-chlorophenyl)-5,5-difluorocyclohex-1-en-1-yl]methyl}piperazin-1-yl)-2-(1H-indazol-4-yloxy)benzamide | 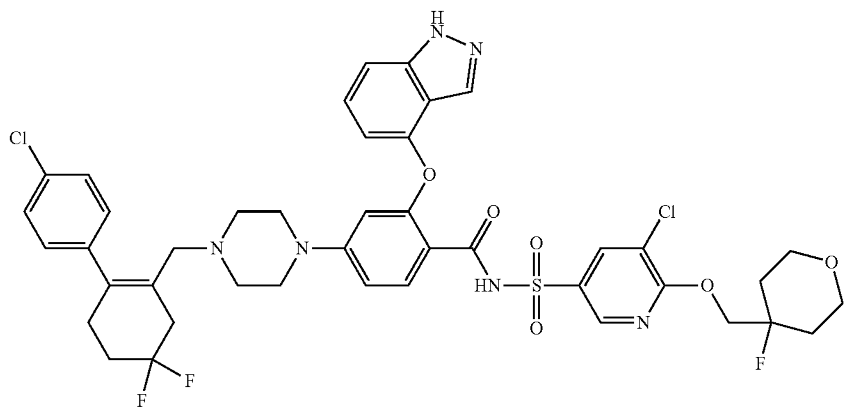 [SMILES: O=C(NS(=O)(=O)c1cnc(OCC2(F)CCOCC2)c(Cl)c1)c1ccc(N2CCN(CC3=C(c4ccc(Cl)cc4)CCC(F)(F)C3)CC2)cc1Oc1cccc2[nH]ncc12] |
| N-[(5-chloro-6-{[4-fluoro-1-(oxetan-3-yl)piperidin-4-yl]methoxy}pyridin-3-yl)sulfonyl]-4-(4-{[2-(4-chlorophenyl)-5,5-difluorocyclohex-1-en-1-yl]methyl}piperazin-1-yl)-2-(1H-indazol-4-yloxy)benzamide | 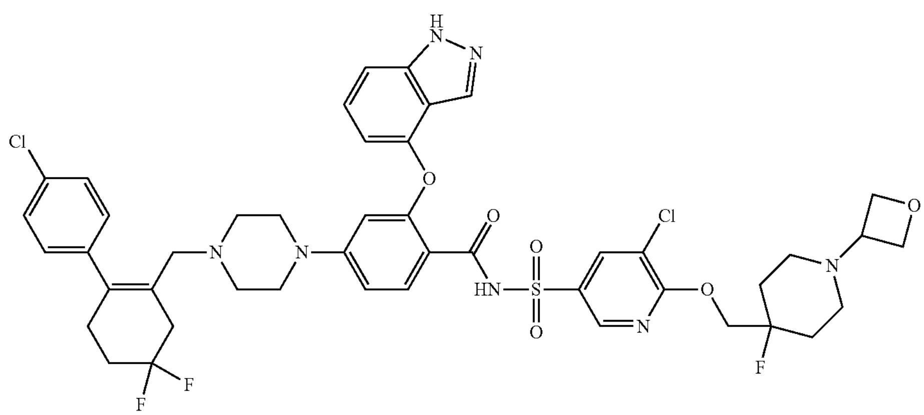 [SMILES: O=C(NS(=O)(=O)c1cnc(OCC2(F)CCN(C3COC3)CC2)c(Cl)c1)c1ccc(N2CCN(CC3=C(c4ccc(Cl)cc4)CCC(F)(F)C3)CC2)cc1Oc1cccc2[nH]ncc12] |
| 2-(1H-benzotriazol-4-yloxy)-4-(4-{[2-(4-chlorophenyl)-4,4-dimethylcyclohex-1-en-1-yl]methyl}piperazin-yl)-N-({3-nitro-4-[(tetrahydro-2H-pyran-4-ylmethyl)amino]phenyl}sulfonyl)benzamide | |

| Name | Structure |
|---|---|
| 4-(4-{[2-(4-chloro-phenyl)-5,5-difluorocyclohex-1-en-1-yl]methyl}piperazin-1-yl)-2-(1H-indazol-4-yloxy)-N-({3-nitro-4-[(tetrahydro-2H-pyran-4-ylmethyl)amino]phenyl}sulfonyl)benzamide | 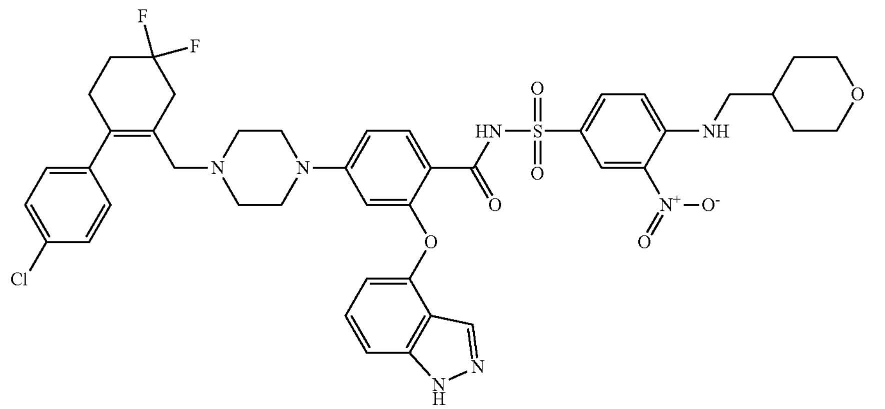 [SMILES: O=C(NS(=O)(=O)c1ccc(NCC2CCOCC2)c([N+](=O)[O-])c1)c1ccc(N2CCN(CC3=C(c4ccc(Cl)cc4)CCC(F)(F)C3)CC2)cc1Oc1cccc2[nH]ncc12] |
| 4-(4-{[2-(4-chloro-phenyl)-4,4-dimethylcyclohex-1-en-1-yl]methyl}piperazin-1-yl)-N-[4-{[(trans-4-hydroxy-4-methylcyclohexyl)methyl]amino}-3-nitrophenyl)sulfonyl]-2-(1H-indazol-4yloxy)benzamide | |
| 4-(4-{[2-(4-chloro-phenyl)-4,4-dimethylcyclohex-1-en-1-yl]methyl)piperazin-1-yl)-N-[(4-{[(cis 4-hydroxy-4-methylcyclohexyl)methyl]amino}-3-nitrophenyl)sulfonyl]-2-(1H-indazol-4-yloxy)benzamide | 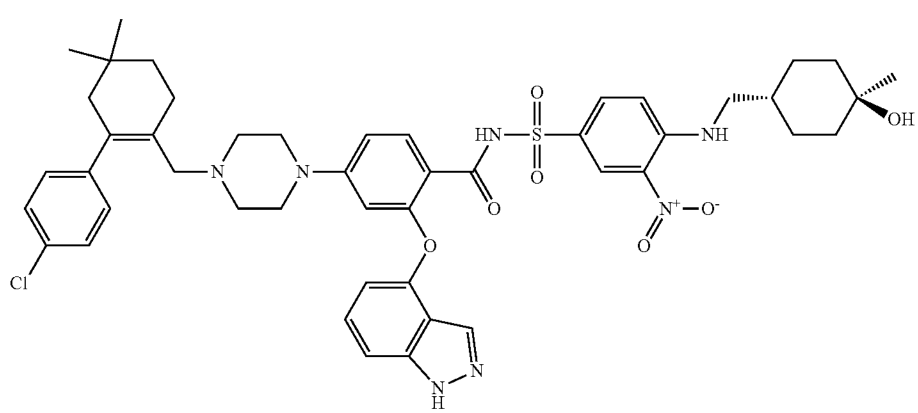 |

| Name | Structure |
|---|---|
| 2-(1H-benzotriazol-4-yloxy)-4-(4-{[2-(4-chlorophenyl)-4,4-dimethylcyclohex-1-en-1-yl]methyl}piperazin-1-yl)-N-{[4-({[(2S)-4-cyclopropylmorpholin-2-yl]methyl}amino)-3-nitrophenyl]sulfonyl}benzamide | |
| N-[(5-chloro-6-{[4-fluoro-1-(oxetan-3-yl)piperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-indazol-4-yloxy)benzamide | 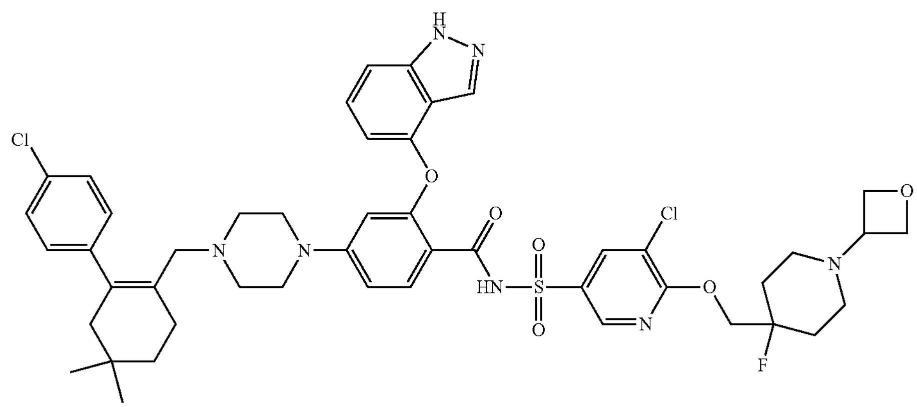 [SMILES: CC1(C)CCC(CN2CCN(c3ccc(C(=O)NS(=O)(=O)c4cnc(OCC5(F)CCN(C6COC6)CC5)c(Cl)c4)c(Oc4cccc5[nH]ncc45)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-{[4-({[(2S)-4-cyclopropylmorpholin-2-yl]methyl}amino)-3-nitrophenyl]sulfonyl}-2-(1H-indazol-4-yloxy)benzamide | 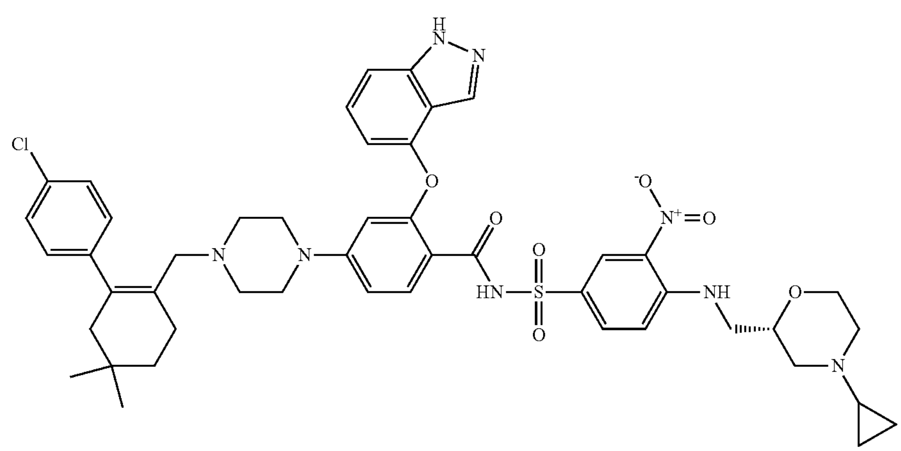 |

-continued

| Name | Structure |
|---|---|
| 2-(1H-benzimidazol-4-yloxy)-4-(4-{[2-(4-chlorophenyl)-4,4-dimethylcyclohex-1-en-1-yl]methyl}piperazin-1-yl)-N-{[4-({[(2S)-4-cyclopropylmorpholin-2-yl]methyl}amino)-3-nitrophenyl]sulfonyl}benzamide | 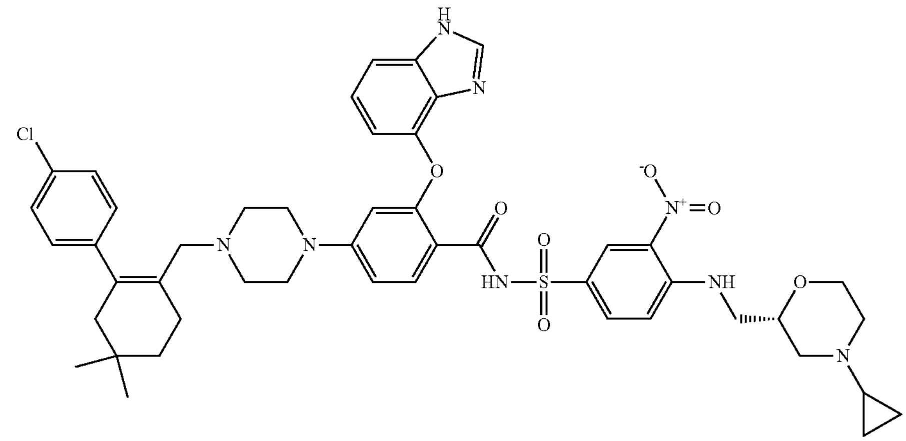 |
| N-({5-chloro-6-[(trans-4-hydroxy-4-methylcyclohexyl)methoxy]pyridin-3-yl}sulfonyl)-4-(4-{[2-(4-chlorophenyl)-5,5-difluorocyclohex-1-en-1-yl]methyl}piperazin-1-yl)-2-(1H-indazol-4-yloxy)benzamide | 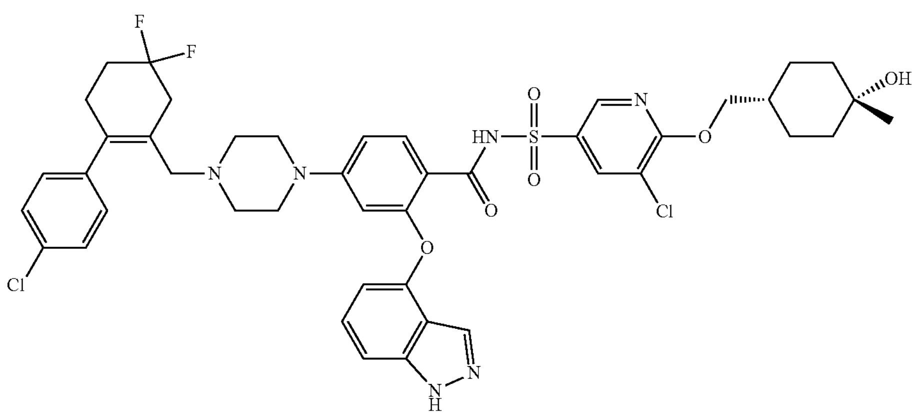 [SMILES: C[C@]1(O)CC[C@@H](COc2ncc(S(=O)(=O)NC(=O)c3ccc(N4CCN(CC5=C(c6ccc(Cl)cc6)CCC(F)(F)C5)CC4)cc3Oc3cccc4[nH]ncc34)cc2Cl)CC1] |
| 4-(4-{[2-(4-chlorophenyl)-4,4-dimethylcyclohex-1-en-1-yl]methyl}piperazin-1-yl)-N-({4-[(cis-4-hydroxy-4-methylcyclohexyl)methoxy]-3-nitrophenyl}sulfonyl)-2-(1H-indazol-4-yloxy)benzamide | 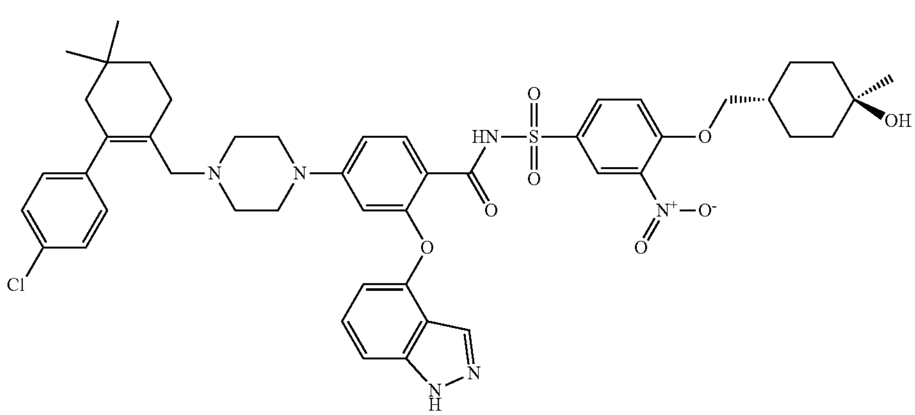 [SMILES: CC1(C)CCC(CN2CCN(c3ccc(C(=O)NS(=O)(=O)c4ccc(OC[C@H]5CC[C@](C)(O)CC5)c([N+](=O)[O-])c4)c(Oc4cccc5[nH]ncc45)c3)CC2)=C(c2ccc(Cl)cc2)C1] |

| Name | Structure |
|---|---|
| 4-(4-{[2-(4-chloro-phenyl)-4,4-dimethylcyclohex-1-en-1-yl]methyl}piperazin-1-yl)-N-({4-[(trans-4-hydroxy-4-methyl-cyclohexyl)methoxy]-3-nitrophenyl}sulfonyl)-2-(1H-indazol-4-yloxy)benzamide | 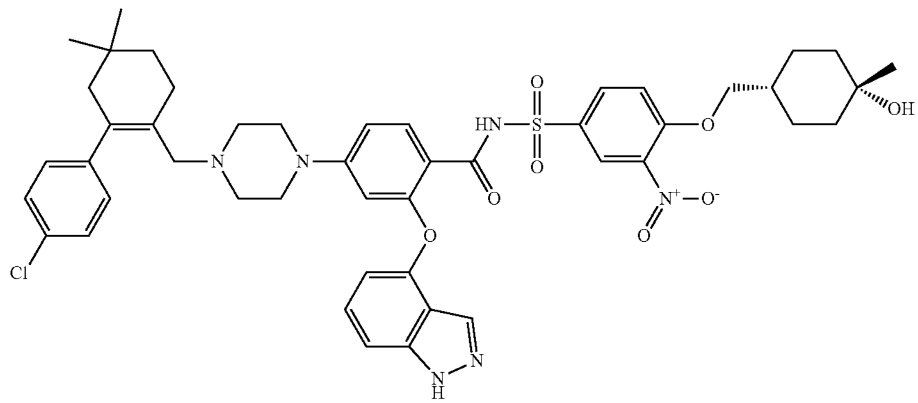 [SMILES: CC1(C)CCC(CN2CCN(c3ccc(C(=O)NS(=O)(=O)c4ccc(OC[C@H]5CC[C@@](C)(O)CC5)c([N+](=O)[O-])c4)c(Oc4cccc5[nH]ncc45)c3)CC2)=C(c2ccc(Cl)cc2)C1] |
| 4-(4-{[2-(4-chloro-phenyl)-4,4-dimethylcyclohex-1-en-1-yl]methyl}piperazin-1-yl)-N-[(3-cyano-4-{[4-fluoro-1-(oxetan-3-yl)piperidin-4-yl]methoxy}phenyl)sulfonyl]-2-(1H-indazol-4-yloxy)benzamide | 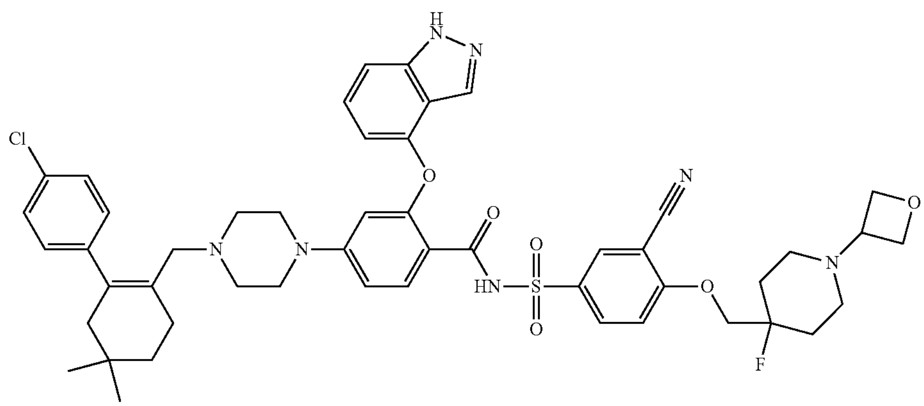 [SMILES: CC1(C)CCC(CN2CCN(c3ccc(C(=O)NS(=O)(=O)c4ccc(OCC5(F)CCN(C6COC6)CC5)c(C#N)c4)c(Oc4cccc5[nH]ncc45)c3)CC2)=C(c2ccc(Cl)cc2)C1] |
| 4-(4-{[2-(4-chloro-phenyl)-4,4-dimethylcyclohex-1-en-1-yl]methyl}piperazin-1-yl)-2-(1H-indazol-4-yloxy)-N-{[3-nitro-4-(2-oxaspiro[3.5]non-7-ylmethoxy)phenyl]sulfonyl}benzamide | 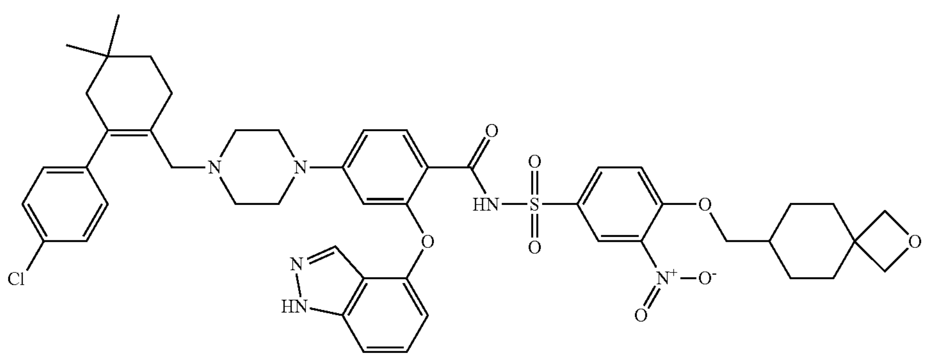 [SMILES: CC1(C)CCC(CN2CCN(c3ccc(C(=O)NS(=O)(=O)c4ccc(OCC5CCC6(CC5)COC6)c([N+](=O)[O-])c4)c(Oc4cccc5[nH]ncc45)c3)CC2)=C(c2ccc(Cl)cc2)C1] |
| 4-(4-{[2-(4-chloro-phenyl)-4,4-dimethylcyclohex-1-en-1-yl]methyl}piperazin-1-yl)-N-{[5-chloro-6-(5,6,7,8-tetrahydro-imidazo[1,2-a]pyridin-6-yl-methoxy)pyridin-3-yl]sulfonyl)-2-(1H-indazol-4-yloxy)benzamide | 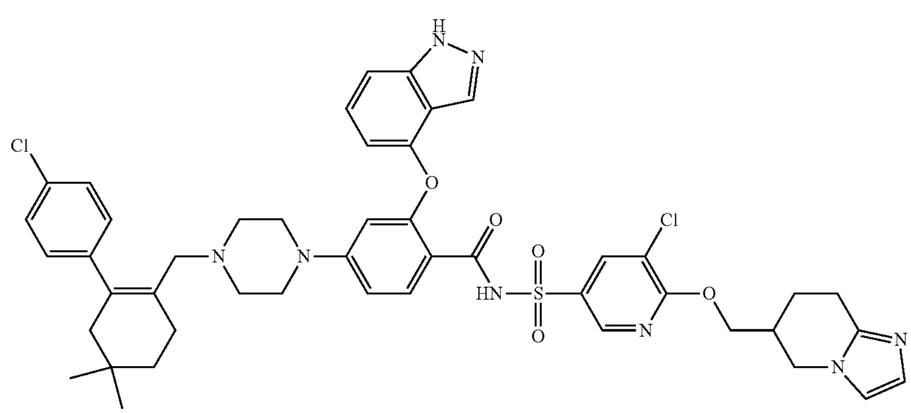 [SMILES: CC1(C)CCC(CN2CCN(c3ccc(C(=O)NS(=O)(=O)c4cnc(OCC5CCc6nccn6C5)c(Cl)c4)c(Oc4cccc5[nH]ncc45)c3)CC2)=C(c2ccc(Cl)cc2)C1] |

| Name | Structure |
|---|---|
| 2-(1H-benzimidazol-4-yloxy)-N-({5-chloro-6-[(trans-4-hydroxy-4-methylcyclohexyl)methoxy]pyridin-3-yl}sulfonyl)-4-(4-{[2-(4-chlorophenyl)-4,4-dimethylcyclohex-{-en-1-yl]methyl}piperazin-1-yl)benzamide | 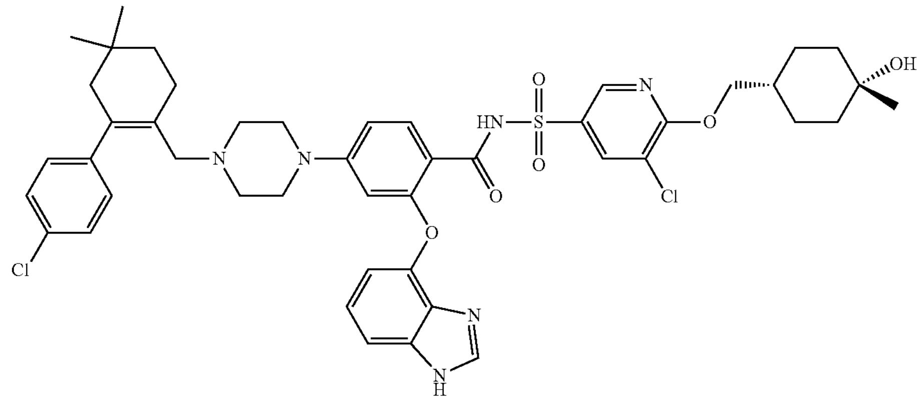 |
| 4-(4-{[2-(4-chlorophenyl)-4,4-dimethylcyclohex-1-en-1-yl]methyl}piperazin-1-yl)-N-[(5-cyano-6-{[4-fluoro-1-(oxetan-3-yl)piperidin-4-yl]methoxy}pyridin-3-yl)sulfonyl]-2-(1H-indazol-4-yloxy)benzamide | 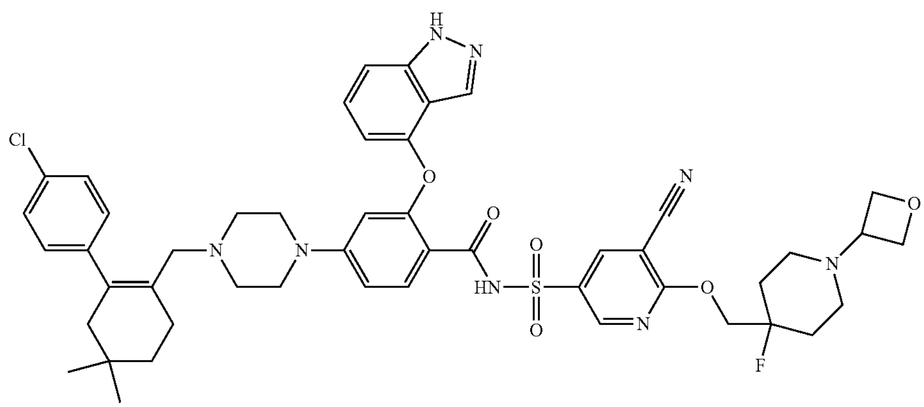 [SMILES: CC1(C)CCC(CN2CCN(c3ccc(C(=O)NS(=O)(=O)c4cnc(OCC5(F)CCN(C6COC6)CC5)c(C#N)c4)c(Oc4cccc5[nH]ncc45)c3)CC2)=C(c2ccc(Cl)cc2)C1] |
| N-({5-chloro-6-[(trans-4-hydroxy-4-methylcyclohexyl)methoxy]pyridin-3-yl}sulfonyl)-4-(4-{[2-(4-chlorophenyl)-5-(methoxymethyl)-5-methylcyclohex-1-en-1-yl]methyl}piperazin-1-yl)-2-(1H-indazol-4-yloxy)benzamide | 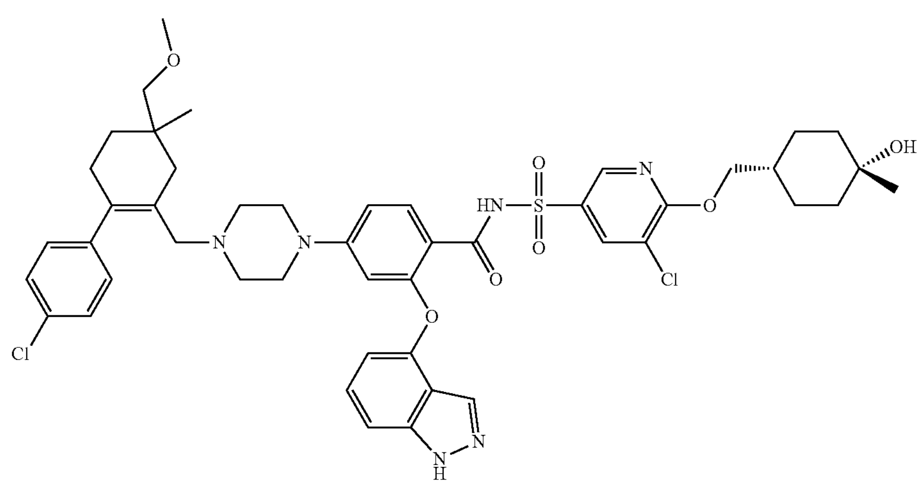 [SMILES: COCC1(C)CCC(c2ccc(Cl)cc2)=C(CN2CCN(c3ccc(C(=O)NS(=O)(=O)c4cnc(OC[C@H]5CC[C@@](C)(O)CC5)c(Cl)c4)c(Oc4cccc5[nH]ncc45)c3)CC2)C1] |

-continued

| Name | Structure |
|---|---|
| 4-(4-{[2-(4-chlorophenyl)-4,4-dimethylcyclohex-1-en-1-yl]methyl}piperazin-1-yl)-2-(1H-indazol-4-yloxy)-N-{[3-nitro-4-((([(2S)-4-(oxetan-3-yl)morpholin-2-yl]methyl}amino)phenyl]sulfonyl}benzamide | |
| 2-(1H-benzimidazol-4-yloxy)-4-(4-{[2-(4-chlorophenyl)-4,4-dimethylcyclohex-1-en-1-yl]methyl}piperazin-1-yl)-N-{[3-nitro-4-({[(2S)-4-(oxetan-3-yl)morpholin-2-yl]methyl}amino)phenyl]sulfonyl}benzamide | |
| N-[(5-chloro-6-{[trans-4-(2-hydroxypropan-2-yl)cyclohexyl]methoxy}pyridin-3-yl)sulfonyl]-4-(4-{[2-(4-chlorophenyl)-4,4-dimethylcyclohex-1-en-1-yl]methyl)piperazin-1-yl)-2-(1H-indazol-4-yloxy)benzamide | |

-continued

| Name | Structure |
|---|---|
| 4-(4-{[2-(4-chloro-phenyl)-4,4-dimethylcyclohex-1-en-1-yl]methyl}piperazin-1-yl)-N-({3-cyano-4-[(trans-4-hydroxy-4-methylcyclohexyl)methoxy]phenyl}sulfonyl)-2-(1H-indazol-4-yloxy)benzamide | 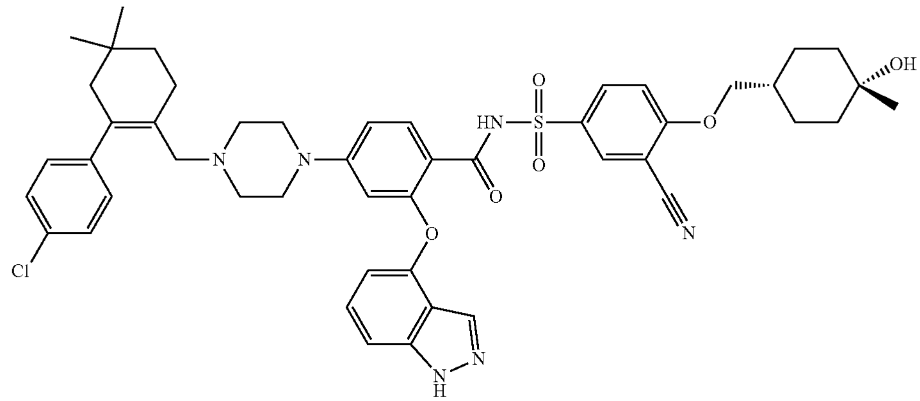 [SMILES: CC1(C)CCC(CN2CCN(c3ccc(C(=O)NS(=O)(=O)c4ccc(OC[C@H]5CC[C@@](C)(O)CC5)c(C#N)c4)c(Oc4cccc5[nH]ncc45)c3)CC2)=C(c2ccc(Cl)cc2)C1] |
| 4-(4-{[2-(4-chloro-phenyl)-4,4-dimethylcyclohex-1-en-1-yl]methyl}piperazin-1-yl)-N-({5-cyano-6-[(trans-4-hydroxy-4-methylcyclohexyl)methoxy]pyridin-3-yl}sulfony})-2-(1H-indazol-4-yloxy)benzamide | |
| 4-(4-{[2-(4-chloro-phenyl)-4,4-dimethylcyclohex-1-en-1-yl]methyl}piperazin-1-yl)-2-(1H-indazol-4-yloxy)-N-({5-nitro-6-(tetrahydro-2H-pyran-4-ylmethyl)amino]pyridin-3-yl}sulfonyl)benzamide | 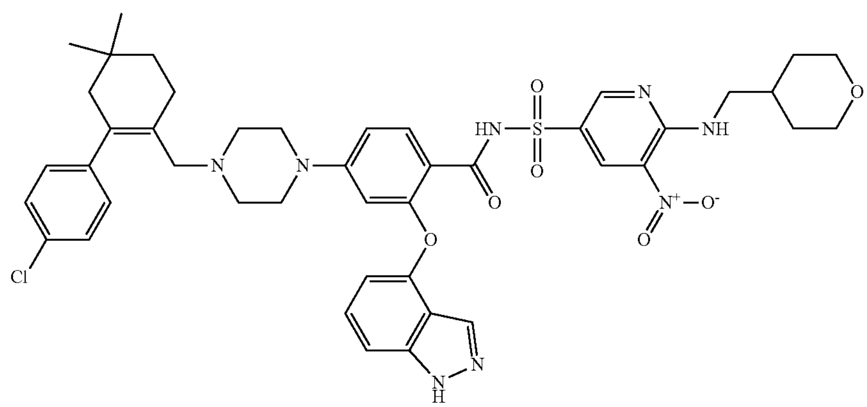 [SMILES: CC1(C)CCC(CN2CCN(c3ccc(C(=O)NS(=O)(=O)c4cnc(NCC5CCOCC5)c([N+](=O)[O-])c4)c(Oc4cccc5[nH]ncc45)c3)CC2)=C(c2ccc(Cl)cc2)C1] |
| 2-(1H-benzotriazol-4-yloxy)-N-({5-chloro-6-[(trans-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)benzamide | |

| Name | Structure |
|---|---|
| N-({3-chloro-4-[(cis-4-cyano-1-fluorocyclohexyl)methoxy]phenyl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide | 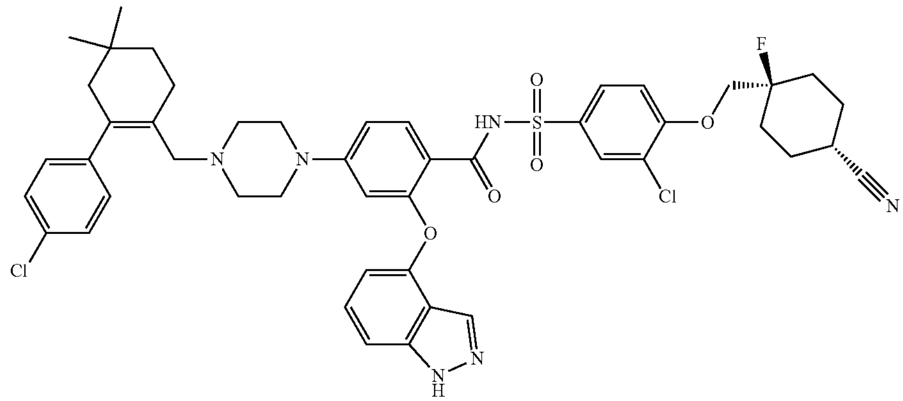 [SMILES: CC1(C)CCC(CN2CCN(c3ccc(C(=O)NS(=O)(=O)c4ccc(OC[C@]5(F)CC[C@H](C#N)CC5)c(Cl)c4)c(Oc4cccc5[nH]ncc45)c3)CC2)=C(c2ccc(Cl)cc2)C1] |
| N-({3-chloro-4-[(trans-4-cyano-1-fluorocyclohexyl)methoxy]phenyl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide | 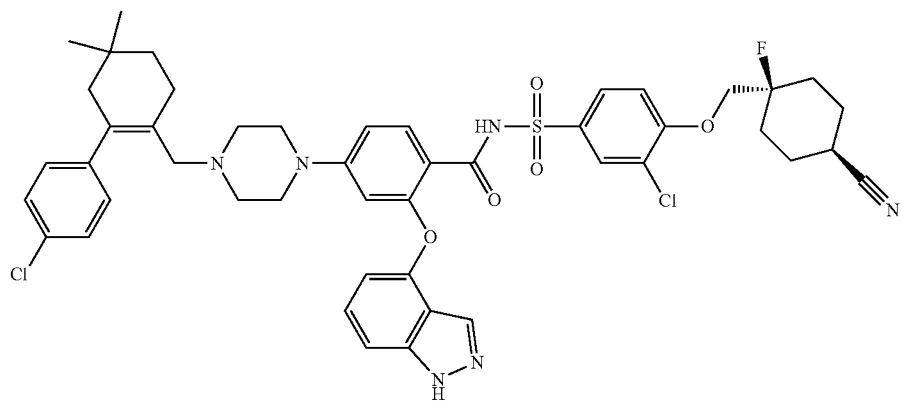 [SMILES: CC1(C)CCC(CN2CCN(c3ccc(C(=O)NS(=O)(=O)c4ccc(OC[C@]5(F)CC[C@@H](C#N)CC5)c(Cl)c4)c(Oc4cccc5[nH]ncc45)c3)CC2)=C(c2ccc(Cl)cc2)C1] |
| N-({5-chloro-6-[(cis-4-cyano-1-fluorocyclohexyl)methoxy]pyridin-3-yl)sulfonyl)-4-(4-{[2-(4-chlorophenyl)-4,4-dimethylcyclohex-1-en-1-yl]methyl}piperazin-1-yl)-2-(1H-indazol-4-yloxy)benzamide | 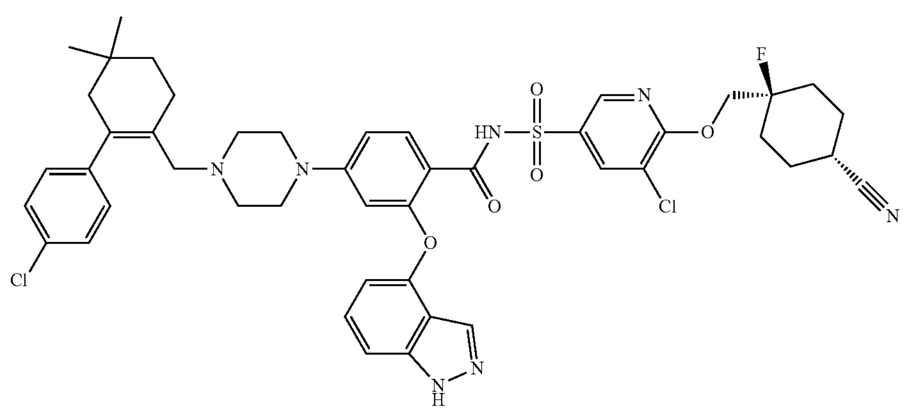 [SMILES: CC1(C)CCC(CN2CCN(c3ccc(C(=O)NS(=O)(=O)c4cnc(OC[C@]5(F)CC[C@H](C#N)CC5)c(Cl)c4)c(Oc4cccc5[nH]ncc45)c3)CC2)=C(c2ccc(Cl)cc2)C1] |

-continued

| Name | Structure |
|---|---|
| N-({5-chloro-6-[(trans-4-cyano-1-fluorocyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide | |
| N-({5-chloro-6-[(trans-4-hydroxy-4-methyl.cyclohexyl)methoxy]pyridin-3-yl}sulfonyl)-4-(4-{[4-(4-chlorophenyl)-6,6-dimethyl-5,6-dihydro-2H-pyran-3-yl]methyl)piperazin-1-yl)-2-(IH-indazol-4-yloxy)benzamide | 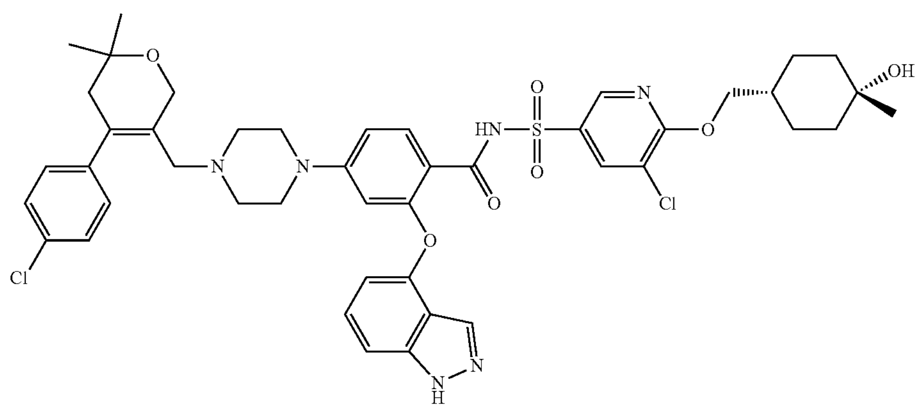 [SMILES: CC1(C)CC(c2ccc(Cl)cc2)=C(CN2CCN(c3ccc(C(=O)NS(=O)(=O)c4cnc(OC[C@H]5CC[C@@](C)(O)CC5)c(Cl)c4)c(Oc4cccc5[nH]ncc45)c3)CC2)CO1] |
| 2-(1H-benzimidazol-4-yloxy)-4-(4-{[2-(4-chlorophenyl)-4,4-dimethylcyclohex-1-en-1-yl]methyl}piperazin-1-yl)-N-[(4-{[(trans-4-hydroxy-4-methylcyclohexyl)methyl]amino]-3-nitrophenyl)sulfonyl]benzamide | 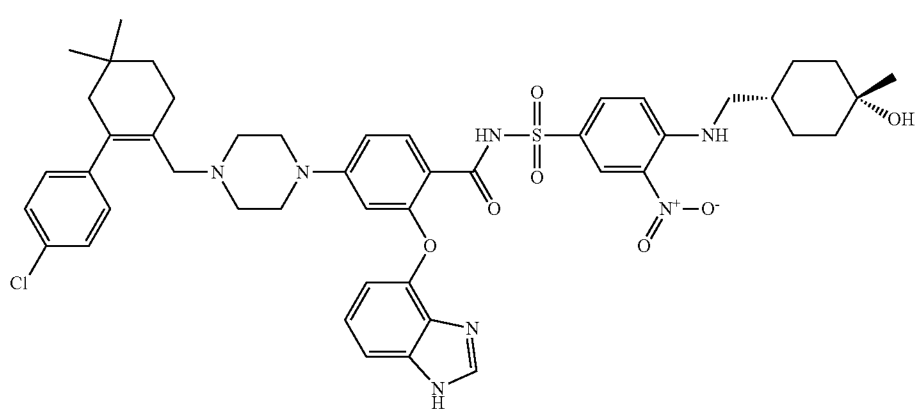 [SMILES: CC1(C)CCC(CN2CCN(c3ccc(C(=O)NS(=O)(=O)c4ccc(NC[C@H]5CC[C@@](C)(O)CC5)c([N+](=O)[O-])c4)c(Oc4cccc5[nH]cnc45)c3)CC2)=C(c2ccc(Cl)cc2)C1] |

| Name | Structure |
|---|---|
| N-({5-chloro-6-[(trans-4-hydroxy-4-methylcyclohexyl)methoxy]pyridin-3-yl}sulfanyl)-4-(4-{[2-(4-chlorophenyl)-5-m.ethoxy-5-methyl-cyclohex-1-en-1-yl]methyl}piperazin-1-yl)-2-(1H-indazol-4-yloxy)benzamide | 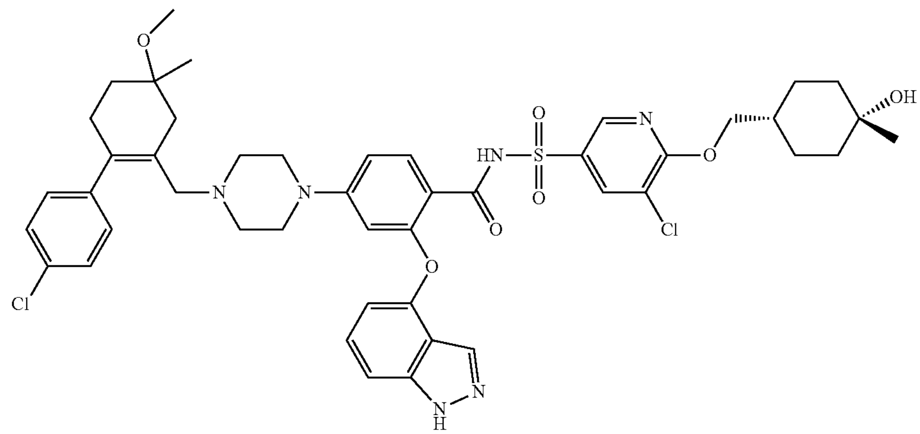 [SMILES: COC1(C)CCC(c2ccc(Cl)cc2)=C(CN2CCN(c3ccc(C(=O)NS(=O)(=O)c4cnc(OC[C@H]5CC[C@@](C)(O)CC5)c(Cl)c4)c(Oc4cccc5[nH]ncc45)c3)CC2)C1] |
| 4-(4-{[2-(4-chloro-phenyl)-4,4-dimethylcyclohex-1-en-1-yl]methyl}piperazin-1-yl)-N-[(5-chloro-6-{[1-(1,3-thiazol-2-yl)piperidin-4-yl]methoxy}pyridin-3-yl)sulfonyl]-2-(1H-indazol-4-yloxy)benzamide | 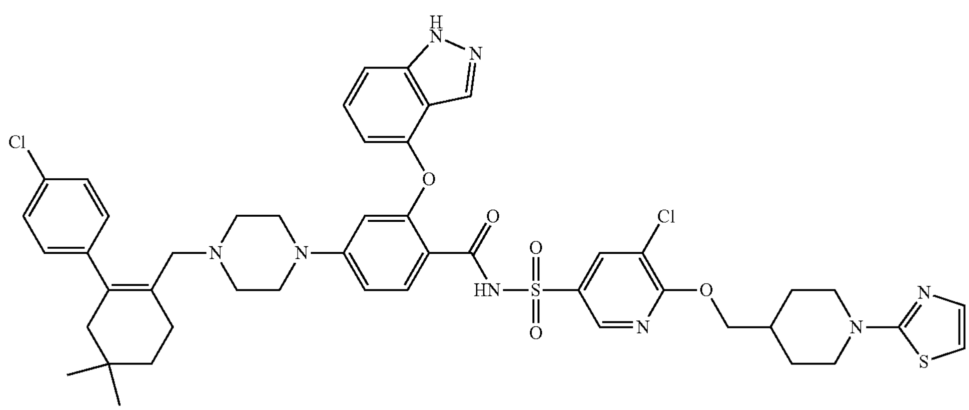 [SMILES: CC1(C)CCC(CN2CCN(c3ccc(C(=O)NS(=O)(=O)c4cnc(OCC5CCN(c6nccs6)CC5)c(Cl)c4)c(Oc4cccc5[nH]ncc45)c3)CC2)=C(c2ccc(Cl)cc2)C1] |
| 4-(4-{[2-(4-chloro-phenyl)-4,4-dimethylcyclohex-1-en-1-yl]methyl}piperazin-1-yl)-N-[(6-{[(cis-4-hydroxy-4-methylcyclohexyl)methyl]amino}-5-nitropyridin-3-yl)sulfonyl]-2-(1H-indazol-4-yloxy)benzamide | 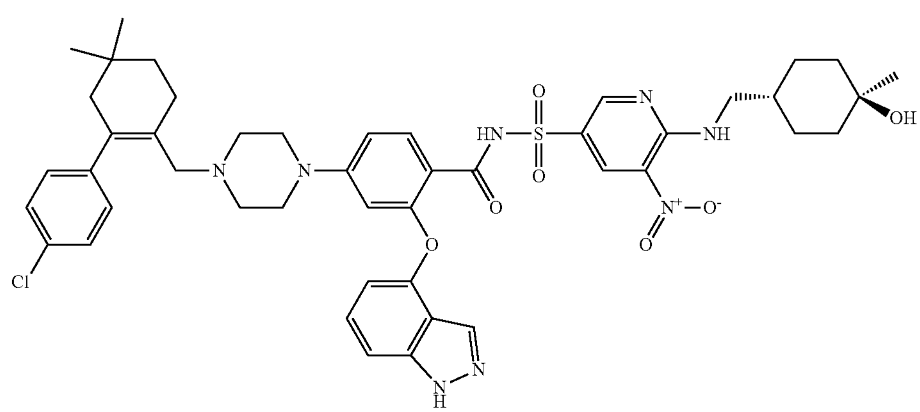 [SMILES: CC1(C)CCC(CN2CCN(c3ccc(C(=O)NS(=O)(=O)c4cnc(NC[C@H]5CC[C@](C)(O)CC5)c([N+](=O)[O-])c4)c(Oc4cccc5[nH]ncc45)c3)CC2)=C(c2ccc(Cl)cc2)C1] |

| Name | Structure |
|---|---|
| 4-(4-{[2-(4-chloro-phenyl)-4,4-dimethylcyclohex-1-en-1-yl]methyl}piperazin-1-yl)-N-({6-[(trans-4-hydroxy-4-methyl-cyclohexyl)methoxy]-5-(trifluoromethyl)pyridin-3-yl}sulfonyl)-2-(1H-indazol-4-yloxy)benzamide | 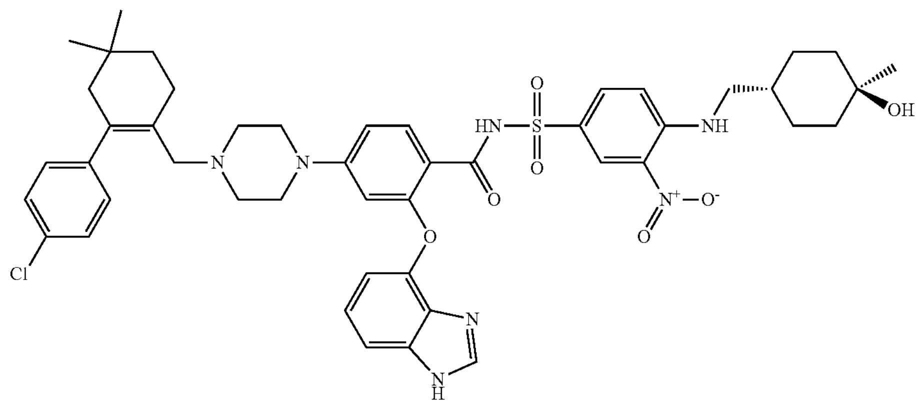 [SMILES: CC1(C)CCC(CN2CCN(c3ccc(C(=O)NS(=O)(=O)c4ccc(NC[C@H]5CC[C@](C)(O)CC5)c([N+](=O)[O-])c4)c(Oc4cccc5[nH]cnc45)c3)CC2)=C(c2ccc(Cl)cc2)C1] |
| 2-(1H-benzimidazol-4-yloxy)-4-(4-{[2-(4-chlorophenyl)-4,4-dimethylcyclohex-1-en-1-yl]methyl}piperazin-1-yl)-N-[(4-{[(cis-4-hydroxy-4-methylcyclohexyl)methyl]amino}-3-nitrophenyl)sulfonyl]benzamide | 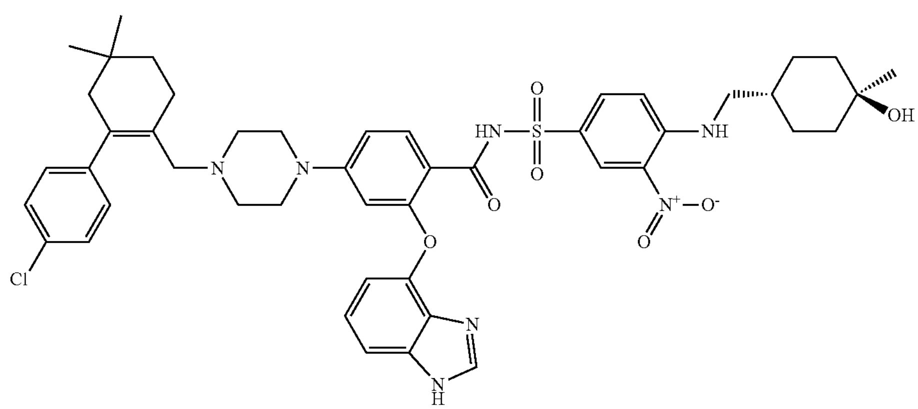 [SMILES: CC1(C)CCC(CN2CCN(c3ccc(C(=O)NS(=O)(=O)c4ccc(NC[C@H]5CC[C@](C)(O)CC5)c([N+](=O)[O-])c4)c(Oc4cccc5[nH]cnc45)c3)CC2)=C(c2ccc(Cl)cc2)C1] |
| N-(4-{[4-(4-{[2-(4-chlorophenyl)-4,4-dimethylcyclohex-1-en-1-yl]methyl}piperazin-1-yl)-2-(1H-indazol-4-yloxy)benzoyl]sulfamoyl}-2-nitrophenyl)-4-cyano-piperidine-1-carboxamide | 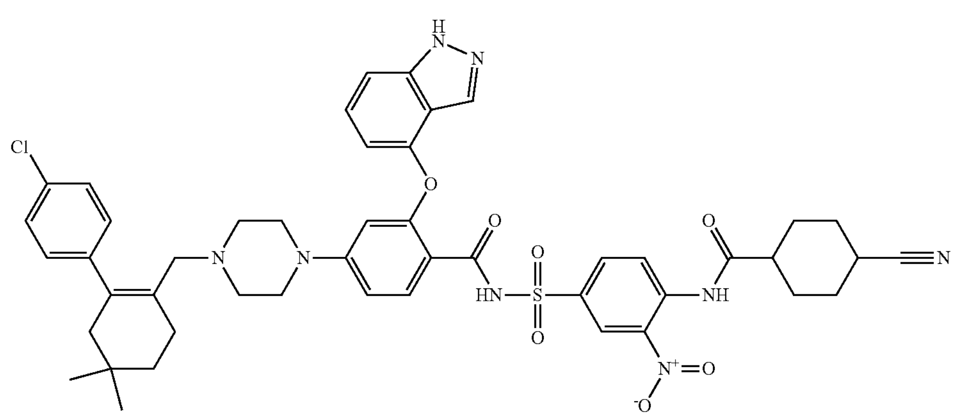 |

In some embodiments, the compound is selected from the group consisting of:

| Name | Structure |
|---|---|
| 4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)-2-phenoxybenzamide | 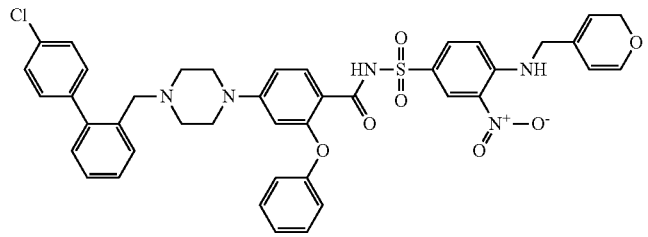 |
| 4-{4-[(4'-chloro-1,1'-biphenyl-2-yl)methyl]piperazin-1-yl}-2-phenoxy-N-({4-[(tetrahydro-2H-pyran-4-ylmethyl)amino]phenyl}sulfonyl)benzamide | 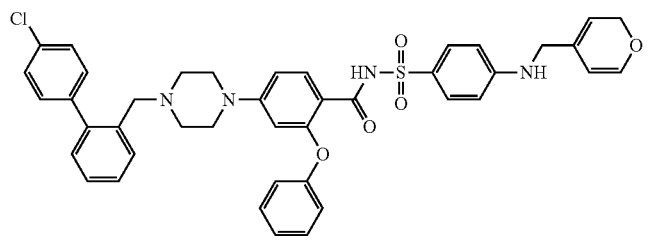 [SMILES: O=C(NS(=O)(=O)c1ccc(NCC2=CCOC=C2)cc1)c1ccc(N2CCN(Cc3ccccc3-c3ccc(Cl)cc3)CC2)cc1Oc1ccccc1] |
| 2-(benzyloxy)-4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)benzamide | 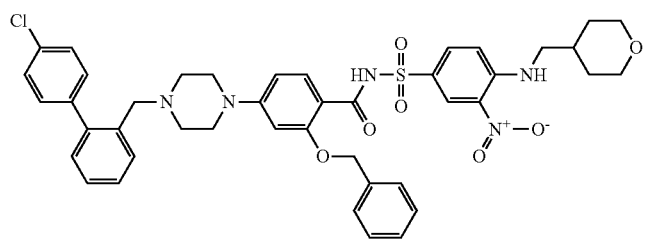 [SMILES: O=C(NS(=O)(=O)c1ccc(NCC2CCOCC2)c([N+](=O)[O-])c1)c1ccc(N2CCN(Cc3ccccc3-c3ccc(Cl)cc3)CC2)cc1OCc1ccccc1] |
| 4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)-2-(2-phenylethoxy)benzamide | 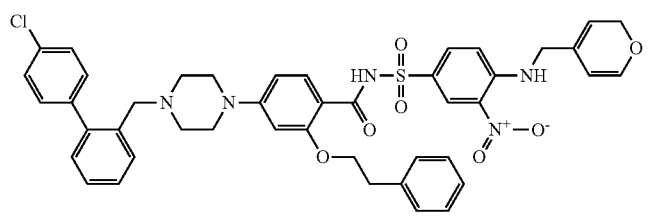 [SMILES: O=C(NS(=O)(=O)c1ccc(NCC2=CCOC=C2)c([N+](=O)[O-])c1)c1ccc(N2CCN(Cc3ccccc3-c3ccc(Cl)cc3)CC2)cc1OCCc1ccccc1] |
| 4-{4-[(4'-chloro 1,1'-biphenyl-2-yl)methyl]piperazin-1-yl}-N-({3-nitro-4-[(tetrahydro-2H-pyran-4-ylmethyl)amino]phenyl}sulfonyl)-2-(phenylthio)benzamide | 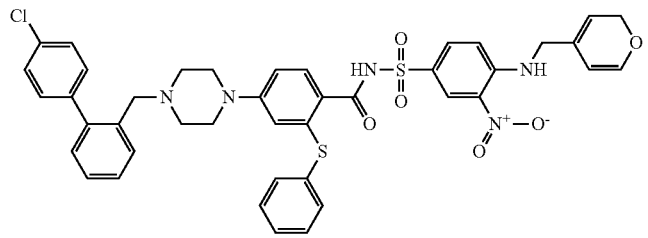 |
| 4-{4-[(4'-chloro-1,1'-biphenyl-2-yl)methyl]piperazin-1-yl}-2-(phenylthio)-N-({4-[(tetrahydro-2H-pyran-4-ylmethyl)amino]phenyl}sulfonyl)benzamide | 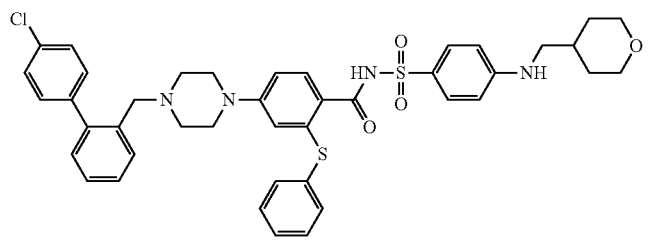 [SMILES: O=C(NS(=O)(=O)c1ccc(NCC2CCOCC2)cc1)c1ccc(N2CCN(Cc3ccccc3-c3ccc(Cl)cc3)CC2)cc1Sc1ccccc1] |

-continued

| Name | Structure |
|---|---|
| 4-{4-[(4'-chloro-1,1'-biphenyl-2-yl)methyl]piperazin-1-yl}-N-({4-[(3-morpholin-4-ylpropyl)amino]-3-nitrophenyl}sulfonyl)-2-(phenylthio)benzamide | 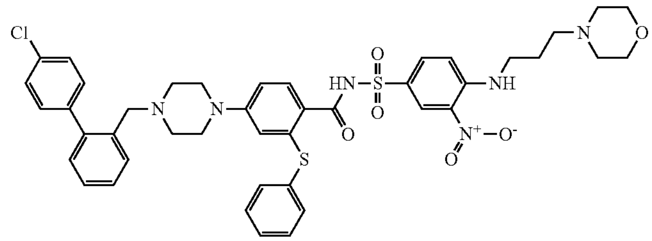 |
| 4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)-2-(phenylsulfonyl)benzamide | |
| 4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)-2-(phenylsulfonyl)benzamide | |
| 2-benzyl-4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)benzamide | 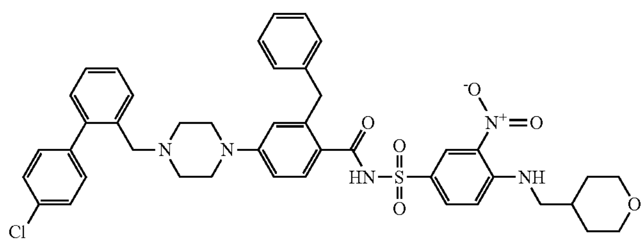 |
| 2-benzyl-4-{4-[(4'-chloro-1,1'-biphenyl-2-yl)methyl]piperazin-1-yl}-N-({4-[(tetrahydro-2H-pyran-4-ylmethyl)amino]phenyl}sulfonyl)benzamide | 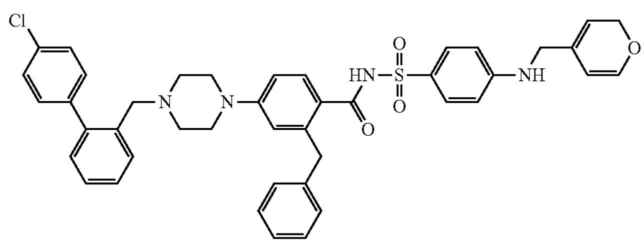 |
| 2-benzyl-4-{4-[(4'-chloro-1,1'-biphenyl-2-yl)methyl]piperazin-1-yl}-N-({4-[(3-morpholin-4-ylpropyl)amino]-3-nitrophenyl}sulfonyl)benzamide | 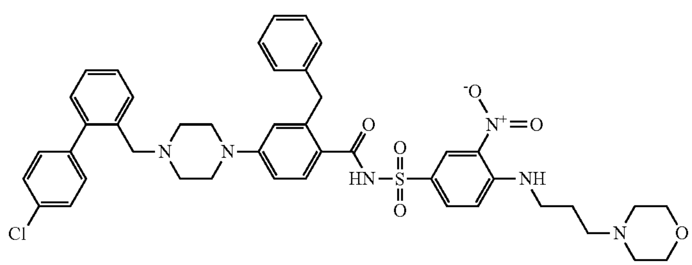 |

-continued

| Name | Structure |
|---|---|
| 4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)-2-(2-phenylethyl)benzamide | 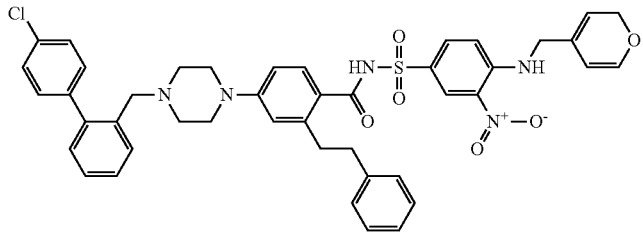 [SMILES: O=C(NS(=O)(=O)c1ccc(NCC2=CCOC=C2)c([N+](=O)[O-])c1)c1ccc(N2CCN(Cc3ccccc3-c3ccc(Cl)cc3)CC2)cc1CCc1ccccc1] |
| 2-(benzylamino)-4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)benzamide | 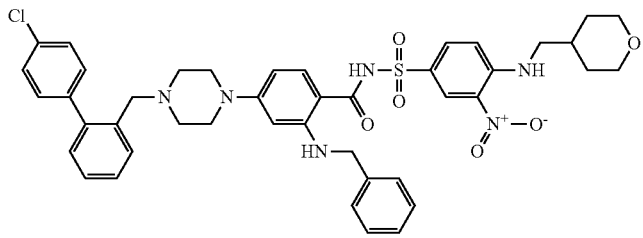 |
| 2-anilino-4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)benzamide | 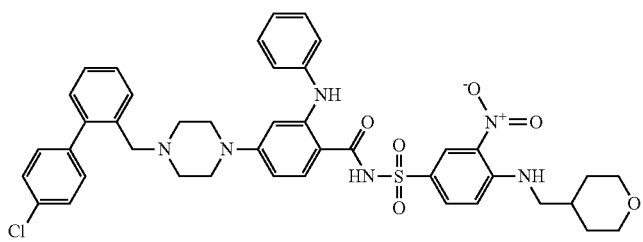 |
| 2-anilino-4-{4-[(4'-chloro-1,1'-biphenyl-2-yl)methyl]piperazin-1-yl}-N-({4-[(tetrahydro-2H-pyran-4-ylmethyl)amino]phenyl}sulfonyl)benzamide | 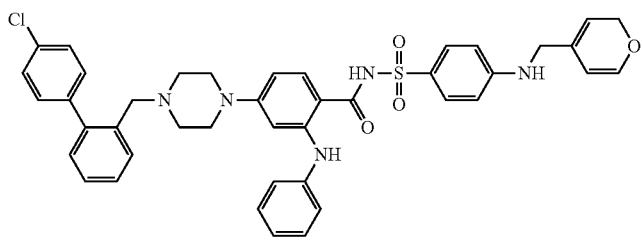 [SMILES: O=C(NS(=O)(=O)c1ccc(NCC2=CCOC=C2)cc1)c1ccc(N2CCN(Cc3ccccc3-c3ccc(Cl)cc3)CC2)cc1Nc1ccccc1] |
| 4-{4-[(4'-chloro-1,1'-biphenyl-2-yl)methyl]piperazin-1-yl}-2-methoxy-N-({3-nitro-4-[(tetrahydro-2H-pyran-4-ylmethyl)amino]phenyl}sulfonyl)benzamide | 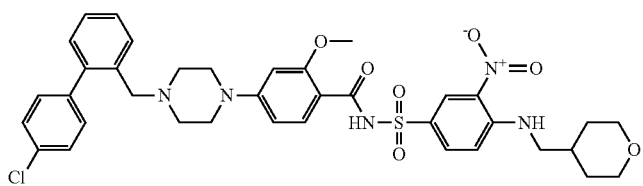 |
| 4-(4-{[2-(4-chlorophenyl)-4,4-dimethylcyclohex-1-en-1-yl]methyl}piperazin-1-yl)-N-({4-[(3-morpholin-4-ylpropyl)amino]-3-nitrophenyl}sulfonyl)-2-phenoxybenzamide | 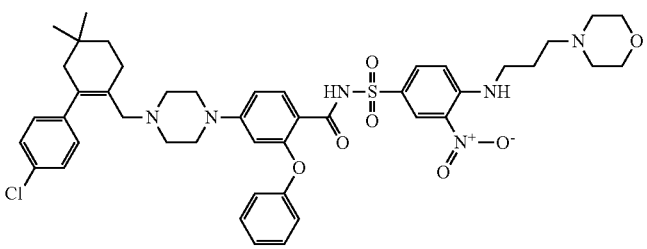 [SMILES: CC1(C)CCC(CN2CCN(c3ccc(C(=O)NS(=O)(=O)c4ccc(NCCCN5CCOCC5)c([N+](=O)[O-])c4)c(Oc4ccccc4)c3)CC2)=C(c2ccc(Cl)cc2)C1] |

-continued

| Name | Structure |
|------|-----------|
| 4-(4-{[2-(4-chlorophenyl)-5,5-dimethylcyclohex-1-en-1-yl]methyl}piperazin-1-yl)-N-({4-[(3-morpholin-4-ylpropyl)amino]-3-nitrophenyl}sulfonyl)-2-phenoxybenzamide | 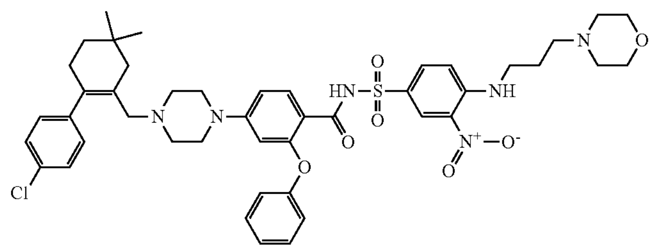 [SMILES: CC1(C)CCC(c2ccc(Cl)cc2)=C(CN2CCN(c3ccc(C(=O)NS(=O)(=O)c4ccc(NCCCN5CCOCC5)c([N+](=O)[O-])c4)c(Oc4ccccc4)c3)CC2)C1] |
| 4-(4-{[2-(4-chlorophenyl)-4,4-dimethylcyclohex-1-en-1-yl]methyl}piperazin-1-yl)-2-(1H-indazol-5-yloxy)-N-({4-[(3-morpholin-4-ylpropyl)amino]-3-nitrophenyl}sulfonyl)benzamide | 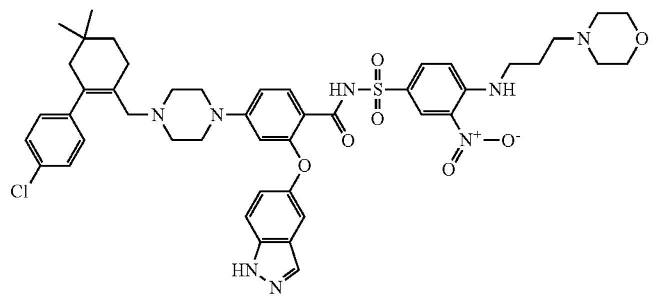 [SMILES: CC1(C)CCC(CN2CCN(c3ccc(C(=O)NS(=O)(=O)c4ccc(NCCCN5CCOCC5)c([N+](=O)[O-])c4)c(Oc4ccc5[nH]ncc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-2-(1H-indazol-5-yloxy)-N-({4-[(1-methylpiperidin-4-yl)amino]-3-nitrophenyl}sulfonyl)benzamide | 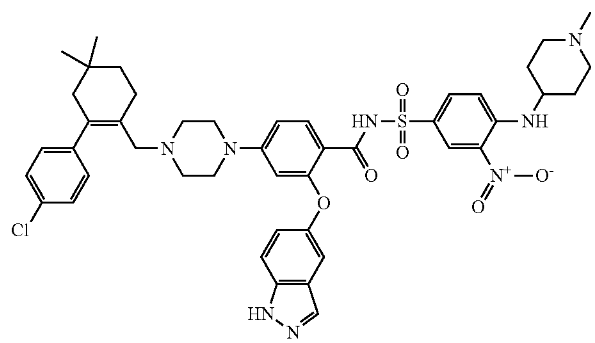 [SMILES: CN1CCC(Nc2ccc(S(=O)(=O)NC(=O)c3ccc(N4CCN(CC5=C(c6ccc(Cl)cc6)CC(C)(C)CC5)CC4)cc3Oc3ccc4[nH]ncc4c3)cc2[N+](=O)[O-])CC1] |
| 4-(4-{[2-(4-chlorophenyl)-4,4-dimethylcyclohex-1-en-1-yl]methyl}piperazin-1-yl)-N-({4-[(3-morpholin-4-ylpropyl)amino]-3-nitrophenyl}sulfonyl)-2-(1,2,3,4-tetrahydroquinolin-6-yloxy)benzamide | 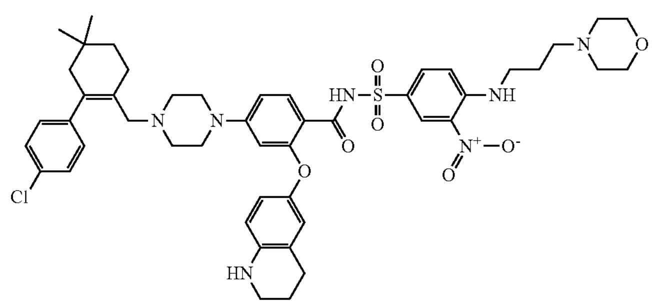 [SMILES: CC1(C)CCC(CN2CCN(c3ccc(C(=O)NS(=O)(=O)c4ccc(NCCCN5CCOCC5)c([N+](=O)[O-])c4)c(Oc4ccc5c(c4)CCCN5)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)-2-(1,2,3,4-tetrahydroquinolin-6-yloxy)benzamide | 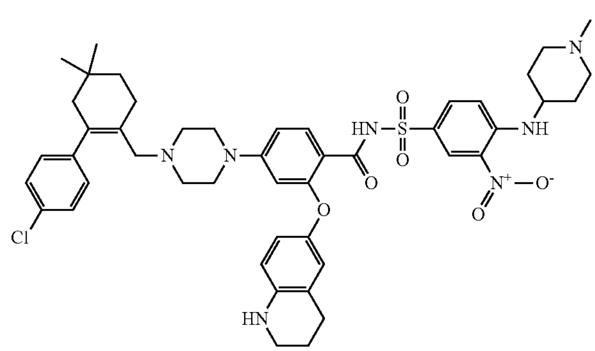 [SMILES: CN1CCC(Nc2ccc(S(=O)(=O)NC(=O)c3ccc(N4CCN(CC5=C(c6ccc(Cl)cc6)CC(C)(C)CC5)CC4)cc3Oc3ccc4c(c3)CCCN4)cc2[N+](=O)[O-])CC1] |

| Name | Structure |
|---|---|
| 4-(4-{[4'-chloro-4-(pyrrolidin-1-ylmethyl)-1,1'-biphenyl-2-yl]methyl}piperazin-1-yl)-2-(1 H-indol-4-yloxy)-N-({3-nitro-4-[(tetrahydro-2H-pyran-4-ylmethyl)amino]phenyl}sulfonyl)benzamide | 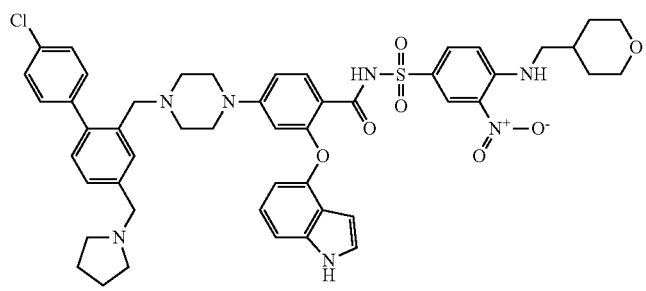 [SMILES: O=C(NS(=O)(=O)c1ccc(NCC2CCOCC2)c([N+](=O)[O-])c1)c1ccc(N2CCN(Cc3cc(CN4CCCC4)ccc3-c3ccc(Cl)cc3)CC2)cc1Oc1cccc2[nH]ccc12] |
| 4-(4-{[4'-chloro-4-(2-pyrrolidin-1-ylethyl)-1,1'-biphenyl-2-yl]methyl}piperazin-1-yl)-2-(1H-indol-4-yloxy)-N-({3-nitro-4-[(tetrahydro-2H-pyran-4-ylmethyl)amino]phenyl}sulfonyl)benzamide | 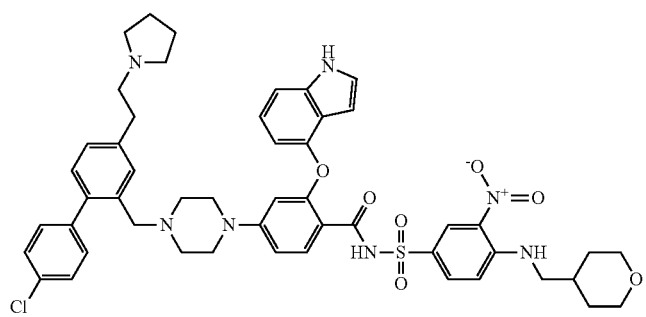 |
| 4-(4-{[2-(4-chlorophenyl)-4,4-dimethylcyclohex-1-en-1-yl]methyl}piperazin-1-yl)-N-({4-[(1-cyclopentylpiperidin-4-yl)amino]-3-nitrophenyl}sulfonyl)-2-(1 H-indol-5-yloxy)benzamide | 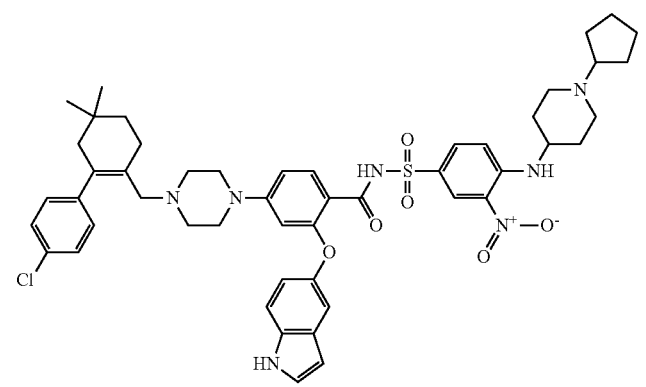 [SMILES: CC1(C)CCC(CN2CCN(c3ccc(C(=O)NS(=O)(=O)c4ccc(NC5CCN(C6CCCC6)CC5)c([N+](=O)[O-])c4)c(Oc4ccc5[nH]ccc5c4)c3)CC2)=C(c2ccc(Cl)cc2)C1] |
| 4-{4-[(4'-chloro-1,1'-biphenyl-2-yl)methyl]-3-isobutylpiperazin-1-yl}-N-({3-nitrol-4-[(tetrahydro-2H-pyran-4-ylmethyl)amino]phenyl}sulfonyl)-2-phenoxybenzamide | 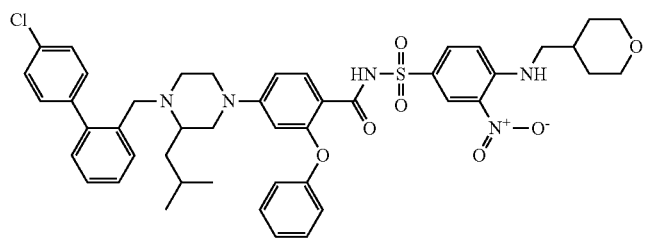 [SMILES: CC(C)CC1CN(c2ccc(C(=O)NS(=O)(=O)c3ccc(NCC4CCOCC4)c([N+](=O)[O-])c3)c(Oc3ccccc3)c2)CCN1Cc1ccccc1-c1ccc(Cl)cc1] |
| 4-{4-[(4'-chloro-1,1'-biphenyl-2-yl)methyl]piperazin-1-yl}-N-{[4-(2,4-dioxo-3-azabicyclo[3.2.0]hept-3-yl)phenyl]sulfonyl}-2-phenoxybenzamide | 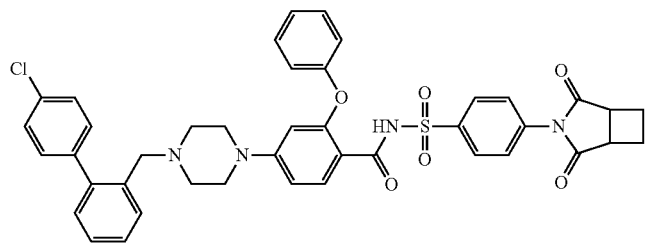 [SMILES: O=C(NS(=O)(=O)c1ccc(N2C(=O)C3CCC3C2=O)cc1)c1ccc(N2CCN(Cc3ccccc3-c3ccc(Cl)cc3)CC2)cc1Oc1ccccc1] |

-continued

| Name | Structure |
|---|---|
| 4-{4-[(4'-chloro-1,1'-biphenyl-2-yl)methyl]piperazin-1-yl}-N-{[4-(4-methyl-6-oxo-1,4,5,6-tetrahydropyridazin-3-yl)phenyl]sulfonyl}-2-phenoxybenzamide | 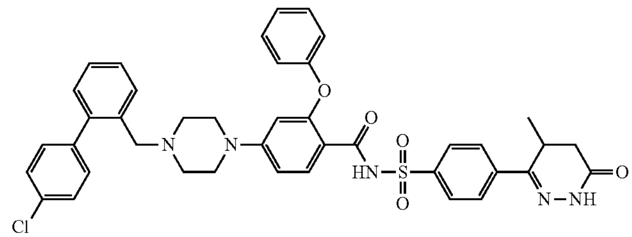 [SMILES: CC1CC(=O)NN=C1c1ccc(S(=O)(=O)NC(=O)c2ccc(N3CCN(Cc4ccccc4-c4ccc(Cl)cc4)CC3)cc2Oc2ccccc2)cc1] |
| 4-{4-[(4'-chloro-1,1'-biphenyl-2-yl)methyl]piperazin-1-yl}-N-{[4-(3,3-dimethyl-2-oxoazetidin-1-yl)phenyl]sulfonyl}-2-phenoxybenzamide | 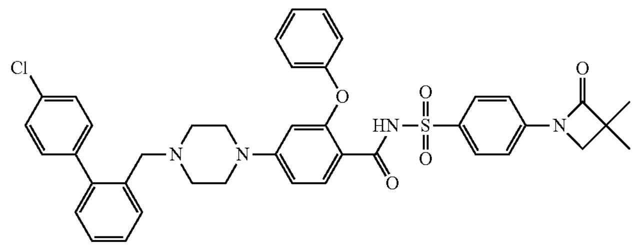 [SMILES: CC1(C)CN(c2ccc(S(=O)(=O)NC(=O)c3ccc(N4CCN(Cc5ccccc5-c5ccc(Cl)cc5)CC4)cc3Oc3ccccc3)cc2)C1=O] |
| 4-{4-[(4'-chloro-1,1'-biphenyl-2-yl)methyl]piperazin-1-yl}-N-{[4-(4-nitro-2H-1,2,3-triazol-2-yl)phenyl]sulfonyl}-2-phenoxybenzamide | 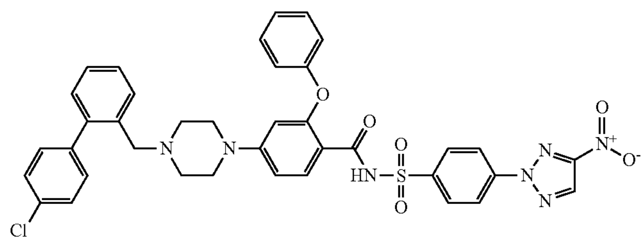 [SMILES: O=C(NS(=O)(=O)c1ccc(-n2ncc([N+](=O)[O-])n2)cc1)c1ccc(N2CCN(Cc3ccccc3-c3ccc(Cl)cc3)CC2)cc1Oc1ccccc1] |
| 4-{4-[(4'-chloro-1,1'-biphenyl-2-yl)methyl]piperazin-1-yl}-2-phenoxy-N-{[2-(2-piperidin-1-ylethoxy)phenyl]sulfonyl}benzamide | 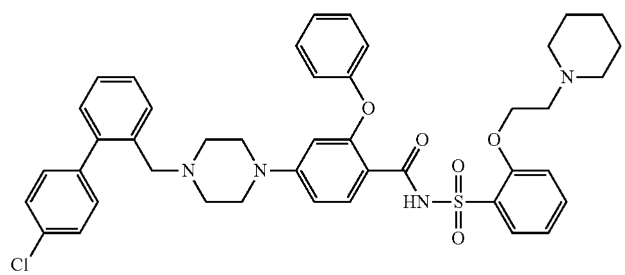 [SMILES: O=C(NS(=O)(=O)c1ccccc1OCCN1CCCCC1)c1ccc(N2CCN(Cc3ccccc3-c3ccc(Cl)cc3)CC2)cc1Oc1ccccc1] |
| 4-{4-[(4'-chloro-1,1'-biphenyl-2-yl)methyl]piperazin-1-yl}-N-{[3-({[(1-ethylpyrrolidin-2-yl)methyl]amino}carbonyl)-4-methoxyphenyl]sulfonyl}-2-phenoxybenzamide | 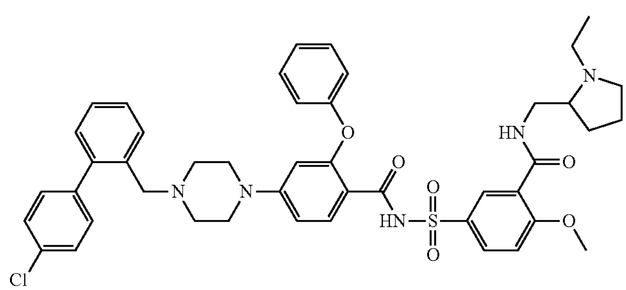 [SMILES: CCN1CCCC1CNC(=O)c1cc(S(=O)(=O)NC(=O)c2ccc(N3CCN(Cc4ccccc4-c4ccc(Cl)cc4)CC3)cc2Oc2ccccc2)ccc1OC] |
| 4-{4-[(4'-chloro-1,1'-biphenyl-2-yl)methyl]piperazin-1-yl}-2-(1-naphthyloxy)-N-({3-nitro-4[(tetrahydro-2H-pyran-4-ylmethyl)amino]phenyl}sulfonyl)benzamide | 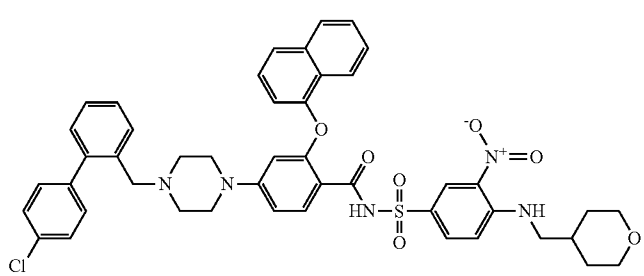 |

| Name | Structure |
|---|---|
| 4-{4-[(4'-chloro-1,1'-biphenyl-2-yl)methyl]piperazin-1-yl}-2-(2-naphthyloxy)-N-({3-nitro-4-[(tetrahydro-2H-pyran-4-ylmethyl)amino]phenyl}sulfonyl)benzamide | 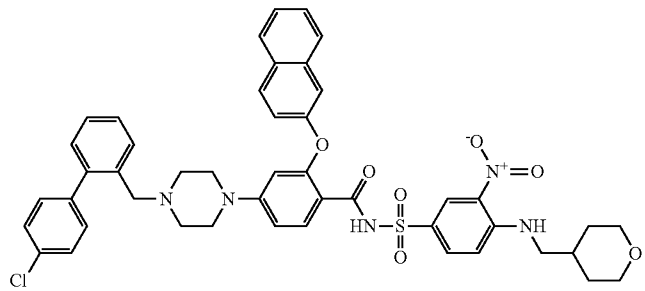 |
| 4-{4-[(4'-chloro-1,1'-biphenyl-2-yl)methyl]piperazin-1-yl}-N-({4-[(3-morpholin-4-ylpropyl)amino]-3-nitrophenyl}sulfonyl)-2-(2-naphthyloxy)benzamide | 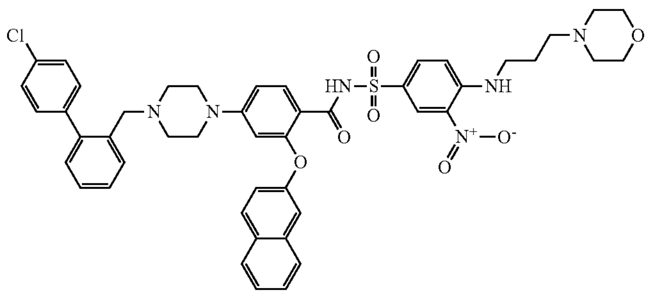 [SMILES: O=C(NS(=O)(=O)c1ccc(NCCCN2CCOCC2)c([N+](=O)[O-])c1)c1ccc(N2CCN(Cc3ccccc3-c3ccc(Cl)cc3)CC2)cc1Oc1ccc2ccccc2c1] |
| 4-{4-[(4'-chloro-1,1'-biphenyl-2-yl)methyl]piperazin-1-yl}-2-(2-naphthyloxy)-N-({4-[(tetrahydro-2H-pyran-4-ylmethyl)amino]-3-[(trifluoromethyl)sulfonyl]phenyl}sulfonyl)benzamide | 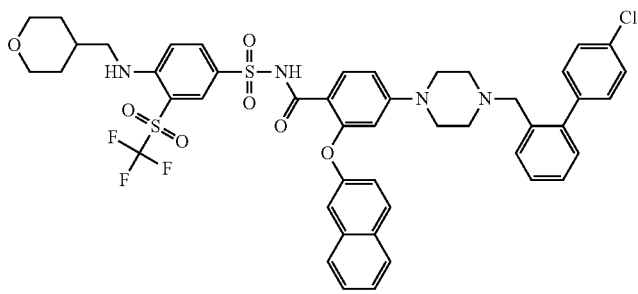 [SMILES: O=C(NS(=O)(=O)c1ccc(NCC2CCOCC2)c(S(=O)(=O)C(F)(F)F)c1)c1ccc(N2CCN(Cc3ccccc3-c3ccc(Cl)cc3)CC2)cc1Oc1ccc2ccccc2c1] |
| 4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)-2-(quinolin-7-yloxy)benzamide | 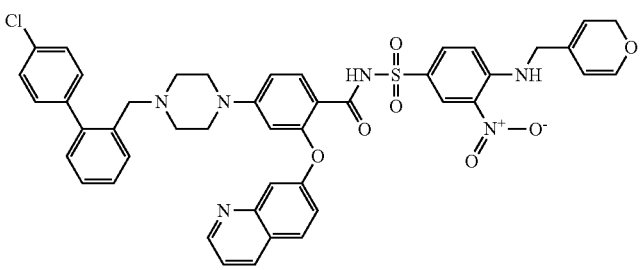 [SMILES: O=C(NS(=O)(=O)c1ccc(NCC2=CCOC=C2)c([N+](=O)[O-])c1)c1ccc(N2CCN(Cc3ccccc3-c3ccc(Cl)cc3)CC2)cc1Oc1ccc2cccnc2c1] |
| 4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)-2-(quinolin-6-yloxy)benzamide | 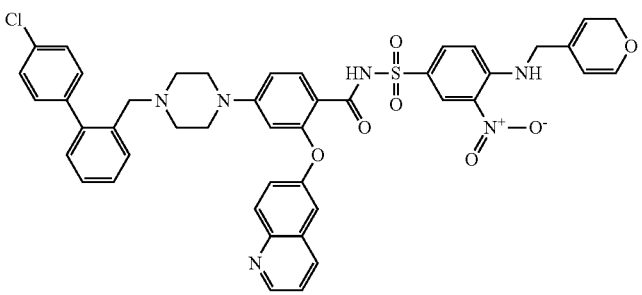 [SMILES: O=C(NS(=O)(=O)c1ccc(NCC2=CCOC=C2)c([N+](=O)[O-])c1)c1ccc(N2CCN(Cc3ccccc3-c3ccc(Cl)cc3)CC2)cc1Oc1ccc2ncccc2c1] |

| Name | Structure |
|---|---|
| 4-{4-[(4'-chloro-1,1'-biphenyl-2-yl)methyl]piperazin-1-yl}-2-(1 H-indol-5-yloxy)-N-({3-nitro-4-[(tetrahydro-2H-pyran-4-ylmethyl)amino]phenyl}sulfonyl)benzamide | 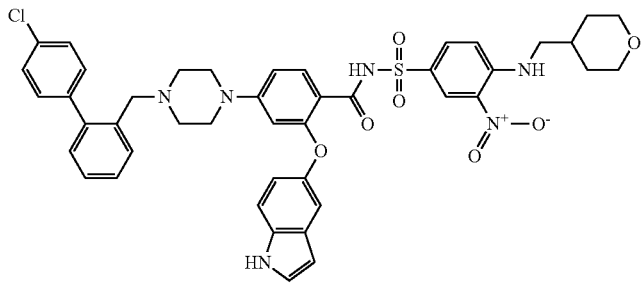 [SMILES: O=C(NS(=O)(=O)c1ccc(NCC2CCOCC2)c([N+](=O)[O-])c1)c1ccc(N2CCN(Cc3ccccc3-c3ccc(Cl)cc3)CC2)cc1Oc1ccc2[nH]ccc2c1] |
| 4-{4-[(4'-chloro-1,1'-biphenyl-2-yl)methyl]piperazin-1-yl}-2-(isoquinolin-5-yloxy)-N-({3-nitro-4-[(tetrahydro-2H-pyran-4-ylmethyl)amino]phenyl}sulfonyl)benzamide | 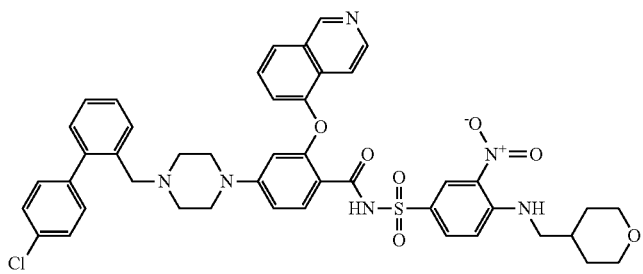 |
| 4-{4-[(4'-chloro-1,1'-biphenyl-2-yl)methyl]piperazin-1-yl}-N-[(4-{[3-(dimethylamino)propyl]amino}-3-nitrophenyl)sulfonyl]-2-(isoquinolin-5-yloxy)benzamide | 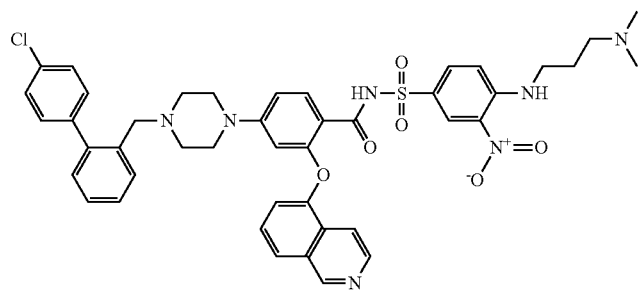 |
| 4-{4-[(4'-chloro-1,1'-biphenyl-2-yl)methyl]piperazin-1-yl}-N-[(4-{[3-(dimethylamino)propyl]amino}-3-nitrophenyl)sulfonyl]-2-(quinolin-6-yloxy)benzamide | 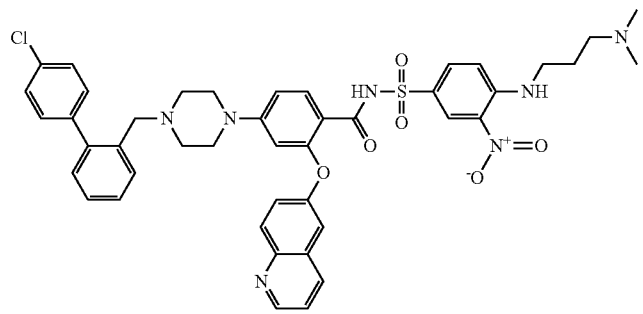 |
| 4-{4-[(4'-chloro-1,1'-biphenyl-2-yl)methyl]piperazin-1-yl}-N-[(4-{[3-(dimethylamino)propyl]amino}-3-nitrophenyl)sulfonyl]-2-(1 H-indol-5-yloxy)benzamide | 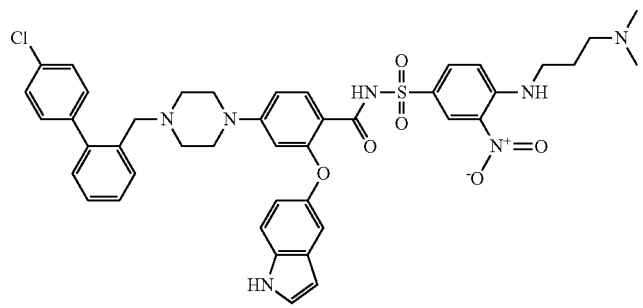 |

| Name | Structure |
|---|---|
| 4-{4-[(4'-chloro-1,1'-biphenyl-2-yl)methyl]piperazin-1-yl}-2-(1H-indol-4-yloxy)-N-({3-nitro-4-[(tetrahydro-2H-pyran-4-ylmethyl)amino]phenyl}sulfonyl)benzamide | 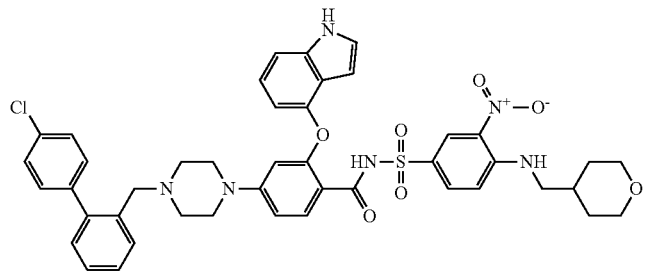 [SMILES: O=C(NS(=O)(=O)c1ccc(NCC2CCOCC2)c([N+](=O)[O-])c1)c1ccc(N2CCN(Cc3ccccc3-c3ccc(Cl)cc3)CC2)cc1Oc1cccc2[nH]ccc12] |
| 4-{4-[(4'-chloro-1,1'-biphenyl-2-yl)methyl]piperazin-1-yl}-N-[(4-{[3-(dimethylamino)propyl]amino}-3-nitrophenyl)sulfonyl]-2-(1H-indol-4-yloxy)benzamide | 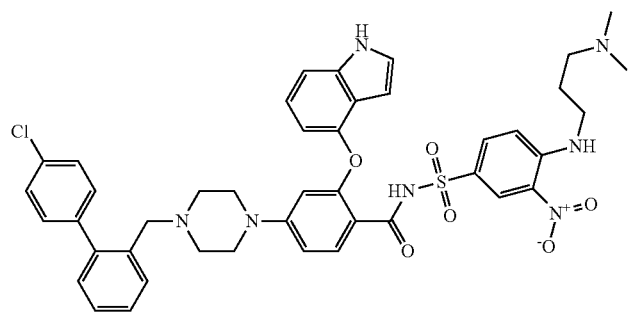 |
| 4-{4-[(4'-chloro-1,1'-biphenyl-2-yl)methyl]piperazin-1-yl}-N-[(4-{[3-(dimethylamino)propyl]amino}-3-nitrophenyl)sulfonyl]-2-(1H-indol-6-yloxy)benzamide | 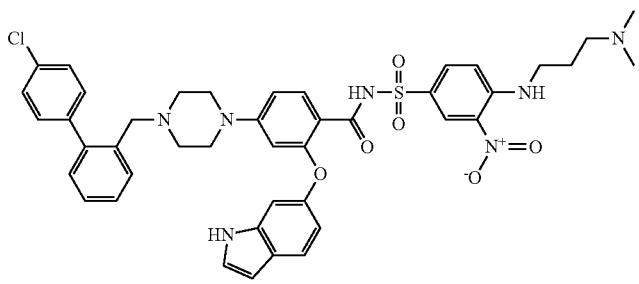 |
| 4-{4-[(4'-chloro-1,1'-biphenyl-2-yl)methyl]piperazin-1-yl}-2-(isoquinolin-7-yloxy)-N-({4-[(3-morpholin-4-ylpropyl)amino]-3-nitrophenyl}sulfonyl)benzamide | 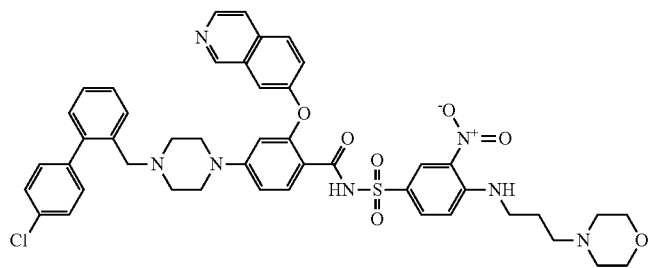 |
| 4-{4-[(4'-chloro-1,1'-biphenyl-2-yl)methyl]piperazin-1-yl}-N-[(4-{[3-(dimethylamino)propyl]amino}-3-nitrophenyl)sulfonyl]-2-(isoquinolin-7-yloxy)benzamide | 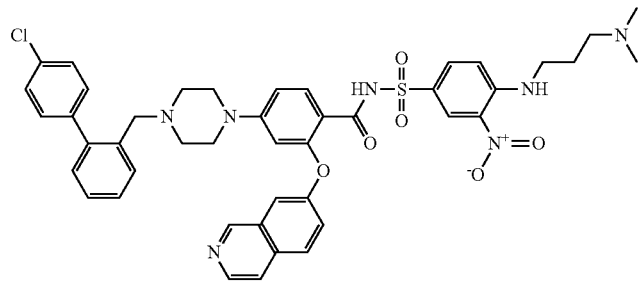 |

-continued

| Name | Structure |
|---|---|
| 4-(4-{[2-(4-chlorophenyl)-5,5-dimethylcyclohex-1-en-1-yl]methyl}piperazin-1-yl)-2-(1H-indol-5-yloxy)-N-({4-[(3-morpholin-4-ylpropyl)amino]-3-nitrophenyl}sulfonyl)benzamide | 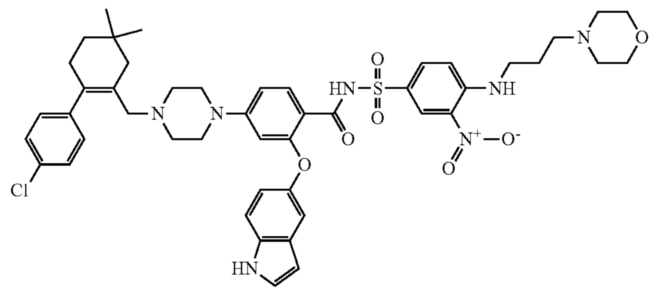 [SMILES: CC1(C)CCC(c2ccc(Cl)cc2)=C(CN2CCN(c3ccc(C(=O)NS(=O)(=O)c4ccc(NCCCN5CCOCC5)c([N+](=O)[O-])c4)c(Oc4ccc5[nH]ccc5c4)c3)CC2)C1] |
| 4-(4-{[2-(4-chlorophenyl)-5,5-dimethylcyclohex-1-en-1-yl]methyl}piperazin-1-yl)-N-[(4-{[3-(dimethylamino)propyl]amino}-3-nitrophenyl)sulfonyl]-2-(1H-indol-5-yloxy)benzamide | 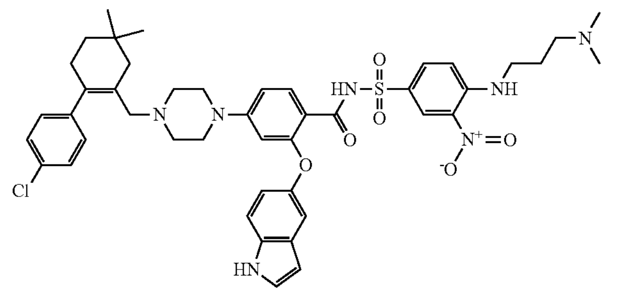 |
| 4-(4-{[2-(4-chlorophenyl)-4,4-dimethylcyclohex-1-en-1-yl]methyl}piperazin-1-yl)-2-(1H-indol-5-yloxy)-N-({4-[(3-morpholin-4-ylpropyl)amino]-3-nitrophenyl}sulfonyl)benzamide | 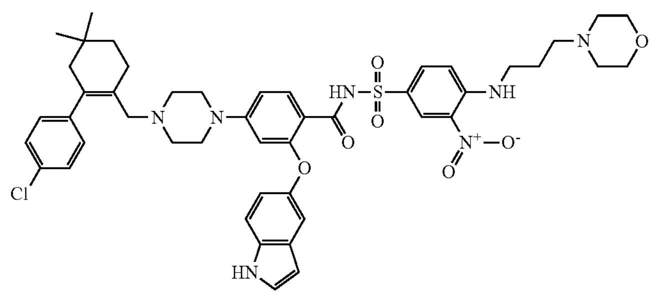 [SMILES: CC1(C)CCC(CN2CCN(c3ccc(C(=O)NS(=O)(=O)c4ccc(NCCCN5CCOCC5)c([N+](=O)[O-])c4)c(Oc4ccc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-[(4-{[3-(dimethylamino)propyl]amino}-3-nitrophenyl)sulfonyl]-2-(1H-indol-5-yloxy)benzamide | 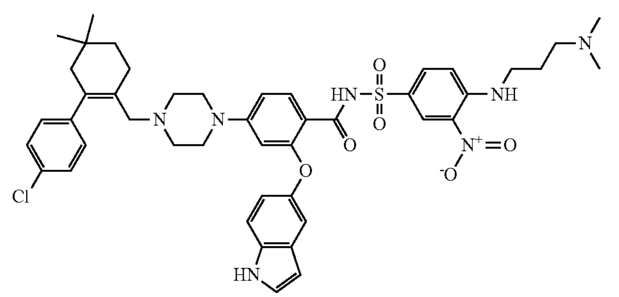 |
| 4-(4-{[2-(4-chlorophenyl)-5,5-dimethylcyclohex-1-en-1-yl]methyl}piperazin-1-yl)-2-(1H-indol-4-yloxy)-N-({4-[(3-morpholin-4-ylpropyl)amino]-3-nitrophenyl}sulfonyl)benzamide | 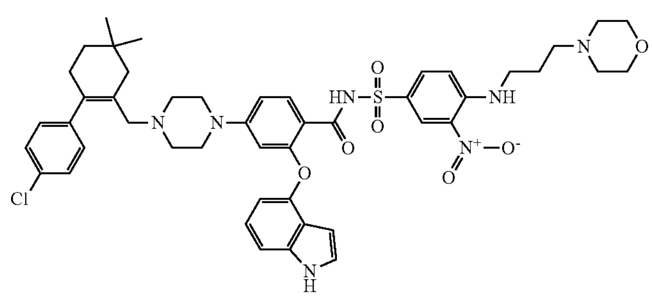 [SMILES: CC1(C)CCC(c2ccc(Cl)cc2)=C(CN2CCN(c3ccc(C(=O)NS(=O)(=O)c4ccc(NCCCN5CCOCC5)c([N+](=O)[O-])c4)c(Oc4cccc5[nH]ccc45)c3)CC2)C1] |

| Name | Structure |
|---|---|
| 4-(4-{[2-(4-chlorophenyl)-4,4-dimethylcyclohex-1-en-1-yl]methyl}piperazin-1-yl)-2-(1H-indol-4-yloxy)-N-({4-[(3-morpholin-4-ylpropylamino]-3-nitrophenyl}sulfonyl)benzamide | 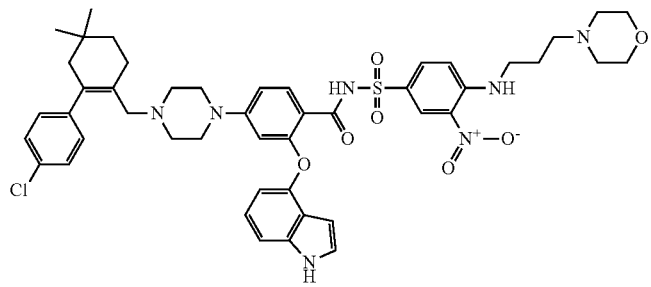 [SMILES: CC1(C)CCC(CN2CCN(c3ccc(C(=O)NS(=O)(=O)c4ccc(NCCCN5CCOCC5)c([N+](=O)[O-])c4)c(Oc4cccc5[nH]ccc45)c3)CC2)=C(c2ccc(Cl)cc2)C1] |
| 4-(4-{[2-(4-chlorophenyl)-5,5-dimethylcyclohex-1-en-1-yl]methyl}piperazin-1-yl)-N-[(4-{[3-(dimethylamino)propyl]amino}-3-nitrophenyl)sulfonyl]-2-(1H-indol-4-yloxy)benzamide | 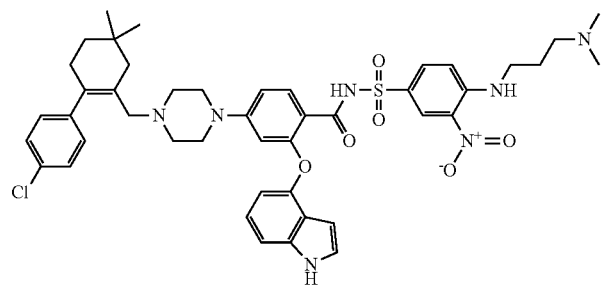 |
| 4-(4-{[2-(4-chlorophenyl)-4,4-dimethylcyclohex-1-en-1-yl]methyl}piperazin-1-yl)-N-[(4-{[3-(dimethylamino)propyl]amino}-3-nitrophenyl)sulfonyl]-2-(1H-indol-4-yloxy)benzamide | 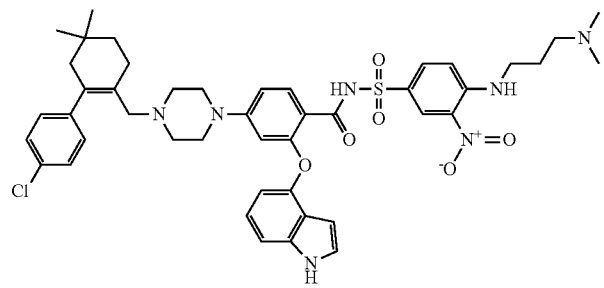 |
| 4-{4-[(4'-chloro-1,1'-biphenyl-2-yl)methyl]piperazin-1-yl}-2-(1H-indol-y-yloxy)-N-({4-[(3-morpholin-4-ylpropyl)amino]-3-nitrophenyl}sulfonyl)benzamide | 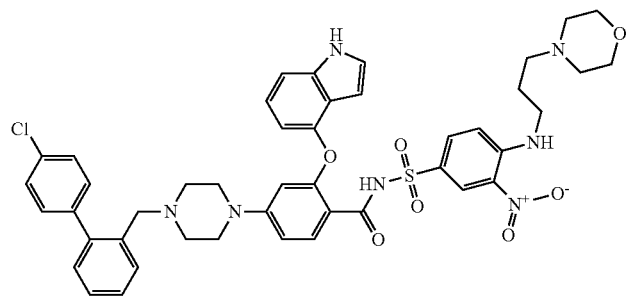 [SMILES: O=C(NS(=O)(=O)c1ccc(NCCCN2CCOCC2)c([N+](=O)[O-])c1)c1ccc(N2CCN(Cc3ccccc3-c3ccc(Cl)cc3)CC2)cc1Oc1cccc2[nH]ccc12] |
| 4-{4-[(4'-chloro-1,1'-biphenyl-2-yl)methyl]piperazin-1-yl}-2-(1H-indol-5-yloxy)-N-({4-[(3-morpholin-4-ylpropyl)amino]-3-nitrophenyl}sulfonyl)benzamide | 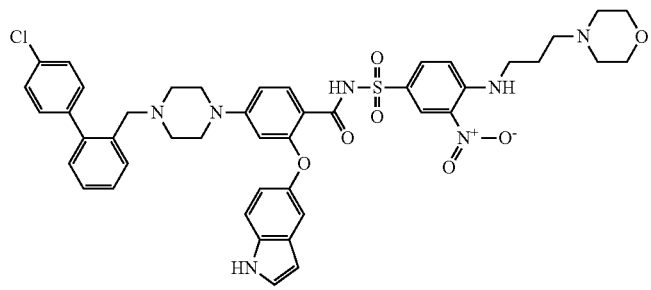 [SMILES: O=C(NS(=O)(=O)c1ccc(NCCCN2CCOCC2)c([N+](=O)[O-])c1)c1ccc(N2CCN(Cc3ccccc3-c3ccc(Cl)cc3)CC2)cc1Oc1ccc2[nH]ccc2c1] |

| Name | Structure |
|---|---|
| 4-{4-[(4'-chloro-1,1'-biphenyl-2-yl)methyl]piperazin-1-yl}-N-[(4-methoxyphenyl)sulfonyl]-2-phenoxybenzamide | 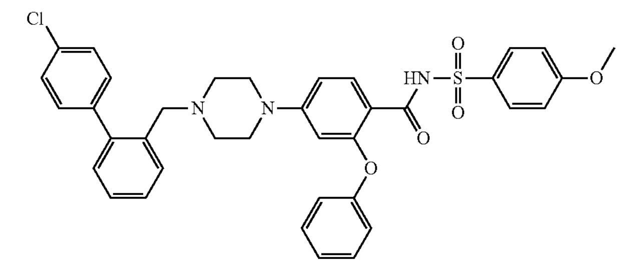 [SMILES: COc1ccc(S(=O)(=O)NC(=O)c2ccc(N3CCN(Cc4ccccc4-c4ccc(Cl)cc4)CC3)cc2Oc2ccccc2)cc1] |
| 4-{4-[(4'-chloro-1,'-biphenyl-2-yl)methyl]piperazin-1-yl}-N-[(4-methylphenyl)sulfonyl]-2-phenoxybenzamide | 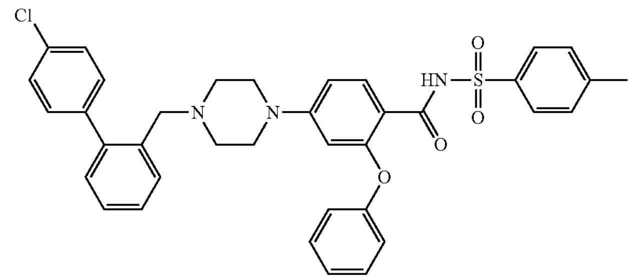 [SMILES: Cc1ccc(S(=O)(=O)NC(=O)c2ccc(N3CCN(Cc4ccccc4-c4ccc(Cl)cc4)CC3)cc2Oc2ccccc2)cc1] |
| 4-{4-[(4'-chloro-1,1'-biphenyl-2-yl)methyl]piperazin-1-yl}-2-(1H-indol-5-yloxy)-N-({4-[(tetrahydro-2H-pyran-4-ylmethyl)amino]-3-[(trifluoromethyl)sulfonyl]phenyl}sulfonyl)benzamide | 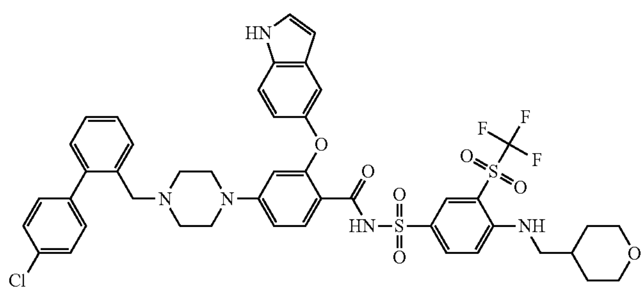 [SMILES: O=C(NS(=O)(=O)c1ccc(NCC2CCOCC2)c(S(=O)(=O)C(F)(F)F)c1)c1ccc(N2CCN(Cc3ccccc3-c3ccc(Cl)cc3)CC2)cc1Oc1ccc2[nH]ccc2c1] |
| 4-{4-[(4'-chloro-1,1'-biphenyl-2-yl)methyl]piperazin-1-yl}-2-(1H-indol-4-yloxy)-N-({4-[(tetrahydro-2H-pyran-4-ylmethyl)amino]-3-[(trifluoromethyl)sulfonyl]phenyl}sulfonyl)benzamide | 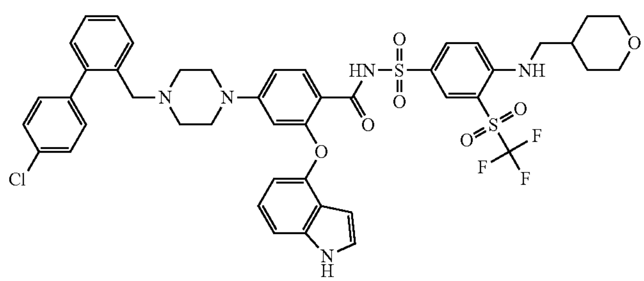 [SMILES: O=C(NS(=O)(=O)c1ccc(NCC2CCOCC2)c(S(=O)(=O)C(F)(F)F)c1)c1ccc(N2CCN(Cc3ccccc3-c3ccc(Cl)cc3)CC2)cc1Oc1cccc2[nH]ccc12] |
| 4-{4-[(4'-chloro-1,1'-biphenyl-2-yl)methyl]piperazin-1-yl}-N-({4-{[3-(dimethylamino)propyl]amino}-3-[(trifluoromethyl)sulfonyl]phenyl}sulfonyl)-2-(1H-indol-5-yloxy)benzamide | 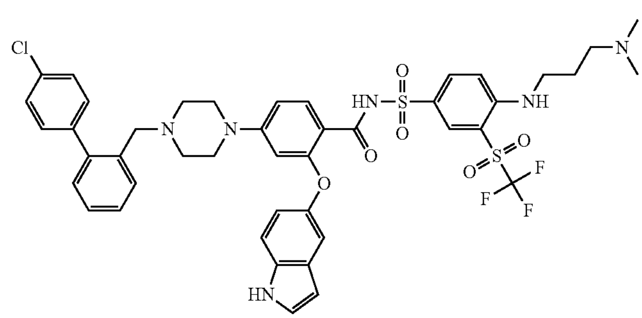 [SMILES: CN(C)CCCNc1ccc(S(=O)(=O)NC(=O)c2ccc(N3CCN(Cc4ccccc4-c4ccc(Cl)cc4)CC3)cc2Oc2ccc3[nH]ccc3c2)cc1S(=O)(=O)C(F)(F)F] |

-continued

| Name | Structure |
|---|---|
| 4-{4-[(4'-chloro-1,1'-biphenyl-2-yl)methyl]piperazin-1-yl}-2-(1H-indol-4-yloxy)-N-({4-[(3-morpholin-4-ylpropyl)amino]-3-[(trifluoromethyl)sulfonyl]phenyl}sulfonyl)benzamide | 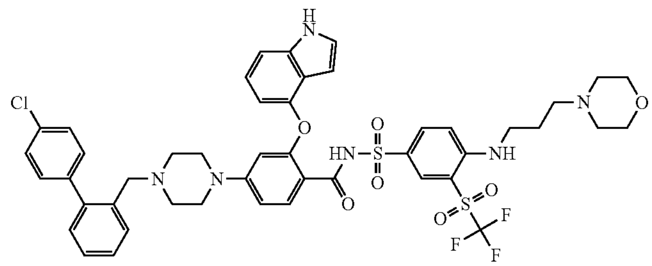 [SMILES: O=C(NS(=O)(=O)c1ccc(NCCCN2CCOCC2)c(S(=O)(=O)C(F)(F)F)c1)c1ccc(N2CCN(Cc3ccccc3-c3ccc(Cl)cc3)CC2)cc1Oc1cccc2[nH]ccc12] |
| N-[(3-{[chloro(difluoro)methyl]sulfonyl}-4-{[3(dimethylamino)propyl]amino}phenyl)sulfonyl]-4-(4-{[2-(4-chlorophenyl)-4,4-dimethylcyclohex-1-en-1-yl]methyl}piperazin-1-yl)-2-(1H-indol-4-yloxy)benzamide | 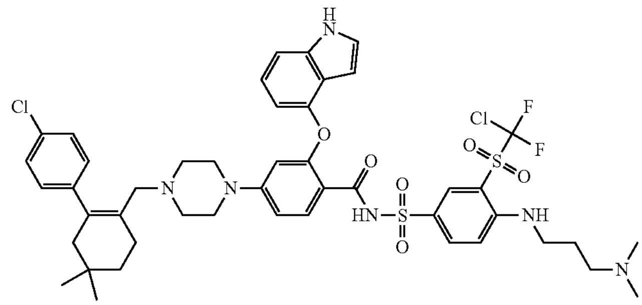 [SMILES: CN(C)CCCNc1ccc(S(=O)(=O)NC(=O)c2ccc(N3CCN(CC4=C(c5ccc(Cl)cc5)CC(C)(C)CC4)CC3)cc2Oc2cccc3[nH]ccc23)cc1S(=O)(=O)C(F)(F)Cl] |
| N-[(3-{[chloro(difluoro)methyl]sulfonyl}-4-{[3-(dimethylamino)propyl]amino}phenyl)sulfonyl]-4-(4-{[2-(4-chlorophenyl)-4,4-dimethylcyclohex-1-en-1-yl]methyl}piperazin-1-yl)-2-(1H-indol-5-yloxy)benzamide | 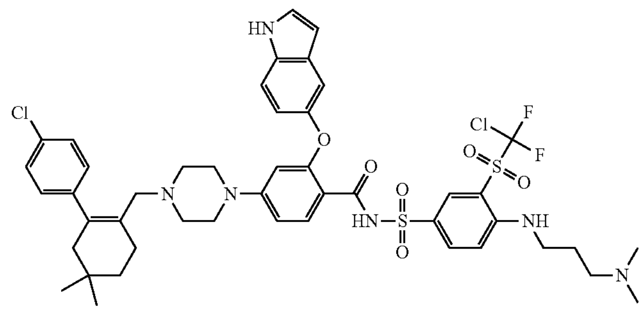 [SMILES: CN(C)CCCNc1ccc(S(=O)(=O)NC(=O)c2ccc(N3CCN(CC4=C(c5ccc(Cl)cc5)CC(C)(C)CC4)CC3)cc2Oc2ccc3[nH]ccc3c2)cc1S(=O)(=O)C(F)(F)Cl] |
| 2-(1H-indol-4-yloxy)-4-(4-{[2-(4-methoxyphenyl)-4,4-dimethylcyclohex-1-en-1-yl]methyl}piperazin-1-yl)-N-({3-nitro-4-[(3-pyrrolidin-1-ylpropyl)amino]phenyl}sulfonyl)benzamide | 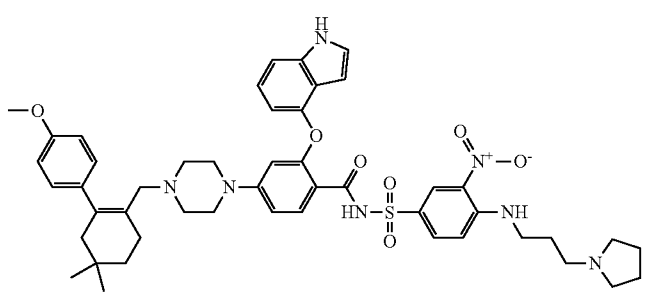 [SMILES: COc1ccc(C2=C(CN3CCN(c4ccc(C(=O)NS(=O)(=O)c5ccc(NCCCN6CCCC6)c([N+](=O)[O-])c5)c(Oc5cccc6[nH]ccc56)c4)CC3)CCC(C)(C)C2)cc1] |
| 4-[4-({4,4-dimethyl-2-[4-(trifluoromethyl)phenyl]cyclohex-1-en-1-yl}methyl)piperazin-1-yl]-2-(1H-indol-4-yloxy)-N-({3-nitro-4-[(3-pyrrolidin-1-ylpropyl)amino]phenyl}sulfonyl)benzamide | 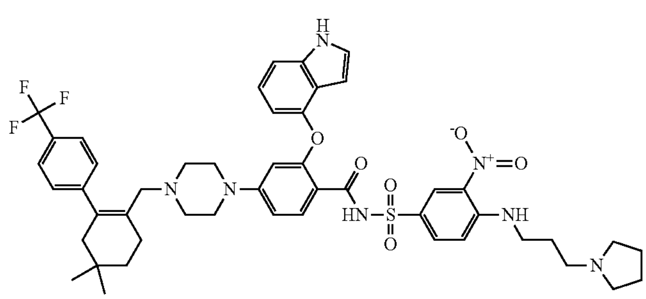 |

| Name | Structure |
|------|-----------|
| 4-[4-({4,4-dimethyl-2-[4-(trifluoromethoxy)phenyl]cyclohex-1-en-1-yl}methyl)piperazin-1-yl]-2-(1H-indol-4-yloxy)-N-({3-nitro-4-[(3-pyrrolidin-1-ylpropyl)amino]phenyl}sulfonyl)benzamide | 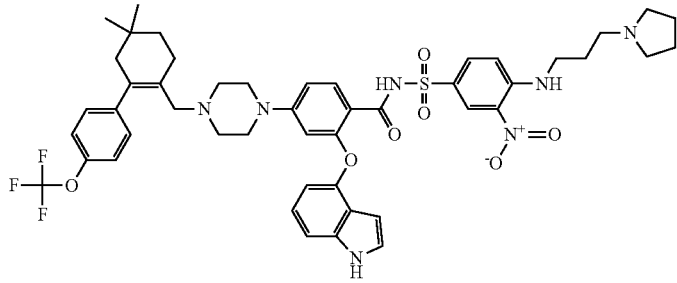 |
| 4-[4-({4,4-dimethyl-2-[3-(trifluoromethyl)phenyl]cyclohex-1-en-1-yl}methyl)piperazin-1-yl]-2-(1H-indol-4-yloxy)-N-({3-nitro-4-[(3-pyrrolidin-1-ylpropyl)amino]phenyl}sulfonyl)benzamide | 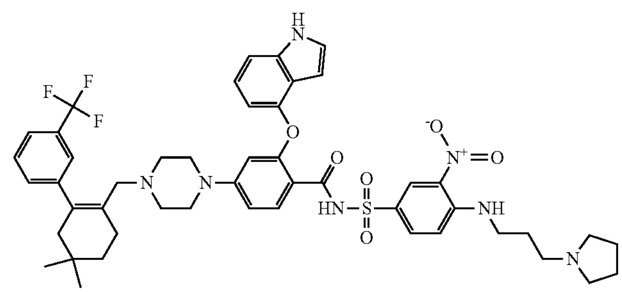 |
| 4-(4-{[2-(3-fluorophenyl)-4,4-dimethylcyclohex-1-en-1-yl]methyl}piperazin-1-yl)-2-(1H-indol-4-yloxy)-N-({3-nitro-4-[(3-pyrrolidin-1-ylpropyl)amino]phenyl}sulfonyl)benzamide | 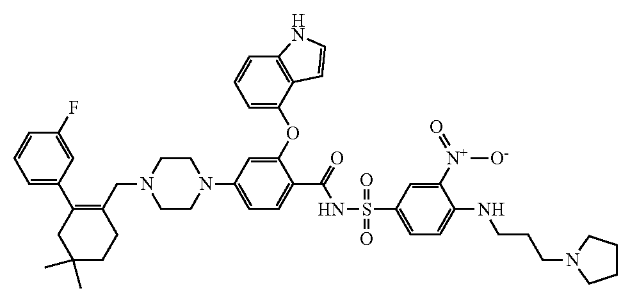 [SMILES: CC1(C)CCC(CN2CCN(c3ccc(C(=O)NS(=O)(=O)c4ccc(NCCCN5CCCC5)c([N+](=O)[O-])c4)c(Oc4cccc5[nH]ccc45)c3)CC2)=C(c2cccc(F)c2)C1] |
| 4-(4-{[2-(4-fluorophenyl)-4,4-dimethylcyclohex-1-en-1-yl]methyl}piperazin-1-yl)-2-(1H-indol-4-yloxy)-N-({3-nitro-4-[(3-pyrrolidin-1-ylpropyl)amino]phenyl}sulfonyl)benzamide | 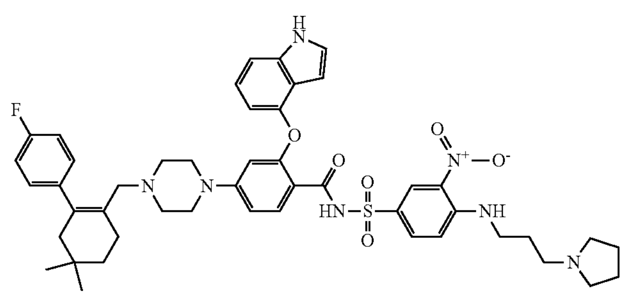 [SMILES: CC1(C)CCC(CN2CCN(c3ccc(C(=O)NS(=O)(=O)c4ccc(NCCCN5CCCC5)c([N+](=O)[O-])c4)c(Oc4cccc5[nH]ccc45)c3)CC2)=C(c2ccc(F)cc2)C1] |
| N-({3-{[chloro(difluoro)methyl]sulfonyl}-4-[(1-methylpiperidin-4-yl)amino]phenyl}sulfonyl)-4-(4-{[2-(4-chlorophenyl)-4,4-dimethylcyclohex-1-en-1-yl]methyl}piperazin-1-yl)-2-(1H-indol-5-yloxy)benzamide | 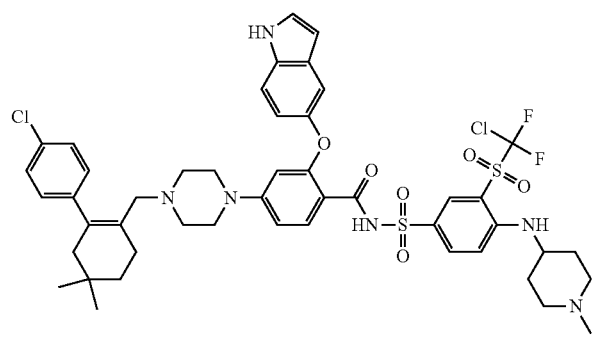 |

| Name | Structure |
|---|---|
| 4-(4-{[2-(4-chlorophenyl)cyclohex-1-en-1-yl]methyl}piperazin-1-yl)-2-(1H-indol-5-yloxy)-N-({4-[(1-methylpiperidin-4-yl)amino]-3-nitrophenyl}sulfonyl)benzamide | 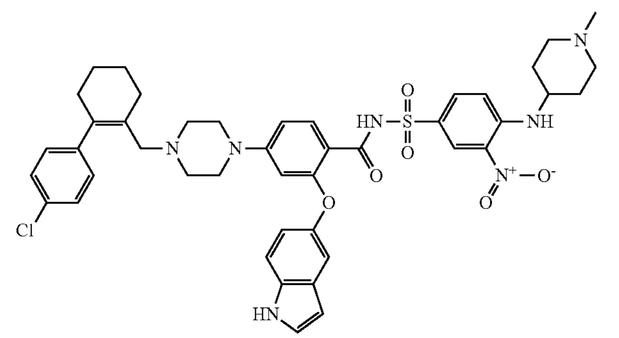 |
| 4-(4-{[2-(4-chlorophenyl)-4,4-dimethylcyclohex-1-en-1-yl]methyl}piperazin-1-yl)-2-(1H-indol-5-yloxy)-N-({4-[(1-methylpiperidin-4-yl)amino]-3-[(trifluoromethyl)sulfonyl]phenyl}sulfonyl)benzamide | 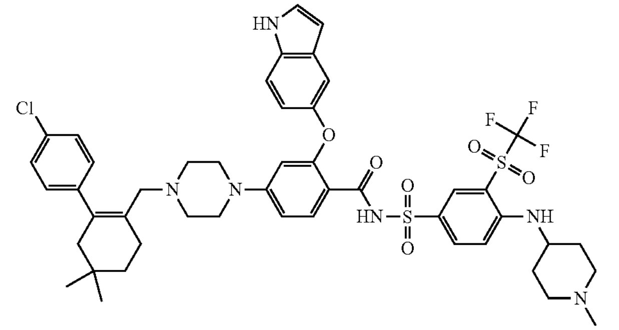 [SMILES: CN1CCC(Nc2ccc(S(=O)(=O)NC(=O)c3ccc(N4CCN(CC5=C(c6ccc(Cl)cc6)CC(C)(C)CC5)CC4)cc3Oc3ccc4[nH]ccc4c3)cc2S(=O)(=O)C(F)(F)F)CC1] |
| 4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)-2-(phenoxymethyl)benzamide | 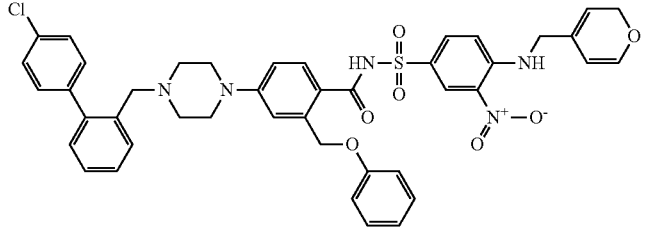 |
| 4-{4-[(4'-chloro-1,1'-biphenyl-2-yl)methyl]piperazin-1-yl}-N-({4-[(3-morpholin-4-ylpropyl)amino]phenyl}sulfonyl)-2-phenoxybenzamide | 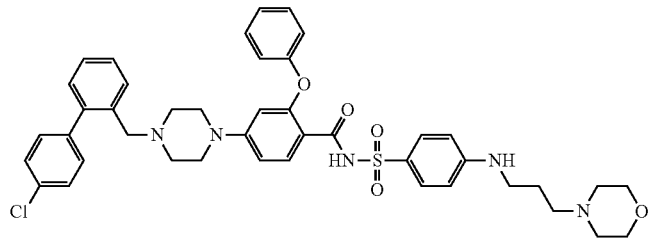 [SMILES: O=C(NS(=O)(=O)c1ccc(NCCCN2CCOCC2)cc1)c1ccc(N2CCN(Cc3ccccc3-c3ccc(Cl)cc3)CC2)cc1Oc1ccccc1] |
| 4-{4-[(4'-chloro-1,1'-biphenyl-2-yl)methyl]piperazin-11-yl}-N-({3-nitro-4-[(tetrahydro-2H-pyran-4-ylmethyl)amino]phenyl}sulfonyl)-2-(pyridin-3-yloxy)benzamide | 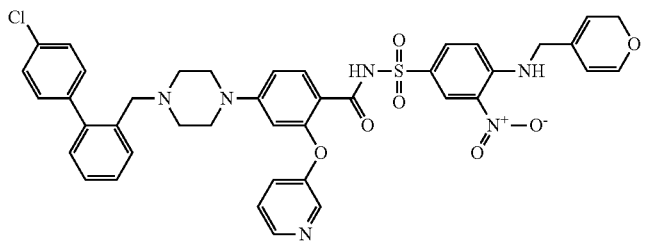 [SMILES: O=C(NS(=O)(=O)c1ccc(NCC2=CCOC=C2)c([N+](=O)[O-])c1)c1ccc(N2CCN(Cc3ccccc3-c3ccc(Cl)cc3)CC2)cc1Oc1cccnc1] |

| Name | Structure |
|---|---|
| 4-{4-[(4'-chloro-1,1'-biphenyl-2-yl)methyl]piperazin-1-yl}-2-(pyridin-3-yloxy)-N-({4-[(tetrahydro-2H-pyran-4-ylmethyl)amino]phenyl}sulfonyl)benzamide | 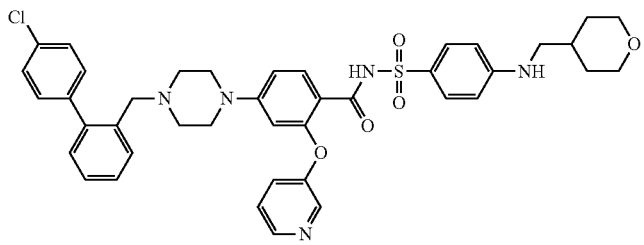 [SMILES: O=C(NS(=O)(=O)c1ccc(NCC2CCOCC2)cc1)c1ccc(N2CCN(Cc3ccccc3-c3ccc(Cl)cc3)CC2)cc1Oc1cccnc1] |
| 4-{4-[(4'-chloro-1,1'-biphenyl-2-yl)methyl]piperazin-1-yl}-N-{[4-([(1R)-3-(dimethylamino)-1-[(phenylthio)methyl]propyl}amino)-3-nitrophenyl]sulfonyl}-2-phenoxybenzamide | 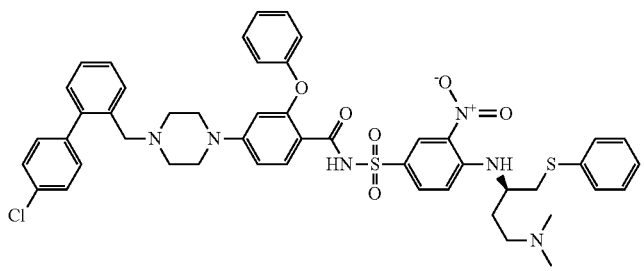 |
| 4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)-2-(pyridin-4-yloxy)benzamide | 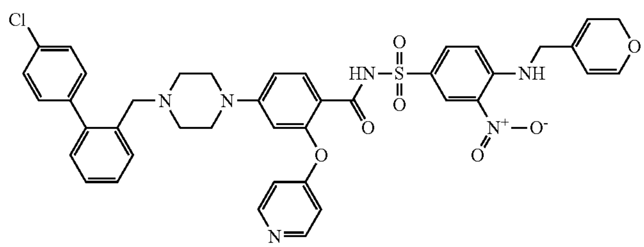 [SMILES: O=C(NS(=O)(=O)c1ccc(NCC2=CCOC=C2)c([N+](=O)[O-])c1)c1ccc(N2CCN(Cc3ccccc3-c3ccc(Cl)cc3)CC2)cc1Oc1ccncc1] |
| 4-{4-[(4'-chloro-1,1'-biphenyl-2-yl)methyl]piperazin-1-yl}-N-({4-[(3-morpholin-4-ylpropyl)amino]-3-nitrophenyl}sulfonyl)-2-(pyridin-3-yloxy)benzamide | 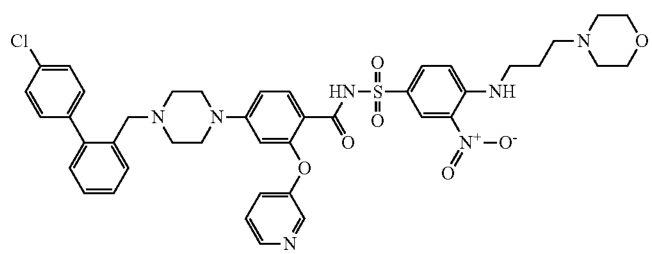 [SMILES: O=C(NS(=O)(=O)c1ccc(NCCCN2CCOCC2)c([N+](=O)[O-])c1)c1ccc(N2CCN(Cc3ccccc3-c3ccc(Cl)cc3)CC2)cc1Oc1cccnc1] |
| 4-{4-[(4'-chloro-1,1'-biphenyl-2-yl)methyl]piperazin-1-yl}-N-({4-[(3-morpholin-4-ylpropyl)amino]-3-nitrophenyl}sulfonyl)-2-(pyridin-4-yloxy)benzamide | 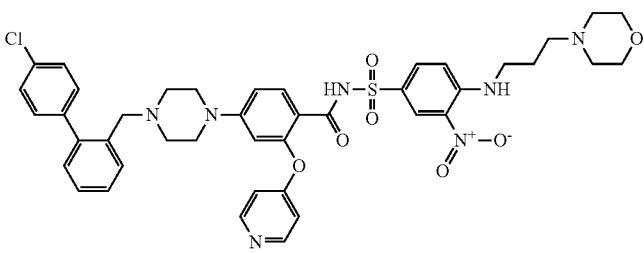 [SMILES: O=C(NS(=O)(=O)c1ccc(NCCCN2CCOCC2)c([N+](=O)[O-])c1)c1ccc(N2CCN(Cc3ccccc3-c3ccc(Cl)cc3)CC2)cc1Oc1ccncc1] |
| 4-{4-[(4'-chloro-1,1'-biphenyl-2-yl)methyl]piperazin-1-yl}-N-[(4-{[2-(4-methylpiperazin-1-yl)ethyl]amino}-3-nitrophenyl)sulfonyl]-2-phenoxybenzamide | 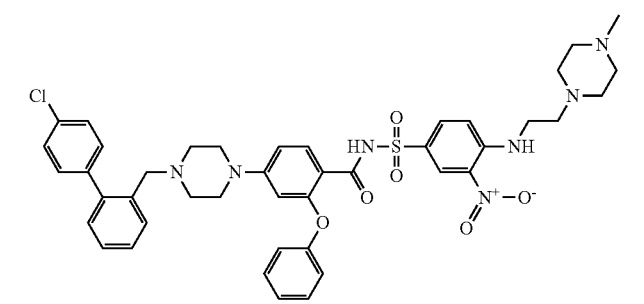 [SMILES: CN1CCN(CCNc2ccc(S(=O)(=O)NC(=O)c3ccc(N4CCN(Cc5ccccc5-c5ccc(Cl)cc5)CC4)cc3Oc3ccccc3)cc2[N+](=O)[O-])CC1] |

-continued

| Name | Structure |
|---|---|
| 4-{4-[(4'-chloro-1,1'-biphenyl-2-yl)methyl]piperazin-1-yl}-N-[(4-{[3-(4-methylpiperazin-1-yl)propyl]amino}-3-nitrophenyl)sulfonyl]-2-phenoxybenzamide | 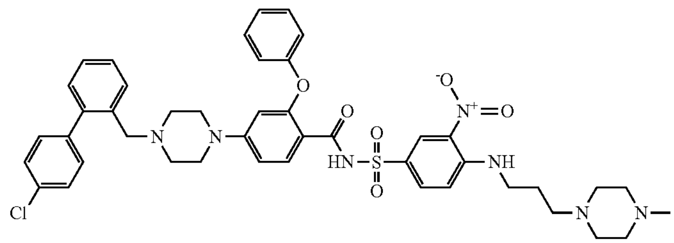 |
| 4-{4-[(4'-chloro-1,1'-biphenyl-2-yl)methyl]piperazin-1-yl}-N-({4-[[3-(dimethylamino)propyl](methyl)amino]-3-nitrophenyl}sulfonyl)-2-phenoxybenzamide | 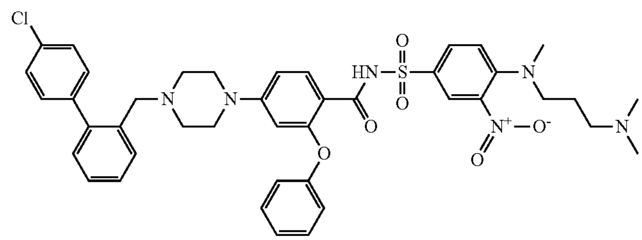 [SMILES: CN(C)CCCN(C)c1ccc(S(=O)(=O)NC(=O)c2ccc(N3CCN(Cc4ccccc4-c4ccc(Cl)cc4)CC3)cc2Oc2ccccc2)cc1[N+](=O)[O-]] |
| 4-{4-[(4'-chloro-1,1'-biphenyl-2-yl)methyl]piperazin-1-yl}-N-[(4-{[(1-methylpiperidin-4-yl)methyl]amino}-3-nitrophenyl)sulfonyl]-2-phenoxybenzamide | 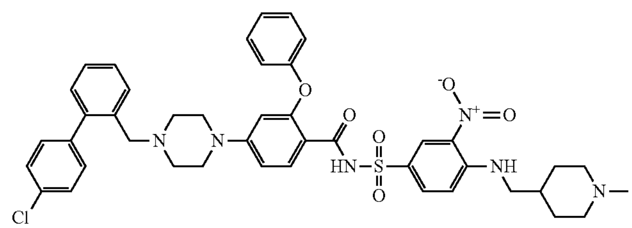 |
| 4-{4-[(4'-chloro-1,1'-biphenyl-2-yl)methyl]piperazin-1-yl}-N-({4-[(1-methylpiperidin-4-yl)amino]-3-nitrophenyl}sulfonyl)-2-phenoxybenzamide | 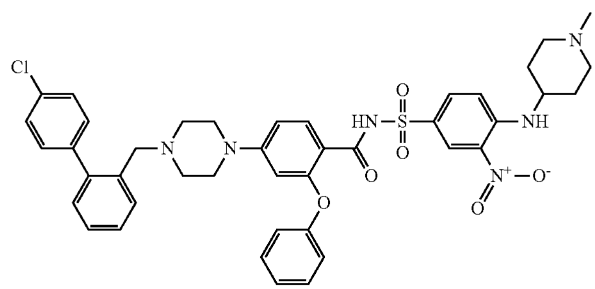 [SMILES: CN1CCC(Nc2ccc(S(=O)(=O)NC(=O)c3ccc(N4CCN(Cc5ccccc5-c5ccc(Cl)cc5)CC4)cc3Oc3ccccc3)cc2[N+](=O)[O-])CC1] |
| 4-{4-[(4'-chloro-1,1'-biphenyl-2-yl)methyl]piperazin-1-yl}-N-[(3-cyano-4-{[3-(dimethylamino)propyl]amino}phenyl)sulfonyl]-2-phenoxybenzamide | 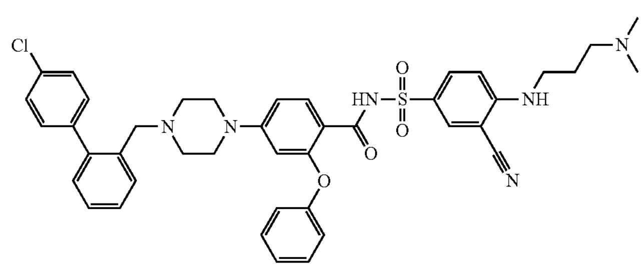 [SMILES: CN(C)CCCNc1ccc(S(=O)(=O)NC(=O)c2ccc(N3CCN(Cc4ccccc4-c4ccc(Cl)cc4)CC3)cc2Oc2ccccc2)cc1C#N] |
| 4-{4-[(4'-chloro-1,1'-biphenyl-2-yl)methyl]piperazin-1-yl}-N-({3-nitro-4-[(3-pyrrolidin-1-ylpropyl)amino]phenyl}sulfonyl)-2-phenoxybenzamide | 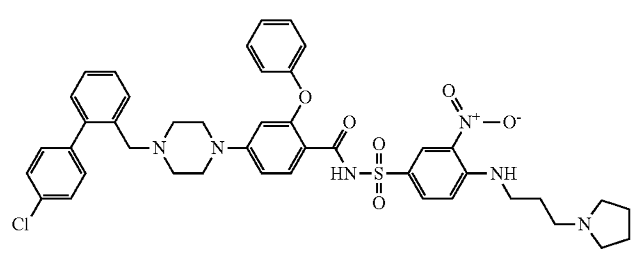 [SMILES: O=C(NS(=O)(=O)c1ccc(NCCCN2CCCC2)c([N+](=O)[O-])c1)c1ccc(N2CCN(Cc3ccccc3-c3ccc(Cl)cc3)CC2)cc1Oc1ccccc1] |

| Name | Structure |
|---|---|
| 4-{4-[(4'-chloro-1,1'-biphenyl-2-yl)methyl]piperazin-1-yl}-N-{[4-{[3-(dimethylamino)propyl]amino}-3-(trifluoromethyl)phenyl]sulfonyl}-2-phenoxybenzamide | 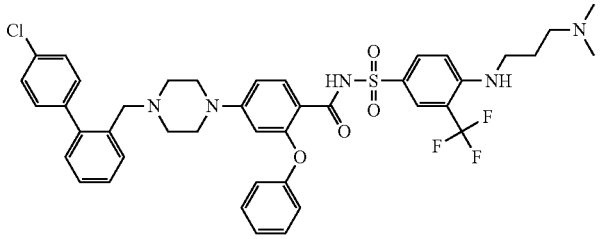 [SMILES: CN(C)CCCNc1ccc(S(=O)(=O)NC(=O)c2ccc(N3CCN(Cc4ccccc4-c4ccc(Cl)cc4)CC3)cc2Oc2ccccc2)cc1C(F)(F)F] |
| 4-{4-[(4'-chloro-1,1'-biphenyl-2-yl)methyl]piperazin-1-yl}-N-{[4-({3-[isopropyl(methyl)amino]propyl}amino)-3-nitrophenyl]sulfonyl}-2-phenoxybenzamide | 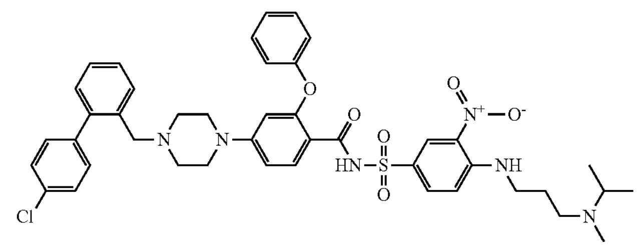 [SMILES: CC(C)N(C)CCCNc1ccc(S(=O)(=O)NC(=O)c2ccc(N3CCN(Cc4ccccc4-c4ccc(Cl)cc4)CC3)cc2Oc2ccccc2)cc1[N+](=O)[O-]] |
| 4-{4-[(4'-chloro-1,1'-biphenyl-2-yl)methyl]piperazin-1-yl}-N-({4-[3-(dimethylamino)propoxy]-3-nitrophenyl}sulfonyl)-2-phenoxybenzamide | 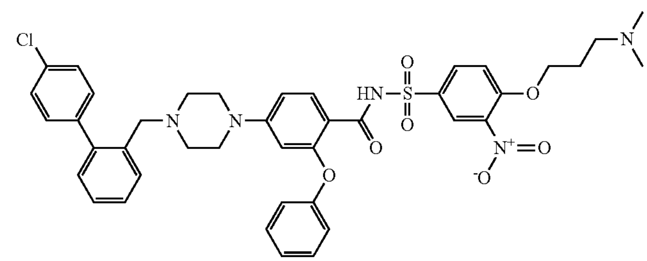 |
| 4-(4-{[2-(4-chlorophenyl)-4,4-dimethylcyclohex-1-en-1-yl]methyl}piperazin-1-yl)-2-(1H-indol-5-yloxy)-N-[(4-{[2-(4-methylpiperazin-1-yl)ethyl]amino}-3-nitrophenyl)sulfonyl]benzamide | 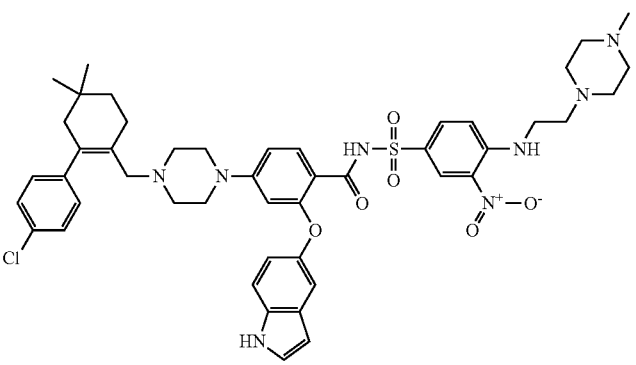 [SMILES: CN1CCN(CCNc2ccc(S(=O)(=O)NC(=O)c3ccc(N4CCN(CC5=C(c6ccc(Cl)cc6)CC(C)(C)CC5)CC4)cc3Oc3ccc4[nH]ccc4c3)cc2[N+](=O)[O-])CC1] |
| 4-(4-{[2-(4-chlorophenyl)-4,4-dimethylcyclohex-1-en-1yl]methyl}piperazin-1-yl)-2-(1H-indol-5-yloxy)-N-[(4-{[3-(4-methylpiperazin-1-yl)propyl]amino}-3-nitrophenyl)sulfonyl]benzamide | 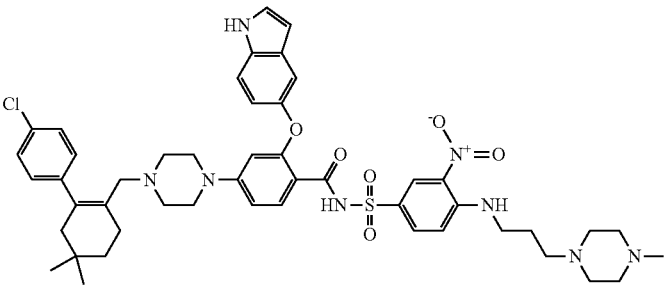 |

-continued

| Name | Structure |
|---|---|
| 4-(4-{[2-(4-chlorophenyl)-4,4-dimethylcyclohex-1-en-1-yl]methyl}piperazin-1-yl)-2-(1H-indol-5-yloxy)-N-({3-nitro-4-[(3-pyrrolidin-1-ylpropyl)amino]phenyl}sulfonyl)benzamide | 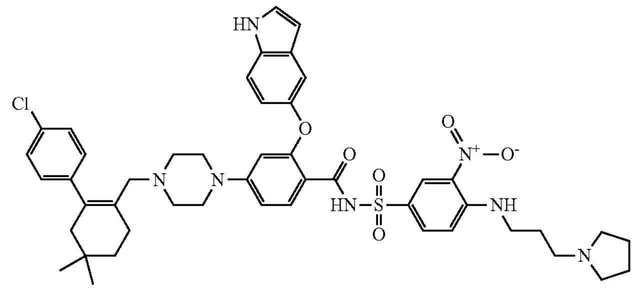 [SMILES: CC1(C)CCC(CN2CCN(c3ccc(C(=O)NS(=O)(=O)c4ccc(NCCCN5CCCC5)c([N+](=O)[O-])c4)c(Oc4ccc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-2-(1H-indol-5-yloxy)-N-({4-[(1-methylpiperidin-4-yl)amino]-3-nitrophenyl}sulfonyl)benzamide | 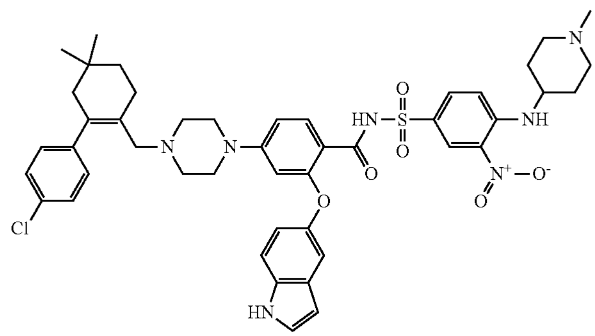 |
| 4-(4-{[2-(4-chlorophenyl)-4,4-dimethylcyclohex-1-en-1-yl]methyl}piperazin-1-yl)-2-(1H-indol-4-yloxy)-N-[(4-{[3-(4-methylpiperazin-1-yl)propyl]amino}-3-nitrophenyl)sulfonyl]benzamide | 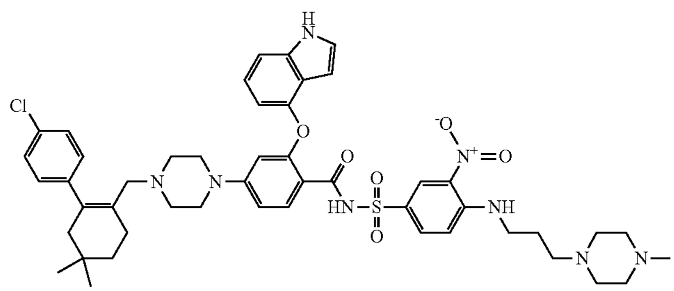 |
| 4-(4-{[2-(4-chlorophenyl)-4,4-dimethylcyclohex-1-en-1-yl]methyl}piperazin-1-yl)-N-({4-[3-(dimethylamino)propoxy]-3-nitrophenyl}sulfonyl)-2-(1H-indol-5-yloxy)benzamide | 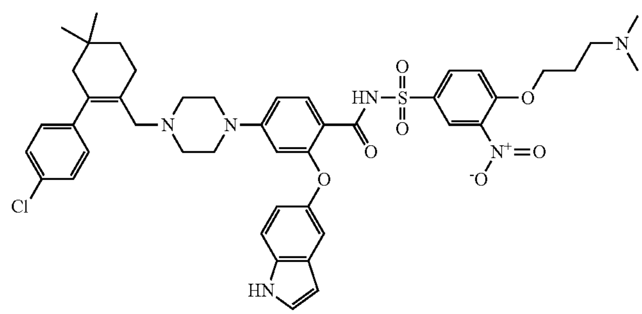 |
| 4-(4-{[2-(4-chlorophenyl)-4,4-dimethylcyclohex-1-en-1-yl]methyl}piperazin-1-yl)-2-(1H-indol-4-yloxy)-N-[(4-{[2-(4-methylpiperazin-1-yl)ethyl]amino}-3-nitrophenyl)sulfonyl]benzamide | 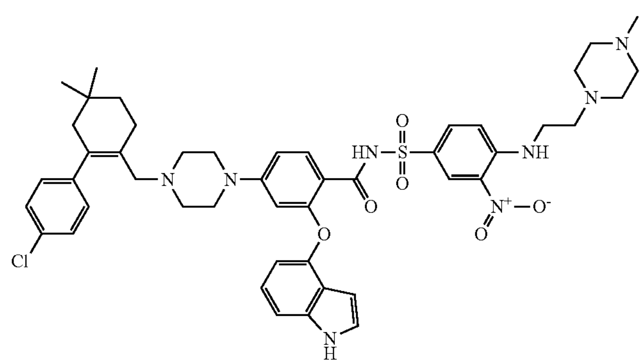 [SMILES: CN1CCN(CCNc2ccc(S(=O)(=O)NC(=O)c3ccc(N4CCN(CC5=C(c6ccc(Cl)cc6)CC(C)(C)CC5)CC4)cc3Oc3cccc4[nH]ccc34)cc2[N+](=O)[O-])CC1] |

| Name | Structure |
|---|---|
| 4-(4-{[2-(4-chlorophenyl)-4,4-dimethylcyclohex-1-en-1-yl]methyl}piperazin-1-yl)-2-(1H-indol-4-yloxy)-N-({3-nitro-4-[(3-pyrrolidin-1-ylpropyl)amino]phenyl}sulfonyl)benzamide | 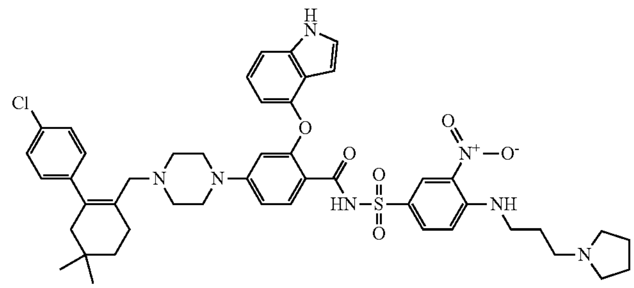 [SMILES: CC1(C)CCC(CN2CCN(c3ccc(C(=O)NS(=O)(=O)c4ccc(NCCCN5CCCC5)c([N+](=O)[O-])c4)c(Oc4cccc5[nH]ccc45)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-2-(1H-indol-4-yloxy)-N-({4-[(1-methylpiperidin-4-yl)amino]-3-nitrophenyl}sulfonyl)benzamide | 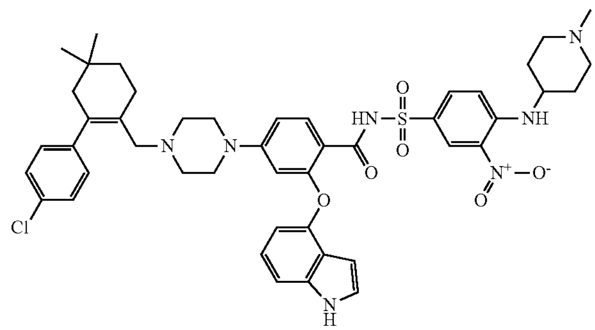 |
| 4-(4-{[2-(4-chlorophenyl)-4,4-dimethylcyclohex-1-en-1-yl]methyl}piperazin-1-yl)-2-(1H-indol-4-yloxy)-N-[(4-{[(1-methylpiperin-4-yl)methyl]amino}-3-nitrophenyl)sulfonyl]benzamide | 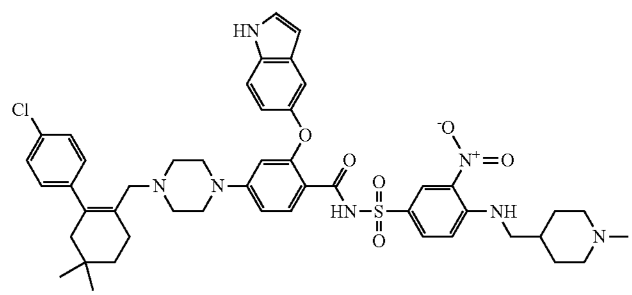 |
| 4-(4-{[2-(4-chlorophenyl)-4,4-dimethylcyclohex-1-en-1-yl]methyl}piperazin-1-yl)-2-(1H-indol-4-yloxy)-N-[(4-{[(1-methylpiperidin-4-yl)methyl]amino}-3-nitrophenyl)sulfonyl]benzamide | 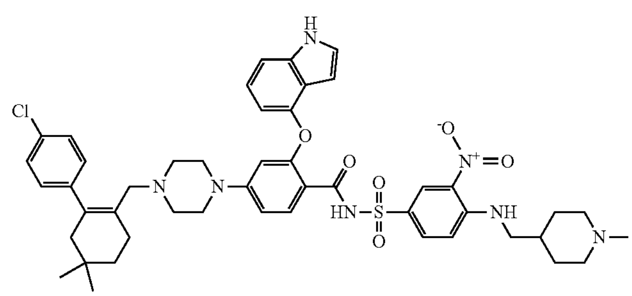 |
| 4-(4-{[2-(4-chlorophenyl)-4,4-dimethylcyclohex-1-en-1-yl]methyl}piperazin-1-yl)-N-({4-[3-(dimethylamino)propoxy]-3-nitrophenyl}sulfonyl)-2-(1H-indol-4-yloxy)benzamide | 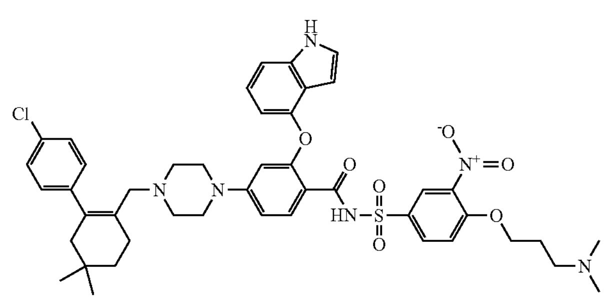 |

| Name | Structure |
|---|---|
| 4-(4-{[2-(4-chlorophenyl)-4,4-dimethylcyclohex-1-en-1-yl]methyl}piperazin-1-yl)-2-(1H-indol-5-yloxy)-N-{[4-(4-methylpiperazin-1-yl)-3-nitrophenyl]sulfonyl}benzamide | 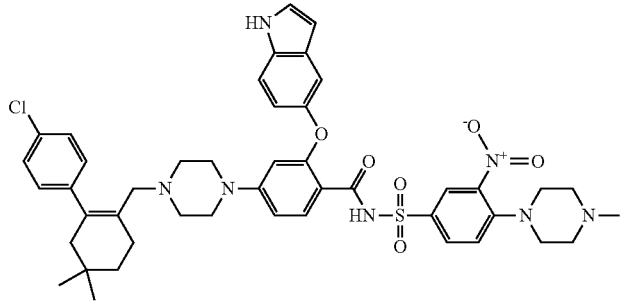 |
| 4-(4-{[2-(4-chlorophenyl)-4,4-dimethylcyclohex-1-en-1-yl]methyl}piperzin-1-yl)-2-(1H-indol-4-yloxy)-N-[(3-nitro-4-{[1-(2,2,2-trifluoroethyl)piperidin-4-yl]amino}phenyl)sulfonyl]benzamide | 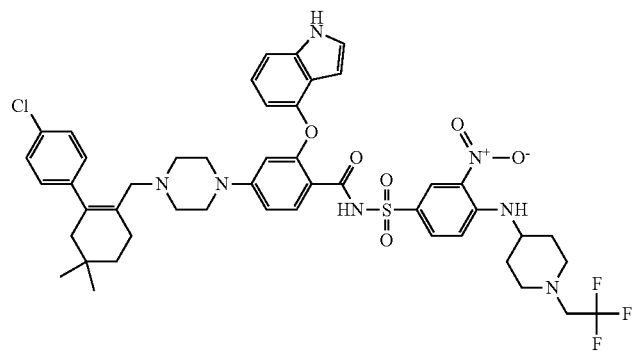 [SMILES: CC1(C)CCC(CN2CCN(c3ccc(C(=O)NS(=O)(=O)c4ccc(NC5CCN(CC(F)(F)F)CC5)c([N+](=O)[O-])c4)c(Oc4cccc5[nH]ccc45)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-{[4-({[4-(dimethylamino)-1-methylpiperidin-4-yl]methyl}amino)-3-nitrophenyl]sulfonyl}-2-(1H-indol-5-yloxy)benzamide | 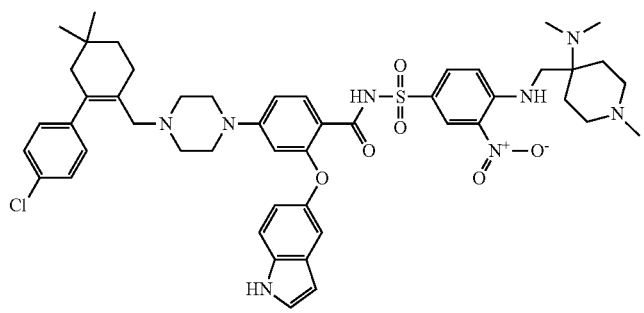 [SMILES: CN1CCC(CNc2ccc(S(=O)(=O)NC(=O)c3ccc(N4CCN(CC5=C(c6ccc(Cl)cc6)CC(C)(C)CC5)CC4)cc3Oc3ccc4[nH]ccc4c3)cc2[N+](=O)[O-])(N(C)C)CC1] |
| 4-{4-[(4'-chloro-1,1'-biphenyl-2-yl)methyl]piperazin-1-yl}-2-(2,3-dihydro-1,4-benzaodioxin-5-yloxy)-N-({3-nitro-4-[(tetrahydro-2H-pyran-4-ylmethyl)amino]phenyl}sulfonyl)benzamide | 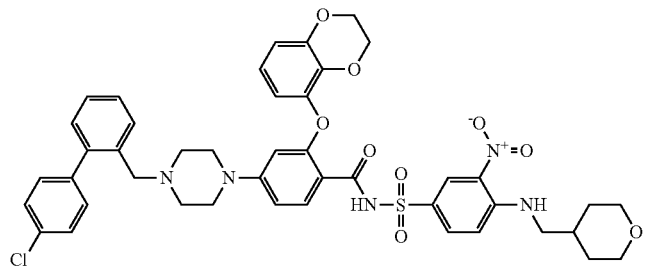 |
| 5-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)-1,1'-biphenyl-2-carboxamide | 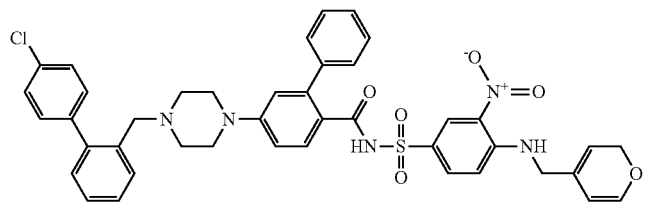 |

| Name | Structure |
|------|-----------|
| 5-{4-[(4'-chloro-1,1'-biphenyl-2-yl)methyl]piperazin-1-yl}-N-[(4-{[3-(dimethylamino)propyl]amino}-3-nitrophenyl)sulfonyl]-1,1'-biphenyl-2-carboxamide | 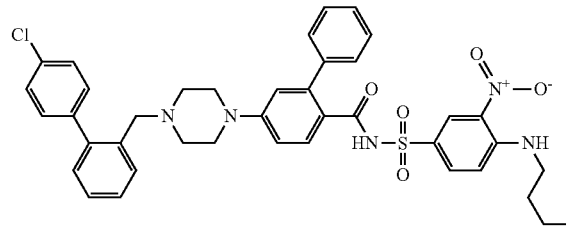 |
| 4-[4-({4'-chloro-4-[2-(dimethylamino)ethoxy]-1,1'-biphenyl-2-yl}methyl)piperazin-1-yl]-N-({3-nitro-4-[(tetrahydro-2H-pyran-4-ylmethyl)amino]phenyl}sulfonyl)-2-phenoxybenzamide | 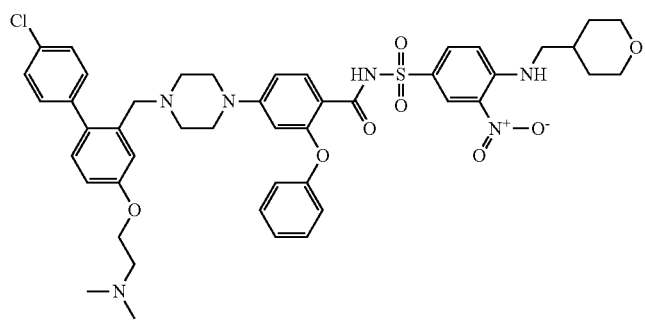 [SMILES: CN(C)CCOc1ccc(-c2ccc(Cl)cc2)c(CN2CCN(c3ccc(C(=O)NS(=O)(=O)c4ccc(NCC5CCOCC5)c([N+](=O)[O-])c4)c(Oc4ccccc4)c3)CC2)c1] |
| 4-(4-{[4'-chloro-4-(3-piperidin-1-ylpropoxy)-1,1'-biphenyl-2-yl]methyl}piperazin-1-yl)-N-({3-nitro-4-[(tetrahydro-2H-pyran-4-ylmethyl)amino]phenyl}sulfonyl)-2-phenoxybenzamide | 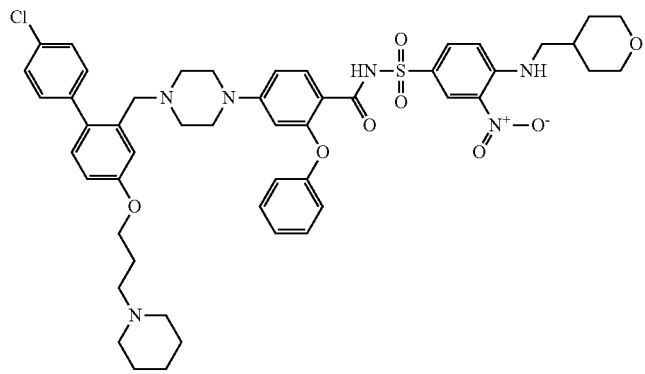 [SMILES: O=C(NS(=O)(=O)c1ccc(NCC2CCOCC2)c([N+](=O)[O-])c1)c1ccc(N2CCN(Cc3cc(OCCCN4CCCCC4)ccc3-c3ccc(Cl)cc3)CC2)cc1Oc1ccccc1] |
| 4-(4-{[4'-chloro-4-(2-morpholin-4-ylethoxy)-1,1'-biphenyl-2-yl]methyl}piperazin-1-yl)-N-({3-nitro-4-[(tetrahydro-2H-pyran-4-ylmethyl)amino]phenyl}sulfonyl)-2-phenoxybenzamide | 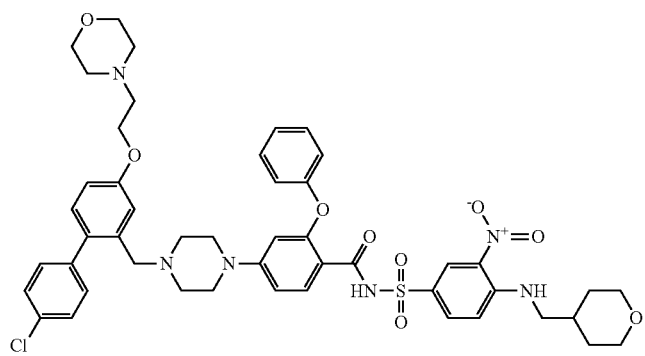 |

| Name | Structure |
|---|---|
| 4-[4-({4'-chloro-4-[3-(dimethylamino)propoxy]-1,1'-biphenyl-2-yl}methyl)piperazin-1-yl]-N-({3-nitro-4-[(tetrahydro-2H-pyran-4-ylmethyl)amino]phenyl}sulfonyl)-2-phenoxybenzamide | 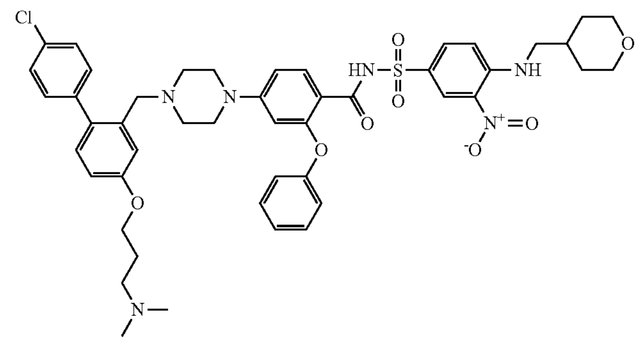 |
| 4-(4-{[4'-chloro-4-(2-morpholin-4-ylethoxy)-1,1'-biphenyl-2-yl]methyl}piperazin-1-yl)-2-phenoxy-N-({4-[(tetrahydro-2H-pyran-4-ylmethyl)amino]-3-[(trifluoromethyl)sulfonyl]phenyl}sulfonyl)benzamide | 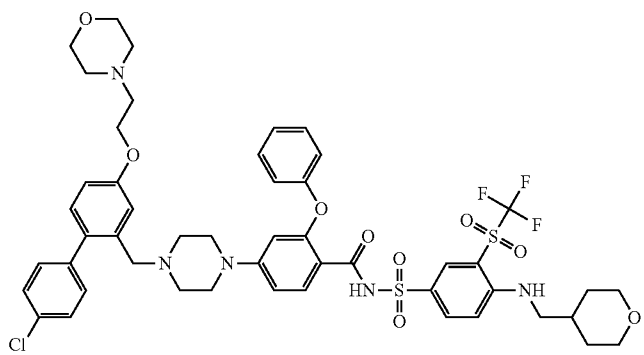 [SMILES: O=C(NS(=O)(=O)c1ccc(NCC2CCOCC2)c(S(=O)(=O)C(F)(F)F)c1)c1ccc(N2CCN(Cc3cc(OCCN4CCOCC4)ccc3-c3ccc(Cl)cc3)CC2)cc1Oc1ccccc1] |
| 4-(4-{[4'-chloro-4-(3-piperidin-1-ylpropoxy)-1,1'-biphenyl-2-yl]methyl}piperazin-1-yl)-2-phenoxy-N-({4-[(tetrahydro-2H-pyran-4-ylmethyl)amino]-3-[(trifluoromethyl)sulfonyl]phenyl}sulfonyl)benzamide | 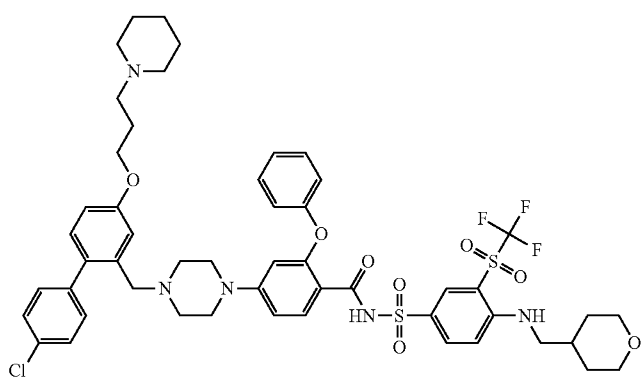 [SMILES: O=C(NS(=O)(=O)c1ccc(NCC2CCOCC2)c(S(=O)(=O)C(F)(F)F)c1)c1ccc(N2CCN(Cc3cc(OCCCN4CCCCC4)ccc3-c3ccc(Cl)cc3)CC2)cc1Oc1ccccc1] |
| 4-[4-({4'-chloro-4-[3-(dimethylamino)propoxy]-1,1'-biphenyl-2-yl}methyl)piperazin-1-yl]-2-phenoxy-N-({4-[(tetrahydro-2H-pyran-4-ylmethyl)amino]-3-[(trifluoromethyl)sulfonyl]phenyl}sulfonyl)benzamide | 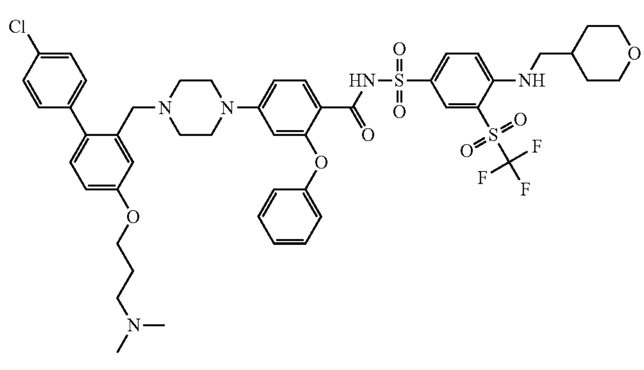 [SMILES: CN(C)CCCOc1ccc(-c2ccc(Cl)cc2)c(CN2CCN(c3ccc(C(=O)NS(=O)(=O)c4ccc(NCC5CCOCC5)c(S(=O)(=O)C(F)(F)F)c4)c(Oc4ccccc4)c3)CC2)c1] |

| Name | Structure |
|---|---|
| 4-[4-({4'-chloro-4-[2-(dimethylamino)ethoxy]-1,1'-biphenyl-2-yl}methyl)piperazin-1-yl]-2-phenoxy-N-({4-[(tetrahydro-2H-pyran-4-ylmethyl)amino]-3-[(trifluoromethyl)sulfonyl]phenyl}sulfonyl)benzamide | 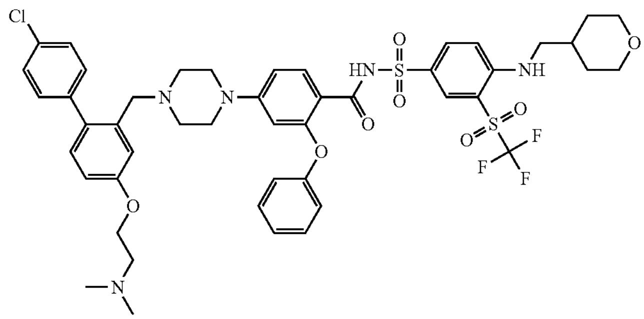 [SMILES: CN(C)CCOc1ccc(-c2ccc(Cl)cc2)c(CN2CCN(c3ccc(C(=O)NS(=O)(=O)c4ccc(NCC5CCOCC5)c(S(=O)(=O)C(F)(F)F)c4)c(Oc4ccccc4)c3)CC2)c1] |
| 4-[4-({4'-chloro-4-[2-(dimethylamino)ethoxy]-1,1'-biphenyl-2-yl}methyl)piperazin-1-yl]-N-({3-nitro-4-[(3-pyrrolidin-1-ylpropyl)amino]phenyl}sulfonyl)-2-phenoxybenzamide | 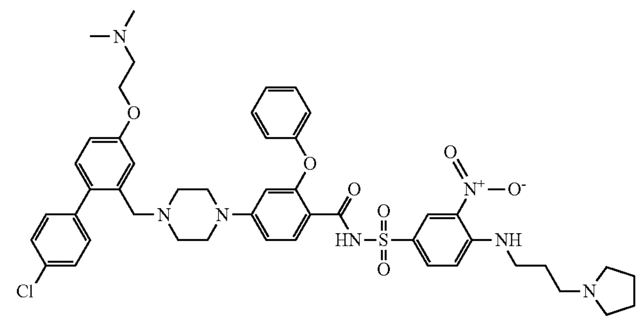 [SMILES: CN(C)CCOc1ccc(-c2ccc(Cl)cc2)c(CN2CCN(c3ccc(C(=O)NS(=O)(=O)c4ccc(NCCCN5CCCC5)c([N+](=O)[O-])c4)c(Oc4ccccc4)c3)CC2)c1] |
| 4-[4-({4'-chloro-3-[2-(dimethylamino)ethoxy]-1,1'-biphenyl-2-yl}methyl)piperazin-1-yl]-N-({3-nitro-4-[(tetrahydro-2H-pyran-4-ylmethyl)amino]phenyl}sulfonyl)-2-phenoxybenzamide | 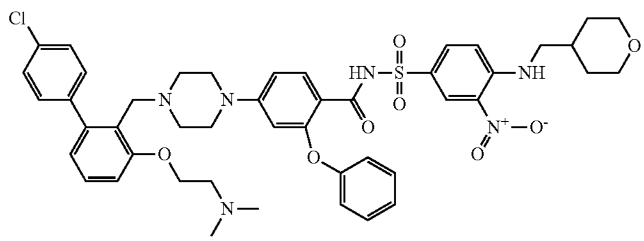 [SMILES: CN(C)CCOc1cccc(-c2ccc(Cl)cc2)c1CN1CCN(c2ccc(C(=O)NS(=O)(=O)c3ccc(NCC4CCOCC4)c([N+](=O)[O-])c3)c(Oc3ccccc3)c2)CC1] |
| 4-[4-({4'-chloro-3-[2-(dimethylamino)ethoxy]-1,1'-biphenyl-2-yl}methyl)piperazin-1-yl]-N-({3-nitro-4-[(3-pyrrolidin-1-ylpropyl)amino]phenyl}sulfonyl)-2-phenoxybenzamide | 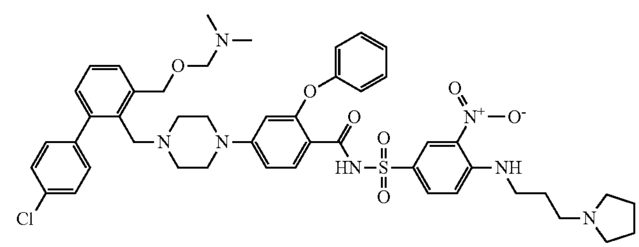 [SMILES: CN(C)COCc1cccc(-c2ccc(Cl)cc2)c1CN1CCN(c2ccc(C(=O)NS(=O)(=O)c3ccc(NCCCN4CCCC4)c([N+](=O)[O-])c3)c(Oc3ccccc3)c2)CC1] |
| 4-[4-({4'-chloro-3-[2-(dimethylamino)ethoxy]-1,1'-biphenyl-2-yl}methyl)piperazin-1-yl]-2-phenoxy-N-({4-[(tetrahydro-2H-pyran-4-ylmethyl)amino]-3-[(trifluoromethyl)sulfonyl]phenyl}sulfonyl)benzamide | 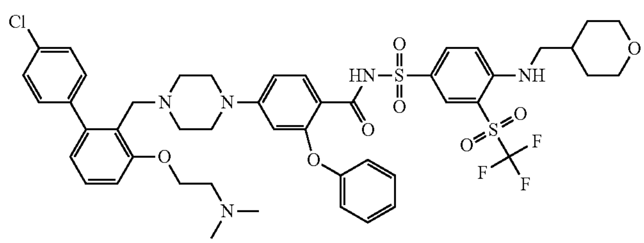 [SMILES: CN(C)CCOc1cccc(-c2ccc(Cl)cc2)c1CN1CCN(c2ccc(C(=O)NS(=O)(=O)c3ccc(NCC4CCOCC4)c(S(=O)(=O)C(F)(F)F)c3)c(Oc3ccccc3)c2)CC1] |

| Name | Structure |
|---|---|
| 4-[4-({4'-chloro-4-[2-(dimethylamino)ethoxy]-1,1'-biphenyl-2-yl}methyl)piperazin-1-yl]-2-(1H-indol-4-yloxy)-N-({3-nitro-4-[(tetrahydro-2H-pyran-4-ylmethyl)amino]phenyl}sulfonyl)benzamide | 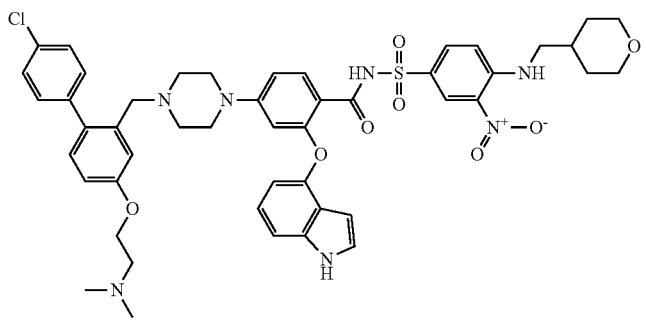 [SMILES: CN(C)CCOc1ccc(-c2ccc(Cl)cc2)c(CN2CCN(c3ccc(C(=O)NS(=O)(=O)c4ccc(NCC5CCOCC5)c([N+](=O)[O-])c4)c(Oc4cccc5[nH]ccc45)c3)CC2)c1] |
| 4-[4-({4'-chloro-4-[2-(dimethylamino)ethoxy]-1,1'-biphenyl-2-yl}methyl)piperazin-1-yl]-2-(1H-indol-5-yloxy)-N-({3-nitro-4-[(tetrahydro-2H-pyran-4-ylmethyl)amino]phenyl}sulfonyl)benzamide | 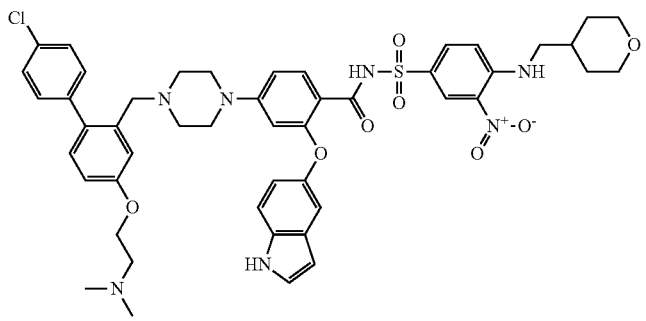 [SMILES: CN(C)CCOc1ccc(-c2ccc(Cl)cc2)c(CN2CCN(c3ccc(C(=O)NS(=O)(=O)c4ccc(NCC5CCOCC5)c([N+](=O)[O-])c4)c(Oc4ccc5[nH]ccc5c4)c3)CC2)c1] |
| 4-(4-{[4'-chloro-4-(2-morpholin-4-ylethoxy)-1,1'-biphenyl-2-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide | 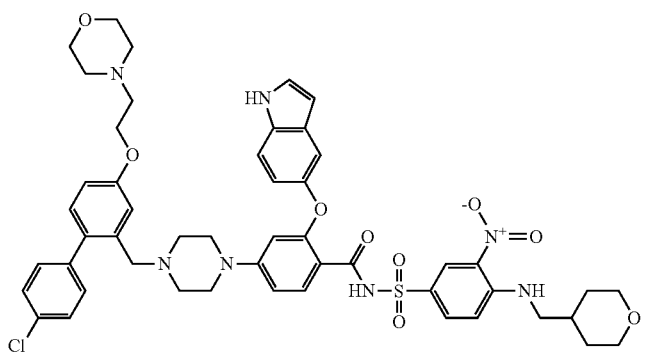 |
| 4-[4-({4'-chloro-3-[2-(dimethylamino)ethoxy-1,1'-biphenyl-2-yl}methyl)piperazin-1-yl]-2-(1H-indol-4-yloxy)-N-({3-nitro-4-[(tetrahydro-2H-pyran-4-ylmethyl)amino]phenyl}sulfonyl)benzamide | 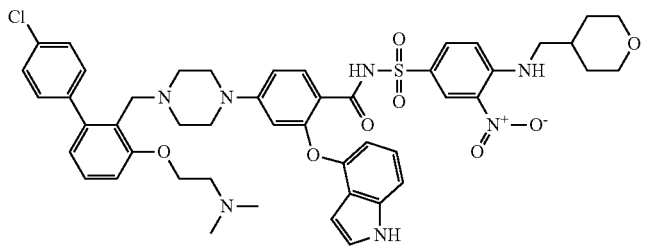 |
| 4-[4-({4'-chloro-3-[2-(dimethylamino)ethoxy]-1,1'-biphenyl-2-yl}methyl)piperazin-1-yl]-2-(1H-indol-5-yloxy)-N-({3-nitro-4-[(tetrahydro-2H-pyran-4-ylmethyl)amino]phenyl}sulfonyl)benzamide | 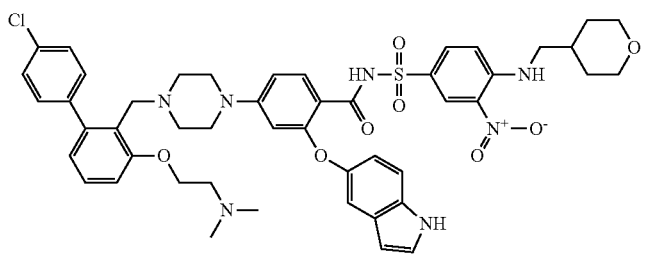 [SMILES: CN(C)CCOc1cccc(-c2ccc(Cl)cc2)c1CN1CCN(c2ccc(C(=O)NS(=O)(=O)c3ccc(NCC4CCOCC4)c([N+](=O)[O-])c3)c(Oc3ccc4[nH]ccc4c3)c2)CC1] |

| Name | Structure |
|---|---|
| 4-(4-{[4'-chloro-4-(2-morpholin-4-ylethoxy)-1,1'-biphenyl-2-yl]methyl}piperazin-1-yl)-2-(1H-indol-4-yloxy)-N-({3-nitro-4-[(tetrahydro-2H-pyran-4-ylmethyl)amino]phenyl}sulfonyl)benzamide | 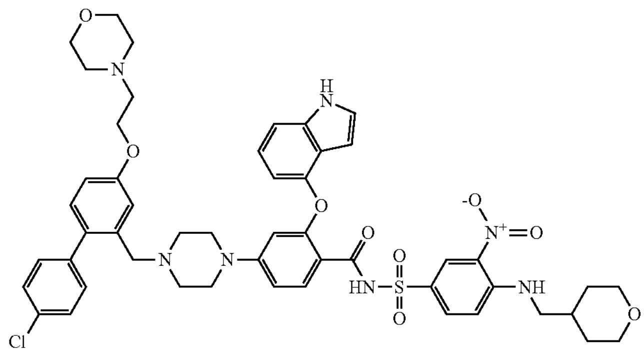 |
| 4-(4-{[4'-chloro-3-(2-morpholin-4-ylethoxy)-1,1'-biphenyl-2-yl]methyl}piperazin-1-yl)-2-(1H-indol-4-yloxy)-N-({3-nitro-4-[(tetrahydro-2H-pyran-4-ylmethyl)amino]phenyl}sulfonyl)benzamide | 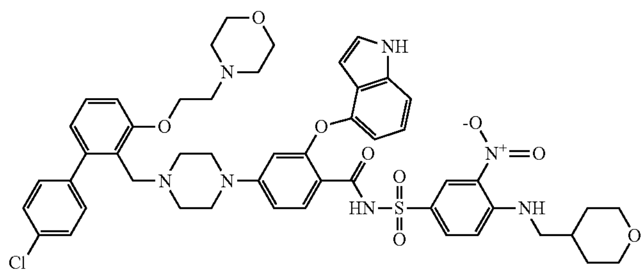 |
| 4-(4-{[4'-chloro-3-(2-morpholin-4-ylethoxy)-1,1'-biphenyl-2-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide | 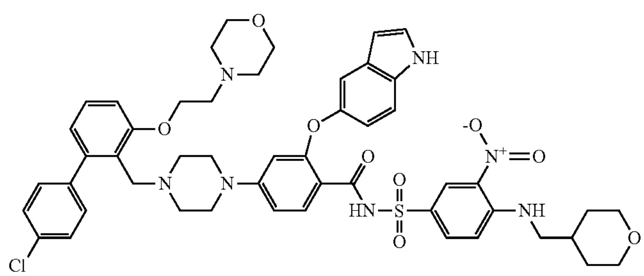 |
| 4-[4-({4'-chloro-4-[2-(dimethylamino)ethoxy]-1,1'-biphenyl-2-yl}methyl)piperazin-1-yl]-N-({4-[(1-methylpiperidin-4-yl)amino]-3-nitrophenyl}sulfonyl)-2-phenoxybenzamide | 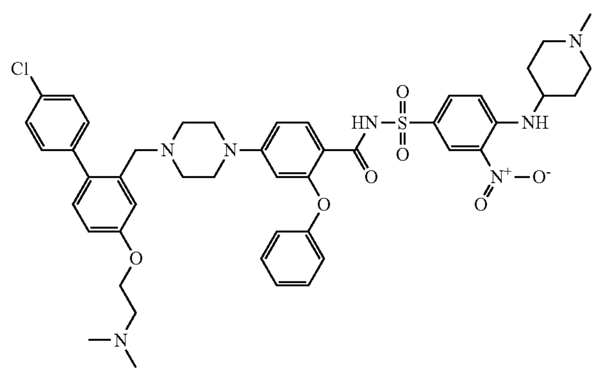 [SMILES: CN(C)CCOc1ccc(-c2ccc(Cl)cc2)c(CN2CCN(c3ccc(C(=O)NS(=O)(=O)c4ccc(NC5CCN(C)CC5)c([N+](=O)[O-])c4)c(Oc4ccccc4)c3)CC2)c1] |
| 4-[4-({4'-chloro-3-[2-(dimethylamino)ethoxy]-1,1'-biphenyl-2-yl}methyl)piperazin-1-yl]-2-(1H-indol-5-yloxy)-N-({3-nitro-4-[(3-pyrrolidin-1-ylpropyl)amino]phenyl}sulfonyl)benzamide | 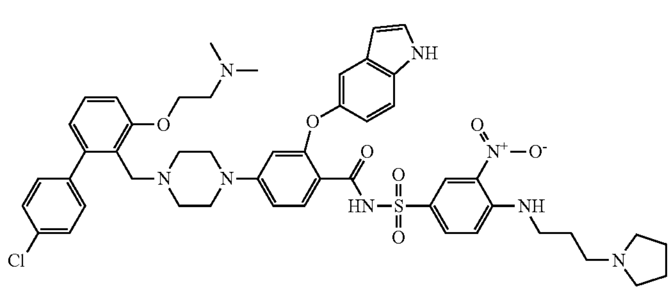 [SMILES: CN(C)CCOc1cccc(-c2ccc(Cl)cc2)c1CN1CCN(c2ccc(C(=O)NS(=O)(=O)c3ccc(NCCCN4CCCC4)c([N+](=O)[O-])c3)c(Oc3ccc4[nH]ccc4c3)c2)CC1] |

-continued

| Name | Structure |
|---|---|
| 4-[4-({4'-chloro-4-[2-(dimethylamino)ethoxy]-1,1'-biphenyl-2-yl}methyl)piperazin-1-yl]-2-(1H-indol-5-yloxy)-N-({3-nitro-4-[(3-pyrrolidin-1-ylpropyl)amno]phenyl}sulfonyl)benzamide | 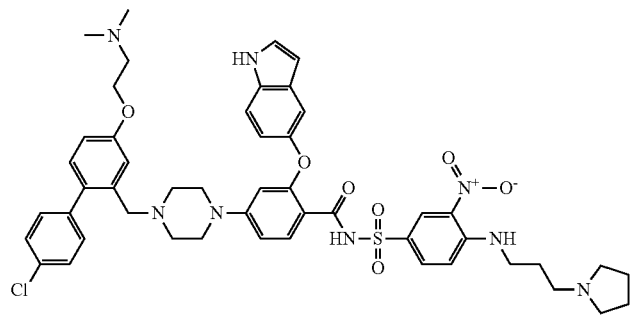 [SMILES: CN(C)CCOc1ccc(-c2ccc(Cl)cc2)c(CN2CCN(c3ccc(C(=O)NS(=O)(=O)c4ccc(NCCCN5CCCC5)c([N+](=O)[O-])c4)c(Oc4ccc5[nH]ccc5c4)c3)CC2)c1] |
| 4-(4-{[4'-chloro-4-(2-morpholin-4-ylethoxy)-1,1'-biphenyl-2-yl]methyl}piperazin-1-yl)-2-(1H-indol-5-yloxy)-N-({3-nitro-4-[(3-pyrrolidin-1-ylpropyl)amino]phenyl}sulfonyl)benzamide | 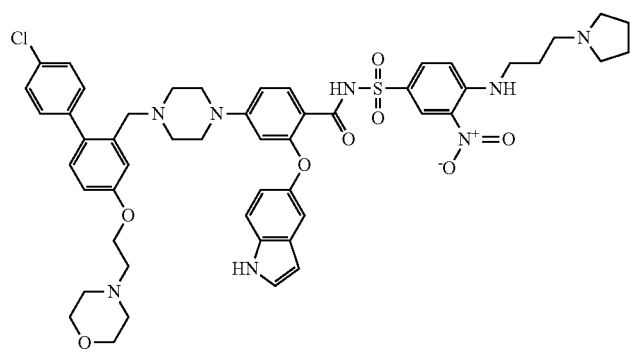 |
| 4-[4-({4'-chloro-4-[2-(dimethylamino)ethoxy]-1,1'-biphenyl-2-yl}methyl)piperazin-1-yl]-N-[(3-nitro-4-{[1-(2,2,2-trifluoroethyl)piperidin-4-yl]amino}phenyl)sulfonyl]-2-phenoxybenzamide | 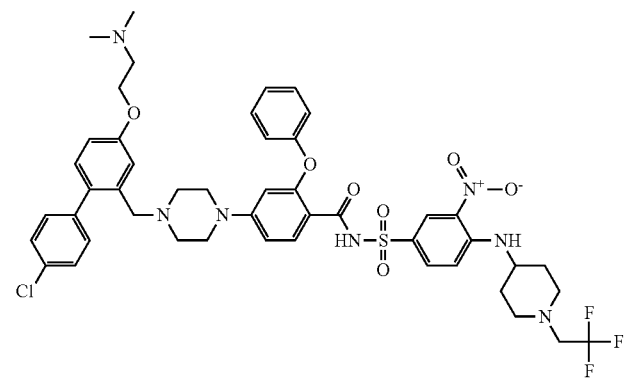 [SMILES: CN(C)CCOc1ccc(-c2ccc(Cl)cc2)c(CN2CCN(c3ccc(C(=O)NS(=O)(=O)c4ccc(NC5CCN(CC(F)(F)F)CC5)c([N+](=O)[O-])c4)c(Oc4ccccc4)c3)CC2)c1] |
| 4-(4-{[4'-chloro-4-(2-pyrrolidin-1-ylethoxy)-1,1'-biphenyl-2-yl]methyl}piperazin-1-yl)-N-({3-nitro-4-[(tetrahydro-2H-pyran-4-ylmethyl)amino]phenyl}sulfonyl)-2-phenoxybenzamide | 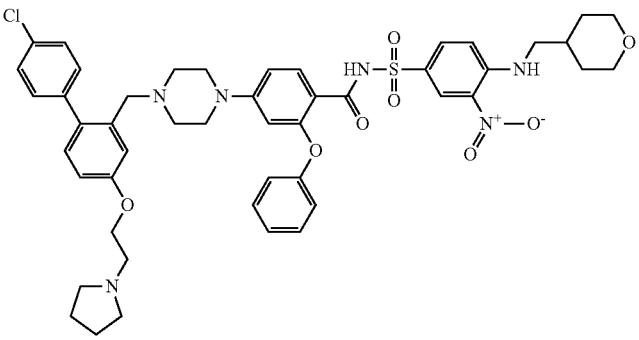 [SMILES: O=C(NS(=O)(=O)c1ccc(NCC2CCOCC2)c([N+](=O)[O-])c1)c1ccc(N2CCN(Cc3cc(OCCN4CCCC4)ccc3-c3ccc(Cl)cc3)CC2)cc1Oc1ccccc1] |

| Name | Structure |
|---|---|
| 4-[4-({4'-chloro-4-[2-(diisopropylamino)ethoxy]-1,1'-biphenyl-2-yl}methyl)piperazin-1-yl]-N-({3-nitro-4-[(tetrahydro-2H-pyran-4-ylmethyl)amino]phenyl}sulfonyl)-2-phenoxybenzamide | 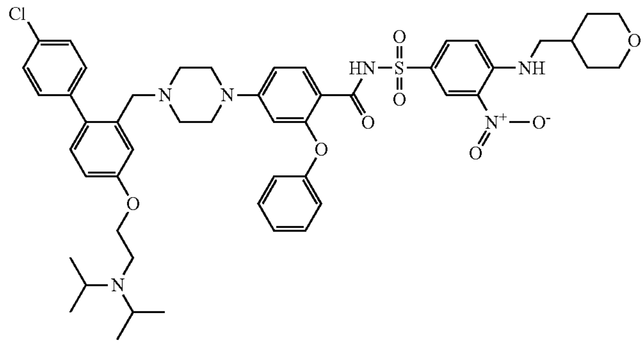 [SMILES: CC(C)N(CCOc1ccc(-c2ccc(Cl)cc2)c(CN2CCN(c3ccc(C(=O)NS(=O)(=O)c4ccc(NCC5CCOCC5)c([N+](=O)[O-])c4)c(Oc4ccccc4)c3)CC2)c1)C(C)C] |
| 4-{4-[(4'-chloro-1,1'-biphenyl-2-yl)methyl]piperazin-1-yl}-2-(2,3-dihydro-1H-indol-5-yloxy)-N-({3-nitro-4-[(tetrahydro-2H-pyran-4-ylmethyl)amino]phenyl}sulfonyl)benzamide | 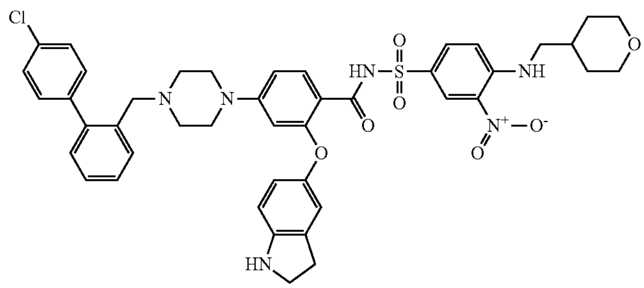 [SMILES: O=C(NS(=O)(=O)c1ccc(NCC2CCOCC2)c([N+](=O)[O-])c1)c1ccc(N2CCN(Cc3ccccc3-c3ccc(Cl)cc3)CC2)cc1Oc1ccc2c(c1)CCN2] |
| 4-(4-{[2-(4-chlorophenyl)cyclohept-1-en-1-yl]methyl}piperazin-1-yl)-2-(1H-indol-4-yloxy)-N-({3-nitro-4-[(3-pyrrolidin-1-ylpropyl)amino]phenyl}sulfonyl)benzamide | 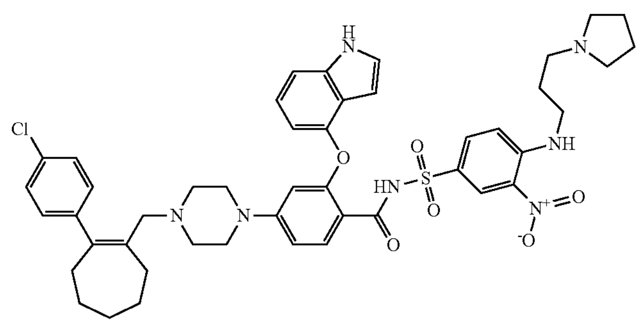 |
| 4-(4-{[2-(4-chlorophenyl)cyclooct-1-en-1-yl]methyl}piperazin-1-yl)-2-(1H-indol-4-yloxy)-N-({3-nitro-4-[(3-pyrrolidin-1-ylpropyl)amino]phenyl}sulfonyl)benzamide | 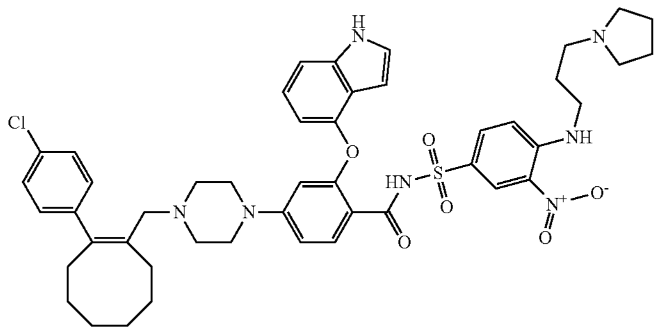 [SMILES: O=C(NS(=O)(=O)c1ccc(NCCCN2CCCC2)c([N+](=O)[O-])c1)c1ccc(N2CCN(C/C3=C(\c4ccc(Cl)cc4)CCCCCC3)CC2)cc1Oc1cccc2[nH]ccc12] |
| 4-(4-{[2-(4-chlorophenyl)cyclopent-1-en-1-yl]methyl}piperazin-1-yl)-2-(1H-indol-4-yloxy)-N-({3-nitro-4-[(3-pyrrolidin-1-ylpropyl)amino]phenyl}sulfonyl)benzamide | 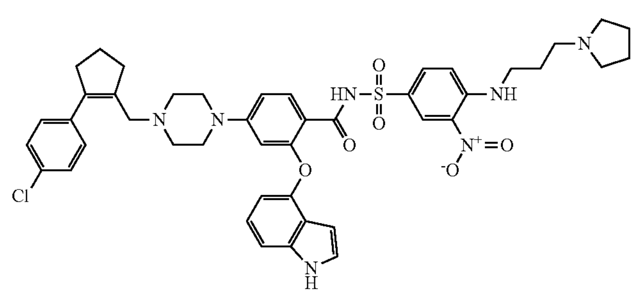 |

-continued

| Name | Structure |
|---|---|
| 4-(4-{[2-(4-chlorophenyl)-4,4-dimethylcyclopent-1-en-1-yl]methyl}piperazin-1-yl)-2-(1H-indol-4-yloxy)-N-({4-[(1-methylpiperidin-4-yl)amino]-3-nitrophenyl}sulfonyl)benzamide | 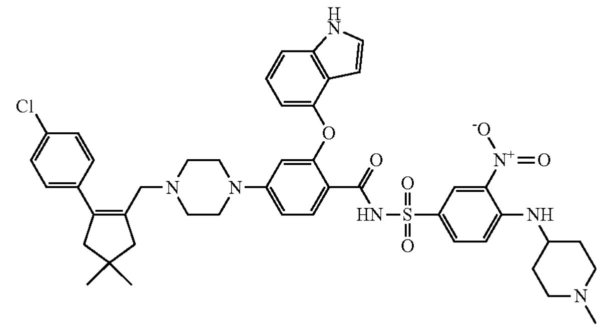 |
| 4-(4-{[4-(4-chlorophenyl)-6,6-dimethyl-5,6-dihydro-2H-pyran-3-yl]methyl}piperazin-1-yl)-2-(1H-indol-4-yloxy)-N-({4-[(1-methylpiperidin-4-yl)amino]-3-nitrophenyl}sulfonyl)benzamide | 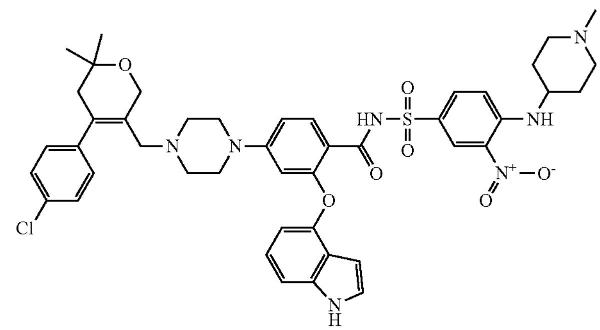 [SMILES: CN1CCC(Nc2ccc(S(=O)(=O)NC(=O)c3ccc(N4CCN(CC5=C(c6ccc(Cl)cc6)CC(C)(C)OC5)CC4)cc3Oc3cccc4[nH]ccc34)cc2[N+](=O)[O-])CC1] |
| 4-(4-{[2-(4-chlorophenyl)cyclooct-1-en-1-yl]methyl}piperazin-1-yl)-2-(1H-indol-4-yloxy)-N-({4-[(1-methylpiperidin-4-yl)amino]-3-nitrophenyl}sulfonyl)benzamide | 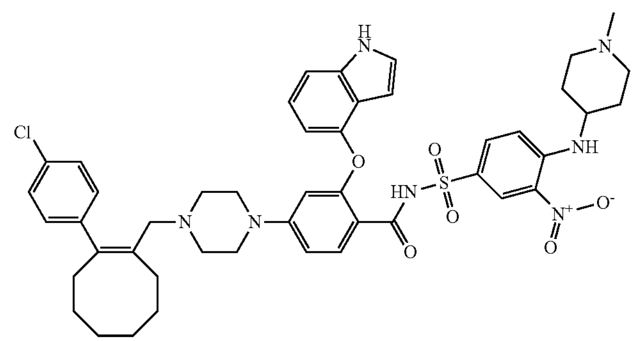 [SMILES: CN1CCC(Nc2ccc(S(=O)(=O)NC(=O)c3ccc(N4CCN(C/C5=C(\c6ccc(Cl)cc6)CCCCCC5)CC4)cc3Oc3cccc4[nH]ccc34)cc2[N+](=O)[O-])CC1] |
| 4-(4-{[2-(4-chlorophenyl)cyclohept-1-en-1-yl]methyl}piperazin-1-yl)-2-(1H-indol-4-yloxy)-N-({4-[(1-methylpiperidin-4-yl)amino]-3-nitrophenyl}sulfonyl)benzamide | 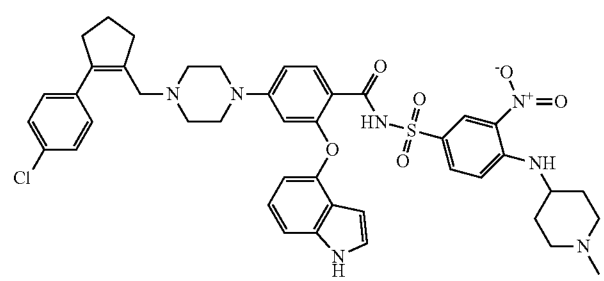 |
| 4-(4-{[2-(4-chlorophenyl)cyclopent-1-en-1-yl]methyl}piperazin-1-yl)-2-(1H-indol-4-yloxy)-N-({4-[(1-methylpiperidin-4-yl)amino]-3-nitrophenyl}sulfonyl)benzamide | 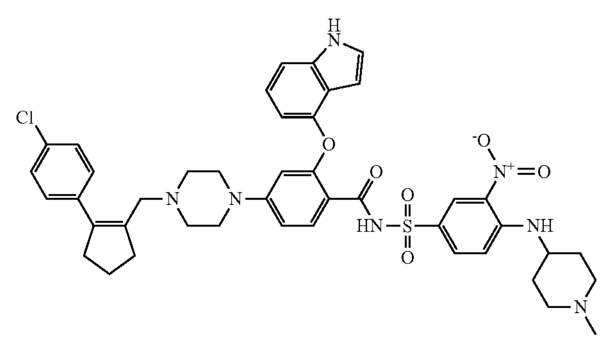 |

| Name | Structure |
|---|---|
| 4-(4-{[2-(4-chlorophenyl)cyclohex-1-en-1-yl]methyl}piperazin-1-yl)-2-(1H-indol-4-yloxy)-N-({4-[(1-methylpiperidin-4-yl)amino]-3-nitrophenyl}sulfonyl)benzamide | 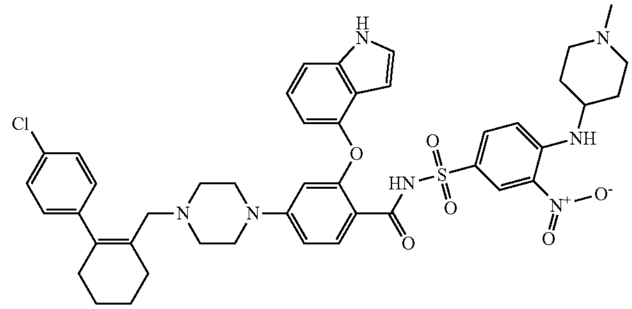 [SMILES: CN1CCC(Nc2ccc(S(=O)(=O)NC(=O)c3ccc(N4CCN(CC5=C(c6ccc(Cl)cc6)CCCC5)CC4)cc3Oc3cccc4[nH]ccc34)cc2[N+](=O)[O-])CC1] |
| 4-(4-{[4-(4-chlorophenyl)-6,6-dimethyl-5,6-dihydro-2H-pyran-3-yl]methyl}piperazin-1-yl)-2-(1H-indol-5-yloxy)-N-({4-[(1-methylpiperidin-4-yl)amino]-3-nitrophenyl}sulfonyl)benzamide | 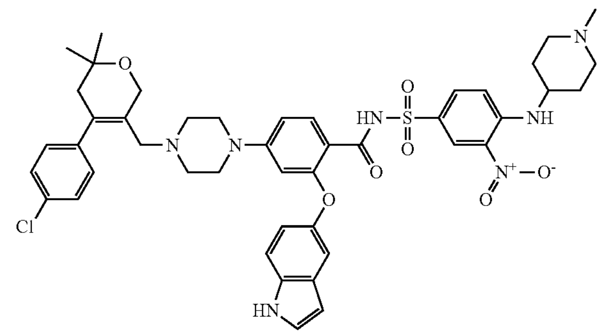 [SMILES: CN1CCC(Nc2ccc(S(=O)(=O)NC(=O)c3ccc(N4CCN(CC5=C(c6ccc(Cl)cc6)CC(C)(C)OC5)CC4)cc3Oc3ccc4[nH]ccc4c3)cc2[N+](=O)[O-])CC1] |
| 4-(4-{[2-(4-chlorophenyl)cyclohept-1-en-1-yl]methyl}piperazin-1-yl)-2-(1H-indol-5-yloxy)-N-({4-[(1-methylpiperidin-4-yl)amino]-3-nitrophenyl}sulfonyl)benzamide | 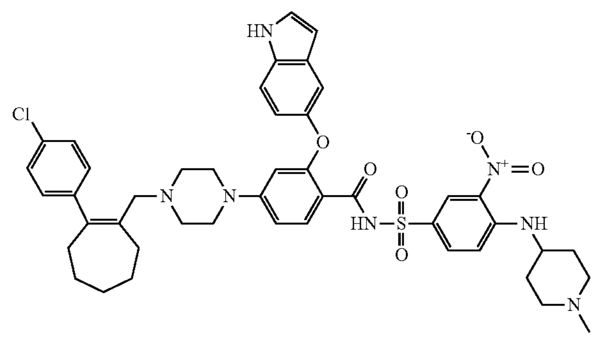 |
| 4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)-2-phenoxybenzamide | 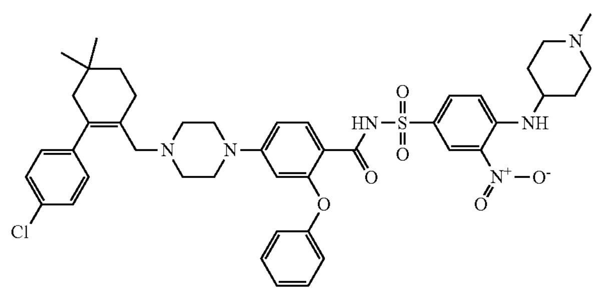 [SMILES: CN1CCC(Nc2ccc(S(=O)(=O)NC(=O)c3ccc(N4CCN(CC5=C(c6ccc(Cl)cc6)CC(C)(C)CC5)CC4)cc3Oc3ccccc3)cc2[N+](=O)[O-])CC1] |
| 4-{4-[(4'-chloro-1,1'-biphenyl-2-yl)methyl]piperazin-1-yl}-N-[(4-{[2-(dimethylamino)ethyl]amino}-3-nitrophenyl)sulfonyl]-2-phenoxybenzamide | 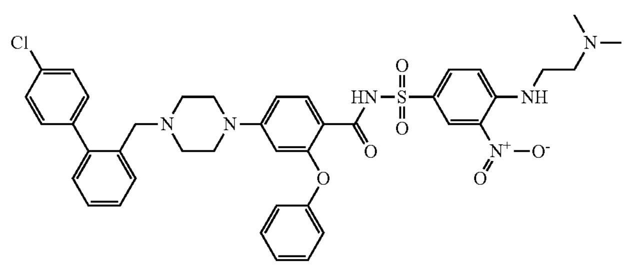 [SMILES: CN(C)CCNc1ccc(S(=O)(=O)NC(=O)c2ccc(N3CCN(Cc4ccccc4-c4ccc(Cl)cc4)CC3)cc2Oc2ccccc2)cc1[N+](=O)[O-]] |

-continued

| Name | Structure |
|------|-----------|
| 4-{4-[(4'-chloro-1,1'-biphenyl-2-yl)methyl]piperazin-1-yl}-N-[(4-{[3-(dimethylamino)propyl]amino}-3-nitrophenyl)sulfonyl]-2-phenoxybenzamide | 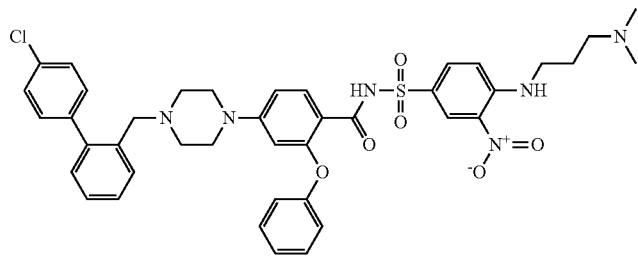 |
| 4-{4-[(4'-chloro-1,1'-biphenyl-2-yl)methyl]piperazin-1-yl}-N-({4-[(3-morpholin-4-ylpropyl)amino]-3-nitrophenyl}sulfonyl)-2-phenoxybenzamide | 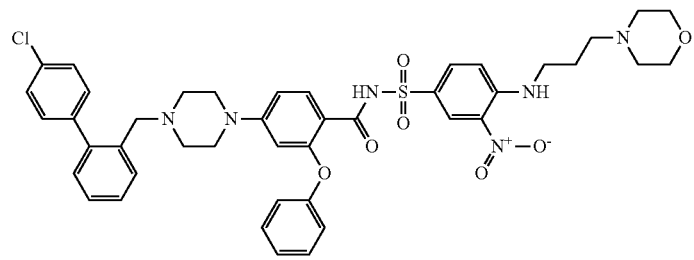 [SMILES: O=C(NS(=O)(=O)c1ccc(NCCCN2CCOCC2)c([N+](=O)[O-])c1)c1ccc(N2CCN(Cc3ccccc3-c3ccc(Cl)cc3)CC2)cc1Oc1ccccc1] |
| 4-{4-[(4'-chloro-1,1'-biphenyl-2-yl)methyl]piperazin-1-yl}-N-[(4-{[4-(dimethylamino)butyl]amino}-3-nitrophenyl)sulfonyl]-2-phenoxybenzamide | 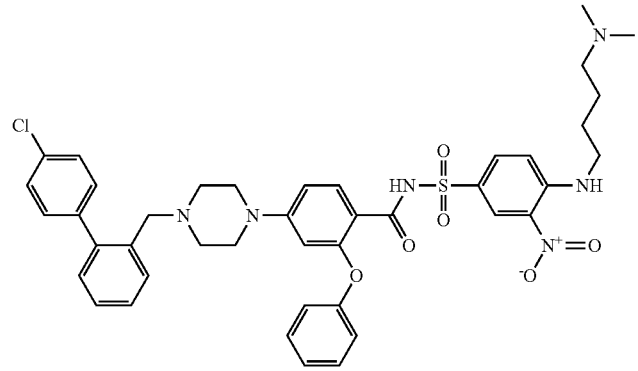 |
| 4-{4-[(4'-chloro-1,1'-biphenyl-2-yl)methyl]piperazin-1-yl}-N-[(3-nitro-4-{[1-(phenylsulfonyl)piperidin-4-yl]amino}phenyl)sulfonyl]-2-phenoxybenzamide | 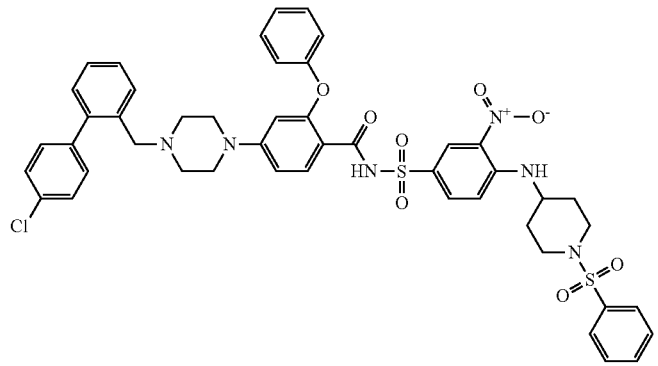 [SMILES: O=C(NS(=O)(=O)c1ccc(NC2CCN(S(=O)(=O)c3ccccc3)CC2)c([N+](=O)[O-])c1)c1ccc(N2CCN(Cc3ccccc3-c3ccc(Cl)cc3)CC2)cc1Oc1ccccc1] |

| Name | Structure |
|---|---|
| 4-{4-[(4'-chloro-1,1'-biphenyl-2-yl)methyl]piperazin-1-yl}-N-[(3-nitro-4-{[1-(quinolin-8-ylsulfonyl)piperidin-4-yl]amino}phenyl)sulfonyl]-2-phenoxybenzamide | 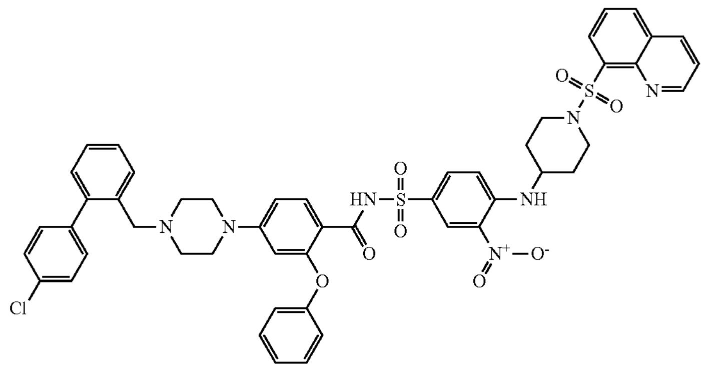 [SMILES: O=C(NS(=O)(=O)c1ccc(NC2CCN(S(=O)(=O)c3cccc4cccnc34)CC2)c([N+](=O)[O-])c1)c1ccc(N2CCN(Cc3ccccc3-c3ccc(Cl)cc3)CC2)cc1Oc1ccccc1] |
| 4-{4-[(4'-chloro-1,1'-biphenyl-2-yl)methyl]piperazin-1-yl}-2-phenoxy-N-({4-{[1-(phenylsulfonyl)piperidin-4-yl]amino}-3-[(trifluoromethyl)sulfonyl]phenyl}sulfonyl)benzamide | 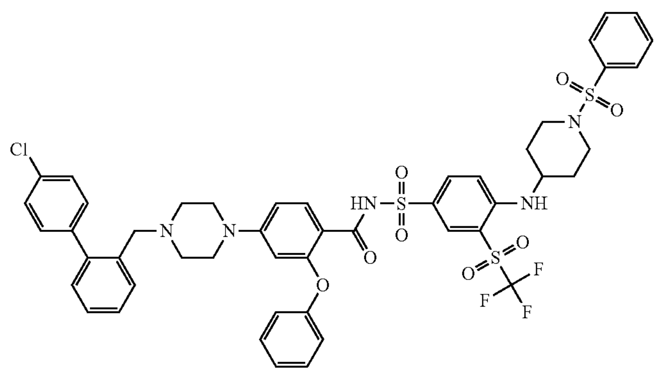 [SMILES: O=C(NS(=O)(=O)c1ccc(NC2CCN(S(=O)(=O)c3ccccc3)CC2)c(S(=O)(=O)C(F)(F)F)c1)c1ccc(N2CCN(Cc3ccccc3-c3ccc(Cl)cc3)CC2)cc1Oc1ccccc1] |
| 4-{4-[(4'-chloro-1,1'-biphenyl-2-yl)methyl]piperazin-1-yl}-2-phenoxy-N-({4-{[1-(quinolin-8-ylsulfonyl)piperidin-4-yl]amino}-3-[(trifluoromethyl)sulfonyl]phenyl}sulfonyl)benzamide | 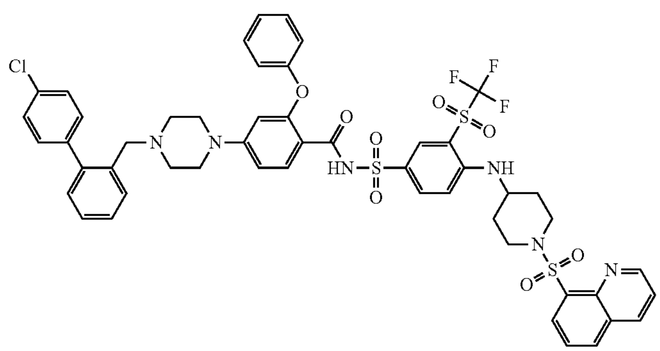 [SMILES: O=C(NS(=O)(=O)c1ccc(NC2CCN(S(=O)(=O)c3cccc4cccnc34)CC2)c(S(=O)(=O)C(F)(F)F)c1)c1ccc(N2CCN(Cc3ccccc3-c3ccc(Cl)cc3)CC2)cc1Oc1ccccc1] |
| 4-{4-[(4'-chloro-1,1'-biphenyl-2-yl)methyl]piperazin-1-yl}-N-[(4-{[(1S)-3-(dimethylamino)-1-thien-2-ylpropyl]amino}-3-nitrophenyl)sulfonyl]-2-phenoxybenzamide | 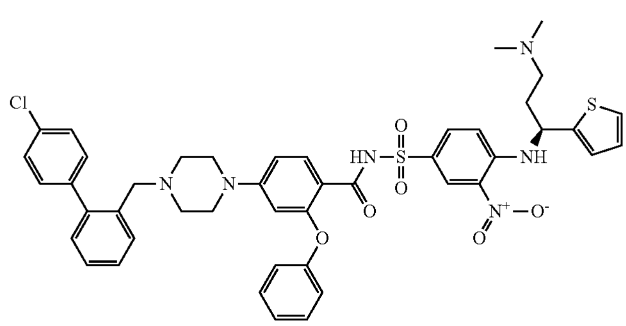 [SMILES: CN(C)CC[C@H](Nc1ccc(S(=O)(=O)NC(=O)c2ccc(N3CCN(Cc4ccccc4-c4ccc(Cl)cc4)CC3)cc2Oc2ccccc2)cc1[N+](=O)[O-])c1cccs1] |

| Name | Structure |
|---|---|
| 4-{4-[(4'-chloro-1,1'-biphenyl-2-yl)methyl]piperazin-1-yl}-N-({3-nitro-4-[(thien-2-ylmethyl)amino]phenyl}sulfonyl)-2-phenoxybenzamide | 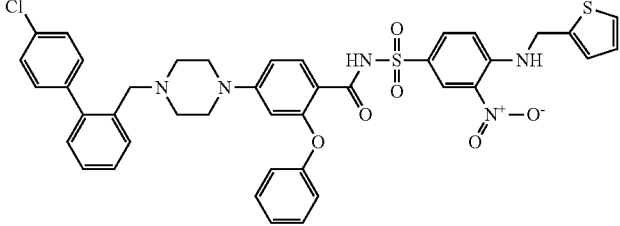 [SMILES: O=C(NS(=O)(=O)c1ccc(NCc2cccs2)c([N+](=O)[O-])c1)c1ccc(N2CCN(Cc3ccccc3-c3ccc(Cl)cc3)CC2)cc1Oc1ccccc1] |
| 4-{4-[(4'-chloro-1,1'-biphenyl-2-yl)methyl]piperazin-1-yl}-2-phenoxy-N-({4-[(tetrahydro-2H-pyran-4-ylmethyl)amino]-3-[(trifluoromethyl)sulfonyl]phenyl}sulfonyl)benzamide | 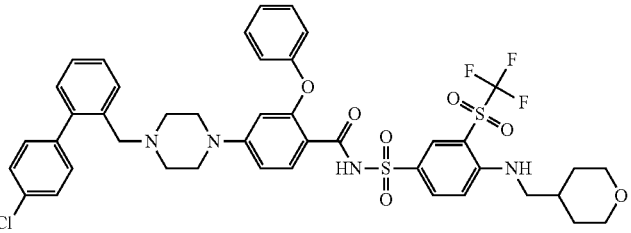 [SMILES: O=C(NS(=O)(=O)c1ccc(NCC2CCOCC2)c(S(=O)(=O)C(F)(F)F)c1)c1ccc(N2CCN(Cc3ccccc3-c3ccc(Cl)cc3)CC2)cc1Oc1ccccc1] |
| 4-{4.[(4'.chloro-1,1'-biphenyl-2-yl)methyl]piperazin-1-yl}-N-[(3-nitro-4-{[2-(1H-1,2,3-triazol-1-yl)ethyl]amino}phenyl)sulfonyl]-2-phenoxybenzamide | 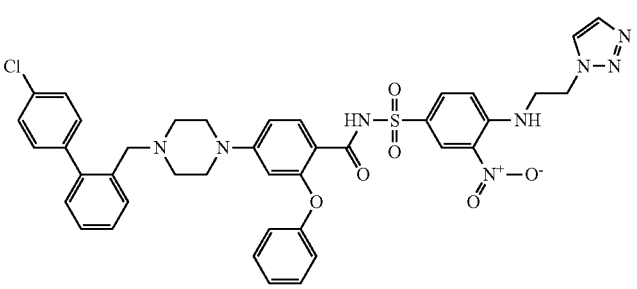 [SMILES: O=C(NS(=O)(=O)c1ccc(NCCn2ccnn2)c([N+](=O)[O-])c1)c1ccc(N2CCN(Cc3ccccc3-c3ccc(Cl)cc3)CC2)cc1Oc1ccccc1] |
| 4-{4-[(4'-chloro-1,1'-biphenyl-2-yl)methyl]piperazin-1-yl}-N-[(3-nitro-4-{[2-(2H-1,2,3-triazol-2-yl)ethyl]amino}phenyl)sulfonyl]-2-phenoxybenzamide | 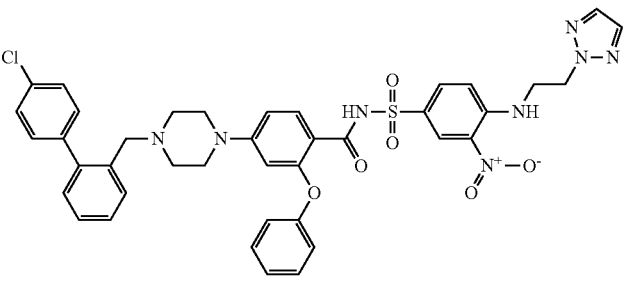 [SMILES: O=C(NS(=O)(=O)c1ccc(NCCn2nccn2)c([N+](=O)[O-])c1)c1ccc(N2CCN(Cc3ccccc3-c3ccc(Cl)cc3)CC2)cc1Oc1ccccc1] |
| 4-{4-[(4'-chloro-1,1'-biphenyl-2-yl)methyl]piperazin-1-yl}-N-[(4-{[3-(dimethylamino)propyl]amino}-3-nitrophenyl)sulfonyl]-2-(2-naphthyloxy)benzamide | 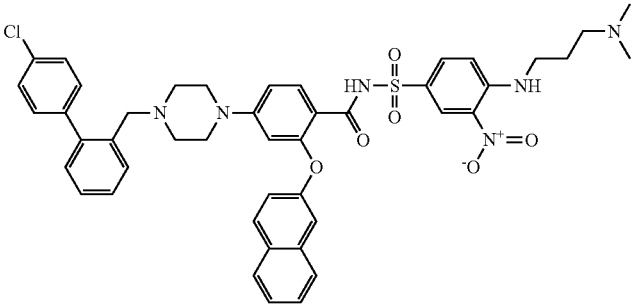 |

-continued

| Name | Structure |
|---|---|
| 4-{4-[(4'-chloro-1,1'-biphenyl-2-yl)methyl]piperazin-1-yl}-N-[(3-nitro-4-{[2-(2-oxopyridin-1(2H)-yl)ethyl]amino}phenyl)sulfonyl]-2-phenoxybenzamide | 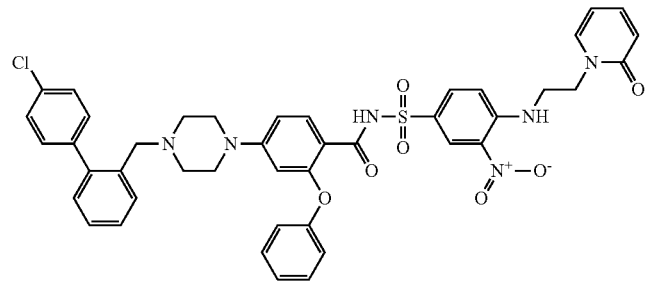 [SMILES: O=C(NS(=O)(=O)c1ccc(NCCn2ccccc2=O)c([N+](=O)[O-])c1)c1ccc(N2CCN(Cc3ccccc3-c3ccc(Cl)cc3)CC2)cc1Oc1ccccc1] |
| 4-{4-[(4'-chloro-1,1'-biphenyl-2-yl)methyl]piperazin-1-yl}-N-[(3-nitro-4-{2-(pyridin-2-yloxy)ethyl]amino}phenyl)sulfonyl]-2-phenoxybenzamide | 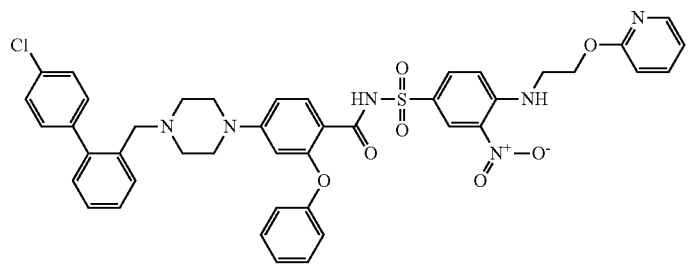 [SMILES: O=C(NS(=O)(=O)c1ccc(NCCOc2ccccn2)c([N+](=O)[O-])c1)c1ccc(N2CCN(Cc3ccccc3-c3ccc(Cl)cc3)CC2)cc1Oc1ccccc1] |
| 4-{4-[(4'-chloro-1,1'-biphenyl-2-yl)methyl]piperazin-1-yl}-N-({3-nitro-4-[(2-pyridin-4-ylethyl)amino]phenyl}sulfonyl)-2-phenoxybenzamide | 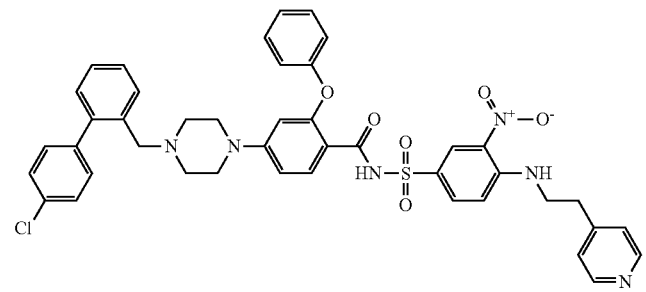 [SMILES: O=C(NS(=O)(=O)c1ccc(NCCc2ccncc2)c([N+](=O)[O-])c1)c1ccc(N2CCN(Cc3ccccc3-c3ccc(Cl)cc3)CC2)cc1Oc1ccccc1] |
| 4-(4-{[2-(4-chlorophenyl)-4,4-dimethylcyclohex-1-en-1-yl]methyl}piperazin-1-yl)-N-({4-{[3-(dimethylamino)propyl]amino}-3-[(trifluoromethyl)sulfonyl]phenyl}sulfonyl)-2-(1H-indol-5-yloxy)benzamide | 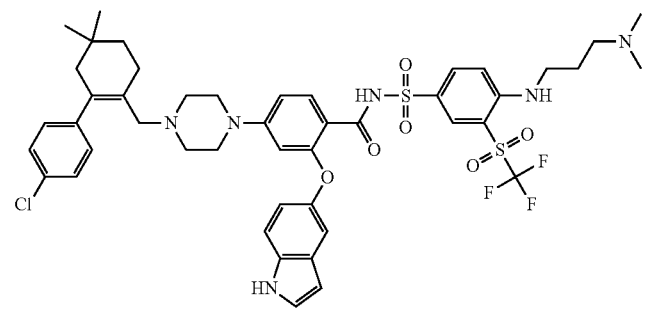 [SMILES: CN(C)CCCNc1ccc(S(=O)(=O)NC(=O)c2ccc(N3CCN(CC4=C(c5ccc(Cl)cc5)CC(C)(C)CC4)CC3)cc2Oc2ccc3[nH]ccc3c2)cc1S(=O)(=O)C(F)(F)F] |
| 4-(4-{[2-(4-chlorophenyl)-4,4-dimethylcyclohex-1-en-1-yl]methyl}piperazin-1-yl)-N-{[4-{[3-(dimethylamino)propyl]amino}-3-(trifluoromethyl)phenyl]sulfonyl}-2-(1H-indol-5-yloxy)benzamide | 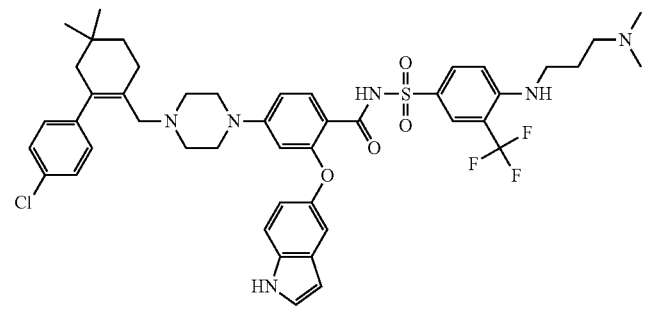 [SMILES: CN(C)CCCNc1ccc(S(=O)(=O)NC(=O)c2ccc(N3CCN(CC4=C(c5ccc(Cl)cc5)CC(C)(C)CC4)CC3)cc2Oc2ccc3[nH]ccc3c2)cc1C(F)(F)F] |

| Name | Structure |
|---|---|
| 4-(4-{[2-(4-chlorophenyl)-4,4-dimethylcyclohex-1-en-1-yl]methyl}piperazin-1-yl)-N-[(3-cyano-4-{[3-(dimethylamino)propyl]amino}phenyl)sulfonyl]-2-(1H-indol-5-yloxy)benzamide | 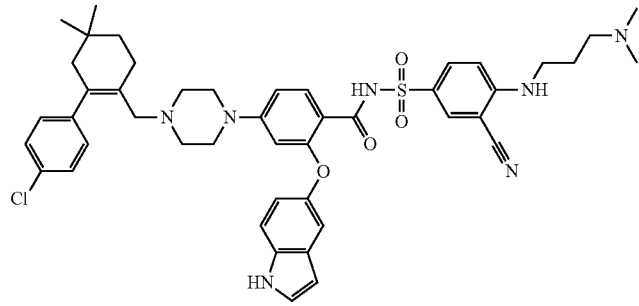 [SMILES: CN(C)CCCNc1ccc(S(=O)(=O)NC(=O)c2ccc(N3CCN(CC4=C(c5ccc(Cl)cc5)CC(C)(C)CC4)CC3)cc2Oc2ccc3[nH]ccc3c2)cc1C#N] |
| 4-(4-{[2-(4-chlorophenyl)-4,4-dimethylcyclohex-1-en-1-yl]methyl}piperazin-1-yl)-2-(1H-indol-5-yloxy)-N-({3-nitro-4-[(1-tetrahydro-2H-pyran-4-ylpiperidin-4-yl)amino]phenyl}sulfonyl)benzamide | 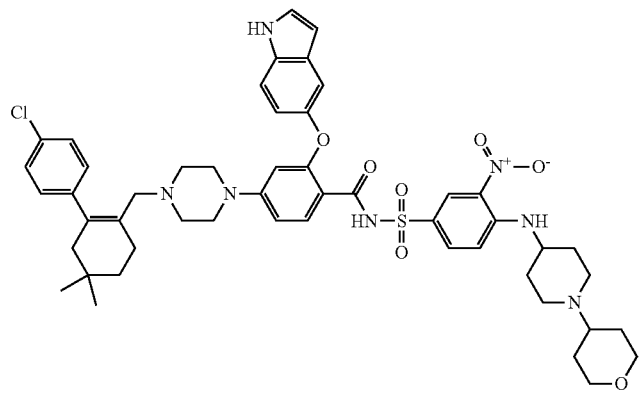 [SMILES: CC1(C)CCC(CN2CCN(c3ccc(C(=O)NS(=O)(=O)c4ccc(NC5CCN(C6CCOCC6)CC5)c([N+](=O)[O-])c4)c(Oc4ccc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-2-(1H-indol-5-yloxy)-N-({4-[(4-methylpiperazin-1-yl)amino]-3-nitrophenyl}sulfonyl)benzamide | 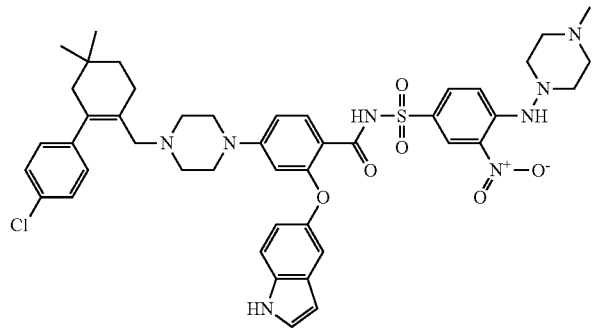 [SMILES: CN1CCN(Nc2ccc(S(=O)(=O)NC(=O)c3ccc(N4CCN(CC5=C(c6ccc(Cl)cc6)CC(C)(C)CC5)CC4)cc3Oc3ccc4[nH]ccc4c3)cc2[N+](=O)[O-])CC1] |
| 4-{4-[1-(4'-chloro-1,1'-biphenyl-2-yl)ethyl]piperazin-1-yl}-2-(1H-indol-4-yloxy)-N-({3-nitro-4-[(tetrahydro-2H-pyran-4-ylmethyl)amino]phenyl}sulfonyl)benzamide | 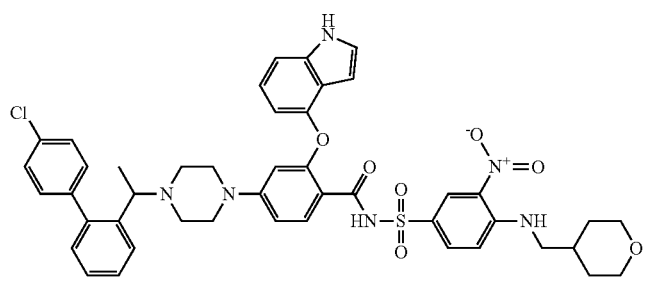 |

-continued

| Name | Structure |
|---|---|
| N-[(4-{[(4-aminotetrahydro-2H-pyran-4-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-indol-4-yloxy)benzamide | 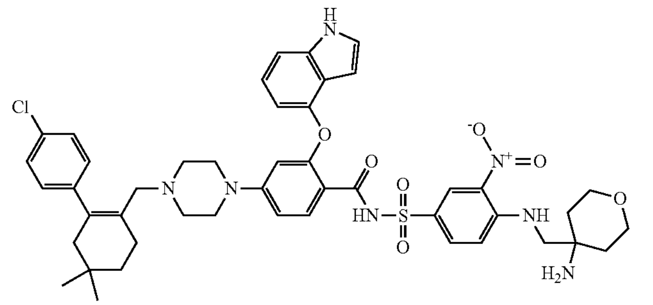 |
| 4-(4-{[2-(4-chlorophenyl)-4,4-dimethylcyclohex-1-en-1-yl]methyl}piperazin-1-yl)-2-(1H indol-5-yloxy)-N-({3-nitro-4-[(tetrahydro-2H-pyran-4-ylmethyl)amino]phenyl}sulfonyl)benzamide | 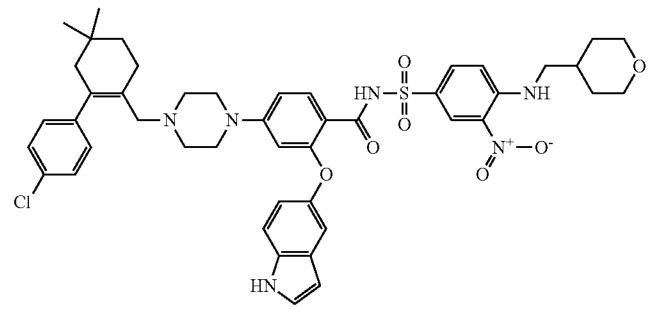 [SMILES: CC1(C)CCC(CN2CCN(c3ccc(C(=O)NS(=O)(=O)c4ccc(NCC5CCOCC5)c([N+](=O)[O-])c4)c(Oc4ccc5[nH]ccc5c4)c3)CC2)=C(c2ccc(Cl)cc2)C1] |
| Trans-4-(4-{[2-(4-chlorophenyl)-4,4-dimethylcyclohex-1-en-1-yl]methyl}piperazin-1-yl)-2-(1H-indol-5-yloxy)-N-({4-[(4-morpholin-4-ylcyclohexyl)amino]-3-nitrophenyl}sulfonyl)benzamide | 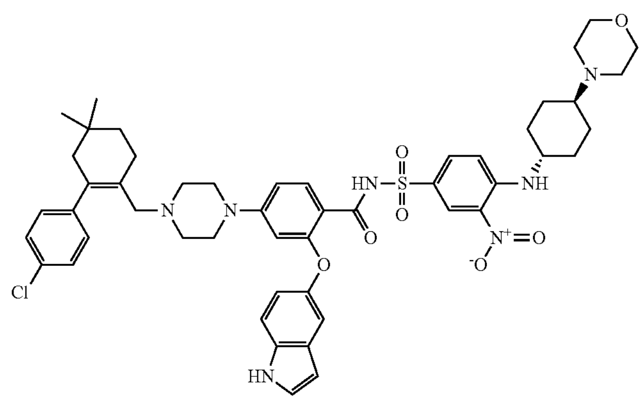 |
| 4-(4-{[2-(4-chlorophenyl)-4,4-dimethylcyclohex-1-en-1-yl]methyl}piperazin-1-yl)-2-(1H-indol-5-yloxy)-N-({4-[(2-methoxyethyl)amino]-3-nitrophenyl}sulfonyl)benzamide | 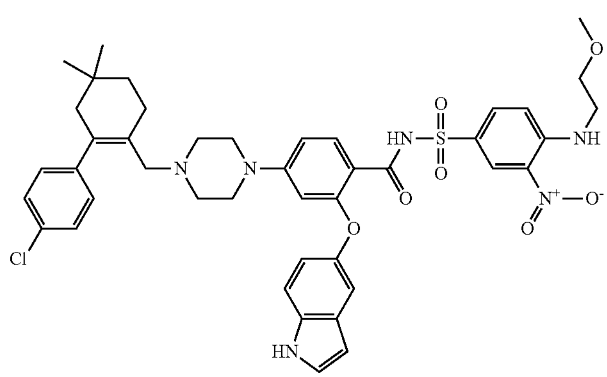 [SMILES: COCCNc1ccc(S(=O)(=O)NC(=O)c2ccc(N3CCN(CC4=C(c5ccc(Cl)cc5)CC(C)(C)CC4)CC3)cc2Oc2ccc3[nH]ccc3c2)cc1[N+](=O)[O-]] |

-continued

| Name | Structure |
|---|---|
| 4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[(3S)-tetrahydro-2H-pyran-3-ylmethyl]amino}phenyl)sulfonyl]benzamide | 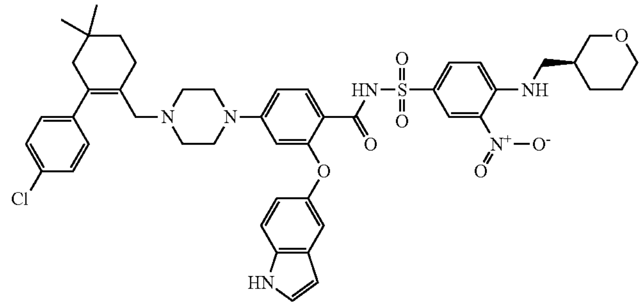 [SMILES: CC1(C)CCC(CN2CCN(c3ccc(C(=O)NS(=O)(=O)c4ccc(NC[C@@H]5CCCOC5)c([N+](=O)[O-])c4)c(Oc4ccc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-2-(1H indol-5-yloxy)-N-[(3-nitro-4-{[(3R)-tetrahydro-2H-pyran-3-ylmethyl]amino}phenyl)sulfonyl]benzamide | 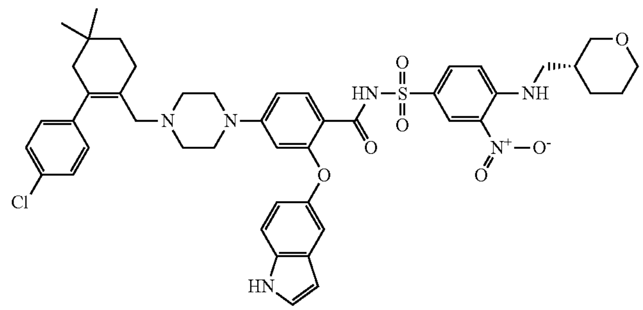 [SMILES: CC1(C)CCC(CN2CCN(c3ccc(C(=O)NS(=O)(=O)c4ccc(NC[C@H]5CCCOC5)c([N+](=O)[O-])c4)c(Oc4ccc5[nH]ccc5c4)c3)CC2)=C(c2ccc(Cl)cc2)C1] |
| 4-(4-{[4-(4-chlorophenyl)-6,6-dimethyl-5,6-dihydro-2H-pyran-3-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide | 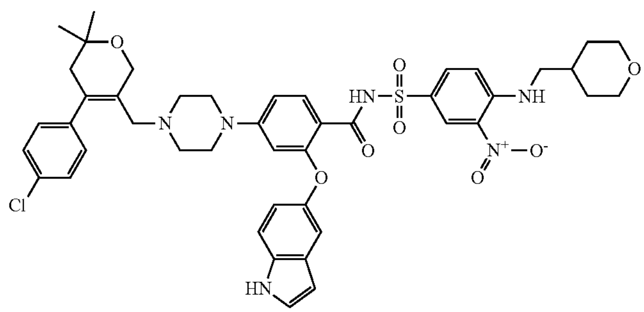 |
| 4-(4-{[2-(4-chlorophenyl)-4,4-dimethylcyclohex-1-en-1-yl]methyl}piperazin-1-yl)-N-[(4-{[(4-hydroxy-1-methylpiperidin-4-yl)methyl]amino}-3-nitrophenyl)sulfonyl]-2-(1H-indol-5-yloxy)benzamide | 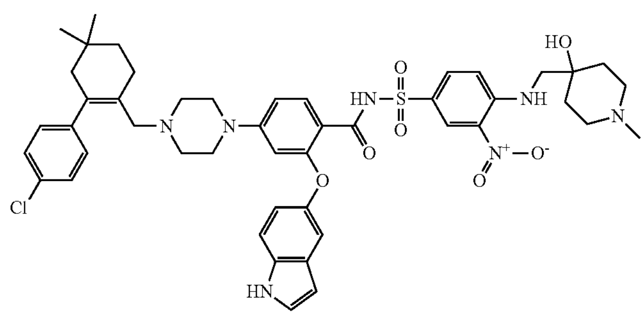 [SMILES: CN1CCC(O)(CNc2ccc(S(=O)(=O)NC(=O)c3ccc(N4CCN(CC5=C(c6ccc(Cl)cc6)CC(C)(C)CC5)CC4)cc3Oc3ccc4[nH]ccc4c3)cc2[N+](=O)[O-])CC1] |
| 4-(4-{[2-(4-chlorophenyl)-4,4-dimethylcyclohex-1-en-1-yl]methyl}piperazin-1-yl)-3-fluoro-2-(1H-indol-5-yloxy)-N-({4-[(1-methylpiperidin-4-yl)amino]-3-nitrophenyl}sulfonyl)benzamide | 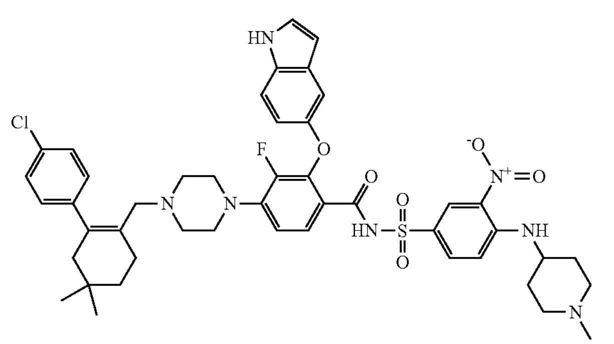 |

| Name | Structure |
|---|---|
| 4-(4-{[2-(4-chlorophenyl)-4,4-dimethylcyclohex-1-en-1-yl]methyl}piperazin-1-yl)-3-fluoro-2-(1H-indol-5-yloxy)-N-({3-nitro-4-[(1-tetrahydro-2H-pyran-4-ylpiperidin-4-yl)amino]phenyl}sulfonyl)benzamide | 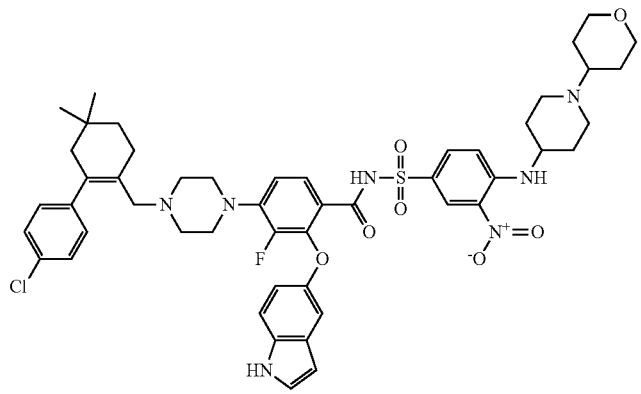 |
| 4-(4-{[2-(4-chlorophenyl)-4,4-dimethylcyclohex-1-en-1-yl]methyl}piperazin-1-yl)-N-[(4-{[(4-hydroxy-1-methylpiperidin-4-yl)methyl]amino}-3-nitrophenyl)sulfonyl]-2-(1H-indol-4-yloxy)benzamide | 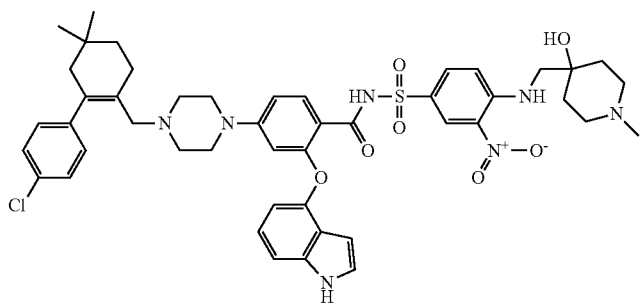 [SMILES: CN1CCC(O)(CNc2ccc(S(=O)(=O)NC(=O)c3ccc(N4CCN(CC5=C(c6ccc(Cl)cc6)CC(C)(C)CC5)CC4)cc3Oc3cccc4[nH]ccc34)cc2[N+](=O)[O-])CC1] |
| N-[(4-{[(3S,4R)-1-benzyl-3-hydroxypiperidin-4-yl]amino}-3-nitrophenyl)sulfonyl]-4-(4-{[2-(4-chlorophenyl)-4,4-dimethylcyclohex-1-en-1-yl]methyl}piperazin-1-yl)-2-(1H-indol-5-yloxy)benzamide | 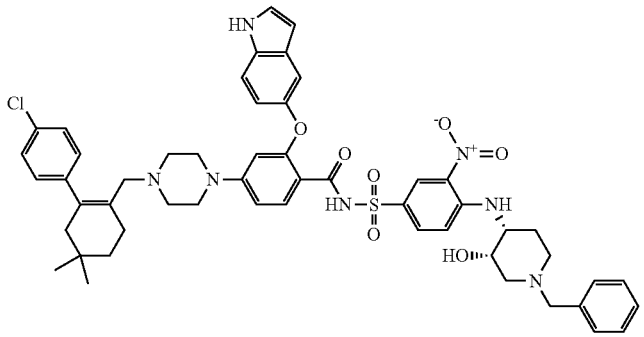 |
| N-[(4-{[(4-aminotetrahydro-2H-pyran-4-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-indol-5-yloxy)benzamide | 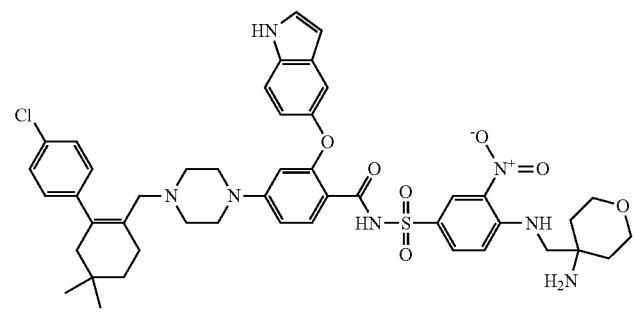 |

| Name | Structure |
|---|---|
| 4-(4-{[2-(4-chlorophenyl)-4,4-dimethylcyclohex-1-en-1-yl]methyl}piperazin-1-yl)-2-(1H-indol-5-yloxy)-N-[(4-{[1-(2-methoxyethyl)piperidin-4-yl]amino}-3-nitrophenyl)sulfonyl]benzamide | 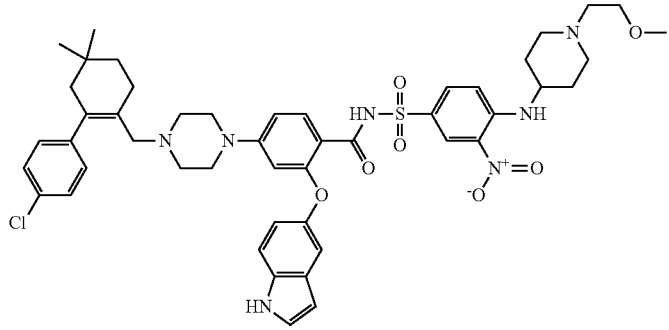 |
| 4-(4-{[2-(4-chlorophenyl)-4,4-dimethylcyclohex-1-en-1-yl]methyl}piperazin-1-yl)-2-(1H-indol-4-yloxy)-N-({4-[(4-methylpiperazin-1-yl)amino]-3-nitrophenyl}sulfonyl)benzamide | 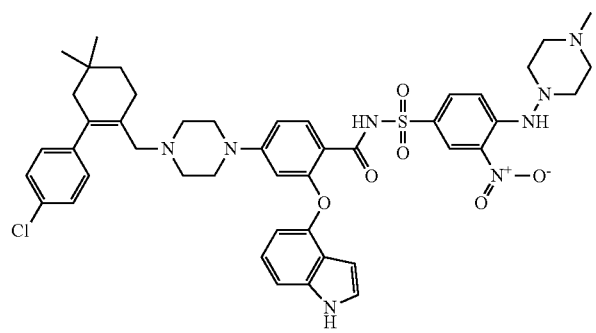 |
| 4-(4-{[2-(4-chlorophenyl)-4,4-dimethylcyclohex-1-en-1-yl]methyl}piperazin-1-yl)-N-[(4-{[1-(2-hydroxyethyl)piperidin-4-yl]amino}-3-nitrophenyl)sulfonyl]-2-(1H-indol-4-yloxy)benzamide | 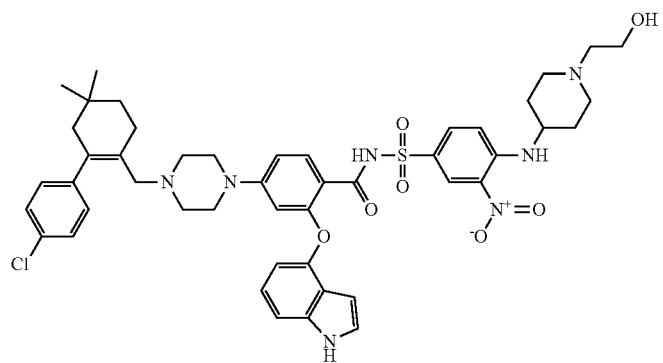 |
| 4-(4-{[2-(4-chlorophenyl)-4,4-dimethylcyclohex-1-en-1-yl]methyl}piperazin-1-yl)-2-(1H-indol-4-yloxy)-N-[(4-{[1-(2-methoxyethyl)piperidin-4-yl]amino}-3-nitrophenyl)sulfonyl]benzamide | 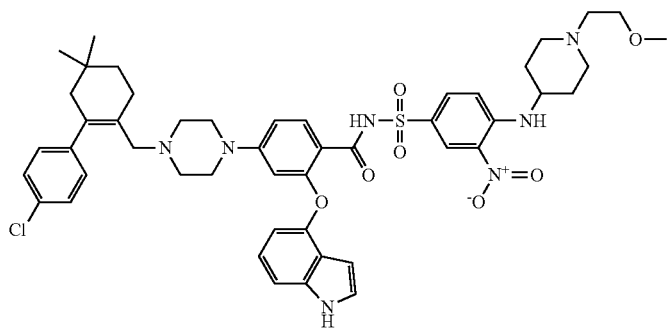 |

| Name | Structure |
|---|---|
| 4-(4-{[2-(4-chlorophenyl)-4,4-dimethylcyclohex-1-en-1-yl]methyl}piperazin-1-yl)-N-[(4-{[1-(3-hydroxypropyl)piperidin-4-yl]amino}-3-nitrophenyl)sulfonyl]-2-(1H-indol-4-yloxy)benzamide | 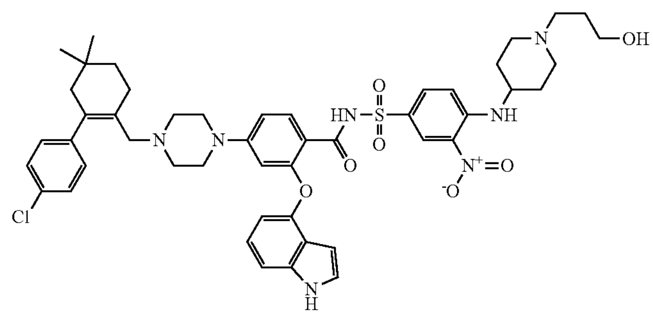 |
| 4-[4-({4'-chloro-3-[3-(dimethylamino)propyl]-1,1'-biphenyl-2-yl}methyl)piperazin-1-yl]-2-(1H-indol-4-yloxy)-N-({3-nitro-4-[(tetrahydro-2H-pyran-4-ylmethyl)amino]phenyl}sulfonyl)benzamide | 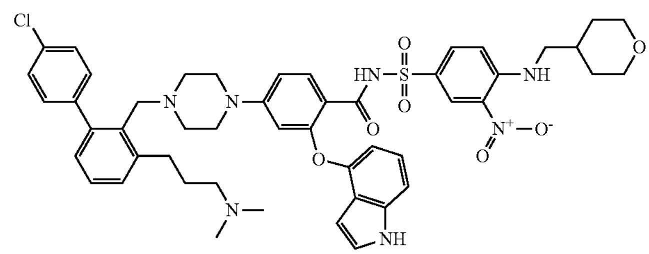 |
| 4-(4-{[2-(4-chlorophenyl)-4,4-dimethylcyclohex-1-en-1-yl]methyl}piperazin-1-yl)-N-[(4-{[1-(3-hydroxypropyl)piperidin-4-yl]amino}-3-nitrophenyl)sulfonyl]-2-(1H-indol-5-yloxy)benzamide | 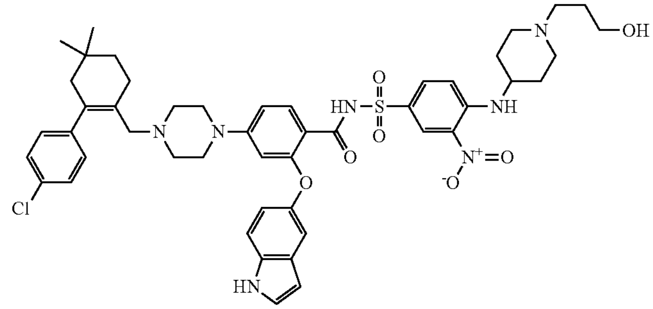 |
| 4-{4-[(4'-chloro-4-morpholin-4-yl-1,1'-biphenyl-2-yl)methyl]piperazin-1-yl}-2-(1H-indol-4-yloxy)-N-({3-nitro-4-[(tetrahydro-2H-pyran-4-ylmethyl)amino]phenyl}sulfonyl)benzamide | 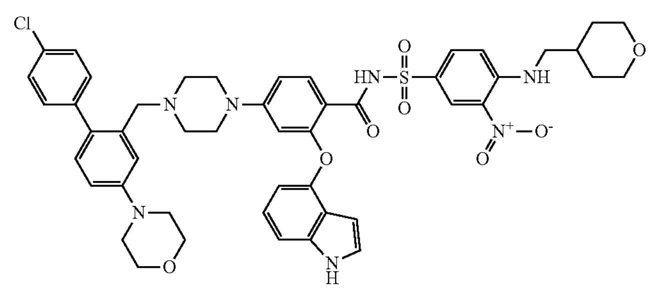 [SMILES: O=C(NS(=O)(=O)c1ccc(NCC2CCOCC2)c([N+](=O)[O-])c1)c1ccc(N2CCN(Cc3cc(N4CCOCC4)ccc3-c3ccc(Cl)cc3)CC2)cc1Oc1cccc2[nH]ccc12] |
| 4-[4-({4'-chloro-3-[2-(dimethylamino)ethoxy]-1,1'-biphenyl-2-yl}methyl)piperazin-1-yl]-2-(1H-indol-4-yloxy)-N-({3-nitro-4-[(1-tetrahydro-2H-pyran-4-ylpiperidin-4-yl)amino]phenyl}sulfonyl)benzamide | 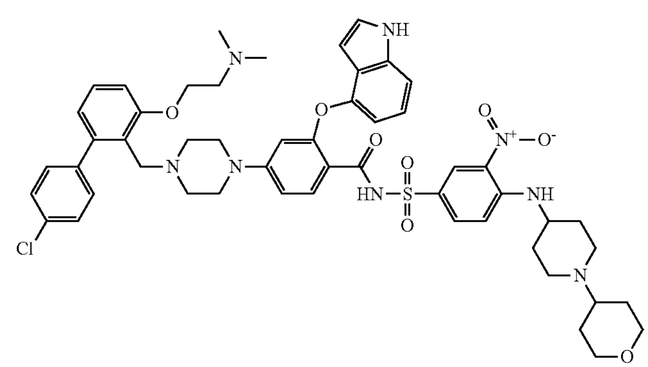 [SMILES: CN(C)CCOc1cccc(-c2ccc(Cl)cc2)c1CN1CCN(c2ccc(C(=O)NS(=O)(=O)c3ccc(NC4CCN(C5CCOCC5)CC4)c([N+](=O)[O-])c3)c(Oc3cccc4[nH]ccc34)c2)CC1] |

| Name | Structure |
|---|---|
| 4-(4-{[2-(4-chlorophenyl)-4,4-dimethylcyclohex-1-en-1-yl]methyl}piperazin-1-yl)-N-[(4-{[4-(diethylamino)cyclohexyl]amino}-3-nitrophenyl)sulfonyl]-2-(1H-indol-5-yloxy)benzamide | 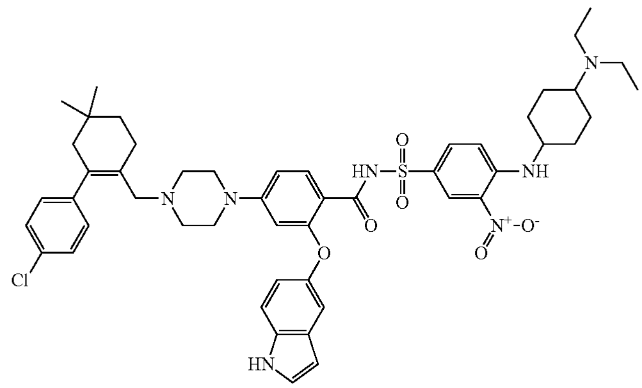 [SMILES: CCN(CC)C1CCC(Nc2ccc(S(=O)(=O)NC(=O)c3ccc(N4CCN(CC5=C(c6ccc(Cl)cc6)CC(C)(C)CC5)CC4)cc3Oc3ccc4[nH]ccc4c3)cc2[N+](=O)[O-])CC1] |
| 4-(4-{[2-(4-chlorophenyl)-4,4-dimethylcyclohex-1-en-1-yl]methyl}piperazin-1-yl)-N-[(4-{[4-(dimethylamino)cyclohexyl]amino}-3-nitrophenyl)sulfonyl]-2-(1H-indol-4-yloxy)benzamide | 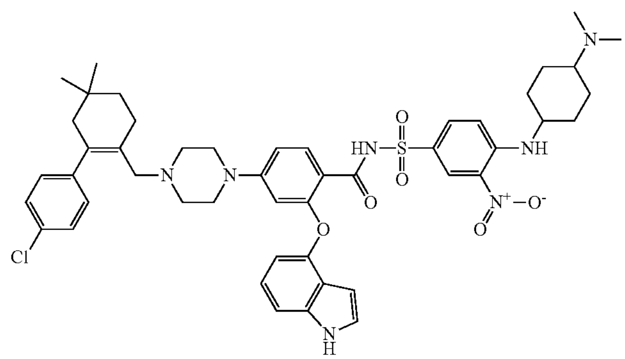 [SMILES: CN(C)C1CCC(Nc2ccc(S(=O)(=O)NC(=O)c3ccc(N4CCN(CC5=C(c6ccc(Cl)cc6)CC(C)(C)CC5)CC4)cc3Oc3cccc4[nH]ccc34)cc2[N+](=O)[O-])CC1] |
| 4-(4-{[2-(4-chlorophenyl)-4,4-dimethylcyclohex-1-en-1-yl]methyl}piperazin-1-yl)-N-[(4-{[4-(diethylamino)cyclohexyl]amino}-3-nitrophenyl)sulfonyl]-2-(1H-indol-4-yloxy)benzamide | 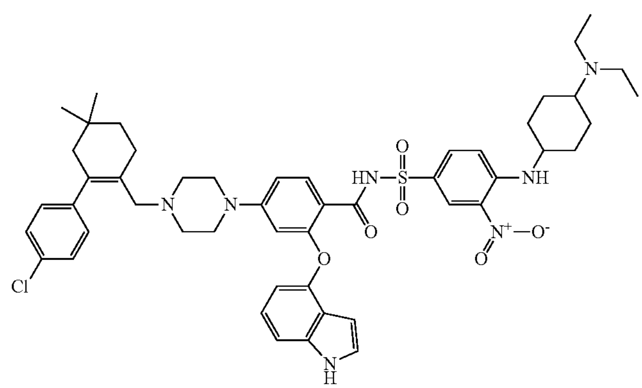 [SMILES: CCN(CC)C1CCC(Nc2ccc(S(=O)(=O)NC(=O)c3ccc(N4CCN(CC5=C(c6ccc(Cl)cc6)CC(C)(C)CC5)CC4)cc3Oc3cccc4[nH]ccc34)cc2[N+](=O)[O-])CC1] |
| Trans-4-(4-{[2-(4-chlorophenyl)-4,4-dimethylcyclohex-1-en-1-yl]methyl}piperazin-1-yl)-2-(1H-indol-4-yloxy)-N-({4-[(4-morpholin-4-ylcyclohexyl)amino]-3-nitrophenyl}sulfonyl)benzamide | 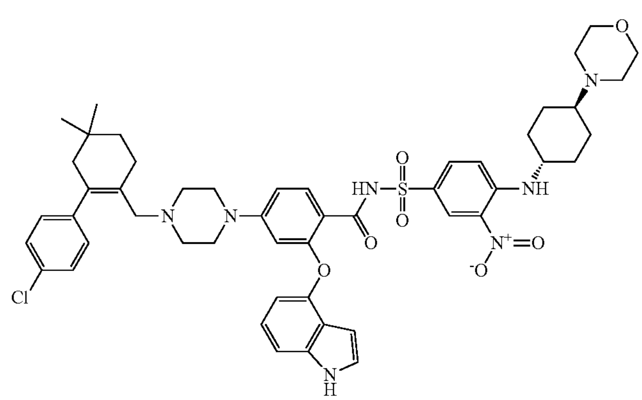 |

-continued

| Name | Structure |
|---|---|
| 4-[4-({4'-chloro-3-[2-(dimethylamino)ethoxy]-1,'-biphenyl-2-yl}methyl)piperazin-1-yl]-2-(1H-indol-4-yloxy)-N-({-[(1-methylpiperidin-4-yl)amino]-3-nitrophenyl}sulfonyl)benzamide | 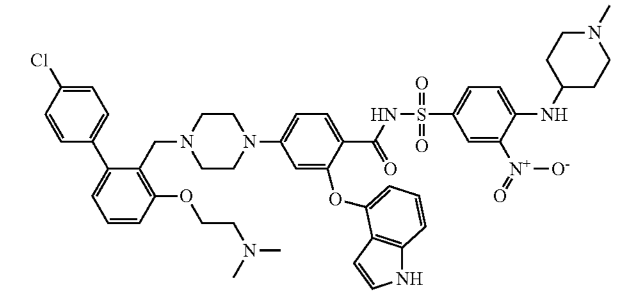 [SMILES: CN(C)CCOc1cccc(-c2ccc(Cl)cc2)c1CN1CCN(c2ccc(C(=O)NS(=O)(=O)c3ccc(NC4CCN(C)CC4)c([N+](=O)[O-])c3)c(Oc3cccc4[nH]ccc34)c2)CC1] |
| 4-{4-[1-(4'-chloro-1,1'-biphenyl-2-yl)ethyl]piperazin-1-yl}-2-(1H-indol-4-yloxy)-N-({4-[(1-methylpiperidin-4-yl)amino]-3-nitrophenyl}sulfonyl)benzamide | 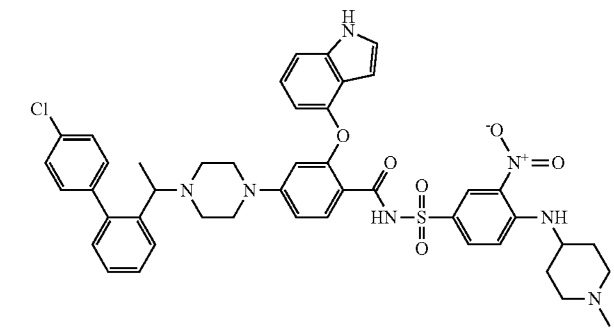 |
| 4-(4-{[2-(4-chlorophenyl)-4,4-dimethylcyclohex-1-en-1-yl]methyl}piperazin-1-yl)-N-{[4-({[4-(dimethylamino)tetrahydro-2H-pyran-4-yl]methyl}amino)-3-nitrophenyl]sulfonyl}-2-(1H-indol-5-yloxy)benzamide | 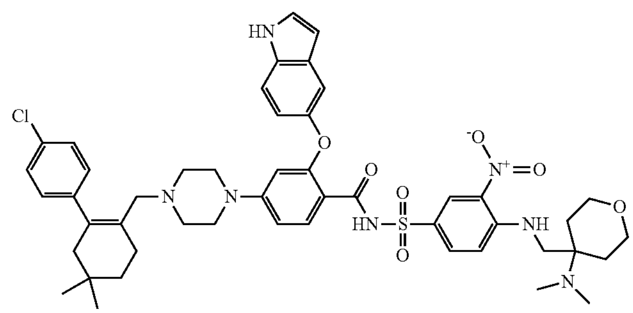 |
| N-({4-[(2-aminocyclohexyl)amino]-3-nitrophenyl}sulfonyl)-4-(4-{[2-(4-chlorophenyl)-4,4-dimethylcyclohex-1-en-1-yl]methyl}piperazin-1-yl)-2-(1H-indol-5-yloxy)benzamide | 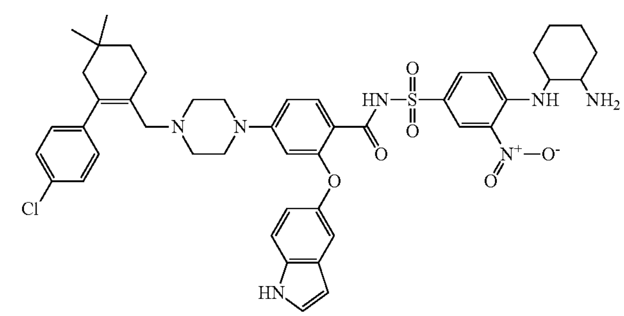 [SMILES: CC1(C)CCC(CN2CCN(c3ccc(C(=O)NS(=O)(=O)c4ccc(NC5CCCCC5N)c([N+](=O)[O-])c4)c(Oc4ccc5[nH]ccc5c4)c3)CC2)=C(c2ccc(Cl)cc2)C1] |
| 4-[4-({4'-chloro-4-[3-(dimethylamino)prop-1-ynyl]-1,1'-biphenyl-2-yl}methyl)piperazin-1-yl]-2-(1H-indol-4-yloxy)-N-({3-nitro-4-[(tetrahydro-2H-pyran-4-ylmethyl)amino]phenyl}sulfonyl)benzamide | 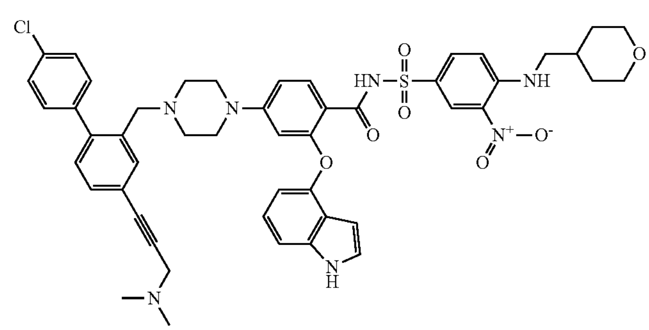 [SMILES: CN(C)CC#Cc1ccc(-c2ccc(Cl)cc2)c(CN2CCN(c3ccc(C(=O)NS(=O)(=O)c4ccc(NCC5CCOCC5)c([N+](=O)[O-])c4)c(Oc4cccc5[nH]ccc45)c3)CC2)c1] |

| Name | Structure |
|---|---|
| 4-(4-{[2-(4-chlorophenyl)-4,4-dimethylcyclohex-1-en-1-yl]methyl}piperazin-1-yl)-2-(1H-indol-4-yloxy)-N-[(3-nitro-4-{[1-(4,4,4-trifluorobutyl)piperidin-4-yl]amino}phenyl)sulfonyl]benzamide | 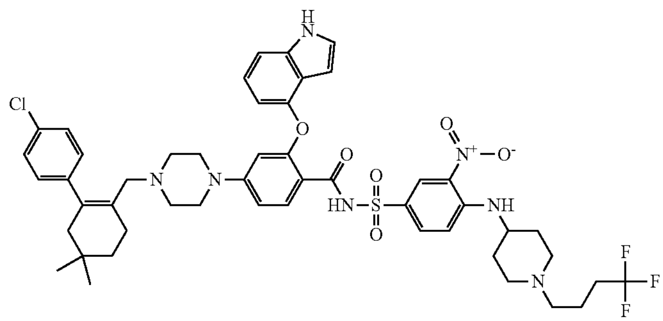 [SMILES: CC1(C)CCC(CN2CCN(c3ccc(C(=O)NS(=O)(=O)c4ccc(NC5CCN(CCCC(F)(F)F)CC5)c([N+](=O)[O-])c4)c(Oc4cccc5[nH]ccc45)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-[(4-{[2-(4-hydroxy-1-methylpiperidin-4-yl)ethyl]amino}-3-nitrophenyl)sulfonyl]-2-(1H-indol-5-yloxy)benzamide | 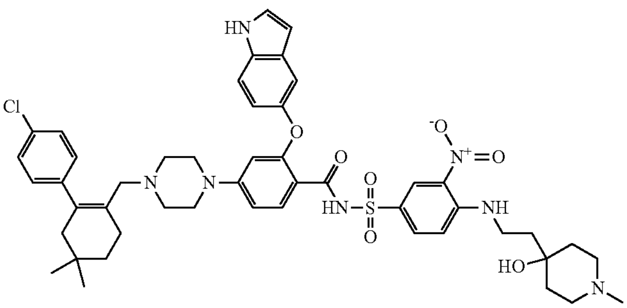 |
| 4-(4-{[2-(4-chlorophenyl)-4,4-dimethylcyclohex-1-en-1-yl]methyl}piperazin-1-yl)-2(1H-indol-5-yloxy)-N-[(3-nitro-4-{[1-(1,3-thiazol-2-yl)piperidin-4-yl]amino}phenyl)sulfonyl]benzamide | 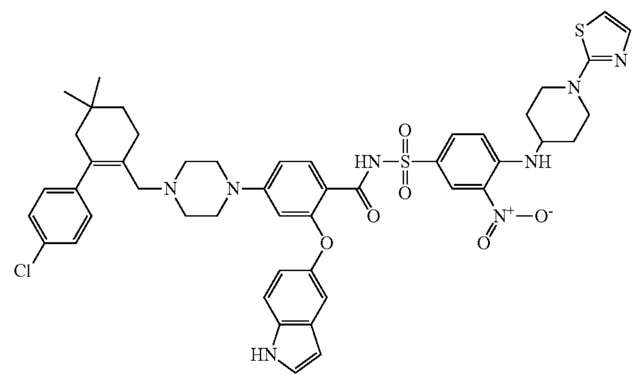 [SMILES: CC1(C)CCC(CN2CCN(c3ccc(C(=O)NS(=O)(=O)c4ccc(NC5CCN(c6nccs6)CC5)c([N+](=O)[O-])c4)c(Oc4ccc5[nH]ccc5c4)c3)CC2)=C(c2ccc(Cl)cc2)C1] |
| 4-(4-{[4'-chloro-4-(2-hydroxyethoxy)-1,1'-biphenyl-2-yl]methyl}piperazin-1-yl)-2-(1H-indol-4-yloxy)-N-({3-nitro-4-[(tetrahydro-2H-pyran-4-ylmethyl)amino]phenyl}sulfonyl)benzamide | 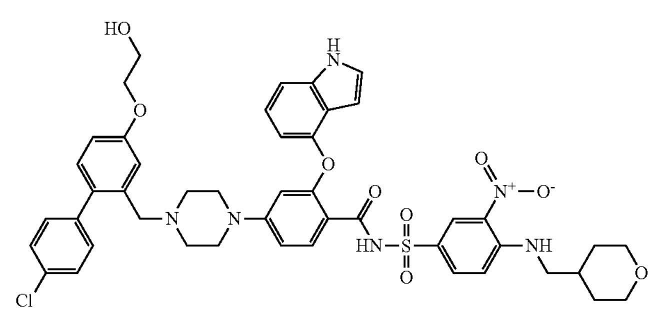 [SMILES: O=C(NS(=O)(=O)c1ccc(NCC2CCOCC2)c([N+](=O)[O-])c1)c1ccc(N2CCN(Cc3cc(OCCO)ccc3-c3ccc(Cl)cc3)CC2)cc1Oc1cccc2[nH]ccc12] |

-continued

| Name | Structure |
|---|---|
| 4-(4-{[2-(4-chlorophenyl)-4,4-dimethylcyclohex-1-en-1-yl]methyl}piperazin-1-yl)-N-[(4-{[1-(cyclopropylmethyl)piperidin-4-yl]amino}-3-nitrophenyl)sulfonyl]-2-(1H-indol-5-yloxy)benzamide | 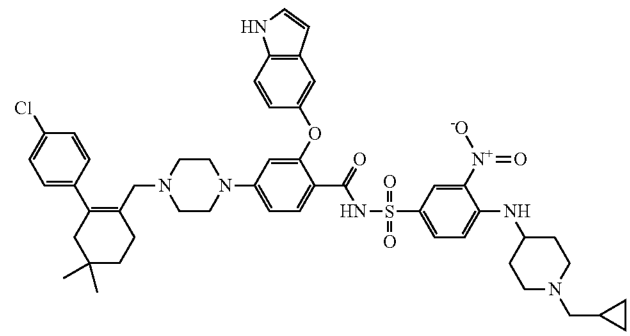 |
| 4-(4-{[2-(4-chlorophenyl)-4,4-dimethylcyclohex-1-en-1-yl]methyl}piperazin-1-yl)-2-(1H-indol-4-yloxy)-N-({4-[(4-methylpiperazin-1-yl)amino]-3-[(trifluoromethyl)sulfonyl]phenyl}sulfonyl)benzamide | 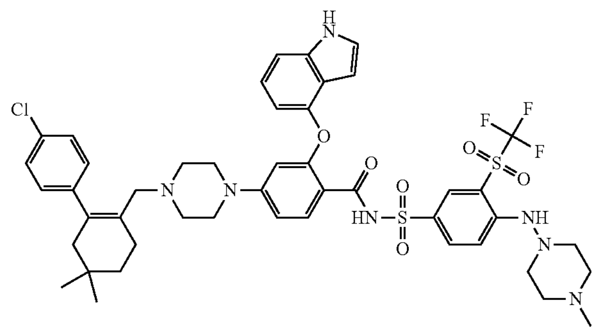 [SMILES: CN1CCN(Nc2ccc(S(=O)(=O)NC(=O)c3ccc(N4CCN(CC5=C(c6ccc(Cl)cc6)CC(C)(C)CC5)CC4)cc3Oc3cccc4[nH]ccc34)cc2S(=O)(=O)C(F)(F)F)CC1] |
| 4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[1-(4,4,4-trifluorobutyl)piperidin-4-yl]amino}phenyl)sulfonyl]benzamide | 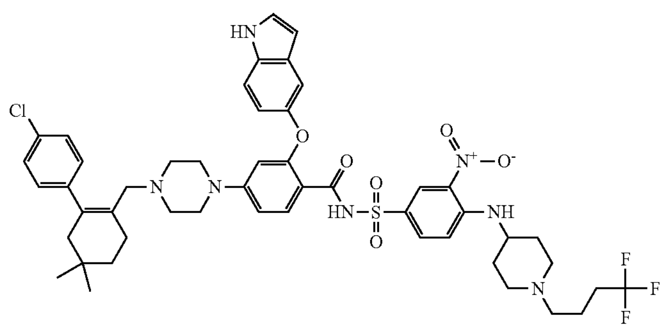 [SMILES: CC1(C)CCC(CN2CCN(c3ccc(C(=O)NS(=O)(=O)c4ccc(NC5CCN(CCCC(F)(F)F)CC5)c([N+](=O)[O-])c4)c(Oc4ccc5[nH]ccc5c4)c3)CC2)=C(c2ccc(Cl)cc2)C1] |
| 4-{4-[1-(4'-chloro-1,1'-biphenyl-2-yl)ethyl]piperazin-1-yl}-2-(1H-indol-4-yloxy)-N-({4-[(4-methylpiperazin-1-yl)amino]-3-nitrophenyl}sulfonyl)benzamide | 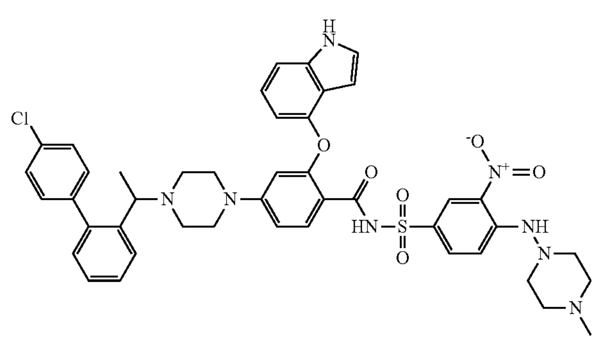 |

| Name | Structure |
|---|---|
| 4-[4-{[2-(4-chlorophenyl)-4,4-dimethylcyclohex-1-en-1-yl]methyl}-3-(hydroxymethyl)piperazin-1-yl]-2-(1H-indol-5-yloxy)-N-({4-[(1-methylpiperidin-4-yl)amino]-3-nitrophenyl}sulfonyl)benzamide | 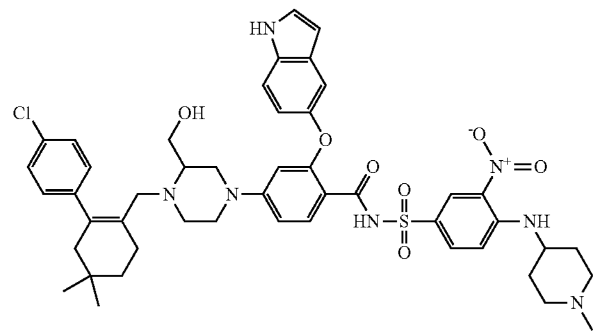 |
| 4-[4-{[2-(4-chlorophenyl)-4,4-dimethylcyclohex-1-en-1-yl]methyl}-3-(hydroxymethyl)piperazin-1-yl]-2-(1H-indol-5-yloxy)-N-({3-nitro-4-[(1-tetrahydro-2H-pyran-4-ylpiperidin-4-yl)amino]phenyl}sulfonyl)benzamide | 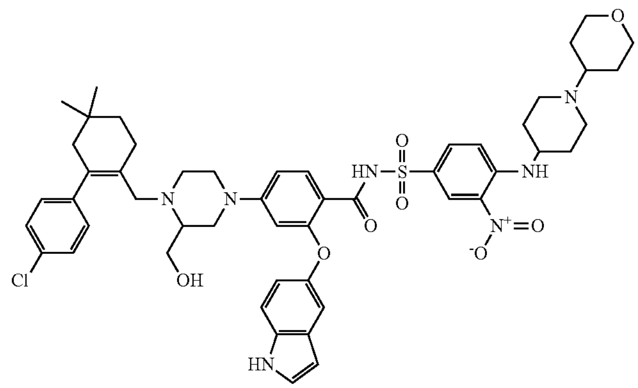 |
| 4-(4-{[2-(4-chlorophenyl)-4,4-dimethylcyclohex-1-en-1-yl]methyl}piperazin-1-yl)-2-(1H-indol-5-yloxy)-N-({4-[(4-methylpiperazin-1-yl)amino]-3-[(trifluoromethyl)sulfonyl]phenyl}sulfonyl)benzamide | 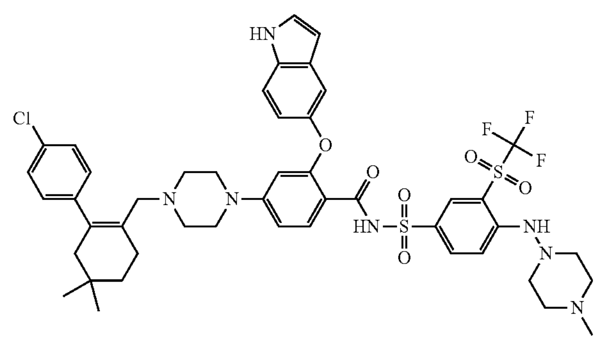 |
| 4-(4-{[4'-chloro-4-(2-hydroxyethoxy)-1,1'-biphenyl-2-yl]methyl}piperazin-1-yl)-2-(1H-indol-4-yloxy)-N-({4-[(1-methylpiperidin-4-yl)amino]-3-nitrophenyl}sulfonyl)benzamide | 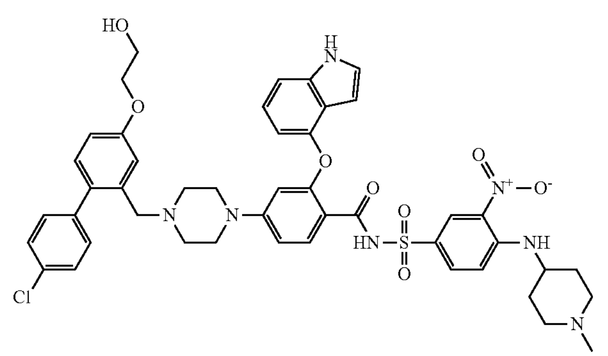 [SMILES: CN1CCC(Nc2ccc(S(=O)(=O)NC(=O)c3ccc(N4CCN(Cc5cc(OCCO)ccc5-c5ccc(Cl)cc5)CC4)cc3Oc3cccc4[nH]ccc34)cc2[N+](=O)[O-])CC1] |

| Name | Structure |
|---|---|
| 4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[3-(3-oxopiperazin-1-yl)propyl]amino}phenyl)sulfonyl]benzamide | 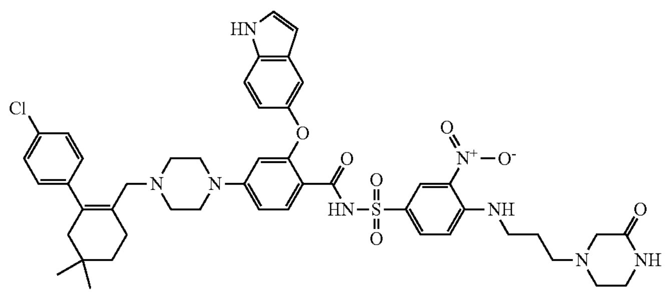 [SMILES: CC1(C)CCC(CN2CCN(c3ccc(C(=O)NS(=O)(=O)c4ccc(NCCCN5CCNC(=O)C5)c([N+](=O)[O-])c4)c(Oc4ccc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-2-(1H-indol-4-yloxy)-N-[(3-nitro-4-{[3-(3-oxopiperazin-1-yl)propyl]amino}phenyl)sulfonyl]benzamide | 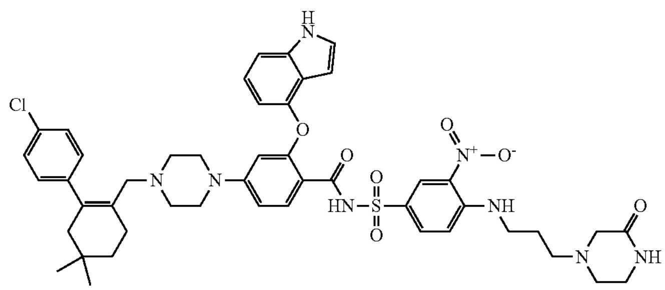 [SMILES: CC1(C)CCC(CN2CCN(c3ccc(C(=O)NS(=O)(=O)c4ccc(NCCCN5CCNC(=O)C5)c([N+](=O)[O-])c4)c(Oc4cccc5[nH]ccc45)c3)CC2)=C(c2ccc(Cl)cc2)C1] |
| 4-(4-{[2-(4-chlorophenyl)-5-hydroxycyclohex-1-en-1-yl]methyl}piperazin-1 yl)-2-(1H-indol-5-yloxy)-N-({4-[(1-methylpiperidin-4-yl)amino]-3-nitrophenyl}sulfonyl)benzamide | 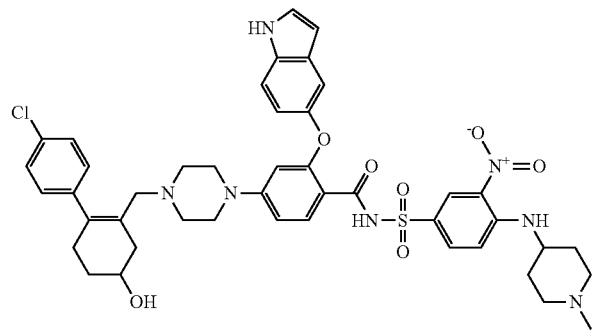 |
| 4-(4-{[2-(4-chlorophenyl-5-hydroxycyclohex-1-en-1-yl]methyl}piperazin-1-yl)-2-(1H-indol-5-yloxy)-N-({3-nitro-4-[(1-tetrahydro-2H-pyran-4-ylpiperidin-4-yl)amino]phenyl}sulfonyl)benzamide | 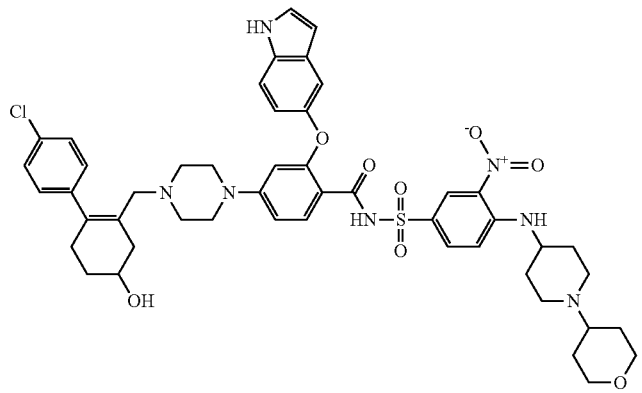 |

| Name | Structure |
|---|---|
| 4-(4-{[2-(4-chlorophenyl)-5-hydroxy cyclohex-1-en-1-yl]methyl} piperazin-1-yl)-2-(1H-indol-5-yloxy)-N-({4-[(4-methylpiperazin-1-yl)amino]-3-nitrophenyl} sulfonyl)benzamide | 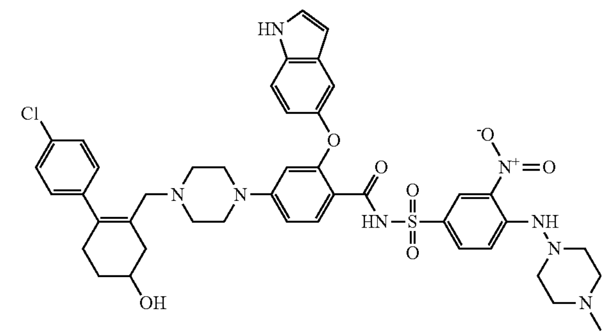 |
| 4-(4-{[2-(4-chlorophenyl)-4,4-dimethylcyclohex-1-en-1-yl]methyl}piperazin-1-yl)-N-[(4-{[1-(2,3-dihydro-1H-inden-2-yl)piperidin-4-yl]amino}-3-nitrophenyl)sulfonyl]-2-(1H-indol-4-yloxy)benzamide | 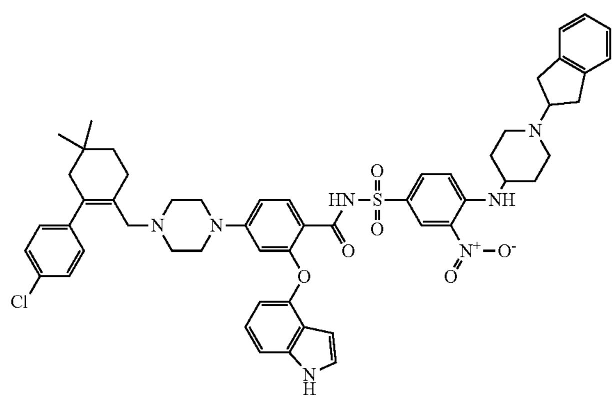 [SMILES: CC1(C)CCC(CN2CCN(c3ccc(C(=O)NS(=O)(=O)c4ccc(NC5CCN(C6Cc7ccccc7C6)CC5)c([N+](=O)[O-])c4)c(Oc4cccc5[nH]ccc45)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-[(4-{[1-(2,3-dihydro-1H-inden-2-yl)piperidin-4-yl]amino}-3-nitrophenyl)sulfonyl]-2-(1H-indol-5-yloxy)benzamide | 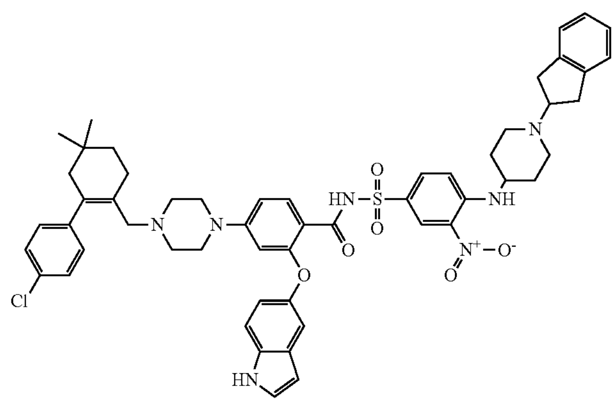 [SMILES: CC1(C)CCC(CN2CCN(c3ccc(C(=O)NS(=O)(=O)c4ccc(NC5CCN(C6Cc7ccccc7C6)CC5)c([N+](=O)[O-])c4)c(Oc4ccc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl} piperazin-1-yl)-2-(1H-indol-5-yloxy)-N-[(4-{[(1-morpholin-4-ylcyclohexyl)methyl]amino}-3-nitrophenyl)sulfonyl]benzamide | 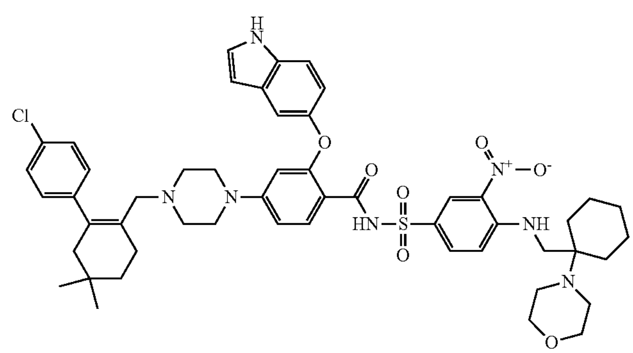 [SMILES: CC1(C)CCC(CN2CCN(c3ccc(C(=O)NS(=O)(=O)c4ccc(NCC5(N6CCOCC6)CCCCC5)c([N+](=O)[O-])c4)c(Oc4ccc5[nH]ccc5c4)c3)CC2)=C(c2ccc(Cl)cc2)C1] |

-continued

| Name | Structure |
|---|---|
| 4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[1-(1,3-thiazol-2-ylmethyl)piperidin-4-yl]amino}phenyl)sulfonyl]benzamide | 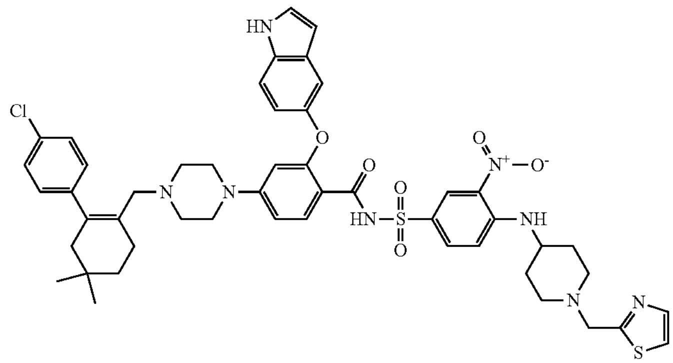 [SMILES: CC1(C)CCC(CN2CCN(c3ccc(C(=O)NS(=O)(=O)c4ccc(NC5CCN(Cc6nccs6)CC5)c([N+](=O)[O-])c4)c(Oc4ccc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-2-(2H-indol-5-yloxy)-N-[(3-nitro-4-{[1-(1,3-thiazol-4-ylmethyl)piperidin-4-yl]amino}phenyl)sulfonyl]benzamide | 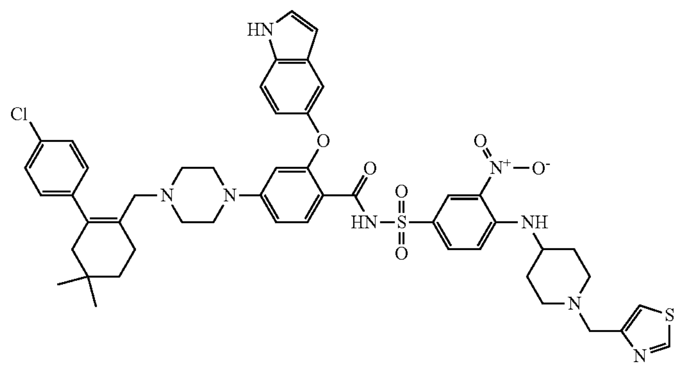 [SMILES: CC1(C)CCC(CN2CCN(c3ccc(C(=O)NS(=O)(=O)c4ccc(NC5CCN(Cc6cscn6)CC5)c([N+](=O)[O-])c4)c(Oc4ccc5[nH]ccc5c4)c3)CC2)=C(c2ccc(Cl)cc2)C1] |
| 4-(4-{[2-(4-chlorophenyl)-4,4-dimetylcyclohex-1-en-1-yl]methyl}piperazin-1-yl)-N-{[4-({[4-(hydroxymethyl)tetrahydro-2H-pyran-4-yl]methyl}amino)-3-nitrophenyl]sulfonyl}-2-(1H-indol-5-yloxy)benzamide | 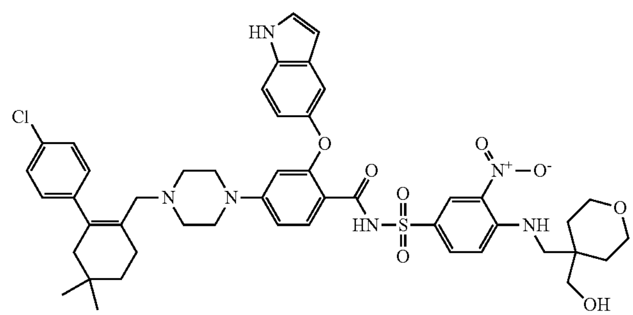 [SMILES: CC1(C)CCC(CN2CCN(c3ccc(C(=O)NS(=O)(=O)c4ccc(NCC5(CO)CCOCC5)c([N+](=O)[O-])c4)c(Oc4ccc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-[(4-{[4-(2-hydroxyethyl)piperazin-1-yl]amino}-3-nitrophenyl)sulfonyl]-2-(1H-indol-5-yloxy)benzamide | 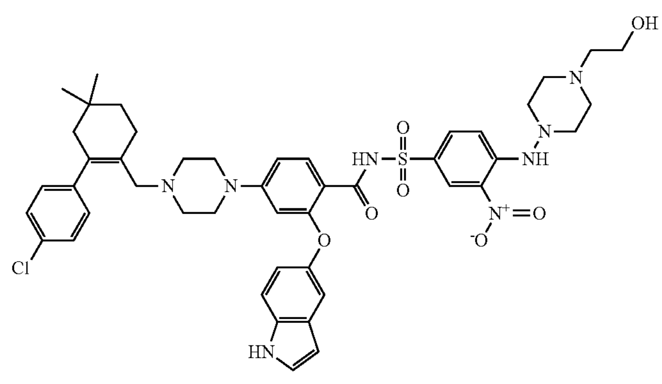 |

-continued

| Name | Structure |
|---|---|
| 4-(4-{[2-(4-chlorophenyl)-4,4-dimethylcyclohex-1-en-1-yl]methyl}piperazin-1-yl)-2-(1H-indol-5-yloxy)-N-[(4-{[(3 S)-1-methylpyrrolidin-3-yl]amino}-3-nitrophenyl)sulfonyl]benzamide | 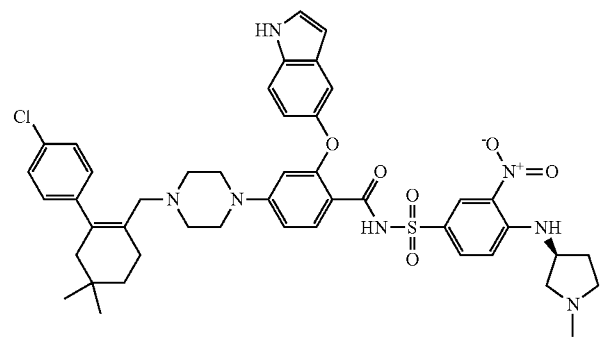 |
| 4-(4-{[2-(4-chlorophenyl)-4,4-dimethylcyclohex-1-en-1-yl]methyl}piperazin-1-yl)-N-[(4-{[1-(3-fluoropropyl)piperidin-4-yl]amino}-3-nitrophenyl)sulfonyl]-2-(1H-indol-5-yloxy)benzamide | 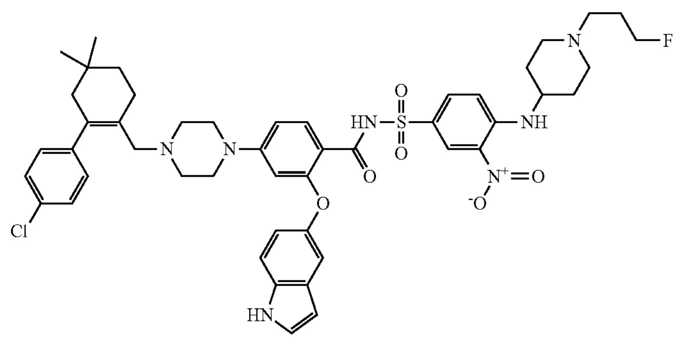 |
| 4-[4-{[2-(4-chlorophenyl)-4,4-dimethylcyclohex-1-en-1-yl]methyl}-3-(hydroxymethyl)piperazin-1-yl]-2-(1H-indol-5-yloxy)-N-({3-nitro-4-[(tetrahydro-2H-pyran-4-ylmethyl)amino]phenyl}sulfonyl)benzamide | 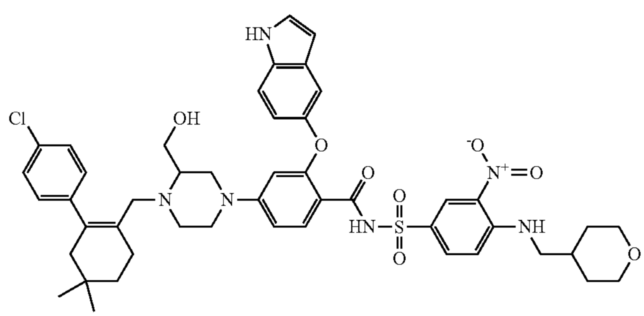 |
| N-[(4-{[(4-aminotetrahydro-2H-pyran-4-yl)methyl]amino}-3-nitrophenyl)sulfonyl]-4-[4-{[2-(4-chlorophenyl)-4,4-dimethylcyclohex-1-en-1-yl]methyl}-3-(hydroxymethyl)piperazin-1-yl]-2-(1H-indol-5-yloxy)benzamide | 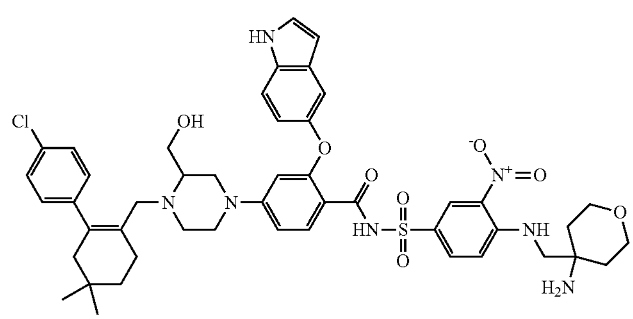 |

| Name | Structure |
|---|---|
| 4-(4-{[2-(4-chlorophenyl)-4,4-dimethylcyclohex-1-en-1-yl]methyl}piperazin-1-yl)-N-[(4-{[(1-hydroxycyclohexyl)methyl]amino}-3-nitrophenyl)sulfonyl]-2-(1H-indol-5-yloxy)benzamide | 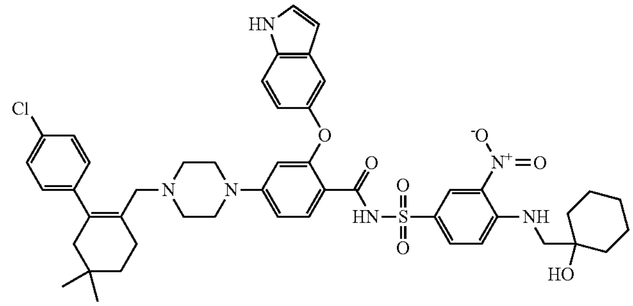 |
| 4-(4-{[2-(4-chlorophenyl)-4,4-dimethylcyclohex-1-en-1-yl]methyl}piperazin-1-yl)-2-(1H-indol-4-yloxy)-N-({4-[(2-methoxyethyl)amino]-3-nitrophenyl}sulfonyl)benzamide | 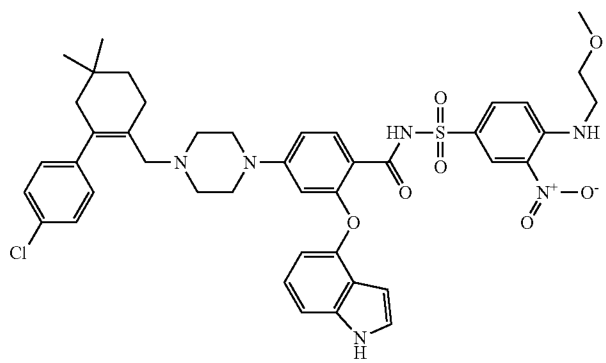 [SMILES: COCCNc1ccc(S(=O)(=O)NC(=O)c2ccc(N3CCN(CC4=C(c5ccc(Cl)cc5)CC(C)(C)CC4)CC3)cc2Oc2cccc3[nH]ccc23)cc1[N+](=O)[O-]] |
| 4-(4-{[2-(4-chlorophenyl)-4,4-dimethylcyclohex-1-en-1-yl]methyl}piperazin-1-yl)-N-[(4-{[4-(hydroxymethyl)tetrahydro-2H-pyran-4-yl]amino}-3-nitrophenyl)sulfonyl]-2-(1H-indol-5-yloxy)benzamide | 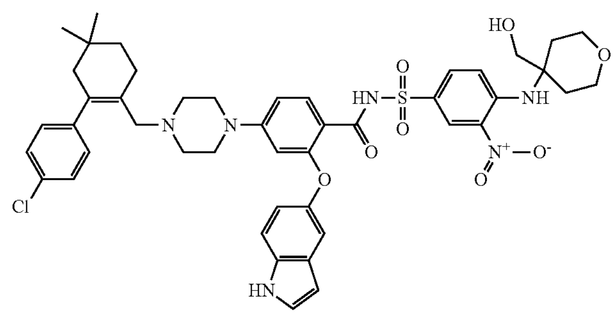 [SMILES: CC1(C)CCC(CN2CCN(c3ccc(C(=O)NS(=O)(=O)c4ccc(NC5(CO)CCOCC5)c([N+](=O)[O-])c4)c(Oc4ccc5[nH]ccc5c4)c3)CC2)=C(c2ccc(Cl)cc2)C1] |
| 4-(4-{[2-(4-chlorophenyl)-4,4-dimethylcyclohex-1-en-1-yl[methyl}piperazin-1-yl)-N-[(4-{[4-(hydroxymthyl)tetrahydro-2H-pyran-4-yl]amino}-3-nitrophenyl)sulfonyl]-2-(1H-indol-4-yloxy)benzamide | 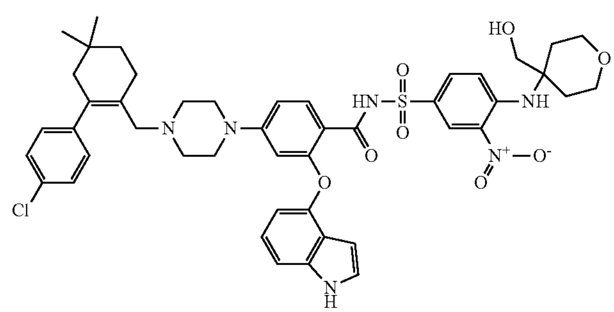 [SMILES: CC1(C)CCC(CN2CCN(c3ccc(C(=O)NS(=O)(=O)c4ccc(NC5(CO)CCOCC5)c([N+](=O)[O-])c4)c(Oc4cccc5[nH]ccc45)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-({4-[(2-hydroxy-1-tetrahydro-2H-pyran-4-ylethyl)amino]-3-nitrophenyl}sulfonyl)-2-(1H-indol-5-yloxy)benzamide | 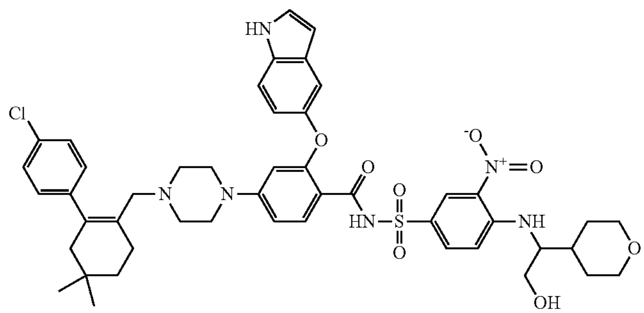 |

| Name | Structure |
|---|---|
| 4-(4-{[2-(4-chlorophenyl)-4,4-dimethylcyclohex-1-en-1-yl]methyl}piperazin-1-yl)-2-(1H-indol-5-yloxy)-N-{[3-nitro-4-({1-[2-(1H-pyrazol-1-yl)ethyl]piperidin-4-yl}amino)phenyl]sulfonyl}benzamide | 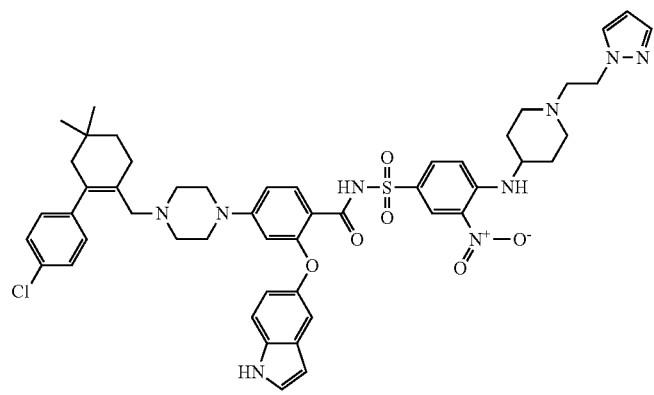 [SMILES: CC1(C)CCC(CN2CCN(c3ccc(C(=O)NS(=O)(=O)c4ccc(NC5CCN(CCn6cccn6)CC5)c([N+](=O)[O-])c4)c(Oc4ccc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-2-(1H-indol-4-yloxy)-N-({3-nitro-4-[(tetrahydro-2H-pyran-4-ylmethyl)amino]phenyl}sulfonyl)benzamide | 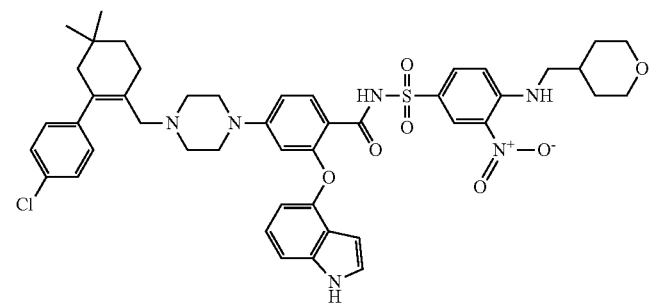 [SMILES: CC1(C)CCC(CN2CCN(c3ccc(C(=O)NS(=O)(=O)c4ccc(NCC5CCOCC5)c([N+](=O)[O-])c4)c(Oc4cccc5[nH]ccc45)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-2-(1H-indol-5-yloxy)-N-{[4-(methylamino)-3-nitrophenyl]sulfonyl}benzamide | 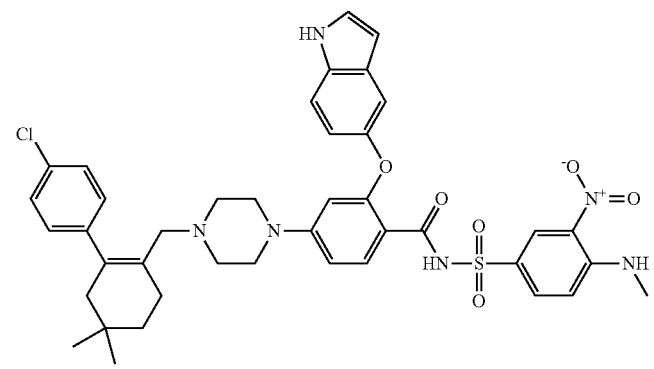 |
| 4-(4-{[2-(4-chlorophenyl)-4,4-dimethylcyclohex-1-en-1-yl]methyl}piperazin-1-yl)-2-(1H-indol-4-yloxy)-N-{[4-(methylamino)-3-nitrophenyl]sulfonyl}benzamide | 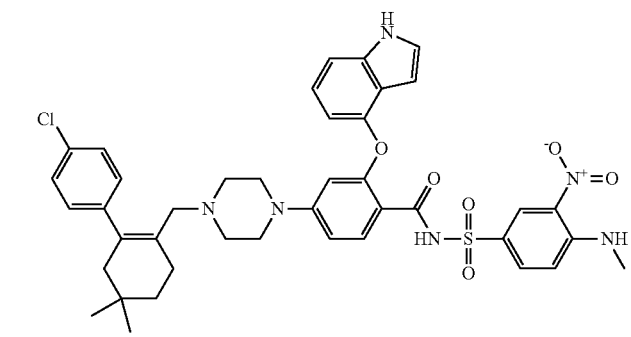 |

-continued

| Name | Structure |
|---|---|
| 4-{4-[1-(4'-chloro-1,1'-biphenyl-2-yl)ethyl]piperazin-1-yl}-2-(1H-indol-4-yloxy)-N-({4-[(3-morpholin-4-ylpropyl)amino]-3-nitrophenyl}sulfonyl)benzamide | 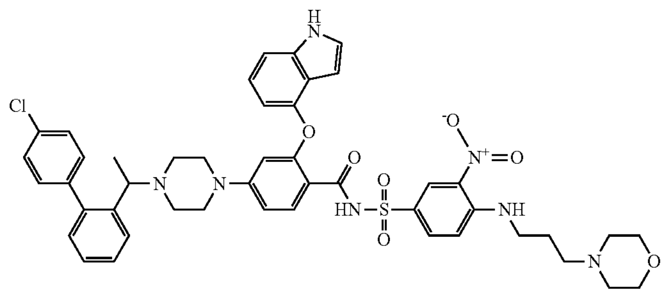 |
| 4-(4-{[2-(4-chlorophenyl)-5-hydroxycyclohex-1-en-1-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide | 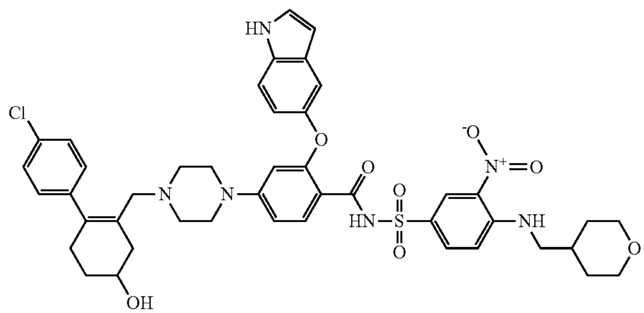 |
| 4-(4-{[2-(4-chlorophenyl)-5-morpholin-4-ylcyclohex-1-en-1-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide | 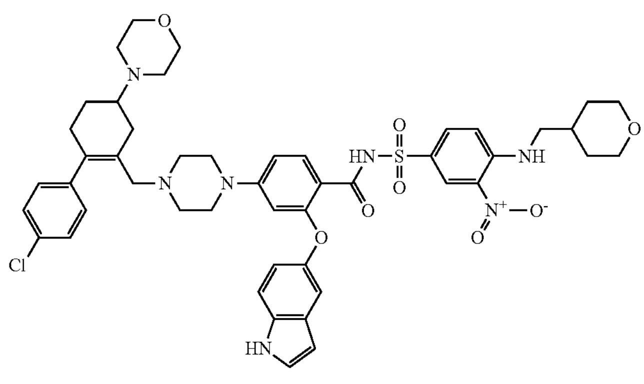 [SMILES: O=C(NS(=O)(=O)c1ccc(NCC2CCOCC2)c([N+](=O)[O-])c1)c1ccc(N2CCN(CC3=C(c4ccc(Cl)cc4)CCC(N4CCOCC4)C3)CC2)cc1Oc1ccc2[nH]ccc2c1] |
| N-[(4-{[(1-aminocyclohexyl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-indol-5-yloxy)benzamide | 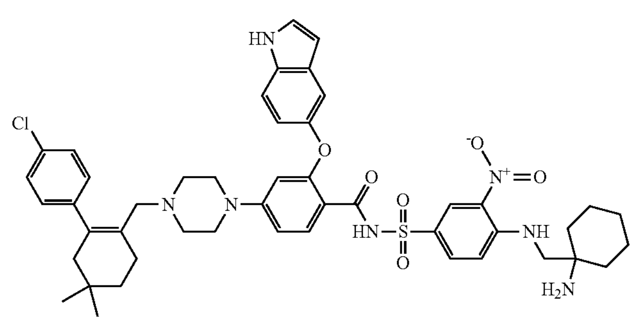 |

| Name | Structure |
|---|---|
| 4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[2-(2-oxopyrrolidin-1-yl)ethyl]amino}phenyl)sulfonyl]benzamide | 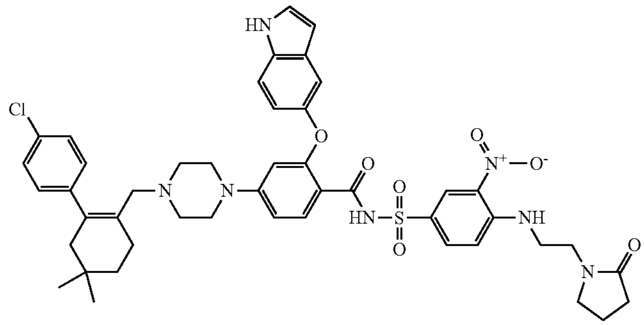 [SMILES: CC1(C)CCC(CN2CCN(c3ccc(C(=O)NS(=O)(=O)c4ccc(NCCN5CCCC5=O)c([N+](=O)[O-])c4)c(Oc4ccc5[nH]ccc5c4)c3)CC2)=C(c2ccc(Cl)cc2)C1] |
| 4-{4-[1-(4'-chloro-1,1'-biphenyl-2-yl)ethyl]piperazin-1-yl}-2-(1H-indol-5-yloxy)-N-({3-nitro-4-[(tetrahydro-2H-pyran-4-ylmethyl)amino]phenyl}sulfonyl)benzamide | 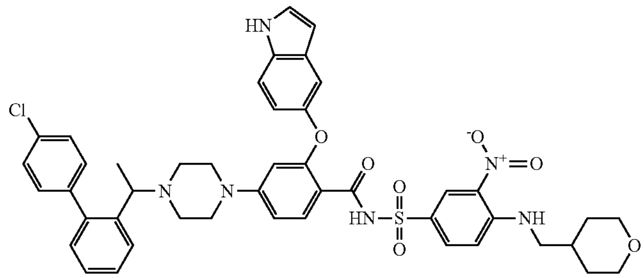 |
| 4-(4-{1-[2-(4-chlorophenyl)-4,4-dimethylcyclohex-1-en-1-yl]ethyl}piperazin-1-yl)-2-(1H-indol-5-yloxy)-N-({3-nitro-4-[(tetrahydro-2H-pyran-4-ylmethyl)amino]phenyl}sulfonyl)benzamide | 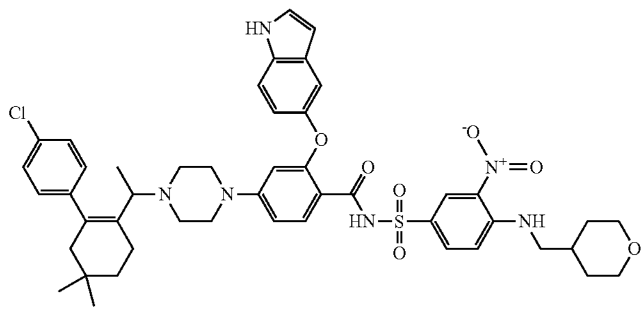 |
| 4-(4-{1-[2-(4-chlorophenyl)-4,4-dimethylcyclohex-1-en-1-yl]ethyl}piperazin-1-yl)-2-(1H-indol-5-yloxy)-N-({4-[(4-methylpiperazin-1-yl)amino]-3-nitrophenyl}sulfonyl)benzamide | 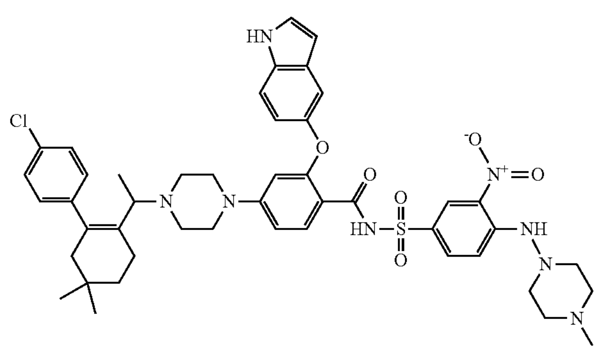 |
| 4-{4-[(1R)-1-(4'-chloro-1,1'-biphenyl-2-yl)ethyl]piperazin-1-yl}-2-(1H-indol-4-yloxy)-N-({3-nitro-4-[(tetrahydro-2H-pyran-4-ylmethyl)amino]phenyl}sulfonyl)benzamide | 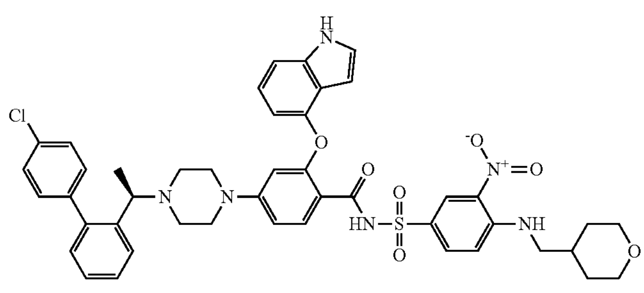 |

-continued

| Name | Structure |
|---|---|
| 4-{4-[(1 S)-1-(4'-chloro-1,1'-biphenyl-2-yl)ethyl]piperazin-1-yl}-2-(1 H-indol-4-yloxy)-N-({3-nitro-4-[(tetrahydro-2H-pyran-4-ylmethyl)amino]phenyl}sulfonyl)benzamide | 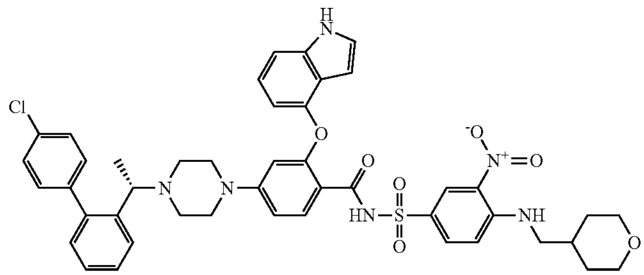 |
| 4-(4-{1-[2-(4-chlorophenyl)-4,4-dimethylcyclohex-1-en-1-yl]ethyl}piperazin-1-yl)-2-(1H-indol-5-yloxy)-N-({4-[(3-morpholin-4-ylpropyl)amino]-3-nitrophenyl}sulfonyl)benzamide | 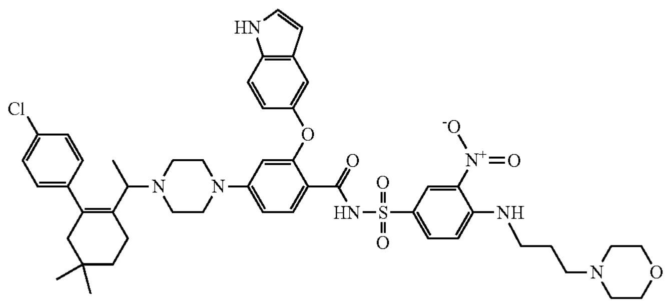 |
| 4-(4-{1-[2-(4-chlorophenyl)-4,4-dimethylcyclohex-1-en-1-yl]ethyl}piperazin-1-yl)-2-(1H-indol-5-yloxy)-N-({3-nitro-4-[(1-tetrahydro-2H-pyran-4-ylpiperidin-4-yl)amino]phenyl}sulfonyl)benzamide | 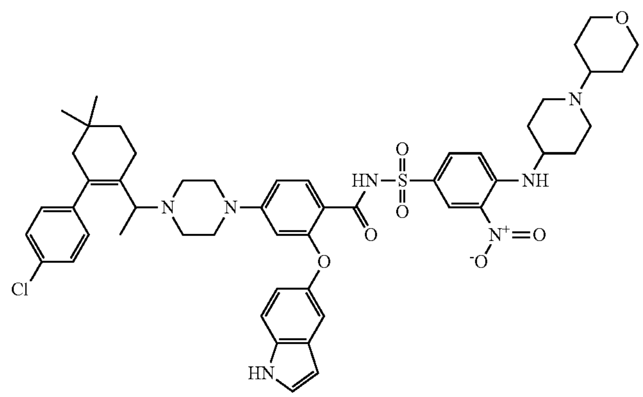 |
| 4-(4-{[2-(4-chlorophenyl)-4,4-dimethylcyclohex-1-en-1-yl]methyl}piperazin-1-yl)-N-({4-[(cyclohexylmethyl)amino]-3-nitrophenyl}sulfonyl)-2-(1H-indol-5-yloxy)benzamide | 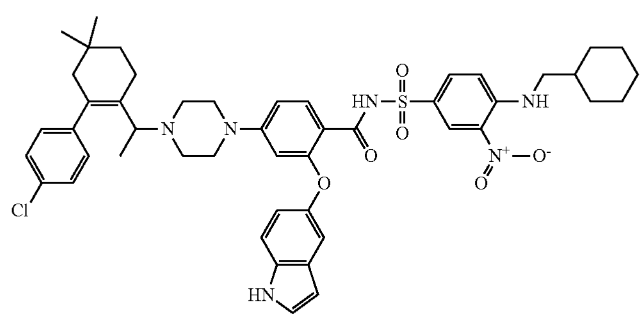 [SMILES: CC(C1=C(c2ccc(Cl)cc2)CC(C)(C)CC1)N1CCN(c2ccc(C(=O)NS(=O)(=O)c3ccc(NCC4CCCCC4)c([N+](=O)[O-])c3)c(Oc3ccc4[nH]ccc4c3)c2)CC1] |
| 4-(4-{[2-(4-chlorophenyl)-4,4-dimethylcyclohex-1-en-1-yl]methyl}piperazin-1-yl)-2-(1H-indol-5-yloxy)-N-{[4-(morpholin-4-ylamino)-3-nitrophenyl]sulfonyl}benzamide | 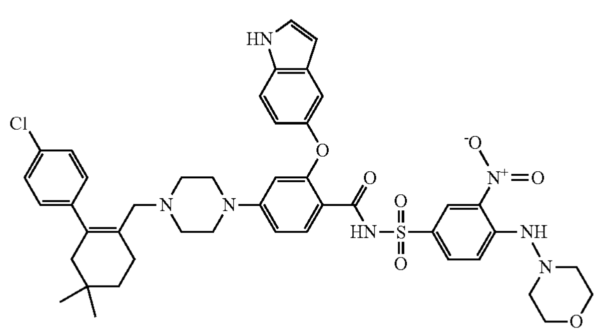 |

| Name | Structure |
|---|---|
| 4-(4-{[2-(4-chlorophenyl)-4,4-dimethylcyclohex-1-en-1-yl]methyl}piperazin-1-yl)-2-(1H-indol-5-yloxy)-N-({3-nitro-4-[(tetrahydro-2H-pyran-3-ylmethyl)amino]phenyl}sulfonyl)benzamide | 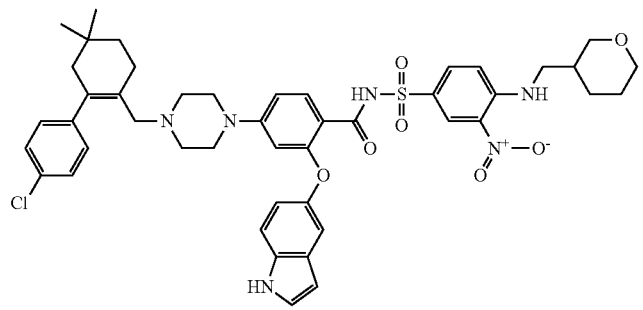 [SMILES: CC1(C)CCC(CN2CCN(c3ccc(C(=O)NS(=O)(=O)c4ccc(NCC5CCCOC5)c([N+](=O)[O-])c4)c(Oc4ccc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-2-(1H-indol-4-yloxy)-N-{[4-(morpholin-4-ylamino)-3-nitrophenyl]sulfonyl}benzamide | 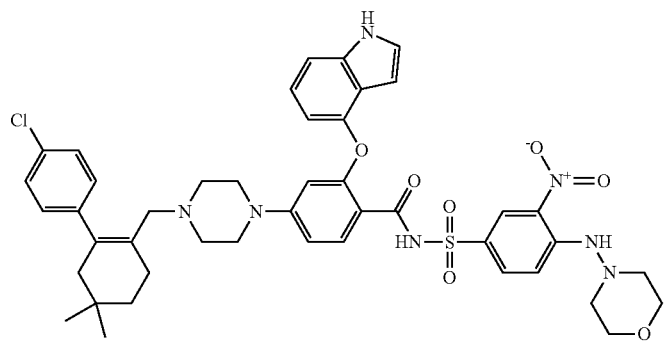 |
| 4-(4-{[2-(4-chlorophenyl)-4,4-dimethylcyclohex-1-en-1-yl]methyl}piperazin-1-yl)-2-(1H-indol-5-yloxy)-N-{[3-nitro-4-(tetrahydro-2H-pyran-4-ylamino)phenyl]sulfonyl}benzamide | 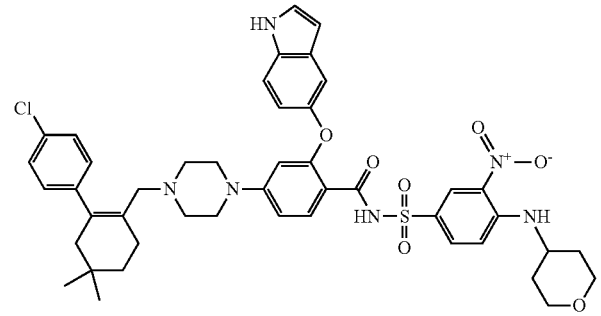 [SMILES: CC1(C)CCC(CN2CCN(c3ccc(C(=O)NS(=O)(=O)c4ccc(NC5CCOCC5)c([N+](=O)[O-])c4)c(Oc4ccc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-2-(1H-indol-5-yloxy)-N-[(4-{[(3-methyloxetan-3-yl)methyl]amino}-3-nitrophenyl)sulfonyl]benzamide | 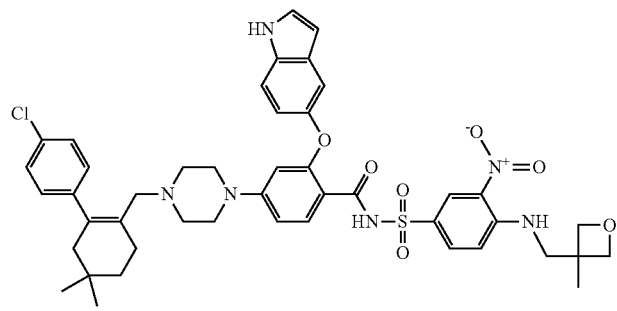 |

-continued

| Name | Structure |
|---|---|
| 4-(4-{[2-(4-chlorophenyl)-4,4-dimethylcyclohex-1-en-1-yl]methyl}piperazin-1-yl)-2-(1H-indol-5-yloxy)-N-({4-[(4-methoxycyclohexyl)amino]-3-nitrophenyl}sulfonyl)benzamide | 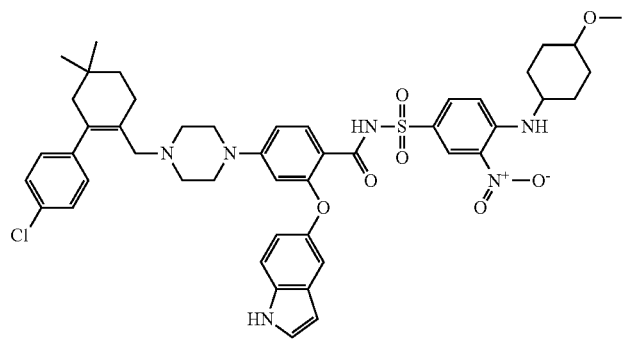 [SMILES: COC1CCC(Nc2ccc(S(=O)(=O)NC(=O)c3ccc(N4CCN(CC5=C(c6ccc(Cl)cc6)CC(C)(C)CC5)CC4)cc3Oc3ccc4[nH]ccc4c3)cc2[N+](=O)[O-])CC1] |
| 4-(4-{[2-(4-chlorophenyl)-4,4-dimethylcyclohex-1-en-1-yl[methyl}piperazin-1-yl)-N-[(4-{[3-(1,1-dioxidothiomorpholin-4-yl)propyl]amino}-3-nitrophenyl)sulfonyl]-2-(1H-indol-5-yloxy)benzamide | 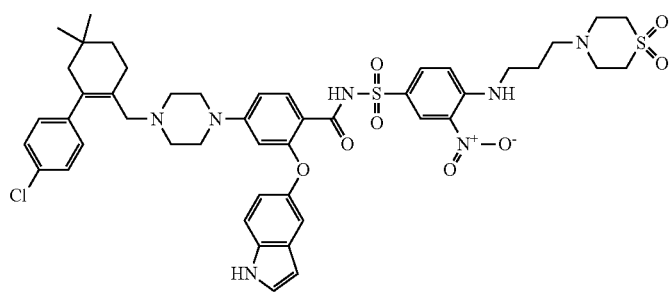 [SMILES: CC1(C)CCC(CN2CCN(c3ccc(C(=O)NS(=O)(=O)c4ccc(NCCCN5CCS(=O)(=O)CC5)c([N+](=O)[O-])c4)c(Oc4ccc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[2-(2-oxopiperidin-1-yl)ethyl]amino}phenyl)sulfonyl]benzamide | 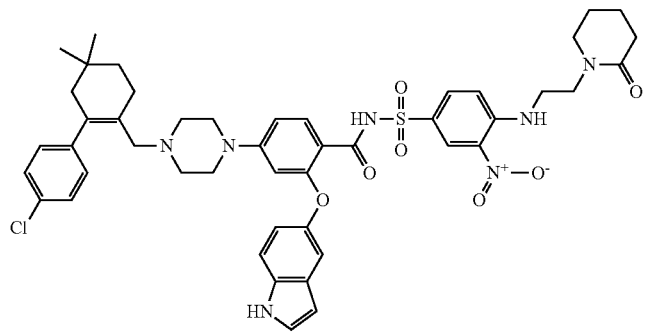 [SMILES: CC1(C)CCC(CN2CCN(c3ccc(C(=O)NS(=O)(=O)c4ccc(NCCN5CCCCC5=O)c([N+](=O)[O-])c4)c(Oc4ccc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[2-(2-oxoimidazolidin-1-yl)ethyl]amino}phenyl)sulfonyl]benzamide | 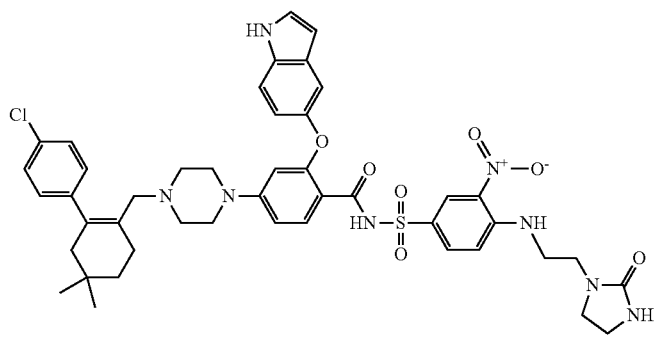 [SMILES: CC1(C)CCC(CN2CCN(c3ccc(C(=O)NS(=O)(=O)c4ccc(NCCN5CCNC5=O)c([N+](=O)[O-])c4)c(Oc4ccc5[nH]ccc5c4)c3)CC2)=C(c2ccc(Cl)cc2)C1] |

-continued

| Name | Structure |
|---|---|
| 4-(4-{[2-(4-chlorophenyl)-4,4-dimethylcyclohex-1-en-1-yl]methyl}piperazin-1-yl)-2-(1H-indol-5-yloxy)-N-({3-nitro-4-[(2-pyridin-4-ylethyl)amino]phenyl}sulfonyl)benzamide | 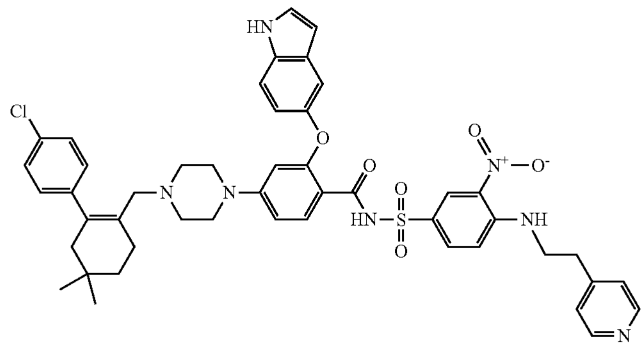 [SMILES: CC1(C)CCC(CN2CCN(c3ccc(C(=O)NS(=O)(=O)c4ccc(NCCc5ccncc5)c([N+](=O)[O-])c4)c(Oc4ccc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-2-(1H-indol-5-yloxy)-N-[(4-morpholin-4-yl-3-nitrophenyl)sulfonyl]benzamide | 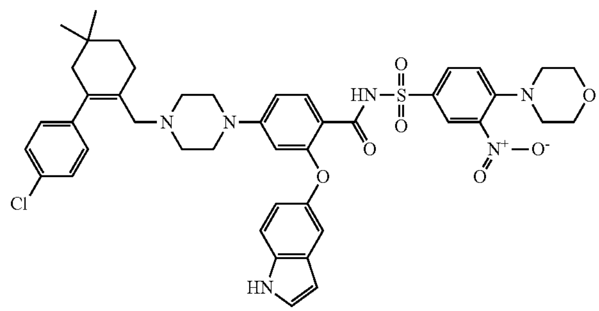 [SMILES: CC1(C)CCC(CN2CCN(c3ccc(C(=O)NS(=O)(=O)c4ccc(N5CCOCC5)c([N+](=O)[O-])c4)c(Oc4ccc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-2-(1H-indol-5-yloxy)-N-{[4-(4-methoxypiperidin-1-yl)-3-nitrophenyl]sulfonyl}benzamide | 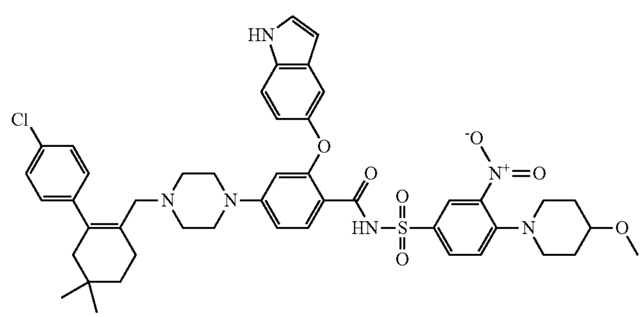 |
| 4-(4-{[2-(4-chlorophenyl)-5-pyrrolidin-1-ylcyclohex-1-en-1-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide | 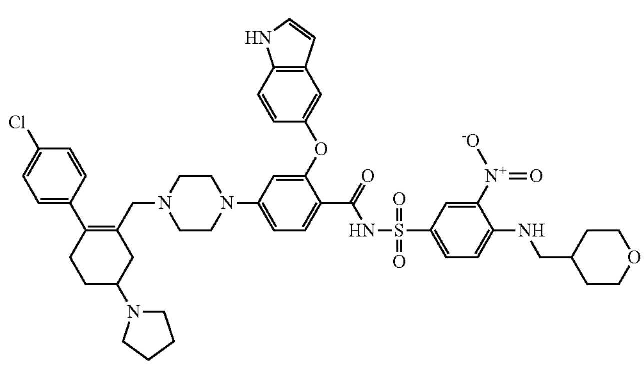 |

-continued

| Name | Structure |
|---|---|
| 4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[2-(3-oxopiperazin-1-yl)ethyl]amino}phenyl)sulfonyl]benzamide | 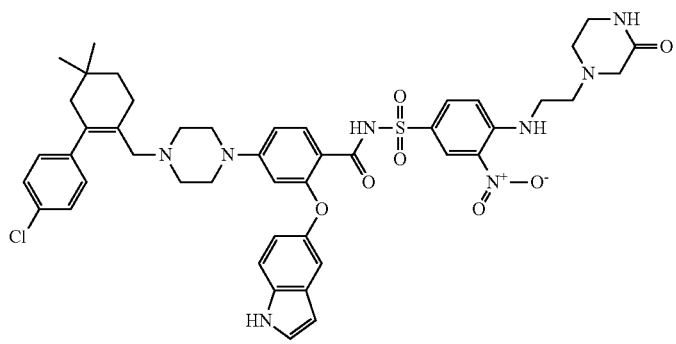 [SMILES: CC1(C)CCC(CN2CCN(c3ccc(C(=O)NS(=O)(=O)c4ccc(NCCN5CCNC(=O)C5)c([N+](=O)[O-])c4)c(Oc4ccc5[nH]ccc5c4)c3)CC2)=C(c2ccc(Cl)cc2)C1] |
| 4-[4-({4'-chloro-4-[2-(dimethylamino)ethoxy]-1,1'-biphenyl-2-yl}methyl)piperazin-1-yl]-2-(1H-indol-4-yloxy)-N-({4-[(4-methylpiperazin-1-yl)amino]-3-nitrophenyl}sulfonyl)benzamide | 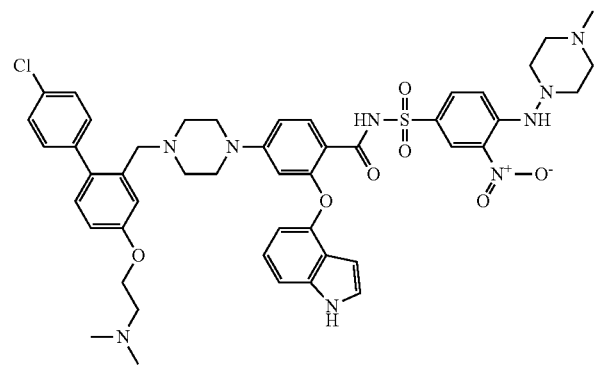 [SMILES: CN(C)CCOc1ccc(-c2ccc(Cl)cc2)c(CN2CCN(c3ccc(C(=O)NS(=O)(=O)c4ccc(NN5CCN(C)CC5)c([N+](=O)[O-])c4)c(Oc4cccc5[nH]ccc45)c3)CC2)c1] |
| 4-(4-{[2-(4-chlorophenyl)-4,4-dimethylcyclohex-1-en-1-yl]methyl}piperazin-1-yl)-N-[(4-{[(1,1-dioxidotetrahydrothien-3-yl)methyl]amino}-3-nitrophenyl)sulfonyl]-2-(1H-indol-5-yloxy)benzamide | 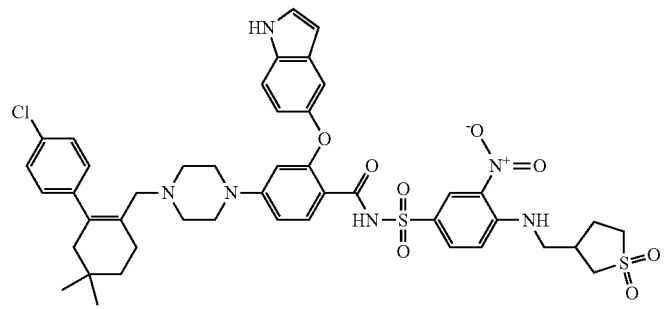 |
| 4-(4-{[2-(4-chlorophenyl)-4,4-dimethylcyclohex-1-en-1-yl]methyl}piperazin-1-yl)-N-({4-[(1,1-dioxidotetrahydrothien-3-yl)amino]-3-nitrophenyl}sulfonyl)-2-(1H-indol-5-yloxy)benzamide | 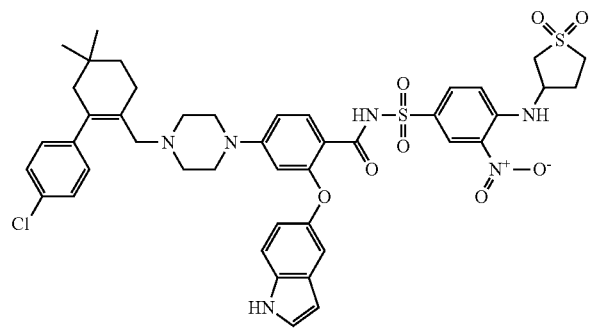 [SMILES: CC1(C)CCC(CN2CCN(c3ccc(C(=O)NS(=O)(=O)c4ccc(NC5CCS(=O)(=O)C5)c([N+](=O)[O-])c4)c(Oc4ccc5[nH]ccc5c4)c3)CC2)=C(c2ccc(Cl)cc2)C1] |

| Name | Structure |
|---|---|
| 4-(4-{[2-(4-chlorophenyl)-4,4-dimethylcyclohex-1-en-1-yl]methyl}piperazin-1-yl)-2-(1H-indol-5-yloxy)-N-{[4-[(tetrahydro-2H-pyran-4-ylmethyl)amino]-3-(trifluoromethyl)phenyl]sulfonyl}benzamide | 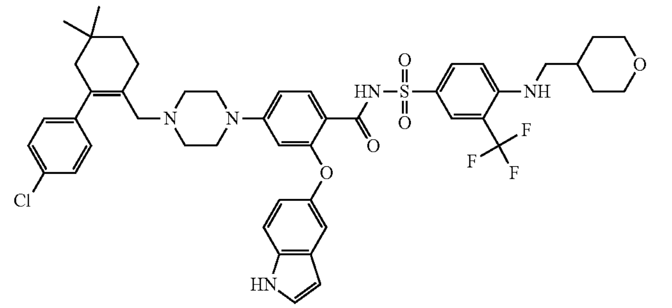 [SMILES: CC1(C)CCC(CN2CCN(c3ccc(C(=O)NS(=O)(=O)c4ccc(NCC5CCOCC5)c(C(F)(F)F)c4)c(Oc4ccc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-({4-[2-(1,3-dioxolan-2-yl)ethyl]-3-nitrophenyl}sulfonyl)-2-(1H-indol-5-yloxy)benzamide | 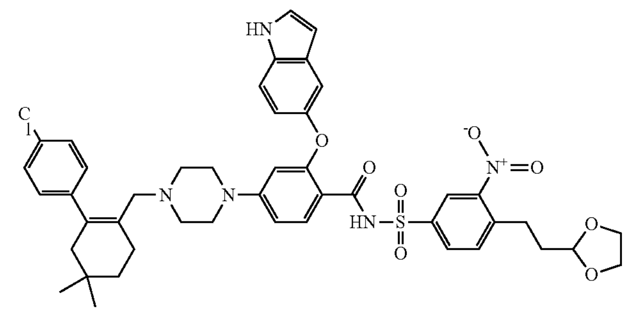 |
| 4-(4-{[2-(4-chlorophenyl)-4,4-dimethylcyclohex-1-en-1-yl]methyl}piperazin-1-yl)-2-(1H-indol-5-yloxy)-N-{[3-nitro-4-(tetrahydro-2H-pyran-4-ylmethoxy)phenyl]sulfonyl}benzamide | 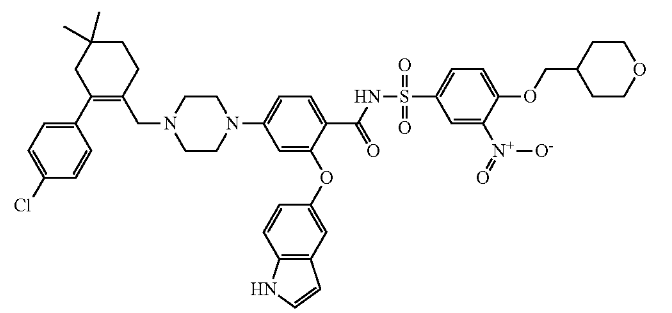 |
| 4-(4-{[2-(4-chlorophenyl)-4,4-dimethylcyclohex-1-en-1-yl]methyl}piperazin-1-yl)-2-(1H-indol-4-yloxy)-N-[(3-nitro-4-{[2-(3-oxopiperazin-1-yl)ethyl]amino}phenyl)sulfonyl]benzamide | 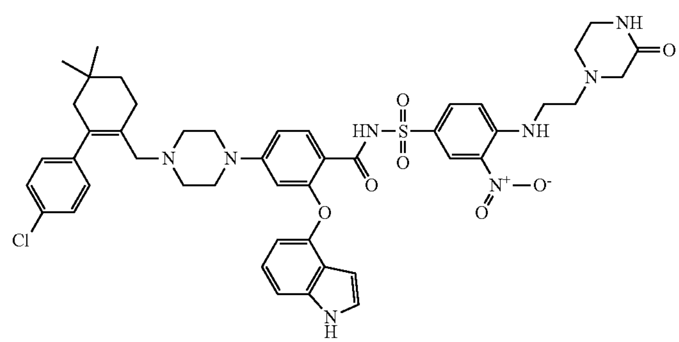 [SMILES: CC1(C)CCC(CN2CCN(c3ccc(C(=O)NS(=O)(=O)c4ccc(NCCN5CCNC(=O)C5)c([N+](=O)[O-])c4)c(Oc4cccc5[nH]ccc45)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-2-(1H-indol-5-yloxy)-N-({4-[(1-methyl-5-oxopyrrolidin-3-yl)amino]-3-nitrophenyl}sulfonyl)benzamide | 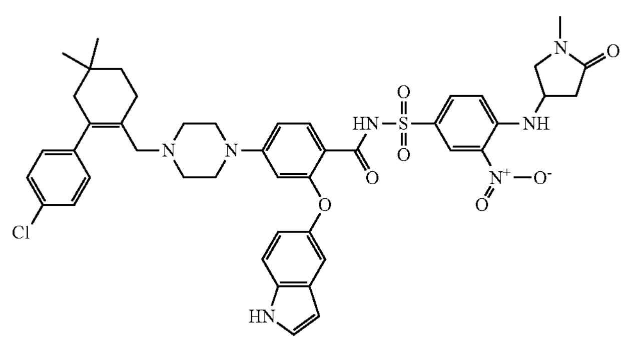 [SMILES: CN1CC(Nc2ccc(S(=O)(=O)NC(=O)c3ccc(N4CCN(CC5=C(c6ccc(Cl)cc6)CC(C)(C)CC5)CC4)cc3Oc3ccc4[nH]ccc4c3)cc2[N+](=O)[O-])CC1=O] |

| Name | Structure |
|---|---|
| 4-(4-{[2-(4-chlorophenyl)-4,4-dimethylcyclohex-1-en-1-yl]methyl}piperazin-1-yl)-2-(1H-indol-5-yloxy)-N-({4-[(1-methyl-6-oxopiperidin-3-yl)amino]-3-nitrophenyl}sulfonyl)benzamide | 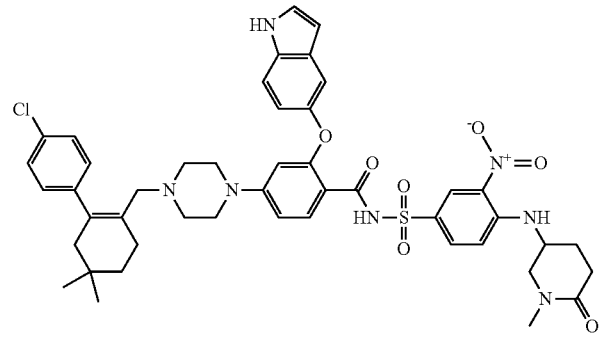 |
| 4-(4-{[2-(4-chlorophenyl)-4,4-dimethylcyclohex-1-en-1-yl]methyl}piperazin-1-yl)-2-(1H-indol-4-yloxy)-N-{[3-nitro-4-(piperidin-1-ylamino)phenyl]sulfonyl}benzamide | 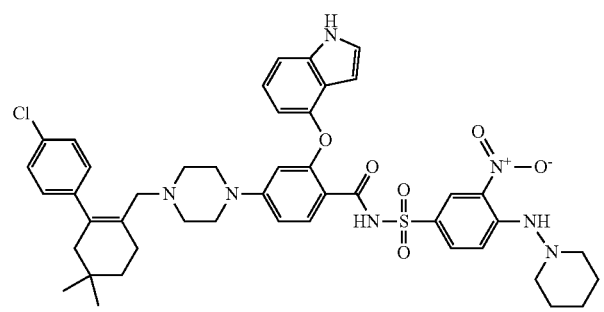 [SMILES: CC1(C)CCC(CN2CCN(c3ccc(C(=O)NS(=O)(=O)c4ccc(NN5CCCCC5)c([N+](=O)[O-])c4)c(Oc4cccc5[nH]ccc45)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-2-(1H-indol-5-yloxy)-N-{[3-nitro-4-(piperidin-1-ylamino)phenyl]sulfonyl}benzamide | 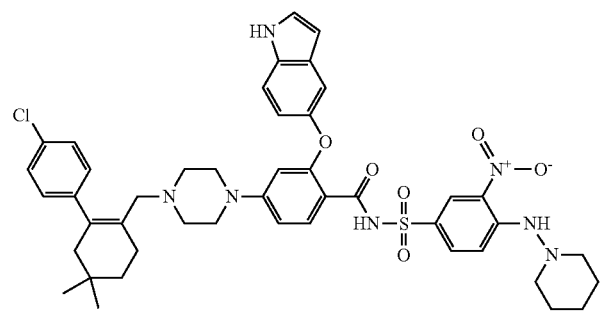 [SMILES: CC1(C)CCC(CN2CCN(c3ccc(C(=O)NS(=O)(=O)c4ccc(NN5CCCCC5)c([N+](=O)[O-])c4)c(Oc4ccc5[nH]ccc5c4)c3)CC2)=C(c2ccc(Cl)cc2)C1] |
| 4-(4-{[4-(4-chlorophenyl)-1-methyl-1H-pyrazol-5-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide | 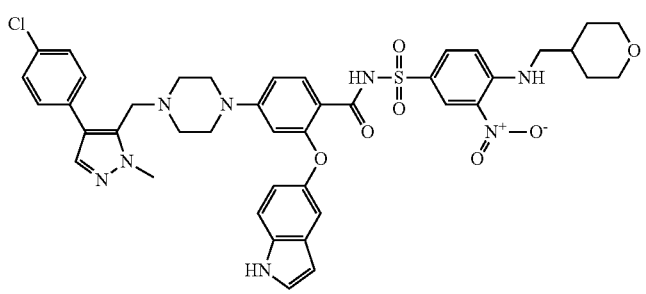 [SMILES: Cn1ncc(-c2ccc(Cl)cc2)c1CN1CCN(c2ccc(C(=O)NS(=O)(=O)c3ccc(NCC4CCOCC4)c([N+](=O)[O-])c3)c(Oc3ccc4[nH]ccc4c3)c2)CC1] |
| 4-(4-{[2-(4-chlorophenyl)-4,4-dimethylcyclohex-1-en-1-yl]methyl}piperazin-1-yl)-2-(1H-indol-5-yloxy)-N-({4-[(3-methyloxetan-3-yl)methoxy]-3-nitrophenyl}sulfonyl)benzamide | 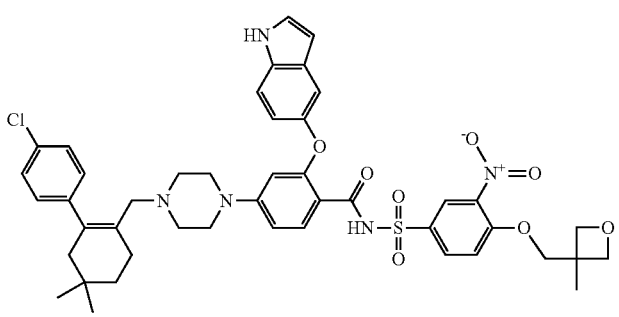 |

-continued

| Name | Structure |
|---|---|
| 4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[(1-oxidotetrahydro-2H-thiopyran-4-yl)methyl]amino}phenyl)sulfonyl]benzamide | 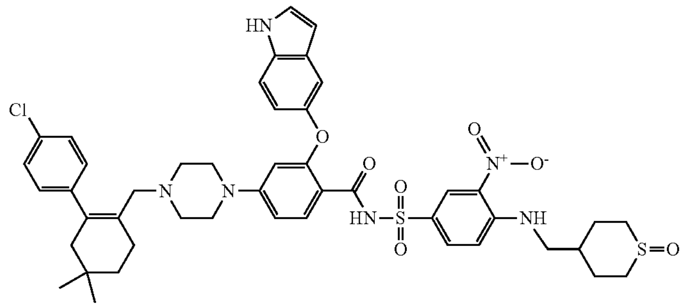 [SMILES: CC1(C)CCC(CN2CCN(c3ccc(C(=O)NS(=O)(=O)c4ccc(NCC5CCS(=O)CC5)c([N+](=O)[O-])c4)c(Oc4ccc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-2-(1H-indol-5-yloxy)-N-({3-nitro-4-[(1,3-thiazol-5-ylmethyl)amino]phenyl}sulfonyl)benzamide | 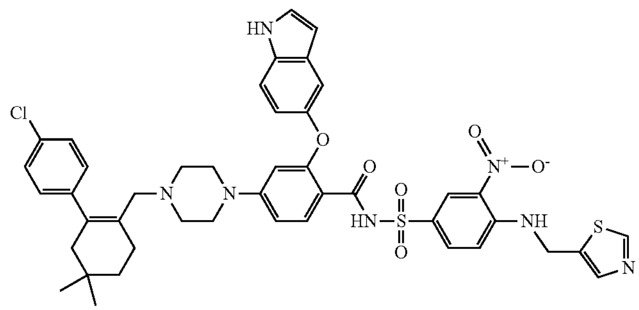 [SMILES: CC1(C)CCC(CN2CCN(c3ccc(C(=O)NS(=O)(=O)c4ccc(NCc5cncs5)c([N+](=O)[O-])c4)c(Oc4ccc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-2-(1H-indol-4-yloxy)-N-{[3-nitro-4-(tetrahydro-2H-pyran-4-ylmethoxy)phenyl]sulfonyl}benzamide | 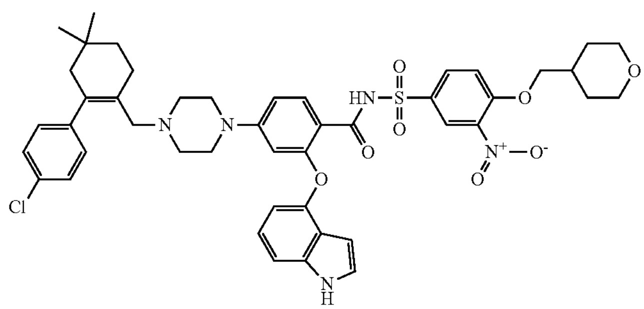 [SMILES: CC1(C)CCC(CN2CCN(c3ccc(C(=O)NS(=O)(=O)c4ccc(OCC5CCOCC5)c([N+](=O)[O-])c4)c(Oc4cccc5[nH]ccc45)c3)CC2)=C(c2ccc(Cl)cc2)C1] |
| 4-(4-{[2-(4-chlorophenyl)-5,5-dimethylcyclohex-1-en-1-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide | 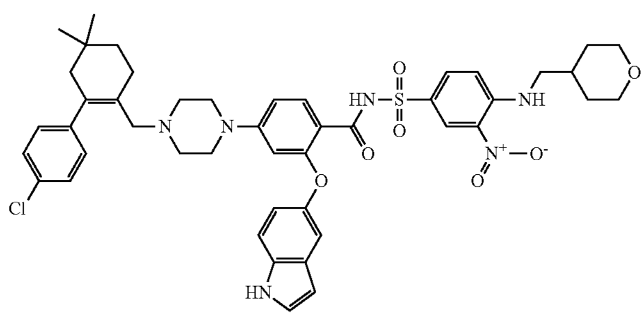 |
| 4-(4-{[2-(4-chlorophenyl)-4,4-dimethylcyclohex-1-en-1-yl]methyl}piperazin-1-yl)-2-(1H-indol-5-yloxy)-N-({3-nitro-4-[(2-tetrahydro-2H-pyran-4-ylethyl)amino]phenyl}sulfonyl)benzamide | 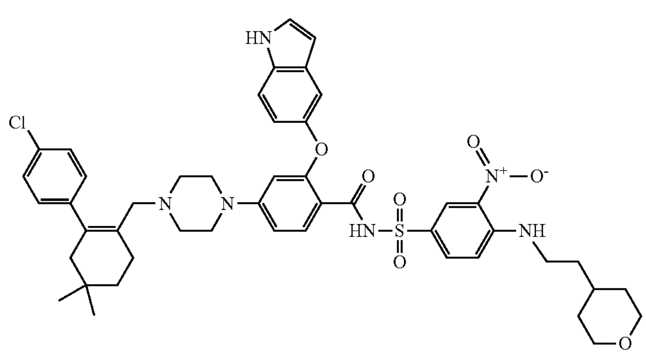 [SMILES: CC1(C)CCC(CN2CCN(c3ccc(C(=O)NS(=O)(=O)c4ccc(NCCC5CCOCC5)c([N+](=O)[O-])c4)c(Oc4ccc5[nH]ccc5c4)c3)CC2)=C(c2ccc(Cl)cc2)C1] |

| Name | Structure |
|---|---|
| 4-(4-{[2-(4-chlorophenyl)-4,4-dimethylcyclohex-1-en-1-yl]methyl}piperazin-1-yl)-2-(1H-indol-4-yloxy)-N-[(3-nitro-4-{[2-(trifluoromethoxy)ethyl]amino}phenyl)sulfonyl]benzamide | 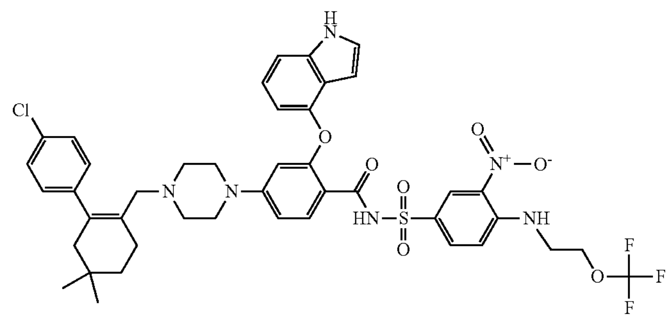 [SMILES: CC1(C)CCC(CN2CCN(c3ccc(C(=O)NS(=O)(=O)c4ccc(NCCOC(F)(F)F)c([N+](=O)[O-])c4)c(Oc4cccc5[nH]ccc45)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-2-(1H-indol-4-yloxy)-N-[(4-{[2-(2-methoxyethoxy)ethyl]amino}-3-nitrophenyl)sulfonyl]benzamide | 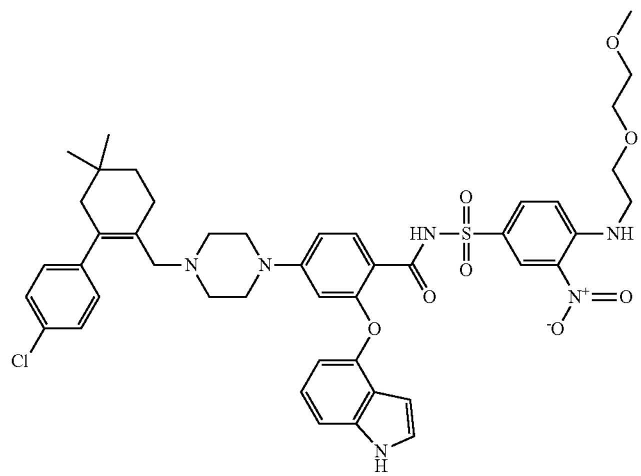 |
| 4-(4-{[2-(4-chlorophenyl)-4,4-dimethylcyclohex-1-en-1-yl]methyl}piperazin-1-yl)-2-(1H-indol-4-yloxy)-N-[(4-{[3-(methylsulfonyl)propyl]amino}-3-nitrophenyl)sulfonyl]benzamide | 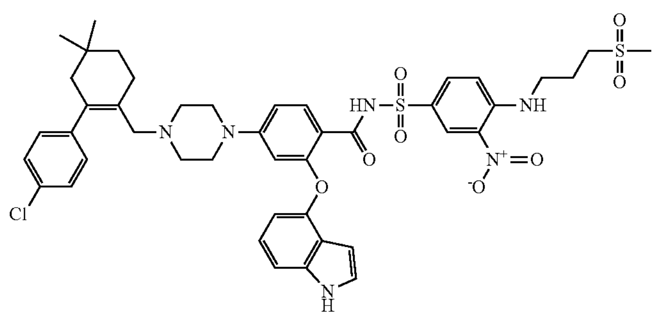 |
| 4-(4-{[2-(4-chlorophenyl)-4,4-dimethylcyclohex-1-en-1-yl]methyl}piperazin-1-yl)-N-[(4-{[3-(1,1-dioxidothiomorpholin-4-yl)propyl]amino}-3-nitrophenyl)sulfonyl]-2-(1H-indol-4-yloxy)benzamide | 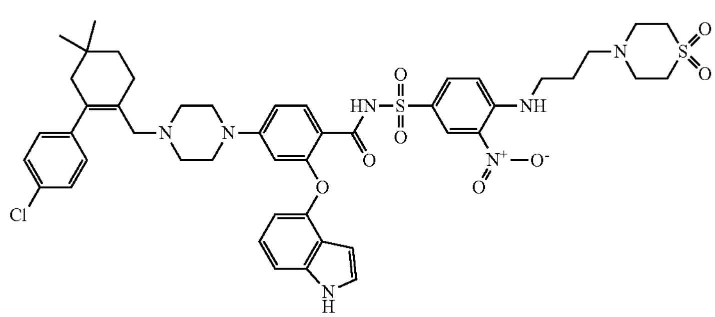 [SMILES: CC1(C)CCC(CN2CCN(c3ccc(C(=O)NS(=O)(=O)c4ccc(NCCCN5CCS(=O)(=O)CC5)c([N+](=O)[O-])c4)c(Oc4cccc5[nH]ccc45)c3)CC2)=C(c2ccc(Cl)cc2)C1] |

| Name | Structure |
|---|---|
| 4-(4-{[2-(4-chlorophenyl)-4,4-dimethylcyclohex-1-en-1-yl]methyl}piperazin-1-yl)-2-(1H-indol-5-yloxy)-N-{[3-nitro-4-(2-tetrahydro-2H-pyran-4-ylethyl)phenyl]sulfonyl}benzamide | 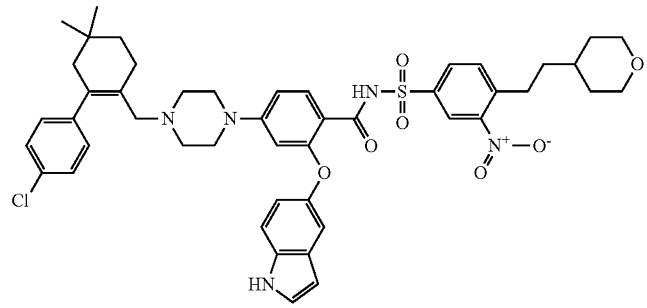 [SMILES: CC1(C)CCC(CN2CCN(c3ccc(C(=O)NS(=O)(=O)c4ccc(CCC5CCOCC5)c([N+](=O)[O-])c4)c(Oc4ccc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-{[4-(1,4-dioxan-2-ylmethoxy)-3-nitrophenyl]sulfonyl}-2-(1H-indol-5-yloxy)benzamide | 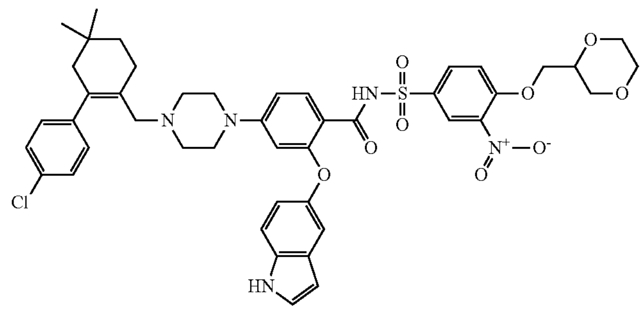 |
| 4-(4-{[2-(4-chlorophenyl)-4,4-dimethylcyclohex-1-en-1-yl]methyl}piperazin-1-yl)-2-(1H-indol-5-yloxy)-N-[(4-{[2-(2-methoxyethoxy)ethyl]amino}-3-nitrophenyl)sulfonyl]benzamide | 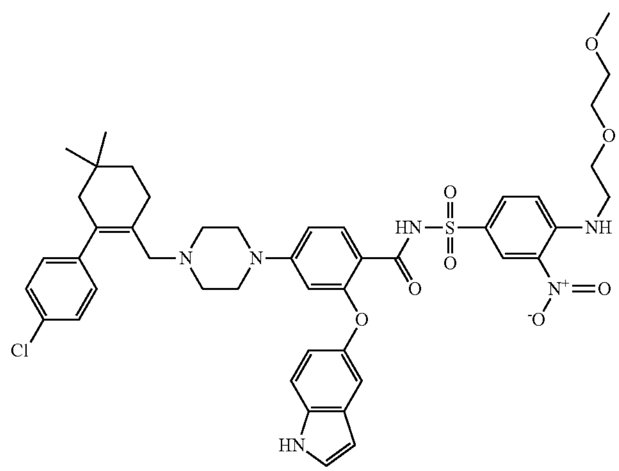 |
| 4-(4-{[2-(4-chlorophenyl)-4,4-dimethylcyclohex-1-en-1-yl]methyl}piperazin-1-yl)-N-({4-[(1,1-dioxidotetrahydrothien-3-yl)amino]-3-nitrophenyl}sulfonyl)-2-(1H-indol-4-yloxy)benzamide | 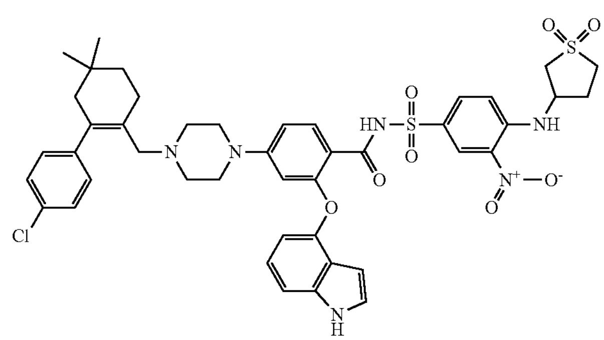 [SMILES: CC1(C)CCC(CN2CCN(c3ccc(C(=O)NS(=O)(=O)c4ccc(NC5CCS(=O)(=O)C5)c([N+](=O)[O-])c4)c(Oc4cccc5[nH]ccc45)c3)CC2)=C(c2ccc(Cl)cc2)C1] |

-continued

| Name | Structure |
|---|---|
| 4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[2-(trifluoromethoxy)ethyl]amino}phenyl)sulfonyl]benzamide | 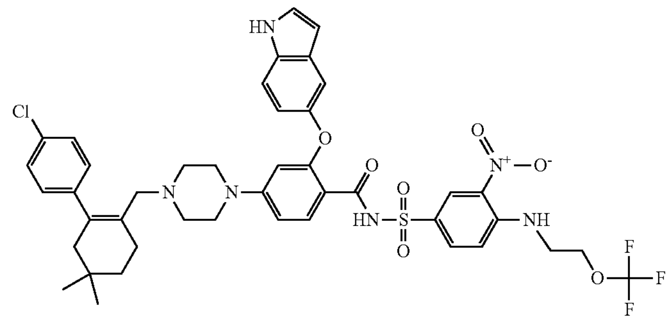 [SMILES: CC1(C)CCC(CN2CCN(c3ccc(C(=O)NS(=O)(=O)c4ccc(NCCOC(F)(F)F)c([N+](=O)[O-])c4)c(Oc4ccc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-[(4-{[(1,1-dioxidotetrahydro-2H-thiopyran-4-yl)methyl]amino}-3-nitrophenyl)sulfonyl]-2-(1H-indol-4-yloxy)benzamide | 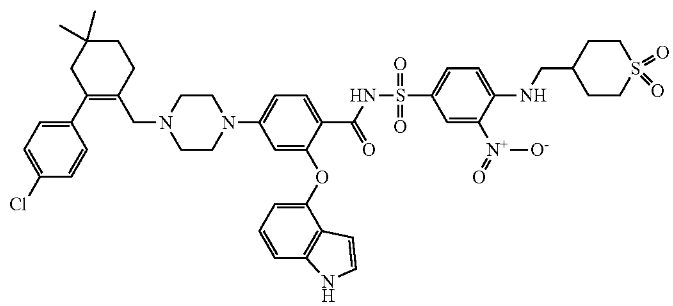 [SMILES: CC1(C)CCC(CN2CCN(c3ccc(C(=O)NS(=O)(=O)c4ccc(NCC5CCS(=O)(=O)CC5)c([N+](=O)[O-])c4)c(Oc4cccc5[nH]ccc45)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-({4-[(2,2-difluoroethyl)amino]-3-nitrophenyl}sulfonyl)-2-(1H-indol-5-yloxy)benzamide | 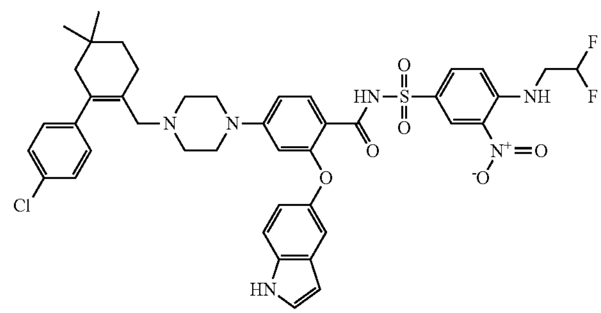 |
| 4-(4-{[2-(4-chlorophenyl)-4,4-dimethylcyclohex-1-en-1-yl]methyl}piperazin-1-yl)-2-(1H-indol-4-yloxy)-N-({4-[(tetrahydro-2H-pyran-4-ylmethyl)amino]-3-[(trifluoromethyl)sulfonyl]phenyl}sulfonyl)benzamide | 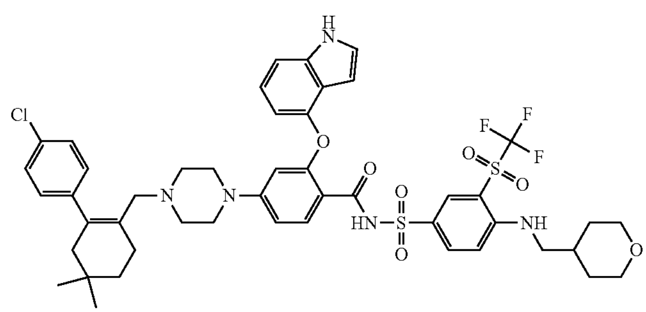 [SMILES: CC1(C)CCC(CN2CCN(c3ccc(C(=O)NS(=O)(=O)c4ccc(NCC5CCOCC5)c(S(=O)(=O)C(F)(F)F)c4)c(Oc4cccc5[nH]ccc45)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-2-(1H-indol-5-yloxy)-N-({4-[(tetrahydro-2H-pyran-4-ylmethyl)amino]-3-[(trifluoromethyl)sulfonyl]phenyl}sulfonyl)benzamide | 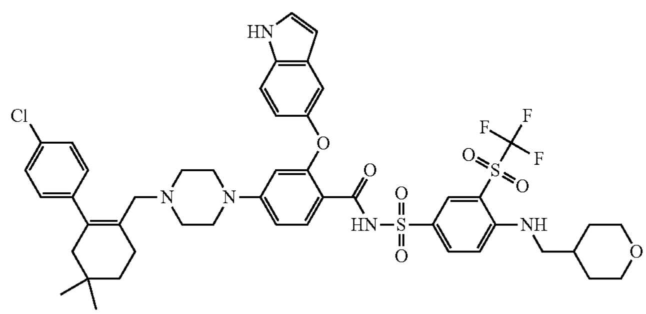 [SMILES: CC1(C)CCC(CN2CCN(c3ccc(C(=O)NS(=O)(=O)c4ccc(NCC5CCOCC5)c(S(=O)(=O)C(F)(F)F)c4)c(Oc4ccc5[nH]ccc5c4)c3)CC2)=C(c2ccc(Cl)cc2)C1] |

-continued

| Name | Structure |
|---|---|
| 4-(4-{[2-(4-chlorophenyl)-4,4-dimethylcyclohex-1-en-1-yl]methyl}piperazin-1-yl)-N-({4-[(4,4-difluorocyclohexyl)amino]-3-nitrophenyl}sulfonyl)-2-(1H-indol-5-yloxy)benzamide | 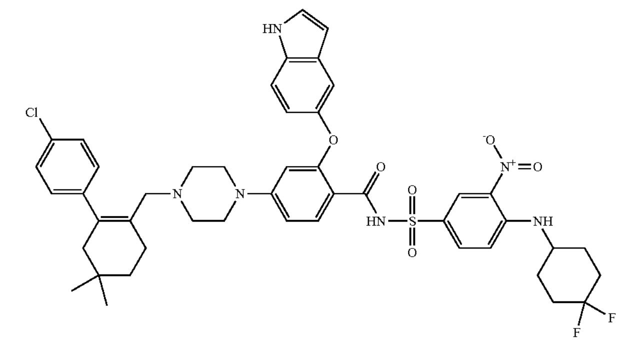 |
| 4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-nitrophenyl}sulfonyl)-2-(1H-indol-4-yloxy)benzamide | 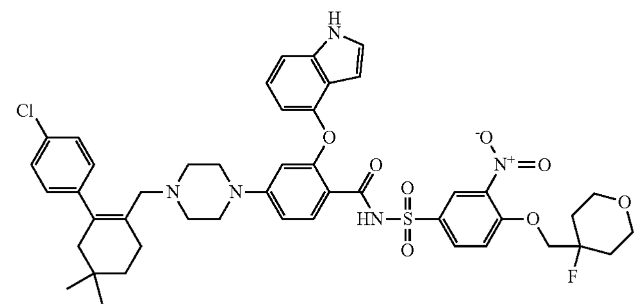 |
| 4-(4-{[4-(4-chlorophenyl)-1-isopropyl-6-oxo-1,6-dihydropyridin-3-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide | 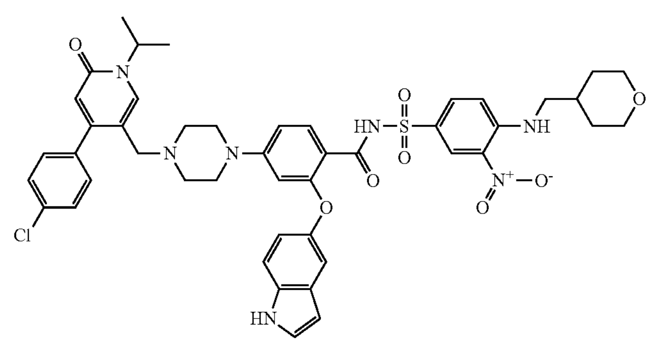 [SMILES: CC(C)n1cc(CN2CCN(c3ccc(C(=O)NS(=O)(=O)c4ccc(NCC5CCOCC5)c([N+](=O)[O-])c4)c(Oc4ccc5[nH]ccc5c4)c3)CC2)c(-c2ccc(Cl)cc2)cc1=O] |
| 4-(4-{[2-(4-chlorophenyl)-4,4-dimethylcyclohex-1-en-1-yl]methyl}piperazin-1-yl)-2-(1H-indol-5-yloxy)-N-[(4-{[(tetrahydro-2H-pyran-4-ylmethyl)amino]carbonyl}phenyl)sulfonyl]benzamide | 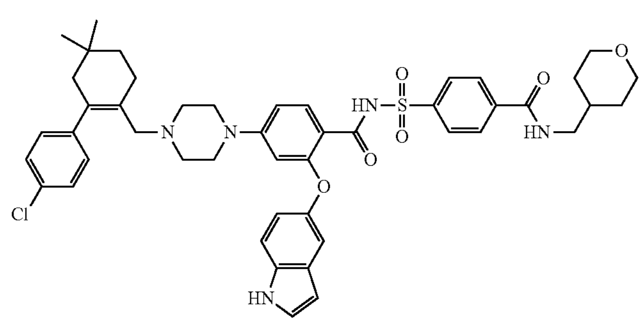 [SMILES: CC1(C)CCC(CN2CCN(c3ccc(C(=O)NS(=O)(=O)c4ccc(C(=O)NCC5CCOCC5)cc4)c(Oc4ccc5[nH]ccc5c4)c3)CC2)=C(c2ccc(Cl)cc2)C1] |

-continued

| Name | Structure |
|---|---|
| 4-(4-{[2-(4-chlorophenyl)-4,4-dimethylcyclohex-1-en-1-yl]methyl}piperazin-1-yl)-2-(1H-indol-4-yloxy)-N-({4-[(2-methoxyethyl)amino]-3-[(trifluoromethyl)sulfonyl]phenyl}sulfonyl)benzamide | 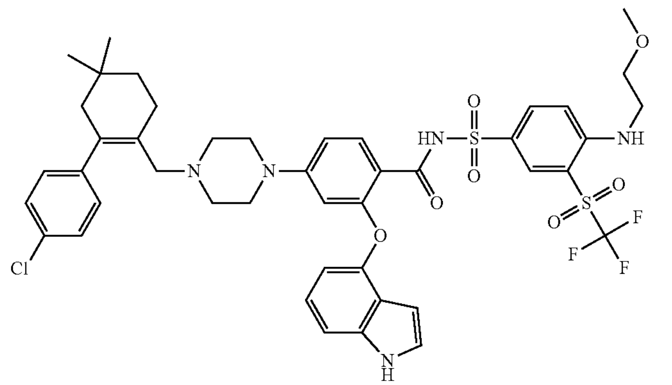 [SMILES: COCCNc1ccc(S(=O)(=O)NC(=O)c2ccc(N3CCN(CC4=C(c5ccc(Cl)cc5)CC(C)(C)CC4)CC3)cc2Oc2cccc3[nH]ccc23)cc1S(=O)(=O)C(F)(F)F] |
| Trans-4-(4-{[2-(4-chlorophenyl)-4,4-dimethylcyclohex-1-en-1-yl]methyl}piperazin-1-yl)-N-[(4-{[(4-hydroxycyclohexyl)methyl]amino}-3-nitrophenyl)sulfonyl]-2-(1H-indol-5-yloxy)benzamide | 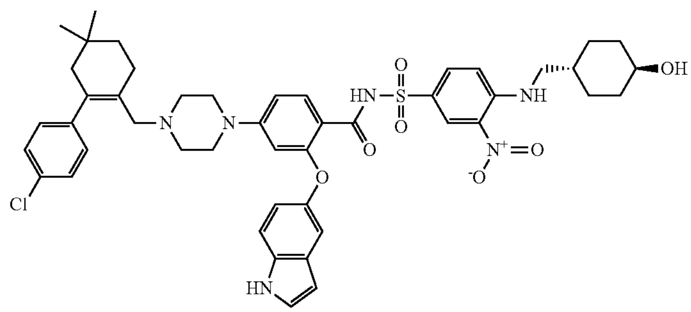 |
| Trans-4-(4-{[2-(4-chlorophenyl)-4,4-dimethylcyclohex-1-en-1-yl]methyl}piperazin-1-yl)-2-(1H-indol-5-yloxy)-N-[(4-{[(4-methoxycyclohexyl)methyl]amino}-3-nitrophenyl)sulfonyl]benzamide | 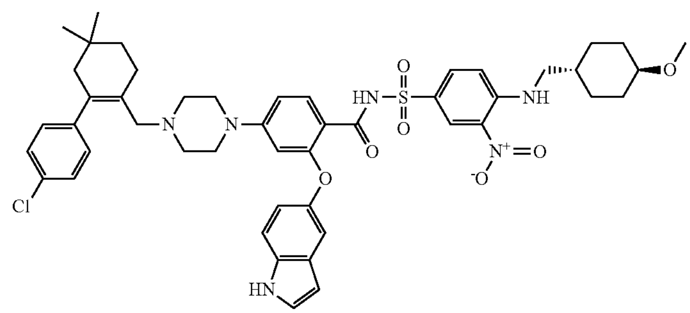 |
| Cis-4-(4-{[2-(4-chlorophenyl)-4,4-dimetylcyclohex-1-en-1-yl]methyl}piperazin-1-yl)-N-[(4-{[(4-hydroxycyclohexyl)methyl]amino}-3-nitrophenyl)sulfonyl]-2-(1H-indol-5-yloxy)benzamide | 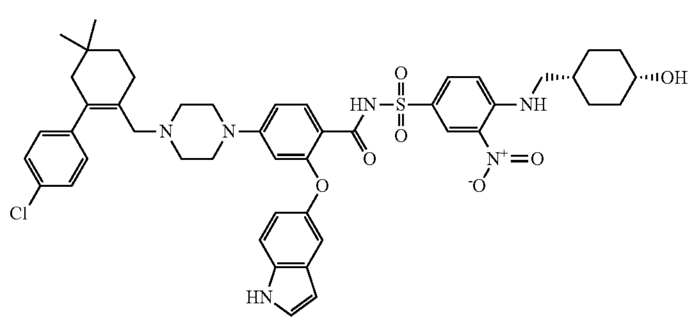 |

| Name | Structure |
|---|---|
| Cis-4-(4-{[2-(4-chlorophenyl)-4,4-dimethylcyclohex-1-en-1-yl]methyl}piperazin-1-yl)-2-(1H-indol-5-yloxy)-N-[(4-{[(4-methoxycyclohexyl)methyl]amino}-3-nitrophenyl)sulfonyl]benzamide | 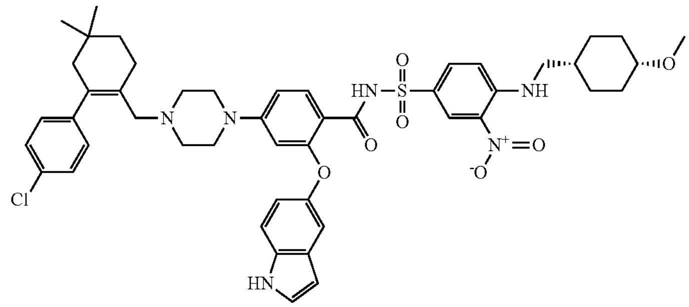 |
| 4-(4-{[2-(4-chlorophenyl)-4,4-dimethylcyclohex-1-en-1-yl]methyl}piperazin-1-yl)-2-(1H-indol-4-yloxy)-N-{[3-nitro-4-(2-tetrahydro-2H-pyran-4-ylethoxy)phenyl]sulfonyl}benzamide | 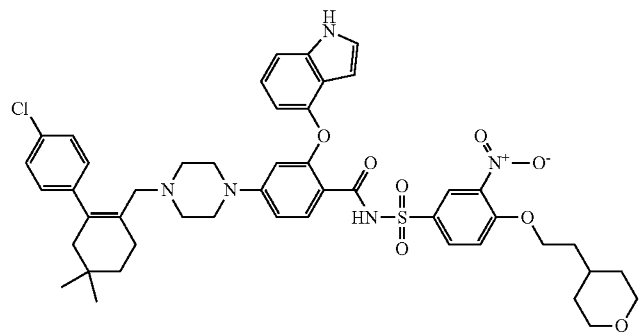 [SMILES: CC1(C)CCC(CN2CCN(c3ccc(C(=O)NS(=O)(=O)c4ccc(OCCC5CCOCC5)c([N+](=O)[O-])c4)c(Oc4cccc5[nH]ccc45)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-2-(1H-indol-5-yloxy)-N-({4-[(2-methoxyethyl)amino]-3-[(trifluoromethyl)sulfonyl]phenyl}sulfonyl)benzamide | 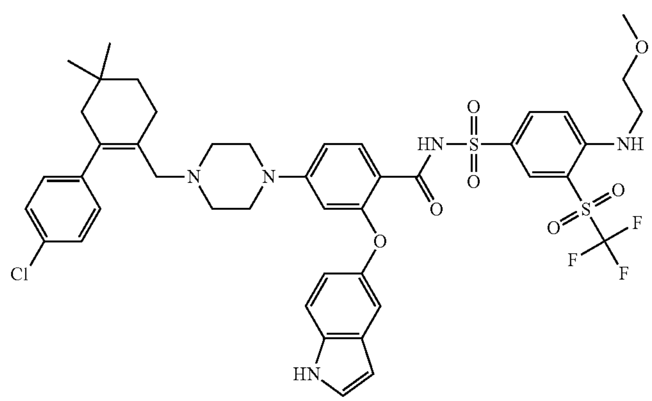 [SMILES: COCCNc1ccc(S(=O)(=O)NC(=O)c2ccc(N3CCN(CC4=C(c5ccc(Cl)cc5)CC(C)(C)CC4)CC3)cc2Oc2ccc3[nH]ccc3c2)cc1S(=O)(=O)C(F)(F)F] |
| 4-(4-{[2-(4-chlorophenyl)-4,4-dimethylcyclohex-1-en-1-yl]methyl}piperazin-1-yl)-2-(1H-indol-4-yloxy)-N-({4-[3-(methylsuflonyl)propyoxy]-3-nitrophenyl}sulfonyl)benzamide | 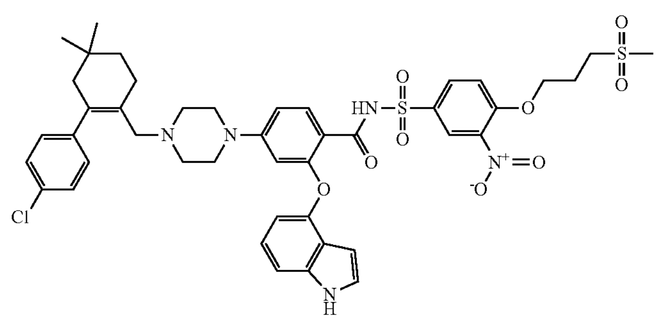 |

| Name | Structure |
|---|---|
| 4-(4-{[2-(4-chlorophenyl)-4,4-dimethylcyclohex-1-en-1-yl]methyl}piperazin-1-yl)-2-(1H-indol-5-yloxy)-N-({4-[(3-methoxypropyl)amino]-3-nitrophenyl}sulfonyl)benzamide | 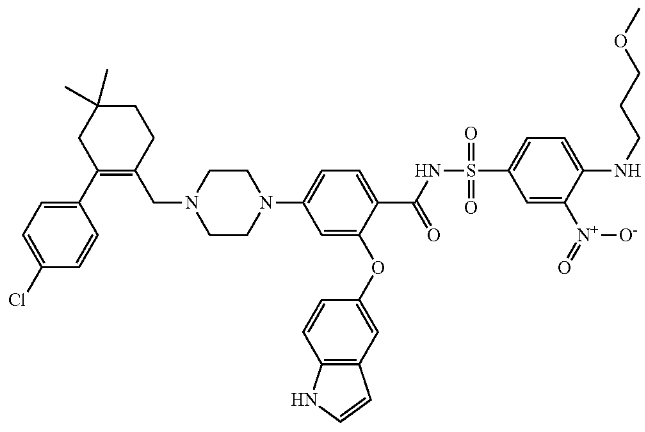 [SMILES: COCCCNc1ccc(S(=O)(=O)NC(=O)c2ccc(N3CCN(CC4=C(c5ccc(Cl)cc5)CC(C)(C)CC4)CC3)cc2Oc2ccc3[nH]ccc3c2)cc1[N+](=O)[O-]] |
| 4-(4-{[2-(4-chlorophenyl)-4,4-dimethylcyclohex-1-en-1-yl]methyl}piperazin-1-yl)-2-(1H-indol-4-yloxy)-N-({4-[(3-methoxypropyl)amino]-3-nitrophenyl}sulfonyl)benzamide | 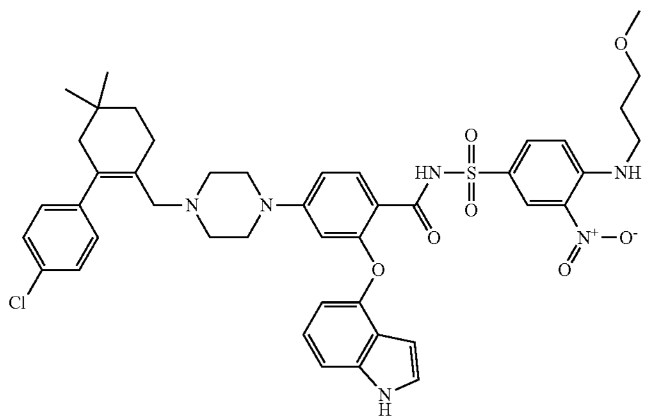 [SMILES: COCCCNc1ccc(S(=O)(=O)NC(=O)c2ccc(N3CCN(CC4=C(c5ccc(Cl)cc5)CC(C)(C)CC4)CC3)cc2Oc2cccc3[nH]ccc23)cc1[N+](=O)[O-]] |
| 4-(4-{[2-(4-chlorophenyl)-4,4-dimethylcyclohex-1-en-1-yl]methyl}piperazin-1-yl)-N-({4-[(2-cyanoethyl)amino]-3-nitrophenyl}sulfonyl)-2-(1H-indol-5-yloxy)benzamide | 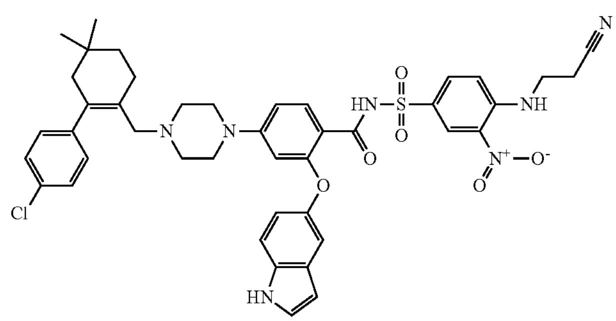 [SMILES: CC1(C)CCC(CN2CCN(c3ccc(C(=O)NS(=O)(=O)c4ccc(NCCC#N)c([N+](=O)[O-])c4)c(Oc4ccc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-({4-[(2-cyanoethyl)amino]-3-nitrophenyl}sulfonyl)-2-(1H-indol-4-yloxy)benzamide | 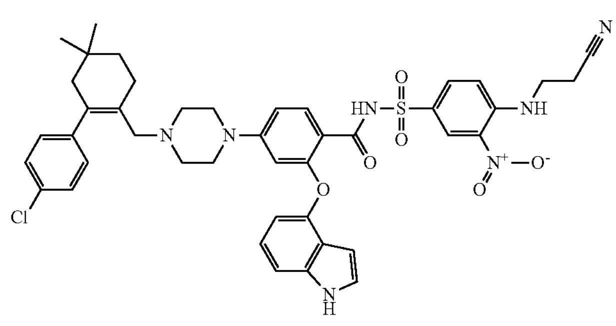 [SMILES: CC1(C)CCC(CN2CCN(c3ccc(C(=O)NS(=O)(=O)c4ccc(NCCC#N)c([N+](=O)[O-])c4)c(Oc4cccc5[nH]ccc45)c3)CC2)=C(c2ccc(Cl)cc2)C1] |

| Name | Structure |
|---|---|
| 4-(4-{[2-(4-chlorophenyl)-4,4-dimethylcyclohex-1-en-1-yl]methyl}piperazin-1-yl)-N-{[4-({[(3R)-4-hydroxy-1-adamanytl]methyl}amino)-3-nitrophenyl]sulfonyl}-2-(1H-indol-5-yloxy)benzamide | 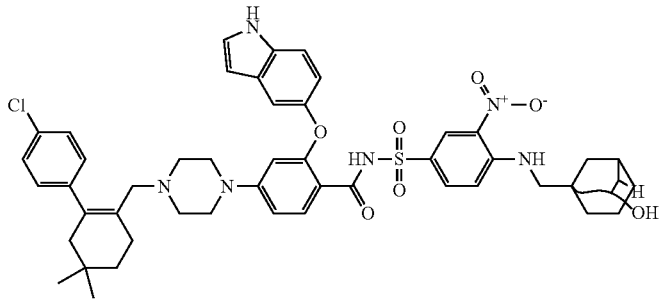 |
| 4-(4-{[2-(4-chlorophenyl)-4,4-dimethylcyclohex-1-en-1-yl]methyl}piperazin-1-yl)-N-{[4-({[Cis-4-hydroxy-1-adamantyl]methyl}amino)-3-nitrophenyl]sulfonyl}-2-(1H-indol-5-yloxy)benzamid | 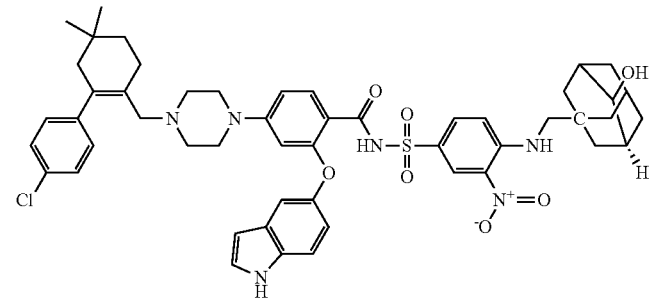 |
| 4-(4-{[2-(4-chlorophenyl)-4,4-dimethylcyclohex-1-en-1-yl]methyl}piperazin-1-yl)-2-(1H-indol-4-yloxy)-N-({3-nitro-4-[(3,3,3-trifluoropropyl)amino]phenyl}sulfonyl)benzamide | 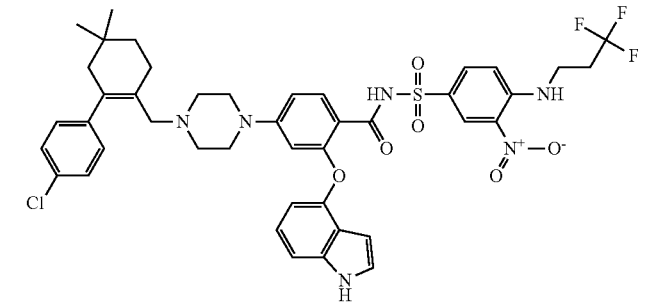 [SMILES: CC1(C)CCC(CN2CCN(c3ccc(C(=O)NS(=O)(=O)c4ccc(NCCC(F)(F)F)c([N+](=O)[O-])c4)c(Oc4cccc5[nH]ccc45)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-2-(1H-indol-5-yloxy)-N-({3-nitro-4-[(3,3,3-trifluoropropyl)amino]phenyl}sulfonyl)benzamide | 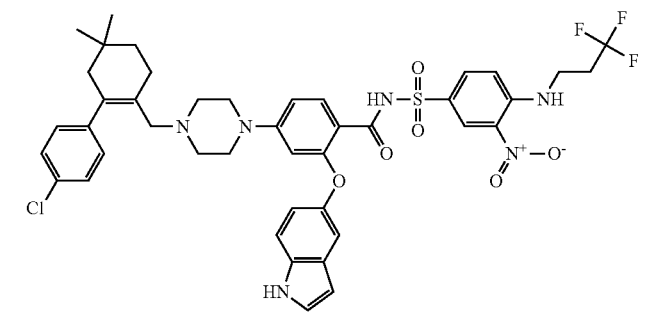 [SMILES: CC1(C)CCC(CN2CCN(c3ccc(C(=O)NS(=O)(=O)c4ccc(NCCC(F)(F)F)c([N+](=O)[O-])c4)c(Oc4ccc5[nH]ccc5c4)c3)CC2)=C(c2ccc(Cl)cc2)C1] |
| N-({5-bromo-6-[(tetrahydro-2H-pyran-4-ylmethyl)amino]pyridin-3-yl}sulfonyl)-4-(4-{[2-(4-chlorophenyl)-4,4-dimethylcyclohex-1-en-1-yl]methyl}piperazin-1-yl)-2-(1H-indol-4-yloxy)benzamide | 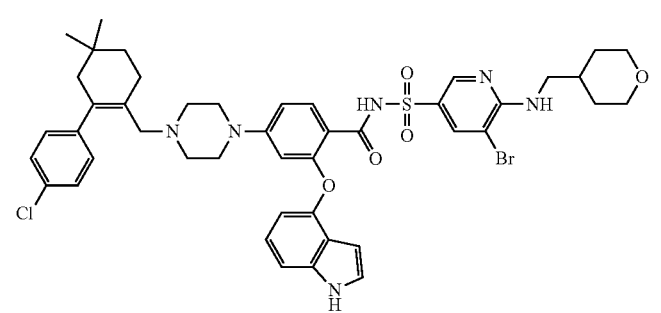 |

| Name | Structure |
|---|---|
| 4-(4-{[2-(4-chlorophenyl)-4,4-dimethylcyclohex-1-en-1-yl]methyl}piperazin-1-yl)-N-[(4-{[(1,1-dioxidotetrahydrothien-3-yl)methyl]amino}-3-nitrophenyl)sulfonyl]-2-(1H-indol-4-yloxy)benzamide | 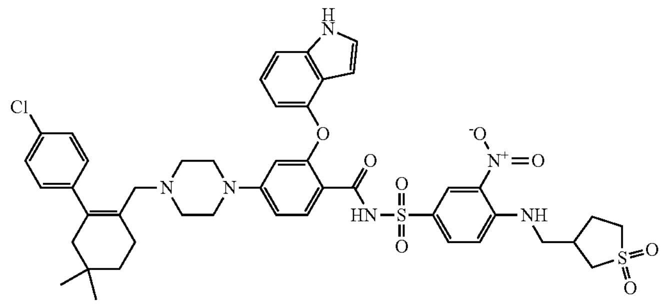 |
| 4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-nitrophenyl}sulfonyl)-2-(1H-indol-5-yloxy)benzamide | 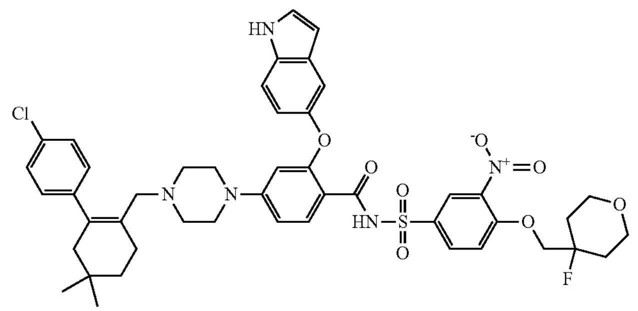 |
| 4-(4-{[2-(4-chlorophenyl)-4,4-dimethylcyclohex-1-en-1-yl]methyl}piperazin-1-yl)-2-(1H-indol-5-yloxy)-N-({4-(methylamino)-3-[(trifluoromethyl)sulfonyl]phenyl}sulfonyl)benzamide | 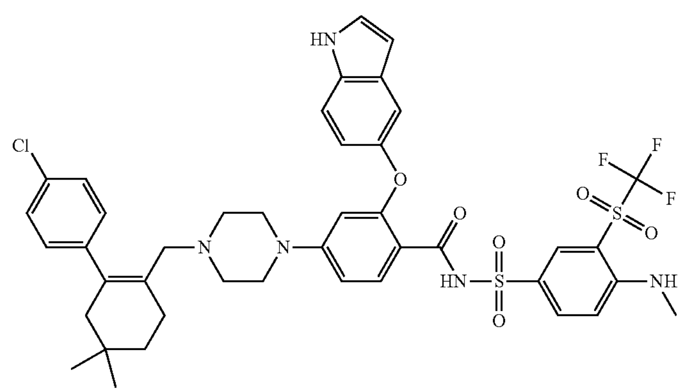 [SMILES: CNc1ccc(S(=O)(=O)NC(=O)c2ccc(N3CCN(CC4=C(c5ccc(Cl)cc5)CC(C)(C)CC4)CC3)cc2Oc2ccc3[nH]ccc3c2)cc1S(=O)(=O)C(F)(F)F] |
| N-{[5-bromo-6-(tetrahydro-2H-pyran-4-ylmethoxy)pyridin-3-yl]sulfonyl}-4-(4-{[2-(4-chlorophenyl)-4,4-dimethylcyclohex-1-en-1-yl]methyl}piperazin-1-yl)-2-(1H-indol-5-yloxy)benzamide | 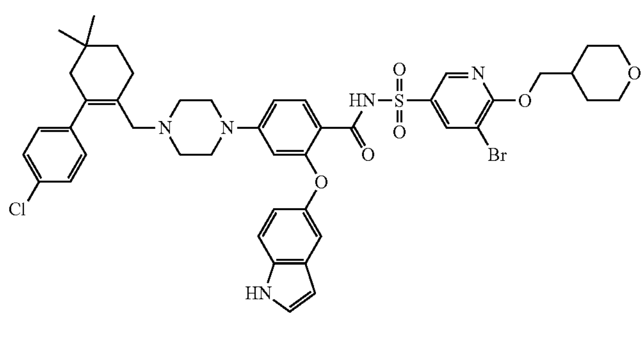 [SMILES: CC1(C)CCC(CN2CCN(c3ccc(C(=O)NS(=O)(=O)c4cnc(OCC5CCOCC5)c(Br)c4)c(Oc4ccc5[nH]ccc5c4)c3)CC2)=C(c2ccc(Cl)cc2)C1] |

-continued

| Name | Structure |
|---|---|
| 4-(4-{[4-(4-chlorophenyl)-6-isopropoxypyridin-3-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide | 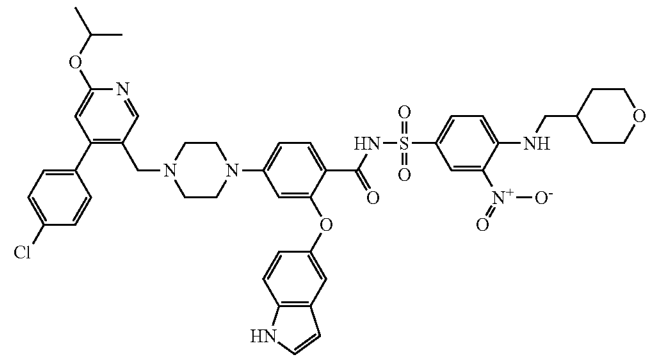 [SMILES: CC(C)Oc1cc(-c2ccc(Cl)cc2)c(CN2CCN(c3ccc(C(=O)NS(=O)(=O)c4ccc(NCC5CCOCC5)c([N+](=O)[O-])c4)c(Oc4ccc5[nH]ccc5c4)c3)CC2)cn1] |
| 4-(4-{[2-(4-chlorophenyl)-4,4-dimethylcyclohex-1-en-1-yl]methyl}piperazin-1-yl)-2-(1H-indol-5-yloxy)-N-{[6-(tetrahydro-2H-pyran-4-ylmethoxy)-5-(1,3-thiazol-2-yl)pyridin-3-yl]sulfonyl}benzamide | 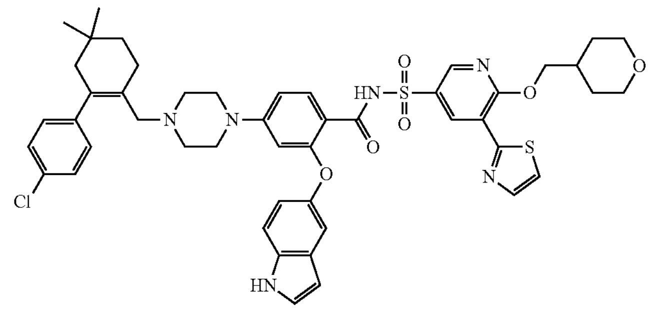 [SMILES: CC1(C)CCC(CN2CCN(c3ccc(C(=O)NS(=O)(=O)c4cnc(OCC5CCOCC5)c(-c5nccs5)c4)c(Oc4ccc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-2-(1H-indol-5-yloxy)-N-[(4-{[(2-methoxyethyl)amino]carbonyl}phenyl)sulfonyl]benzamide | 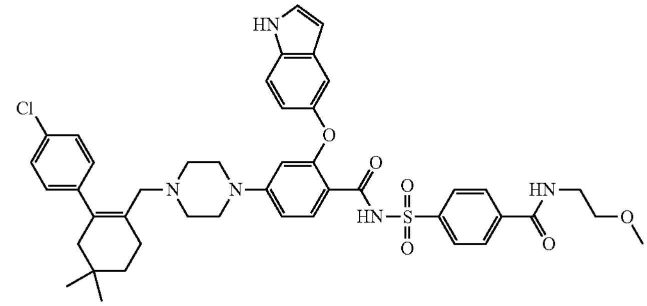 [SMILES: COCCNC(=O)c1ccc(S(=O)(=O)NC(=O)c2ccc(N3CCN(CC4=C(c5ccc(Cl)cc5)CC(C)(C)CC4)CC3)cc2Oc2ccc3[nH]ccc3c2)cc1] |
| 4-(4-{[2-(4-chlorophenyl)-4,4-dimethylcyclohex-1-en-1-yl]methyl}piperazin-1-yl)-N-{[5-cyano-6-(tetrahydro-2H-pyran-4-ylmethoxy)pyridin-3-yl]sulfonyl}-2-(1H-indol-5-yloxy)benzamide | 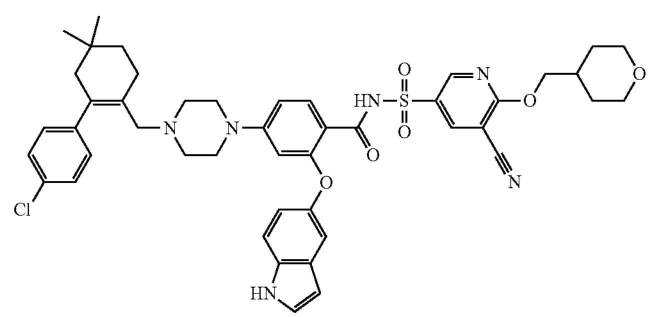 [SMILES: CC1(C)CCC(CN2CCN(c3ccc(C(=O)NS(=O)(=O)c4cnc(OCC5CCOCC5)c(C#N)c4)c(Oc4ccc5[nH]ccc5c4)c3)CC2)=C(c2ccc(Cl)cc2)C1] |

-continued

| Name | Structure |
|---|---|
| N-({4-[(1-acetylpiperidin-4-yl)amino]-3-nitrophenyl}sulfonyl)-4-(4-{[2-(4-chlorophenyl)-4,4-dimethylcyclohex-1-en-1-yl]methyl}piperazin-1-yl)-2-(1H-indol-5-yloxy)benzamide | 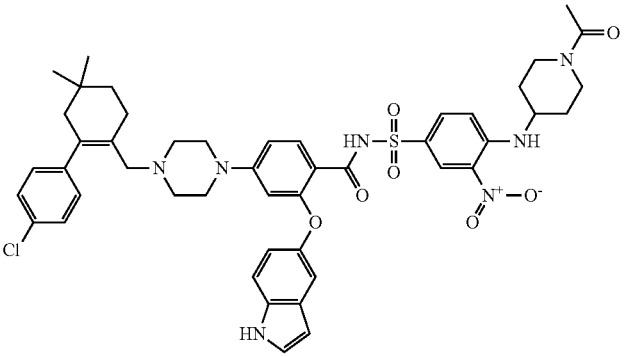 [SMILES: CC(=O)N1CCC(Nc2ccc(S(=O)(=O)NC(=O)c3ccc(N4CCN(CC5=C(c6ccc(Cl)cc6)CC(C)(C)CC5)CC4)cc3Oc3ccc4[nH]ccc4c3)cc2[N+](=O)[O-])CC1] |
| 4-(4-{[2-(4-chlorophenyl)-4,4-dimethylcyclohex-1-en-1-yl]methyl}piperazin-1-yl)-2-(1H-indol-5-yloxy)-N-[(4-{[1-(methylsuflonyl)piperidin-4-yl]amino}-3-nitrophenyl)sulfonyl]benzamide | 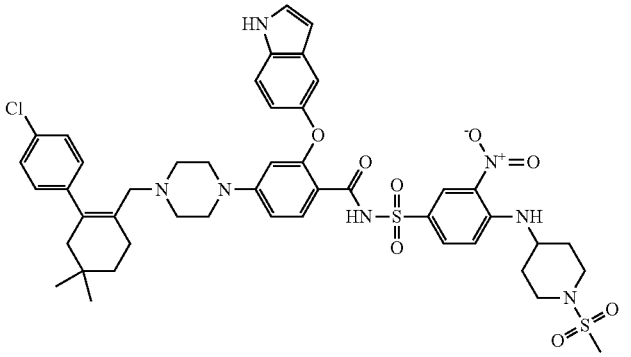 |
| 4-(4-{[2-(4-chlorophenyl)-4,4-dimethylcyclohex-1-en-1-yl]methyl}piperazin-1-yl)-N-({4-[(1,4-dioxan-2-ylmethyl)amino]-3-nitrophenyl}sulfonyl)-2-(1H-indol-5-yloxy)benzamide | 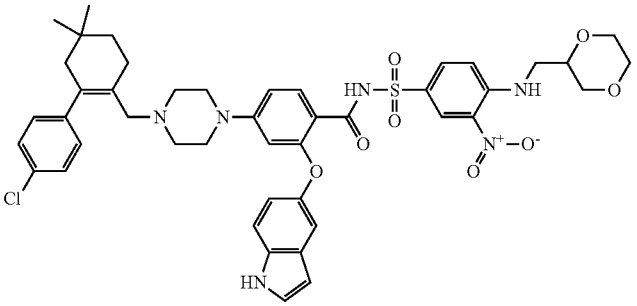 |
| N-({4-[(1-acetylpiperidin-4-yl)amino]-3-nitrophenyl}sulfonyl)-4-(4-{[2-(4-chlorophenyl)-4,4-dimethylcyclohex-1-en-1-yl]methyl}piperazin-1-yl)-2-(1H-indol-4-yloxy)benzamide | 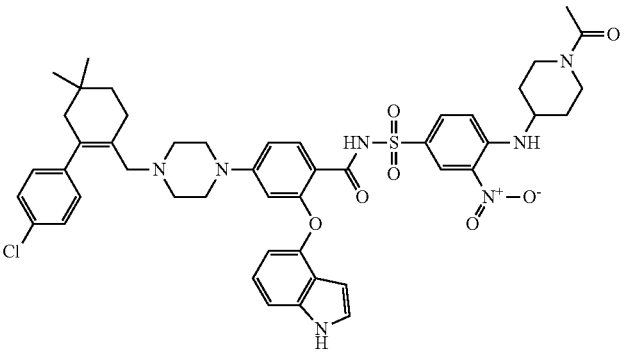 [SMILES: CC(=O)N1CCC(Nc2ccc(S(=O)(=O)NC(=O)c3ccc(N4CCN(CC5=C(c6ccc(Cl)cc6)CC(C)(C)CC5)CC4)cc3Oc3cccc4[nH]ccc34)cc2[N+](=O)[O-])CC1] |

-continued

| Name | Structure |
|---|---|
| 4-(4-{[2-(4-chlorophenyl)-4,4-dimethylcyclohex-1-en-1-yl]methyl}piperazin-1-yl)-2-(1H-indol-4-yloxy)-N-[(4-{[1-(methylsulfonyl)piperidin-4-yl]amino}-3-nitrophenyl)sulfonyl]benzamide | 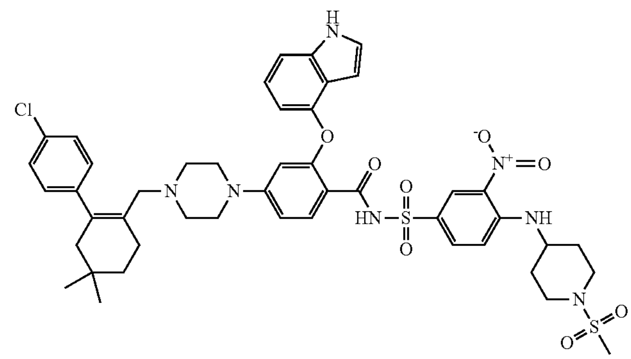 |
| 4-(4-{[4'-chloro-5-(trifluoromethyl)-1,1'-biphenyl-2-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide | 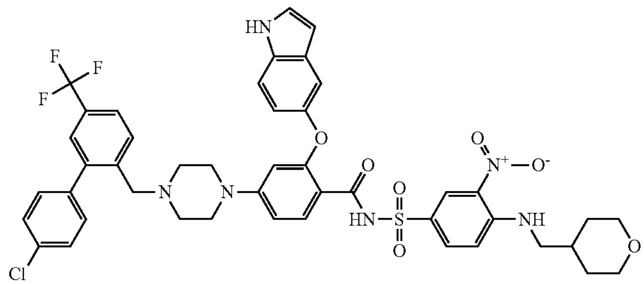 [SMILES: O=C(NS(=O)(=O)c1ccc(NCC2CCOCC2)c([N+](=O)[O-])c1)c1ccc(N2CCN(Cc3ccc(C(F)(F)F)cc3-c3ccc(Cl)cc3)CC2)cc1Oc1ccc2[nH]ccc2c1] |
| 4-(4-{[4'-chloro-5-(trifluoromethyl)-1,1'-biphenyl-2-yl]methyl}piperazin-1-yl)-2-(1H-indol-5-yloxy)-N-{[3-nitro-4-(tetrahydro-2H-pyran-4-ylmethoxy)phenyl]sulfonyl}benzamide | 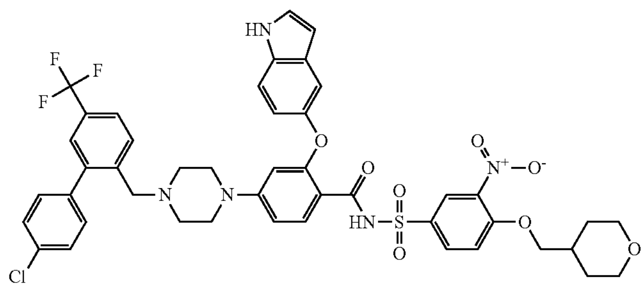 [SMILES: O=C(NS(=O)(=O)c1ccc(OCC2CCOCC2)c([N+](=O)[O-])c1)c1ccc(N2CCN(Cc3ccc(C(F)(F)F)cc3-c3ccc(Cl)cc3)CC2)cc1Oc1ccc2[nH]ccc2c1] |
| 4-{4-[(5-tert-butyl-4'-chloro-1,1'-biphenyl-2-yl)methyl]piperazin-1-yl}-2-(1H-indol-5-yloxy)-N-({3-nitro-4-[(tetrahydro-2H-pyran-4-ylmethyl)amino]phenyl}sulfonyl)benzamide | 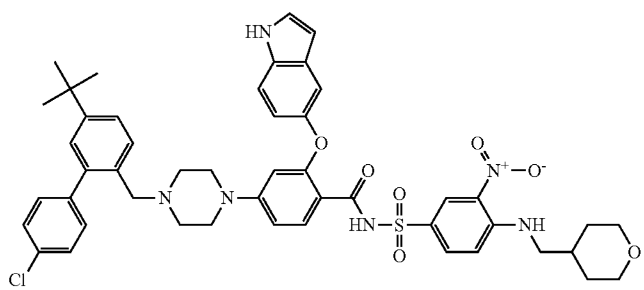 [SMILES: CC(C)(C)c1ccc(CN2CCN(c3ccc(C(=O)NS(=O)(=O)c4ccc(NCC5CCOCC5)c([N+](=O)[O-])c4)c(Oc4ccc5[nH]ccc5c4)c3)CC2)c(-c2ccc(Cl)cc2)c1] |
| 4-{4-[(5-tert-butyl-4'-chloro-1,1'-biphenyl-2-yl)methyl]piperazin-1-yl}-2-(1H-indol-5-yloxy)-N-{[3-nitro-4-(tetrahydro-2H-pyran-4-ylmethoxy)phenyl]sulfonyl}benzamide | 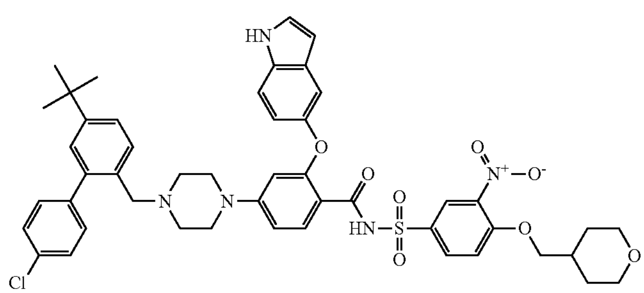 [SMILES: CC(C)(C)c1ccc(CN2CCN(c3ccc(C(=O)NS(=O)(=O)c4ccc(OCC5CCOCC5)c([N+](=O)[O-])c4)c(Oc4ccc5[nH]ccc5c4)c3)CC2)c(-c2ccc(Cl)cc2)c1] |

-continued

| Name | Structure |
|---|---|
| 4-(4-{[2-(4-chlorophenyl)-4,4-dimethylcyclohex-1-en-1-yl]methyl}piperazin-1-yl)-2-(1H-indol-4-yloxy)-N-({3-nitro-4-[(2,2,2-trifluoroethyl)amino]phenyl}sulfonyl)benzamide | 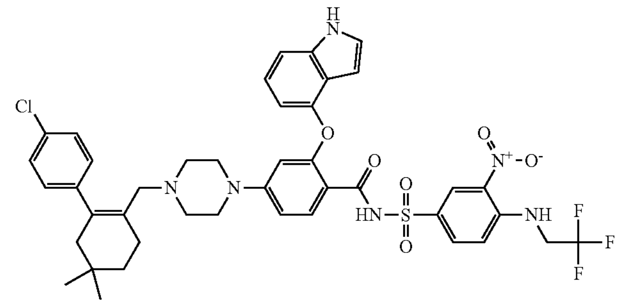 [SMILES: CC1(C)CCC(CN2CCN(c3ccc(C(=O)NS(=O)(=O)c4ccc(NCC(F)(F)F)c([N+](=O)[O-])c4)c(Oc4cccc5[nH]ccc45)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-2-(1H-indol-5-yloxy)-N-({3-nitro-4-[(2,2,2-trifluoroethyl)amino]phenyl}sulfonyl)benzamide | 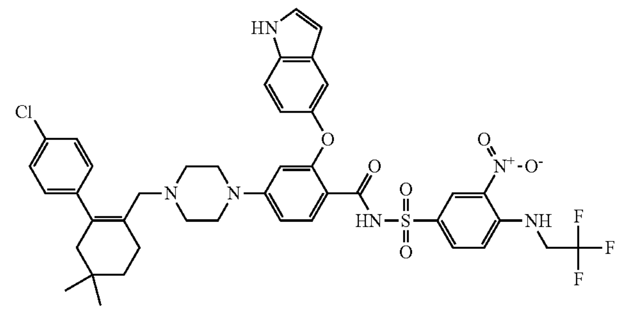 [SMILES: CC1(C)CCC(CN2CCN(c3ccc(C(=O)NS(=O)(=O)c4ccc(NCC(F)(F)F)c([N+](=O)[O-])c4)c(Oc4ccc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-2-(1H-indol-5-yloxy)-N-[(3-{[(tetrahydro-2H-pyran-4-ylmethyl)amino]carbonyl}phenyl)sulfonyl]benzamide | 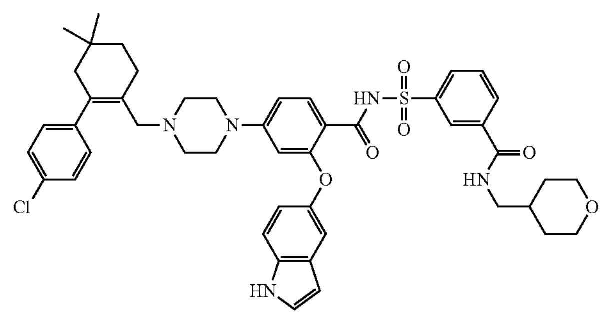 [SMILES: CC1(C)CCC(CN2CCN(c3ccc(C(=O)NS(=O)(=O)c4cccc(C(=O)NCC5CCOCC5)c4)c(Oc4ccc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-({4-[(2R)-1,4-dioxan-2-ylmethoxy]-3-nitrophenyl}sulfonyl)-2-(1H-indol-5-yloxy)benzamide | 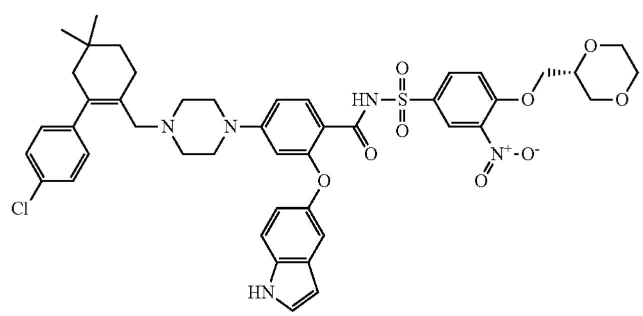 [SMILES: CC1(C)CCC(CN2CCN(c3ccc(C(=O)NS(=O)(=O)c4ccc(OC[C@H]5COCCO5)c([N+](=O)[O-])c4)c(Oc4ccc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-({4-[(2S)-1,4-dioxan-2-ymethoxy]-3-nitrophenyl}sulfonyl)-2-(1H-indol-5-yloxy)benzamide | 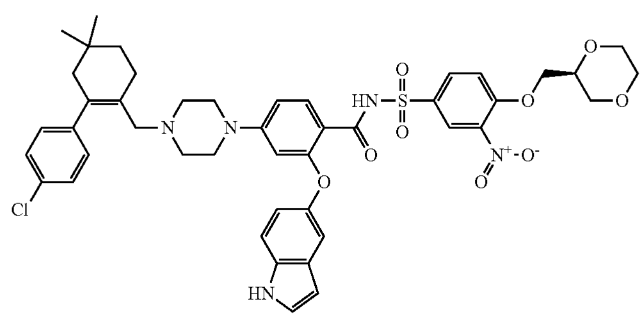 [SMILES: CC1(C)CCC(CN2CCN(c3ccc(C(=O)NS(=O)(=O)c4ccc(OC[C@@H]5COCCO5)c([N+](=O)[O-])c4)c(Oc4ccc5[nH]ccc5c4)c3)CC2)=C(c2ccc(Cl)cc2)C1] |

-continued

| Name | Structure |
|---|---|
| 4-(4-{[2-(4-chlorophenyl)-4,4-dimethylcyclohex-1-en-1-yl]methyl}piperazin-1-yl)-2-(1H-indol-5-yloxy)-N-({4-[(3-morpholin-4-ylpropyl)amino]-3-[(trifluoromethyl)sulfonyl]phenyl}sulfonyl)benzamide | 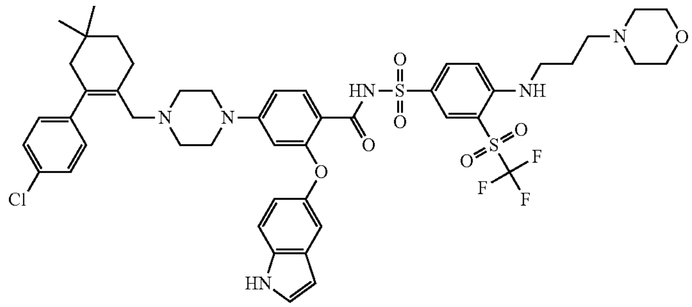 [SMILES: CC1(C)CCC(CN2CCN(c3ccc(C(=O)NS(=O)(=O)c4ccc(NCCCN5CCOCC5)c(S(=O)(=O)C(F)(F)F)c4)c(Oc4ccc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-2-(1H-indol-4-yloxy)-N-({4-[(3-morpholin-4-ylpropyl)amino]-3-[(trifluoromethyl)sulfonyl]phenyl}sulfonyl)benzamide | 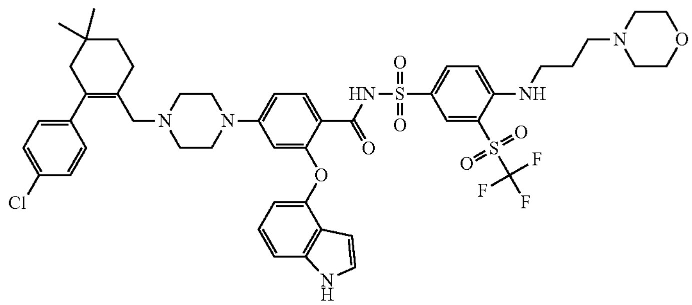 [SMILES: CC1(C)CCC(CN2CCN(c3ccc(C(=O)NS(=O)(=O)c4ccc(NCCCN5CCOCC5)c(S(=O)(=O)C(F)(F)F)c4)c(Oc4cccc5[nH]ccc45)c3)CC2)=C(c2ccc(Cl)cc2)C1] |
| N-({5-bromo-6-[(tetrahydro-2H-pyran-4-ylmethyl)amino]pyridin-3-yl}sulfonyl)-4-(4-{[2-(4-chlorophenyl)-4,4-dimethylcyclohex-1-en-1-yl]methyl}piperazin-1-yl)-2-(1H-indol-5-yloxy)benzamide | 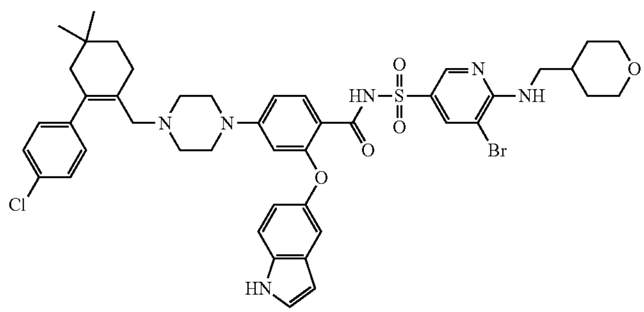 |
| 4-(4-{[2-(4-chlorophenyl)-4,4-dimethylcyclohex-1-en-1-yl]methyl}piperazin-1-yl)-2-(1H-indol-5-yloxy)-N-({4-[(2-morpholin-4-ylethyl)amino]-3-[(trifluoromethyl)sulfonyl]phenyl}sulfonyl)benzamide | 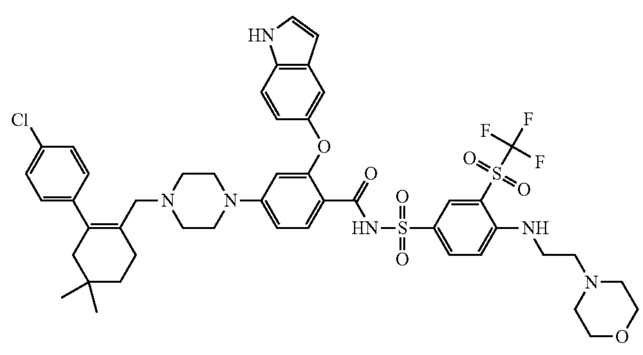 [SMILES: CC1(C)CCC(CN2CCN(c3ccc(C(=O)NS(=O)(=O)c4ccc(NCCN5CCOCC5)c(S(=O)(=O)C(F)(F)F)c4)c(Oc4ccc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-{5-cyano-6-[(tetrahydro-2H-pyran-4-ylmethyl)amino]pyridin-3-yl}sulfonyl)-2-(1H-indol-5-yloxy)benzamide | 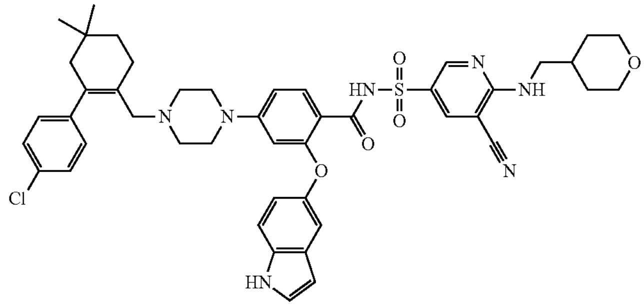 |

-continued

| Name | Structure |
|---|---|
| 4-(4-{[2-(4-chlorophenyl)-4,4-dimethylcyclohex-1-en-1-yl]methyl]piperazin-1-yl)-2-(1H-indol-5-yloxy)-N-({4-[(1-methylpiperidin-4-yl)oxy]-3-nitrophenyl}sulfonyl)benzamide | 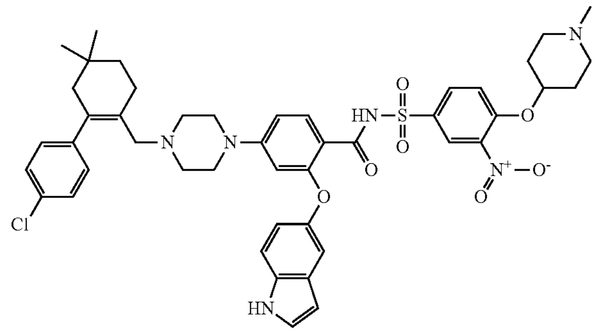 |
| 4-(4-{[2-(4-chlorophenyl)-4,4-dimethylcyclohex-1-en-1-yl]methyl}piperazin-1-yl)-2-(1H-indol-5-yloxy)-N-({4-[(1-methylpiperidin-4-yl)methoxy]-3-nitrophenyl}sulfonyl)benzamide | 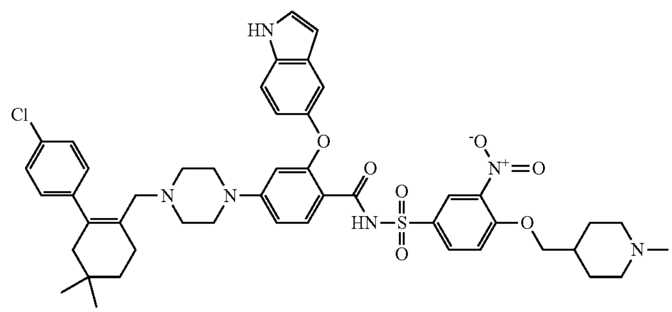 |
| 4-(4-{[4-(4-chlorophenyl)-1-(3-hydroxypropyl)-1,2,5,6-tetrahydropyridin-3-yl]methyl}piperazin-1-yl)-2-(1H-indol-4-yloxy)-N-({3-nitro-4-[(tetrahydro-2H-pyran-4-ylmethyl)amino]phenyl}sulfonyl)benzamide | 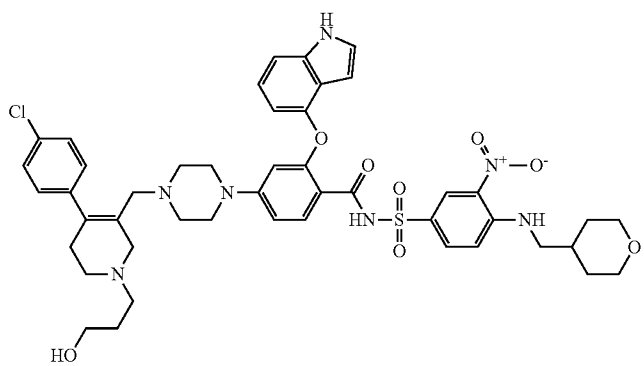 [SMILES: O=C(NS(=O)(=O)c1ccc(NCC2CCOCC2)c([N+](=O)[O-])c1)c1ccc(N2CCN(CC3=C(c4ccc(Cl)cc4)CCN(CCCO)C3)CC2)cc1Oc1cccc2[nH]ccc12] |
| benzyl 4-({[4-({[4-(4-{[2-(4-chlorophenyl)-4,4-dimethylcyclohex-1-en-1-yl]methyl}piperazin-1-yl)-2-(1H-indol-5-yloxy)benzoyl}amino}sulfonyl)-2-nitrophenyl]amino}methyl)piperidine-1-carboxylate | 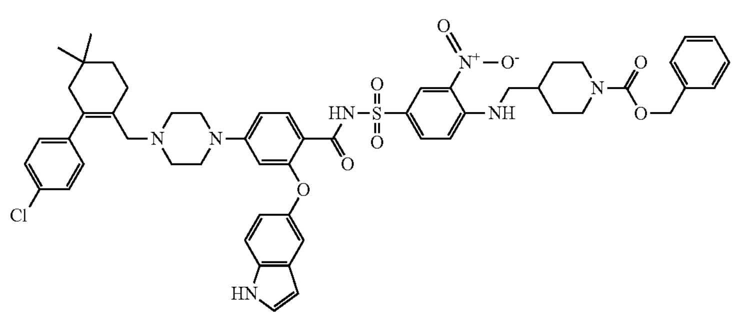 [SMILES: CC1(C)CCC(CN2CCN(c3ccc(C(=O)NS(=O)(=O)c4ccc(NCC5CCN(C(=O)OCc6ccccc6)CC5)c([N+](=O)[O-])c4)c(Oc4ccc5[nH]ccc5c4)c3)CC2)=C(c2ccc(Cl)cc2)C1] |

-continued

| Name | Structure |
|---|---|
| N-{[3-(aminocarbonyl)-4-(tetrahydro-2H-pyran-4-ylmethoxy)phenyl]sulfonyl}-4-(4-{[2-(4-chlorophenyl)-4,4-dimethylcyclohex-1-en-1-yl]methyl}piperazin-1-yl)-2-(1H-indol-5-yloxy)benzamide | 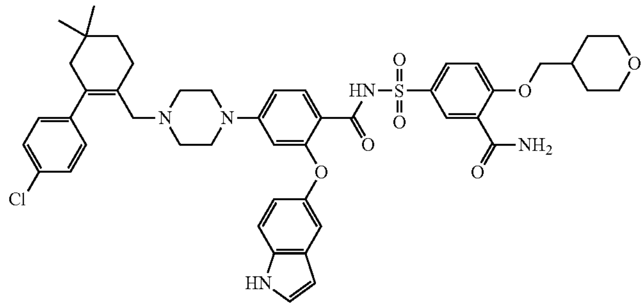 [SMILES: CC1(C)CCC(CN2CCN(c3ccc(C(=O)NS(=O)(=O)c4ccc(OCC5CCOCC5)c(C(N)=O)c4)c(Oc4ccc5[nH]ccc5c4)c3)CC2)=C(c2ccc(Cl)cc2)C1] |
| 4-(4-{[4'-chloro-5-(trifluoromethyl)-1,1'-biphenyl-2-yl]methyl}piperazin-1-yl)-2-(1H-indol-5-yloxy)-N-({3-nitro-4-[(1-tetrahydro-2H-pyran-4-ylpiperidin-4-yl)amino]phenyl}sulfonyl)benzamide | 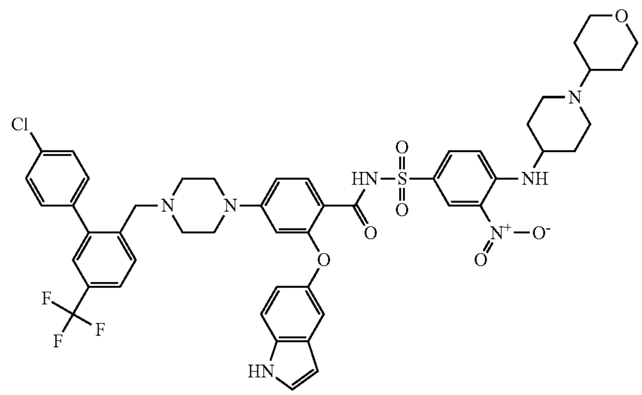 [SMILES: CC(C)(C)c1ccc(CN2CCN(c3ccc(C(=O)NS(=O)(=O)c4ccc(NC5CCN(C6CCOCC6)CC5)c([N+](=O)[O-])c4)c(Oc4ccc5[nH]ccc5c4)c3)CC2)c(-c2ccc(Cl)cc2)c1] |
| 4-{4-[(5-tert-butyl-4'-chloro-1,1'-biphenyl-2-yl)methyl]piperazin-1-yl}-2-(1H-indol-5-yloxy)-N-({3-nitro-4-[(1-tetrahydro-2H-pyran-4-ylpiperidin-4-yl)amino]phenyl}sulfonyl)benzamide | 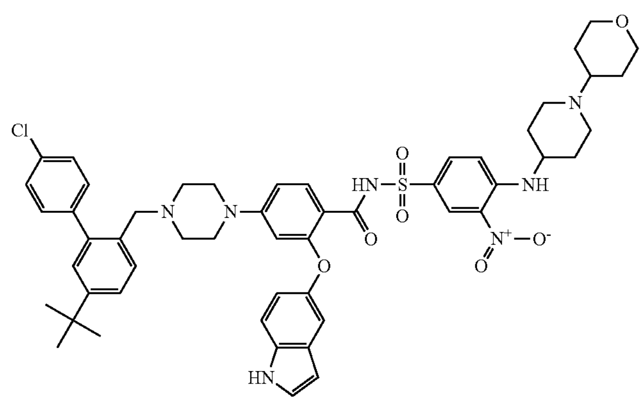 |
| 4-(4-{[2-(4-chlorophenyl)-4,4-dimethylcyclohex-1-en-1-yl]methyl}piperazin-1-yl)-2-(1H-indol-5-yloxy)-N-[(4-{[(1-methyl-1H-imidazol-5-yl)methyl]amino}-3-nitrophenyl)sulfonyl]benzamide | 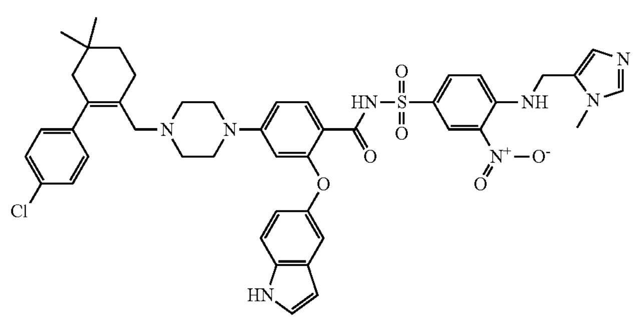 [SMILES: Cn1cncc1CNc1ccc(S(=O)(=O)NC(=O)c2ccc(N3CCN(CC4=C(c5ccc(Cl)cc5)CC(C)(C)CC4)CC3)cc2Oc2ccc3[nH]ccc3c2)cc1[N+](=O)[O-]] |

| Name | Structure |
|---|---|
| 4-(4-{[2-(4-chlorophenyl)-4,4-dimethylcyclohex-1-en-1-yl]methyl}piperazin-1-yl)-2-(1H-indol-5-yloxy)-N-{[4-(morpholin-4-ylsulfonyl)phenyl]sulfonyl}benzamide | 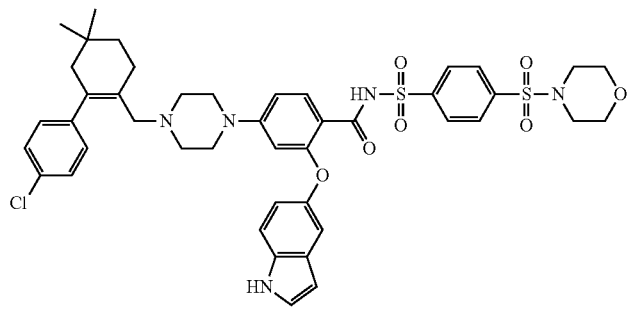 [SMILES: CC1(C)CCC(CN2CCN(c3ccc(C(=O)NS(=O)(=O)c4ccc(S(=O)(=O)N5CCOCC5)cc4)c(Oc4ccc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-({4-[(1,1-dioxidothiomorpholin-4-yl)amino]-3-nitrophenyl}sulfonyl)-2-(1H-indol-5-yloxy)benzamide | 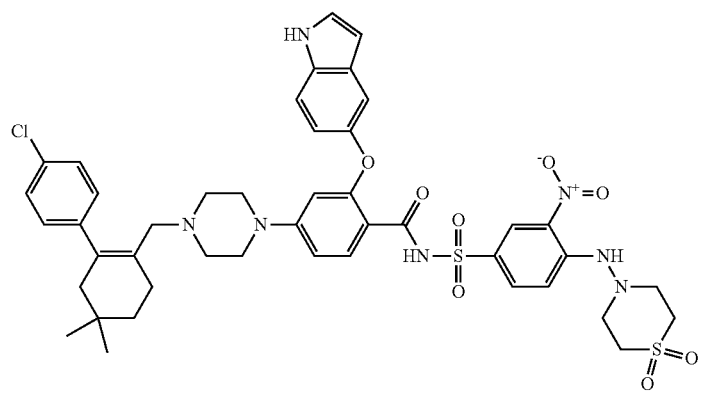 |
| 4-(4-{[2-(4-chlorophenyl)-4,4-dimethylcyclohex-1-en-1-yl]methyl}piperazin-1-yl)-2-(1H-indol-5-yloxy)-N-({4-[(4-morpholin-4-ylcyclohexyl)amino]-3-nitrophenyl}sulfonyl)benzamide | 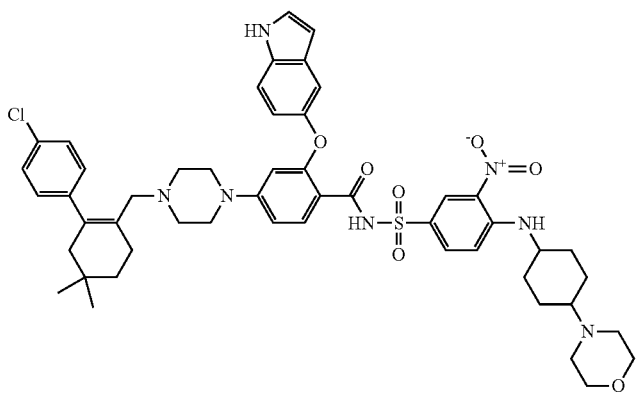 |
| N-{[5-bromo-6-(tetrahydro-2H-pyran-4-ylmethoxy)pyridin-3-yl]sulfonyl}-4-(4-{[2-(4-chlorophenyl)-4,4-dimethylcyclohex-1-en-1-yl]methyl}piperazin-1-yl)-2-(1H-indol-4-yloxy)benzamide | 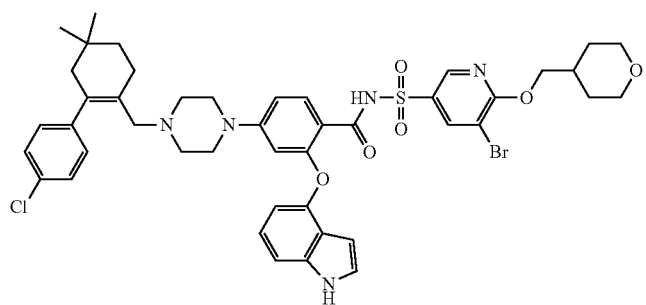 [SMILES: CC1(C)CCC(CN2CCN(c3ccc(C(=O)NS(=O)(=O)c4cnc(OCC5CCOCC5)c(Br)c4)c(Oc4cccc5[nH]ccc45)c3)CC2)=C(c2ccc(Cl)cc2)C1] |

| Name | Structure |
|---|---|
| 4-(4-{[2-(4-chlorophenyl)-4,4-dimethylcyclohex-1-en-1-yl]methyl}piperazin-1-yl)-2-(1H-indol-4-yloxy)-N-{[6-[(tetrahydro-2H-pyran-4-ylmethyl)amino]-5-(1,3-thiazol-2-yl)pyridin-3-yl]sulfonyl}benzamide | 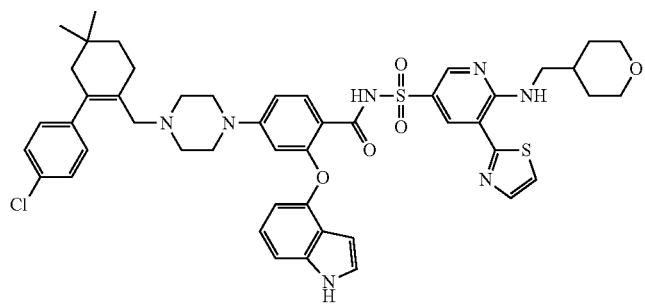 [SMILES: CC1(C)CCC(CN2CCN(c3ccc(C(=O)NS(=O)(=O)c4cnc(NCC5CCOCC5)c(-c5nccs5)c4)c(Oc4cccc5[nH]ccc45)c3)CC2)=C(c2ccc(Cl)cc2)C1] |
| 4-(4-{[2-(4-chlorophenyl)-4,4-dimetylcyclohex-1-en-1-yl]methyl}piperazin-1-yl)-N-({3-cyano-4-[(tetrahydro-2H-pyran-4-ylmethyl)amino]phenyl}sulfonyl)-2-(1H-indol-4-yloxy)benzamide | 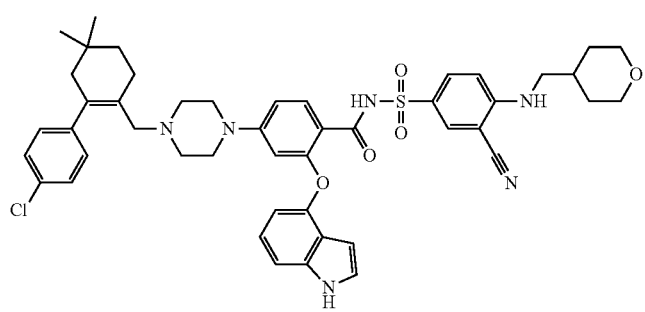 [SMILES: CC1(C)CCC(CN2CCN(c3ccc(C(=O)NS(=O)(=O)c4ccc(NCC5CCOCC5)c(C#N)c4)c(Oc4cccc5[nH]ccc45)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-({3-cyano-4-[(tetrahydro-2H-pyran-4-ylmethyl)amino]phenyl}sulfonyl)-2-(1H-indol-5-yloxy)benzamide | 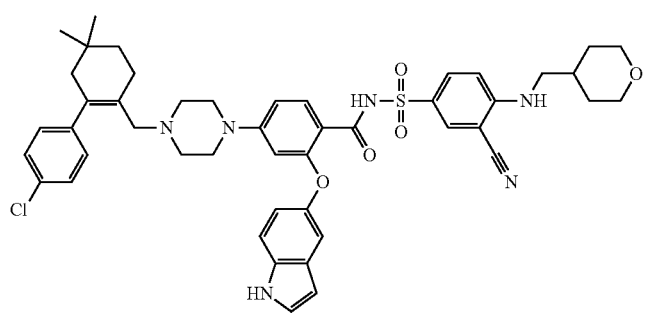 [SMILES: CC1(C)CCC(CN2CCN(c3ccc(C(=O)NS(=O)(=O)c4ccc(NCC5CCOCC5)c(C#N)c4)c(Oc4ccc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-({4-[(3,3-dimethylbutyl)amino]-3-nitrophenyl}sulfonyl)-2-(1H-indol-5-yloxy)benzamide | 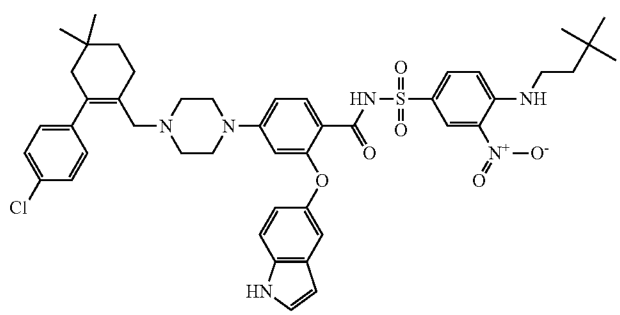 [SMILES: CC(C)(C)CCNc1ccc(S(=O)(=O)NC(=O)c2ccc(N3CCN(CC4=C(c5ccc(Cl)cc5)CC(C)(C)CC4)CC3)cc2Oc2ccc3[nH]ccc3c2)cc1[N+](=O)[O-]] |
| 4-(4-{[2-(4-chlorophenyl)-4,4-dimethylcyclohex-1-en-1-yl]methyl}piperazin-1-yl)-N-[(4-{[(1S)-1-(hydroxymethyl)-3-methylbutyl]amino}-3-nitrophenyl)sulfonyl]-2-(1H-indol-5-yloxy)benzamide | 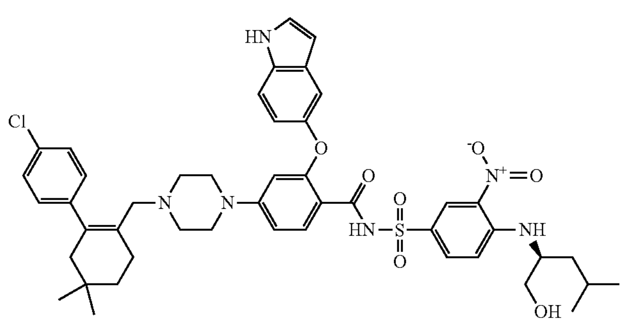 |

-continued

| Name | Structure |
|---|---|
| 4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[(2R)-tetrahydrofuran-2-ylmethyl]amino}phenyl)sulfonyl]benzamide | 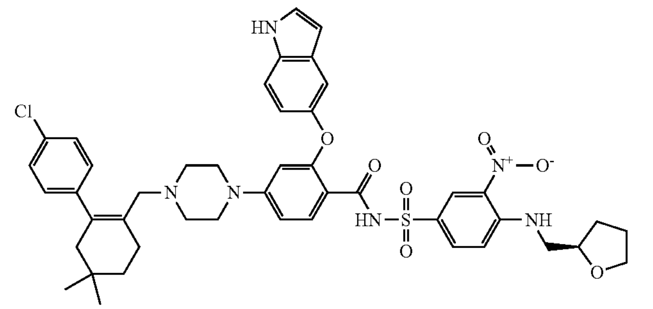 [SMILES: CC1(C)CCC(CN2CCN(c3ccc(C(=O)NS(=O)(=O)c4ccc(NC[C@H]5CCCO5)c([N+](=O)[O-])c4)c(Oc4ccc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-[(4-{[(1R)-1-(hydroxymethyl)-2-methylpropyl]amino}-3-nitrophenyl)sulfonyl]-2-(1H-indol-5-yloxy)benzamide | 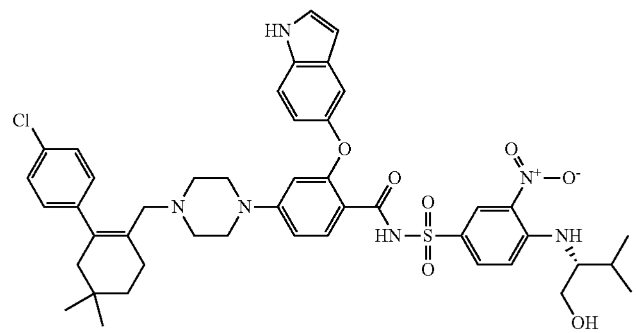 [SMILES: CC(C)[C@H](CO)Nc1ccc(S(=O)(=O)NC(=O)c2ccc(N3CCN(CC4=C(c5ccc(Cl)cc5)CC(C)(C)CC4)CC3)cc2Oc2ccc3[nH]ccc3c2)cc1[N+](=O)[O-]] |
| 4-(4-{[2-(4-chlorophenyl)-4,4-dimethylcyclohex-1-en-1-yl]methyl}piperazin-1-yl)-2-(1H-indol-5-yloxy)-N-({4-[(4-methoxyphenyl)amino]-3-nitrophenyl}sulfonyl)benzamide | 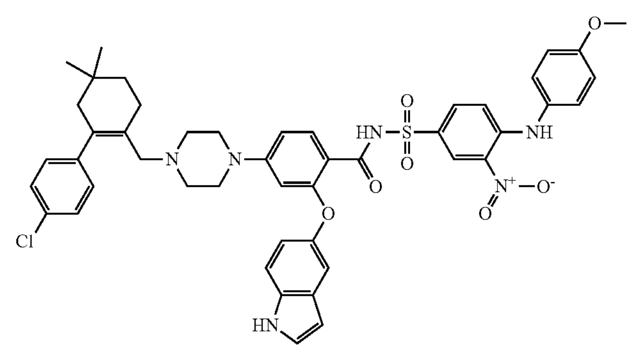 [SMILES: COc1ccc(Nc2ccc(S(=O)(=O)NC(=O)c3ccc(N4CCN(CC5=C(c6ccc(Cl)cc6)CC(C)(C)CC5)CC4)cc3Oc3ccc4[nH]ccc4c3)cc2[N+](=O)[O-])cc1] |
| N-[(4-{[2-(1,3-benzodioxol-5-yl)ethyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-indol-5-yloxy)benzamide | 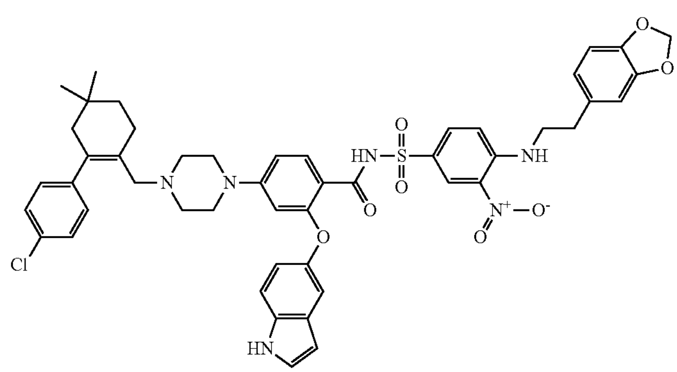 [SMILES: CC1(C)CCC(CN2CCN(c3ccc(C(=O)NS(=O)(=O)c4ccc(NCCc5ccc6c(c5)OCO6)c([N+](=O)[O-])c4)c(Oc4ccc5[nH]ccc5c4)c3)CC2)=C(c2ccc(Cl)cc2)C1] |

| Name | Structure |
|---|---|
| 4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[3-(2-oxopyrrolidin-1-yl)propyl]amino}phenyl)sulfonyl]benzamide | 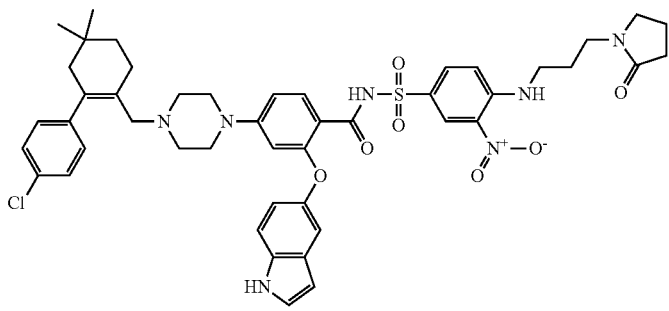 [SMILES: CC1(C)CCC(CN2CCN(c3ccc(C(=O)NS(=O)(=O)c4ccc(NCCCN5CCCC5=O)c([N+](=O)[O-])c4)c(Oc4ccc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-({4-[(4-hydroxyphenyl)amino]-3-nitrophenyl}sulfonyl)-2-(1H-indol-5-yloxy)benzamide | 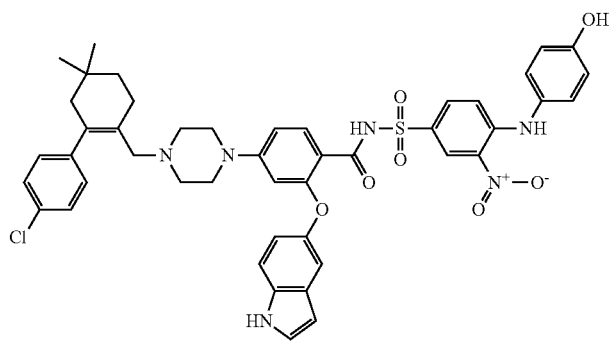 [SMILES: CC1(C)CCC(CN2CCN(c3ccc(C(=O)NS(=O)(=O)c4ccc(Nc5ccc(O)cc5)c([N+](=O)[O-])c4)c(Oc4ccc5[nH]ccc5c4)c3)CC2)=C(c2ccc(Cl)cc2)C1] |
| N-{[4-({2-[4-(aminosulfonyl)phenyl]ethyl}amino)-3-nitrophenyl]sulfonyl}-4-(4-{[2-(4-chlorophenyl)-4,4-dimethylcyclohex-1-en-1-yl]methyl}piperazin-1-yl)-2-(1H-indol-5-yloxy)benzamide | 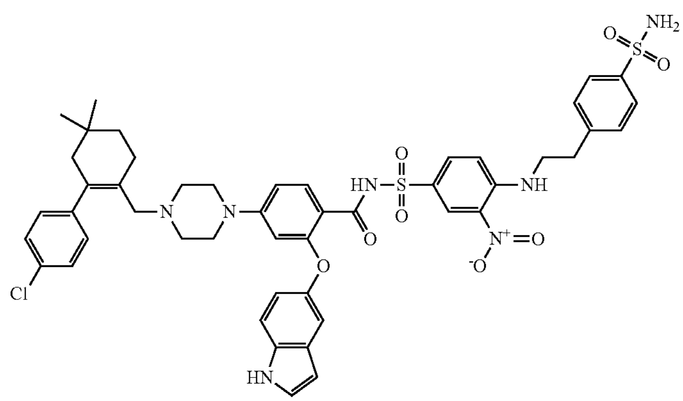 |
| 4-(4-{[2-(4-chlorophenyl)-4,4-dimethylcyclohex-1-en-1-yl]methyl}piperazin-1-yl)-N-[(4-{[3-(1H-imidazol-1-yl)propyl]amino}-3-nitrophenyl)sulfonyl]-2-(1H-indol-5-yloxy)benzamide | 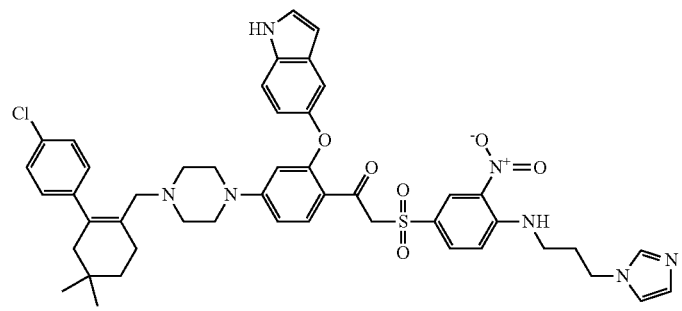 |

| Name | Structure |
|---|---|
| 4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[(1S)-1-phenylethyl]amino}phenyl)sulfonyl]benzamide | 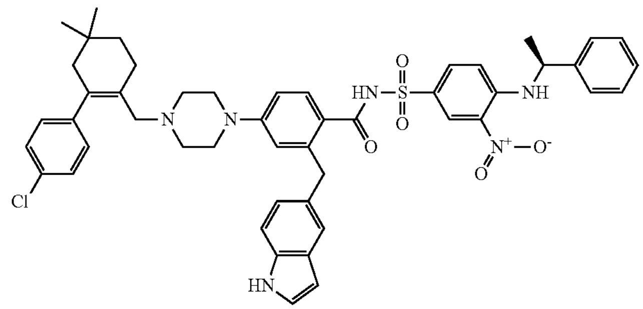 [SMILES: C[C@H](Nc1ccc(S(=O)(=O)NC(=O)c2ccc(N3CCN(CC4=C(c5ccc(Cl)cc5)CC(C)(C)CC4)CC3)cc2Cc2ccc3[nH]ccc3c2)cc1[N+](=O)[O-])c1ccccc1] |
| N-({2-chloro-5-fluoro-4-[(tetrahydro-2H-pyran-4-ylmethyl)amino]phenyl}sulfonyl)-4-(4-{[2-(4-chlorophenyl)-4,4-dimethylcyclohex-1-en-1-yl]methyl}piperazin-1-yl)-2-(1H-indol-5-yloxy)benzamide | 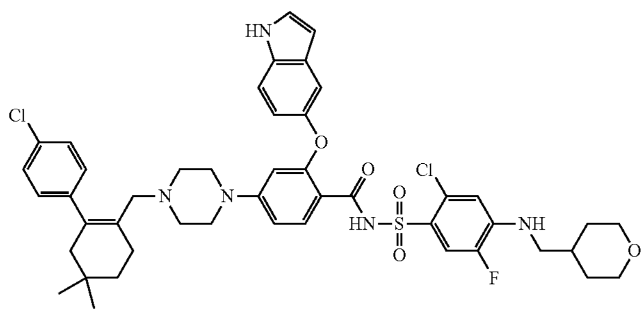 [SMILES: CC1(C)CCC(CN2CCN(c3ccc(C(=O)NS(=O)(=O)c4cc(F)c(NCC5CCOCC5)cc4Cl)c(Oc4ccc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-2-(1H-indol-5-yloxy)-N-[(4-{[2-(2-methoxyethoxy)ethyl]thio}-3-nitrophenyl)sulfonyl]benzamide | 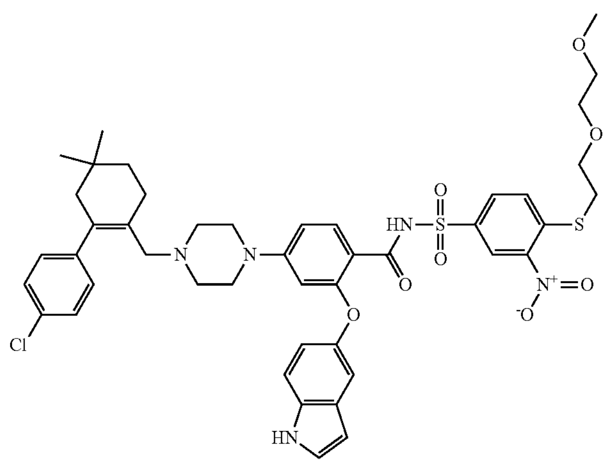 |
| 4-(4-{[2-(4-chlorophenyl)-4,4-dimethylcyclohex-1-en-1-yl]methyl}piperazin-1-yl)-2-(1H-indol-4-yloxy)-N-[(4-{[2-(2-methoxyethoxy)ethyl]thio}-3-nitrophenyl)sulfonyl]benzamide | 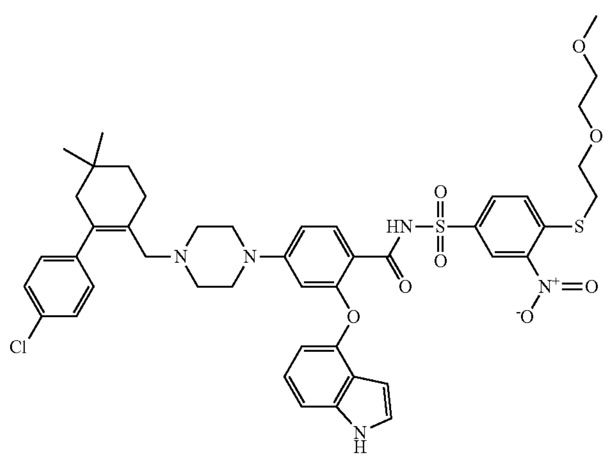 |

-continued

| Name | Structure |
|---|---|
| 4-(4-{[2-(4-chlorophenyl)-4,4-dimethylcyclohex-1-en-1-yl]methyl}piperazin-1-yl)-2-(1H-indol-5-yloxy)-N-{[4-(methylsulfonyl)phenyl]sulfonyl}benzamide | 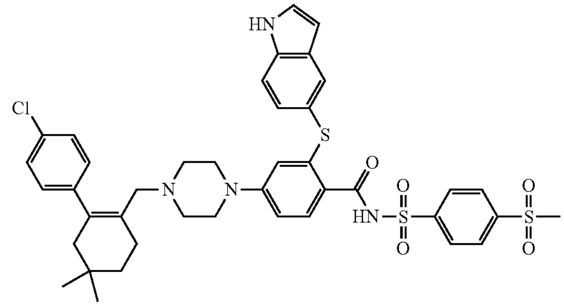 [SMILES: CC1(C)CCC(CN2CCN(c3ccc(C(=O)NS(=O)(=O)c4ccc(S(C)(=O)=O)cc4)c(Sc4ccc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-2-(1H-indol-4-yloxy)-N-{[4-(methylsulfonyl)phenyl]sulfonyl}benzamide | 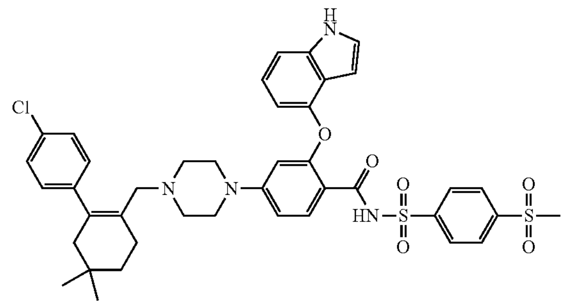 [SMILES: CC1(C)CCC(CN2CCN(c3ccc(C(=O)NS(=O)(=O)c4ccc(S(C)(=O)=O)cc4)c(Oc4cccc5[nH]ccc45)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-({4-[(2,2-dimethyltetrahydro-2H-pyran-4-yl)methoxy]-3-nitrophenyl}sulfonyl)-2-(1H-indol-5-yloxy)benzamide | 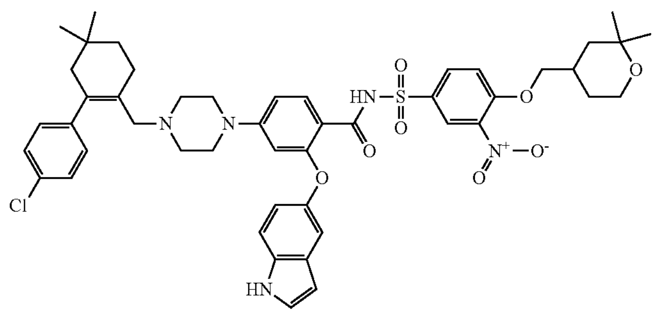 [SMILES: CC1(C)CCC(CN2CCN(c3ccc(C(=O)NS(=O)(=O)c4ccc(OCC5CCOC(C)(C)C5)c([N+](=O)[O-])c4)c(Oc4ccc5[nH]ccc5c4)c3)CC2)=C(c2ccc(Cl)cc2)C1] |
| 4-(4-{[2-(4-chlorophenyl)-4,4-dimethylcyclohx-1-en-1-yl]methyl}piperazin-1-yl)-N-({5-cyano-6-[(4-fluorotetrahydro-2H-pyran-4-yl)methoxy]pyridin-3-yl}sulfonyl)-2-(1H-indol-5-yloxy)benzamide | 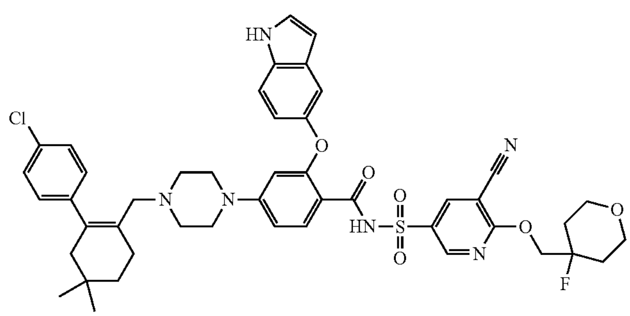 [SMILES: CC1(C)CCC(CN2CCN(c3ccc(C(=O)NS(=O)(=O)c4cnc(OCC5(F)CCOCC5)c(C#N)c4)c(Oc4ccc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-{[5-cyano-6-(tetrahydro-2H-pyran-4-ylmethoxy)pyridin-3-yl]sulfonyl}-2-(1H-indol-4-yloxy)benzamide | 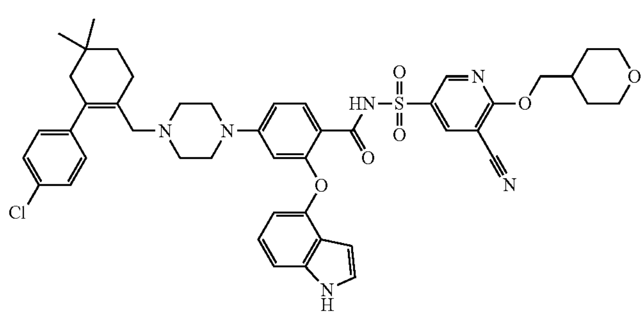 [SMILES: CC1(C)CCC(CN2CCN(c3ccc(C(=O)NS(=O)(=O)c4cnc(OCC5CCOCC5)c(C#N)c4)c(Oc4cccc5[nH]ccc45)c3)CC2)=C(c2ccc(Cl)cc2)C1] |

| Name | Structure |
|---|---|
| 4-(4-{[2-(4-chlorophenyl)-4,4-dimethylcyclohex-1-en-1-yl]methyl}piperazin-1-yl)-N-{[5-chloro-6-(tetrahydro-2H-pyran-4-ylmethoxy)pyridin-3-yl]sulfonyl}-2-(1H-indol-4-yloxy)benzamide | 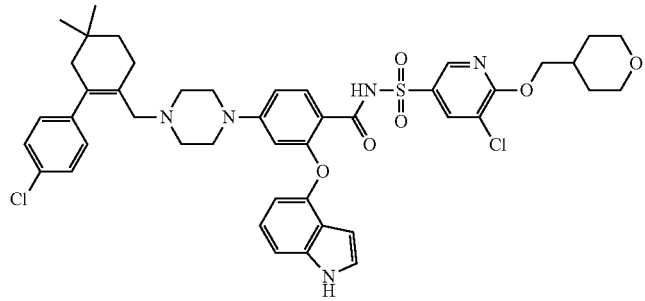 [SMILES: CC1(C)CCC(CN2CCN(c3ccc(C(=O)NS(=O)(=O)c4cnc(OCC5CCOCC5)c(Cl)c4)c(Oc4cccc5[nH]ccc45)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-{[5-cyano-6-(2-morpholin-4-ylethoxy)pyridin-3-yl]sulfonyl}-2-(1H-indol-5-yloxy)benzamide | 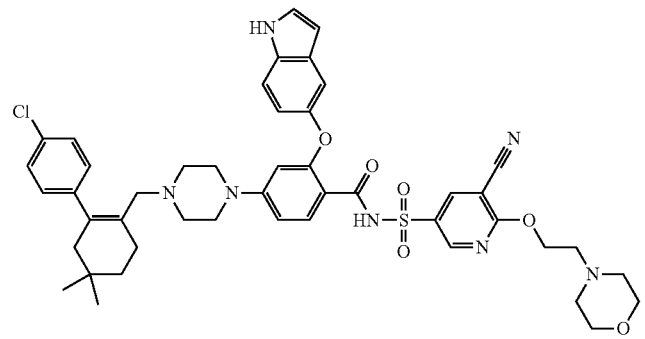 [SMILES: CC1(C)CCC(CN2CCN(c3ccc(C(=O)NS(=O)(=O)c4cnc(OCCN5CCOCC5)c(C#N)c4)c(Oc4ccc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-2-(1H-indol-5-yloxy)-N-({3-nitro-4-[(1-tetrahydro-2H-pyran-4-ylpiperidin-4-yl)oxy]phenyl}sulfonyl)benzamide | 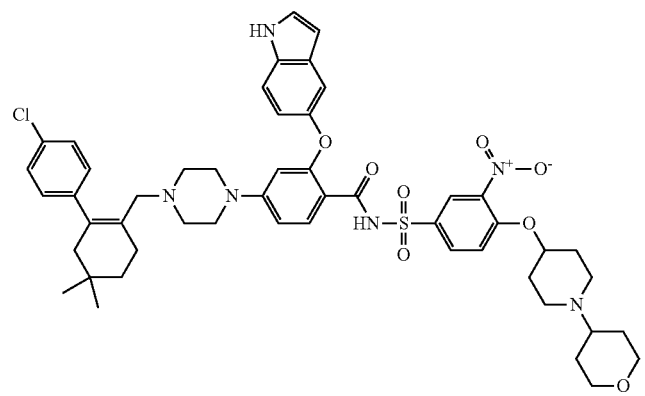 [SMILES: CC1(C)CCC(CN2CCN(c3ccc(C(=O)NS(=O)(=O)c4ccc(OC5CCN(C6CCOCC6)CC5)c([N+](=O)[O-])c4)c(Oc4ccc5[nH]ccc5c4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-2-(1H-indol-5-yloxy)-N-{{4-[(4-morpholin-4-ylbut-2-ynyl)oxy]-3-nitrophenyl}sulfonyl)benzamide | 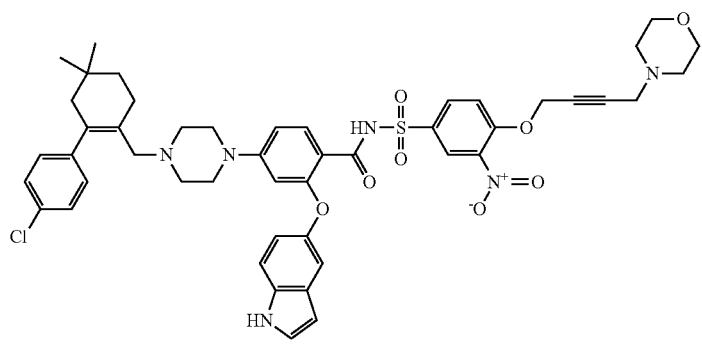 |

| Name | Structure |
|---|---|
| 4-(4-{[2-(4-chlorophenyl)-4,4-dimethylcyclohex-1-en-1-yl]methyl}piperazin-1-yl)-N-{[5-ethynyl-6-(tetrahydro-2H-pyran-4-ylmethoxy)pyridin-3-yl]sulfonyl}-2-(1H-indol-4-yloxy)benzamide | 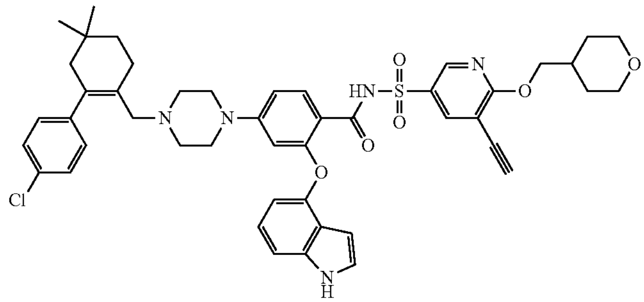 [SMILES: C#Cc1cc(S(=O)(=O)NC(=O)c2ccc(N3CCN(CC4=C(c5ccc(Cl)cc5)CC(C)(C)CC4)CC3)cc2Oc2cccc3[nH]ccc23)cnc1OCC1CCOCC1] |
| 4-(4-{[2-(4-chlorophenyl)-4,4-dimethylcyclohex-1-en-1-yl]methyl}piperazin-1-yl)-N-{[5-cyano-6-(2-morpholin-4-ylethoxy)pyridin-3-yl]sulfonyl}-2-(1H-indol-4-yloxy)benzamide | 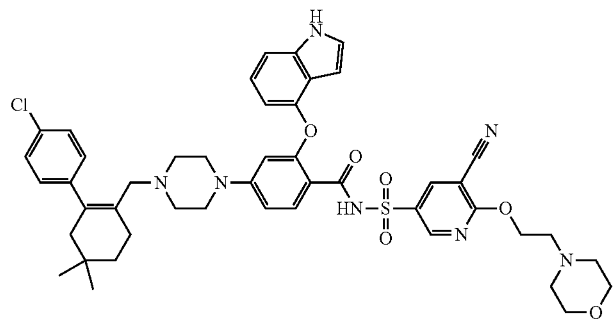 [SMILES: CC1(C)CCC(CN2CCN(c3ccc(C(=O)NS(=O)(=O)c4cnc(OCCN5CCOCC5)c(C#N)c4)c(Oc4cccc5[nH]ccc45)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-({5-cyano-6-[(4-fluorotetrahydro-2H-pyran-4-yl)methoxy]pyridin-3-yl}sulfonyl)-2-(1H-indol-4-yloxy)benzamide | 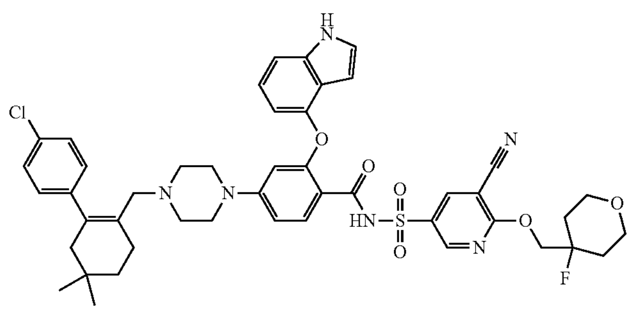 [SMILES: CC1(C)CCC(CN2CCN(c3ccc(C(=O)NS(=O)(=O)c4cnc(OCC5(F)CCOCC5)c(C#N)c4)c(Oc4cccc5[nH]ccc45)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-({4-[(3-hydroxy-4-methoxyphenyl)amino]-3-nitrophenyl}sulfonyl)-2-(1H-indol-5-yloxy)benzamide | 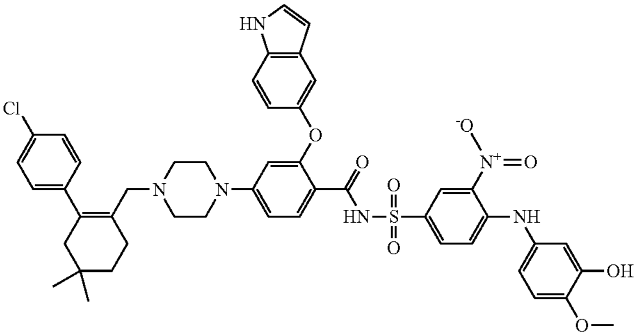 |

| Name | Structure |
|---|---|
| 4-(4-{[2-(4-chlorophenyl)-4,4-dimethylcyclohex-1-en-1-yl]methyl}piperazin-1-yl)-2-(2,3-dihydro-1H-indol-4-yloxy)-N-({4-[(1-methylpiperidin-4-yl)amino]-3-nitrophenyl}sulfonyl)benzamide | 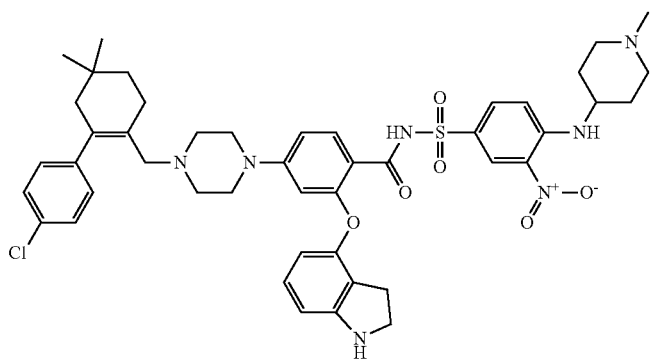 [SMILES: CN1CCC(Nc2ccc(S(=O)(=O)NC(=O)c3ccc(N4CCN(CC5=C(c6ccc(Cl)cc6)CC(C)(C)CC5)CC4)cc3Oc3cccc4c3CCN4)cc2[N+](=O)[O-])CC1] |
| 4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)-2-(pyridin-3-ylamino)benzamide | 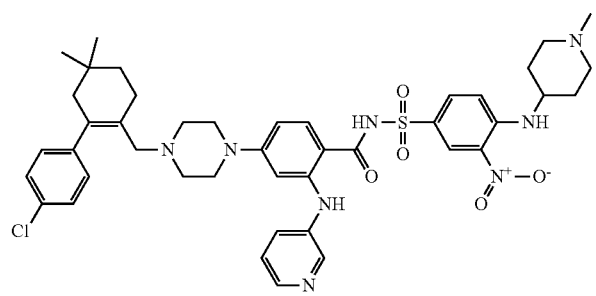 [SMILES: CN1CCC(Nc2ccc(S(=O)(=O)NC(=O)c3ccc(N4CCN(CC5=C(c6ccc(Cl)cc6)CC(C)(C)CC5)CC4)cc3Nc3cccnc3)cc2[N+](=O)[O-])CC1] |
| 4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)-2-(pyridin-3-ylamino)benzamide | 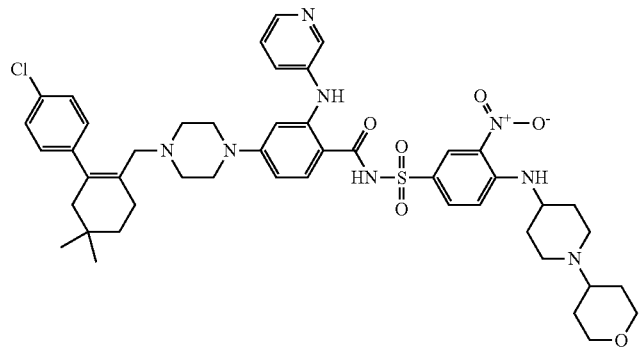 [SMILES: CC1(C)CCC(CN2CCN(c3ccc(C(=O)NS(=O)(=O)c4ccc(NC5CCN(C6CCOCC6)CC5)c([N+](=O)[O-])c4)c(Nc4cccnc4)c3)CC2)=C(c2ccc(Cl)cc2)C1] |
| 4-(4-{[2-(4-chlorophenyl)-4,4-dimetylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)-2-(pyridin-3-yloxy)benzamide | 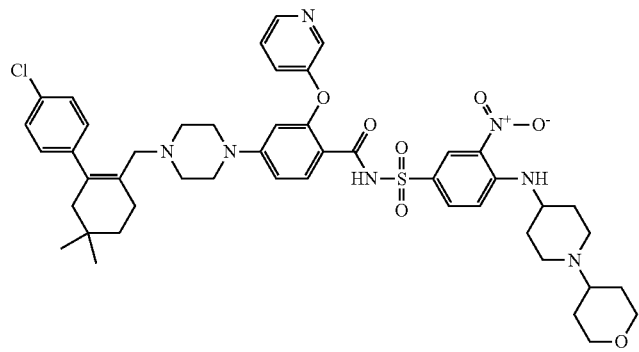 [SMILES: CC1(C)CCC(CN2CCN(c3ccc(C(=O)NS(=O)(=O)c4ccc(NC5CCN(C6CCOCC6)CC5)c([N+](=O)[O-])c4)c(Oc4cccnc4)c3)CC2)=C(c2ccc(Cl)cc2)C1] |

| Name | Structure |
|---|---|
| 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1,2,3,4-tetrahydroisoquinolin-5-yloxy)benzamide | 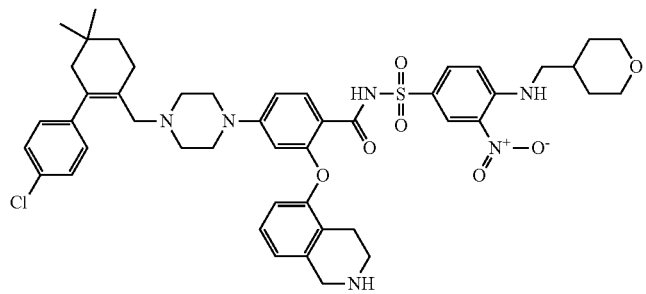 [SMILES: CC1(C)CCC(CN2CCN(c3ccc(C(=O)NS(=O)(=O)c4ccc(NCC5CCOCC5)c([N+](=O)[O-])c4)c(Oc4cccc5c4CCNC5)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-2-(1H-indazol-4-yloxy)-N-({3-nitro-4-[(tetrahydro-2H-pyran-4-ylmethyl)amino]phenyl}sulfonyl)benzamide | 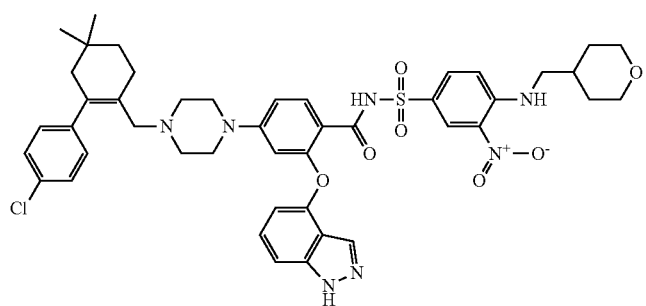 [SMILES: CC1(C)CCC(CN2CCN(c3ccc(C(=O)NS(=O)(=O)c4ccc(NCC5CCOCC5)c([N+](=O)[O-])c4)c(Oc4cccc5[nH]ncc45)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-2-(1H-indazol-4-yloxy)-N-({3-nitro-4-[(1-tetrahydro-2H-pyran-4-ylpiperidin-4-yl)amino]phenyl}sulfonyl)benzamide | 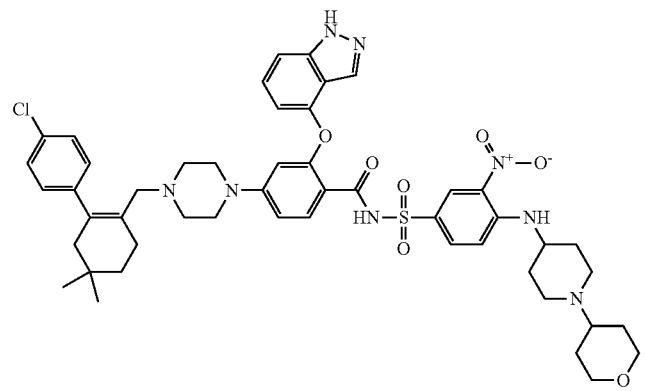 [SMILES: CC1(C)CCC(CN2CCN(c3ccc(C(=O)NS(=O)(=O)c4ccc(NC5CCN(C6CCOCC6)CC5)c([N+](=O)[O-])c4)c(Oc4cccc5[nH]ncc45)c3)CC2)=C(c2ccc(Cl)cc2)C1] |
| Trans-4-(4-{[2-(4-chlorophenyl)-4,4-dimethylcyclohex-1-en-1-yl]methyl}piperazin-1-yl)-2-(1H-indazol-4-yloxy)-N-({4-[(4-morpholin-4-ylcyclohexyl)amino]-3-nitrophenyl}sulfonyl)benzamide | 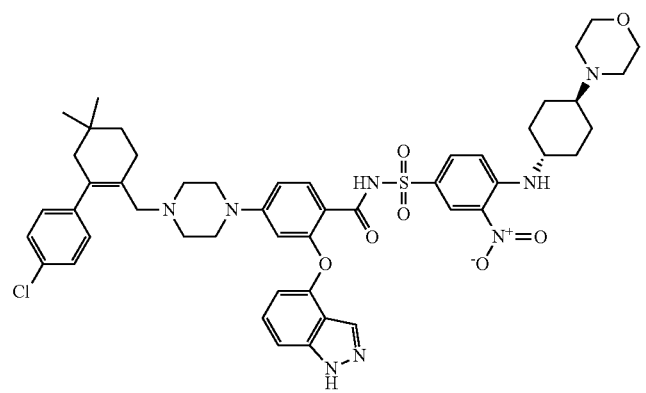 |

| Name | Structure |
|---|---|
| 2-(1H-benimidazol-4-yloxy)-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide | 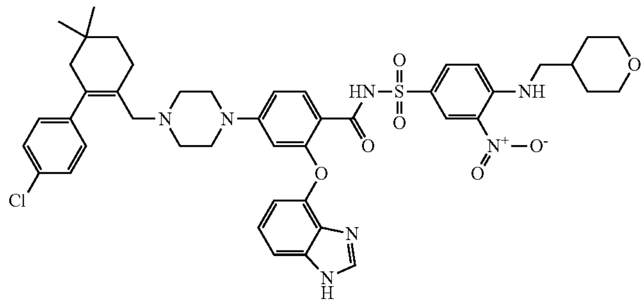 [SMILES: CC1(C)CCC(CN2CCN(c3ccc(C(=O)NS(=O)(=O)c4ccc(NCC5CCOCC5)c([N+](=O)[O-])c4)c(Oc4cccc5[nH]cnc45)c3)CC2)=C(c2ccc(Cl)cc2)C1] |
| N-({5-chloro-6-[(4-fluorotetrahydro-2H-pyran-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide | 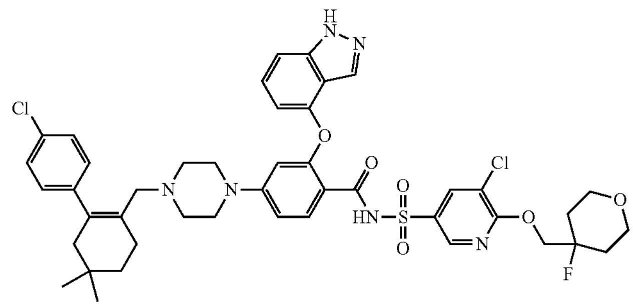 [SMILES: CC1(C)CCC(CN2CCN(c3ccc(C(=O)NS(=O)(=O)c4cnc(OCC5(F)CCOCC5)c(Cl)c4)c(Oc4cccc5[nH]ncc45)c3)CC2)=C(c2ccc(Cl)cc2)C1] |
| N-({5-chloro-6-[(4-fluorotetrahydro-2H-pyran-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indol-4-yloxy)benzamide | 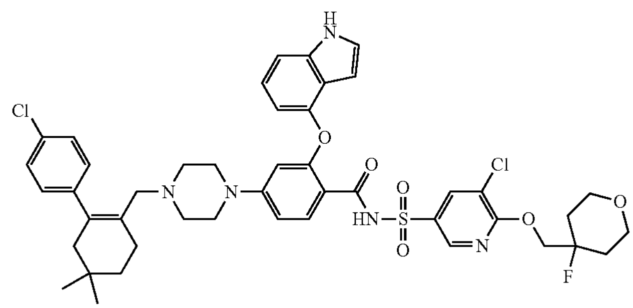 [SMILES: CC1(C)CCC(CN2CCN(c3ccc(C(=O)NS(=O)(=O)c4cnc(OCC5(F)CCOCC5)c(Cl)c4)c(Oc4cccc5[nH]ccc45)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-({5-cyano-6-[(4-fluorotetrahydro-2H-pyran-4-yl)methoxy]pyridin-3-yl}sulfonyl)-2-(1H-indazol-4-yloxy)benzamide | 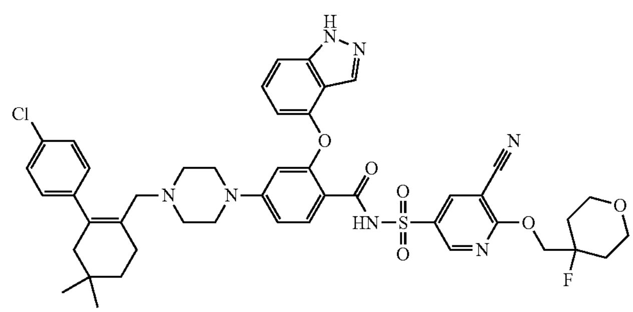 |
| 2-(1H-benzimidazol-4-yloxy)-4-(4-{[2-(4-chlorophenyl)-4,4-dimethylcyclohex-1-en-1-yl]methyl}piperazin-1-yl)-N-[(4-{[(3R)-1-(2,2-difluoroethyl)pyrrolidin-3-yl]amino}-3-nitrophenyl)sulfonyl]benzamide | 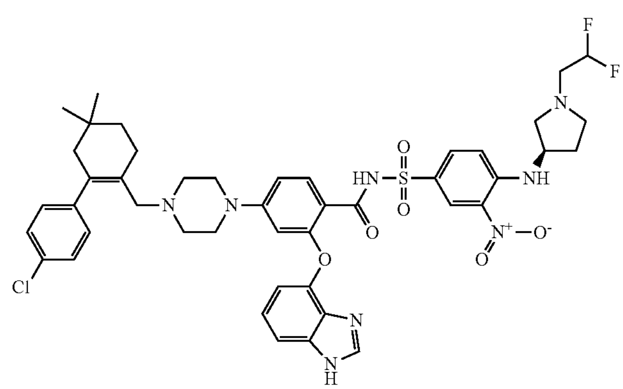 [SMILES: CC1(C)CCC(CN2CCN(c3ccc(C(=O)NS(=O)(=O)c4ccc(N[C@@H]5CCN(CC(F)F)C5)c([N+](=O)[O-])c4)c(Oc4cccc5[nH]cnc45)c3)CC2)=C(c2ccc(Cl)cc2)C1] |

-continued

| Name | Structure |
|---|---|
| 2-(1H-benzimidazol-4-yloxy)-4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-nitrophenyl}sulfonyl)benzamide | 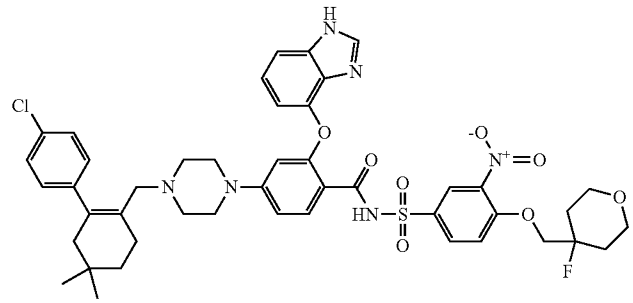 |
| 4-(4-{[2-(4-chlorophenyl)-4,4-dimethylcyclohex-1-en-1-yl]methyl}piperazin-1-yl)-N-[(4-{[(4-fluorotetrahydro-2H-pyran-4-yl)methyl]amino}-3-nitrophenyl)sulfonyl]-2-(1H-indazol-4-yloxy)benzamide | 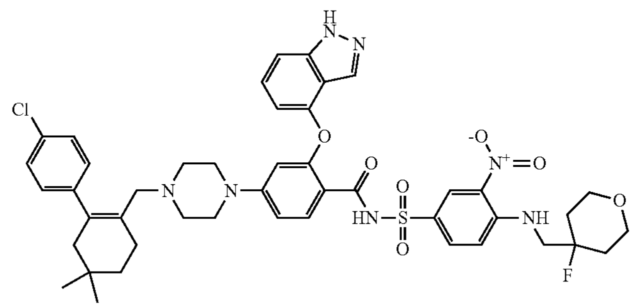 |
| 4-(4-{[2-(4-chlorophenyl)-4,4-dimethylcyclohex-1-en-1-yl]methyl}piperazin-1-yl)-N-{[6-[(4-fluorotetrahydro-2H-pyran-4-yl)methoxy]-5-(trifluoromethyl)pyridin-3-yl]sulfonyl}-2-(1H-indazol-4-yloxy)benzamide | 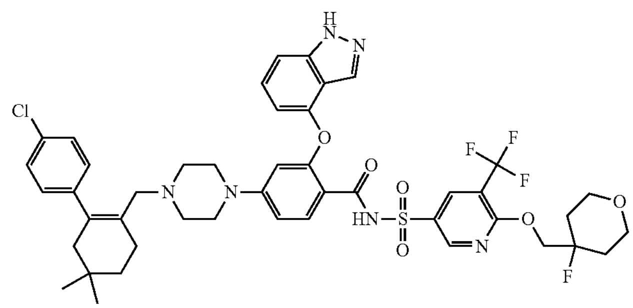 [SMILES: CC1(C)CCC(CN2CCN(c3ccc(C(=O)NS(=O)(=O)c4cnc(OCC5(F)CCOCC5)c(C(F)(F)F)c4)c(Oc4cccc5[nH]ncc45)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-[(4-{[(4-cyclopropylmorpholin-2-yl)methyl]amino}-3-nitrophenyl)sulfonyl]-2-(1H-indazol-4-yloxy)benzamide | 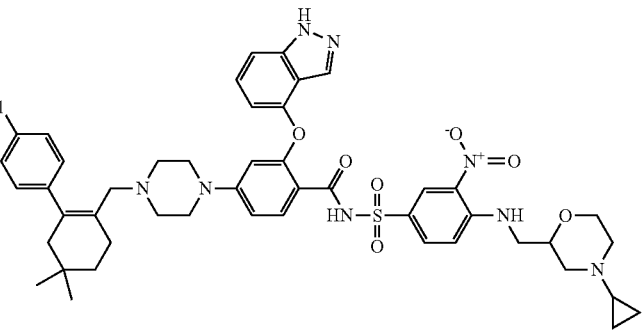 |
| 4-(4-{[2-(4-chlorophenyl)-4,4-dimethylcyclohex-1-en-1-yl]methyl}piperazin-1-yl)-N-[(4-{[(4,4-difluorocyclohexyl)methyl]amino}-3-nitrophenyl)sulfonyl]-2-(1H-indazol-4-yloxy)benzamide | 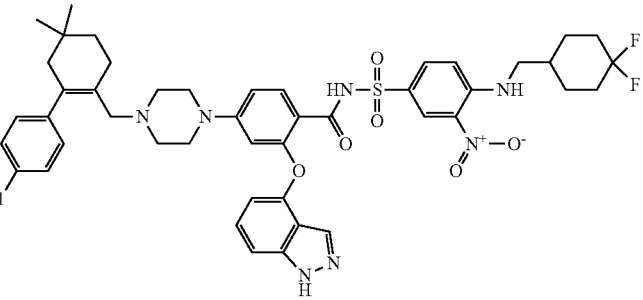 |

| Name | Structure |
|---|---|
| N-[(5-chloro-6-{[(4-fluorotetrahydro-2H-pyran-4-yl)methyl]amino}pyridin-3-yl)sulfonyl]-4-(4-{[2-(4-chlorophenyl)-4,4-dimethylcyclohex-1-en-1-yl]methyl}piperazin-1-yl)-2-(1H-indazol-4-yloxy)benzamide | 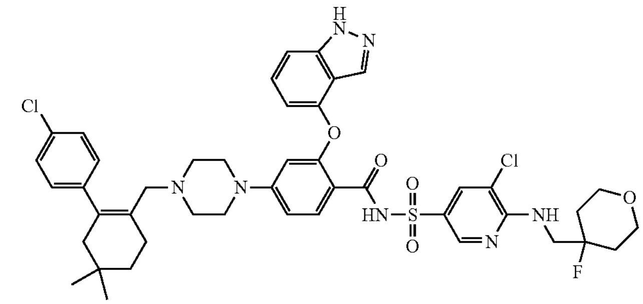 |
| Trans-N-({5-chloro-6-[(4-methoxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide | 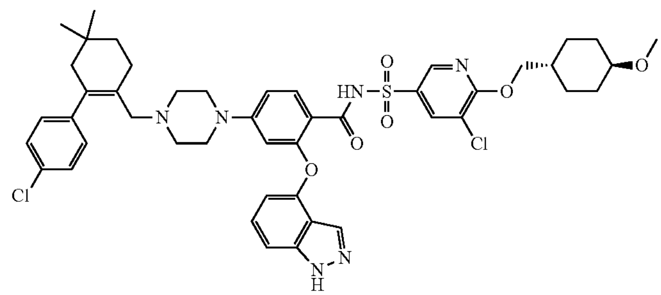 [SMILES: CO[C@H]1CC[C@H](COc2ncc(S(=O)(=O)NC(=O)c3ccc(N4CCN(CC5=C(c6ccc(Cl)cc6)CC(C)(C)CC5)CC4)cc3Oc3cccc4[nH]ncc34)cc2Cl)CC1] |
| 2-(1H-benzimidazol-4-yloxy)-4-(4-{[2-(4-chlorophenyl)-4,4-dimethylcyclohex-1-en-1-yl]methyl}piperazin-1-yl)-N-{[4-({[4-(2,2-difluoroethyl)morpholin-2-yl]methyl}amino)-3-nitrophenyl]sulfonyl}benzamide | 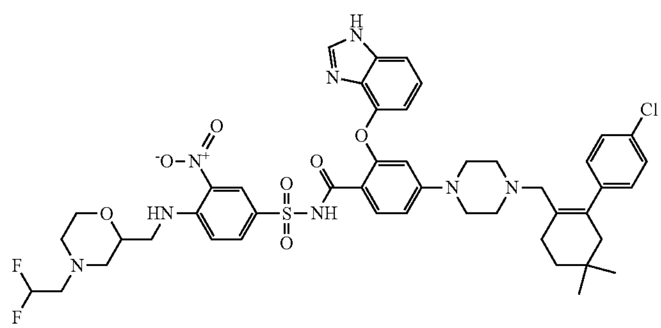 |
| 4-(4-{[2-(4-chlorophenyl)-4,4-dimethylcyclohex-1-en-1-yl]methyl}piperazin-1-yl)-N-({5-fluoro-6-[(4-fluorotetrahydro-2H-pyran-4-yl)methoxy]pyridin-3-yl}sulfonyl)-2-(1H-indazol-4-yloxy)benzamide | 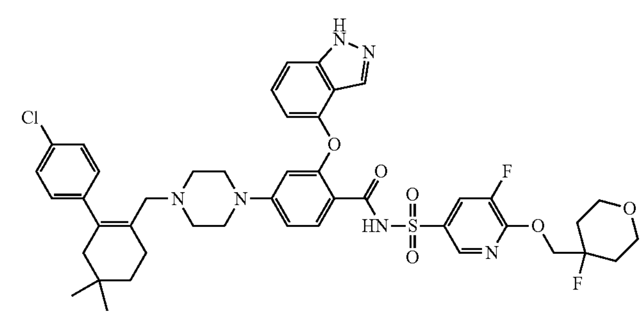 [SMILES: CC1(C)CCC(CN2CCN(c3ccc(C(=O)NS(=O)(=O)c4cnc(OCC5(F)CCOCC5)c(F)c4)c(Oc4cccc5[nH]ncc45)c3)CC2)=C(c2ccc(Cl)cc2)C1] |

-continued

| Name | Structure |
|---|---|
| 2-(1H-benzimidazol-4-yloxy)-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide | 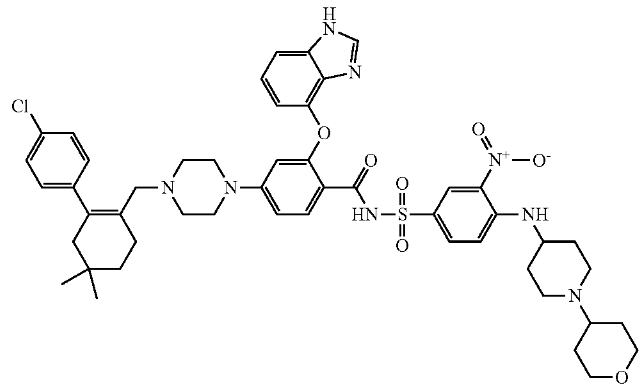 [SMILES: CC1(C)CCC(CN2CCN(c3ccc(C(=O)NS(=O)(=O)c4ccc(NC5CCN(C6CCOCC6)CC5)c([N+](=O)[O-])c4)c(Oc4cccc5[nH]cnc45)c3)CC2)=C(c2ccc(Cl)cc2)C1] |
| 2-(1H-benzimidazol-4-yloxy)-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide | 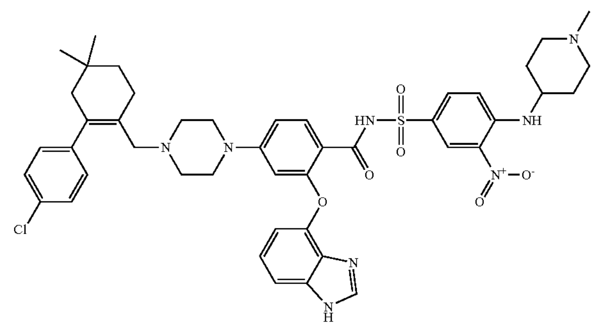 |
| N-[(5-chloro-6-{[1-(cyanomethyl)-4-fluoropiperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-indazol-4-yloxy)benzamide | 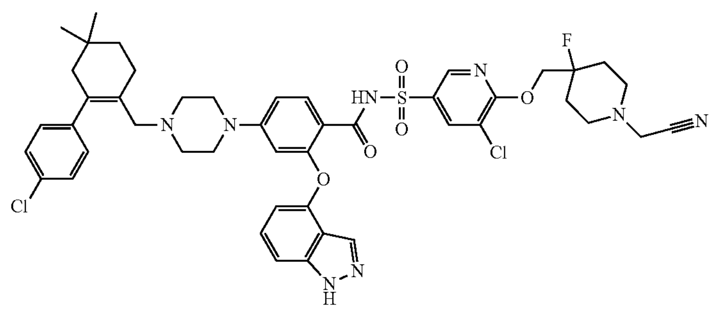 [SMILES: CC1(C)CCC(CN2CCN(c3ccc(C(=O)NS(=O)(=O)c4cnc(OCC5(F)CCN(CC#N)CC5)c(Cl)c4)c(Oc4cccc5[nH]ncc45)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-{[5-chloro-6-(tetrahydrofuran-3-ylmethoxy)pyridin-3-yl]sulfonyl}-2-(1H-indazol-4-yloxy)benzamide | 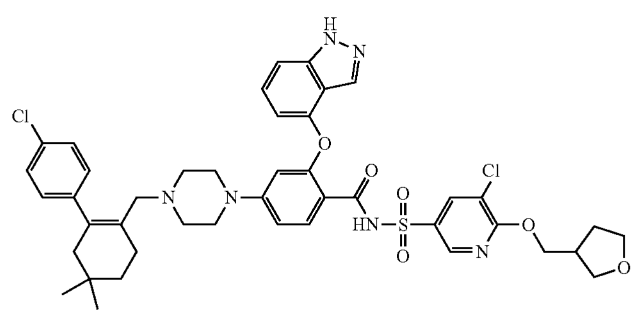 [SMILES: CC1(C)CCC(CN2CCN(c3ccc(C(=O)NS(=O)(=O)c4cnc(OCC5CCOC5)c(Cl)c4)c(Oc4cccc5[nH]ncc45)c3)CC2)=C(c2ccc(Cl)cc2)C1] |

| Name | Structure |
|---|---|
| Trans-N-({5-chloro-6-[(4-hydroxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide | 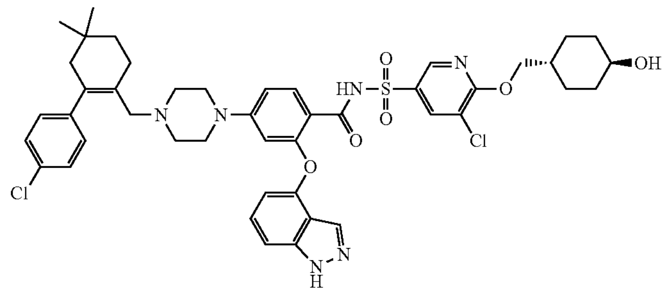 [SMILES: CC1(C)CCC(CN2CCN(c3ccc(C(=O)NS(=O)(=O)c4cnc(OC[C@H]5CC[C@H](O)CC5)c(Cl)c4)c(Oc4cccc5[nH]ncc45)c3)CC2)=C(c2ccc(Cl)cc2)C1] |
| N-[(5-chloro-6-{[(3R)-1-(2,2-difluoroethyl)pyrrolidin-3-yl]oxy}pyridin-3-yl)sulfonyl]-4-(4-{[2-(4-chlorophenyl)-4,4-dimethylcyclohex-1-en-1-yl]methyl}piperazin-1-yl)-2-(1H-indazol-4-yloxy)benzamide | 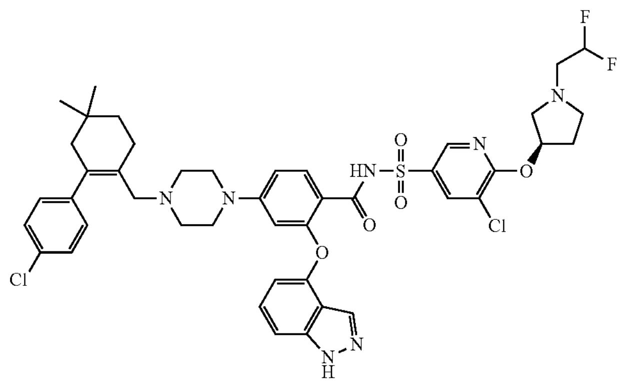 [SMILES: CC1(C)CCC(CN2CCN(c3ccc(C(=O)NS(=O)(=O)c4cnc(O[C@@H]5CCN(CC(F)F)C5)c(Cl)c4)c(Oc4cccc5[nH]ncc45)c3)CC2)=C(c2ccc(Cl)cc2)C1] |
| 2-(1H-benzimidazol-4-yloxy)-N-[(5-chloro-6-{[(2S)-4-(N,N-dimethylglycyl)morpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)benzamide | 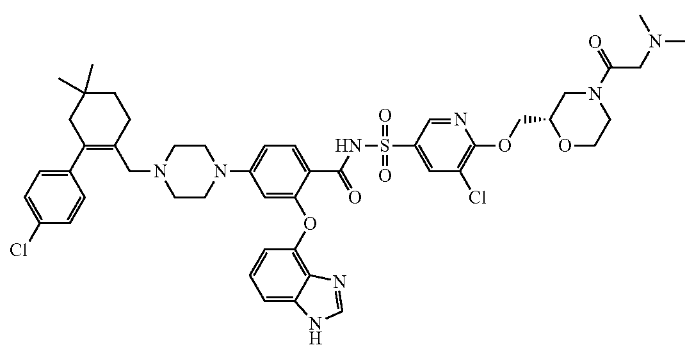 [SMILES: CN(C)CC(=O)N1CCO[C@H](COc2ncc(S(=O)(=O)NC(=O)c3ccc(N4CCN(CC5=C(c6ccc(Cl)cc6)CC(C)(C)CC5)CC4)cc3Oc3cccc4[nH]cnc34)cc2Cl)C1] |
| 2-(1H-benzimidazol-4-yloxy)-N-[(5-chloro-6-{[(2R)-4-(N,N-dimethylglycyl)morpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)benzamide | 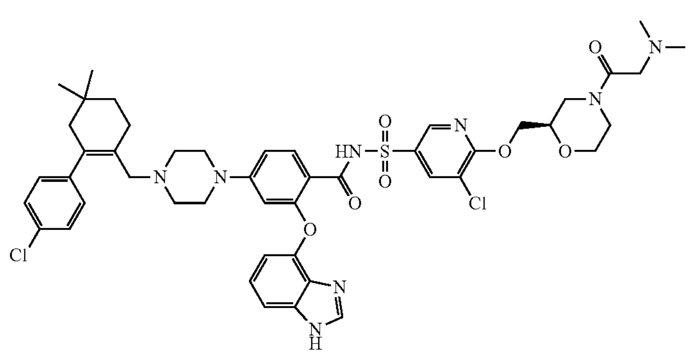 [SMILES: CN(C)CC(=O)N1CCO[C@@H](COc2ncc(S(=O)(=O)NC(=O)c3ccc(N4CCN(CC5=C(c6ccc(Cl)cc6)CC(C)(C)CC5)CC4)cc3Oc3cccc4[nH]cnc34)cc2Cl)C1] |

-continued

| Name | Structure |
|---|---|
| N-[(5-chloro-6-{[(2S)-4-(N,N-dimethylglycyl)morpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-indazol-4-yloxy)benzamide | 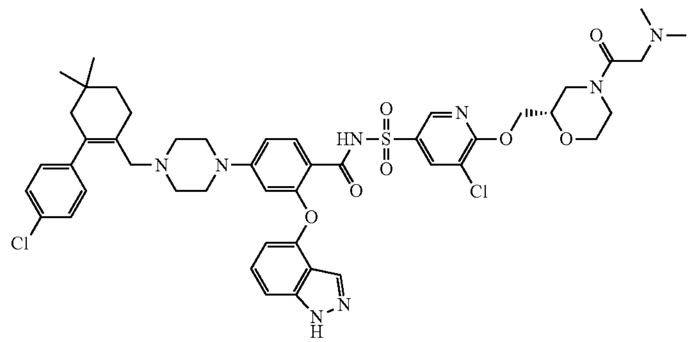 [SMILES: CN(C)CC(=O)N1CCO[C@H](COc2ncc(S(=O)(=O)NC(=O)c3ccc(N4CCN(CC5=C(c6ccc(Cl)cc6)CC(C)(C)CC5)CC4)cc3Oc3cccc4[nH]ncc34)cc2Cl)C1] |
| N-[(5-chloro-6-{[(2R)-4-(N,N-dimethylglycyl)morpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-indazol-4-yloxy)benzamide | 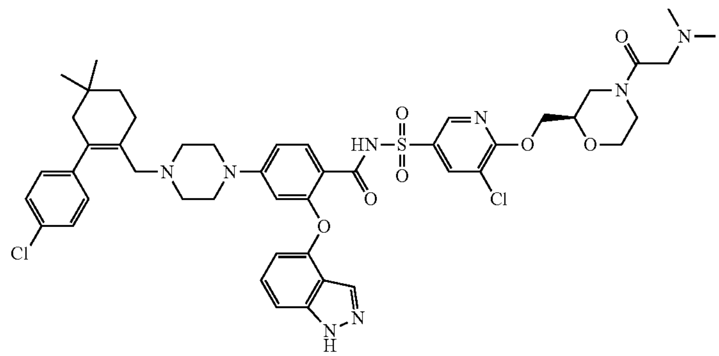 [SMILES: CN(C)CC(=O)N1CCO[C@@H](COc2ncc(S(=O)(=O)NC(=O)c3ccc(N4CCN(CC5=C(c6ccc(Cl)cc6)CC(C)(C)CC5)CC4)cc3Oc3cccc4[nH]ncc34)cc2Cl)C1] |
| 4-(4-{[2-(4-chlorophenyl)-4,4-dimethylcyclohex-1-en-1-yl]methyl}piperazin-1-yl)-N-{[5-chloro-6-(tetrahydro-2H-pyran-4-ylmethoxy)pyridin-3-yl]sulfonyl}-2-(1H-indazol-4-yloxy)benzamide | 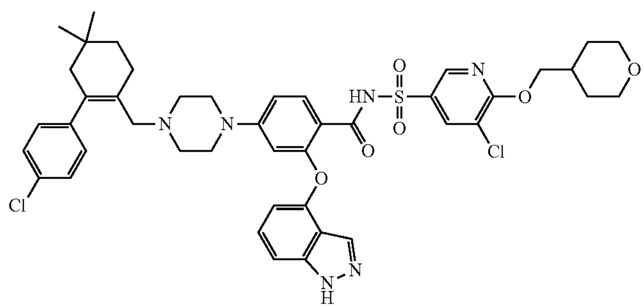 |
| 2-(1H-benzimidazol-4-yloxy)-4-(4-{[2-(4-chlorophenyl)-4,4-dimethylcyclohex-1-en-1-yl]methyl}piperazin-1-yl)-N-[(4-{[(3R)-1-(cyanomethyl)pyrrolidin-3-yl]aminio}-3-nitrophenyl)sulfonyl]benzamide | 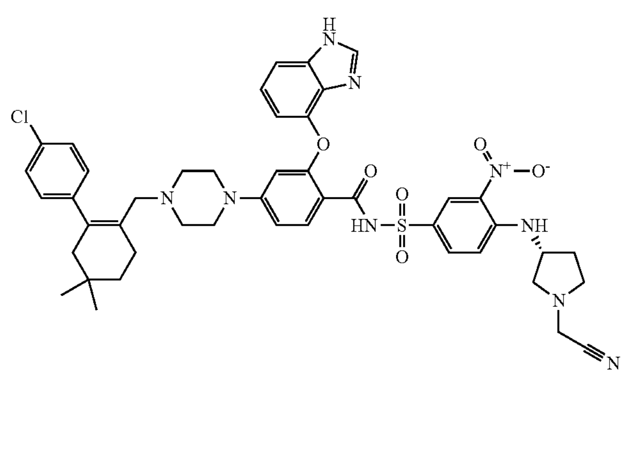 [SMILES: CC1(C)CCC(CN2CCN(c3ccc(C(=O)NS(=O)(=O)c4ccc(N[C@@H]5CCN(CC#N)C5)c([N+](=O)[O-])c4)c(Oc4cccc5[nH]cnc45)c3)CC2)=C(c2ccc(Cl)cc2)C1] |

-continued

| Name | Structure |
|---|---|
| 2-(1H-benzimidazol-4-yloxy)-4-(4-{[2-(4-chlorophenyl)-4,4-dimethylcyclohex-1-en-1-yl]methyl}piperazin-1-yl)-N-{[4-({(3R)-1-[2-(2-methoxyethoxy)ethyl]pyrrolidin-3-yl}amino)-3-nitrophenyl]sulfonyl}benzamide | 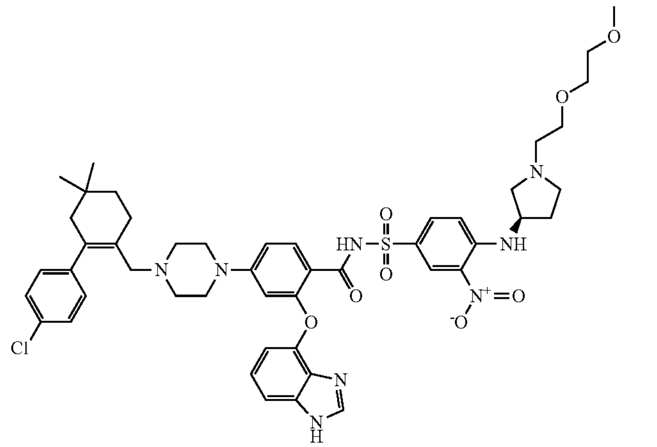 |
| 2-(1H-benzimidazol-4-yloxy)-4-(4-{[2-(4-chlorophenyl)-4,4-dimethylcyclohex-1-en-1-yl]methyl}piperazin-1-yl)-N-[(4-{[(3R)-1-(N,N-dimethylglycyl)pyrrolidin-3-yl]amino}-3-nitrophenyl)sulfonyl]benzamide | 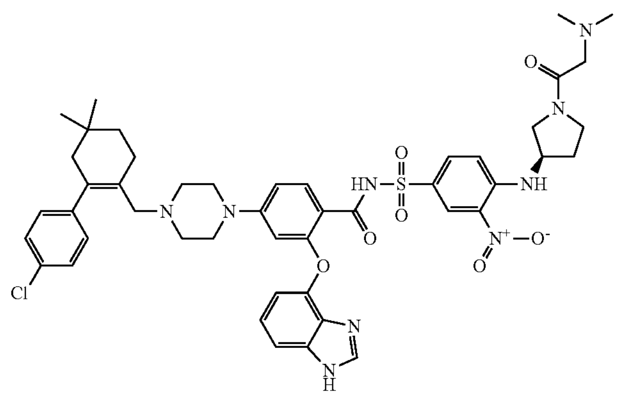 [SMILES: CN(C)CC(=O)N1CC[C@@H](Nc2ccc(S(=O)(=O)NC(=O)c3ccc(N4CCN(CC5=C(c6ccc(Cl)cc6)CC(C)(C)CC5)CC4)cc3Oc3cccc4[nH]cnc34)cc2[N+](=O)[O-])C1] |
| 2-(1H-benzimidazol-4-yloxy)-4-(4-{[2-(4-chlorophenyl)-4,4-dimethylcyclohex-1-en-1-yl]methyl}piperazin-1-yl)-N-{[4-({[4-(cyanomethyl)morpholin-2-yl]methyl}amino)-3-nitrophenyl]sulfonyl}benzamide | 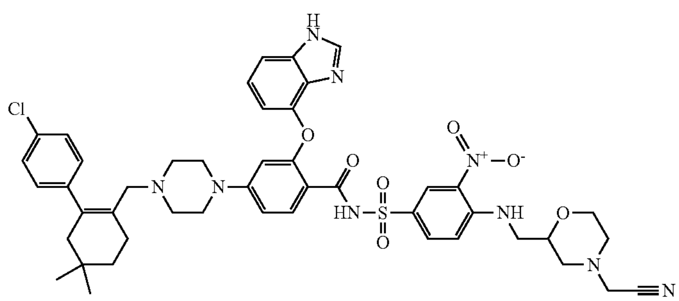 [SMILES: CC1(C)CCC(CN2CCN(c3ccc(C(=O)NS(=O)(=O)c4ccc(NCC5CN(CC#N)CCO5)c([N+](=O)[O-])c4)c(Oc4cccc5[nH]cnc45)c3)CC2)=C(c2ccc(Cl)cc2)C1] |
| 2-(1H-benzimidazol-4-yloxy)-4-(4-{[2-(4-chlorophenyl)-4,4-dimethylcyclohex-1-en-1-yl]methyl}piperazin-1-yl)-N-[(4-{[(4-cyclopropylmorpholin-2-yl)methyl]amino}-3-nitrophenyl)sulfonyl]benzamide | 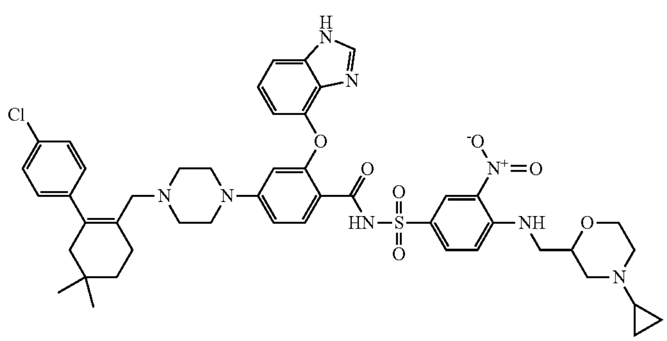 |

| Name | Structure |
|---|---|
| 2-(1H-benzimidazol-4-yloxy)-4-(4-{[2-(4-chlorophenyl)-4,4-dimethylcyclohex-1-en-1-yl]methyl}piperazin-1-yl)-N-[(3-nitro-4-{[(4-oxetan-3-ylmorpholin-2-yl)methyl]amino}phenyl)sulfonyl]benzamide | 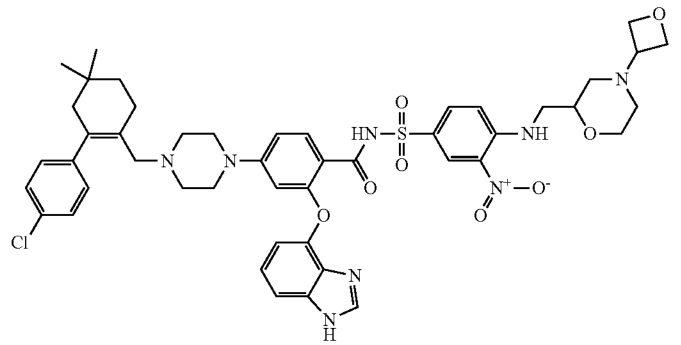 [SMILES: CC1(C)CCC(CN2CCN(c3ccc(C(=O)NS(=O)(=O)c4ccc(NCC5CN(C6COC6)CCO5)c([N+](=O)[O-])c4)c(Oc4cccc5[nH]cnc45)c3)CC2)=C(c2ccc(Cl)cc2)C1] |
| N-{[5-chloro-6-(((3R)-1-[2-fluoro-1-(fluoromethyl)ethyl]pyrrolidin-3-yl)oxy)pyridin-3-yl]sulfonyl}-4-(4-{[2-(4-chlorophenyl)-4,4-dimetylcyclohex-1-en-1-yl]methyl}piperazin-1-yl)-2-(1H-indazol-4-yloxy)benzamide | 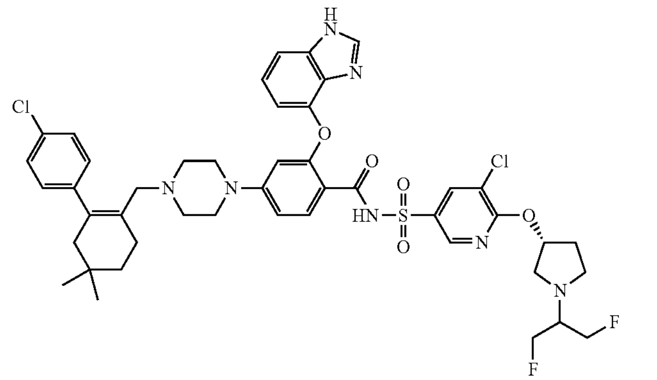 [SMILES: CC1(C)CCC(CN2CCN(c3ccc(C(=O)NS(=O)(=O)c4cnc(O[C@@H]5CCN(C(CF)CF)C5)c(Cl)c4)c(Oc4cccc5[nH]cnc45)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-{[4-(((3R)-1-[2-fluoro-1-(fluoromethyl)ethyl]pyrrolidin-3-yl)amino)-3-nitrophenyl]sulfonyl}-2-(1H-indazol-4-yloxy)benzamide | 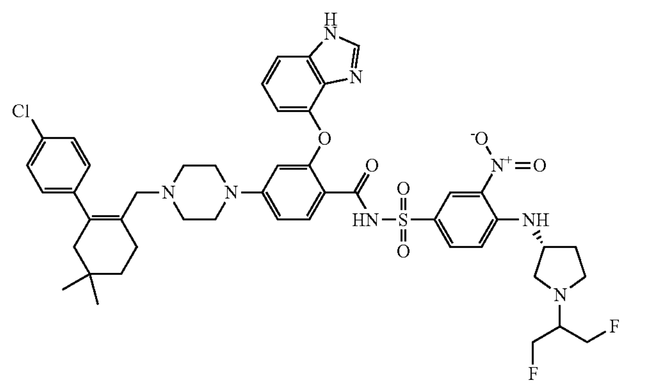 |
| 4-(4-{[2-(4-chlorophenyl)-4,4-dimethylcyclohex-1-en-1-yl]methyl}piperazin-1-yl)-N-({4-[(1-cyclopropylpiperidin-4-yl)amino]-3-nitrophenyl}sulfonyl)-2-(1H-indazol-4-yloxy)benzamide | 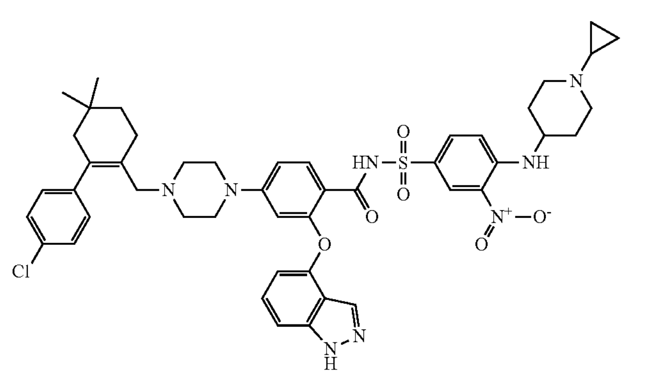 [SMILES: CC1(C)CCC(CN2CCN(c3ccc(C(=O)NS(=O)(=O)c4ccc(NC5CCN(C6CC6)CC5)c([N+](=O)[O-])c4)c(Oc4cccc5[nH]ncc45)c3)CC2)=C(c2ccc(Cl)cc2)C1] |

| Name | Structure |
|---|---|
| 2-(1H-benzimidazol-4-yloxy)-4-(4-{[2-(4-chlorophenyl)-4,4-dimethylcyclohex-1-en-1-yl]methyl}piperazin-1-yl)-N-{[4-({[(2R)-4-(N,N-dimethylglycyl)morpholin-2-yl]methyl}amino)-3-nitrophenyl]sulfonyl}benzamide | 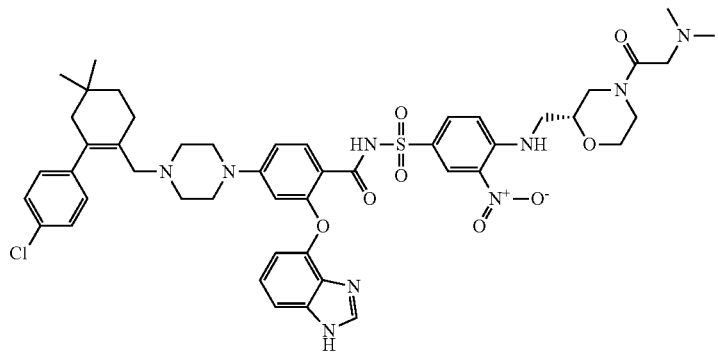 [SMILES: CN(C)CC(=O)N1CCO[C@H](CNc2ccc(S(=O)(=O)NC(=O)c3ccc(N4CCN(CC5=C(c6ccc(Cl)cc6)CC(C)(C)CC5)CC4)cc3Oc3cccc4[nH]cnc34)cc2[N+](=O)[O-])C1] |
| 2-(1H-benzimidazol-4-yloxy)-4-(4-{[2-(4-chlorophenyl)-4,4-dimethylcyclohex-1-en-1-yl]methyl}piperazin-1-yl)-N-{[4-({[(2S)-4-(N,N-dimethylglycyl)morpholin-2-yl]methyl}amino)-3-nitrophenyl]sulfonyl}benzamide | 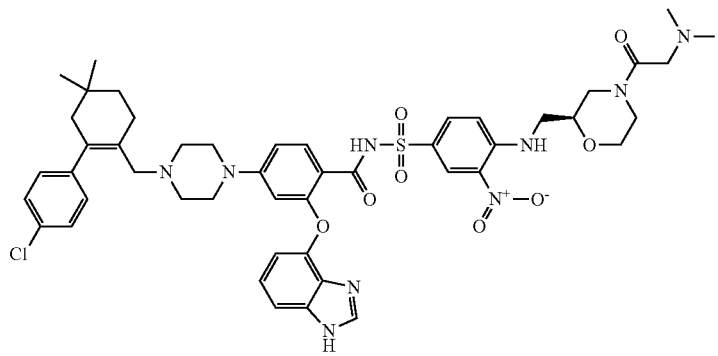 [SMILES: CN(C)CC(=O)N1CCO[C@@H](CNc2ccc(S(=O)(=O)NC(=O)c3ccc(N4CCN(CC5=C(c6ccc(Cl)cc6)CC(C)(C)CC5)CC4)cc3Oc3cccc4[nH]cnc34)cc2[N+](=O)[O-])C1] |
| 2-(1H-benzimidazol-4-yloxy)-4-(4-{[2-(4-chlorophenyl)-4,4-dimethylcyclohex-1-en-1-yl]methyl}piperazin-1-yl)-N-({3-nitro-4-[(tetrahydrofuran-3-ylmethyl)amino]phenyl}sulfonyl)benzamide | 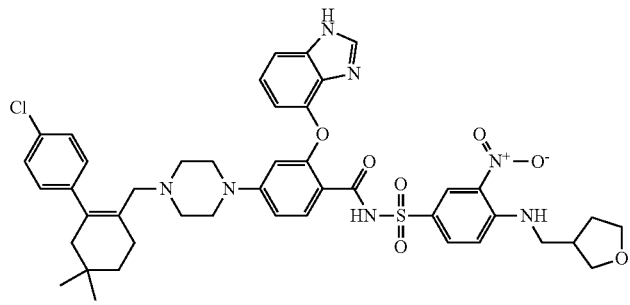 [SMILES: CC1(C)CCC(CN2CCN(c3ccc(C(=O)NS(=O)(=O)c4ccc(NCC5CCOC5)c([N+](=O)[O-])c4)c(Oc4cccc5[nH]cnc45)c3)CC2)=C(c2ccc(Cl)cc2)C1] |
| Trans-2-(1H-benzimidazol-4-yloxy)-4-(4-{[2-(4-chlorophenyl)-4,4-dimethylcyclohex-1-en-1-yl]methyl}piperazin-1-yl)-N-[(4-{[(4-methoxycyclohexyl)methyl]amino}-3-nitrophenyl)sulfonyl]benzamide | 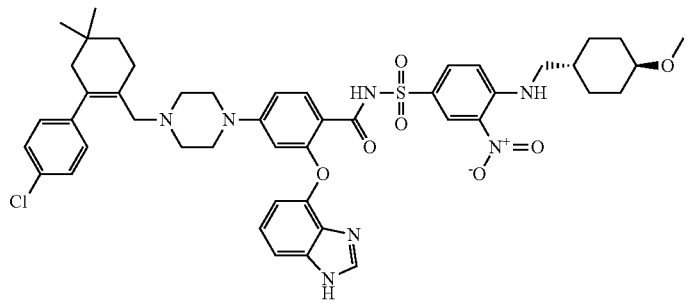 |

| Name | Structure |
|---|---|
| 2-(1H-benzimidazol-4-yloxy)-4-(4-{[2-(4-chlorophenyl)-4,4-dimethylcyclohex-1-en-1-yl]methyl}piperazin-1-yl)-N-[(4-{[(4-fluorotetrahydro-2H-pyran-4-yl)methyl]amino}-3-nitrophenyl)sulfonyl]benzamide | 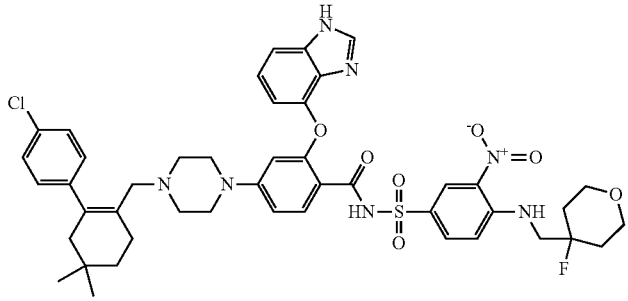 |
| 2-(1H-benzimidazol-4-yloxy)-4-(4-{[2-(4-chlorophenyl)-4,4-dimethylcyclohex-1-en-1-yl]methyl}piperazin-1-yl)-N-({5-fluoro-6-[(4-fluorotetrahydro-2H-pyran-4-yl)methoxy]pyridin-3-yl}sulfonyl)benzamide | 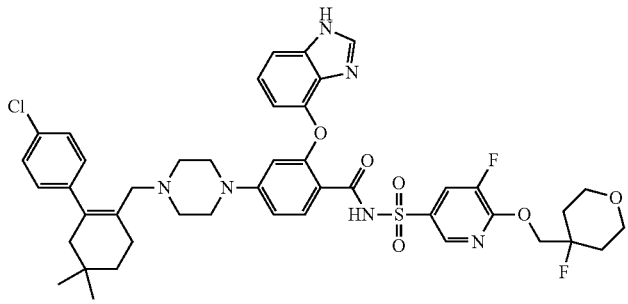 [SMILES: CC1(C)CCC(CN2CCN(c3ccc(C(=O)NS(=O)(=O)c4cnc(OCC5(F)CCOCC5)c(Cl)c4)c(Oc4cccc5[nH]cnc45)c3)CC2)=C(c2ccc(Cl)cc2)C1] |
| 2-(1H-benzimidazol-4-yloxy)-N-({5-chloro-6-[(4-fluorotetrahydro-2H-pyran-4-yl)methoxy]pyridin-3-yl}sulfonyl)-4-(4-{[2-(4-chlorophenyl)-4,4-dimethylcyclohex-1-en-1-yl]methyl}piperazin-1-yl)benzamide | 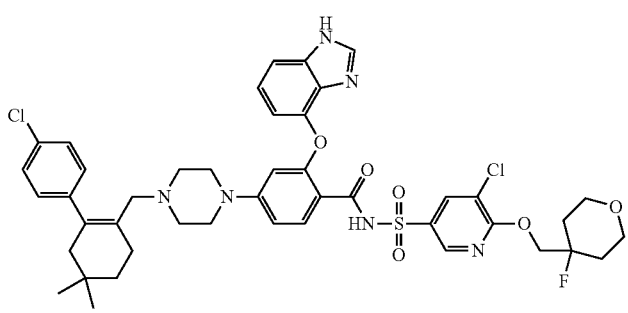 |
| N-{[5-chloro-6-(((3R)-1-[2-fluoro-1-(fluoromethyl)ethyl]pyrrolidin-3-yl)methoxy)pyridin-3-yl]sulfonyl}-4-(4-{[2-(4-chlorophneyl)-4,4-dimethylcyclohex-1-en-1-yl]methyl}piperazin-1-yl)-2-(1H-indazol-4-yloxy)benzamide | 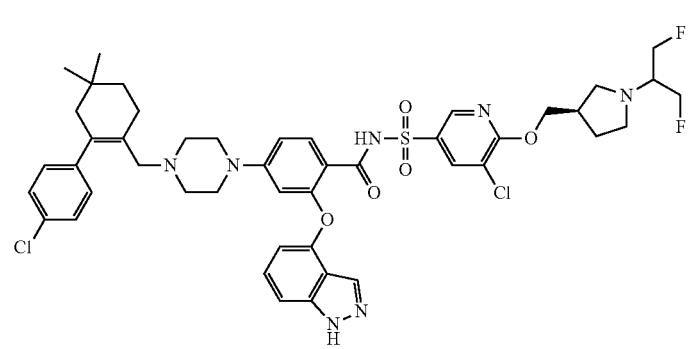 [SMILES: CC1(C)CCC(CN2CCN(c3ccc(C(=O)NS(=O)(=O)c4cnc(OC[C@@H]5CCN(C(CF)CF)C5)c(Cl)c4)c(Oc4cccc5[nH]ncc45)c3)CC2)=C(c2ccc(Cl)cc2)C1] |
| N-[(5-chloro-6-{[(3R)-1-(2,2-difluoroethyl)pyrrolidin-3-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-indazol-4-yloxy)benzamide | 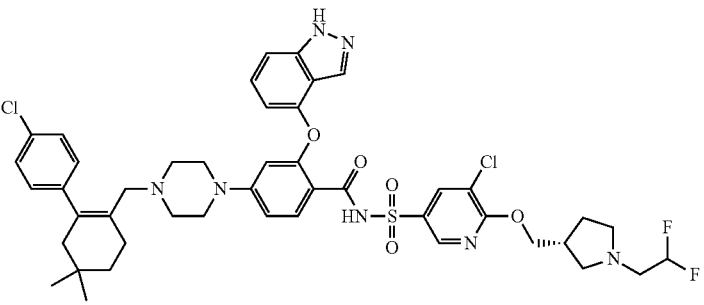 [SMILES: CC1(C)CCC(CN2CCN(c3ccc(C(=O)NS(=O)(=O)c4cnc(OC[C@@H]5CCN(CC(F)F)C5)c(Cl)c4)c(Oc4cccc5[nH]ncc45)c3)CC2)=C(c2ccc(Cl)cc2)C1] |

-continued

| Name | Structure |
|---|---|
| Trans-4-(4-{[2-(4-chlorophenyl)-4,4-dimethylcyclohex-1-en-1-yl]methyl}piperazin-1-yl)-2-(1H-indazol-4-yloxy)-N-[(4-{[(4-methoxycyclohexyl)methyl]amino}-3-nitrophenyl)sulfonyl]benzamide | 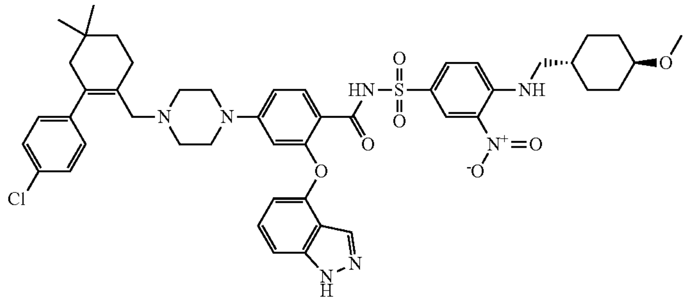 |
| 4-(4-{[2-(4-chlorophenyl)-4,4-dimethylcyclohex-1-en-1-yl]methyl}piperazin-1-yl)-N-{[4-(1,4-dioxan-2-ylmethoxy)-3-nitrophenyl]sulfonyl}-2-(1H-indazol-4-yloxy)benzamide | 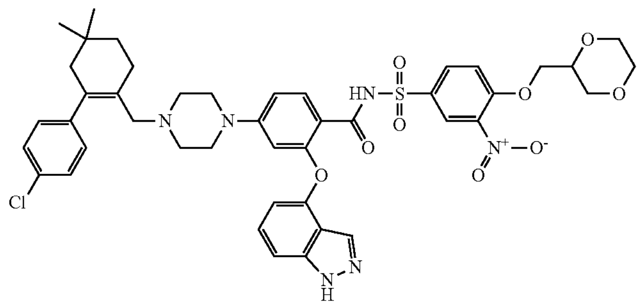 [SMILES: CC1(C)CCC(CN2CCN(c3ccc(C(=O)NS(=O)(=O)c4ccc(OCC5COCCO5)c([N+](=O)[O-])c4)c(Oc4cccc5[nH]ncc45)c3)CC2)=C(c2ccc(Cl)cc2)C1] |
| N-({5-chloro-6-[(1-cyclopropylpiperidin-4-yl)amino]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide | 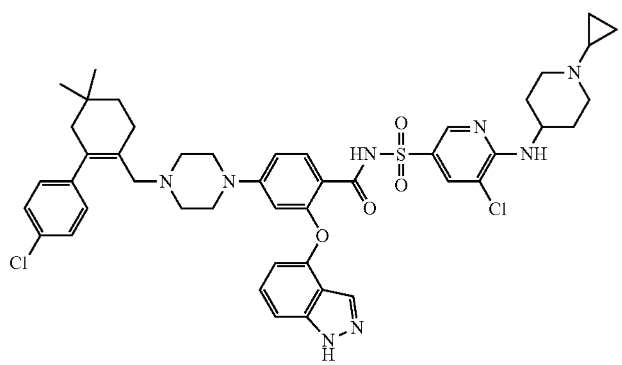 [SMILES: CC1(C)CCC(CN2CCN(c3ccc(C(=O)NS(=O)(=O)c4cnc(NC5CCN(C6CC6)CC5)c(Cl)c4)c(Oc4cccc5[nH]ncc45)c3)CC2)=C(c2ccc(Cl)cc2)C1] |
| 2-(1H-benzimidazol-4-yloxy)-N-({5-chloro-6-[(1-cyclopropylpiperidin-4-yl)amino]pyridin-3-yl}sulfonyl)-4-(4-{[2-(4-chlorophenyl)-4,4-dimethylcyclohex-1-en-1-yl]methyl}piperazin-1-yl)benzamide | 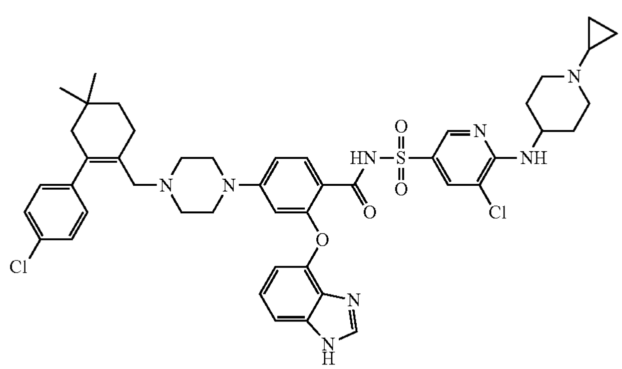 [SMILES: CC1(C)CCC(CN2CCN(c3ccc(C(=O)NS(=O)(=O)c4cnc(NC5CCN(C6CC6)CC5)c(Cl)c4)c(Oc4cccc5[nH]cnc45)c3)CC2)=C(c2ccc(Cl)cc2)C1] |

| Name | Structure |
|---|---|
| 2-(1H-benzimidazol-4-yloxy)-4-(4-{[2-(4-chlorophenyl)-4,4-dimethylcyclohex-1-en-1-yl]methyl}piperazin-1-yl)-N-({4-[(1,4-dioxan-2-ylmethyl)amino]-3-nitrophenyl}sulfonyl)benzamide | 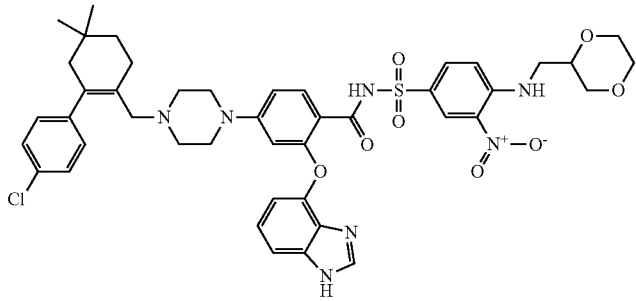 [SMILES: CC1(C)CCC(CN2CCN(c3ccc(C(=O)NS(=O)(=O)c4ccc(NCC5COCCO5)c([N+](=O)[O-])c4)c(Oc4cccc5[nH]cnc45)c3)CC2)=C(c2ccc(Cl)cc2)C1] |
| 2-(1H-benzimidazol-4-yloxy)-4-(4-{[2-(4-chlorophenyl)-4,4-dimethylcyclohex-1-en-1-yl]methyl}piperazin-1-yl)-N-({4-[(1-cyclopropylpiperidin-4-yl)amino]-3-nitrophenyl}sulfonyl)benzamide | 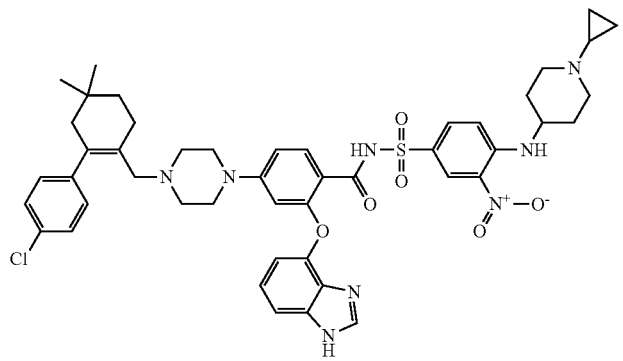 [SMILES: CC1(C)CCC(CN2CCN(c3ccc(C(=O)NS(=O)(=O)c4ccc(NC5CCN(C6CC6)CC5)c([N+](=O)[O-])c4)c(Oc4cccc5[nH]cnc45)c3)CC2)=C(c2ccc(Cl)cc2)C1] |
| Trans-2-(1H-benzimidazol-4-yloxy)-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)benzamide | 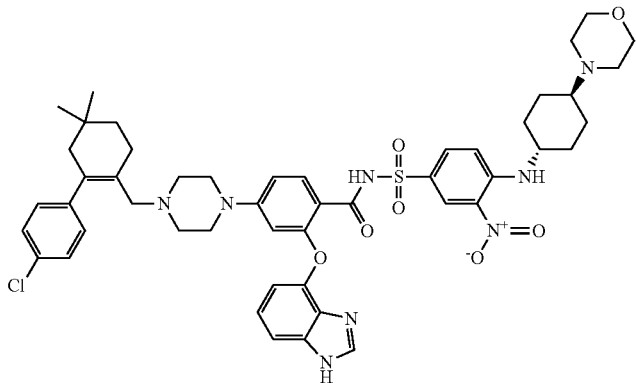 |
| 2-(1H-benzimidazol-4-yloxy)-4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)benzamide | 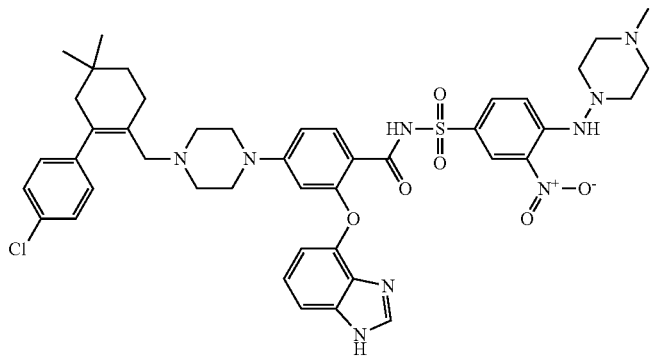 [SMILES: CN1CCN(Nc2ccc(S(=O)(=O)NC(=O)c3ccc(N4CCN(CC5=C(c6ccc(Cl)cc6)CC(C)(C)CC5)CC4)cc3Oc3cccc4[nH]cnc34)cc2[N+](=O)[O-])CC1] |

| Name | Structure |
|---|---|
| 2-(1H-benzimidazol-4-yloxy)-4-(4-{[2-(4-chlorophenyl)-4,4-dimethylcyclohex-1-en-1-yl]methyl}piperazin-1-yl)-N-[(4-{[(1-methylpiperidin-4-yl)methyl]amino}-3-nitrophenyl)sulfonyl]benzamide | 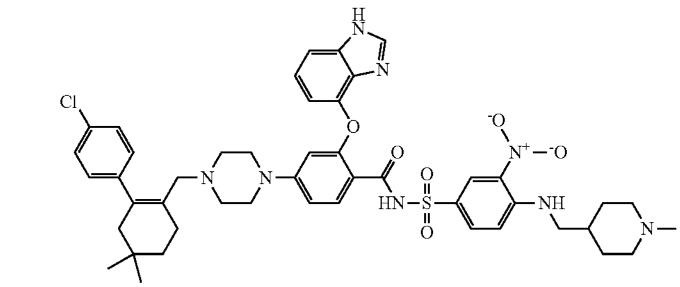 |
| 2-(1H-benimidazol-4-yloxy)-4-(4-{[-2(4-chlorophenyl)-4,4-dimethylcyclohex-1-en-1-yl]methyl}piperazin-1-yl)-N-({4-[({(2R)-4-[2-(2-methoxyethoxy)ethyl]morpholin-2-yl}methyl)amino]-3-nitrophenyl}sulfonyl)benzamide | 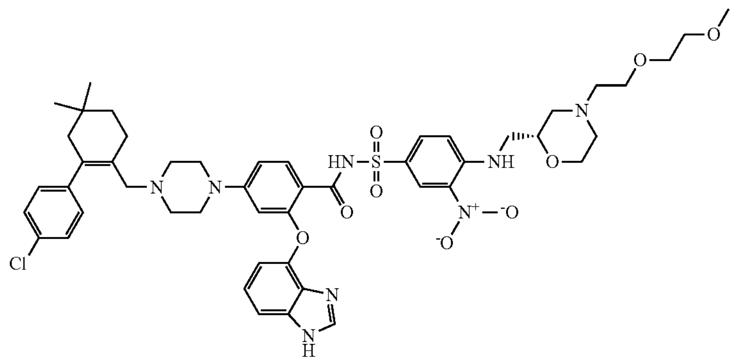 |
| 2-(1H-benimidazol-4-yloxy)-4-(4-{[2-(4-chlorophenyl)-4,4-dimethylcyclohex-1-en-1-yl]methyl}piperazin-1-yl)-N-[(4-{[(4,4-difluorocyclohexyl)methyl]amino}-3-nitrophenyl)sulfonyl]benzamide | 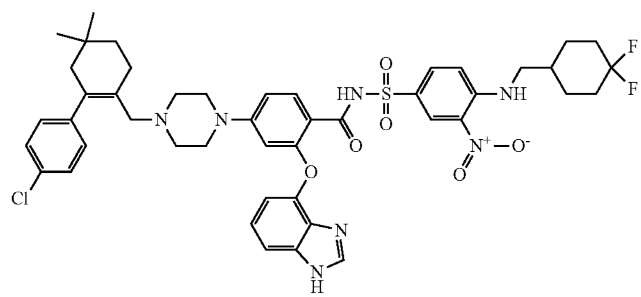 [SMILES: CC1(C)CCC(CN2CCN(c3ccc(C(=O)NS(=O)(=O)c4ccc(NCC5CCC(F)(F)CC5)c([N+](=O)[O-])c4)c(Oc4cccc5[nH]cnc45)c3)CC2)=C(c2ccc(Cl)cc2)C1] |
| N-[(4-{[(4-acetylmorpholin-2-yl)methyl]amino}-3-nitrophenyl)sulfonyl]-2-(1H-benzimidazol-4-yloxy)-4-(4-{[2-(4-chlorophenyl)-4,4-dimethylcyclohex-1-en-1-yl]methyl}piperazin-1-yl)benzamide | 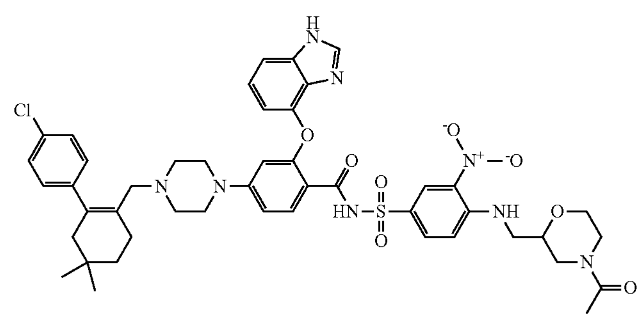 |
| 2-(1H-benzimidazol-4-yloxy)-4-(4-{[2-(4-chlorophenyl)-4,4-dimethylcyclohex-1-en-1-yl]methyl}piperazin-1-yl)-N-{[4-({[4-(methylsulfonyl)morpholin-2-yl]methyl}amino)-3-nitrophenyl]sulfonyl}benzamide | 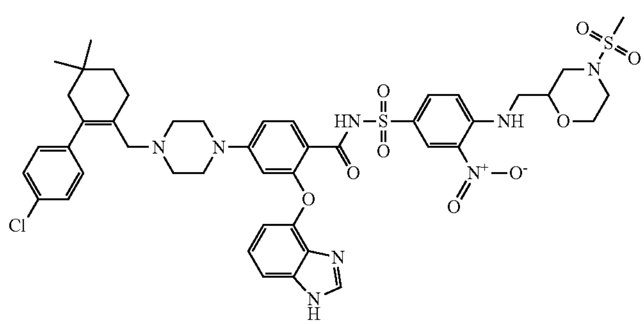 [SMILES: CC1(C)CCC(CN2CCN(c3ccc(C(=O)NS(=O)(=O)c4ccc(NCC5CN(S(C)(=O)=O)CCO5)c([N+](=O)[O-])c4)c(Oc4cccc5[nH]cnc45)c3)CC2)=C(c2ccc(Cl)cc2)C1] |

| Name | Structure |
|---|---|
| 4-(4-{[2-(4-chlorophenyl)-4,4-dimethylcyclohex-1-en-1-yl]methyl}piperazin-1-yl)-N-{[6-({4-fluoro-1-[2-fluoro-1-(fluoromethyl)ethyl]piperidin-4-yl}methoxy)-5-(trifluoromethyl)pyridin-3-yl]sulfonyl}-2-(1H-indazol-4-yloxy)benzamide | 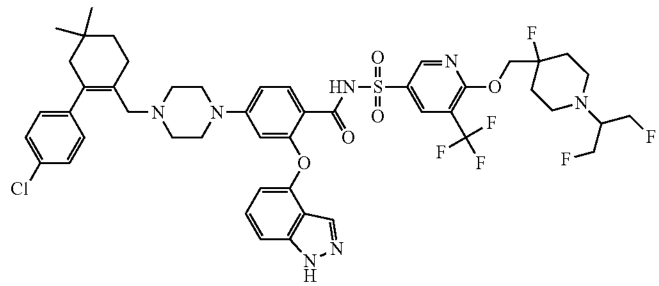 [SMILES: CC1(C)CCC(CN2CCN(c3ccc(C(=O)NS(=O)(=O)c4cnc(OCC5(F)CCN(C(CF)CF)CC5)c(C(F)(F)F)c4)c(Oc4cccc5[nH]ncc45)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-phenoxybenzamide | 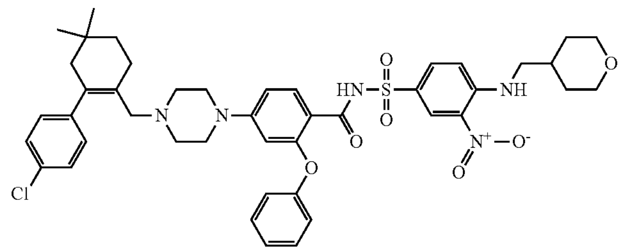 [SMILES: CC1(C)CCC(CN2CCN(c3ccc(C(=O)NS(=O)(=O)c4ccc(NCC5CCOCC5)c([N+](=O)[O-])c4)c(Oc4ccccc4)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-N-{[5-chloro-6-(2-tetrahydrofuran-2-ylethoxy)pyridin-3-yl]sulfonyl}-2-(1H-indazol-4-yloxy)benzamide | 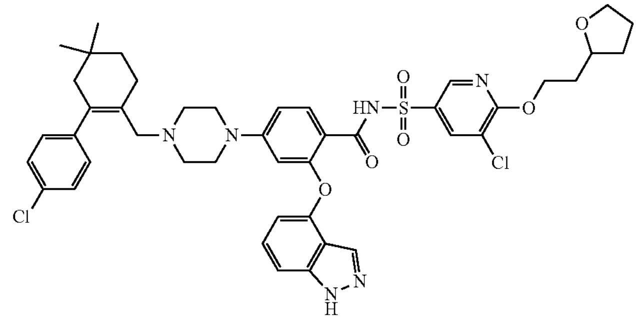 [SMILES: CC1(C)CCC(CN2CCN(c3ccc(C(=O)NS(=O)(=O)c4cnc(OCCC5CCCO5)c(Cl)c4)c(Oc4cccc5[nH]ncc45)c3)CC2)=C(c2ccc(Cl)cc2)C1] |
| Trans-2-(1H-benzimidazol-4-yloxy)-4-(4-{[2-(4-chlorophenyl)-4,4-dimethylcyclohex-1-en-1-yl]methyl}piperazin-1-yl)-N-[(4-{[(4-cyanocyclohexyl)methyl]amino}-3-nitrophenyl)sulfonyl]benzamide | |
| 2-(1H-benzimidazol-4-yloxy)-N-({5-chloro-6-[(4,4-difluorocyclohexyl)methoxy]pyridin-3-yl}sulfonyl)-4-(4-{[2-(4-chlorophenyl)-4,4-dimethylcyclohex-1-en-1-yl]methyl}piperazin-1-yl)benzamide | 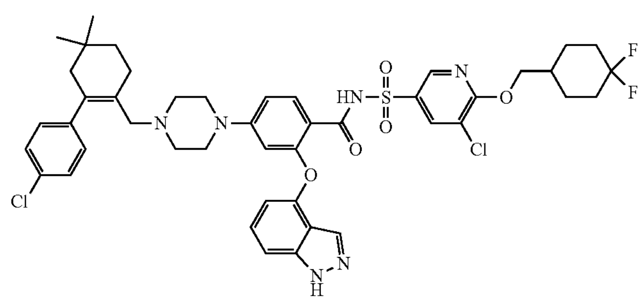 [SMILES: CC1(C)CCC(CN2CCN(c3ccc(C(=O)NS(=O)(=O)c4cnc(OCC5CCC(F)(F)CC5)c(Cl)c4)c(Oc4cccc5[nH]ncc45)c3)CC2)=C(c2ccc(Cl)cc2)C1] |
| N-({3-chloro-4-[(4-fluorotetrahydro-2H-pyran-4-yl)methoxy]phenyl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide | 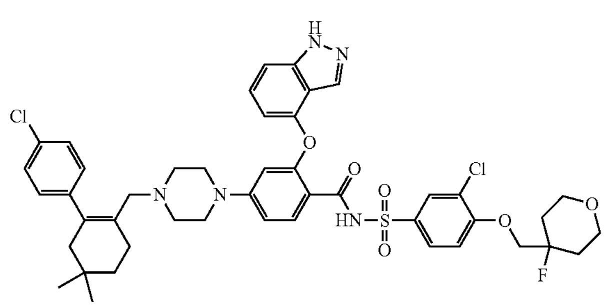 [SMILES: CC1(C)CCC(CN2CCN(c3ccc(C(=O)NS(=O)(=O)c4ccc(OCC5(F)CCOCC5)c(Cl)c4)c(Oc4cccc5[nH]ncc45)c3)CC2)=C(c2ccc(Cl)cc2)C1] |

| Name | Structure |
|---|---|
| N-({5-chloro-6-[(4-fluorotetrahydro-2H-pyran-4-yl)methoxy]pyridin-3-yl}sulfonyl)-4-(4-{[4-(4-chlorophenyl)-6,6-dimethyl-5,6-dihydro-2H-pyran-3-yl]methyl}piperazin-1-yl)-2-(1H-indazol-4-yloxy)benzamide | 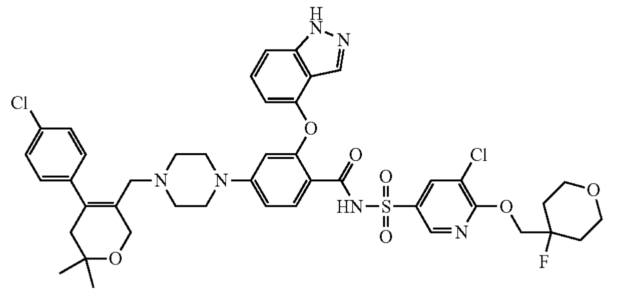 |
| 4-(4-{[2-(4-chlorophenyl)-4,4-dimethylcyclohex-1-en-1-yl]methyl}piperazin-1-yl)-N-{[5-cyano-6-(2-tetrahydro-2H-pyran-4-ylethoxy)pyridin-3-yl]sulfonyl}-2-(1H-indazol-4-yloxy)benzamide | 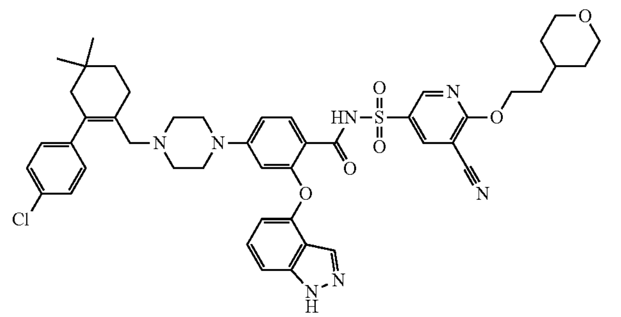 [SMILES: CC1(C)CCC(CN2CCN(c3ccc(C(=O)NS(=O)(=O)c4cnc(OCCC5CCOCC5)c(C#N)c4)c(Oc4cccc5[nH]ncc45)c3)CC2)=C(c2ccc(Cl)cc2)C1] |
| 4-(4-{[2-(4-chlorophenyl)-4,4-dimethylcyclohex-1-en-1-yl]methyl}piperazin-1-yl)-2-(1H-indol-5-yloxy)-N-[(4-{[(1R,5S)-8-methyl-8-azabicylco[3.2.1]oct-3-yl]amino}-3-nitrophenyl)sulfonyl]benzamide | 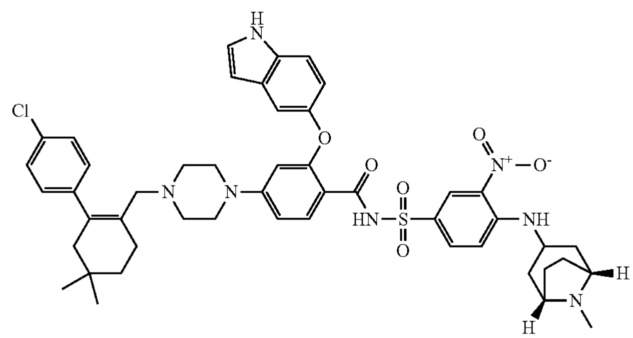 [SMILES: CN1[C@@H]2CC[C@H]1CC(Nc1ccc(S(=O)(=O)NC(=O)c3ccc(N4CCN(CC5=C(c6ccc(Cl)cc6)CC(C)(C)CC5)CC4)cc3Oc3ccc4[nH]ccc4c3)cc1[N+](=O)[O-])C2] |
| N-({3-nitro-4-[(tetrahydro-2H-pyran-4-ylmethyl)amino]phenyl}sulfonyl)-2-phenoxy-4-(4-{(3-phenylpropanoyl)[(1S,2S,3S,5R)-2,6,6-trimethylbicyclo[3.1.1]hept-3-yl]amino}piperidin-1-yl)benzamide | 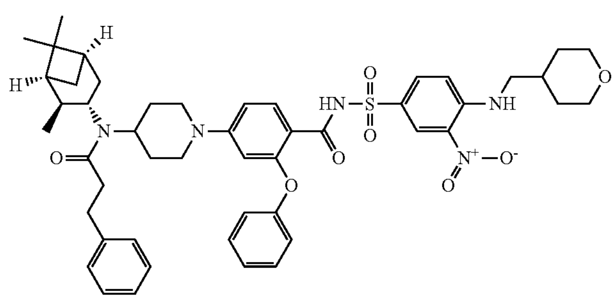 [SMILES: C[C@@H]1[C@@H](N(C(=O)CCc2ccccc2)C2CCN(c3ccc(C(=O)NS(=O)(=O)c4ccc(NCC5CCOCC5)c([N+](=O)[O-])c4)c(Oc4ccccc4)c3)CC2)C[C@H]2C[C@@H]1C2(C)C] |
| N-({4-[(3-morpholin-4-ylpropyl)amino]-3-nitrophenyl}sulfonyl)-2-phenoxy-4-(4-{(3-phenylpropanoyl)[(1S,2S,3S,5R)-2,6,6-trimethylbicyclo[3.1.1]hept-3-yl]amino}piperidin-1-yl)benzamide | 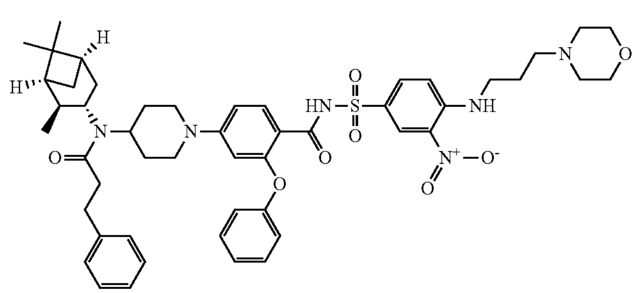 [SMILES: C[C@@H]1[C@@H](N(C(=O)CCc2ccccc2)C2CCN(c3ccc(C(=O)NS(=O)(=O)c4ccc(NCCCN5CCOCC5)c([N+](=O)[O-])c4)c(Oc4ccccc4)c3)CC2)C[C@H]2C[C@@H]1C2(C)C] |

| Name | Structure |
|------|-----------|
| N-({3-nitro-4-[(tetrahydro-2H-pyran-4-ylmethyl)amino]phenyl}sulfonyl)-2-phenoxy-4-(4-{(3-phenylpropyl)[(1S,2S,3S,5R)-2,6,6-trimethylbicyclo[3.1.1]hept-3-yl]amino}piperidin-1-yl)benzamide | 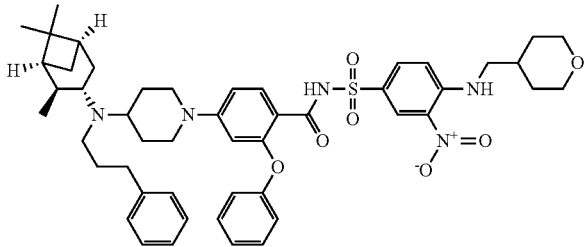 |
| N-({4-[(3-morpholin-4-ylpropyl)amino]-3-nitrophenyl}sulfonyl)-2-phenoxy-4-(4-{(3-phenylpropyl)[(1S,2S,3S,5R)-2,6,6-trimethylbicyclo[3.1.1]hept-3-yl]amino}piperidin-1-yl)benzamide | 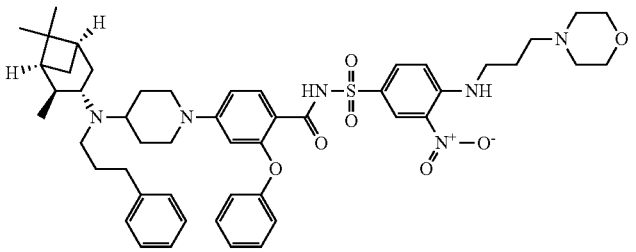 [SMILES: C[C@@H]1[C@@H](N(CCCc2ccccc2)C2CCN(c3ccc(C(=O)NS(=O)(=O)c4ccc(NCCCN5CCOCC5)c([N+](=O)[O-])c4)c(Oc4ccccc4)c3)CC2)C[C@H]2C[C@@H]1C2(C)C] |
| 4-[4-(2-{[(1R,5S)-8-methyl-8-azabicyclo[3.2.1]oct-3-yl]amino}benzyl)piperazin-1-yl]-N-({4-[(3-morpholin-4-ylpropyl)amino]-3-nitrophenyl}sulfonyl)-2-phenoxybenzamide | 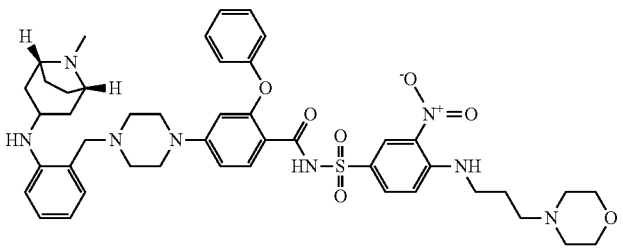 |
| 4-[4-(2-{[(1R,5S)-8-methyl-8-azabicyclo[3.2.1]oct-3-yl]amino}benzyl)piperazin-1-yl]-N-({3-nitro-4-[(tetrahydro-2H-pyran-4-ylmethyl)amino]phenyl}sulfonyl)-2-phenoxybenzamide | 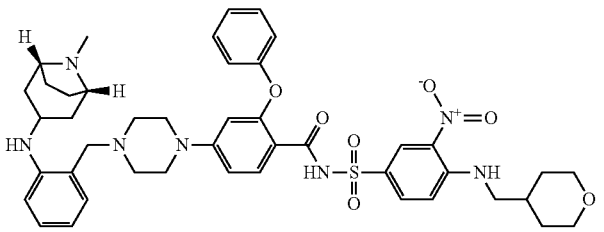 |
| 4-{4-[2-(3-azabicyclo[3.2.2]non-3-yl)benzyl]piperazin-1-yl}-N-({3-nitro-4-[(tetrahydro-2H-pyran-4-ylmethyl)amino]phenyl}sulfonyl)-2-phenoxybenzamide | 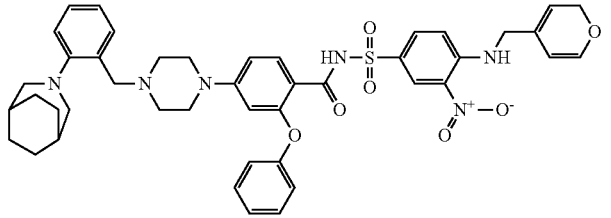 [SMILES: O=C(NS(=O)(=O)c1ccc(NCC2=CCOC=C2)c([N+](=O)[O-])c1)c1ccc(N2CCN(Cc3ccccc3N3CC4CCC(CC4)C3)CC2)cc1Oc1ccccc1] |
| 4-{4-[2-(3-azabicyclo[3.2.2]non-3-yl)benzyl]piperazin-1-yl}-2-phenoxy-N-({4-[(tetrahydro-2H-pyran-4-ylmethyl)amino]-3-[(trifluoromethyl)sulfonyl]phenyl}sulfonyl)benzamide | 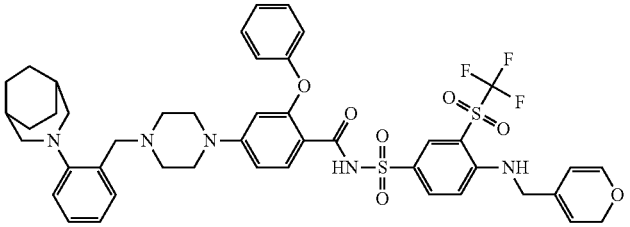 [SMILES: O=C(NS(=O)(=O)c1ccc(NCC2=CCOC=C2)c(S(=O)(=O)C(F)(F)F)c1)c1ccc(N2CCN(Cc3ccccc3N3CC4CCC(CC4)C3)CC2)cc1Oc1ccccc1] |

-continued

| Name | Structure |
|---|---|
| 4-{4-[2-(3-azabicyclo[3.2.2]non-3-yl)benzyl]piperazin-1-yl}-2-phenoxy-N-({4-[(tetrahydro-2H-pyran-4-ylmethyl)amino]phenyl}sulfonyl)benzamide | 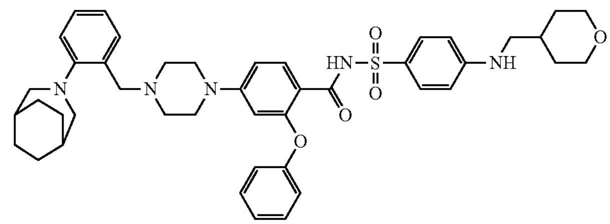 [SMILES: O=C(NS(=O)(=O)c1ccc(NCC2CCOCC2)cc1)c1ccc(N2CCN(Cc3ccccc3N3CC4CCC(CC4)C3)CC2)cc1Oc1ccccc1] |
| 4-{4-[2-(3-azabicylo[3.2.2]non-3-yl)benzyl]piperazin-1-yl}-N-({4-[(3-morpholin-4-ylpropyl)amino]-3-nitrophenyl}sulfonyl)-2-phenoxybenzamide | |
| 4-(4-{2-[(4R,7S)-2,3,3a,4,7,7a-hexahydro-1H-4,7-methanoinden-5-yl]benzyl}piperazin-1-yl)-N-({3-nitro-4-[(tetrahydro-2H-pyran-4-ylmethyl)amino]phenyl}sulfonyl)-2-phenoxybenzamide | 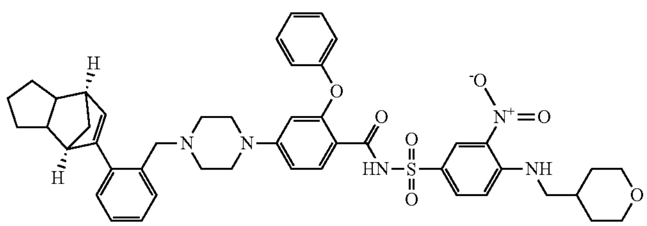 |
| 4-[4-(2-{5-[(1R,5S)-8-azabicyclo[3.2.1]oct-8-ylmethyl]thien-2-yl}benzyl)piperazin-1-yl]-N-({3-nitro-4-[(tetrahydro-2H-pyran-4-ylmethyl)amino]phenyl}sulfonyl)-2-phenoxybenzamide | 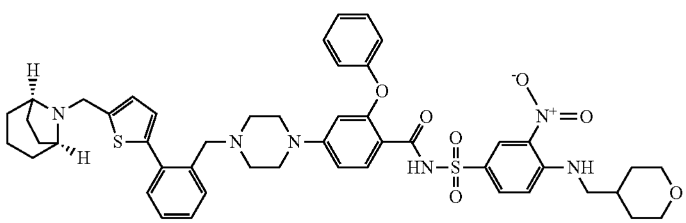 |
| 4-[4-(2-{5-[(1R,5S)-8-azabicyclo[3.2.1]oct-8-ylmethyl]thien-2-yl}benzylidene)piperidin-1-yl]-N-({3-nitro-4-[(tetrahydro-2H-pyran-4-ylmethyl)amino]phenyl}sulfonyl)-2-phenoxybenzamide | 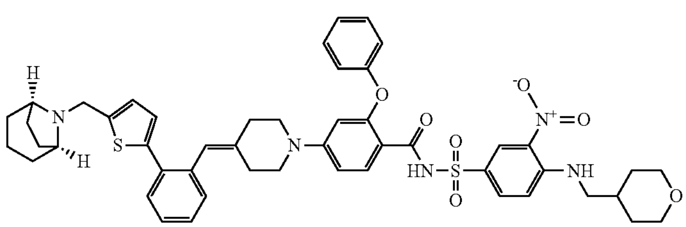 |
| 4-[4-(3-{5-[(1R,5S)-8-azabicyclo[3.2.1]oct-8-ylmethyl]thien-2-yl}benzyl)piperazin-1-yl]-N-({3-nitro-4-[(tetrahydro-2H-pyran-4-ylmethyl)amino]phenyl}sulfonyl)-2-phenoxybenzamide | 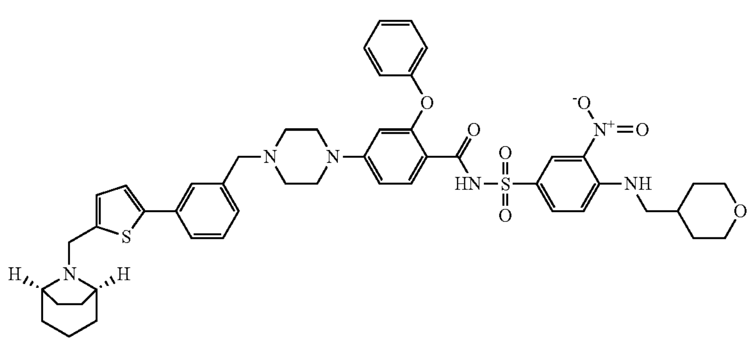 |

In some embodiments, the compound is selected from the group consisting of:

| Name | Structure |
|---|---|
| 4-[4-(cyclohexylmethyl)-4-methoxypiperidin-1-yl]-N-{[5-({(1R)-3-(dimethylamino)-1-[(phenylthio)methyl]propyl}amino)-4-nitrothien-2-yl]sulfonyl}benzamide | 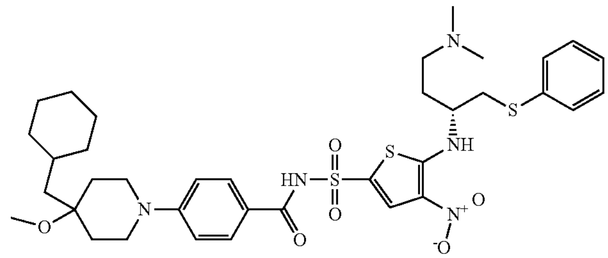 |
| N-{[5-({(1R)-3-(dimethylamino)-1-[(phenylthio)methyl]propyl}amino)-4-nitrothien-2-yl]sulfonyl}-4-[4-methoxy-4-(3-methylbenzyl)piperidin-1-yl]benzamide | 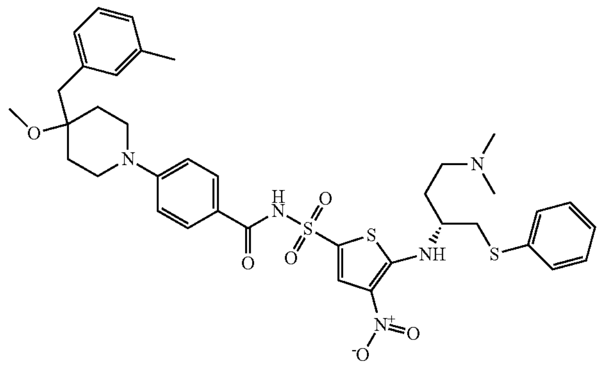 |
| N-{[5-({(1R)-3-(dimethylamino)-1-[(phenylthio)methyl]propyl}amino)-4-nitrothien-2-yl]sulfonyl}-4-[4-(3,3-diphenylprop-2-enyl)piperazin-1-yl]benzamide | 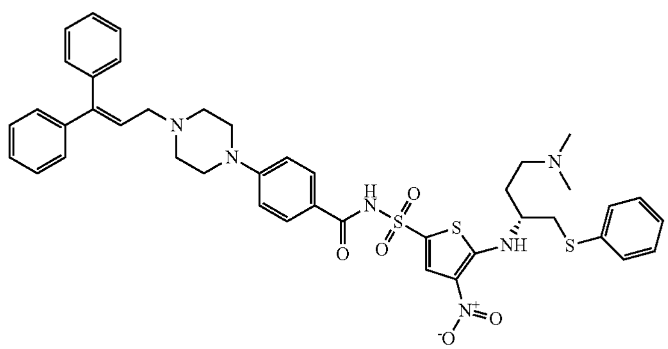 |
| 4-{4-[(4'-chloro-1,1'-biphenyl-2-yl)methyl]piperazin-1-yl}-N-[(4-{[2-(phenylthio)ethyl]amino}piperidin-1-yl)sulfonyl]benzamide | 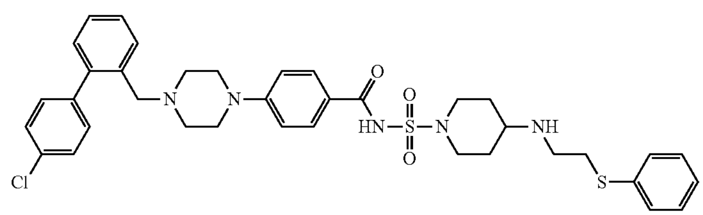 [SMILES: O=C(NS(=O)(=O)N1CCC(NCCSc2ccccc2)CC1)c1ccc(N2CCN(Cc3ccccc3-c3ccc(Cl)cc3)CC2)cc1] |
| N-[(4-{acetyl[2-(phenylthio)ethyl]amino}piperidin-1-yl)sulfonyl]-4-{4-[(4'-chloro-1,1'-biphenyl-2-yl)methyl]piperazin-1-yl}benzamide | 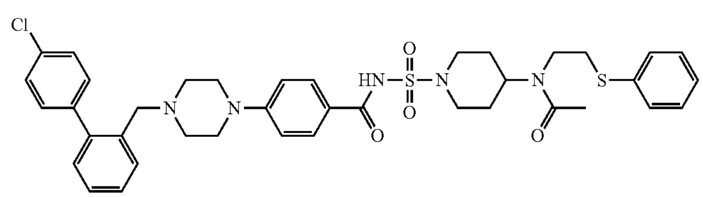 [SMILES: CC(=O)N(CCSc1ccccc1)C1CCN(S(=O)(=O)NC(=O)c2ccc(N3CCN(Cc4ccccc4-c4ccc(Cl)cc4)CC3)cc2)CC1] |
| 4-{4-[(4'-chloro-1,1'-biphenyl-2-yl)methyl]piperazin-1-yl}-N-[(4-{methyl[2-(phenylthio)ethyl]amino}piperidin-1-yl)sulfonyl]benzamide | na |

| Name | Structure |
|---|---|
| 4-{4-[(4'-chloro-1,1'-biphenyl-2-yl)methyl]piperazin-1-yl}-N-{[5-({(1R)-3-[isopropyl(methyl)amino]-1-[(phenylthio)methyl]propyl}amino)-4-nitrothien-2-yl]sulfonyl}benzamide | 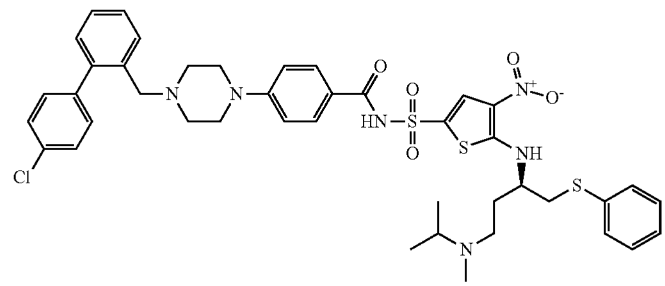 [SMILES: CC(C)N(C)CC[C@H](CSc1ccccc1)Nc1sc(S(=O)(=O)NC(=O)c2ccc(N3CCN(Cc4ccccc4-c4ccc(Cl)cc4)CC3)cc2)cc1[N+](=O)[O-]] |
| 4-(4-{[2-(4-chlorophenyl)cyclohex-1-en-1-yl]methyl}piperazin-1-yl)-N-{[5-({(1R)-3-[isopropyl(methyl)amino]-1-[(phenylthio)methyl]propyl}amino)-4-nitrothien-2-yl]sulfonyl}benzamide | 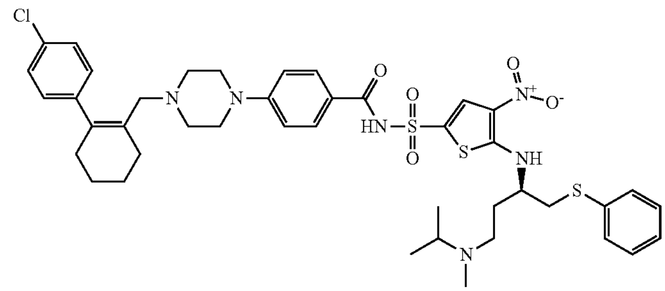 [SMILES: CC(C)N(C)CC[C@H](CSc1ccccc1)Nc1sc(S(=O)(=O)NC(=O)c2ccc(N3CCN(CC4=C(c5ccc(Cl)cc5)CCCC4)CC3)cc2)cc1[N+](=O)[O-]] |
| 4-(4-{[2-(4-chlorophenyl)-5,5-dimethylcyclohex-1-en-1-yl]methyl}piperazin-1-yl)-N-{[5-({(1R)-3-[isopropyl(methyl)amino]-1-[(phenylthio)methyl]propyl}amino)-4-nitrothien-2-yl]sulfonyl}benzamide | 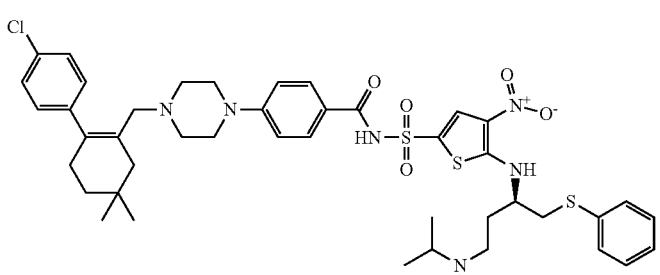 |
| N-{[(5Z)-5-(acetylimino)-4-methyl-4,5-dihydro-1,3,4-thiadiazol-2-yl]sulfonyl}-4-{4-[(4'-chloro-1,1'-biphenyl-2-yl)methyl]piperazin-1-yl}benzamide | 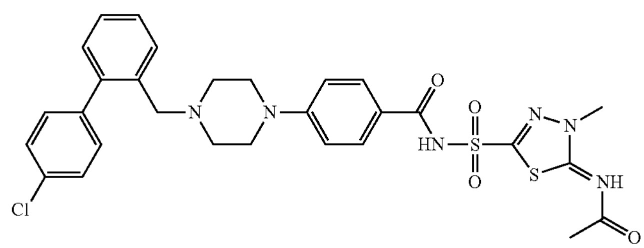 [SMILES: CC(=O)/N=c1\sc(S(=O)(=O)NC(=O)c2ccc(N3CCN(Cc4ccccc4-c4ccc(Cl)cc4)CC3)cc2)nn1C] |
| N-{[2-(acetylamino)-4-methyl-1,3-thiazol-5-yl]sulfonyl}-4-{4-[(4'-chloro-1,1'-biphenyl-2-yl)methyl]piperazin-1-yl}benzamide | 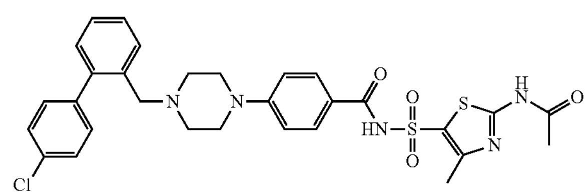 [SMILES: CC(=O)Nc1nc(C)c(S(=O)(=O)NC(=O)c2ccc(N3CCN(Cc4ccccc4-c4ccc(Cl)cc4)CC3)cc2)s1] |
| N-({5-[(benzoylamino)methyl]thien-2-yl}sulfonyl)-4-{4-[(4'-chloro-1,1'-biphenyl-2-yl)methyl]piperazin-1-yl}benzamide | 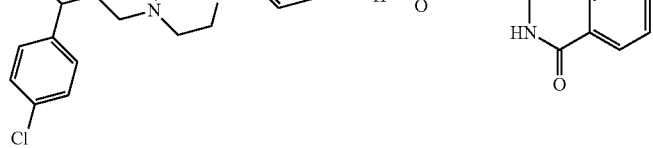 |

-continued

| Name | Structure |
|---|---|
| 4-{4-[(4'-chloro-1,1'-biphenyl-2-yl)methyl]piperazin-1-yl}-N-[(6-chloroimidazo[2,1-b][1,3]thiazol-5-yl)sulfonyl]benzamide | 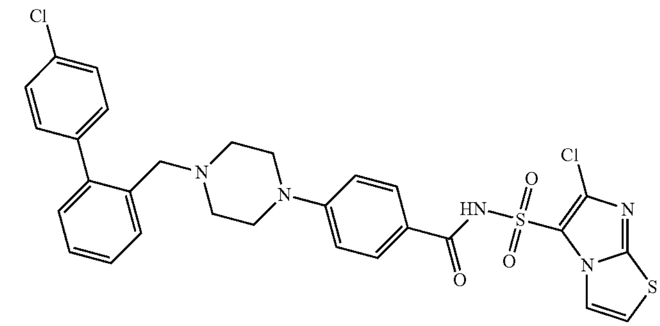 [SMILES: O=C(NS(=O)(=O)c1c(Cl)nc2sccn12)c1ccc(N2CCN(Cc3ccccc3-c3ccc(Cl)cc3)CC2)cc1] |
| 4-{4-[(4'-chloro-1,1'-biphenyl-2-yl)methyl]piperazin-1-yl}-N-(morpholin-4-ylsulfonyl)benzamide | 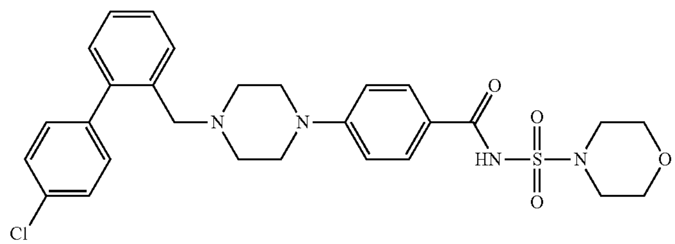 [SMILES: O=C(NS(=O)(=O)N1CCOCC1)c1ccc(N2CCN(Cc3ccccc3-c3ccc(Cl)cc3)CC2)cc1] |
| 4-{4-[(4'-chloro-1,1'-biphenyl-2-yl)methyl]piperazin-1-yl}-N-[(2,4-dimethyl-1,3-thiazol-5-yl)sulfonyl]benzamide | 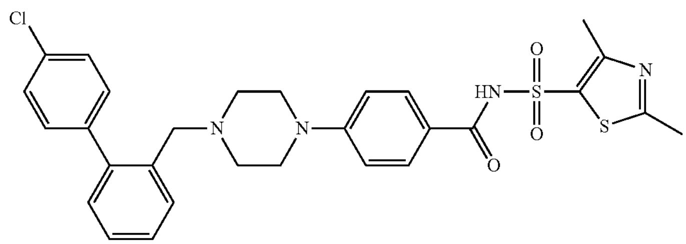 [SMILES: Cc1nc(C)c(S(=O)(=O)NC(=O)c2ccc(N3CCN(Cc4ccccc4-c4ccc(Cl)cc4)CC3)cc2)s1] |
| 4-{4-[(4'-chloro-1,1'-biphenyl-2-yl)methyl]piperazin-1-yl}-N-{[4-phenyl-5-(trifluoromethyl)thien-3-yl]sulfonyl}benzamide | 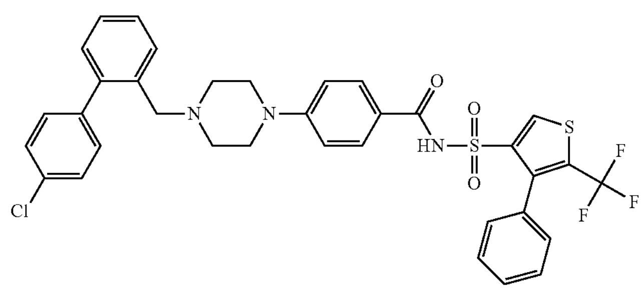 [SMILES: O=C(NS(=O)(=O)c1csc(C(F)(F)F)c1-c1ccccc1)c1ccc(N2CCN(Cc3ccccc3-c3ccc(Cl)cc3)CC2)cc1] |
| 4-{4-[(4'-chloro-1,1'-biphenyl-2-yl)methyl]piperazin-1-yl}-N-[(5-fluoro-3-methyl-1-benzothien-2-yl)sulfonyl]benzamide | 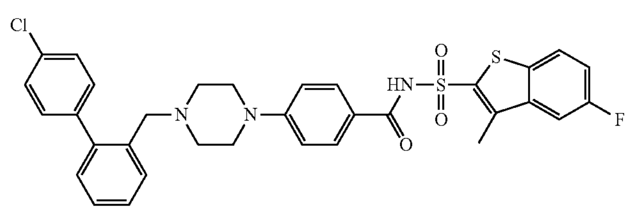 [SMILES: Cc1c(S(=O)(=O)NC(=O)c2ccc(N3CCN(Cc4ccccc4-c4ccc(Cl)cc4)CC3)cc2)sc2ccc(F)cc12] |
| N-(1,3-benzothiazol-2-ylsulfonyl-4-{4-[(4'-chloro-1,1'-biphenyl-2-yl)methyl]piperazin-1-yl}benzamide | 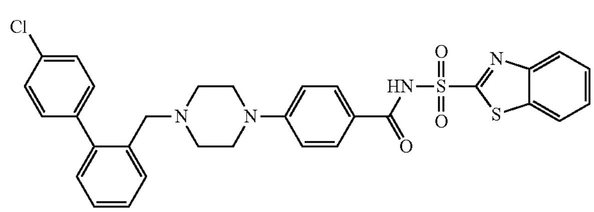 [SMILES: O=C(NS(=O)(=O)c1nc2ccccc2s1)c1ccc(N2CCN(Cc3ccccc3-c3ccc(Cl)cc3)CC2)cc1] |

-continued

| Name | Structure |
|---|---|
| 4-{4-[(4'-chloro-1,1'-biphenyl-2-yl)methyl]piperazin-1-yl}-N-(thien-2-ylsulfonyl)benzamide | 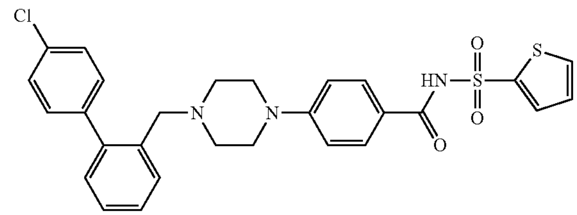 [SMILES: O=C(NS(=O)(=O)c1cccs1)c1ccc(N2CCN(Cc3ccccc3-c3ccc(Cl)cc3)CC2)cc1] |
| 4-{4-[(4'-chloro-1,1'-biphenyl-2-yl)methyl]piperazin-1-yl}-N-[(5,7-dimethyl[1,2,4]thiazolo[1,5-a]pyrimidin-2-yl)sulfonyl]benzamide | 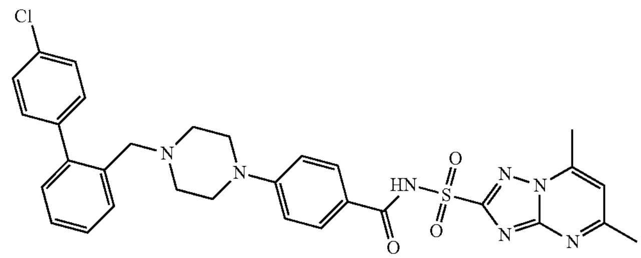 [SMILES: Cc1cc(C)n2nc(S(=O)(=O)NC(=O)c3ccc(N4CCN(Cc5ccccc5-c5ccc(Cl)cc5)CC4)cc3)nc2n1] |
| ethyl 4-{[(4-{4-[(4'-chloro-1,1'-biphenyl-2-yl)methyl]piperazin-1-yl}benzoyl)amino]sulfonyl}-5-methyl-1,2-diphenyl-1H-pyrrole-3-carboxylate | 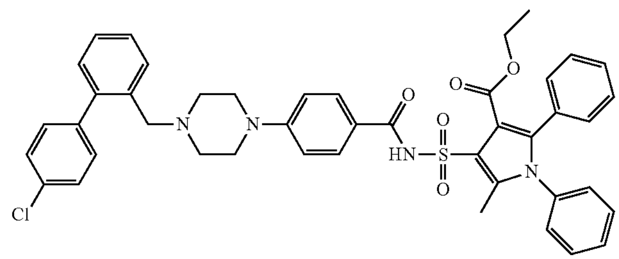 [SMILES: CCOC(=O)c1c(S(=O)(=O)NC(=O)c2ccc(N3CCN(Cc4ccccc4-c4ccc(Cl)cc4)CC3)cc2)c(C)n(-c2ccccc2)c1-c1ccccc1] |
| methyl 5-{[(4-{4-[(4'-chloro-1,1'-biphenyl-2-yl)methyl]piperazin-1-yl}benzoyl)amino]sulfonyl}-1-methyl-1H-pyrrole-2-carboxylate | 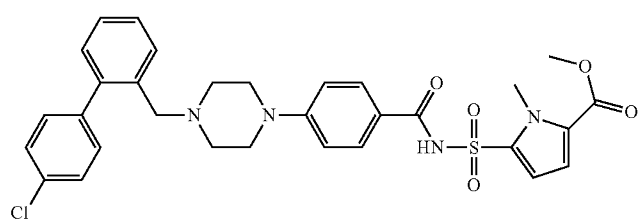 [SMILES: COC(=O)c1ccc(S(=O)(=O)NC(=O)c2ccc(N3CCN(Cc4ccccc4-c4ccc(Cl)cc4)CC3)cc2)n1C] |
| 4-{4-[(4'-chloro-1,1'-biphenyl-2-yl)methyl]piperazin-1-yl}-N-{[5-(1,3-dimethyl-1H-pyrazol-5-yl)isoxazol-4-yl]sulfonyl}benzamide | 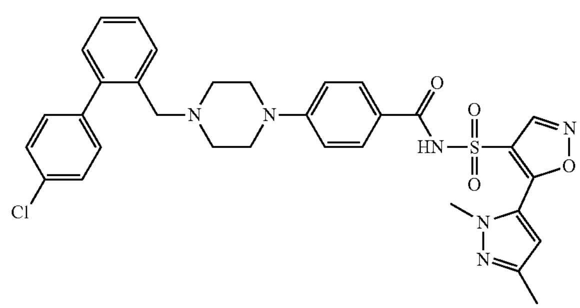 [SMILES: Cc1cc(-c2oncc2S(=O)(=O)NC(=O)c2ccc(N3CCN(Cc4ccccc4-c4ccc(Cl)cc4)CC3)cc2)n(C)n1] |
| 4-{4-[(4'-chloro-1,1'-biphenyl-2-yl)methyl]piperazin-1-yl}-N-[(4-chloro-3-methylisothiazol-5-yl)sulfonyl]benzamide | 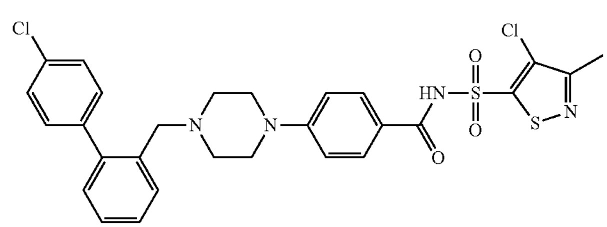 [SMILES: Cc1nsc(S(=O)(=O)NC(=O)c2ccc(N3CCN(Cc4ccccc4-c4ccc(Cl)cc4)CC3)cc2)c1Cl] |

-continued

| Name | Structure |
|---|---|
| N-[(5-bromo-3-methyl-1-benzothien-2-yl)sulfonyl]-4-{4-[(4'-chloro-1,1'-biphenyl-2-yl)methyl]piperazin-1-yl}benzamide | 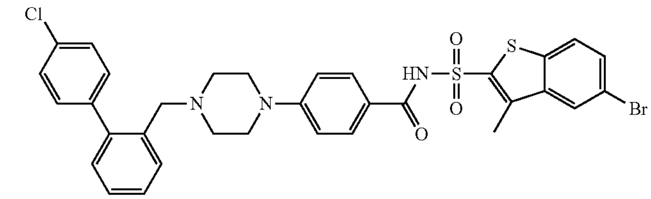 [SMILES: Cc1c(S(=O)(=O)NC(=O)c2ccc(N3CCN(Cc4ccccc4-c4ccc(Cl)cc4)CC3)cc2)sc2ccc(Br)cc12] |
| 4-{4-[(4'-chloro-1,1'-biphenyl-2-yl)methyl]piperazin-1-yl}-N-({5-[(E)-2-(1,2,4-oxadiazol-3-yl)vinyl]thien-2-yl}sulfonyl)benzamide | 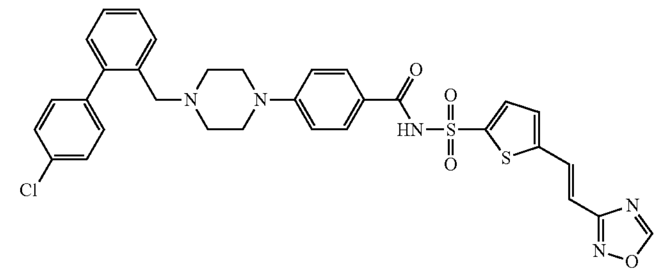 [SMILES: O=C(NS(=O)(=O)c1ccc(/C=C/c2ncon2)s1)c1ccc(N2CCN(Cc3ccccc3-c3ccc(Cl)cc3)CC2)cc1] |
| 4-{4-[(4'-chloro-1,1'-biphenyl-2-yl)methyl]piperazin-1-yl}-N-{[1-(2-chloroethyl)-3,5-dimethyl-1H-pyrazol-4-yl]sulfonyl}benzamide | 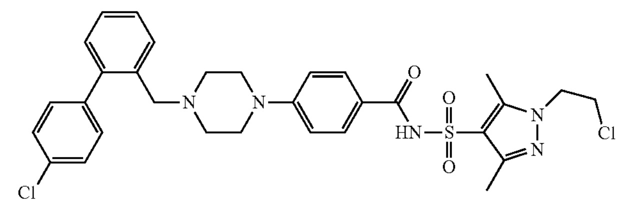 [SMILES: Cc1nn(CCCl)c(C)c1S(=O)(=O)NC(=O)c1ccc(N2CCN(Cc3ccccc3-c3ccc(Cl)cc3)CC2)cc1] |
| 5-{[(4-{4-[(4'-chloro-1,1'-biphenyl-2-yl)methyl]piperazin-1-yl}benzoyl)amino]sulfonyl}-N-(1-ethylpropyl)-1,3,4-thiadiazole-2-carboxamide | 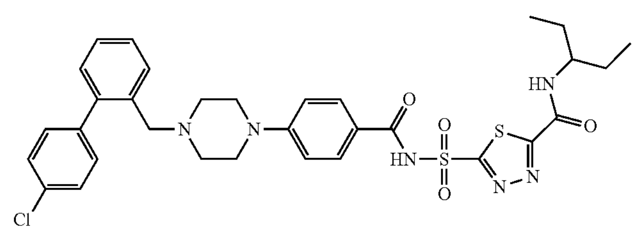 [SMILES: CCC(CC)NC(=O)c1nnc(S(=O)(=O)NC(=O)c2ccc(N3CCN(Cc4ccccc4-c4ccc(Cl)cc4)CC3)cc2)s1] |
| 4-{4-[(4'-chloro-1,1'-biphenyl-2-yl)methyl]piperazin-1-yl}-N-[(5-chloro-1,3-dimethyl-1H-pyrazol-4-yl)sulfonyl]benzamide | 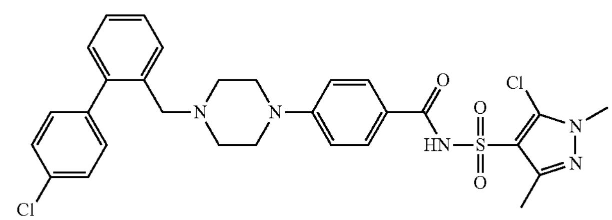 [SMILES: Cc1nn(C)c(Cl)c1S(=O)(=O)NC(=O)c1ccc(N2CCN(Cc3ccccc3-c3ccc(Cl)cc3)CC2)cc1] |
| 4-{4-[(4'-chloro-1,1'-biphenyl-2-yl)methyl]piperazin-1-yl}-N-[(4-nitro-5-piperidin-1-ylthien-2-yl)sulfonyl]benzamide | 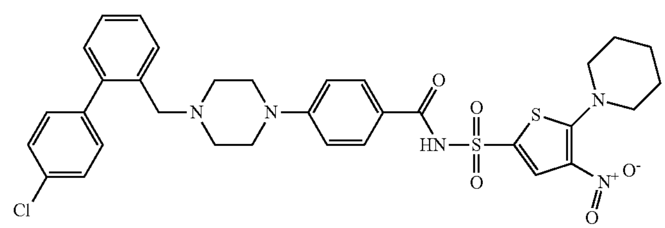 |
| 4-{4-[(4'-chloro-1,1'-biphenyl-2-yl)methyl]piperazin-1-yl}-N-[(5-isoxazol-5-yl-2-furyl)sulfonyl]benzamide | 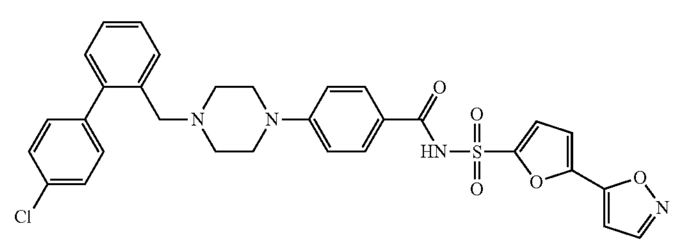 [SMILES: O=C(NS(=O)(=O)c1ccc(-c2ccno2)o1)c1ccc(N2CCN(Cc3ccccc3-c3ccc(Cl)cc3)CC2)cc1] |

-continued

| Name | Structure |
|---|---|
| 4-{4-[(4'-chloro-1,1'-biphenyl-2-yl)methyl]piperazin-1-yl}-N-[(3,5-dimethylisoxazol-4-yl)sulfonyl]benzamide | 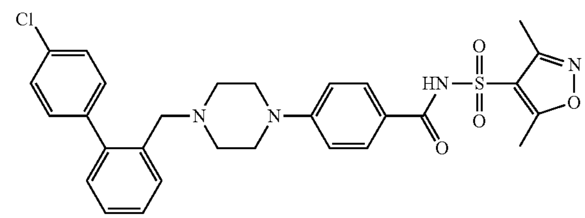 [SMILES: Cc1noc(C)c1S(=O)(=O)NC(=O)c1ccc(N2CCN(Cc3ccccc3-c3ccc(Cl)cc3)CC2)cc1] |
| 4-(4-{[2-(4-chlorophenyl)-4,4-dimethylcyclohex-1-en-1-yl]methyl}piperazin-1-yl)-2-(1H-indol-5-yloxy)-N-({4-nitro-5-[(3-pyrrolidin-1-ylpropyl)amino]thien-2-yl}sulfonyl)benzamide | 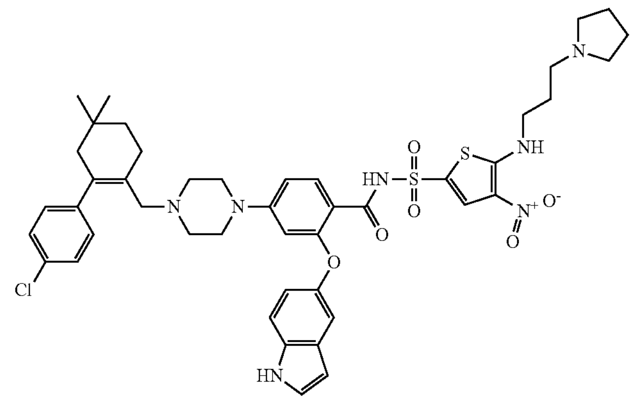 |
| 4-(4-{[2-(4-chlorophenyl)-4,4-dimethylcyclohex-1-en-1-yl]methyl}piperazin-1-yl)-N-[(5-{[3-(dimethylamino)propyl]amino}-4-nitrothien-2-yl)sulfonyl]-2-(1H-indol-5-yloxy)benzamide | 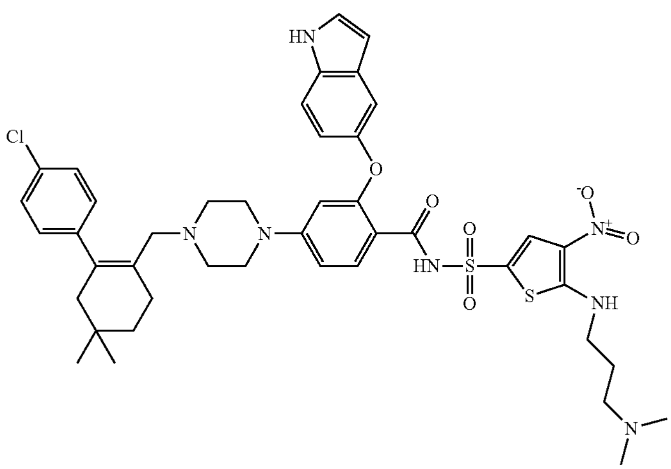 |
| 4-(4-{[2-(4-chlorophenyl)-4,4-dimethylcyclohex-1-en-1-yl]methyl}piperazin-1-yl)-2-(1H-indol-5-yloxy)-N-({5-[(3-morpholin-4-ylpropyl)amino]-4-nitrothien-2-yl}sulfonyl)benzamide | 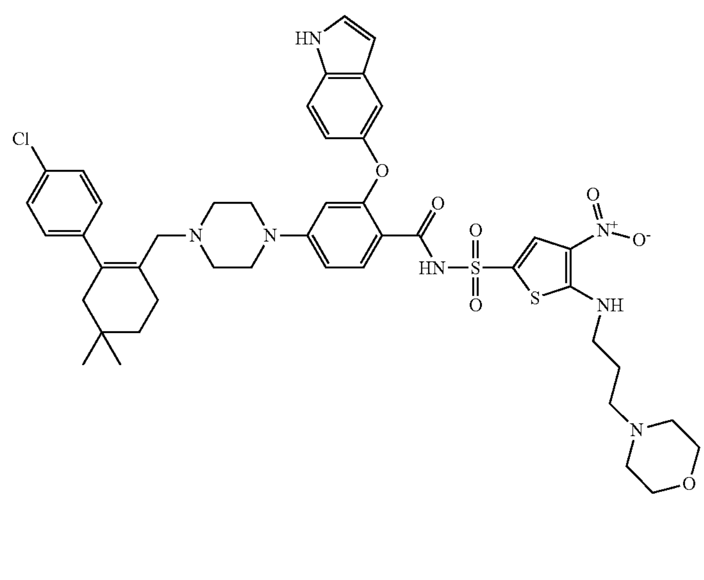 [SMILES: CC1(C)CCC(CN2CCN(c3ccc(C(=O)NS(=O)(=O)c4cc([N+](=O)[O-])c(NCCCN5CCOCC5)s4)c(Oc4ccc5[nH]ccc5c4)c3)CC2)=C(c2ccc(Cl)cc2)C1] |

-continued

| Name | Structure |
|---|---|
| N-{[5-({(1R)-3-(dimethylamino)-1-[(phenylthio)methyl]propyl}amino)-4-nitrothien-2-yl]sulfonyl}-4-{4-[2-(trifluoromethyl)benzylidene]piperadin-1-yl}benzamide | 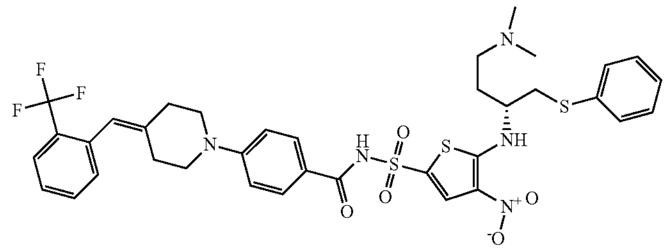 |
| 4-{4-[(4'-chloro-1,1'-biphenyl-2-yl)methylene]piperidin-1-yl}-N-[(1,1-dioxidotetrahydrothien-3-yl)sulfonyl]benzamide | 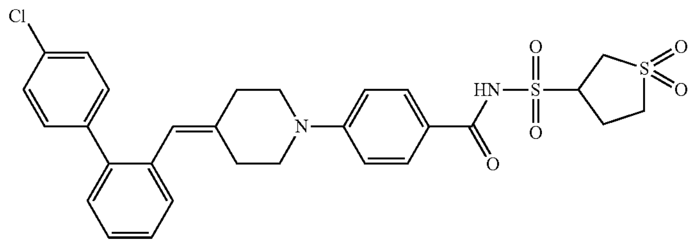 [SMILES: O=C(NS(=O)(=O)C1CCS(=O)(=O)C1)c1ccc(N2CCC(=Cc3ccccc3-c3ccc(Cl)cc3)CC2)cc1] |
| 4-{4-[(4'-chloro-1,1'-biphenyl-2-yl)methylene]piperidin-1-yl}-N-[(5-chloro-3-methyl-1-benzothien-2-yl)sulfonyl]benzamide | 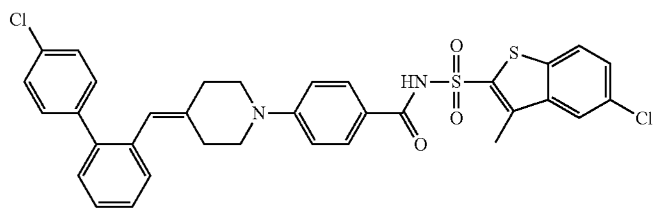 [SMILES: Cc1c(S(=O)(=O)NC(=O)c2ccc(N3CCC(=Cc4ccccc4-c4ccc(Cl)cc4)CC3)cc2)sc2ccc(Cl)cc12] |
| 4-{4-[(4'-chloro-1,1'-biphenyl-2-yl)methyl]piperazin-1-yl}-N-[(5-chloro-3-methyl-1-benzothien-2-yl)sulfonyl]-2-phenoxybenzamide | 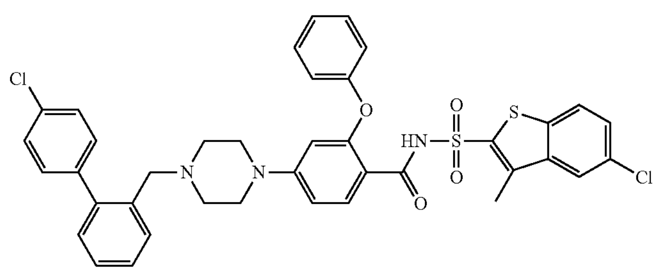 [SMILES: Cc1c(S(=O)(=O)NC(=O)c2ccc(N3CCN(Cc4ccccc4-c4ccc(Cl)cc4)CC3)cc2Oc2ccccc2)sc2ccc(Cl)cc12] |
| 2-(3-chlorophenoxy)-4-(4-{[2-(4-chlorophenyl)-4,4-dimethylcyclohex-1-en-1-yl]methyl}piperazin-1-yl)-N-[(5,7-dimethyl[1,2,4]thiazolo[1,5-a]pyrimidin-2-yl)sulfonyl]benzamide | 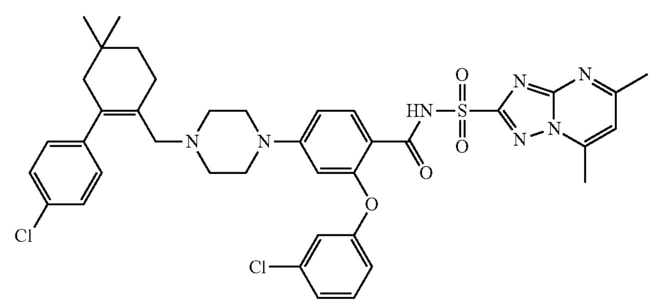 [SMILES: Cc1cc(C)n2nc(S(=O)(=O)NC(=O)c3ccc(N4CCN(CC5=C(c6ccc(Cl)cc6)CC(C)(C)CC5)CC4)cc3Oc3cccc(Cl)c3)nc2n1] |

-continued

| Name | Structure |
|---|---|
| 4-(4-{[2-(4-chlorophenyl)-4,4-dimethylcyclohex-1-en-1-yl]methyl}piperazin-1-yl)-N-[(5,7-dimethyl[1,2,4]triazolo[1,5-a]pyrimidin-2-yl)sulfonyl]-2-[(6-fluoro-1H-indol-5-yl)oxy]benzamide | 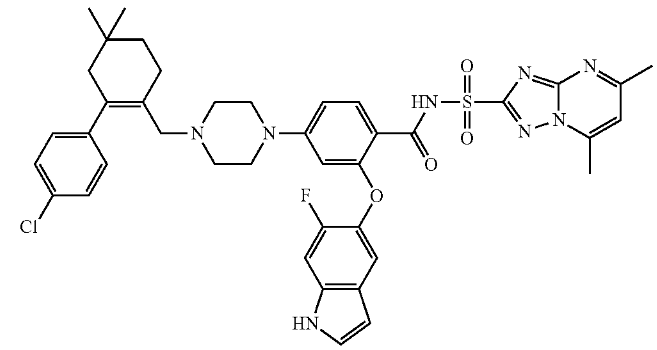 [SMILES: Cc1cc(C)n2nc(S(=O)(=O)NC(=O)c3ccc(N4CCN(CC5=C(c6ccc(Cl)cc6)CC(C)(C)CC5)CC4)cc3Oc3cc4cc[nH]c4cc3F)nc2n1] |
| 4-(4-{[2-(4-chlorophenyl)-4,4-dimethylcyclohex-1-en-1-yl]methyl}piperazin-1-yl)-2-[(6,7-difluoro-1H-indol-5-yl)oxy]-N-[(5,7-dimethyl[1,2,4]triazolo[1,5-a]pyrimidn-2-yl)sulfonyl]benzamide | 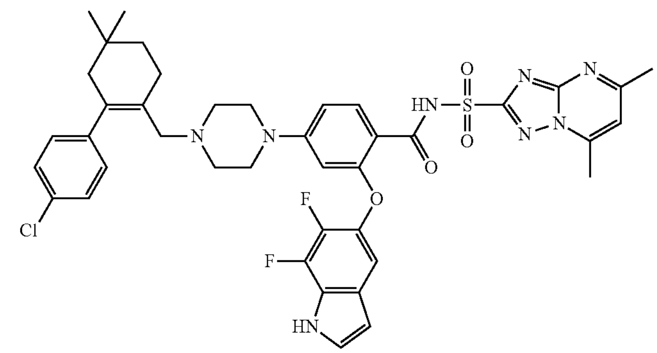 [SMILES: Cc1cc(C)n2nc(S(=O)(=O)NC(=O)c3ccc(N4CCN(CC5=C(c6ccc(Cl)cc6)CC(C)(C)CC5)CC4)cc3Oc3cc4cc[nH]c4c(F)c3F)nc2n1] |
| tert-butyl (2S)-2-{[(5-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-4-methyl-1,3-thiazol-2-yl)oxy]methyl}morpholine-4-carboxylate | 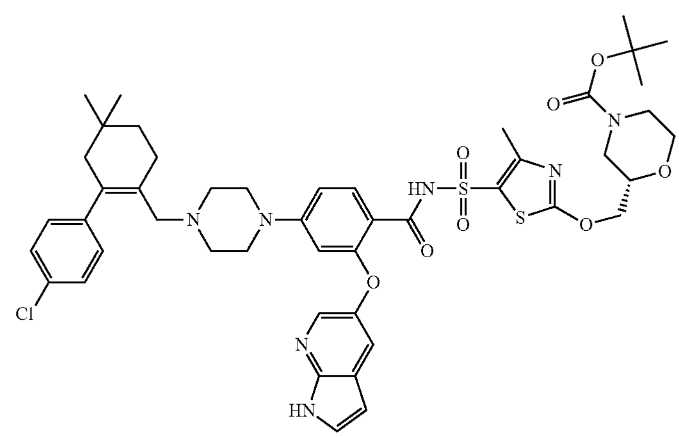 [SMILES: Cc1nc(OC[C@@H]2CN(C(=O)OC(C)(C)C)CCO2)sc1S(=O)(=O)NC(=O)c1ccc(N2CCN(CC3=C(c4ccc(Cl)cc4)CC(C)(C)CC3)CC2)cc1Oc1cnc2[nH]ccc2c1] |
| tert-butyl (2S)-2-{[(5-{[2-(1H-benzimidazol-4-yloxy)-4-(4-{[2-(4-chlorophenyl)-4,4-dimethylcyclohex-1-en-1-yl]methyl}piperazin-1-yl)benzoyl]sulfamoyl}-4-methyl-1,3-thiazol-2-yl)oxy]methyl}morpholine-4-carboxylate | 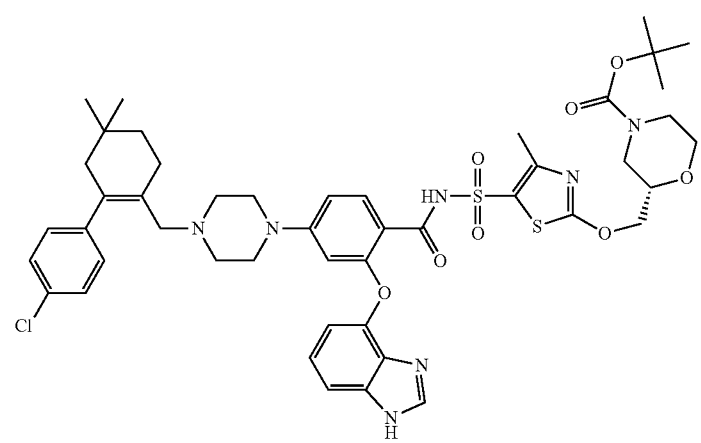 [SMILES: Cc1nc(OC[C@@H]2CN(C(=O)OC(C)(C)C)CCO2)sc1S(=O)(=O)NC(=O)c1ccc(N2CCN(CC3=C(c4ccc(Cl)cc4)CC(C)(C)CC3)CC2)cc1Oc1cccc2[nH]cnc12] |

| Name | Structure |
|---|---|
| 4-(4-{[2-(4-chlorophenyl)-4,4-dimethylcyclohex-1-en-1-yl]methyl}piperazin-1-yl)-N-({2-[(4-fluorotetrahydro-2H-pyran-4-yl)methoxy]-4-methyl-1,3-thiazol-5-yl}sulfonyl)-2-(1H-pyrrolo[2,3-b]pyridin-5-yloxy)benzamide | 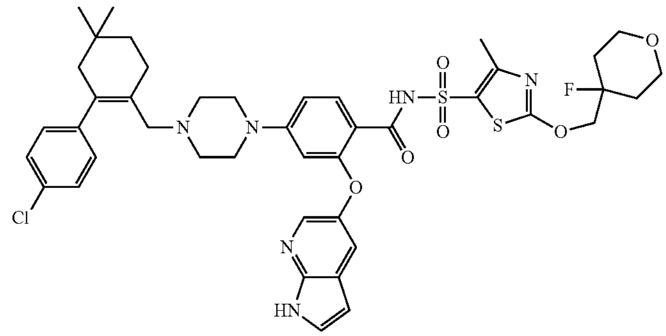 [SMILES: Cc1nc(OCC2(F)CCOCC2)sc1S(=O)(=O)NC(=O)c1ccc(N2CCN(CC3=C(c4ccc(Cl)cc4)CC(C)(C)CC3)CC2)cc1Oc1cnc2[nH]ccc2c1] |
| 2-(1H-benzimidazol-4-yloxy)-4-(4-{[2-(4-chlorophenyl)-4,4-dimethylcyclohex-1-en-1-yl]methyl}piperazin-1-yl)-N-({2-[(4-fluorotetrahydro-2H-pyran-4-yl)methoxy]-4-methyl-1,3-thiazol-5-yl}sulfonyl)benzamide | 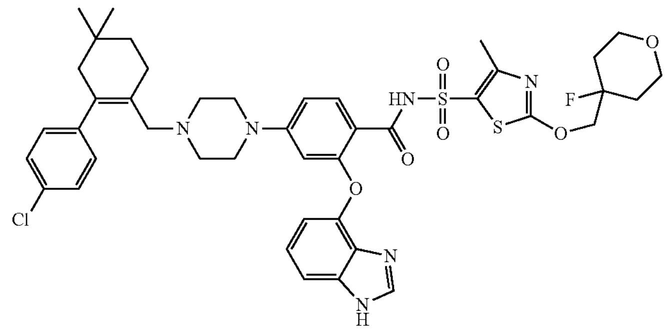 [SMILES: Cc1nc(OCC2(F)CCOCC2)sc1S(=O)(=O)NC(=O)c1ccc(N2CCN(CC3=C(c4ccc(Cl)cc4)CC(C)(C)CC3)CC2)cc1Oc1cccc2[nH]cnc12] |
| (S)-tert-butyl 2-((5-(N-(2-(1H-indazol-4-yloxy)-4-(4-((2-(4-chlorophenyl)-4,4-dimethylcyclohex-1-enyl)methyl)piperazin-1-yl)benzoyl)sulfamoyl)-4-methylthiazol-2-yloxy)methyl)morpholine-4-carboxylate | 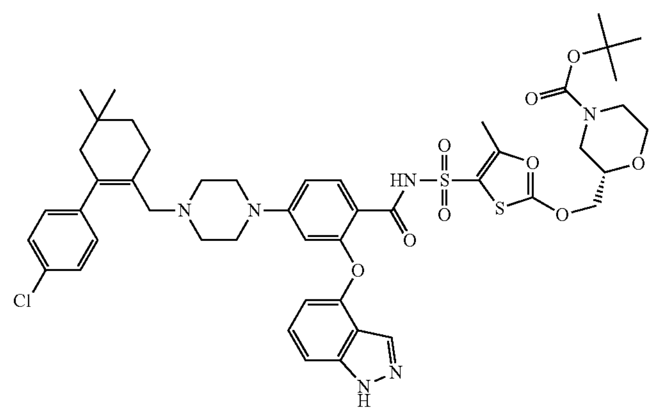 |
| 2-(1H-indazol-4-yloxy)-4-(4-((2-(4-chlorophenyl)-4,4-dimethylcyclohex-1-enyl)methyl)piperazin-1-yl)-N-(2-((4-fluorotetrahydro-2H-pyran-4-yl)methoxy)-4-methylthiazol-5-ylsulfonyl)benzamide | 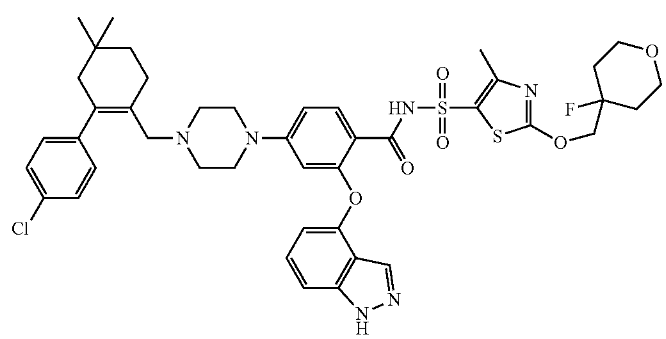 [SMILES: Cc1nc(OCC2(F)CCOCC2)sc1S(=O)(=O)NC(=O)c1ccc(N2CCN(CC3=C(c4ccc(Cl)cc4)CC(C)(C)CC3)CC2)cc1Oc1cccc2[nH]ncc12] |

In some embodiments, the compound is selected from the group consisting of:
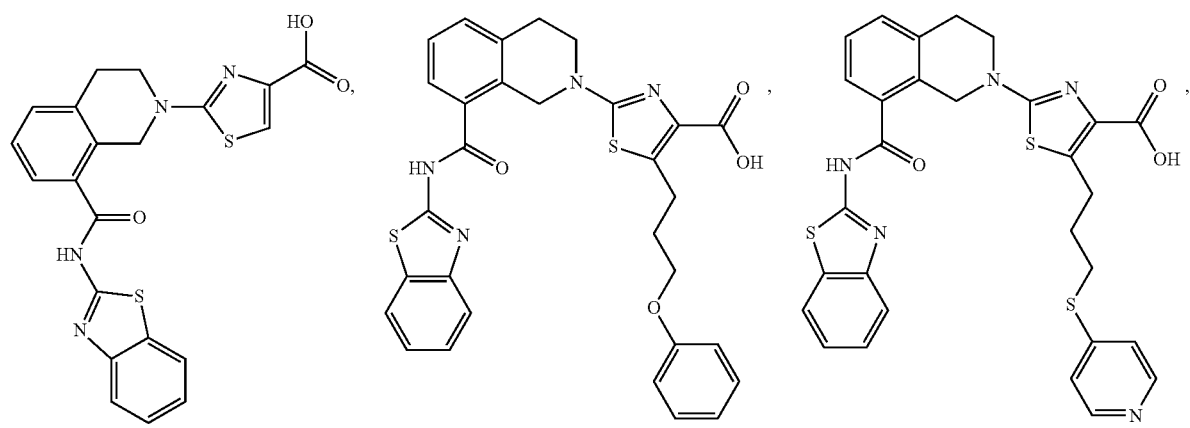
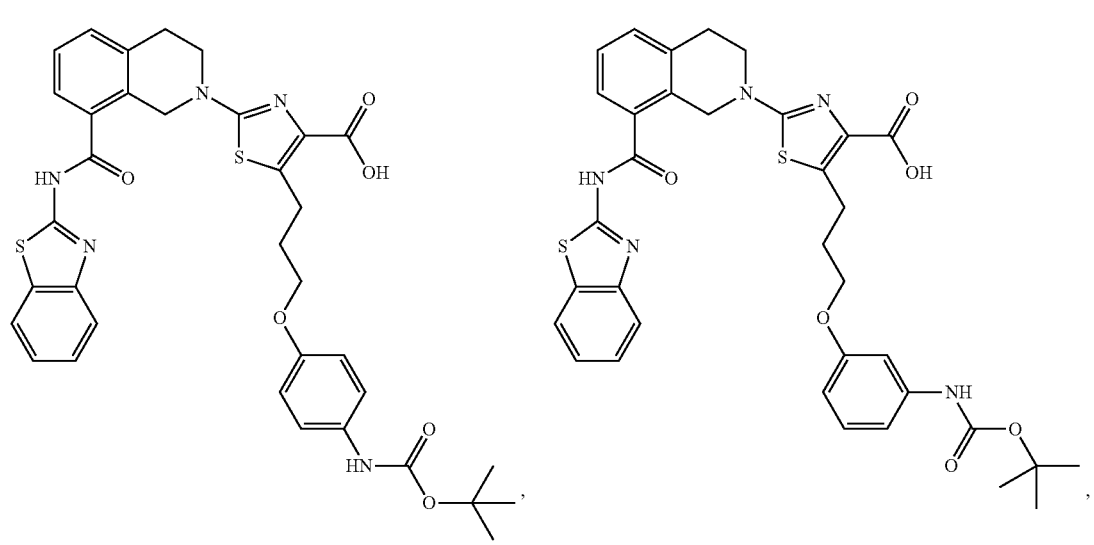
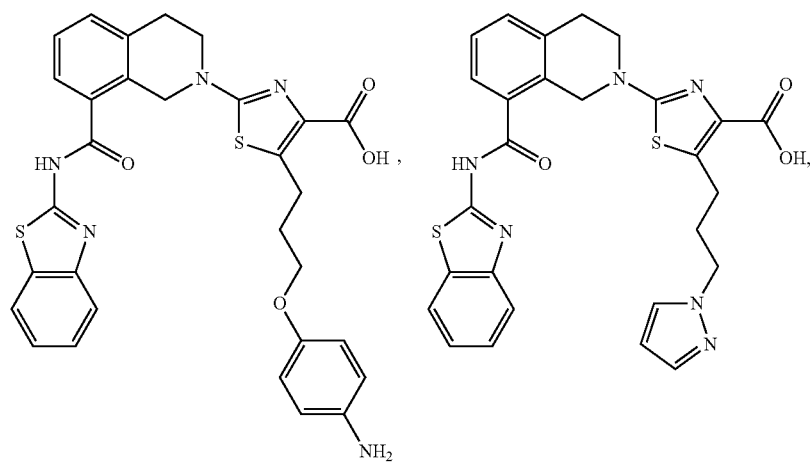

1277
1278
-continued
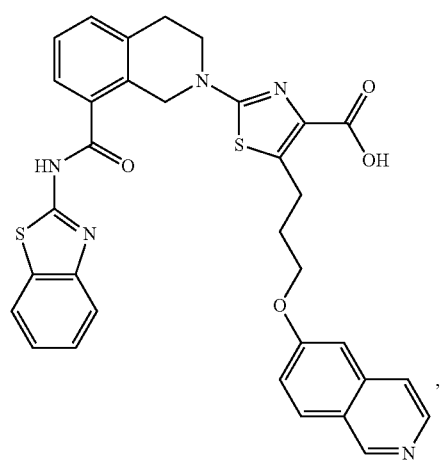
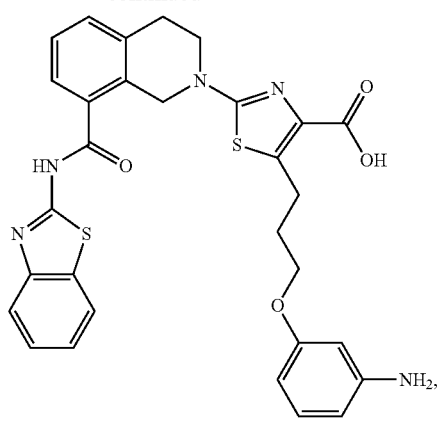
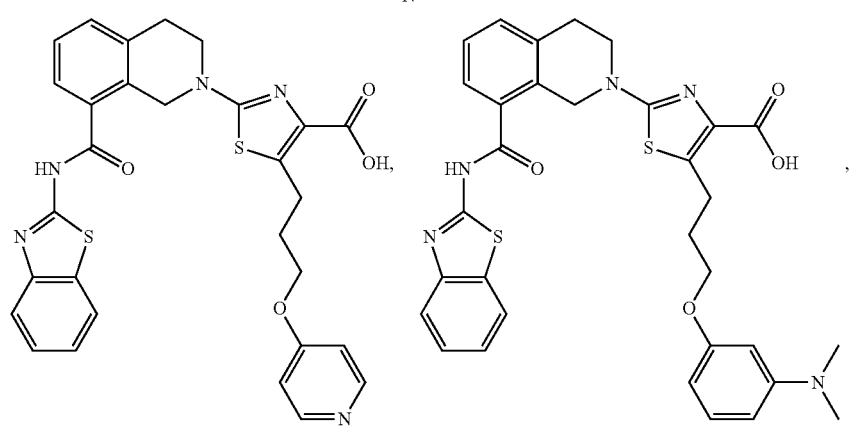
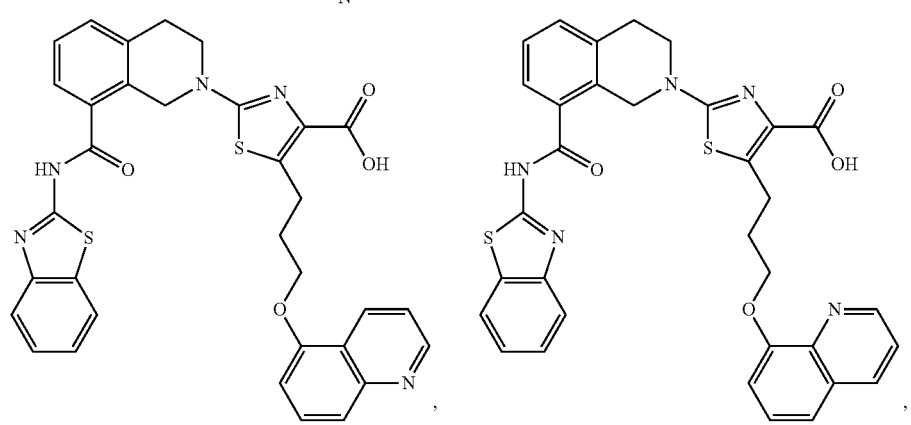
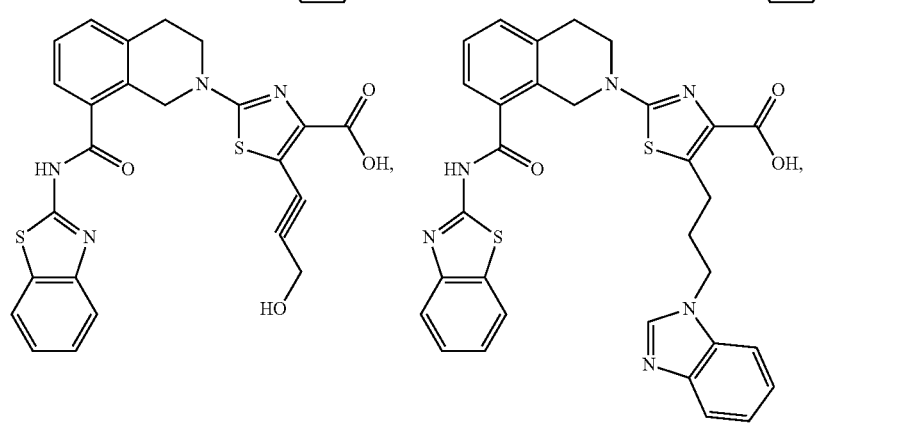

1279 1280
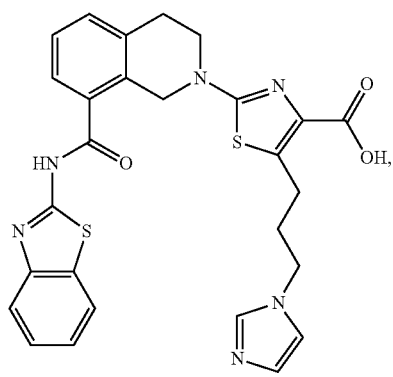
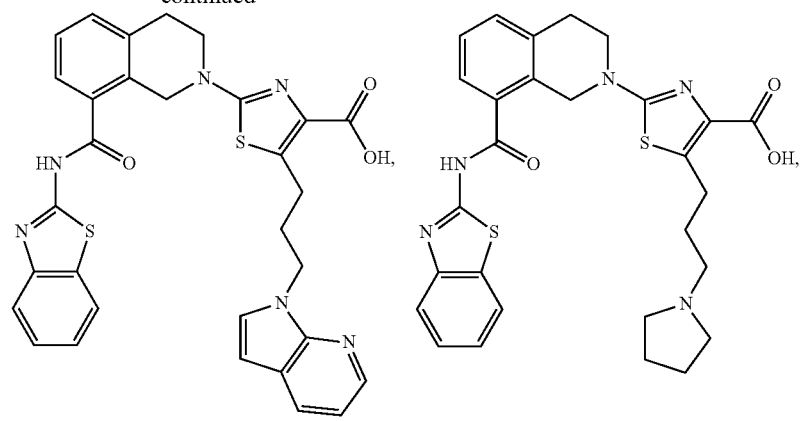
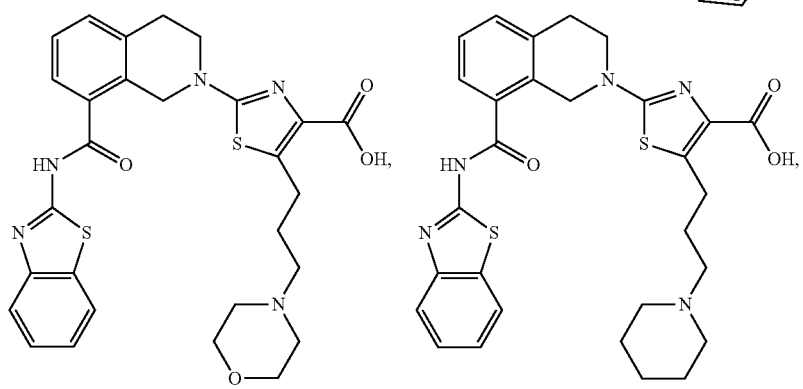
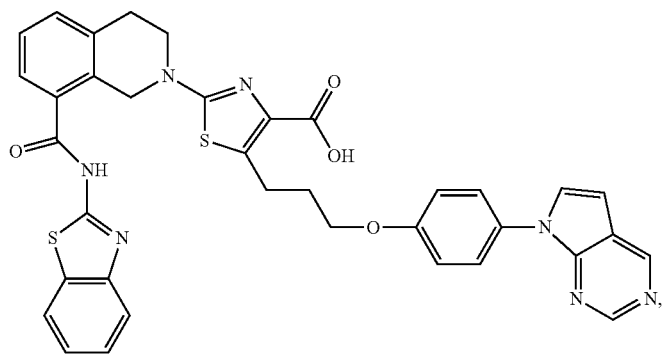
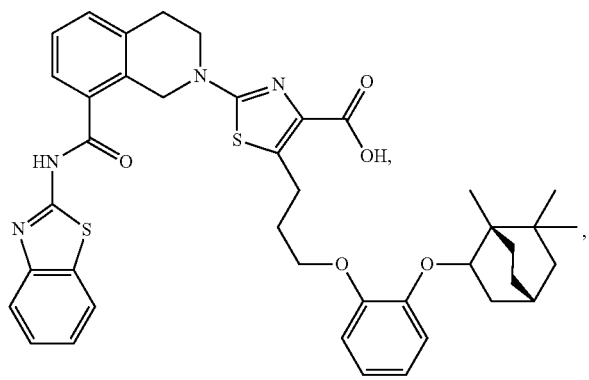

1281 1282
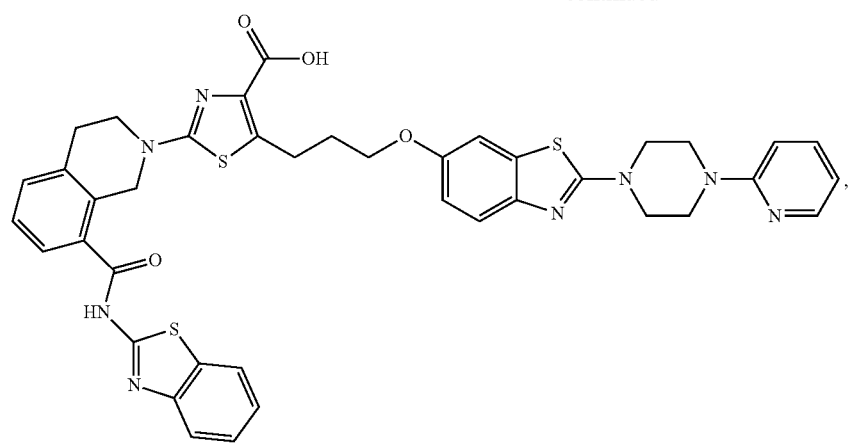
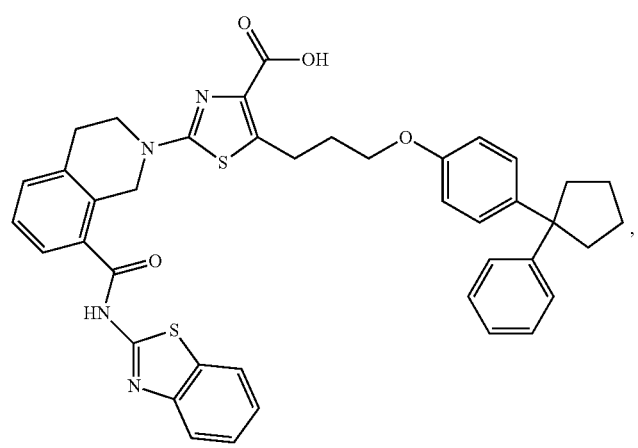
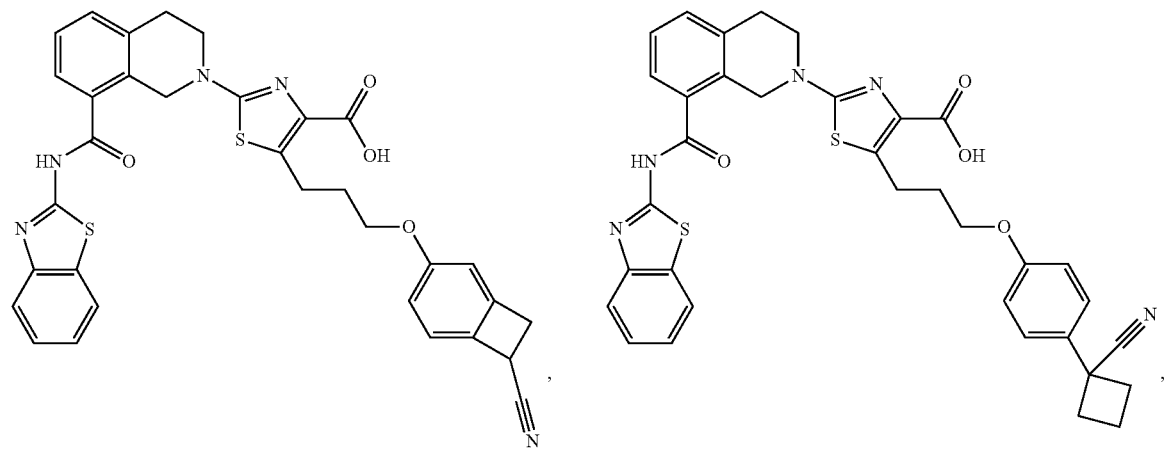

1283
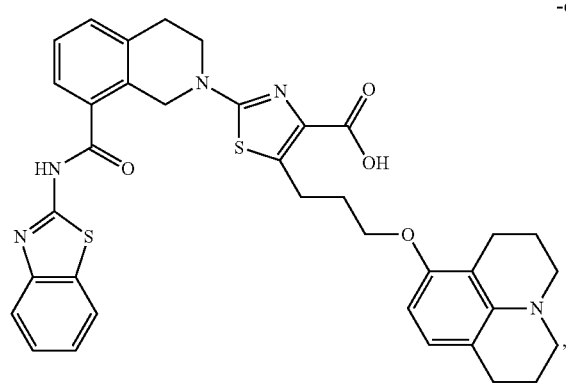
1284
-continued
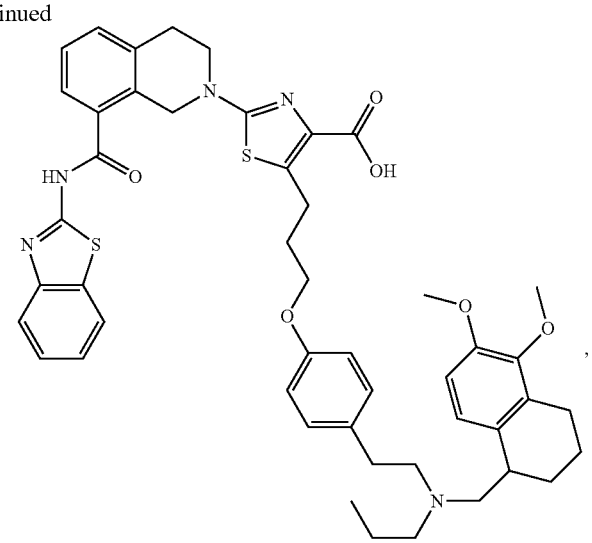
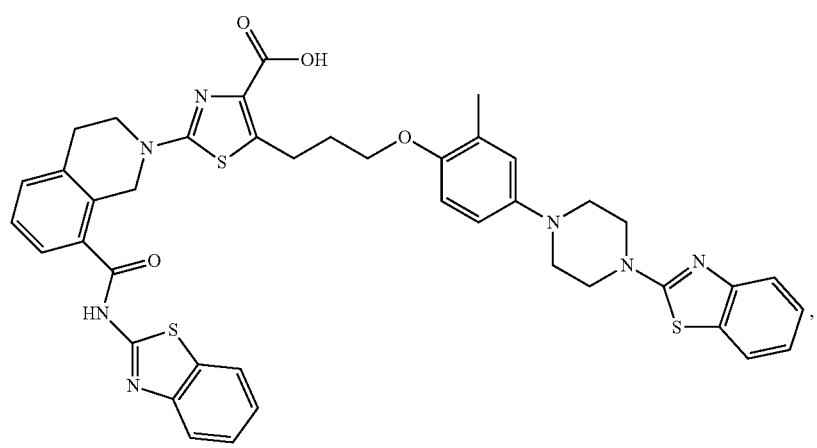
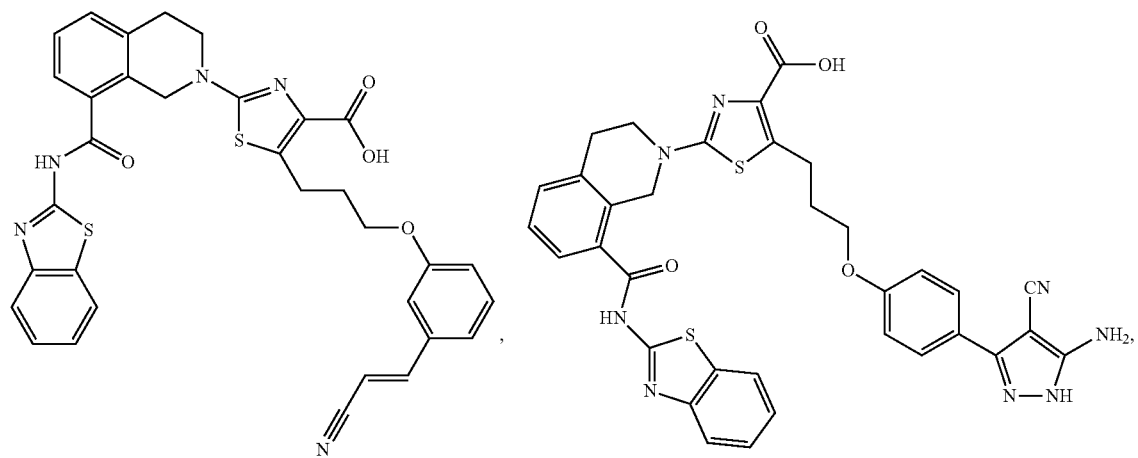

1285
1286
-continued
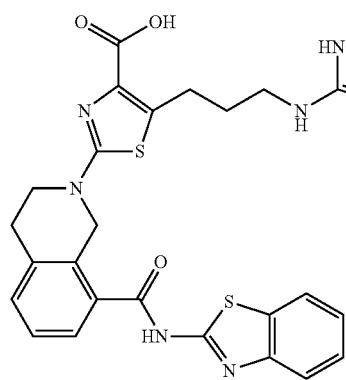
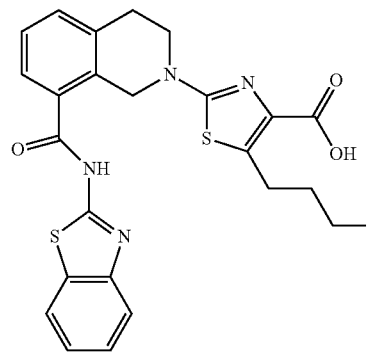
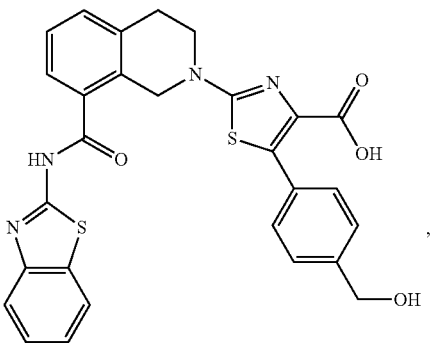
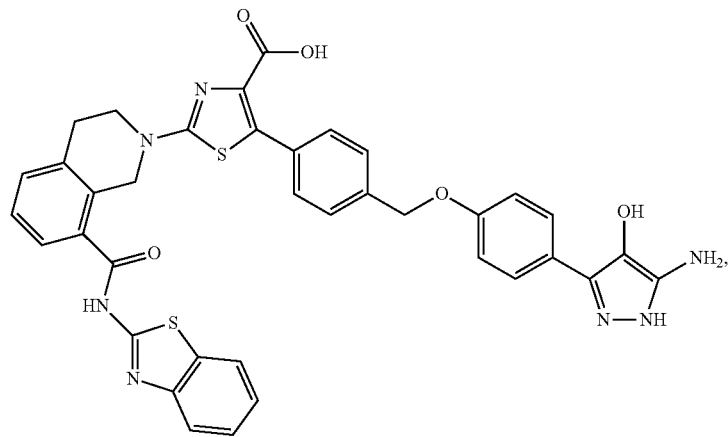
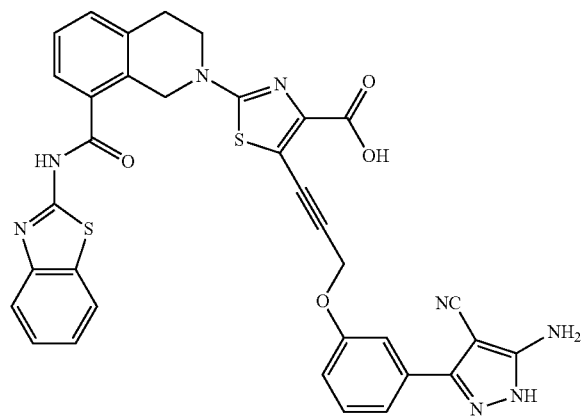
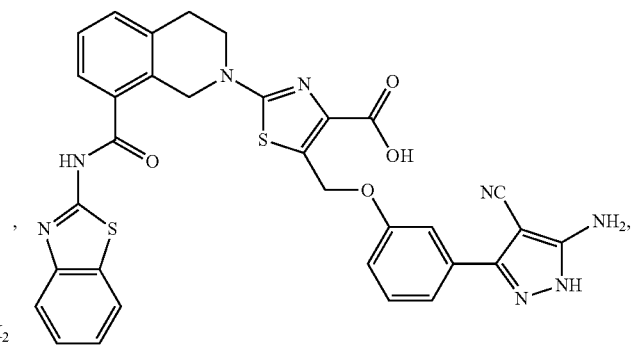

1287
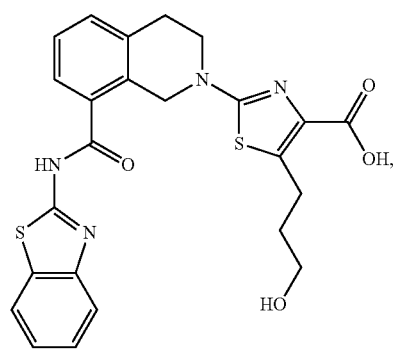
1288
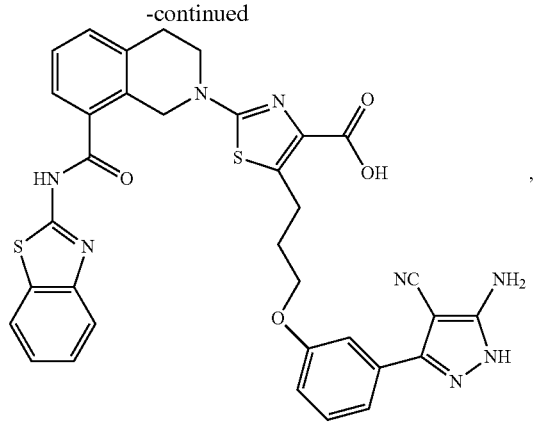
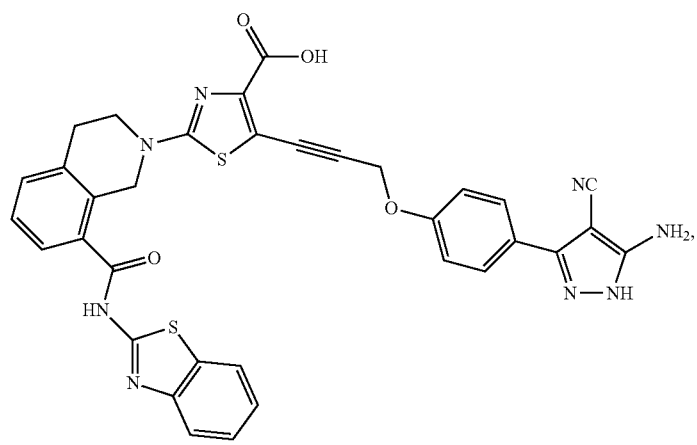
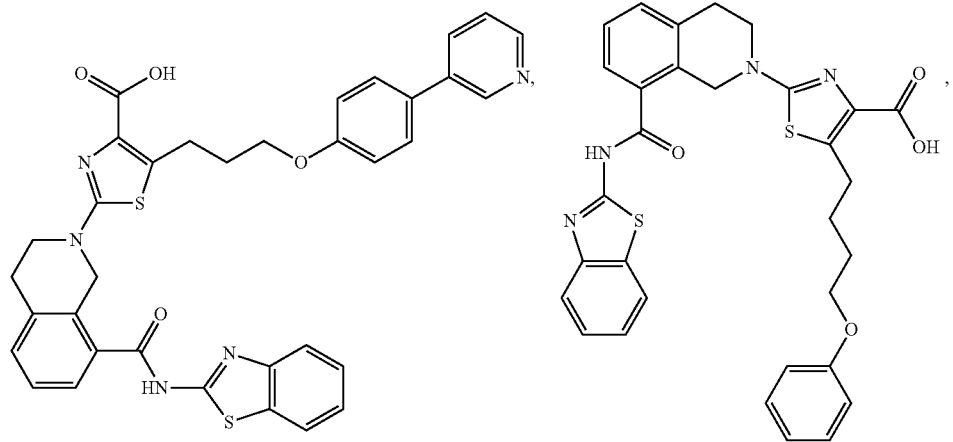
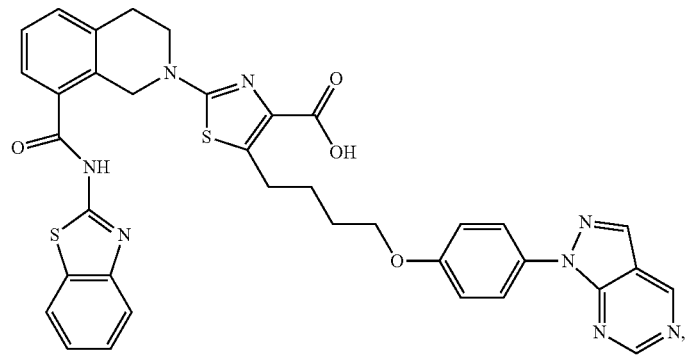

1289 1290
-continued
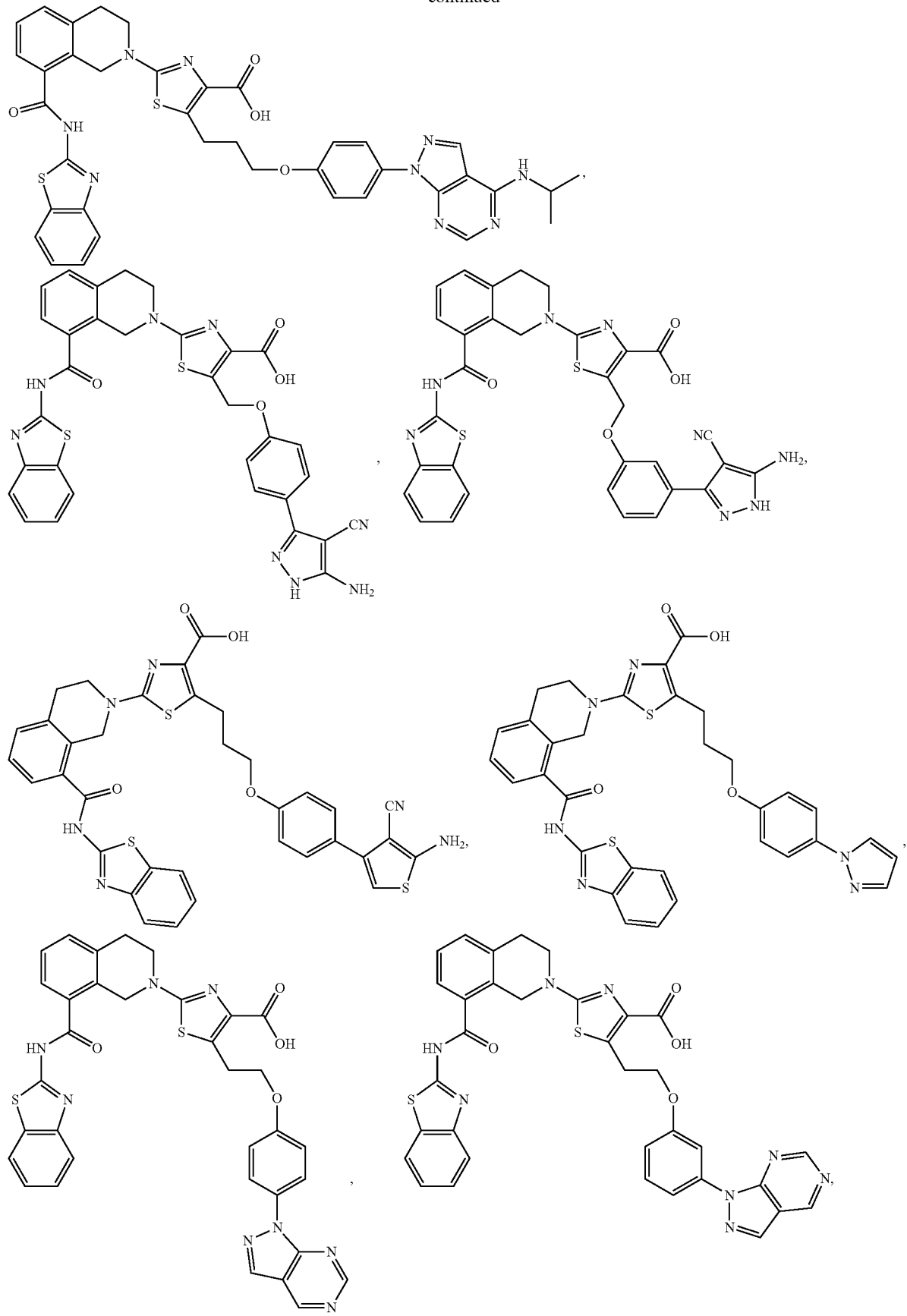

1291
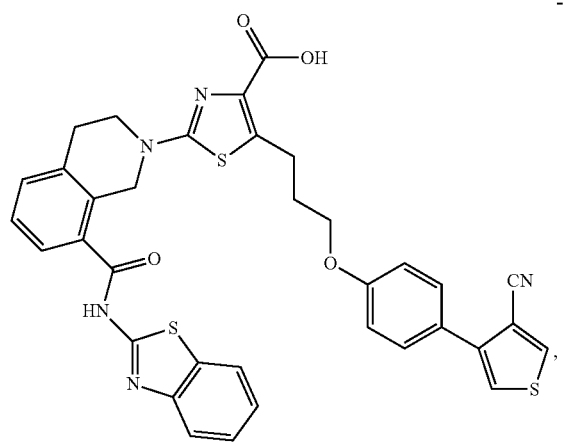
1292
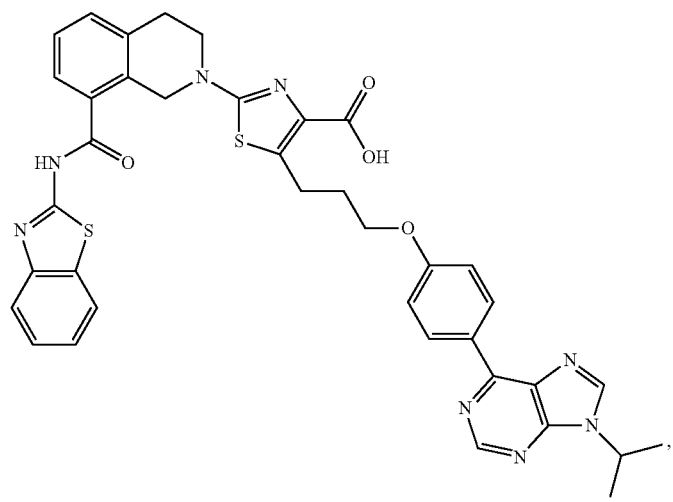
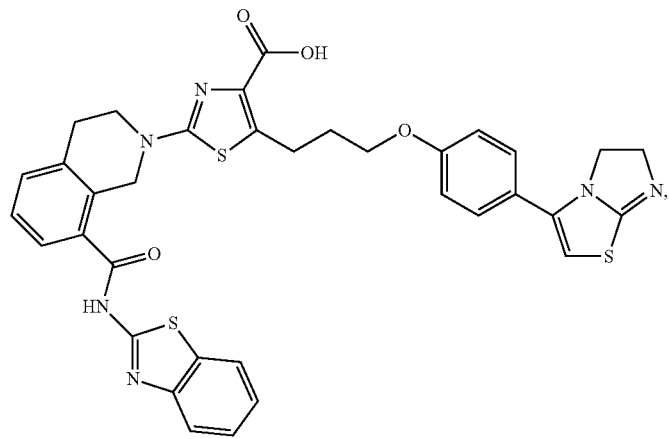

1293
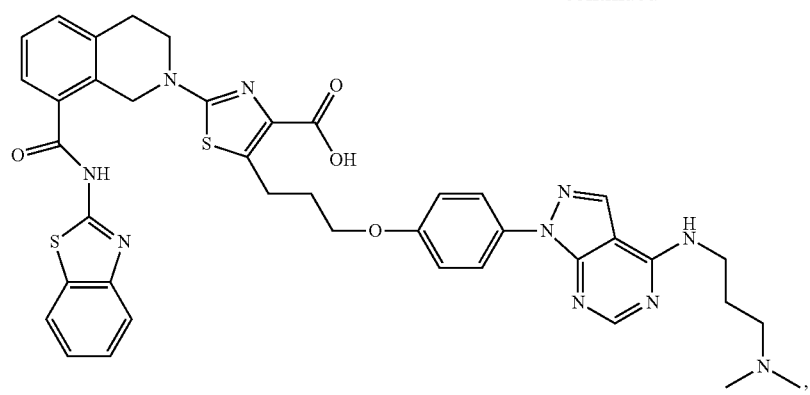
1294
-continued
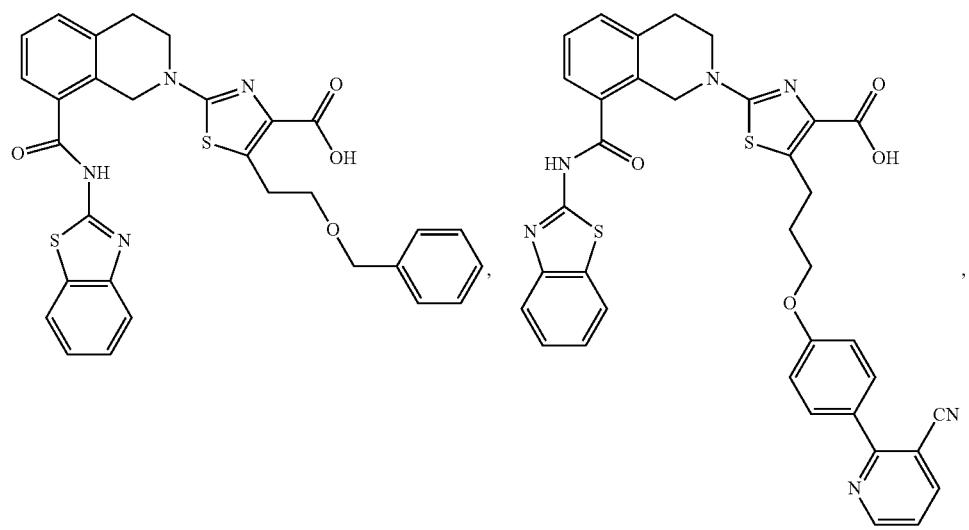
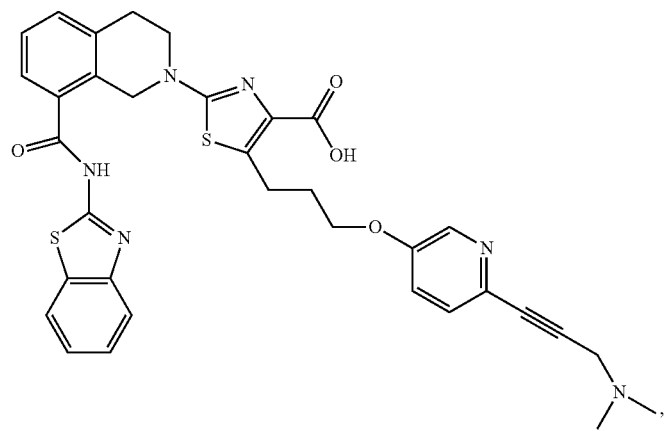

1295 1296
-continued
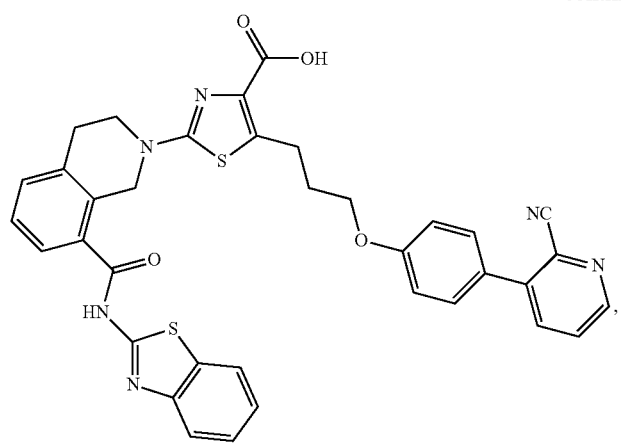
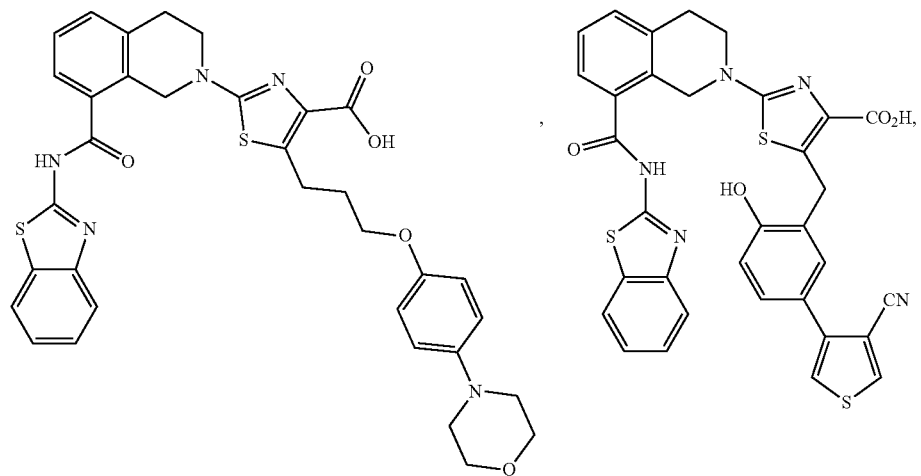
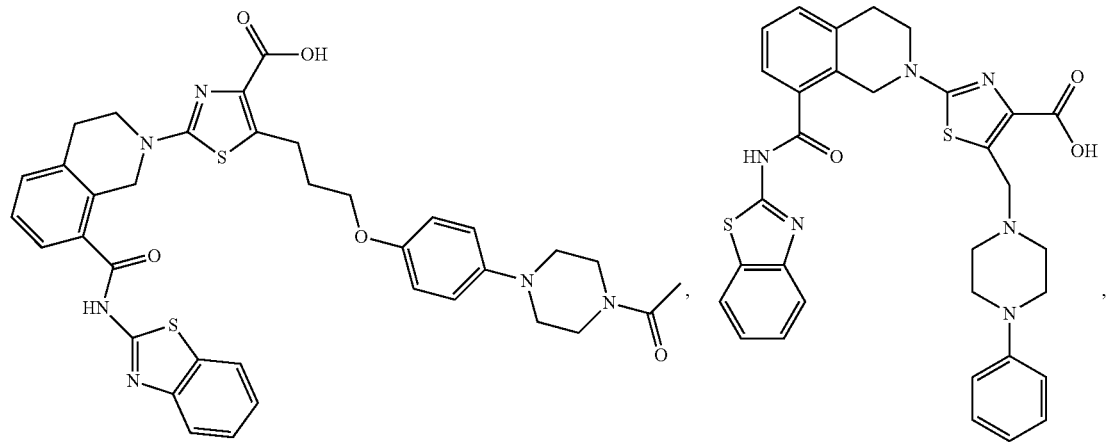

1297
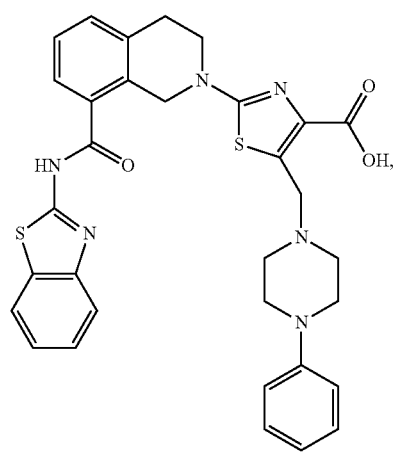
1298
-continued
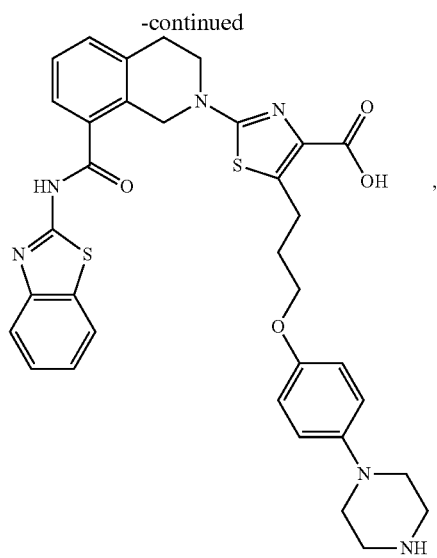
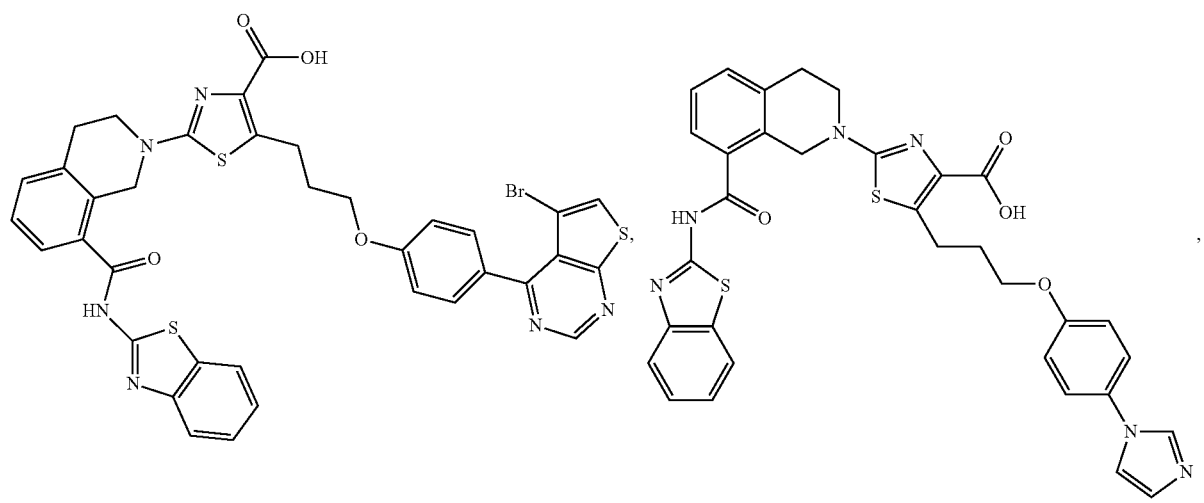
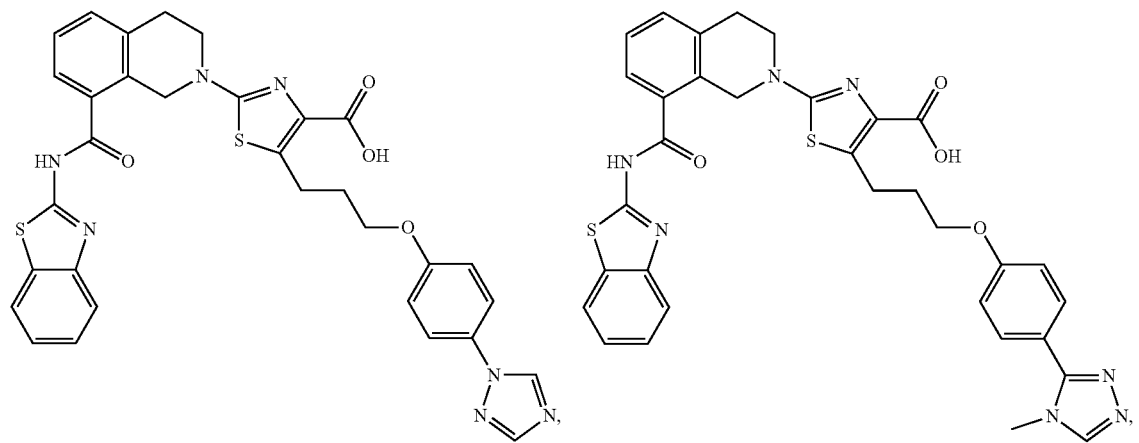

1299 1300
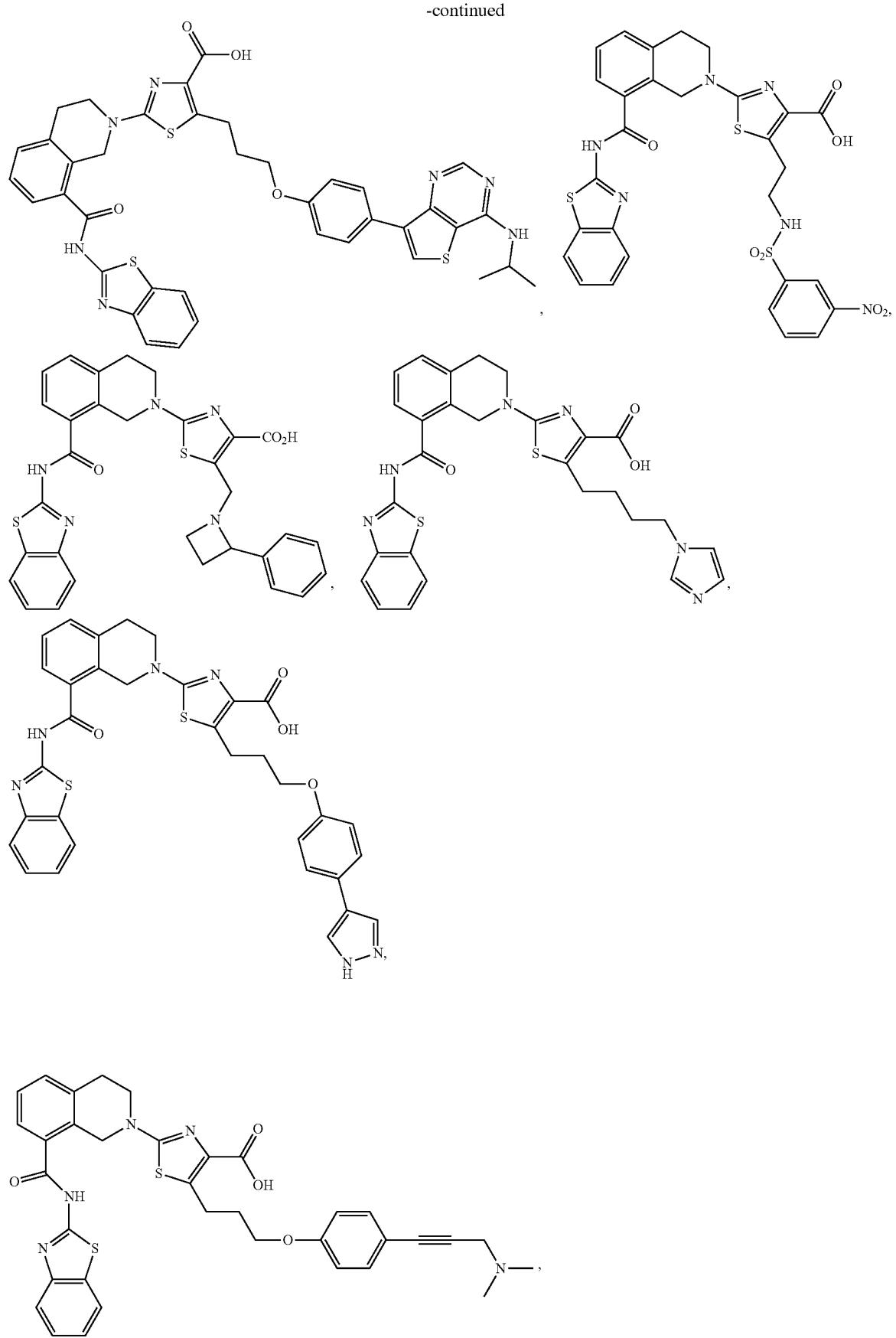

1301
1302
-continued
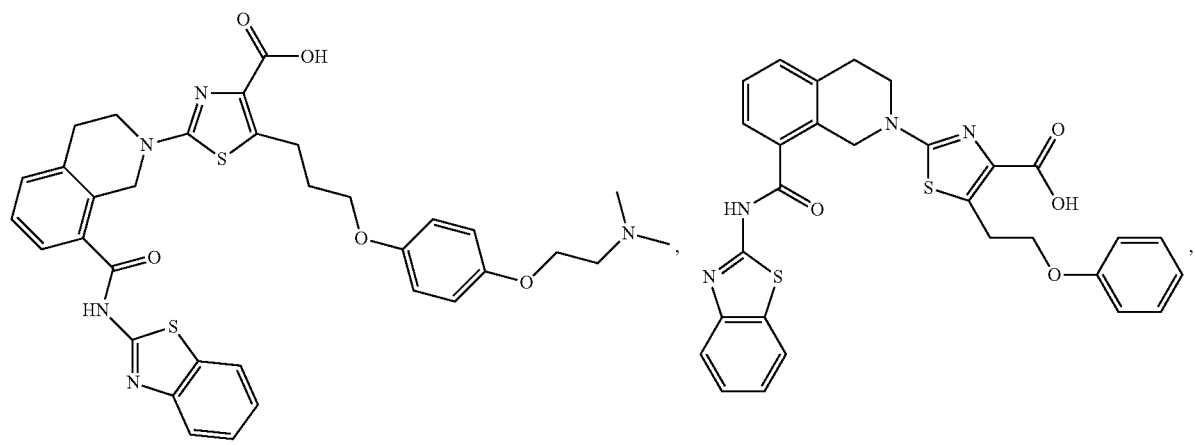
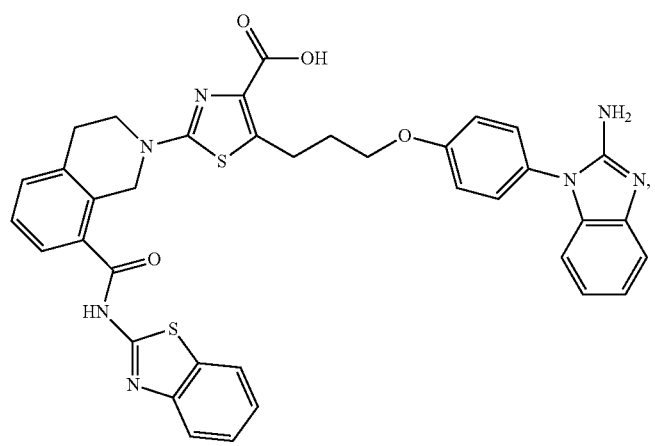
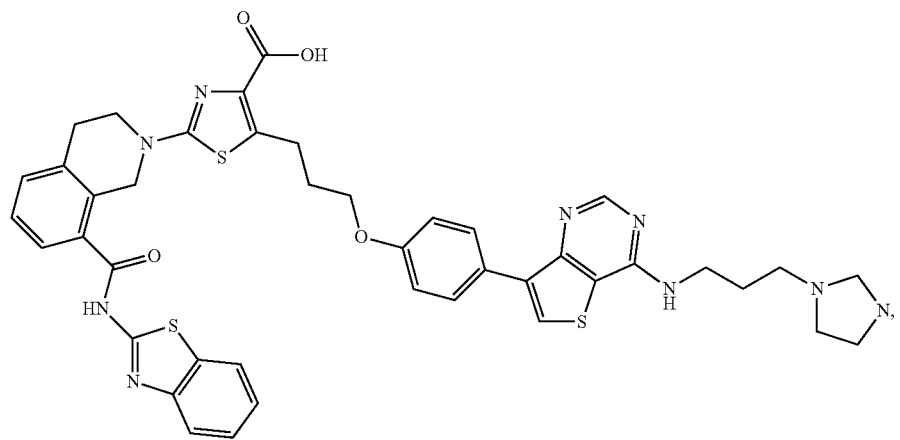

1303 1304
-continued
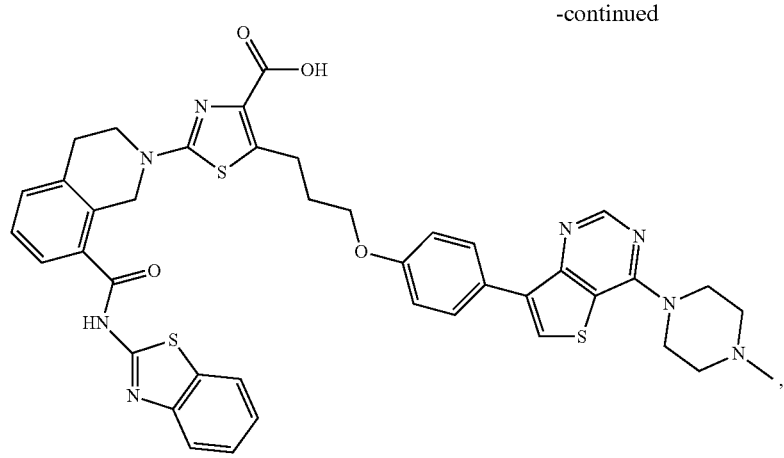
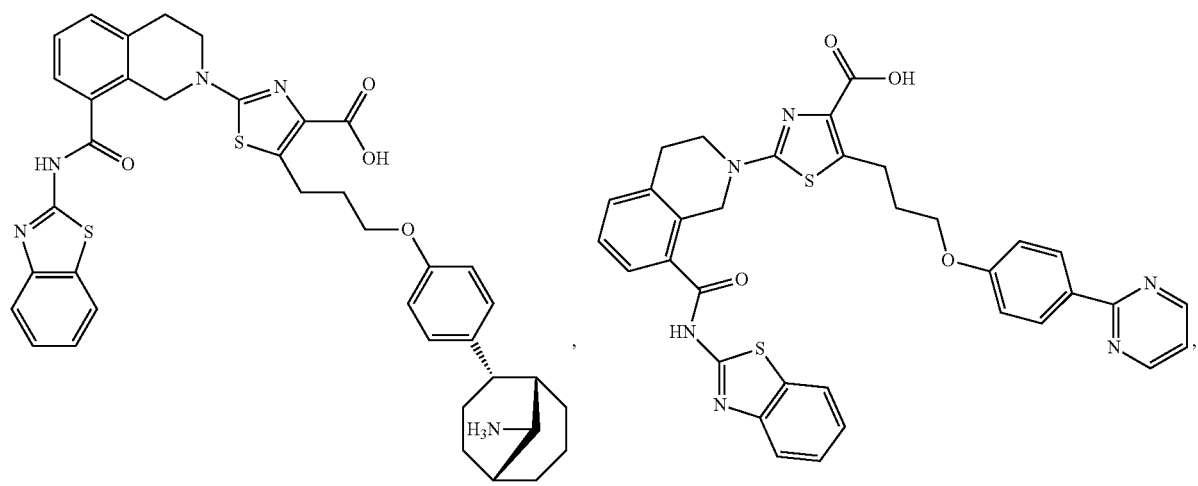
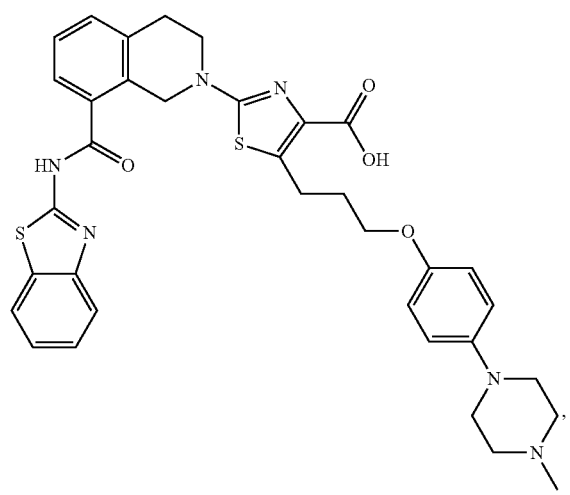

1305                                                                 1306
-continued
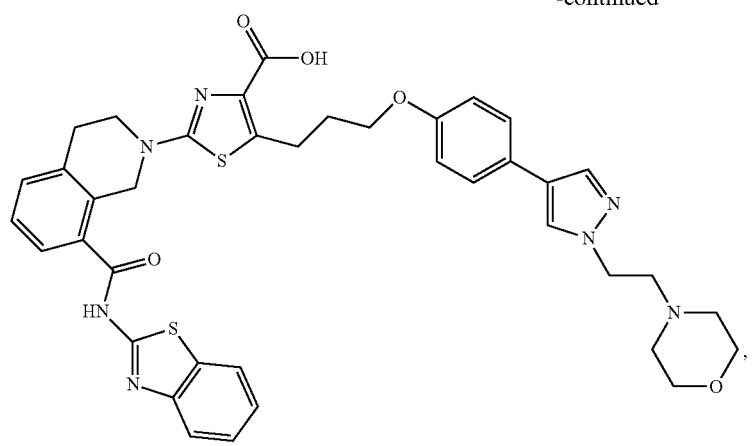
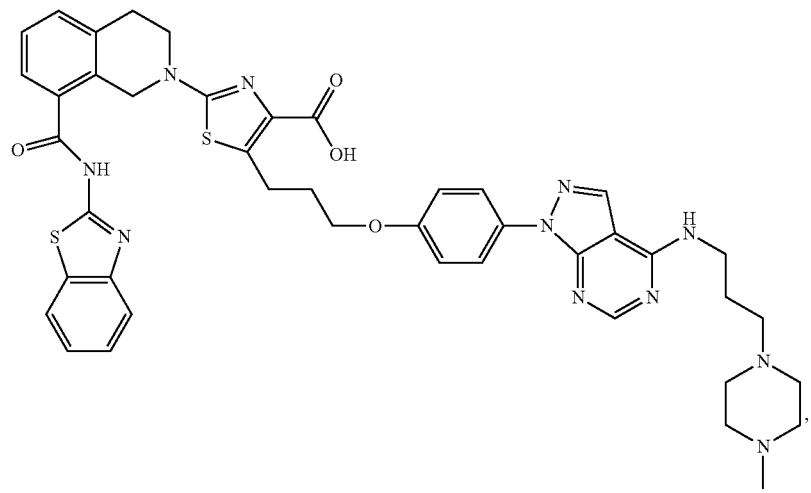
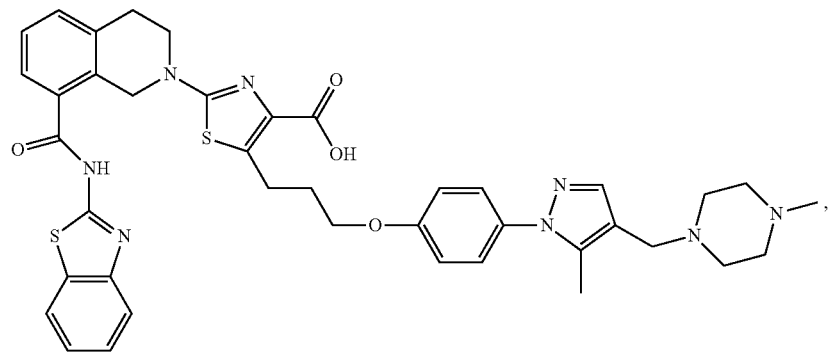
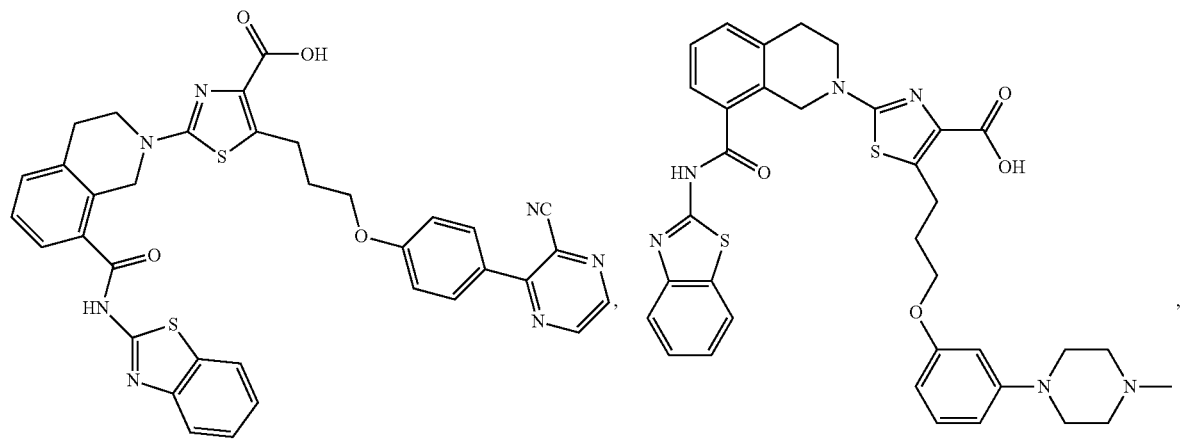

1307
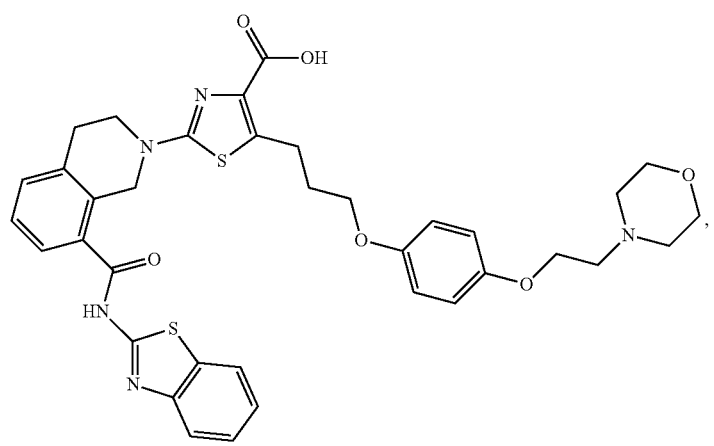
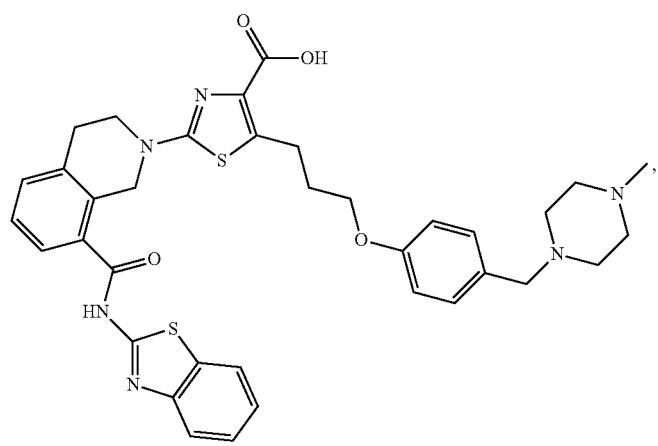
1308
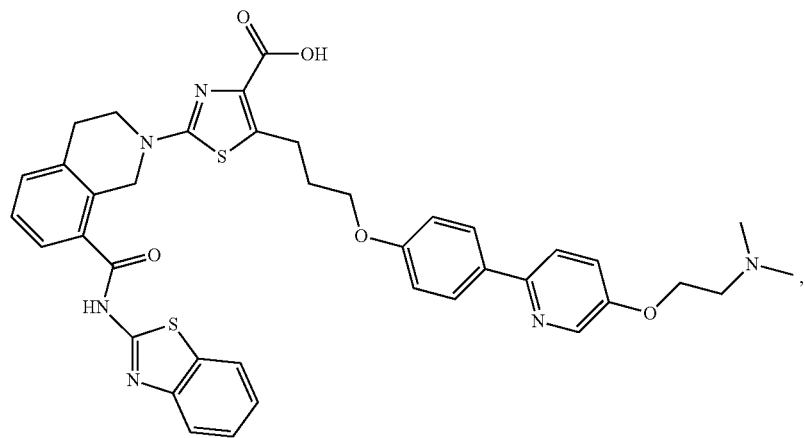

1309
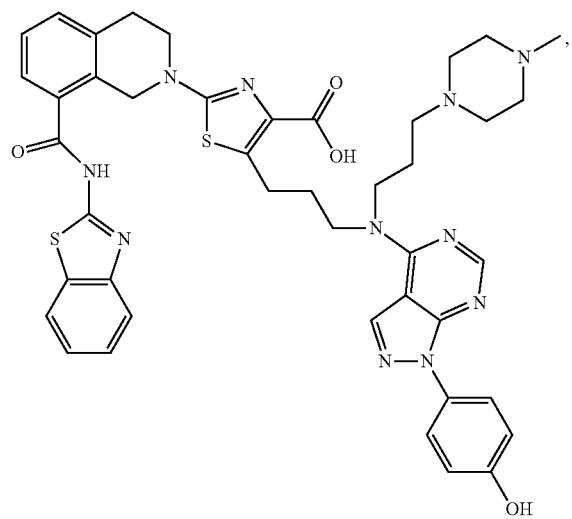
-continued
1310
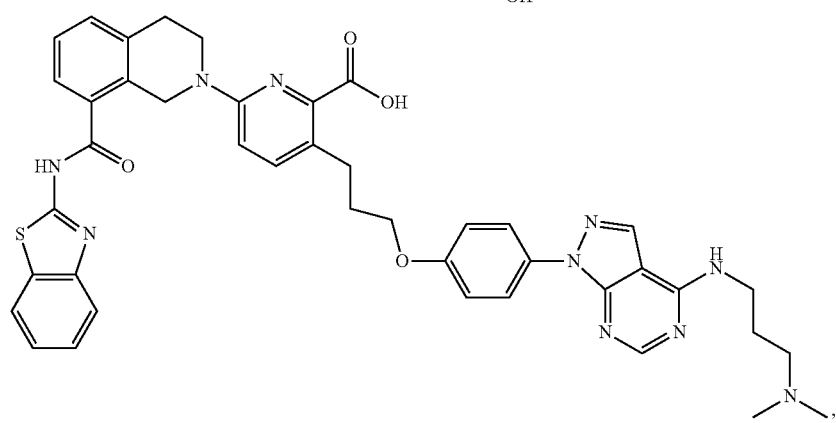
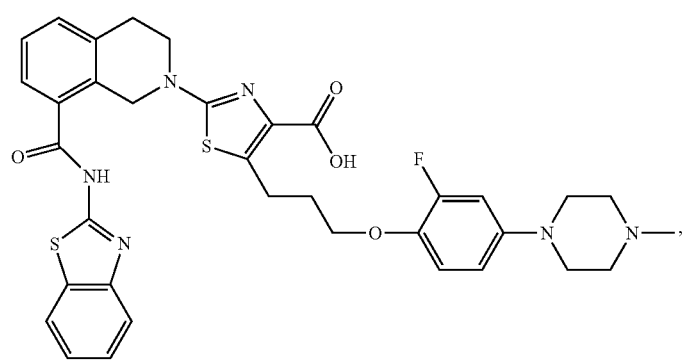
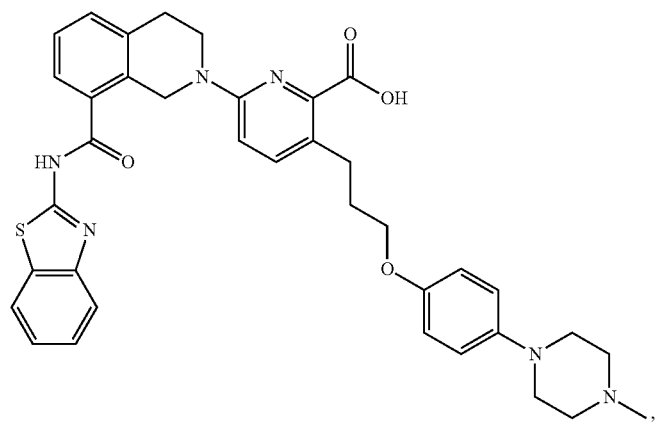

1311
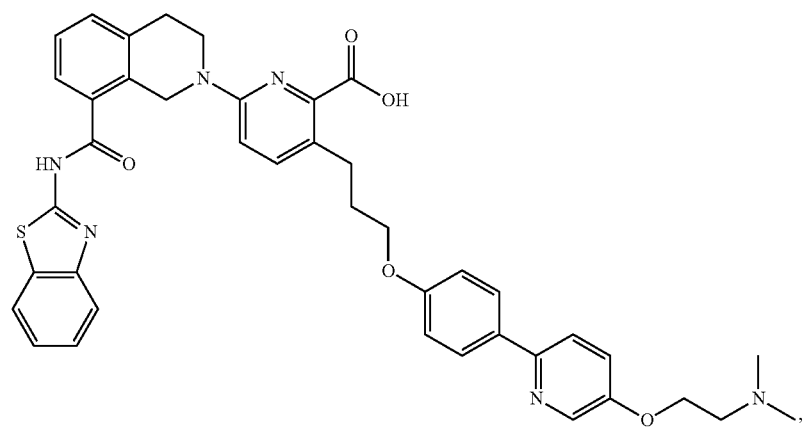
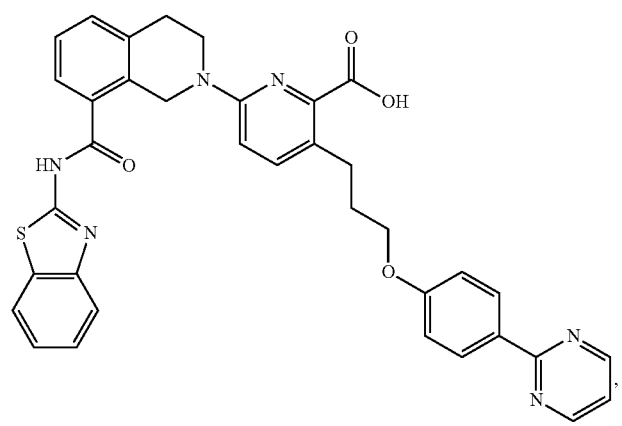
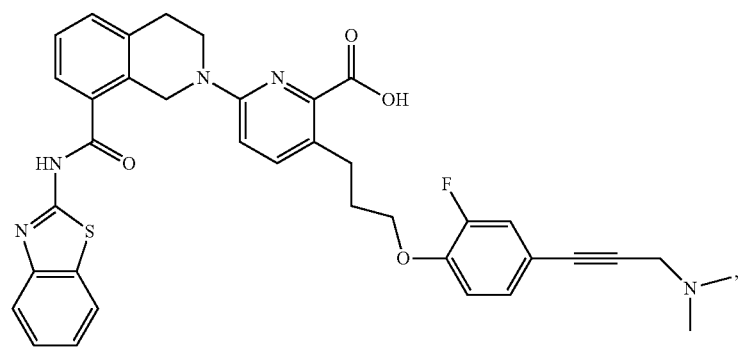
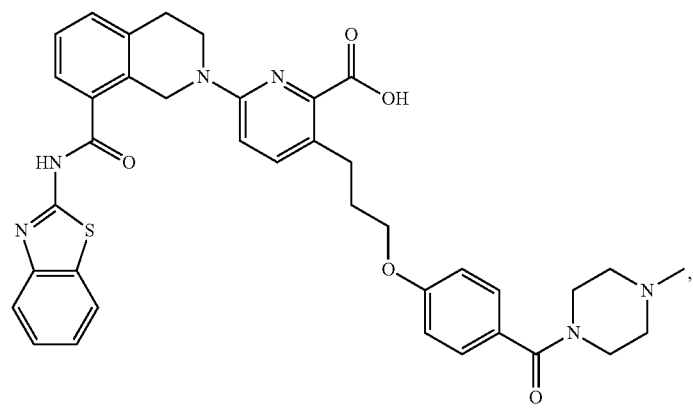
1312
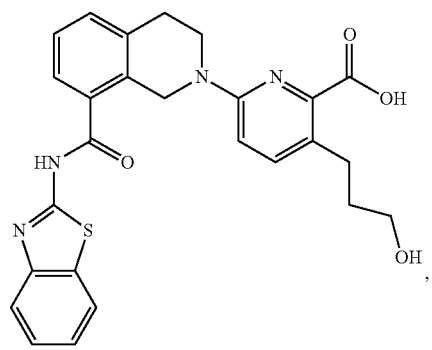

1313
-continued
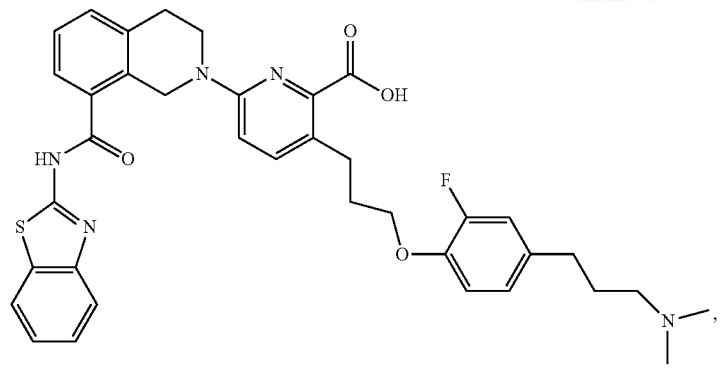
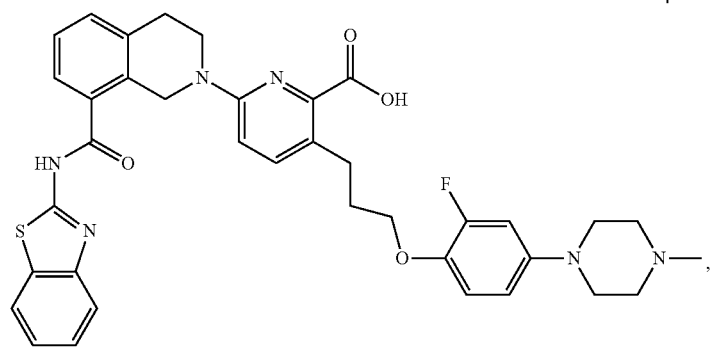
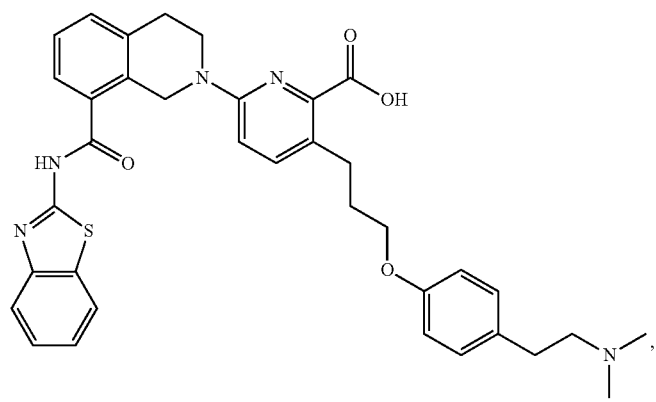
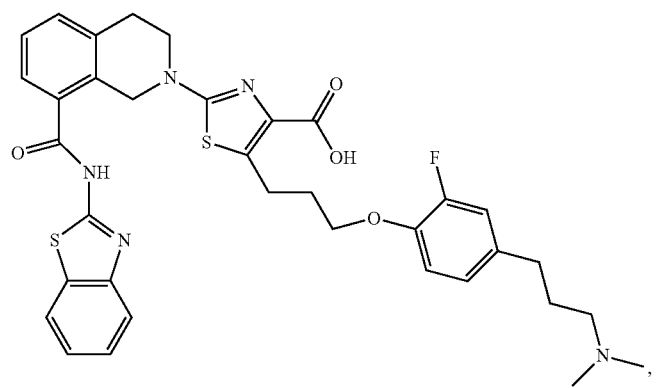
1314

1315
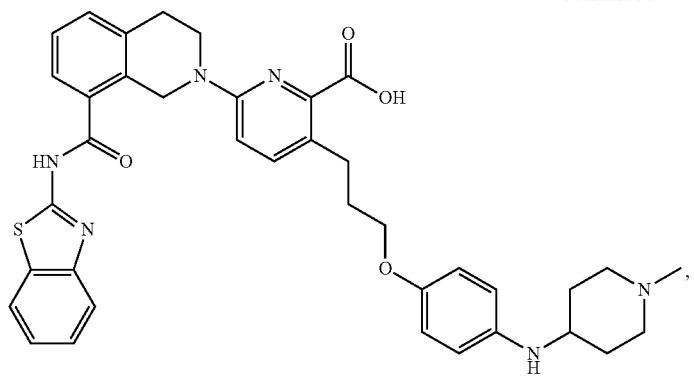
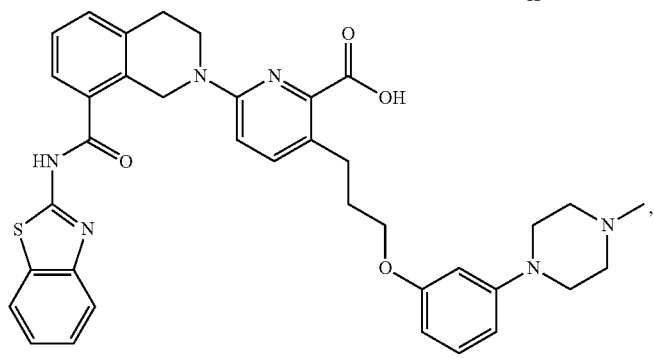
-continued
1316
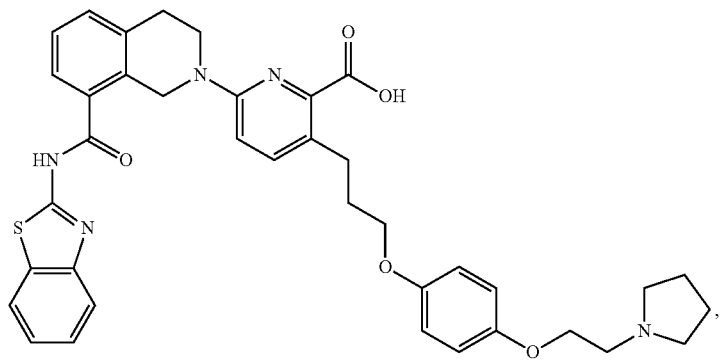
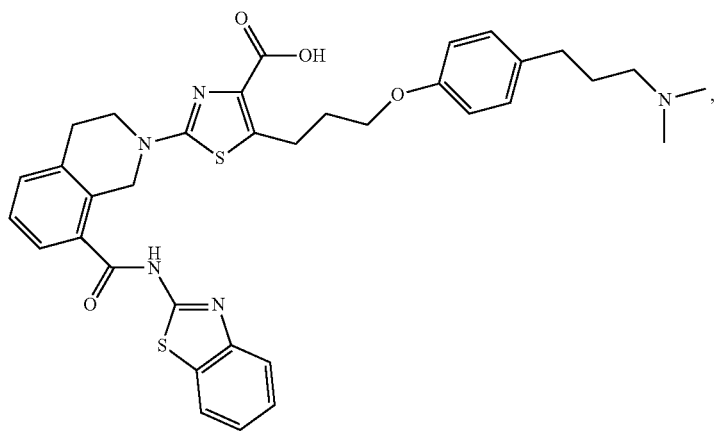

1317 1318
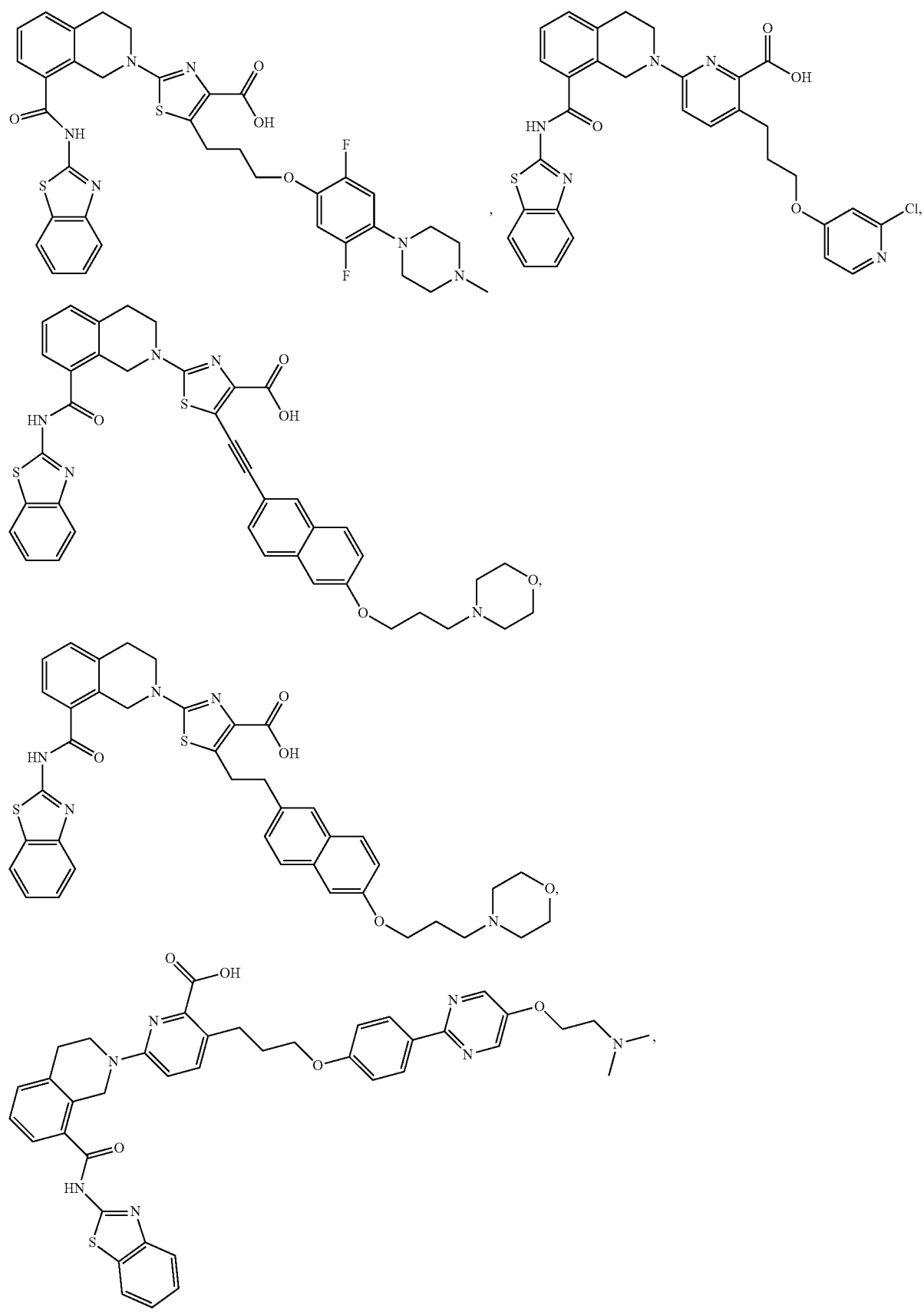

-continued
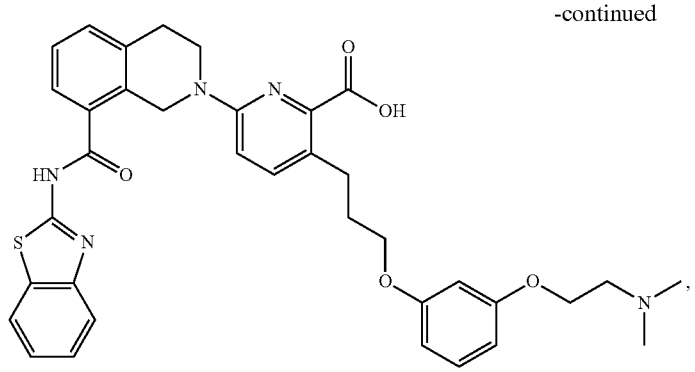
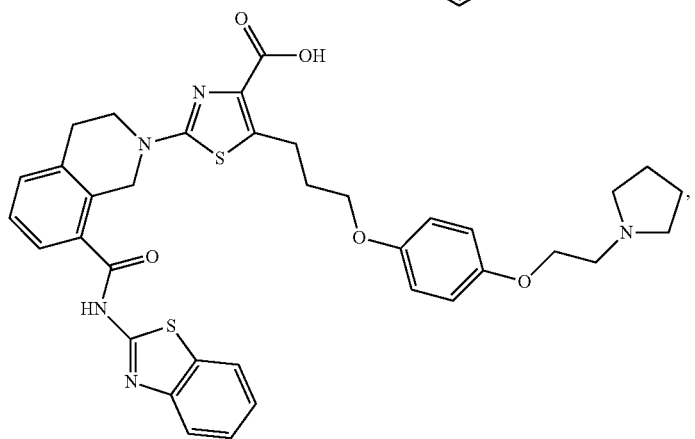
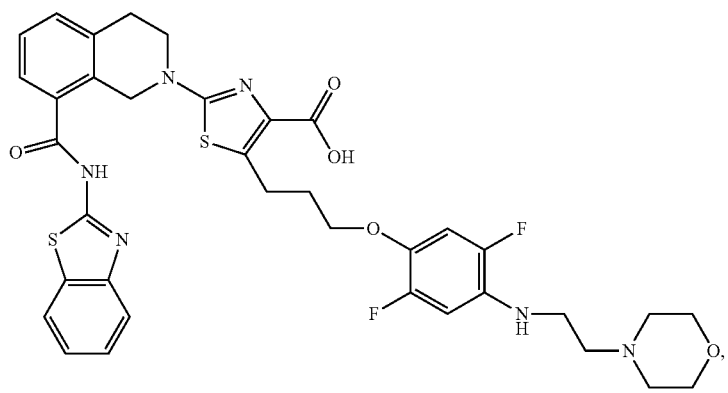
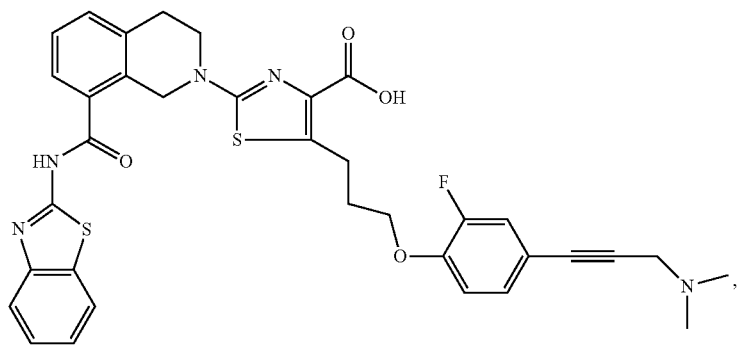

1321                                        1322
-continued
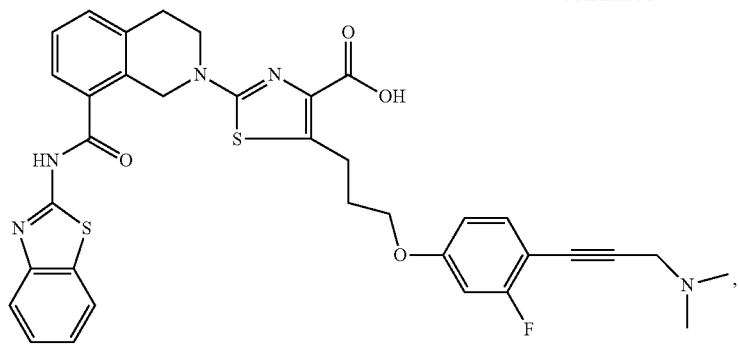
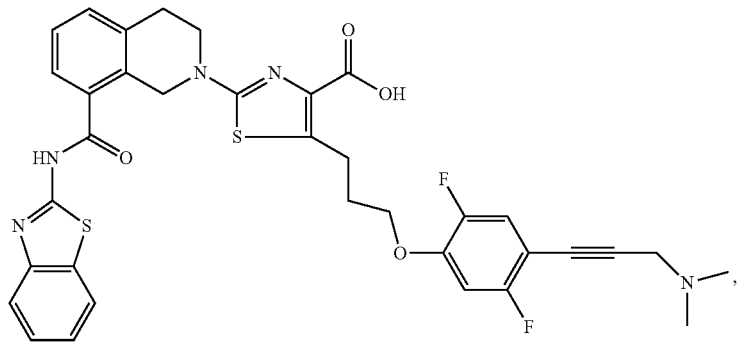
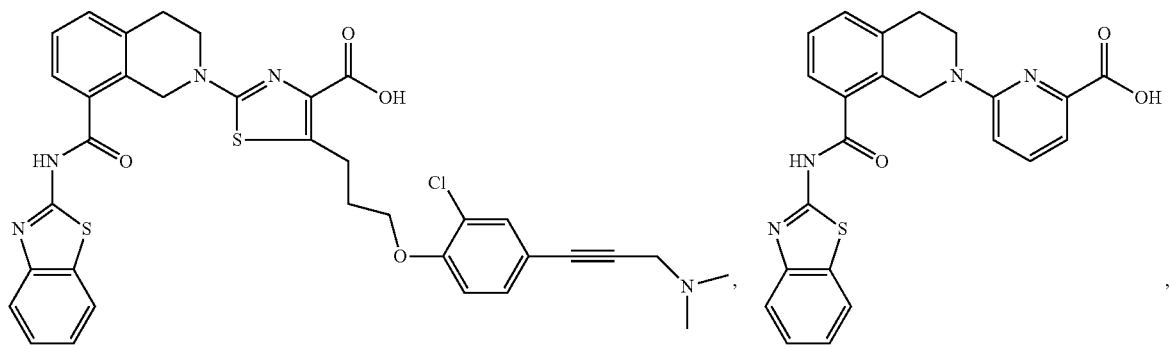
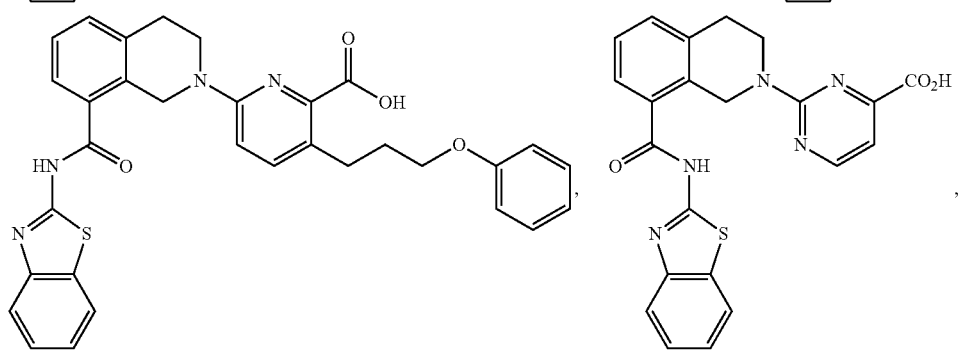
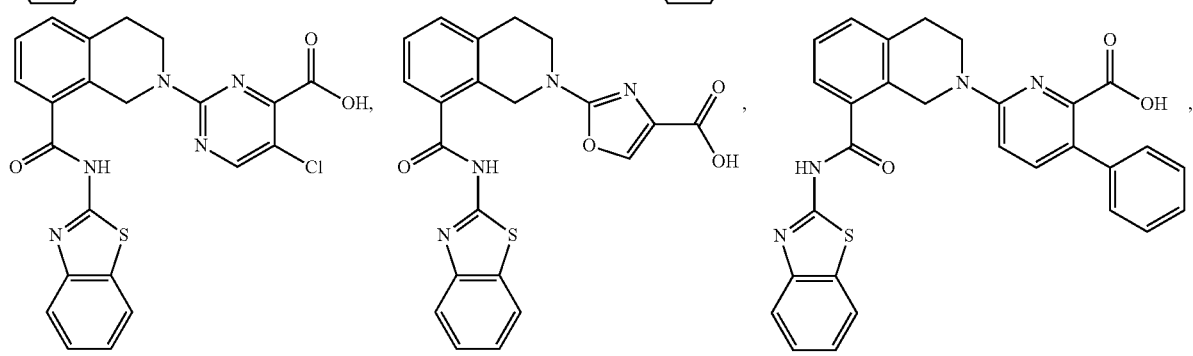

1323
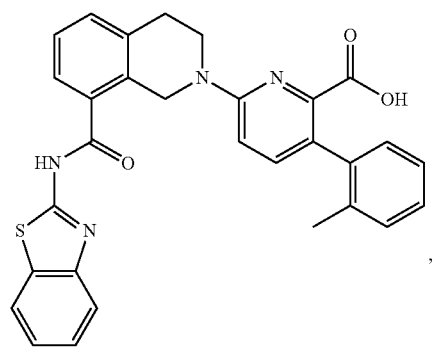
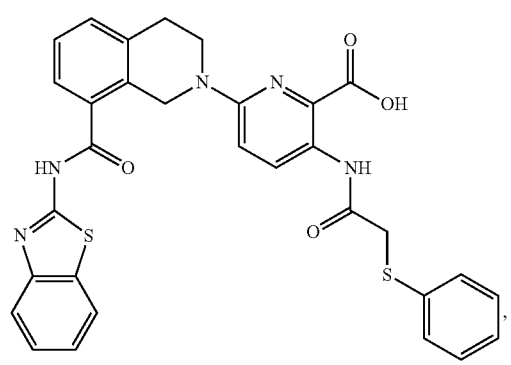
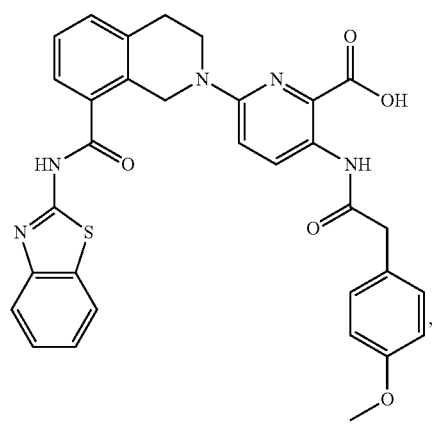
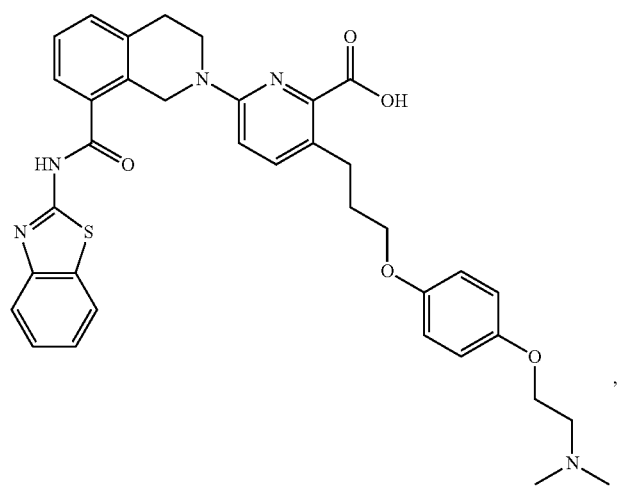
1324
-continued
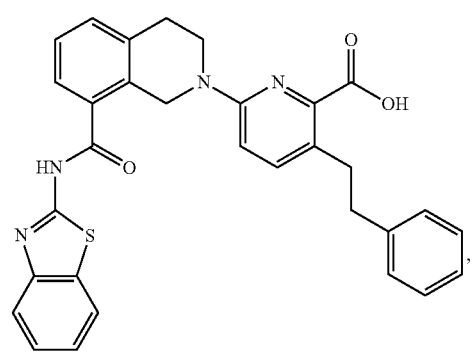
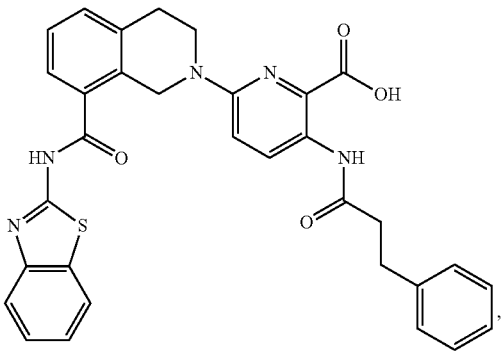
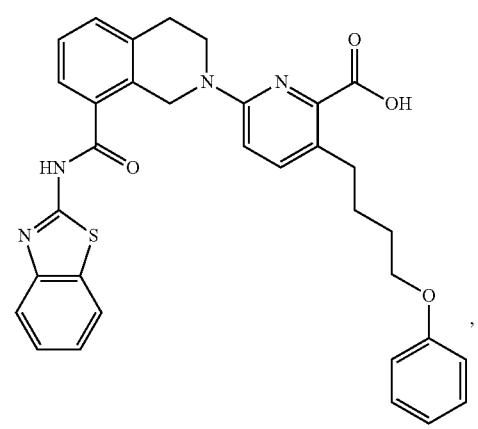

1325
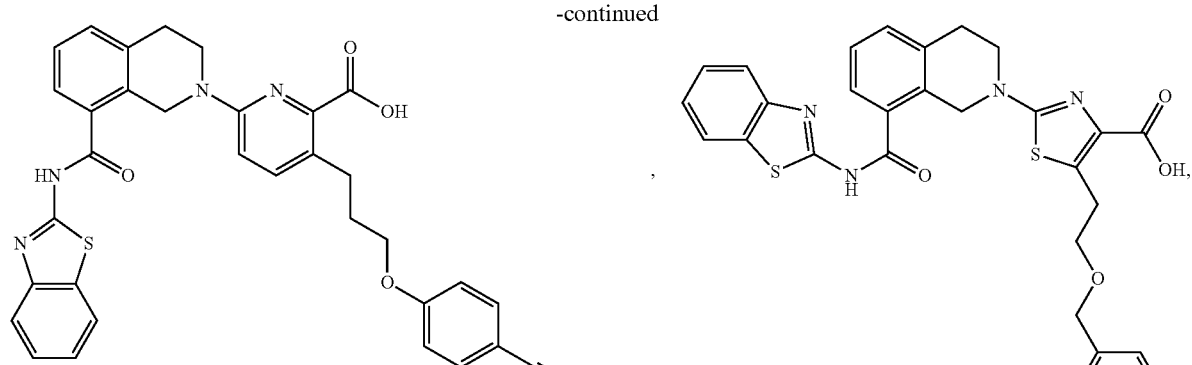
1326
-continued
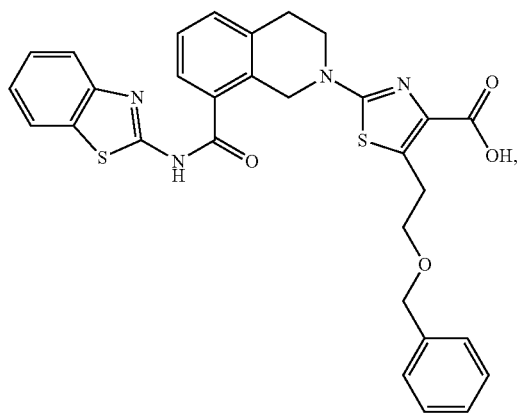

1327
-continued
1328
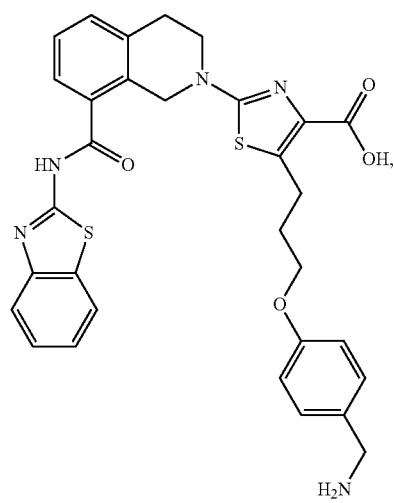
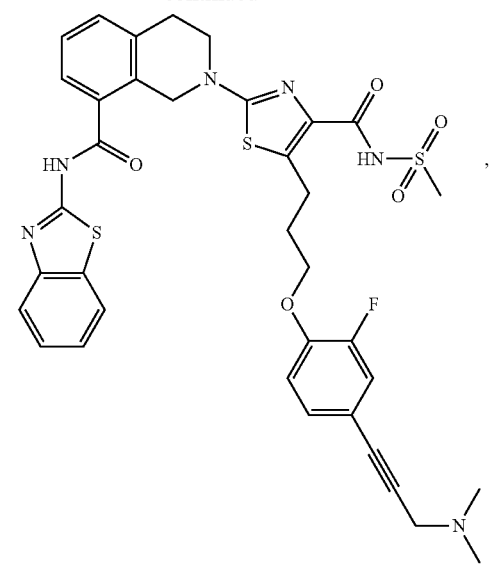
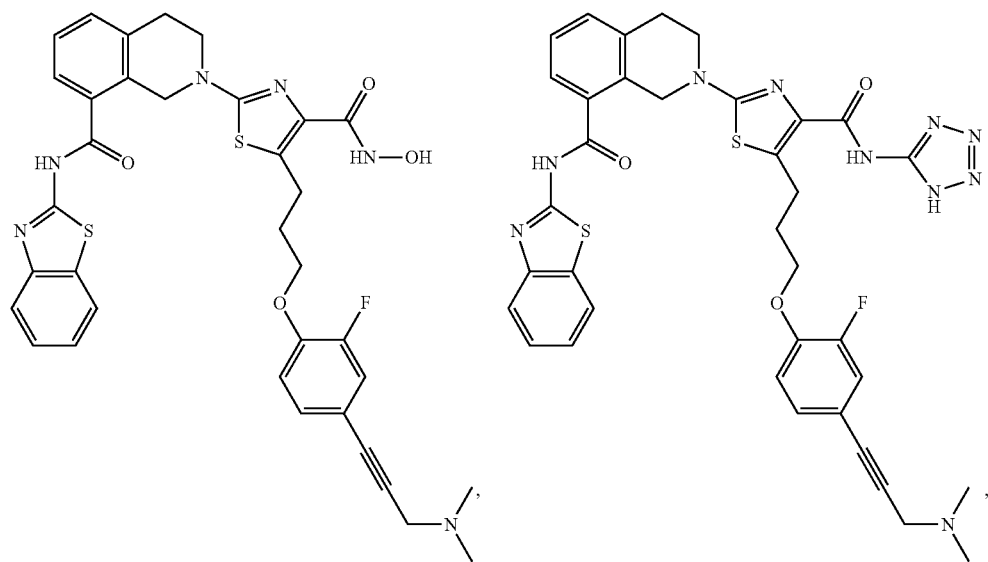
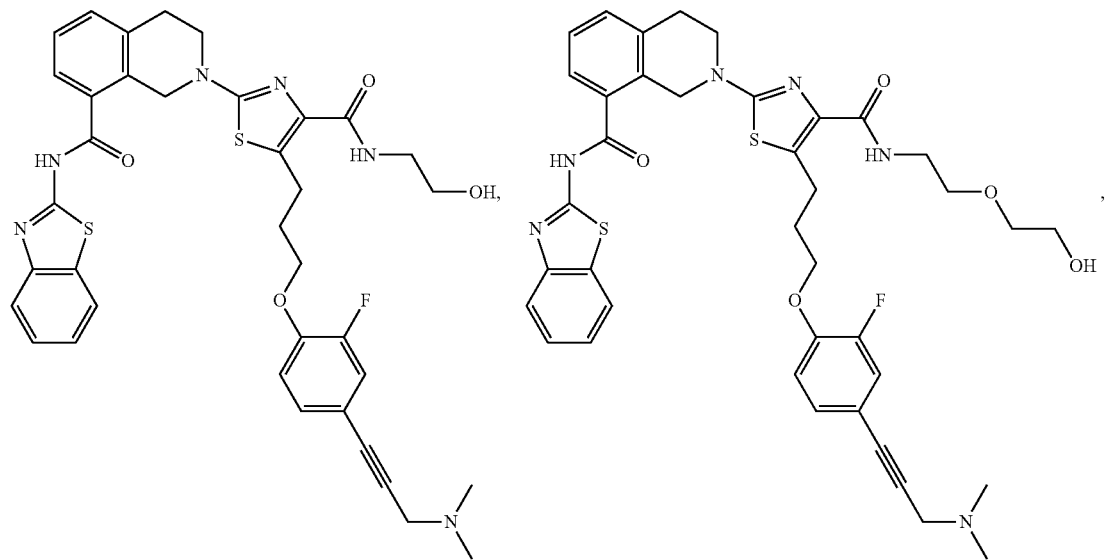

1329
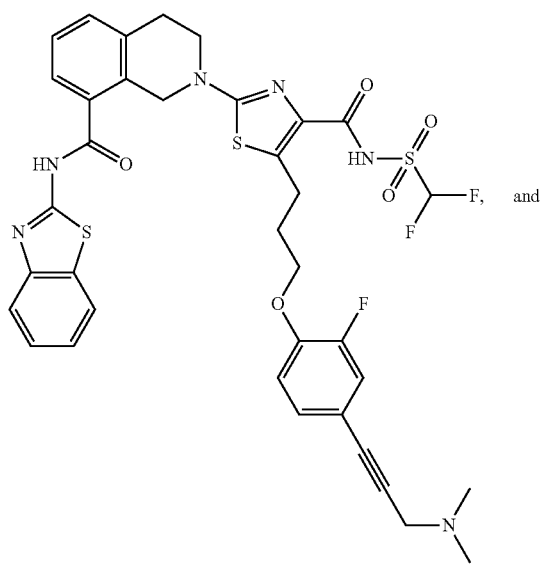
and
1330
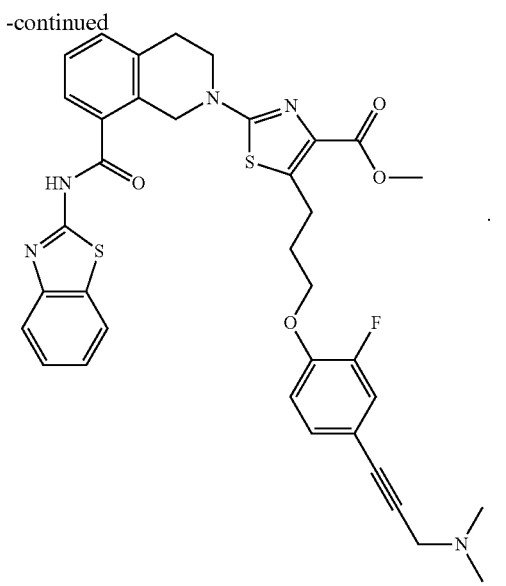
In some embodiments, the compound is selected from the group consisting of:
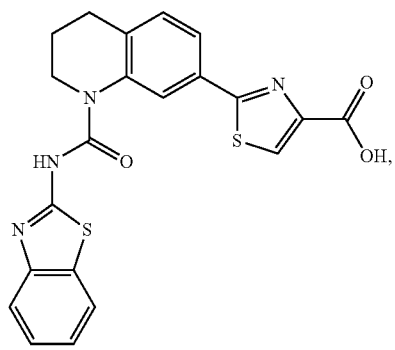
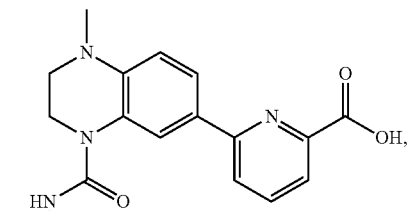
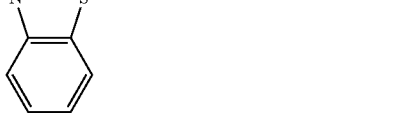
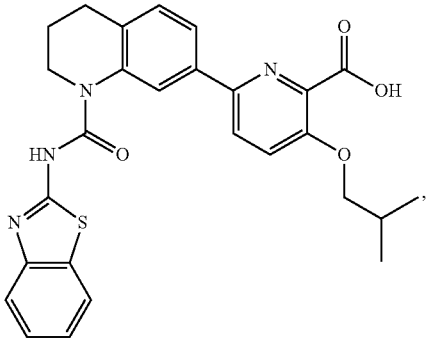
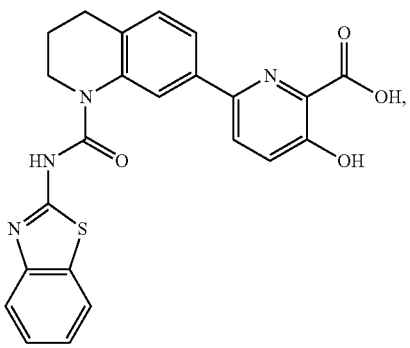
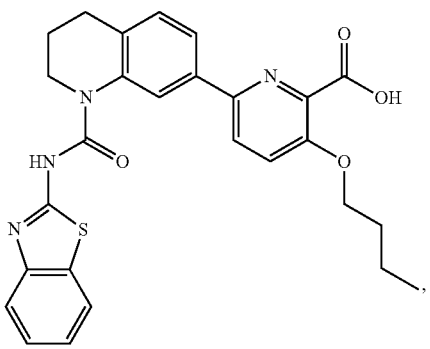

1331
-continued
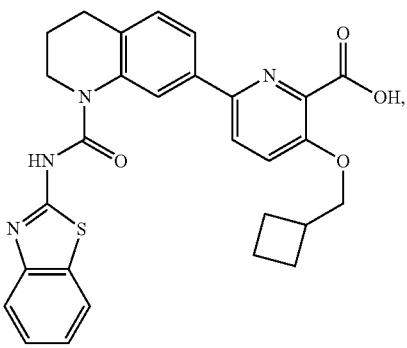
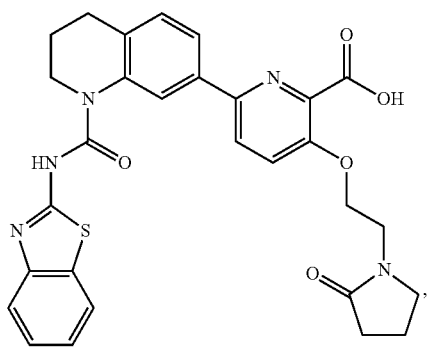
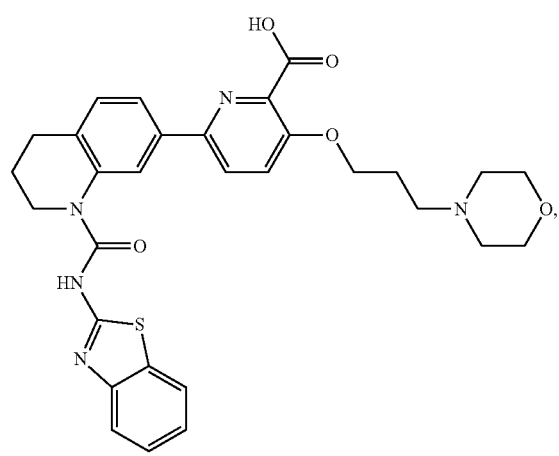
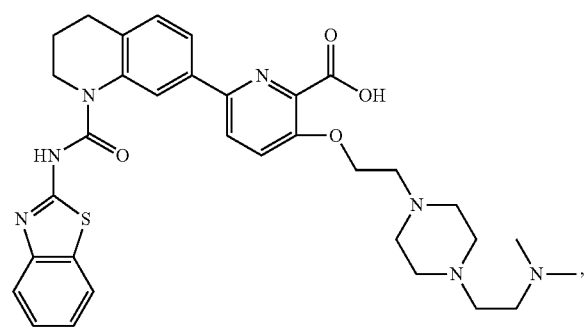
1332
-continued
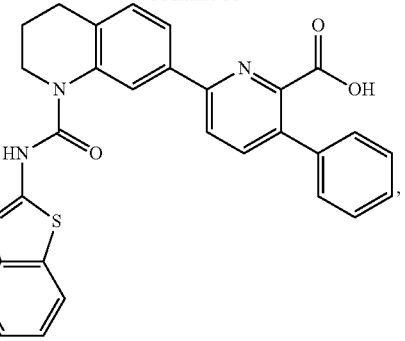
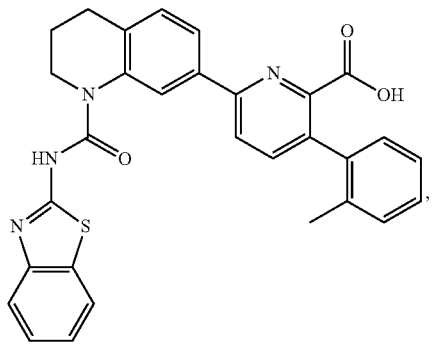
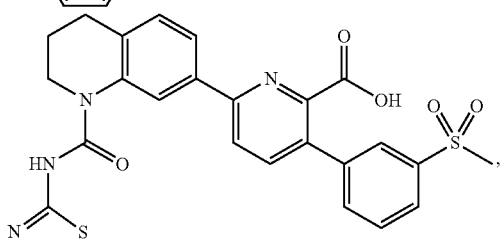
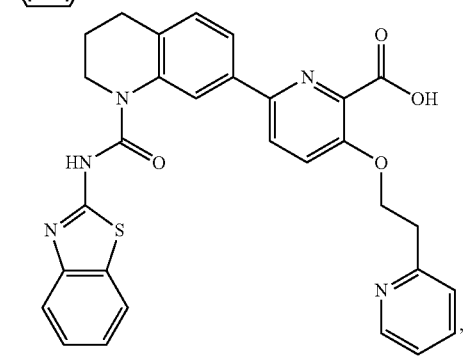
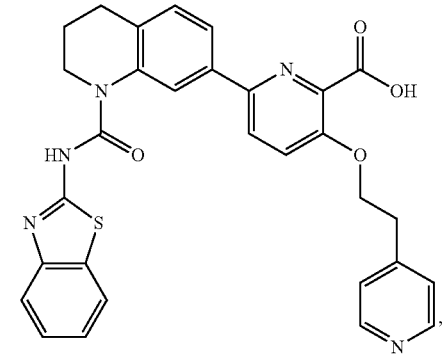

1333
-continued
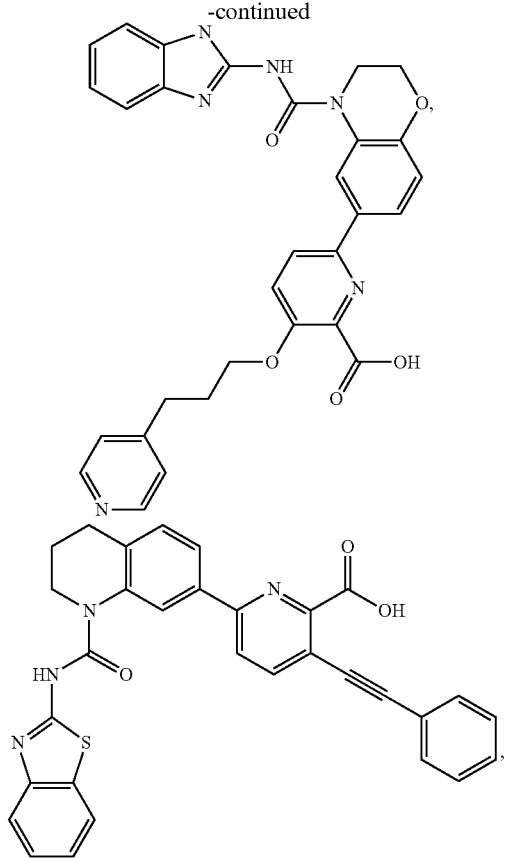
1334
-continued
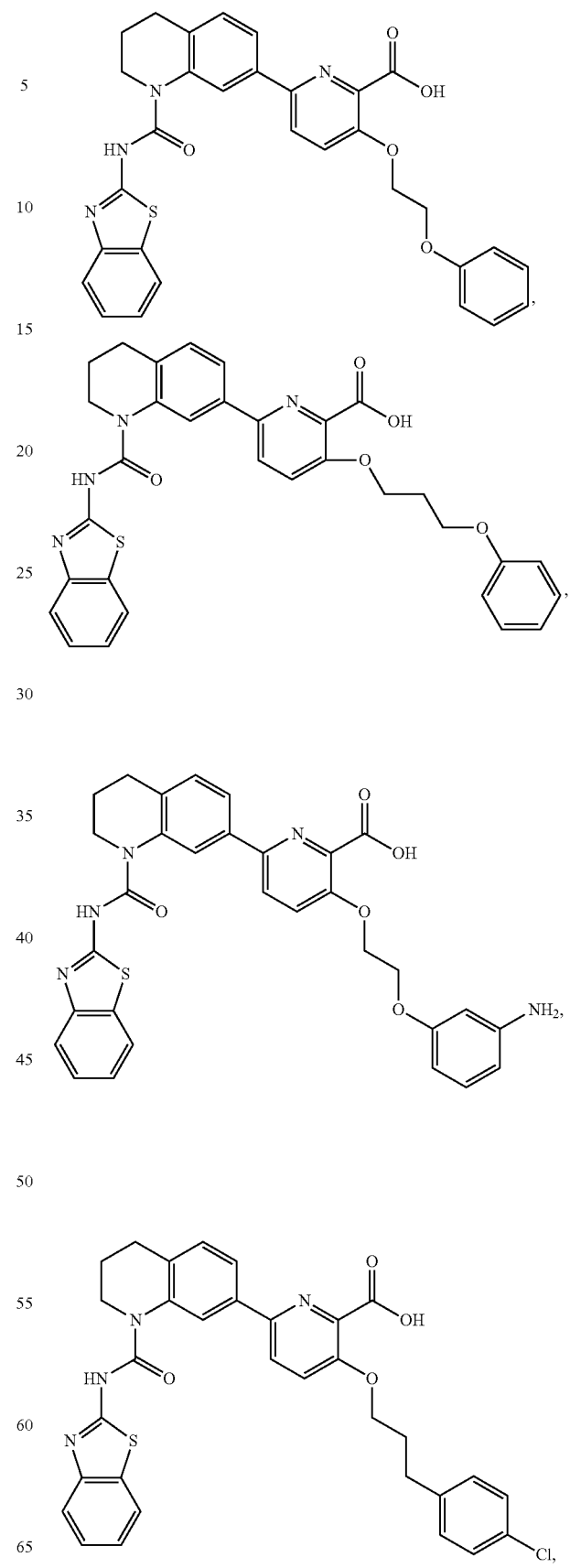

1335
-continued
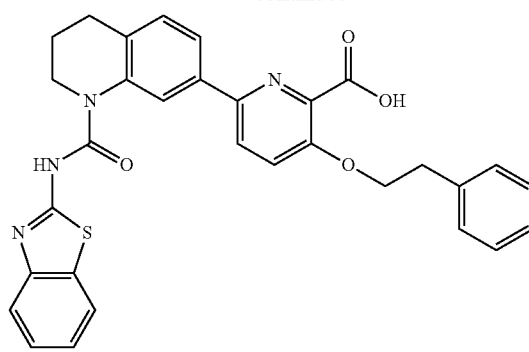
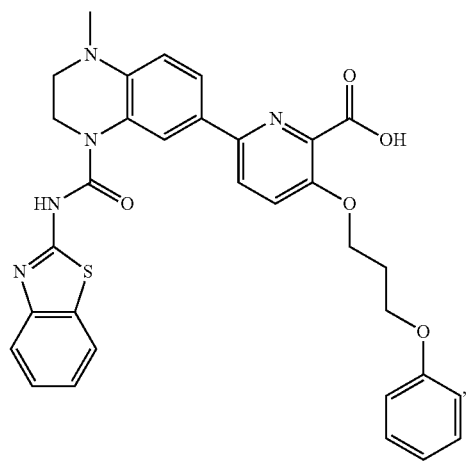
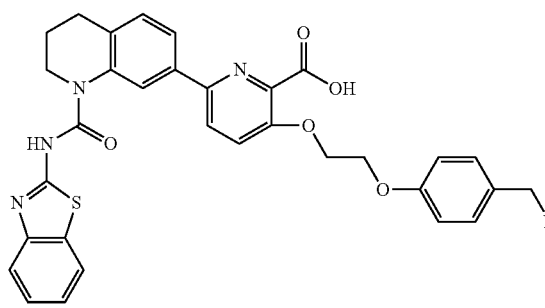
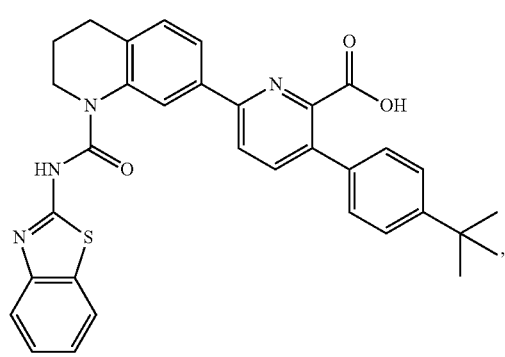
1336
-continued
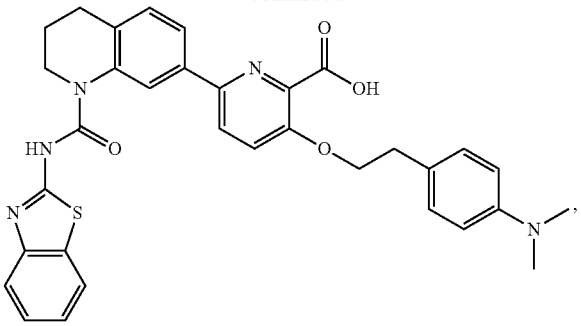
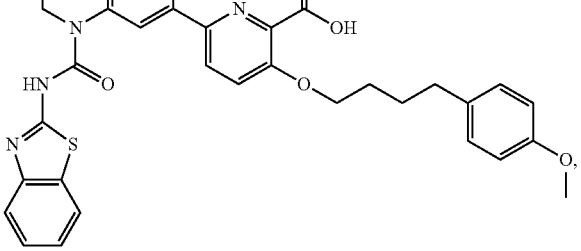
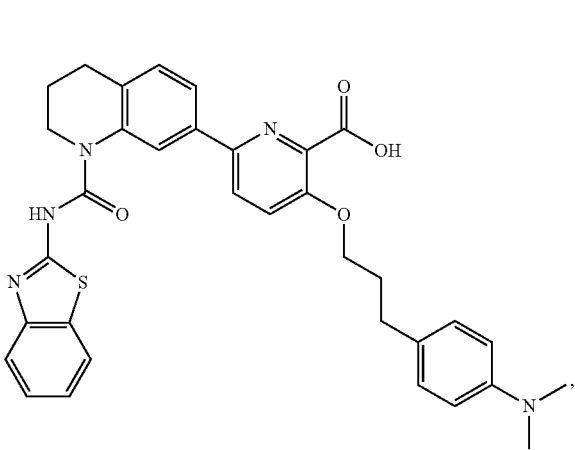

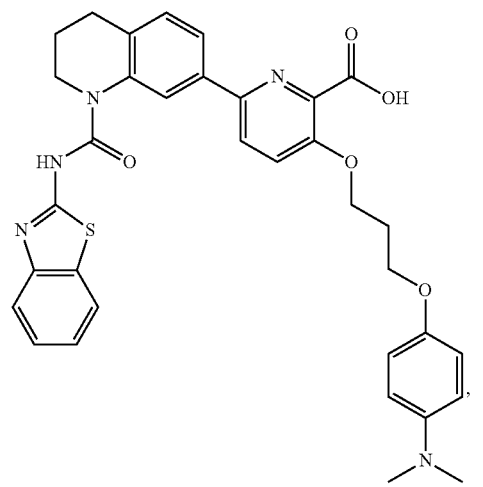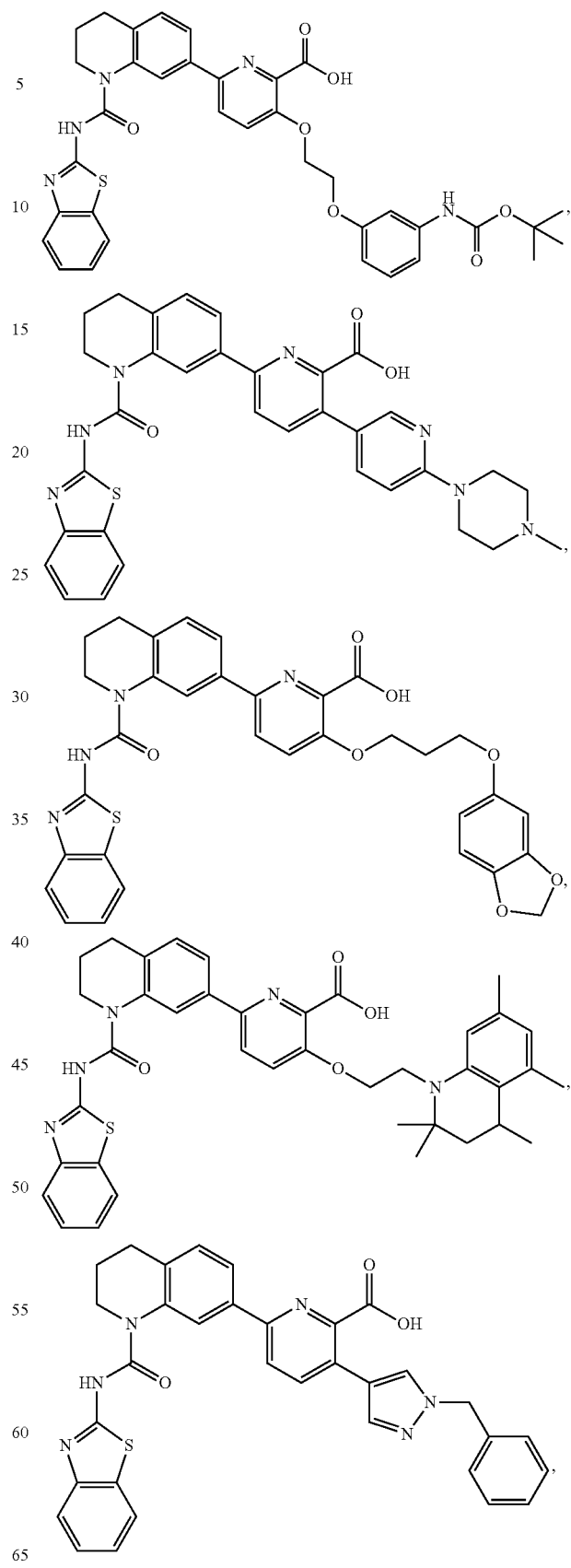

1339
-continued
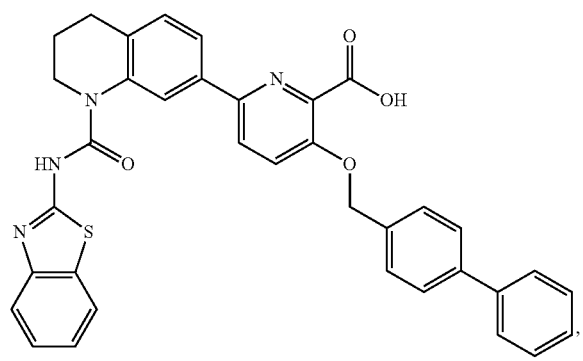
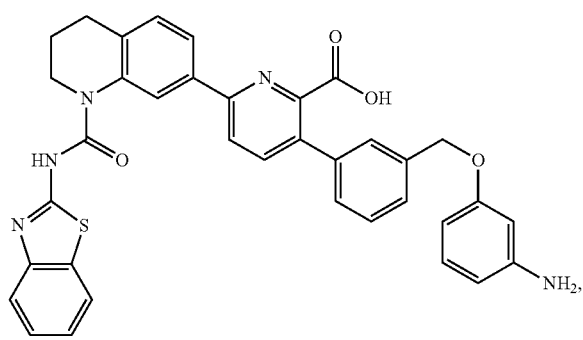
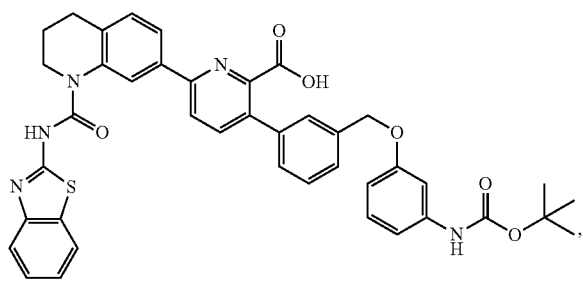
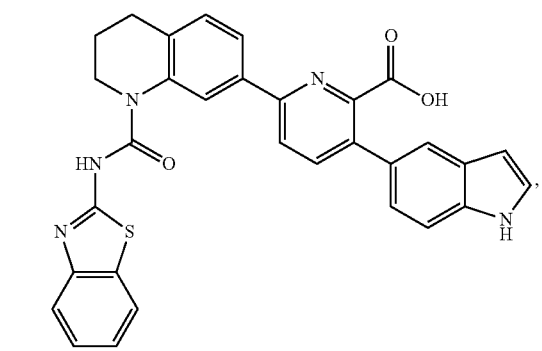
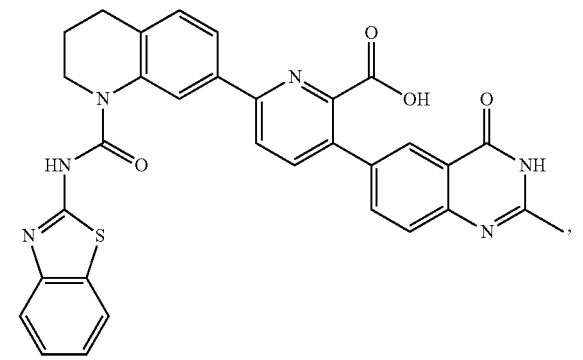
1340
-continued
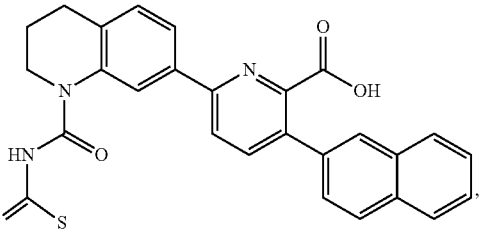
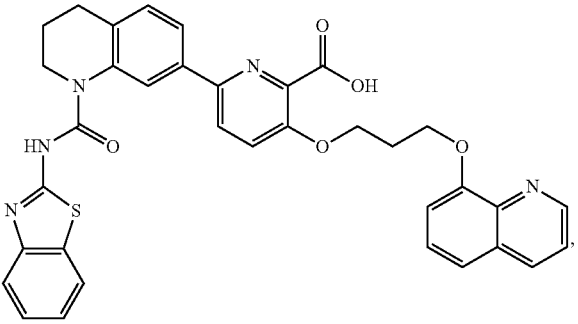
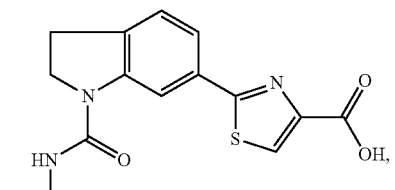
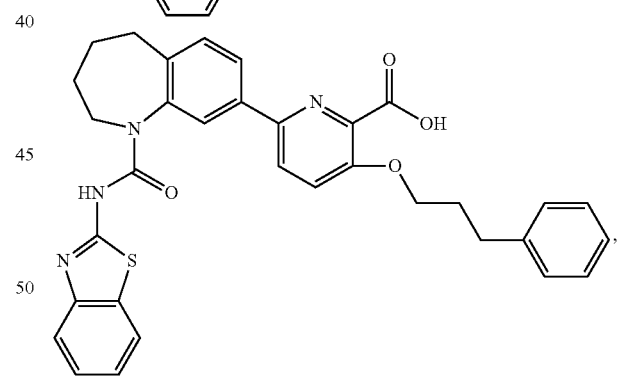
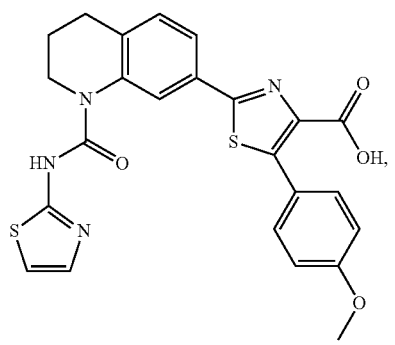

1341
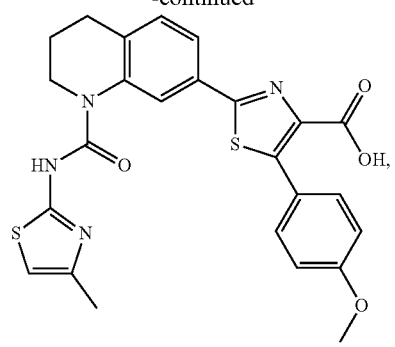
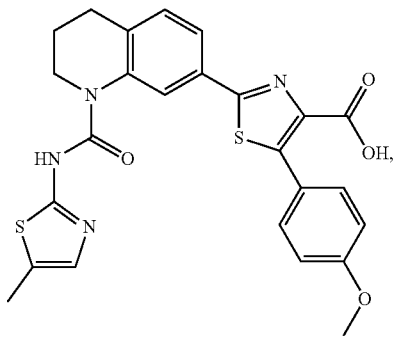
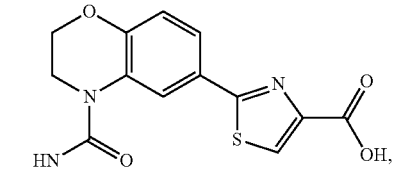
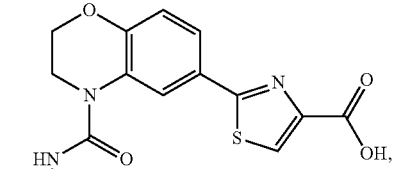
1342
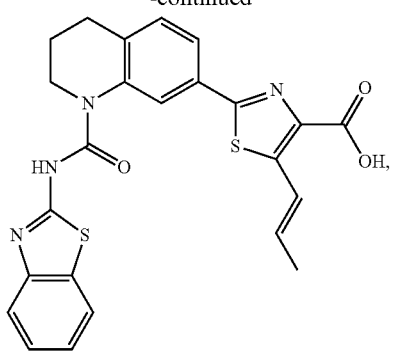
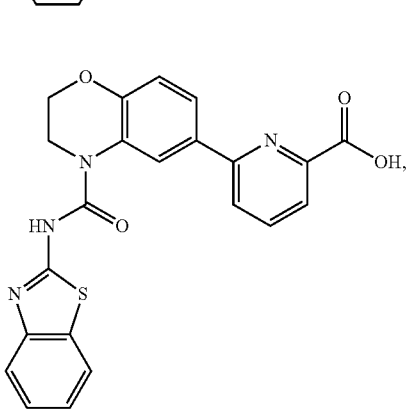
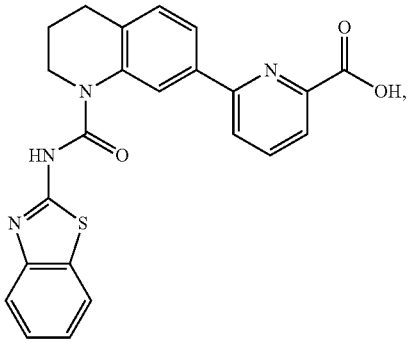
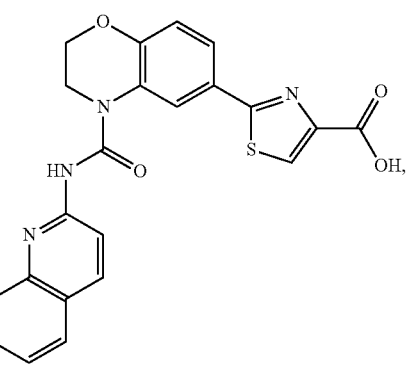

1343
-continued
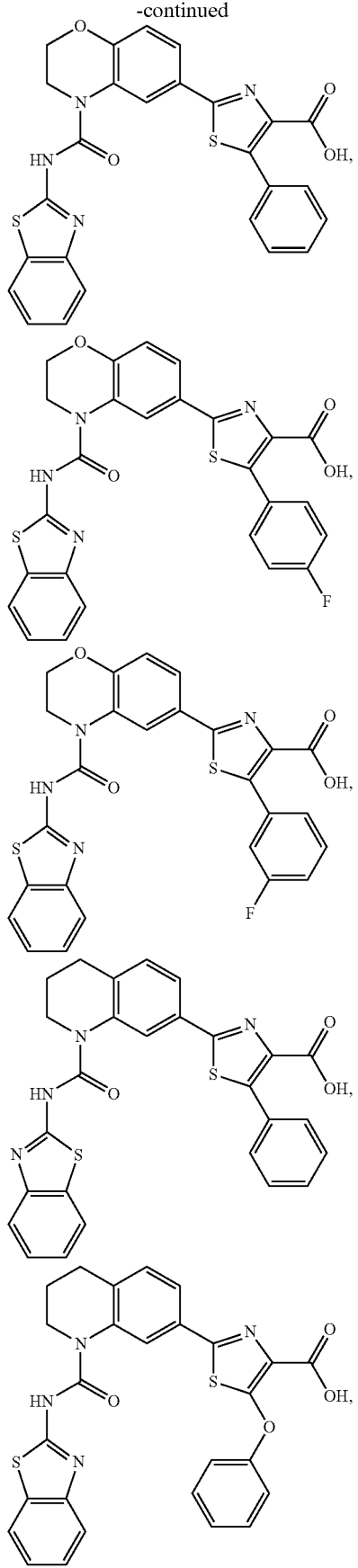
1344
-continued
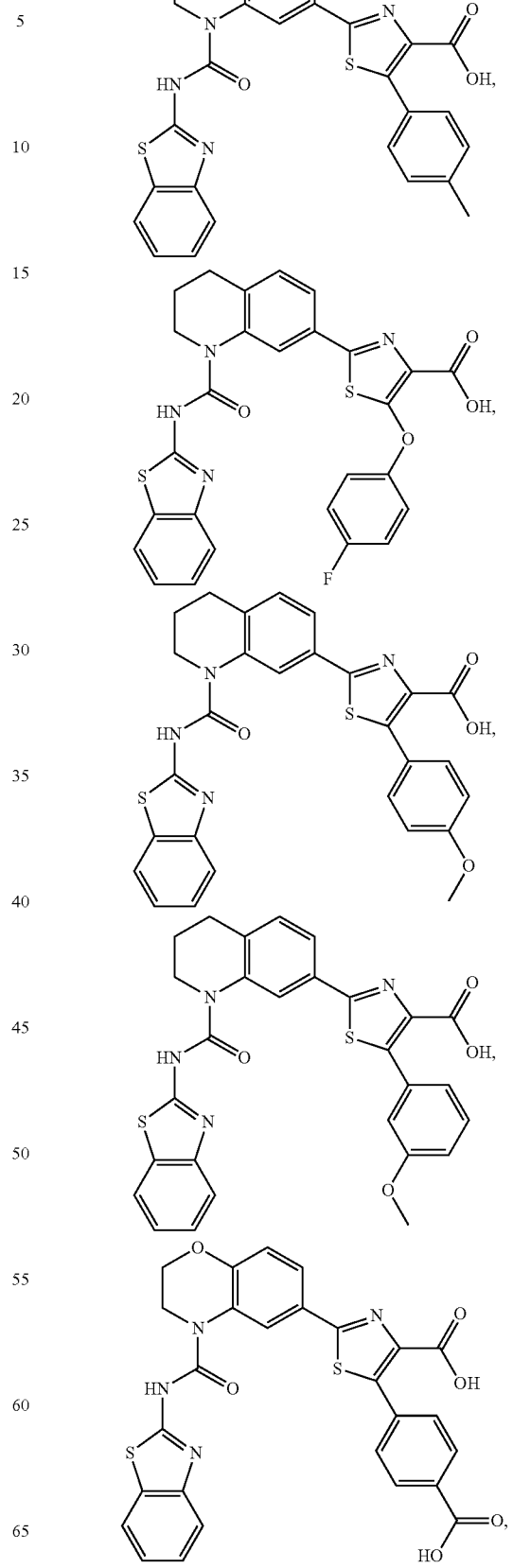

1345
-continued
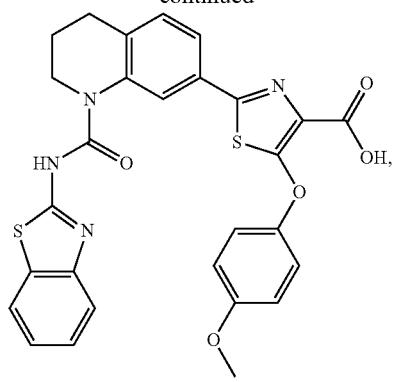
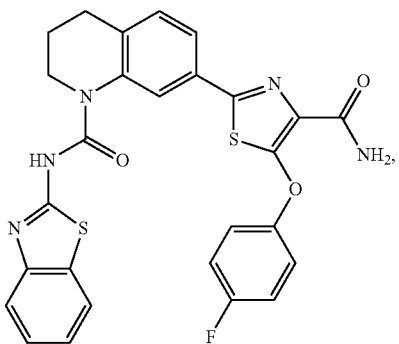
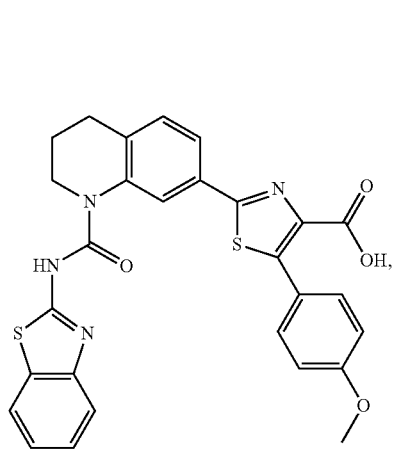
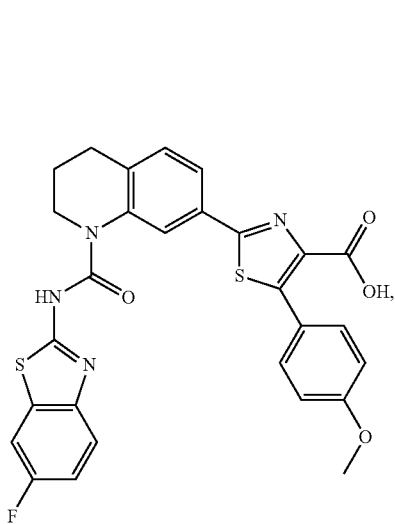
1346
-continued
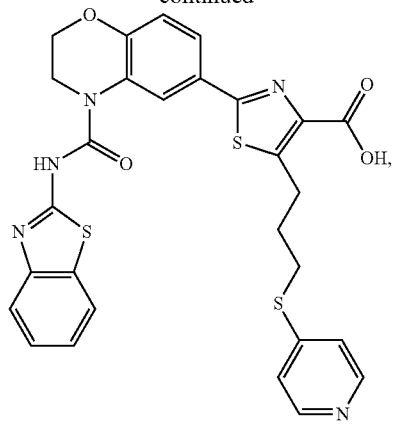
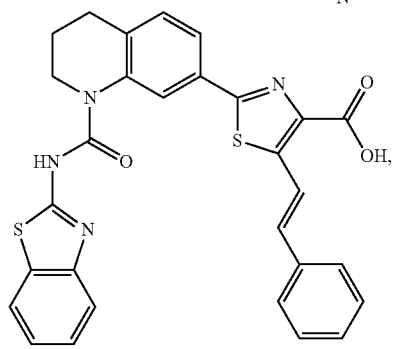
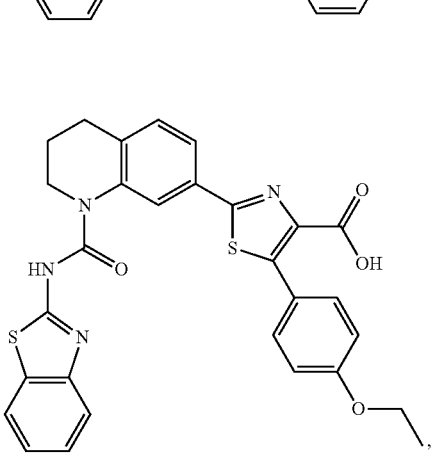
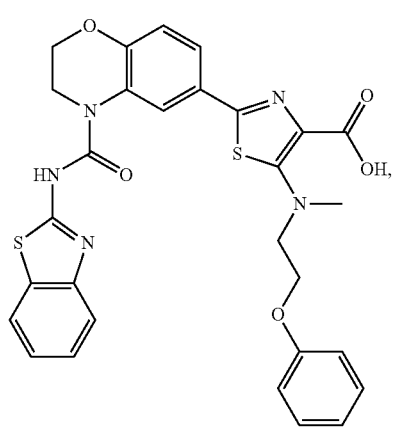

1347
-continued
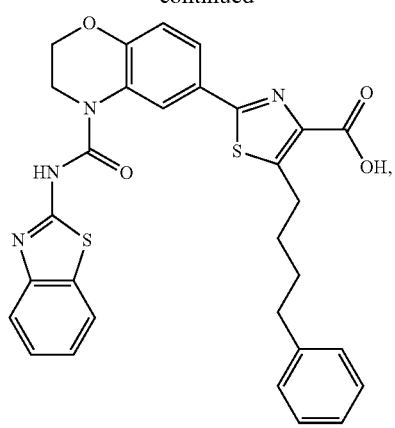
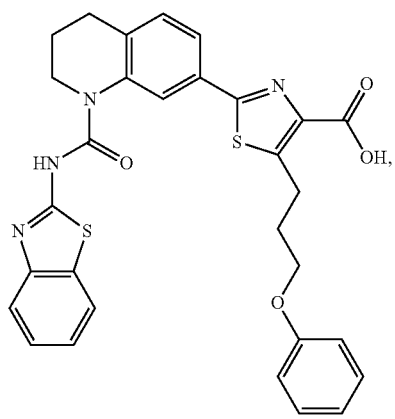
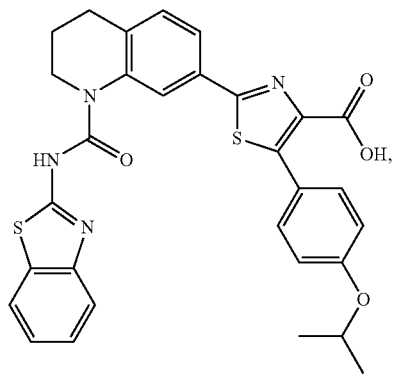
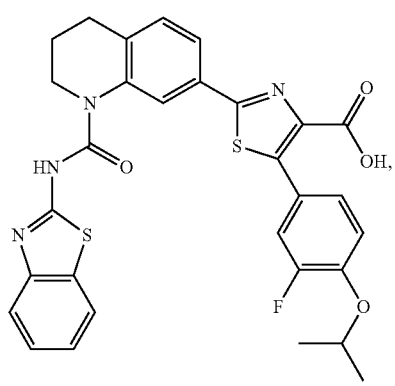
1348
-continued
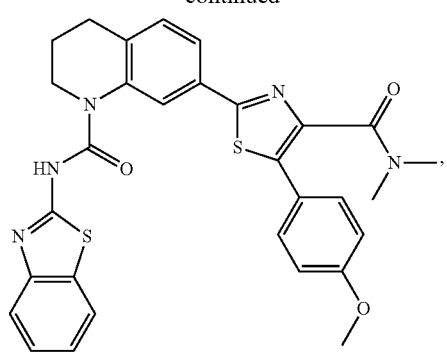
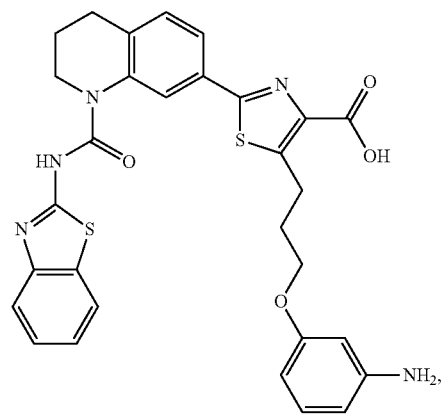
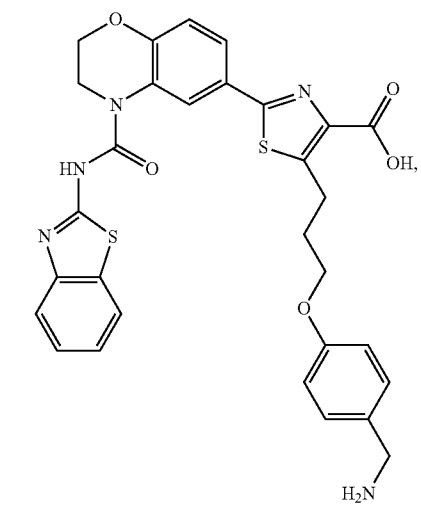

1349
-continued
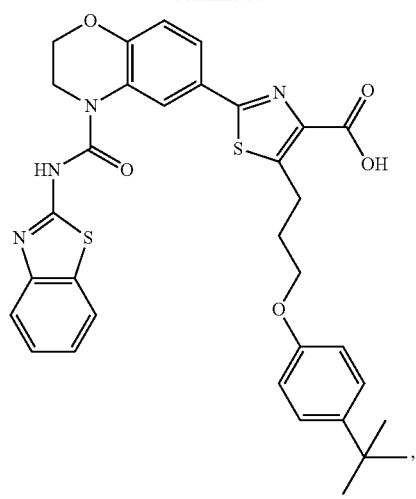
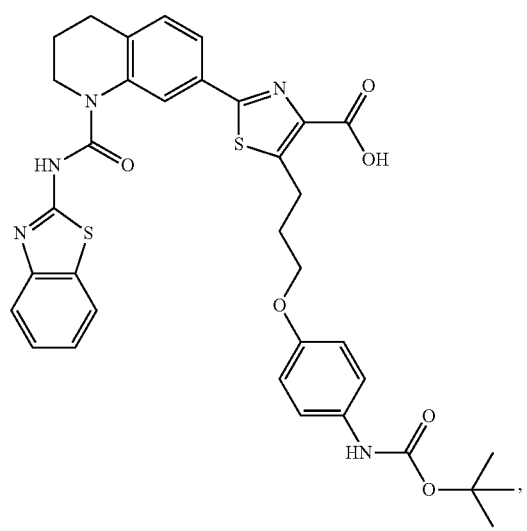
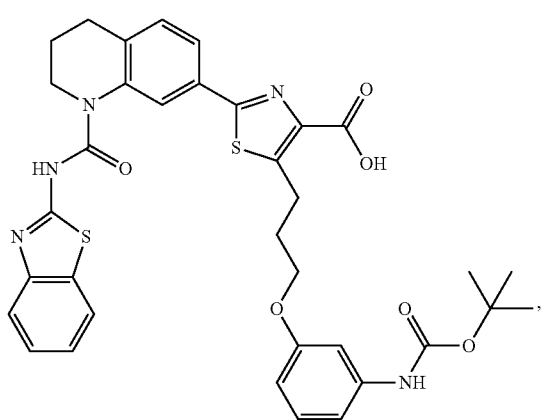
1350
-continued
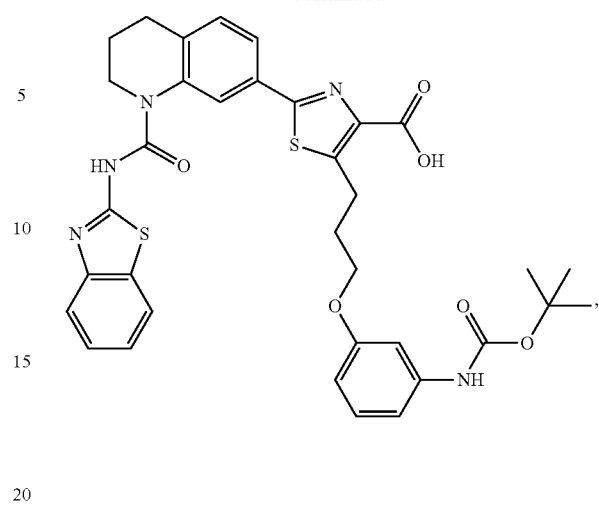
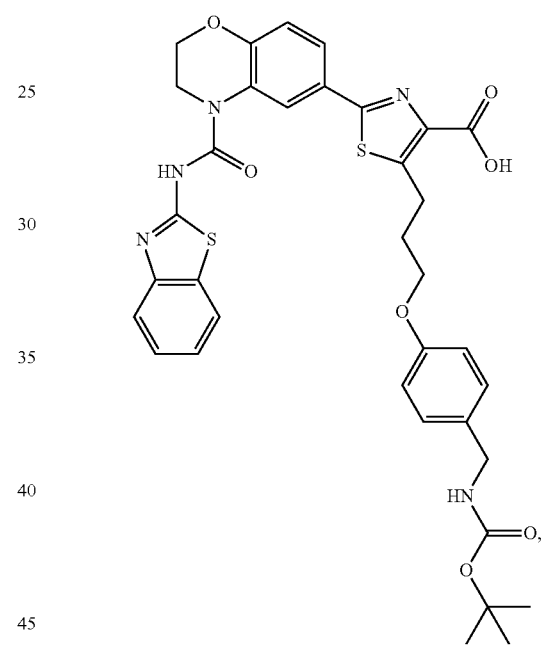
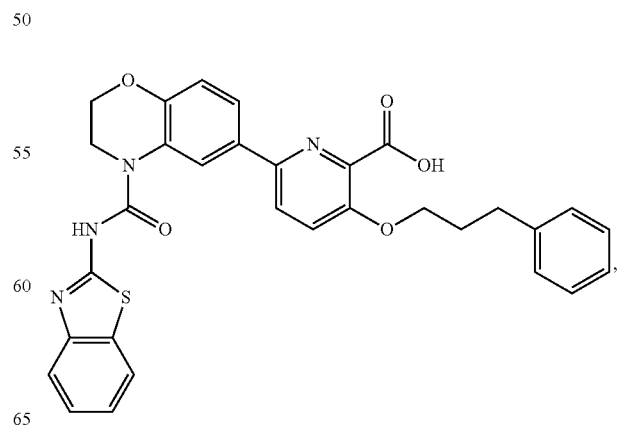

1351
-continued
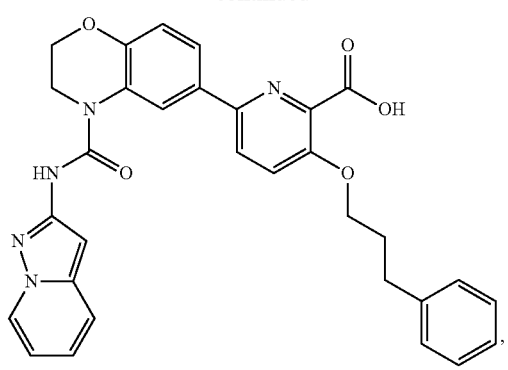
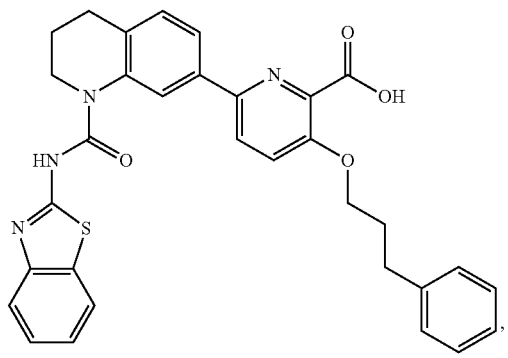
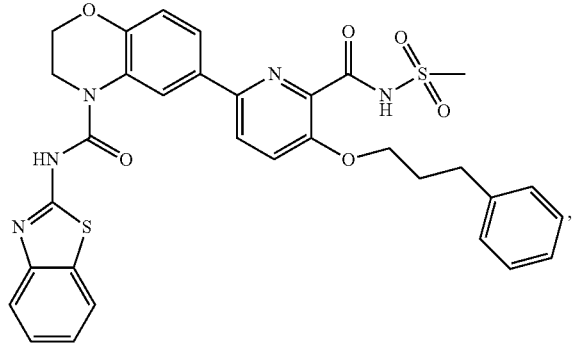
1352
-continued
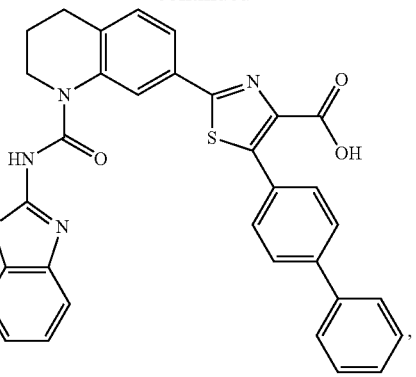
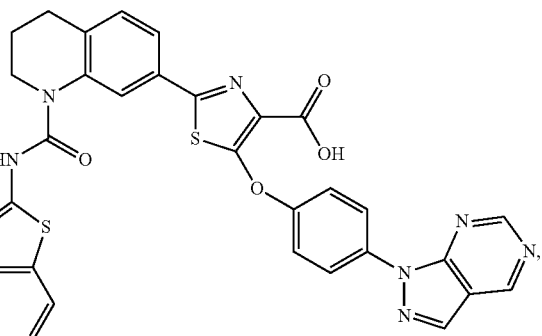
and
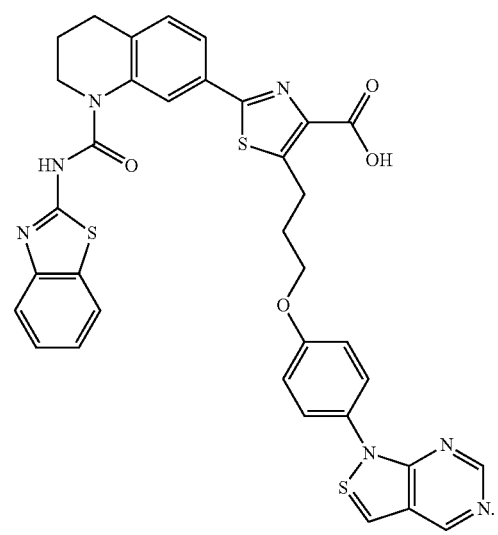
In some embodiments, the compound is selected from the group consisting of:

| Name | Structure |
|---|---|
| N-(4-(4-(((1,1'-biphenyl)-2-ylmethyl)piperazin-1-yl)benzoyl)-4-(((1R)-3-(dimethylamino)-1-((phenylsulfanyl)methyl)propyl)amino)-3-nitrobenzenesulfonamide | |
| N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide | 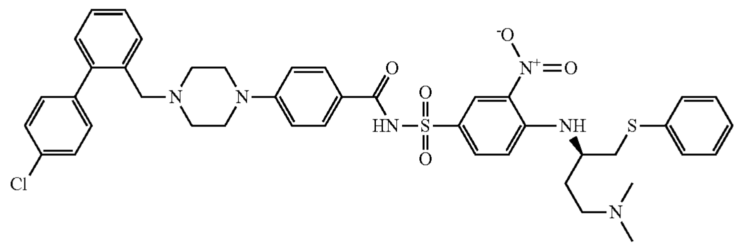 |
| 4-(((1R)-3-(dimethylamino)-1-((phenylsulfanyl)methyl)propyl)amino)-N-(4-(4-((4'-methoxy(1,1'-biphenyl)-2-yl)methyl)piperazin-1-yl)benzoyl)-3-nitrobenzenesulfonamide | 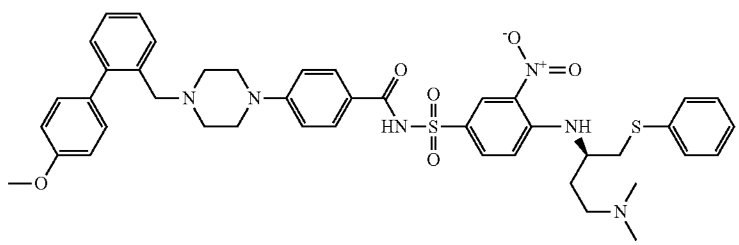 |
| 4-(((1R)-3-(dimethylamino)-1-((phenylsulfanyl)methyl)propyl)amino)-N-(4-(4-((4'-fluoro(1,1'-biphenyl)-2-yl)methyl)piperazin-1-yl)benzoyl)-3-nitrobenzenesulfonamide | 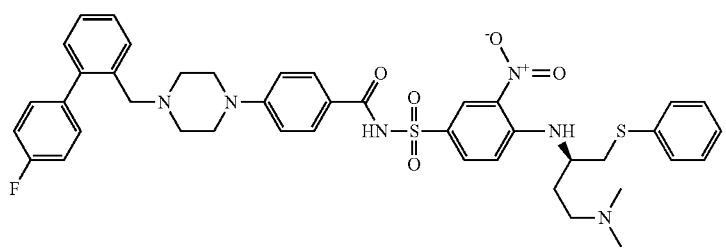 |
| 4-(((1R)-3-(dimethylamino)-1-((phenylsulfanyl)methyl)propyl)amino)-N-(4-(4-((4'-(methylsulfanyl)(1,1'-biphenyl)-2-yl)methyl)piperazin-1-yl)benzoyl)-3-nitrobenzenesulfonamide | 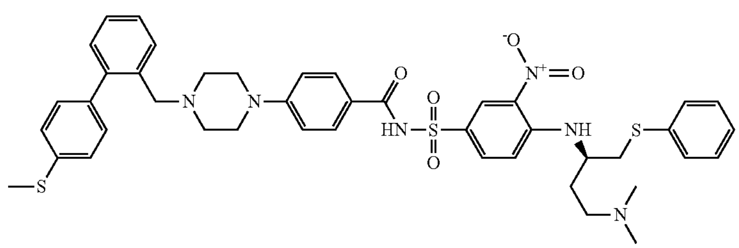 |
| N-((4-(((1R)-3-(dimethylamino)-((phenylsulfanyl)methyl)propyl)amino)-3-nitrophenyl)sulfonyl)-4-(4-(4'-phenyl-1,1'-biphenyl-2-ylmethyl)piperazin-1-yl)benzamide | 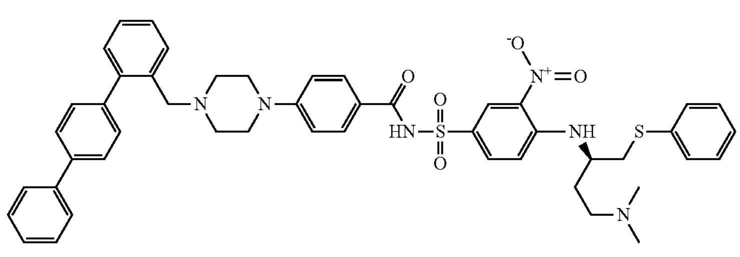 |

| Name | Structure |
|---|---|
| 4-(((1R)-3-(dimethylamino)-1-((phenylsulfanyl)methyl)propyl)amino)-3-nitro-N-(4-(4-((4'-phenoxy(1,1'-biphenyl)-2-yl)methyl)piperazin-1-yl)benzoyl)benzenesulfonamide | 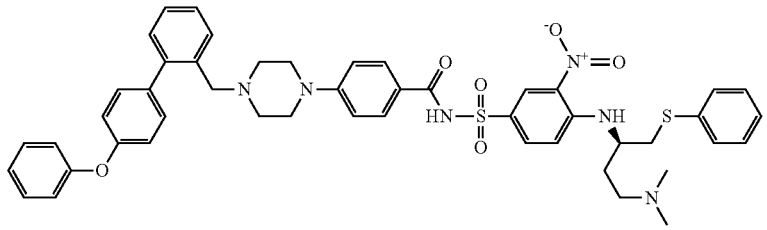 |
| N-(4-(4-((1,1'-biphenyl)-2-ylmethyl)piperazin-1-yl)benzoyl)-4-((1,1-dimethyl-2-(phenylsulfanyl)ethyl)amino)-3-nitrobenzenesulfonamide | 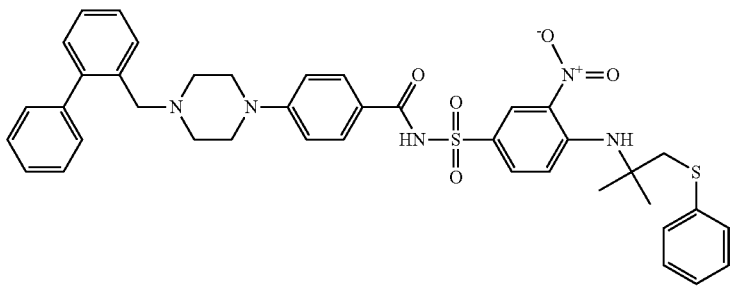 |
| N-(4-(4-((1,1'-biphenyl)-2-ylmethyl)piperazin-1-yl)benzoyl)-4-(((1R)-3-(morpholin-4-yl)-1-((phenylsulfanyl)methyl)propyl)amino)-3-nitrobenzenesulfonamide | 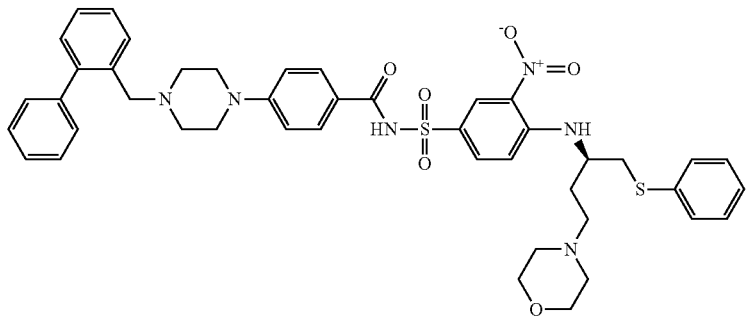 |
| N-(4-(4-((1,1'-biphenyl)-2-ylmethyl)piperazin-1-yl)benzoyl)-3-nitro-4-((2-(phenylsulfanyl)ethyl)amino)benzenesulfonamide | 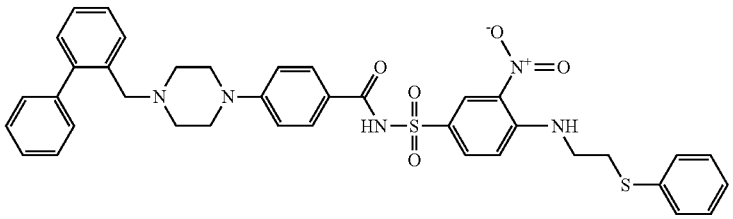 |
| N-(4-(4-((4'-chloro(1,1'-biphenyl)-2-yl)methyl)piperazin-1-yl)benzoyl)-3-nitro-4-((2-(phenylsulfanyl)ethyl)amino)benzenesulfonamide | 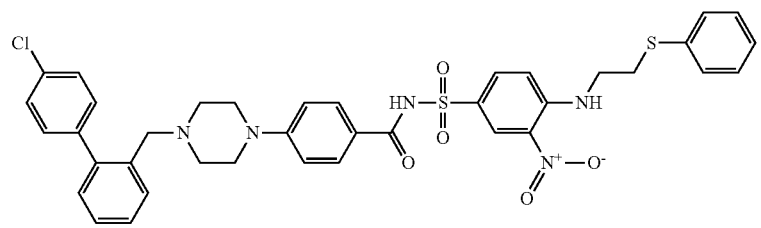 [SMILES: O=C(NS(=O)(=O)c1ccc(NCCSc2ccccc2)c([N+](=O)[O-])c1)c1ccc(N2CCN(Cc3ccccc3-c3ccc(Cl)cc3)CC2)cc1] |

-continued

| Name | Structure |
|---|---|
| N-(4-(4-((4'-chloro(1,1'-biphenyl)-2-yl)methyl)piperazin-1-yl)benzoyl)-4-(((1R)-3-(morpholin-4-yl)-1-((phenylsulfanyl)methyl)propyl)amino)-3-nitrobenzenesulfonamide | 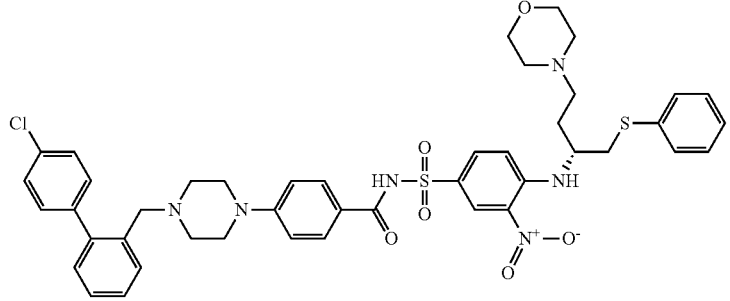 |
| N-(4-(4-((4'-chloro(1,1'-biphenyl)-2-yl)methyl)piperazin-1-yl)benzoyl)-4-((1,1-dimethyl-2-(phenylsulfanyl)ethyl)amino)-3-nitrobenzenesulfonamide | 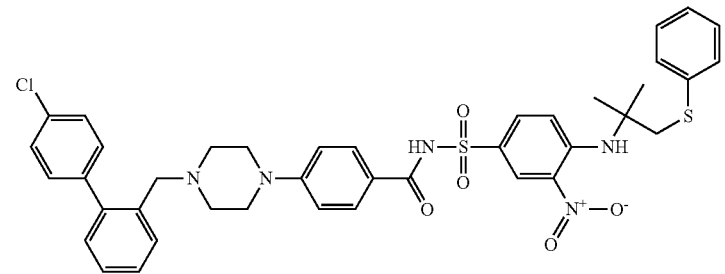 [SMILES: CC(C)(CSc1ccccc1)Nc1ccc(S(=O)(=O)NC(=O)c2ccc(N3CCN(Cc4ccccc4-c4ccc(Cl)cc4)CC3)cc2)cc1[N+](=O)[O-]] |
| N-(4-(4-((4'-chloro(1,1'-biphenyl)-2-yl)methyl)piperazin-1-yl)benzoyl)-4-(((1R)-4-(dimethylamino)-1-((phenylsulfanyl)methyl)butyl)amino)-3-nitrobenzenesulfonamide | 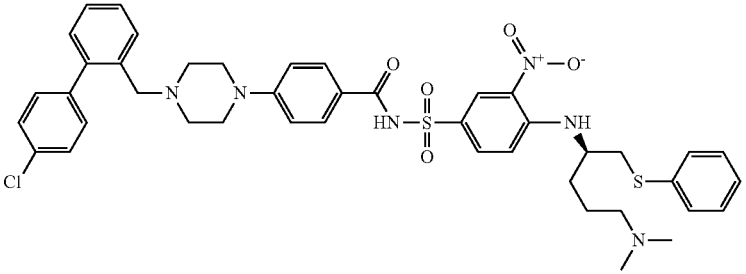 [SMILES: CN(C)CCC[C@H](CSc1ccccc1)Nc1ccc(S(=O)(=O)NC(=O)c2ccc(N3CCN(Cc4ccccc4-c4ccc(Cl)cc4)CC3)cc2)cc1[N+](=O)[O-]] |
| N-(4-(4-((4'-chloro(1,1'-biphenyl)-2-yl)methyl)piperazin-1-yl)benzoyl)-4-(((1R)-5-(dimethylamino)-1-((phenylsulfanyl)methyl)pentyl)amino)-3-nitrobenzenesulfonamide | 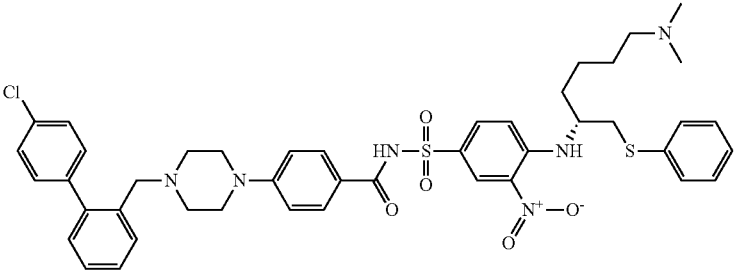 |
| N-(4-(4-((4'-fluoro(1,1'-biphenyl)-2-yl)methyl)piperazin-1-yl)benzoyl)-4-(((1R)-3-(morpholin-4-yl)-1-((phenylsulfanyl)methyl)propyl)amino)-3-nitrobenzenesulfonamide | 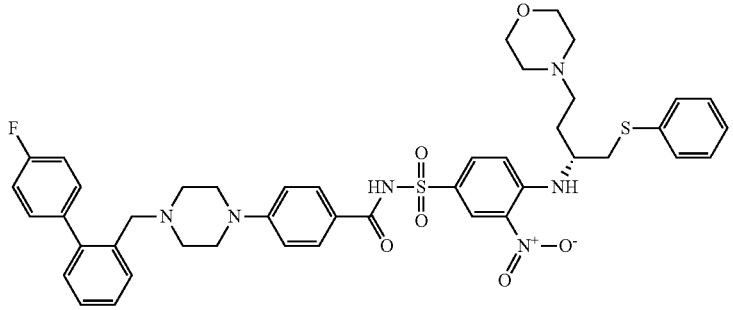 [SMILES: O=C(NS(=O)(=O)c1ccc(N[C@H](CCN2CCOCC2)CSc2ccccc2)c([N+](=O)[O-])c1)c1ccc(N2CCN(Cc3ccccc3-c3ccc(F)cc3)CC2)cc1] |

| Name | Structure |
|---|---|
| N-(4-(4-((4'-chloro-4-fluoro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide | 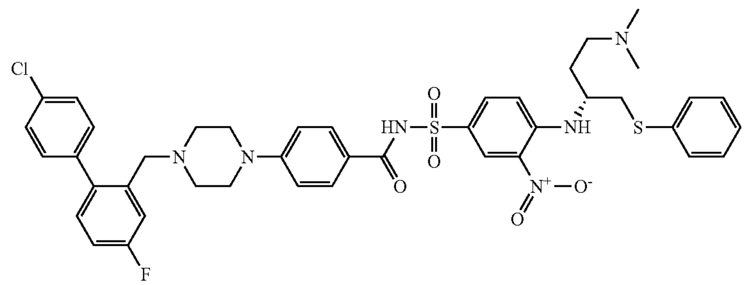 [SMILES: CN(C)CC[C@H](CSc1ccccc1)Nc1ccc(S(=O)(=O)NC(=O)c2ccc(N3CCN(Cc4cc(F)ccc4-c4ccc(Cl)cc4)CC3)cc2)cc1[N+](=O)[O-]] |
| N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-(trifluoromethyl)benzenesulfonamide | 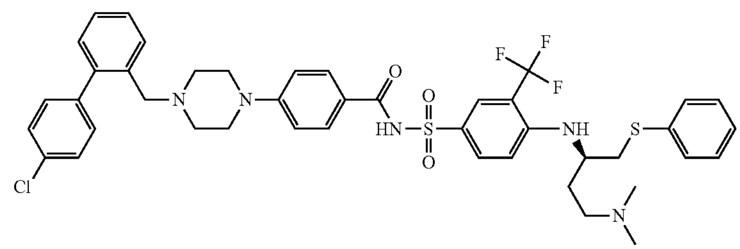 [SMILES: CN(C)CC[C@H](CSc1ccccc1)Nc1ccc(S(=O)(=O)NC(=O)c2ccc(N3CCN(Cc4ccccc4-c4ccc(Cl)cc4)CC3)cc2)cc1C(F)(F)F] |
| N-(4-(4-((4'-chloro(1,1'-biphenyl)-2-yl)methyl)piperazin-1-yl)benzoyl)-4-(((1R)-3-(morpholin-4-yl)-1-((phenylsulfanyl)methyl)propyl)amino)-3-(trifluoromethyl)benzenesulfonamide | 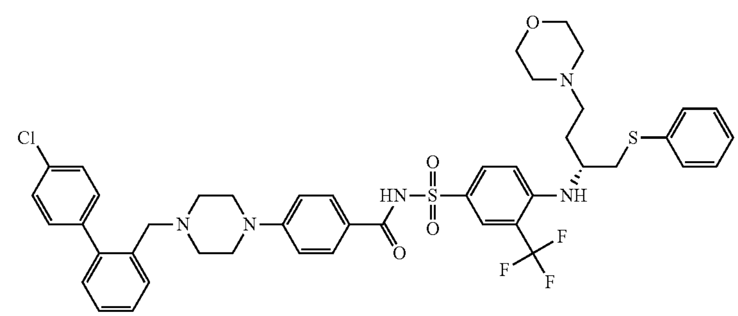 [SMILES: O=C(NS(=O)(=O)c1ccc(N[C@H](CCN2CCOCC2)CSc2ccccc2)c(C(F)(F)F)c1)c1ccc(N2CCN(Cc3ccccc3-c3ccc(Cl)cc3)CC2)cc1] |
| N-(4-(4-((4'-chloro(1,1'-biphenyl)-2-yl)methyl)piperazin-1-yl)benzoyl)-3-nitro-4-(((1R)-1-((phenylsulfanyl)methyl)-3-(pyrrolidin-1-yl)propyl)amino)benzenesulfonamide | 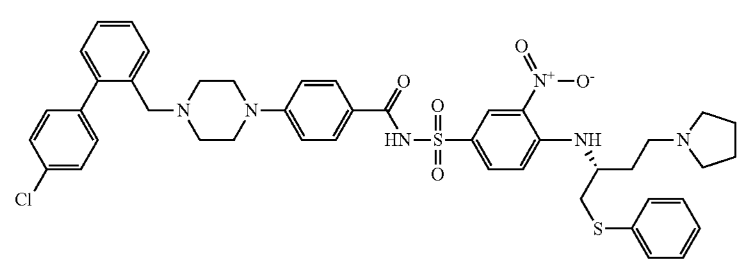 [SMILES: O=C(NS(=O)(=O)c1ccc(N[C@H](CCN2CCCC2)CSc2ccccc2)c([N+](=O)[O-])c1)c1ccc(N2CCN(Cc3ccccc3-c3ccc(Cl)cc3)CC2)cc1] |
| N-(4-(4-((4'-chloro(1,1'-biphenyl)-2-yl)methyl)piperazin-1-yl)benzoyl)-4-((1,1-dimethyl-2-(1,3-thiazol-2-ylsulfanyl)ethyl)amino)-3-nitrobenzenesulfonamide | 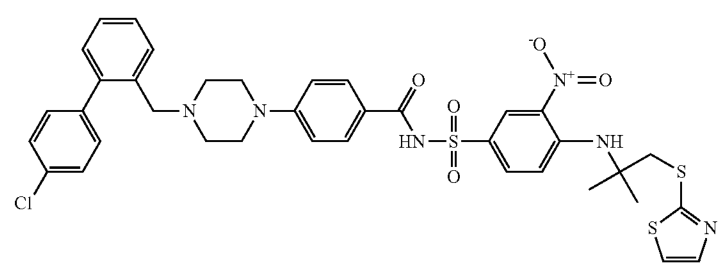 |

-continued

| Name | Structure |
|------|-----------|
| N-(4-(4-((4'-chloro(1,1'-biphenyl)-2-yl)methyl)piperazin-1-yl)benzoyl)-4-(((1R)-3-(dimethylamino)-1-((1,3-thiazol-2-ylsulfanyl)methyl)propyl)amino)-3-nitrobenzenesulfonamide | 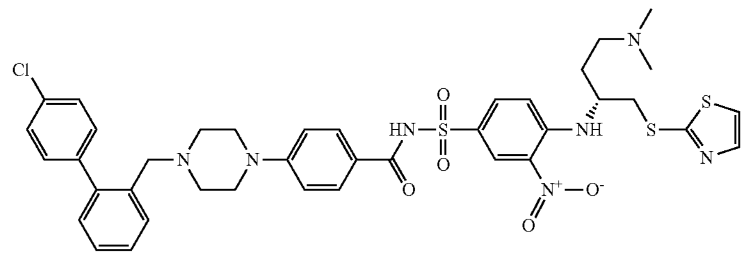 [SMILES: CN(C)CC[C@H](CSc1nccs1)Nc1ccc(S(=O)(=O)NC(=O)c2ccc(N3CCN(Cc4ccccc4-c4ccc(Cl)cc4)CC3)cc2)cc1[N+](=O)[O-]] |
| N-(4-(4-((4'-chloro(1,1'-biphenyl)-2-yl)methyl)piperazin-1-yl)benzoyl)-4-(((1R)-3-(dimethylamino)-1-((thien-2-ylsulfanyl)methyl)propyl)amino)-3-nitrobenzenesulfonamide | 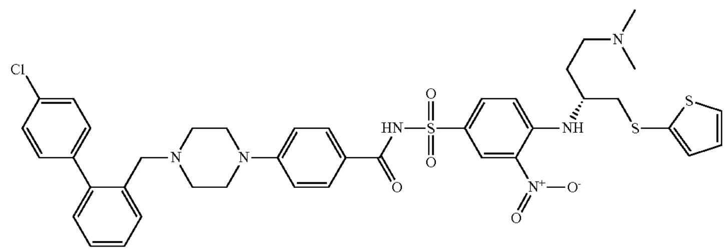 |
| N-(4-(4-((4'-chloro(1,1'-biphenyl)-2-yl)methyl)piperazin-1-yl)benzoyl)-4-(((1R)-2-(2-(dimethylamino)ethoxy)-1-((phenylsulfanyl)methyl)ethyl)amino)-3-nitrobenzenesulfonamide | 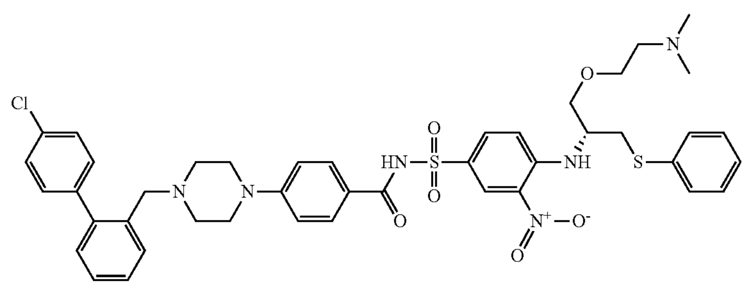 [SMILES: CN(C)CCOC[C@H](CSc1ccccc1)Nc1ccc(S(=O)(=O)NC(=O)c2ccc(N3CCN(Cc4ccccc4-c4ccc(Cl)cc4)CC3)cc2)cc1[N+](=O)[O-]] |
| N-(4-(4-((4'-chloro(1,1'-biphenyl)-2-yl)methyl)piperazin-1-yl)benzoyl)-4-(((1S)-3-(dimethylamino)-1-methyl-1-((phenylsulfanyl)methyl)propyl)amino)-3-nitrobenzenesulfonamide | 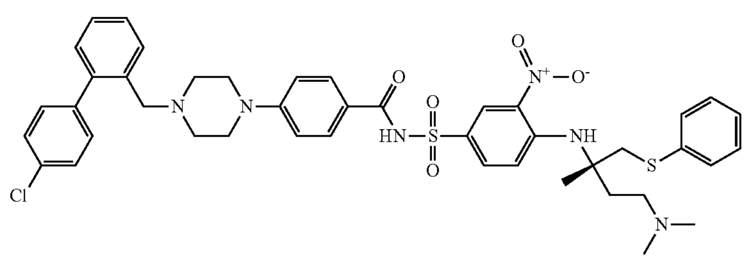 [SMILES: CN(C)CC[C@@](C)(CSc1ccccc1)Nc1ccc(S(=O)(=O)NC(=O)c2ccc(N3CCN(Cc4ccccc4-c4ccc(Cl)cc4)CC3)cc2)cc1[N+](=O)[O-]] |
| N-(4-(4-((4'-chloro(1,1'-biphenyl)-2-yl)methyl)piperazin-1-yl)benzoyl)-4-(((1R)-3-(methylamino)-1-((phenylsulfanyl)methyl)propyl)amino)-3-nitrobenzenesulfonamide | 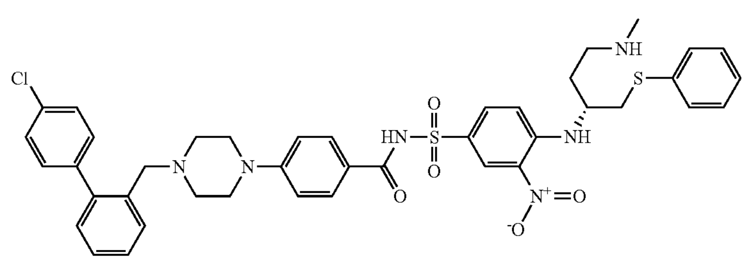 |
| (3R)-3-(4-(((4-(4-((4'-chloro(1,1'-biphenyl)-2-yl)methyl)piperazin-1-yl)benzoyl)amino)sulfonyl)-2-nitroanilino)-4-(phenylsulfanyl)butanoic acid | 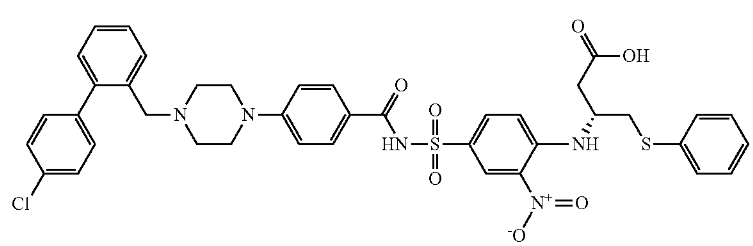 |

| Name | Structure |
|---|---|
| (3R)-3-(4-(((4-(4-((4'-chloro(1,1'-biphenyl)-2-yl)methyl)piperazin-1-yl)benzoyl)amino)sulfonyl)-2-nitroanilino)-N-isopropyl-4-(phenylsulfanyl)butanamide | 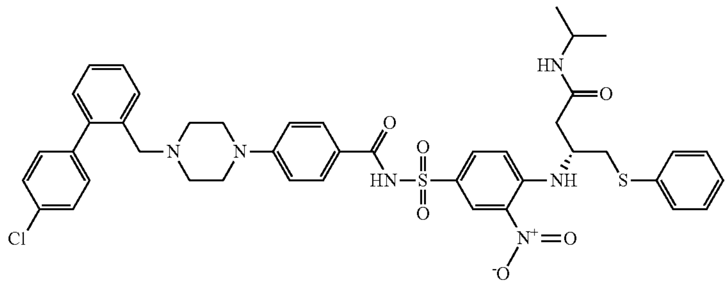 |
| N-(4-(4-((4'-chloro(1,1'-biphenyl)-2-yl)methyl)piperazin-1-yl)benzoyl)-4-(((1R)-3-(diisopropylamino)-1-((phenylsulfanyl)methyl)propyl)amino)-3-nitrobenzenesulfonamide | 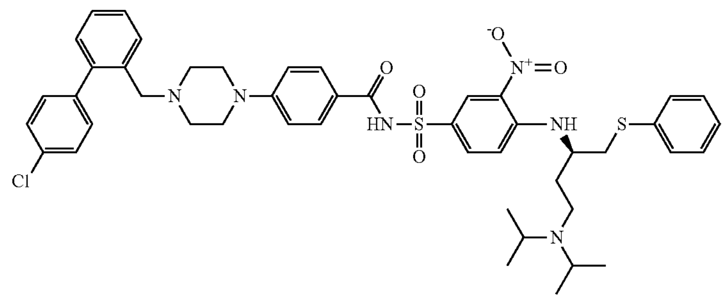 |
| 4-(((1R)-3-(azetidin-1-yl)-1-((phenylsulfanyl)methyl)propyl)amino)-N-(4-(4-((4'-chloro(1,1'-biphenyl)-2-yl)methyl)piperazin-1-yl)benzoyl)-3-nitrobenzenesulfonamide | 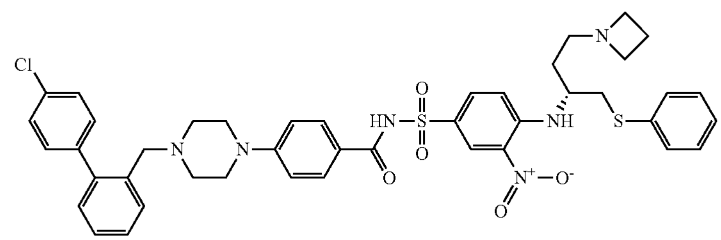 [SMILES: O=C(NS(=O)(=O)c1ccc(N[C@H](CCN2CCC2)CSc2ccccc2)c([N+](=O)[O-])c1)c1ccc(N2CCN(Cc3ccccc3-c3ccc(Cl)cc3)CC2)cc1] |
| N-(4-(4-((4'-chloro(1,1'-biphenyl)-2-yl)methyl)piperazin-1-yl)benzoyl)-3-nitro-4-((4-(phenylsulfanyl)tetrahydro-3-furanyl)amino)benzenesulfonamide | 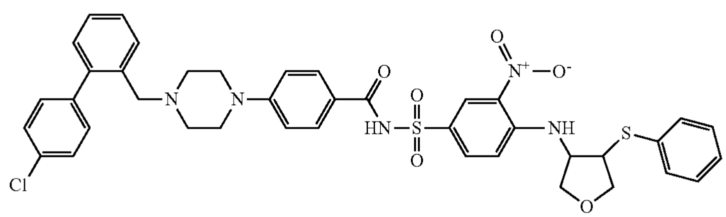 [SMILES: O=C(NS(=O)(=O)c1ccc(NC2COCC2Sc2ccccc2)c([N+](=O)[O-])c1)c1ccc(N2CCN(Cc3ccccc3-c3ccc(Cl)cc3)CC2)cc1] |
| N-(4-(4-((4'-chloro(1,1'-biphenyl)-2-yl)methyl-4-methoxypiperidin-1-yl)benzoyl)-4-(((1R)-3-(dimethylamino)-1-((phenylsulfanyl)methyl)propyl)amino)-3-nitrobenzenesulfonamide | |
| N-(4-(4-((4'-chloro(1,1'-biphenyl)-2-yl)methyl-4-methoxypiperidin-1-yl)benzoyl)-4-(((1R)-3-(morpholin-4-yl)-1-((phenylsulfanyl)methyl)propyl)amino)-3-nitrobenzenesulfonamide | |

| Name | Structure |
|---|---|
| N-(4-(4-((4'-chloro(1,1'-biphenyl)-2-yl)methyl)piperazin-1-yl)benzoyl)-4-(((1R)-3-hydroxy-1-((phenylsulfanyl)methyl)propyl)amino)-3-nitrobenzenesulfonamide | 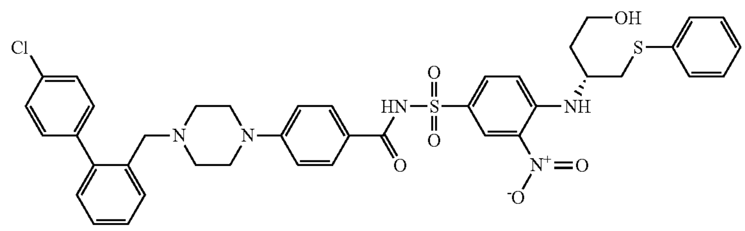 |
| N-(4-(4-((4'-chloro(1,1'-biphenyl)-2-yl)methyl)piperazin-1-yl)benzoyl)-4-(((1R)-3-(isopropylamino)-1-((phenylsulfanyl)methyl)propyl)amino)-3-nitrobenzenesulfonamide | 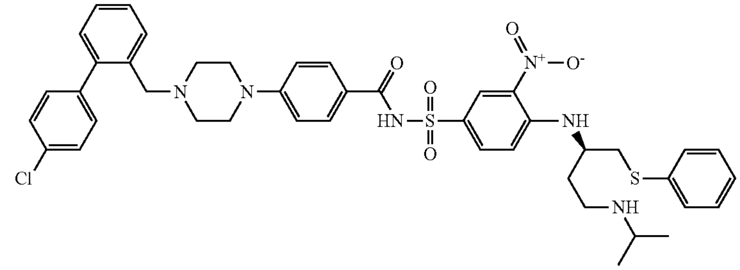 [SMILES: CC(C)NCC[C@H](CSc1ccccc1)Nc1ccc(S(=O)(=O)NC(=O)c2ccc(N3CCN(Cc4ccccc4-c4ccc(Cl)cc4)CC3)cc2)cc1[N+](=O)[O-]] |
| 4-(((1R)-3-(dimethylamino)-1-((phenylsulfanyl)methyl)propyl)amino)-N-(4-(4-(2-(2-naphthyl)benzyl)piperazin-1-yl)benzoyl)-3-nitrobenzenesulfonamide | 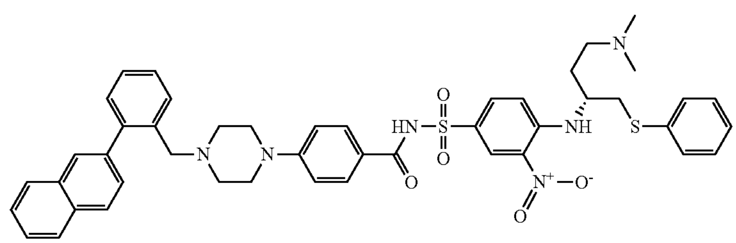 [SMILES: CN(C)CC[C@H](CSc1ccccc1)Nc1ccc(S(=O)(=O)NC(=O)c2ccc(N3CCN(Cc4ccccc4-c4ccc5ccccc5c4)CC3)cc2)cc1[N+](=O)[O-]] |
| 4-(((1R)-3-(dimethylamino)-1-((phenylsulfanyl)methyl)propyl)amino)-N-(4-(4-(2-(1-naphthyl)benzyl)piperazin-1-yl)benzoyl)-3-nitrobenzenesulfonamide | 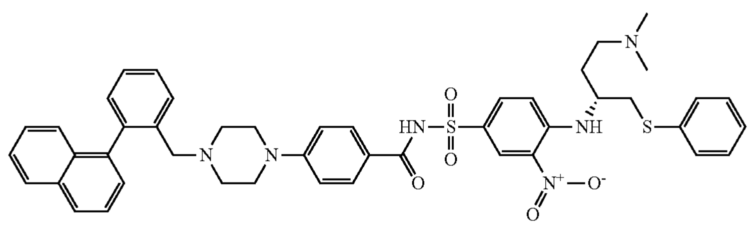 [SMILES: CN(C)CC[C@H](CSc1ccccc1)Nc1ccc(S(=O)(=O)NC(=O)c2ccc(N3CCN(Cc4ccccc4-c4cccc5ccccc45)CC3)cc2)cc1[N+](=O)[O-]] |
| N-(4-(4-((3'-cyano(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide | 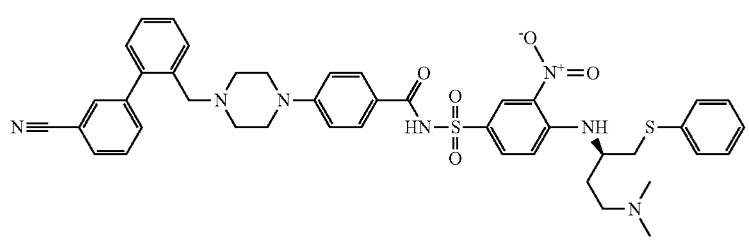 |
| 4-(((1R)-3-(dimethylamino)-1-((phenylsulfanyl)methyl)propyl)amino)-N-(4-(4-((3'-methoxy(1,1'-biphenyl)-2-yl)methyl)piperazin-1-yl)benzoyl)-3-nitrobenzenesulfonamide | 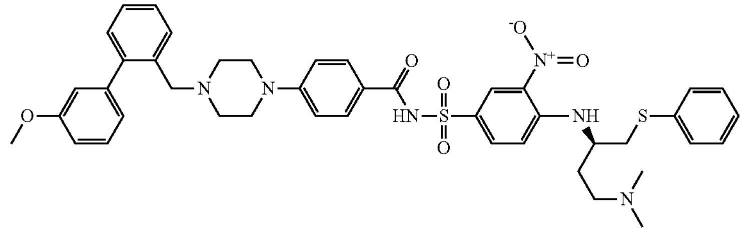 |

-continued

| Name | Structure |
|---|---|
| N-(4-(4-((3'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide | 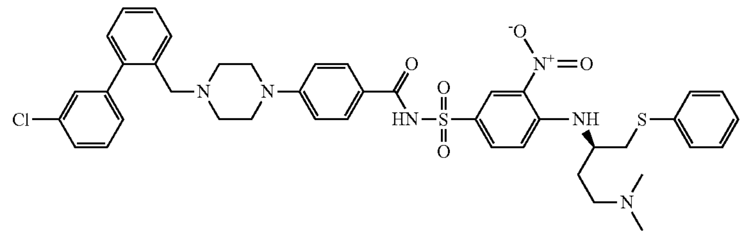 |
| N-(4-(4-((2'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide | 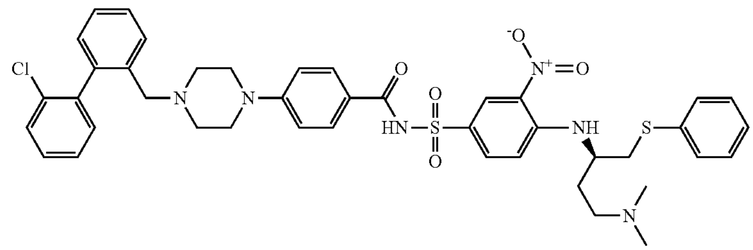 |
| N-(4-(4-(2-(1,3-benzodioxol-5-yl)benzyl)piperazin-1-yl)benzoyl)-4-(((1R)-3-(dimethylamino)-1-((phenylsulfanyl)methyl)propyl)amino)-3-nitrobenzenesulfonamide | 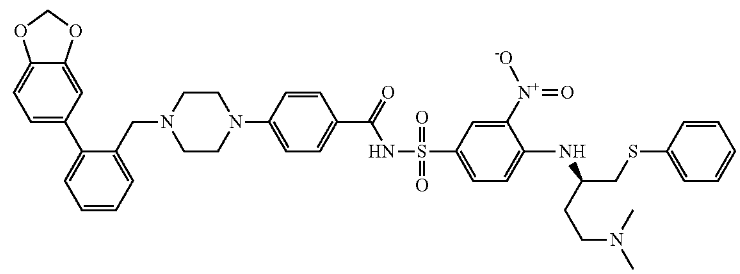 |
| 4-(((1R)-3-(dimethylamino)-1-((phenylsulfanyl)methyl)propyl)amino)-3-nitro-N-(4-(4-(2-(3-thienyl)benzyl)piperazin-1-yl)benzoyl)benzenesulfonamide | 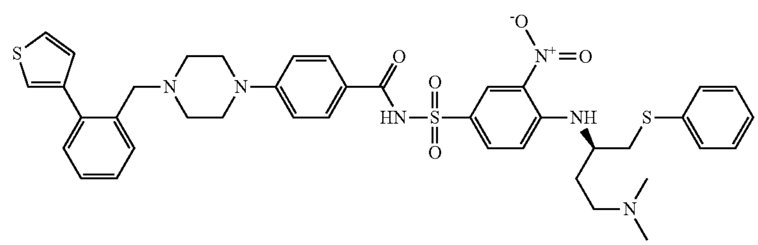 |
| 4-(((1R)-3-(dimethylamino)-1-((phenylsulfanyl)methyl)propyl)amino)-3-nitro-N-(4-(4-(2-(pyridin-3-yl)benzyl)piperazin-1-yl)benzoyl)benzenesulfonamide | 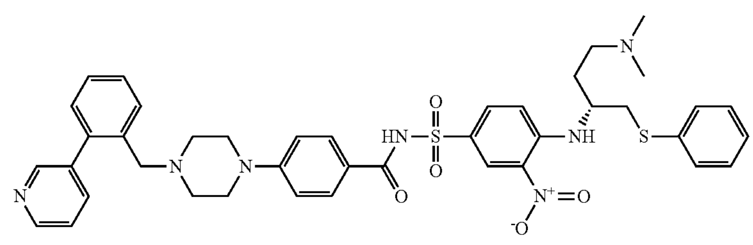 |
| 4-(((1R)-3-(dimethylamino)-1-((phenylsulfanyl)methyl)propyl)amino)-3-nitro-N-(4-(4-(2-(quinolin-8-yl)benzyl)piperazin-1-yl)benzoyl)benzenesulfonamide | 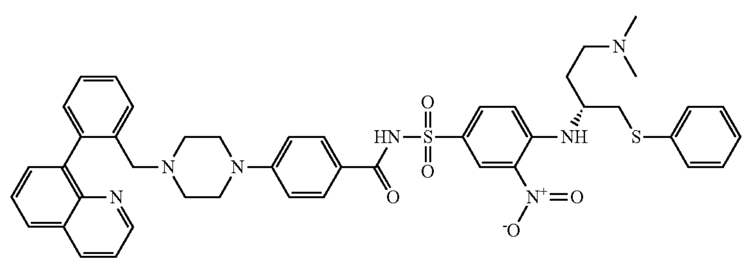 |

| Name | Structure |
|---|---|
| N-(4-(4-(2-(1-benzofuran-2-yl)benzyl)piperazin-1-yl)benzoyl)-4-(((1R)-3-(dimethylamino)-1-((phenylsulfanyl)methyl)propyl)amino)-3-nitrobenzenesulfonamide | 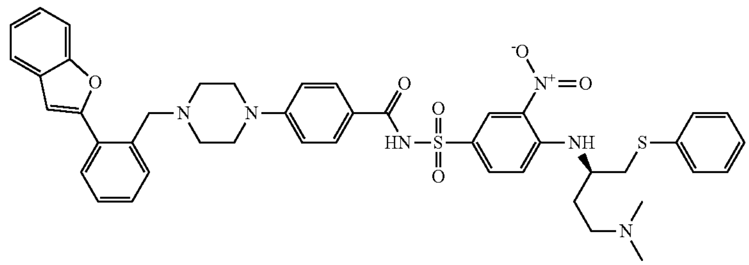 |
| 4-(((1R)-3-(dimethylamino)-1-((phenylsulfanyl)methyl)propyl)amino)-N-(4-(4-((2'-methyl(1,1'-biphenyl)-2-yl)methyl)piperazin-1-yl)benzoyl)-3-nitrobenzenesulfonamide | 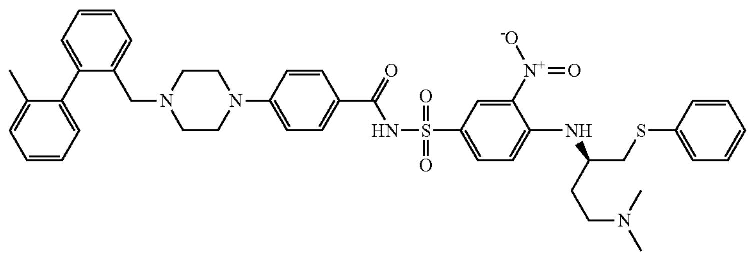 |
| 4-(((1R)-3-(dimethylamino)-1-((phenylsulfanyl)methyl)propyl)amino)-3-nitro-N-(4-(4-(2-(quinolin-3-yl)benzyl)piperazin-1-yl)benzoyl)benzenesulfonamide | 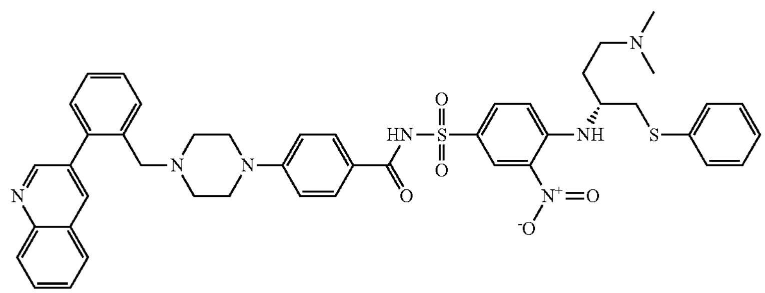 |
| N-(4-(4-((1-(4-chlorophenyl)-2-naphthyl)methyl)piperazin-1-yl)benzoyl)-3-nitro-4-((2-(phenylsulfanyl)ethyl)amino)benzenesulfonamide | 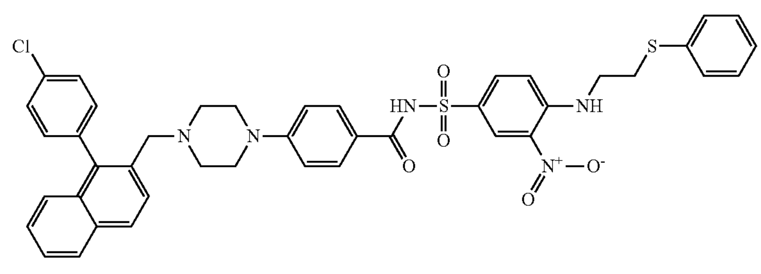 [SMILES: O=C(NS(=O)(=O)c1ccc(NCCSc2ccccc2)c([N+](=O)[O-])c1)c1ccc(N2CCN(Cc3ccc4ccccc4c3-c3ccc(Cl)cc3)CC2)cc1] |
| N-(4-(4-((1-(4-chlorophenyl)-2-naphthyl)methyl)piperazin-1-yl)benzoyl)-4-(((1R)-3-(dimethylamino)-1-((phenylsulfanyl)methyl)propyl)amino)-3-nitrobenzenesulfonamide | 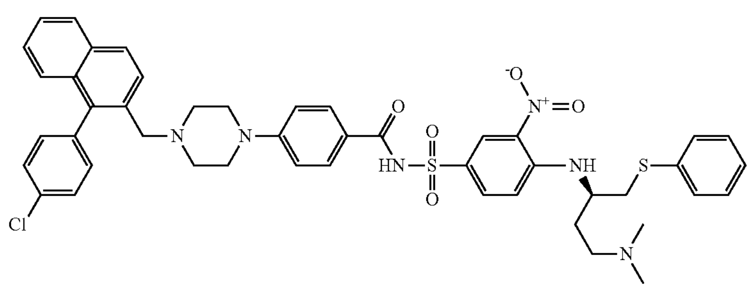 |

-continued

| Name | Structure |
|---|---|
| N-(4-(4-((1-(4-chlorophenyl)-2-naphthyl)methyl)piperazin-1-yl)benzoyl)-4-(((1R)-3-(morpholin-4-yl)-1-((phenylsulfanyl)methyl)propyl)amino)-3-nitrobenzenesulfonamide | 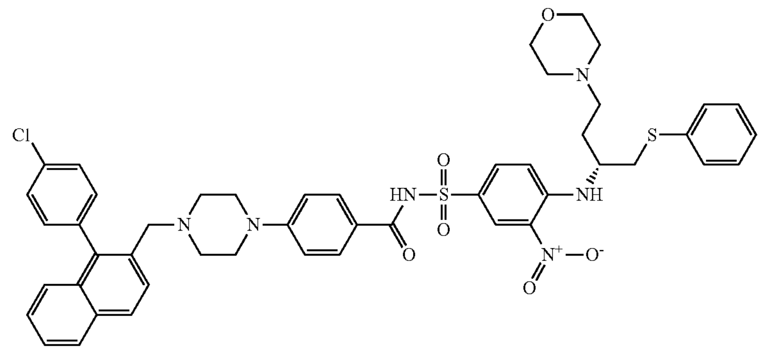 [SMILES: O=C(NS(=O)(=O)c1ccc(N[C@H](CCN2CCOCC2)CSc2ccccc2)c([N+](=O)[O-])c1)c1ccc(N2CCN(Cc3ccc4ccccc4c3-c3ccc(Cl)cc3)CC2)cc1] |
| N-(4-(4-((4'-chloro(1,1'-biphenyl)-2-yl)methyl)piperazin-1-yl)benzoyl)-3-nitro-4-((2-(phenylsulfanyl)cyclopentyl)amino)benzenesulfonamide | 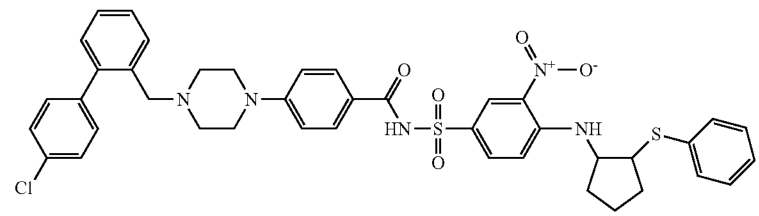 [SMILES: O=C(NS(=O)(=O)c1ccc(NC2CCCC2Sc2ccccc2)c([N+](=O)[O-])c1)c1ccc(N2CCN(Cc3ccccc3-c3ccc(Cl)cc3)CC2)cc1] |
| N-(4-(4-((1,1'-biphenyl)-2-ylmethyl)-4-methoxypiperidin-1-yl)benzoyl)-3-nitro-4-((2-(phenylsulfanyl)cyclopentyl)amino)benzenesulfonamide | 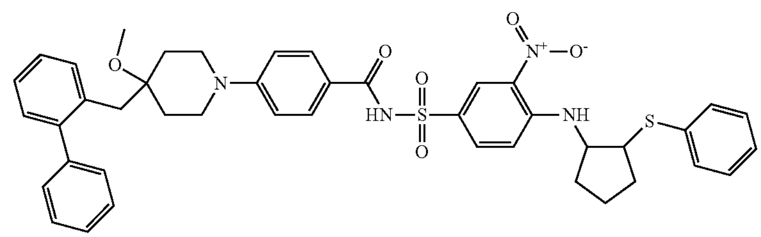 [SMILES: COC1(Cc2ccccc2-c2ccccc2)CCN(c2ccc(C(=O)NS(=O)(=O)c3ccc(NC4CCCC4Sc4ccccc4)c([N+](=O)[O-])c3)cc2)CC1] |
| N-(4-(4-((4'-fluoro(1,1'-biphenyl)-2-yl)methyl)piperazin-1-yl)benzoyl)-3-nitro-4-((2-(phenylsulfanyl)ethyl)amino)benzenesulfonamide | 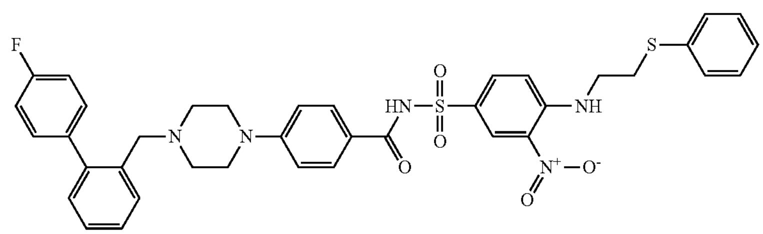 [SMILES: O=C(NS(=O)(=O)c1ccc(NCCSc2ccccc2)c([N+](=O)[O-])c1)c1ccc(N2CCN(Cc3ccccc3-c3ccc(F)cc3)CC2)cc1] |
| N-(4-(4-((3',4'-dichloro(1,1'-biphenyl)-2-yl)methyl)piperazin-1-yl)benzoyl)-3-nitro-4-((2-(phenylsulfanyl)ethyl)amino)benzenesulfonamide | 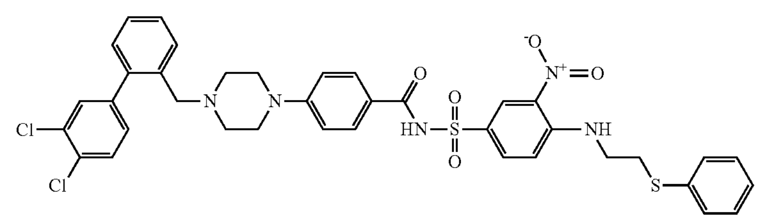 |
| N-(4-(4-((3',4'-dichloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide | 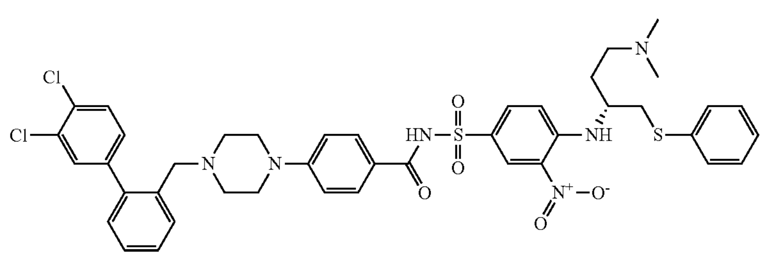 [SMILES: CN(C)CC[C@H](CSc1ccccc1)Nc1ccc(S(=O)(=O)NC(=O)c2ccc(N3CCN(Cc4ccccc4-c4ccc(Cl)c(Cl)c4)CC3)cc2)cc1[N+](=O)[O-]] |

| Name | Structure |
|---|---|
| N-(4-(4-((3',4'-dichloro(1,1'-biphenyl)-2-yl)methyl)piperazin-1-yl)benzoyl)-4-(((1R)-3-(morpholin-4-yl)-1-((phenylsulfanyl)methyl)propyl)amino)-3-nitrobenzenesulfonamide | 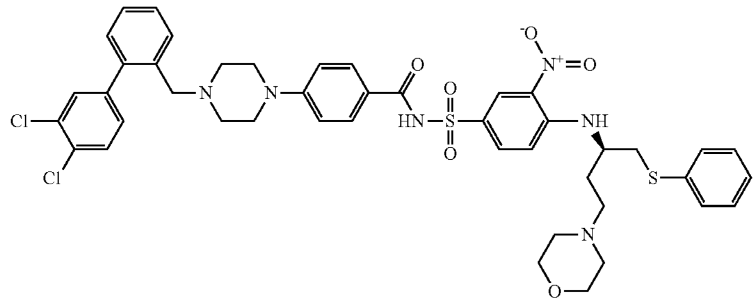 |
| 3-nitro-4-((2-(phenylsulfanyl)ethyl)amino)-N-(4-(4-((4'-(trifluoromethyl)(1,1'-biphenyl)-2-yl)methyl)piperazin-1-yl)benzoyl)benzenesulfonamide | 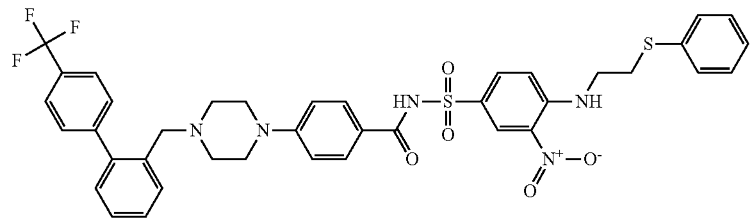 [SMILES: O=C(NS(=O)(=O)c1ccc(NCCSc2ccccc2)c([N+](=O)[O-])c1)c1ccc(N2CCN(Cc3ccccc3-c3ccc(C(F)(F)F)cc3)CC2)cc1] |
| 4-(((1R)-3-(dimethylamino)-1-((phenylsulfanyl)methyl)propyl)amino)-3-nitro-N-(4-(4-((4'-(trifluoromethyl)(1,1'-biphenyl)-2-yl)methyl)piperazin-1-yl)benzoyl)benzenesulfonamide | 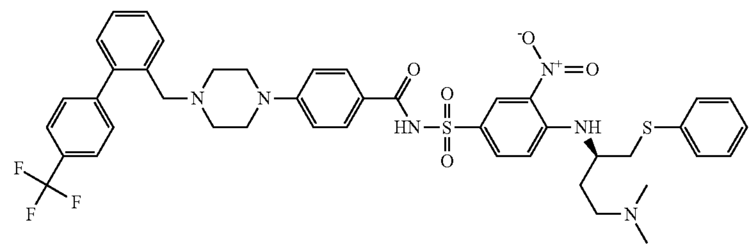 |
| 4-(((1R)-3-(morpholin-4-yl)-1-((phenylsulfanyl)methyl)propyl)amino)-3-nitro-N-(4-(4-((4'-(trifluoromethyl)(1,1'-biphenyl)-2-yl)methyl)piperazin-1-yl)benzoyl)benzenesulfonamide | 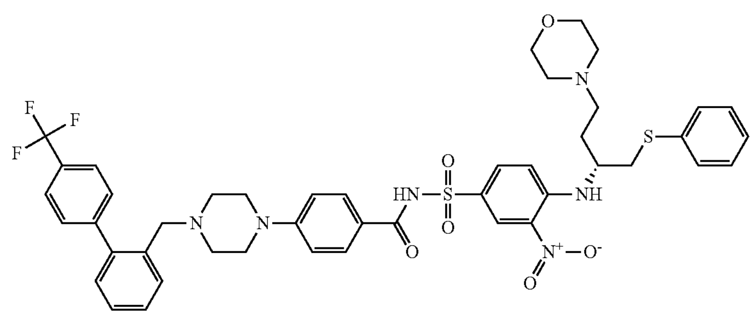 [SMILES: O=C(NS(=O)(=O)c1ccc(N[C@H](CCN2CCOCC2)CSc2ccccc2)c([N+](=O)[O-])c1)c1ccc(N2CCN(Cc3ccccc3-c3ccc(C(F)(F)F)cc3)CC2)cc1] |
| 3-nitro-4-((2-(phenylsulfanyl)ethyl)amino)-N-(4-(4-((4'-(trifluoromethoxy)(1,1'-biphenyl)-2-yl)methyl)piperazin-1-yl)benzoyl)benzenesulfonamide | |
| 3-nitro-4-((2-(phenylsulfanyl)ethyl)amino)-N-(4-(4-((4'-(trifluoromethoxy)(1,1'-biphenyl)-2-yl)methyl)piperazin-1-yl)benzoyl)benzenesulfonamide | |

| Name | Structure |
|---|---|
| 4-(((1R)-3-(morpholin-4-yl)-1-((phenylsulfanyl)methyl)propyl)amino)-3-nitro-N-(4-(4-((4'-(trifluoromethoxy)(1,1'-biphenyl)-2-yl)methyl)piperazin-1-yl)benzoyl)benzenesulfonamide | 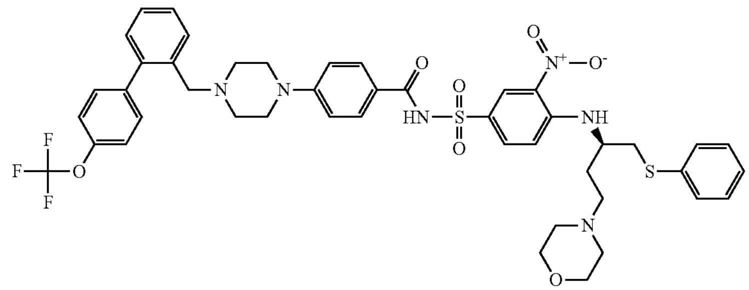 [SMILES: O=C(NS(=O)(=O)c1ccc(N[C@H](CCN2CCOCC2)CSc2ccccc2)c([N+](=O)[O-])c1)c1ccc(N2CCN(Cc3ccccc3-c3ccc(OC(F)(F)F)cc3)CC2)cc1] |
| 3-nitro-N-(4-(4-((4'-phenoxy(1,1'-biphenyl)-2-yl)methyl)piperazin-1-yl)benzoyl)-4-((2-(phenylsulfanyl)ethyl)amino)benzenesulfonamide | 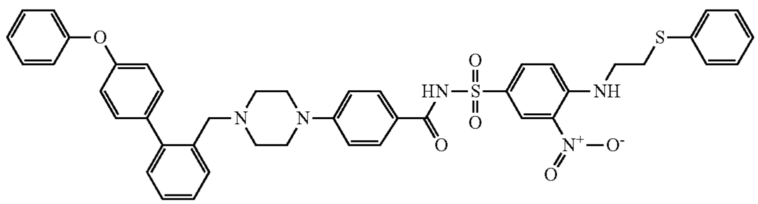 [SMILES: O=C(NS(=O)(=O)c1ccc(NCCSc2ccccc2)c([N+](=O)[O-])c1)c1ccc(N2CCN(Cc3ccccc3-c3ccc(Oc4ccccc4)cc3)CC2)cc1] |
| 4-(((1R)-3-(morpholin-4-yl)-1-((phenylsulfanyl)methyl)propyl)amino)-3-nitro-N-(4-(4-((4'-phenoxy(1,1'-biphenyl)-2-yl)methyl)piperazin-1-yl)benzoyl)benzenesulfonamide | 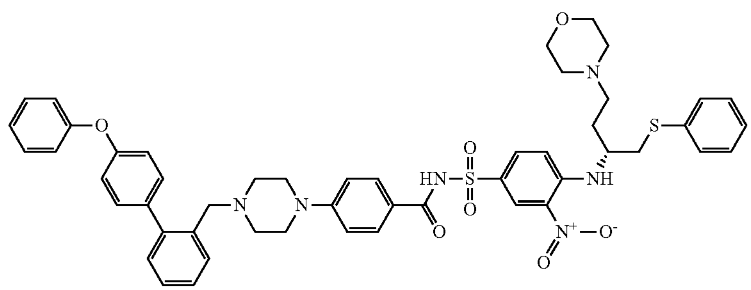 [SMILES: O=C(NS(=O)(=O)c1ccc(N[C@H](CCN2CCOCC2)CSc2ccccc2)c([N+](=O)[O-])c1)c1ccc(N2CCN(Cc3ccccc3-c3ccc(Oc4ccccc4)cc3)CC2)cc1] |
| N-(4-(4-((4'-chloro(1,1'-biphenyl)-2-yl)methyl)piperazin-1-yl)benzoyl)-4-(((1S)-3-(dimethylamino)-1-((phenylsulfanyl)methyl)propyl)amino)-3-nitrobenzenesulfonamide | 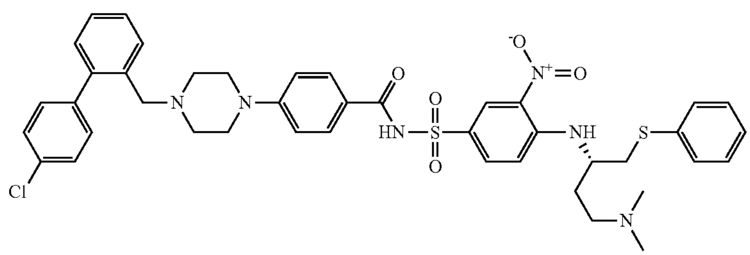 |
| N-(4-(4-((4'-chloro(1,1'-biphenyl)-2-yl)methyl)piperazin-1-yl)benzoyl)-4-((1,1-dimethyl-2-(phenylsulfonyl)ethyl)amino)-3-nitrobenzenesulfonamide | 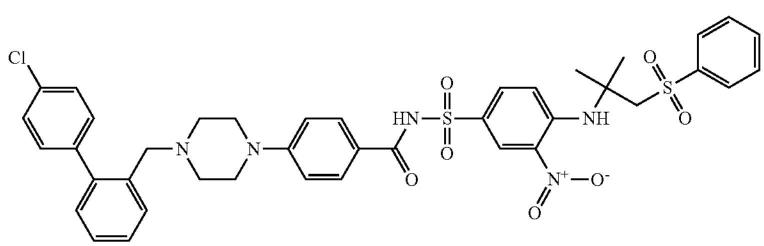 [SMILES: CC(C)(CS(=O)(=O)c1ccccc1)Nc1ccc(S(=O)(=O)NC(=O)c2ccc(N3CCN(Cc4ccccc4-c4ccc(Cl)cc4)CC3)cc2)cc1[N+](=O)[O-]] |
| N-(4-(4-((2',4'-dichloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide | 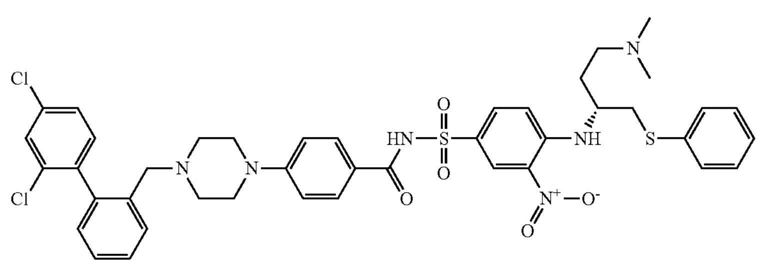 [SMILES: CN(C)CC[C@H](CSc1ccccc1)Nc1ccc(S(=O)(=O)NC(=O)c2ccc(N3CCN(Cc4ccccc4-c4ccc(Cl)cc4Cl)CC3)cc2)cc1[N+](=O)[O-]] |

| Name | Structure |
|---|---|
| 4-(((1R)-3-(dimethylamino)-1-((phenylsulfanyl)methyl)propyl)amino)-3-nitro-N-(4-(4-(2-(2-thienyl)benzyl)piperazin-1-yl)benzoyl)benzenesulfonamide | 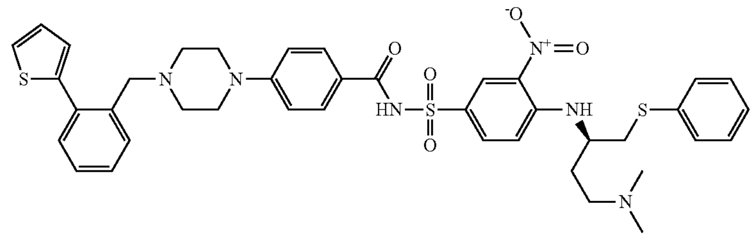 |
| N-(4-(4-((4'-chloro-2'-methyl(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide | 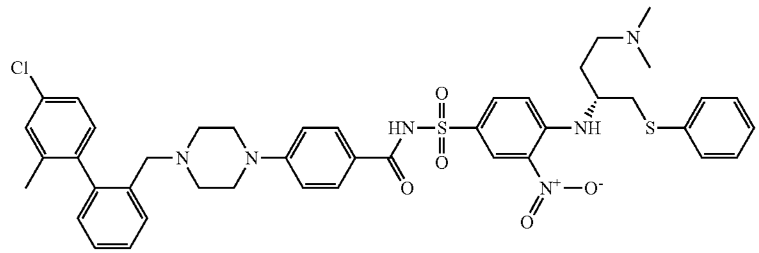 [SMILES: Cc1cc(Cl)ccc1-c1ccccc1CN1CCN(c2ccc(C(=O)NS(=O)(=O)c3ccc(N[C@H](CCN(C)C)CSc4ccccc4)c([N+](=O)[O-])c3)cc2)CC1] |
| N-(4-(4-((2',4'-difluoro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide | 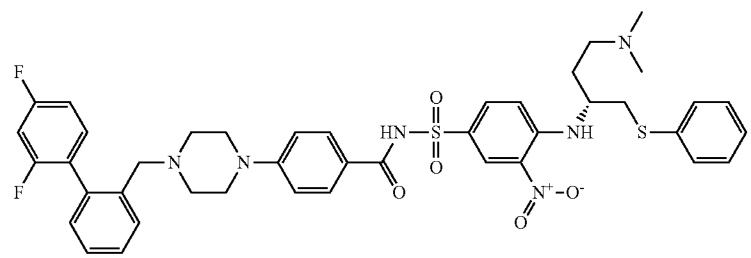 [SMILES: CN(C)CC[C@H](CSc1ccccc1)Nc1ccc(S(=O)(=O)NC(=O)c2ccc(N3CCN(Cc4ccccc4-c4ccc(F)cc4F)CC3)cc2)cc1[N+](=O)[O-]] |
| N-(4-(4-((1,1'-biphenyl)-2-ylmethyl)piperazin-1-yl)benzoyl)-3-nitro-4-((2-(phenylsulfonyl)ethyl)amino)benzenesulfonamide | 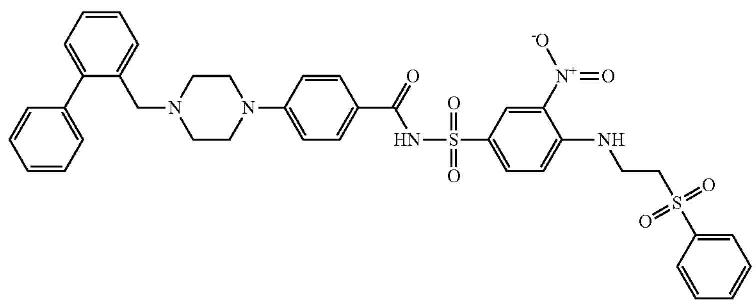 |
| N-(4-(4-((4'-chloro(1,1'-biphenyl)-2-yl)methyl)piperazin-1-yl)benzoyl)-3-nitro-4-((2-(phenylsulfonyl)ethyl)amino)benzenesulfonamide | 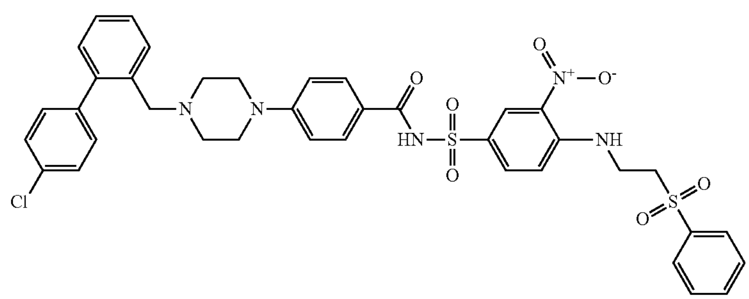 [SMILES: O=C(NS(=O)(=O)c1ccc(NCCS(=O)(=O)c2ccccc2)c([N+](=O)[O-])c1)c1ccc(N2CCN(Cc3ccccc3-c3ccc(Cl)cc3)CC2)cc1] |
| N-(4-(4-((1,1'-biphenyl)-2-ylmethyl)piperazin-1-yl)benzoyl)-3-nitro-4-((4-(phenylsulfanyl)tetrahydro-3-furanyl)amino)benzenesulfonamide | 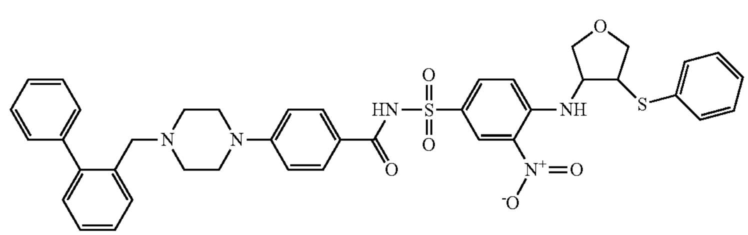 |

| Name | Structure |
|---|---|
| 4-(((1R)-3-(dimethylamino)-1-((phenylsulfanyl)methyl)propyl)amino)-N-(4-(4-(2-(5-methyl-2-thienyl)benzyl)piperazin-1-yl)benzoyl)-3-nitrobenzenesulfonamide | 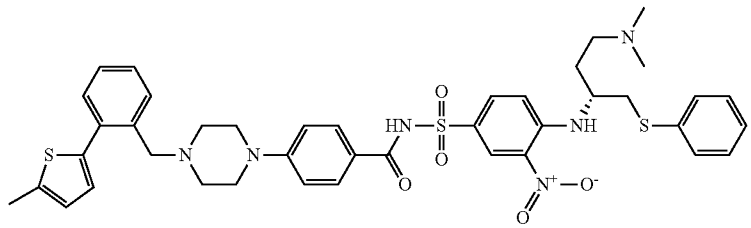 [SMILES: Cc1ccc(-c2ccccc2CN2CCN(c3ccc(C(=O)NS(=O)(=O)c4ccc(N[C@H](CCN(C)C)CSc5ccccc5)c([N+](=O)[O-])c4)cc3)CC2)s1] |
| N-(4-(4-((4'-chloro(1,1'-biphenyl)-2-yl)methyl)piperazin-1-yl)benzoyl)-3-nitro-4-((4-(phenylsulfonyl)tetrahydro-3-furanyl)amino)benzenesulfonamide | 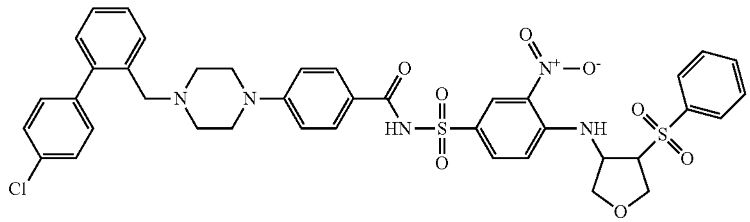 [SMILES: O=C(NS(=O)(=O)c1ccc(NC2COCC2S(=O)(=O)c2ccccc2)c([N+](=O)[O-])c1)c1ccc(N2CCN(Cc3ccccc3-c3ccc(Cl)cc3)CC2)cc1] |
| N-(4-(4-((1,1'-biphenyl)-2-ylmethyl)piperazin-1-yl)benzoyl)-3-nitro-4-((4-(phenylsulfonyl)tetrahydro-3-furanyl)amino)benzenesulfonamide | 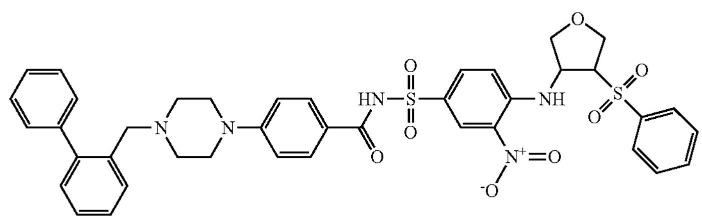 |
| N-(4-(4-((4'-chloro(1,1'-biphenyl)-2-yl)methyl)piperazin-1-yl)benzoyl)-4-((1-methyl-4-(phenylsulfanyl)pyrrolidin-3-yl)amino)-3-nitrobenzenesulfonamide | 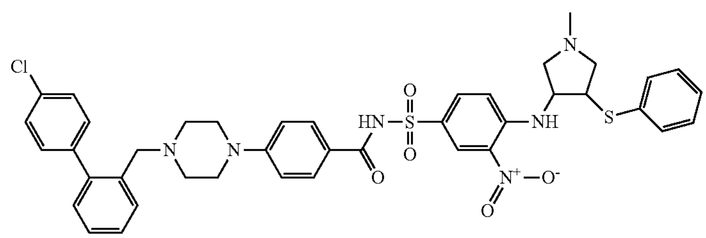 [SMILES: CN1CC(Nc2ccc(S(=O)(=O)NC(=O)c3ccc(N4CCN(Cc5ccccc5-c5ccc(Cl)cc5)CC4)cc3)cc2[N+](=O)[O-])C(Sc2ccccc2)C1] |
| N-(4-(4-((2-(4-chlorophenyl)-1-cyclohexen-1-yl)methyl)piperazin-1-yl)benzoyl)-4-(((1R)-3-(morpholin-4-yl)-1-((phenylsulfanyl)methyl)propyl)amino)-3-nitrobenzenesulfonamide | |
| N-(4-(4-((2-(4-chlorophenyl)-1-cyclohexen-1-yl)methyl)piperazin-1-yl)benzoyl)-4-(((1R)-3-(morpholin-4-yl)-1-((phenylsulfanyl)methyl)propyl)amino)-3-nitrobenzenesulfonamide | |

| Name | Structure |
|---|---|
| N-(4-(4-((4'-bromo(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide | 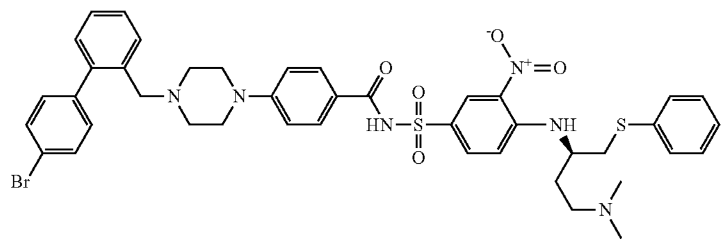 |
| N-(4-(4-(1-(4'-chloro(1,1'-biphenyl)-2-yl)cyclopropyl)piperazin-1-yl)benzoyl)-4-(((1R)-3-(dimethylamino)-1-((phenylsulfanyl)methyl)propyl)amino)-3-nitrobenzenesulfonamide | 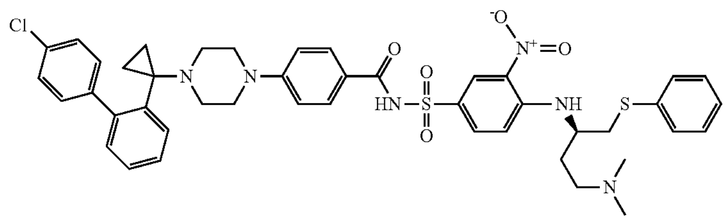 |
| N-(4-(4-((2-(4-chlorophenyl)-1-cyclohexen-1-yl)methyl)piperazin-1-yl)benzoyl)-4-(((1R)-2-(dimethylamino)-1-((phenylsulfanyl)methyl)ethyl)amino)-3-nitrobenzenesulfonamide | 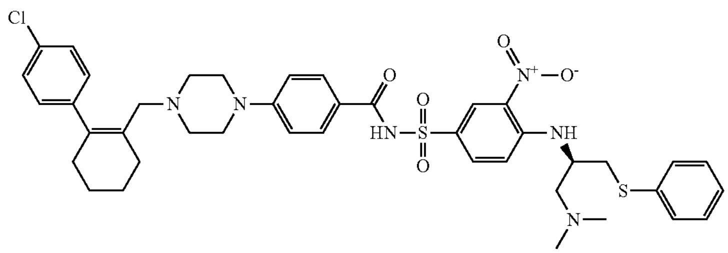 [SMILES: CN(C)C[C@H](CSc1ccccc1)Nc1ccc(S(=O)(=O)NC(=O)c2ccc(N3CCN(CC4=C(c5ccc(Cl)cc5)CCCC4)CC3)cc2)cc1[N+](=O)[O-]] |
| N-(4-(4-((4'-chloro(1,1'-biphenyl)-2-yl)methyl)piperazin-1-yl)benzoyl)-4-(((1R)-2-(dimethylamino)-1-((phenylsulfanyl)methyl)ethyl)amino)-3-nitrobenzenesulfonamide | 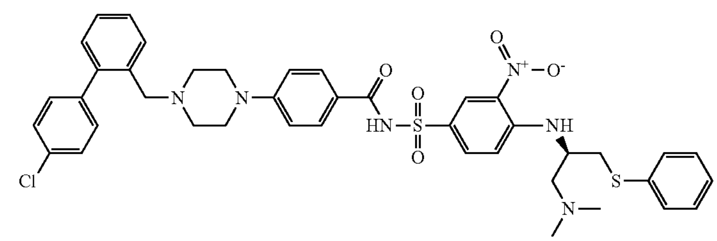 [SMILES: CN(C)C[C@H](CSc1ccccc1)Nc1ccc(S(=O)(=O)NC(=O)c2ccc(N3CCN(Cc4ccccc4-c4ccc(Cl)cc4)CC3)cc2)cc1[N+](=O)[O-]] |
| N-(4-(4-((4'-chloro(1,1'-biphenyl)-2-yl)methyl)piperazin-1-yl)benzoyl)-4-(((1R)-2-(diethylamino)-1-((phenylsulfanyl)methyl)ethyl)amino)-3-nitrobenzenesulfonamide | 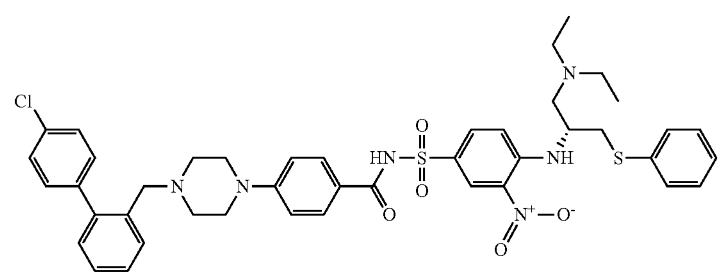 [SMILES: CCN(CC)C[C@H](CSc1ccccc1)Nc1ccc(S(=O)(=O)NC(=O)c2ccc(N3CCN(Cc4ccccc4-c4ccc(Cl)cc4)CC3)cc2)cc1[N+](=O)[O-]] |
| N-(4-(4-((4'-chloro(1,1'-biphenyl)-2-yl)methyl)piperazin-1-yl)benzoyl)-4-(((1R)-2-(morpholin-4-yl)-1-((phenylsulfanyl)methyl)ethyl)amino)-3-nitrobenzenesulfonamide | 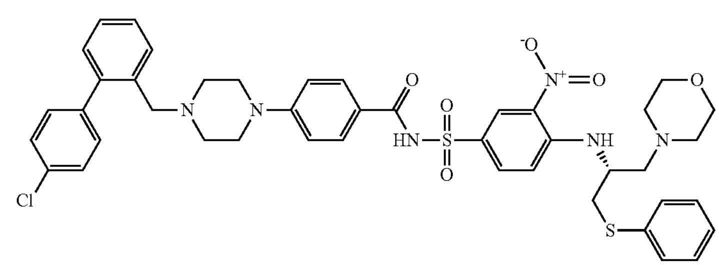 |

-continued

| Name | Structure |
|---|---|
| N-(4-(4-((2-(4-chlorophenyl)-1-cyclohexen-1-yl)methyl)piperazin-1-yl)benzoyl)-4-(((1R)-2-(diethylamino)-1-((phenylsulfanyl)methyl)ethyl)amino)-3-nitrobenzenesulfonamide | 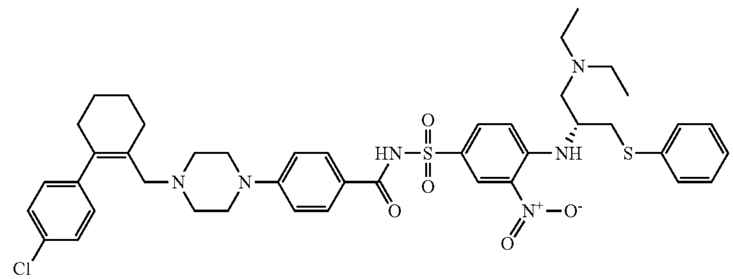 [SMILES: CCN(CC)C[C@H](CSc1ccccc1)Nc1ccc(S(=O)(=O)NC(=O)c2ccc(N3CCN(CC4=C(c5ccc(Cl)cc5)CCCC4)CC3)cc2)cc1[N+](=O)[O-]] |
| N-(4-(4-((2-(4-chlorophenyl)-1-cyclohexen-1-yl)methyl)piperazin-1-yl)benzoyl)-4-(((1R)-2-(morpholin-4-yl)-1-((phenylsulfanyl)methyl)ethyl)amino)-3-nitrobenzenesulfonamide | 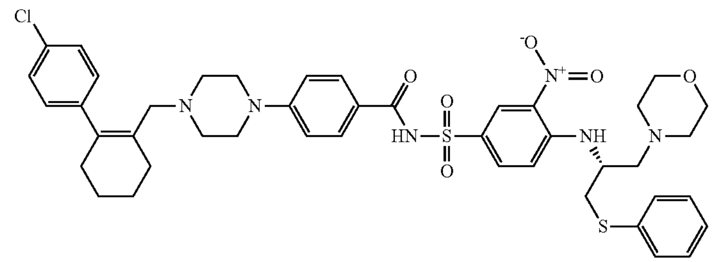 |
| N-(4-(4-((4'-chloro(1,1'-biphenyl)-2-yl)methyl)piperazin-1-yl)benzoyl)-4-(((1R)-3-(cyclopropyl(methyl)amino)-1-((phenylsulfanyl)methyl)propyl)amino)-3-nitrobenzenesulfonamide | 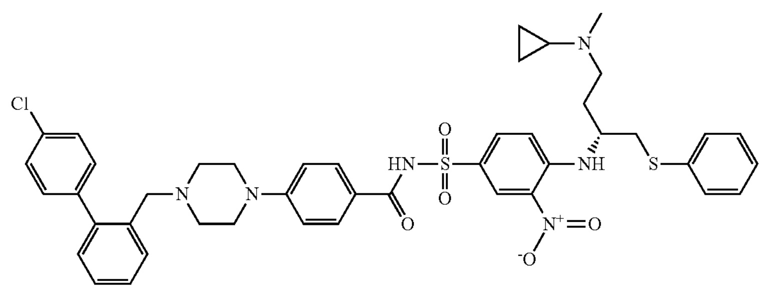 |
| N-(4-(4-((1,1'-biphenyl)-2-ylmethyl)-4-methoxypiperidin-1-yl)benzoyl)-4-(((1R)-3-(dimethylamino)-1-((phenylsulfanyl)methyl)propyl)amino)-3-nitrobenzenesulfonamide | 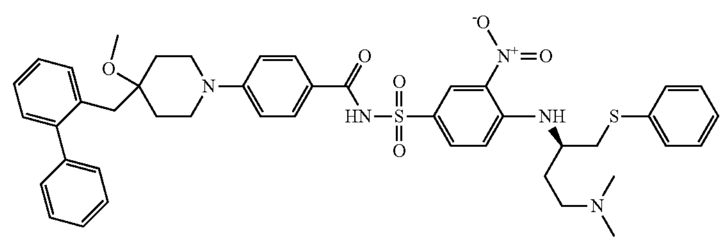 |
| 4-(((1R)-3-(dimethylamino)-1-((phenylsulfanyl)methyl)propyl)amino)-N-(4-(4-methoxy-4-(2-(pyridin-3-yl)benzyl)piperidin-1-yl)benzoyl)-3-nitrobenzenesulfonamide | 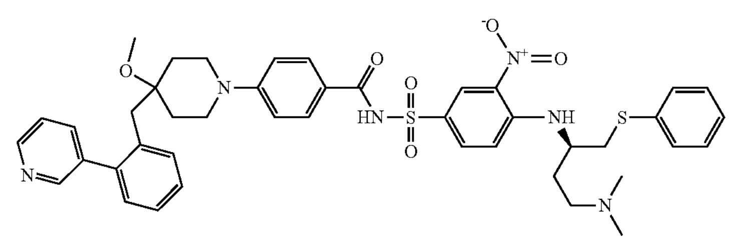 |
| 4-(((1R)-3-(dimethylamino)-1-((phenylsulfanyl)methyl)propyl)amino)-N-(4-(4-methoxy-4-(2-(pyridin-4-yl)benzyl)piperidin-1-yl)benzoyl)-3-nitrobenzenesulfonamide | 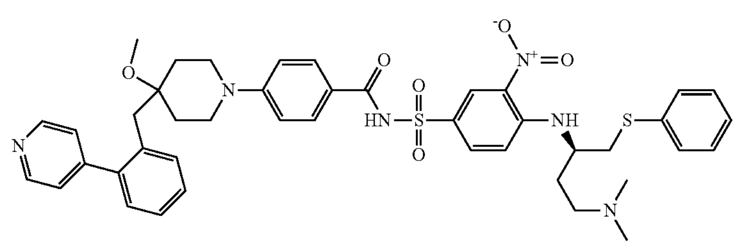 |

-continued

| Name | Structure |
|---|---|
| 4-(((1R)-3-(dimethylamino)-1-((phenylsulfanyl)methyl)propyl)amino)-N-(4-(4-methoxy-4-(2-(2-thienyl)benzyl)piperidin-1-yl)benzoyl)-3-nitrobenzenesulfonamide | 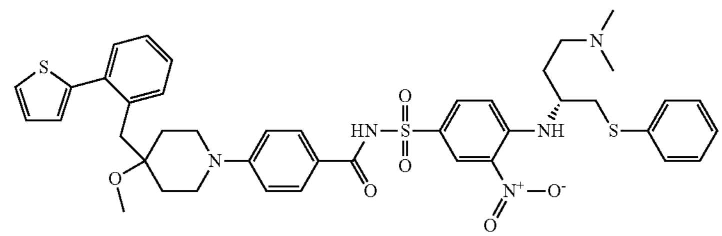 [SMILES: COC1(Cc2ccccc2-c2cccs2)CCN(c2ccc(C(=O)NS(=O)(=O)c3ccc(N[C@H](CCN(C)C)CSc4ccccc4)c([N+](=O)[O-])c3)cc2)CC1] |
| 4-(((1R)-3-(dimethylamino)-1-((phenylsulfanyl)methyl)propyl)amino)-N-(4-(4-methoxy-4-(2-(3-thienyl)benzyl)piperidin-1-yl)benzoyl)-3-nitrobenzenesulfonamide | 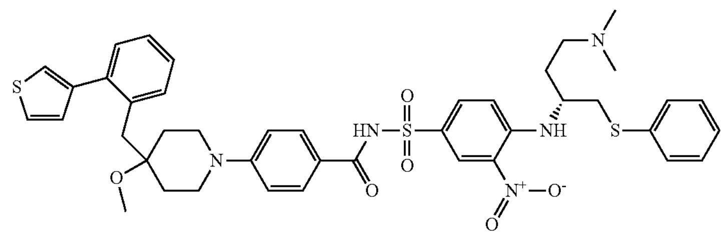 [SMILES: COC1(Cc2ccccc2-c2ccsc2)CCN(c2ccc(C(=O)NS(=O)(=O)c3ccc(N[C@H](CCN(C)C)CSc4ccccc4)c([N+](=O)[O-])c3)cc2)CC1] |
| 4-(((1R)-3-(azetidin-1-yl)-1-((phenylsulfanyl)methyl)propyl)amino)-N-(4-(4-((4'-chloro(1,1'-biphenyl)-2-yl)methyl)piperazin-1-yl)benzoyl)-3-nitrobenzenesulfonamide | 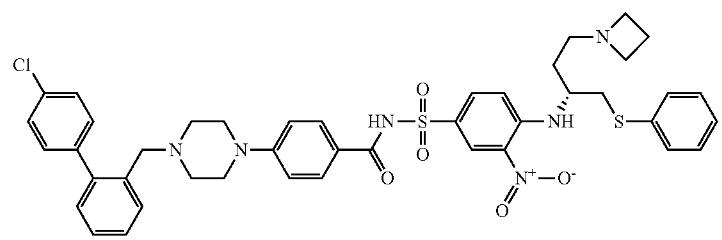 [SMILES: O=C(NS(=O)(=O)c1ccc(N[C@H](CCN2CCC2)CSc2ccccc2)c([N+](=O)[O-])c1)c1ccc(N2CCN(Cc3ccccc3-c3ccc(Cl)cc3)CC2)cc1] |
| N-(4-(4-((4'-chloro(1,1'-biphenyl)-2-yl)methyl)piperazin-1-yl)benzoyl)-3-nitro-4-(((1R)-1-((phenylsulfanyl)methyl)-3-((2,2,2-trifluoroethyl)amino)propyl)amino)benzenesulfonamide | 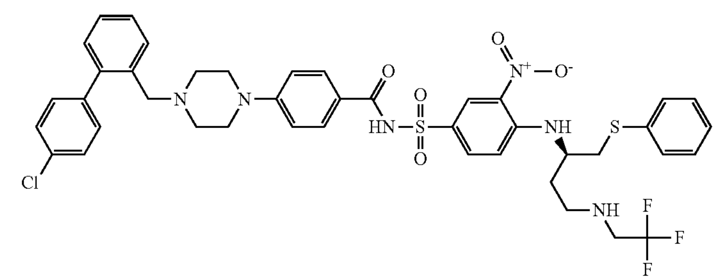 [SMILES: O=C(NS(=O)(=O)c1ccc(N[C@H](CCNCC(F)(F)F)CSc2ccccc2)c([N+](=O)[O-])c1)c1ccc(N2CCN(Cc3ccccc3-c3ccc(Cl)cc3)CC2)cc1] |
| N-(4-(4-((4'-chloro(1,1'-biphenyl)-2-yl)methyl)piperazin-1-yl)benzoyl)-4-(((1R)-3-(methyl(2,2,2-trifluoroethyl)amino)-1-((phenylsulfanyl)methyl)propyl)amino)-3-nitrobenzenesulfonamide | 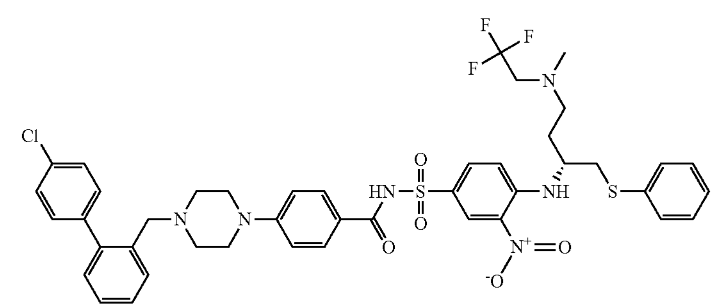 |
| N-(4-(4-((4'-chloro(1,1'-biphenyl)-2-yl)methyl)-4-methoxypiperidin-1-yl)benzoyl)-4-(((1R)-3-(morpholin-4-yl)-1-((phenylsulfanyl)methyl)propyl)amino)-3-nitrobenzenesulfonamide | 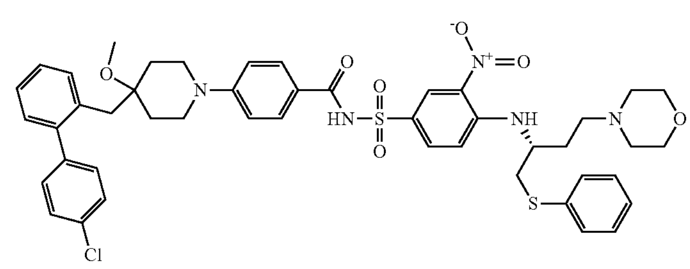 |

| Name | Structure |
|---|---|
| N-(4-(4-((4'-chloro(1,1'-biphenyl)-2-yl)methyl)-4-methoxypiperidin-1-yl)benzoyl)-3-nitro-4-((2-(phenylsulfanyl)ethyl)amino)benzenesulfonamide | 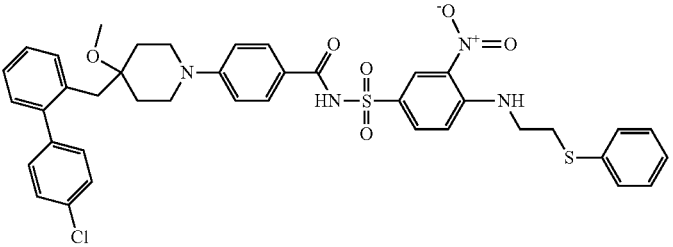 |
| N-(4-(4-((4'-chloro(1,1'-biphenyl)-2-yl)methyl)piperazin-1-yl)benzoyl)-4-(((1R)-3-(ethyl(2,2,2-trifluoroethyl)amino)-1-((phenylsulfanyl)methyl)propyl)amino)-3-nitrobenzenesulfonamide | 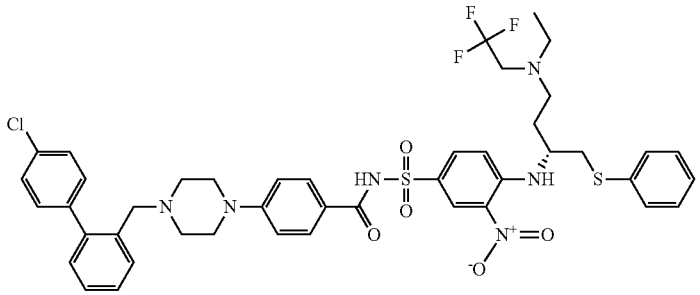 |
| N-(4-(4-((4'-chloro(1,1'-biphenyl)-2-yl)methyl)piperazin-1-yl)benzoyl)-4-(((1R)-3-((2-fluoroethyl)amino)-1-((phenylsulfanyl)methyl)propyl)amino)-3-nitrobenzenesulfonamide | 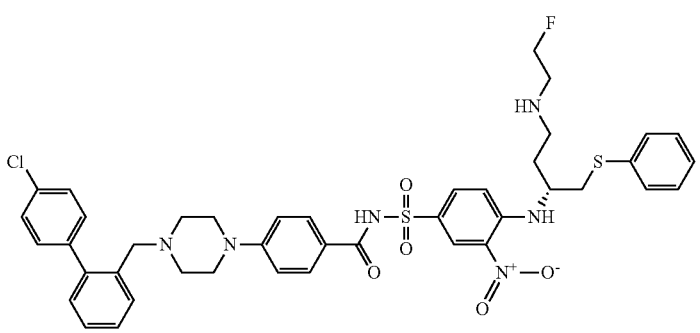 [SMILES: O=C(NS(=O)(=O)c1ccc(N[C@H](CCNCCF)CSc2ccccc2)c([N+](=O)[O-])c1)c1ccc(N2CCN(Cc3ccccc3-c3ccc(Cl)cc3)CC2)cc1] |
| N-(4-(4-((4'-chloro(1,1'-biphenyl)-2-yl)methyl)piperazin-1-yl)benzoyl)-4-(((1R)-3-((2,2-difluoroethyl)amino)-1-((phenylsulfanyl)methyl)propyl)amino)-3-nitrobenzenesulfonamide | 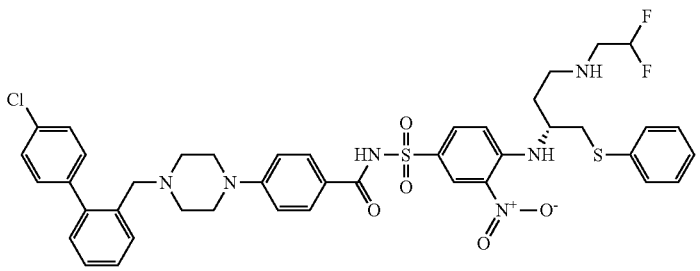 [SMILES: O=C(NS(=O)(=O)c1ccc(N[C@H](CCNCC(F)F)CSc2ccccc2)c([N+](=O)[O-])c1)c1ccc(N2CCN(Cc3ccccc3-c3ccc(Cl)cc3)CC2)cc1] |
| N-(4-(4-((4'-chloro(1,1'-biphenyl)-2-yl)methyl)piperazin-1-yl)benzoyl)-1-((1R)-3-(dimethylamino)-1-((phenylsulfanyl)methyl)propyl)-1H-benzimidazole-5-sulfonamide | 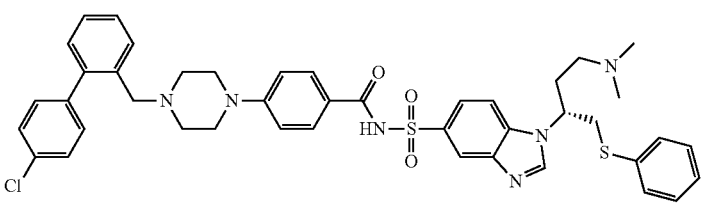 [SMILES: CN(C)CC[C@H](CSc1ccccc1)n1cnc2cc(S(=O)(=O)NC(=O)c3ccc(N4CCN(Cc5ccccc5-c5ccc(Cl)cc5)CC4)cc3)ccc21] |
| N-(4-(4-((4'-chloro(1,1'-biphenyl)-2-yl)methyl)piperazin-1-yl)benzoyl)-1-((1R)-3-(dimethylamino)-1-((phenylsulfanyl)methyl)propyl)-1H-1,2,3-benzotriazole-5-sulfonamide | 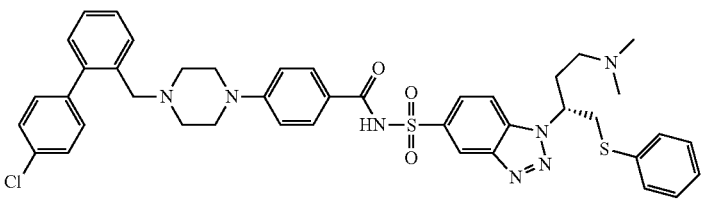 |

-continued

| Name | Structure |
|---|---|
| 5-(((4-(4-((4'-chloro(1,1'-biphenyl)-2-yl)methyl)piperazin-1-yl)benzoyl)amino)sulfonyl)-2-(((1R)-3-(dimethylamino)-1-((phenylsulfanyl)methyl)propyl)amino)benzamide | 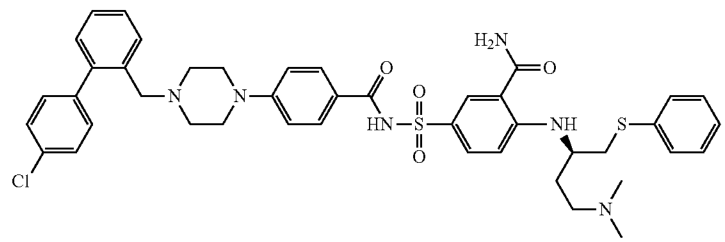 [SMILES: CN(C)CC[C@H](CSc1ccccc1)Nc1ccc(S(=O)(=O)NC(=O)c2ccc(N3CCN(Cc4ccccc4-c4ccc(Cl)cc4)CC3)cc2)cc1C(N)=O] |
| N-(4-(4-((4'-(dimethylamino)(1,1'-biphenyl)-2-yl)carbonyl)piperazin-1-yl)benzoyl)-4-(((1R)-3-(dimethylamino)-1-((phenylsulfanyl)methyl)propyl)amino)-3-nitrobenzenesulfonamide | 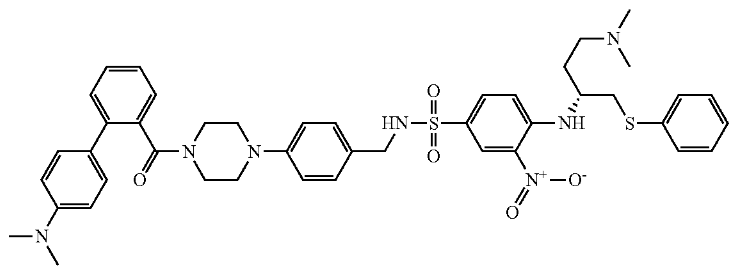 [SMILES: CN(C)CC[C@H](CSc1ccccc1)Nc1ccc(S(=O)(=O)NCc2ccc(N3CCN(C(=O)c4ccccc4-c4ccc(N(C)C)cc4)CC3)cc2)cc1[N+](=O)[O-]] |
| 4-(((1R)-3-(dimethylamino)-1-((phenylsulfanyl)methyl)propyl)amino)-N-(4-(4-((4'-(methylsulfanyl)(1,1'-biphenyl)-2-yl)carbonyl)piperazin-1-yl)benzoyl)-3-nitrobenzenesulfonamide | |
| 4-(((1R)-3-(dimethylamino)-1-((phenylsulfanyl)methyl)propyl)amino)-N-(4-(4-((4'-(methylsulfanyl)(1,1'-biphenyl)-2-yl)carbonyl)piperazin-1-yl)benzoyl)-3-nitrobenzenesulfonamide | |
| N-(4-(4-((4'-chloro(1,1'-biphenyl)-2-yl)methyl)piperazin-1-yl)benzoyl)-3-cyano-4-(((1R)-3-(dimethylamino)-1-((phenylsulfanyl)methyl)propyl)amino)benzenesulfonamide | 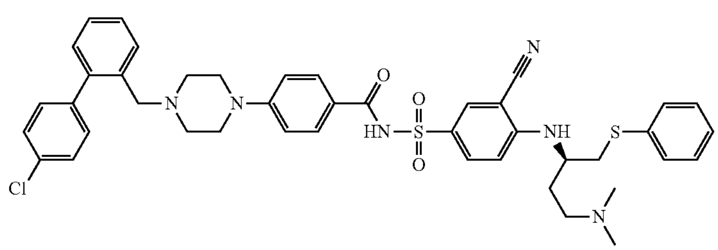 |
| N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)oxy)-3-nitrobenzenesulfonamide | 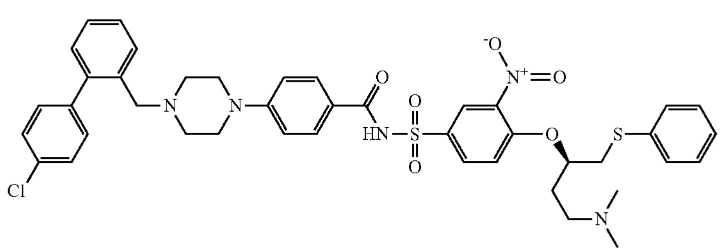 |

| Name | Structure |
|---|---|
| N-(4-(4-((4'-chloro(1,1'-biphenyl)-2-yl)methyl)piperazin-1-yl)benzoyl)-4-(((1R)-3-(4,4-dimethyl-4,5-dihydro-1H-imidazol-1-yl)-1-((phenylsulfanyl)methyl)propyl)amino)-3-nitrobenzenesulfonamide | 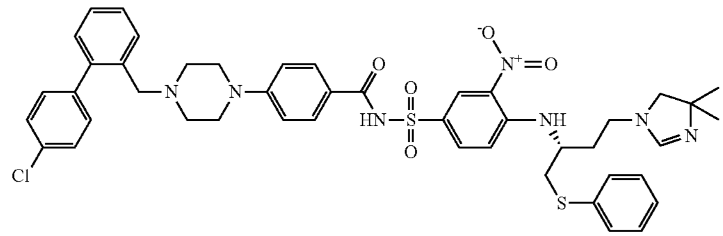 |
| N-(4-(4-((4'-chloro(1,1'-biphenyl)-2-yl)methyl)piperazin-1-yl)benzoyl)-4-(((1R)-3-(5,6-dihydro-1(4H)-pyrimidin-1-yl)-1-((phenylsulfanyl)methyl)propyl)amino)-3-nitrobenzenesulfonamide | |
| N-(4-(4-((4'-chloro(1,1'-biphenyl)-2-yl)methyl)piperazin-1-yl)benzoyl)-4-(((1R)-3-(2-methyl-4,5-dihydro-1H-imidazol-1-yl)-1-((phenylsulfanyl)methyl)propyl)amino)-3-nitrobenzenesulfonamide | 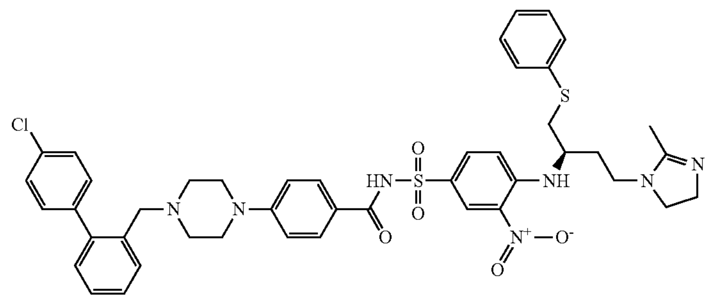 [SMILES: CC1=NCCN1CC[C@H](CSc1ccccc1)Nc1ccc(S(=O)(=O)NC(=O)c2ccc(N3CCN(Cc4ccccc4-c4ccc(Cl)cc4)CC3)cc2)cc1[N+](=O)[O-]] |
| N-(4-(4-((4'-chloro(1,1'-biphenyl)-2-yl)methyl)piperazin-1-yl)benzoyl)-4-(((1R)-3-(5,6-dihydro-1-(4H)-pyrimidin-1-yl)-1-((phenylsulfanyl)methyl)propyl)amino)-3-(trifluoromethyl)benzenesulfonamide | |
| N-(4-(4-((4'-chloro(1,1'-biphenyl)-2-yl)methyl)piperazin-1-yl)benzoyl)-4-(((1R)-3-(2,4-dimethyl-4,5-dihydro-1H-imidazol-1-yl)-1-((phenylsulfanyl)methyl)propyl)amino)-3-(trifluoromethyl)benzenesulfonamide | 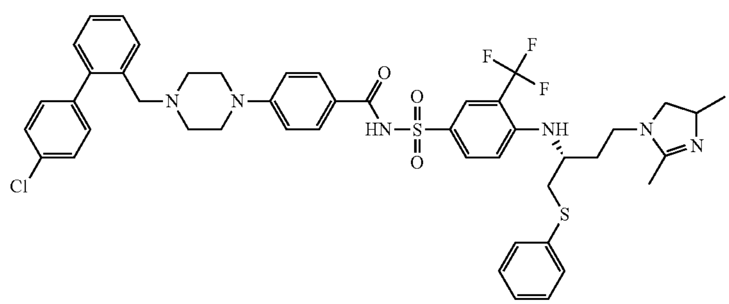 [SMILES: CC1=NC(C)CN1CC[C@H](CSc1ccccc1)Nc1ccc(S(=O)(=O)NC(=O)c2ccc(N3CCN(Cc4ccccc4-c4ccc(Cl)cc4)CC3)cc2)cc1C(F)(F)F] |
| N-(4-(4-((4'-chloro(1,1'-biphenyl)-2-yl)methyl)piperazin-1-yl)benzoyl)-4-(((1R)-3-(2-methyl-4,5-dihydro-1H-imidazol-1-yl)-1-((phenylsulfanyl)methyl)propyl)amino)-3-(trifluoromethyl)benzenesulfonamide | 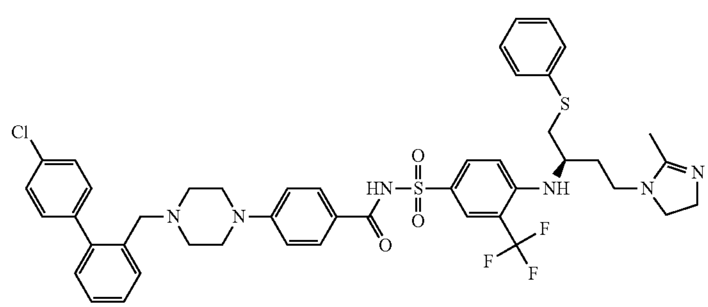 [SMILES: CC1=NCCN1CC[C@H](CSc1ccccc1)Nc1ccc(S(=O)(=O)NC(=O)c2ccc(N3CCN(Cc4ccccc4-c4ccc(Cl)cc4)CC3)cc2)cc1C(F)(F)F] |

| Name | Structure |
|---|---|
| N-(4-(4-((4'-chloro(1,1'-biphenyl)-2-yl)methyl)piperazin-1-yl)benzoyl)-4-(((1R)-3-(4,4-dimethyl-4,5-dihydro-1H-imidazol-1-yl)-1-((phenylsulfanyl)methyl)propyl)amino)-3-(trifluoromethyl)benzenesulfonamide | 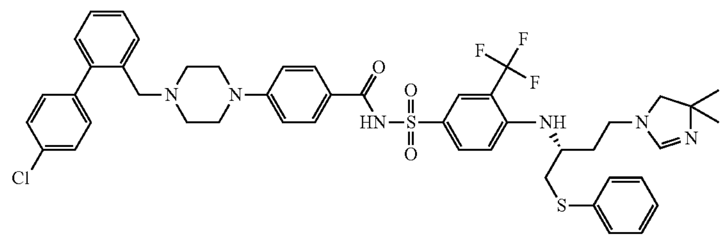 [SMILES: CC1(C)CN(CC[C@H](CSc2ccccc2)Nc2ccc(S(=O)(=O)NC(=O)c3ccc(N4CCN(Cc5ccccc5-c5ccc(Cl)cc5)CC4)cc3)cc2C(F)(F)F)C=N1] |
| N-(4-(4-((2-(4-chlorophenyl)-1-cyclohexen-1-yl)methyl)piperazin-1-yl)benzoyl)-4-(((1R)-3-(dimethylamino)-1-((phenylsulfanyl)methyl)propyl)oxy)-3-(trifluoromethyl)benzenesulfonamide | 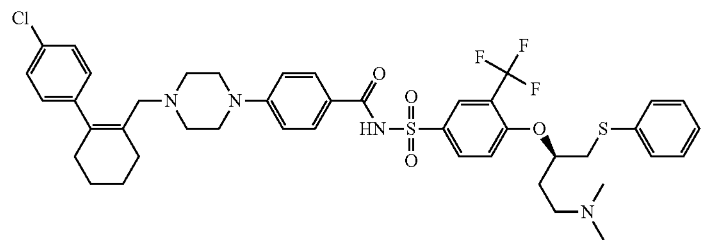 |
| N-(4-(4-((2-(4-chlorophenyl)cyclohept-1-en-1-yl)methyl)piperazin-1-yl)benzoyl)-4-(((1R)-3-(dimethylamino)-1-((phenylsulfanyl)methyl)propyl)amino)-3-(trifluoromethyl)benzenesulfonamide | 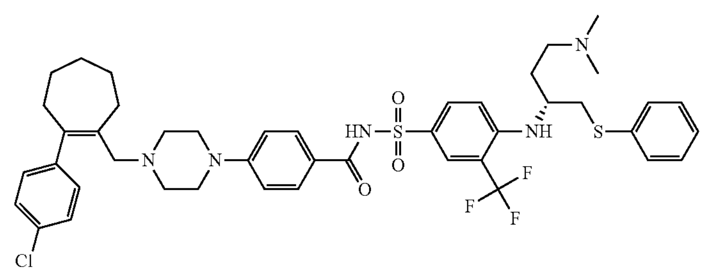 [SMILES: CN(C)CC[C@H](CSc1ccccc1)Nc1ccc(S(=O)(=O)NC(=O)c2ccc(N3CCN(CC4=C(c5ccc(Cl)cc5)CCCCC4)CC3)cc2)cc1C(F)(F)F] |
| 4-(((1R)-3-(bis(2-methoxyethyl)amino)-1-((phenylsulfanyl)methyl)propyl)amino)-N-(4-(4-((4'-chloro(1,1'-biphenyl)-2-yl)methyl)piperazin-1-yl)benzoyl)-3-nitrobenzenesulfonamide | 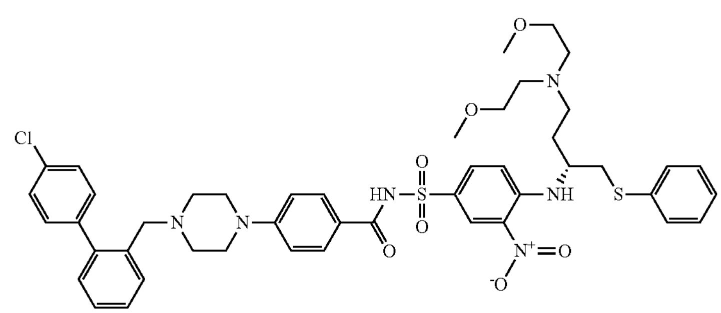 |
| 4-(((1R)-3-(bis(2-methoxyethyl)amino)-1-((phenylsulfanyl)methyl)propyl)amino)-N-(4-(4-((4'-chloro(1,1'-biphenyl)-2-yl)methyl)piperazin-1-yl)benzoyl)-3-(trifluoromethyl)benzenesulfonamide | 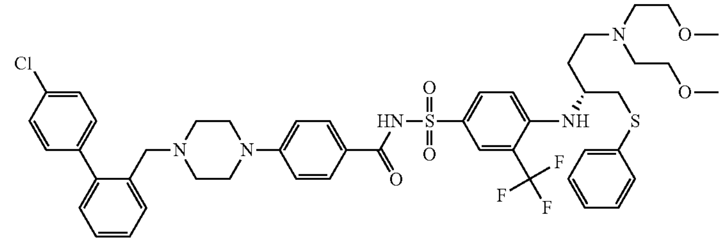 [SMILES: COCCN(CCOC)CC[C@H](CSc1ccccc1)Nc1ccc(S(=O)(=O)NC(=O)c2ccc(N3CCN(Cc4ccccc4-c4ccc(Cl)cc4)CC3)cc2)cc1C(F)(F)F] |

| Name | Structure |
|---|---|
| 4-(((1R)-5-amino-1-((phenylsulfanyl)methyl)pentyl)amino)-N-(4-(4-((4'-chloro(1,1'-biphenyl)-4-yl)methyl)-1-piperazinyl)benzoyl)-3-nitrobenzenesulfonamide | 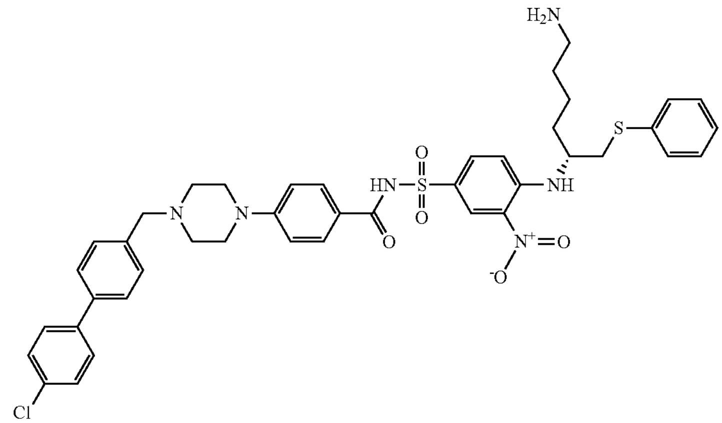 |
| N-(4-(4-((1,1'-biphenyl)-2-ylmethyl)piperazin-1-yl)benzoyl)-4-(((1R)-4-methyl-1-((phenylsulfanyl)methyl)pentyl)amino)-3-nitrobenzenesulfonamide, | 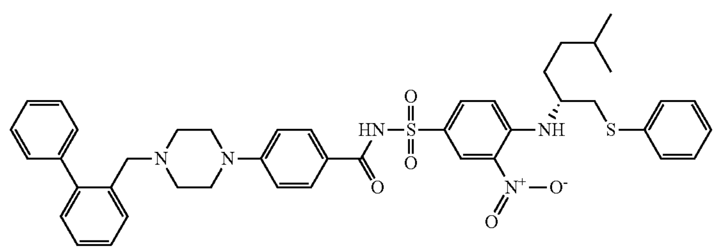 [SMILES: CC(C)CC[C@H](CSc1ccccc1)Nc1ccc(S(=O)(=O)NC(=O)c2ccc(N3CCN(Cc4ccccc4-c4ccccc4)CC3)cc2)cc1[N+](=O)[O-]] |
| tert-butyl(5R)-5-(4-(((4-(4-((4'-chloro(1,1'-biphenyl)-2-yl)methyl)piperazin-1-yl)benzoyl)amino)sulfonyl)-2-nitroanilino)-6-(phenylsulfanyl)hexylcarbamate | 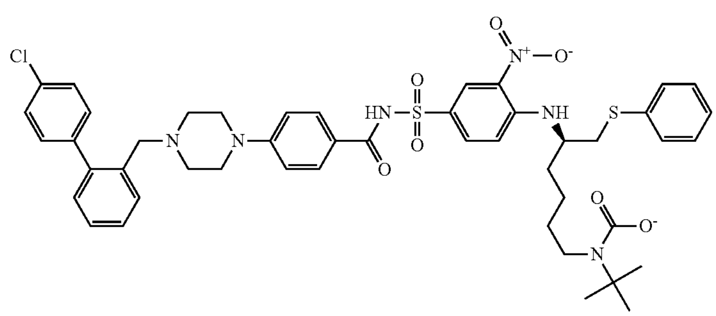 [SMILES: CC(C)(C)N(CCCC[C@H](CSc1ccccc1)Nc1ccc(S(=O)(=O)NC(=O)c2ccc(N3CCN(Cc4ccccc4-c4ccc(Cl)cc4)CC3)cc2)cc1[N+](=O)[O-])C(=O)[O-]] |
| 4-(((1R)-5-amino-1-((phenylsulfanyl)methyl)pentyl)amino)-N-(4-(4-((4'-chloro(1,1'-biphenyl)-2-yl)methyl)piperazin-1-yl)benzoyl)-3-nitrobenzenesulfonamide | 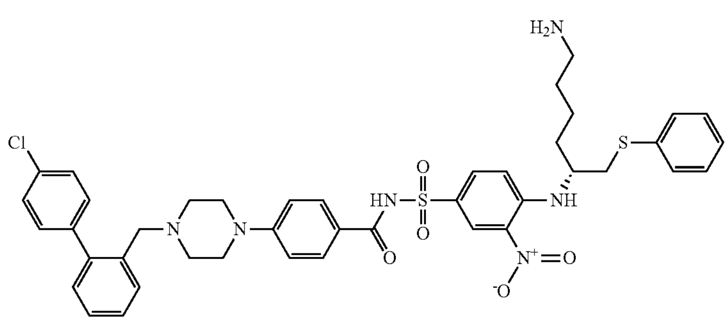 |

| Name | Structure |
|---|---|
| N-(4-(4-((4'-chloro(1,1'-biphenyl)-2-yl)methyl)piperazin-1-yl)benzoyl)-4-(((1R)-5-((methylsulfonyl)amino)-1-((phenylsulfanyl)methyl)pentyl)amino)-3-nitrobenzenesulfonamide | 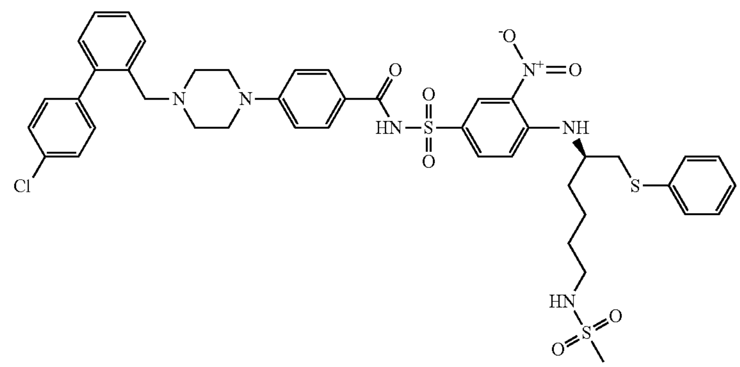 |
| 4-(((1R)-5-((aminocarbonyl)amino)-1-((phenylsulfanyl)methyl)pentyl)amino)-N-(4-(4-((4'-chloro(1,1'-biphenyl)-2-yl)methyl)piperazin-1-yl)benzoyl)-3-nitrobenzenesulfonamide | 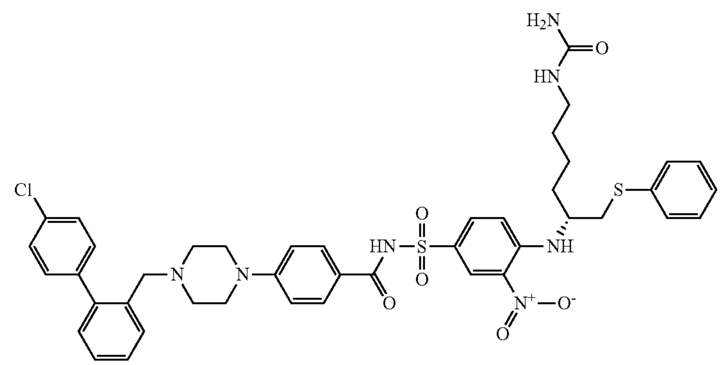 [SMILES: NC(=O)NCCCC[C@H](CSc1ccccc1)Nc1ccc(S(=O)(=O)NC(=O)c2ccc(N3CCN(Cc4ccccc4-c4ccc(Cl)cc4)CC3)cc2)cc1[N+](=O)[O-]] |
| 4-(((1R)-3-(dimethylamino)-1-((phenylsulfanyl)methyl)propyl)amino)-N-(4-(4-(2-(methylsulfanyl)benzyl)piperazin-1-yl)benzoyl)-3-nitrobenzenesulfonamide | 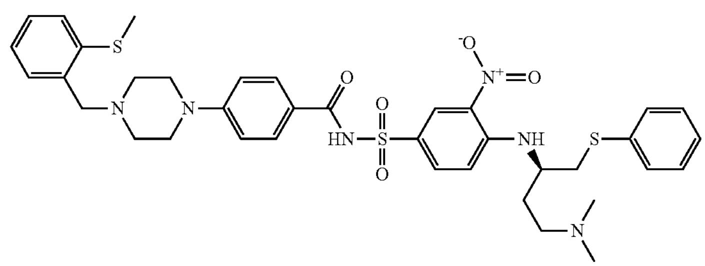 |
| 4-(((1R)-3-(dimethylamino)-1-((phenylsulfanyl)methyl)propyl)amino)-N-(4-(4-(2-(methylsulfonyl)benzyl)piperazin-1-yl)benzoyl)-3-nitrobenzenesulfonamide | 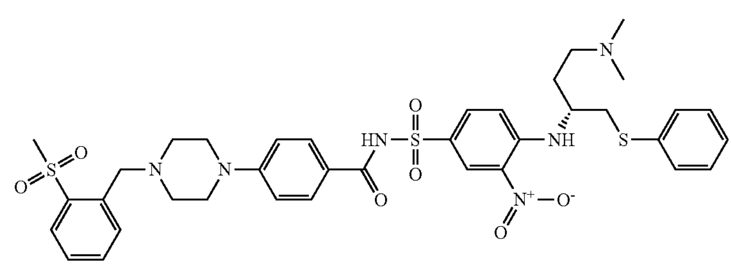 [SMILES: CN(C)CC[C@H](CSc1ccccc1)Nc1ccc(S(=O)(=O)NC(=O)c2ccc(N3CCN(Cc4ccccc4S(C)(=O)=O)CC3)cc2)cc1[N+](=O)[O-]] |
| 4-(((1R)-3-(dimethylamino)-1-((phenylsulfanyl)methyl)propyl)amino)-N-(4-(4-(2-(5,5-dimethyl-2-oxo-1,3-oxazolidin-3-yl)benzyl)piperazin-1-yl)benzoyl)-3-nitrobenzenesulfonamide | 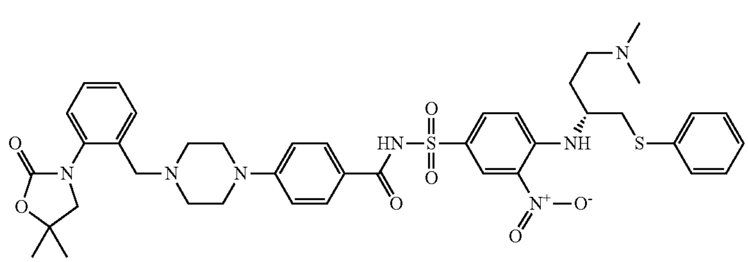 [SMILES: CN(C)CC[C@H](CSc1ccccc1)Nc1ccc(S(=O)(=O)NC(=O)c2ccc(N3CCN(Cc4ccccc4N4CC(C)(C)OC4=O)CC3)cc2)cc1[N+](=O)[O-]] |

-continued

| Name | Structure |
|---|---|
| N-(4-(4-(2-cyclohexylbenzyl)piperazin-1-yl)benzoyl)-4-(((1R)-3-(dimethylamino)-1-((phenylsulfanyl)methyl)propyl)amino)-3-nitrobenzenesulfonamide | 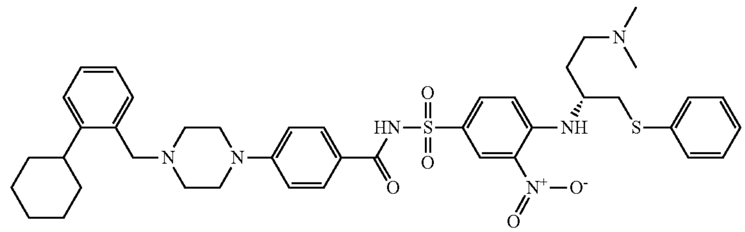 [SMILES: CN(C)CC[C@H](CSc1ccccc1)Nc1ccc(S(=O)(=O)NC(=O)c2ccc(N3CCN(Cc4ccccc4C4CCCCC4)CC3)cc2)cc1[N+](=O)[O-]] |
| 4-(((1R)-3-(dimethylamino)-1-((phenylsulfanyl)methyl)propyl)amino)-N-(4-(4-(2-(morpholin-4-yl)benzyl)piperazin-1-yl)benzoyl)-3-nitrobenzenesulfonamide | 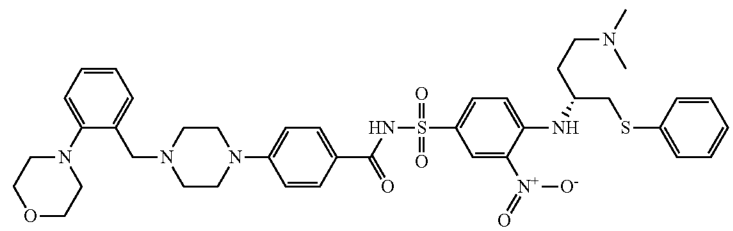 [SMILES: CN(C)CC[C@H](CSc1ccccc1)Nc1ccc(S(=O)(=O)NC(=O)c2ccc(N3CCN(Cc4ccccc4N4CCOCC4)CC3)cc2)cc1[N+](=O)[O-]] |
| 4-(((1R)-3-(dimethylamino)-1-((phenylsulfanyl)methyl)propyl)amino)-N-(4-(4-(2-(isopropylsulfanyl)benzyl)piperazin-1-yl)benzoyl)-3-nitrobenzenesulfonamide | 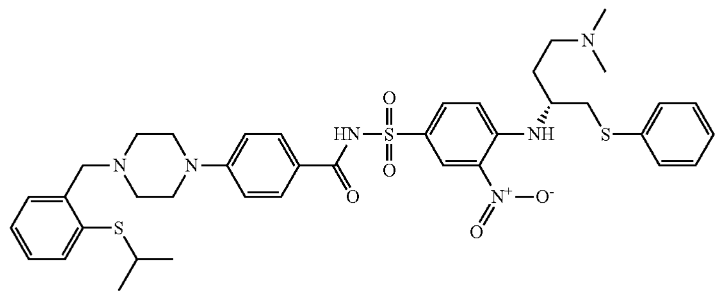 [SMILES: CC(C)Sc1ccccc1CN1CCN(c2ccc(C(=O)NS(=O)(=O)c3ccc(N[C@H](CCN(C)C)CSc4ccccc4)c([N+](=O)[O-])c3)cc2)CC1] |
| N-(4-(4-((2-(4-chlorophenyl)-1-cyclohexen-1-yl)methyl)piperazin-1-yl)benzoyl)-4-(((1R)-3-(isopropyl(methyl)amino)-1-((phenylsulfanyl)methyl)propyl)amino)-3-nitrobenzenesulfonamide | 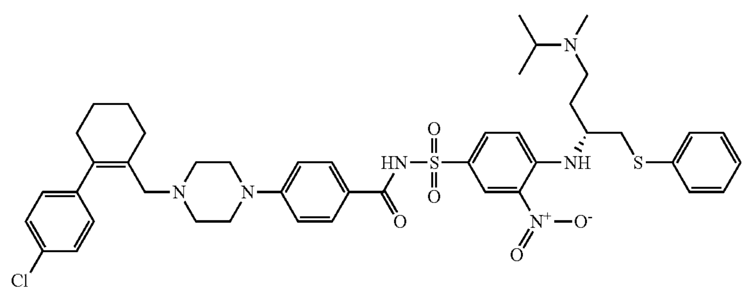 [SMILES: CC(C)N(C)CC[C@H](CSc1ccccc1)Nc1ccc(S(=O)(=O)NC(=O)c2ccc(N3CCN(CC4=C(c5ccc(Cl)cc5)CCCC4)CC3)cc2)cc1[N+](=O)[O-]] |
| N-(4-(4-((2-(4-chlorophenyl)-1-cyclohexen-1-yl)methyl)piperazin-1-yl)benzoyl)-4-(((1R)-3-(dipropylamino)-1-((phenylsulfanyl)methyl)propyl)amino)-3-nitrobenzenesulfonamide | 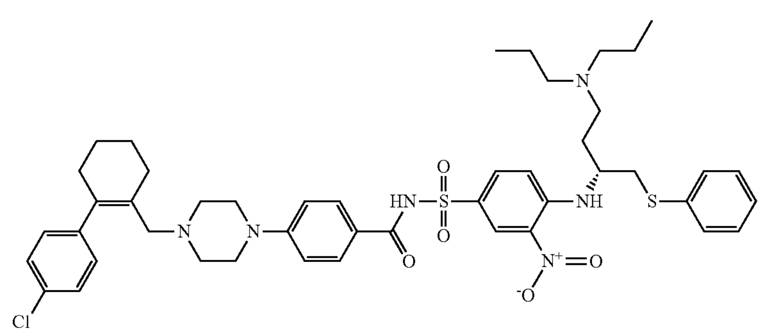 |

-continued

| Name | Structure |
|---|---|
| N-(4-(4-((4'-chloro(1,1'-biphenyl)-2-yl)methyl)piperazin-1-yl)benzoyl)-4-(((1R)-3-(dipropylamino)-1-((phenylsulfanyl)methyl)propyl)amino)-3-nitrobenzenesulfonamide | 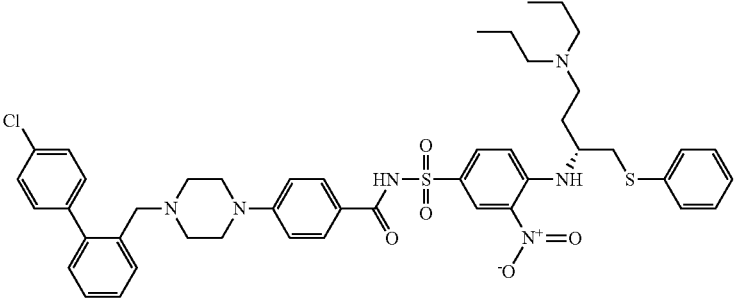 |
| N-(4-(4-((2-(4-chlorophenyl)-1-cyclohexen-1-yl)methyl)piperazin-1-yl)benzoyl)-4-(((1R)-3-(diethylamino)-1-((phenylsulfanyl)methyl)propyl)amino)-3-nitrobenzenesulfonamide | 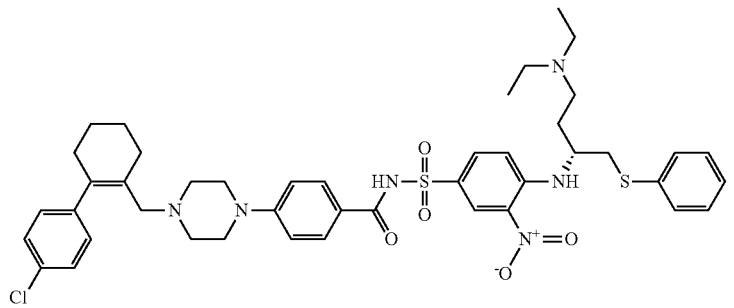 |
| N-(4-(4-((4'-chloro(1,1'-biphenyl)-2-yl)methyl)piperazin-1-yl)benzoyl)-4-(((1R)-3-(diethylamino)-1-((phenylsulfanyl)methyl)propyl)amino)-3-nitrobenzenesulfonamide | 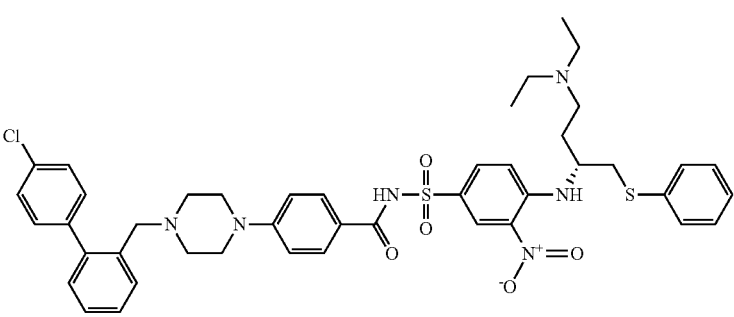 |
| N-(4-(4-((1,1'-biphenyl)-3-ylmethyl)piperazin-1-yl)benzoyl)-3-nitro-4-((2-(phenylsulfanyl)ethyl)amino)benzenesulfonamide | 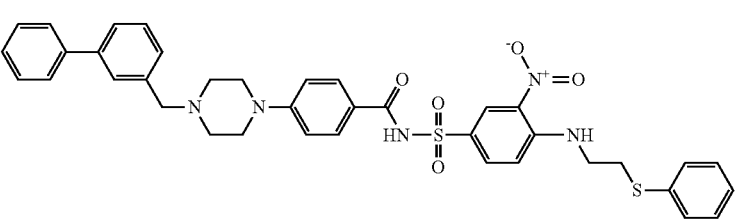 |
| N-(4-(4-((1,1'-biphenyl)-3-ylmethyl)piperazin-1-yl)benzoyl)-4-(((1R)-3-(dimethylamino)-1-((phenylsulfanyl)methyl)propyl)amino)-3-nitrobenzenesulfonamide | 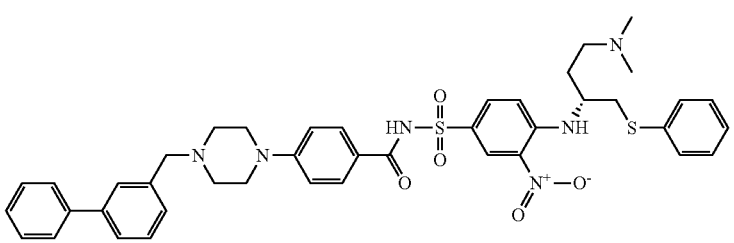 [SMILES: CN(C)CC[C@H](CSc1ccccc1)Nc1ccc(S(=O)(=O)NC(=O)c2ccc(N3CCN(Cc4cccc(-c5ccccc5)c4)CC3)cc2)cc1[N+](=O)[O-]] |

-continued

| Name | Structure |
|---|---|
| N-(4-(4-((1,1'-biphenyl)-3-ylmethyl)piperazin-1-yl)benzoyl)-4-(((1R)-3-(morpholin-4-yl)-1-((phenylsulfanyl)methyl)propyl)amino)-3-nitrobenzenesulfonamide | 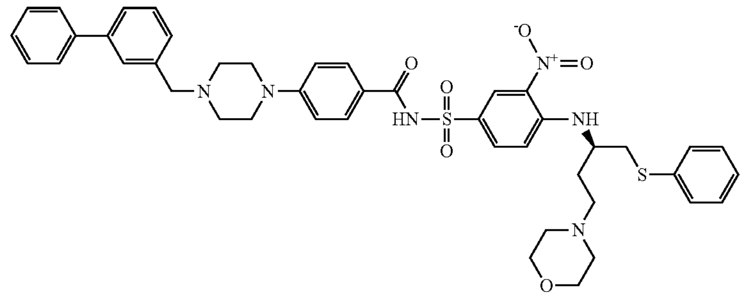 |
| N-(4-(4-((1,1'-biphenyl)-2-ylmethyl)piperazin-1-yl)-3-fluorobenzoyl)-4-(((1R)-3-(dimethylamino)-1-((phenylsulfanyl)methyl)propyl)amino)-3-nitrobenzenesulfonamide | 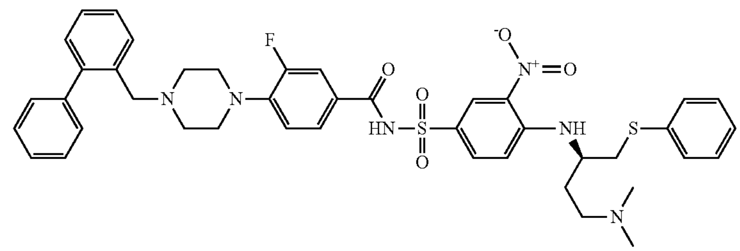 |
| N-(4-(4-((1,1'-biphenyl)-2-ylmethyl)piperazin-1-yl)-3-fluorobenzoyl)-3-nitro-4-((2-(phenylsulfanyl)ethyl)amino)benzenesulfonamide | 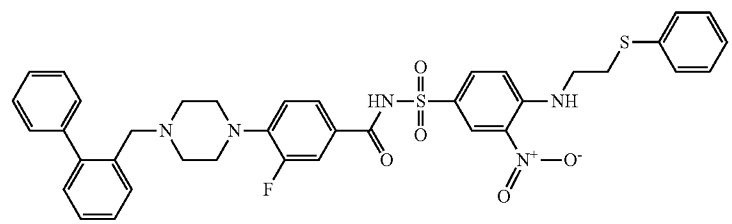 [SMILES: O=C(NS(=O)(=O)c1ccc(NCCSc2ccccc2)c([N+](=O)[O-])c1)c1ccc(N2CCN(Cc3ccccc3-c3ccccc3)CC2)c(F)c1] |
| N-(4-(4-((1,1'-biphenyl)-2-ylmethyl)piperazin-1-yl)-3-fluorobenzoyl)-4-(((1R)-3-(morpholin-4-yl)-1-((phenylsulfanyl)methyl)propyl)amino)-3-nitrobenzenesulfonamide | 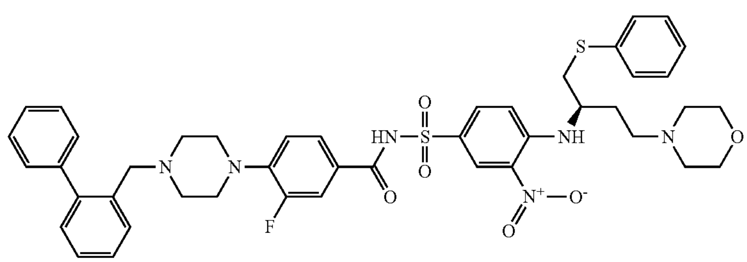 [SMILES: O=C(NS(=O)(=O)c1ccc(N[C@H](CCN2CCOCC2)CSc2ccccc2)c([N+](=O)[O-])c1)c1ccc(N2CCN(Cc3ccccc3-c3ccccc3)CC2)c(F)c1] |
| N-(4-(4-((1,1'-biphenyl)-2-ylmethyl)piperazin-1-yl)-3,5-difluorobenzoyl)-4-(((1R)-3-(dimethylamino)-1-((phenylsulfanyl)methyl)propyl)amino)-3-nitrobenzenesulfonamide | 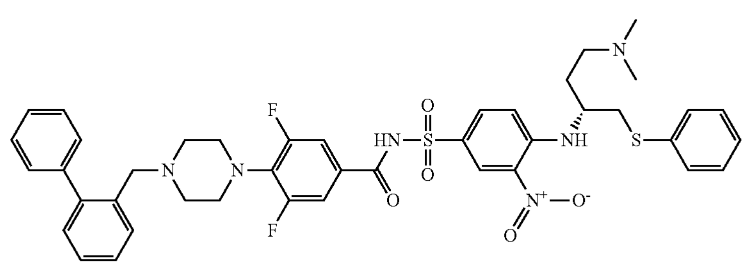 |
| N-(4-(4-((1,1'-biphenyl)-2-ylmethyl)piperazin-1-yl)-3,5-difluorobenzoyl)-3-nitro-4-((2-(phenylsulfanyl)ethyl)amino)benzenesulfonamide | 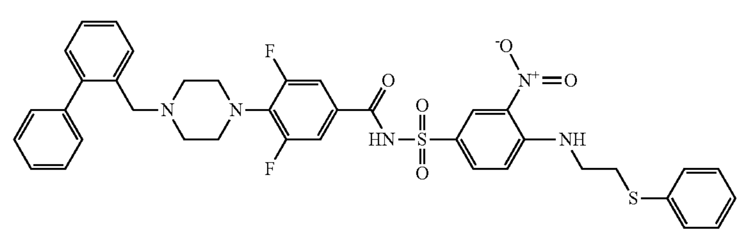 |

-continued

| Name | Structure |
|---|---|
| N-(4-(4-((1,1'-biphenyl)-2-ylmethyl)piperazin-1-yl)-3,5-difluorobenzoyl)-4-(((1R)-3-(morpholin-4-yl)-1-((phenylsulfanyl)methyl)propyl)amino)-3-nitrobenzenesulfonamide | 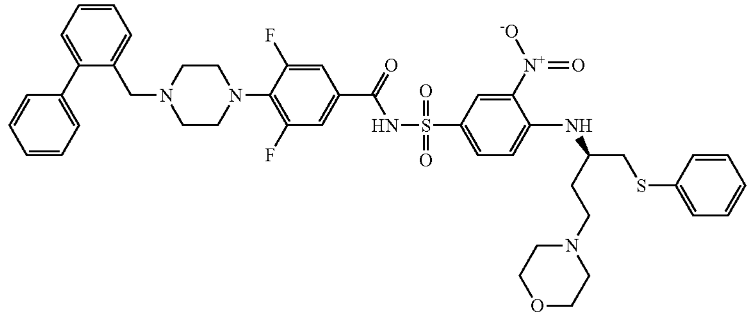 |
| 3-nitro-N-(4-(4-((1-phenyl-1H-imidazol-2-yl)methyl)piperazin-1-yl)benzoyl)-4-((2-(phenylsulfanyl)ethyl)amino)benzenesulfonamide | 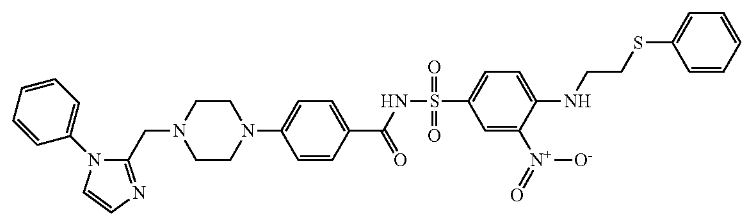 [SMILES: O=C(NS(=O)(=O)c1ccc(NCCSc2ccccc2)c([N+](=O)[O-])c1)c1ccc(N2CCN(Cc3nccn3-c3ccccc3)CC2)cc1] |
| 4-(((1R)-3-(morpholin-4-yl)-1-((phenylsulfanyl)methyl)propyl)amino)-3-nitro-N-(4-(4-((1-phenyl-1H-imidazol-2-yl)methyl)piperazin-1-yl)benzoyl)benzenesulfonamide | 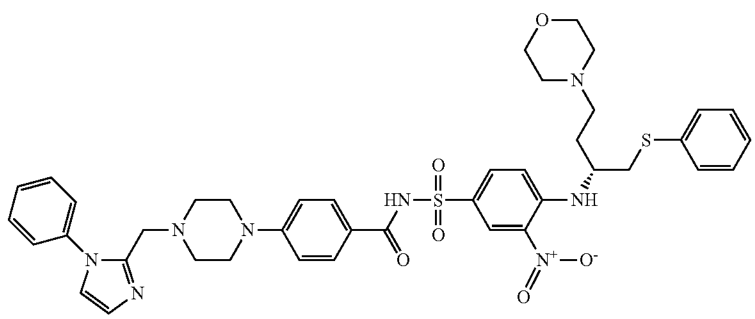 [SMILES: O=C(NS(=O)(=O)c1ccc(N[C@H](CCN2CCOCC2)CSc2ccccc2)c([N+](=O)[O-])c1)c1ccc(N2CCN(Cc3nccn3-c3ccccc3)CC2)cc1] |
| 3-nitro-N-(4-(4-((1-phenyl-1H-pyrazol-5-yl)methyl)piperazin-1-yl)benzoyl)-4-((2-(phenylsulfanyl)ethyl)amino)benzenesulfonamide | 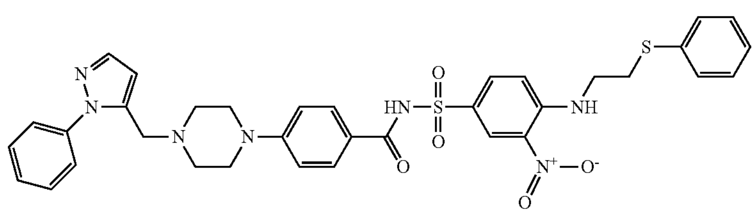 [SMILES: O=C(NS(=O)(=O)c1ccc(NCCSc2ccccc2)c([N+](=O)[O-])c1)c1ccc(N2CCN(Cc3ccnn3-c3ccccc3)CC2)cc1] |
| 4-(((1R)-3-(morpholin-4-yl)-1-((phenylsulfanyl)methyl)propyl)amino)-3-nitro-N-(4-(4-((1-phenyl-1H-pyrazol-5-yl)methyl)piperazin-1-yl)benzoyl)benzenesulfonamide | |

-continued

| Name | Structure |
|---|---|
| 4-(((1R)-3-(morpholin-4-yl)-1-((phenylsulfanyl)methyl)propyl)amino)-3-nitro-N-(4-(4-((1-phenyl-1H-pyrazol-5-yl)methyl)piperazin-1-yl)benzoyl)benzenesulfonamide | 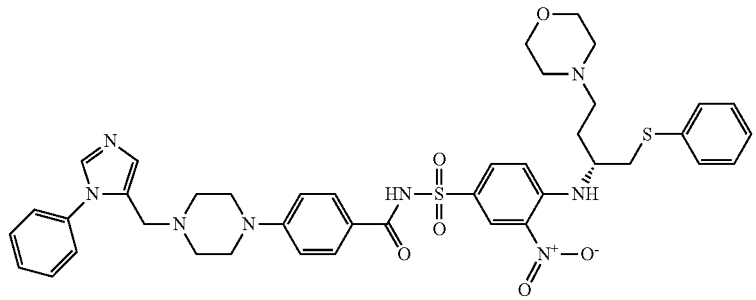 [SMILES: O=C(NS(=O)(=O)c1ccc(N[C@H](CCN2CCOCC2)CSc2ccccc2)c([N+](=O)[O-])c1)c1ccc(N2CCN(Cc3cncn3-c3ccccc3)CC2)cc1] |
| 4-(((1R)-3-(morpholin-4-yl)-1-((phenylsulfanyl)methyl)propyl)amino)-3-nitro-N-(4-(4-((1-phenyl-1H-imidazol-5-yl)methyl)piperazin-1-yl)benzoyl)benzenesulfonamide | 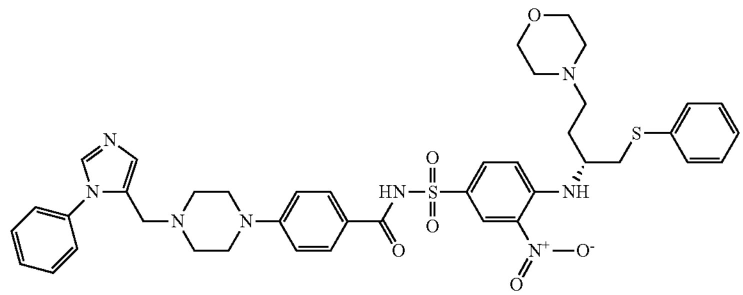 [SMILES: O=C(NS(=O)(=O)c1ccc(N[C@H](CCN2CCOCC2)CSc2ccccc2)c([N+](=O)[O-])c1)c1ccc(N2CCN(Cc3cncn3-c3ccccc3)CC2)cc1] |
| 1-((3R)-3-(4-(((4-(4-((4'-chloro(1,1'-biphenyl)-2-yl)methyl)piperazin-1-yl)benzoyl)amino)sulfonyl)-2-nitroanilino)-4-(phenylsulfanyl)butyl)-3-azetidinecarboxylic acid | 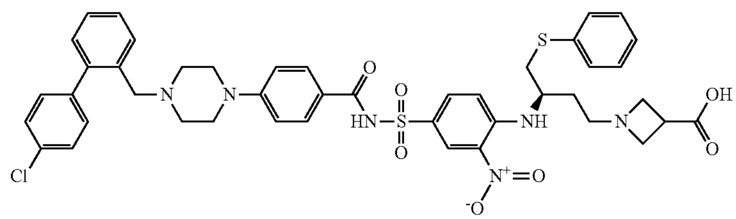 |
| N-(4-(4-((4'-chloro(1,1'-biphenyl)-2-yl)methyl)piperazin-1-yl)benzoyl)-4-(((1R)-3-((2-hydroxy-2-methylpropyl)amino)-1-((phenylsulfanyl)methyl)propyl)amino)-3-nitrobenzenesulfonamide | 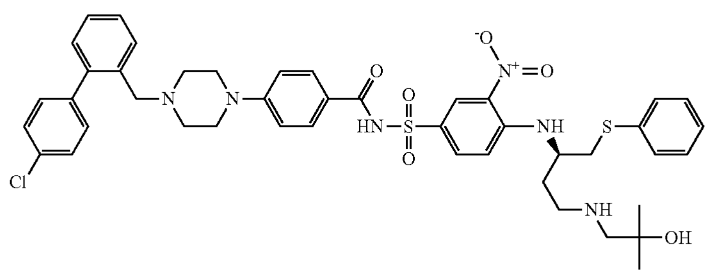 |
| (((3R)-3-(4-(((4-(4-((4'-chloro(1,1'-biphenyl)-2-yl)methyl)piperazin-1-yl)benzoyl)amino)sulfonyl)-2-nitroanilino)-4-(phenylsulfanyl)butyl)(methyl)amino)acetic acid | 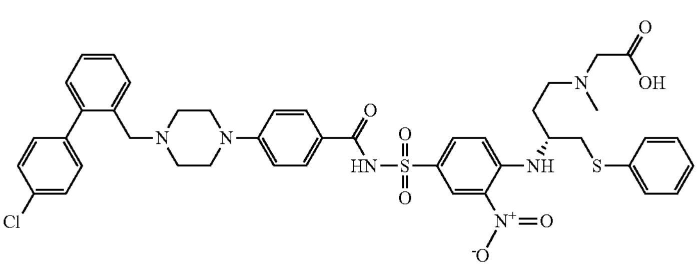 |

| Name | Structure |
|---|---|
| (2R)-1-((3R)-3-(4-(((4-(4-((4'-chloro(1,1'-biphenyl)-2-yl)methyl)piperazin-1-yl)benzoyl)amino)sulfonyl)-2-nitroanilino)-4-(phenylsulfanyl)butyl)-2-pyrrolidinecarboxylic acid | 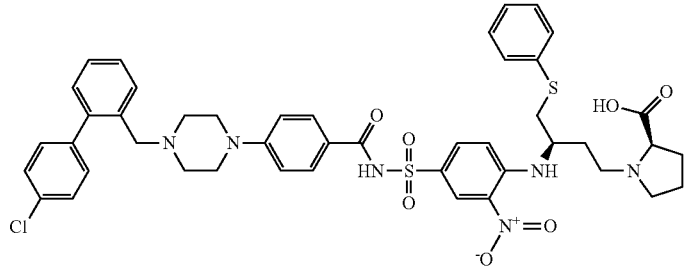 |
| 1-((3R)-3-(4-(((4-(4-((4'-chloro(1,1'-biphenyl)-2-yl)methyl)piperazin-1-yl)benzoyl)amino)sulfonyl)-2-nitroanilino)-4-(phenylsulfanyl)butyl)-4-piperidinecarboxylic acid | 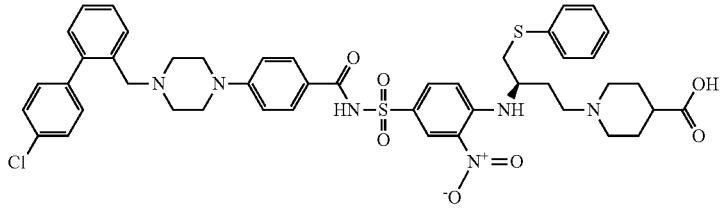 |
| N-(4-(4-((4'-chloro(1,1'-biphenyl)-2-yl)methyl)piperazin-1-yl)benzoyl)-4-(((1R)-3-((2-hydroxyethyl)(methyl)amino)-1-((phenylsulfanyl)methyl)propyl)amino)-3-nitrobenzenesulfonamide | 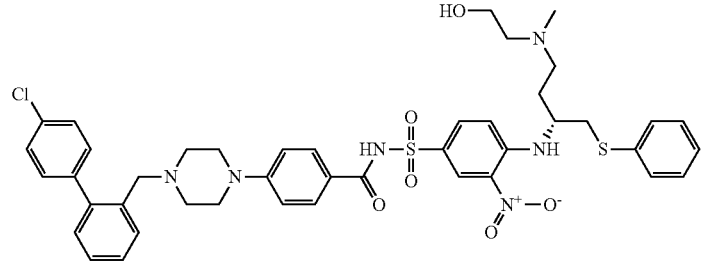 [SMILES: CN(CCO)CC[C@H](CSc1ccccc1)Nc1ccc(S(=O)(=O)NC(=O)c2ccc(N3CCN(Cc4ccccc4-c4ccc(Cl)cc4)CC3)cc2)cc1[N+](=O)[O-]] |
| (2S)-1-((3R)-3-(4-(((4-(4-((4'-chloro(1,1'-biphenyl)-2-yl)methyl)piperazin-1-yl)benzoyl)amino)sulfonyl)-2-nitroanilino)-4-(phenylsulfanyl)butyl)-2-pyrrolidinecarboxylic acid | 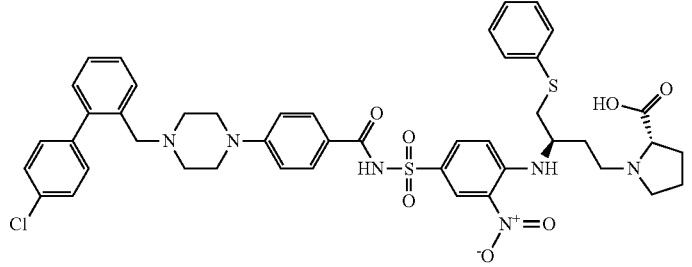 |
| N-(4-(4-((4'-chloro(1,1'-biphenyl)-2-yl)methyl)piperazin-1-yl)benzoyl)-3-nitro-4-(((1R)-1-((phenylsulfanyl)methyl)-3-(3-(2H-tetrazol-5-yl)azetidin-1-yl)propyl)amino)benzenesulfonamide | 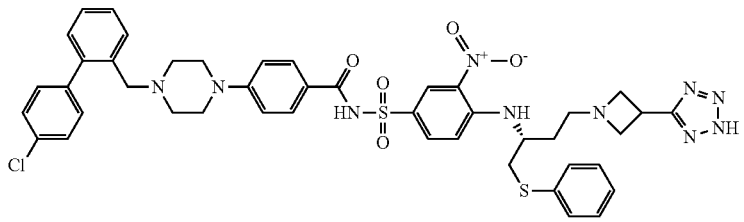 [SMILES: O=C(NS(=O)(=O)c1ccc(N[C@H](CCN2CC(c3nn[nH]n3)C2)CSc2ccccc2)c([N+](=O)[O-])c1)c1ccc(N2CCN(Cc3ccccc3-c3ccc(Cl)cc3)CC2)cc1] |

-continued

| Name | Structure |
|---|---|
| (2S)-2-amino-N-((1S)-2-(((3R)-3-(4-(((4-(4-((4'-chloro(1,1'-biphenyl)-2-yl)methyl)piperazin-1-yl)benzoyl)amino)sulfonyl)-2-nitroanilino)-4-(phenylsulfanyl)butyl)amino)-1-methyl-2-oxoethyl)propanamide | 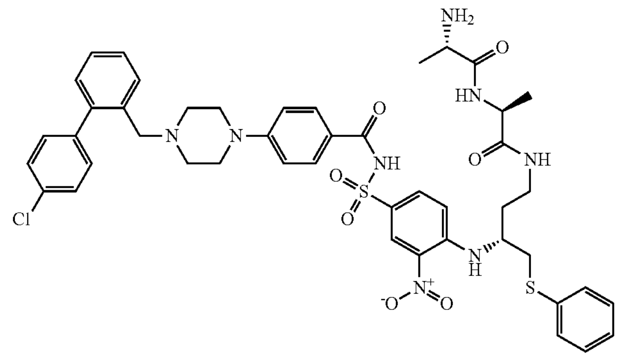 |
| N-(4-(4-((4'-chloro(1,1'-biphenyl)-2-yl)methyl)piperazin-1-yl)benzoyl)-3-nitro-4-(((1R)-1-((phenylsulfanyl)methyl)-3-(2-(2H-tetrazol-5-yl)pyrrolidin-1-yl)propyl)amino)benzenesulfonamide | 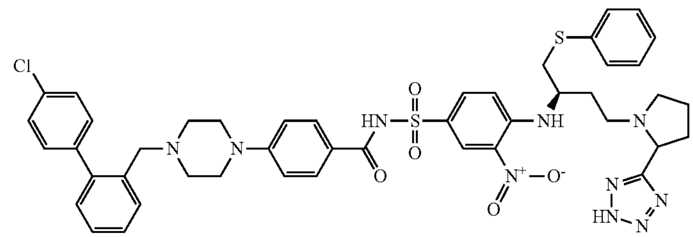 [SMILES: O=C(NS(=O)(=O)c1ccc(N[C@H](CCN2CCCC2c2nn[nH]n2)CSc2ccccc2)c([N+](=O)[O-])c1)c1ccc(N2CCN(Cc3ccccc3-c3ccc(Cl)cc3)CC2)cc1] |
| N-(4-(4-((4'-chloro(1,1'-biphenyl)-2-yl)methyl)piperazin-1-yl)benzoyl)-4-(((1R)-3-(4-(((methylsulfonyl)amino)carbonyl)piperidin-1-yl)-1-((phenylsulfanyl)methyl)propyl)amino)-3-nitrobenzenesulfonamide | 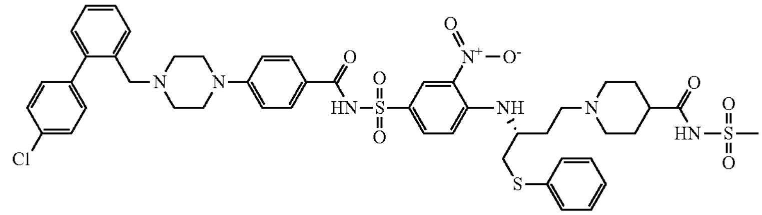 [SMILES: CS(=O)(=O)NC(=O)C1CCN(CC[C@H](CSc2ccccc2)Nc2ccc(S(=O)(=O)NC(=O)c3ccc(N4CCN(Cc5ccccc5-c5ccc(Cl)cc5)CC4)cc3)cc2[N+](=O)[O-])CC1] |
| N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)benzenesulfonamide | 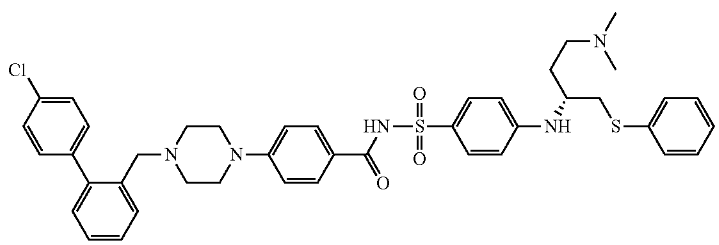 [SMILES: CN(C)CC[C@H](CSc1ccccc1)Nc1ccc(S(=O)(=O)NC(=O)c2ccc(N3CCN(Cc4ccccc4-c4ccc(Cl)cc4)CC3)cc2)cc1] |
| 1-((3R)-3-(4-(((4-(4-((4'-chloro(1,1'-biphenyl)-2-yl)methyl)piperazin-1-yl)benzoyl)amino)sulfonyl)-2-nitroanilino)-4-(phenylsulfanyl)butyl)-N-hydroxy-4-piperidinecarboxamide | 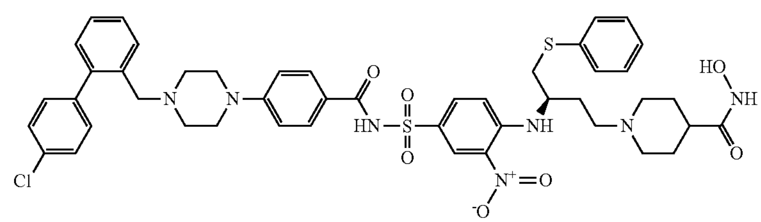 |
| 2-chloro-N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)benzenesulfonamide | 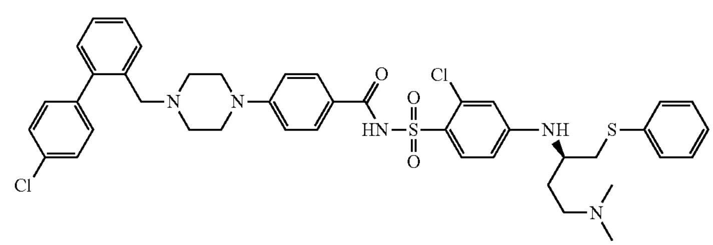 [SMILES: CN(C)CC[C@H](CSc1ccccc1)Nc1ccc(S(=O)(=O)NC(=O)c2ccc(N3CCN(Cc4ccccc4-c4ccc(Cl)cc4)CC3)cc2)c(Cl)c1] |

| Name | Structure |
|------|-----------|
| 2,6-dichloro-N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)benzenesulfonamide | 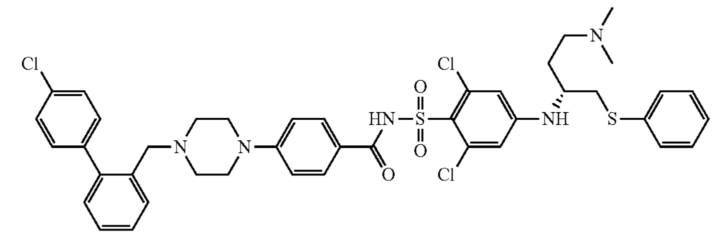 |
| 4-(((1R)-3-((1R,5S)-8-azabicyclo[3.2.1]oct-8-yl)-1-((phenylsulfanyl)methyl)propyl)amino)-N-(4-(4-((4'-chloro(1,1'-biphenyl)-2-yl)methyl)piperazin-1-yl)benzoyl)-3-nitrobenzenesulfonamide | 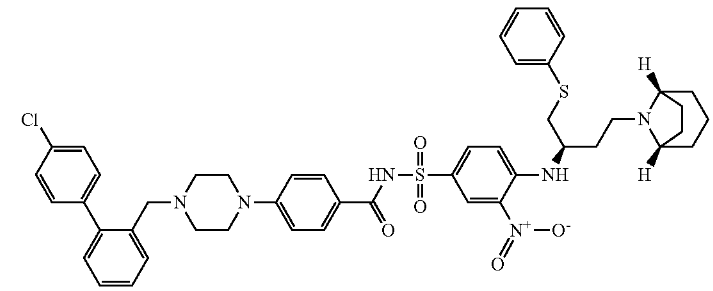 [SMILES: O=C(NS(=O)(=O)c1ccc(N[C@H](CCN2[C@@H]3CCC[C@H]2CC3)CSc2ccccc2)c([N+](=O)[O-])c1)c1ccc(N2CCN(Cc3ccccc3-c3ccc(Cl)cc3)CC2)cc1] |
| 4-(((1R)-3-(7-azabicyclo[2.2.1]hept-7-yl)-1-((phenylsulfanyl)methyl)propyl)amino)-N-(4-(4-((4'-chloro(1,1'-biphenyl)-2-yl)methyl)piperazin-1-yl)benzoyl)-3-nitrobenzenesulfonamide | 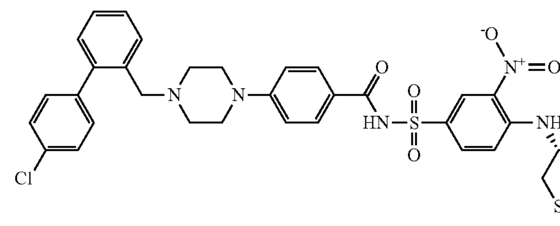 |
| N-(4-(4-((4'-chloro(1,1'-biphenyl)-2-yl)methyl)piperazin-1-yl)benzoyl)-3-nitro-4-(2-(phenylsulfanyl)ethoxy)benzenesulfonamide | 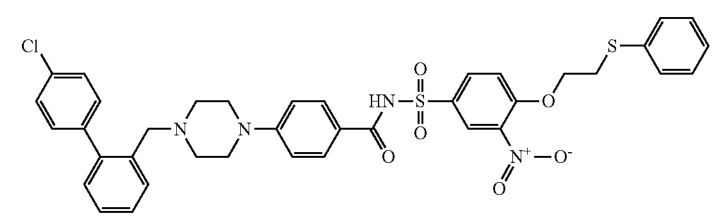 [SMILES: O=C(NS(=O)(=O)c1ccc(OCCSc2ccccc2)c([N+](=O)[O-])c1)c1ccc(N2CCN(Cc3ccccc3-c3ccc(Cl)cc3)CC2)cc1] |
| N-(4-(4-((4'-chloro(1,1'-biphenyl)-2-yl)methyl)piperazin-1-yl)benzoyl)-4-(2-(phenylsulfanyl)ethoxy)-3-(trifluoromethyl)benzenesulfonamide | 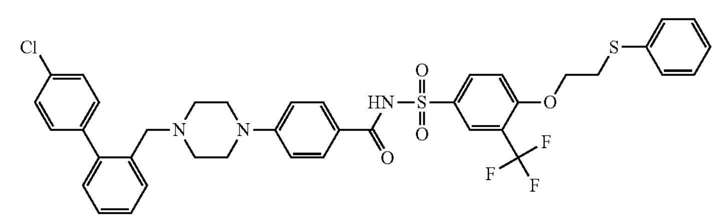 [SMILES: O=C(NS(=O)(=O)c1ccc(OCCSc2ccccc2)c(C(F)(F)F)c1)c1ccc(N2CCN(Cc3ccccc3-c3ccc(Cl)cc3)CC2)cc1] |
| N-(4-(4-((4'-chloro(1,1'-biphenyl)-2-yl)methyl)piperazin-1-yl)benzoyl)-3-nitro-4-(((1R)-3-((1S,4S)-2-oxa-5-azabicyclo[2.2.1]hept-5-yl)-1-((phenylsulfanyl)methyl)propyl)amino)benzenesulfonamide | 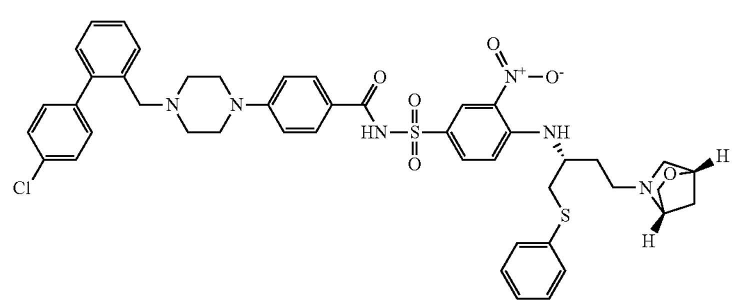 [SMILES: O=C(NS(=O)(=O)c1ccc(N[C@H](CCN2C[C@@H]3C[C@H]2CO3)CSc2ccccc2)c([N+](=O)[O-])c1)c1ccc(N2CCN(Cc3ccccc3-c3ccc(Cl)cc3)CC2)cc1] |

-continued

| Name | Structure |
|---|---|
| N-(4-(4-((4'-chloro(1,1'-biphenyl)-2-yl)methyl)piperazin-1-yl)benzoyl)-3-nitro-4-(((1R)-3-((1R,4R)-2-oxa-5-azabicyclo[2.2.1]hept-5-yl)-1-((phenylsulfanyl)methyl)propyl)amino)benzenesulfonamide | 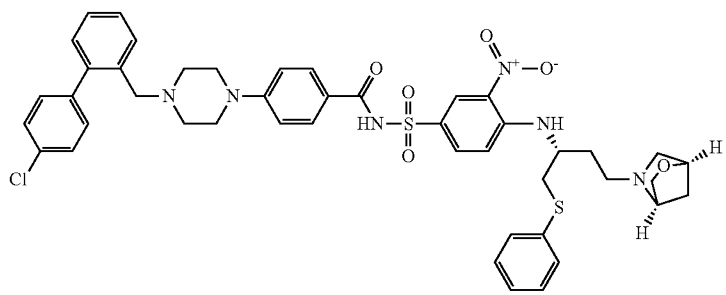 [SMILES: O=C(NS(=O)(=O)c1ccc(N[C@H](CCN2C[C@H]3C[C@@H]2CO3)CSc2ccccc2)c([N+](=O)[O-])c1)c1ccc(N2CCN(Cc3ccccc3-c3ccc(Cl)cc3)CC2)cc1] |
| N-(4-(4-((2-(4-chlorophenyl)-1-cyclohexen-1-yl)methyl)piperazin-1-yl)benzoyl)-3-nitro-4-(((1R)-3-((1S,4S)-2-oxa-5-azabicyclo[2.2.1]hept-5-yl)-1-((phenylsulfanyl)methyl)propyl)amino)benzenesulfonamide | 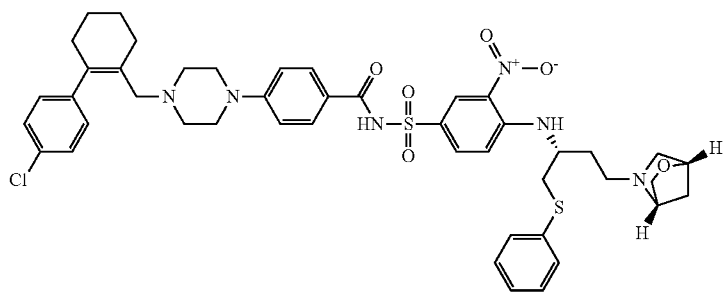 [SMILES: O=C(NS(=O)(=O)c1ccc(N[C@H](CCN2C[C@@H]3C[C@H]2CO3)CSc2ccccc2)c([N+](=O)[O-])c1)c1ccc(N2CCN(CC3=C(c4ccc(Cl)cc4)CCCC3)CC2)cc1] |
| N-(4-(4-((2-(4-chlorophenyl)-1-cyclohexen-1-yl)methyl)piperazin-1-yl)benzoyl)-3-nitro-4-(((1R)-3-((1R,4R)-2-oxa-5-azabicyclo[2.2.1]hept-5-yl)-1-((phenylsulfanyl)methyl)propyl)amino)benzenesulfonamide | 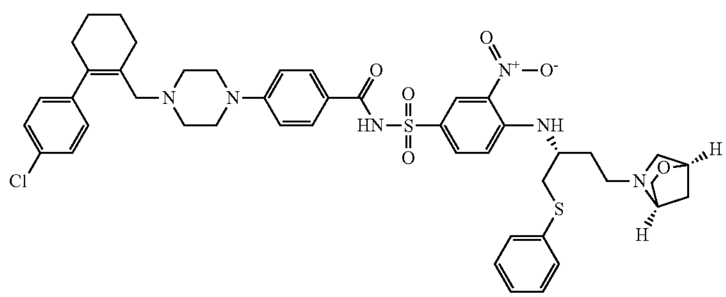 [SMILES: O=C(NS(=O)(=O)c1ccc(N[C@H](CCN2C[C@H]3C[C@@H]2CO3)CSc2ccccc2)c([N+](=O)[O-])c1)c1ccc(N2CCN(CC3=C(c4ccc(Cl)cc4)CCCC3)CC2)cc1] |
| 4-(((1R)-3-(7-azabicyclo[2.2.1]hept-7-yl)-1-((phenylsulfanyl)methyl)propyl)amino)-N-(4-(4-((2-(4-chlorophenyl)-1-cyclohexen-1-yl)methyl)piperazin-1-yl)benzoyl)-3-nitrobenzenesulfonamide | 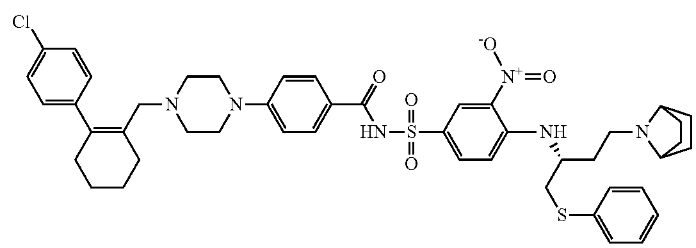 |
| N-(4-(4-((2-(4-chlorophenyl)-1-cyclohexen-1-yl)methyl)piperazin-1-yl)benzoyl)-4-(((1R)-3-((2R,5S)-2,5-dimethylpyrrolidin-1-yl)-1-((phenylsulfanyl)methyl)propyl)amino)-3-nitrobenzenesulfonamide | 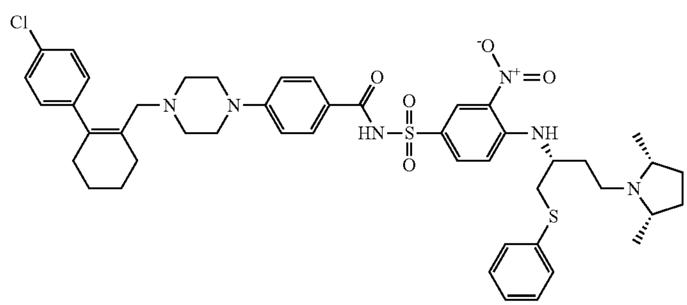 |

| Name | Structure |
|---|---|
| N-(4-(4-((4'-chloro(1,1'-biphenyl)-2-yl)methyl)piperazin-1-yl)benzoyl)-3-nitro-4-(((1R)-3-((1R,4R)-2-oxa-5-azabicyclo[2.2.1]hept-5-yl)-1-((phenylsulfanyl)methyl)propyl)amino)benzenesulfonamide | 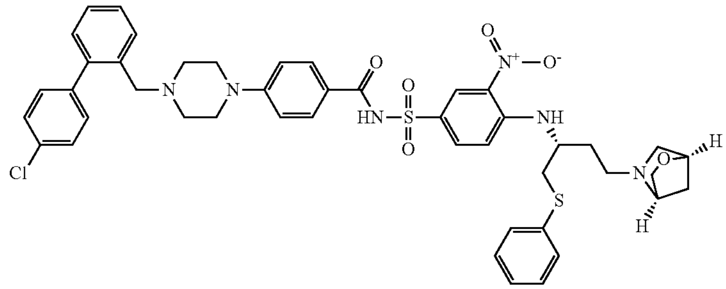 [SMILES: O=C(NS(=O)(=O)c1ccc(N[C@H](CCN2C[C@H]3C[C@@H]2CO3)CSc2ccccc2)c([N+](=O)[O-])c1)c1ccc(N2CCN(Cc3ccccc3-c3ccc(Cl)cc3)CC2)cc1] |
| N-(4-(4-((1,1'-biphenyl)-2-ylmethyl)piperazin-1-yl)benzoyl)-4-(cyclohexyloxy)-3-nitrobenzenesulfonamide | 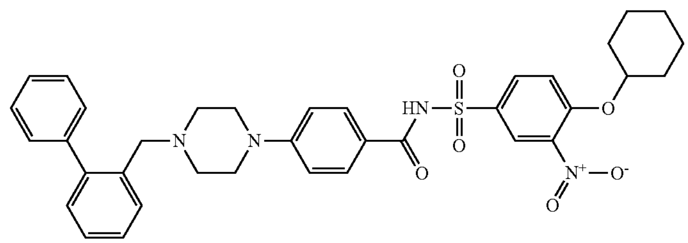 [SMILES: O=C(NS(=O)(=O)c1ccc(OC2CCCCC2)c([N+](=O)[O-])c1)c1ccc(N2CCN(Cc3ccccc3-c3ccccc3)CC2)cc1] |
| N-(4-(4-((1,1'-biphenyl)-2-ylmethyl)piperazin-1-yl)benzoyl)-4-(cyclohexylmethoxy)-3-nitrobenzenesulfonamide | 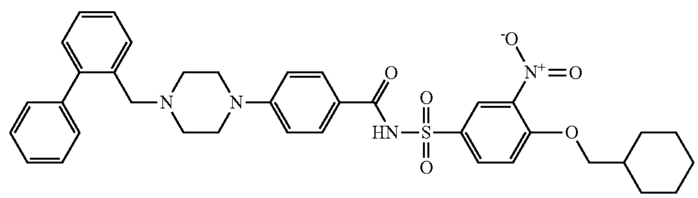 |
| N-(4-(4-((1,1'-biphenyl)-2-ylmethyl)piperazin-1-yl)benzoyl)-4-(2-cyclohexylethoxy)-3-nitrobenzenesulfonamide | 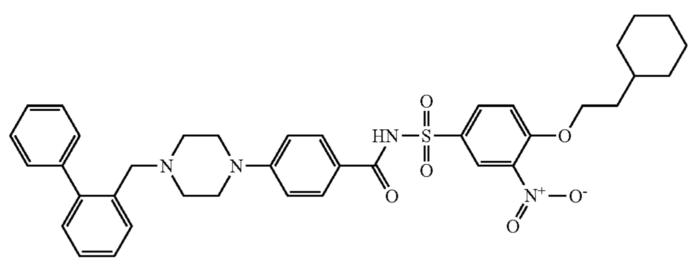 [SMILES: O=C(NS(=O)(=O)c1ccc(OCCC2CCCCC2)c([N+](=O)[O-])c1)c1ccc(N2CCN(Cc3ccccc3-c3ccccc3)CC2)cc1] |
| N-(4-(4-((1,1'-biphenyl)-2-ylmethyl)piperazin-1-yl)benzoyl)-3-nitro-4-(tetrahydro-2H-pyran-4-ylamino)benzenesulfonamide | 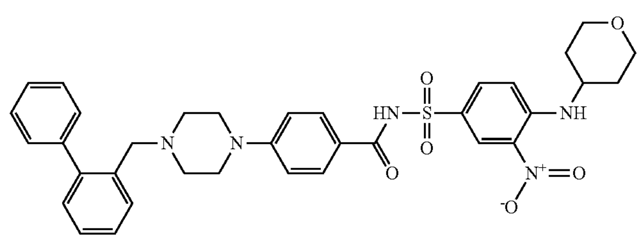 |
| N-(4-(4-((1,1'-biphenyl)-2-ylmethyl)piperazin-1-yl)benzoyl)-4-((2-cyclohexylethyl)amino)-3-nitrobenzenesulfonamide | 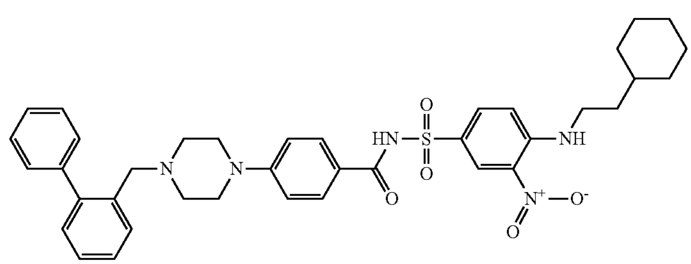 |

| Name | Structure |
|---|---|
| N-(4-(4-((1,1'-biphenyl)-2-ylmethyl)piperazin-1-yl)benzoyl)-4-(cyclohexyl(methyl)amino)-3-nitrobenzenesulfonamide | 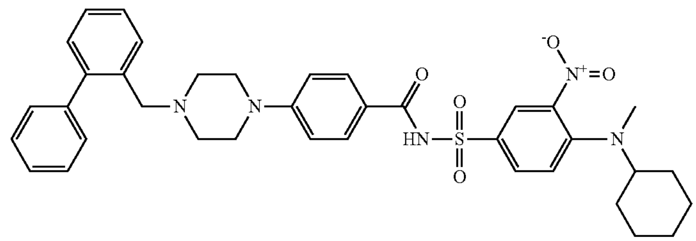 |
| N-(4-(4-((1,1'-biphenyl)-2-ylmethyl)piperazin-1-yl)benzoyl)-4-(4,4-dimethylpiperidin-1-yl)-3-nitrobenzenesulfonamide | 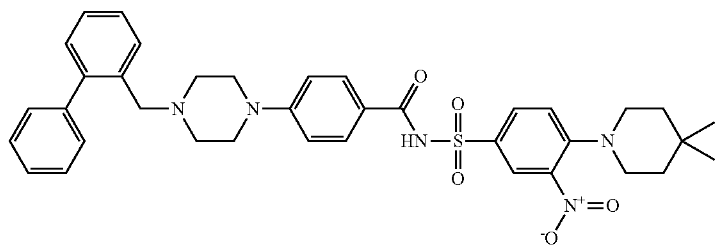 |
| tert-butyl 4-(4-(((4-(4-((1,1'-biphenyl)-2-ylmethyl)piperazin-1-yl)benzoyl)amino)sulfonyl)-2-nitrophenoxy)-1-piperidinecarboxylate | 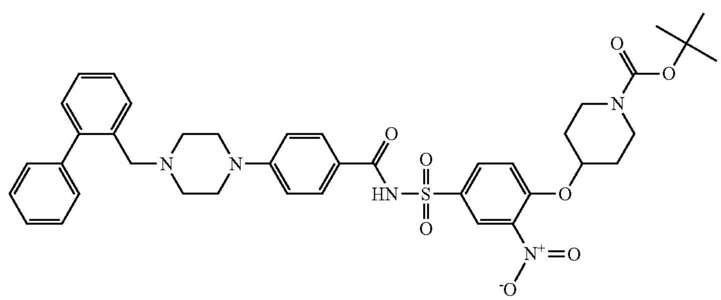 |
| N-(4-(4-((1,1'-biphenyl)-2-ylmethyl)piperazin-1-yl)benzoyl)-3-nitro-4-(piperidin-4-yloxy)benzenesulfonamide | 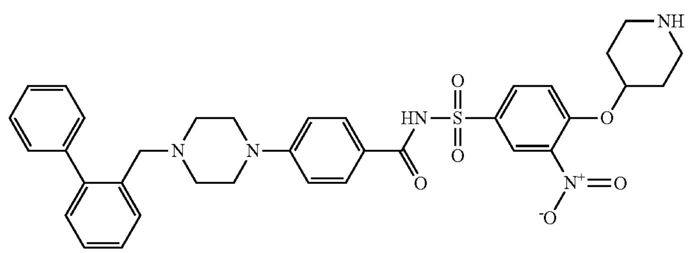 |
| N-(4-(4-((1,1'-biphenyl)-2-ylmethyl)piperazin-1-yl)benzoyl)-4-((1-methylpiperidin-4-yl)oxy)-3-nitrobenzenesulfonamide | 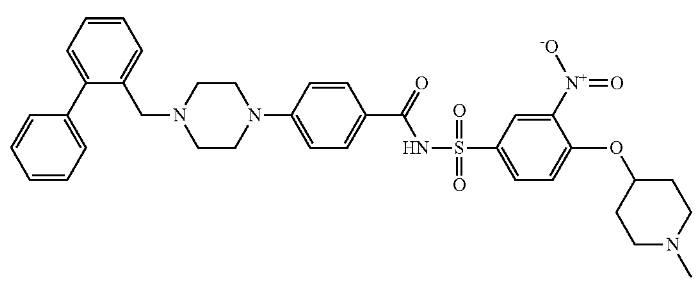 |
| N-(4-(4-((4'-chloro(1,1'-biphenyl)-2-yl)methyl)piperazin-1-yl)benzoyl)-4-((cyclohexylmethyl)amino)-3-nitrobenzenesulfonamide | 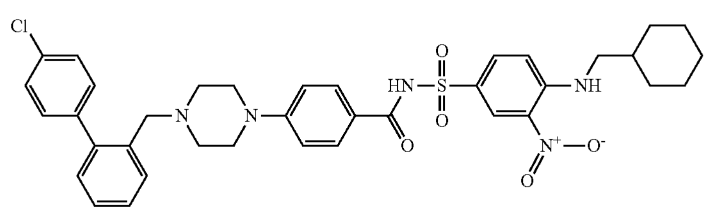 [SMILES: O=C(NS(=O)(=O)c1ccc(NCC2CCCCC2)c([N+](=O)[O-])c1)c1ccc(N2CCN(Cc3ccccc3-c3ccc(Cl)cc3)CC2)cc1] |

-continued

| Name | Structure |
|---|---|
| N-(4-(4-((4'-chloro(1,1'-biphenyl)-2-yl)methyl)piperazin-1-yl)benzoyl)-4-((cyclohexylmethyl)(propyl)amino)-3-nitrobenzenesulfonamide | 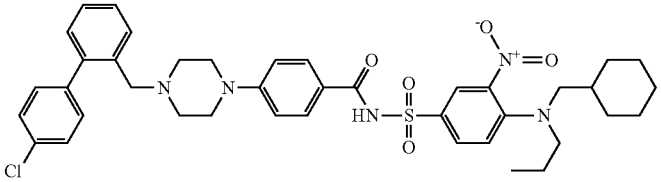 |
| 4-(((1-benzylpiperidin-4-yl)methyl)amino)-N-(4-(4-((1,1'-biphenyl)-2-ylmethyl)piperazin-1-yl)benzoyl)-3-nitrobenzenesulfonamide | 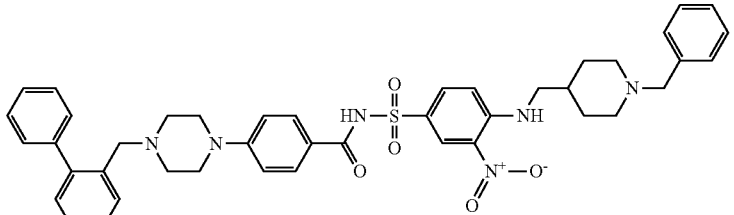 |
| N-(4-(4-((1,1'-biphenyl)-2-ylmethyl)piperazin-1-yl)benzoyl)-4-((cyclohexylmethyl)(methyl)amino)-3-nitrobenzenesulfonamide | 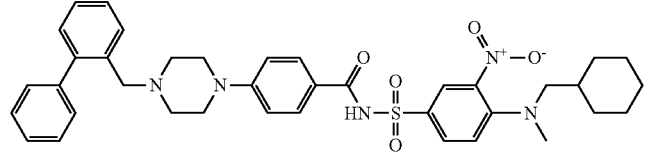 [SMILES: CN(CC1CCCCC1)c1ccc(S(=O)(=O)NC(=O)c2ccc(N3CCN(Cc4ccccc4-c4ccccc4)CC3)cc2)cc1[N+](=O)[O-]] |
| 4-((1-benzylpiperidin-4-yl)amino)-N-(4-(4-((1,1'-biphenyl)-2-ylmethyl)piperazin-1-yl)benzoyl)-3-nitrobenzenesulfonamide | 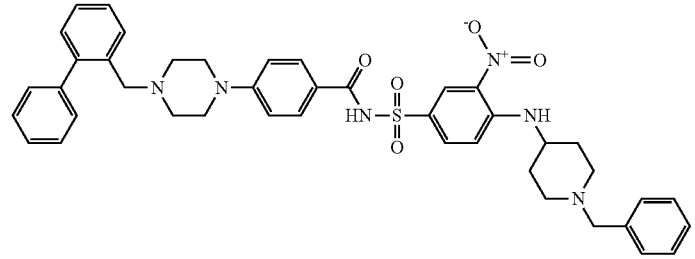 |
| N-(4-(4-((1,1'-biphenyl)-2-ylmethyl)piperazin-1-yl)benzoyl)-3-nitro-4-(tetrahydro-2H-sulfanylpyran-4-ylamino)benzenesulfonamide | 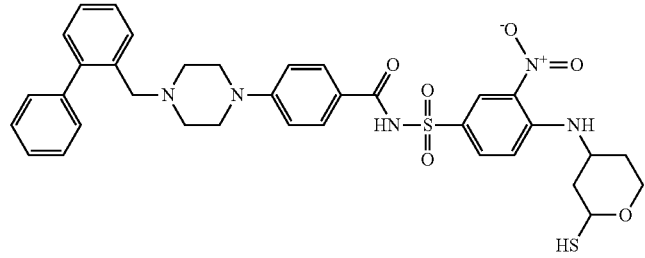 |
| ethyl 4-(4-(((4-(4-((1,1'-biphenyl)-2-ylmethyl)piperazin-1-yl)benzoyl)amino)sulfonyl)-2-nitroanilino)-1-piperidinecarboxylate | 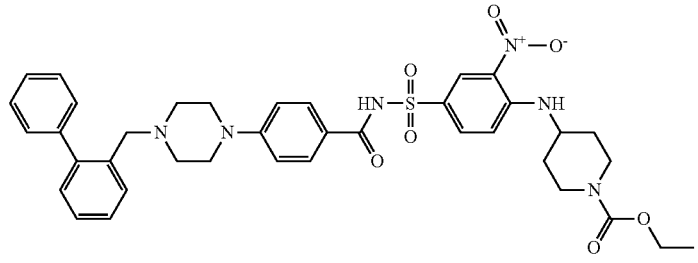 [SMILES: CCOC(=O)N1CCC(Nc2ccc(S(=O)(=O)NC(=O)c3ccc(N4CCN(Cc5ccccc5-c5ccccc5)CC4)cc3)cc2[N+](=O)[O-])CC1] |
| N-(4-(4-((1,1'-biphenyl)-2-ylmethyl)piperazin-1-yl)benzoyl)-3-nitro-4-(((1-propylpiperidine-4-yl)methyl)amino)benzenesulfonamide | 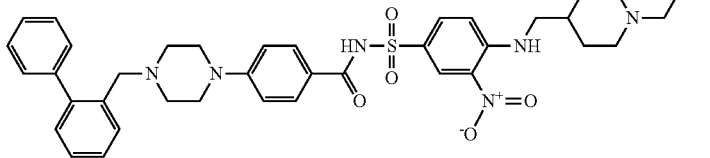 |

| Name | Structure |
|---|---|
| N-(4-(4-((1,1'-biphenyl)-2-ylmethyl)piperazin-1-yl)benzoyl)-4-(isopropylamino)-3-nitrobenzenesulfonamide | 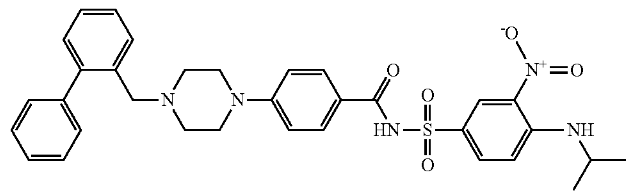 |
| N-(4-(4-((1,1'-biphenyl)-2-ylmethyl)piperazin-1-yl)benzoyl)-3-nitro-4-((2-(1,3-thiazol-2-ylsulfanyl)ethyl)amino)benzenesulfonamide | 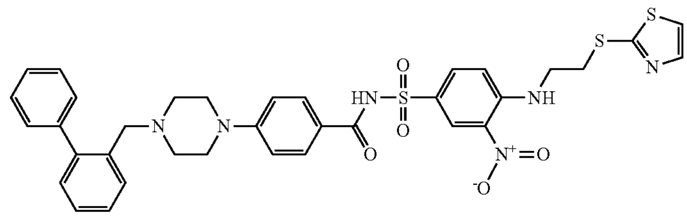 |
| N-(4-(4-((1,1'-biphenyl)-2-ylmethyl)piperazin-1-yl)benzoyl)-3-nitro-4-((2-((4-phenyl-1,3-thiazol-2-yl)sulfanyl)ethyl)amino)benzenesulfonamide | 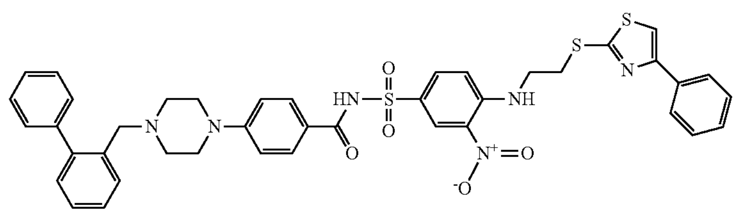 |
| 4-((2-(1,3-benzothiazol-2-ylsulfanyl)ethyl)amino)-N-(4-(4-((1,1'-biphenyl)-2-ylmethyl)piperazin-1-yl)benzoyl)-3-nitrobenzenesulfonamide | 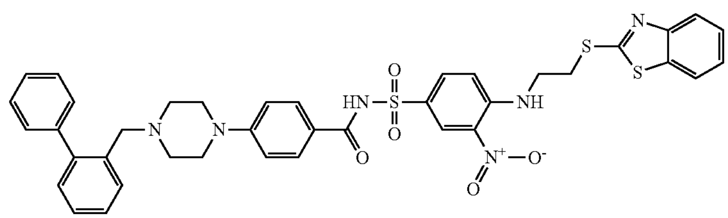 [SMILES: O=C(NS(=O)(=O)c1ccc(NCCSc2nc3ccccc3s2)c([N+](=O)[O-])c1)c1ccc(N2CCN(Cc3ccccc3-c3ccccc3)CC2)cc1] |
| N-(4-(4-((4'-chloro(1,1'-biphenyl)-2-yl)methyl)piperazin-1-yl)benzoyl)-3-nitro-4-((2-(1,3-thiazol-2-ylsulfanyl)ethyl)amino)benzenesulfonamide | 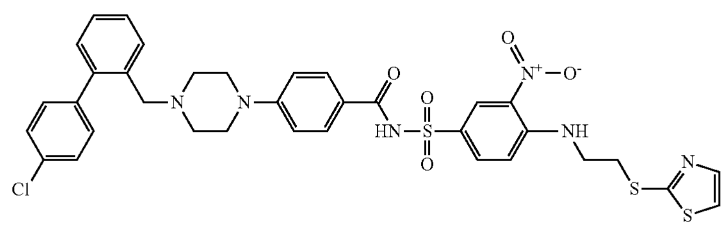 [SMILES: O=C(NS(=O)(=O)c1ccc(NCCSc2nccs2)c([N+](=O)[O-])c1)c1ccc(N2CCN(Cc3ccccc3-c3ccc(Cl)cc3)CC2)cc1] |
| 4-((2-(1,3-benzoxazol-2-ylsulfanyl)ethyl)amino)-N-(4-(4-((4'-chloro(1,1'-biphenyl)-2-yl)methyl)piperazin-1-yl)benzoyl)-3-nitrobenzenesulfonamide | 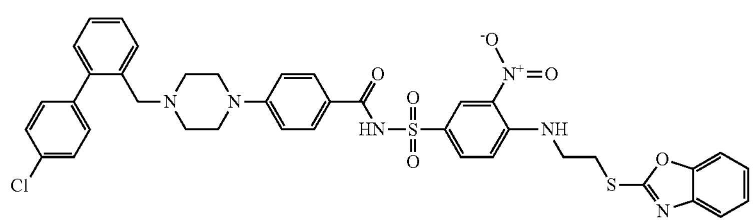 |
| 4-((2-(1,3-benzothiazol-2-ylsulfanyl)ethyl)amino)-N-(4-(4-((4'-chloro(1,1'-biphenyl)-2-yl)methyl)piperazin-1-yl)benzoyl)-3-nitrobenzenesulfonamide | 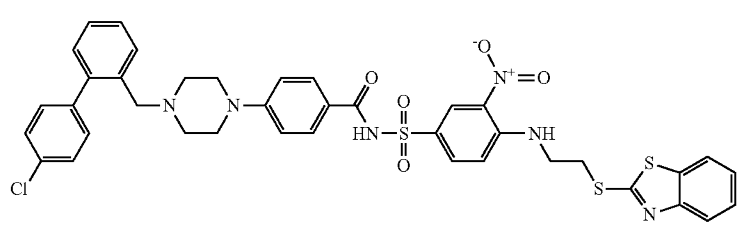 |

-continued

| Name | Structure |
|---|---|
| N-(4-(4-((4'-chloro(1,1'-biphenyl)-2-yl)methyl)piperazin-1-yl)benzoyl)-3-nitro-4-((2-(pyrimidin-2-ylsulfanyl)ethyl)amino)benzenesulfonamide | 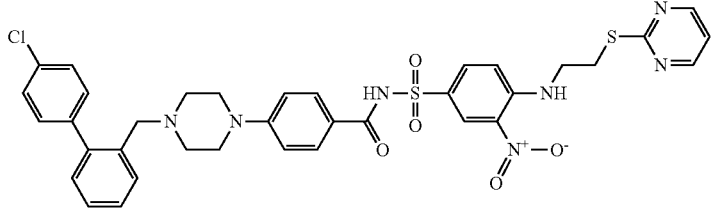 [SMILES: O=C(NS(=O)(=O)c1ccc(NCCSc2ncccn2)c([N+](=O)[O-])c1)c1ccc(N2CCN(Cc3ccccc3-c3ccc(Cl)cc3)CC2)cc1] |
| 4-(((1R)-3-(morpholin-4-yl)-1-((phenylsulfanyl)methyl)propyl)amino)-3-nitro-N-(4-(4-((1-phenyl-1H-pyrazol-5-yl)methyl)piperazin-1-yl)benzoyl)benzenesulfonamide | 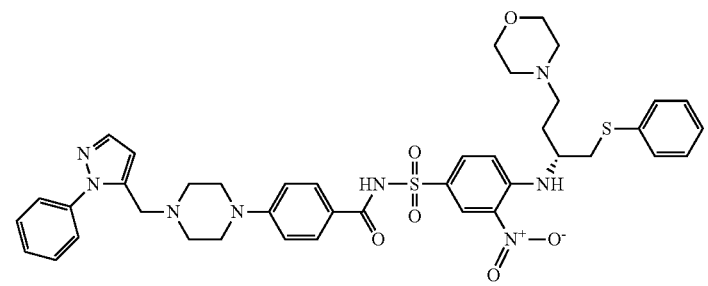 [SMILES: O=C(NS(=O)(=O)c1ccc(N[C@H](CCN2CCOCC2)CSc2ccccc2)c([N+](=O)[O-])c1)c1ccc(N2CCN(Cc3ccnn3-c3ccccc3)CC2)cc1] |
| 4-(((1-benzylpiperidin-4-yl)methyl)amino)-N-(4-(4-((4'-chloro(1,1'-biphenyl)-2-yl)methyl)piperazin-1-yl)benzoyl)-3-nitrobenzenesulfonamide | 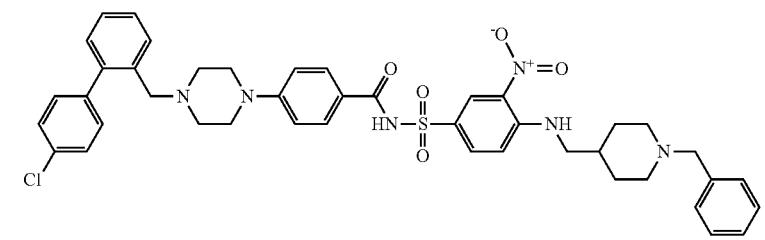 |
| N-(4-(4-((1,1'-biphenyl)-2-ylmethyl)piperazin-1-yl)benzoyl)-4-((2-bromoethyl)amino)-3-nitrobenzenesulfonamide | 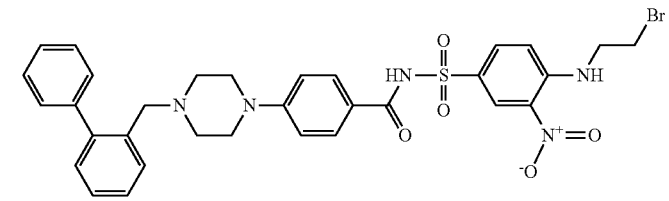 |
| N-(4-(4-((4'-chloro(1,1'-biphenyl)-2-yl)methyl)piperazin-1-yl)benzoyl)-4-((2-((4-methyl-1,3-thiazol-2-yl)sulfanyl)ethyl)amino)-3-nitrobenzenesulfonamide | 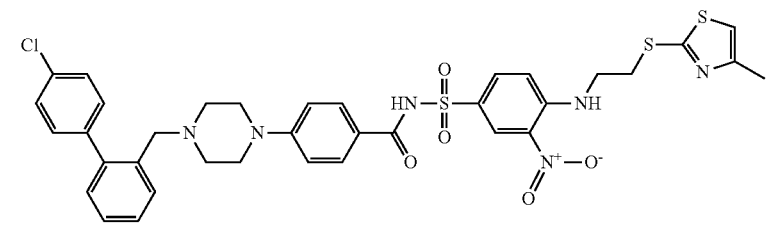 [SMILES: Cc1csc(SCCNc2ccc(S(=O)(=O)NC(=O)c3ccc(N4CCN(Cc5ccccc5-c5ccc(Cl)cc5)CC4)cc3)cc2[N+](=O)[O-])n1] |
| N-(4-(4-((4'-chloro(1,1'-biphenyl)-2-yl)methyl)piperazin-1-yl)benzoyl)-4-(((4-methoxycyclohexyl)methyl)amino)-3-nitrobenzenesulfonamide | 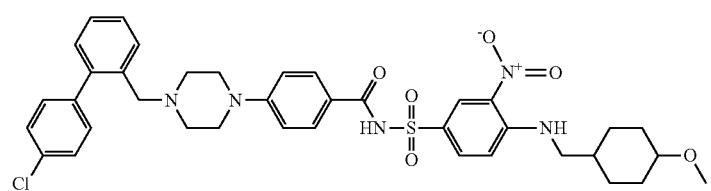 |

| Name | Structure |
|---|---|
| N-(4-(4-((1,1'-biphenyl)-2-ylmethyl)piperazin-1-yl)benzoyl)-3-nitro-4-((2-(2-thienylsulfanyl)ethyl)amino)benzenesulfonamide | 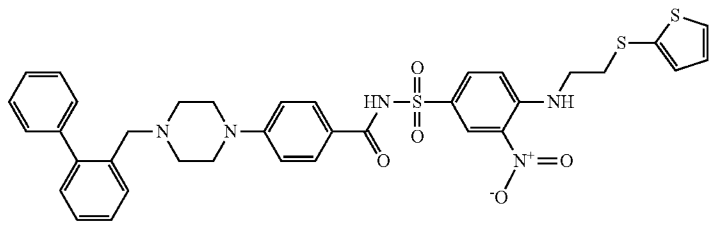 |
| N-(4-(4-((4'-chloro(1,1'-biphenyl)-2-yl)methyl)piperazin-1-yl)benzoyl)-4-(((1,1-dimethyl-2-(2-thienylsulfanyl)ethyl)amino)-3-nitrobenzenesulfonamide | |
| N-(4-(4-((4'-chloro(1,1'-biphenyl)-2-yl)methyl)piperazin-1-yl)benzoyl)-4-(((1R)-3-(morpholin-4-yl)-1-((1,3-thiazol-2-ylsulfanyl)methyl)propyl)amino)-3-nitrobenzenesulfonamide | 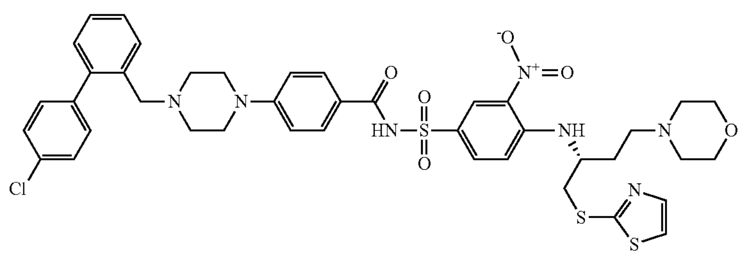 |
| (3R)-3-(4-(((4-(4-((4'-chloro(1,1'-biphenyl)-2-yl)methyl)piperazin-1-yl)benzoyl)amino)sulfonyl)-2-nitroanilino)-N,N-dimethyl-4-(pyrimidin-2-ylsulfanyl)butanamide | 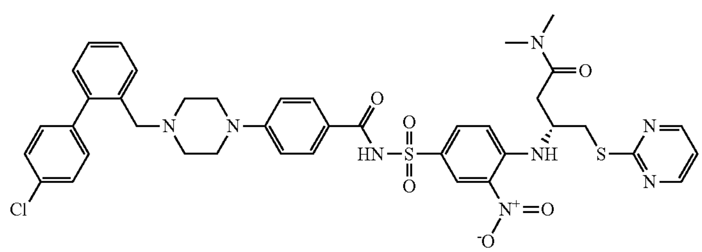 |
| N-(4-(4-((4'-chloro(1,1'-biphenyl)-2-yl)methyl)piperazin-1-yl)benzoyl)-4-(((1R)-3-(morpholin-4-yl)-3-oxo-1-((2-thienylsulfanyl)methyl)propyl)amino)-3-nitrobenzenesulfonamide | 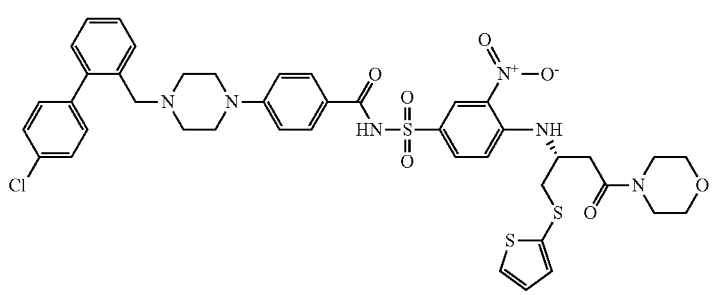 [SMILES: O=C(NS(=O)(=O)c1ccc(N[C@@H](CSc2cccs2)CC(=O)N2CCOCC2)c([N+](=O)[O-])c1)c1ccc(N2CCN(Cc3ccccc3-c3ccc(Cl)cc3)CC2)cc1] |
| N-(4-(4-((4'-chloro(1,1'-biphenyl)-2-yl)methyl)piperazin-1-yl)benzoyl)-4-(((1,1-dimethyl-2-(pyrimidin-2-ylsulfanyl)ethyl)amino)-3-nitrobenzenesulfonamide | |

-continued

| Name | Structure |
|------|-----------|
| (3R)-3-(4-(((4-(4-((4'-chloro(1,1'-biphenyl)-2-yl)methyl)piperazin-1-yl)benzoyl)amino)sulfonyl)-2-nitroanilino)-N,N-dimethyl-4-(1,3-thiazol-2-ylsulfanyl)butanamide | 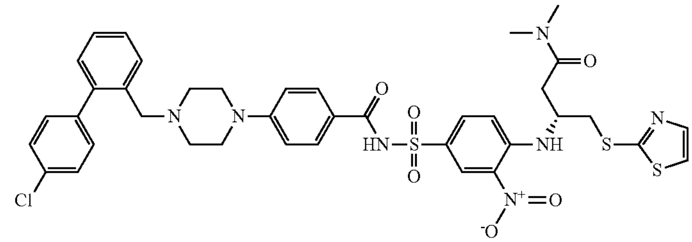 |
| N-(4-(4-((4'-chloro(1,1'-biphenyl)-2-yl)methyl)piperazin-1-yl)benzoyl)-4-(((1R)-3-(morpholin-4-yl)-1-((2-thienylsulfanyl)methyl)propyl)amino)-3-nitrobenzenesulfonamide | 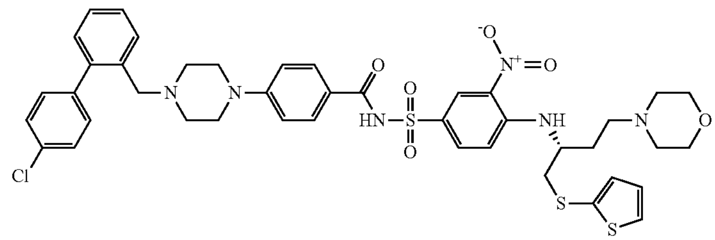 |
| N-(4-(4-((4'-chloro(1,1'-biphenyl)-2-yl)methyl)piperazin-1-yl)benzoyl)-4-(((1R)-3-(dimethylamino)-1-(((4-(trifluoromethoxy)phenyl)sulfanyl)methyl)propyl)amino)-3-nitrobenzenesulfonamide | 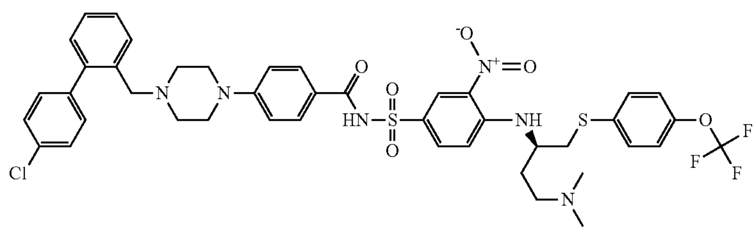 |
| N-(4-(4-((4'-chloro(1,1'-biphenyl)-2-yl)methyl)piperazin-1-yl)benzoyl)-3-nitro-4-((2-phenoxyethyl)amino)benzenesulfonamide | 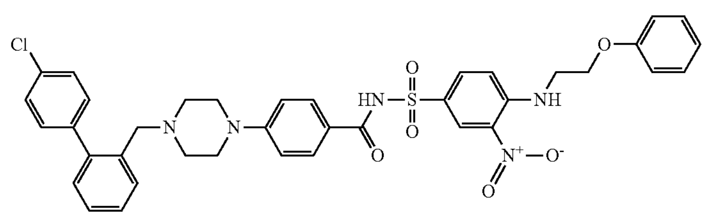 [SMILES: O=C(NS(=O)(=O)c1ccc(NCCOc2ccccc2)c([N+](=O)[O-])c1)c1ccc(N2CCN(Cc3ccccc3-c3ccc(Cl)cc3)CC2)cc1] |
| N-(4-(4-((4'-chloro(1,1'-biphenyl)-2-yl)methyl)piperazin-1-yl)benzoyl)-4-(((1R)-3-(morpholin-4-yl)-1-(((4-(trifluoromethoxy)phenyl)sulfanyl)methyl)propyl)amino)-3-nitrobenzenesulfonamide | 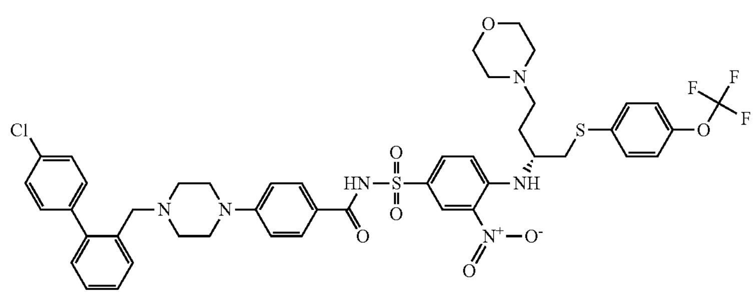 [SMILES: O=C(NS(=O)(=O)c1ccc(N[C@H](CCN2CCOCC2)CSc2ccc(OC(F)(F)F)cc2)c([N+](=O)[O-])c1)c1ccc(N2CCN(Cc3ccccc3-c3ccc(Cl)cc3)CC2)cc1] |
| N-(4-(4-((4'-chloro(1,1'-biphenyl)-2-yl)methyl)piperazin-1-yl)benzoyl)-4-(((1R)-1-(((4-methoxyphenyl)sulfanyl)methyl)-3-(morpholin-4-yl)propyl)amino)-3-nitrobenzenesulfonamide | 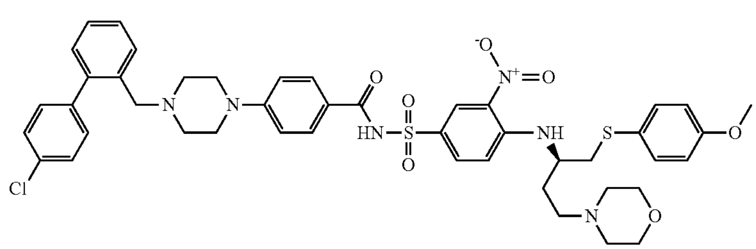 |

| Name | Structure |
|---|---|
| N-(4-(4-((4'-chloro(1,1'-biphenyl)-2-yl)methyl)piperazin-1-yl)benzoyl)-4-(((1R)-1-(((4-methylphenyl)sulfanyl)methyl)-3-(morpholin-4-yl)propyl)amino)-3-nitrobenzenesulfonamide | 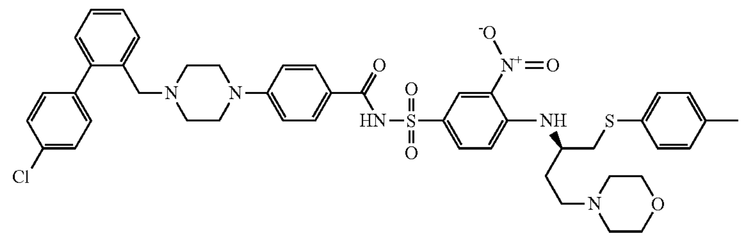 |
| N-(4-(4-((4'-chloro(1,1'-biphenyl)-2-yl)methyl)piperazin-1-yl)benzoyl)-4-(((1R)-3-(dimethylamino)-1-((2-thienylsulfanyl)methyl)propyl)amino)-3-(trifluoromethyl)benzenesulfonamide | 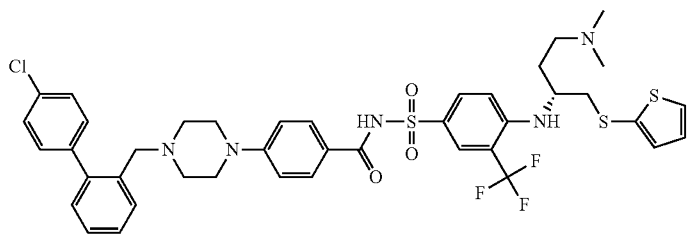 [SMILES: CN(C)CC[C@H](CSc1cccs1)Nc1ccc(S(=O)(=O)NC(=O)c2ccc(N3CCN(Cc4ccccc4-c4ccc(Cl)cc4)CC3)cc2)cc1C(F)(F)F] |
| N-(4-(4-((4'-chloro(1,1'-biphenyl)-2-yl)methyl)piperazin-1-yl)benzoyl)-4-(((1R)-1-(((4-chlorophenyl)sulfanyl)methyl)-3-(morpholin-4-yl)propyl)amino)-3-nitrobenzenesulfonamide | 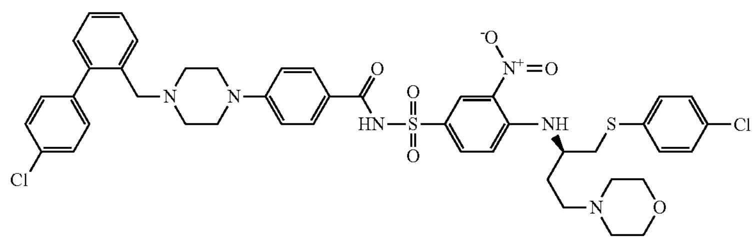 |
| N-(4-(4-((4'-chloro(1,1'-biphenyl)-2-yl)methyl)piperazin-1-yl)benzoyl)-4-(((1R)-3-(dimethylamino)-1-(((4-fluorophenyl)sulfanyl)methyl)propyl)amino)-3-nitrobenzenesulfonamide | 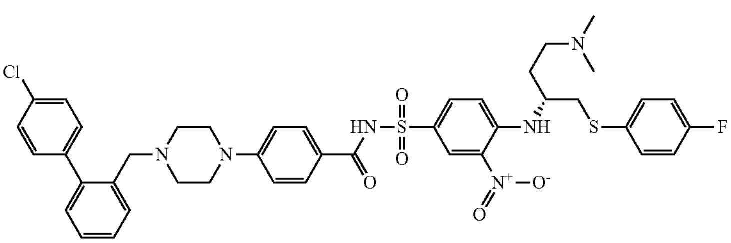 [SMILES: CN(C)CC[C@H](CSc1ccc(F)cc1)Nc1ccc(S(=O)(=O)NC(=O)c2ccc(N3CCN(Cc4ccccc4-c4ccc(Cl)cc4)CC3)cc2)cc1[N+](=O)[O-]] |
| N-(4-(4-((4'-chloro(1,1'-biphenyl)-2-yl)methyl)piperazin-1-yl)benzoyl)-4-(((1R)-1-(((4-fluorophenyl)sulfanyl)methyl)-3-(morpholin-4-yl)propyl)amino)-3-nitrobenzenesulfonamide | 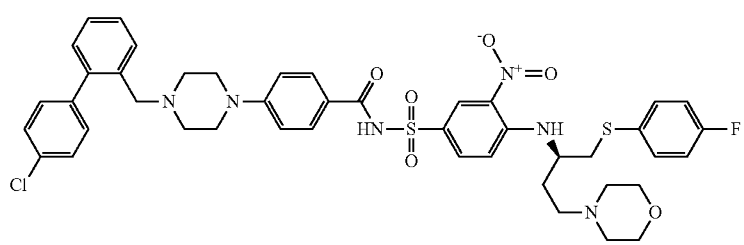 |
| N-(4-(4-((4'-chloro(1,1'-biphenyl)-2-yl)methyl)piperazin-1-yl)-2-fluorobenzoyl)-4-(((1R)-3-(dimethylamino)-1-((phenylsulfanyl)methyl)propyl)amino)-3-nitrobenzenesulfonamide | 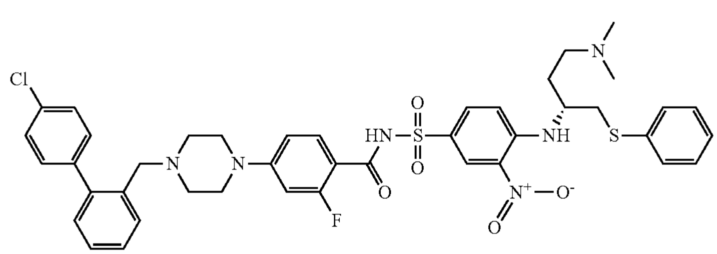 [SMILES: CN(C)CC[C@H](CSc1ccccc1)Nc1ccc(S(=O)(=O)NC(=O)c2ccc(N3CCN(Cc4ccccc4-c4ccc(Cl)cc4)CC3)cc2F)cc1[N+](=O)[O-]] |

| Name | Structure |
|---|---|
| N-(4-(1-((4'-chloro(1,1'-biphenyl)-2-yl)methyl)-1,2,3,6-tetrahydropyridin-4-yl)benzoyl)-4-(((1R)-3-(dimethylamino)-1-((phenylsulfanyl)methyl)propyl)amino)-3-nitrobenzenesulfonamide | 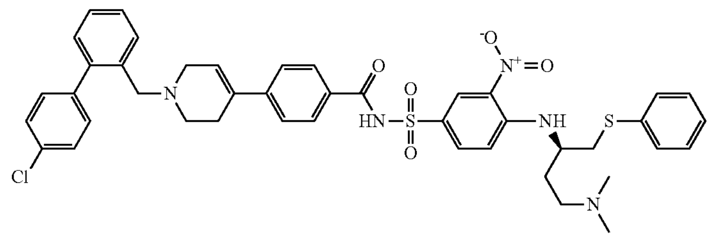 |
| N-(4-(1-((4'-chloro(1,1'-biphenyl)-2-yl)methyl)-1,2,3,6-tetrahydropyridin-4-yl)benzoyl)-4-(((1R)-3-(morpholin-4-yl)-1-((phenylsulfanyl)methyl)propyl)amino)-3-nitrobenzenesulfonamide | 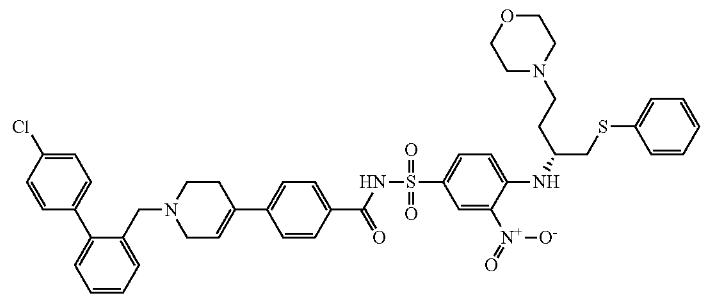 [SMILES: O=C(NS(=O)(=O)c1ccc(N[C@H](CCN2CCOCC2)CSc2ccccc2)c([N+](=O)[O-])c1)c1ccc(C2=CCN(Cc3ccccc3-c3ccc(Cl)cc3)CC2)cc1] |
| N-(4-(4-((4'-chloro(1,1'-biphenyl)-2-yl)methyl)piperazin-1-yl)-2-fluorobenzoyl)-4-(((1R)-3-(dimethylamino)-1-((phenylsulfanyl)methyl)propyl)amino)-3-(trifluoromethyl)benzenesulfonamide | 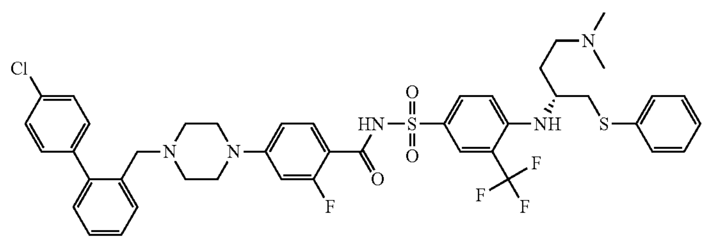 [SMILES: CN(C)CC[C@H](CSc1ccccc1)Nc1ccc(S(=O)(=O)NC(=O)c2ccc(N3CCN(Cc4ccccc4-c4ccc(Cl)cc4)CC3)cc2F)cc1C(F)(F)F] |
| N-((6-(4-((4'-chloro(1,1'-biphenyl)-2-yl)methyl)piperazin-1-yl)pyridin-3-yl)carbonyl)-4-(((1R)-3-(dimethylamino)-1-((phenylsulfanyl)methyl)propyl)amino)-3-nitrobenzenesulfonamide | 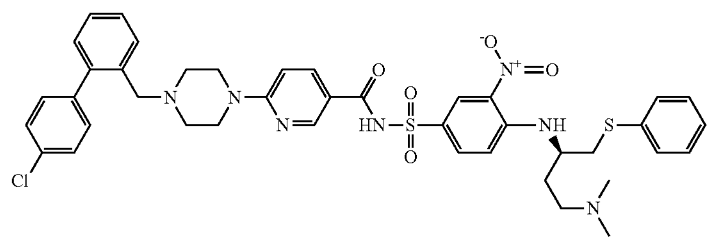 |
| N-(4-(1-((4'-chloro(1,1'-biphenyl)-2-yl)methyl)piperidin-4-yl)benzoyl)-4-(((1R)-3-(dimethylamino)-1-((phenylsulfanyl)methyl)propyl)amino)-3-nitrobenzenesulfonamide | 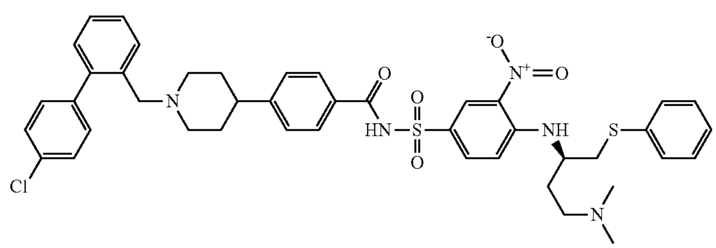 |
| N-(4-(1-((4'-chloro(1,1'-biphenyl)-2-yl)methyl)piperidin-4-yl)benzoyl)-4-(((1R)-3-(morpholin-4-yl)-1-((phenylsulfanyl)methyl)propyl)amino)-3-nitrobenzenesulfonamide | 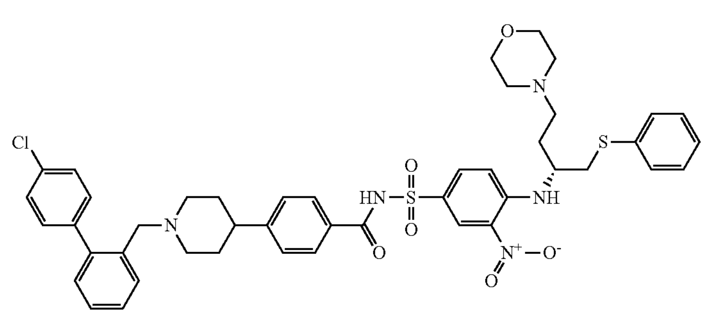 [SMILES: O=C(NS(=O)(=O)c1ccc(N[C@H](CCN2CCOCC2)CSc2ccccc2)c([N+](=O)[O-])c1)c1ccc(C2CCN(Cc3ccccc3-c3ccc(Cl)cc3)CC2)cc1] |

| Name | Structure |
|---|---|
| N-(4-(1-((4'-chloro(1,1'-biphenyl)-2-yl)methyl)-1,2,3,6-tetrahydropyridin-4-yl)benzoyl)-4-(((1R)-3-(dimethylamino)-1-((phenylsulfanyl)methyl)propyl)amino)-3-(trifluoromethyl)benzenesulfonamide | 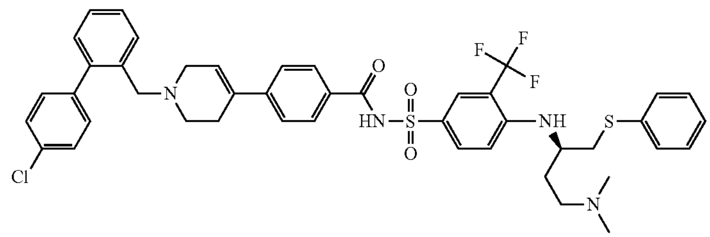 |
| N-((6-(4-((4'-chloro(1,1'-biphenyl)-2-yl)methyl)piperazin-1-yl)pyridin-3-yl)carbonyl)-4-(((1R)-3-(morpholin-4-yl)-1-((phenylsulfanyl)methyl)propyl)amino)-3-nitrobenzenesulfonamide | 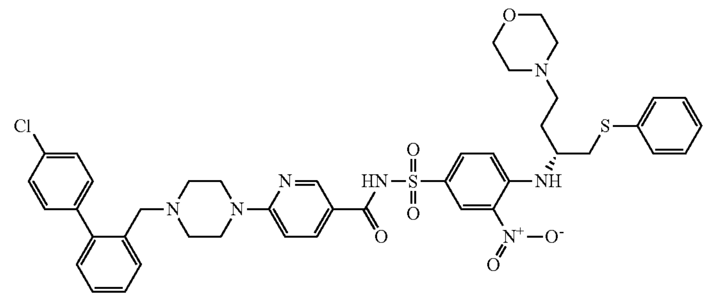 [SMILES: O=C(NS(=O)(=O)c1ccc(N[C@H](CCN2CCOCC2)CSc2ccccc2)c([N+](=O)[O-])c1)c1ccc(N2CCN(Cc3ccccc3-c3ccc(Cl)cc3)CC2)nc1] |
| N-((6-(4-((4'-chloro(1,1'-biphenyl)-2-yl)methyl)piperazin-1-yl)pyridin-3-yl)carbonyl)-4-(((1R)-3-(dimethylamino)-1-((phenylsulfanyl)methyl)propyl)amino)-3-(trifluoromethyl)benzenesulfonamide | 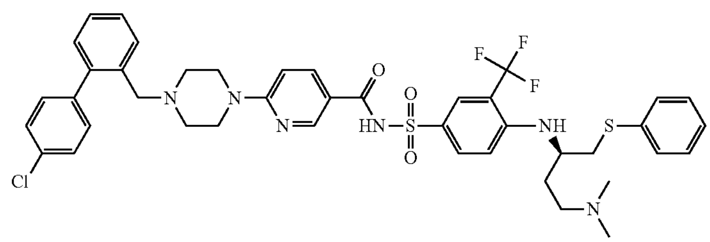 [SMILES: CN(C)CC[C@H](CSc1ccccc1)Nc1ccc(S(=O)(=O)NC(=O)c2ccc(N3CCN(Cc4ccccc4-c4ccc(Cl)cc4)CC3)nc2)cc1C(F)(F)F] |
| N-(4-(4-((4'-chloro(1,1'-biphenyl)-2-yl)methyl)piperidin-1-yl)benzoyl)-4-(((1R)-3-(dimethylamino)-1-((phenylsulfanyl)methyl)propyl)amino)-3-nitrobenzenesulfonamide | 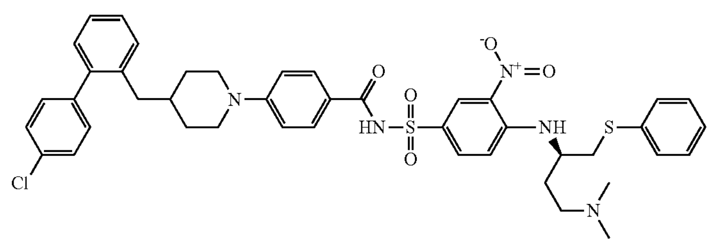 |
| N-(4-(4-((4'-chloro(1,1'-biphenyl)-2-yl)methyl)piperidin-1-yl)benzoyl)-4-(((1R)-3-(morpholin-4-yl)-1-((phenylsulfanyl)methyl)propyl)amino)-3-nitrobenzenesulfonamide | 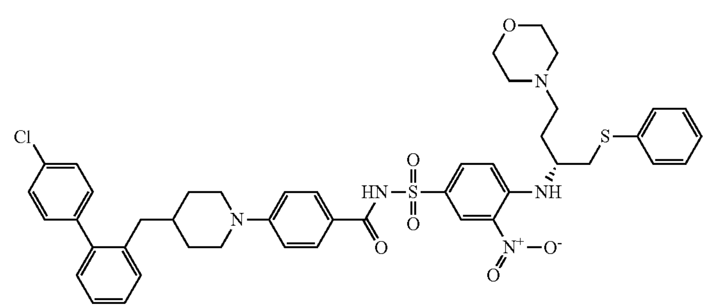 |
| N-((5-(4-((4'-chloro(1,1'-biphenyl)-2-yl)methyl)piperazin-1-yl)pyridin-2-yl)carbonyl)-4-(((1R)-3-(dimethylamino)-1-((phenylsulfanyl)methyl)propyl)amino)-3-nitrobenzenesulfonamide | 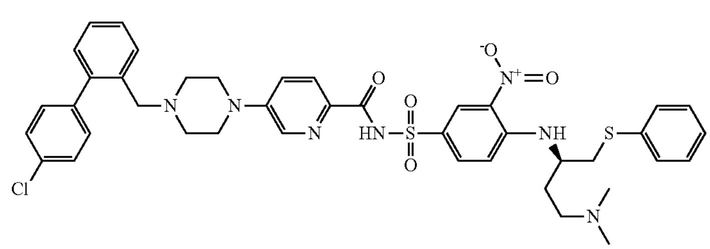 |

| Name | Structure |
|---|---|
| N-((5-(4-((4'-chloro(1,1'-biphenyl)-2-yl)methyl)piperazin-1-yl)pyridin-2-yl)carbonyl)-4-(((1R)-3-(morpholin-4-yl)-1-((phenylsulfanyl)methyl)propyl)amino)-3-nitrobenzenesulfonamide | 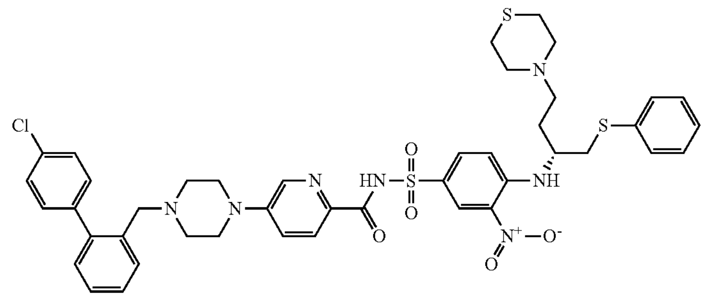 |
| N-(4-(1-((2-(4-chlorophenyl)-5,5-dimethyl-1-cyclohexen-1-yl)methyl)-1,2,3,6-tetrahydropyridin-4-yl)benzoyl)-4-(((1R)-3-(dimethylamino)-1-((phenylsulfanyl)methyl)propyl)amino)-3-nitrobenzenesulfonamide | 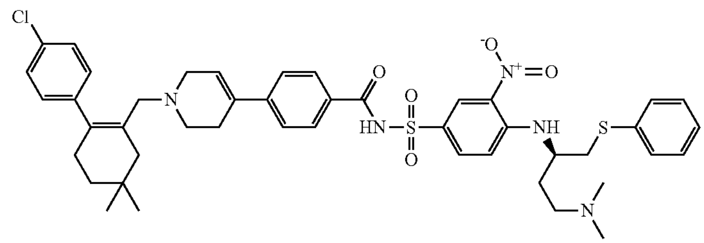 |
| N-(4-(1-((2-(4-chlorophenyl)-1-cyclohexen-1-yl)methyl)-1,2,3,6-tetrahydropyridin-4-yl)benzoyl)-4-(((1R)-3-(dimethylamino)-1-((phenylsulfanyl)methyl)propyl)amino)-3-nitrobenzenesulfonamide | 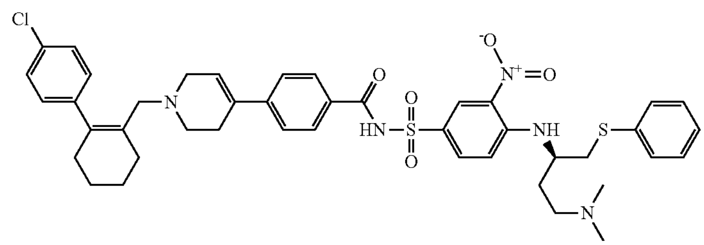 |
| N-(4-(1-((2-(4-chlorophenyl)-1-cyclohexen-1-yl)methyl)-1,2,3,6-tetrahydropyridin-4-yl)benzoyl)-4-(((1R)-3-(morpholin-4-yl)-1-((phenylsulfanyl)methyl)propyl)amino)-3-nitrobenzenesulfonamide | 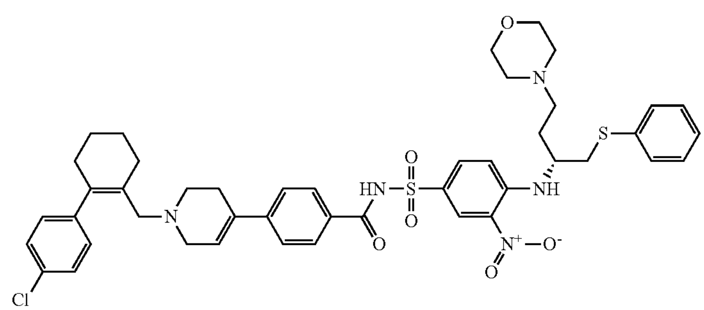 [SMILES: O=C(NS(=O)(=O)c1ccc(N[C@H](CCN2CCOCC2)CSc2ccccc2)c([N+](=O)[O-])c1)c1ccc(C2=CCN(CC3=C(c4ccc(Cl)cc4)CCCC3)CC2)cc1] |
| N-(4-(1-((2-(4-chlorophenyl)-5,5-dimethyl-1-cyclohexen-1-yl)methyl)-1,2,3,6-tetrahydropyridin-4-yl)benzoyl)-4-(((1R)-3-(morpholin-4-yl)-1-((phenylsulfanyl)methyl)propyl)amino)-3-nitrobenzenesulfonamide | 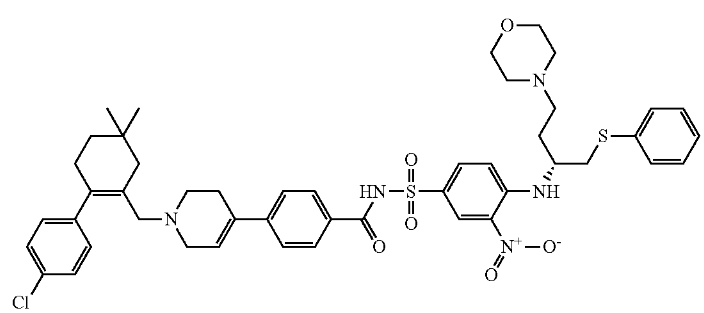 [SMILES: CC1(C)CCC(c2ccc(Cl)cc2)=C(CN2CC=C(c3ccc(C(=O)NS(=O)(=O)c4ccc(N[C@H](CCN5CCOCC5)CSc5ccccc5)c([N+](=O)[O-])c4)cc3)CC2)C1] |

| Name | Structure |
|---|---|
| N-(4-(4-((4'-chloro(1,1'-biphenyl)-2-yl)methyl)-1-cyclohexen-1-yl)benzoyl)-4-(((1R)-3-(dimethylamino)-1-((phenylsulfanyl)methyl)propyl)amino)-3-nitrobenzenesulfonamide | 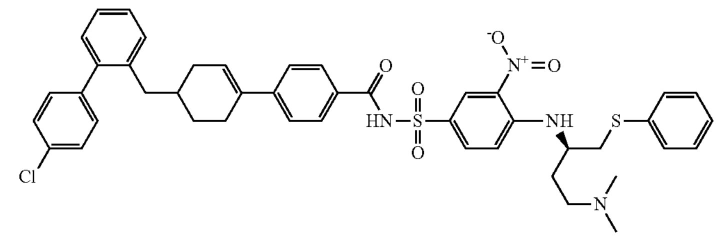 |
| N-(4-(4-((4'-chloro(1,1'-biphenyl)-2-yl)methyl)-1-cyclohexen-1-yl)benzoyl)-4-(((1R)-3-(morpholin-4-yl)-1-((phenylsulfanyl)methyl)propyl)amino)-3-nitrobenzenesulfonamide | 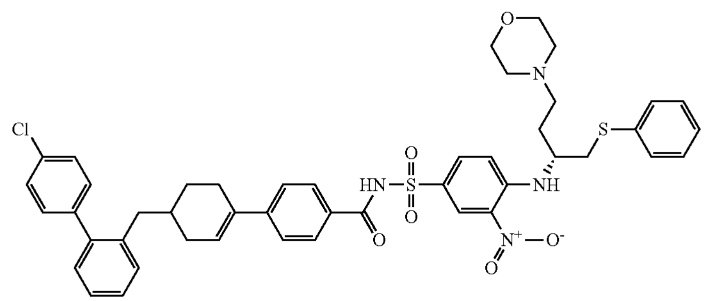 [SMILES: O=C(NS(=O)(=O)c1ccc(N[C@H](CCN2CCOCC2)CSc2ccccc2)c([N+](=O)[O-])c1)c1ccc(C2=CCC(Cc3ccccc3-c3ccc(Cl)cc3)CC2)cc1] |
| N-(4-((3aR,6aS)-5-((4'-chloro(1,1'-biphenyl)-2-yl)methyl)hexahydropyrrolo[3,4-c]pyrrol-2(1H)-yl)benzoyl)-4-(((1R)-3-(dimethylamino)-1-((phenylsulfanyl)methyl)propyl)amino)-3-nitrobenzenesulfonamide | 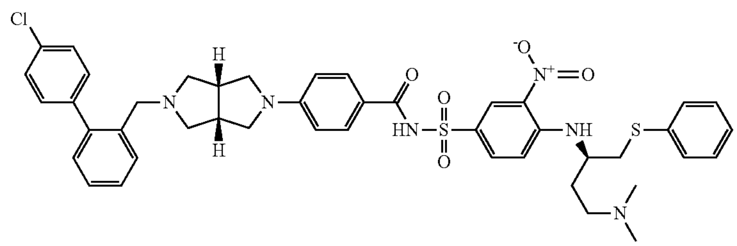 |
| N-(4-(4-((1,1'-biphenyl)-2-ylmethyl)piperazin-1-yl)benzoyl)-4-(methyl((methyl-4-(trifluoromethoxy)anilino)carbonyl)amino)-3-nitrobenzenesulfonamide | 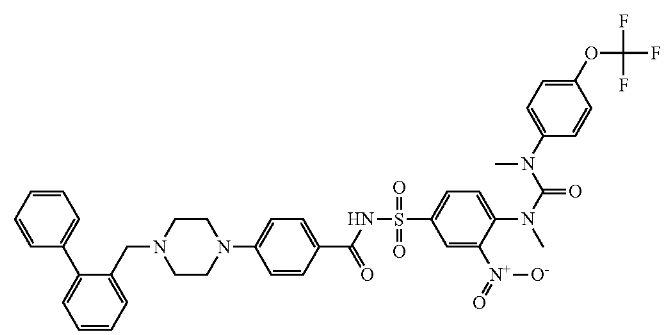 [SMILES: CN(C(=O)N(C)c1ccc(S(=O)(=O)NC(=O)c2ccc(N3CCN(Cc4ccccc4-c4ccccc4)CC3)cc2)cc1[N+](=O)[O-])c1ccc(OC(F)(F)F)cc1] |
| N-(4-(4-((1,1'-biphenyl)-2-ylmethyl)piperazin-1-yl)benzoyl)-4-(((2-dimethylanilino)carbonyl)(methyl)amino)-3-nitrobenzenesulfonamide | |
| N-(4-(4-((1,1'-biphenyl)-2-ylmethyl)piperazin-1-yl)benzoyl)-4-(((4-methoxy(methyl)anilino)carbonyl)(methyl)amino)-3-nitrobenzenesulfonamide | 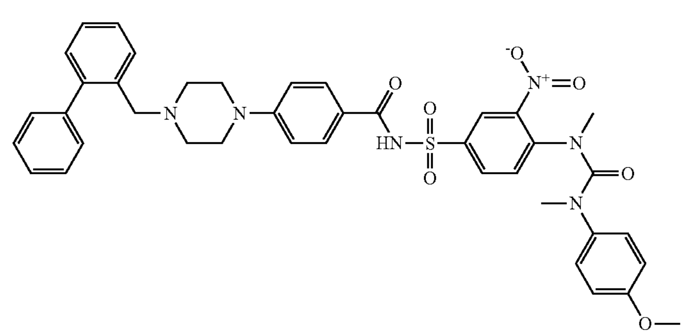 |

| Name | Structure |
|---|---|
| N-((4-((1,1'-biphenyl)-2-ylmethyl)piperazin-1-yl)benzoyl)-4-(((4-dimethylanilino)carbonyl)(methyl)amino)-3-nitrobenzenesulfonamide | |
| 4-(((benzhydryl(methyl)amino)carbonyl)(methyl)amino)-N-(4-(4-((1,1'-biphenyl)-2-ylmethyl)piperazin-1-yl)benzoyl)-3-nitrobenzenesulfonamide | 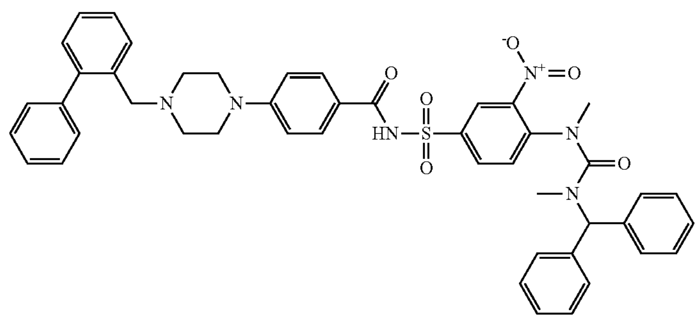 |
| N-(4-(4-((1,1'-biphenyl)-2-ylmethyl)piperazin-1-yl)benzoyl)-4-(methyl((methyl((1S)-1-phenylethyl)amino)carbonyl)amino)-3-nitrobenzenesulfonamide | 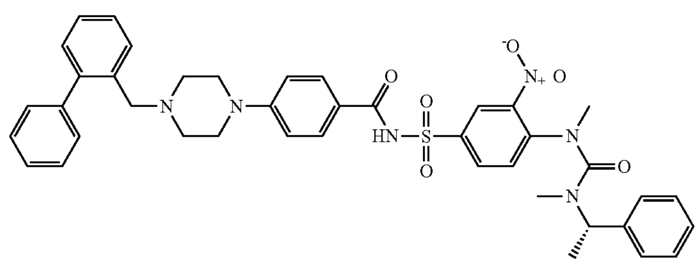 |
| N-(4-(4-((1,1'-biphenyl)-2-ylmethyl)piperazin-1-yl)benzoyl)-4-(methyl((methyl(2-(4-methylpiperazin-1-yl)-1-phenylethyl)amino)carbonyl)amino)-3-nitrobenzenesulfonamide | 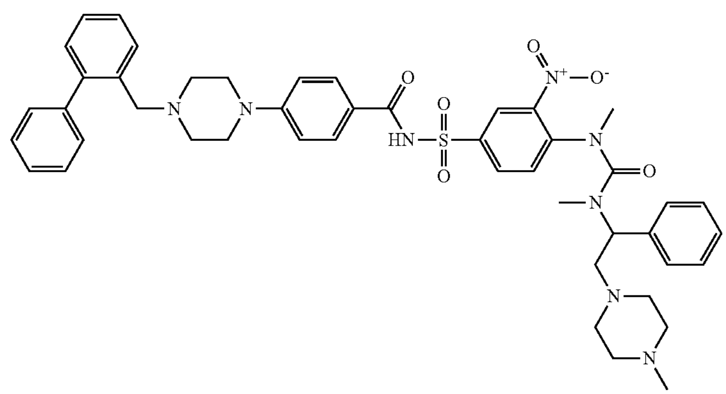 [SMILES: CN1CCN(CC(c2ccccc2)N(C)C(=O)N(C)c2ccc(S(=O)(=O)NC(=O)c3ccc(N4CCN(Cc5ccccc5-c5ccccc5)CC4)cc3)cc2[N+](=O)[O-])CC1] |
| N-(4-(4-((1,1'-biphenyl)-2-ylmethyl)piperazin-1-yl)benzoyl)-4-(methyl((methyl(2-(morpholin-4-yl)-1-phenylethyl)amino)carbonyl)amino)-3-nitrobenzenesulfonamide | 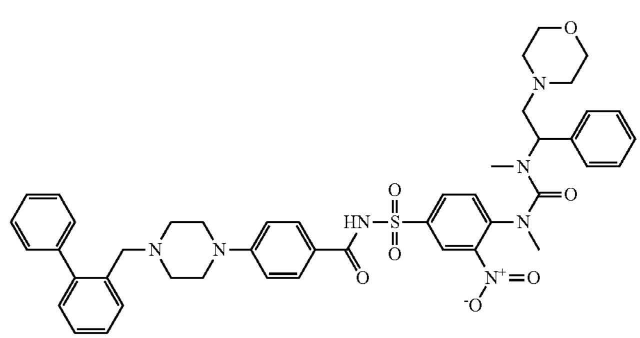 |

| Name | Structure |
|---|---|
| N-(4-(4-((1,1'-biphenyl)-2-ylmethyl) piperazin-1-yl)benzoyl)-4-((((1,2-diphenylethyl)(methyl)amino)carbonyl) (methyl)amino)-3-nitrobenzenesulfonamide | 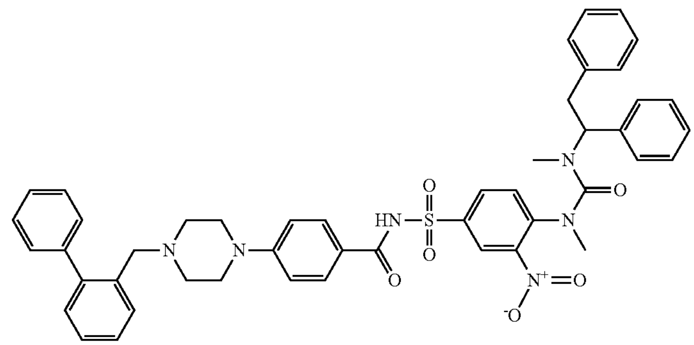 |
| N-(4-(4-((1,1'-biphenyl)-2-ylmethyl) piperazin-1-yl)benzoyl)-4-((((2-(dimethylamino)-1-phenylethyl) (methyl)amino)carbonyl)(methyl) amino)-3-nitrobenzenesulfonamide | 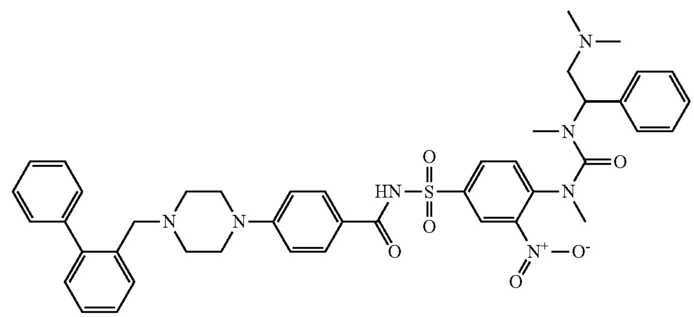 [SMILES: CN(C)CC(c1ccccc1)N(C)C(=O)N(C)c1ccc(S(=O)(=O)NC(=O)c2ccc(N3CCN(Cc4ccccc4-c4ccccc4)CC3)cc2)cc1[N+](=O)[O-]] |
| 3-amino-N-(4-(4-((4'-chloro(1,1'-biphenyl)-2-yl)methyl)piperazin-1-yl) benzoyl)-4-((2-(phenylsulfanyl)ethyl) amino)benzenesulfonamide | 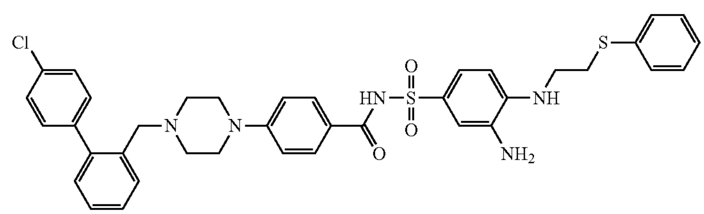 [SMILES: Nc1cc(S(=O)(=O)NC(=O)c2ccc(N3CCN(Cc4ccccc4-c4ccc(Cl)cc4)CC3)cc2)ccc1NCCSc1ccccc1] |
| N-(4-(4-((4'-chloro(1,1'-biphenyl)-2-yl)methyl)piperazin-1-yl)benzoyl)-1-(2-(phenylsulfanyl)ethyl)-1H-1,2,3-benzotriazole-5-sulfonamide | 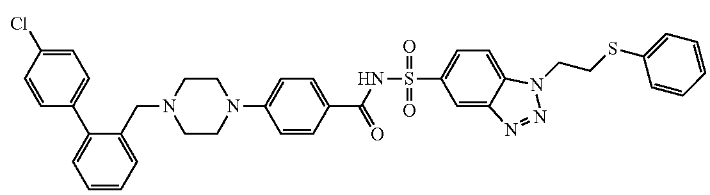 |
| N-(4-(4-((4'-chloro(1,1'-biphenyl)-2-yl)methyl)piperazin-1-yl)benzoyl)-1-(2-(phenylsulfanyl)ethyl)-1H-benzimidazole-5-sulfonamide | 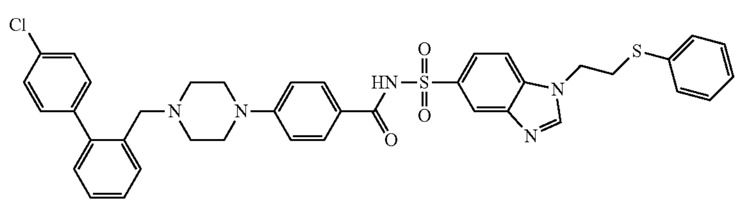 [SMILES: O=C(NS(=O)(=O)c1ccc2c(c1)ncn2CCSc1ccccc1)c1ccc(N2CCN(Cc3ccccc3-c3ccc(Cl)cc3)CC2)cc1] |
| N-(4-(4-((1,1'-biphenyl)-2-ylmethyl)-4-methoxypiperidin-1-yl)benzoyl)-4-((cyclohexylmethyl)amino)-3-nitrobenzenesulfonamide | 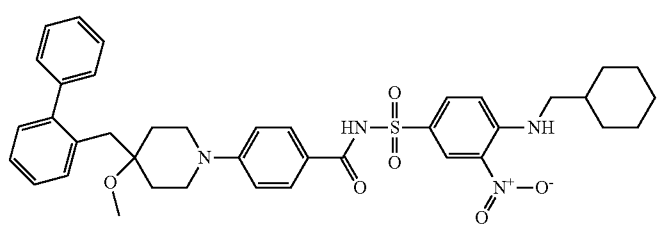 [SMILES: COC1(Cc2ccccc2-c2ccccc2)CCN(c2ccc(C(=O)NS(=O)(=O)c3ccc(NCC4CCCCC4)c([N+](=O)[O-])c3)cc2)CC1] |

| Name | Structure |
|---|---|
| N-(4-(4-((1,1'-biphenyl)-2-ylmethyl)-4-methoxypiperidin-1-yl)benzoyl)-4-(cyclohexylamino)-3-nitrobenzenesulfonamide | 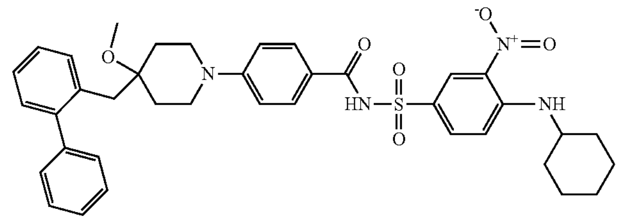 |
| N-(4-(4-((1,1'-biphenyl)-2-ylmethyl)-4-methoxypiperidin-1-yl)benzoyl)-4-((1,1-dimethyl-2-(phenylsulfanyl)ethyl)amino)-3-nitrobenzenesulfonamide | 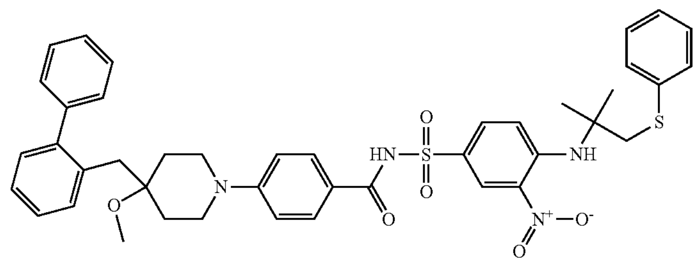 [SMILES: COC1(Cc2ccccc2-c2ccccc2)CCN(c2ccc(C(=O)NS(=O)(=O)c3ccc(NC(C)(C)CSc4ccccc4)c([N+](=O)[O-])c3)cc2)CC1] |
| N-(4-(4-((1,1'-biphenyl)-2-ylmethyl)piperazin-1-yl)benzoyl)-3-nitro-4-((1-((phenylsulfanyl)methyl)cyclopentyl)amino)benzene-sulfonamide | 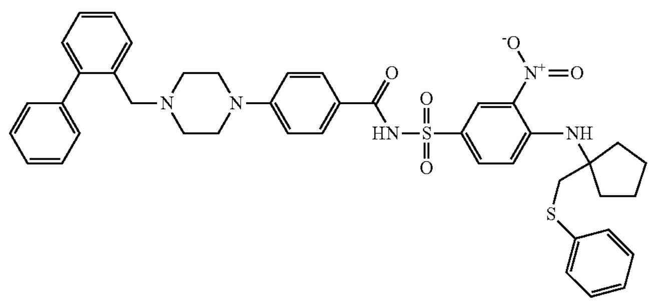 |
| N-(4-(4-((1,1'-biphenyl)-2-ylmethyl)-4-methoxypiperidin-1-yl)benzoyl)-3-nitro-4-((1-((phenylsulfanyl)methyl)cyclopentyl)amino)benzene-sulfonamide | 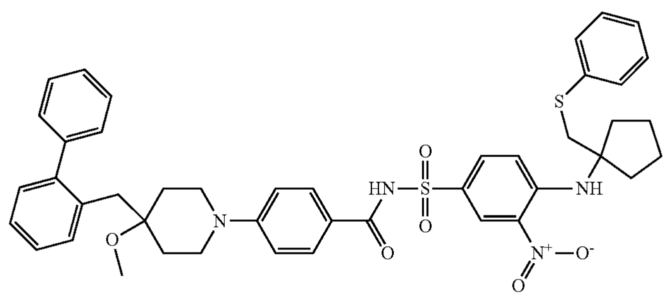 [SMILES: COC1(Cc2ccccc2-c2ccccc2)CCN(c2ccc(C(=O)NS(=O)(=O)c3ccc(NC4(CSc5ccccc5)CCCC4)c([N+](=O)[O-])c3)cc2)CC1] |
| N-(4-(4-((4'-chloro(1,1'-biphenyl)-2-yl)methyl)piperazin-1-yl)benzoyl)-3-nitro-4-((1-((phenylsulfanyl)methyl)cyclopentyl)amino)benzene-sulfonamide | 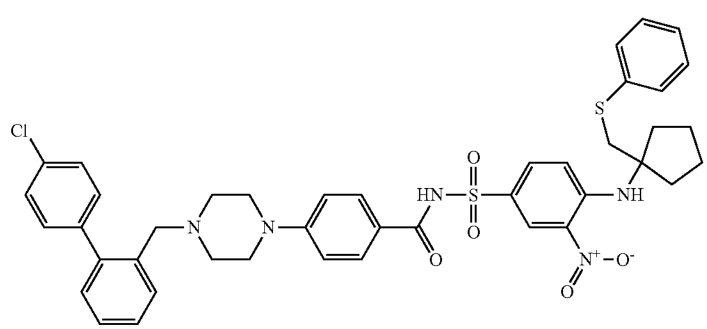 [SMILES: O=C(NS(=O)(=O)c1ccc(NC2(CSc3ccccc3)CCCC2)c([N+](=O)[O-])c1)c1ccc(N2CCN(Cc3ccccc3-c3ccc(Cl)cc3)CC2)cc1] |

-continued

| Name | Structure |
|------|-----------|
| N-(4-(4-((4'-chloro(1,1'-biphenyl)-2-yl)methyl)piperazin-1-yl)benzoyl)-3-nitro-4-(((1S)-1-((phenylsulfanyl)methyl)propyl)amino) benzenesulfonamide | 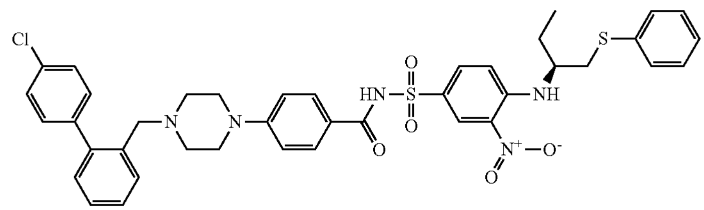 [SMILES: CC[C@@H](CSc1ccccc1)Nc1ccc(S(=O)(=O)NC(=O)c2ccc(N3CCN(Cc4ccccc4-c4ccc(Cl)cc4)CC3)cc2)cc1[N+](=O)[O-]] |
| N-(4-(4-((1,1'-biphenyl)-2-ylmethyl)-4-methoxypiperidin-1-yl)benzoyl)-3-nitro-4-(((1S)-1-((phenylsulfanyl)methyl)propyl)amino) benzenesulfonamide | 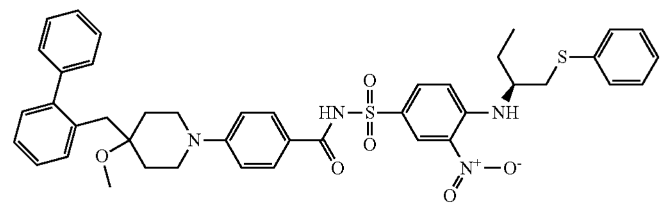 [SMILES: CC[C@@H](CSc1ccccc1)Nc1ccc(S(=O)(=O)NC(=O)c2ccc(N3CCC(Cc4ccccc4-c4ccccc4)(OC)CC3)cc2)cc1[N+](=O)[O-]] |
| N-(4-(4-((4'-chloro(1,1'-biphenyl)-2-yl)methyl)piperazin-1-yl)benzoyl)-4-(((1R)-3-(morpholin-4-yl)-1-((phenylsulfanyl)methyl)propyl)amino)-3-nitrobenzenesulfonamide | 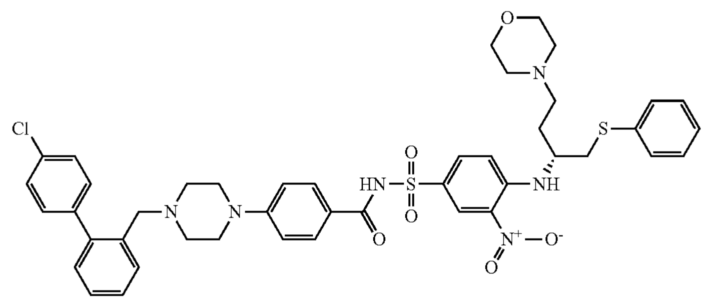 |
| N-(4-(4-((4'-chloro(1,1'-biphenyl)-2-yl)methyl)piperazin-1-yl)benzoyl)-4-(((1S)-3-methyl-1-((phenylsulfanyl)methyl)butyl)amino)-3-nitrobenzenesulfonamide | 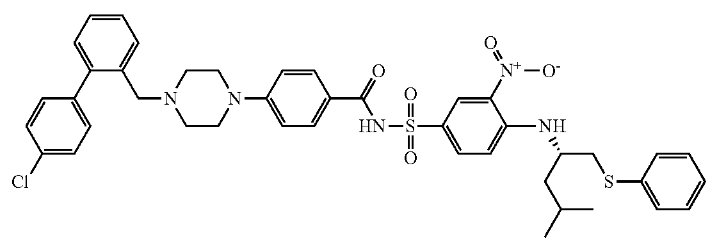 [SMILES: CC(C)C[C@@H](CSc1ccccc1)Nc1ccc(S(=O)(=O)NC(=O)c2ccc(N3CCN(Cc4ccccc4-c4ccc(Cl)cc4)CC3)cc2)cc1[N+](=O)[O-]] |
| N-(4-(4-((1,1'-biphenyl)-2-ylmethyl)-4-methoxypiperidin-1-yl)benzoyl)-4-(((1S)-3-methyl-1-((phenylsulfanyl)methyl)butyl)amino)-3-nitrobenzenesulfonamide | 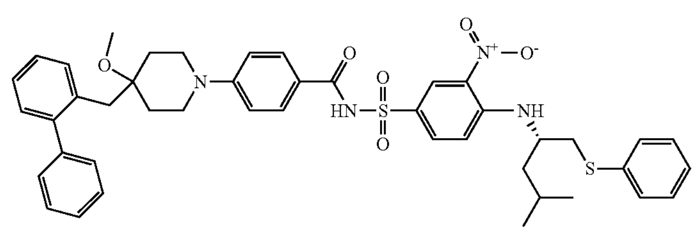 [SMILES: COC1(Cc2ccccc2-c2ccccc2)CCN(c2ccc(C(=O)NS(=O)(=O)c3ccc(N[C@H](CSc4ccccc4)CC(C)C)c([N+](=O)[O-])c3)cc2)CC1] |
| N-(4-(4-((4'-chloro(1,1'-biphenyl)-2-yl)methyl)piperazin-1-yl)benzoyl)-3-nitro-4-((1-((phenylsulfanyl)methyl)cyclopropyl)amino)benzene-sulfonamide | 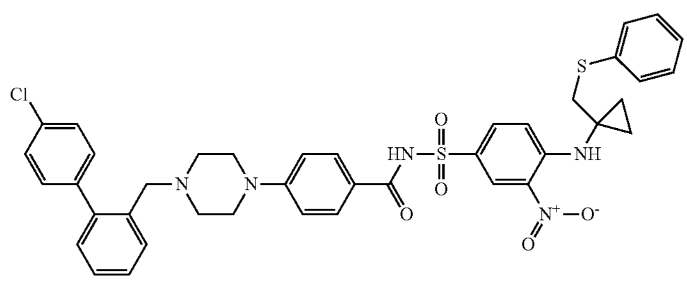 [SMILES: O=C(NS(=O)(=O)c1ccc(NC2(CSc3ccccc3)CC2)c([N+](=O)[O-])c1)c1ccc(N2CCN(Cc3ccccc3-c3ccc(Cl)cc3)CC2)cc1] |

| Name | Structure |
|---|---|
| N-(4-(4-((4'-chloro(1,1'-biphenyl)-2-yl)methyl)piperazin-1-yl)benzoyl)-3-nitro-4-((1-((phenylsulfanyl)methyl)cyclohexyl)amino)benzene-sulfonamide | 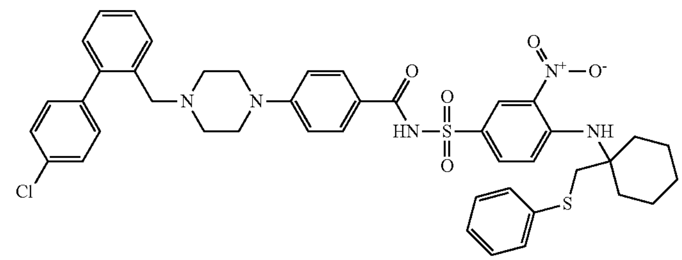 [SMILES: O=C(NS(=O)(=O)c1ccc(NC2(CSc3ccccc3)CCCCC2)c([N+](=O)[O-])c1)c1ccc(N2CCN(Cc3ccccc3-c3ccc(Cl)cc3)CC2)cc1] |
| N-(4-(4-((4'-chloro(1,1'-biphenyl)-2-yl)methyl)piperazin-1-yl)benzoyl)-4-(((1R)-1-methyl-2-(phenylsulfanyl)ethyl)amino)-3-nitrobenzenesulfonamide | 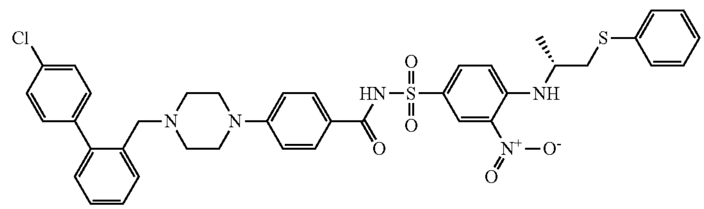 |
| N-(4-(4-((1,1'-biphenyl)-2-ylmethyl)piperazin-1-yl)benzoyl)-4-(((1S)-1-methyl-2-(phenylsulfanyl)ethyl)amino)-3-nitrobenzenesulfonamide | 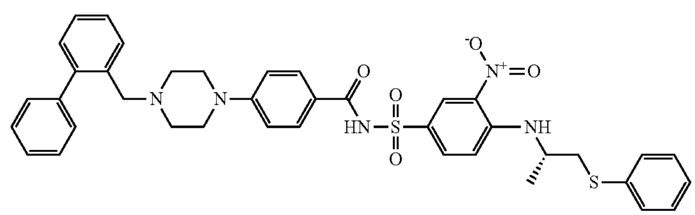 |
| N-(4-(4-((1,1'-biphenyl)-2-ylmethyl)piperazin-1-yl)benzoyl)-3-nitro-4-(((1R,2S)-2-(phenylsulfanyl)cyclohexyl)amino)benzenesulfonamide | 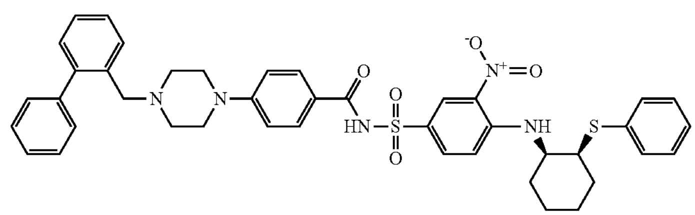 |
| N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-(trifluoromethyl)benzenesulfonamide | 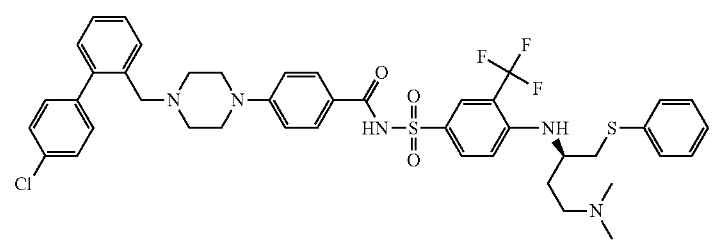 [SMILES: CN(C)CC[C@H](CSc1ccccc1)Nc1ccc(S(=O)(=O)NC(=O)c2ccc(N3CCN(Cc4ccccc4-c4ccc(Cl)cc4)CC3)cc2)cc1C(F)(F)F] |
| 4-(((1R)-5-amino-1-((phenylsulfanyl)methyl)pentyl)amino)-N-(4-(4-((4'-chloro(1,1'-biphenyl)-2-yl)methyl)piperazin-1-yl)benzoyl)-3-nitrobenzenesulfonamide | 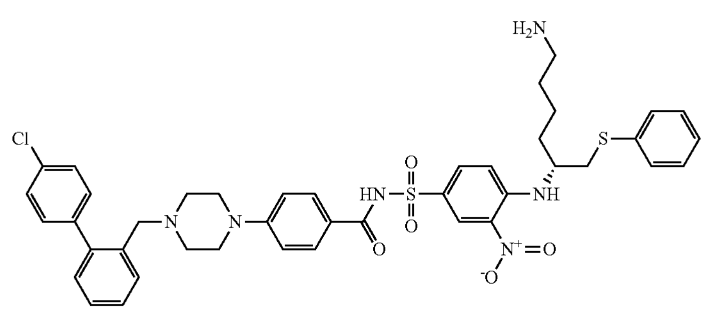 |

| Name | Structure |
|---|---|
| N-(4-(4-((1,1'-biphenyl)-2-ylmethyl)piperazin-1-yl)benzoyl)-3-nitro-4-(((1S)-2-(phenylsulfanyl)-1-(pyridin-3-ylmethyl)ethyl)amino)benzenesulfonamide | 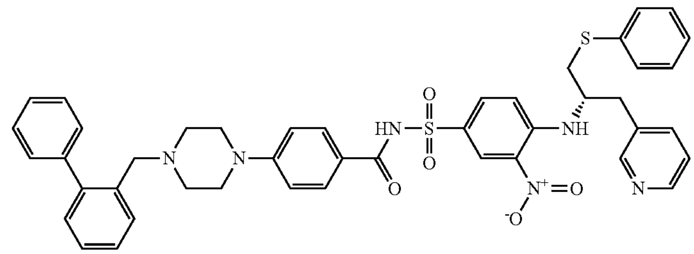 |
| N-(4-(4-((1,1'-biphenyl)-2-ylmethyl)-4-methoxypiperidin-1-yl)benzoyl)-3-nitro-4-(((1S)-2-(phenylsulfanyl)-1-(pyridin-3-ylmethyl)ethyl)amino)benzenesulfonamide | 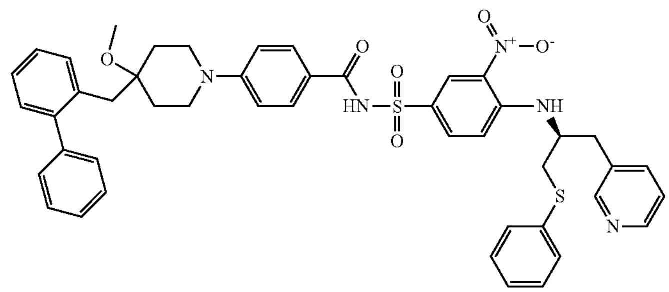 [SMILES: COC1(Cc2ccccc2-c2ccccc2)CCN(c2ccc(C(=O)NS(=O)(=O)c3ccc(N[C@H](CSc4ccccc4)Cc4cccnc4)c([N+](=O)[O-])c3)cc2)CC1] |
| N-(4-(4-((1,1'-biphenyl)-2-ylmethyl)piperazin-1-yl)benzoyl)-3-nitro-4-(((1S,2R)-2-(phenylsulfanyl)cyclohexyl)amino)benzenesulfonamide | 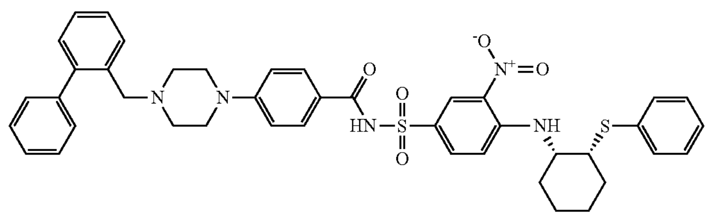 |
| N-(4-(4-((1,1'-biphenyl)-2-ylmethyl)piperazin-1-yl)benzoyl)-4-((1-(((2-methyl-3-furyl)sulfanyl)methyl)cyclopentyl)amino)-3-nitrobenzenesulfonamide | 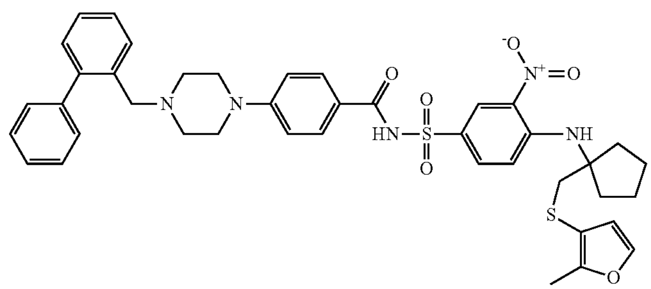 |
| N-(4-(4-((4'-chloro(1,1'-biphenyl)-2-yl)methyl)piperazin-1-yl)benzoyl)-4-((1-(((2-methyl-3-furyl)sulfanyl)methyl)cyclopentyl)amino)-3-nitrobenzenesulfonamide | 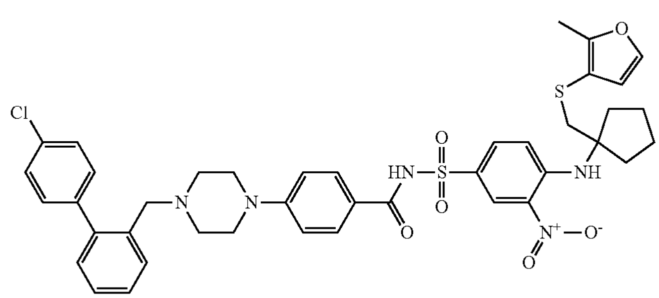 [SMILES: Cc1occc1SCC1(Nc2ccc(S(=O)(=O)NC(=O)c3ccc(N4CCN(Cc5ccccc5-c5ccc(Cl)cc5)CC4)cc3)cc2[N+](=O)[O-])CCCC1] |
| N-(4-(4-((4'-chloro(1,1'-biphenyl)-2-yl)methyl)piperazin-1-yl)benzoyl)-3-nitro-4-(((1S)-2-(phenylsulfanyl)-1-(pyridin-3-ylmethyl)ethyl)amino)benzenesulfonamide | 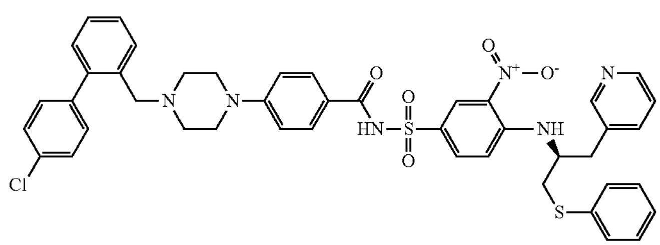 [SMILES: O=C(NS(=O)(=O)c1ccc(N[C@H](CSc2ccccc2)Cc2cccnc2)c([N+](=O)[O-])c1)c1ccc(N2CCN(Cc3ccccc3-c3ccc(Cl)cc3)CC2)cc1] |

| Name | Structure |
|---|---|
| N-(4-(4-((2-(4-chlorophenyl)-3-pyridin-3-yl)methyl)piperazin-1-yl)benzoyl)-4-(((1R)-(dimethylamino)-1-((phenylsulfanyl)methyl)propyl)amino)-3-nitrobenzenesulfonamide | |
| N-(4-(4-((2-(4-chlorophenyl)pyridin-3-yl)methyl)piperazin-1-yl)benzoyl)-3-nitro-4-((2-(phenylsulfanyl)ethyl)amino)benzenesulfonamide | 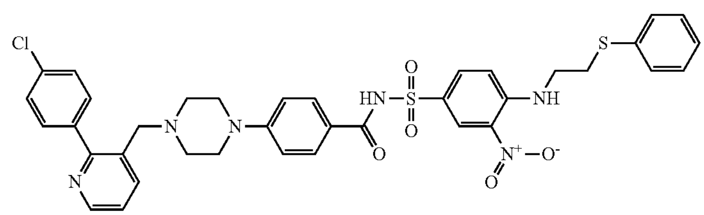 |
| N-(4-(4-((2-(4-chlorophenyl)pyridin-3-yl)methyl)piperazin-1-yl)benzoyl)-4-(((1R)-3-(morpholin-4-yl)-1-((phenylsulfanyl)methyl)propyl)amino)-3-nitrobenzenesulfonamide | 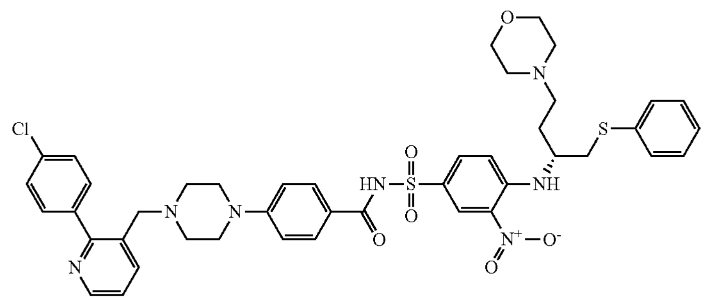 |
| 3-nitro-N-(4-(4-((2-phenylpyridin-3-yl)methyl)piperazin-1-yl)benzoyl)-4-((2-(phenylsulfanyl)ethyl)amino)benzenesulfonamide | 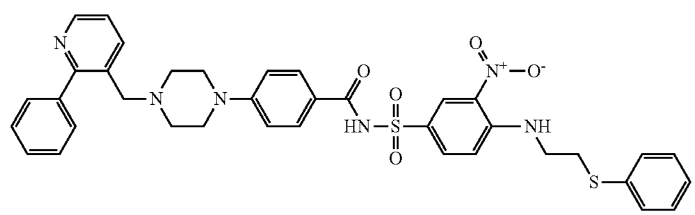 [SMILES: O=C(NS(=O)(=O)c1ccc(NCCSc2ccccc2)c([N+](=O)[O-])c1)c1ccc(N2CCN(Cc3cccnc3-c3ccccc3)CC2)cc1] |
| 4-(((1R)-3-(morpholin-4-yl)-1-((phenylsulfanyl)methyl)propyl)amino)-3-nitro-N-(4-(4-((2-phenylpyridin-3-yl)methyl)piperazin-1-yl)benzoyl)benzenesulfonamide | 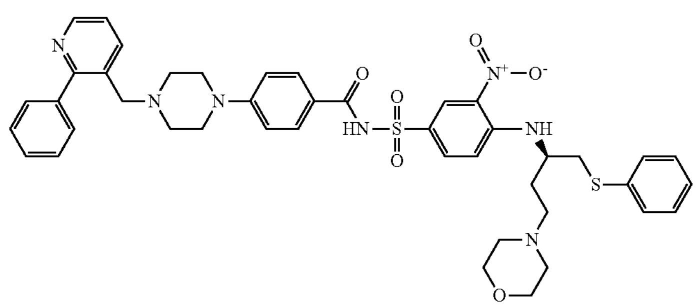 [SMILES: O=C(NS(=O)(=O)c1ccc(N[C@H](CCN2CCOCC2)CSc2ccccc2)c([N+](=O)[O-])c1)c1ccc(N2CCN(Cc3cccnc3-c3ccccc3)CC2)cc1] |
| 4-(((1R)-3-(dimethylamino)-1-((phenylsulfanyl)methyl)propyl)amino)-3-nitro-N-(4-(4-((2-phenylpyridin-3-yl)methyl)piperazin-1-yl)benzoyl)benzenesulfonamide | 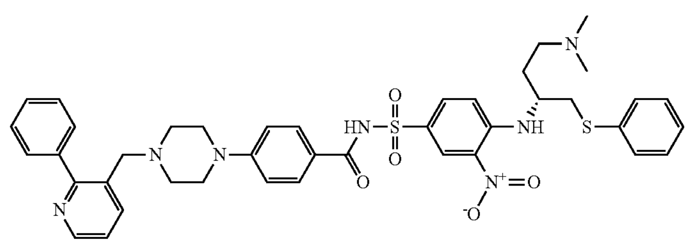 |

| Name | Structure |
|---|---|
| 4-(((1R)-3-(dimethylamino)-1-((phenylsulfanyl)methyl)propyl)amino)-N-(4-(4-((2-(4-(methylsulfanyl)phenyl)pyridin-3-yl)methyl)piperazin-1-yl)benzoyl)-3-nitrobenzenesulfonamide | 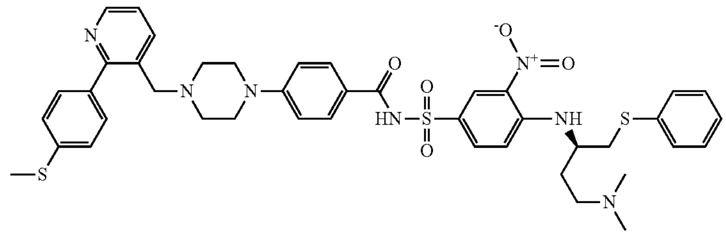 |
| 4-(((1R)-3-(dimethylamino)-1-((phenylsulfanyl)methyl)propyl)amino)-N-(4-(4-((2-(4-methoxyphenyl)pyridin-3-yl)methyl)piperazin-1-yl)benzoyl)-3-nitrobenzenesulfonamide | 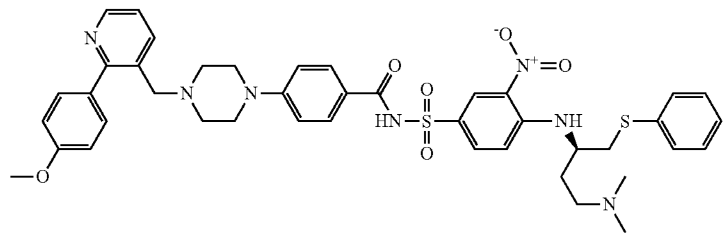 |
| N-(4-(4-((2-(4-(dimethylamino)phenyl)pyridin-3-yl)methyl)piperazin-1-yl)benzoyl)-4-(((1R)-3-(dimethylamino)-1-((phenylsulfanyl)methyl)propyl)amino)-3-nitrobenzenesulfonamide | 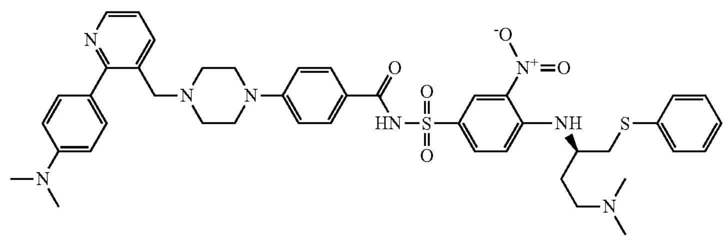 |
| 4-(((1R)-3-(dimethylamino)-1-((phenylsulfanyl)methyl)propyl)amino)-N-(4-(4-((2-(4-fluorophenyl)pyridin-3-yl)methyl)piperazin-1-yl)benzoyl)-3-nitrobenzenesulfonamide | 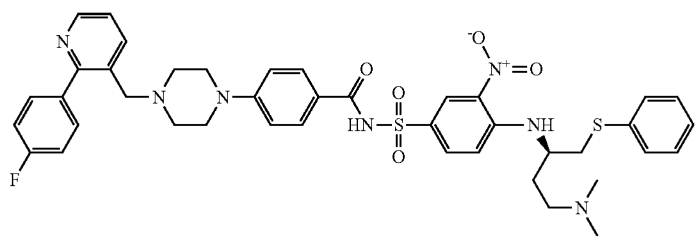 |
| 4-(((1R)-3-(dimethylamino)-1-((phenylsulfanyl)methyl)propyl)amino)-N-(4-(4-((2-(4-(methylsulfonyl)phenyl)pyridin-3-yl)methyl)piperazin-1-yl)benzoyl)-3-nitrobenzenesulfonamide | 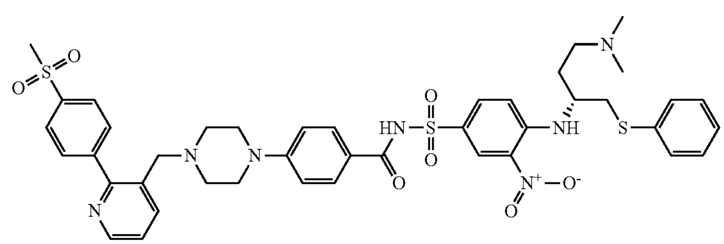 [SMILES: CN(C)CC[C@H](CSc1ccccc1)Nc1ccc(S(=O)(=O)NC(=O)c2ccc(N3CCN(Cc4cccnc4-c4ccc(S(C)(=O)=O)cc4)CC3)cc2)cc1[N+](=O)[O-]] |
| N-(4-(4-((4'-chloro(1,1'-biphenyl)-2-yl)methyl)piperazin-1-yl)benzoyl)-3-nitro-4-((2-(pyridin-4-ylsulfanyl)ethyl)amino)benzenesulfonamide | 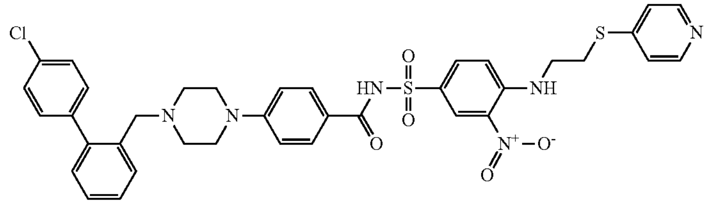 [SMILES: O=C(NS(=O)(=O)c1ccc(NCCSc2ccncc2)c([N+](=O)[O-])c1)c1ccc(N2CCN(Cc3ccccc3-c3ccc(Cl)cc3)CC2)cc1] |

-continued

| Name | Structure |
|---|---|
| 4-(((1R)-3-(dimethylamino)-1-((phenylsulfanyl)methyl)propyl)amino)-N-(4-(4-((4'-(methylsulfonyl)(1,1'-biphenyl)-2-yl)methyl)piperazin-1-yl)benzoyl)-3-nitrobenzenesulfonamide | 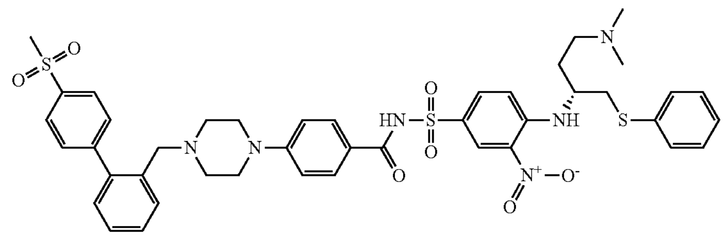 |
| N-(4-(4-((4'-(methylsulfonyl)(1,1'-biphenyl)-2-yl)methyl)piperazin-1-yl)benzoyl)-4-(((1R)-3-(morpholin-4-yl)-1-((phenylsulfanyl)methyl)propyl)amino)-3-nitrobenzenesulfonamide | 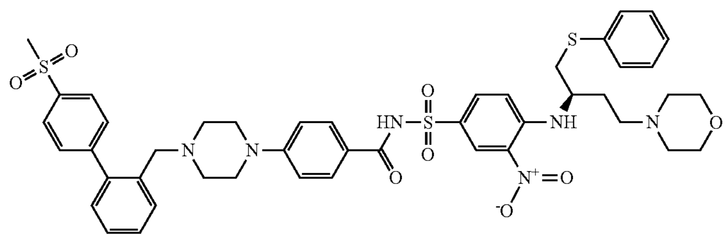 |
| N-(4-(4-((4'-chloro(1,1'-biphenyl)-2-yl)methyl)piperazin-1-yl)benzoyl)-4-(((1R)-3-(morpholin-4-yl)-1-((phenylsulfonyl)methyl)propyl)amino)-3-nitrobenzenesulfonamide | 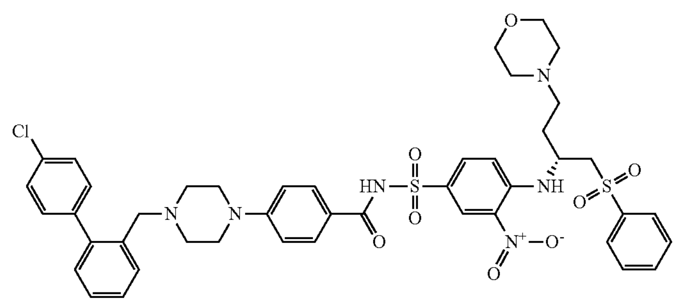 [SMILES: O=C(NS(=O)(=O)c1ccc(N[C@H](CCN2CCOCC2)CS(=O)(=O)c2ccccc2)c([N+](=O)[O-])c1)c1ccc(N2CCN(Cc3ccccc3-c3ccc(Cl)cc3)CC2)cc1] |
| N-(4-(4-((4'-(dimethylamino)(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide | 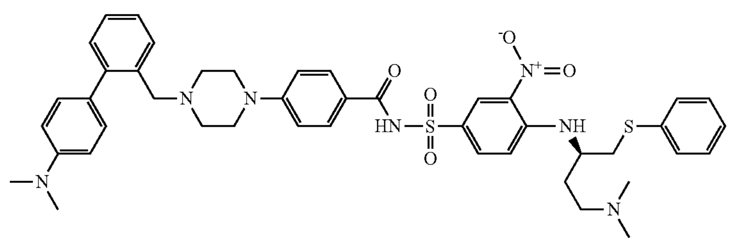 |
| (3R)-3-(4-(((4-(4-((4'-chloro(1,1'-biphenyl)-2-yl)methyl)piperazin-1-yl)benzoyl)amino)sulfonyl)-2-nitroanilino)-N,N-dimethyl-4-(phenylsulfonyl)butanamide | 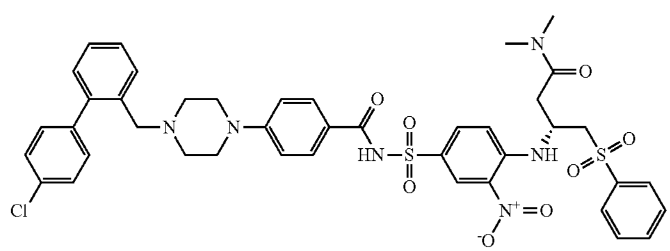 |
| N-(4-(4-((4'-chloro(1,1'-biphenyl)-2-yl)methyl)piperazin-1-yl)benzoyl)-3-nitro-4-(((3S,4R)-(phenylsulfanyl)pyrrolidin-4-yl)amino)benzenesulfonamide | 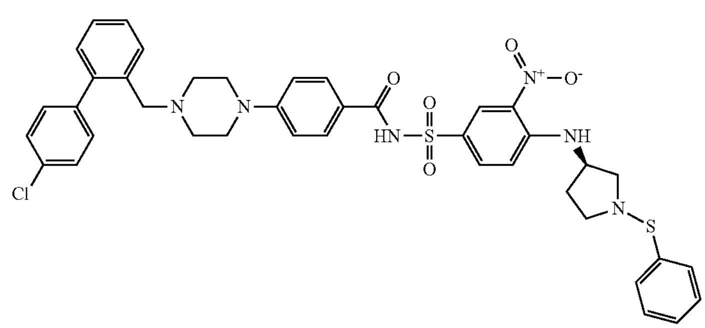 [SMILES: O=C(NS(=O)(=O)c1ccc(N[C@@H]2CCN(Sc3ccccc3)C2)c([N+](=O)[O-])c1)c1ccc(N2CCN(Cc3ccccc3-c3ccc(Cl)cc3)CC2)cc1] |

| Name | Structure |
|---|---|
| N-(4-(4-((4'-chloro(1,1'-biphenyl)-2-yl)methyl)piperazin-1-yl)benzoyl)-3-nitro-4-(((1R)-1-((phenylsulfanyl)methyl)-3-(pyridin-4-ylsulfanyl)propyl)amino)benzenesulfonamide | 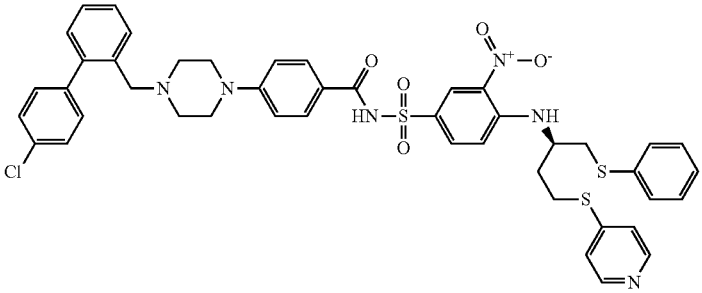 [SMILES: O=C(NS(=O)(=O)c1ccc(N[C@H](CCSc2ccncc2)CSc2ccccc2)c([N+](=O)[O-])c1)c1ccc(N2CCN(Cc3ccccc3-c3ccc(Cl)cc3)CC2)cc1] |
| N-(4-(4-((3-(4-chlorophenyl)pyridin-4-yl)methyl)piperazin-1-yl)benzoyl)-4-(((1R)-3-(dimethylamino)-1-((phenylsulfanyl)methyl)propyl)amino)-3-nitrobenzenesulfonamide | 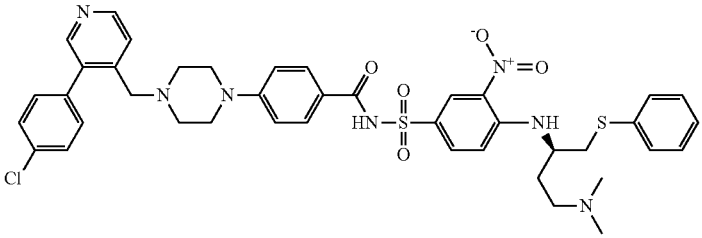 |
| N-(4-(4-((3-(4-chlorophenyl)pyridin-4-yl)methyl)piperazin-1-yl)benzoyl)-3-nitro-4-((2-(phenylsulfanyl)ethyl)amino)benzenesulfonamide | 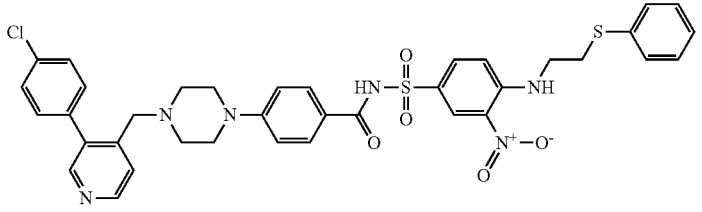 [SMILES: O=C(NS(=O)(=O)c1ccc(NCCSc2ccccc2)c([N+](=O)[O-])c1)c1ccc(N2CCN(Cc3ccncc3-c3ccc(Cl)cc3)CC2)cc1] |
| N-(4-(4-((2-(4-chlorophenyl)-1-cyclopenten-1-yl)methyl)piperazin-1-yl)benzoyl)-4-(((1R)-3-(dimethylamino)-1-((phenylsulfanyl)methyl)propyl)amino)-3-nitrobenzenesulfonamide | 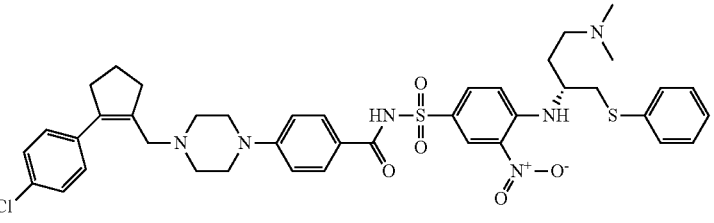 |
| N-(4-(4-((2-(4-chlorophenyl)-1-cyclohexen-1-yl)methyl)piperazin-1-yl)benzoyl)-4-(((1R)-3-(dimethylamino)-1-((phenylsulfanyl)methyl)propyl)amino)-3-nitrobenzenesulfonamide | 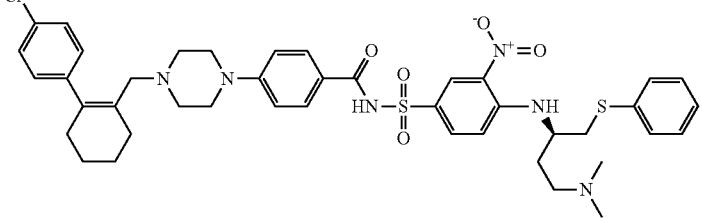 |
| N-(4-(4-((2-bromo-1-cyclopenten-1-yl)methyl)piperazin-1-yl)benzoyl)-4-(((1R)-3-(dimethylamino)-1-((phenylsulfanyl)methyl)propyl)amino)-3-nitrobenzenesulfonamide | 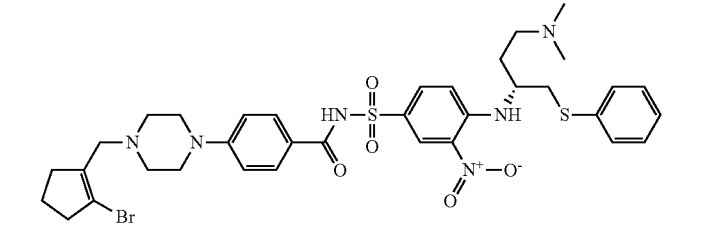 [SMILES: CN(C)CC[C@H](CSc1ccccc1)Nc1ccc(S(=O)(=O)NC(=O)c2ccc(N3CCN(CC4=C(Br)CCC4)CC3)cc2)cc1[N+](=O)[O-]] |

| Name | Structure |
|---|---|
| N-(4-(4-((2-(4-chlorophenyl)-1-cyclohexen-1-yl)methyl)piperazin-1-yl)benzoyl)-4-(((1R)-3-(morpholin-4-yl)-1-((phenylsulfanyl)methyl)propyl)amino)-3-nitrobenzenesulfonamide | 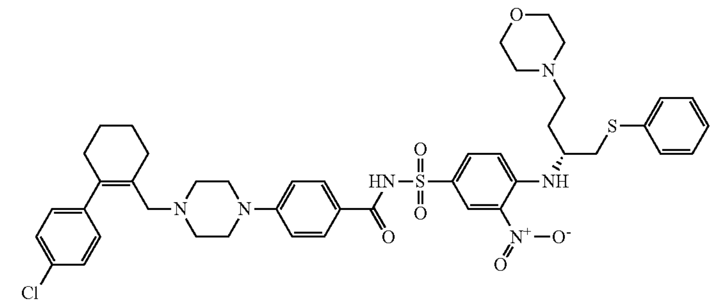 [SMILES: O=C(NS(=O)(=O)c1ccc(N[C@H](CCN2CCOCC2)CSc2ccccc2)c([N+](=O)[O-])c1)c1ccc(N2CCN(CC3=C(c4ccc(Cl)cc4)CCCC3)CC2)cc1] |
| N-(4-(4-((2-(4-chlorophenyl)-1-cyclohexen-1-yl)methyl)piperazin-1-yl)benzoyl)-4-(((1R)-3-(dimethylamino)-1-((phenylsulfanyl)methyl)propyl)amino)-3-(trifluoromethyl)benzenesulfonamide | 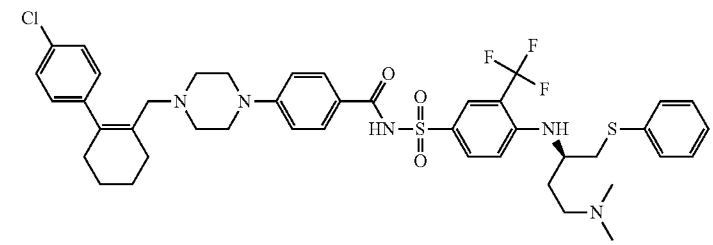 [SMILES: CN(C)CC[C@H](CSc1ccccc1)Nc1ccc(S(=O)(=O)NC(=O)c2ccc(N3CCN(CC4=C(c5ccc(Cl)cc5)CCCC4)CC3)cc2)cc1C(F)(F)F] |
| N-(4-(4-((2-bromo-1-cyclohexen-1-yl)methyl)piperazin-1-yl)benzoyl)-4-(((1R)-3-(dimethylamino)-1-((phenylsulfanyl)methyl)propyl)amino)-3-nitrobenzenesulfonamide | 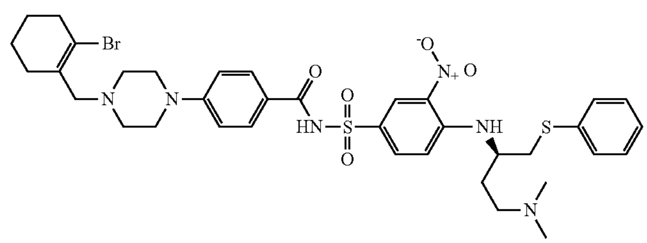 |
| N-(4-(4-((4-(4-chlorophenyl)-5,6-dihydro-2H-pyran-3-yl)methyl)piperazin-1-yl)benzoyl)-4-(((1R)-3-(dimethylamino)-1-((phenylsulfanyl)methyl)propyl)amino)-3-nitrobenzenesulfonamide | 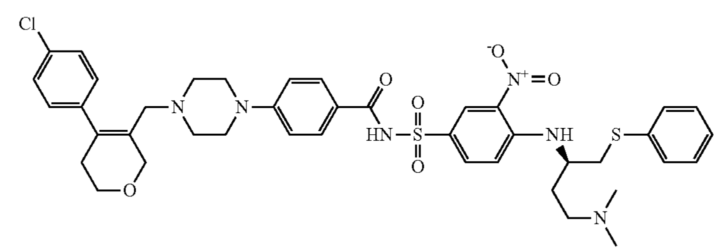 |
| 4-(((1R)-3-(dimethylamino)-1-((phenylsulfanyl)methyl)propyl)amino)-N-(4-(4-((2-(4-methoxyphenyl)-1-cyclohexen-1-yl)methyl)piperazin-1-yl)benzoyl)-3-nitrobenzenesulfonamide | 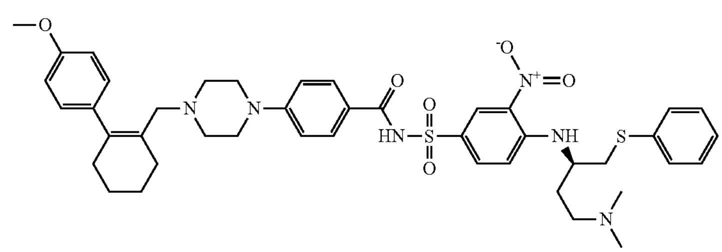 |
| 4-(((1R)-3-(dimethylamino)-1-((phenylsulfanyl)methyl)propyl)amino)-N-(4-(4-((2-(4-fluorophenyl)-1-cyclohexen-1-yl)methyl)piperazin-1-yl)benzoyl)-3-nitrobenzenesulfonamide | 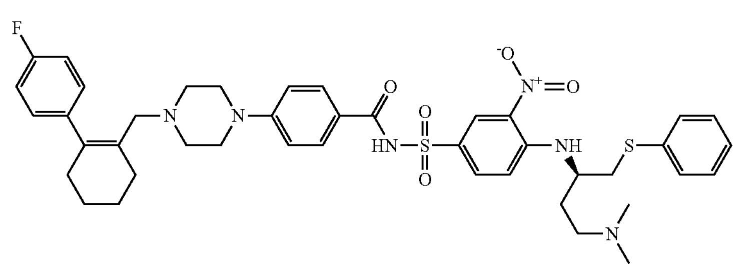 |

| Name | Structure |
|---|---|
| 4-(((1R)-3-(dimethylamino)-1-((phenylsulfanyl)methyl)propyl)amino)-3-nitro-N-(4-(4-((2-phenyl-1-cyclohexen-1-yl)methyl)piperazin-1-yl)benzoyl)benzenesulfonamide | 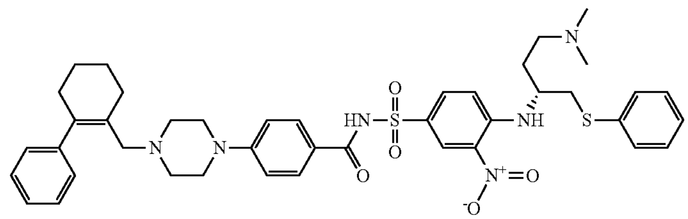 |
| N-(4-(4-((2-(4-chlorophenyl)-1-cyclooccten-1-yl)methyl)piperazin-1-yl)benzoyl)-4-(((1R)-3-(dimethylamino)-1-((phenylsulfanyl)methyl)propyl)amino)-3-nitrobenzenesulfonamide | |
| 4-(((1R)-3-(dimethylamino)-1-((phenylsulfanyl)methyl)propyl)amino)-N-(4-(4-((2-(4-(methylsulfanyl)phenyl)-1-cyclohexen-1-yl)methyl)piperazin-1-yl)benzoyl)-3-nitrobenzenesulfonamide | 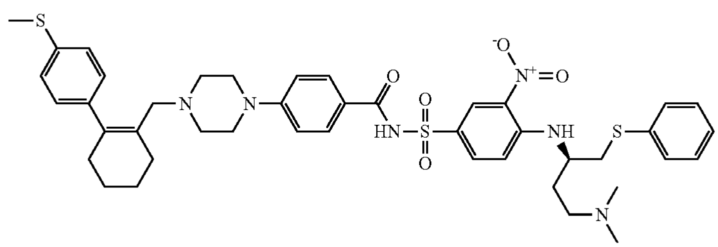 |
| N-(4-(4-((2-(4-chlorophenyl)-1-cyclohepten-1-yl)methyl)piperazin-1-yl)benzoyl)-4-(((1R)-3-(dimethylamino)-1-((phenylsulfanyl)methyl)propyl)amino)-3-nitrobenzenesulfonamide | 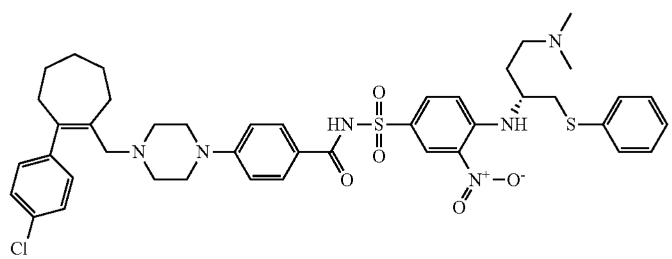 [SMILES: CN(C)CC[C@H](CSc1ccccc1)Nc1ccc(S(=O)(=O)NC(=O)c2ccc(N3CCN(CC4=C(c5ccc(Cl)cc5)CCCCC4)CC3)cc2)cc1[N+](=O)[O-]] |
| N-(4-(4-((2-(4-chlorophenyl)-1-cyclohepten-1-yl)methyl)piperazin-1-yl)benzoyl)-4-(((1R)-3-(morpholin-4-yl)-1-((phenylsulfanyl)methyl)propyl)amino)-3-nitrobenzenesulfonamide | 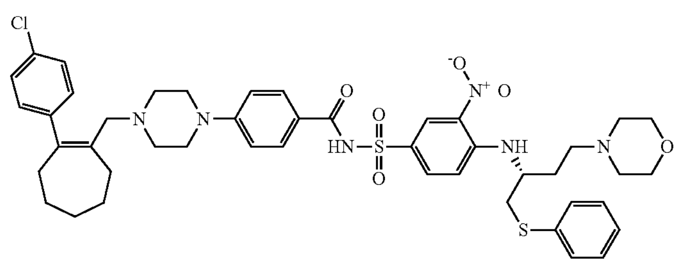 |
| N-(4-(4-((2-(4-chlorophenyl)-5,5-dimethyl-1-cyclohexen-1-yl)methyl)piperazin-1-yl)benzoyl)-4-(((1R)-3-(dimethylamino)-1-((phenylsulfanyl)methyl)propyl)amino)-3-nitrobenzenesulfonamide | 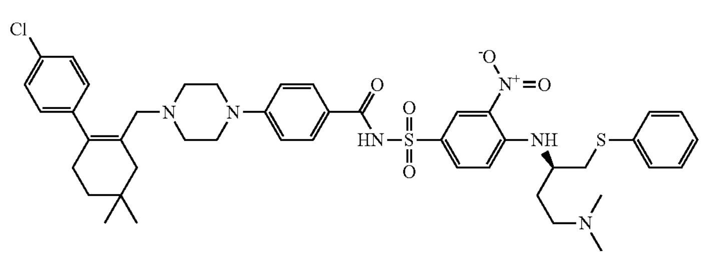 |

-continued

| Name | Structure |
|---|---|
| N-(4-(4-((2-(4-chlorophenyl)-5,5-dimethyl-1-cyclohexen-1-yl)methyl)piperazin-1-yl)benzoyl)-4-(((1R)-3-(morpholin-4-yl)-1-((phenylsulfanyl)methyl)propyl)amino)-3-nitrobenzenesulfonamide | 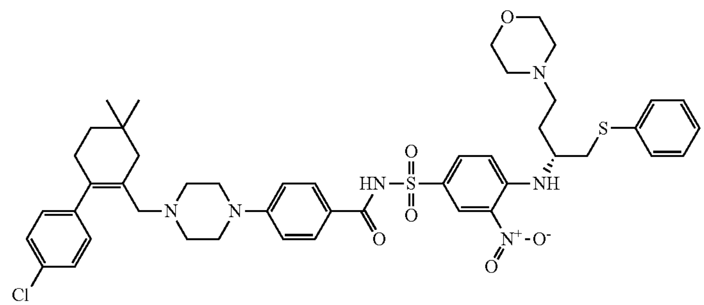 [SMILES: CC1(C)CCC(c2ccc(Cl)cc2)=C(CN2CCN(c3ccc(C(=O)NS(=O)(=O)c4ccc(N[C@H](CCN5CCOCC5)CSc5ccccc5)c([N+](=O)[O-])c4)cc3)CC2)C1] |
| N-(4-(4-((1,1'-biphenyl)-2-ylmethyl)-4-(2-(morpholin-4-yl)ethoxy)piperidin-1-yl)benzoyl)-4-((1,1-dimethyl-2-(phenylsulfanyl)ethyl)amino)-3-nitrobenzenesulfonamide | 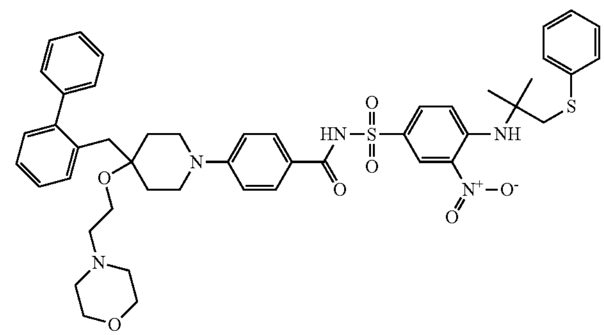 [SMILES: CC(C)(CSc1ccccc1)Nc1ccc(S(=O)(=O)NC(=O)c2ccc(N3CCC(Cc4ccccc4-c4ccccc4)(OCCN4CCOCC4)CC3)cc2)cc1[N+](=O)[O-]] |
| N-(4-(4-((1,1'-biphenyl)-2-ylmethyl)-4-(2-(morpholin-4-yl)ethoxy)piperidin-1-yl)benzoyl)-3-nitro-4-((2-(phenylsulfanyl)ethyl)amino)benzenesulfonamide | 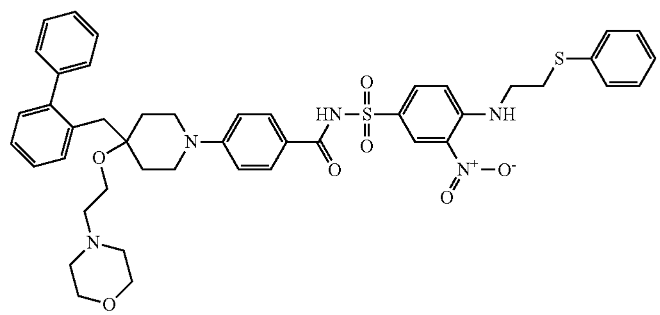 [SMILES: O=C(NS(=O)(=O)c1ccc(NCCSc2ccccc2)c([N+](=O)[O-])c1)c1ccc(N2CCC(Cc3ccccc3-c3ccccc3)(OCCN3CCOCC3)CC2)cc1] |
| N-(4-(4-((1,1'-biphenyl)-2-ylmethyl)-4-(2-(pyrrolidin-1-yl)ethoxy)piperidin-1-yl)benzoyl)-4-((1,1-dimethyl-2-(phenylsulfanyl)ethyl)amino)-3-nitrobenzenesulfonamide | 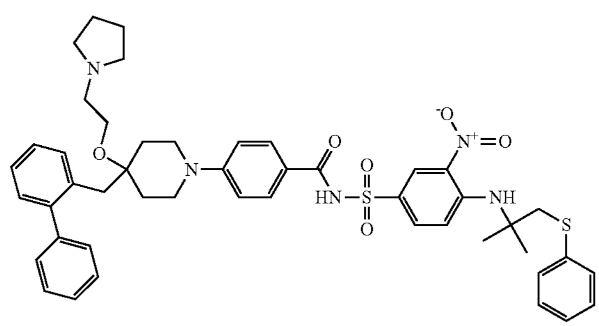 |
| N-(4-(4-((1,1'-biphenyl)-2-ylmethyl)-4-(2-(pyrrolidin-1-yl)ethoxy)piperidin-1-yl)benzoyl)-3-nitro-4-((2-(phenylsulfanyl)ethyl)amino)benzenesulfonamide | 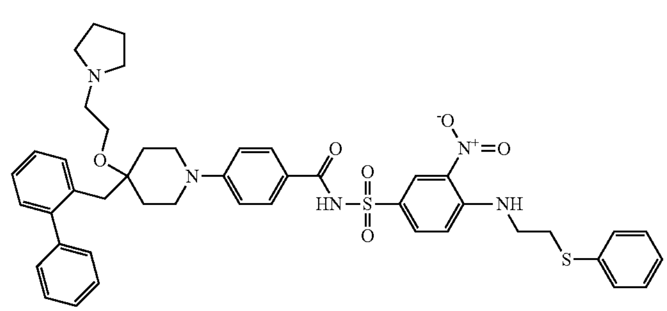 |

| Name | Structure |
|------|-----------|
| N-(4-(4-((1,1'-biphenyl)-2-ylmethyl)-4-(2-(pyrrolidin-1-yl)ethoxy)piperidin-1-yl)benzoyl)-3-nitro-4-((1-((phenylsulfanyl)methyl)cyclopentyl)amino)benzene-sulfonamide | 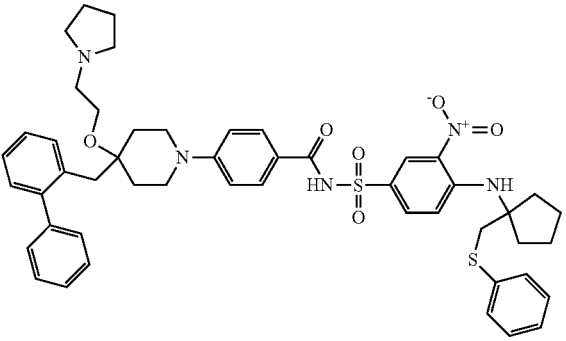 |
| N-(4-(4-((1,1'-biphenyl)-2-ylmethyl)-4-(2-(dimethylamino)ethoxy)piperidin-1-yl)benzoyl)-4-((1,1-dimethyl-2-(phenylsulfanyl)ethyl)amino)-3-nitrobenzenesulfonamide | 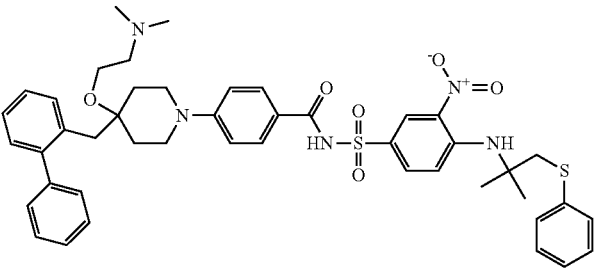 |
| N-(4-(4-((1,1'-biphenyl)-2-ylmethyl)-4-(2-(dimethylamino)ethoxy)piperidin-1-yl)benzoyl)-3-nitro-4-((2-(phenylsulfanyl)ethyl)amino)benzenesulfonamide | 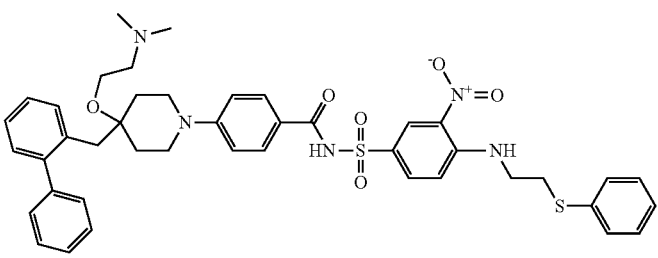 |
| N-(4-(4-((1,1'-biphenyl)-2-ylmethyl)-4-(2-(dimethylamino)ethoxy)piperidin-1-yl)benzoyl)-3-nitro-4-((1-((phenylsulfanyl)methyl)cyclopentyl)amino)benzene-sulfonamide | 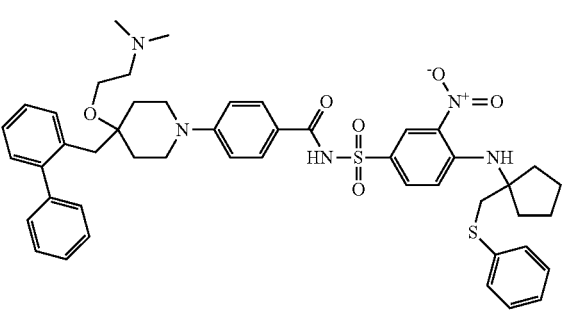 |
| N-(4-(4-((1,1'-biphenyl)-2-ylmethyl)-4-(2-(piperidin-1-yl)ethoxy)piperidin-1-yl)benzoyl)-4-((1,1-dimethyl-2-(phenylsulfanyl)ethyl)amino)-3-nitrobenzenesulfonamide | 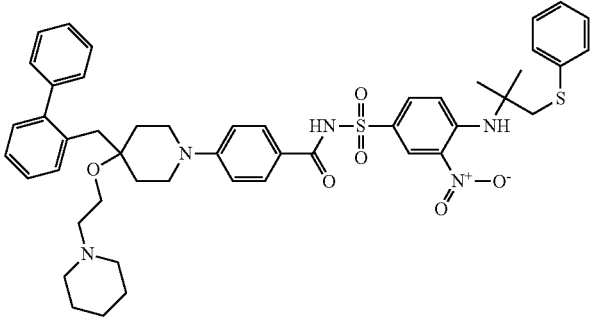 [SMILES: CC(C)(CSc1ccccc1)Nc1ccc(S(=O)(=O)NC(=O)c2ccc(N3CCC(Cc4ccccc4-c4ccccc4)(OCCN4CCCCC4)CC3)cc2)cc1[N+](=O)[O-]] |

| Name | Structure |
|---|---|
| N-(4-(4-((1,1'-biphenyl)-2-ylmethyl)-4-(2-(piperidin-1-yl)ethoxy)piperidin-1-yl)benzoyl)-3-nitro-4-((2-(phenylsulfanyl)ethyl)amino)benzenesulfonamide | 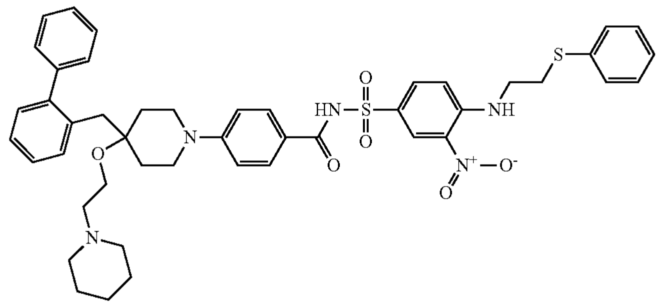 [SMILES: O=C(NS(=O)(=O)c1ccc(NCCSc2ccccc2)c([N+](=O)[O-])c1)c1ccc(N2CCC(Cc3ccccc3-c3ccccc3)(OCCN3CCCCC3)CC2)cc1] |
| N-(4-(4-((1,1'-biphenyl)-2-ylmethyl)-4-(2-(piperidin-1-yl)ethoxy)piperidin-1-yl)benzoyl)-3-nitro-4-((1-((phenylsulfanyl)methyl)cyclopentyl)amino)benzene-sulfonamide | 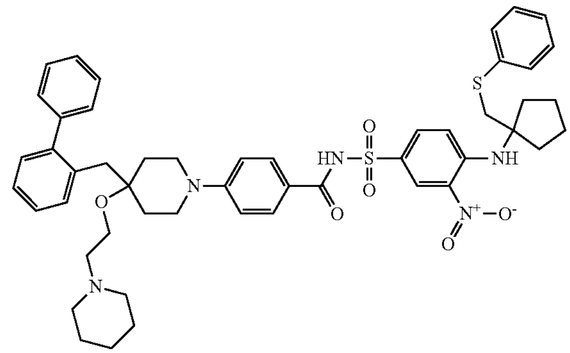 [SMILES: O=C(NS(=O)(=O)c1ccc(NC2(CSc3ccccc3)CCCC2)c([N+](=O)[O-])c1)c1ccc(N2CCC(Cc3ccccc3-c3ccccc3)(OCCN3CCCCC3)CC2)cc1] |
| N-(4-(4-((1,1'-biphenyl)-2-ylmethyl)piperazin-1-yl)benzoyl)-4-(((1S)-3-(morpholin-4-yl)-1-((phenylsulfanyl)methyl)propyl)amino)-3-nitrobenzenesulfonamide | 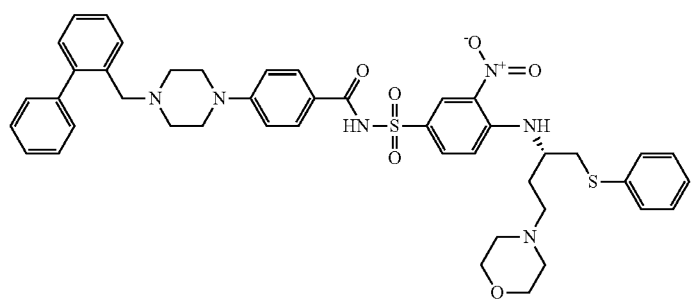 |
| N-(4-(4-((4'-(2-(dimethylamino)ethoxy)(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide | 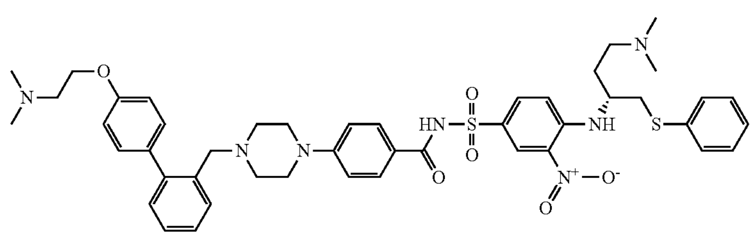 [SMILES: CN(C)CCOc1ccc(-c2ccccc2CN2CCN(c3ccc(C(=O)NS(=O)(=O)c4ccc(N[C@H](CCN(C)C)CSc5ccccc5)c([N+](=O)[O-])c4)cc3)CC2)cc1] |
| N-(4-(4-((4'-(2-(dimethylamino)ethoxy)(1,1'-biphenyl)-2-yl)methyl)piperazin-1-yl)benzoyl)-4-(((1R)-3-(morpholin-4-yl)-1-((phenylsulfanyl)methyl)propyl)amino)-3-nitrobenzenesulfonamide | 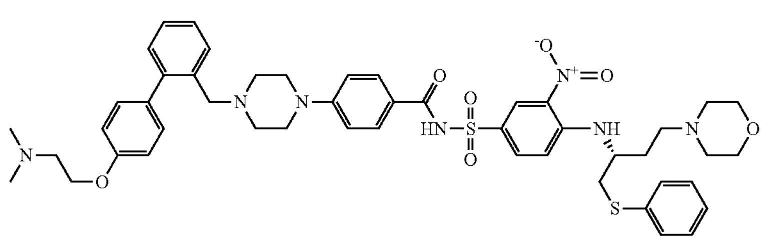 |

| Name | Structure |
|---|---|
| N-(4-(4-((4'-(2-(dimethylamino)ethoxy)(1,1'-biphenyl)-2-yl)methyl)piperazin-1-yl)benzoyl)-4-((1,1-dimethyl-2-(phenylsulfanyl)ethyl)amino)-3-nitrobenzenesulfonamide | 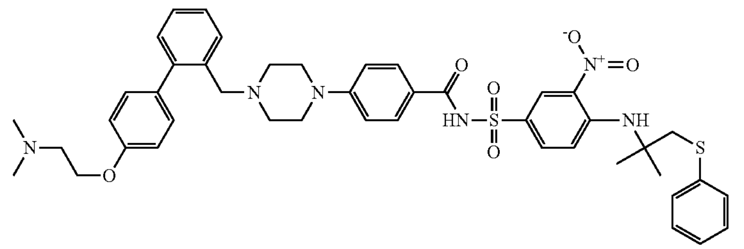 |
| N-(4-(4-((4'-(2-(dimethylamino)ethoxy)(1,1'-biphenyl)-2-yl)methyl)piperazin-1-yl)benzoyl)-3-nitro-4-((2-(phenylsulfanyl)ethyl)amino)benzenesulfonamide | 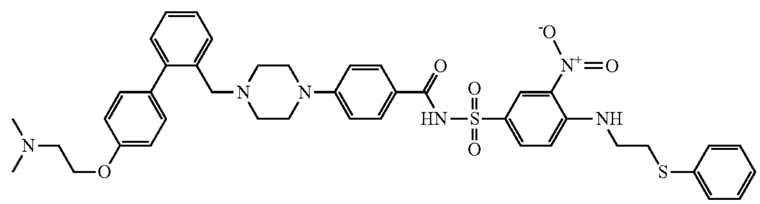 |
| 4-(((1R)-3-(dimethylamino)-1-((phenylsulfanyl)methyl)propyl)amino)-N-(4-(4-((4'-(2-(morpholin-4-yl)ethoxy)(1,1'-biphenyl)-2-yl)methyl)piperazin-1-yl)benzoyl)-3-nitrobenzenesulfonamide | 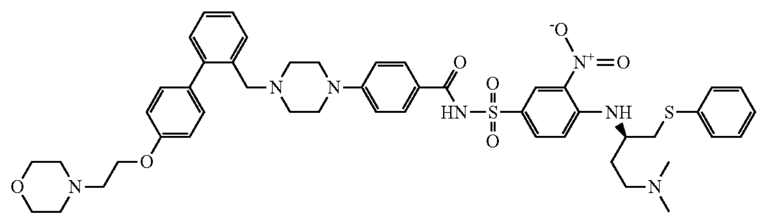 |
| N-(4-(4-((4'-(2-(morpholin-4-yl)ethoxy)(1,1'-biphenyl)-2-yl)methyl)piperazin-1-yl)benzoyl)-4-(((1R)-3-(morpholin-4-yl)-1-((phenylsulfanyl)methyl)propyl)amino)-3-nitrobenzenesulfonamide | 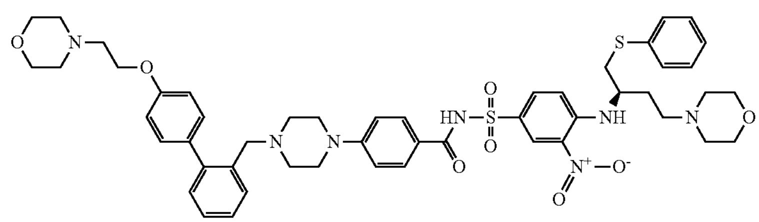 [SMILES: O=C(NS(=O)(=O)c1ccc(N[C@H](CCN2CCOCC2)CSc2ccccc2)c([N+](=O)[O-])c1)c1ccc(N2CCN(Cc3ccccc3-c3ccc(OCCN4CCOCC4)cc3)CC2)cc1] |
| 4-((1,1-dimethyl-2-(phenylsulfanyl)ethyl)amino)-N-(4-(4-((4'-(2-(morpholin-4-yl)ethoxy)(1,1'-biphenyl)-2-yl)methyl)piperazin-1-yl)benzoyl)-3-nitrobenzenesulfonamide | 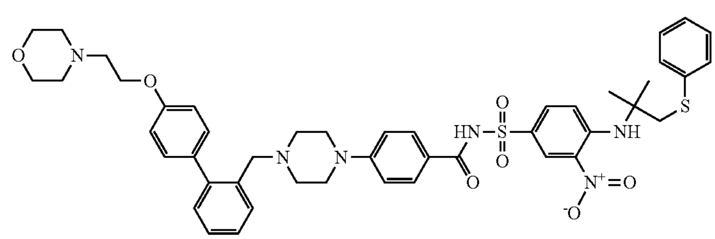 |
| N-(4-(4-((4'-(2-(morpholin-4-yl)ethoxy)(1,1'-biphenyl)-2-yl)methyl)piperazin-1-yl)benzoyl)-3-nitro-4-((2-(phenylsulfanyl)ethyl)amino)benzenesulfonamide | 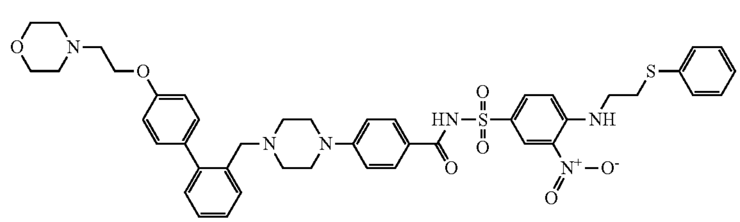 [SMILES: O=C(NS(=O)(=O)c1ccc(NCCSc2ccccc2)c([N+](=O)[O-])c1)c1ccc(N2CCN(Cc3ccccc3-c3ccc(OCCN4CCOCC4)cc3)CC2)cc1] |
| N-(4-(4-((4'-chloro(1,1'-biphenyl)-2-yl)methyl)piperazin-1-yl)benzoyl)-4-(((1R)-3-(1H-imidazol-1-yl)-1-((phenylsulfanyl)methyl)propyl)amino)-3-nitrobenzenesulfonamide | 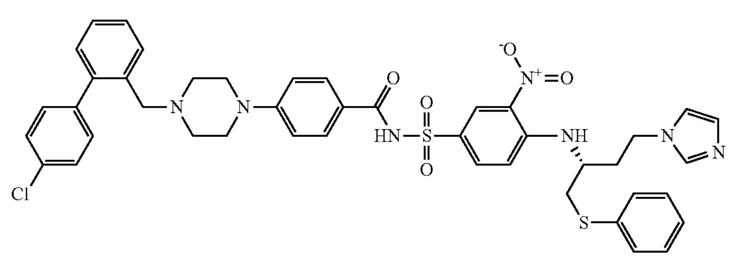 |

| Name | Structure |
|---|---|
| N-(4-(4-((1,1'-biphenyl)-2-ylmethyl)piperazin-1-yl)benzoyl)-4-(((1R)-3-(1H-imidazol-1-yl)-1-((phenylsulfanyl)methyl)propyl)amino)-3-nitrobenzenesulfonamide | 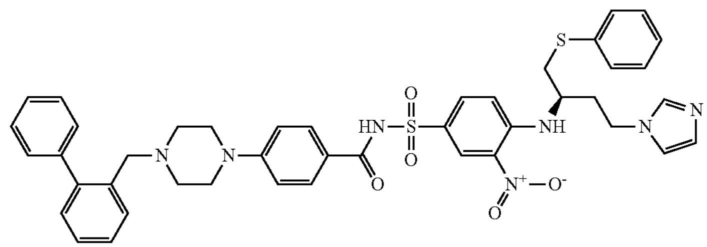 [SMILES: O=C(NS(=O)(=O)c1ccc(N[C@H](CCn2ccnc2)CSc2ccccc2)c([N+](=O)[O-])c1)c1ccc(N2CCN(Cc3ccccc3-c3ccccc3)CC2)cc1] |
| N-(4-(4-((1,1'-biphenyl)-2-ylmethyl)-4-methoxy-piperidin-1-yl)benzoyl)-4-(((1R)-3-(1H-imidazol-1-yl)-1-((phenylsulfanyl)methyl)propyl)amino)-3-nitrobenzenesulfonamide | 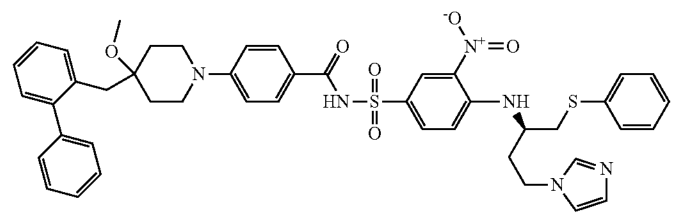 |
| N-(4-(4-((4'-chloro(1,1'-biphenyl)-2-yl)methyl)piperazin-1-yl)benzoyl)-4-(((1R)-4-(4-methylpiperazin-1-yl)-1-((phenylsulfanyl)methyl)butyl)amino)-3-nitrobenzenesulfonamide | 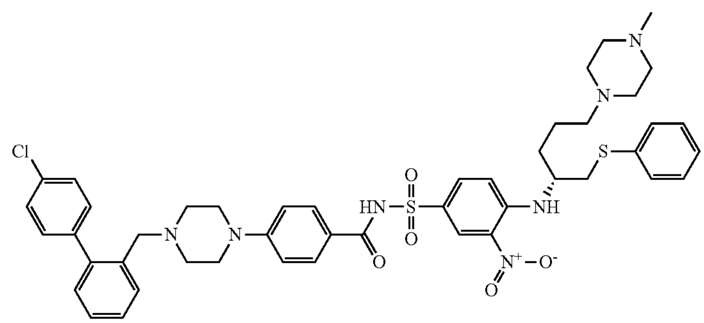 [SMILES: CN1CCN(CCC[C@H](CSc2ccccc2)Nc2ccc(S(=O)(=O)NC(=O)c3ccc(N4CCN(Cc5ccccc5-c5ccc(Cl)cc5)CC4)cc3)cc2[N+](=O)[O-])CC1] |
| N-(4-(4-((4'-chloro(1,1'-biphenyl)-2-yl)methyl)piperazin-1-yl)benzoyl)-4-(((1R)-2-((2-(dimethylamino)ethyl)(methyl)amino)-1-((phenylsulfanyl)methyl)ethyl)amino)-3-nitrobenzenesulfonamide | 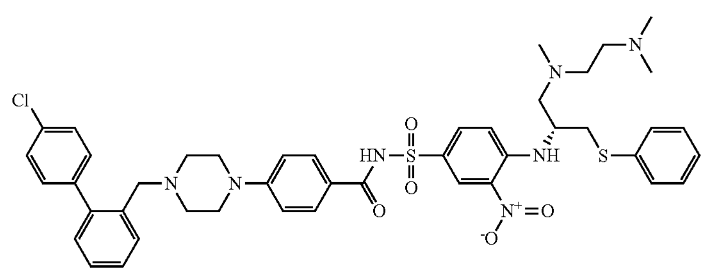 |
| (4R)-4-(4-(((4-(4-((4'-chloro(1,1'-biphenyl)-2-yl)methyl)piperazin-1-yl)benzoyl)amino)sulfonyl)-2-nitroanilino)-N,N-dimethyl-5-(phenylsulfanyl)pentanamide | 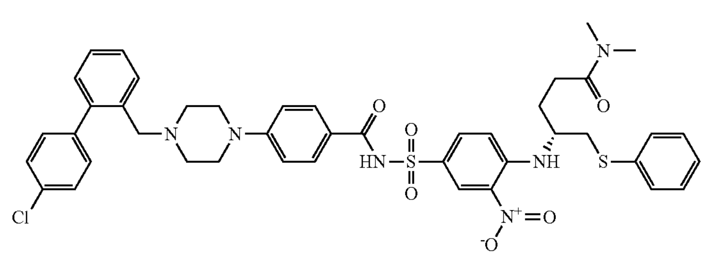 |

-continued

| Name | Structure |
|---|---|
| N-(4-(4-((4'-chloro(1,1'-biphenyl)-2-yl)methyl)piperazin-1-yl)benzoyl)-4-(((1R)-4-(dimethylamino)-1-((phenylsulfonyl)methyl)butyl)amino)-3-nitrobenzenesulfonamide | 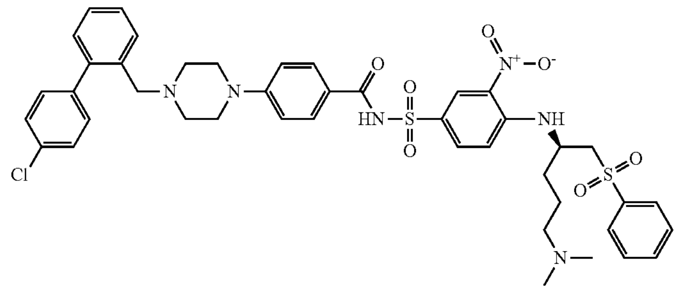 [SMILES: CN(C)CCC[C@H](CS(=O)(=O)c1ccccc1)Nc1ccc(S(=O)(=O)NC(=O)c2ccc(N3CCN(Cc4ccccc4-c4ccc(Cl)cc4)CC3)cc2)cc1[N+](=O)[O-]] |
| 2-(((3R)-3-(4-(((4-(4-((4'-chloro(1,1'-biphenyl)-2-yl)methyl)piperazin-1-yl)benzoyl)amino)sulfonyl)-2-nitroanilino)-4-(phenylsulfanyl)butyl)(methyl)amino)-N,N-dimethylacetamide | 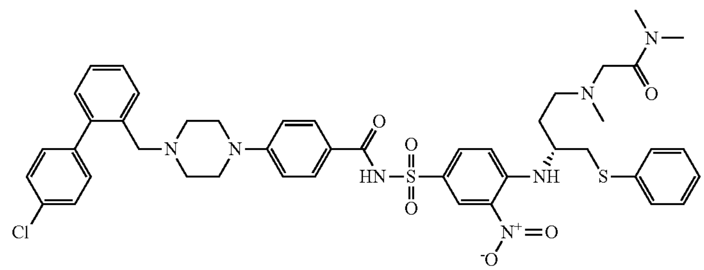 |
| (3R)-N-(tert-butyl)-3-(4-(((4-(4-((4'-chloro(1,1'-biphenyl)-2-yl)methyl)piperazin-1-yl)benzoyl)amino)sulfonyl)-2-nitroanilino)-4-(phenylsulfanyl)butanamide | 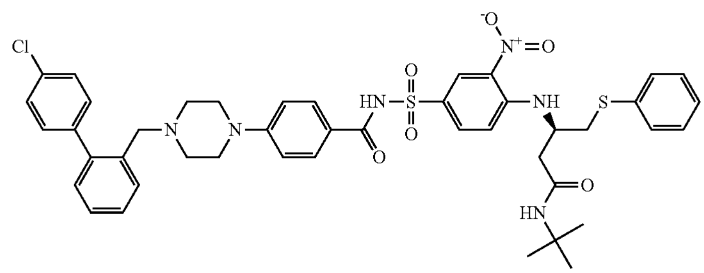 |
| (3R)-3-(4-(((4-(4-((4'-chloro(1,1'-biphenyl)-2-yl)methyl)piperazin-1-yl)benzoyl)amino)sulfonyl)-2-nitroanilino)-N,N-diisopropyl-4-(phenylsulfanyl)butanamide | 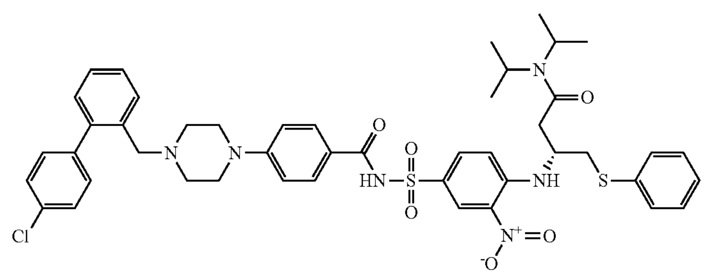 |
| (3R)-N-(tert-butyl)-3-(4-(((4-(4-((4'-chloro(1,1'-biphenyl)-2-yl)methyl)piperazin-1-yl)benzoyl)amino)sulfonyl)-2-nitroanilino)-N-methyl-4-(phenylsulfanyl)butanamide | 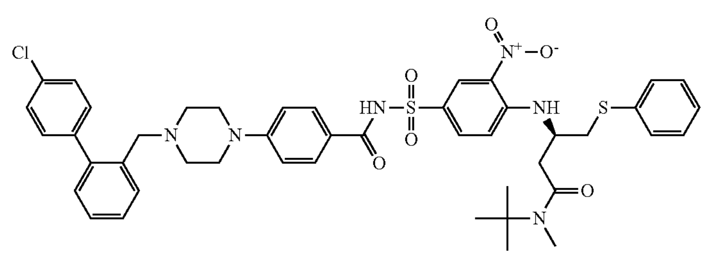 [SMILES: CN(C(=O)C[C@H](CSc1ccccc1)Nc1ccc(S(=O)(=O)NC(=O)c2ccc(N3CCN(Cc4ccccc4-c4ccc(Cl)cc4)CC3)cc2)cc1[N+](=O)[O-])C(C)(C)C] |
| (3R)-3-(4-(((4-(4-((4'-chloro(1,1'-biphenyl)-2-yl)methyl)piperazin-1-yl)benzoyl)amino)sulfonyl)-2-nitroanilino)-N-isopropyl-N-methyl-4-(phenylsulfanyl)butanamide | 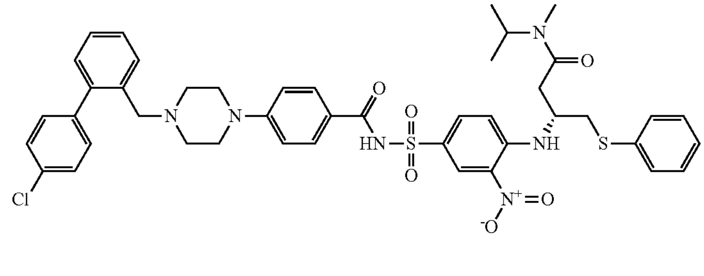 |

| Name | Structure |
|---|---|
| N-(4-(4-((4'-chloro(1,1'-biphenyl)-2-yl)methyl)piperazin-1-yl)benzoyl)-3-nitro-4-(((1R)-3-oxo-1-((phenylsulfanyl)methyl)-3-(piperidin-1-yl)propyl)amino)benzenesulfonamide | 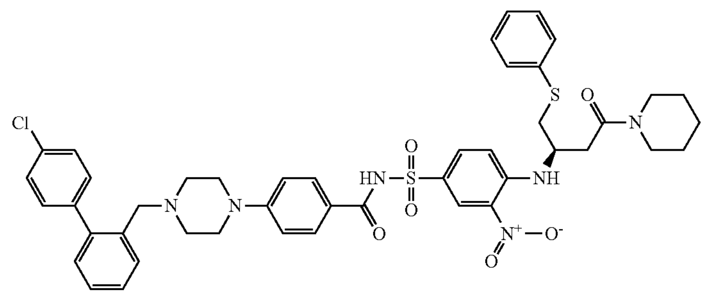 [SMILES: O=C(NS(=O)(=O)c1ccc(N[C@@H](CSc2ccccc2)CC(=O)N2CCCCC2)c([N+](=O)[O-])c1)c1ccc(N2CCN(Cc3ccccc3-c3ccc(Cl)cc3)CC2)cc1] |
| N-((5R)-5-(4-(((4-(4-((4'-chloro(1,1'-biphenyl)-2-yl)methyl)piperazin-1-yl)benzoyl)amino)sulfonyl)-2-nitroanilino)-6-(phenylsulfanyl)hexyl)-2-(dimethylamino)acetamide | 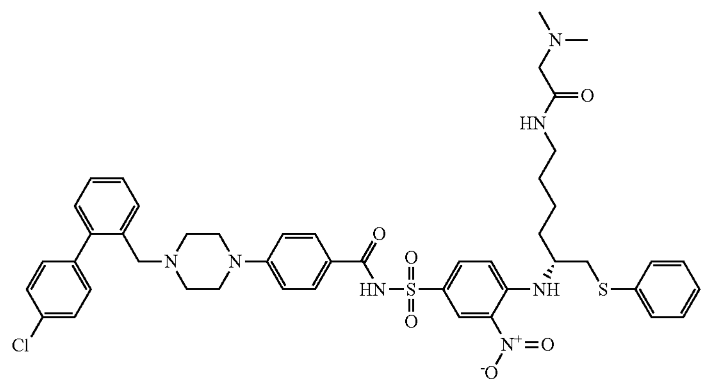 |
| (3R)-3-(4-(((4-(4-((4'-chloro(1,1'-biphenyl)-2-yl)methyl)piperazin-1-yl)benzoyl)amino)sulfonyl)-2-nitroanilino)-N,N-dimethyl-4-(phenylsulfanyl)butanamide | 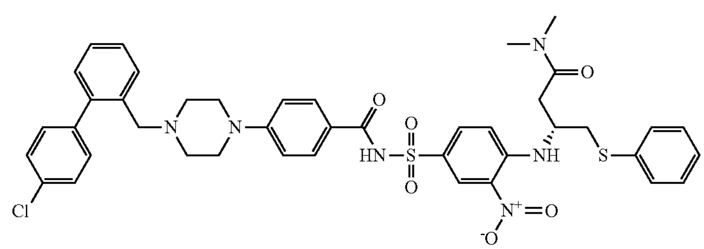 |
| N-(4-(4-((4'-chloro(1,1'-biphenyl)-2-yl)methyl)piperazin-1-yl)benzoyl)-4-(((1R)-3-(1,1-dioxidothiomorpholin-4-yl)-3-oxo-1-((phenylsulfanyl)methyl)propyl)amino)-3-nitrobenzenesulfonamide | 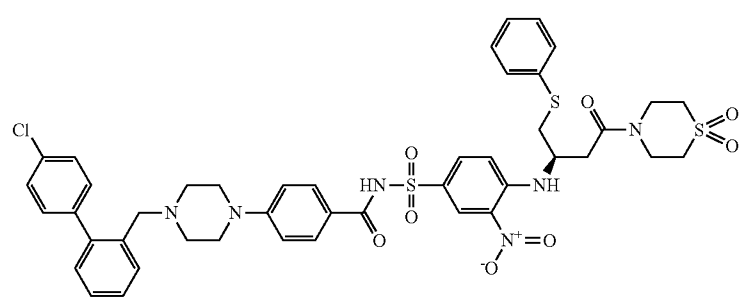 |
| (3R)-3-(4-(((4-(4-((4'-chloro(1,1'-biphenyl)-2-yl)methyl)piperazin-1-yl)benzoyl)amino)sulfonyl)-2-nitroanilino)-4-(phenylsulfanyl)butanamide | 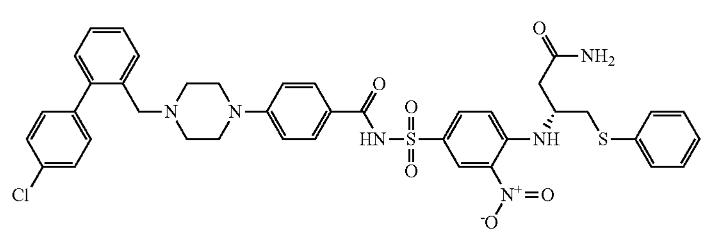 |

-continued

| Name | Structure |
|---|---|
| (3R)-3-(4-(((4-(4-((4'-chloro(1,1'-biphenyl)-2-yl)methyl)piperazin-1-yl)benzoyl)amino)sulfonyl)-2-nitroanilino)-N-cyclopropyl-4-(phenylsulfanyl)butanamide | 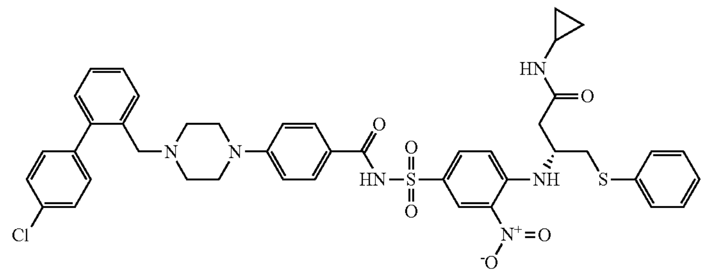 |
| (3R)-3-(4-(((4-(4-((4'-chloro(1,1'-biphenyl)-2-yl)methyl)piperazin-1-yl)benzoyl)amino)sulfonyl)-2-nitroanilino)-N-cyclobutyl-4-(phenylsulfanyl)butanamide | 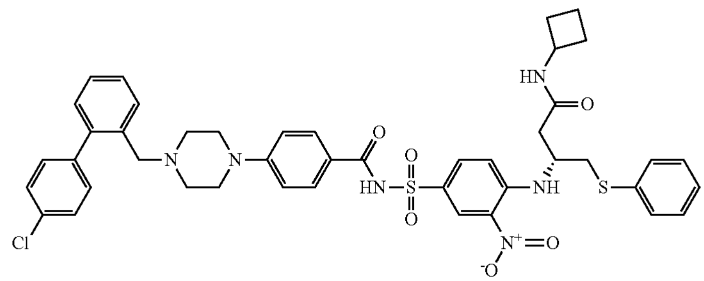 |
| N-(4-(4-((4'-chloro(1,1'-biphenyl)-2-yl)methyl)piperazin-1-yl)benzoyl)-4-(((1R)-3-(4-methylpiperazin-1-yl)-3-oxo-1-((phenylsulfanyl)methyl)propyl)amino)-3-nitrobenzenesulfonamide | 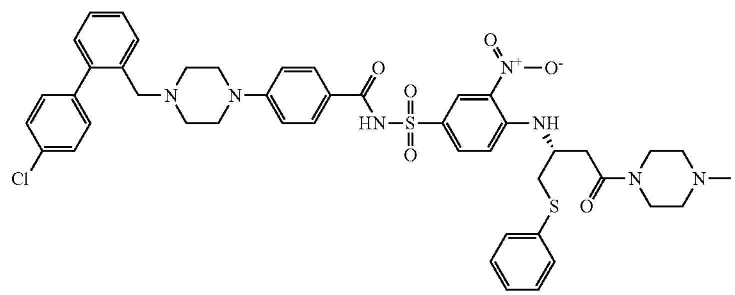 [SMILES: CN1CCN(C(=O)C[C@H](CSc2ccccc2)Nc2ccc(S(=O)(=O)NC(=O)c3ccc(N4CCN(Cc5ccccc5-c5ccc(Cl)cc5)CC4)cc3)cc2[N+](=O)[O-])CC1] |
| N-(4-(4-((4'-chloro(1,1'-biphenyl)-2-yl)methyl)piperazin-1-yl)benzoyl)-4-(((1R)-3-(morpholin-4-yl)-3-oxo-1-((phenylsulfanyl)methyl)propyl)amino)-3-nitrobenzenesulfonamide | 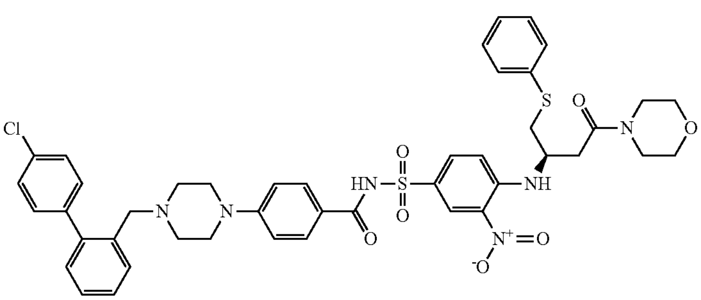 |
| 4-(((1R)-3-(azetidin-1-yl)-3-oxo-1-((phenylsulfanyl)methyl)propyl)amino)-N-(4-(4-((4'-chloro(1,1'-biphenyl)-2-yl)methyl)piperazin-1-yl)benzoyl)-3-nitrobenzenesulfonamide | 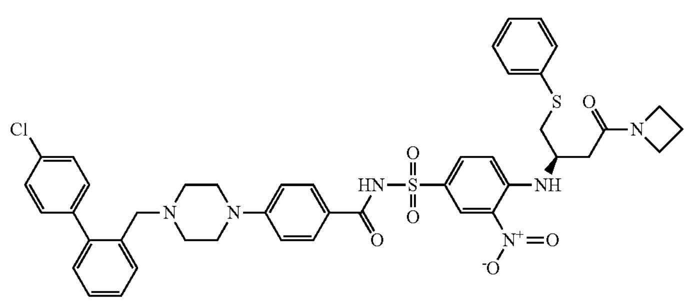 |

| Name | Structure |
|---|---|
| (3R)-3-(4-(((4-(4-((4'-chloro(1,1'-biphenyl)-2-yl)methyl)piperazin-1-yl)benzoyl)amino)sulfonyl)-2-nitroanilino)-N-(2-(morpholin-4-yl)ethyl)-4-(phenylsulfanyl)butanamide | 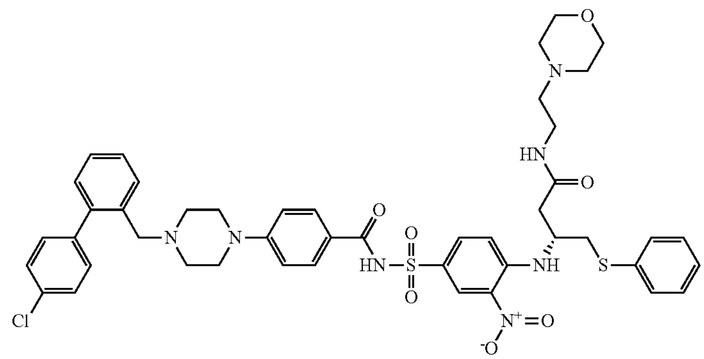 |
| (3R)-3-(4-(((4-(4-((4'-chloro(1,1'-biphenyl)-2-yl)methyl)piperazin-1-yl)benzoyl)amino)sulfonyl)-2-nitroanilino)-N-methyl-4-(phenylsulfanyl)butanamide | 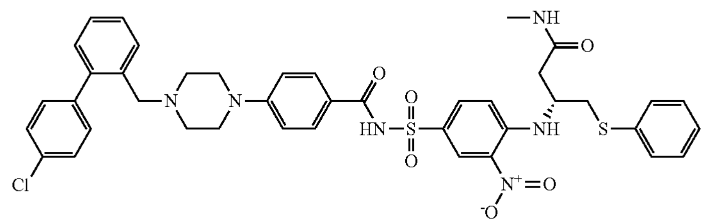 |
| 4-(((1R)-3-amino-1-((phenylsulfanyl)methyl)propyl)amino)-N-(4-(4-((4'-chloro(1,1'-biphenyl)-2-yl)methyl)piperazin-1-yl)benzoyl)-3-nitrobenzenesulfonamide | 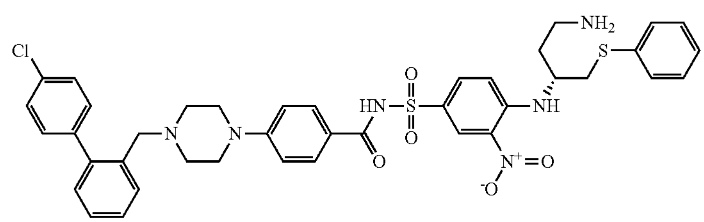 |
| N-(4-(4-((4'-chloro(1,1'-biphenyl)-2-yl)methyl)piperazin-1-yl)benzoyl)-4-(((1R)-3-cyano-1-((phenylsulfanyl)methyl)propyl)amino)-3-nitrobenzenesulfonamide | 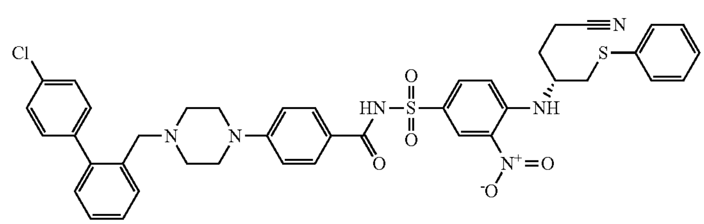 |
| 4-(((1R)-3-(tert-butylamino)-1-((phenylsulfanyl)methyl)propyl)amino)-N-(4-(4-((4'-chloro(1,1'-biphenyl)-2-yl)methyl)piperazin-1-yl)benzoyl)-3-nitrobenzenesulfonamide | 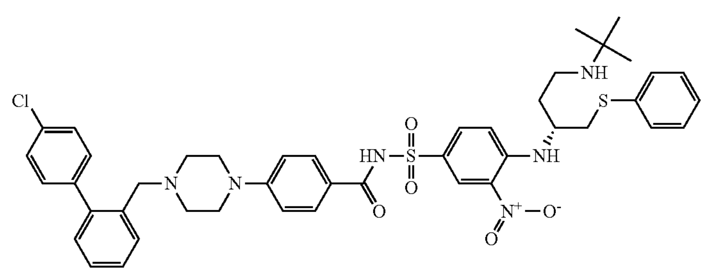 [SMILES: CC(C)(C)NCC[C@H](CSc1ccccc1)Nc1ccc(S(=O)(=O)NC(=O)c2ccc(N3CCN(Cc4ccccc4-c4ccc(Cl)cc4)CC3)cc2)cc1[N+](=O)[O-]] |
| N-(4-(4-((4'-chloro(1,1'-biphenyl)-2-yl)methyl)piperazin-1-yl)benzoyl)-4-(((1R)-3-(cyclopropylamino)-1-((phenylsulfanyl)methyl)propyl)amino)-3-nitrobenzenesulfonamide | 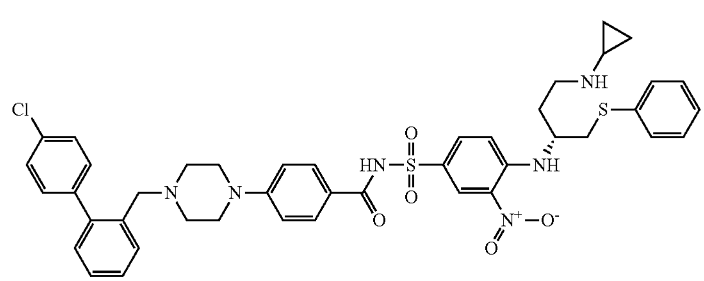 [SMILES: O=C(NS(=O)(=O)c1ccc(N[C@H](CCNC2CC2)CSc2ccccc2)c([N+](=O)[O-])c1)c1ccc(N2CCN(Cc3ccccc3-c3ccc(Cl)cc3)CC2)cc1] |

| Name | Structure |
|---|---|
| N-(4-(4-((4'-chloro(1,1'-biphenyl)-2-yl)methyl)piperazin-1-yl)benzoyl)-4-(((1R)-3-(cyclobutylamino)-1-((phenylsulfanyl)methyl)propyl)amino)-3-nitrobenzenesulfonamide | 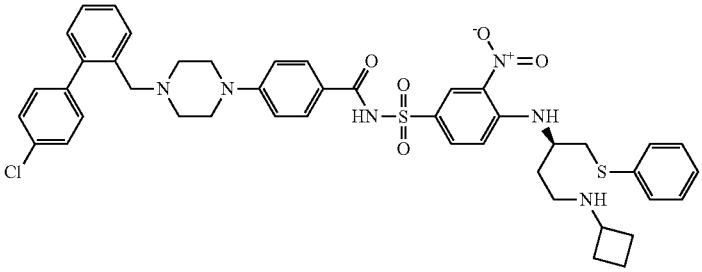 |
| N-(4-(4-((4'-chloro(1,1'-biphenyl)-2-yl)methyl)piperazin-1-yl)benzoyl)-4-(((1R)-3-(diethylamino)-1-((phenylsulfanyl)methyl)propyl)amino)-3-nitrobenzenesulfonamide | 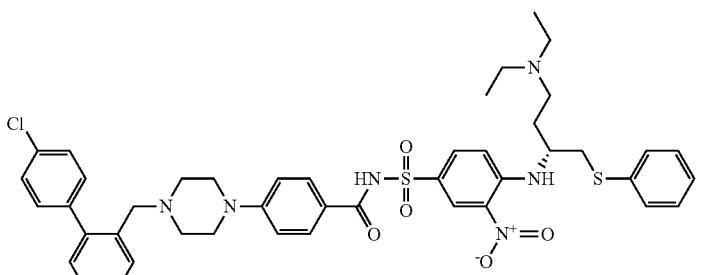 |
| N-(4-(4-((4'-chloro(1,1'-biphenyl)-2-yl)methyl)piperazin-1-yl)benzoyl)-4-(((1R)-3-(isopropyl(methyl)amino)-1-((phenylsulfanyl)methyl)propyl)amino)-3-nitrobenzenesulfonamide | 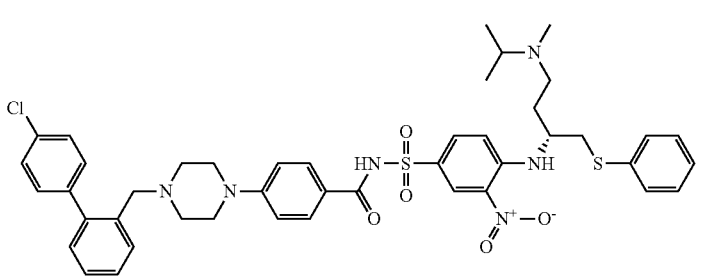 [SMILES: CC(C)N(C)CC[C@H](CSc1ccccc1)Nc1ccc(S(=O)(=O)NC(=O)c2ccc(N3CCN(Cc4ccccc4-c4ccc(Cl)cc4)CC3)cc2)cc1[N+](=O)[O-]] |
| 4-(((1R)-3-(tert-butyl(methyl)amino)-1-((phenylsulfanyl)methyl)propyl)amino)-N-(4-(4-((4'-chloro(1,1'-biphenyl)-2-yl)methyl)piperazin-1-yl)benzoyl)-3-nitrobenzenesulfonamide | 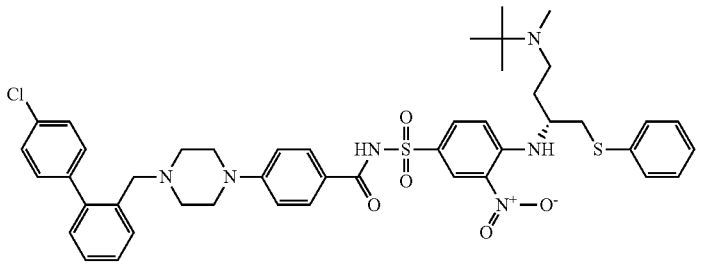 [SMILES: CN(CC[C@H](CSc1ccccc1)Nc1ccc(S(=O)(=O)NC(=O)c2ccc(N3CCN(Cc4ccccc4-c4ccc(Cl)cc4)CC3)cc2)cc1[N+](=O)[O-])C(C)(C)C] |
| N-(4-(4-((4'-chloro(1,1'-biphenyl)-2-yl)methyl)piperazin-1-yl)benzoyl)-3-nitro-4-(((1R)-1-((phenylsulfanyl)methyl)-3-(piperidin-1-yl)propyl)amino)benzenesulfonamide | 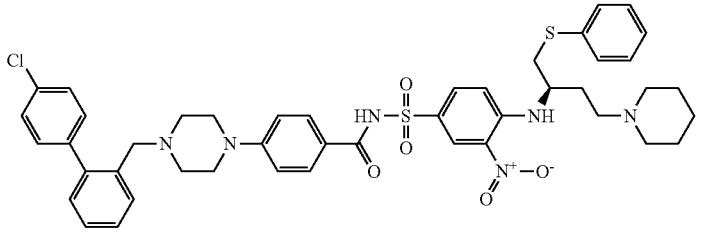 [SMILES: O=C(NS(=O)(=O)c1ccc(N[C@H](CCN2CCCCC2)CSc2ccccc2)c([N+](=O)[O-])c1)c1ccc(N2CCN(Cc3ccccc3-c3ccc(Cl)cc3)CC2)cc1] |
| N-(4-(4-((4'-chloro(1,1'-biphenyl)-2-yl)methyl)piperazin-1-yl)benzoyl)-4-(((1R)-3-(4-hydroxypiperidin-1-yl)-1-((phenylsulfanyl)methyl)propyl)amino)-3-nitrobenzenesulfonamide | 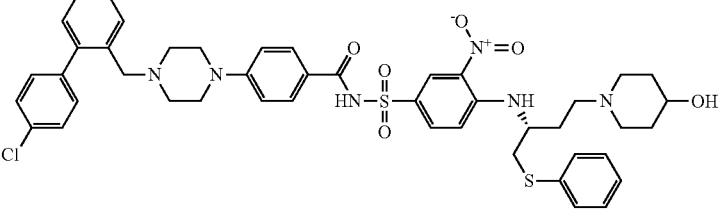 |

| Name | Structure |
|---|---|
| 4-(((1R)-3-(4-acetylpiperazin-1-yl)-1-((phenylsulfanyl)methyl)propyl)amino)-N-(4-(4-((4'-chloro(1,1'-biphenyl)-2-yl)methyl)piperazin-1-yl)benzoyl)-3-nitrobenzenesulfonamide | 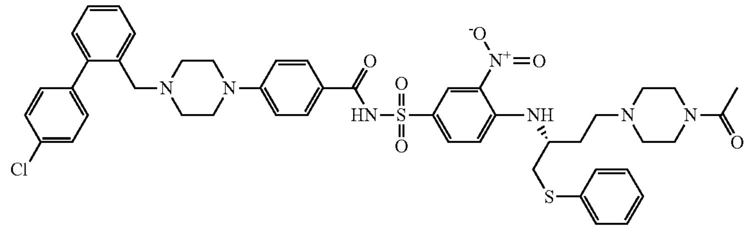 |
| N-(4-(4-((4'-chloro(1,1'-biphenyl)-2-yl)methyl)piperazin-1-yl)benzoyl)-3-nitro-4-(((1R)-1-((phenylsulfanyl)methyl)-3-(thiomorpholin-4-yl)propyl)amino)benzenesulfonamide | 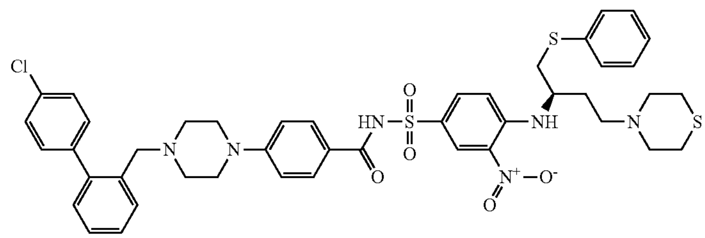 [SMILES: O=C(NS(=O)(=O)c1ccc(N[C@H](CCN2CCSCC2)CSc2ccccc2)c([N+](=O)[O-])c1)c1ccc(N2CCN(Cc3ccccc3-c3ccc(Cl)cc3)CC2)cc1] |
| N-(4-(4-((4'-chloro(1,1'-biphenyl)-2-yl)methyl)piperazin-1-yl)benzoyl)-4-(((1R)-3-((2-(morpholin-4-yl)ethyl)amino)-1-((phenylsulfanyl)methyl)propyl)amino)-3-nitrobenzenesulfonamide | 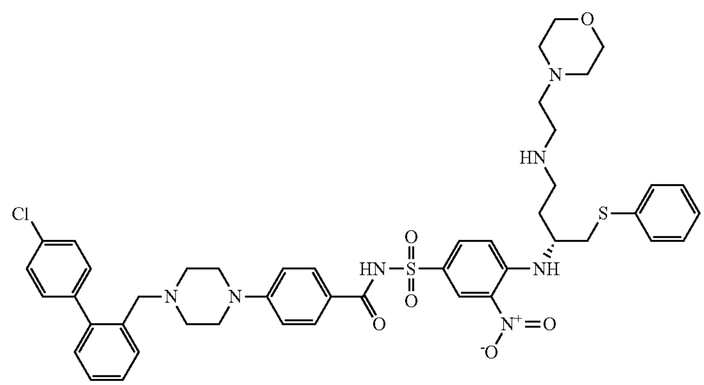 |
| N-(4-(4-((4'-chloro(1,1'-biphenyl)-2-yl)methyl)piperazin-1-yl)benzoyl)-3-nitro-4-(((1R)-1-((phenylsulfanyl)methyl)-3-(piperazin-1-yl)propyl)amino)benzenesulfonamide | 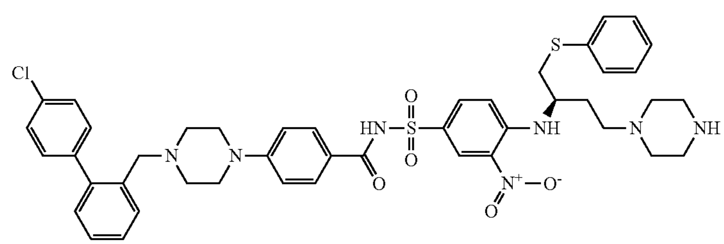 [SMILES: O=C(NS(=O)(=O)c1ccc(N[C@H](CCN2CCNCC2)CSc2ccccc2)c([N+](=O)[O-])c1)c1ccc(N2CCN(Cc3ccccc3-c3ccc(Cl)cc3)CC2)cc1] |
| N-(4-(4-((4'-chloro(1,1'-biphenyl)-2-yl)methyl)piperazin-1-yl)benzoyl)-4-(((1R)-3-((3R)-3-hydroxypyrrolidin-1-yl)-1-((phenylsulfanyl)methyl)propyl)amino)-3-nitrobenzenesulfonamide | 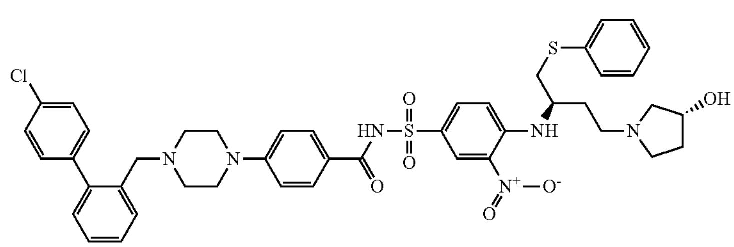 [SMILES: O=C(NS(=O)(=O)c1ccc(N[C@H](CCN2CC[C@@H](O)C2)CSc2ccccc2)c([N+](=O)[O-])c1)c1ccc(N2CCN(Cc3ccccc3-c3ccc(Cl)cc3)CC2)cc1] |
| 4-(((1R)-3-((3R)-3-aminopyrrolidin-1-yl)-1-((phenylsulfanyl)methyl)propyl)amino)-N-(4-(4-((4'-chloro(1,1'-biphenyl)-2-yl)methyl)piperazin-1-yl)benzoyl)-3-nitrobenzenesulfonamide | 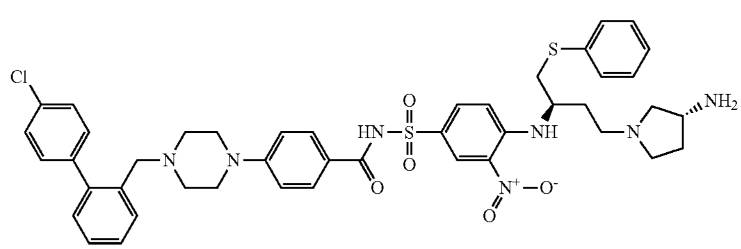 [SMILES: N[C@@H]1CCN(CC[C@H](CSc2ccccc2)Nc2ccc(S(=O)(=O)NC(=O)c3ccc(N4CCN(Cc5ccccc5-c5ccc(Cl)cc5)CC4)cc3)cc2[N+](=O)[O-])C1] |

-continued

| Name | Structure |
|---|---|
| N-(4-(4-((4'-chloro(1,1'-biphenyl)-2-yl)methyl)piperazin-1-yl)benzoyl)-4-(((1R)-3-(3-hydroxyazetidin-1-yl)-1-((phenylsulfanyl)methyl)propyl)amino)-3-nitrobenzenesulfonamide | 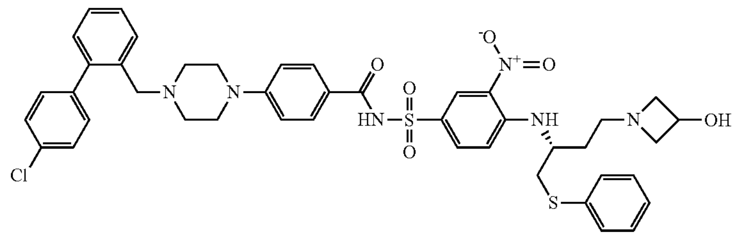 |
| N-(4-(4-((4'-chloro(1,1'-biphenyl)-2-yl)methyl)piperazin-1-yl)benzoyl)-4-(((1R)-3-(4-methylpiperazin-1-yl)-1-((phenylsulfanyl)methyl)propyl)amino)-3-nitrobenzenesulfonamide | 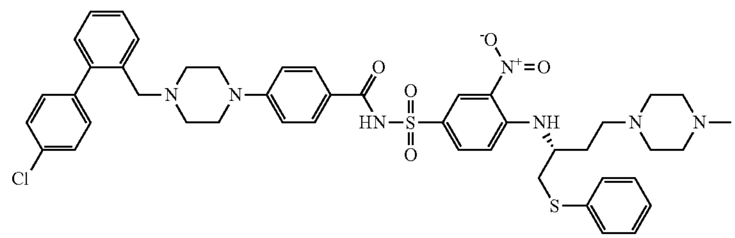 |
| N-(4-(4-((4'-chloro(1,1'-biphenyl)-2-yl)methyl)piperazin-1-yl)benzoyl)-4-(((1R)-3-(1,1-dioxidothiomorpholin-4-yl)-1-((phenylsulfanyl)methyl)propyl)amino)-3-nitrobenzenesulfonamide | 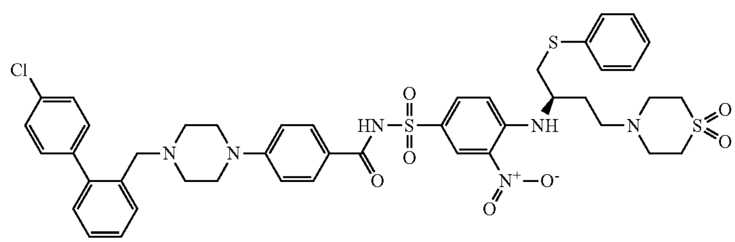 [SMILES: O=C(NS(=O)(=O)c1ccc(N[C@H](CCN2CCS(=O)(=O)CC2)CSc2ccccc2)c([N+](=O)[O-])c1)c1ccc(N2CCN(Cc3ccccc3-c3ccc(Cl)cc3)CC2)cc1] |
| 4-(((1R)-3-(1,3-benzodioxol-5-ylamino)-1-((phenylsulfanyl)methyl)propyl)amino)-N-(4-(4-((4'-chloro(1,1'-biphenyl)-2-yl)methyl)piperazin-1-yl)benzoyl)-3-nitrobenzenesulfonamide | 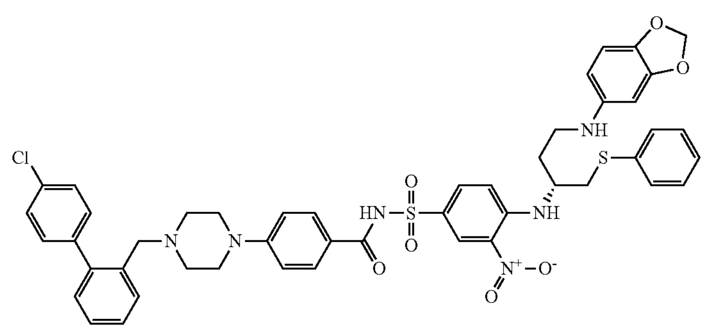 [SMILES: O=C(NS(=O)(=O)c1ccc(N[C@H](CCNc2ccc3c(c2)OCO3)CSc2ccccc2)c([N+](=O)[O-])c1)c1ccc(N2CCN(Cc3ccccc3-c3ccc(Cl)cc3)CC2)cc1] |
| 4-(((1R)-3-((1,3-benzodioxol-4-ylmethyl)amino)-1-((phenylsulfanyl)methyl)propyl)amino)-N-(4-(4-((4'-chloro(1,1'-biphenyl)-2-yl)methyl)piperazin-1-yl)benzoyl)-3-nitrobenzenesulfonamide | 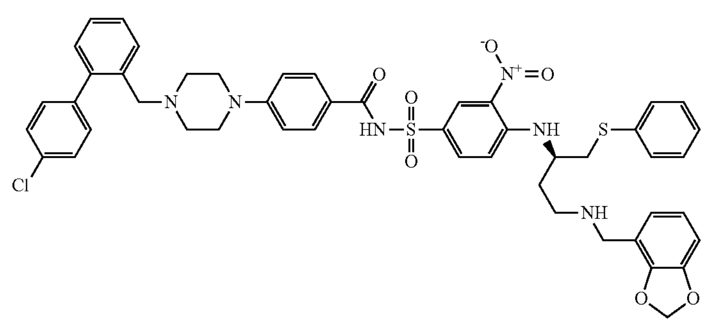 |

-continued

| Name | Structure |
|---|---|
| N-(4-(4-((4'-chloro(1,1'-biphenyl)-2-yl)methyl)piperazin-1-yl)benzoyl)-3-nitro-4-(((1R)-1-((phenylsulfanyl)methyl)-3-((pyridin-2-ylmethyl)amino)propyl)amino)benzenesulfonamide | 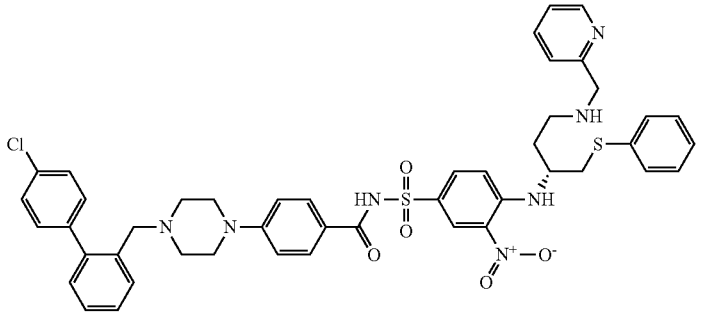 [SMILES: O=C(NS(=O)(=O)c1ccc(N[C@H](CCNCc2ccccn2)CSc2ccccc2)c([N+](=O)[O-])c1)c1ccc(N2CCN(Cc3ccccc3-c3ccc(Cl)cc3)CC2)cc1] |
| N-(4-(4-((4'-chloro(1,1'-biphenyl)-2-yl)methyl)piperazin-1-yl)benzoyl)-3-nitro-4-(((1R)-1-((phenylsulfanyl)methyl)-3-((2-(pyridin-2-yl)ethyl)amino)propyl)amino)benzenesulfonamide | 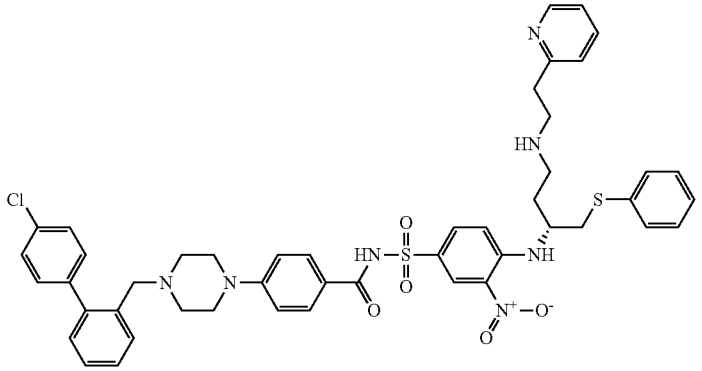 [SMILES: O=C(NS(=O)(=O)c1ccc(N[C@H](CCNCCc2ccccn2)CSc2ccccc2)c([N+](=O)[O-])c1)c1ccc(N2CCN(Cc3ccccc3-c3ccc(Cl)cc3)CC2)cc1] |
| N-(4-(4-((4'-chloro(1,1'-biphenyl)-2-yl)methyl)piperazin-1-yl)benzoyl)-3-nitro-4-(((1R)-1-((phenylsulfanyl)methyl)-3-((pyridin-4-ylmethyl)amino)propyl)amino)benzenesulfonamide | 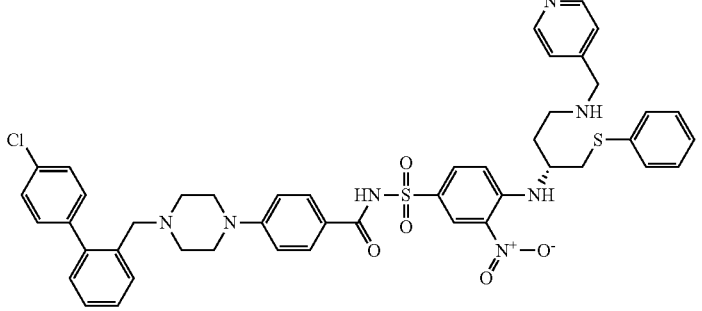 |
| N-(4-(4-((4'-chloro(1,1'-biphenyl)-2-yl)methyl)piperazin-1-yl)benzoyl)-4-(((1R)-3-(morpholin-4-ylamino)-1-((phenylsulfanyl)methyl)propyl)amino)-3-nitrobenzenesulfonamide | 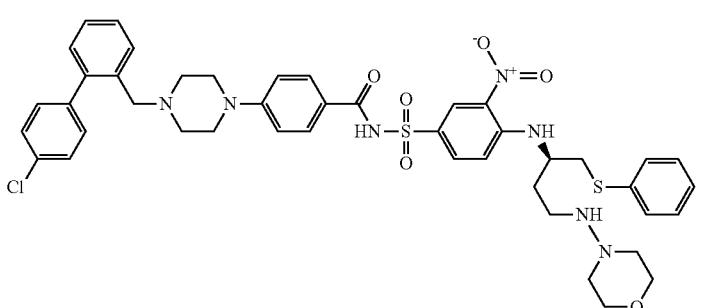 |

| Name | Structure |
| --- | --- |
| N-(4-(4-((4'-chloro(1,1'-biphenyl)-2-yl)methyl)piperazin-1-yl)benzoyl)-4-(((1R)-3-(methyl(pyridin-4-yl)amino)-1-((phenylsulfanyl)methyl)propyl)amino)-3-nitrobenzenesulfonamide | 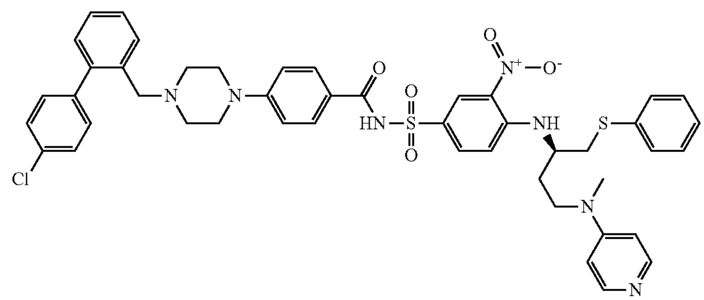 [SMILES: CN(CC[C@H](CSc1ccccc1)Nc1ccc(S(=O)(=O)NC(=O)c2ccc(N3CCN(Cc4ccccc4-c4ccc(Cl)cc4)CC3)cc2)cc1[N+](=O)[O-])c1ccncc1] |
| N-(4-(4-((4'-chloro(1,1'-biphenyl)-2-yl)methyl)piperazin-1-yl)benzoyl)-3-nitro-4-(((1R)-1-((phenylsulfanyl)methyl)-3-(pyridin-3-ylamino)propyl)amino)benzenesulfonamide | 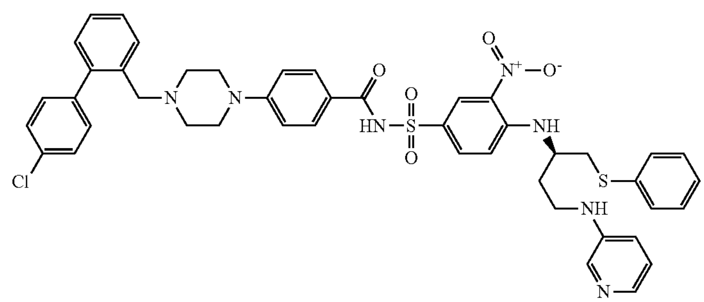 [SMILES: O=C(NS(=O)(=O)c1ccc(N[C@H](CCNc2cccnc2)CSc2ccccc2)c([N+](=O)[O-])c1)c1ccc(N2CCN(Cc3ccccc3-c3ccc(Cl)cc3)CC2)cc1] |
| N-(4-(4-((4'-chloro(1,1'-biphenyl)-2-yl)methyl)piperazin-1-yl)benzoyl)-4-(((1R)-3-(2,6-dimethylpiperidin-1-yl)-1-((phenylsulfanyl)methyl)propyl)amino)-3-nitrobenzenesulfonamide | 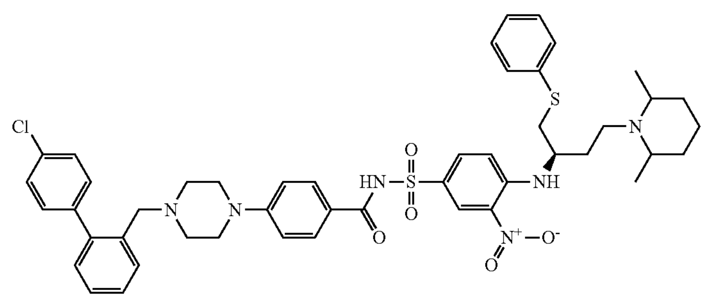 [SMILES: CC1CCCC(C)N1CC[C@H](CSc1ccccc1)Nc1ccc(S(=O)(=O)NC(=O)c2ccc(N3CCN(Cc4ccccc4-c4ccc(Cl)cc4)CC3)cc2)cc1[N+](=O)[O-]] |
| N-(4-(4-((4'-chloro(1,1'-biphenyl)-2-yl)methyl)piperazin-1-yl)benzoyl)-4-(((1R)-3-((2R,6S)-2,6-dimethylpiperidin-1-yl)-1-((phenylsulfanyl)methyl)propyl)amino)-3-nitrobenzenesulfonamide | 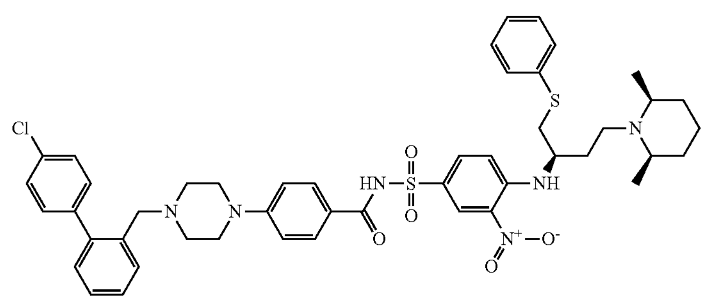 [SMILES: C[C@@H]1CCC[C@H](C)N1CC[C@H](CSc1ccccc1)Nc1ccc(S(=O)(=O)NC(=O)c2ccc(N3CCN(Cc4ccccc4-c4ccc(Cl)cc4)CC3)cc2)cc1[N+](=O)[O-]] |
| N-(4-(4-((4'-chloro(1,1'-biphenyl)-2-yl)methyl)piperazin-1-yl)benzoyl)-3-nitro-4-(((1R)-1-((phenylsulfanyl)methyl)-3-(pyrrolidin-1-ylamino)propyl)amino)benzenesulfonamide | 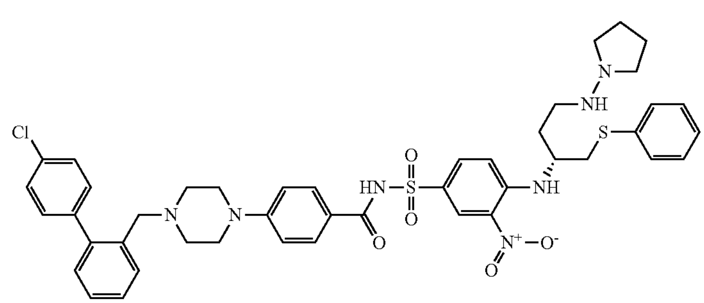 [SMILES: O=C(NS(=O)(=O)c1ccc(N[C@H](CCNN2CCCC2)CSc2ccccc2)c([N+](=O)[O-])c1)c1ccc(N2CCN(Cc3ccccc3-c3ccc(Cl)cc3)CC2)cc1] |

-continued

| Name | Structure |
|---|---|
| N-(4-(4-((4'-chloro(1,1'-biphenyl)-2-yl)methyl)piperazin-1-yl)benzoyl)-4-(((1R)-3-(4-(methoxyimino)piperidin-1-yl)-1-((phenylsulfanyl)methyl)propyl)amino)-3-nitrobenzenesulfonamide | 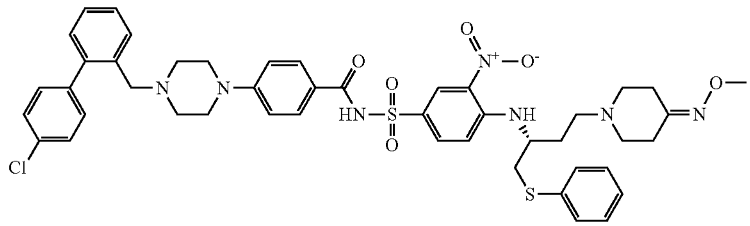 [SMILES: CON=C1CCN(CC[C@H](CSc2ccccc2)Nc2ccc(S(=O)(=O)NC(=O)c3ccc(N4CCN(Cc5ccccc5-c5ccc(Cl)cc5)CC4)cc3)cc2[N+](=O)[O-])CC1] |
| N-(4-(4-((4'-chloro(1,1'-biphenyl)-2-yl)methyl)piperazin-1-yl)benzoyl)-3-nitro-4-(((1R)-1-((phenylsulfanyl)methyl)-3-(2H-tetrazol-5-yl)propyl)amino)benzenesulfonamide | 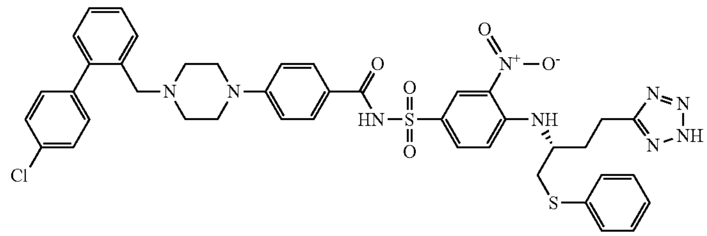 [SMILES: O=C(NS(=O)(=O)c1ccc(N[C@H](CCc2nn[nH]n2)CSc2ccccc2)c([N+](=O)[O-])c1)c1ccc(N2CCN(Cc3ccccc3-c3ccc(Cl)cc3)CC2)cc1] |
| N-(4-(4-((4'-chloro(1,1'-biphenyl)-2-yl)methyl)piperazin-1-yl)benzoyl)-4-(((1R)-3-(diisopropylamino)-1-((phenylsulfanyl)methyl)propyl)amino)-3-(trifluoromethyl)benzenesulfonamide | 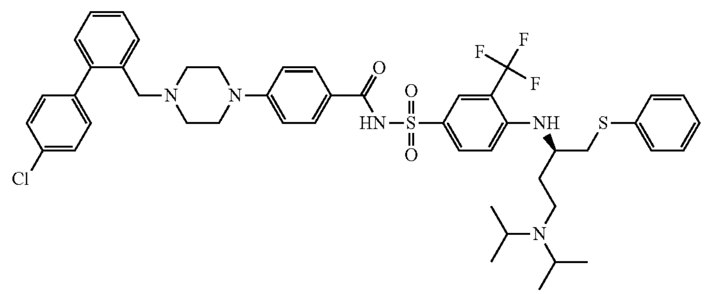 [SMILES: CC(C)N(CC[C@H](CSc1ccccc1)Nc1ccc(S(=O)(=O)NC(=O)c2ccc(N3CCN(Cc4ccccc4-c4ccc(Cl)cc4)CC3)cc2)cc1C(F)(F)F)C(C)C] |
| N-(4-(4-((4'-chloro(1,1'-biphenyl)-2-yl)methyl)piperazin-1-yl)benzoyl)-4-(((1R)-3-(isopropylamino)-1-((phenylsulfanyl)methyl)propyl)amino)-3-(trifluoromethyl)benzenesulfonamide | 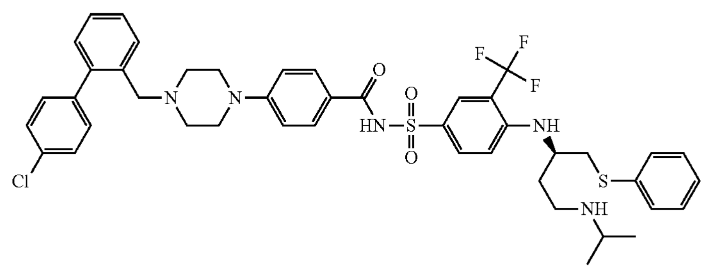 [SMILES: CC(C)NCC[C@H](CSc1ccccc1)Nc1ccc(S(=O)(=O)NC(=O)c2ccc(N3CCN(Cc4ccccc4-c4ccc(Cl)cc4)CC3)cc2)cc1C(F)(F)F] |
| 4-(((1R)-3-(bis(2-hydroxyethyl)amino)-1-((phenylsulfanyl)methyl)propyl)amino)-N-(4-(4-((4'-chloro(1,1'-biphenyl)-2-yl)methyl)piperazin-1-yl)benzoyl)-3-nitrobenzenesulfonamide | 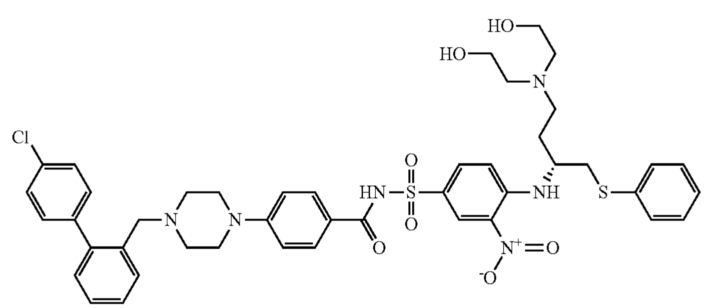 |
| N-(4-(4-((4'-chloro(1,1'-biphenyl)-2-yl)methyl)piperazin-1-yl)benzoyl)-3-(((1R)-3-(dimethylamino)-1-((phenylsulfanyl)methyl)propyl)amino)-4-(trifluoromethoxy)benzenesulfonamide | 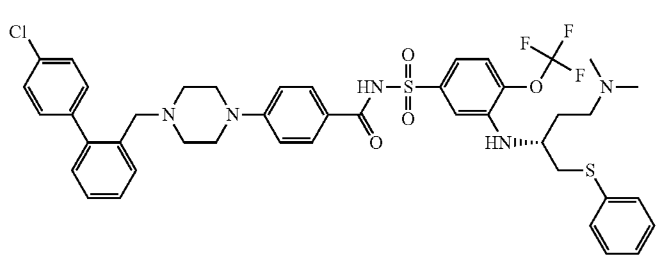 [SMILES: CN(C)CC[C@H](CSc1ccccc1)Nc1cc(S(=O)(=O)NC(=O)c2ccc(N3CCN(Cc4ccccc4-c4ccc(Cl)cc4)CC3)cc2)ccc1OC(F)(F)F] |

| Name | Structure |
|---|---|
| N-(4-(4-((4'-chloro(1,1'-biphenyl)-2-yl)methyl)piperazin-1-yl)benzoyl)-4-(((1R)-3-(isopropyl(methyl)amino)-1-((phenylsulfanyl)methyl)propyl)amino)-3-(trifluoromethyl)benzenesulfonamide | 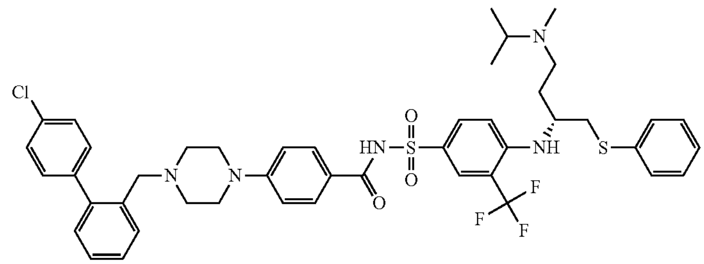 [SMILES: CC(C)N(C)CC[C@H](CSc1ccccc1)Nc1ccc(S(=O)(=O)NC(=O)c2ccc(N3CCN(Cc4ccccc4-c4ccc(Cl)cc4)CC3)cc2)cc1C(F)(F)F] |
| N-(4-(4-((4'-chloro(1,1'-biphenyl)-2-yl)methyl)piperazin-1-yl)benzoyl)-4-(((1R)-3-(diethylamino)-1-((phenylsulfanyl)methyl)propyl)amino)-3-(trifluoromethyl)benzenesulfonamide | 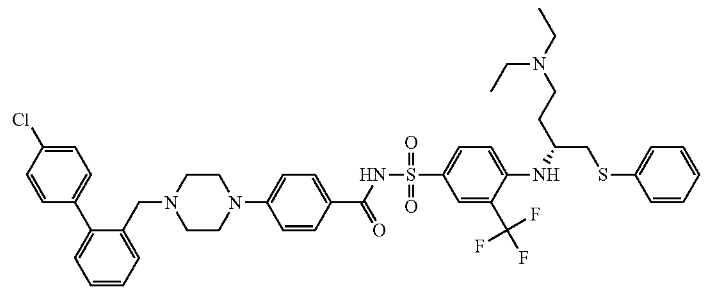 [SMILES: CCN(CC)CC[C@H](CSc1ccccc1)Nc1ccc(S(=O)(=O)NC(=O)c2ccc(N3CCN(Cc4ccccc4-c4ccc(Cl)cc4)CC3)cc2)cc1C(F)(F)F] |
| N-(4-(4-((4'-chloro(1,1'-biphenyl)-2-yl)methyl)piperazin-1-yl)benzoyl)-4-(((1R)-3-(2,5-dimethylpyrrolidin-1-yl)-1-((phenylsulfanyl)methyl)propyl)amino)-3-nitrobenzenesulfonamide | 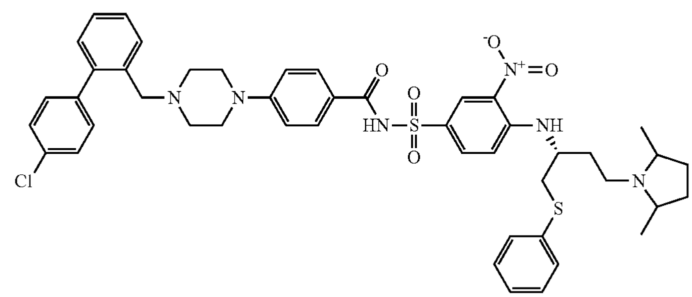 |
| 4-(((1R)-3-amino-1-((phenylsulfanyl)methyl)propyl)amino)-N-(4-(4-((4'-chloro(1,1'-biphenyl)-2-yl)methyl)piperazin-1-yl)benzoyl)-3-(trifluoromethyl)benzenesulfonamide | 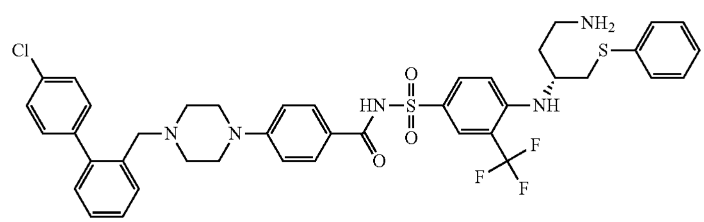 |
| N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-2-(trifluoromethyl)benzenesulfonamide | 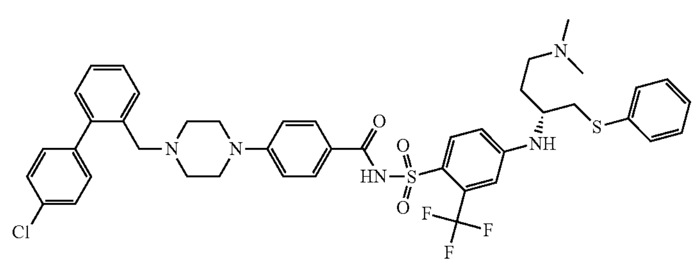 [SMILES: CN(C)CC[C@H](CSc1ccccc1)Nc1ccc(S(=O)(=O)NC(=O)c2ccc(N3CCN(Cc4ccccc4-c4ccc(Cl)cc4)CC3)cc2)c(C(F)(F)F)c1] |
| N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-fluorobenzenesulfonamide | 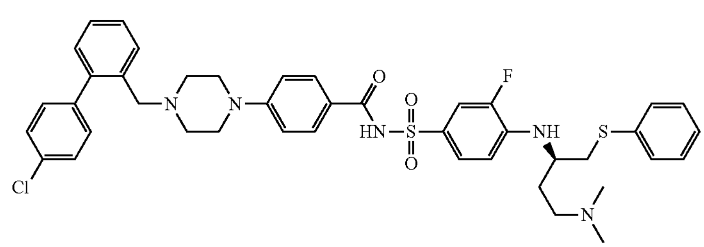 |

-continued

| Name | Structure |
|---|---|
| N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-2-(trifluoromethoxy)benzenesulfonamide | 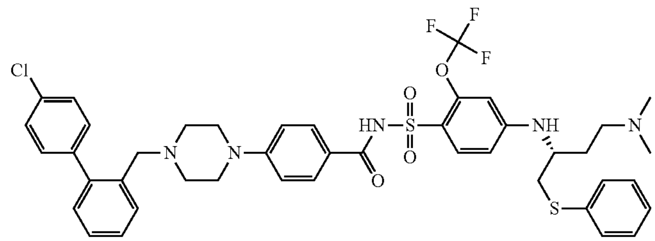 [SMILES: CN(C)CC[C@H](CSc1ccccc1)Nc1ccc(S(=O)(=O)NC(=O)c2ccc(N3CCN(Cc4ccccc4-c4ccc(Cl)cc4)CC3)cc2)c(OC(F)(F)F)c1] |
| N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-2,5-difluorobenzenesulfonamide | 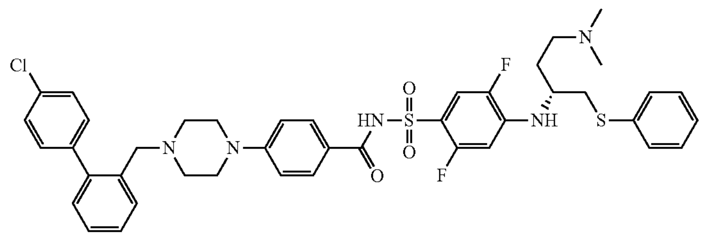 [SMILES: CN(C)CC[C@H](CSc1ccccc1)Nc1cc(F)c(S(=O)(=O)NC(=O)c2ccc(N3CCN(Cc4ccccc4-c4ccc(Cl)cc4)CC3)cc2)cc1F] |
| N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-methylbenzenesulfonamide | 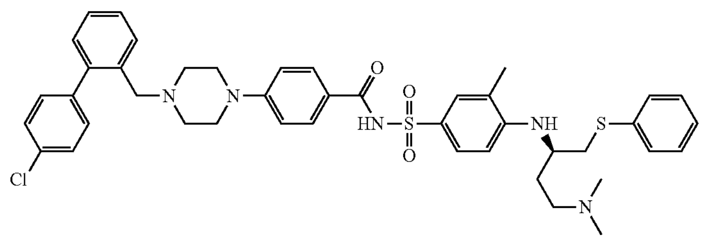 [SMILES: Cc1cc(S(=O)(=O)NC(=O)c2ccc(N3CCN(Cc4ccccc4-c4ccc(Cl)cc4)CC3)cc2)ccc1N[C@H](CCN(C)C)CSc1ccccc1] |
| N-(4-(4-((2-(4-chlorophenyl)-1-cyclohexen-1-yl)methyl)piperazin-1-yl)benzoyl)-4-(((1R)-3-(diisopropylamino)-1-((phenylsulfanyl)methyl)propyl)amino)-3-nitrobenzenesulfonamide | 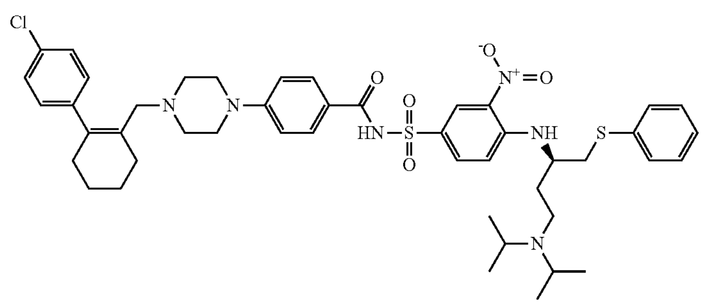 |
| N-(4-(4-((4'-chloro(1,1'-biphenyl)-2-yl)methyl)piperazin-1-yl)benzoyl)-4-(((1R)-3-((2R,5R)-2,5-dimethylpyrrolidin-1-yl)-1-((phenylsulfanyl)methyl)propyl)amino)-3-nitrobenzenesulfonamide | 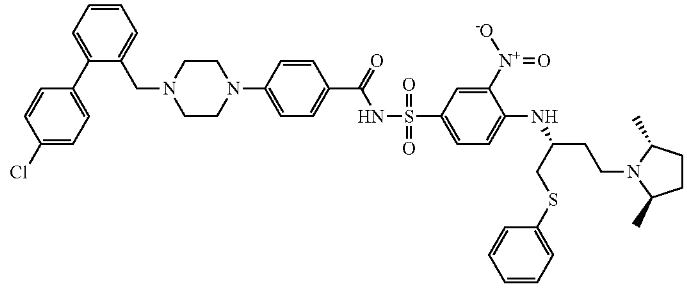 |

| Name | Structure |
|---|---|
| N-(4-(4-((4'-chloro(1,1'-biphenyl)-2-yl)methyl)piperazin-1-yl)benzoyl)-4-(((1R)-3-((2S,5S)-2,5-dimethylpyrrolidin-1-yl)-1-((phenylsulfanyl)methyl)propyl)amino)-3-nitrobenzenesulfonamide | 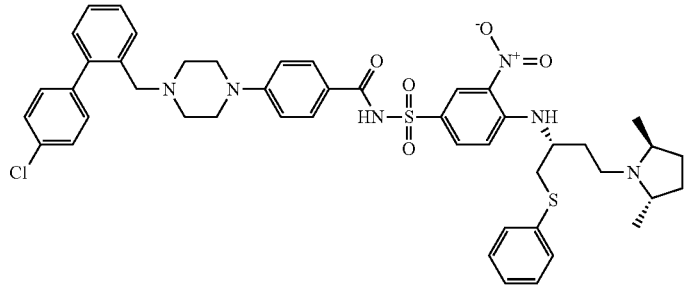 |
| N-(4-(4-((4'-chloro(1,1'-biphenyl)-2-yl)methyl)piperazin-1-yl)benzoyl)-4-(((1R)-3-((2R,5S)-2,5-dimethylpyrrolidin-1-yl)-1-((phenylsulfanyl)methyl)propyl)amino)-3-nitrobenzenesulfonamide | 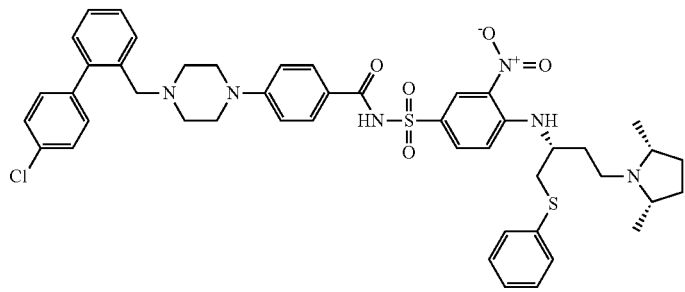 |
| N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitro-5-(trifluoromethyl)benzenesulfonamide | 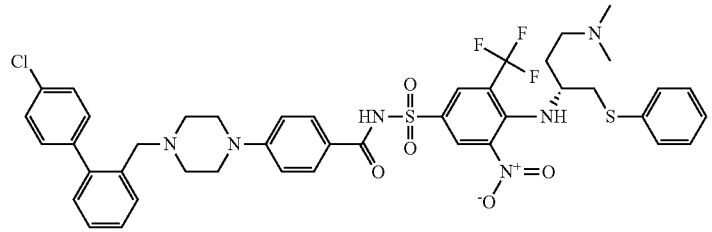 |
| N-(4-(4-((2-(4-chlorophenyl)-1-cyclohexen-1-yl)methyl)piperazin-1-yl)benzoyl)-4-(((1R)-3-(dimethylamino)-1-((phenylsulfanyl)methyl)propyl)amino)-3-nitro-5-(trifluoromethyl)benzenesulfonamide | 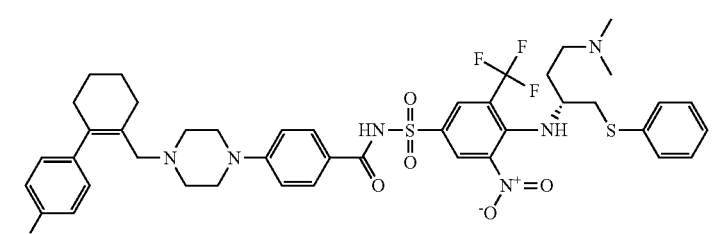 |
| N-(4-(4-((2-(4-chlorophenyl)-1-cyclohepten-1-yl)methyl)piperazin-1-yl)benzoyl)-4-(((1R)-3-(dimethylamino)-1-((phenylsulfanyl)methyl)propyl)amino)-3-nitro-5-(trifluoromethyl)benzenesulfonamide | 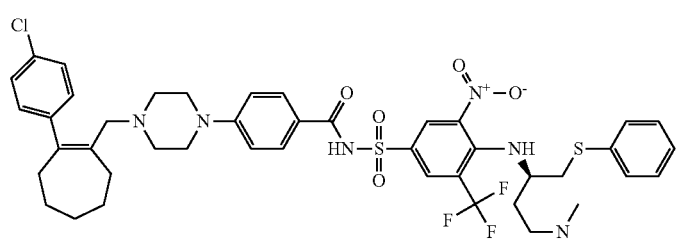 |

-continued

| Name | Structure |
|------|-----------|
| N-(4-(4-((4'-chloro(1,1'-biphenyl)-2-yl)methyl)piperazin-1-yl)benzoyl)-3-(((1R)-3-(dimethylamino)-1-((phenylsulfanyl)methyl)propyl)amino)-4-nitrobenzenesulfonamide | 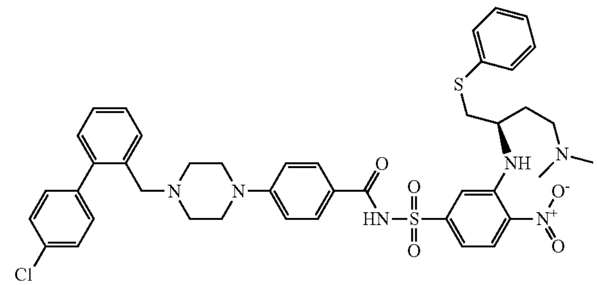 [SMILES: CN(C)CC[C@H](CSc1ccccc1)Nc1cc(S(=O)(=O)NC(=O)c2ccc(N3CCN(Cc4ccccc4-c4ccc(Cl)cc4)CC3)cc2)ccc1[N+](=O)[O-]] |
| N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3,5-difluorobenzenesulfonamide | 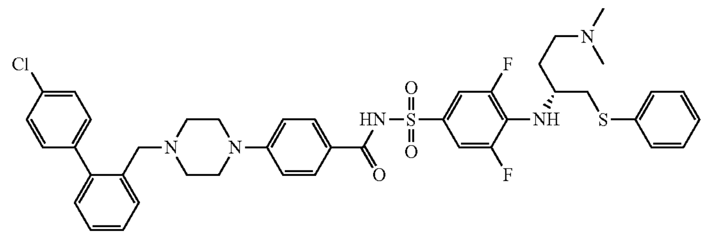 |
| methyl 5-(((4-(4-((4'-chloro(1,1'-biphenyl)-2-yl)methyl)piperazin-1-yl)benzoyl)amino)sulfonyl)-2-(((1R)-3-(dimethylamino)-1-((phenylsulfanyl)methyl)propyl)amino)-3-nitrobenzoate | 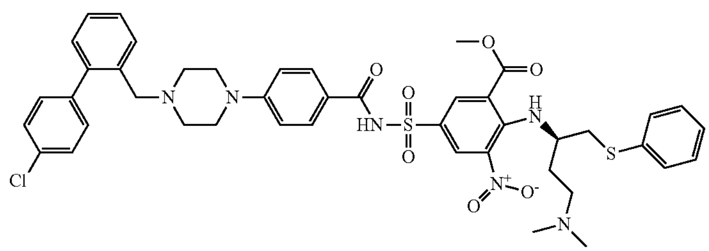 [SMILES: COC(=O)c1cc(S(=O)(=O)NC(=O)c2ccc(N3CCN(Cc4ccccc4-c4ccc(Cl)cc4)CC3)cc2)cc([N+](=O)[O-])c1N[C@H](CCN(C)C)CSc1ccccc1] |
| 5-(((4-(4-((4'-chloro(1,1'-biphenyl)-2-yl)methyl)piperazin-1-yl)benzoyl)amino)sulfonyl)-2-(((1R)-3-(dimethylamino)-1-((phenylsulfanyl)methyl)propyl)amino)-3-nitrobenzoic acid | |
| 5-(((4-(4-((4'-chloro(1,1'-biphenyl)-2-yl)methyl)piperazin-1-yl)benzoyl)amino)sulfonyl)-2-(((1R)-3-(dimethylamino)-1-((phenylsulfanyl)methyl)propyl)amino)-3-nitrobenzoic acid | |
| 5-(((4-(4-((2-(4-chlorophenyl)-1-cyclohexen-1-yl)methyl)piperazin-1-yl)benzoyl)amino)sulfonyl)-2-(((1R)-3-(dimethylamino)-1-((phenylsulfanyl)methyl)propyl)amino)-3-nitrobenzoic acid | 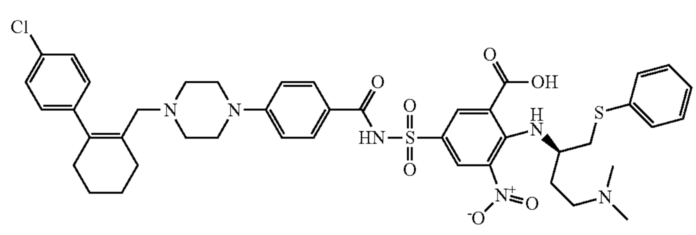 |

-continued

| Name | Structure |
|---|---|
| 5-(((4-(4-((2-(4-chlorophenyl)-1-cyclohexen-1-yl)methyl)piperazin-1-yl)benzoyl)amino)sulfonyl)-2-(((1R)-3-(dimethylamino)-1-((phenylsulfanyl)methyl)propyl)amino)-3-nitrobenzamide | 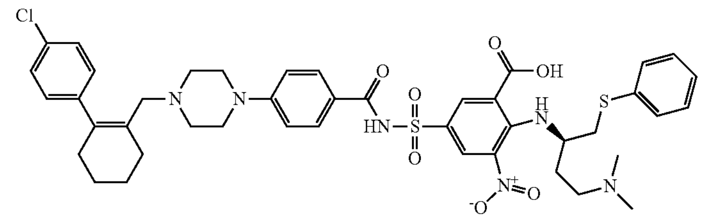 |
| 5-(((4-(4-((4'-chloro(1,1'-biphenyl)-2-yl)methyl)piperazin-1-yl)benzoyl)amino)sulfonyl)-2-(((1R)-3-(dimethylamino)-1-((phenylsulfanyl)methyl)propyl)amino)-3-nitrobenzamide | 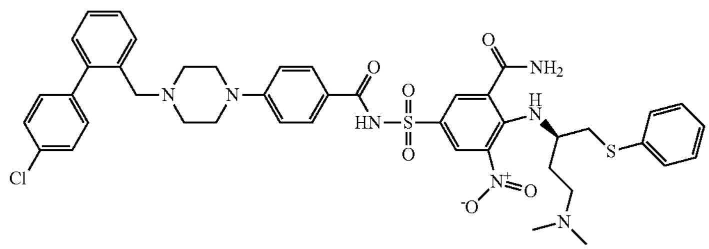 |
| methyl 5-(((4-(4-((2-(4-chlorophenyl)-1-cyclohexen-1-yl)methyl)piperazin-1-yl)benzoyl)amino)sulfonyl)-2-(((1R)-3-(dimethylamino)-1-((phenylsulfanyl)methyl)propyl)amino)-3-(trifluoromethyl)benzoate | 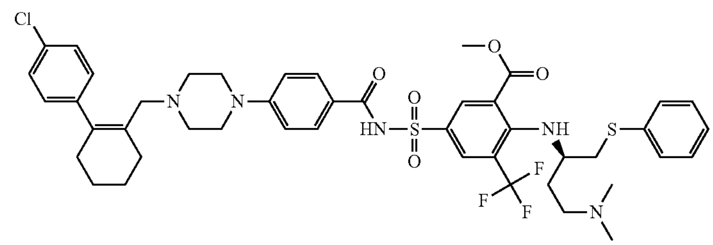 [SMILES: COC(=O)c1cc(S(=O)(=O)NC(=O)c2ccc(N3CCN(CC4=C(c5ccc(Cl)cc5)CCCC4)CC3)cc2)cc(C(F)(F)F)c1N[C@H](CCN(C)C)CSc1ccccc1] |
| methyl 5-(((4-(4-((4-(4-chlorophenyl)-5,6-dihydro-2H-pyran-3-yl)methyl)piperazin-1-yl)benzoyl)amino)sulfonyl)-2-(((1R)-3-(dimethylamino)-1-((phenylsulfanyl)methyl)propyl)amino)-3-(trifluoromethyl)benzoate | 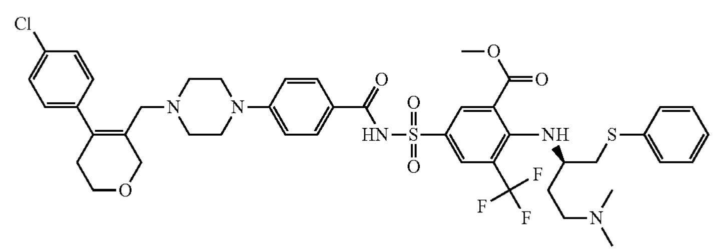 [SMILES: COC(=O)c1cc(S(=O)(=O)NC(=O)c2ccc(N3CCN(CC4=C(c5ccc(Cl)cc5)CCOC4)CC3)cc2)cc(C(F)(F)F)c1N[C@H](CCN(C)C)CSc1ccccc1] |
| methyl 5-(((4-(4-((4'-chloro(1,1'-biphenyl)-2-yl)methyl)piperazin-1-yl)benzoyl)amino)sulfonyl)-2-(((1R)-3-(dimethylamino)-1-((phenylsulfanyl)methyl)propyl)amino)-3-(trifluoromethyl)benzoate | 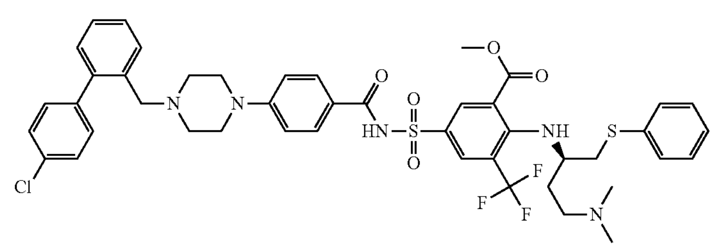 [SMILES: COC(=O)c1cc(S(=O)(=O)NC(=O)c2ccc(N3CCN(Cc4ccccc4-c4ccc(Cl)cc4)CC3)cc2)cc(C(F)(F)F)c1N[C@H](CCN(C)C)CSc1ccccc1] |
| N-(4-(4-((2-(4-chlorophenyl)-1-cyclohexen-1-yl)methyl)piperazin-1-yl)benzoyl)-4-(((1R)-4-((2R,5S)-2,5-dimethylpyrrolidin-1-yl)-1-((phenylsulfanyl)methyl)butyl)amino)-3-nitrobenzenesulfonamide | 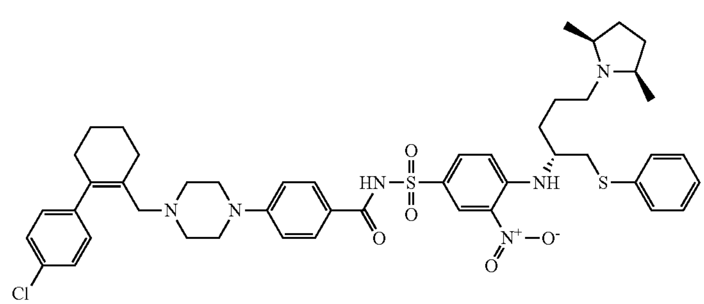 [SMILES: C[C@@H]1CC[C@H](C)N1CCC[C@H](CSc1ccccc1)Nc1ccc(S(=O)(=O)NC(=O)c2ccc(N3CCN(CC4=C(c5ccc(Cl)cc5)CCOC4)CC3)cc2)cc1[N+](=O)[O-]] |

| Name | Structure |
|---|---|
| N-(4-(4-((4-(4-chlorophenyl)-5,6-dihydro-2H-pyran-3-yl)methyl)piperazin-1-yl)benzoyl)-4-(((1R)-4-((2R,5S)-2,5-dimethylpyrrolidin-1-yl)-1-((phenylsulfanyl)methyl)butyl)amino)-3-nitrobenzenesulfonamide | 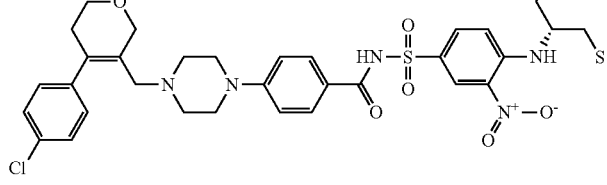 |
| tert-butyl 3-((4-(4-((((4-(((1R)-3-(dimethylamino)-1-((phenylsulfanyl)methyl)propyl)amino)-3-nitrophenyl)sulfonyl)amino)carbonyl)phenyl)piperazin-1-yl)carbonyl)phenylcarbamate | 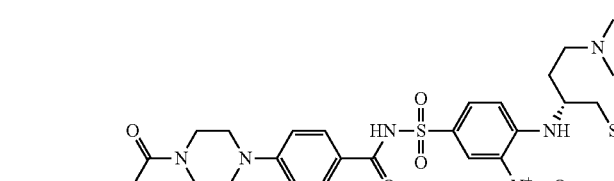 |
| N-(4-(4-(3-(dimethylamino)benzoyl)piperazin-1-yl)benzoyl)-4-(((1R)-3-(dimethylamino)-1-((phenylsulfanyl)methyl)propyl)amino)-3-nitrobenzenesulfonamide | 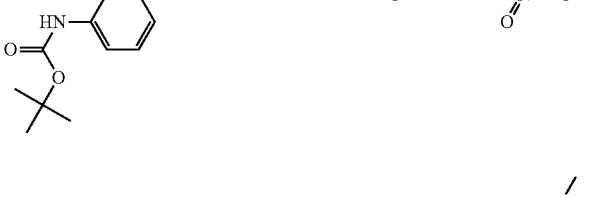 |
| N-(4-(4-((1,1'-biphenyl)-2-ylmethyl)piperazin-1-yl)benzoyl)-4-(((1R)-3-(dimethylamino)-1-methyl-1-((phenylsulfanyl)methyl)propyl)amino)-3-nitrobenzenesulfonamide | 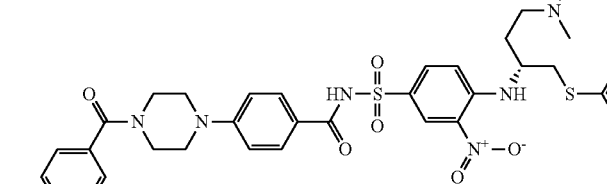 |
| N-(4-(4-((1,1'-biphenyl)-2-ylmethyl)piperazin-1-yl)benzoyl)-4-(((1S)-3-(dimethylamino)-1-methyl-1-((phenylsulfanyl)methyl)propyl)amino)-3-nitrobenzenesulfonamide | 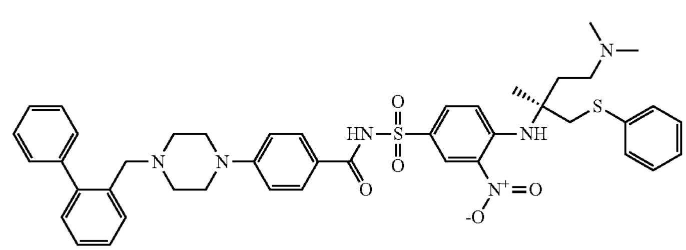 |

| Name | Structure |
|---|---|
| N-(4-(4-(2-(1,3-dihydro-2H-isoindol-2-yl)benzyl)piperazin-1-yl)benzoyl)-4-(((1R)-3-(dimethylamino)-1-((phenylsulfanyl)methyl)propyl)amino)-3-nitrobenzenesulfonamide | 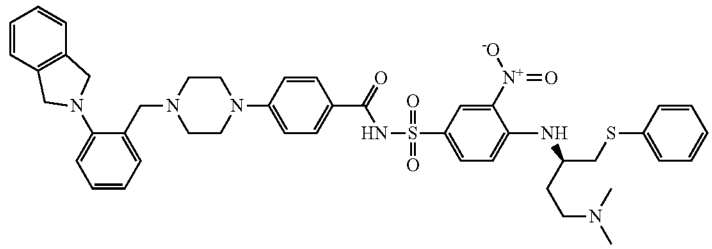 |
| N-(4-(4-(2-(cyclohexylamino)benzyl)piperazin-1-yl)benzoyl)-4-(((1R)-3-(dimethylamino)-1-((phenylsulfanyl)methyl)propyl)amino)-3-nitrobenzenesulfonamide | 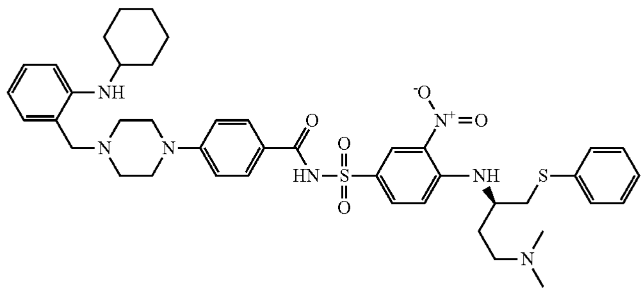 |
| 4-(((1R)-3-(dimethylamino)-1-((phenylsulfanyl)methyl)propyl)amino)-N-(4-(4-(2-(isopropylamino)benzyl)piperazin-1-yl)benzoyl)-3-nitrobenzenesulfonamide | 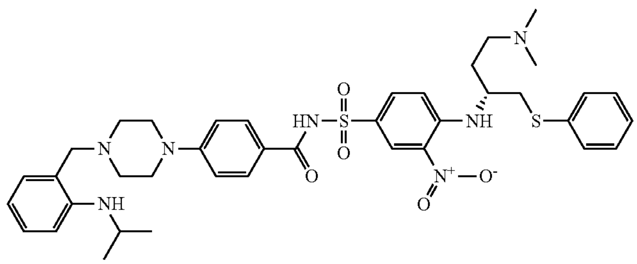 [SMILES: CC(C)Nc1ccccc1CN1CCN(c2ccc(C(=O)NS(=O)(=O)c3ccc(N[C@H](CCN(C)C)CSc4ccccc4)c([N+](=O)[O-])c3)cc2)CC1] |
| N-(4-(4-(2-(benzylamino)benzyl)piperazin-1-yl)benzoyl)-4-(((1R)-3-(dimethylamino)-1-((phenylsulfanyl)methyl)propyl)amino)-3-nitrobenzenesulfonamide | 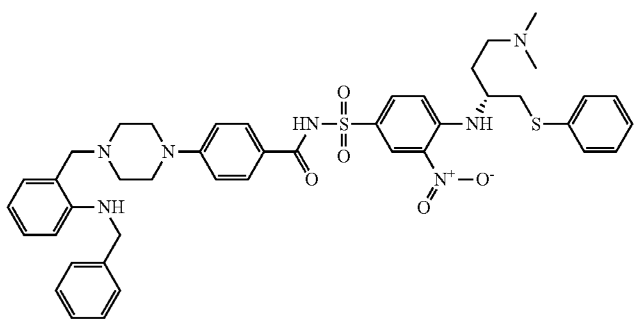 [SMILES: CN(C)CC[C@H](CSc1ccccc1)Nc1ccc(S(=O)(=O)NC(=O)c2ccc(N3CCN(Cc4ccccc4NCc4ccccc4)CC3)cc2)cc1[N+](=O)[O-]] |
| 4-(((1R)-3-(dimethylamino)-1-((phenylsulfanyl)methyl)propyl)amino)-3-nitro-N-(4-(4-(2-(piperidin-1-yl)benzyl)piperazin-1-yl)benzoyl)benzenesulfonamide | 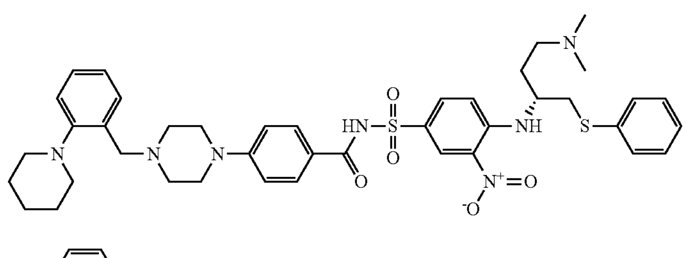 |
| N-(4-(4-((1,1'-biphenyl)-2-ylmethyl)piperazin-1-yl)benzoyl)-3-nitro-4-((2-(phenylsulfanyl)ethyl)amino)benzenesulfonamide | 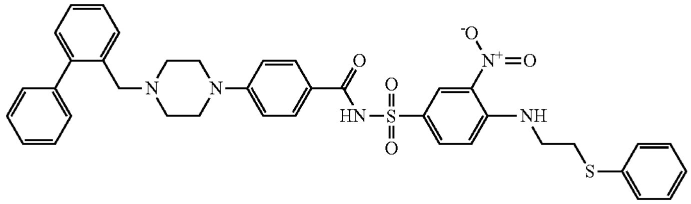 |

-continued

| Name | Structure |
|---|---|
| N-(4-(4-((1,1'-biphenyl)-2-ylmethyl)piperazin-1-yl)benzoyl)-4-((cyclohexylmethyl)amino)-3-nitrobenzenesulfonamide | 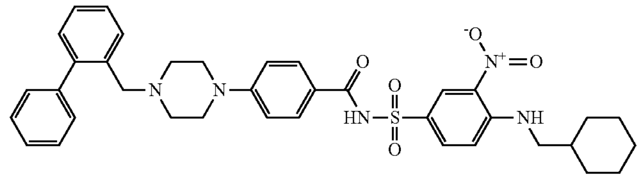 |
| N-(4-(4-((1,1'-biphenyl)-2-ylmethyl)-4-methoxypiperidin-1-yl)benzoyl)-4-(((1R)-3-(morpholin-4-yl)-1-((phenylsulfanyl)methyl)propyl)amino)-3-nitrobenzenesulfonamide | 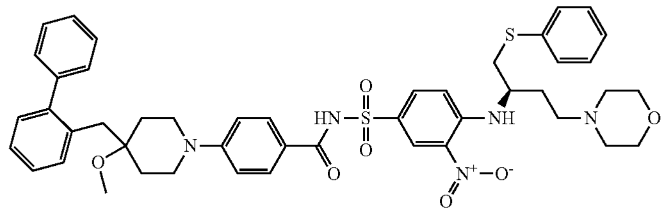 [SMILES: COC1(Cc2ccccc2-c2ccccc2)CCN(c2ccc(C(=O)NS(=O)(=O)c3ccc(N[C@H](CCN4CCOCC4)CSc4ccccc4)c([N+](=O)[O-])c3)cc2)CC1] |
| N-(4-(4-((1,1'-biphenyl)-2-ylmethyl)-4-methoxypiperidin-1-yl)benzoyl)-3-nitro-4-((2-(phenylsulfanyl)ethyl)amino)benzenesulfonamide | 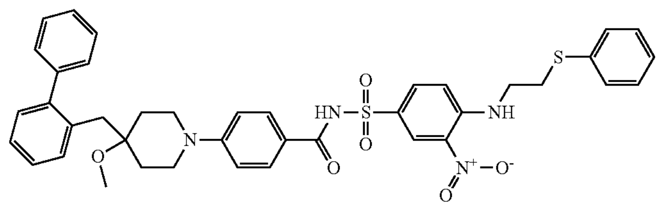 [SMILES: COC1(Cc2ccccc2-c2ccccc2)CCN(c2ccc(C(=O)NS(=O)(=O)c3ccc(NCCSc4ccccc4)c([N+](=O)[O-])c3)cc2)CC1] |
| N-(4-(4-((4'-chloro(1,1'-biphenyl)-2-yl)methyl)piperazin-1-yl)benzoyl)-4-(((1S)-3-(dimethylamino)-1-((phenylsulfanyl)methyl)propyl)amino)-3-nitrobenzenesulfonamide | 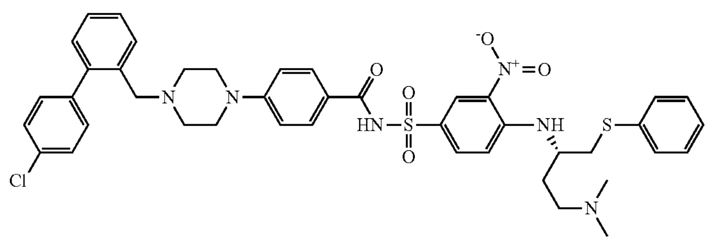 |
| N-(4-(4-((4'-chloro(1,1'-biphenyl)-2-yl)methyl)piperazin-1-yl)benzoyl)-4-(((1R)-1-((phenylsulfanyl)methyl)-3-(pyrrolidin-1-yl)propyl)amino)-3-(trifluoromethyl)benzenesulfonamide | 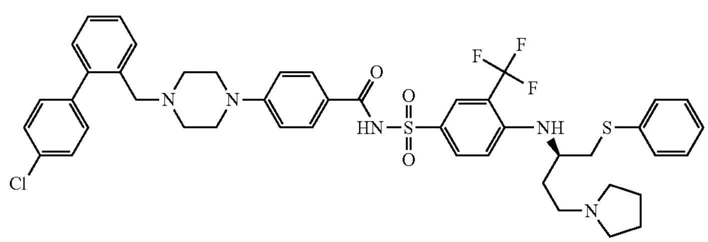 [SMILES: O=C(NS(=O)(=O)c1ccc(N[C@H](CCN2CCCC2)CSc2ccccc2)c(C(F)(F)F)c1)c1ccc(N2CCN(Cc3ccccc3-c3ccc(Cl)cc3)CC2)cc1] |
| N-(4-(4-((4-(4-chlorophenyl)pyridin-3-yl)methyl)piperazin-1-yl)benzoyl)-4-(((1R)-3-(dimethylamino)-1-((phenylsulfanyl)methyl)propyl)amino)-3-nitrobenzenesulfonamide | 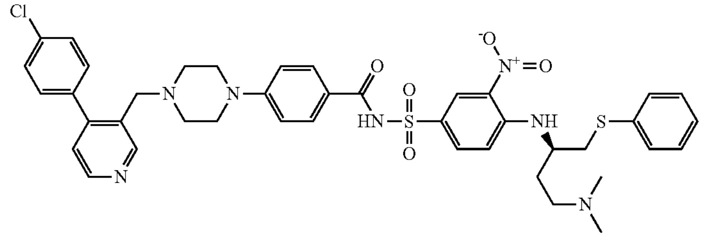 |

| Name | Structure |
|---|---|
| N-(4-(4-((4-(4-chlorophenyl)pyridin-3-yl)methyl)piperazin-1-yl)benzoyl)-4-(((1R)-3-(morpholin-4-yl)-1-((phenylsulfanyl)methyl)propyl)amino)-3-nitrobenzenesulfonamide | 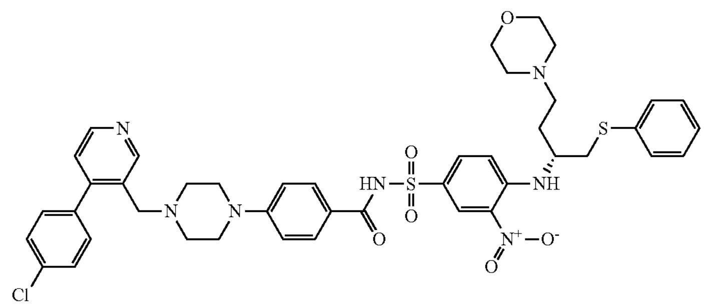 [SMILES: O=C(NS(=O)(=O)c1ccc(N[C@H](CCN2CCOCC2)CSc2ccccc2)c([N+](=O)[O-])c1)c1ccc(N2CCN(Cc3cnccc3-c3ccc(Cl)cc3)CC2)cc1] |
| N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-2-fluoro-3-(trifluoromethyl)benzenesulfonamide | 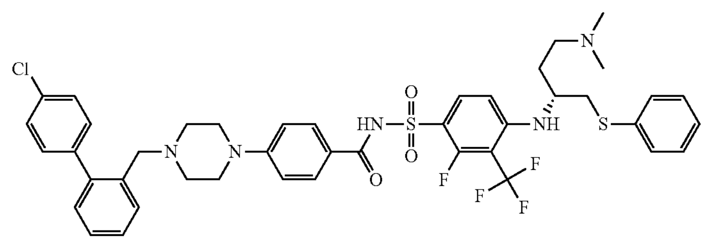 [SMILES: CN(C)CC[C@H](CSc1ccccc1)Nc1ccc(S(=O)(=O)NC(=O)c2ccc(N3CCN(Cc4ccccc4-c4ccc(Cl)cc4)CC3)cc2)c(F)c1C(F)(F)F] |
| N-(6-(4-((4'-chloro(1,1'-biphenyl)-2-yl)methyl)piperazin-1-yl)-1,2-benzisoxazol-3-yl)-3-nitro-4-((2-(phenylsulfanyl)ethyl)amino)benzenesulfonamide | 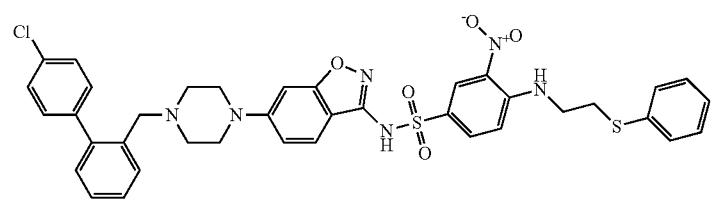 |
| N-(6-(4-((4'-chloro(1,1'-biphenyl)-2-yl)methyl)piperazin-1-yl)-1,2-benzisoxazol-3-yl)-4-(((1R)-3-(morpholin-4-yl)-1-((phenylsulfanyl)methyl)propyl)amino)-3-nitrobenzenesulfonamide | 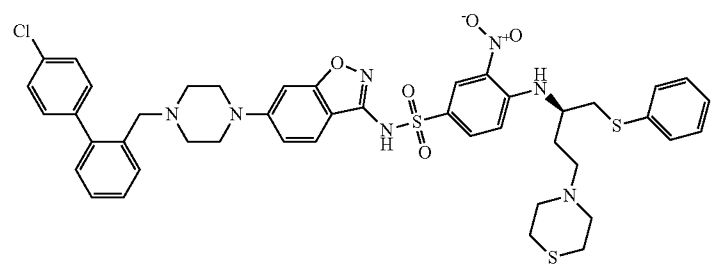 |
| N-(6-(4,4-dimethylpiperidin-1-yl)-1,2-benzisoxazol-3-yl)-3-nitro-4-((2-(phenylsulfanyl)ethyl)amino)benzenesulfonamide | 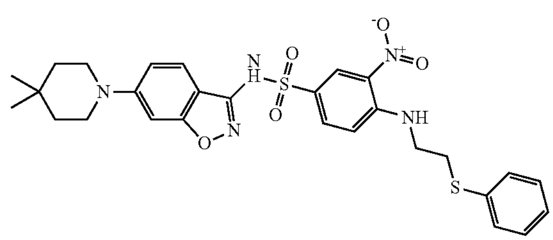 |
| N-(6-(4,4-dimethylpiperidin-1-yl)-1,2-benzisoxazol-3-yl)-4-(((1R)-3-(morpholin-4-yl)-1-((phenylsulfanyl)methyl)propyl)amino)-3-nitrobenzenesulfonamide | 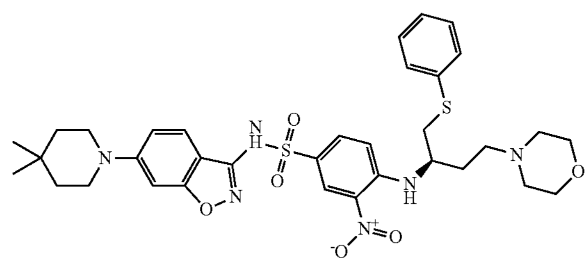 |

-continued

| Name | Structure |
|---|---|
| N-(6-(4-(3,3-diphenylpropen-2-yl)piperazin-1-yl)-1,2-benzisoxazol-3-yl)-4-(((1R)-3-(morpholin-4-yl)-1-((phenylsulfanyl)methyl)propyl)amino)-3-nitrobenzenesulfonamide | 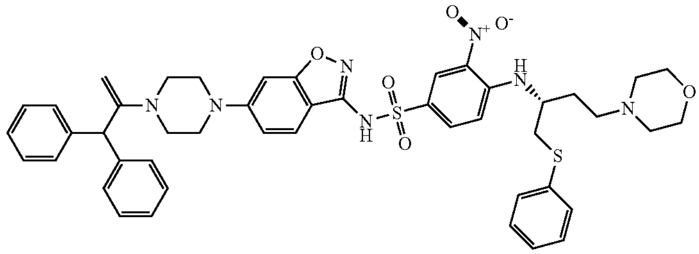 |
| N-(6-(4-(3,3-diphenylpropen-2-yl)piperazin-1-yl)-1,2-benzisoxazol-3-yl)-3-nitro-4-((2-(phenylsulfanyl)ethyl)amino)benzenesulfonamide | 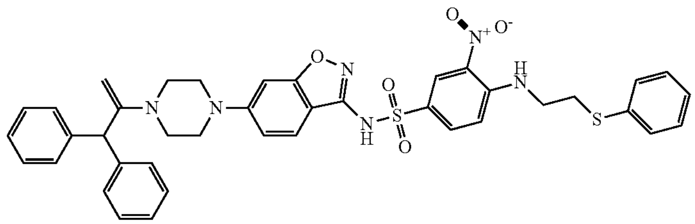 |
| N-(6-(4-((4'-chloro(1,1'-biphenyl)-2-yl)methyl)piperazin-1-yl)-1,2-benzisoxazol-3-yl)-4-(((1R)-3-(dimethylamino)-1-((phenylsulfanyl)methyl)propyl)amino)-3-nitrobenzenesulfonamide | 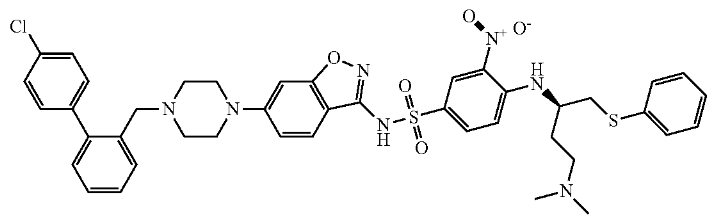 |
| 4-(((1R)-3-(dimethylamino)-1-((phenylsulfanyl)methyl)propyl)amino)-N-(6-(4,4-dimethylpiperidin-1-yl)-1,2-benzisoxazol-3-yl)-3-nitrobenzenesulfonamide | 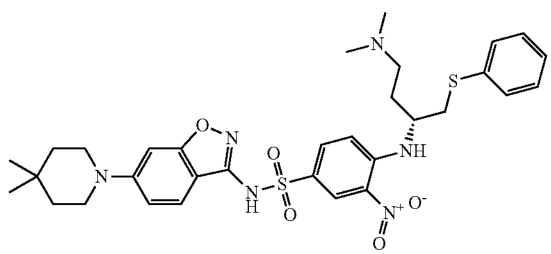 |
| N-(6-(4-((4'-chloro(1,1'-biphenyl)-2-yl)methyl)piperazin-1-yl)-1-methyl-1H-indazol-3-yl)-3-nitro-4-((2-(phenylsulfanyl)ethyl)amino)benzenesulfonamide | 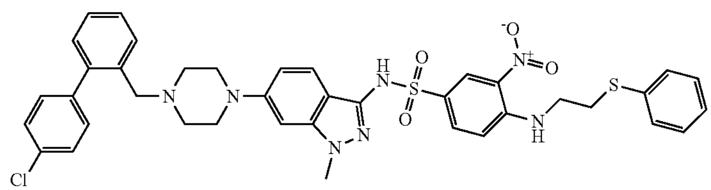 |
| N-(6-(4-((4'-chloro(1,1'-biphenyl)-2-yl)methyl)piperazin-1-yl)-1-methyl-1H-indazol-3-yl)-4-((1,1-dimethyl-2-(phenylsulfanyl)ethyl)amino)-3-nitrobenzenesulfonamide | 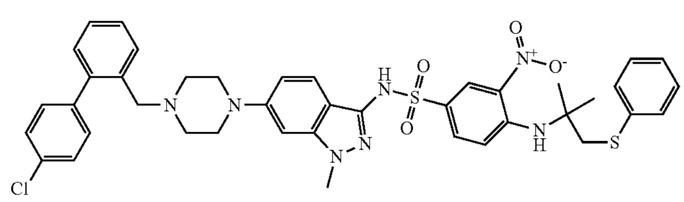 [SMILES: Cn1nc(NS(=O)(=O)c2ccc(NC(C)(C)CSc3ccccc3)c([N+](=O)[O-])c2)c2ccc(N3CCN(Cc4ccccc4-c4ccc(Cl)cc4)CC3)cc21] |
| N-(6-(4-((4'-chloro(1,1'-biphenyl)-2-yl)methyl)piperazin-1-yl)-1-methyl-1H-indazol-3-yl)-4-(((1R)-3-(dimethylamino)-1-((phenylsulfanyl)methyl)propyl)amino)-3-nitrobenzenesulfonamide | 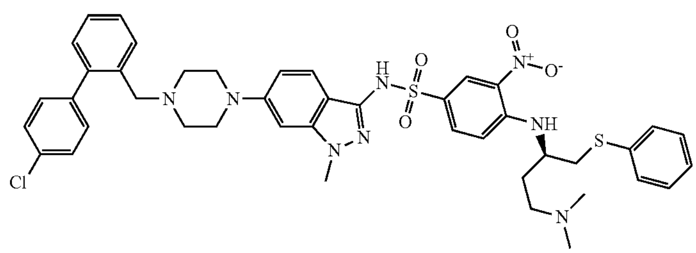 [SMILES: CN(C)CC[C@H](CSc1ccccc1)Nc1ccc(S(=O)(=O)Nc2nn(C)c3cc(N4CCN(Cc5ccccc5-c5ccc(Cl)cc5)CC4)ccc23)cc1[N+](=O)[O-]] |

-continued

| Name | Structure |
|---|---|
| N-(6-(4-((4'-chloro(1,1'-biphenyl)-2-yl)methyl)piperazin-1-yl)-1-methyl-1H-indazol-3-yl)-4-(((1R)-3-(morpholin-4-yl)-1-((phenylsulfanyl)methyl)propyl)amino)-3-nitrobenzenesulfonamide | 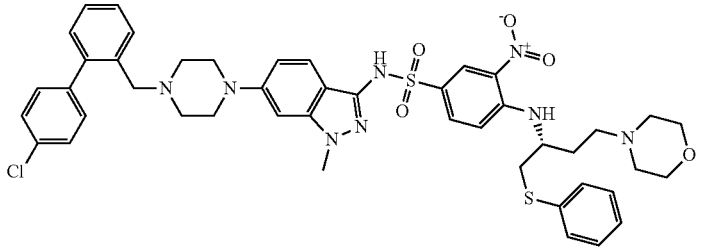 |
| N-(6-(4-((4'-chloro(1,1'-biphenyl)-2-yl)methyl)piperazin-1-yl)-1H-indazol-3-yl)-3-nitro-4-((2-(phenylsulfanyl)ethyl)amino)benzenesulfonamide | 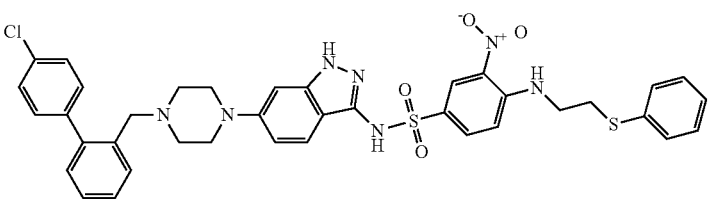 |
| N-(6-(4-((4'-chloro(1,1'-biphenyl)-2-yl)methyl)piperazin-1-yl)-1H-indazol-3-yl)-4-(((1R)-3-(dimethylamino)-1-((phenylsulfanyl)methyl)propyl)amino)-3-nitrobenzenesulfonamide, and | |
| N-(6-(4-((4'-chloro(1,1'-biphenyl)-2-yl)methyl)piperazin-1-yl)-1H-indazol-3-yl)-4-(((1R)-3-(morpholin-4-yl)-1-((phenylsulfanyl)methyl)propyl)amino)-3-nitrobenzenesulfonamide | 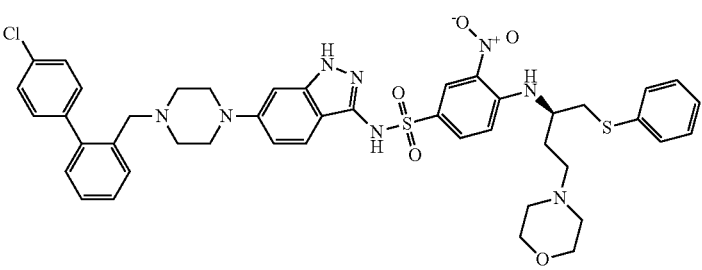 |
| N-(4-(4-((4'-chloro(1,1'-biphenyl)-2-yl)methyl)piperazin-1-yl)benzoyl)-3-(methylsulfonyl)-4-((2-(phenylsulfanyl)ethyl)amino)benzenesulfonamide | 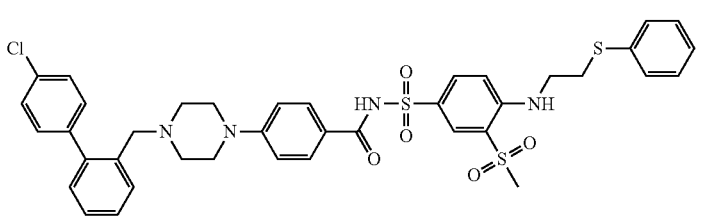 [SMILES: CS(=O)(=O)c1cc(S(=O)(=O)NC(=O)c2ccc(N3CCN(Cc4ccccc4-c4ccc(Cl)cc4)CC3)cc2)ccc1NCCSc1ccccc1] |
| N-(4-(4-((4'-chloro(1,1'-biphenyl)-2-yl)methyl)piperazin-1-yl)benzoyl)-4-((1,1-dimethyl-2-(phenylsulfanyl)ethyl)amino)-3-(methylsulfonyl)benzenesulfonamide | 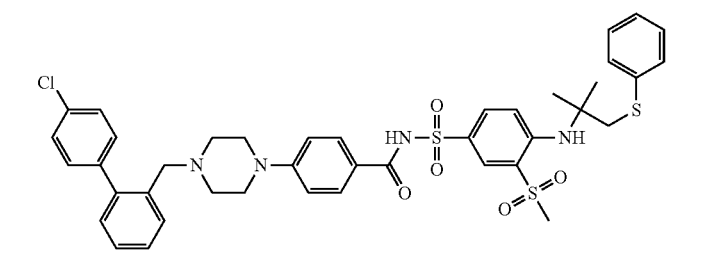 [SMILES: CC(C)(CSc1ccccc1)Nc1ccc(S(=O)(=O)NC(=O)c2ccc(N3CCN(Cc4ccccc4-c4ccc(Cl)cc4)CC3)cc2)cc1S(C)(=O)=O] |
| N-(4-(4-((4'-chloro(1,1'-biphenyl)-2-yl)methyl)piperazin-1-yl)benzoyl)-3-(methylsulfonyl)-4-(((1R)-3-(morpholin-4-yl)-1-((phenylsulfanyl)methyl)propyl)amino)benzenesulfonamide | 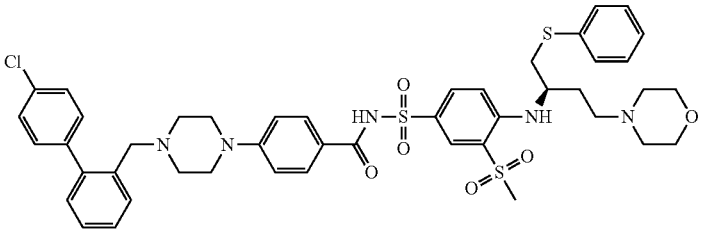 [SMILES: CS(=O)(=O)c1cc(S(=O)(=O)NC(=O)c2ccc(N3CCN(Cc4ccccc4-c4ccc(Cl)cc4)CC3)cc2)ccc1N[C@H](CCN1CCOCC1)CSc1ccccc1] |

-continued

| Name | Structure |
|---|---|
| N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-(ethylsulfonyl)benzenesulfonamide | 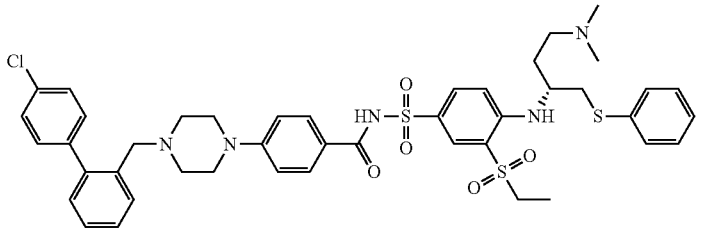 [SMILES: CCS(=O)(=O)c1cc(S(=O)(=O)NC(=O)c2ccc(N3CCN(Cc4ccccc4-c4ccc(Cl)cc4)CC3)cc2)ccc1N[C@H](CCN(C)C)CSc1ccccc1] |
| N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-(methylsulfonyl)benzenesulfonamide | 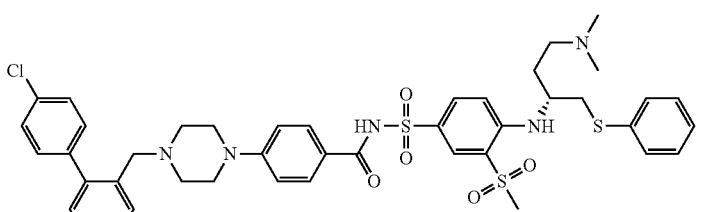 |
| N-(4-(4-((4'-chloro(1,1'-biphenyl)-2-yl)methyl)piperazin-1-yl)benzoyl)-4-(((1R)-3-(diisopropylamino)-1-((phenylsulfanyl)methyl)propyl)amino)-3-((trifluoromethyl)sulfonyl)benzenesulfonamide | 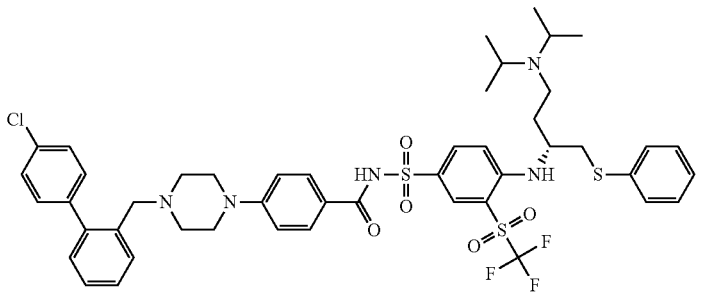 [SMILES: CC(C)N(CC[C@H](CSc1ccccc1)Nc1ccc(S(=O)(=O)NC(=O)c2ccc(N3CCN(Cc4ccccc4-c4ccc(Cl)cc4)CC3)cc2)cc1S(=O)(=O)C(F)(F)F)C(C)C] |
| N-(4-(4-((2-(4-chlorophenyl)cyclohex-1-en-1-yl)methyl)piperazin-1-yl)benzoyl)-4-(((1R)-3-(diisopropylamino)-1-((phenylsulfanyl)methyl)propyl)amino)-3-((trifluoromethyl)sulfonyl)benzenesulfonamide | 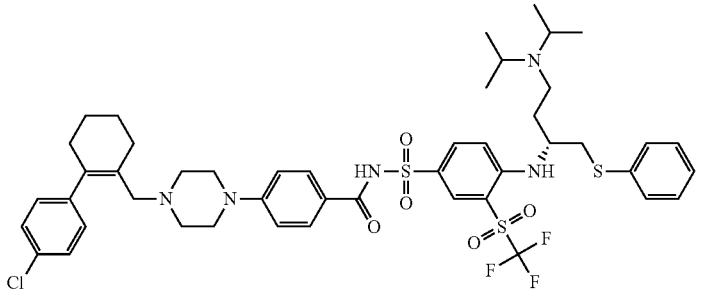 |
| N-(4-(4-((2-(4-chlorophenyl)cyclohex-1-en-1-yl)methyl)piperazin-1-yl)benzoyl)-4-(((1R)-3-((2R,5S)-2,5-dimethylpyrrolidin-1-yl)-1-((phenylsulfanyl)methyl)propyl)amino)-3-((trifluoromethyl)sulfonyl)benzenesulfonamide | 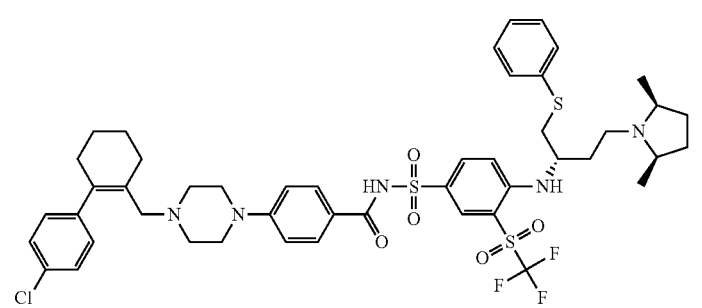 [SMILES: C[C@@H]1CC[C@H](C)N1CC[C@@H](CSc1ccccc1)Nc1ccc(S(=O)(=O)NC(=O)c2ccc(N3CCN(CC4=C(c5ccc(Cl)cc5)CCCC4)CC3)cc2)cc1S(=O)(=O)C(F)(F)F] |

-continued

| Name | Structure |
|---|---|
| 4-(((1R)-4-(7-azabicyclo[2.2.1] hept-7-yl)-1-((phenylsulfanyl)methyl) butyl)amino)-N-(4-(4-((2-(4-chlorophenyl)cyclohex-1-en-1-yl)methyl)piperazin-1-yl)benzoyl)-3-((trifluoromethyl)sulfonyl) benzenesulfonamide | 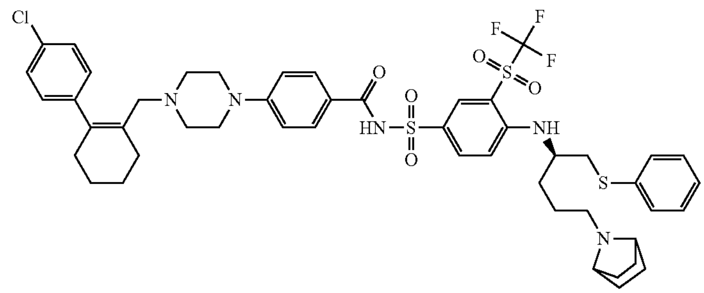 |
| 4-(((1R)-4-(7-azabicyclo[2.2.1] hept-7-yl)-1-((phenylsulfanyl) methyl)butyl)amino)-N-(4-(4-((4-(4-chlorophenyl)-5,6-dihydro-2H-pyran-3-yl)methyl)piperazin-1-yl)benzoyl)-3-((trifluoromethyl) sulfonyl)benzenesulfonamide | 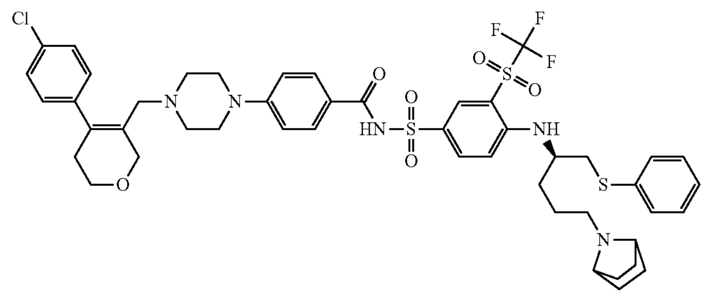 [SMILES: O=C(NS(=O)(=O)c1ccc(N[C@H](CCCN2C3CCC2CC3)CSc2ccccc2)c(S(=O)(=O)C(F)(F)F)c1)c1ccc(N2CCN(CC3=C(c4ccc(Cl)cc4)CCCC3)CC2)cc1] |
| N-(4-(4-((4-(4-chlorophenyl)-5,6-dihydro-2H-pyran-3-yl)methyl) piperazin-1-yl)benzoyl)-4-(((1R)-4-((2R,5S)-2,5-dimethylpyrrolidin-1-yl)-1-((phenylsulfanyl)methyl) butyl)amino)-3-((trifluoromethyl) sulfonyl)benzenesulfonamide | 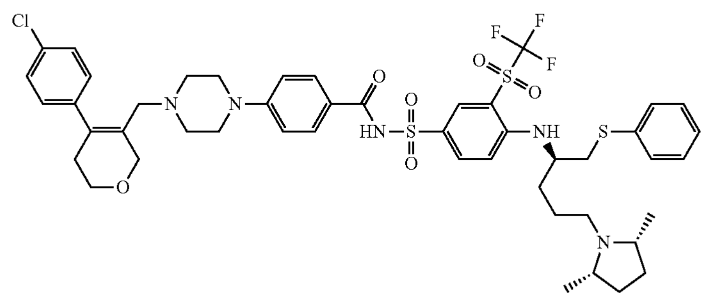 |
| N-(4-(4-((2-(4-chlorophenyl)cyclohex-1-en-1-yl)methyl)piperazin-1-yl) benzoyl)-4-(((1R)-4-(diisopropylamino)-1-((phenylsulfanyl)methyl)butyl)amino)-3-((trifluoromethyl)sulfonyl) benzenesulfonamide | 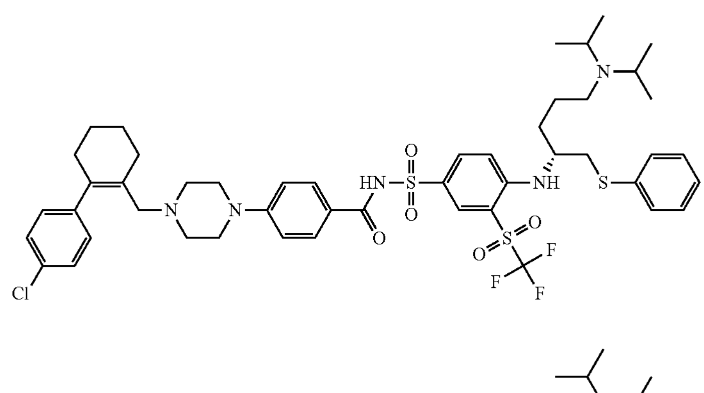 |
| N-(4-(4-((4-(4-chlorophenyl)-5,6-dihydro-2H-pyran-3-yl)methyl)piperazin-1-yl)benzoyl)-4-(((1R)-4-(diisopropylamino)-1-((phenylsulfanyl)methyl)butyl) amino)-3-((trifluoromethyl) sulfonyl)benzenesulfonamide | 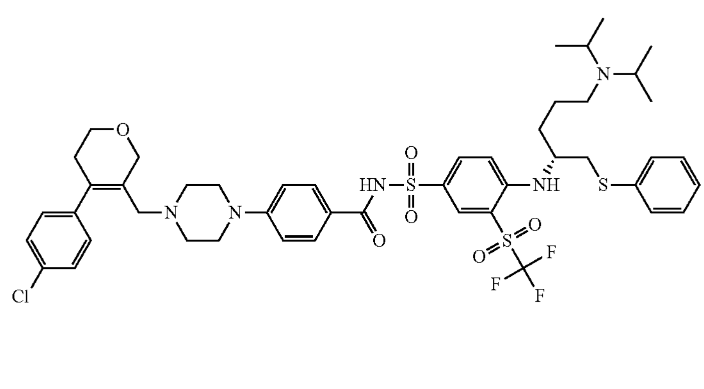 [SMILES: CC(C)N(CCC[C@H](CSc1ccccc1)Nc1ccc(S(=O)(=O)NC(=O)c2ccc(N3CCN(CC4=C(c5ccc(Cl)cc5)CCOC4)CC3)cc2)cc1S(=O)(=O)C(F)(F)F)C(C)C] |

| Name | Structure |
|---|---|
| N-(4-(4-((2-(4-chlorophenyl)cyclohex-1-en-1-yl)methyl)piperazin-1-yl)benzoyl)-4-(((1R)-4-(dimethylamino)-1-((phenylsulfanyl)methyl)butyl)amino)-3-((trifluoromethyl)sulfonyl)benzenesulfonamide | 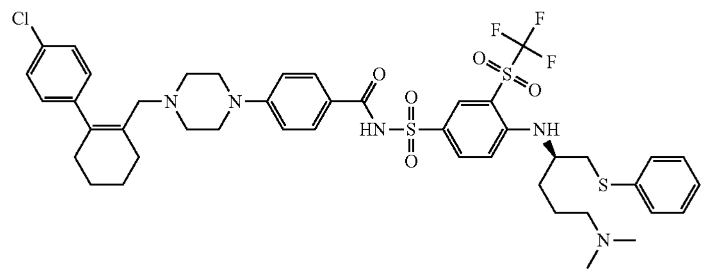 |
| N-(4-(4-((4-(4-chlorophenyl)-5,6-dihydro-2H-pyran-3-yl)methyl)piperazin-1-yl)benzoyl)-4-(((1R)-4-(dimethylamino)-1-((phenylsulfanyl)methyl)butyl)amino)-3-((trifluoromethyl)sulfonyl)benzenesulfonamide | 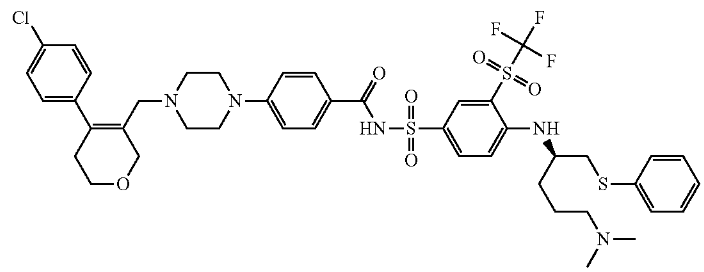 [SMILES: CN(C)CCC[C@H](CSc1ccccc1)Nc1ccc(S(=O)(=O)NC(=O)c2ccc(N3CCN(CC4=C(c5ccc(Cl)cc5)CCCC4)CC3)cc2)cc1S(=O)(=O)C(F)(F)F] |
| N-(4-(4-((2-(4-chlorophenyl)cyclohex-1-en-1-yl)methyl)piperazin-1-yl)benzoyl)-4-(((1R)-4-((2R,5S)-2,5-dimethylpyrrolidin-1-yl)-1-((phenylsulfanyl)methyl)butyl)amino)-3-((trifluoromethyl)sulfonyl)benzenesulfonamide | 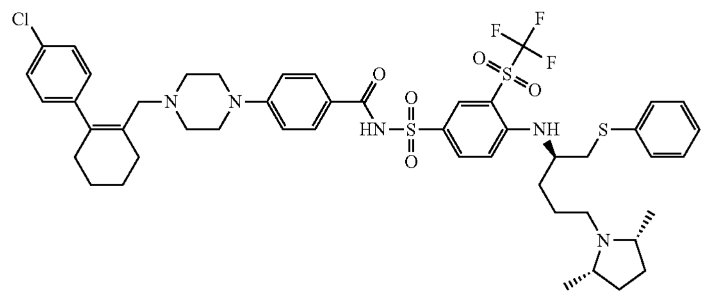 [SMILES: C[C@@H]1CC[C@H](C)N1CCC[C@H](CSc1ccccc1)Nc1ccc(S(=O)(=O)NC(=O)c2ccc(N3CCN(CC4=C(c5ccc(Cl)cc5)CCCC4)CC3)cc2)cc1S(=O)(=O)C(F)(F)F] |
| 4-(((1R)-3-(1-azetidinyl)-1-((phenylsulfanyl)methyl)propyl)amino)-N-(4-(4-((2-(4-chlorophenyl)cyclohex-1-en-1-yl)methyl)piperazin-1-yl)benzoyl)-3-((trifluoromethyl)sulfonyl)benzenesulfonamide | 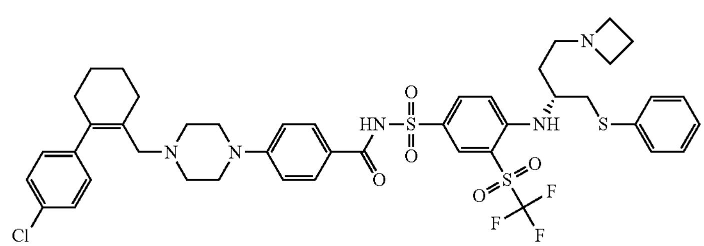 [SMILES: O=C(NS(=O)(=O)c1ccc(N[C@H](CCN2CCC2)CSc2ccccc2)c(S(=O)(=O)C(F)(F)F)c1)c1ccc(N2CCN(CC3=C(c4ccc(Cl)cc4)CCCC3)CC2)cc1] |
| 4-(((1R)-3-(1-azetidinyl)-1-((phenylsulfanyl)methyl)propyl)amino)-N-(4-(4-((4-(4-chlorophenyl)-5,6-dihydro-2H-pyran-3-yl)methyl)piperazin-1-yl)benzoyl)-3-((trifluoromethyl)sulfonyl)benzenesulfonamide | 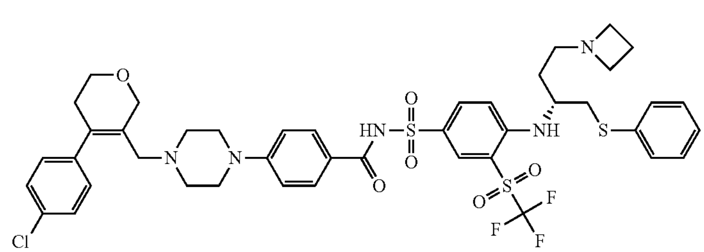 [SMILES: O=C(NS(=O)(=O)c1ccc(N[C@H](CCN2CCC2)CSc2ccccc2)c(S(=O)(=O)C(F)(F)F)c1)c1ccc(N2CCN(CC3=C(c4ccc(Cl)cc4)CCOC3)CC2)cc1] |

-continued

| Name | Structure |
|---|---|
| 4-(((1R)-3-((3aR,6aS)-tetrahydro-1H-furo[3,4-c]pyrrol-5(3H)-yl)-1-((phenylsulfanyl)methyl)propyl)amino)-N-(4-(4-((2-(4-chlorophenyl)cyclohex-1-en-1-yl)methyl)piperazin-1-yl)benzoyl)-3-((trifluoromethyl)sulfonyl)benzenesulfonamide | 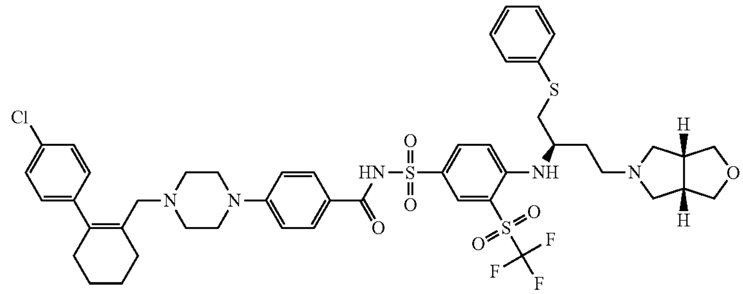 [SMILES: O=C(NS(=O)(=O)c1ccc(N[C@H](CCN2C[C@H]3COC[C@H]3C2)CSc2ccccc2)c(S(=O)(=O)C(F)(F)F)c1)c1ccc(N2CCN(CC3=C(c4ccc(Cl)cc4)CCCC3)CC2)cc1] |
| 4-(((1R)-3-((3aR,6aS)-tetrahydro-1H-furo[3,4-c]pyrrol-5(3H)-yl)-1-((phenylsulfanyl)methyl)propyl)amino)-N-(4-(4-((4-(4-chlorophenyl)-5,6-dihydro-2H-pyran-3-yl)methyl)piperazin-1-yl)benzoyl)-3-((trifluoromethyl)sulfonyl)benzenesulfonamide | 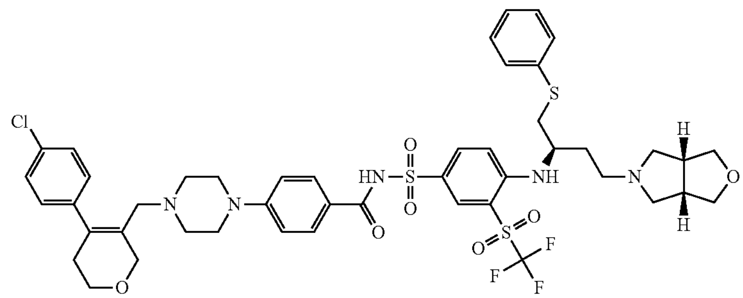 [SMILES: O=C(NS(=O)(=O)c1ccc(N[C@H](CCN2C[C@H]3COC[C@H]3C2)CSc2ccccc2)c(S(=O)(=O)C(F)(F)F)c1)c1ccc(N2CCN(CC3=C(c4ccc(Cl)cc4)CCOC3)CC2)cc1] |
| N-(4-(4-((2-(4-chlorophenyl)cyclohex-1-en-1-yl)methyl)piperazin-1-yl)benzoyl)-4-(((1R)-3-(8-oxa-3-azabicyclo[3.2.1]oct-3-yl)-1-((phenylsulfanyl)methyl)propyl)amino)-3-((trifluoromethyl)sulfonyl)benzenesulfonamide | 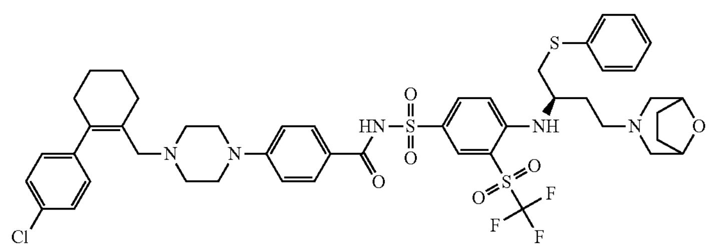 [SMILES: O=C(NS(=O)(=O)c1ccc(N[C@H](CCN2CC3CCC(C2)O3)CSc2ccccc2)c(S(=O)(=O)C(F)(F)F)c1)c1ccc(N2CCN(CC3=C(c4ccc(Cl)cc4)CCCC3)CC2)cc1] |
| N-(4-(4-((4-(4-chlorophenyl)-5,6-dihydro-2H-pyran-3-yl)methyl)piperazin-1-yl)benzoyl)-4-(((1R)-3-(8-oxa-3-azabicyclo[3.2.1]oct-3-yl)-1-((phenylsulfanyl)methyl)propyl)amino)-3-((trifluoromethyl)sulfonyl)benzenesulfonamide | 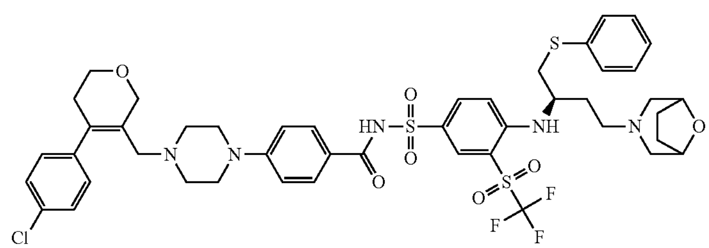 [SMILES: O=C(NS(=O)(=O)c1ccc(N[C@H](CCN2CC3CCC(C2)O3)CSc2ccccc2)c(S(=O)(=O)C(F)(F)F)c1)c1ccc(N2CCN(CC3=C(c4ccc(Cl)cc4)CCOC3)CC2)cc1] |
| N-(4-(4-((2-(4-chlorophenyl)cyclohex-1-en-1-yl)methyl)piperazin-1-yl)benzoyl)-4-(((1R)-4-(morpholin-4-yl)-1-((phenylsulfanyl)methyl)butyl)amino)-3-((trifluoromethyl)sulfonyl)benzenesulfonamide | 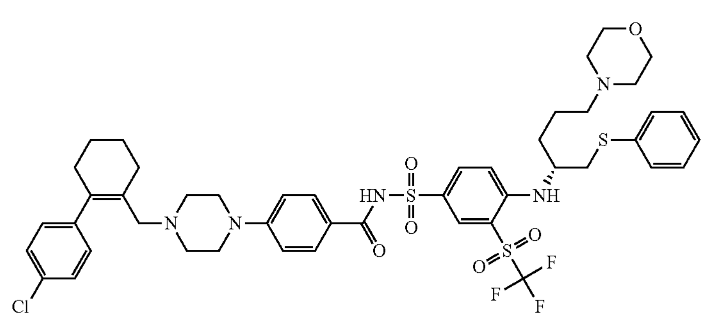 [SMILES: O=C(NS(=O)(=O)c1ccc(N[C@H](CCCN2CCOCC2)CSc2ccccc2)c(S(=O)(=O)C(F)(F)F)c1)c1ccc(N2CCN(CC3=C(c4ccc(Cl)cc4)CCCC3)CC2)cc1] |

| Name | Structure |
|---|---|
| N-(4-(4-((2-(4-chlorophenyl)-5,5-dimethylcyclohex-1-en-1-yl)methyl)piperazin-1-yl)benzoyl)-4-(((1R)-4-(morpholin-4-yl)-1-((phenylsulfanyl)methyl)butyl)amino)-3-((trifluoromethyl)sulfonyl)benzenesulfonamide | 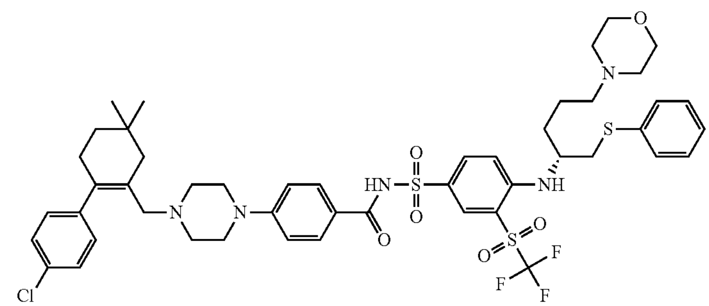 [SMILES: CC1(C)CCC(c2ccc(Cl)cc2)=C(CN2CCN(c3ccc(C(=O)NS(=O)(=O)c4ccc(N[C@H](CCCN5CCOCC5)CSc5ccccc5)c(S(=O)(=O)C(F)(F)F)c4)cc3)CC2)C1] |
| N-(4-((3R,5S)-4-((4'-chloro(1,1'-biphenyl)-2-yl)methyl)-3,5-dimethylpiperazinyl)benzoyl)-4-(((1R)-3-(isopropyl(methyl)amino)-1-((phenylsulfanyl)methyl)propyl)amino)-3-((trifluoromethyl)sulfonyl)benzenesulfonamide | 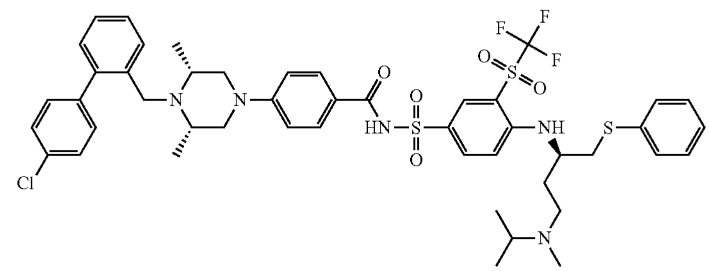 [SMILES: CC(C)N(C)CC[C@H](CSc1ccccc1)Nc1ccc(S(=O)(=O)NC(=O)c2ccc(N3C[C@@H](C)N(Cc4ccccc4-c4ccc(Cl)cc4)[C@@H](C)C3)cc2)cc1S(=O)(=O)C(F)(F)F] |
| N-(4-((3R,5S)-4-((4'-chloro(1,1'-biphenyl)-2-yl)methyl)-3,5-dimethylpiperazinyl)benzoyl)-3-((chloro(difluoro)methyl)sulfonyl)-4-(((1R)-3-((1S,4S)-2-oxa-5-azabicyclo[2.2.1]hept-5-yl)-1-((phenylsulfanyl)methyl)propyl)amino)benzenesulfonamide | 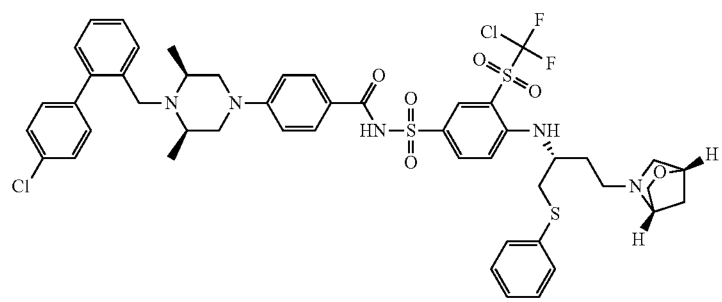 [SMILES: C[C@@H]1CN(c2ccc(C(=O)NS(=O)(=O)c3ccc(N[C@H](CCN4C[C@@H]5C[C@H]4CO5)CSc4ccccc4)c(S(=O)(=O)C(F)(F)Cl)c3)cc2)C[C@H](C)N1Cc1ccccc1-c1ccc(Cl)cc1] |
| 4-(((1R)-3-(7-azabicyclo[2.2.1]hept-7-yl)-1-((phenylsulfanyl)methyl)propyl)amino)-N-(4-(4-((2-(4-chlorophenyl)-1-cyclohepten-1-yl)methyl)piperazin-1-yl)benzoyl)-3-((trifluoromethyl)sulfonyl)benzenesulfonamide | 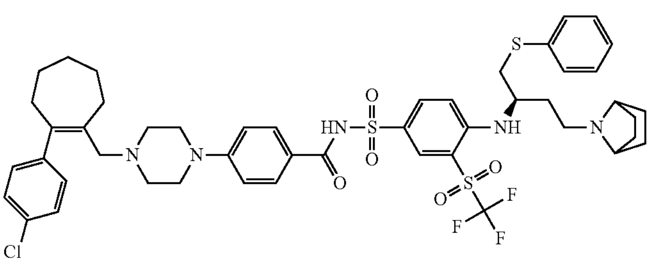 [SMILES: O=C(NS(=O)(=O)c1ccc(N[C@H](CCN2C3CCC2CC3)CSc2ccccc2)c(S(=O)(=O)C(F)(F)F)c1)c1ccc(N2CCN(CC3=C(c4ccc(Cl)cc4)CCCCC3)CC2)cc1] |
| N-(4-(4-((4-(4-chlorophenyl)-5,6-dihydro-2H-pyran-3-yl)methyl)piperazin-1-yl)benzoyl)-4-(((1R)-3-(2-oxa-5-azabicyclo[2.2.1]hept-5-yl)-1-((phenylsulfanyl)methyl)propyl)amino)-3-((trifluoromethyl)sulfonyl)benzenesulfonamide | 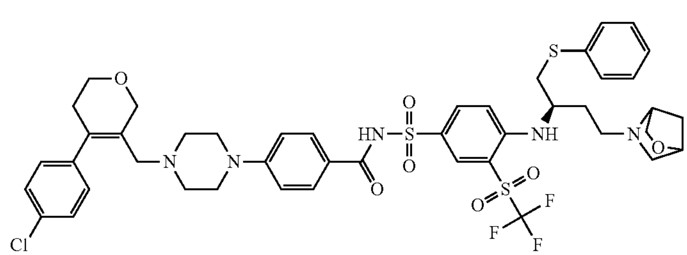 [SMILES: O=C(NS(=O)(=O)c1ccc(N[C@H](CCN2CC3CC2CO3)CSc2ccccc2)c(S(=O)(=O)C(F)(F)F)c1)c1ccc(N2CCN(CC3=C(c4ccc(Cl)cc4)CCOC3)CC2)cc1] |

-continued

| Name | Structure |
|---|---|
| 4-(((1R)-3-(7-azabicyclo[2.2.1]hept-7-yl)-1-((phenylsulfanyl)methyl)propyl)amino)-N-(4-(4-((4-(4-chlorophenyl)-5,6-dihydro-2H-pyran-3-yl)methyl)piperazin-1-yl)benzoyl)-3-((trifluoromethyl)sulfonyl)benzenesulfonamide | 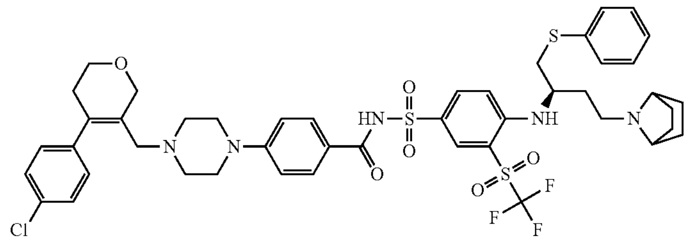 [SMILES: O=C(NS(=O)(=O)c1ccc(N[C@H](CCN2C3CCC2CC3)CSc2ccccc2)c(S(=O)(=O)C(F)(F)F)c1)c1ccc(N2CCN(CC3=C(c4ccc(Cl)cc4)CCOC3)CC2)cc1] |
| N-(4-(4-((2-(4-chlorophenyl)cyclohex-1-en-1-yl)methyl)piperazin-1-yl)benzoyl)-4-(((1R)-1-((phenylsulfanyl)methyl)-3-(pyrrolidin-1-yl)propyl)amino)-3-((trifluoromethyl)sulfonyl)benzenesulfonamide | 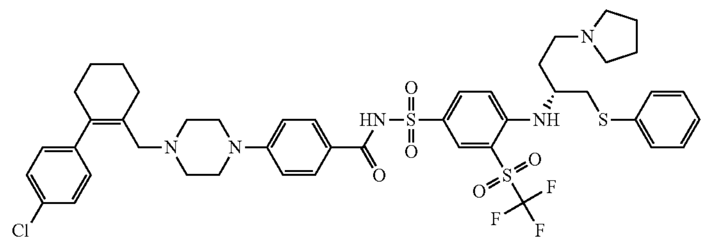 [SMILES: O=C(NS(=O)(=O)c1ccc(N[C@H](CCN2CCCC2)CSc2ccccc2)c(S(=O)(=O)C(F)(F)F)c1)c1ccc(N2CCN(CC3=C(c4ccc(Cl)cc4)CCCC3)CC2)cc1] |
| 4-(((1R)-3-((1S,4R)-2-azabicyclo[2.2.1]hept-2-yl)-1-((phenylsulfanyl)methyl)propyl)amino)-N-(4-(4-((2-(4-chlorophenyl)cyclohex-1-en-1-yl)methyl)piperazin-1-yl)benzoyl)-3-((trifluoromethyl)sulfonyl)benzenesulfonamide | 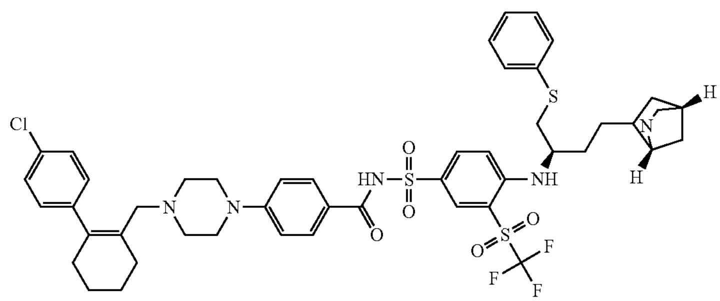 [SMILES: O=C(NS(=O)(=O)c1ccc(N[C@H](CCC2C[C@H]3CN[C@@H]2C3)CSc2ccccc2)c(S(=O)(=O)C(F)(F)F)c1)c1ccc(N2CCN(CC3=C(c4ccc(Cl)cc4)CCCC3)CC2)cc1] |
| N-(4-(4-((4'-chloro(1,1'-biphenyl)-2-yl)methyl)piperazin-1-yl)benzoyl)-4-(((1R)-3-hydroxy-1-((phenylsulfanyl)methyl)propyl)amino)-3-(methylsulfonyl)benzenesulfonamide | 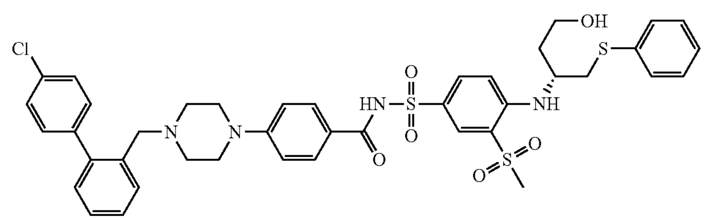 [SMILES: CS(=O)(=O)c1cc(S(=O)(=O)NC(=O)c2ccc(N3CCN(Cc4ccccc4-c4ccc(Cl)cc4)CC3)cc2)ccc1N[C@H](CCO)CSc1ccccc1] |
| N-(4-(4-((4'-chloro(1,1'-biphenyl)-2-yl)methyl)piperazin-1-yl)benzoyl)-4-(((1R)-3-(diisopropylamino)-1-((phenylsulfanyl)methyl)propyl)amino)-3-(methylsulfonyl)benzenesulfonamide | 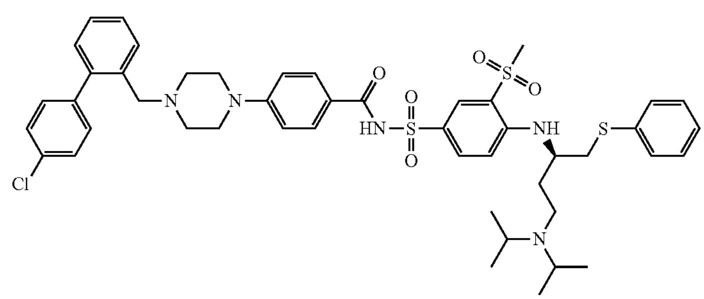 [SMILES: CC(C)N(CC[C@H](CSc1ccccc1)Nc1ccc(S(=O)(=O)NC(=O)c2ccc(N3CCN(Cc4ccccc4-c4ccc(Cl)cc4)CC3)cc2)cc1S(C)(=O)=O)C(C)C] |
| N-(4-(4-((4'-chloro(1,1'-biphenyl)-2-yl)methyl)piperazin-1-yl)benzoyl)-3-(methylsulfonyl)-4-(((1R)-1-((phenylsulfanyl)methyl)-3-(pyrrolidin-1-yl)propyl)amino)benzenesulfonamide | 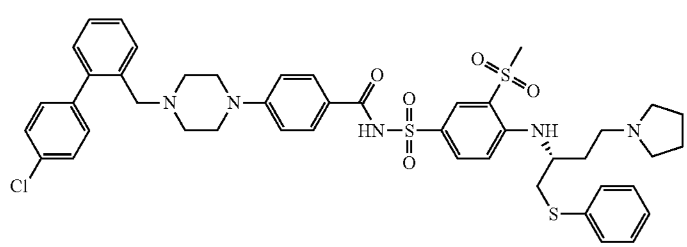 [SMILES: CS(=O)(=O)c1cc(S(=O)(=O)NC(=O)c2ccc(N3CCN(Cc4ccccc4-c4ccc(Cl)cc4)CC3)cc2)ccc1N[C@H](CCN1CCCC1)CSc1ccccc1] |

| Name | Structure |
|---|---|
| (3R)-3-(4-(((4-(4-((4'-chloro(1,1'-biphenyl)-2-yl)methyl)piperazin-1-yl)benzoyl)amino)sulfonyl)-2-(methylsulfonyl)anilino)-N,N-diisopropyl-4-(phenylsulfanyl)butanamide | 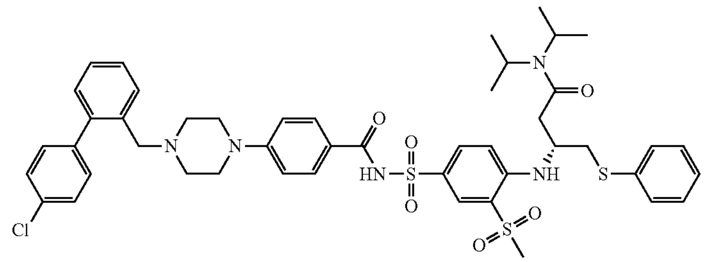 [SMILES: CC(C)N(C(=O)C[C@H](CSc1ccccc1)Nc1ccc(S(=O)(=O)NC(=O)c2ccc(N3CCN(Cc4ccccc4-c4ccc(Cl)cc4)CC3)cc2)cc1S(C)(=O)=O)C(C)C] |
| (3R)-3-(4-(((4-(4-((4'-chloro(1,1'-biphenyl)-2-yl)methyl)piperazin-1-yl)benzoyl)amino)sulfonyl)-2-(methylsulfonyl)anilino)-N-isopropyl-N-methyl-4-(phenylsulfanyl)butanamide | 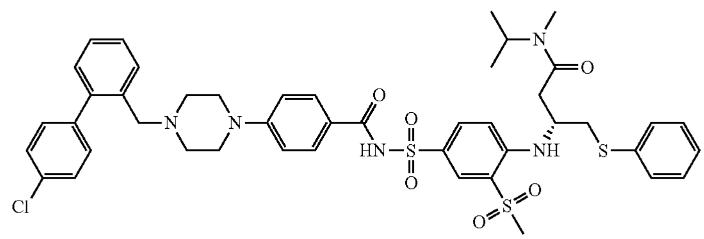 [SMILES: CC(C)N(C)C(=O)C[C@H](CSc1ccccc1)Nc1ccc(S(=O)(=O)NC(=O)c2ccc(N3CCN(Cc4ccccc4-c4ccc(Cl)cc4)CC3)cc2)cc1S(C)(=O)=O] |
| 4-(((1R)-3-(azetidin-1-yl)-3-oxo-1-((phenylsulfanyl)methyl)propyl)amino)-N-(4-(4-((4'-chloro(1,1'-biphenyl)-2-yl)methyl)piperazin-1-yl)benzoyl)-3-(methylsulfonyl)benzenesulfonamide | 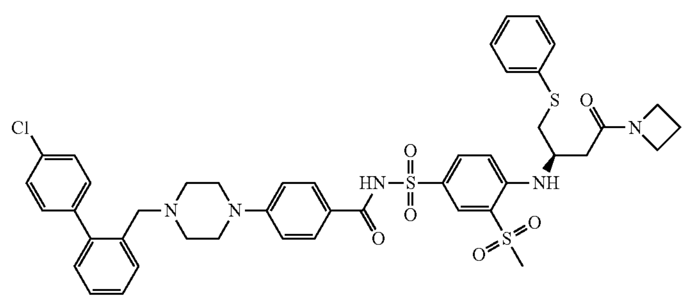 [SMILES: CS(=O)(=O)c1cc(S(=O)(=O)NC(=O)c2ccc(N3CCN(Cc4ccccc4-c4ccc(Cl)cc4)CC3)cc2)ccc1N[C@@H](CSc1ccccc1)CC(=O)N1CCC1] |
| N-(4-(4-((4'-chloro(1,1'-biphenyl)-2-yl)methyl)piperazin-1-yl)benzoyl)-4-(((1R)-3-(diethylamino)-1-((phenylsulfanyl)methyl)propyl)amino)-3-(methylsulfonyl)benzenesulfonamide | 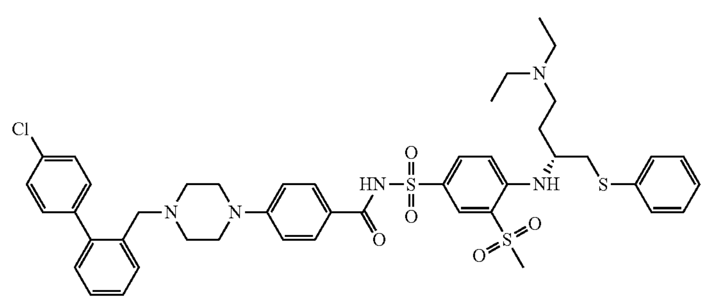 [SMILES: CCN(CC)CC[C@H](CSc1ccccc1)Nc1ccc(S(=O)(=O)NC(=O)c2ccc(N3CCN(Cc4ccccc4-c4ccc(Cl)cc4)CC3)cc2)cc1S(C)(=O)=O] |
| N-(4-(4-((4'-chloro(1,1'-biphenyl)-2-yl)methyl)piperazin-1-yl)benzoyl)-4-(((1R)-3-(isopropyl(methyl)amino)-1-((phenylsulfanyl)methyl)propyl)amino)-3-(methylsulfonyl)benzenesulfonamide | 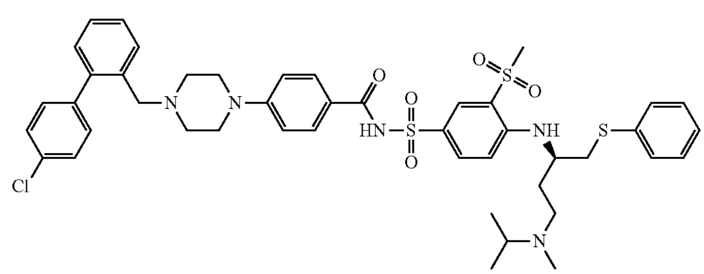 [SMILES: CC(C)N(C)CC[C@H](CSc1ccccc1)Nc1ccc(S(=O)(=O)NC(=O)c2ccc(N3CCN(Cc4ccccc4-c4ccc(Cl)cc4)CC3)cc2)cc1S(C)(=O)=O] |
| 4-(((1R)-3-(azetidin-1-yl)-1-((phenylsulfanyl)methyl)propyl)amino)-N-(4-(4-((4'-chloro(1,1'-biphenyl)-2-yl)methyl)piperazin-1-yl)benzoyl)-3-(methylsulfonyl)benzenesulfonamide | 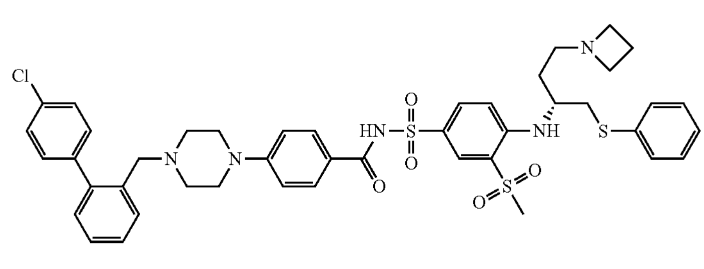 [SMILES: CS(=O)(=O)c1cc(S(=O)(=O)NC(=O)c2ccc(N3CCN(Cc4ccccc4-c4ccc(Cl)cc4)CC3)cc2)ccc1N[C@H](CCN1CCC1)CSc1ccccc1] |

-continued

| Name | Structure |
|---|---|
| N-(4-(4-((4'-chloro(1,1'-biphenyl)-2-yl)methyl)piperazin-1-yl)benzoyl)-3-(methylsulfonyl)-4-(((1R)-3-oxo-1-((phenylsulfanyl)methyl)-3-(pyrrolidin-1-yl)propyl)amino)benzenesulfonamide | 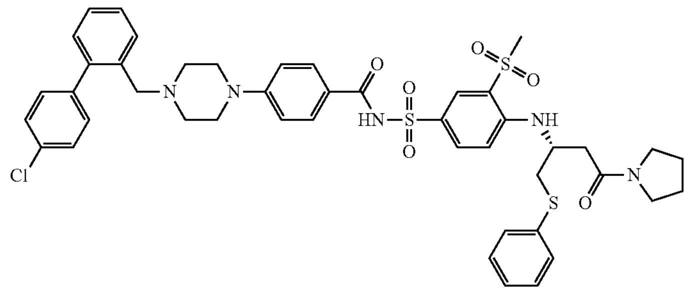 [SMILES: CS(=O)(=O)c1cc(S(=O)(=O)NC(=O)c2ccc(N3CCN(Cc4ccccc4-c4ccc(Cl)cc4)CC3)cc2)ccc1N[C@@H](CSc1ccccc1)CC(=O)N1CCCC1] |
| N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-((1,1,2,2,2-pentafluoroethyl)sulfonyl)benzenesulfonamide | 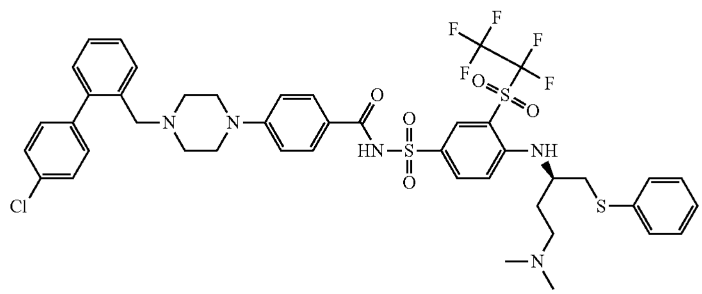 [SMILES: CN(C)CC[C@H](CSc1ccccc1)Nc1ccc(S(=O)(=O)NC(=O)c2ccc(N3CCN(Cc4ccccc4-c4ccc(Cl)cc4)CC3)cc2)cc1S(=O)(=O)C(F)(F)C(F)(F)F] |
| N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-((1,1,2,2,3,3,3-heptafluoropropyl)sulfonyl)benzenesulfonamide | 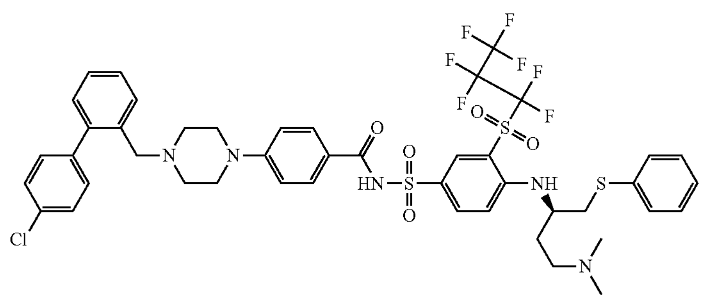 [SMILES: CN(C)CC[C@H](CSc1ccccc1)Nc1ccc(S(=O)(=O)NC(=O)c2ccc(N3CCN(Cc4ccccc4-c4ccc(Cl)cc4)CC3)cc2)cc1S(=O)(=O)C(F)(F)C(F)(F)C(F)(F)F] |
| N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-((1,2,2,2-tetrafluoro-1-(trifluoromethyl)ethyl)sulfonyl)benzenesulfonamide | 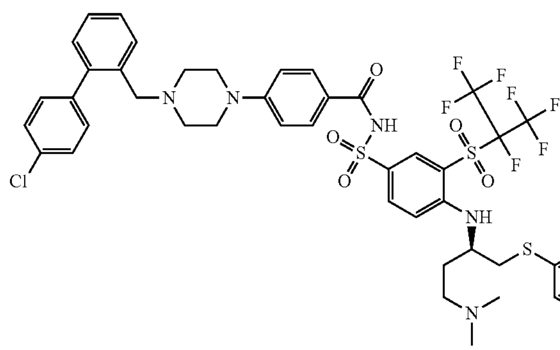 |
| N-(4-(4-((4'-chloro(1,1'-biphenyl)-2-yl)methyl)piperazin-1-yl)benzoyl)-4-(((1R)-3-(4,4-dimethyl-4,5-dihydro-1H-imidazol-1-yl)-1-((phenylsulfanyl)methyl)propyl)amino)-3-((trifluoromethyl)sulfonyl)benzenesulfonamide | 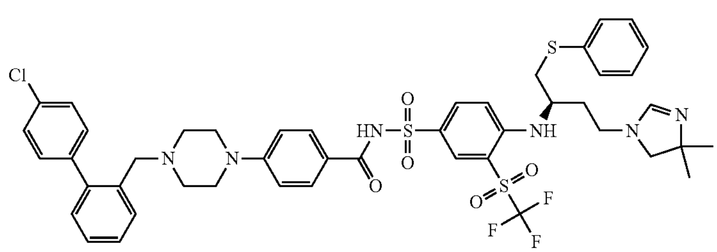 [SMILES: CC1(C)CN(CC[C@H](CSc2ccccc2)Nc2ccc(S(=O)(=O)NC(=O)c3ccc(N4CCN(Cc5ccccc5-c5ccc(Cl)cc5)CC4)cc3)cc2S(=O)(=O)C(F)(F)F)C=N1] |
| N-(4-(4-((4'-chloro(1,1'-biphenyl)-2-yl)methyl)piperazin-1-yl)benzoyl)-4-(((1R)-3-(5,6-dihydro-1(4H)-pyrimidin-1-yl)-1-((phenylsulfanyl)methyl)propyl) | |

| Name | Structure |
|---|---|
| amino)-3-((trifluoromethyl)sulfonyl) benzenesulfonamide | |
| N-(4-(4-((4'-chloro(1,1'-biphenyl)-2-yl)methyl)piperazin-1-yl)benzoyl)-4-(((1R)-3-(2,4-dimethyl-4,5-dihydro-1H-imidazol-1-yl)-1-((phenylsulfanyl)methyl)propyl)amino)-3-((trifluoromethyl)sulfonyl)benzenesulfonamide | 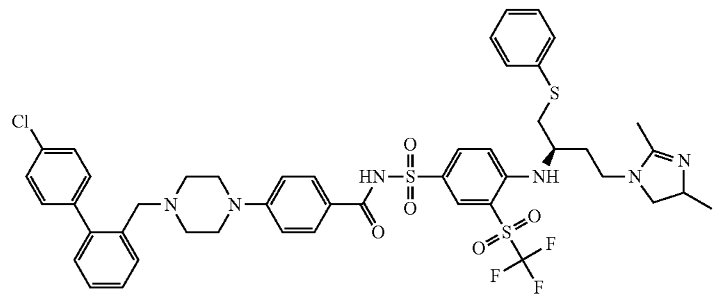 [SMILES: CC1=NC(C)CN1CC[C@H](CSc1ccccc1)Nc1ccc(S(=O)(=O)NC(=O)c2ccc(N3CCN(Cc4ccccc4-c4ccc(Cl)cc4)CC3)cc2)cc1S(=O)(=O)C(F)(F)F] |
| N-(4-(4-((4'-chloro(1,1'-biphenyl)-2-yl)methyl)piperazin-1-yl)benzoyl)-4-(((1R)-3-(2-methyl-4,5-dihydro-1H-imidazol-1-yl)-1-((phenylsulfanyl)methyl)propyl)amino)-3-((trifluoromethyl)sulfonyl)benzenesulfonamide | 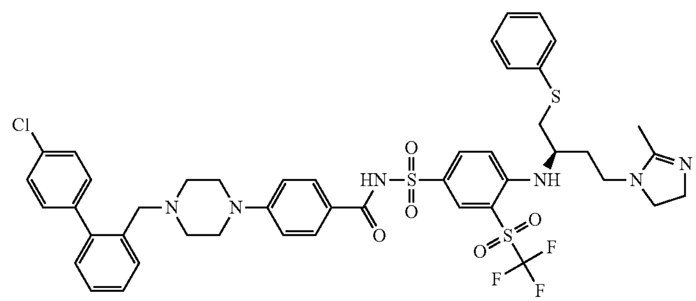 [SMILES: CC1=NCCN1CC[C@H](CSc1ccccc1)Nc1ccc(S(=O)(=O)NC(=O)c2ccc(N3CCN(Cc4ccccc4-c4ccc(Cl)cc4)CC3)cc2)cc1S(=O)(=O)C(F)(F)F] |
| N-(4-(4-((4'-chloro(1,1'-biphenyl)-2-yl)methyl)piperazin-1-yl)benzoyl)-4-(((1R)-3-(2,5-dimethylpyrrolidin-1-yl)-1-((phenylsulfanyl)methyl)propyl)amino)-3-((trifluoromethyl)sulfonyl)benzenesulfonamide | 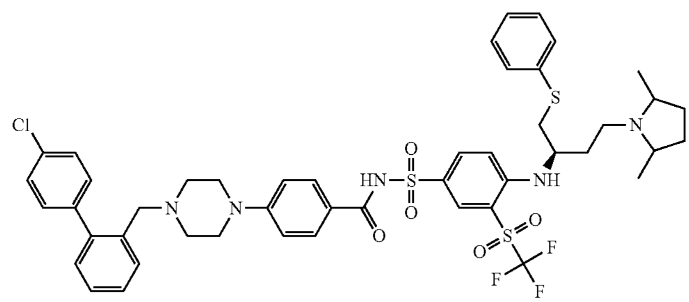 [SMILES: CC1CCC(C)N1CC[C@H](CSc1ccccc1)Nc1ccc(S(=O)(=O)NC(=O)c2ccc(N3CCN(Cc4ccccc4-c4ccc(Cl)cc4)CC3)cc2)cc1S(=O)(=O)C(F)(F)F] |
| N-(4-(4-((4'-chloro(1,1'-biphenyl)-2-yl)methyl)piperazin-1-yl)benzoyl)-4-(((1R)-3-(isopropyl(methyl)amino)-1-((phenylsulfanyl)methyl)propyl)amino)-3-((trifluoromethyl)sulfonyl)benzenesulfonamide | 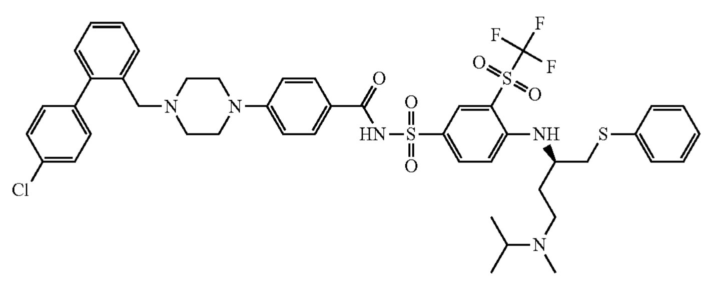 [SMILES: CC(C)N(C)CC[C@H](CSc1ccccc1)Nc1ccc(S(=O)(=O)NC(=O)c2ccc(N3CCN(Cc4ccccc4-c4ccc(Cl)cc4)CC3)cc2)cc1S(=O)(=O)C(F)(F)F] |
| N-(4-(4-((2-(4-chlorophenyl)cyclohept-1-en-1-yl)methyl)piperazin-1-yl)benzoyl)-4-(((1R)-3-(diisopropylamino)-1-((phenylsulfanyl)methyl)propyl)amino)-3-((trifluoromethyl)sulfonyl)benzenesulfonamide | 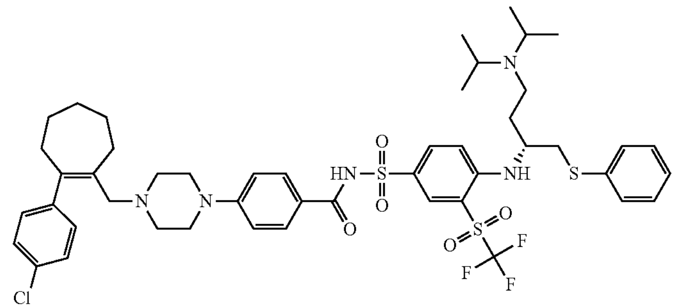 [SMILES: CC(C)N(CC[C@H](CSc1ccccc1)Nc1ccc(S(=O)(=O)NC(=O)c2ccc(N3CCN(CC4=C(c5ccc(Cl)cc5)CCCCC4)CC3)cc2)cc1S(=O)(=O)C(F)(F)F)C(C)C] |

-continued

| Name | Structure |
|---|---|
| 4-(((1R)-3-(bis(2-methoxyethyl)amino)-1-((phenylsulfanyl)methyl)propyl)amino)-N-(4-(4-((2-(4-chlorophenyl)cyclohex-1-en-1-yl)methyl)piperazin-1-yl)benzoyl)-3-((trifluoromethyl)sulfonyl)benzenesulfonamide | 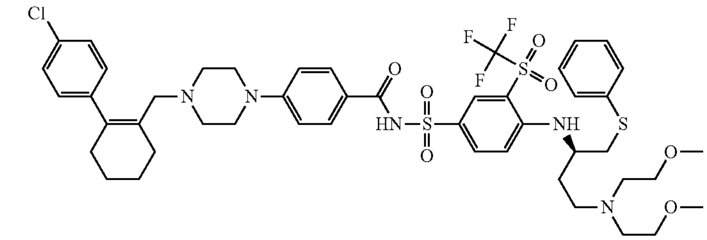 [SMILES: COCCN(CCOC)CC[C@H](CSc1ccccc1)Nc1ccc(S(=O)(=O)NC(=O)c2ccc(N3CCN(CC4=C(c5ccc(Cl)cc5)CCCC4)CC3)cc2)cc1S(=O)(=O)C(F)(F)F] |
| N-(4-(4-((2-(4-chlorophenyl)cyclohex-1-en-1-yl)methyl)piperazin-1-yl)benzoyl)-4-(((1R)-3-(1,4,7-dioxazonan-7-yl)-1-((phenylsulfanyl)methyl)propyl)amino)-3-((trifluoromethyl)sulfonyl)benzenesulfonamide | 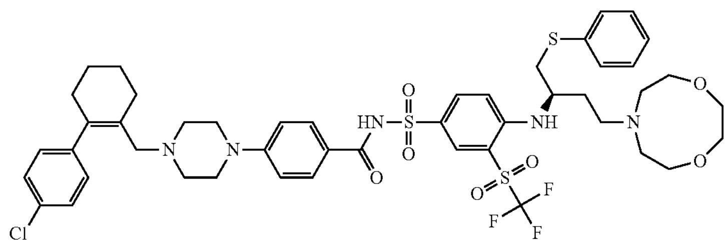 [SMILES: O=C(NS(=O)(=O)c1ccc(N[C@H](CCN2CCOCCOCC2)CSc2ccccc2)c(S(=O)(=O)C(F)(F)F)c1)c1ccc(N2CCN(CC3=C(c4ccc(Cl)cc4)CCCC3)CC2)cc1] |
| N-(4-(4-((2-(4-chlorophenyl)cyclohex-1-en-1-yl)methyl)piperazin-1-yl)benzoyl)-4-(((1R)-3-(2-methylpyrrolidin-1-yl)-1-((phenylsulfanyl)methyl)propyl)amino)-3-((trifluoromethyl)sulfonyl)benzenesulfonamide | 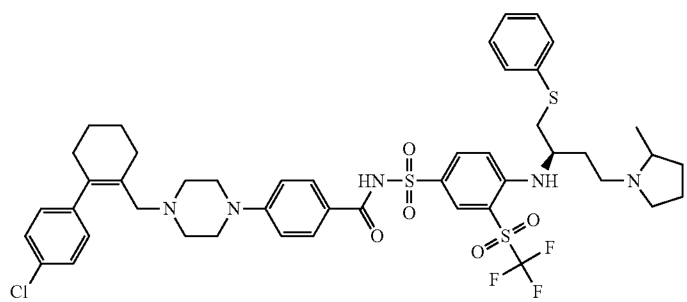 [SMILES: CC1CCCN1CC[C@H](CSc1ccccc1)Nc1ccc(S(=O)(=O)NC(=O)c2ccc(N3CCN(CC4=C(c5ccc(Cl)cc5)CCCC4)CC3)cc2)cc1S(=O)(=O)C(F)(F)F] |
| N-(4-(4-((2-(4-chlorophenyl)cyclohex-1-en-1-yl)methyl)piperazin-1-yl)benzoyl)-4-(((1R)-3-(4,4-difluoropiperidin-1-yl)-1-((phenylsulfanyl)methyl)propyl)amino)-3-((trifluoromethyl)sulfonyl)benzenesulfonamide | 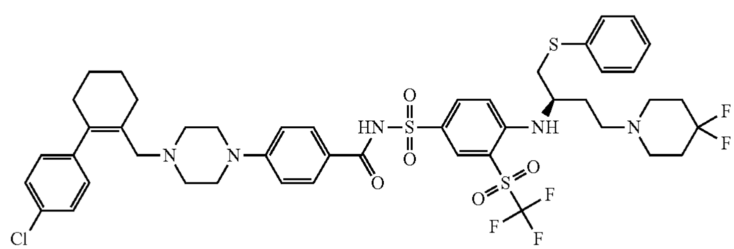 [SMILES: O=C(NS(=O)(=O)c1ccc(N[C@H](CCN2CCC(F)(F)CC2)CSc2ccccc2)c(S(=O)(=O)C(F)(F)F)c1)c1ccc(N2CCN(CC3=C(c4ccc(Cl)cc4)CCCC3)CC2)cc1] |
| N-(4-(4-((2-(4-chlorophenyl)cyclohex-1-en-1-yl)methyl)piperazin-1-yl)benzoyl)-4-(((1R)-3-((3R,5S)-3,5-dimethoxypiperidin-1-yl)-1-((phenylsulfanyl)methyl)propyl)amino)-3-((trifluoromethyl)sulfonyl)benzenesulfonamide | 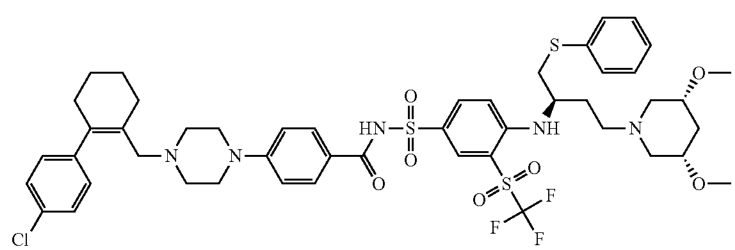 [SMILES: CO[C@@H]1C[C@H](OC)CN(CC[C@H](CSc2ccccc2)Nc2ccc(S(=O)(=O)NC(=O)c3ccc(N4CCN(CC5=C(c6ccc(Cl)cc6)CCCC5)CC4)cc3)cc2S(=O)(=O)C(F)(F)F)C1] |
| N-(4-(4-((2-(4-chlorophenyl)cyclohex-1-en-1-yl)methyl)piperazin-1-yl)benzoyl)-4-(((1R)-3-((2S)-2-(methoxymethyl)pyrrolidin-1-yl)-1-((phenylsulfanyl)methyl)propyl)amino)-3-((trifluoromethyl)sulfonyl)benzenesulfonamide | 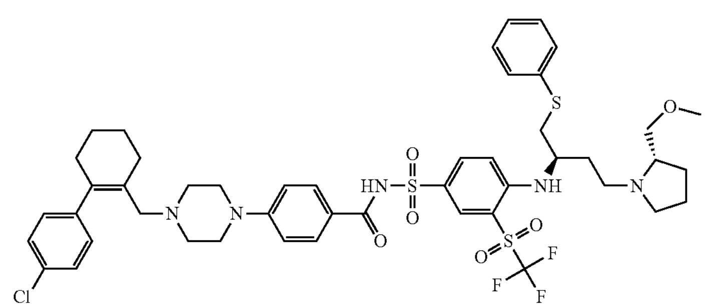 [SMILES: COC[C@@H]1CCCN1CC[C@H](CSc1ccccc1)Nc1ccc(S(=O)(=O)NC(=O)c2ccc(N3CCN(CC4=C(c5ccc(Cl)cc5)CCCC4)CC3)cc2)cc1S(=O)(=O)C(F)(F)F] |

-continued

| Name | Structure |
|---|---|
| N-(4-(4-((2-(4-chlorophenyl)cyclohex-1-en-1-yl)methyl)piperazin-1-yl)benzoyl)-4-(((1R)-1-((phenylsulfanyl)methyl)-3-(1,3-thiazolidin-3-yl)propyl)amino)-3-((trifluoromethyl)sulfonyl)benzenesulfonamide | 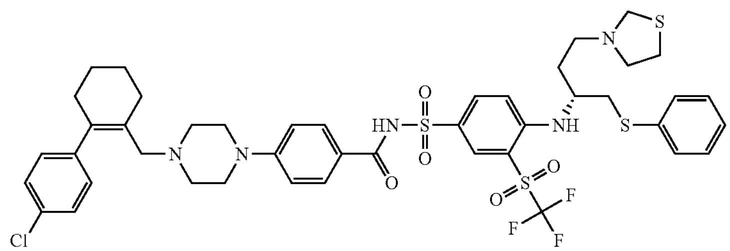 |
| N-(4-(4-((2-(4-chlorophenyl)cyclohex-1-en-1-yl)methyl)piperazin-1-yl)benzoyl)-4-(((1R)-3-((3S)-3-methylmorpholin-4-yl)-1-((phenylsulfanyl)methyl)propyl)amino)-3-((trifluoromethyl)sulfonyl)benzenesulfonamide | 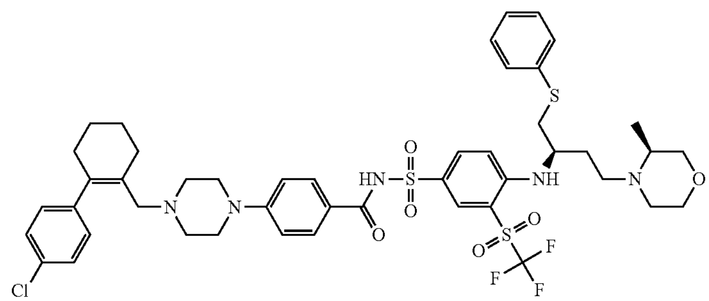 [SMILES: C[C@H]1COCCN1CC[C@H](CSc1ccccc1)Nc1ccc(S(=O)(=O)NC(=O)c2ccc(N3CCN(CC4=C(c5ccc(Cl)cc5)CCCC4)CC3)cc2)cc1S(=O)(=O)C(F)(F)F] |
| N-(4-(4-((2-(4-chlorophenyl)cyclohex-1-en-1-yl)methyl)piperazin-1-yl)benzoyl)-4-(((1R)-3-(1-hydroxy-3,7-dioxa-9-azabicyclo[3.3.1]non-9-yl)-1-((phenylsulfanyl)methyl)propyl)amino)-3-((trifluoromethyl)sulfonyl)benzenesulfonamide | 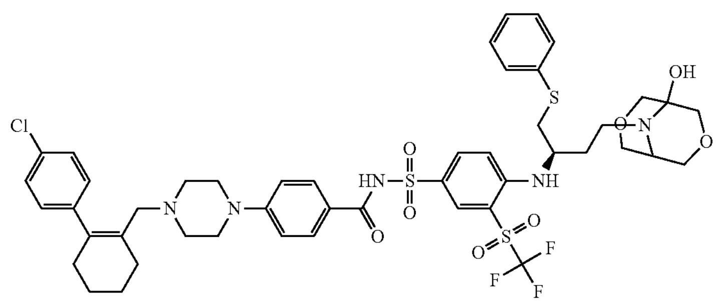 [SMILES: O=C(NS(=O)(=O)c1ccc(N[C@H](CCN2C3COCC2(O)COC3)CSc2ccccc2)c(S(=O)(=O)C(F)(F)F)c1)c1ccc(N2CCN(CC3=C(c4ccc(Cl)cc4)CCCC3)CC2)cc1] |
| N-(4-(4-((2-(4-chlorophenyl)cyclohex-1-en-1-yl)methyl)piperazin-1-yl)benzoyl)-4-(((1S)-3-(3,7-dioxa-9-azabicyclo[3.3.1]non-9-yl)-1-(2-phenylethyl)propyl)amino)-3-((trifluoromethyl)sulfonyl)benzenesulfonamide | 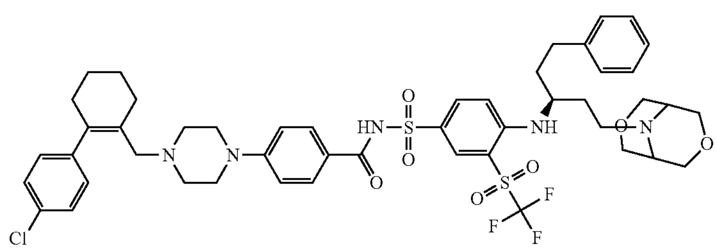 [SMILES: O=C(NS(=O)(=O)c1ccc(N[C@@H](CCc2ccccc2)CCN2C3COCC2COC3)c(S(=O)(=O)C(F)(F)F)c1)c1ccc(N2CCN(CC3=C(c4ccc(Cl)cc4)CCCC3)CC2)cc1] |
| N-(4-(4-((2-(4-chlorophenyl)cyclohex-1-en-1-yl)methyl)piperazin-1-yl)benzoyl)-3-((difluoromethyl)sulfonyl)-4-(((1R)-3-(morpholin-4-yl)-1-((phenylsulfanyl)methyl)propyl)amino)benzenesulfonamide | 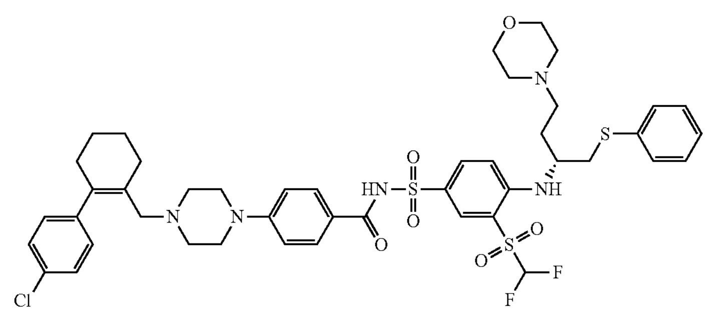 [SMILES: O=C(NS(=O)(=O)c1ccc(N[C@H](CCN2CCOCC2)CSc2ccccc2)c(S(=O)(=O)C(F)F)c1)c1ccc(N2CCN(CC3=C(c4ccc(Cl)cc4)CCCC3)CC2)cc1] |

| Name | Structure |
|---|---|
| N-(4-(4-((2-(4-chlorophenyl)cyclohex-1-en-1-yl)methyl)piperazin-1-yl)benzoyl)-3-((difluoromethyl)sulfonyl)-4-(((1R)-3-(dimethylamino)-1-((phenylsulfanyl)methyl)propyl)amino)benzenesulfonamide | 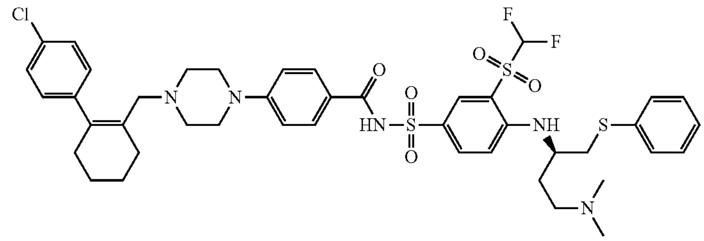 [SMILES: CN(C)CC[C@H](CSc1ccccc1)Nc1ccc(S(=O)(=O)NC(=O)c2ccc(N3CCN(CC4=C(c5ccc(Cl)cc5)CCCC4)CC3)cc2)cc1S(=O)(=O)C(F)F] |
| N-(4-(4-((2-(4-chlorophenyl)cyclohex-1-en-1-yl)methyl)piperazin-1-yl)benzoyl)-4-(((1R)-3-(dimethylamino)-1-((phenylsulfanyl)methyl)propyl)oxy)-3-(ethylsulfonyl)benzenesulfonamide | 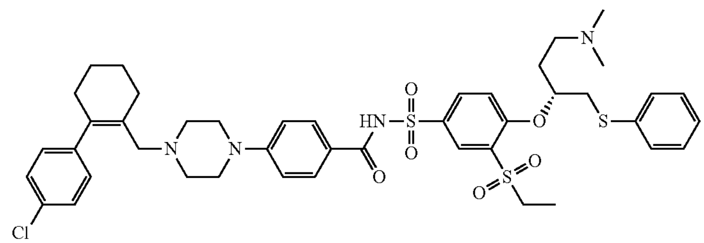 |
| 3-((chloro(difluoro)methyl)sulfonyl)-N-(4-(4-((4-(4-chlorophenyl)-5,6-dihydro-2H-pyran-3-yl)methyl)piperazin-1-yl)benzoyl)-4-(((1R)-3-(dimethylamino)-1-((phenylsulfanyl)methyl)propyl)amino)benzenesulfonamide | 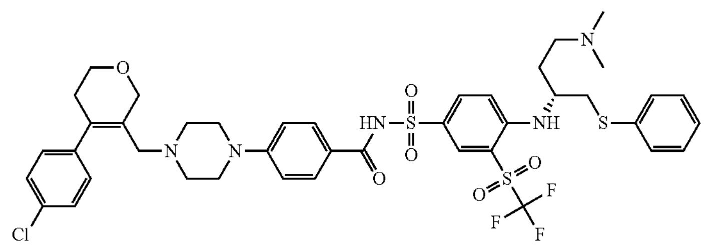 |
| N-(4-(4-((4-(4-chlorophenyl)-5,6-dihydro-2H-pyran-3-yl)methyl)piperazin-1-yl)benzoyl)-3-((difluoromethyl)sulfonyl)-4-(((1R)-3-(dimethylamino)-1-((phenylsulfanyl)methyl)propyl)amino)benzenesulfonamide | 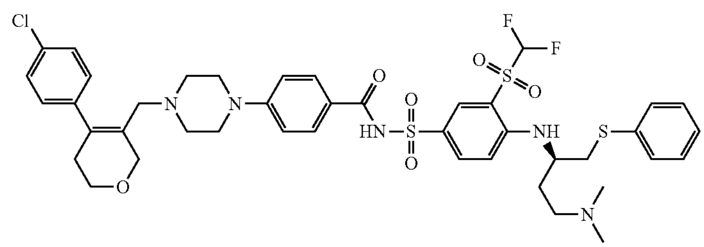 [SMILES: CN(C)CC[C@H](CSc1ccccc1)Nc1ccc(S(=O)(=O)NC(=O)c2ccc(N3CCN(CC4=C(c5ccc(Cl)cc5)CCOC4)CC3)cc2)cc1S(=O)(=O)C(F)F] |
| 3-((chloro(difluoro)methyl)sulfonyl)-N-(4-(4-((4-(4-chlorophenyl)-5,6-dihydro-2H-pyran-3-yl)methyl)piperazin-1-yl)benzoyl)-4-(((1R)-3-(morpholin-4-yl)-1-((phenylsulfanyl)methyl)propyl)amino)benzenesulfonamide | 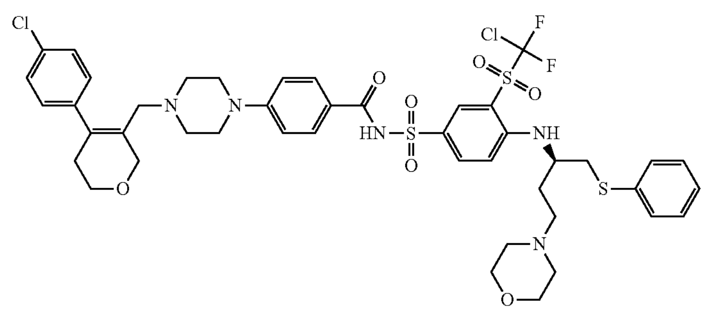 |
| N-(4-(4-((4-(4-chlorophenyl)-5,6-dihydro-2H-pyran-3-yl)methyl)piperazin-1-yl)benzoyl)-4-(((1R)-3-(dimethylamino)-1-((phenylsulfanyl)methyl)propyl)oxy)-3-(ethylsulfonyl)benzenesulfonamide | 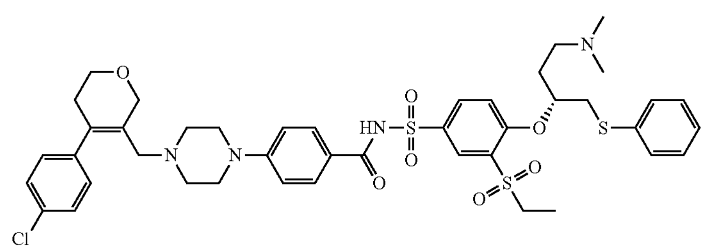 [SMILES: CCS(=O)(=O)c1cc(S(=O)(=O)NC(=O)c2ccc(N3CCN(CC4=C(c5ccc(Cl)cc5)CCOC4)CC3)cc2)ccc1O[C@H](CCN(C)C)CSc1ccccc1] |

-continued

| Name | Structure |
|---|---|
| N-(4-(4-((4-(4-chlorophenyl)-5,6-dihydro-2H-pyran-3-yl)methyl)piperazin-1-yl)benzoyl)-3-((difluoromethyl)sulfonyl)-4-(((1R)-3-(morpholin-4-yl)-1-((phenylsulfanyl)methyl)propyl)amino)benzenesulfonamide | 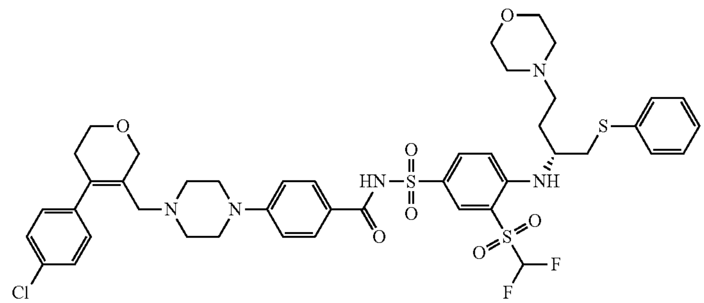 |
| N-(4-(4-((2-(4-chlorophenyl)-5,5-dimethylcyclohex-1-en-1-yl)methyl)piperazin-1-yl)benzoyl)-4-(((1R)-3-(1,4-oxazepan-4-yl)-1-((phenylsulfanyl)methyl)propyl)amino)-3-((trifluoromethyl)sulfonyl)benzenesulfonamide | 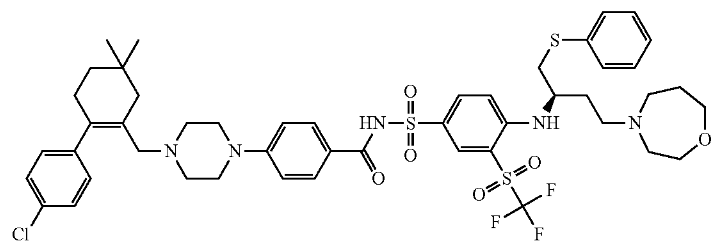 |
| N-(4-(4-((2-(4-chlorophenyl)cyclohept-1-en-1-yl)methyl)piperazin-1-yl)benzoyl)-4-(((1R)-3-(1,4-oxazepan-4-yl)-1-((phenylsulfanyl)methyl)propyl)amino)-3-((trifluoromethyl)sulfonyl)benzenesulfonamide | 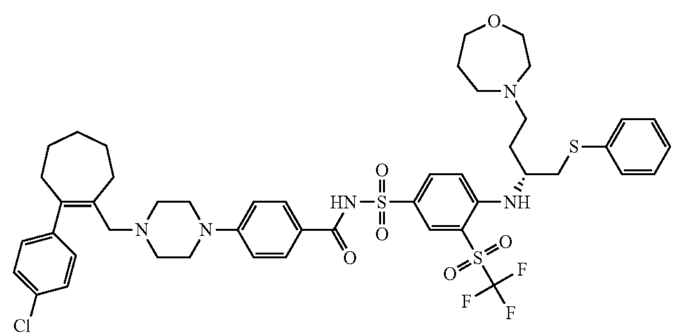 [SMILES: O=C(NS(=O)(=O)c1ccc(N[C@H](CCN2CCCOCC2)CSc2ccccc2)c(S(=O)(=O)C(F)(F)F)c1)c1ccc(N2CCN(CC3=C(c4ccc(Cl)cc4)CCCCC3)CC2)cc1] |
| 3-((chloro(difluoro)methyl)sulfonyl)-N-(4-(4-((2-(4-chlorophenyl)cyclohept-1-en-1-yl)methyl)piperazin-1-yl)benzoyl)-4-(((1R)-3-(dimethylamino)-1-((phenylsulfanyl)methyl)propyl)amino)benzenesulfonamide | 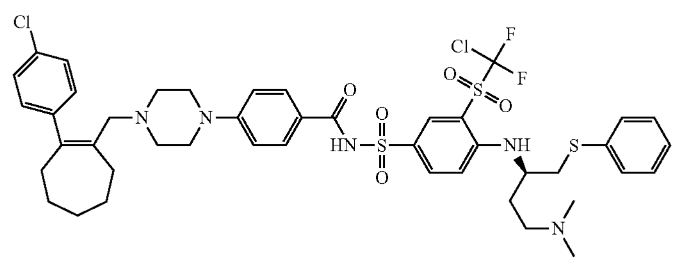 |
| 3-((chloro(difluoro)methyl)sulfonyl)-N-(4-(4-((2-(4-chlorophenyl)cyclohept-1-en-1-yl)methyl)piperazin-1-yl)benzoyl)-4-(((1R)-3-(morpholin-4-yl)-1-((phenylsulfanyl)methyl)propyl)amino)benzenesulfonamide | 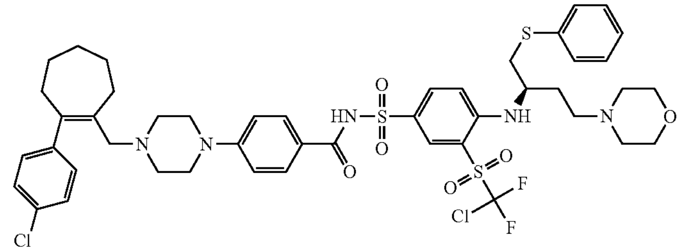 |

-continued

| Name | Structure |
|---|---|
| 3-((chloro(difluoro)methyl)sulfonyl)-N-(4-(4-((2-(4-chlorophenyl)-5,5-dimethylcyclohex-1-en-1-yl)methyl)piperazin-1-yl)benzoyl)-4-(((1R)-3-(dimethylamino)-1-((phenylsulfanyl)methyl)propyl)amino)benzenesulfonamide | 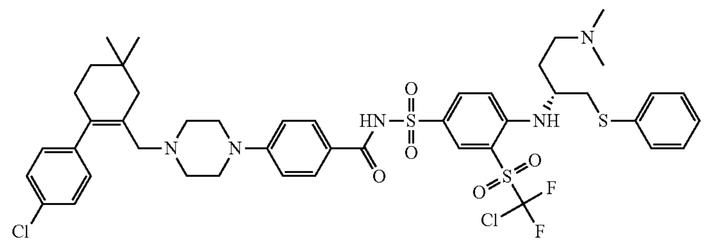 |
| 3-((chloro(difluoro)methyl)sulfonyl)-N-(4-(4-((2-(4-chlorophenyl)cyclohex-1-en-1-yl)methyl)piperazin-1-yl)benzoyl)-4-(((1R)-3-(1,4-oxazepan-4-yl)-1-((phenylsulfanyl)methyl)propyl)amino)benzenesulfonamide | 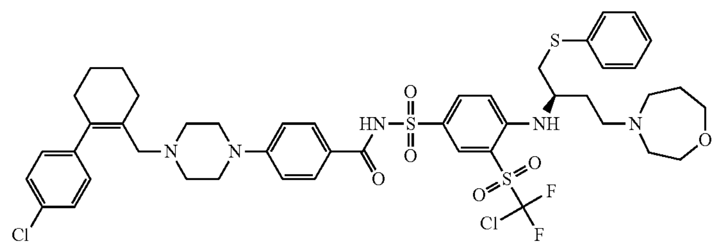 |
| 3-((chloro(difluoro)methyl)sulfonyl)-N-(4-(4-((2-(4-chlorophenyl)cyclohept-1-en-1-yl)methyl)piperazin-1-yl)benzoyl)-4-(((1R)-3-(1,4-oxazepan-4-yl)-1-((phenylsulfanyl)methyl)propyl)amino)benzenesulfonamide | 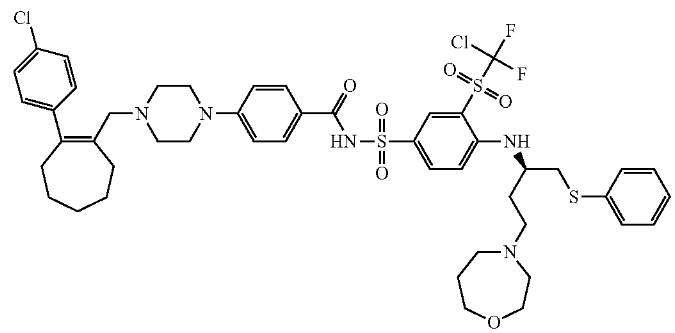 [SMILES: O=C(NS(=O)(=O)c1ccc(N[C@H](CCN2CCCOCC2)CSc2ccccc2)c(S(=O)(=O)C(F)(F)Cl)c1)c1ccc(N2CCN(CC3=C(c4ccc(Cl)cc4)CCCCC3)CC2)cc1] |
| 3-((chloro(difluoro)methyl)sulfonyl)-N-(4-(4-((2-(4-chlorophenyl)-5,5-dimethylcyclohex-1-en-1-yl)methyl)piperazin-1-yl)benzoyl)-4-(((1R)-3-(1,4-oxazepan-4-yl)-1-((phenylsulfanyl)methyl)propyl)amino)benzenesulfonamide | 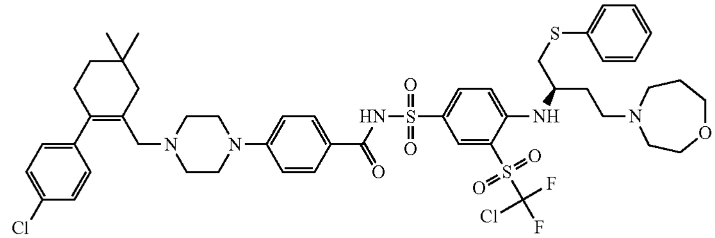 |
| 3-((chloro(difluoro)methyl)sulfonyl)-N-(4-(4-((2-(4-chlorophenyl)-4,4-dimethylcyclohex-1-en-1-yl)methyl)piperazin-1-yl)benzoyl)-4-(((1R)-3-(1,4-oxazepan-4-yl)-1-((phenylsulfanyl)methyl)propyl)amino)benzenesulfonamide | 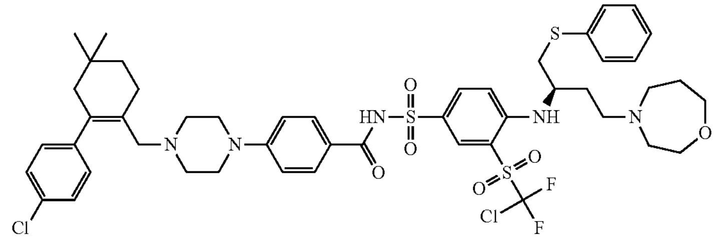 [SMILES: CC1(C)CCC(CN2CCN(c3ccc(C(=O)NS(=O)(=O)c4ccc(N[C@H](CCN5CCCOCC5)CSc5ccccc5)c(S(=O)(=O)C(F)(F)Cl)c4)cc3)CC2)=C(c2ccc(Cl)cc2)C1] |
| 3-((chloro(difluoro)methyl)sulfonyl)-N-(4-(4-((2-(4-chlorophenyl)cyclohex-1-en-1-yl)methyl)piperazin-1-yl)benzoyl)-4-(((1R)-3-(isopropyl(methyl)amino)-1-((phenylsulfanyl)methyl)propyl)amino)benzenesulfonamide | 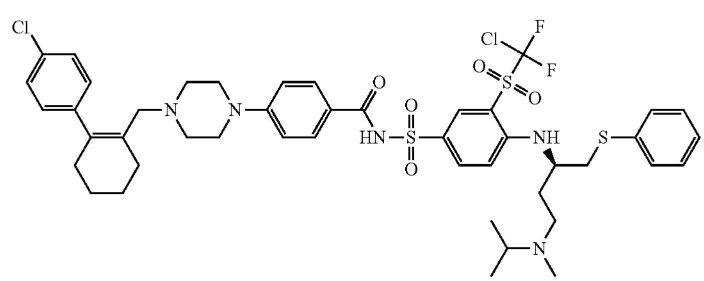 |

| Name | Structure |
|---|---|
| 3-((chloro(difluoro)methyl)sulfonyl)-N-(4-(4-((2-(4-chlorophenyl)cyclohept-1-en-1-yl)methyl)piperazin-1-yl)benzoyl)-4-(((1R)-3-(isopropyl(methyl)amino)-1-((phenylsulfanyl)methyl)propyl)amino)benzenesulfonamide | 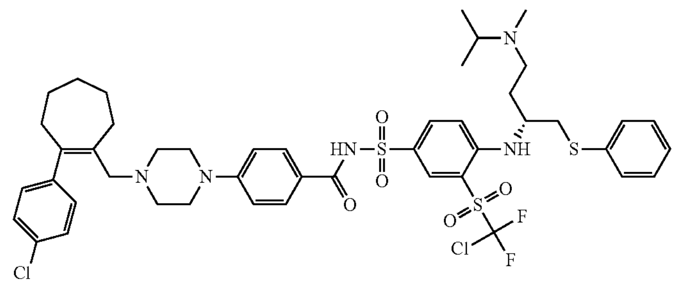 [SMILES: CC(C)N(C)CC[C@H](CSc1ccccc1)Nc1ccc(S(=O)(=O)NC(=O)c2ccc(N3CCN(CC4=C(c5ccc(Cl)cc5)CCCCC4)CC3)cc2)cc1S(=O)(=O)C(F)(F)Cl] |
| N-(4-(4-((2-(4-chlorophenyl)-4,4-dimethylcyclohex-1-en-1-yl)methyl)piperazin-1-yl)benzoyl)-4-(((1R)-3-(1,4-oxazepan-4-yl)-1-((phenylsulfanyl)methyl)propyl)amino)-3-((trifluoromethyl)sulfonyl)benzenesulfonamide | 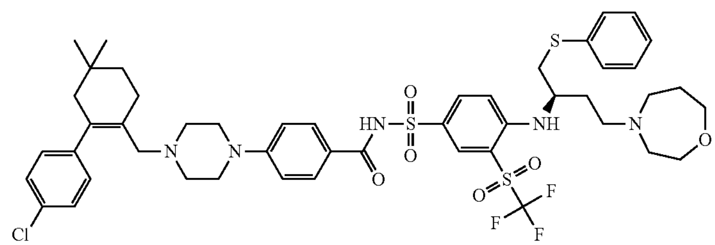 |
| N-(4-(4-((4-(4-chlorophenyl)-5,6-dihydro-2H-pyran-3-yl)methyl)piperazin-1-yl)benzoyl)-4-(((1R)-3-(dimethylamino)-1-((phenylsulfanyl)methyl)propyl)amino)-3-((trifluoromethyl)sulfonyl)benzenesulfonamide | 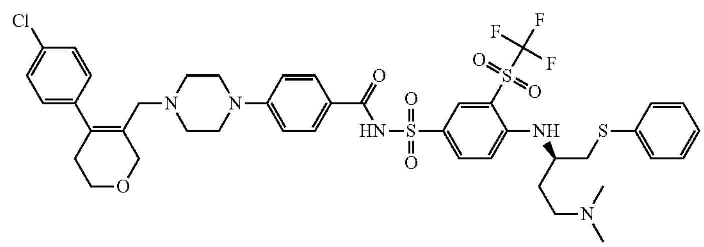 [SMILES: CN(C)CC[C@H](CSc1ccccc1)Nc1ccc(S(=O)(=O)NC(=O)c2ccc(N3CCN(CC4=C(c5ccc(Cl)cc5)CCOC4)CC3)cc2)cc1S(=O)(=O)C(F)(F)F] |
| 4-(((1R)-3-(7-azabicyclo[2.2.1]hept-7-yl)-1-((phenylsulfanyl)methyl)propyl)amino)-N-(4-(4-((2-(4-chlorophenyl)-5,5-dimethylcyclohex-1-en-1-yl)methyl)piperazin-1-yl)benzoyl)-3-((trifluoromethyl)sulfonyl)benzenesulfonamide | 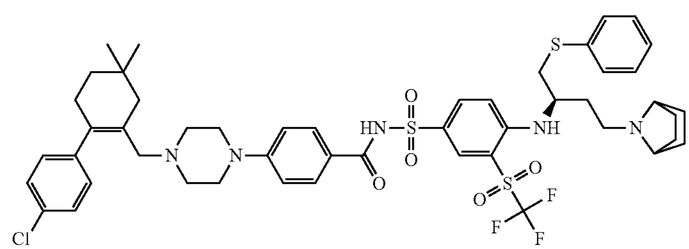 [SMILES: CC1(C)CCC(c2ccc(Cl)cc2)=C(CN2CCN(c3ccc(C(=O)NS(=O)(=O)c4ccc(N[C@H](CCN5C6CCC5CC6)CSc5ccccc5)c(S(=O)(=O)C(F)(F)F)c4)cc3)CC2)C1] |
| N-(4-(4-((4-(4-chlorophenyl)-5,6-dihydro-2H-pyran-3-yl)methyl)piperazin-1-yl)benzoyl)-4-(((1R)-3-(isopropyl(methyl)amino)-1-((phenylsulfanyl)methyl)propyl)amino)-3-((trifluoromethyl)sulfonyl)benzenesulfonamide | 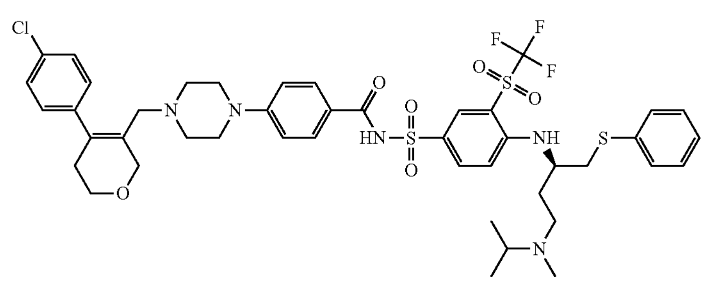 [SMILES: CC(C)N(C)CC[C@H](CSc1ccccc1)Nc1ccc(S(=O)(=O)NC(=O)c2ccc(N3CCN(CC4=C(c5ccc(Cl)cc5)CCOC4)CC3)cc2)cc1S(=O)(=O)C(F)(F)F] |

-continued

| Name | Structure |
|---|---|
| tert-butyl 4-(4-chlorophenyl)-5-((4-(4-((((4-(((1R)-3-(morpholin-4-yl)-1-((phenylsulfanyl)methyl)propyl)amino)-3-((trifluoromethyl)sulfonyl)phenyl)sulfonyl)amino)carbonyl)phenyl)piperazin-1-yl)methyl)-3,6-dihydro-1(2H)-pyridinecarboxylate | 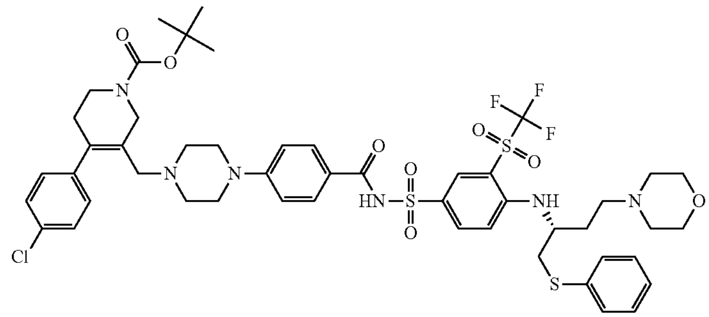 [SMILES: CC(C)(C)OC(=O)N1CCC(c2ccc(Cl)cc2)=C(CN2CCN(c3ccc(C(=O)NS(=O)(=O)c4ccc(N[C@H](CCN5CCOCC5)CSc5ccccc5)c(S(=O)(=O)C(F)(F)F)c4)cc3)CC2)C1] |
| tert-butyl 4-(4-chlorophenyl)-5-((4-(4-((((4-(((1R)-3-(dimethylamino)-1-((phenylsulfanyl)methyl)propyl)amino)-3-((trifluoromethyl)sulfonyl)phenyl)sulfonyl)amino)carbonyl)phenyl)piperazin-1-yl)methyl)-3,6-dihydro-1(2H)-pyridinecarboxylate | 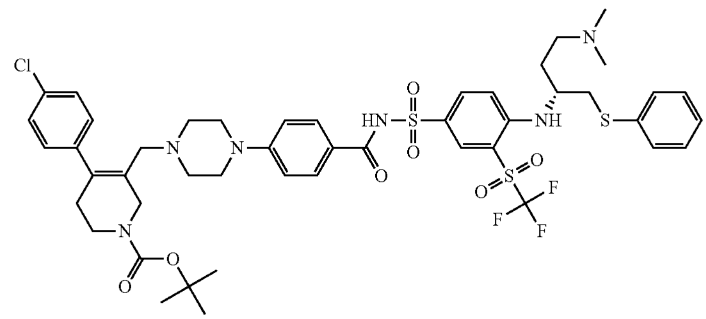 [SMILES: CN(C)CC[C@H](CSc1ccccc1)Nc1ccc(S(=O)(=O)NC(=O)c2ccc(N3CCN(CC4=C(c5ccc(Cl)cc5)CCN(C(=O)OC(C)(C)C)C4)CC3)cc2)cc1S(=O)(=O)C(F)(F)F] |
| N-(4-(4-((4-(4-chlorophenyl)-1,2,5,6-tetrahydro-3-pyridinyl)methyl)piperazin-1-yl)benzoyl)-4-(((1R)-3-(dimethylamino)-1-((phenylsulfanyl)methyl)propyl)amino)-3-((trifluoromethyl)sulfonyl)benzenesulfonamide | 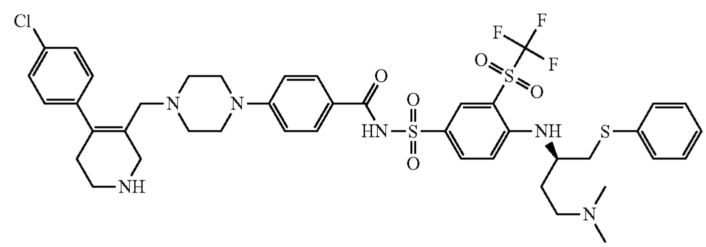 |
| N-(4-(4-((4-(4-chlorophenyl)-1,2,5,6-tetrahydro-3-pyridinyl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide | 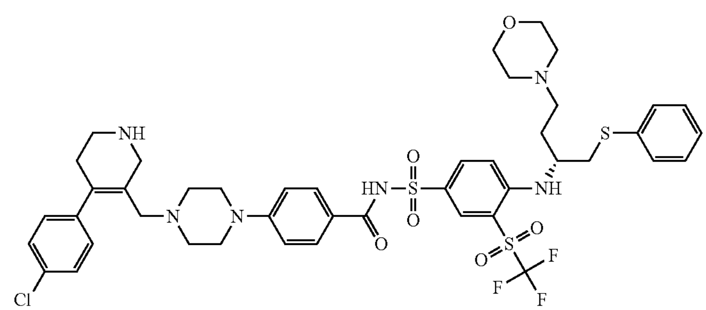 |
| N-(4-(4-((1-acetyl-4-(4-chlorophenyl)-1,2,5,6-tetrahydro-3-pyridinyl)methyl)piperazin-1-yl)benzoyl)-4-(((1R)-3-(dimethylamino)-1-((phenylsulfanyl)methyl)propyl)amino)-3-((trifluoromethyl)sulfonyl)benzenesulfonamide | 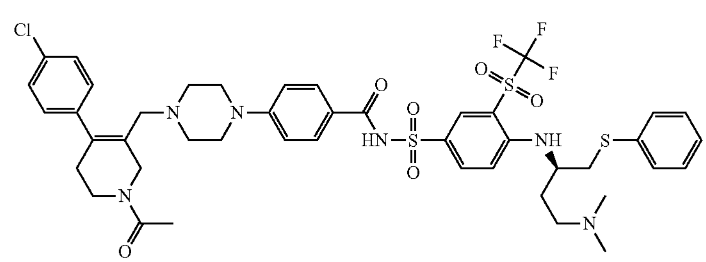 [SMILES: CC(=O)N1CCC(c2ccc(Cl)cc2)=C(CN2CCN(c3ccc(C(=O)NS(=O)(=O)c4ccc(N[C@H](CCN(C)C)CSc5ccccc5)c(S(=O)(=O)C(F)(F)F)c4)cc3)CC2)C1] |

| Name | Structure |
|---|---|
| N-(4-(4-((4-(4-chlorophenyl)-1-methyl-1,2,5,6-tetrahydro-3-pyridinyl)methyl)piperazin-1-yl)benzoyl)-4-(((1R)-3-(dimethylamino)-1-((phenylsulfanyl)methyl)propyl)amino)-3-((trifluoromethyl)sulfonyl)benzenesulfonamide | 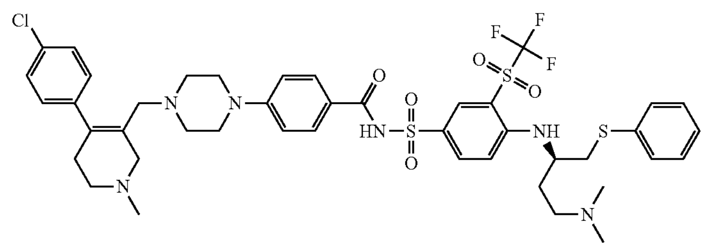 |
| N-(4-(4-((4-(4-chlorophenyl)-1-(cyclohexylmethyl)-1,2,5,6-tetrahydro-3-pyridinyl)methyl)piperazin-1-yl)benzoyl)-4-(((1R)-3-(dimethylamino)-1-((phenylsulfanyl)methyl)propyl)amino)-3-((trifluoromethyl)sulfonyl)benzenesulfonamide | 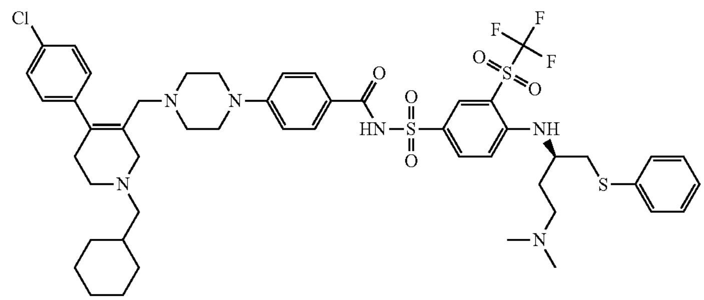 [SMILES: CN(C)CC[C@H](CSc1ccccc1)Nc1ccc(S(=O)(=O)NC(=O)c2ccc(N3CCN(CC4=C(c5ccc(Cl)cc5)CCN(CC5CCCCC5)C4)CC3)cc2)cc1S(=O)(=O)C(F)(F)F] |
| N-(4-(4-((1-acetyl-4-(4-chlorophenyl)-1,2,5,6-tetrahydro-3-pyridinyl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide | 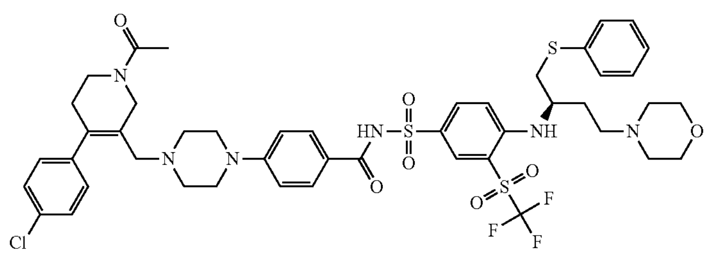 [SMILES: CC(=O)N1CCC(c2ccc(Cl)cc2)=C(CN2CCN(c3ccc(C(=O)NS(=O)(=O)c4ccc(N[C@H](CCN5CCOCC5)CSc5ccccc5)c(S(=O)(=O)C(F)(F)F)c4)cc3)CC2)C1] |
| N-(4-(4-((4-(4-chlorophenyl)-1-methyl-1,2,5,6-tetrahydro-3-pyridinyl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide | 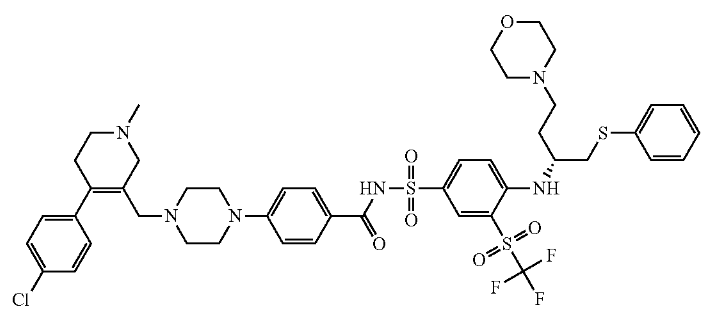 [SMILES: CN1CCC(c2ccc(Cl)cc2)=C(CN2CCN(c3ccc(C(=O)NS(=O)(=O)c4ccc(N[C@H](CCN5CCOCC5)CSc5ccccc5)c(S(=O)(=O)C(F)(F)F)c4)cc3)CC2)C1] |
| N-(4-(4-((2-(4-chlorophenyl)-4,4-dimethylcyclohex-1-en-1-yl)methyl)piperazin-1-yl)benzoyl)-4-(((1R)-3-(diethylamino)-1-((phenylsulfanyl)methyl)propyl)amino)-3-((trifluoromethyl)sulfonyl)benzenesulfonamide | 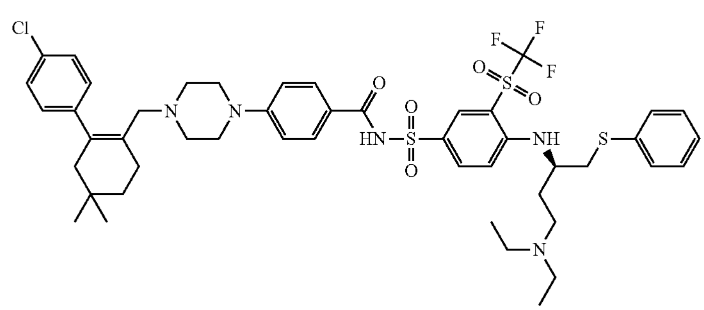 [SMILES: CCN(CC)CC[C@H](CSc1ccccc1)Nc1ccc(S(=O)(=O)NC(=O)c2ccc(N3CCN(CC4=C(c5ccc(Cl)cc5)CC(C)(C)CC4)CC3)cc2)cc1S(=O)(=O)C(F)(F)F] |

-continued

| Name | Structure |
|------|-----------|
| N-(4-(4-(((1R,2R)-2-(4-chlorophenyl)cyclohexyl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide | 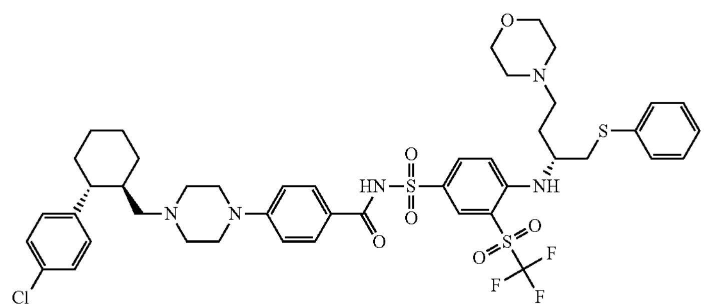 [SMILES: O=C(NS(=O)(=O)c1ccc(N[C@H](CCN2CCOCC2)CSc2ccccc2)c(S(=O)(=O)C(F)(F)F)c1)c1ccc(N2CCN(C[C@@H]3CCCC[C@H]3c3ccc(Cl)cc3)CC2)cc1] |
| 3-((chloro(difluoro)methyl)sulfonyl)-4-(((1R)-3-(morpholin-4-yl)-1-((phenylsulfanyl)methyl)propyl)amino)-N-(4-(4-((4-(4-(trifluoromethyl)phenyl)-5,6-dihydro-2H-pyran-3-yl)methyl)piperazin-1-yl)benzoyl)benzenesulfonamide | 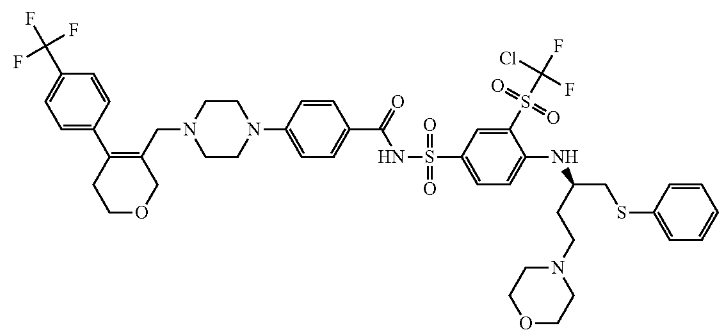 [SMILES: O=C(NS(=O)(=O)c1ccc(N[C@H](CCN2CCOCC2)CSc2ccccc2)c(S(=O)(=O)C(F)(F)Cl)c1)c1ccc(N2CCN(CC3=C(c4ccc(C(F)(F)F)cc4)CCOC3)CC2)cc1] |
| 4-(((1R)-3-(morpholin-4-yl)-1-((phenylsulfanyl)methyl)propyl)amino)-N-(4-(4-((4-(4-(trifluoromethyl)phenyl)-5,6-dihydro-2H-pyran-3-yl)methyl)piperazin-1-yl)benzoyl)-3-((trifluoromethyl)sulfonyl)benzenesulfonamide | 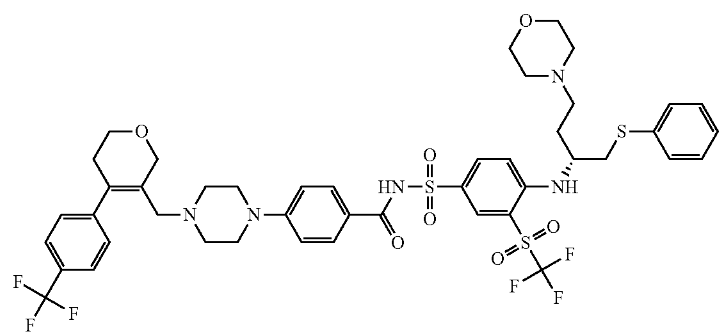 [SMILES: O=C(NS(=O)(=O)c1ccc(N[C@H](CCN2CCOCC2)CSc2ccccc2)c(S(=O)(=O)C(F)(F)F)c1)c1ccc(N2CCN(CC3=C(c4ccc(C(F)(F)F)cc4)CCOC3)CC2)cc1] |
| 3-((chloro(difluoro)methyl)sulfonyl)-N-(4-(4-((2-(4-chlorophenyl)-4,4-diethylcyclohex-1-en-1-yl)methyl)piperazin-1-yl)benzoyl)-4-(((1R)-3-(morpholin-4-yl)-1-((phenylsulfanyl)methyl)propyl)amino)benzenesulfonamide | 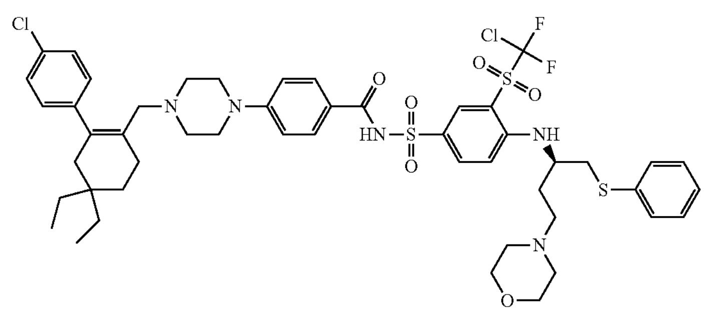 [SMILES: CCC1(CC)CCC(CN2CCN(c3ccc(C(=O)NS(=O)(=O)c4ccc(N[C@H](CCN5CCOCC5)CSc5ccccc5)c(S(=O)(=O)C(F)(F)Cl)c4)cc3)CC2)=C(c2ccc(Cl)cc2)C1] |
| N-(4-(1-((4'-chloro(1,1'-biphenyl)-2-yl)methyl)-1,2,3,6-tetrahydropyridin-4-yl)benzoyl)-4-(((1R)-3-(dimethylamino)-1-((phenylsulfanyl)methyl)propyl)amino)-3-((trifluoromethyl)sulfonyl)benzenesulfonamide | 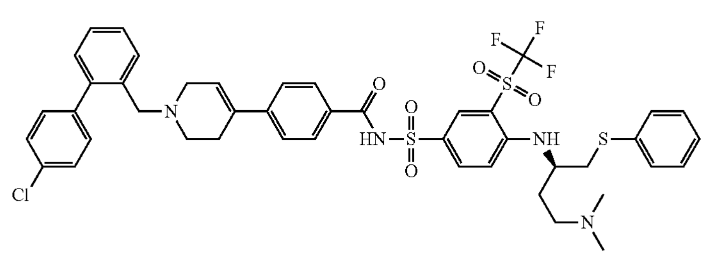 |

| Name | Structure |
|---|---|
| N-(4-(1-((4'-chloro(1,1'-biphenyl)-2-yl)methyl)-1,2,3,6-tetrahydropyridin-4-yl)benzoyl)-4-(((1R)-3-(morpholin-4-yl)-1-((phenylsulfanyl)methyl)propyl)amino)-3-((trifluoromethyl)sulfonyl)benzenesulfonamide | 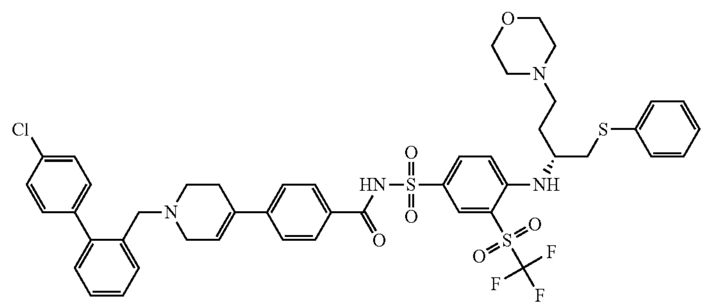 [SMILES: O=C(NS(=O)(=O)c1ccc(N[C@H](CCN2CCOCC2)CSc2ccccc2)c(S(=O)(=O)C(F)(F)F)c1)c1ccc(C2=CCN(Cc3ccccc3-c3ccc(Cl)cc3)CC2)cc1] |
| N-(4-(1-((4'-chloro(1,1'-biphenyl)-2-yl)methyl)-1,2,3,6-tetrahydropyridin-4-yl)benzoyl)-4-(((1R)-3-(diisopropylamino)-1-((phenylsulfanyl)methyl)propyl)amino)-3-((trifluoromethyl)sulfonyl)benzenesulfonamide | 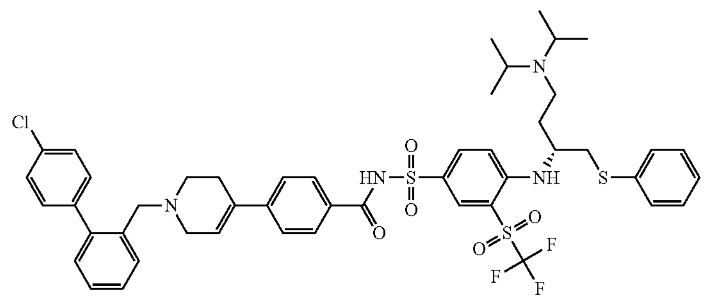 |
| N-(4-(1-((4'-chloro(1,1'-biphenyl)-2-yl)methyl)-1,2,3,6-tetrahydropyridin-4-yl)benzoyl)-4-(((1R)-3-(isopropyl(methyl)amino)-1-((phenylsulfanyl)methyl)propyl)amino)-3-((trifluoromethyl)sulfonyl)benzenesulfonamide | 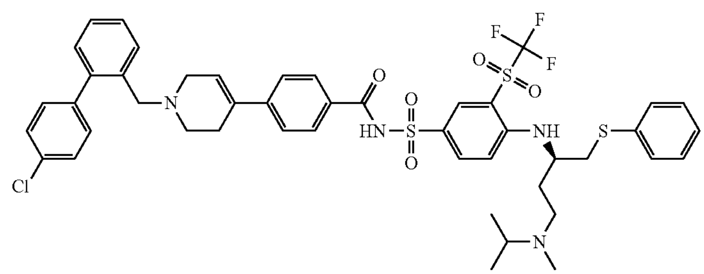 [SMILES: CC(C)N(C)CC[C@H](CSc1ccccc1)Nc1ccc(S(=O)(=O)NC(=O)c2ccc(C3=CCN(Cc4ccccc4-c4ccc(Cl)cc4)CC3)cc2)cc1S(=O)(=O)C(F)(F)F] |
| N-(4-(1-((2-(4-chlorophenyl)-1-cyclohex-1-en-1-yl)methyl)-1,2,3,6-tetrahydropyridin-4-yl)benzoyl)-4-(((1R)-3-(dimethylamino)-1-((phenylsulfanyl)methyl)propyl)amino)-3-((trifluoromethyl)sulfonyl)benzenesulfonamide | 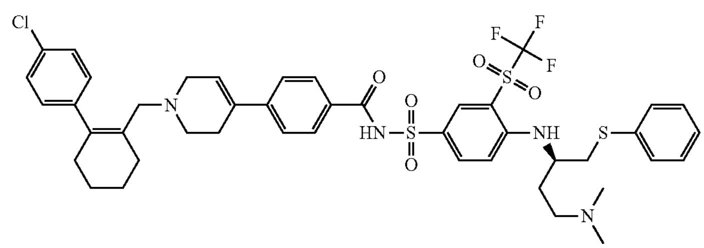 |
| N-(4-(1-((2-(4-chlorophenyl)-1-cyclohex-1-en-1-yl)methyl)-1,2,3,6-tetrahydropyridin-4-yl)benzoyl)-4-(((1R)-3-(morpholin-4-yl)-1-((phenylsulfanyl)methyl)propyl)amino)-3-((trifluoromethyl)sulfonyl)benzenesulfonamide | 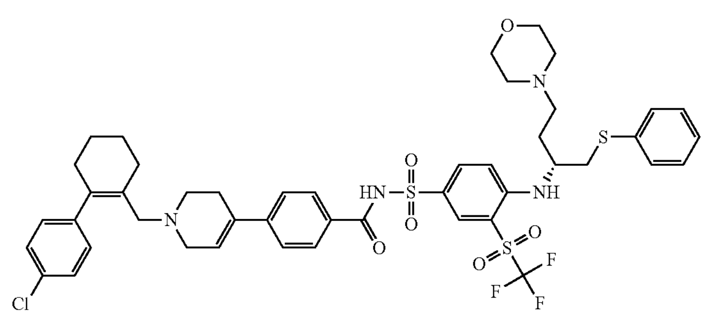 [SMILES: O=C(NS(=O)(=O)c1ccc(N[C@H](CCN2CCOCC2)CSc2ccccc2)c(S(=O)(=O)C(F)(F)F)c1)c1ccc(C2=CCN(CC3=C(c4ccc(Cl)cc4)CCCC3)CC2)cc1] |

| Name | Structure |
|---|---|
| N-(4-(1-((2-(4-chlorophenyl)-1-cyclohex-1-en-1-yl)methyl)-1,2,3,6-tetrahydropyridin-4-yl)benzoyl)-4-(((1R)-3-(diisopropylamino)-1-((phenylsulfanyl)methyl)propyl)amino)-3-((trifluoromethyl)sulfonyl)benzenesulfonamide | 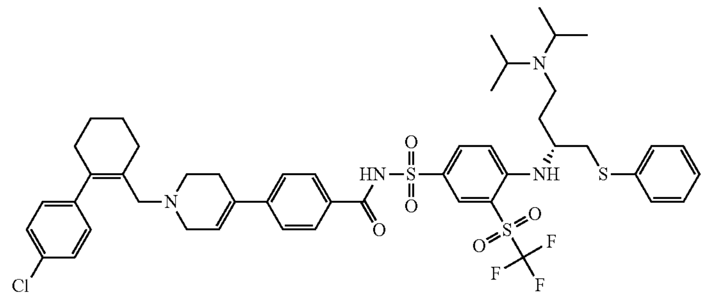 [SMILES: CC(C)N(CC[C@H](CSc1ccccc1)Nc1ccc(S(=O)(=O)NC(=O)c2ccc(C3=CCN(CC4=C(c5ccc(Cl)cc5)CCCC4)CC3)cc2)cc1S(=O)(=O)C(F)(F)F)C(C)C] |
| N-(4-(1-((2-(4-chlorophenyl)-1-cyclohex-1-en-1-yl)methyl)-1,2,3,6-tetrahydropyridin-4-yl)benzoyl)-4-(((1R)-3-(isopropyl(methyl)amino)-1-((phenylsulfanyl)methyl)propyl)amino)-3-((trifluoromethyl)sulfonyl)benzenesulfonamide | 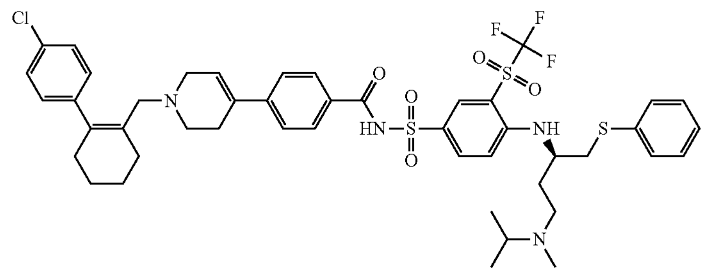 [SMILES: CC(C)N(C)CC[C@H](CSc1ccccc1)Nc1ccc(S(=O)(=O)NC(=O)c2ccc(C3=CCN(CC4=C(c5ccc(Cl)cc5)CCCC4)CC3)cc2)cc1S(=O)(=O)C(F)(F)F] |
| N-(4-(1-((2-(4-chlorophenyl)-1-cyclohept-1-en-1-yl)methyl)-1,2,3,6-tetrahydropyridin-4-yl)benzoyl)-4-(((1R)-3-(dimethylamino)-1-((phenylsulfanyl)methyl)propyl)amino)-3-((trifluoromethyl)sulfonyl)benzenesulfonamide | 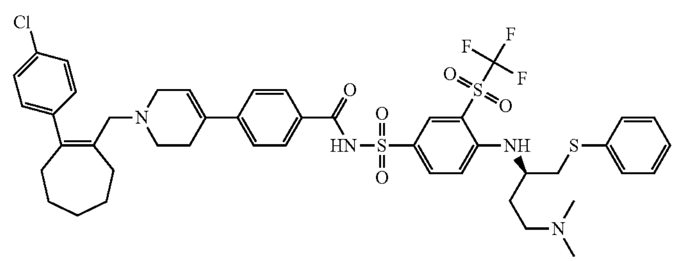 |
| N-(4-(1-((2-(4-chlorophenyl)-1-cyclohept-1-en-1-yl)methyl)-1,2,3,6-tetrahydropyridin-4-yl)benzoyl)-4-(((1R)-3-(morpholin-4-yl)-1-((phenylsulfanyl)methyl)propyl)amino)-3-((trifluoromethyl)sulfonyl)benzenesulfonamide | 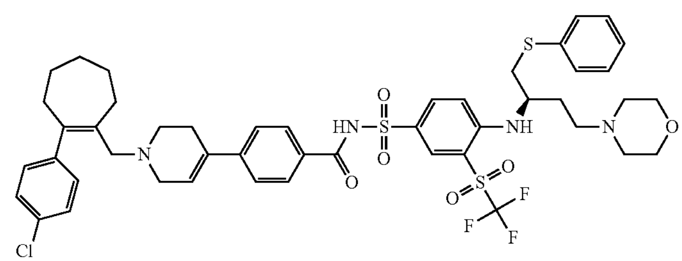 [SMILES: O=C(NS(=O)(=O)c1ccc(N[C@H](CCN2CCOCC2)CSc2ccccc2)c(S(=O)(=O)C(F)(F)F)c1)c1ccc(C2=CCN(CC3=C(c4ccc(Cl)cc4)CCCCC3)CC2)cc1] |
| N-(4-(1-((4'-chloro(1,1'-biphenyl)-2-yl)methyl)piperidin-4-yl)benzoyl)-4-(((1R)-3-(dimethylamino)-1-((phenylsulfanyl)methyl)propyl)amino)-3-((trifluoromethyl)sulfonyl)benzenesulfonamide | 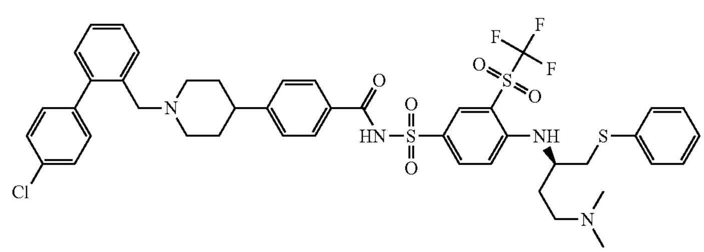 |
| N-(4-(4-((4'-chloro(1,1'-biphenyl)-2-yl)methyl)piperidin-1-yl)benzoyl)-4-(((1R)-3-(dimethylamino)-1-((phenylsulfanyl)methyl)propyl)amino)-3-((trifluoromethyl)sulfonyl)benzenesulfonamide | 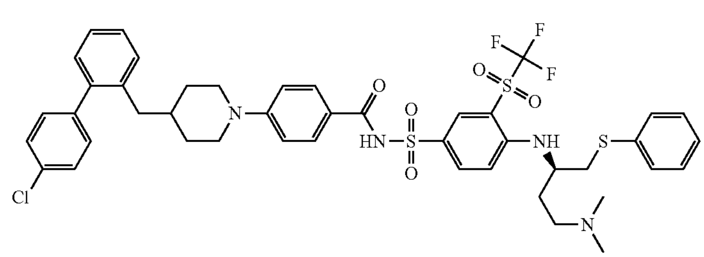 |

| Name | Structure |
|---|---|
| N-(4-(4-((4'-chloro(1,1'-biphenyl)-2-yl)methyl)-1-cyclohex-1-en-1-yl)benzoyl)-4-(((1R)-3-(dimethylamino)-1-((phenylsulfanyl)methyl)propyl)amino)-3-((trifluoromethyl)sulfonyl)benzenesulfonamide | |
| N-(4-(4-((2-(4-chlorophenyl)cyclohept-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide | 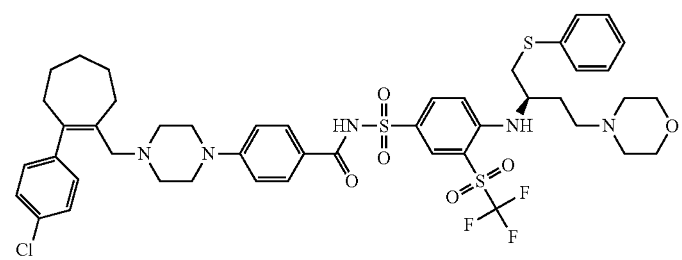 [SMILES: O=C(NS(=O)(=O)c1ccc(N[C@H](CCN2CCOCC2)CSc2ccccc2)c(S(=O)(=O)C(F)(F)F)c1)c1ccc(N2CCN(CC3=C(c4ccc(Cl)cc4)CCCCC3)CC2)cc1] |
| N-(4-(4-((2-(4-chlorophenyl)cyclohex-1-en-1-yl)methyl)piperazin-1-yl)benzoyl)-4-(((1R)-2-(dimethylamino)-1-((phenylsulfanyl)methyl)ethyl)amino)-3-((trifluoromethyl)sulfonyl)benzenesulfonamide | 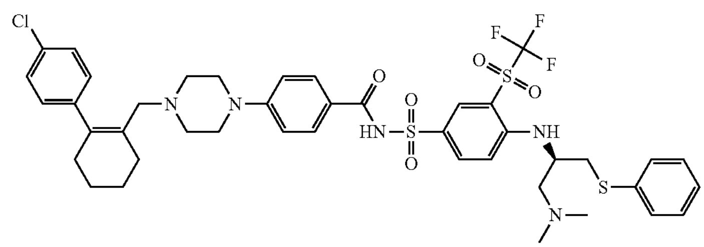 [SMILES: CN(C)C[C@H](CSc1ccccc1)Nc1ccc(S(=O)(=O)NC(=O)c2ccc(N3CCN(CC4=C(c5ccc(Cl)cc5)CCCC4)CC3)cc2)cc1S(=O)(=O)C(F)(F)F] |
| N-(4-(4-((4'-chloro(1,1'-biphenyl)-2-yl)methyl)piperazin-1-yl)benzoyl)-4-(((1R)-2-(dimethylamino)-1-((phenylsulfanyl)methyl)ethyl)amino)-3-((trifluoromethyl)sulfonyl)benzenesulfonamide | 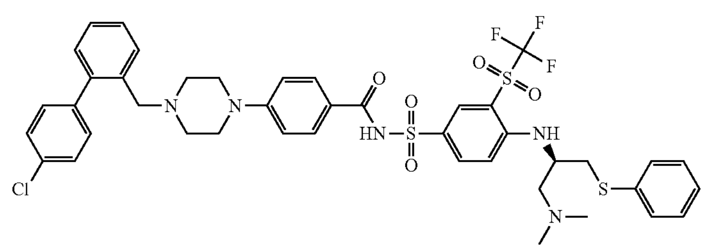 [SMILES: CN(C)C[C@H](CSc1ccccc1)Nc1ccc(S(=O)(=O)NC(=O)c2ccc(N3CCN(Cc4ccccc4-c4ccc(Cl)cc4)CC3)cc2)cc1S(=O)(=O)C(F)(F)F] |
| N-(4-(4-((4'-chloro(1,1'-biphenyl)-2-yl)methyl)piperazin-1-yl)benzoyl)-4-(((1R)-2-(diethylamino)-1-((phenylsulfanyl)methyl)ethyl)amino)-3-((trifluoromethyl)sulfonyl)benzenesulfonamide | 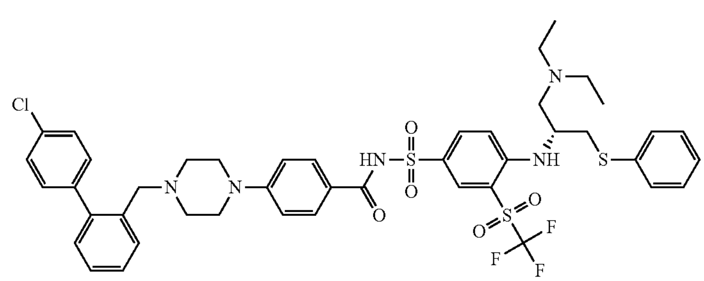 [SMILES: CCN(CC)C[C@H](CSc1ccccc1)Nc1ccc(S(=O)(=O)NC(=O)c2ccc(N3CCN(Cc4ccccc4-c4ccc(Cl)cc4)CC3)cc2)cc1S(=O)(=O)C(F)(F)F] |
| N-(4-(4-((4'-chloro(1,1'-biphenyl)-2-yl)methyl)piperazin-1-yl)benzoyl)-4-(((1R)-2-(morpholin-4-yl)-1-((phenylsulfanyl)methyl)ethyl)amino)-3-((trifluoromethyl)sulfonyl)benzenesulfonamide | 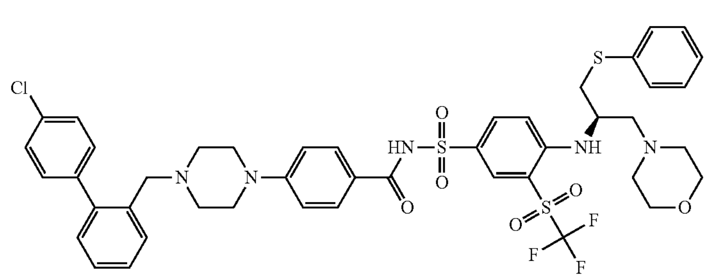 [SMILES: O=C(NS(=O)(=O)c1ccc(N[C@@H](CSc2ccccc2)CN2CCOCC2)c(S(=O)(=O)C(F)(F)F)c1)c1ccc(N2CCN(Cc3ccccc3-c3ccc(Cl)cc3)CC2)cc1] |

-continued

| Name | Structure |
|---|---|
| N-(4-(4-((2-(4-chlorophenyl)cyclohex-1-en-1-yl)methyl)piperazin-1-yl)benzoyl)-4-(((1R)-2-(diethylamino)-1-((phenylsulfanyl)methyl)ethyl)amino)-3-((trifluoromethyl)sulfonyl)benzenesulfonamide | 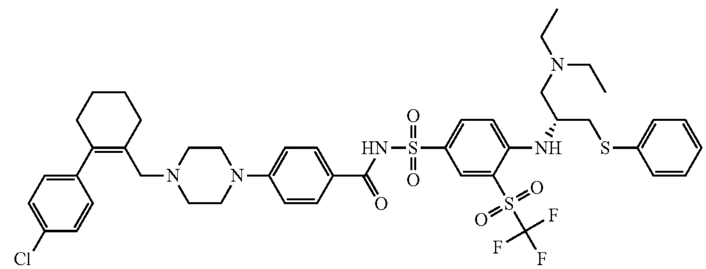 [SMILES: CCN(CC)C[C@H](CSc1ccccc1)Nc1ccc(S(=O)(=O)NC(=O)c2ccc(N3CCN(CC4=C(c5ccc(Cl)cc5)CCCC4)CC3)cc2)cc1S(=O)(=O)C(F)(F)F] |
| N-(4-(4-((2-(4-chlorophenyl)cyclohex-1-en-1-yl)methyl)piperazin-1-yl)benzoyl)-4-(((1R)-2-(morpholin-4-yl)-1-((phenylsulfanyl)methyl)ethyl)amino)-3-((trifluoromethyl)sulfonyl)benzenesulfonamide | 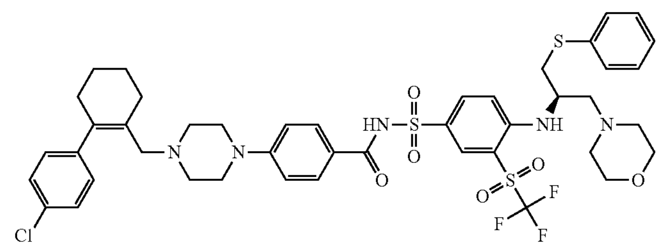 [SMILES: O=C(NS(=O)(=O)c1ccc(N[C@@H](CSc2ccccc2)CN2CCOCC2)c(S(=O)(=O)C(F)(F)F)c1)c1ccc(N2CCN(CC3=C(c4ccc(Cl)cc4)CCCC3)CC2)cc1] |
| N-(4-(4-((2-(4-chlorophenyl)cyclohex-1-en-1-yl)methyl)piperazin-1-yl)benzoyl)-4-(((1R)-3-((2R,6S)-2,6-dimethylmorpholin-1-yl)-1-((phenylsulfanyl)methyl)propyl)amino)-3-((trifluoromethyl)sulfonyl)benzenesulfonamide | 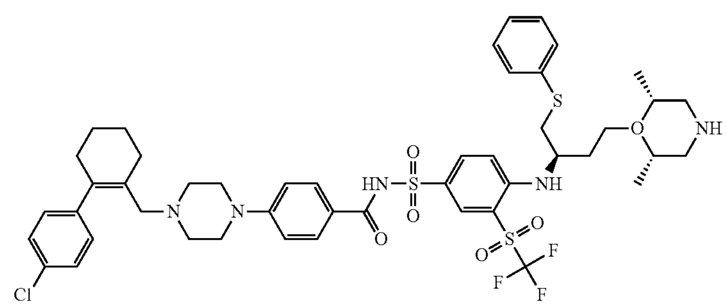 |
| N-(4-(4-((2-(4-chlorophenyl)cyclohex-1-en-1-yl)methyl)piperazin-1-yl)benzoyl)-4-(((1R)-3-(2,6-dimethylmorpholin-4-yl)-1-((phenylsulfanyl)methyl)propyl)amino)-3-((trifluoromethyl)sulfonyl)benzenesulfonamide | 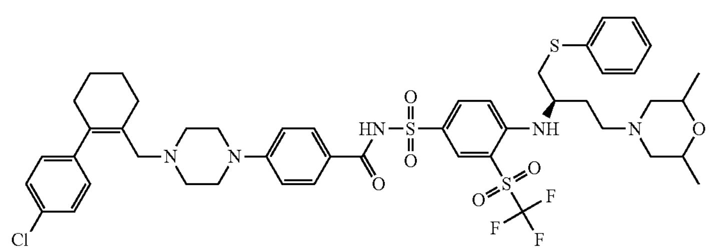 [SMILES: CC1CN(CC[C@H](CSc2ccccc2)Nc2ccc(S(=O)(=O)NC(=O)c3ccc(N4CCN(CC5=C(c6ccc(Cl)cc6)CCCC5)CC4)cc3)cc2S(=O)(=O)C(F)(F)F)CC(C)O1] |
| N-(4-(4-((2-(4-chlorophenyl)cyclohept-1-en-1-yl)methyl)piperazin-1-yl)benzoyl)-4-(((1R)-3-((2R,6S)-2,6-dimethylmorpholin-4-yl)-1-((phenylsulfanyl)methyl)propyl)amino)-3-((trifluoromethyl)sulfonyl)benzenesulfonamide | 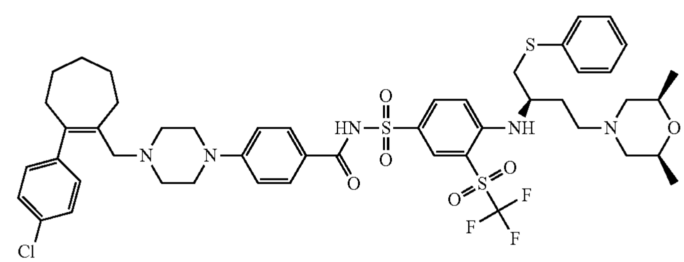 [SMILES: C[C@@H]1CN(CC[C@H](CSc2ccccc2)Nc2ccc(S(=O)(=O)NC(=O)c3ccc(N4CCN(CC5=C(c6ccc(Cl)cc6)CCCCC5)CC4)cc3)cc2S(=O)(=O)C(F)(F)F)C[C@H](C)O1] |
| N-(4-(4-((2-(4-chlorophenyl)cyclohept-1-en-1-yl)methyl)piperazin-1-yl)benzoyl)-4-(((1R)-3-(2,6-dimethylmorpholin-4-yl)-1-((phenylsulfanyl)methyl)propyl)amino)-3-((trifluoromethyl)sulfonyl)benzenesulfonamide | 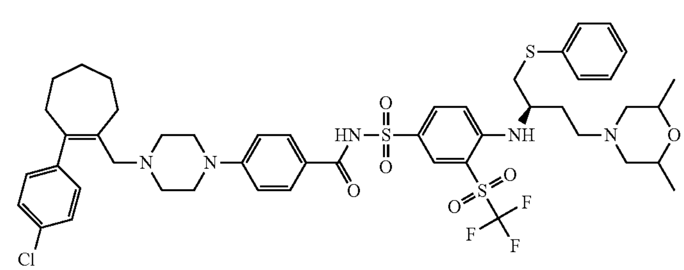 [SMILES: CC1CN(CC[C@H](CSc2ccccc2)Nc2ccc(S(=O)(=O)NC(=O)c3ccc(N4CCN(CC5=C(c6ccc(Cl)cc6)CCCCC5)CC4)cc3)cc2S(=O)(=O)C(F)(F)F)CC(C)O1] |

| Name | Structure |
|---|---|
| N-(4-(4-((1-(4-chlorophenyl)piperidin-2-yl)methyl)piperazin-1-yl)benzoyl)-4-(((1R)-3-(dimethylamino)-1-((phenylsulfanyl)methyl)propyl)amino)-3-((trifluoromethyl)sulfonyl)benzenesulfonamide | 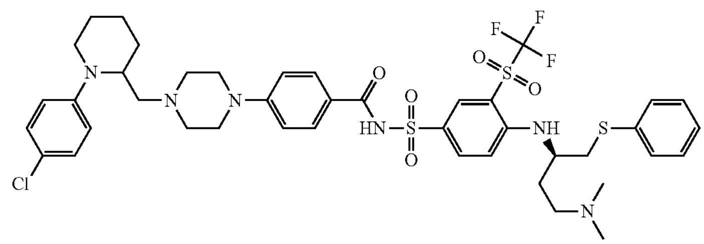 [SMILES: CN(C)CC[C@H](CSc1ccccc1)Nc1ccc(S(=O)(=O)NC(=O)c2ccc(N3CCN(CC4CCCCN4c4ccc(Cl)cc4)CC3)cc2)cc1S(=O)(=O)C(F)(F)F] |
| N-(4-(4-((2-(4-chlorophenyl)cyclohex-1-en-1-yl)methyl)piperazin-1-yl)benzoyl)-4-(((1R)-3-(cyclopropylamino)-1-((phenylsulfanyl)methyl)propyl)amino)-3-((trifluoromethyl)sulfonyl)benzenesulfonamide | 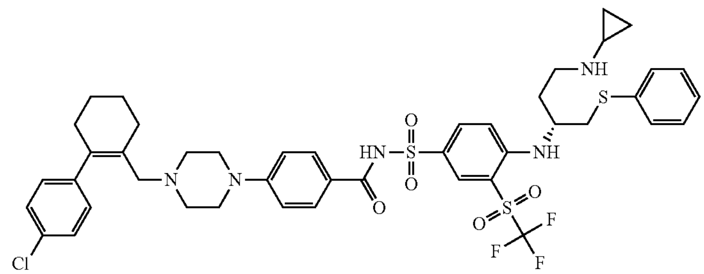 [SMILES: O=C(NS(=O)(=O)c1ccc(N[C@H](CCNC2CC2)CSc2ccccc2)c(S(=O)(=O)C(F)(F)F)c1)c1ccc(N2CCN(CC3=C(c4ccc(Cl)cc4)CCCC3)CC2)cc1] |
| N-(4-(4-((2-(4-chlorophenyl)cyclohex-1-en-1-yl)methyl)piperazin-1-yl)benzoyl)-4-(((1R)-3-(cyclopropyl(cyclopropylmethyl)amino)-1-((phenylsulfanyl)methyl)propyl)amino)-3-((trifluoromethyl)sulfonyl)benzenesulfonamide | 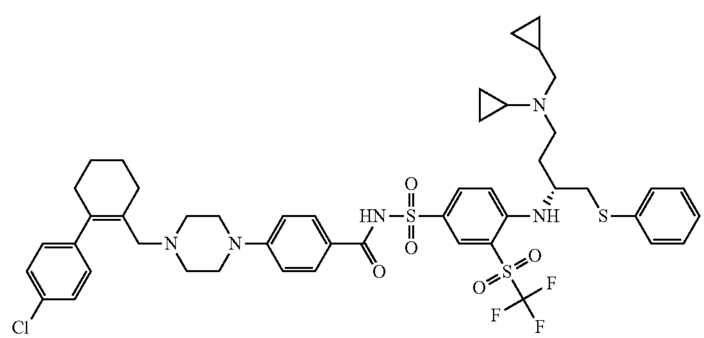 [SMILES: O=C(NS(=O)(=O)c1ccc(N[C@H](CCN(CC2CC2)C2CC2)CSc2ccccc2)c(S(=O)(=O)C(F)(F)F)c1)c1ccc(N2CCN(CC3=C(c4ccc(Cl)cc4)CCCC3)CC2)cc1] |
| N-(4-(4-((2-(4-chlorophenyl)cyclohex-1-en-1-yl)methyl)piperazin-1-yl)benzoyl)-4-(((1R)-3-(cyclopropyl(methyl)amino)-1-((phenylsulfanyl)methyl)propyl)amino)-3-((trifluoromethyl)sulfonyl)benzenesulfonamide | 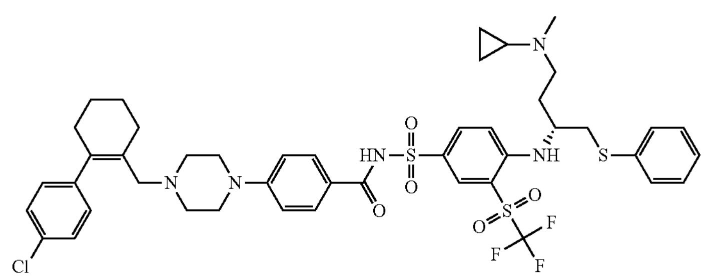 [SMILES: CN(CC[C@H](CSc1ccccc1)Nc1ccc(S(=O)(=O)NC(=O)c2ccc(N3CCN(CC4=C(c5ccc(Cl)cc5)CCCC4)CC3)cc2)cc1S(=O)(=O)C(F)(F)F)C1CC1] |
| N-(4-(4-((2-(4-chlorophenyl)cyclohex-1-en-1-yl)methyl)piperazin-1-yl)benzoyl)-4-(((1R)-3-((cyclopentylmethyl)(cyclopropyl)amino)-1-((phenylsulfanyl)methyl)propyl)amino)-3-((trifluoromethyl)sulfonyl)benzenesulfonamide | 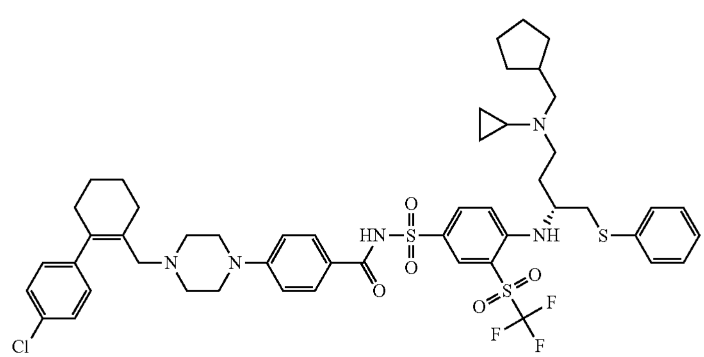 [SMILES: O=C(NS(=O)(=O)c1ccc(N[C@H](CCN(CC2CCCC2)C2CC2)CSc2ccccc2)c(S(=O)(=O)C(F)(F)F)c1)c1ccc(N2CCN(CC3=C(c4ccc(Cl)cc4)CCCC3)CC2)cc1] |

| Name | Structure |
|---|---|
| N-(4-(4-((2-(4-chlorophenyl)cyclohex-1-en-1-yl)methyl)piperazin-1-yl)benzoyl)-4-(((1R)-3-((cyclohexylmethyl)(cyclopropyl)amino)-1-((phenylsulfanyl)methyl)propyl)amino)-3-((trifluoromethyl)sulfonyl)benzenesulfonamide | 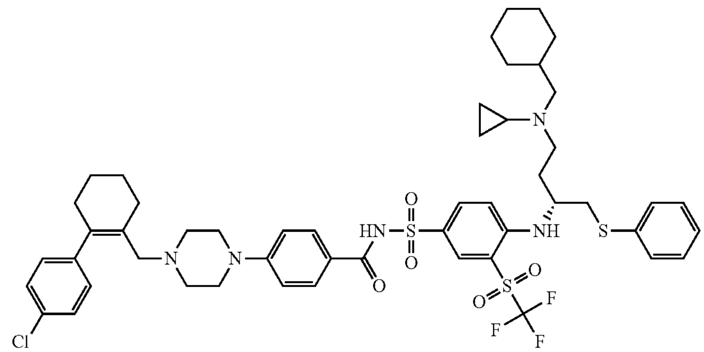 [SMILES: O=C(NS(=O)(=O)c1ccc(N[C@H](CCN(CC2CCCCC2)C2CC2)CSc2ccccc2)c(S(=O)(=O)C(F)(F)F)c1)c1ccc(N2CCN(CC3=C(c4ccc(Cl)cc4)CCCC3)CC2)cc1] |
| N-(4-(4-((2-(4-chlorophenyl)cyclohex-1-en-1-yl)methyl)piperazin-1-yl)benzoyl)-4-(((1R)-3-(cyclopropyl(tetrahydrofuran-3-ylmethyl)amino)-1-((phenylsulfanyl)methyl)propyl)amino)-3-((trifluoromethyl)sulfonyl)benzenesulfonamide | 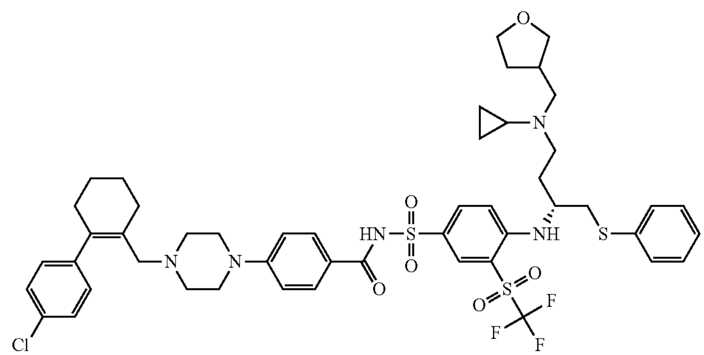 [SMILES: O=C(NS(=O)(=O)c1ccc(N[C@H](CCN(CC2CCOC2)C2CC2)CSc2ccccc2)c(S(=O)(=O)C(F)(F)F)c1)c1ccc(N2CCN(CC3=C(c4ccc(Cl)cc4)CCCC3)CC2)cc1] |
| 4-(((1R)-3-(benzyl(cyclopropyl)amino)-1-((phenylsulfanyl)methyl)propyl)amino)-N-(4-(4-((2-(4-chlorophenyl)cyclohex-1-en-1-yl)methyl)piperazin-1-yl)benzoyl)-3-((trifluoromethyl)sulfonyl)benzenesulfonamide | 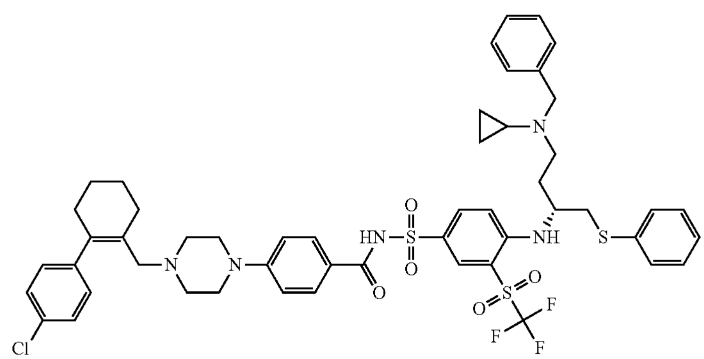 [SMILES: O=C(NS(=O)(=O)c1ccc(N[C@H](CCN(Cc2ccccc2)C2CC2)CSc2ccccc2)c(S(=O)(=O)C(F)(F)F)c1)c1ccc(N2CCN(CC3=C(c4ccc(Cl)cc4)CCCC3)CC2)cc1] |
| N-(4-(4-((2-(4-chlorophenyl)cyclohex-1-en-1-yl)methyl)piperazin-1-yl)benzoyl)-4-(((1R)-3-(cyclopropyl(isobutyl)amino)-1-((phenylsulfanyl)methyl)propyl)amino)-3-((trifluoromethyl)sulfonyl)benzenesulfonamide | 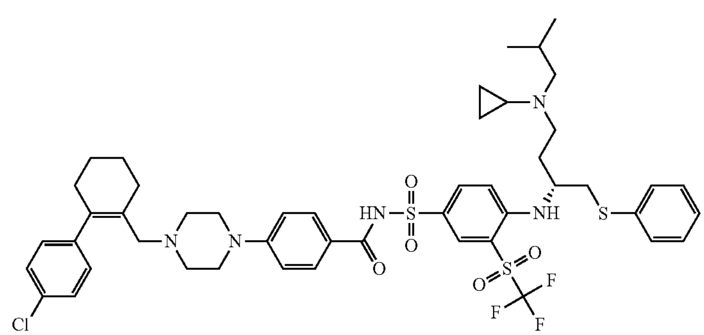 [SMILES: CC(C)CN(CC[C@H](CSc1ccccc1)Nc1ccc(S(=O)(=O)NC(=O)c2ccc(N3CCN(CC4=C(c5ccc(Cl)cc5)CCCC4)CC3)cc2)cc1S(=O)(=O)C(F)(F)F)C1CC1] |

| Name | Structure |
|---|---|
| N-(4-(4-((2-(4-chlorophenyl)cyclohex-1-en-1-yl)methyl)piperazin-1-yl)benzoyl)-4-(((1R)-3-(cyclopropyl(tetrahydro-2H-pyran-4-yl)amino)-1-((phenylsulfanyl)methyl)propyl)amino)-3-((trifluoromethyl)sulfonyl)benzenesulfonamide | 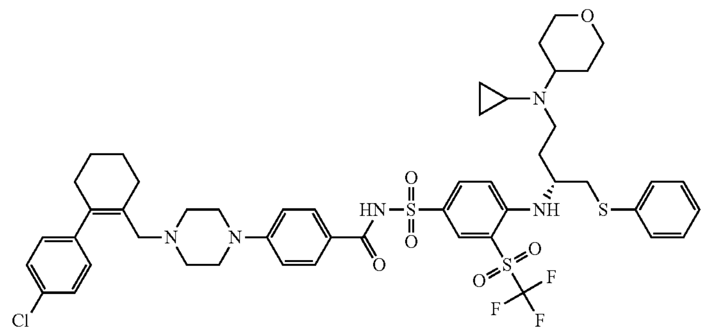 [SMILES: O=C(NS(=O)(=O)c1ccc(N[C@H](CCN(C2CCOCC2)C2CC2)CSc2ccccc2)c(S(=O)(=O)C(F)(F)F)c1)c1ccc(N2CCN(CC3=C(c4ccc(Cl)cc4)CCCC3)CC2)cc1] |
| 3-((chloro(difluoro)methyl)sulfonyl)-N-(4-(4-((2-(4-chlorophenyl)-4,4-diethylcyclohex-1-en-1-yl)methyl)piperazin-1-yl)benzoyl)-4-(((1R)-3-(dimethylamino)-1-((phenylsulfanyl)methyl)propyl)amino)benzenesulfonamide | 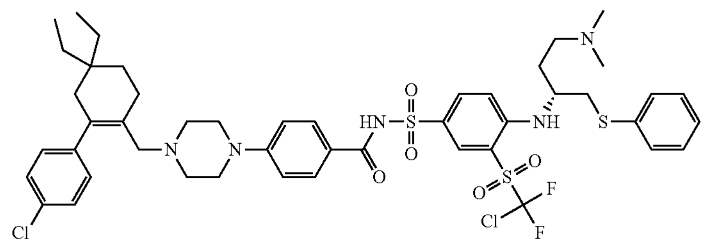 [SMILES: CCC1(CC)CCC(CN2CCN(c3ccc(C(=O)NS(=O)(=O)c4ccc(N[C@H](CCN(C)C)CSc5ccccc5)c(S(=O)(=O)C(F)(F)Cl)c4)cc3)CC2)=C(c2ccc(Cl)cc2)C1] |
| N-(4-(4-((2-(4-chlorophenyl)-4,4-diethylcyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide | 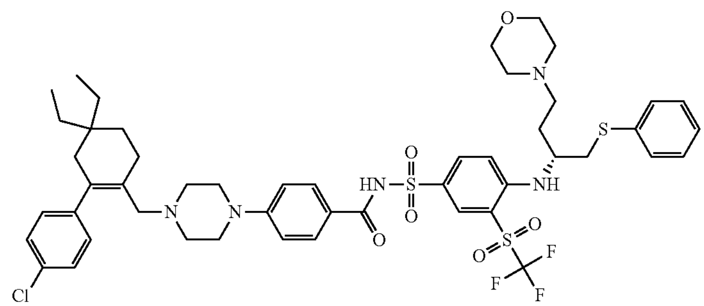 [SMILES: CCC1(CC)CCC(CN2CCN(c3ccc(C(=O)NS(=O)(=O)c4ccc(N[C@H](CCN5CCOCC5)CSc5ccccc5)c(S(=O)(=O)C(F)(F)F)c4)cc3)CC2)=C(c2ccc(Cl)cc2)C1] |
| (4-(cyclohexylmethoxy)-N-((4'-fluoro(1,1'-biphenyl)-4-yl)carbonyl)-3-(methylsulfonyl)benzenesulfonamide | 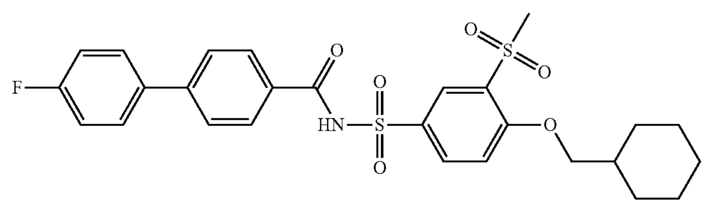 [SMILES: CS(=O)(=O)c1cc(S(=O)(=O)NC(=O)c2ccc(-c3ccc(F)cc3)cc2)ccc1OCC1CCCCC1] |
| N-(4-(4-(((1R,2R)-2-(4-chlorophenyl)cyclohexyl)methyl)piperazin-1-yl)benzoyl)-4-(((1R)-3-(dimethylamino)-1-((phenylsulfanyl)methyl)propyl)amino)-3-((trifluoromethyl)sulfonyl)benzenesulfonamide | 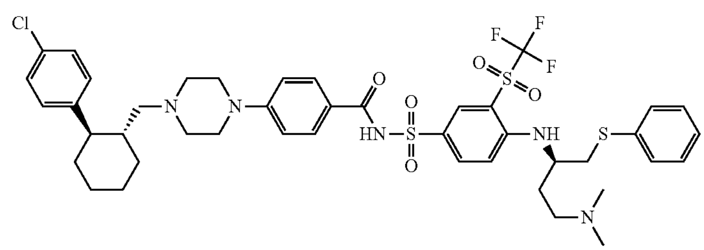 [SMILES: CN(C)CC[C@H](CSc1ccccc1)Nc1ccc(S(=O)(=O)NC(=O)c2ccc(N3CCN(C[C@@H]4CCCC[C@H]4c4ccc(Cl)cc4)CC3)cc2)cc1S(=O)(=O)C(F)(F)F] |
| N-(4-(4-(((1S,2S)-2-(4-chlorophenyl)cyclohexyl)methyl)piperazin-1-yl)benzoyl)-4-(((1R)-3-(dimethylamino)-1-((phenylsulfanyl)methyl)propyl)amino)-3-((trifluoromethyl)sulfonyl)benzenesulfonamide | 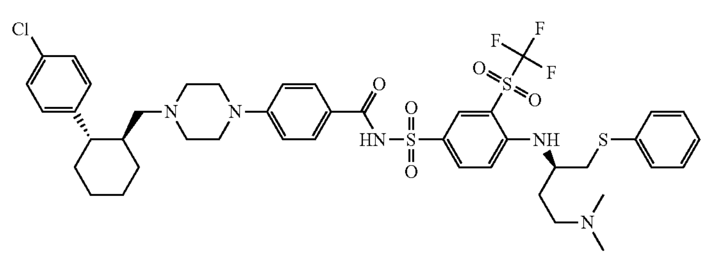 [SMILES: CN(C)CC[C@H](CSc1ccccc1)Nc1ccc(S(=O)(=O)NC(=O)c2ccc(N3CCN(C[C@H]4CCCC[C@@H]4c4ccc(Cl)cc4)CC3)cc2)cc1S(=O)(=O)C(F)(F)F] |

-continued

| Name | Structure |
|------|-----------|
| N-(4-(4-(((1R,2S)-2-(4-chlorophenyl)cyclohexyl)methyl)piperazin-1-yl)benzoyl)-4-(((1R)-3-(dimethylamino)-1-((phenylsulfanyl)methyl)propyl)amino)-3-((trifluoromethyl)sulfonyl)benzenesulfonamide | 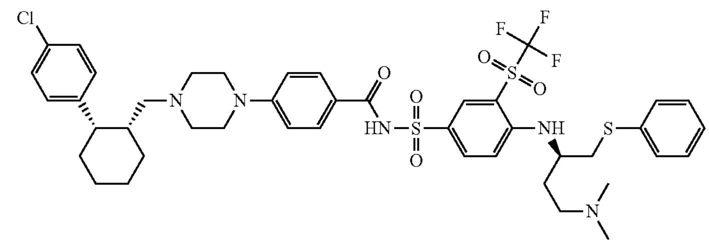 |
| N-(4-(4-(((1S,2S)-2-(4-chlorophenyl)cyclohexyl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide | 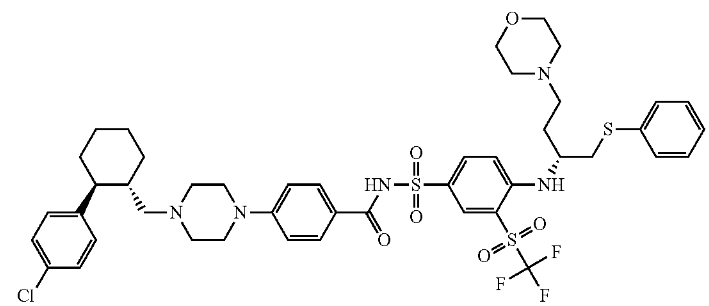 [SMILES: O=C(NS(=O)(=O)c1ccc(N[C@H](CCN2CCOCC2)CSc2ccccc2)c(S(=O)(=O)C(F)(F)F)c1)c1ccc(N2CCN(C[C@H]3CCCC[C@@H]3c3ccc(Cl)cc3)CC2)cc1] |
| N-(4-(4-(((1R,2S)-2-(4-chlorophenyl)cyclohexyl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide | 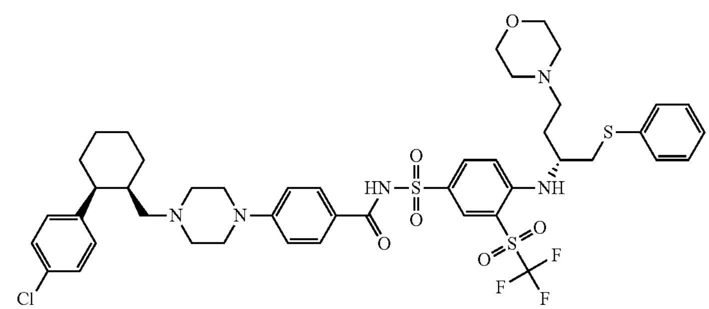 [SMILES: O=C(NS(=O)(=O)c1ccc(N[C@H](CCN2CCOCC2)CSc2ccccc2)c(S(=O)(=O)C(F)(F)F)c1)c1ccc(N2CCN(C[C@@H]3CCCC[C@@H]3c3ccc(Cl)cc3)CC2)cc1] |
| N-(4-(4-((4'-chloro(1,1'-biphenyl)-2-yl)methyl)piperazin-1-yl)benzoyl)-4-(((1R)-3-(dipropylamino)-1-((phenylsulfanyl)methyl)propyl)amino)-3-((trifluoromethyl)sulfonyl)benzenesulfonamide | 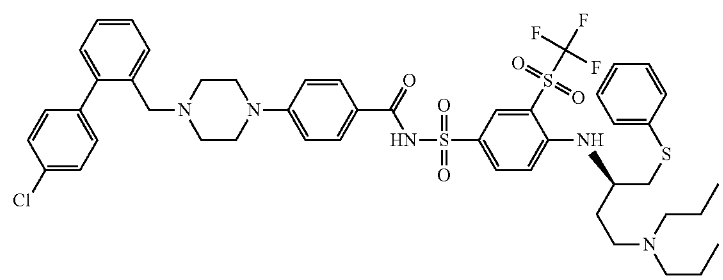 [SMILES: CCCN(CCC)CC[C@H](CSc1ccccc1)Nc1ccc(S(=O)(=O)NC(=O)c2ccc(N3CCN(Cc4ccccc4-c4ccc(Cl)cc4)CC3)cc2)cc1S(=O)(=O)C(F)(F)F] |
| N-(4-(4-((2-(4-chlorophenyl)cyclohex-1-en-1-yl)methyl)piperazin-1-yl)benzoyl)-4-(((1R)-3-(dipropylamino)-1-((phenylsulfanyl)methyl)propyl)amino)-3-((trifluoromethyl)sulfonyl)benzenesulfonamide | 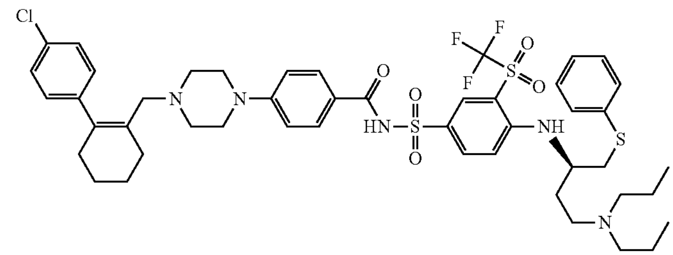 [SMILES: CCCN(CCC)CC[C@H](CSc1ccccc1)Nc1ccc(S(=O)(=O)NC(=O)c2ccc(N3CCN(CC4=C(c5ccc(Cl)cc5)CCCC4)CC3)cc2)cc1S(=O)(=O)C(F)(F)F] |

| Name | Structure |
|---|---|
| N-(4-(4-((4'-chloro(1,1'-biphenyl)-2-yl)methyl)piperazin-1-yl)benzoyl)-4-(((1R)-3-(diethylamino)-1-((phenylsulfanyl)methyl)propyl)amino)-3-((trifluoromethyl)sulfonyl)benzenesulfonamide | 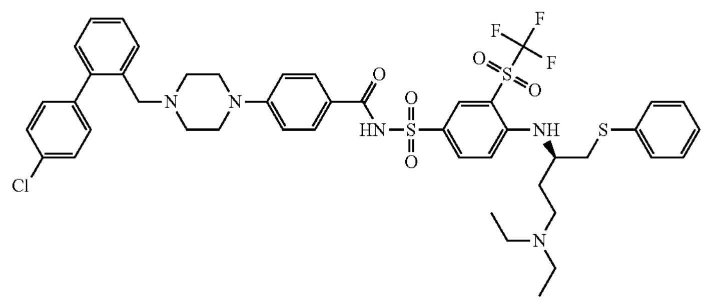 [SMILES: CCN(CC)CC[C@H](CSc1ccccc1)Nc1ccc(S(=O)(=O)NC(=O)c2ccc(N3CCN(Cc4ccccc4-c4ccc(Cl)cc4)CC3)cc2)cc1S(=O)(=O)C(F)(F)F] |
| N-(4-(4-((2-(4-chlorophenyl)cyclohex-1-en-1-yl)methyl)piperazin-1-yl)benzoyl)-4-(((1R)-3-(diethylamino)-1-((phenylsulfanyl)methyl)propyl)amino)-3-((trifluoromethyl)sulfonyl)benzenesulfonamide | 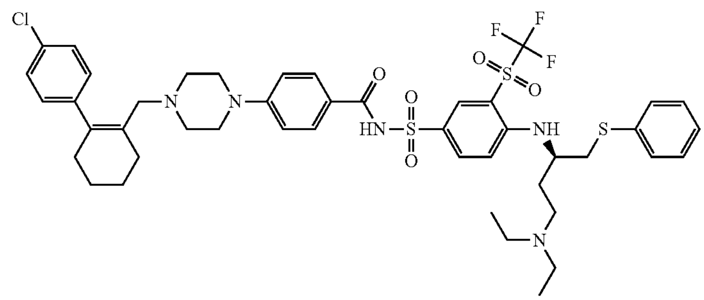 |
| N-(4-(4-((2-(4-chlorophenyl)-5,5-dimethylcyclohex-1-en-1-yl)methyl)piperazin-1-yl)benzoyl)-4-(((1R)-3-(diethylamino)-1-((phenylsulfanyl)methyl)propyl)amino)-3-((trifluoromethyl)sulfonyl)benzenesulfonamide | 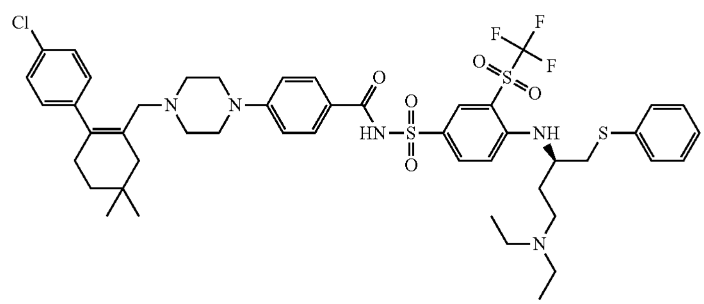 [SMILES: CCN(CC)CC[C@H](CSc1ccccc1)Nc1ccc(S(=O)(=O)NC(=O)c2ccc(N3CCN(CC4=C(c5ccc(Cl)cc5)CCC(C)(C)C4)CC3)cc2)cc1S(=O)(=O)C(F)(F)F] |
| N-(4-(4-((2-(4-chlorophenyl)cyclohept-1-en-1-yl)methyl)piperazin-1-yl)benzoyl)-4-(((1R)-3-(diethylamino)-1-((phenylsulfanyl)methyl)propyl)amino)-3-((trifluoromethyl)sulfonyl)benzenesulfonamide | 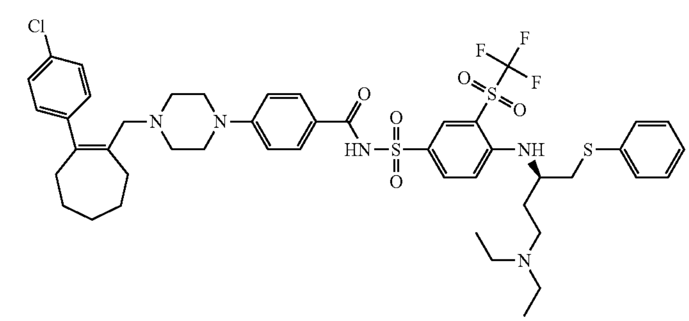 [SMILES: CCN(CC)CC[C@H](CSc1ccccc1)Nc1ccc(S(=O)(=O)NC(=O)c2ccc(N3CCN(CC4=C(c5ccc(Cl)cc5)CCCCC4)CC3)cc2)cc1S(=O)(=O)C(F)(F)F] |
| N-(4-(4-((4'-chloro(1,1'-biphenyl)-2-yl)methyl)piperazin-1-yl)benzoyl)-3-((chloro(difluoro)methyl)sulfonyl)-4-(((1R)-3-(diethylamino)-1-((phenylsulfanyl)methyl)propyl)amino)benzenesulfonamide | 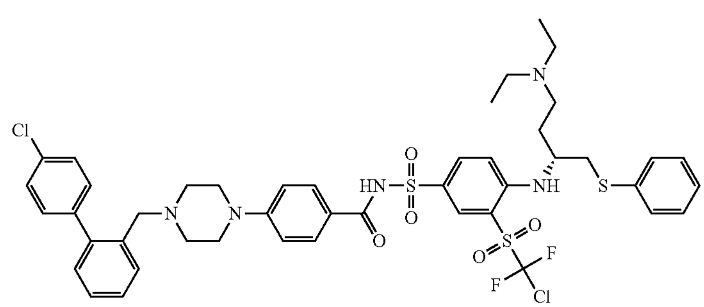 [SMILES: CCN(CC)CC[C@H](CSc1ccccc1)Nc1ccc(S(=O)(=O)NC(=O)c2ccc(N3CCN(Cc4ccccc4-c4ccc(Cl)cc4)CC3)cc2)cc1S(=O)(=O)C(F)(F)Cl] |

| Name | Structure |
|---|---|
| 3-((chloro(difluoro)methyl)sulfonyl)-N-(4-(4-((2-(4-chlorophenyl)cyclohex-1-en-1-yl)methyl)piperazin-1-yl)benzoyl)-4-(((1R)-3-(diethylamino)-1-((phenylsulfanyl)methyl)propyl)amino)benzenesulfonamide | 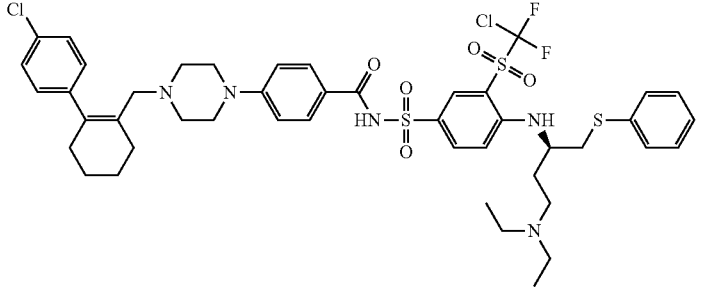 [SMILES: CCN(CC)CC[C@H](CSc1ccccc1)Nc1ccc(S(=O)(=O)NC(=O)c2ccc(N3CCN(CC4=C(c5ccc(Cl)cc5)CCCC4)CC3)cc2)cc1S(=O)(=O)C(F)(F)Cl] |
| 3-((chloro(difluoro)methyl)sulfonyl)-N-(4-(4-((2-(4-chlorophenyl)cyclohept-1-en-1-yl)methyl)piperazin-1-yl)benzoyl)-4-(((1R)-3-(diethylamino)-1-((phenylsulfanyl)methyl)propyl)amino)benzenesulfonamide | 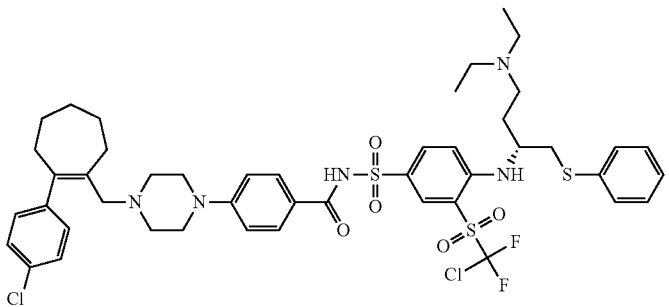 [SMILES: CCN(CC)CC[C@H](CSc1ccccc1)Nc1ccc(S(=O)(=O)NC(=O)c2ccc(N3CCN(CC4=C(c5ccc(Cl)cc5)CCCCC4)CC3)cc2)cc1S(=O)(=O)C(F)(F)Cl] |
| (((((4-chlorobutyl)((3R)-3-(4-(((4-(4-((2-(4-chlorophenyl)-1-cyclohexen-1-yl)methyl)-1-piperazinyl)benzoyl)amino)sulfonyl)-2-((trifluoromethyl)sulfonyl)anilino)-4-(phenylsulfanyl)butyl)amino)carbonyl)oxy)methyl pivalate | 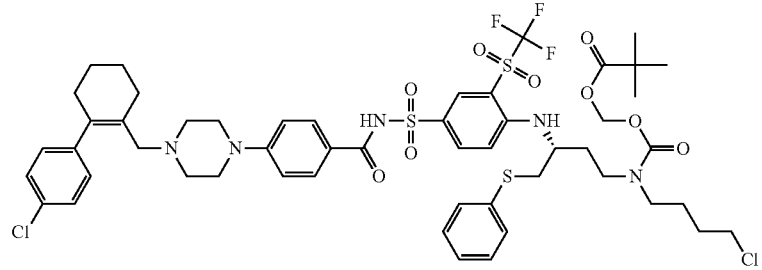 [SMILES: CC(C)(C)C(=O)OCOC(=O)N(CCCCCl)CC[C@H](CSc1ccccc1)Nc1ccc(S(=O)(=O)NC(=O)c2ccc(N3CCN(CC4=C(c5ccc(Cl)cc5)CCCC4)CC3)cc2)cc1S(=O)(=O)C(F)(F)F] |
| (phosphonooxy)methyl 4-chlorobutyl((3R)-3-(4-(((4-(4-((2-(4-chlorophenyl)-1-cyclohexen-1-yl)methyl)-1-piperazinyl)benzoyl)amino)sulfonyl)-2-((trifluoromethyl)sulfonyl)anilino)-4-(phenylsulfanyl)butyl)carbamate | 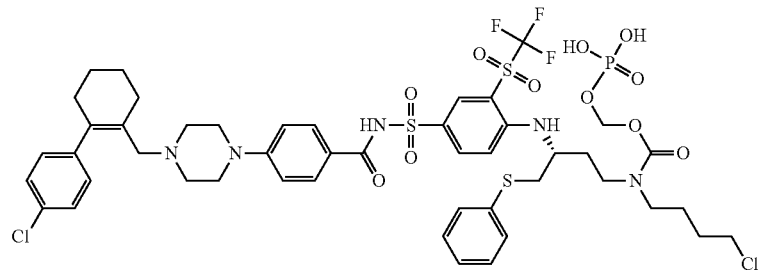 [SMILES: O=C(NS(=O)(=O)c1ccc(N[C@H](CCN(CCCCCl)C(=O)OCOP(=O)(O)O)CSc2ccccc2)c(S(=O)(=O)C(F)(F)F)c1)c1ccc(N2CCN(CC3=C(c4ccc(Cl)cc4)CCCC3)CC2)cc1] |
| N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide | 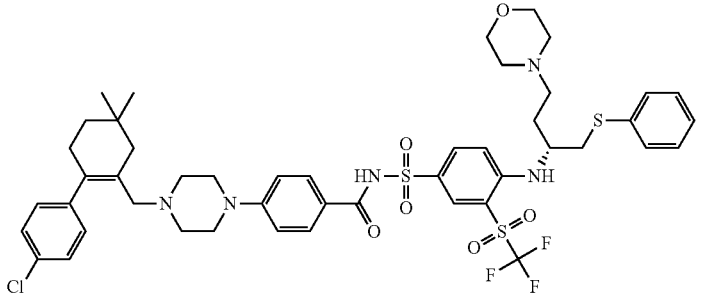 [SMILES: CC1(C)CCC(c2ccc(Cl)cc2)=C(CN2CCN(c3ccc(C(=O)NS(=O)(=O)c4ccc(N[C@H](CCN5CCOCC5)CSc5ccccc5)c(S(=O)(=O)C(F)(F)F)c4)cc3)CC2)C1] |

-continued

| Name | Structure |
|---|---|
| 3-((chloro(difluoro)methyl)sulfonyl)-N-(4-(4-((2-(4-chlorophenyl)-4,4-dimethylcyclohex-1-en-1-yl)methyl)piperazin-1-yl)benzoyl)-4-(((1R)-3-(morpholin-4-yl)-1-((phenylsulfanyl)methyl)propyl)amino)benzenesulfonamide | 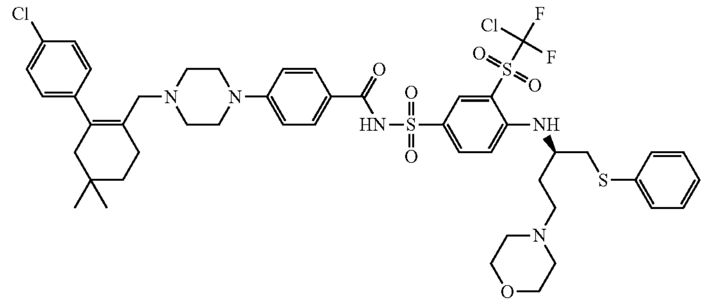 [SMILES: CC1(C)CCC(CN2CCN(c3ccc(C(=O)NS(=O)(=O)c4ccc(N[C@H](CCN5CCOCC5)CSc5ccccc5)c(S(=O)(=O)C(F)(F)Cl)c4)cc3)CC2)=C(c2ccc(Cl)cc2)C1] |
| 3-((chloro(difluoro)methyl)sulfonyl)-N-(4-(4-((2-(4-chlorophenyl)-1-cyclohex-1-en-1-yl)methyl)piperazin-1-yl)benzoyl)-4-(((1R)-3-(morpholin-4-yl)-1-((phenylsulfanyl)methyl)propyl)amino)benzenesulfonamide | 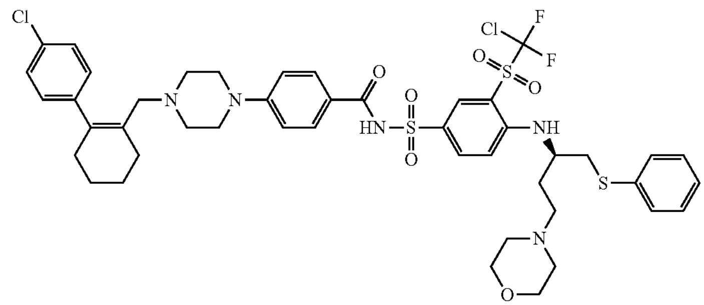 |
| N-(4-(4-((2-(4-chlorophenyl)-5,5-dimethylcyclohex-1-en-1-yl)methyl)piperazin-1-yl)benzoyl)-4-(((1R)-3-(isopropyl(methyl)amino)-1-((phenylsulfanyl)methyl)propyl)amino)-3-((trifluoromethyl)sulfonyl)benzenesulfonamide | 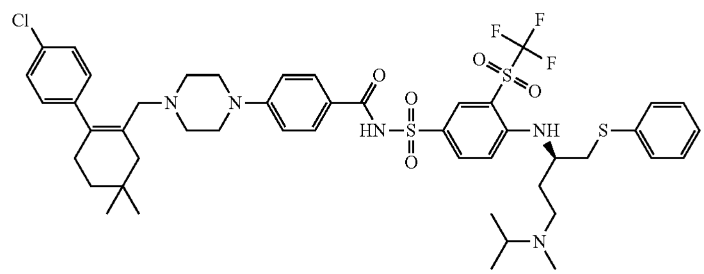 |
| N-(4-(4-((2-(4-chlorophenyl)-1-cyclohepten-1-yl)methyl)piperazin-1-yl)benzoyl)-4-(((1R)-3-(isopropyl(methyl)amino)-1-((phenylsulfanyl)methyl)propyl)amino)-3-((trifluoromethyl)sulfonyl)benzenesulfonamide | 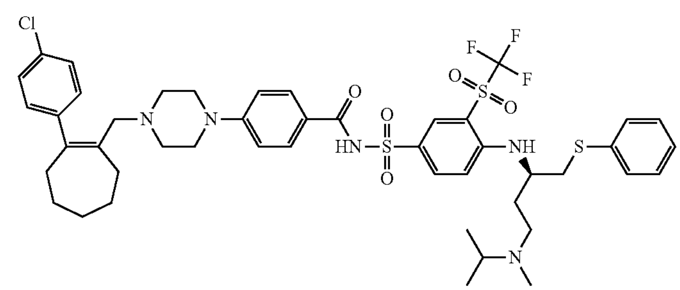 [SMILES: CC(C)N(C)CC[C@H](CSc1ccccc1)Nc1ccc(S(=O)(=O)NC(=O)c2ccc(N3CCN(CC4=C(c5ccc(Cl)cc5)CCCCC4)CC3)cc2)cc1S(=O)(=O)C(F)(F)F] |
| 3-((chloro(difluoro)methyl)sulfonyl)-N-(4-(4-((2-(4-chlorophenyl)cyclohex-1-en-1-yl)methyl)piperazin-1-yl)benzoyl)-4-(((1R)-3-((1S,4S)-2-oxa-5-azabicyclo[2.2.1]hept-5-yl)-1-((phenylsulfanyl)methyl)propyl)amino)benzenesulfonamide | 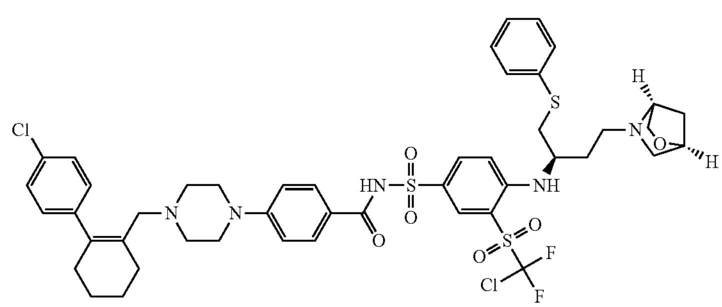 [SMILES: O=C(NS(=O)(=O)c1ccc(N[C@H](CCN2C[C@@H]3C[C@H]2CO3)CSc2ccccc2)c(S(=O)(=O)C(F)(F)Cl)c1)c1ccc(N2CCN(CC3=C(c4ccc(Cl)cc4)CCCC3)CC2)cc1] |

-continued

| Name | Structure |
|---|---|
| N-(4-(4-((2-(4-chlorophenyl)cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide | 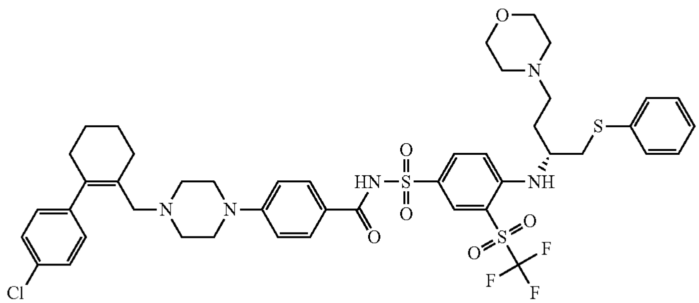 [SMILES: O=C(NS(=O)(=O)c1ccc(N[C@H](CCN2CCOCC2)CSc2ccccc2)c(S(=O)(=O)C(F)(F)F)c1)c1ccc(N2CCN(CC3=C(c4ccc(Cl)cc4)CCCC3)CC2)cc1] |
| 4-(((1R)-3-(7-azabicyclo[2.2.1]hept-7-yl)-1-((phenylsulfanyl)methyl)propyl)amino)-N-(4-(4-((2-(4-chlorophenyl)cyclohex-1-en-1-yl)methyl)piperazin-1-yl)benzoyl)-3-((trifluoromethyl)sulfonyl)benzenesulfonamide | 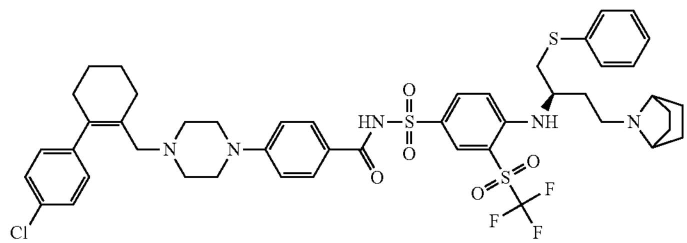 |
| N-(4-(4-((2-(4-chlorophenyl)cyclohex-1-en-1-yl)methyl)piperazin-1-yl)benzoyl)-4-(((1R)-3-(2-oxa-5-azabicyclo[2.2.1]hept-5-yl)-1-((phenylsulfanyl)methyl)propyl)amino)-3-((trifluoromethyl)sulfonyl)benzenesulfonamide | 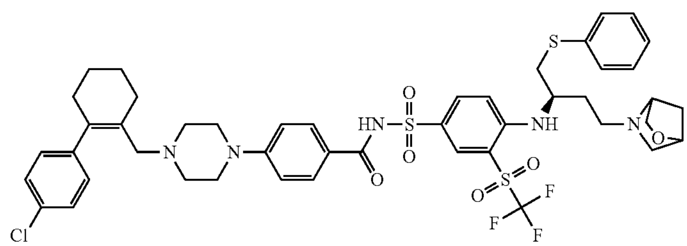 [SMILES: O=C(NS(=O)(=O)c1ccc(N[C@H](CCN2CC3CC2CO3)CSc2ccccc2)c(S(=O)(=O)C(F)(F)F)c1)c1ccc(N2CCN(CC3=C(c4ccc(Cl)cc4)CCCC3)CC2)cc1] |
| N-(4-(4-((2-(4-chlorophenyl)-5,5-dimethylcyclohex-1-en-1-yl)methyl)piperazin-1-yl)benzoyl)-4-(((1R)-3-(2-oxa-5-azabicyclo[2.2.1]hept-5-yl)-1-((phenylsulfanyl)methyl)propyl)amino)-3-((trifluoromethyl)sulfonyl)benzenesulfonamide | 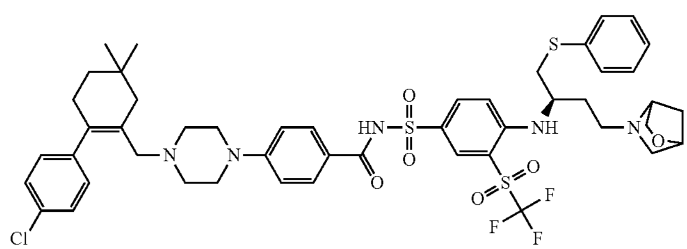 |
| 3-((chloro(difluoro)methyl)sulfonyl)-N-(4-(4-((2-(4-chlorophenyl)-5,5-dimethylcyclohex-1-en-1-yl)methyl)piperazin-1-yl)benzoyl)-4-(((1R)-3-(2-oxa-5-azabicyclo[2.2.1]hept-5-yl)-1-((phenylsulfanyl)methyl)propyl)amino)benzenesulfonamide | 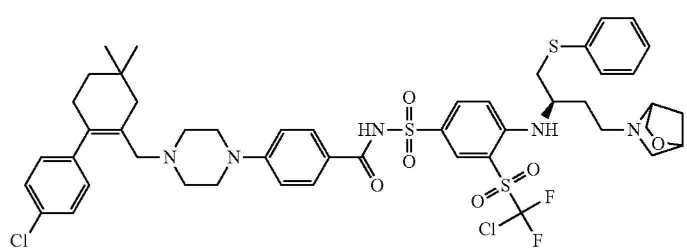 |
| N-(4-(4-((2-(4-chlorophenyl)cyclohept-1-en-1-yl)methyl)piperazin-1-yl)benzoyl)-4-(((1R)-3-(2-oxa-5-azabicyclo[2.2.1]hept-5-yl)-1-((phenylsulfanyl)methyl)propyl)amino)-3-((trifluoromethyl)sulfonyl)benzenesulfonamide | 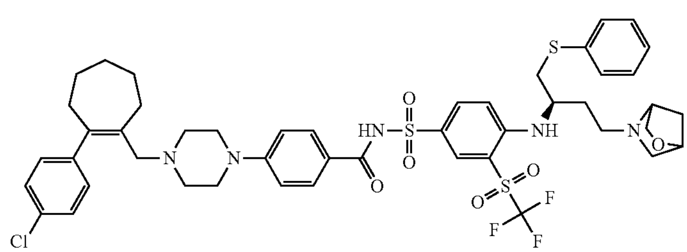 [SMILES: O=C(NS(=O)(=O)c1ccc(N[C@H](CCN2CC3CC2CO3)CSc2ccccc2)c(S(=O)(=O)C(F)(F)F)c1)c1ccc(N2CCN(CC3=C(c4ccc(Cl)cc4)CCCCC3)CC2)cc1] |

| Name | Structure |
|---|---|
| 3-((chloro(difluoro)methyl)sulfonyl)-N-(4-(4-((2-(4-chlorophenyl)cyclohept-1-en-1-yl)methyl)piperazin-1-yl)benzoyl)-4-(((1R)-3-(2-oxa-5-azabicyclo[2.2.1]hept-5-yl)-1-((phenylsulfanyl)methyl)propyl)amino)benzenesulfonamide | 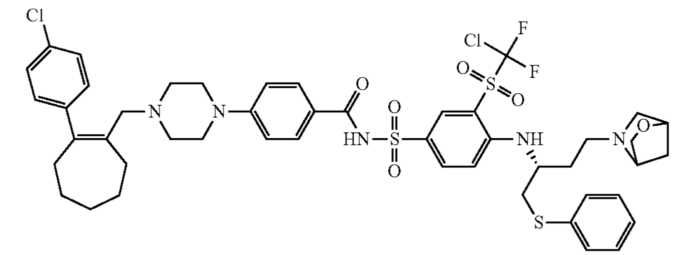 [SMILES: O=C(NS(=O)(=O)c1ccc(N[C@H](CCN2CC3CC2CO3)CSc2ccccc2)c(S(=O)(=O)C(F)(F)Cl)c1)c1ccc(N2CCN(CC3=C(c4ccc(Cl)cc4)CCCCC3)CC2)cc1] |
| N-(4-(4-((2-(4-chlorophenyl)-4,4-dimethylcyclohex-1-en-1-yl)methyl)piperazin-1-yl)benzoyl)-4-(((1R)-3-(isopropyl(methyl)amino)-1-((phenylsulfanyl)methyl)propyl)amino)-3-((trifluoromethyl)sulfonyl)benzenesulfonamide | 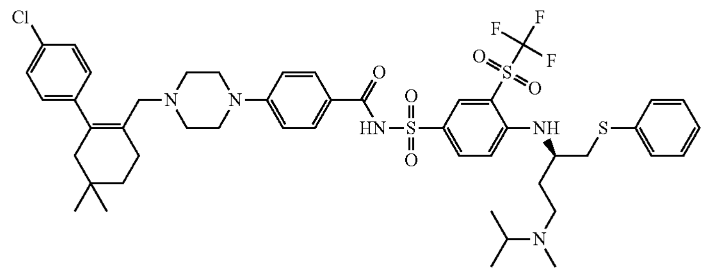 [SMILES: CC(C)N(C)CC[C@H](CSc1ccccc1)Nc1ccc(S(=O)(=O)NC(=O)c2ccc(N3CCN(CC4=C(c5ccc(Cl)cc5)CC(C)(C)CC4)CC3)cc2)cc1S(=O)(=O)C(F)(F)F] |
| N-(4-(4-((2-(4-chlorophenyl)cyclohex-1-en-1-yl)methyl)piperazin-1-yl)benzoyl)-4-(((1R)-3-(1,4-oxazepan-4-yl)-1-((phenylsulfanyl)methyl)propyl)amino)-3-((trifluoromethyl)sulfonyl)benzenesulfonamide | 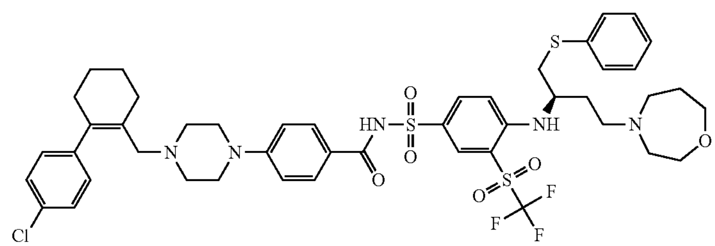 [SMILES: O=C(NS(=O)(=O)c1ccc(N[C@H](CCN2CCCOCC2)CSc2ccccc2)c(S(=O)(=O)C(F)(F)F)c1)c1ccc(N2CCN(CC3=C(c4ccc(Cl)cc4)CCCC3)CC2)cc1] |
| 4-(((1R)-3-(azepan-1-yl)-1-((phenylsulfanyl)methyl)propyl)amino)-N-(4-(4-((2-(4-chlorophenyl)-1-cyclohex-1-en-1-yl)methyl)piperazin-1-yl)benzoyl)-3-((trifluoromethyl)sulfonyl)benzenesulfonamide | 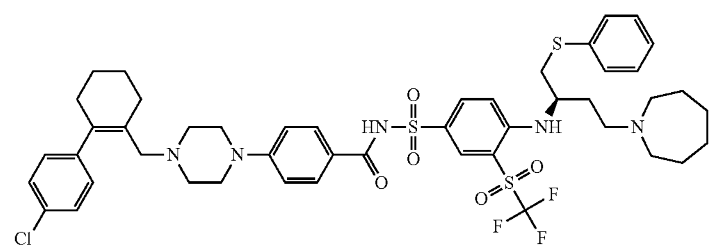 [SMILES: O=C(NS(=O)(=O)c1ccc(N[C@H](CCN2CCCCCC2)CSc2ccccc2)c(S(=O)(=O)C(F)(F)F)c1)c1ccc(N2CCN(CC3=C(c4ccc(Cl)cc4)CCCC3)CC2)cc1] |
| N-(4-(4-((2-(4-chlorophenyl)cyclohept-1-en-1-yl)methyl)piperazin-1-yl)benzoyl)-4-(((1R)-3-(dimethylamino)-1-((phenylsulfanyl)methyl)propyl)amino)-3-((trifluoromethyl)sulfonyl)benzenesulfonamide | 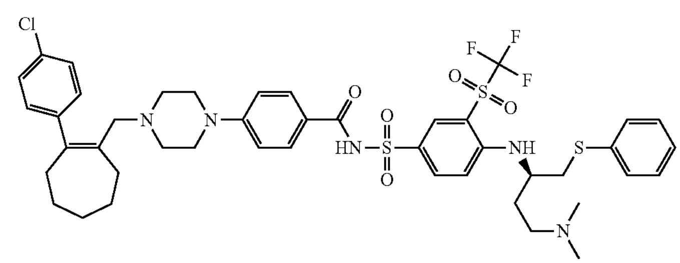 [SMILES: CN(C)CC[C@H](CSc1ccccc1)Nc1ccc(S(=O)(=O)NC(=O)c2ccc(N3CCN(CC4=C(c5ccc(Cl)cc5)CCCCC4)CC3)cc2)cc1S(=O)(=O)C(F)(F)F] |
| 3-((chloro(difluoro)methyl)sulfonyl)-N-(4-(4-((2-(4-chlorophenyl)cyclohex-1-en-1-yl)methyl)piperazin-1-yl)benzoyl)-4-(((1R)-3-(dimethylamino)-1-((phenylsulfanyl)methyl)propyl)amino)benzenesulfonamide | 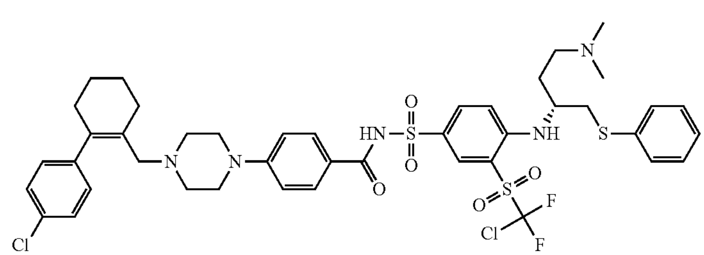 |

| Name | Structure |
|---|---|
| 3-((chloro(difluoro)methyl)sulfonyl)-N-(4-(4-((2-(4-chlorophenyl)-5,5-dimethylcyclohex-1-en-1-yl)methyl)piperazin-1-yl)benzoyl)-4-(((1R)-3-(morpholin-4-yl)-1-((phenylsulfanyl)methyl)propyl)amino)benzenesulfonamide | 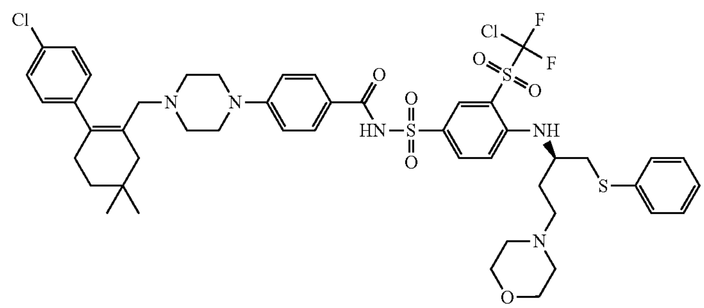 [SMILES: CC1(C)CCC(c2ccc(Cl)cc2)=C(CN2CCN(c3ccc(C(=O)NS(=O)(=O)c4ccc(N[C@H](CCN5CCOCC5)CSc5ccccc5)c(S(=O)(=O)C(F)(F)Cl)c4)cc3)CC2)C1] |
| N-(4-(4-((2-(4-chlorophenyl)-5,5-dimethyl-1-cyclohex-1-en-1-yl)methyl)piperazin-1-yl)benzoyl)-4-(((1R)-3-(dimethylamino)-1-((phenylsulfanyl)methyl)propyl)amino)-3-((trifluoromethyl)sulfonyl)benzenesulfonamide | 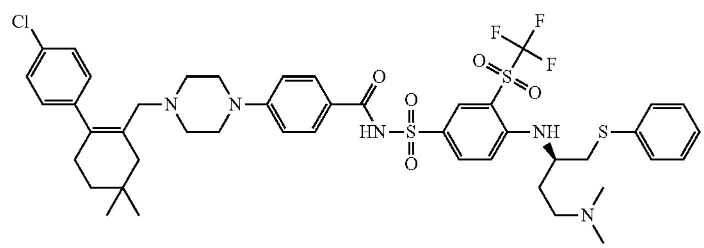 [SMILES: CN(C)CC[C@H](CSc1ccccc1)Nc1ccc(S(=O)(=O)NC(=O)c2ccc(N3CCN(CC4=C(c5ccc(Cl)cc5)CCC(C)(C)C4)CC3)cc2)cc1S(=O)(=O)C(F)(F)F] |
| N-(4-(4-((4-(4-chlorophenyl)-5,6-dihydro-2H-pyran-3-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide | 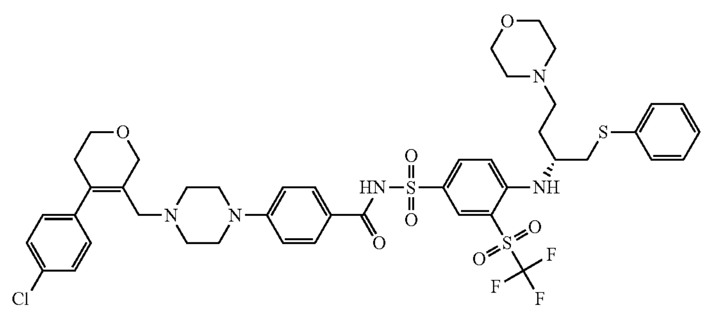 |
| 3-((chloro(difluoro)methyl)sulfonyl)-N-(4-(4-((2-(4-chlorophenyl)-4,4-dimethylcyclohex-1-en-1-yl)methyl)piperazin-1-yl)benzoyl)-4-(((1R)-3-(isopropyl(methyl)amino)-1-((phenylsulfanyl)methyl)propyl)amino)benzenesulfonamide | 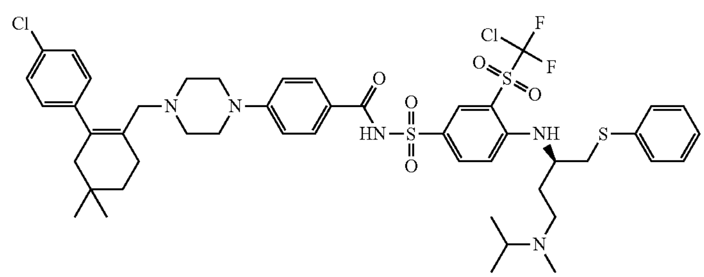 [SMILES: CC(C)N(C)CC[C@H](CSc1ccccc1)Nc1ccc(S(=O)(=O)NC(=O)c2ccc(N3CCN(CC4=C(c5ccc(Cl)cc5)CC(C)(C)CC4)CC3)cc2)cc1S(=O)(=O)C(F)(F)Cl] |
| 3-((chloro(difluoro)methyl)sulfonyl)-N-(4-(4-((2-(4-chlorophenyl)-5,5-dimethylcyclohex-1-en-1-yl)methyl)piperazin-1-yl)benzoyl)-4-(((1R)-3-(isopropyl(methyl)amino)-1-((phenylsulfanyl)methyl)propyl)amino)benzenesulfonamide | 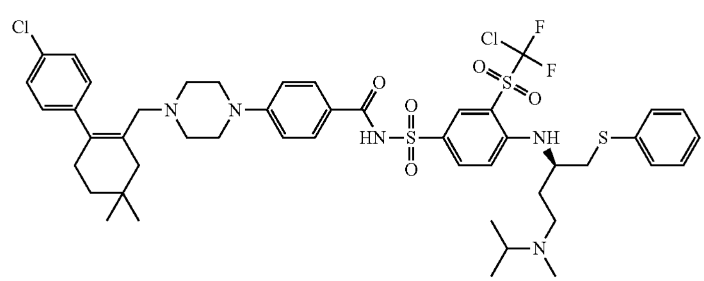 |

-continued

| Name | Structure |
|---|---|
| N-(4-(4-((2-(4-chlorophenyl)-4,4-dimethylcyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide | 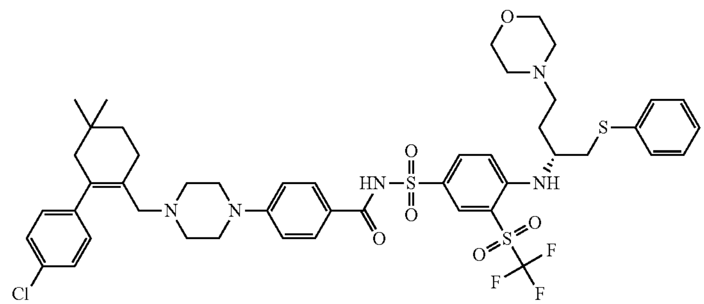 [SMILES: CC1(C)CCC(CN2CCN(c3ccc(C(=O)NS(=O)(=O)c4ccc(N[C@H](CCN5CCOCC5)CSc5ccccc5)c(S(=O)(=O)C(F)(F)F)c4)cc3)CC2)=C(c2ccc(Cl)cc2)C1] |
| 3-((chloro(difluoro)methyl)sulfonyl)-N-(4-(4-((2-(4-chlorophenyl)-4,4-dimethylcyclohex-1-en-1-yl)methyl)piperazin-1-yl)benzoyl)-4-(((1R)-3-((1S,4S)-2-oxa-5-azabicyclo[2.2.1]hept-5-yl)-1-((phenylsulfanyl)methyl)propyl)amino)benzenesulfonamide | 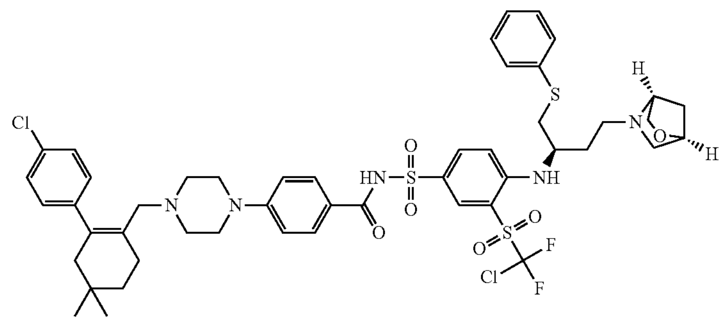 [SMILES: CC1(C)CCC(CN2CCN(c3ccc(C(=O)NS(=O)(=O)c4ccc(N[C@H](CCN5C[C@@H]6C[C@H]5CO6)CSc5ccccc5)c(S(=O)(=O)C(F)(F)Cl)c4)cc3)CC2)=C(c2ccc(Cl)cc2)C1] |
| N-(4-(4-((2-(4-chlorophenyl)cyclohex-1-en-1-yl)methyl)piperazin-1-yl)benzoyl)-4-(((1R)-3-(dimethylamino)-1-((phenylsulfanyl)methyl)propyl)amino)-3-((trifluoromethyl)sulfonyl)benzenesulfonamide | 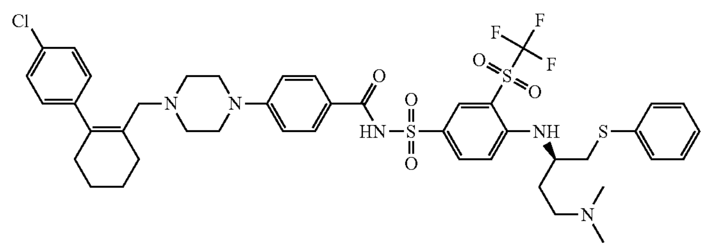 |
| N-(4-(4-((2-(4-chlorophenyl)cyclohex-1-en-1-yl)methyl)piperazin-1-yl)benzoyl)-4-(((1R)-1-((phenylsulfanyl)methyl)-3-(pyrrolidin-1-yl)propyl)amino)-3-((trifluoromethyl)sulfonyl)benzenesulfonamide | 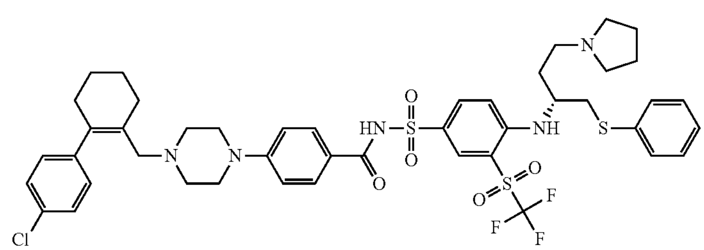 [SMILES: O=C(NS(=O)(=O)c1ccc(N[C@H](CCN2CCCC2)CSc2ccccc2)c(S(=O)(=O)C(F)(F)F)c1)c1ccc(N2CCN(CC3=C(c4ccc(Cl)cc4)CCCC3)CC2)cc1] |
| 3-((chloro(difluoro)methyl)sulfonyl)-N-(4-(4-((2-(4-chlorophenyl)-4,4-dimethylcyclohex-1-en-1-yl)methyl)piperazin-1-yl)benzoyl)-4-(((1R)-3-(dimethylamino)-1-((phenylsulfanyl)methyl)propyl)amino)benzenesulfonamide | 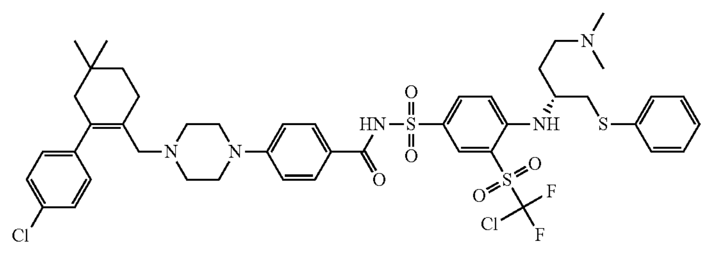 |

-continued

| Name | Structure |
|------|-----------|
| N-(4-(4-((2-(4-chlorophenyl)cyclohept-1-en-1-yl)methyl)piperazin-1-yl)benzoyl)-4-(((1R)-1-((phenylsulfanyl)methyl)-3-(pyrrolidin-1-yl)propyl)amino)-3-((trifluoromethyl)sulfonyl)benzenesulfonamide | 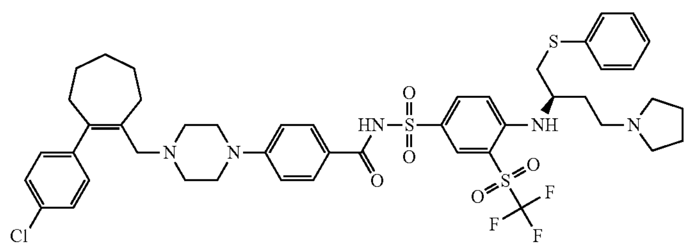 [SMILES: O=C(NS(=O)(=O)c1ccc(N[C@H](CCN2CCCC2)CSc2ccccc2)c(S(=O)(=O)C(F)(F)F)c1)c1ccc(N2CCN(CC3=C(c4ccc(Cl)cc4)CCCCC3)CC2)cc1] |
| 3-((chloro(difluoro)methyl)sulfonyl)-N-(4-(4-((2-(4-chlorophenyl)-5,5-dimethylcyclohex-1-en-1-yl)methyl)piperazin-1-yl)benzoyl)-4-(((1R)-1-((phenylsulfanyl)methyl)-3-(pyrrolidin-1-yl)propyl)amino)benzenesulfonamide | 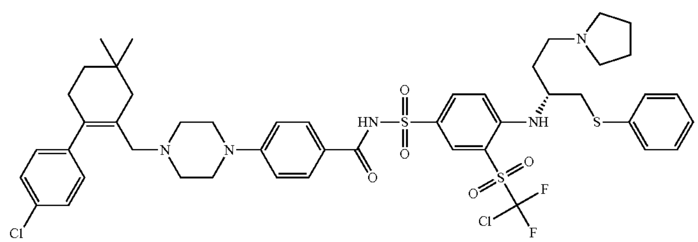 |
| 3-((chloro(difluoro)methyl)sulfonyl)-N-(4-(4-((2-(4-chlorophenyl)-4,4-dimethylcyclohex-1-en-1-yl)methyl)piperazin-1-yl)benzoyl)-4-(((1R)-1-((phenylsulfanyl)methyl)-3-(pyrrolidin-1-yl)propyl)amino)benzenesulfonamide | 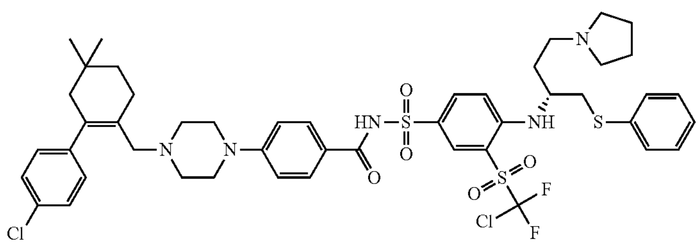 [SMILES: CC1(C)CCC(CN2CCN(c3ccc(C(=O)NS(=O)(=O)c4ccc(N[C@H](CCN5CCCC5)CSc5ccccc5)c(S(=O)(=O)C(F)(F)Cl)c4)cc3)CC2)=C(c2ccc(Cl)cc2)C1] |
| 3-((chloro(difluoro)methyl)sulfonyl)-N-(4-(4-((2-(4-chlorophenyl)cyclohept-1-en-1-yl)methyl)piperazin-1-yl)benzoyl)-4-(((1R)-1-((phenylsulfanyl)methyl)-3-(pyrrolidin-1-yl)propyl)amino)benzenesulfonamide | 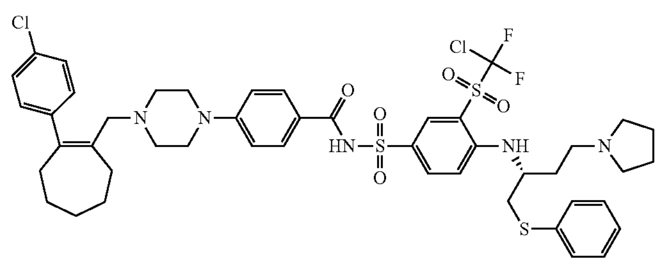 [SMILES: O=C(NS(=O)(=O)c1ccc(N[C@H](CCN2CCCC2)CSc2ccccc2)c(S(=O)(=O)C(F)(F)Cl)c1)c1ccc(N2CCN(CC3=C(c4ccc(Cl)cc4)CCCCC3)CC2)cc1] |
| N-(4-(4-((2-(4-chlorophenyl)cyclohex-1-en-1-yl)methyl)piperazin-1-yl)benzoyl)-4-(((1R)-3-(isopropyl(methyl)amino)-1-((phenylsulfanyl)methyl)propyl)amino)-3-((trifluoromethyl)sulfonyl)benzenesulfonamide | 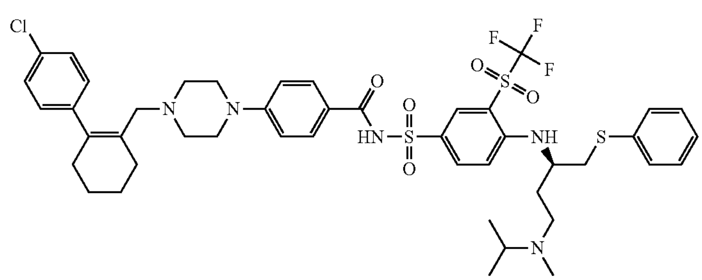 |
| N-(4-(4-((2-(4-chlorophenyl)-4,4-dimethylcyclohex-1-en-1-yl)methyl)piperazin-1-yl)benzoyl)-4-(((1R)-1-((phenylsulfanyl)methyl)-3-(pyrrolidin-1-yl)propyl)amino)-3-((trifluoromethyl)sulfonyl)benzenesulfonamide | 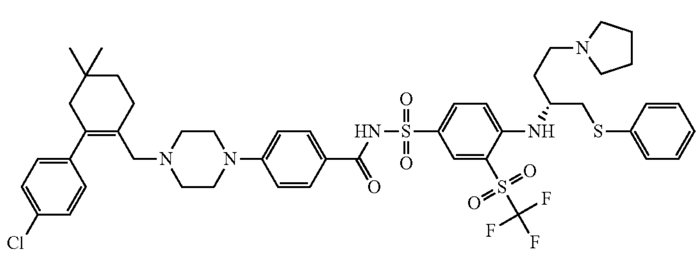 [SMILES: CC1(C)CCC(CN2CCN(c3ccc(C(=O)NS(=O)(=O)c4ccc(N[C@H](CCN5CCCC5)CSc5ccccc5)c(S(=O)(=O)C(F)(F)F)c4)cc3)CC2)=C(c2ccc(Cl)cc2)C1] |

-continued

| Name | Structure |
|---|---|
| 3-((chloro(difluoro)methyl)sulfonyl)-N-(4-(4-((2-(4-chlorophenyl)cyclohex-1-en-1-yl)methyl)piperazin-1-yl)benzoyl)-4-(((1R)-1-((phenylsulfanyl)methyl)-3-(pyrrolidin-1-yl)propyl)amino)benzenesulfonamide | 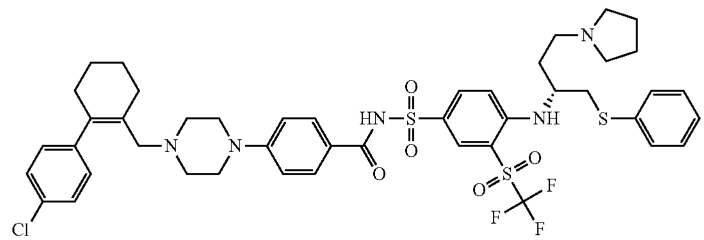 [SMILES: O=C(NS(=O)(=O)c1ccc(N[C@H](CCN2CCCC2)CSc2ccccc2)c(S(=O)(=O)C(F)(F)F)c1)c1ccc(N2CCN(CC3=C(c4ccc(Cl)cc4)CCCC3)CC2)cc1] |
| N-(4-(4-((2-(4-chlorophenyl)-4,4-dimethylcyclohex-1-en-1-yl)methyl)piperazin-1-yl)benzoyl)-4-(((1R)-3-(dimethylamino)-1-((phenylsulfanyl)methyl)propyl)amino)-3-((trifluoromethyl)sulfonyl)benzenesulfonamide | 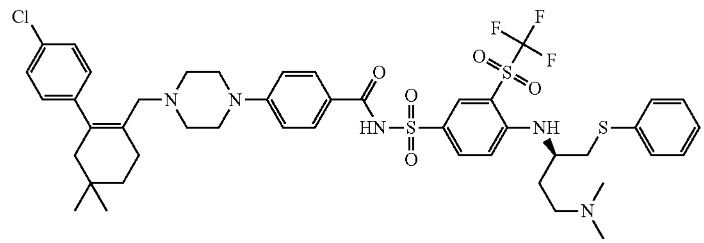 [SMILES: CN(C)CC[C@H](CSc1ccccc1)Nc1ccc(S(=O)(=O)NC(=O)c2ccc(N3CCN(CC4=C(c5ccc(Cl)cc5)CC(C)(C)CC4)CC3)cc2)cc1S(=O)(=O)C(F)(F)F] |
| N-(4-(4-((2-(4-chlorophenyl)-4,4-dimethylcyclohex-1-en-1-yl)methyl)piperazin-1-yl)benzoyl)-4-(((1R)-3-((1S,4S)-2-oxa-5-azabicyclo[2.2.1]hept-5-yl)-1-((phenylsulfanyl)methyl)propyl)amino)-3-((trifluoromethyl)sulfonyl)benzenesulfonamide | 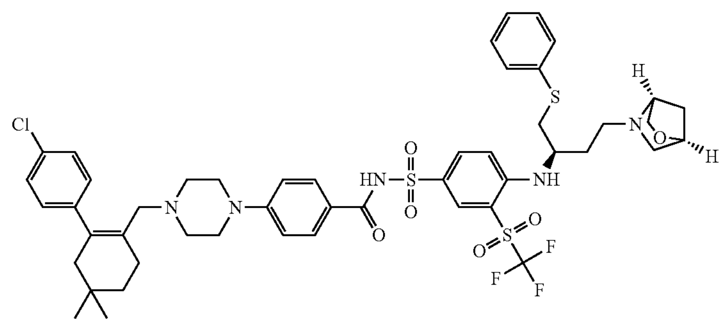 |
| N-(4-(4-((4'-chloro(1,1'-biphenyl)-2-yl)methyl)-1-piperazinyl)benzoyl)-4-(((1R)-3-(dimethylamino)-1-((phenylsulfanyl)methyl)propyl)amino)-3-((trifluoromethyl)sulfonyl)benzenesulfonamide and | 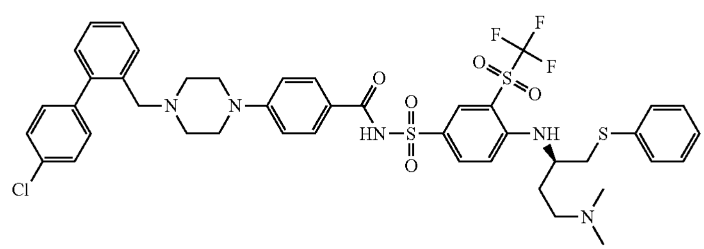 [SMILES: CN(C)CC[C@H](CSc1ccccc1)Nc1ccc(S(=O)(=O)NC(=O)c2ccc(N3CCN(Cc4ccccc4-c4ccc(Cl)cc4)CC3)cc2)cc1S(=O)(=O)C(F)(F)F] |
| N-(4-(4-((4'-chloro(1,1'-biphenyl)-2-yl)methyl)-1-piperazinyl)benzoyl)-4-(((1R)-3-(4-morpholinyl)-1-((phenylsulfanyl)methyl)propyl)amino)-3-((trifluoromethyl)sulfonyl)benzenesulfonamide | 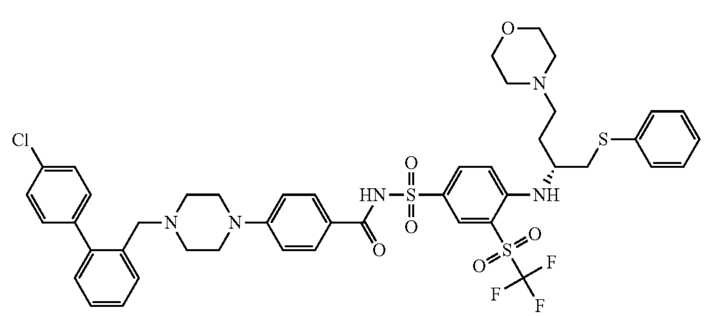 [SMILES: O=C(NS(=O)(=O)c1ccc(N[C@H](CCN2CCOCC2)CSc2ccccc2)c(S(=O)(=O)C(F)(F)F)c1)c1ccc(N2CCN(Cc3ccccc3-c3ccc(Cl)cc3)CC2)cc1] |

In some embodiments, the compound is selected from the group consisting of:

| $R_1$ | $R_2$ | A | $R^8$ |
|---|---|---|---|
| H | Me | O | 2-Me |
| H | Me | O | H |
| H | Me | O | 4-Cl |
| H | Me | O | 6-Cl |
| H | Me | O | 6-$NO_2$ |
| H | Et | O | H |
| H | Me | S | 6-$NO_2$ |
| H | Me | S | 6-Cl |
| H | iBu | O | 6-Cl |
| H | iPr | O | 6-Cl |
| H | Et | O | 6-Cl |
| H | Me | NMe | 6-Cl |
| H | Me | NH | 6-Cl |
| H | Bu | O | 6-Cl |
| H | Me | O | 5-COOH |
| H | Me | O | 6-$NH_2$ |
| H | Me | O | 6-$NHCOC_6H_5$ |
| H | Me | O | 6-NHCOMe |
| H | Me | O | 6-$NHCOCH_2C_6H_4$(4-OMe) |
| 6-F | Me | O | 4-Cl |
| 6-F | Me | O | 2-Me |
| H | Me | O | 2-Cl |
| H | Me | O | 6-COOH |
| H | Me | O | 6-NHCOBenzyl |
| H | Me | O | 6-$NHCOCH_2CH_2C_6H_4$(4-OMe) |
| 6-Br | Me | O | 6-Cl |
| 6-Cl | Me | O | 6-Cl |
| 6-$CF_3$ | Me | O | 6-Cl |
| 5-Cl, 6-F | Me | O | 6-Cl |
| 5-Br | Me | O | 6-Cl |
| 4-Br, 6-$CF_3$O | Me | O | 6-Cl |
| 6-MeO | Me | O | 6-Cl |
| 4-F | Me | O | 6-Cl |
| 4,6-$Cl_2$ | Me | O | 6-Cl |
| 4,6-$Me_2$ | Me | O | 6-Cl |
| H | Me | O | 6-$NHCOCH_2CH_2C_6H_5$ |
| H | Me | O | 6-$NHCOCH_2SC_6H_5$ |
| H | Me | O | 6-$NHCO(CH_2)_3C_6H_5$ |
| H | Me | S | 2-Me |
| H | Me | O | 6-OH |
| H | $CH_2OH$ | O | H |

In some embodiments, the compound is selected from the group consisting of:

| $R_2$ | $R_9$ | $R_{9'}$ | L | Z |
|---|---|---|---|---|
| Me | H | H | $OCH_2$ | COOH |
| Me | H | H | $NHCH_2$ | COOH |
| $CH_2CH_2CH_2$ | H | H | $OCH_2$ | COOH |
| Me | H | H | CH=CH | COOH |
| $CH_2CH_2$ | H | H | $OCH(CH_3)$ | COOH |
| $CH_2CH_2CH_2$ | H | H | $OCH_2$ | COOH |
| Me | H | $NO_2$ | $NHCH_2$ | COOH |
| iPr | H | H | $OCH_2$ | COOH |
| $CH_2CH_2CH_2$ | H | H | $OCH_2$ | $CONHSO_2Me$ |
| $CH_2CH_2CH_2$ | H | H | $OCH_2$ | $CONHSO_2CH_2C_6H_5$ |
| Me | H | H | $SCH_2$ | COOH |
| Me | H | H | $SO_2CH_2$ | COOH |
| Me | H | H | NHCO | COOH |

In some embodiments, the compound is selected from the group consisting of:

| A | $R^8$ | Z |
|---|---|---|
| O | H | $SO_2$NHCOMe |
| NMe | 6-Cl | $CONHSO_2Me$ |
| O | H | $CH_2CO_2H$ |
| NMe | 6-Cl | $CONHSO_2C_6H_4$(4-Br) |
| O | H | $SO_2NHCO(CH_2)_2$Phenyl |
| O | H | $SO_2NHCO(CH_2)_3$Phenyl |
| S | H | $SO_2$NHCOMe |
| O | H | $SO_2$NHCOPhenyl |
| O | H | $SO_2$NHCOBenzyl |
| O | H | $SO_2$NHCOCH(diPhenyl) |
| S | 6-Cl | $CONHSO_2Me$ |
| O | 6-Cl | $CONHSO_2Me$ |
| O | H | $SO_2NHCOC_6H_4$(3-Phenyl) |
| O | H | $SO_2NHCOC_6H_4$(4-Phenyl) |
| O | 6-Cl | $CONHSO_2CH_2$Phenyl |
| O | 6-Cl | $CONHSO_2(CH_2)_2$Phenyl |
| O | 6-Cl | $CONHSO_2(CH_2)_3$Phenyl |
| O | H | $SO_2NHCOCH_2OCH_2$Phenyl |
| O | H | $SO_2NHCO(CH_2)_2O$Phenyl |
| O | H | $SO_2NHCO(CH_2)_2S$Phenyl |
| O | H | $SO_2NHCOCH(NH_2)(CH_2)_2$Phenyl |
| O | H | $SO_2NHCO(CH_2)_4$Phenyl |
| O | H | $SO_2NHCO(CH_2)_5$Phenyl |
| O | H | $SO_2$NHCOCH=$CHCH_2$Phenyl |
| O | H | $SO_2NHCO(CH_2)_3C_6H_4$(4-OMe) |
| O | H | $SO_2NHCO(CH_2)_3C_6H_4$(4-I) |
| O | H | $SO_2NHCO(CH_2)_3C_6H_3$[3,4-$(OMe)_2$] |
| O | H | $SO_2NHCO(CH_2)_3C_6H_3$[2,5-$(OMe)_2$] |
| O | H | $SO_2NHCO(CH_2)_3C_6H_4$(4-$NO_2$) |
| O | H | $SO_2NHCOCH_2CH$(NHBoc)Benzyl enantiomer |
| O | H | $SO_2NHCOCH_2CH$(NHBoc)Benzyl enantiomer |
| O | H | $SO_2NHCOCH_2CH(NH_2)$Benzyl enantiomer |
| S | H | $CH_2SO_2$NHCOMe |
| S | H | $CH_2SO_2$NHCOPhenyl |
| S | H | $CH_2SO_2$NHCOBenzyl |
| S | H | $CH_2SO_2NHCO(CH_2)_2$Phenyl |
| S | H | $CH_2SO_2NHCO(CH_2)_3$Phenyl |

-continued

| A | R⁸ | Z |
|---|---|---|
| O | H | CONHSO₂Me |
| O | H | CONHSO₂Benzyl |
| O | H | SO₂NHCOCH₂CH(NH₂)Benzyl enantiomer |
| O | H | SO₂NHCOCH(NH₂)CH₂SPhenyl |
| O | H | SO₂NHCO(CH₂)₃C₆H₄(4-Me) |
| O | H | SO₂NHCO(CH₂)₂Me |
| O | H | SO₂NHCO(CH₂)₃C₆H₄ (3-Phenyl) |
| O | H | SO₂NHCOCH(NH₂)(CH₂)₂Phenyl |
| O | H | SO₂NHCOCH₂CH(NH₂)Me |
| O | H | SO₂NHCO(CH₂)₃NH₂ |
| S | H | CONH SO₂Me |
| S | H | CONH SO₂Benzyl |
| O | 6-Cl | CONHSO₂(CH₂)₄Phenyl |
| O | H | CONHSO₂(CH₂)₄Phenyl |
| O | H | SO₂NHCO(CH₂)₃C₆H₄(4-Phenyl) |
| O | H | SO₂NHCO(CH₂)₃C₆H₄(3-Br) |
| O | H | SO₂NHCO(CH₂)₃C₆H₃(3,4-OCH₂CH₂O) |
| S | H | SO₂NHCO(CH₂)₂SPhenyl |
| O | 4-Cl | SO₂NHCOMe |
| O | 4-Me | SO₂NHCOMe |
| O | 4-Me | SO₂NHCO(CH₂)₂SPhenyl |
| O | 6-Cl | SO₂NHCOMe |
| O | 6-Cl | SO₂NHCO(CH₂)₂SPhenyl |
| O | H | SO₂NHCOCH(NHBoc)CH₂SCH₂CH₂Phenyl |
| O | H | SO₂NHCOCH(NH₂)CH₂SCH₂CH₂Phenyl |
| O | H | SO₂NHCOCH₂CH₂SCH₂CH(Me)₂ |
| O | H | SO₂NHCOCH₂CH₂SPropyl |
| O | H | SO₂NHCOCH₂CH₂SCH(Me)₂ |
| O | H | SO₂NHCOCH₂CH₂SEt |
| O | H | SO₂NHCOButyl |
| O | H | SO₂NHCOCH₂CH₂CH(Me)₂ |
| O | H | SO₂NHCOCH₂CH(Me)₂ |
| O | H | SO₂NHCO(CH₂)₂SC₆H₄(4-OMe) |
| O | H | SO₂NHCOCH(NH₂)CH₂SCH(Me)₂ |
| O | H | SO₂NHCO(CH₂)₂NH₂ |
| O | H | SO₂NHCOCH(NH₂)CH₂-1-Naphthyl |
| O | H | SO₂NHCOCH(NH₂)CH₂SBenzyl |
| O | H | SO₂NHCOCH(NH₂)CH₂CH₂SBenzyl |
| O | H | SO₂NHCO(CH₂)₃C₆H₄(2-Phenyl) |
| O | H | SO₂NHCOC₆H₄[3-(CH₂)₂Phenyl] |
| O | H | SO₂NHCOC₆H₄(3-CH=CHPhenyl) |
| O | H | SO₂NHCOC₆H₄(3-Benzyl) |
| O | H | SO₂NHCOC₆H₄(4-Benzyl) |
| O | H | SO₂NHCOCH(NH₂)Benzyl |
| O | H | SO₂NHCOCH(NH₂)CH₂OBenzyl |
| O | H | SO₂NHCO(CH₂)₂SC₆H₄(4-F) |
| O | H | SO₂NHCOCH(NH₂)CH₂SCH(Me)₂ |
| O | H | SO₂NHCOCH(NH₂)CH₂SPropyl |
| O | H | SO₂NHCOCH(NH₂)CH₂SEthyl |
| O | H | SO₂NHCOCH(NH₂)CH₂SMethyl |
| O | H | SO₃H |
| O | H | SO₂NHC₆H₃(2-NO₂, 4-CF₃) |
| O | H | SO₂NH-2-pyrimidyl |
| O | H | SO₂NH-2-benzothiazolyl |

In some embodiments, the compound is selected from the group consisting of:

| R₁ | A | Z |
|---|---|---|
| H | O | COOH |
| H | S | COOH |

In some embodiments, the compound is selected from the group consisting of:

| G | Group A | Z |
|---|---|---|
| 1,3-phenyl | CH | COOH |
| 3-methyl-5-hydroxy-1,4pyrazolyl | CH | COOH |
| 2,5-thienyl | N | COOH |
| 1,3-phenyl | CH | SO₂NHCOMe |

In some embodiments, the compound is selected from the group consisting of:

| R² | R⁸ᵇ | Group A | Z |
|---|---|---|---|
| Me | H | N | COOH |
| Me | H | N | CONHSO₂(CH₂)₃Phenyl |
| Me | H | N | COOEt |
| Me | H | N | CO₂CH₂CH₂N(CH₂CH₂)₂O |
| Me | H | N | CO₂CH₂CH₂OSi(Me)₂tBu |
| Me | H | N | CO₂CH₂CH₂OH |
| CH₂CH₂ | | CH | COOH |
| Me | H | N | Tetrazol-5-yl |
| Me | H | N | CONHSO₂Me |
| Me | H | N | CONH(tetrazol-5-yl) |
| CH₂CH₂ | | N | COOH |
| CH₂CH₂CH₂ | | N | COOH |
| | | N | COOH |
| Me | H | N | SO₂NHCOMe |
| CH₂CH₂CH₂ | | CH | COOH |
| CH₂CH₂CH₂ | | N | SO₂NHCOMe |
| CH₂CH₂CH₂ | | N | SO₂NHCO(CH₂)₃Phenyl |
| CH₂CH₂CH₂ | | N | CONHSO₂(CH₂)₃Phenyl |
| CH₂CH₂CH₂ | | N | NHSO₂C₆H₄(4-Me) |
| CH₂CH₂CH₂ | | N | NHSO₂Me |
| Me | H | N | NHSO₂Me |
| CH₂CH₂CH₂ | | N | NHSO₂CF₃ |
| Me | H | N | NHSO₂C₆H₄(4-Me) |
| Me | H | N | NHSO₂CF₃ |

1591

-continued

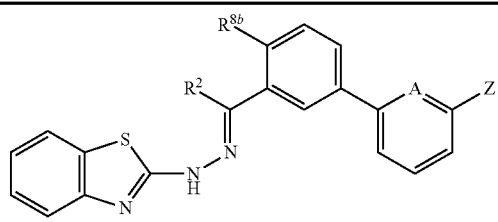

| R² | R⁸ᵇ | Group A | Z |
|---|---|---|---|
| CH₂CH₂CH₂ | | N | COOEt |
| CH₂CH₂N(Et) | | N | COOH |
| CH₂CH₂NH | | N | COOH |
| CH₂CH₂S | | N | COOH |
| CH₂CH₂CH₂CH₂ | | N | COOH |
| CH₂CH₂CH₂ | | N | CO₂CH₂CH₂N(CH₂CH₂)₂O |
| CH₂CH₂SO | | N | COOH |
| CH₂CH₂SO₂ | | N | COOH |
| CH₂CH₂S | | N | CO₂CH₂CH₂N(CH₂CH₂)₂O |
| CH₂CH(CF₃)NH | | N | COOH |
| CHC(Me)O | | N | COOH |
| CH(Me)CH₂CH₂ | | N | COOH |
| C(Me)₂CH₂CH₂ | | N | COOH |
| CH₂CH(Me)CH₂ | | N | COOH |
| CH₂CH₂CH₂O | | N | COOH |
| C(=O)NMe | | N | COOH |

In some embodiments, the compound is selected from the group consisting of:

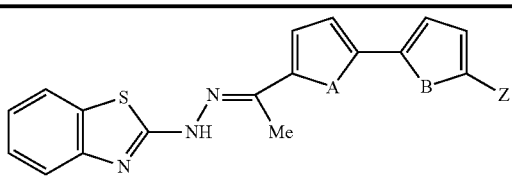

| A | B | Z |
|---|---|---|
| S | O | COOH |
| S | S | COOH |

In some embodiments, the compound is selected from the group consisting of:

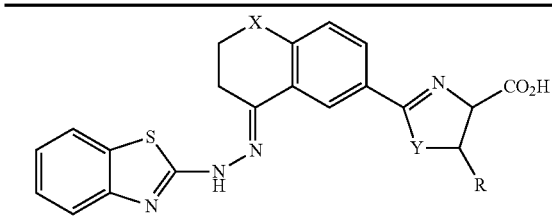

| X | Y | R |
|---|---|---|
| CH₂ | S | H |
| CH₂ | O | H |
| O | S | H |
| CH₂CH₂ | S | H |
| CH₂ | N=CH | H |

In some embodiments, the compound is selected from the group consisting of:

1592

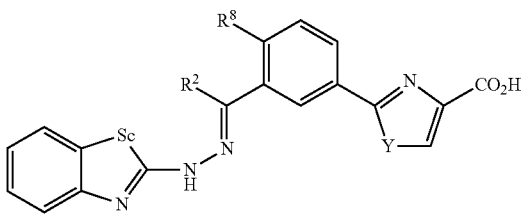

| R² | R⁸ | Y |
|---|---|---|
| Me | H | CH=CH |
| CH₂CH₂CH₂ | | CH=CH |
| CH₂CH₂S | | CH=CH |

In some embodiments, the compound is selected from the group consisting of:

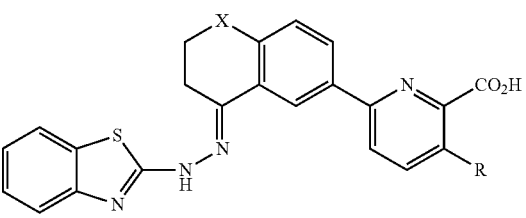

| X | R |
|---|---|
| CH₂ | OH |
| CH₂ | OCOMe |
| CH₂ | OCH₂CH₂OPhenyl |
| CH₂ | OMe |

In some embodiments, the compound is selected from the group consisting of:

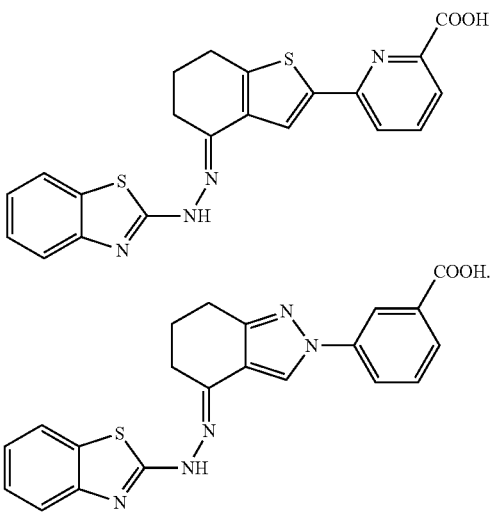

In some embodiments, the compound is selected from the group consisting of:

N-{7-[4-(4'-Chloro-biphenyl-2-ylmethyl)-piperazin-1-yl]-quinazolin-4-yl}-4-((R)-3-dimethylamino-1-phenyl-sulfanylmethyl-propylamino)-3-nitro-benzenesulfonamide

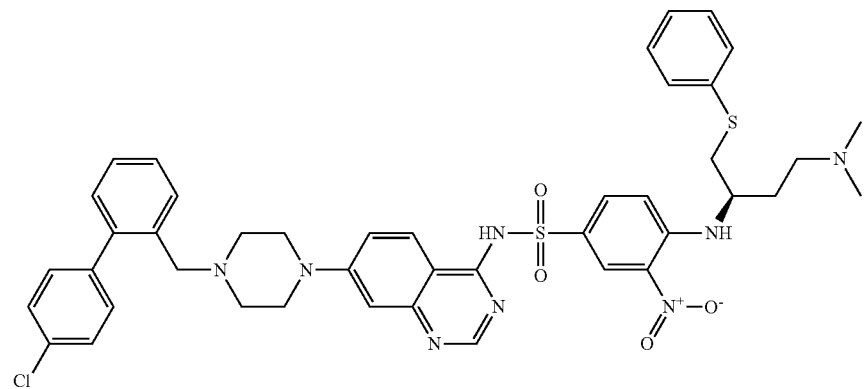 [SMILES: CN(C)CC[C@H](CSc1ccccc1)Nc1ccc(S(=O)(=O)Nc2ncnc3cc(N4CCN(Cc5ccccc5-c5ccc(Cl)cc5)CC4)ccc23)cc1[N+](=O)[O-]]

N-{7-[4-(4'-Chloro-biphenyl-2-ylmethyl)-piperazin-1-yl]-quinazolin-4-yl}-4-((R)-3-dimethylamino-1-phenyl-sulfanylmethyl-propylamino)-3-trifluoromethanesulfonyl-benzenesulfonamide

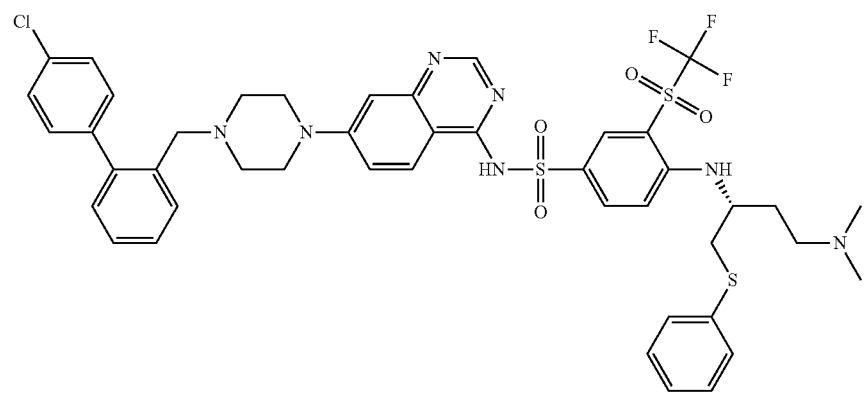 [SMILES: CN(C)CC[C@H](CSc1ccccc1)Nc1ccc(S(=O)(=O)Nc2ncnc3cc(N4CCN(Cc5ccccc5-c5ccc(Cl)cc5)CC4)ccc23)cc1S(=O)(=O)C(F)(F)F]

N-{7-[4-(4'-Chloro-biphenyl-2-ylmethyl)-piperazin-1-yl]-quinazolin-4-yl}-4-((R)-3-morpholin-4-yl-1-phenylsulfanylmethyl-propylamino)-3-nitro-benzenesulfonamide

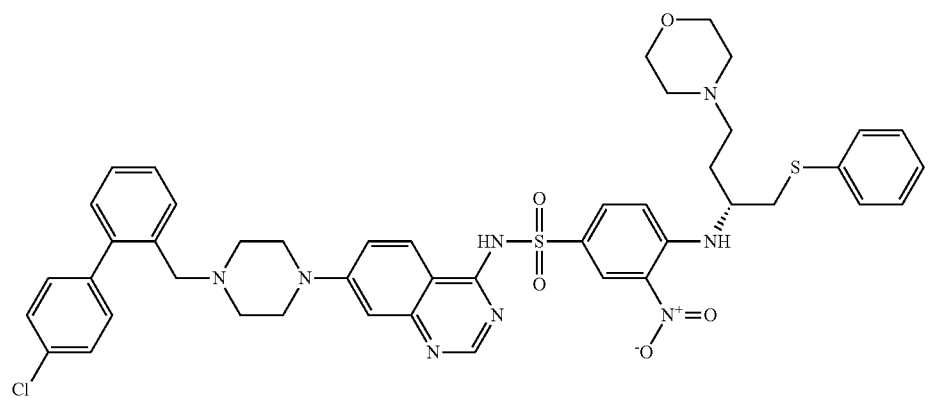

N-{7-[4-(4'-Chloro-biphenyl-2-ylmethyl)-piperazin-1-yl]-quinazolin-4-yl}-4-((R)-3-morpholin-4-yl-1-phenylsulfanylmethyl-propylamino)-3-trifluoro-methanesulfonyl-benzenesulfonamide

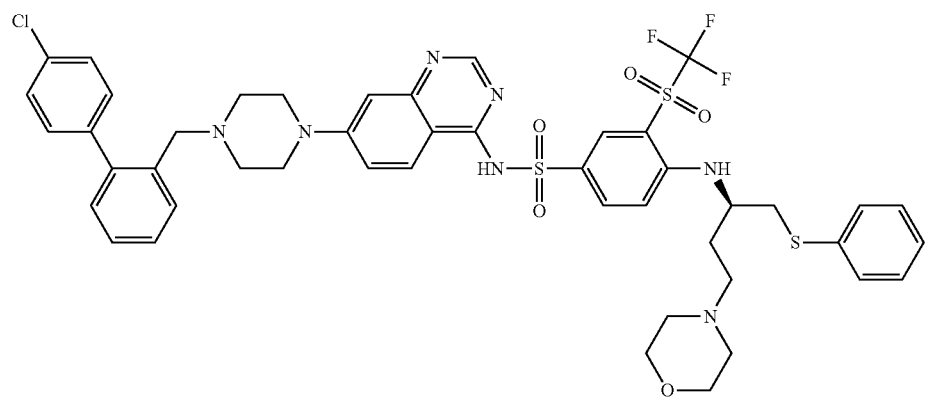 [SMILES: O=S(=O)(Nc1ncnc2cc(N3CCN(Cc4ccccc4-c4ccc(Cl)cc4)CC3)ccc12)c1ccc(N[C@H](CCN2CCOCC2)CSc2ccccc2)c(S(=O)(=O)C(F)(F)F)c1]

N-(7-{4-[2-(4-Chloro-phenyl)-5,5-dimethyl-cyclohex-1-enylmethyl]-piperazin-1-yl}-quinazolin-4-yl)-4-((R)-3-dimethyl-amino-1-phenylsulfanyl-methyl-propylamino)-3-nitro-benzenesulfonamide

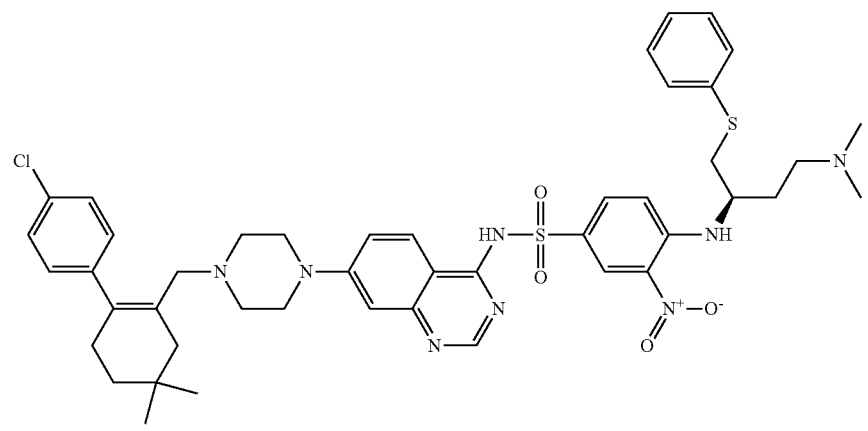 [SMILES: CN(C)CC[C@H](CSc1ccccc1)Nc1ccc(S(=O)(=O)Nc2ncnc3cc(N4CCN(CC5=C(c6ccc(Cl)cc6)CCC(C)(C)C5)CC4)ccc23)cc1[N+](=O)[O-]]

N-(7-{4-[2-(4-Chloro-phenyl)-5,5-dimethyl-cyclohex-1-enylmethyl]-piperazin-1-yl}-quinazolin-4-yl)-4-((R)-3-dimethyl-amino-1-phenylsulfanyl-methyl-propylamino)-3-trifluoromethanesulfonyl-benzenesulfonamide

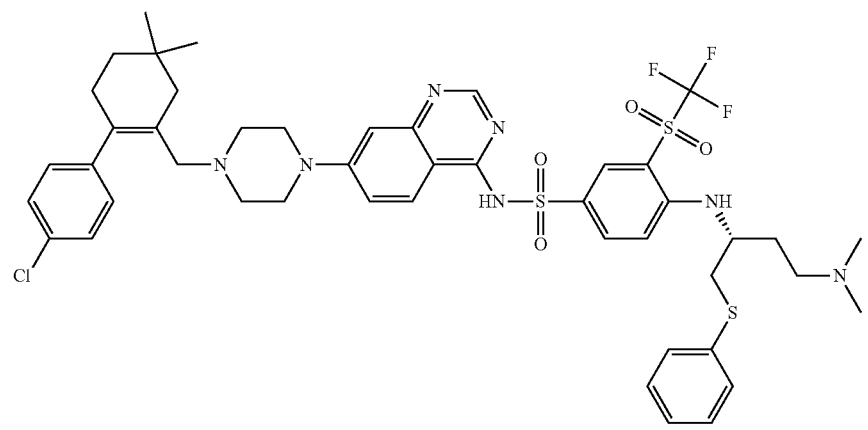 [SMILES: CN(C)CC[C@H](CSc1ccccc1)Nc1ccc(S(=O)(=O)Nc2ncnc3cc(N4CCN(CC5=C(c6ccc(Cl)cc6)CCC(C)(C)C5)CC4)ccc23)cc1S(=O)(=O)C(F)(F)F]

N-(7-{4-[2-(4-Chloro-phenyl)-5,5-dimethyl-cyclohex-1-enylmethyl]-piperazin-1-yl}-quinazolin-4-yl)-4-((R)-3-morpholin-4-yl-1-phenylsulfanylmethyl-propylamino)-3-nitro-benzenesulfonamide

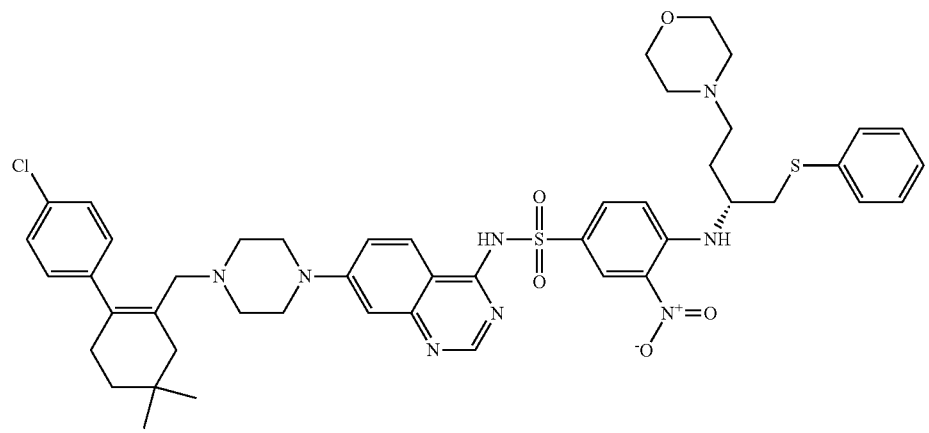

-continued

| N-(7-{4-[2-(4-Chloro-phenyl)-5,5-dimethyl-cyclohex-1-enylmethyl]-piperazin-1-yl}-quinazolin-4-yl)-4-((R)-3-morpholin-4-yl-1-phenylsulfanyl-methylpropylamino)-3-trifluoromethanesulfonyl benzenesulfonamide | 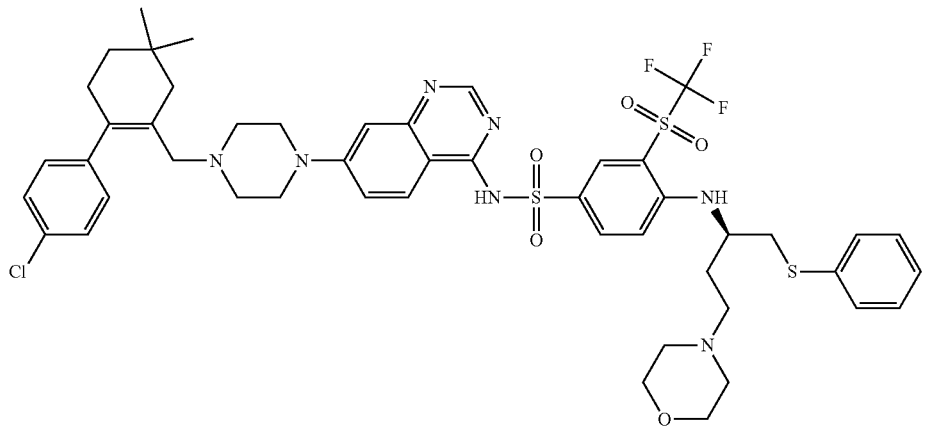 |
|---|---|
| (R)-N-(7-(4-((4'-chlorobiphenyl-2-yl)methyl)piperazin-1-yl)quinazolin-4-yl)-4-(4-(dimethylamino)-1-(phenylthio)butan-2-ylamino)-3-nitrobenzene-sulfonamide |  |

In some embodiments, the compound is selected from the group consisting of:

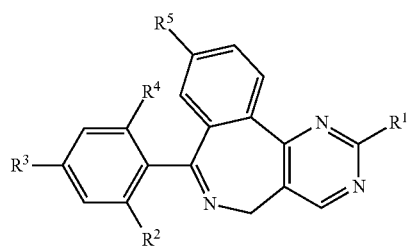

wherein

R1 is an amino or an alkyl group, optionally substituted with at least one C1-C6alkyl group;

R2 is H or halogen;

R3 is H, halogen, hydroxyl group, or alkyl group; $CH_3$,

R4 is H or halogen;

R5 is halogen; and salt thereof.

In some embodiments, the compound is

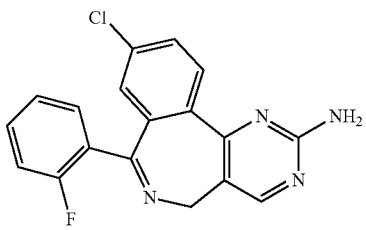 [SMILES: Nc1ncc2c(n1)-c1ccc(Cl)cc1C(c1ccccc1F)=NC2]

In some embodiments, the compound is selected from the group consisting of:

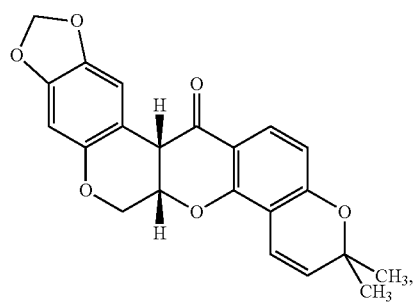

Chiral

1599
-continued
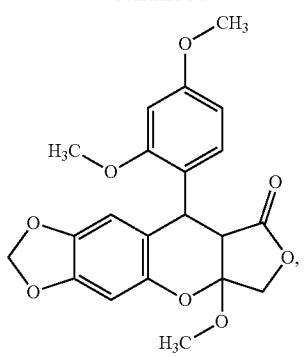
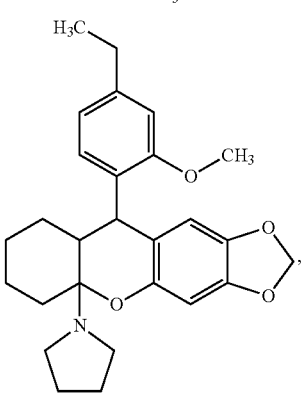
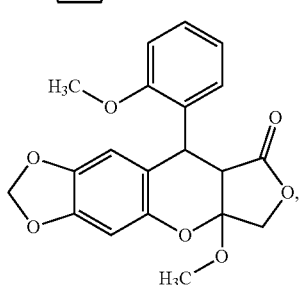
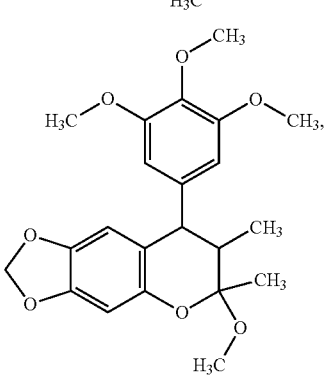
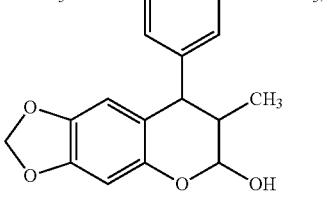
1600
-continued
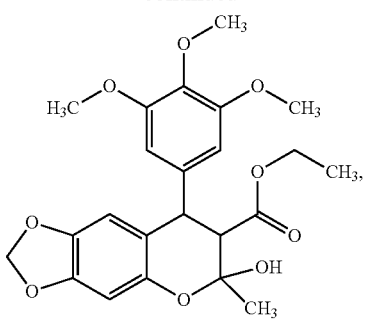
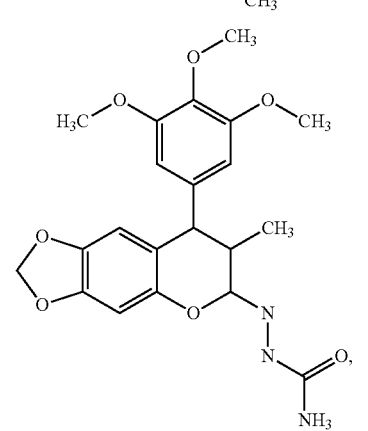
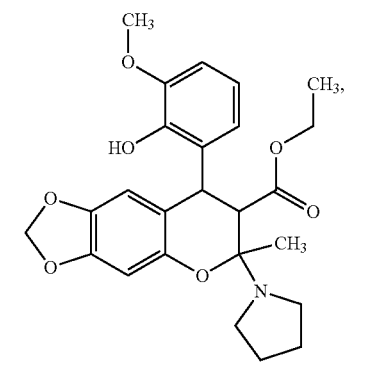
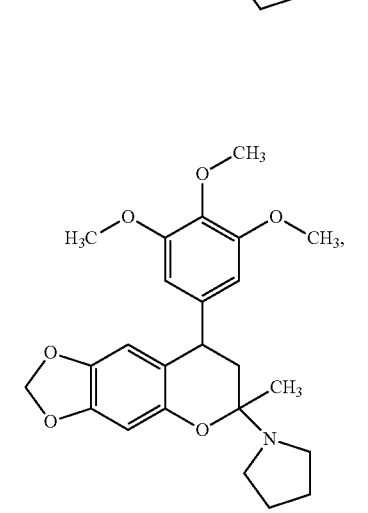

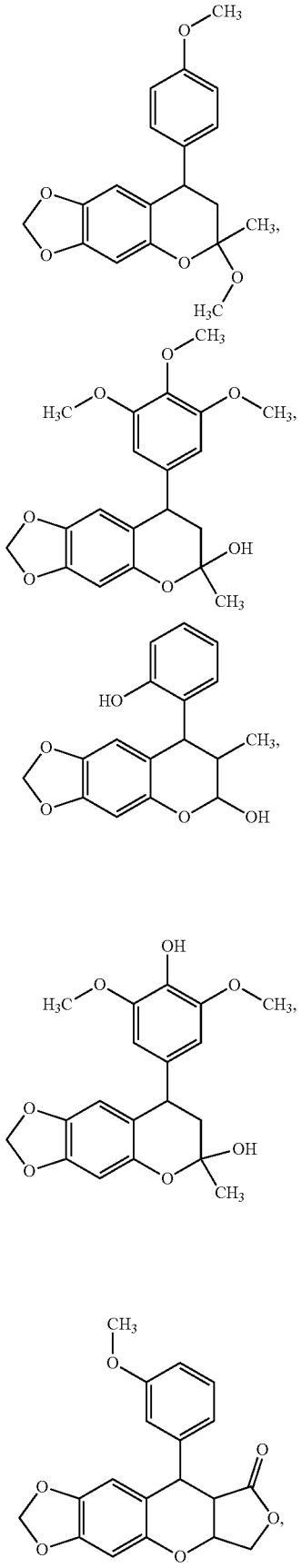
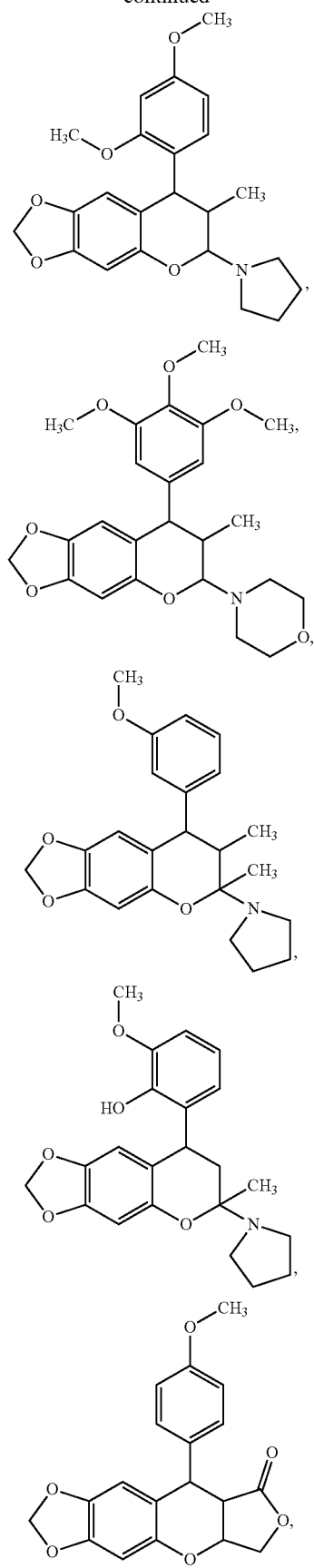

1603
-continued
1604
-continued
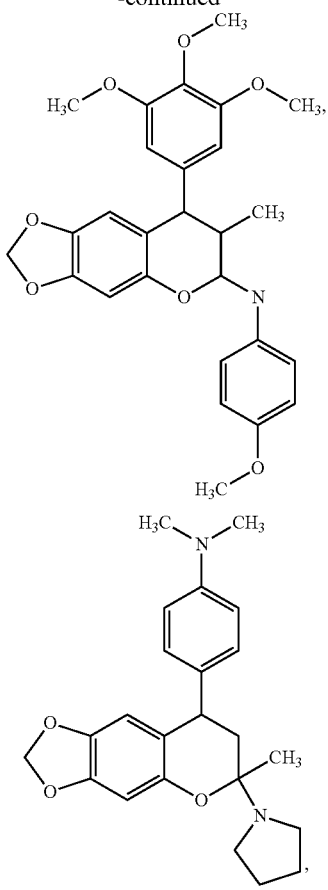
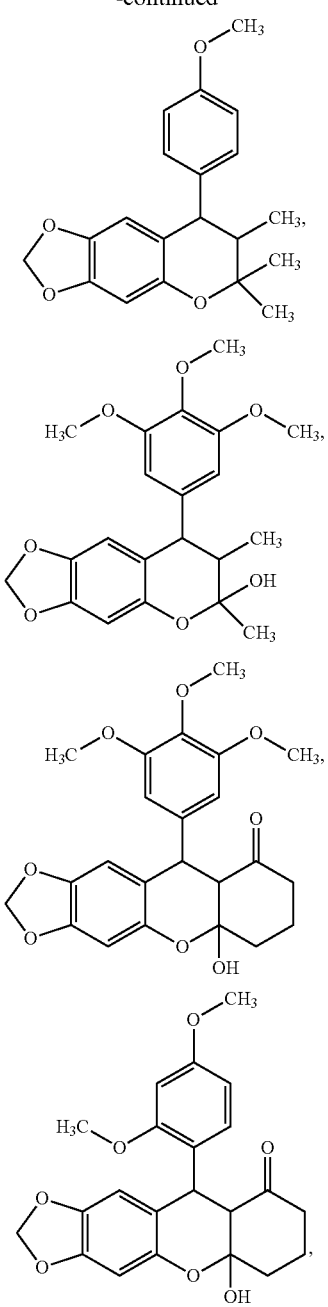
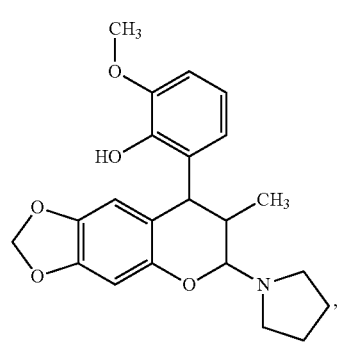

1605
-continued
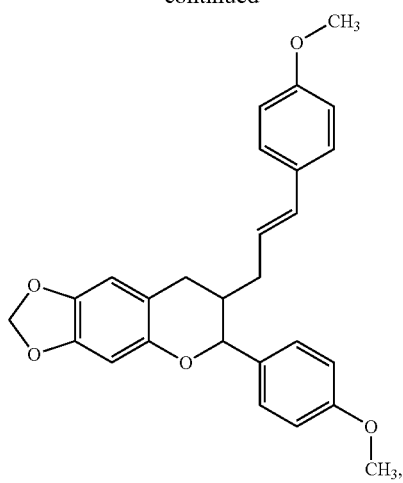
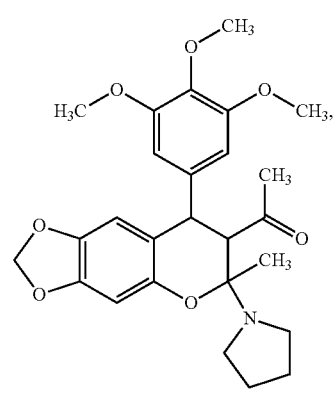
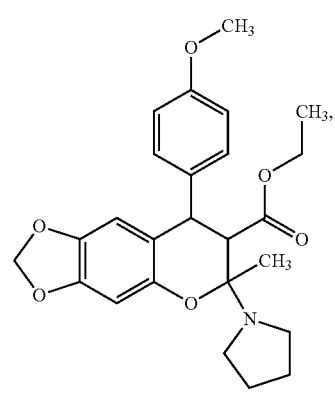
1606
-continued
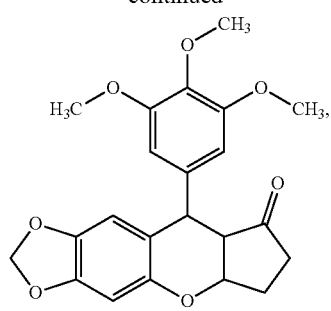
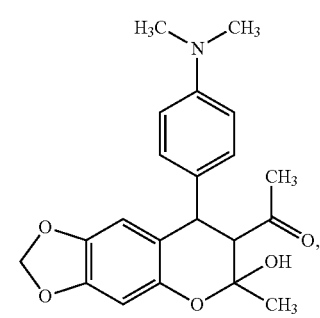
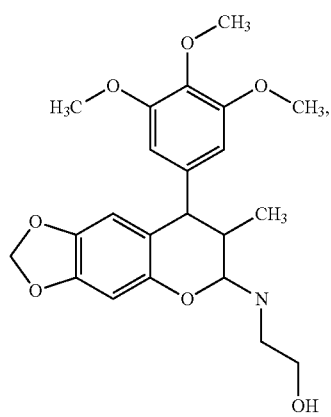

1607
-continued
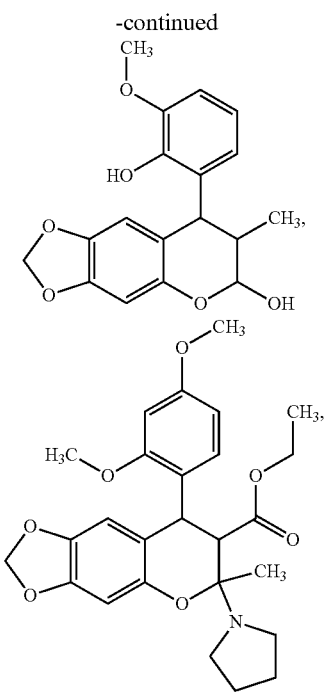
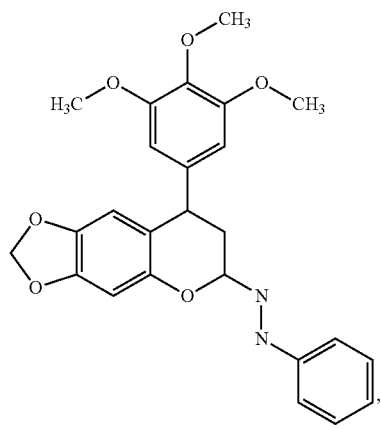
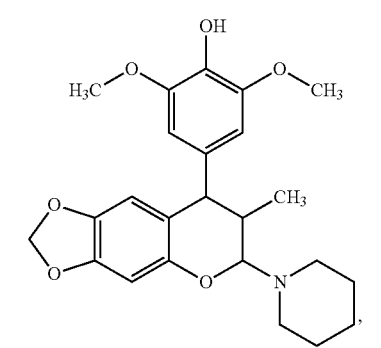
1608
-continued
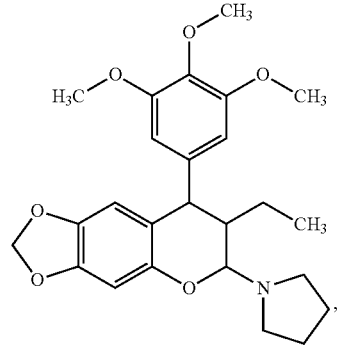
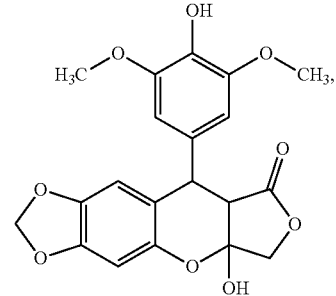
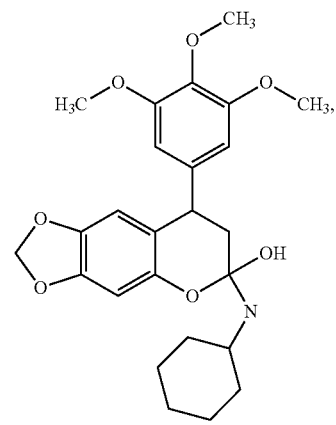
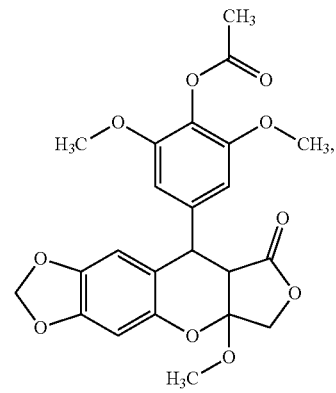

1609
-continued
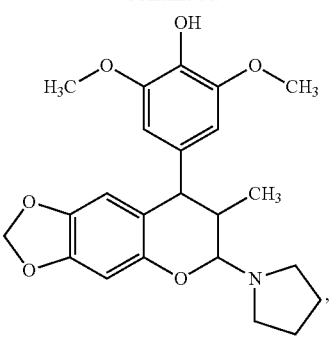
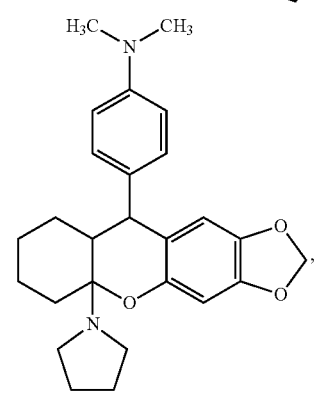
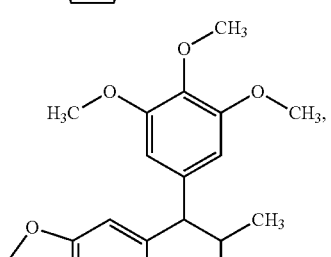
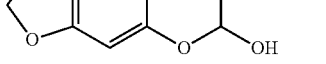
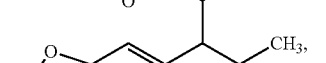
1610
-continued
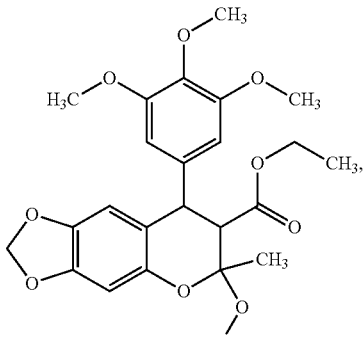
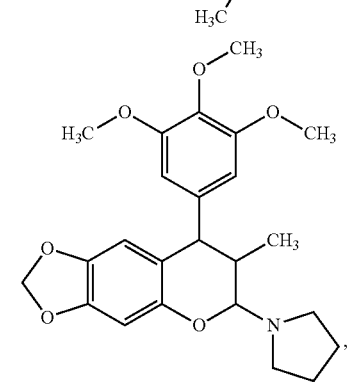
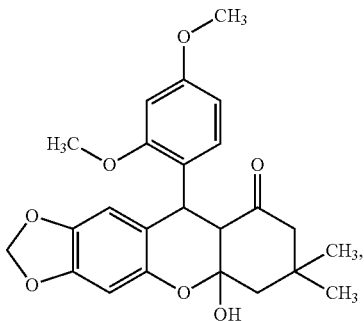
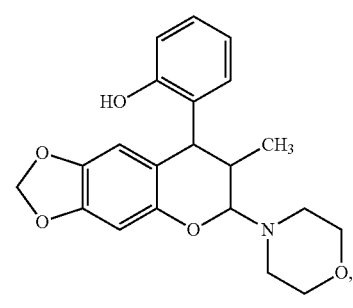
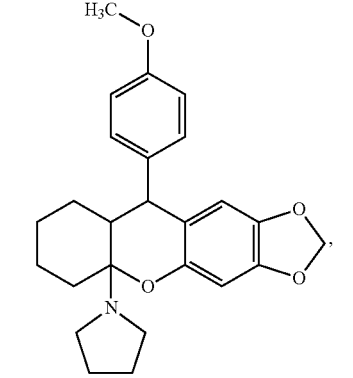

1611
-continued
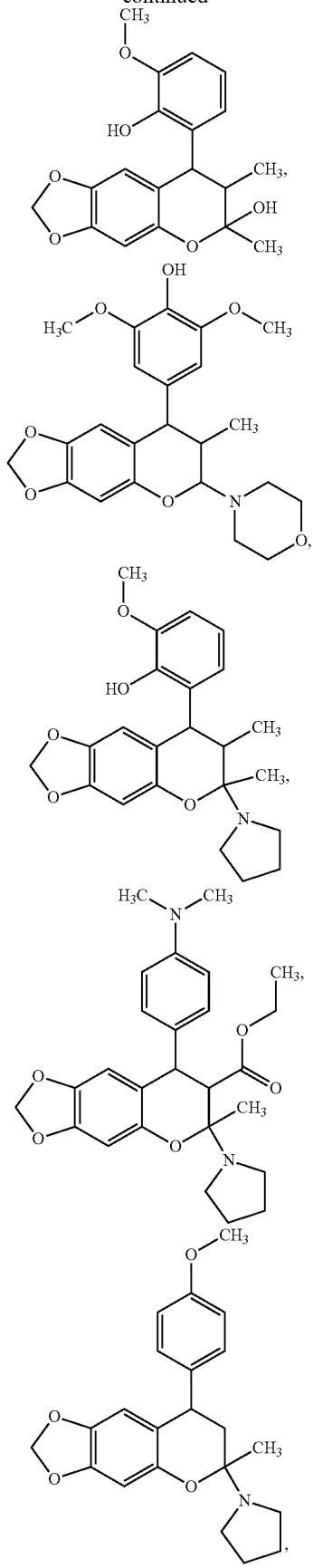
1612
-continued
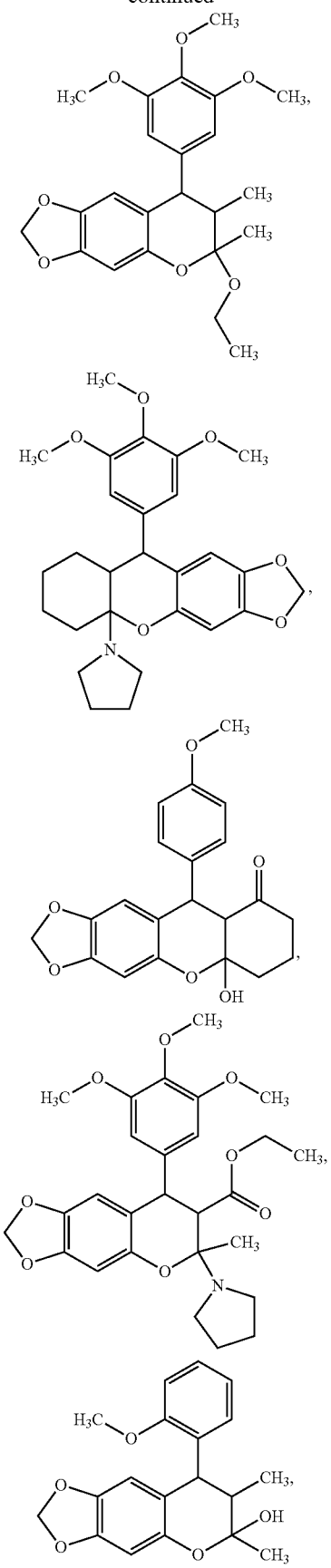

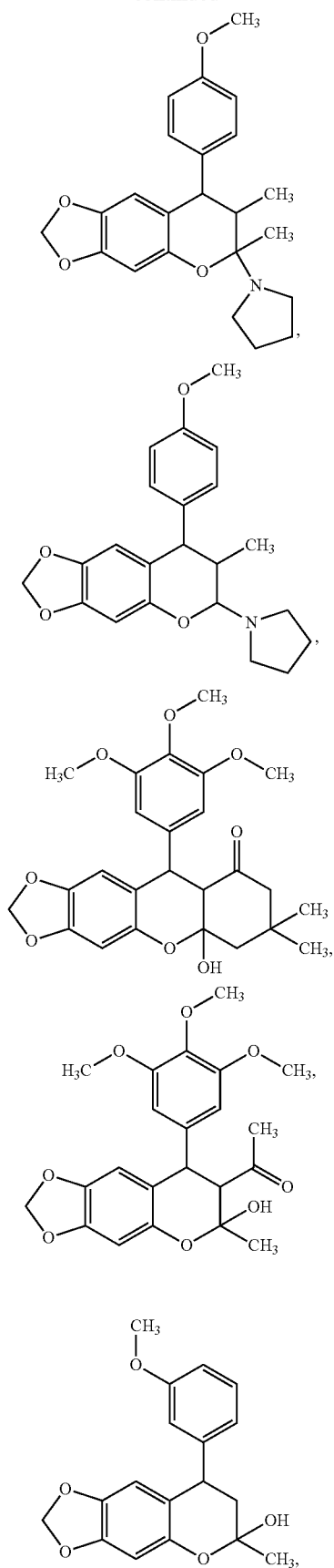
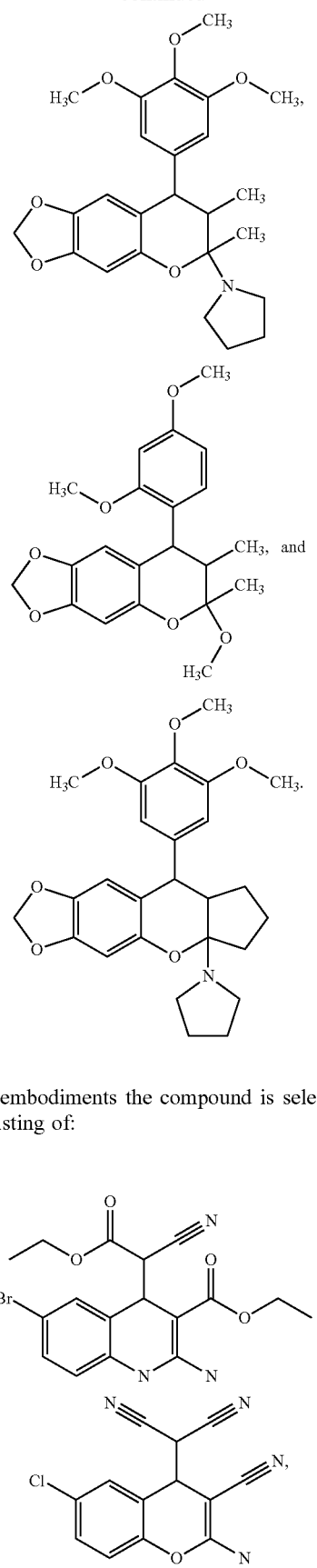
In some embodiments the compound is selected from a group consisting of:
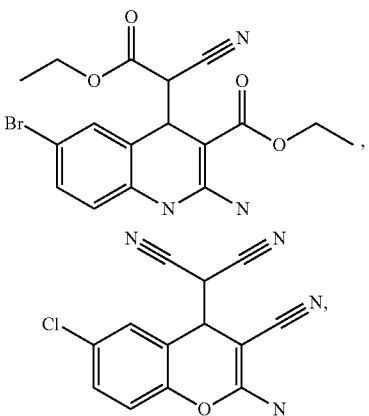

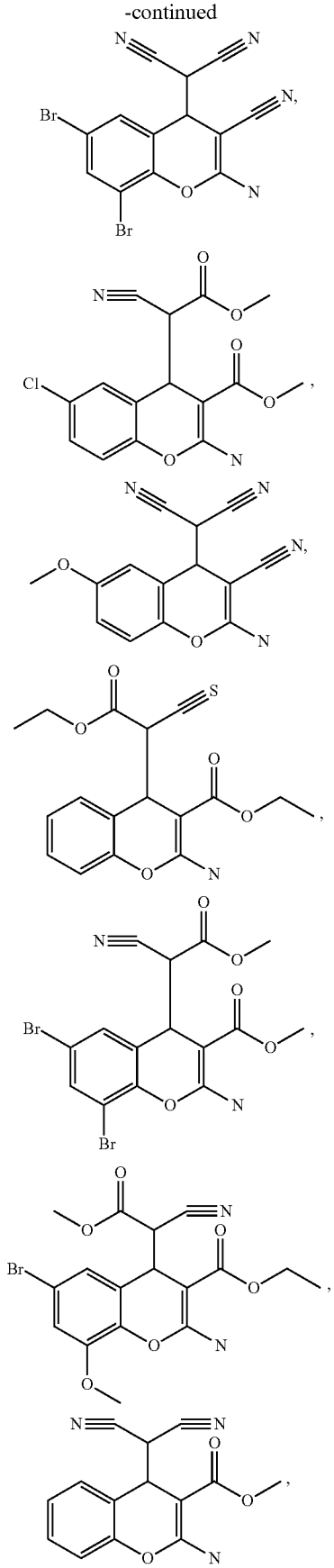
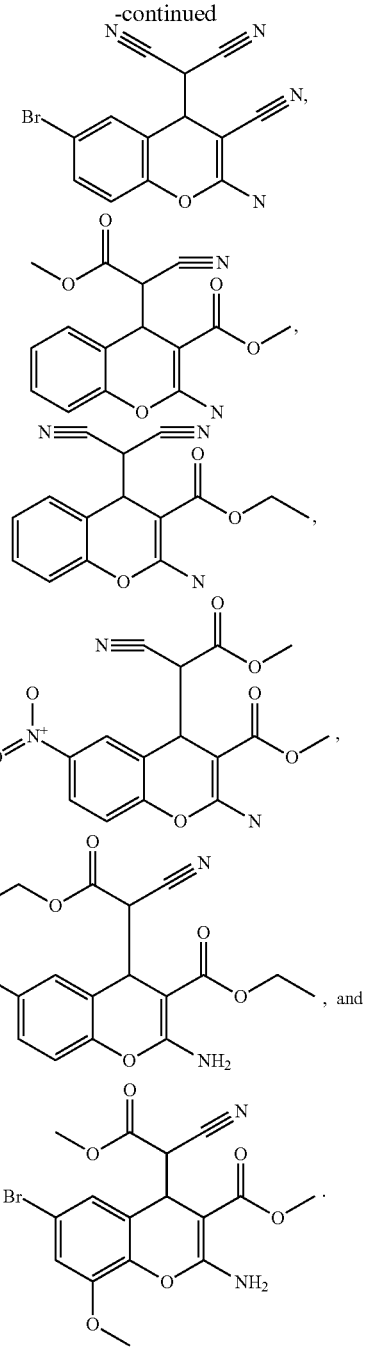
In some embodiments, the compound is selected from the group consisting of:
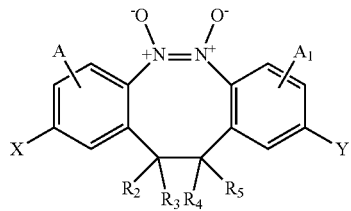

wherein
X and Y are each independently hydrogen, OR or $OR_1$;
R and R1 are each independently hydrogen, $C_1$-$C_6$alkyl, $C_2$-$C_6$alkenyl, $C_3$-$C_8$cycloalkyl, phenyl or trifluoromethyl;
$R_2$, $R_3$, $R_4$, and $R_5$ are each independently hydrogen, hydroxy, $C_1$-$C_6$alkyl, $C_2$-$C_6$alkenyl. $C_3$-$C_8$cycloalkyl, phenyl, $C_1$-$C_6$alkoxy, trifluoromethyl, amino, $C_1$-$C_6$monoalkylamino or $C_1$-$C_6$dialkylamino;
A and A2 are each independently 1 to 3 substituents selected from the group consisting of hydrogen, $C_1$-$C_6$alkyl, $C_2$-$C_6$alkenyl, fluorine, chlorine, bromine, iodine, $C_1$-$C_6$alkyl-alkoxy, amino, $C_1$-$C_6$alkylamino and $C_1$-$C_6$dialkylamino; and pharmaceutically acceptable salts thereof.

In some embodiments, the compound is:

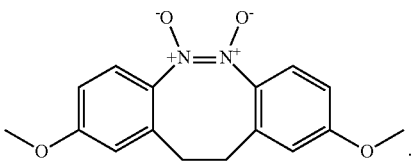

In some embodiments, the compound is selected from the group consisting of:

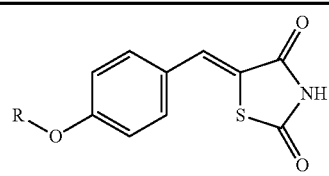

R

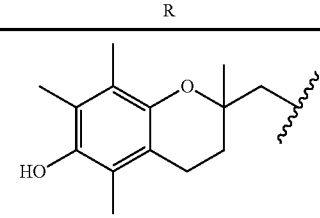

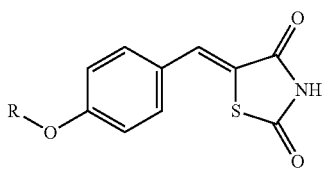

R

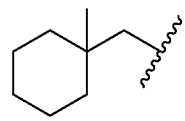 [SMILES: *CC1(C)CCCCC1]

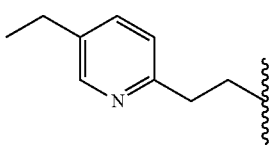 [SMILES: *CCc1ccc(CC)cn1]

In some embodiments, the compound is selected from the group consisting of:

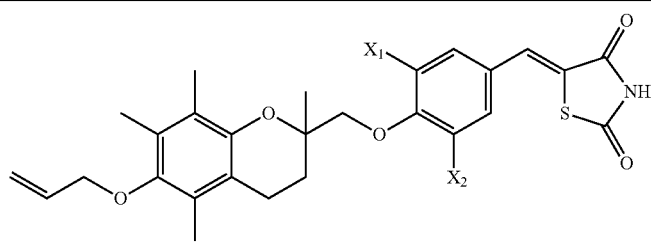

| $X_1$ | $X_2$ |
|---|---|
| H | H |
| Br | H |
| OMe | H |
| Me | H |
| Me | Me |
| Br | OMe |
| OEt | H |
| Br | Br |

-continued
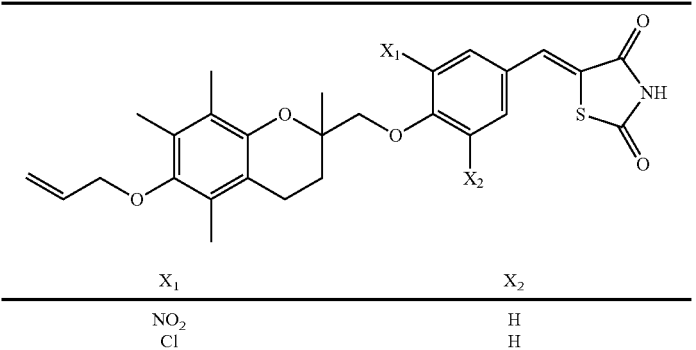
| X₁ | X₂ |
|---|---|
| NO₂ | H |
| Cl | H |
In some embodiments, the compound is selected from the group consisting of:
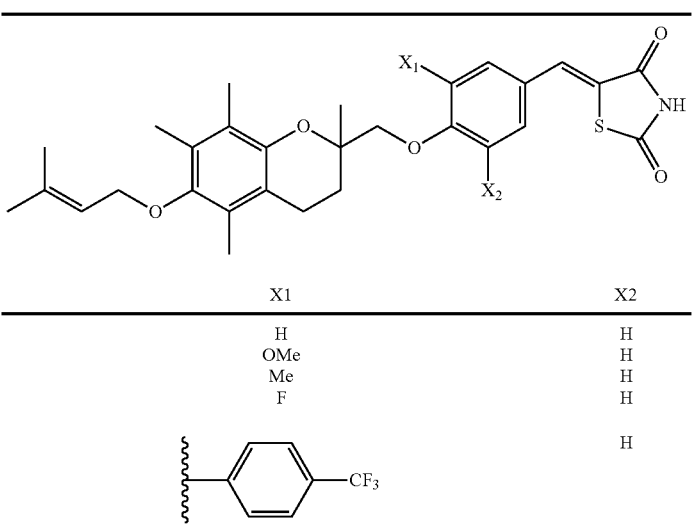
| X1 | X2 |
|---|---|
| H | H |
| OMe | H |
| Me | H |
| F | H |
| 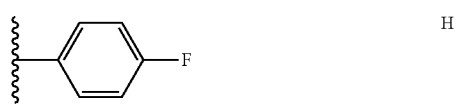 | H |
| 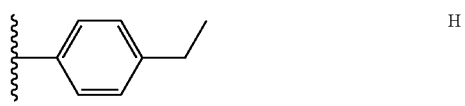 | H |
|  | H |
| Br | Br |
| NO₂ | H |
| Br | OMe |
| OEt | H |
| Br | H |
| Me | Me |
| Cl | H |

In some embodiments, the compound is selected from the group consisting of:
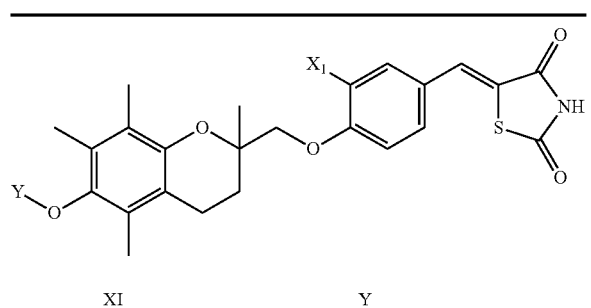
| XI | Y |
|---|---|
| H | 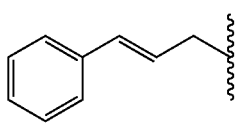 [SMILES: *C/C=C/c1ccccc1] |
| Br | 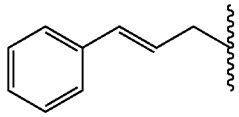 [SMILES: *C/C=C/c1ccccc1] |
| H | 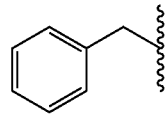 [SMILES: *Cc1ccccc1] |
| H | 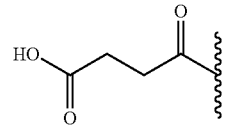 |
| Br | 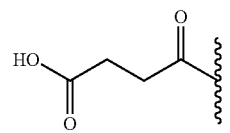 [SMILES: *C(=O)CCC(=O)O] |
| H | 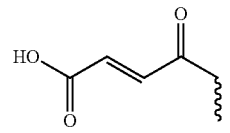 |
| Br | 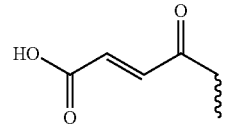 |
| H | 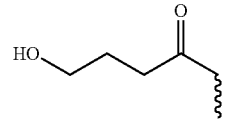 |
| Br | 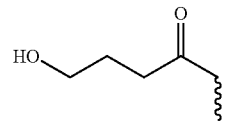 |
-continued
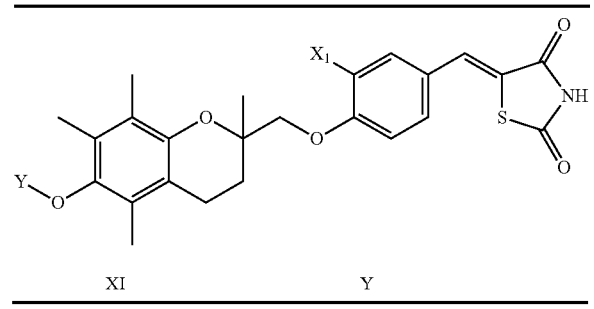
| XI | Y |
|---|---|
| Br | 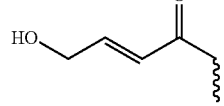 |
In some embodiments, the compound is selected from the group consisting of:
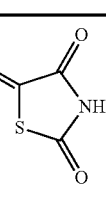
| $X_1$ | Y |
|---|---|
| H | 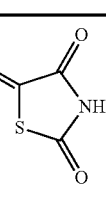 |
| Br | 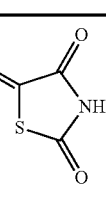 |
In some embodiments, the compound is selected from the group consisting of:
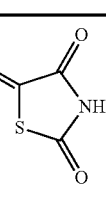
| $X_1$ | Z |
|---|---|
| H | 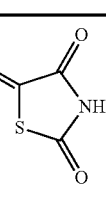 |

| | 1623 -continued | | 1624 -continued |
|---|---|---|---|
| H | | H | |
| OMe | | OMe | |
| OEt | 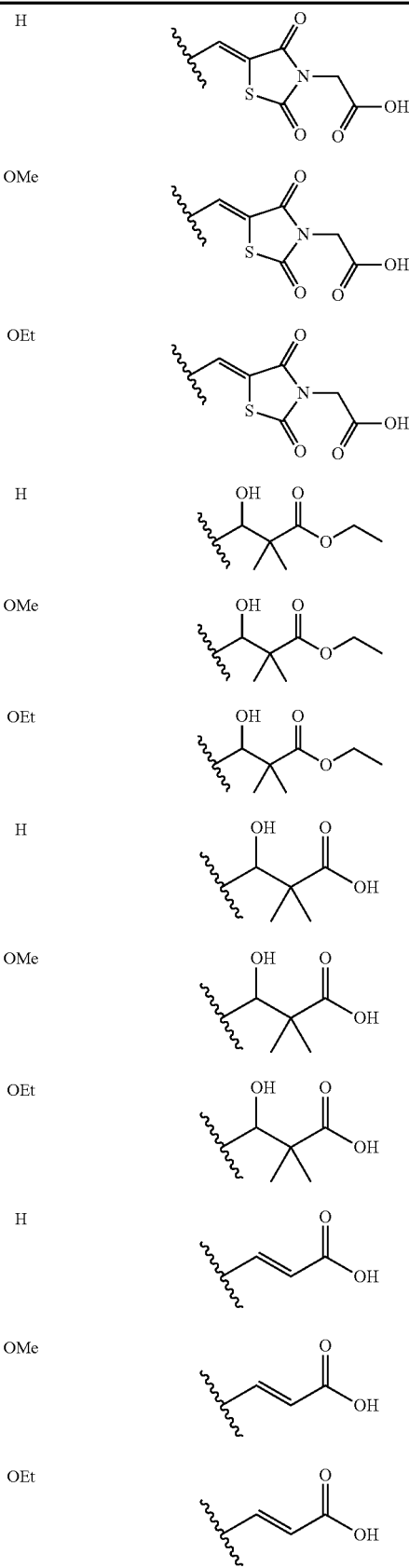 | OEt | 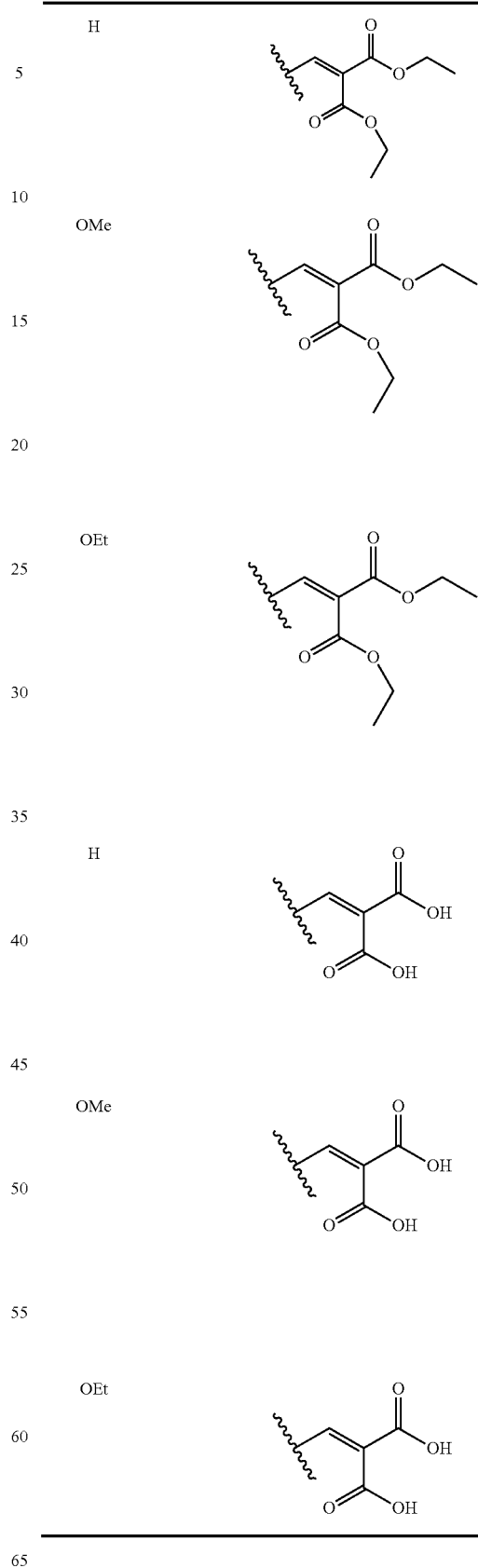 |
| H | | | |
| OMe | | | |
| OEt | | H | |
| H | | OMe | |
| OMe | | | |
| OEt | | OEt | |
| H | | | |
| OMe | | | |
| OEt | | | |
In some embodiments, the compound is selected from the group consisting of:

1625
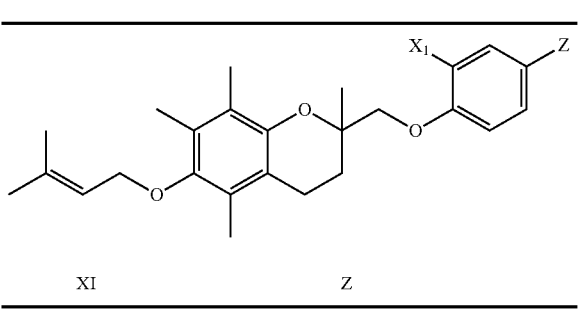
| XI | Z |
|---|---|
| Br | 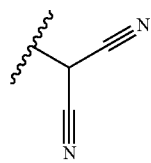 [SMILES: *C(C#N)C#N] |
| Br | 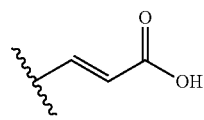 [SMILES: */C=C/C(=O)O] |
| Br | 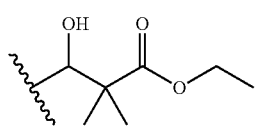 [SMILES: *C(O)C(C)(C)C(=O)OCC] |
| Br | 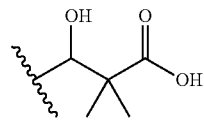 [SMILES: *C(O)C(C)(C)C(=O)O] |
| Br | 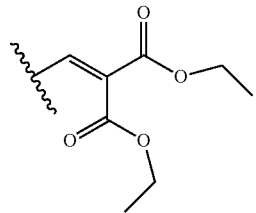 [SMILES: *C=C(C(=O)OCC)C(=O)OCC] |
| Br | 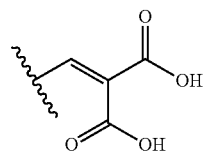 [SMILES: *C=C(C(=O)O)C(=O)O] |
| H | 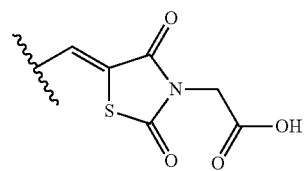 [SMILES: */C=C1\SC(=O)N(CC(=O)O)C1=O] |
| Br | 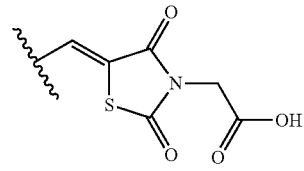 [SMILES: */C=C1\SC(=O)N(CC(=O)O)C1=O] |
1626
-continued
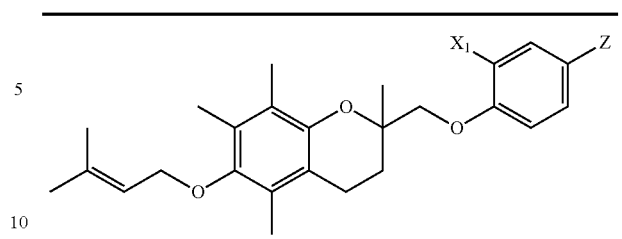
| XI | Z |
|---|---|
| Cl | 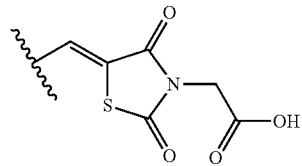 [SMILES: */C=C1\SC(=O)N(CC(=O)O)C1=O] |
In some embodiments, the compound is selected from the group consisting of:
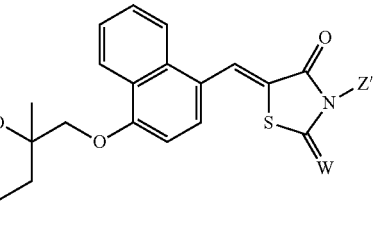
| W | Y | Z' |
|---|---|---|
| O | 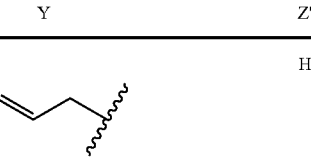 | H |
| S |  | H |
| O |  | H |
| O |  | CH₂COOH |
In some embodiments, the compound is selected from the group consisting of:

| 1627 | 1628 -continued |
|---|---|
| 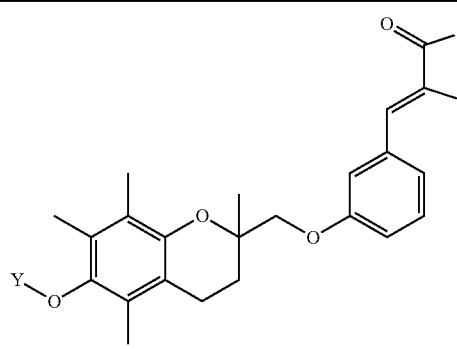 | 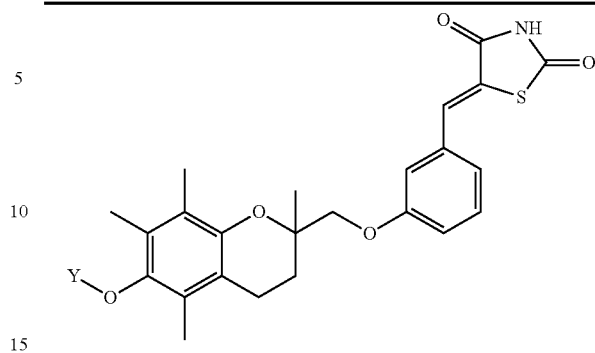 |
| Y | Y |
| 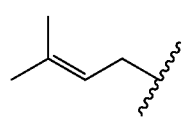 [SMILES: *CC=C(C)C] | 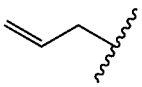 [SMILES: *CC=C] |
In some embodiments, the compound is selected from the group consisting of:
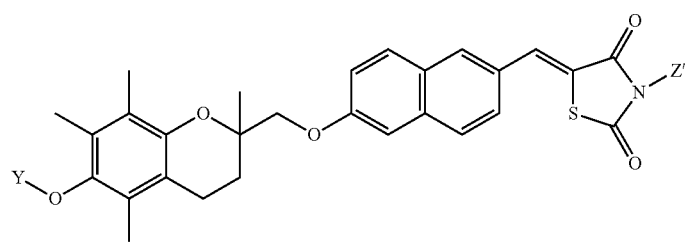
| Y | Z' |
|---|---|
| 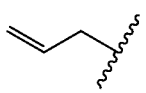 [SMILES: *CC=C] | H |
| 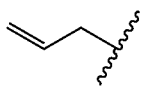 | CH₂COOH |
| 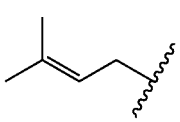 [SMILES: *CC=C(C)C] | H |

In some embodiments, the compound is selected from the group consisting of:

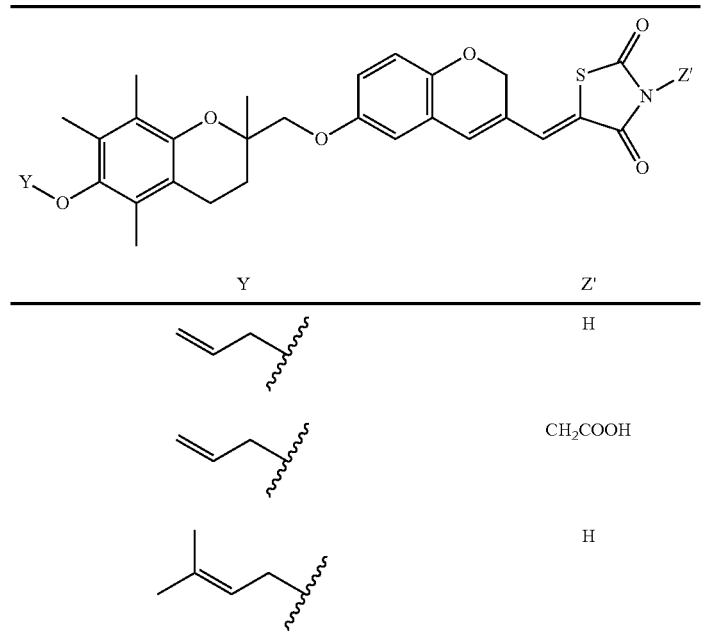

| Y | Z' |
|---|---|
| (allyl) | H |
| (allyl) | CH$_2$COOH |
| (prenyl) | H |

In some embodiments, the compound is selected from the group consisting of:

3,5-Dichloro-N-(3-((3,5-dichloro-2-hydroxyphenylsulfonamido)methyl)benzyl)-N-(4-fluorobenzyl)-2-hydroxybenzenesulfonamide;

N-(3-((3,5-Dichloro-N-(4-fluorobenzyl)-2-hydroxyphenylsulfonamido)methyl)benzyl)-2,6-dihydroxyisonicotinamide;

N-(Biphenyl-4-ylmethyl)-3,5-dichloro-N-(3-((3,5-dichloro-2-hydroxyphenylsulfonamido)methyl)benzyl)-2-hydroxybenzenesulfonamide;

N-(Biphenyl-4-ylmethyl)-3,5-dichloro-N-(3-((4-cyanophenylsulfonamido)methyl)benzyl)-2-hydroxybenzenesulfonamide;

3,5-Dichloro-N-(4-(4-fluorophenoxy)benzyl)-2-hydroxy-N-(3-((4-methylphenylsulfonamido)methyl)benzyl)benzenesulfonamide;

3,5-Dichloro-N-(3-((3,5-dichloro-2-hydroxyphenylsulfonamido)methyl)benzyl)-2-hydroxy-N (3-(trifluoromethoxy)benzyl)benzenesulfonamide;

3,5-Dichloro-N-(3-((3,5-dichloro-N-isobutylphenylsulfonamido)methyl)-5-(4-fluorophenoxy)benzyl)-N-(4-fluorobenzyl)-2-hydroxybenzenesulfonamide;

3,5-Dichloro-N-(4-fluorobenzyl)-N-(3-(4-fluorophenoxy)-5-((N-isobutyl-4-methylphenylsulfonamido)methyl)benzyl)-2-hydroxybenzenesulfonamide;

N-(3-((N-(Biphenyl-4-ylmethyl)-3,5-dichloro-2-hydroxyphenylsulfonamido)methyl)benzyl)-3,4,5-trihydroxybenzamide;

3,5-Dichloro-N-(3-((3-(2,4-difluorophenyl)ureido)methyl)benzyl)-2-hydroxy-N-(4-(trifluoromethyl)benzyl)benzenesulfonamide;

N-(3-((3-Biphenyl-4-ylureido)methyl)benzyl)-3,5-dichloro-2-hydroxy-N-(4-(trifluoromethyl)benzyl)benzenesulfonamide;

4-(2-Chlorophenyl)-N-(3-((3,5-dichloro-2-hydroxy-N-(4-(trifluoromethyl)benzyl)phenylsulfonamido)methyl)benzyl)piperazine-1-carboxamide;

3,5-Dichloro-N-((4'-fluoro-5-((N-(4-fluorobenzyl)-4-methylphenylsulfonamido)methyl)biphenyl-3-yl)methyl)-2-hydroxybenzenesulfonamide;

N,N'-(5-Cyclopropyl-1,3-phenylene)bis(methylene)bis(3,5-dichloro-N-(4-fluorobenzyl)-2-hydroxybenzenesulfonamide;

tert-Butyl 3-chloro-5-((3,5-dichloro-2-hydroxy-N-isobutylphenylsulfonamido)methyl)benzyl(isobutyl)carbamate;

3,5-Dichloro-N-(3-chloro-5-((N-isobutyl-4-methylphenylsulfonamido)methyl)benzyl)-2-hydroxy-N-isobutylbenzenesulfonamide;

6-Chloro-N-(3-chloro-5-((3,5-dichloro-2-hydroxy-N-isobutylphenylsulfonamido)methyl)benzyl)-N-isobutylnicotinamide;

3,5-Dichloro-N-(3-((3,5-dichloro-2-hydroxyphenylsulfonamido)methyl)-5-(4-fluorophenoxy)benzyl)-N-(4-fluorobenzyl)-2-hydroxybenzenesulfonamide;

N-(3-((3,5-Dichloro-N-(4-fluorobenzyl)-2-hydroxyphenylsulfonamido)methyl)-5-(4-fluorophenoxy)benzyl)-N-isobutylnicotinamide;

3-((3-((3,5-Dichloro-N-(4-fluorobenzyl)-2-hydroxyphenylsulfonamido)methyl)-5-(4-fluorophenoxy)benzyl) (isobutyl)carbamoyl)pyridine 1-oxide;

3,5-Dichloro-N-(3-((3-(2,4-difluorophenyl)ureido)methyl)-5-(4-fluorophenoxy)benzyl)-N-(4-fluorobenzyl)-2-hydroxybenzenesulfonamide;

N-(4-Fluoro-benzyl)-N-(3-{[(4-fluoro-benzyl)-(3,5-dichloro-2-hydroxybenzene)sulfonyl-amino]-methyl}-benzyl)-3,5-dichloro-2-hydroxybenzenesulfonamide;

N-(4-Fluoro-benzyl)-N-(4-{[(4-fluoro-benzyl)-(3,5-dichloro-2-hydroxybenzene)carbamoyl]-methyl}-benzyl)-3,5-dichloro-2-hydroxybenzamide;

N-(4-Fluoro-benzyl)-N-(3-chloro-5-{[(4-fluoro-benzyl)-(3,5-dichloro-2-hydroxybenzene)sulfonyl-amino]-methyl}-benzyl)-3,5-dichloro-2-hydroxybenzenesulfonamide;

5-(N-(3-((N-(Biphenyl-4-ylmethyl)-3,5-dichloro-2-hydroxyphenylsulfonamido)methyl)benzyl) sulfamoyl)-2-methylbenzoic acid;

N-(3-((3,5-dichloro-2-hydroxyphenylsulfonamido)methyl)benzyl)-N-(4-fluorobenzyl)-2,6-dihydroxyisonicotinamide;

N-(3-((3,5-dichloro-2-hydroxy-N-(4-(trifluoromethyl)benzyl)benzamide)methyl)benzyl)-2,6-dihydroxyisonicotinamide;

N-(3-((3,5-dichloro-2-hydroxy-N-(4-(trifluoromethyl)benzyl)phenylsulfonamido)methyl)benzyl)-2,3-dioxo-1,2,3,4-tetrahydroquinoxaline-6-carboxamide;

3,5-dichloro-N-(3-((5-chloro-2-methoxyphenylsulfonamido)methyl)-5-(4-fluorophenoxy)benzyl)-N-(4-fluorobenzyl)-2-hydroxybenzenesulfonamide;

tert-butyl 3-((3,5-dichloro-N-(4-fluorobenzyl)-2-hydroxyphenylsulfonamido)methyl)benzylcarbamate;

tert-butyl 3-((N-(biphenyl-4-ylmethyl)-3,5-dichloro-2-hydroxyphenylsulfonamido)methyl)benzylcarbamate;

N-(3-((3,5-dichloro-N-(4-fluorobenzyl)-2-hydroxyphenylsulfonamido)methyl)benzyl)-3,4,5-trihydroxybenzamide;

N-(biphenyl-4-ylmethyl)-3,5-dichloro-2-hydroxy-N-(3-((4-(pyridin-4-yloxy)phenylsulfonamido)methyl)benzyl)benzenesulfonamide;

5-(N-(3-((N-(biphenyl-4-ylmethyl)-3,5-dichloro-2-hydroxyphenylsulfonamido)methyl)benzyl)sulfamoyl)-2-hydroxybenzoic acid;

3-(N-(3-((N-(biphenyl-4-ylmethyl)-3,5-dichloro-2-hydroxyphenylsulfonamido)methyl)benzyl)sulfamoyl)benzoic acid;

N1-(3-((N-(biphenyl-4-ylmethyl)-3,5-dichloro-2-hydroxyphenylsulfonamido)methyl)benzyl)-4-chlorobenzene-1,3-disulfonamide;

N-(biphenyl-4-ylmethyl)-3,5-dichloro-2-hydroxy-N-(3-((3-(1,3,3-trimethylureido)phenylsulfonamido)methyl)benzyl)benzenesulfonamide;

N-(3-((N-(biphenyl-4-ylmethyl)-3,5-dichloro-2-hydroxyphenylsulfonamido)methyl)benzyl)-4-((1,3-dihydroxypropan-2-ylamino)methyl)benzamide;

N-(3-((N-(biphenyl-4-ylmethyl)-3,5-dichloro-2-hydroxyphenylsulfonamido)methyl)benzyl)-2-methoxy-5-sulfamoylbenzamide;

N-(biphenyl-4-ylmethyl)-3,5-dichloro-2-hydroxy-N-(3-((4-(pyridin-3-yloxy)phenylsulfonamido)methyl)benzyl)benzenesulfonamide;

3,5-dichloro-N-(3-((3,5-dichloro-N-(4-fluorobenzyl)-2-hydroxyphenylsulfonamido)methyl)benzyl)-N-(4-fluorophenethyl)-2-hydroxybenzenesulfonamide;

3,5-dichloro-N-(3-((3,5-dichloro-2-hydroxy-N-isobutylphenylsulfonamido)methyl)benzyl)-N-(4-fluorophenethyl)-2-hydroxybenzenesulfonamide;

(R)-tert-butyl 1-(3-((5-chloro-N-(4-fluorobenzyl)-2-methoxyphenylsulfonamido)methyl)benzylamino)-1-oxo-3-phenylpropan-2-ylcarbamate;

3,5-dichloro-N-(4-fluorobenzyl)-2-hydroxy-N-(3-((4-methylphenylsulfonamido)methyl)benzyl)benzenesulfonamide;

N-(3-((3,5-dichloro-N-(4-fluorobenzyl)-2-hydroxyphenylsulfonamido)methyl)benzyl)-4-methylbenzamide;

N-(3-((N-(biphenyl-4-ylmethyl)-3,5-dichloro-2-hydroxyphenylsulfonamido)methyl)benzyl)-3,5-dichloro-2-hydroxybenzamide;

N-(biphenyl-4-ylmethyl)-3,5-dichloro-N-(3-((3,5-dichlorophenylsulfonamido)methyl)benzyl)-2-hydroxybenzenesulfonamide;

N-(3-((N-(biphenyl-4-ylmethyl)-3,5-dichloro-2-hydroxyphenylsulfonamido)methyl)benzyl) naphthalene-2-sulfonamide;

4-(N-(3-((N-(biphenyl-4-ylmethyl)-3,5-dichloro-2-hydroxyphenylsulfonamido)methyl)benzyl)sulfamoyl)benzoic acid;

3,5-dichloro-N-(3-((3,5-dichloro-2-hydroxyphenylsulfonamido)methyl)benzyl)-N-(4-(4-fluorophenoxy)benzyl)-2-hydroxybenzenesulfonamide;

3,5-dichloro-N-(3-((3,5-dichloro-2-hydroxyphenylsulfonamido)methyl)benzyl)-N-(4-(difluoromethoxy)benzyl)-2-hydroxybenzenesulfonamide;

N-(biphenyl-4-ylmethyl)-3,5-dichloro-2-hydroxy-N-(3-(phenylsulfonamido methyl)benzyl)benzenesulfonamide;

3,5-dichloro-N-(3-((3,5-dichloro-2-hydroxyphenylsulfonamido)methyl)benzyl)-2-hydroxy-N-(4-(methylthio)benzyl)benzenesulfonamide;

3,5-dichloro-N-(3-((3,5-dichloro-2-hydroxyphenylsulfonamido)methyl)benzyl)-N-(3-ethoxybenzyl)-2-hydroxybenzenesulfonamide;

3-(N-(3-((N-(biphenyl-4-ylmethyl)-3,5-dichloro-2-hydroxyphenylsulfonamido)methyl)benzyl)sulfamoyl)-4-chlorobenzoic acid;

3,5-dichloro-N-(3-((3,5-dichloro-2-hydroxyphenylsulfonamido)methyl)benzyl)-2-hydroxy-N-(4-(methylsulfonyl)benzyl)benzenesulfonamide;

5-(N-(3-((N-(biphenyl-4-ylmethyl)-3,5-dichloro-2-hydroxyphenylsulfonamido)methyl)benzyl) sulfamoyl)-2-chloro-4-fluorobenzoic acid;

3,5-dichloro-N-(3-((3,5-dichloro-2-hydroxyphenylsulfonamido)methyl)benzyl)-2-hydroxy-N-(3-(2-hydroxyethoxy)benzyl)benzenesulfonamide;

3,5-dichloro-N-(3-((3,5-dichloro-2-hydroxyphenylsulfonamido)methyl)benzyl)-2-hydroxy-N-(3,4,5-trimethoxybenzyl)benzenesulfonamide;

2-chloro-5-(N-(3-chloro-5-((3,5-dichloro-N-(4-fluorobenzyl)-2-hydroxyphenylsulfonamido)methyl)benzyl)-N-(4-fluorobenzyl)sulfamoyl)-4-fluorobenzoic acid;

3,5-dichloro-N-(3-((3,5-dichloro-2-hydroxyphenylsulfonamido)methyl)benzyl)-N-(4-(2-(diethylamino) ethoxy) benzyl)-2-hydroxybenzenesulfonamide;

2-(3-((3,5-dichloro-N-(3-((3,5-dichloro-2-hydroxyphenylsulfonamido)methyl)benzyl)-2-hydroxyphenylsulfonamido)methyl)phenoxy)acetic acid;

N-(3-((N-(biphenyl-4-ylmethyl)-3,5-dichloro-2-hydroxyphenylsulfonamido)methyl)benzyl)-4-(trifluoromethylthio)benzamide;

3,5-dichloro-N-(3-((3,5-dichloro-2-hydroxyphenylsulfonamido)methyl)benzyl)-2-hydroxy-N-(2-(trifluoromethylthio)benzyl)benzenesulfonamide;

3,5-dichloro-N-(3-((3,5-dichloro-2-hydroxyphenylsulfonamido)methyl)benzyl)-2-hydroxy-N-(3-(trifluoro methylthio)benzyl)benzenesulfonamide;

N-(biphenyl-4-ylmethyl)-3,5-dichloro-N-(3-((4-fluoro-3-(trifluoromethylsulfonyl)phenylsulfonamido)methyl)benzyl)-2-hydroxybenzenesulfonamide;

N,N'-(5-chloro-1,3-phenylene)bis(methylene)bis(3,5-dichloro-2-hydroxy-N-isobutylbenzenesulfonamide;

4-(N-(3-((N-(biphenyl-4-ylmethyl)-3,5-dichloro-2-hydroxyphenylsulfonamido)methyl)benzyl)sulfamoyl)-3-(trifluoromethylsulfonyl)benzene-1-sulfonyl fluoride;

3,5-dichloro-N-(3-chloro-5-((N-(4-fluorobenzyl)-4-methylphenylsulfonamido)methyl)benzyl)-N-(4-fluorobenzyl)-2-hydroxybenzenesulfonamide;

3,5-dichloro-N-(3-chloro-5-((3-cyano-N-(4-fluorobenzyl) phenylsulfonamido)methyl)benzyl)-N-(4-fluorobenzyl)-2-hydroxybenzenesulfonamide;

N-(3-chloro-5-((3,5-dichloro-2-hydroxy-N-isobutylphenylsulfonamido)methyl)benzyl)-N-isobutyl-4-(trifluoromethylthio)benzamide;

N-(3-chloro-5-((3,5-dichloro-2-hydroxy-N-isobutylphenylsulfonamido)methyl)benzyl)-N-isobutyl-3-(trifluoromethylthio)benzamide;
N-(3-chloro-5-((3,5-dichloro-2-hydroxy-N-isobutylphenylsulfonamido)methyl)benzyl)-N-isobutyl-3-(trifluoromethylsulfonyl)benzamide;
3,5-dichloro-N-(3-((3-cyanophenylsulfonamido)methyl)-5-(4-fluorophenoxy)benzyl)-2-hydroxy-N-(3-(methylsulfonyl)benzyl)benzenesulfonamide;
3,5-dichloro-N-(3-(4-fluorophenoxy)-5-((4-methylphenylsulfonamido)methyl)benzyl)-2-hydroxy-N-(3-(methylsulfonyl)benzyl)benzenesulfonamide;
N-(3-((3,5-dichloro-2-hydroxy-N-(3-(methylsulfonyl)benzyl)phenylsulfonamido)methyl)-5-(4-fluorophenoxy)benzyl)-2-fluoro-3-methoxybenzamide;
N-(3-((3,5-dichloro-2-hydroxy-N-(3-(methylsulfonyl)benzyl)phenylsulfonamido)methyl)-5-(4-fluorophenoxy)benzyl)-3-phenoxybenzamide;
N-(3-((3,5-dichloro-2-hydroxy-N-(4-(methylsulfonyl)benzyl)phenylsulfonamido)methyl)-5-(4-fluorophenoxy)benzyl)-3-phenoxybenzamide;
N-(3-((3,5-dichloro-2-hydroxy-N-(4-(methylsulfonyl)benzyl)phenylsulfonamido)methyl)-5-(4-fluorophenoxy)benzyl)-2-fluoro-3-methoxybenzamide;
3,5-dichloro-N-(3-((3-cyanophenylsulfonamido)methyl)-5-(4-fluorophenoxy)benzyl)-2-hydroxy-N-(4-(methylsulfonyl)benzyl)benzenesulfonamide;
3,5-dichloro-N-(3-(4-fluorophenoxy)-5-((4-methylphenylsulfonamido)methyl)benzyl)-2-hydroxy-N-(4-(methylsulfonyl)benzyl)benzenesulfonamide;
N-(3-((3,5-dichloro-2-hydroxy-N-(4-(methylsulfonyl)benzyl)phenylsulfonamido)methyl)-5-(4-fluorophenoxy)benzyl)-3-(trifluoromethylsulfonyl)benzamide;
N-(3-((3,5-dichloro-N-(4-fluorobenzyl)-2-hydroxyphenylsulfonamido)methyl)-5-(4-fluorophenoxy)benzyl)-N-(4-(methylsulfonyl)benzyl)-3-(trifluoromethylthio)benzamide;
3,5-dichloro-N-(3-((3,5-dichloro-2-hydroxyphenylsulfonamido)methyl)-5-(4-fluorophenoxy)benzyl)-2-hydroxy-N-(4-(methylsulfonyl)benzyl)benzenesulfonamide;
N-(3-((3,5-dichloro-N-(4-fluorobenzyl)-2-hydroxyphenylsulfonamido)methyl)-5-(4-fluorophenoxy)benzyl)-N-(4-(methylsulfonyl)benzyl)-3-(trifluoromethylthio)benzamide;
N-(3-((3,5-dichloro-N-(4-fluorobenzyl)-2-hydroxyphenylsulfonamido)methyl)-5-(4-fluorophenoxy)benzyl)-N-(4-(methylsulfonyl)benzyl)-3-(trifluoromethylsulfinyl)benzamide;
6-chloro-N-(3-((3,5-dichloro-N-(4-fluorobenzyl)-2-hydroxyphenylsulfonamido)methyl)-5-(4-fluorophenoxy)benzyl)-N-isobutylnicotinamide;
N-(3-((3,5-dichloro-N-(4-fluorobenzyl)-2-hydroxyphenylsulfonamido)methyl)-5-(4-fluorophenoxy)benzyl)nicotinamide;
3-(3-((3,5-dichloro-N-(4-fluorobenzyl)-2-hydroxyphenylsulfonamido)methyl)-5-(4-fluorophenoxy)benzylcarbamoyl)pyridine 1-oxide;
3,5-dichloro-N-(3-chloro-5-((3,5-dichloro-N-(4-fluorobenzyl)phenylsulfonamido)methyl)benzyl)-N-(4-fluorobenzyl)-2-hydroxybenzenesulfonamide;
3,5-dichloro-N-((6-((3,5-dichloro-N-(4-fluorobenzyl)phenylsulfonamido)methyl)pyridin-2-yl)methyl)-N-(4-fluorobenzyl)-2-hydroxybenzenesulfonamide;
2-((3,5-dichloro-N-(4-fluorobenzyl)-2-hydroxyphenylsulfonamido)methyl)-6-((3,5-dichloro-N-(4-fluorobenzyl)phenylsulfonamido)methyl)pyridine 1-oxide;
3,5-dichloro-N-(3-((3,5-dichloro-N-isobutylphenylsulfonamido)methyl)benzyl)-N-((4'-fluorobiphenyl-4-yl)methyl)-2-hydroxybenzenesulfonamide;
3,5-Dichloro-N-(3-(N-(3,5-dichlorobenzyl)-N-(4-fluorobenzyl)sulfamoyl)benzyl)-N-(4-fluorobenzyl)-2-hydroxybenzenesulfonamide;
3-((3,5-Dichloro-N-(4-fluorobenzyl)-2-hydroxyphenylsulfonamido)methyl)-N-(3,5-dichlorobenzyl)-N-(4-fluorobenzyl)benzamide;
N-(4-Fluoro-benzyl)-N-(4-{[(4-fluoro-benzyl)-(3,5-dichloro-2-hydroxybenzene)sulfonyl-amino]-methyl}-benzyl)-3,5-dichloro-2-hydroxybenzenesulfonamide;
N-Isobutyl-N-{4-[(isobutyl-(3,5-dichloro-2-hydroxybenzene) sulfonyl-amino)-methyl]-benzyl}-(3,5-dichloro-2-hydroxybenzene) sulfonamide;
3,5-Dichloro-N-(4-((3,5-dichlorophenylsulfonamido)methyl)benzyl)-N-(4-fluorobenzyl)-2-hydroxybenzenesulfonamide;
3,5-Dichloro-N-(4-((3,5-dichloro-N-(4-fluorobenzyl)phenylsulfonamido)methyl)benzyl)-N-(4-fluorobenzyl)-2-hydroxybenzenesulfonamide;
N-(4-((3,5-Dichloro-N-(4-fluorobenzyl)-2-hydroxyphenylsulfonamido)methyl)benzyl)-N-(4-fluorobenzyl)-6-(trifluoromethyl)pyridine-3-sulfonamide;
N-(Biphenyl-4-ylmethyl)-3,5-dichloro-2-hydroxy-N-(3-((4-methylphenylsulfonamido)methyl)benzyl)benzenesulfonamide;
3,5-Dichloro-N-(3-((3,5-dichloro-N-(4-fluorobenzyl)phenylsulfonamido)-methyl)benzyl)-2-hydroxy-N-(naphthalen-1-ylmethyl)-benzenesulfonamide;
3-Chloro-5-((3,5-dichloro-N-(4-fluorophenethyl)-2-hydroxyphenylsulfonamido)methyl)-N-(3,5-dichlorobenzyl)-N-(4-fluorobenzyl)benzamide;
4-((3,5-Dichloro-N-(4-fluorobenzyl)-2-hydroxyphenylsulfonamido)methyl)-N-(3,5-dichlorobenzyl)-N-(4-fluorobenzyl)benzamide;
N-Benzyl-4-((3,5-dichloro-N-(4-fluorobenzyl)-2-hydroxyphenylsulfonamido)methyl)-N-isopropylbenzamide;
N-Benzyl-4-((3,5-dichloro-N-(4-fluorobenzyl)-2-hydroxyphenylsulfonamido)methyl)-N-methylbenzamide;
N,N-Dibutyl-4-((3,5-dichloro-N-(4-fluorobenzyl)-2-hydroxyphenylsulfonamido)methyl)-benzamide;
4-((3,5-Dichloro-N-(4-fluorobenzyl)-2-hydroxyphenylsulfonamido)methyl)-N-(4-fluorobenzyl)-N-isopentylbenzamide;
N-Cyclopentyl-4-((3,5-dichloro-N-(4-fluorobenzyl)-2-hydroxyphenylsulfonamido)methyl)-N-(4-fluorobenzyl)benzamide;
N-Cyclopropyl-4-((3,5-dichloro-N-(4-fluorobenzyl)-2-hydroxyphenylsulfonamido)methyl)-N-(4-fluorobenzyl)benzamide;
4-((3,5-Dichloro-N-(4-fluorobenzyl)-2-hydroxyphenylsulfonamido)methyl)-N-(4-fluorobenzyl)-N-isopropylbenzamide;
4-((3,5-Dichloro-N-(4-fluorobenzyl)-2-hydroxyphenylsulfonamido)methyl)-N-(4-fluorobenzyl)-N-(2-hydroxyethyl)benzamide;
4-((3,5-Dichloro-N-(4-fluorobenzyl)-2-hydroxyphenylsulfonamido)methyl)-N-(4-fluorobenzyl)-N-isobutylbenzamide;
N-(Cyclopropylmethyl)-4-((3,5-dichloro-N-(4-fluorobenzyl)-2-hydroxyphenylsulfonamido)methyl)-N-(4-fluorobenzyl)benzamide;
4-((3,5-Dichloro-N-(4-fluorobenzyl)-2-hydroxyphenylsulfonamido)methyl)-N-(4-fluorobenzyl)-N-(pyridin-3-ylmethyl)benzamide;

4-((3,5-Dichloro-N-(4-fluorobenzyl)-2-hydroxyphenylsulfonamido)methyl)-N-(4-fluorobenzyl)-N-(2-morpholinoethyl)benzamide;
4-((3,5-Dichloro-N-(4-fluorobenzyl)-2-hydroxyphenylsulfonamido)methyl)-N-(4-(dimethylamino)phenyl)-N-(4-fluorobenzyl)benzamide;
4-((3,5-Dichloro-N-(4-fluorobenzyl)-2-hydroxyphenylsulfonamido)methyl)-N-isopentyl-N-methylbenzamide;
N-(2-(Benzo[d]thiazol-2-yl)ethyl)-4-((3,5-dichloro-N-(4-fluorobenzyl)-2-hydroxyphenylsulfonamido)methyl)-benzamide;
3,5-Dichloro-N-(4-fluorobenzyl)-2-hydroxy-N-(4-(4-phenylpiperidine-1-carbonyl)benzyl)benzenesulfonamide;
N-(4-(4-Benzylpiperidine-1-carbonyl)benzyl)-3,5-dichloro-N-(4-fluorobenzyl)-2-hydroxybenzenesulfonamide;
4-((3,5-Dichloro-N-(4-fluorobenzyl)-2-hydroxyphenylsulfonamido)methyl)-N-(2,2-diphenylethyl)benzamide;
3,5-Dichloro-N-(4-(4-(2-chlorophenyl)piperazine-1-carbonyl)benzyl)-N-(4-fluorobenzyl)-2-hydroxybenzenesulfonamide;
N-(Biphenyl-3-ylmethyl)-4-((3,5-dichloro-N-(4-fluorobenzyl)-2-hydroxyphenylsulfonamido)methyl)-benzamide;
N-(Biphenyl-4-ylmethyl)-4-((3,5-dichloro-N-(4-fluorobenzyl)-2-hydroxyphenylsulfonamido)methyl)-benzamide;
N-Cyclohexyl-4-((3,5-dichloro-N-(4-fluorobenzyl)-2-hydroxyphenylsulfonamido)methyl)-benzamide;
3,5-Dichloro-N-(4-fluorobenzyl)-2-hydroxy-N-(4-(4-phenylpiperazine-1-carbonyl)benzyl)benzenesulfonamide;
3,5-Dichloro-N-(4-fluorobenzyl)-2-hydroxy-N-(4-(piperidine-1-carbonyl)benzyl)benzenesulfonamide;
4-((3,5-Dichloro-N-(4-fluorobenzyl)-2-hydroxyphenylsulfonamido)methyl)-N-isopropylbenzamide;
4-((3,5-Dichloro-N-(4-fluorobenzyl)-2-hydroxyphenylsulfonamido)methyl)-N-isobutylbenzamide;
4-((3,5-Dichloro-N-(4-fluorobenzyl)-2-hydroxyphenylsulfonamido)methyl)-N-ethylbenzamide;
4-((3,5-Dichloro-N-(4-fluorobenzyl)-2-hydroxyphenylsulfonamido)methyl)-N-phenethylbenzamide;
4-((3,5-Dichloro-N-(4-fluorobenzyl)-2-hydroxyphenylsulfonamido)methyl)-N-isopentylbenzamide;
4-((3,5-Dichloro-N-(4-fluorobenzyl)-2-hydroxyphenylsulfonamido)methyl)-N-(3-phenylpropyl)benzamide;
4-((3,5-Dichloro-N-(4-fluorobenzyl)-2-hydroxyphenylsulfonamido)methyl)-N-methyl-N-phenethylbenzamide;
N-Butyl-4-((3,5-dichloro-N-(4-fluorobenzyl)-2-hydroxyphenylsulfonamido)methyl)-benzamide;
N-(4-(4-Benzhydrylpiperazine-1-carbonyl)benzyl)-3,5-dichloro-N-(4-fluorobenzyl)-2-hydroxybenzenesulfonamide;
3,5-Dichloro-N-(4-fluorobenzyl)-2-hydroxy-N-(4-(4-(pyrazin-2-yl)piperazine-1-carbonyl)benzyl)benzenesulfonamide;
4-((3,5-Dichloro-N-(4-fluorobenzyl)-2-hydroxyphenylsulfonamido)methyl)-N-(2-phenoxyethyl)benzamide;
4-((3,5-Dichloro-N-(4-fluorobenzyl)-2-hydroxyphenylsulfonamido)methyl)-N-(3-(trifluoromethoxy)benzyl)benzamide;
4-((3,5-Dichloro-N-(4-fluorobenzyl)-2-hydroxyphenylsulfonamido)methyl)-N-((1S,2R)-2-phenylcyclopropyl)benzamide;
3,5-Dichloro-N-(4-fluorobenzyl)-2-hydroxy-N-(4-(3-phenylpyrrolidine-1-carbonyl)benzyl)benzenesulfonamide;
N-(4-(4-Benzylpiperazine-1-carbonyl)benzyl)-3,5-dichloro-N-(4-fluorobenzyl)-2-hydroxybenzenesulfonamide;
4-((3,5-Dichloro-N-(4-fluorobenzyl)-2-hydroxyphenylsulfonamido)methyl)-N-methyl-N-(2-(pyridin-2-yl)ethyl)benzamide;
4-((3,5-Dichloro-N-(4-fluorobenzyl)-2-hydroxyphenylsulfonamido)methyl)-N-(4-sulfamoylbenzyl)benzamide;
4-((3,5-Dichloro-N-(4-fluorobenzyl)-2-hydroxyphenylsulfonamido)methyl)-N-(4-phenoxybenzyl)benzamide;
3,5-Dichloro-N-(4-fluorobenzyl)-2-hydroxy-N-(4-(4-(2-hydroxyethyl)piperidine-1-carbonyl)benzyl)benzenesulfonamide;
4-((3,5-Dichloro-N-(4-fluorobenzyl)-2-hydroxyphenylsulfonamido)methyl)-N-(4-(dimethylamino)benzyl)benzamide;
4-((3,5-Dichloro-N-(4-fluorobenzyl)-2-hydroxyphenylsulfonamido)methyl)-N-(1,2,3,4-tetrahydronaphthalen-1-yl)benzamide;
4-((3,5-Dichloro-N-(4-fluorobenzyl)-2-hydroxyphenylsulfonamido)methyl)-N-(4-(trifluoromethoxy)benzyl)benzamide;
4-((3,5-Dichloro-N-(4-fluorobenzyl)-2-hydroxyphenylsulfonamido)methyl)-N-((2-phenylthiazol-4-yl)methyl)benzamide;
N-tert-Butyl-4-((3,5-dichloro-N-(4-fluorobenzyl)-2-hydroxyphenylsulfonamido)methyl)-benzamide;
4-((3,5-Dichloro-N-(4-fluorobenzyl)-2-hydroxyphenylsulfonamido)methyl)-N-(1-phenylethyl)benzamide;
N-Benzyl-4-((3,5-dichloro-N-(4-fluorobenzyl)-2-hydroxyphenylsulfonamido)methyl)-benzamide;
4-((3,5-Dichloro-N-(4-fluorobenzyl)-2-hydroxyphenylsulfonamido)methyl)-N-neopentylbenzamide;
4-((3,5-Dichloro-N-(4-fluorobenzyl)-2-hydroxyphenylsulfonamido)methyl)-N-(4-(trifluoromethyl)benzyl)benzamide;
4-((3,5-Dichloro-N-(4-fluorobenzyl)-2-hydroxyphenylsulfonamido)methyl)-N-isobutyl-N-methylbenzamide;
4-((3,5-Dichloro-N-(4-fluorobenzyl)-2-hydroxyphenylsulfonamido)methyl)-N-isopropyl-N-methylbenzamide;
N-(Benzo[d]thiazol-6-yl)-4-((3,5-dichloro-N-(4-fluorobenzyl)-2-hydroxyphenylsulfonamido)methyl)-benzamide;
4-((3,5-Dichloro-N-(4-fluorobenzyl)-2-hydroxyphenylsulfonamido)methyl)-N-(4-(dimethylamino)phenyl)benzamide;
Ethyl 3-(4-((3,5-dichloro-N-(4-fluorobenzyl)-2-hydroxyphenylsulfonamido)methyl)-benzamido)butanoate;
(S,Z)-4-((3,5-Dichloro-N-(4-fluorobenzyl)-2-hydroxyphenylsulfonamido)methyl)-N-(1-methyl-2-oxo-5-phenyl-2,3-dihydro-1H-benzo[e][1,4]diazepin-3-yl)benzamide;
(R,Z)-4-((3,5-Dichloro-N-(4-fluorobenzyl)-2-hydroxyphenylsulfonamido)methyl)-N-(1-methyl-2-oxo-5-phenyl-2,3-dihydro-1H-benzo[e][1,4]diazepin-3-yl)benzamide;
4-((3,5-Dichloro-N-(4-fluorobenzyl)-2-hydroxyphenylsulfonamido)methyl)-N-(3,5-dichlorobenzyl)-N-(4-fluorobenzyl)-3-methoxybenzamide;
4-((3,5-Dichloro-2-hydroxy-N-isobutylphenylsulfonamido)methyl)-N-(3,5-dichlorobenzyl)-N-(4-fluorobenzyl)benzamide;
4-((3,5-Dichloro-2-hydroxy-N-isopentylphenylsulfonamido)methyl)-N-(3,5-dichlorobenzyl)-N-(4-fluorobenzyl)benzamide;
4-((3,5-Dichloro-2-hydroxy-N-(4-methylpentyl)phenylsulfonamido)meth-yl)-N-(3,5-dichlorobenzyl)-N-(4-fluorobenzyl)benzamide;
4-((3,5-Dichloro-N-(cyclohexylmethyl)-2-hydroxyphenylsulfonamido)methyl)-N-(3,5-dichlorobenzyl)-N-(4-fluorobenzyl)benzamide;
4-((3,5-Dichloro-2-hydroxy-N-(3-methylbut-2-enyl)phenylsulfonamido)methyl)-N-(3,5-dichlorobenzyl)-N-(4-fluorobenzyl)benzamide;

4-((3,5-Dichloro-2-hydroxy-N-(4-isobutoxybenzyl)phenyl-sulfonamido)-methyl)-N-(3,5-dichlorobenzyl)-N-(4-fluorobenzyl)benzamide;

4-((3,5-Dichloro-2-hydroxy-N-(3-isobutoxybenzyl)phenyl-sulfonamido)-methyl)-N-(3,5-dichlorobenzyl)-N-(4-fluorobenzyl)benzamide;

4-((3,5-Dichloro-N-((4'-chlorobiphenyl-3-yl)methyl)-2-hydroxyphenylsulfonamido)methyl)-N-(3,5-dichlorobenzyl)-N-(4-fluorobenzyl)benzamide;

4-(3,5-Dichloro-N-(4-fluorobenzyl)-2-hydroxyphenylsulfonamido)-N-(3,5-dichlorobenzyl)-N-(4-fluorobenzyl)benzamide;

3,5-Dichloro-N-(4-((3,5-dichloro-N-(2-hydroxyethyl)phenylsulfonamido)methyl)benzyl)-N-(4-fluorobenzyl)-2-hydroxybenzenesulfonamide;

3,5-Dichloro-N-(4-fluorobenzyl)-N-(4-((N-(4-fluorobenzyl)phenylsulfonamido)-methyl)benzyl)-2-hydroxybenzenesulfonamide;

N-(4-((Bis(pyridin-4-ylmethyl)amino)methyl)benzyl)-3,5-dichloro-N-(4-fluorobenzyl)-2-hydroxybenzenesulfonamide;

3,5-Dichloro-N-(4-((3,5-dichloro-N-(pyridin-2-ylmethyl)phenylsulfonamido)methyl)-benzyl)-N-(4-fluorobenzyl)-2-hydroxybenzenesulfonamide;

N-(4-Benzoylbenzyl)-3,5-dichloro-N-(4-fluorobenzyl)-2-hydroxybenzenesulfonamide (180);

3,5-Dichloro-N-(4-fluorobenzyl)-2-hydroxy-N-(4-(4-methylbenzoyl)benzyl)benzenesulfonamide;

3,5-Dichloro-N-(4-fluorobenzyl)-2-hydroxy-N-(4-(hydroxy(phenyl)methyl)benzyl)benzenesulfonamide;

N-(4-Benzylbenzyl)-3,5-dichloro-N-(4-fluorobenzyl)-2-hydroxybenzenesulfonamide;

N-(3-((3,5-Dichloro-N-((4'-fluorobiphenyl-4-yl)methyl)-2-hydroxyphenylsulfonamido)methyl)benzyl)-N-isobutyl-2-phenoxybenzamide;

N-(3-((3,5-Dichloro-N-((4'-fluorobiphenyl-4-yl)methyl)-2-hydroxyphenylsulfonamido)methyl)benzyl)-N-isobutyl-6-(piperidin-1-yl)nicotinamide;

N-(3-((3,5-Dichloro-N-((4'-fluorobiphenyl-4-yl)methyl)-2-hydroxyphenylsulfonamido)methyl)-benzyl)-N-isobutyl-1H-indole-4-carboxamide;

4-Cyclohexyl-N-(3-((3,5-dichloro-N-((4'-fluorobiphenyl-4-yl)methyl)-2-hydroxyphenylsulfonamido)methyl)-benzyl)-N-isobutylbenzamide;

3-Chloro-N-(3-((3,5-dichloro-N-((4'-fluorobiphenyl-4-yl)methyl)-2-hydroxyphenylsulfonamido)methyl)-benzyl)-N-isobutyl-4-nitrobenzamide;

N-(3-((3,5-Dichloro-N-((4'-fluorobiphenyl-4-yl)methyl)-2-hydroxyphenylsulfonamido)methyl)-benzyl)-N-isobutyl-2-naphthamide;

N-(3-((3,5-Dichloro-N-((4'-fluorobiphenyl-4-yl)methyl)-2-hydroxyphenylsulfonamido)methyl)-benzyl)-N-isobutyl-2,3-dioxo-1,2,3,4-tetrahydroquinoxaline-6-carboxamide;

N-(3-((3,5-Dichloro-N-((4'-fluorobiphenyl-4-yl)methyl)-2-hydroxyphenylsulfonamido)methyl)-benzyl)-N-isobutyl-benzo[d]thiazole-2-carboxamide;

N-(3-((3,5-Dichloro-N-((4'-fluorobiphenyl-4-yl)methyl)-2-hydroxyphenylsulfonamido)methyl)-benzyl)-N-isobutyl-4-(pyridin-4-yl)benzamide;

N-(3-((3,5-Dichloro-N-((4'-fluorobiphenyl-4-yl)methyl)-2-hydroxyphenylsulfonamido)methyl)-benzyl)-N-isobutyl-biphenyl-4-carboxamide;

3,5-Dichloro-N-(3-((3-(2,3-dichlorophenyl)-1-isobutylureido)methyl)benzyl)-N-((4'-fluorobiphenyl-4-yl)methyl)-2-hydroxybenzenesulfonamide;

N-(3-((3-(Biphenyl-2-O-1-isobutylureido)methyl)benzyl)-3,5-dichloro-N-((4'-fluorobiphenyl-4-yl)methyl)-2-hydroxybenzenesulfonamide;

3,5-Dichloro-N-((4'-fluorobiphenyl-4-yl)methyl)-2-hydroxy-N-(3-((1-isobutyl-3-(3-methoxyphenyl) ureido)methyl)-benzyl)benzenesulfonamide;

N-(3-((3-(4-(Benzyloxy)phenyl)-1-isobutylureido)methyl)benzyl)-3,5-dichloro-N-((4'-fluorobiphenyl-4-yl)methyl)-2-hydroxybenzenesulfonamide;

N-(3-((3-(2-tert-Butyl-6-methylphenyl)-1-isobutylureido)methyl)benzyl)-3,5-dichloro-N-((4'-fluorobiphenyl-4-yl)methyl)-2-hydroxybenzenesulfonamide;

3,5-Dichloro-N-(3-((3-(2,6-diisopropylphenyl)-1-isobutylureido)methyl)benzyl)-N-((4'-fluorobiphenyl-4-yl)methyl)-2-hydroxybenzenesulfonamide;

3,5-Dichloro-N-((4'-fluorobiphenyl-4-yl)methyl)-2-hydroxy-N-(3-((1-isobutyl-3-(2-isopropylphenyl)ureido)methyl)-benzyl)benzenesulfonamide;

3,5-Dichloro-N-(3-((3-(2,5-difluorophenyl)-1-isobutylureido)methyl)benzyl)-N-((4'-fluorobiphenyl-4-yl)methyl)-2-hydroxybenzenesulfonamide;

3,5-Dichloro-N-((4'-fluorobiphenyl-4-yl)methyl)-2-hydroxy-N-(3-((1-isobutyl-3,3-dimethylureido)methyl)benzyl)-benzenesulfonamide;

N-(3-((3-(Biphenyl-2-yl)-1-isobutyl-3-methylureido)methyl)benzyl)-3,5-dichloro-N-((4'-fluorobiphenyl-4-yl)methyl)-2-hydroxybenzenesulfonamide;

3,5-Dichloro-N-(3-((3-(2,3-dichlorophenyl)-1-isobutyl-3-methylureido)methyl)benzyl)-N-((4'-fluorobiphenyl-4-yl)methyl)-2-hydroxybenzenesulfonamide;

3,5-Dichloro-N-(3-((3-(2,5-difluorophenyl)-1-isobutyl-3-methylureido)methyl)benzyl)-N-((4'-fluorobiphenyl-4-yl)methyl)-2-hydroxybenzenesulfonamide;

3,5-Dichloro-N-(2-((3,5-dichloro-N-(4-fluorobenzyl)phenylsulfonamido)-methyl)benzyl)-N-(4-fluorobenzyl)-2-hydroxybenzenesulfonamide;

N-Benzyl-3-chloro-5-(N-((4'-chlorobiphenyl-3-yl)methyl)-N-(4-fluorobenzyl)sulfamoyl)-4-hydroxybenzamide;

5-Chloro-3-(N-(4-fluorobenzyl)-N-(4-(4-(trifluoromethyl)phenoxy)benzyl)sulfamoyl)-2-hydroxy-N-phenylbenzamide;

3,5-Dichloro-N-(3-(4-fluorophenoxy)benzyl)-2-hydroxy-N-(4-phenylbutyl)benzenesulfonamide;

3-Chloro-5-(N-((4'-chlorobiphenyl-3-yl)methyl)-N-(4-fluorobenzyl)-sulfamoyl)-4-hydroxy-N-phenylbenzamide;

3-Chloro-5-(N-((4'-chlorobiphenyl-3-yl)methyl)-N-(4-fluorobenzyl)-sulfamoyl)-4-hydroxy-N-isopropylbenzamide;

3-Chloro-5-(N-((4'-chlorobiphenyl-3-yl)methyl)-N-(4-fluorobenzyl)-sulfamoyl)-4-hydroxybenzamide;

3-Chloro-5-(N-((4'-chlorobiphenyl-3-yl)methyl)-N-(4-fluorobenzyl)-sulfamoyl)-4-hydroxy-N-(3-hydroxypropyl)benzamide;

3-Chloro-5-(N-((4'-chlorobiphenyl-3-yl)methyl)-N-(4-fluorobenzyl)-sulfamoyl)-N-(2,3-dihydroxypropyl)-4-hydroxybenzamide;

3-Chloro-5-(N-((4'-chlorobiphenyl-3-yl)methyl)-N-(4-fluorobenzyl)-sulfamoyl)-4-hydroxy-N-(4-(2-hydroxyethyl)phenyl)benzamide;

Methyl 3-chloro-5-(N-((4'-chloro-biphenyl-3-yl)methyl)-N-(4-fluorobenzyl)sulfamoyl)-4-hydroxybenzoate;

4-Aminophenethyl 3-chloro-5-(N-((4'-chlorobiphenyl-3-yl)methyl)-N-(4-fluorobenzyl)sulfamoyl)-4-hydroxybenzoate;

N-Benzyl-3-chloro-5-(N-((4',5-dichloro-6-methoxybiphenyl-3-yl)methyl)-N-(4-fluorobenzyl)sulfamoyl)-4-hydroxybenzamide;

N-Benzyl-3-chloro-5-(N-(4-fluoro-benzyl)-N-(4-(4-(trifluoromethyl)-phenoxy)benzyl)sulfamoyl)-4-hydroxybenzamide;
N-Benzyl-3-chloro-5-(N-((4',5-dichloro-6-methoxybiphenyl-3-yl)methyl)-N-(4-(4-fluorophenoxy)benzyl)sulfamoyl)-4-hydroxybenzamide;
N-Benzyl-3-chloro-5-(N-((4',5-dichloro-6-methoxybiphenyl-3-yl)methyl)-N-(4-(4-(trifluoromethyl)phenoxy)benzyl)-sulfamoyl)-4-hydroxybenzamide;
3-(N-(2-(1H-Indol-1-yl)ethyl)-N-((4',5-dichloro-6-methoxybiphenyl-3-yl)methyl)sulfamoyl)-N-benzyl-5-chloro-4-hydroxybenzamide;
5-Chloro-3-(N-((4'-chlorobiphenyl-3-yl)methyl)-N-(4-fluorobenzyl)-sulfamoyl)-2-hydroxy-N-phenylbenzamide;
N-Benzyl-5-chloro-3-(N-((4'-chlorobiphenyl-3-yl)methyl)-N-(4-fluorobenzyl)sulfamoyl)-2-hydroxybenzamide;
5-Chloro-3-(N-((4'-chlorobiphenyl-3-yl)methyl)-N-(4-fluorobenzyl)-sulfamoyl)-N-(2,3-dihydroxypropyl)-2-hydroxybenzamide;
Methyl 5-chloro-3-(N-((4'-chloro-biphenyl-3-yl)methyl)-N-(4-fluorobenzyl)sulfamoyl)-2-hydroxybenzoate;
5-Chloro-3-(N-((4'-chlorobiphenyl-3-yl)methyl)-N-(4-fluorobenzyl)-sulfamoyl)-2-hydroxy-N-(1H-pyrazol-4-yl)benzamide;
5-Chloro-3-(N-((4'-chlorobiphenyl-3-yl)methyl)-N-(4-fluorobenzyl)-sulfamoyl)-2-hydroxy-N-(1H-indol-4-yl)benzamide;
5-Chloro-3-(N-((4'-chlorobiphenyl-3-yl)methyl)-N-(4-fluorobenzyl)-sulfamoyl)-2-hydroxy-N-(2-hydroxyethyl)benzamide;
N-((4'-Aminobiphenyl-3-yl)methyl)-3,5-dichloro-N-(4-fluorobenzyl)-2-hydroxybenzenesulfonamide;
N-((4'-Azidobiphenyl-3-yl)methyl)-3,5-dichloro-N-(4-fluorobenzyl)-2-hydroxybenzenesulfonamide;
3,5-Dichloro-N-((4'-chlorobiphenyl-3-yl)methyl)-N-(4-fluorobenzyl)-2-hydroxybenzenesulfonamide;
3-Chloro-N-((4'-chlorobiphenyl-3-yl)methyl)-N-(4-fluorobenzyl)-2-hydroxy-5-(trifluoromethyl)benzenesulfonamide;
5-Chloro-N-((4'-chlorobiphenyl-3-yl)methyl)-N-(4-fluorobenzyl)-2-hydroxy-3-(trifluoromethyl)benzenesulfonamide;
3,5-Dichloro-N-(3-(4-fluorophenoxy)benzyl)-2-hydroxy-N-(4-octylbenzyl)benzenesulfonamide;
3,5-Dichloro-N-(3-(4-fluorophenoxy)-benzyl)-2-hydroxy-N-(4-pentyl-benzyl)benzenesulfonamide;
3,5-Dichloro-N-(3-(4-fluorophenoxy)-benzyl)-2-hydroxy-N-nonyl-benzenesulfonamide;
3,5-Dichloro-N-(2,6-dimethylhept-5-enyl)-N-(3-(4-fluorophenoxy)-benzyl)-2-hydroxybenzene-sulfonamide;
3,5-Dichloro-N-(3-(4-fluorophenoxy)-benzyl)-2-hydroxy-N-(3,5,5-trimethylhexyl)benzenesulfonamide;
3,5-Dichloro-N-((4'-chloro-2-methoxybiphenyl-3-yl)methyl)-N-(4-fluorobenzyl)-2-hydroxybenzenesulfonamide;
3,5-Dichloro-N-((4',6-dichlorobiphenyl-3-yl)methyl)-N-(4-fluorobenzyl)-2-hydroxybenzenesulfonamide;
3,5-Dichloro-N-((4',5-dichloro-biphenyl-3-yl)methyl)-N-(4-fluorobenzyl)-2-hydroxybenzene-sulfonamide;
3,5-Dichloro-N-((4,4'-dichloro-biphenyl-3-yl)methyl)-N-(4-fluorobenzyl)-2-hydroxybenzene-sulfonamide;
3,5-Dichloro-N-((4'-chloro-6-methyl-biphenyl-3-yl)methyl)-N-(4-fluorobenzyl)-2-hydroxybenzene-sulfonamide;
N-((5-Bromo-4'-chlorobiphenyl-3-yl)methyl)-3,5-dichloro-N-(4-fluoro-benzyl)-2-hydroxybenzene-sulfonamide;
3,5-Dichloro-N-((4'-chloro-5-methoxybiphenyl-3-yl)methyl)-N-(4-fluorobenzyl)-2-hydroxybenzene-sulfonamide;
3,5-Dichloro-N-((4'-chloro-4-methoxybiphenyl-3-yl)methyl)-N-(4-fluorobenzyl)-2-hydroxybenzene-sulfonamide;
3,5-Dichloro-N-((4'-chloro-5,6-dimethoxybiphenyl-3-yl)methyl)-N-(4-fluorobenzyl)-2-hydroxy-benzenesulfonamide;
3,5-Dichloro-N-((4',5-dichloro-6-methoxybiphenyl-3-yl)methyl)-N-(4-fluorobenzyl)-2-hydroxybenzenesulfonamide;
3,5-Dichloro-N-((4'-chloro-6-methoxybiphenyl-3-yl)methyl)-N-(4-fluorobenzyl)-2-hydroxy-benzenesulfonamide;
3,5-Dichloro-N-(4-fluorobenzyl)-2-hydroxy-N-(4-(4-(trifluoro-methyl)phenoxy)benzyl)benzene-sulfonamide;
3,5-Dichloro-N-((4',5-dichloro-6-methoxybiphenyl-3-yl)methyl)-2-hydroxy-N-(4-(4-(trifluoromethyl)phenoxy)benzyl)-benzenesulfonamide;
3,5-Dichloro-N-(4-fluorobenzyl)-2-hydroxy-N-((4'-(trifluoromethyl)-biphenyl-4-yl)methyl)benzene-sulfonamide;
N-((4'-tert-Butylbiphenyl-3-yl)methyl)-3,5-dichloro-N-(4-fluorobenzyl)-2-hydroxybenzene-sulfonamide;
3,5-Dichloro-N-((3'-chlorobiphenyl-3-yl)methyl)-N-(4-fluorobenzyl)-2-hydroxybenzenesulfonamide;
N-((4'-Butylbiphenyl-3-yl)methyl)-3,5-dichloro-N-(4-fluorobenzyl)-2-hydroxybenzenesulfonamide;
3,5-Dichloro-N-((2'-chlorobiphenyl-3-yl)methyl)-N-(4-fluorobenzyl)-2-hydroxybenzenesulfonamide;
3,5-Dichloro-N-((4'-chlorobiphenyl-4-yl)methyl)-N-(4-fluorobenzyl)-2-hydroxybenzenesulfonamide;
3,5-Dichloro-N-((4'-chlorobiphenyl-3-yl)methyl)-2-hydroxy-N-(4-(trifluoromethyl)benzyl)benzene-sulfonamide;
3,5-Dichloro-N-((4'-chlorobiphenyl-3-yl)methyl)-N-(4-fluorophenethyl)-2-hydroxybenzenesulfonamide;
3,5-Dichloro-N-((4'-chlorobiphenyl-3-yl)methyl)-N-(2,3-dihydro-1H-inden-2-yl)-2-hydroxybenzenesulfonamide;
N-(2-(1H-Indol-1-yl)ethyl)-3,5-dichloro-N-((4'-chlorobiphenyl-3-yl)methyl)-2-hydroxybenzenesulfonamide;
N-(2-(1H-Indol-1-yl)ethyl)-3,5-dichloro-N-((4',5-dichloro-6-methoxybiphenyl-3-yl)methyl)-hydroxybenzenesulfonamide;
3,5-Dichloro-N-((4'-chlorobiphenyl-3-yl)methyl)-N-(4-(4-fluorophenoxy)benzyl)-2-hydroxybenzenesulfonamide;
3,5-Dichloro-N-(4-fluoro-3-(trifluoromethyl)benzyl)-N-(4-fluorobenzyl)-2-hydroxybenzenesulfonamide;
3,5-Dichloro-N-(4-fluorobenzyl)-2-hydroxy-N-(3-methylbenzyl)benzenesulfonamide (266);
3,5-Dichloro-N-(4-fluorophenethyl)-2-hydroxy-N-(3-(phenethylthiomethyl)benzyl)benzenesulfonamide;
3,5-Dichloro-N-(4-fluorophenethyl)-2-hydroxy-N-(4-(phenethylthiomethyl)benzyl)-benzenesulfonamide;
3,5-Dichloro-N-(4-fluorophenethyl)-2-hydroxy-N-(3-nitro-4-(phenethylthiomethyl)benzyl)-benzenesulfonamide;
6-((3,5-Dichloro-N-(4-fluorobenzyl)-2-hydroxyphenylsulfonamido)methyl)-N-(3,5-dichlorobenzyl)-N-(4-fluorobenzyl)picolinamide;
6-((3,5-Dichloro-N-(4-fluorobenzyl)-2-hydroxyphenylsulfonamido)methyl)-N-(4-fluorobenzyl)picolinamide;
3,5-Dichloro-N-((6-(4-chlorobenzyl)pyridin-2-yl)methyl)-N-(4-fluorobenzyl)-2-hydroxybenzenesulfonamide;
3,5-Dichloro-N-((6-(4-chlorophenoxy)pyridin-2-yl)methyl)-N-(4-fluorobenzyl)-2-hydroxybenzenesulfonamide;

3,5-Dichloro-N-(4-chlorobenzyl)-N-((6-(4-chlorophenyl)pyridin-2-yl)methyl)-2-hydroxybenzenesulfonamide;

3,5-Dichloro-N-((6-(4-chlorophenyl)pyridin-2-yl)methyl)-N-(4-fluorobenzyl)-2-hydroxybenzenesulfonamide.

In some embodiments, the compound is selected from the group consisting of:

1-Benzyl-3-pyridin-2-ylmethyl-1,3-dihydro-benzoimidazol-2-ylideneamine;

1-Benzyl-3-pyridin-3-ylmethyl-1,3-dihydro-benzoimidazol-2-ylideneamine;

1-Benzyl-3-pyridin-4-ylmethyl-1,3-dihydro-benzoimidazol-2-ylideneamine;

1-Benzyl-3-(tetrahydro-pyran-4-ylmethyl)-1,3-dihydro-benzoimidazol-2-ylideneamine;

1-(4-Bromo-benzyl)-3-[3-(4-fluoro-phenoxy)-propyl]-1,3-dihydro-benzoimidazol-2-ylideneamine;

1-(3-Bromo-benzyl)-3-[3-(4-fluoro-phenoxy)-propyl]-1,3-dihydro-benzoimidazol-2-ylideneamine;

1-(4-Bromo-benzyl)-3-(2-phenylsulfanyl-ethyl)-1,3-dihydro-benzoimidazol-2-ylideneamine;

{3-[3-(4-Fluoro-phenoxy)-propyl]-2-imino-2,3-dihydro-benzoimidazol-1-yl}-acetic acid ethyl ester;

1-[3-(4-Chloro-phenoxy)-propyl]-3-pyridin-4-ylmethyl-1,3-dihydro-benzoimidazol-2-ylideneamine;

1-(3-Chloro-benzyl)-3-[3-(4-fluoro-phenoxy)-propyl]-1,3-dihydro-benzoimidazol-2-ylideneamine;

1-(3,4-Dichloro-benzyl)-3-[3-(4-fluoro-phenoxy)-propyl]-1,3-dihydro-benzoimidazol-2-ylideneamine;

1-(4-Bromo-benzyl)-3-[3-(4-chloro-phenoxy)-propyl]-1,3-dihydro-benzoimidazol-2-ylideneamine;

1-(4-Bromo-benzyl)-3-(2,3-dihydro-benzo[1,4]dioxin-2-ylmethyl)-1,3-dihydro-benzoimidazol-2-ylideneamine;

1-(4-Bromo-benzyl)-3-[3-(4-nitro-phenoxy)-propyl]-1,3-dihydro-benzoimidazol-2-ylideneamine;

3-{3-[3-(4-Fluoro-phenoxy)-propyl]-2-imino-2,3-dihydro-benzoimidazol-1-ylmethyl}-benzoic acid methyl ester;

1-(4'-Fluoro-biphenyl-4-ylmethyl)-3-[3-(4-fluoro-phenoxy)-propyl]-1,3-dihydro-benzoimidazol-2-ylideneamine;

1-[4-(4-Biphenyl-2-ylmethyl-piperazin-1-yl)-benzyl]-3-methyl-1,3-dihydro-benzoimidazol-2-ylideneamine;

1-Benzyl-3-[4-(4-biphenyl-2-ylmethyl-piperazin-1-yl)-benzyl]-1,3-dihydro-benzoimidazol-2-ylideneamine;

1-{4-[4-(4-Chloro-benzyl)-piperazin-1-yl]-benzyl}-3-[3-(4-fluoro-phenoxy)-propyl]-1,3-dihydro-benzoimidazol-2-ylideneamine;

1-{4-[4-(2-Chloro-benzyl)-piperazin-1-yl]-benzyl}-3-[3-(4-fluoro-phenoxy)-propyl]-1,3-dihydro-benzoimidazol-2-ylideneamine;

1-{4-[4-(3-Chloro-benzyl)-piperazin-1-yl]-benzyl}-3-[3-(4-fluoro-phenoxy)-propyl]-1,3-dihydro-benzoimidazol-2-ylideneamine;

1-[4-(4-Benzyl-piperazin-1-yl)-benzyl]-3-[3-(4-fluoro-phenoxy)-propyl]-1,3-dihydro-benzoimidazol-2-ylideneamine;

1-(4-{4-[2-(4-Chloro-phenyl)-5,5-dimethyl-cyclohex-1-enylmethyl]-piperazin-1-yl}-benzyl)-3-[3-(4-fluoro-phenoxy)-propyl]-1,3-dihydro-benzoimidazol-2-ylideneamine;

1-{4-[4-(4'-Chloro-biphenyl-2-ylmethyl)-piperazin-1-yl]-benzyl}-3-[3-(4-fluoro-phenoxy)-propyl]-1,3-dihydro-benzoimidazol-2-ylideneamine;

1-[4-(4-Biphenyl-2-ylmethyl-piperazin-1-O-benzyl]-3-[3-(4-fluoro-phenoxy)-propyl]-1,3-dihydro-benzoimidazol-2-ylideneamine;

1-[3-(4-Biphenyl-2-ylmethyl-piperazin-1-O-benzyl]-3-[3-(4-fluoro-phenoxy)-propyl]-1,3-dihydro-benzoimidazol-2-ylideneamine;

1-{3-[4-(4'-Chloro-biphenyl-2-ylmethyl)-piperazin-1-yl]-benzyl}-3-[3-(4-fluoro-phenoxy)-propyl]-1,3-dihydro-benzoimidazol-2-ylideneamine;

1-[4-(4-Biphenyl-2-ylmethyl-piperazin-1-O-benzyl]-3-(3-phenoxy-propyl)-1,3-dihydro-benzoimidazol-2-ylideneamine;

1-[3-(4-Biphenyl-2-ylmethyl-piperazin-1-O-benzyl]-3-(3-phenoxy-propyl)-1,3-dihydro-benzoimidazol-2-ylideneamine;

1-{4-[4-(4'-Chloro-biphenyl-2-ylmethyl)-piperazin-1-yl]-benzyl}-3-(3-phenoxy-propyl)-1,3-dihydro-benzoimidazol-2-ylideneamine;

1-(3-{4-[2-(4-Chloro-phenyl)-5,5-dimethyl-cyclohex-1-enylmethyl]-piperazin-1-yl}-benzyl)-3-[3-(4-fluoro-phenoxy)-propyl]-1,3-dihydro-benzoimidazol-2-ylideneamine;

1-(4-{4-[2-(4-Chloro-phenyl)-5,5-dimethyl-cyclohex-1-enylmethyl]-piperazin-1-yl}-benzyl)-3-(3-phenoxy-propyl)-1,3-dihydro-benzoimidazol-2-ylideneamine;

1-{4-[4-(4'-Chloro-biphenyl-2-ylmethyl)-piperazin-1-yl]-benzyl}-3-(2-phenylsulfanyl-ethyl)-1,3-dihydro-benzoimidazol-2-ylideneamine;

1-(2-Chloro-thiazol-4-ylmethyl)-3-[3-(4-fluoro-phenoxy)-propyl]-1,3-dihydro-benzoimidazol-2-ylideneamine;

1-[2-(4-Biphenyl-2-ylmethyl-piperazin-1-yl)-thiazol-4-ylmethyl]-3-[3-(4-fluoro-phenoxy)-propyl]-1,3-dihydro-benzoimidazol-2-ylideneamine;

1-{2-[4-(4'-Chloro-biphenyl-2-ylmethyl)-piperazin-1-yl]-thiazol-4-ylmethyl}-3-[3-(4-fluoro-phenoxy)-propyl]-1,3-dihydro-benzoimidazol-2-ylideneamine;

1-(2-{4-[2-(4-Chloro-phenyl)-5,5-dimethyl-cyclohex-1-enylmethyl]-piperazin-1-yl}-thiazol-4-ylmethyl)-3-[3-(4-fluoro-phenoxy)-propyl]-1,3-dihydro-benzoimidazol-2-ylideneamine;

1-[2-(4-Biphenyl-2-ylmethyl-piperazin-1-yl)-benzyl]-3-[3-(4-fluoro-phenoxy)-propyl]-1,3-dihydro-benzoimidazol-2-ylideneamine;

1-{4-[4-(4-Chloro-benzyl)-piperazin-1-ylmethyl]-benzyl}-3-[3-(4-fluoro-phenoxy)-propyl]-1,3-dihydro-benzoimidazol-2-ylideneamine;

1-[3-(4-Fluoro-phenoxy)-propyl]-3-[4-(4-phenyl-piperazin-1-ylmethyl)-benzyl]-1,3-dihydro-benzoimidazol-2-ylideneamine;

1-{4-[4-(3-Chloro-phenyl)-piperazin-1-ylmethyl]-benzyl}-3-[3-(4-fluoro-phenoxy)-propyl]-1,3-dihydro-benzoimidazol-2-ylideneamine;

1-{4-[4-(4-Chloro-phenyl)-piperazin-1-ylmethyl]-benzyl}-3-[3-(4-fluoro-phenoxy)-propyl]-1,3-dihydro-benzoimidazol-2-ylideneamine;

N-(2-Chloro-phenyl)-2-(4-{3-[3-(4-fluoro-phenoxy)-propyl]-2-imino-2,3-dihydro-benzoimidazol-1-ylmethyl}-benzylamino)-acetamide;

1-{4-[4-(2-Chloro-phenyl)-piperazin-1-ylmethyl]-benzyl}-3-[3-(4-fluoro-phenoxy)-propyl]-1,3-dihydro-benzoimidazol-2-ylideneamine;

N-(4-Chloro-phenyl)-2-(4-{3-[3-(4-fluoro-phenoxy)-propyl]-2-imino-2,3-dihydro-benzoimidazol-1-ylmethyl}-benzylamino)-acetamide;

1-[4-(4-Benzyl-piperazin-1-ylmethyl)-benzyl]-3-[3-(4-fluoro-phenoxy)-propyl]-1,3-dihydro-benzoimidazol-2-ylideneamine;

1-{4-[4-(3-Chloro-benzyl)-piperazin-1-ylmethyl]-benzyl}-3-[3-(4-fluoro-phenoxy)-propyl]-1,3-dihydro-benzoimidazol-2-ylideneamine;

1-{4-[4-(2-Chloro-benzyl)-piperazin-1-ylmethyl]-benzyl}-3-[3-(4-fluoro-phenoxy)-propyl]-1,3-dihydro-benzoimidazol-2-ylideneamine;

1-[4-(4-Biphenyl-2-ylmethyl-piperazin-1-ylmethyl)-benzyl]-3-[3-(4-fluoro-phenoxy)-propyl]-1,3-dihydro-benzoimidazol-2-ylideneamine;

N-(3-Chloro-phenyl)-2-(4-{3-[3-(4-fluoro-phenoxy)-propyl]-2-imino-2,3-dihydro-benzoimidazol-1-ylmethyl}-benzylamino)-acetamide;

2-(4-{3-[3-(4-Fluoro-phenoxy)-propyl]-2-imino-2,3-dihydro-benzoimidazol-1-ylmethyl}-benzylamino)-N-phenyl-acetamide;

1-(6-Chloro-pyridin-3-ylmethyl)-3-[3-(4-fluoro-phenoxy)-propyl]-1,3-dihydro-benzoimidazol-2-ylideneamine;

1-[6-(4-Benzyl-piperazin-1-yl)-pyridin-3-ylmethyl]-3-[3-(4-fluoro-phenoxy)-propyl]-1,3-dihydro-benzoimidazol-2-ylideneamine;

1-{6-[4-(3-Chloro-benzyl)-piperazin-1-yl]-pyridin-3-ylmethyl}-3-[3-(4-fluoro-phenoxy)-propyl]-1,3-dihydro-benzoimidazol-2-ylideneamine;

1-{6-[4-(4-Chloro-benzyl)-piperazin-1-yl]-pyridin-3-ylmethyl}-3-[3-(4-fluoro-phenoxy)-propyl]-1,3-dihydro-benzoimidazol-2-ylideneamine;

1-[6-(4-Biphenyl-2-ylmethyl-piperazin-1-yl)-pyridin-3-ylmethyl]-3-[3-(4-fluoro-phenoxy)-propyl]-1,3-dihydro-benzoimidazol-2-ylideneamine;

1-{6-[4-(2-Chloro-benzyl)-piperazin-1-yl]-pyridin-3-ylmethyl}-3-[3-(4-fluoro-phenoxy)-propyl]-1,3-dihydro-benzoimidazol-2-ylideneamine;

3-(4-Bromo-benzyl)-1-[3-(4-fluoro-phenoxy)-propyl]-5-methyl-1,3-dihydro-benzoimidazol-2-ylideneamine;

3-(4-Bromo-benzyl)-5-fluoro-1-[3-(4-fluoro-phenoxy)-propyl]-1,3-dihydro-benzoimidazol-2-ylideneamine;

1-(4-Bromo-benzyl)-3-[3-(4-fluoro-phenoxy)-propyl]-5-trifluoromethyl-1,3-dihydro-benzoimidazol-2-ylideneamine;

1-(4-Bromo-benzyl)-5-fluoro-3-[3-(4-fluoro-phenoxy)-propyl]-1,3-dihydro-benzoimidazol-2-ylideneamine;

3-[4-(4-Biphenyl-2-ylmethyl-piperazin-1-yl)-benzyl]-1-[3-(4-fluoro-phenoxy)-propyl]-5-methyl-1,3-dihydro-benzoimidazol-2-ylideneamine;

3-[4-(4-Biphenyl-2-ylmethyl-piperazin-1-yl)-benzyl]-5-fluoro-1-[3-(4-fluoro-phenoxy)-propyl]-1,3-dihydro-benzoimidazol-2-ylideneamine;

3-(4-{4-[2-(4-Chloro-phenyl)-5,5-dimethyl-cyclohex-1-enylmethyl]-piperazin-1-yl}-benzyl)-5-fluoro-1-[3-(4-fluoro-phenoxy)-propyl]-1,3-dihydro-benzoimidazol-2-ylideneamine;

3-{3-[3-(4-Bromo-benzyl)-2-imino-2,3-dihydro-benzoimidazol-1-yl]-propoxy}-benzoic acid ethyl ester;

4-{3-[3-(4-Bromo-benzyl)-2-imino-2,3-dihydro-benzoimidazol-1-yl]-propoxy}-benzoic acid methyl ester;

4-{3-[3-(3-Bromo-benzyl)-2-imino-2,3-dihydro-benzoimidazol-1-yl]-propoxy}-benzoic acid methyl ester;

3-{3-[3-(3-Bromo-benzyl)-2-imino-2,3-dihydro-benzoimidazol-1-yl]-propoxy}-benzoic acid ethyl ester;

3-(3-{3-[4-(4-Biphenyl-2-ylmethyl-piperazin-1-yl)-benzyl]-2-imino-2,3-dihydro-benzoimidazol-1-yl}-propoxy)-benzoic acid ethyl ester;

3-(3-{3-[4-(4-Biphenyl-2-ylmethyl-piperazin-1-yl)-benzyl]-2-imino-2,3-dihydro-benzoimidazol-1-yl}-propoxy)-benzoic acid;

3-[3-(3-Benzyl-2-imino-2,3-dihydro-benzoimidazol-1-yl)-propoxy]-benzoic acid ethyl ester;

3-{3-[3-(4-Fluoro-phenoxy)-propyl]-2-imino-2,3-dihydro-benzoimidazol-1-ylmethyl}-benzoic acid;

3-[3-(3-{4-[4-(4'-Chloro-biphenyl-2-ylmethyl)-piperazin-1-yl]-benzyl}-2-imino-2,3-dihydro-benzoimidazol-1-yl)-propoxy]-benzoic acid ethyl ester;

3-[3-(3-{4-[4-(4'-Chloro-biphenyl-2-ylmethyl)-piperazin-1-yl]-benzyl}-2-imino-2,3-dihydro-benzoimidazol-1-yl)-propoxy]-benzoic acid;

3-{3-[3-(3-{4-[2-(4-Chloro-phenyl)-5,5-dimethyl-cyclohex-1-enylmethyl]-piperazin-1-yl}-benzyl)-2-imino-2,3-dihydro-benzoimidazol-1-yl]-propoxy}-benzoic acid;

1-[3-(3-Bromo-benzyl)-2-imino-2,3-dihydro-benzoimidazol-1-yl]-3-(4-fluoro-phenoxy)-propan-2-ol;

1-[3-(4-Bromo-benzyl)-2-imino-2,3-dihydro-benzoimidazol-1-yl]-3-(4-fluoro-phenoxy)-propan-2-ol;

1-(3-Benzyl-2-imino-2,3-dihydro-benzoimidazol-1-yl)-3-phenoxy-propan-2-ol;

1-{3-[4-(4-Biphenyl-2-ylmethyl-piperazin-1-yl)-benzyl]-2-imino-2,3-dihydro-benzoimidazol-1-yl}-3-(4-fluoro-phenoxy)-propan-2-ol;

1-{3-[4-(4-Biphenyl-2-ylmethyl-piperazin-1-yl)-benzyl]-2-imino-2,3-dihydro-benzoimidazol-1-yl}-3-(4-fluoro-phenoxy)-propan-2-ol;

3-{3-[3-(3-Bromo-benzyl)-2-imino-2,3-dihydro-benzoimidazol-1-yl]-propoxy}-benzoic acid;

3-{3-[3-(4-Bromo-benzyl)-2-imino-2,3-dihydro-benzoimidazol-1-yl]-propoxy}-benzoic acid; and N-(3-{3-[3-(3-Bromo-benzyl)-2-imino-2,3-dihydro-benzoimidazol-1-yl]-propoxy}-benzoyl)-methanesulfonamide.

In some embodiments, the compound is selected from the group consisting of:

N-{7-[1-(4'-Chloro-1-biphenyl-2-ylmethyl)-piperidin-4-yl]-5,6,7,8-tetrahydro-pyrido[3,4-d]pyrimidin-4-yl}-4-((R)-3-dimethylamino-1-phenylsulfanylmethyl-propylamino)-3-nitro-benzenesulfonamide;

(R)—N-(7-(1-((2-(4-chlorphenyl)-5,5-dimethyl-cyclohex-1-enyl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-nitrobenzenesulfonamide;

N-(7-((2S)-1((4'-chlorobiphenyl-2-yl)methyl)-2-methylpiperidin-4-yl)-5,6,7,8-tetrahydropyrido[3,4-d]pyrimidin-4-yl)-4-((R)-4-(dimethylamino)-1-(phenylthio)butan-2-ylamino)-3-nitrobenzene-sulfonamide;

N-(7-((2S)-1-(4'-chlorobiphenyl-2-yl)methyl)-2-methylpiperidin-4-yl)-5,6,7,8-tetrahydropyrido[3,4-d]pyrimidin-4-yl)-4-((R)-4-(dimethylamino)-1-(phenylthio)butan-2-ylamino)-3-(trifluoromethyl-sulfonyl)benzenesulfonamide, trifluoroacetate salt;

(R)-4-(4-(dimethylamino)-1-(phenylthio)butan-2-ylamino)-N-(7-(1-((4'-fluorobiphenyl-2-yl)methyl)piperidin-4-yl)-5,6,7,8-tetrahydropyrido[3,4-d]pyrimidin-4-yl)-3-(trifluoromethylsulfonyl)benzenesulfonamide;

(R)—N-(7-(1-((4'-bromobiphenyl-2-yl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide;

(R)—N-(7-(1-(2-bromobenzyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide;

N-(7-[2-(4-Chloro-phenyl)-5,5-dimethyl-cyclohex-1-enylmethyl]-5,6,7,8-tetrahydro-pyrido[3,4-d]pyrimidin-4-yl)-4-((R)-3-morpholin-4-yl-1-phenylsulfanylmethyl-propylamino)-3-trifluoromethanesulfonylbenzenesulfonamide;

(R)—N-(7-(1-((4'-chlorobiphenyl-2-yl)methyl)piperidin-4-yl)-5,6,7,8-tetrahydropyrido[3,4-d]pyrimidin-4-yl)-4-(4-morpholino-1-(phenylthio)butan-2-ylamino)-3-(trifluoromethylsulfonyl)benzenesulfonamide;

(R)—N-(7-(1-((2-(4-chlorphenyl)-5,5-dimethylcyclohex-1-enyl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide;

(R)—N-(7-(1-((4'-chlorobiphenyl-2-yl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide;

(R)—N-(7-(1-((4'-chlorobiphenyl-2-yl)methyl)piperidin-4-yl)-5,6,7,8-tetrahydropyrido[3,4-d]pyrimidin-4-yl)-4-(4-(dimethylamino)-1-(phenylthio)butan-2-ylamino)-3,5-difluorobenzenesulfonamide;

N-(7-(1-((2-(4-chlorophenyl)-5,5-dimethylcyclohex-1-enyl)methyl)piperidin-4-yl)-5,6,7,8-tetrahydropyrido[3,4-d]pyrimidin-4-yl)-4-(1-(phenylthio)butan-2-ylamino)-3-(trifluoromethylsulfonyl)benzenesulfonamide;

N-(7-(1-((2-(4-chlorophenyl)-4,4-dimethylcyclohex-1-enyl)methyl)piperidin-4-yl)-5,6,7,8-tetrahydropyrido[3,4-d]pyrimidin-4-yl)-4-(1-(phenylthio)butan-2-ylamino)-3-(trifluoromethylsulfonyl)benzenesulfonamide;

N-(4-(N-(7-(1-((4'-chloro-4-fluorobiphenyl-2-yl)methyl)piperidin-4-yl)-5,6,7,8-tetrahydropyrido[3,4-d]pyrimidin-4-yl) sulfamoyl)-2-(trifluoromethylsulfonyl)phenyl)-N-(2-(phenylthio)ethyl)acetamide;

(R)—N-(7-(1-((2-(4-chlorphenyl)-4,4-dimethylcyclohex-1-enyl)methyl)piperidin-4-yl)-5,6,7,8-tetrahydropyrido[3,4-d]pyrimidin-4-yl)-4-(4-morpholino-1-(phenylthio)butan-2-ylamino)-3-(trifluoromethylsulfonyl)benzenesulfonamide;

(R)—N-(7-(1-((2-(4-chlorphenyl)-4,4-dimethylcyclohex-1-enyl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide;

N-(7-(1-((2-(4-chlorophenyl)-4,4-dimethylcyclohex-1-enyl)methyl)piperidin-4-yl)-5,6,7,8-tetrahydropyrido[3,4-d]pyrimidin-4-yl)-4-(1-(phenylthio)pentan-2-ylamino)-3-(trifluoromethylsulfonyl)benzenesulfonamide;

(R)—N-(7-(1-((4'-chloro-5-fluorobiphenyl-2-yl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide;

(R)—N-(7-(1-((4'-chloro-4-fluorobiphenyl-2-yl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide;

(R)—N-(7-(1-((4'-chloro-3-fluorobiphenyl-2-yl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide;

(R)-3-(4-(N-(7-(1-((4'-chlorobiphenyl-2-yl)methyl)piperidin-4-yl)-5,6,7,8-tetrahydropyrido[3,4-d]pyrimidin-4-yl)sulfamoyl)-2-nitrophenylamino)-N,N-dimethyl-4-(phenylthio)butanamide;

N-{7-[1-(4'-Chloro-biphenyl-2-ylmethyl)-piperidin-4-yl]-5,6,7,8-tetrahydro-pyrido[3,4-d]pyrimidin-4-yl}-4-[(R)-3-(4-ethyl-piperazin-1-yl)-1-phenylsulfanylmethyl-propylamino]-3-trifluoromethanesulfonyl-benzenesulfonamide;

N-(7-(1-(1-(4'-chlorobiphenyl-2-yl)ethyl)piperidin-4-yl)-5,6,7,8-tetrahydropyrido[3,4-d]pyrimidin-4-yl)-4-((R)-4-morpholino-1-(phenylthio)butan-2-ylamino)-3-(trifluoromethylsulfonyl)benzenesulfonamide;

4-((R)-1-Benzyloxymethyl-3-dimethylamino-propylamino)-N-{7-[1-(4'-chloro-biphenyl-2-ylmethyl)-piperidin-4-yl]-5,6,7,8-tetrahydro-pyrido[3,4-d]pyrimidin-4-yl}-3-trifluoromethanesulfonyl-benzenesulfonamide;

N-{7-[1-(4'-Chloro-biphenyl-2-ylmethyl)-piperidin-4-yl]-5,6,7,8-tetrahydro-pyrido[3,4-d]pyrimidin-4-yl}-4-[(R)-1-(3-chloro-phenylsulfanylmethyl)-3-dimethylamino-propylamino]-3-trifluoromethanesulfonyl-benzenesulfonamide;

N-(7-(1-((2-(4-chlorophenyl)-4,4-dimethylcyclohex-1-enyl)methyl)-2-methylpiperidin-4-yl)-5,6,7,8-tetrahydropyrido[3,4-d]pyrimidin-4-yl)-4-((R)-4-morpholino-1-(phenylthio)butan-2-ylamino)-3-(trifluoromethylsulfonyl)benzenesulfonamide;

(R)—N-(7-(1-((2-(4-chlorophenyl)-4,4-dimethylcyclohex-1-enyl)methyl)piperidin-4-yl)-5,6,7,8-tetrahydropyrido[3,4-d]pyrimidin-4-yl)-4-(1-(2-chlorophenylthio)-4-(dimethylamino)butan-2-ylamino)-3-(trifluoromethylsulfonyl)benzenesulfonamide;

N-(7-(1-(1-(4'-chlorobiphenyl-2-yl)ethyl)piperidin-4-yl)-5,6,7,8-tetrahydropyrido[3,4-d]pyrimidin-4-yl)-4-((R)-1-(2-chlorophenylthio)-4-(dimethylamino)butan-2-ylamino)-3-(trifluoromethylsulfonyl)benzenesulfonamide;

(R)—N-(7-(1-((4'-chlorobiphenyl-2-yl)methyl)piperidin-4-yl)-5,6,7,8-tetrahydropyrido[3,4-d]pyrimidin-4-yl)-4-(1-(phenylthio)-4-(piperidin-1-yl)butan-2-ylamino)-3-(trifluoromethylsulfonyl)benzenesulfonamide;

N-(7-(1-(1-(4'-chloro-4-fluorobiphenyl-2-yl)ethyl)piperidin-4-yl)-5,6,7,8-tetrahydropyrido[3,4-d]pyrimidin-4-yl)-4-((R)-4-morpholino-1-(phenylthio)butan-2-ylamino)-3-(trifluoromethylsulfonyl)benzenesulfonamide;

(R)—N-(7-(1-((2-(4-chlorophenyl)-4,4-dimethylcyclohex-1-enyl)methyl)piperidin-4-yl)-2-(trifluoromethyl)-5,6,7,8-tetrahydropyrido[3,4-d]pyrimidin-4-yl)-4-(1-(2-chlorophenylthio)-4-(dimethylamino)butan-2-ylamino)-3-(trifluoromethylsulfonyl)benzenesulfonamide;

(R)—N-(7-(1-((4'-chlorobiphenyl-2-yl)methyl)piperidin-4-yl)-2-(trifluoromethyl)-5,6,7,8-tetrahydropyrido[3,4-d]pyrimidin-4-yl)-4-(1-(2-chlorophenylthio)-4-(dimethylamino)butan-2-ylamino)-3-(trifluoromethylsulfonyl)benzenesulfonamide;

N-(7-(1-(1-(4'-chlorobiphenyl-2-yl)ethyl)piperidin-4-yl)-2-(trifluoromethyl)-5,6,7,8-tetrahydropyrido[3,4-d]pyrimidin-4-yl)-4-((R)-1-(2-chlorophenylthio)-4-(dimethylamino) butan-2-ylamino)-3-(trifluoromethylsulfonyl)benzenesulfonamide;

N-(7-(1-(1-(4'-chloro-4-fluorobiphenyl-2-yl)ethyl)piperidin-4-yl)-5,6,7,8-tetrahydropyrido[3,4-d]pyrimidin-4-yl)-4-((R)-4-(4-methylpiperazin-1-yl)-1-(phenylthio)butan-2-ylamino)-3-(trifluoromethylsulfonyl)benzenesulfonamide;

(R)—N-(7-(1-((4'-chloro-4-methoxybiphenyl-2-yl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide;

N-{7-[1-(4'-Chloro-biphenyl-2-ylmethyl)-piperidin-4-yl]-5,6,7,8-tetrahydro-pyrido[3,4-d]pyrimidin-4-yl}-4-[(R)-3-dimethylamino-1-(4-fluoro-phenylsulfanylmethyl)-propylamino]-3-trifluoromethanesulfonyl-benzenesulfonamide;

(R)—N-(7-(1-((4'-chlorobiphenyl-2-yl)methyl)piperidin-4-yl)-5,6,7,8-tetrahydropyrido[3,4-d]pyrimidin-4-yl)-4-(1-(2,6-dichlorophenylthio)-4-(dimethylamino)butan-2-ylamino)-3-(trifluoromethylsulfonyl)benzenesulfonamide;

N-(7-[1-(4'-Chlorobiphenyl-2-ylmethyl)-piperidin-4-yl]-5,6,7,8-tetrahydro-pyrido[3,4-d]pyrimidin-4-yl)-4-[(R)-1-(3,4-dichloro-phenylsulfanylmethyl)-3-dimethylamino-propylamino]-3-trifluoromethanesulfonyl-benzene-sulfonamide;

(R)—N-(7-(1-((4'-chlorobiphenyl-2-yl)methyl)piperidin-4-yl)-5,6,7,8-tetrahydropyrido[3,4-d]pyrimidin-4-yl)-4-(1-(2-chlorophenylthio)-4-(dimethylamino)butan-2-ylamino)-3-(trifluoromethylsulfonyl)benzenesulfonamide;

(R)—N-(7-(1-((4'-chlorobiphenyl-2-yl)methyl)piperidin-4-yl)-5,6,7,8-tetrahydropyrido[3,4-d]pyrimidin-4-yl)-4-(1-(3,5-dichlorophenylthio)-4-(dimethylamino)butan-2-ylamino)-3-(trifluoromethylsulfonyl)benzenesulfonamide;

N-(7-(1-(1-(4'-chlorobiphenyl-2-yl)ethyl)piperidin-4-yl)-5,6,7,8-tetrahydropyrido[3,4-d]pyrimidin-4-yl)-4-((R)-4-morpholino-1-(phenylthio)butan-2-ylamino)-3-(trifluoromethylsulfonyl)benzenesulfonamide;

(R)—N-(7-(1-((4'-chlorobiphenyl-2-yl)methyl)piperidin-4-yl)-5,6,7,8-tetrahydropyrido[3,4-d]pyrimidin-4-yl)-4-(1-(phenylthio)pentan-2-ylamino)-3-(trifluoromethylsulfonyl)benzenesulfonamide;

N-(7-(1((4'-chlorobiphenyl-2-yl)methyl)piperidin-4-yl)-5,6,7,8-tetrahydropyrido[3,4-d]pyrimidin-4-yl)-4-(1-(phenylthio)propan-2-ylamino)-3-(trifluoromethylsulfonyl)benzenesulfonamide;

N-(7-(1-((2-(4-chlorophenyl)-4,4-dimethylcyclohex-1-enyl)methyl)piperidin-4-yl)-5,6,7,8-tetrahydropyrido[3,4-d]pyrimidin-4-yl)-4-(1-(phenylthio)propan-2-ylamino)-3-(trifluoromethylsulfonyl)benzenesulfonamide;

(R)—N-(7-(1-(2-(but-2-ynyloxy)benzyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide, trifluoroacetate salt;

N-{7-[1-(4'-Chloro-biphenyl-2-ylmethyl)-piperidin-4-yl]-5,6,7,8-tetrahydro-pyrido[3,4-d]pyrimidin-4-yl}-4-[(R)-3-dimethylamino-1-(2-fluoro-phenylsulfanylmethyl)-propylamino]-3-trifluoromethanesulfonyl-benzenesulfonamide;

N—{(S)-7-[1-(4'-Chloro-biphenyl-2-ylmethyl)-piperidin-4-yl]-6-methyl-5,6,7,8-tetrahydro-pyrido[3,4-d]pyrimidin-4-yl}-4-((R)-3-dimethylamino-1-phenylsulfanylmethyl-propylamino)-3trifluoromethanesulfonyl-benzene sulfonamide;

N—{(R)-7-[1-(4'-Chloro-biphenyl-2-ylmethyl)-piperidin-4-yl]-6-methyl-5,6,7,8-tetrahydro-pyrido[3,4-d]pyrimidin-4-yl}-4-((R)-3-dimethylamino-1-phenylsulfanylmethyl-propylamino)-3-trifluoromethanesulfonyl-benzene sulfonamide;

(R)—N-(2-chloro-7-(1-((4'-chlorobiphenyl-2-yl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide;

N-(7-(1-(1-(4'-chlorobiphenyl-2-yl)ethyl)piperidin-4-yl)-5,6,7,8-tetrahydropyrido[3,4-d]pyrimidin-4-yl)-4-((R)-4-(dimethylamino)-1-(phenylthio)butan-2-ylamino)-3-(trifluoromethylsulfonyl)benzenesulfonamide;

N-(7-(1-((4'-chlorobiphenyl-2-yl)methyl)piperidin-4-yl)-5,6,7,8-tetrahydropyrido[3,4-d]pyrimidin-4-yl)-4-(2-(phenylthio)ethylamino)-3-(trifluoromethylsulfonyl)benzenesulfonamide;

(R)—N-(7-(1-((4'-chlorobiphenyl-2-yl)methyl)piperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethyl)benzenesulfonamide;

(R)—N-(7-(1-((4'-chlorobiphenyl-2-yl)methyl)piperidin-4-yl)-5,6,7,8-tetrahydropyrido[3,4-d]pyrimidin-4-yl)-3-cyano-4-(4-(dimethylamino)-1-(phenylthio)butan-2-ylamino)benzenesulfonamide;

(R)—N-(7-(1-((2-(4-chlorophenyl)-4,4-dimethylcyclohex-1-enyl)methyl)piperidin-4-yl)-5,6,7,8-tetrahydropyrido[3,4-d]pyrimidin-4-yl)-4-(1-(2-fluorophenylthio)-4-(4-methylpiperazin-1-yl)butan-2-ylamino)-3-(trifluoromethylsulfonyl)benzenesulfonamide;

(R)—N-(7-(1-((4'-chlorobiphenyl-2-yl)methyl)piperidin-4-yl)-5,6,7,8-tetrahydropyrido[3,4-d]pyrimidin-4-yl)-4-(1-(2-fluorophenylthio)-4-(4-methylpiperazin-1-yl)butan-2-ylamino)-3-(trifluoromethylsulfonyl)benzenesulfonamide;

N-{7-[1-(4'-Fluoro-biphenyl-2-ylmethyl)-piperidin-4-yl]-5,6,7,8-tetrahydro-pyrido[3,4-d]pyrimidin-4-yl}-4-[(R)-1-(3-chloro-phenylsulfanylmethyl)-3-dimethylamino-propylamino]-3-trifluoromethanesulfonyl-benzenesulfonamide;

(R)—N-(7-(1-((4'-chlorobiphenyl-2-yl)methyl)piperidin-4-yl)-5,6,7,8-tetrahydropyrido[3,4-d]pyrimidin-4-yl)-4-(4-morpholino-1-(phenylthio)butan-2-ylamino)-3-nitrobenzenesulfonamide;

N-(7-(1-((2-(4-chlorophenyl)-4,4-dimethylcyclohex-1-enyl)methyl)piperidin-4-yl)-5,6,7,8-tetrahydropyrido[3,4-d]pyrimidin-4-yl)-4-(1-(phenylthio)pentan-2-ylamino)-3-(trifluoromethylsulfonyl)benzenesulfonamide;

(R)—N-(7-(4-(4'-chlorobiphenyl-2-yl)methyl)-4-methoxycyclohexyl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide;

(R)—N-(7-(4-(2-bromobenzyl)-4-methoxycyclohexyl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide;

N-(7-(4-((4'-chlorobiphenyl-2-yl)methylene)cyclohexyl)-5,6,7,8-tetrahydropyrido[3,4-d]pyrimidin-4-yl)-4-((R)-4-(dimethylamino)-1-(phenylthio)butan-2-ylamino)-3-(trifluoromethylsulfonyl)benzenesulfonamide;

N-(7-(4-benzylidenecyclohexyl)-5,6,7,8-tetrahydropyrido[3,4-d]pyrimidin-4-yl)-4-((R)-4-(dimethylamino)-1-(phenylthio)butan-2-ylamino)-3trifluoromethylsulfonyl)benzenesulfonamide;

(R)—N-(7-(4-((4'-chlorobiphenyl-2-yl)methyl)-4-hydroxycyclohexyl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide;

N-(7-(1-((4'-Chlorobiphenyl-2-yl)methyl)-3-fluoropiperidin-4-yl)-5,6,7,8-tetrahydropyrido[3,4-d]pyrimidin-4-yl)-4-((R)-4-morpholino-1-(phenylthio)butan-2-ylamino)-3-(trifluoromethylsulfonyl)benzenesulfonamide;

N-(7-(1-((4'-chlorobiphenyl-2-yl)methyl)-3-fluoropiperidin-4-yl)-5,6,7,8-tetrahydropyrido[3,4-d]pyrimidin-4-yl)-4-((R)-4-(dimethylamino)-1-(phenylthio)butan-2-ylamino)-3-(trifluoromethylsulfonyl)benzenesulfonamide;

(R)—N-(7-(1-((4'-chlorobiphenyl-2-yl)methyl)piperidin-4-yl)-2-(trifluoromethyl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide;

(R)—N-(7-(1-((4'-chlorobiphenyl-2-yl)methyl)piperidin-4-yl)-2-(trifluoromethyl)-5,6,7,8-tetrahydropyrido[3,4-d]

pyrimidin-4-yl)-4-(4-morpholino-1-(phenylthio)butan-2-ylamino)-3-(trifluoromethylsulfonyl)benzenesulfonamide;

N-(7-(1-((4'-chlorobiphenyl-2-yl)methyl)-3-fluoropiperidin-4-yl)-2-(trifluoromethyl)-5,6,7,8-tetrahydropyrido[3,4-d]pyrimidin-4-yl)-4((R)-4-(dimethylamino)-1-(phenylthio)butan-2-ylamino)-3-(trifluoromethylsulfonyl)benzenesulfonamide;

(R)—N-(7-(1-((2-(4-chlorophenyl)-5,5-dimethylcyclohex-1-enyl)methyl)piperidin-4-yl)-2-(trifluoromethyl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide;

(R)—N-(7-(1-((4'-chlorobiphenyl-2-yl)methyl)piperidin-4-yl)-2-(trifluoromethyl)-5,6,7,8-tetrahydropyrido[3,4-d]pyrimidin-4-yl)-4-(4-(dimethylamino)-1-(phenylthio)butan-2-ylamino)-3-nitrobenzenesulfonamide;

(R)—N-(6-(1-((4'-chlorobiphenyl-2-yl)methyl)piperidin-4-yl)-6,7-dihydro-5H-pyrrolo[3,4-d]pyrimidin-4-yl)-4-(4-morpholino-1-(phenylthio)butan-2-ylamino)-3-(trifluoromethylsulfonyl)benzenesulfonamide;

(R)—N-(7-(1-((4'-chloro-4-fluorobiphenyl-2-yl)methyl)-4-deuteropiperidin-4-yl)-5,6,7,8-tetrahydropyrido[3,4-d]pyrimidin-4-yl)-4-(4-(dimethylamino)-1-(phenylthio)butan-2-ylamino)-3-(trifluoromethylsulfonyl)benzenesulfonamide;

N-(7-(1-((S)-1-(4'-chlorobiphenyl-2-yl)ethyl)-4-deuteropiperidin-4-yl)-2-(trifluoromethyl)-5,6,7,8-tetrahydropyrido[3,4-d]pyrimidin-4-yl)-4-((R)-1-(2-fluorophenylthio)-4-(4-methylpiperazin-1-yl)butan-2-ylamino)-3-(trifluoromethylsulfonyl)benzenesulfonamide;

(R)—N-(7-(1-((2-(4-chlorophenyl)-4,4-dimethylcyclohex-1-enyl)methyl)-4-deuteropiperidin-4-yl)-2-(dimethylamino)-5,6,7,8-tetrahydropyrido[3,4-d]pyrimidin-4-yl)-4-(1-(2-fluorophenylthio)-4-(4-methylpiperazin-1-yl)butan-2-ylamino)-3-(trifluoromethylsulfonyl)benzenesulfonamide;

(R)—N-(7-(4-((4'-chlorobiphenyl-2-yl)methyl)-4-methoxy-1-deuterocyclohexyl)-5,6,7,8-tetrahydropyrido[3,4-d]pyrimidin-4-yl)-4-(1-(2-fluorophenylthio)-4-(4-methylpiperazin-1-yl)butan-2-ylamino)-3-(trifluoromethylsulfonyl)benzenesulfonamide;

4-((R)-1-Benzyloxymethyl-3-dimethylamino-propylamino)-N-{7-[4-deutero-1-(4'-chloro-4-fluoro-biphenyl-2-ylmethyl)-piperidin-4-yl]-5,6,7,8-tetrahydro-pyrido[3,4-d]pyrimidin-4-yl}-3-trifluoromethanesulfonyl-benzenesulfonamide;

N-(7-{1-[2-(4-Chloro-phenyl)-4,4-dimethyl-cyclohex-1-enylmethyl]-4-deutero-piperidin-4-yl}-5,6,7,8-tetrahydro-pyrido[3,4-d]pyrimidin-4-yl)-4-[(R)-3-(isopropyl-methyl-amino)-1-phenylsulfanylmethyl-propylamino]-3-trifluoromethanesulfonyl-benzenesulfonamide;

4-((R)-3-amino-1-phenylsulfanylmethyl-propylamino)-N-{7-[4-deutero-1-(4'-chloro-4-fluoro-biphenyl-2-ylmethyl)-piperidin-4-yl]-5,6,7,8-tetrahydro-pyrido[3,4-d]pyrimidin-4-yl}-3-trifluoromethanesulfonyl-benzenesulfonamide;

4-((2R)-4-(8-oxa-3-azabicyclo[3.2.1]octan-3-yl)-1-(phenylthio)butan-2-ylamino)-N-(7-(1-((4'-chloro-4-fluorobiphenyl-2-yl)methyl)-4-deuteropiperidin-4-yl)-5,6,7,8-tetrahydropyrido[3,4-d]pyrimidin-4-yl)-3-(trifluoromethylsulfonyl)benzenesulfonamide;

4-((2R)-4-(8-oxa-3-azabicyclo[3.2.1]octan-3-yl)-1-(phenylthio)butan-2-ylamino)-N-(7-(1-((2-(4-chlorophenyl)-4,4-dimethylcyclohex-1-enyl)methyl)-4-deuteropiperidin-4-yl)-5,6,7,8-tetrahydropyrido[3,4-d]pyrimidin-4-yl)-3-(trifluoromethylsulfonyl)benzenesulfonamide;

(R)—N-(7-(1-((4'-chloro-4-fluorobiphenyl-2-yl)methyl)-4-deuteropiperidin-4-yl)-5,6,7,8-tetrahydropyrido[3,4-d]pyrimidin-4-yl)-4-(1-(phenylthio)-4-(pyrrolidin-1-yl)butan-2-ylamino)-3-(trifluoromethylsulfonyl)benzenesulfonamide;

(R)—N-(7-(1-((2-4-chlorophenyl)-4,4-dimethylcyclohex-1-enyl)methyl)-4-deuteropiperidin-4-yl)-5,6,7,8-tetrahydropyrido[3,4-d]pyrimidin-4-yl)-4-(1-(2-fluorophenylthio)-4-(4-methylpiperazin-1-yl)butan-2-ylamino)-3-(trifluoromethylsulfonyl)benzenesulfonamide;

N-{7-[4-Deutero-1-(4'-chloro-4-fluoro-biphenyl-2-ylmethyl)-piperidin-4-yl]-5,6,7,8-tetrahydro-pyrido[3,4-d]pyrimidin-4-yl}-4-((R)-3-dimethylamino-1-phenylsulfanylmethyl-propylamino)-3-trifluoromethanesulfonyl-benzenesulfonamide;

(R)—N-(7-(1-((2-(4-chlorophenyl)-4,4-dimethylcyclohex-1-enyl)methyl)-4-deuteropiperidin-4-yl)-5,6,7,8-tetrahydropyrido[3,4-d]pyrimidin-4-yl)-4-(1-(phenylthio)-4-(pyrrolidin-1-yl)butan-2-ylamino)-3-(trifluoromethylsulfonyl)benzenesulfonamide;

N-(7-{1-[(R)-1-(4'-Chloro-biphenyl-2-yl)-ethyl]-4-deuteropiperidin-4-yl}-5,6,7,8-tetrahydro-pyrido[3,4-d]pyrimidin-4-yl)-4-((R)-3-morpholin-4-yl-1-phenylsulfanylmethyl-propylamino)-3-trifluoromethanesulfonyl-benzenesulfonamide;

(R)—N-(7-(1-((4'-chloro-4-fluorobiphenyl-2-yl)methyl)-4-deuteropiperidin-4-yl)-5,6,7,8-tetrahydropyrido[3,4-d]pyrimidin-4-yl)-4-(1-(2-fluorophenylthio)-4-(4-methylpiperazin-1-yl)butan-2-ylamino)-3-(trifluoromethylsulfonyl)benzenesulfonamide;

N-(7-{1-[(S)-1-(4'-Chloro-biphenyl-2-yl)-ethyl]-4-deuteropiperidin-4-yl}-5,6,7,8-tetrahydro-pyrido[3,4-d]pyrimidin-4-yl)-4-((R)-3-morpholin-4-yl-1-phenylsulfanylmethyl-propylamino)-3-trifluoromethanesulfonyl-benzenesulfonamide;

(R)—N-(7-(1-((4'-chloro-4-fluorobiphenyl-2-yl)methyl)-4-deuteropiperidin-4-yl)-5,6,7,8-tetrahydropyrido[3,4-d]pyrimidin-4-yl)-4-(4-(4-ethylpiperazin-1-yl)-1-(phenylthio)butan-2-ylamino)-3-(trifluoromethylsulfonyl)benzenesulfonamide;

N-(7-(1-(1-(2-(4-chlorophenyl)-4,4-dimethylcyclohex-1-enyl)ethyl)4-deuteropiperidin-4-yl)-5,6,7,8-tetrahydropyrido[3,4-d]pyrimidin-4-yl)-4-((R)-4-D-morpholino-1-(phenylthio)butan-2-ylamino)-3-(trifluoromethylsulfonyl)benzenesulfonamide;

(R)—N-(7-(1-((2-(4-chlorophenyl)-4,4-dimethylcyclohex-1-enyl)methyl)-4-deuteropiperidin-4-yl)-5,6,7,8-tetrahydropyrido[3,4-d]pyrimidin-4-yl)-4-(4-morpholino-1-(phenylthio)butan-2-ylamino)-3-(trifluoromethylsulfonyl)benzenesulfonamide;

N-{6-[1-(4'-Chloro-biphenyl-2-ylmethyl)-piperidin-4-yl]-5,6,7,8-tetrahydro-4H-1,2,3a,6-tetraaza-azulen-3-yl}-4-((R)-3-morpholin-4-yl-1-phenylsulfanylmethyl-propylamino)-3-trifluoromethanesulfonyl-benzenesulfonamide;

N-{6-[1-(4'-Chloro-biphenyl-2-ylmethyl)-piperidin-4-yl]-5,6,7,8-tetrahydro-4H-1,2,3a,6-tetraaza-azulen-3-yl}-4-((R)-3-dimethylamino-1-phenyl-sulfanylmethyl-propylamino)-3-trifluoromethanesulfonyl-benzenesulfonamide;

N-{7-[1-(4'-Chloro-biphenyl-2-ylmethyl)-piperidin-4-yl]-5,6,7,8-tetrahydro-[1,2,4]triazolo[4,3-a]pyrazin-3-yl}-4-((R)-3-morpholin-4-yl-1-phenylsulfanylmethyl-propylamino)-3-trifluoromethanesulfonyl-benzenesulfonamide;

N-{7-[1-(4'-Chloro-biphenyl-2-ylmethyl)-azepan-4-yl]-5,6,7,8-tetrahydro-[|1,2,4]triazolo[4,3-a]pyrazin-3-yl}-4-

((R)-3-morpholin-4-yl-1-phenylsulfanylmethyl-propylamino)-3-trifluoromethanesulfonyl-benzenesulfonamide;

N-{7-[1-(4'-Chloro-biphenyl-2-ylmethyl)-2-methyl-piperidin-4-yl]-5,6,7,8-tetrahydro-[1,2,4]triazolo[4,3-a]pyrazin-3-yl}-4-((R)-3-morpholin-4-yl-1-phenylsulfanylmethyl-propylamino)-3-trifluoromethanesulfonyl-benzenesulfonamide trifluoroacetate salt;

N-(7-[1-(3'-Chloro-biphenyl-2-ylmethyl)-piperidin-4-yl]-5,6,7,8-tetrahydro-pyrido[3,4-d]pyrimidin-4-yl)-4-((R)-3-dimethylamino-1-phenylsulfanylmethyl-propylamino)-3-trifluoromethanesulfonyl-benzenesulfonamide;

N-(7-(1-((2'-chlorobiphenyl-2-yl)methyl)piperidin-4-yl)-5,6,7,8-tetrahydropyrido[3,4-d]pyrimidin-4-yl)-4-((R)-4-(dimethylamino)-1-(phenylthio)butan-2-ylamino)-3-(trifluoromethylsulfonyl)benzenesulfonamide; and (R)-4-(4-(dimethylamino)-1-(phenylthio)butan-2-ylamino)-N-(7-(1-((4'-(trifluoromethyl)biphenyl-2-yl)methyl)piperidin-4-yl)-5,6,7,8-tetrahydropyrido[3,4-d]pyrimidin-4-yl)-3-(trifluoromethylsulfonyl)benzenesulfonamide.

In some embodiments, the compound is selected from the group consisting of:

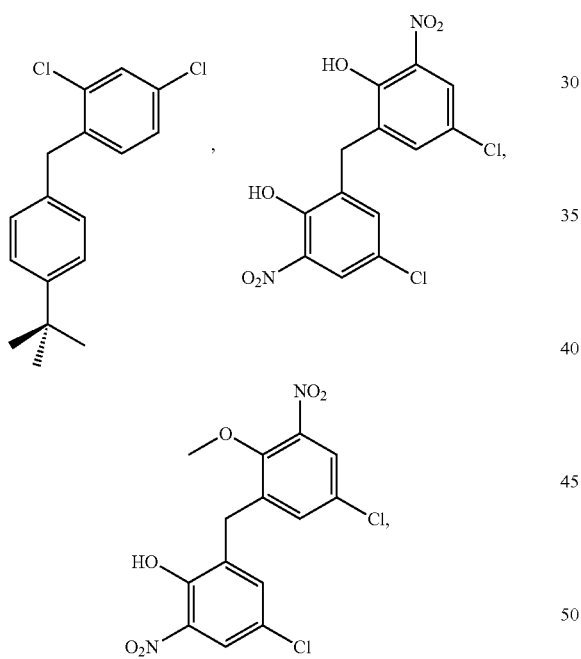

-continued

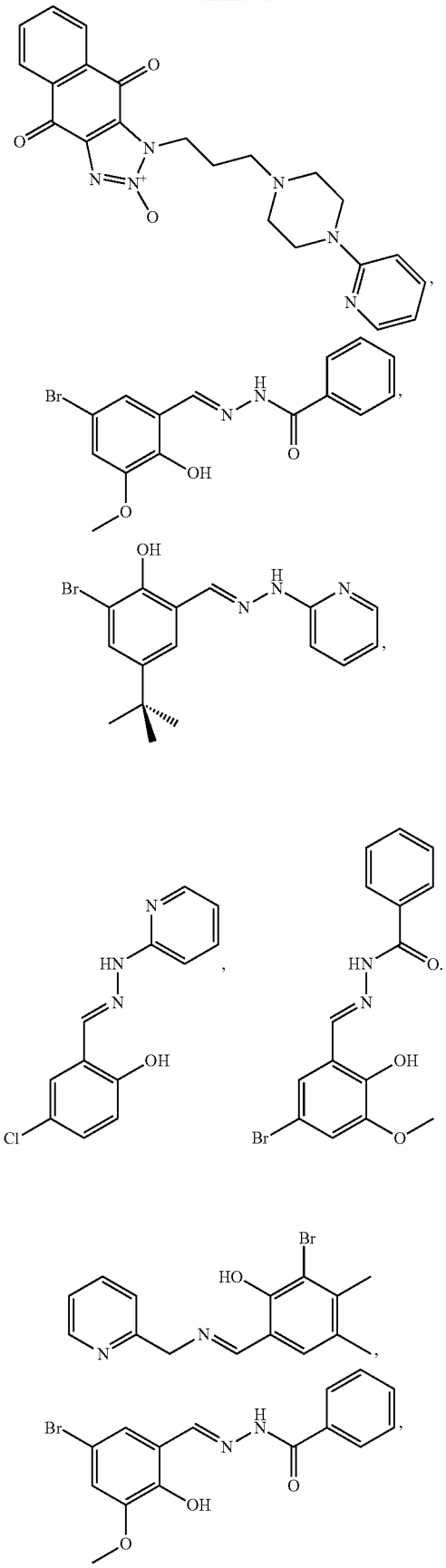

1653
-continued
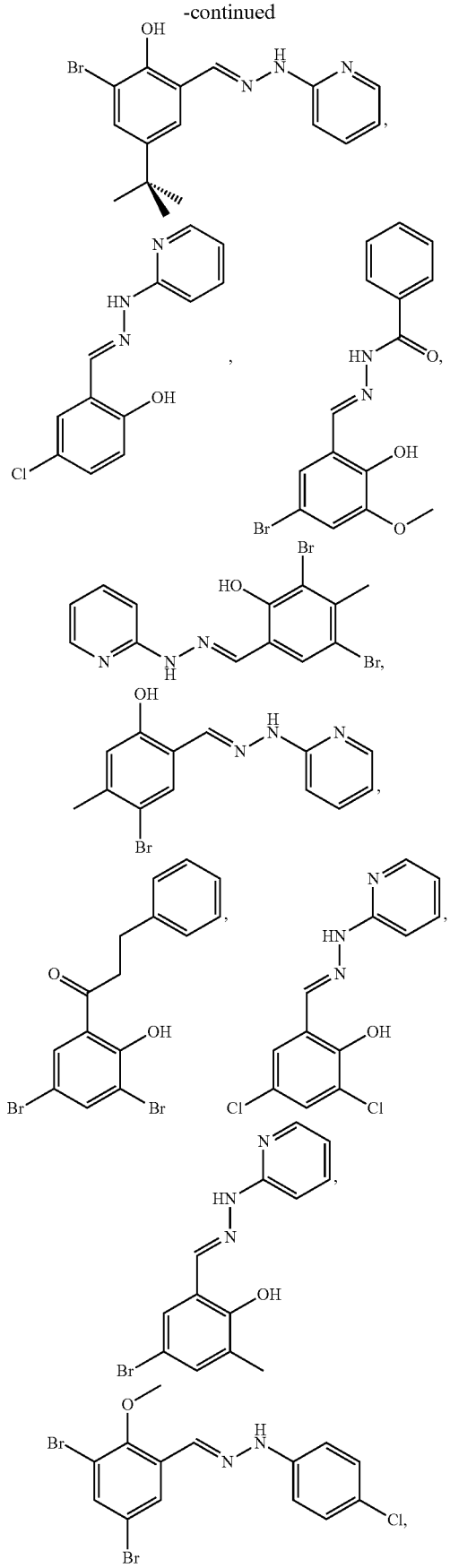
1654
-continued
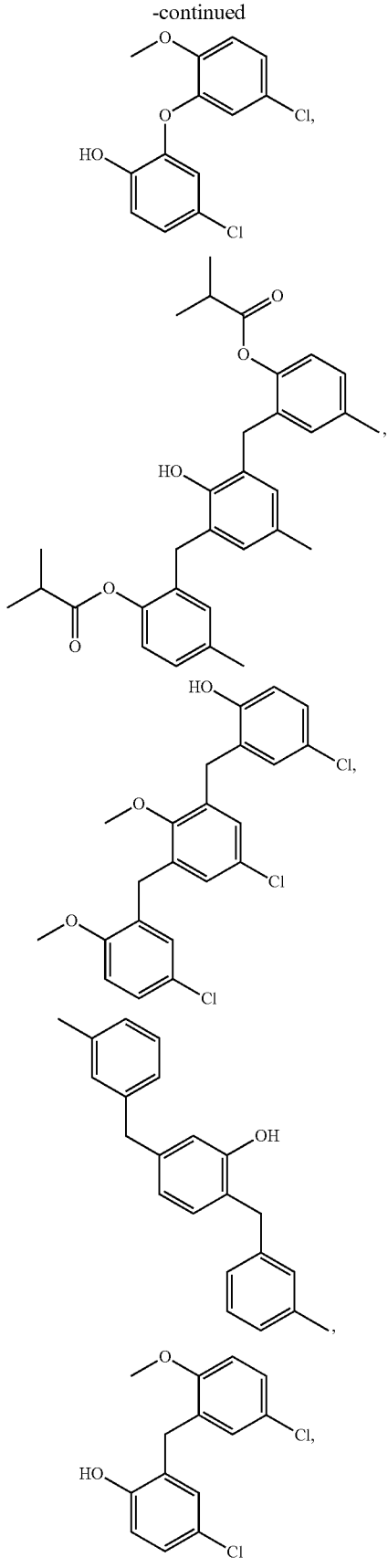

1655
-continued
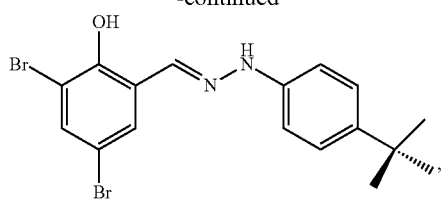
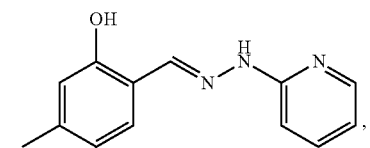
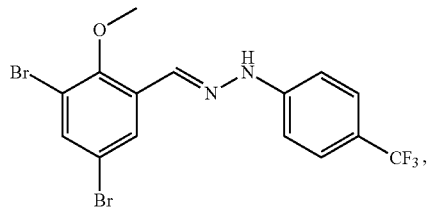
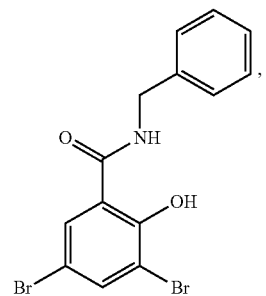
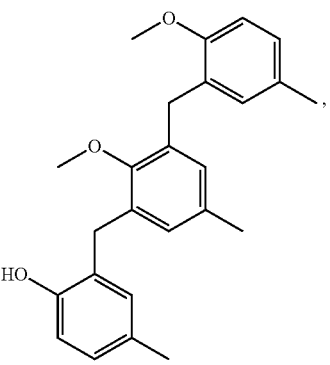
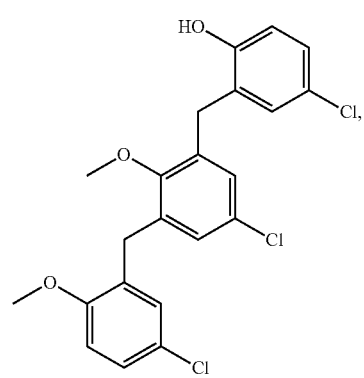
1656
-continued
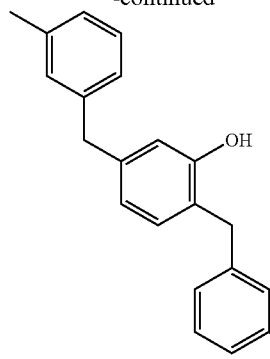
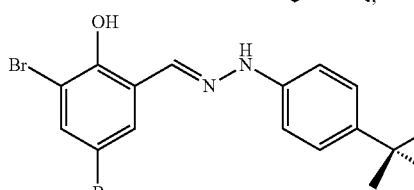
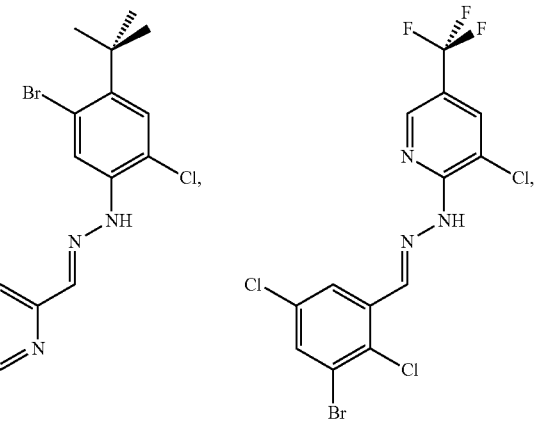
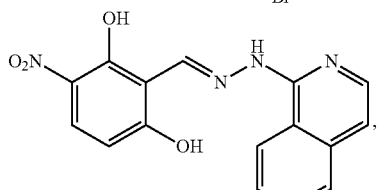
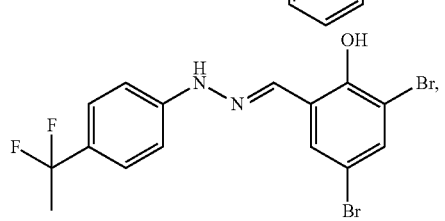
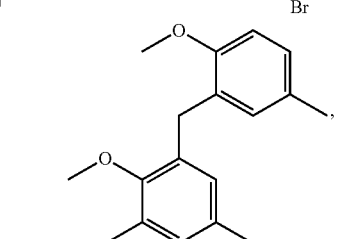
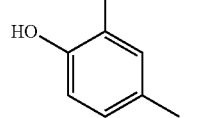

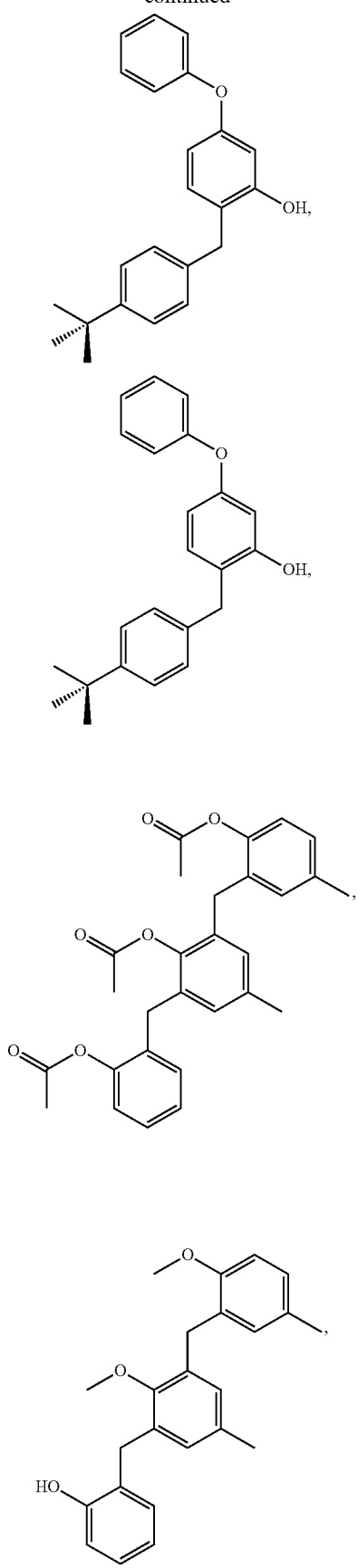
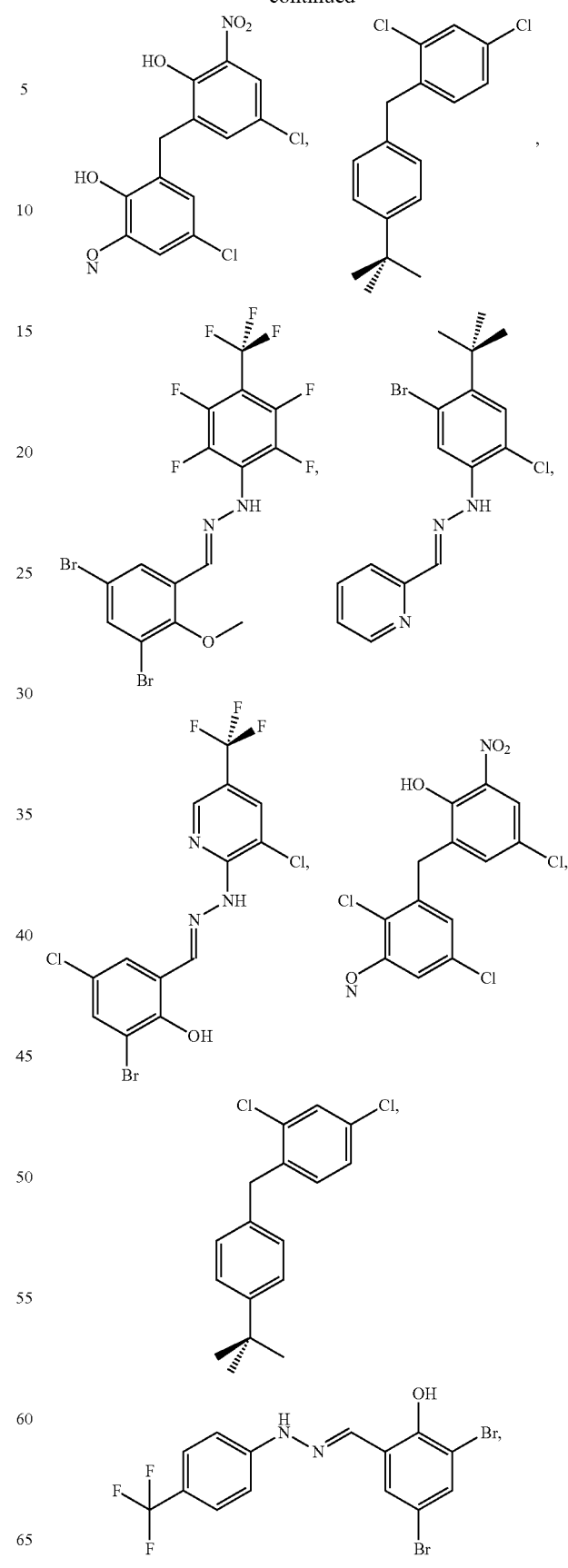

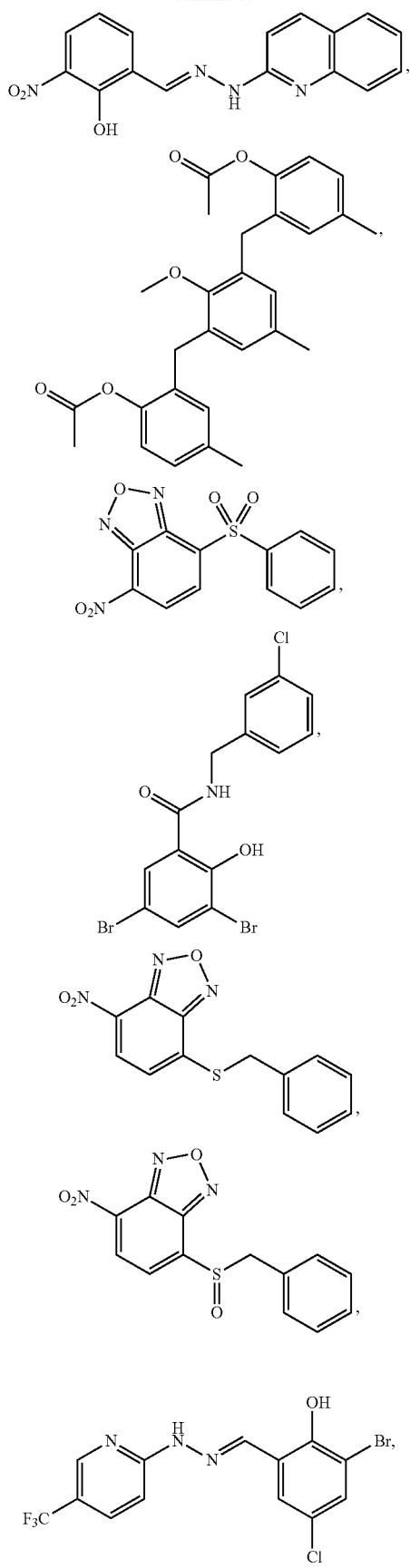
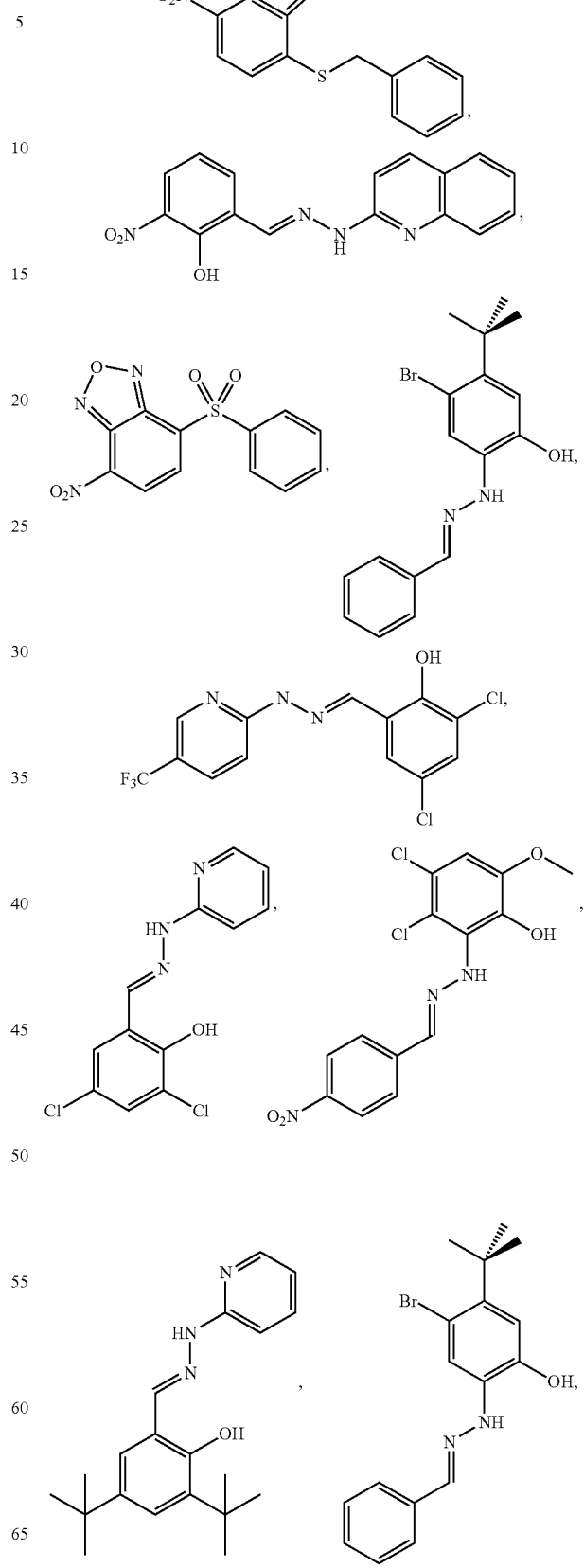

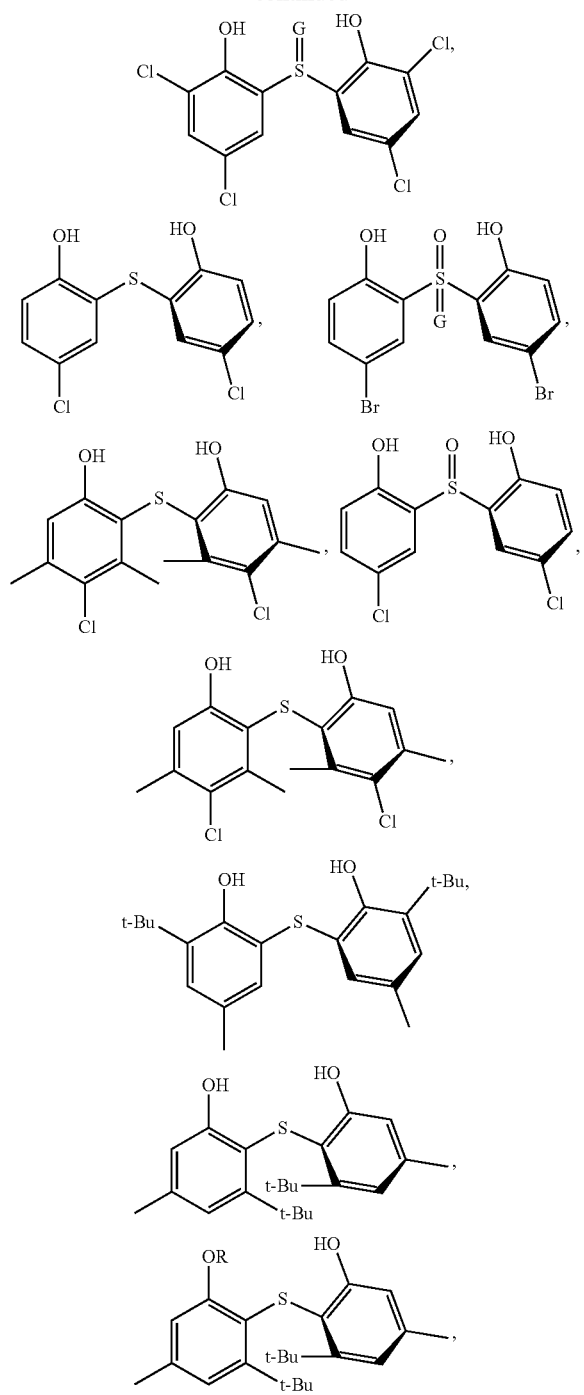
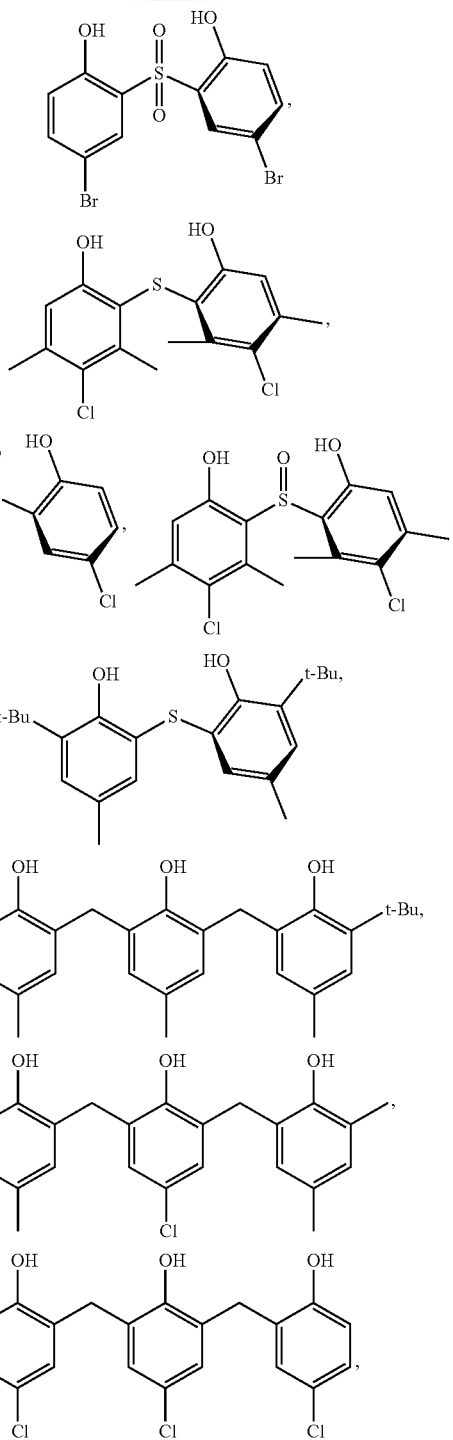
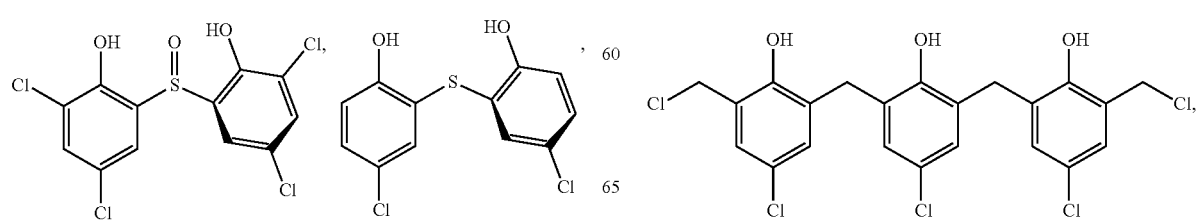

-continued
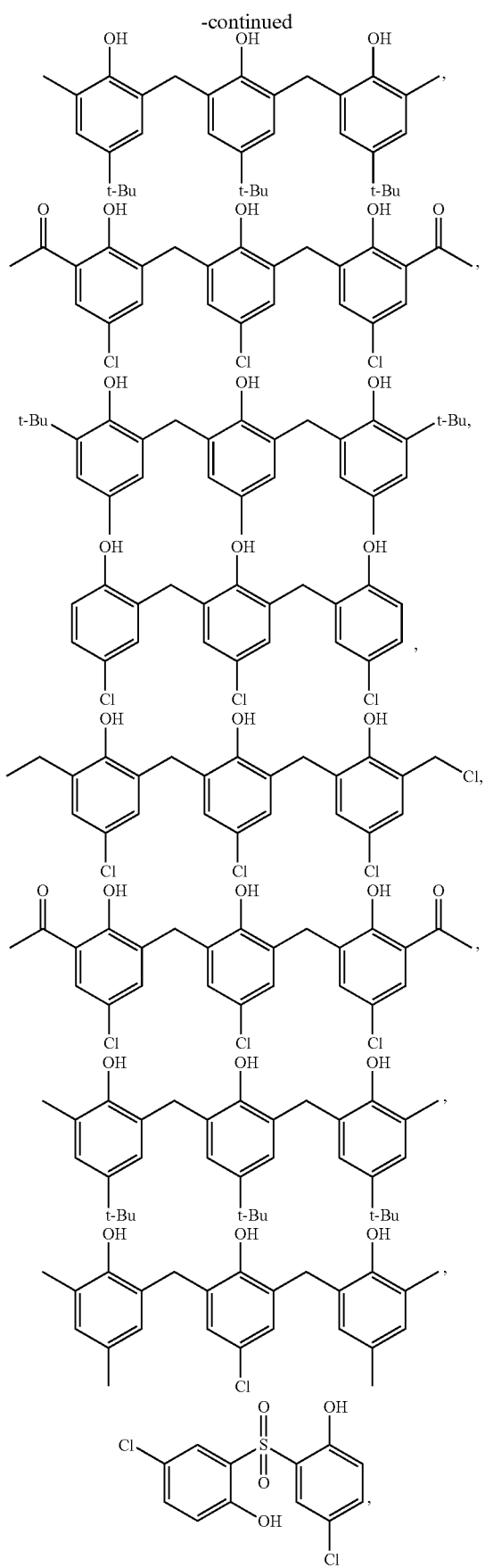
-continued
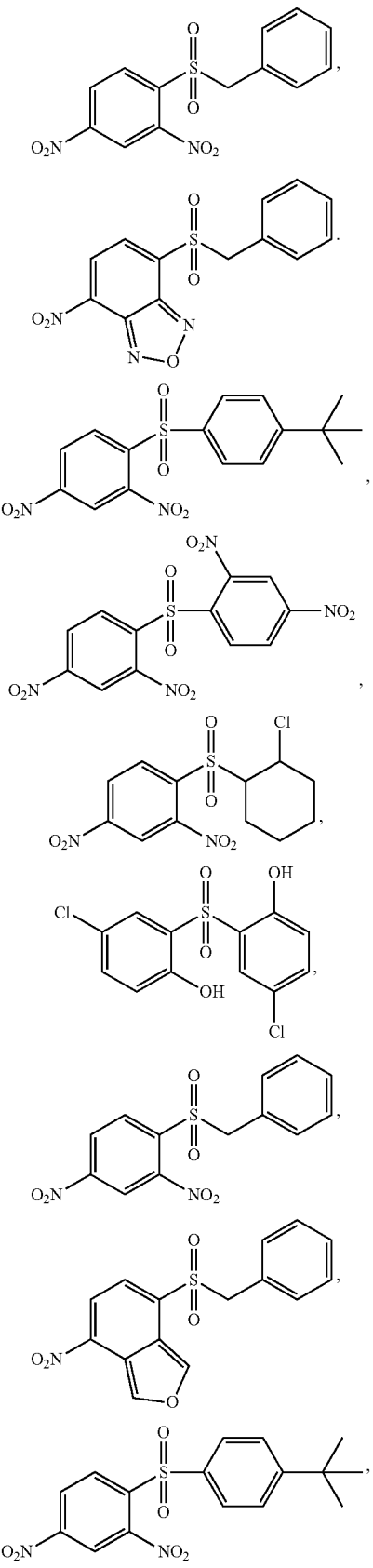

-continued
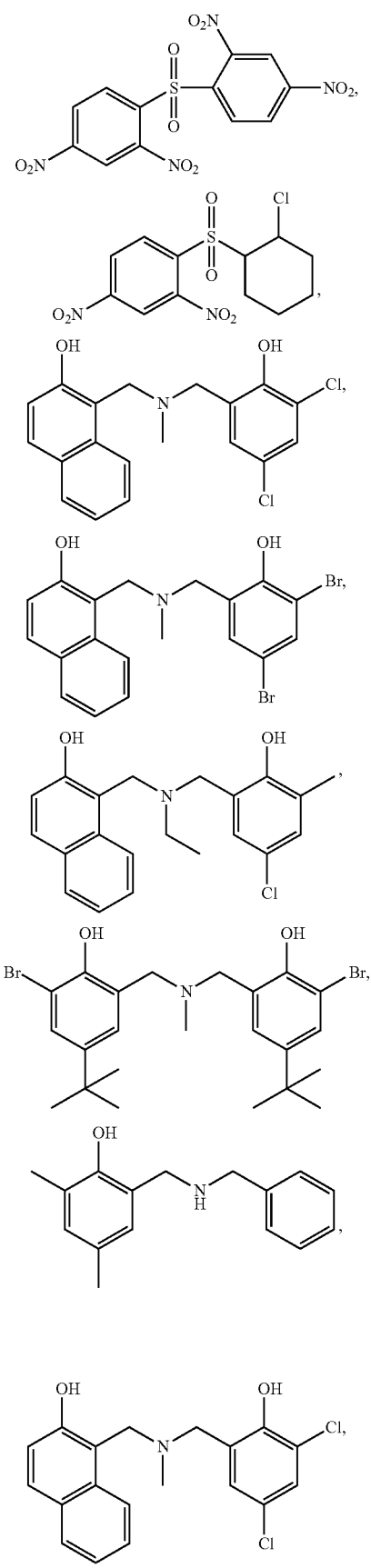
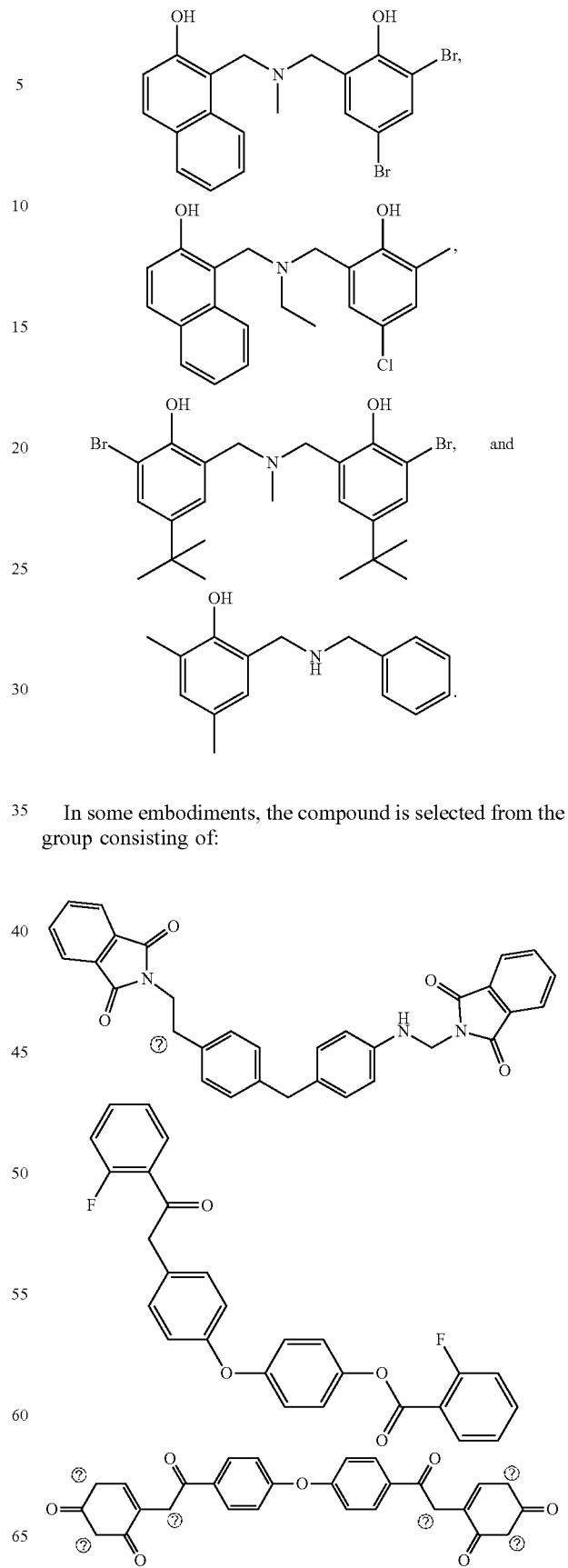
In some embodiments, the compound is selected from the group consisting of:

1667
-continued

1668
-continued

1669
-continued
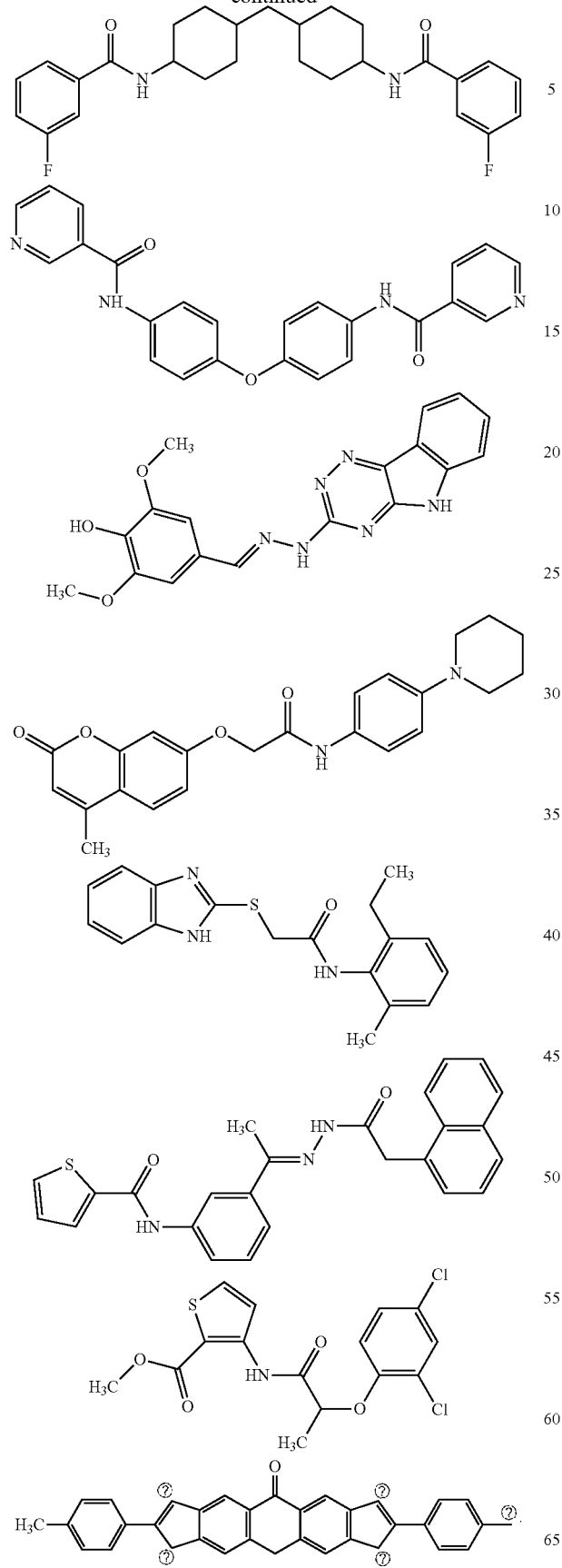
1670
-continued
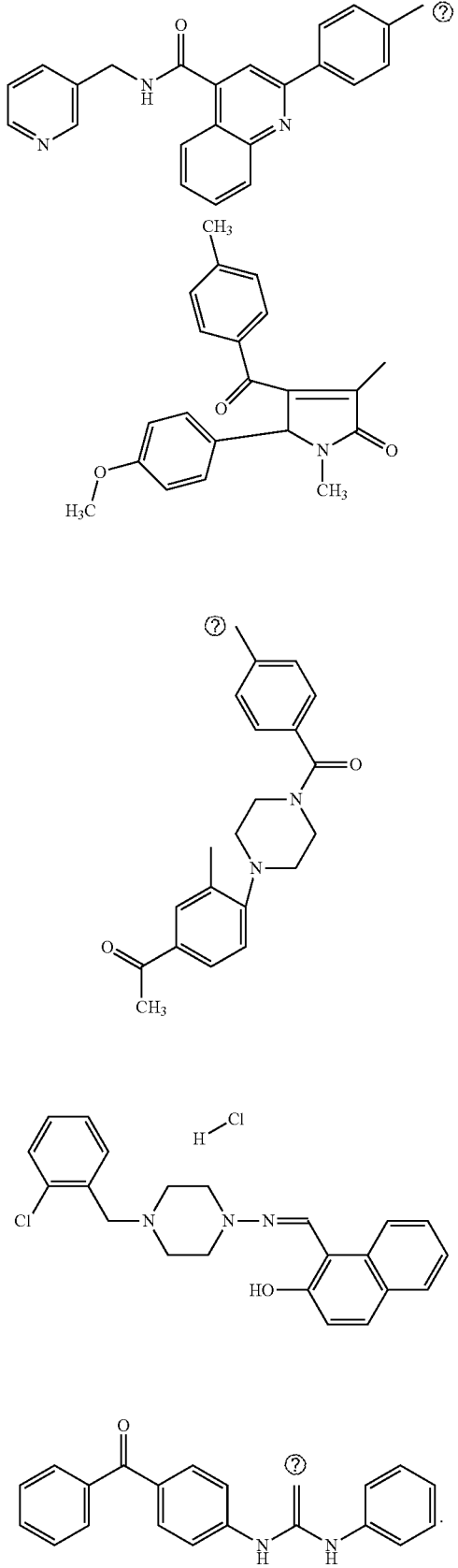

1671
-continued
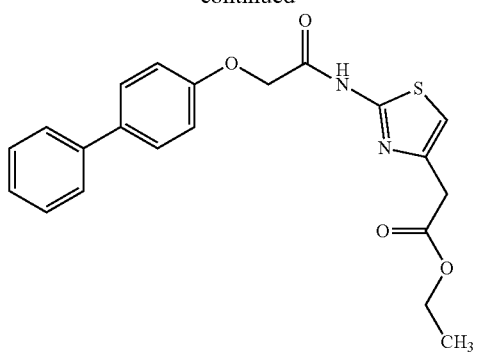
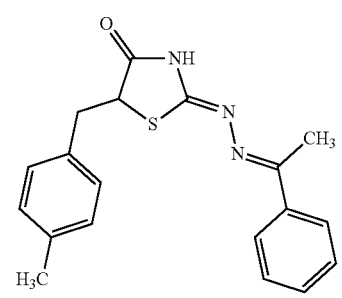
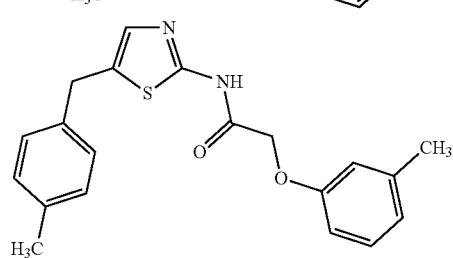
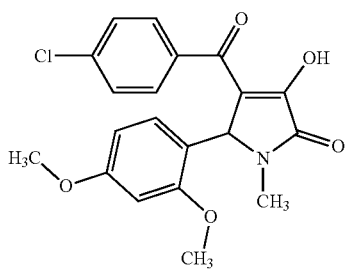
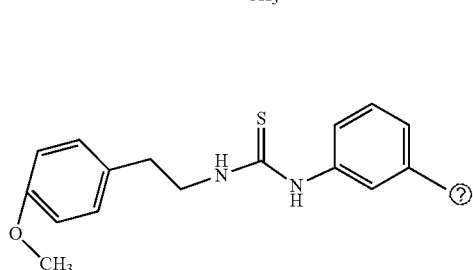
1672
-continued
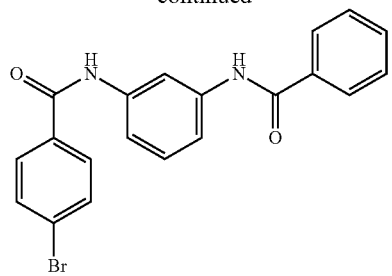
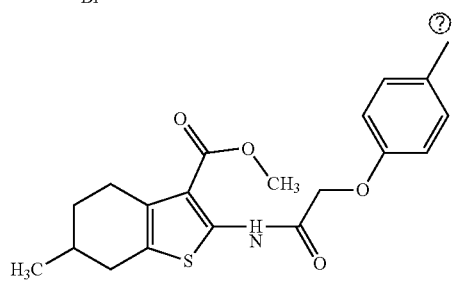
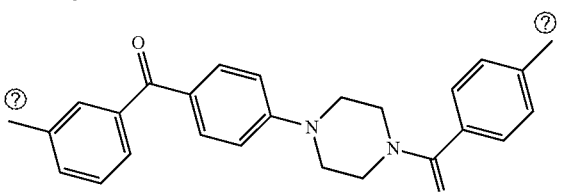
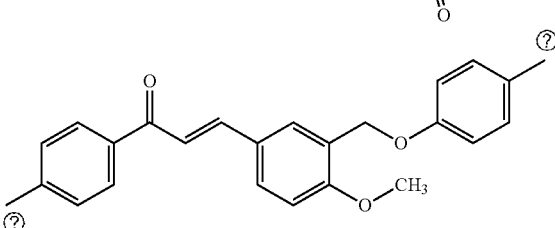
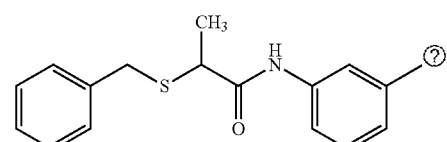
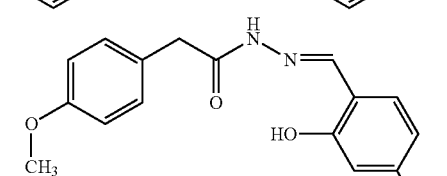
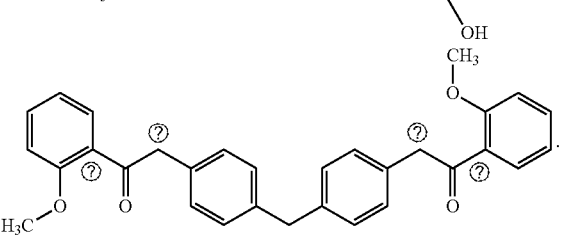
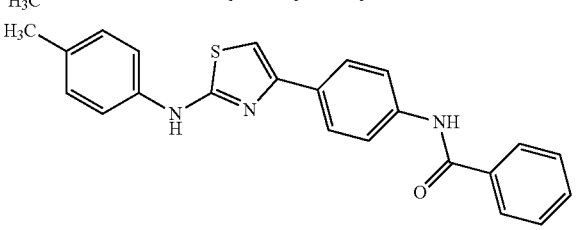

1673
-continued
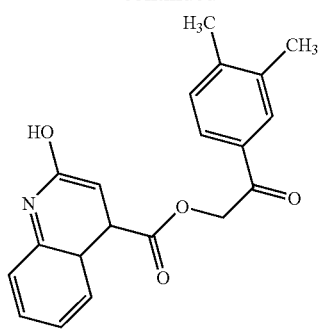
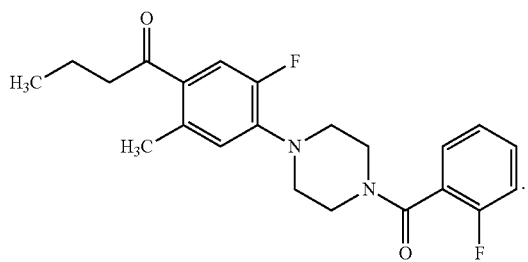
1674
-continued
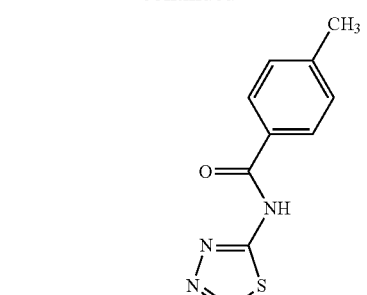
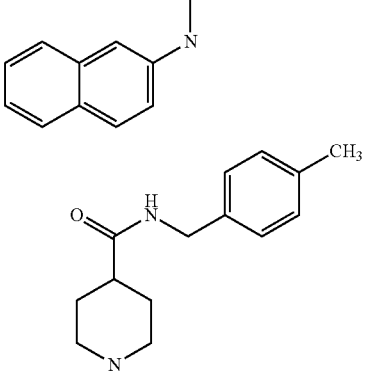
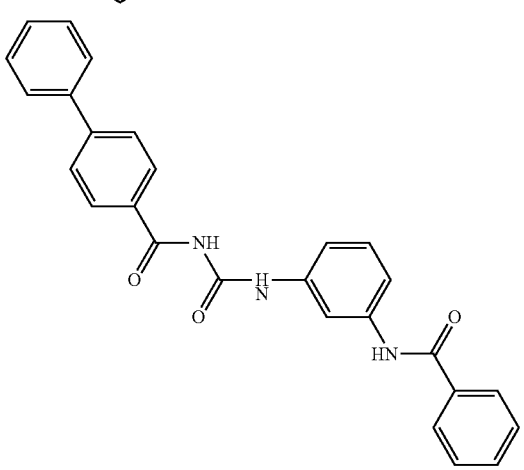
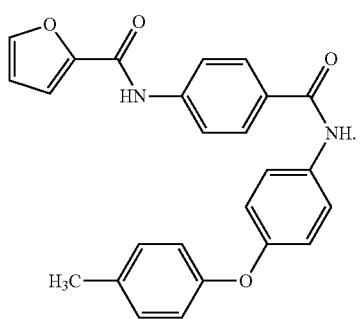

1675
-continued
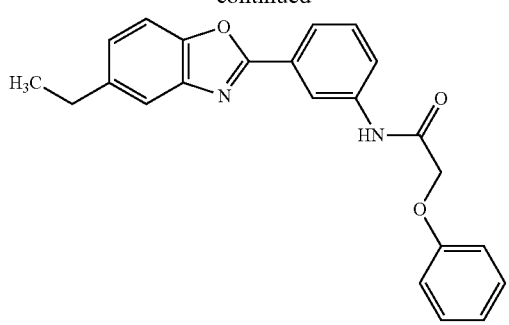
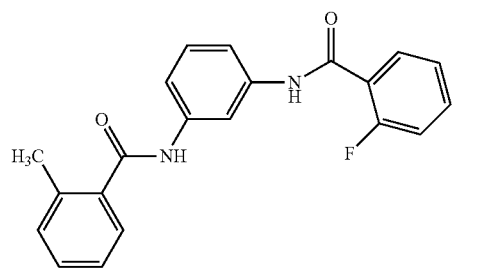
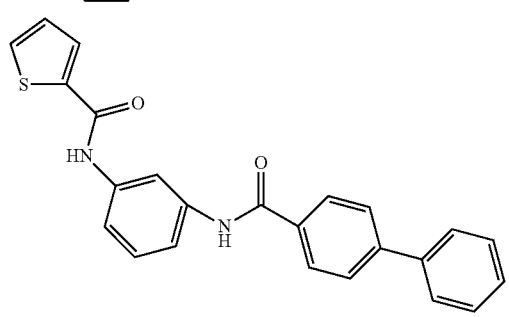
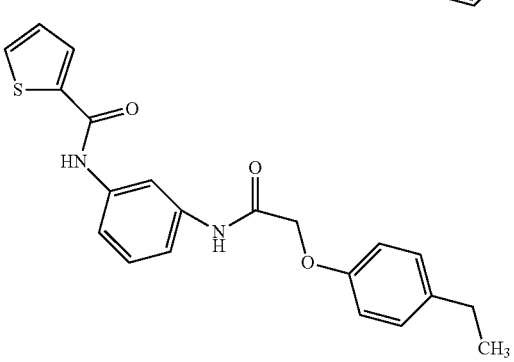
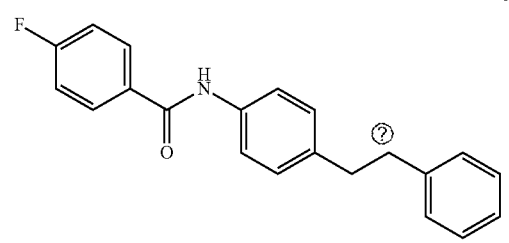
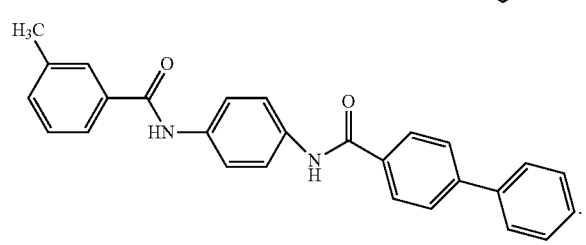
1676
-continued
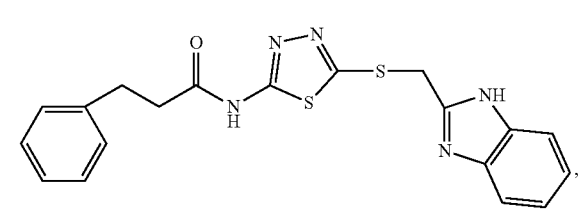

1677
-continued
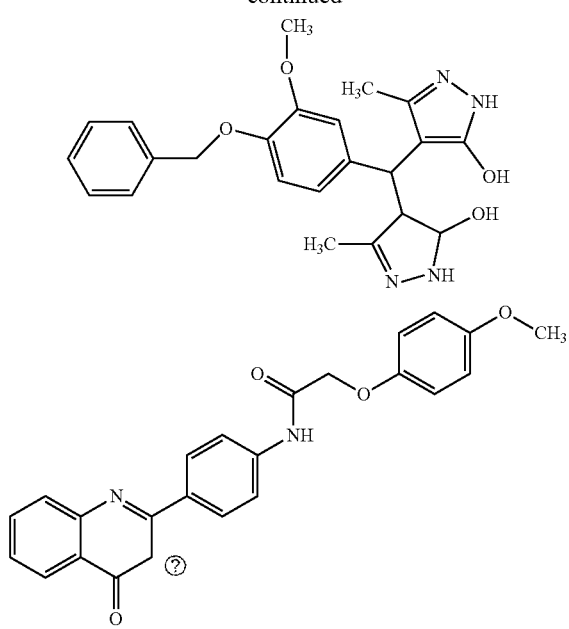
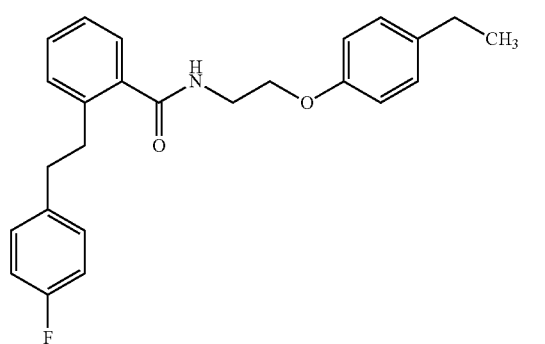
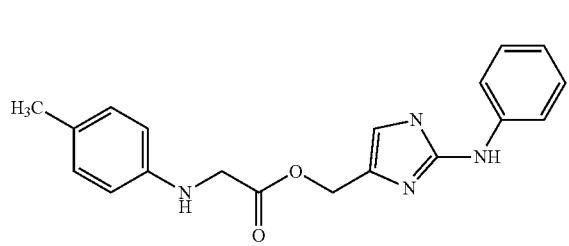
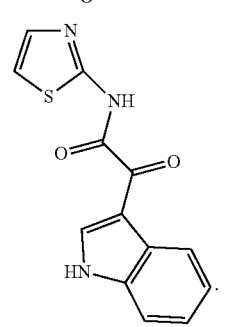
1678
-continued
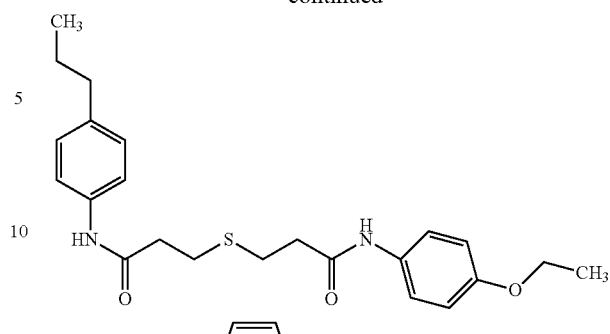
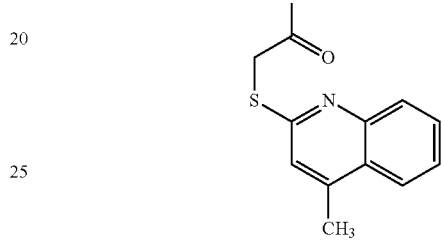
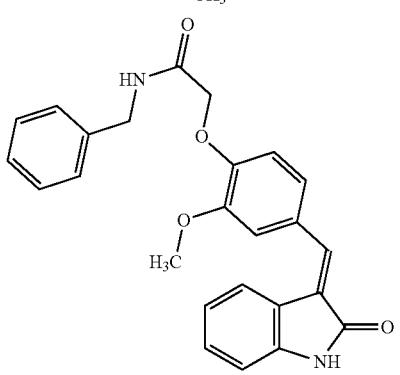
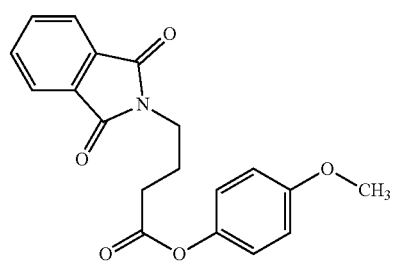
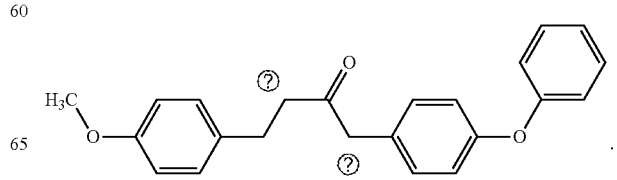

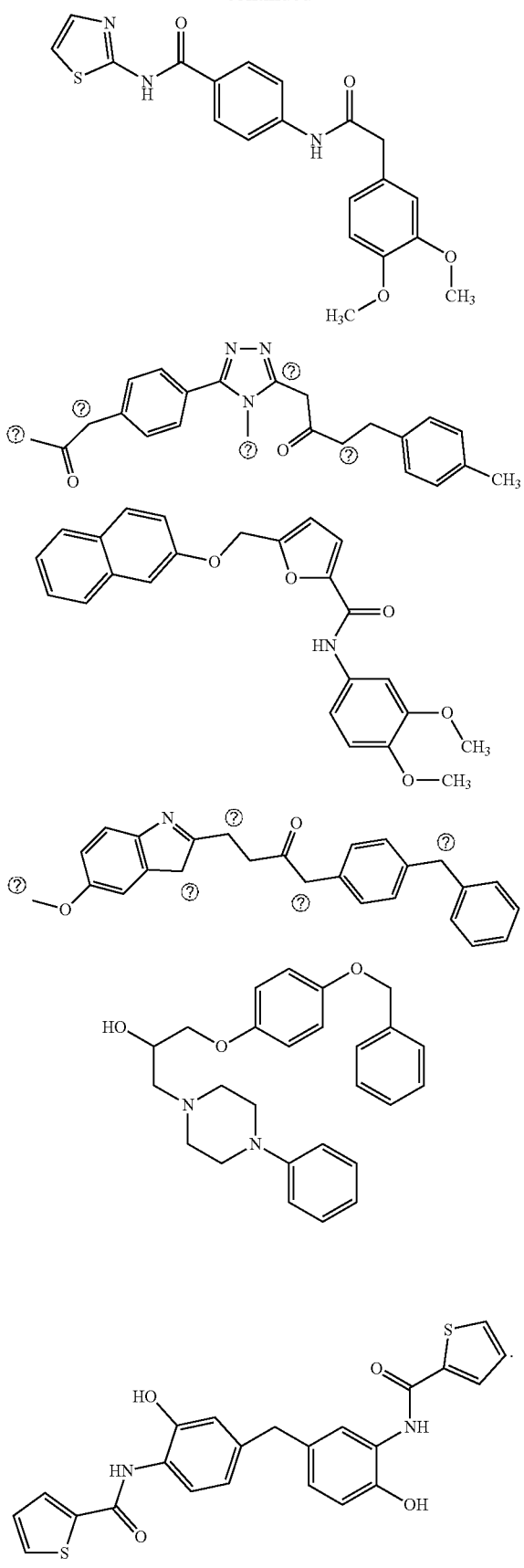

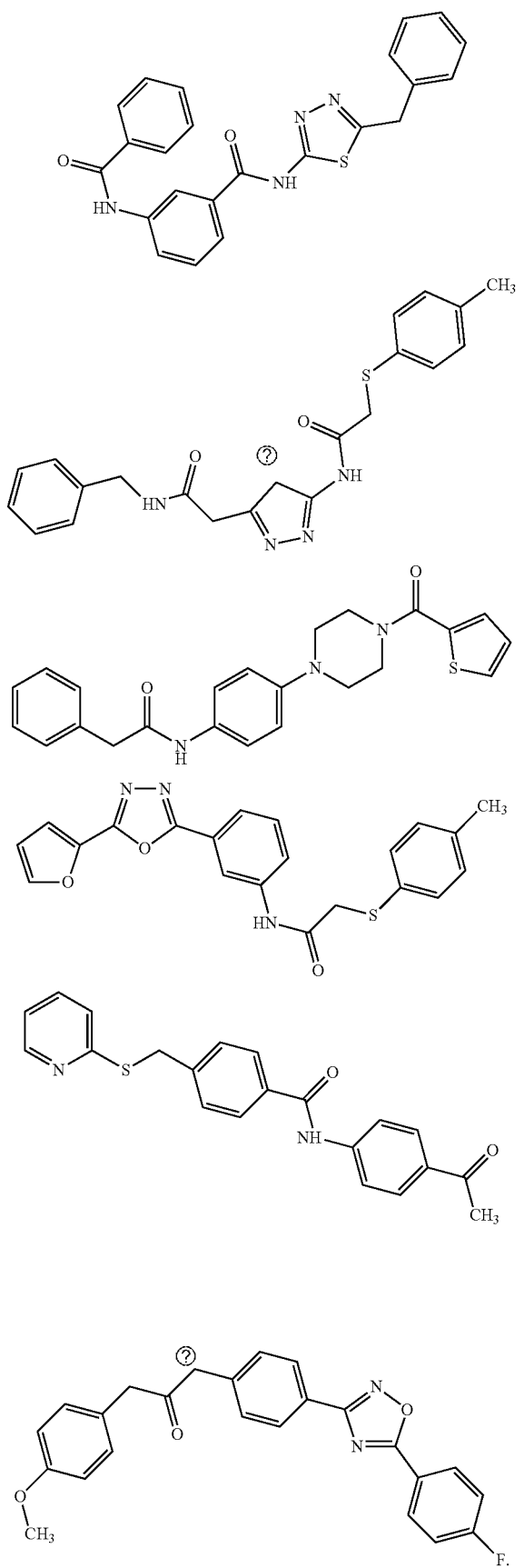
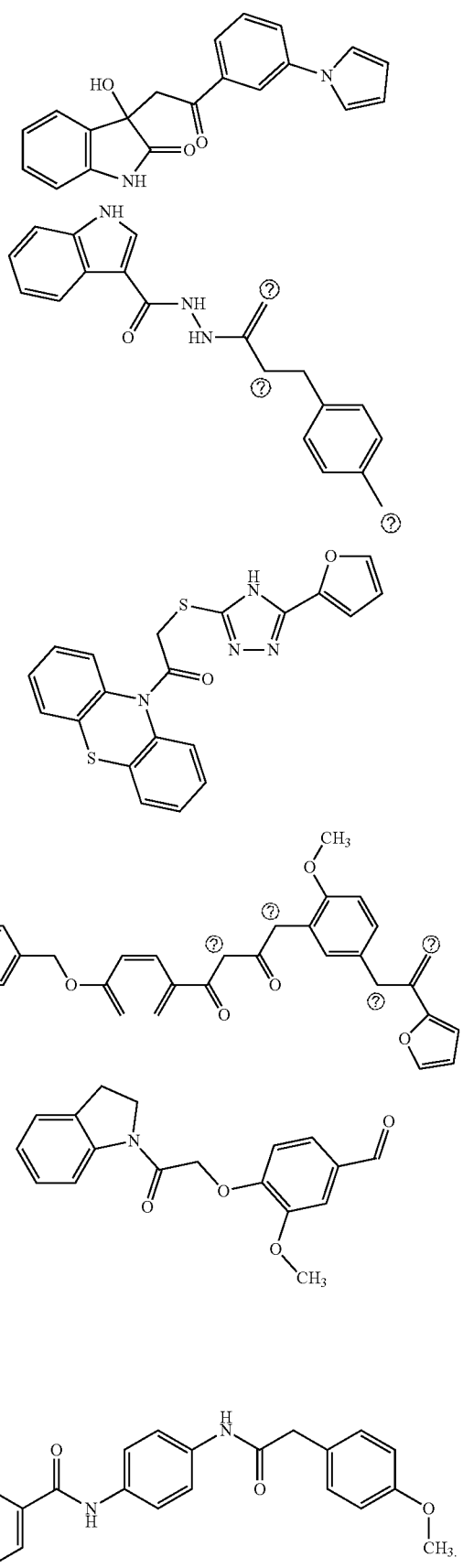

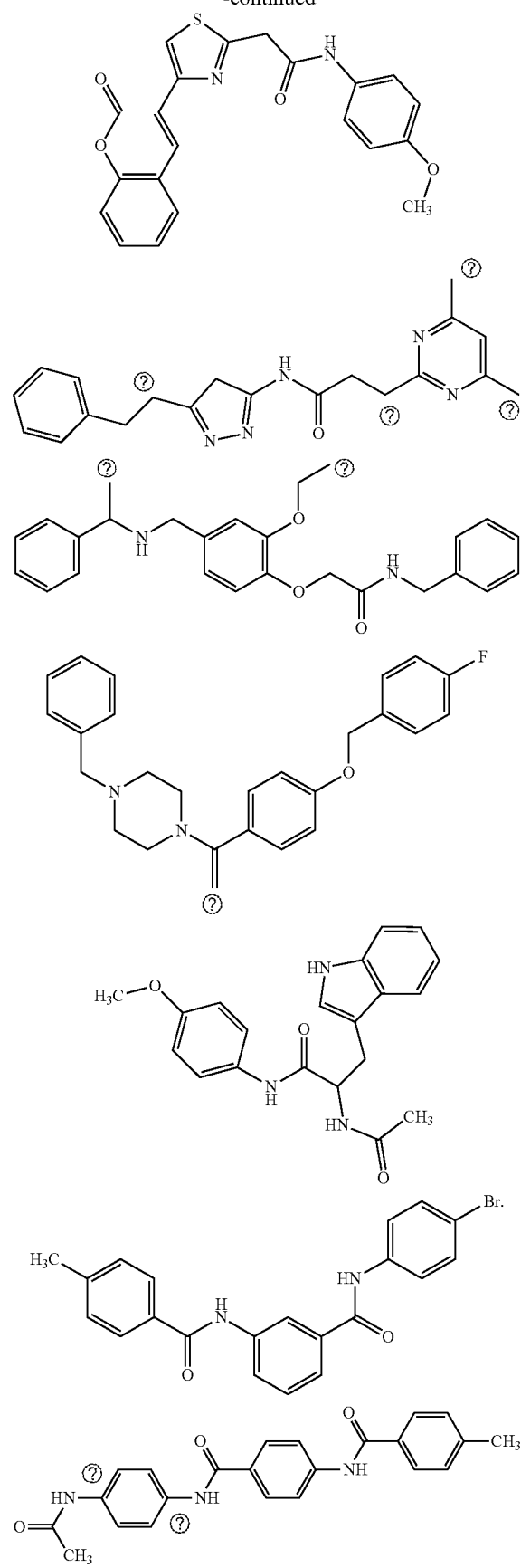

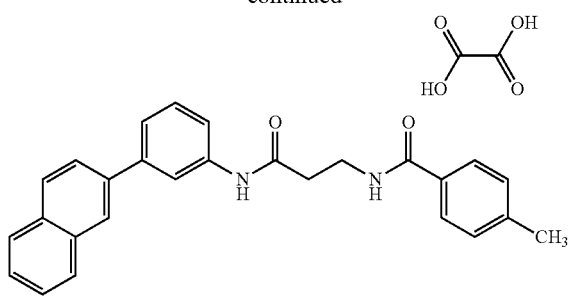
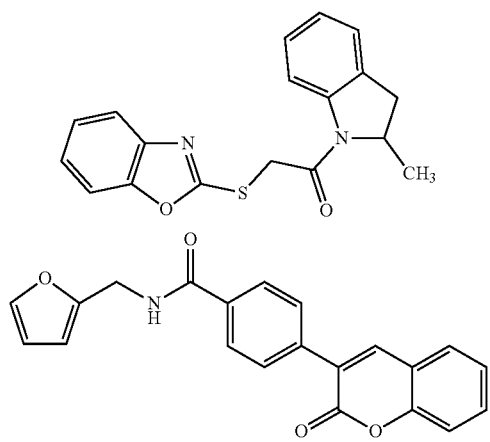
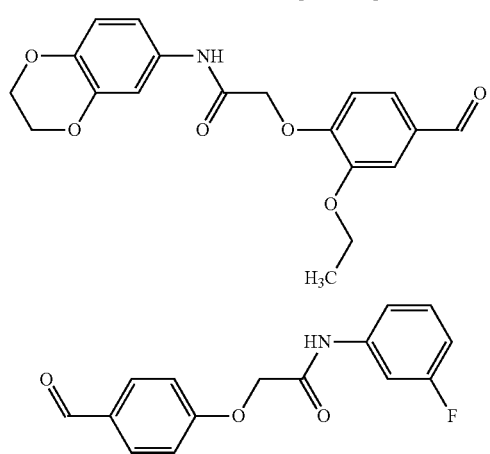
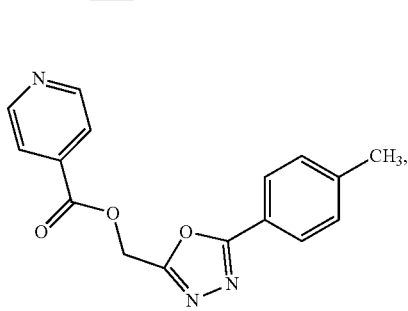
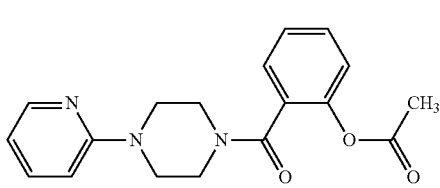

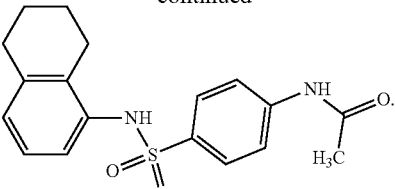

In some embodiments, the compound is selected from the group consisting of:
3-thiomorpholinyl-8-oxo-8H-acenaphtho[1,2-b]pyrrole-9-carbonitrile,
3-(4-aminophenylthio)-8-oxo-8H-acenaphtho[1,2-b]pyrrole-9-carbonitrile,
4-(thienyl-2-methoxyl)-8-oxo-8H-acenaphtho[1,2-b]pyrrole-9-carbonitrile,
4-(thienyl-2-methylamino)-8-oxo-8H-acenaphtho[1,2-b]pyrrole-9-carbonitrile,
3-(4-bromophenylthio)-8-oxo-8H-acenaphtho[1,2-b]pyrrole-9-carbonitrile,
8-oxo-8H-acenaphtho[1,2-b]pyrrole-9-carbonitrile,
3,6-di(4-bromophenylthio)-8-oxo-8H-acenaphtho[1,2-b]pyrrole-9-carbonitrile,
3-(4-aminophenylthio)-8-oxo-8H-acenaphtho[1,2-b]pyrrole-9-carbonitrile,
6-(4-aminophenylthio)-8-oxo-8H-acenaphtho[1,2-b]pyrrole-9-carbonitrile,
3-(p-methylphenoxy)-8-oxo-8H-2-hydroxypropyl-acenaphtho[1,2-b]pyrrole-9-carbonitrile,
3-(4-aminophenylthio)-8-oxo-8H-2-hydroxypropyl-acenaphtho[1,2-b]pyrrole-9-carbonitrile,
3-phenoxy-8-oxo-8H-acenaphtho[1,2-2-hydroxy-propyl-b]pyrrole-9-carboxylate,
3-(4-methoxyphenoxy)-8-oxo-8H-2-hydroxypropyl-acenaphtho[1,2-b]pyrrole-9-carbonitrile,
4-(4-isopropylphenoxy)-8-oxo-8H-2-hydroxypropyl-acenaphtho[1,2-b]pyrrole-9-carbonitrile,
3-(4-bromophenylthio)-8-oxo-8H-2-hydroxypropyl-acenaphtho[1,2-b]pyrrole-9-carbonitrile,
6-(thienyl-2-methoxy)-8-oxo-8H-methyl-acenaphtho[1,2-b]pyrrole-9-carbonitrile,
6-(tetrahydro-2H-pyranyl-4-oxy)-8-methyl-oxo-8H-acenaphtho[1,2-b]pyrrole-9-carbonitrile,
6-(thienyl-2-methylamino)-8-oxo-8H-methyl-acenaphtho[1,2-b]pyrrole-9-carbonitrile,
3-(4-bromophenylthio)-8-oxo-8H-methyl-acenaphtho[1,2-b]pyrrole-9-carbonitrile,
3-(4-aminophenylthio)-8-oxo-8H-methyl-acenaphtho[1,2-b]pyrrole-9-carbonitrile,
6-(4-aminophenylthio)-8-oxo-8H-methyl-acenaphtho[1,2-b]pyrrole-9-carbonitrile,
3-(4-bromophenylthio)-8-oxo-8H-hydroxypropyl-acenaphtho[1,2-b]pyrrole-9-carbonitrile,
3-phenylthio-8-oxo-8H-acenaphtho[1,hydroxypropyl-2-b]pyrrole-9-carbonitrile,
3-(4-bromophenylthio)-8-oxo-8H-hydroxypropyl-acenaphtho[1,2-b]pyrrole-9-carbonitrile,
3-(4-bromophenylthio)-8-oxo-8H-hydroxypropyl-acenaphtho[1,2-b]pyrrole-9-carbonitrile,
3-(4-aminophenylthio)-8-oxo-8H-hydroxypropyl-acenaphtho[1,2-b]pyrrole-9-carbonitrile,
6-(4-aminophenylthio)-8-oxo-8H-hydroxypropyl-acenaphtho[1,2-b]pyrrole-9-carbonitrile, 3-(p-methylphenoxy)-8-oxo-8H-acenaphtho[1,2-b]pyrrole-9-carboxamide,
3-(4-bromophenylthio)-8-oxo-8H-acenaphtho[1,2-b]pyrrole-9-carboxylicacid,
3-thiomorpholinyl-8-oxo-8H-acenaphtho[1,2-b]pyrrole-9-carboxamide,
3-(p-methylphenoxy)-8-oxo-8H-2-hydroxypropyl-acenaphtho[1,2-b]pyrrole-9-carboxamide,
3-(4-bromophenylthio)-8-oxo-8H-methyl-acenaphtho[1,2-b]pyrrole-9-carboxylicacid,
3-thiomorpholinyl-8-oxo-8H-hydroxypropyl-acenaphtho[1,2-b]pyrrole-9-carboxamide,
8-oxo-8H-acenaphtho[1,2-b]pyrrole-9-carbonitrile,
3-(4-bromophenylthio)-8-oxo-8H-acenaphtho[1,2-b]pyrrole-9-carbonitrile,
6-(4-aminophenylthio)-8-oxo-8H-acenaphtho[1,2-b]pyrrole-9-carbonitrile,
3,6-di(4-bromophenylthio)-8-oxo-8H-acenaphtho[1,2-b]pyrrole-9-carbonitrile,
3,6-di(4-aminophenylthio)-8-oxo-8H-acenaphtho[1,2-b]pyrrole-9-carbonitrile,
3-(tetrahydro-2H-pyranyl-4-oxy)-8-oxo-8H-acenaphtho[1,2-b]pyrrole-9-carbonitrile,
4-phenoxy-8-oxo-8H-acenaphtho[1,2-b]pyrrole-9-carbonitrile,
6-(thienyl-2-methoxy)-8-oxo-8H-acenaphtho[1,2-b]pyrrole-9-carbonitrile,
3-phenoxy-8-oxo-8H-acenaphtho[1,2-b]pyrrole-9-carboxylate.

In some embodiments, the compound is selected from the group consisting of:

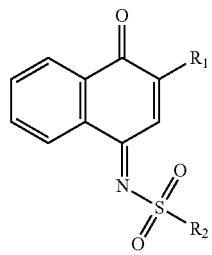

| R₁ | R₂ |
|---|---|
| 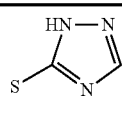 | 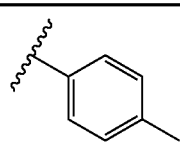 |
| 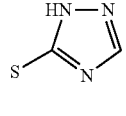 | 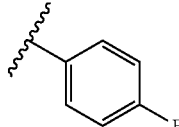 |
| CL | 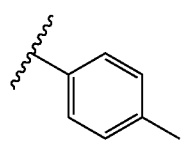 |
| S—CN | 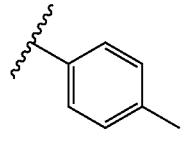 |

-continued

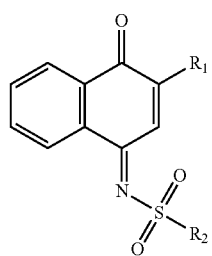

| R₁ | R₂ |
|---|---|
| 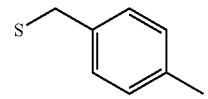 | 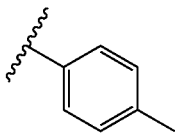 [SMILES: *c1ccc(C)cc1] |
| H | 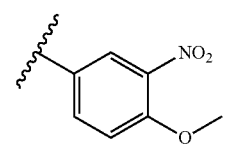 [SMILES: *c1ccc(OC)c([N+](=O)[O-])c1] |
| H | 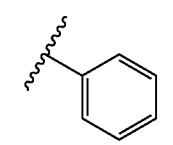 [SMILES: *c1ccccc1] |
| H | 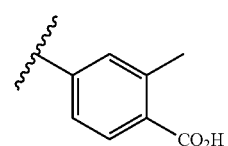 |
| H |  |
| H | 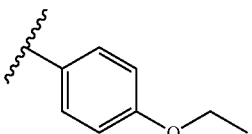 |
| H | 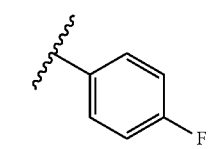 [SMILES: *c1ccc(F)cc1] |

1689
-continued
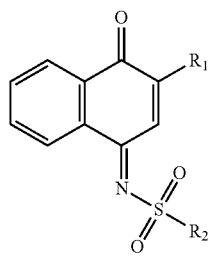
| R₁ | R₂ |
|---|---|
| H | 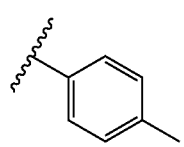 |
1690
-continued
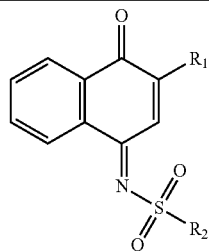
| R₁ | R₂ |
|---|---|
| 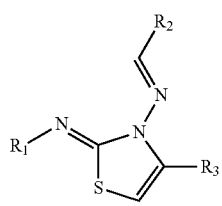 | |
In some embodiments, the compound is selected from the group consisting of:
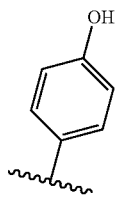 [SMILES: *c1ccc(O)cc1]
| R₁ | R₂ | R₃ |
|---|---|---|
| CH₃ | 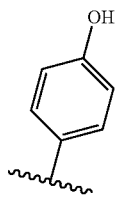 [SMILES: *c1ccc(O)cc1] | CH₃ |
| CH₃ | 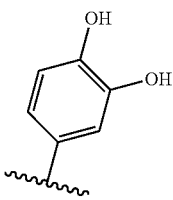 [SMILES: *c1ccc(O)c(O)c1] | CH₃ |
| CH₃ | 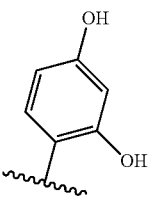 [SMILES: *c1ccc(O)cc1O] | CH₃ |

-continued
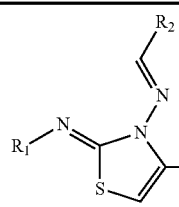
| R₁ | R₂ | R₃ |
|---|---|---|
| CH₃ | 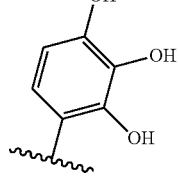 | CH₃ |
| CH₂CH₃ | 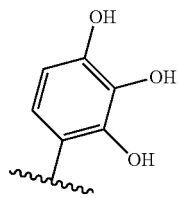 [SMILES: *c1ccc(O)c(O)c1O] | CH₃ |
| CH₃ | 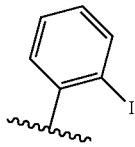 [SMILES: *c1ccccc1I] | CH₃ |
| CH₃ | 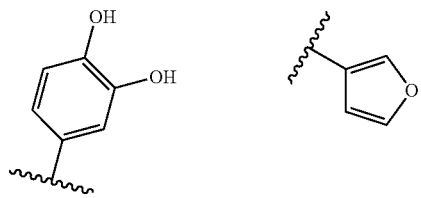 | |
| 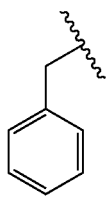 | 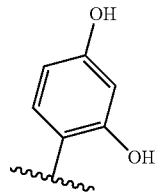 [SMILES: *c1ccc(O)cc1O] | |
| CH₃ | 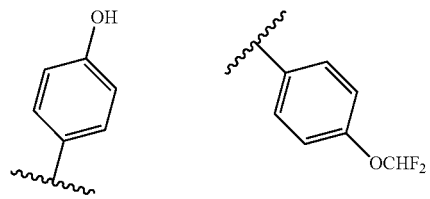 | |
| 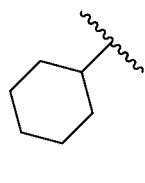 [SMILES: *C1CCCCC1] | 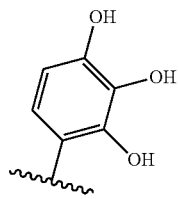 [SMILES: *c1ccc(O)c(O)c1O] | CH₃ |

-continued
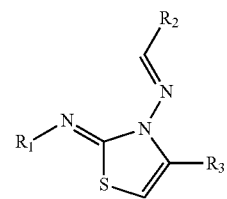
| R₁ | R₂ | R₃ |
|---|---|---|
| iPr | 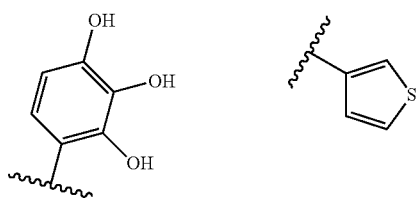 | 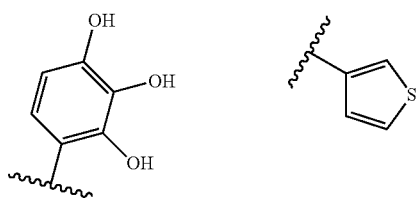 |
| CH₃ | 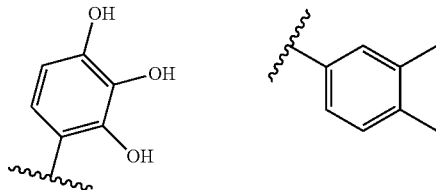 | 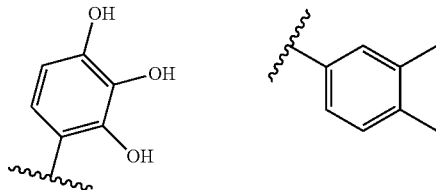 |
| CH₃ | 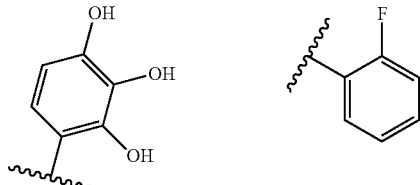 | 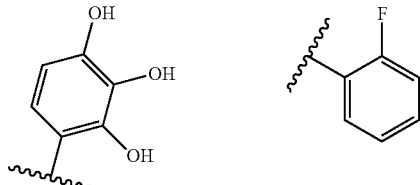 |
| CH₃ | 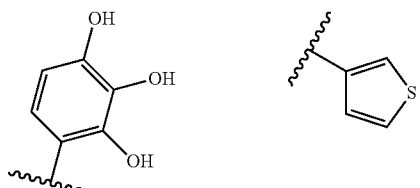 | 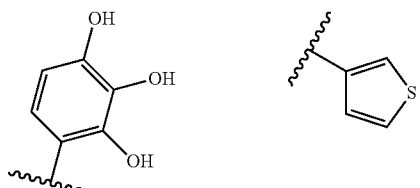 |
| CH₃ | 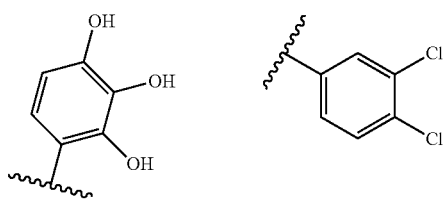 | 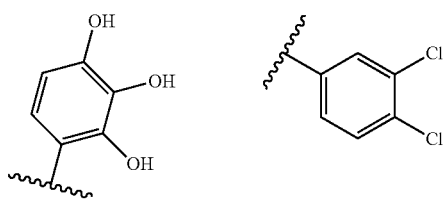 |
| nPr | 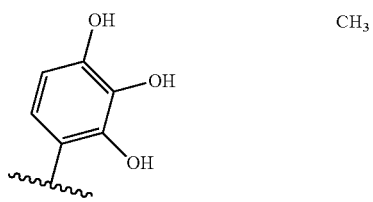 | CH₃ |

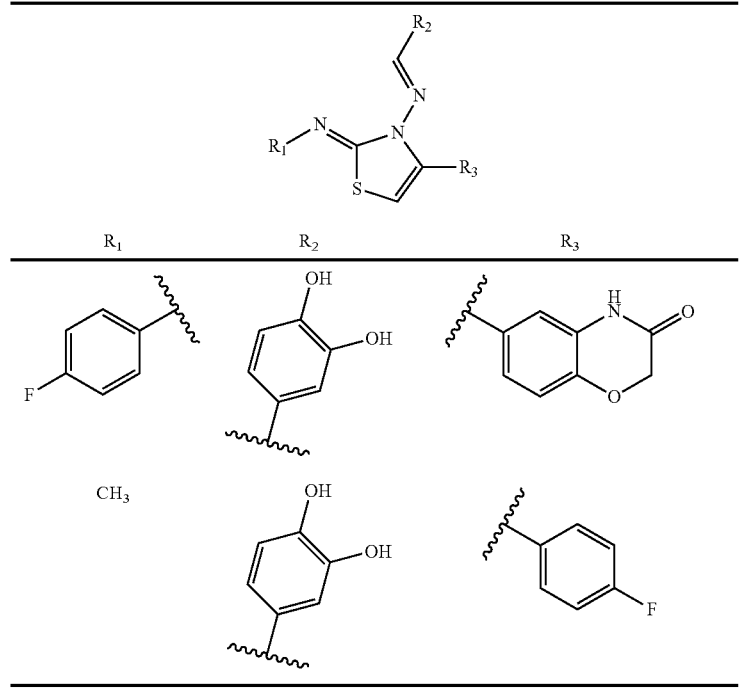
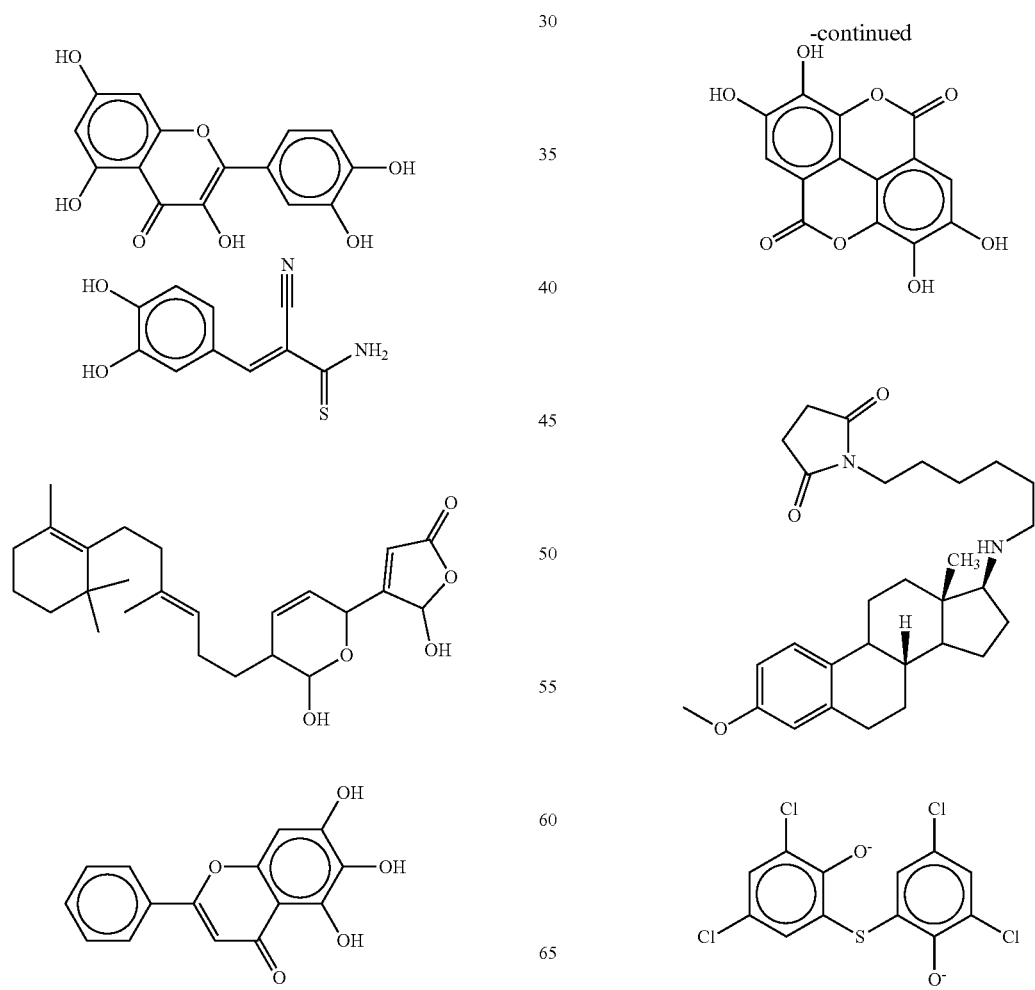

1697
-continued
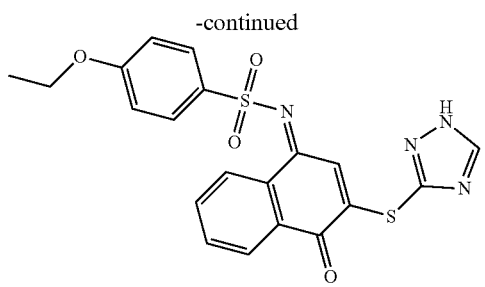
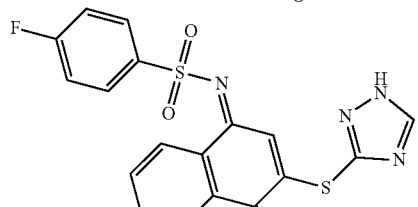
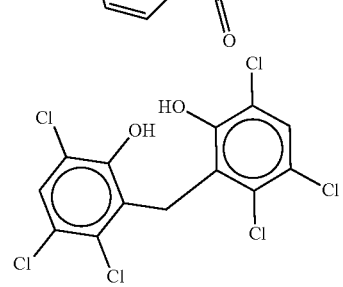
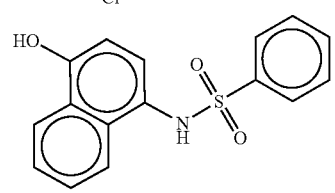
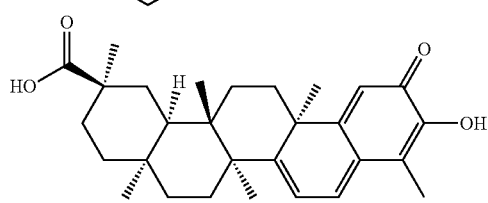
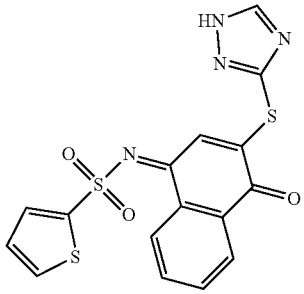
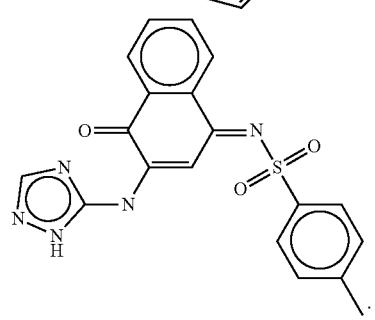
1698
-continued
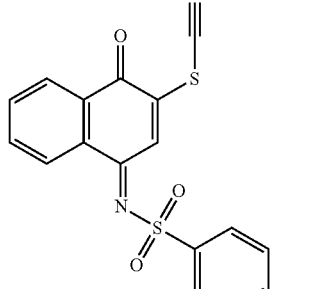
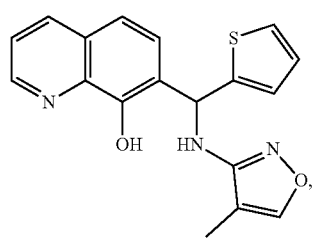
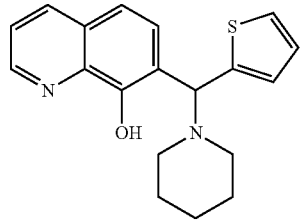
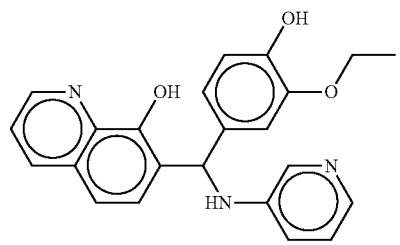
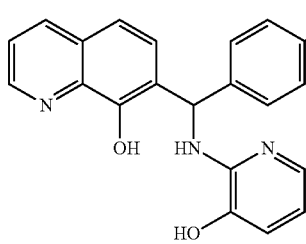
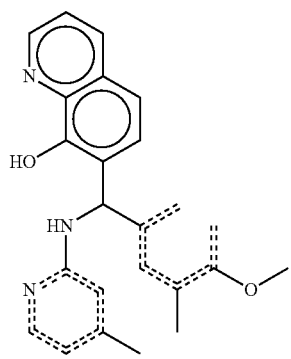

1699
-continued
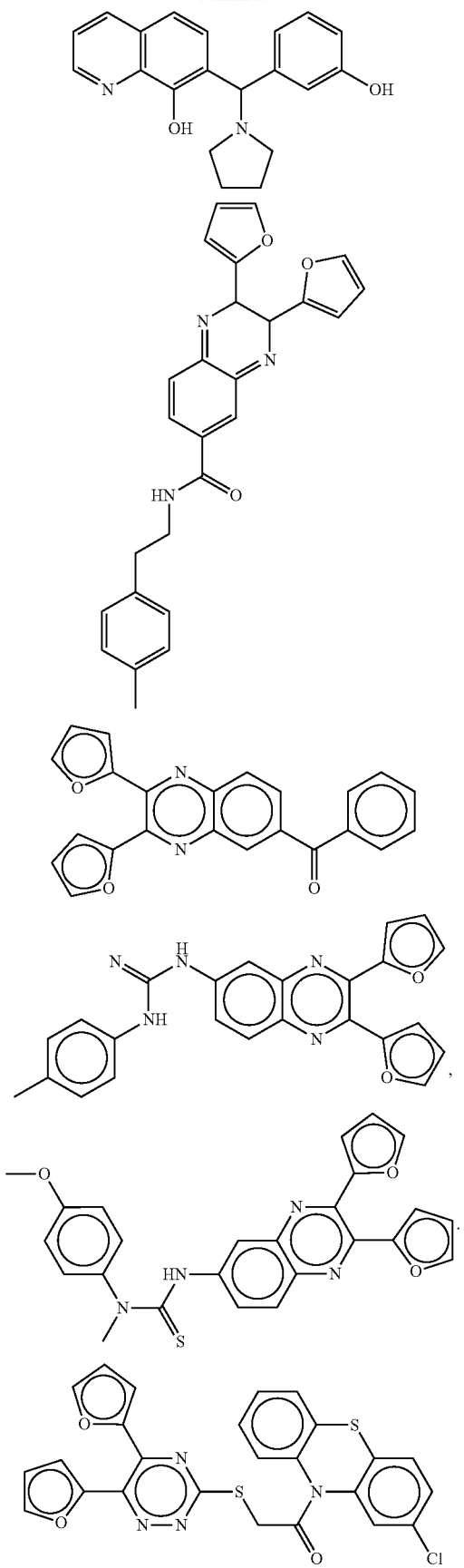
1700
-continued
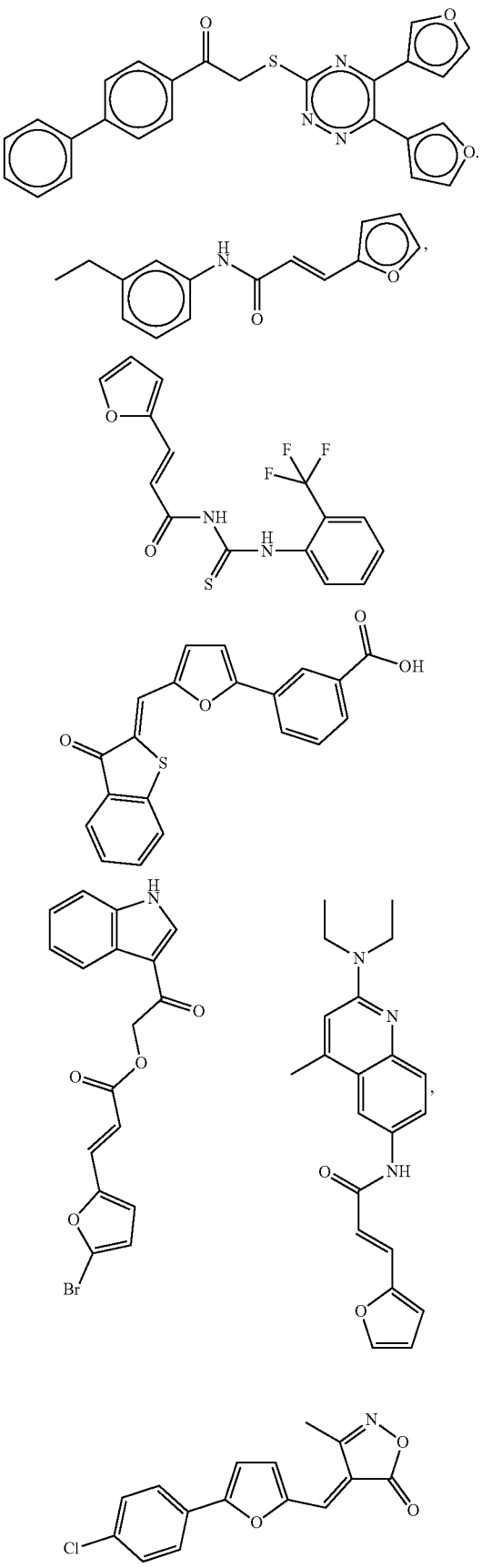

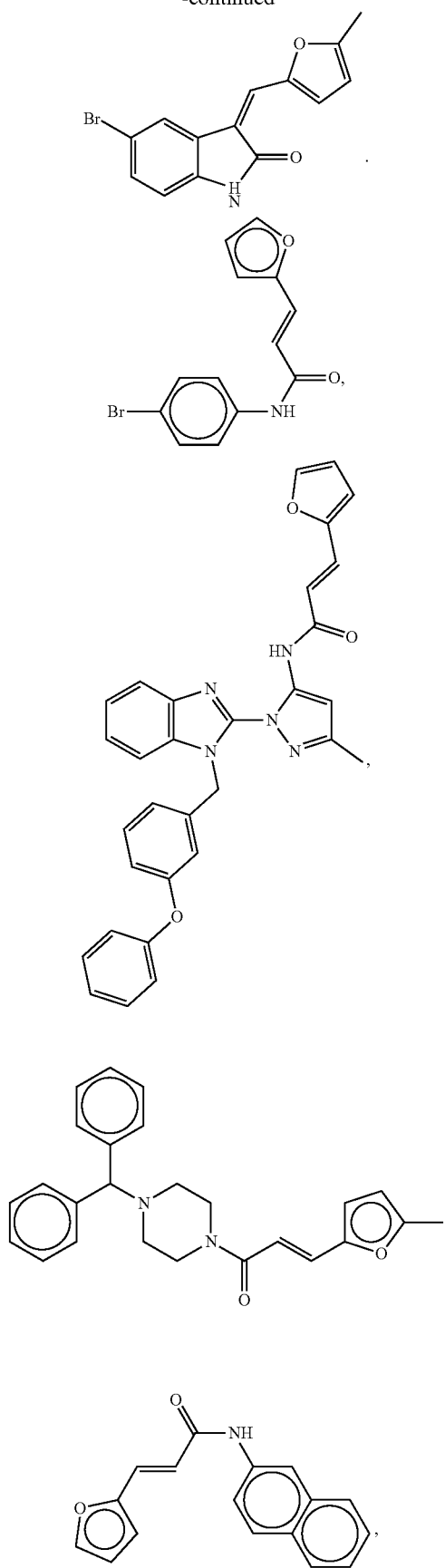
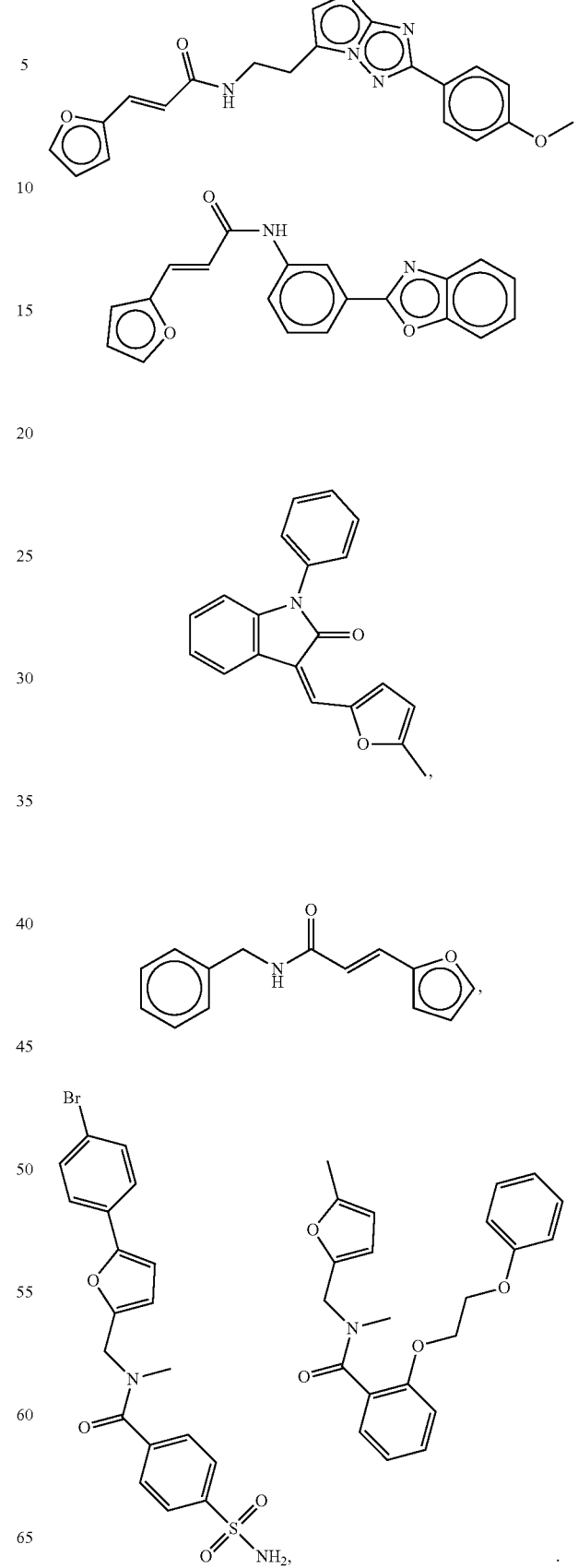

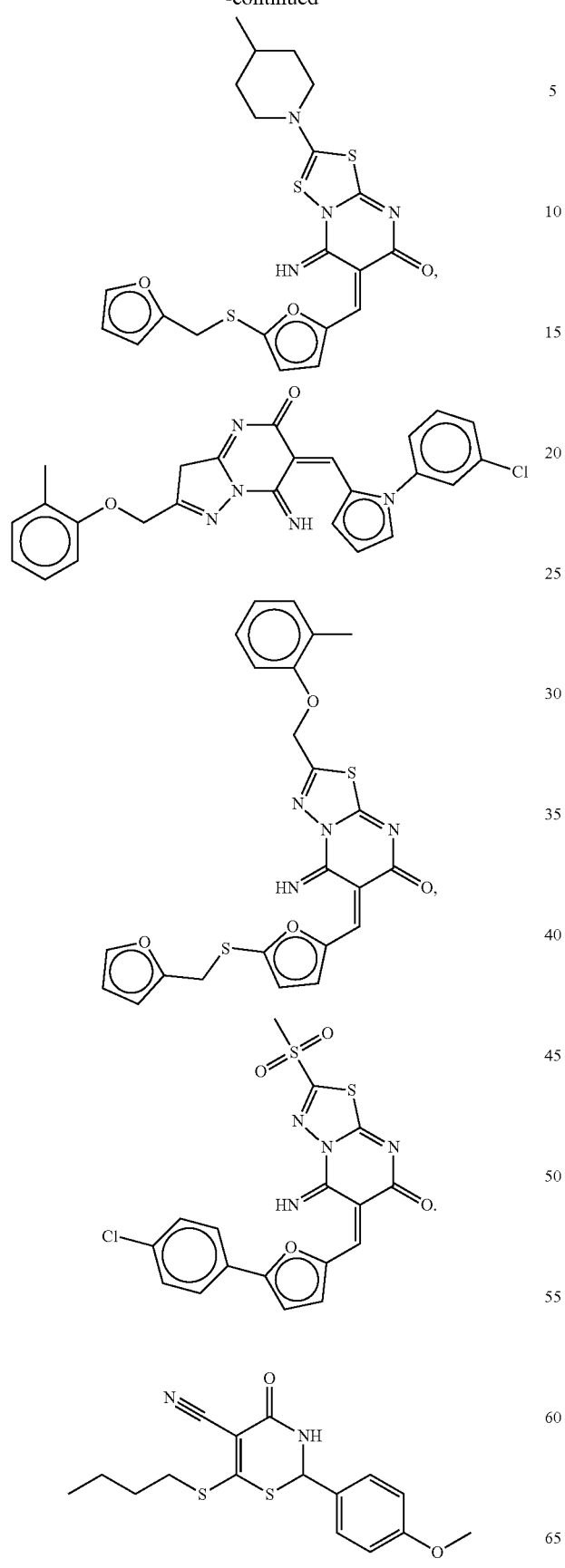
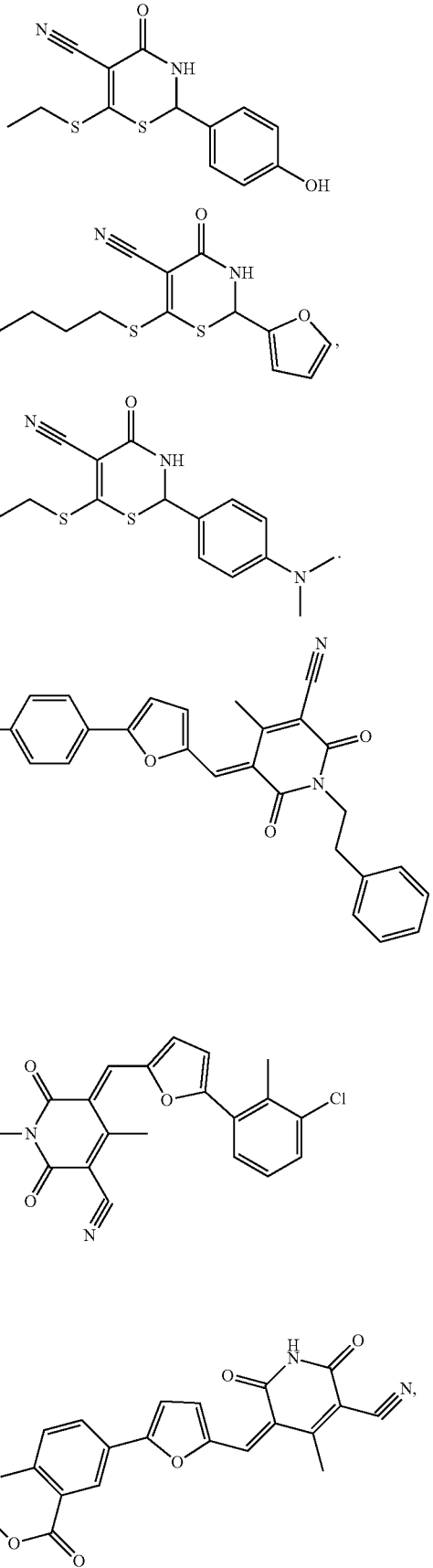

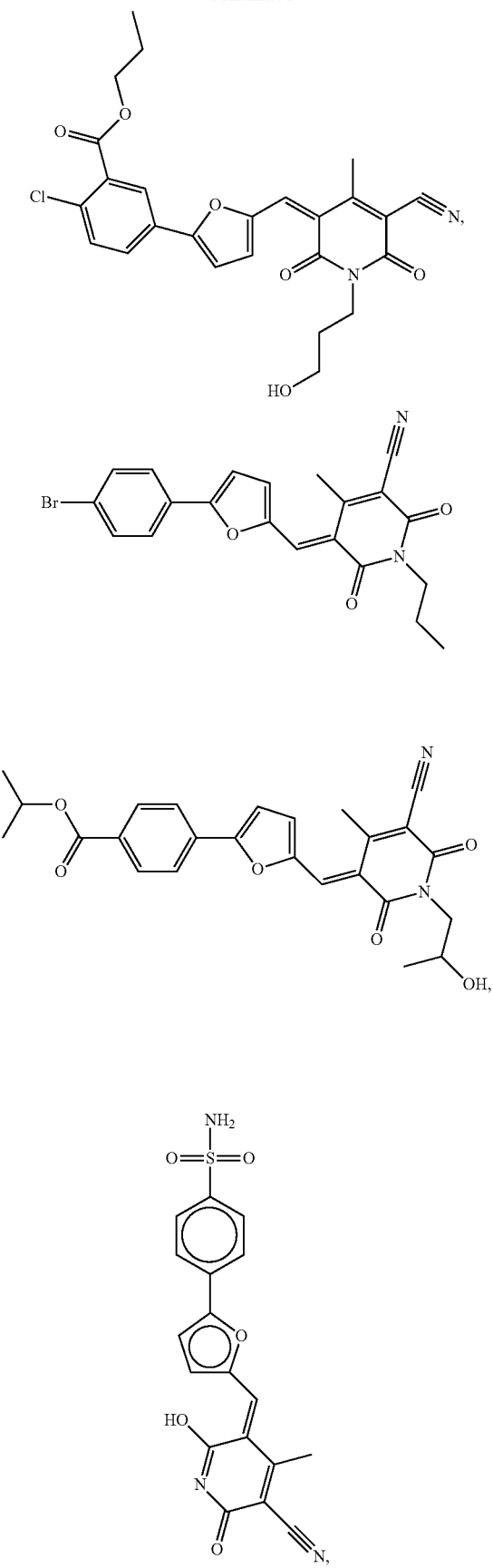
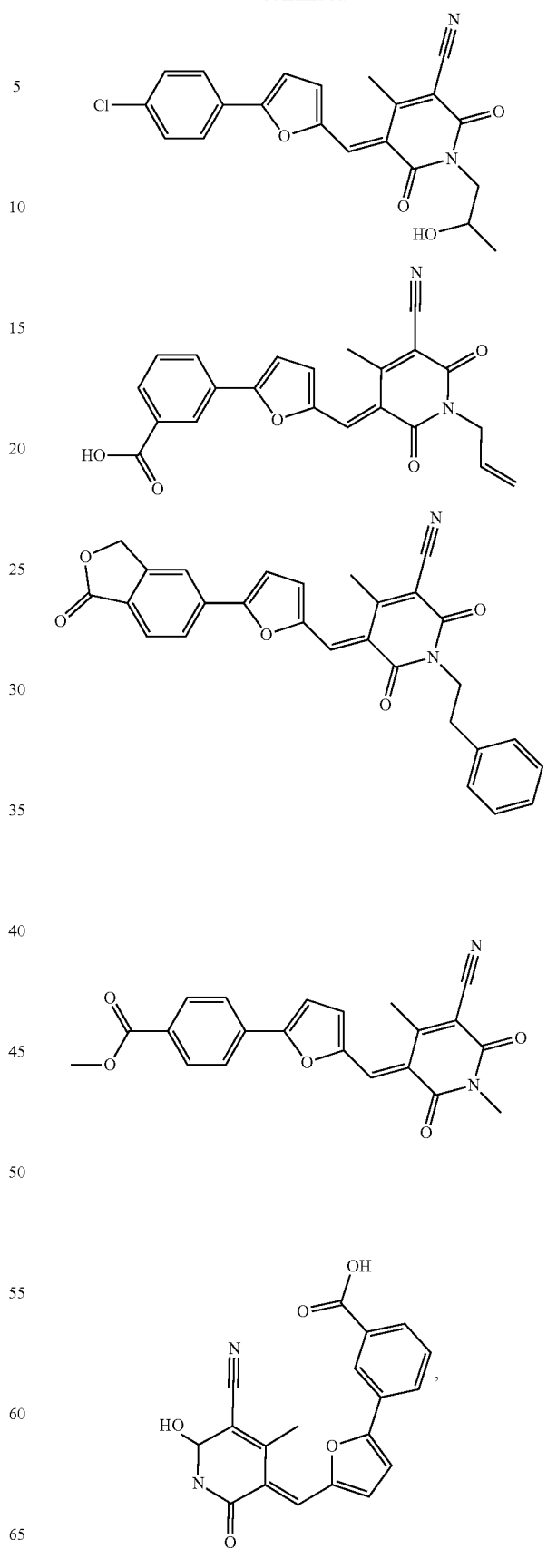

1707
-continued
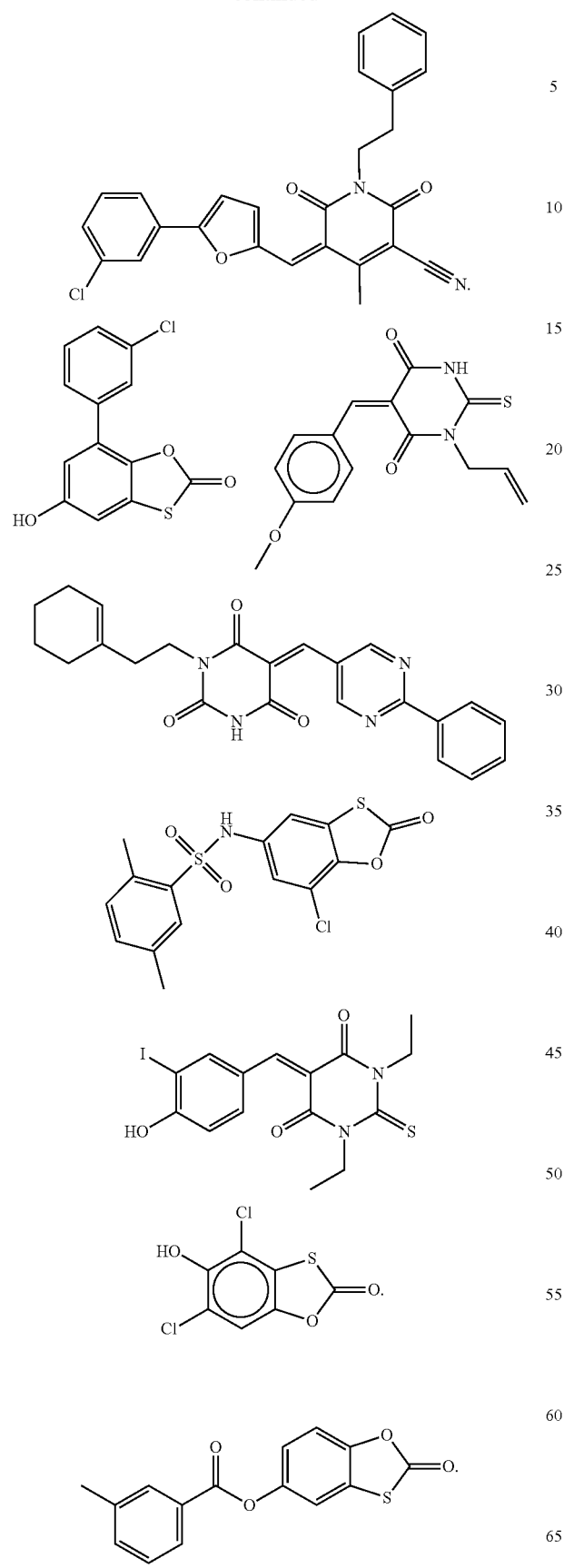
1708
-continued
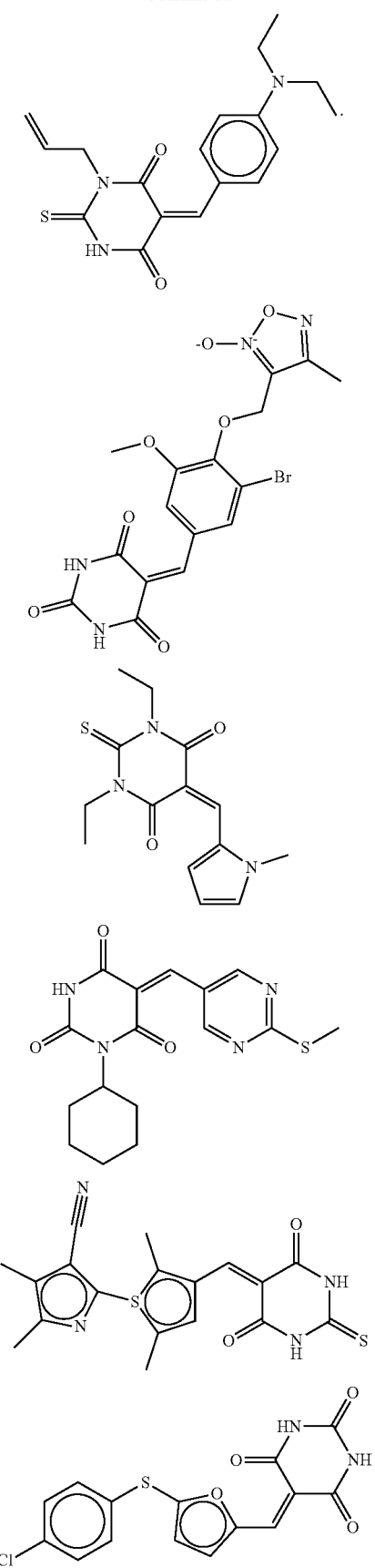

1709 -continued
1710 -continued
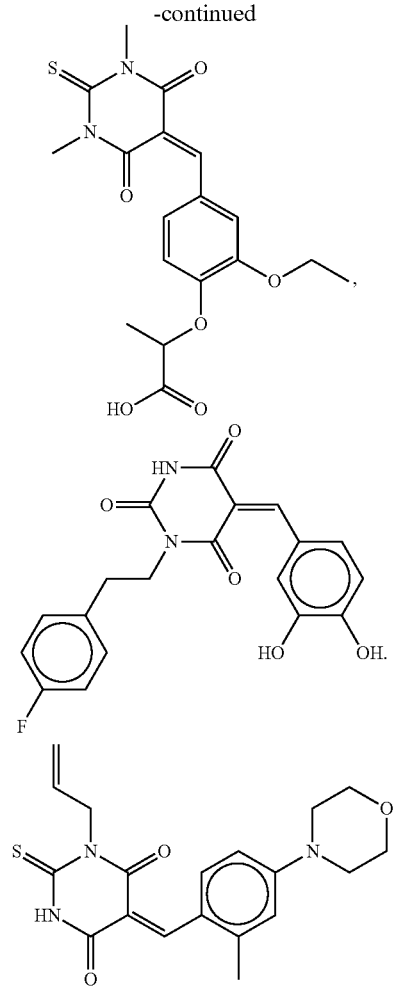
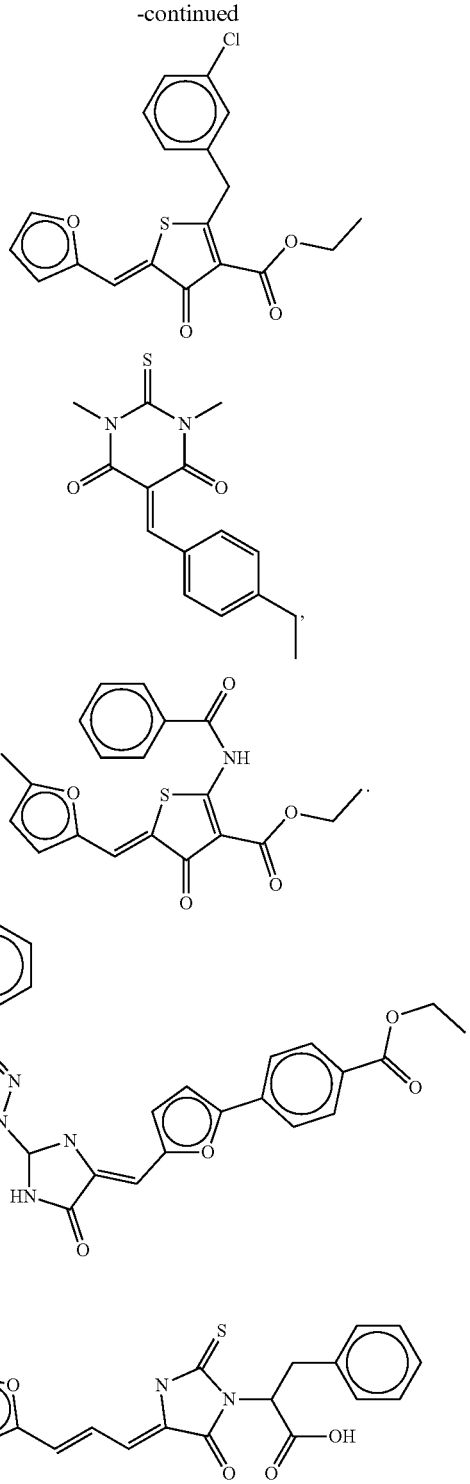
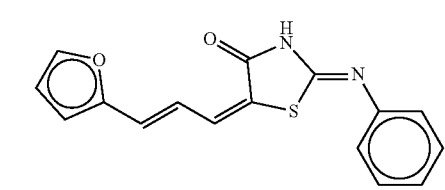

1711
-continued
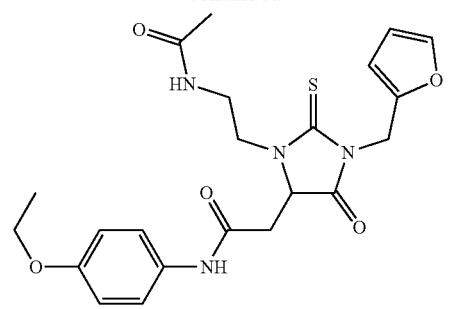
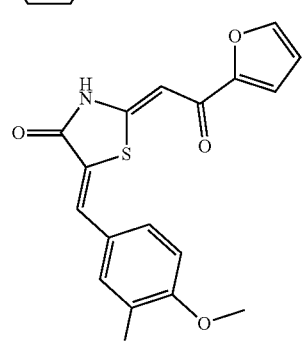
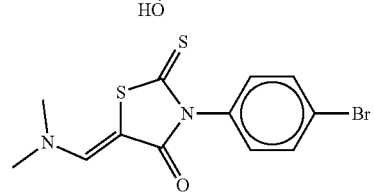
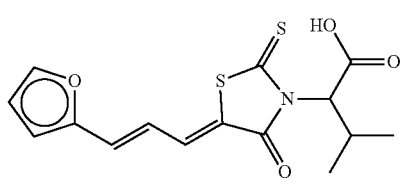
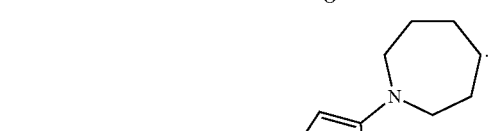
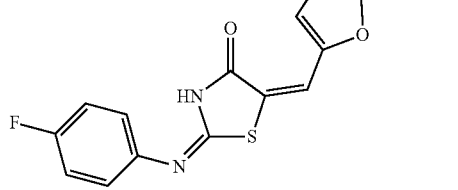
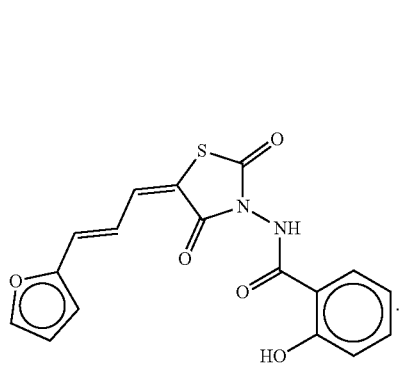
1712
-continued
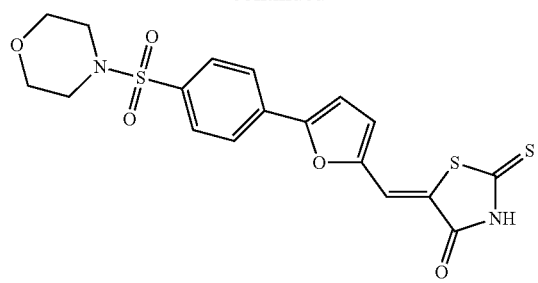
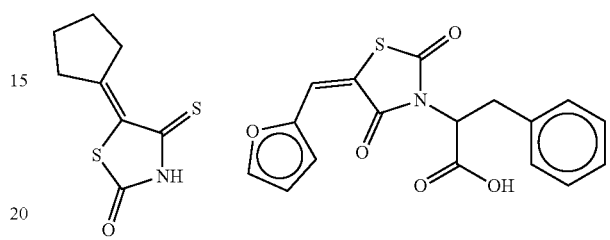
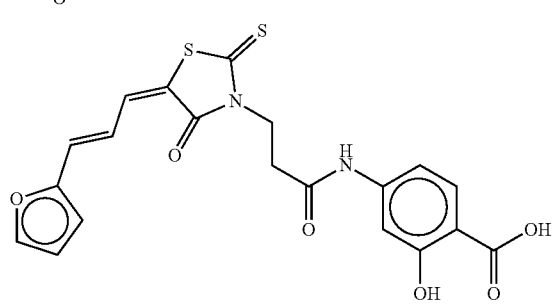
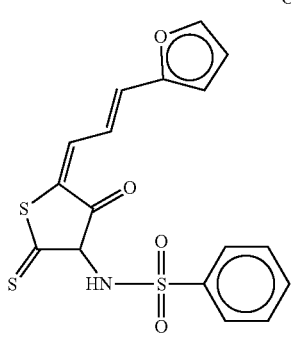
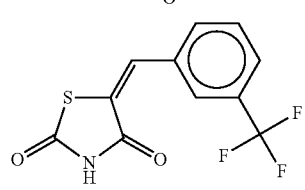
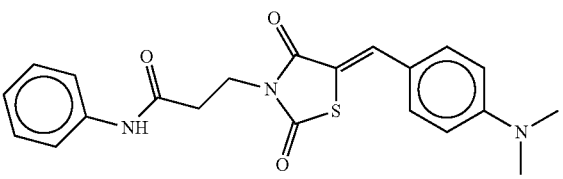

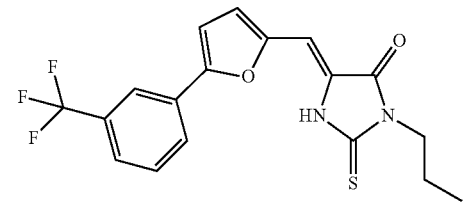
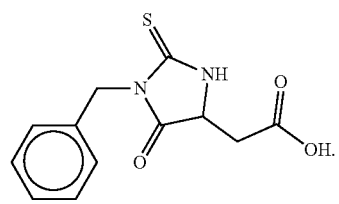
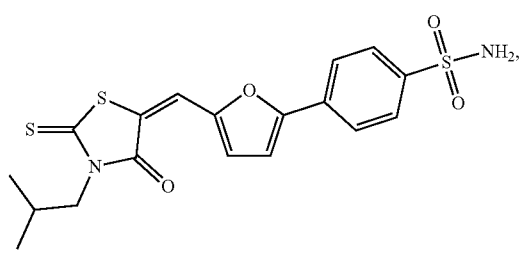
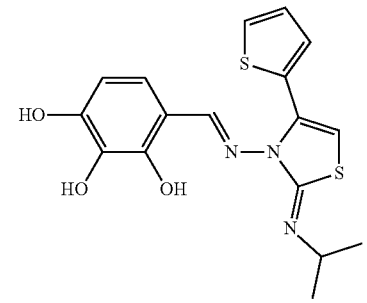
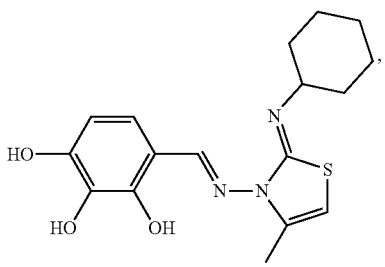
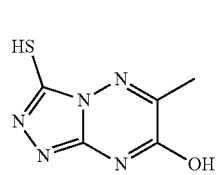
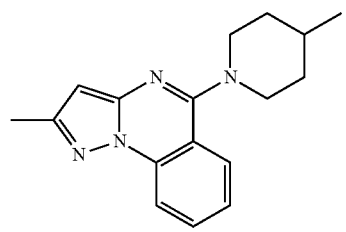
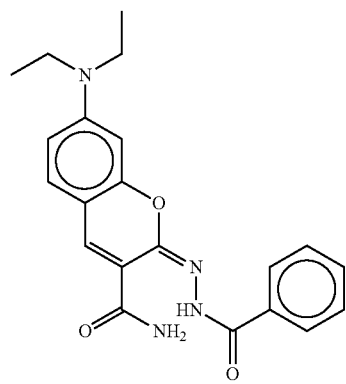
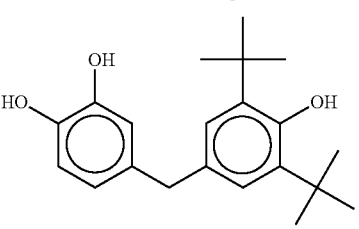
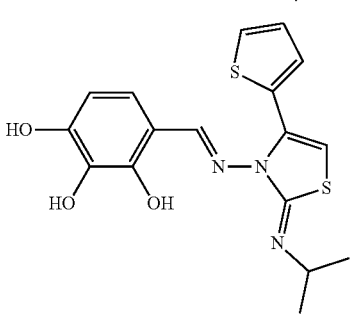
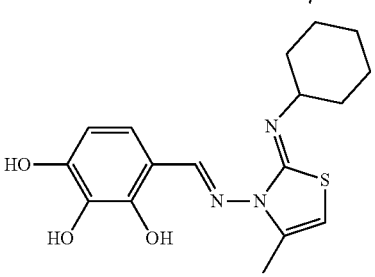
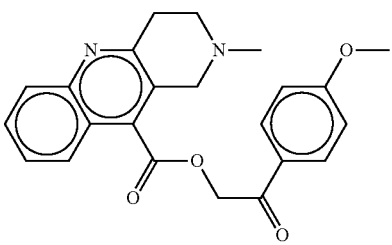
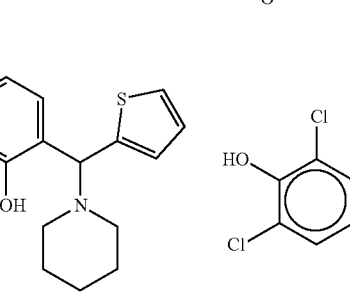

1715
-continued
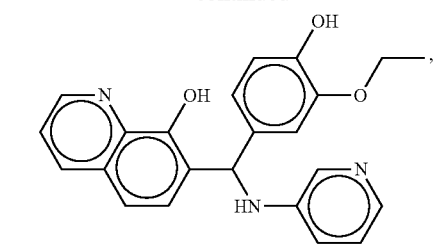
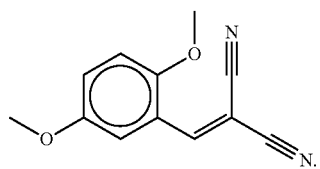
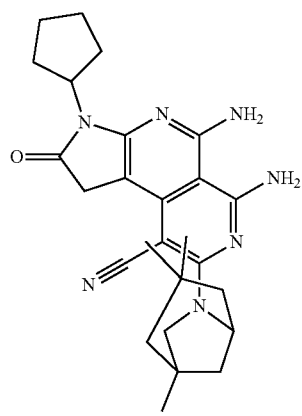
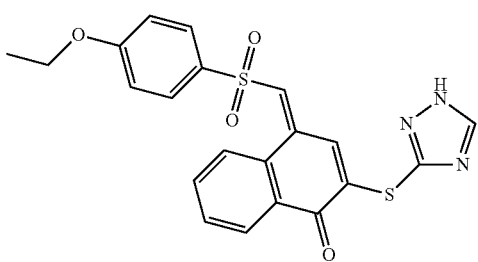
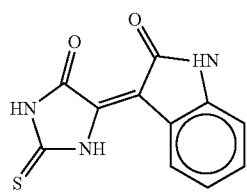
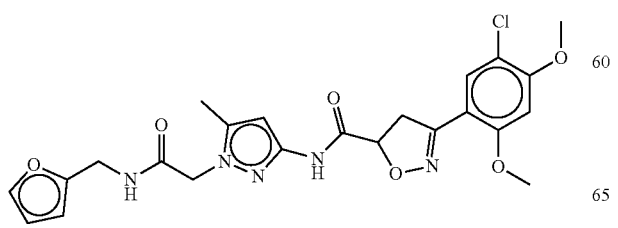
1716
-continued
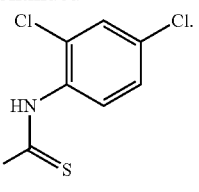
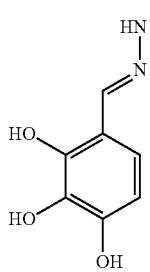
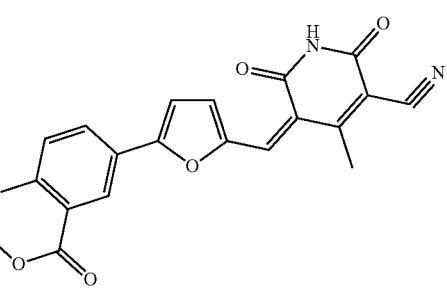
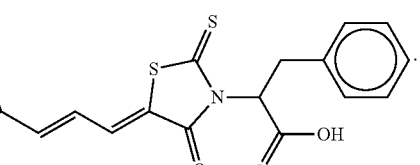
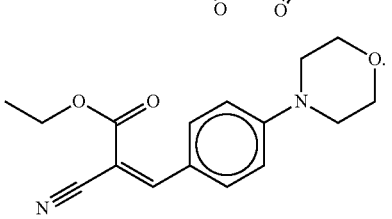
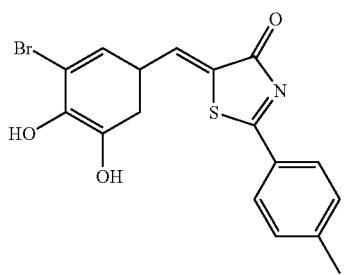
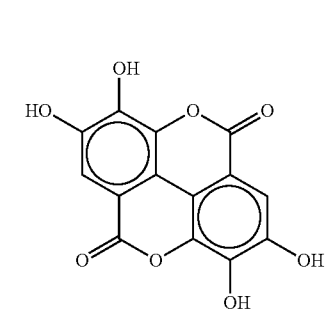

1717
-continued
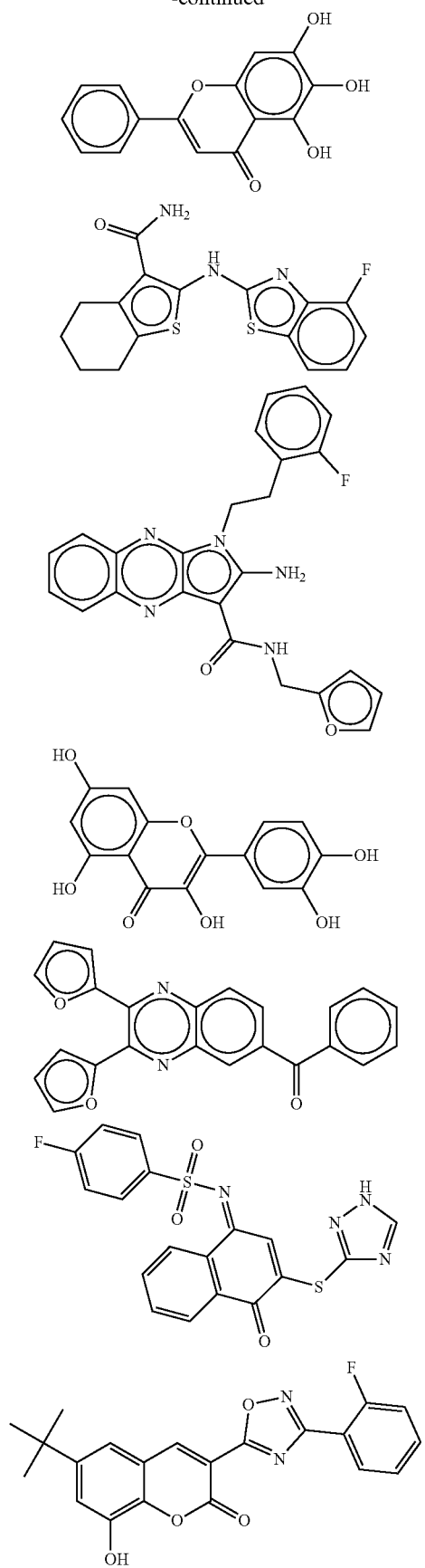
1718
-continued
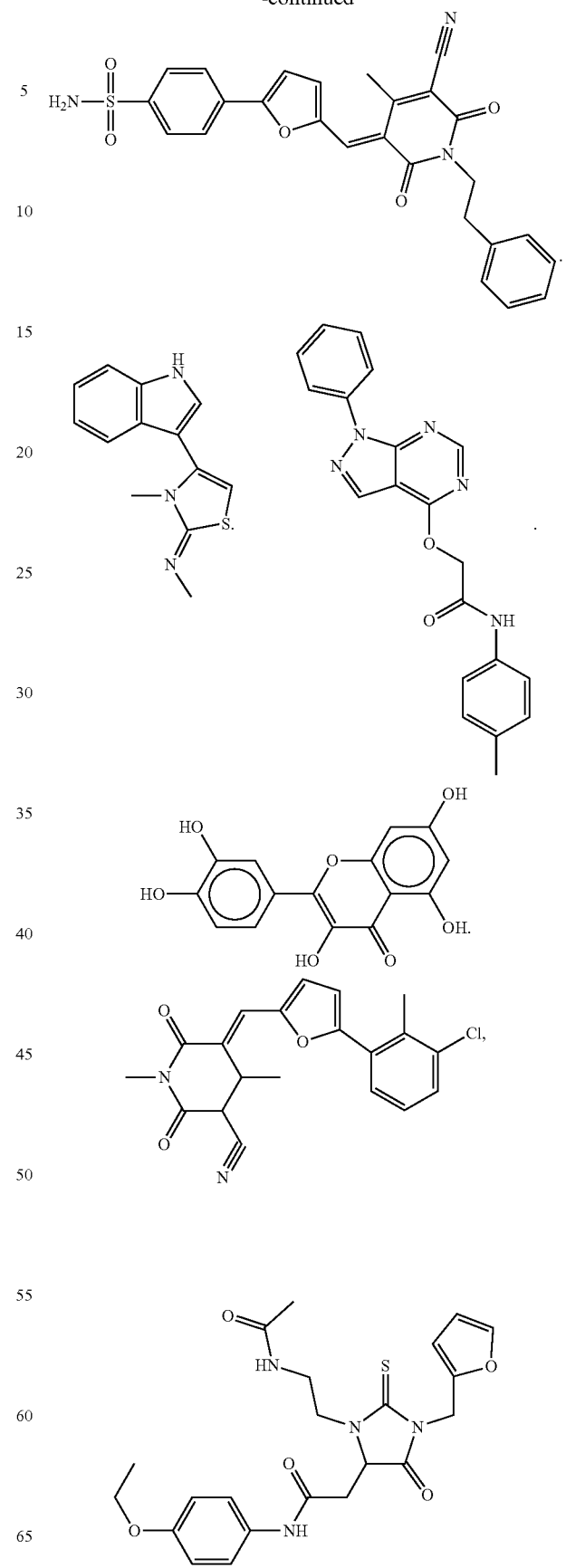

1719
-continued
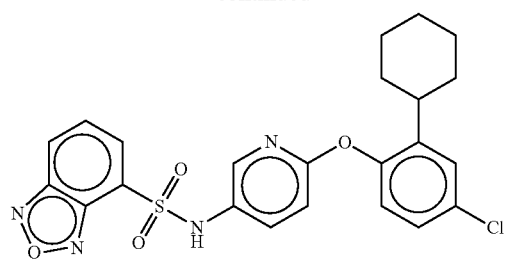
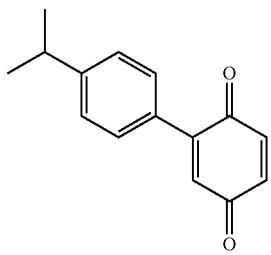
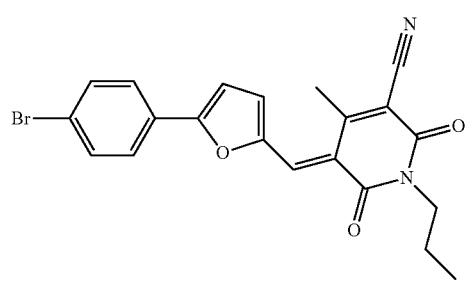
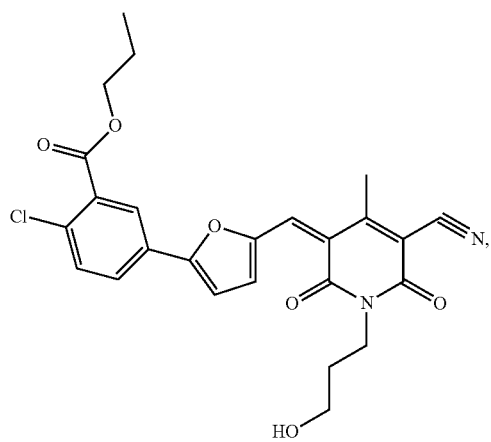
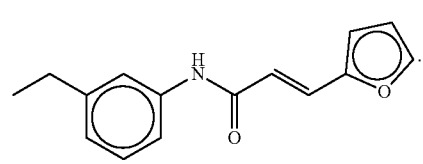
1720
-continued
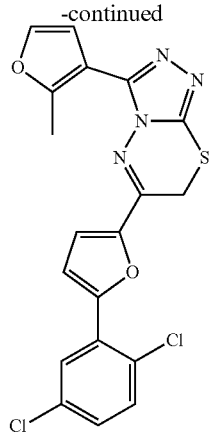
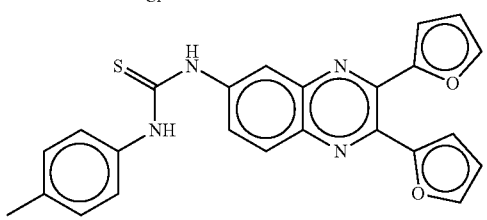
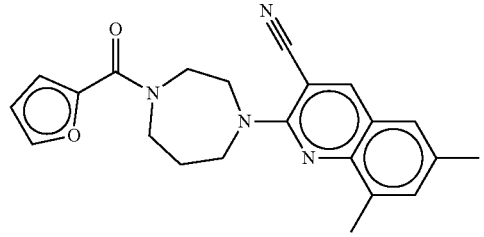
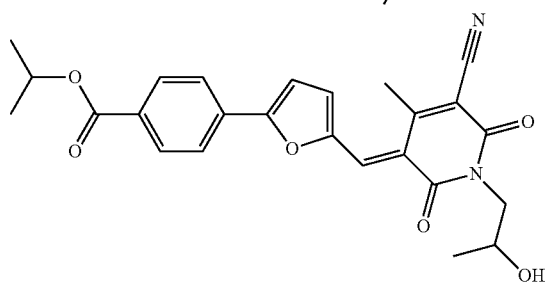
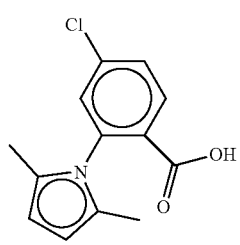
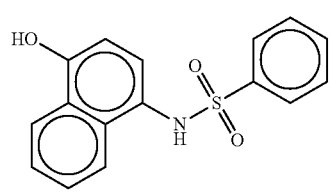

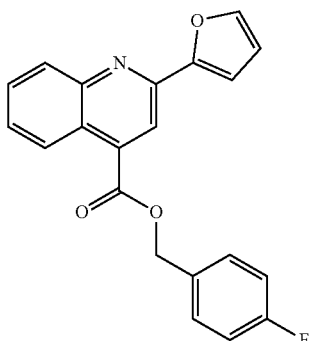
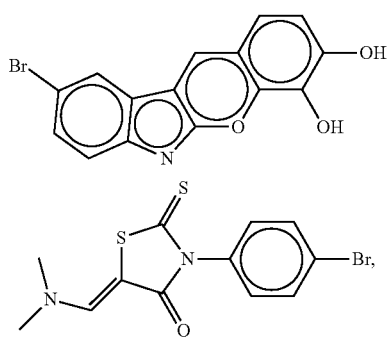
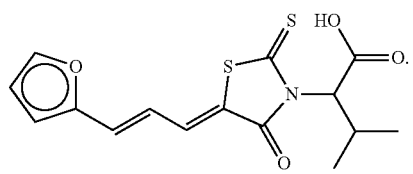
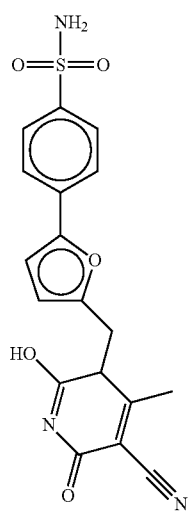
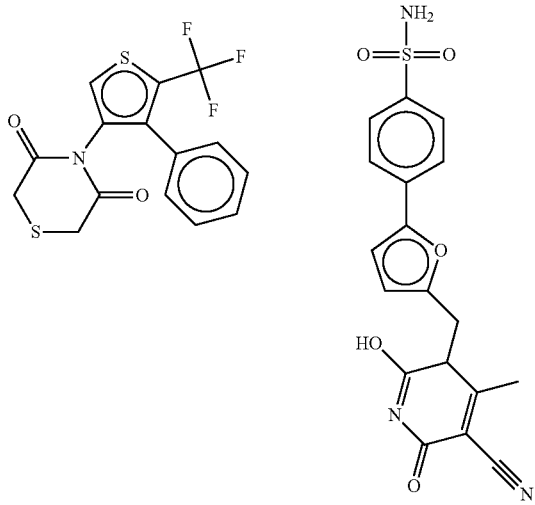
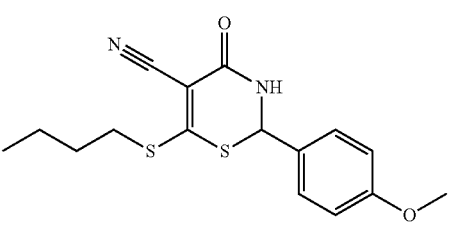
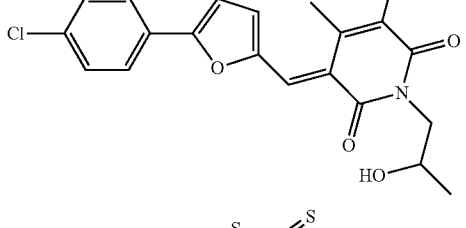
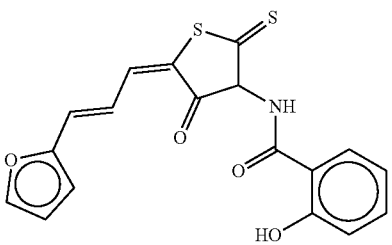
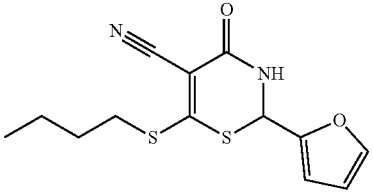
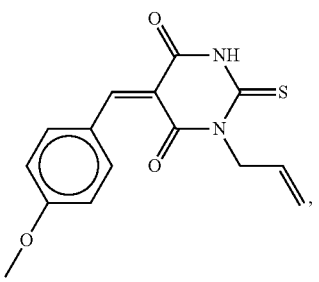

1723
-continued
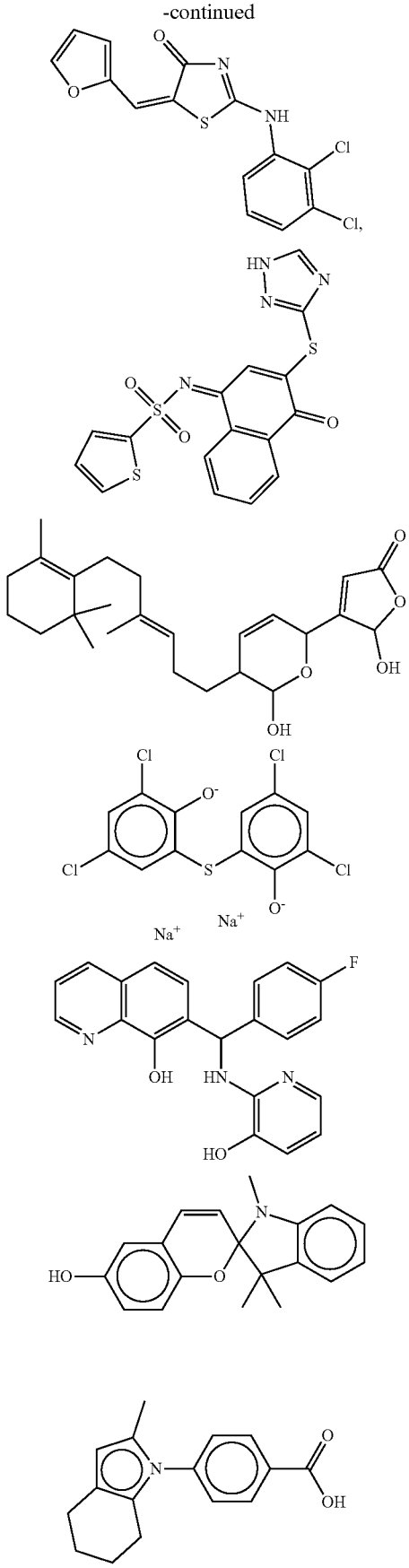
1724
-continued
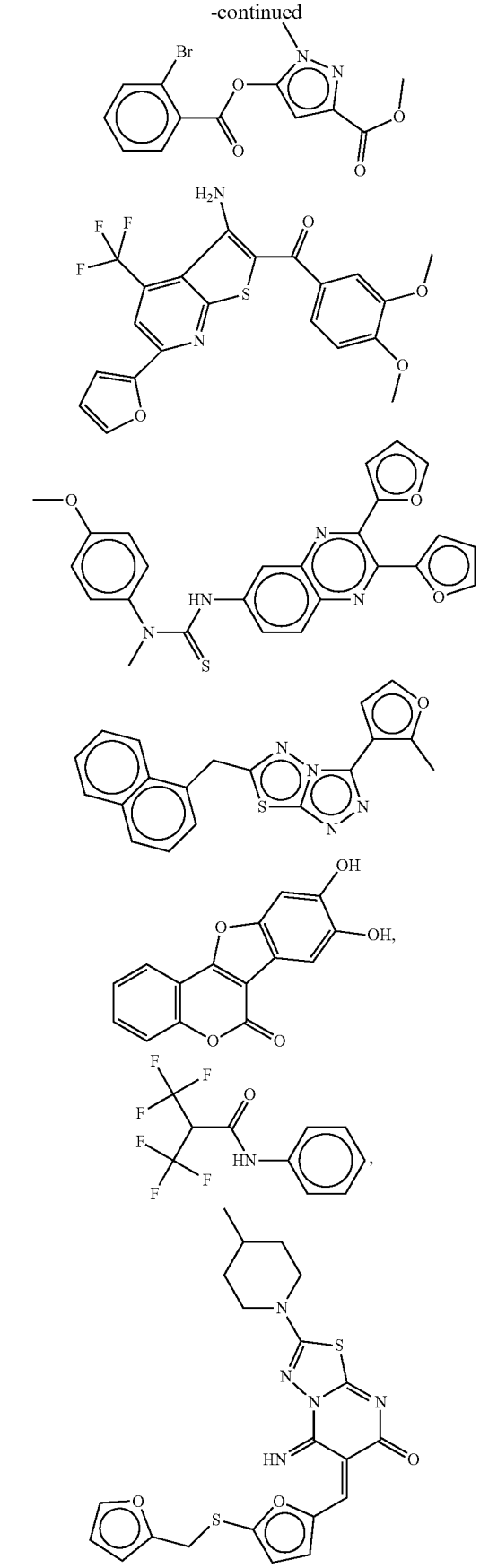

1725
-continued
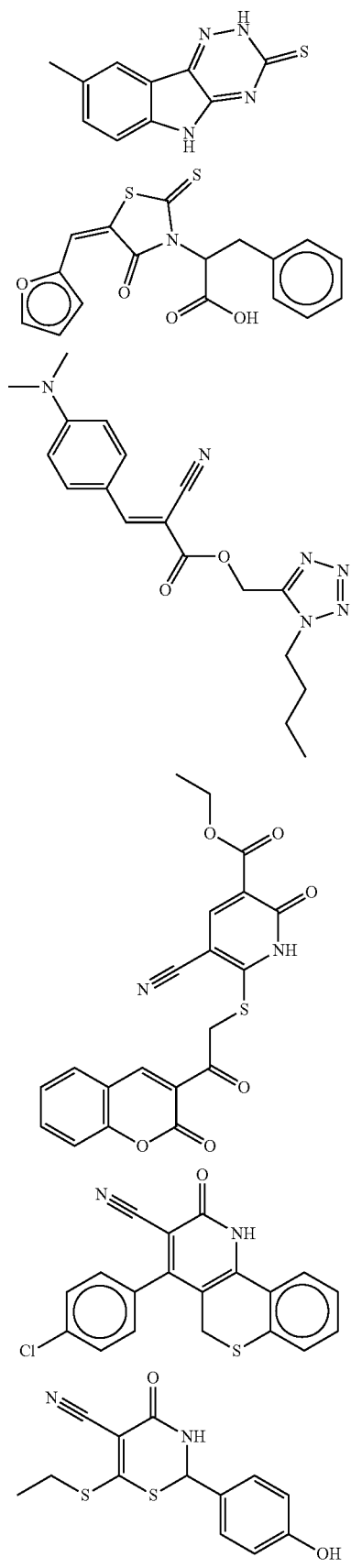
1726
-continued
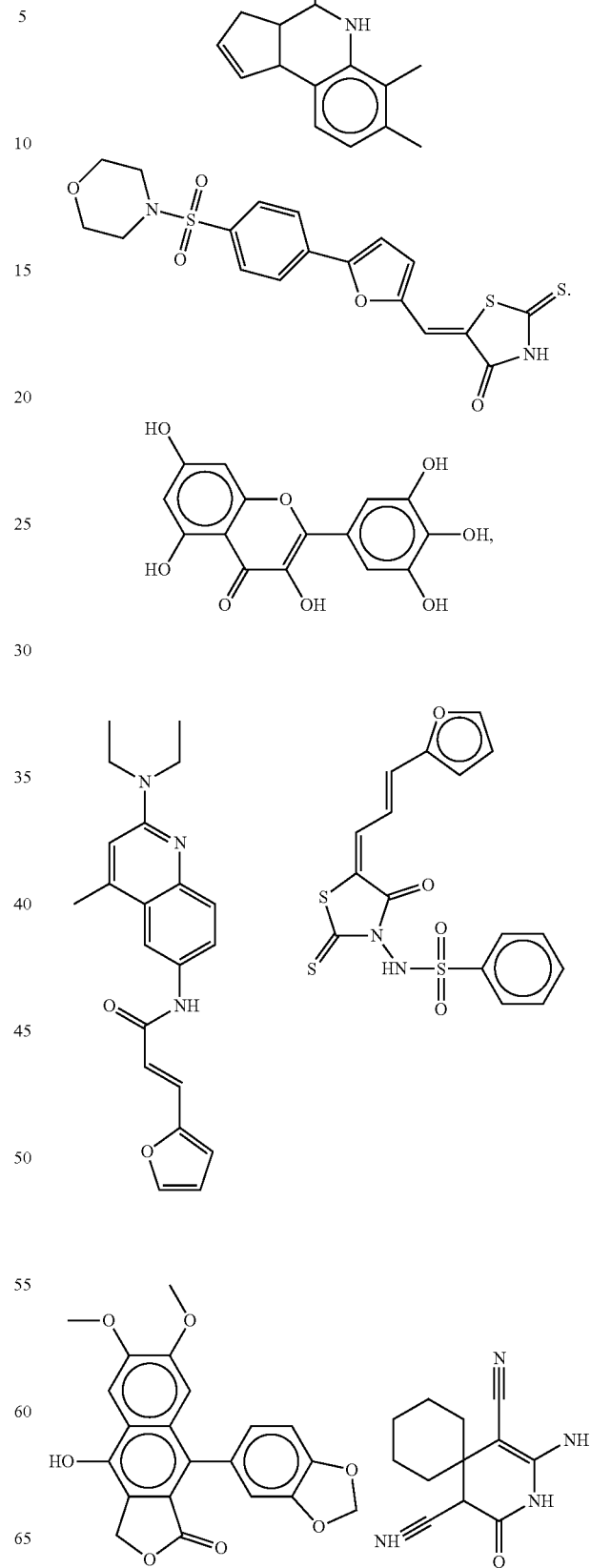

1727
-continued
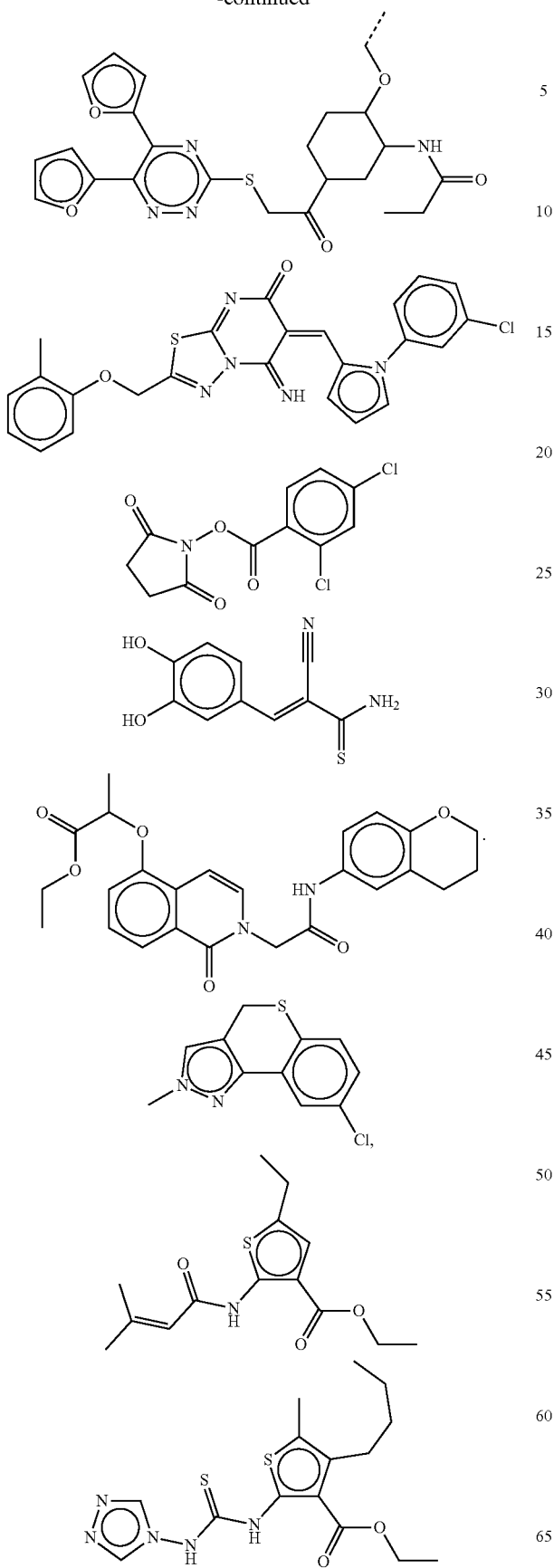
1728
-continued
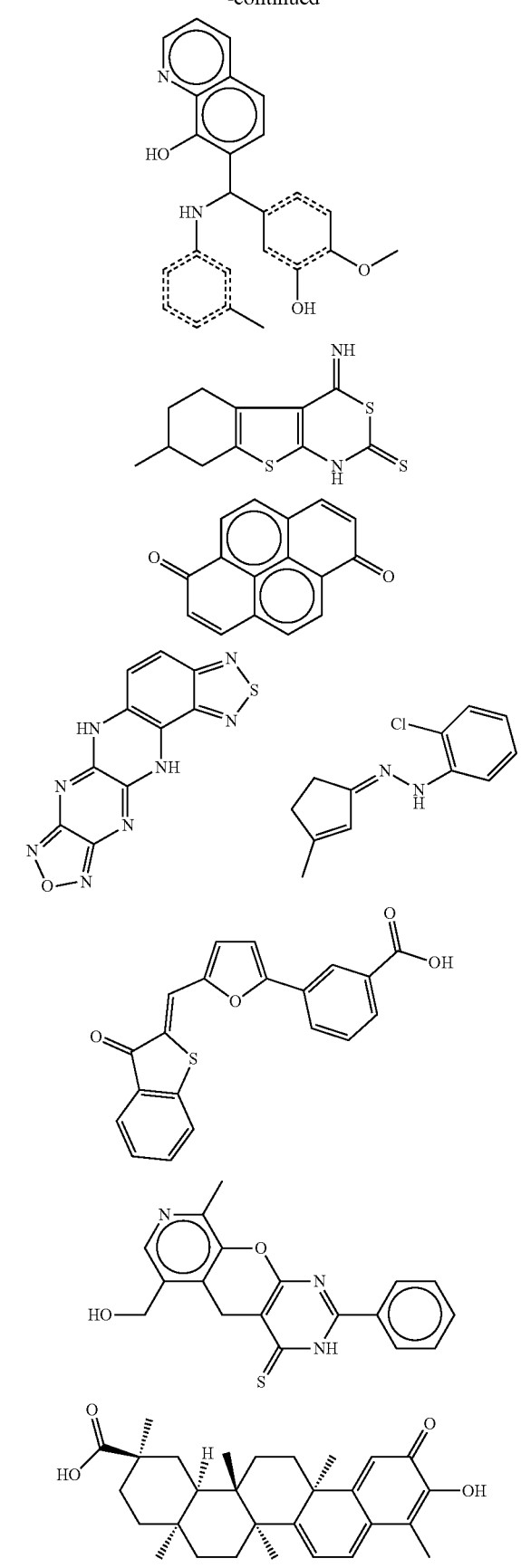

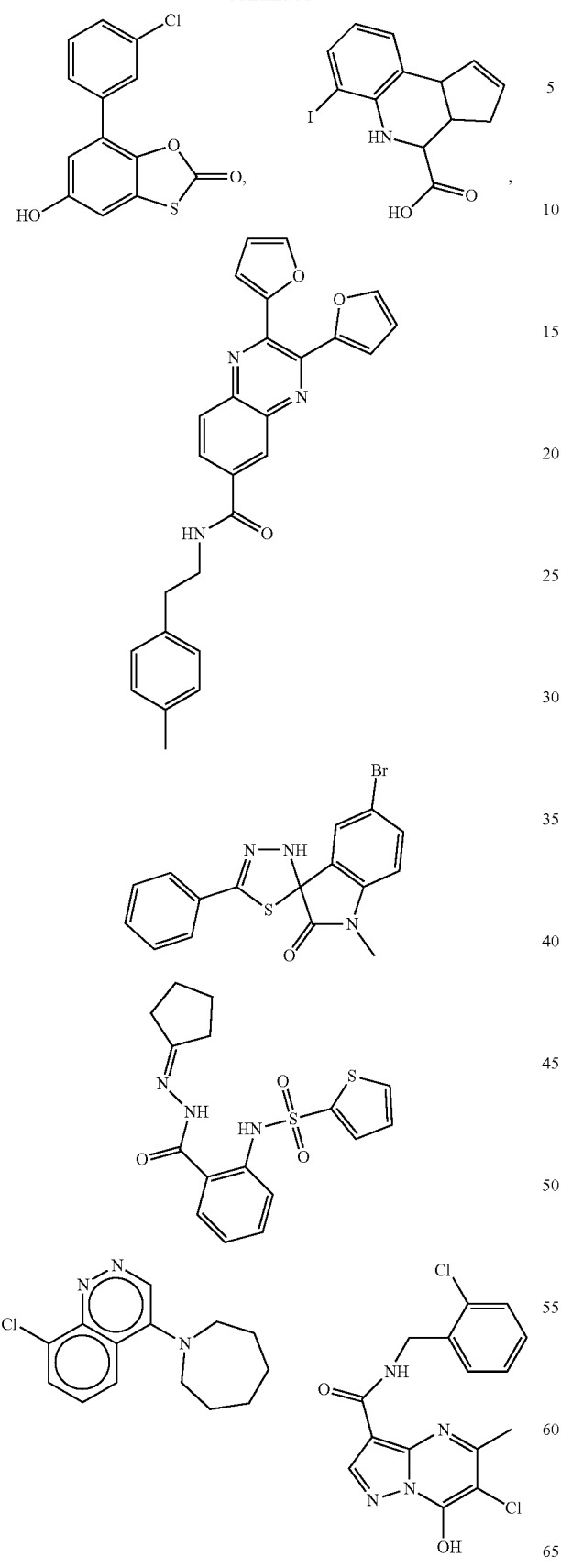
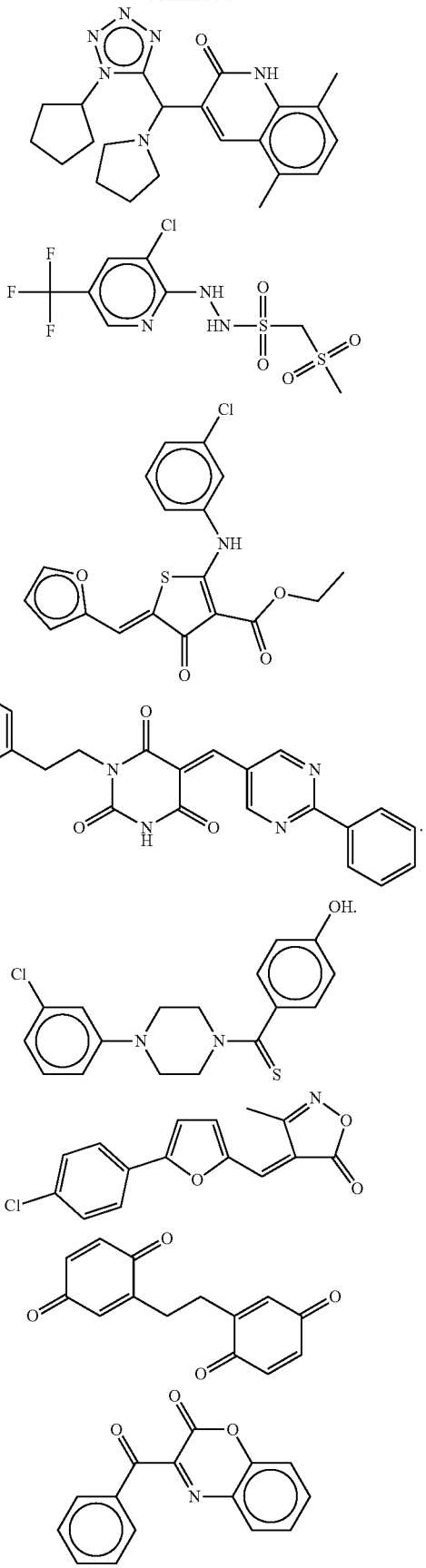

1731
-continued
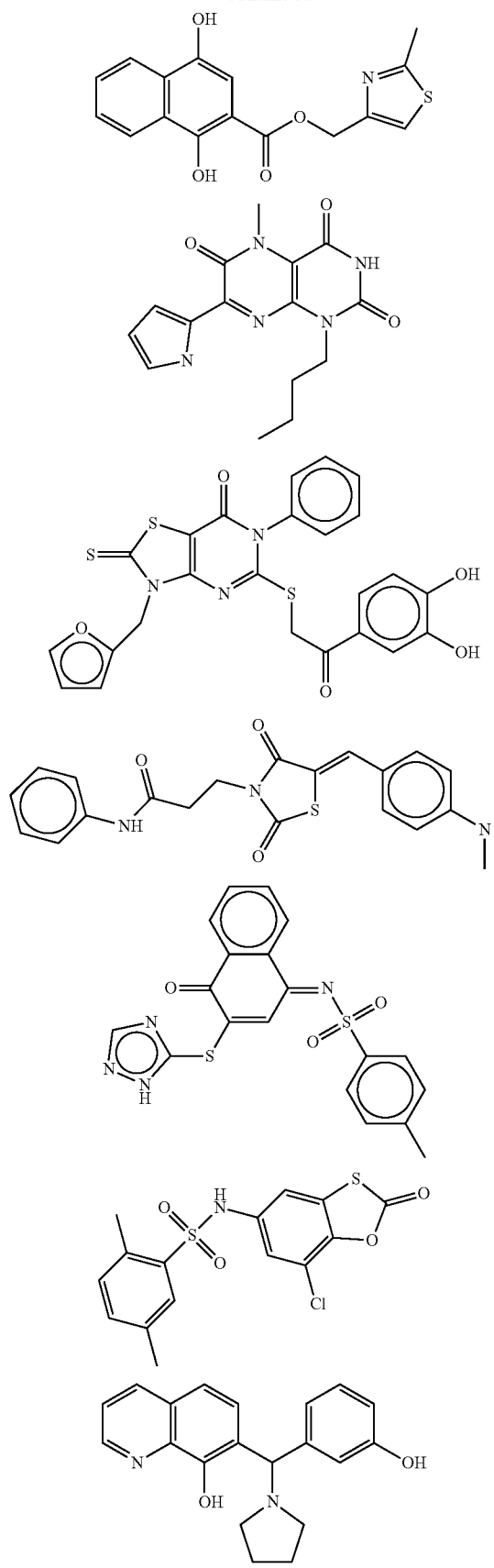
1732
-continued
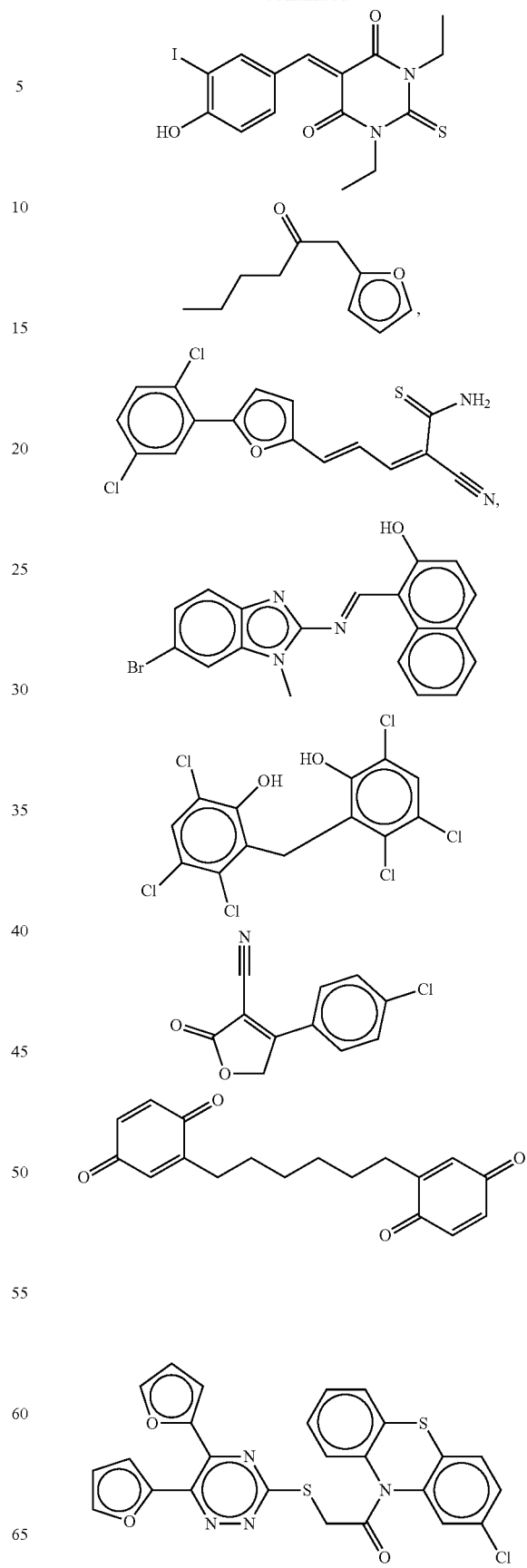

1733
-continued
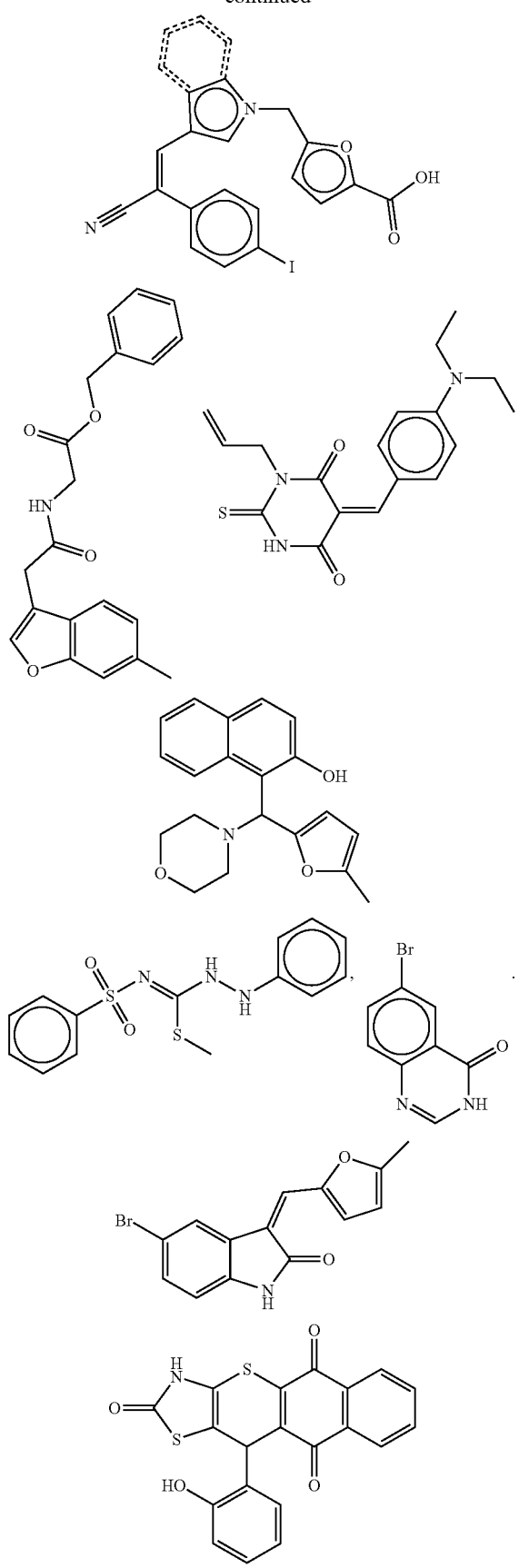
1734
-continued
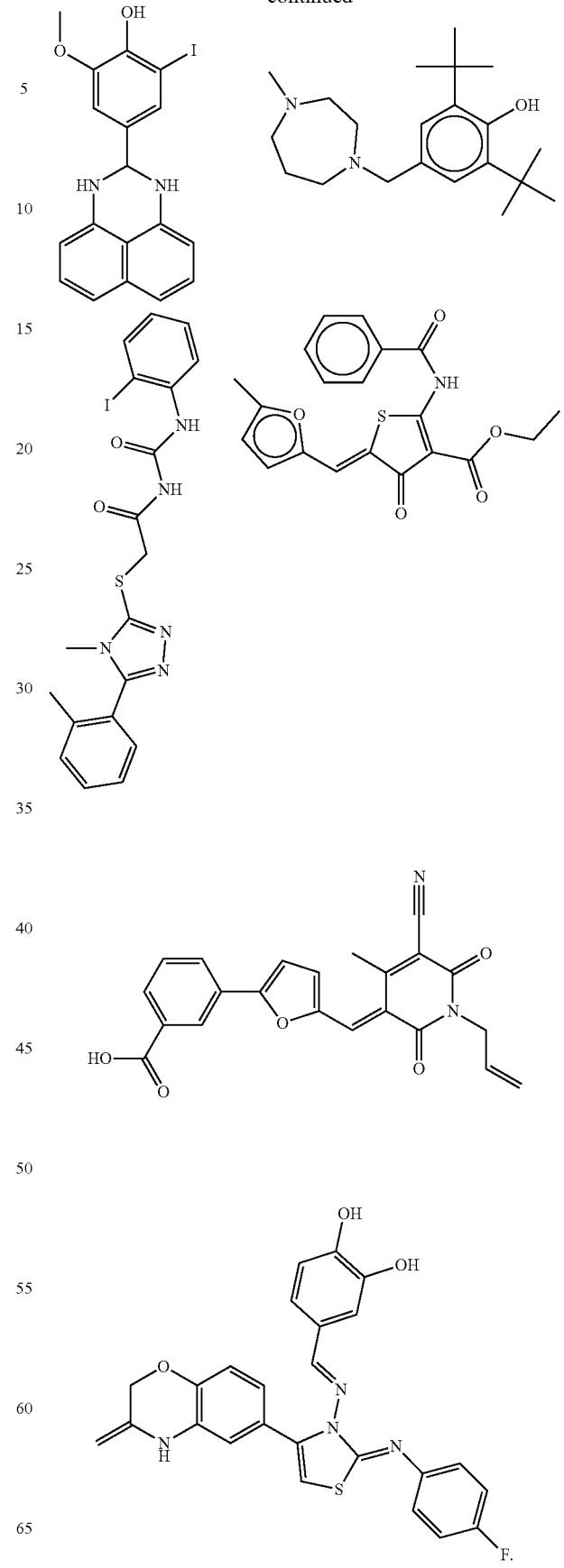

1735 -continued

1736 -continued

1737
-continued
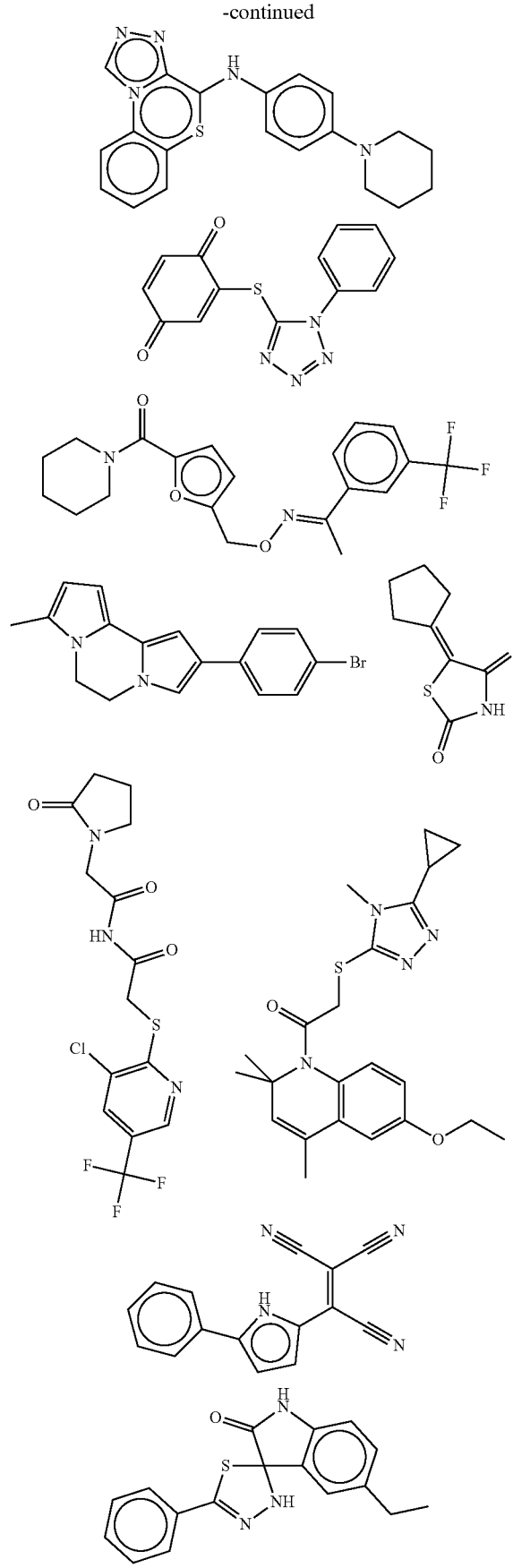
1738
-continued
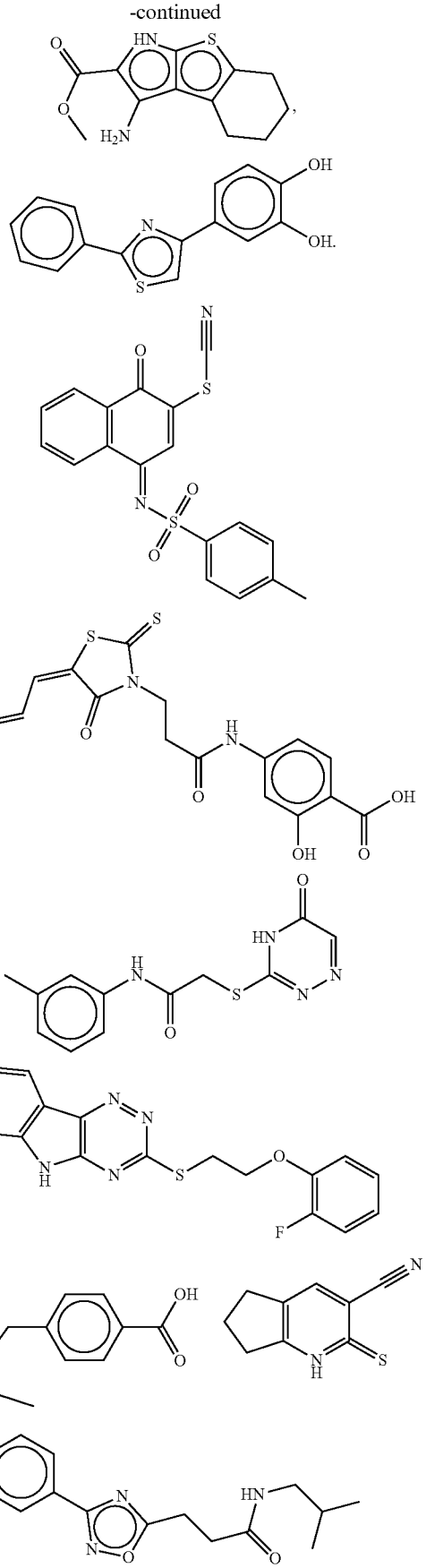

1739
-continued
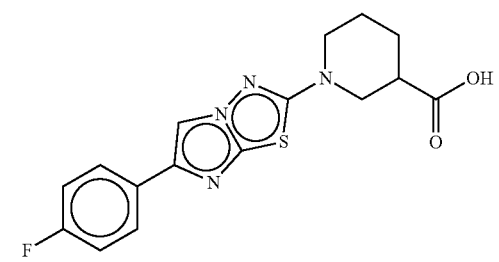
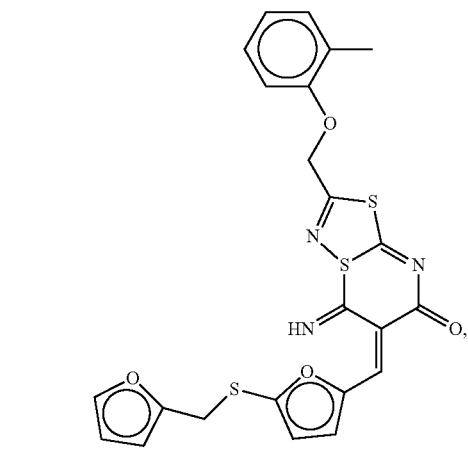
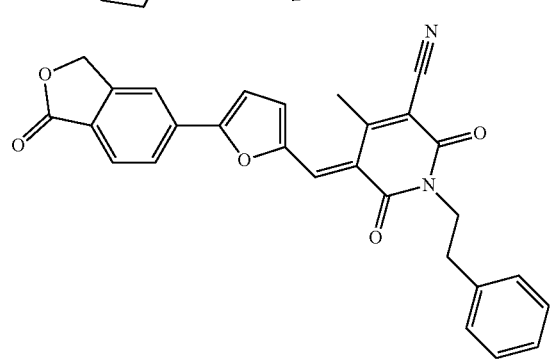
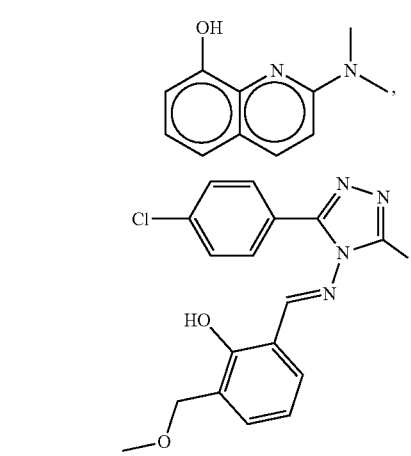
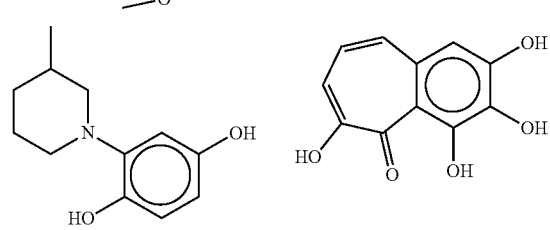
1740
-continued
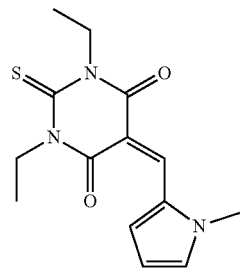
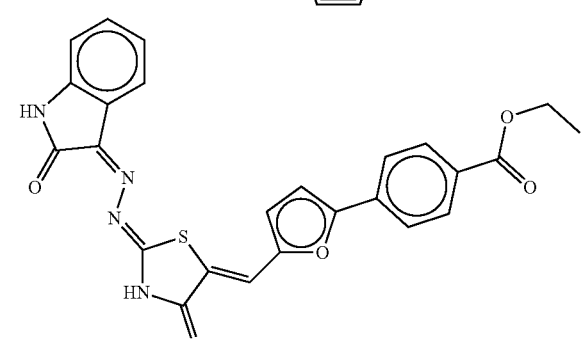
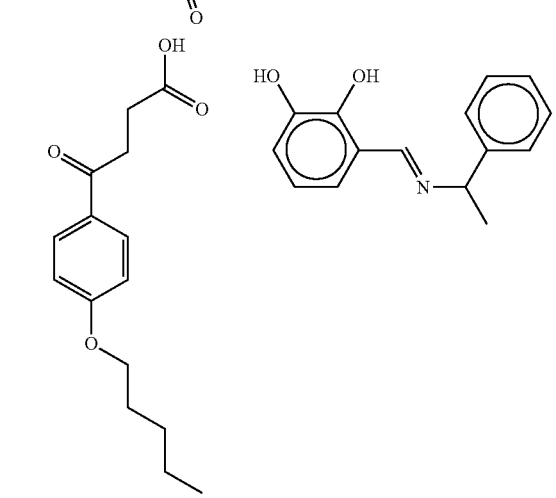
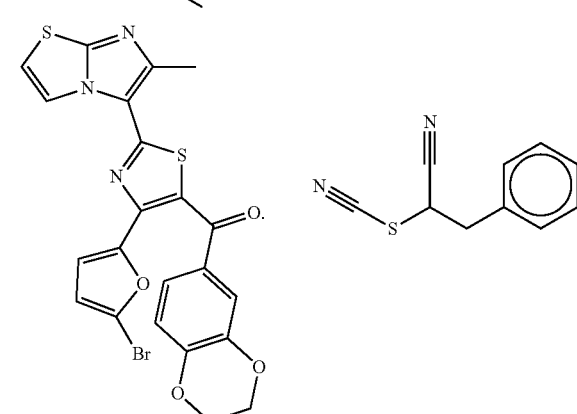
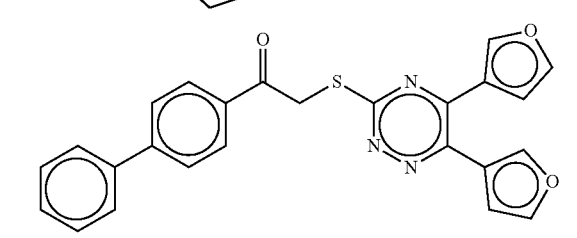

1741
-continued
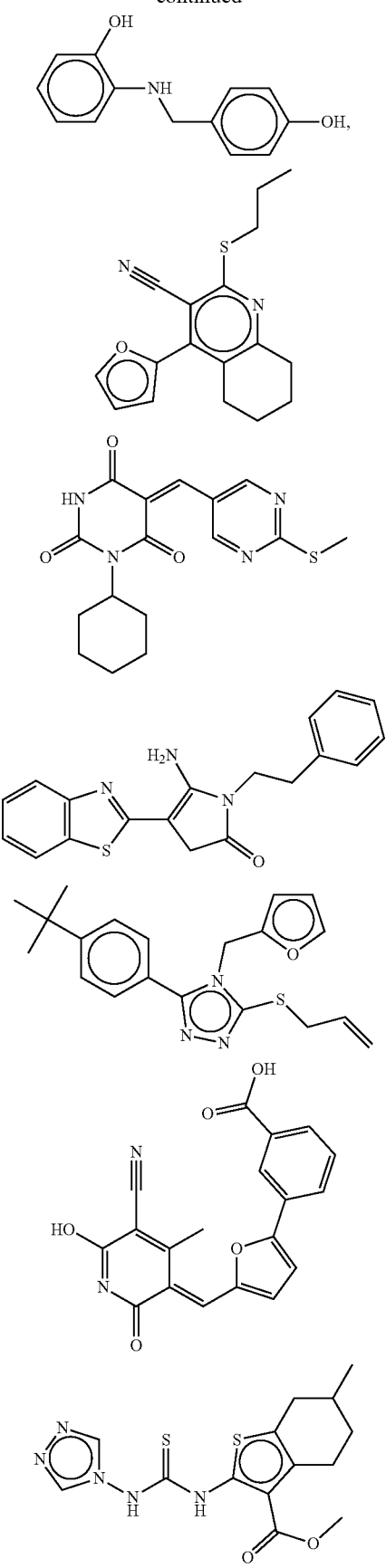
1742
-continued
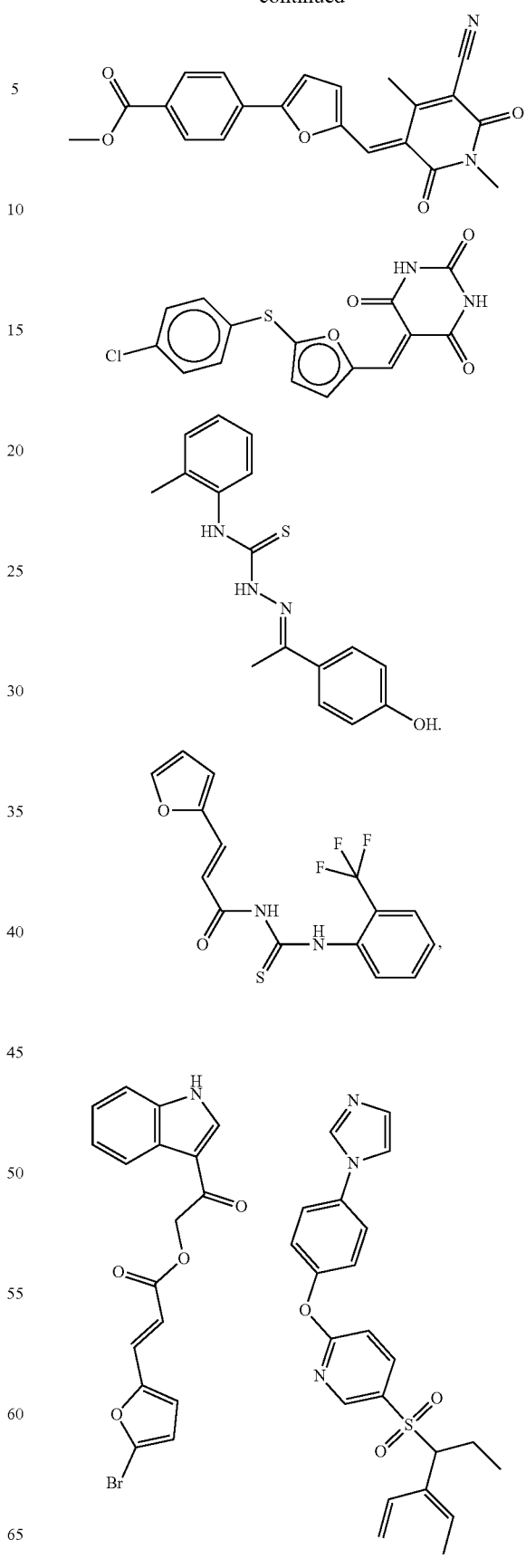

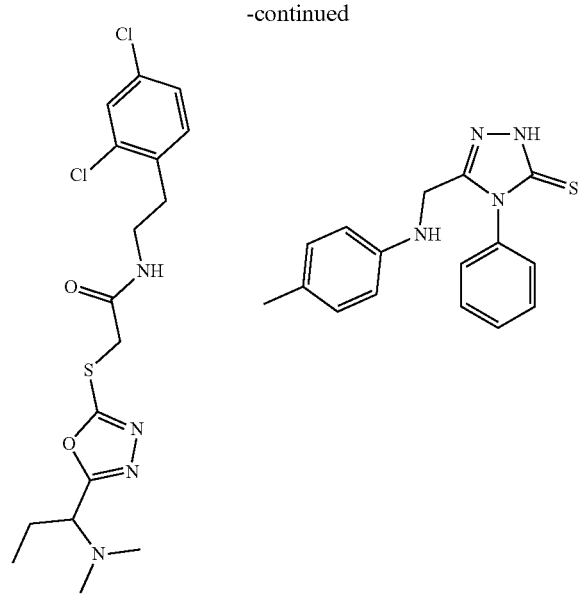
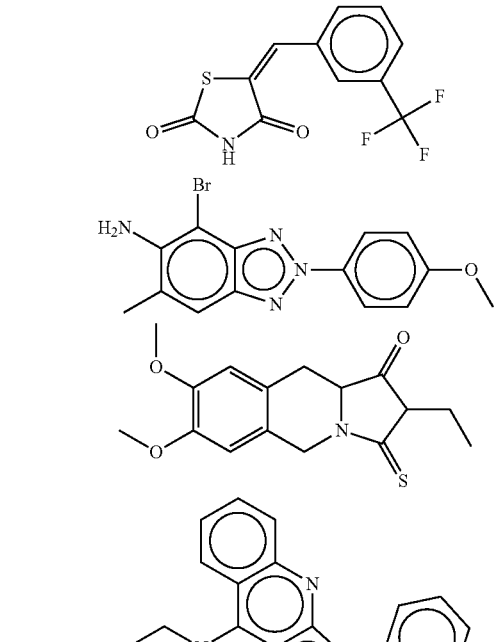
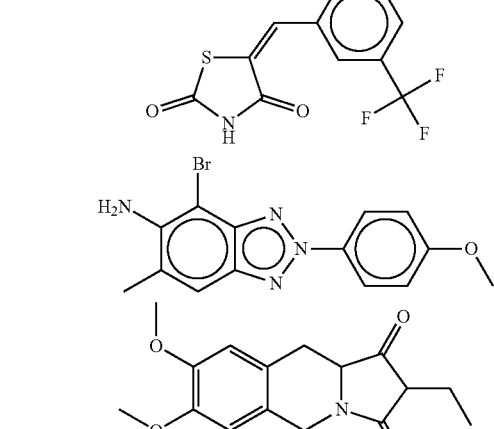
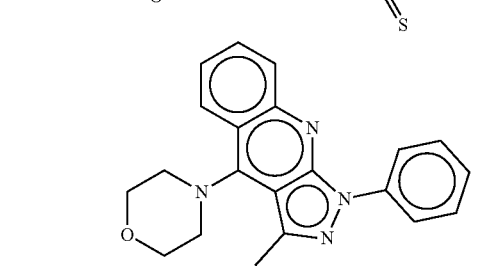
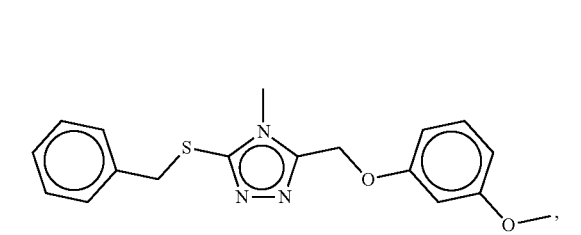
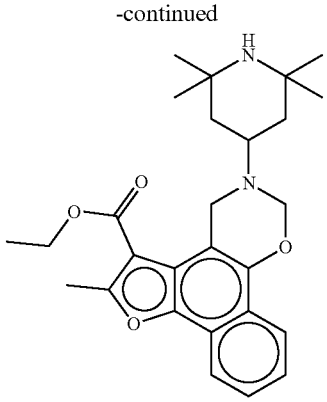
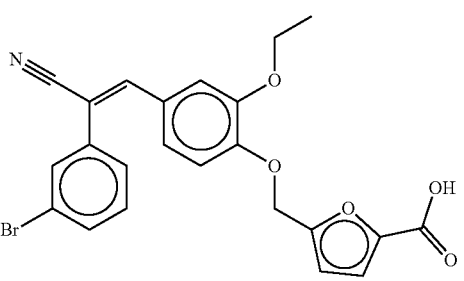
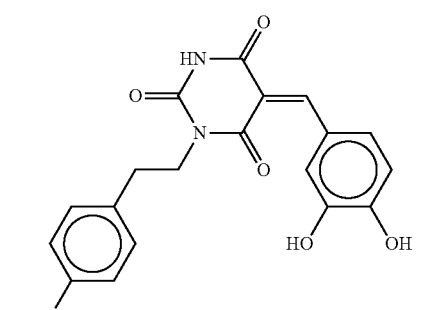
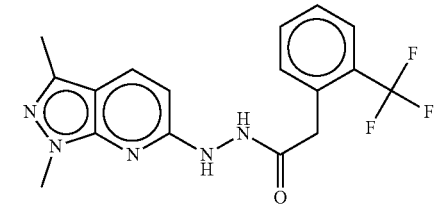
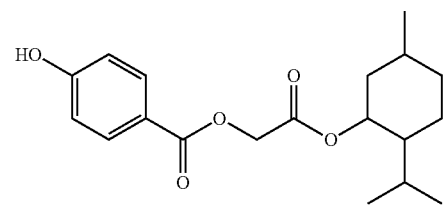

1745
-continued
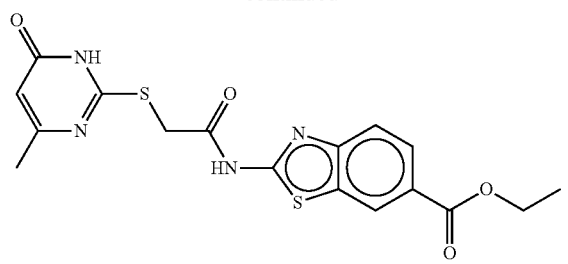
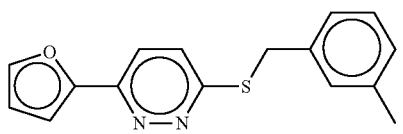
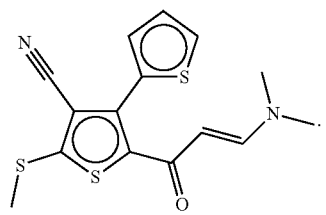
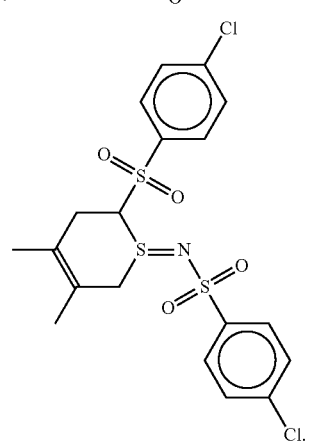
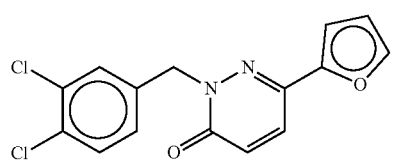
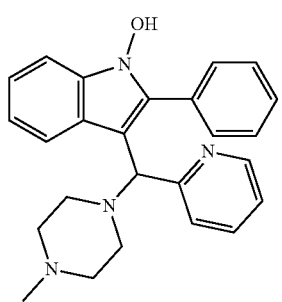
1746
-continued
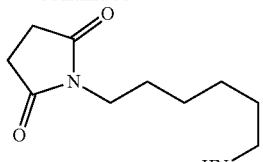
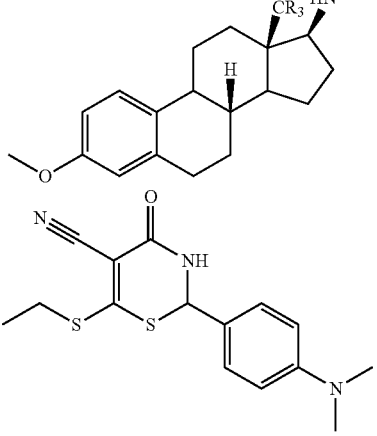
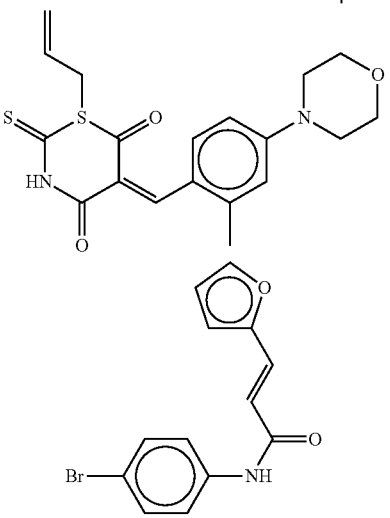
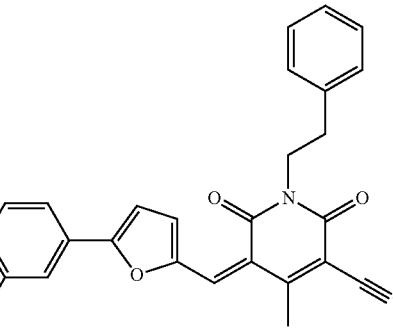
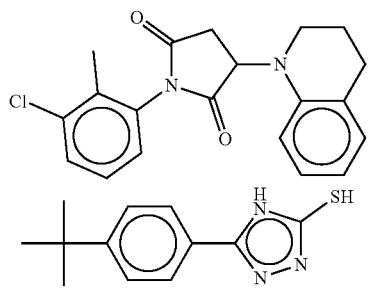
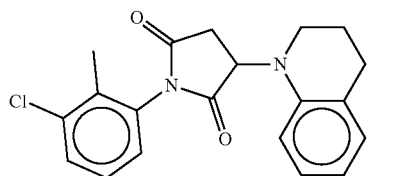
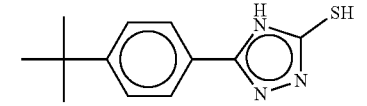

1747
-continued
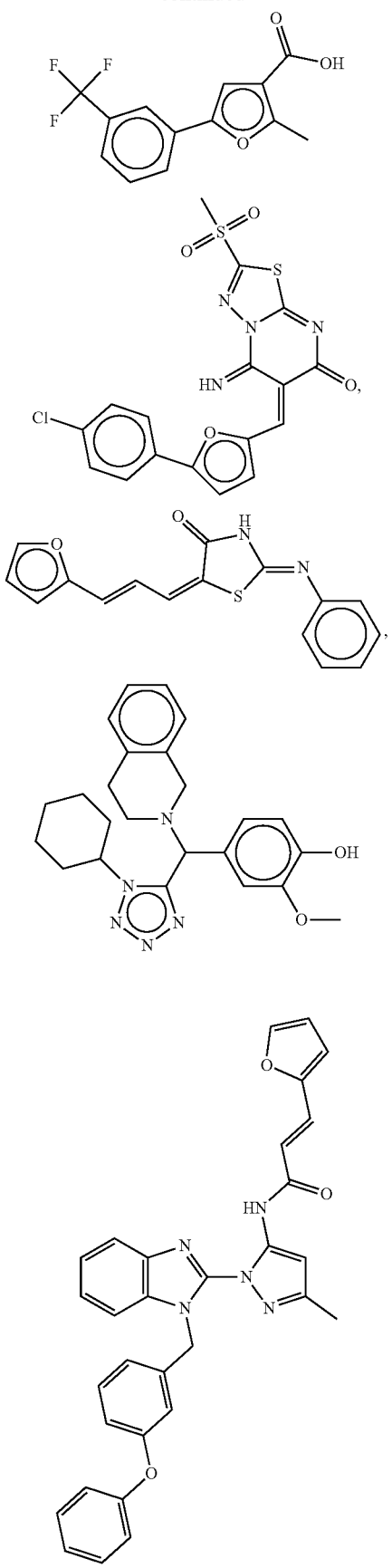
1748
-continued
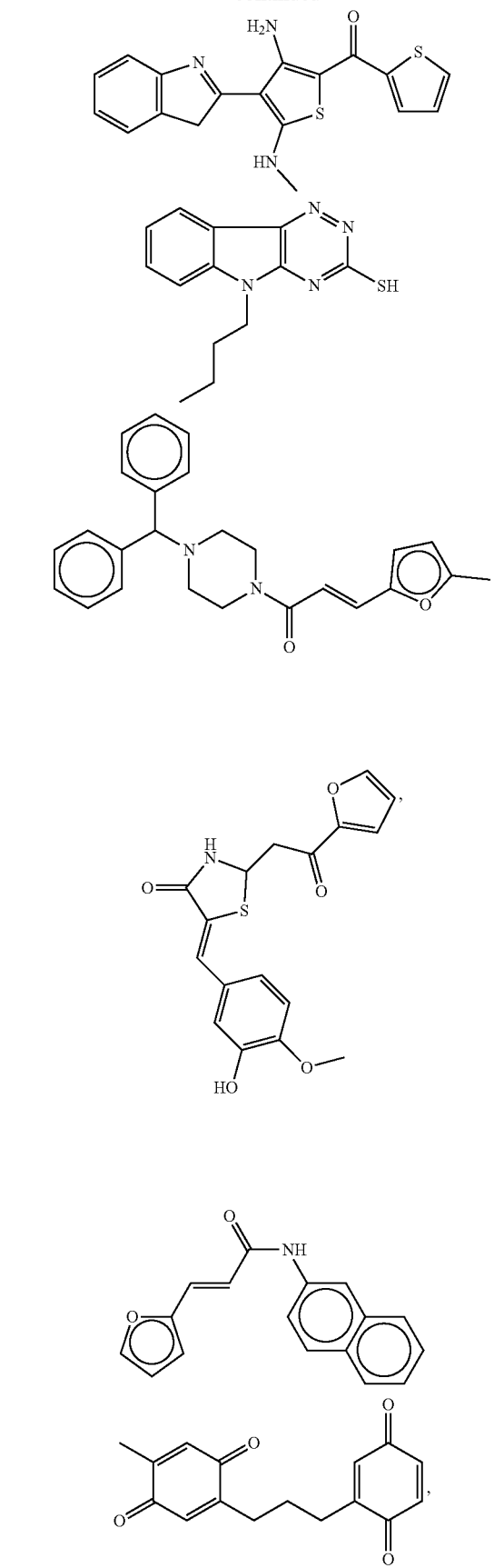

1749
-continued
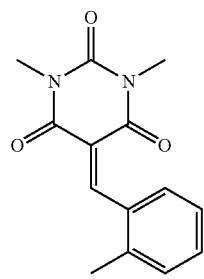 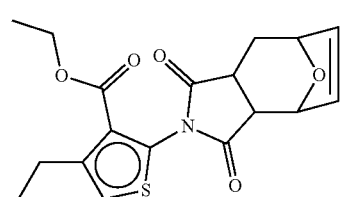
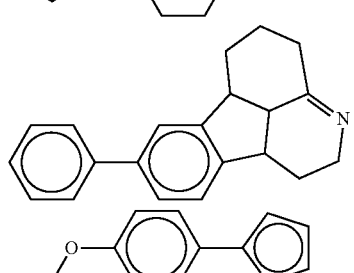
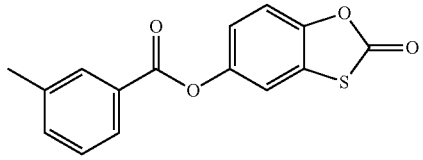
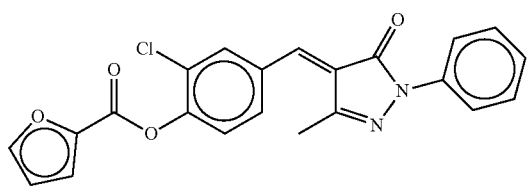
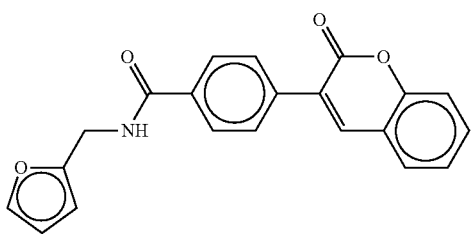
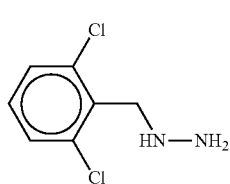 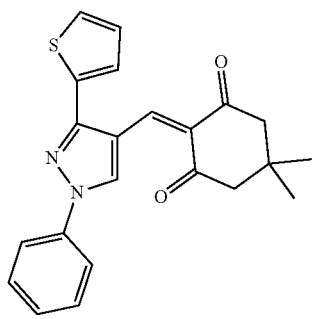
1750
-continued
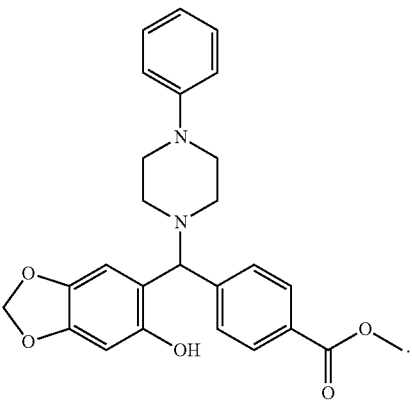
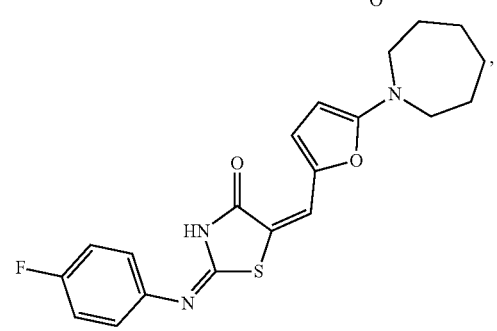
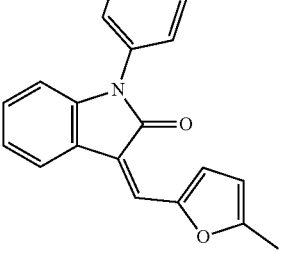
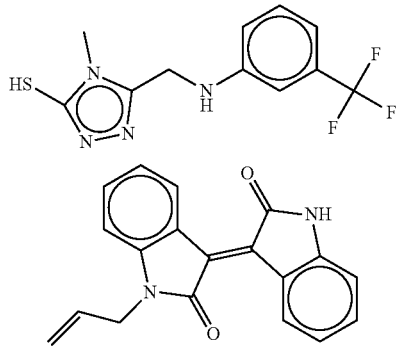
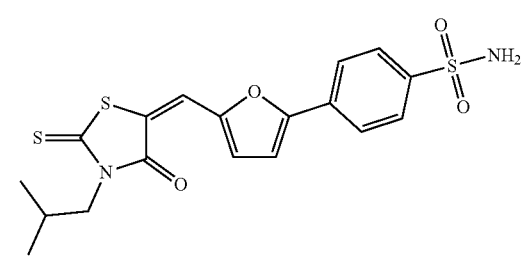

1751 1752
-continued -continued
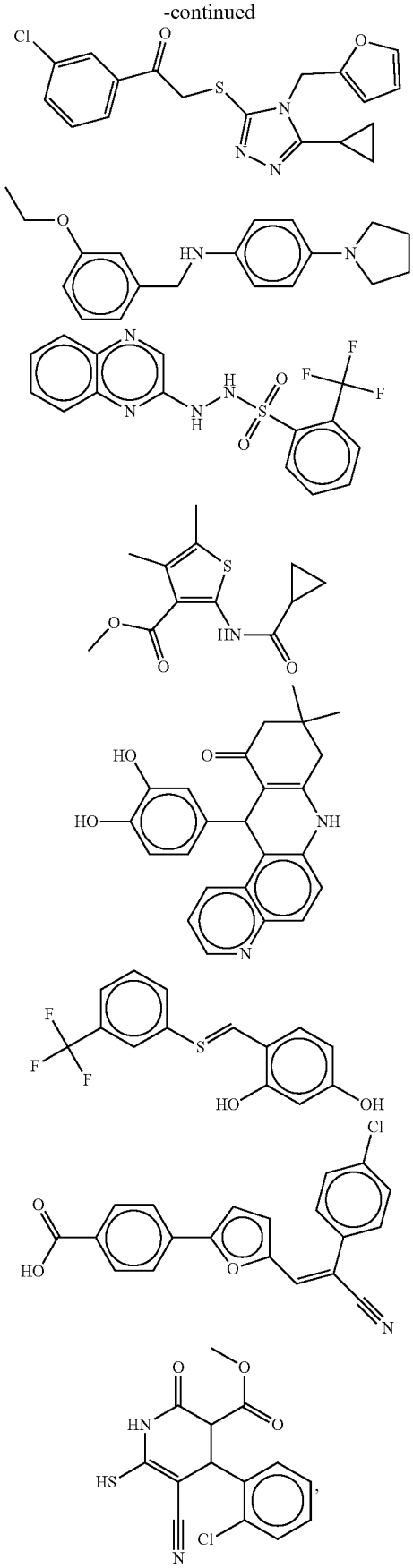
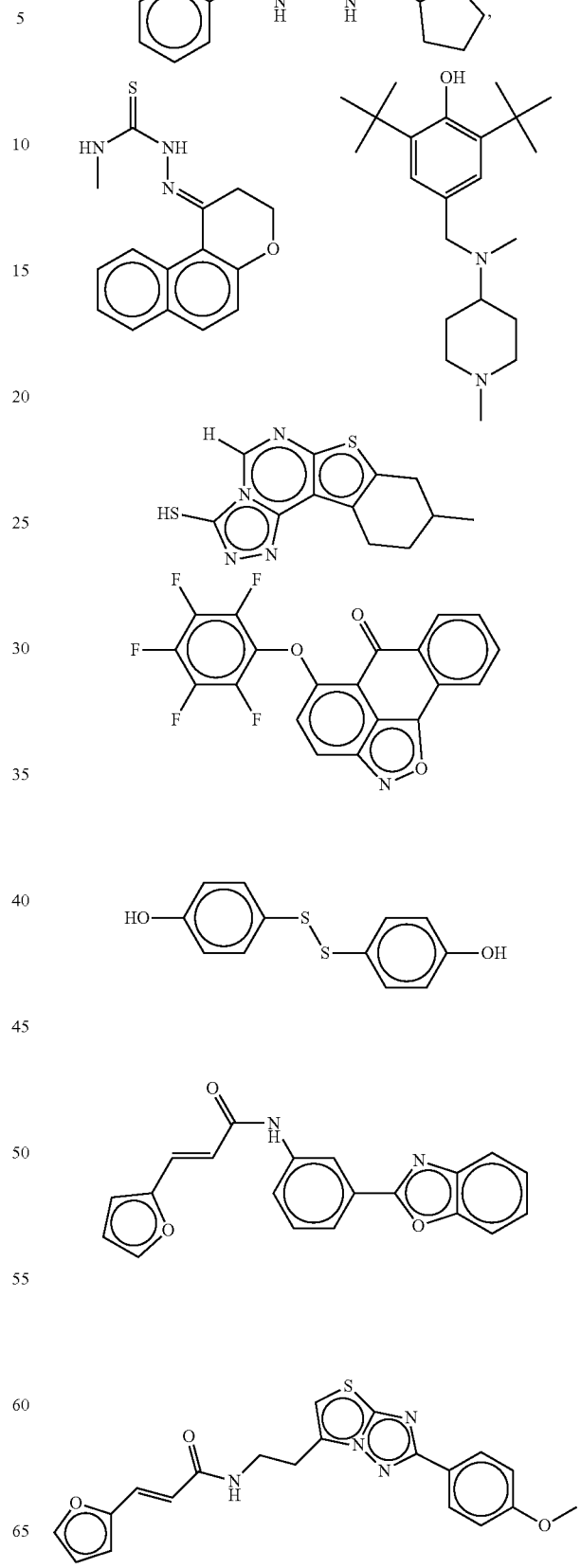

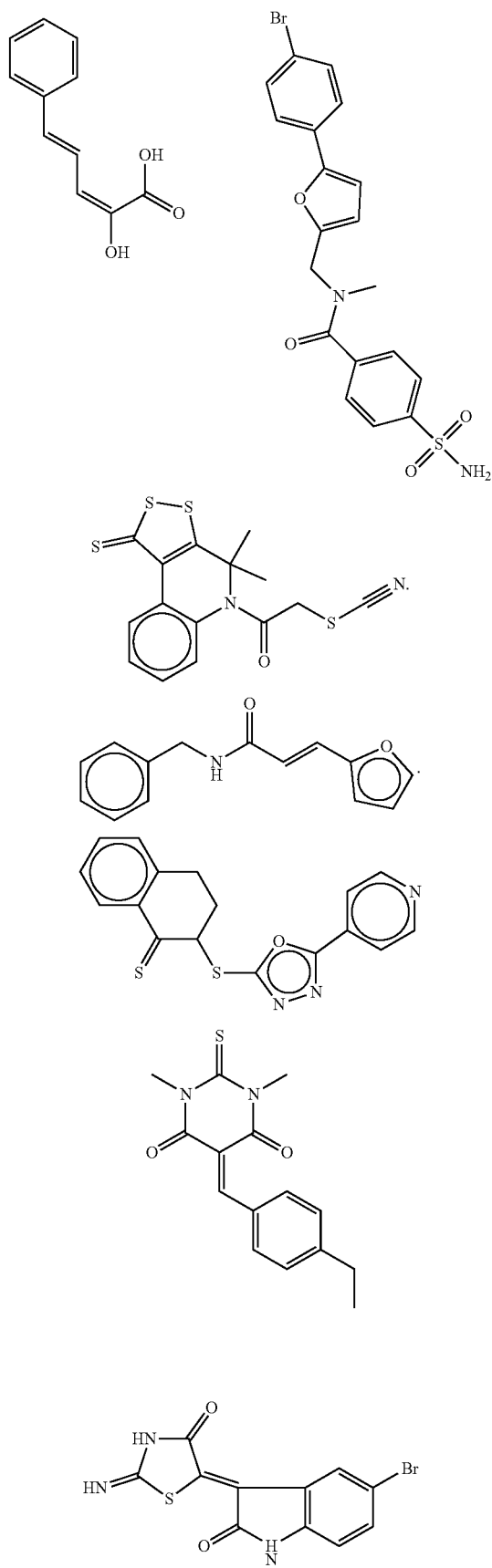
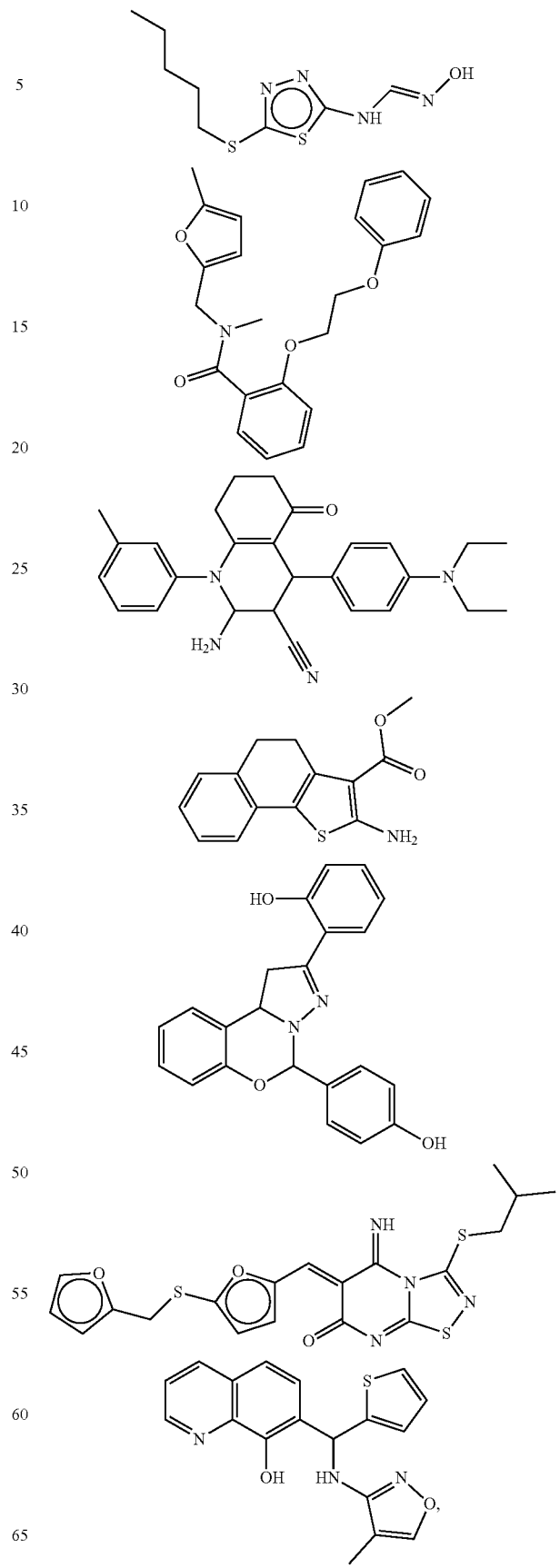

1755
-continued
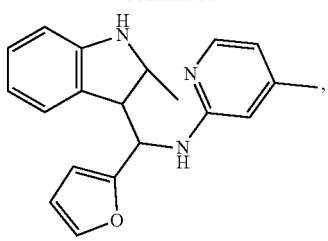
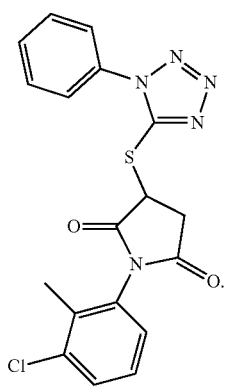
In some embodiments, the compound is:
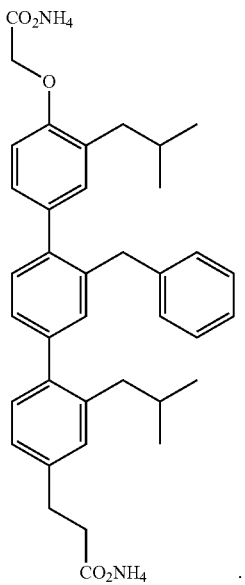
1756
In some embodiments, the compound is selected from the group consisting of:
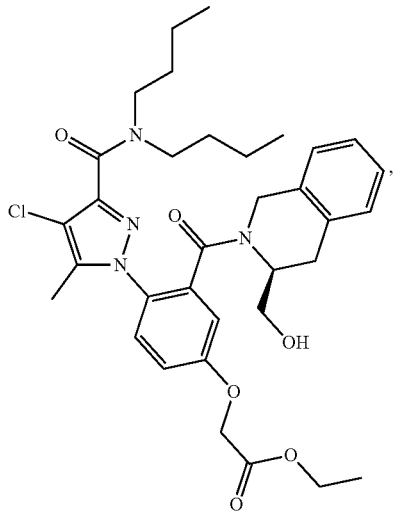
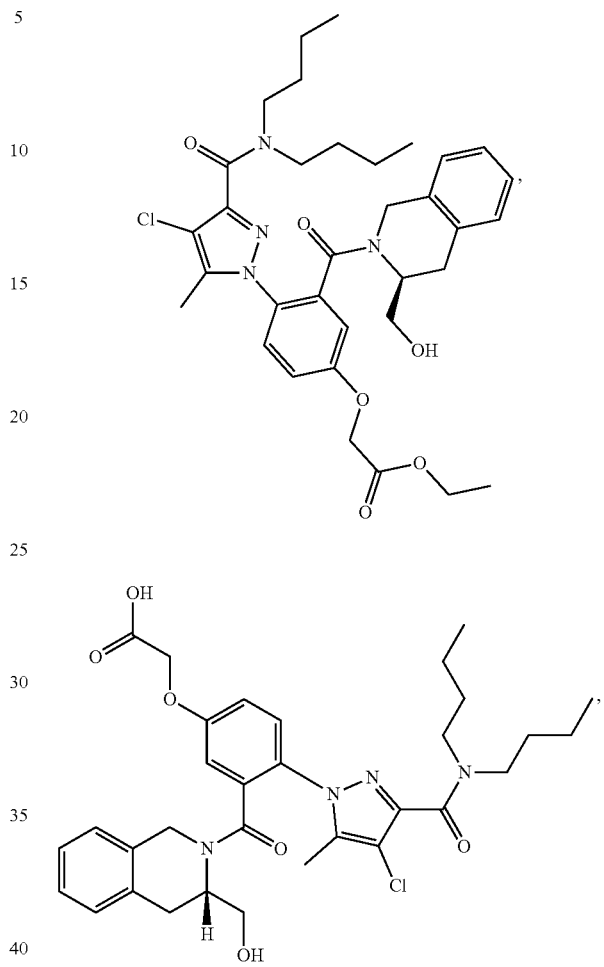
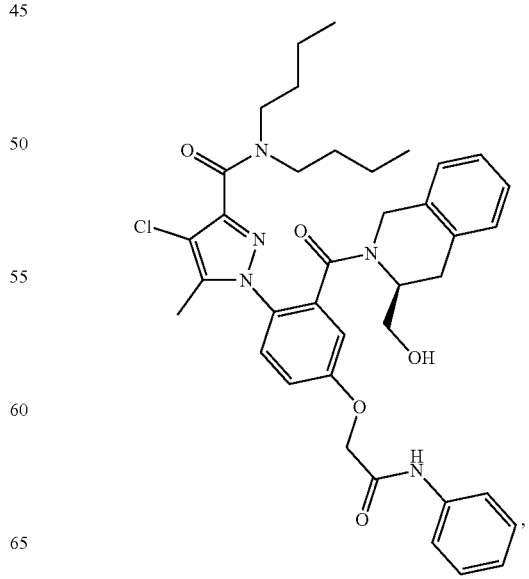

1757
-continued
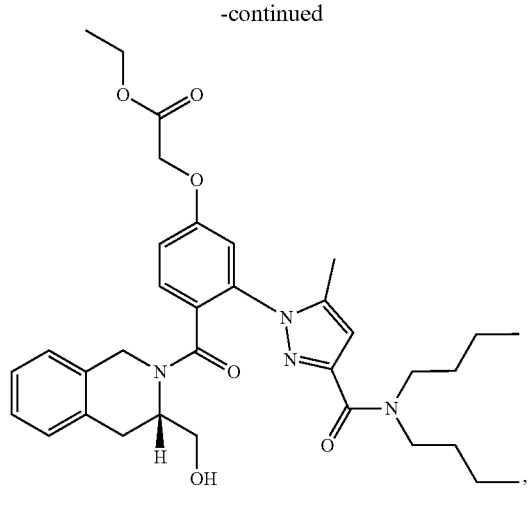
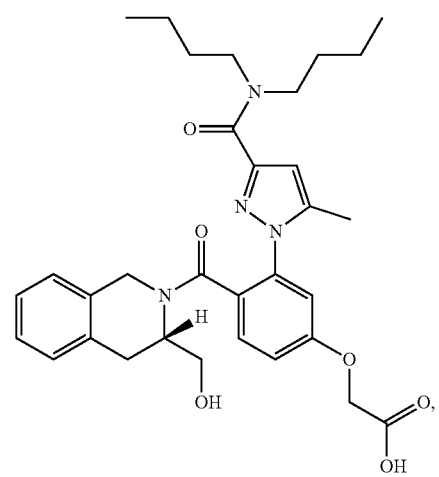
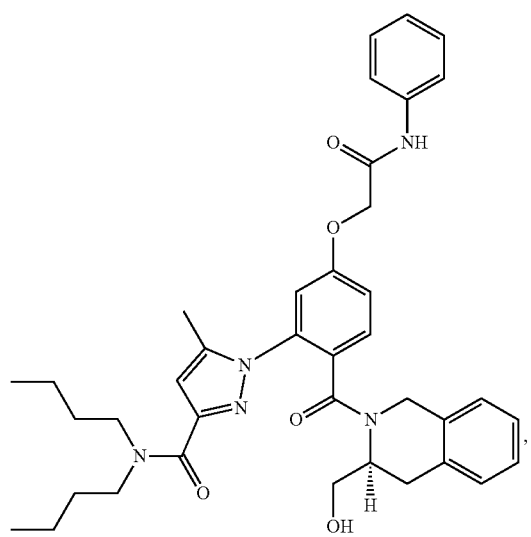
1758
-continued
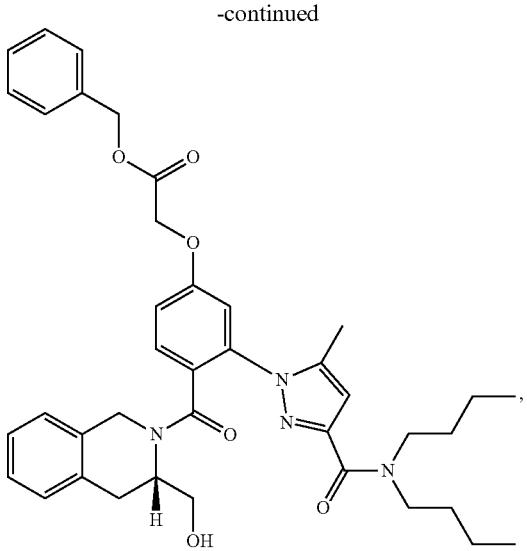
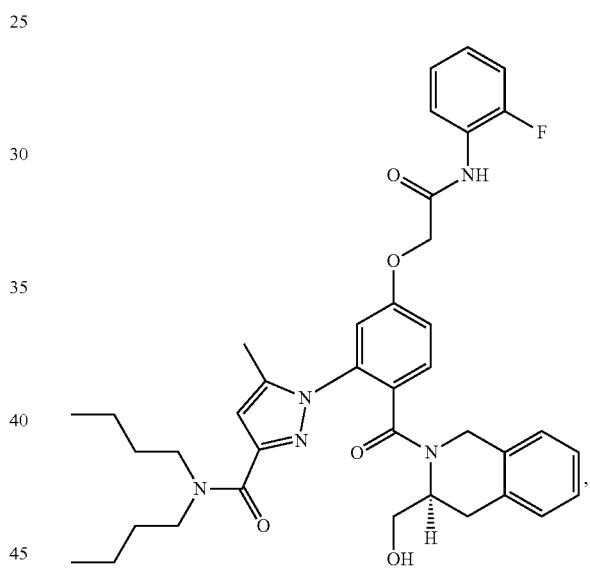
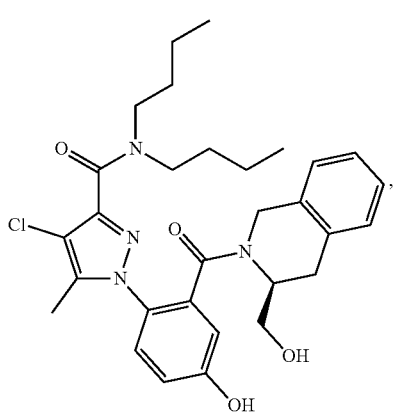

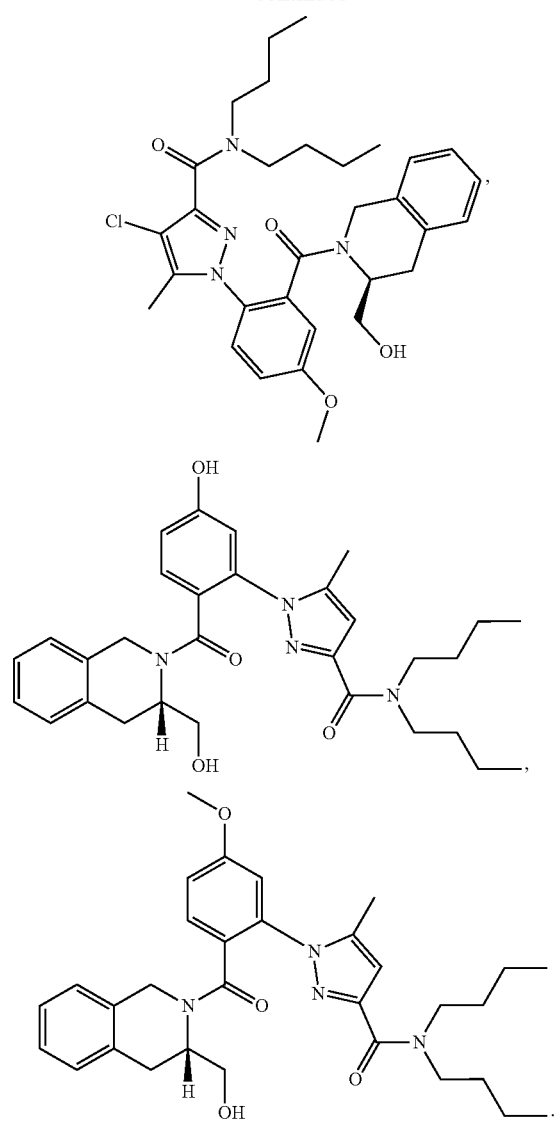
In some embodiments, the compound is selected from the group consisting of:
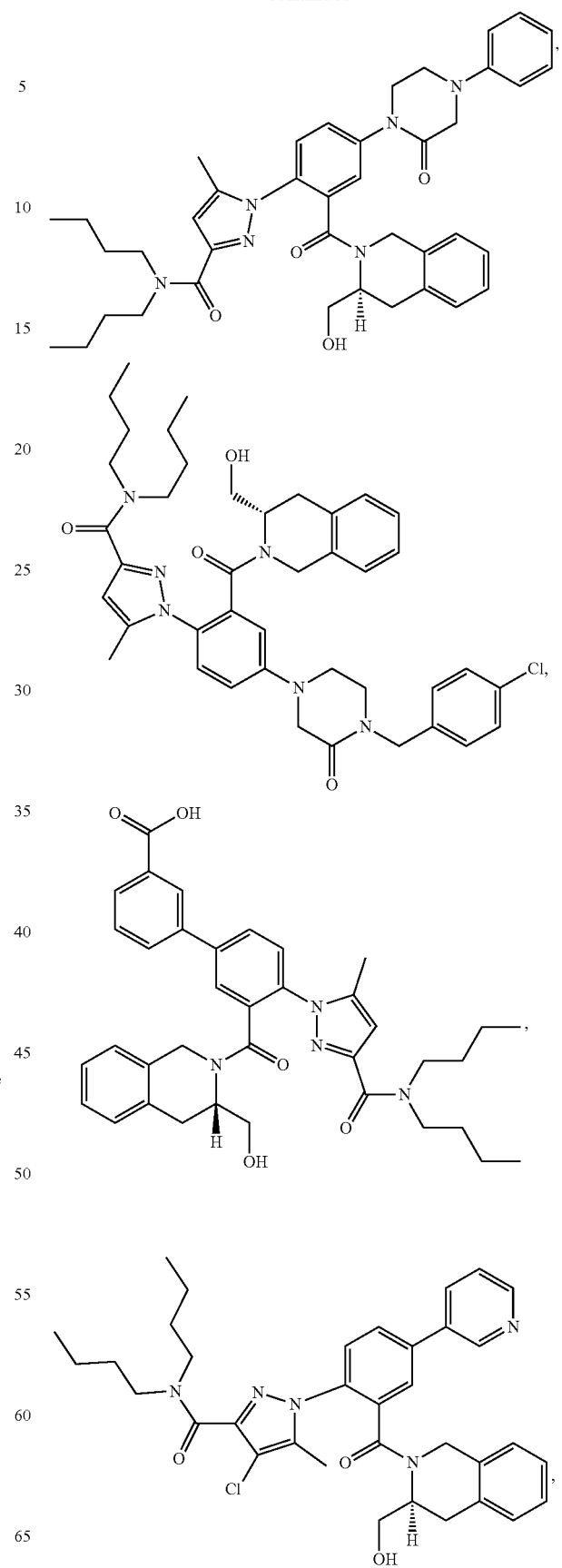

1761
-continued
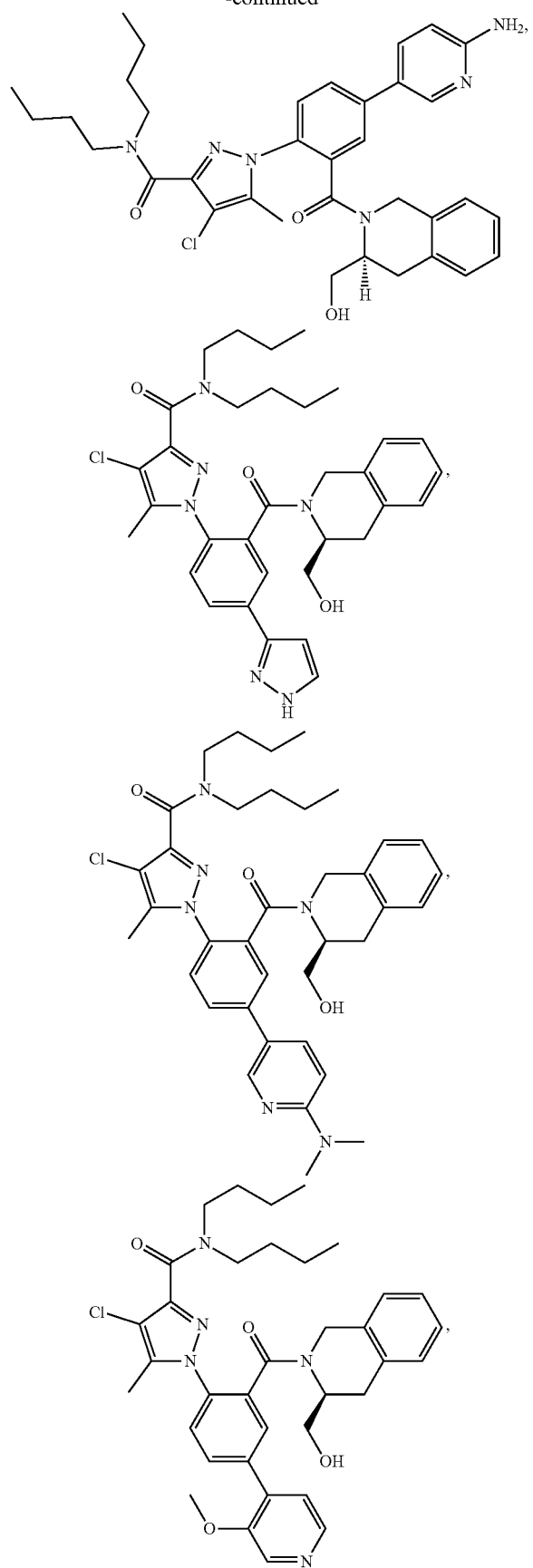
1762
-continued
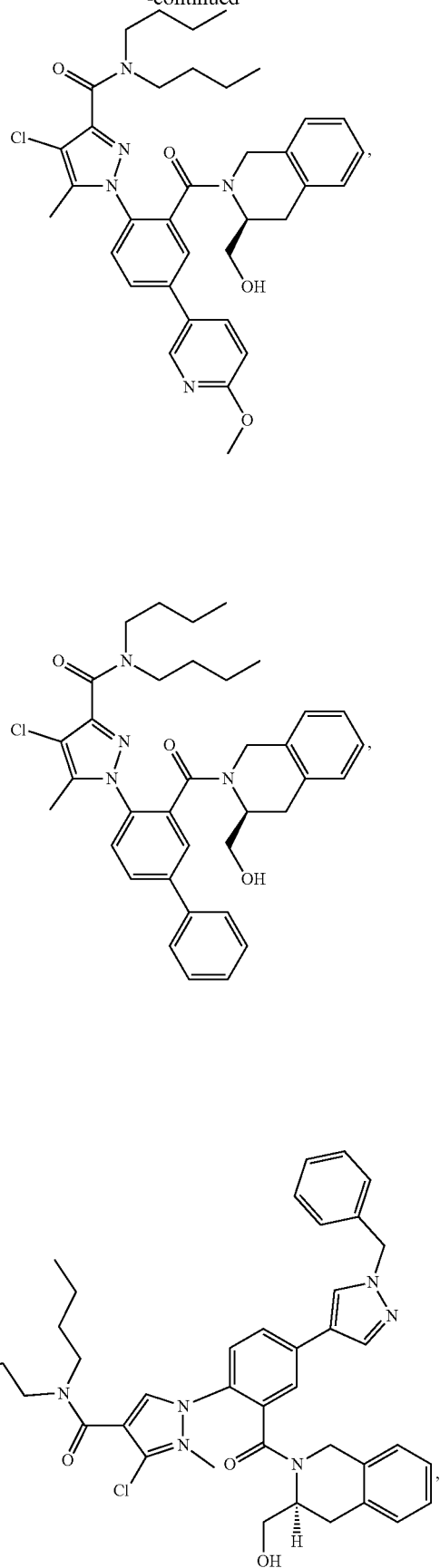

1763
-continued
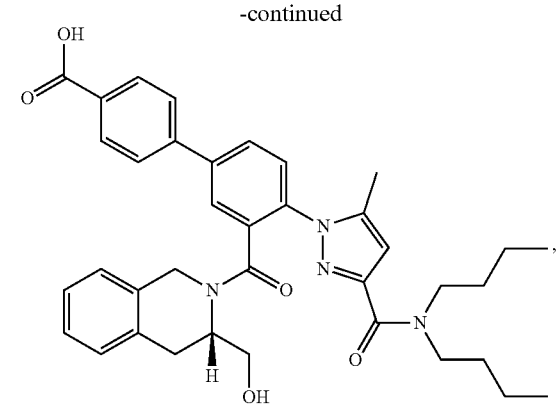
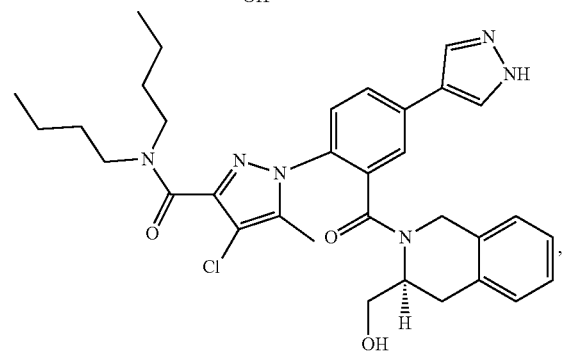
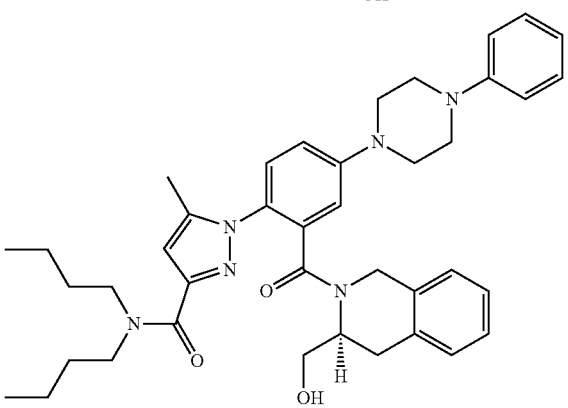
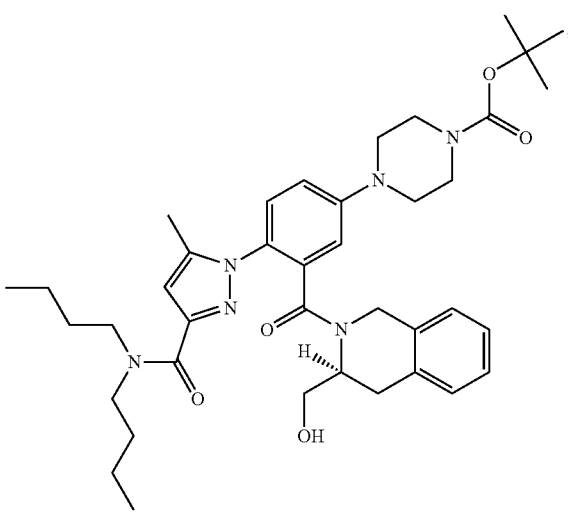
1764
-continued
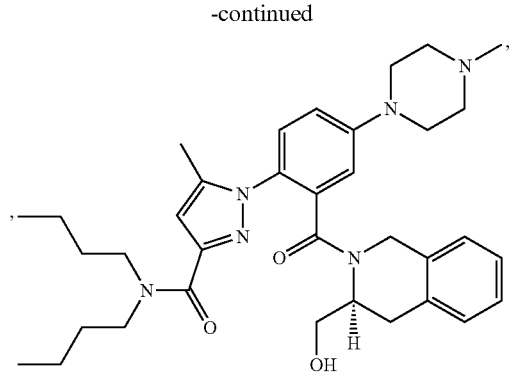
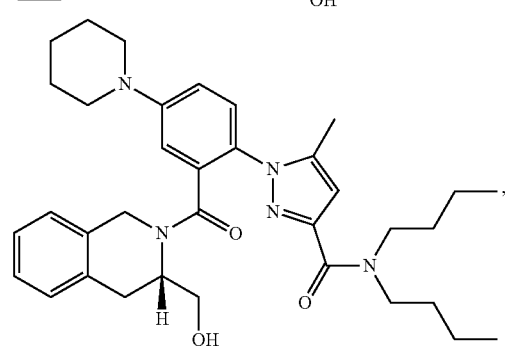
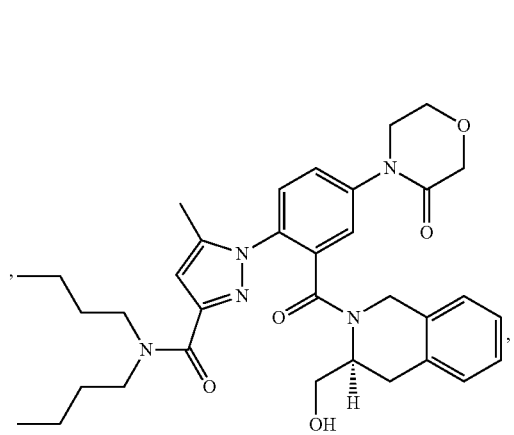
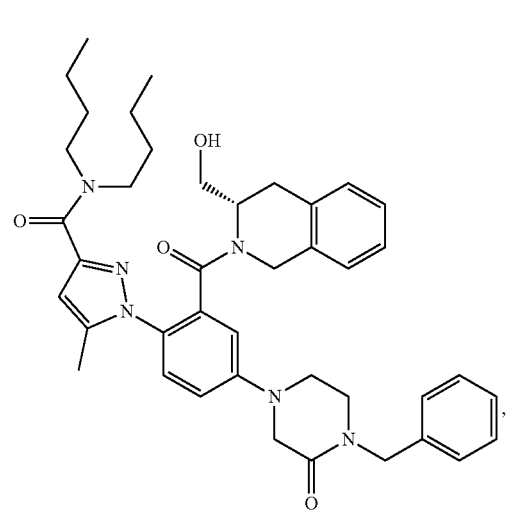

1765
-continued
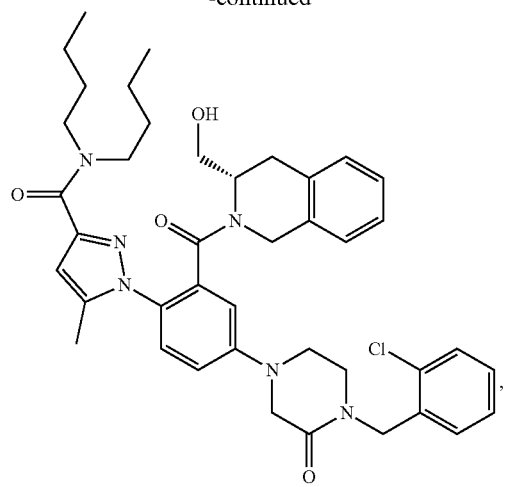
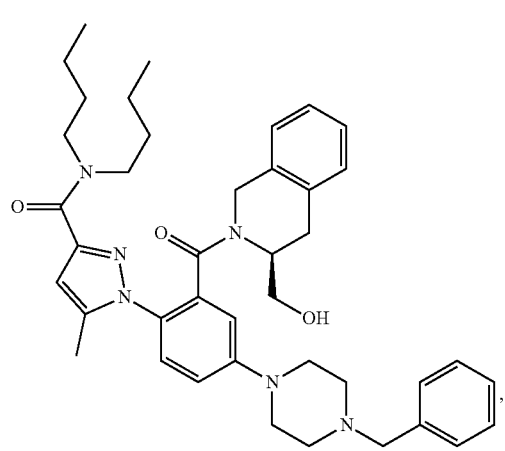
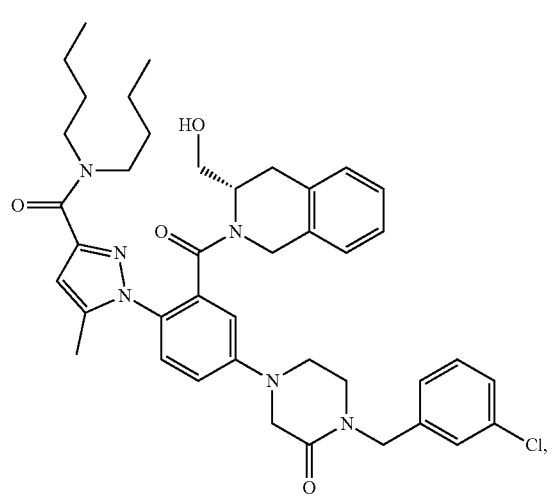
1766
-continued
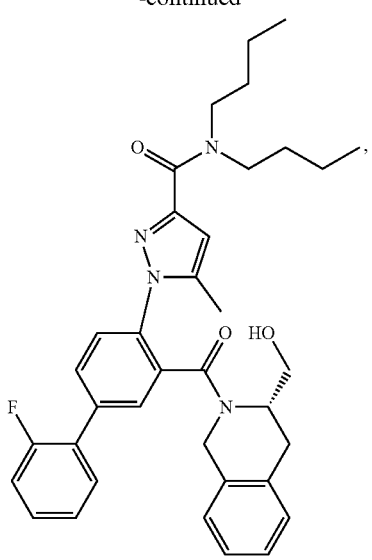
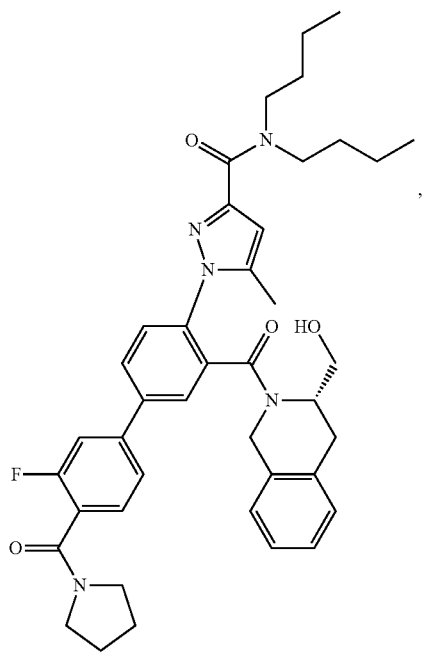

| 1767 -continued | 1768 -continued |
|---|---|
| 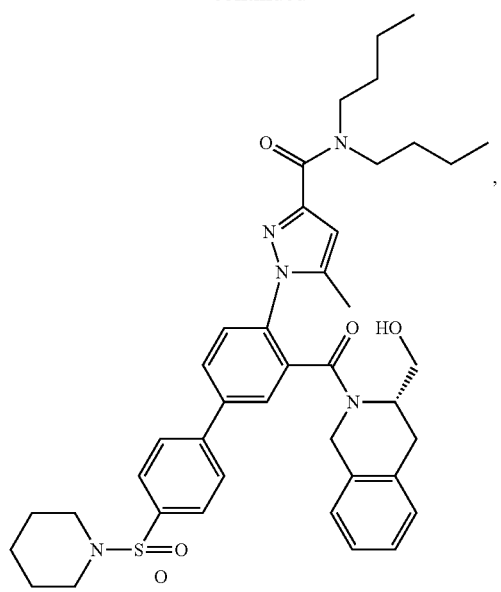 | 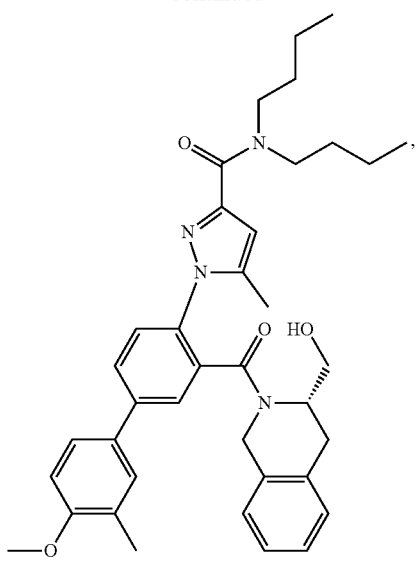 |

1769
-continued
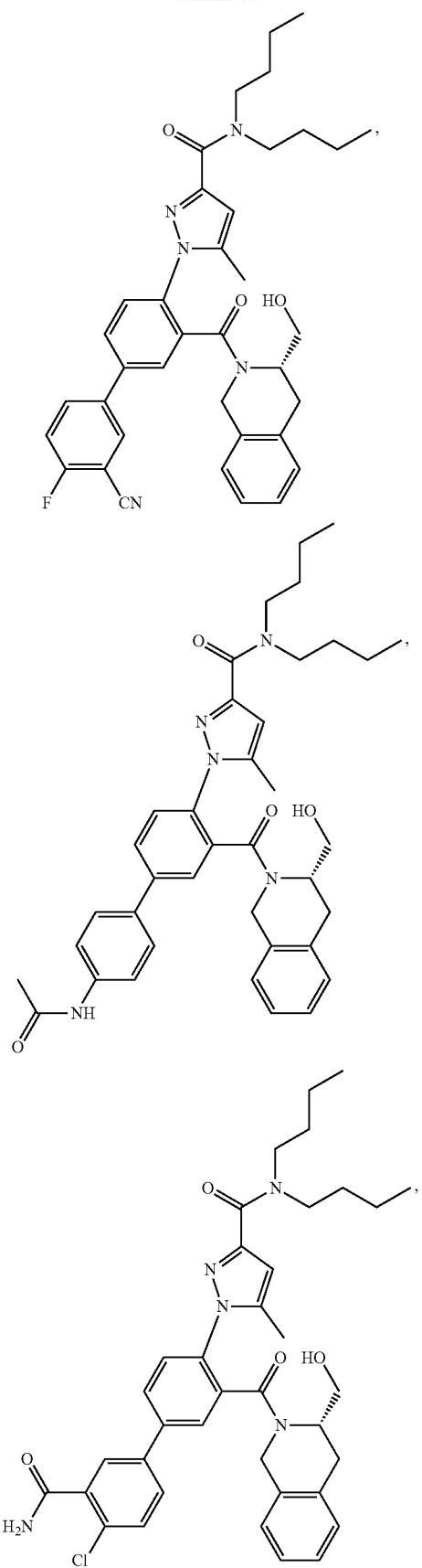
1770
-continued
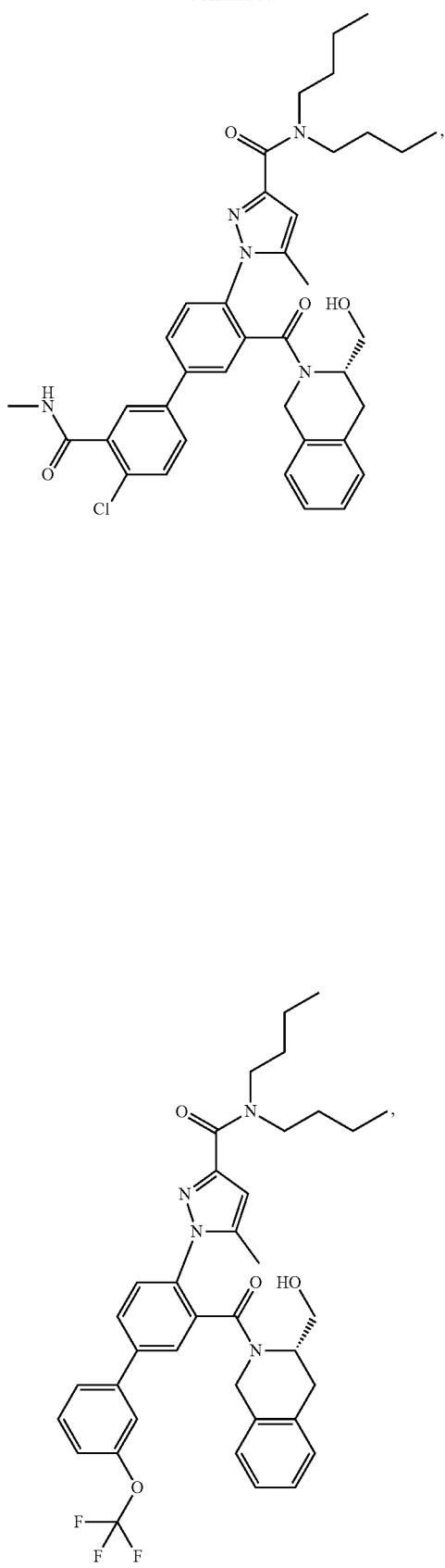

1771
-continued
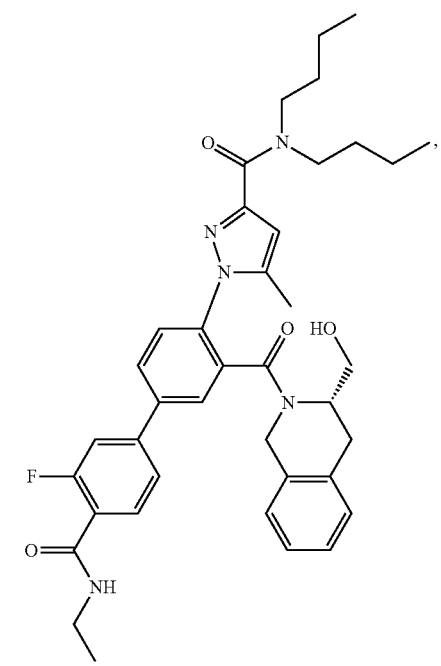
1772
-continued
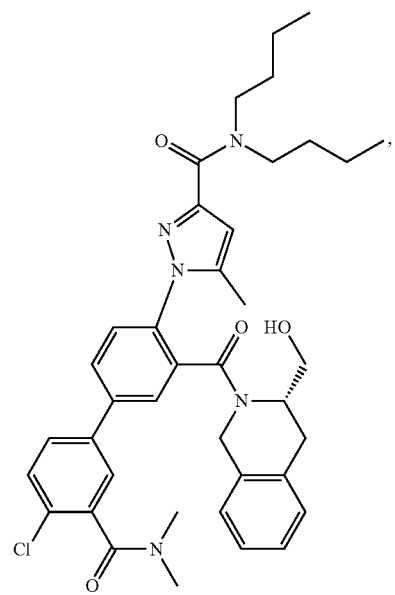
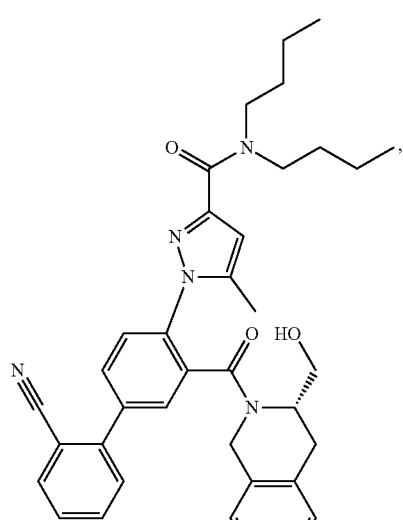
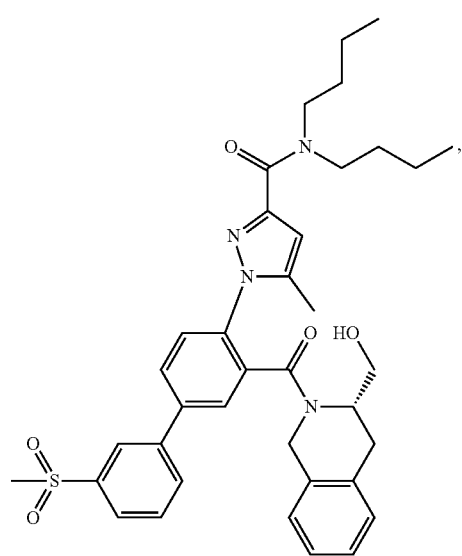
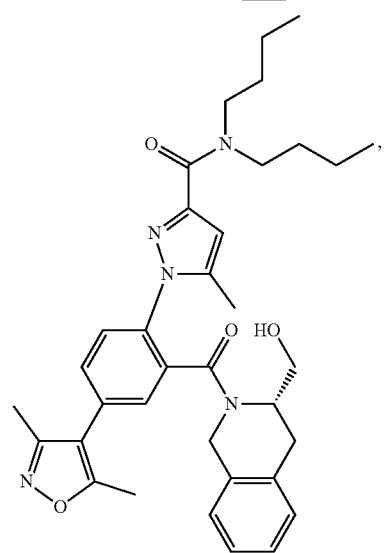

1773
-continued
1774
-continued
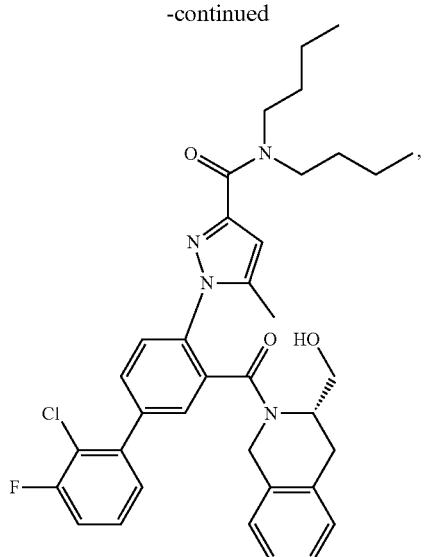
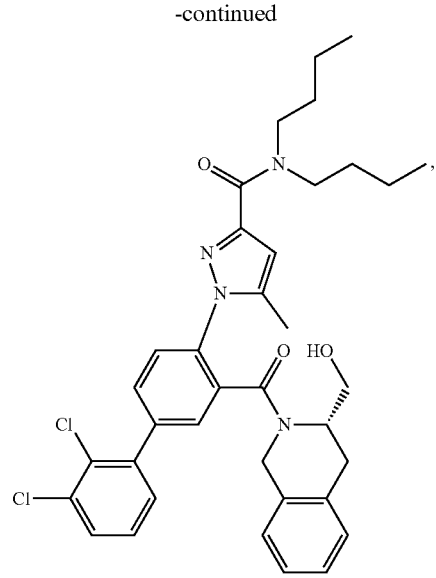

1775
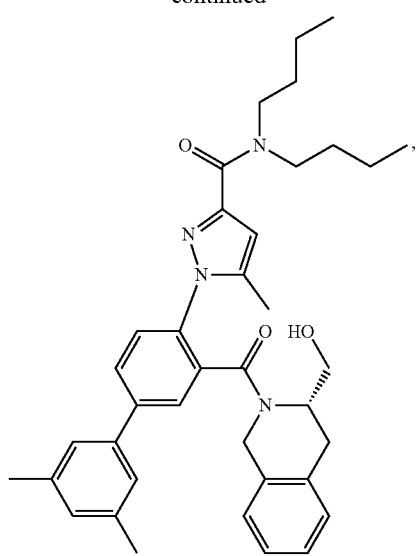
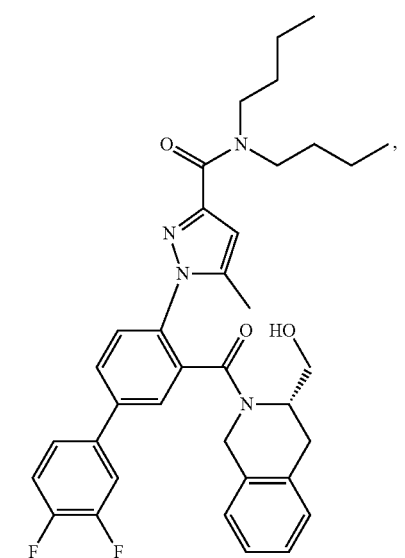
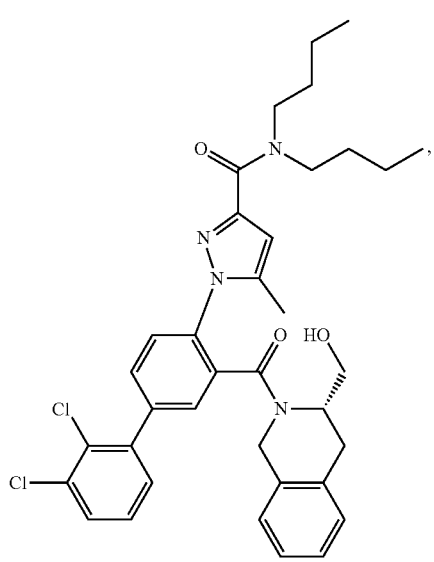
1776
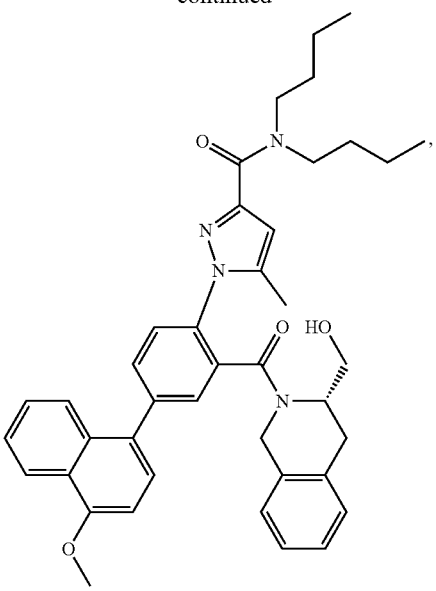
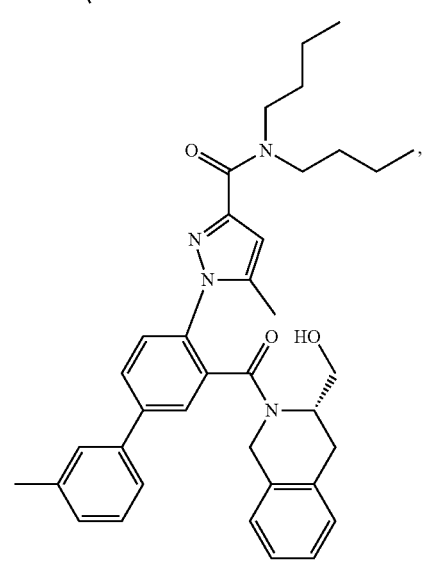
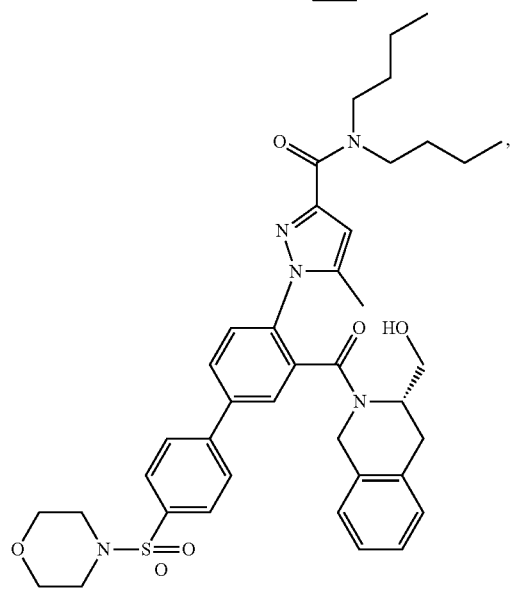

1777
-continued
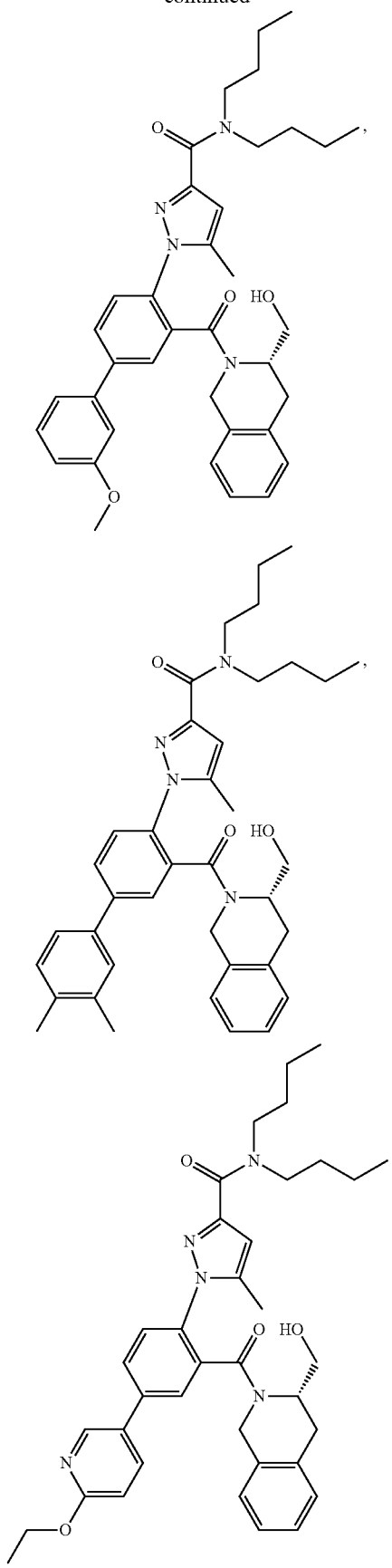
1778
-continued
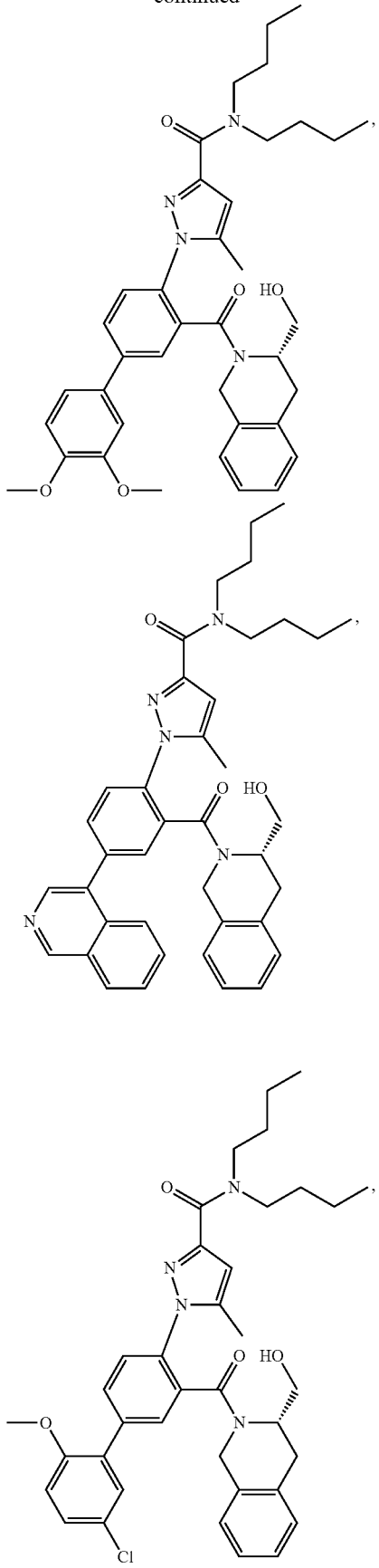

1779
-continued
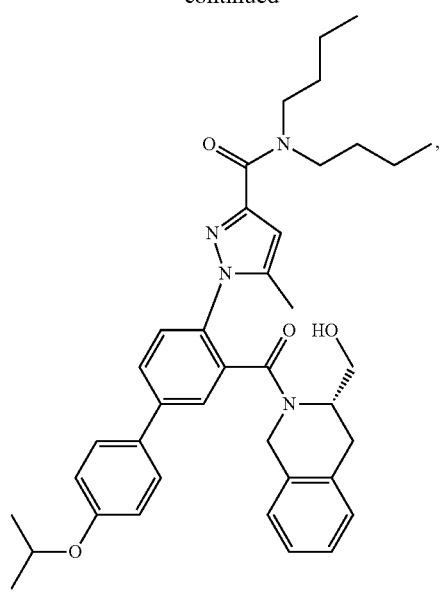
1780
-continued
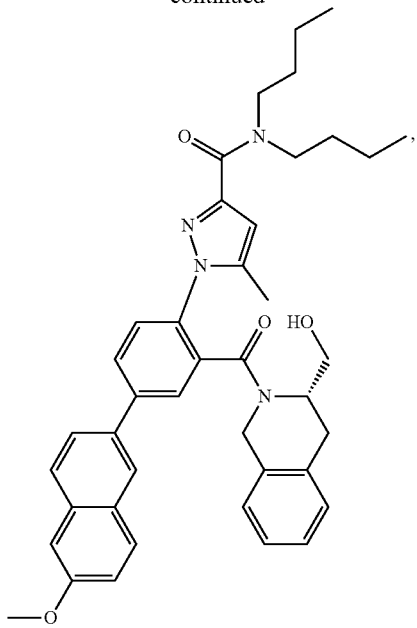
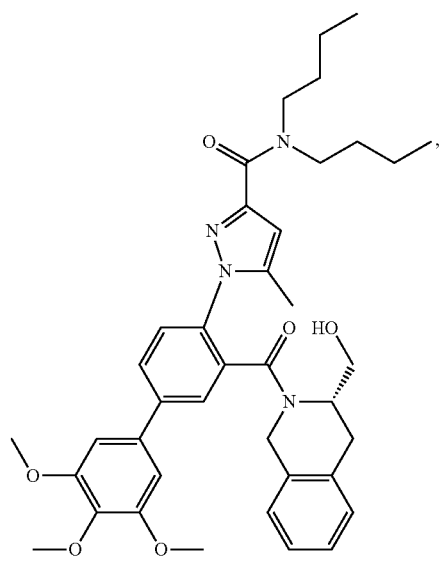
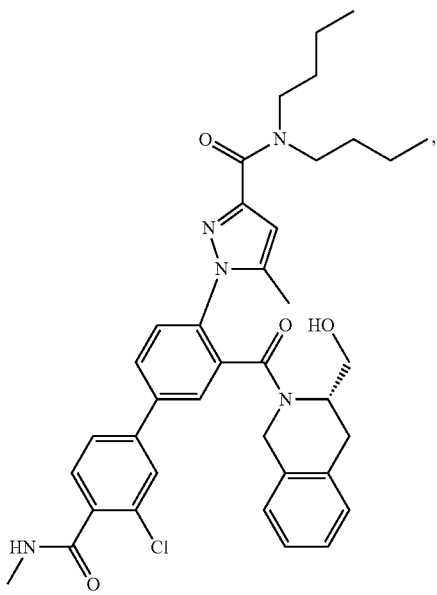

1781
-continued
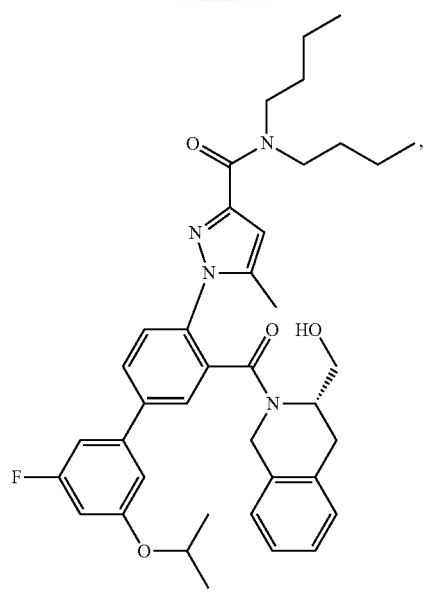
1782
-continued
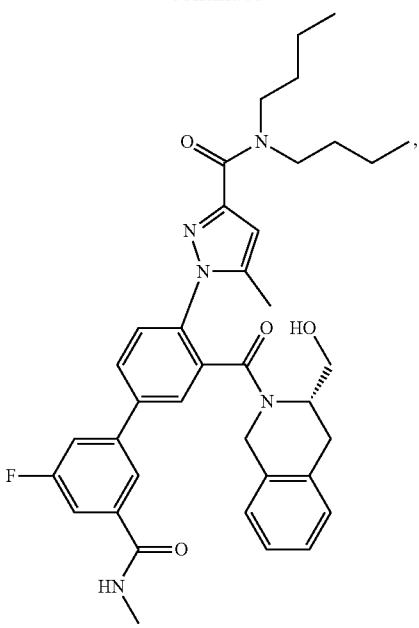
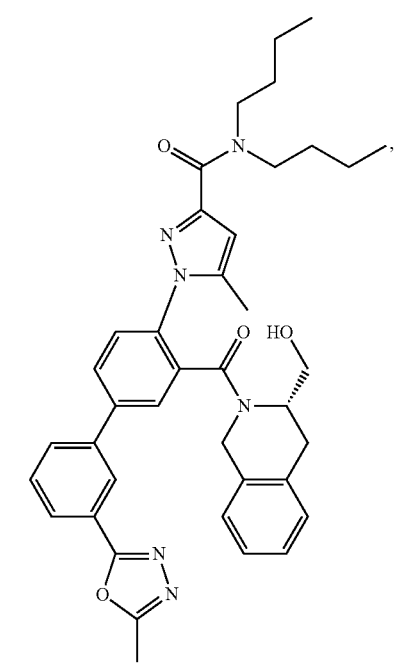

1783
-continued
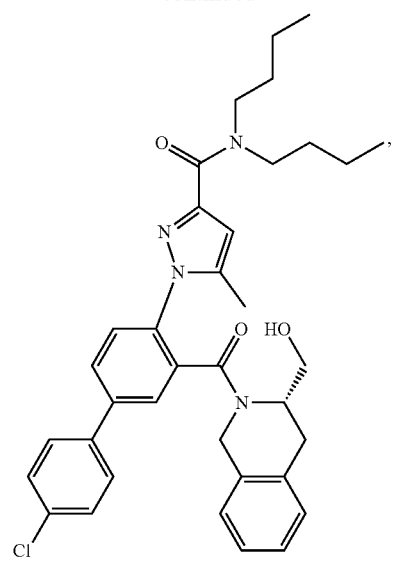
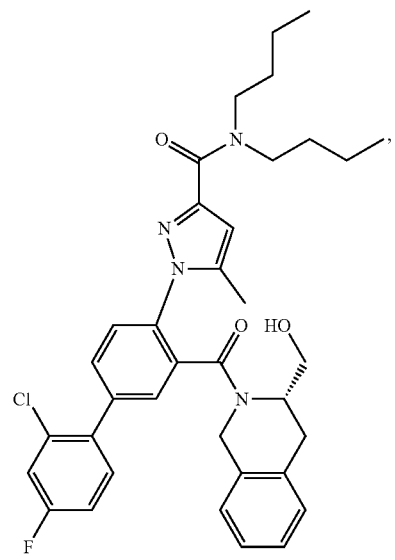
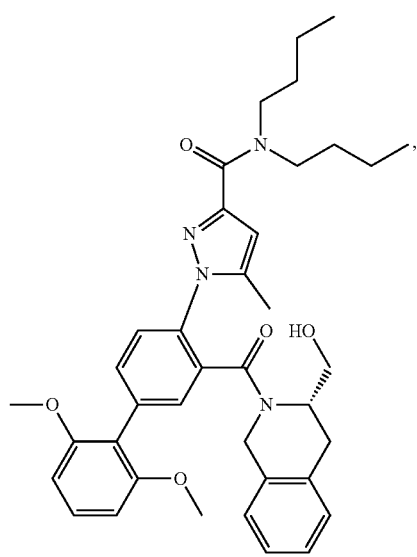
1784
-continued
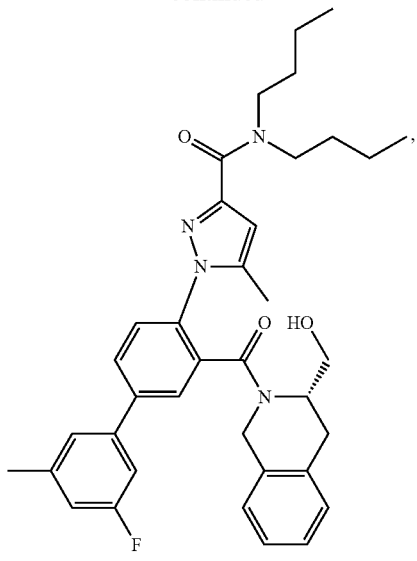
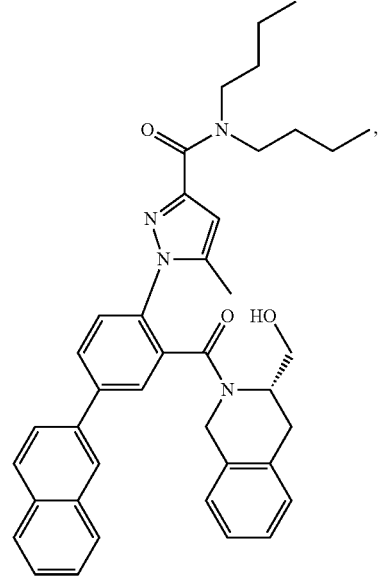
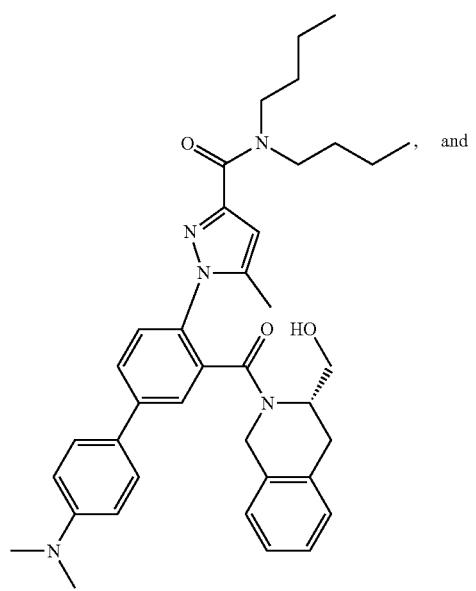
, and

1785
-continued
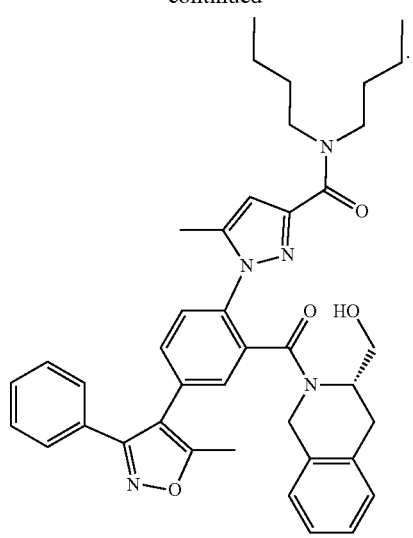
1786
-continued
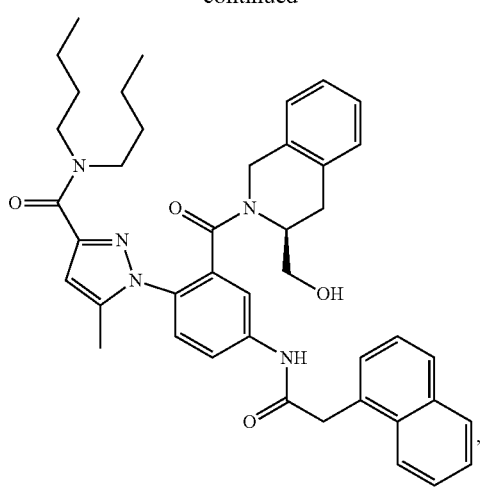
In some embodiments, the compound is selected from the group consisting of:
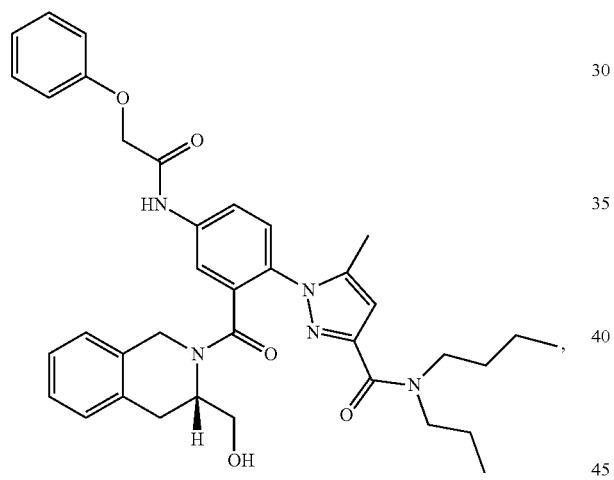
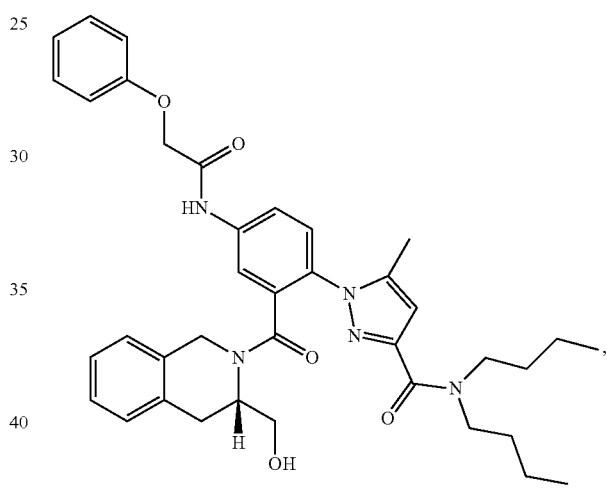
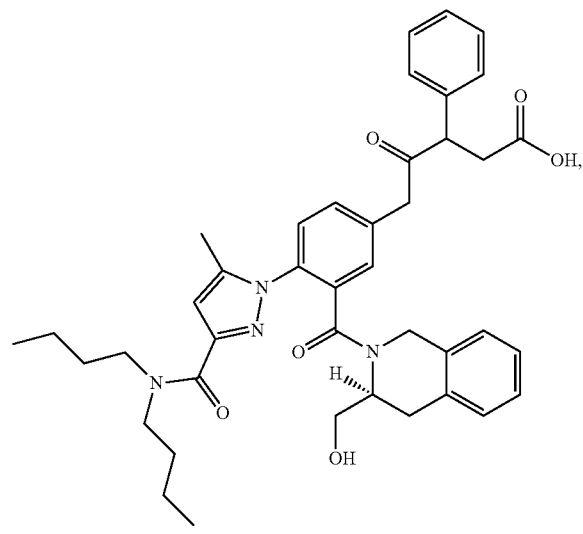
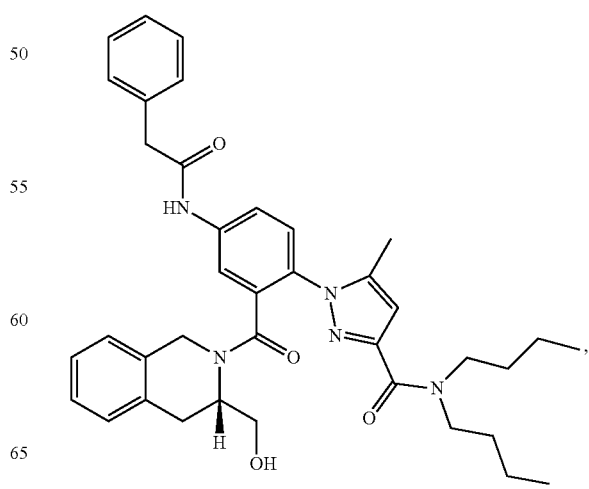

1787
-continued
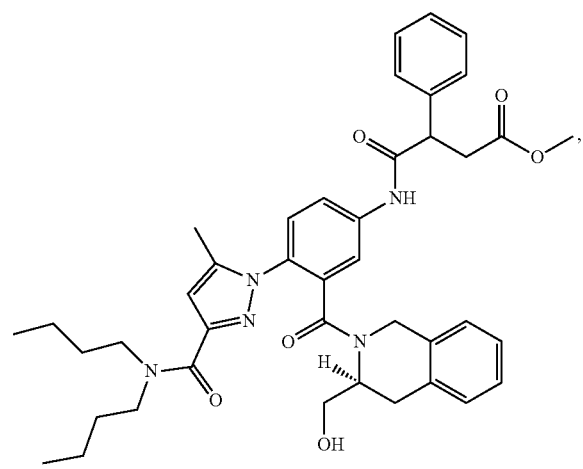
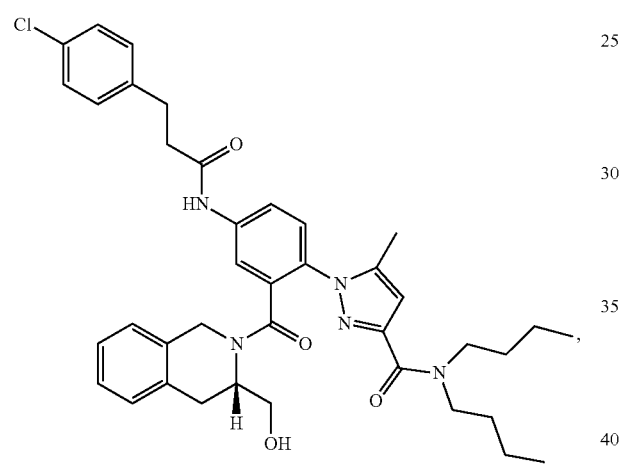
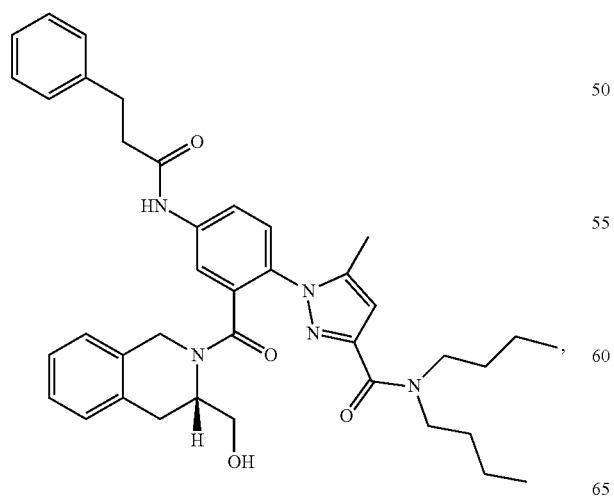
1788
-continued
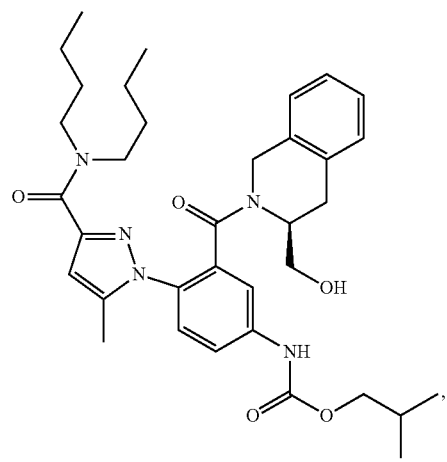
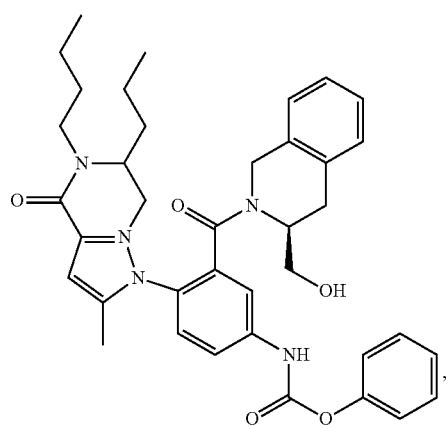
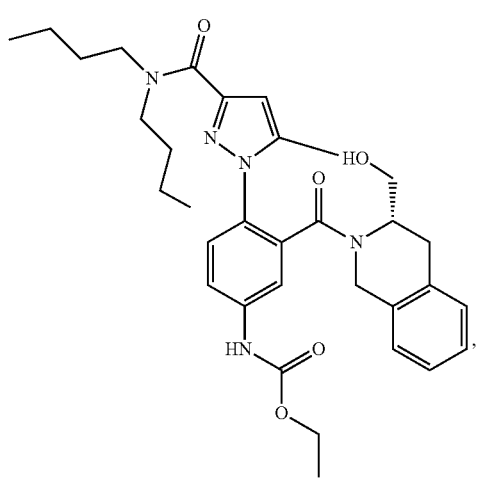

1789
-continued
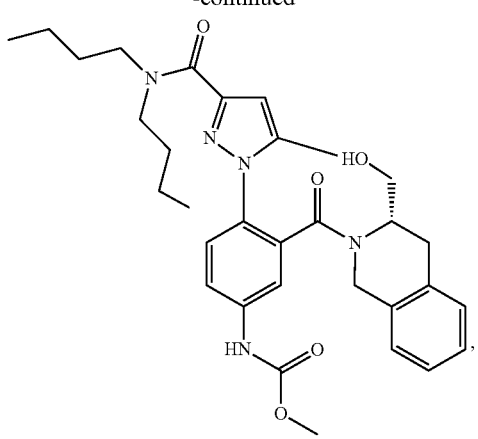
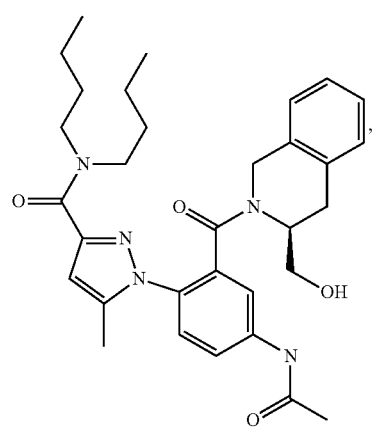
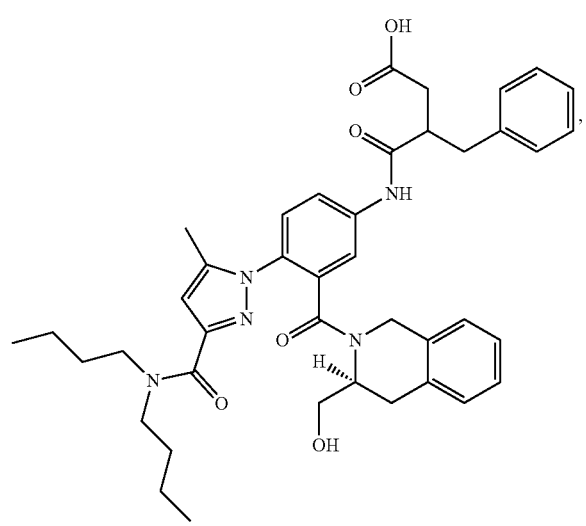
1790
-continued
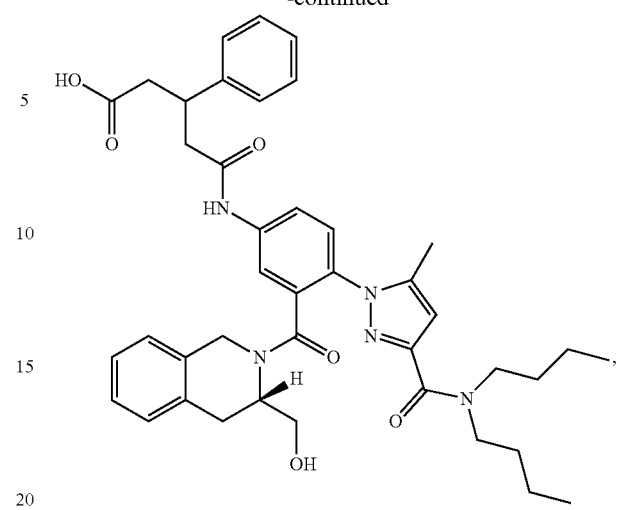
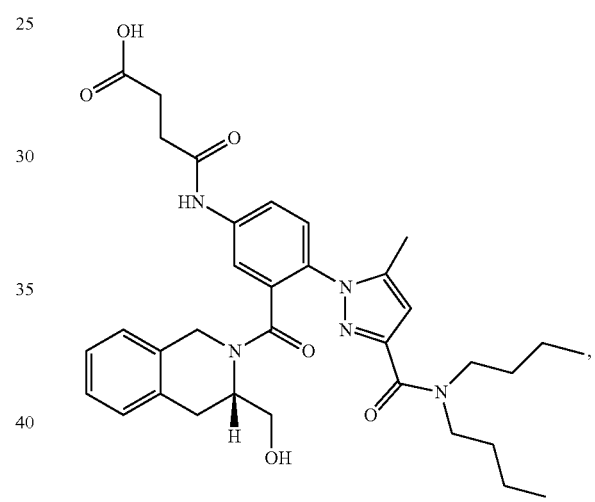
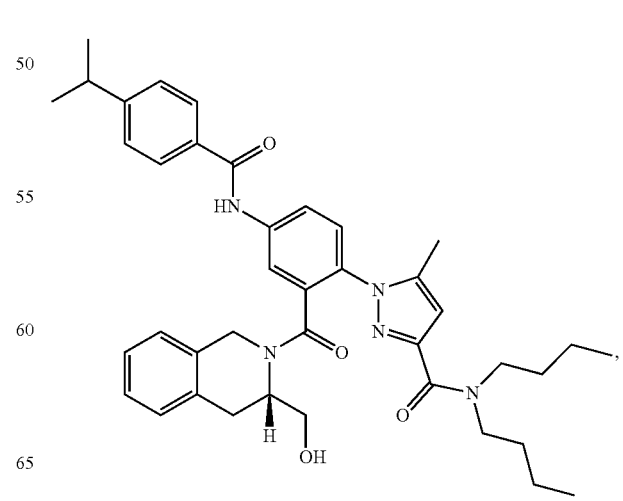

1791
-continued
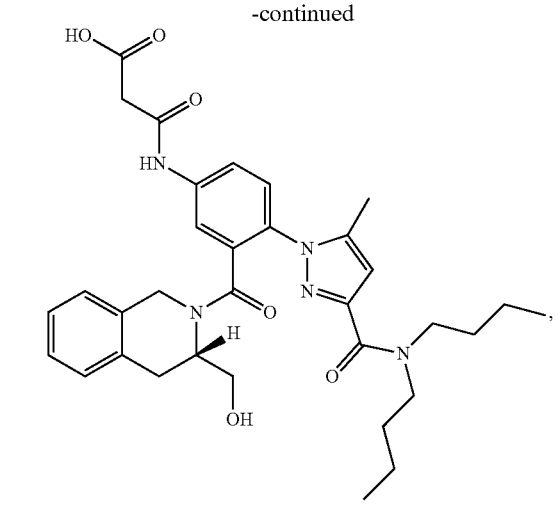
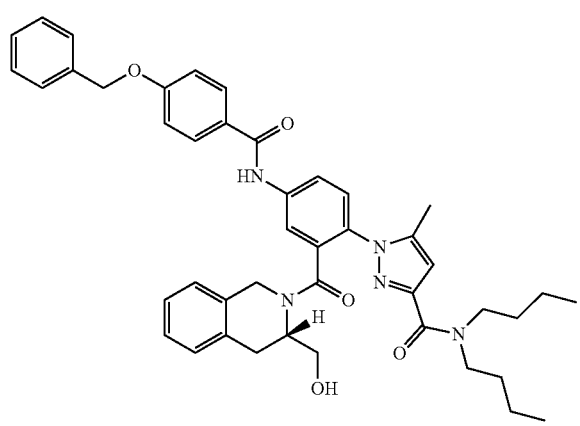
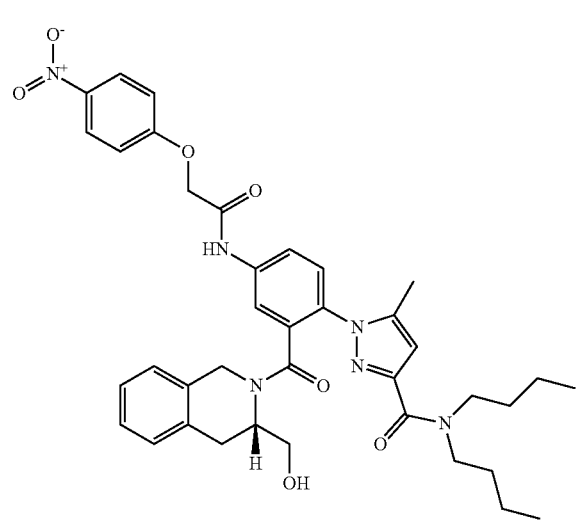
1792
-continued
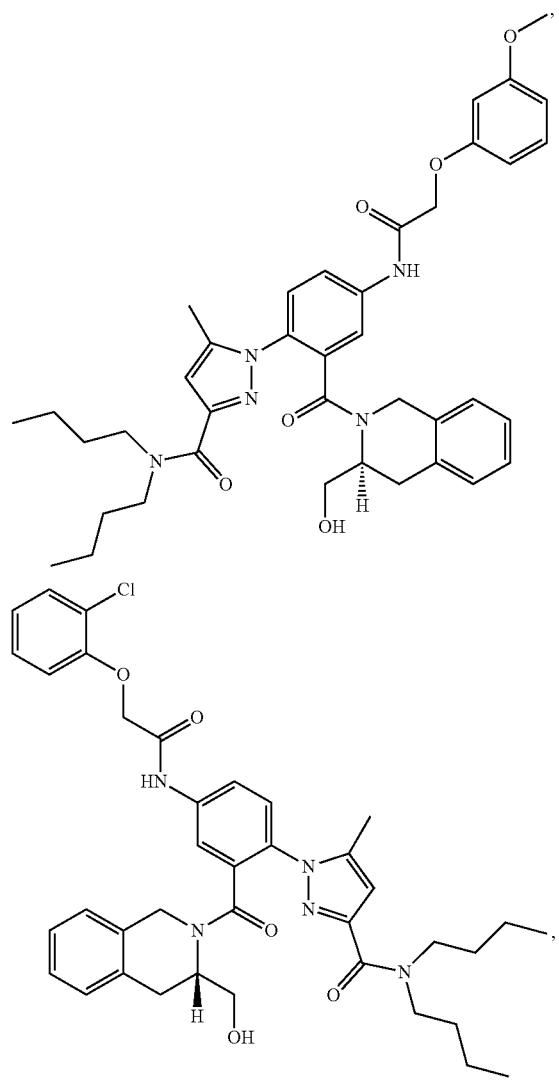
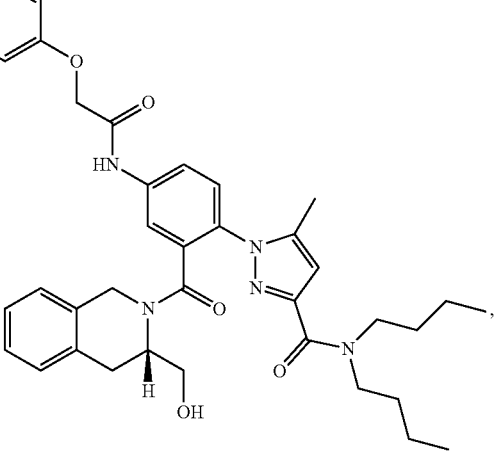

1793
-continued
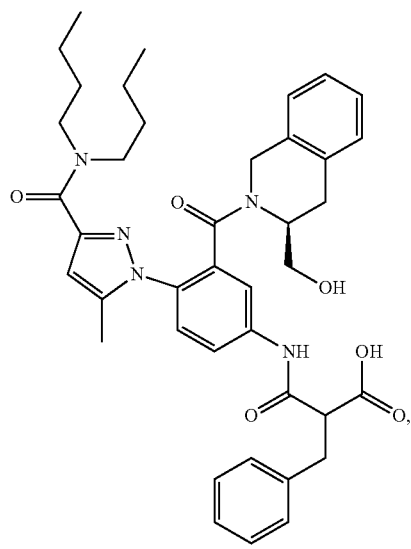
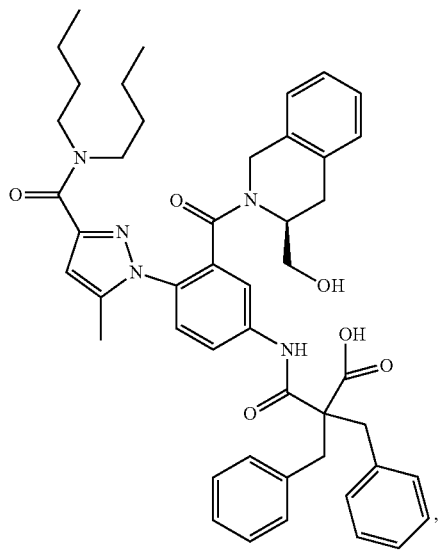
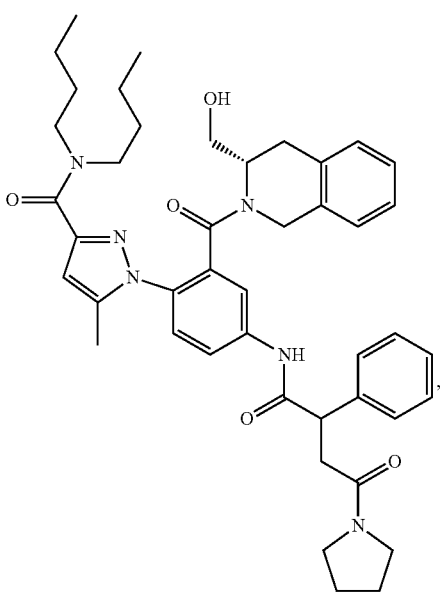
1794
-continued
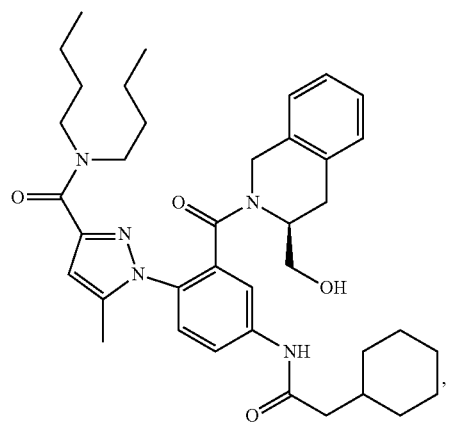
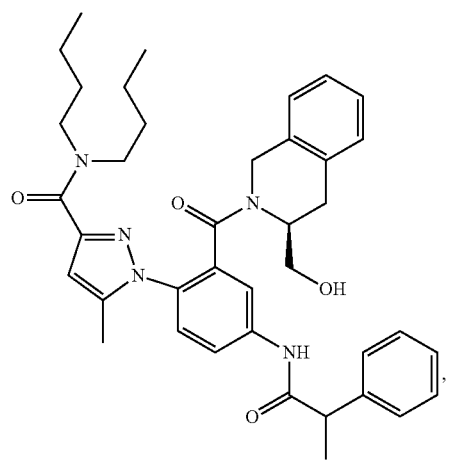
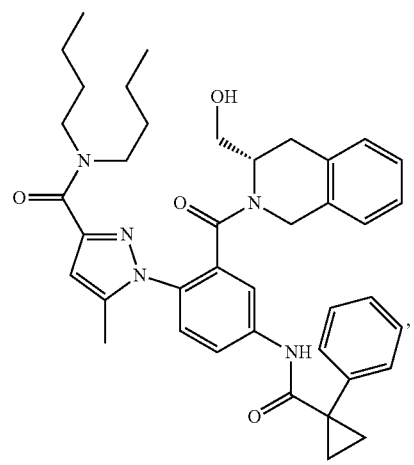

1795
-continued
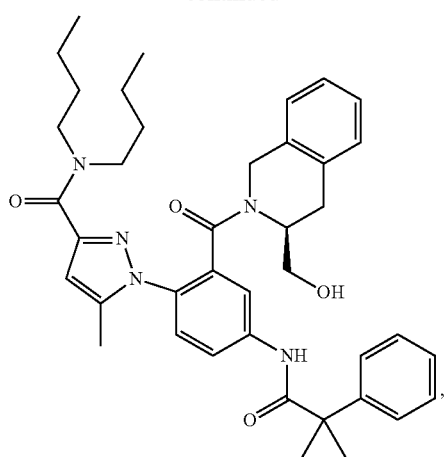
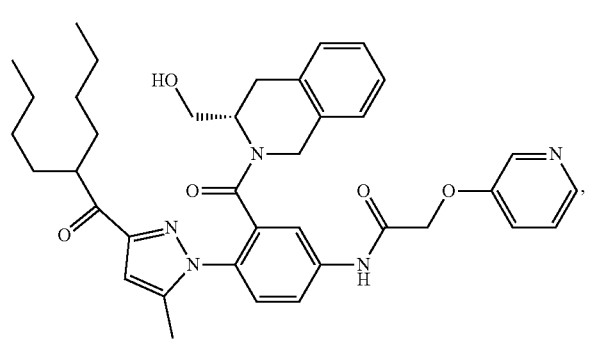
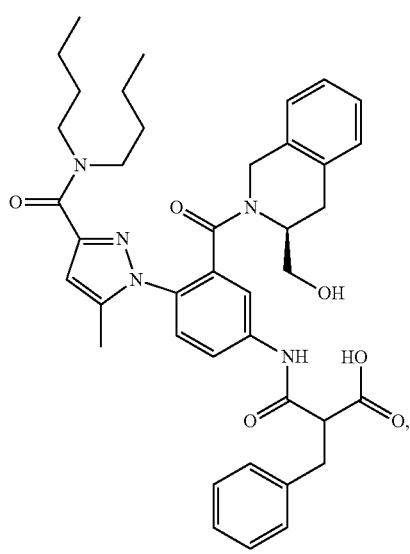
1796
-continued
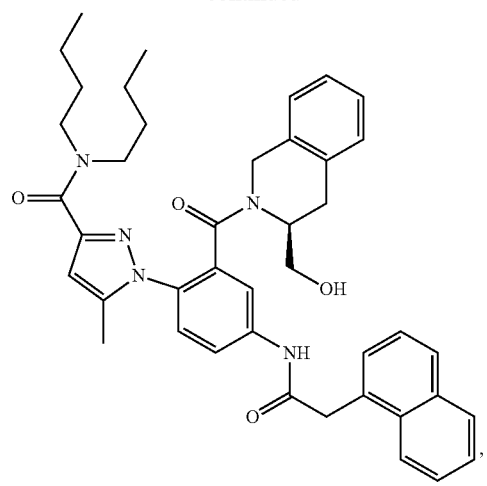
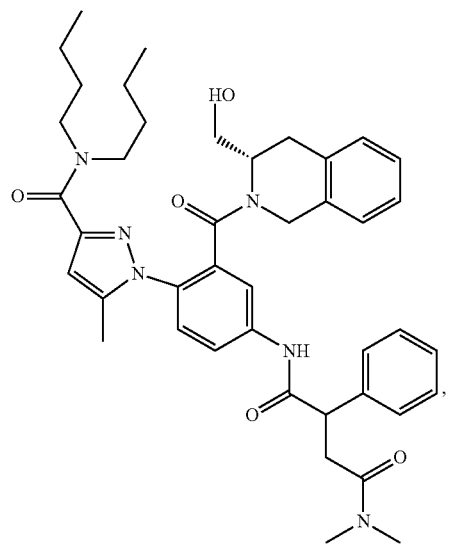
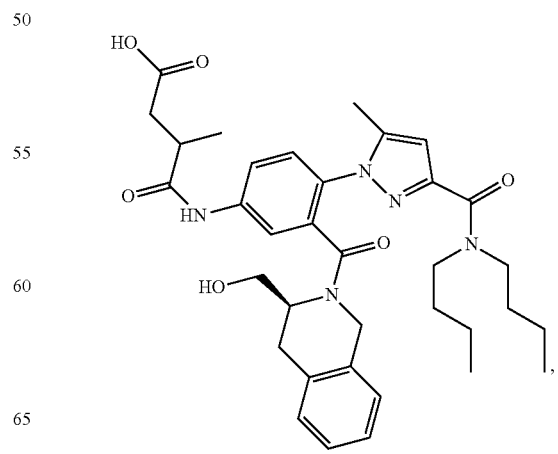

1797
-continued
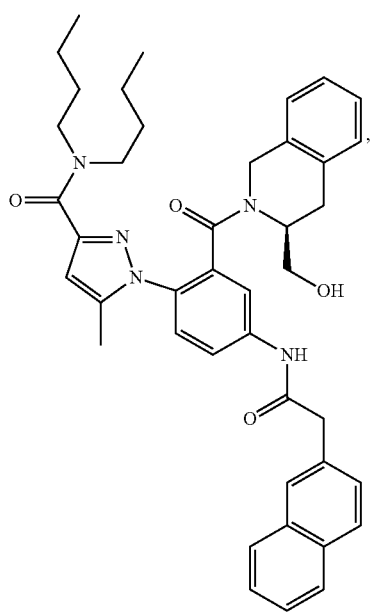
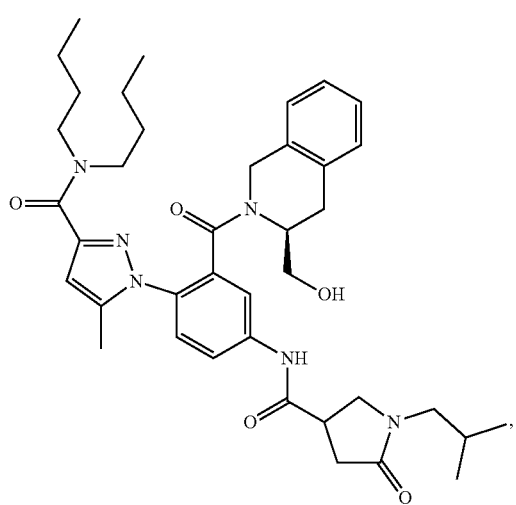
1798
-continued
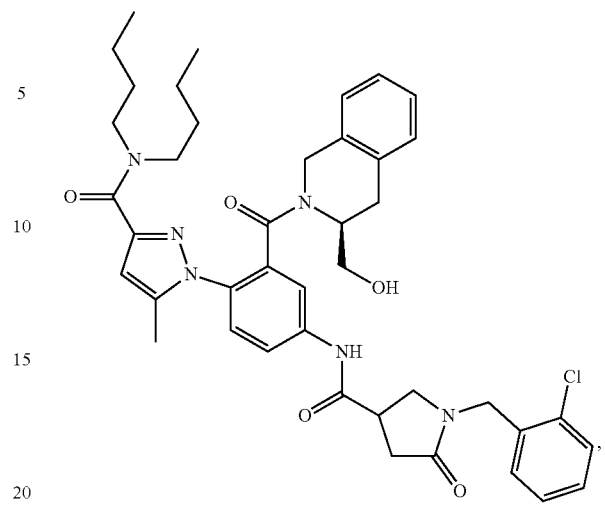
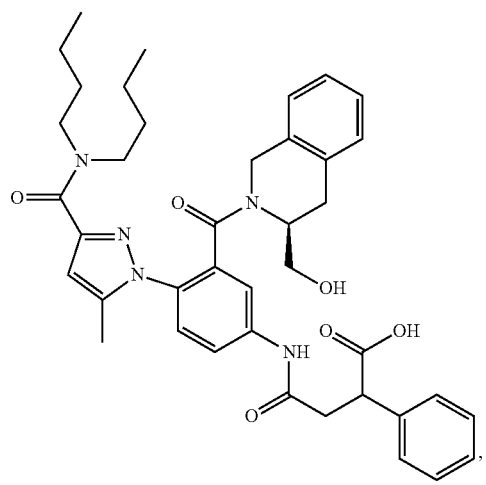
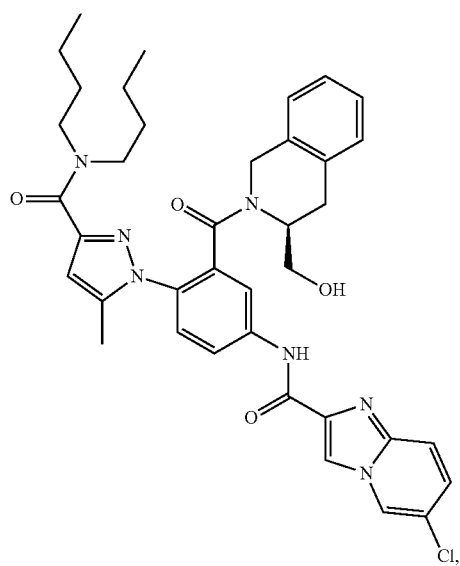

1799
-continued
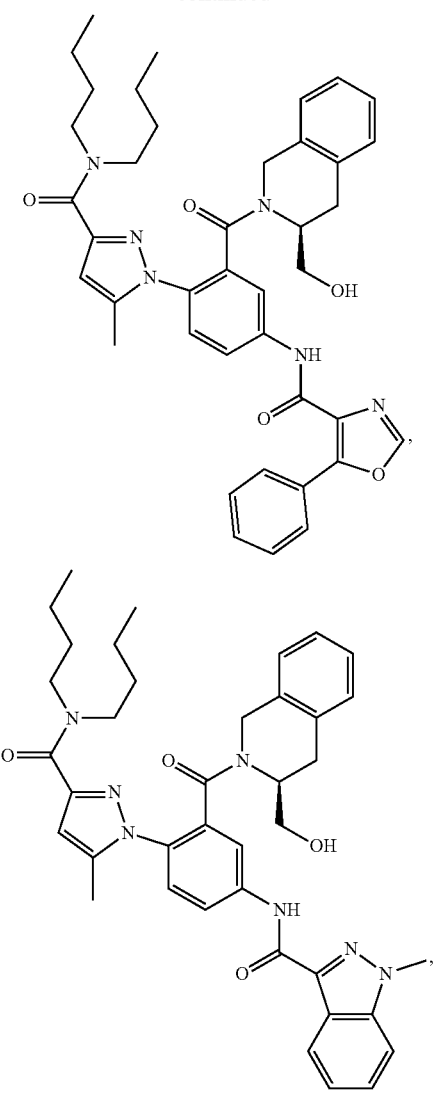
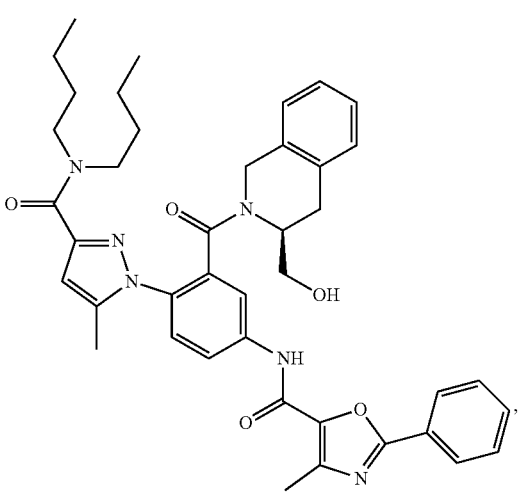
1800
-continued
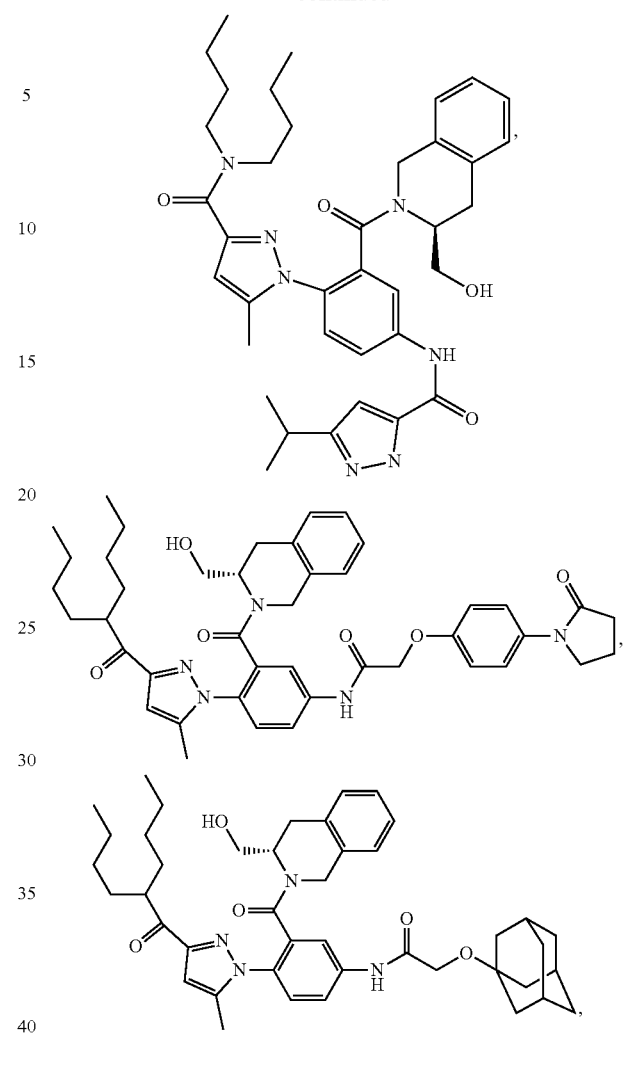
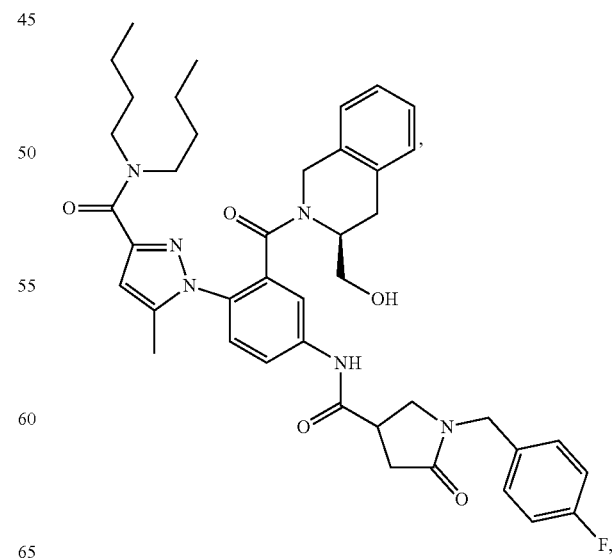

1801
-continued
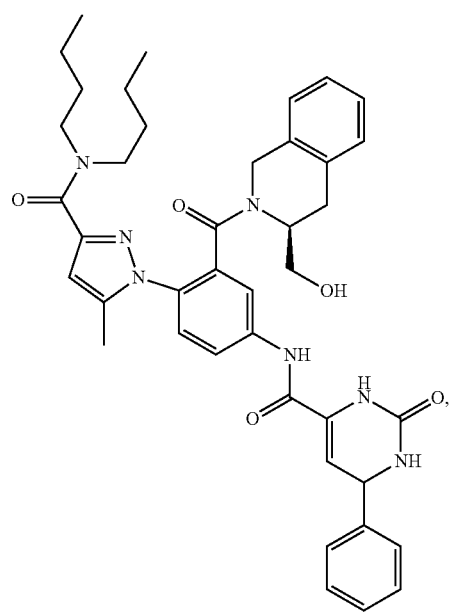
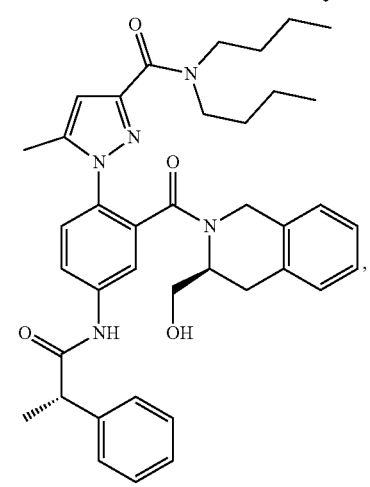
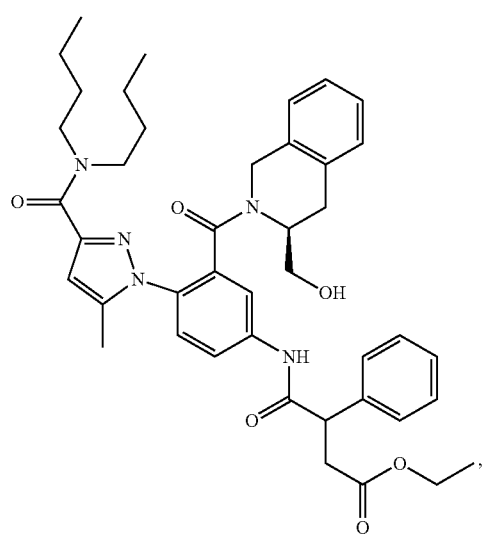
1802
-continued
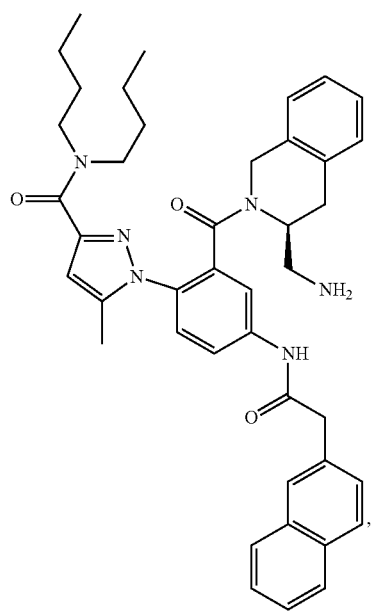
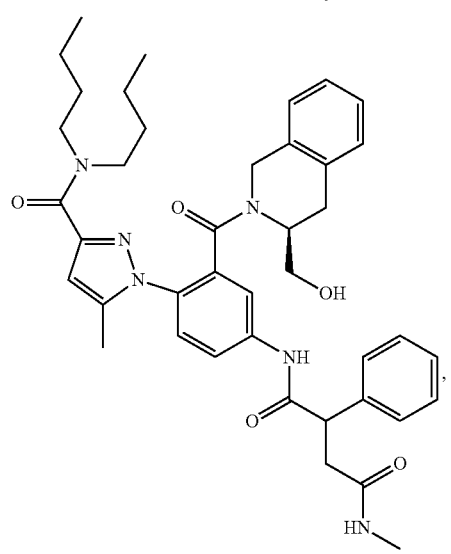
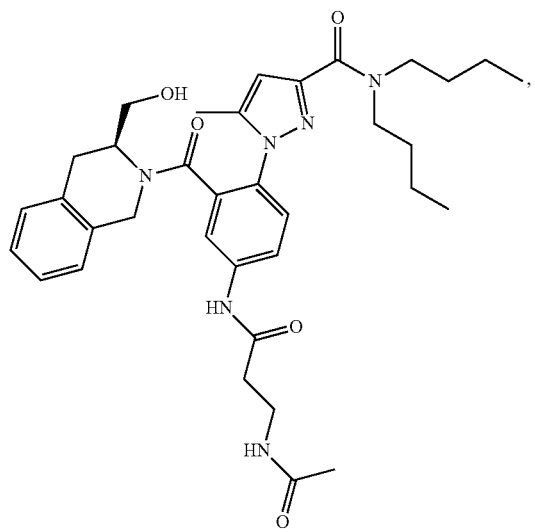

1803
-continued
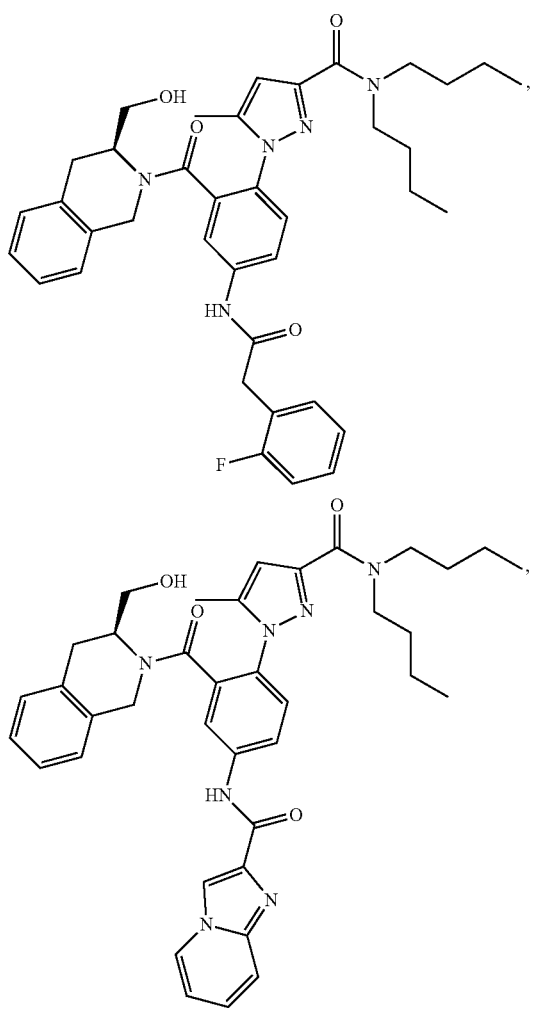
1804
-continued
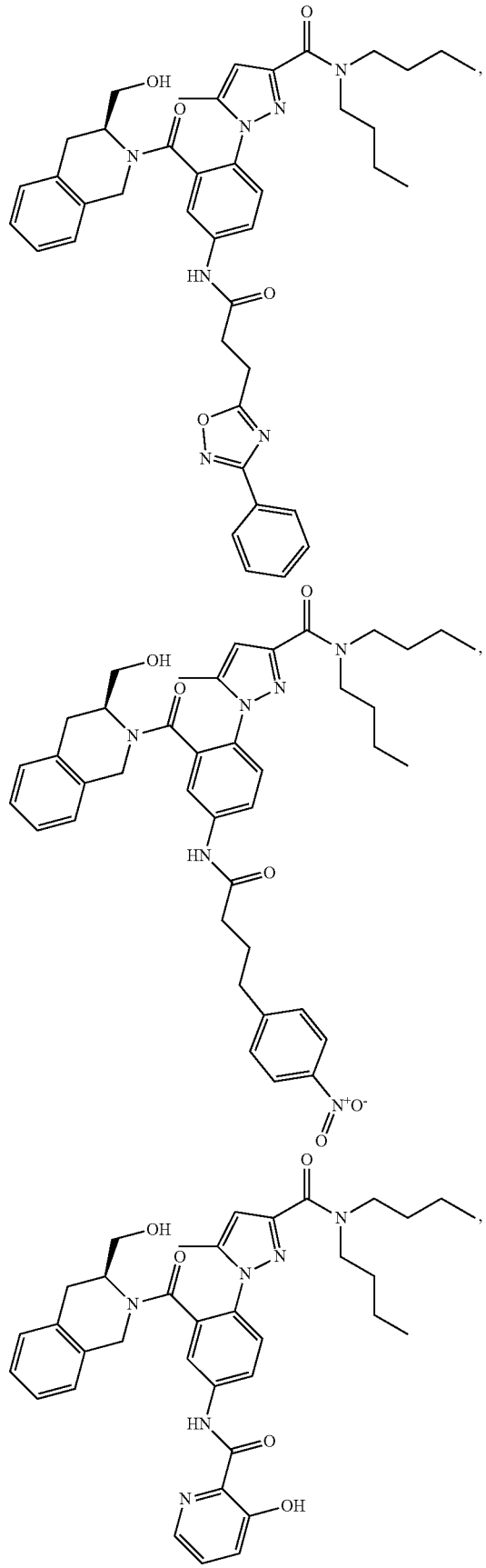

1805
-continued
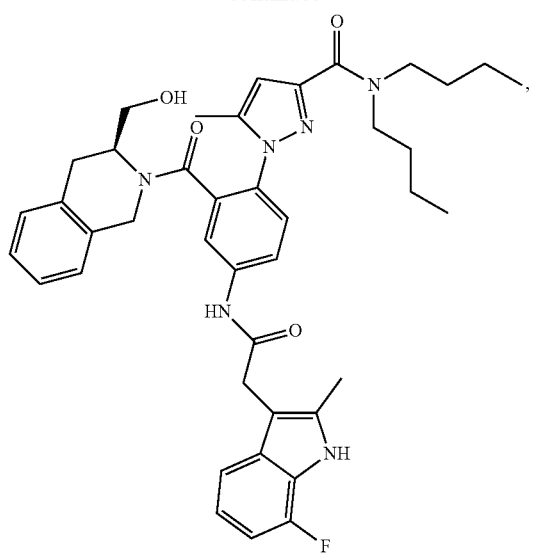
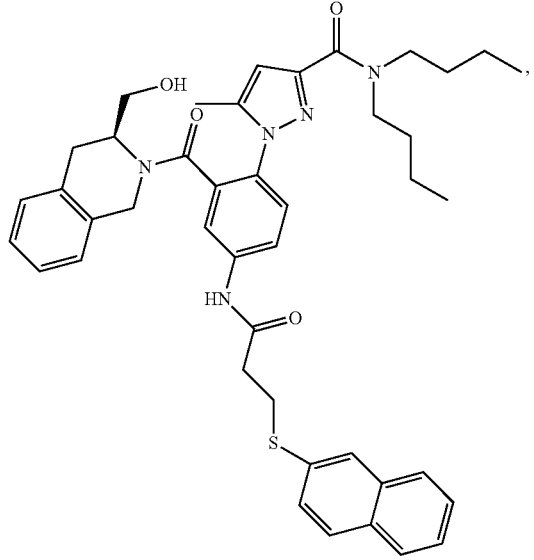
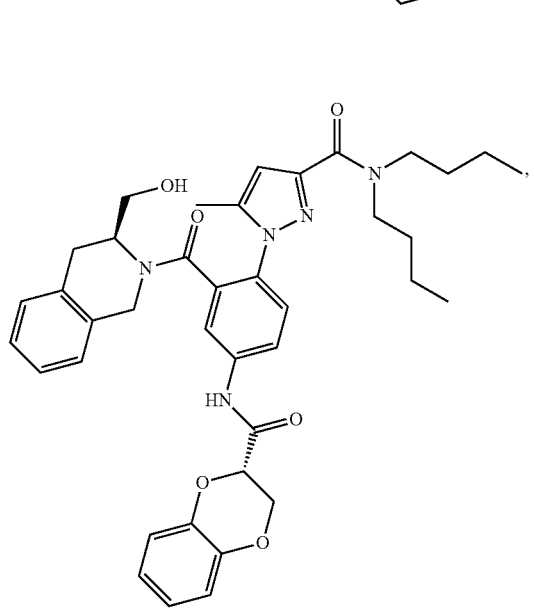
1806
-continued
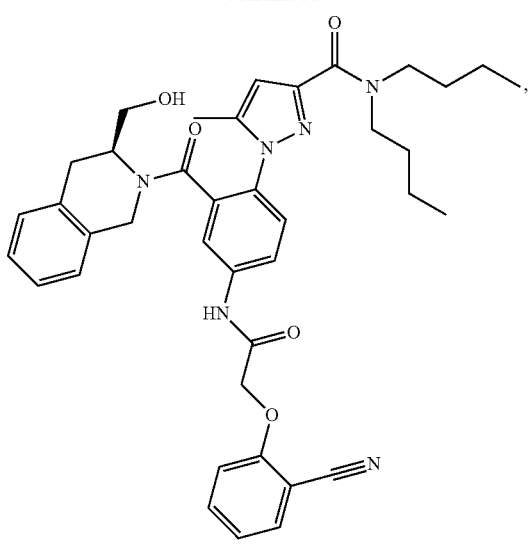
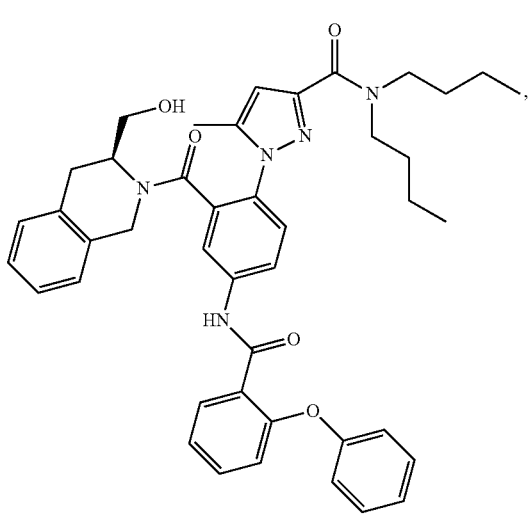
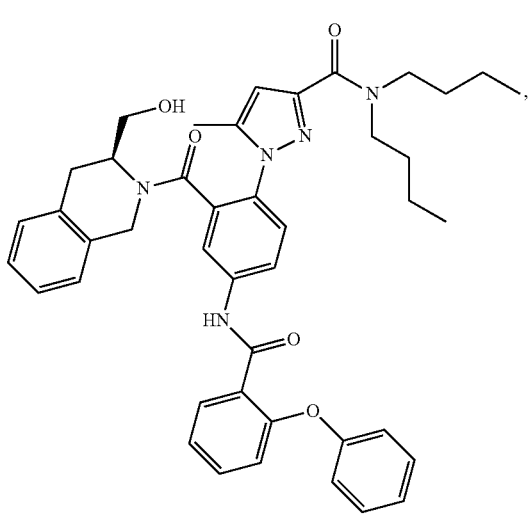

1807
-continued
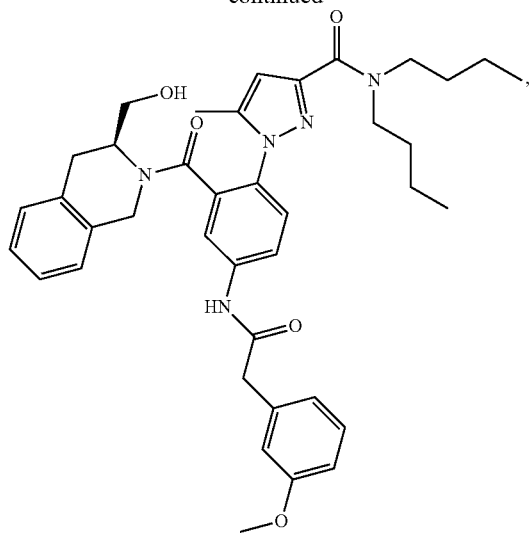
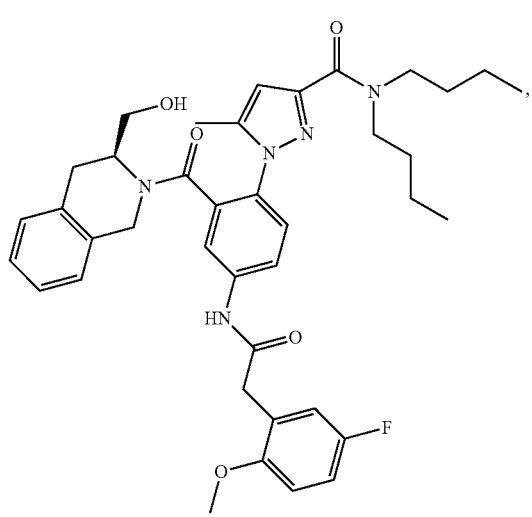
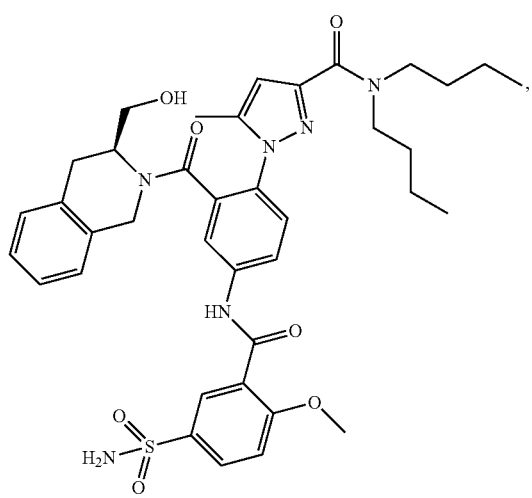
1808
-continued
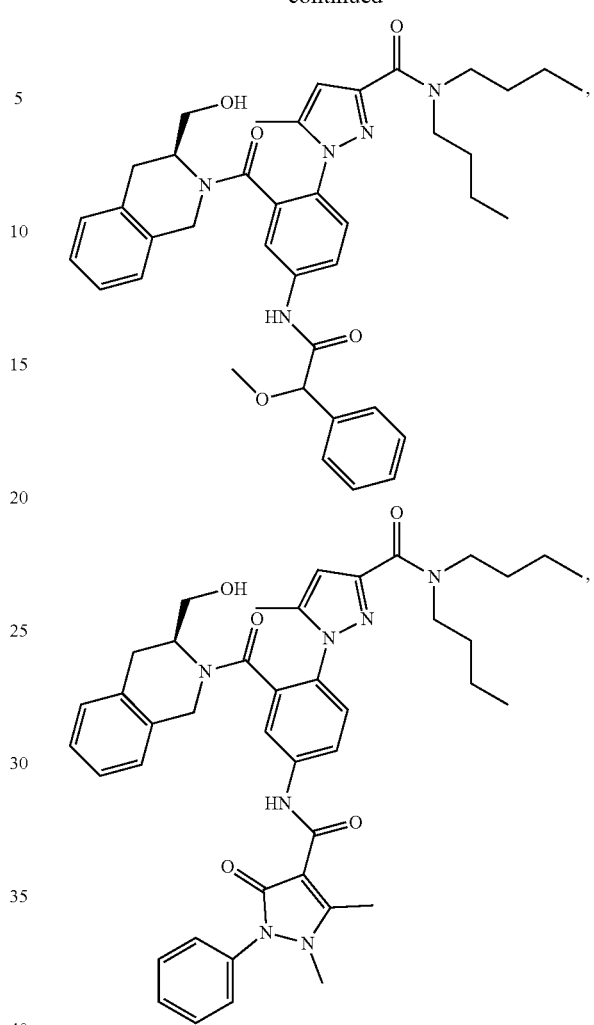
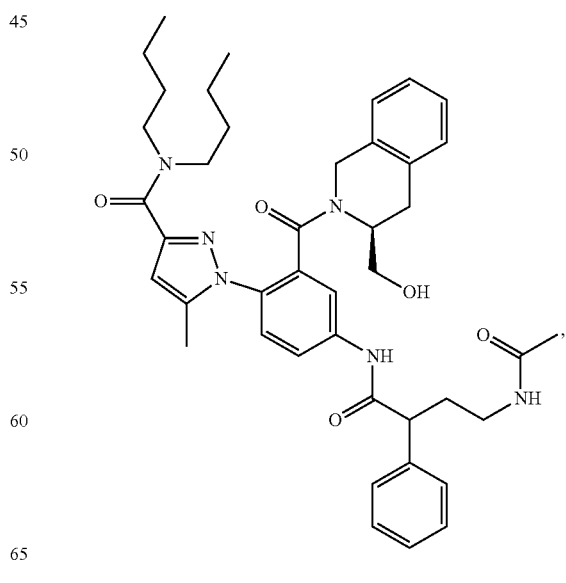

1809
-continued
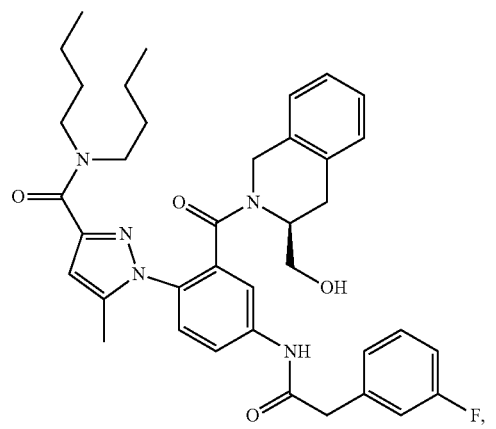
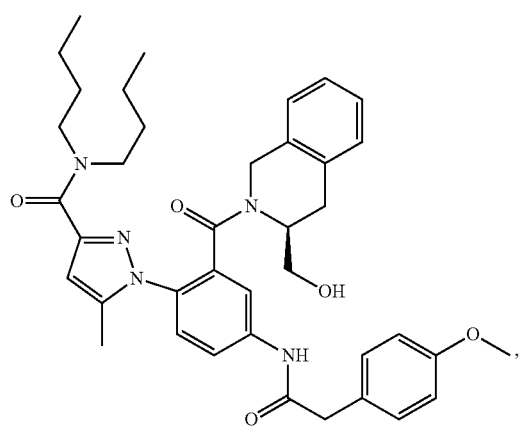
1810
-continued
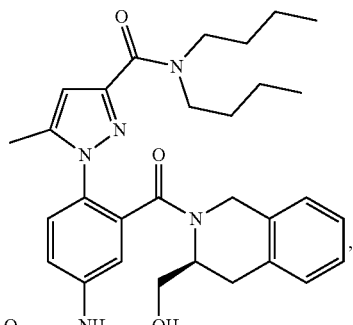
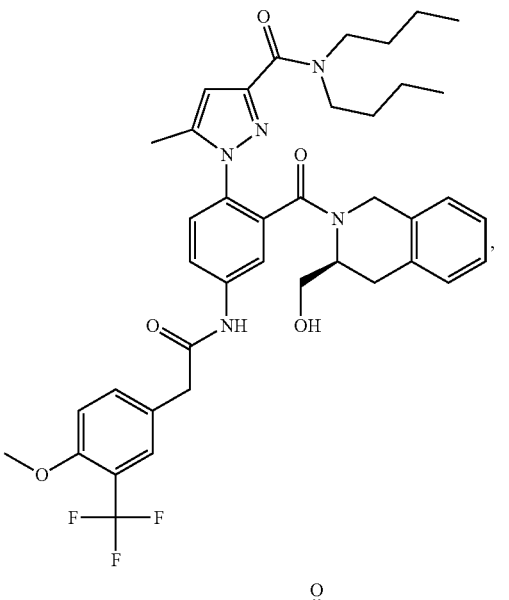
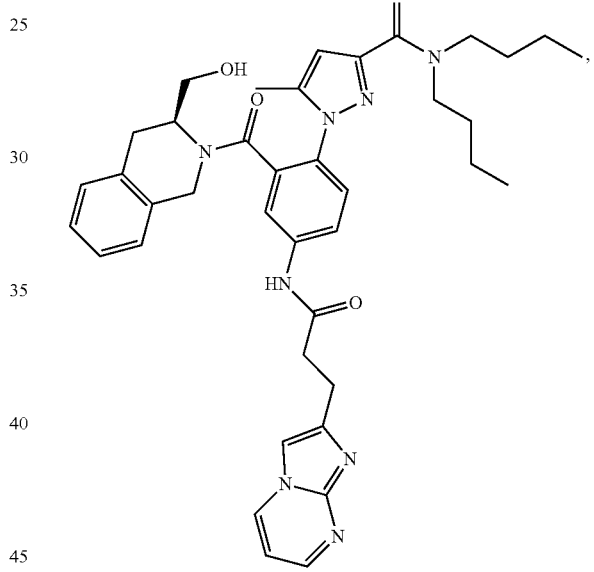
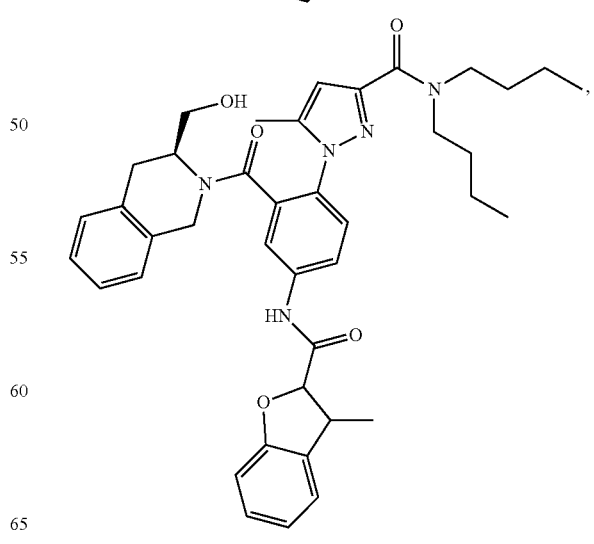

1811
-continued
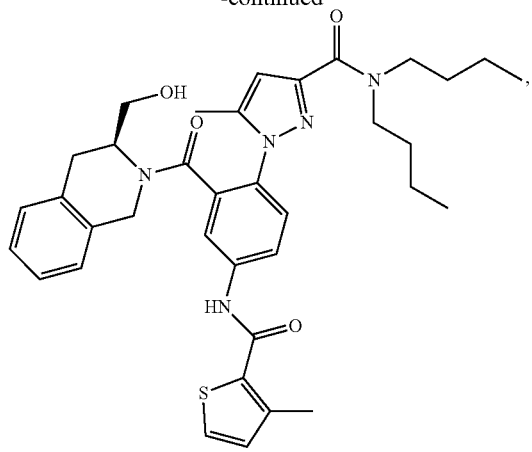
1812
-continued
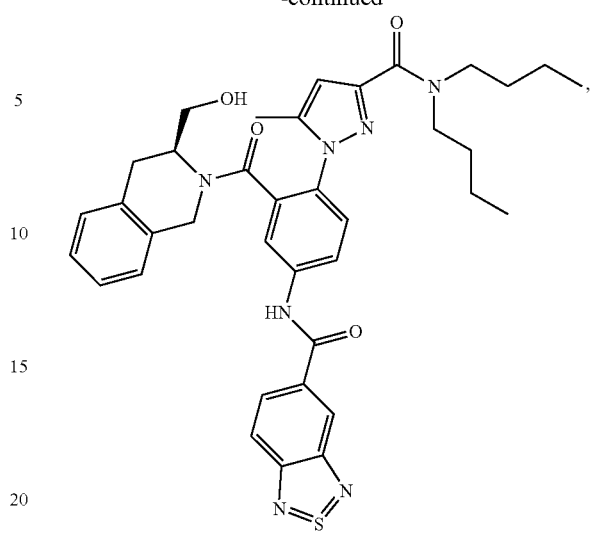
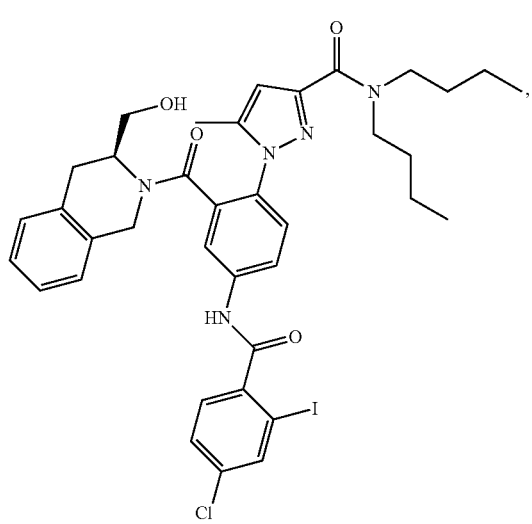
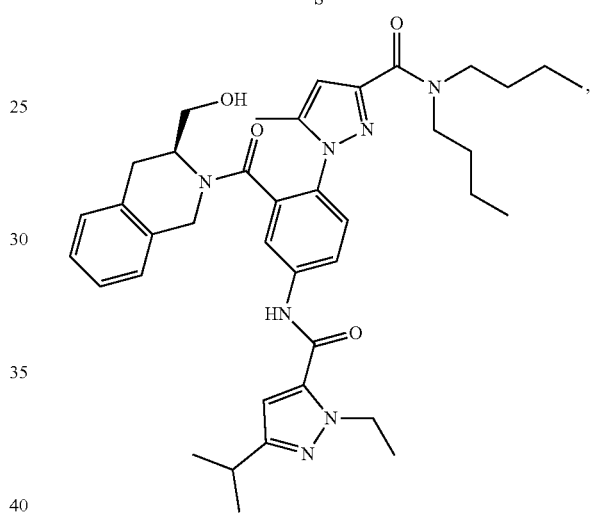
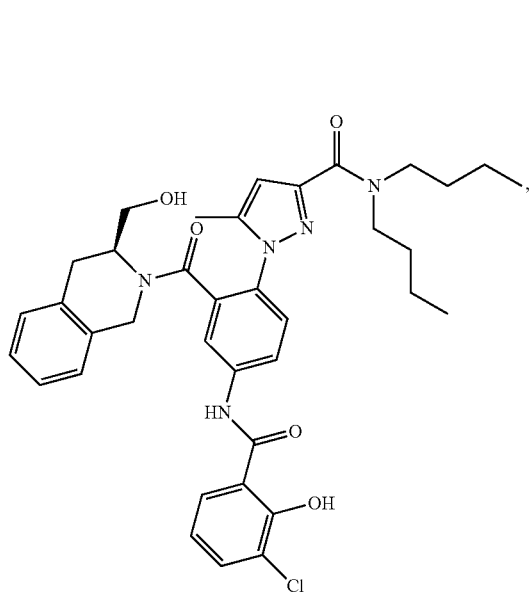
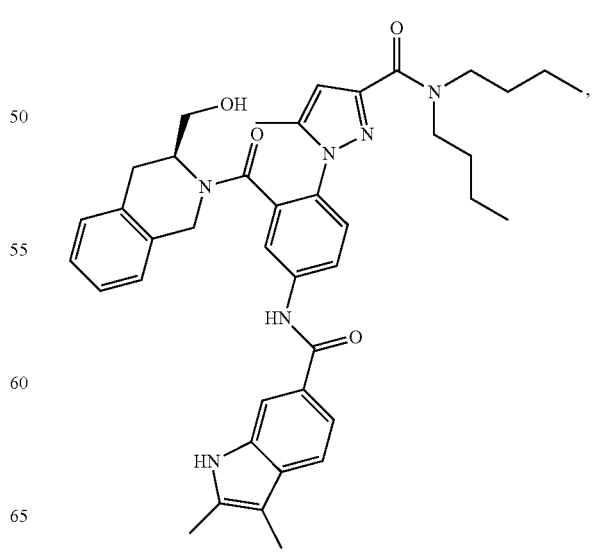

-continued
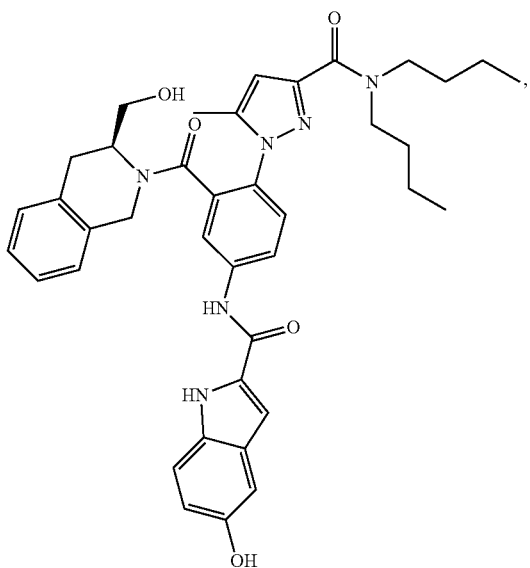
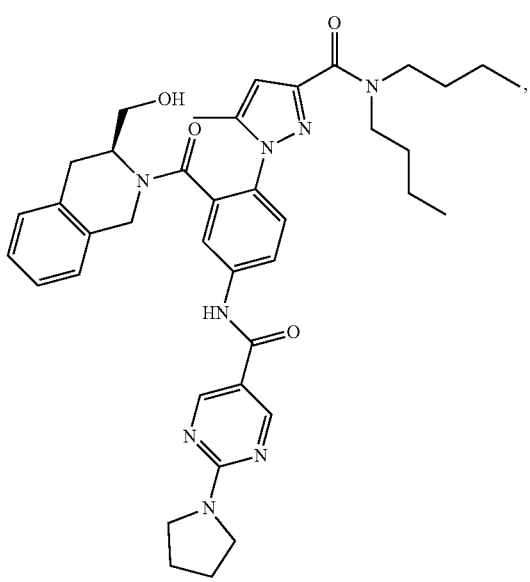
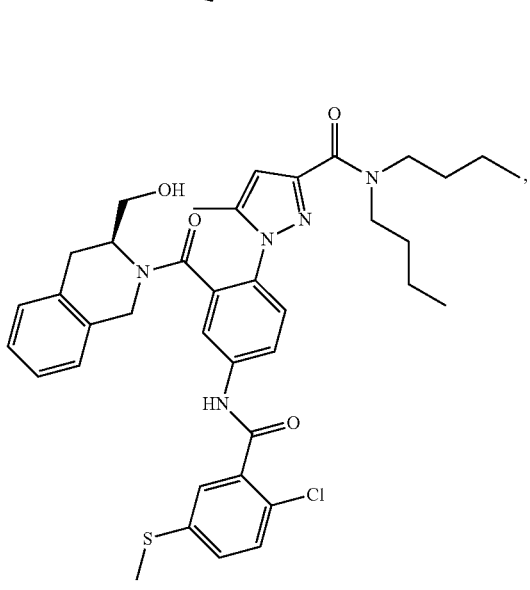
-continued
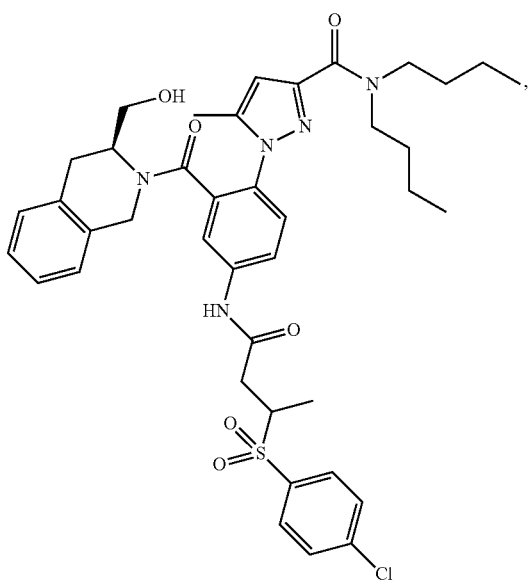
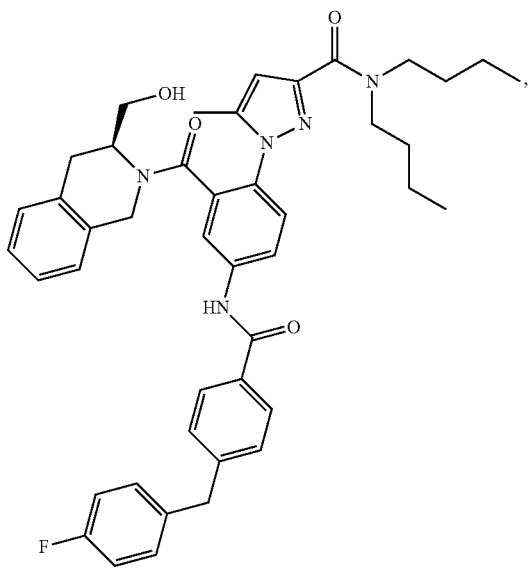
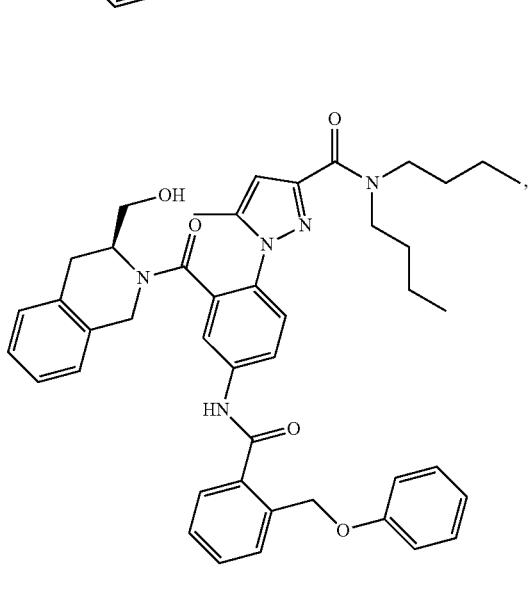

1815
-continued
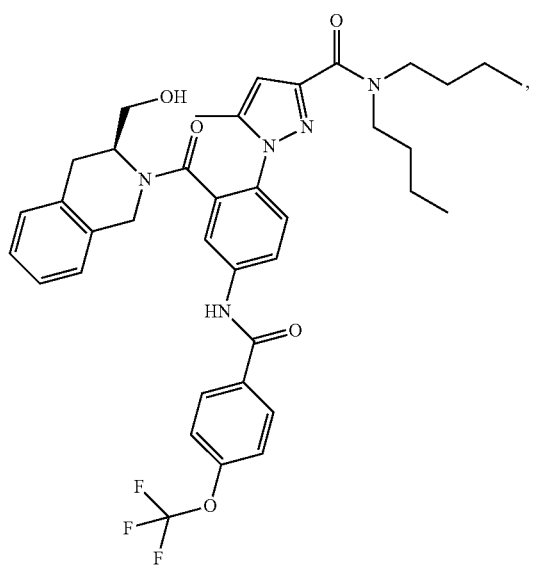
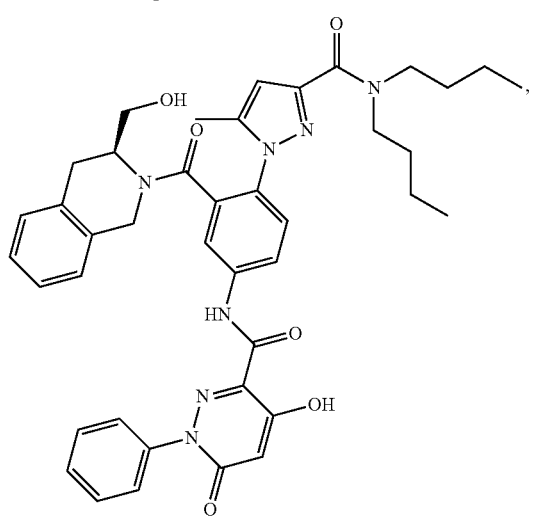
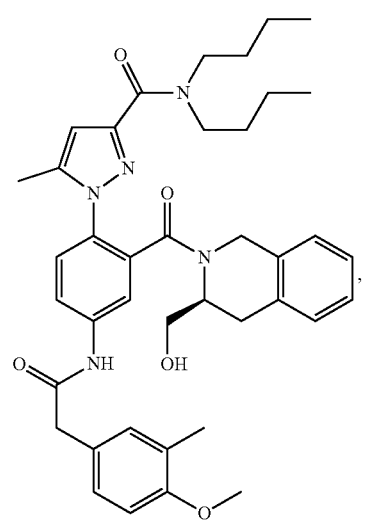
1816
-continued
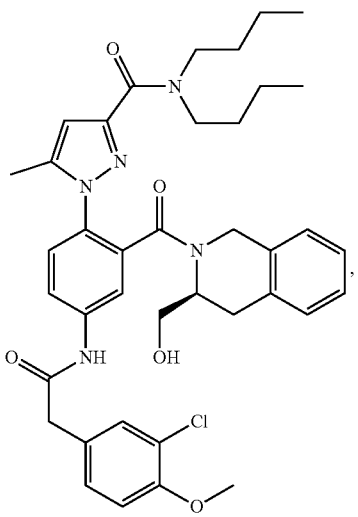
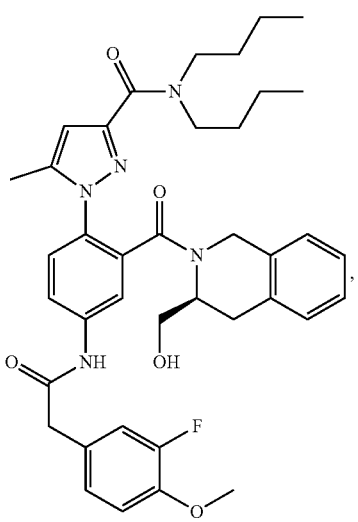
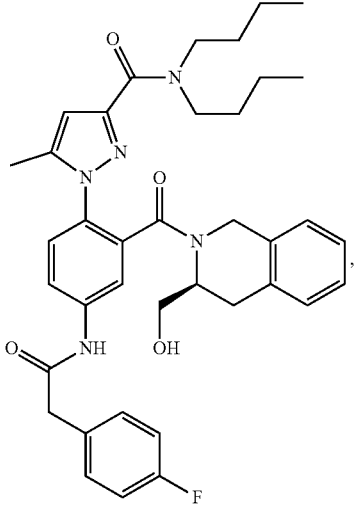

1817
-continued
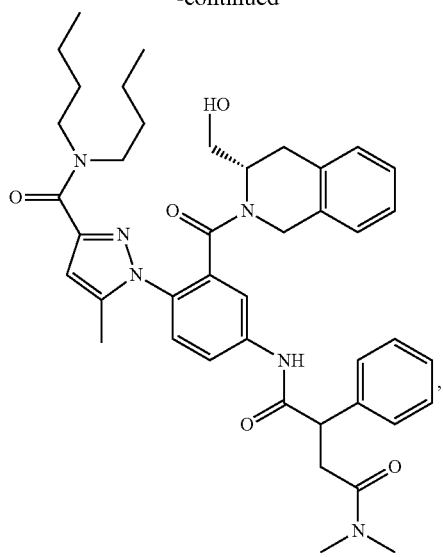
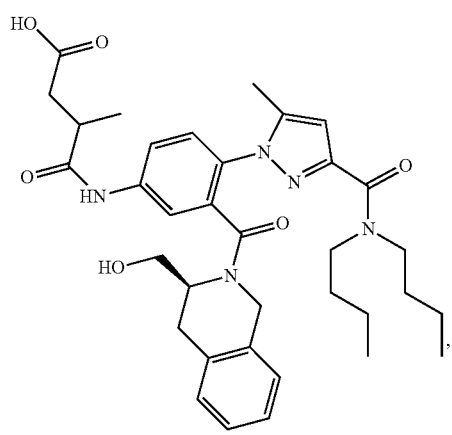
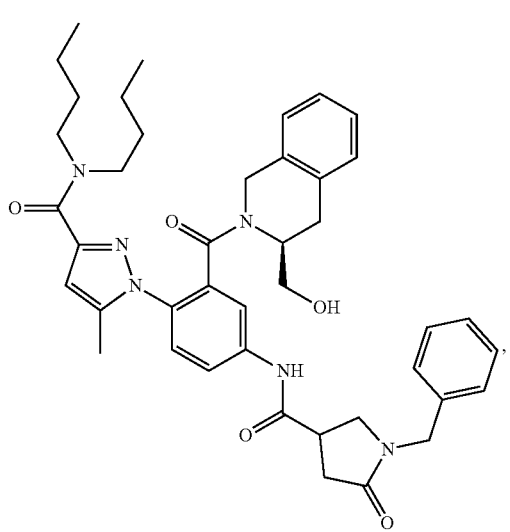
1818
-continued
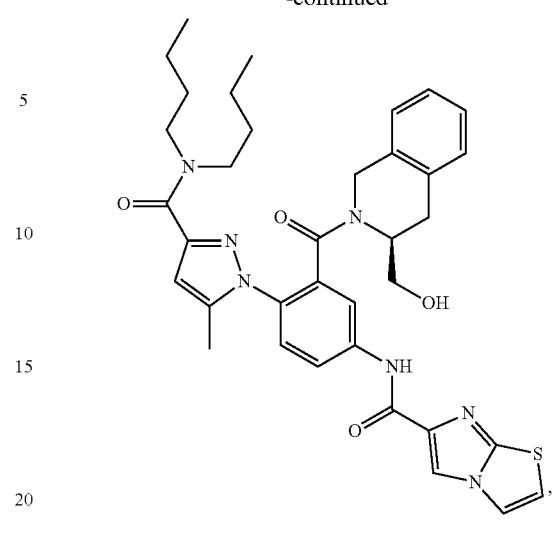
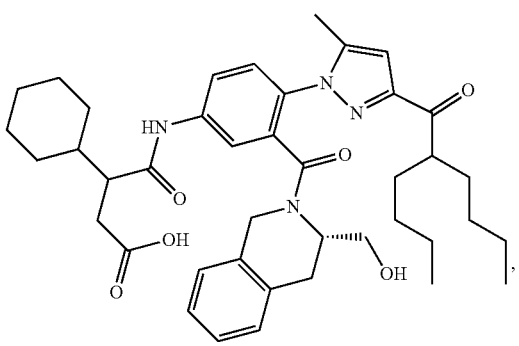
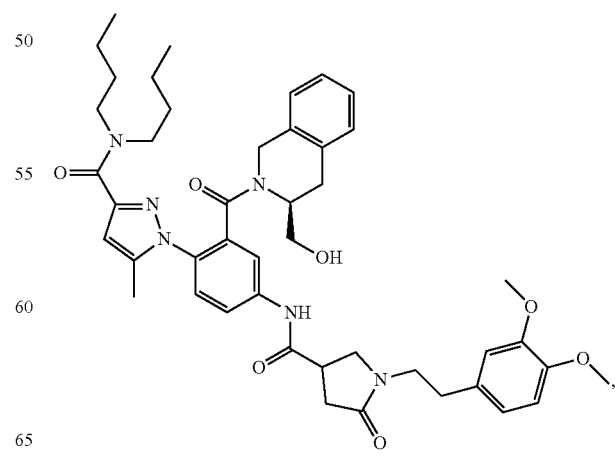

1819
-continued
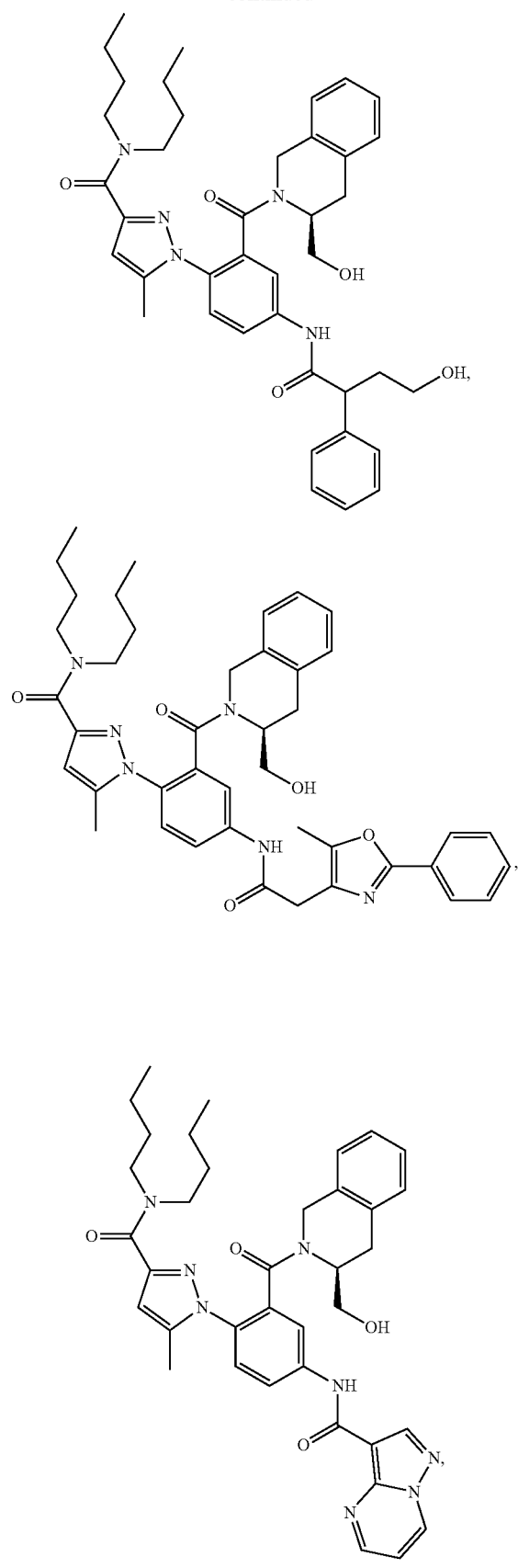
1820
-continued
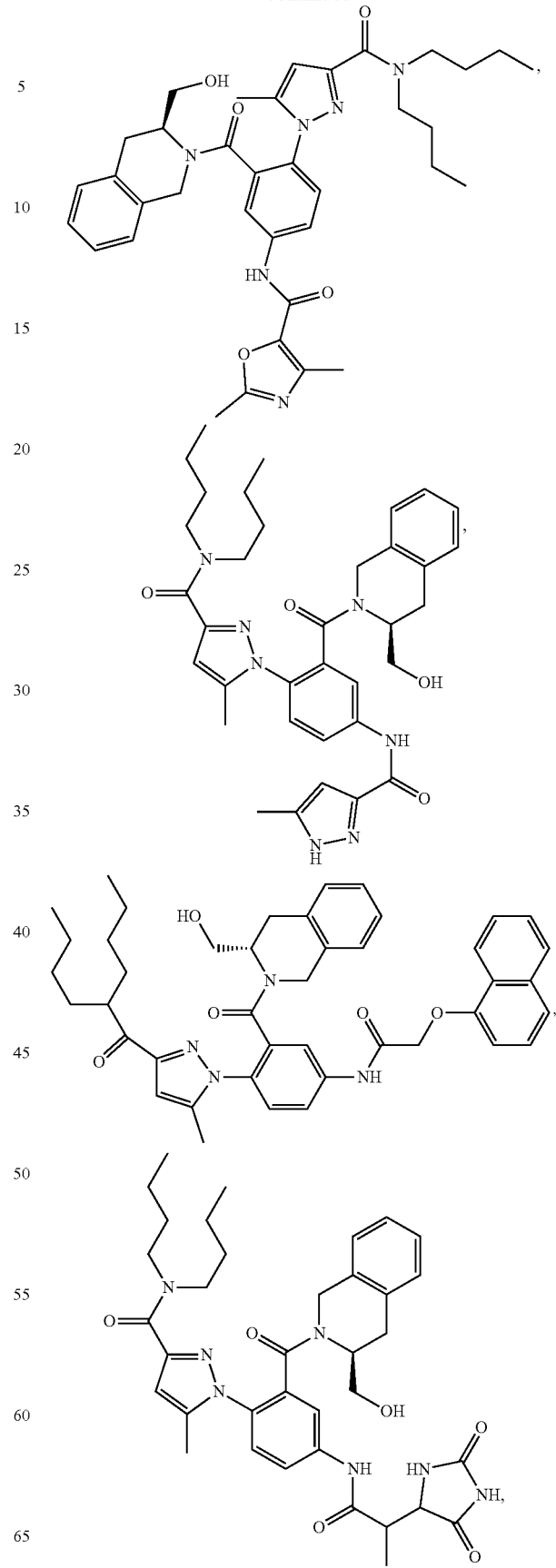

| 1821 | 1822 |
|---|---|
| -continued | -continued |
| 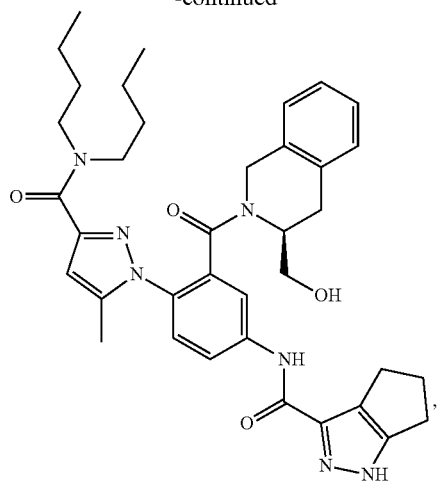 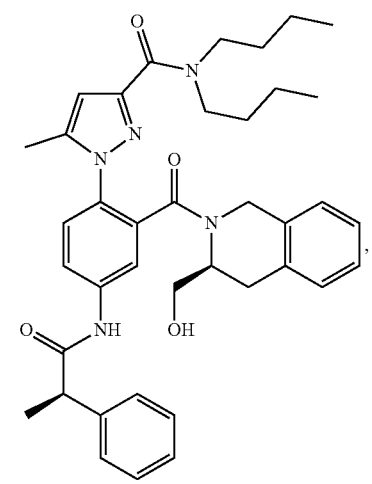 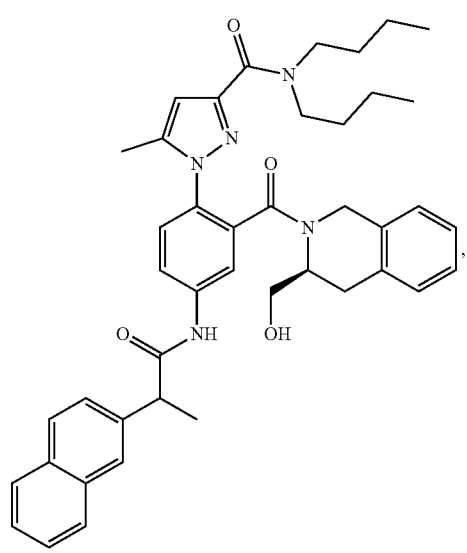 | 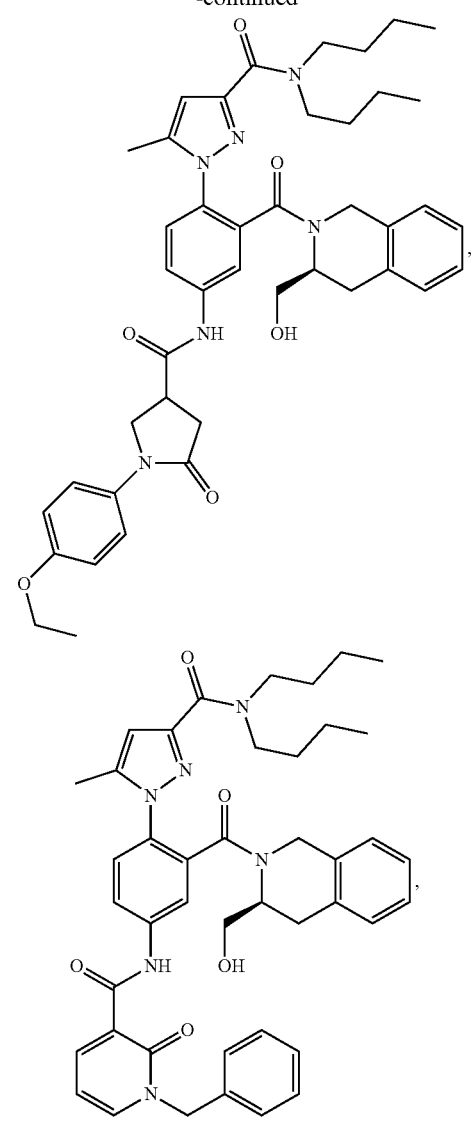 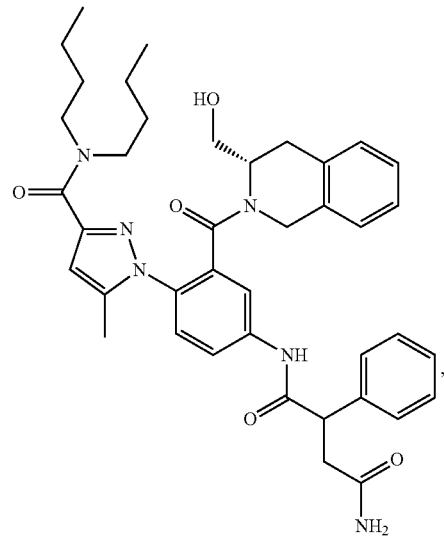 |

1823
-continued
1824
-continued
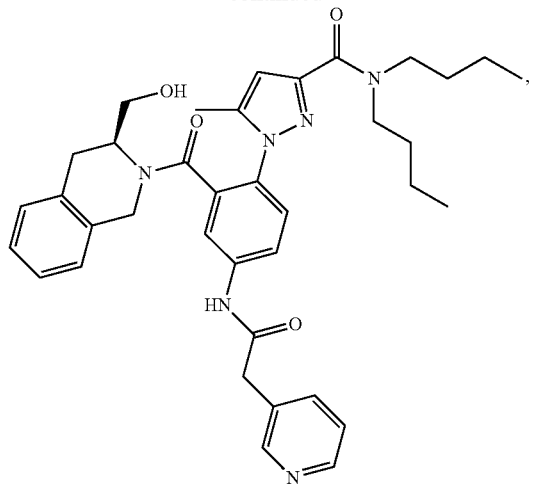
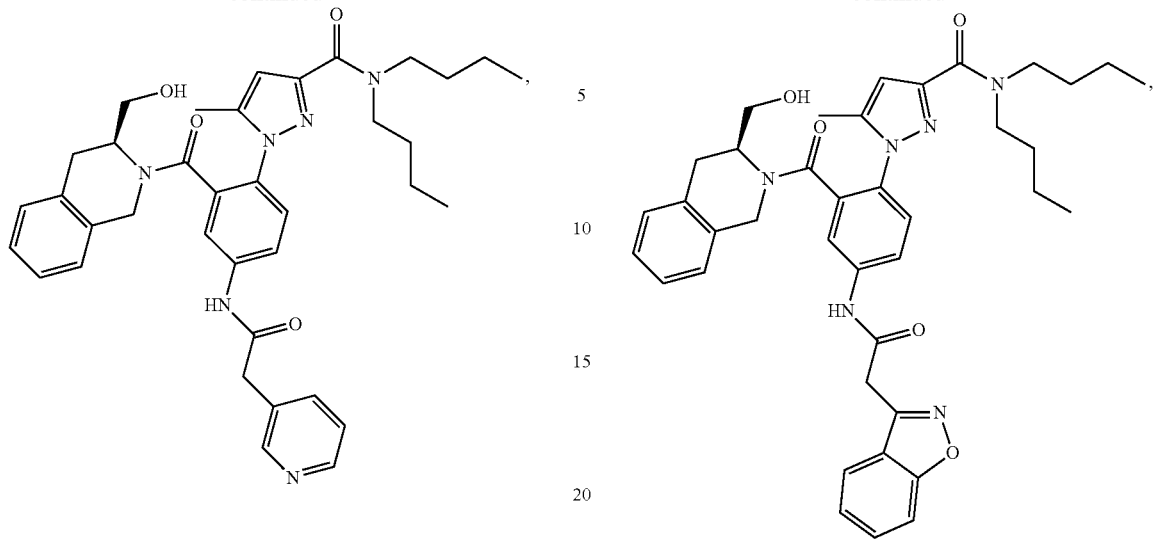
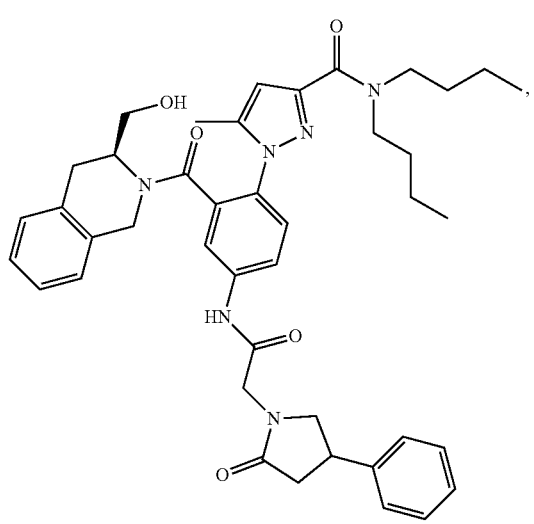
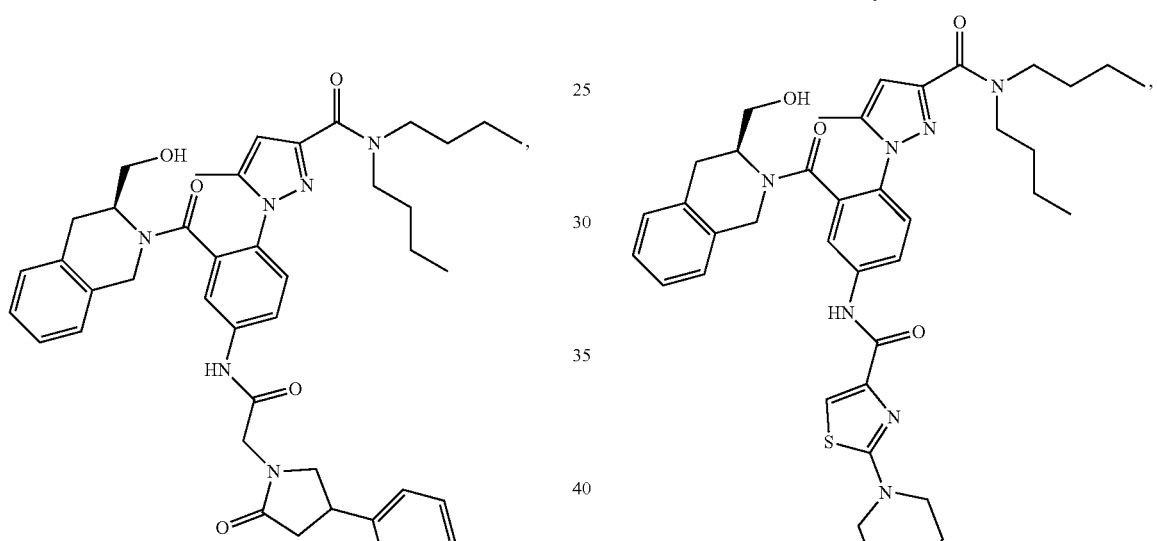
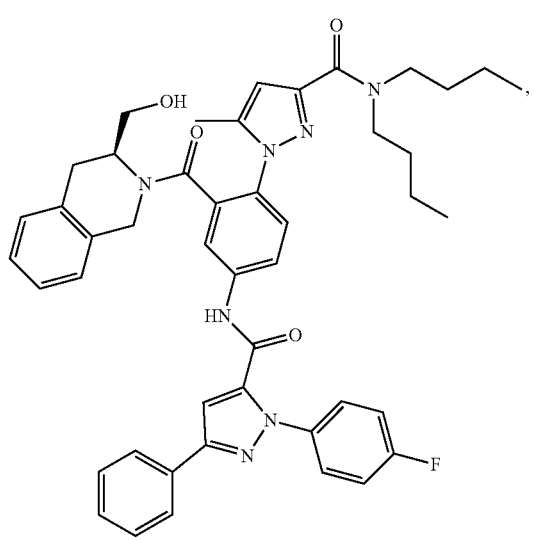
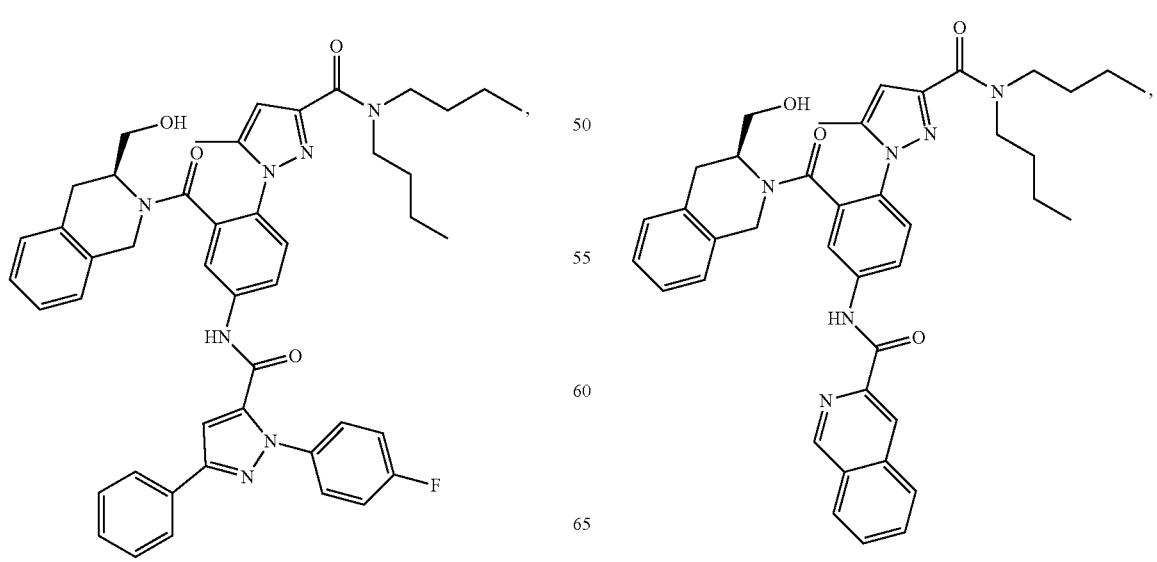

1825 -continued
1826 -continued
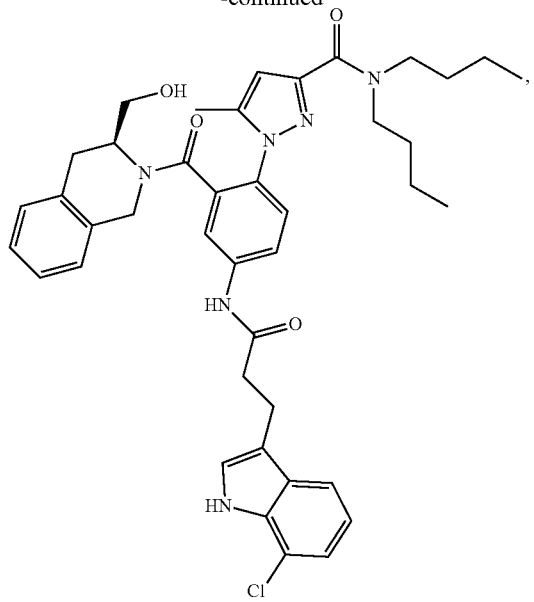
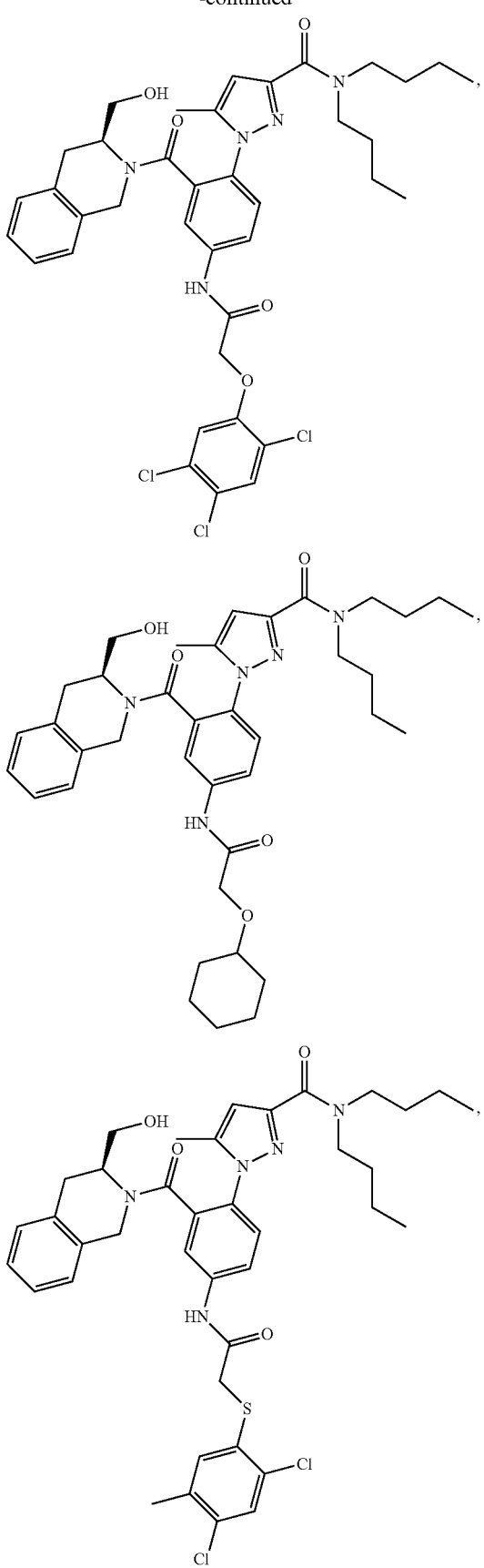

1827
-continued
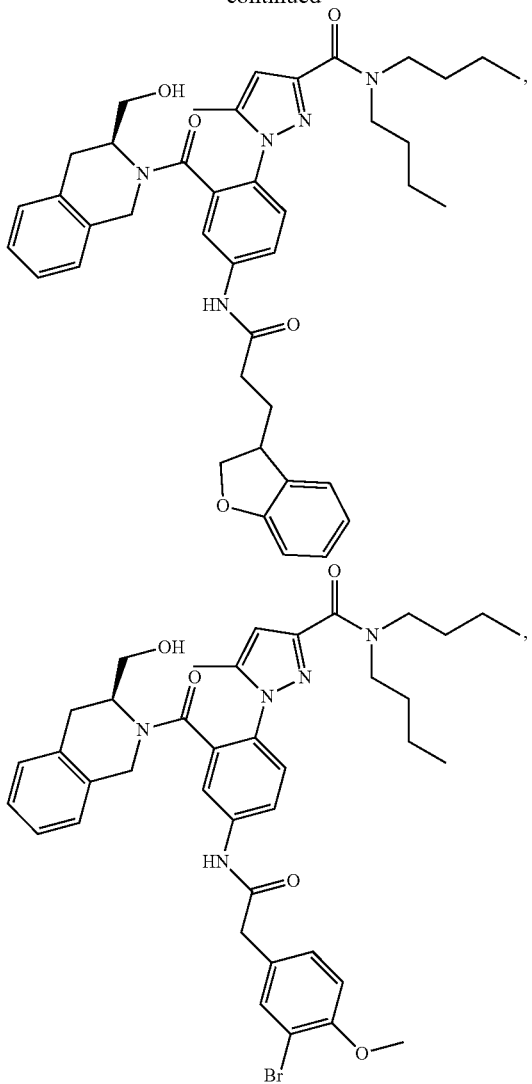
1828
-continued
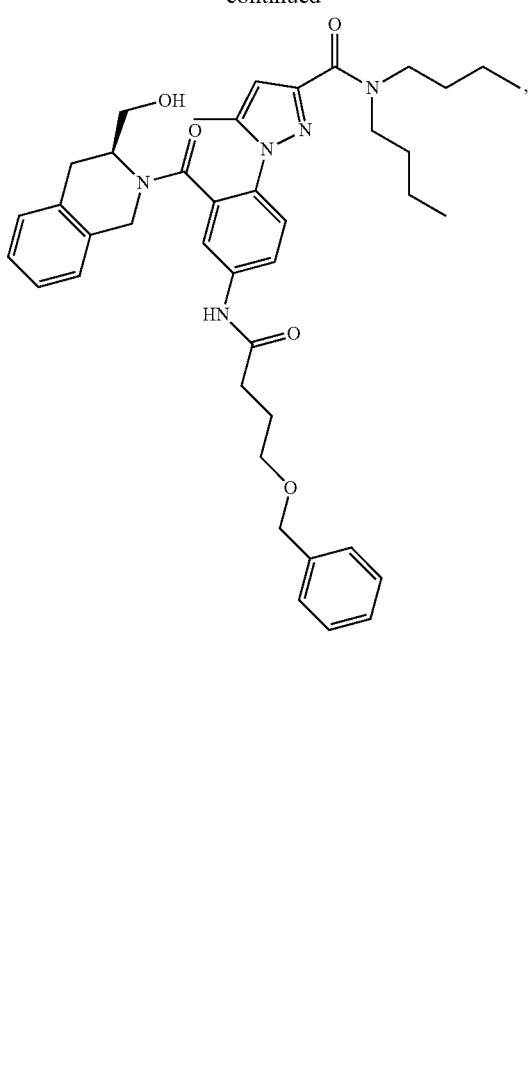
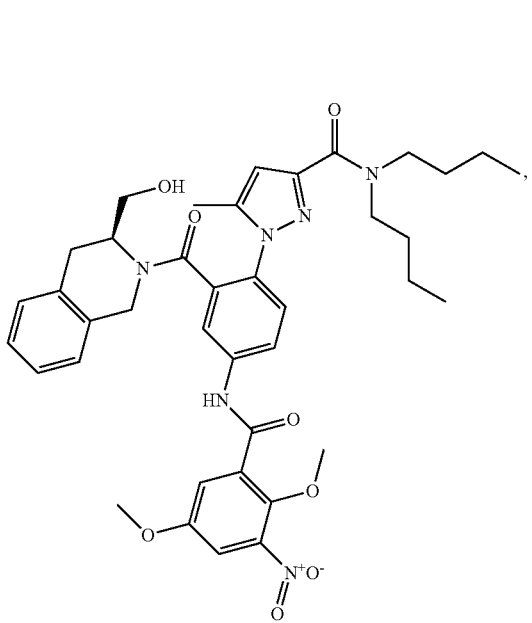

1829
-continued
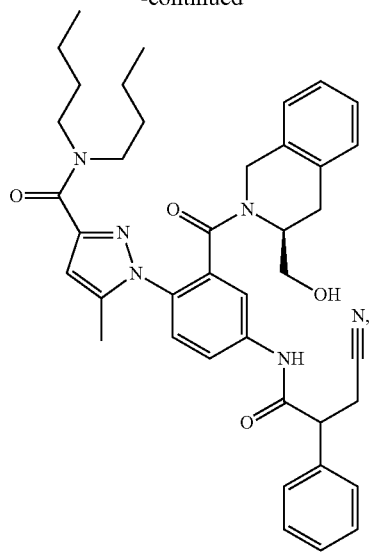
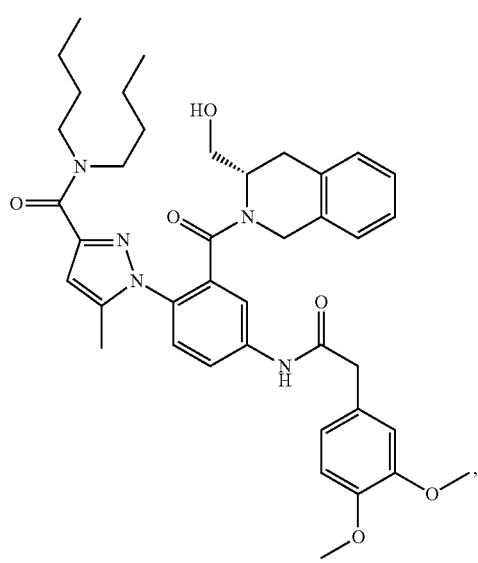
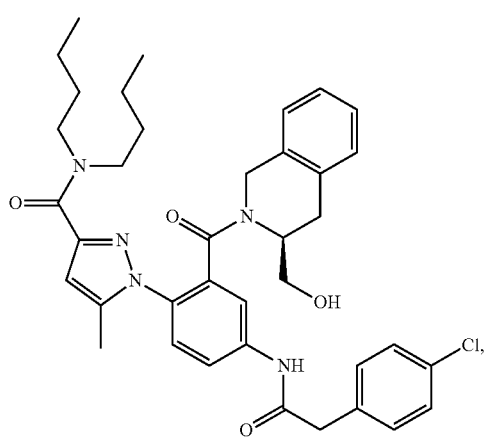
1830
-continued
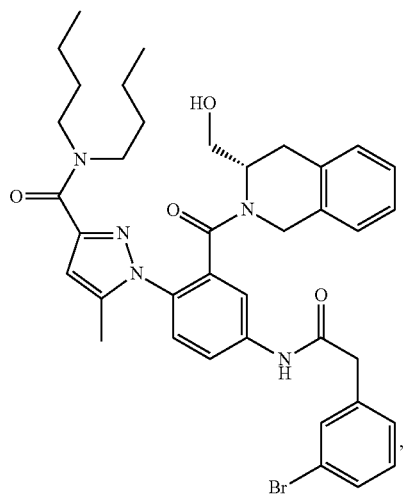
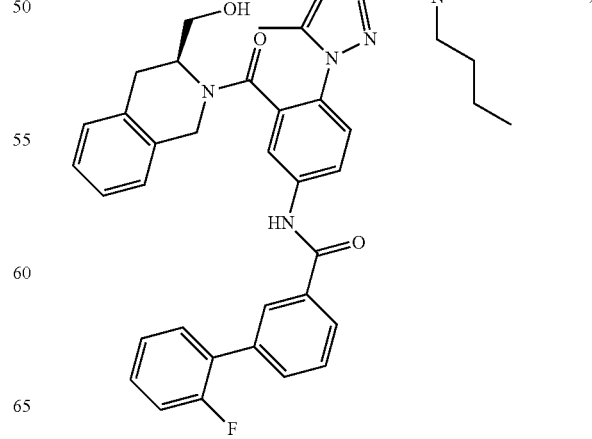

1831
-continued
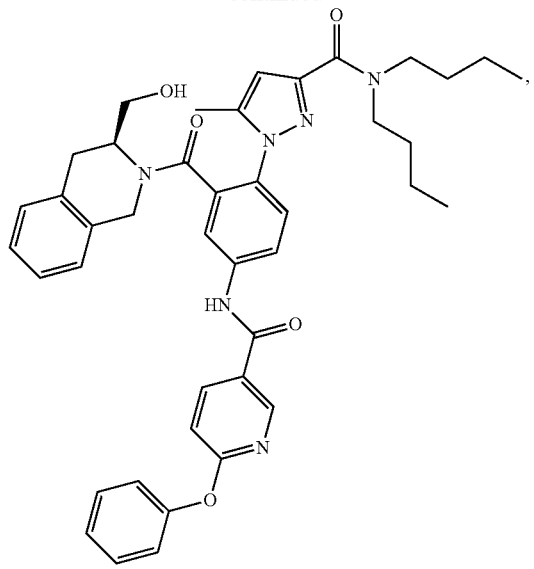
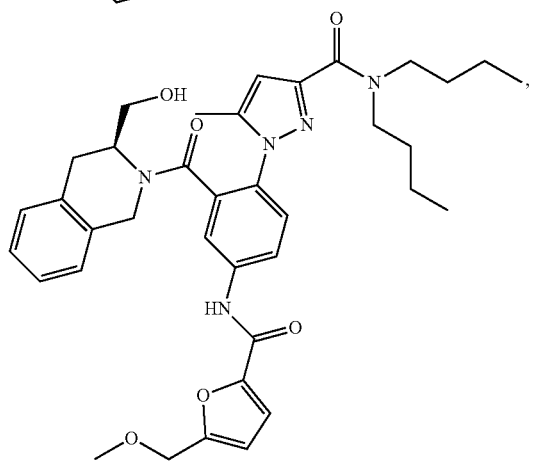
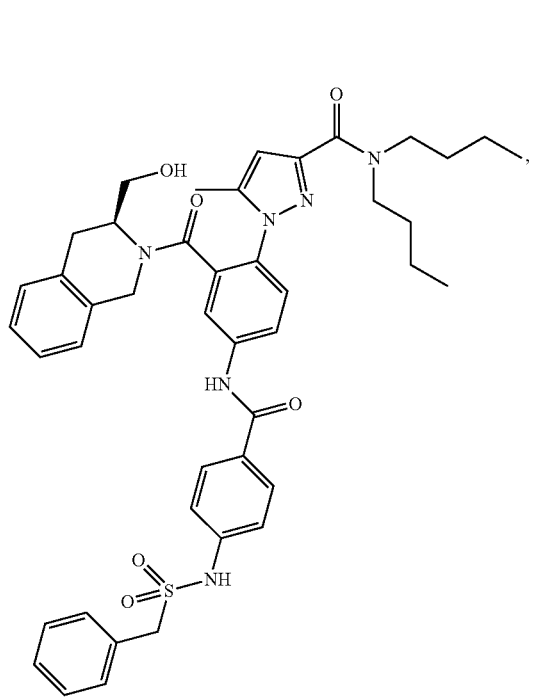
1832
-continued
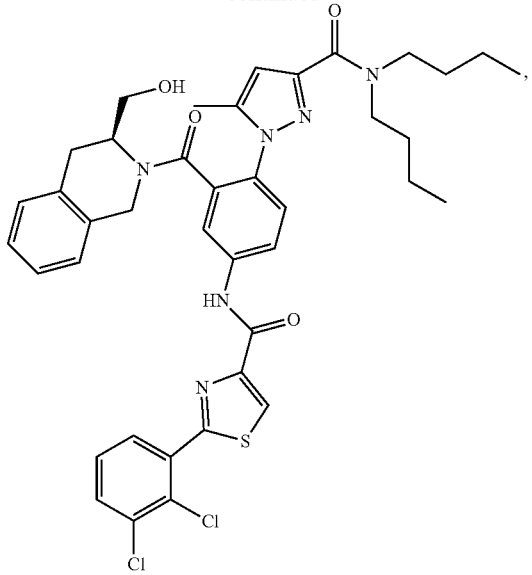
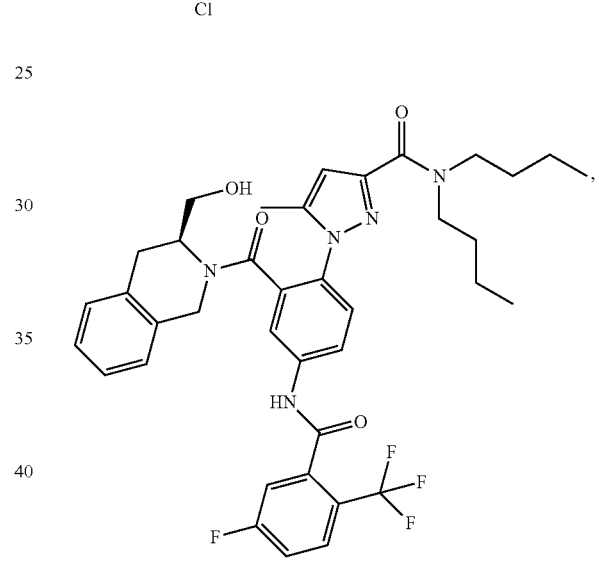
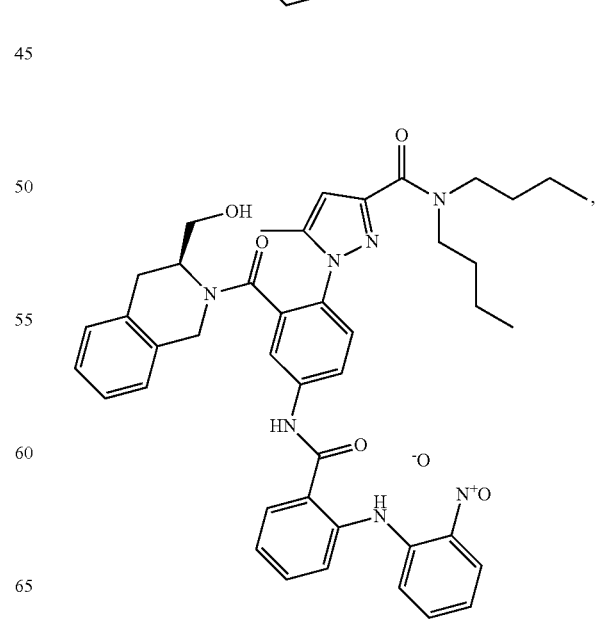

-continued
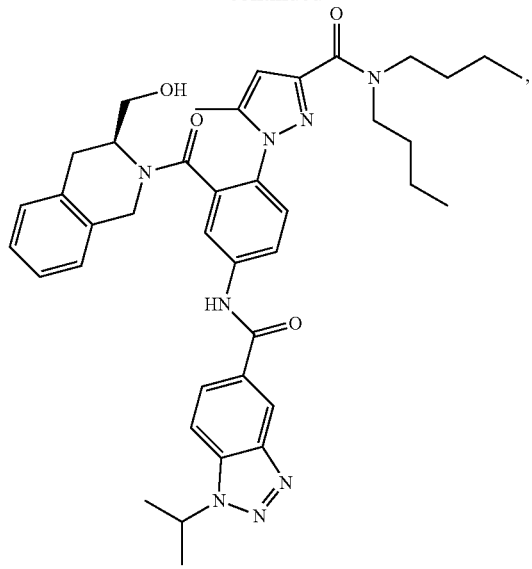
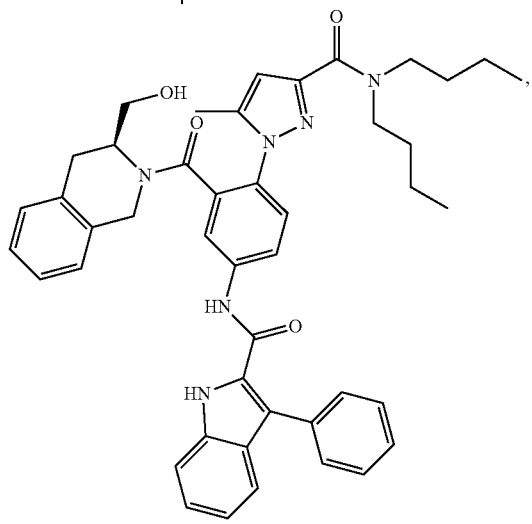
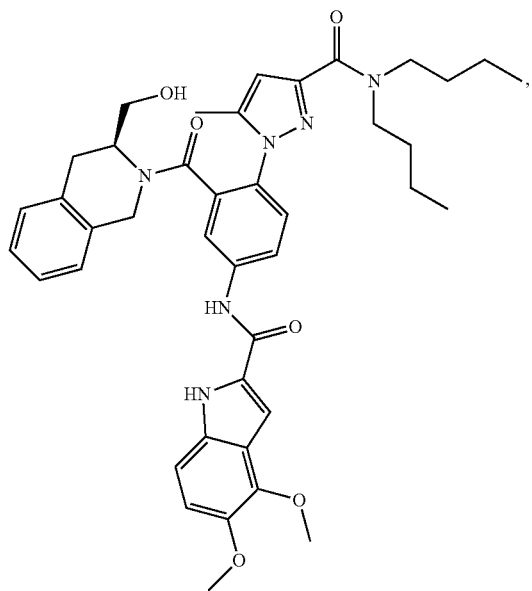
-continued
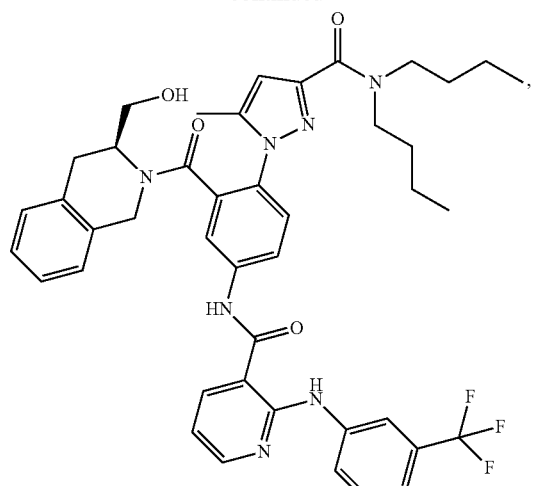
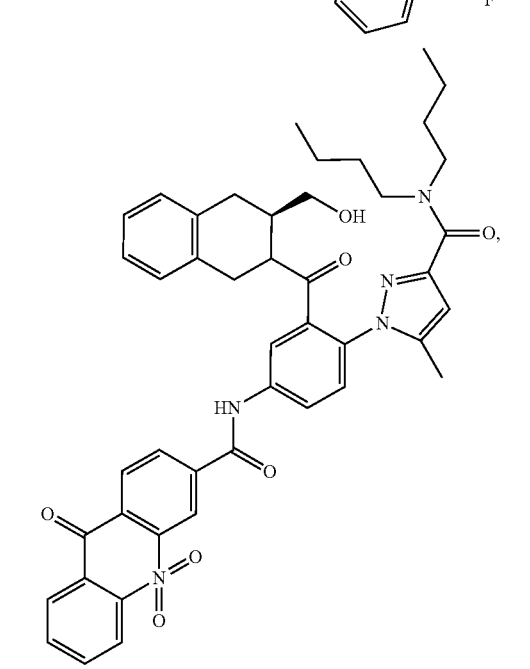
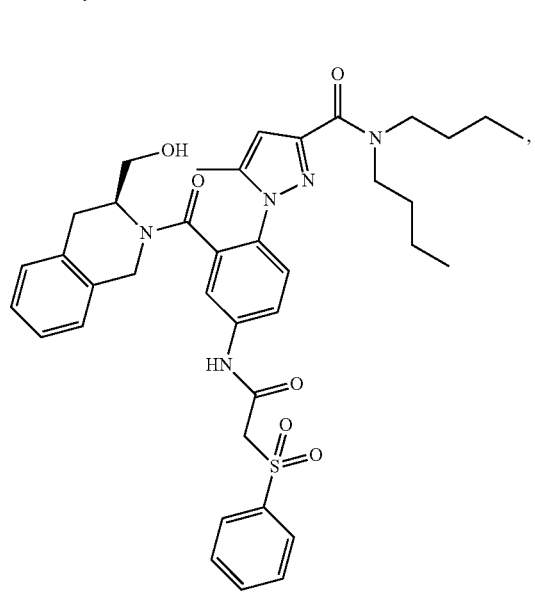

1835
-continued
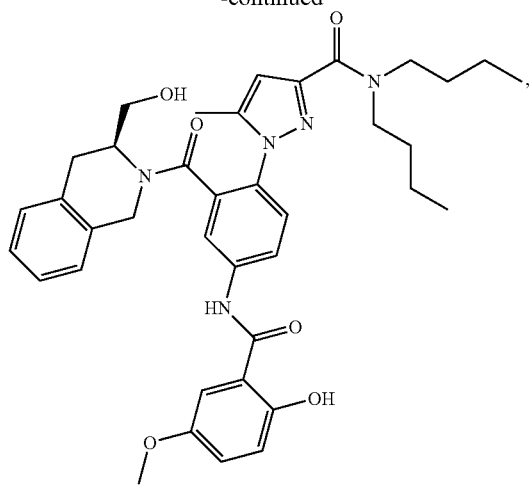
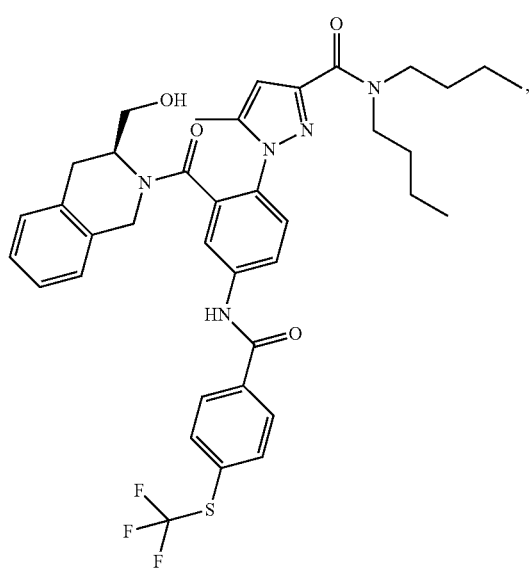
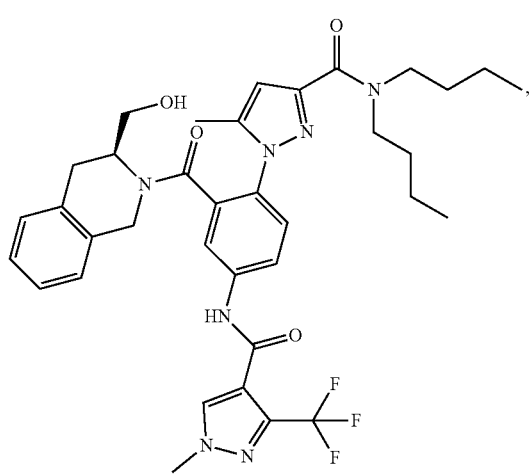
1836
-continued
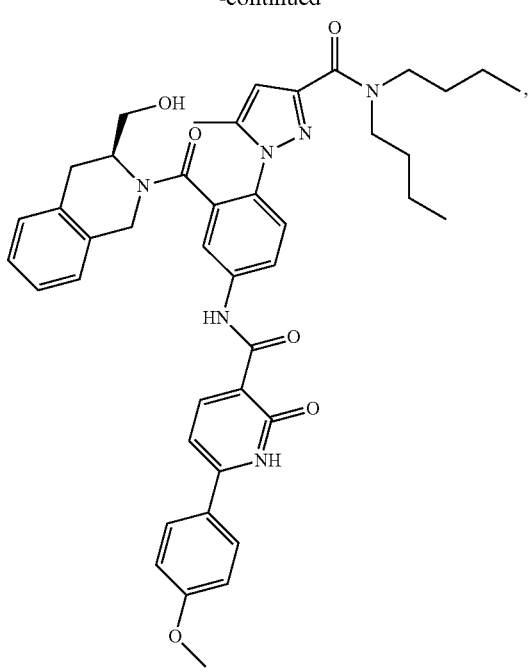
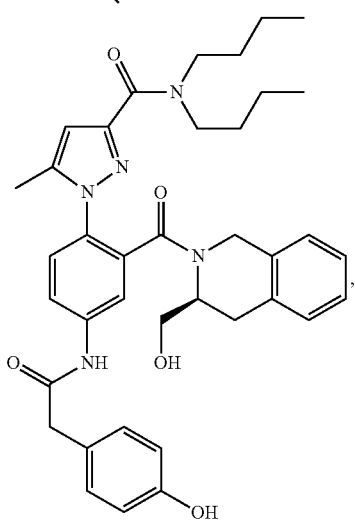
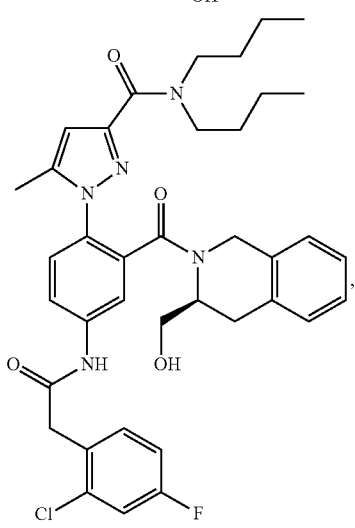

1837
-continued
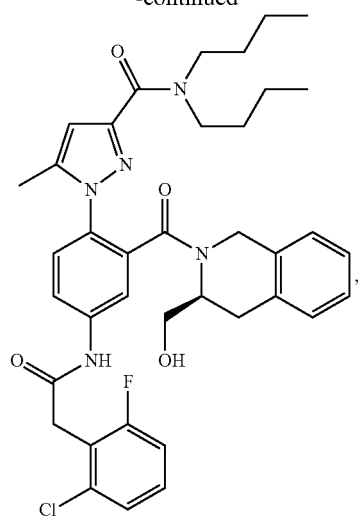
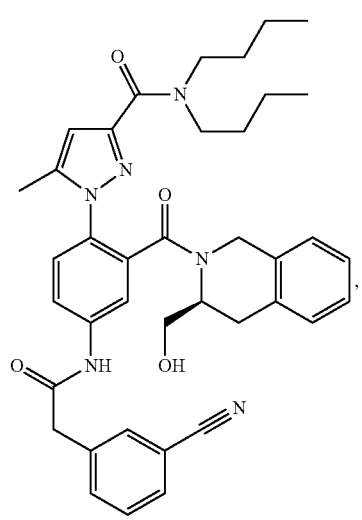
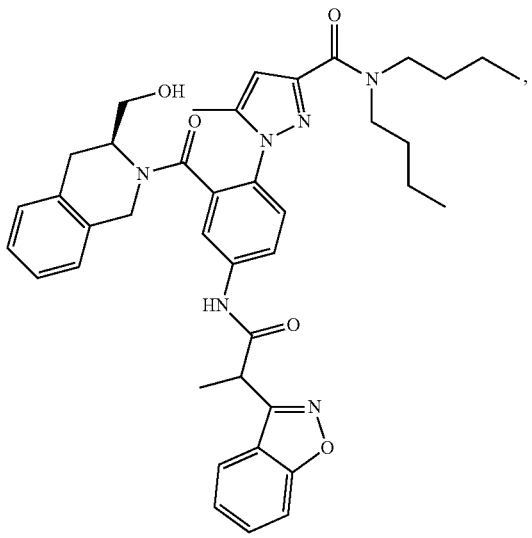
1838
-continued
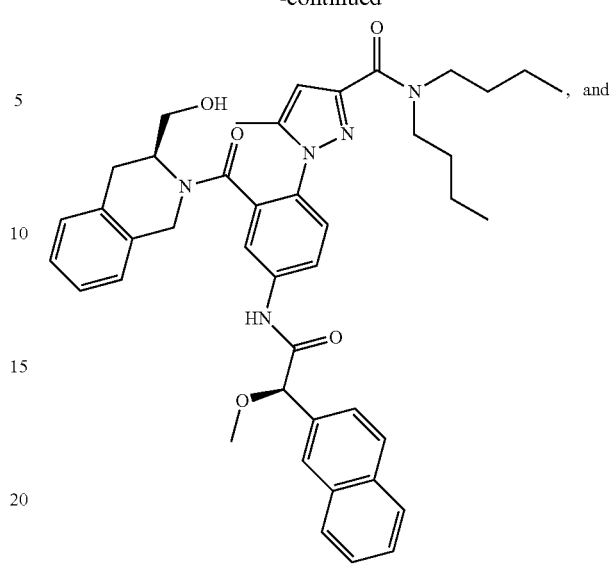, and
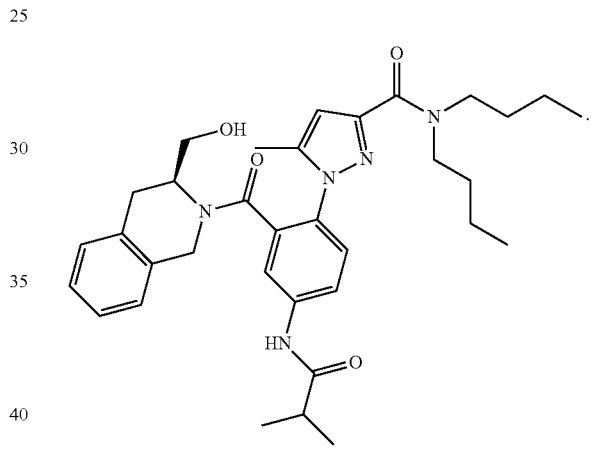.
In some embodiments, the compound is selected from the group consisting of:
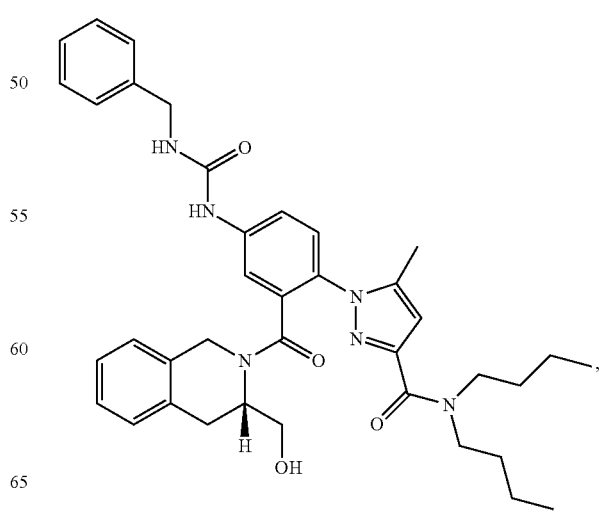, 1839
-continued
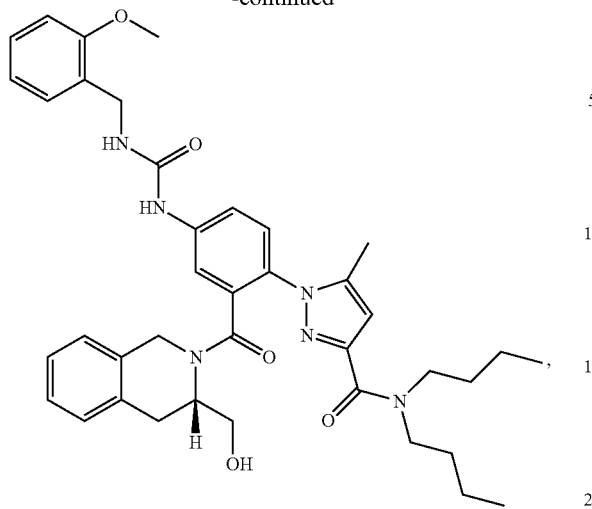
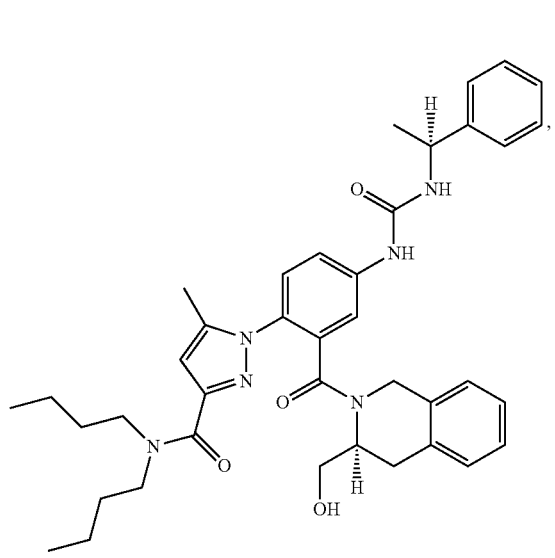
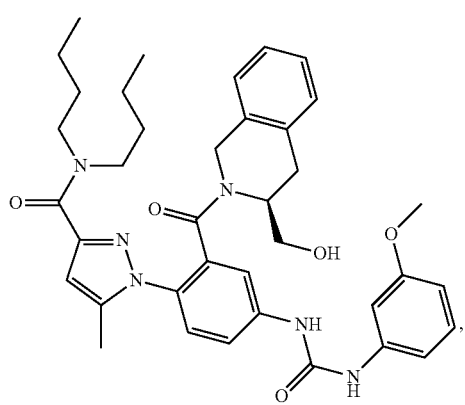
1840
-continued
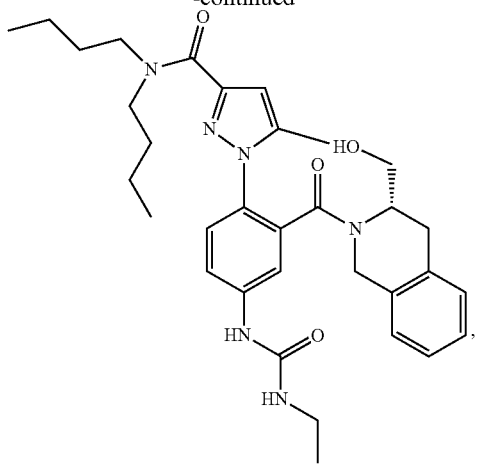
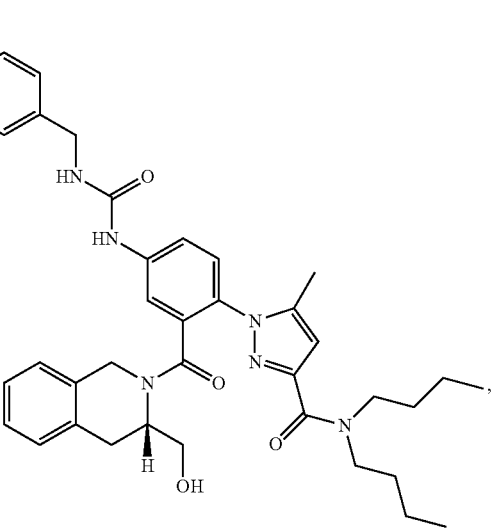
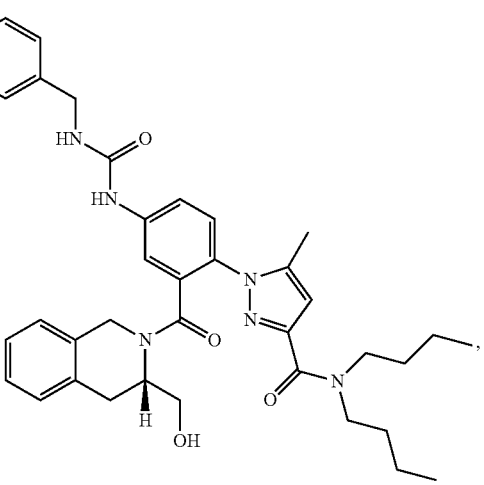

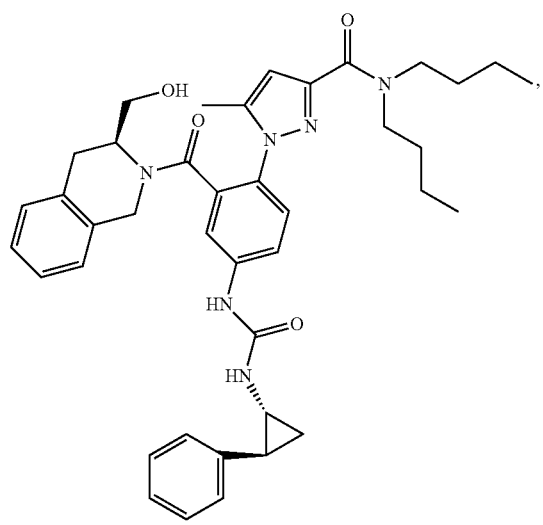
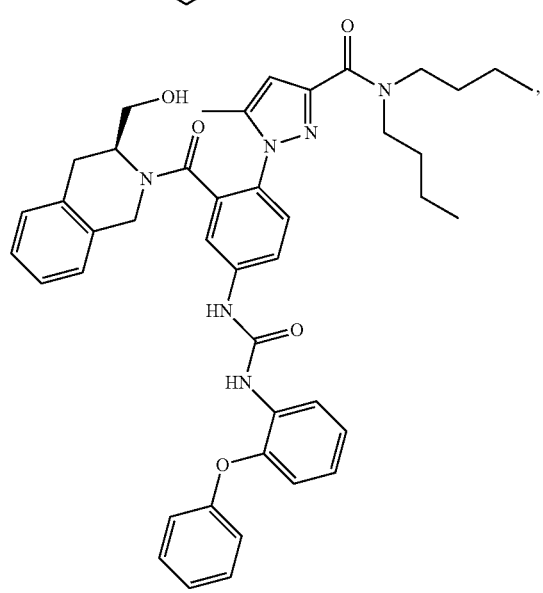
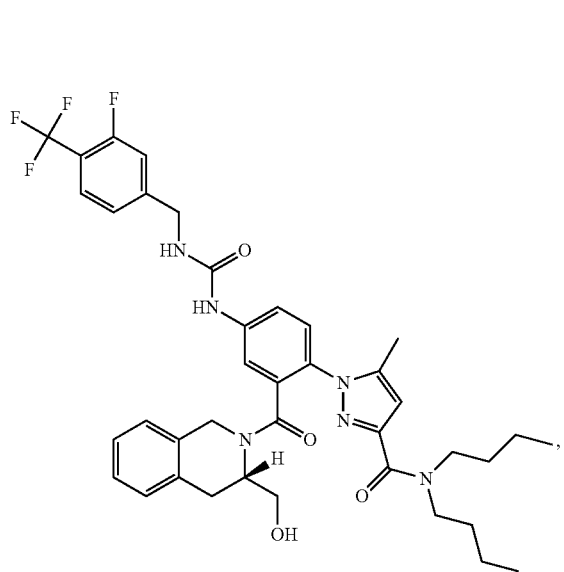
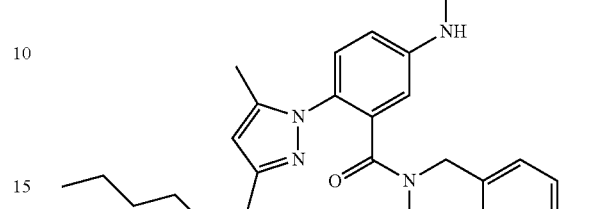
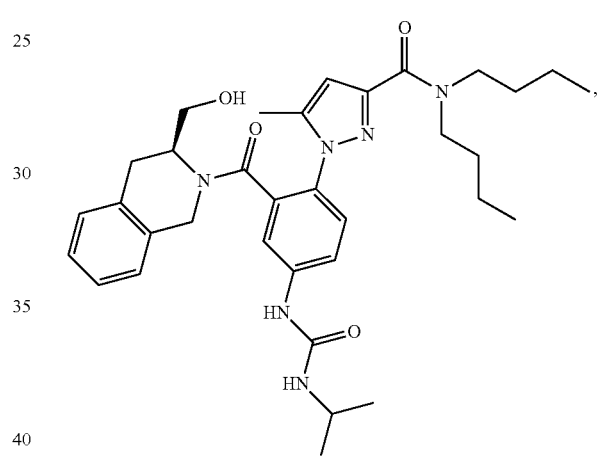
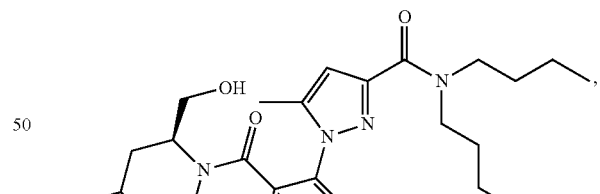
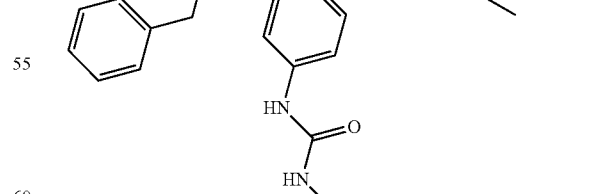
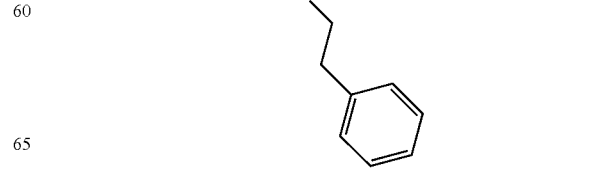

1843
-continued
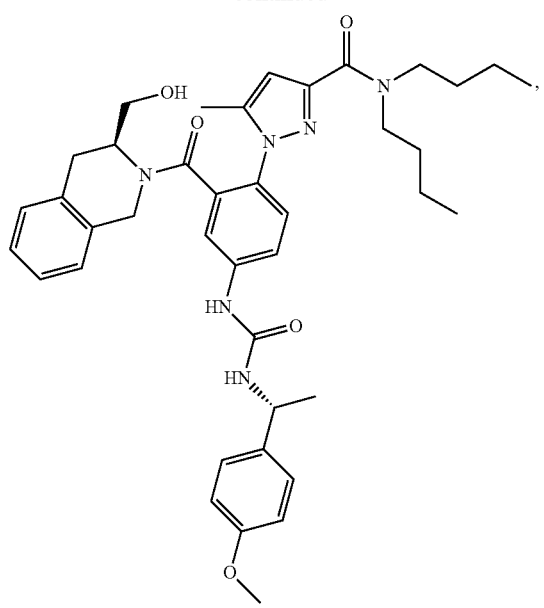
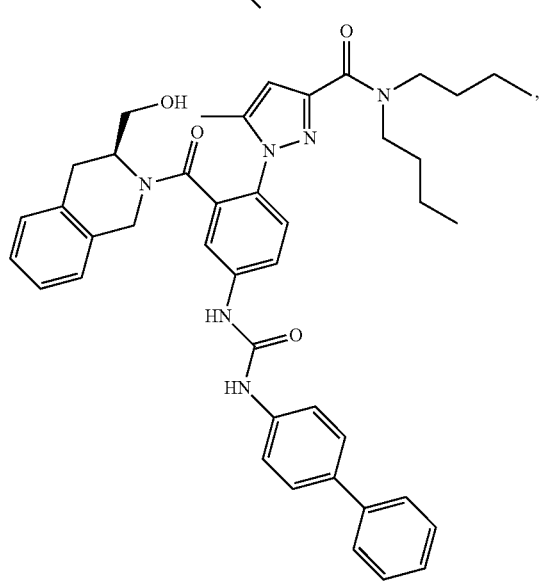
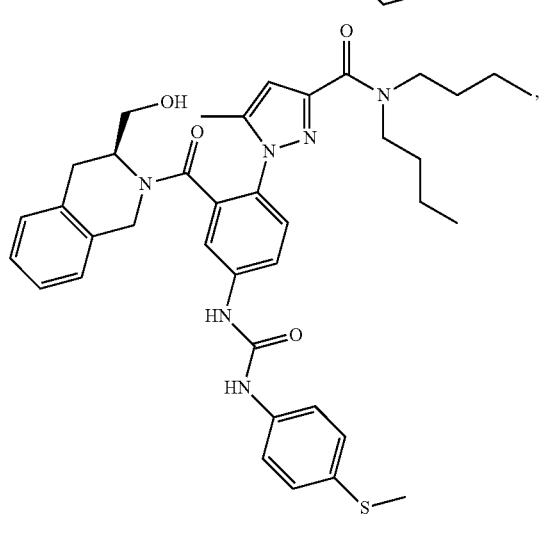
1844
-continued
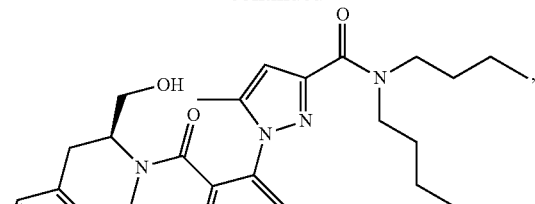
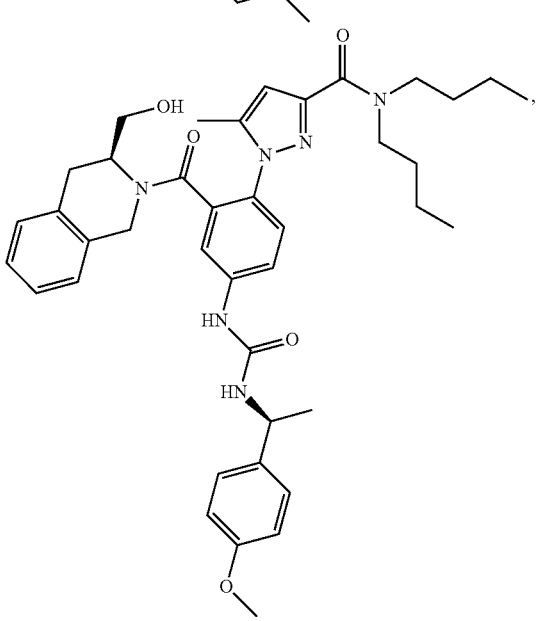
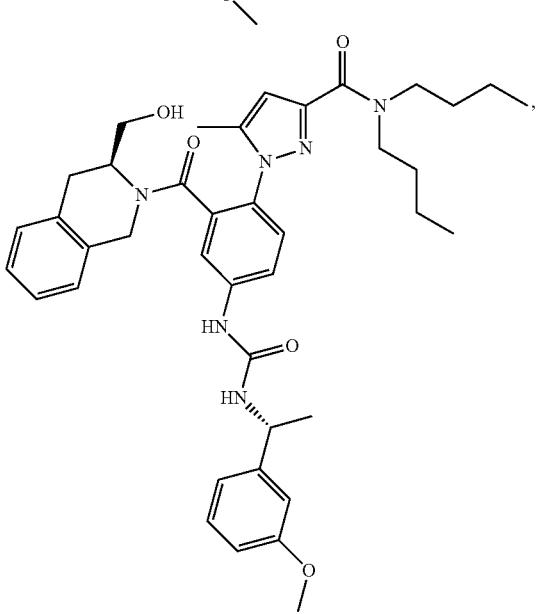

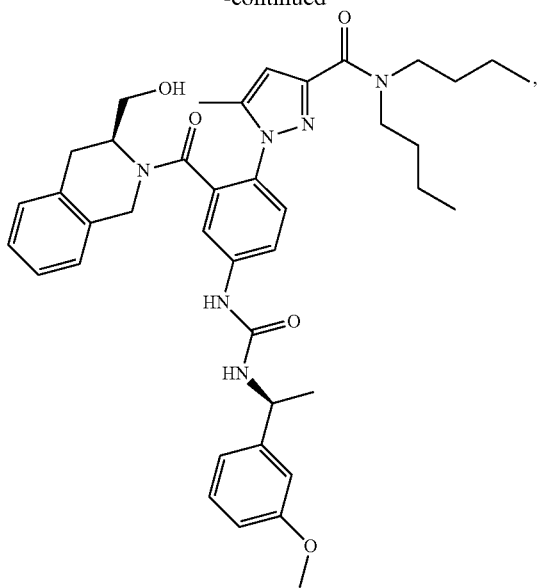
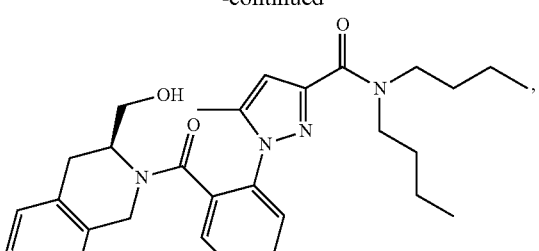
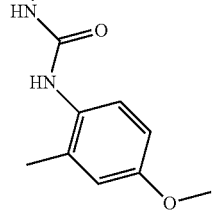
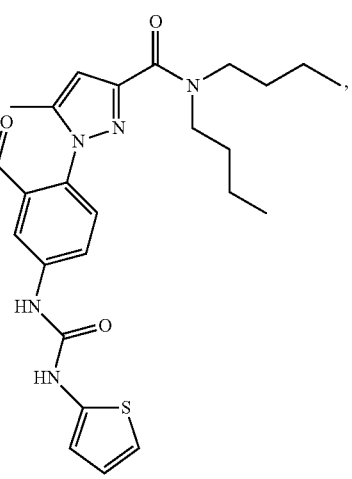

1847
-continued
1848
-continued
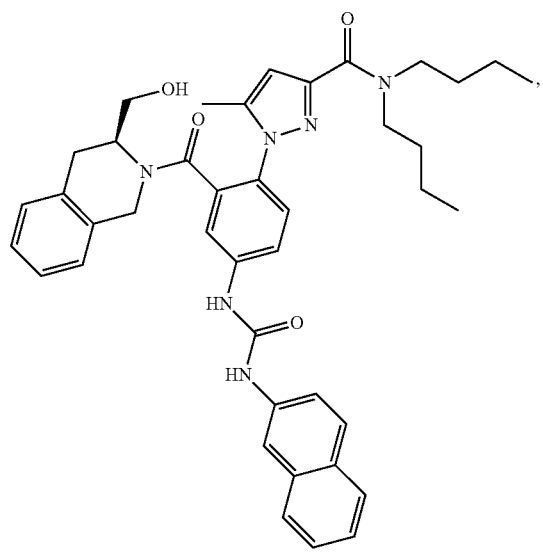
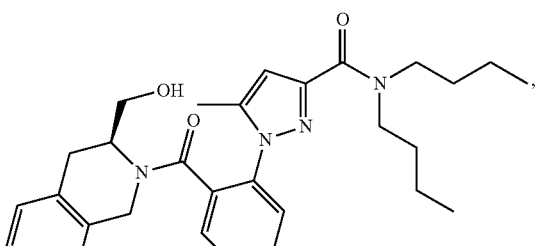
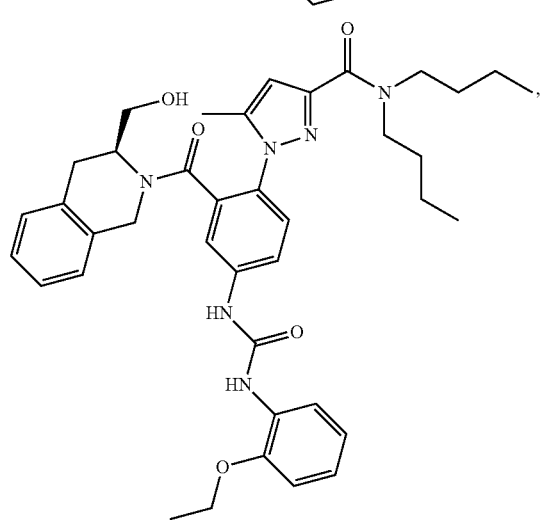
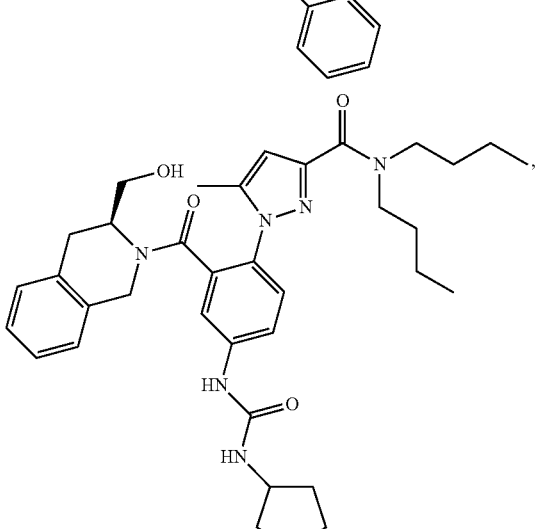
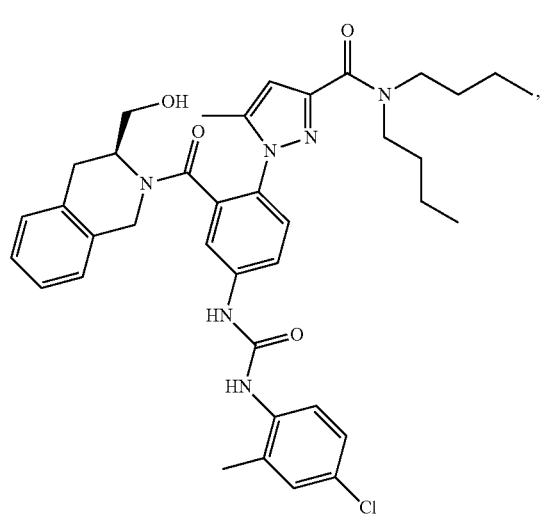
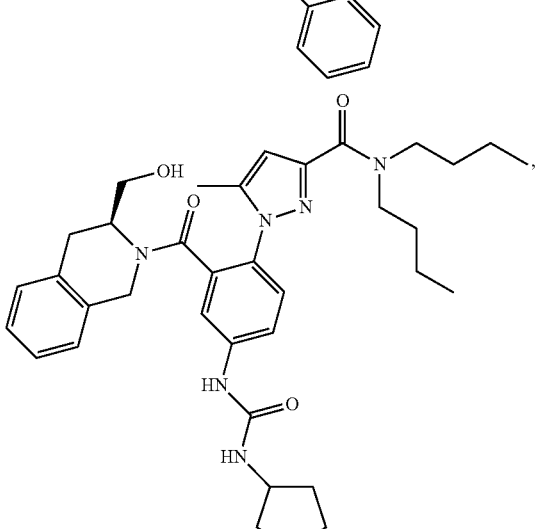

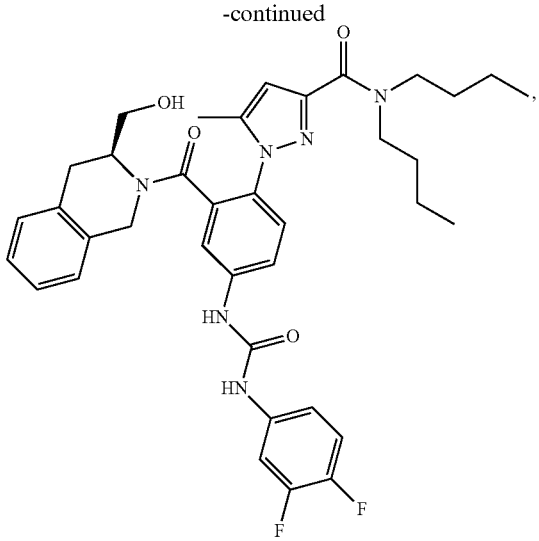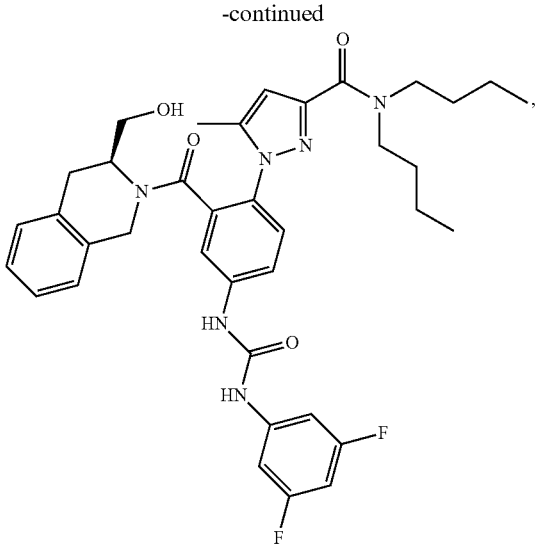

1851
-continued

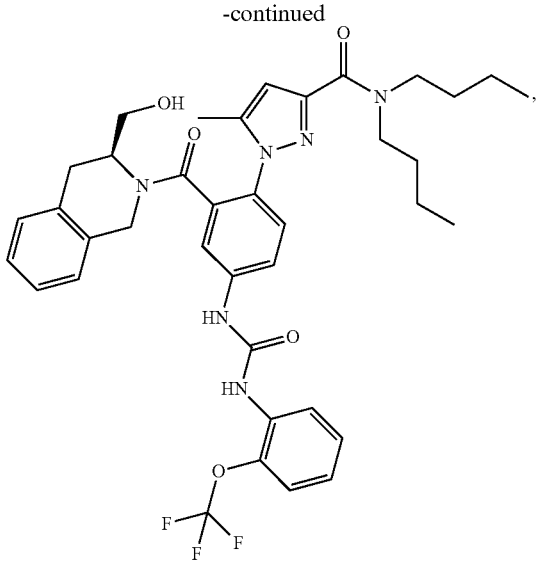

1852
-continued

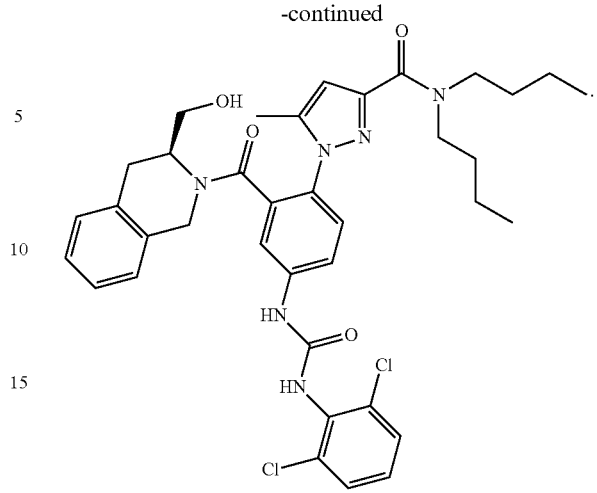

In some embodiments, the compound is selected from the group consisting of:

| Name | Chemical Structure |
| --- | --- |
| (R)-4-(4-((4'-chloro-biphenyl-2-yl)methyl)piperazin-1-yl)-N-(4-(4-((2-(hydroxyamino)-2-oxoethyl)(methyl)amino)-1-(phenylthio)-butan-2-ylamino)-3-nitrophenylsulfonyl)benzamide | 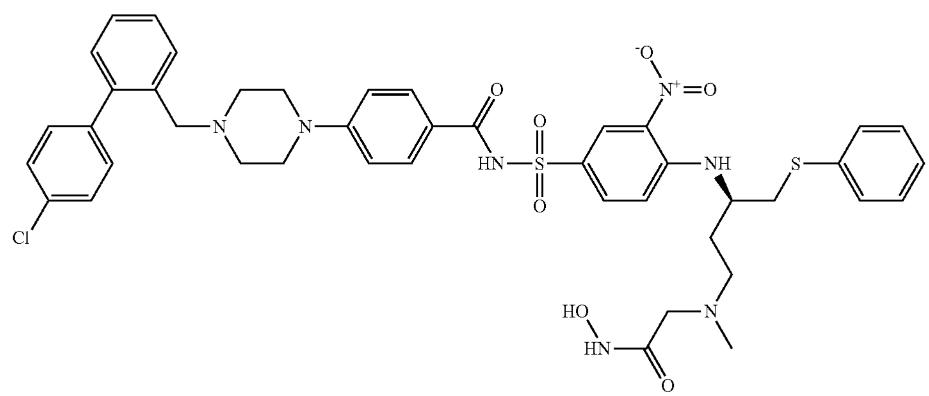 |
| (R)-4-(4-((4'-chloro-biphenyl-2-yl)methyl)piperazin-1-yl)-N-(4-(4-((3-(hydroxyamino)-3-oxopropyl)(methyl)amino)-1-(phenylthio)-butan-2-ylamino)-3-nitrophenylsulfonyl)benzamide | 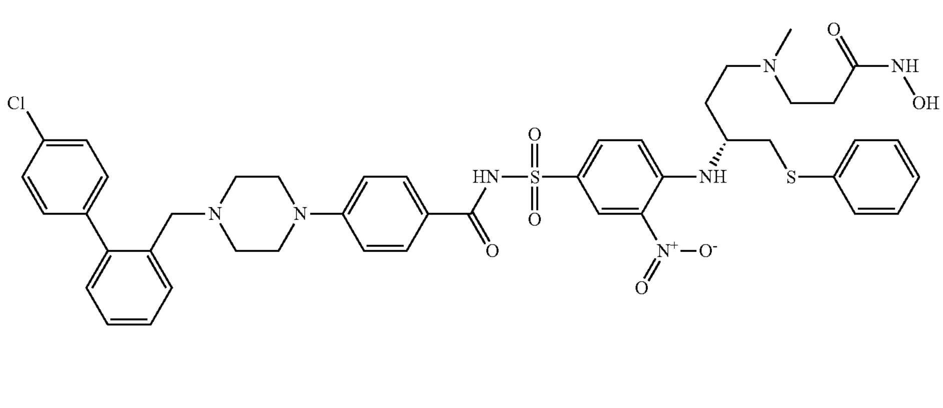 [SMILES: CN(CCC(=O)NO)CC[C@H](CSc1ccccc1)Nc1ccc(S(=O)(=O)NC(=O)c2ccc(N3CCN(Cc4ccccc4-c4ccc(Cl)cc4)CC3)cc2)cc1[N+](=O)[O-]] |

-continued

| Name | Chemical Structure |
|---|---|
| (R)-4-(4-((4'-chloro-biphenyl-2-yl)methyl)-piperazin-1-yl)-N-(4-(4-((4-(hydroxyamino)-4-oxobutyl)(methyl)amino)-1-(phenylthio)butan-2-ylamino)-3-nitrophenyl-sulfonyl)benzamide | 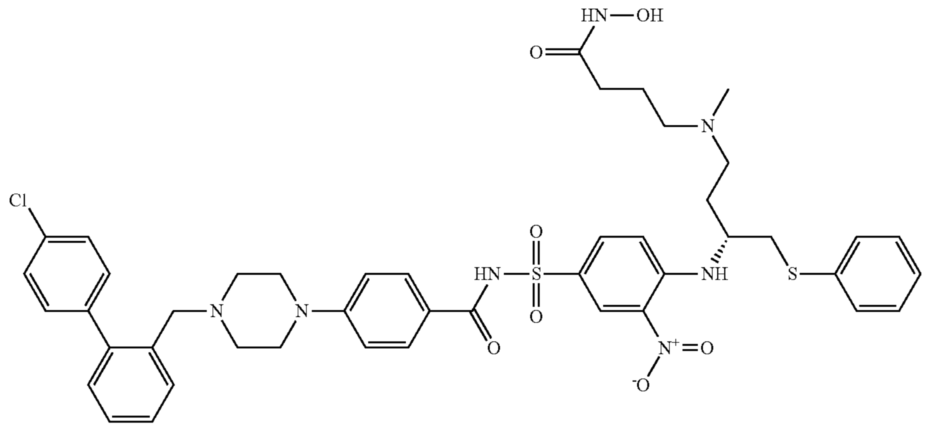 |
| (R)-4-(4-((4'-chloro-biphenyl-2-yl)methyl)-piperazin-1-yl)-N-(4-(4-((5-(hydroxyamino)-5-oxopentyl)(methyl)amino)-1-(phenylthio)butan-2-ylamino)-3-nitrophenyl-sulfonyl)benzamide | 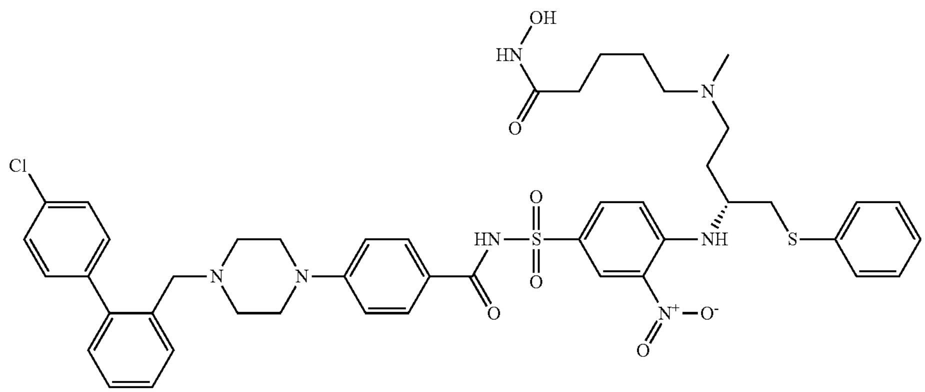 [SMILES: CN(CCCCC(=O)NO)CC[C@H](CSc1ccccc1)Nc1ccc(S(=O)(=O)NC(=O)c2ccc(N3CCN(Cc4ccccc4-c4ccc(Cl)cc4)CC3)cc2)cc1[N+](=O)[O-]] |
| (R)-4-(4-((4'-chloro-biphenyl-2-yl)methyl)-piperazin-1-yl)-N-(4-(4-((6-(hydroxyamino)-6-oxohexyl)(methyl)amino)-1-(phenylthio)butan-2-ylamino)-3-nitrophenylsulfonyl)benzamide | 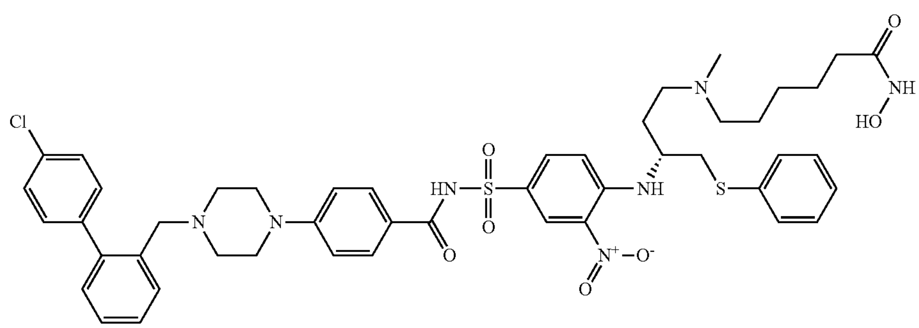 [SMILES: CN(CCCCCC(=O)NO)CC[C@H](CSc1ccccc1)Nc1ccc(S(=O)(=O)NC(=O)c2ccc(N3CCN(Cc4ccccc4-c4ccc(Cl)cc4)CC3)cc2)cc1[N+](=O)[O-]] |
| (R)-$N^1$-(2-(4-((4'-chloro-biphenyl-2-yl)methyl)-piperazin-1-yl)-5-(4-(4-(dimethylamino)-1-(phenylthio)butan-2-ylamino)-3-nitrophenylsulfonyl-carbamoyl)phenyl)-$N^5$-hydroxyglutaramide | 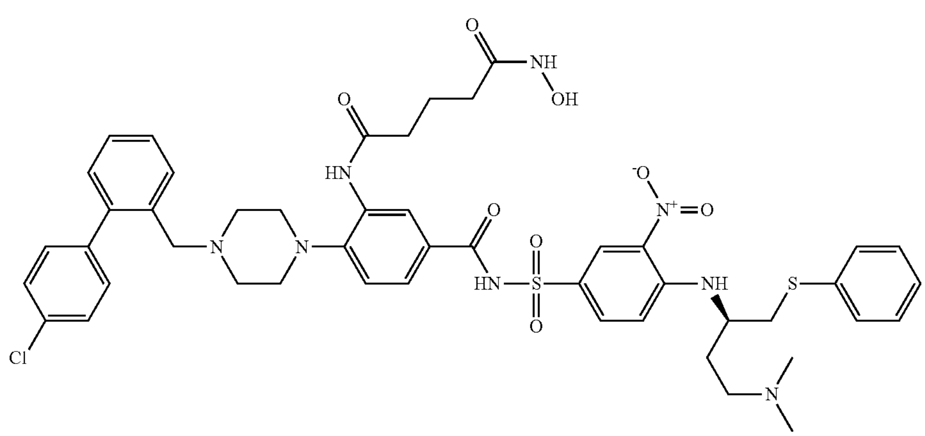 |

-continued

| Name | Chemical Structure |
|---|---|
| (R)-N¹-(2-(4-((4'-chloro-biphenyl-2-yl)methyl)-piperazin-1-yl)-5-(4-(4-(dimethylamino)-1-(phenylthio)butan-2-ylamino)-3-nitrophenylsulfonyl-carbamoyl)phenyl)-N⁶-hydroxyadipamide | |
| (R)-N1-(2-(4-((4'-chloro-biphenyl-2-yl)methyl)piperazin-1-yl)-5-(4-(1-(dimethylamino)-5-(phenylthio)pentan-3-ylamino)-3-nitrophenylsulfonyl-carbamoyl)phenyl)-N8-hydroxyoctanediamide | 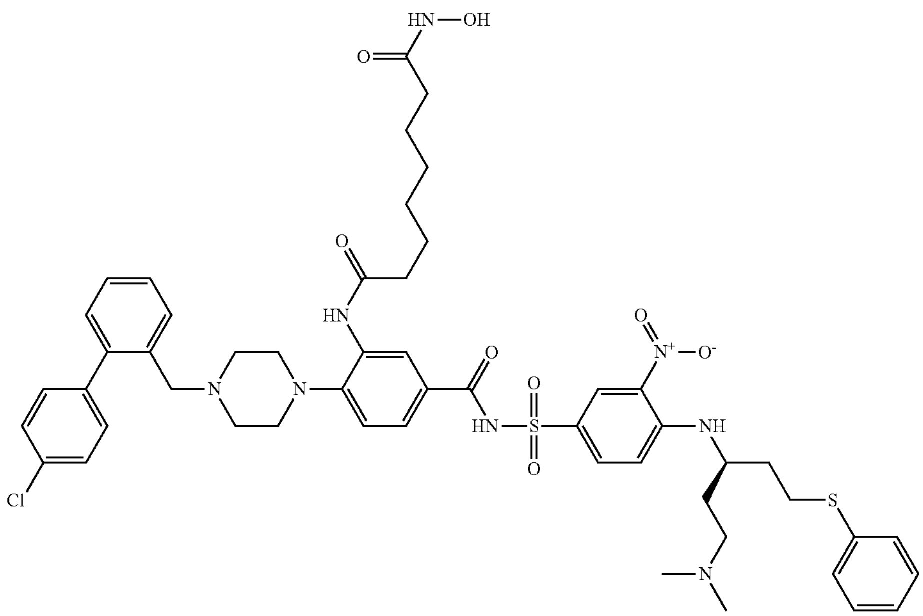 [SMILES: CN(C)CC[C@H](CCSc1ccccc1)Nc1ccc(S(=O)(=O)NC(=O)c2ccc(N3CCN(Cc4ccccc4-c4ccc(Cl)cc4)CC3)c(NC(=O)CCCCCCC(=O)NO)c2)cc1[N+](=O)[O-]] |

In some embodiments, the compound is selected from the group consisting of:

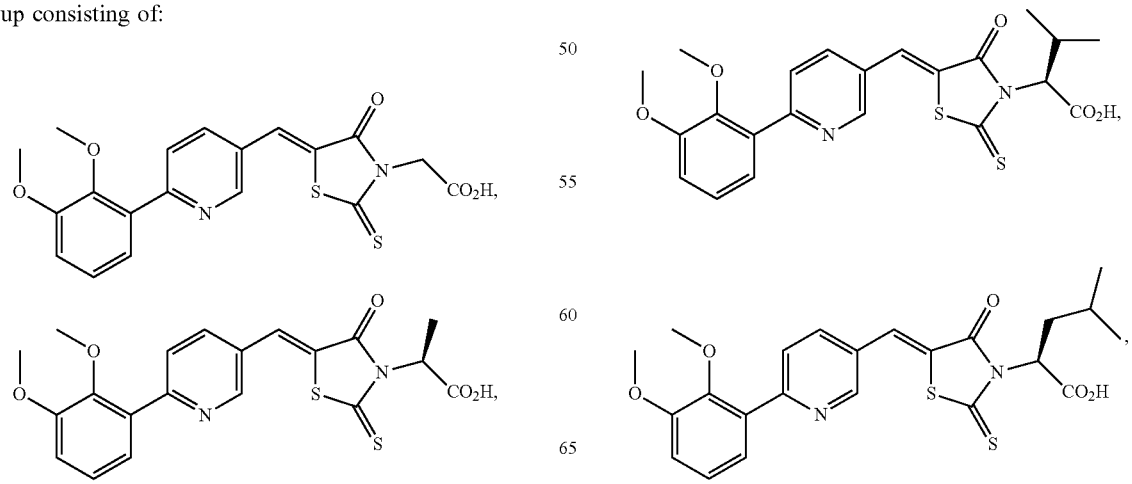

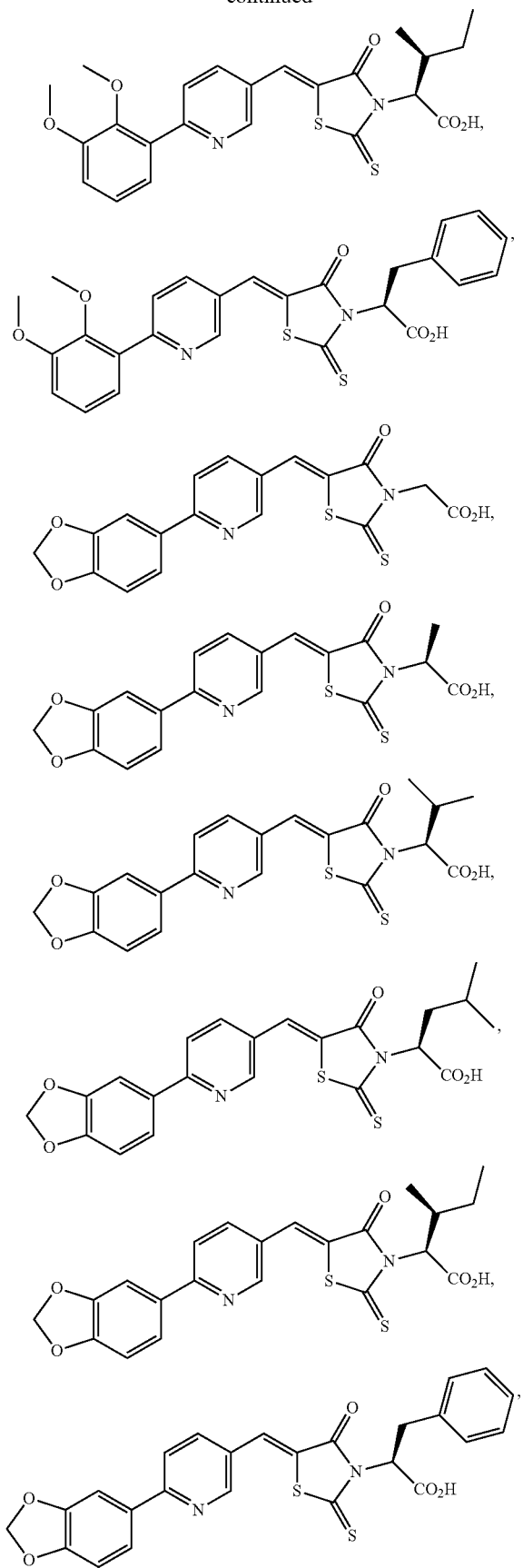
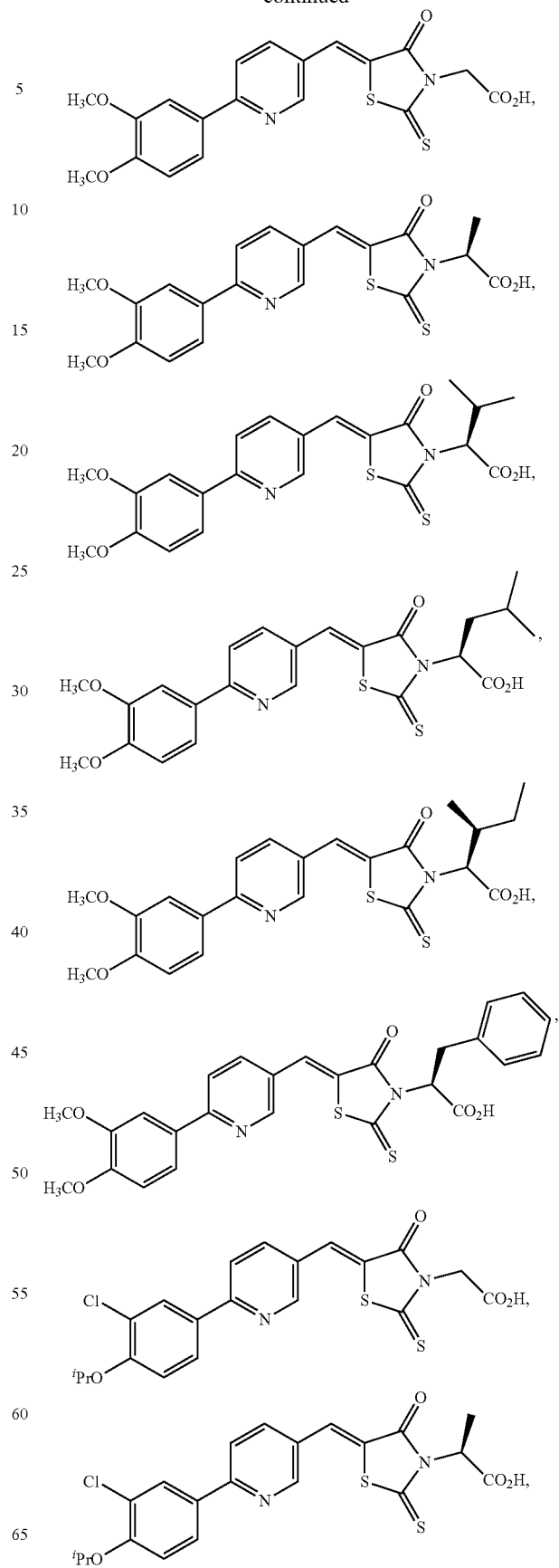

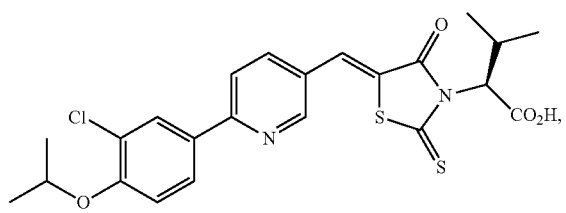
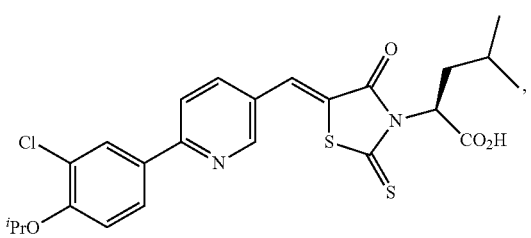
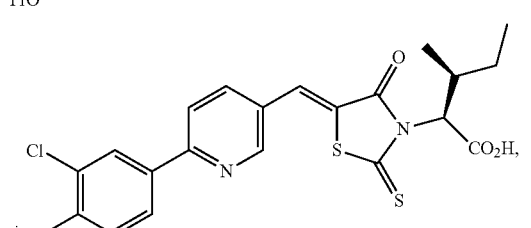
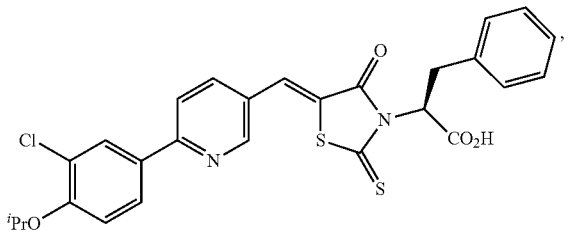
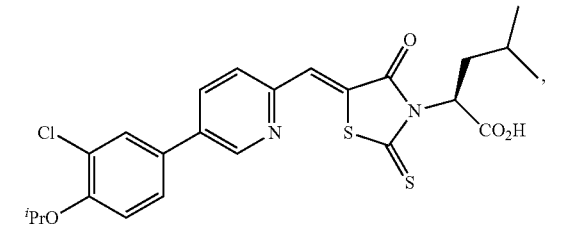
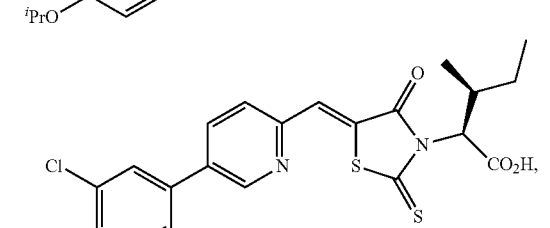
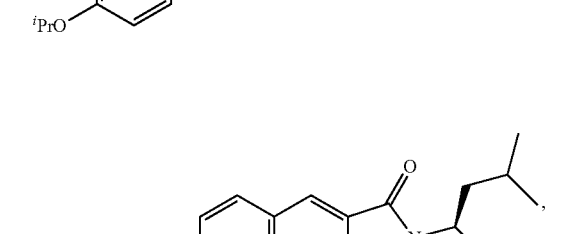
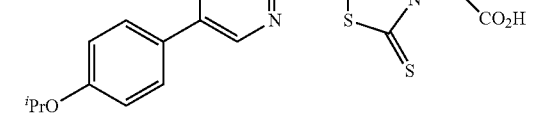
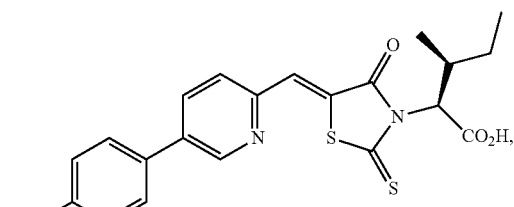
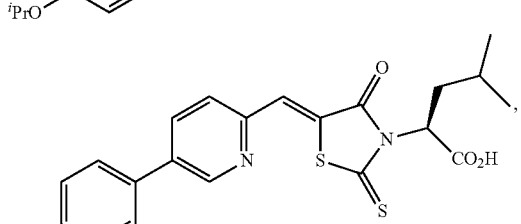
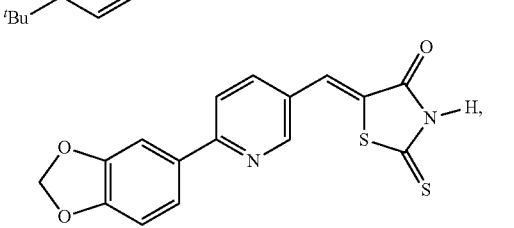
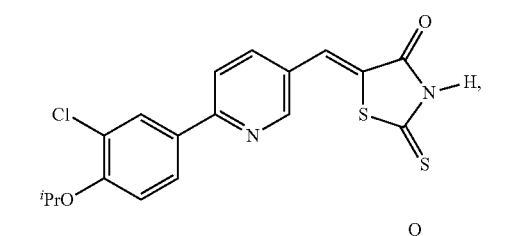
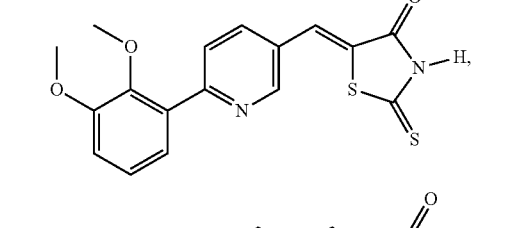
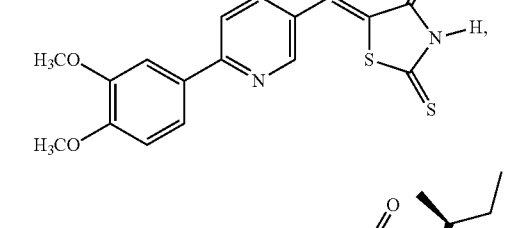
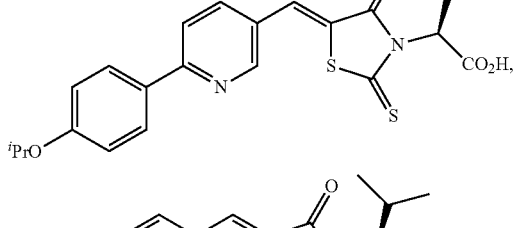
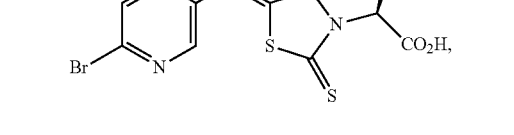

-continued
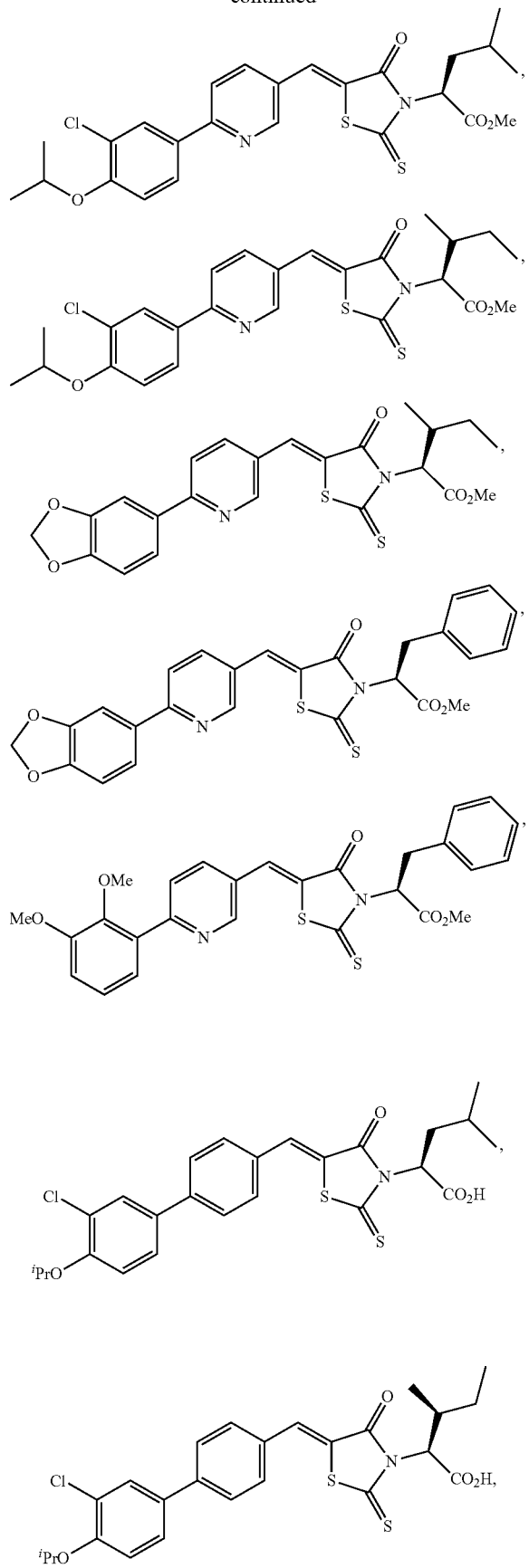
-continued
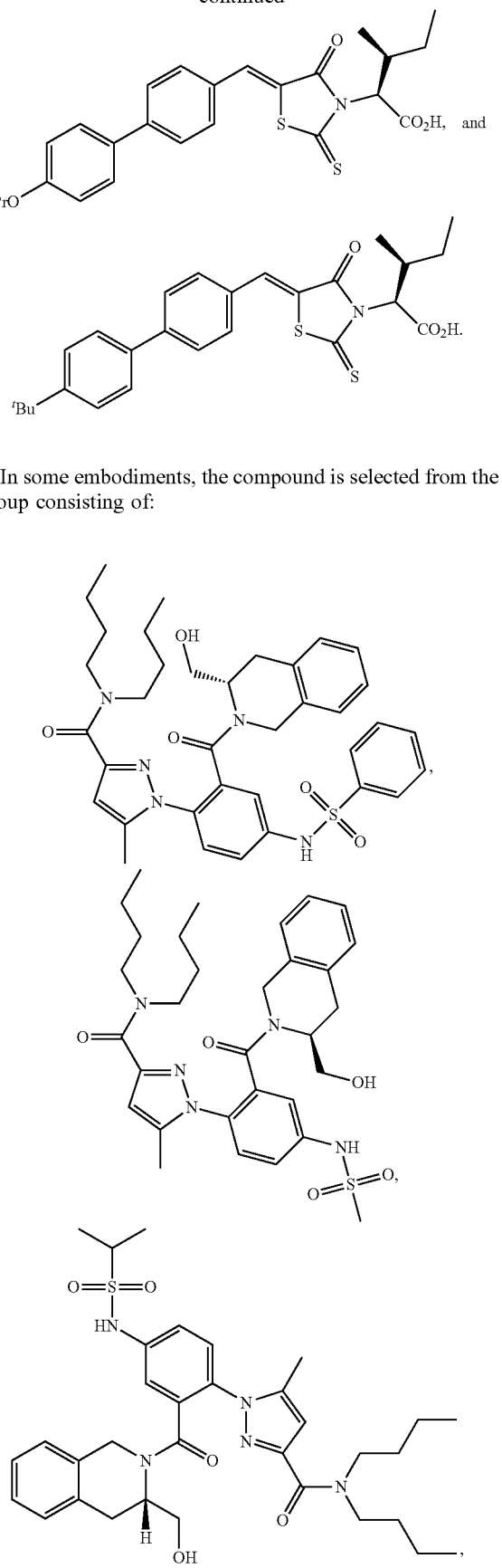
In some embodiments, the compound is selected from the group consisting of:

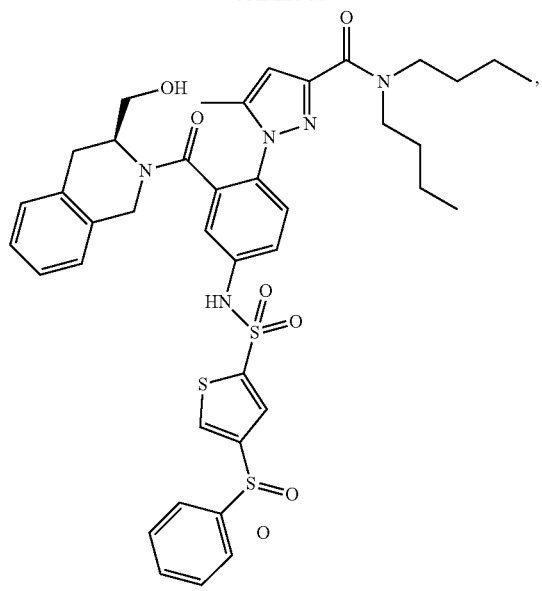
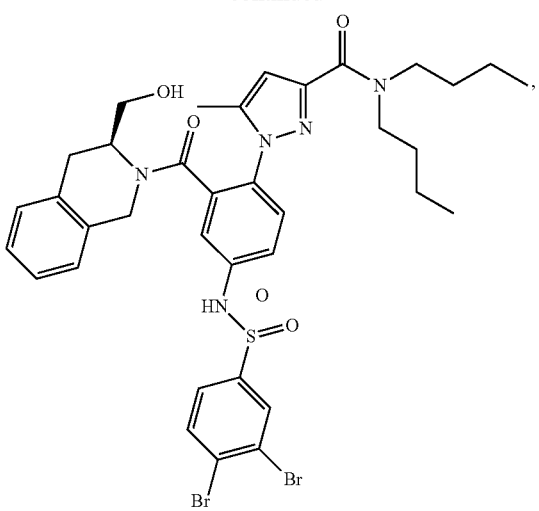
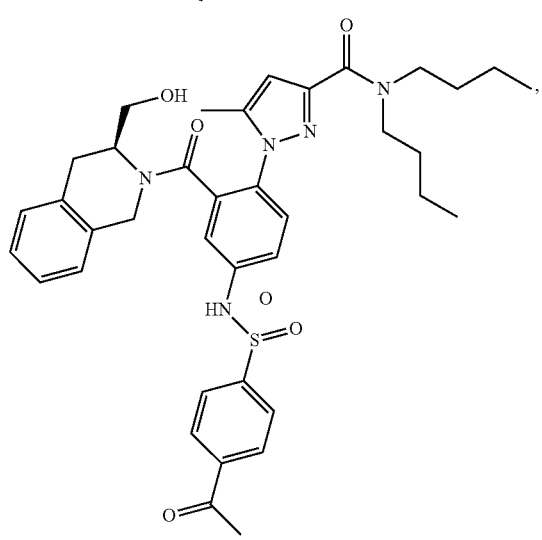
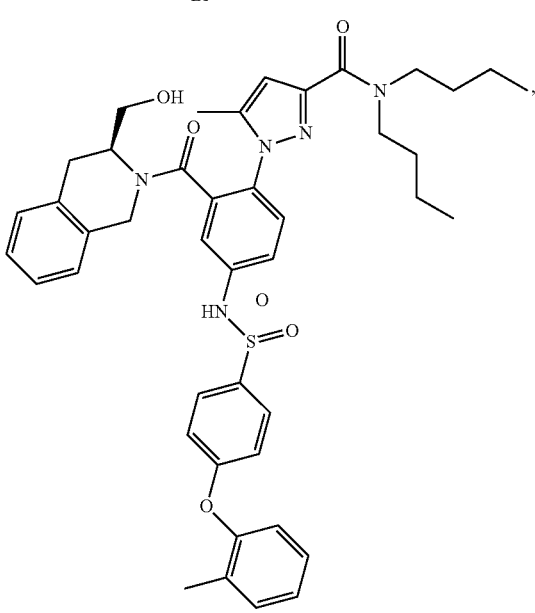
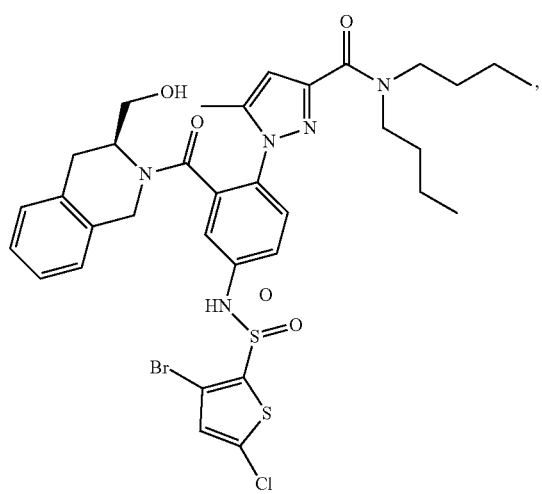
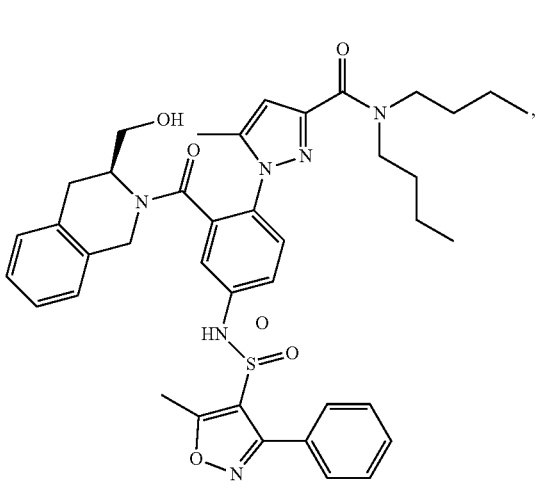

1865
-continued
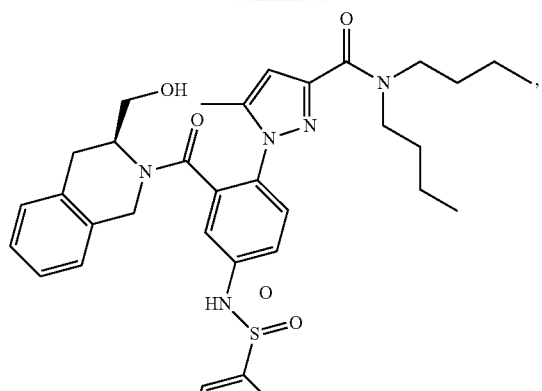
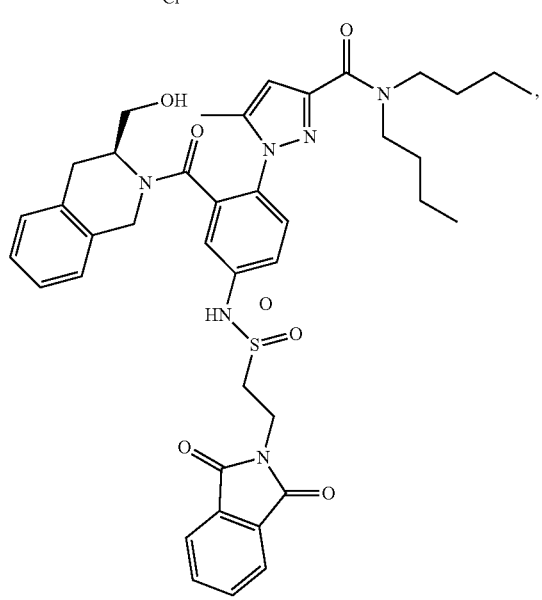
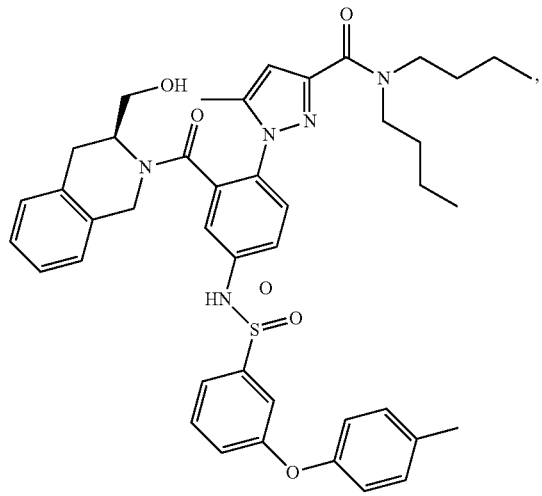
1866
-continued
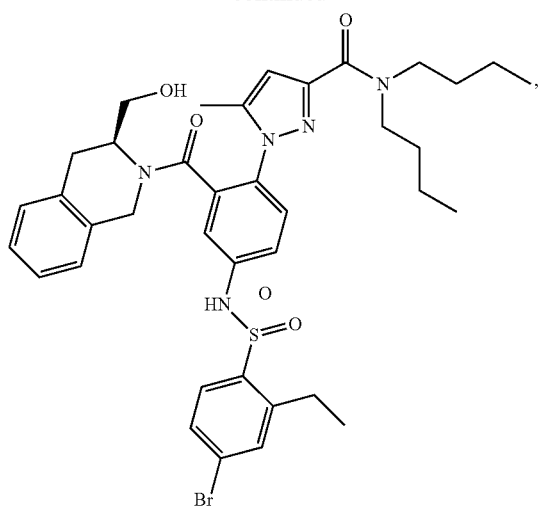
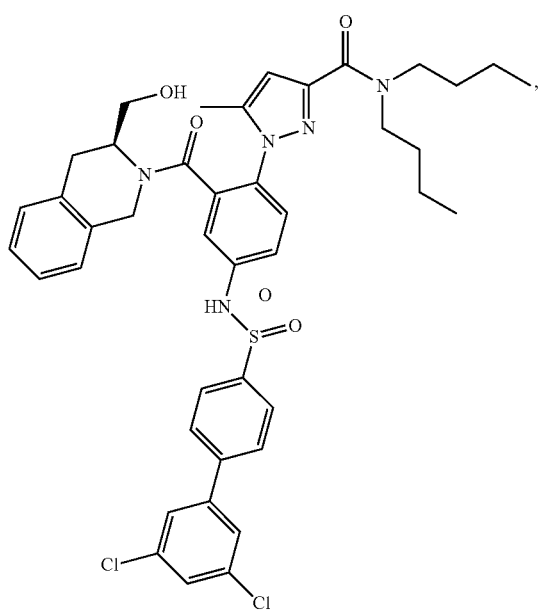
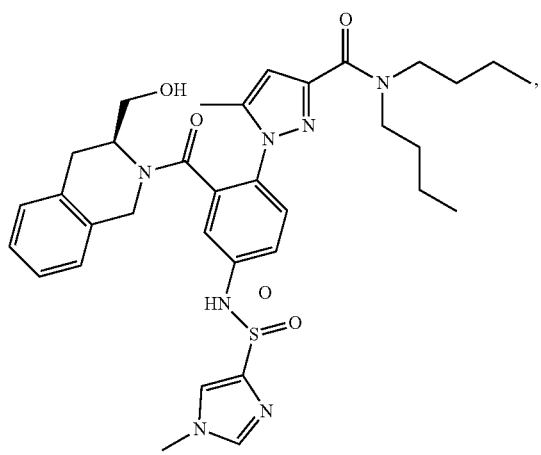

1867
-continued
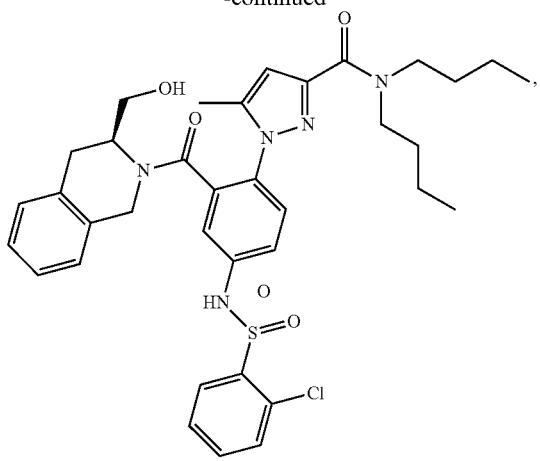
1868
-continued
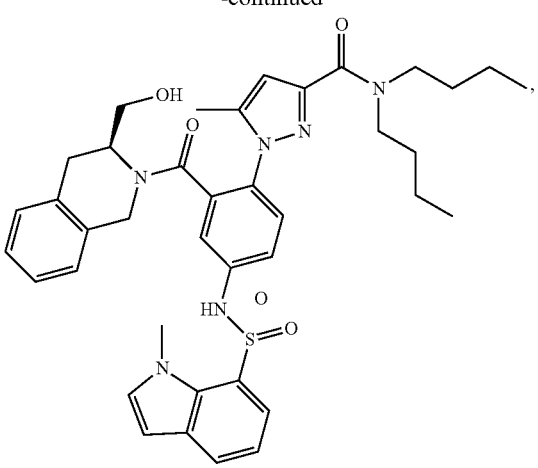
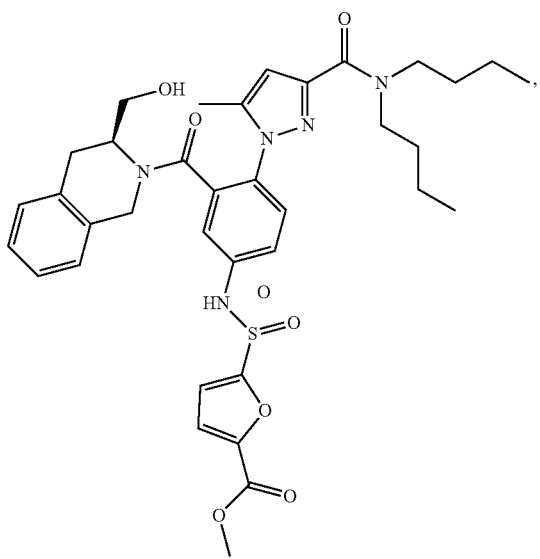

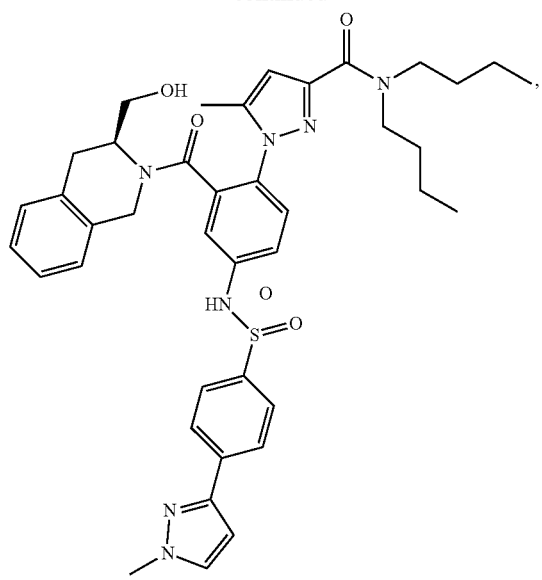
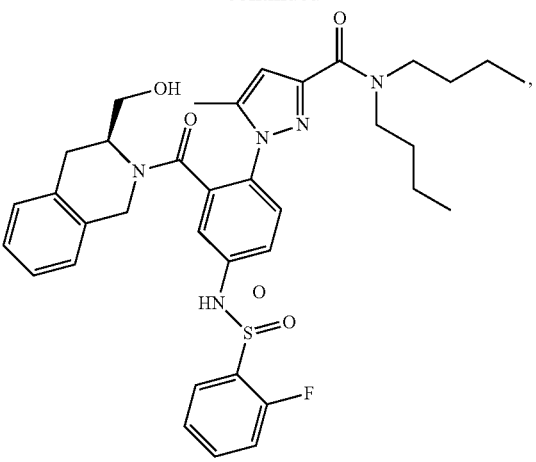
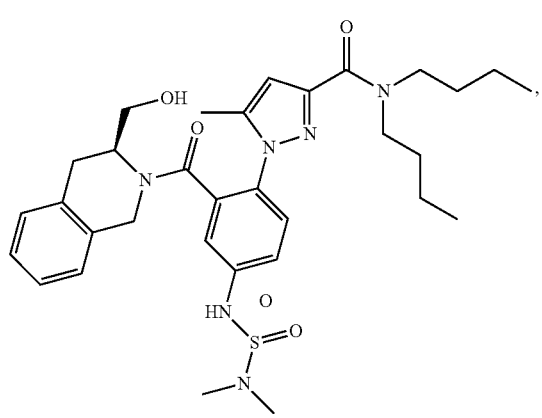
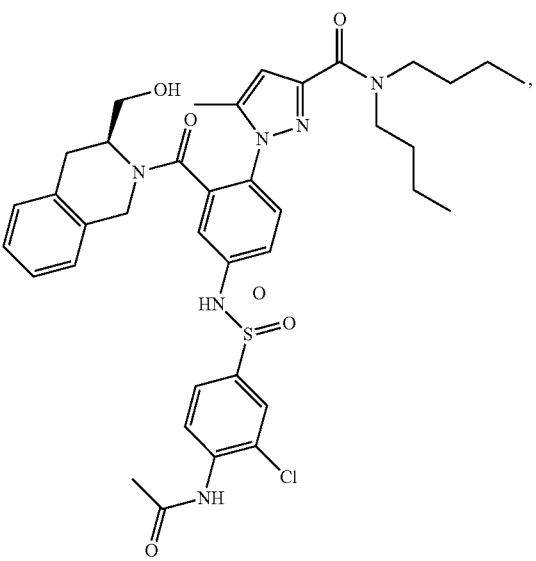
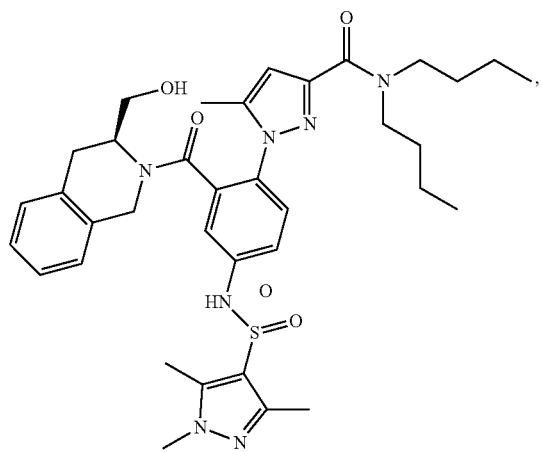
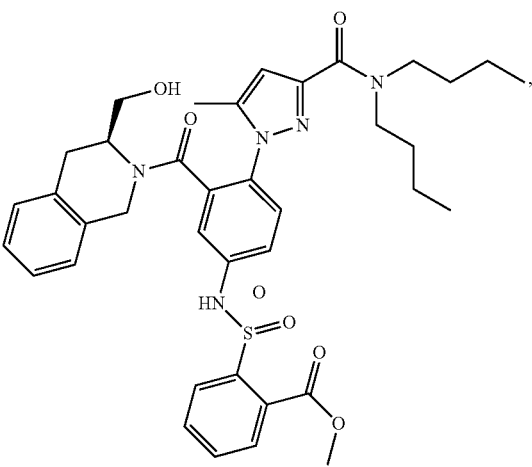

1871
-continued
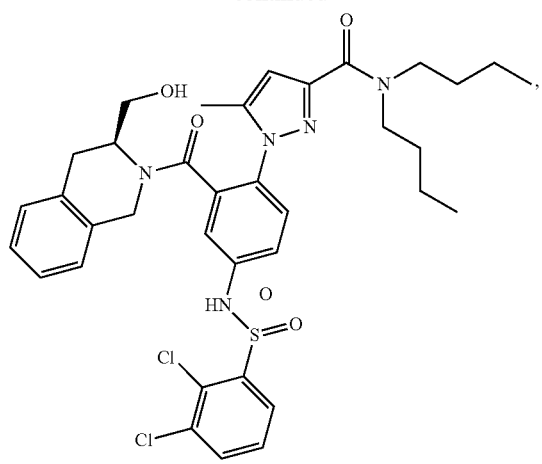
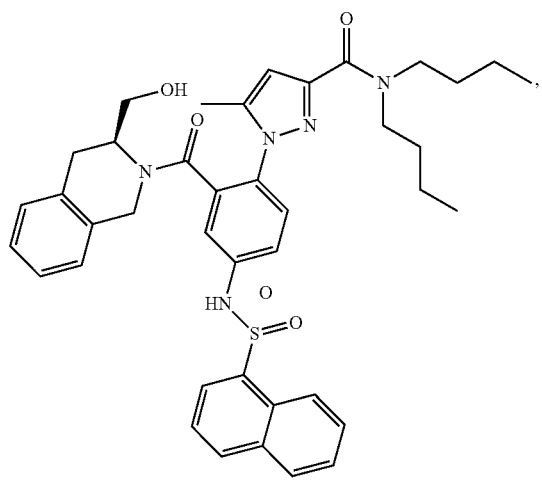
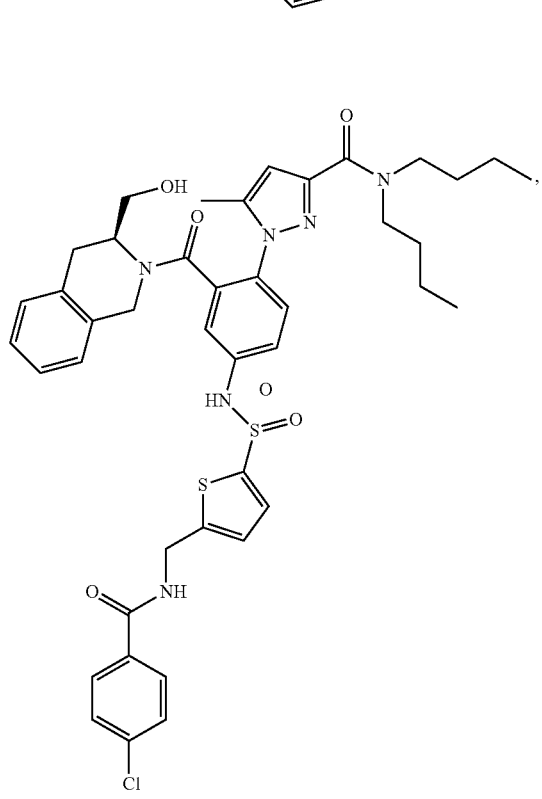
1872
-continued
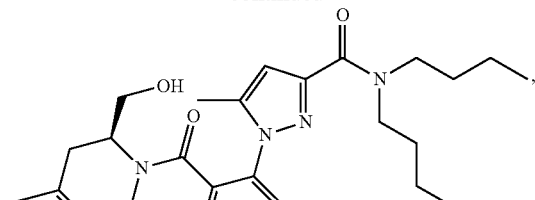
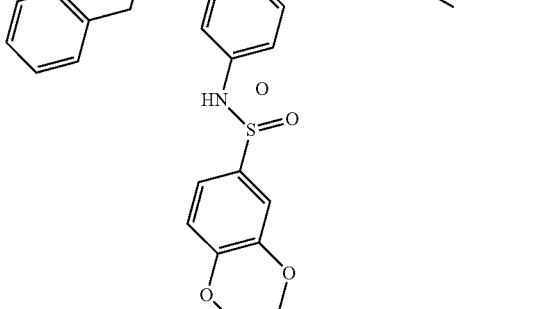
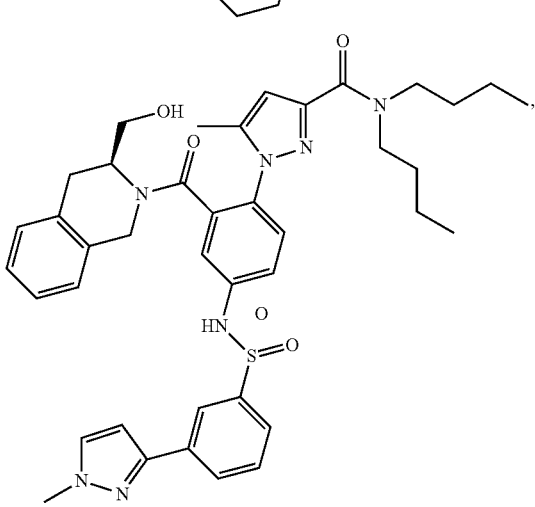
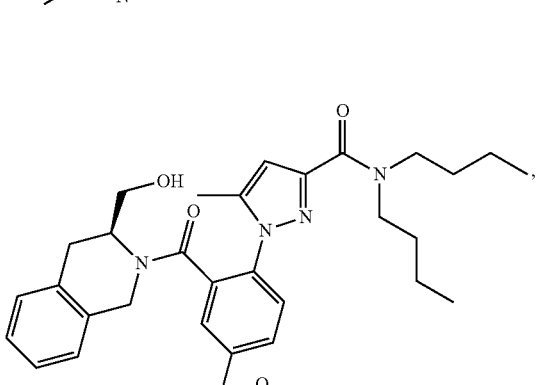
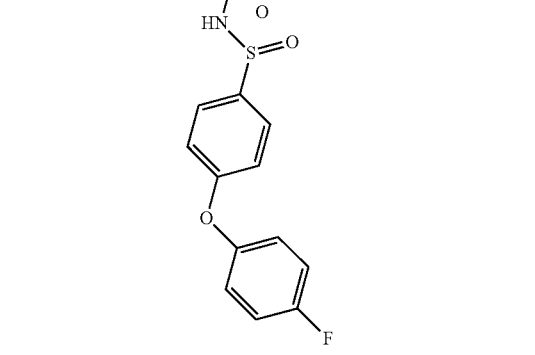

1873
-continued
1874
-continued
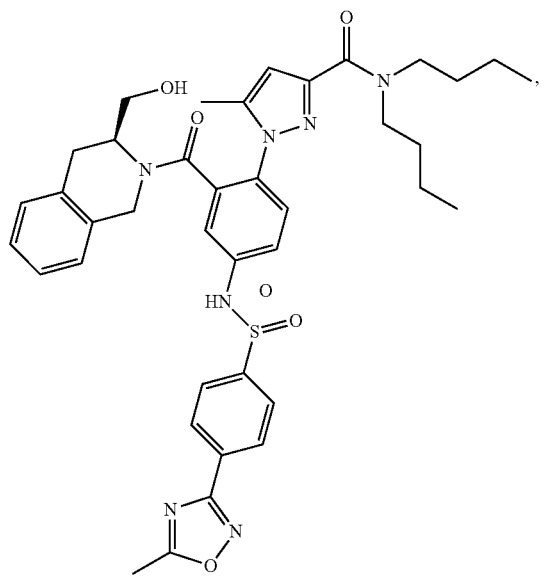
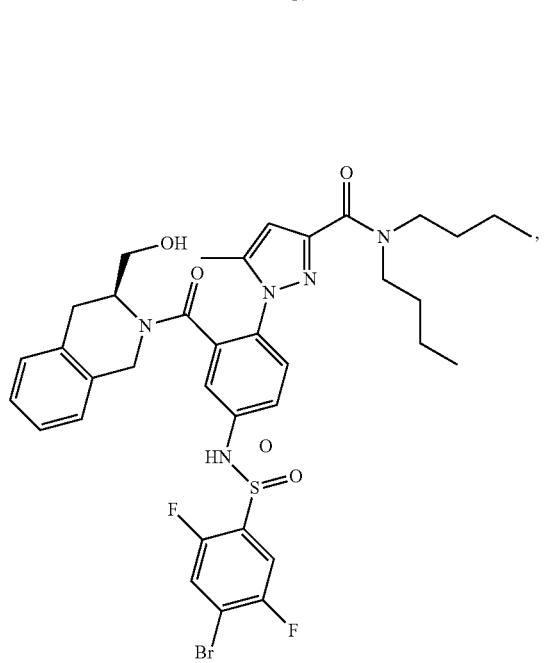
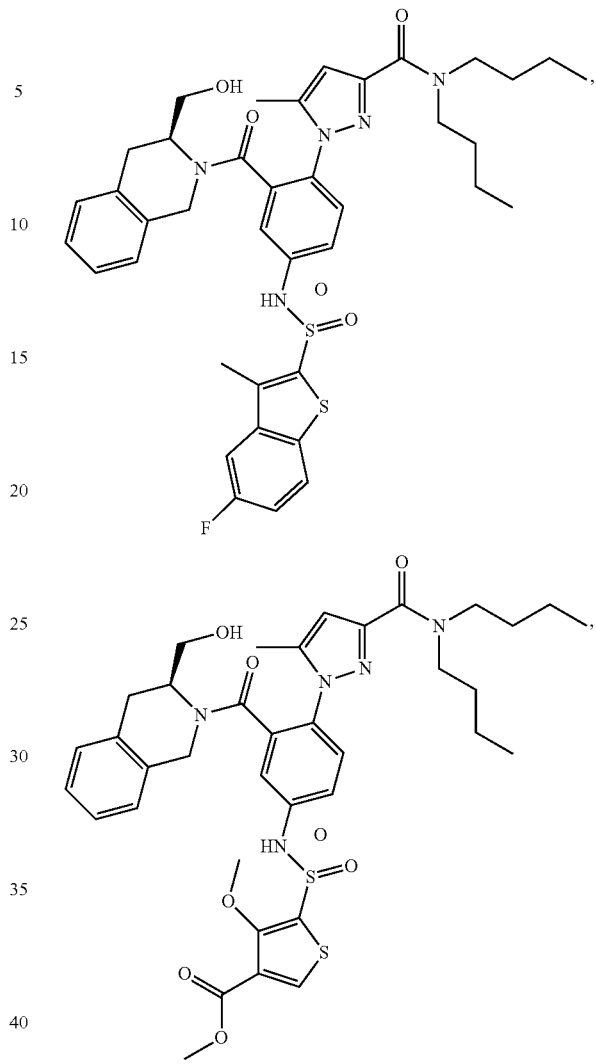

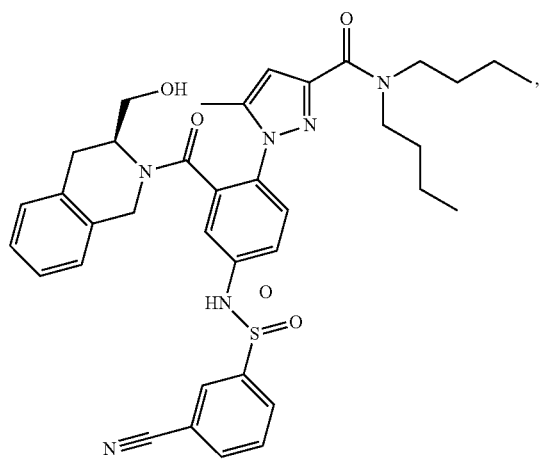
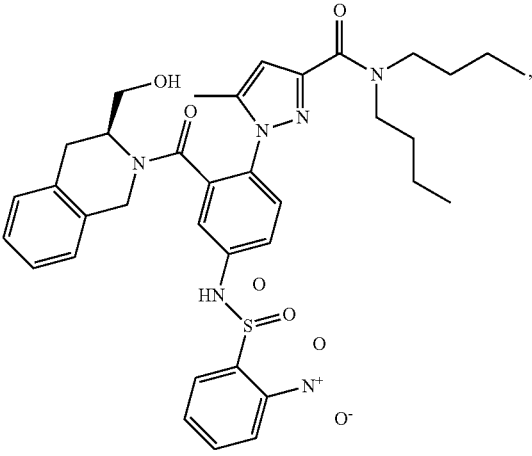
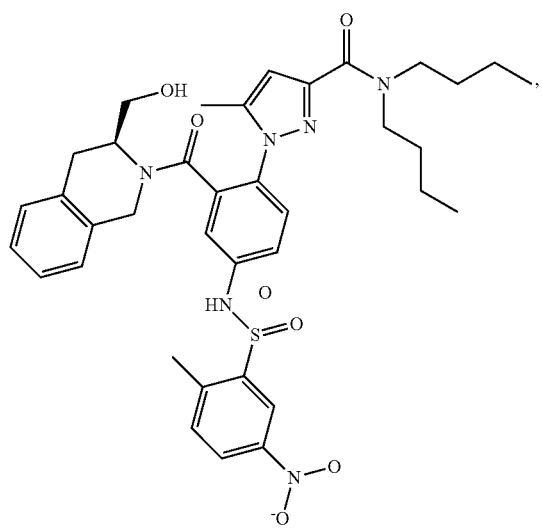
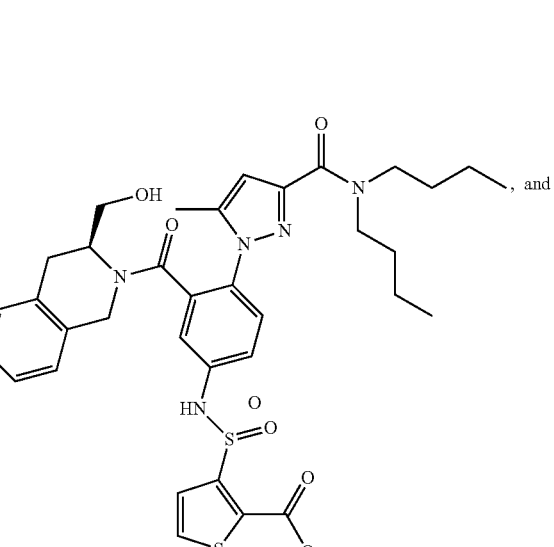
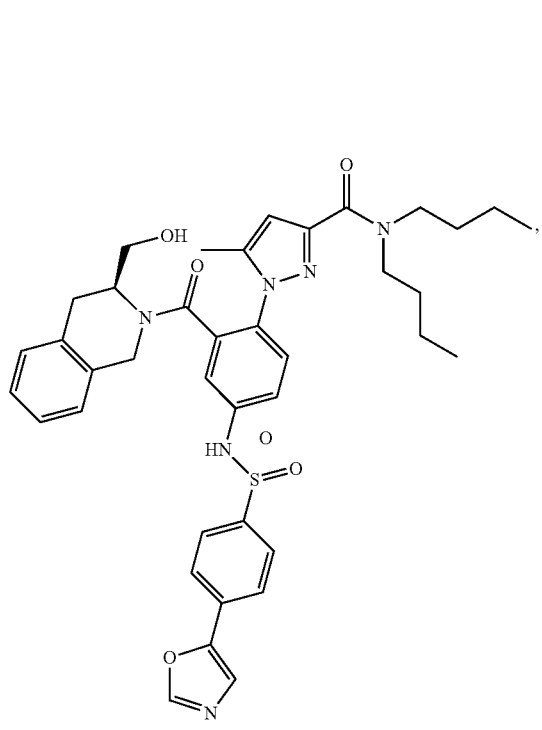

1877
-continued
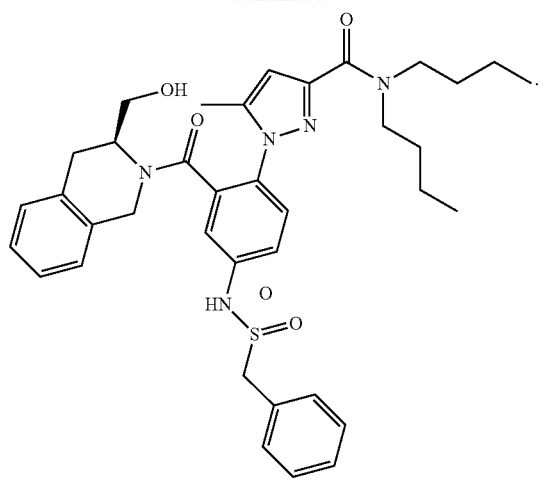
In some embodiments, the compound is selected from the group consisting of:
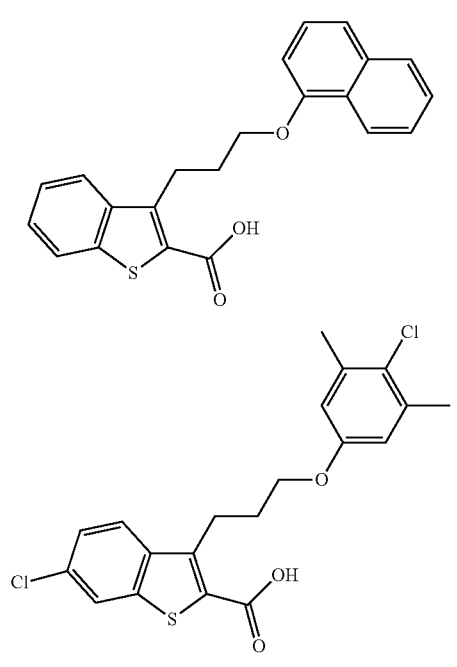
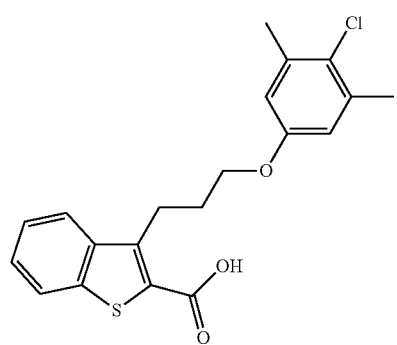
1878
-continued
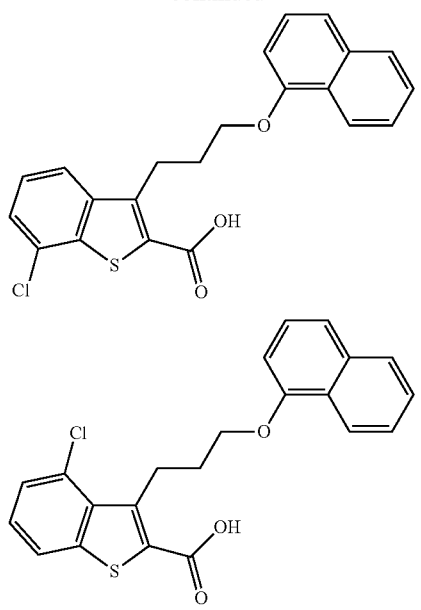
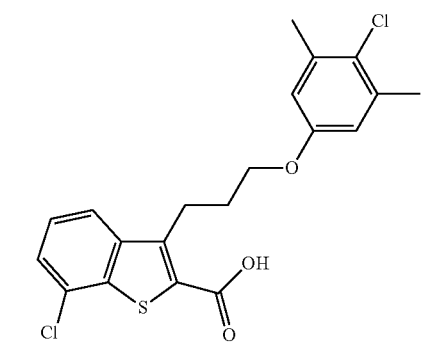
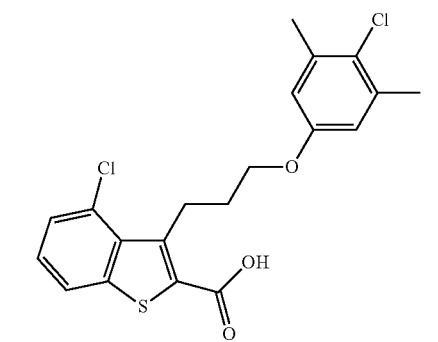

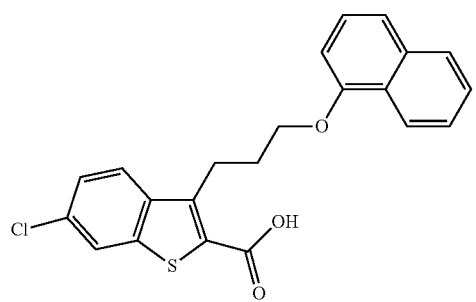
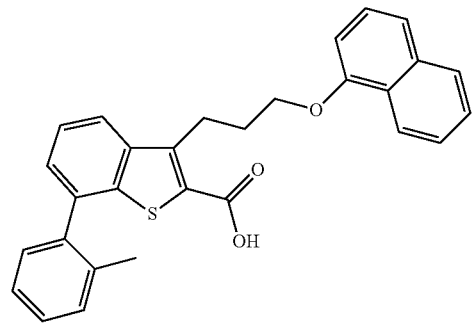
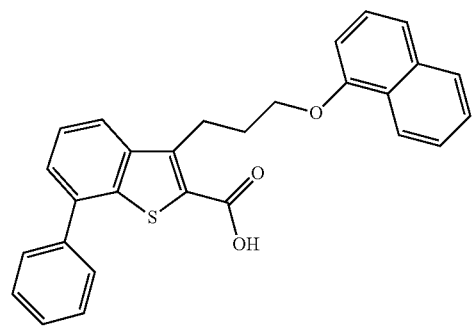
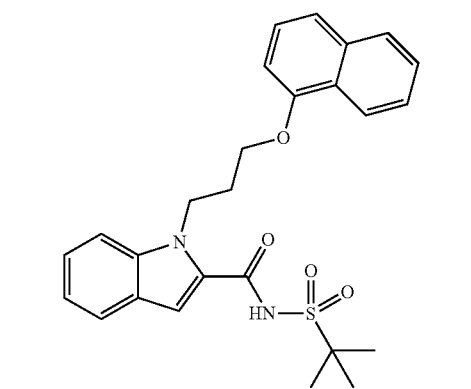
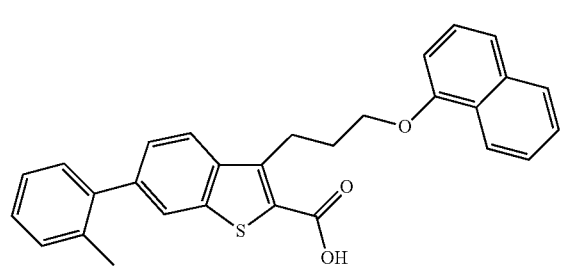
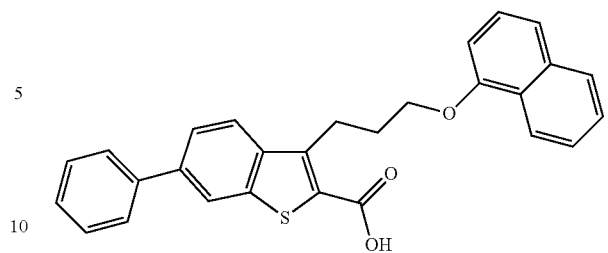
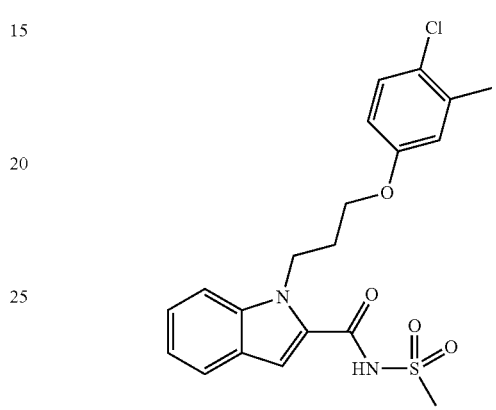
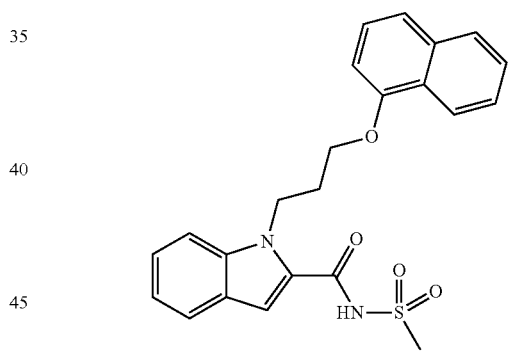
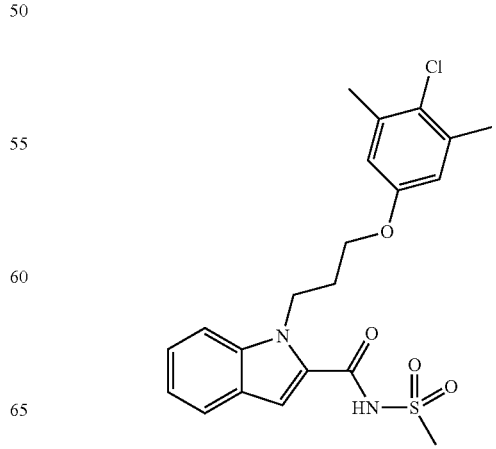

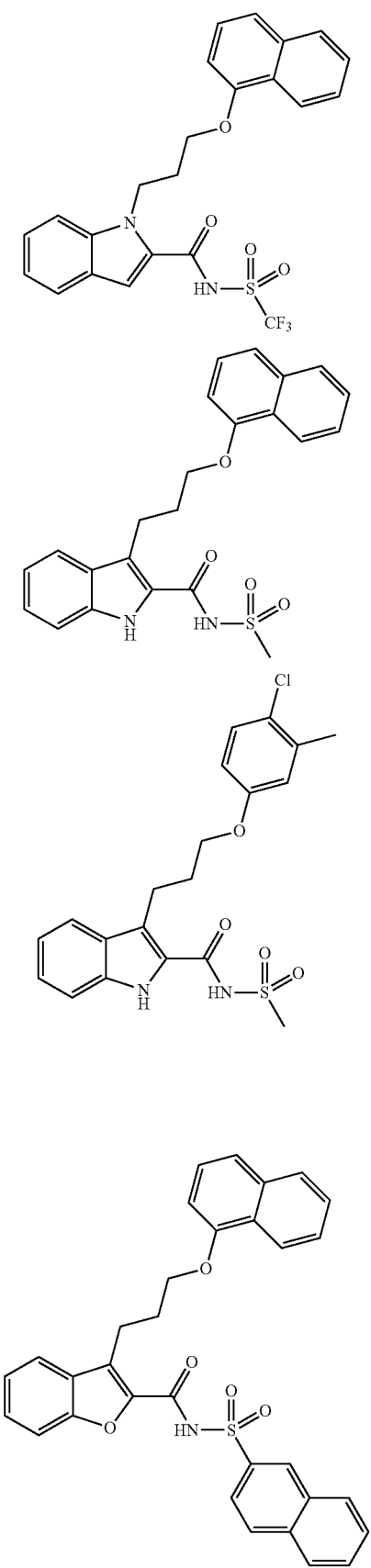
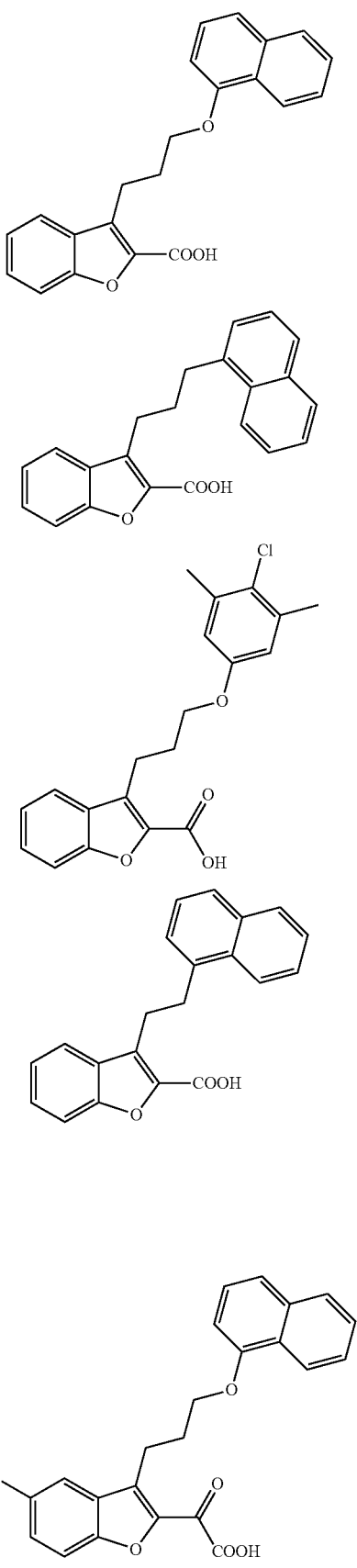

1883
-continued
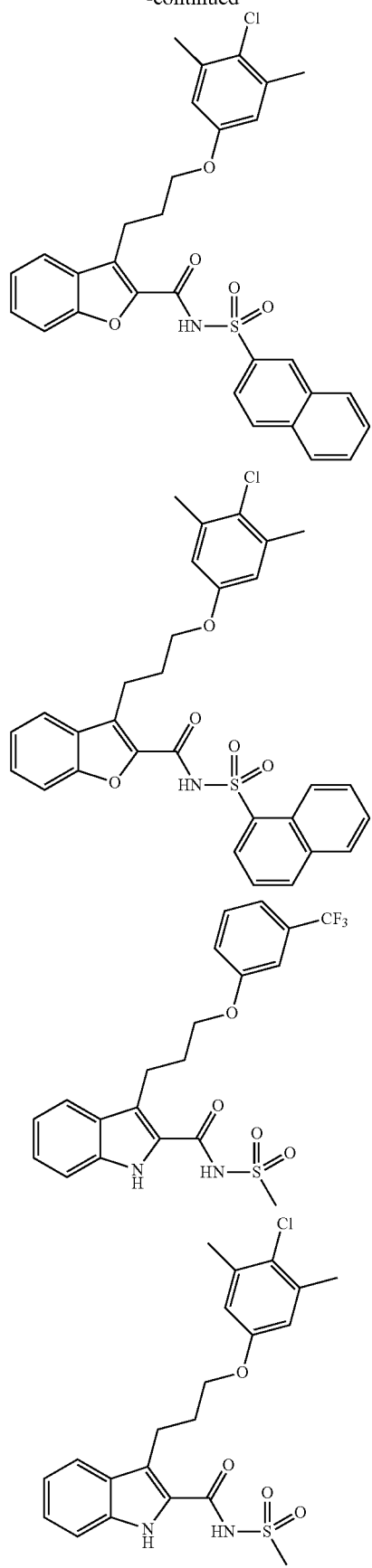
1884
-continued
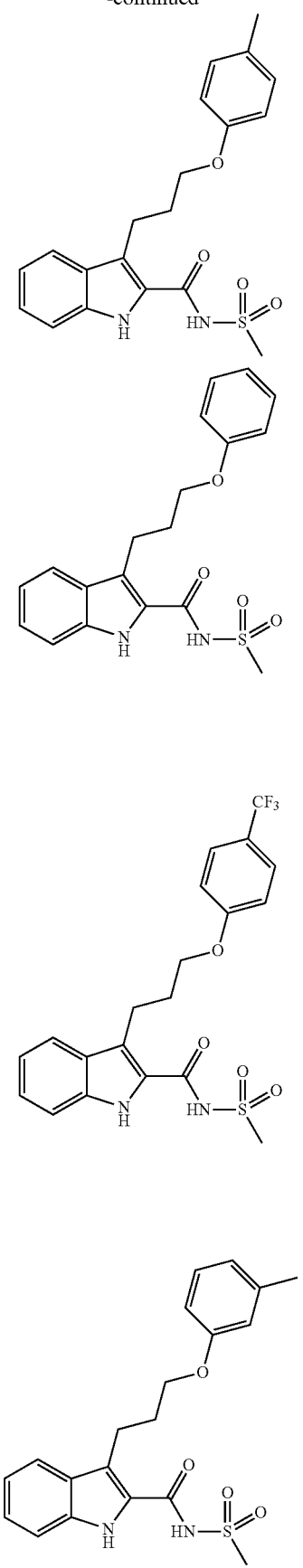

1885
-continued
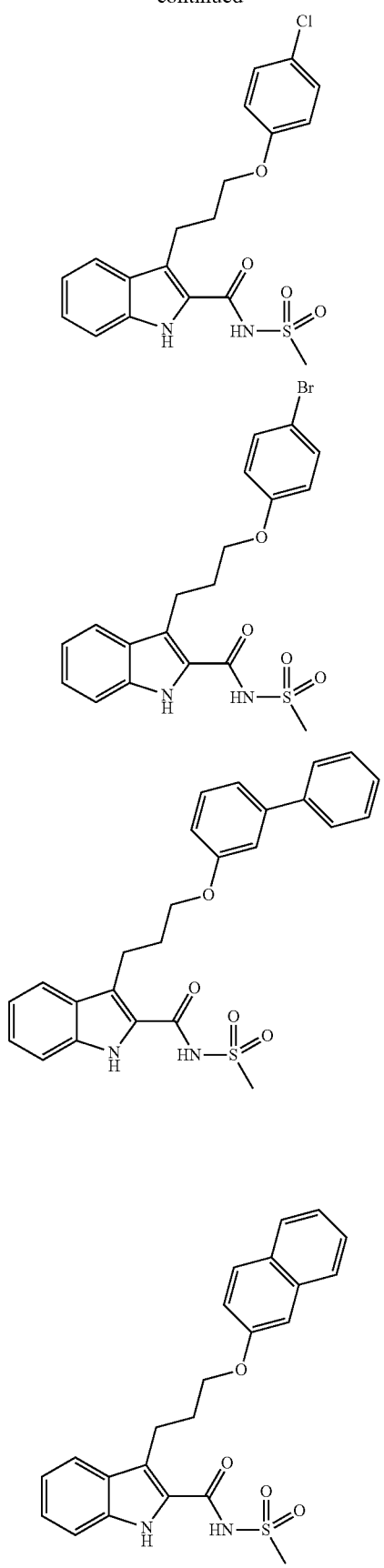
1886
-continued
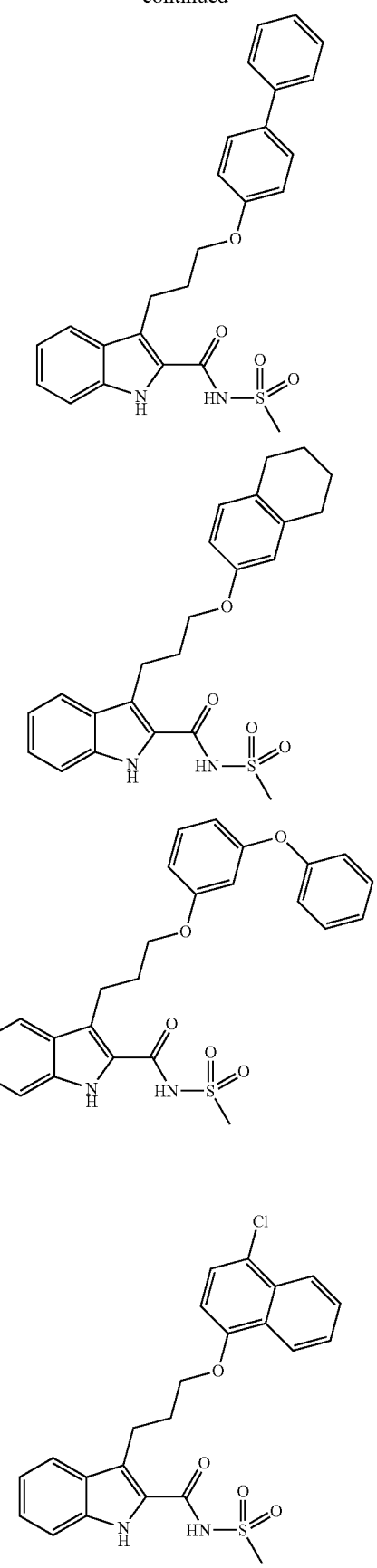

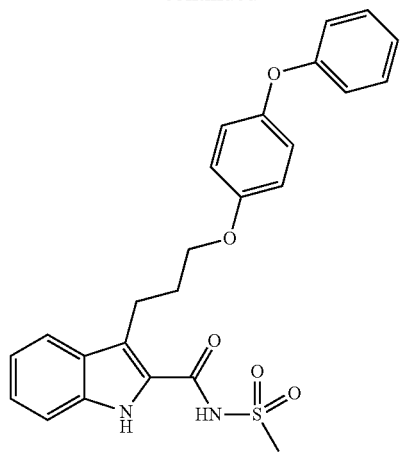
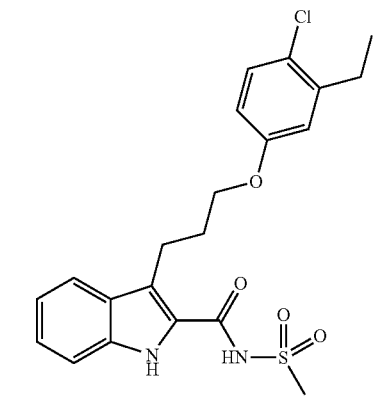
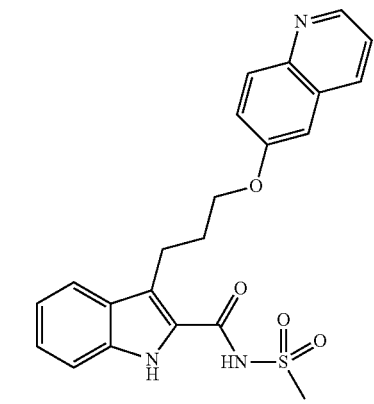
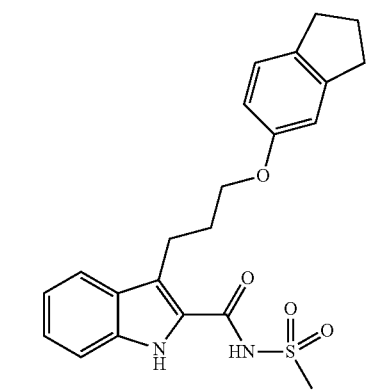
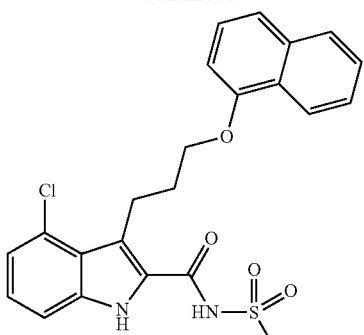
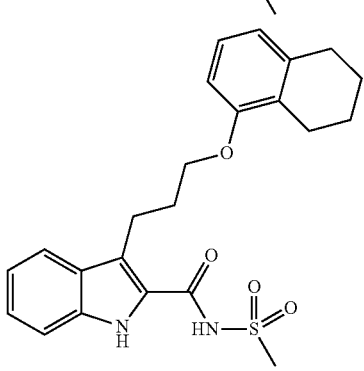
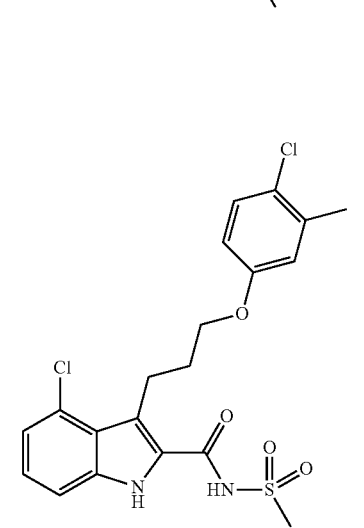
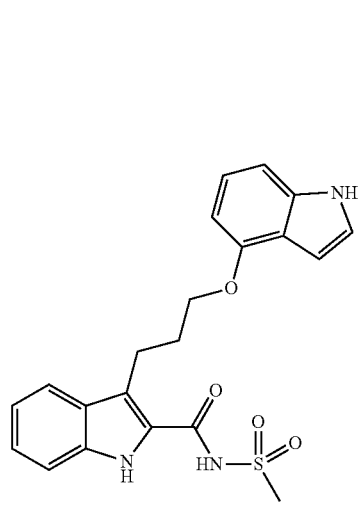

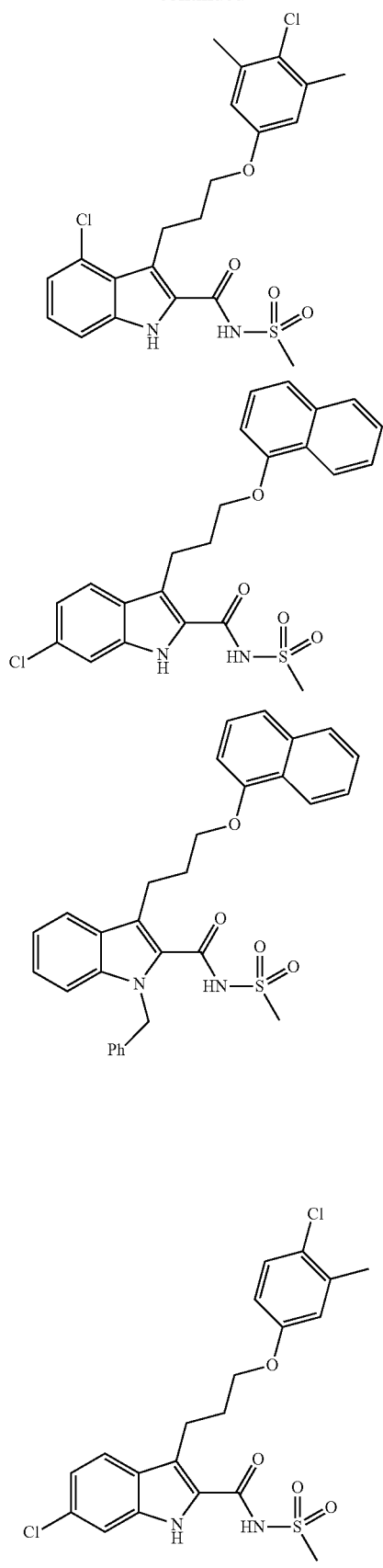
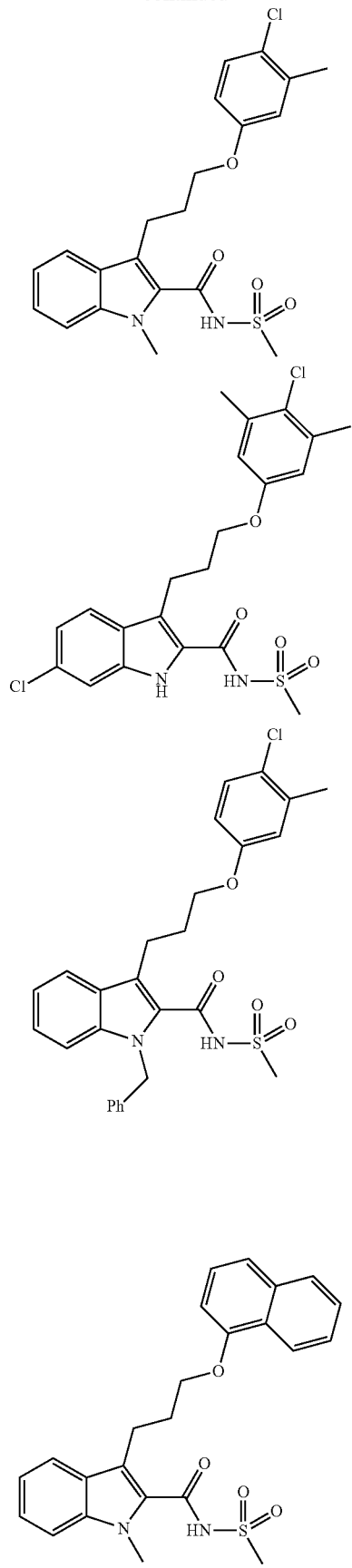

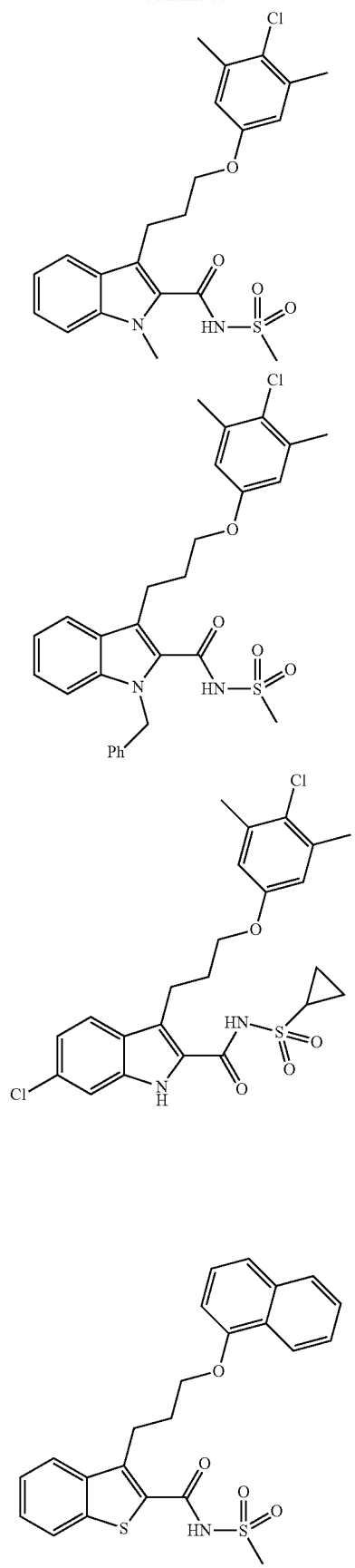
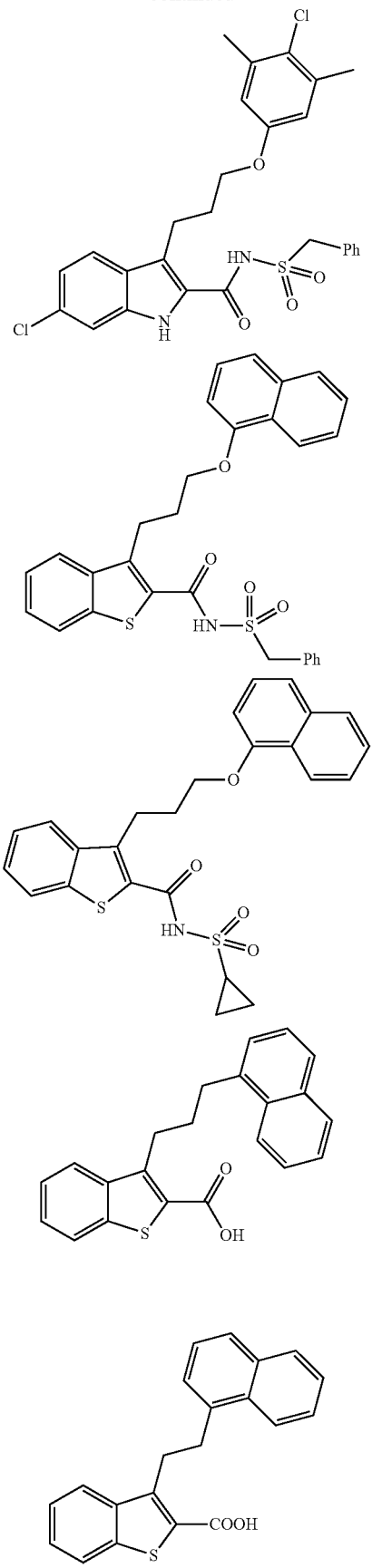

-continued
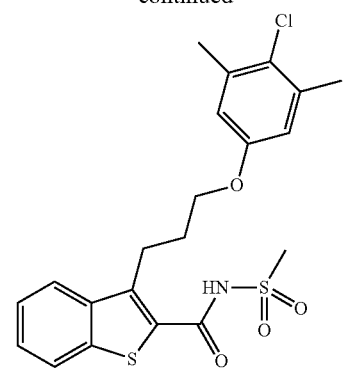
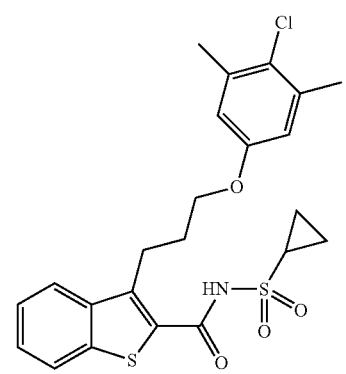
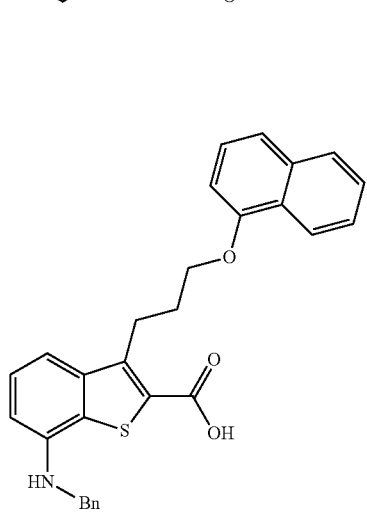
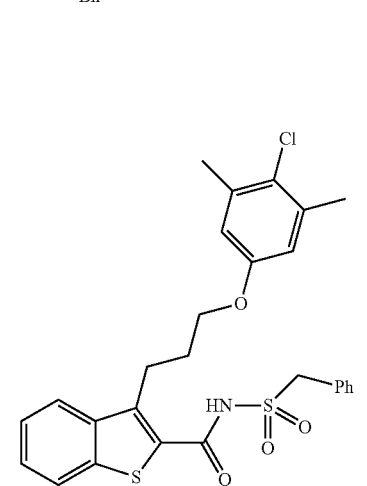
-continued
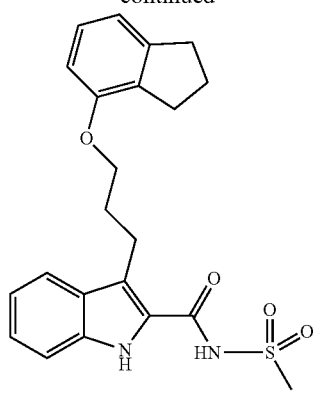
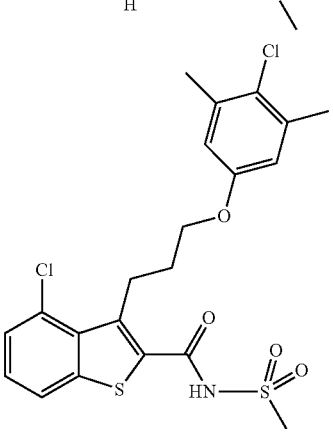
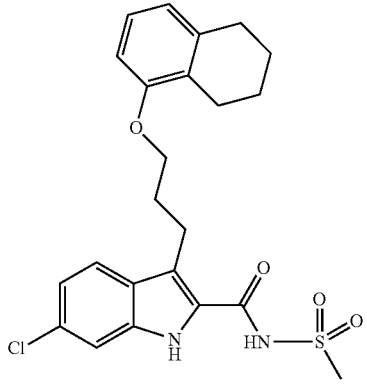
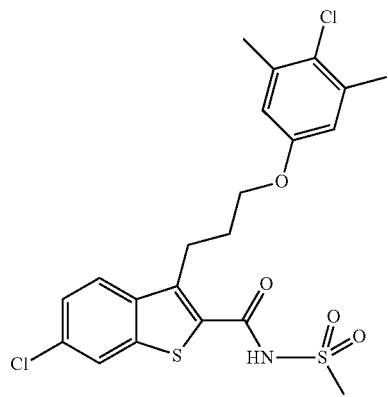

1895
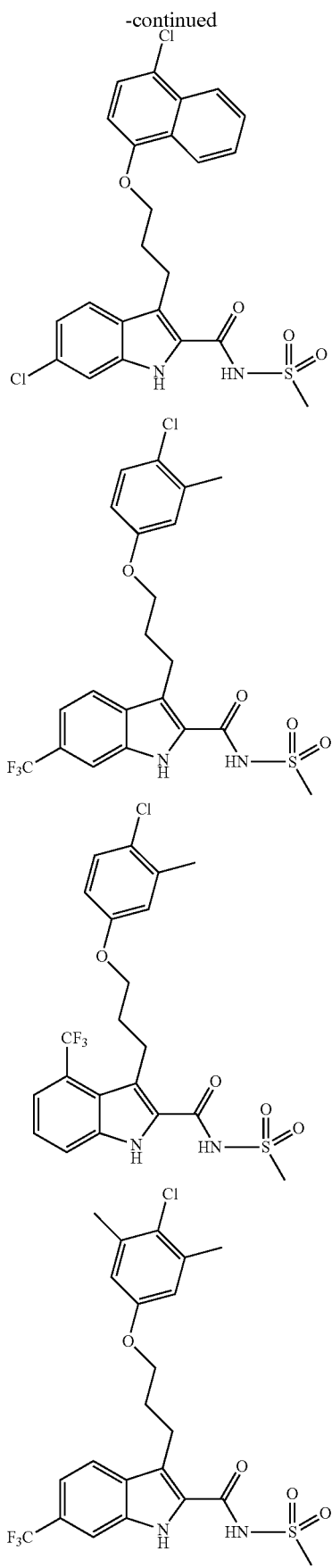
1896
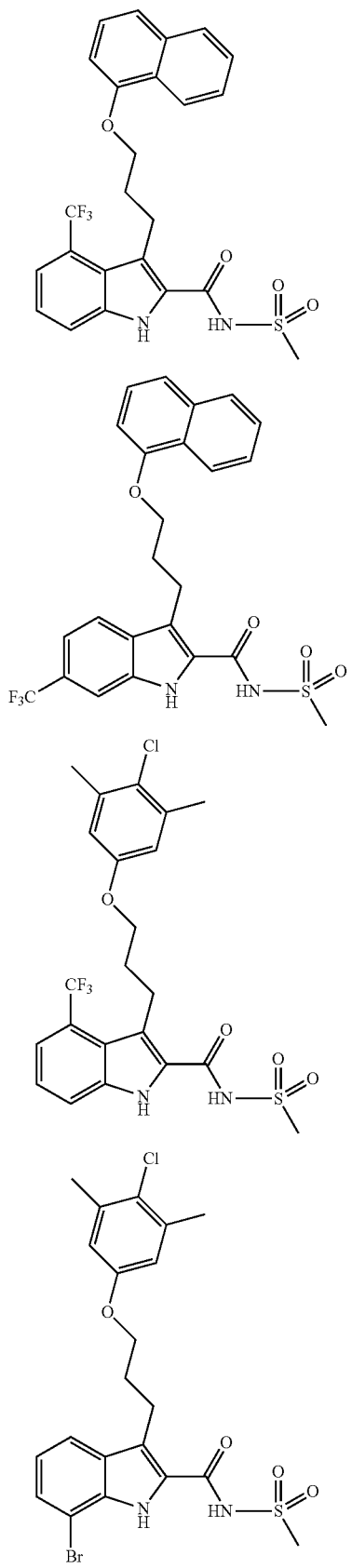

1897
-continued
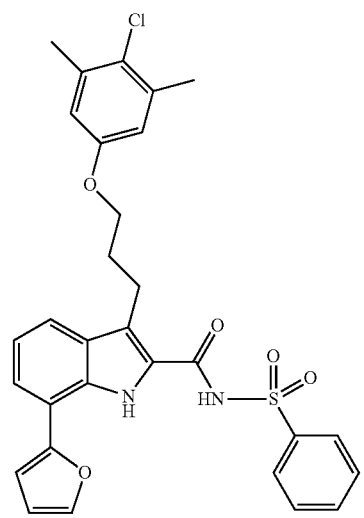
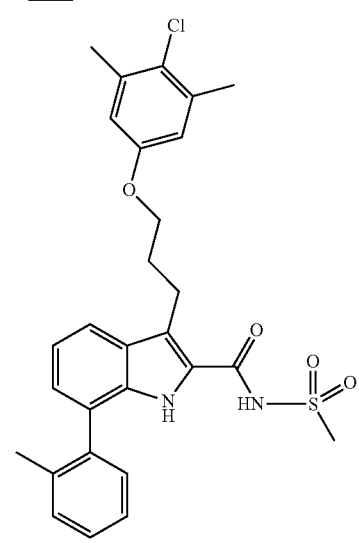
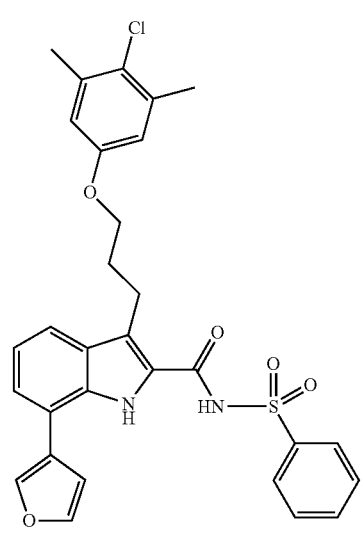
1898
-continued
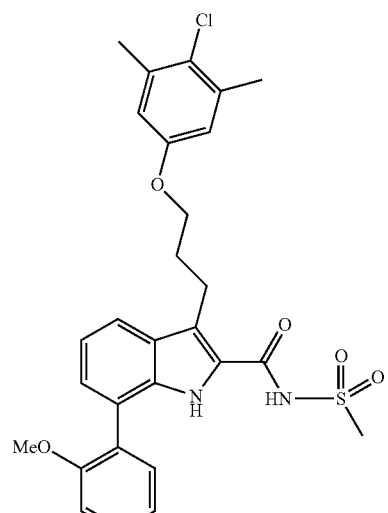
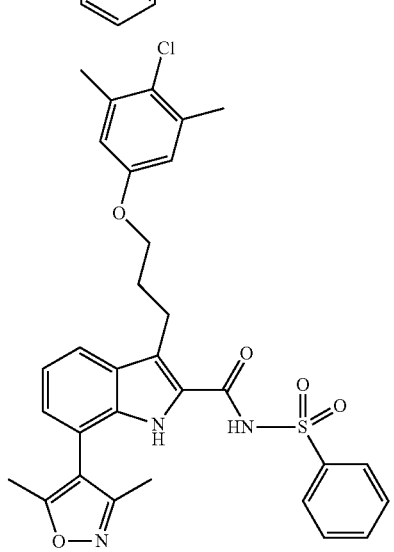
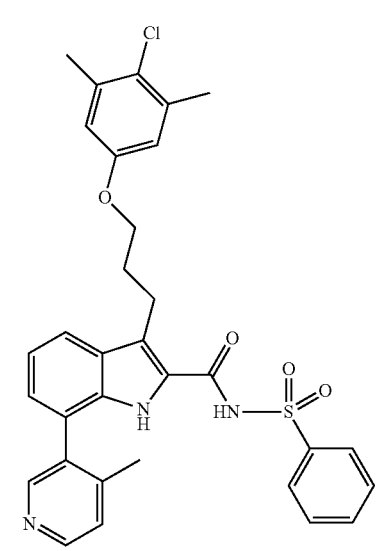

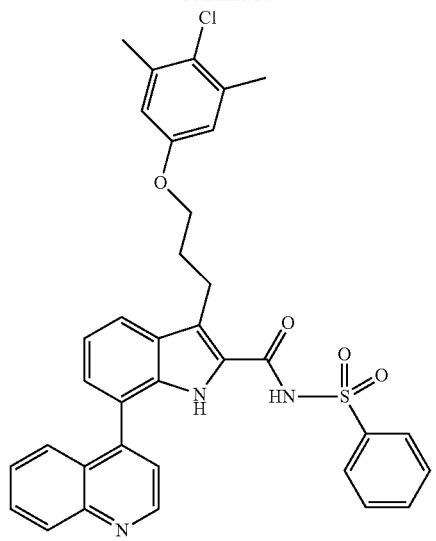
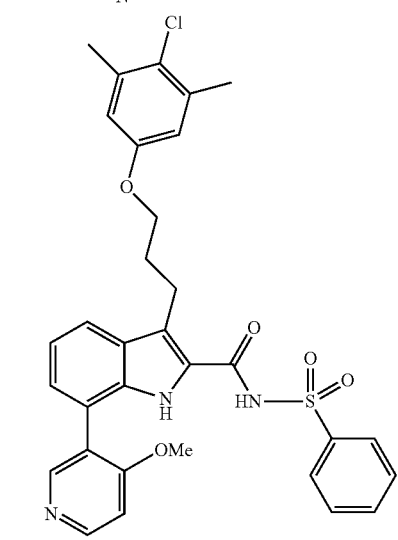
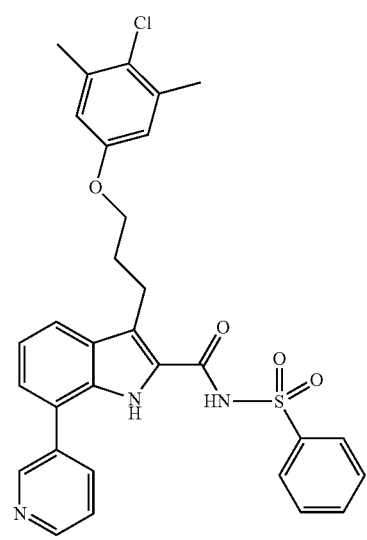
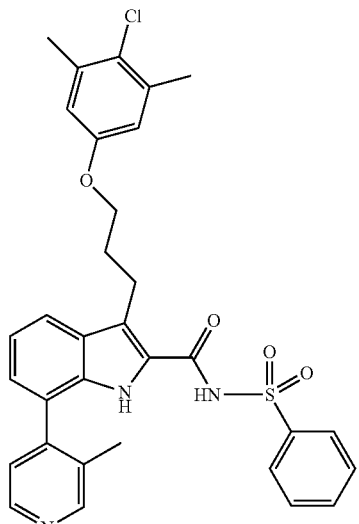
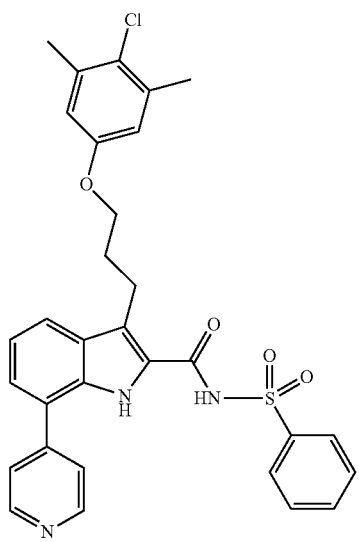
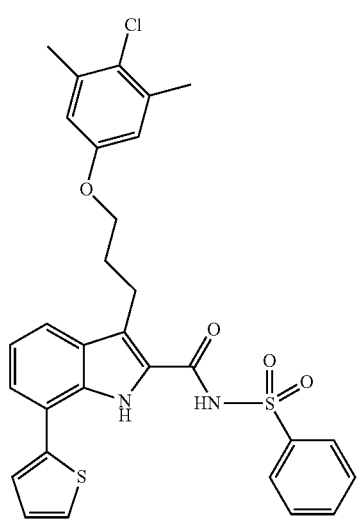

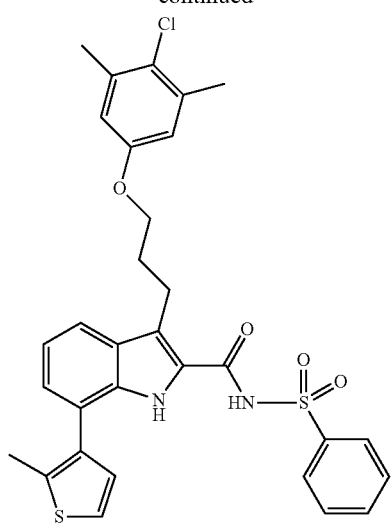
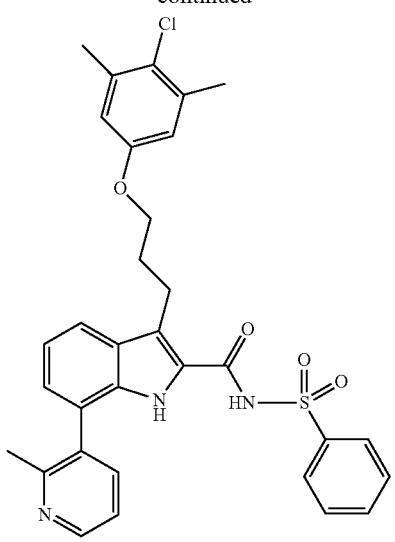
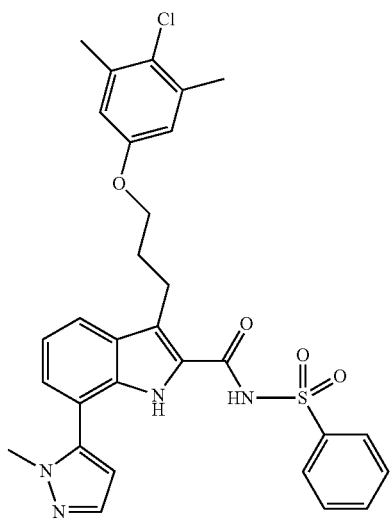
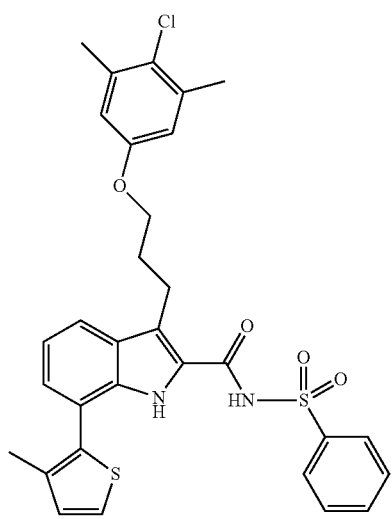

1903
-continued
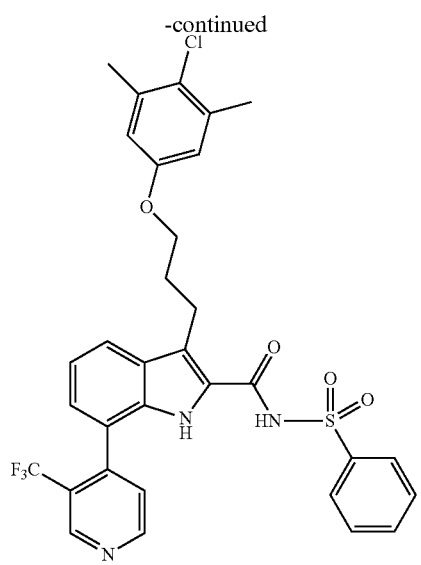
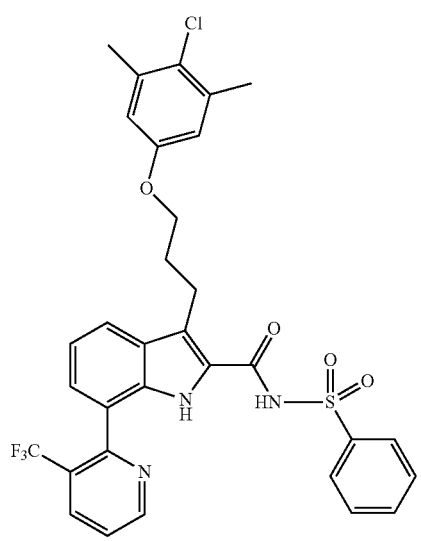
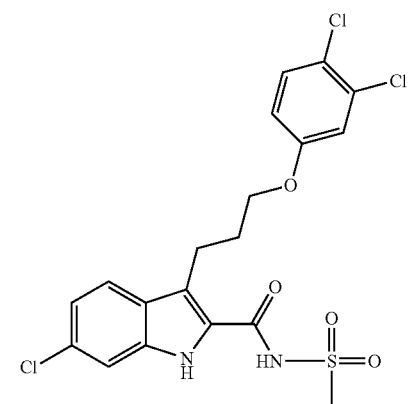
1904
-continued
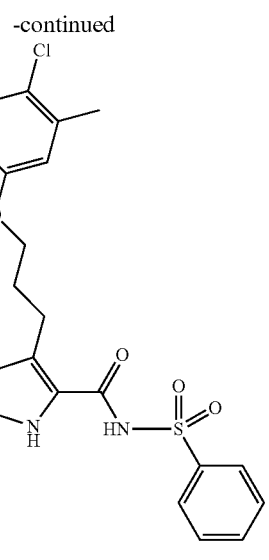
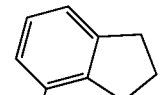
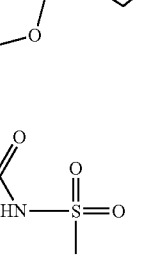
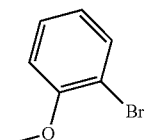
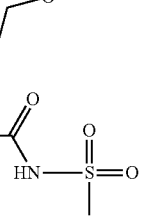
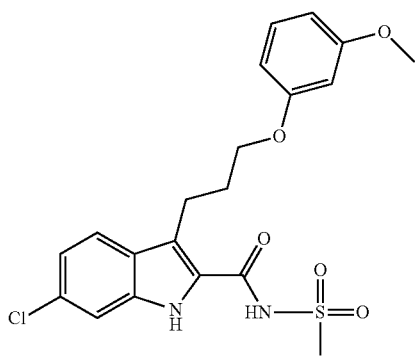

1905
-continued
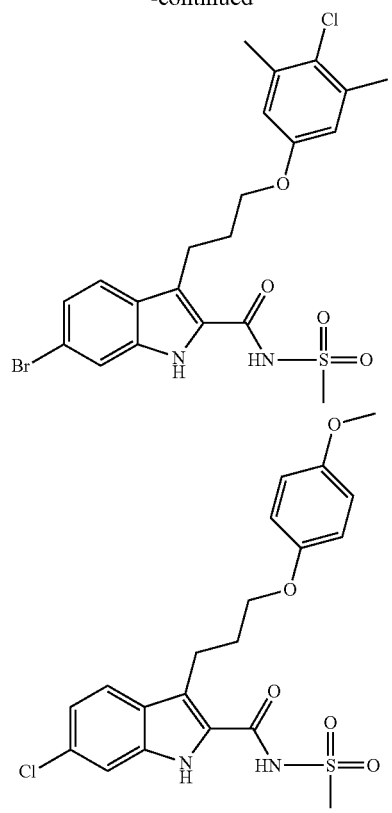
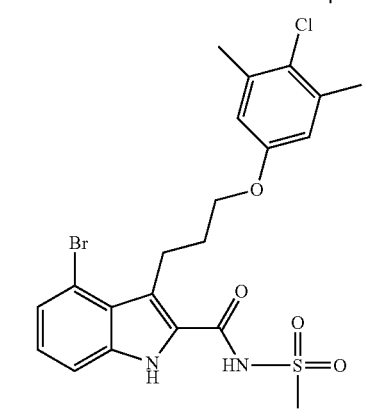
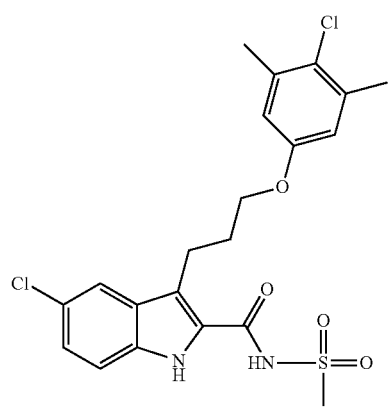
1906
-continued
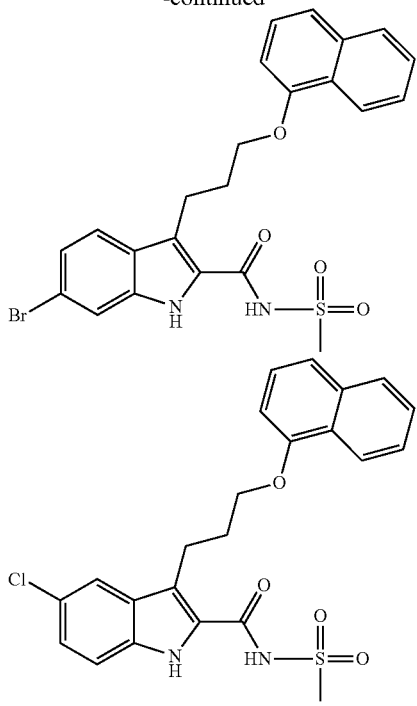
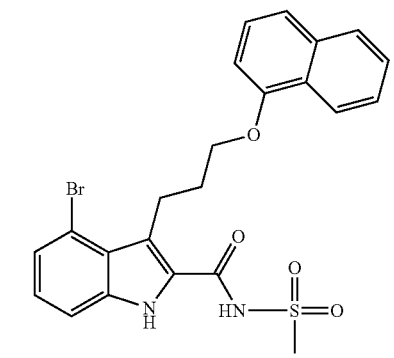
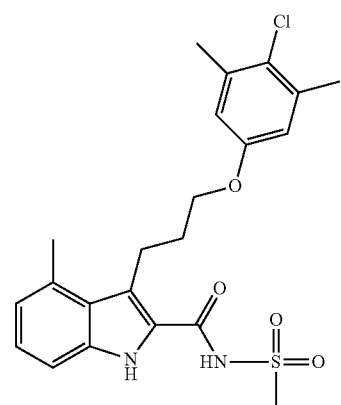

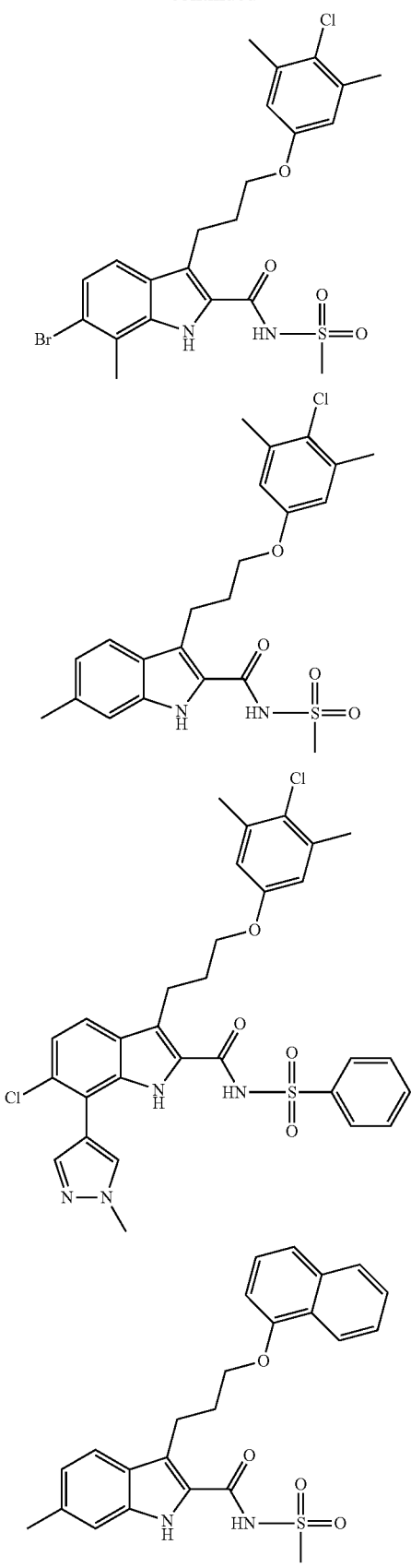
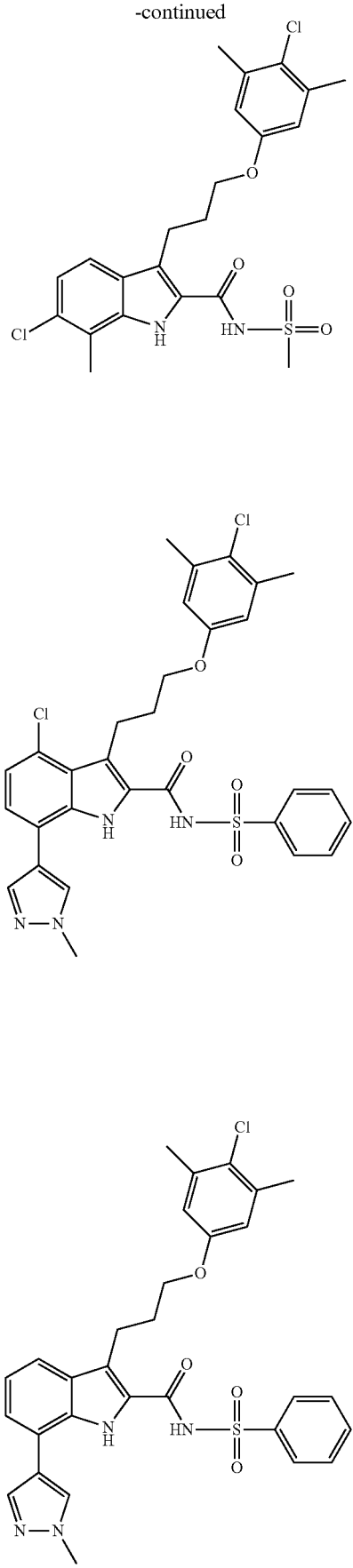

1909
-continued
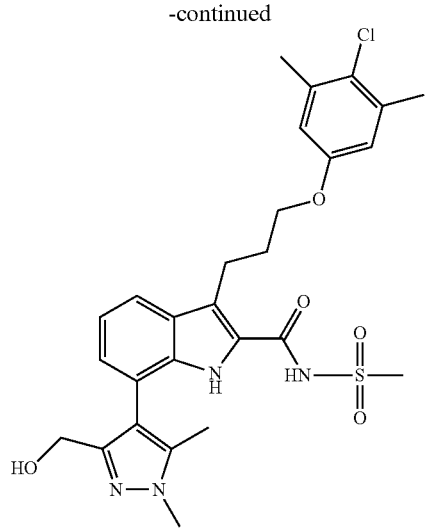
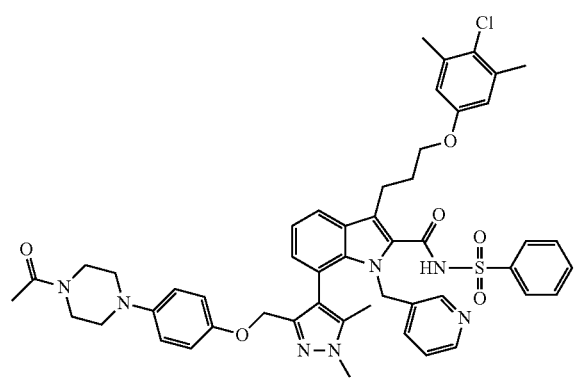
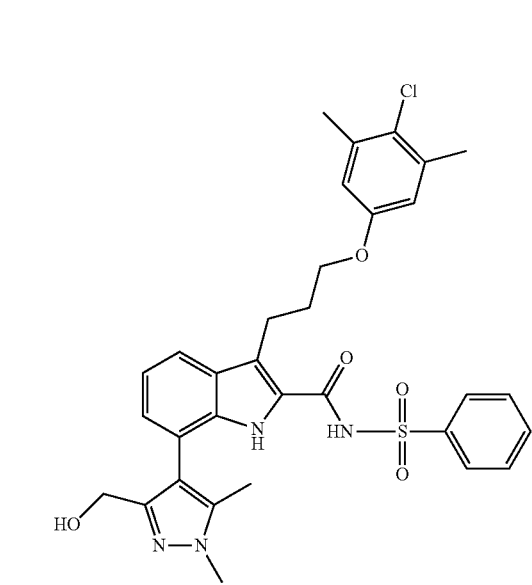
1910
-continued
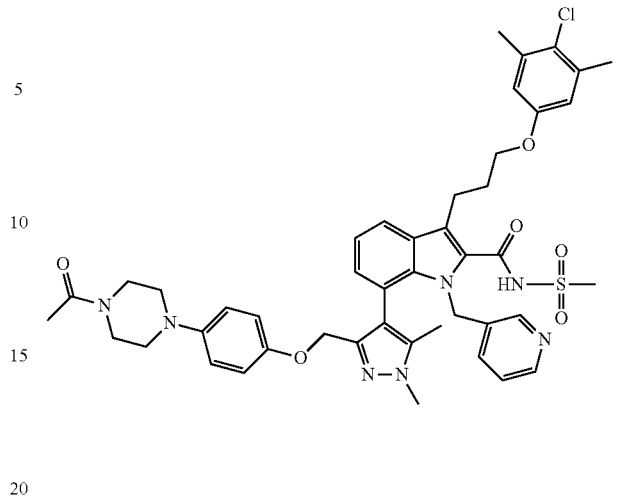
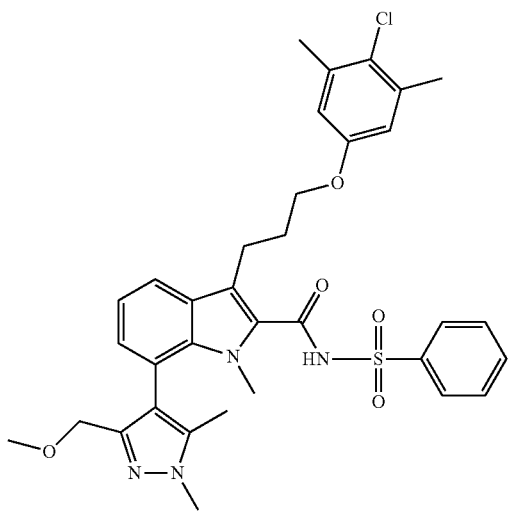

1911
-continued
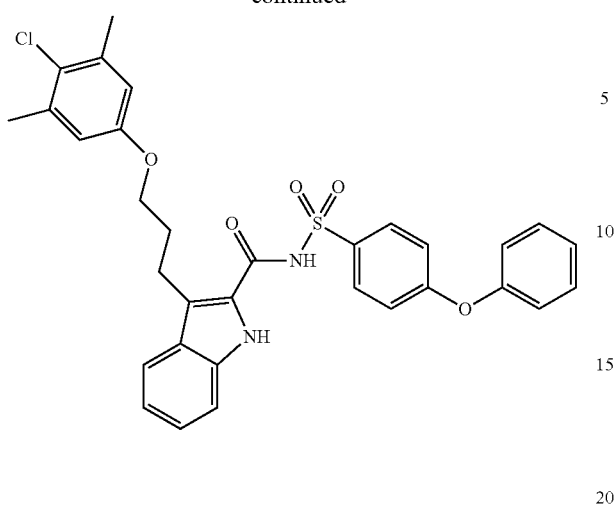
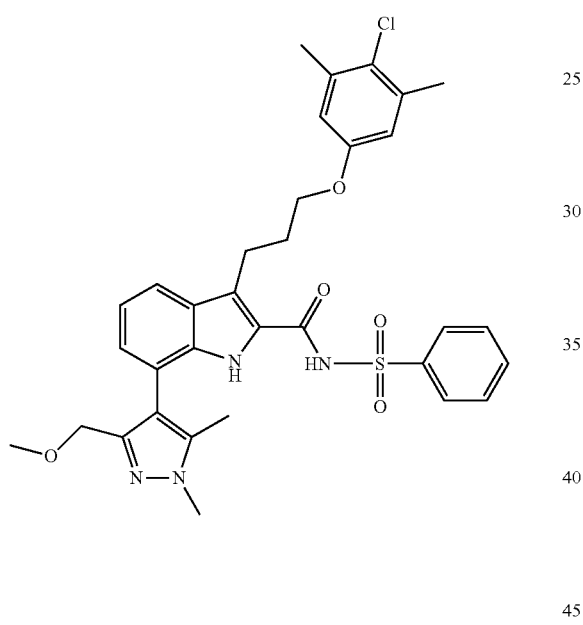
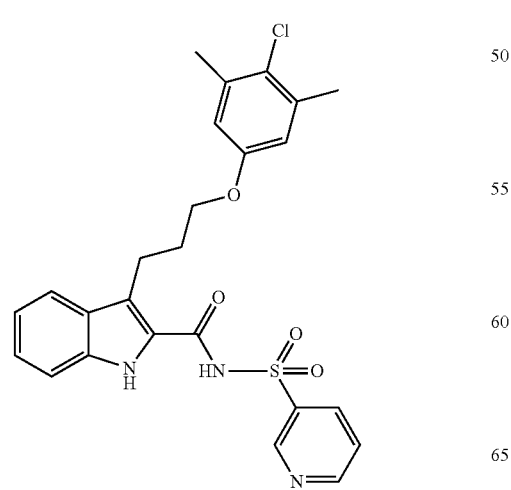
1912
-continued
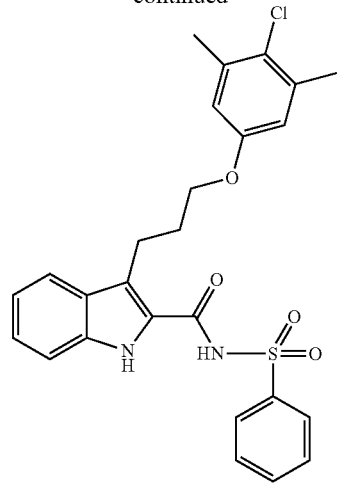
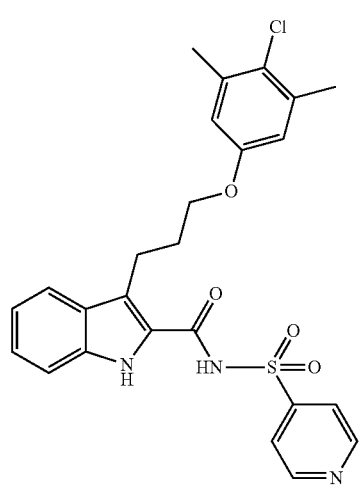
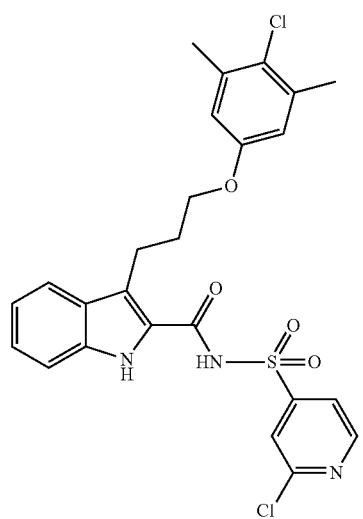

1913
-continued
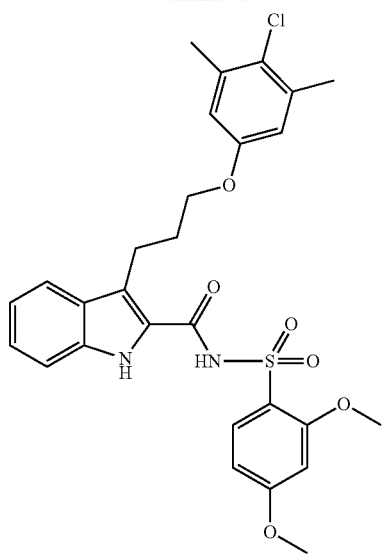
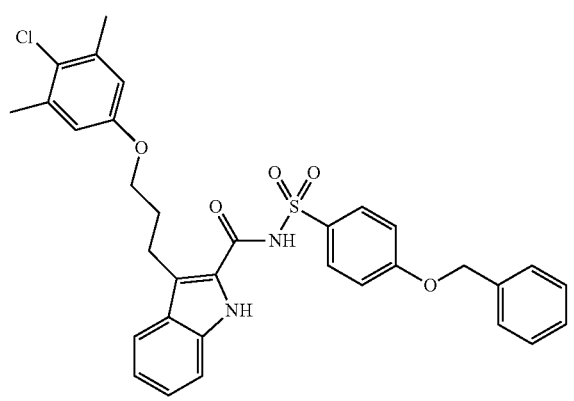
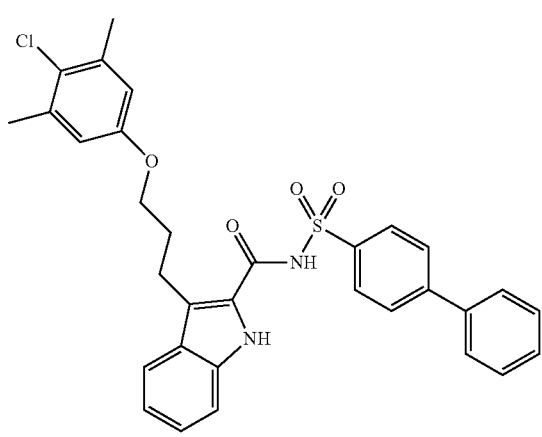
1914
-continued
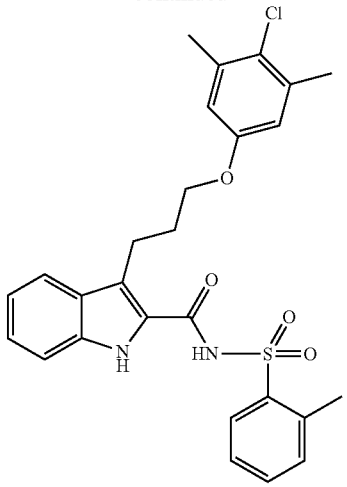
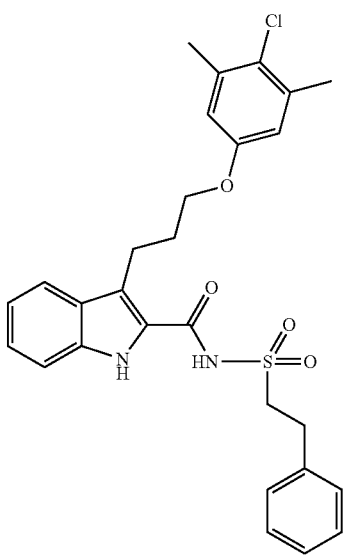
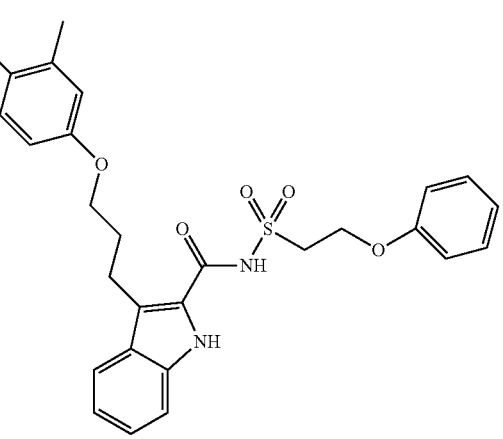

1915
-continued
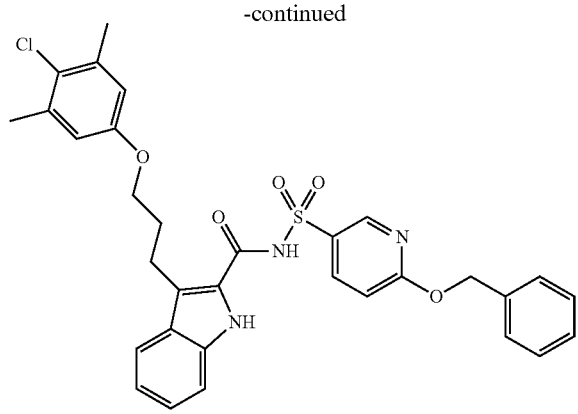
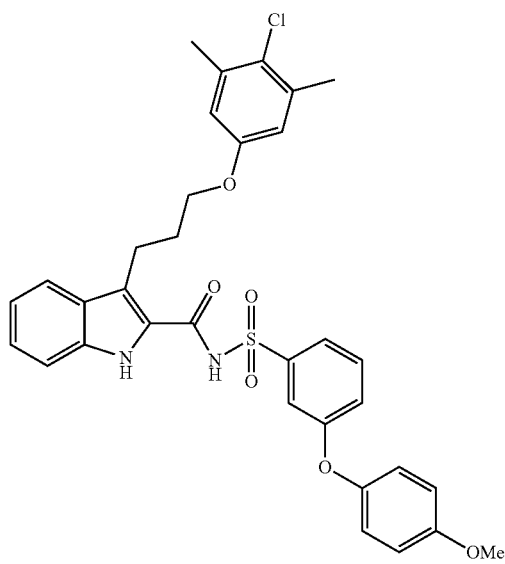
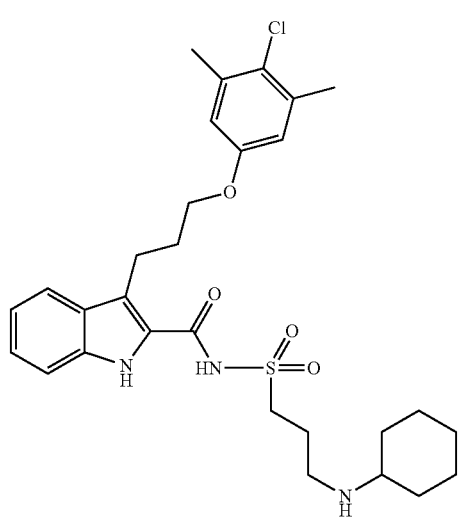
1916
-continued
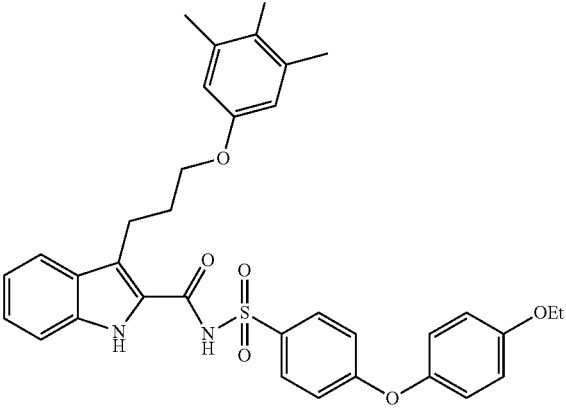
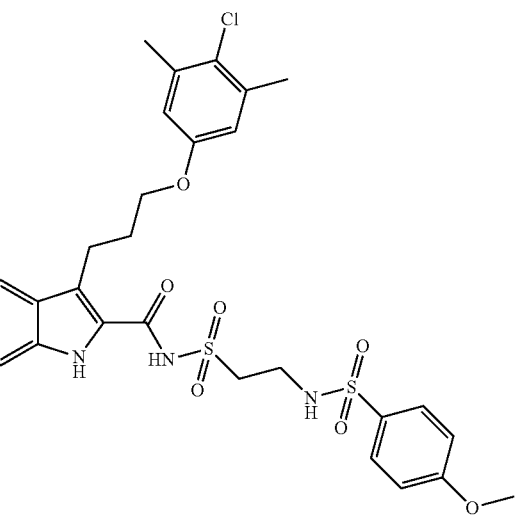

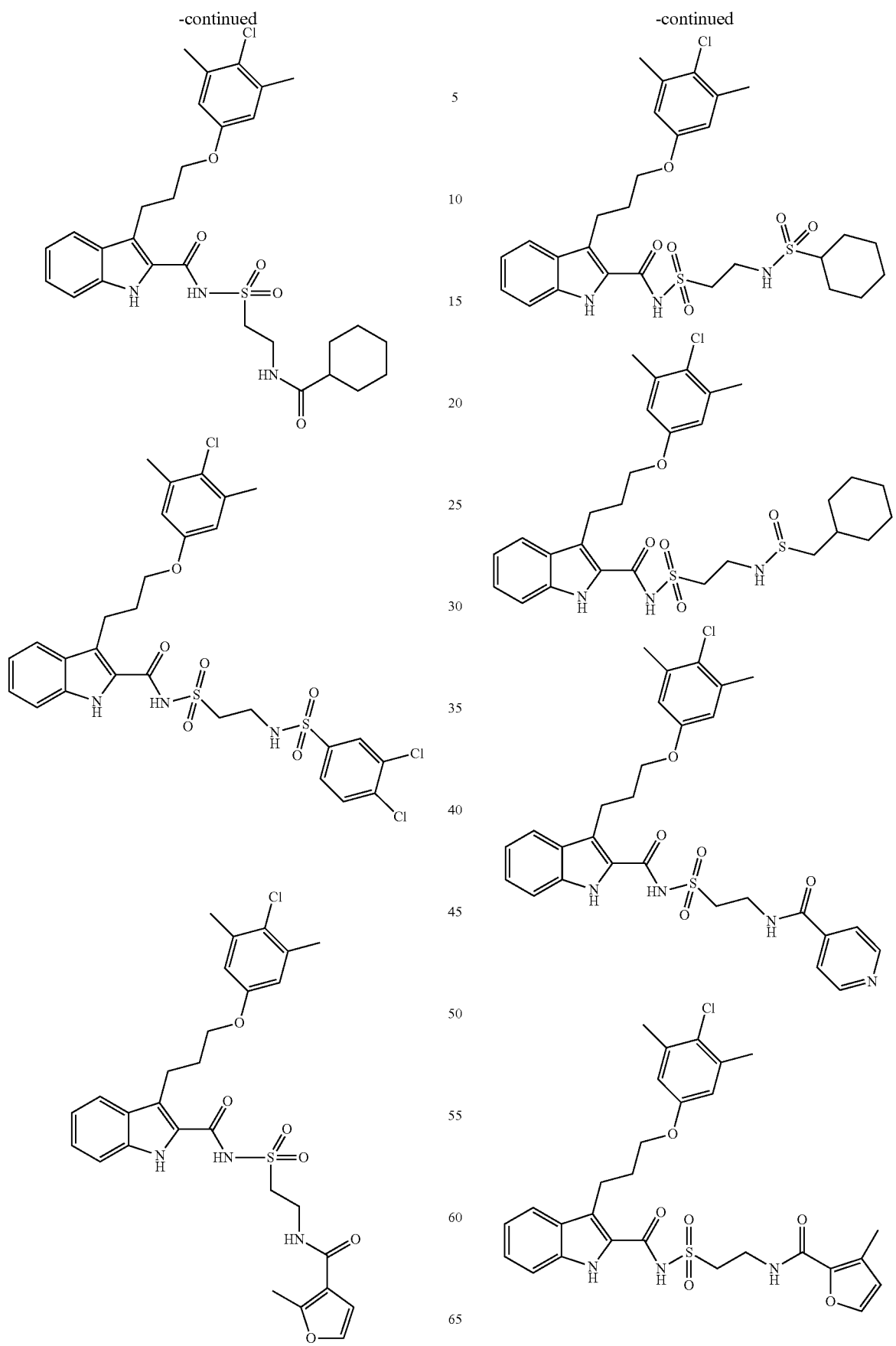

1919
-continued
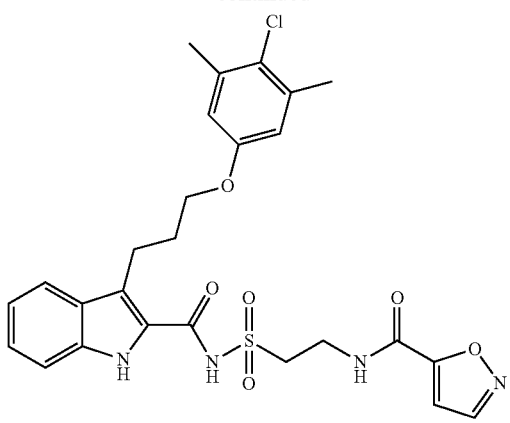
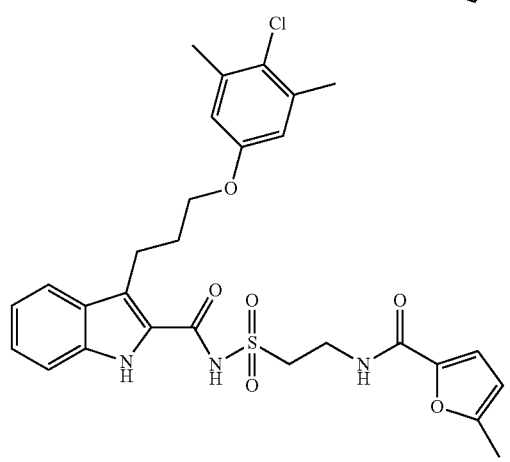
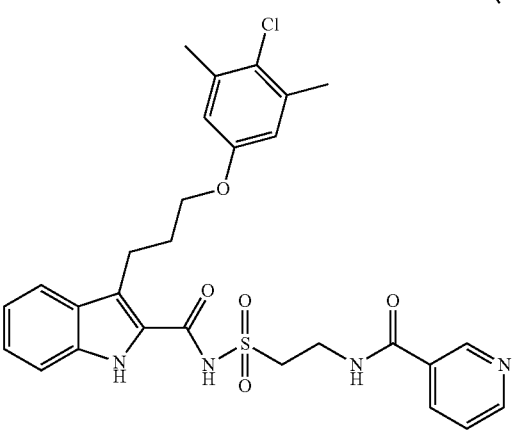
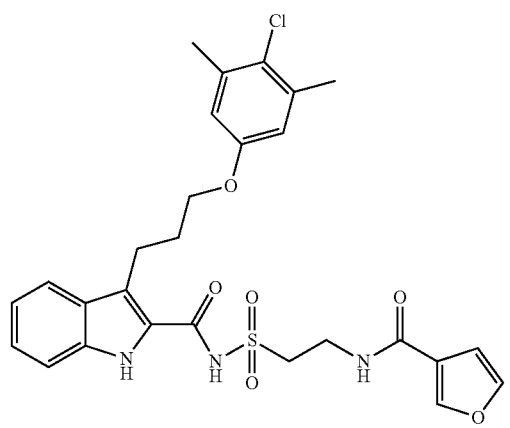
1920
-continued
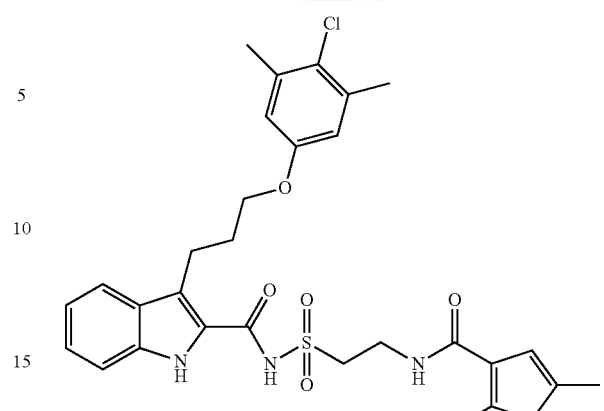
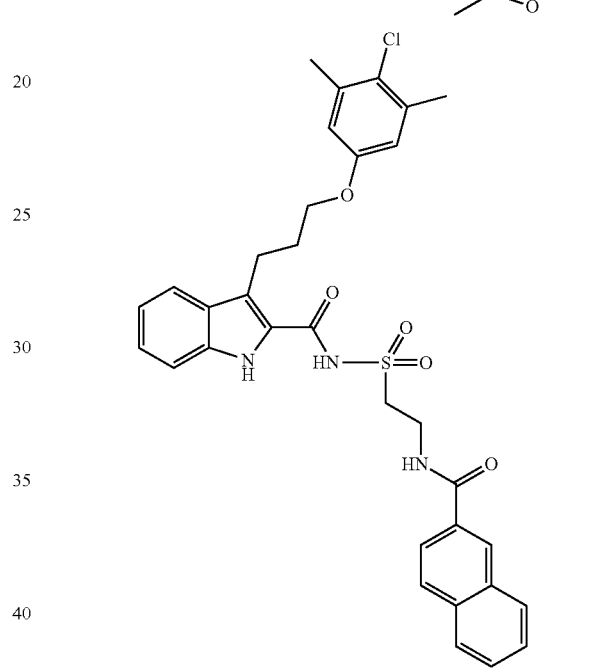
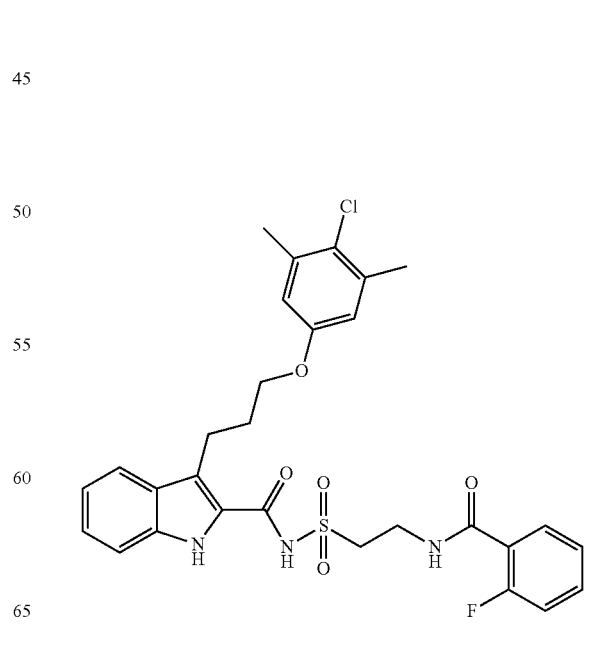

1921
-continued
1922
-continued
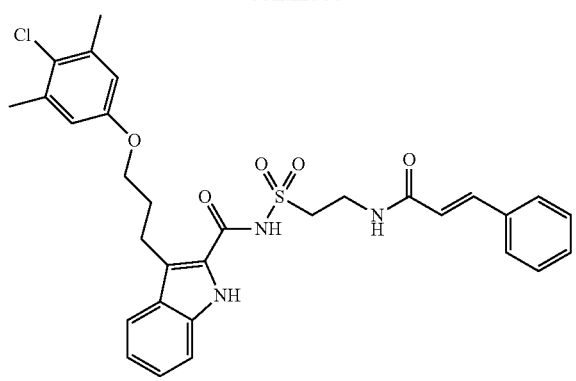
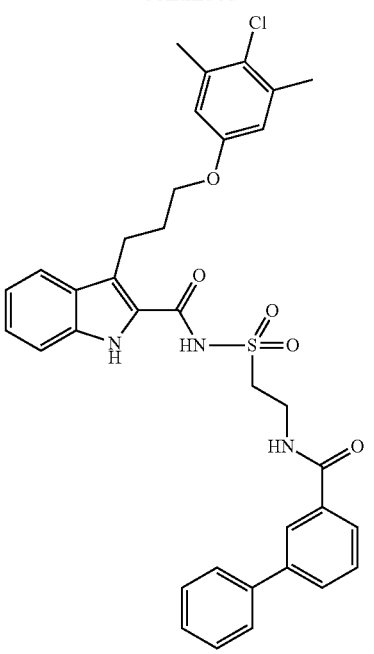
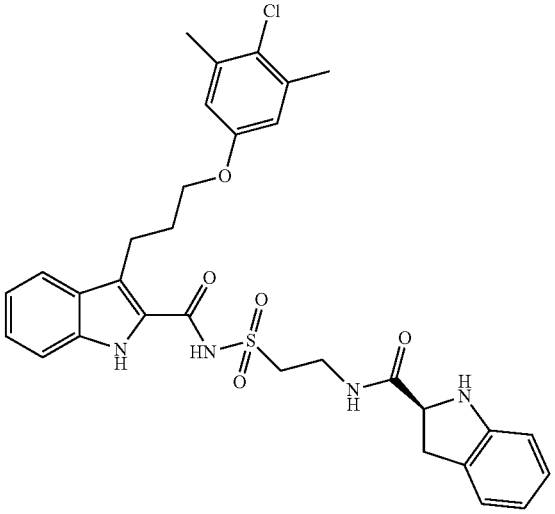
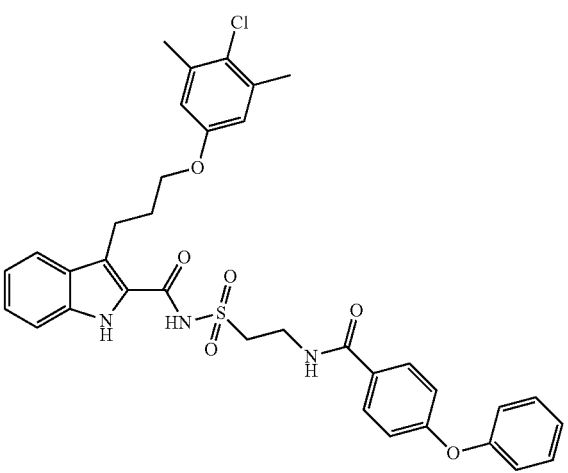

1923
-continued
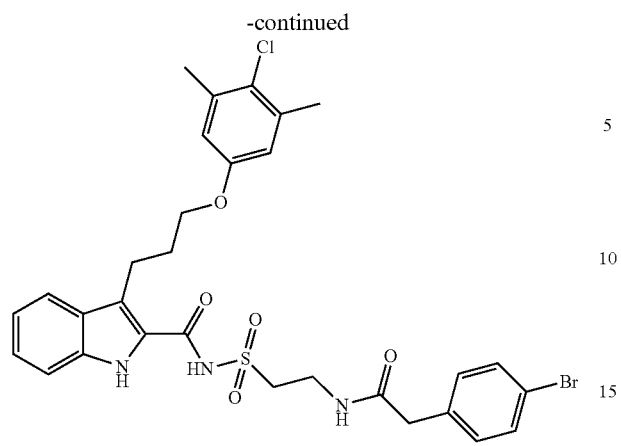
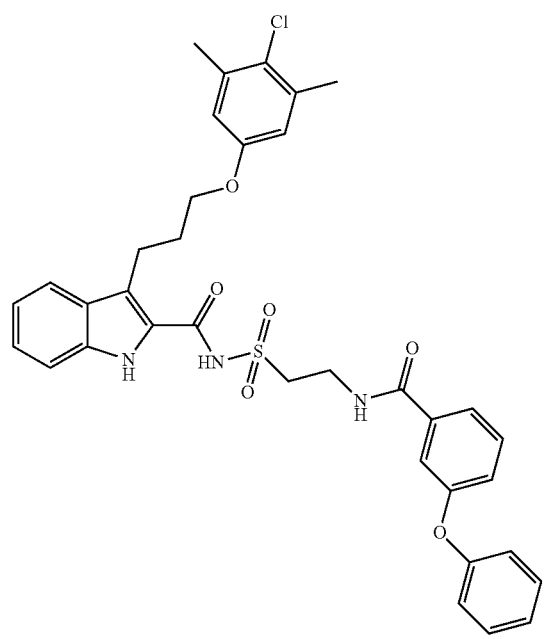
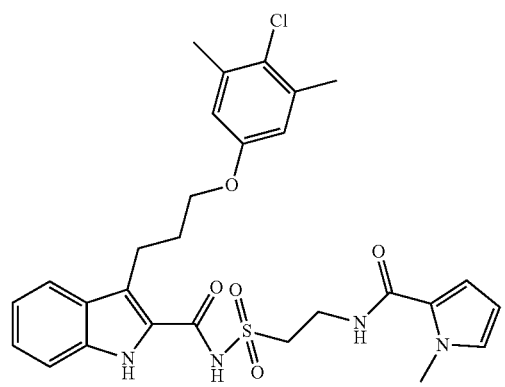
1924
-continued
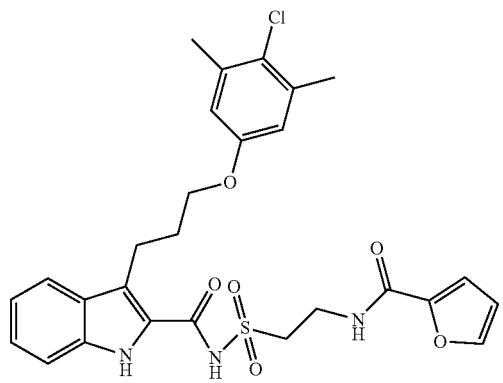
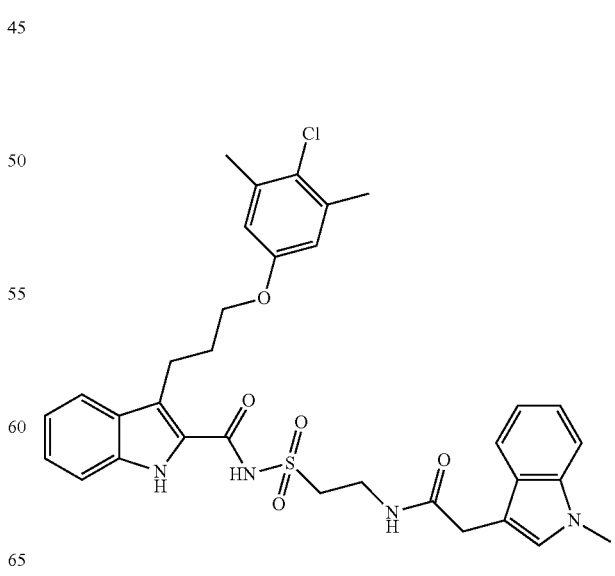

1925
-continued
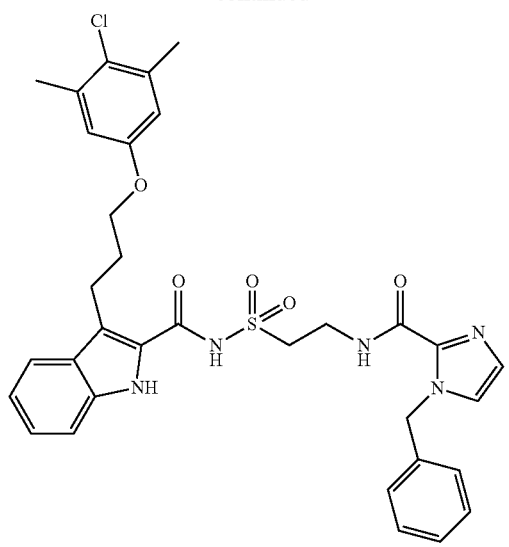
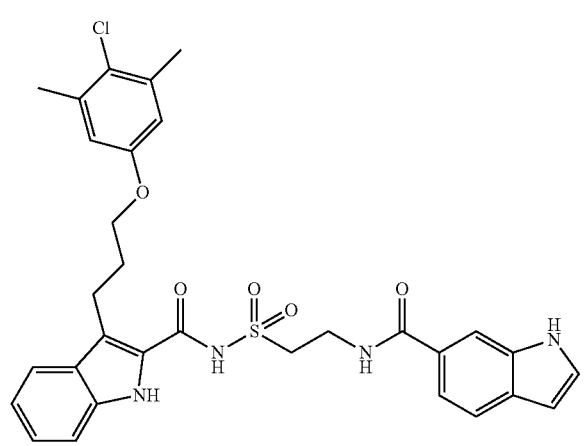
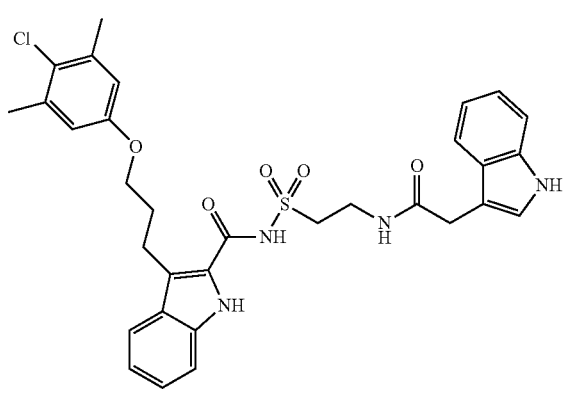
1926
-continued
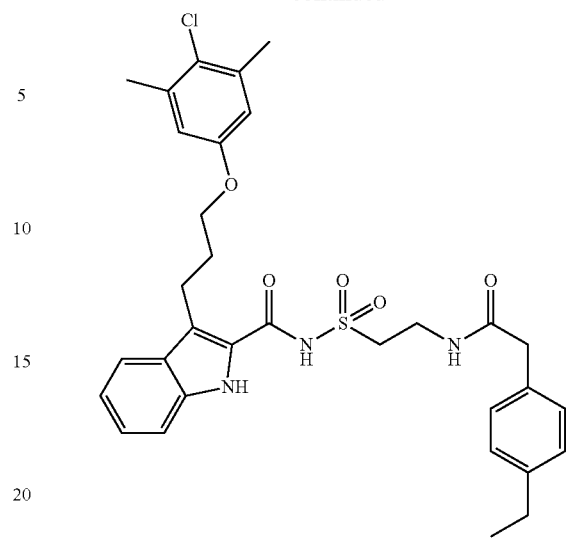
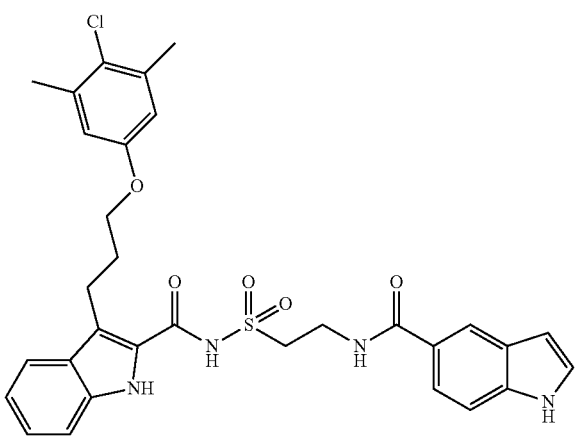
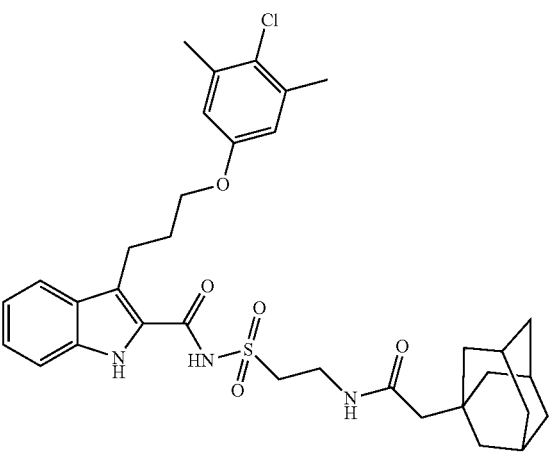

1927
1928
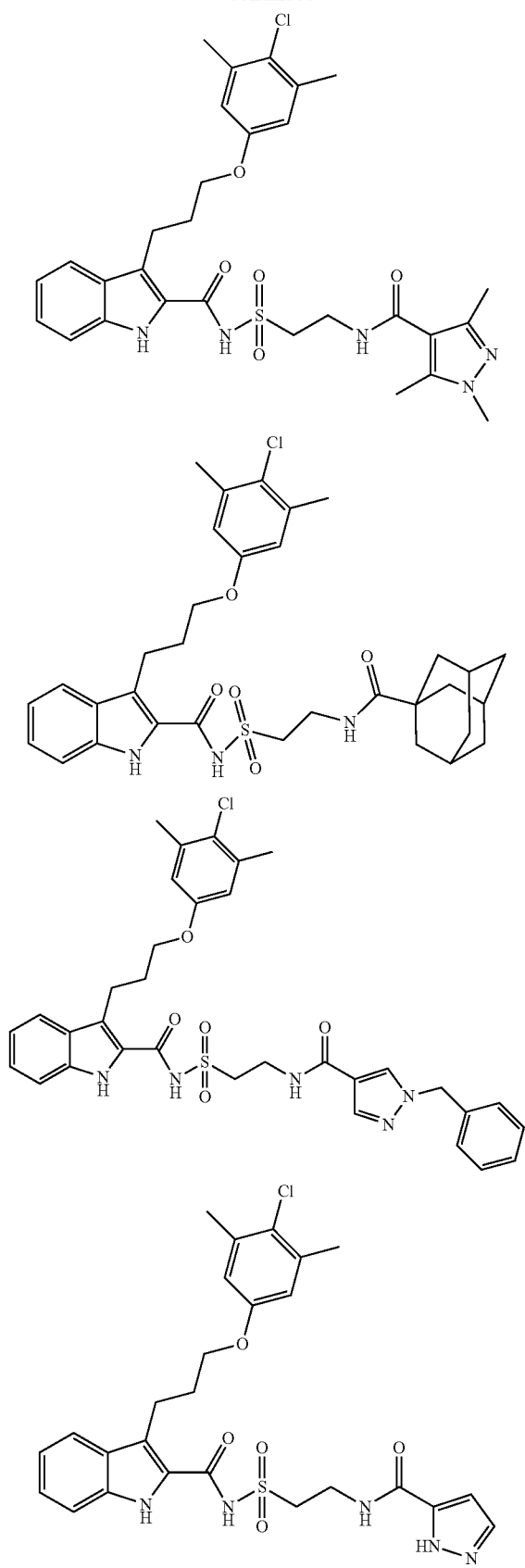
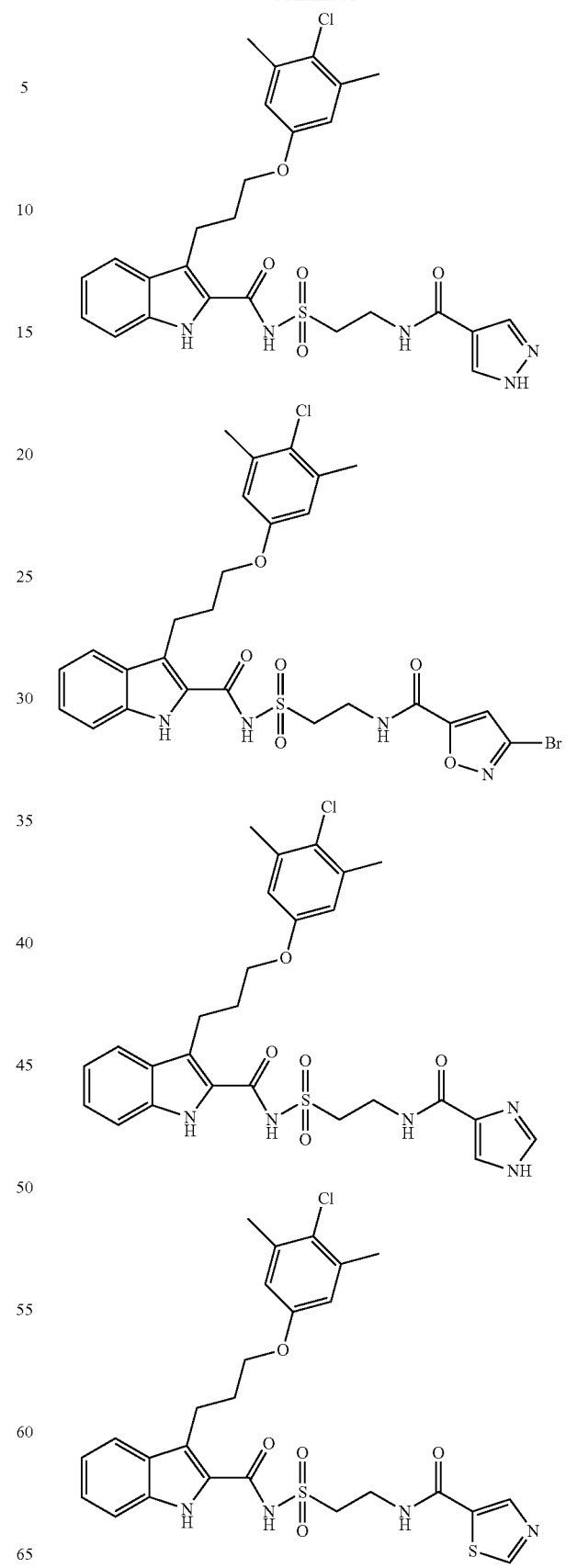

-continued
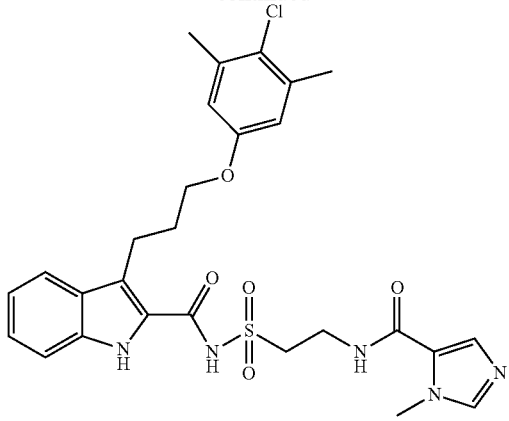
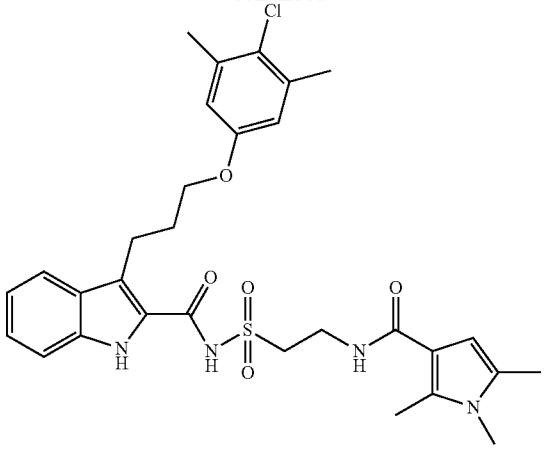
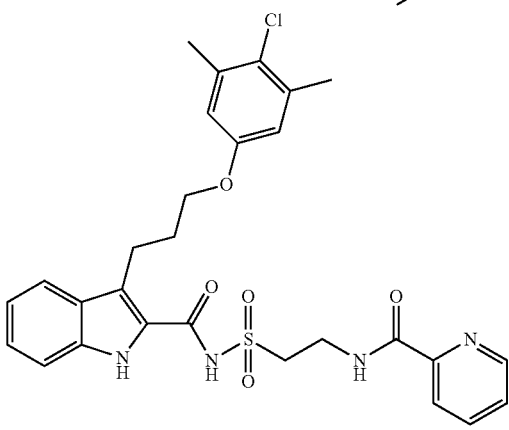
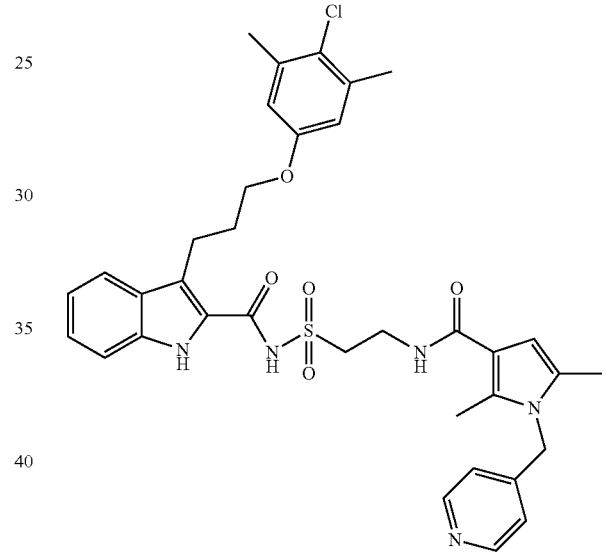
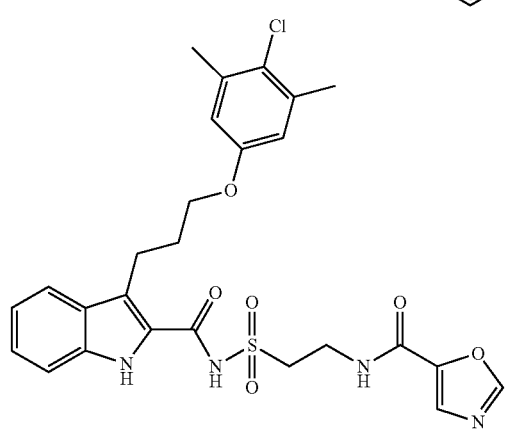
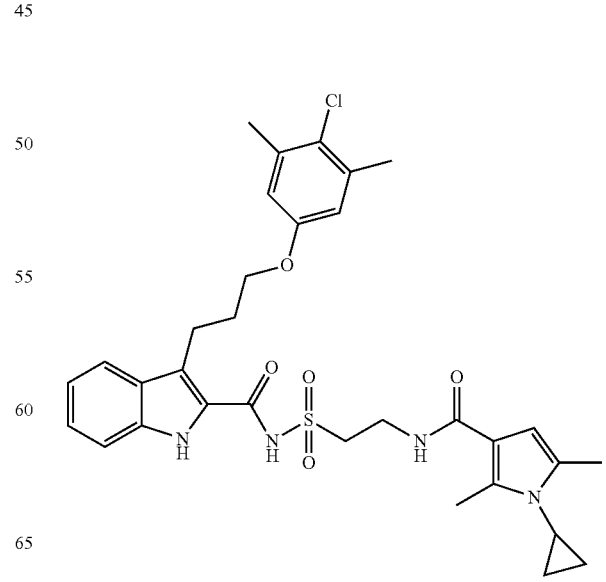
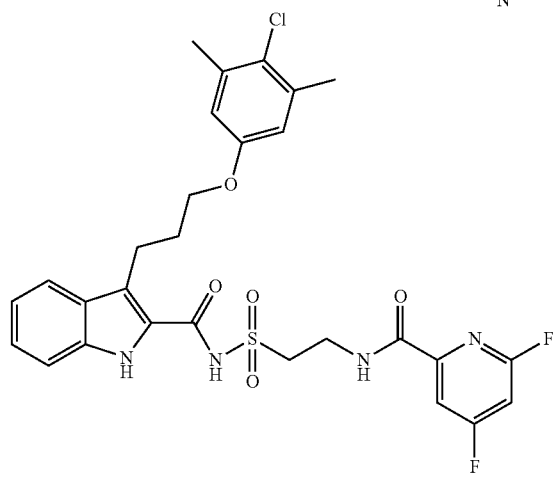

1931
-continued
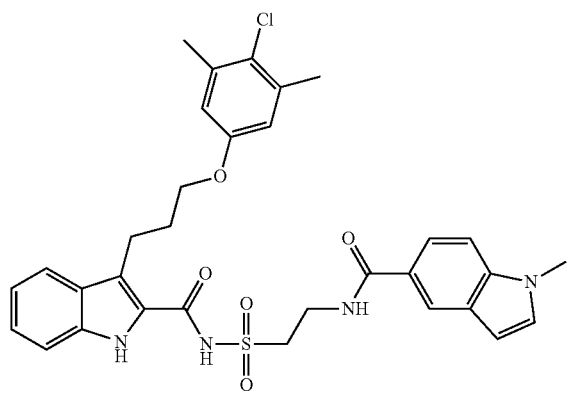
1932
-continued
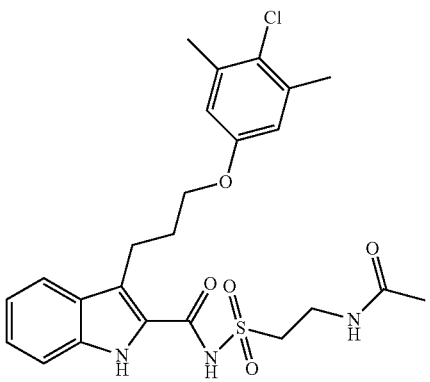
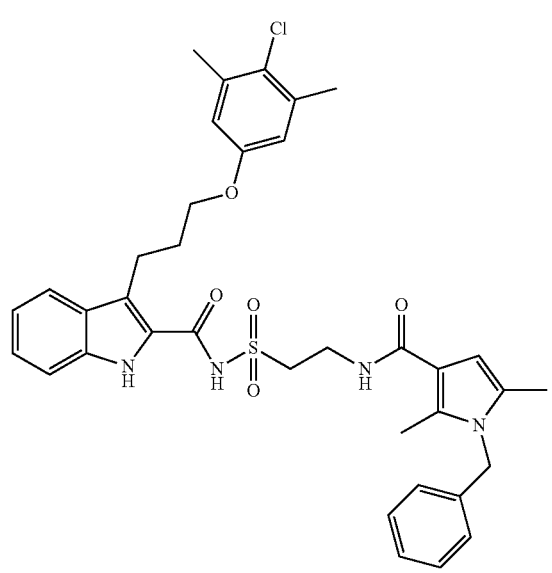
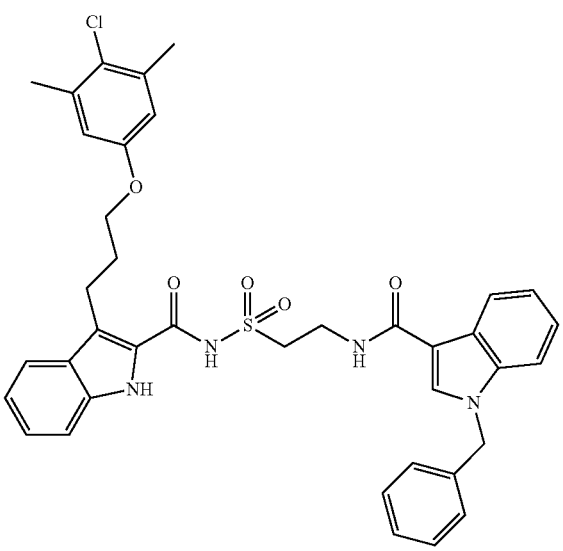
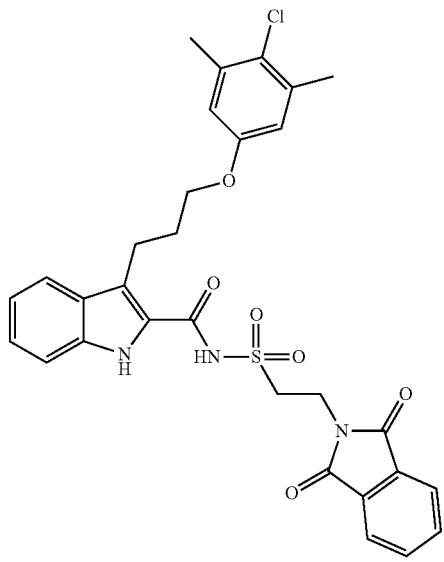
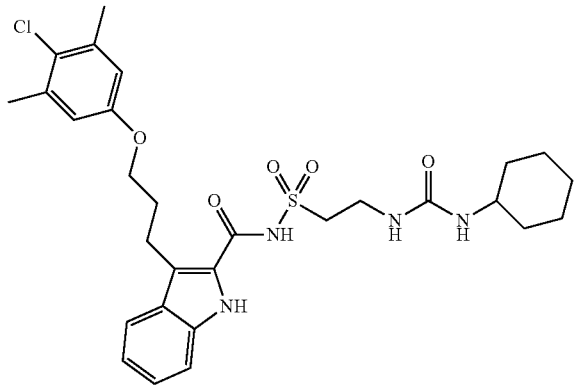

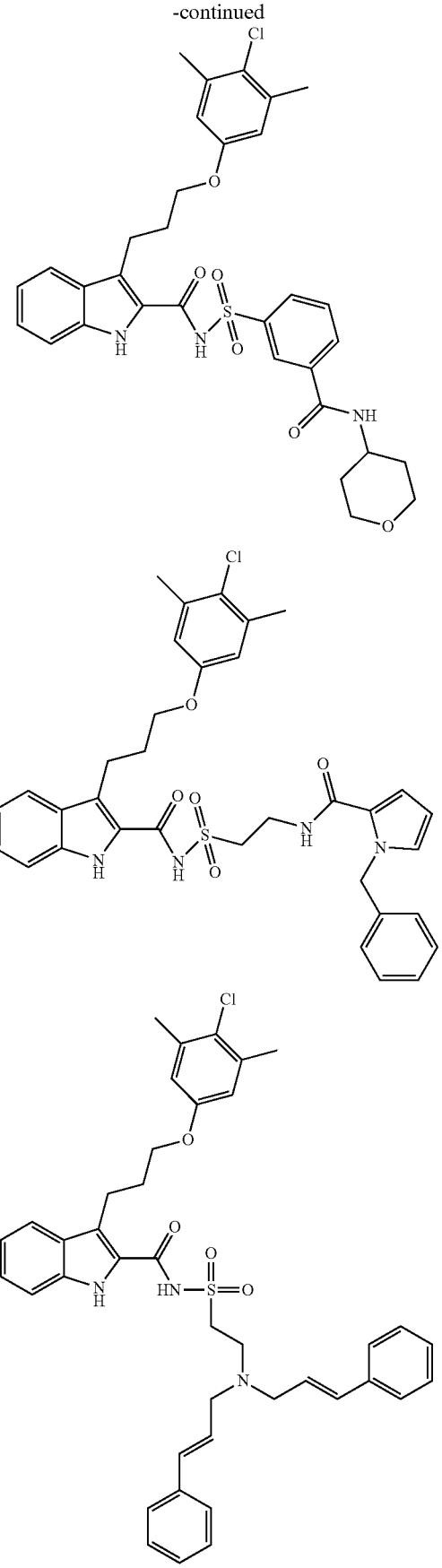
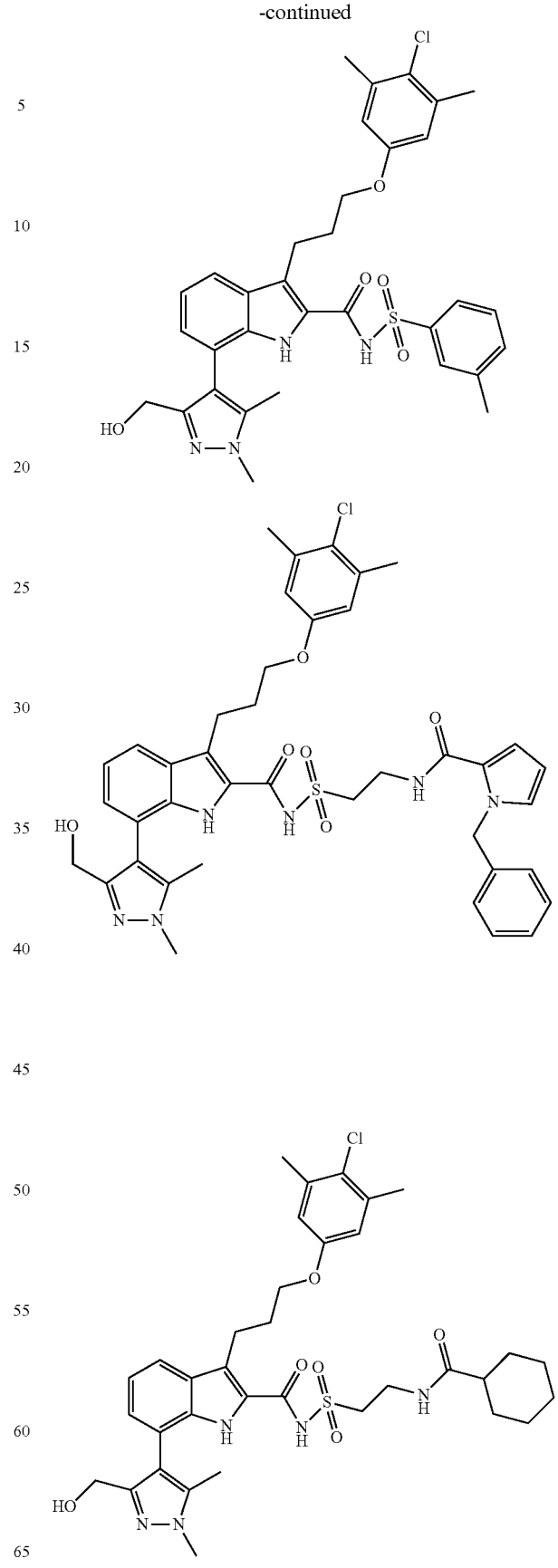

1935
-continued
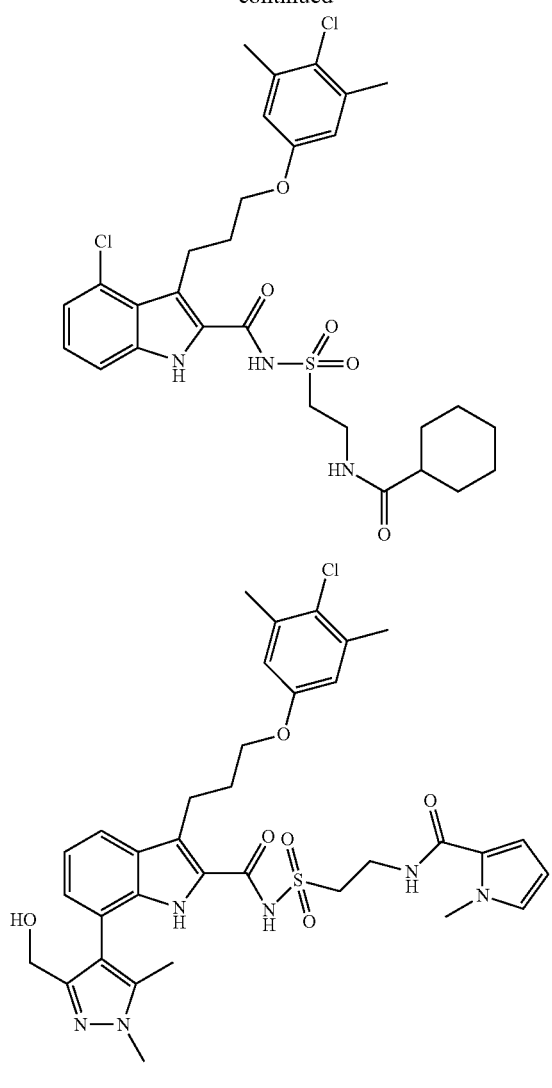
1936
-continued
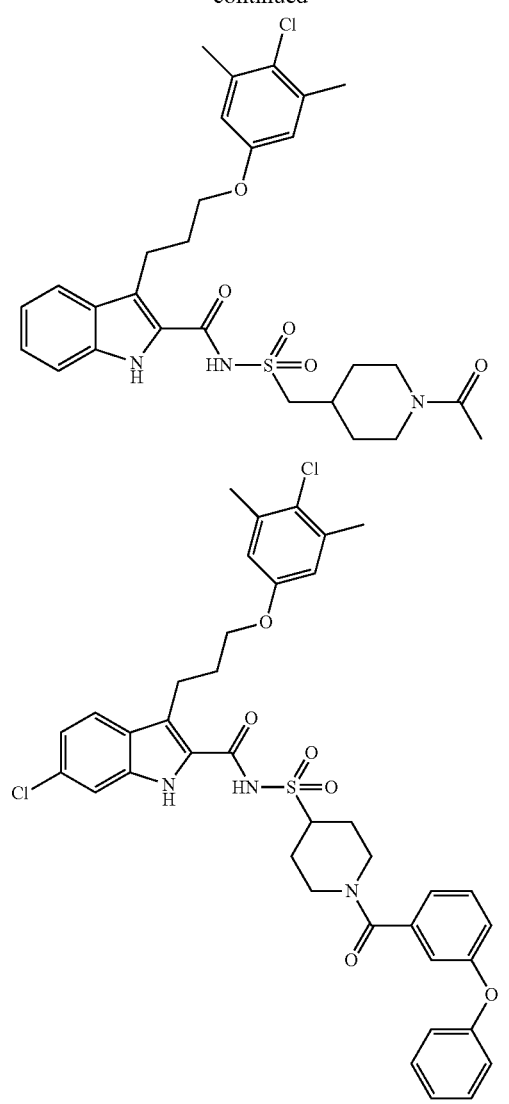
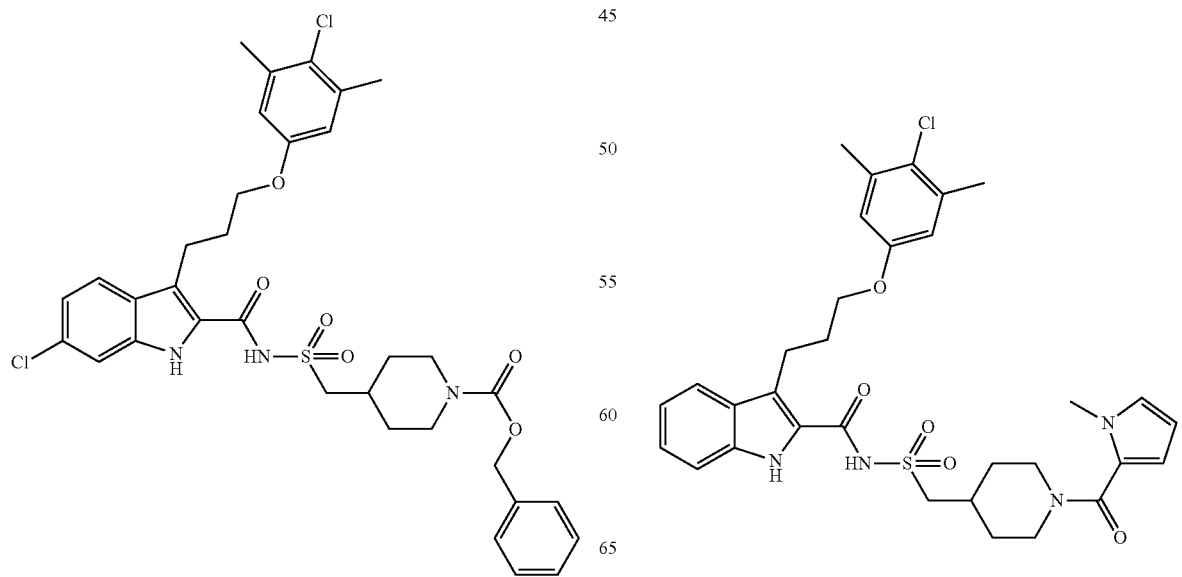

1937
-continued
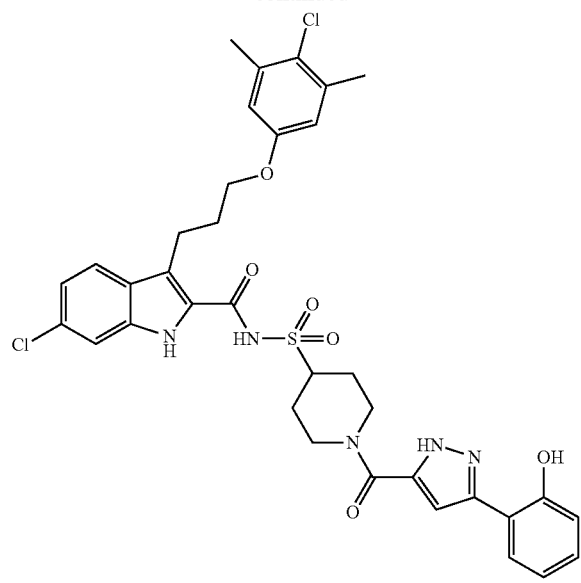
1938
-continued
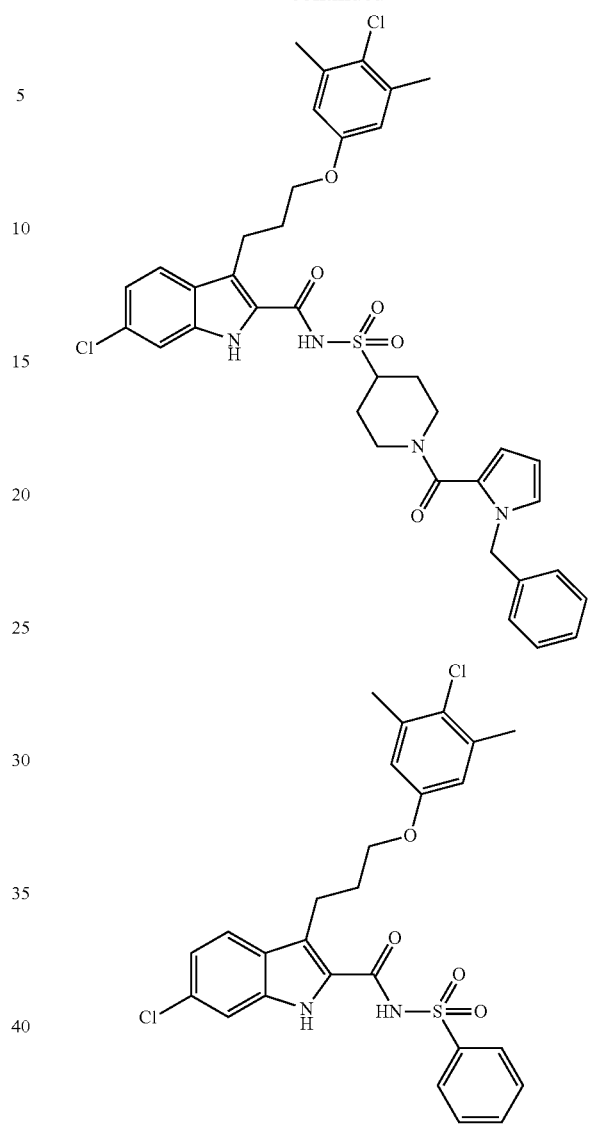
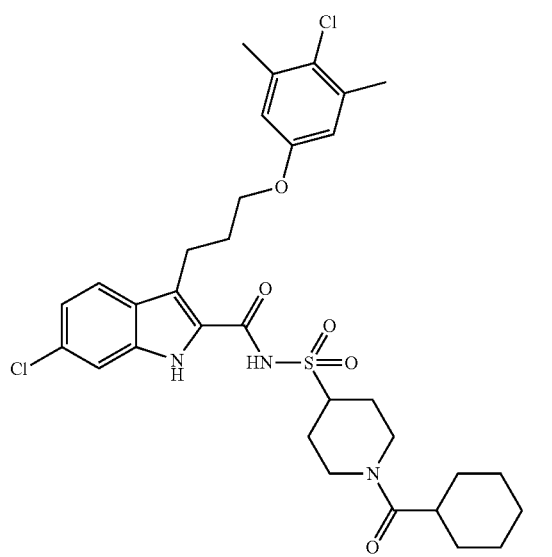
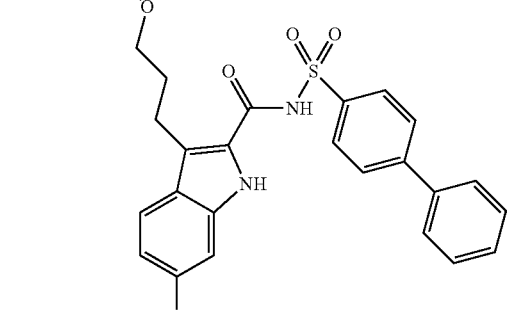

1939
-continued
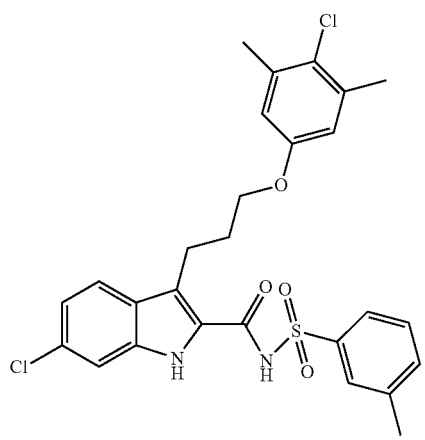
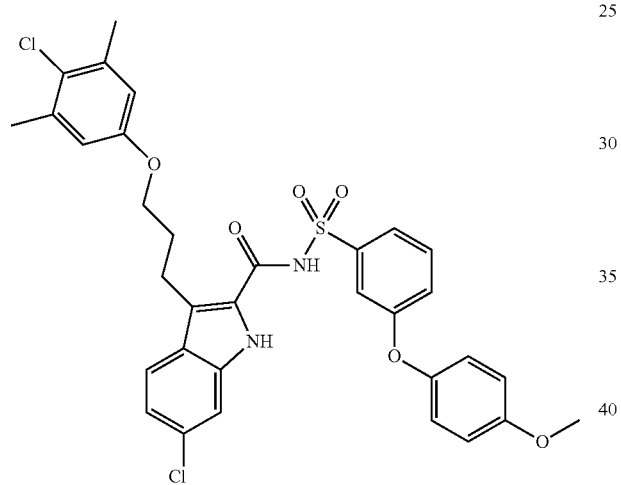
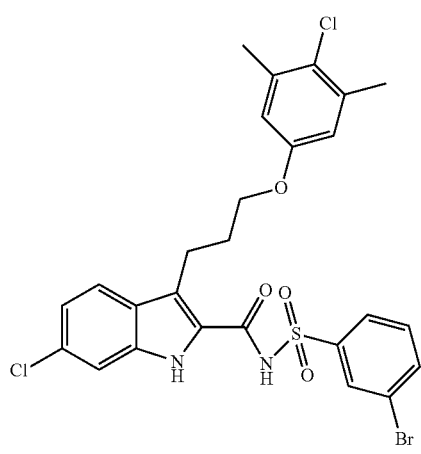
1940
-continued
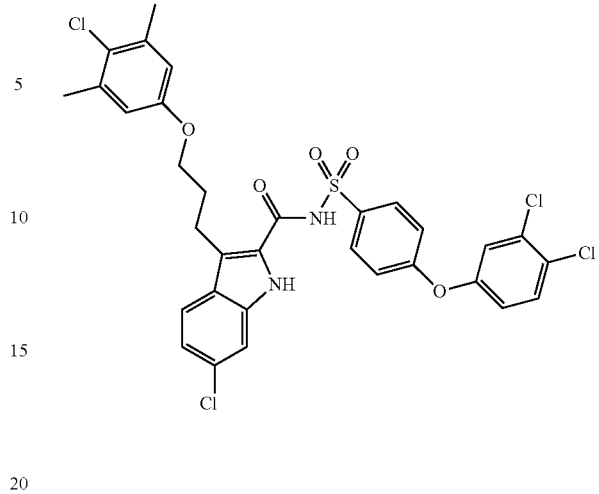
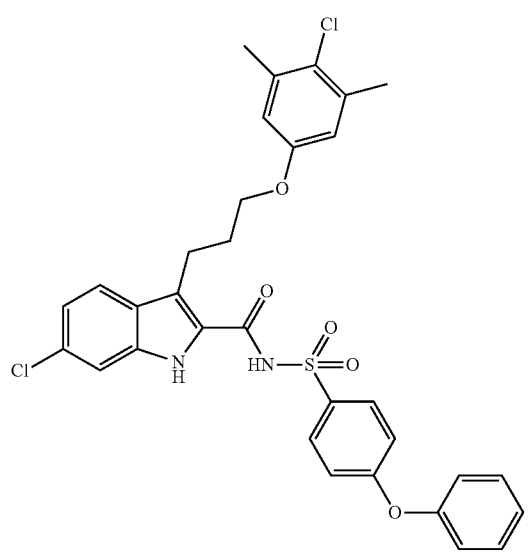
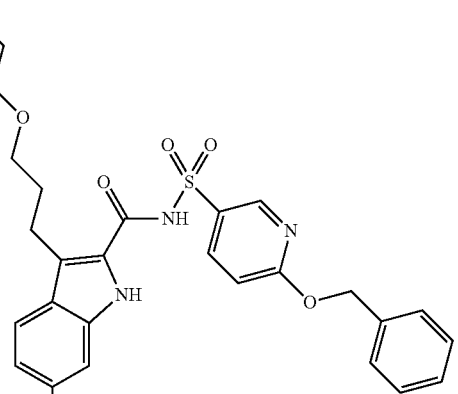

1941
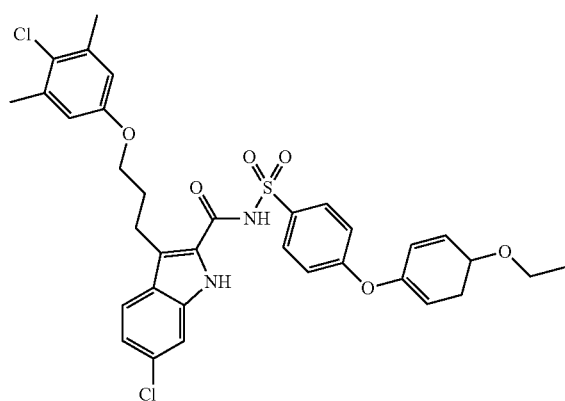
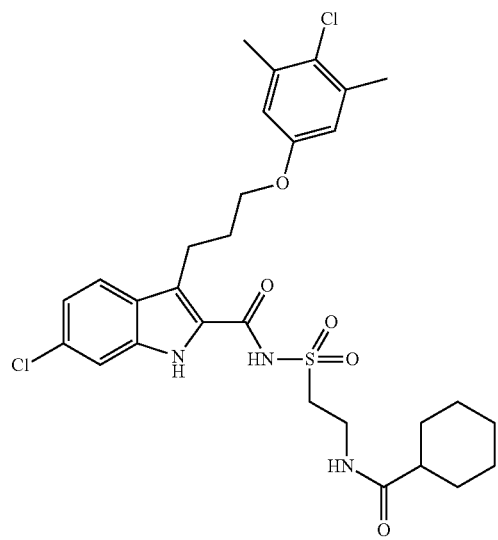
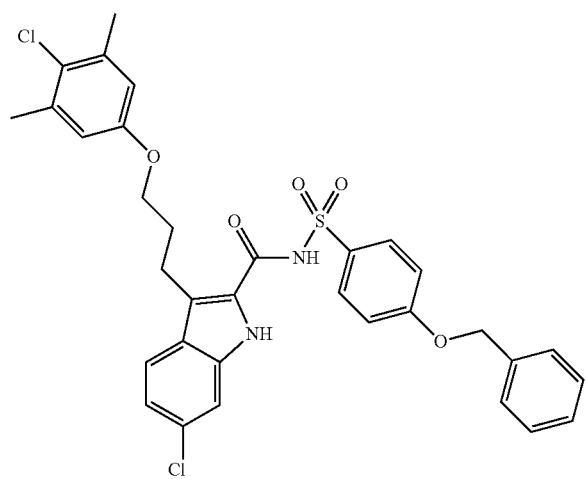
1942
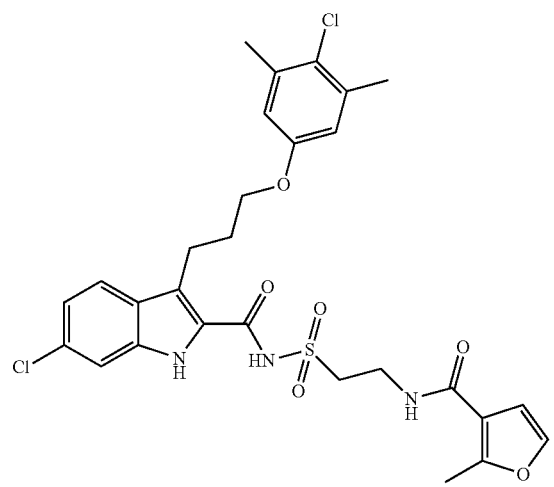
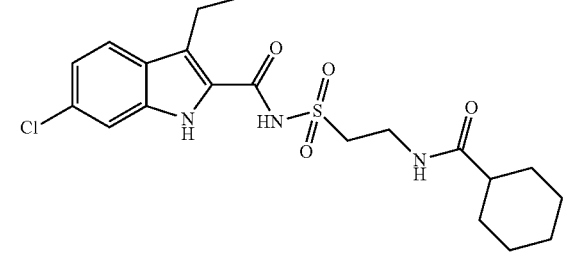
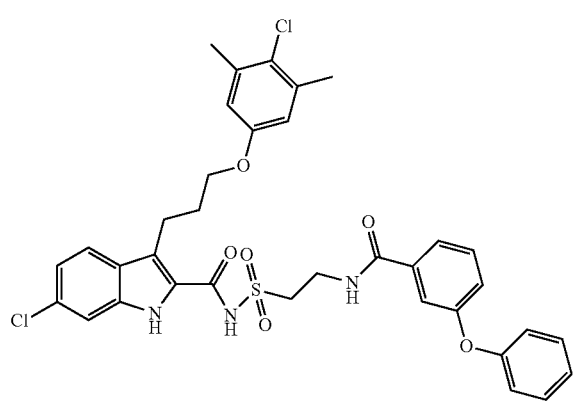

1943
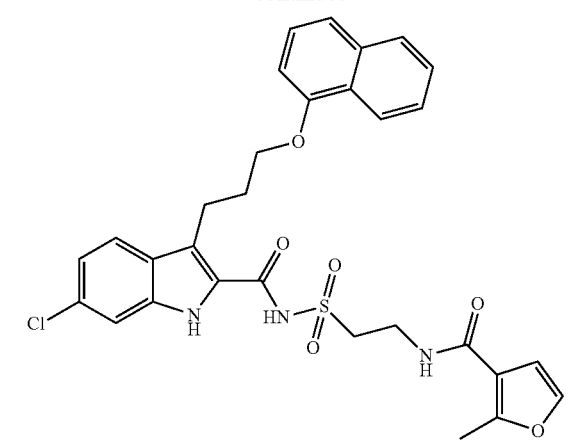
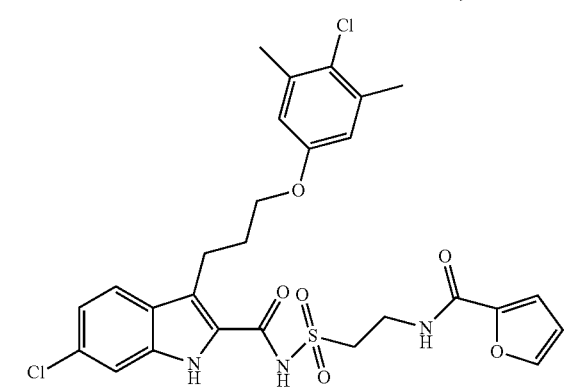
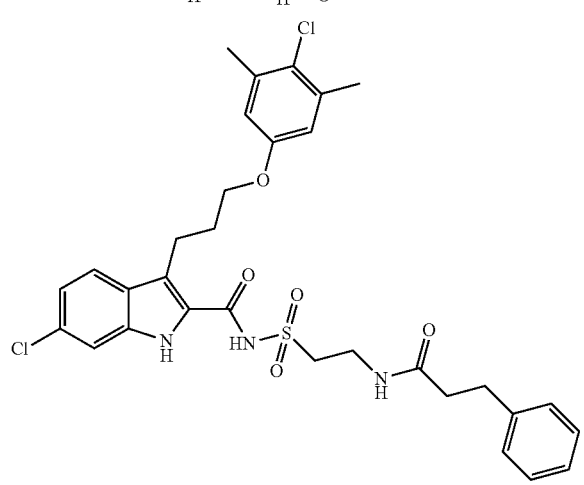
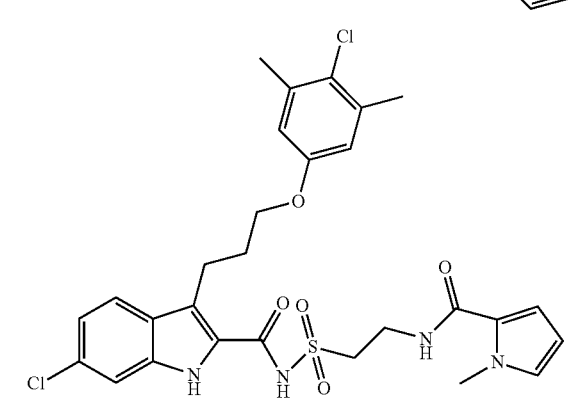
1944
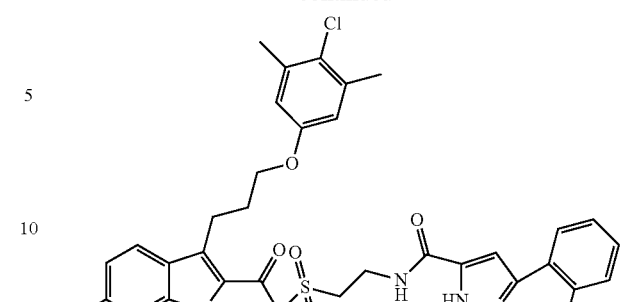
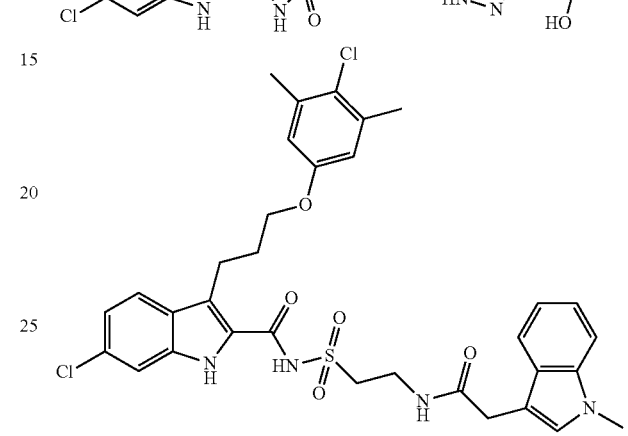
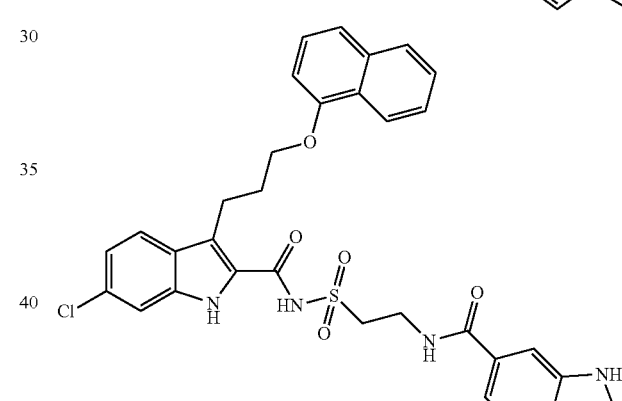
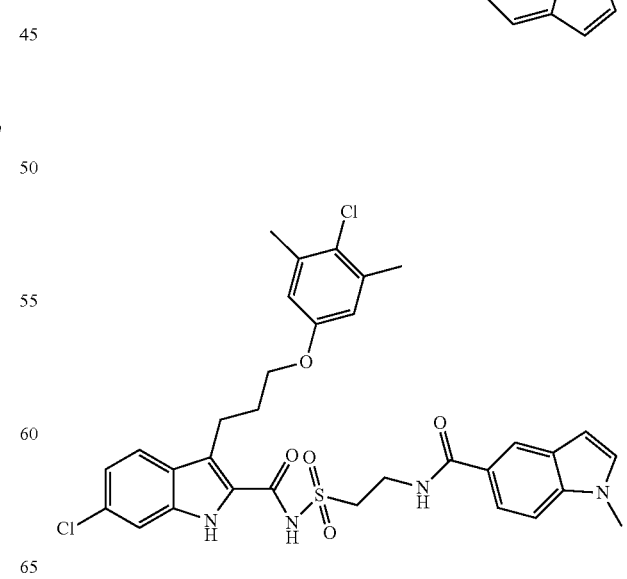

1945
-continued
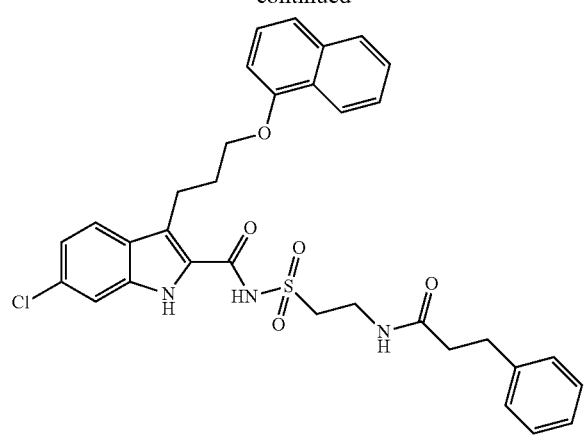
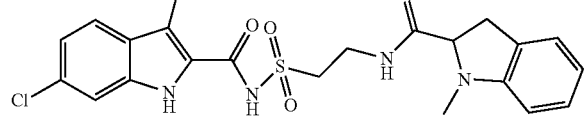
1946
-continued
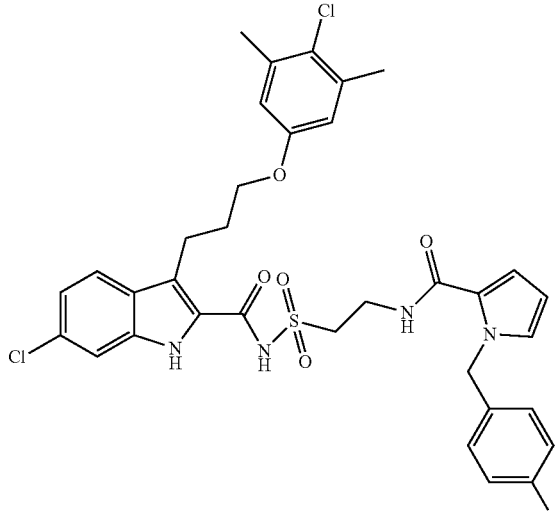
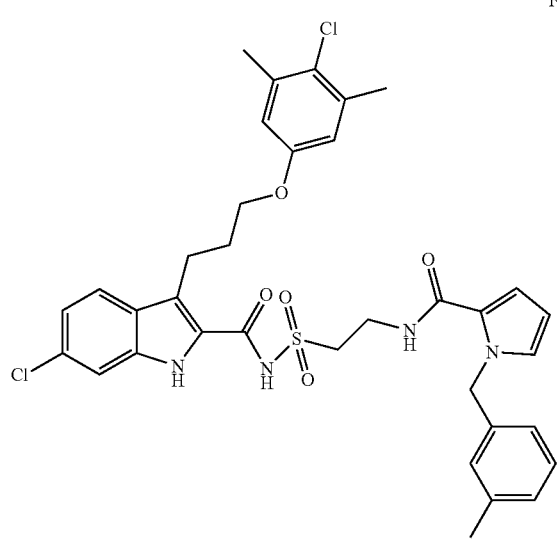
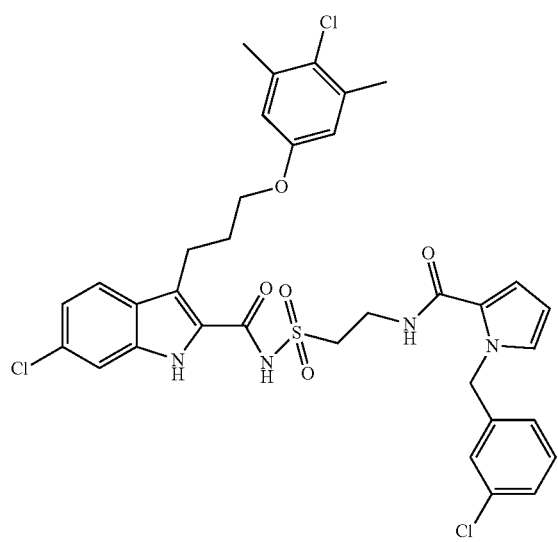

1947
-continued
1948
-continued
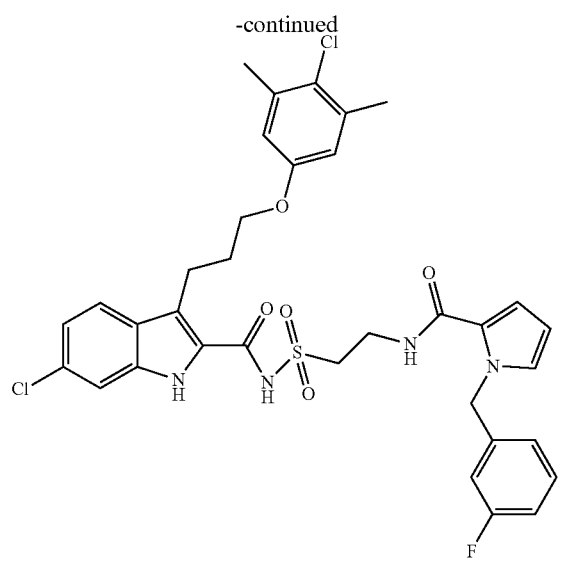
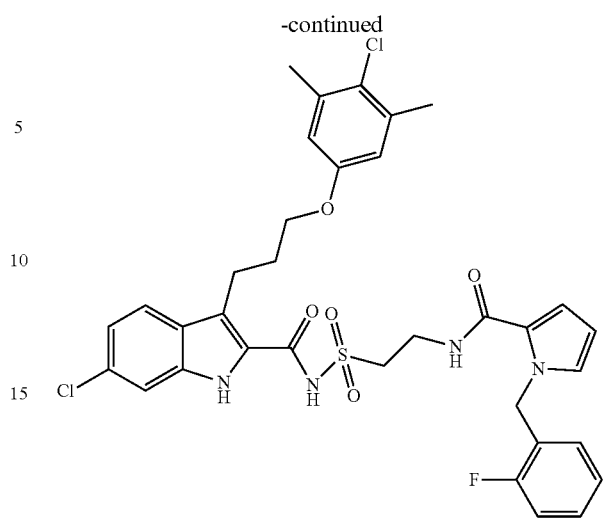
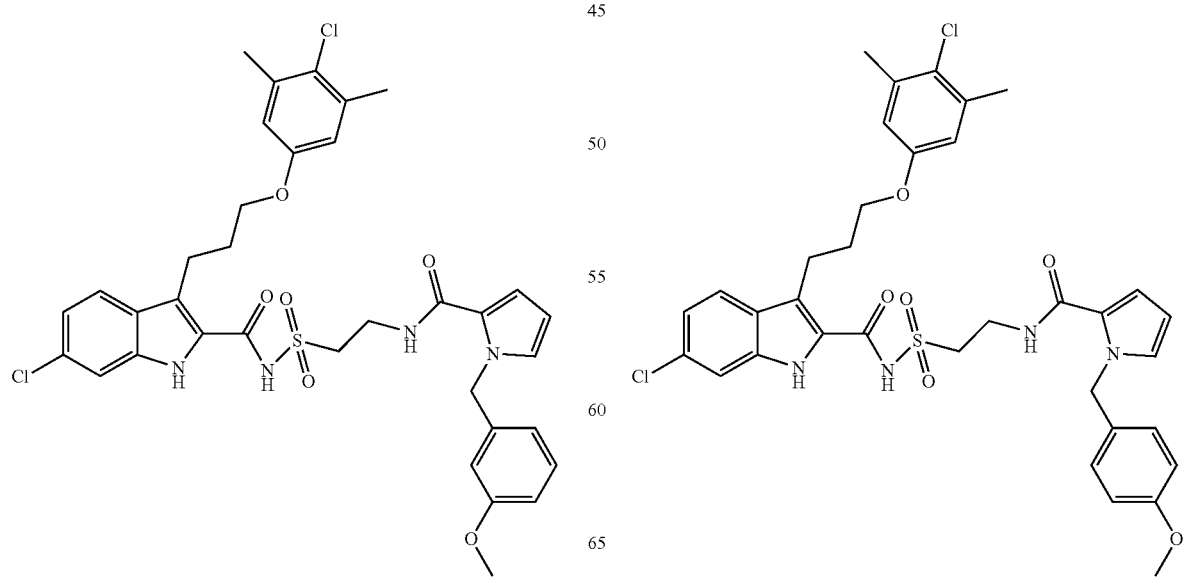

1949
-continued
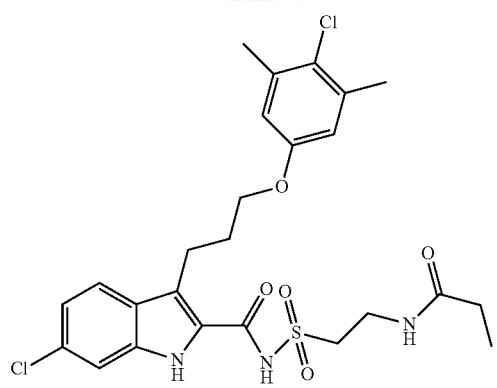
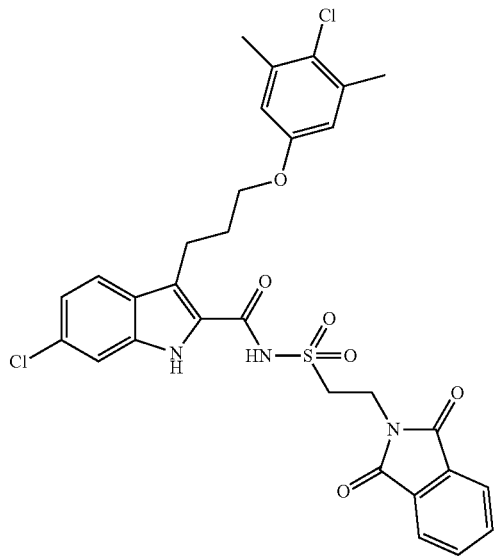
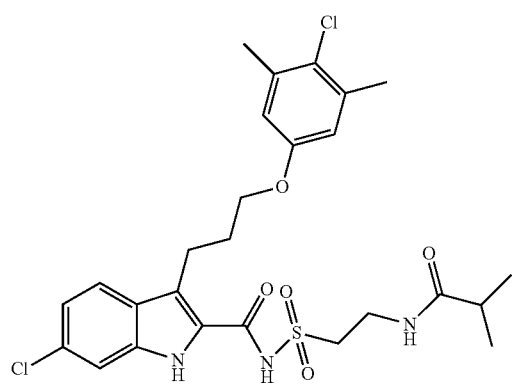
1950
-continued
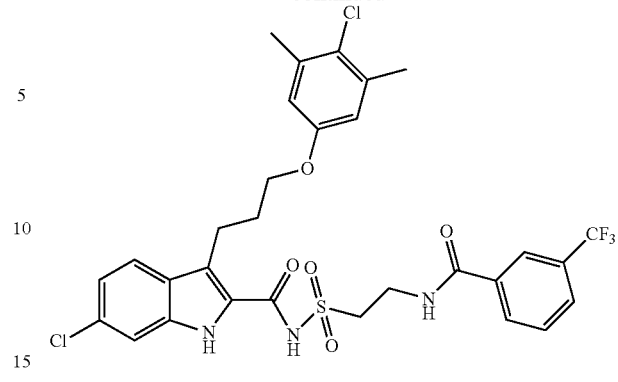
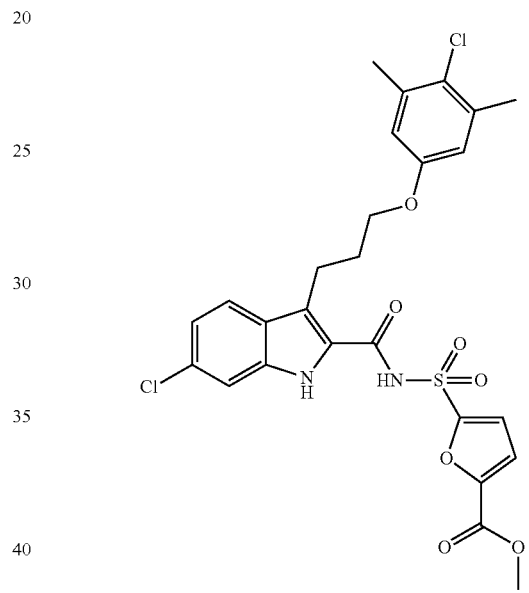
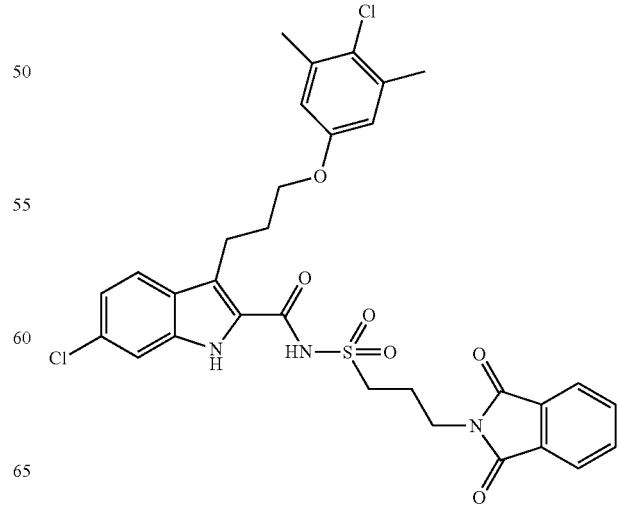

1951 -continued
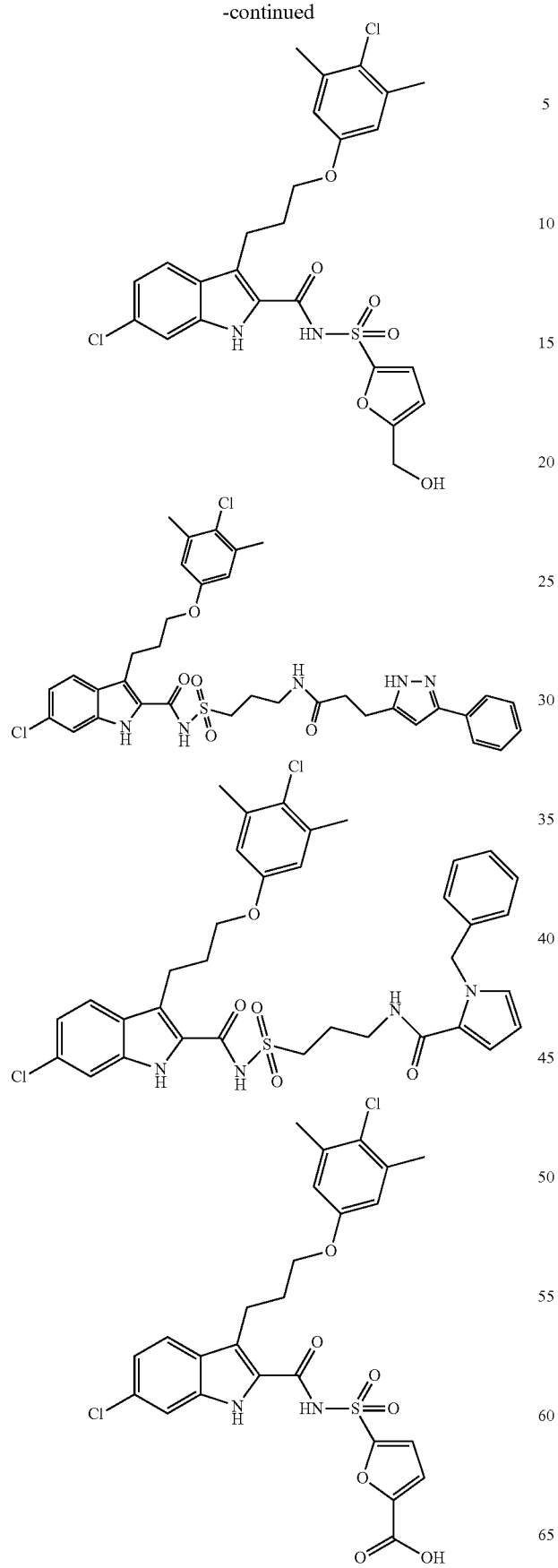
1952 -continued
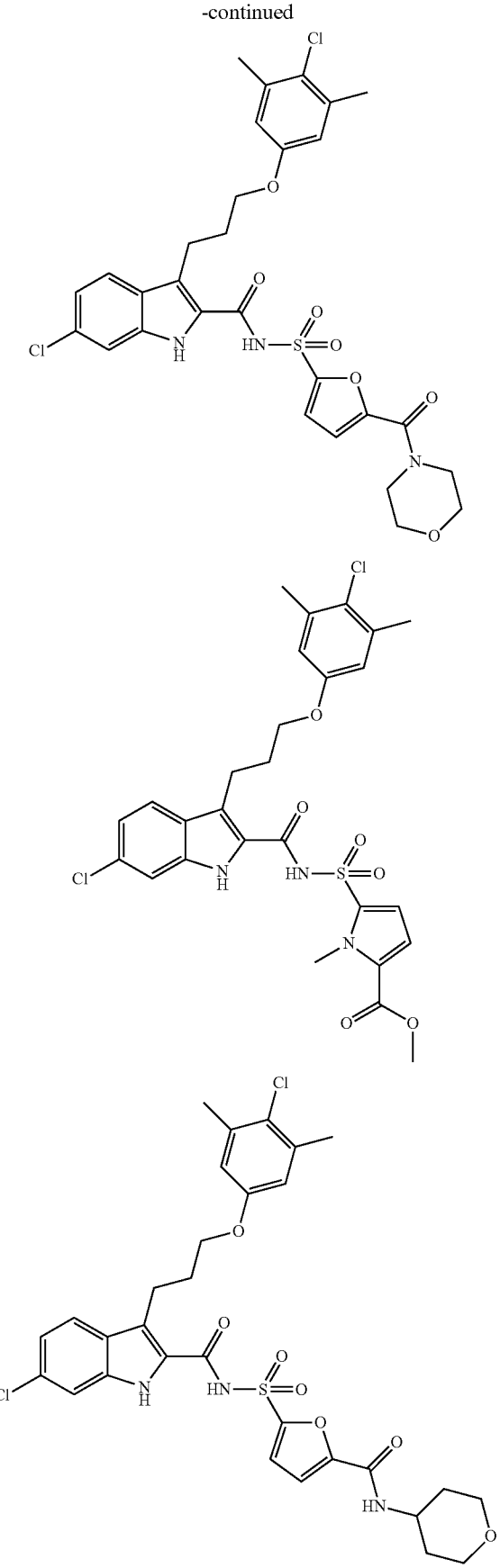

1953
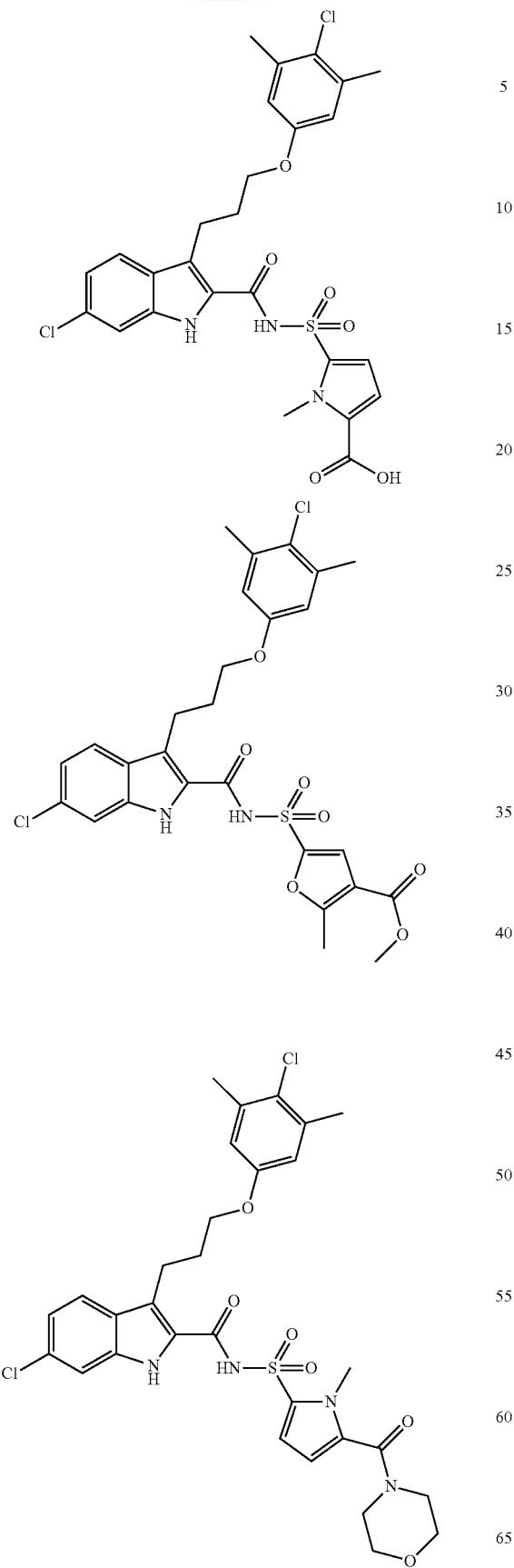
1954
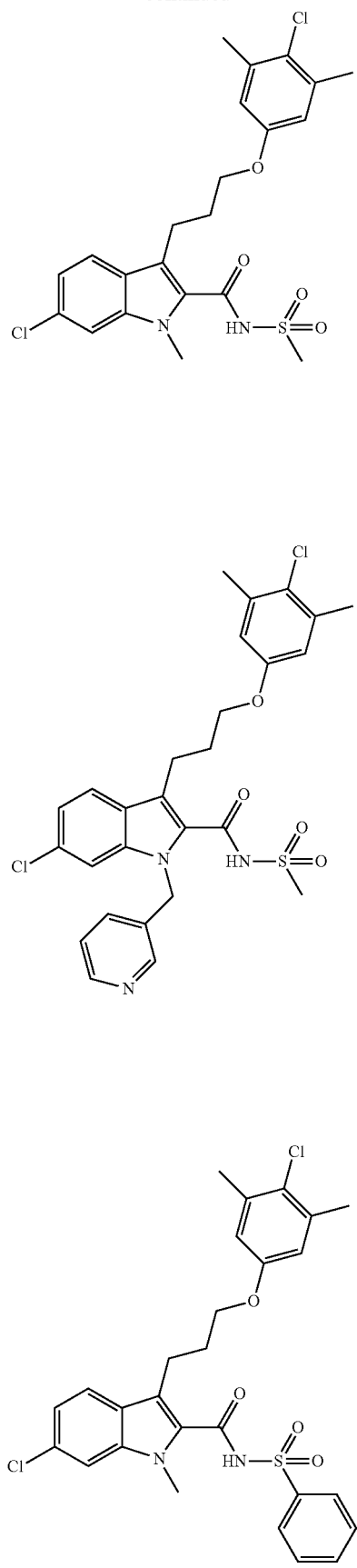

1955
-continued
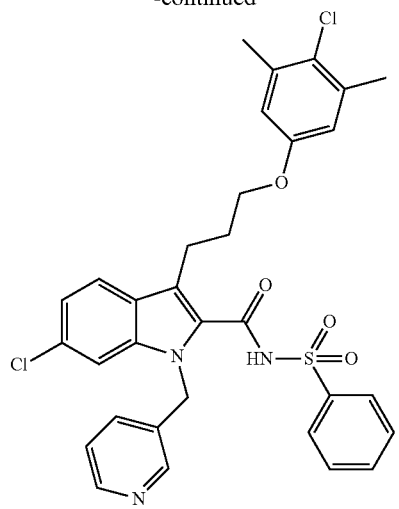
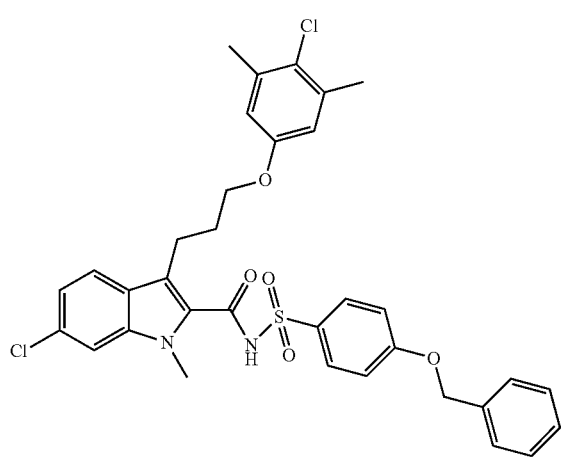
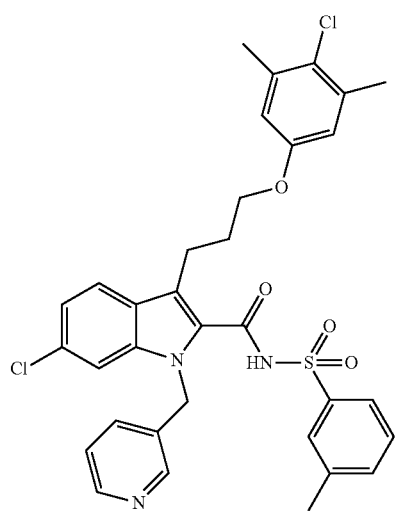
1956
-continued
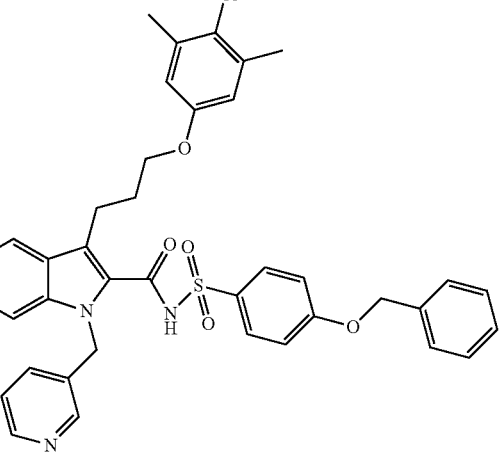
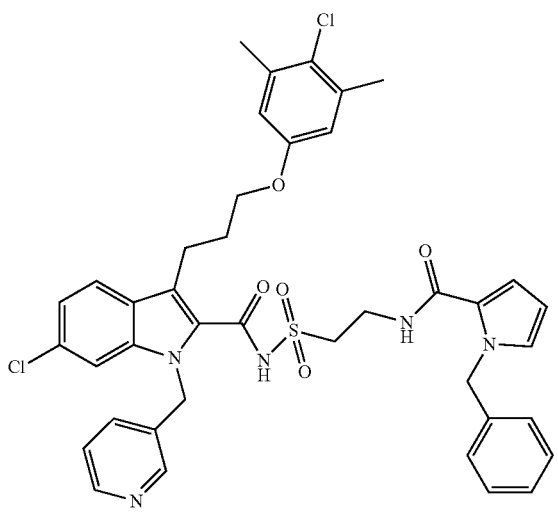
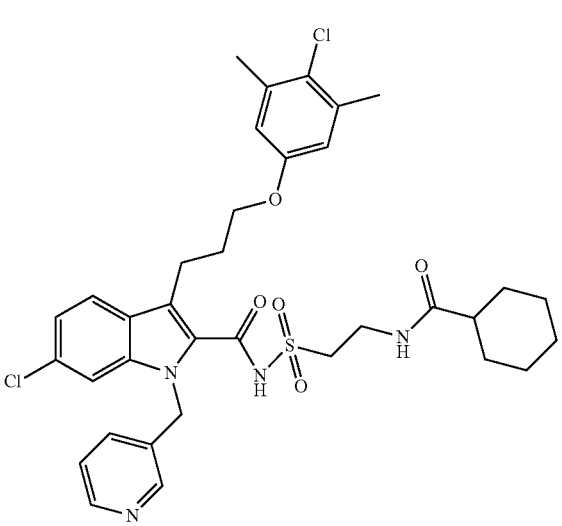

1957
-continued
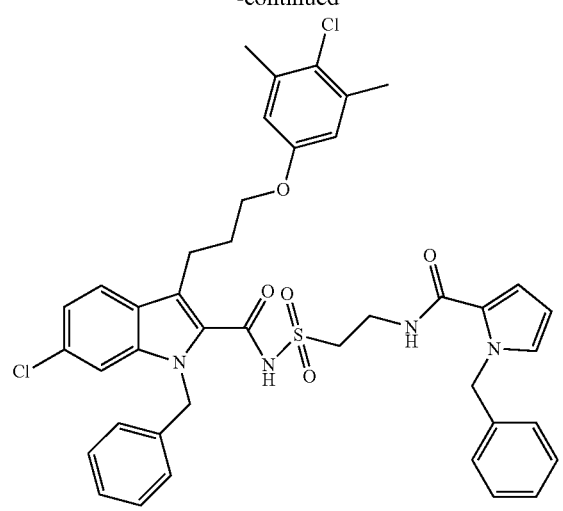
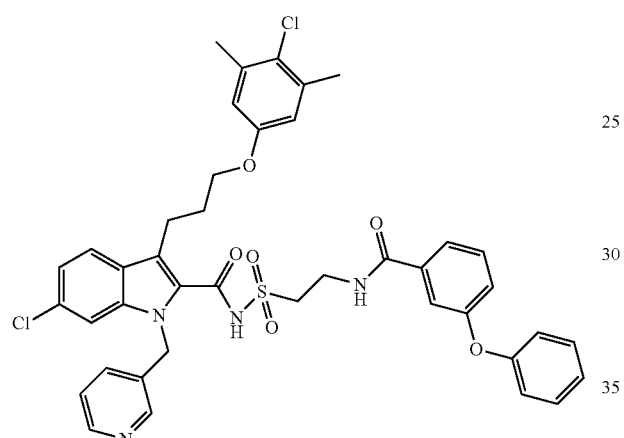
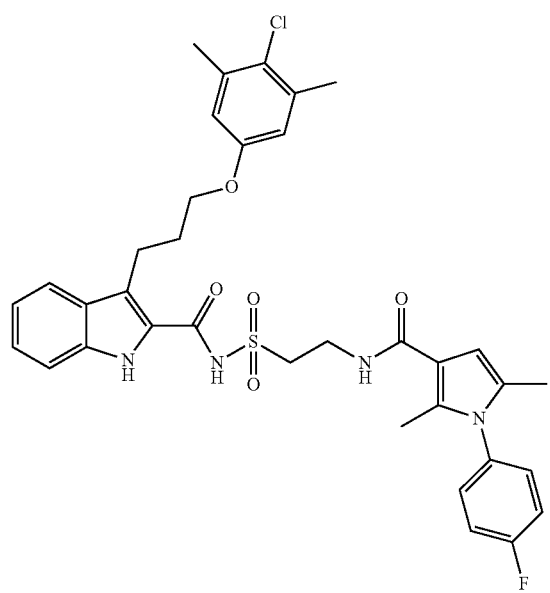
1958
-continued
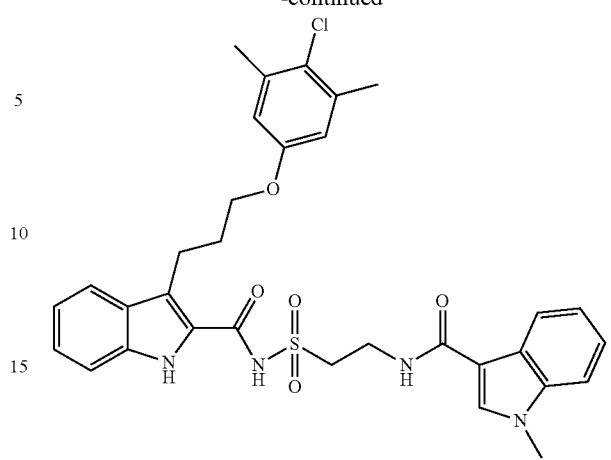
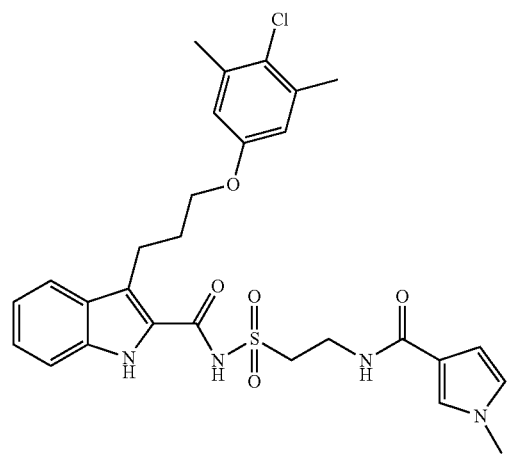
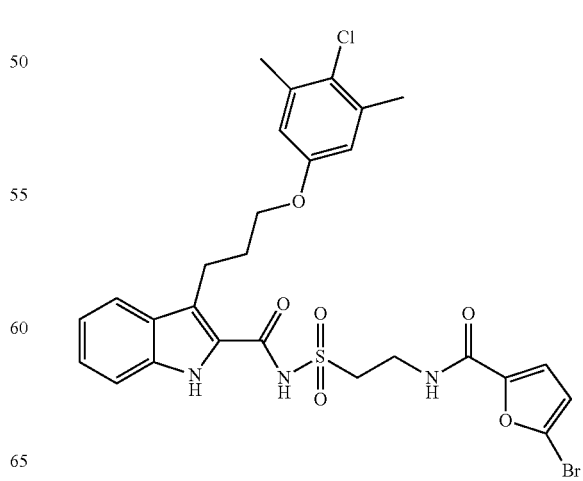

1959
-continued
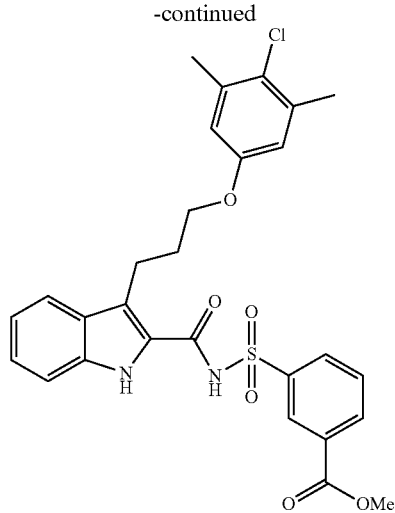
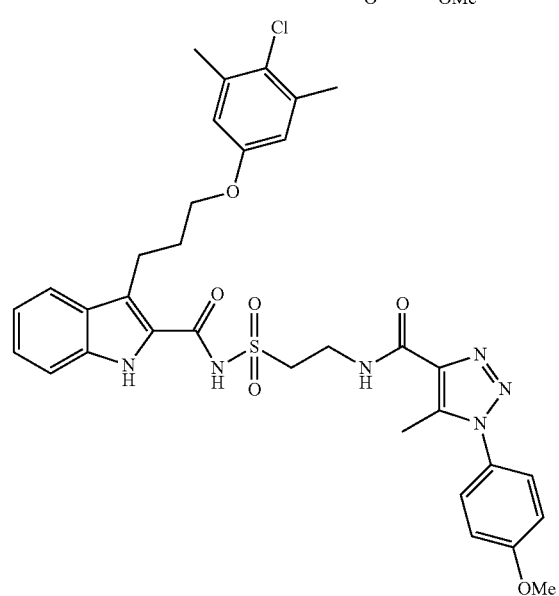
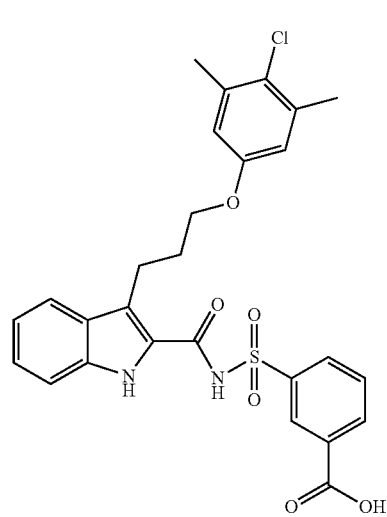
1960
-continued
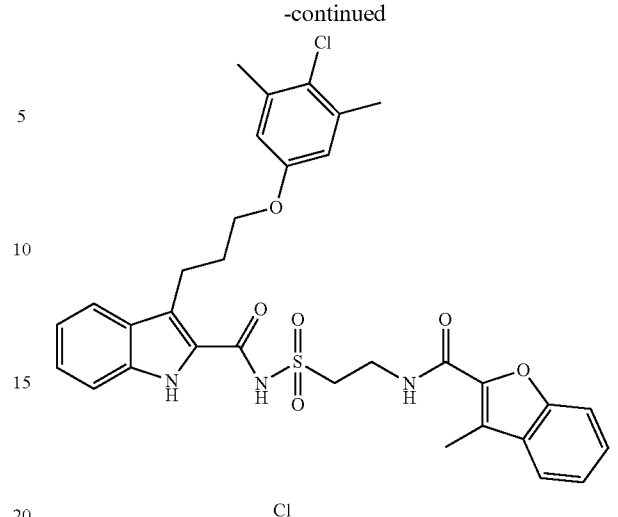
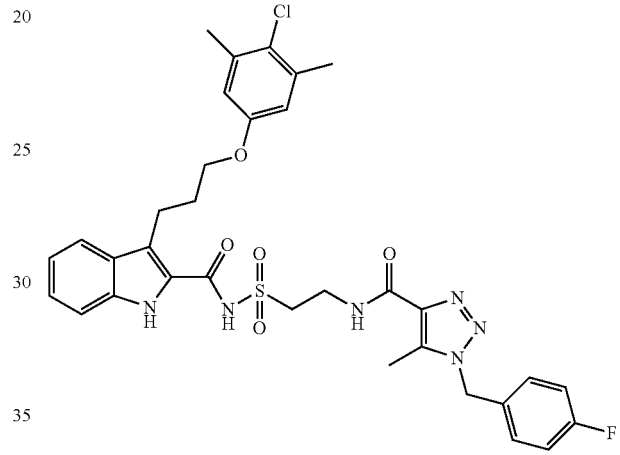
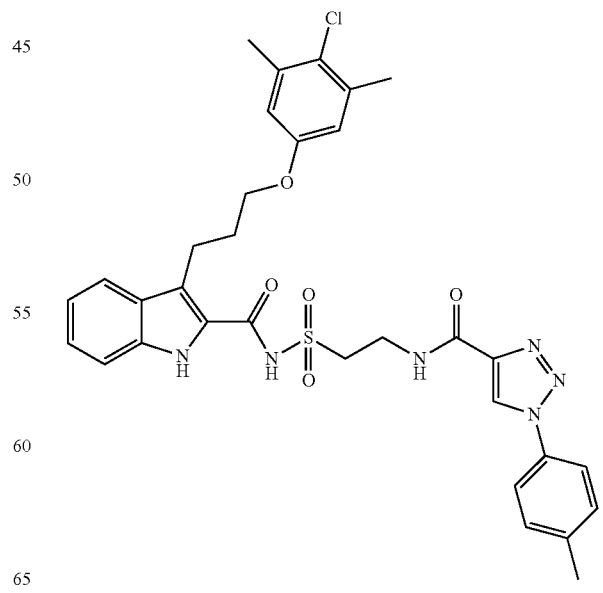

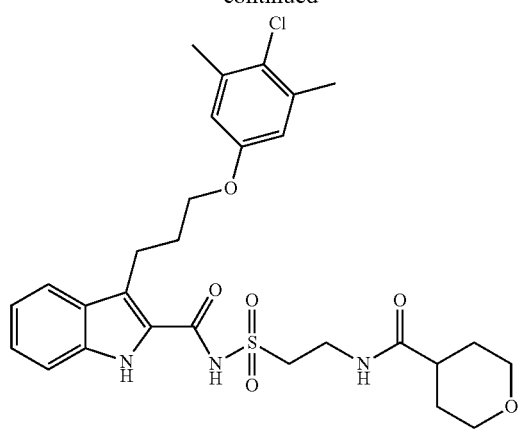
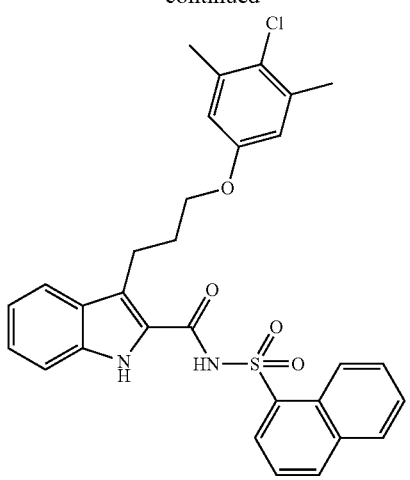
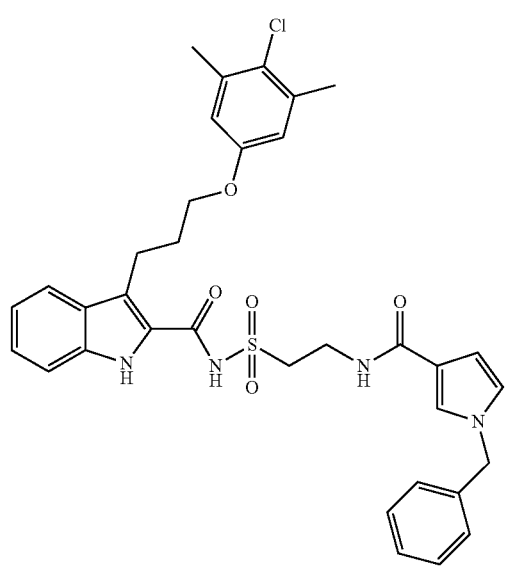
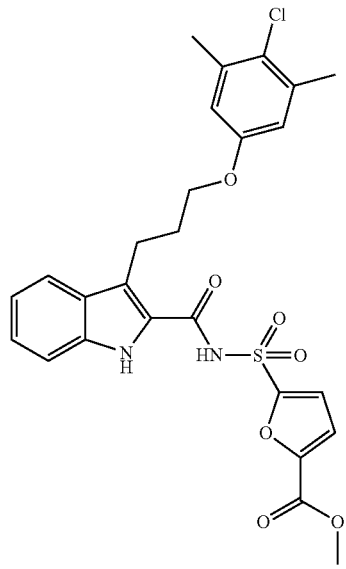
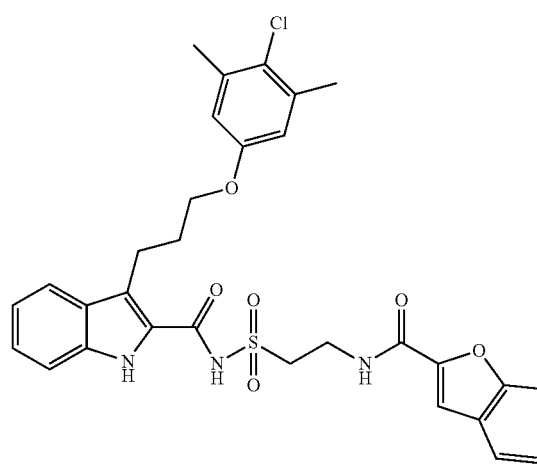
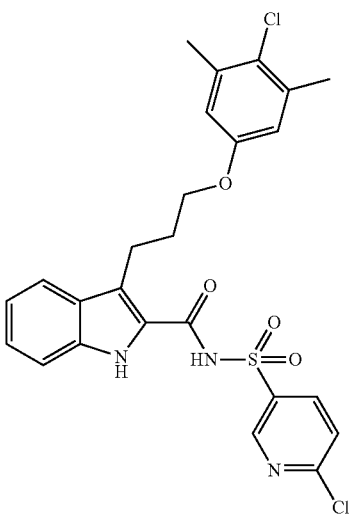

-continued
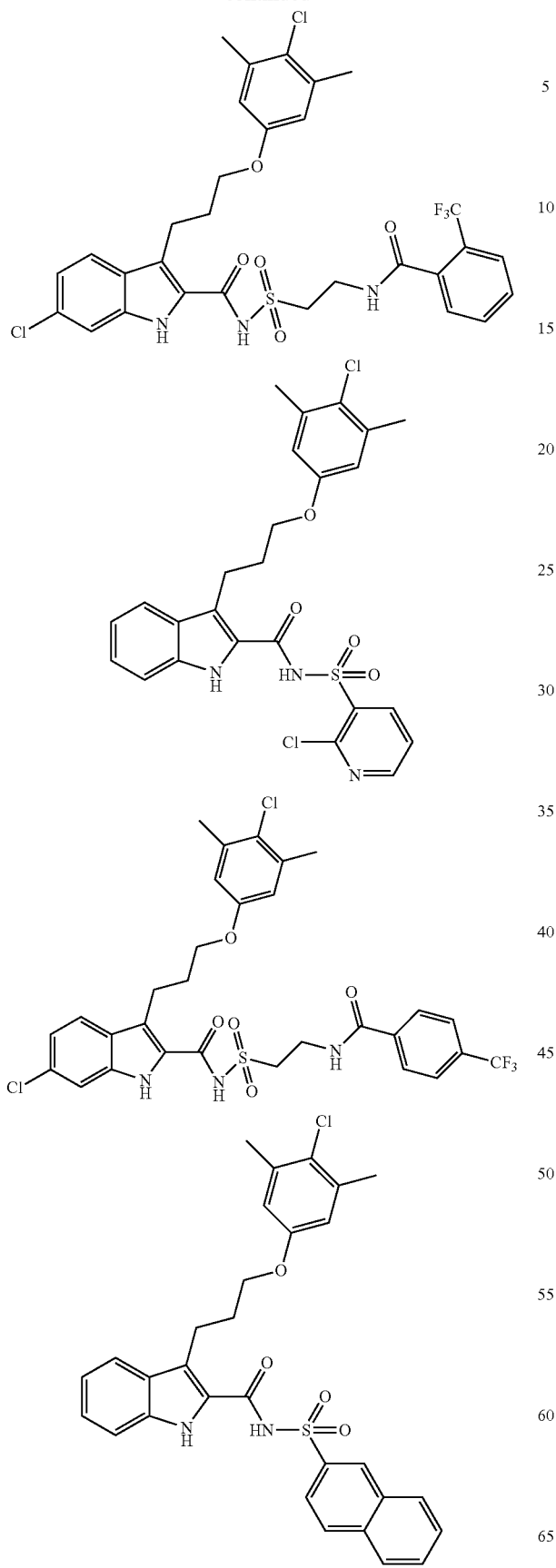
-continued
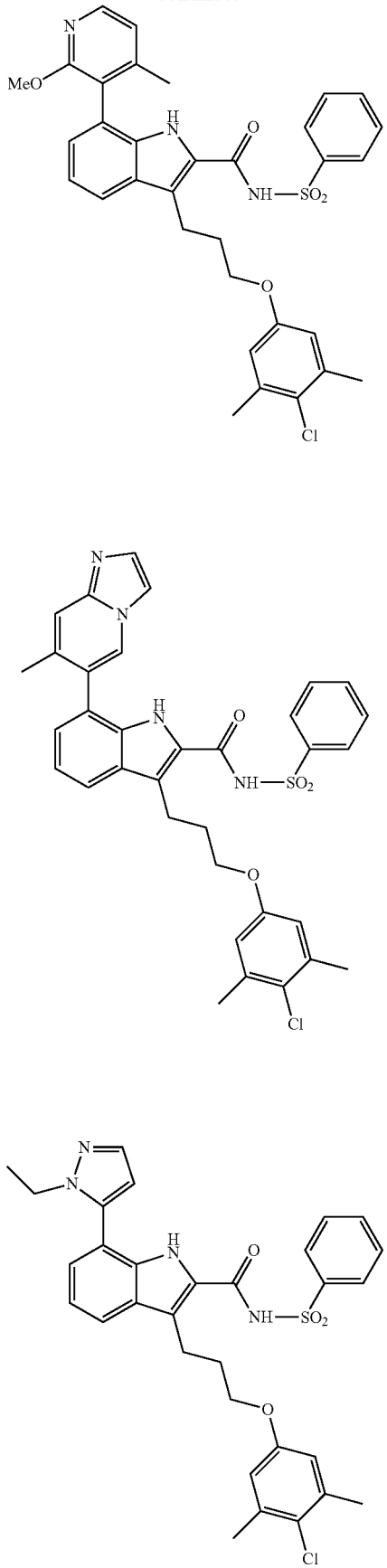

1965
-continued
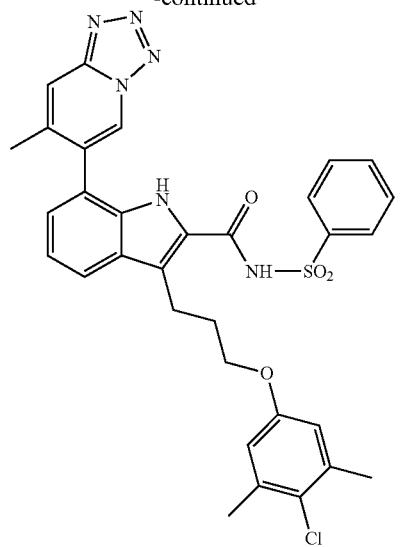
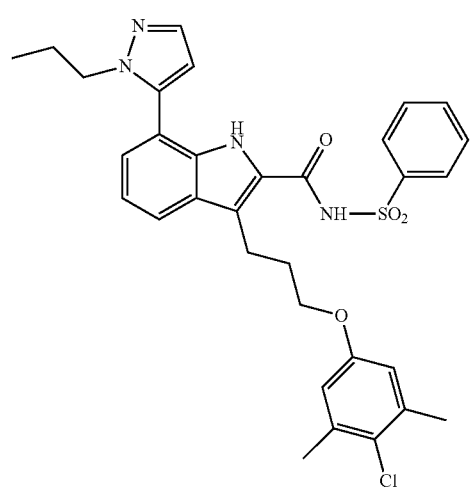
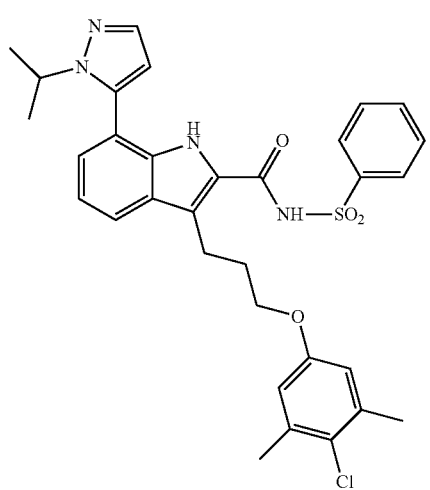
1966
-continued
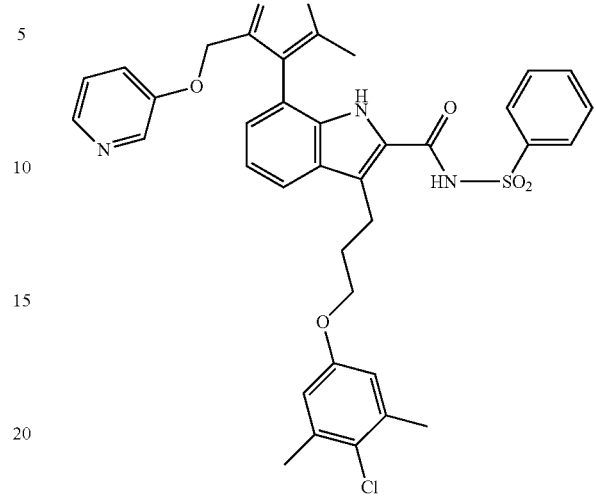

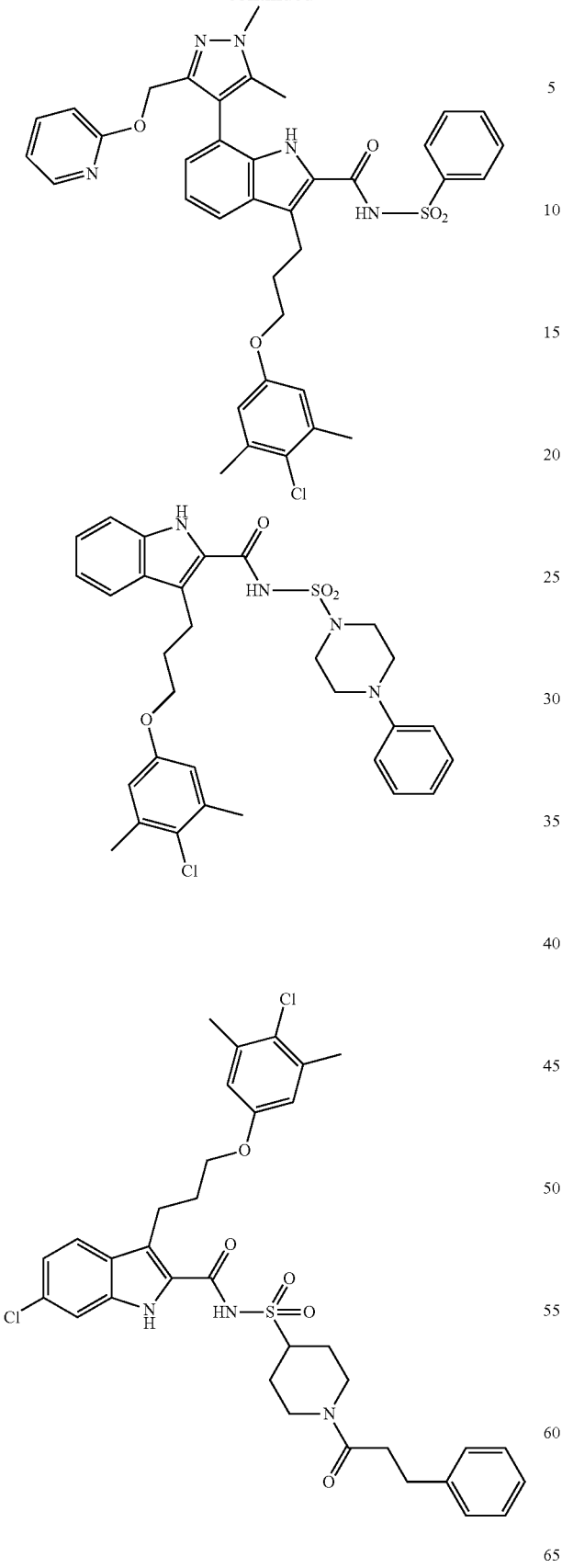
In some embodiments, the compound is selected from the group consisting of:
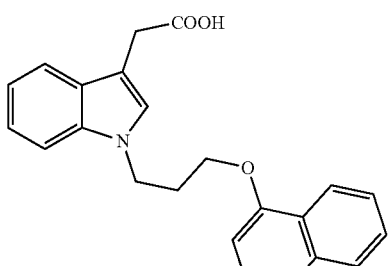
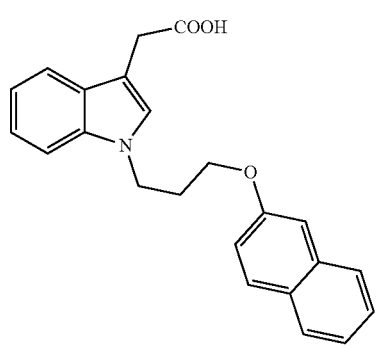
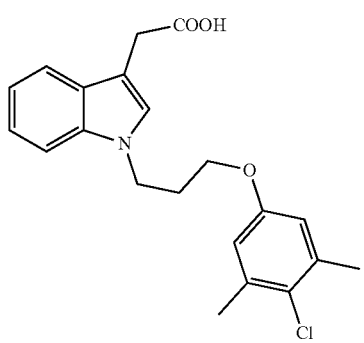
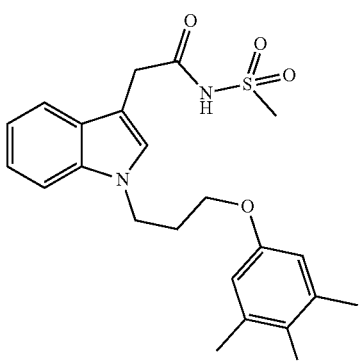
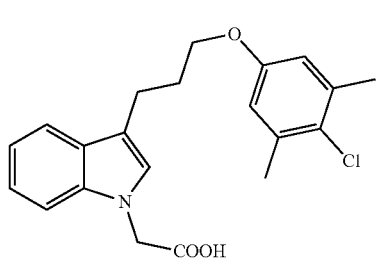

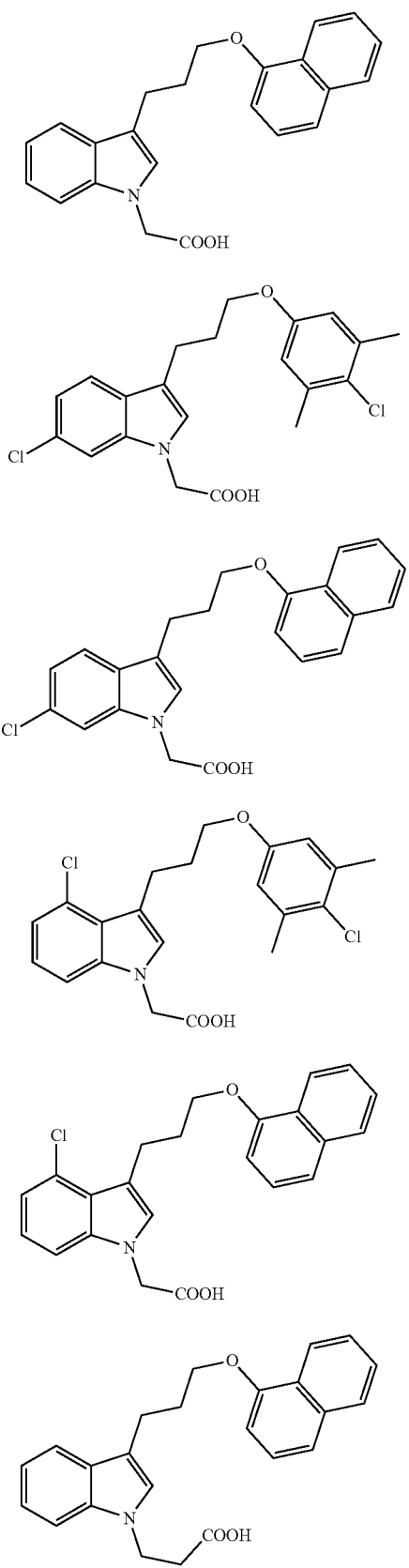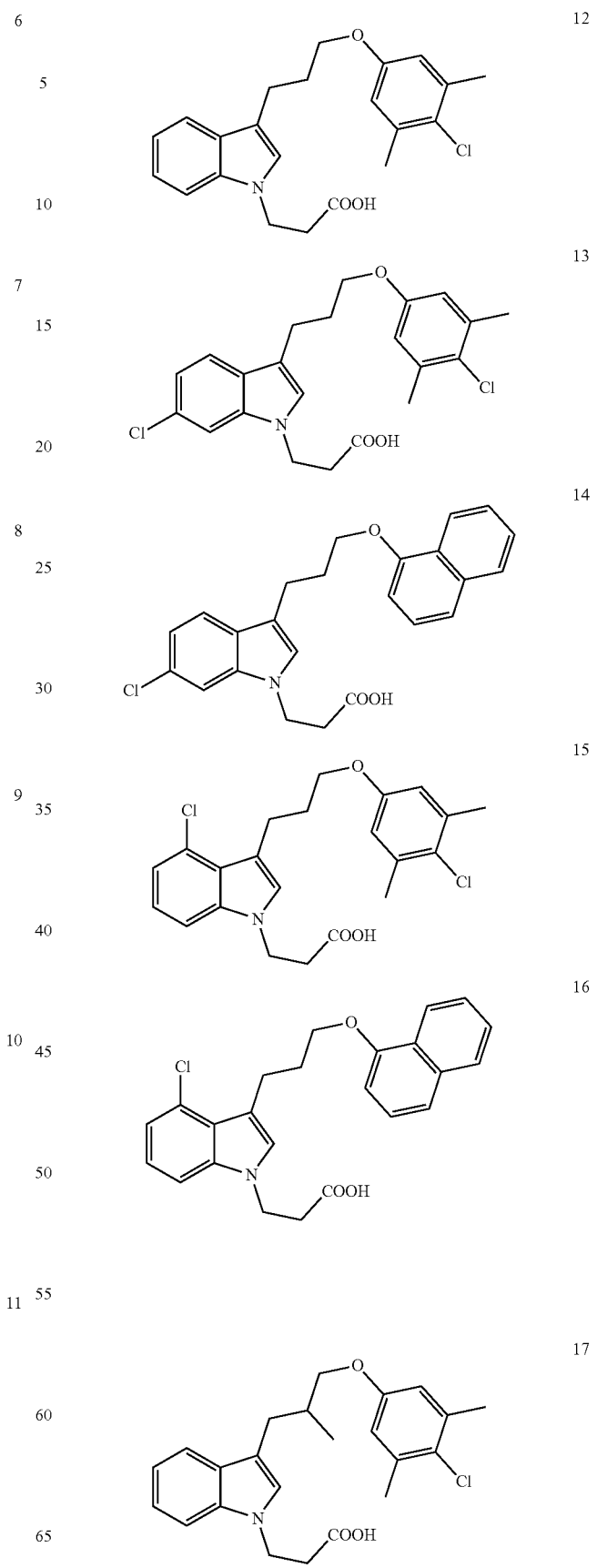

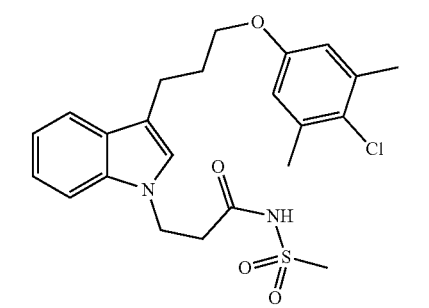
18
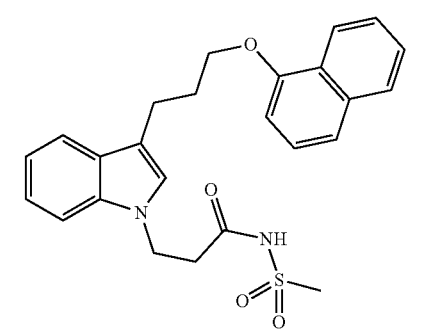
19
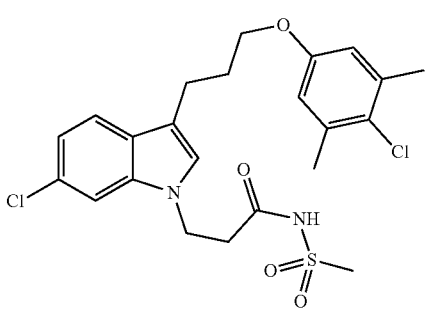
20
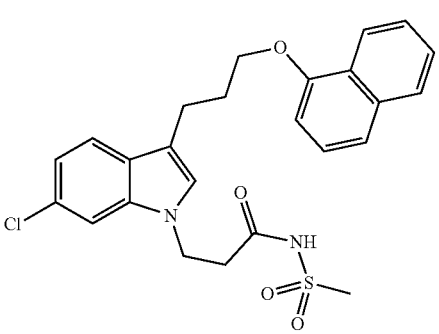
21
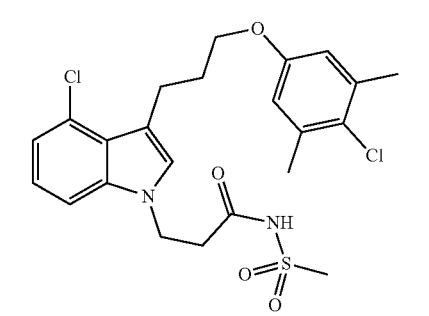
22
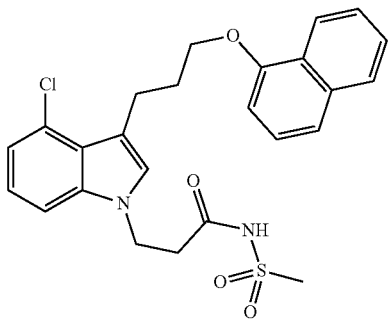
23
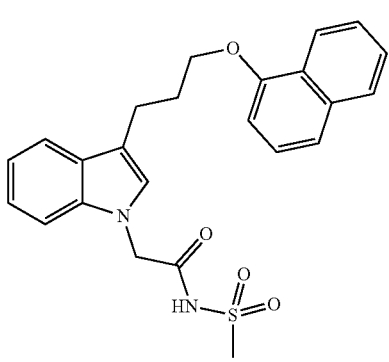
24
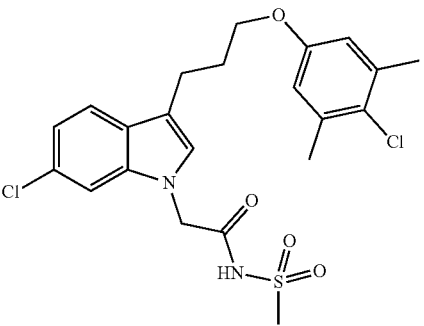
25
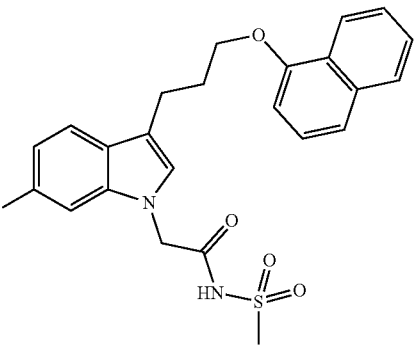
26

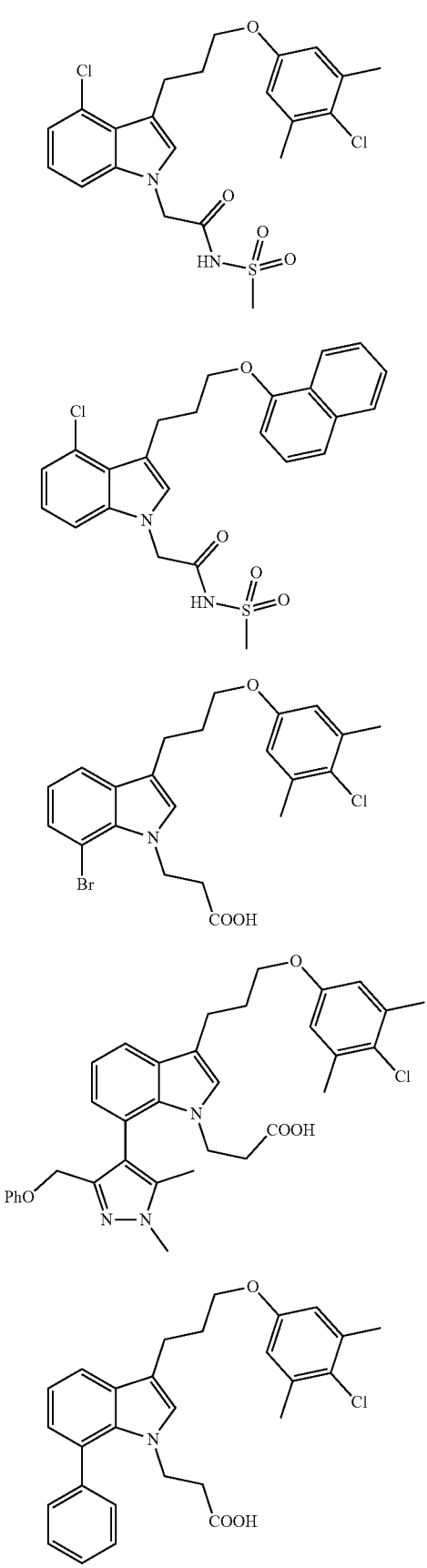
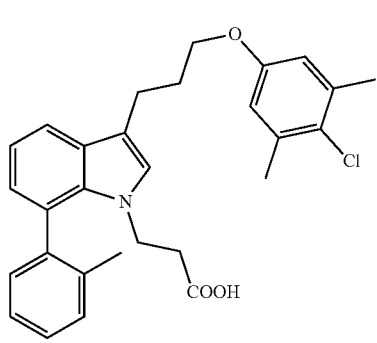
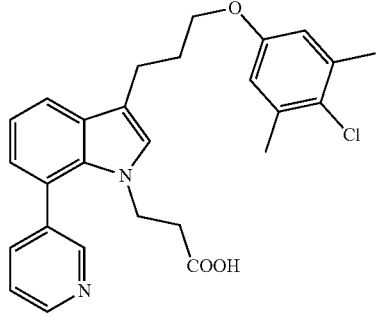
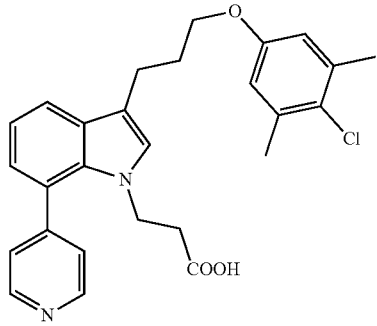
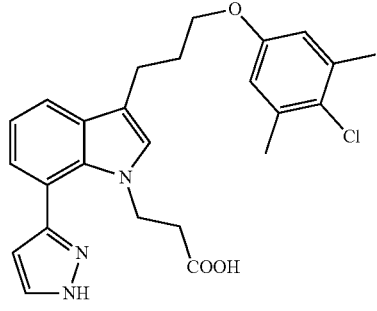
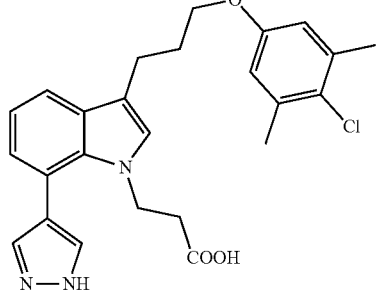

1975
37
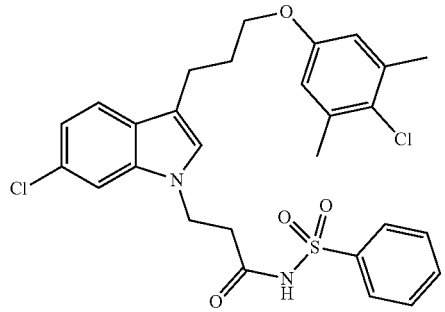
38
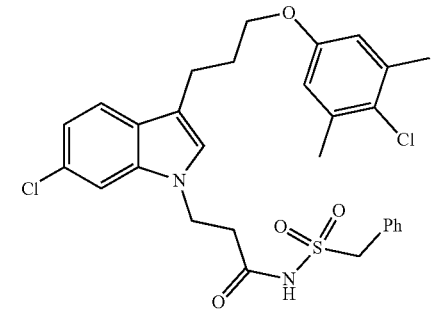
39
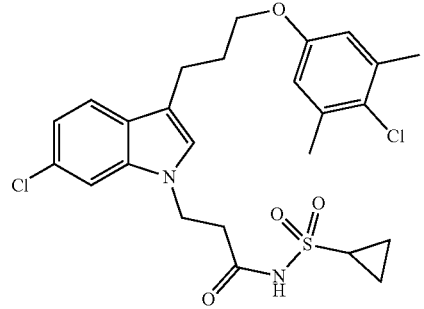
40
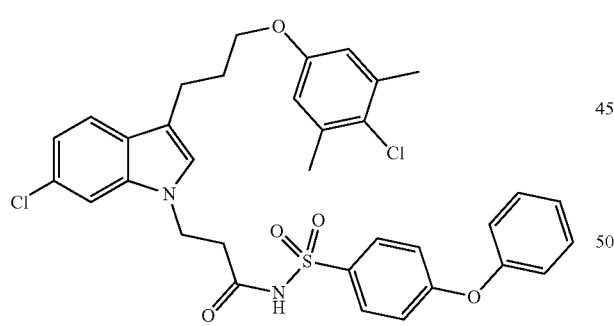
41
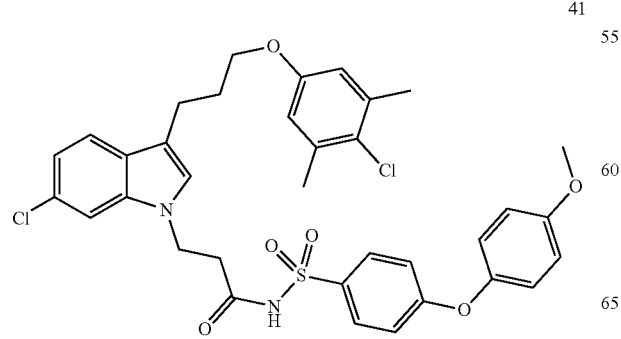
1976
42
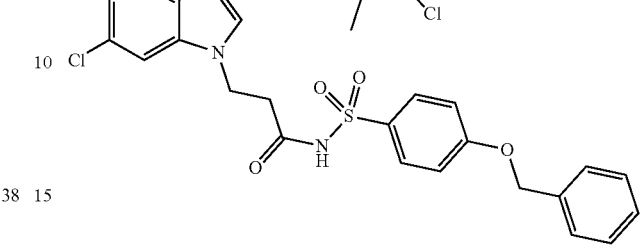
43
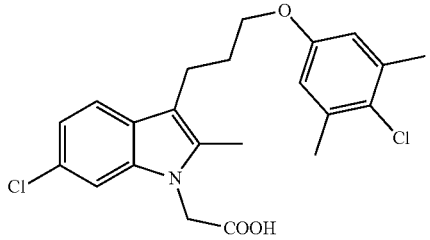
44
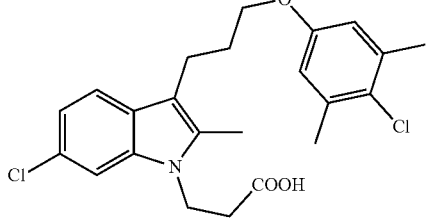
45
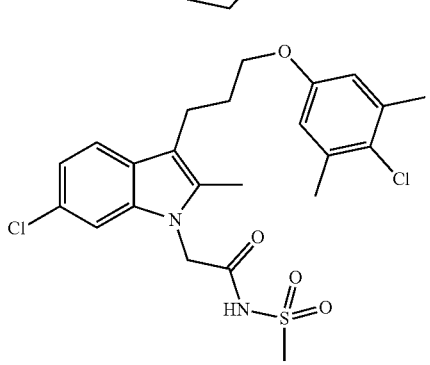
46
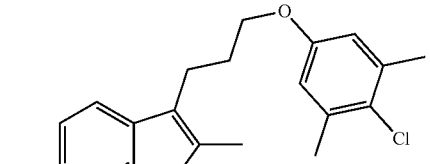

47
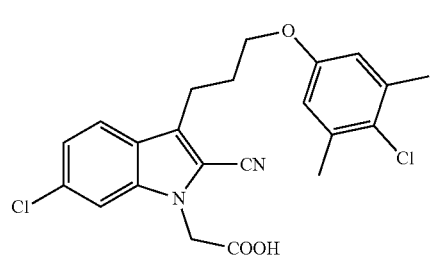
48
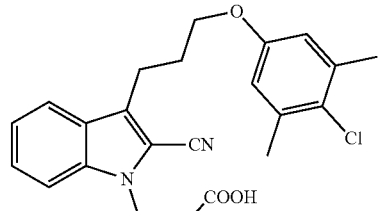
49
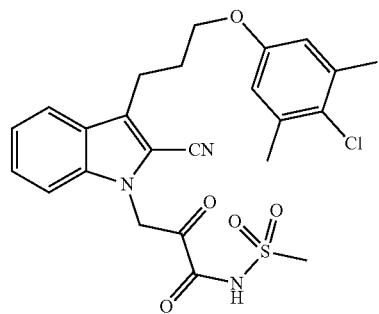
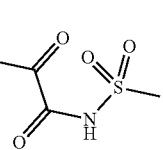
50
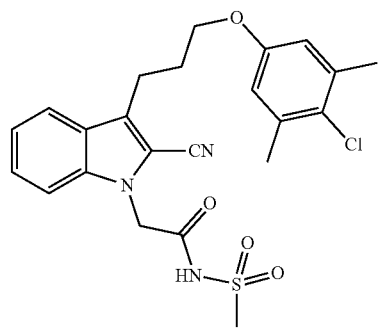
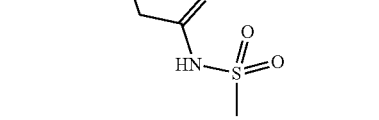
51
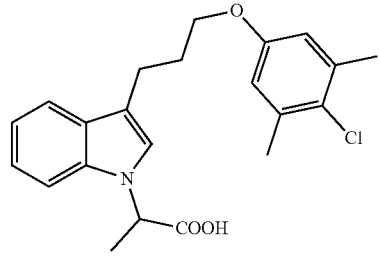
52
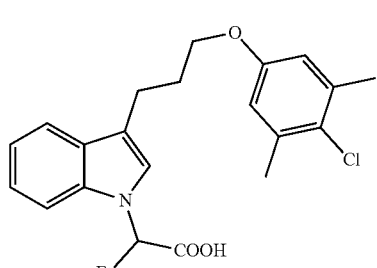
53
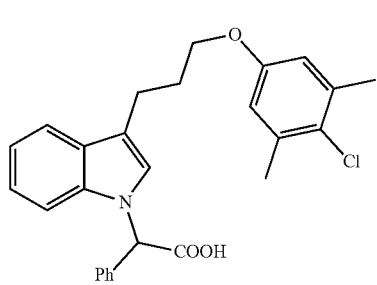
54
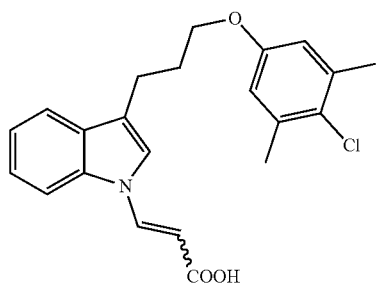
55
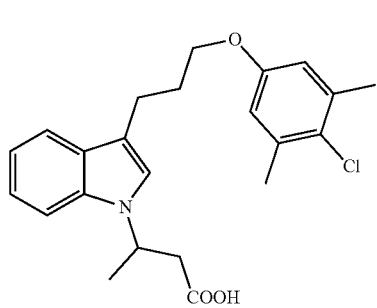
56
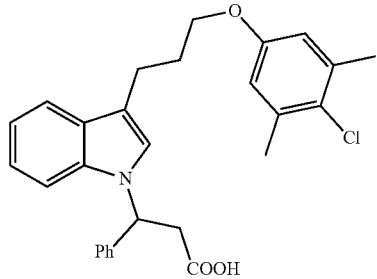

1979
-continued
57
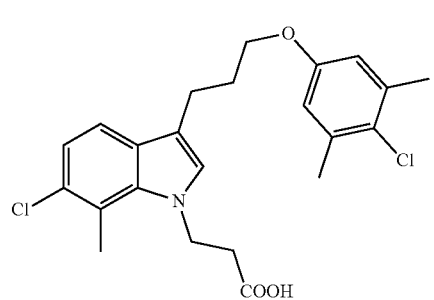
58
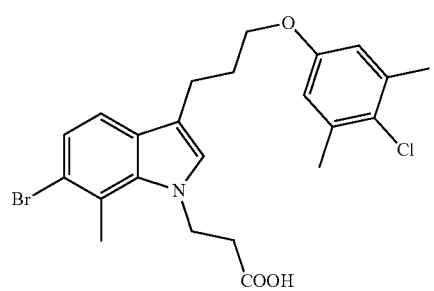
59
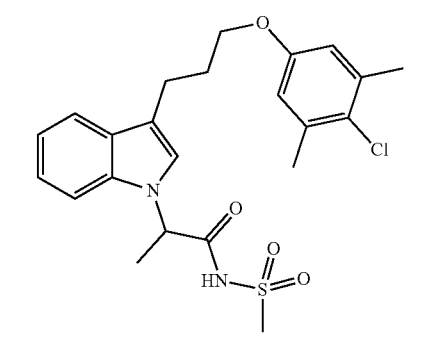
60
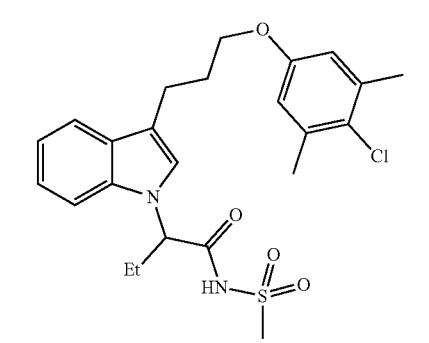
61
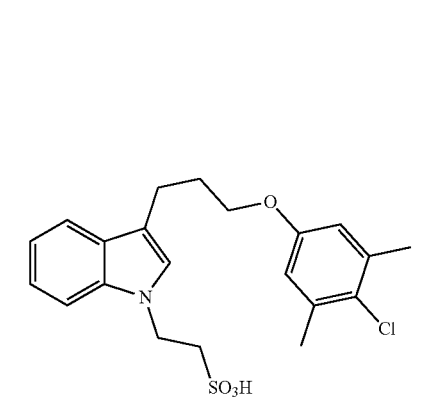
1980
-continued
62
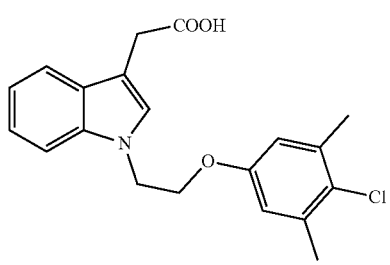
63
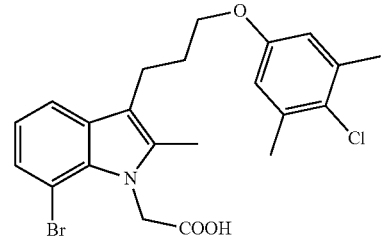
64
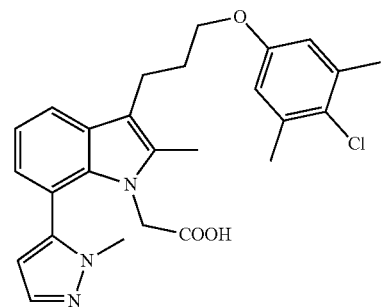
65
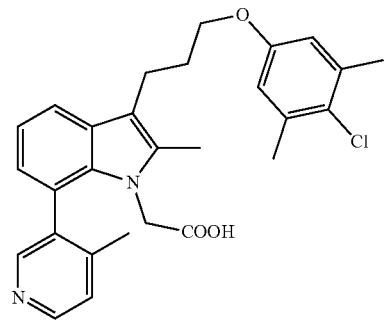
66
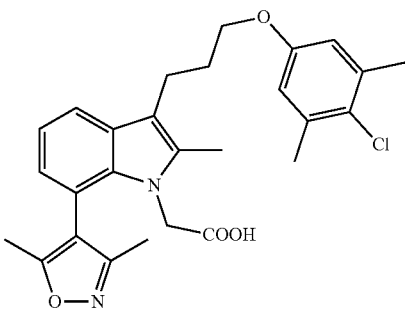

-continued
67
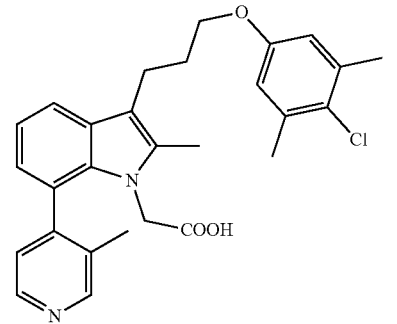
68
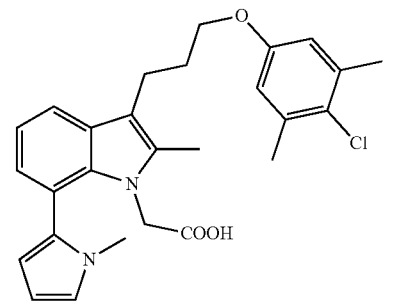
69
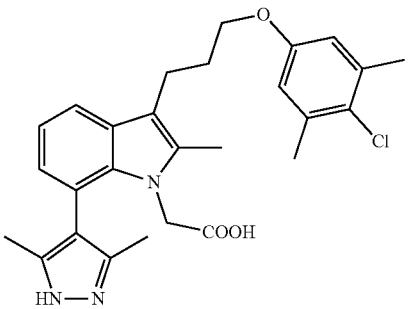
70
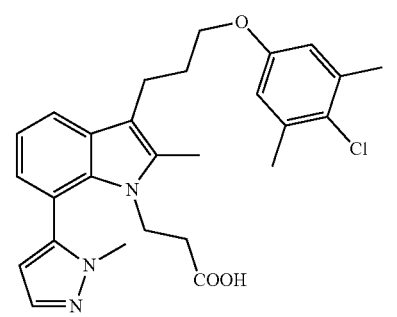
71
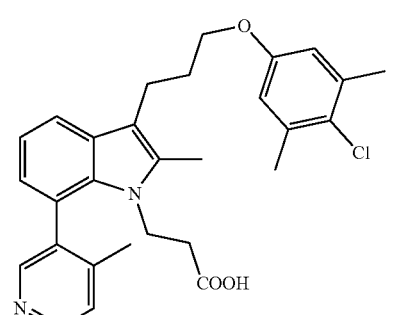
-continued
72
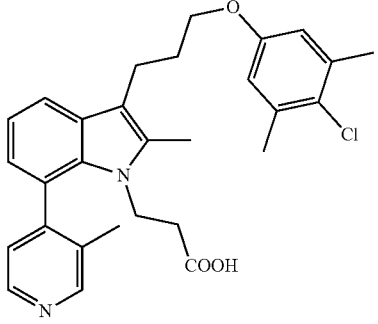
73
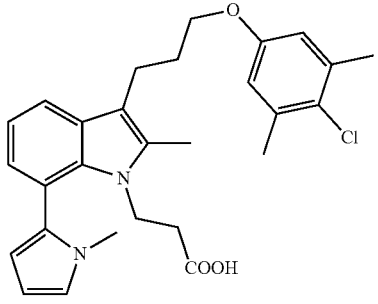
74
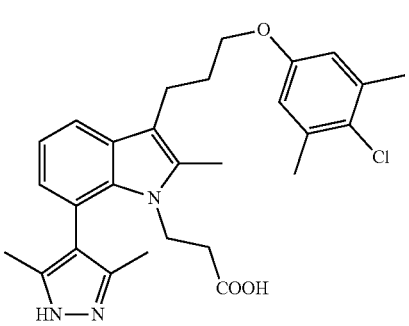
75
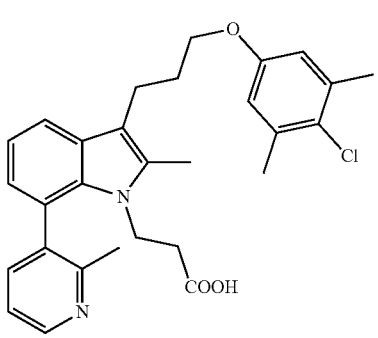
76
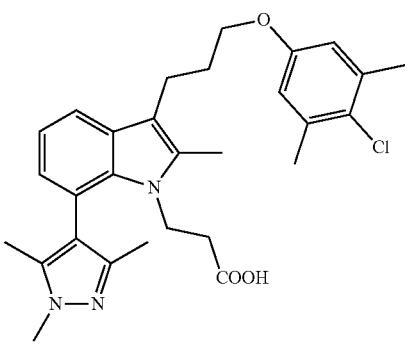

77
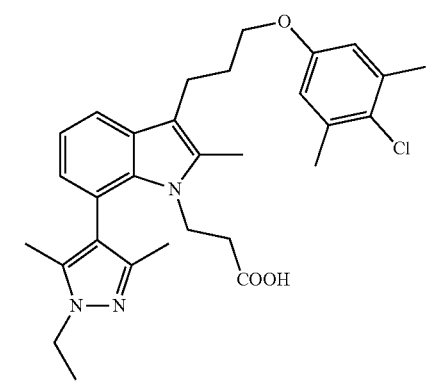
78
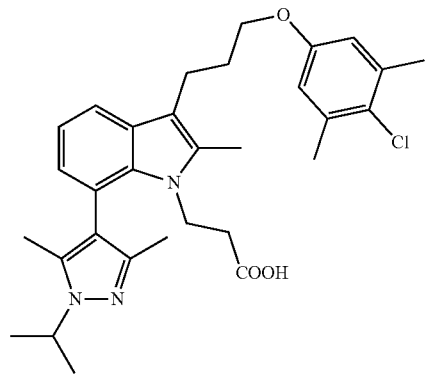
79
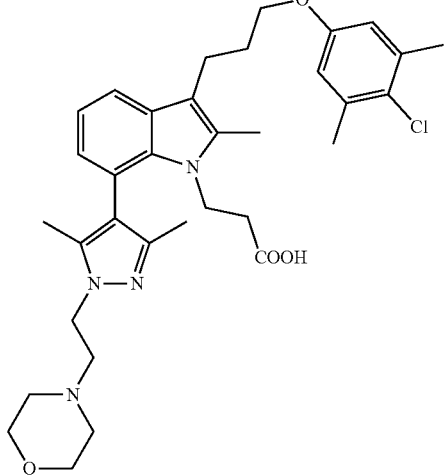
80
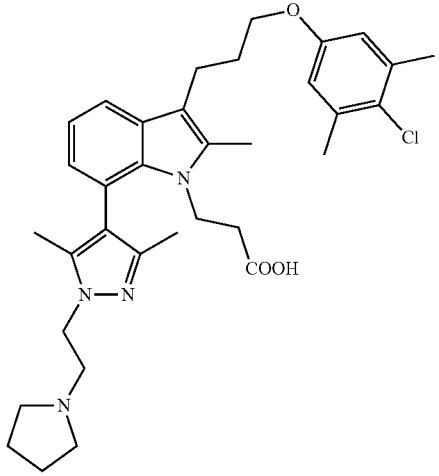
81
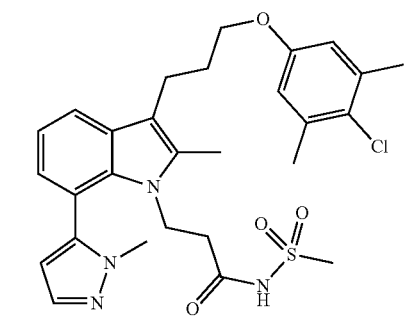
82
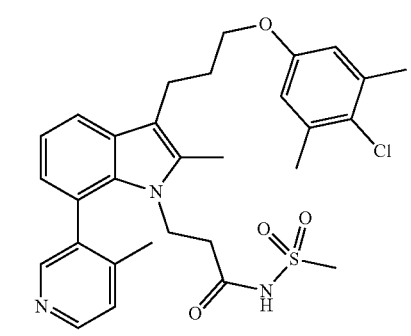
83
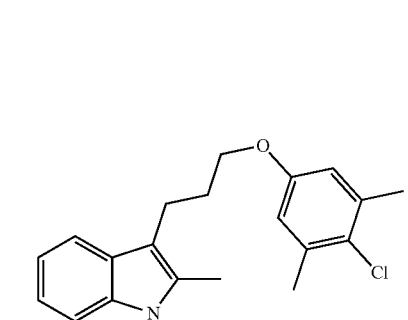

1985
-continued
84
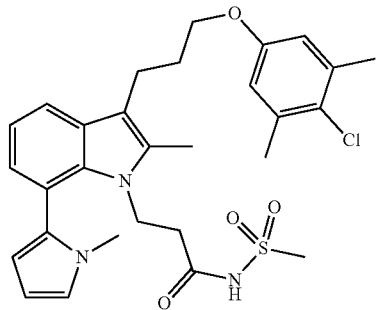
85
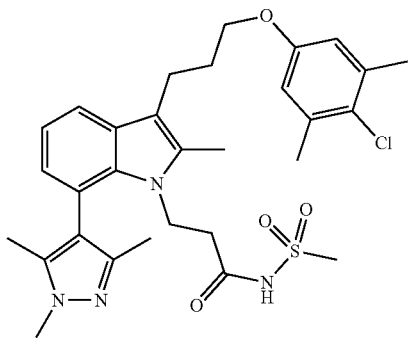
86
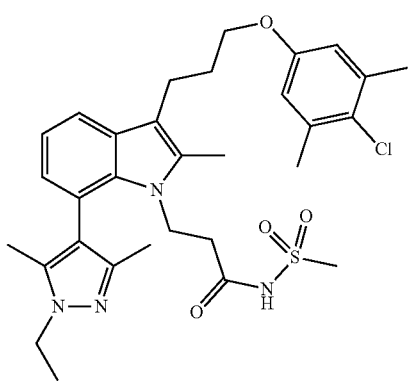
87
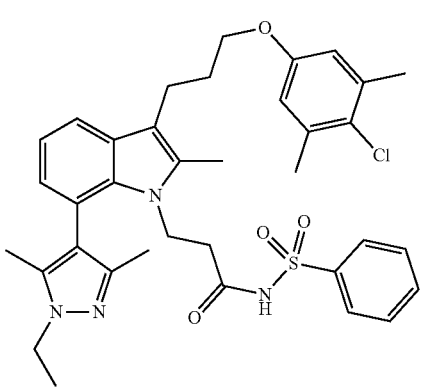
1986
-continued
88
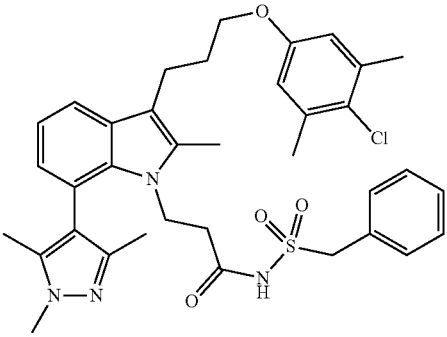
89
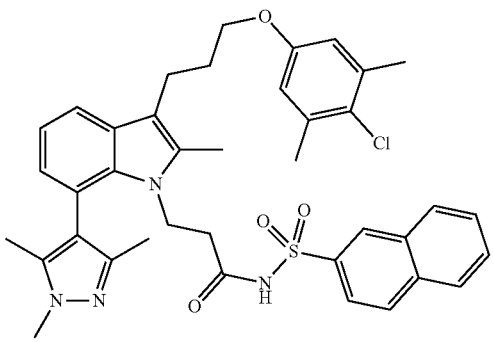
90
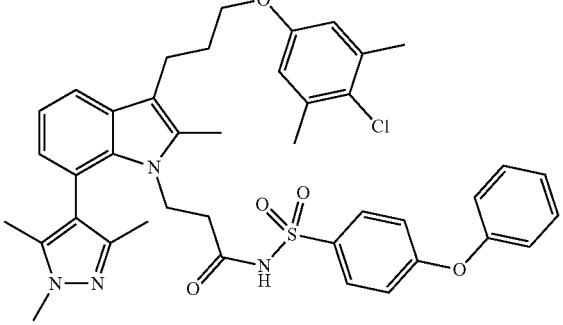
91
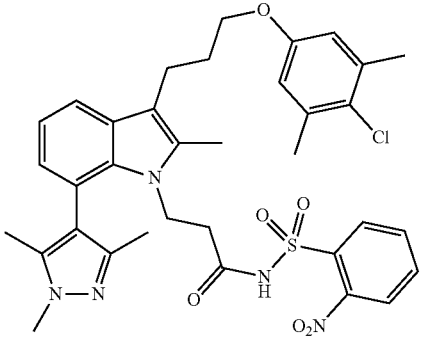

1987
-continued
92
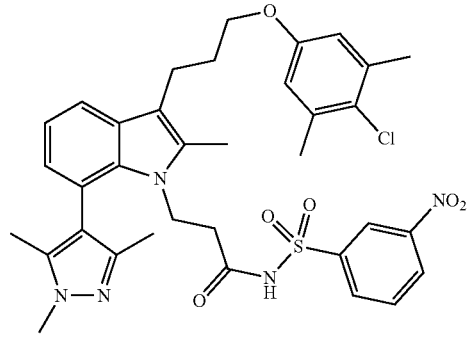
93
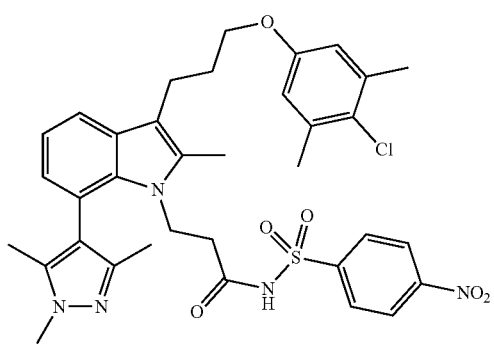
94
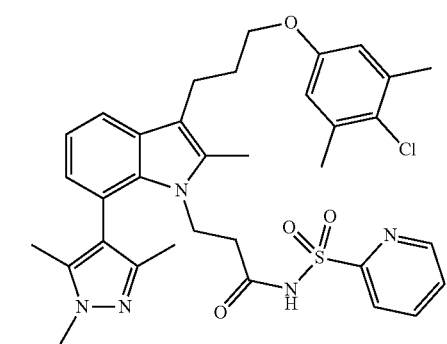
95
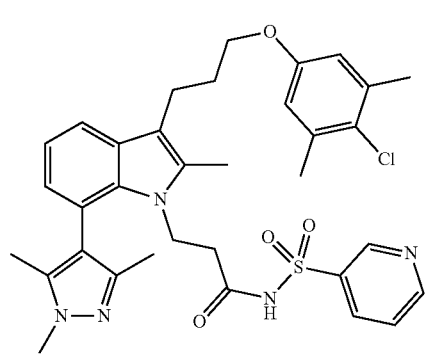
1988
-continued
96
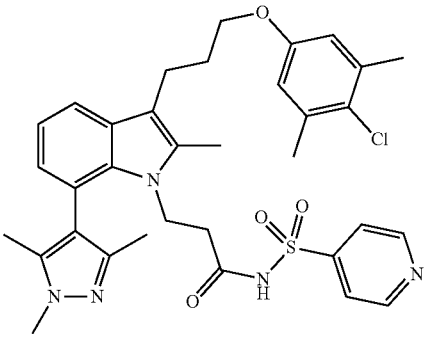
97
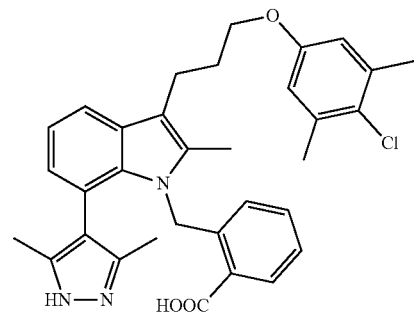
98
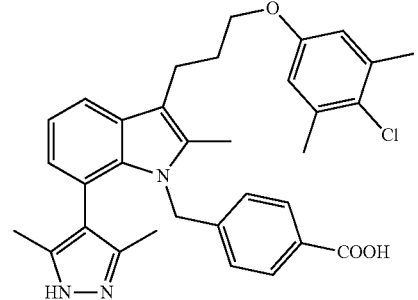
99
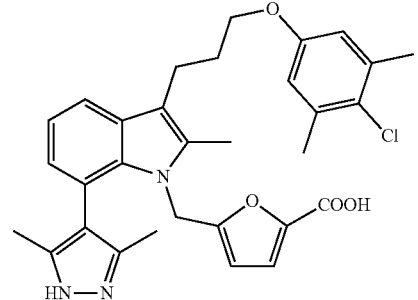
100
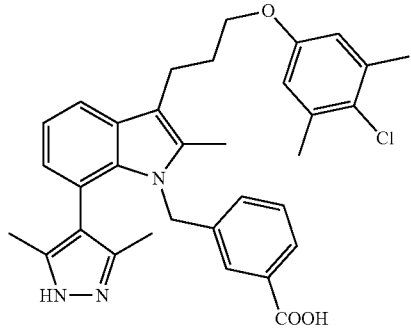

1989
-continued
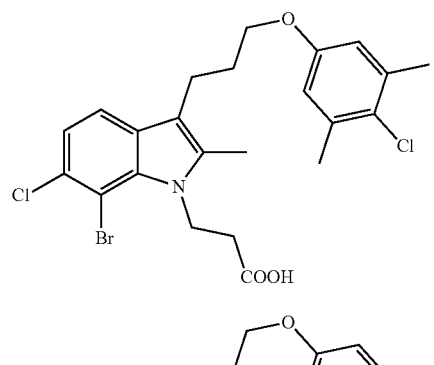
101
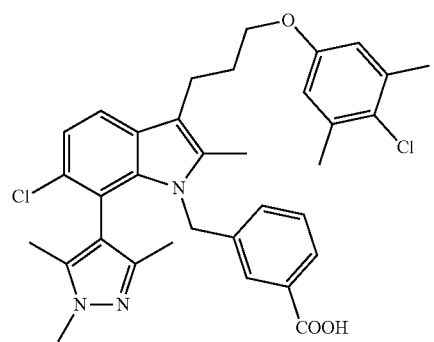
102
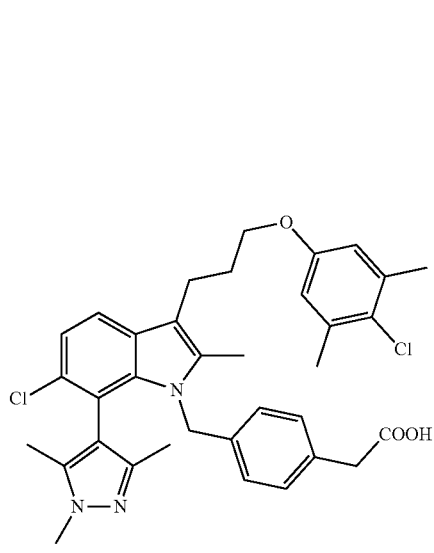
103
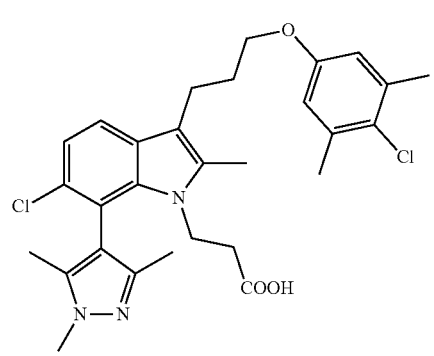
104
1990
-continued
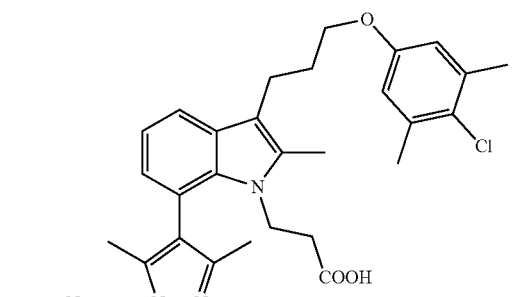
105
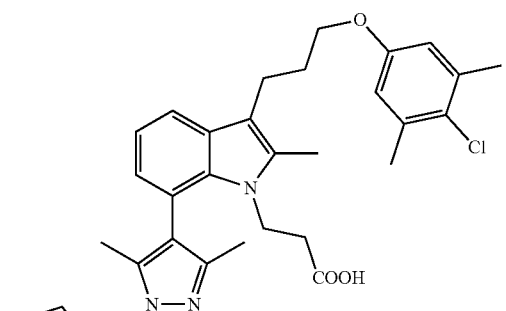
106
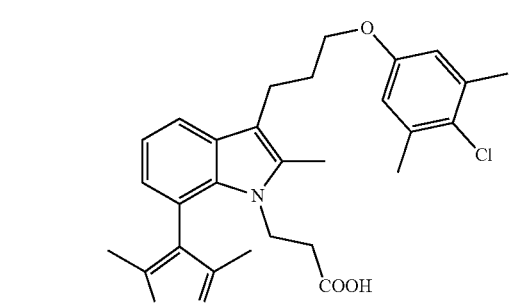
107
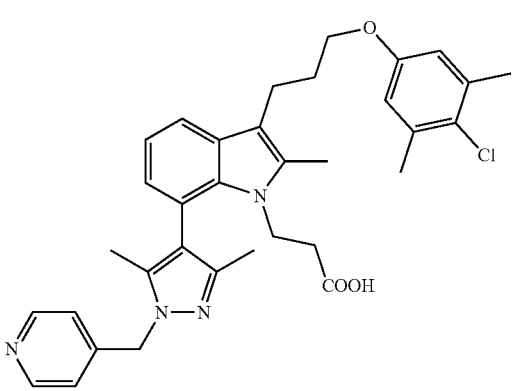
108

1991 -continued
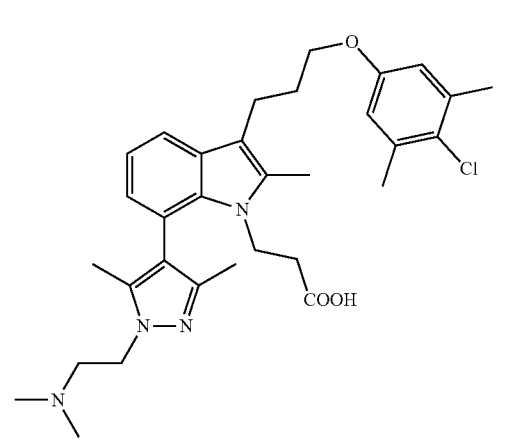
109
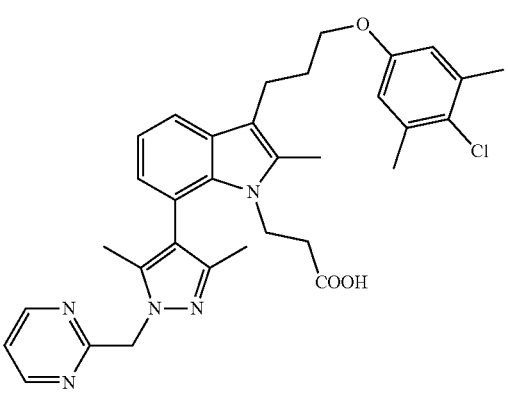
110
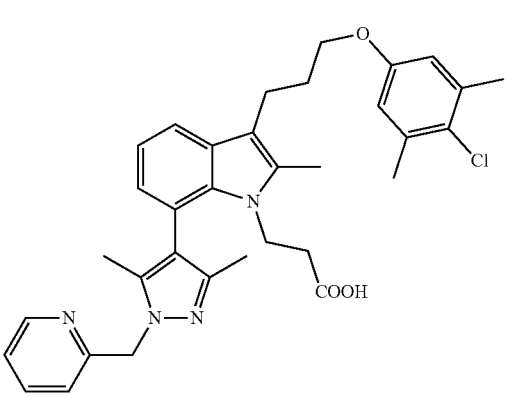
111
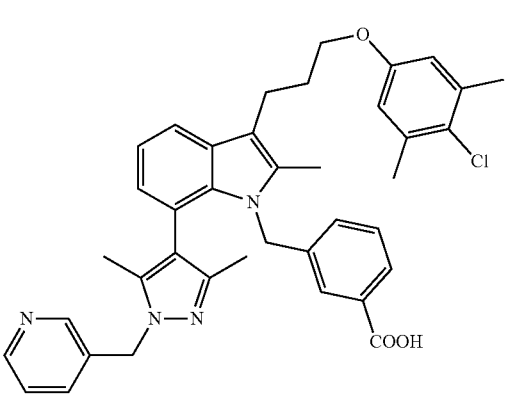
112
1992 -continued
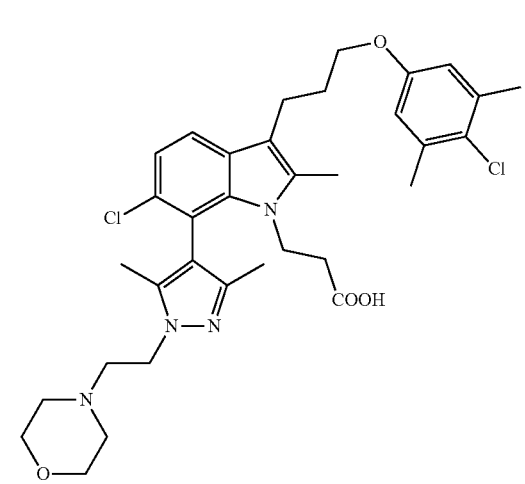
113
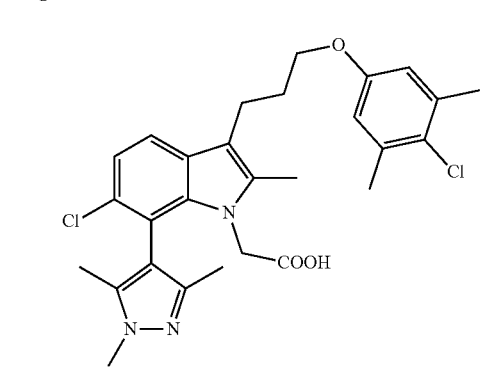
114
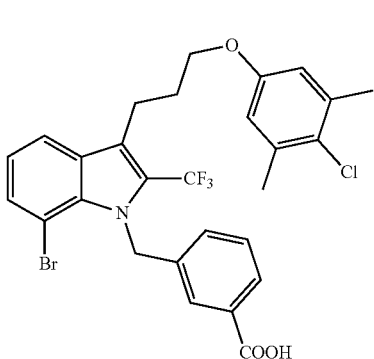
115
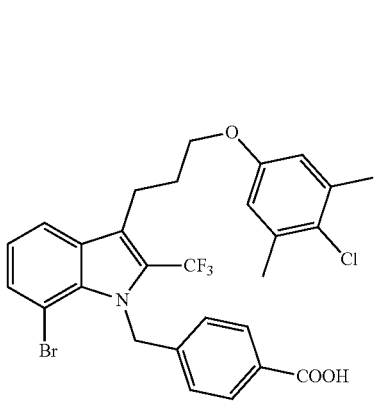
116

1993 -continued
117
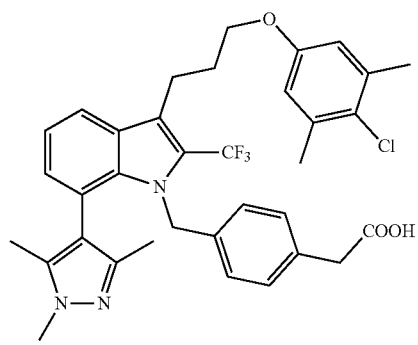
118
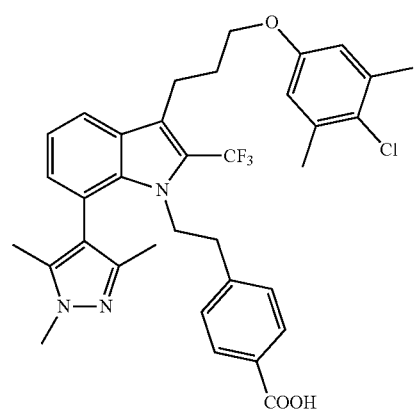
119
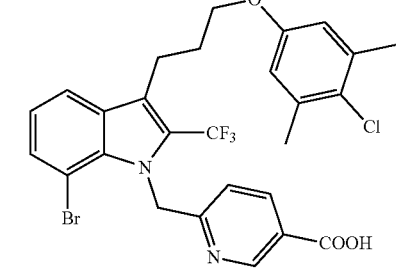
120
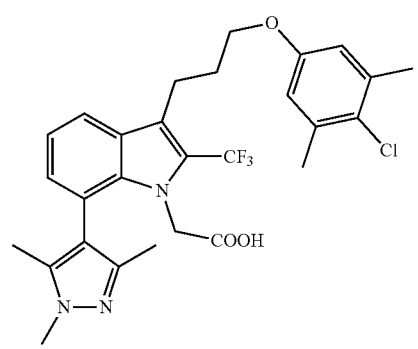
1994 -continued
121
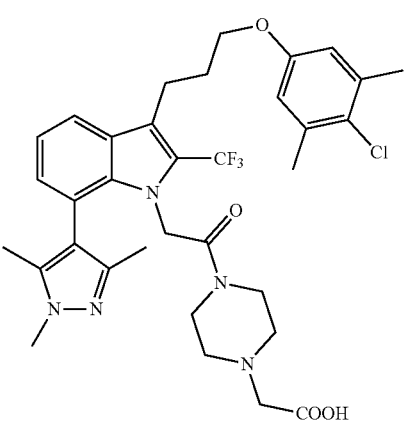
122
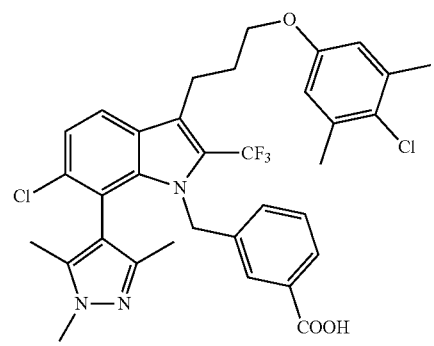
123
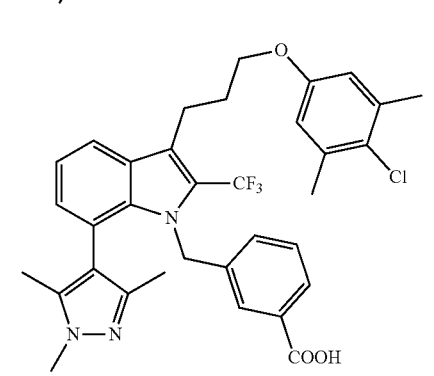
124
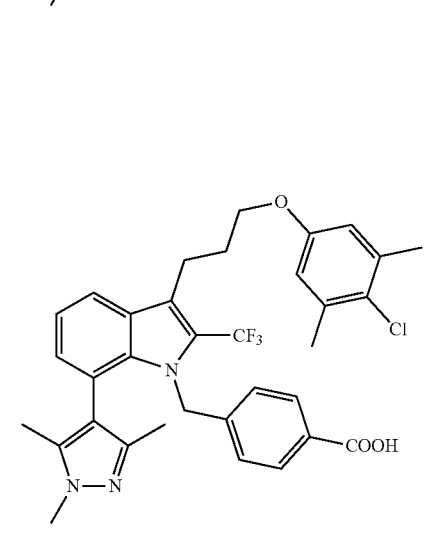

1995
-continued
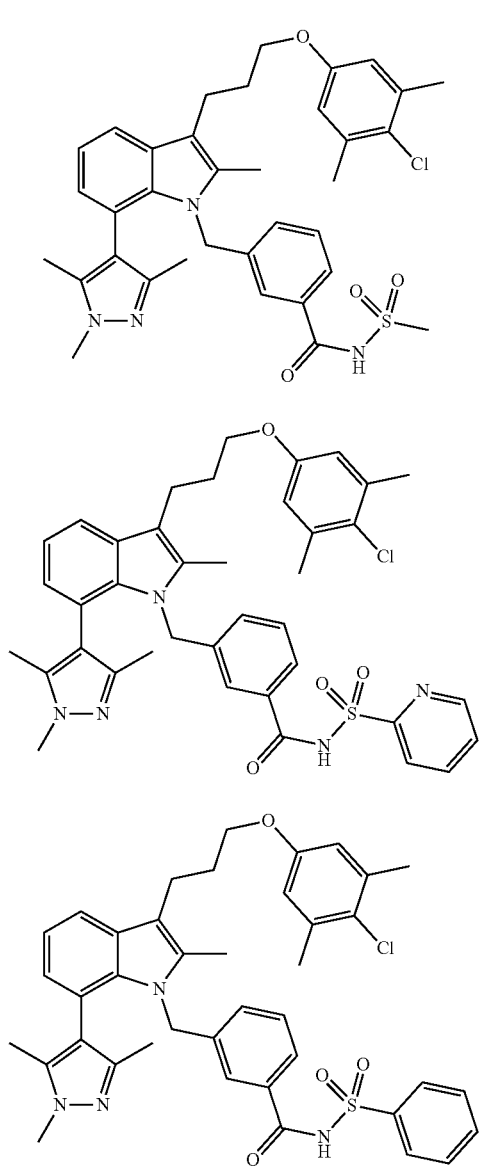
1996
-continued
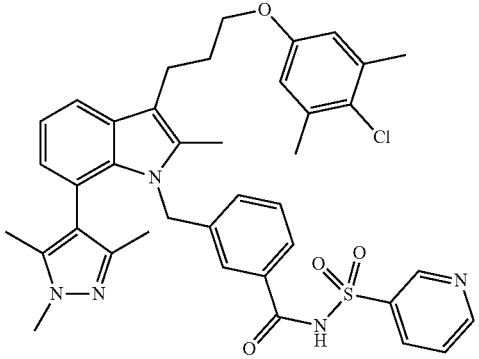
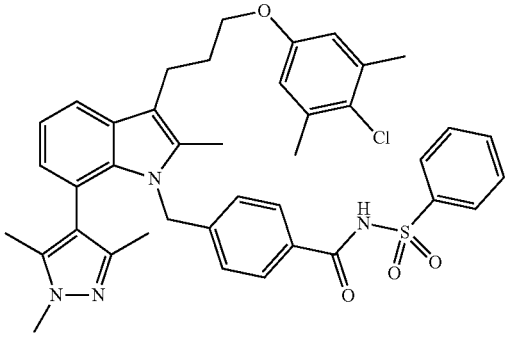
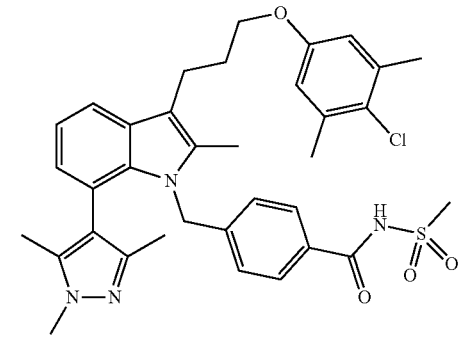

1997
-continued
132
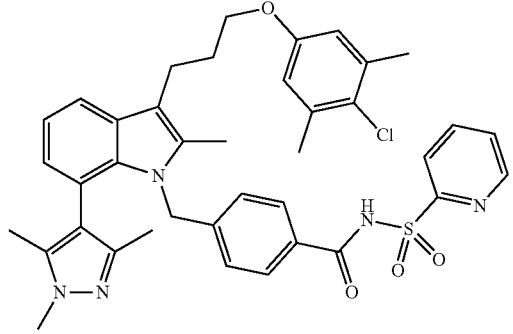
133
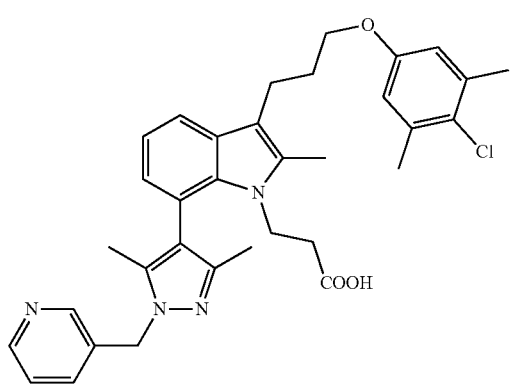
1998
-continued
134
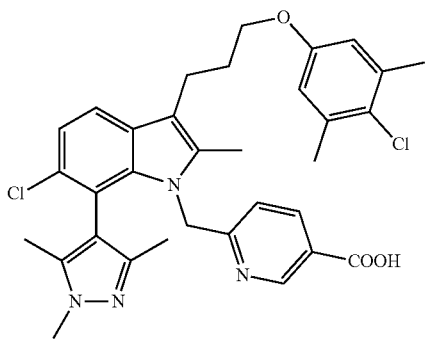
135
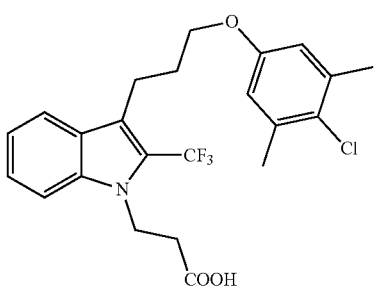
In some embodiments, the compound is selected from the group consisting of:
| Name | Structure |
|---|---|
| (R)-4-(4-benzhydryl-piperazin-1-yl)-N-(4-(4-(dimethylamino)-1-(phenylthio)butan-2-ylamino)-3-nitrophenylsulfonyl)benzamide | |
| (R)-4-(4-(bis(4-fluorophenyl)methyl)piperazin-1-yl)N-(4-(4-(dimethyl-amino)-1-(phenylthio)butan-2-ylamino)-3-nitrophenylsulfonyl)benzamide | 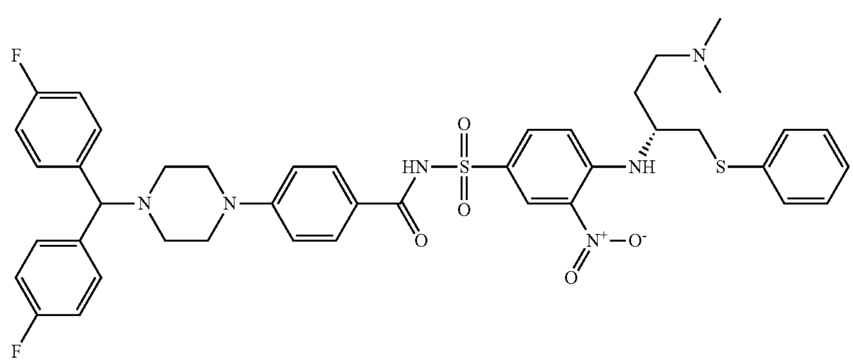 [SMILES: CN(C)CC[C@H](CSc1ccccc1)Nc1ccc(S(=O)(=O)NC(=O)c2ccc(N3CCN(C(c4ccc(F)cc4)c4ccc(F)cc4)CC3)cc2)cc1[N+](=O)[O-]] |

-continued

| Name | Structure |
|---|---|
| (R)-2-bromo-N-(1-(4-(4-(4-(dimethylamino)-1-(phenylthio)butan-2-ylamino)-3-nitrophenylsulfonylcarbamoyl)phenyl)piperidin-4-yl)benzamide | 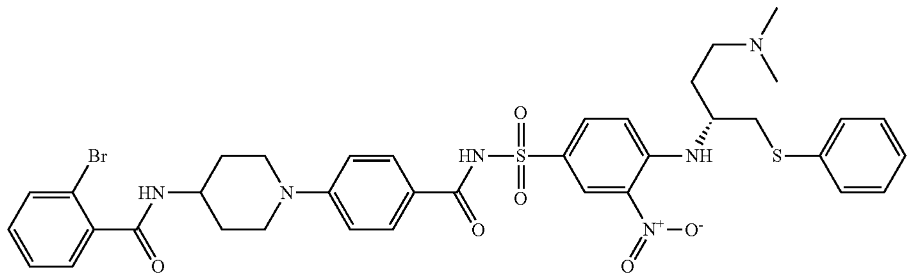 [SMILES: CN(C)CC[C@H](CSc1ccccc1)Nc1ccc(S(=O)(=O)NC(=O)c2ccc(N3CCC(NC(=O)c4ccccc4Br)CC3)cc2)cc1[N+](=O)[O-]] |
| N-benzyl-N-(1-(4-(4-(4-(dimethylamino)-1-(phenylthio)butan-2-ylamino)-3-nitrophenylsulfonylcarbamoyl)phenyl)piperidin-4-yl)benzamide | 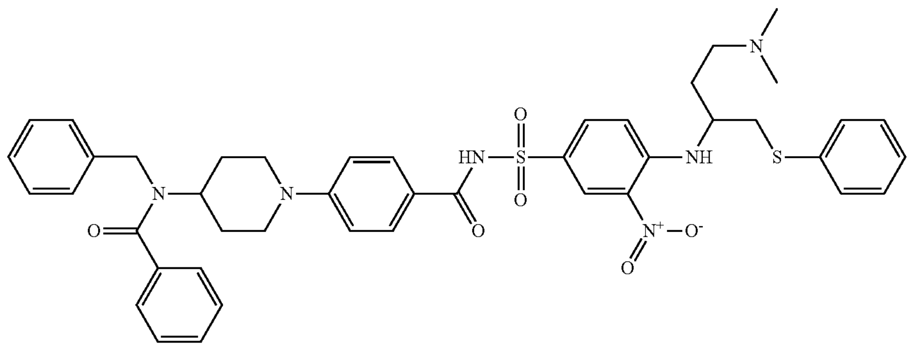 [SMILES: CN(C)CCC(CSc1ccccc1)Nc1ccc(S(=O)(=O)NC(=O)c2ccc(N3CCC(N(Cc4ccccc4)C(=O)c4ccccc4)CC3)cc2)cc1[N+](=O)[O-]] |
| 4-(4-(benzyl(methyl)amino)piperidin-1-yl)-N-(4-(4-(dimethylamino)-1-(phenylthio)butan-2-ylamino)-3-nitrophenylsulfonyl)benzamide | 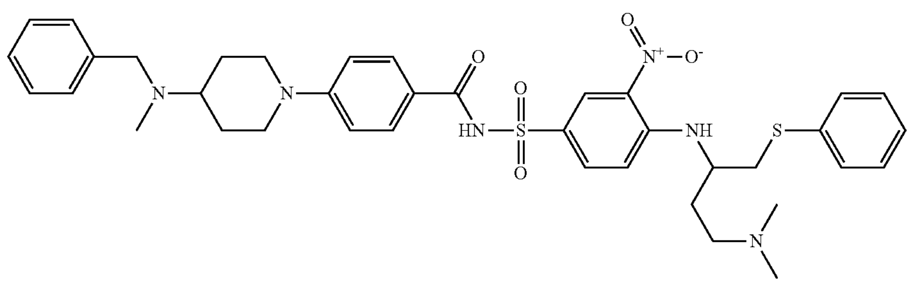 [SMILES: CN(C)CCC(CSc1ccccc1)Nc1ccc(S(=O)(=O)NC(=O)c2ccc(N3CCC(N(C)Cc4ccccc4)CC3)cc2)cc1[N+](=O)[O-]] |
| 4-(4-(N-benzylacetamido)piperidin-1-yl)-N-(4-(4-(dimethylamino)-1-(phenylthio)butan-2-ylamino)-3-nitrophenylsulfonyl)benzamide | 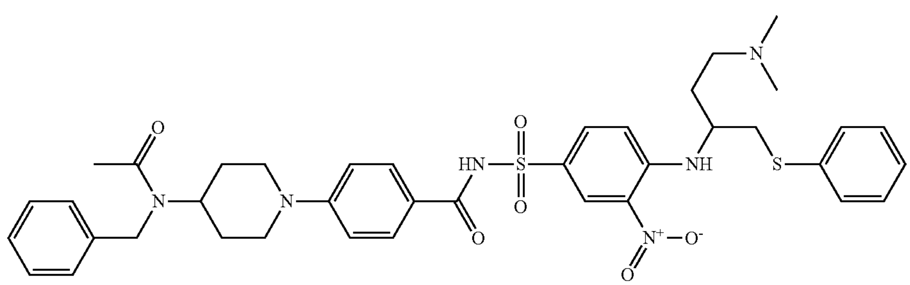 [SMILES: CC(=O)N(Cc1ccccc1)C1CCN(c2ccc(C(=O)NS(=O)(=O)c3ccc(NC(CCN(C)C)CSc4ccccc4)c([N+](=O)[O-])c3)cc2)CC1] |
| 4-(4-(benzylamino)piperidin-1-yl)-N-(4-(4-(dimethylamino)-1-(phenylthio)butan-2-ylamino)-3-nitrophenylsulfonyl)benzamide | 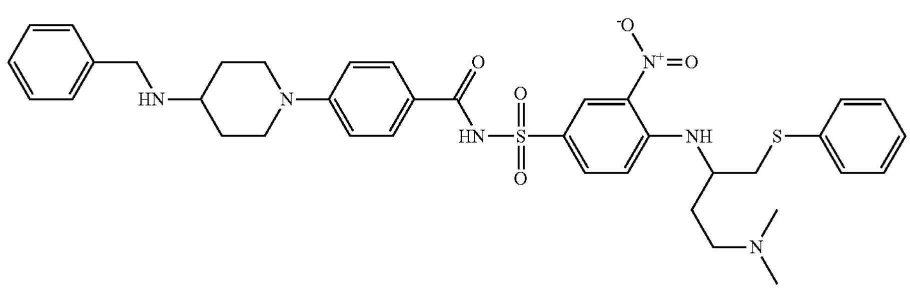 |

| Name | Structure |
|---|---|
| (S)-4-(4-((4'-chloro-biphenyl-2-yl)methylamino)piperidin-1-yl)-N-(4-(4-(dimethylamino)-1-(phenylthio)butan-2-ylamino)-3-nitrophenylsulfonyl)benzamide | 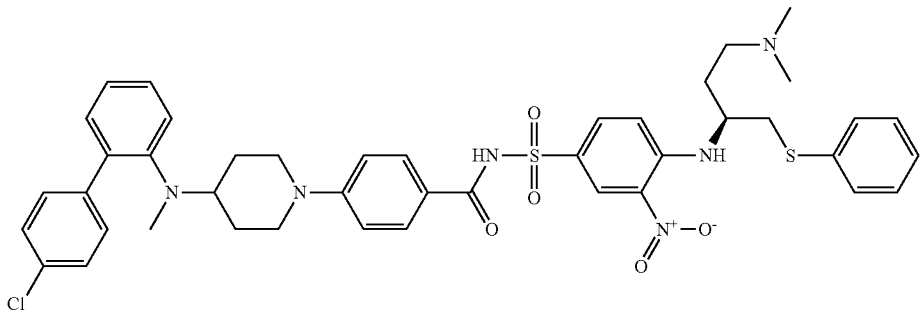 [SMILES: CN(C)CC[C@@H](CSc1ccccc1)Nc1ccc(S(=O)(=O)NC(=O)c2ccc(N3CCC(N(C)c4ccccc4-c4ccc(Cl)cc4)CC3)cc2)cc1[N+](=O)[O-]] |
| (S)-4-(4-(((4'-chloro-biphenyl-2-yl)methyl)(methyl)amino)piperidin-1-yl)-N-(4-(4-(dimethylamino)-1-(phenylthio)butan-2-ylamino)-3-nitrophenylsulfonyl)benzamide | 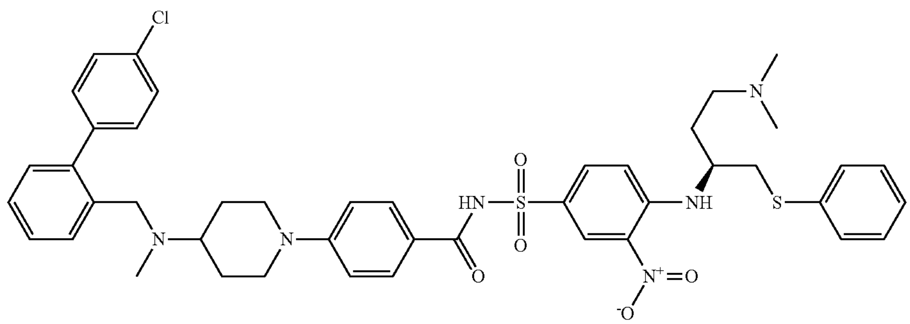 |
| (S)-4'-chloro-N-(1-(4-(4-(4-(dimethylamino)-1-(phenylthio)butan-2-ylamino)-3-nitrophenyl-sulfonylcarbamoyl)phenyl)piperidin-4-yl)biphenyl-2-carboxamide | 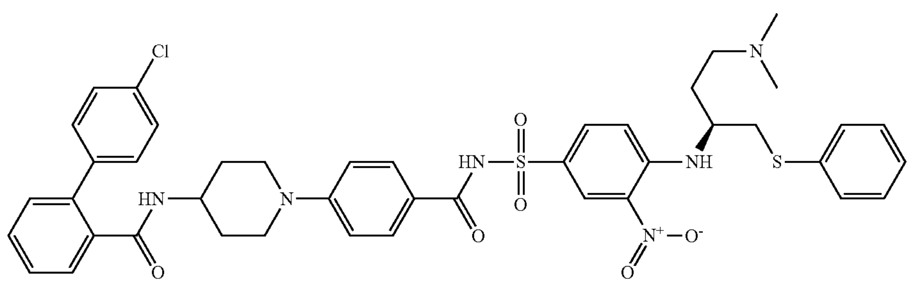 [SMILES: CN(C)CC[C@@H](CSc1ccccc1)Nc1ccc(S(=O)(=O)NC(=O)c2ccc(N3CCC(NC(=O)c4ccccc4-c4ccc(Cl)cc4)CC3)cc2)cc1[N+](=O)[O-]] |

In some embodiments, the compound is selected from the group consisting of:

N,N-Dibutyl-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide;

N,N-dibutyl-4-chloro-1-(4-(5-chloronaphthalen-2-ylsulfonylcarbamoyl)-2-(1,2,3,4-tetrahydroisoquinoline-2-carbonyl)phenyl)-5-methyl-1H-pyrazole-3-carboxamide;

N,N-dibutyl-4-chloro-1-(4-(6-(dimethylamino)naphthalen-2-ylsulfonylcarbamoyl)-2-(1,2,3,4-tetrahydroisoquinoline-2-carbonyl)phenyl)-5-methyl-1H-pyrazole-3-carboxamide;

N,N-dibutyl-4-chloro-1-(4-(5-(dimethylamino)naphthalen-1-ylsulfonylcarbamoyl)-2-(1,2,3,4-tetrahydroisoquinoline-2-carbonyl)phenyl)-5-methyl-1H-pyrazole-3-carboxamide;

N,N-dibutyl-4-chloro-1-(4-(8-chloronaphthalen-2-ylsulfonylcarbamoyl)-2-(1,2,3,4-tetrahydroisoquinoline-2-carbonyl)phenyl)-5-methyl-1H-pyrazole-3-carboxamide;

N,N-dibutyl-4-chloro-1-(4-(6-chloronaphthalen-2-ylsulfonylcarbamoyl)-2-(1,2,3,4-tetrahydroisoquinoline-2-carbonyl)phenyl)-5-methyl-1H-pyrazole-3-carboxamide;

N,N-dibutyl-4-chloro-1-(4-(8-iodonaphthalen-2-ylsulfonylcarbamoyl)-2-(1,2,3,4-tetrahydroisoquinoline-2-carbonyl)phenyl)-5-methyl-1H-pyrazole-3-carboxamide;

N,N-dibutyl-4-chloro-1-(4-(8-cyanonaphthalen-2-ylsulfonylcarbamoyl)-2-(1,2,3,4-tetrahydroisoquinoline-2-carbonyl)phenyl)-5-methyl-1H-pyrazole-3-carboxamide;

ethyl 7-(N-(4-(4-chloro-3-(dibutylcarbamoyl)-5-methyl-1H-pyrazol-1-yl)-3-(1,2,3,4-tetrahydroisoquinoline-2-carbonyl)benzoyl)sulfamoyl)-1-naphthoate;

N,N-dibutyl-4-chloro-1-(4-(7-chloronaphthalen-2-ylsulfonylcarbamoyl)-2-(1,2,3,4-tetrahydroisoquinoline-2-carbonyl)phenyl)-5-methyl-1H-pyrazole-3-carboxamide (10);

N,N-dibutyl-4-chloro-1-(4-(7-iodonaphthalen-2-ylsulfonylcarbamoyl)-2-(1,2,3,4-tetrahydroisoquinoline-2-carbonyl)phenyl)-5-methyl-1H-pyrazole-3-carboxamide;

N,N-dibutyl-4-chloro-5-methyl-1-(4-(5-nitronaphthalen-1-ylsulfonylcarbamoyl)-2-(1,2,3,4-tetrahydroisoquinoline-2-carbonyl)phenyl)-1H-pyrazole-3-carboxamide;

N,N-dibutyl-4-chloro-5-methyl-1-(4-(4-(5-nitronaphthalen-2-ylsulfonylcarbamoyl)-2-(1,2,3,4-tetrahydroisoquinoline-2-carbonyl)phenyl)-1H-pyrazole-3-carboxamide;

N,N-dibutyl-4-chloro-1-(4-(6-chloronaphthalen-2-ylsulfonylcarbamoyl)-2-(1,2,3,4-tetrahydroisoquinoline-2-carbonyl)phenyl)-5-methyl-1H-pyrazole-3-carboxamide;

N,N-dibutyl-4-chloro-1-(4-(7-cyanonaphthalen-2-ylsulfonylcarbamoyl)-2-(1,2,3,4-tetrahydroisoquinoline-2-carbonyl)phenyl)-5-methyl-1H-pyrazole-3-carboxamide;

ethyl 7-(N-(4-(4-chloro-3-(dibutylcarbamoyl)-5-methyl-1H-pyrazol-1-yl)-3-(1,2,3,4-tetrahydroisoquinoline-2-carbonyl)benzoyl)sulfamoyl)-2-naphthoate;

ethyl 7-(N-(4-(4-chloro-3-(dibutylcarbamoyl)-5-methyl-1H-pyrazol-1-yl)-3-(1,2,3,4-tetrahydroisoquinoline-2-carbonyl)benzoyl)sulfamoyl)-2-naphthoate;

1-(4-(7-(benzyloxy)naphthalen-2-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide;

N,N-dibutyl-4-chloro-1-(4-(8-(3,4-dichlorobenzamido)naphthalen-2-ylsulfonylcarbamoyl)-2-(1,2,3,4-tetrahydroisoquinoline-2-carbonyl)phenyl)-5-methyl-1H-pyrazole-3-carboxamide;

N,N-dibutyl-4-chloro-5-methyl-1-(4-(7-(4-(methylsulfonyl)benzyloxy)-naphthalen-2-ylsulfonylcarbamoyl)-2-(1,2,3,4-tetrahydroisoquinoline-2-carbonyl)phenyl)-1H-pyrazole-3-carboxamide;

N,N-dibutyl-4-chloro-1-(4-(8-(3,4-dichlorobenzyloxy)naphthalen-2-ylsulfonylcarbamoyl)-2-(1,2,3,4-tetrahydroisoquinoline-2-carbonyl)phenyl)-5-methyl-1H-pyrazole-3-carboxamide;

N,N-dibutyl-4-chloro-1-(4-(7-(3,4-dichlorobenzyloxy)naphthalen-2-ylsulfonylcarbamoyl)-2-(1,2,3,4-tetrahydroisoquinoline-2-carbonyl)phenyl)-5-methyl-1H-pyrazole-3-carboxamide;

N,N-dibutyl-4-chloro-5-methyl-1-(4-(7-((tetrahydrofuran-2-yl)methoxy) naphthalen-2-ylsulfonylcarbamoyl)-2-(1,2,3,4-tetrahydroisoquinoline-2-carbonyl)phenyl)-1H-pyrazole-3-carboxamide;

N,N-dibutyl-4-chloro-1-(4-(7-isopropoxynaphthalene-2-ylsulfonylcarbamoyl)-2-(1,2,3,4-tetrahydroisoquinoline-2-carbonyl)phenyl)-5-methyl-1H-pyrazole-3-carboxamide;

N,N-dibutyl-4-chloro-5-methyl-1-(4-(7-(2-phenoxyethoxy)naphthalen-2-ylsulfonylcarbamoyl)-2-(1,2,3,4-tetrahydroisoquinoline-2-carbonyl)phenyl)-1H-pyrazole-3-carboxamide;

methyl 4-((7-(N-(4-(4-chloro-3-(dibutylcarbamoyl)-5-methyl-1H-pyrazol-1-yl)-3-(1,2,3,4-tetrahydroisoquinoline-2-carbonyl)benzoyl)sulfamoyl)naphthalen-1-yloxy)methyl)benzoate;

N,N-dibutyl-4-chloro-5-methyl-1-(4-(8-(2-morpholinoethoxy)naphthalen-2-ylsulfonylcarbamoyl)-2-(1,2,3,4-tetrahydroisoquinoline-2-carbonyl)phenyl)-1H-pyrazole-3-carboxamide;

N,N-dibutyl-4-chloro-1-(4-(7-(2-methoxyethoxy)naphthalen-2-ylsulfonylcarbamoyl)-2-(1,2,3,4-tetrahydroisoquinoline-2-carbonyl)phenyl)-5-methyl-1H-pyrazole-3-carboxamide;

N,N-dibutyl-4-chloro-1-(4-(7-methoxynaphthalen-2-ylsulfonylcarbamoyl)-2-(1,2,3,4-tetrahydroisoquinoline-2-carbonyl)phenyl)-5-methyl-1H-pyrazole-3-carboxamide;

N,N-dibutyl-4-chloro-1-(4-(7-(2-ethoxyethoxy) naphthalen-2-ylsulfonylcarbamoyl)-2-(1,2,3,4-tetrahydroisoquinoline-2-carbonyl)phenyl)-5-methyl-1H-pyrazole-3-carboxamide;

1-(4-(8-bromo-5-(dimethylamino)naphthalen-2-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide;

N,N-dibutyl-4-chloro-5-methyl-1-(4-(8-(3-morpholinopropoxy)naphthalen-2-ylsulfonylcarbamoyl)-2-(1,2,3,4-tetrahydroisoquinoline-2-carbonyl)phenyl)-1H-pyrazole-3-carboxamide;

N,N-dibutyl-4-chloro-5-methyl-1-(4-(7-(2-morpholinoethoxy)naphthalen-2-ylsulfonylcarbamoyl)-2-(1,2,3,4-tetrahydroisoquinoline-2-carbonyl)phenyl)-1H-pyrazole-3-carboxamide;

N,N-dibutyl-4-chloro-5-methyl-1-(4-(7-(3-morpholinopropoxy)naphthalen-2-ylsulfonylcarbamoyl)-2-(1,2,3,4-tetrahydroisoquinoline-2-carbonyl)phenyl)-1H-pyrazole-3-carboxamide;

N,N-dibutyl-4-chloro-5-methyl-1-(4-(7-(3-(4-methylpiperazin-1-yl)propoxy)naphthalen-2-ylsulfonylcarbamoyl)-2-(1,2,3,4-tetrahydroisoquinoline-2-carbonyl)phenyl)-1H-pyrazole-3-carboxamide;

N,N-dibutyl-4-chloro-5-methyl-1-(4-(7-((1-methyl-1H-imidazol-2-yl)methoxy)naphthalen-2-ylsulfonylcarbamoyl)-2-(1,2,3,4-tetrahydroisoquinoline-2-carbonyl)phenyl)-1H-pyrazole-3-carboxamide;

N,N-dibutyl-4-chloro-1-(4-(7-(1-(dimethylamino)propan-2-yloxy)naphthalen-2-ylsulfonylcarbamoyl)-2-(1,2,3,4-tetrahydroisoquinoline-2-carbonyl)phenyl)-5-methyl-1H-pyrazole-3-carboxamide;

N,N-dibutyl-4-chloro-5-methyl-1-(4-((7-(2-(1-methylpyrrolidin-2-yl)ethoxy)naphthalene-2-sulfonamido)methyl)-2-(1,2,3,4-tetrahydroisoquinoline-2-carbonyl)phenyl)-1H-pyrazole-3-carboxamide;

N,N-dibutyl-4-chloro-1-(4-(7-(3-(dimethylamino)propoxy)-naphthalen-2-ylsulfonylcarbamoyl)-2-(1,2,3,4-tetrahydroisoquinoline-2-carbonyl)phenyl)-5-methyl-1H-pyrazole-3-carboxamide;

N,N-dibutyl-4-chloro-5-methyl-1-(4-(7-(3-(pyrrolidin-1-yl)propoxy)naphthalen-2-ylsulfonylcarbamoyl)-2-(1,2,3,4-tetrahydroisoquinoline-2-carbonyl)phenyl)-1H-pyrazole-3-carboxamide;

N,N-dibutyl-4-chloro-5-methyl-1-(4-(7-(3-(piperidin-1-yl)propoxy)naphthalen-2-ylsulfonylcarbamoyl)-2-(1,2,3,4-tetrahydroisoquinoline-2-carbonyl)phenyl)-1H-pyrazole-3-carboxamide;

N,N-Dibutyl-4-chloro-5-methyl-1-(4-(7-(3-(pyridin-4-yl)propoxy)naphthalen-2-ylsulfonylcarbamoyl)-2-(1,2,3,4-tetrahydroisoquinoline-2-carbonyl)phenyl)-1H-pyrazole-3-carboxamide;

1-(4-(8-bromo-5-chloronaphthalen-2-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide;

N,N-dibutyl-4-chloro-1-(4-(5,8-dichloronaphthalen-2-ylsulfonylcarbamoyl)-2-(1,2,3,4-tetrahydroisoquinoline-2-carbonyl)phenyl)-5-methyl-1H-pyrazole-3-carboxamide (44);

7-(N-(4-(4-Chloro-3-(dibutylcarbamoyl)-5-methyl-1H-pyrazol-1-yl)-3-(1,2,3,4-tetrahydroisoquinoline-2-carbonyl)benzoyl)sulfamoyl)-1-naphthoic acid;

N,N-Dibutyl-4-chloro-5-methyl-1-(4-(7-(4-methylpiperazine-1-carbonyl)naphthalen-2-ylsulfonylcarbamoyl)-2-(1,2,3,4-tetrahydroisoquinoline-2-carbonyl)phenyl)-1H-pyrazole-3-carboxamide;

N,N-Dibutyl-4-chloro-5-methyl-1-(4-(7-(morpholine-4-carbonyl)naphthalen-2-ylsulfonylcarbamoyl)-2-(1,2,3,4-tetrahydroisoquinoline-2-carbonyl)phenyl)-1H-pyrazole-3-carboxamide;

N,N-Dibutyl-4-chloro-1-(4-(7-(dimethylcarbamoyl)naphthalen-2-ylsulfonylcarbamoyl)-2-(1,2,3,4-tetrahydroisoquinoline-2-carbonyl)phenyl)-5-methyl-1H-pyrazole-3-carboxamide;

4-((7-(N-(4-(4-Chloro-3-(dibutylcarbamoyl)-5-methyl-1H-pyrazol-1-yl)-3-(1,2,3,4-tetrahydroisoquinoline-2-carbonyl)benzoyl)sulfamoyl)naphthalen-1-yloxy)methyl)benzoic acid;

N,N-Dibutyl-4-chloro-1-(4-(7-(2-hydroxyethoxy)naphthalen-2-ylsulfonylcarbamoyl)-2-(1,2,3,4-tetrahydroisoquinoline-2-carbonyl)phenyl)-5-methyl-1H-pyrazole-3-carboxamide;

N,N-Dibutyl-4-chloro-1-(4-(7-hydroxynaphthalen-2-ylsulfonylcarbamoyl)-2-(1,2,3,4-tetrahydroisoquinoline-2-carbonyl)phenyl)-5-methyl-1H-pyrazole-3-carboxamide;

N,N-Dibutyl-4-chloro-1-(4-(indolin-5-ylsulfonylcarbamoyl)-2-(1,2,3,4-tetrahydroisoquinoline-2-carbonyl)phenyl)-5-methyl-1H-pyrazole-3-carboxamide;

N,N-dibutyl-4-chloro-1-(4-(1-ethylindolin-5-ylsulfonylcarbamoyl)-2-(1,2,3,4-tetrahydroisoquinoline-2-carbonyl)phenyl)-5-methyl-1H-pyrazole-3-carboxamide;

1-(4-(1H-indol-5-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide;

N,N-dibutyl-4-chloro-1-(4-(1-(cyclohexanecarbonyl)indolin-5-ylsulfonylcarbamoyl)-2-(1,2,3,4-tetrahydroisoquinoline-2-carbonyl)phenyl)-5-methyl-1H-pyrazole-3-carboxamide;

N,N-dibutyl-4-chloro-1-(4-(1-ethyl-1H-indol-5-ylsulfonylcarbamoyl)-2-(1,2,3,4-tetrahydroisoquinoline-2-carbonyl)phenyl)-5-methyl-1H-pyrazole-3-carboxamide;

N,N-dibutyl-4-chloro-1-(4-(1-(cyclohexylmethyl)indolin-5-ylsulfonylcarbamoyl)-2-(1,2,3,4-tetrahydroisoquinoline-2-carbonyl)phenyl)-5-methyl-1H-pyrazole-3-carboxamide;

N,N-dibutyl-4-chloro-1-(4-(1-(3,4-dichlorobenzoyl)indolin-5-ylsulfonylcarbamoyl)-2-(1,2,3,4-tetrahydroisoquinoline-2-carbonyl)phenyl)-5-methyl-1H-pyrazole-3-carboxamide;

N,N-dibutyl-4-chloro-1-(4-(1-(3,4-dichlorobenzyl)indolin-5-ylsulfonylcarbamoyl)-2-(1,2,3,4-tetrahydroisoquinoline-2-carbonyl)phenyl)-5-methyl-1H-pyrazole-3-carboxamide;

1-(4-(1-acetylindolin-6-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide;

1-(4-(1-benzylindolin-5-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide;

N,N-dibutyl-4-chloro-1-(4-(1-(3,4-difluorobenzyl) indolin-5-ylsulfonylcarbamoyl)-2-(1,2,3,4-tetrahydroisoquinoline-2-carbonyl)phenyl)-5-methyl-1H-pyrazole-3-carboxamide;

N,N-dibutyl-4-chloro-1-(4-(1-ethylindolin-6-ylsulfonylcarbamoyl)-2-(1,2,3,4-tetrahydroisoquinoline-2-carbonyl)phenyl)-5-methyl-1H-pyrazole-3-carboxamide;

N,N-dibutyl-4-chloro-1-(4-(1-(2-(3,4-dichlorophenyl)acetyl)indolin-5-ylsulfonylcarbamoyl)-2-(1,2,3,4-tetrahydroisoquinoline-2-carbonyl)phenyl)-5-methyl-1H-pyrazole-3-carboxamide;

N,N-dibutyl-4-chloro-1-(4-(1-(3,4-dichlorophenethyl)indolin-5-ylsulfonylcarbamoyl)-2-(1,2,3,4-tetrahydroisoquinoline-2-carbonyl)phenyl)-5-methyl-1H-pyrazole-3-carboxamide;

N,N-dibutyl-4-chloro-5-methyl-1-(4-(1-(2-(phenylthio)acetyl)indolin-5-ylsulfonylcarbamoyl)-2-(1,2,3,4-tetrahydroisoquinoline-2-carbonyl)phenyl)-1H-pyrazole-3-carboxamide;

N,N-dibutyl-4-chloro-5-methyl-1-(4-(1-(2-(phenylthio)ethyl)indolin-5-ylsulfonylcarbamoyl)-2-(1,2,3,4-tetrahydroisoquinoline-2-carbonyl)phenyl)-1H-pyrazole-3-carboxamide;

N,N-dibutyl-4-chloro-1-(4-(1-(3,4-dichlorobenzyl)-1H-indol-5-ylsulfonylcarbamoyl)-2-(1,2,3,4-tetrahydroisoquinoline-2-carbonyl)phenyl)-5-methyl-1H-pyrazole-3-carboxamide;

N,N-dibutyl-4-chloro-1-(4-(1-((6-chloropyridin-2-yl)methyl)indolin-5-ylsulfonylcarbamoyl)-2-(1,2,3,4-tetrahydroisoquinoline-2-carbonyl)phenyl)-5-methyl-1H-pyrazole-3-carboxamide;

N,N-dibutyl-4-chloro-5-methyl-1-(4-(1-((1-methyl-1H-indol-6-yl)methyl) indolin-5-ylsulfonylcarbamoyl)-2-(1,2,3,4-tetrahydroisoquinoline-2-carbonyl)phenyl)-1H-pyrazole-3-carboxamide;

1-(4-(5-bromo-1-ethylindolin-6-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide;

1-(4-(5-bromo-1-(3,4-dichlorobenzyl)indolin-6-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide;

methyl 5-(N-(4-(4-chloro-3-(dibutylcarbamoyl)-5-methyl-1H-pyrazol-1-yl)-3-(1,2,3,4-tetrahydroisoquinoline-2-carbonyl)benzoyl)sulfamoyl)-1-(3,4-dichlorobenzyl)indoline-2-carboxylate;

N,N-dibutyl-4-chloro-5-methyl-1-(4-(1-(morpholine-4-carbonyl)indolin-5-ylsulfonylcarbamoyl)-2-(1,2,3,4-tetrahydroisoquinoline-2-carbonyl)phenyl)-1H-pyrazole-3-carboxamide;

N,N-dibutyl-4-chloro-5-methyl-1-(4-(1-(2-morpholinoacetyl)indolin-5-ylsulfonylcarbamoyl)-2-(1,2,3,4-tetrahydroisoquinoline-2-carbonyl)phenyl)-1H-pyrazole-3-carboxamide;

1-(4-(7-bromo-1-ethylindolin-5-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide;

N,N-dibutyl-4-chloro-5-methyl-1-(4-(1-(2-morpholinoethyl)indolin-5-ylsulfonylcarbamoyl)-2-(1,2,3,4-tetrahydroisoquinoline-2-carbonyl)phenyl)-1H-pyrazole-3-carboxamide;

N,N-dibutyl-4-chloro-5-methyl-1-(4-(1-((2-(2-morpholinoethoxy)pyridin-3-yl)methyl)indolin-5-ylsulfonylcarbamoyl)-2-(1,2,3,4-tetrahydroisoquinoline-2-carbonyl)phenyl)-1H-pyrazole-3-carboxamide;

1-(4-(3-bromo-1H-indol-5-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide;

1-(4-(3-bromo-1-ethyl-1H-indol-5-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide;

N,N-dibutyl-4-chloro-5-methyl-1-(4-(1-(3-morpholinopropanoyl)indolin-5-ylsulfonylcarbamoyl)-2-(1,2,3,4-tetrahydroisoquinoline-2-carbonyl)phenyl)-1H-pyrazole-3-carboxamide;

N,N-dibutyl-4-chloro-5-methyl-1-(4-(1-(3-morpholinopropyl)-1H-indol-5-ylsulfonylcarbamoyl)-2-(1,2,3,4-tetrahydroisoquinoline-2-carbonyl)phenyl)-1H-pyrazole-3-carboxamide;

N,N-dibutyl-4-chloro-1-(4-(3-chloro-1-ethyl-1H-indol-5-ylsulfonylcarbamoyl)-2-(1,2,3,4-tetrahydroisoquinoline-2-carbonyl)phenyl)-5-methyl-1H-pyrazole-3-carboxamide;

N,N-dibutyl-4-chloro-1-(4-(1-ethyl-3-iodo-1H-indol-5-ylsulfonylcarbamoyl)-2-(1,2,3,4-tetrahydroisoquinoline-2-carbonyl)phenyl)-5-methyl-1H-pyrazole-3-carboxamide;

N,N-dibutyl-4-chloro-1-(4-(3,7-dibromo-1-ethyl-1H-indol-5-ylsulfonylcarbamoyl)-2-(1,2,3,4-tetrahydroisoquinoline-2-carbonyl)phenyl)-5-methyl-1H-pyrazole-3-carboxamide;

N,N-Dibutyl-4-chloro-1-(4-(indolin-6-ylsulfonylcarbamoyl)-2-(1,2,3,4-tetrahydroisoquinoline-2-carbonyl)phenyl)-5-methyl-1H-pyrazole-3-carboxamide;

(E)-1-(4-(5-(But-1-enyl)-1-ethylindolin-6-ylsulfonylcarbamoyl)-2-(1,2,3,4-tetrahydroisoquinoline-2-carbonyl)phenyl)-N,N-dibutyl-4-chloro-5-methyl-1H-pyrazole-3-carboxamide;

N,N-Dibutyl-4-chloro-1-(4-(1-ethyl-5-morpholinoindolin-6-ylsulfonylcarbamoyl)-2-(1,2,3,4-tetrahydroisoquinoline-2-carbonyl)phenyl)-5-methyl-1H-pyrazole-3-carboxamide;

(E)-N,N-Dibutyl-4-chloro-1-(4-(1-ethyl-5-(prop-1-enyl)indolin-6-ylsulfonylcarbamoyl)-2-(1,2,3,4-tetrahydroisoquinoline-2-carbonyl)phenyl)-5-methyl-1H-pyrazole-3-carboxamide;

N,N-Dibutyl-4-chloro-1-(4-(1-(3,4-dichlorobenzyl)indolin-6-ylsulfonylcarbamoyl)-2-(1,2,3,4-tetrahydroisoquinoline-2-carbonyl)phenyl)-5-methyl-1H-pyrazole-3-carboxamide;

N,N-Dibutyl-4-chloro-1-(2-((S)-3-(hydroxymethyl)-1,2,3,4-tetrahydroisoquinoline-2-carbonyl)-4-(naphthalen-2-ylsulfonylcarbamoyl)phenyl)-5-methyl-1H-pyrazole-3-carboxamide;

1-(2-((S)-3-(Aminomethyl)-1,2,3,4-tetrahydroisoquinoline-2-carbonyl)-4-(naphthalen-2-ylsulfonylcarbamoyl)phenyl)-N,N-dibutyl-4-chloro-5-methyl-1H-pyrazole-3-carboxamide;

(3R)-2-(2-(4-Chloro-3-(dibutylcarbamoyl)-5-methyl-1H-pyrazol-1-yl)-5-(naphthalen-2-ylsulfonylcarbamoyl)benzoyl)-1,2,3,4-tetrahydroisoquinoline-3-carboxylic acid;

(3 S)-2-(2-(4-Chloro-3-(dibutylcarbamoyl)-5-methyl-1H-pyrazol-1-yl)-5-(naphthalen-2-ylsulfonylcarbamoyl)benzoyl)-1,2,3,4-tetrahydroisoquinoline-3-carboxylic acid;

N,N-Dibutyl-4-chloro-1-(2-((R)-3-(hydroxymethyl)-1,2,3,4-tetrahydroisoquinoline-2-carbonyl)-4-(naphthalen-2-ylsulfonylcarbamoyl)phenyl)-5-methyl-1H-pyrazole-3-carboxamide;

N,N-Dibutyl-4-chloro-1-(2-(3,4-dihydro-2H-benzo[e][1,3]oxazine-3-carbonyl)-4-(naphthalen-2-ylsulfonylcarbamoyl)phenyl)-5-methyl-1H-pyrazole-3-carboxamide;

N,N-Dibutyl-4-chloro-5-methyl-1-(2-(1-methyl-1,2,3,4-tetrahydroisoquinoline-2-carbonyl)-4-(naphthalen-2-ylsulfonylcarbamoyl)phenyl)-1H-pyrazole-3-carboxamide;

N,N-Dibutyl-4-chloro-1-(2-(4,4-dimethyl-1,2,3,4-tetrahydroisoquinoline-2-carbonyl)-4-(naphthalen-2-ylsulfonylcarbamoyl)phenyl)-5-methyl-1H-pyrazole-3-carboxamide;

1-(2-(7-Bromo-1,2,3,4-tetrahydroisoquinoline-2-carbonyl)-4-(naphthalen-2-ylsulfonylcarbamoyl)phenyl)-N,N-dibutyl-4-chloro-5-methyl-1H-pyrazole-3-carboxamide;

2-(2-(4-Chloro-3-(dibutylcarbamoyl)-5-methyl-1H-pyrazol-1-yl)-5-(naphthalen-2-ylsulfonylcarbamoyl)benzoyl)-1,2,3,4-tetrahydroisoquinoline-7-carboxylic acid;

N,N-Dibutyl-4-chloro-5-methyl-1-(4-(naphthalen-2-ylsulfonylcarbamoyl)-2-(7-(trifluoromethyl)-1,2,3,4-tetrahydroisoquinoline-2-carbonyl)phenyl)-1H-pyrazole-3-carboxamide;

1-(2-(3-Bromo-5,6,7,8-tetrahydro-1,6-naphthyridine-6-carbonyl)-4-(naphthalen-2-ylsulfonylcarbamoyl)phenyl)-N,N-dibutyl-4-chloro-5-methyl-1H-pyrazole-3-carboxamide;

N,N-Dibutyl-4-chloro-5-methyl-1-(4-(naphthalen-2-ylsulfonylcarbamoyl)-2-(1,2,3,4-tetrahydroquinazoline-3-carbonyl)phenyl)-1H-pyrazole-3-carboxamide;

N,N-Dibutyl-4-chloro-1-(2-(1,1-dioxido-3,4-dihydro-2H-benzo[e][1,3]thiazine-3-carbonyl)-4-(naphthalen-2-ylsulfonylcarbamoyl)phenyl)-5-methyl-1H-pyrazole-3-carboxamide;

N,N-Dibutyl-4-chloro-1-(2-((S)-3-((3-methoxypropoxy)methyl)-1,2,3,4-tetrahydroisoquinoline-2-carbonyl)-4-(naphthalen-2-ylsulfonylcarbamoyl)phenyl)-5-methyl-1H-pyrazole-3-carboxamide;

N,N-Dibutyl-4-chloro-5-methyl-1-(2-((S)-3-((1-methylpiperidin-4-ylamino)methyl)-1,2,3,4-tetrahydroisoquinoline-2-carbonyl)-4-(naphthalen-2-ylsulfonylcarbamoyl)phenyl)-1H-pyrazole-3-carboxamide;

N,N-Dibutyl-4-chloro-5-methyl-1-(4-(naphthalen-2-ylsulfonylcarbamoyl)-2-((S)-3-((piperidin-4-ylamino)methyl)-1,2,3,4-tetrahydroisoquinoline-2-carbonyl)phenyl)-1H-pyrazole-3-carboxamide;

N,N-dibutyl-4-chloro-1-(2-((S)-3-((dimethylamino)methyl)-1,2,3,4-tetrahydroisoquinoline-2-carbonyl)-4-(naphthalen-2-ylsulfonylcarbamoyl)phenyl)-5-methyl-1H-pyrazole-3-carboxamide;

N,N-dibutyl-4-chloro-5-methyl-1-(2-((S)-3-(morpholinomethyl)-1,2,3,4-tetrahydroisoquinoline-2-carbonyl)-4-(naphthalen-2-ylsulfonylcarbamoyl)phenyl)-1H-pyrazole-3-carboxamide;

N,N-dibutyl-4-chloro-1-(2-((S)-3-((4-hydroxypiperidin-1-yl)methyl)-1,2,3,4-tetrahydroisoquinoline-2-carbonyl)-4-(naphthalen-2-ylsulfonylcarbamoyl)phenyl)-5-methyl-1H-pyrazole-3-carboxamide;

N,N-dibutyl-4-chloro-5-methyl-1-(4-(naphthalen-2-ylsulfonylcarbamoyl)-2-((S)-3-(pyrrolidin-1-ylmethyl)-1,2,3,4-tetrahydroisoquinoline-2-carbonyl)phenyl)-1H-pyrazole-3-carboxamide;

N,N-dibutyl-4-chloro-5-methyl-1-(2-((S)-3-((4-methylpiperazin-1-yl)methyl)-1,2,3,4-tetrahydroisoquinoline-2-carbonyl)-4-(naphthalen-2-ylsulfonylcarbamoyl)phenyl)-1H-pyrazole-3-carboxamide;

N,N-dibutyl-4-chloro-1-(2-((S)-3-(((2-methoxyethyl)(methyl)amino)-methyl)-1,2,3,4-tetrahydroisoquinoline-2-carbonyl)-4-(naphthalen-2-ylsulfonylcarbamoyl)phenyl)-5-methyl-1H-pyrazole-3-carboxamide;

N,N-dibutyl-4-chloro-1-(2-((S)-3-(((2-hydroxyethyl)(methyl)amino)-methyl)-1,2,3,4-tetrahydroisoquinoline-2-carbonyl)-4-(naphthalen-2-ylsulfonylcarbamoyl)phenyl)-5-methyl-1H-pyrazole-3-carboxamide;

N,N-dibutyl-4-chloro-1-(2-((S)-3-((4-(2-hydroxyethyl)piperazin-1-yl)methyl)-1,2,3,4-tetrahydroisoquinoline-2-carbonyl)-4-(naphthalen-2-ylsulfonylcarbamoyl)phenyl)-5-methyl-1H-pyrazole-3-carboxamide;

N,N-dibutyl-4-chloro-1-(2-((S)-3-((2-(dimethylamino)ethoxy)methyl)-1,2,3,4-tetrahydroisoquinoline-2-carbonyl)-4-(naphthalen-2-ylsulfonylcarbamoyl)phenyl)-5-methyl-1H-pyrazole-3-carboxamide;

1-(2-((S)-3-((2-(benzyloxy)ethoxy)methyl)-1,2,3,4-tetrahydroisoquinoline-2-carbonyl)-4-(naphthalen-2-ylsulfonylcarbamoyl)phenyl)-N,N-dibutyl-4-chloro-5-methyl-1H-pyrazole-3-carboxamide;

N,N-dibutyl-4-chloro-5-methyl-1-(2-(3-((4-methylpiperazin-1-yl)methyl)-1,2,3,4-tetrahydroisoquinoline-2-carbonyl)-4-(naphthalen-2-ylsulfonylcarbamoyl)phenyl)-1H-pyrazole-3-carboxamide;

N,N-Dibutyl-4-chloro-1-(2-((S)-3-((2-hydroxyethoxy)methyl)-1,2,3,4-tetrahydroisoquinoline-2-carbonyl)-4-(naphthalen-2-ylsulfonylcarbamoyl)phenyl)-5-methyl-1H-pyrazole-3-carboxamide;

N,N-Dibutyl-4-chloro-1-(2-(3-(dimethylamino)-2,5-dihydro-1H-benzo[e][1,3]diazepine-2-carbonyl)-4-(naphthalen-2-ylsulfonylcarbamoyl)phenyl)-5-methyl-1H-pyrazole-3-carboxamide;

(Z)—N,N-Dibutyl-4-chloro-1-(2-(3-((2-methoxyethyl)(methyl)amino)-2,5-dihydro-1H-benzo[e][1,3]diazepine-2-carbonyl)-4-(naphthalen-2-ylsulfonylcarbamoyl)phenyl)-5-methyl-1H-pyrazole-3-carboxamide;

3-(4-(N-Butyl-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamido)phenyl)propanoic acid;

N-Butyl-4-chloro-N-(4-iodophenyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide;

1-(3-(4-(N-Butyl-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamido)phenyl)propanoyl)piperidine-4-carboxylic acid;

4-Chloro-N-(3,4-dichlorobenzyl)-N,5-dimethyl-1-(4-(naphthalen-2-ylsulfonylcarbamoyl)-2-(1,2,3,4-tetrahydroisoquinoline-2-carbonyl)phenyl)-1H-pyrazole-3-carboxamide;

N-butyl-4-chloro-N-(3,4-dichlorobenzyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide;

N-butyl-4-chloro-N-(3,4-dichlorophenethyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide;

N-butyl-4-chloro-5-methyl-1-(4-(naphthalen-2-ylsulfonylcarbamoyl)-2-(1,2,3,4-tetrahydroisoquinoline-2-carbonyl)phenyl)-N-(4,4,4-trifluorobutyl)-1H-pyrazole-3-carboxamide;

4-chloro-5-methyl-1-(4-(naphthalen-2-ylsulfonylcarbamoyl)-2-(1,2,3,4-tetrahydroisoquinoline-2-carbonyl)phenyl)-N,N-bis(4,4,4-trifluorobutyl)-1H-pyrazole-3-carboxamide;

4-chloro-5-methyl-1-(4-(naphthalen-2-ylsulfonylcarbamoyl)-2-(1,2,3,4-tetrahydroisoquinoline-2-carbonyl)phenyl)-N,N-bis(3,3,3-trifluoropropyl)-1H-pyrazole-3-carboxamide;

N-butyl-4-chloro-N-(3-isopropoxybenzyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide;

N-butyl-4-chloro-N-(3-(4-chlorophenoxy)benzyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide;

N-(4-butoxybenzyl)-N-butyl-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide;

N-butyl-4-chloro-N-(3,4-dichlorophenyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide;

N-butyl-4-chloro-N-(3-chlorobenzyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide;

N-butyl-4-chloro-N-(4-chlorobenzyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide;

N-butyl-4-chloro-N-(4-(4-fluorophenoxy)phenyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide;

N-butyl-4-chloro-N-(4-(4-chlorophenoxy)phenyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide;

N-butyl-4-chloro-5-methyl-N-(1-methyl-1H-indol-2-yl)-1-(4-(naphthalen-2-ylsulfonylcarbamoyl)-2-(1,2,3,4-tetrahydroisoquinoline-2-carbonyl)phenyl)-1H-pyrazole-3-carboxamide;

N-butyl-4-chloro-N-(3,4-dimethoxyphenyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide;

N-butyl-4-chloro-N-(4-isopropoxyphenyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide;

N-butyl-4-chloro-N-(3-chloro-4-methylphenyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide;

N-(biphenyl-4-yl)-N-butyl-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide;

N-butyl-4-chloro-N-(4-methoxyphenyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide;

N-butyl-4-chloro-N-(3-methoxyphenyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide;

N-butyl-N-(3-tert-butylphenyl)-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide;

N-(biphenyl-3-yl)-N-butyl-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide;

N-butyl-N-(4-tert-butylphenyl)-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide;

N-butyl-4-chloro-N-(2,3-dihydrobenzo[b][1,4]dioxin-6-yl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide;

N-butyl-4-chloro-N-(3-isopropoxyphenyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide;

N-butyl-4-chloro-5-methyl-N-(naphthalen-2-ylmethyl)-1-(4-(naphthalen-2-ylsulfonylcarbamoyl)-2-(1,2,3,4-tetrahydroisoquinoline-2-carbonyl)phenyl)-1H-pyrazole-3-carboxamide;

N-butyl-4-chloro-N-(3'-chlorobiphenyl-3-yl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide;

N-butyl-4-chloro-N-(4'-chlorobiphenyl-3-yl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide;

methyl 4-(N-butyl-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamido)benzoate;

4-(N-butyl-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamido)benzyl propionate;

N-Butyl-4-chloro-5-methyl-1-(4-(naphthalen-2-ylsulfonylcarbamoyl)-2-(1,2,3,4-tetrahydroisoquinoline-2-carbonyl)phenyl)-N-phenyl-1H-pyrazole-3-carboxamide;

N-Benzyl-N-butyl-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide;

N-Butyl-4-chloro-5-methyl-N-(3-(2-(4-methylpiperazin-1-yl)ethylamino)-3-oxopropyl)-1-(4-(naphthalen-2-ylsulfonylcarbamoyl)-2-(1,2,3,4-tetrahydroisoquinoline-2-carbonyl)phenyl)-1H-pyrazole-3-carboxamide;

N-Butyl-4-chloro-N-(3-(1,3-dihydroxypropan-2-ylamino)-3-oxopropyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide;

N-Butyl-4-chloro-N-(3-(1,3-dihydroxy-2-(hydroxymethyl)propan-2-ylamino)-3-oxopropyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide;

4-(N-Butyl-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamido)benzoic acid;

2-(4-(N-Butyl-4-chloro-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamido)phenyl)acetic acid;

4-Bromo-N,N-dibutyl-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide;

N,N-Dibutyl-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide;

N,N-Dibutyl-4-(hydroxymethyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide;

3-(3-(Dibutylcarbamoyl)-5-methyl-1-(4-(naphthalen-2-ylsulfonylcarbamoyl)-2-(1,2,3,4-tetrahydroisoquinoline-2-carbonyl)phenyl)-1H-pyrazol-4-yl)propanoic acid;

N,N-Dibutyl-4-(3-(dimethylamino)propyl)-5-methyl-1-(4-(naphthalen-2-ylsulfonylcarbamoyl)-2-(1,2,3,4-tetrahydroisoquinoline-2-carbonyl)phenyl)-1H-pyrazole-3-carboxamide;

N,N-Dibutyl-1-(4-(naphthalen-2-ylsulfonylcarbamoyl)-2-(1,2,3,4-tetrahydroisoquinoline-2-carbonyl)phenyl)-1H-pyrazole-3-carboxamide;

N,N-Dibutyl-4-chloro-1-(4-(naphthalen-2-ylsulfonylcarbamoyl)-2-(1,2,3,4-tetrahydroisoquinoline-2-carbonyl)phenyl)-1H-pyrazole-3-carboxamide;

N,N-Dibutyl-4-chloro-5-(2-hydroxyethyl)-1-(4-(naphthalen-2-ylsulfonylcarbamoyl)-2-(1,2,3,4-tetrahydroisoquinoline-2-carbonyl)phenyl)-1H-pyrazole-3-carboxamide;

2-(4-Chloro-3-(dibutylcarbamoyl)-1-(4-(naphthalen-2-ylsulfonylcarbamoyl)-2-(1,2,3,4-tetrahydroisoquinoline-2-carbonyl)phenyl)-1H-pyrazol-5-yl)acetic acid;

N,N-Dibutyl-4-chloro-5-(2-(cyclopropanesulfonamido)-2-oxoethyl)-1-(4-(naphthalen-2-ylsulfonylcarbamoyl)-2-(1,2,3,4-tetrahydroisoquinoline-2-carbonyl)phenyl)-1H-pyrazole-3-carboxamide;

2-(4-Chloro-3-(dibutylcarbamoyl)-1-(4-(naphthalen-2-ylsulfonylcarbamoyl)-2-(1,2,3,4-tetrahydroisoquinoline-2-carbonyl)phenyl)-1H-pyrazol-5-yl)ethyl carbamate;

2-(4-Chloro-3-(dibutylcarbamoyl)-1-(4-(naphthalen-2-ylsulfonylcarbamoyl)-2-(1,2,3,4-tetrahydroisoquinoline-2-carbonyl)phenyl)-1H-pyrazol-5-yl)ethyl 4-methylpiperazine-1-carboxylate;

2-(4-Chloro-3-(dibutylcarbamoyl)-1-(4-(naphthalen-2-ylsulfonylcarbamoyl)-2-(1,2,3,4-tetrahydroisoquinoline-2-carbonyl)phenyl)-1H-pyrazol-5-yl)ethyl 2-(4-methylpiperazin-1-yl)ethylcarbamate;

tent-Butyl 3-(N-butyl-4-chloro-1-(4-(7-iodonaphthalen-2-ylsulfonylcarbamoyl)-2-(1,2,3,4-tetrahydroisoquinoline-2-carbonyl)phenyl)-5-methyl-1H-pyrazole-3-carboxamido)propanoate;

N,N-Dibutyl-4-chloro-1-(4-(8-chloronaphthalen-2-ylsulfonylcarbamoyl)-2-((S)-3-(hydroxymethyl)-1,2,3,4-tetrahydroisoquinoline-2-carbonyl)phenyl)-5-methyl-1H-pyrazole-3-carboxamide;

N-Butyl-4-chloro-N-(3,4-dichlorobenzyl)-1-(4-(8-(ethylsulfonyl)naphthalen-2-ylsulfonylcarbamoyl)-2-(1,2,3,4-tetrahydroisoquinoline-2-carbonyl)phenyl)-5-methyl-1H-pyrazole-3-carboxamide;

N-Butyl-4-chloro-N-(3,4-dichlorobenzyl)-1-(4-(7-iodonaphthalen-2-ylsulfonylcarbamoyl)-2-(1,2,3,4-tetrahydroisoquinoline-2-carbonyl)phenyl)-5-methyl-1H-pyrazole-3-carboxamide;

N-Butyl-4-chloro-N-(3,4-dichlorobenzyl)-5-methyl-1-(4-(7-(4-methylpiperazine-1-carbonyl)naphthalen-2-ylsulfonylcarbamoyl)-2-(1,2,3,4-tetrahydroisoquinoline-2-carbonyl)phenyl)-1H-pyrazole-3-carboxamide;

N-Butyl-4-chloro-1-(4-(8-chloronaphthalen-2-ylsulfonylcarbamoyl)-2-((S)-3-(hydroxymethyl)-1,2,3,4-tetrahydroisoquinoline-2-carbonyl)phenyl)-N-(3,4-dichlorobenzyl)-5-methyl-1H-pyrazole-3-carboxamide;

N-Butyl-4-chloro-1-(4-(8-chloronaphthalen-2-ylsulfonylcarbamoyl)-2-((S)-3-(((2-hydroxyethyl)(methyl)amino)methyl)-1,2,3,4-tetrahydroisoquinoline-2-carbonyl)phenyl)-N-(3,4-dichlorobenzyl)-5-methyl-1H-pyrazole-3-carboxamide;

N,N-Dibutyl-4-chloro-1-(2-((S)-3-(hydroxymethyl)-1,2,3,4-tetrahydroisoquinoline-2-carbonyl)-4-(8-(2-morpholinoethoxy)naphthalen-2-ylsulfonylcarbamoyl)phenyl)-5-methyl-1H-pyrazole-3-carboxamide;

N,N-Dibutyl-4-chloro-1-(2-((S)-3-((dimethylamino)methyl)-1,2,3,4-tetrahydroisoquinoline-2-carbonyl)-4-(8-(2-morpholinoethoxy) naphthalen-2-ylsulfonylcarbamoyl)phenyl)-5-methyl-1H-pyrazole-3-carboxamide;

N,N-Dibutyl-4-chloro-5-methyl-1-(4-(8-(2-morpholinoethoxy)naphthalen-2-ylsulfonylcarbamoyl)-2-((S)-3-(morpholinomethyl)-1,2,3,4-tetrahydroisoquinoline-2-carbonyl)phenyl)-1H-pyrazole-3-carboxamide;

N-Butyl-4-chloro-N-(3,4-dichlorobenzyl)-5-methyl-1-(4-(8-(2-morpholinoethoxy)naphthalen-2-ylsulfonylcarbamoyl)-2-((S)-3-(morpholinomethyl)-1,2,3,4-tetrahydroisoquinoline-2-carbonyl)phenyl)-1H-pyrazole-3-carboxamide;

N-Butyl-4-chloro-N-(3,4-dichlorobenzyl)-1-(2-((S)-3-(hydroxymethyl)-1,2,3,4-tetrahydroisoquinoline-2-carbonyl)-4-(8-(2-morpholinoethoxy)naphthalen-2-ylsulfonylcarbamoyl)phenyl)-5-methyl-1H-pyrazole-3-carboxamide;

1-(2-((S)-3-(Aminomethyl)-1,2,3,4-tetrahydroisoquinoline-2-carbonyl)-4-(8-(2-morpholinoethoxy)naphthalen-2-ylsulfonylcarbamoyl)phenyl)-N-butyl-4-chloro-N-(3,4-dichlorobenzyl)-5-methyl-1H-pyrazole-3-carboxamide;

N,N-Dibutyl-4-chloro-1-(4-(1-(3,4-dichlorobenzyl)indolin-5-ylsulfonylcarbamoyl)-2-((S)-3-(hydroxymethyl)-1,2,3,4-tetrahydroisoquinoline-2-carbonyl)phenyl)-5-methyl-1H-pyrazole-3-carboxamide;

N,N-Dibutyl-4-chloro-1-(4-(1-ethylindolin-5-ylsulfonylcarbamoyl)-2-((S)-3-(hydroxymethyl)-1,2,3,4-tetrahydroisoquinoline-2-carbonyl)phenyl)-5-methyl-1H-pyrazole-3-carboxamide;

4-(4-Chloro-3-(dibutylamino)-5-methyl-1H-pyrazol-1-yl)-N-(naphthalen-2-ylsulfonyl)-3-(1,2,3,4-tetrahydroisoquinoline-2-carbonyl)benzamide;

4-(4-Chloro-3-(dipropylamino)-5-methyl-1H-pyrazol-1-yl)-3-((S)-3-(hydroxymethyl)-1,2,3,4-tetrahydroisoquinoline-2-carbonyl)-N-(naphthalen-2-ylsulfonyl)benzamide;

4-(4-Chloro-3-(dipropylamino)-5-methyl-1H-pyrazol-1-yl)-N-(8-chloronaphthalen-2-ylsulfonyl)-3-((S)-3-(hydroxymethyl)-1,2,3,4-tetrahydroisoquinoline-2-carbonyl)benzamide;

3-((S)-3-(Aminomethyl)-1,2,3,4-tetrahydroisoquinoline-2-carbonyl)-4-(4-chloro-3-(dipropylamino)-5-methyl-1H-pyrazol-1-yl)-N-(8-chloronaphthalen-2-ylsulfonyl)benzamide;

4-(4-Chloro-3-(dipropylamino)-5-(trifluoromethyl)-1H-pyrazol-1-yl)-N-(8-chloronaphthalen-2-ylsulfonyl)-3-((S)-3-(hydroxymethyl)-1,2,3,4-tetrahydroisoquinoline-2-carbonyl)benzamide;

4-(4-Chloro-3-(dipropylamino)-5-(trifluoromethyl)-1H-pyrazol-1-yl)-N-(8-chloronaphthalen-2-ylsulfonyl)-3-(1,2,3,4-tetrahydroisoquinoline-2-carbonyl)benzamide;

3-(N-butyl-4-chloro-1-(4-(1-(3,4-dichlorobenzyl)indolin-5-ylsulfonylcarbamoyl)-2-(1,2,3,4-tetrahydroisoquinoline-2-carbonyl)phenyl)-5-methyl-1H-pyrazole-3-carboxamido) propanoic acid;

N,N-dibutyl-4-chloro-1-(4-(1-(3,4-dichlorobenzyl)-1H-indol-5-ylsulfonylcarbamoyl)-2-((S)-3-(hydroxymethyl)-1,2,3,4-tetrahydroisoquinoline-2-carbonyl)phenyl)-5-methyl-1H-pyrazole-3-carboxamide;

1-(4-(3-bromo-1-(3,4-dichlorobenzyl)-1H-indol-5-ylsulfonylcarbamoyl)-2-((S)-3-(hydroxymethyl)-1,2,3,4-tetrahydroisoquinoline-2-carbonyl)phenyl)-N,N-dibutyl-4-chloro-5-methyl-1H-pyrazole-3-carboxamide;

N-butyl-4-chloro-1-(4-(1-(3,4-dichlorobenzyl)indolin-5-ylsulfonylcarbamoyl)-2-(1,2,3,4-tetrahydroisoquinoline-2-carbonyl)phenyl)-5-methyl-N-(3-(2-(4-methylpiperazin-1-yl)ethylamino)-3-oxopropyl)-1H-pyrazole-3-carboxamide;

1-(2-((S)-3-(aminomethyl)-1,2,3,4-tetrahydroisoquinoline-2-carbonyl)-4-(3-bromo-1-(3,4-dichlorobenzyl)-1H-indol-5-ylsulfonylcarbamoyl)phenyl)-N,N-dibutyl-4-chloro-5-methyl-1H-pyrazole-3-carboxamide;

N,N-dibutyl-4-chloro-1-(4-(8-chloronaphthalen-2-ylsulfonylcarbamoyl)-2-((S)-3-((3-methoxypropoxy)methyl)-1,2,3,4-tetrahydroisoquinoline-2-carbonyl)phenyl)-5-methyl-1H-pyrazole-3-carboxamide;

1-(2-((S)-3-(aminomethyl)-1,2,3,4-tetrahydroisoquinoline-2-carbonyl)-4-(8-chloronaphthalen-2-ylsulfonylcarbamoyl)phenyl)-N,N-dibutyl-4-chloro-5-methyl-1H-pyrazole-3-carboxamide;

(Z)—N-(8-bromo-5-chloronaphthalen-2-ylsulfonyl)-4-(4-chloro-3-(dipropylamino)-5-methyl-1H-pyrazol-1-yl)-3-(3-(dimethylamino)-2,5-dihydro-1H-benzo[e][1,3]diazepine-2-carbonyl)benzamide;

1-(4-(7-bromo-1-ethylindolin-5-ylsulfonylcarbamoyl)-2-((S)-3-(hydroxymethyl)-1,2,3,4-tetrahydroisoquinoline-2-carbonyl)phenyl)-N,N-dibutyl-4-chloro-5-methyl-1H-pyrazole-3-carboxamide;

4-chloro-1-(4-(1-ethylindolin-5-ylsulfonylcarbamoyl)-2-((S)-3-(hydroxymethyl)-1,2,3,4-tetrahydroisoquinoline-2-carbonyl)phenyl)-5-methyl-N,N-dipropyl-1H-pyrazole-3-carboxamide;

N-(8-bromo-5-chloronaphthalen-2-ylsulfonyl)-4-(4-chloro-3-(dipropylamino)-5-methyl-1H-pyrazol-1-yl)-3-((S)-3-(hydroxymethyl)-1,2,3,4-tetrahydroisoquinoline-2-carbonyl)benzamide;

1-(4-(7-bromo-1-ethyl-1H-indol-5-ylsulfonylcarbamoyl)-2-((S)-3-(hydroxymethyl)-1,2,3,4-tetrahydroisoquinoline-2-carbonyl)phenyl)-N,N-dibutyl-4-chloro-5-methyl-1H-pyrazole-3-carboxamide;

1-(4-(7-bromo-1-ethylindolin-5-ylsulfonylcarbamoyl)-2-((S)-3-(hydroxymethyl)-1,2,3,4-tetrahydroisoquinoline-2-carbonyl)phenyl)-4-chloro-5-methyl-N,N-dipropyl-1H-pyrazole-3-carboxamide;

N,N-dibutyl-4-chloro-1-(4-(3,7-dibromo-1-ethyl-1H-indol-5-ylsulfonylcarbamoyl)-2-((S)-3-(hydroxymethyl)-1,2,3,4-tetrahydroisoquinoline-2-carbonyl)phenyl)-5-methyl-1H-pyrazole-3-carboxamide;

1-(2-(6-bromo-1,2,3,4-tetrahydroisoquinoline-2-carbonyl)-4-(1-(3,4-dichlorobenzyl)indolin-5-ylsulfonylcarbamoyl)phenyl)-N,N-dibutyl-4-chloro-5-methyl-1H-pyrazole-3-carboxamide;

N,N-dibutyl-4-chloro-1-(4-(1-(3,4-dichlorobenzyl)indolin-5-ylsulfonylcarbamoyl)-2-(6,7-dimethoxy-1,2,3,4-tetrahydroisoquinoline-2-carbonyl)phenyl)-5-methyl-1H-pyrazole-3-carboxamide;

2-(4'-((N-butyl-4-chloro-1-(4-(1-(3,4-dichlorobenzyl)indolin-5-ylsulfonylcarbamoyl)-2-(1,2,3,4-tetrahydroisoquinoline-2-carbonyl)phenyl)-5-methyl-1H-pyrazole-3-carboxamido)methyl) biphenyl-4-yl)acetic acid;

2-(4'-((4-chloro-1-(4-(1-(3,4-dichlorobenzyl)indolin-5-ylsulfonylcarbamoyl)-2-(1,2,3,4-tetrahydroisoquinoline-2-carbonyl)phenyl)-5-methyl-1H-pyrazole-3-carboxamido)methyl)biphenyl-4-yl)acetic acid;

4-(3-(dibutylcarbamoyl)-1-(4-(1-(3,4-dichlorobenzyl)indolin-5-ylsulfonylcarbamoyl)-2-(1,2,3,4-tetrahydroisoquinoline-2-carbonyl)phenyl)-5-methyl-1H-pyrazol-4-yl) benzoic acid;

4-chloro-1-(4-(1-(3,4-dichlorobenzyl)indolin-5-ylsulfonylcarbamoyl)-2-(1,2,3,4-tetrahydroisoquinoline-2-carbonyl)phenyl)-5-methyl-N,N-dipropyl-1H-pyrazole-3-carboxamide;

1-(4-(8-bromo-5-chloronaphthalen-2-ylsulfonylcarbamoyl)-2-(1,2,3,4-tetrahydroisoquinoline-2-carbonyl)phenyl)-N-butyl-4-chloro-N-(4'-chlorobiphenyl-3-yl)-5-methyl-1H-pyrazole-3-carboxamide;

1-(4-(8-bromo-5-chloronaphthalen-2-ylsulfonylcarbamoyl)-2-(1,2,3,4-tetrahydroisoquinoline-2-carbonyl)phenyl)-N-butyl-4-chloro-N-(3'-chlorobiphenyl-3-yl)-5-methyl-1H-pyrazole-3-carboxamide;

N-butyl-4-chloro-N-((4'-chlorobiphenyl-4-yl)methyl)-1-(4-(1-(3,4-dichlorobenzyl)indolin-5-ylsulfonylcarbamoyl)-2-(1,2,3,4-tetrahydroisoquinoline-2-carbonyl)phenyl)-5-methyl-1H-pyrazole-3-carboxamide;

N-butyl-4-chloro-N-(4-(4-chlorophenoxy)phenyl)-1-(4-(1-(3,4-dichlorobenzyl)indolin-5-ylsulfonylcarbamoyl)-2-(1,2,3,4-tetrahydroisoquinoline-2-carbonyl)phenyl)-5-methyl-1H-pyrazole-3-carboxamide;

N-butyl-4-chloro-N-(4'-chlorobiphenyl-3-yl)-1-(4-(5,8-dichloronaphthalen-2-ylsulfonylcarbamoyl)-2-(1,2,3,4-tetrahydroisoquinoline-2-carbonyl)phenyl)-5-methyl-1H-pyrazole-3-carboxamide;

N-butyl-4-chloro-N-(3'-chlorobiphenyl-3-yl)-1-(4-(5,8-dichloronaphthalen-2-ylsulfonylcarbamoyl)-2-(1,2,3,4-tetrahydroisoquinoline-2-carbonyl)phenyl)-5-methyl-1H-pyrazole-3-carboxamide;
Ethyl 5-butyl-4-(4-(naphthalen-2-ylsulfonylcarbamoyl)-2-(1,2,3,4-tetrahydroisoquinoline-2-carbonyl)phenyl)-1-phenyl-1H-pyrazole-3-carboxylate;
Ethyl 5-methyl-4-(4-(naphthalen-2-ylsulfonylcarbamoyl)-2-(1,2,3,4-tetrahydroisoquinoline-2-carbonyl)phenyl)-1-phenyl-1H-pyrazole-3-carboxylate;
Ethyl 5-butyl-1-(4-methoxyphenyl)-4-(4-(naphthalen-2-ylsulfonylcarbamoyl)-2-(1,2,3,4-tetrahydroisoquinoline-2-carbonyl)phenyl)-1H-pyrazole-3-carboxylate;
Ethyl 5-butyl-1-(4-isopropylphenyl)-4-(4-(naphthalen-2-ylsulfonylcarbamoyl)-2-(1,2,3,4-tetrahydroisoquinoline-2-carbonyl)phenyl)-1H-pyrazole-3-carboxylate;
Ethyl 5-butyl-4-(4-(naphthalen-2-ylsulfonylcarbamoyl)-2-(1,2,3,4-tetrahydroisoquinoline-2-carbonyl)phenyl)-1-(3-phenoxyphenyl)-1H-pyrazole-3-carboxylate;
Ethyl 5-butyl-4-(4-(naphthalen-2-ylsulfonylcarbamoyl)-2-(1,2,3,4-tetrahydroisoquinoline-2-carbonyl)phenyl)-1-(4-phenoxyphenyl)-1H-pyrazole-3-carboxylate;
Ethyl 5-butyl-1-(4-(4-chlorophenoxy)phenyl)-4-(4-(naphthalen-2-ylsulfonylcarbamoyl)-2-(1,2,3,4-tetrahydroisoquinoline-2-carbonyl)phenyl)-1H-pyrazole-3-carboxylate;
Ethyl 5-butyl-1-(4-(3-chlorophenoxy)phenyl)-4-(4-(naphthalen-2-ylsulfonylcarbamoyl)-2-(1,2,3,4-tetrahydroisoquinoline-2-carbonyl)phenyl)-1H-pyrazole-3-carboxylate;
Ethyl 1-(4-butoxyphenyl)-5-butyl-4-(4-(naphthalen-2-ylsulfonylcarbamoyl)-2-(1,2,3,4-tetrahydroisoquinoline-2-carbonyl)phenyl)-1H-pyrazole-3-carboxylate;
Ethyl 5-butyl-1-(4-(2-hydroxyethyl)phenyl)-4-(4-(naphthalen-2-ylsulfonylcarbamoyl)-2-(1,2,3,4-tetrahydroisoquinoline-2-carbonyl)phenyl)-1H-pyrazole-3-carboxylate;
Ethyl 1-(4-(allyloxy)phenyl)-5-butyl-4-(4-(naphthalen-2-ylsulfonylcarbamoyl)-2-(1,2,3,4-tetrahydroisoquinoline-2-carbonyl)phenyl)-1H-pyrazole-3-carboxylate;
Ethyl 1-(biphenyl-4-yl)-5-butyl-4-(4-(naphthalen-2-ylsulfonylcarbamoyl)-2-(1,2,3,4-tetrahydroisoquinoline-2-carbonyl)phenyl)-1H-pyrazole-3-carboxylate;
Ethyl 5-butyl-1-(3-(methoxycarbonyl)phenyl)-4-(4-(naphthalen-2-ylsulfonylcarbamoyl)-2-(1,2,3,4-tetrahydroisoquinoline-2-carbonyl)phenyl)-1H-pyrazole-3-carboxylate;
4-(5-Butyl-3-(hydroxymethyl)-1-phenyl-1H-pyrazol-4-yl)-N-(naphthalen-2-ylsulfonyl)-3-(1,2,3,4-tetrahydroisoquinoline-2-carbonyl)benzamide;
5-Butyl-4-(4-(naphthalen-2-ylsulfonylcarbamoyl)-2-(1,2,3,4-tetrahydroisoquinoline-2-carbonyl)phenyl)-1-phenyl-1H-pyrazole-3-carboxylic acid;
4-(5-Butyl-3-(hydroxymethyl)-1-(3-(hydroxymethyl)phenyl)-1H-pyrazol-4-yl)-N-(naphthalen-2-ylsulfonyl)-3-(1,2,3,4-tetrahydroisoquinoline-2-carbonyl)benzamide;
Ethyl 5-butyl-1-phenyl-4-(2-(1,2,3,4-tetrahydroisoquinoline-2-carbonyl)-4-(2-(trimethylsilyl)ethylsulfonylcarbamoyl)phenyl)-1H-pyrazole-3-carboxylate;
4-(5-Butyl-3-(hydroxymethyl)-1-phenyl-1H-pyrazol-4-yl)-3-(1,2,3,4-tetrahydroisoquinoline-2-carbonyl)-N-(2-(trimethylsilyl)ethylsulfonyl)benzamide;
4-(5-butyl-3-(hydroxymethyl)-1-(4-phenoxyphenyl)-1H-pyrazol-4-yl)-N-(naphthalen-2-ylsulfonyl)-3-(1,2,3,4-tetrahydroisoquinoline-2-carbonyl)benzamide;
4-(5-butyl-1-(4-(4-chlorophenoxy)phenyl)-3-(hydroxymethyl)-1H-pyrazol-4-yl)-N-(naphthalen-2-ylsulfonyl)-3-(1,2,3,4-tetrahydroisoquinoline-2-carbonyl)benzamide;
4-(5-butyl-1-(4-(3-chlorophenoxy)phenyl)-3-(hydroxymethyl)-1H-pyrazol-4-yl)-N-(naphthalen-2-ylsulfonyl)-3-(1,2,3,4-tetrahydroisoquinoline-2-carbonyl)benzamide;
4-(5-butyl-1-(4-butoxyphenyl)-3-(hydroxymethyl)-1H-pyrazol-4-yl)-N-(naphthalen-2-ylsulfonyl)-3-(1,2,3,4-tetrahydroisoquinoline-2-carbonyl)benzamide;
4-(5-butyl-1-(4-(2-hydroxyethyl)phenyl)-3-(hydroxymethyl)-1H-pyrazol-4-yl)-N-(naphthalen-2-ylsulfonyl)-3-(1,2,3,4-tetrahydroisoquinoline-2-carbonyl)benzamide;
4-(1-(4-(allyloxy)phenyl)-5-butyl-3-(hydroxymethyl)-1H-pyrazol-4-yl)-N-(naphthalen-2-ylsulfonyl)-3-(1,2,3,4-tetrahydroisoquinoline-2-carbonyl)benzamide;
4-(1-(biphenyl-4-yl)-5-butyl-3-(hydroxymethyl)-1H-pyrazol-4-yl)-N-(naphthalen-2-ylsulfonyl)-3-(1,2,3,4-tetrahydroisoquinoline-2-carbonyl)benzamide;
ethyl 5-butyl-4-(4-(8-chloronaphthalen-2-ylsulfonylcarbamoyl)-2-(1,2,3,4-tetrahydroisoquinoline-2-carbonyl)phenyl)-1-(4-(3-chlorophenoxy)phenyl)-1H-pyrazole-3-carboxylate;
ethyl 5-butyl-1-(4-(3-chlorophenoxy)phenyl)-4-(4-(ethylsulfonylcarbamoyl)-2-(1,2,3,4-tetrahydroisoquinoline-2-carbonyl)phenyl)-1H-pyrazole-3-carboxylate;
ethyl 5-butyl-1-(4-(3-chlorophenoxy)phenyl)-4-(4-(pentylsulfonylcarbamoyl)-2-(1,2,3,4-tetrahydroisoquinoline-2-carbonyl)phenyl)-1H-pyrazole-3-carboxylate;
ethyl 4-(4-(8-bromo-5-chloronaphthalen-2-ylsulfonylcarbamoyl)-2-(1,2,3,4-tetrahydroisoquinoline-2-carbonyl)phenyl)-5-butyl-1-(4-(3-chlorophenoxy)phenyl)-1H-pyrazole-3-carboxylate;
4-(5-butyl-1-(4-(3-chlorophenoxy)phenyl)-3-(hydroxymethyl)-1H-pyrazol-4-yl)-N-(8-chloronaphthalen-2-ylsulfonyl)-3-(1,2,3,4-tetrahydroisoquinoline-2-carbonyl)benzamide;
4-(5-butyl-1-(4-(3-chlorophenoxy)phenyl)-3-(hydroxymethyl)-1H-pyrazol-4-yl)-N-(ethylsulfonyl)-3-(1,2,3,4-tetrahydroisoquinoline-2-carbonyl)benzamide;
4-(5-butyl-1-(4-(3-chlorophenoxy)phenyl)-3-(hydroxymethyl)-1H-pyrazol-4-yl)-N-(pentylsulfonyl)-3-(1,2,3,4-tetrahydroisoquinoline-2-carbonyl)benzamide;
N-(8-bromo-5-chloronaphthalen-2-ylsulfonyl)-4-(5-butyl-1-(4-(3-chlorophenoxy)phenyl)-3-(hydroxymethyl)-1H-pyrazol-4-yl)-3-(1,2,3,4-tetrahydroisoquinoline-2-carbonyl)benzamide;
4-(5-Butyl-3-(hydroxymethyl)-1-(4-hydroxyphenyl)-1H-pyrazol-4-yl)-N-(naphthalen-2-ylsulfonyl)-3-(1,2,3,4-tetrahydroisoquinoline-2-carbonyl)benzamide;
4-(5-Butyl-3-(hydroxymethyl)-1-(4-(3-hydroxypropoxy)phenyl)-1H-pyrazol-4-yl)-N-(naphthalen-2-ylsulfonyl)-3-(1,2,3,4-tetrahydroisoquinoline-2-carbonyl)benzamide;
(±)-4-(5-Butyl-1-(4-(2,3-dihydroxypropoxy)phenyl)-3-(hydroxymethyl)-1H-pyrazol-4-yl)-N-(naphthalen-2-ylsulfonyl)-3-(1,2,3,4-tetrahydroisoquinoline-2-carbonyl)benzamide;
Ethyl 5-butyl-4-(2-((S)-3-(hydroxymethyl)-1,2,3,4-tetrahydroisoquinoline-2-carbonyl)-4-(naphthalen-2-ylsulfonylcarbamoyl)phenyl)-1-phenyl-1H-pyrazole-3-carboxylate;
4-(5-Butyl-3-(hydroxymethyl)-1-phenyl-1H-pyrazol-4-yl)-3-((S)-3-(hydroxymethyl)-1,2,3,4-tetrahydroisoquinoline-2-carbonyl)-N-(naphthalen-2-ylsulfonyl)benzamide;
Ethyl 4-(2-((S)-3-(azidomethyl)-1,2,3,4-tetrahydroisoquinoline-2-carbonyl)-4-(naphthalen-2-ylsulfonylcarbamoyl)phenyl)-5-butyl-1-phenyl-1H-pyrazole-3-carboxylate;
Ethyl 4-(2-((S)-3-(aminomethyl)-1,2,3,4-tetrahydroisoquinoline-2-carbonyl)-4-(naphthalen-2-ylsulfonylcarbamoyl)phenyl)-5-butyl-1-phenyl-1H-pyrazole-3-carboxylate;

3-((S)-3-(Aminomethyl)-1,2,3,4-tetrahydroisoquinoline-2-carbonyl)-4-(5-butyl-3-(hydroxymethyl)-1-phenyl-1H-pyrazol-4-yl)-N-(naphthalen-2-ylsulfonyl)benzamide;

N,N-Dibutyl-1-methyl-2-(4-(naphthalen-2-ylsulfonylcarbamoyl)-2-(1,2,3,4-tetrahydroisoquinoline-2-carbonyl)phenyl)-1H-imidazole-4-carboxamide;

N,N-Dibutyl-1-(2-(methylamino)-2-oxoethyl)-2-(4-(naphthalen-2-ylsulfonylcarbamoyl)-2-(1,2,3,4-tetrahydroisoquinoline-2-carbonyl)phenyl)-1H-imidazole-4-carboxamide;

N,N-Dibutyl-1-(3-hydroxypropyl)-2-(4-(naphthalen-2-ylsulfonylcarbamoyl)-2-(1,2,3,4-tetrahydroisoquinoline-2-carbonyl)phenyl)-1H-imidazole-4-carboxamide;

N,N-Dibutyl-1-(3-(dimethylamino)propyl)-2-(4-(naphthalen-2-ylsulfonylcarbamoyl)-2-(1,2,3,4-tetrahydroisoquinoline-2-carbonyl)phenyl)-1H-imidazole-4-carboxamide;

N,N-Dibutyl-2-(4-(naphthalen-2-ylsulfonylcarbamoyl)-2-(1,2,3,4-tetrahydroisoquinoline-2-carbonyl)phenyl)-1-((2-(trimethylsilyl)ethoxy)methyl)-1H-imidazole-4-carboxamide;

2-(4-(Dibutylcarbamoyl)-2-(4-(naphthalen-1-ylsulfonylcarbamoyl)-2-(1,2,3,4-tetrahydroisoquinoline-2-carbonyl)phenyl)-1H-imidazol-1-yl)acetic acid;

N,N-Dibutyl-2-(4-(8-iodonaphthalen-2-ylsulfonylcarbamoyl)-2-(1,2,3,4-tetrahydroisoquinoline-2-carbonyl)phenyl)-1-methyl-1H-imidazole-4-carboxamide;

N,N-Dibutyl-2-(4-(8-chloronaphthalen-2-ylsulfonylcarbamoyl)-2-((S)-3-(hydroxymethyl)-1,2,3,4-tetrahydroisoquinoline-2-carbonyl)phenyl)-1-phenethyl-1H-imidazole-4-carboxamide;

N,N-Dibutyl-2-(4-(8-chloronaphthalen-2-ylsulfonylcarbamoyl)-2-((S)-3-(hydroxymethyl)-1,2,3,4-tetrahydroisoquinoline-2-carbonyl)phenyl)-1-(3-phenylpropyl)-1H-imidazole-4-carboxamide;

1-Benzyl-N,N-dibutyl-2-(4-(8-chloronaphthalen-2-ylsulfonylcarbamoyl)-2-((S)-3-(hydroxymethyl)-1,2,3,4-tetrahydroisoquinoline-2-carbonyl)phenyl)-1H-imidazole-4-carboxamide;

N,N-Dibutyl-1-(2-hydroxyethyl)-2-(2-((S)-3-(hydroxymethyl)-1,2,3,4-tetrahydroisoquinoline-2-carbonyl)-4-(naphthalen-2-ylsulfonylcarbamoyl)phenyl)-1H-imidazole-4-carboxamide;

N,N-Dibutyl-2-(2-((S)-3-(hydroxymethyl)-1,2,3,4-tetrahydroisoquinoline-2-carbonyl)-4-(naphthalen-2-ylsulfonylcarbamoyl)phenyl)-1-(2-methoxyethyl)-1H-imidazole-4-carboxamide;

N,N-Dibutyl-1-(2-(2-hydroxyethoxy)ethyl)-2-(2-((S)-3-(hydroxymethyl)-1,2,3,4-tetrahydroisoquinoline-2-carbonyl)-4-(naphthalen-2-ylsulfonylcarbamoyl)phenyl)-1H-imidazole-4-carboxamide;

N,N-Dibutyl-2-(2-((S)-3-(hydroxymethyl)-1,2,3,4-tetrahydroisoquinoline-2-carbonyl)-4-(naphthalen-2-ylsulfonylcarbamoyl)phenyl)-1-(2-morpholinoethyl)-1H-imidazole-4-carboxamide;

N,N-Dibutyl-2-(2-((S)-3-(hydroxymethyl)-1,2,3,4-tetrahydroisoquinoline-2-carbonyl)-4-(naphthalen-2-ylsulfonylcarbamoyl)phenyl)-1-(3-morpholinopropyl)-1H-imidazole-4-carboxamide;

N,N-Dibutyl-2-(2-((S)-3-(hydroxymethyl)-1,2,3,4-tetrahydroisoquinoline-2-carbonyl)-4-(naphthalen-2-ylsulfonylcarbamoyl)phenyl)-1-(3-(4-methylpiperazin-1-yl)propyl)-1H-imidazole-4-carboxamide;

N,N-Dibutyl-2-(2-((S)-3-(hydroxymethyl)-1,2,3,4-tetrahydroisoquinoline-2-carbonyl)-4-(naphthalen-2-ylsulfonylcarbamoyl)phenyl)-1-(2-(4-methylpiperazin-1-yl)ethyl)-1H-imidazole-4-carboxamide;

2-(2-((S)-3-(Aminomethyl)-1,2,3,4-tetrahydroisoquinoline-2-carbonyl)-4-(naphthalen-2-ylsulfonylcarbamoyl)phenyl)-N,N-dibutyl-1-methyl-1H-imidazole-4-carboxamide;

2-(2-((S)-3-(Aminomethyl)-1,2,3,4-tetrahydroisoquinoline-2-carbonyl)-4-(8-iodonaphthalen-2-ylsulfonylcarbamoyl)phenyl)-N,N-dibutyl-1-methyl-1H-imidazole-4-carboxamide;

N,N-Dibutyl-2-(4-(8-chloronaphthalen-2-ylsulfonylcarbamoyl)-2-((S)-3-(hydroxymethyl)-1,2,3,4-tetrahydroisoquinoline-2-carbonyl)phenyl)-1-methyl-1H-imidazole-4-carboxamide;

N,N-Dibutyl-5-(4-(8-iodonaphthalen-2-ylsulfonylcarbamoyl)-2-(1,2,3,4-tetrahydroisoquinoline-2-carbonyl)phenyl)-1-methyl-1H-imidazole-4-carboxamide;

N,N-Dibutyl-5-(4-(8-chloronaphthalen-2-ylsulfonylcarbamoyl)-2-(1,2,3,4-tetrahydroisoquinoline-2-carbonyl)phenyl)-1-methyl-1H-imidazole-4-carboxamide;

N,N-Dibutyl-6-(4-(naphthalen-2-ylsulfonylcarbamoyl)-2-(1,2,3,4-tetrahydroisoquinoline-2-carbonyl)phenyl)picolinamide;

4-(6-(Dibutylamino)pyridin-2-yl)-N-(naphthalen-2-ylsulfonyl)-3-(1,2,3,4-tetrahydroisoquinoline-2-carbonyl)benzamide;

4-(3-Bromo-6-(dibutylamino)pyridin-2-yl)-N-(7-chloronaphthalen-2-ylsulfonyl)-3-(1,2,3,4-tetrahydroisoquinoline-2-carbonyl)benzamide;

4-(3-Bromo-6-(dibutylamino)pyridin-2-yl)-N-(8-chloronaphthalen-2-ylsulfonyl)-3-(1,2,3,4-tetrahydroisoquinoline-2-carbonyl)benzamide;

4-(3-Bromo-6-(dibutylamino)pyridin-2-yl)-N-(1-(3,4-dichlorobenzyl)indolin-5-ylsulfonyl)-3-(1,2,3,4-tetrahydroisoquinoline-2-carbonyl)benzamide;

4-(2-(Dibutylamino)pyrimidin-4-yl)-N-(naphthalen-2-ylsulfonyl)-3-(1,2,3,4-tetrahydroisoquinoline-2-carbonyl)benzamide;

N-(8-chloronaphthalen-2-ylsulfonyl)-4-(2-(dibutylamino)pyrimidin-4-yl)-3-(1,2,3,4-tetrahydroisoquinoline-2-carbonyl)benzamide;

4-(2-(dibutylamino)pyrimidin-4-yl)-N-(7-iodonaphthalen-2-ylsulfonyl)-3-(1,2,3,4-tetrahydroisoquinoline-2-carbonyl)benzamide;

4-(2-(dibutylamino)pyrimidin-4-yl)-N-(1-ethyl-1H-indol-5-ylsulfonyl)-3-(1,2,3,4-tetrahydroisoquinoline-2-carbonyl)benzamide;

4-(2-(dibutylamino)pyrimidin-4-yl)-N-(1-(3,4-dichlorobenzyl)-1H-indol-5-ylsulfonyl)-3-(1,2,3,4-tetrahydroisoquinoline-2-carbonyl)benzamide;

4-(2-(dipentylamino)pyrimidin-4-yl)-N-(naphthalen-2-ylsulfonyl)-3-(1,2,3,4-tetrahydroisoquinoline-2-carbonyl)benzamide;

N-(naphthalen-2-ylsulfonyl)-4-(2-(3-propylpyrrolidin-1-yl)pyrimidin-4-yl)-3-(1,2,3,4-tetrahydroisoquinoline-2-carbonyl)benzamide;

4-(2-(butyl(3,4-dichlorobenzyl)amino)pyrimidin-4-yl)-N-(naphthalen-2-ylsulfonyl)-3-(1,2,3,4-tetrahydroisoquinoline-2-carbonyl)benzamide;

4-(2-(dipropylamino)pyrimidin-4-yl)-N-(naphthalen-2-ylsulfonyl)-3-(1,2,3,4-tetrahydroisoquinoline-2-carbonyl)benzamide;

4-(2-((cyclopropylmethyl)(propyl)amino)pyrimidin-4-yl)-N-(naphthalen-2-ylsulfonyl)-3-(1,2,3,4-tetrahydroisoquinoline-2-carbonyl)benzamide;

4-(2-(diethylamino)pyrimidin-4-yl)-N-(naphthalen-2-ylsulfonyl)-3-(1,2,3,4-tetrahydroisoquinoline-2-carbonyl)benzamide;

N-(naphthalen-2-ylsulfonyl)-4-(2-(3-phenethylpyrrolidin-1-yl)pyrimidin-4-yl)-3-(1,2,3,4-tetrahydroisoquinoline-2-carbonyl)benzamide;
(S)-4-(2-(Dibutylamino)pyrimidin-4-yl)-3-(3-(hydroxymethyl)-1,2,3,4-tetrahydroisoquinoline-2-carbonyl)-N-(naphthalen-2-ylsulfonyl)benzamide;
(S)-3-(3-(Aminomethyl)-1,2,3,4-tetrahydroisoquinoline-2-carbonyl)-4-(2-(dibutylamino)pyrimidin-4-yl)-N-(naphthalen-2-ylsulfonyl)benzamide;
4-(2-(dibutylamino)pyrimidin-4-yl)-3-(isoindoline-2-carbonyl)-N-(naphthalen-2-ylsulfonyl)benzamide;
4-(2-(dibutylamino)pyrimidin-4-yl)-N-(naphthalen-2-ylsulfonyl)-3-(7-(trifluoromethyl)-1,2,3,4-tetrahydroisoquinoline-2-carbonyl)benzamide;
4-(2-(dibutylamino)pyrimidin-4-yl)-N3,N3-dimethyl-N1-(naphthalen-2-ylsulfonyl) isophthalamide;
(S)—N-(8-Chloronaphthalen-2-ylsulfonyl)-4-(2-(dibutylamino)pyrimidin-4-yl)-3-(3-(hydroxymethyl)-1,2,3,4-tetrahydroisoquinoline-2-carbonyl)benzamide;
(S)-4-(2-(Dibutylamino)pyrimidin-4-yl)-3-(3-(hydroxymethyl)-1,2,3,4-tetrahydroisoquinoline-2-carbonyl)-N-(7-iodonaphthalen-2-ylsulfonyl)benzamide;
(S)-4-(2-(Dibutylamino)pyrimidin-4-yl)-N-(1-ethylindolin-5-ylsulfonyl)-3-(3-(hydroxymethyl)-1,2,3,4-tetrahydroisoquinoline-2-carbonyl)benzamide;
4-(5-Chloro-2-(dibutylamino)pyrimidin-4-yl)-N-(naphthalen-2-ylsulfonyl)-3-(1,2,3,4-tetrahydroisoquinoline-2-carbonyl)benzamide;
4-(2-(Dibutylamino)-5-methylpyrimidin-4-yl)-N-(naphthalen-2-ylsulfonyl)-3-(1,2,3,4-tetrahydroisoquinoline-2-carbonyl)benzamide;
4-(5-Chloro-2-(dibutylamino)pyrimidin-4-yl)-N-(8-chloronaphthalen-2-ylsulfonyl)-3-(1,2,3,4-tetrahydroisoquinoline-2-carbonyl)benzamide;
N-(8-Chloronaphthalen-2-ylsulfonyl)-4-(2-(dibutylamino)-5-methylpyrimidin-4-yl)-3-(1,2,3,4-tetrahydroisoquinoline-2-carbonyl)benzamide;
4-(5-Chloro-2-(dibutylamino)pyrimidin-4-yl)-3-((S)-3-(hydroxymethyl)-1,2,3,4-tetrahydroisoquinoline-2-carbonyl)-N-(naphthalen-2-ylsulfonyl)benzamide;
4-(5-Bromo-2-(dibutylamino)pyrimidin-4-yl)-3-((S)-3-(hydroxymethyl)-1,2,3,4-tetrahydroisoquinoline-2-carbonyl)-N-(naphthalen-2-ylsulfonyl)benzamide;
4-(5-Bromo-2-(dibutylamino)pyrimidin-4-yl)-N-(8-chloronaphthalen-2-ylsulfonyl)-3-(1,2,3,4-tetrahydroisoquinoline-2-carbonyl)benzamide;
4-(5-Chloro-2-(dibutylamino)pyrimidin-4-yl)-N-(7-chloronaphthalen-2-ylsulfonyl)-3-(1,2,3,4-tetrahydroisoquinoline-2-carbonyl)benzamide;
Ethyl 4-(4-(7-chloronaphthalen-2-ylsulfonylcarbamoyl)-2-(1,2,3,4-tetrahydroisoquinoline-2-carbonyl)phenyl)-2-(dibutylamino)pyrimidine-5-carboxylate;
4-(4-(7-Chloronaphthalen-2-ylsulfonylcarbamoyl)-2-(1,2,3,4-tetrahydroisoquinoline-2-carbonyl)phenyl)-2-(dibutylamino)pyrimidine-5-carboxylic acid;
4-(5-Chloro-2-(dibutylamino)pyrimidin-4-yl)-N-(1-(3,4-dichlorobenzyl)indolin-5-ylsulfonyl)-3-(1,2,3,4-tetrahydroisoquinoline-2-carbonyl)benzamide;
4-(2-(Butyl(3,4-dichlorobenzyl)amino)-5-chloropyrimidin-4-yl)-N-(8-chloronaphthalen-2-ylsulfonyl)-3-(1,2,3,4-tetrahydroisoquinoline-2-carbonyl)benzamide;
4-(5-Chloro-2-(dipropylamino)pyrimidin-4-yl)-N-(naphthalen-2-ylsulfonyl)-3-(1,2,3,4-tetrahydroisoquinoline-2-carbonyl)benzamide;
4-(5-Chloro-2-(dipropylamino)pyrimidin-4-yl)-3-(S)-3-(hydroxymethyl)-1,2,3,4-tetrahydroisoquinoline-2-carbonyl)-N-(naphthalen-2-ylsulfonyl)benzamide;
4-(5-Bromo-2-(dipropylamino)pyrimidin-4-yl)-3-((S)-3-(hydroxymethyl)-1,2,3,4-tetrahydroisoquinoline-2-carbonyl)-N-(naphthalen-2-ylsulfonyl)benzamide;
4-(5-Chloro-2-((cyclopropylmethyl)(propyl)amino)pyrimidin-4-yl)-3-((S)-3-(hydroxymethyl)-1,2,3,4-tetrahydroisoquinoline-2-carbonyl)-N-(naphthalen-2-ylsulfonyl)benzamide;
3-((S)-3-(Aminomethyl)-1,2,3,4-tetrahydroisoquinoline-2-carbonyl)-4-(5-chloro-2-(dipropylamino)pyrimidin-4-yl)-N-(naphthalen-2-ylsulfonyl)benzamide;
4-(5-Chloro-2-(dipropylamino)pyrimidin-4-yl)-N-(8-chloronaphthalen-2-ylsulfonyl)-3-((S)-3-(hydroxymethyl)-1,2,3,4-tetrahydroisoquinoline-2-carbonyl)benzamide;
3-((S)-3-(Aminomethyl)-1,2,3,4-tetrahydroisoquinoline-2-carbonyl)-4-(5-chloro-2-(dipropylamino)pyrimidin-4-yl)-N-(8-chloronaphthalen-2-ylsulfonyl)benzamide;
1-(4-(((1-((2-Aminoethyl)thio)isoquinolin-6-yl)sulfonyl)carbamoyl)-2-(1,2,3,4-tetrahydroisoquinoline-2-carbonyl)phenyl)-N,N-dibutyl-4-chloro-5-methyl-1H-pyrazole-3-carboxamide; and
2-((6-(N-(4-(4-Chloro-3-(dibutylcarbamoyl)-5-methyl-1H-pyrazol-1-yl)-3-(1,2,3,4-tetrahydroisoquinoline-2-carbonyl)benzoyl)sulfamoyl) isoquinolin-1-yl)thio)acetic acid.

In some embodiments, the compound is selected from the group consisting of:

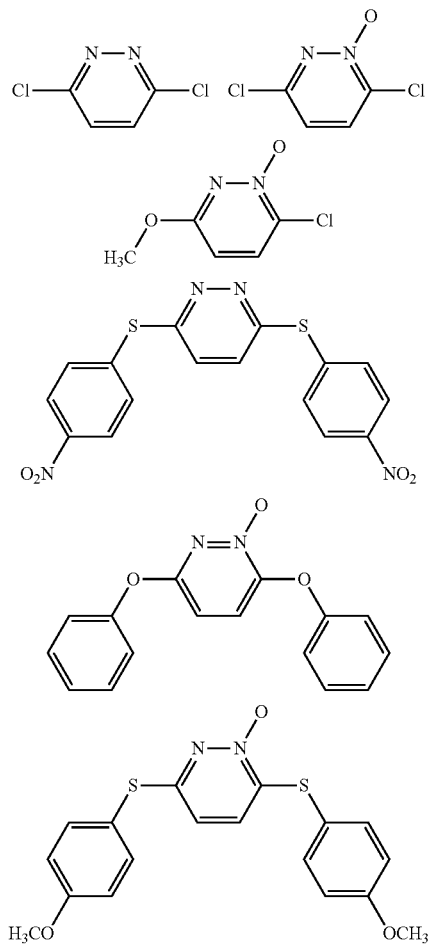

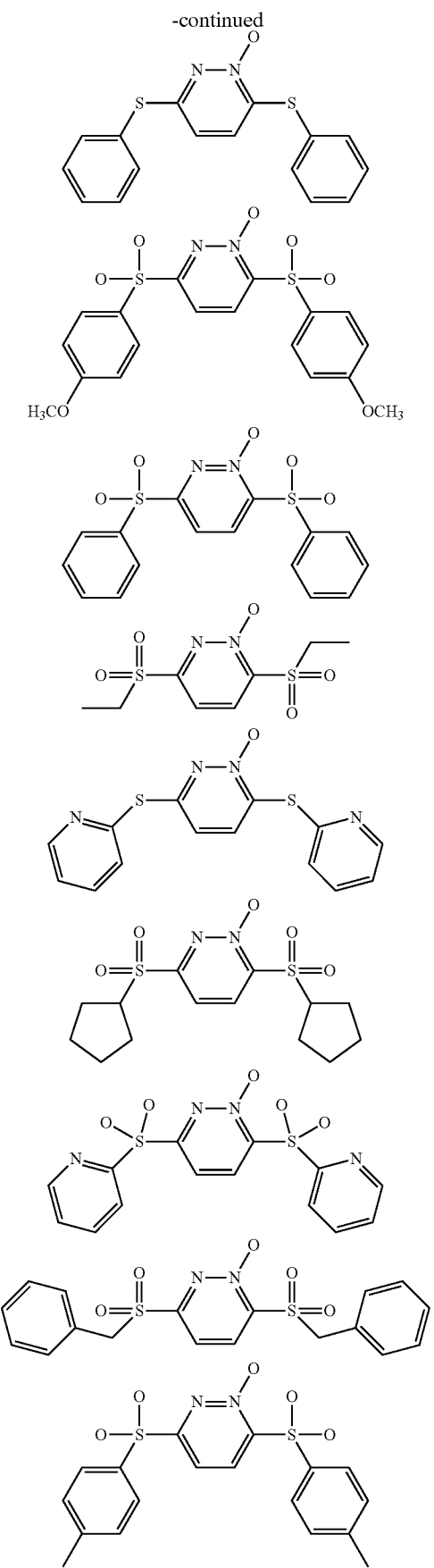
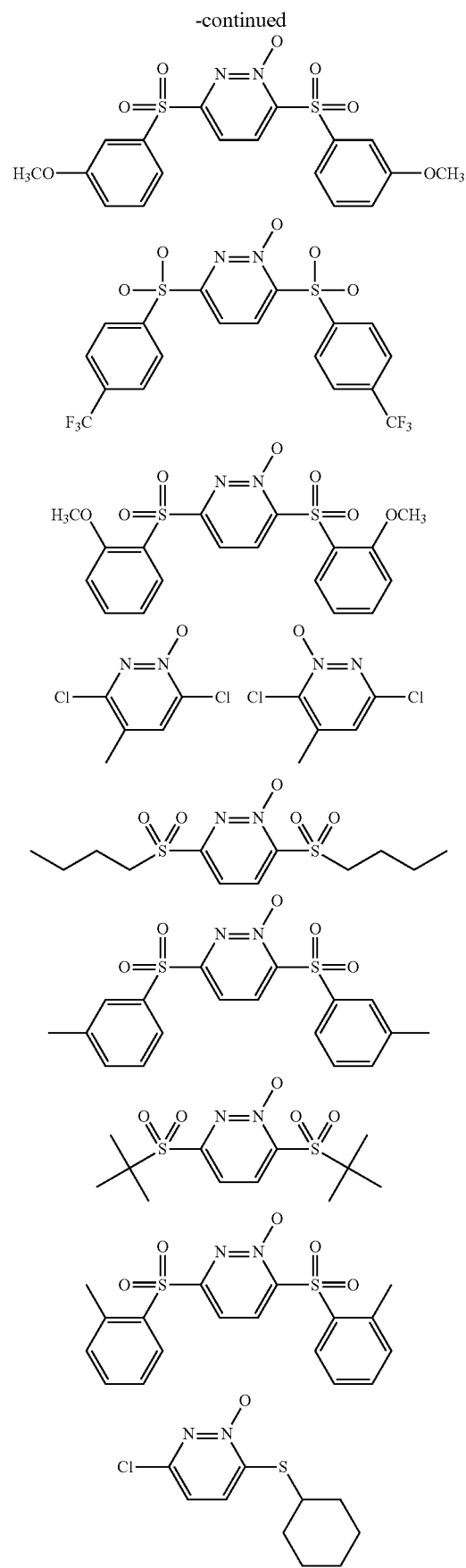

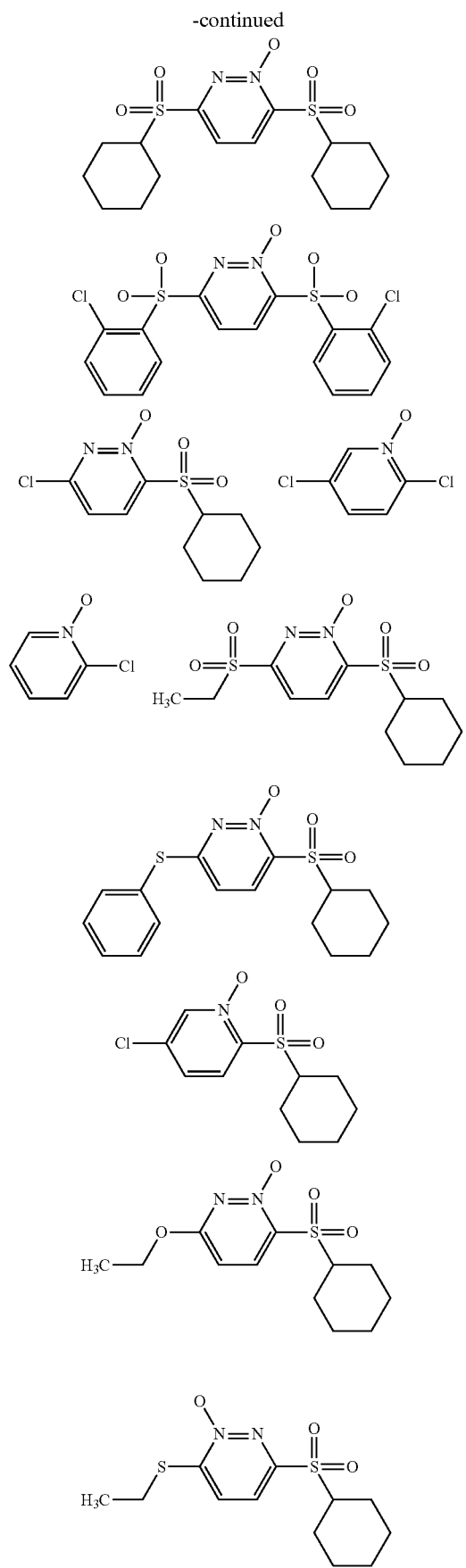
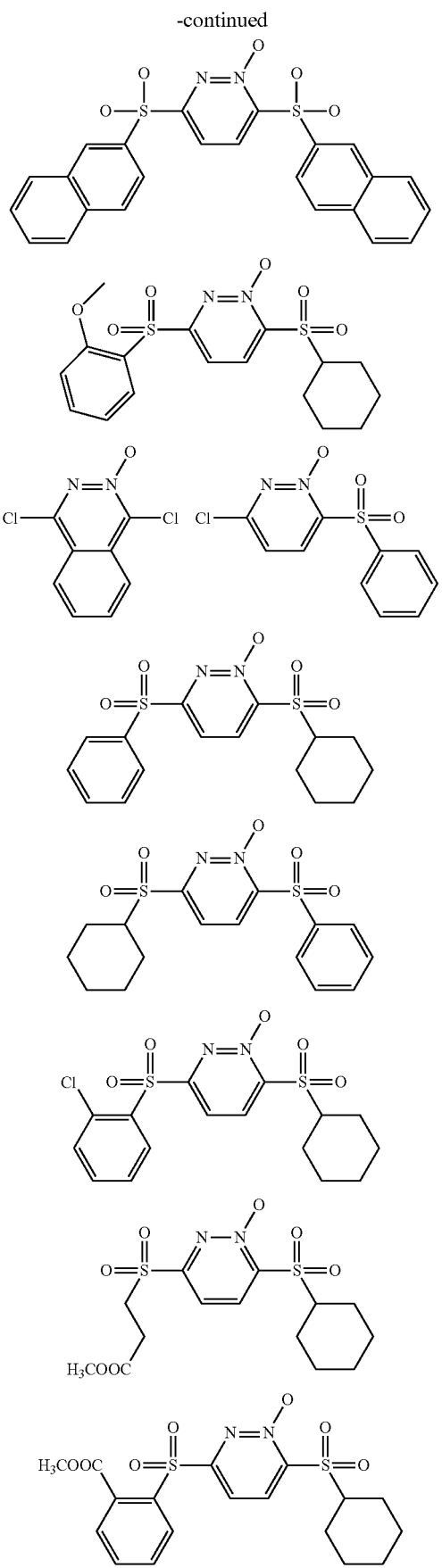

| 2025 | 2026 |
|---|---|
| -continued | -continued |
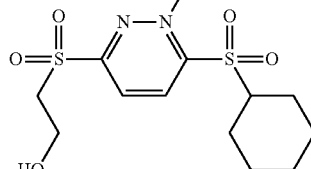
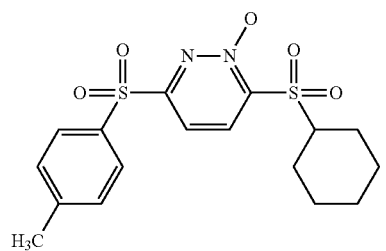
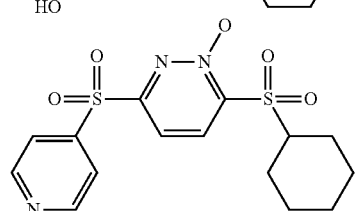
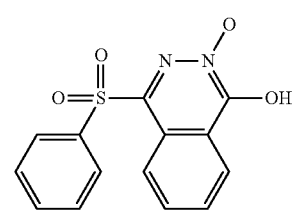
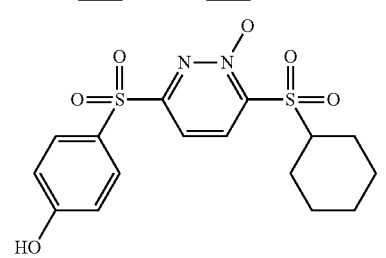
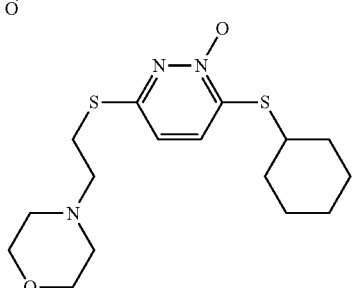
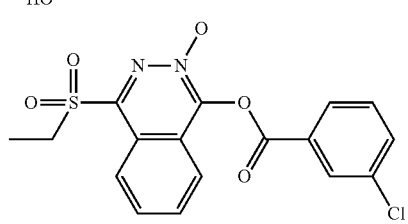
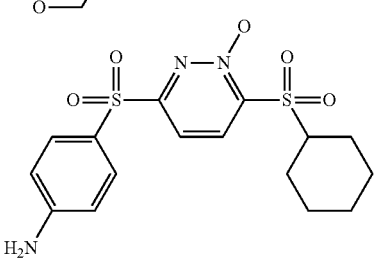
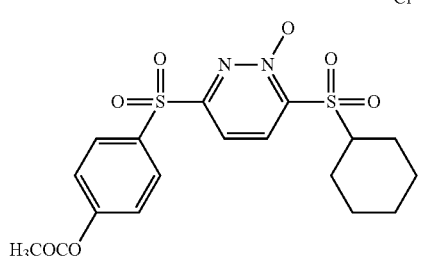
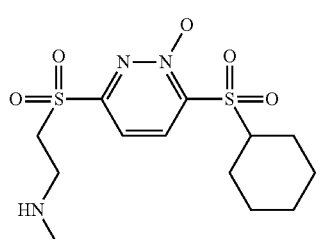
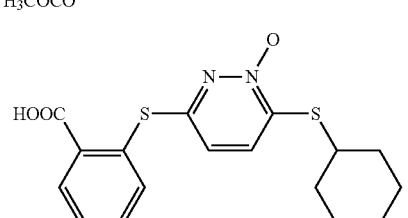
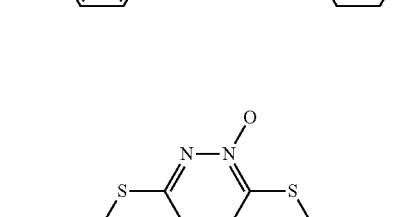
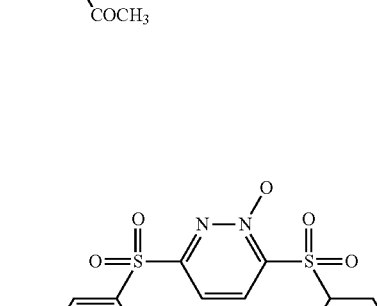
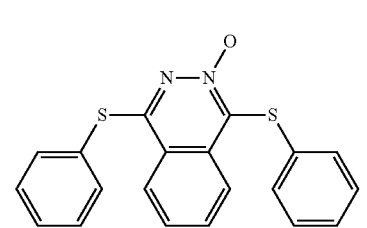
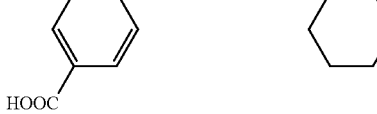

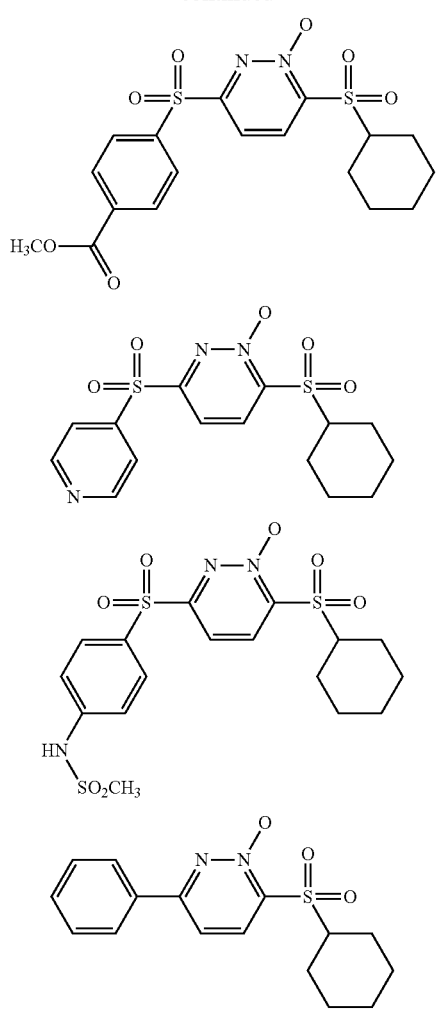
In some embodiments, the compound is selected from the group consisting of:
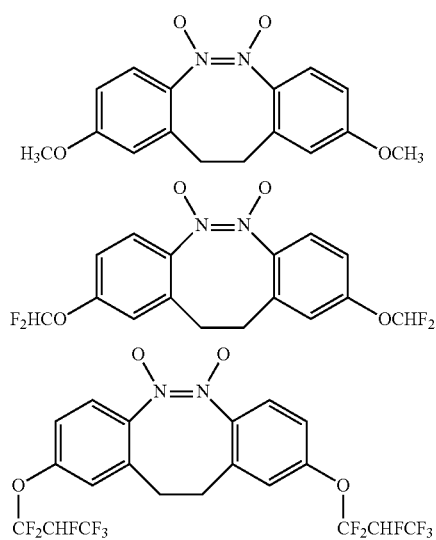
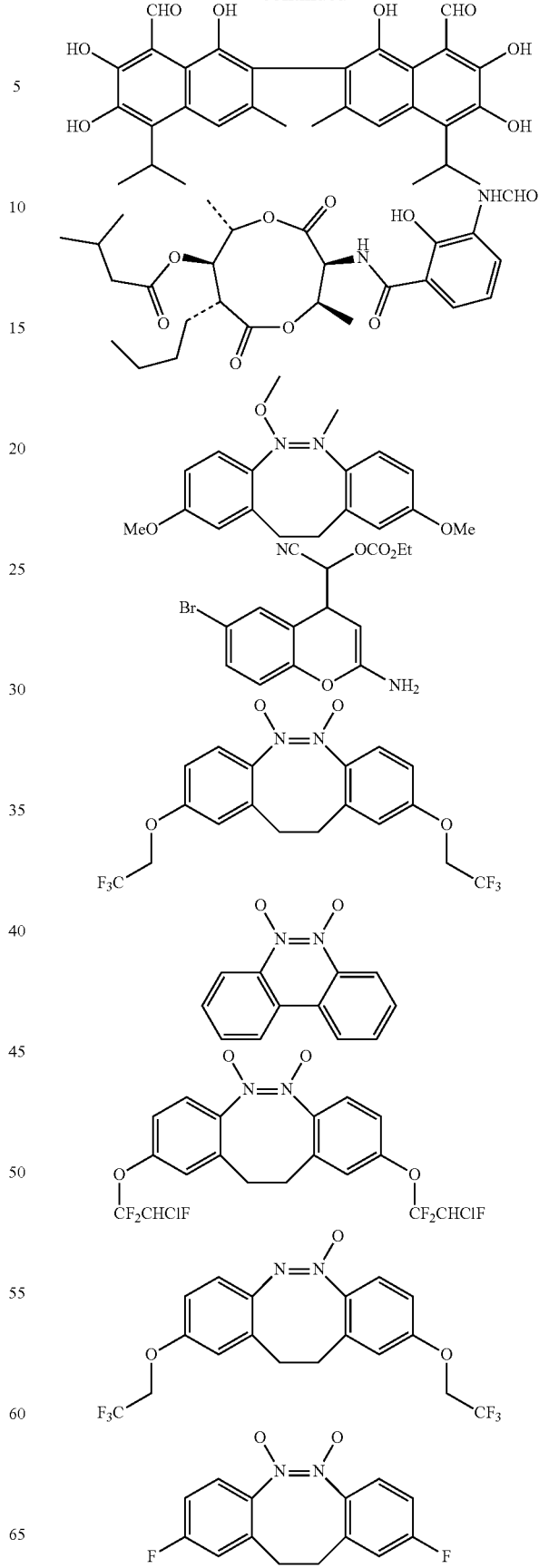

2029
-continued
2030
-continued
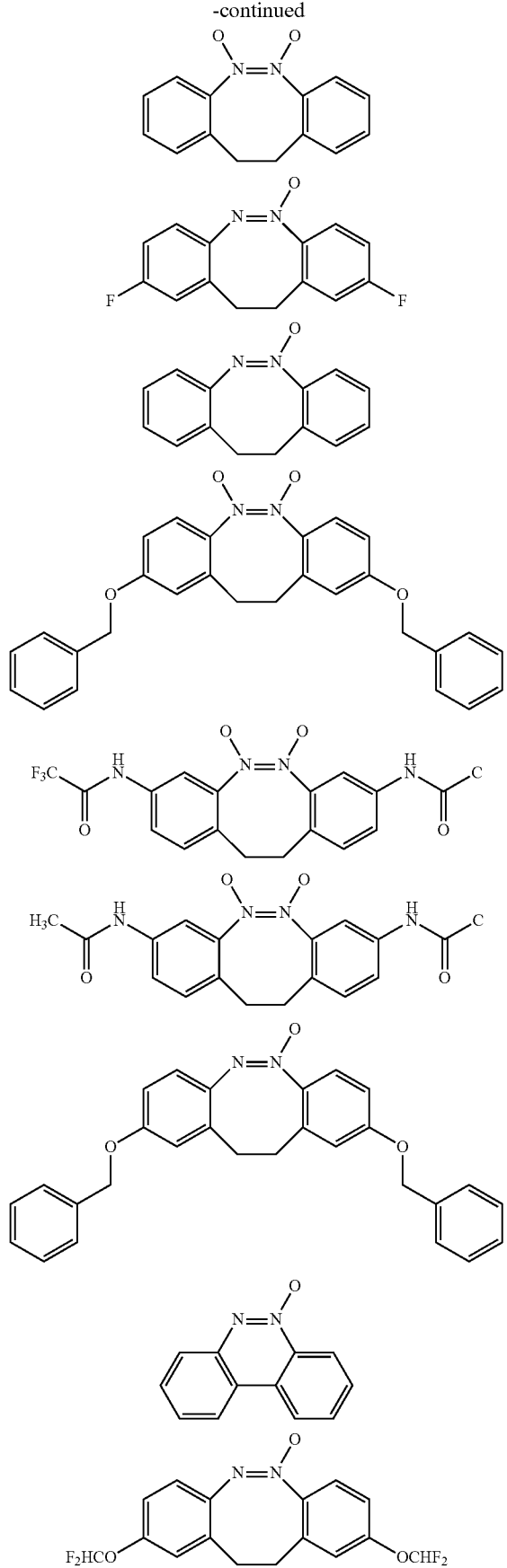
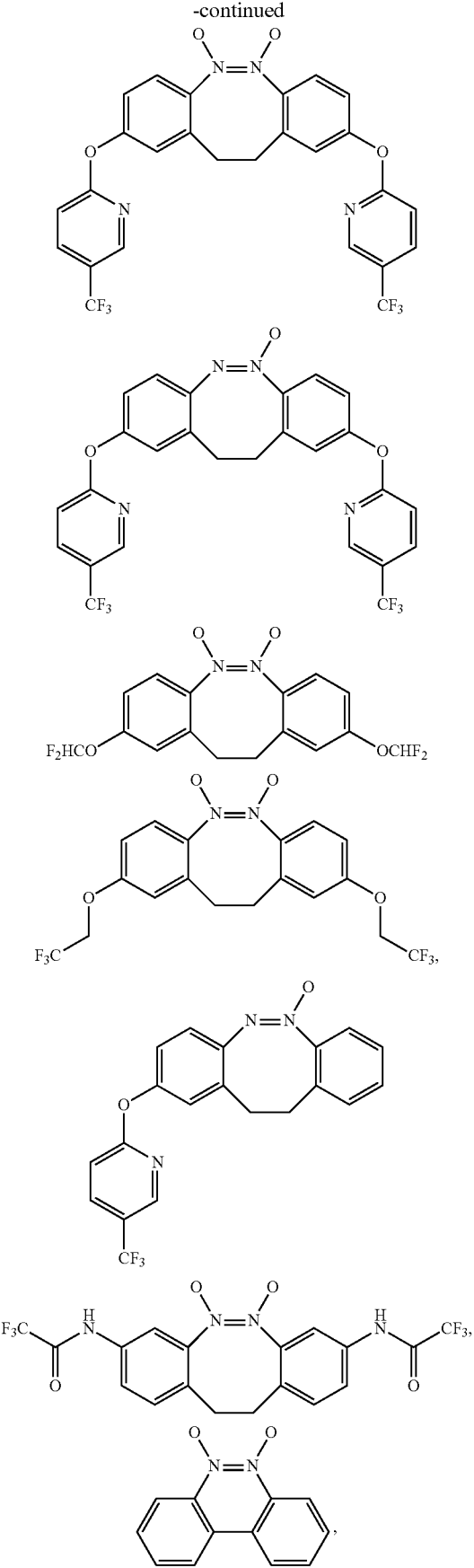

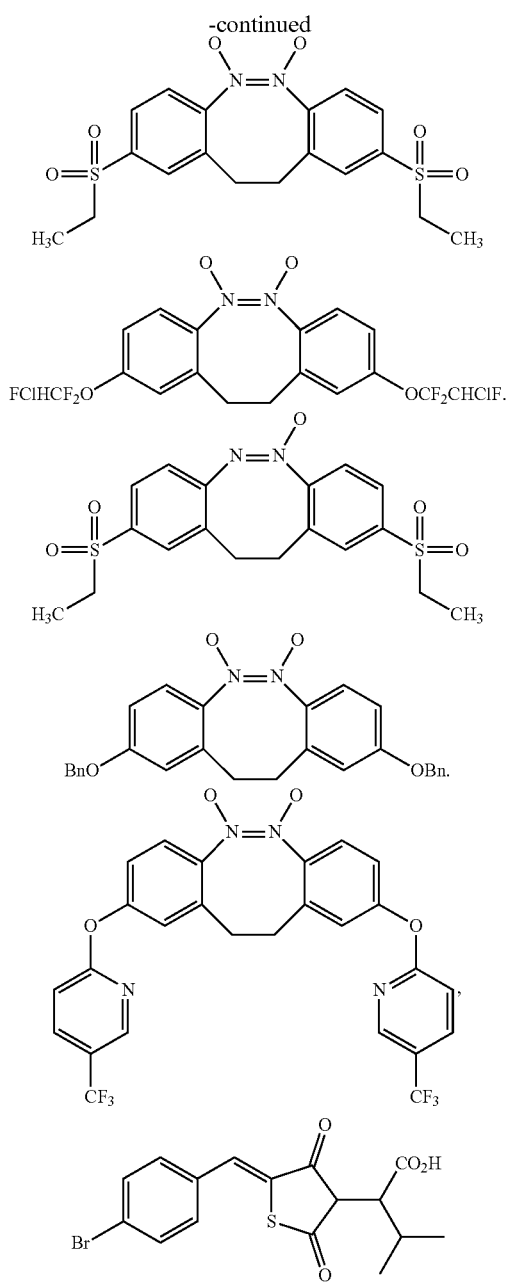
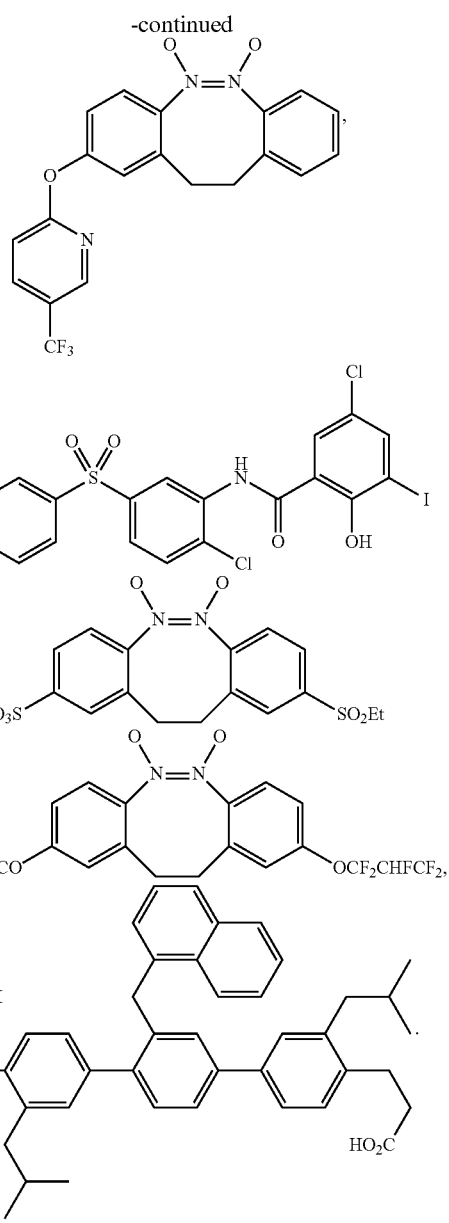
In some embodiments, the compound is selected from the group consisting of:
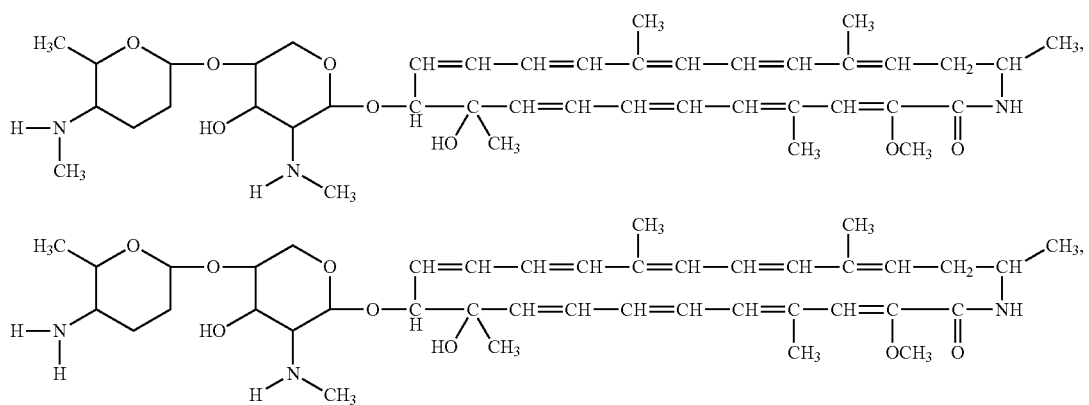

-continued
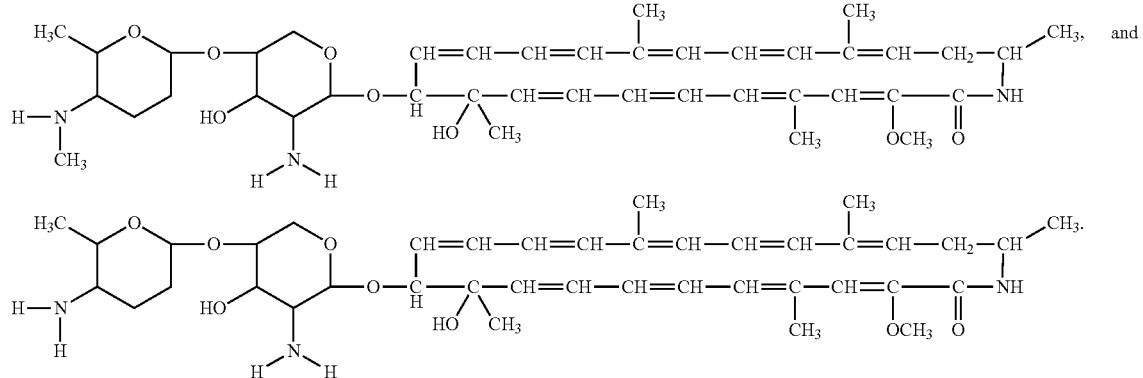
In some embodiments, the compound is selected from the group consisting of:
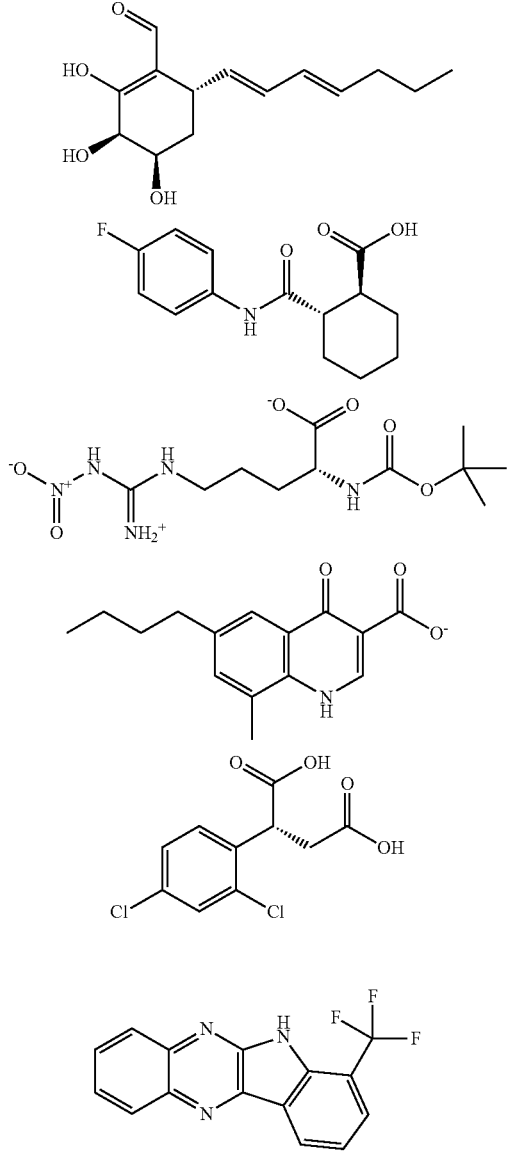
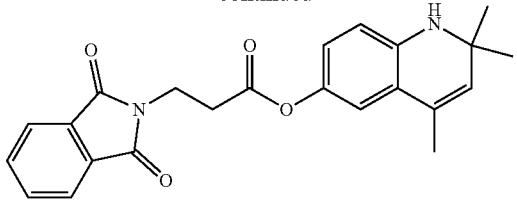
-continued
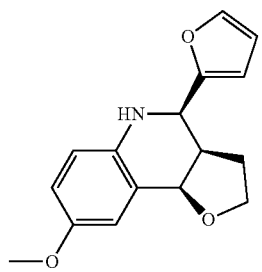
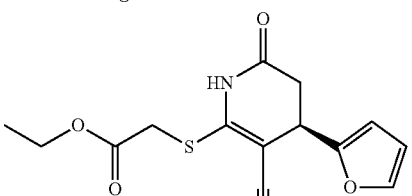
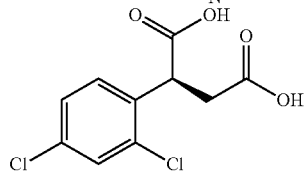
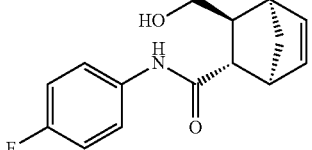
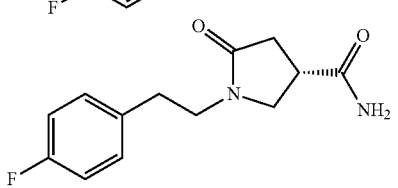

2035
-continued
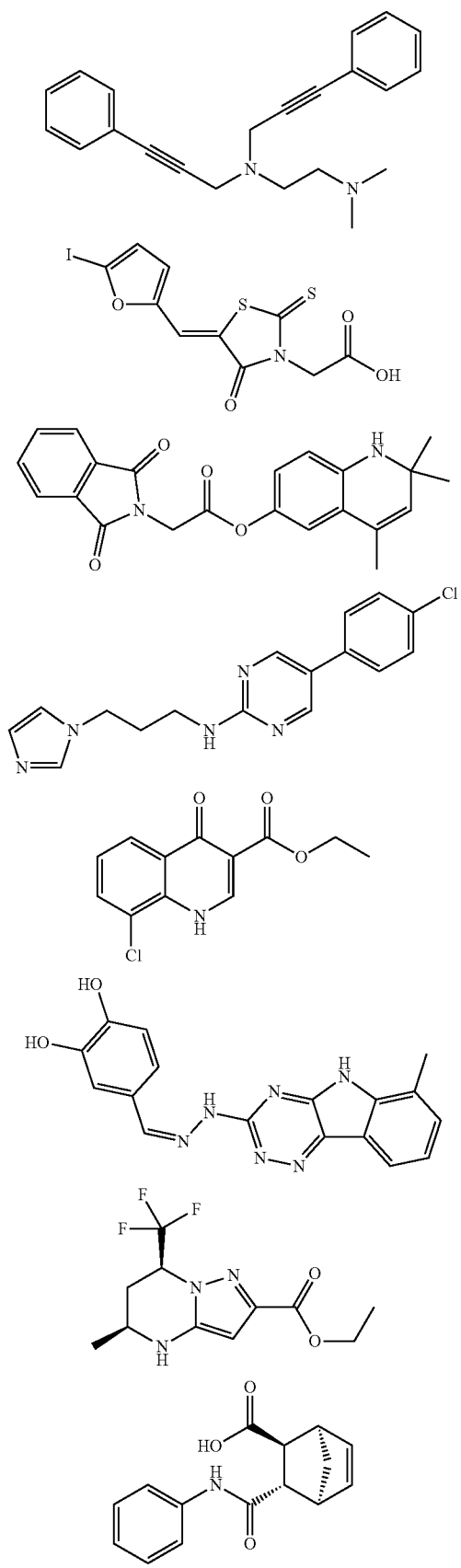
2036
-continued
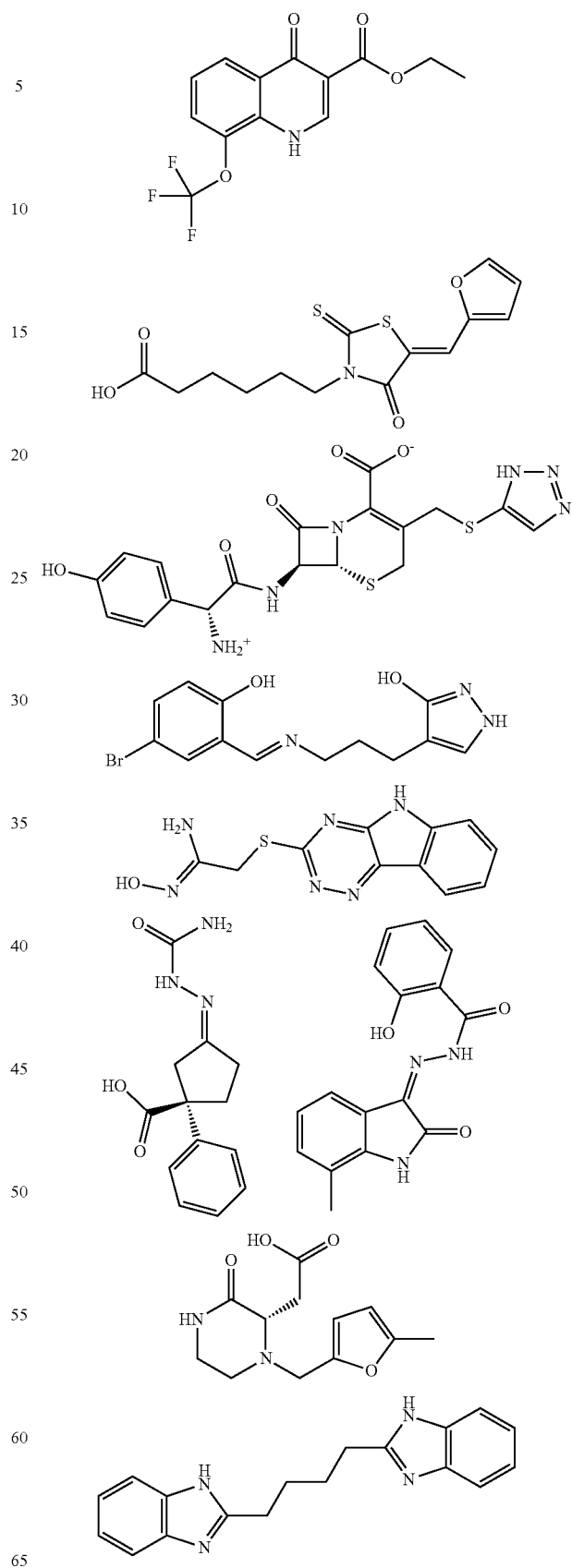

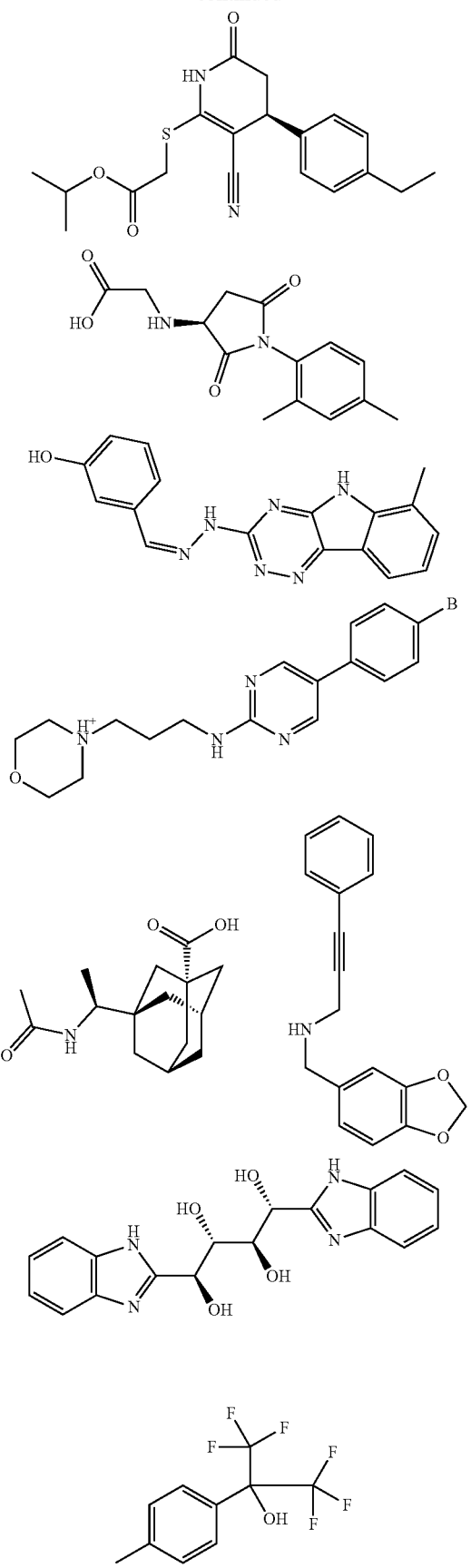
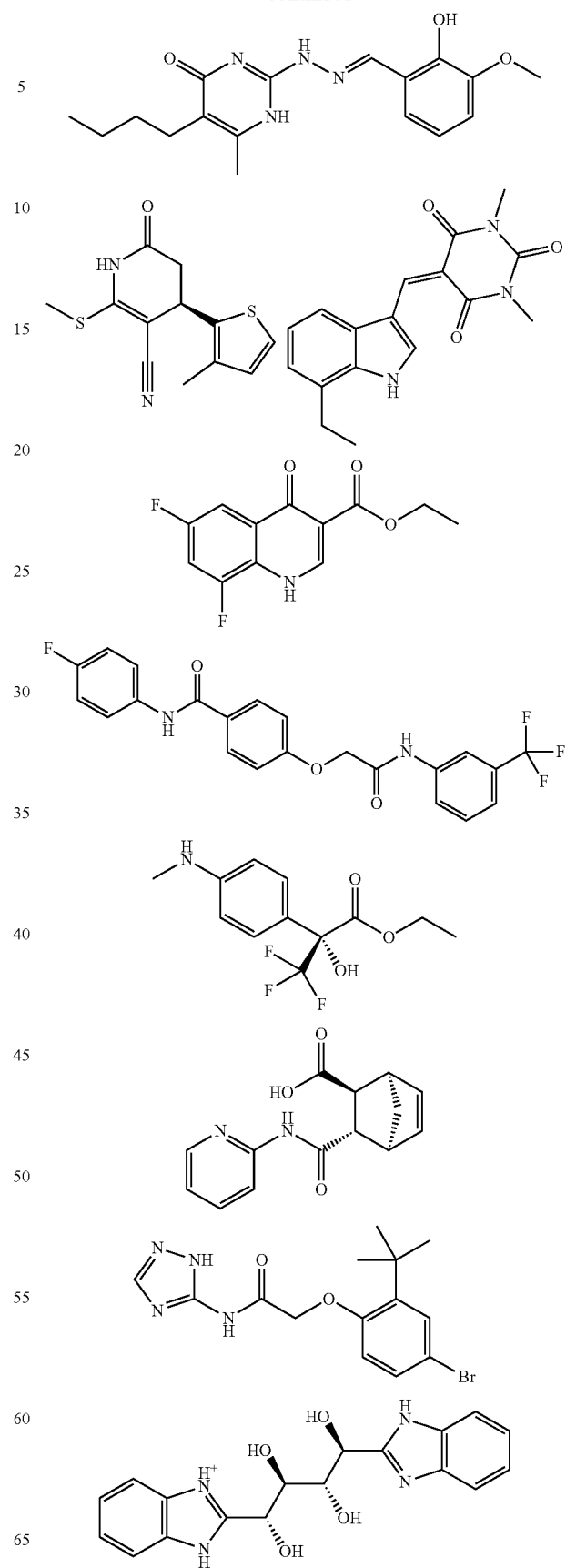

2039
-continued
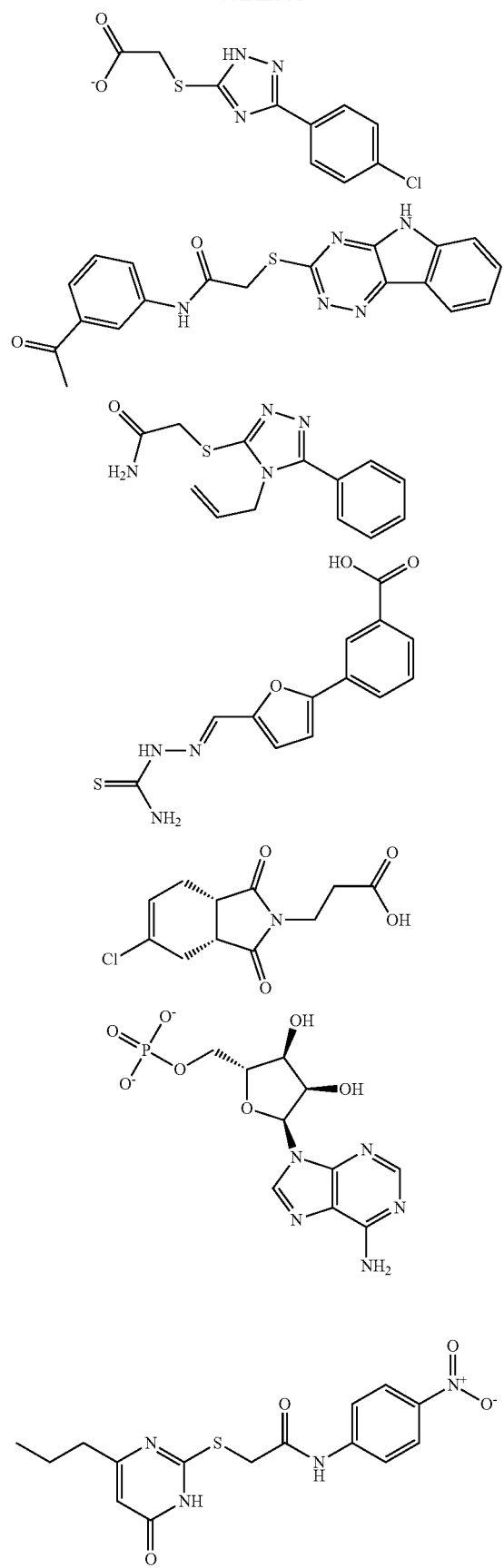
2040
-continued
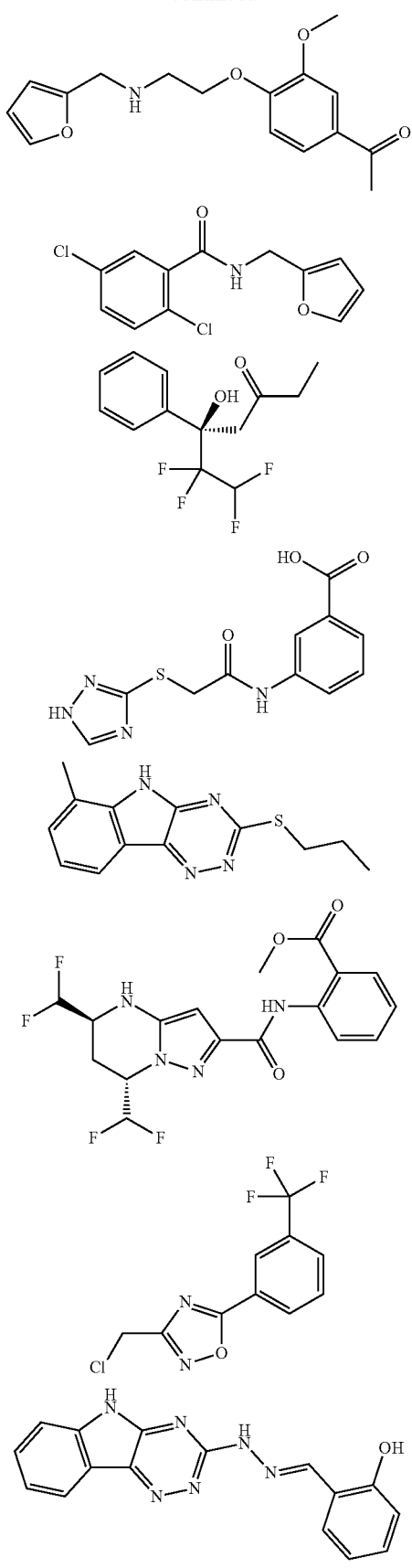

2041
-continued
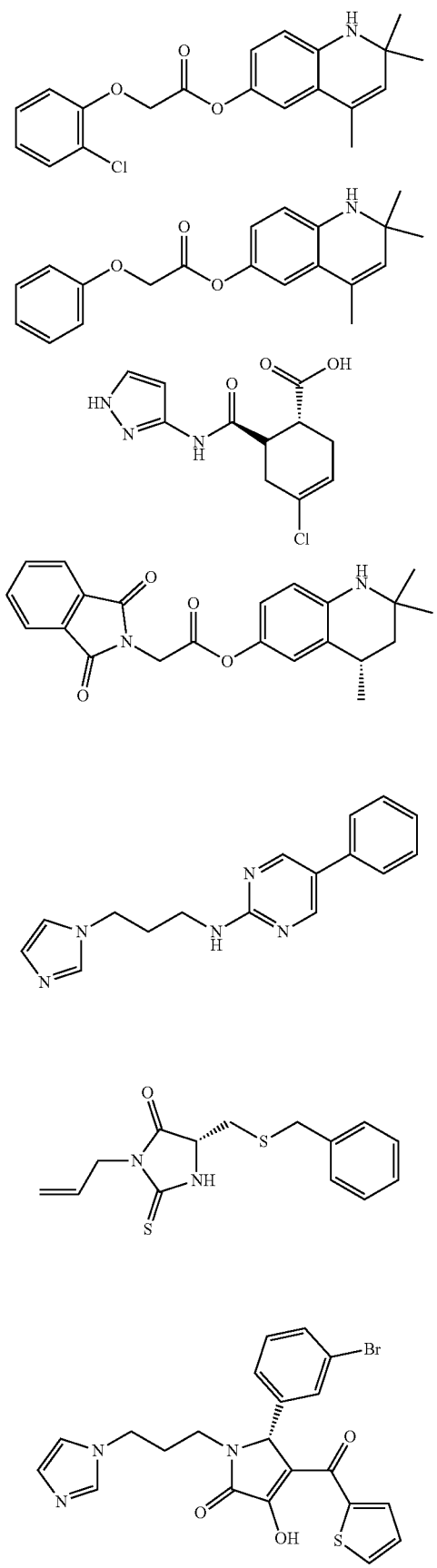
2042
-continued
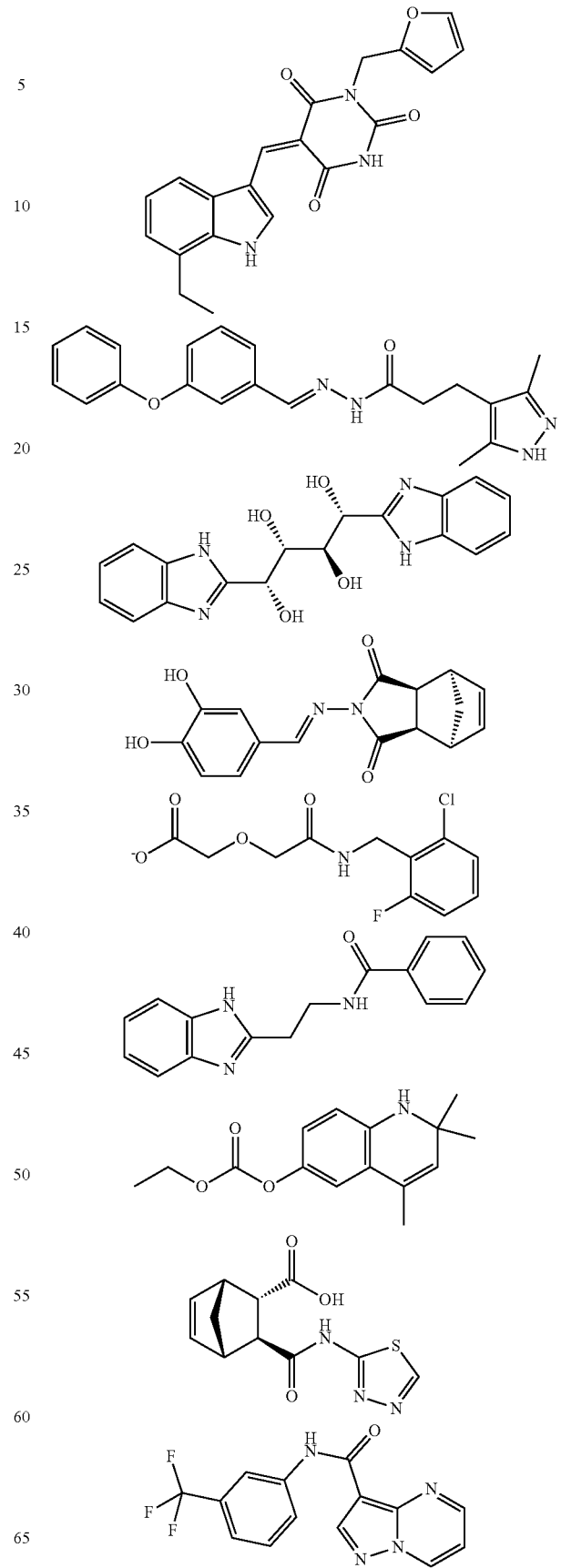

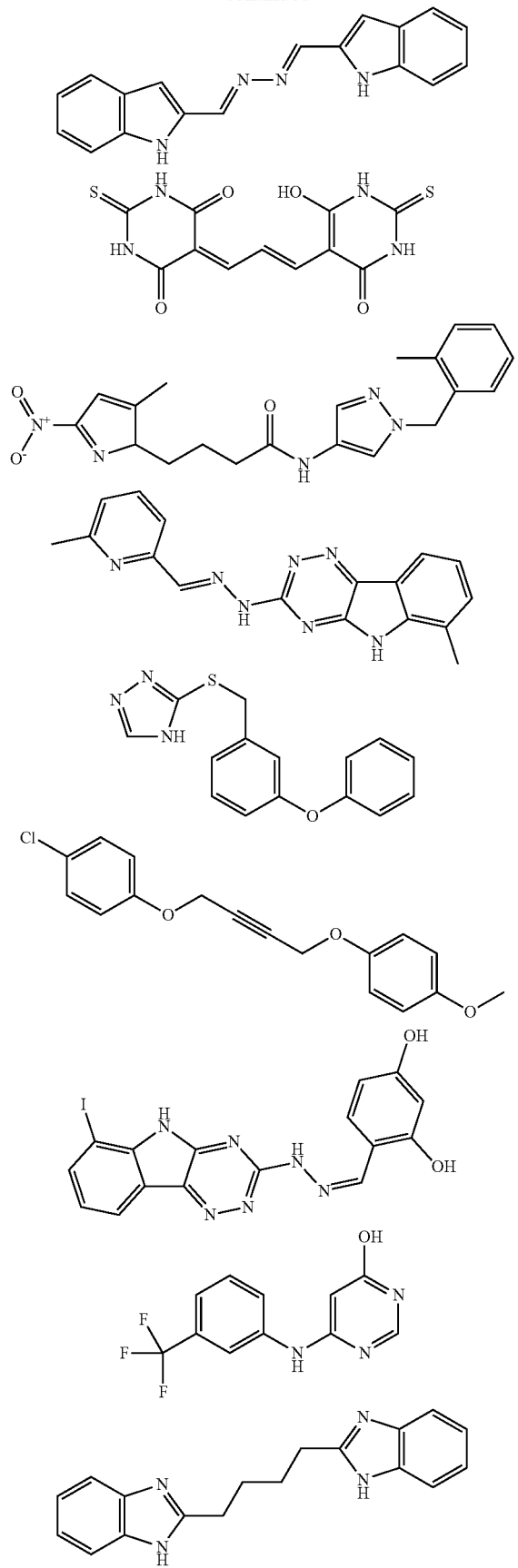
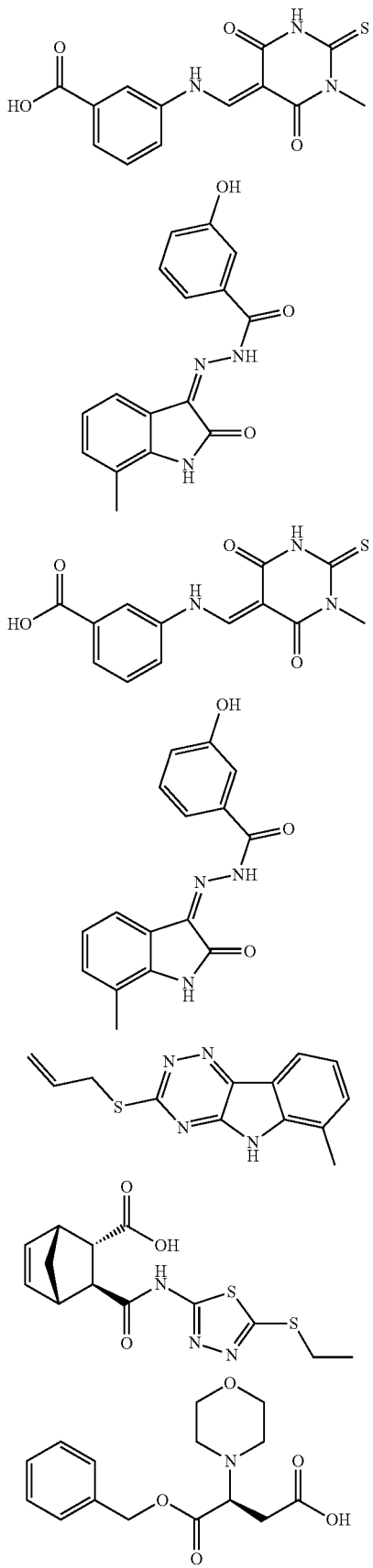

-continued
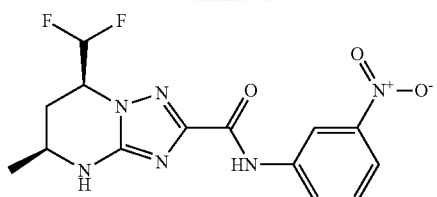
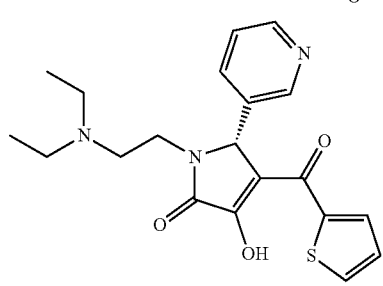
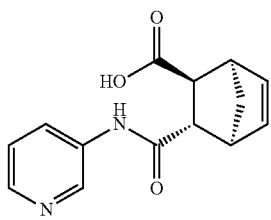
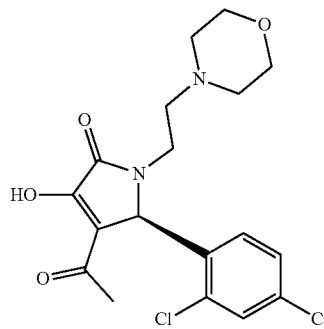
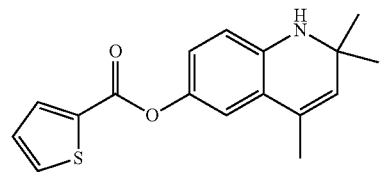
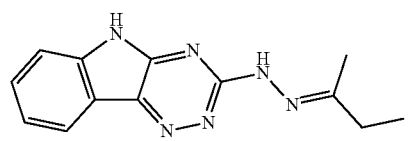
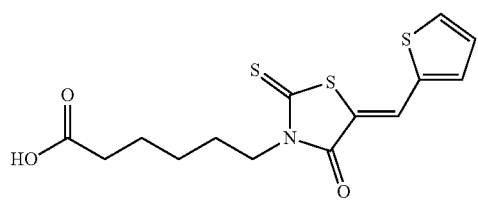
-continued
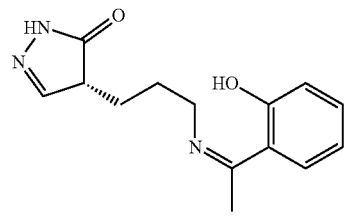
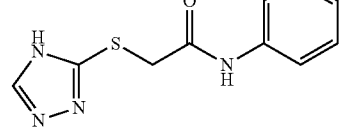
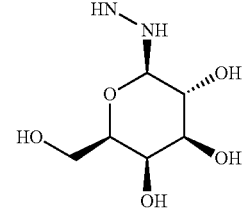
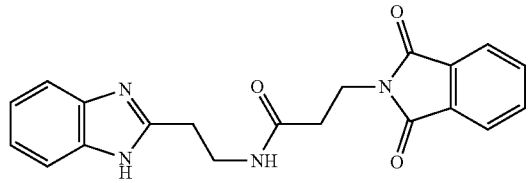
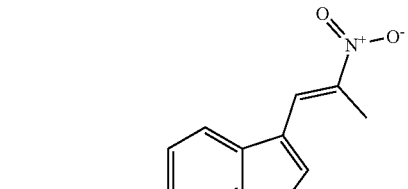
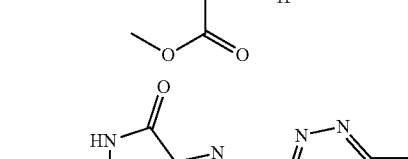
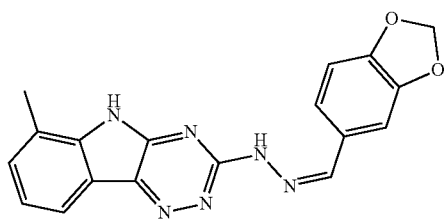

-continued
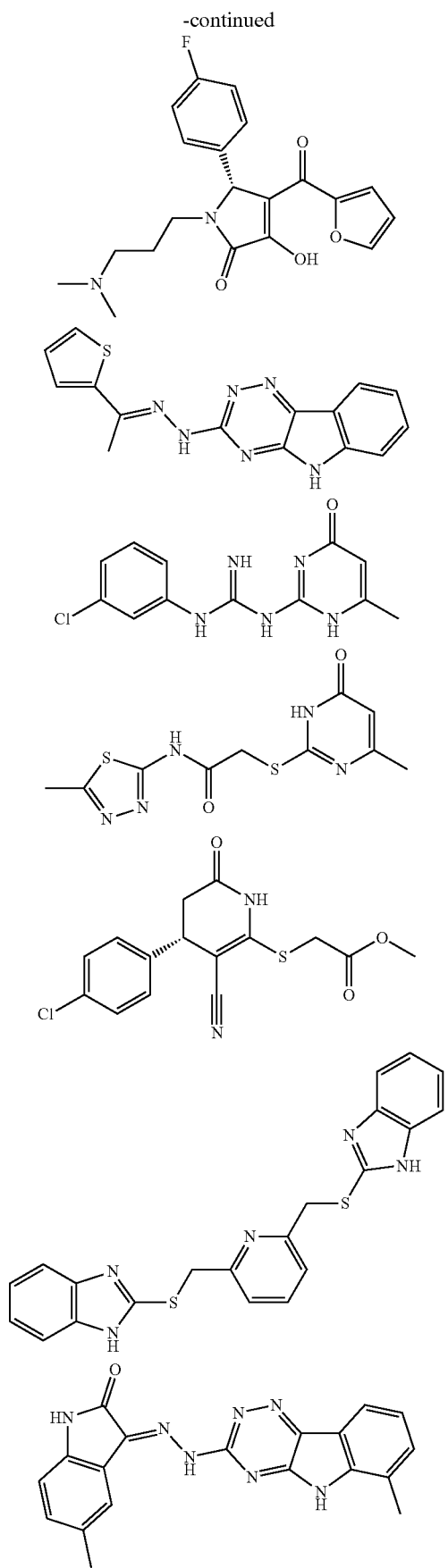
-continued
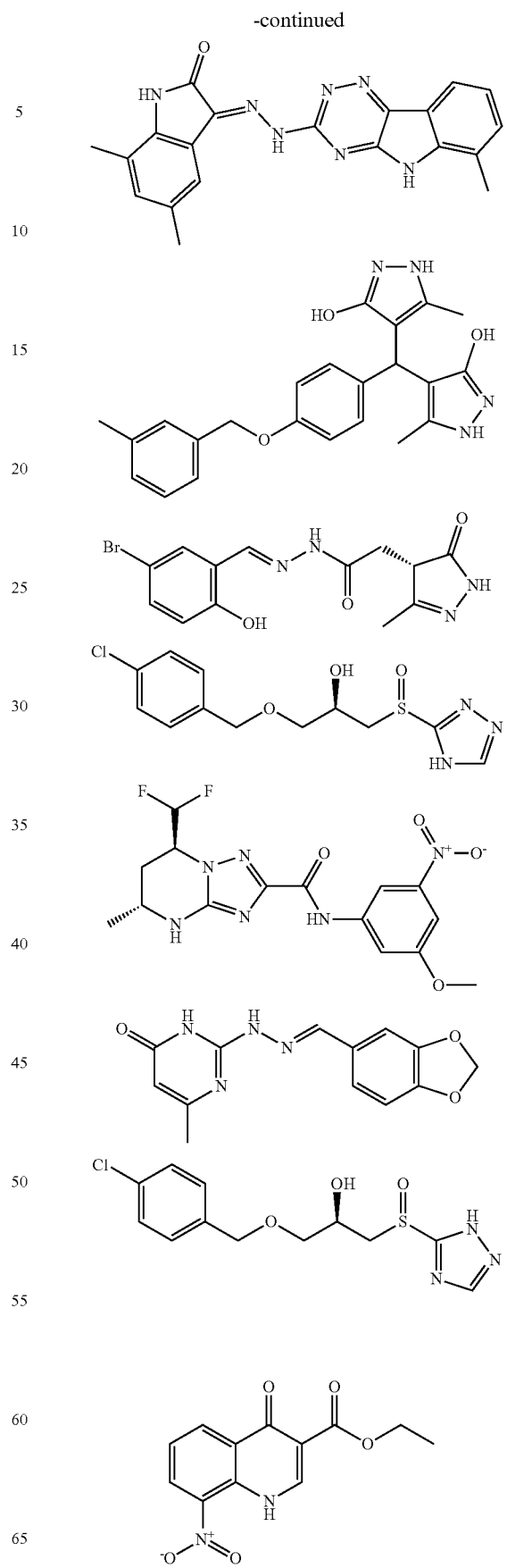

2049
-continued
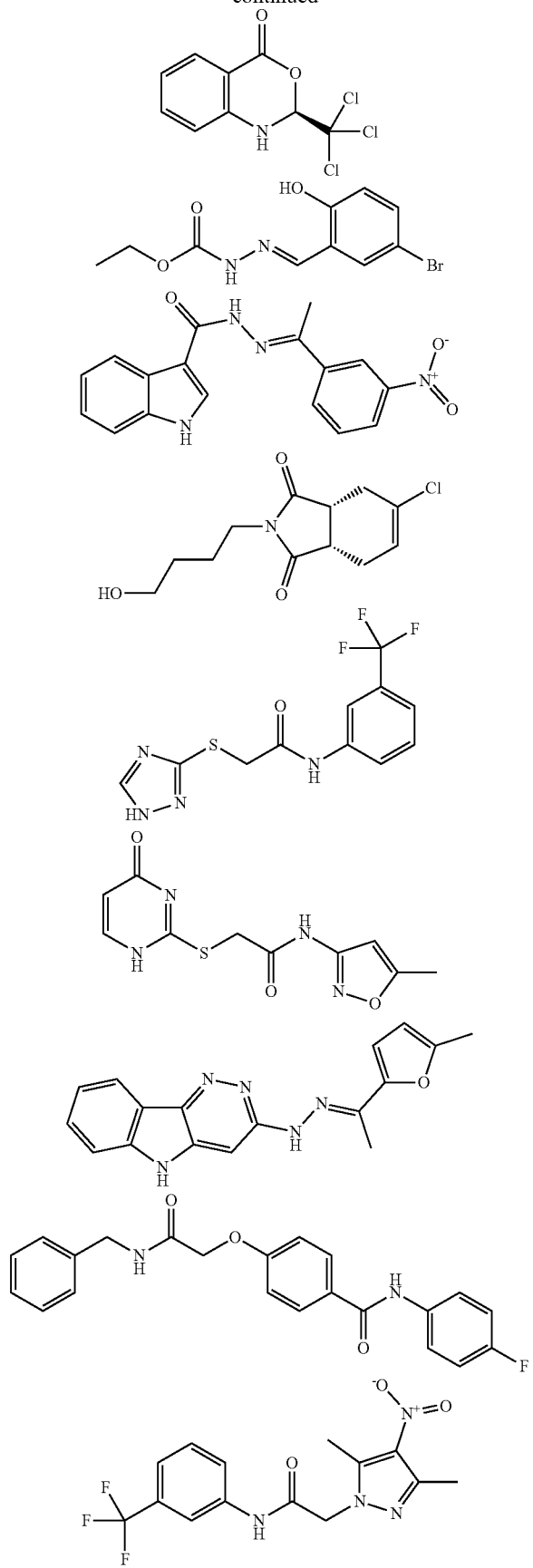
2050
-continued
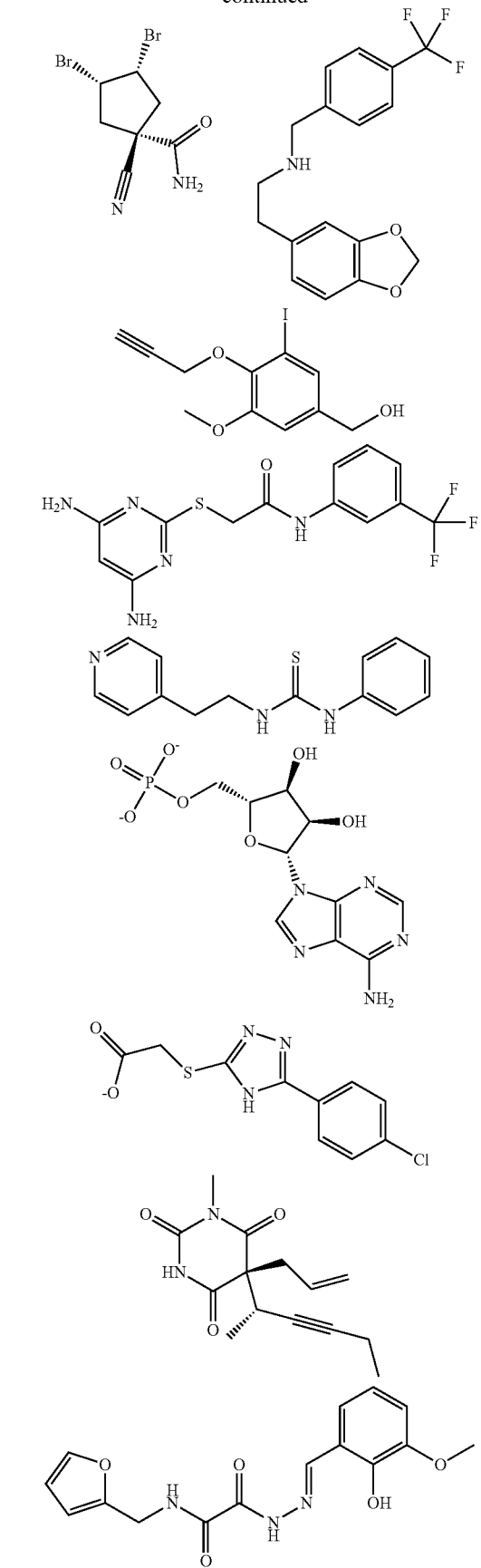

2051
-continued
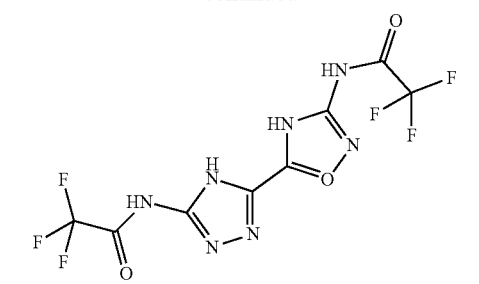
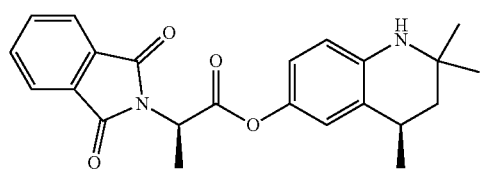
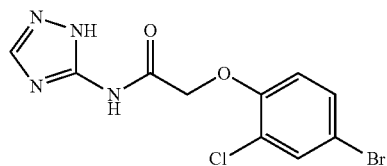
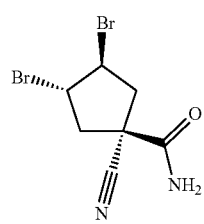
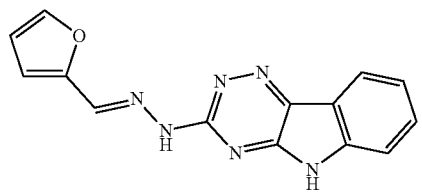
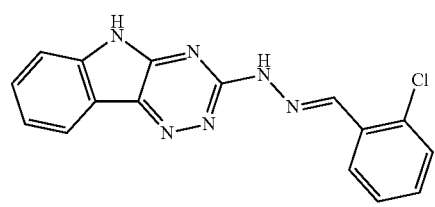
2052
-continued
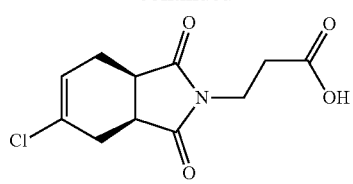
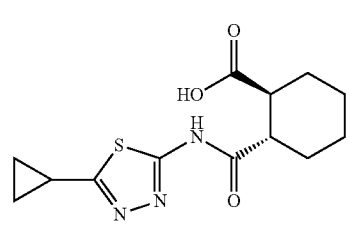
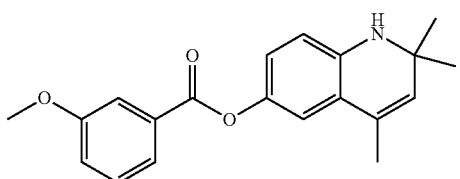
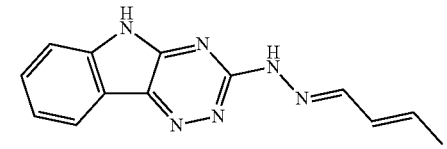
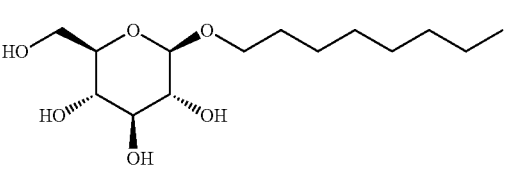
In some embodiments, the compound is selected from the group consisting of:

2053 2054
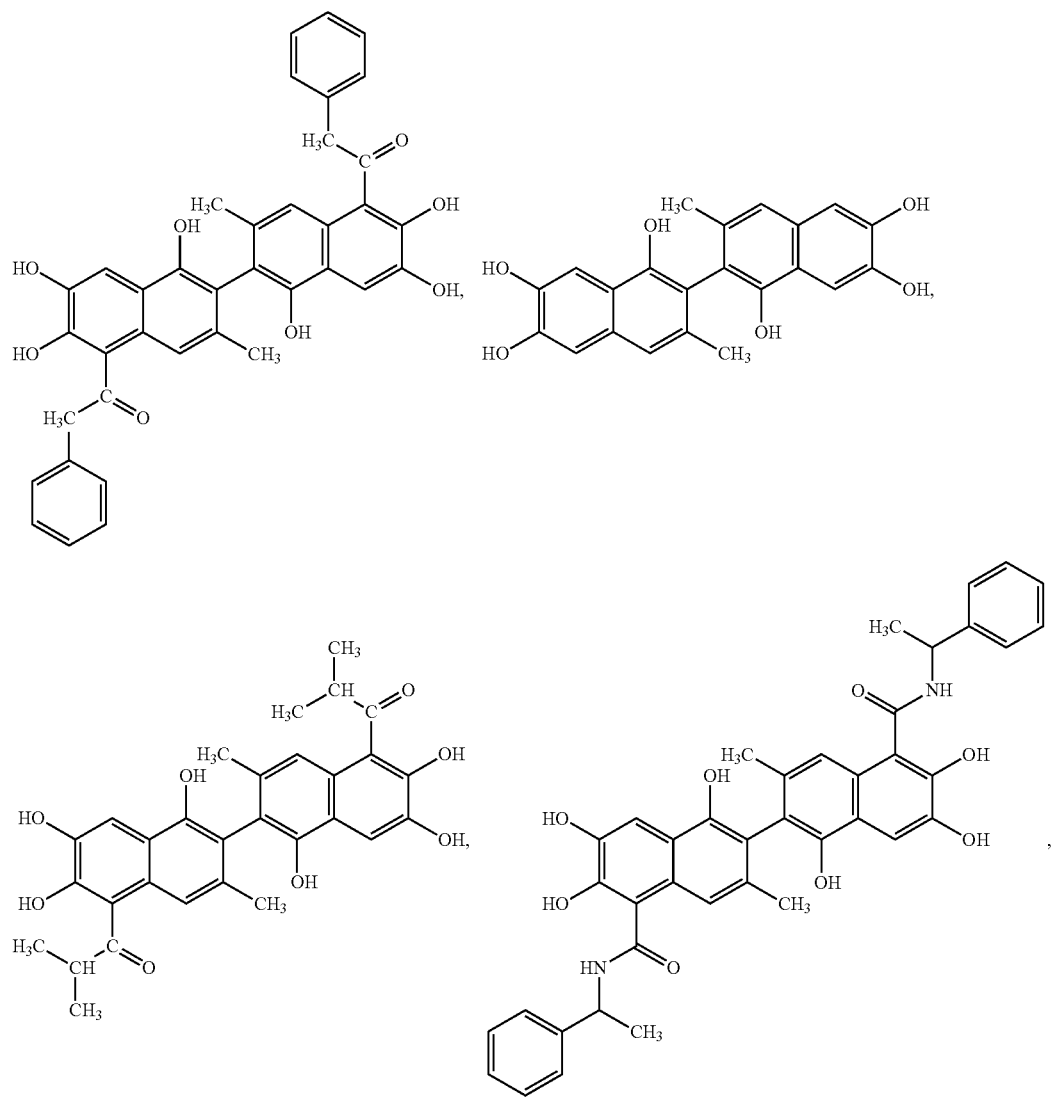
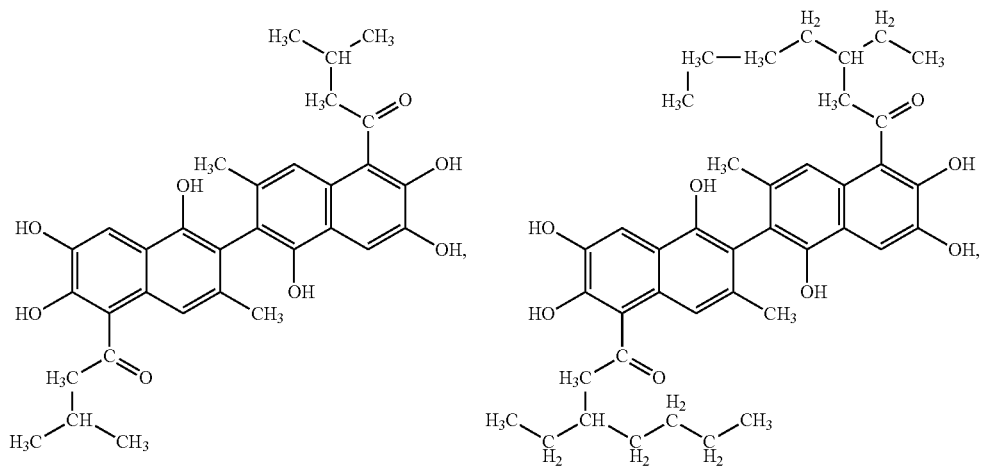

2055     -continued     2056
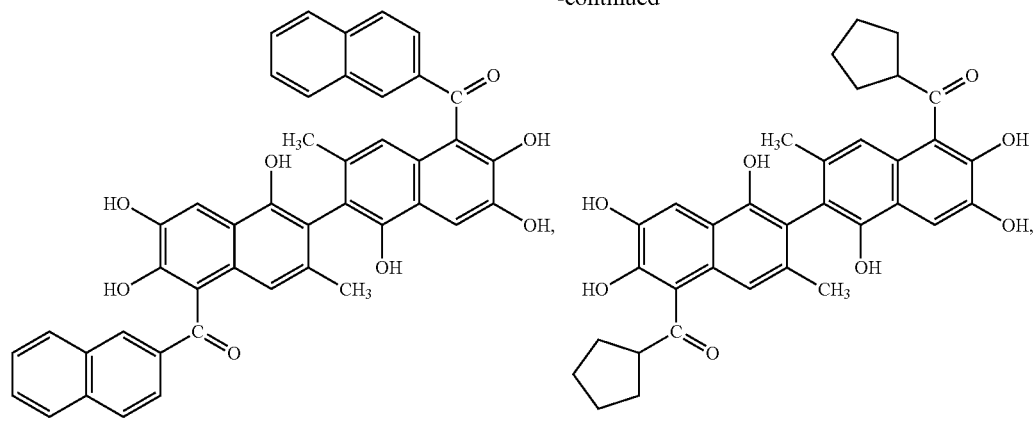
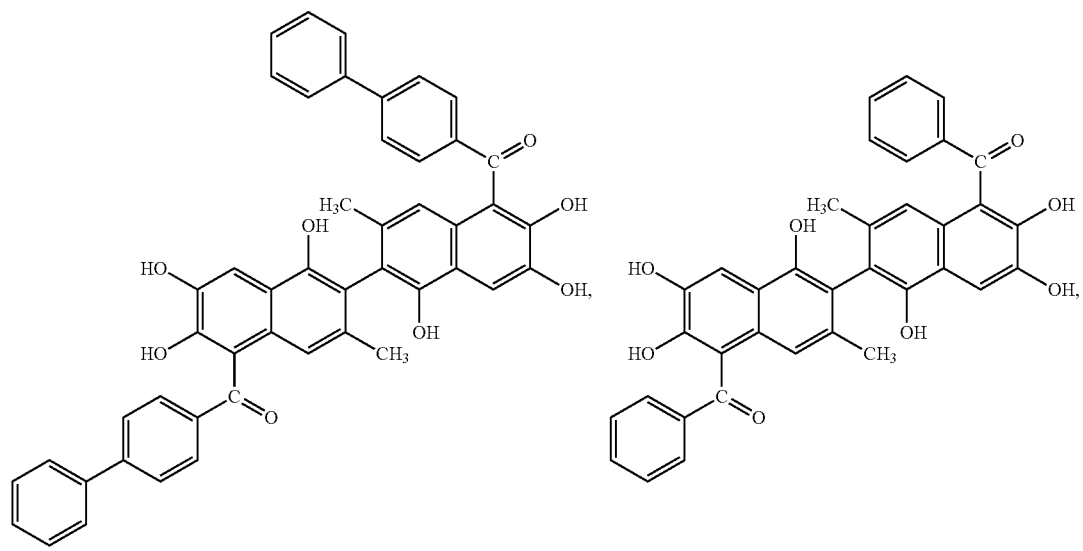
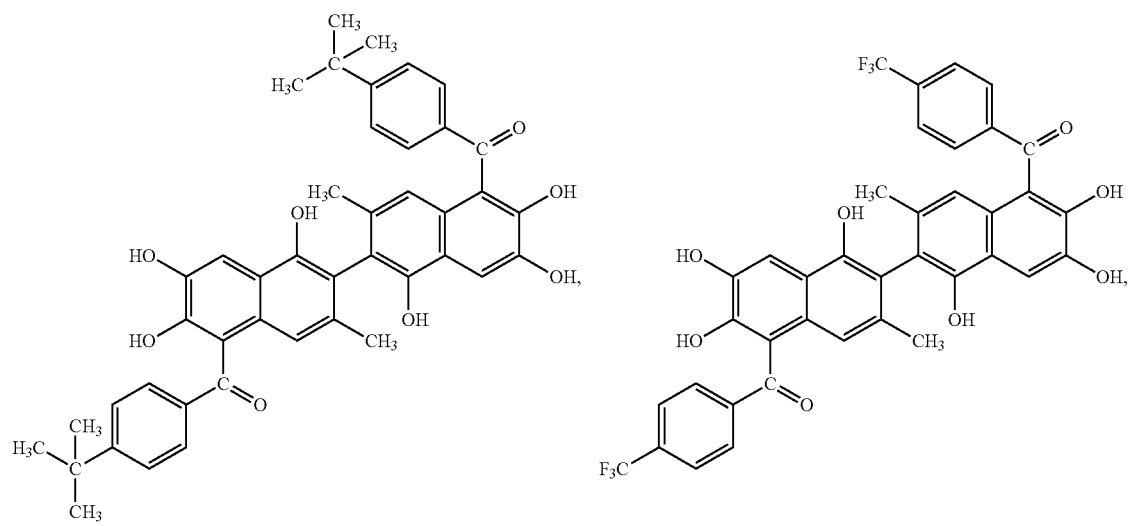

2057
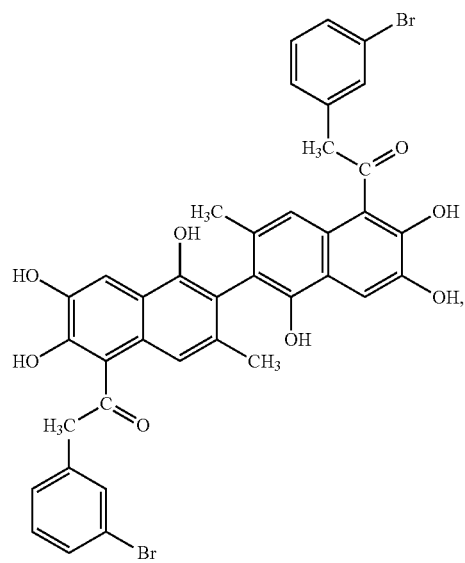
2058
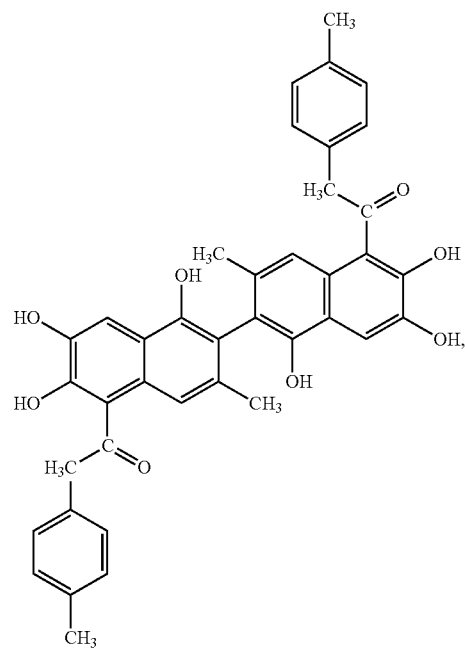
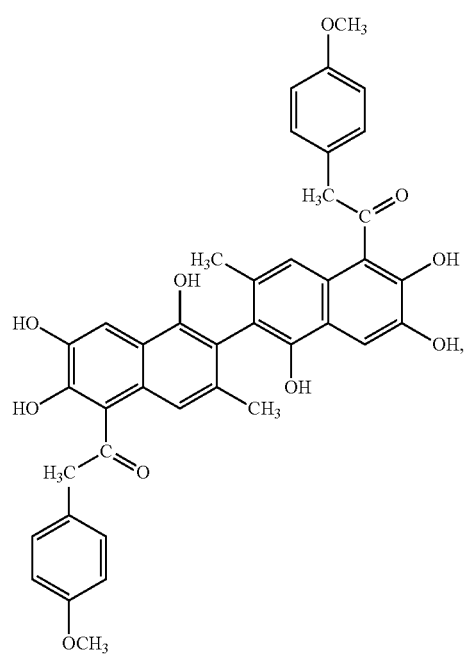
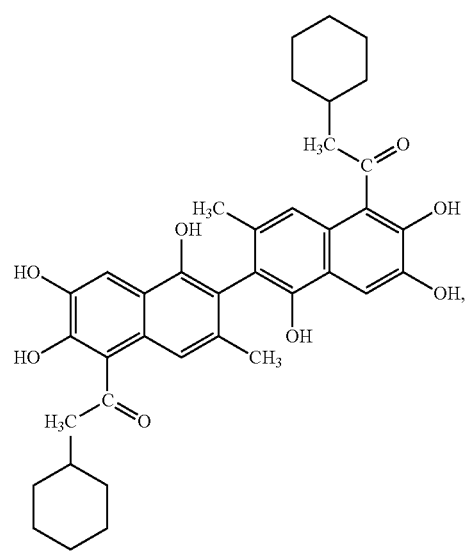

2059
-continued
2060
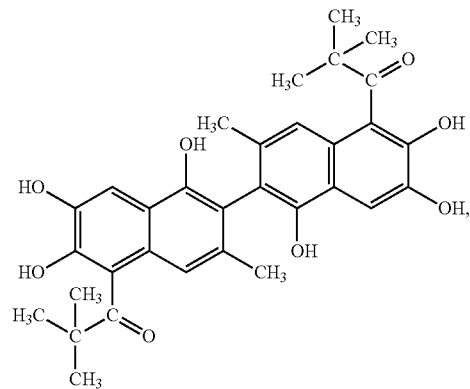
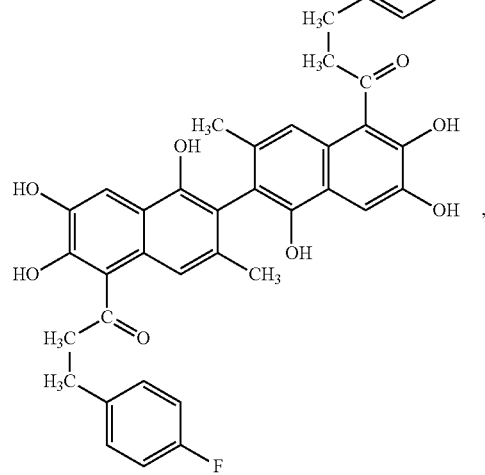
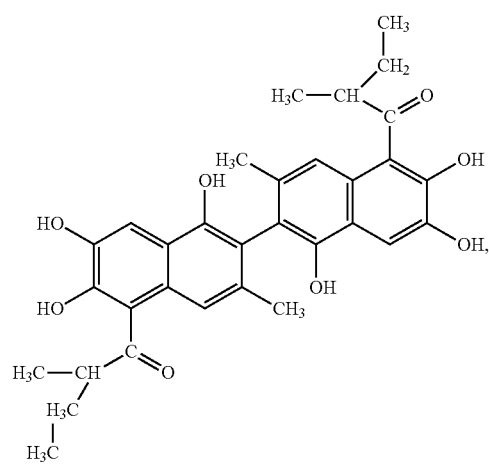
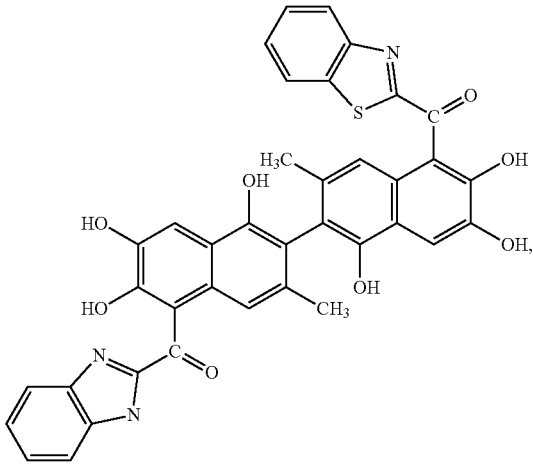
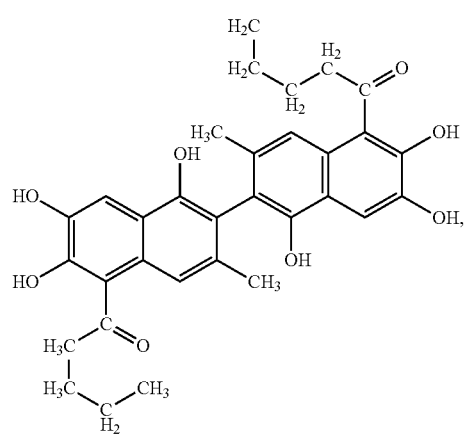
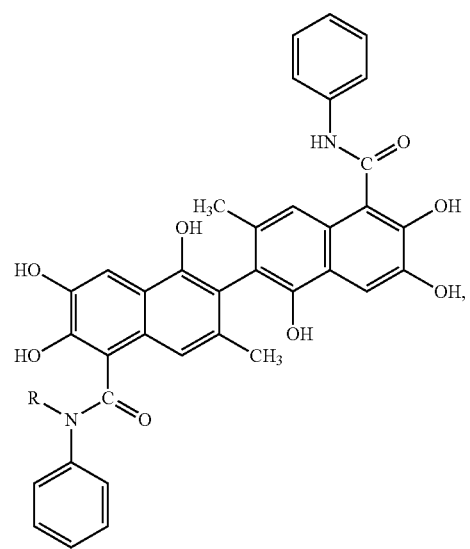

-continued
2061
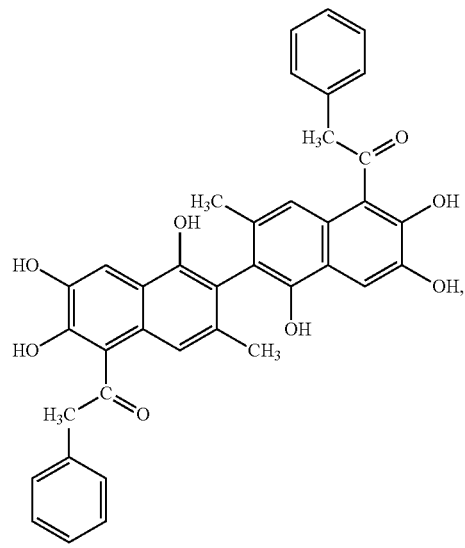
2062
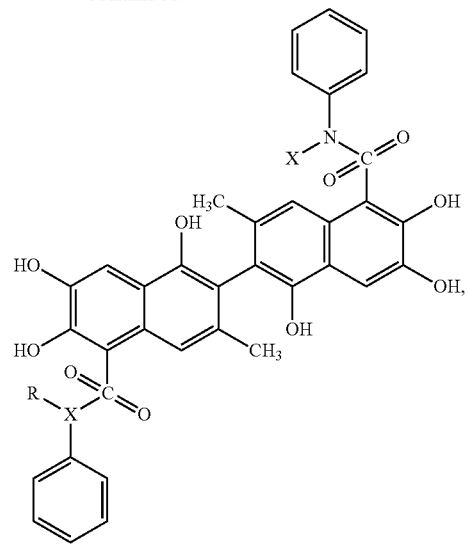
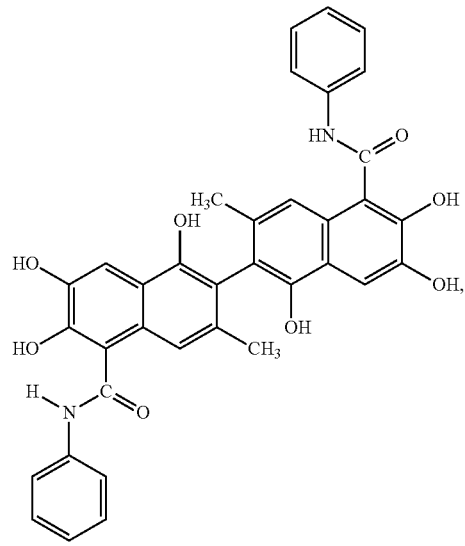
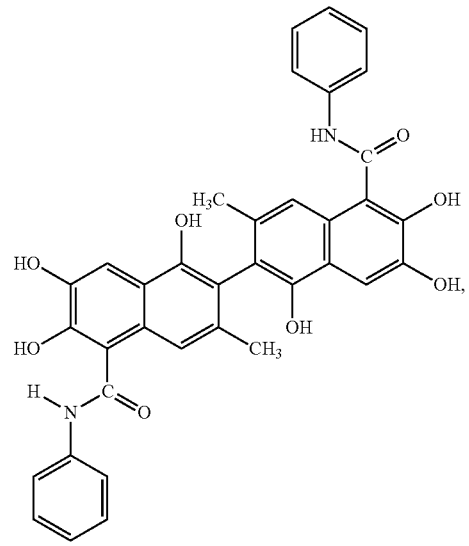
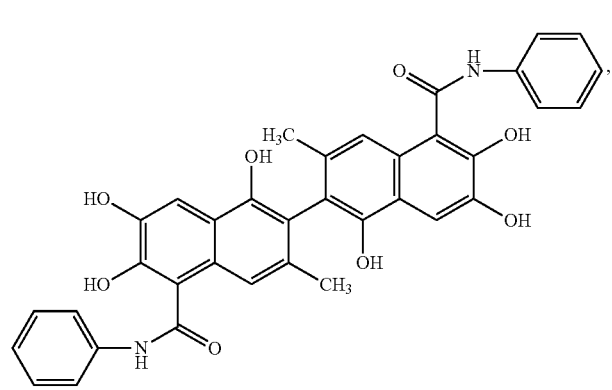
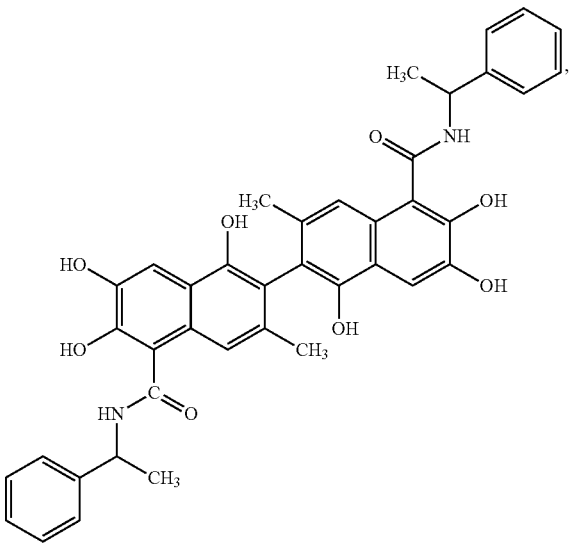

-continued
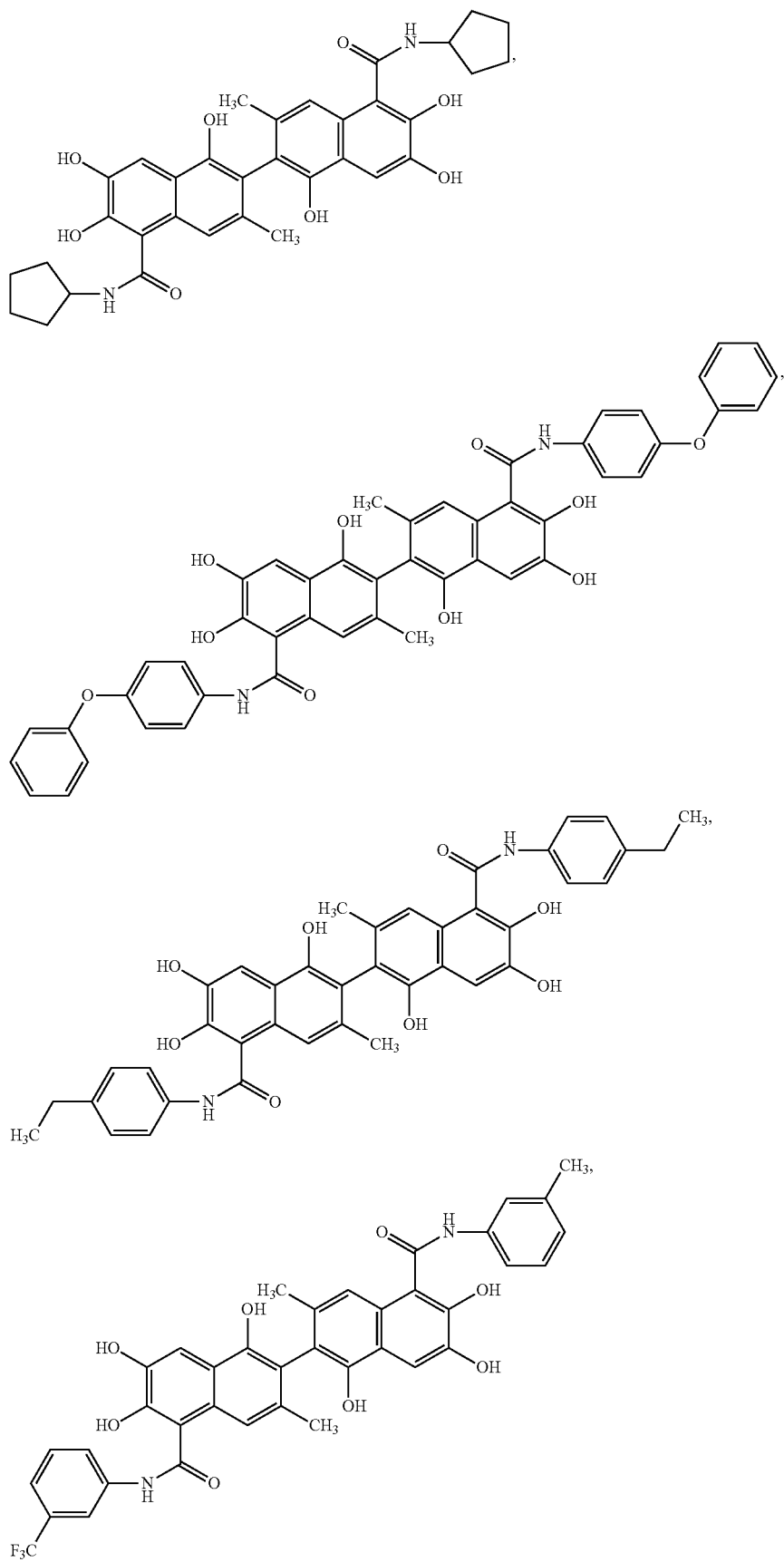

-continued
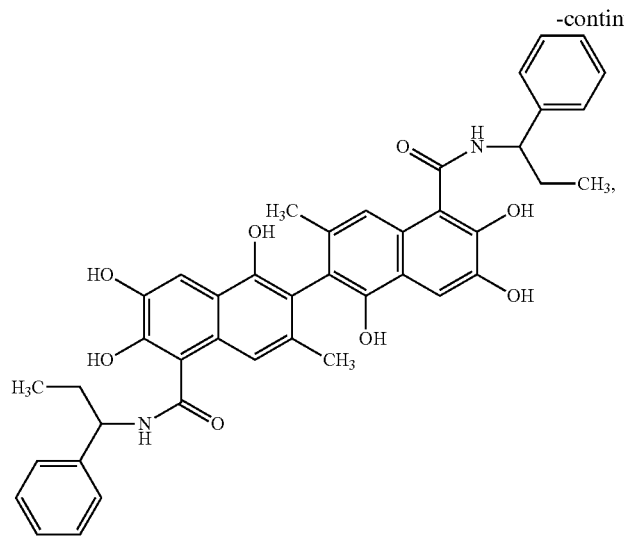
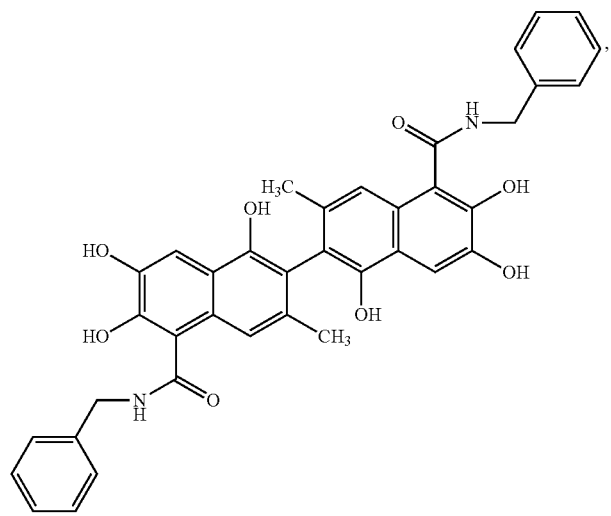
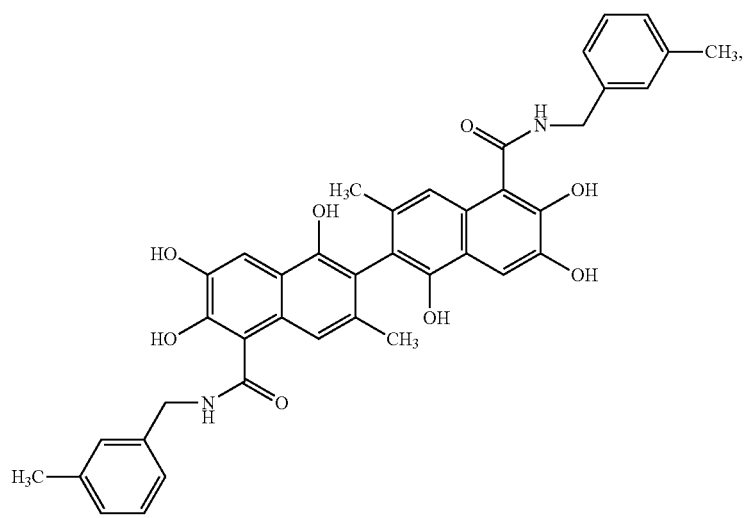

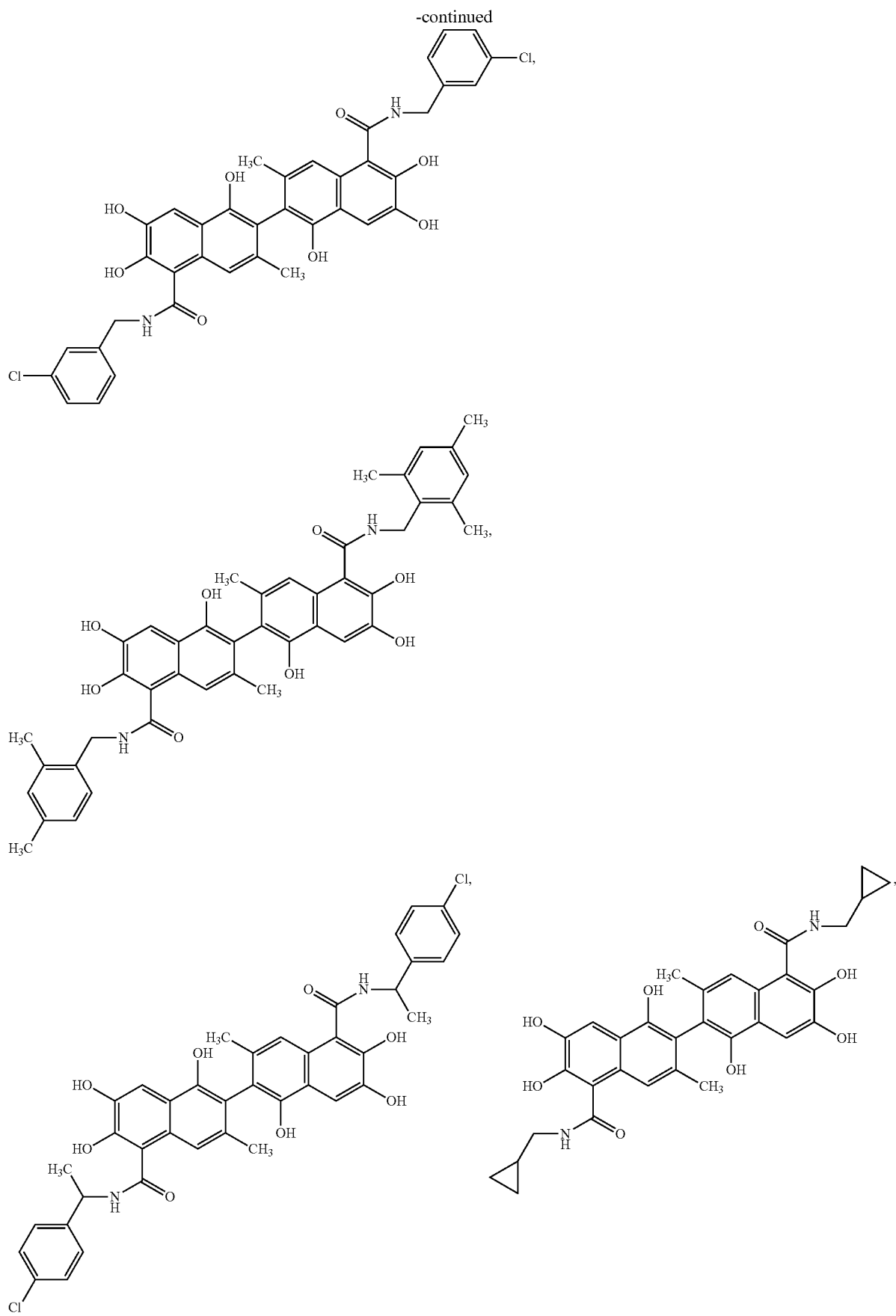

-continued
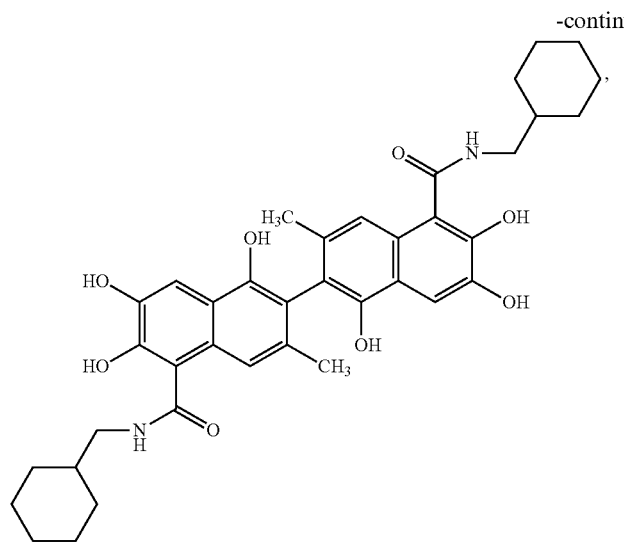
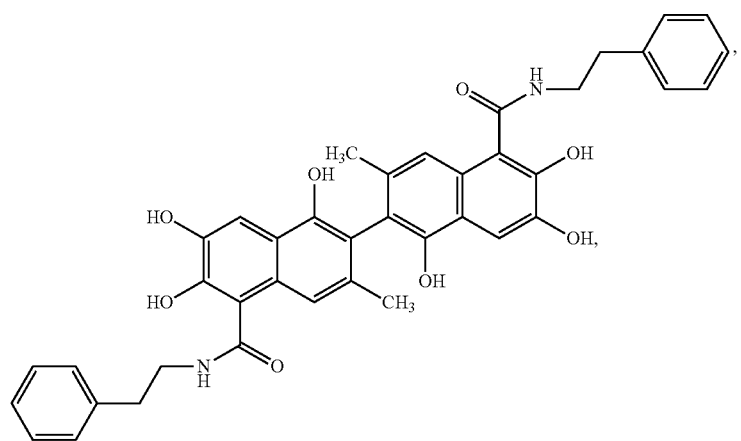
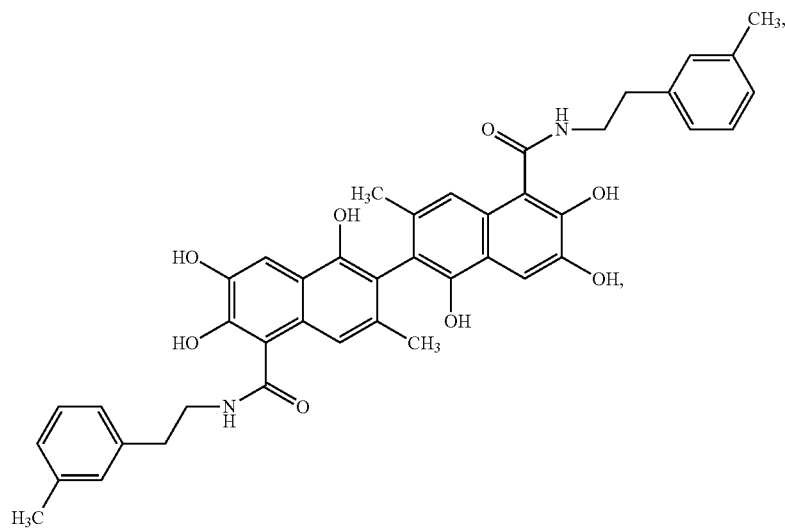

-continued
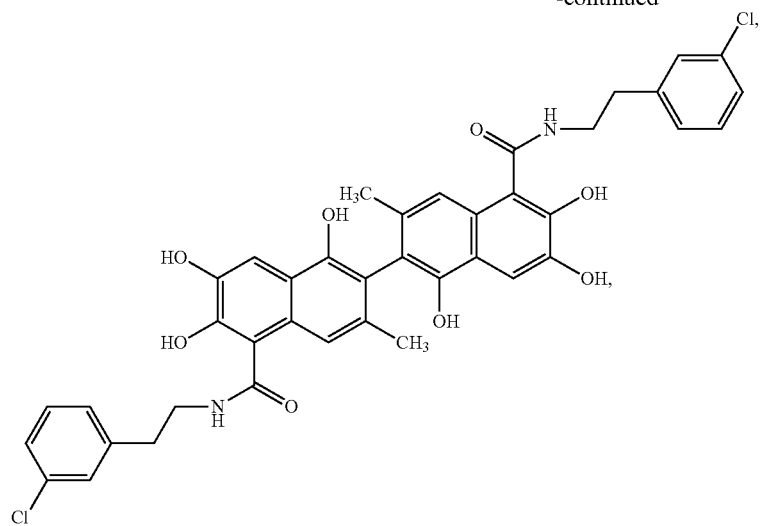
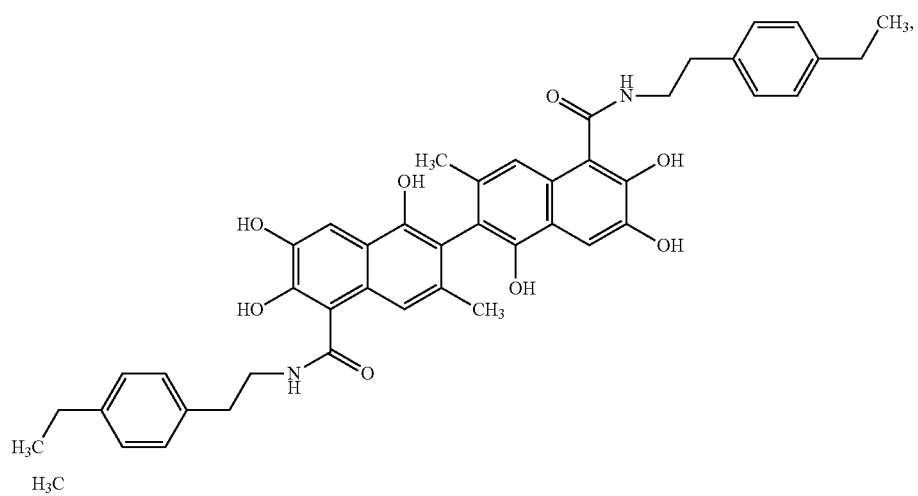
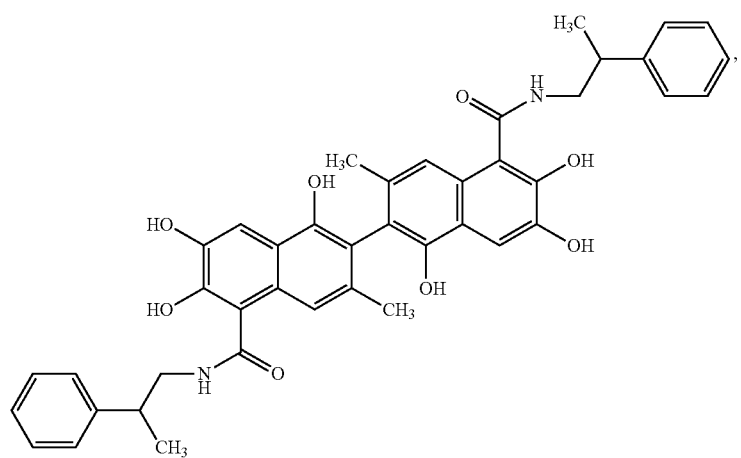

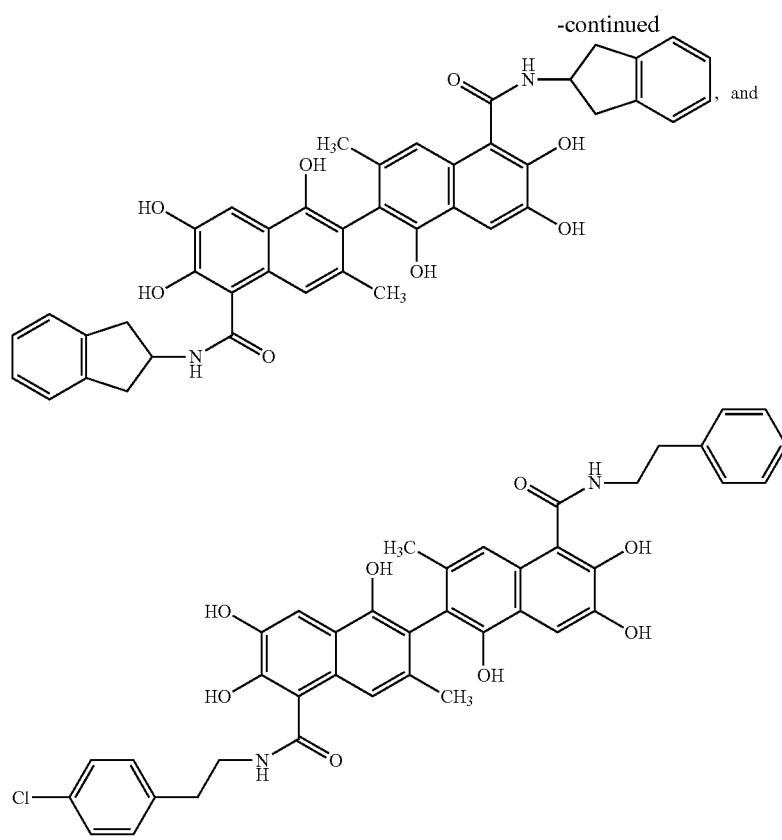
In some embodiments, the compound is selected from the group consisting of:
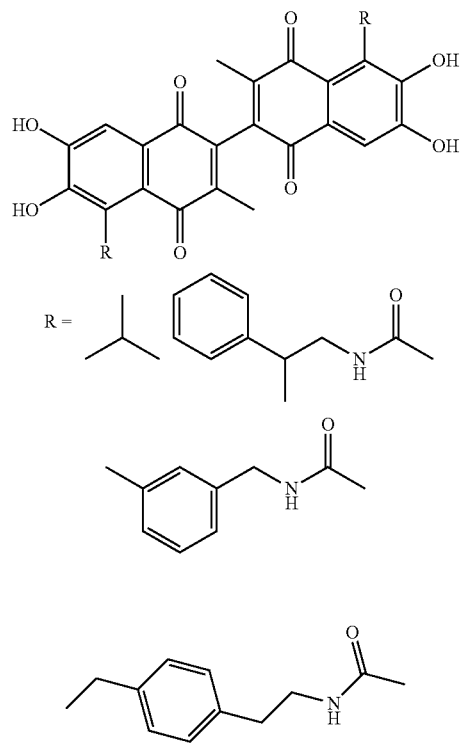
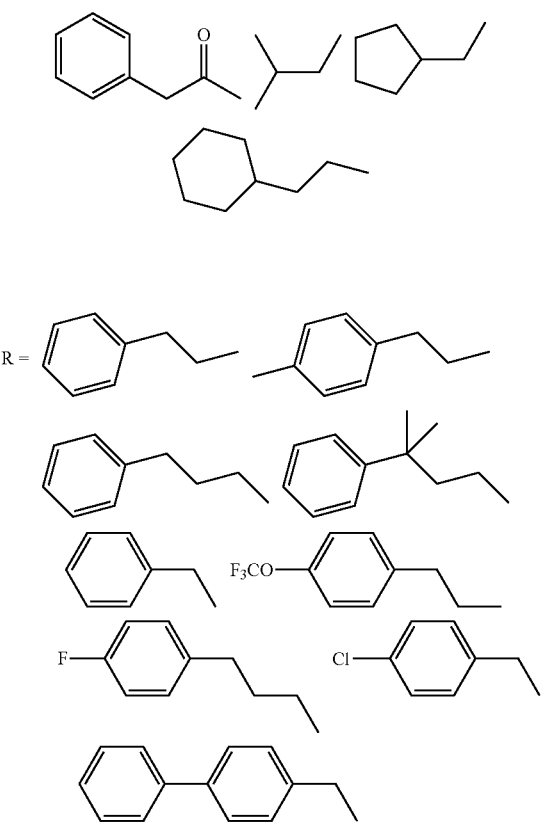

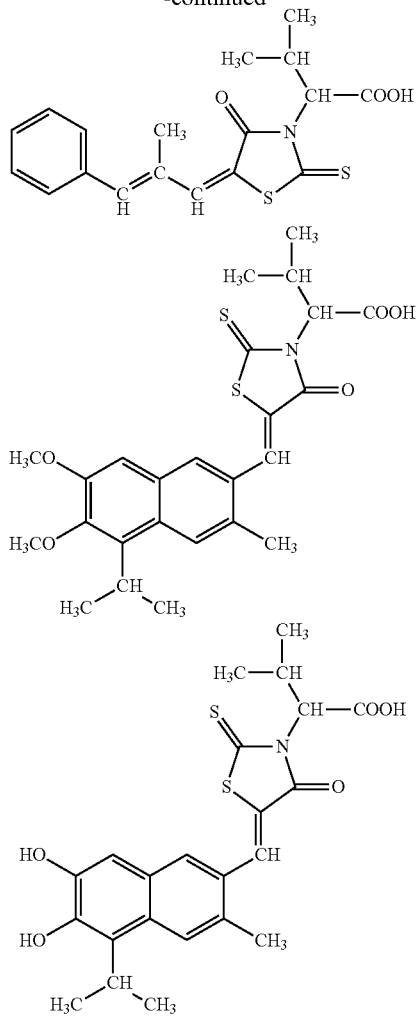
In some embodiments, the compound is selected from the group consisting of:
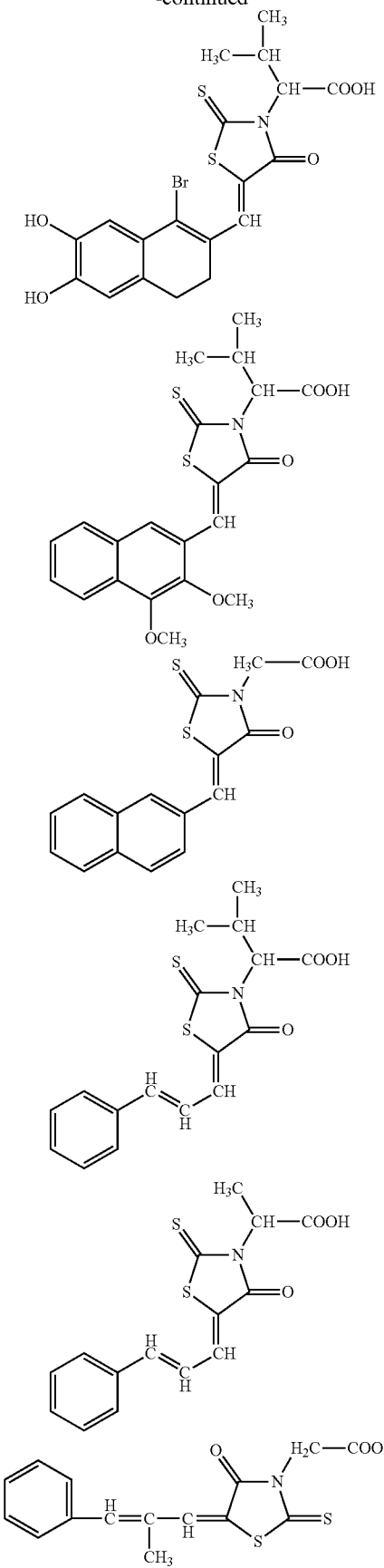

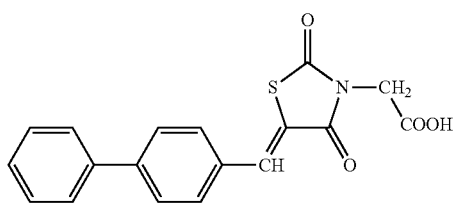
In some embodiments, the compound is selected from the group consisting of:
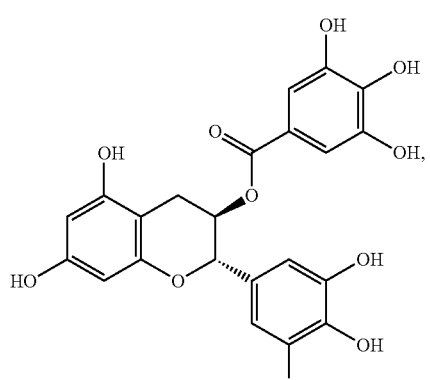
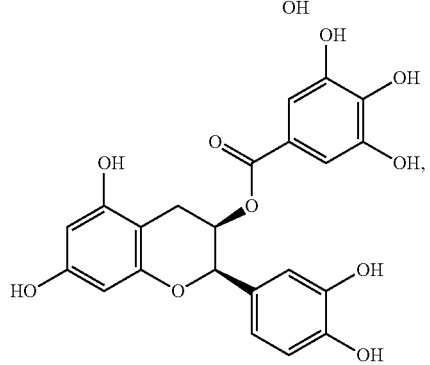
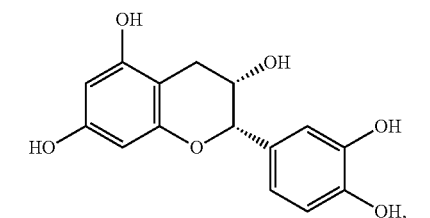
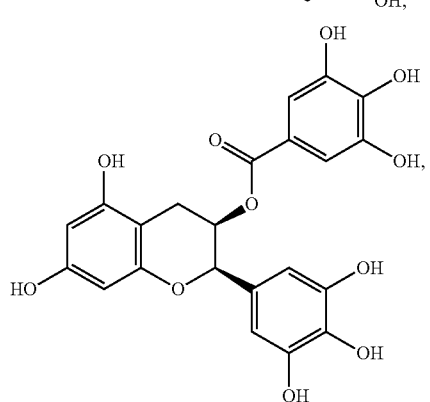
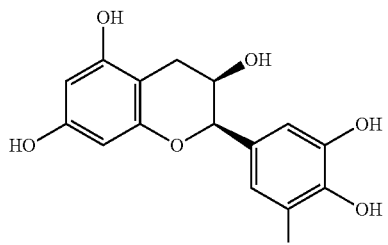
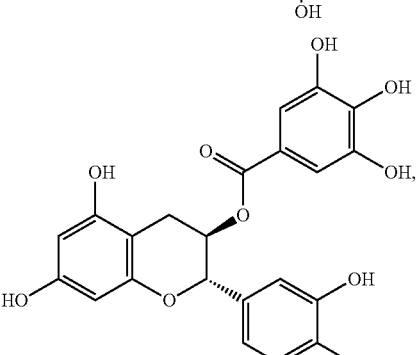
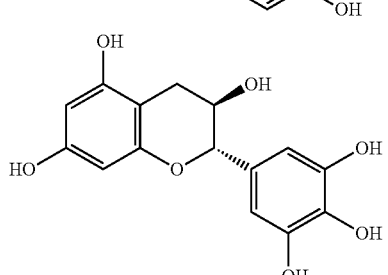
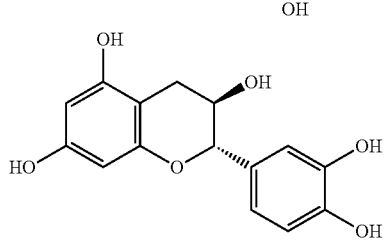

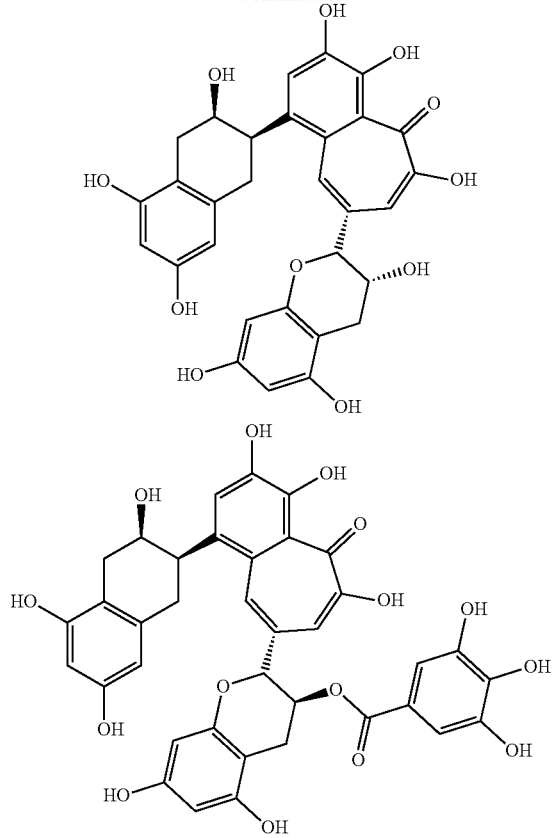

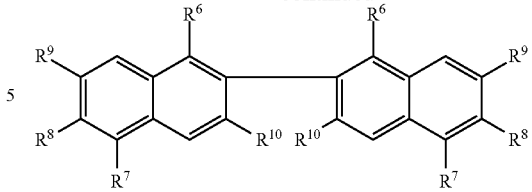

wherein:
each $R^6$, $R^8$, $R^9$ and $R^{10}$ are independently hydrogen, hydroxyl, —($C_1$-$C_6$)alkyl, —O($C_1$-$C_6$)alkyl, —($C_1$-$C_6$)alkylhalo, —OC(O)($C_1$-$C_6$)alkyl, or halo; ech $R^7$ is independently hydrogen, —($C_3$-$C_8$)cycloalkyl, —($C_6$-$C_{10}$)aryl, or —($C_1$-$C_6$)alkyl($C_6$-$C_{10}$)aryl; or a pharmaceutically acceptable salt thereof.

The composition can be formulated with one or more pharmaceutically-acceptable excipients in the form of a pharmaceutical formulation.

A compound described herein can be at least 1% pure, at least 2% pure, at least 3% pure, at least 4% pure, at least 5% pure, at least 6% pure, at least 7% pure, at least 8% pure, at least 9% pure, at least 10% pure, at least 11% pure, at least 12% pure, at least 13% pure, at least 14% pure, at least 15% pure, at least 16% pure, at least 17% pure, at least 18% pure, at least 19% pure, at least 20% pure, at least 21% pure, at least 22% pure, at least 23% pure, at least 24% pure, at least 25% pure, at least 26% pure, at least 27% pure, at least 28% pure, at least 29% pure, at least 30% pure, at least 31% pure, at least 32% pure, at least 33% pure, at least 34% pure, at least 35% pure, at least 36% pure, at least 37% pure, at least 38% pure, at least 39% pure, at least 40% pure, at least 41% pure, at least 42% pure, at least 43% pure, at least 44% pure, at least 45% pure, at least 46% pure, at least 47% pure, at least 48% pure, at least 49% pure, at least 50% pure, at least 51% pure, at least 52% pure, at least 53% pure, at least 54% pure, at least 55% pure, at least 56% pure, at least 57% pure,

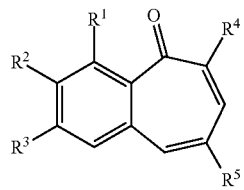

| CMPD | $R_1$ | $R_2$ | $R_3$ | $R_4$ | $R_5$ |
|---|---|---|---|---|---|
| Purparogallin | —OH | —OH | —OH | —OH | —H |
| 5D1 | —H | —OH | —OH | —OH | —COOC$_2$H$_5$ |
| 1163 | —H | —OH | —OH | —OH | —COOCH$_3$ |
| 1142 | —H | —OH | —OH | —OH | —COOH |
| 6A1 | —OCH$_3$ | —OCH$_3$ | —OCH$_3$ | —OCH$_3$ | —H |
| 6A7 | —OCH$_3$ | —OCH$_3$ | —OH | —OCH$_3$ | —H |

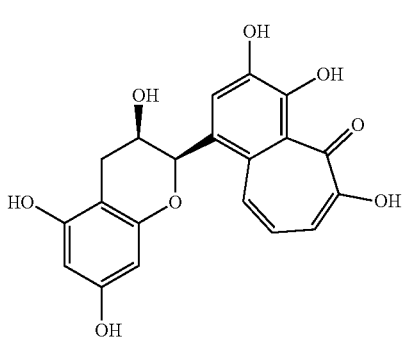

at least 58% pure, at least 59% pure, at least 60% pure, at least 61% pure, at least 62% pure, at least 63% pure, at least 64% pure, at least 65% pure, at least 66% pure, at least 67% pure, at least 68% pure, at least 69% pure, at least 70% pure, at least 71% pure, at least 72% pure, at least 73% pure, at least 74% pure, at least 75% pure, at least 76% pure, at least 77% pure, at least 78% pure, at least 79% pure, at least 80% pure, at least 81% pure, at least 82% pure, at least 83% pure, at least 84% pure, at least 85% pure, at least 86% pure, at least 87% pure, at least 88% pure, at least 89% pure, at least 90% pure, at least 91% pure, at least 92% pure, at least 93% pure, at least 94% pure, at least 95% pure, at least 96% pure, at least 97% pure, at least 98% pure, at least 99% pure, at least 99.1% pure, at least 99.2% pure, at least 99.3% pure, at least 99.4% pure, at least 99.5% pure, at least 99.6% pure, at least 99.7% pure, at least 99.8% pure, or at least 99.9% pure on a chemical, optical, isomeric, enantiomeric, or diastereomeric basis.

The invention provides the use of pharmaceutically-acceptable salts of any therapeutic compound described herein. Pharmaceutically-acceptable salts include, for example, acid-addition salts and base-addition salts. The acid that is added to a compound described herein to form an acid-addition salt can be an organic acid or an inorganic acid. A base that is added to a compound described herein to form a base-addition salt can be an organic base or an inorganic base. In some embodiments, a pharmaceutically-acceptable salt is a metal salt. In some embodiments, a pharmaceutically-acceptable salt is an ammonium salt.

Metal salts can arise from the addition of an inorganic base to a compound described herein of the invention. The inorganic base consists of a metal cation paired with a basic counterion, such as, for example, hydroxide, carbonate, bicarbonate, or phosphate. The metal can be an alkali metal, alkaline earth metal, transition metal, or main group metal. In some embodiments, the metal is lithium, sodium, potassium, cesium, cerium, magnesium, manganese, iron, calcium, strontium, cobalt, titanium, aluminum, copper, cadmium, or zinc.

In some embodiments, a metal salt is a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt, a cadmium salt, or a zinc salt.

Ammonium salts can arise from the addition of ammonia or an organic amine to a compound described herein of the invention. In some embodiments, the organic amine is triethyl amine, diisopropyl amine, ethanol amine, diethanol amine, triethanol amine, morpholine, N-methylmorpholine, piperidine, N-methylpiperidine, N-ethylpiperidine, dibenzylamine, piperazine, pyridine, pyrrazole, pipyrrazole, imidazole, pyrazine, or pipyrazine.

In some embodiments, an ammonium salt is a triethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzylamine salt, a piperazine salt, a pyridine salt, a pyrrazole salt, a pipyrrazole salt, an imidazole salt, a pyrazine salt, or a pipyrazine salt.

Acid addition salts can arise from the addition of an acid to a compound described herein of the invention. In some embodiments, the acid is organic. In some embodiments, the acid is inorganic. In some embodiments, the acid is hydrochloric acid, hydrobromic acid, hydroiodic acid, nitric acid, nitrous acid, sulfuric acid, sulfurous acid, a phosphoric acid, isonicotinic acid, lactic acid, salicylic acid, tartaric acid, ascorbic acid, gentisinic acid, gluconic acid, glucaronic acid, saccaric acid, formic acid, benzoic acid, glutamic acid, pantothenic acid, acetic acid, propionic acid, butyric acid, fumaric acid, succinic acid, methanesulfonic acid, ethanesulfonic acid, benzenesulfonic acid, p-toluenesulfonic acid, citric acid, oxalic acid, or maleic acid.

In some embodiments, the salt is a hydrochloride salt, a hydrobromide salt, a hydroiodide salt, a nitrate salt, a nitrite salt, a sulfate salt, a sulfite salt, a phosphate salt, isonicotinate salt, a lactate salt, a salicylate salt, a tartrate salt, an ascorbate salt, a gentisinate salt, a gluconate salt, a glucaronate salt, a saccarate salt, a formate salt, a benzoate salt, a glutamate salt, a pantothenate salt, an acetate salt, a propionate salt, a butyrate salt, a fumarate salt, a succinate salt, a methanesulfonate (mesylate) salt, an ethanesulfonate salt, a benzenesulfonate salt, a p-toluenesulfonate salt, a citrate salt, an oxalate salt, or a maleate salt.

Pharmaceutical Formulations.

A pharmaceutical composition of the disclosure can be a combination of any pharmaceutical formulation of a compound described herein with other chemical components, such as carriers, stabilizers, diluents, dispersing agents, suspending agents, thickening agents, and/or excipients. The pharmaceutical composition facilitates administration of a compound described herein to an organism. Pharmaceutical compositions can be administered in therapeutically-effective amounts as pharmaceutical compositions by any form and route known in the art including, for example, intravenous, subcutaneous, intramuscular, oral, rectal, parenteral, ophthalmic, pulmonary, transdermal, vaginal, otic, nasal, and topical administration.

A pharmaceutical composition can be administered in a local or systemic manner, for example, via injection of a compound described herein directly into an organ, optionally in a depot or sustained release formulation. Pharmaceutical compositions can be provided in the form of a rapid release formulation, in the form of an extended release formulation, or in the form of an intermediate release formulation. A rapid release form can provide an immediate release. An extended release formulation can provide a controlled release or a sustained delayed release.

For oral administration, pharmaceutical compositions can be formulated by combining a compound described herein with pharmaceutically acceptable carriers or excipients. Such carriers can be used to formulate liquids, gels, syrups, elixirs, slurries, or suspensions for oral ingestion by a subject. Non-limiting examples of solvents used in an oral dissolvable formulation can include water, ethanol, isopropanol, saline, physiological saline, DMSO, dimethylformamide, potassium phosphate buffer, phosphate buffer saline (PBS), sodium phosphate buffer, 4-2-hydroxyethyl-1-piperazineethanesulfonic acid buffer (HEPES), 3-(N-morpholino)propanesulfonic acid buffer (MOPS), piperazine-N, N'-bis(2-ethanesulfonic acid) buffer (PIPES), and saline sodium citrate buffer (SSC). Non-limiting examples of co-solvents used in an oral dissolvable formulation can include sucrose, urea, cremaphor, DMSO, and potassium phosphate buffer.

Pharmaceutical preparations can be formulated for intravenous administration. The pharmaceutical compositions can be in a form suitable for parenteral injection as a sterile suspension, solution or emulsion in oily or aqueous vehicles, and can contain formulatory agents such as suspending, stabilizing and/or dispersing agents. Pharmaceutical formulations for parenteral administration include aqueous solutions of a compound described herein in water-soluble form. Suspensions of a compound described herein can be prepared as oily injection suspensions. Suitable lipophilic solvents or vehicles include fatty oils such as sesame oil, or synthetic fatty acid esters, such as ethyl oleate or triglycerides, or liposomes. The suspension can also contain suitable stabilizers or agents which increase the solubility of a compound described herein to allow for the preparation of highly concentrated solutions. Alternatively, the active ingredient can be in powder form for constitution with a suitable vehicle, e.g., sterile pyrogen-free water, before use.

A compound described herein can be administered topically and can be formulated into a variety of topically administrable compositions, such as solutions, suspensions, lotions, gels, pastes, medicated sticks, balms, creams, and ointments. Such pharmaceutical compositions can contain solubilizers, stabilizers, tonicity enhancing agents, buffers and preservatives.

A compound described herein can also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, and PEG. In suppository forms of the compositions, a low-melting wax such as a mixture of fatty acid glycerides, optionally in combination with cocoa butter, is first melted.

In practicing the methods of treatment or use provided herein, therapeutically-effective amounts of a compound described herein is administered in pharmaceutical compositions to a subject having a disease or condition to be treated. In some embodiments, the subject is a mammal such as a human. A therapeutically-effective amount can vary widely depending on the severity of the disease, the age and relative health of the subject, the potency of a compound described herein used, and other factors.

Pharmaceutical compositions can be formulated using one or more physiologically-acceptable carriers comprising excipients and auxiliaries, which facilitate processing of a compound described herein into preparations that can be used pharmaceutically. Formulation can be modified depending upon the route of administration chosen. Pharmaceutical compositions comprising a compound described herein can be manufactured in a conventional manner, for example, by means of conventional mixing, dissolving, granulating, or emulsifying.

The pharmaceutical compositions can include at least one pharmaceutically acceptable carrier, diluent, or excipient and a compound described herein or pharmaceutically-acceptable salt form.

Methods for the preparation of compositions comprising a compound described herein can include formulating a compound described herein with one or more inert, pharmaceutically-acceptable excipients. Liquid compositions include, for example, solutions in which a compound described herein is dissolved, emulsions comprising a compound described herein, or a solution containing liposomes, micelles, or nanoparticles comprising a compound described herein as disclosed herein. Semi-solid compositions include, for example, gels, suspensions and creams. The compositions can be in liquid solutions or suspensions, solid forms suitable for solution or suspension in a liquid prior to use, or as emulsions. These compositions can also contain minor amounts of nontoxic, auxiliary substances, such as wetting or emulsifying agents, pH buffering agents, and other pharmaceutically-acceptable additives.

A compound described herein can be delivered via liposomal technology. The use of liposomes as drug carriers can increase the therapeutic index of a compound described hereins. Liposomes are composed of natural phospholipids, and can contain mixed lipid chains with surfactant properties (e.g., egg phosphatidylethanolamine). A liposome design can employ surface ligands for attaching to unhealthy tissue. Non-limiting examples of liposomes include the multilamellar vesicle (MLV), the small unilamellar vesicle (SUV), and the large unilamellar vesicle (LUV). Liposomal physicochemical properties can be modulated to optimize penetration through biological barriers and retention at the site of administration, and to reduce a likelihood of developing premature degradation and toxicity to non-target tissues. Optimal liposomal properties depend on the administration route: large-sized liposomes show good retention upon local injection, small-sized liposomes are better suited to achieve passive targeting. PEGylation reduces the uptake of the liposomes by the liver and spleen, and increases the circulation time, resulting in increased localization at the inflamed site due to the enhanced permeability and retention (EPR) effect. Additionally, liposomal surfaces can be modified to achieve selective delivery of the encapsulated drug to specific target cells. Non-limiting examples of targeting ligands include monoclonal antibodies, vitamins, peptides, and polysaccharides specific for receptors concentrated on the surface of cells associated with the disease.

Non-limiting examples of dosage forms suitable for use in the disclosure include liquid, elixir, nanosuspension, aqueous or oily suspensions, drops, syrups, and any combination thereof. Non-limiting examples of pharmaceutically-acceptable excipients suitable for use in the disclosure include granulating agents, binding agents, lubricating agents, disintegrating agents, sweetening agents, glidants, anti-adherents, anti-static agents, surfactants, anti-oxidants, gums, coating agents, coloring agents, flavouring agents, coating agents, plasticizers, preservatives, suspending agents, emulsifying agents, plant cellulosic material and spheronization agents, and any combination thereof.

Non-limiting examples of pharmaceutically-acceptable excipients can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), each of which is incorporated by reference in its entirety.

Compositions of the invention can be packaged as a kit. In some embodiments, a kit includes written instructions on the administration/use of the composition. The written material can be, for example, a label. The written material can suggest conditions methods of administration. The instructions provide the subject and the supervising physician with the best guidance for achieving the optimal clinical outcome from the administration of the therapy. The written material can be a label. In some embodiments, the label can be approved by a regulatory agency, for example the U.S. Food and Drug Administration (FDA), the European Medicines Agency (EMA), or other regulatory agencies.

Dosing.

Pharmaceutical compositions described herein can be in unit dosage forms suitable for single administration of precise dosages. In unit dosage form, the formulation is divided into unit doses containing appropriate quantities of one or more compounds described herein. The unit dosage can be in the form of a package containing discrete quantities of the formulation. Non-limiting examples are liquids in vials or ampoules. Aqueous suspension compositions can be packaged in single-dose non-reclosable containers. Multiple-dose reclosable containers can be used, for example, in combination with a preservative. Formulations for parenteral injection can be presented in unit dosage form, for example, in ampoules, or in multi-dose containers with a preservative.

A compound described herein can be present in a composition in a range of from about 1 mg to about 2000 mg; from about 100 mg to about 2000 mg; from about 10 mg to about 2000 mg; from about 5 mg to about 1000 mg, from about 10 mg to about 500 mg, from about 50 mg to about 250 mg, from about 100 mg to about 200 mg, from about 1 mg to about 50 mg, from about 50 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 550 mg, from about 550 mg to about 600 mg, from about 600 mg to about 650 mg, from about 650 mg to about 700 mg, from about 700 mg to about 750 mg, from about 750 mg to about 800 mg, from about 800 mg to about 850 mg, from about 850 mg to about 900 mg, from about 900 mg to about 950 mg, or from about 950 mg to about 1000 mg.

A compound described herein can be present in a composition in an amount of about 1 mg, about 2 mg, about 3 mg, about 4 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg.

In some embodiments, a dose can be expressed in terms of an amount of the drug divided by the mass of the subject, for example, milligrams of drug per kilograms of subject body mass. In some embodiments, a compound described herein is present in a composition in an amount ranging from about 250 mg/kg to about 2000 mg/kg, about 10 mg/kg to about 800 mg/kg, about 50 mg/kg to about 400 mg/kg, about 100 mg/kg to about 300 mg/kg, or about 150 mg/kg to about 200 mg/kg.

The foregoing ranges are merely suggestive. Dosages can be altered depending on a number of variables, including, for example, the activity of a compound used, the disease or condition to be treated, the mode of administration, the requirements of the individual subject, the severity of the disease or condition being treated, and the judgment of the practitioner.

In some embodiments, are methods for treating diseases or disorders comprising administering a compound described herein to a subject in need thereof. In some embodiments, a compound described herein is administered in a manner that would be considered ineffective for treating any condition herein. In some embodiments, a compound described herein is administered in a decreased cumulative dose, over multiple therapeutic cycles compared with the amount required for cancer therapy.

In some embodiments, a compound described herein is administered within a treatment cycle, which treatment cycle comprises a treatment course followed by a non-treatment interval. One or more doses of a compound described herein can be administered on one or more days.

In some embodiments, the methods comprise administering a compound described herein in at least two treatment cycles. A non-treatment interval can be at least about 2 weeks or about 0.5 to about 12 months, such as at least about one month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months. The non-treatment interval can be about 1 to about 2 years or about 1 to about 3 years, or longer. Each treatment course can be, for example, no longer than about 1 month, no longer than about 2 months, or no longer than about 3 months; or is no longer than 1, 2, 3, 4, 5, 6, 7, 8, 9, 10, 11, 12, 13, 14, 15, 16, 17, 18, 19, 20, 21, 22, 23, 24, 25, 26, 26, 27, 28, 29, 30, or 31 days.

In some embodiments, the treatment window is about one day. In some embodiments, a single treatment course occurs over no longer than 2, 3, 4, 5, 6, 7, 8, 9, 10, 11, 12, 13, 14, 15, 16, 17, 18, 19, 20, 21, 22, 23, 24, 25, 26, 26, 27, 28, 29, 30, or 31 days. During such treatment windows, a compound described herein can be administered at least on 2, 3, 4, 5, 6, 7, 8, 9, 10, 11, 12, 13, 14, 15, 16, 17, 18, 19, 20, 21, 22, 23, 24, 25, 26, 26, 27, 28, 29, 30, or 31 days with a variable number of days on which a compound described herein is not administered. For example, administration can be discontinued for 2, 3, 4, 5, 6, 7, 8, 9, 10, 11, 12, 13, 14, 15, 16, 17, 18, 19, 20, 21, 22, 23, 24, 25, 26, 26, 27, 28, 29, 30, or 31 days, and a discontinuation can occur at any time during the protocol. Intervals can be chosen as appropriate for the disease being treated, a compound described herein being administered, the health status of the subject, and other relevant factors.

A daily dose of a compound described herein can be a single administration or the dose can be divided into 2, 3, 4, or 5 separate administrations to provide the total daily dose of a compound described herein.

A treatment cycle can be repeated as often as needed. For example, a treatment cycle can be repeated at least once, at least twice, at least three times, at least four times, at least five times, at least six times, at least seven times, at least eight times, at least nine times, at least ten times, or more often as needed. Consecutive cycles can have the same, similar, or different durations, dosages, or protocols. Treatment course or a treatment cycle can be repeated, such as when the disease or disorder recurs, or when symptoms or sequelae of the disease or disorder that were significantly diminished by one treatment course as described above have increased or are detectable, or when the symptoms or sequelae of the disease or disorder are exacerbated, a treatment course can be repeated.

A compound described herein can be administered to a subject to reduce likelihood of occurrence or development, or to delay onset, progression, or severity of the disease, and a cycle useful for that purpose can be administered.

In some embodiments, a compound described herein is administered in a treatment window comprising 21 days. In some embodiments, a compound described herein is administered daily for 14 days followed by 7 days off. In some embodiments, a compound described herein is administered daily for 13 days followed by 8 days off. In some embodiments, a compound described herein is administered daily for 12 days followed by 9 days off. In some embodiments, a compound described herein is administered daily for 11 days followed by 10 days off. In some embodiments, a compound described herein is administered daily for 10 days followed by 11 days off. In some embodiments, a compound described herein is administered daily for 9 days followed by 12 days off. In some embodiments, a compound described herein is administered daily for 8 days followed by 13 days off. In some embodiments, a compound described herein is administered daily for 7 days followed by 14 days off. In some embodiments, a compound described herein is administered daily for 6 days followed by 15 days off. In some embodiments, a compound described herein is administered daily for 5 days followed by 16 days off. In some embodiments, a compound described herein is administered daily for 4 days followed by 17 days off. In some embodiments, a compound described herein is administered daily for 3 days followed by 18 days off. In some embodiments, a compound described herein is administered daily for 2 days followed by 19 days off. In some embodiments, a compound described herein is administered for 1 day followed by 20 days off.

In some embodiments, a compound described herein is administered daily for about 21, about 14, or about 7 days in a dose of about 150 mg to about 325 mg. In some embodiments, a compound described herein is administered daily for about 21, about 14, or about 7 days in a dose of about 150 mg to about 300 mg. In some embodiments, a compound described herein is administered daily for about 21, about 14, or about 7 days in a dose of about 150 mg to about 275 mg. In some embodiments, a compound described herein is administered daily for about 21, about 14, or about 7 days in a dose of about 150 mg to about 250 mg. In some embodiments, a compound described herein is administered daily for about 21, about 14, or about 7 days in a dose of about 150 mg to about 225 mg. In some embodiments, a compound described herein is administered daily for about 21, about 14, or about 7 days in a dose of about 150 mg to about 200 mg. In some embodiments, a compound described herein is administered daily for about 21, about 14, or about 7 days in a dose of about 150 mg to about 175 mg. In some embodiments, a compound described herein is administered daily for about 21, about 14, or about 7 days in a dose of about 150 mg. In some embodiments, a compound described herein is administered daily for about 21, about 14, or about 7 days in a dose of about 125 mg. In some embodiments, a compound described herein is administered daily for about 21, about 14, or about 7 days in a dose of about 100 mg. In some embodiments, a compound described herein is administered daily for about 21, about 14, or about 7 days in a dose of about 75 mg. In some embodiments, a compound described herein is administered daily for about 21, about 14, or about 7 days in a dose of about 50 mg. In some embodiments, a compound described herein is administered daily for about 21, about 14, or about 7 days in a dose of about 25 mg.

In some embodiments, a compound described herein is administered in a treatment window of 28 days. In some embodiments, a compound described herein is administered daily for 10 days, followed by 18 days off, daily for 9 days, followed by 19 days off, daily for 8 days, followed by 20 days off daily for 7 days, followed by 21 days off, daily for 6 days, followed by 22 days off, daily for 5 days, followed by 23 days off, daily for 4 days, followed by 24 days off, daily for 3 days, followed by 25 days off daily for 2 days, followed by 26 days off, or for 1 day, followed by 27 days off.

In some specific embodiments, a compound described herein is administered daily for about 10 days in a dose of about 20 mg/m$^2$, about 19 mg/m$^2$, about 18 mg/m$^2$, about 17 mg/m$^2$, about 16 mg/m$^2$, about 15 mg/m$^2$, about 14 mg/m$^2$, about 13 mg/m$^2$, about 12 mg/m$^2$, about 11 mg/m$^2$, about 10 mg/m$^2$, about 9 mg/m$^2$, about 8 mg/m$^2$, about 7 mg/m$^2$, about 6 mg/m$^2$, about 5 mg/m$^2$, about 4 mg/m$^2$, about 3 mg/m$^2$, about 2 mg/m$^2$, about 1 mg/m$^2$, about 0.75 mg/m$^2$, about 0.5 mg/m$^2$, about 0.25 mg/m$^2$, about 0.1 mg/m$^2$, or about 0.01 mg/m$^2$. A compound described herein can be administered for 5, 6, 7, 8, 9, 10, 11, 12, 13, or 14 days at the doses described above.

EXAMPLES

Example 1: Efficacy of a Test Compound in an Animal Model of Osteoarthritis

C57BL/6J mice undergo surgery to cut the anterior cruciate ligament of one rear limb to induce osteoarthritis in the joint of that limb. At week 2 post-surgery, mice receive 2.5 µg of test compound to the operated knee by intra-articular injection, qd for 5 days, with a second treatment (2.5 µg test compound—qd for 5 days) during week 4 post-surgery. At the end of 4 weeks post-surgery, operated joints of the mice are assessed for function, monitored for markers of inflammation, and undergo histological assessment.

Two control groups of mice are included: one group comprising C57BL/6J mice that undergo a sham surgery, for example, surgical procedures are followed except for cutting the ACL, and receive intra-articular injections of vehicle parallel to the treated group; and one group comprising C57BL/6J that undergo an ACL surgery and receive intra-articular injections of vehicle.

Function of the limbs are assessed at 4 weeks post-surgery by a weight bearing test to determine which leg the mice favor. The mice are allowed to acclimate to the chamber on at least 3 occasions prior to taking measurements. Mice are maneuvered inside the chamber to stand with 1 hind paw on each scale. The weight that is placed on each hind limb is measured over a 3-second period. At least 3 separate measurements are made for each animal at each time point. The results are expressed as the percentage of the weight placed on the operated limb versus the contralateral unoperated limb.

The function of the limbs are also assessed at 4 weeks post-surgery by hotplate analysis to show sensitivity and reaction to pain stimulus. In brief, a mouse is placed on a hotplate at 55° C. When placed on the hot surface of the plate, mice will lift their paws and lick them (paw-lick response) due to attainment of pain threshold. The latency period for the hind limb response (paw-lick response) is recorded as response time.

Histopathology of the proteoglycan layer is also analyzed.

Example 2: Efficacy of a Test Compound in an Animal Model of Cardiac Stress Resistance At 12 months of age, mice are injected three times per week with a test compound, while a control group receives vehicle. At 18 months, subsets of male and female mice are subjected to a cardiac stress test, in which mice are injected with a lethal dose of isoproterenol (680 mg/kg) and the time to cardiac arrest is recorded. The time to cardiac arrest is compared between treated and untreated animals.

Example 3: Efficacy of a Test Compound in an Animal Model of Atherosclerosis

LDL$^{-/-}$ mice from 10 weeks of age are fed a high fat diet having 42% calories from fat beginning at Week 0 until Week 12.5. The mice are then switched to a normal chow diet. Mice are treated with a test compound or a vehicle from week 12.5 over the next 100 days, with each treatment cycle comprising 5 days of test compound described herein (25 mg/kg intraperitoneally daily) and 14 days off. At the end of the 100 day treatment period, mice are sacrificed, plasma and tissues are collected, and atherosclerosis is quantitated. Descending aortas are dissected and stained with Sudan IV to visualize the plaque lipids. The percentage of the aorta covered in plaques is measured by area, and is compared between the treated and untreated animals.

Example 4: Efficacy of a Test Compound in Animal Models of Pulmonary Disease

To assess the efficacy of a test compound in treating pulmonary diseases, a model of bleomycin-induced injury is used. In this model, mice develop lung fibrosis within 7-14 days after bleomycin treatment.

Bleomycin is administered to anesthetized 6-8 week-old mice by intratracheal aspiration (2.5 U/kg of bleomycin in 50 µl PBS) using a microsprayer syringe. Control mice are administered saline. The day following bleomycin treatment, a test compound (25 mg/kg in PBS) or vehicle is administered. Mice are treated via intraperitoneal injection for 5 consecutive days, followed by 5 days of rest, followed by a second treatment cycle of 5 consecutive days. Untreated mice receive an equal volume of vehicle. At 7, 14, and 21 days post-bleomycin treatment, lung function is assessed by monitoring oxygen saturation using the MouseSTAT PhysioSuite pulse oximeter. Animals are anesthetized with isoflurane (1.5%) and a toe clip is applied. Mice are monitored for 30 seconds and the average peripheral capillary oxygen saturation ($SpO_2$) measurement over this duration is calculated.

At 21 days post-bleomycin treatment, airway hyper-reactivity (AHR) of mice is examined. AHR of mice is measured by methacholine challenge while other parameters of lung function (airway mechanics, lung volume and lung compliance) are determined using a ventilator. While under ketamine/xylazine anesthesia and subjected to cannulation of the trachea via a tracheostomy (19Fr blunt Luer cannula), airway resistance (elastance) and compliance of mice are assessed at baseline and in response to increasing concentrations of methacholine (0 to 50 mg/mL in PBS) delivered via nebulization. Animals are maintained at 37° C., and while under muscle paralysis (pancuronium); airway function is measured by using a ventilator and lung mechanics system.

Mice are euthanized by i.p injection of pentobarbital. Bronchoalveolar lavage (BAL) fluids and lungs are obtained and analyzed. Hydroxyproline content of lungs is measured and quantitative histopathology is performed.

In a second animal model for pulmonary diseases (e.g., COPD), mice are exposed to cigarette smoke. The effect of a test compound on the mice exposed to smoke is assessed by lung function and histopathology.

Six week-old mice are chronically exposed to cigarette smoke from a Teague TE-10 system, an automatically-controlled cigarette smoking machine that produces a combination of side-stream and mainstream cigarette smoke in a chamber, which is transported to a collecting and mixing chamber where varying amounts of air is mixed with the smoke mixture. Mice receive a total of 6 hours of cigarette smoke exposure per day, 5 days a week for 6 months. Each lighted cigarette is puffed for 2 seconds and once every minute for a total of 8 puffs, with the flow rate of 1.05 L/min, to provide a standard puff of 35 $cm^3$. The smoke machine is adjusted to produce a mixture of side stream smoke (89%) and mainstream smoke (11%) by smoldering 2 cigarettes at one time. The smoke chamber atmosphere is monitored for total suspended particulates (80-120 mg/$m^3$) and carbon monoxide (350 ppm). Beginning at day 7, mice are treated with a test compound or vehicle (3× per week) (5 consecutive days of treatment followed by 16 days off drug, repeated until the end of the experiment), respectively. An equal number of mice received the corresponding vehicle.

After two months of cigarette smoke exposure, lung function is assessed by monitoring oxygen saturation using the MouseSTAT PhysioSuite pulse oximeter. Animals are anesthetized with isoflurane (1.5%) and the toe clip is applied. Mice are monitored for 30 seconds and the average peripheral capillary oxygen saturation ($SpO_2$) measurement over this duration is calculated.

At the end of the experimental period, airway hyper-reactivity (AHR) of mice to methacholine challenge using a ventilator and lung mechanics system is examined as described above. After AHR measurement, mice are killed by i.p. injection of pentobarbital for in-depth analysis of lung histopathology. Briefly, lungs are inflated with 0.5% low-melting agarose at a constant pressure of 25 cm. Lungs are fixed in 10% buffered formalin and embedded in paraffin. Sections (5 µm) are stained with hematoxylin and eosin. Mean alveolar diameter, alveolar length, and mean linear intercepts are determined by computer-assisted morphometry with Image Pro Plus software.

Example 5: Efficacy of a Test Compound in Treating Chemotherapy-Induced Side Effects Paclitaxel is administered to mice. Groups of mice (n=4) are treated three times every two days with 20 mg/kg paclitaxel or vehicle. Two days after the third dose of paclitaxel, a test compound is administered daily for three days (days 1, 2, and 3) intraperitoneally at 25 mg/kg. Two days after the last dose of a test compound, all groups of animals are housed in metabolic cages to monitor voluntary exercise as determined by wheel counts. Data are collected and analyzed two days later. Wheel count reduction as caused by chemotherapy is observed for restoration by the test compound.

Example 6: Efficacy of a Test Compound in Improving Glucose Tolerance and Insulin Sensitivity Groups of mice (n=9) are fed a high fat diet for four months mice or a regular chow diet. Animals are then treated with a test compound (3 rounds of 25 mg/kg test compound administered daily for five consecutive days) or vehicle. A glucose bolus is given at time zero, and blood glucose is monitored at 20, 30, 60, and 120 minutes after delivering glucose to determine glucose disposal. AUC is quantitated, with a higher AUC value indicating glucose intolerance. Hemoglobin A1c level is also measured for assessing glucose tolerance. Insulin sensitivity is also determined (Insulin Tolerance Testing (ITT)). Changes in weight, body composition, and food intake are also monitored.

What is claimed is:

1. A method of killing a senescent cell, the senescent cell being characterized as a non-cancerous cell in replicative arrest, the method comprising contacting the senescent cell with an effective amount of a senolytic compound that is lethal to the senescent cell, wherein the senolytic compound is apogossypol or a pharmaceutical salt thereof.

2. The method of claim 1, wherein the senescent cell is a fibroblast.

3. The method of claim 1, wherein the senescent cell is a preadipocyte.

4. The method of claim 1, wherein the senescent cell is a chondrocyte.

5. A method of killing senescent cells in a mixed cell population, the senescent cells being characterized as non-cancerous cells in replicative arrest, the method comprising administering to the mixed cell population an effective amount of a senolytic compound, wherein the senolytic compound is apogossypol or a pharmaceutical salt thereof.

6. The method of claim 5, wherein the mixed cell population is present in an organ or tissue.

7. The method of claim 5, wherein the compound kills at least 25% of the senescent cells in the mixed cell population.

8. The method of claim 5, wherein the compound is administered to the mixed cell population in a timed-release formulation.

* * * * *